US012545659B2

(12) United States Patent
Mainolfi et al.

(10) Patent No.: US 12,545,659 B2
(45) Date of Patent: Feb. 10, 2026

(54) IRAK DEGRADERS AND USES THEREOF

(71) Applicant: Kymera Therapeutics, Inc., Watertown, MA (US)

(72) Inventors: Nello Mainolfi, Belmont, MA (US); Nan Ji, Arlington, MA (US); Matthew M. Weiss, Boston, MA (US); Xiaozhang Zheng, Lexington, MA (US); Yi Zhang, Belmont, MA (US); Paul R. Fleming, Lexington, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 794 days.

(21) Appl. No.: 17/597,165

(22) PCT Filed: Jun. 29, 2020

(86) PCT No.: PCT/US2020/040125
§ 371 (c)(1),
(2) Date: Dec. 28, 2021

(87) PCT Pub. No.: WO2020/264499
PCT Pub. Date: Dec. 30, 2020

(65) Prior Publication Data
US 2023/0069104 A1 Mar. 2, 2023

Related U.S. Application Data

(60) Provisional application No. 63/040,891, filed on Jun. 18, 2020, provisional application No. 62/964,955, filed on Jan. 23, 2020, provisional application No. 62/958,980, filed on Jan. 9, 2020, provisional application No. 62/948,968, filed on Dec. 17, 2019, provisional application No. 62/944,834, filed on Dec. 6, 2019, provisional application No. 62/908,153, filed on Sep. 30, 2019, provisional application No. 62/875,407, filed on Jul. 17, 2019, provisional application No. 62/868,609, filed on Jun. 28, 2019.

(51) Int. Cl.
*C07D 401/14* (2006.01)
*C07D 413/14* (2006.01)
*C07D 471/10* (2006.01)
*C07D 487/04* (2006.01)

(52) U.S. Cl.
CPC ......... *C07D 401/14* (2013.01); *C07D 413/14* (2013.01); *C07D 471/10* (2013.01); *C07D 487/04* (2013.01)

(58) Field of Classification Search
CPC .. C07D 401/14; C07D 413/14; C07D 471/10; C07D 487/04; C07D 407/14; C07D 417/14; C07D 487/08; C07D 487/10; C07D 491/08; C07D 497/10; C07D 471/04; C07D 405/14; C07D 498/04; A61K 31/4545; A61K 31/519; A61K 31/5365; A61K 31/5377; A61K 47/55; A61P 29/00; A61P 35/00
See application file for complete search history.

(56) References Cited

U.S. PATENT DOCUMENTS

| | | | |
|---|---|---|---|
| 4,045,485 A | 8/1977 | Fried et al. |
| 4,650,750 A | 3/1987 | Giese |
| 4,709,016 A | 11/1987 | Giese |
| 5,217,866 A | 6/1993 | Summerton et al. |
| 5,360,811 A | 11/1994 | Tegeler et al. |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,721,246 A | 2/1998 | Yoshino et al. |
| 6,306,663 B1 | 10/2001 | Kenten et al. |
| 6,552,065 B2 | 4/2003 | Remiszewski et al. |
| 6,559,280 B2 | 5/2003 | Kenten et al. |
| 6,627,754 B2 | 9/2003 | Blumenkopf et al. |
| 6,949,537 B2 | 9/2005 | Garlich et al. |
| 7,041,298 B2 | 5/2006 | Deshaies et al. |
| 7,071,189 B2 | 7/2006 | Kawashima et al. |
| 7,074,620 B2 | 7/2006 | Kenten et al. |
| 7,173,015 B2 | 2/2007 | Schreiber et al. |
| 7,208,157 B2 | 4/2007 | Dashaies et al. |
| 7,273,920 B2 | 9/2007 | Kenten et al. |

(Continued)

FOREIGN PATENT DOCUMENTS

| | | |
|---|---|---|
| CN | 105085620 B | 5/2018 |
| CN | 114437035 A | 5/2022 |

(Continued)

OTHER PUBLICATIONS

CAS STN Abstract, RN 1787975-60-3 (Pub. Jun. 24, 2015).

(Continued)

*Primary Examiner* — Joseph K McKane
*Assistant Examiner* — David M Shim
(74) *Attorney, Agent, or Firm* — Dechert LLP; Andrea L.C. Reid; Todd K. Macklin

(57) ABSTRACT

The present invention provides compounds, compositions thereof, and methods of using the same. The compounds include an IRAK binding moiety capable of binding to IRAK4 and a degradation inducing moiety (DIM). The DIM could be DTM a ligase binding moiety (LBM) or lysine mimetic. The compounds could be useful as IRAK protein kinase inhibitors and applied to IRAK mediated disorders.

14 Claims, No Drawings

(56) References Cited

U.S. PATENT DOCUMENTS

| | | | |
|---|---|---|---|
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,449,458 | B2 | 11/2008 | Bhamidipati et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,557,210 | B2 | 7/2009 | Singh et al. |
| 7,598,257 | B2 | 10/2009 | Rodgers et al. |
| 7,622,496 | B2 | 11/2009 | Larsen et al. |
| 7,667,039 | B2 | 2/2010 | Garcia-Echeverria et al. |
| 7,713,943 | B2 | 5/2010 | Klippel-Giese et al. |
| 7,781,433 | B2 | 8/2010 | Chuckowree et al. |
| 7,932,260 | B2 | 4/2011 | Fowler et al. |
| 7,989,622 | B2 | 8/2011 | Bajjalieh et al. |
| 8,138,347 | B2 | 3/2012 | Knight et al. |
| 8,185,616 | B2 | 5/2012 | Nagata et al. |
| 8,217,035 | B2 | 7/2012 | Burger et al. |
| 8,338,439 | B2 | 12/2012 | Singh et al. |
| 8,486,941 | B2 | 7/2013 | Burns et al. |
| 8,906,682 | B2 | 12/2014 | June et al. |
| 9,334,320 | B2 | 5/2016 | Okun et al. |
| 9,500,653 | B2 | 11/2016 | Crews et al. |
| 9,632,089 | B2 | 4/2017 | Crews et al. |
| 9,694,084 | B2 | 7/2017 | Bradner et al. |
| 9,750,816 | B2 | 9/2017 | Bradner et al. |
| 9,770,512 | B2 | 9/2017 | Bradner et al. |
| 9,821,068 | B2 | 11/2017 | Bradner et al. |
| 9,969,710 | B2 | 5/2018 | Jorand-Lebrun et al. |
| 10,125,114 | B2 | 11/2018 | Bradner et al. |
| 10,294,229 | B2 | 5/2019 | Gardner et al. |
| 10,336,744 | B2 | 7/2019 | Harling et al. |
| 10,874,743 | B2 | 12/2020 | Mainolfi et al. |
| 11,065,231 | B2 | 7/2021 | Crew et al. |
| 11,117,889 | B1 | 9/2021 | Mainolfi et al. |
| 11,292,792 | B2 | 4/2022 | Ji et al. |
| 11,318,205 | B1 | 5/2022 | Mainolfi et al. |
| 11,352,350 | B2 | 6/2022 | Mainolfi et al. |
| 11,358,948 | B2 | 6/2022 | Mainolfi et al. |
| 11,512,080 | B2 | 11/2022 | Mainolfi et al. |
| 11,542,261 | B2 | 1/2023 | Starczynowski et al. |
| 11,591,332 | B2 | 2/2023 | Weiss et al. |
| 11,685,750 | B2 | 6/2023 | Zheng et al. |
| 11,707,457 | B2 | 7/2023 | Weiss |
| 11,723,980 | B2 | 8/2023 | Mainolfi et al. |
| 11,746,120 | B2 | 9/2023 | Mainolfi et al. |
| 11,773,103 | B2 | 10/2023 | Rong et al. |
| 11,779,578 | B2 | 10/2023 | Weiss |
| 11,807,636 | B2 | 11/2023 | Mainolfi et al. |
| 11,857,535 | B2 | 1/2024 | Walker |
| 12,091,411 | B2 | 9/2024 | Mainolfi et al. |
| 12,150,995 | B2 | 11/2024 | Mainolfi et al. |
| 12,168,057 | B2 | 12/2024 | Mainolfi et al. |
| 12,171,768 | B2 | 12/2024 | Gollob et al. |
| 12,187,744 | B2 | 1/2025 | Leong et al. |
| 12,258,341 | B2 | 3/2025 | Mainolfi et al. |
| 2001/0053782 | A1 | 12/2001 | Blumenkopf et al. |
| 2002/0042427 | A1 | 4/2002 | Tang et al. |
| 2002/0068063 | A1 | 6/2002 | Deshaies et al. |
| 2002/0183360 | A1 | 12/2002 | Muller et al. |
| 2003/0045552 | A1 | 3/2003 | Robarge et al. |
| 2003/0136944 | A1 | 7/2003 | Takehara et al. |
| 2004/0029902 | A1 | 2/2004 | Singh et al. |
| 2004/0048859 | A1 | 3/2004 | Germann et al. |
| 2004/0106569 | A1 | 6/2004 | Klippel-Giese et al. |
| 2004/0116421 | A1 | 6/2004 | Kawashima et al. |
| 2004/0242631 | A1 | 12/2004 | Garlich et al. |
| 2005/0014802 | A1 | 1/2005 | Attardo et al. |
| 2005/0075306 | A1 | 4/2005 | Schreiber et al. |
| 2006/0211657 | A1 | 9/2006 | Singh et al. |
| 2007/0098719 | A1 | 5/2007 | Smith et al. |
| 2007/0135461 | A1 | 6/2007 | Rodgers et al. |
| 2007/0191405 | A1 | 8/2007 | Noronha et al. |
| 2008/0076768 | A1 | 3/2008 | Chuckowree et al. |
| 2008/0108636 | A1 | 5/2008 | Honigberg et al. |
| 2008/0194579 | A1 | 8/2008 | Garcia-Echeverria et al. |
| 2008/0275067 | A1 | 11/2008 | Fowler et al. |
| 2009/0055944 | A1 | 2/2009 | Korman et al. |
| 2009/0136494 | A1 | 5/2009 | Ponath et al. |
| 2009/0171093 | A1 | 7/2009 | Takeuchi et al. |
| 2009/0233903 | A1 | 9/2009 | Rodgers et al. |
| 2010/0087440 | A1 | 4/2010 | Bajalieh et al. |
| 2010/0150892 | A1 | 6/2010 | Han |
| 2010/0197671 | A1 | 8/2010 | Burns et al. |
| 2010/0197686 | A1 | 8/2010 | Xing et al. |
| 2010/0203056 | A1 | 8/2010 | Irving et al. |
| 2010/0233183 | A1 | 9/2010 | Triebel et al. |
| 2010/0234377 | A1 | 9/2010 | Aicher et al. |
| 2010/0247554 | A1 | 9/2010 | Lemke et al. |
| 2010/0249092 | A1 | 9/2010 | Singh et al. |
| 2010/0249126 | A1 | 9/2010 | Burger et al. |
| 2010/0279316 | A1 | 11/2010 | Gorelik et al. |
| 2011/0008331 | A1 | 1/2011 | Triebel |
| 2011/0053941 | A1 | 3/2011 | Mautino et al. |
| 2011/0136796 | A1 | 6/2011 | Mautino et al. |
| 2011/0165156 | A1 | 7/2011 | Dimoudis et al. |
| 2011/0196150 | A1 | 8/2011 | Man et al. |
| 2011/0223611 | A1 | 9/2011 | Salamone et al. |
| 2011/0274683 | A1 | 11/2011 | Wong et al. |
| 2012/0015962 | A1 | 1/2012 | Arora et al. |
| 2012/0189639 | A1 | 7/2012 | Schebye et al. |
| 2012/0277217 | A1 | 11/2012 | Mautino et al. |
| 2012/0283238 | A1 | 11/2012 | Romero et al. |
| 2012/0329997 | A1 | 12/2012 | Fertig et al. |
| 2013/0005949 | A1 | 1/2013 | Fertig et al. |
| 2013/0149236 | A1 | 6/2013 | Johnson et al. |
| 2013/0190340 | A1 | 7/2013 | Hedstrom et al. |
| 2013/0231328 | A1 | 9/2013 | Harriman et al. |
| 2013/0274241 | A1 | 10/2013 | Jorand-Lebrun et al. |
| 2014/0018343 | A1 | 1/2014 | Romero et al. |
| 2014/0018357 | A1 | 1/2014 | Harriman et al. |
| 2014/0018361 | A1 | 1/2014 | Harriman et al. |
| 2014/0066625 | A1 | 3/2014 | Mautino et al. |
| 2014/0079699 | A1 | 3/2014 | Wong et al. |
| 2014/0079706 | A1 | 3/2014 | Cannarile et al. |
| 2014/0093511 | A1 | 4/2014 | Lonberg et al. |
| 2014/0155379 | A1 | 6/2014 | Ho et al. |
| 2014/0194404 | A1 | 7/2014 | McElroy et al. |
| 2014/0302523 | A1 | 10/2014 | Crews et al. |
| 2014/0329799 | A1 | 11/2014 | Seganish et al. |
| 2014/0336363 | A1 | 11/2014 | Fertig et al. |
| 2014/0341917 | A1 | 11/2014 | Nastri et al. |
| 2014/0356322 | A1 | 12/2014 | Crews et al. |
| 2015/0011532 | A1 | 1/2015 | Paidi et al. |
| 2015/0018344 | A1 | 1/2015 | Paidi et al. |
| 2015/0025093 | A1 | 1/2015 | Romero et al. |
| 2015/0045347 | A1 | 2/2015 | Dodd et al. |
| 2015/0094305 | A1 | 4/2015 | Romero et al. |
| 2015/0133451 | A1 | 5/2015 | Yoshida et al. |
| 2015/0141396 | A1 | 5/2015 | Crosignani et al. |
| 2015/0191464 | A1 | 7/2015 | Santella et al. |
| 2015/0225410 | A1 | 8/2015 | Castro et al. |
| 2015/0225449 | A1 | 8/2015 | Donnell et al. |
| 2015/0274708 | A1 | 10/2015 | Seganish et al. |
| 2015/0274738 | A1 | 10/2015 | Gray et al. |
| 2015/0284382 | A1 | 10/2015 | Bhide et al. |
| 2015/0284405 | A1 | 10/2015 | Trzupek et al. |
| 2015/0291562 | A1 | 10/2015 | Crew et al. |
| 2015/0299224 | A1 | 10/2015 | Seganish et al. |
| 2015/0329498 | A1 | 11/2015 | Romero et al. |
| 2015/0374678 | A1 | 12/2015 | Chamberlain et al. |
| 2015/0376167 | A1 | 12/2015 | Jorand-Lebrun et al. |
| 2015/0376206 | A1 | 12/2015 | Jorand-Lebrun et al. |
| 2016/0002265 | A1 | 1/2016 | Jenkins et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0145252 | A1 | 5/2016 | Jorand-Lebrun et al. |
| 2016/0176916 | A1 | 6/2016 | Bradner et al. |
| 2016/0214972 | A1 | 7/2016 | Jin et al. |
| 2016/0235730 | A1 | 8/2016 | Bradner et al. |
| 2016/0235731 | A1 | 8/2016 | Bradner et al. |
| 2016/0243247 | A1 | 8/2016 | Bradner et al. |
| 2016/0256468 | A1 | 9/2016 | Schafer et al. |

(56) References Cited

U.S. PATENT DOCUMENTS

| | | | |
|---|---|---|---|
| 2016/0272596 | A1 | 9/2016 | Chen et al. |
| 2016/0272639 | A1 | 9/2016 | Crew et al. |
| 2016/0311833 | A1 | 10/2016 | Bothe et al. |
| 2016/0311839 | A1 | 10/2016 | Kelley et al. |
| 2016/0326151 | A1 | 11/2016 | Gummadi et al. |
| 2016/0340366 | A1 | 11/2016 | Gummadi et al. |
| 2017/0001990 | A1 | 1/2017 | Chen et al. |
| 2017/0008896 | A1 | 1/2017 | Dahmann et al. |
| 2017/0008904 | A1 | 1/2017 | Crew et al. |
| 2017/0022189 | A1 | 1/2017 | Zhang |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0152263 | A1 | 6/2017 | Gummadi et al. |
| 2017/0152273 | A1 | 6/2017 | Merchant et al. |
| 2017/0204093 | A1 | 7/2017 | Chan et al. |
| 2017/0247388 | A1 | 8/2017 | Altman et al. |
| 2017/0281784 | A1 | 10/2017 | Wang et al. |
| 2017/0327469 | A1 | 11/2017 | Crew et al. |
| 2017/0369476 | A1 | 12/2017 | Chen et al. |
| 2018/0009779 | A1 | 1/2018 | Bradner et al. |
| 2018/0015087 | A1 | 1/2018 | Liu et al. |
| 2018/0051027 | A1 | 2/2018 | Lim et al. |
| 2018/0051028 | A1 | 2/2018 | Lim et al. |
| 2018/0051029 | A1 | 2/2018 | Lim et al. |
| 2018/0051030 | A1 | 2/2018 | Lim et al. |
| 2018/0051035 | A1 | 2/2018 | Lim et al. |
| 2018/0085465 | A1 | 3/2018 | Bradner et al. |
| 2018/0118733 | A1 | 5/2018 | Harling et al. |
| 2018/0127432 | A1 | 5/2018 | Trzupek et al. |
| 2018/0134684 | A1 | 5/2018 | Bradner et al. |
| 2018/0147202 | A1 | 5/2018 | Crew et al. |
| 2018/0169097 | A1 | 6/2018 | Hammerman et al. |
| 2018/0186799 | A1 | 7/2018 | Gardner et al. |
| 2018/0194724 | A1 | 7/2018 | Kemp et al. |
| 2018/0201609 | A1 | 7/2018 | Gummadi et al. |
| 2018/0208605 | A1 | 7/2018 | Gummadi et al. |
| 2018/0228907 | A1 | 8/2018 | Crew et al. |
| 2018/0230157 | A1 | 8/2018 | Bacon et al. |
| 2018/0298015 | A1 | 10/2018 | Bryan et al. |
| 2018/0327419 | A1 | 11/2018 | Bradner et al. |
| 2018/0353501 | A1 | 12/2018 | Crew et al. |
| 2018/0370988 | A1 | 12/2018 | Gummadi et al. |
| 2019/0071415 | A1 | 3/2019 | Bradner et al. |
| 2019/0071432 | A1 | 3/2019 | Bothe et al. |
| 2019/0076539 | A1 | 3/2019 | Phillips et al. |
| 2019/0076540 | A1 | 3/2019 | Phillips et al. |
| 2019/0076541 | A1 | 3/2019 | Phillips et al. |
| 2019/0076542 | A1 | 3/2019 | Phillips et al. |
| 2019/0105322 | A1 | 4/2019 | Macdonald et al. |
| 2019/0151295 | A1 | 5/2019 | Crew et al. |
| 2019/0151457 | A1 | 5/2019 | Bradner et al. |
| 2019/0192532 | A1 | 6/2019 | Bradner et al. |
| 2019/0192668 | A1 | 6/2019 | Mainolfi et al. |
| 2019/0276474 | A1 | 9/2019 | Chan et al. |
| 2019/0374528 | A1 | 12/2019 | Gray et al. |
| 2020/0010468 | A1 | 1/2020 | Ji et al. |
| 2020/0103418 | A1 | 4/2020 | Hackney et al. |
| 2020/0306273 | A1 | 10/2020 | Yang et al. |
| 2020/0347045 | A1 | 11/2020 | Mainolfi et al. |
| 2020/0377469 | A1 | 12/2020 | Mainolfi et al. |
| 2021/0002296 | A1 | 1/2021 | Mainolfi et al. |
| 2021/0032250 | A1 | 2/2021 | Long et al. |
| 2021/0147382 | A1 | 5/2021 | Bellenie et al. |
| 2021/0228562 | A1 | 7/2021 | Weiss |
| 2021/0323952 | A1 | 10/2021 | Mainolfi et al. |
| 2021/0340124 | A1 | 11/2021 | Xue et al. |
| 2021/0395273 | A1 | 12/2021 | Zheng et al. |
| 2022/0054453 | A1 | 2/2022 | Walker |
| 2022/0056046 | A1 | 2/2022 | Gummadi et al. |
| 2022/0273668 | A1 | 9/2022 | Gollob et al. |
| 2022/0274993 | A1 | 9/2022 | Rong et al. |
| 2022/0306631 | A1 | 9/2022 | Ji et al. |
| 2022/0324854 | A1 | 10/2022 | Mainolfi et al. |
| 2022/0340570 | A1 | 10/2022 | Weiss et al. |
| 2023/0038512 | A1 | 2/2023 | Mainolfi et al. |
| 2023/0089916 | A1 | 3/2023 | Mainolfi et al. |
| 2023/0096599 | A1 | 3/2023 | Zheng et al. |
| 2023/0101353 | A1 | 3/2023 | Mainolfi et al. |
| 2023/0106066 | A1 | 4/2023 | Mainolfi et al. |
| 2023/0122219 | A1 | 4/2023 | Weiss et al. |
| 2023/0132715 | A1 | 5/2023 | Ji et al. |
| 2023/0144292 | A1 | 5/2023 | Weiss |
| 2023/0190940 | A1 | 6/2023 | Zhang et al. |
| 2023/0192655 | A1 | 6/2023 | Feng et al. |
| 2023/0219945 | A1 | 7/2023 | Mainolfi et al. |
| 2023/0234936 | A1 | 7/2023 | Feng et al. |
| 2023/0234950 | A1 | 7/2023 | Mainolfi et al. |
| 2023/0234953 | A1 | 7/2023 | Weiss et al. |
| 2023/0241075 | A1 | 8/2023 | Campbell et al. |
| 2023/0250110 | A1 | 8/2023 | Zheng |
| 2023/0257399 | A1 | 8/2023 | Leong et al. |
| 2023/0277519 | A1 | 9/2023 | Gollob et al. |
| 2023/0303526 | A1 | 9/2023 | Mainolfi et al. |
| 2023/0365562 | A1 | 11/2023 | Mainolfi et al. |
| 2023/0398223 | A1 | 12/2023 | Mainolfi et al. |
| 2023/0405012 | A1 | 12/2023 | Rong et al. |
| 2023/0406866 | A1 | 12/2023 | Rong et al. |
| 2023/0416242 | A1 | 12/2023 | Weiss et al. |
| 2024/0059674 | A1 | 2/2024 | Mainolfi et al. |
| 2024/0131016 | A1 | 4/2024 | Weiss |
| 2024/0239777 | A1 | 7/2024 | Mainolfi et al. |
| 2024/0252656 | A1 | 8/2024 | Hencken |
| 2024/0383887 | A1 | 11/2024 | Weiss |
| 2025/0000985 | A1 | 1/2025 | Mainolfi et al. |
| 2025/0011325 | A1 | 1/2025 | Mainolfi et al. |
| 2025/0059164 | A1 | 2/2025 | Zheng et al. |
| 2025/0082645 | A1 | 3/2025 | Gollob et al. |
| 2025/0084105 | A1 | 3/2025 | Leong et al. |

FOREIGN PATENT DOCUMENTS

| | | | |
|---|---|---|---|
| CN | 116925085 | A | 10/2023 |
| CN | 117164583 | A | 12/2023 |
| CN | 118047758 | A | 5/2024 |
| CN | 118440056 | A | 8/2024 |
| WO | 9607655 | A1 | 3/1996 |
| WO | 0110858 | A1 | 2/2001 |
| WO | WO-2001042246 | A2 | 6/2001 |
| WO | WO-2002020740 | A2 | 3/2002 |
| WO | WO-2002088112 | A1 | 11/2002 |
| WO | WO-2003063794 | A2 | 8/2003 |
| WO | WO-2004019973 | A1 | 3/2004 |
| WO | WO-2004089925 | A1 | 10/2004 |
| WO | WO-2004106328 | A1 | 12/2004 |
| WO | WO-2005007623 | A2 | 1/2005 |
| WO | WO-2005113554 | A2 | 12/2005 |
| WO | WO-2006029879 | A2 | 3/2006 |
| WO | WO-2006078846 | A1 | 7/2006 |
| WO | WO-2006105021 | A2 | 10/2006 |
| WO | WO-2006122806 | A2 | 11/2006 |
| WO | WO-2007005874 | A2 | 1/2007 |
| WO | WO-2007016176 | A2 | 2/2007 |
| WO | WO-2007044729 | A2 | 4/2007 |
| WO | WO-2007053452 | A1 | 5/2007 |
| WO | WO-2007070514 | A1 | 6/2007 |
| WO | WO-2007084786 | A1 | 7/2007 |
| WO | WO-2007129161 | A2 | 11/2007 |
| WO | WO-2008039218 | A2 | 4/2008 |
| WO | WO-2008109943 | A1 | 9/2008 |
| WO | WO-2008118802 | A1 | 10/2008 |
| WO | WO-2008132601 | A1 | 11/2008 |
| WO | WO-2009009116 | A2 | 1/2009 |
| WO | WO-2009044273 | A2 | 4/2009 |
| WO | WO-2009073620 | A2 | 6/2009 |
| WO | WO-2009114512 | A1 | 9/2009 |
| WO | WO-2009132238 | A3 | 10/2009 |
| WO | WO-2010019570 | A2 | 2/2010 |
| WO | WO-2010077634 | A1 | 7/2010 |
| WO | WO-2011028683 | A1 | 3/2011 |
| WO | WO-2011043371 | A1 | 4/2011 |
| WO | WO-2011056652 | A1 | 5/2011 |
| WO | WO-2011070024 | A1 | 6/2011 |
| WO | WO-2011090760 | A1 | 7/2011 |

(56) References Cited

FOREIGN PATENT DOCUMENTS

| | | | | |
|---|---|---|---|---|
| WO | WO-2011107553 | A1 | 9/2011 | |
| WO | WO-2011109400 | A2 | 9/2011 | |
| WO | WO-2011131407 | A1 | 10/2011 | |
| WO | WO-2011140249 | A2 | 11/2011 | |
| WO | WO-2012003281 | A3 | 1/2012 | |
| WO | WO-2012007375 | A1 | 1/2012 | |
| WO | WO-2012032433 | A1 | 3/2012 | |
| WO | WO-2012068546 | A1 | 5/2012 | |
| WO | WO-2012078559 | A2 | 6/2012 | |
| WO | WO-2012084704 | A1 | 6/2012 | |
| WO | WO-2012097013 | A1 | 7/2012 | |
| WO | WO-2012129258 | | 9/2012 | |
| WO | WO-2012142237 | A1 | 10/2012 | |
| WO | WO-2012145493 | A1 | 10/2012 | |
| WO | WO-2013042137 | A1 | 3/2013 | |
| WO | WO-2013066729 | A1 | 5/2013 | |
| WO | WO-2013079174 | A1 | 6/2013 | |
| WO | WO-2013087699 | A1 | 6/2013 | |
| WO | WO-2013106535 | A1 | 7/2013 | |
| WO | WO-2013106612 | A1 | 7/2013 | |
| WO | WO-2013106614 | A1 | 7/2013 | |
| WO | WO-2013106641 | A1 | 7/2013 | |
| WO | WO-2013106643 | A2 | 7/2013 | |
| WO | WO-2013106646 | A2 | 7/2013 | |
| WO | WO-2013119716 | A1 | 8/2013 | |
| WO | WO-2013132044 | A1 | 9/2013 | |
| WO | WO-2013169264 | A1 | 11/2013 | |
| WO | WO-2014008218 | A1 | 1/2014 | |
| WO | WO-2014008992 | A1 | 1/2014 | |
| WO | WO-2014011902 | A1 | 1/2014 | |
| WO | WO-2014011906 | A2 | 1/2014 | |
| WO | WO-2014011911 | A2 | 1/2014 | |
| WO | WO-2014036357 | A1 | 3/2014 | |
| WO | WO-2014044622 | A1 | 3/2014 | |
| WO | WO-2014058685 | A1 | 4/2014 | |
| WO | WO-2014058691 | A1 | 4/2014 | |
| WO | WO-2014063061 | A1 | 4/2014 | |
| WO | 2014074660 | A1 | 5/2014 | |
| WO | WO-2014074675 | A1 | 5/2014 | |
| WO | WO-2014108452 | A1 | 7/2014 | |
| WO | WO-2014121931 | A1 | 8/2014 | |
| WO | WO-2014121942 | A1 | 8/2014 | |
| WO | 2014142237 | A1 | 9/2014 | |
| WO | WO-2014143672 | A1 | 9/2014 | |
| WO | WO-2015048281 | A1 | 4/2015 | |
| WO | WO-2015068856 | A1 | 5/2015 | |
| WO | WO-2015071393 | A1 | 5/2015 | |
| WO | WO-2015091426 | A1 | 6/2015 | |
| WO | WO-2015103453 | A1 | 7/2015 | |
| WO | WO-2015104662 | A1 | 7/2015 | |
| WO | WO-2015104688 | A1 | 7/2015 | |
| WO | WO-2015150995 | A1 | 10/2015 | |
| WO | WO-2015160845 | A3 | 10/2015 | |
| WO | WO-2015164374 | A1 | 10/2015 | |
| WO | WO-2015193846 | A1 | 12/2015 | |
| WO | WO-2016011390 | A1 | 1/2016 | |
| WO | WO-2016053769 | A1 | 4/2016 | |
| WO | WO-2016053770 | A1 | 4/2016 | |
| WO | WO-2016053771 | A1 | 4/2016 | |
| WO | WO-2016053772 | A1 | 4/2016 | |
| WO | WO-2016081679 | A1 | 5/2016 | |
| WO | WO-2016105518 | A1 | 6/2016 | |
| WO | WO-2016118666 | A1 | 7/2016 | |
| WO | WO-2016144844 | A1 | 9/2016 | |
| WO | WO-2016144846 | A1 | 9/2016 | |
| WO | WO-2016144847 | A1 | 9/2016 | |
| WO | WO-2016144848 | A1 | 9/2016 | |
| WO | WO-2016144849 | A1 | 9/2016 | |
| WO | WO-2016149668 | A1 | 9/2016 | |
| WO | WO-2016169989 | A1 | 10/2016 | |
| WO | WO-2016172560 | A1 | 10/2016 | |
| WO | WO-2016174183 | A1 | 11/2016 | |
| WO | WO-2016197032 | A1 | 12/2016 | |
| WO | WO-2016197114 | A1 | 12/2016 | |
| WO | WO-2016210034 | A1 | 12/2016 | |
| WO | WO-2017004133 | A1 | 1/2017 | |
| WO | WO-2017004134 | | 1/2017 | |
| WO | WO-2017007612 | A1 | 1/2017 | |
| WO | WO-2017009798 | A1 | 1/2017 | |
| WO | WO-2017009806 | A1 | 1/2017 | |
| WO | WO-2017011371 | A1 | 1/2017 | |
| WO | WO-2017011590 | A1 | 1/2017 | |
| WO | WO-2017030814 | A1 | 2/2017 | |
| WO | 2017046036 | A1 | 3/2017 | |
| WO | WO-2017033093 | A1 | 3/2017 | |
| WO | WO-2017049068 | A1 | 3/2017 | |
| WO | WO-2017059280 | A1 | 4/2017 | |
| WO | WO-2017079267 | A1 | 5/2017 | |
| WO | 2017108744 | A1 | 6/2017 | |
| WO | WO-2017108723 | A2 | 6/2017 | |
| WO | WO-2017117473 | A1 | 7/2017 | |
| WO | WO-2017117474 | A1 | 7/2017 | |
| WO | WO-2017127430 | A1 | 7/2017 | |
| WO | 2017148902 | A1 | 9/2017 | |
| WO | WO-2017161119 | A1 | 9/2017 | |
| WO | WO-2017176708 | A1 | 10/2017 | |
| WO | WO-2017176957 | A1 | 10/2017 | |
| WO | WO-2017176958 | A1 | 10/2017 | |
| WO | WO-2017197036 | A1 | 11/2017 | |
| WO | WO-2017197046 | A1 | 11/2017 | |
| WO | WO-2017197051 | A1 | 11/2017 | |
| WO | WO-2017197055 | A1 | 11/2017 | |
| WO | WO-2017197056 | A1 | 11/2017 | |
| WO | WO-2017201449 | A1 | 11/2017 | |
| WO | WO-2017205762 | A1 | 11/2017 | |
| WO | WO-2017205766 | A1 | 11/2017 | |
| WO | WO-2017207385 | A1 | 12/2017 | |
| WO | WO-2017211924 | A1 | 12/2017 | |
| WO | WO-2018052058 | A1 | 3/2018 | |
| WO | 2018071606 | A1 | 4/2018 | |
| WO | WO-2018089736 | A1 | 5/2018 | |
| WO | WO-2018098367 | A1 | 5/2018 | |
| WO | 2018119441 | A1 | 6/2018 | |
| WO | 2018140809 | A1 | 8/2018 | |
| WO | WO-2018144649 | A1 | 8/2018 | |
| WO | WO-2018209012 | A1 | 11/2018 | |
| WO | WO-2018237026 | A1 | 12/2018 | |
| WO | WO-2019043214 | A1 | 3/2019 | |
| WO | WO-2019060693 | A1 | 3/2019 | |
| WO | WO-2019060742 | A1 | 3/2019 | |
| WO | 2019094772 | A1 | 5/2019 | |
| WO | WO 2019/099926 | A1 * | 5/2019 | ........... C07D 401/14 |
| WO | WO-2019084026 | A1 | 5/2019 | |
| WO | WO-2019084030 | A1 | 5/2019 | |
| WO | WO-2019099868 | A1 | 5/2019 | |
| WO | 2019111218 | A1 | 6/2019 | |
| WO | WO-2019133531 | A1 | 7/2019 | |
| WO | WO-2019140380 | A1 | 7/2019 | |
| WO | WO-2019140387 | A1 | 7/2019 | |
| WO | WO-2019160915 | A1 | 8/2019 | |
| WO | WO-2019165229 | A1 | 8/2019 | |
| WO | WO-2019236483 | | 12/2019 | |
| WO | WO-2020010177 | A1 | 1/2020 | |
| WO | WO-2020010210 | A1 | 1/2020 | |
| WO | WO-2020010227 | A1 | 1/2020 | |
| WO | WO-2020018788 | A1 | 1/2020 | |
| WO | 2020028258 | A1 | 2/2020 | |
| WO | 2020038415 | A1 | 2/2020 | |
| WO | 2020041331 | A1 | 2/2020 | |
| WO | 2020092907 | A1 | 5/2020 | |
| WO | WO 2020/113233 | A1 * | 6/2020 | ........... A61K 39/395 |
| WO | 2020150626 | A1 | 7/2020 | |
| WO | WO-2020251969 | A1 | 12/2020 | |
| WO | WO-2020251971 | A1 | 12/2020 | |
| WO | WO-2020251972 | A1 | 12/2020 | |
| WO | WO-2020251974 | A1 | 12/2020 | |
| WO | WO-2020264490 | A1 | 12/2020 | |
| WO | WO-2020264499 | A1 | 12/2020 | |
| WO | WO-2021011631 | A1 | 1/2021 | |
| WO | WO-2021011634 | A1 | 1/2021 | |
| WO | WO-2021011868 | A1 | 1/2021 | |
| WO | WO-2021011871 | A1 | 1/2021 | |
| WO | 2021018118 | A1 | 2/2021 | |
| WO | WO-2021053555 | A1 | 3/2021 | |

(56) References Cited

FOREIGN PATENT DOCUMENTS

| | | | |
|---|---|---|---|
| WO | 2021119159 | A1 | 6/2021 |
| WO | WO-2021127190 | A1 | 6/2021 |
| WO | WO-2021127278 | A1 | 6/2021 |
| WO | WO-2021127283 | A2 | 6/2021 |
| WO | 2021158634 | A1 | 8/2021 |
| WO | 2021168197 | A1 | 8/2021 |
| WO | 2021222366 | A1 | 11/2021 |
| WO | 2021247897 | A1 | 12/2021 |
| WO | 2021247899 | A1 | 12/2021 |
| WO | 2021257914 | A1 | 12/2021 |
| WO | 2022027058 | A1 | 2/2022 |
| WO | 2022028547 | A1 | 2/2022 |
| WO | 2022087216 | A1 | 4/2022 |
| WO | 2022088551 | A1 | 5/2022 |
| WO | 2022125790 | A1 | 6/2022 |
| WO | 2022147465 | A1 | 7/2022 |
| WO | 2022161414 | A1 | 8/2022 |
| WO | 2022174268 | A1 | 8/2022 |
| WO | 2022174269 | A1 | 8/2022 |
| WO | 2022236339 | A1 | 11/2022 |
| WO | 2022266258 | A1 | 12/2022 |
| WO | 2023274390 | A1 | 1/2023 |
| WO | 2023283372 | A1 | 1/2023 |
| WO | 2023283610 | A1 | 1/2023 |
| WO | 2023023255 | A1 | 2/2023 |
| WO | 2023025159 | A1 | 3/2023 |
| WO | 2023036175 | A1 | 3/2023 |
| WO | 2023045978 | A1 | 3/2023 |
| WO | 2023076556 | A1 | 5/2023 |
| WO | 2023131167 | A1 | 7/2023 |
| WO | 2023137439 | A1 | 7/2023 |
| WO | 2023147594 | A2 | 8/2023 |
| WO | 2023186069 | A1 | 10/2023 |
| WO | 2023192586 | A1 | 10/2023 |
| WO | 2023201272 | A1 | 10/2023 |
| WO | 2023201274 | A1 | 10/2023 |
| WO | 2023237049 | A1 | 12/2023 |
| WO | 2023241644 | A1 | 12/2023 |
| WO | 2024020084 | A1 | 1/2024 |
| WO | 2024020522 | A1 | 1/2024 |
| WO | 2024067845 | A1 | 4/2024 |
| WO | 2024081893 | A1 | 4/2024 |
| WO | 2024094190 | A1 | 5/2024 |
| WO | 2024129879 | A1 | 6/2024 |
| WO | 2024183650 | A1 | 9/2024 |
| WO | 2024188209 | A1 | 9/2024 |
| WO | 2024208256 | A1 | 10/2024 |
| WO | 2024209044 | A1 | 10/2024 |
| WO | 2024264017 | A2 | 12/2024 |
| WO | 2025024305 | A2 | 1/2025 |
| WO | 2025080300 | A1 | 4/2025 |

OTHER PUBLICATIONS

CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STn Abstract, RN 779303-42-3 (Pub. Nov. 12, 2004).
Matyskiela et al., "A Cereblon Modulator (CC-220) with Improved Degradation of Ikaros and Aiolos," J Med Chem., 2018, 61(2):535-542.
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Seitz et al., "Sulfenylation and Halogenation of Di-and Trianions Derived from Substituted Glutarimides," Synthetic Communications, 1977, 7(6):367-374.
Xia and Chen, "Iron-catalyzed N-alkylation of azoles via cleavage of an sp3 C-H bond adjacent to a nitrogen atom," J Org Chem., 2012, 77(20):9366-9373.
Zinc 170596280, Date Added Aug. 8, 2015, https://zinc.docking.org/substances/ZINC000170596280/. Date Accessed: Jan. 10, 2022.
International Search Report received from PCT/US2023/061673, dated Jul. 25, 2023, 4 pages.
PCT International Preliminary Report on Patentability from PCT/US2020/065628, dated Jun. 30, 2022, 9 pages.
PCT International Search Report and Written Opinion from PCT/US2021/029578, dated Aug. 6, 2021, 09 pages.
PCT International Search Report and Written Opinion from PCT/US2021/035745, dated Sep. 27, 2021.
PCT International Search Report and Written Opinion from PCT/US2021/035747, dated Sep. 27, 2021.
PCT International Search Report and Written Opinion from PCT/US2021/037952, dated Sep. 29, 2021, 11 pages.
PCT International Search Report and Written Opinion from PCT/US2021/055971, dated Feb. 2, 2022, 08 pages.
PCT International Search Report and Written Opinion from PCT/US2021/071048, dated Nov. 5, 2021, 09 pages.
PCT International Search Report and Written Opinion from PCT/US2021/073186, dated May 3, 2022, 16 pages.
PCT International Search Report and Written Opinion from PCT/US2022/048163, dated Mar. 10, 2023, 11 pages.
PCT International Search Report and Written Opinion from PCT/US2022/070662, dated Apr. 18, 2022.
PCT International Search Report and Written Opinion from PCT/US2022/070664, dated May 3, 2022.
PCT International Search Report and Written Opinion from PCT/US2022/072194, dated Sep. 6, 2022, 10 pages.
PCT International Search Report and Written Opinion from PCT/US2023/017087, dated Jun. 12, 2023, 08 pages.
PCT International Search Report and Written Opinion from PCT/US2023/060645, dated Mar. 31, 2023.
PCT International Search Report and Written Opinion from PCT/US2021/016377, dated Jun. 15, 2021.
Mullard, "IRAK4 degrader to take on innate immunity", Nature Biotechnology, 2020, 38(11):1221-1223.
PCT International Search Report and Written Opinion received from PCT/US2023/076862, dated Feb. 27, 2024, 12 pages.
PCT International Search Report and Written Opinion received from PCT/US2023/077743, dated Mar. 6, 2024, 13 pages.
McElroy, "Interleukin-1 receptor-associated kinase 4 (IRAK4) inhibitors: an updated patent review," Expert Opinion on Therapeutic Patents, 2019, 29(4): 243-259.
PCT International Search Report and Written Opinion received from PCT/US2023/083863, dated Apr. 2, 2024.
"Acute Leukemia", Merck Manual (Online Edition), 2013, 6 pages.
Ali et al., "Design, synthesis, molecular modelling and biological evaluation of novel 3-(2-naphthyl)-1-phenyl-1H-pyrazole derivatives as potent antioxidants and 15-Lipoxygenase inhibitors", J Enzyme Inhib Med Chem., 2020, 35 (1):847-863.
Blake et al., "Studies with deuterated drugs," J Pharm Sci. 1975,64(3):367-391.
Chou and Talalay, "Quantitative analysis of dose-effect relationships: the combined effects of multiple drugs or enzyme inhibitors," Adv Enzyme Regul., 1984, 22:27-55.
Collins, "Chemical approaches to targeted protein degradation through modulation of the ubiquitin-proteasome pathway", Biochemical Journal, 2017, 474(7):1127-1147.
Cushing et al., "Interleukin 1/Toll-like receptor-induced autophosphorylation activates interleukin 1 receptor-associated kinase 4 and controls cytokine induction in a cell type-specific manner," J Biol Chem. 2014, 289(15):10865-10875.

(56) References Cited

OTHER PUBLICATIONS

Damasio, "Alzheimer's Disease and related dementias", Cecil Textbook of Medicine, 20th Edition, 1996, vol. 2, pp. 1992-1996.
De Nardo et al. "Interleukin-1 receptor-associated kinase 4 (IRAK4) plays a dual role in myddosome formation and Toll-like receptor signaling," J Biol Chem. 2018, 293(39):15195-15207.
Dorwald F., "Side Reactions in Organic Synthesis", 2005, Wiley: VCH, Weinheim p. I? of Preface p. 1-15.
Fisher et al., "The complexities inherent in attempts to decrease drug clearance by blocking sites of CYP-mediated metabolism," Curr Opin Drug Discov Devel., 2006, 9(1):101-109.
Foster, "Deuterium isotope effects in the metabolism of drugs and xenobiotics: implications for drug design," Advances in Drug Research, 1985, 14:1-40.
Fukuto et al., "Determination of the mechanism of demethylenation of (methylenedioxy)phenyl compounds by cytochrome P450 using deuterium isotope effects," J Med Chem., 1991, 34(9):2871-2876.
Gura T., "Systems for identifying new drugs are often faulty," Science, 1997, 278(5340):1041-1042.
Harvey, et al., "Management of organic impurities in small molecule medicinal products: Deriving safe limits for use in early development", Regulatory Toxicology and Pharmacology, 2017, 84:116-123.
Huang et al., "A Chemoproteomic Approach to Query the Degradable Kinome Using a Multi-kinase Degrader", Cell Chem Biol., 2018, 25(1):88-99.
J. G. Cannon, Chapter Nineteen in Burger's Medicinal Chemistry and Drug Discovery, Fifth Edition, vol. I: Principles and Practice, Wiley-Interscience 1995, pp. 783-802, 784.
Johnson et al., "Relationships between drug activity in NCI preclinical in vitro and in vivo models and early clinical trials," British Journal of Cancer, 2001, 84(10): 1424-1431.
Kushner et al., "Pharmacological uses and perspectives of heavy water and deuterated compounds," Can J Physiol Pharmacol., 1999, 77(2):79-88.
Layzer, Robert B., "Degenerative diseases of the nervous system", Cecil Textbook of Medicine, 20th Edition, 1996, vol. 2, pp. 2050-2057.
Patra and Choi, "Recent Progress in the Molecular Recognition and Therapeutic Importance of Interleukin-1 Receptor-Associated Kinase 4," Molecules. 2016, 21(11):1529.
Pearce et al., "Failure modes in anticancer drug discovery and development," Cancer Drug Design and Discovery, Edited by Stephen Neidle, Chapter 18, 2008, pp. 424-435.
Simone, "Oncology: Introduction", Cecil Textbook of Medicine, 20th Edition, 1996, vol. 1, pp. 1004-1010.
Slavin et al., "Identification of highly potent and selective Interlukin-1 receptor associated kinase 4 (IRAK4) degraders for the treatment suppurativa", Feb. 2020, 1 page. Retrived from https://www.kymeratx.com/wp-content/uploads/2020/07/EHSF_Kymera_2020_Final.pdf.
Stieger et al., "Recrystallization of Active Pharmaceutical Ingredients", Crystallization—Science and Technology, 2012, pp. 183-201.
Tinworth et al., "Small molecule-mediated protein knockdown as a new approach to drug discovery", Med. Chern. Commun., 2016, 7:2206-2216.
Troup, "Current strategies for the design of PROTAC linkers: a critical review", Explor Target Antitumor Ther., 2020, 1 (5):273-312.
Venkatesh et al., "Role of the development scientist in compound lead selection and optimization", J Pharm Sci., 2000, 89(2):145-154.
Extended European Search report received in EP Patent Application No. 18858547.5, mailed on Aug. 11, 2021, 16 pages.
Extended European Search report received in EP Patent Application No. 19738412.6, mailed on Dec. 8, 2021, 12 pages.
Extended European Search report received in EP Patent Application No. 19830838.9, mailed on Jul. 25, 2022, 8 pages.
PCT International Preliminary Report on Patentability from PCT/US2018/052181, dated Apr. 2, 2020, 8 pages.
PCT International Preliminary Report on Patentability from PCT/US2019/013491, dated Jul. 23, 2020, 7 pages.
PCT International Preliminary Report on Patentability from PCT/US2019/064070, dated Jun. 10, 2021, 7 pages.
PCT International Preliminary Report on Patentability from PCT/US2020/040101, dated Jan. 6, 2022, 8 pages.
PCT International Preliminary Report on Patentability from PCT/US2020/040125, dated Jan. 21, 2021.
PCT International Preliminary Report on Patentability from PCT/US2020/042530, dated Jan. 27, 2022, 6 pages.
PCT International Preliminary Report on Patentability from PCT/US2020/064061, dated Jun. 23, 2022, 13 pages.
PCT International Preliminary Report on Patentability from PCT/US2020/065752, dated Jun. 30, 2022, 7 pages.
PCT International Preliminary Report on Patentability from PCT/US2020/065757, dated Jun. 30, 2022, 9 pages.
PCT International Preliminary Report on Patentability from PCT/US2021/016377, dated Aug. 18, 2022, 8 pages.
PCT International Preliminary Report on Patentability from PCT/US2021/029578, dated Nov. 10, 2022, 7 pages.
PCT International Preliminary Report on Patentability from PCT/US2021/035745, dated Dec. 15, 2022, 6 pages.
PCT International Preliminary Report on Patentability from PCT/US2021/035747, dated Dec. 15, 2022, 6 pages.
PCT International Preliminary Report on Patentability from PCT/US2021/037952, dated Dec. 29, 2022, 9 pages.
PCT International Preliminary Report on Patentability from PCT/US2021/055971, dated May 4, 2023, 06 pages.
PCT International Preliminary Report on Patentability from PCT/US2021/062640, dated Jun. 22, 2023, 06 pages.
PCT International Preliminary Report on Patentability from PCT/US2021/071048, dated Feb. 9, 2023, 07 pages.
PCT International Preliminary Report on Patentability from PCT/US2021/073186, dated Jul. 13, 2023, 12 pages.
PCT International Preliminary Report on Patentability from PCT/US2022/070662, dated Aug. 24, 2023, 6 pages.
PCT International Preliminary Report on Patentability from PCT/US2022/070664, dated Aug. 24, 2023, 7 pages.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
Pubmed Compound Summary for CID 101524675, "(2R)-3-Fluoro-2-(2-methylpropyl)-3-phenyl-1,3-azasilinan-6-one," *U.S. National Library of Medicine*, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl)piperidine-2,6-dione, *U.S. Library of Medicine*, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl) piperidine-2,6-dione, U.S. Library of Medicine, created Jan. 18, 2016, https://pubchem.ncbi.nlm.nih.gov/compound/110491555. Date Accessed: Feb. 25, 2020 (7 pages).

(56) References Cited

OTHER PUBLICATIONS

Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," *U.S. National Library of Medicine*, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," *U.S. National Library of Medicine*, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).
PCT International Search Report and Written Opinion from PCT/US2020/040101, dated Nov. 10, 2020.
PCT International Search Report and Written Opinion from PCT/US2020/040125, dated Nov. 13, 2020.
PCT International Search Report and Written Opinion from PCT/US2020/042530, dated Oct. 16, 2020.
Moynagh, "The Pellino Family: IRAK E3 ligases with emerging roles in innate immune signalling," Trends Immunol. 2009, 30(1): 33-42.
Charrier et al., "Desulfonylative Radical Ring Closure onto Aromatics. A Modular Route to Benzazepin-2-ones and 5-Arylpiperidin-2-ones," Org. Lett. 2012, 14(8):2018-2021.
Devi et al., "Medicinal Attributes of Imidazo[1,2-a]pyridine Derivatives: An Update," Curr Top Med Chem, 2016, 16(26):2963-2994.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9): 4683-4702.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/042105, dated Nov. 20, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065752, dated Mar. 25, 2021.
Kargbo, "Protac Degradation of IRAK4 for the Treatment of Cancer," ACS Med. Chem. Lett., 2019, 10(10):1370-1371.
Ohoka et al., "Development of Small Molecule Chimeras That Recruit AhR E3 Ligase to Target Proteins,"ACS Chem. Biol. 2019, 14(12):2822-2832.
Rusnac et al., "Recognition of the Diglycine C-End Degron by CRL2 KLHDC2 Ubiquitin Ligase," Mol. Cell. 2018, 72(5):813-822.e4.
Tong et al., "Targeted Protein Degradation via a Covalent Reversible Degrader Based on Bardoxolone", ChemRxiv. First Posted Online: Apr. 2, 2020.
PCT International Search Report and Written Opinion from PCT/US2018/067304, dated Apr. 30, 2019.
Zou et al., "PD-L1 (B7-H1) and PD-1 pathway blockade for cancer therapy: Mechanisms, response biomarkers, and combinations," Sci. Transl. Med. 2016;8(328):328rv4.
Adams et al., "Big opportunities for small molecules in immuno-oncology," Nat Rev Drug Discov. 2015;14(9):603-22.
Aruri et al., "Metal-free Cross-Dehydrogenative Coupling of HN-azoles with a-C(sp3)-H Amides via C-H Activation and Its Mechanistic and Application Studies," J Org Chem. 2017;82(2):1000-1012.
Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.
Berge et al., "Pharmaceutical salts," J Pharm Sci. Jan. 1977;66(1):1-19.
Berndsen et al., "New insights into ubiquitin E3 ligase mechanism," Nat Struct Mol Biol. 2014;21(4):301-7.
Boichenko et al., "A FRET-Based Assay for the Identification and Characterization of Cereblon Ligands," J Med Chem. 2016;59(2):770-4.
Buckley et al., "IRAK-4 inhibitors. Part 1: a series of amides," Bioorg Med Chem Lett. 2008;18(11):3211-4.
Buckley et al., "IRAK-4 inhibitors. Part II: a structure-based assessment of imidazo[1,2-a]pyridine binding," Bioorg Med Chem Lett. 2008;18(11):3291-5.
Buckley et al., "IRAK-4 inhibitors. Part III: A series of imidazo[1,2-a]pyridines," Bioorg Med Chem Lett. 2008;18(12):3656-60.
Cameron et al., "Loss of Interleukin Receptor-Associated Kinase 4 Signaling Suppresses Amyloid Pathology and Alters Microglial Phenotype in a Mouse Model of Alzheimer's Disease," J Neurosci. 2012;32(43):15112-23.
Cario, "Therapeutic Impact of Toll-like Receptors on Inflammatory Bowel Diseases: A Multiple-edged Sword," Inflamm Bowel Dis. 2008;14(3):411-21.
Chang et al., "What is the functional role of the thalidomide binding protein cereblon?" Int J Biochem Mol Biol. 2011;2(3):287-94.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem. 2015;58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol. 2011; 186(2):1279-88.
Cohen, "Targeting protein kinases for the development of anti-inflammatory drugs," Curr Opin Cell Biol. 2009;21(2):17-24.
Connolly et al., "Complexities of TGF-beta Targeted Cancer Therapy," Int J Biol Sci. 2012;8(7):964-978.

(56) References Cited

OTHER PUBLICATIONS

Contino-Pepin et al., "Preliminary biological evaluations of new thalidomide analogues for multiple sclerosis application," Bioorg Med Chem Lett. 2009;19(3):878-81.
Crews, "Targeting the Undruggable Proteome: The Small Molecules of My Dreams," Chem Biol. 2010;17(6):551-5.
Cushing et al., "IRAK4 kinase controls Toll-like receptor induced inflammation through the transcription factor IRF5 in primary human monocytes," J Biol Chem. 2017;292(45):18689-18698.
Dalbeth et al., "Hyperuricaemia and gout: state of the art and future perspectives," Ann Rheum Dis. 2014;73(9):1598-600.
Degorce et al., "Optimization of permeability in a series of pyrrolotriazine inhibitors of IRAK4," Bioorg Med Chem. 2018;26(4):913-924.
Deshaies and Joazeiro, "RING domain E3 ubiquitin ligases," Annu Rev Biochem. 2009;78:399-434.
Dinarello, "Interleukin-18 and the Pathogenesis of Inflammatory Diseases," Semin Nephrol. 2007;27(1):98-114.
Dinarello, "IL-1: Discoveries, controversies and future directions," Eur J Immunol. 2010:40(3):599-606.
Dinarello, "Interleukin 1 and interleukin 18 as mediators of inflammation and the aging process," Am J Clin Nutr. 2006; 83(suppl):447S-55S.
Dudhgaonkar et al., "Selective IRAK4 Inhibition Attenuates Disease in Murine Lupus Models and Demonstrates Steroid Sparing Activity," J Immunol. 2017; 198(3):1308-1319.
Dunne et al., "IRAK1 and IRAK4 Promote Phosphorylation, Ubiquitation, and Degradation of MyD88 Adaptor-like (Mal)," J Biol Chem. 2010;285(24):18276-82.
Fischer et al., "Structure of the DDB1-CRBN E3 ubiquitin ligase in complex with thalidomide," Nature. 2014;512(7512):49-53.
Flannery et al., "The interleukin-1 receptor-associated kinases: Critical regulators of innate immune signaling," Biochem Pharmacol. 2010;80(12):1981-91.
Gearing, "Targeting toll-like receptors for drug development: a summary of commercial approaches," Immunol Cell Biol. 2007;85(6):490-4.
Geyer and Müller-Ladner, "Actual status of antiinterleukin-1 therapies in rheumatic diseases," Curr Opin Rheumatol. 2010;22(3):246-51.
Gottipati et al., "IRAK1: A critical signaling mediator of innate immunity," Cell Signal. 2008;20(2):269-76.
Hagner et al., "CC-122, a pleiotropic pathway modifier, mimics an interferon response and has antitumor activity in DLBCL," Blood. 2015;126(6):779-89.
Hennessy et al., "Targeting Toll-like receptors: emerging therapeutics?" Nat Rev Drug Discov. 2010;9(4):293-307.
Hines et al., "MDM2-Recruiting PROTAC Offers Superior, Synergistic Antiproliferative Activity via Simultaneous Degradation of BRD4 and Stabilization of p53," Cancer Res. 2019;79(1): 251-262.
Hoffman et al., "Efficacy and Safety of Rilonacept (Interleukin-1 Trap) in Patients with Cryopyrin-Associated Periodic Syndromes," Arthritis Rheum. 2008;58(8):2443-5.
Iannello et al., "Role of Interleukin-18 in the Development and Pathogenesis of Aids," Aids Rev. 2009;11(3):115-25.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science. 2010;327(5971):1345-50.
Kelly et al., "Selective interleukin-1 receptor-associated kinase 4 inhibitors for the treatment of autoimmune disorders and lymphoid malignancy," J Exp Med. 2015;212(13):2189-201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Kim et al., "A critical role for IRAK4 kinase activity in Toll-like receptor-mediated innate immunity," J Exp Med. 2007;204(5):1025-36.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol. 2014;387(10): 909-19.
Kou et al., "Effects of RuPeng15 Powder (RPP15) on Monosodium Urate Crystal-Induced Gouty Arthritis in Rats," Evid Based Complement Alternat Med. 2015;2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem. 2007;282(18):13552-60.
Krönke et al., "Lenalidomide causes selective degradation of IKZF1 and IKZF3 in multiple myeloma cells" Science. 2014;343(6168):301-305.
Ku et al., "Selective predisposition to bacterial infections in IRAK-4-deficient children: IRAK-4-dependent TLRs are otherwise redundant in protective immunity," J Exp Med. 2007;204(10):2407-2422.
Kubo-Murai et al., "IRAK-4-dependent Degradation of IRAK-1 is a Negative Feedback Signal for TLR-mediated NF-KB Activation," J Biochem. 2008; 143(3):295-302.
Küppers, "IRAK inhibition to shut down TLR signaling in autoimmunity and MyD88-dependent lymphomas," J Exp Med. 2015;212(13):2184.
Lebakken et al., "A Fluorescence Lifetime Based Binding Assay to Characterize Kinase Inhibitors," J Biomol Screen. 2007;12(6):828-41.
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Li et al., "Targeting interleukin-1 receptor-associated kinase for human hepatocellular carcinoma," J Exp Clin Cancer Res. 2016;35(1):140.
Li et al., "IRAK-4: A novel member of the IRAK family with the properties of an IRAK-kinase," Proc Natl Acad Sci USA. 2002;99(8):5567-72.
Li, "IRAK4 in TLR/IL-1R signaling: Possible clinical applications," Eur J Immunol. 2008;38(3):614-8.
Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015;6(6):683-688.
Lin et al., "Helical assembly in the MyD88-IRAK4-IRAK2 complex in TLR /IL-1R signalling," Nature. 2010:465(7300):885-90.
Lu et al., "Hijacking the E3 Ubiquitin Ligase Cereblon to Efficiently Target BRD4," Chem Biol. 2015;2(6):755-63.
Lu et al., "Discovery of a Keap1-dependent peptide PROTAC to knockdown Tau by ubiquitination-proteasome degradation pathway," Euro J Med Chem. 2018;46:251-9.
Lu et al., "The myeloma drug lenalidomide promotes the cereblon-dependent destruction of Ikaros proteins," Science. 2014;343(6168):305-309.
Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clin Proc. 2009;84(2):114-22.
Martinon et al., "Gout-associated uric acid crystals activate the NALP3 inflammasome," Nature. 2006;440(7081):237-41.
Maschera et al., "Overexpression of an enzymatically inactive interleukin-1-receptor-associated kinase activates nuclear factor-kB," Biochem J. 1999;339(Pt2):227-31.
McElroy et al., "Discovery and hit-to-lead optimization of 2,6-diaminopyrimidine Inhibitors of interleukin-1 receptor-associated kinase 4," Bioorg Med Chem Lett. 2015;25(9):1836-41.

(56) References Cited

OTHER PUBLICATIONS

McElroy et al., "Potent and Selective Amidopyrazole Inhibitors of IRAK4 That Are Efficacious in a Rodent Model of Inflammation," ACS Med Chem Lett. 2015;6(6):677-682.
Muller et al., "Amino-Substituted Thalidomide Analogs: Potent Inhibitors of TNF-? Production," Bioorg Med Chem Lett. 1999;9(11): 1625-30.
Ngo et al., "Oncogenically active MYD88 mutations in human lymphoma," Nature. 2011;470(7332):115-9.
Nunes et al., "Targeting IRAK4 for Degradation with PROTACTSs," ACS Med Chem Lett. 2019;10(7):1081-1085.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.
Okazaki et al., "A rheostat for immune responses: the unique properties of PD-1 and their advantages for clinical application," Nat. Immunol. 2013; 14(12): 1212-1218.
PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2020/066859, dated May 4, 2021.
Picard et al., "Clinical features and outcome of patients with IRAK-4 and MyD88 deficiency," Medicine (Baltimore). 2010;89(6):403-425.
Picard et al., "Inherited human IRAK-4 deficiency: an update," Immunol Res. 2007;38(1-3):347-52.
Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood. 2016; 126(23): 675-676.
Powers et al., "Discovery and initial SAR of inhibitors of interleukin-1 receptor-associated kinase-4," Bioorg Med Chem Lett. 2006;16(11):2842-5.
Priyadarshini et al., "Copper catalyzed oxidative cross-coupling of aromatic amines with 2-pyrrolidinone: a facile synthesis of N-aryl-r-amino-r-lactams," Tetrahedron. 2014;70(36): 6068-6074.
Raina et al., "Chemical Inducers of Targeted Protein Degradation," J Biol Chem. 2010;285(15):11057-60.
Ramirez et al., "Defining causative factors contributing in the activiation of hedgehog signaling in diffuse large B-cell lymphoma," Leuk Res. 2012;36(10):1267-73.
Rokosz et al., "Kinase inhibitors as drugs for chronic inflammatory and immunological diseases: progress and challenges," Expert Opin Ther Targets. 2008;12(7):883-903.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS ONE. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Schnnekloth et al., "Chemical approaches to controlling intracellular protein degradation," Chembiochem. 2005;6(1):40-46.
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017;60(24):10071-10091.
Seganish et al., "Discovery and Structure Enabled Synthesis of 2,6-diaminopyrimidine-4-one IRAK4 Inhibitors," ACS Med Chem Lett. 2015;6(8): 942-947.
Seganish et al., "Initial optimization and series evolution of diaminopyrimidine inhibitors of interleukin-1 receptor associated kinase 4," Bioorg Med Chem Lett. 2015;25(16):3203-3207.
Sen et al., "Transcriptional signaling by double-stranded RNA: role of TLR3," Cytokine Growth Factor Rev. 2005; 16(1):1-14.
Shanmugasundaram et al., "A modular PROTAC design for target destruction using a degradation signal based on a single amino acid," J Biol Chem. 2019;294(41):15172-15175.
Smith et al., "Identification of quinazoline based inhibitors of IRAK4 for the treatment of inflammation," Bioorg Med Chem Lett. 2017;27(12):2721-2726.
So et al., "A pilot study of IL-1 inhibition by anakinra in acute gout," Arthritis Res Ther. 2007;9(2):R28.
Song et al., "The kinase activities of interleukin-e receptor associated kinase (IRAK)-1 and 4 are redundant in the control of inflammatory cytokine expression in human cells," Mol Immunol. 2009;46(7):1458-66.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Sun et al., "Carbohydrate and protein immobilization onto solid surfaces by sequential Diels-Alder and azide-alkyne cycloadditions," Bioconjug Chem. 2006;17(1):52-7.
Suzuki et al., "IRAK-4 as the central TIR signaling mediator in innate immunity," Trends Immunol. 2002;23(10):503-6.
Suzuki et al., "Severe impairment of interleukin-1 and Toll-like receptor signalling in mice lacking IRAK-4," Nature. 2002;416(6882):750-6.
Swantek et al., "IL-1 Receptor-Associated Kinase Modulates Host Responsiveness to Endotoxin," Journal of Immunology 164: 4301-4306, J Immunol. 2000;164(8):4301-6.
Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009;68(10):1613-7.
Terkeltaub, "Update on gout: new therapeutic strategies and options," Nat Rev Rheumatol. 2010;6(1):30-8.
Toogood, "Small molecule immuno-oncology therapeutic agents," Bioorg. Med. Chem. Lett. 2018;28(3):319-329.
Torres et al., "Hyperalgesia, synovitis and multiple biomarkers of inflammation are suppressed by interleukin 1 inhibition in a novel animal model of gouty arthritis," Ann Rheum Dis. 2009;68(10):1602-8.
Toure and Crews, "Small-Molecule PROTACS: New Approaches to Protein Degradation, " Angew Chem Int Ed Engl. 2016;55(6):1966-73.
Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Trøseid et al., "The role of interleukin-18 in the metabolic syndrome," Cardiovasc Diabetol. 2010;9:11.
Tumey et al., "Identification and optimization of indolo[2,3-c]quinoline inhibitors of IRAK4," Bioorg Med Chem Lett. 2014;24(9):2066-72.
Uehara et al., "Selective degradation of splicing factor CAPER? by anticancer sulfonamides," Nat Chem Biol. 2017;13(6):675-680.
Varfolomeev et al., "IAP antagonists induce autoubiquitination of c-IAPs, NF-kappaB activation, and TNFalpha-dependent apoptosis," Cell. 2007;131(4):669-81.
Vollmer et al., "The mechanism of activation of IRAK1 and IRAK4 by interleukin-1 and Toll-like receptor agonists," Biochem J. 2017;474(12):2027-2038.
Wang et al., "Crystal Structure of IRAK-4 Kinase in Complex with Inhibitors: Serine/Threonine Kinase with Tyrosine as a Gatekeeper," Structure. 2006;14(12):1835-44.
Wang et al., "Discovery of potent, selective, and orally bioavailable inhibitors of interleukin-1 receptor-associated kinase 4," Bioorg Med Chem Lett. 2015;25(23):5546-5550.
Wang et al., "IRAK-4 Inhibitors for Inflammation," Curr Top Med Chem. 2009;9(8):724-37.

(56) References Cited

OTHER PUBLICATIONS

Wang et al., "Roles of F-box proteins in cancer," Nat Rev Cancer. 2014;14(4):233-47.
Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med. 2008;75 Suppl 5:S9-12.
Winter et al., "Selective Target Protein Degradation via Phthalimide Conjugation," Science. 2015;348(6241):1376-1381.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-KB and JAK/STAT signaling and induces apoptosis of cells expressing the MYD88 L265P mutation in Waldenstrom's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell. 2012;21(6):723-37.
Zhang et al., "Constitutive IRAK4 Activation Underlies Poor Prognosis and Chemoresistance in Pancreatic Ductal Adenocarcinoma," Clin Cancer Res. 2017;23(7):1748-1759.
Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., "Targets of curcumin," Curr Drug Targets. 2011; 12(3):332-347.
PCT International Search Report and Written Opinion from PCT/US2020/065628, dated May 28, 2021.
El-Gamal et al., "Recent Advances of Colony-Stimulating Factor-1 Receptor (CSF-1R) Kinase and Its Inhibitors," J Med Chem. 2018;61(13):5450-5466.
Pubmed Compound Summary for CID 5426, "Thalidomide," created Mar. 25, 2005.
PCT International Search Report and Written Opinion from PCT/US2020/065757, dated May 28, 2021.
PCT International Search Report and Written Opinion from PCT/US2021/062640, dated Feb. 8, 2022.
PCT International Search Report and Written Opinion from PCT/US2020/042109, dated Dec. 10, 2020.
Anonymous, "Targeted protein degradation: treating inflammatory diseases in a new way", STAT—Reporting from the frontiers of health and medicine, Retrieved from: https://www.statnews.com/sponsor/2020/01/29/targeted-protein-degradation-treating-inflammatory-diseases-in-a-new-way/, Jan. 29, 2020, 5 pages.
Campbell et al., "A First-in-Class Selective and Potent IRAK4 Degrader Demonstrates Robust in Vitro and in Vivo Inhibition of TLR/IL-1R Activation and Inflammation", ACR, Oral poster presentation Kymera Therapeutics, Nov. 11, 2019, 14 pages.
Campbell et al., "Abstract No. 1768: A First-in-class Selective and Potent IRAK4 Degrader Demonstrates Robust in Vitro and in Vivo Inhibition of TLR/IL-1R Activation and Inflammation", ACR/ARP Annual Meeting, Nov. 11, 2019, 2 pages.
CAS Registry No. 2432994-31-3, KT474, IUPHAR (Pub. 2024), 2 pages.
Chen et al., "Research progress of small molecule IRAK-4 Inhibitors", Central South Pharmacy, Oct. 2015, 13 (10):1017-1024.
Phelan et al., "A multiprotein supercomplex controlling oncogenic signaling in lymphoma", Nature, 2018, 560 (7718):387-391.
Prnewswire, "Kymera Therapeutics to Present Preclinical Data on its First-in-Class Selective and Potent Oral IRAK4 Degraders in Cutaneous Inflammation", Retrieved from: https://www.prnewswire.com/news-releases/kymera-therapeutics-to-present-preclinical-data-on-its-first-in-class-selective-and-potent-oral-irak4-degraders-in-cutaneous-inflammation-300998974.html, Feb. 5, 2020, 3 pages.
Slavin et al., "Abstract 588: Identification of highly potent and selective Interlukin-1 receptor associated kinase 4 (IRAK4) degraders for the treatment suppurativa", Journal of Investigative Dermatology, 2020, 140(7):S80.
PCT International Preliminary Report on Patentability received for PCT Patent Application No. PCT/US2022/048163, dated May 10, 2024, 8 pages.
PCT International Preliminary Report on Patentability received for PCT Patent Application No. PCT/US2022/072194, dated Nov. 16, 2023, 7 pages.
PCT International Search Report and Written Opinion received for PCT Patent Application No. PCT/US2024/025026, dated Jul. 25, 2024, 8 pages.
U.S. Appl. No. 18/559,492 of Weiss, filed Nov. 7, 2023.
U.S. Appl. No. 18/582,218 of Mainolfi et al., filed Feb. 20, 2024.
U.S. Appl. No. 18/751,286 of Zheng et al., filed Jun. 23, 2024.
U.S. Appl. No. 18/799,238 of Mainolfi et al., filed Aug. 9, 2024.
U.S. Appl. No. 18/912,154 of Mainolfi et al., filed Oct. 10, 2024.
Bastin et al.: "Salt selection and Optimisation Procedures for Pharmaceutical New Chemical Entities", Organic Process Research & Development, 2000, 4:427-435.
Cyrus et al., "Impact of linker length on the activity of PROTACs", Molecular BioSystems, 2011, 7(2):359-364.
Field et al., "Novel highly specific anti-periostin antibodies uncover the functional importance of the fascilin 1-1 domain and highlight preferential expression of periostin in aggressive breast cancer", Int J Cancer. Apr. 15, 2016, 138 (8):1959-1970.
Kummerer, "Pharmaceuticals in the environment", Annual Review of Environment and Resources, 2010, 35:57-75.
Kyutoku et al., "Role of periostin in cancer progression and metastasis: inhibition of breast cancer progression and metastasis by anti-periostin antibody in a murine model", Int J Mol Med., Aug. 2011, 28(2):181-186.
Naito et al., "Chemical protein knockdown: Development of SNIPER compounds that induce degradation of target proteins", Medchem News, 2018, 28(1):29-35.
Ohoka Nobumichi "Development of Protein Knockdown Technology as Emerging Drug Discovery Strategy", Pharmaceutical Magazine, Sep. 1, 2018, 138(9):1135-1143.
Orecchia et al., "Identification of a novel cell binding site of periostin involved in tumour growth", Eur J Cancer, Sep. 2011, 47(14):2221-2229.
Steinebach et al., "A MedChem toolbox for cereblon-directed PROTACs", Med. Chem. Commun., 2019, 10 (6):1037-1041.
Ackerman et al., "Extended Data Fig. 1: Identification of KT-474 (SAR444656) as a potent and selective degrader of IRAK4. From: IRAK4 degrader in hidradenitis suppurativa and atopic dermatitis: a phase 1 trial", Nature Medicine, Retrieved from URL:https://www.nature.com/articles/s41591-023-02635-7/figures/5, 2023, pp. 1-3.
Ackerman et al., "IRAK4 degrader in hidradenitis suppurativa and atopic dermatitis: a phase 1 trial", Nature Medicine, Retrieved from: URL:https://www.nature.com/articles/s41591-023-02635-7.pdf>, 2023, 29:3127-3136.
Anonymous: "Kymera Therapeutics to Present Interim Results from a Non-Interventional Study Characterizing IRAK4 Expression and Demonstrating Proof of Mechanism of an IRAK4 Degrader in Patients with Hidradenitis Suppurativa", Kymera, Retrieved from: URL:https://www.globenewswire.com/news-release/2020/10/09/2106256/0/en/Kymera-Therapeutics-to-Present-Interim-Results-from-a-Non-Interventional-Study-Characterizing-IRAK4-Expression-and-Demonstrating-Proof-of-Mechanism-of-an-IRAK4-Degrader-in-Patients.html, Oct. 9, 2020, pp. 1-7.
Zhang et al., "Assessing IRAK4 Functions in ABC DLBCL by IRAK4 Kinase Inhibition and Protein Degradation", Cell Chemical Biology, Dec. 17, 2020, 27(12):1500-1509.
International Search Report and Written Opinion received for PCT Application No. PCT/US2024/035160, dated Nov. 20, 2024, 13 pages.
International Search Report and Written Opinion received for PCT Application No. PCT/US2024/038827, dated Apr. 2, 2025, 11 pages.
U.S. Appl. No. 19/012,355 of Mainolfi et al., filed Jan. 7, 2025.

(56) References Cited

OTHER PUBLICATIONS

U.S. Appl. No. 19/027,791 of Mainolfi et al., filed Jan. 17, 2025.
U.S. Appl. No. 19/056,013 of Zheng et al., filed Feb. 18, 2025.
U.S. Appl. No. 19/178,057 of Weiss et al., filed Apr. 14, 2025.

* cited by examiner

IRAK DEGRADERS AND USES THEREOF

CROSS-REFERENCE TO RELATED APPLICATIONS

This application is a § 371 National Stage of PCT Application No. PCT/US2020/040125, filed Jun. 29, 2020, which claims the benefit under 35 U.S.C. § 119(e) to U.S. Provisional Application No. 63/040,891, filed on Jun. 18, 2020, U.S. Provisional Application No. 62/964,955, filed on Jan. 23, 2020, U.S. Provisional Application No. 62/958,980, filed on Jan. 9, 2020, U.S. Provisional Application No. 62/948,968, filed on Dec. 17, 2019, U.S. Provisional Application No. 62/944,834, filed on Dec. 6, 2019, U.S. Provisional Application No. 62/908,153, filed on Sep. 30, 2019, U.S. Provisional Application 62/875,407, filed on Jul. 17, 2019, and U.S. Provisional Application No. 62/868,609, filed on Jun. 28, 2019, the contents of each of which is hereby incorporated by reference.

TECHNICAL FIELD OF THE INVENTION

The present invention relates to compounds and methods useful for the modulation of one or more interleukin-1 receptor-associated kinases ("IRAK") via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth JS Jr., Chembiochem, 2005, 6(1):40-46).

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target cancer-associated proteins such as interleukin-1 receptor-associated kinases ("IRAK") hold promise as therapeutic agents. Accordingly, there remains a need to find compounds that are TRAK degraders useful as therapeutic agents.

SUMMARY OF THE INVENTION

The present application relates novel bifunctional compounds, which function to recruit IRAK kinases to E3 Ubiquitin Ligase for degradation, and methods of preparation and uses thereof. In particular, the present disclosure provides bifunctional compounds, which find utility as modulators of targeted ubiquitination of IRAK kinases, which are then degraded and/or otherwise inhibited by the bifunctional compounds as described herein. Also provided are monovalent compounds, which find utility as inducers of targeted ubiquitination of IRAK kinases, which are then degraded and/or otherwise inhibited by the monovalent compounds as described herein. An advantage of the compounds provided herein is that a broad range of pharmacological activities is possible, consistent with the degradation/inhibition of IRAK kinases. In addition, the description provides methods of using an effective amount of the compounds as described herein for the treatment or amelioration of a disease condition, such as cancer, e.g., multiple myeloma.

The present application further relates to targeted degradation of IRAK kinases through the use of bifunctional molecules, including bifunctional molecules that link a degradation inducing moiety to a ligand that binds IRAK kinases having the following general formula I.

I

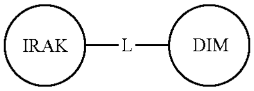

or a pharmaceutically acceptable salt thereof, wherein each variable is as defined and described herein.

It has now been found that compounds of this invention, and pharmaceutically acceptable compositions thereof, are effective for the modulation of targeted ubiquitination. Such compounds have the formula I-a or I-b:

I-a

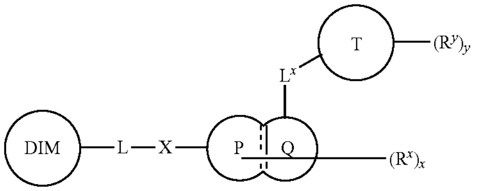

I-b

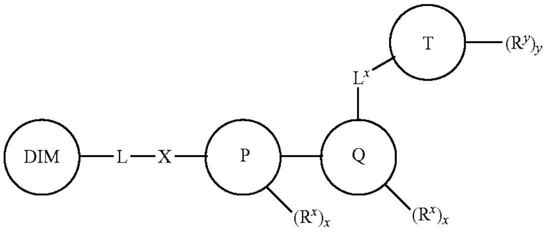

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of RAK enzymes in biological and pathological phenomena; the study of intracellular signal transduction pathways occurring in bodily tissues; and the comparative evaluation of new IRAK inhibitors or IRAK degraders or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as degraders and/or inhibitors of one or more IRAK protein kinases. In some embodiments, a provided compound degrades and/or inhibits IRAK-1/2/3/4.

In certain embodiments, the present invention provides a compound of formula I.

I

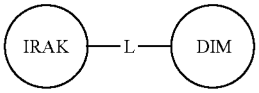

or a pharmaceutically acceptable salt thereof, wherein:

IRAK is an IRAK binding moiety capable of binding to one or more of IRAK-1, -2, -3, or -4;

L is a bivalent moiety that connects IRAK to DIM; and

DIM is a degradation inducing moiety.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

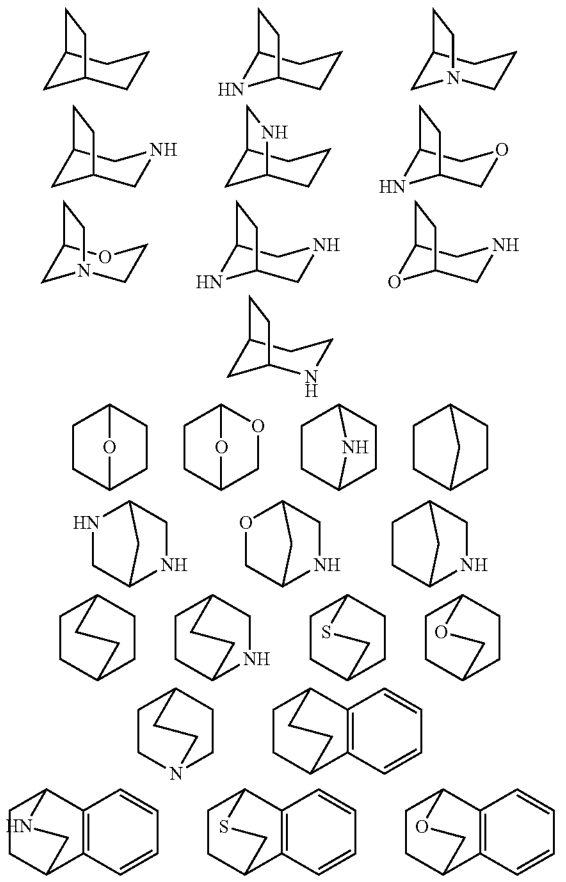

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of

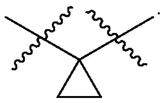 [SMILES: *C1(*)CC1]

the following structure:

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or *NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}(CH_2)_{0-1}Ph$ which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$: $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}0C(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}C(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^{03}$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)^\circ$; $—_1Ph$, $—CH_2—$(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; $—O($halo$R^\bullet)$, $—CN$, $—N_3$, $—(CH_2)_{0-2}C(O)R^*$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}\ NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}—O$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), $—OH$, $—OR^\bullet$, $—O($halo$R^\bullet)$, $—CN$, $—C(O)OH$, $—C(O)OR^\bullet$, $—NH_2$, $—NHR^\bullet$, $—NR^\bullet_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, -(halo$R^•$), —OH, —$OR^•$, —O(halo$R^•$), —CN, —C(O)OH, —$C(O)OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention As used herein, the term "inhibitor" is defined as a compound that binds to and/or inhibits an IRAK kinase with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

As used herein, the term "degrader" is defined as a heterobifunctional or monovalent compound that binds to and/or inhibits both an IRAK kinase and an E3 ligase with measurable affinity resulting in the ubiqitination and subsequent degradation of the IRAK kinase. In certain embodiments, a degrader has an $DC_{50}$ of less than about 50 μM, less than about 1 μM, less than about 500 nM, less than about 100 nM, less than about 10 nM, or less than about 1 nM. As used herein, the term "monovalent" refers to a degrader compound without an appended E3 ligase binding moiety.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$ $^{33}P$ $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Embodiments

As described above, in certain embodiments, the present invention provides a compound of formula I:

I

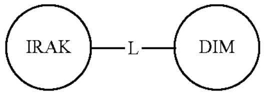

or a pharmaceutically acceptable salt thereof, wherein:

IRAK is an IRAK binding moiety capable of binding to one or more of IRAK-1, -2, -3, or -4;

L is a bivalent moiety that connects IRAK to DIM; and

DIM is a degradation inducing moiety.

In some embodiments, the present invention provides a compound of formula I:

I

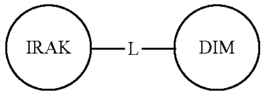

or a pharmaceutically acceptable salt thereof, wherein:

IRAK is an IRAK-4 binding moiety;

L is a bivalent moiety that connects IRAK to DIM; and

DIM is LBM, a lysine mimetic, or a hydrogen atom.

IRAK Binding Moiety (IRAK)

In certain embodiments, the present invention provides a compound of formula I, where IRAK is a IRAK-4 binding moiety thereby forming a compound of formulae I-a or I-b:

I-a

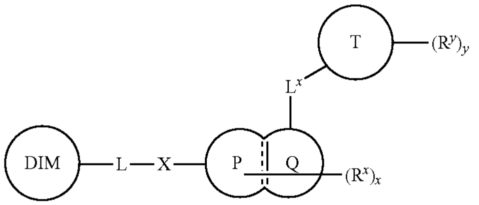

I-b

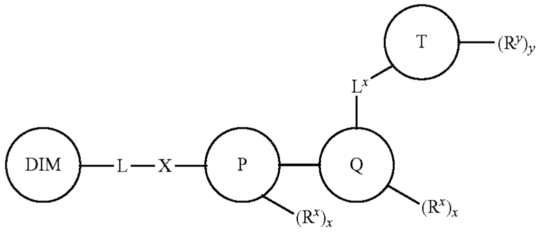

or a pharmaceutically acceptable salt thereof, wherein DIM and L are as defined and described herein, and wherein:

each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —$C(O)NR_2$, —$C(S)NR_2$, —C(O)N(R)OR, —OC(O)R, —OC(O)$NR_2$, —N(R)C(O)OR, —N(R)C(O)R, —N(R)C(O)$NR_2$, —$N(R)S(O)_2R$, —$N^{+6}$ $(O^-)R_2$, —$OP(O)R_2$, $-OP(O)(OR)_2$, $-OP(O)(OR)NR_2$, $-OP(O)(NR_2)_2$, $-P(O)R_2$, $-SiR_3$, $-Si(OR)R_2$, or $NR_2$ or

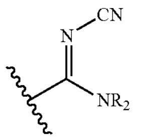

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, $-CN$, $-NO_2$, $-OR$, $-SR$, $-NR_2$, $-S(O)_2R$, $-S(O)_2NR_2$, $-S(O)R$, $-CF_2R$, $-CF_3$, $-CR_2(OR)$, $-CR_2(NR_2)$, $-C(O)R$, $-C(O)OR$, $-C(O)NR_2$, $-C(S)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)S(O)_2R$, $-OP(O)R_2$, $-OP(O)(OR)_2$, $-OP(O)(OR)NR_2$, $-OP(O)(NR_2)_2$, $-SiR_3$, or

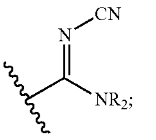

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P and Ring Q are optionally fused rings independently selected from phenyl or benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P and Ring Q are independently and optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with $-Cy^x-$, $-O-$, $-S-$, $-C(O)-$, $-C(S)-$, $-CR_2-$, $-CRF-$, $-CF_2-$, $-NR-$, $-N{=}CR-$, $-CR{=}CR-$, or $-S(O)_2-$, wherein R of $-CR_2-$, $-CRF-$, $-NR-$, $-N{=}CR-$, or $-CR{=}CR-$ can combine with $R^x$ or $R^y$ to form a 4-7 membered saturated or partially unsaturated carbocyclic or heterocyclic ring having 1-3 heteroatoms independently selected from nitrogen, oxygen, and sulfur;

$-Cy^x-$ is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein $-Cy^x-$ is optionally substituted with 1-2 oxo groups;

X is a covalent bond or a 4-6 membered saturated or partially unsaturated carbocyclic or heterocyclic ring having 1-2 heteroatoms independently selected from nitrogen, oxygen, and sulfur;

==== is a single or double bond;

each x is 0, 1, 2, 3 or 4; and each y is 0, 1, 2, 3 or 4.

In certain embodiments, the present invention provides a compound of formula I, where IRAK is a IRAK-4 binding moiety thereby forming a compound of formulae I'-a or I'-b:

I'-a

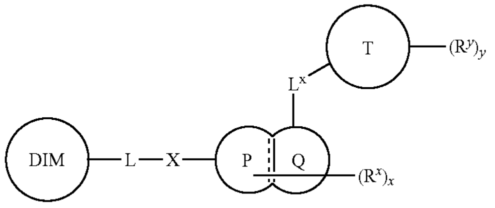

I'-b

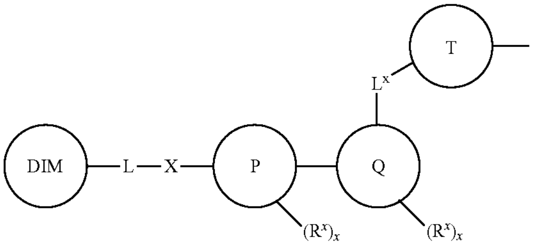

or a pharmaceutically acceptable salt thereof, wherein DIM and L are as defined and described herein, and wherein:

each $R^x$ is independently hydrogen, deuterium, $R^z$, halogen, $-CN$, $-NO_2$, $-OR$, $-SR$, $-NR_2$, $-S(O)_2R$, $-S(O)_2NR_2$, $-S(O)R$, $-CFR_2$, $-CF_2R$, $-CF_3$, $-CR_2(OR)$, $-CR_2(NR_2)$, $-C(O)R$, $-C(O)OR$, $-C(O)NR_2$, $-C(S)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)S(O)_2R$, $-N^{+6}(O^-)R_2$, —OP(O)$R_2$, —OP(O)(OR)$_2$, —OP(O)(OR)$NR_2$, —OP(O)($NR_2$)$_2$, —P(O)$R_2$, —$SiR_3$, —Si(OR)$R_2$, or

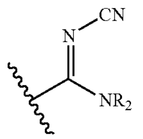

or two $R^x$ groups are optionally taken together to form an optionally substituted 5-6 membered partially unsaturated or aryl fused ring having 0-3 heteroatoms independently selected from nitrogen, oxygen, or sulfur, or a 3-5 membered saturated or partially unsaturated carbocyclic or heterocyclic spiro fused ring having 0-3 heteroatoms independently selected from nitrogen, oxygen, or sulfur, each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atoms to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^y$ is independently hydrogen, deuterium, $R^z$, halogen, —CN, —$NO_2$, —OR, —SR, —$NR_2$, —S(O)$_2$R, —S(O)$_2NR_2$, —S(O)R, —$CFR_2$, —$CF_2$R, —$CF_3$, —$CR_2$(OR), —$CR_2$($NR_2$), —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)S(O)$_2$R, —OP(O)$R_2$, —OP(O)(OR)$_2$, —OP(O)(OR)$NR_2$, —OP(O)($NR_2$)$_2$, —$SiR_3$, —$SF_5$, or

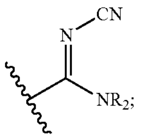

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P and Ring Q are optionally fused rings independently selected from phenyl or benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P and Ring Q are independently and optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with -$Cy^x$-, —O—, —S—, —C(O)—, —C(S)—, —$CR_2$—, —CRF—, —$CF_2$—, —NR—, —N═CR—, —CR═CR—, or —S(O)$_2$—, wherein R of —$CR_2$—, —CRF—, —NR—, —N═CR—, or —CR═CR— can combine with $R^x$ or $R^y$ to form a 4-7 membered saturated or partially unsaturated carbocyclic or heterocyclic ring having 1-3 heteroatoms independently selected from nitrogen, oxygen, and sulfur;

-$Cy^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -$Cy^x$- is optionally substituted with 1-2 oxo groups;

X is a covalent bond or a 4-6 membered saturated or partially unsaturated carbocyclic or heterocyclic ring having 1-2 heteroatoms independently selected from nitrogen, oxygen, and sulfur;

$=\!=\!=$ is a single or double bond;

each x is 0, 1, 2, 3 or 4; and each y is 0, 1, 2, 3 or 4.

In certain embodiments, the present invention provides a compound of formula I, where IRAK is a IRAK-4 binding moiety thereby forming a compound of formulae I''-a or I''-b:

I''-a

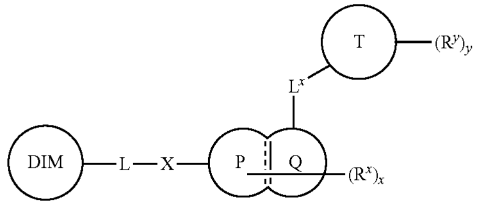

I''-b

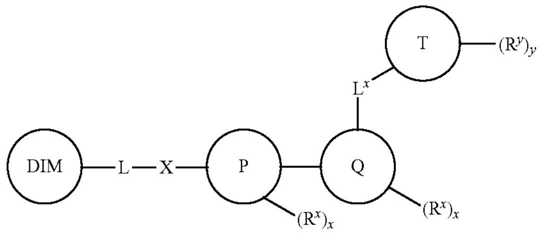

or a pharmaceutically acceptable salt thereof, wherein DIM and L are as defined and described herein, and wherein:

each $R^x$ is independently hydrogen, deuterium, $R^z$, halogen, $-CN$, $-NO_2$, $-OR$, $-SR$, $-NR_2$, $-S(O)_2R$, $-S(O)_2NR_2$, $-S(O)R$, $-CFR_2$, $-CF_2R$, $-CF_3$, $-CR_2(OR)$, $-CR_2(NR_2)$, $-C(O)R$, $-C(O)OR$, $-C(O)NR_2$, $-C(S)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)S(O)_2R$, $-N^{+6}(O^-)R_2$, $-OP(O)R_2$, $-OP(O)(OR)_2$, $-OP(O)(OR)NR_2$, $-OP(O)(NR_2)_2$, $-P(O)R_2$, $-SiR_3$, $-Si(OR)R_2$, or

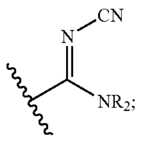

or two $R^x$ groups are optionally taken together to form an optionally substituted 5-6 membered partially unsaturated or aryl fused ring having 0-3 heteroatoms independently selected from nitrogen, oxygen, or sulfur, or a 3-5 membered saturated or partially unsaturated carbocyclic or heterocyclic spiro fused ring having 0-3 heteroatoms independently selected from nitrogen, oxygen, or sulfur, each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atoms to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^y$ is independently hydrogen, deuterium, $R^z$, halogen, $-CN$, $-NO_2$, $-OR$, $-SR$, $-NR_2$, $-S(O)_2R$, $-S(O)_2NR_2$, $-S(O)R$, $-CFR_2$, $-CF_2R$, $-CF_3$, $-CR_2(OR)$, $-CR_2(NR_2)$, $-C(O)R$, $-C(O)OR$, $-C(O)NR_2$, $-C(S)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)S(O)_2R$, $-OP(O)R_2$, $-OP(O)(OR)_2$, $-OP(O)(OR)NR_2$, $-OP(O)(NR_2)_2$, $-SiR_3$, $-SF_5$, or

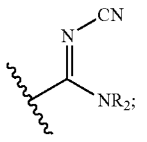

or a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur;

each $R^z$ is independently an optionally substituted group selected from $C_{1-6}$ aliphatic, phenyl, a 4-9 membered saturated or partially unsaturated carbocyclic or heterocyclic monocyclic, bicyclic, bridged bicyclic, or spirocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P and Ring Q are optionally fused rings independently selected from phenyl or benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P and Ring Q are independently and optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with $-Cy^x-$, $-O-$, $-S-$, $-C(O)-$, $-C(S)-$, $-CR_2-$, $-CRF-$, $-CF_2-$, $-NR-$, $-N{=}CR-$, $-CR{=}CR-$, or $-S(O)_2-$, wherein R of $-CR_2-$, $-CRF-$, $-NR-$, $-N{=}CR-$, or $-CR{=}CR-$ can combine with $R^x$ or R to form a 4-7 membered saturated or partially unsaturated carbocyclic or heterocyclic ring having 1-3 heteroatoms independently selected from nitrogen, oxygen, and sulfur;

$-Cy^x-$ is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein $-Cy^x-$ is optionally substituted with 1-2 oxo groups;

X is a covalent bond or a 4-6 membered saturated or partially unsaturated carbocyclic or heterocyclic ring having 1-2 heteroatoms independently selected from nitrogen, oxygen, and sulfur;

$\overline{====}$ is a single or double bond;

each x is 0, 1, 2, 3 or 4; and each y is 0, 1, 2, 3 or 4.

As described herein, a core structure depicted as

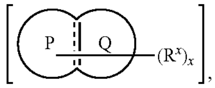, includes for example, structures

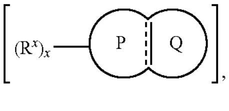, 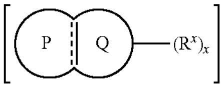, and

-continued

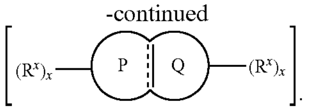

As defined generally above, each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$N^+$ $(O^-)R_2$, —OP(O)$R_2$, —OP(O)$(OR)_2$, —OP(O)(OR)$NR_2$, —OP(O)$(NR_2)_2$, —P(O)$R_2$, —$SiR_3$, —Si(OR)$R_2$, or

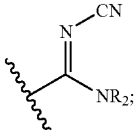

or two $R^x$ groups are optionally taken together to form an optionally substituted 5-6 membered partially unsaturated or aryl fused ring having 0-3 heteroatoms independently selected from nitrogen, oxygen, or sulfur, or a 3-5 membered saturated or partially unsaturated carbocyclic or heterocyclic spiro fused ring having 0-3 heteroatoms independently selected from nitrogen, oxygen, or sulfur.

In some embodiments, each $R^x$ is independently hydrogen. In some embodiments, $R^x$ is deuterium. In some embodiments, each $R^x$ is independently $R^z$. In some embodiments, each $R^x$ is independently halogen. In some embodiments, each $R^x$ is independently —CN. In some embodiments, each $R^x$ is independently —$NO_2$. In some embodiments, each $R^x$ is independently —OR. In some embodiments, each $R^x$ is independently —SR. In some embodiments, each $R^x$ is independently —$NR_2$. In some embodiments, each $R^x$ is independently —$S(O)_2R$. In some embodiments, each $R^x$ is independently —$S(O)_2NR_2$. In some embodiments, each $R^x$ is independently —S(O)R. In some embodiments, each $R^x$ is independently —$CFR_2$. In some embodiments, each $R^x$ is independently —$CF_2R$. In some embodiments, each $R^x$ is independently —$CF_3$. In some embodiments, each $R^x$ is independently —$CR_2(OR)$. In some embodiments, each $R^x$ is independently —$CR_2(NR_2)$. In some embodiments, each $R^x$ is independently —C(O)R. In some embodiments, each $R^x$ is independently —C(O)OR. In some embodiments, each $R^x$ is independently —C(O)$NR_2$. In some embodiments, each $R^x$ is independently —$N^+$ $(O^-)R_2$. In some embodiments, each $R^x$ is independently —OP(O)$R_2$. In some embodiments, each $R^x$ is independently —OP(O)$(OR)_2$. In some embodiments, each $R^x$ is independently —OP(O)(OR)$NR_2$. In some embodiments, each $R^x$ is independently —OP(O)$(NR_2)_2$. In some embodiments each $R^x$ is independently —P(O)$R_2$. In some embodiments, each $R^x$ is independently —$SiR_3$. In some embodiments, each $R^x$ is independently —Si(OR)$R_2$. In some embodiments, each $R^x$ is

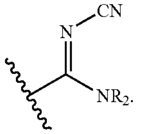

independently —$SF_5$. In some embodiments, each $R^x$ is independently $NR_2$. In some embodiments, two $R^x$ groups are optionally taken together to form an optionally substituted 5-6 membered partially unsaturated or aryl fused ring having 0-3 heteroatoms independently selected from nitrogen, oxygen, or sulfur. In some embodiments, two $R^x$ groups are optionally taken together to form an optionally substituted 3-5 membered saturated or partially unsaturated carbocyclic or heterocyclic spiro fused ring having 0-3 heteroatoms independently selected from nitrogen, oxygen, or sulfur, In some embodiments, $R^x$ is

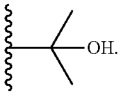

In some embodiments, $R^x$ is fluoro. In some embodiments, $R^x$ is —$CF_2H$. In some embodiments, $R^x$ is —OMe. In some embodiments, $R^x$ is —SMe. In some embodiments, $R^x$ is -Me. In some embodiments, $R^x$ is —$OCF_2H$. In some embodiments, $R^x$ is —$OCF_3$. In some embodiments, $R^x$ is —$S(O)_2Me$. In some embodiments, $R^x$ is

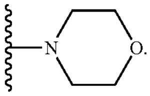 [SMILES: *N1CCOCC1]

In some embodiments, $R^x$ is

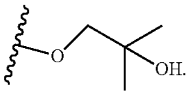 [SMILES: *OCC(C)(C)O]

In some embodiments, $R^x$ is

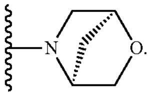

In some embodiments, $R^x$ is

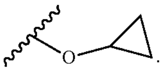 [SMILES: *OC1CC1]

In some embodiments, $R^x$ is

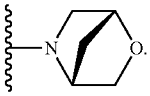

In some embodiments, $R^x$ is

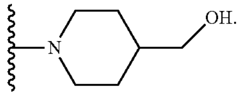 [SMILES: *N1CCC(CO)CC1]

In some embodiments, $R^x$ is

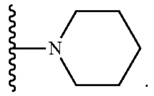 [SMILES: *N1CCCCC1]

In some embodiments, $R^x$ is

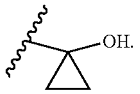 [SMILES: *C1(O)CC1]

In some embodiments, $R^x$ is

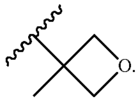

In some embodiments, $R^x$ is

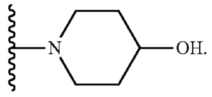 [SMILES: *N1CCC(O)CC1]

In some embodiments, $R^x$ is -OEt. In some embodiments, $R^x$ is -OiPr. In some embodiments, $R^x$ is

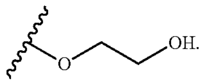 [SMILES: *OCCO]

In some embodiments, $R^x$ is

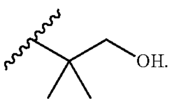 [SMILES: *C(C)(C)CO]

In some embodiments, $R^x$ is

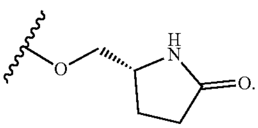 [SMILES: *OC[C@H]1CCC(=O)N1]

In some embodiments, $R^x$ is

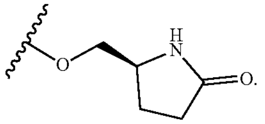 [SMILES: *OC[C@@H]1CCC(=O)N1]

In some embodiments, $R^x$ is

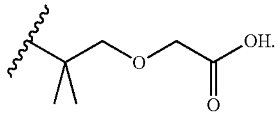 [SMILES: *C(C)(C)COCC(=O)O]

In some embodiments, $R^x$ is

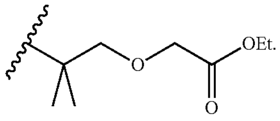 [SMILES: *C(C)(C)COCC(=O)OCC]

In some embodiments, $R^x$ is

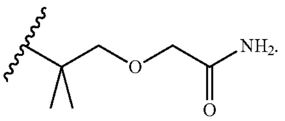 [SMILES: *C(C)(C)COCC(N)=O]

In some embodiments, each $R^x$ is selected from those depicted in Table 1, below.

As generally defined above, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same atom are optionally taken together with their intervening atom to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur.

In some embodiments, each R is independently hydrogen. In some embodiments, each R is an optionally substituted group selected from $C_{1-6}$ aliphatic. In some embodiments, each R is an optionally substituted phenyl. In some embodiments, each R is an optionally substituted 4-7 membered saturated or partially unsaturated heterocyclic having 1-2 heteroatoms independently selected from nitrogen, oxygen, and sulfur. In some embodiments, each R is an optionally substituted 5-6 membered heteroaryl ring having 1-4 heteroatoms independently selected from nitrogen, oxygen, and sulfur. In some embodiments, two R groups on the same atom are optionally taken together with their intervening atom to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur.

In some embodiments, each R is selected from those depicted in Table 1, below.

As defined generally above, each $R^y$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$N^{+6}$ $(O^-)R_2$, —OP(O)$R_2$, —OP(O)$(OR)_2$, —OP(O)(OR)$NR_2$, —OP(O)$(NR_2)_2$, —P(O)$R_2$, —$SiR_3$, —Si(OR)$R_2$, —$SF_5$, or

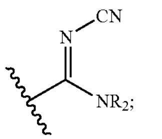

or two R groups are optionally taken together to form an optionally substituted 5-6 membered partially unsaturated or aryl fused ring having 0-3 heteroatoms independently selected from nitrogen, oxygen, or sulfur; or a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur.

In some embodiments, each $R^y$ is independently hydrogen. In some embodiments, $R^y$ is deuterium. In some embodiments, each $R^y$ is independently $R^z$. In some embodiments, each $R^y$ is independently halogen. In some embodiments, each $R^y$ is independently —CN. In some embodiments, each $R^y$ is independently —$NO_2$. In some embodiments, each $R^y$ is independently —OR. In some embodiments, each $R^y$ is independently —SR. In some embodiments, each $R^y$ is independently —$NR_2$. In some embodiments, each $R^y$ is independently —$S(O)_2R$. In some embodiments, each $R^y$ is independently —$S(O)_2NR_2$. In some embodiments, each $R^y$ is independently —S(O)R. In some embodiments, each $R^y$ is independently —$CFR_2$. In some embodiments, each $R^y$ is independently —$CF_2R$. In some embodiments, each $R^x$ is independently —$CF_3$. In some embodiments, each $R^y$ is independently —$CR_2(OR)$. In some embodiments, each $R^y$ is independently —$CR_2(NR_2)$. In some embodiments, each $R^y$ is independently —C(O)R. In some embodiments, each $R^y$ is independently —C(O)OR. In some embodiments, each $R^y$ is independently —C(O)$NR_2$. In some embodiments, each $R^y$ is independently —$N^+$ $(O^-)R_2$. In some embodiments, each $R^y$ is independently —OP(O)$R_2$. In some embodiments, each $R^y$ is independently —OP(O)$(OR)_2$. In some embodiments, each $R^y$ is independently —OP(O)(OR)$NR_2$. In some embodiments, each $R^y$ is independently —OP(O)$(NR_2)_2$. In some embodiments each $R^y$ is independently —P(O)$R_2$. In some embodiments, each $R^y$ is independently —$SiR_3$. In some embodiments, each $R^y$ is independently —Si(OR)$R_2$. In some embodiments, each $R^y$ is independently —$SF_5$. In some embodiments, each $R^y$ is independently

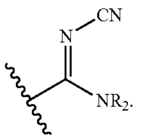

In some embodiments, two $R^y$ groups are optionally taken together to form an optionally substituted 5-6 membered partially unsaturated or aryl fused ring having 0-3 heteroatoms independently selected from nitrogen, oxygen, or sulfur. In some embodiments, a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur.

In some embodiments, $R^y$ is fluoro. In some embodiments, $R^y$ is chloro. In some embodiments, $R^y$ is —CN. In some embodiments, $R^y$ is —$CF_2Me$. In some embodiments, $R^y$ is —$CFMe_2$. In some embodiments, $R^y$ is -Me. In some embodiments, $R^y$ is —$OCF_3$. In some embodiments, $R^y$ is fluoro. In some embodiments, $R^y$ is cyclopropyl. In some embodiments, $R^y$ is

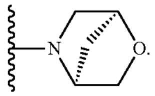 [SMILES: *N1C[C@@H]2C[C@H]1CO2]

In some embodiments, $R^y$ is

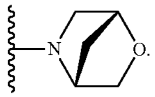 [SMILES: *N1C[C@H]2C[C@@H]1CO2]

In some embodiments, $R^y$ and $R^x$ taken together is

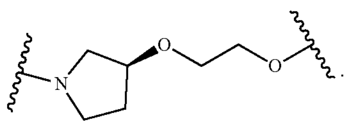 [SMILES: *OCCO[C@H]1CCN(*)C1]

In some embodiments, $R^y$ and $R^x$ taken together is

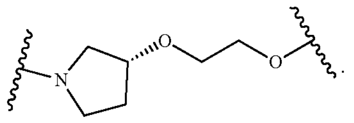 [SMILES: *OCCO[C@@H]1CCN(*)C1]

In some embodiments, $R^y$ and $R^x$ taken together is

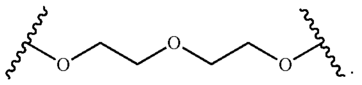 [SMILES: *OCCOCCO*]

In some embodiments, $R^y$ and $R^x$ taken together is

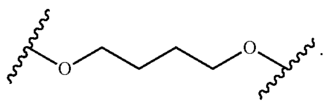 [SMILES: *OCCCCO*]

In some embodiments, $R^y$ and $R^x$ taken together is

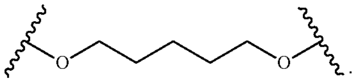 [SMILES: *OCCCCCO*]

In some embodiments, each R is selected from those depicted in Table 1, below.

As generally defined above, each $R^z$ is independently an optionally substituted group selected from $C_{1-6}$ aliphatic, phenyl, a 4-9 membered saturated or partially unsaturated carbocyclic or heterocyclic monocyclic, bicyclic, bridged bicyclic, or spirocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, each $R^z$ is independently an optionally substituted group selected from $C_{1-6}$ aliphatic. In some embodiments, each $R^z$ is independently an optionally substituted phenyl. In some embodiments, each $R^z$ is independently an optionally substituted 4-9 membered saturated or partially unsaturated carbocyclic or heterocyclic monocyclic, bicyclic, bridged bicyclic, or spirocyclic ring having 1-2 heteroatoms independently selected from nitrogen, oxygen, and sulfur. In some embodiments, each $R^z$ is independently an optionally substituted 5-6 membered heteroaryl ring having 1-4 heteroatoms independently selected from nitrogen, oxygen, and sulfur.

In some embodiments, each $R^z$ is selected from those depicted in Table 1, below.

As generally defined above, Ring P and Ring Q are optionally fused rings independently selected from phenyl or benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P and Ring Q are independently and optionally substituted with 1-2 oxo groups.

In some embodiments, Ring P and Ring Q are independently phenyl or benzo. In some embodiments, Ring P and Ring Q are independently a 4-7 membered saturated or partially unsaturated carbocyclic or heterocyclic ring having 1-3 heteroatoms independently selected from nitrogen, oxygen, and sulfur. In some embodiments, Ring P and Ring Q are independently a 5-6 membered heteroaryl ring having 1-4 heteroatoms independently selected from nitrogen, oxygen, and sulfur. In some embodiments, Ring P and Ring Q are independently and optionally substituted with 1-2 oxo groups.

In some embodiments, Ring P and Ring Q are

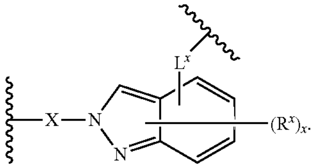

In some embodiments, Ring P and Ring Q are

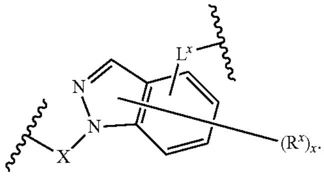

In some embodiments, Ring P and Ring Q are

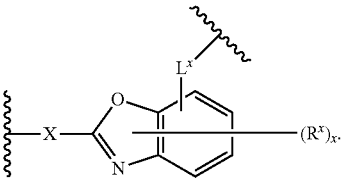

In some embodiments, Ring P and Ring Q are

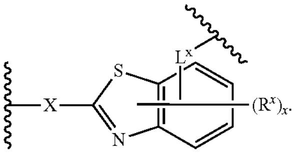

In some embodiments, Ring P and Ring Q are

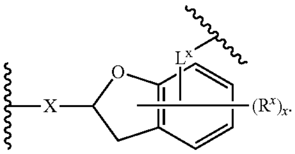

In some embodiments, Ring P and Ring Q are

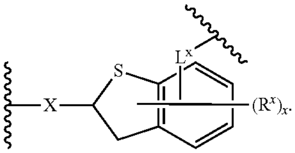

In some embodiments, Ring P and Ring Q are

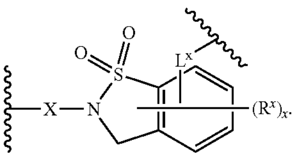

In some embodiments, Ring P and Ring Q are

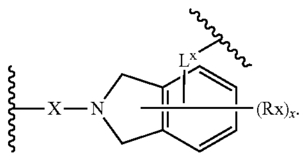

In some embodiments, Ring P and Ring Q are

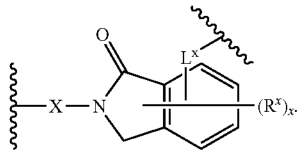

In some embodiments, Ring P and Ring Q are

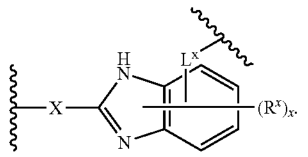

In some embodiments, Ring P and Ring Q are

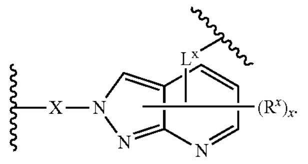

In some embodiments, Ring P and Ring Q are

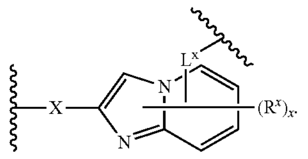

In some embodiments, Ring P and Ring Q are selected from those depicted in Table 1, below.

As generally defined above, Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups.

In some embodiments, Ring T is from phenyl. In some embodiments, Ring T is a 4-7 membered saturated or partially unsaturated carbocyclic or heterocyclic ring having 1-3 heteroatoms independently selected from nitrogen, oxygen, and sulfur. In some embodiments, Ring T is a 5-9 membered mono- or bicyclic heteroaryl ring having 1-4 heteroatoms independently selected from nitrogen, oxygen, and sulfur. In some embodiments, Ring T is further optionally substituted with 1-2 oxo groups.

In some embodiments, Ring T is

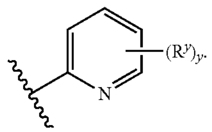

In some embodiments, Ring T is

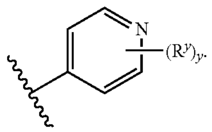

In some embodiments, Ring T is

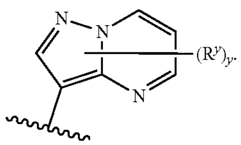

In some embodiments, Ring T is

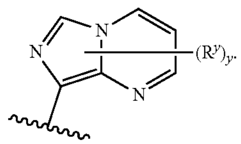

In some embodiments, Ring T is

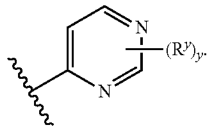

In some embodiments, Ring T is

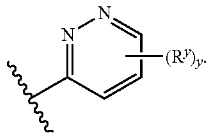

In some embodiments, Ring T is phenyl. In some embodiments, Ring T is

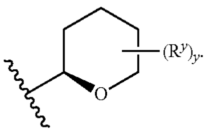

In some embodiments, Ring T is

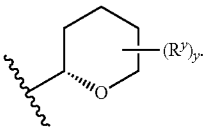

In some embodiments, Ring T is

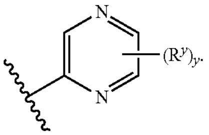

In some embodiments, Ring T is

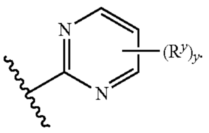

In some embodiments, Ring T is

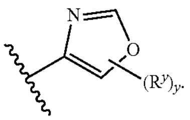

In some embodiments, Ring T is

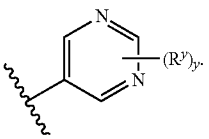

In some embodiments, Ring T is

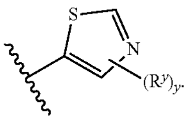

In some embodiments, Ring T is

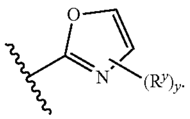

In some embodiments, Ring T is

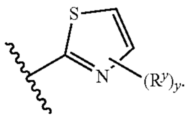

In some embodiments, Ring T is

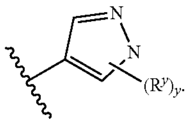

In some embodiments, Ring T is selected from those depicted in Table 1, below.

As generally defined above, $L^x$ is a covalent bond or a $C_{1-3}$ bivalent straight or branched saturated or unsaturated hydrocarbon chain wherein 1-2 methylene units of the chain are independently and optionally replaced with -$Cy^x$-, —O—, —S—, —C(O)—, —C(S)—, —$CR_2$—, —CRF—, —$CF_2$—, —NR—, —N═CR—, —CR═CR—, or —$S(O)_2$—, wherein R of —$CR_2$—, —CRF—, —NR—, —N═CR—, or —CR═CR— can combine with $R^x$ or $R^y$ to form a 4-7 membered saturated or partially unsaturated carbocyclic or heterocyclic ring having 1-3 heteroatoms independently selected from nitrogen, oxygen, and sulfur.

In some embodiments, $L^x$ is a covalent bond. In some embodiments, $L^x$ is a $C_{1-3}$ bivalent straight or branched saturated or unsaturated hydrocarbon chain wherein 1-2 methylene units of the chain are independently and optionally replaced with -$Cy^x$-, —O—, —S—, —C(O)—, —C(S)—, —$CR_2$—, —CRF—, —$CF_2$—, —NR—, —N═CR—, —CR═CR—, or —$S(O)_2$—. In some embodiments, R of —$CR_2$—, —CRF—, —NR—, —N═CR—, or —CR═CR— can combine with $R^x$ or $R^y$ to form a 4-7 membered saturated or partially unsaturated carbocyclic or heterocyclic ring having 1-3 heteroatoms independently selected from nitrogen, oxygen, and sulfur.

In some embodiments, Ring $L^x$ is —C(O)N(H)—. In some embodiments, Ring $L^x$ is —$CH_2C(O)N(H)$—. In some embodiments, $L^x$ combines with $R^y$ to form

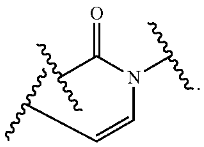 [SMILES: */C=C\N(*)C(*)=O]

In some embodiments, $L^x$ combines with $R^y$ to form

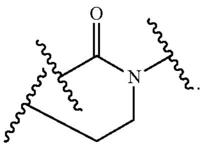 [SMILES: *CCN(*)C(*)=O]

In some embodiments, Ring $L^x$ is selected from those depicted in Table 1, below.

As generally defined above, -$Cy^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -$Cy^x$- is optionally substituted with 1-2 oxo groups.

In some embodiments, -$Cy^x$- is an optionally substituted ring selected from a 3-5 membered saturated or partially unsaturated carbocyclic or heterocyclic ring having 0-3 heteroatoms independently selected from nitrogen, oxygen, and sulfur. In some embodiments, -$Cy^x$— is a 5 membered heteroaryl ring having 1-4 heteroatoms independently selected from nitrogen, oxygen, and sulfur. In some embodiments, -$Cy^x$- is optionally substituted with 1-2 oxo groups.

In some embodiments, Ring -$Cy^x$- is selected from those depicted in Table 1, below.

As described above, X is a covalent bond or a 4-6 membered saturated or partially unsaturated carbocyclic or heterocyclic ring having 1-2 heteroatoms independently selected from nitrogen, oxygen, and sulfur.

In some embodiments, X is a covalent bond. In some embodiments, X is a 4-6 membered saturated or partially unsaturated carbocyclic or heterocyclic ring having 1-2 heteroatoms independently selected from nitrogen, oxygen, and sulfur.

In some embodiments, X is

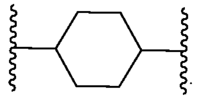 [SMILES: *C1CCC(*)CC1]

In some embodiments, X is

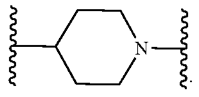 [SMILES: *C1CCN(*)CC1]

In some embodiments, X is selected from those depicted in Table 1, below.

As generally defined above, - - - - is a single or double bond.

In some embodiments, - - - - is a single. In some embodiments, - - - - is a double bond.

In some embodiments, Ring - - - - is selected from those depicted in Table 1, below.

As generally defined above, each x and y are independently 0, 1, 2, 3 or 4.

In some embodiments, each x and y are independently 0. In some embodiments, each x and y are independently 1. In some embodiments, each x and y are independently 2. In some embodiments, each x and y are independently 3. In some embodiments, each x and y are independently 4.

In some embodiments, each x and y are selected from those depicted in Table 1, below.

In some embodiments, the present invention provides a compound of formula I-a, wherein $L^x$ is an amide as shown, to provide a compound of formula I-c-1:

I-c-1

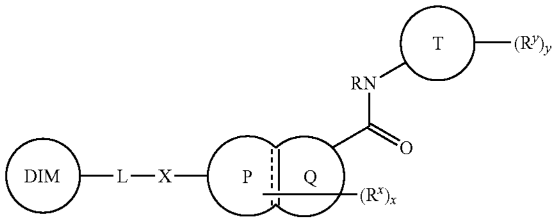

or a pharmaceutically acceptable salt thereof, wherein each of DIM, L, X, R, $R^x$, $R^y$, Ring P, Ring Q, Ring T, - - - -, x, and y is as defined above and described in embodiments herein, both singly and in combination.

In some embodiments, the present invention provides a compound of formula I-a, wherein $L^x$ is a thioamide as shown, to provide a compound of formula I-c-2:

I-c-2

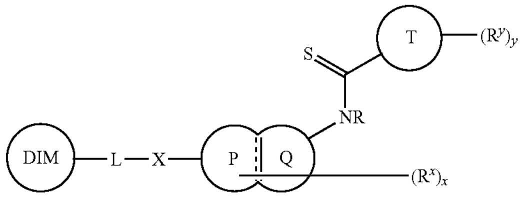

or a pharmaceutically acceptable salt thereof, wherein each of DIM, L, X, R, $R^x$, $R^Y$, Ring P, Ring Q, Ring T, - - - -, x, and y is as defined above and described in embodiments herein, both singly and in combination.

In some embodiments, the present invention provides a compound of formula I-a, wherein $L^x$ is a 1,2,4-triazole as shown, to provide a compound of formula I-c-3:

I-c-3

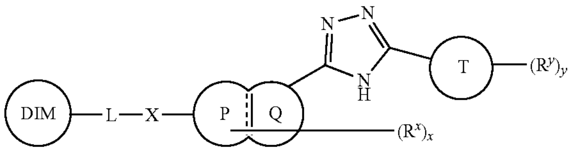

or a pharmaceutically acceptable salt thereof, wherein each of DIM, L, X, $R^x$, $R^Y$, Ring P, Ring Q, Ring T, - - - -, x, and y is as defined above and described in embodiments herein, both singly and in combination.

In some embodiments, the present invention provides a compound of formula I-a, wherein $L^x$ is a 1,3,4-oxadiazole as shown, to provide a compound of formula I-c-4:

I-c-4

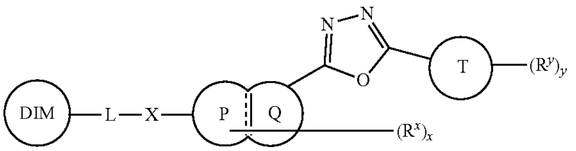

or a pharmaceutically acceptable salt thereof, wherein each of DIM, L, X, $R^x$, $R^Y$, Ring P, Ring Q, Ring T, $\overline{----}$, x, and y is as defined above and described in embodiments herein, both singly and in combination.

In some embodiments, the present invention provides a compound of formula I-a, wherein $L^x$ is an oxazole as shown, to provide a compound of formula I-c-5:

I-c-5

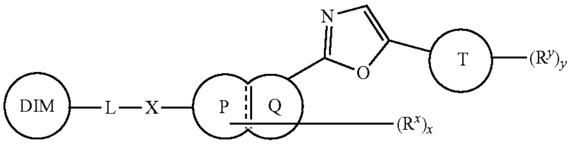

or a pharmaceutically acceptable salt thereof, wherein each of DIM, L, X, $R^x$, $R^y$, Ring P, Ring Q, Ring T, $\overline{----}$, x, and y is as defined above and described in embodiments herein, both singly and in combination.

In some embodiments, the present invention provides a compound of formula I-a, wherein $L^x$ is a thiazole as shown, to provide a compound of formula I-c-6:

I-c-6

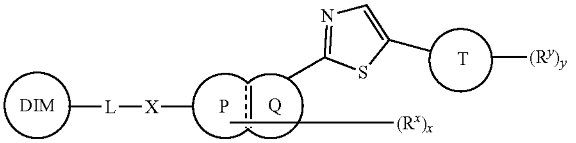

or a pharmaceutically acceptable salt thereof, wherein each of DIM, L, X, $R^x$, $R^y$, Ring P, Ring Q, Ring T, $\overline{----}$, x, and y is as defined above and described in embodiments herein, both singly and in combination.

In some embodiments, the present invention provides a compound of formula I-a, wherein $L^x$ is an imidazole as shown, to provide a compound of formula I-c-7:

I-c-7

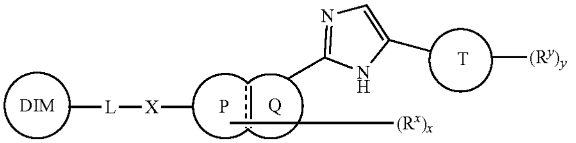

or a pharmaceutically acceptable salt thereof, wherein each of DIM, L, X, $R^x$, $R^y$, Ring P, Ring Q, Ring T, $\overline{----}$, x, and y is as defined above and described in embodiments herein, both singly and in combination.

In some embodiments, the present invention provides a compound of formula I-a, wherein Ring P and Ring Q form a benzoxazole ring as shown, to provide a compound of formula I-d-1:

I-d-1

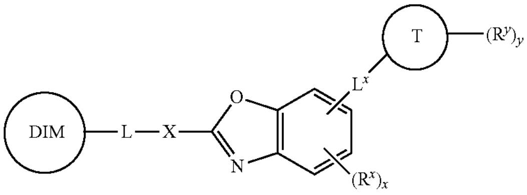

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form an indazole ring as shown, to provide a compound of formula I-d-2:

I-d-2

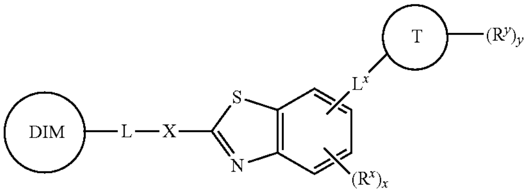

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a indazole ring as shown, to provide a compound of formula I-d-3:

I-d-3

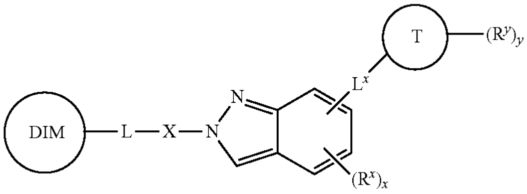

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a pyrazolopyridine ring as shown, to provide a compound of formula I-d-4:

I-d-4

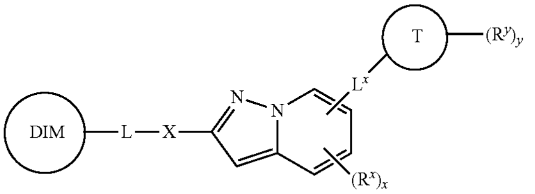

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a 5-azaindazole ring as shown, to provide a compound of formula I-d-5:

I-d-5

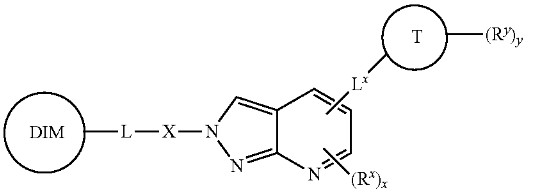

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form an imidazo[1,2-a]pyridine ring as shown, to provide a compound of formula I-d-6:

I-d-6

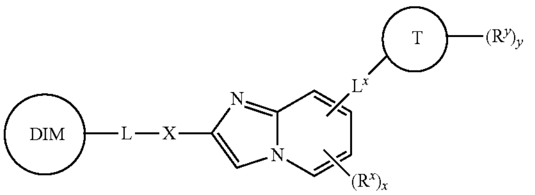

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form an indazole ring, and $R^x$ is

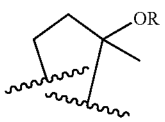

as shown, to provide a compound of formula I-e-1:

I-e-1

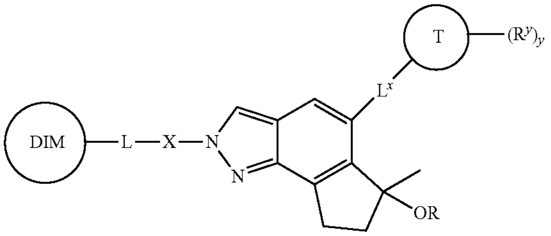

or a pharmaceutically acceptable salt thereof, wherein each of DIM, L, $L^x$, X, $R^Y$, Ring T, and y is as defined above and described in embodiments herein, both singly and in combination.

In some embodiments, the present invention provides a compound of formula I-a, wherein Ring Q is benzo, a single $R^x$ is —OR, and X is cyclohexyl as shown, to provide a compound of formula I-e-2:

I-e-2

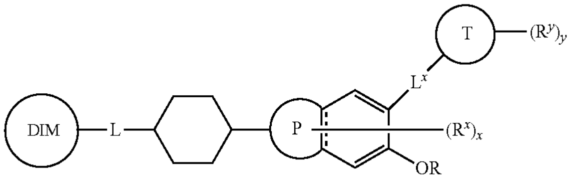

or a pharmaceutically acceptable salt thereof, wherein each of DIM, L, $L^x$, $R^x$, $R^Y$, Ring P, Ring T, x, and y is as defined above and described in embodiments herein, both singly and in combination.

In some embodiments, the present invention provides a compound of formula I-a, wherein Ring P and Ring Q form an indazole ring, a single $R^x$ is —OR, and X is cyclohexyl as shown, to provide a compound of formula I-e-3:

I-e-3

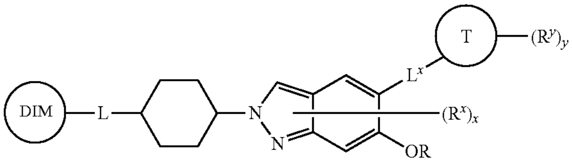

or a pharmaceutically acceptable salt thereof, wherein each of DIM, L, $L^x$, $R^x$, $R^Y$, Ring T, x, and y is as defined above and described in embodiments herein, both singly and in combination.

In some embodiments, the present invention provides a compound of formula I-a, wherein Ring P and Ring Q form an indazole ring and Ring T is cyclohexyl as shown, to provide a compound of formula I-f-1:

I-f-1

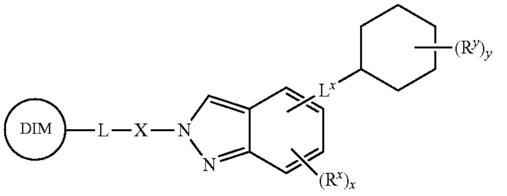

or a pharmaceutically acceptable salt thereof, wherein each of DIM, L, $L^x$, X, $R^x$, $R^y$, x, and y is as defined above and described in embodiments herein, both singly and in combination.

In some embodiments, the present invention provides a compound of formula I-a, wherein Ring P and Ring Q form a 4,5,6,7-tetrahydro-2H-indazole ring as shown, to provide a compound of formula I-f-2:

I-f-2

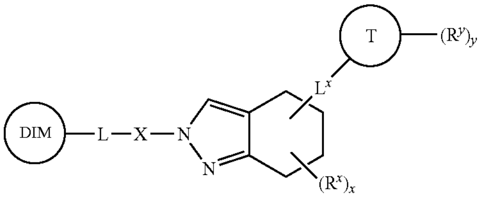

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a isoindolin-1-one ring as shown, to provide a compound of formula I-f-3:

I-f-3

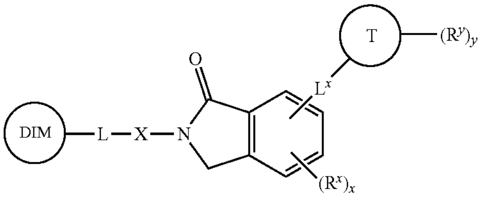

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a quinoline ring as shown, to provide a compound of formula I-g-1:

I-g-1

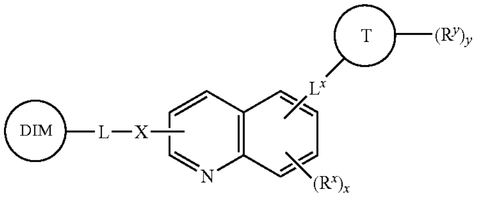

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a 2H-thieno[2,3-c]pyrazole ring as shown, to provide a compound of formula I-g-2:

I-g-2

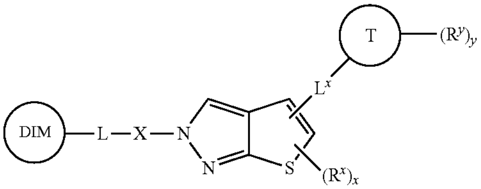

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P is pyridine and Ring Q is phenyl as shown, to provide a compound of formula I-h-1:

I-h-1

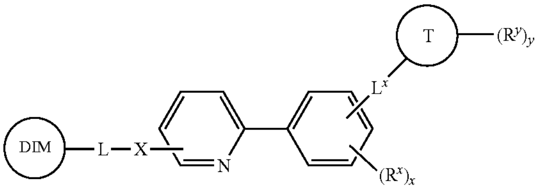

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P is pyrazole and Ring Q is phenyl as shown, to provide a compound of formula I-h-2:

I-h-2

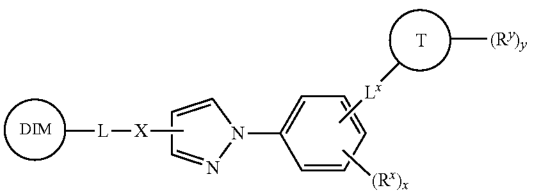

or a pharmaceutically acceptable salt thereof, wherein each of DIM, L, $L^x$, X, $R^x$, $R^y$, Ring T, x, and y is as defined above and described in embodiments herein, both singly and in combination.

In certain embodiments, the present invention provides a compound of formula I, wherein TRAK is an TRAK-4 binding moiety thereby forming a compound of formula I-i:

I-i

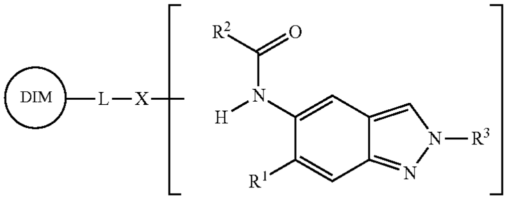

or a pharmaceutically acceptable salt thereof, wherein L and DIM are as defined above and described in embodiments herein, and wherein each of the variables $R^1$, $R^2$, and $R^3$ is as described and defined in WO 2017/148902 and US 2019/071432, the entirety of each of which is herein incorporated by reference.

In certain embodiments, the present invention provides a compound of formula I, wherein TRAK is an TRAK-4 binding moiety thereby forming a compound of formula I-j:

I-j

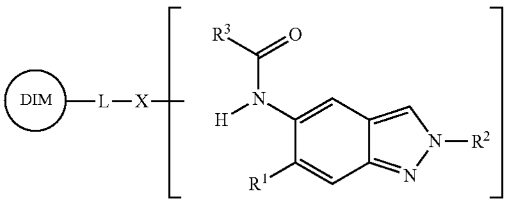

or a pharmaceutically acceptable salt thereof, wherein L and DIM are as defined above and described in embodiments herein, and wherein each of the variables $R^1$, $R^2$, and $R^3$ is as described and defined in WO 2017/108744, the entirety of each of which is herein incorporated by reference.

In some embodiments, IRAK is

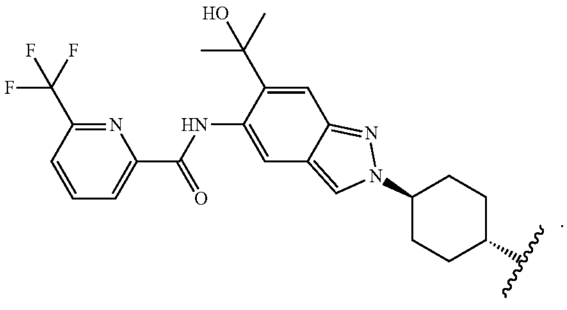 [SMILES: *[C@H]1CC[C@H](n2cc3cc(NC(=O)c4cccc(C(F)(F)F)n4)c(C(C)(C)O)cc3n2)CC1]

In some embodiments, IRAK is

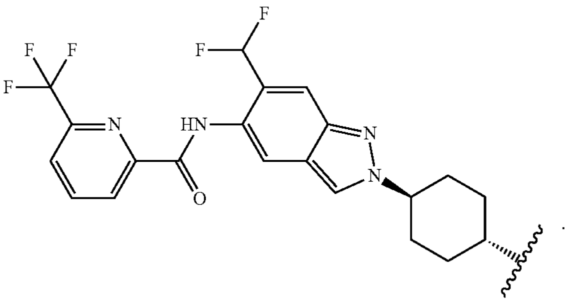 [SMILES: *[C@H]1CC[C@H](n2cc3cc(NC(=O)c4cccc(C(F)(F)F)n4)c(C(F)F)cc3n2)CC1]

In some embodiments, IRAK is

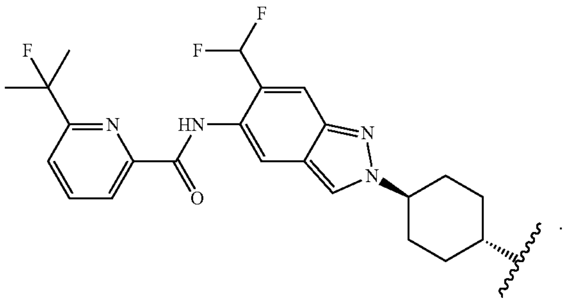 [SMILES: *[C@H]1CC[C@H](n2cc3cc(NC(=O)c4cccc(C(C)(C)F)n4)c(C(F)F)cc3n2)CC1]

In some embodiments, IRAK is

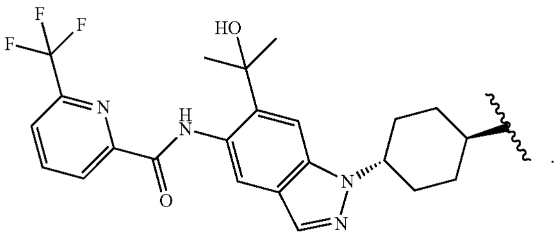 [SMILES: *[C@H]1CC[C@H](n2ncc3cc(NC(=O)c4cccc(C(F)(F)F)n4)c(C(C)(C)O)cc32)CC1]

In some embodiments, IRAK is
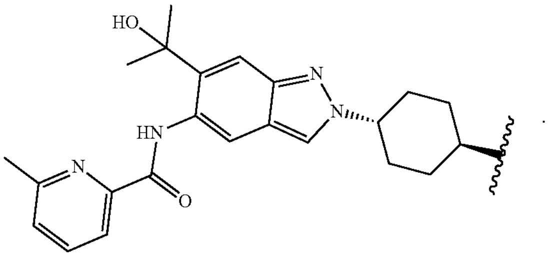 [SMILES: *[C@H]1CC[C@H](n2cc3cc(NC(=O)c4cccc(C)n4)c(C(C)(C)O)cc3n2)CC1]
In some embodiments, IRAK is
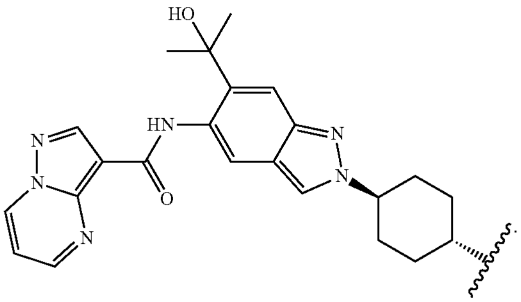 [SMILES: *[C@H]1CC[C@H](n2cc3cc(NC(=O)c4cnn5cccnc45)c(C(C)(C)O)cc3n2)CC1]
In some embodiments, IRAK is
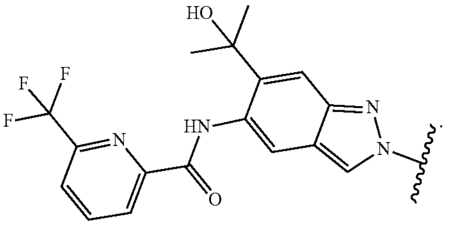 [SMILES: *n1cc2cc(NC(=O)c3cccc(C(F)(F)F)n3)c(C(C)(C)O)cc2n1]
In some embodiments, IRAK is
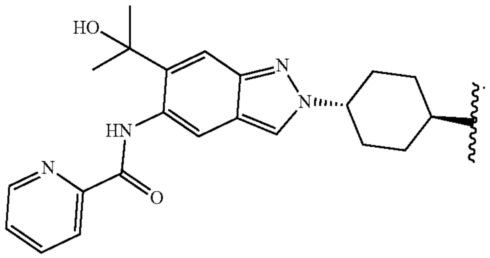 [SMILES: *[C@H]1CC[C@H](n2cc3cc(NC(=O)c4ccccn4)c(C(C)(C)O)cc3n2)CC1]
In some embodiments, IRAK is
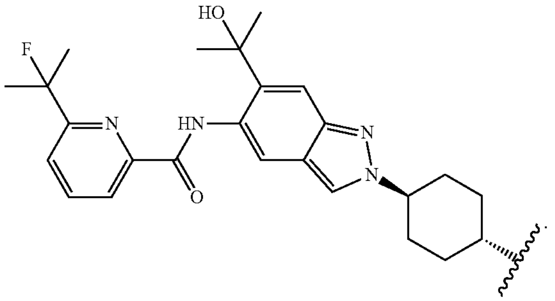 [SMILES: *[C@H]1CC[C@H](n2cc3cc(NC(=O)c4cccc(C(C)(C)F)n4)c(C(C)(C)O)cc3n2)CC1]
In some embodiments, IRAK is
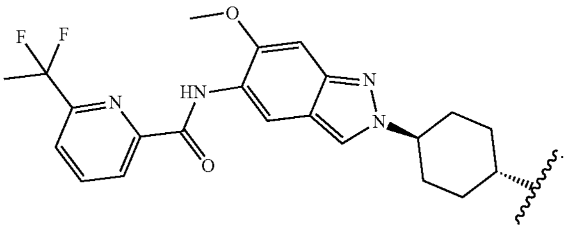 [SMILES: *[C@H]1CC[C@H](n2cc3cc(NC(=O)c4cccc(C(C)(F)F)n4)c(OC)cc3n2)CC1]
In some embodiments, IRAK is
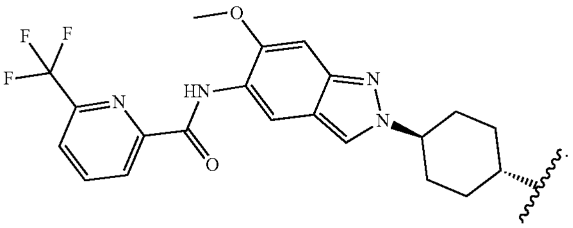 [SMILES: *[C@H]1CC[C@H](n2cc3cc(NC(=O)c4cccc(C(F)(F)F)n4)c(OC)cc3n2)CC1]
In some embodiments, TRAK is
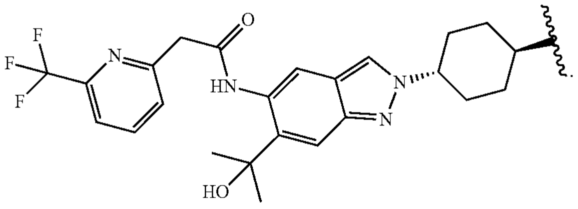 [SMILES: *[C@H]1CC[C@H](n2cc3cc(NC(=O)Cc4cccc(C(F)(F)F)n4)c(C(C)(C)O)cc3n2)CC1]
In some embodiments, IRAK is
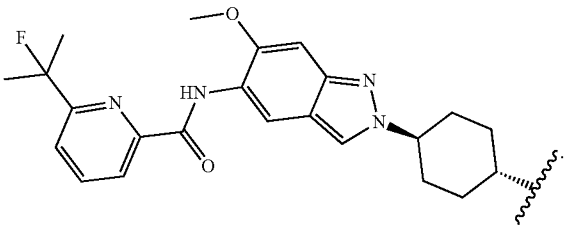 [SMILES: *[C@H]1CC[C@H](n2cc3cc(NC(=O)c4cccc(C(C)(C)F)n4)c(OC)cc3n2)CC1]

In some embodiments, IRAK is
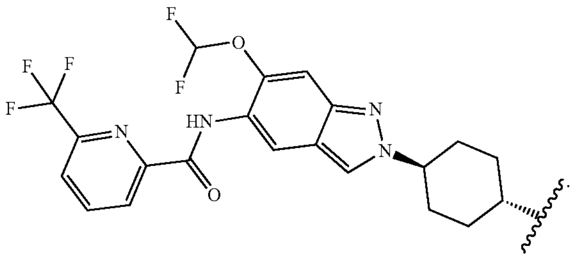 [SMILES: *[C@H]1CC[C@H](n2cc3cc(NC(=O)c4cccc(C(F)(F)F)n4)c(OC(F)F)cc3n2)CC1]
In some embodiments, IRAK is
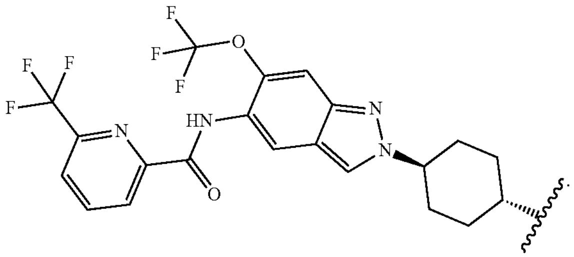 [SMILES: *[C@H]1CC[C@H](n2cc3cc(NC(=O)c4cccc(C(F)(F)F)n4)c(OC(F)(F)F)cc3n2)CC1]
In some embodiments, IRAK is
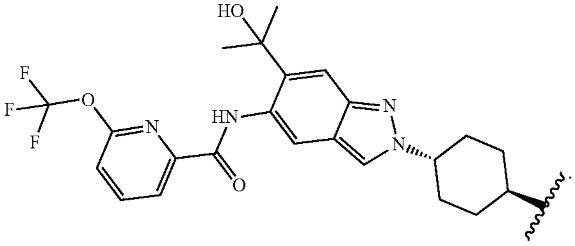 [SMILES: *[C@H]1CC[C@H](n2cc3cc(NC(=O)c4cccc(OC(F)(F)F)n4)c(C(C)(C)O)cc3n2)CC1]
In some embodiments, IRAK is
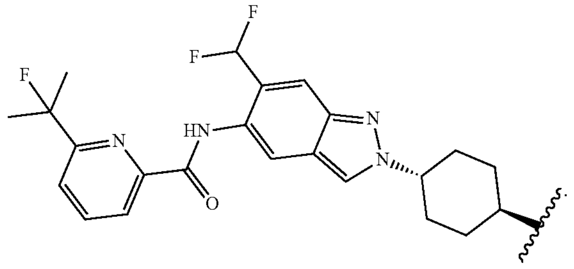 [SMILES: *[C@H]1CC[C@H](n2cc3cc(NC(=O)c4cccc(C(C)(C)F)n4)c(C(F)F)cc3n2)CC1]
In some embodiments, TRAK is
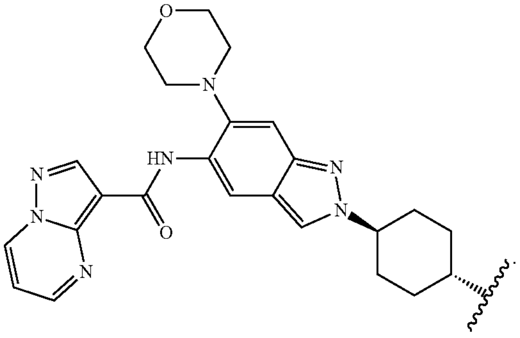 [SMILES: *[C@H]1CC[C@H](n2cc3cc(NC(=O)c4cnn5cccnc45)c(N4CCOCC4)cc3n2)CC1]
In some embodiments, IRAK is
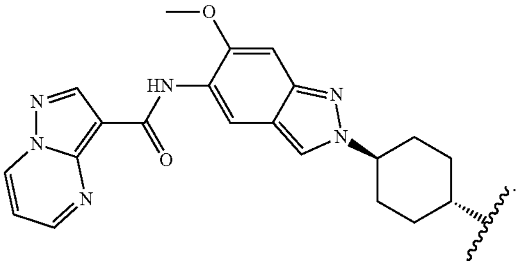 [SMILES: *[C@H]1CC[C@H](n2cc3cc(NC(=O)c4cnn5cccnc45)c(OC)cc3n2)CC1]
In some embodiments, IRAK is
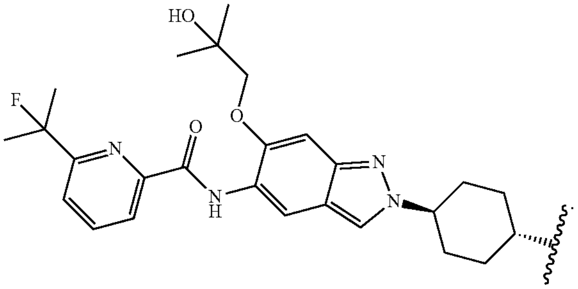 [SMILES: *[C@H]1CC[C@H](n2cc3cc(NC(=O)c4cccc(C(C)(C)F)n4)c(OCC(C)(C)O)cc3n2)CC1]
In some embodiments, IRAK is
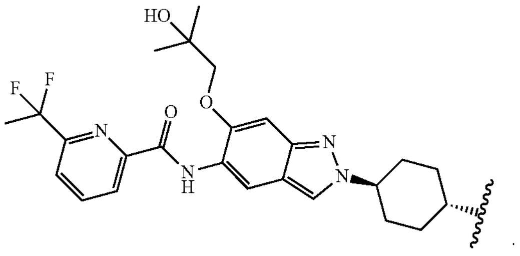 [SMILES: *[C@H]1CC[C@H](n2cc3cc(NC(=O)c4cccc(C(C)(F)F)n4)c(OCC(C)(C)O)cc3n2)CC1]

In some embodiments, IRAK is
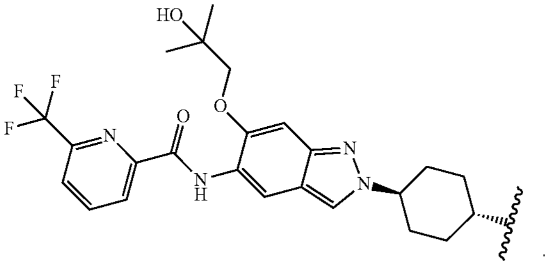 [SMILES: *[C@H]1CC[C@H](n2cc3cc(NC(=O)c4cccc(C(F)(F)F)n4)c(OCC(C)(C)O)cc3n2)CC1]
In some embodiments, IRAK is
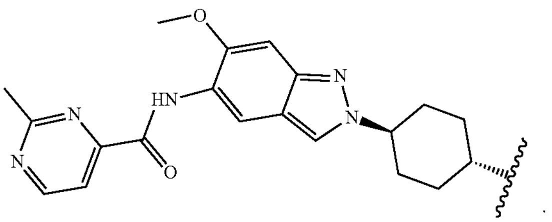 [SMILES: *[C@H]1CC[C@H](n2cc3cc(NC(=O)c4ccnc(C)n4)c(OC)cc3n2)CC1]
In some embodiments, IRAK is
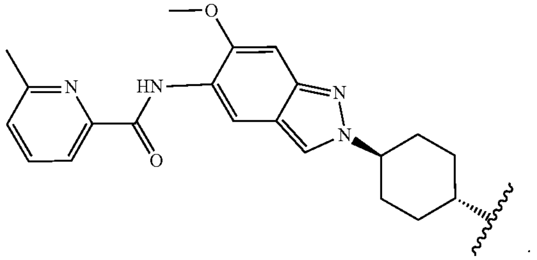 [SMILES: *[C@H]1CC[C@H](n2cc3cc(NC(=O)c4cccc(C)n4)c(OC)cc3n2)CC1]
In some embodiments, IRAK is
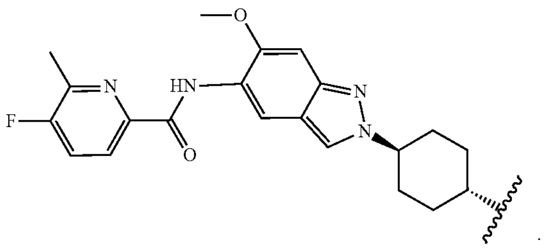 [SMILES: *[C@H]1CC[C@H](n2cc3cc(NC(=O)c4ccc(F)c(C)n4)c(OC)cc3n2)CC1]
In some embodiments, IRAK is
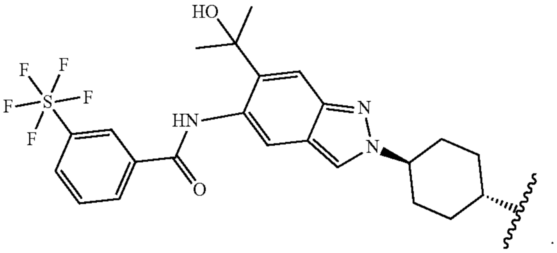 [SMILES: *[C@H]1CC[C@H](n2cc3cc(NC(=O)c4cccc(S(F)(F)(F)(F)F)c4)c(C(C)(C)O)cc3n2)CC1]
In some embodiments, IRAK is
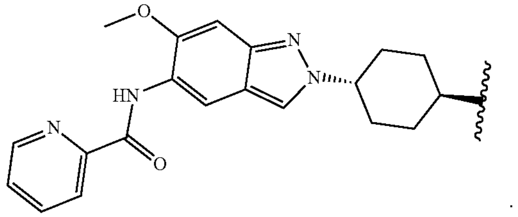 [SMILES: *[C@H]1CC[C@H](n2cc3cc(NC(=O)c4ccccn4)c(OC)cc3n2)CC1]
In some embodiments, IRAK is
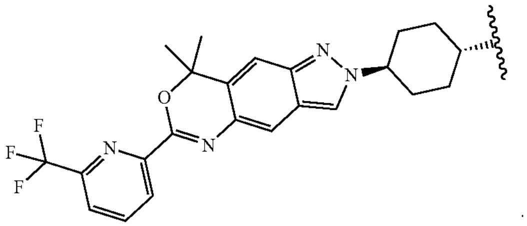 [SMILES: *[C@H]1CC[C@H](n2cc3cc4c(cc3n2)C(C)(C)OC(c2cccc(C(F)(F)F)n2)=N4)CC1]
In some embodiments, IRAK is
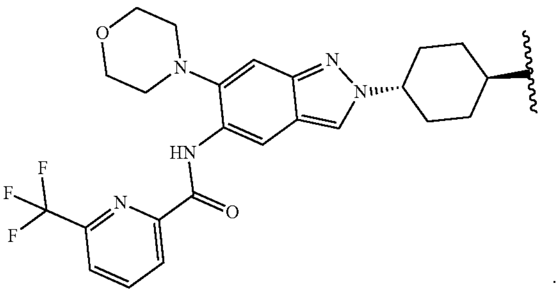 [SMILES: *[C@H]1CC[C@H](n2cc3cc(NC(=O)c4cccc(C(F)(F)F)n4)c(N4CCOCC4)cc3n2)CC1]
In some embodiments, IRAK is
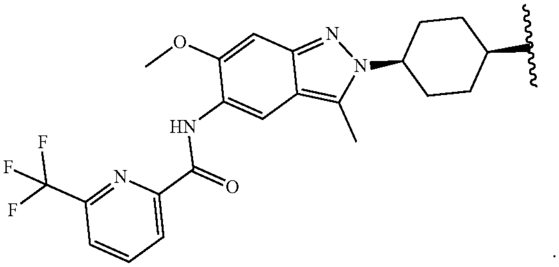 [SMILES: *[C@H]1CC[C@@H](n2nc3cc(OC)c(NC(=O)c4cccc(C(F)(F)F)n4)cc3c2C)CC1]
In some embodiments, IRAK is
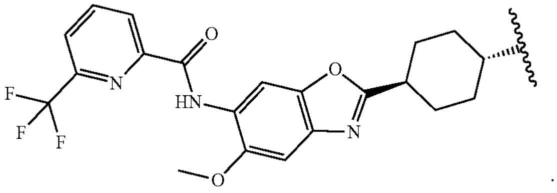 [SMILES: *[C@H]1CC[C@H](c2nc3cc(OC)c(NC(=O)c4cccc(C(F)(F)F)n4)cc3o2)CC1]

In some embodiments, IRAK is
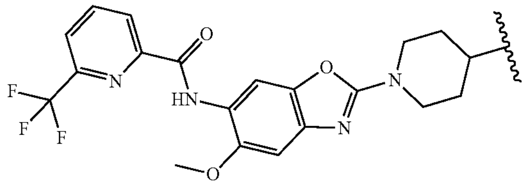
.
In some embodiments, IRAK is
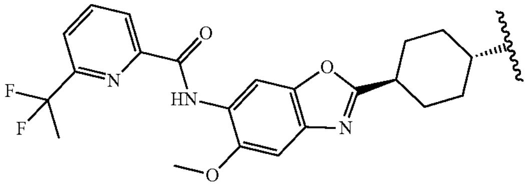
.
In some embodiments, IRAK is
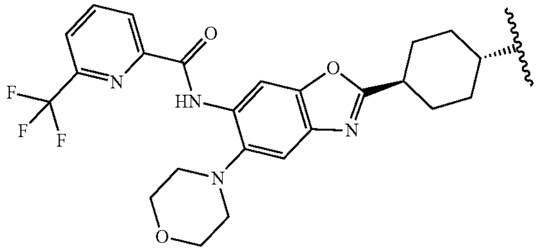
.
In some embodiments, IRAK is
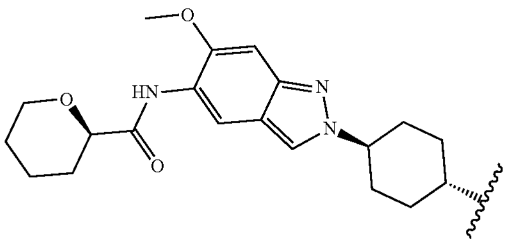
.
In some embodiments, IRAK is
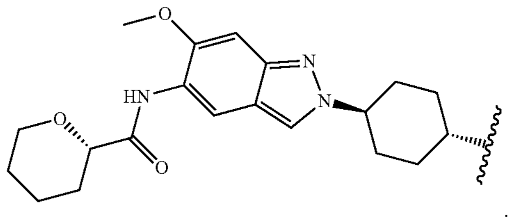 [SMILES: *[C@H]1CC[C@H](n2cc3cc(NC(=O)[C@@H]4CCCCO4)c(OC)cc3n2)CC1]
.
In some embodiments, TRAK is
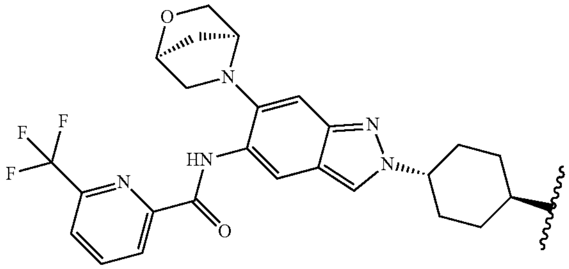
.
In some embodiments, IRAK is
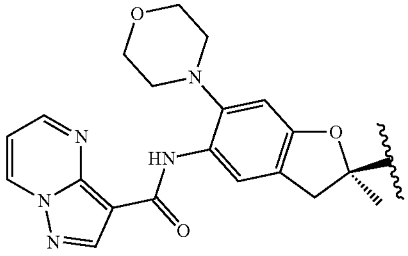
.
In some embodiments, IRAK is
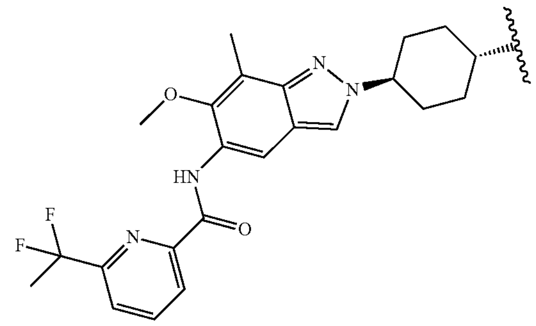
.
In some embodiments, IRAK is
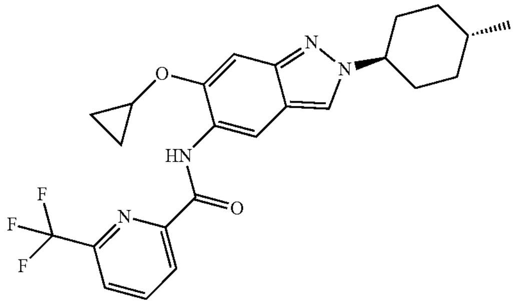
.

In some embodiments, IRAK is
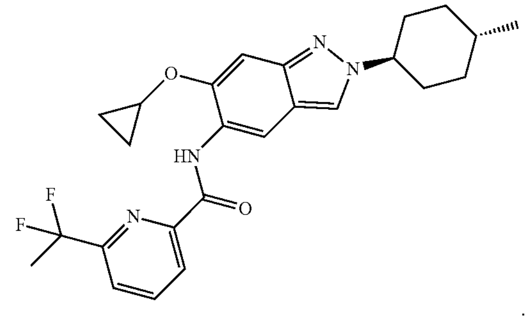 [SMILES: CC(F)(F)c1cccc(C(=O)Nc2cc3cn([C@H]4CC[C@H](C)CC4)nc3cc2OC2CC2)n1]
In some embodiments, TRAK is
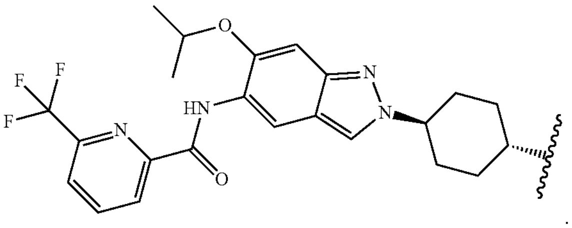 [SMILES: *[C@H]1CC[C@H](n2cc3cc(NC(=O)c4cccc(C(F)(F)F)n4)c(OC(C)C)cc3n2)CC1]
In some embodiments, TRAK is
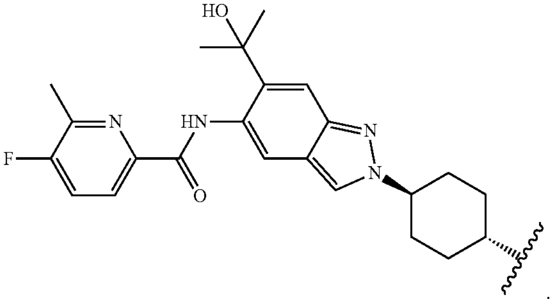 [SMILES: *[C@H]1CC[C@H](n2cc3cc(NC(=O)c4ccc(F)c(C)n4)c(C(C)(C)O)cc3n2)CC1]
In some embodiments, IRAK is
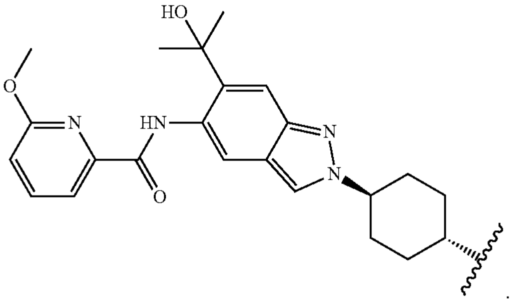 [SMILES: *[C@H]1CC[C@H](n2cc3cc(NC(=O)c4cccc(OC)n4)c(C(C)(C)O)cc3n2)CC1]
In some embodiments, IRAK is
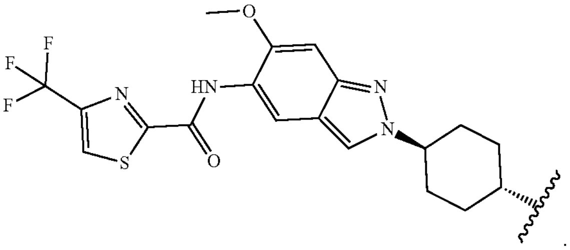 [SMILES: *[C@H]1CC[C@H](n2cc3cc(NC(=O)c4nc(C(F)(F)F)cs4)c(OC)cc3n2)CC1]
In some embodiments, IRAK is
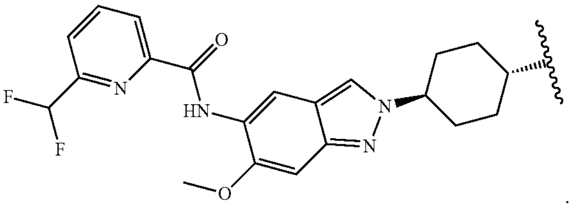 [SMILES: *[C@H]1CC[C@H](n2cc3cc(NC(=O)c4cccc(C(F)F)n4)c(OC)cc3n2)CC1]
In some embodiments, IRAK is
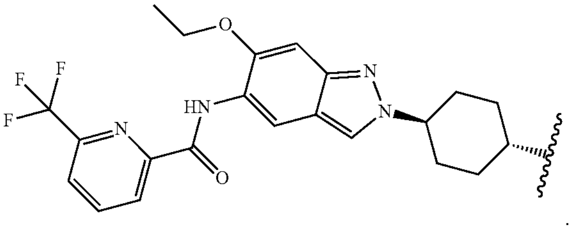 [SMILES: *[C@H]1CC[C@H](n2cc3cc(NC(=O)c4cccc(C(F)(F)F)n4)c(OCC)cc3n2)CC1]
In some embodiments, IRAK is
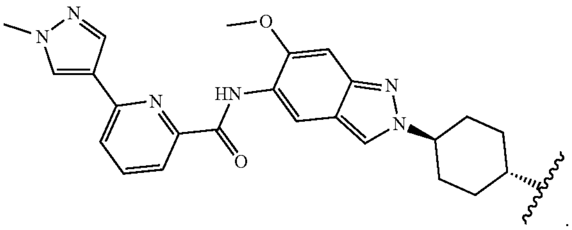 [SMILES: *[C@H]1CC[C@H](n2cc3cc(NC(=O)c4cccc(-c5cnn(C)c5)n4)c(OC)cc3n2)CC1]
In some embodiments, IRAK is
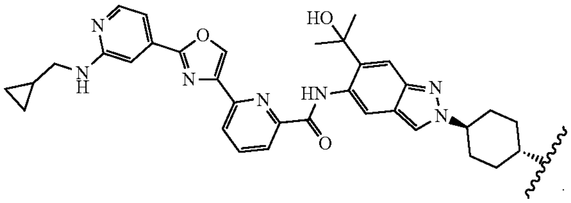 [SMILES: *[C@H]1CC[C@H](n2cc3cc(NC(=O)c4cccc(-c5coc(-c6ccnc(NCC7CC7)c6)n5)n4)c(C(C)(C)O)cc3n2)CC1]

In some embodiments, IRAK is
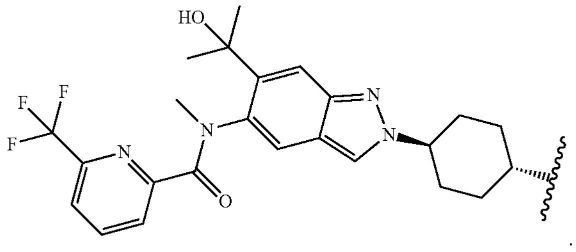 [SMILES: *[C@H]1CC[C@H](n2cc3cc(N(C)C(=O)c4cccc(C(F)(F)F)n4)c(C(C)(C)O)cc3n2)CC1]
In some embodiments, IRAK is
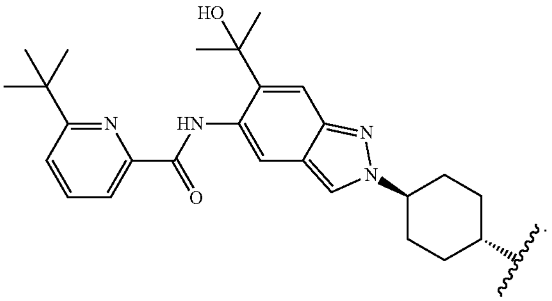
In some embodiments, IRAK is
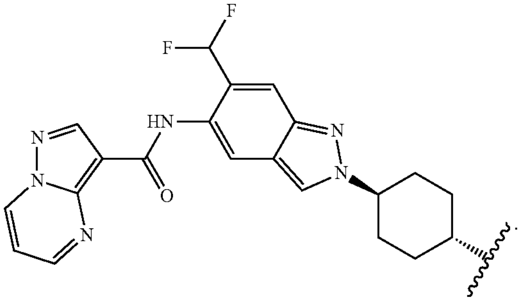 [SMILES: *[C@H]1CC[C@H](n2cc3cc(NC(=O)c4cnn5cccnc45)c(C(F)F)cc3n2)CC1]
In some embodiments, IRAK is
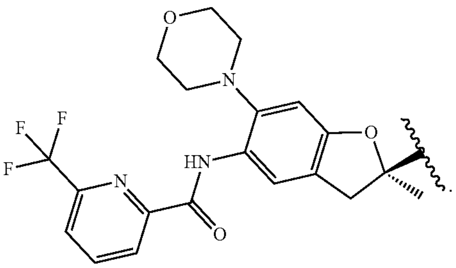 [SMILES: *[C@@]1(C)Cc2cc(NC(=O)c3cccc(C(F)(F)F)n3)c(N3CCOCC3)cc2O1]
In some embodiments, IRAK is
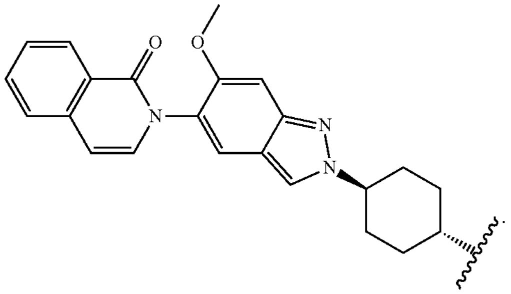 [SMILES: *[C@H]1CC[C@H](n2cc3cc(-n4ccc5ccccc5c4=O)c(OC)cc3n2)CC1]
In some embodiments, IRAK is
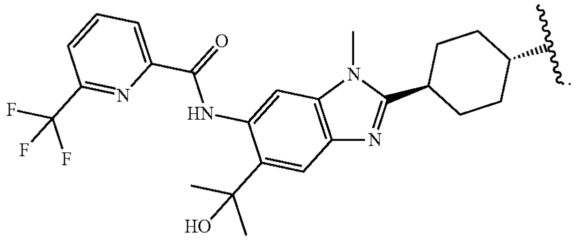 [SMILES: *[C@H]1CC[C@H](c2nc3cc(C(C)(C)O)c(NC(=O)c4cccc(C(F)(F)F)n4)cc3n2C)CC1]
In some embodiments, IRAK is
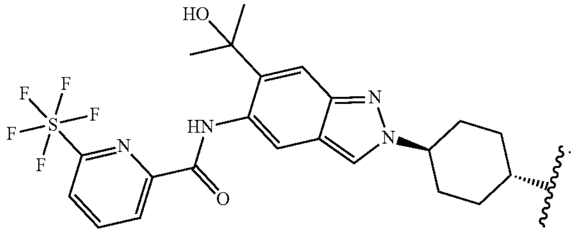 [SMILES: *[C@H]1CC[C@H](n2cc3cc(NC(=O)c4cccc(S(F)(F)(F)(F)F)n4)c(C(C)(C)O)cc3n2)CC1]
In some embodiments, IRAK is
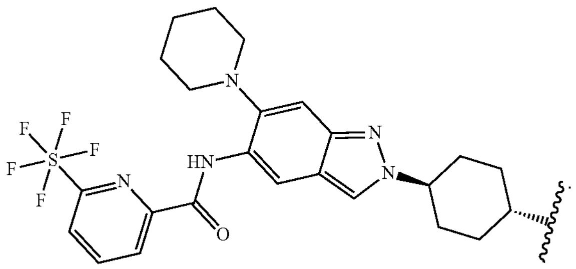 [SMILES: *[C@H]1CC[C@H](n2cc3cc(NC(=O)c4cccc(S(F)(F)(F)(F)F)n4)c(N4CCCCC4)cc3n2)CC1]

In some embodiments, IRAK is
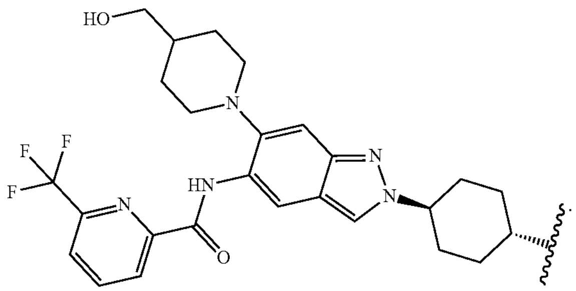 [SMILES: *[C@H]1CC[C@H](n2cc3cc(NC(=O)c4cccc(C(F)(F)F)n4)c(N4CCC(CO)CC4)cc3n2)CC1]
In some embodiments, IRAK is
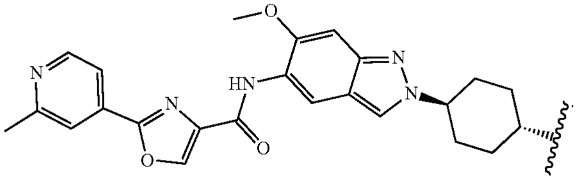 [SMILES: *[C@H]1CC[C@H](n2cc3cc(NC(=O)c4coc(-c5ccnc(C)c5)n4)c(OC)cc3n2)CC1]
In some embodiments, IRAK is
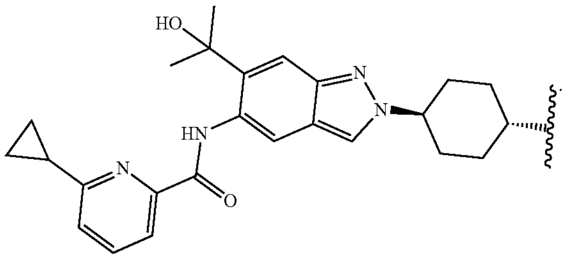 [SMILES: *[C@H]1CC[C@H](n2cc3cc(NC(=O)c4cccc(C5CC5)n4)c(C(C)(C)O)cc3n2)CC1]
In some embodiments, IRAK is
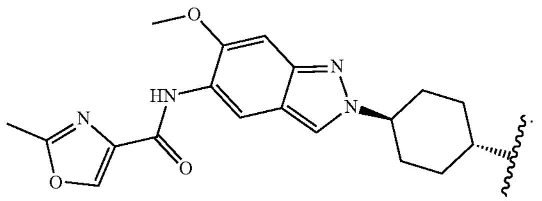 [SMILES: *[C@H]1CC[C@H](n2cc3cc(NC(=O)c4coc(C)n4)c(OC)cc3n2)CC1]
In some embodiments, IRAK is
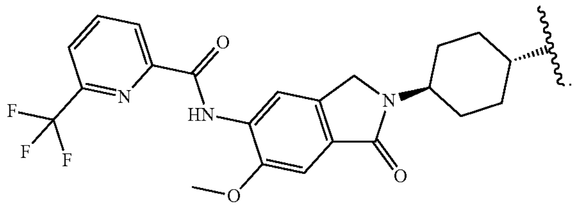 [SMILES: *[C@H]1CC[C@H](N2Cc3cc(NC(=O)c4cccc(C(F)(F)F)n4)c(OC)cc3C2=O)CC1]
In some embodiments, IRAK is
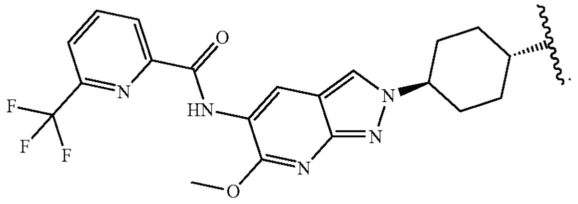 [SMILES: *[C@H]1CC[C@H](n2cc3cc(NC(=O)c4cccc(C(F)(F)F)n4)c(OC)nc3n2)CC1]
In some embodiments, TRAK is
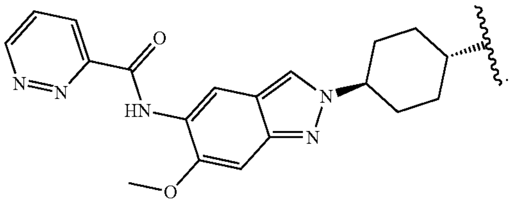 [SMILES: *[C@H]1CC[C@H](n2cc3cc(NC(=O)c4cccnn4)c(OC)cc3n2)CC1]
In some embodiments, IRAK is
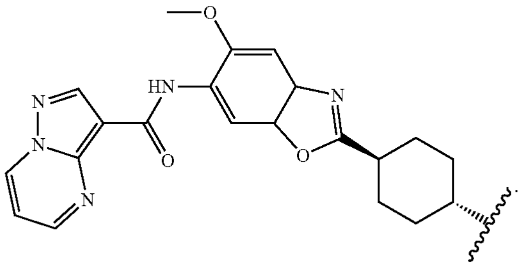 [SMILES: *[C@H]1CC[C@H](C2=NC3C=C(OC)C(NC(=O)c4cnn5cccnc45)=CC3O2)CC1]
In some embodiments, TRAK is
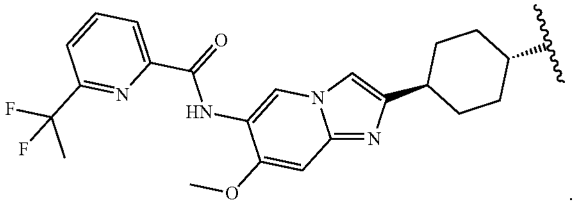 [SMILES: *[C@H]1CC[C@H](c2cn3cc(NC(=O)c4cccc(C(C)(F)F)n4)c(OC)cc3n2)CC1]
In some embodiments, IRAK is
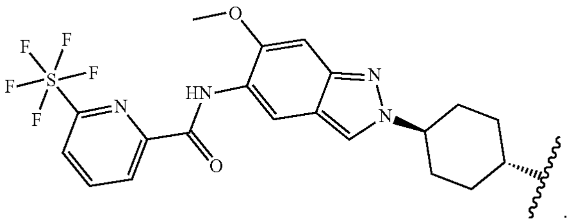 [SMILES: *[C@H]1CC[C@H](n2cc3cc(NC(=O)c4cccc(S(F)(F)(F)(F)F)n4)c(OC)cc3n2)CC1]

In some embodiments, IRAK is
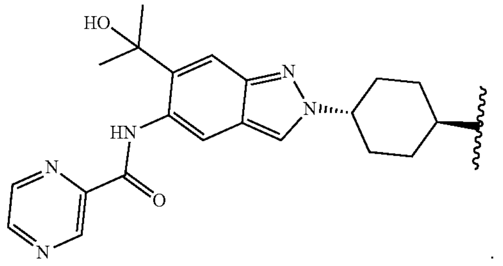 [SMILES: *[C@H]1CC[C@H](n2cc3cc(NC(=O)c4cnccn4)c(C(C)(C)O)cc3n2)CC1]
In some embodiments, IRAK is
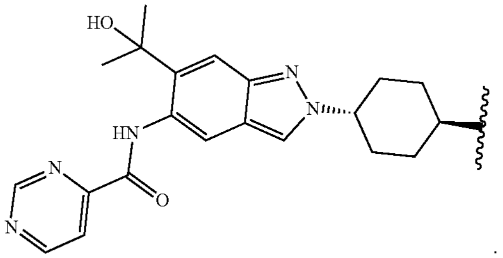 [SMILES: *[C@H]1CC[C@H](n2cc3cc(NC(=O)c4ccncn4)c(C(C)(C)O)cc3n2)CC1]
In some embodiments, IRAK is
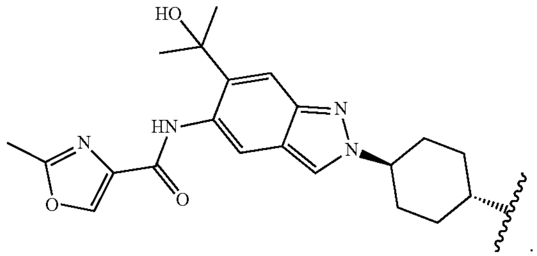 [SMILES: *[C@H]1CC[C@H](n2cc3cc(NC(=O)c4coc(C)n4)c(C(C)(C)O)cc3n2)CC1]
In some embodiments, IRAK is
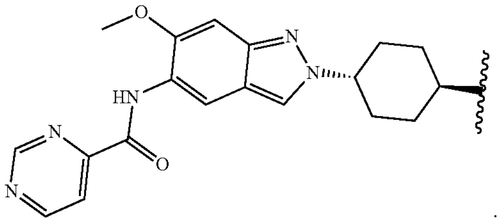 [SMILES: *[C@H]1CC[C@H](n2cc3cc(NC(=O)c4ccncn4)c(OC)cc3n2)CC1]
In some embodiments, IRAK is
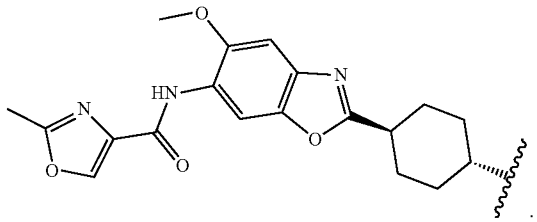 [SMILES: *[C@H]1CC[C@H](c2nc3cc(OC)c(NC(=O)c4coc(C)n4)cc3o2)CC1]
In some embodiments, IRAK is
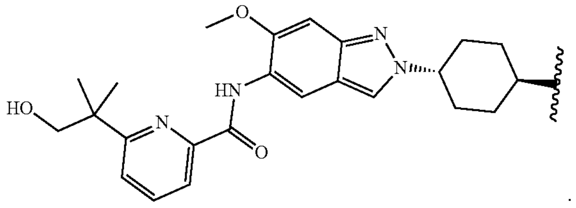 [SMILES: *[C@H]1CC[C@H](n2cc3cc(NC(=O)c4cccc(C(C)(C)CO)n4)c(OC)cc3n2)CC1]
In some embodiments, IRAK is
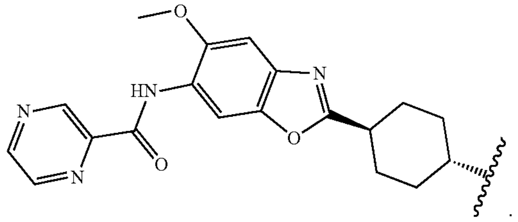 [SMILES: *[C@H]1CC[C@H](c2nc3cc(OC)c(NC(=O)c4cnccn4)cc3o2)CC1]
In some embodiments, IRAK is
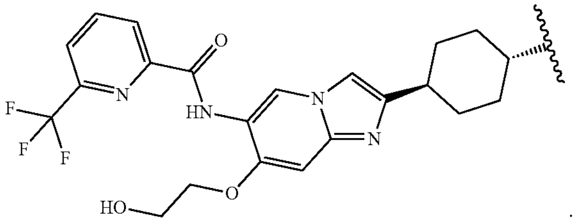 [SMILES: *[C@H]1CC[C@H](c2cn3cc(NC(=O)c4cccc(C(F)(F)F)n4)c(OCCO)cc3n2)CC1]
In some embodiments, IRAK is
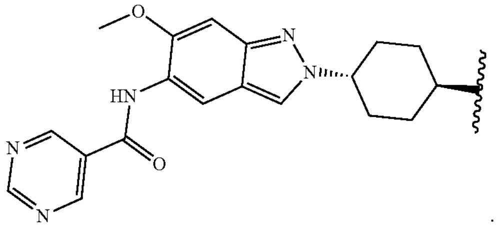 [SMILES: *[C@H]1CC[C@H](n2cc3cc(NC(=O)c4cncnc4)c(OC)cc3n2)CC1]
In some embodiments, IRAK is
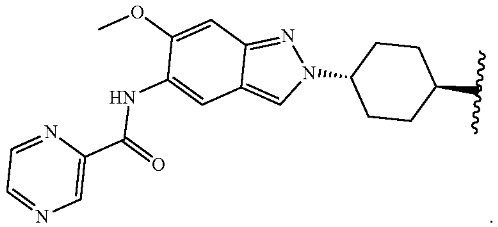 [SMILES: *[C@H]1CC[C@H](n2cc3cc(NC(=O)c4cnccn4)c(OC)cc3n2)CC1]

In some embodiments, TRAK is
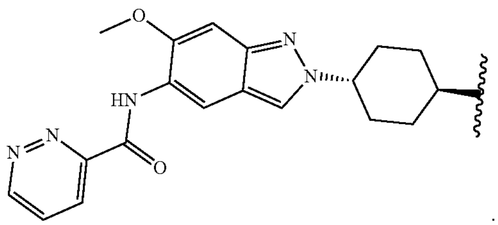 [SMILES: *[C@H]1CC[C@H](n2cc3cc(NC(=O)c4cccnn4)c(OC)cc3n2)CC1]
.
In some embodiments, IRAK is
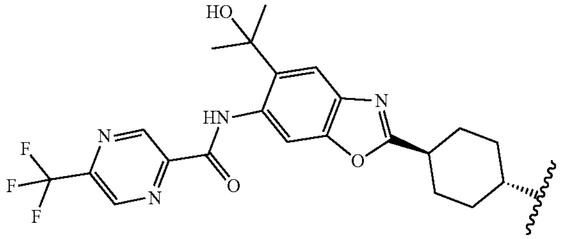 [SMILES: *[C@H]1CC[C@H](c2nc3cc(C(C)(C)O)c(NC(=O)c4cnc(C(F)(F)F)cn4)cc3o2)CC1]
.
In some embodiments, IRAK is
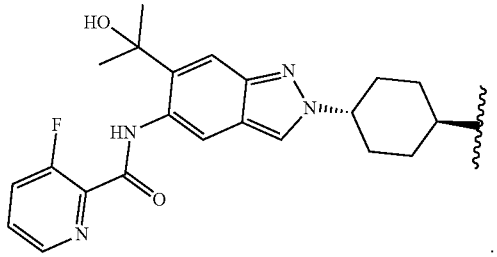 [SMILES: *[C@H]1CC[C@H](n2cc3cc(NC(=O)c4ncccc4F)c(C(C)(C)O)cc3n2)CC1]
.
In some embodiments, IRAK is
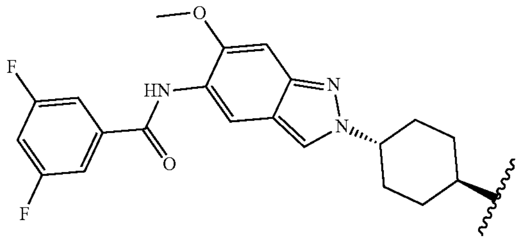
.
F In some embodiments, IRAK is
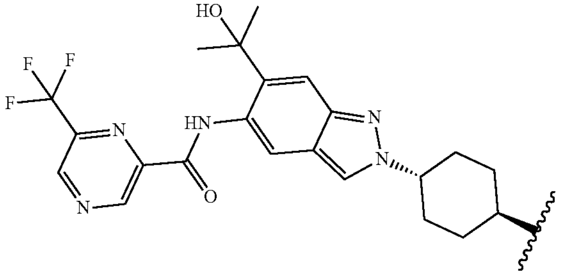
.
In some embodiments, IRAK is
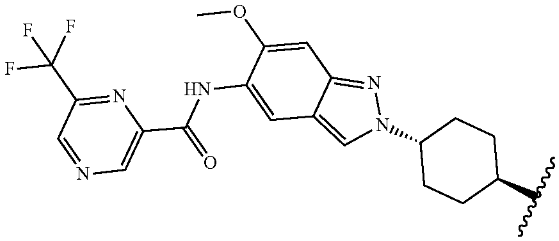
.
In some embodiments, IRAK is
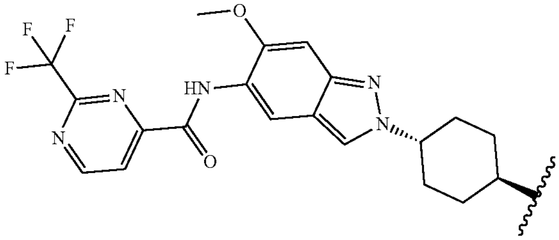
.
In some embodiments, IRAK is
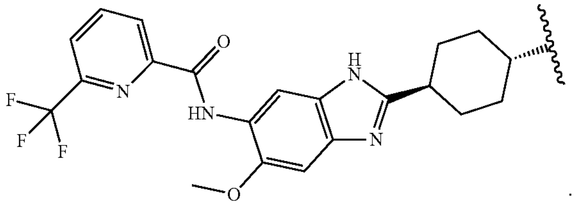 [SMILES: *[C@H]1CC[C@H](c2nc3cc(OC)c(NC(=O)c4cccc(C(F)(F)F)n4)cc3[nH]2)CC1]
.
In some embodiments, IRAK is
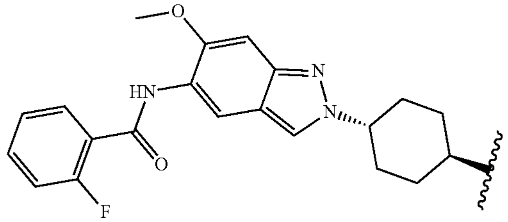
.
In some embodiments, IRAK is
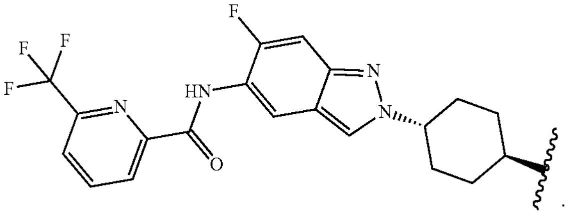 [SMILES: *[C@H]1CC[C@H](n2cc3cc(NC(=O)c4cccc(C(F)(F)F)n4)c(F)cc3n2)CC1]
.

In some embodiments, IRAK is
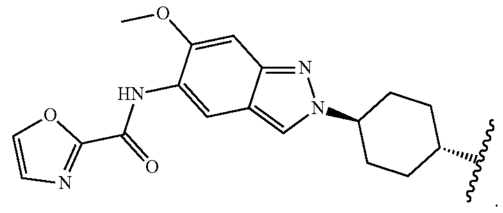 [SMILES: *[C@H]1CC[C@H](n2cc3cc(NC(=O)c4ncco4)c(OC)cc3n2)CC1]
In some embodiments, IRAK is
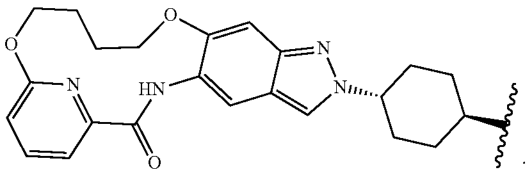 [SMILES: *[C@H]1CC[C@H](n2cc3cc4c(cc3n2)OCCCCOc2cccc(n2)C(=O)N4)CC1]
In some embodiments, IRAK is
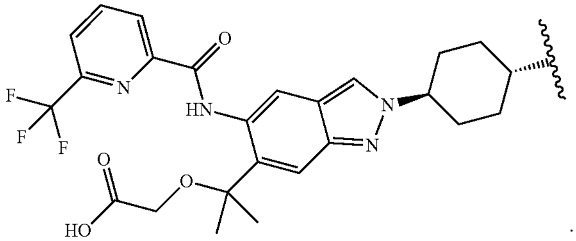 [SMILES: *[C@H]1CC[C@H](n2cc3cc(NC(=O)c4cccc(C(F)(F)F)n4)c(C(C)(C)OCC(=O)O)cc3n2)CC1]
In some embodiments, IRAK is
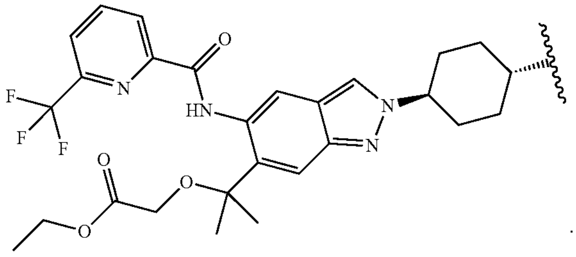 [SMILES: *[C@H]1CC[C@H](n2cc3cc(NC(=O)c4cccc(C(F)(F)F)n4)c(C(C)(C)OCC(=O)OCC)cc3n2)CC1]
In some embodiments, IRAK is
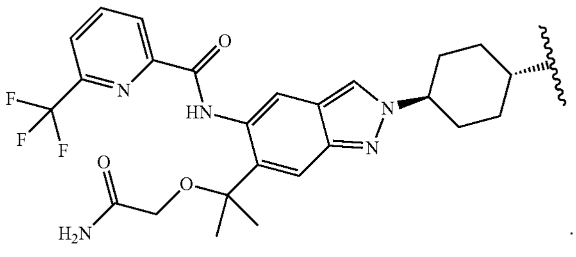 [SMILES: *[C@H]1CC[C@H](n2cc3cc(NC(=O)c4cccc(C(F)(F)F)n4)c(C(C)(C)OCC(N)=O)cc3n2)CC1]
In some embodiments, IRAK is
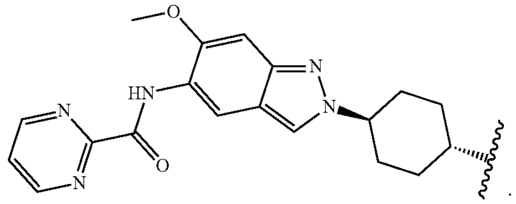 [SMILES: *[C@H]1CC[C@H](n2cc3cc(NC(=O)c4ncccn4)c(OC)cc3n2)CC1]
In some embodiments, IRAK is
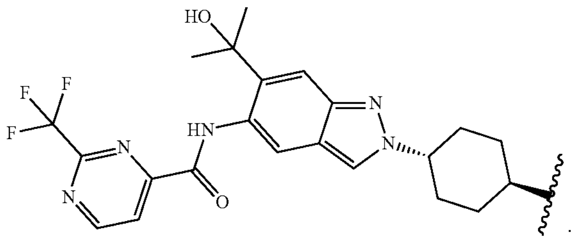 [SMILES: *[C@H]1CC[C@H](n2cc3cc(NC(=O)c4ccnc(C(F)(F)F)n4)c(C(C)(C)O)cc3n2)CC1]
In some embodiments, IRAK is
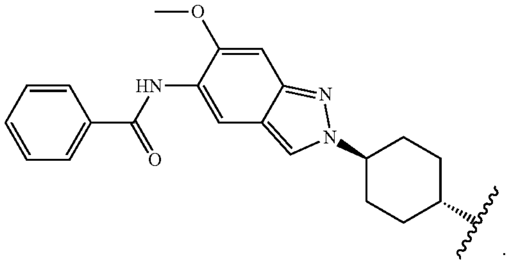 [SMILES: *[C@H]1CC[C@H](n2cc3cc(NC(=O)c4ccccc4)c(OC)cc3n2)CC1]
In some embodiments, IRAK is
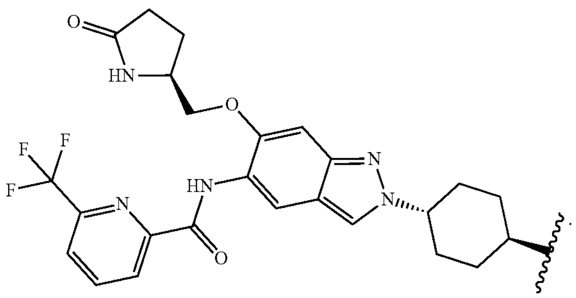 [SMILES: *[C@H]1CC[C@H](n2cc3cc(NC(=O)c4cccc(C(F)(F)F)n4)c(OC[C@@H]4CCC(=O)N4)cc3n2)CC1]

In some embodiments, IRAK is
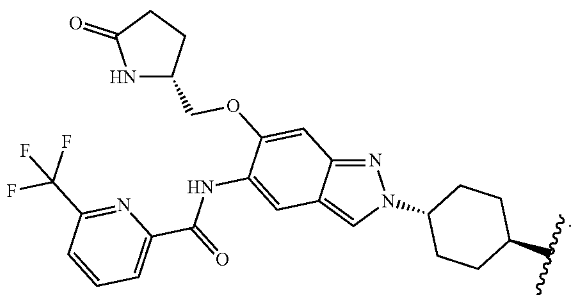 [SMILES: *[C@H]1CC[C@H](n2cc3cc(NC(=O)c4cccc(C(F)(F)F)n4)c(OC[C@H]4CCC(=O)N4)cc3n2)CC1]
In some embodiments, IRAK is
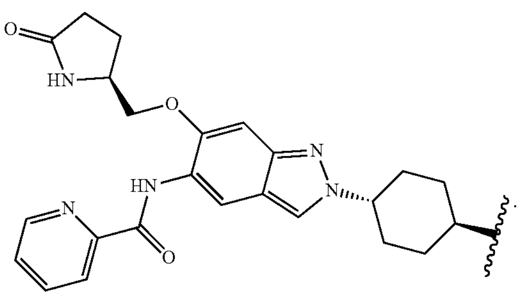 [SMILES: *[C@H]1CC[C@H](n2cc3cc(NC(=O)c4ccccn4)c(OC[C@@H]4CCC(=O)N4)cc3n2)CC1]
In some embodiments, IRAK is
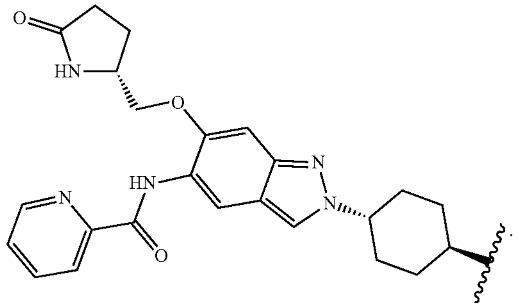 [SMILES: *[C@H]1CC[C@H](n2cc3cc(NC(=O)c4ccccn4)c(OC[C@H]4CCC(=O)N4)cc3n2)CC1]
In some embodiments, IRAK is
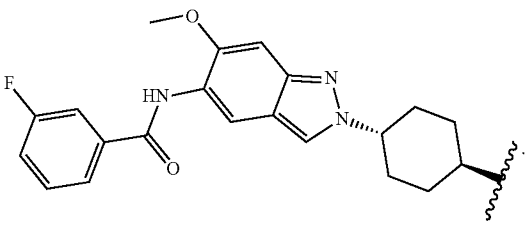 [SMILES: *[C@H]1CC[C@H](n2cc3cc(NC(=O)c4cccc(F)c4)c(OC)cc3n2)CC1]
In some embodiments, IRAK is
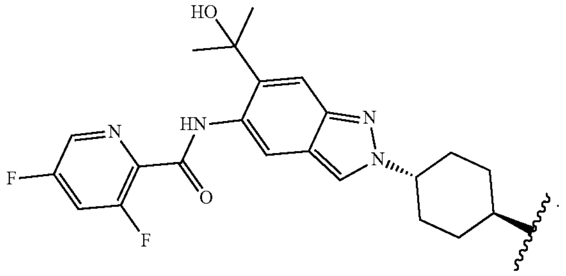 [SMILES: *[C@H]1CC[C@H](n2cc3cc(NC(=O)c4ncc(F)cc4F)c(C(C)(C)O)cc3n2)CC1]
In some embodiments, IRAK is
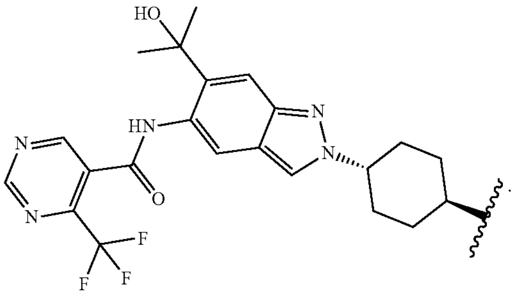 [SMILES: *[C@H]1CC[C@H](n2cc3cc(NC(=O)c4cncnc4C(F)(F)F)c(C(C)(C)O)cc3n2)CC1]
In some embodiments, IRAK is
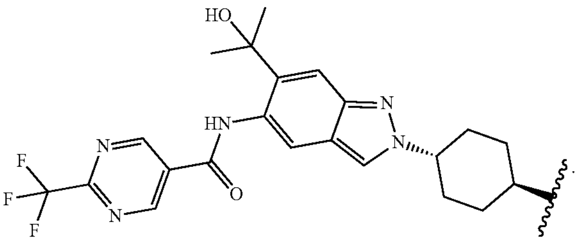 [SMILES: *[C@H]1CC[C@H](n2cc3cc(NC(=O)c4cnc(C(F)(F)F)nc4)c(C(C)(C)O)cc3n2)CC1]
In some embodiments, IRAK is
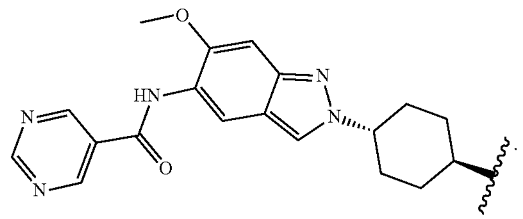 [SMILES: *[C@H]1CC[C@H](n2cc3cc(NC(=O)c4cncnc4)c(OC)cc3n2)CC1]
In some embodiments, IRAK is
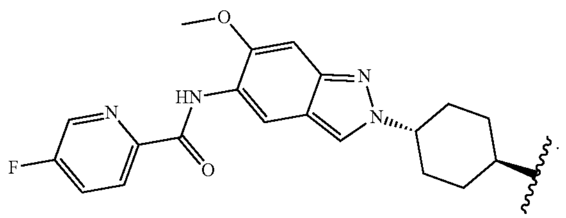 [SMILES: *[C@H]1CC[C@H](n2cc3cc(NC(=O)c4ccc(F)cn4)c(OC)cc3n2)CC1]

In some embodiments, IRAK is
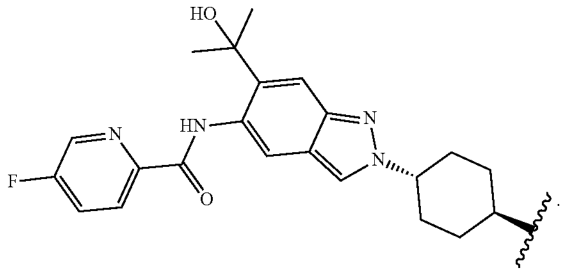 [SMILES: *[C@H]1CC[C@H](n2cc3cc(NC(=O)c4ccc(F)cn4)c(C(C)(C)O)cc3n2)CC1]
In some embodiments, IRAK is
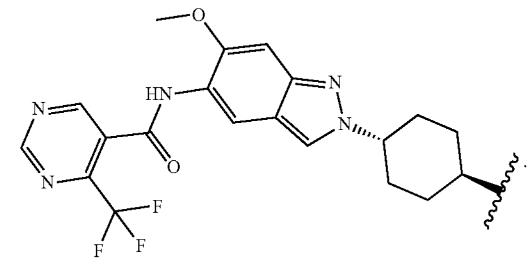 [SMILES: *[C@H]1CC[C@H](n2cc3cc(NC(=O)c4cncnc4C(F)(F)F)c(OC)cc3n2)CC1]
In some embodiments, IRAK is
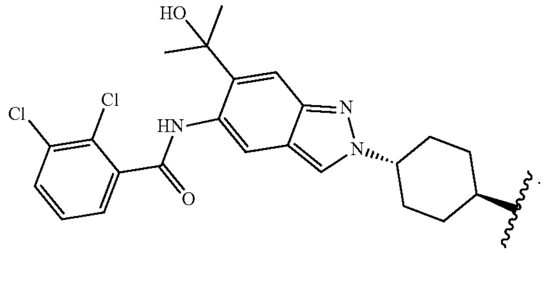 [SMILES: *[C@H]1CC[C@H](n2cc3cc(NC(=O)c4cccc(Cl)c4Cl)c(C(C)(C)O)cc3n2)CC1]
In some embodiments, IRAK is
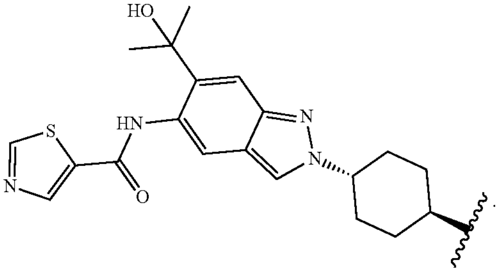 [SMILES: *[C@H]1CC[C@H](n2cc3cc(NC(=O)c4cncs4)c(C(C)(C)O)cc3n2)CC1]
In some embodiments, IRAK is
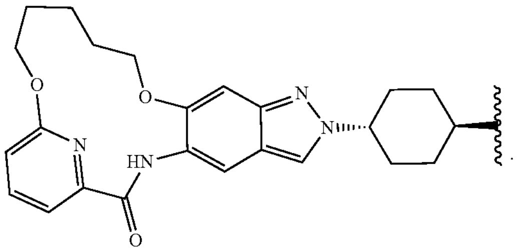 [SMILES: *[C@H]1CC[C@H](n2cc3cc4c(cc3n2)OCCCCCOc2cccc(n2)C(=O)N4)CC1]
In some embodiments, IRAK is
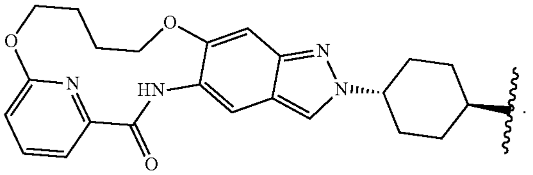 [SMILES: *[C@H]1CC[C@H](n2cc3cc4c(cc3n2)OCCCCOc2cccc(n2)C(=O)N4)CC1]
In some embodiments, IRAK is
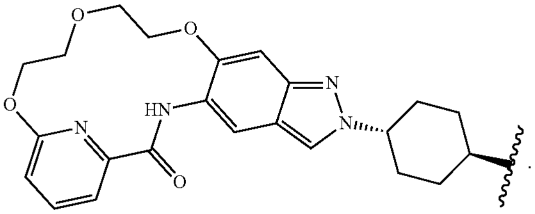 [SMILES: *[C@H]1CC[C@H](n2cc3cc4c(cc3n2)OCCOCCOc2cccc(n2)C(=O)N4)CC1]
In some embodiments, IRAK is
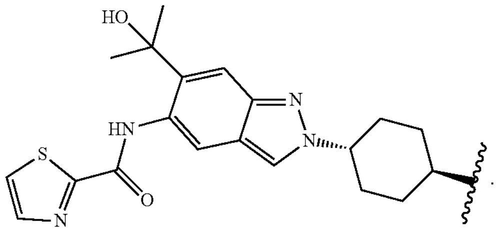 [SMILES: *[C@H]1CC[C@H](n2cc3cc(NC(=O)c4nccs4)c(C(C)(C)O)cc3n2)CC1]
In some embodiments, IRAK is
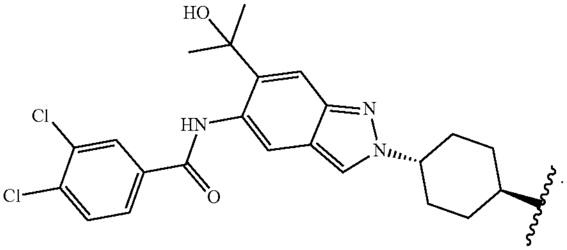 [SMILES: *[C@H]1CC[C@H](n2cc3cc(NC(=O)c4ccc(Cl)c(Cl)c4)c(C(C)(C)O)cc3n2)CC1]

In some embodiments, IRAK is
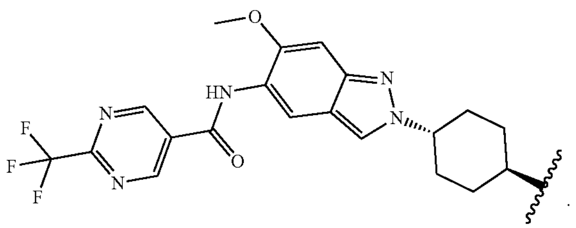 [SMILES: *[C@H]1CC[C@H](n2cc3cc(NC(=O)c4cnc(C(F)(F)F)nc4)c(OC)cc3n2)CC1]
In some embodiments, TRAK is
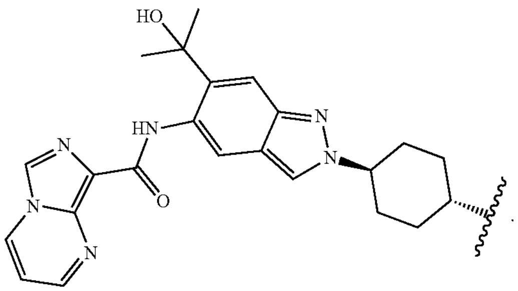 [SMILES: *[C@H]1CC[C@H](n2cc3cc(NC(=O)c4ncn5cccnc45)c(C(C)(C)O)cc3n2)CC1]
In some embodiments, TRAK is
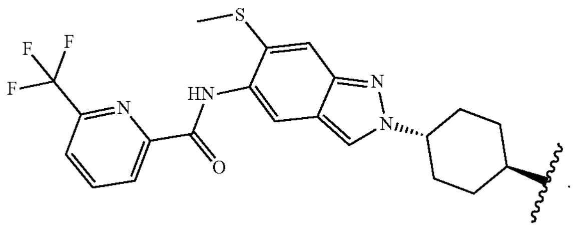 [SMILES: *[C@H]1CC[C@H](n2cc3cc(NC(=O)c4cccc(C(F)(F)F)n4)c(SC)cc3n2)CC1]
In some embodiments, IRAK is
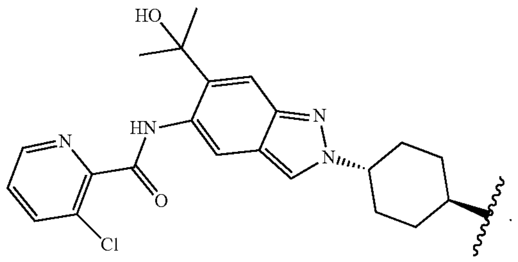 [SMILES: *[C@H]1CC[C@H](n2cc3cc(NC(=O)c4ncccc4Cl)c(C(C)(C)O)cc3n2)CC1]
In some embodiments, IRAK is
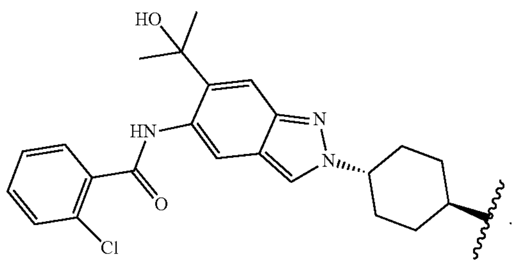 [SMILES: *[C@H]1CC[C@H](n2cc3cc(NC(=O)c4ccccc4Cl)c(C(C)(C)O)cc3n2)CC1]
In some embodiments, IRAK is
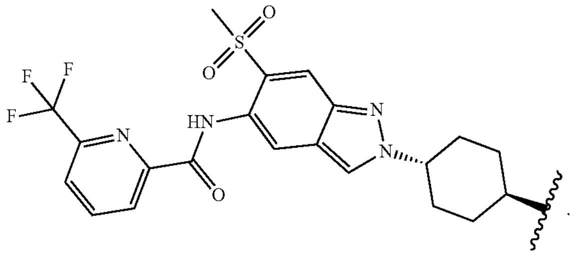 [SMILES: *[C@H]1CC[C@H](n2cc3cc(NC(=O)c4cccc(C(F)(F)F)n4)c(S(C)(=O)=O)cc3n2)CC1]
In some embodiments, IRAK is
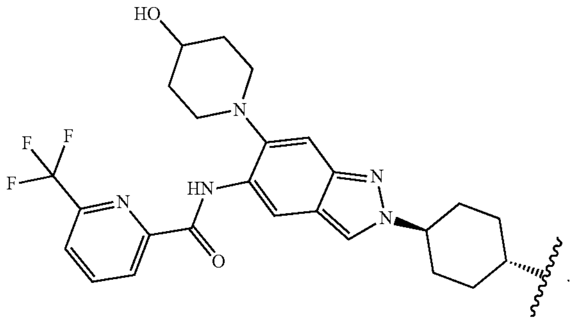 [SMILES: *[C@H]1CC[C@H](n2cc3cc(NC(=O)c4cccc(C(F)(F)F)n4)c(N4CCC(O)CC4)cc3n2)CC1]
In some embodiments, IRAK is
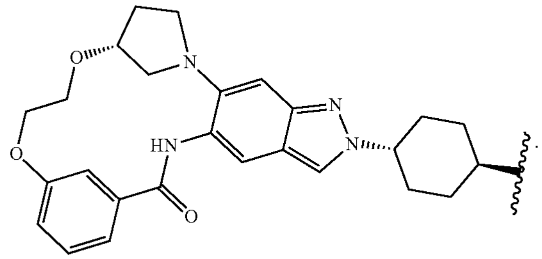 [SMILES: *[C@H]1CC[C@H](n2cc3cc4c(cc3n2)N2CC[C@H](C2)OCCOc2cccc(c2)C(=O)N4)CC1]
In some embodiments, IRAK is
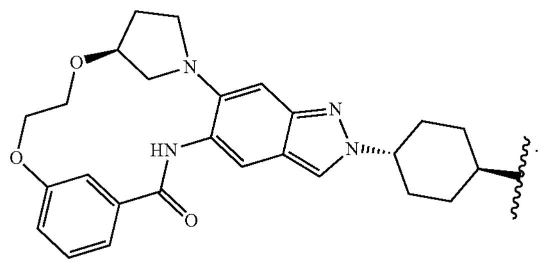 [SMILES: *[C@H]1CC[C@H](n2cc3cc4c(cc3n2)N2CC[C@@H](C2)OCCOc2cccc(c2)C(=O)N4)CC1]

In some embodiments, IRAK is
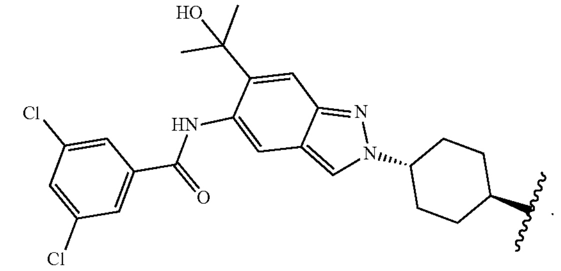 [SMILES: *[C@H]1CC[C@H](n2cc3cc(NC(=O)c4cc(Cl)cc(Cl)c4)c(C(C)(C)O)cc3n2)CC1]
In some embodiments, IRAK is
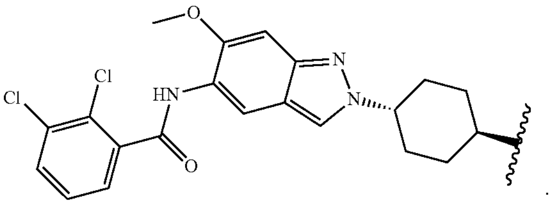
In some embodiments, IRAK is
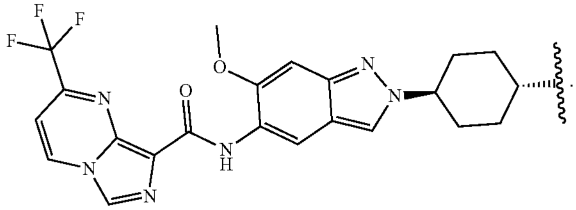 [SMILES: *[C@H]1CC[C@H](n2cc3cc(NC(=O)c4ncn5ccc(C(F)(F)F)nc45)c(OC)cc3n2)CC1]
In some embodiments, IRAK is
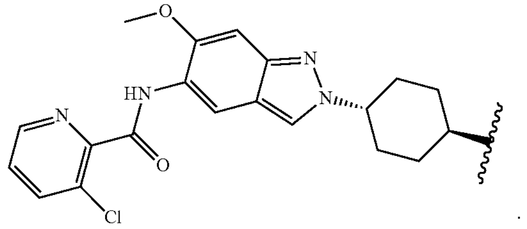
In some embodiments, IRAK is
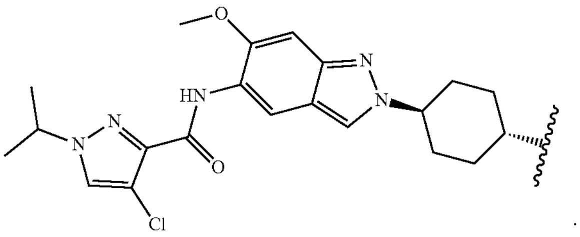 [SMILES: *[C@H]1CC[C@H](n2cc3cc(NC(=O)c4nn(C(C)C)cc4Cl)c(OC)cc3n2)CC1]
In some embodiments, IRAK is
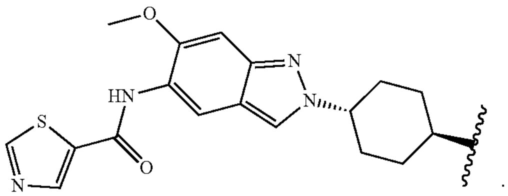
In some embodiments, IRAK is
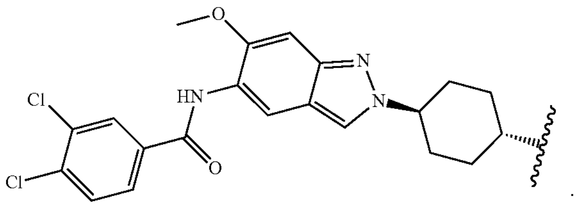 [SMILES: *[C@H]1CC[C@H](n2cc3cc(NC(=O)c4ccc(Cl)c(Cl)c4)c(OC)cc3n2)CC1]
In some embodiments, IRAK is
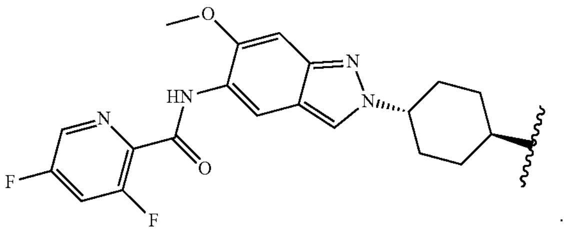
In some embodiments, IRAK is
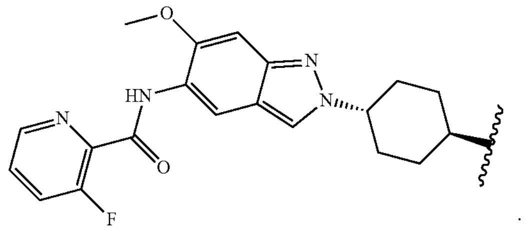 [SMILES: *[C@H]1CC[C@H](n2cc3cc(NC(=O)c4ncccc4F)c(OC)cc3n2)CC1]
In some embodiments, TRAK is
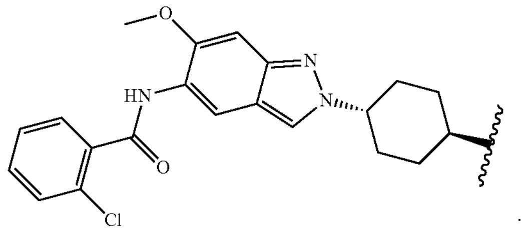 [SMILES: *[C@H]1CC[C@H](n2cc3cc(NC(=O)c4ccccc4Cl)c(OC)cc3n2)CC1]

In some embodiments, TRAK is
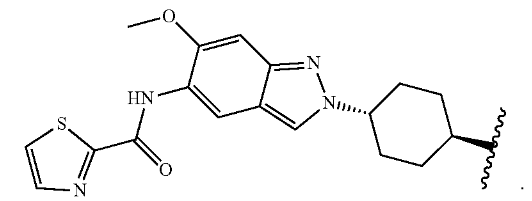 [SMILES: *[C@H]1CC[C@H](n2cc3cc(NC(=O)c4nccs4)c(OC)cc3n2)CC1]
In some embodiments, TRAK is
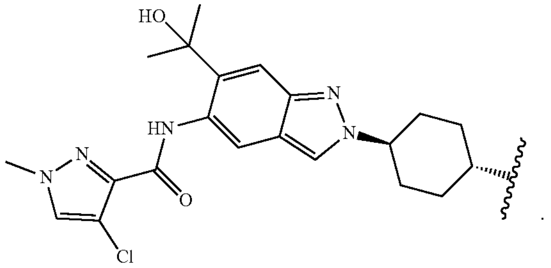 [SMILES: *[C@H]1CC[C@H](n2cc3cc(NC(=O)c4nn(C)cc4Cl)c(C(C)(C)O)cc3n2)CC1]
In some embodiments, TRAK is
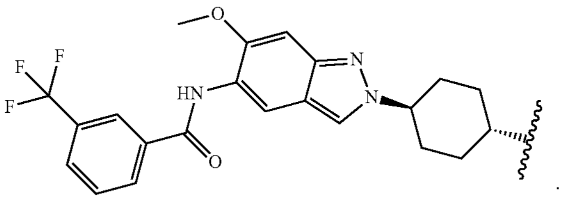 [SMILES: *[C@H]1CC[C@H](n2cc3cc(NC(=O)c4cccc(C(F)(F)F)c4)c(OC)cc3n2)CC1]
In some embodiments, TRAK is
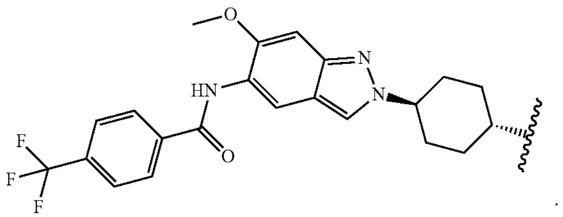 [SMILES: *[C@H]1CC[C@H](n2cc3cc(NC(=O)c4ccc(C(F)(F)F)cc4)c(OC)cc3n2)CC1]
In some embodiments, IRAK is
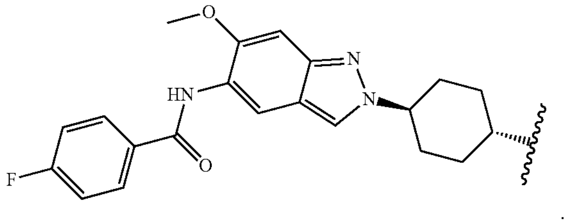 [SMILES: *[C@H]1CC[C@H](n2cc3cc(NC(=O)c4ccc(F)cc4)c(OC)cc3n2)CC1]
In some embodiments, IRAK is
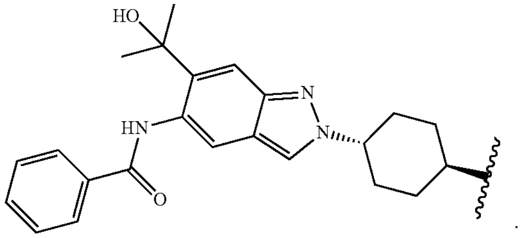 [SMILES: *[C@H]1CC[C@H](n2cc3cc(NC(=O)c4ccccc4)c(C(C)(C)O)cc3n2)CC1]
In some embodiments, IRAK is
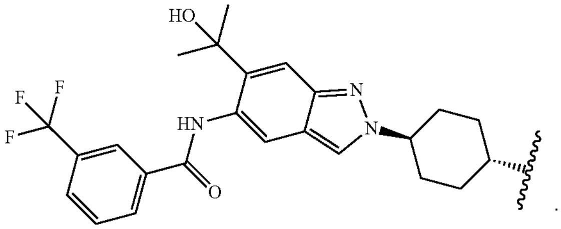 [SMILES: *[C@H]1CC[C@H](n2cc3cc(NC(=O)c4cccc(C(F)(F)F)c4)c(C(C)(C)O)cc3n2)CC1]
In some embodiments, IRAK is
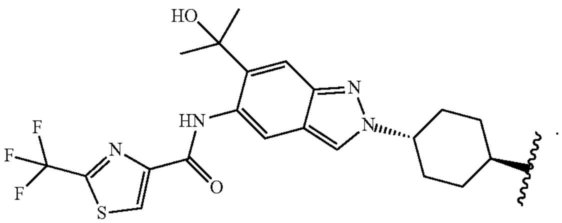
In some embodiments, IRAK is
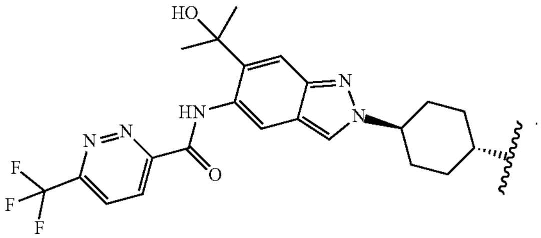
In some embodiments, IRAK is
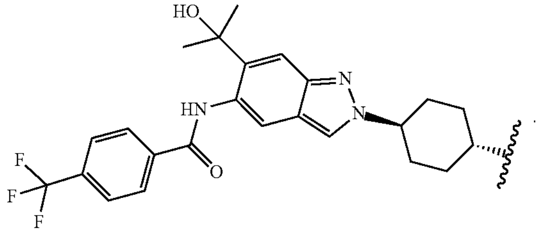

In some embodiments, IRAK is
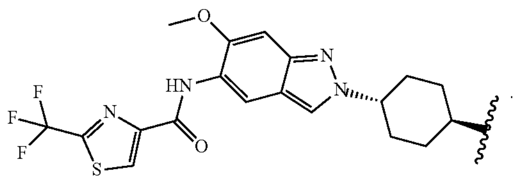
In some embodiments, IRAK is
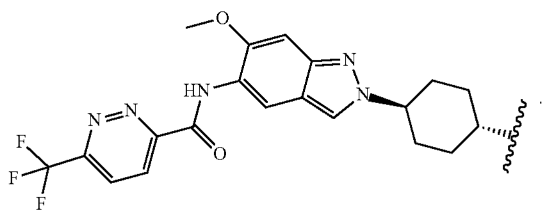
In some embodiments, IRAK is
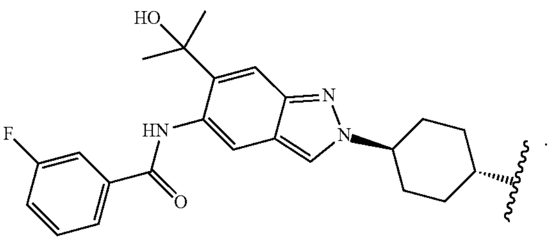
In some embodiments, IRAK is
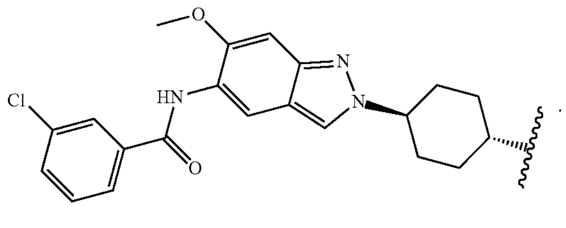
In some embodiments, IRAK is
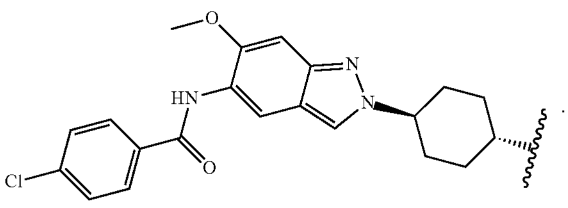
In some embodiments, IRAK is
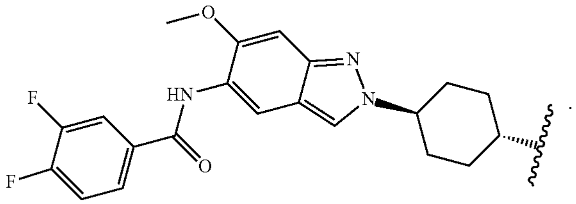
In some embodiments, IRAK is
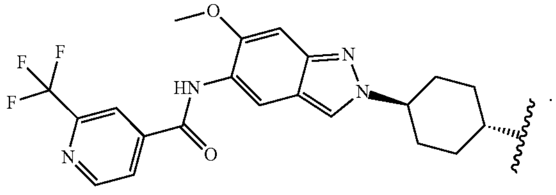
In some embodiments, IRAK is
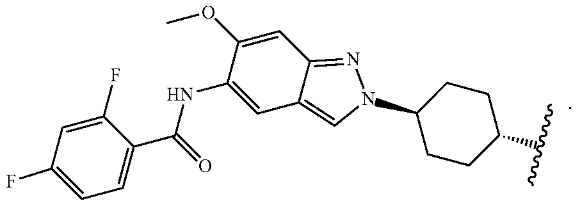
In some embodiments, IRAK is
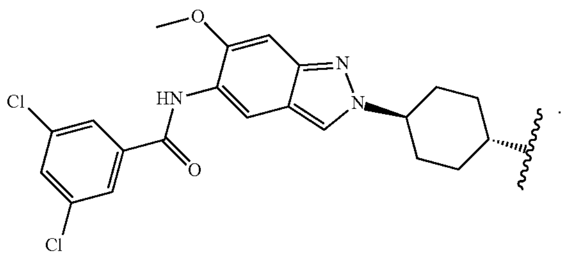
In some embodiments, IRAK is
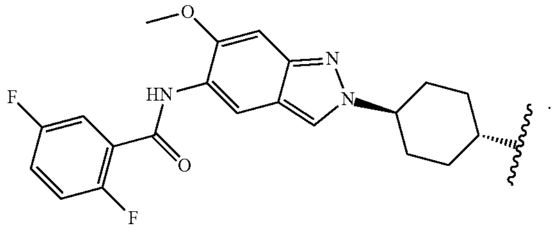

In some embodiments, IRAK is
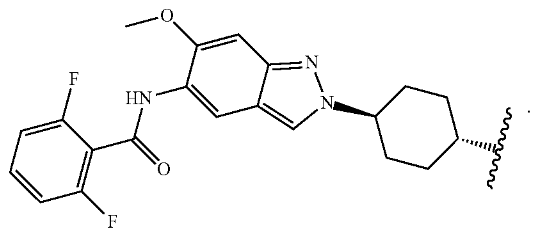
In some embodiments, IRAK is
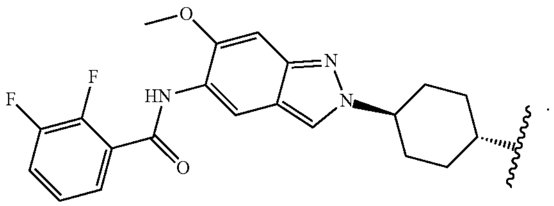
In some embodiments, IRAK is
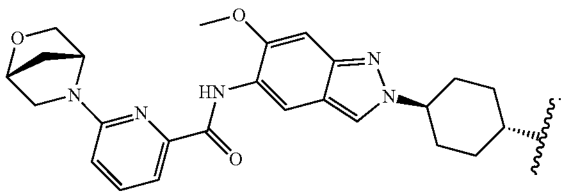 [SMILES: *[C@H]1CC[C@H](n2cc3cc(NC(=O)c4cccc(N5C[C@H]6C[C@@H]5CO6)n4)c(OC)cc3n2)CC1]
In some embodiments, IRAK is
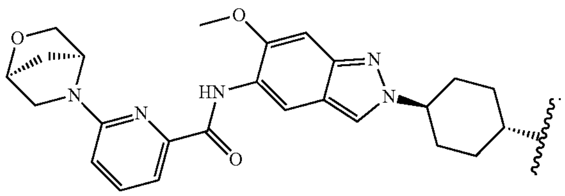 [SMILES: *[C@H]1CC[C@H](n2cc3cc(NC(=O)c4cccc(N5C[C@@H]6C[C@H]5CO6)n4)c(OC)cc3n2)CC1]
In some embodiments, IRAK is
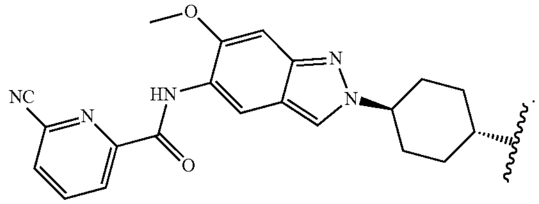
In some embodiments, IRAK is
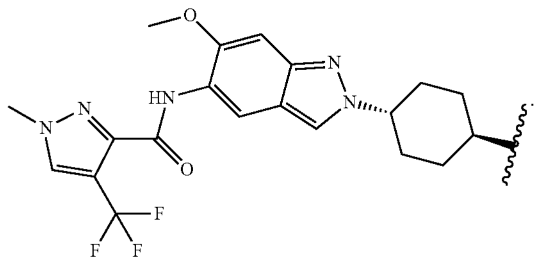 [SMILES: *[C@H]1CC[C@H](n2cc3cc(NC(=O)c4nn(C)cc4C(F)(F)F)c(OC)cc3n2)CC1]
In some embodiments, TRAK is
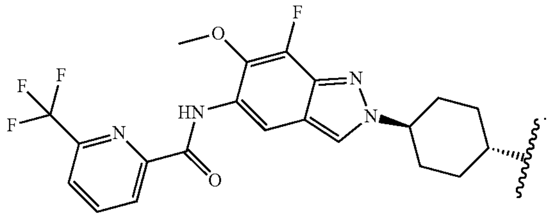 [SMILES: *[C@H]1CC[C@H](n2cc3cc(NC(=O)c4cccc(C(F)(F)F)n4)c(OC)c(F)c3n2)CC1]
In some embodiments, IRAK is
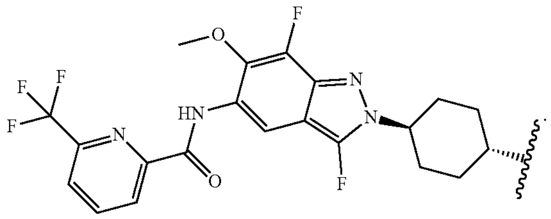
In some embodiments, IRAK is
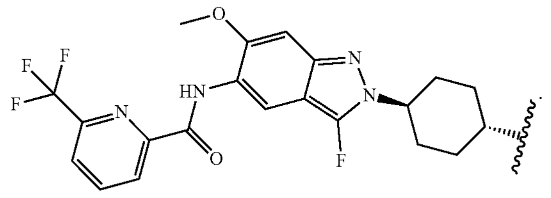 [SMILES: *[C@H]1CC[C@H](n2nc3cc(OC)c(NC(=O)c4cccc(C(F)(F)F)n4)cc3c2F)CC1]
In some embodiments, IRAK is
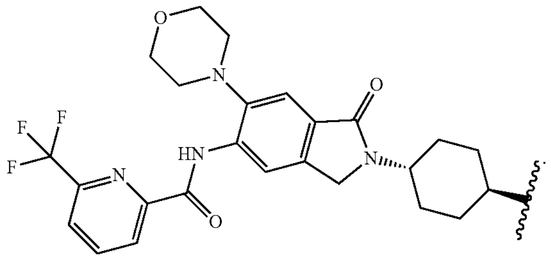 [SMILES: *[C@H]1CC[C@H](N2Cc3cc(NC(=O)c4cccc(C(F)(F)F)n4)c(N4CCOCC4)cc3C2=O)CC1]

In some embodiments, IRAK is

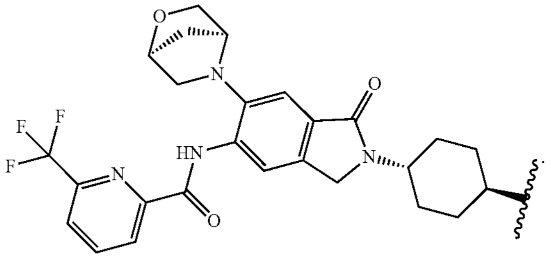 [SMILES: *[C@H]1CC[C@H](N2Cc3cc(NC(=O)c4cccc(C(F)(F)F)n4)c(N4C[C@@H]5C[C@H]4CO5)cc3C2=O)CC1]

In some embodiments, IRAK is

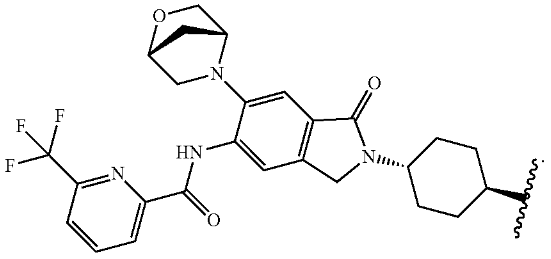 [SMILES: *[C@H]1CC[C@H](N2Cc3cc(NC(=O)c4cccc(C(F)(F)F)n4)c(N4C[C@H]5C[C@@H]4CO5)cc3C2=O)CC1]

In some embodiments, IRAK is

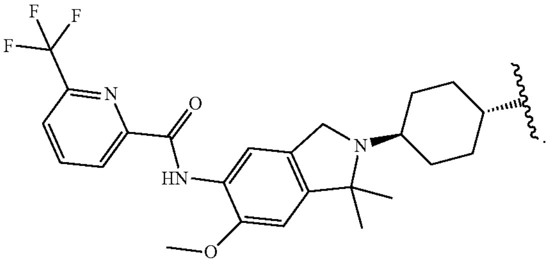 [SMILES: *[C@H]1CC[C@H](N2Cc3cc(NC(=O)c4cccc(C(F)(F)F)n4)c(OC)cc3C2(C)C)CC1]

In some embodiments, IRAK is selected from those depicted in Table 1, below.

Ligase Binding Moiety (LBM)

As defined herein and described below wherein a formula is depicted using square brackets, e.g,

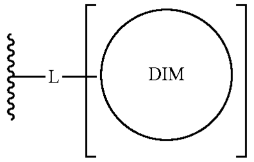

or

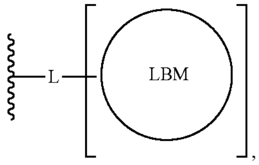

,

L is attached to a modifiable carbon, oxygen, or nitrogen atom within DIM or LBM including substitution or replacement of a defined group in DIM or LBM.

In some embodiments, DIM is LBM. In certain embodiments, the present invention provides a compound of formula I, wherein LBM is an E3 ubiquitin ligase (cereblon) binding moiety thereby forming a compound of formula I-aa:

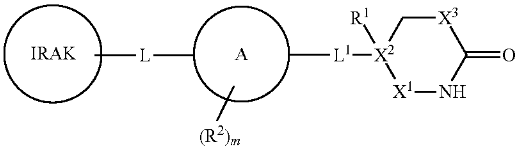

or a pharmaceutically acceptable salt thereof, wherein L and IRAK are as defined above and described herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

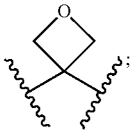

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —N(R)$_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

each $R^2$ is independently hydrogen, deuterium, —$R^6$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)($NR_2$), —OP(O)($NR_2$)$_2$—, —N(R)C(O)OR, —N(R)C(O)R, —N(R)C(O)N(R)$_2$, —N(R)S(O)$_2$R, —NP(O)$R_2$, —N(R)P(O)(OR)$_2$, —N(R)P(O)(OR)($NR_2$), —N(R)P(O)($NR_2$)$_2$, or —N(R)S(O)$_2$R;

Ring A is a bi- or tricyclic ring selected from

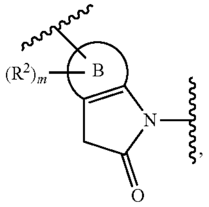

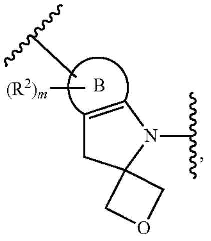

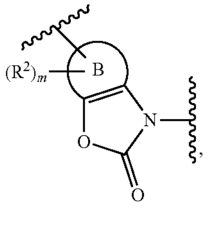

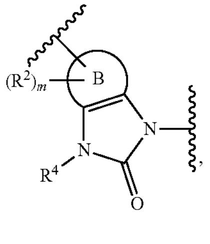

-continued
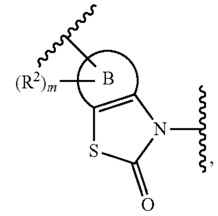
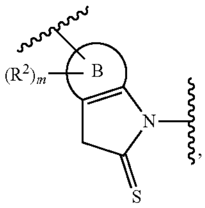
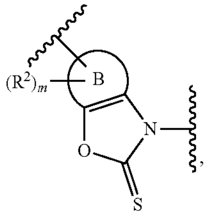
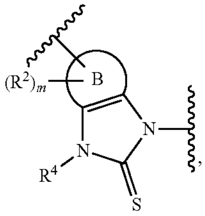
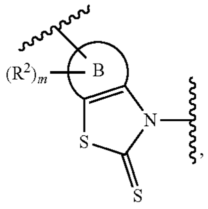
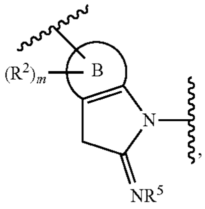
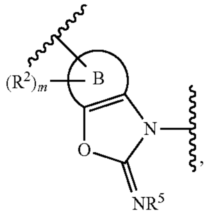
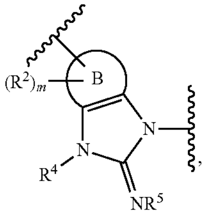
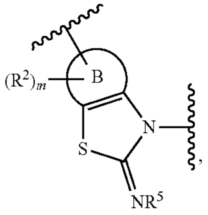
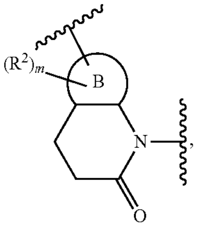
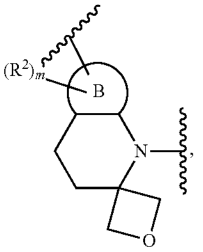
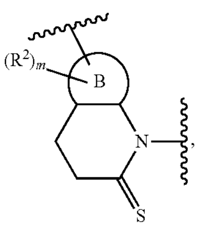
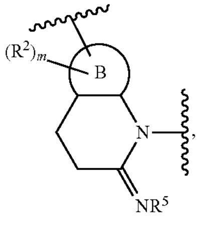
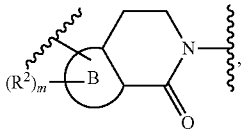
-continued
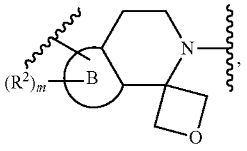
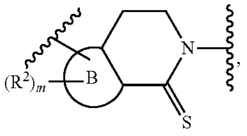
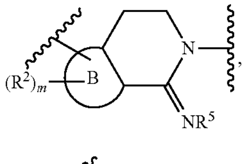
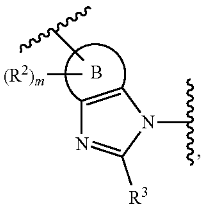
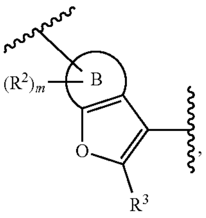
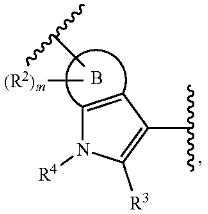
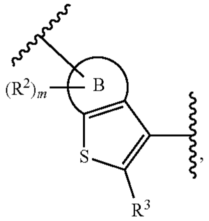
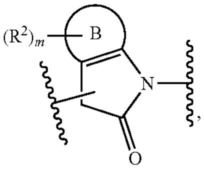
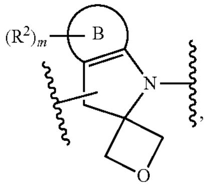
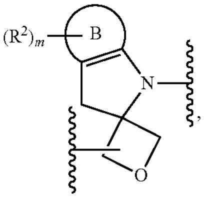
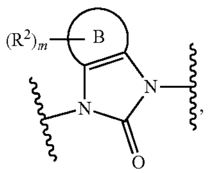
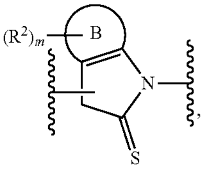
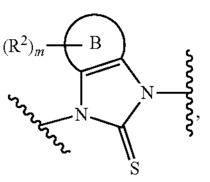
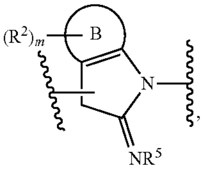
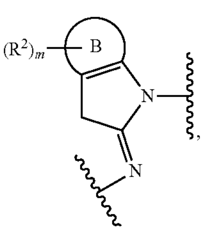
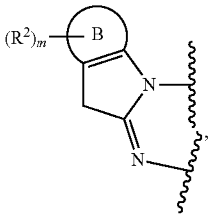

-continued

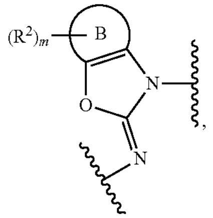
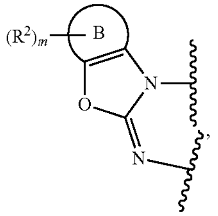
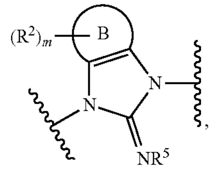
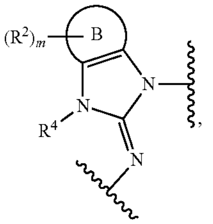
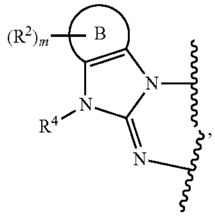
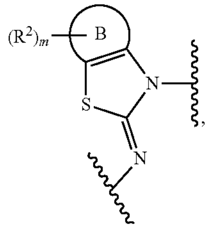
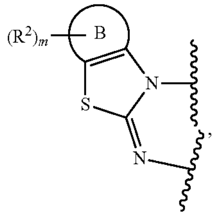
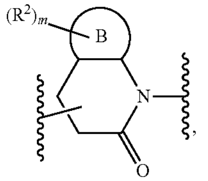
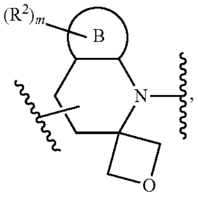
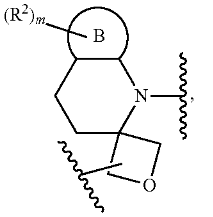
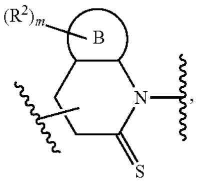
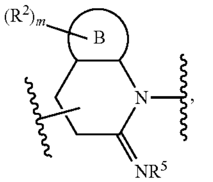
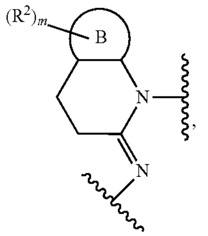
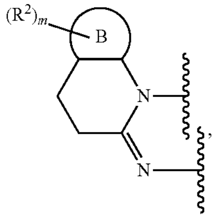
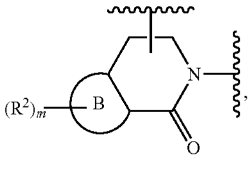
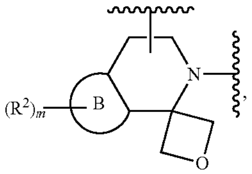

-continued

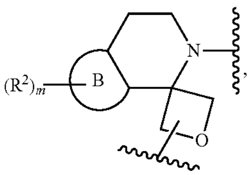
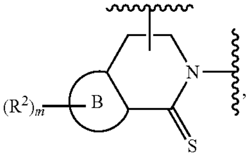
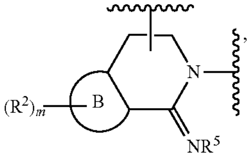
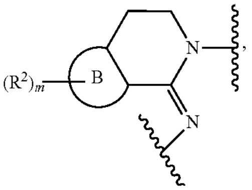
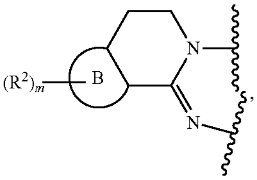
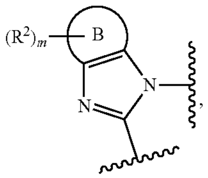
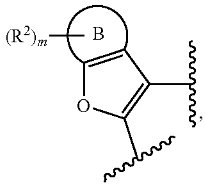
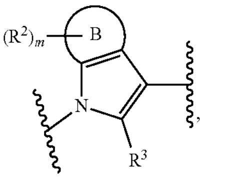
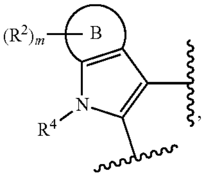

or

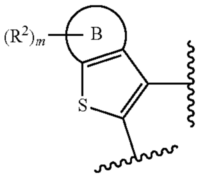

wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —$NO_2$, —OR, —SR, —$NR_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3 or 4;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or $R^5$, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, a compound of formula I-aa above is provided as a compound of formula I-aa' or formula I-aa":

I-aa'

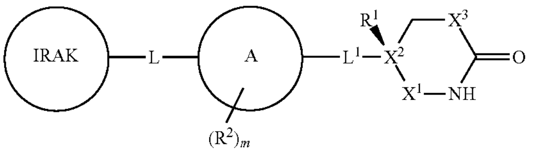

I-aa''

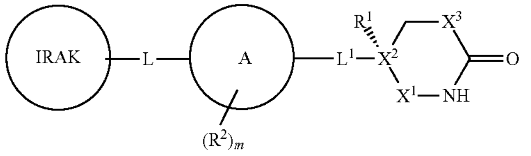

or a pharmaceutically acceptable salt thereof, wherein: each of IRAK, Ring A, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-bb:

I-bb

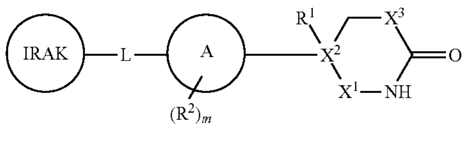

or a pharmaceutically acceptable salt thereof, wherein L and IRAK are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

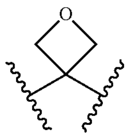 ;

$X^2$ is a carbon atom or silicon atom;

$X^3$ is a bivalent moiety selected from —$CR_2$—, —NR—, —O—, —S—, or —$Si(R_2)$—;

$R^1$ is hydrogen, deuterium, halogen, —CN, —OR, —SR, —S(O)R, —$S(O)_2R$, —$N(R)_2$, —$P(O)(OR)_2$, —P(O)$(NR_2)$OR, —$P(O)(NR_2)_2$, —$Si(OH)_2R$, —$Si(OH)(R)_2$, —$Si(R)_3$, or an optionally substituted $C_{1-4}$ aliphatic;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —OP(O)(OR)$(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —N(R)P(O)(OR)$(NR_2)$, —$N(R)P(O)(NR_2)_2$, or —$N(R)S(O)_2R$;

Ring A is a bi- or tricyclic ring selected from

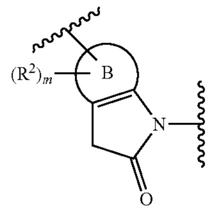

wherein Ring B is other than imidazo or benzo,

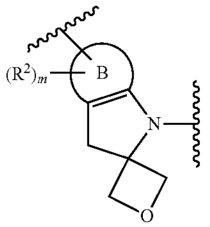 ,

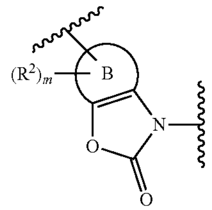

wherein Ring B is other than benzo,
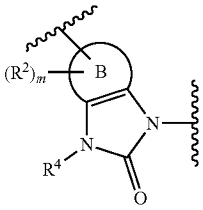
wherein Ring B is other than benzo
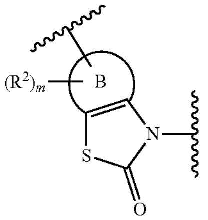,
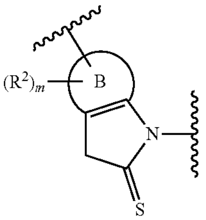,
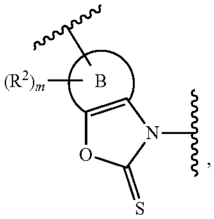,
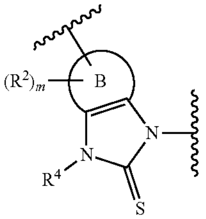,
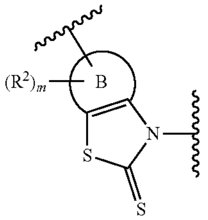,
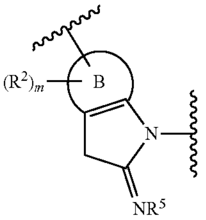,
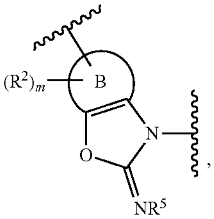,
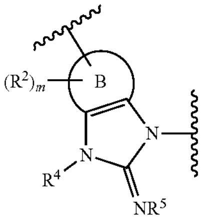,
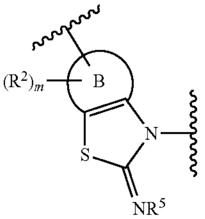,
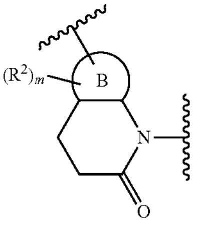,
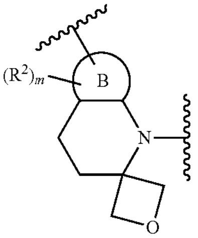,
-continued
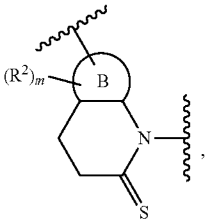,
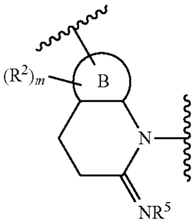,
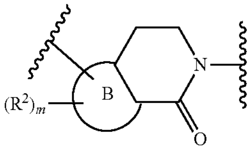
wherein Ring B is other than benzo,
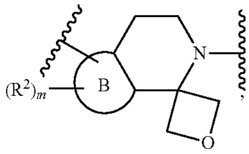,
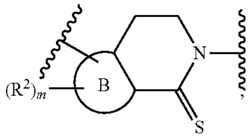,
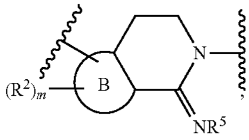,
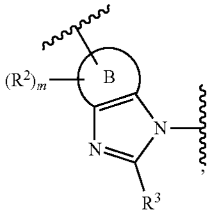,
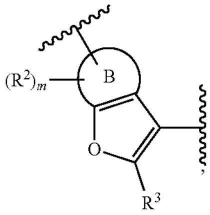,
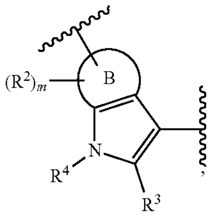, -continued
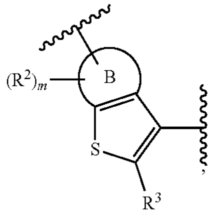
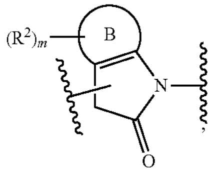
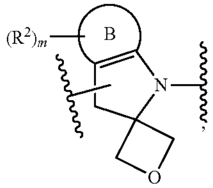
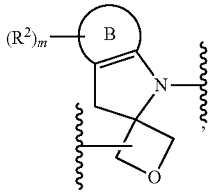
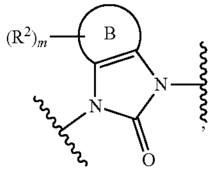
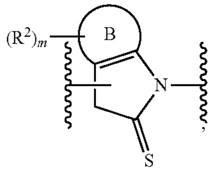
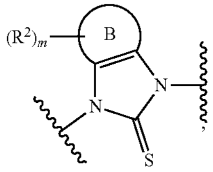
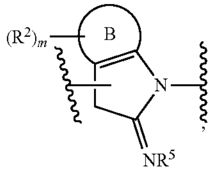
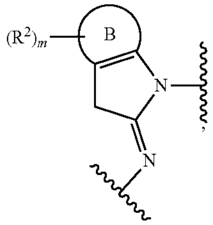
-continued
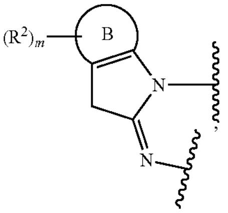
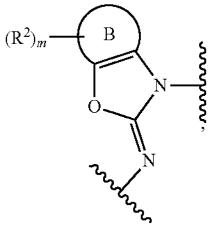
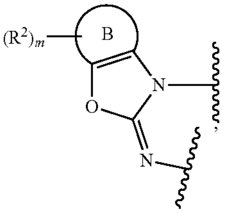
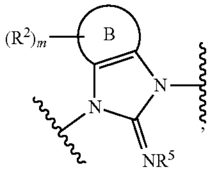
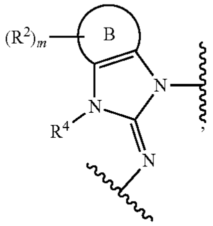
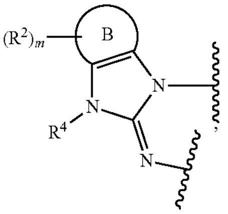
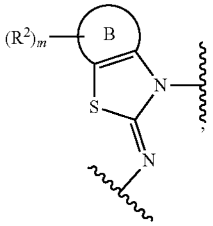
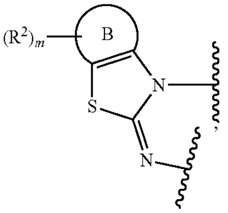

-continued
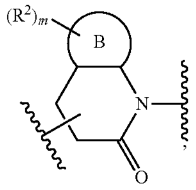
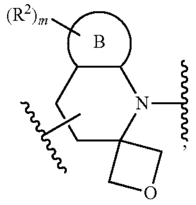
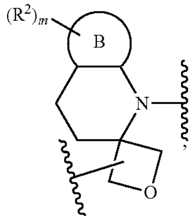
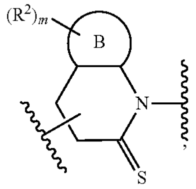
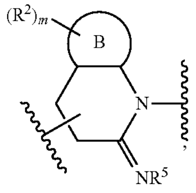
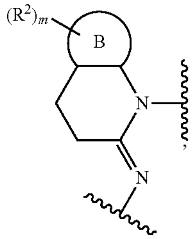
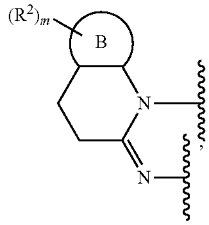
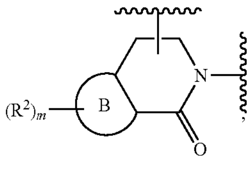
-continued
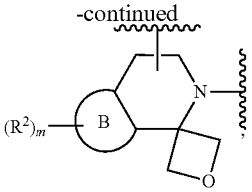
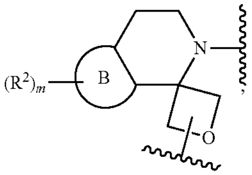
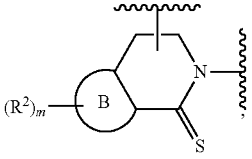
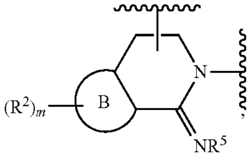
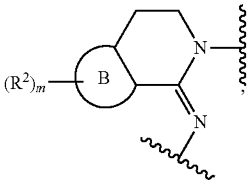
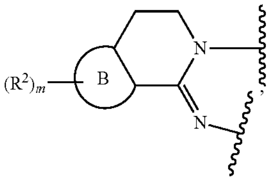
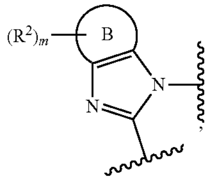
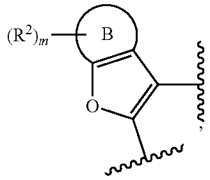
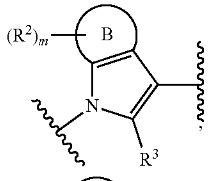
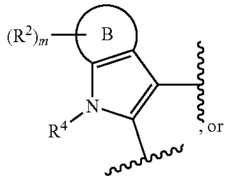
, or -continued

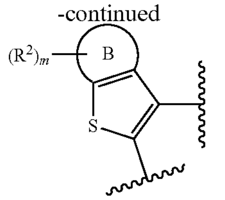

wherein

Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —$N(R)_2$, or —SR;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or $R^5$, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, the compound of formula I-bb above is provided as a compound of formula I-bb' or formula I-bb".

I-bb'

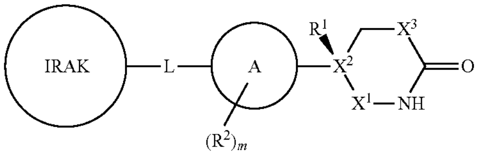

I-bb"

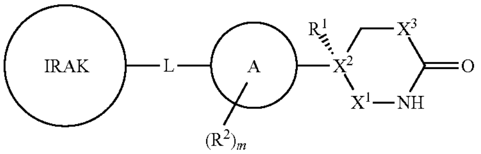

or a pharmaceutically acceptable salt thereof, wherein:

each of IRAK, Ring A, L, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-cc:

I-cc

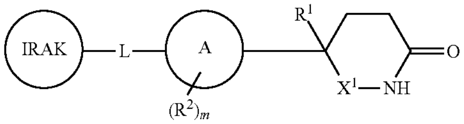

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

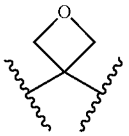

;

$R^1$ is hydrogen, deuterium, halogen, —CN, —OR, —SR, —S(O)R, —$S(O)_2R$, —$NR_2$, or an optionally substituted $C_{1-4}$ aliphatic;

each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring A is a bi- or tricyclic ring selected from

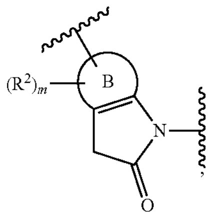

,

-continued
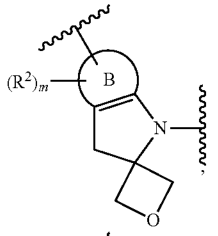
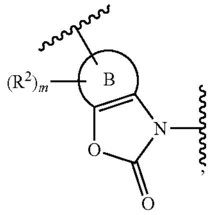
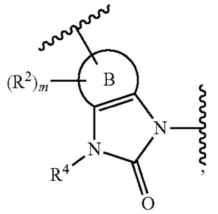
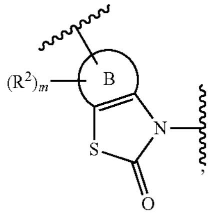
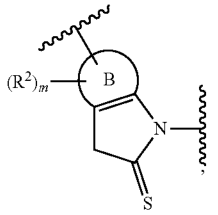
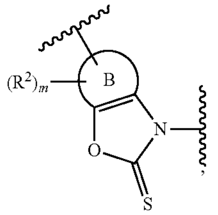
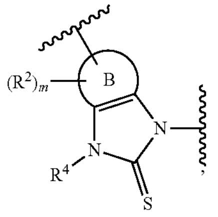
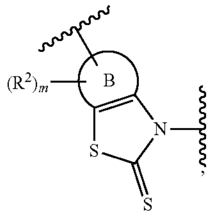
-continued
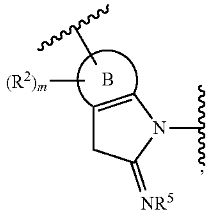
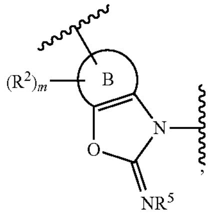
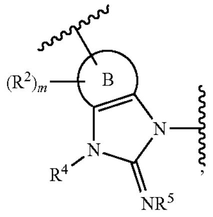
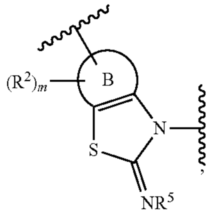
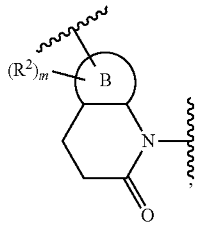
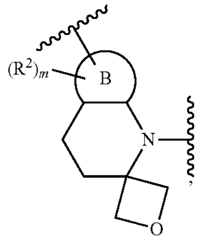
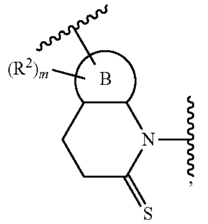

-continued
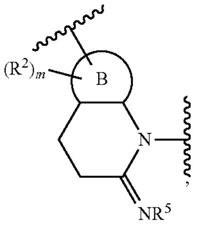
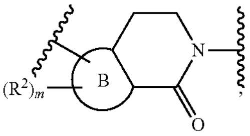
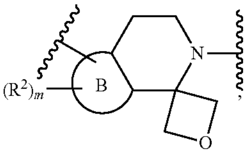
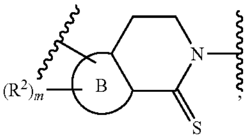
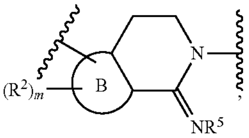
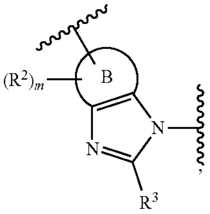
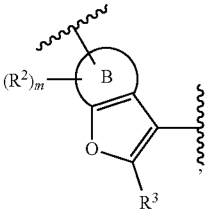
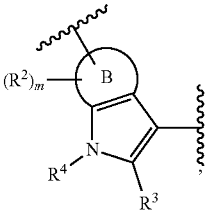
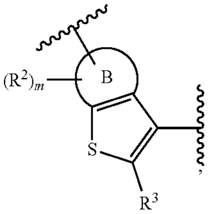
-continued
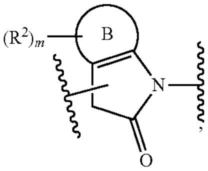
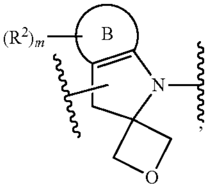
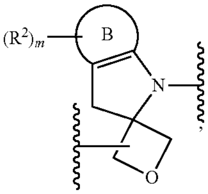
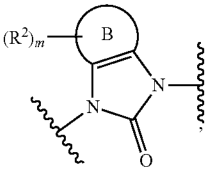
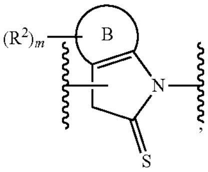
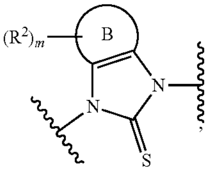
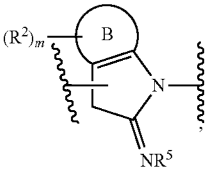
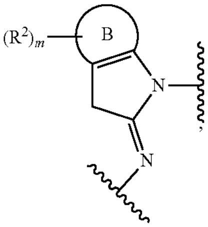
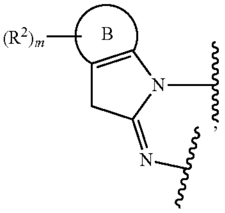

-continued
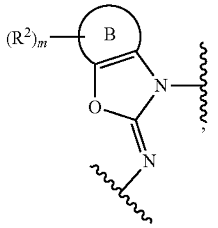
,
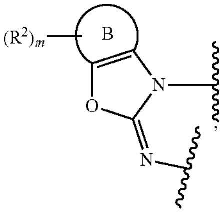
,
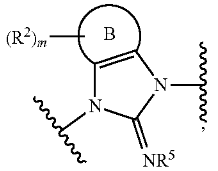
,
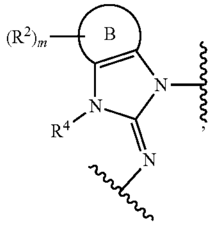
,
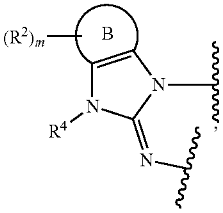
,
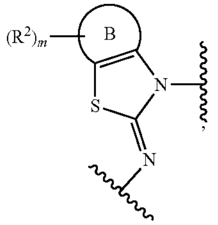
,
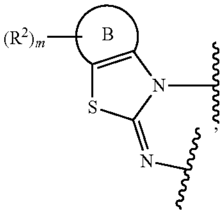
,
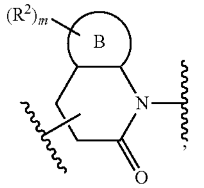
,
-continued
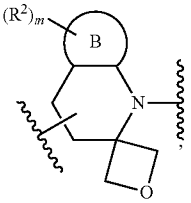
,
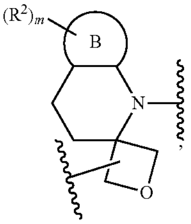
,
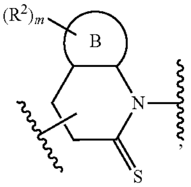
,
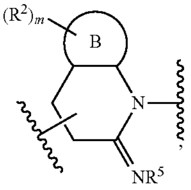
,
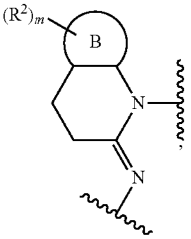
,
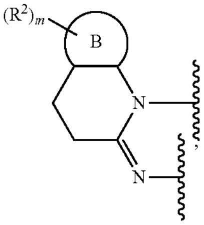
,
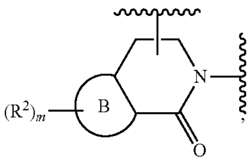
,
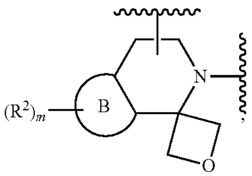
, -continued

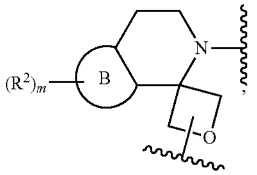

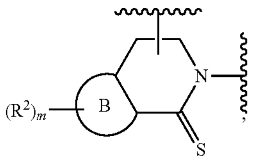

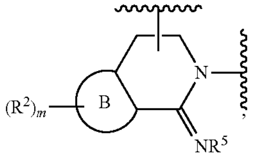

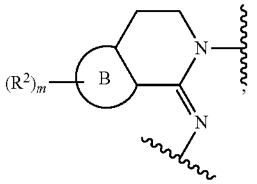

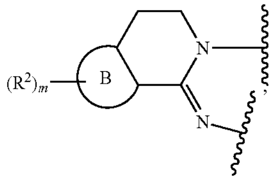

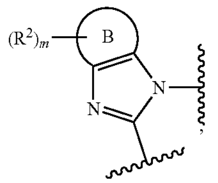

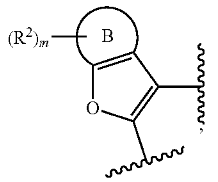

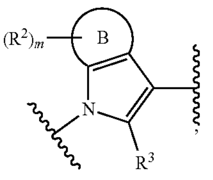

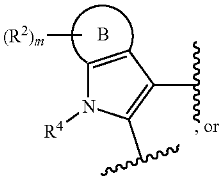

or

-continued

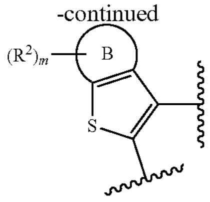

wherein

Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur $R^3$ is selected from hydrogen, halogen, —OR, —$N(R)_2$, or —SR;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or $R^5$, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, the compound of formula I-cc above is provided as a compound of formula I-cc' or formula I-cc":

I-cc'

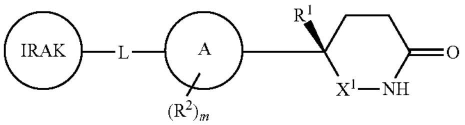

I-cc''

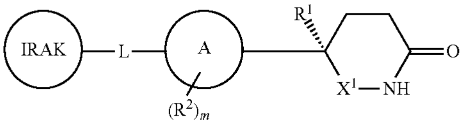

or a pharmaceutically acceptable salt thereof, wherein:

each of IRAK, Ring A, L, $R^1$, $R^2$, $X^1$, and m is as defined above.

In certain embodiments, the present invention provides a compound of formula I, wherein LBM is an E3 ubiquitin ligase (cereblon) binding moiety thereby forming a compound of formula I-dd:

I-dd

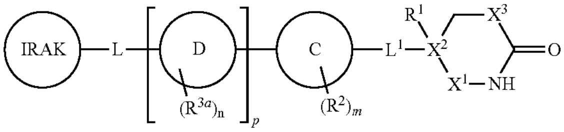

or a pharmaceutically acceptable salt thereof, wherein, L and IRAK are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

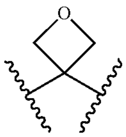

;

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

Ring C is a mono- or bicyclic ring selected from

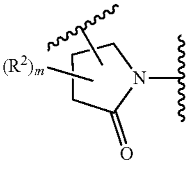, 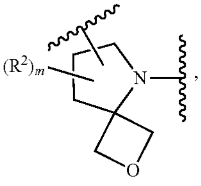,

-continued

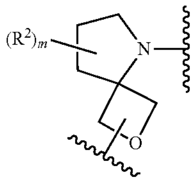, 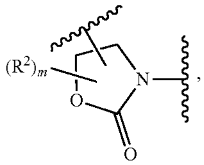,

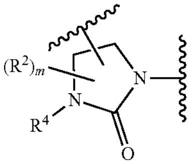, 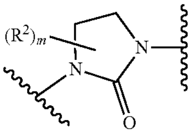,

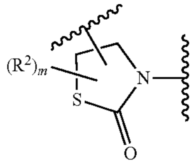, 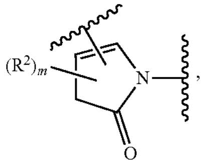,

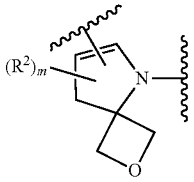, 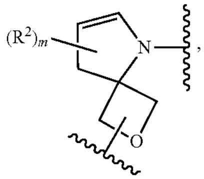,

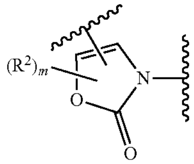, 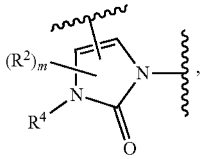,

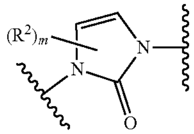, 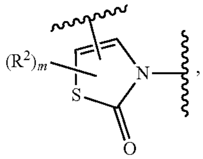,

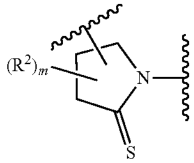, 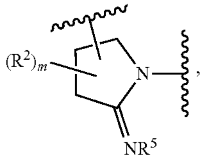,

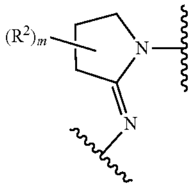, 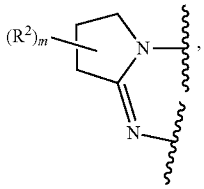,

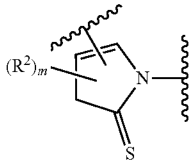, 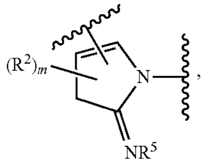,

-continued

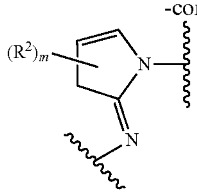, 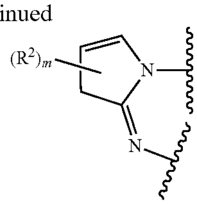,

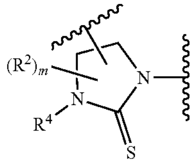, 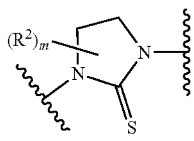,

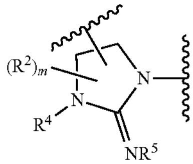, 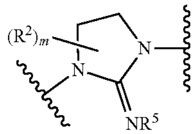,

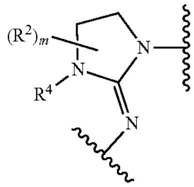, 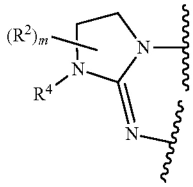,

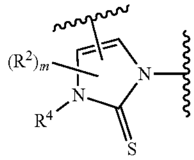, 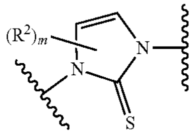,

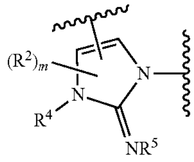, 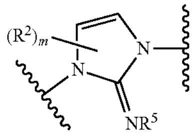,

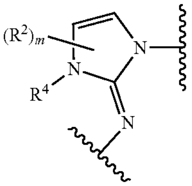, 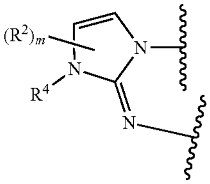,

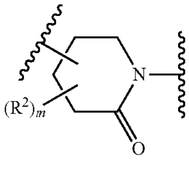, 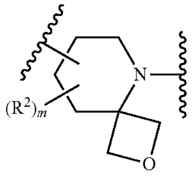,

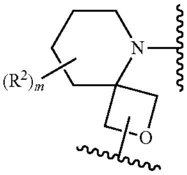, 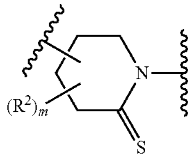,

-continued

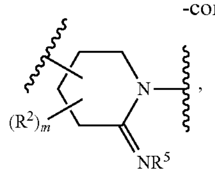, 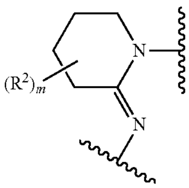, or

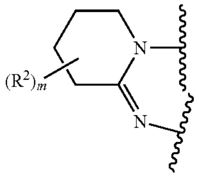;

each of $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

Ring D is selected from a 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3 or 4;

n is 0, 1, 2, 3 or 4;

p is 0 or 1, wherein when p is 0, the bond connecting Ring C and Ring D is connected to

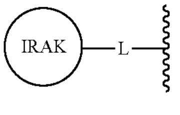;

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-dd above is provided as a compound of formula I-dd' or formula I-dd":

I-dd'

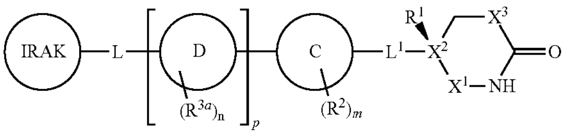

I-dd"

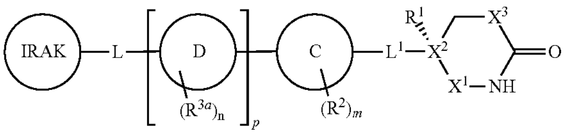

or a pharmaceutically acceptable salt thereof, wherein: each of IRAK, Ring C, Ring D, L, $L^1$, $R^1$, $R^2$, $R^{3a}$, $X^1$, $X^2$, $X^3$, n, m, and p is as defined above.

In certain embodiments, the present invention provides a compound of Formula I, wherein LBM is an E3 ubiquitin ligase (cereblon) binding moiety thereby forming a compound of formula I-ee:

I-ee

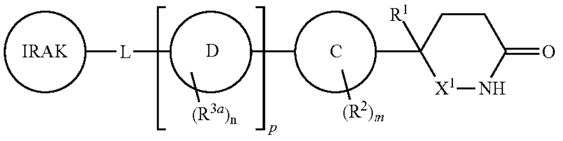

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

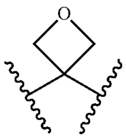

;

$R^1$ is hydrogen, deuterium, halogen, —CN, —OR, —SR, —S(O)R, —$S(O)_2$R, —$NR_2$, or an optionally substituted $C_{1-4}$ aliphatic;

Ring C is a mono- or bicyclic ring selected from

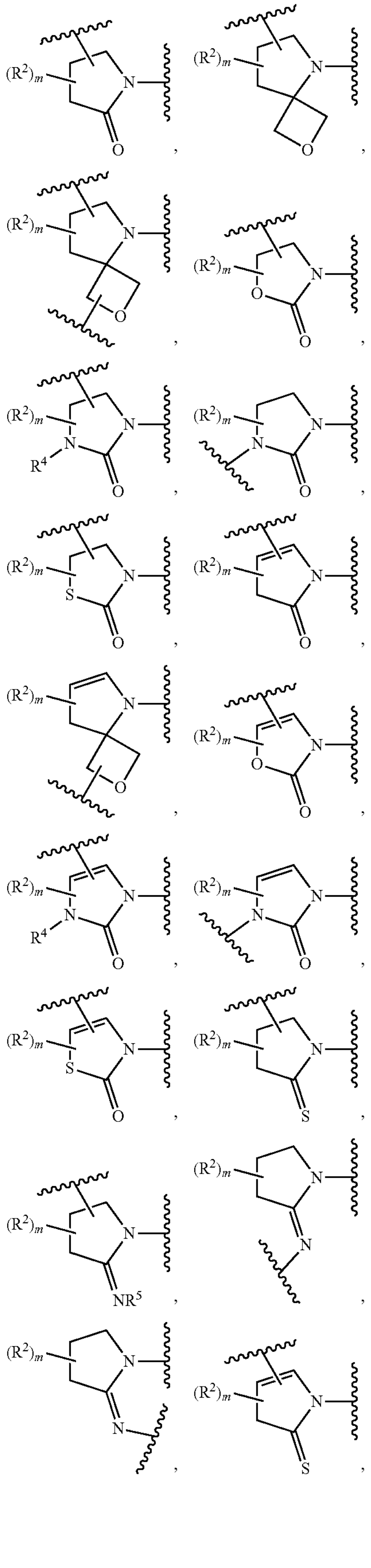

-continued

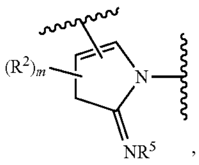, 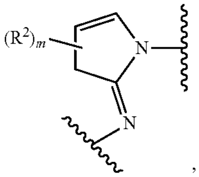,

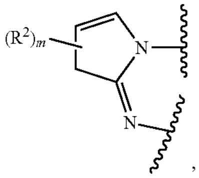, 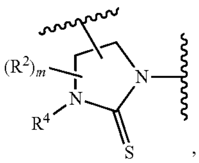,

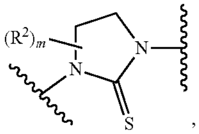, 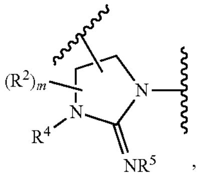,

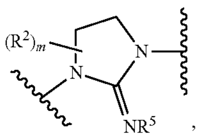, 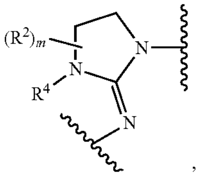,

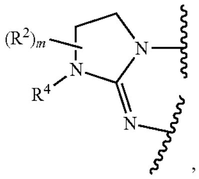, 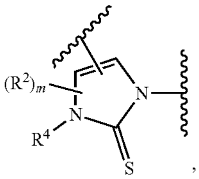,

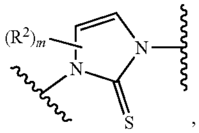, 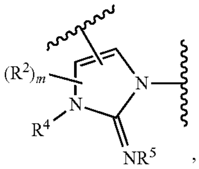,

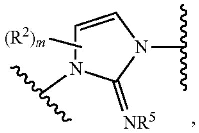, 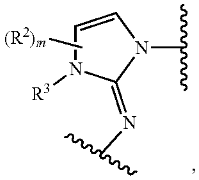,

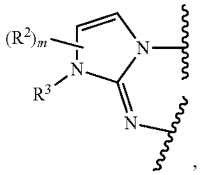, 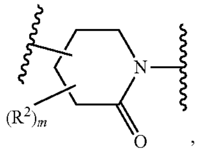,

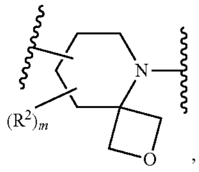, 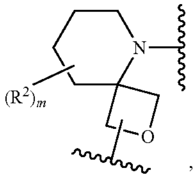,

-continued

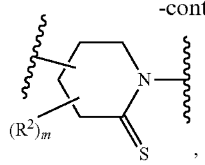, 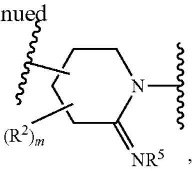,

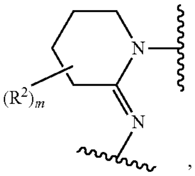, or 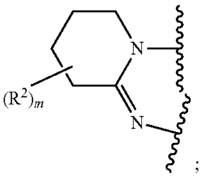;

each of $R^2$ and $R^{3a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3 or 4;

p is 0 or 1, wherein when p is 0, the bond connecting Ring C and Ring D is connected to

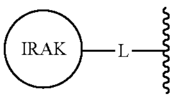;

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ee above is provided as a compound of formula I-ee' or formula I-ee'':

I-ee'

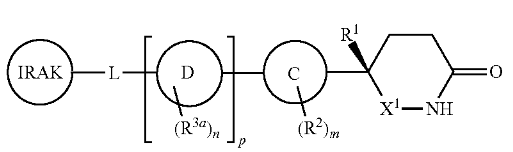

I-ee''

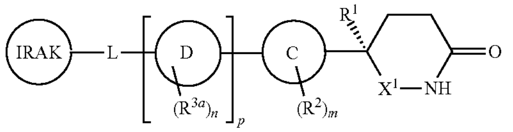

or a pharmaceutically acceptable salt thereof, wherein:

each of IRAK, Ring C, Ring D, L, $R^1$, $R^2$, $R^{3a}$, $X^1$, n, m, and p is as defined above.

In certain embodiments, the present invention provides a compound of formula I, wherein LBM is an E3 ubiquitin ligase (cereblon) binding moiety thereby forming a compound of formula I-ff:

I-ff

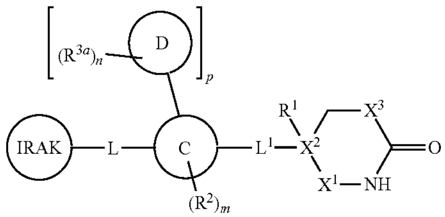

or a pharmaceutically acceptable salt thereof, wherein L and IRAK are as defined above and described in embodiments herein, and wherein:

$X^1$ is a bivalent moiety selected from a covalent bond, $-CH_2-$, $-CHCF_3-$, $-SO_2-$, $-S(O)-$, $-P(O)R-$, $-P(O)OR-$, $-P(O)NR_2-$, $-C(O)-$, $-C(S)-$, or

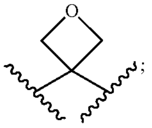 [SMILES: *C1(*)COC1]

$X^2$ is a carbon atom or silicon atom;

$X^3$ is a bivalent moiety selected from $-CR_2-$, $-NR-$, $-O-$, $-S-$, or $-Si(R_2)-$;

$R^1$ is hydrogen, deuterium, halogen, $-CN$, $-OR$, $-SR$, $-S(O)R$, $-S(O)_2R$, $-NR_2$, $-P(O)(OR)_2$, $-P(O)(NR_2)OR$, $-P(O)(NR_2)_2$, $-Si(OH)_2R$, $-Si(OH)(R)_2$, $-Si(R)_3$, or an optionally substituted $C_{1-4}$ aliphatic;

Ring C is a mono- or bicyclic ring selected from

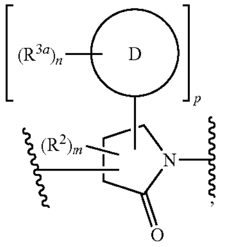

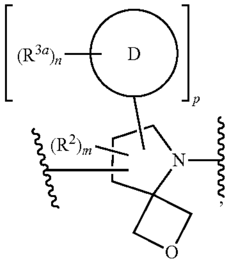

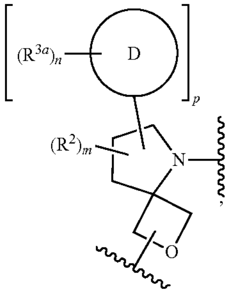

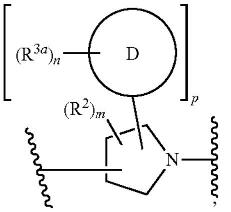

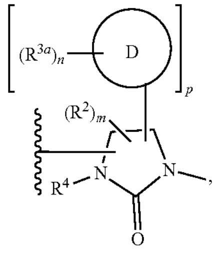

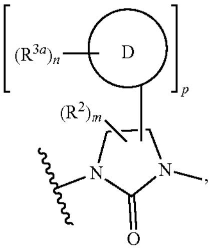

-continued
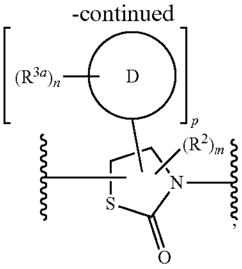
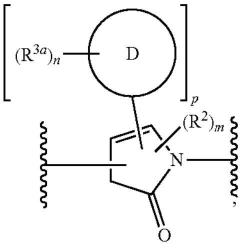
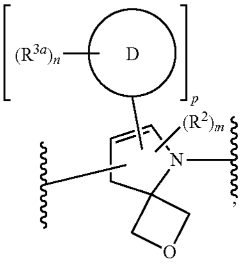
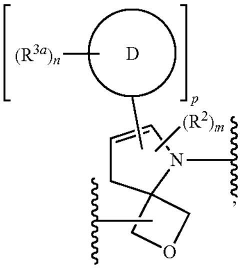
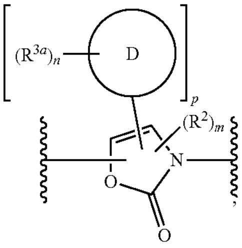
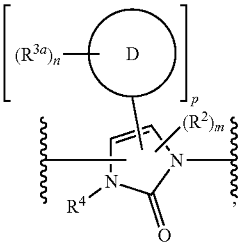
-continued
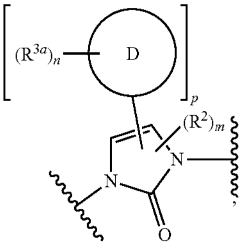
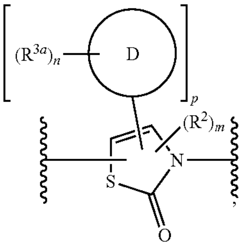
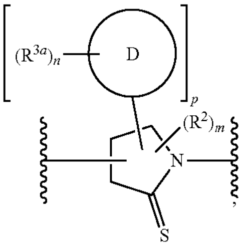
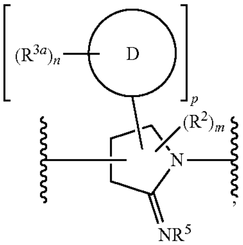
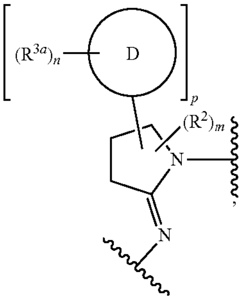
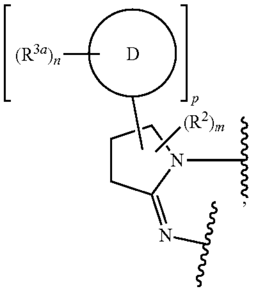

-continued
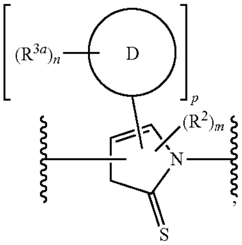
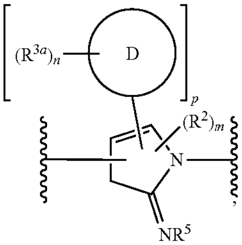
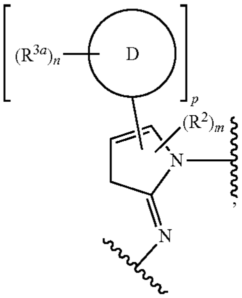
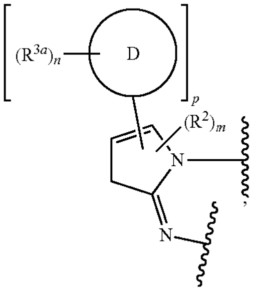
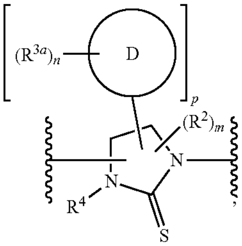
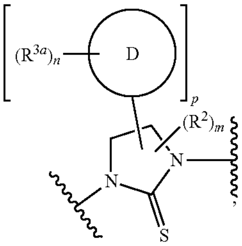
-continued
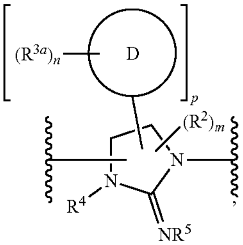
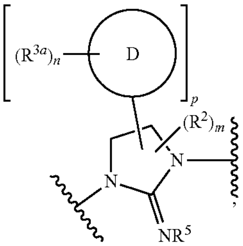
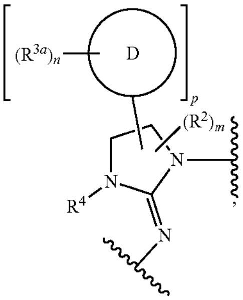
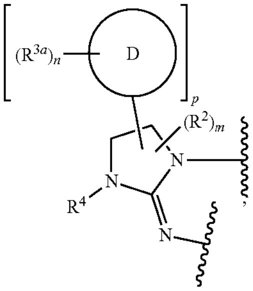
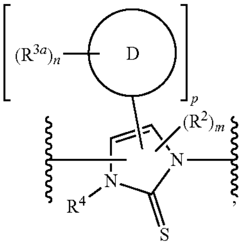
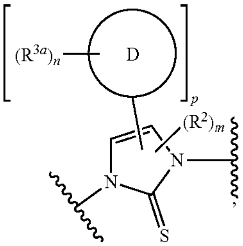

-continued

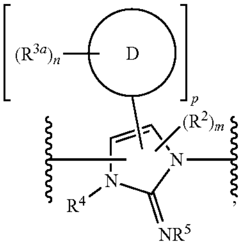

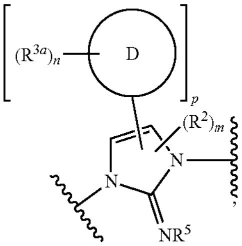

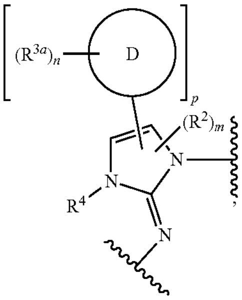

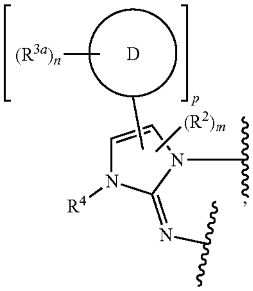

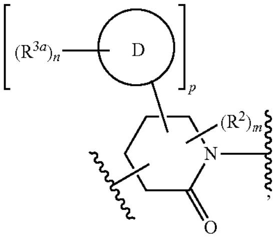

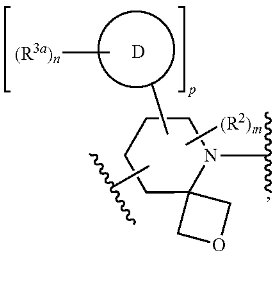

-continued

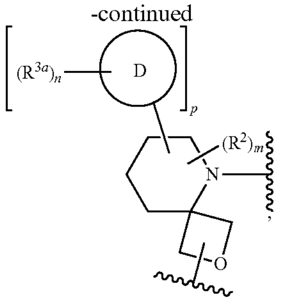

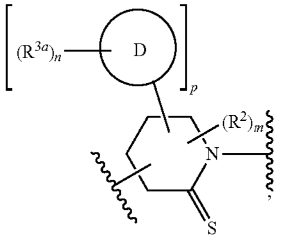

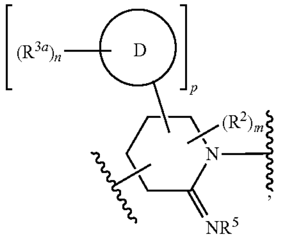

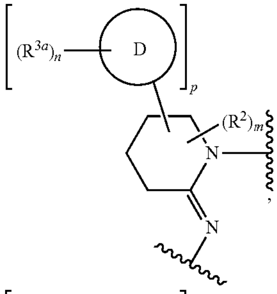

, or

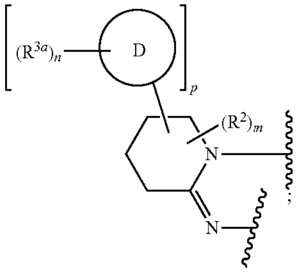

each or $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2$ N(R)C(O)R, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3 or 4;

n is 0, 1, 2, 3 or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ff above is provided as a compound of formula I-ff' or formula I-ff'':

I-ff'

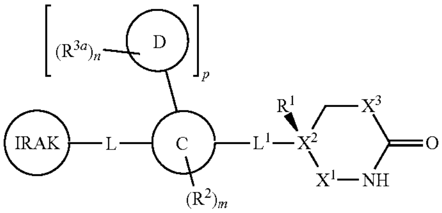

I-ff''

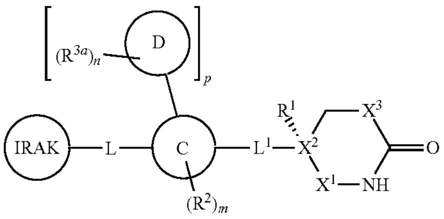

or a pharmaceutically acceptable salt thereof, wherein: each of IRAK, Ring C, Ring D, L, $L^1$, $R^1$, $R^2$, $R^{3a}$, $X^1$, $X^2$, $X^3$, m, n, and p is as defined above.

In certain embodiments, the present invention provides a compound of Formula I, wherein LBM is an E3 ubiquitin ligase (cereblon) binding moiety thereby forming a compound of formula I-gg:

I-gg

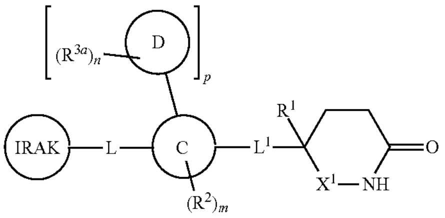

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

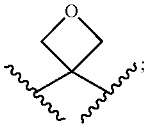 [SMILES: *C1(*)COC1]

$R^1$ is hydrogen, deuterium, halogen, —CN, —OR, —SR, —S(O)R, —$S(O)_2R$, —$NR_2$, or an optionally substituted $C_{1-4}$ aliphatic;

Ring C is a mono- or bicyclic ring selected from

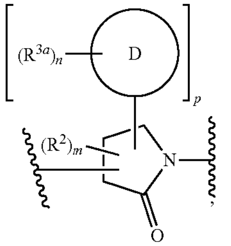

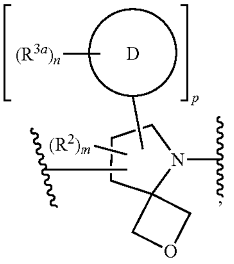

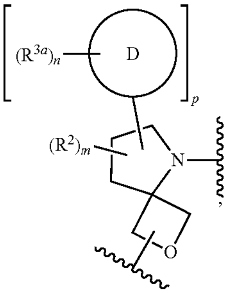

-continued
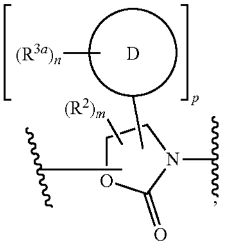
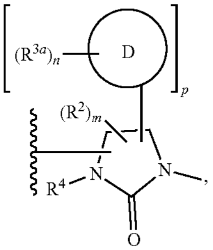
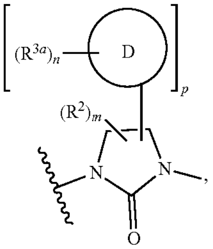
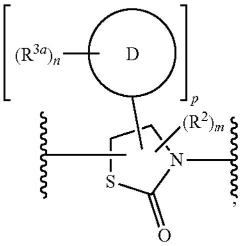
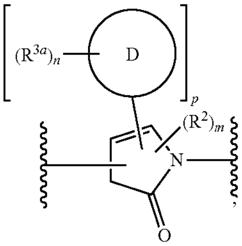
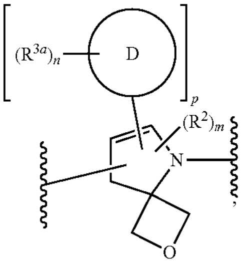
-continued
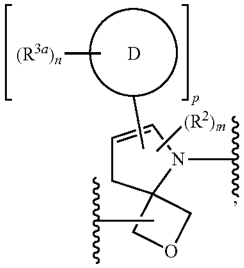
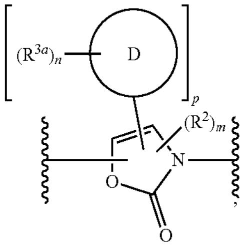
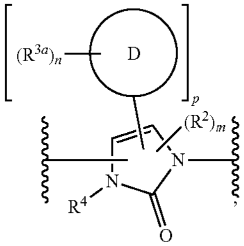
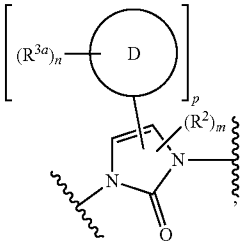
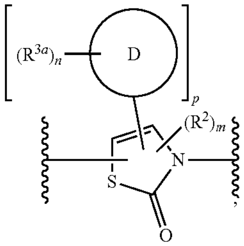
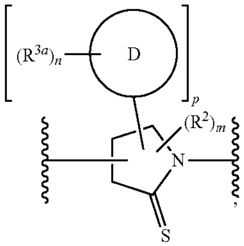

-continued
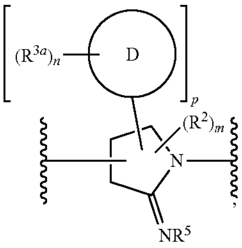
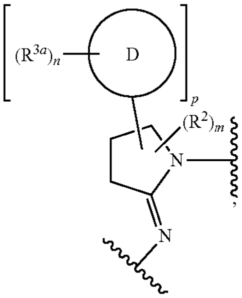
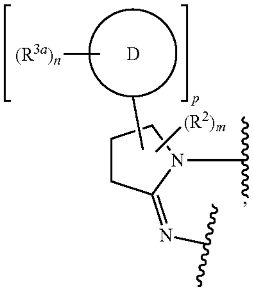
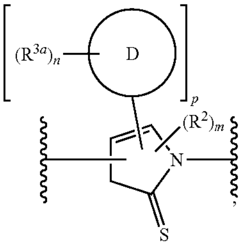
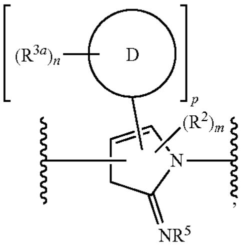
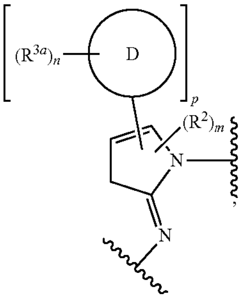
-continued
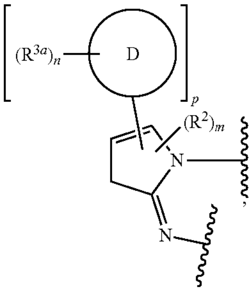
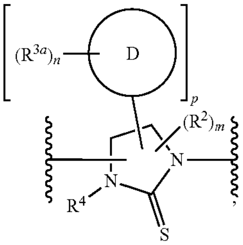
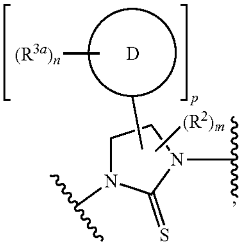
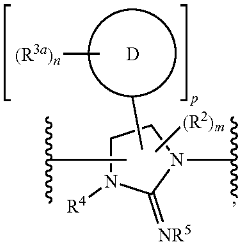
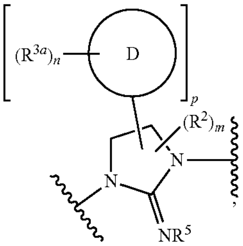
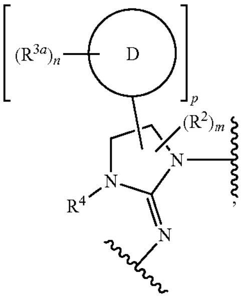

-continued
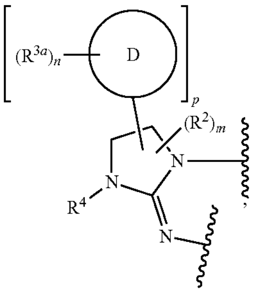
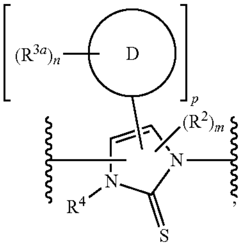
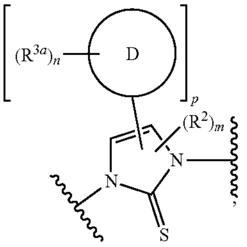
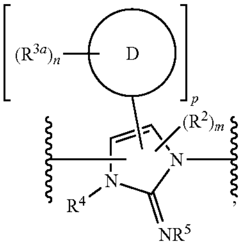
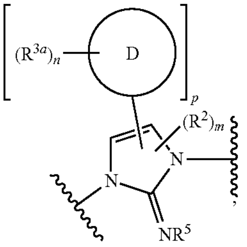
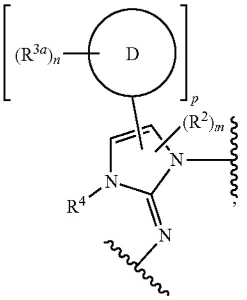
-continued
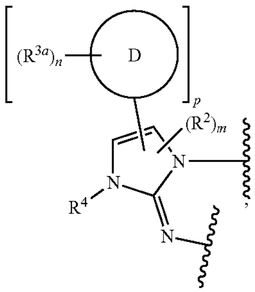
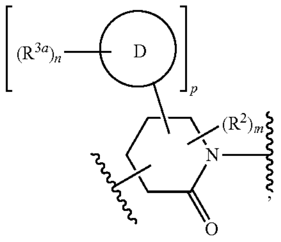
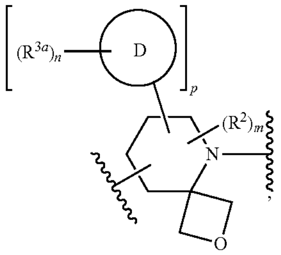
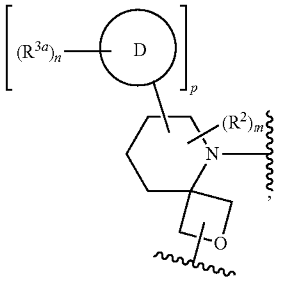
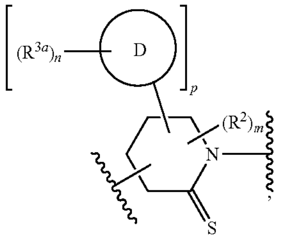
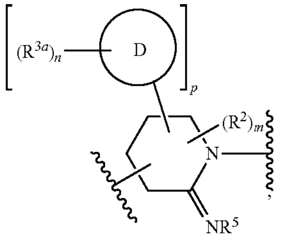

-continued

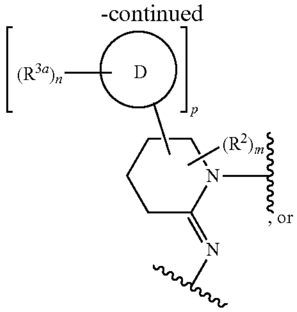

, or

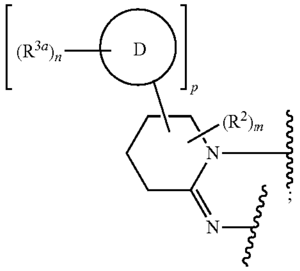

;

each of $R^2$, $R^{3a}$, and $R^4$ is independently hydrogen, —$R_6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-gg above is provided as a compound of formula I-gg' or formula I-gg'':

I-gg'

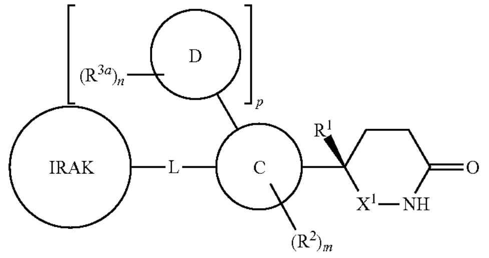

I-gg''

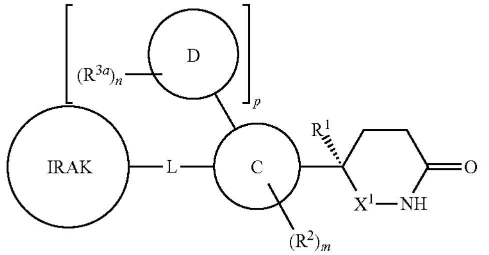

or a pharmaceutically acceptable salt thereof, wherein: each of IRAK, Ring C, Ring D, L, $R^1$, $R^2$, $R^{3a}$, $X^1$, m, n, and p is as defined above.

In certain embodiments, the present invention provides a compound of Formula I, wherein LBM is an E3 ubiquitin ligase (cereblon) binding moiety thereby forming a compound of formula I-hh:

I-hh

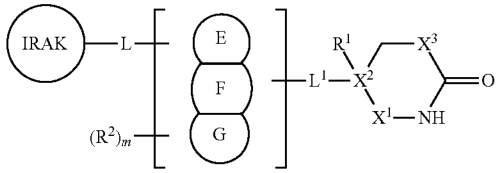

or a pharmaceutically acceptable salt thereof, wherein L and IRAK are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —$P(O)NR_2$—, —C(O)—, —C(S)—, or

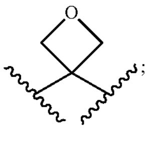 [SMILES: *C1(*)COC1]

;

$X^2$ is a carbon atom, nitrogen atom, or silicon atom;

$X^3$ is a bivalent moiety selected from a covalent bond, —$CR_2$—, —NR—, —O—, —S—, or —$SiR_2$—;

$R^1$ is absent, hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)R_2$, —$SiR_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —$C(R)_2N(R)C(O)R$, —$C(R)_2N(R)C(O)N(R)_2$, —OC(O)R, —OC(O)N$(R)_2$, —OP(O)$R_2$, —OP(O)$(OR)_2$, —OP(O)(OR)$NR_2$, —OP(O)$(NR_2)_2$—, —N(R)C(O)OR, —N(R)C(O)R, —N(R)C(O)$NR_2$, —N(R)$S(O)_2R$, —NP(O)$R_2$, —N(R)P(O)$(OR)_2$, —N(R)P(O)(OR)$NR_2$, —N(R)P(O)$(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—; and m is 0, 1, 2, 3, 4, 5, 6, 7, 8, 9, 10, 11, 12, 13, 14, 15, or 16.

Where a point of attachment of

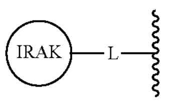

is depicted on Ring E, Ring F, or Ring G, it is intended, and one of ordinary skill in the art would appreciate, that the point of attachment of

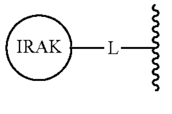

may be on any available carbon or nitrogen atom on Ring E, Ring F, or Ring G, including the ring to which Ring E or Ring G is fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G is fused to Ring F.

Where a point of attachment of

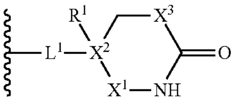

is depicted on Ring E, Ring F, or Ring G, it is intended, and one of ordinary skill in the art would appreciate, that the point of attachment of

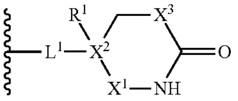

may be on any available carbon or nitrogen atom on Ring E, Ring F, or Ring G, including the carbon atom to which Ring E or Ring G is fused to Ring F.

In some embodiments, a compound of formula I-hh above is provided as a compound of formula I-hh' or formula I-hh":

I-hh'

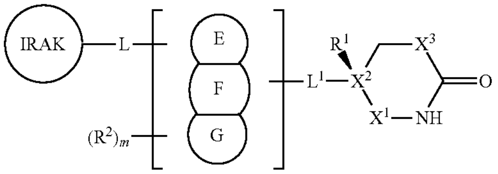

I-hh"

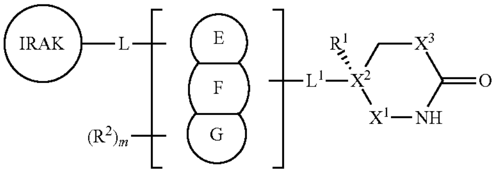

or a pharmaceutically acceptable salt thereof, wherein: each of IRAK, Ring E, Ring F, Ring G, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-hh-1 or I-hh-2:

I-hh-1

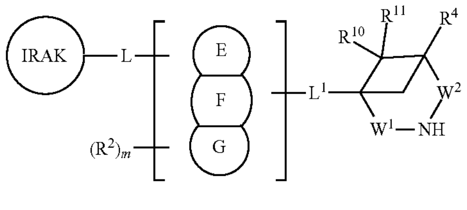

-continued

I-hh-2

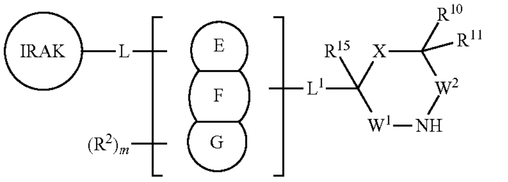

or a pharmaceutically acceptable salt thereof, wherein L and IRAK are as defined above and described in embodiments herein, and wherein:

each $R^2$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —$C(R)_2N(R)C(O)R$, —$C(R)_2N(R)C(O)N(R)_2$, —OC(O)R, —OC(O)N$(R)_2$, —OP(O)$R_2$, —OP(O)$(OR)_2$, —OP(O)(OR)$NR_2$, —OP(O)$(NR_2)_2$—, —N(R)C(O)OR, —N(R)C(O)R, —N(R)C(O)$NR_2$, —N(R)$S(O)_2R$, —NP(O)$R_2$, —N(R)P(O)$(OR)_2$, —N(R)P(O)(OR)$NR_2$, —N(R)P(O)$(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3, 4, 5, 6, 7, 8, 9, 10, 11, 12, 13, 14, 15, or 16; and $R^4$, $R^{10}$, $R^{11}$, $R^{15}$, $W^1$, $W^2$, and X is as defined in WO 2019/099868, the entirety of each of which is herein incorporated by reference.

Where a point of attachment of

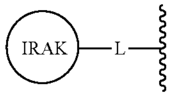

is depicted on Ring E, Ring F, or Ring G, it is intended, and one of ordinary skill in the art would appreciate, that the point of attachment of

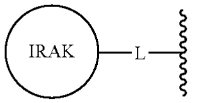

may be on any available carbon or nitrogen atom on Ring E, Ring F, or Ring G, including the ring to which Ring E or Ring G is fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G is fused to Ring F.

Where a point of attachment of

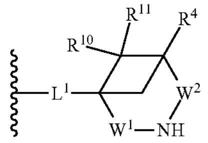

or

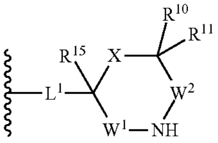

is depicted on Ring E, Ring F, or Ring G, it is intended, and one of ordinary skill in the art would appreciate, that the point of attachment of

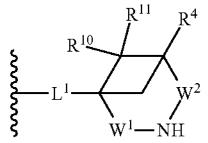

or

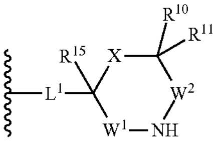

may be on any available carbon or nitrogen atom on Ring E, Ring F, or Ring G, including the carbon atom to which Ring E or Ring G is fused to Ring F.

In certain embodiments, the present invention provides a compound of Formula I, wherein LBM is an E3 ubiquitin ligase (cereblon) binding moiety thereby forming a compound of formula I-ii:

I-ii

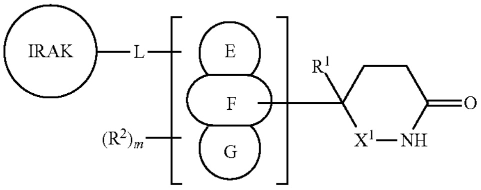

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

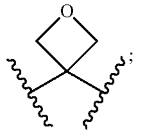 [SMILES: *C1(*)COC1]

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2N(R)C(O)R$, —$C(R)_2N(R)C(O)N(R)_2$, —OC(O)R, —OC(O)$N(R)_2$, —N(R)C(O)OR, —N(R)C(O)R, —N(R)C(O)$N(R)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl containing 0-3 nitrogens, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur, wherein Ring E, Ring F, and Ring G is independently and optionally substituted with 1-2 oxo groups; and m is 0, 1, 2, 3, or 4.

Where a point of attachment of

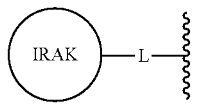

is depicted on Ring E, Ring F, or Ring G, it is intended, and one of ordinary skill in the art would appreciate, that the point of attachment of

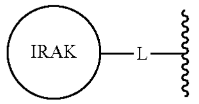

may be on any available carbon or nitrogen atom on Ring E, Ring F, or Ring G, including the ring to which Ring E or Ring G is fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G is fused to Ring F.

In some embodiments, a compound of formula I-ii above is provided as a compound of formula I-ii' or formula I-ii":

I-ii'

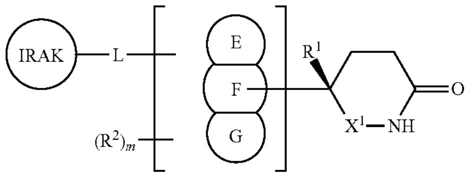

I-ii"

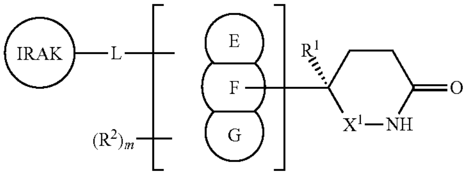

or a pharmaceutically acceptable salt thereof, wherein: each of IRAK, L, Ring E, Ring F, Ring G, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-jj:

I-jj

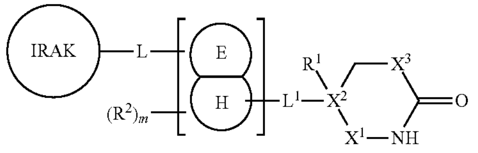

or a pharmaceutically acceptable salt thereof, wherein L and IRAK are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

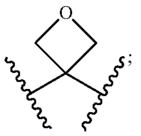 [SMILES: *C1(*)COC1]

$X^2$ is a carbon atom, nitrogen atom, or silicon atom;

$X^3$ is a bivalent moiety selected from a covalent bond, —$CR_2$—, —NR—, —O—, —S—, or —$SiR_2$—;

$R^1$ is absent, hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)R_2$, —$SiR_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3, or 4.

Where a point of attachment of

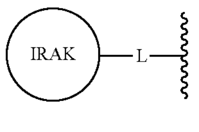

is depicted on Ring E or Ring H, it is intended, and one of ordinary skill in the art would appreciate, that the point of attachment of

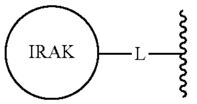

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

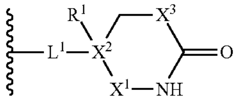

is depicted on Ring E and Ring H, it is intended, and one of ordinary skill in the art would appreciate, that the point of attachment of

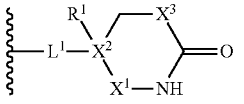

may be on any available carbon or nitrogen atom on Ring E or Ring H including the carbon atom to which Ring E and Ring H are fused.

In some embodiments, a compound of formula I-jj above is provided as a compound of formula I-jj' or formula I-jj":

I-jj'

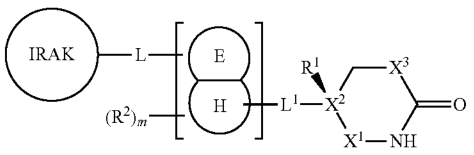

I-jj"

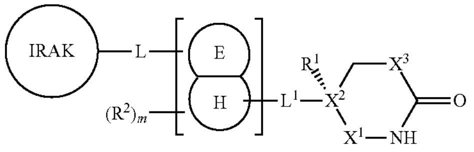

or a pharmaceutically acceptable salt thereof, wherein:

each of IRAK, Ring E, Ring H, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-kk:

I-kk

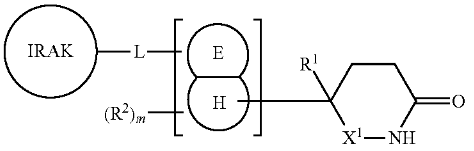

or a pharmaceutically acceptable salt thereof, wherein L and IRAK are as defined above and described in embodiments herein, and wherein:

$X^1$ is a bivalent moiety selected from a covalent bond, $—CH_2—$, —C(O)—, —C(S)—, or

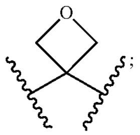 [SMILES: *C1(*)COC1]

$R^1$ is hydrogen, deuterium, halogen, —CN, —OR, —SR, —S(O)R, $—S(O)_2R$, $—N(R)_2$, $—Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $—R^6$, halogen, —CN, $—NO_2$, —OR, —SR, $—N(R)_2$, $—Si(R)_3$, $—S(O)_2R$, $—S(O)_2N(R)_2$, —S(O)R, —C(O)R, —C(O)OR, $—C(O)N(R)_2$, —C(O)N(R)OR, $—C(R)_2N(R)C(O)R$, $—C(R)_2N(R)C(O)N(R)_2$, —OC(O)R, $—OC(O)N(R)_2$, —N(R)C(O)OR, —N(R)C(O)R, $—N(R)C(O)N(R)_2$, or $—N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups; and m is 0, 1, 2, 3, or 4.

Where a point of attachment of

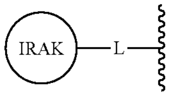

is depicted on Ring E or Ring H, it is intended, and one of ordinary skill in the art would appreciate, that the point of attachment of

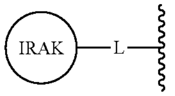

may be on any available carbon or nitrogen atom on Ring E or Ring H including the carbon atom to which Ring E and Ring H are fused.

Where a point of attachment of $—(R^2)_m$ is depicted on Ring E and Ring H, it is intended, and one of ordinary skill in the art would appreciate, that the point of attachment of $—(R^2)_m$ may be on any available carbon or nitrogen atom on Ring E or Ring H including the carbon atom to which Ring E and Ring H are fused.

Where a point of attachment of

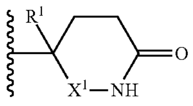

is depicted on Ring E and Ring H, it is intended, and one of ordinary skill in the art would appreciate, that the point of attachment of

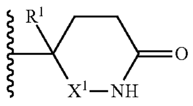

may be on any available carbon or nitrogen atom on Ring E or Ring H including the carbon atom to which Ring E and Ring H are fused.

In some embodiments, a compound of formula I-kk above is provided as a compound of formula I-kk' or formula I-kk".

I-kk'

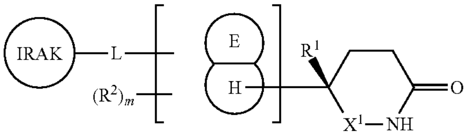

-continued

I-kk''

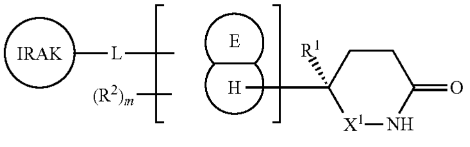

or a pharmaceutically acceptable salt thereof, wherein: each of IRAK, Ring E, Ring H, L, $R^1$, $R^2$, $X^1$, and m is as defined above.

In some embodiments, the present invention provides the compound of formula I-kk wherein Ring H is 1,3-dihydro-2H-1,4-diazepin-2-one, thereby forming a compound of formula I-kk-1:

I-kk-1

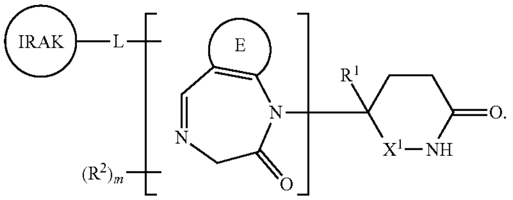

or a pharmaceutically acceptable salt thereof, wherein: each of IRAK, L, Ring E, $X^1$, $R^1$, $R^2$, and m is as defined above.

In certain embodiments, the present invention provides a compound of Formula I, wherein LBM is an E3 ubiquitin ligase (cereblon) binding moiety thereby forming a compound of formula I-ll:

I-ll

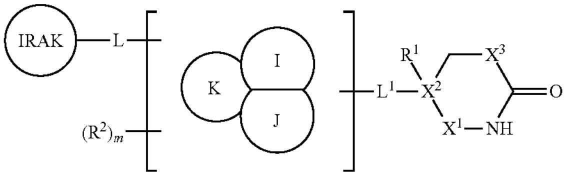

or a pharmaceutically acceptable salt thereof, wherein L and IRAK are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

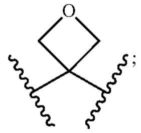 [SMILES: *C1(*)COC1]

;

$X^2$ is a carbon atom, nitrogen atom, or silicon atom;

$X^3$ is a bivalent moiety selected from a covalent bond, —$CR_2$—, —NR—, —O—, —S—, or —$SiR_2$—;

$R^1$ is absent, hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)R_2$, —$SiR_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—; and m is 0, 1, 2, 3, or 4.

Where a point of attachment of

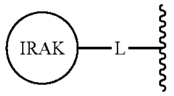

is depicted on Ring I, Ring J, and Ring K, it is intended, and one of ordinary skill in the art would appreciate, that the point of attachment of

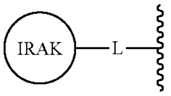

may be on any available carbon or nitrogen atom on Ring I, Ring J, or Ring K, including the carbon atom to which Ring I, Ring J, and Ring K are fused.

Where a point of attachment of —$(R^2)_m$ is depicted on Ring I, Ring J, and Ring K, it is intended, and one of ordinary skill in the art would appreciate, that the point of attachment of —$(R^2)_m$ may be on any available carbon or nitrogen atom on Ring I, Ring J, or Ring K, including the carbon atom to which Ring I, Ring J, and Ring K are fused.

Where a point of

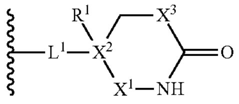

is depicted on Ring I, Ring J, and Ring K, it is intended, and one of ordinary skill in the art would appreciate, that the point of attachment of

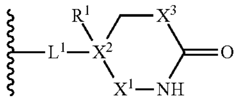

may be on any available carbon or nitrogen atom on Ring I, Ring J, or Ring K, including the carbon atom to which Ring I, Ring J, and Ring K are fused.

In some embodiments, a compound of formula I-ll above is provided as a compound of formula I-ll' or formula I-ll''.

I-ll'

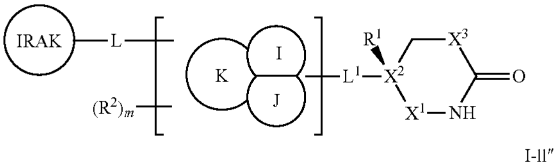

I-ll''

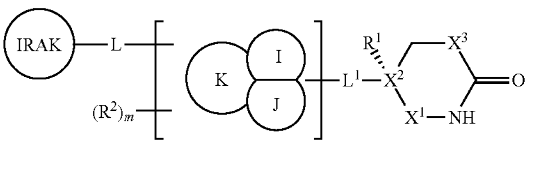

or a pharmaceutically acceptable salt thereof, wherein:

each of IRAK, Ring I, Ring J, Ring K, L, $L^1$, $R^1$, $R^2$, $X^1$, $X^2$, $X^3$, and m is as defined above.

In certain embodiments, the present invention provides a compound of formula I-mm:

I-mm

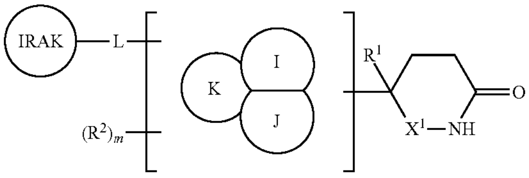

or a pharmaceutically acceptable salt thereof, wherein L and IRAK are as defined above and described in embodiments herein, and wherein:

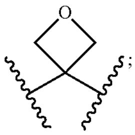 [SMILES: *C1(*)COC1]

;

$X^1$ is a bivalent moiety selected from a covalent bond, —$CH_2$—, —C(O)—, —C(S)—, or $R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups; and m is 0, 1, 2, 3, or 4.

Where a point of attachment of

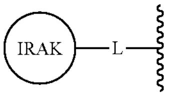

is depicted on Ring I, Ring J, and Ring K, it is intended, and one of ordinary skill in the art would appreciate, that the point of attachment of

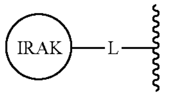

may be on any available carbon or nitrogen atom on Ring I, Ring J, or Ring K, including the carbon atom to which Ring I, Ring J, and Ring K are fused.

Where a point of attachment of —$(R^2)_m$ is depicted on Ring I, Ring J, and Ring K, it is intended, and one of ordinary skill in the art would appreciate, that the point of attachment of —$(R^2)_m$ may be on any available carbon or nitrogen atom on Ring I, Ring J, or Ring K, including the carbon atom to which Ring I, Ring J, and Ring K are fused.

Where a point of attachment of

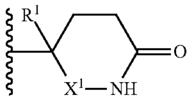

is depicted on Ring I, Ring J, and Ring K, it is intended, and one of ordinary skill in the art would appreciate, that the point of attachment of

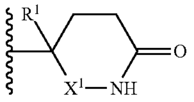

may be on any available carbon or nitrogen atom on Ring I, Ring J, or Ring K, including the carbon atom to which Ring I, Ring J, and Ring K are fused.

In some embodiments, a compound of formula I-mm above is provided as a compound of formula I-mm' or formula I-mm"

I-mm'

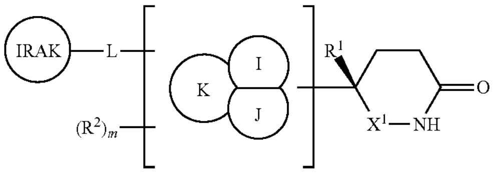

-continued

I-mm"

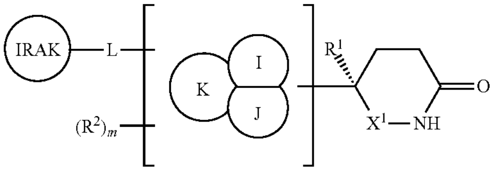

or a pharmaceutically acceptable salt thereof, wherein:

each of IRAK, Ring I, Ring J, Ring K, L, $R^1$, $R^2$, $X^1$, and m is as defined above.

In some embodiments, the present invention provides the compound of formula I-mm wherein Ring J is pyrrole, thereby forming a compound of formula I-mm-1:

I-mm-1

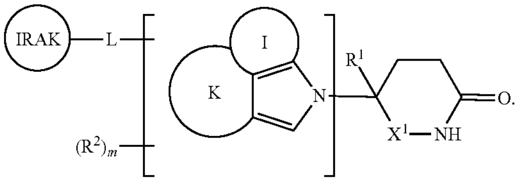

or a pharmaceutically acceptable salt thereof, wherein:

each of IRAK, L, Ring I, Ring K, $X^1$, $R^1$, $R^2$, and m is as defined above.

As described above, in another aspect, the present invention provides a compound of Formula I-nn:

I-nn

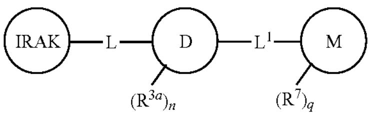

or a pharmaceutically acceptable salt thereof, wherein:

Ring M is selected from

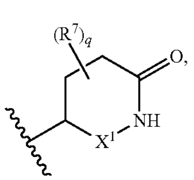
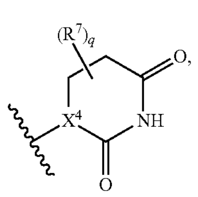
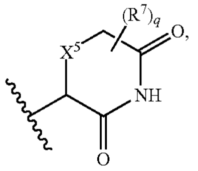
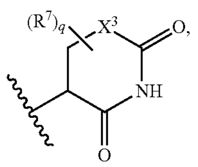
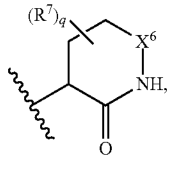

-continued

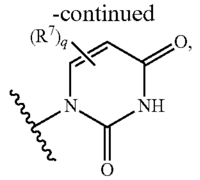

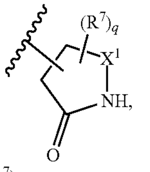

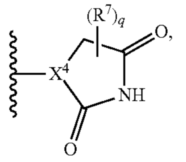

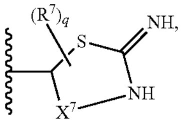

or

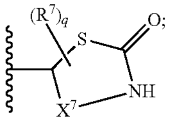

each of $X^1$, $X^6$, and $X^7$ is independently a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

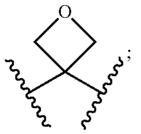 [SMILES: *C1(*)COC1]

;

each of $X^3$ and $X^5$ is independently a bivalent moiety selected from a covalent bond, —$CR_2$—, —NR—, —O—, —S—, or —$SiR_2$—;

$X^4$ is a trivalent moiety selected from

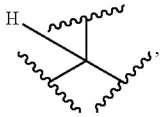

,

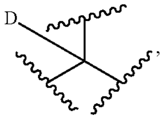

,

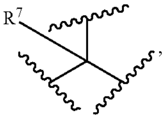

,

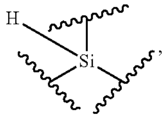

,

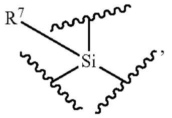

,

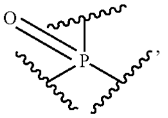

, or

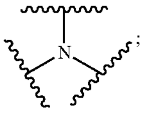

;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^{3a}$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —$C(R)_2N(R)C(O)R$, —$C(R)_2N(R)C(O)N(R)_2$, —OC(O)R, —OC(O)N$(R)_2$, —$OP(O)R_2$, —$OP(O)(OR)_2$, —OP(O)(OR)$NR_2$, —$OP(O)(NR_2)_2$—, —N(R)C(O)OR, —N(R)C(O)R, —N(R)C(O)$NR_2$, —N(R)$S(O)_2R$, —$NP(O)R_2$, —N(R)$P(O)(OR)_2$, —N(R)P(O)(OR)$NR_2$, —N(R)P$(O)(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^7$ is independently hydrogen, deuterium, halogen, —CN, —OR, —SR, —S(O)R, —$S(O)_2R$, —$NR_2$, —$P(O)(OR)_2$, —P(O)$(NR_2)$OR, —$P(O)(NR_2)_2$, —Si$(OH)R_2$, —$Si(OH)_2R$, —$SiR_3$, or an optionally substituted $C_{1-4}$ aliphatic; or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur;

two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur;

two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur; $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

n is 0, 1, 2, 3, or 4; and q is 0, 1, 2, 3, or 4.

As defined above and described herein, each of $X^1$, $X^6$, and $X^7$ is independently a bivalent moiety selected from a covalent bond, —$CH_2$—, —$C(R)_2$—, —C(O)—, —C(S)—, —CH(R)—, —$CH(CF_3)$—, —P(O)(OR)—, —P(O)(R)—, —P(O)$(NR_2)$—, —S(O)—, —$S(O)_2$—, or

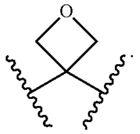 [SMILES: *C1(*)COC1]

In some embodiments, each of $X^1$, $X^6$, and $X^7$ is independently a covalent bond. In some embodiments, each of $X^1$, $X^6$, and $X^7$ is independently —$CH_2$—. In some embodiments, each of $X^1$, $X^6$, and $X^7$ is independently —$CR_2$—. In some embodiments, each of $X^1$, $X^6$, and $X^7$ is independently —C(O)—. In some embodiments, each of $X^1$, $X^6$, and $X^7$ is independently —C(S)—. In some embodiments, each of $X^1$, $X^6$, and $X^7$ is independently —CH(R)—. In some embodiments, each of $X^1$, $X^6$, and $X^7$ is independently —CH($CF_3$)—. In some embodiments, each of $X^1$, $X^6$, and $X^7$ is independently —P(O)(OR)—. In some embodiments, each of $X^1$, $X^6$, and $X^7$ is independently —P(O)(R)—. In some embodiments, each of $X^1$, $X^6$, and $X^7$ is independently —P(O)$NR_2$—. In some embodiments, each of $X^1$, $X^6$, and $X^7$ is independently —S(O)—. In some embodiments, each of $X^1$, $X^6$, and $X^7$ is independently —$S(O)_2$—. In some embodiments, each of $X^1$, $X^6$, and $X^7$ is independently

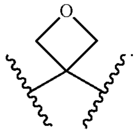 [SMILES: *C1(*)COC1]

In some embodiments, each of $X^1$, $X^6$, and $X^7$ is independently selected from those depicted in Table 1 below.

As defined above and described herein, $X^2$ is a carbon atom, nitrogen atom, or silicon atom.

In some embodiments, $X^2$ is a carbon atom. In some embodiments, $X^2$ is a nitrogen atom. In some embodiments, $X^2$ is a silicon atom.

In some embodiments, $X^2$ is selected from those depicted in Table 1 below.

As defined above and described herein, $X^3$ is a bivalent moiety selected from —$CH_2$—, —$CR_2$—, —NR—, —$CF_2$—, —CHF—, —S—, —CH(R)—, —$SiR_2$—, or —O—.

In some embodiments, each of $X^3$ and $X^5$ is independently —$CH_2$—. In some embodiments, each of $X^3$ and $X^5$ is independently —$CR_2$—. In some embodiments, each of $X^3$ and $X^5$ is independently —NR—. In some embodiments, each of $X^3$ and $X^5$ is independently —$CF_2$—. In some embodiments, each of $X^3$ and $X^5$ is independently —CHF—. In some embodiments, each of $X^3$ and $X^5$ is independently —S—. In some embodiments, each of $X^3$ and $X^5$ is independently —CH(R)—. In some embodiments, each of $X^3$ and $X^5$ is independently —$SiR_2$—. In some embodiments, each of $X^3$ and $X^5$ is independently —O—.

In some embodiments, each of $X^3$ and $X^5$ is independently selected from those depicted in Table 1 below.

As defined above and described herein, $X^4$ is a trivalent moiety selected from

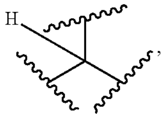, 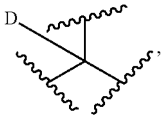, 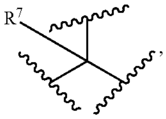,

-continued

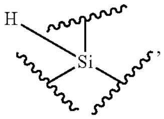, 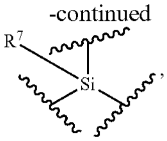, 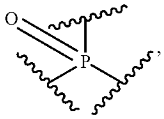, or

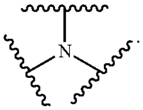

In some embodiments, $X^4$ is

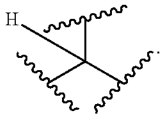

In some embodiments, $X^4$ is

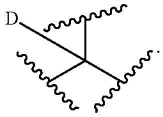

In some embodiments, $X^4$ is

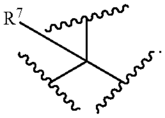

In some embodiments $X^4$ is

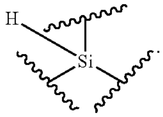

In some embodiments, $X^4$ is

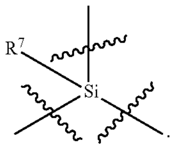

In some embodiments, $X^4$ is

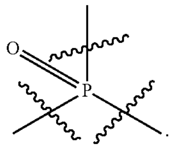 [SMILES: *P(*)(*)=C=O]

In some embodiments, $X^4$ is

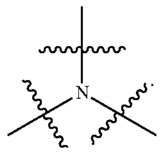 [SMILES: *N(*)*]

In some embodiments, $X^4$ is selected from those depicted in Table 1 below.

As defined above and described herein, $R^1$ is hydrogen, deuterium, halogen, —CN, —OR, —SR, —S(O)R, —$S(O)_2$R, —$NR_2$, —$P(O)(OR)_2$, —$P(O)(NR_2)$OR, —$P(O)(NR_2)_2$, —$Si(OH)_2$R, —$Si(OH)R_2$, —$SiR_3$, an optionally substituted $C_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —$S(O)_2$R. In some embodiments, $R^1$ is —$NR_2$. In some embodiments, $R^1$ is —$P(O)(OR)_2$. In some embodiments, $R^1$ is —$P(O)(NR_2)$OR. In some embodiments, $R^1$ is —$P(O)(NR_2)_2$. In some embodiments, $R^1$ is —$Si(OH)_2$R. In some embodiments, $R^1$ is —$Si(OH)R_2$. In some embodiments, $R^1$ is —$SiR_3$. In some embodiments, $R^1$ is an optionally substituted $C_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1 below.

As defined above and described herein, each R is independently hydrogen, deuterium, or an optionally substituted group selected from $C_{1-6}$ aliphatic, phenyl, a 4-7 membered saturated or partially unsaturated heterocyclic having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is hydrogen. In some embodiments, R is deuterium. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-3 heteroatoms independently selected from boron, nitrogen, oxygen, silicon, and sulfur. In some embodiments, R is optionally substituted 5-6 membered heteroaryl ring having 1-4 heteroatoms independently selected from boron, nitrogen, oxygen, silicon, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is selected from those depicted in Table 1 below.

As defined above and described herein, each of $R^2$ and $R^{3a}$ is independently hydrogen, deuterium, —$R^6$, halogen, —CN, —$NO_2$, —OR, —$Si(OH)_2$R, —$Si(OH)R_2$, —SR, —$NR_2$, —$SiR_3$, —$S(O)_2$R, —$S(O)_2NR_2$, —S(O)R, —C(O)R, —C(O)OR, —C(O)$NR_2$, —C(O)N(R)OR, —$C(R)_2$N(R)C(O)R, —$C(R)_2$N(R)C(O)$NR_2$, —OC(O)R, —OC(O)$NR_2$, —OP(O)$R_2$, —OP(O)$(OR)_2$, —OP(O)(OR)$NR_2$, —OP(O)$(NR_2)_2$—, —N(R)C(O)OR, —N(R)C(O)R, —N(R)C(O)$NR_2$, —N(R)$S(O)_2$R, —NP(O)$R_2$, —N(R)P(O)$(OR)_2$, —N(R)P(O)(OR)$NR_2$, —N(R)P(O)$(NR_2)_2$, or —N(R)$S(O)_2$R.

In some embodiments, $R^2$ and $R^{3a}$ is independently hydrogen. In some embodiments, $R^2$ and $R^{3a}$ is independently deuterium. In some embodiments, $R^2$ and $R^{3a}$ is independently —$R^6$. In some embodiments, $R^2$ and $R^{3a}$ is independently halogen. In some embodiments, $R^2$ and $R^{3a}$ is independently —CN. In some embodiments, $R^2$ and $R^{3a}$ is independently —$NO_2$. In some embodiments, $R^2$ and $R^{3a}$ is independently —OR. In some embodiments, $R^2$ and $R^{3a}$ is independently —$Si(OH)_2$R. In some embodiments, $R^2$ and $R^{3a}$ is independently —$Si(OH)R_2$. In some embodiments, $R^2$ and $R^{3a}$ is independently —SR. In some embodiments, $R^2$ and $R^{3a}$ is independently —$NR_2$. In some embodiments, $R^2$ and $R^{3a}$ is independently —$SiR_3$. In some embodiments, $R^2$ and $R^{3a}$ is independently —$S(O)_2$R. In some embodiments, $R^2$ and $R^{3a}$ is independently —$S(O)_2NR_2$. In some embodiments, $R^2$ and $R^{3a}$ is independently —S(O)R. In some embodiments, $R^2$ and $R^{3a}$ is independently —C(O)R. In some embodiments, $R^2$ and $R^{3a}$ is independently —C(O)OR. In some embodiments, $R^2$ and $R^{3a}$ is independently —C(O)$NR_2$. In some embodiments, $R^2$ and $R^{3a}$ is independently —C(O)N(R)OR. In some embodiments, $R^2$ and $R^{3a}$ is independently —$C(R)_2$N(R)C(O)R. In some embodiments, $R^2$ and $R^{3a}$ is independently —$C(R)_2$N(R)C(O)$NR_2$. In some embodiments, $R^2$ and $R^{3a}$ is independently —OC(O)R. In some embodiments, $R^2$ and $R^{3a}$ is independently —OC(O)$NR_2$. In some embodiments, $R^2$ and $R^{3a}$ is independently —OP(O)$R_2$. In some embodiments, $R^2$ and $R^{3a}$ is independently —OP(O)$(OR)_2$. In some embodiments, $R^2$ and $R^{3a}$ is independently —OP(O)(OR)$NR_2$. In some embodiments, $R^2$ and $R^{3a}$ is independently —OP(O)$(NR_2)_2$—. In some embodiments, $R^2$ and $R^{3a}$ is independently —N(R)C(O)OR. In some embodiments, $R^2$ and $R^{3a}$ is independently —N(R)C(O)R. In some embodiments, $R^2$ and $R^{3a}$ is independently —N(R)C(O)$NR_2$. In some embodiments, $R^2$ and $R^{3a}$ is independently —NP(O)$R_2$. In some embodiments, $R^2$ and $R^{3a}$ is independently —N(R)P(O)$(OR)_2$. In some embodiments, $R^2$ and $R^{3a}$ is independently —N(R)P(O)(OR)$NR_2$. In some embodiments, $R^2$ and $R^{3a}$ is independently —N(R)P(O)$(NR_2)_2$. In some embodiments, $R^2$ and $R^{3a}$ is independently —N(R)$S(O)_2$R.

In some embodiments, $R^2$ and $R^{3a}$ is independently —OH. In some embodiments, $R^2$ and $R^{3a}$ is independently —$NH_2$. In some embodiments, $R^2$ and $R^{3a}$ is independently —$CH_2NH_2$. In some embodiments, $R^2$ and $R^{3a}$ is independently —$CH_2$NHCOMe. In some embodiments, $R^2$ and $R^{3a}$ is independently —$CH_2$NHCONHMe. In some embodiments, $R^2$ and $R^{3a}$ is independently —NHCOMe. In some embodiments, $R^2$ and $R^{3a}$ is independently —NHCONHEt. In some embodiments, $R^2$ and $R^{3a}$ is independently —$SiMe_3$. In some embodiments, $R^2$ and $R^{3a}$ is independently —$SiMe_2$OH. In some embodiments, $R^2$ and $R^{3a}$ is independently —$SiMe(OH)_2$. In some embodiments $R^2$ and $R^{3a}$ is independently

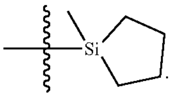

In some embodiments, $R^2$ and $R^{3a}$ is independently Br. In some embodiments, $R^2$ and $R^{3a}$ is independently Cl. In some embodiments, $R^2$ and $R^{3a}$ is independently F. In some embodiments, $R^2$ and $R^{3a}$ is independently Me. In some embodiments, $R^2$ and $R^{3a}$ is independently —NHMe. In some embodiments, $R^2$ and $R^{3a}$ is independently —$NMe_2$. In some embodiments, $R^2$ and $R^{3a}$ is independently —$NHCO_2Et$. In some embodiments, $R^2$ and $R^{3a}$ is independently —CN. In some embodiments, $R^2$ and $R^{3a}$ is independently —$CH_2Ph$. In some embodiments, $R^2$ and $R^{3a}$ is independently —$NHCO_2tBu$. In some embodiments, $R^2$ and $R^{3a}$ is independently —$CO_2tBu$. In some embodiments, $R^2$ and $R^{3a}$ is independently —OMe. In some embodiments, $R^2$ and $R^{3a}$ is independently —$CF_3$.

In some embodiments, $R^2$ or $R^{3a}$ is selected from those depicted in Table 1 below.

As defined above and described herein, $R^3$ is hydrogen, deuterium, halogen, —CN, —$NO_2$, —OR, —$NR_2$, —SR, —$S(O)_2R$, —$S(O)_2NR_2$, —S(O)R, —C(O)R, —C(O)OR, —$C(O)NR_2$, —C(O)NR(OR), —OC(O)R, —$OC(O)NR_2$, —$OP(O)(OR)_2$, —$OP(O)(NR_2)_2$, —$OP(O)(OR)NR_2$, —N(R)C(O)R, —N(R)C(O)OR, —$N(R)C(O)NR_2$, —$N(R)S(O)_2R$, —$N(R)S(O)_2NR_2$, —$N(R)P(O)(OR)_2$, —$N(R)P(O)(OR)NR_2$, —$P(O)(OR)_2$, —$P(O)(NR_2)OR$, —$P(O)(NR_2)_2$, —$Si(OH)_2R$, —$Si(OH)(R)_2$, or —$Si(R)_3$.

In some embodiments, $R^3$ is hydrogen. In some embodiments, $R^3$ is deuterium. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —$NR_2$. In some embodiments, $R^3$ is —SR. In some embodiments, $R^3$ is —$S(O)_2R$. In some embodiments, $R^3$ is —$S(O)_2NR_2$. In some embodiments, $R^3$ is —S(O)R. In some embodiments, $R^3$ is —C(O)R. In some embodiments, $R^3$ is —C(O)OR. In some embodiments, $R^3$ is —$C(O)NR_2$. In some embodiments, $R^3$ is —C(O)NR(OR). In some embodiments, $R^3$ is —OC(O)R. In some embodiments, $R^3$ is —$OC(O)NR_2$. In some embodiments, $R^3$ is —$OP(O)(OR)_2$. In some embodiments, $R^3$ is —$OP(O)(NR_2)_2$. In some embodiments, $R^3$ is —$OP(O)(OR)NR_2$. In some embodiments, $R^3$ is —N(R)C(O)R. In some embodiments, $R^3$ is —N(R)C(O)OR. In some embodiments, $R^3$ is —$N(R)C(O)NR_2$. In some embodiments, $R^3$ is —$N(R)S(O)_2R$. In some embodiments, $R^3$ is —$N(R)S(O)_2NR_2$. In some embodiments, $R^3$ is —$N(R)P(O)(OR)_2$. In some embodiments, $R^3$ is —$N(R)P(O)(OR)NR_2$. In some embodiments, $R^3$ is —$P(O)(OR)_2$. In some embodiments, $R^3$ is —$P(O)(NR_2)OR$. In some embodiments, $R^3$ is —$P(O)(NR_2)_2$. In some embodiments, $R^3$ is —$Si(OH)_2R$. In some embodiments, $R^3$ is —$Si(OH)(R)_2$. In some embodiments, $R^3$ is —$Si(R)_3$.

In some embodiments, $R^3$ is methyl. In some embodiments, $R^3$ is —$OCH_3$. In some embodiments, $R^3$ is chloro.

In some embodiments, $R^3$ is selected from those depicted in Table 1.

As defined above and described herein, each $R^4$ is independently hydrogen, deuterium, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$P(O)(OR)_2$, —$P(O)(NR_2)OR$, or —$P(O)(NR_2)_2$.

In some embodiments, $R^4$ is hydrogen. In some embodiments, $R^4$ is —$R^6$. In some embodiments, $R^4$ is halogen. In some embodiments, $R^4$ is —CN. In some embodiments, $R^4$ is —$NO_2$. In some embodiments, $R^4$ is —OR. In some embodiments, $R^4$ is —SR. In some embodiments, $R^4$ is —$NR_2$. In some embodiments, $R^4$ is —$S(O)_2R$. In some embodiments, $R^4$ is —$S(O)_2NR_2$. In some embodiments, $R^4$ is —S(O)R. In some embodiments, $R^4$ is —C(O)R. In some embodiments, $R^4$ is —C(O)OR. In some embodiments, $R^4$ is —$C(O)NR_2$. In some embodiments, $R^4$ is —C(O)N(R)OR. In some embodiments, $R^4$ is —OC(O)R. In some embodiments, $R^4$ is —$OC(O)NR_2$. In some embodiments, $R^4$ is —N(R)C(O)OR. In some embodiments, $R^4$ is —N(R)C(O)R. In some embodiments, $R^4$ is —$N(R)C(O)NR_2$. In some embodiments, $R^4$ is —$N(R)S(O)_2R$. In some embodiments, $R^4$ is —$P(O)(OR)_2$. In some embodiments, $R^4$ is —$P(O)(NR_2)OR$. In some embodiments, $R^4$ is —$P(O)(NR_2)_2$.

In some embodiments, $R^4$ is methyl. In some embodiments, $R^4$ is ethyl. In some embodiments, $R^4$ is cyclopropyl.

In some embodiments, $R^4$ is selected from those depicted in Table 1.

As defined above and described herein, $R^5$ is hydrogen, deuterium, an optionally substitute $C_{1-4}$ aliphatic, or —CN.

In some embodiments, $R^5$ is hydrogen. In some embodiments, $R^5$ is deuterium. In some embodiments, $R^5$ is an optionally substituted $C_{1-4}$ aliphatic. In some embodiments, $R^5$ is —CN.

In some embodiments, $R^5$ is selected from those depicted in Table 1.

As defined above and described herein, each $R^6$ is independently an optionally substituted group selected from $C_{1-9}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, $R^6$ is an optionally substituted $C_{1-6}$ aliphatic. In some embodiments, $R^6$ is an optionally substituted phenyl. In some embodiments, $R^6$ is an optionally substituted 4-7 membered saturated or partially unsaturated heterocyclic ring having 1-3 heteroatoms independently selected from boron, nitrogen, oxygen, silicon, and sulfur. In some embodiments, $R^6$ is an optionally substituted 5-6 membered heteroaryl ring having 1-4 heteroatoms independently selected from boron, nitrogen, oxygen, silicon, and sulfur.

In some embodiments, $R^6$ is selected from those depicted in Table 1.

As defined generally above, each $R^7$ is independently hydrogen, deuterium, halogen, —CN, —OR, —SR, —S(O)R, —$S(O)_2R$, —$N(R)_2$, —$P(O)(R)_2$, —$P(O)(OR)_2$, —$P(O)(NR_2)OR$, —$P(O)(NR_2)_2$, —$Si(OH)R_2$, —$Si(OH)_2R$, —$SiR_3$, or an optionally substituted $C_{1-4}$ aliphatic, or $R^1$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur, or two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur, or two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —SR. In some embodiments, $R^7$ is —S(O)R. In some embodiments, $R^7$ is —$S(O)_2R$. In some embodiments, $R^7$ is —$NR_2$. In some embodiments, $R^7$ is —$Si(R)_3$. In some embodiments, $R^7$ is —$P(O)(R)_2$. In some embodiments, $R^7$ is —$P(O)(OR)_2$. In some embodiments, $R^7$ is —$P(O)(NR_2)$OR. In some embodiments, $R^7$ is —$P(O)(NR_2)_2$. In some embodiments, $R^7$ is —$Si(OH)R_2$. In some embodiments, $R^7$ is —$Si(OH)_2R$. In some embodiments, $R^7$ is an optionally substituted $C_{1-4}$ aliphatic. In some embodiments, $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur. In some embodiments, two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur. In some embodiments, two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur. In some embodiments, two $R^7$ groups on adjacent carbon atoms are optionally taken together with their intervening atoms to form a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, $R^7$ is selected from hydrogen, halogen, —CN, —OR, —$NR_2$, or $C_{1-4}$ alkyl. In some embodiments, $R^7$ is selected from hydrogen, halogen, —CN, or $C_{1-4}$ alkyl. In some embodiments, $R^7$ is fluoro. In some embodiments, two $R^7$ groups on the same carbon are optionally taken together with their intervening atoms to form a 3- or 4- membered spiro fused ring.

In some embodiments, $R^7$ is selected from those depicted in Table 1 below.

As defined above and described herein, Ring A is a bi- or tricyclic ring selected from

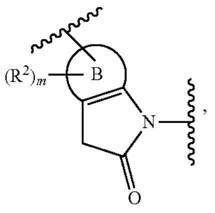
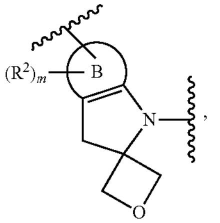
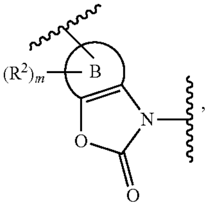
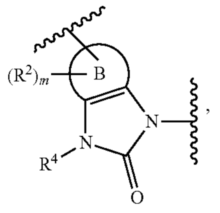

-continued

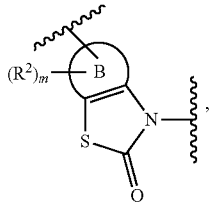
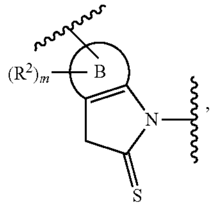
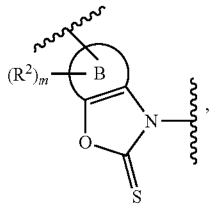
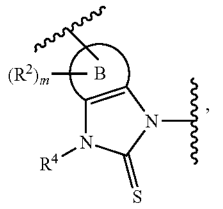
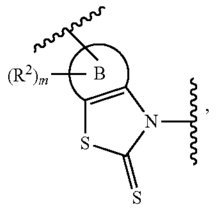
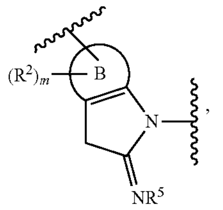
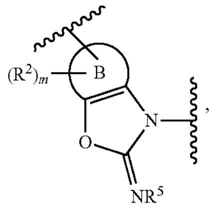
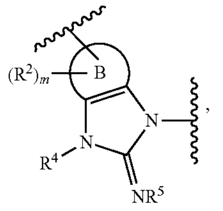
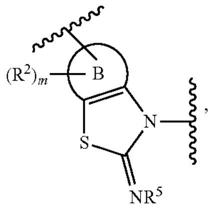
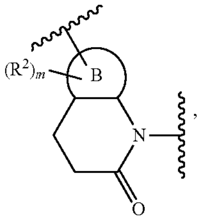
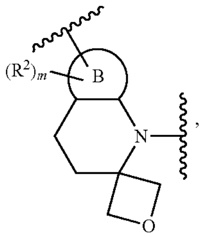
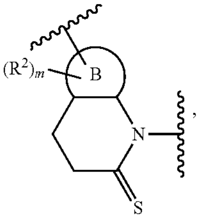
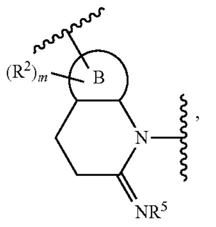
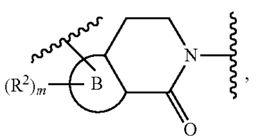
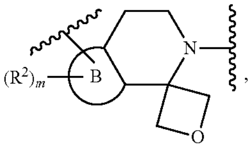
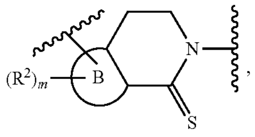

-continued
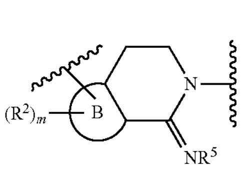, 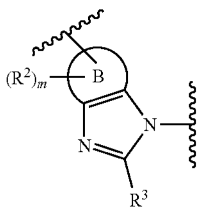,
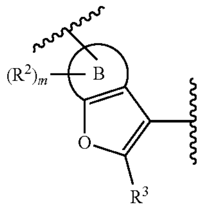, 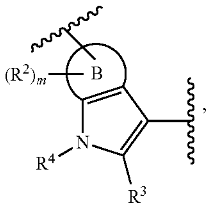, or
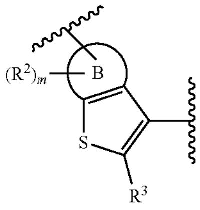.
In some embodiments, Ring A
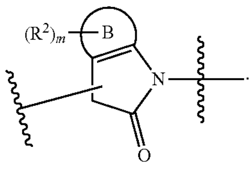.
In some embodiments, Ring A is
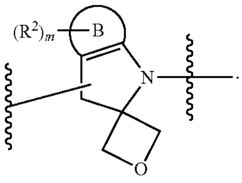.
In some embodiments, Ring A is
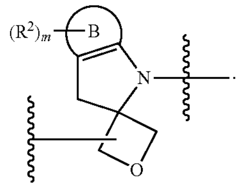.
In some embodiments, Ring A is
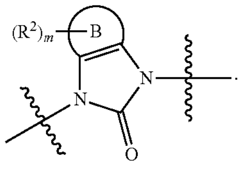.
In some embodiments, Ring A is
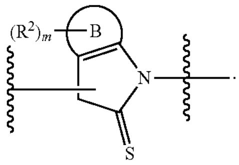.
In some embodiments, Ring A is
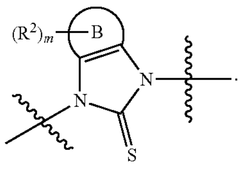.
In some embodiments, Ring A is
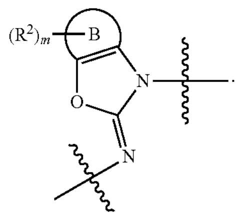.
In some embodiments, Ring A is
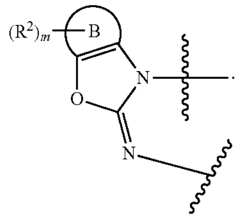.
In some embodiments, Ring A is
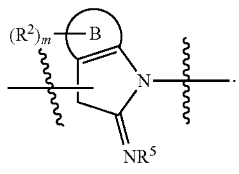.

In some embodiments, Ring A is
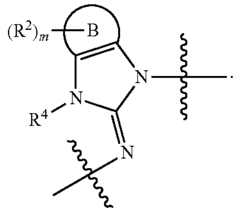
In some embodiments, Ring A is
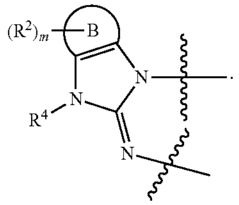
In some embodiments, Ring A is
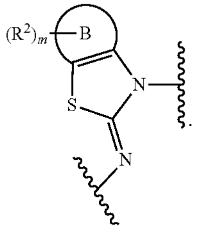
In some embodiments, Ring A is
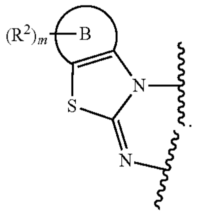
In some embodiments, Ring A is
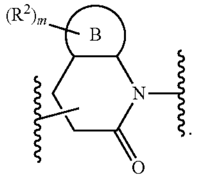
In some embodiments, Ring A is
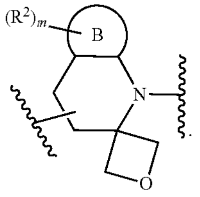
In some embodiments, Ring A is
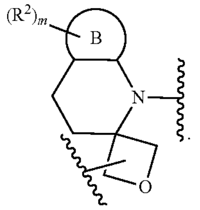
In some embodiments, Ring A is
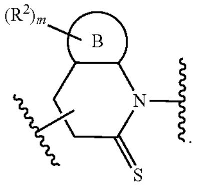
In some embodiments, Ring A is
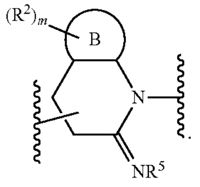
In some embodiments, Ring A
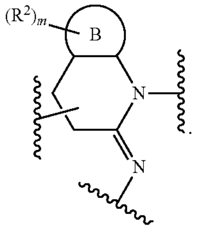

In some embodiments. Ring A is
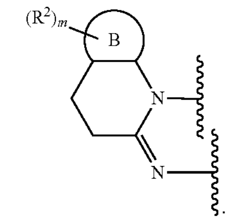
In some embodiments, Ring A is
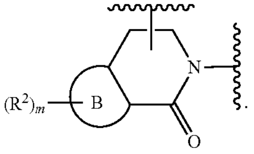
In some embodiments, Ring A is
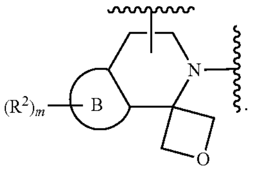
In some embodiments, Ring A is
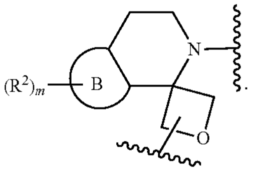
In some embodiments, Ring A is
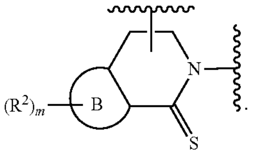
In some embodiments, Ring A is
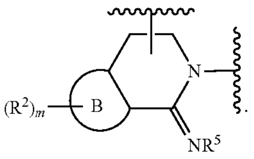
In some embodiments, Ring A is
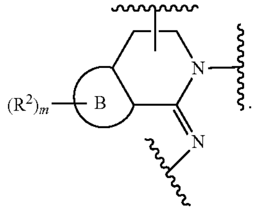
In some embodiments, Ring A is
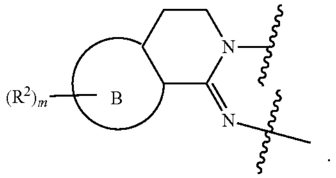
In some embodiments, Ring A is
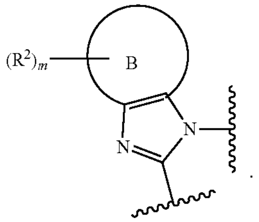
In some embodiments, Ring A is
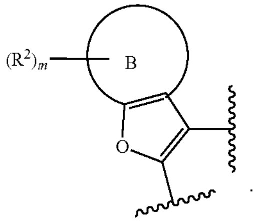
In some embodiments, Ring A is
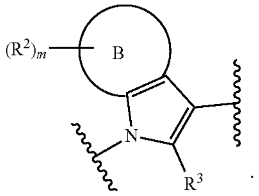

In some embodiments, Ring A is

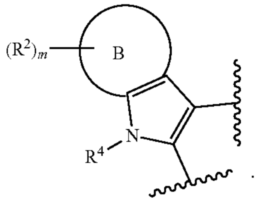

In some embodiments, Ring A is

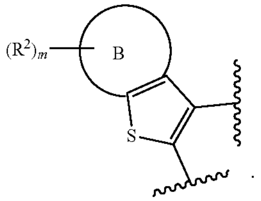

In some embodiments, Ring A is selected from those depicted in Table 1 below.

As defined above and described herein, Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring B is a fused 6-membered aryl. In some embodiments, Ring B is a fused 6-membered heteroaryl containing 1-4 heteroatoms independently selected from nitrogen, oxygen, or sulfur. In some embodiments, Ring B is a fused 5 to 7-membered saturated or partially unsaturated carbocyclyl. In some embodiments, Ring B is fused 5 to 7-membered saturated or partially saturated heterocyclyl with 1-3 heteroatoms independently selected from boron, nitrogen, oxygen, silicon, or sulfur. In some embodiments, Ring B is fused 5-membered heteroaryl with 1-4 heteroatoms independently selected from boron, nitrogen, oxygen, silicon, or sulfur.

In some embodiments, Ring B is

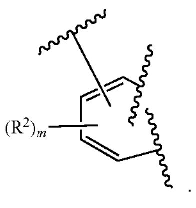

In some embodiments, Ring B is

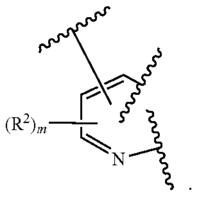

In some embodiments, Ring B is

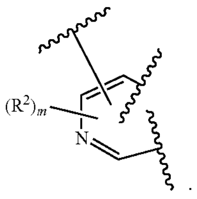

In some embodiments, Ring B is

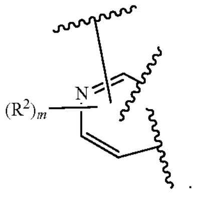

In some embodiments, Ring B is

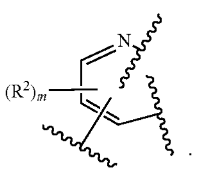

In some embodiments, each Ring B is

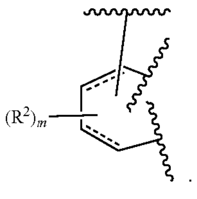

In some embodiments, each Ring B is
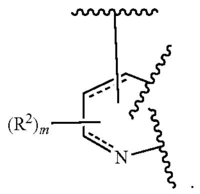
In some embodiments, each Ring B is
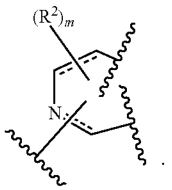
In some embodiments each Ring B is
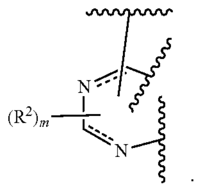
In some embodiments, Ring B is
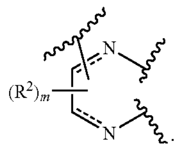
In some embodiments, Ring B
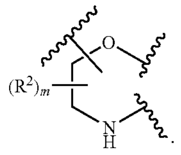
In some embodiments, Ring B is
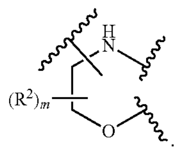
In some embodiments, Ring B is
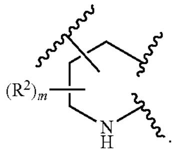
In some embodiments, Ring B is
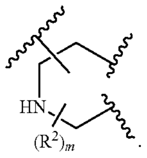
In some embodiments, Ring B is
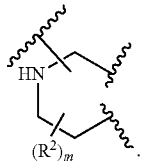
In some embodiments, Ring B is
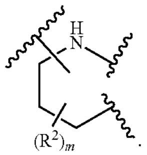
In some embodiments, Ring B is
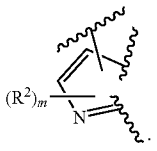
In some embodiments, Ring B is
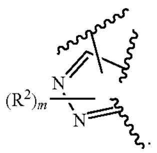

In some embodiments, Ring B is

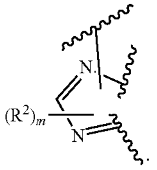

In some embodiments, Ring B is

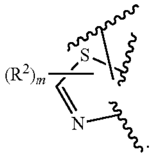

In some embodiments, Ring B is

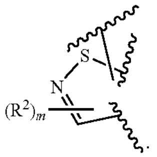

In some embodiments, Ring B is

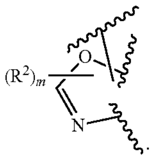

In some embodiments, Ring B is

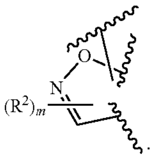

In some embodiments, Ring B is

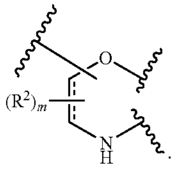

In some embodiments, Ring B

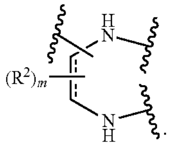

In some embodiments, Ring B is

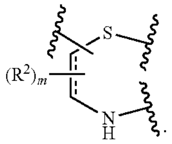

In some embodiments, Ring B is

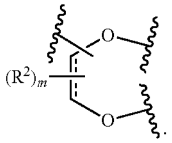

In some embodiments, Ring B is

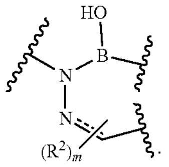

In some embodiments, Ring B is selected from those depicted in Table 1 below.

As defined above and described herein, Ring C is a mono- or bicyclic ring selected from

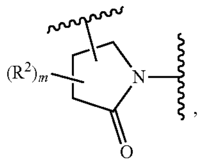

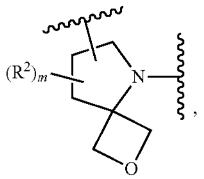

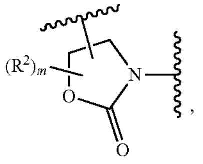

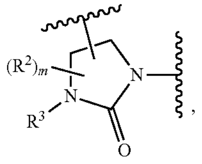

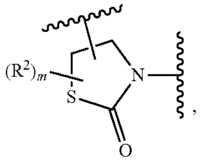

-continued
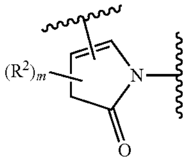
,
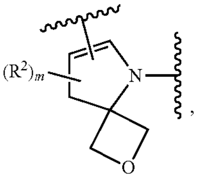
,
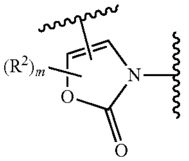
,
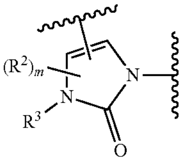
,
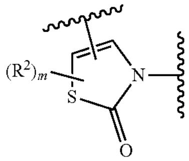
,
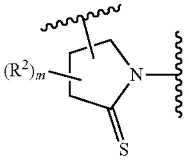
,
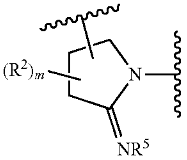
,
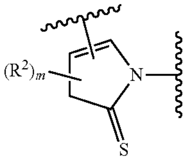
,
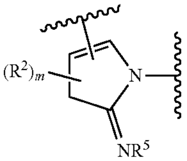
,
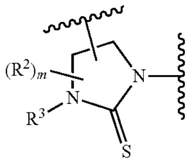
,
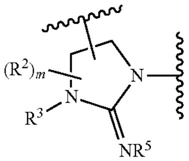
,
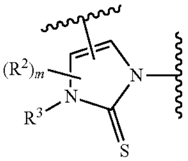
,
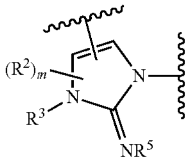
,
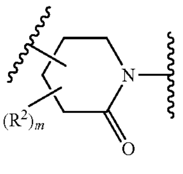
,
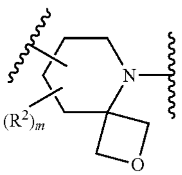
,
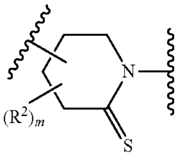
or
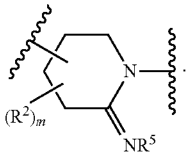
.
In some embodiments, Ring C is
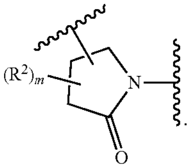
.
In some embodiments, Ring C is
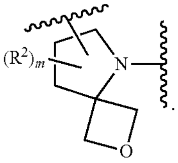
.
In some embodiments, Ring C is
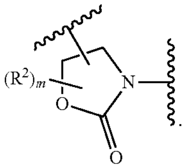
.
In some embodiments, Ring C is
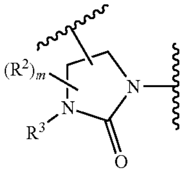
.
In some embodiments, Ring C
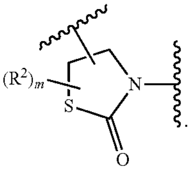
.
In some embodiments, Ring C is
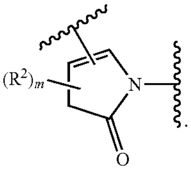
.

In some embodiments, Ring C is
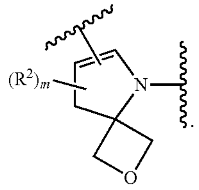
In some embodiments, Ring C is
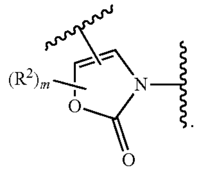
In some embodiments, Ring C is
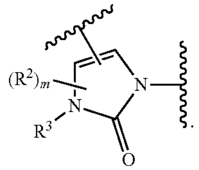
In some embodiments, Ring C is
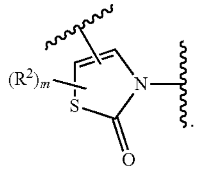
In some embodiments, Ring C is
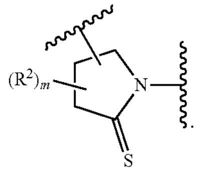
In some embodiments, Ring C is
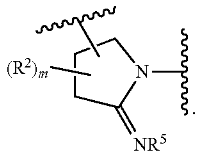
In some embodiments, Ring C is
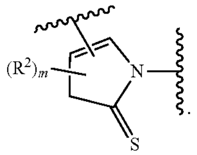
In some embodiments, Ring C is
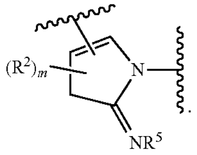
In some embodiments, Ring C is
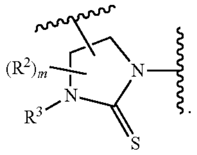
In some embodiments, Ring C is
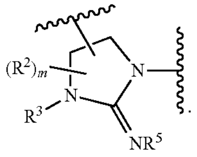
In some embodiments, Ring C is
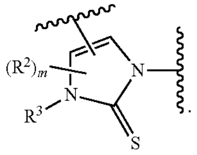
In some embodiments, Ring C is
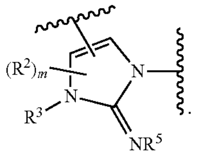

In some embodiments, Ring C is
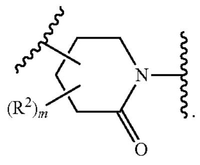
In some embodiments, Ring C is
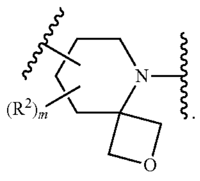
In some embodiments, Ring C is
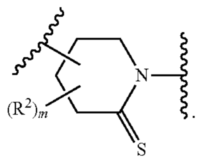
In some embodiments, Ring C is
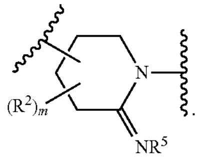
In some embodiments, Ring C is
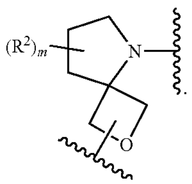
In some embodiments, Ring C is
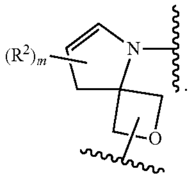
In some embodiments, Ring C is
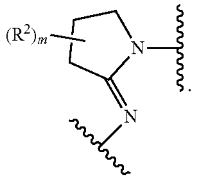
In some embodiments, Ring C is
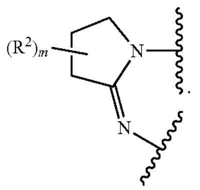
In some embodiments, Ring C is
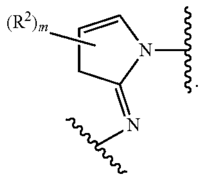
In some embodiments, Ring C is
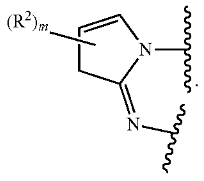
In some embodiments, Ring C is
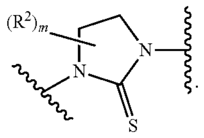
In some embodiments, Ring C is
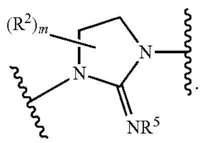

In some embodiments, Ring C is
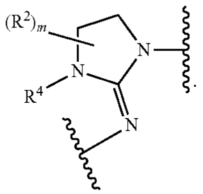
In some embodiments, Ring C is
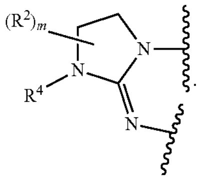
In some embodiments, Ring C is
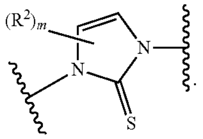
In some embodiments, Ring C is
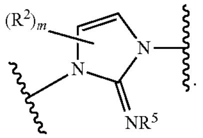
In some embodiments, Ring C is
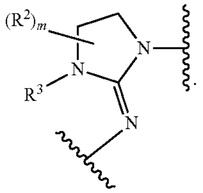
In some embodiments, Ring C
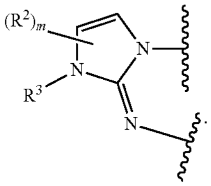
In some embodiments, Ring C is
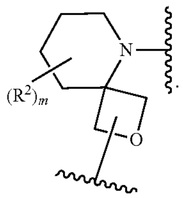
In some embodiments, Ring C is
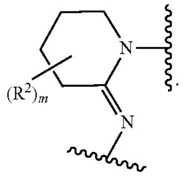
In some embodiments, Ring C is
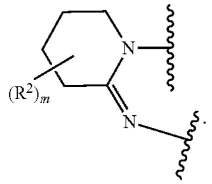
In some embodiments, Ring C is a mono- or bicyclic ring selected from
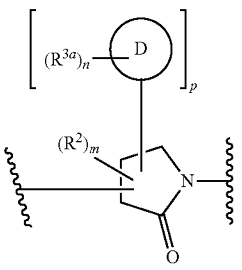
,
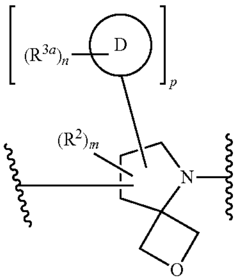
,
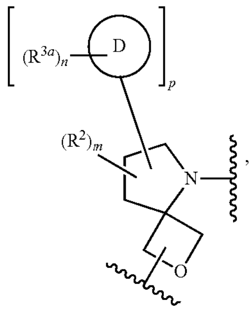
,
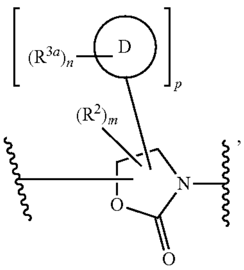
, -continued
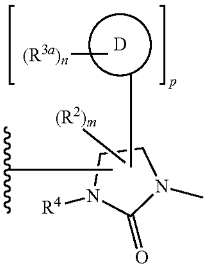,
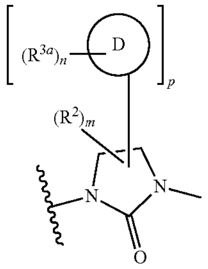,
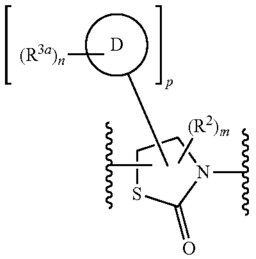,
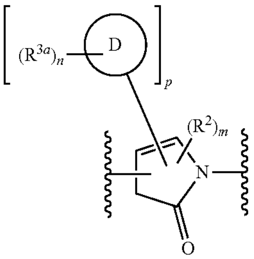,
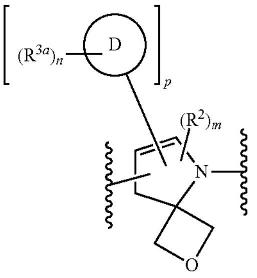,
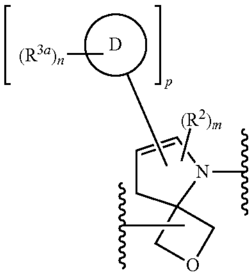,
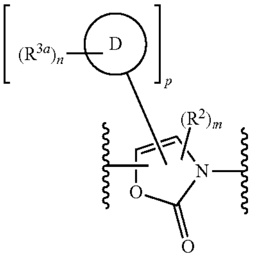,
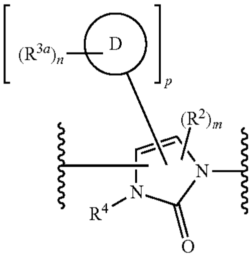,
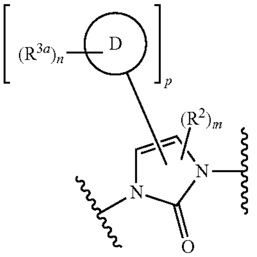,
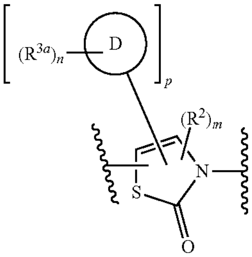,
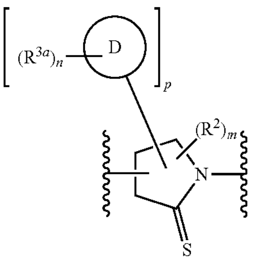,
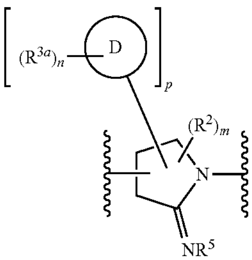,
-continued
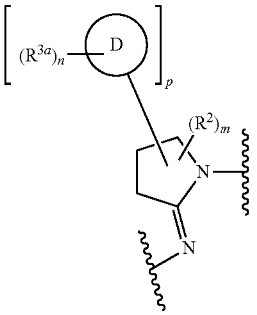,
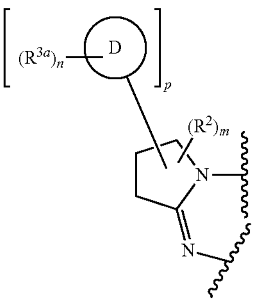,
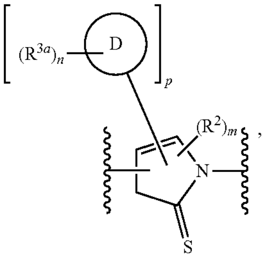,
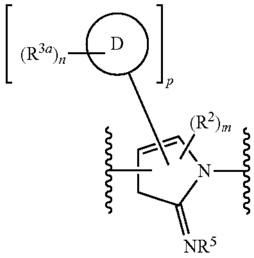,
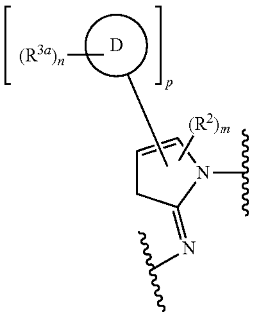,
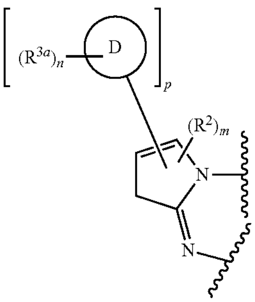,
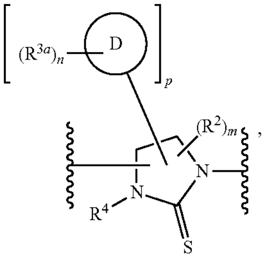,
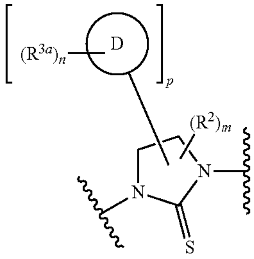,
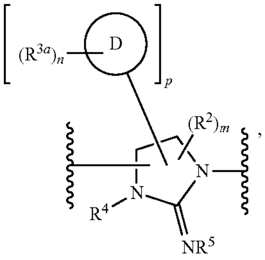,
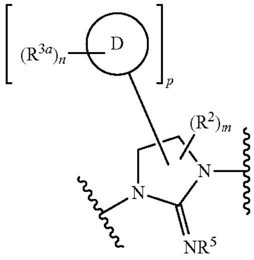,
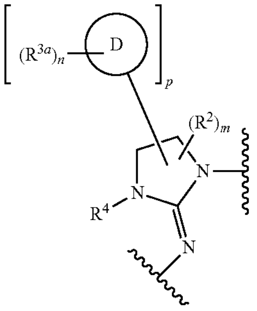,
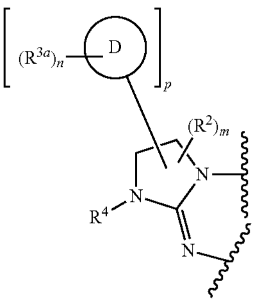, -continued

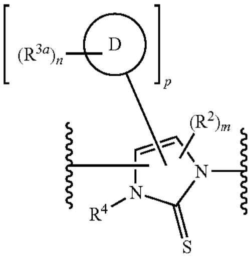
,
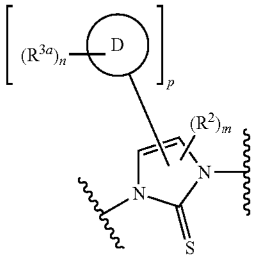
,
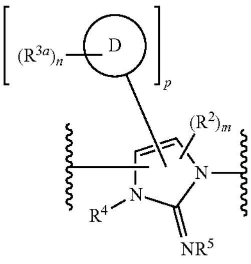
,
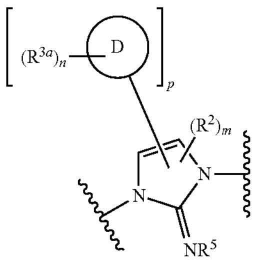
,
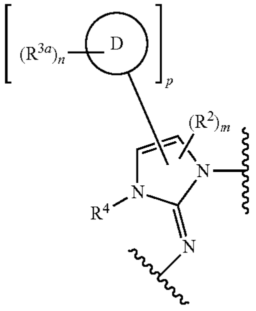
,
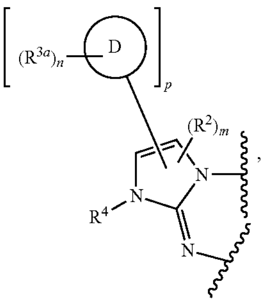
,
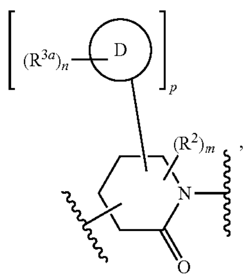
,
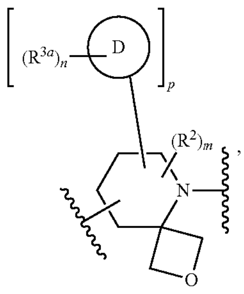
,
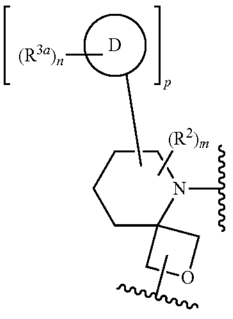
,
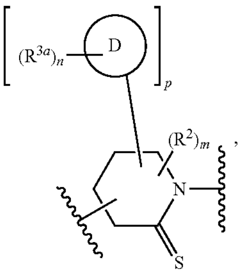
, -continued

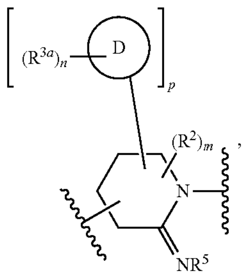
,
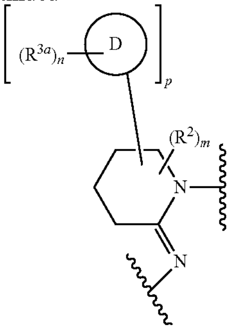
or
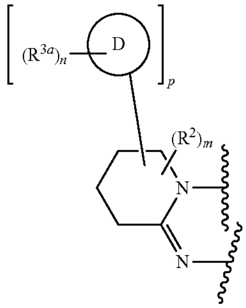
.

In some embodiments, Ring C is selected from those depicted in Table 1 below.

As defined above and described herein, Ring D is a ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring D is a 6-membered aryl. In some embodiments, Ring D is a 6-membered heteroaryl containing 1-4 heteroatoms independently selected from nitrogen, oxygen, or sulfur. In some embodiments, Ring D is a 5 to 7-membered saturated or partially unsaturated carbocyclyl. In some embodiments, Ring D is 5 to 7-membered saturated or partially saturated heterocyclyl with 1-3 heteroatoms independently selected from boron, nitrogen, oxygen, silicon, or sulfur. In some embodiments, Ring D is 5-membered heteroaryl with 1-4 heteroatoms independently selected from boron, nitrogen, oxygen, silicon, or sulfur.

In some embodiments, Ring D is selected from those depicted in Table 1 below.

As defined above and described herein, each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups.

In some embodiments, each of Ring E, Ring F, and Ring G is independently a fused ring selected from 6-membered aryl. In some embodiments, each of Ring E, Ring F, and Ring G is independently a fused ring selected from 6-membered heteroaryl containing 1-4 heteroatoms independently selected from nitrogen, oxygen, or sulfur. In some embodiments, each of Ring E, Ring F, and Ring G is independently a fused ring selected from a 5 to 7-membered saturated or partially unsaturated carbocyclyl. In some embodiments, each of Ring E, Ring F, and Ring G is independently a fused ring selected from a 5 to 7-membered saturated or partially unsaturated heterocyclyl with 1-3 heteroatoms independently selected from boron, nitrogen, oxygen, silicon, or sulfur. In some embodiments, each of Ring E, Ring F, and Ring G is independently a fused ring selected from a 5-membered heteroaryl with 1-4 heteroatoms independently selected from nitrogen, oxygen or sulfur. In some embodiments, Ring E, Ring F, and Ring G is independently and optionally substituted with 1-2 oxo groups.

In some embodiments, Ring F is

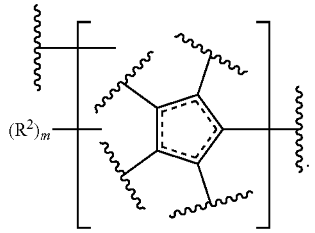

In some embodiments, Ring F is

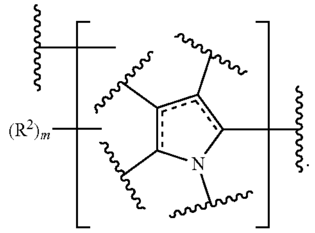

In some embodiments, Ring F is

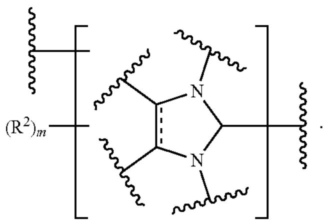

In some embodiments, Ring F is

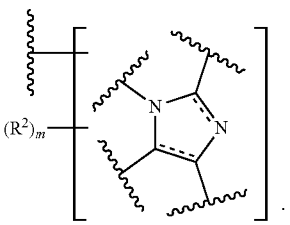

In some embodiments, Ring F is

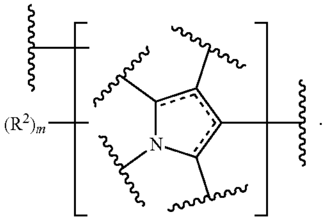

In some embodiments, Ring F is

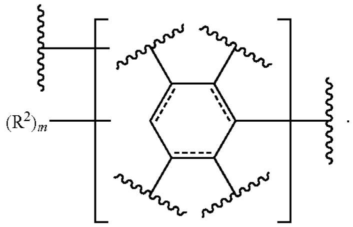

In some embodiments, Ring F is

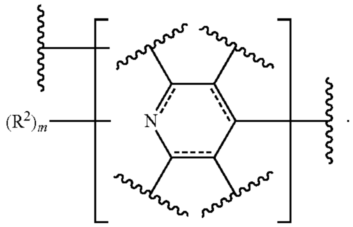

In some embodiments, Ring F is

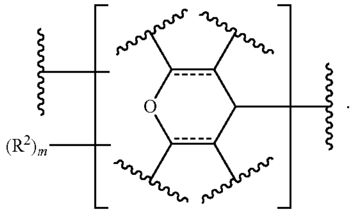

In some embodiments, Ring F

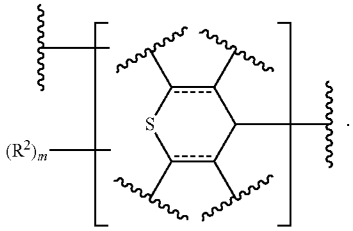

In some embodiments, Ring F is
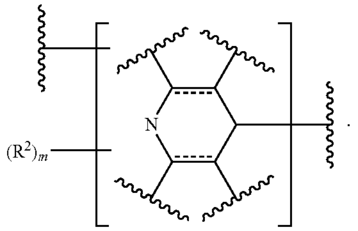
In some embodiments, Ring F is
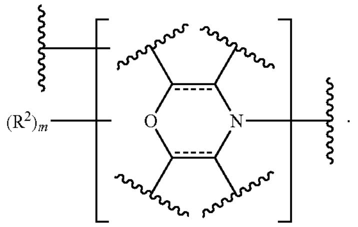
In some embodiments, Ring F is
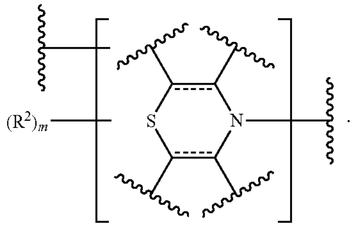
In some embodiments, Ring F is
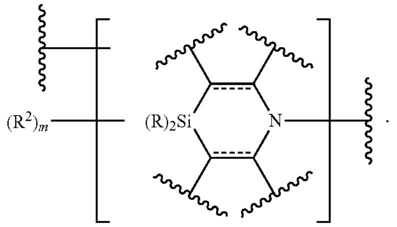
In some embodiments, Ring F is
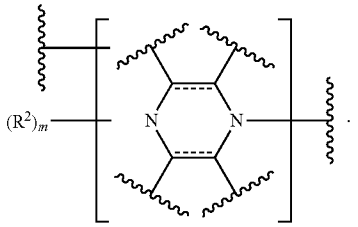
In some embodiments, Ring F is
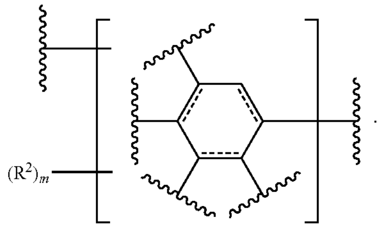
In some embodiments, Ring F is
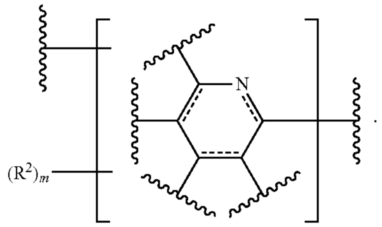
In some embodiments, Ring F is
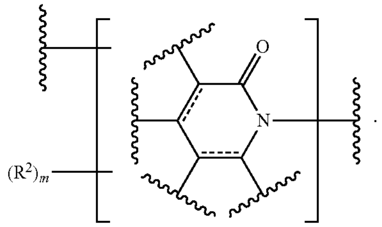
In some embodiments, Ring F is
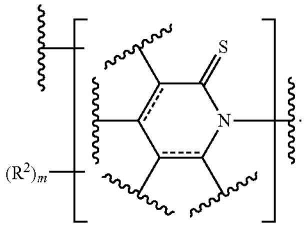
In some embodiments, Ring F is
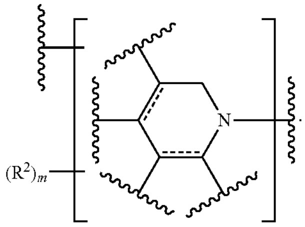

In some embodiments, Ring F is
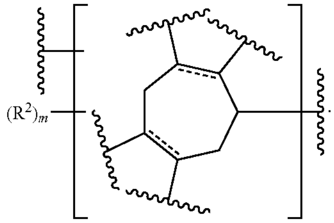
In some embodiments, Ring F is
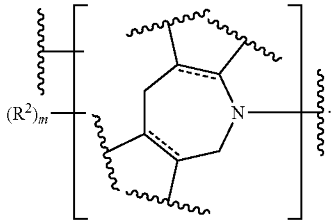
In some embodiments, Ring F is
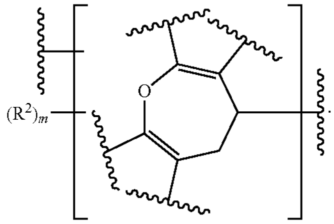
In some embodiments, Ring F is
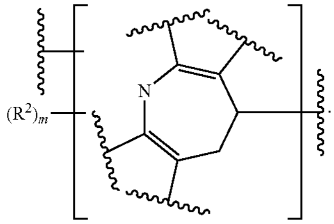
In some embodiments, Ring F is
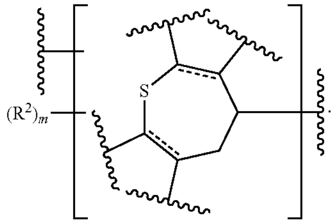
In some embodiments, Ring F is
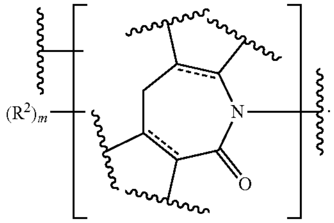
In some embodiments, Ring F is
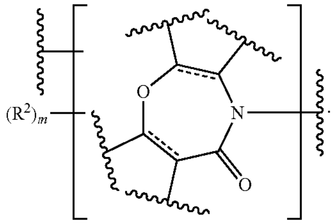
In some embodiments, Ring F is
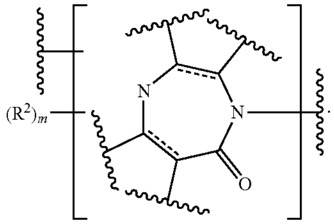
In some embodiments, Ring F is
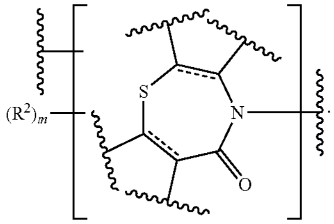
In some embodiments, Ring F is
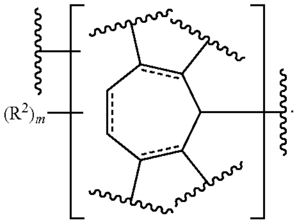

In some embodiments, Ring F is

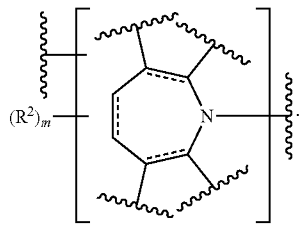

In some embodiments, Ring F is

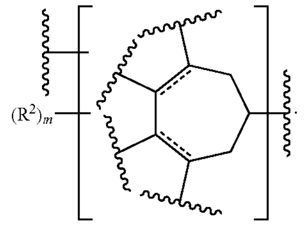

In some embodiments, Ring F is

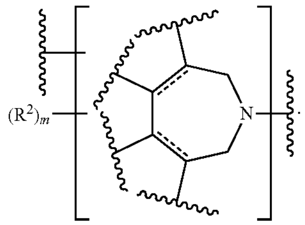

In some embodiments, Ring F is

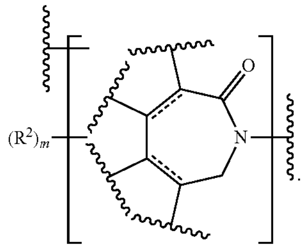

In some embodiments, Ring F is

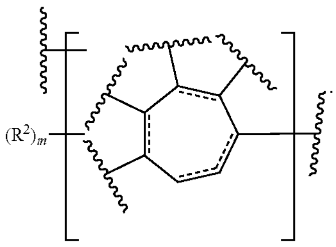

In some embodiments, Ring F is

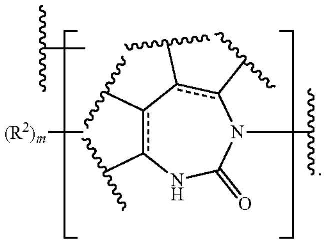

In some embodiments, Ring F is

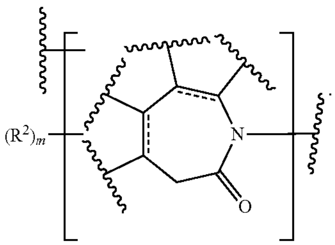

In some embodiments, each of Ring E and Ring G is independently

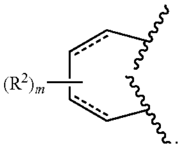

In some embodiments, each of Ring E and Ring G is independently

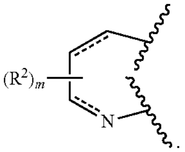

In some embodiments, each of Ring E and Ring G is independently

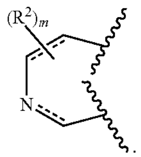

In some embodiments, each of Ring E and Ring G is independently

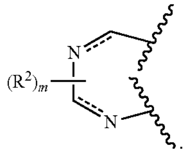

In some embodiments, each of Ring E and Ring G is independently

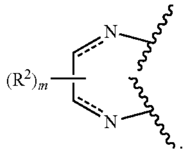

In some embodiments, each of Ring E and Ring G is independently is

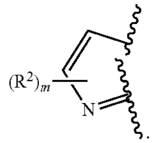

In some embodiments, each of Ring E and Ring G is independently

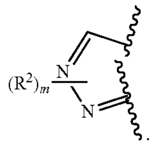

In some embodiments, each of Ring E and Ring G is independently

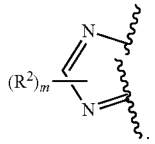

In some embodiments, each of Ring E and Ring G is independently

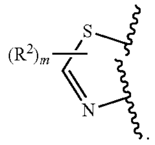

In some embodiments, each of Ring E and Ring G is independently

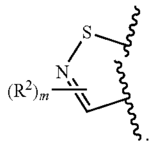

In some embodiments, each of Ring E and Ring G is independently

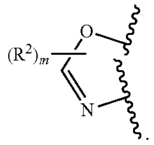

In some embodiments, each of Ring E and Ring G is independently

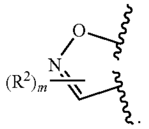

some embodiments, each of Ring E and Ring G is independently

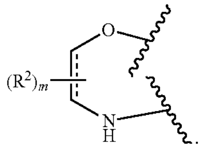

In some embodiments, each of Ring E and Ring G is independently

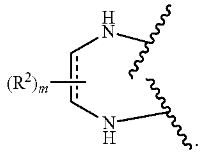

In some embodiments, each of Ring E and Ring G is independently

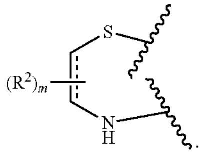

In some embodiments, each of Ring E and Ring G is independently

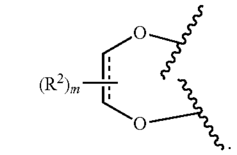

In some embodiments, each of Ring E and Ring G is independently

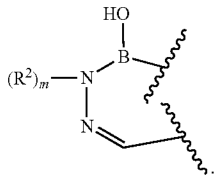

In some embodiments, Ring E, Ring F, and Ring G is

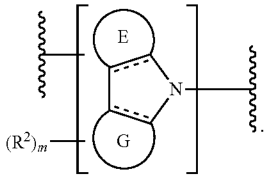

In some embodiments, Ring E, Ring F, and Ring G is

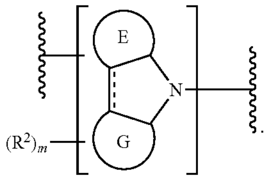

In some embodiment, Ring E, Ring F, and Ring G is

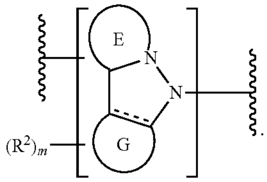

In some embodiments, Ring E, Ring F, and Ring G is

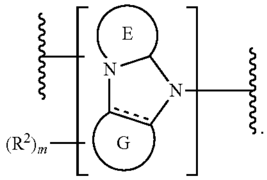

In some embodiments, Ring E, Ring F, and Ring G is

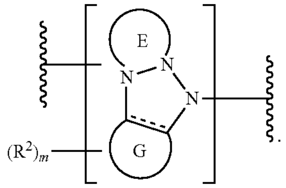

In some embodiments, Ring E, Ring F, and Ring G is

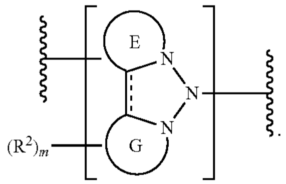

In some embodiments, Ring E, Ring F, and Ring G is

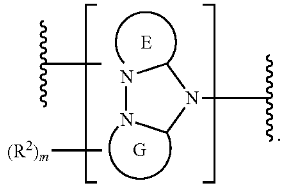

In some embodiments, Ring E, Ring F, and Ring G is

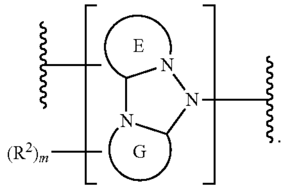

In some embodiments, Ring E, Ring F, and Ring G is

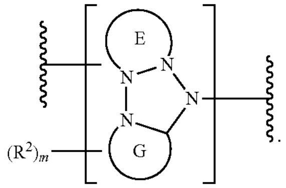

In some embodiments, Ring E, Ring F, and Ring G is

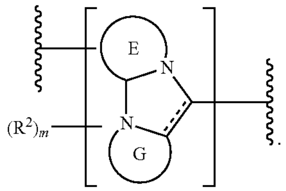

In some embodiments, Ring E, Ring F, and Ring G is

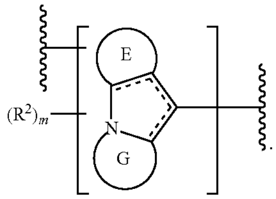

In some embodiments, Ring E, Ring F, and Ring G is

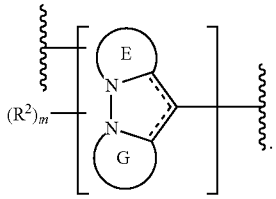

In some embodiments, Ring E, Ring F, and Ring G is

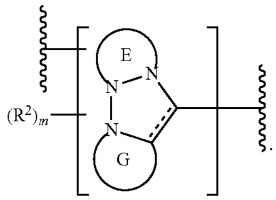

In some embodiments, Ring E, Ring F, and Ring G is

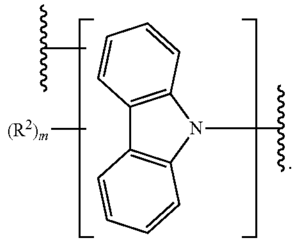

In some embodiments, Ring E, Ring F, and Ring G is

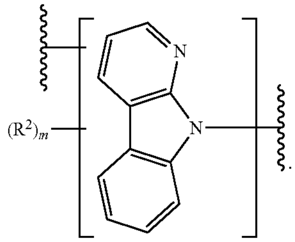

In some embodiments, Ring E, Ring F, and Ring G is

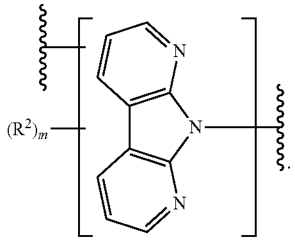

In some embodiments, Ring E, Ring F, and Ring G is

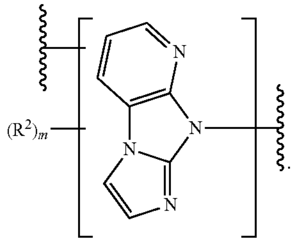

In some embodiments, Ring E, Ring F, and Ring G is

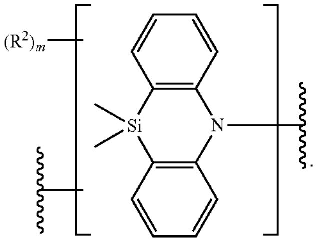

In some embodiments, Ring E, Ring F, and Ring G is

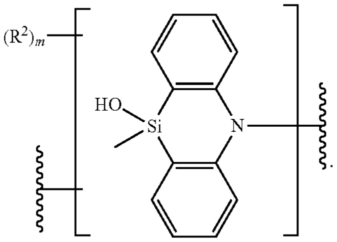

In some embodiments, Ring E, Ring F, and Ring G is

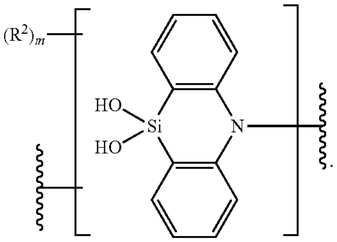

In some embodiments, Ring E, Ring F, and Ring G is

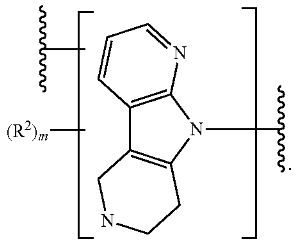

In some embodiments, Ring E, Ring F, and Ring G is

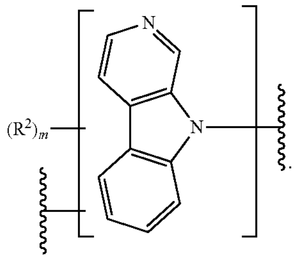

In some embodiments, Ring E, Ring F, and Ring G is

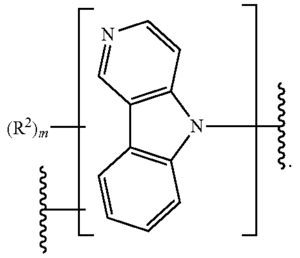

In some embodiments, Ring E, Ring F, and Ring G is

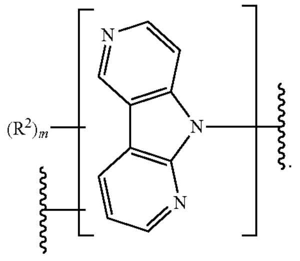

In some embodiments, Ring E, Ring F, and Ring G is

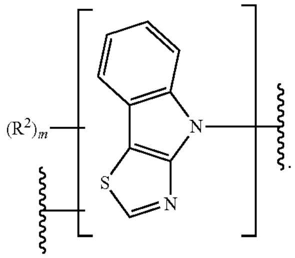

In some embodiments, Ring E, Ring F, and Ring G is

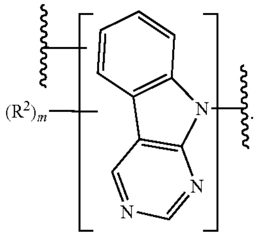

In some embodiments, Ring E, Ring F, and Ring G is

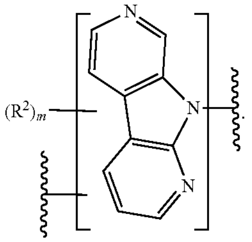

In some embodiments, Ring E, Ring F, and Ring G is

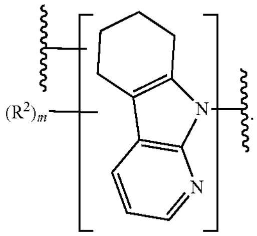

In some embodiments, Ring E, Ring F, and Ring G is

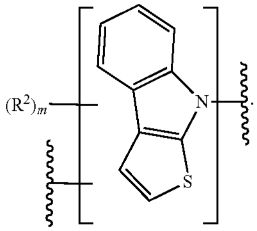

In some embodiments, Ring E, Ring F, and Ring G is

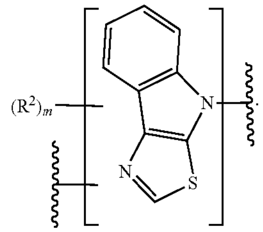

In some embodiments, Ring E, Ring F, and Ring G is

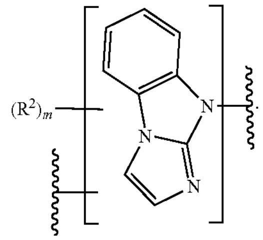

In some embodiments, Ring E, Ring F, and Ring G is

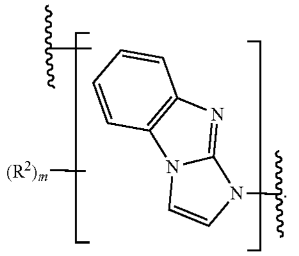

In some embodiments, Ring E, Ring F, and Ring G is

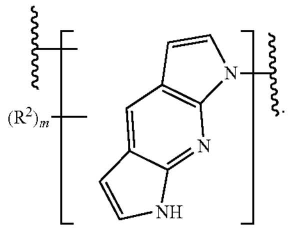

In some embodiments, Ring E, Ring F, and Ring G is

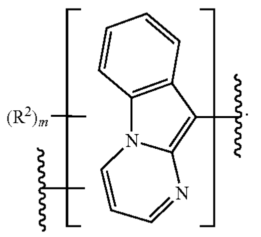

In some embodiments, Ring E, Ring F, and Ring G is

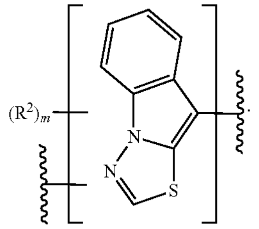

In some embodiments, Ring E, Ring F, and Ring G is selected from those depicted in Table 1, below.

As defined above and described herein, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

In some embodiments, Ring H is

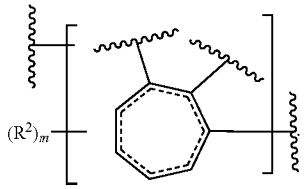

In some embodiments, Ring H is

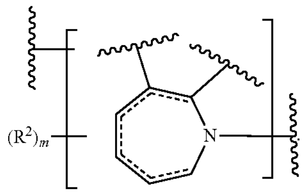

In some embodiments, Ring H is

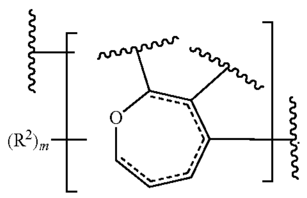

In some embodiments, Ring H is
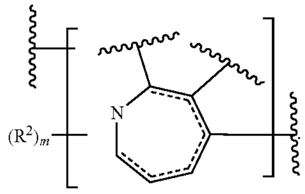
In some embodiments, Ring H is
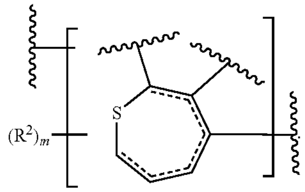
In some embodiments, Ring H is
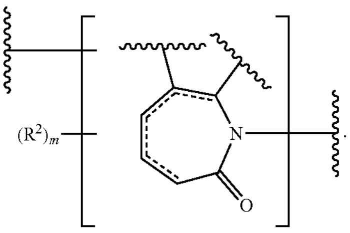
In some embodiments, Ring H is
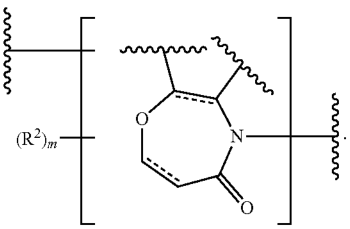
In some embodiments, Ring H is
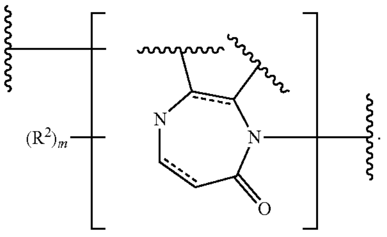
In some embodiments, Ring H is
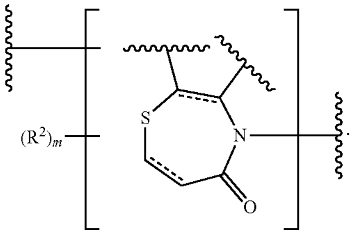
some embodiments Ring H is
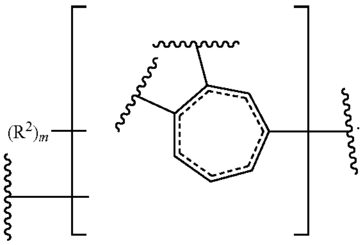
In some embodiments, Ring H is
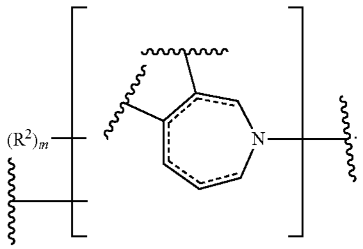
In some embodiments, Ring H is
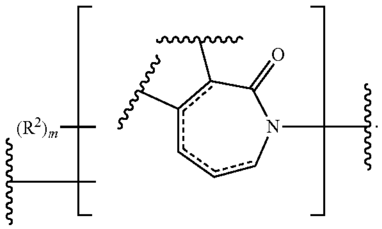
In some embodiments, Ring H is
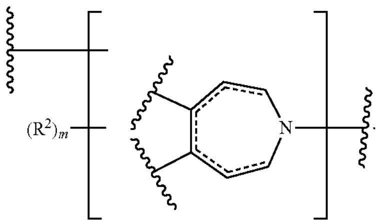

In some embodiments, Ring H is

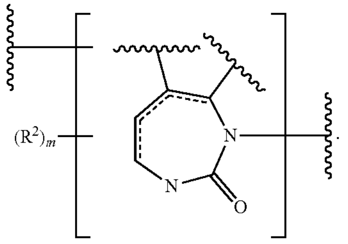

In some embodiments, Ring H is

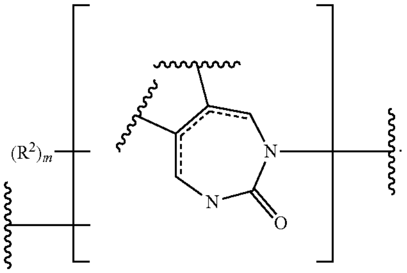

In some embodiments, Ring H is

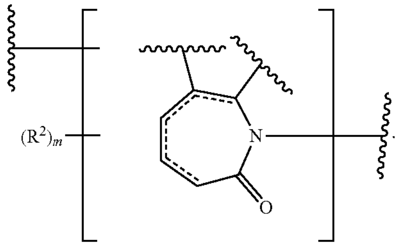

In some embodiments, Ring H is

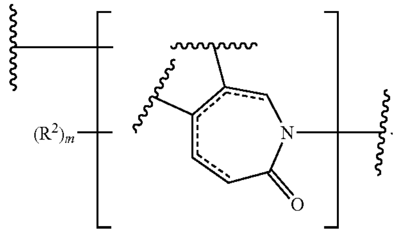

In some embodiments, Ring H is

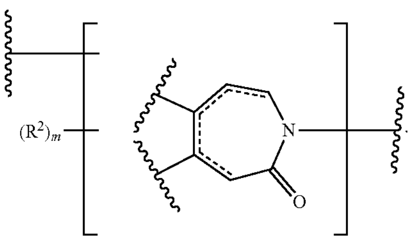

In some embodiments Ring H is

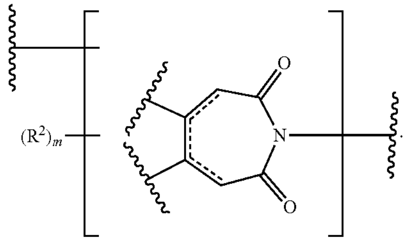

In some embodiments, Ring H is

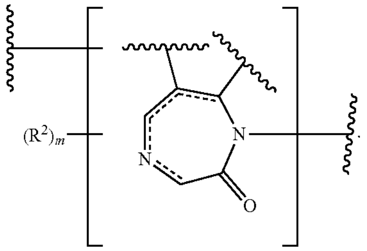

In some embodiments, Ring H is

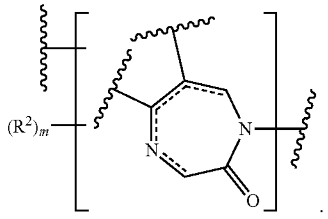

In some embodiments, Ring H is selected from those depicted in Table 1, below.

In some embodiments, Ring E and Ring H is

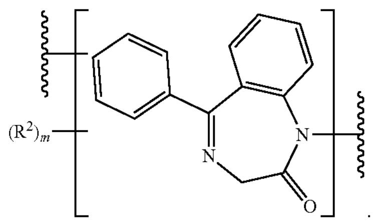

As defined above and described herein, each of Ring I and Ring J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring I and Ring J is independently a 6-membered aryl. In some embodiments, each of Ring I and Ring J is independently a 6-membered heteroaryl containing 1-4 heteroatoms independently selected from nitrogen, oxygen, or sulfur. In some embodiments, each of Ring I and Ring J is independently a 5 to 7-membered saturated or partially unsaturated carbocyclyl. In some embodiments, each of Ring I and Ring J is independently a 5 to 7-membered saturated or partially unsaturated heterocyclyl with 1-3 heteroatoms independently selected from boron, nitrogen, oxygen, silicon, or sulfur. In some embodiments, each of Ring I and Ring J is independently a 5-membered heteroaryl with 1-3 heteroatoms independently selected from nitrogen, oxygen or sulfur.

In some embodiments, each of Ring I and Ring J is independently

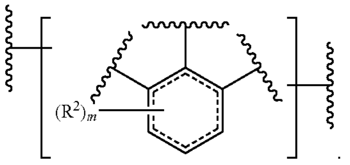

In some embodiments, each of Ring I and Ring J is independently

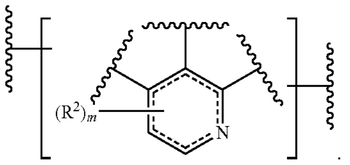

In some embodiments, each of Ring I and Ring J is independently

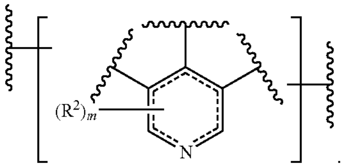

In some embodiments, each of Ring I and Ring J is independently

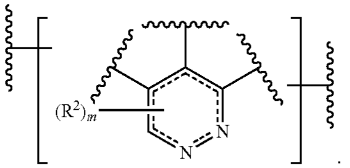

In some embodiments, each of Ring I and Ring J is independently

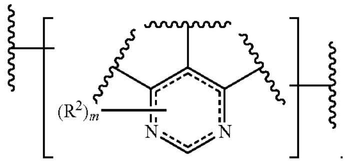

In some embodiments, Ring I and Ring J is independently is

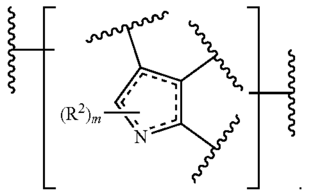

In some embodiments, Ring I and Ring J is independently

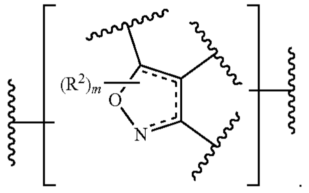

In some embodiments, Ring I and Ring J is independently

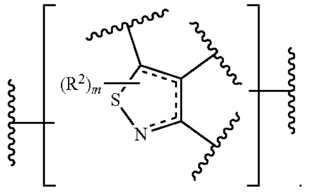

In some embodiments, Ring I and Ring J is selected from those depicted in Table 1, below.

As defined above and described herein, Ring K is a fused ring selected from a 7-12 membered saturated or partially unsaturated carbocyclyl or heterocyclyl with 1-3 heteroatoms independently selected from boron, nitrogen, oxygen, silicon, or sulfur, wherein Ring H is optionally further substituted with 1-2 oxo groups.

In some embodiments, Ring K is a fused ring selected from a 7-12 membered saturated or partially unsaturated carbocyclyl. In some embodiments, Ring K is a 7-12 membered saturated or partially unsaturated heterocyclyl ring with 1-3 heteroatoms independently selected from boron, nitrogen, oxygen, silicon, or sulfur. In some embodiments, Ring K is optionally further substituted with 1-2 oxo groups.

In some embodiments, Ring K is
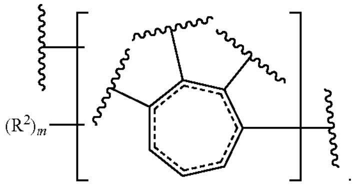
In some embodiments, Ring K is
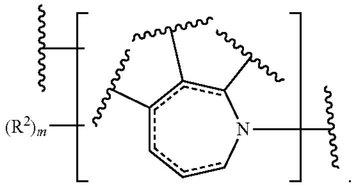
In some embodiments, Ring K is
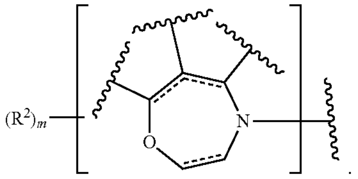
In some embodiments, Ring K is
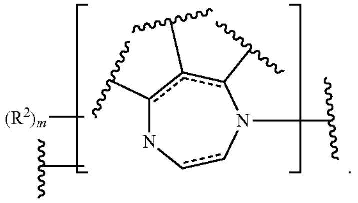
In some embodiments, Ring K is
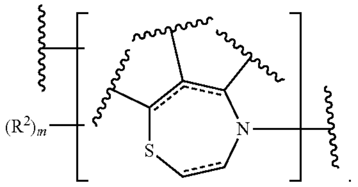
In some embodiments, Ring K is
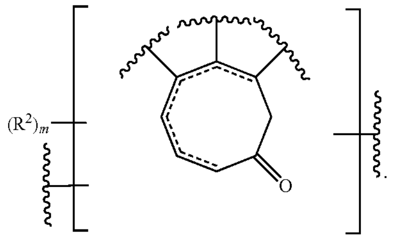
In some embodiments Ring K is
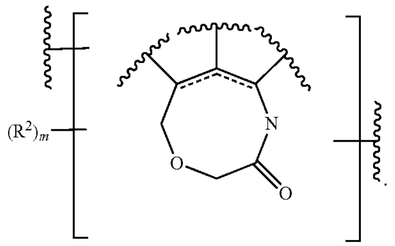
In some embodiments, Ring K is
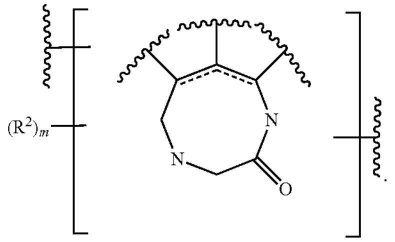
In some embodiments, Ring K is
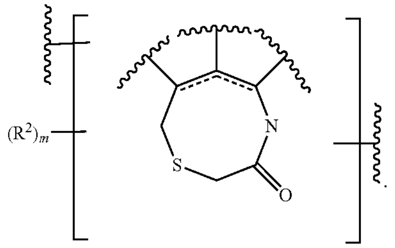
some embodiments, Ring K is
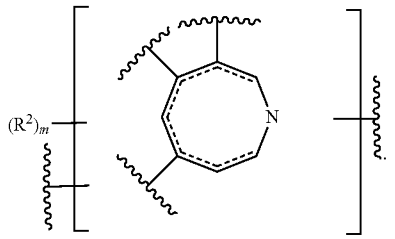

In some embodiments, Ring K is
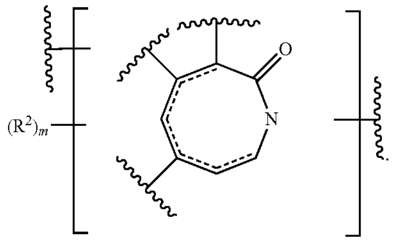
In some embodiments, Ring K is
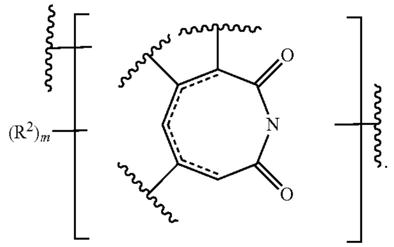
In some embodiments, Ring K is
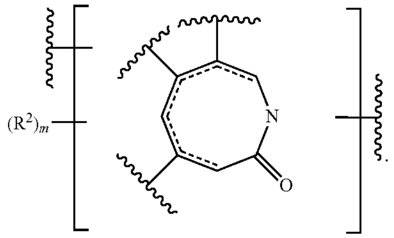
In some embodiments, Ring K is
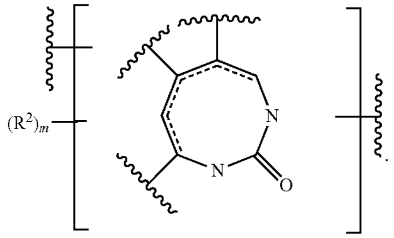
In some embodiments, Ring K is
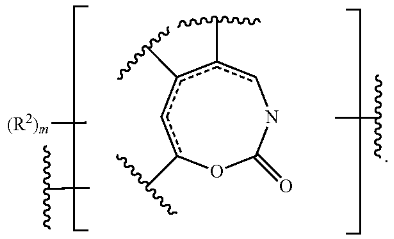
In some embodiments, Ring K is selected from those depicted in Table 1 below.
In some embodiments, Ring I, Ring J, and Ring K is
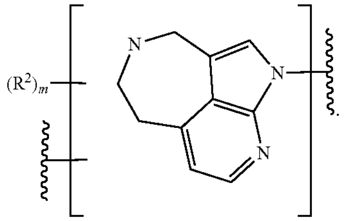
As defined above and described herein, Ring M is selected from
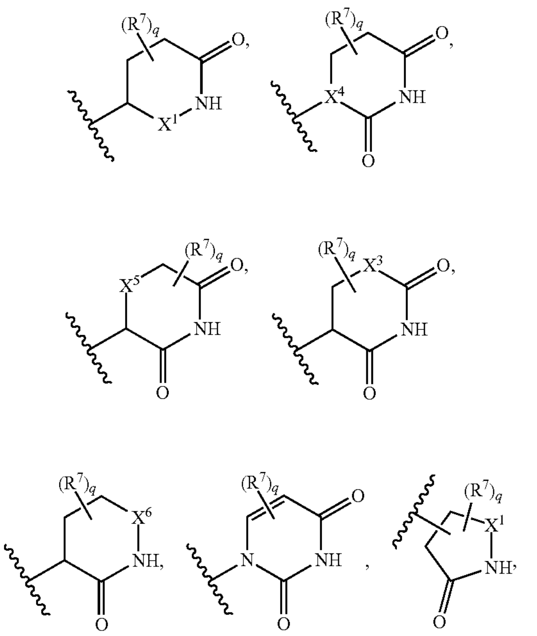
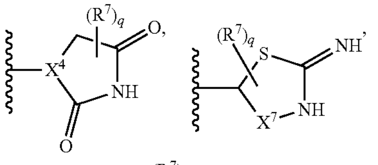
or
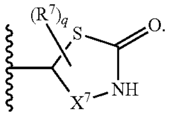
In some embodiments, Ring M is
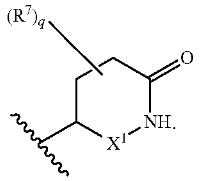

In some embodiments, Ring M is

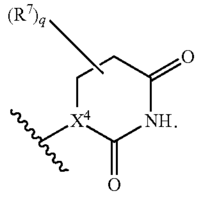

In some embodiments, Ring M is

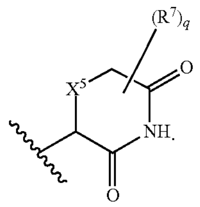

In some embodiments, Ring M is

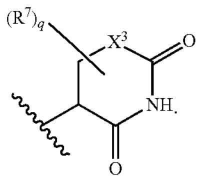

In some embodiments, Ring M is

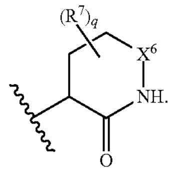

In some embodiments, Ring M is

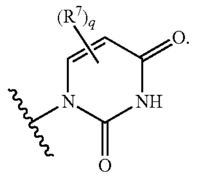

In some embodiments, Ring M is

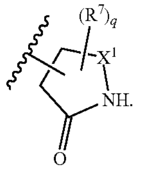

In some embodiments, Ring M is

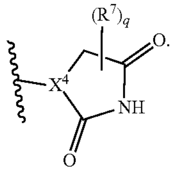

In some embodiments, Ring M is

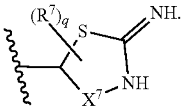

In some embodiments, Ring M is

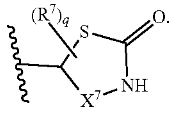

In some embodiments, Ring M is selected from those depicted in Table 1 below.

As defined above and described here, $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

In some embodiments, $L^1$ is a covalent bond. In some embodiments, $L^1$ is a $C_{1-3}$ aliphatic. In some embodiments, $L^1$ is —$CH_2$—. In some embodiments, $L^1$ is —C(D)(H)—. In some embodiments, $L^1$ is —$C(D)_2$-. In some embodiments, $L^1$ is —$CH_2CH_2$—. In some embodiments, $L^1$ is —NR—. In some embodiments, $L^1$ is —$CH_2NR$—. In some embodiments, $L^1$ is or —O—. In some embodiments, $L^1$ is —$CH_2O$—. In some embodiments, $L^1$ is —S—. In some embodiments, $L^1$ is —OC(O)—. In some embodiments, $L^1$ is —C(O)O—. In some embodiments, $L^1$ is —C(O)—. In some embodiments, $L^1$ is —S(O)—. In some embodiments, $L^1$ is —$S(O)_2$—. In some embodiments, $L^1$ is —$NRS(O)_2$—. In some embodiments, $L^1$ is —$S(O)_2NR$—. In some embodiments, $L^1$ is —NRC(O)—. In some embodiments, $L^1$ is —C(O)NR—.

In some embodiments, Ring $L^1$ is selected from those depicted in Table 1 below.

As defined above and described herein, ┅┅ is a single or double bond.

In some embodiments, ┅┅ is a single bond. In some embodiments, ┅┅ is a double bond.

In some embodiments, ┅┅ is selected from those depicted in Table 1 below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1 below.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In some embodiments, n is selected from those depicted in Table 1 below.

As defined above and described herein, p is 0 or 1.

In some embodiments, p is 0. In some embodiments, p is 1.

In some embodiments, p is selected from those depicted in Table 1 below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1 below.

In some embodiments, LBM is

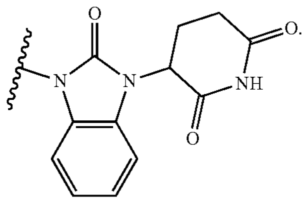 [SMILES: *n1c(=O)n(C2CCC(=O)NC2=O)c2ccccc21]

In some embodiments, LBM is

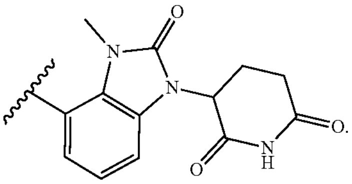 [SMILES: *c1cccc2c1n(C)c(=O)n2C1CCC(=O)NC1=O]

In some embodiments, LBM is

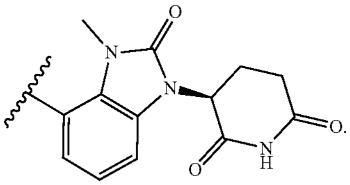 [SMILES: *c1cccc2c1n(C)c(=O)n2[C@H]1CCC(=O)NC1=O]

In some embodiments, LBM is

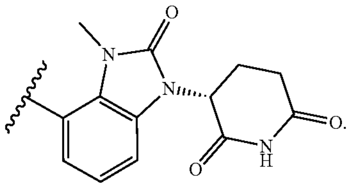 [SMILES: *c1cccc2c1n(C)c(=O)n2[C@@H]1CCC(=O)NC1=O]

In some embodiments, LBM is

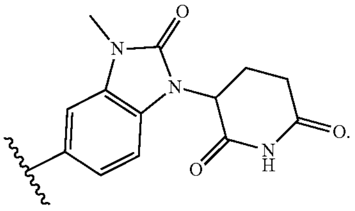 [SMILES: *c1ccc2c(c1)n(C)c(=O)n2C1CCC(=O)NC1=O]

In some embodiments, LBM is

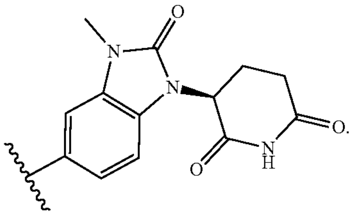 [SMILES: *c1ccc2c(c1)n(C)c(=O)n2[C@H]1CCC(=O)NC1=O]

In some embodiments, LBM is

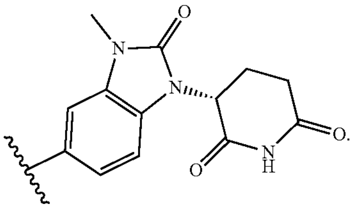 [SMILES: *c1ccc2c(c1)n(C)c(=O)n2[C@@H]1CCC(=O)NC1=O]

In some embodiments, LBM is

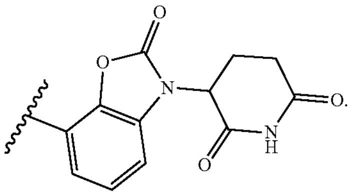 [SMILES: *c1cccc2c1oc(=O)n2C1CCC(=O)NC1=O]

In some embodiments, LBM is
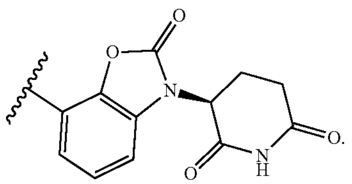 [SMILES: *c1cccc2c1oc(=O)n2[C@H]1CCC(=O)NC1=O]
In some embodiments, LBM is
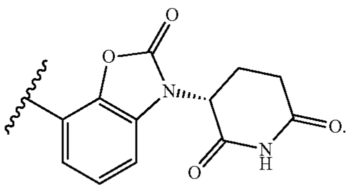 [SMILES: *c1cccc2c1oc(=O)n2[C@@H]1CCC(=O)NC1=O]
In some embodiments, LBM is
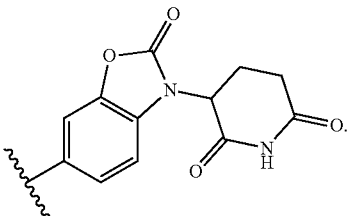 [SMILES: *c1ccc2c(c1)oc(=O)n2C1CCC(=O)NC1=O]
In some embodiments, LBM is
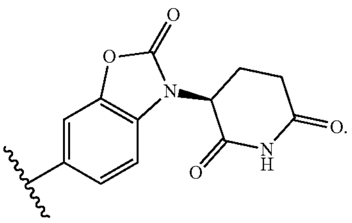 [SMILES: *c1ccc2c(c1)oc(=O)n2[C@H]1CCC(=O)NC1=O]
In some embodiments, LBM is
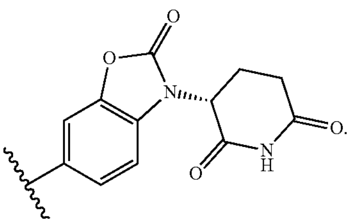 [SMILES: *c1ccc2c(c1)oc(=O)n2[C@@H]1CCC(=O)NC1=O]
In some embodiments, LBM is
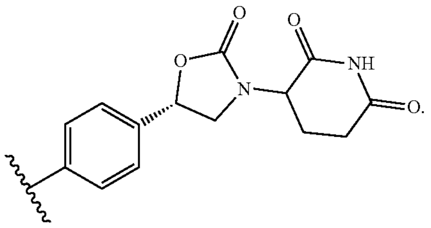 [SMILES: *c1ccc([C@H]2CN(C3CCC(=O)NC3=O)C(=O)O2)cc1]
In some embodiments, LBM is
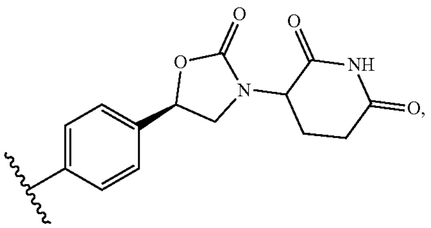
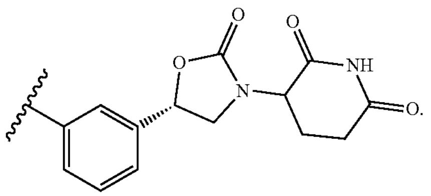
In some embodiments, LBM is
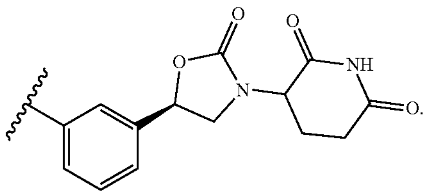 [SMILES: *c1cccc([C@@H]2CN(C3CCC(=O)NC3=O)C(=O)O2)c1]
In some embodiments, LBM is
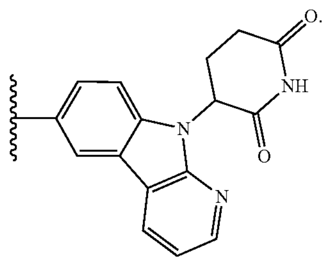 [SMILES: *c1ccc2c(c1)c1cccnc1n2C1CCC(=O)NC1=O]

In some embodiments, LBM is
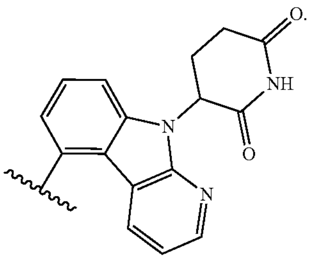 [SMILES: *c1cccc2c1c1cccnc1n2C1CCC(=O)NC1=O]
In some embodiments, LBM is
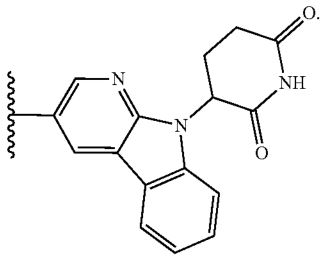 [SMILES: *c1cnc2c(c1)c1ccccc1n2C1CCC(=O)NC1=O]
In some embodiments, LBM is
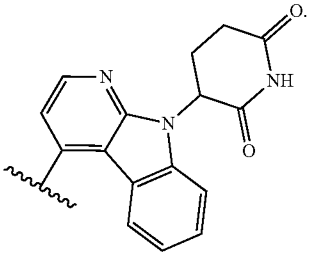 [SMILES: *c1ccnc2c1c1ccccc1n2C1CCC(=O)NC1=O]
In some embodiments, LBM is
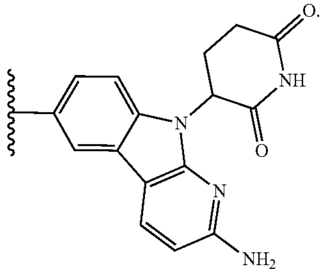 [SMILES: *c1ccc2c(c1)c1ccc(N)nc1n2C1CCC(=O)NC1=O]
In some embodiments, LBM is
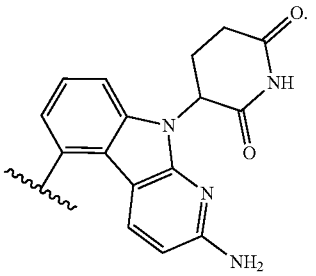 [SMILES: *c1cccc2c1c1ccc(N)nc1n2C1CCC(=O)NC1=O]
In some embodiments, LBM is
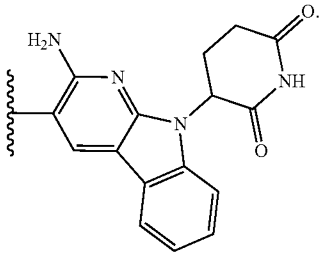 [SMILES: *c1cc2c3ccccc3n(C3CCC(=O)NC3=O)c2nc1N]
In some embodiments, LBM is
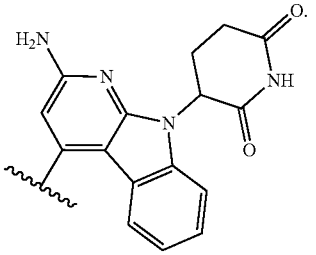 [SMILES: *c1cc(N)nc2c1c1ccccc1n2C1CCC(=O)NC1=O]
In some embodiments, LBM is
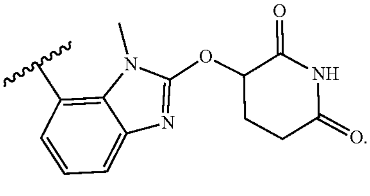 [SMILES: *c1cccc2nc(OC3CCC(=O)NC3=O)n(C)c12]
In some embodiments, LBM is
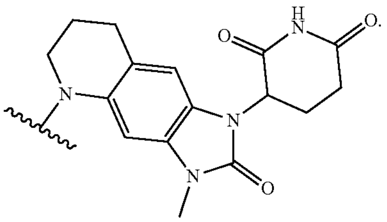 [SMILES: *N1CCCc2cc3c(cc21)n(C)c(=O)n3C1CCC(=O)NC1=O]

In some embodiments, LBM is selected from those in Table 1 below.

In some embodiments, the present invention provides the compound of formula I-a or I'-a, wherein LBM is

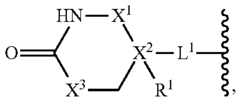

Ring Q is benzo, a single $R^x$ is —OR, and X is cyclohexyl as shown, to provide a compound of formula I-e-4:

I-e-4

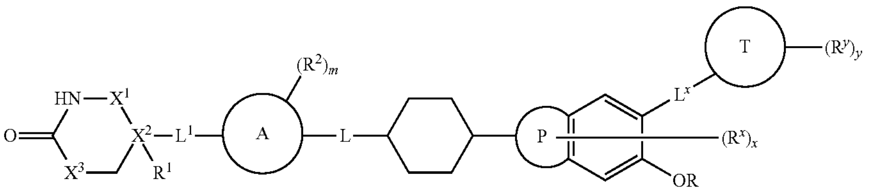

or a pharmaceutically acceptable salt thereof, wherein each of $X^1$, $X^2$, $X^3$, $R^1$, $R^2$, $L^1$, Ring A, and m of the LBM, L, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a or I'-a, wherein LBM is

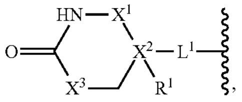

Ring Q and Ring P form an indazole ring, a single $R^x$ is —OR, and X is cyclohexyl as shown, to provide a compound of formula I-e-5:

I-e-5

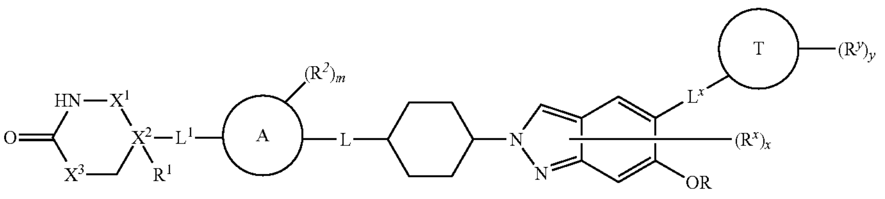

or a pharmaceutically acceptable salt thereof, wherein each of $X^1$, $X^2$, $X^3$, $R^1$, $R^2$, $L^1$, Ring A, and m of the LBM, L, and $L^x$, Ring T, R, $R^x$, $R^y$, x, and y of the IRAK moiety is as defined above and described in embodiments herein, both singly and in combination.

In some embodiments, the present invention provides the compound of formula I-a or I'-a, wherein LBM is

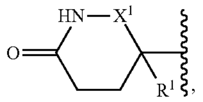

Ring Q is benzo, a single $R^x$ is —OR, and X is cyclohexyl as shown, to provide a compound of formula I-e-6:

I-e-6

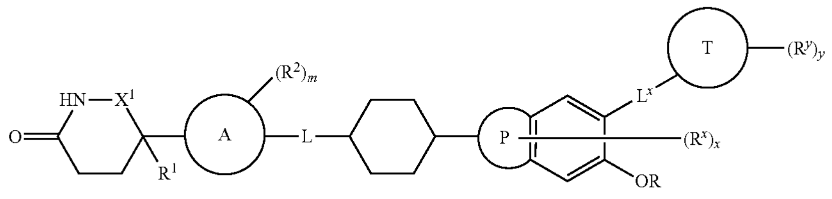

or a pharmaceutically acceptable salt thereof, wherein each of $X^1$, $R^1$, $R^2$, Ring A, and m of the LBM, L, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a or I'-a, wherein LBM is

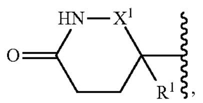

Ring Q and Ring P form an indazole ring, a single $R^x$ is —OR, and X is cyclohexyl as shown, to provide a compound of formula I-e-7:

I-e-7

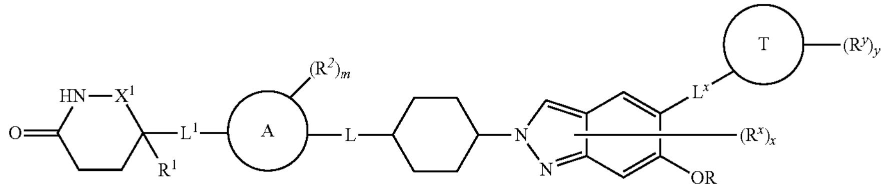

or a pharmaceutically acceptable salt thereof, wherein each of $X^1$, $R^1$, $R^2$, Ring A, and m of the LBM, L, and $L^x$, Ring T, R, $R^x$, $R^y$, x, and y of the IRAK moiety is as defined above and described in embodiments herein, both singly and in combination.

In some embodiments, the present invention provides the compound of formula I-a or I'-a, wherein LBM is

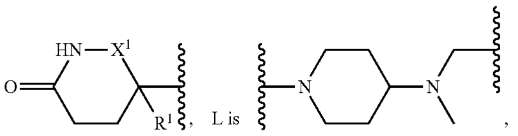

Ring Q is benzo, a single $R^x$ is —OR, and X is cyclohexyl as shown, to provide a compound of formula as a compound of formula I-e-8:

I-e-8

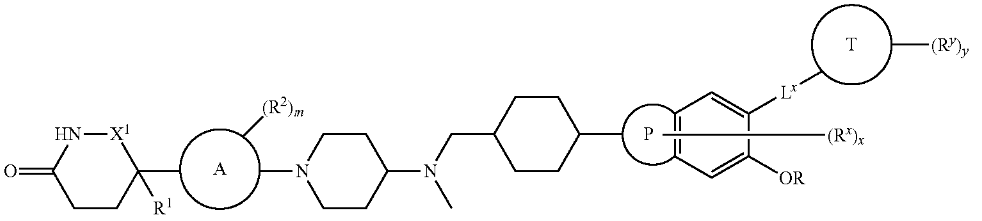

or a pharmaceutically acceptable salt thereof, wherein each of $X^1$, $R^1$, $R^2$, Ring A, and m of the LBM, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a or I'-a, wherein LBM is

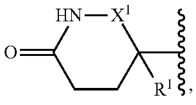, L is 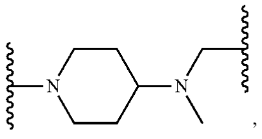,

Ring Q and Ring P form an indazole ring, a single $R^x$ is —OR, and X is cyclohexyl as shown, to provide a compound of formula as a compound of formula I-e-9:

Ring Q is benzo, a single $R^x$ is —OR, and X is cyclohexyl as shown, to provide a compound of formula as a compound of formula I-e-10:

I-e-10

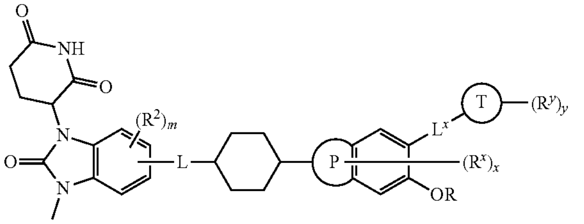

or a pharmaceutically acceptable salt thereof, wherein each of $R^2$ and m of the LBM, L, and $L^x$, Ring P, Ring T, R, $R^x$, I-e-9

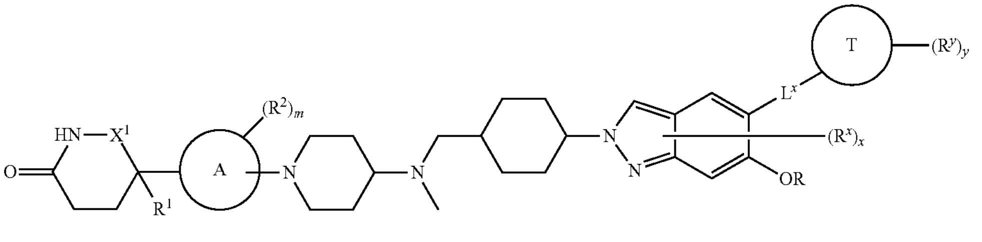

or a pharmaceutically acceptable salt thereof, wherein each of $X^1$, $R^1$, $R^2$, Ring A, and m of the LBM, and $L^x$, Ring T, R, $R^x$, $R^y$, x, and y of the IRAK moiety is as defined above and described in embodiments herein, both singly and in combination.

In some embodiments, the present invention provides the compound of formula I-a or I'-a, wherein LBM is

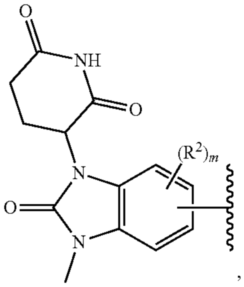, $R^y$, x, and y of the IRAK moiety is as defined above and described in embodiments herein, both singly and in combination.

In some embodiments, the present invention provides the compound of formula I-a or I'-a, wherein LBM is

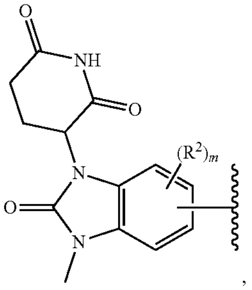,

Ring Q and Ring P form an indazole ring, a single $R^x$ is —OR, and X is cyclohexyl as shown, to provide a compound of formula as a compound of formula I-e-11:

I-e-11

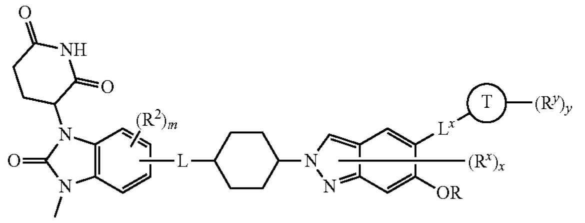

or a pharmaceutically acceptable salt thereof, wherein each of $R^2$ and m of the LBM, L, and $L^x$, Ring T, R, $R^x$, $R^y$, x, and y of the IRAK moiety is as defined above and described in embodiments herein, both singly and in combination.

In some embodiments, LBM is an E3 ligase ligand well known to one of ordinary skill in the art including those described in M. Toure, C. M. Crews, *Angew. Chem. Int. Ed.* 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, US 2019/0076540, WO 2017/197046, US 2019/0076542, WO 2017/197051, US 2019/0076539, WO 2017/197055, US 2019/0076541, and WO 2017/197056, the entirety of each of which is herein incorporated by reference.

In certain embodiments, the present invention provides a compound of Formula I, wherein LBM is an E3 ubiquitin ligase (cereblon) binding moiety thereby forming a compound of formula I-oo-1, I-oo-2, I-oo-3, I-oo-4, I-oo-5, I-oo-6, I-oo-7, I-oo-8, I-oo-9, or I-oo-10 respectively:

I-oo-1

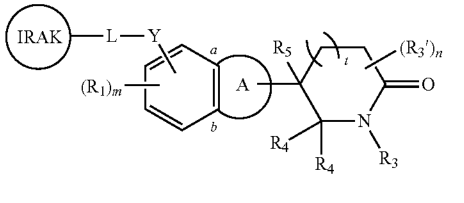

I-oo-2

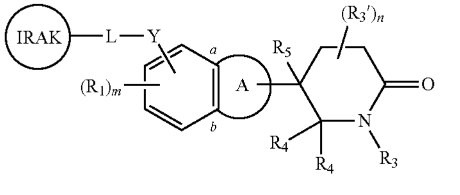

-continued

I-oo-3

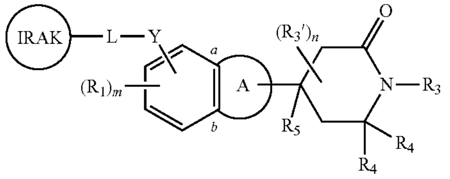

I-oo-4

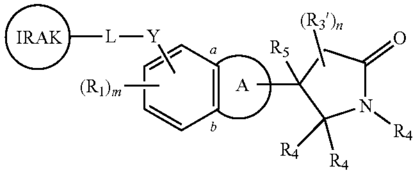

I-oo-5

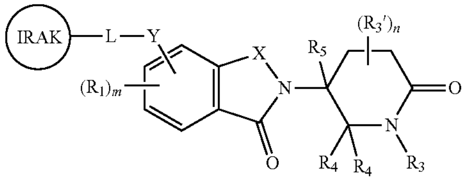

I-oo-6

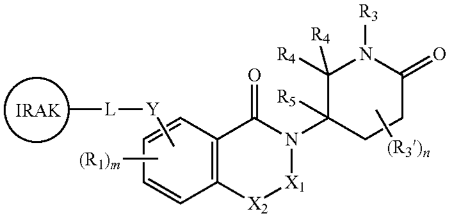

I-oo-7

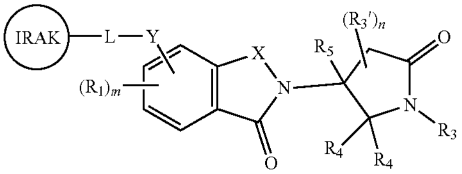

I-oo-8

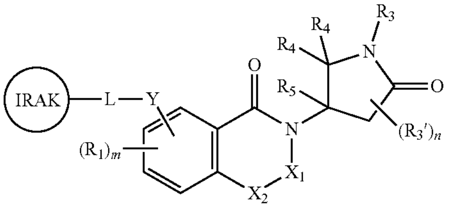

I-oo-9

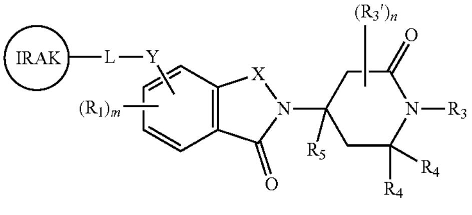

-continued
I-oo-10
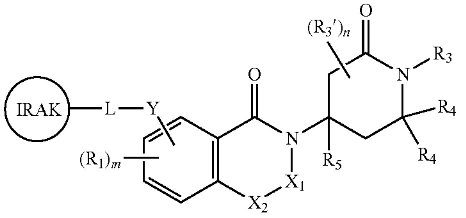
or a compound of formula I-oo'-1, I-oo'-2, I-oo'-3, I-oo'-4, I-oo'-5, I-oo'-6, I-oo'-7, I-oo'-8, I-00'-9, or I-oo'-10 respectively:
I-oo'-1
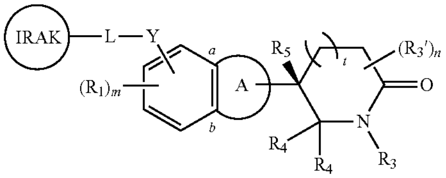
I-oo'-2
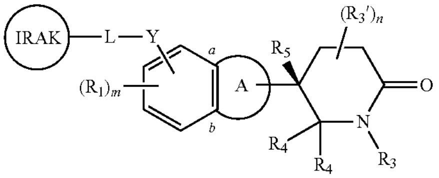
I-oo'-3
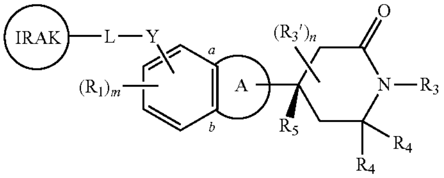
I-oo'-4
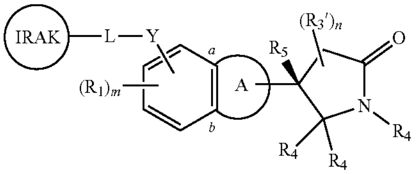
I-oo'-5
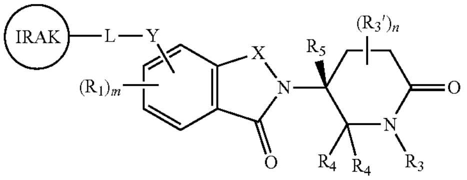
I-oo'-6
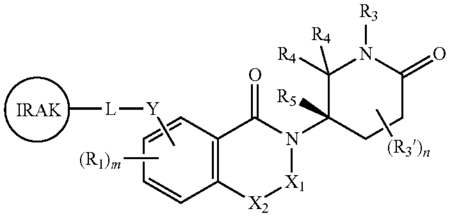
-continued
I-oo'-7
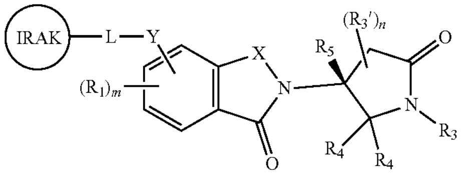
I-oo'-8
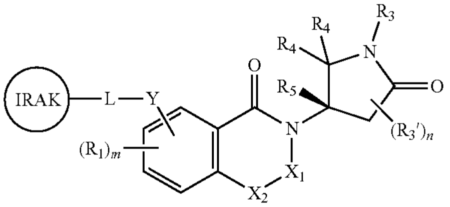
I-oo'-9
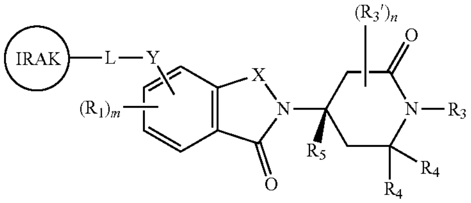
I-oo'-10
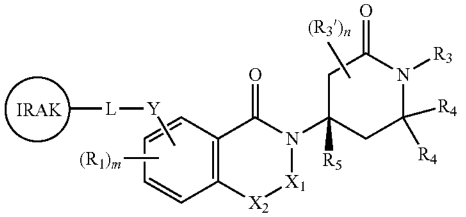
or a compound of formula I-oo"-1, I-oo"-2, I-oo"-3, I-oo"-4, I-oo"-5, I-oo"-6, I-oo"-7, I-oo"-8, I-oo"-9, or I-oo"-10 respectively:
I-oo"-1
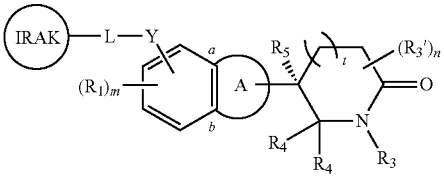
I-oo"-2
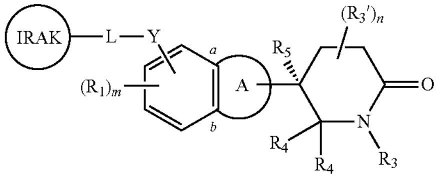
I-oo"-3
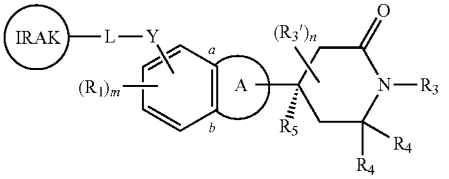

-continued

I-oo"-4

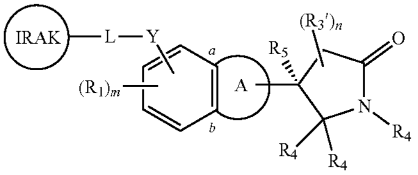

I-oo"-5

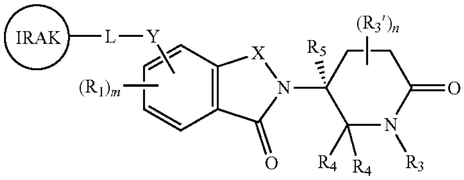

I-oo"-6

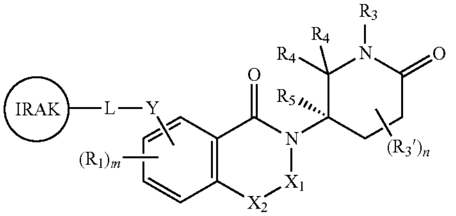

I-oo"-7

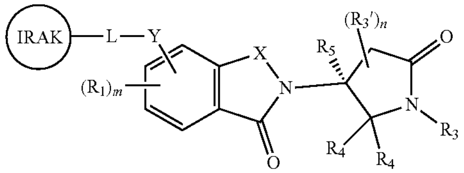

I-oo"-8

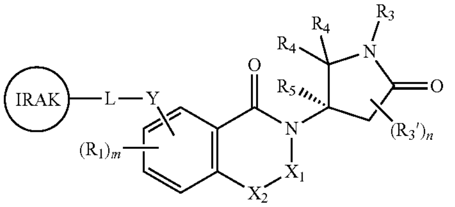

I-oo"-9

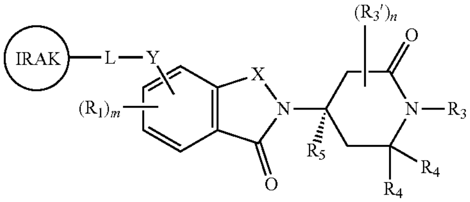

I-oo"-10

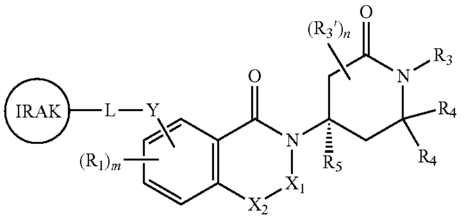

or a pharmaceutically acceptable salt thereof, wherein L and IRAK are as defined above and described in embodiments herein, and wherein each of the variables

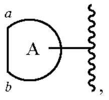

X, $X_1$, $X_2$, Y, $R_1$, $R_3$, $R_3'$, $R_4$, $R_5$, t, m and n is as defined and described in WO 2017/007612 and US 2018/0134684, the entirety of each of which is herein incorporated by reference.

In certain embodiments, the present invention provides a compound of Formula I, wherein LBM is an E3 ubiquitin ligase (cereblon) binding moiety thereby forming a compound of formula I-pp-1, I-pp-2, I-pp-3, I-pp-4, I-pp-5, or I-pp-6 respectively:

I-pp-1

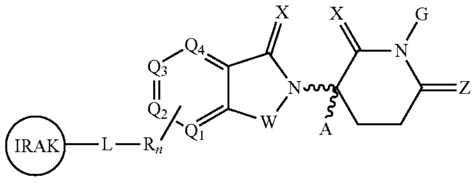

I-pp-2

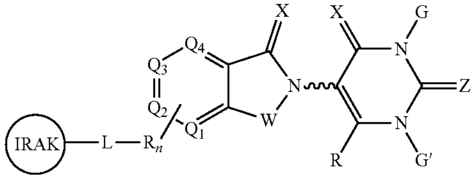

I-pp-3

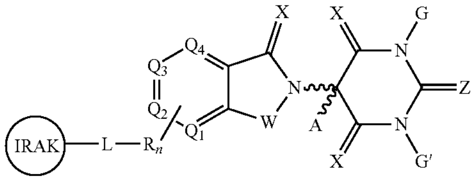

I-pp-4

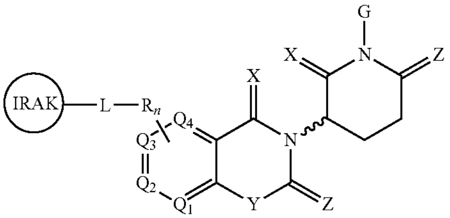

I-pp-5

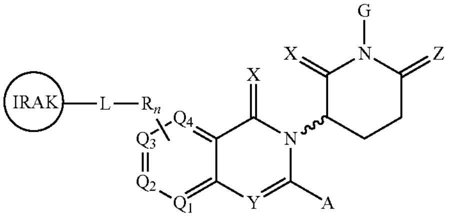

I-pp-6

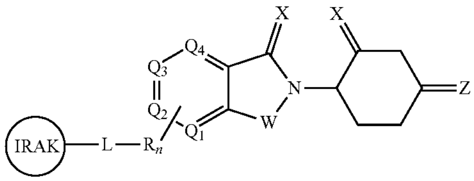

or a pharmaceutically acceptable salt thereof, wherein L and IRAK are as defined above and described in embodiments herein, and wherein each of the variables A, G, G', $Q_1$, $Q_2$, $Q_3$, $Q_4$, R, R', W, X, Y, Z, ∿∿∿, and n is as defined and described in WO 2016/197114 and US 2018/0147202, the entirety of each of which is herein incorporated by reference.

In some embodiments, LBM is

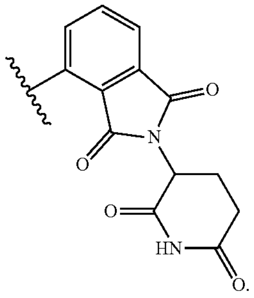 [SMILES: *c1cccc2c1C(=O)N(C1CCC(=O)NC1=O)C2=O]

In some embodiments, LBM is

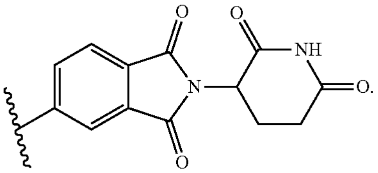 [SMILES: *c1ccc2c(c1)C(=O)N(C1CCC(=O)NC1=O)C2=O]

In some embodiments, LBM is

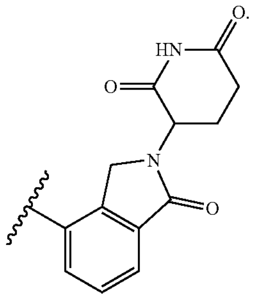 [SMILES: *c1cccc2c1CN(C1CCC(=O)NC1=O)C2=O]

In some embodiments, LBM is

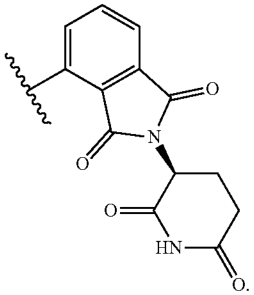 [SMILES: *c1cccc2c1C(=O)N([C@H]1CCC(=O)NC1=O)C2=O]

In some embodiments, LBM is

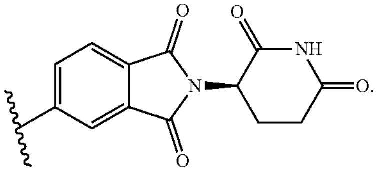 [SMILES: *c1ccc2c(c1)C(=O)N([C@@H]1CCC(=O)NC1=O)C2=O]

In some embodiments, LBM is

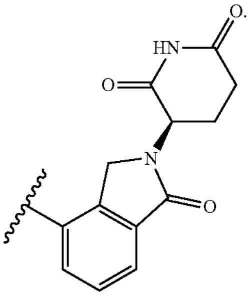 [SMILES: *c1cccc2c1CN([C@@H]1CCC(=O)NC1=O)C2=O]

In some embodiments, LBM is

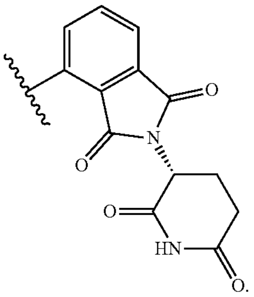 [SMILES: *c1cccc2c1C(=O)N([C@@H]1CCC(=O)NC1=O)C2=O]

In some embodiments, LBM is

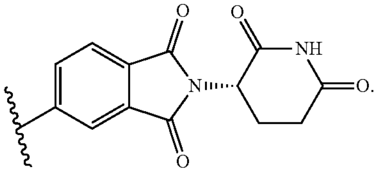 [SMILES: *c1ccc2c(c1)C(=O)N([C@H]1CCC(=O)NC1=O)C2=O]

In some embodiments, LBM is

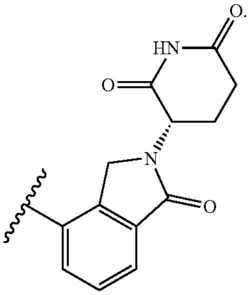

In some embodiments, LBM is selected from those in Table 1 below.

In some embodiments, the present invention provides a compound of formula I-a or I'-a, wherein LBM is thalidomide and $L^x$ is an amide as shown, to provide a compound of formula I-i-1:

I-i-1

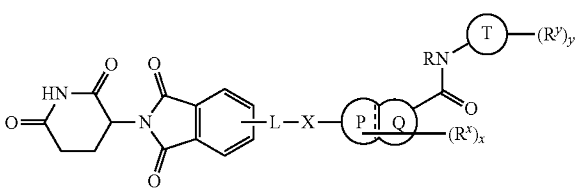

or a pharmaceutically acceptable salt thereof, wherein each of L, X, R, $R^x$, $R^y$, Ring P, Ring Q, Ring T, ----, x, and y is as defined above and described in embodiments herein, both singly and in combination.

In some embodiments, the present invention provides a compound of formula I-a or I'-a, wherein LBM is thalidomide and L is a thioamide as shown, to provide a compound of formula I-i-2:

I-i-2

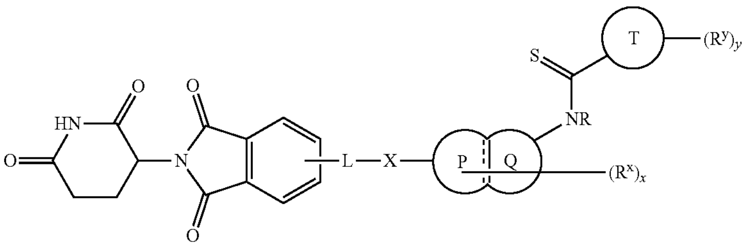

or a pharmaceutically acceptable salt thereof, wherein each of L, X, R, $R^x$, $R^y$, Ring P, Ring Q, Ring T, ----, x, and y is as defined above and described in embodiments herein, both singly and in combination.

In some embodiments, the present invention provides a compound of formula I-a or I'-a, wherein LBM is thalidomide and $L^x$ is a 1,2,4-triazole as shown, to provide a compound of formula I-i-3:

I-i-3

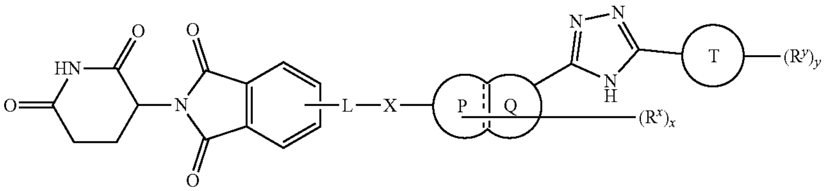

or a pharmaceutically acceptable salt thereof, wherein each of L, X, $R^x$, $R^y$, Ring P, Ring Q, Ring T, ----, x, and y is as defined above and described in embodiments herein, both singly and in combination.

In some embodiments, the present invention provides a compound of formula I-a or I'-a, wherein LBM is thalidomide and $L^x$ is a 1,3,4-oxadiazole as shown, to provide a compound of formula I-i-4:

I-i-4

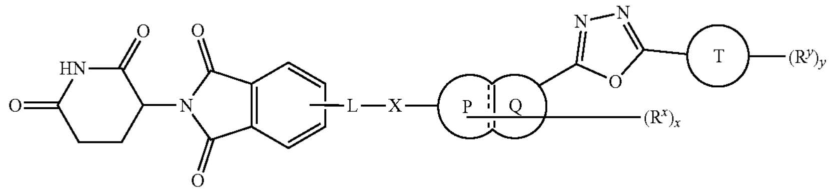

or a pharmaceutically acceptable salt thereof, wherein each of L, X, $R^x$, $R^y$, Ring P, Ring Q, Ring T, $\overline{\overline{----}}$, x, and y is as defined above and described in embodiments herein, both singly and in combination.

In some embodiments, the present invention provides a compound of formula I-a or I'-a, wherein LBM is thalidomide and $L^x$ is an oxazole as shown, to provide a compound of formula I-i-5:

I-i-5

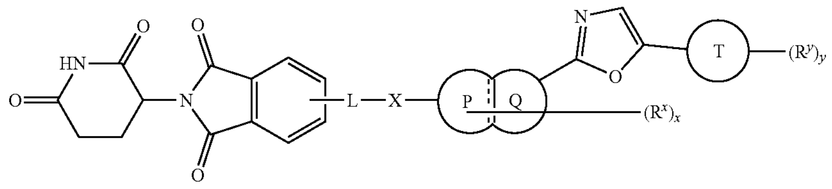

or a pharmaceutically acceptable salt thereof, wherein each of L, X, $R^x$, $R^y$, Ring P, Ring Q, Ring T, $\overline{\overline{----}}$, x, and y is as defined above and described in embodiments herein, both singly and in combination.

In some embodiments, the present invention provides a compound of formula I-a or I'-a, wherein LBM is thalidomide and $L^x$ is a thiazole as shown, to provide a compound of formula I-i-6:

I-i-6

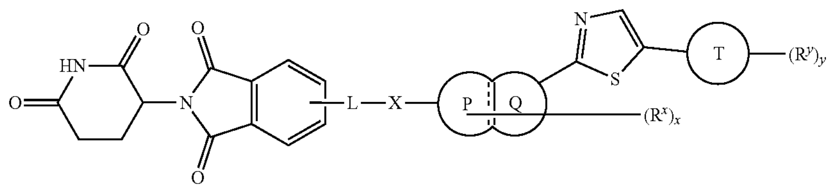

or a pharmaceutically acceptable salt thereof, wherein each of L, X, $R^x$, $R^y$, Ring P, Ring Q, Ring T, $\overline{\overline{----}}$, x, and y is as defined above and described in embodiments herein, both singly and in combination.

In some embodiments, the present invention provides a compound of formula I-a or I'-a, wherein LBM is thalidomide and $L^x$ is an imidazole as shown, to provide a compound of formula I-i-7:

I-i-7

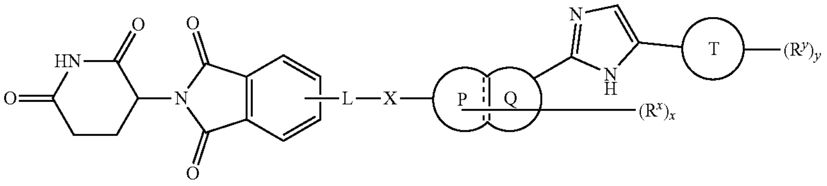

or a pharmaceutically acceptable salt thereof, wherein each of L, X, $R^x$, $R^y$, Ring P, Ring Q, Ring T, ----, x, and y is as defined above and described in embodiments herein, both singly and in combination.

In some embodiments, the present invention provides a compound of formula I-a or I'-a, wherein LBM is thalidomide and Ring P and Ring Q form a benzoxazole ring as shown, to provide a compound of formula I-j-1:

I-j-1

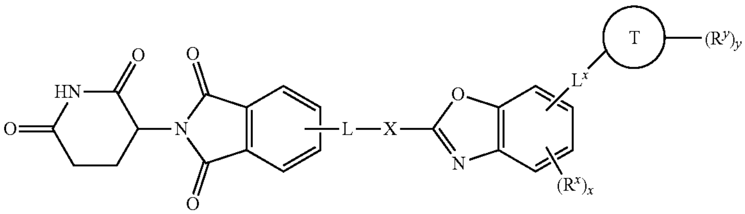

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide and Ring P and Ring Q form a benzothiazole ring as shown, to provide a compound of formula I-j-2:

I-j-2

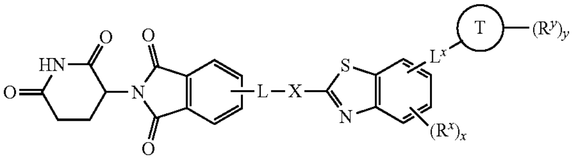

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide and Ring P and Ring Q form an indazole ring as shown, to provide a compound of formula I-j-3:

I-j-3

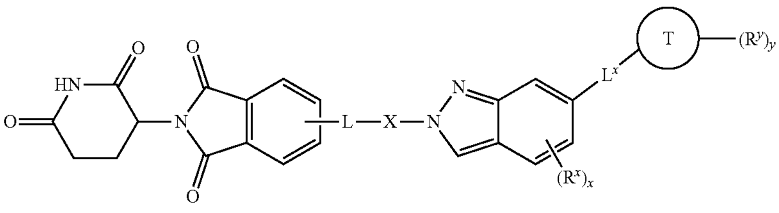

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide and Ring P and Ring Q form a pyrazolopyridine ring as shown, to provide a compound of formula I-j-4:

I-j-4

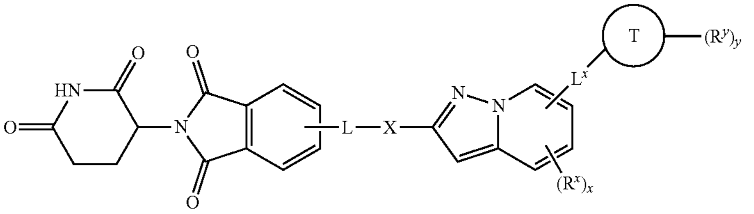

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide, Ring P and Ring Q form an indazole ring, and $R^x$ is

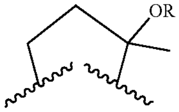

as shown, to provide a compound of formula I-k-1:

I-k-1

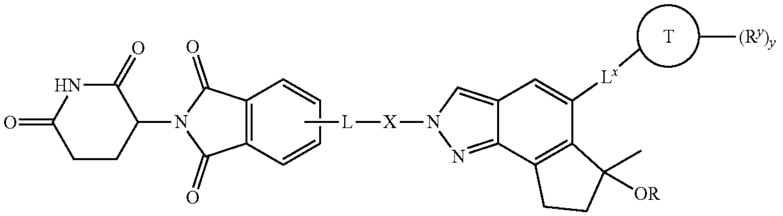

or a pharmaceutically acceptable salt thereof, wherein each of L, $L^x$, X, R, $R^y$, Ring T, and y is as defined above and described in embodiments herein, both singly and in combination.

In some embodiments, the present invention provides a compound of formula I-a or I'-a, wherein LBM is thalidomide or

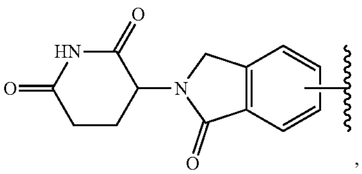

,

Ring Q is

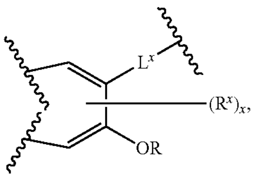

a single $R^x$ is —OR, and X is cyclohexyl as shown, to provide a compound of formula I-k-2 or I-k-3:

I-k-2

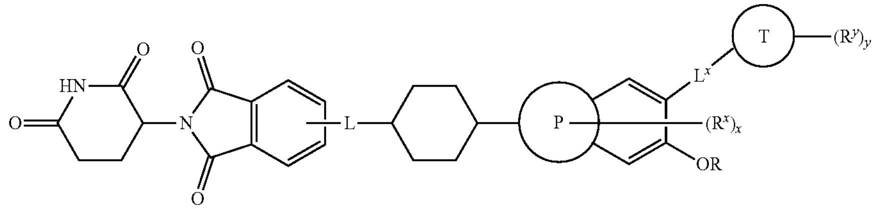

I-k-3

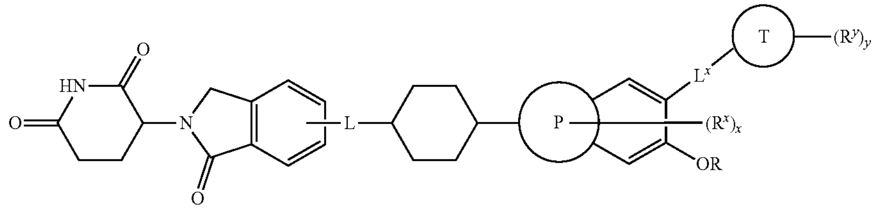

or a pharmaceutically acceptable salt thereof, wherein L is as defined and described herein, and wherein:

each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2$(OR), —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$N^{+6}$ ($O^-$)$R_2$, —OP(O)$R_2$, —OP(O)$(OR)_2$, —OP(O)(OR)$NR_2$, —OP(O)$(NR_2)_2$, —P(O)$R_2$, —$SiR_3$, —Si(OR)$R_2$, or

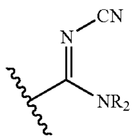

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2$(OR), —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —$SiR_3$, —$SF_5$, or

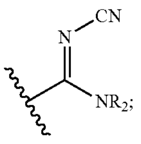

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P is selected from benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P is optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with -$Cy^x$-, —O—, —S—, —C(O)—, —C(S)—, —$CR_2$—, —CRF—, —$CF_2$—, —NR—, —N═CR—, —CR═CR—, or —$S(O)_2$—, wherein R of —$CR_2$—, —CRF—, —NR—, —N═CR—, or —CR═CR— can combine with $R^x$ or R to form a 4-7 membered saturated or partially unsaturated carbocyclic or heterocyclic ring having 1-3 heteroatoms independently selected from nitrogen, oxygen, and sulfur;

$Cy^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -$Cy^x$- is optionally substituted with 1-2 oxo groups;

each x is 0, 1, 2, 3 or 4; and each y is 0, 1, 2, 3 or 4.

In certain embodiments, the present invention provides a compound of formula I-k-2 or I-k-3 above, wherein $L^x$ is amide, Ring P is pyrazolyl, Ring T is pyridyl, R is Me, and $R^y$ is —$CF_3$.

In some embodiments, the present invention provides a compound of formula I-a or I'-a, wherein LBM is thalidomide or

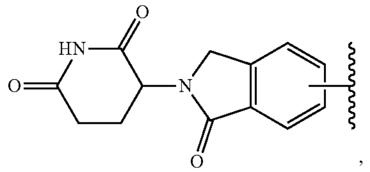

,

Ring P and Ring Q form an indazole ring, a single $R^x$ is —OR, and X is cyclohexyl as shown, to provide a compound of formula I-k-4 or I-k-5:

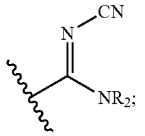

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, I-k-4

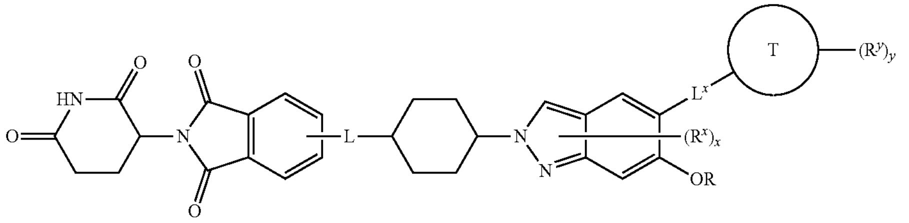

I-k-5

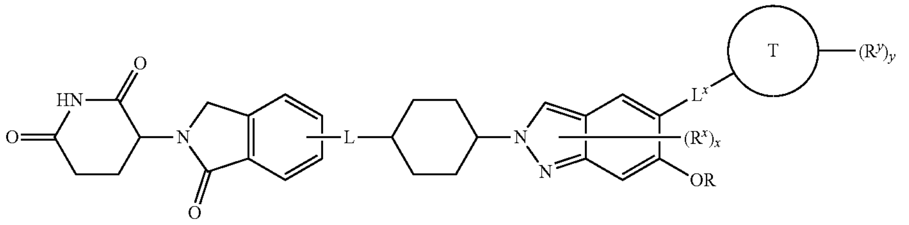

or a pharmaceutically acceptable salt thereof, wherein L is as defined and described herein, and wherein:

each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —$C(O)NR_2$, —$C(S)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$N^{+6}$ $(O^-)R_2$, —$OP(O)R_2$, —$OP(O)(OR)_2$, —$OP(O)(OR)NR_2$, —$OP(O)(NR_2)_2$, —$P(O)R_2$, —$SiR_3$, —$Si(OR)R_2$, or —$CR_2(NR_2)$, —C(O)R, —C(O)OR, —$C(O)NR_2$, —$C(S)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, —$SiR_3$, —$SF_5$, or

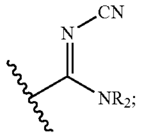

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with -$Cy^x$-, —O—, —S—, —C(O)—, —C(S)—, —$CR_2$—, —CRF—, —$CF_2$—, —NR—, —N═CR—, —CR═CR—, or —$S(O)_2$—, wherein R of —$CR_2$—, —CRF—, —NR—, —N═CR—, or —CR═CR— can combine with $R^x$ or R to form a 4-7 membered saturated or partially unsaturated carbocyclic or heterocyclic ring having 1-3 heteroatoms independently selected from nitrogen, oxygen, and sulfur;

-$Cy^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -$Cy^x$- is optionally substituted with 1-2 oxo groups;

each x is 0, 1, 2, 3 or 4; and each y is 0, 1, 2, 3 or 4.

In certain embodiments, the present invention provides a compound of formula I-k-6 or I-k-7 above, wherein $L^x$ is amide, Ring T is pyridyl, R is Me, and $R^y$ is —$CF_3$.

In some embodiments, the present invention provides a compound of formula I-a or I'-a, wherein LBM is thalidomide or

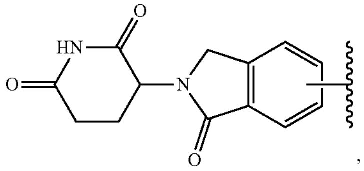

,

Ring Q is

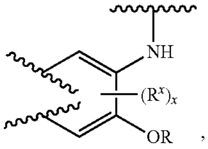

, a, $L^x$ is amide, a single $R^x$ is —OR, and X is cyclohexyl as shown, to provide a compound of formula I-k-6 or I-k-7:

I-k-6

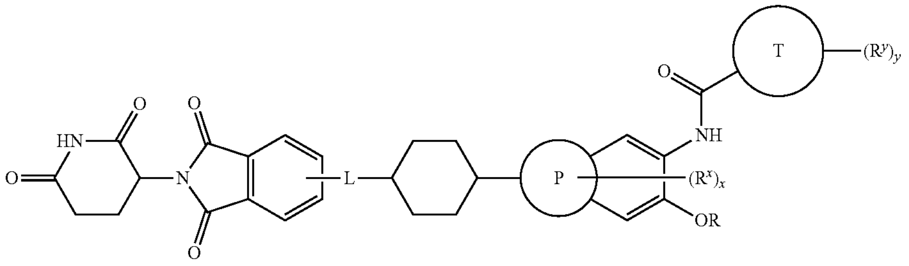

I-k-7

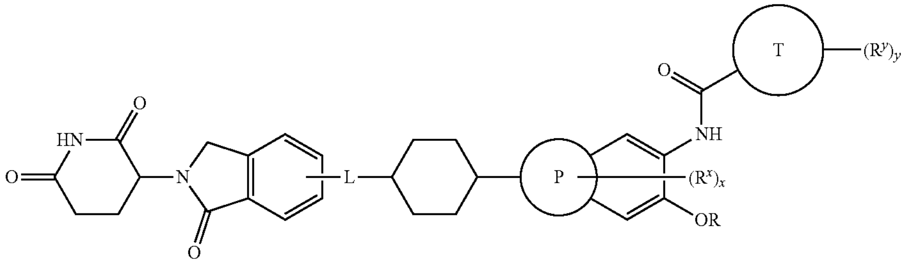

or a pharmaceutically acceptable salt thereof, wherein L is as defined and described herein, and wherein:

each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$N^+$ $(O^-)R_2$, —OP(O)$R_2$, —OP(O)$(OR)_2$, —OP(O)(OR)$NR_2$, —OP(O)$(NR_2)_2$, —P(O)$R_2$, —$SiR_3$, —Si(OR)$R_2$, or

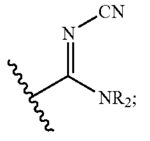

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —$SiR_3$, —$SF_5$, or

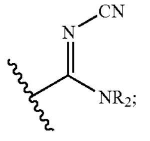

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P is selected from benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P is optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

each x is 0, 1, 2, 3 or 4; and each y is 0, 1, 2, 3 or 4.

In certain embodiments, the present invention provides a compound of formula I-k-6 or I-k-7 above, wherein Ring P is pyrazolyl, Ring T is pyridyl, R is Me, and $R^y$ is —$CF_3$.

In some embodiments, the present invention provides a compound of formula I-a or I'-a, wherein LBM is thalidomide or

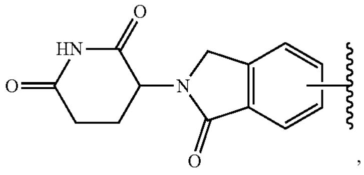

,

Ring P and Ring Q form an indazole ring, $L^x$ is amide, a single $R^x$ is —OR, and X is cyclohexyl as shown, to provide a compound of formula I-k-8 or I-k-9:

I-k-8

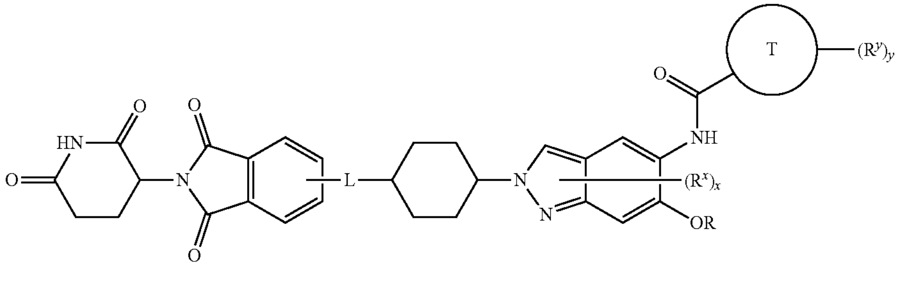

-continued

I-k-9

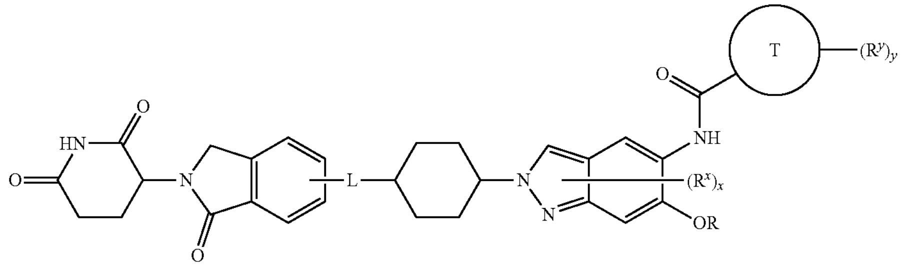

or a pharmaceutically acceptable salt thereof, wherein L is as defined and described herein, and wherein:

each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —$C(O)NR_2$, —$C(S)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$N^{+6}$ $(O^-)R_2$, —$OP(O)R_2$, —$OP(O)(OR)_2$, —$OP(O)(OR)NR_2$, —$OP(O)(NR_2)_2$, —$P(O)R_2$, —$SiR_3$, —$Si(OR)R_2$, or

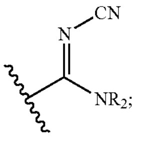

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —$C(O)NR_2$, —$C(S)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, —$SiR_3$, —$SF_5$, or

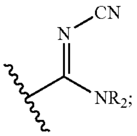

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

each x is 0, 1, 2, 3 or 4; and each y is 0, 1, 2, 3 or 4.

In certain embodiments, the present invention provides a compound of formula I-k-8 or I-k-9 above, wherein Ring T is pyridyl, R is Me, and $R^y$ is —$CF_3$.

In some embodiments, the present invention provides a compound of formula I-a or I'-a, wherein LBM is thalidomide or

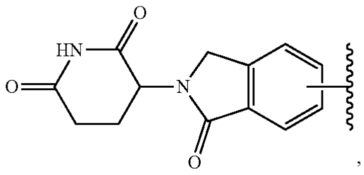

,

Ring P and Ring Q form an indazole ring, Ring T is pyridyl, $L^x$ is amide, a single $R^x$ is —OR, and X is cyclohexyl as shown, to provide a compound of formula I-k-10 or I-k-11:

I-k-10

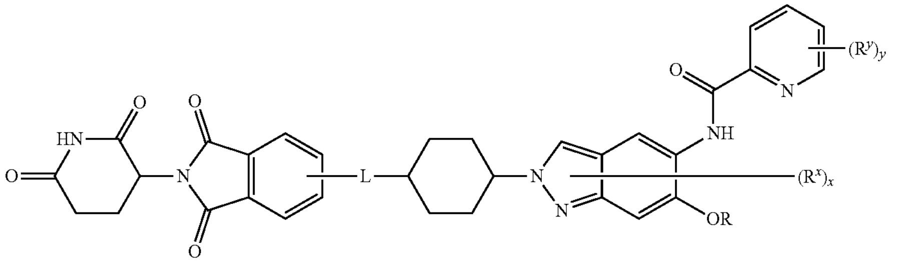

I-k-11

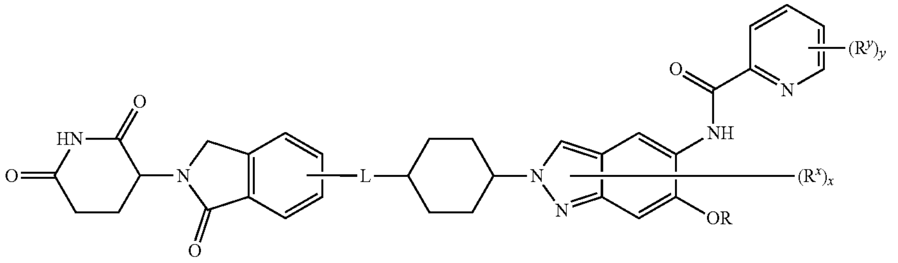

or a pharmaceutically acceptable salt thereof, wherein L is as defined and described herein, and wherein:

each $R^x$ is independently hydrogen, deuterium, $R^z$, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$N^{+6}$ $(O^-)R_2$, —OP(O)$R_2$, —OP(O)$(OR)_2$, —OP(O)(OR)$NR_2$, —OP(O)$(NR_2)_2$, —P(O)$R_2$, —$SiR_3$, —Si(OR)$R_2$, or

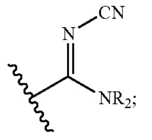

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —$SiR_3$, —$SF_5$, or

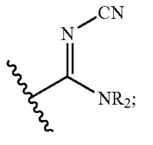

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each x is 0, 1, 2, 3 or 4; and each y is 0, 1, 2, 3 or 4.

In certain embodiments, the present invention provides a compound of formula I-k-10 or T-k-11 above, wherein R is Me and $R^y$ is —$CF_3$.

In some embodiments, the present invention provides a compound of formula I-a or I'-a, wherein LBM is

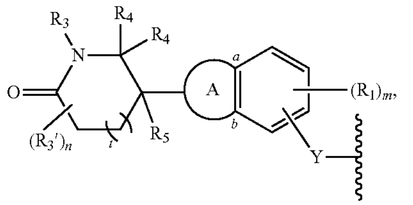

Ring Q is

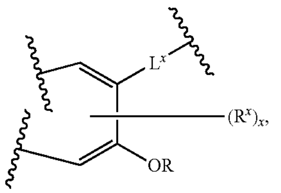

a single $R^x$ is —OR, and X is cyclohexyl as shown, to provide a compound of formula I-k-12:

I-k-12

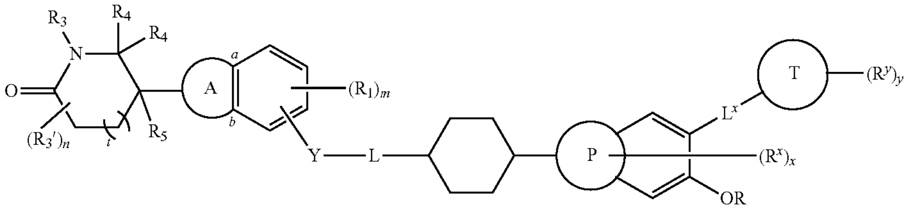

or a pharmaceutically acceptable salt thereof, wherein each of variables

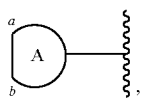

Y, $R_1$, $R_3$, $R_3'$, $R_4$, $R_5$, t, m, n, Ring P, Ring T, L, $L^x$, $R^x$, $R^y$, x, and y is as defined above and described in embodiments herein, both singly and in combination.

In some embodiments, the present invention provides a compound of formula I-a or I'-a, wherein LBM is

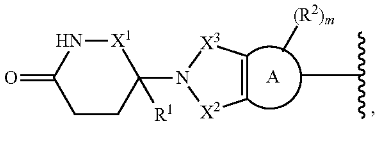

Ring Q is

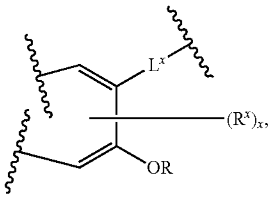

a single $R^x$ is —OR, and X is cyclohexyl as shown, to provide a compound of formula I-k-13:

I-k-13

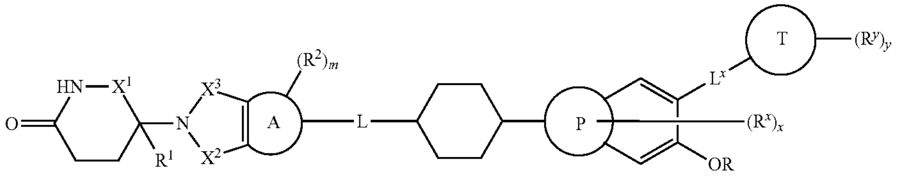

or a pharmaceutically acceptable salt thereof, wherein each of variables $X^1$, $X^2$, $X^3$, $R^1$, $R^2$, Ring A, m, Ring P, Ring T, L, $L^x$, $R^x$, $R^y$, x, and y is as defined above and described in embodiments herein, both singly and in combination.

In some embodiments, the present invention provides a compound of formula I-a or I'-a, wherein LBM is

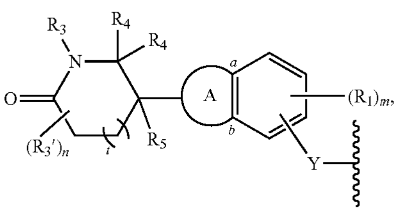

Ring P and Ring Q form an indazole ring, a single $R^x$ is —OR, and X is cyclohexyl as shown, to provide a compound of formula I-k-14:

I-k-14

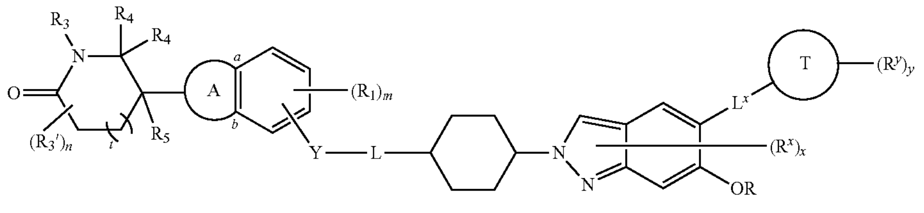

or a pharmaceutically acceptable salt thereof, wherein each of variables

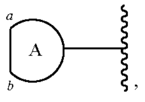

Y, $R_1$, $R_3$, $R_3'$, $R_4$, $R_5$, t, m, n, Ring T, L, $L^x$, $R^x$, $R^y$, x, and y is as defined above and described in embodiments herein, both singly and in combination.

In some embodiments, the present invention provides a compound of formula I-a or I'-a, wherein LBM is

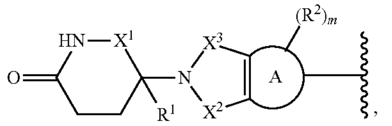

Ring P and Ring Q form an indazole ring, a single $R^x$ is —OR, and X is cyclohexyl as shown, to provide a compound of formula I-k-15:

I-k-15

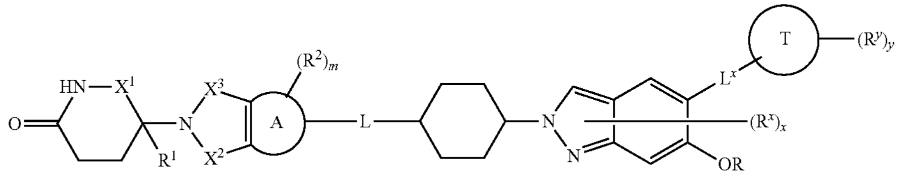

or a pharmaceutically acceptable salt thereof, wherein each of variables $X^1$, $X^2$, $X^3$, $R^1$, $R^2$, Ring A, m, Ring T, L, $L^x$, $R^x$, $R^y$, x, and y is as defined above and described in embodiments herein, both singly and in combination.

In some embodiments, the present invention provides a compound of formula I-a or I'-a, wherein LBM is thalidomide, Ring P and Ring Q form an indazole ring, and Ring T is cyclohexyl as shown, to provide a compound of formula I-l-1:

I-l-1

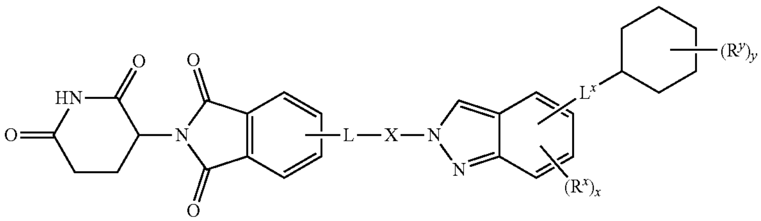

or a pharmaceutically acceptable salt thereof, wherein each of L, $L^x$, X, $R^x$, $R^y$, x, and y is as defined above and described in embodiments herein, both singly and in combination.

In some embodiments, the present invention provides a compound of formula I-a or I'-a, wherein LBM is thalidomide, Ring P and Ring Q form a 4,5,6,7-tetrahydro-2H-indazole ring as shown, to provide a compound of formula I-l-2:

I-1-2

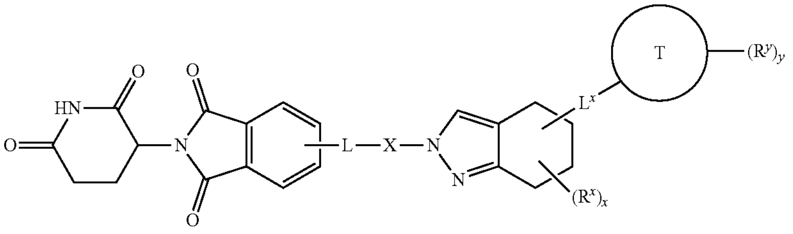

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide, Ring P and Ring Q form an isoindolin-1-one ring as shown, to provide a compound of formula I-1-3:

I-1-3

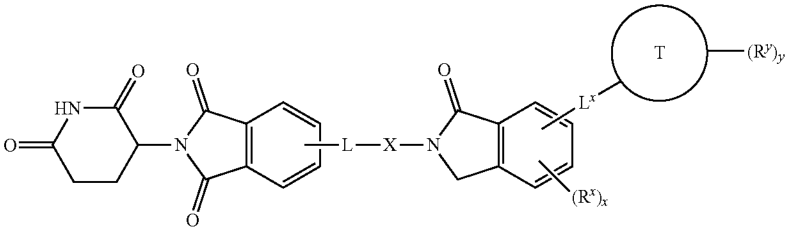

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide and Ring P and Ring Q form a quinoline ring as shown, to provide a compound of formula I-m-1:

I-m-1

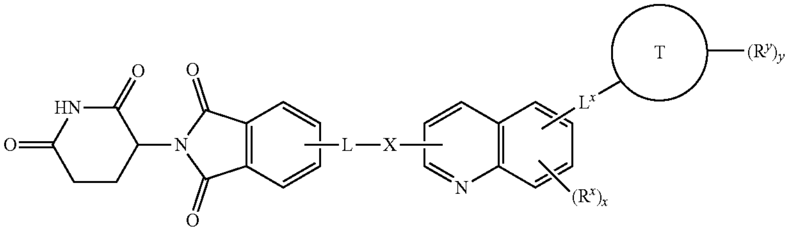

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a or I'-a, wherein LBM is thalidomide, Ring P and Ring Q form a 2H-thieno[2,3-c]pyrazole ring as shown, to provide a compound of formula I-m-1:

I-m-2

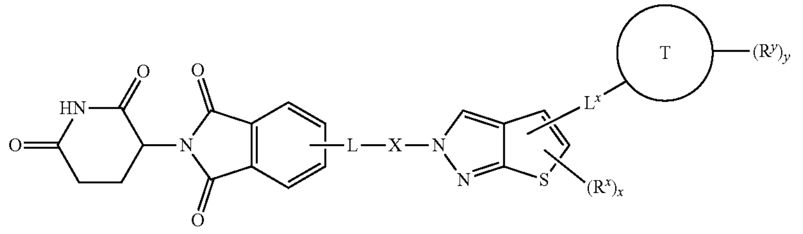

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-b or I'-b, wherein LBM is thalidomide, Ring P is pyridine, and Ring Q is phenyl as shown, to provide a compound of formula I-n-1:

I-n-1

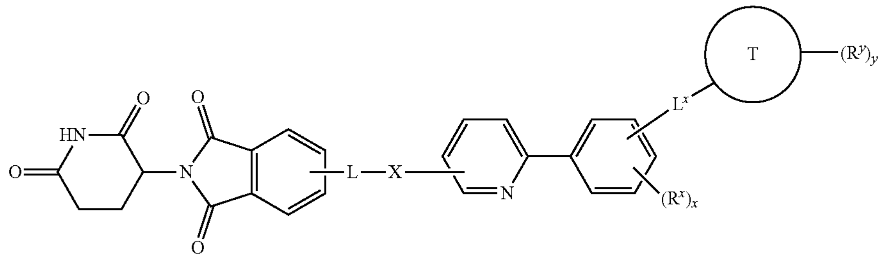

or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-b or I'-b, wherein LBM is thalidomide, Ring P is pyrazole, and Ring Q is phenyl as shown, to provide a compound of formula I-n-2:

I-n-2

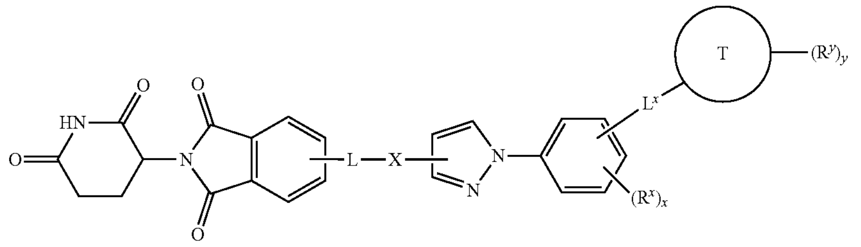

or a pharmaceutically acceptable salt thereof, wherein each of L, $L^x$, X, $R^x$, $R^y$, Ring T, x, and y is as defined above and described in embodiments herein, both singly and in combination.

In certain embodiments, the present invention provides a compound of Formula I, wherein LBM is an E3 ubiquitin ligase (cereblon) binding moiety thereby forming a compound of formula I-qq-1, I-qq-2, or I-qq-3 respectively:

I-qq-1

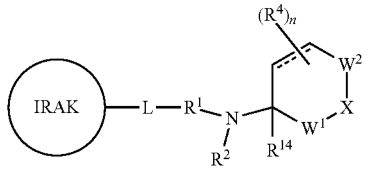

-continued

I-qq-2

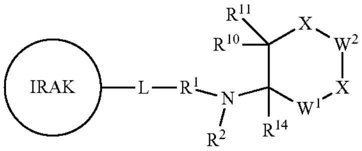

I-qq-3

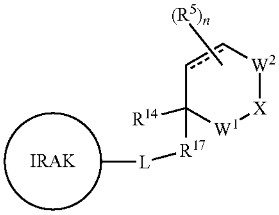

or a pharmaceutically acceptable salt thereof, wherein L and IRAK are as defined above and described herein, and wherein each of the variables $R^1$, $R^2$, $R^4$, $R^5$, $R^{10}$, $R^{11}$, $R^{14}$, $R^{17}$, $W^1$, $W^2$, X, - - - -, and n is as defined in WO 2017/197051 which is herein incorporated by reference in its entirety and wherein

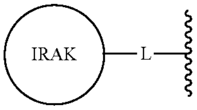

is attached to $R^1$, the ring formed by combining $R^1$ and $R^2$ or $R^{17}$ at the site of attachment of $R^{12}$ as defined in WO 2017/197051 such that

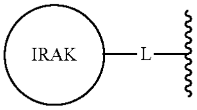

takes the place of the $R^{12}$ substituent.

In some embodiments, the present invention provides a compound of formula I, wherein LBM is an E3 ubiquitin ligase (cereblon) binding moiety thereby forming a compound of formula I-rr-1, I-rr-2, I-rr-3, or I-rr-4, respectively:

I-rr-1

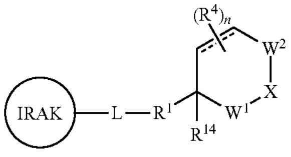

I-rr-2

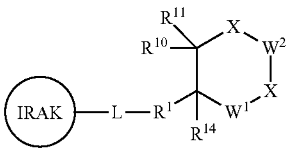

-continued

I-rr-3

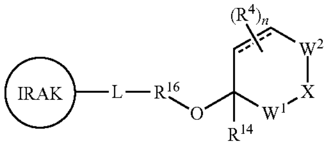

I-rr-4

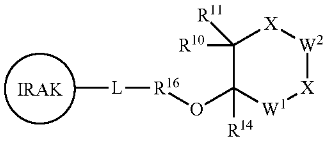

or a pharmaceutically acceptable salt thereof, wherein L and IRAK are as defined above and described herein, and wherein each of the variables $R^1$, $R^4$, $R^{10}$, $R^{11}$, $R^{14}$, $R^{16}$, $W^1$, $W^2$, X, - - - -, and n is as defined in WO 2018/237026, the entirety of each of which is herein incorporated by reference, and wherein

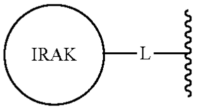

is attached to $R^1$ or $R^{16}$ at the site of attachment of $R^{12}$ as defined in WO 2018/237026, such that

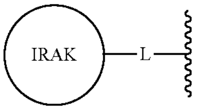

takes the place of the $R^{12}$ substituent.

In some embodiments, the present invention provides a compound of formula I, wherein LBM is an E3 ubiquitin ligase (cereblon) binding moiety thereby forming a compound of formula I-ss-1 or I-ss-3, respectively:

I-ss-1

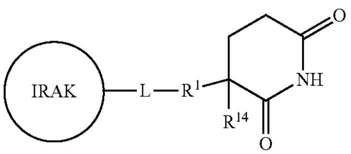

I-ss-3

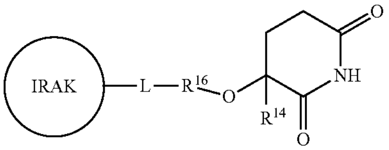

or a pharmaceutically acceptable salt thereof, wherein L and IRAK are as defined above and described herein, and wherein each of the variables $R^1$, $R^{14}$, and $R^{16}$ is as defined in WO 2018/237026, the entirety of each of which is herein incorporated by reference, and wherein

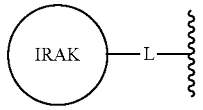

is attached to $R^1$ or $R^{16}$ at the site of attachment of $R^{12}$ as defined in WO 2018/237026, such that

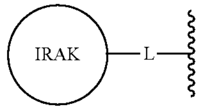

takes the place of the $R^{12}$ substituent.

In certain embodiments, the present invention provides a compound of formula I, wherein LBM is an E3 ubiquitin ligase (cereblon) binding moiety thereby forming a compound of formula I-tt-1, I-tt-2, I-tt-3, I-tt-4, I-tt-5, I-tt-6, I-tt-7, or I-tt-8:

I-tt-1

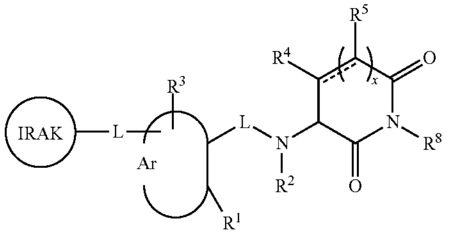

I-tt-2

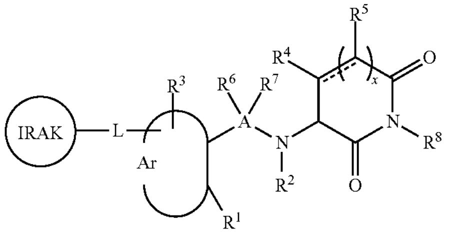

I-tt-3

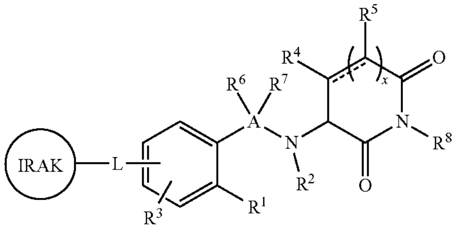

I-tt-4

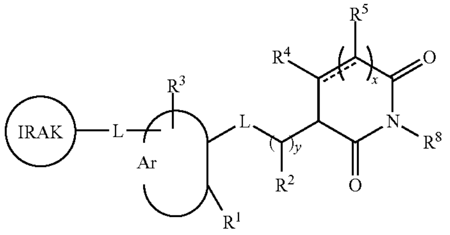

-continued

I-tt-5

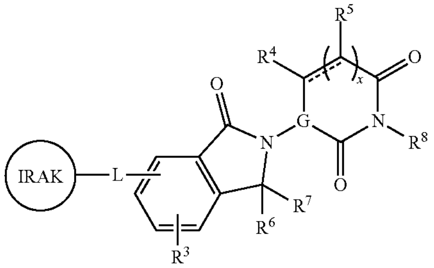

I-tt-6

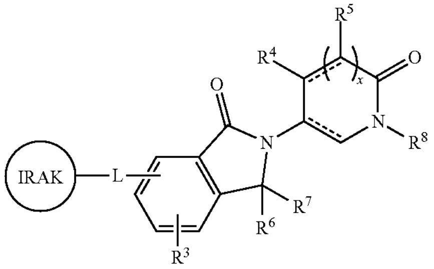

I-tt-7

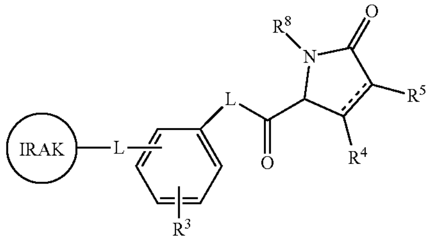

I-tt-8

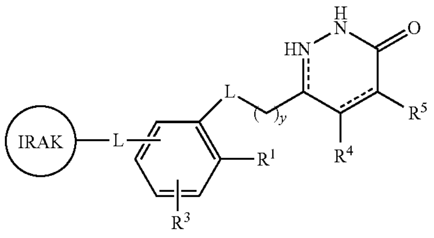

or a pharmaceutically acceptable salt thereof, wherein L and IRAK are as defined above and described in embodiments herein, and wherein each of the variables Ar, $R^1$, $R^2$, $R^3$, $R^4$, $R^5$, $R^6$, $R^7$, $R^8$, A, L, x, y, and ---- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety thereby forming a compound of formula I-uu:

I-uu

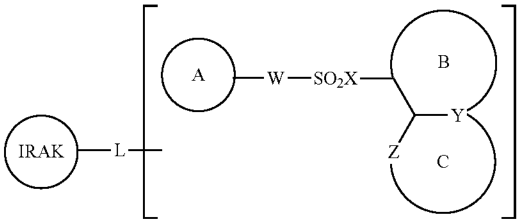

or a pharmaceutically acceptable salt thereof, wherein L and IRAK are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of formula I, wherein LBM is an E3 ubiquitin ligase (cereblon) binding moiety thereby forming a compound of formula I-vv:

I-vv

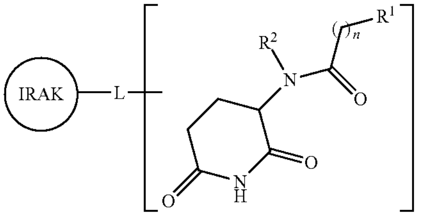

or a pharmaceutically acceptable salt thereof, wherein L and IRAK are as defined above and described in embodiments herein, and wherein each of the variables $R_1$, $R_2$, and n is as described and defined in WO 2019/043214, the entirety of each of which is herein incorporated by reference.

In some embodiments, LBM is a IAP E3 Ubiquitin ligase binding moiety recited in Varfolomeev, E. et al., *IAP Antagonists Induce Autoubiquitination of c-IAPs, NF-κB* activation, and TNFα-*Dependent Apoptosis*, Cell, 2007, 131(4): 669-81, such as, for example:

MV1

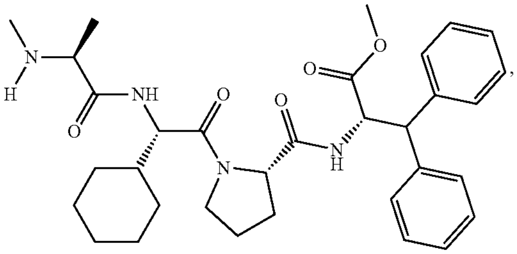

, and

BV6

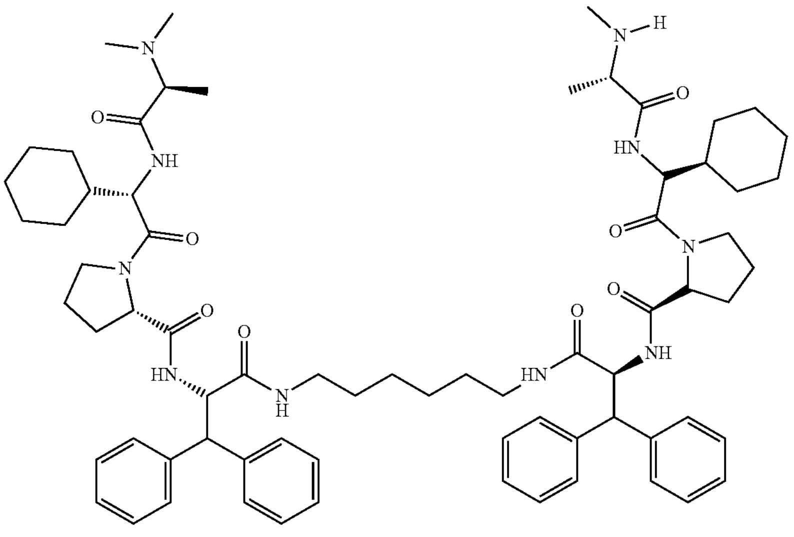

wherein

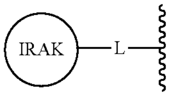

is attached to a modifiable carbon, oxygen, nitrogen or sulfur atom.

In certain embodiments, the present invention provides a compound of Formula I, wherein LBM is a VHL E3 ubiquitin ligase binding moiety thereby forming a compound of formula I-ww-1, I-ww-2, I-ww-3, I-ww-4, or I-ww-5 respectively:

I-ww-1

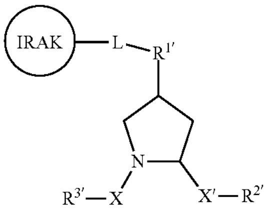

-continued

I-ww-2

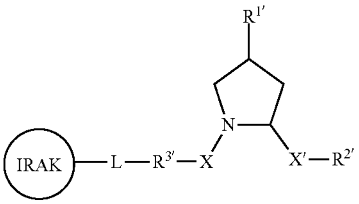

I-ww-3

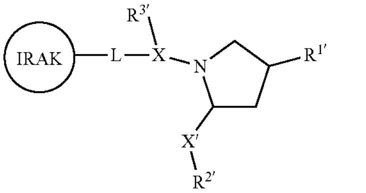

I-ww-4

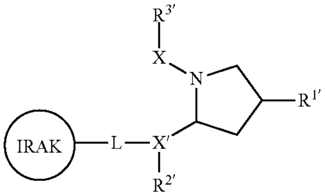

I-ww-5

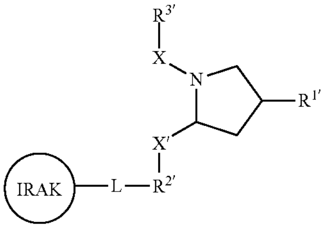

or a pharmaceutically acceptable salt thereof, wherein L and IRAK are as defined above and described in embodiments herein, and wherein each of the variables $R^{1'}$, $R^{2'}$, $R^{3'}$, X, and X' is as defined and described in WO 2013/106643 and US 2014/0356322, the entirety of each of which is herein incorporated by reference.

In certain embodiments, the present invention provides a compound of Formula I, wherein LBM is a VHL E3 ubiquitin ligase binding moiety thereby forming a compound of formula I-xx-1, I-xx-2, I-xx-3, I-xx-4, I-xx-5 or I-xx-6 respectively:

I-xx-1

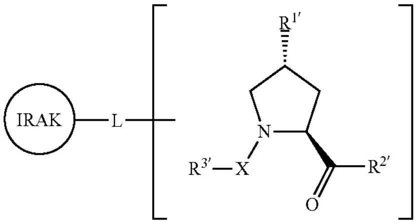

-continued

I-xx-2

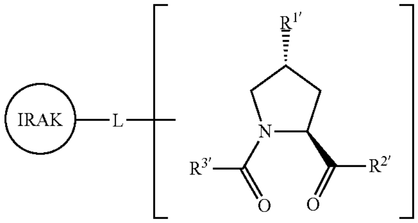

I-xx-3

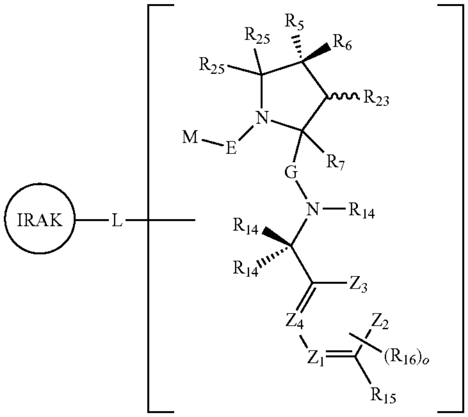

I-xx-4

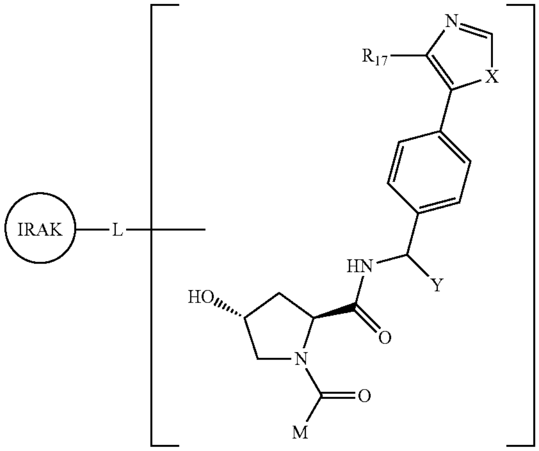

I-xx-5

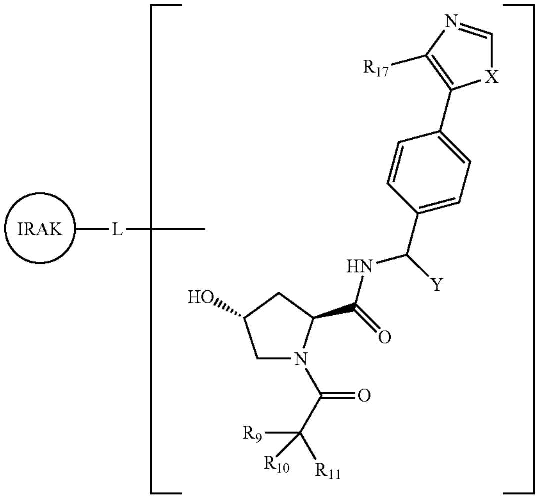

-continued

I-xx-6

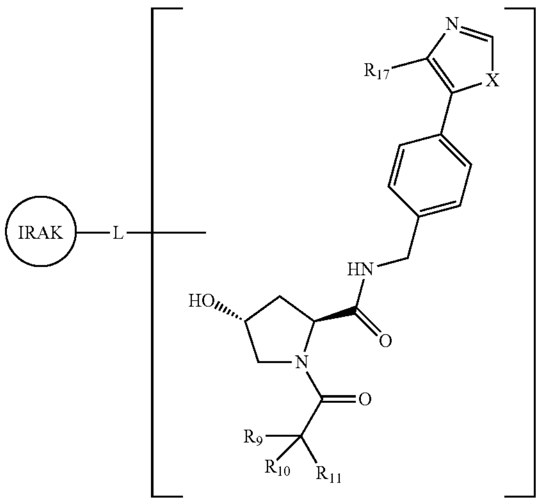

or a pharmaceutically acceptable salt thereof, wherein L and IRAK are as defined above and described in embodiments herein, and wherein each of the variables $R^1$, $R^{2'}$, $R^{3'}$, $R_5$, $R_6$, $R_7$, $R_9$, $R_{10}$, $R_{11}$, $R_{14}$, $R_{15}$, $R_{16}$, $R_{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

As used herein, depiction of brackets around any LBM

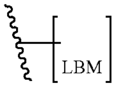

means that the

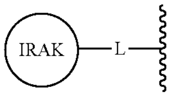

moiety is covalently attached to said LBM at any available modifiable carbon, nitrogen, oxygen, or sulfur atom. For purposes of clarity and by way of example, such available modifiable carbon, nitrogen, oxygen, or sulfur atoms in the following LBM compound structure are depicted below, wherein each wavy bond defines the point of attachment to said

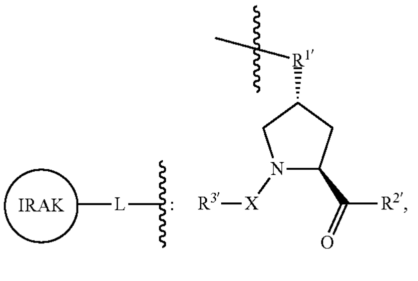

-continued

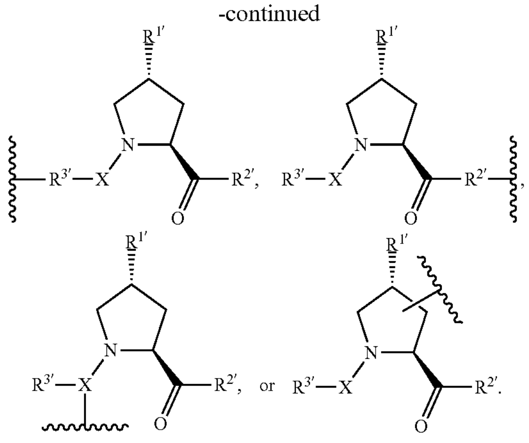

In certain embodiments, the present invention provides a compound of Formula I, wherein LBM is a VHL E3 ubiquitin ligase binding moiety thereby forming a compound of formula I-yy-1, I-yy-2, or I-yy-3 respectively:

I-yy-1

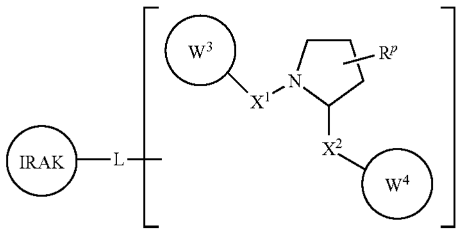

I-yy-2

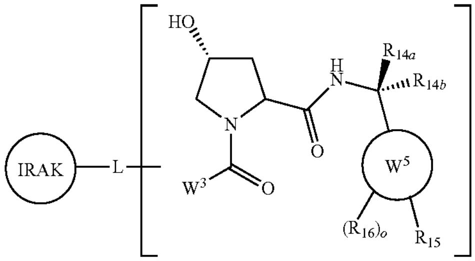

I-yy-3

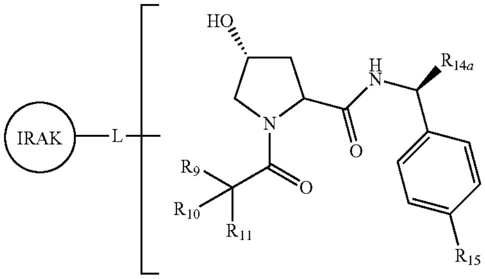

or a pharmaceutically acceptable salt thereof, wherein L and IRAK are as defined above and described in embodiments herein, and wherein each of the variables $R^P$, $R_9$, $R_{10}$, $R_{11}$, $R_{14a}$, $R_{14b}$, $R_{15}$, $R_{16}$, $W^3$, $W^4$, $W^5$, $X^1$, $X^2$, and o is as defined and described in WO 2016/118666 and US 2016/0214972, the entirety of each of which is herein incorporated by reference.

In certain embodiments, the present invention provides a compound of Formula I, wherein LBM is a CRBN or VHL E3 ubiquitin ligase binding moiety thereby forming a compound of formula I-zz-1, I-zz-2, I-zz-3, I-zz-4, I-zz-5, I-zz-6, or I-zz-7 respectively:

I-zz-1

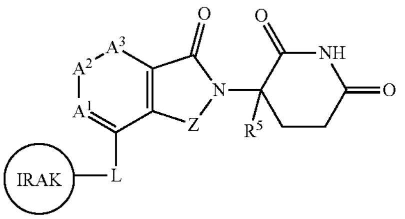

I-zz-2

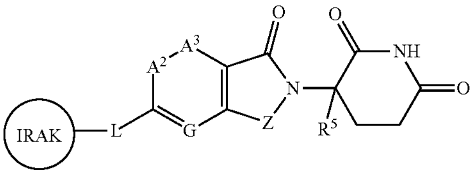

I-zz-3

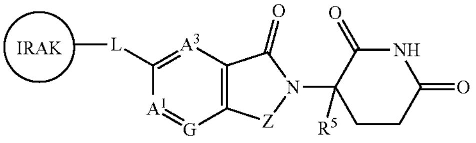

I-zz-4

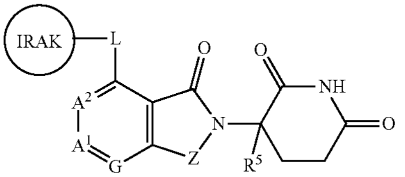

I-zz-5

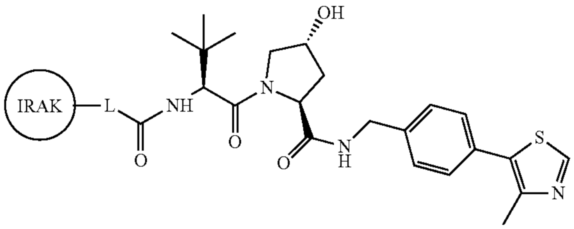

I-zz-6

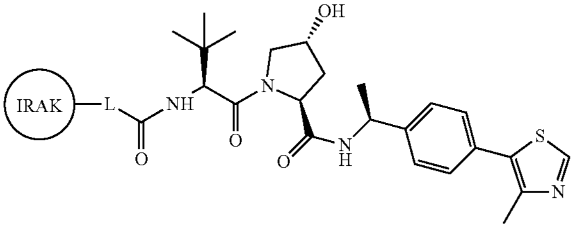

I-zz-7

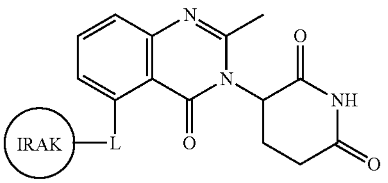

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958.

In certain embodiments, the present invention provides a compound of Formula I, wherein LBM is a CRBN E3 ubiquitin ligase binding moiety thereby forming a compound of formula I-zz'-1, I-zz"-1, I-zz'-2, I-zz'-2, I-zz'-3, I-zz"-3, I-zz'-4, I-zz"-4, I-zz'-7 or I-zz"-7 respectively:

I-zz'-1

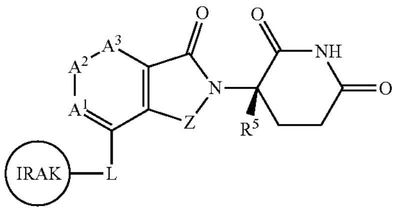

I-zz"-1

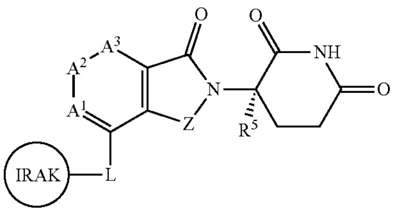

I-zz'-2

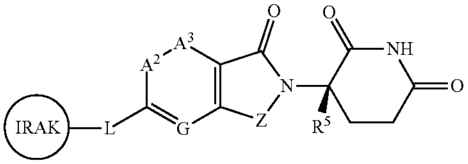

I-zz"-2

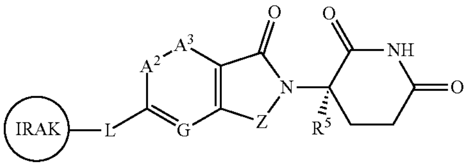

I-zz'-3

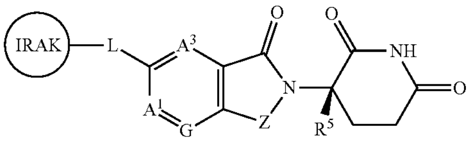

I-zz"-3

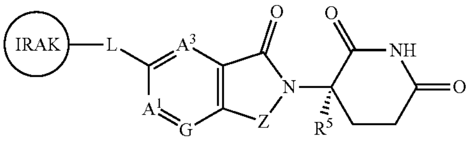

I-zz'-4

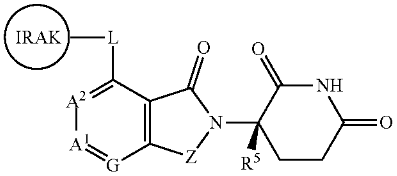

-continued

I-zz″-4

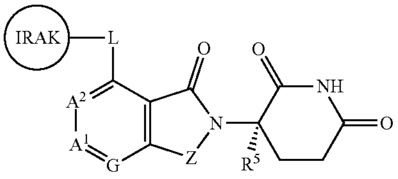

I-zz′-7

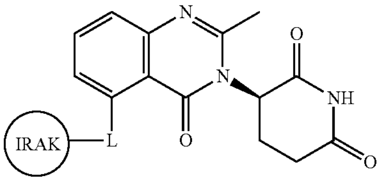

I-zz″-7

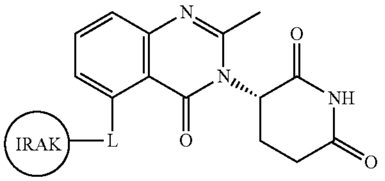

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958, the entirety of which is herein incorporated by reference.

In certain embodiments, the present invention provides a compound of Formula I, wherein LBM is a MDM2 (i.e. human double minute 2 or HDM2) E3 ligase binding moiety thereby forming a compound of formula I-aaa-1, I-aaa-2, I-aaa-3, I-aaa-4, I-aaa-5, I-aaa-6, I-aaa-7, I-aaa-8, I-aaa-9, I-aaa-10, I-aaa-11, I-aaa-12, I-aaa-13, I-aaa-14, I-aaa-15, I-aaa-16, I-aaa-17, or I-aaa-18 respectively:

I-aaa-1

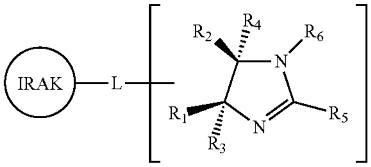

I-aaa-2

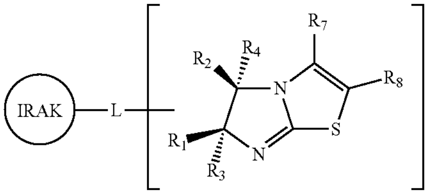

I-aaa-3

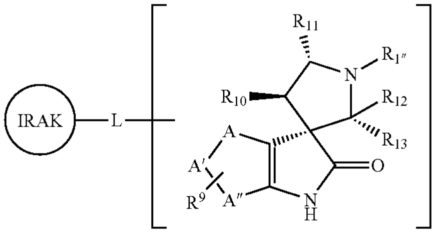

-continued

I-aaa-4

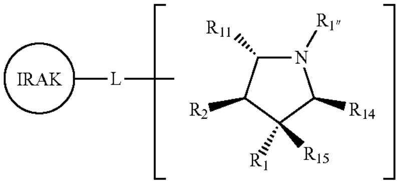

I-aaa-5

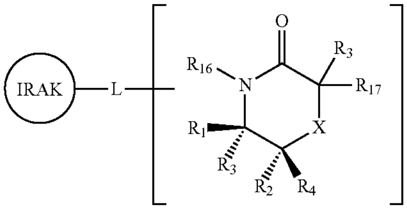

I-aaa-6

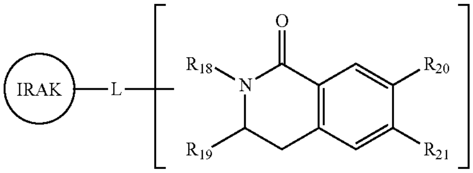

I-aaa-7

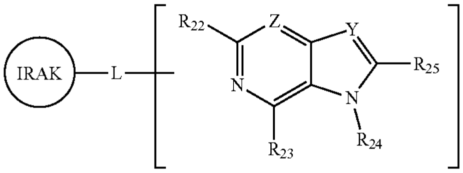

I-aaa-8

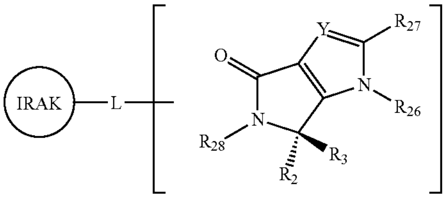

I-aaa-9

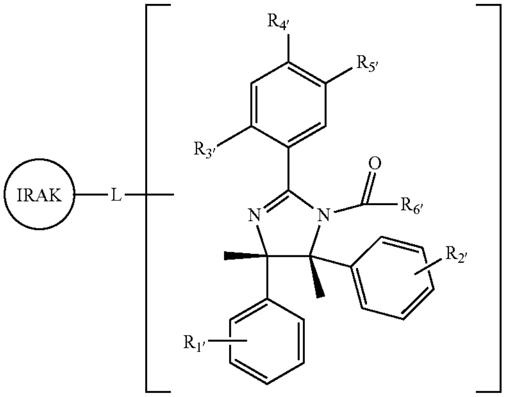

I-aaa-10
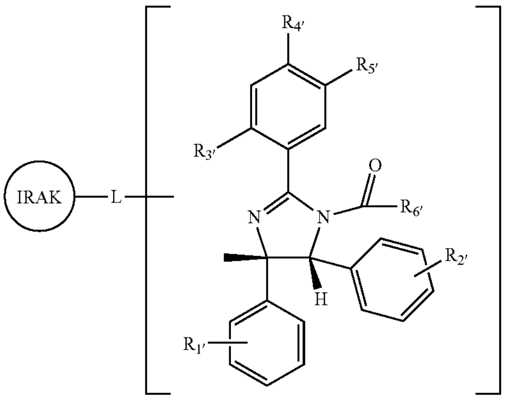
I-aaa-11
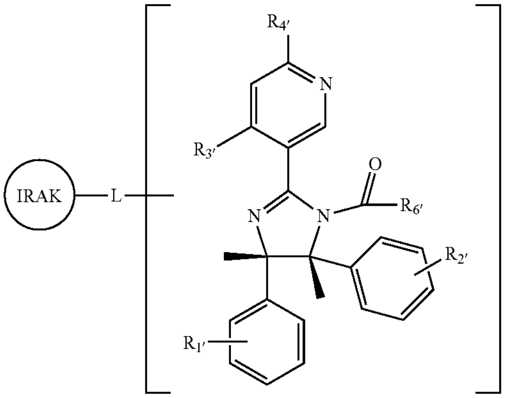
I-aaa-12
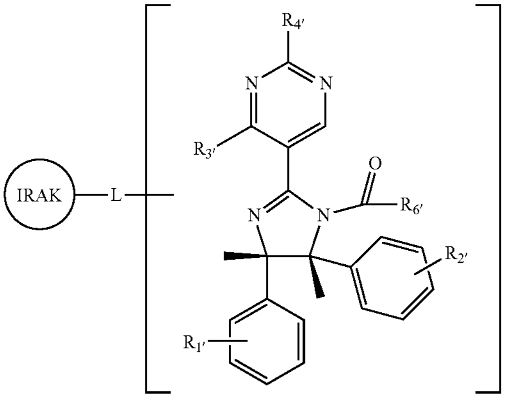
I-aaa-13
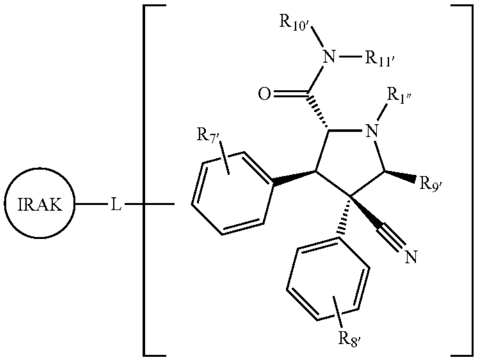
I-aaa-14
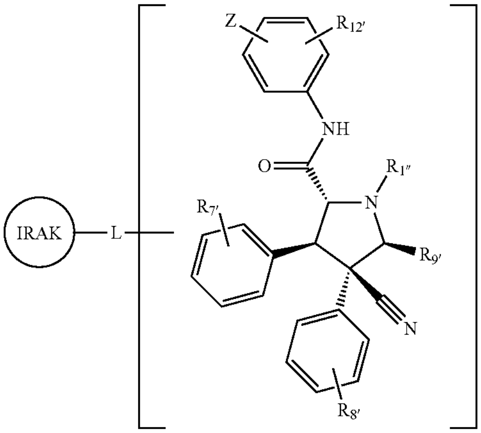
I-aaa-15
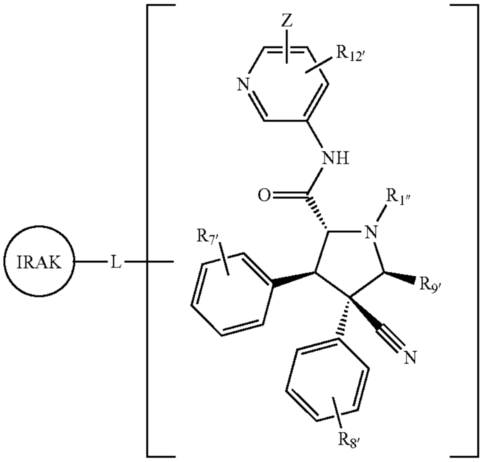
I-aaa-16
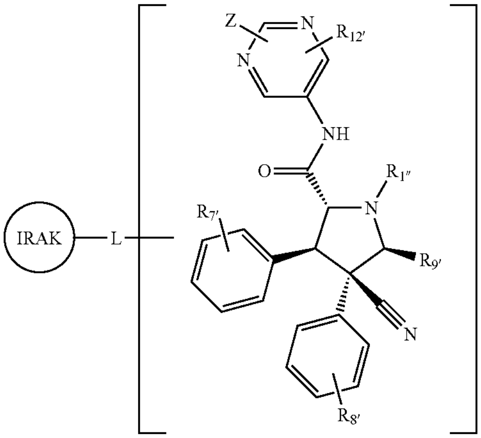

-continued

I-aaa-17

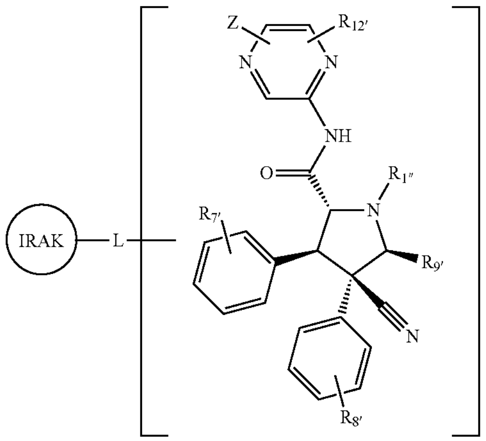

I-aaa-18

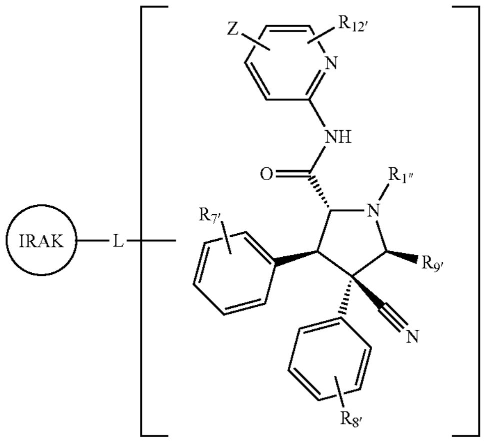

or a pharmaceutically acceptable salt thereof, wherein L and IRAK are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R_{3'}$, $R_{4'}$, $R_{5'}$, $R_{6'}$, $R_{7'}$, $R_{8'}$, $R_{9'}$, $R_{10'}$, $R_{11'}$, $R_{12'}$, $R_{1''}$, A, A', A", X, Y, and Z is as defined and described in WO 2017/011371 and US 2017/0008904, the entirety of each of which is herein incorporated by reference.

In certain embodiments, the present invention provides a compound of Formula I, wherein LBM is an IAP E3 ubiquitin ligase binding moiety thereby forming a compound of formula I-bbb-1, I-bbb-2, I-bbb-3, or I-bbb-4 respectively:

I-bbb-1

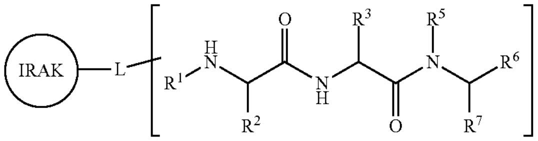

-continued

I-bbb-2

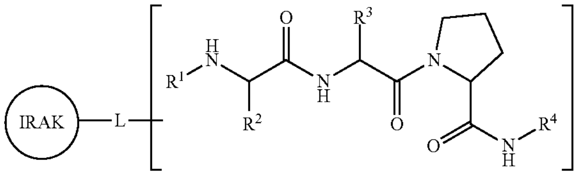

I-bbb-3

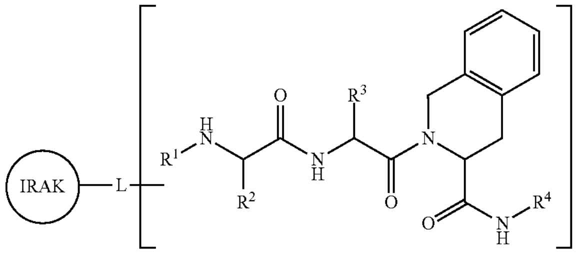

I-bbb-4

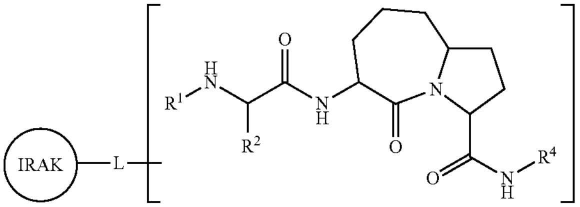

or a pharmaceutically acceptable salt thereof, wherein L and IRAK are as defined above and described in embodiments herein, and wherein each of the variables $R^1$, $R^2$, $R^3$, $R^4$, $R^5$, R, and $R^7$, is as defined and described in WO 2017/011590 and US 2017/0037004, the entirety of each of which is herein incorporated by reference.

In certain embodiments, the present invention provides a compound of Formula I, wherein LBM is an E3 ubiquitin ligase (cereblon) binding moiety, a DCAF15 E3 ubiquitin ligase binding moiety, or a VHL E3 ubiquitin ligase binding moiety; thereby forming a compound of formula I-ccc-1, I-ccc-2, or I-ccc-3:

I-ccc-1

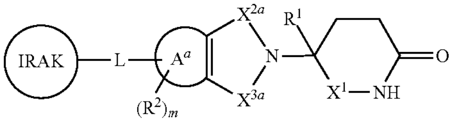

I-ccc-2

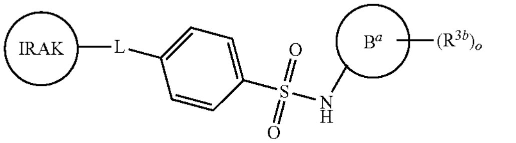

-continued

I-ccc-3

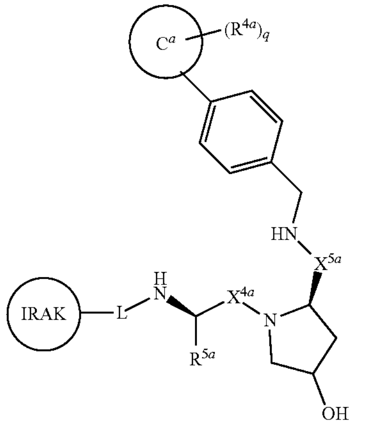

or a pharmaceutically acceptable salt thereof, wherein L and IRAK is as defined above and described in embodiments herein, and wherein:

each of $X^1$, $X^{2a}$, and $X^{3a}$ is independently a bivalent moiety selected from a covalent bond, —$CH_2$—, —C(O)—, —C(S)—, or

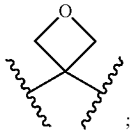 [SMILES: *C1(*)COC1]

;

each of $X^{4a}$ and $X^{5a}$ is independently a bivalent moiety selected from —$CH_2$—, —C(O)—, —C(S)—, or

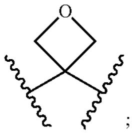

;

$R^1$ is hydrogen, deuterium, halogen, —CN, —OR, —SR, —S(O)R, —$S(O)_2R$, —$NR_2$, or an optionally substituted $C_{1-4}$ aliphatic;

each of $R^2$, $R^{3b}$, and $R^{4a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^{5a}$ is hydrogen or $C_{1-6}$ aliphatic;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring $B^a$ is selected from 6-membered aryl containing 0-2 nitrogen atoms or a 8-10 membered bicyclic heteroaryl having 1-5 heteroatoms independently selected from nitrogen, oxygen, or sulfur;

Ring $C^a$ is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;

o is 0, 1, 2, 3 or 4;

q is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I-ccc-1, wherein LBM is an E3 ubiquitin ligase (cereblon) binding moiety thereby forming a compound of formula I-ccc'-1 or I-ccc"-1:

I-ccc'-1

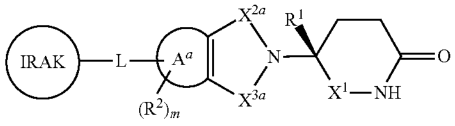

I-ccc"-1

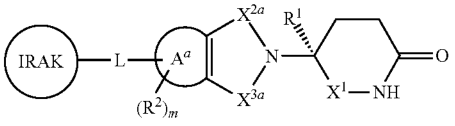

or a pharmaceutically acceptable salt thereof, wherein IRAK, L, Ring $A^a$, $X^1$, $X^{2a}$, $X^{3a}$, $R^1$, $R^2$ and m are as described above.

As defined above and described herein, each of $X^1$, $X^{2a}$, and $X^{3a}$ is independently a bivalent moiety selected from a covalent bond, —$CH_2$—, —C(O)—, —C(S)—, or

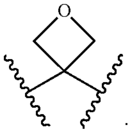 [SMILES: *C1(*)COC1]

.

In some embodiments, $X^1$ is a covalent bond, —$CH_2$—, —C(O)—, —C(S)—, or

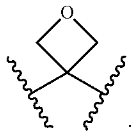 [SMILES: *C1(*)COC1]

In some embodiments, $X^1$ is selected from those depicted in Table 1, below.

In some embodiments, $X^{2a}$ is a covalent bond, —$CH_2$—, —C(O)—, —C(S)—, or

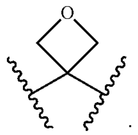 [SMILES: *C1(*)COC1]

In some embodiments, $X^{2a}$ is selected from those depicted in Table 1, below.

In some embodiments, $X^{3a}$ is a covalent bond, —$CH_2$—, —C(O)—, —C(S)—, or

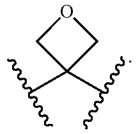 [SMILES: *C1(*)COC1]

In some embodiments, $X^{3a}$ is selected from those depicted in Table 1, below.

As defined above and described herein, each of $X^4$ and $X^5$ is independently a bivalent moiety selected from —$CH_2$—, —C(O)—, —C(S)—, or

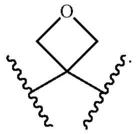

In some embodiments, $X^{4a}$ is —$CH_2$—, —C(O)—, —C(S)—, or

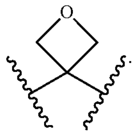 [SMILES: *C1(*)COC1]

In some embodiments, $X^{4a}$ is selected from those depicted in Table 1, below.

In some embodiments, $X^{5a}$ is —$CH_2$—, —C(O)—, —C(S)—, or

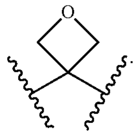 [SMILES: *C1(*)COC1]

In some embodiments, $X^{5a}$ is selected from those depicted in Table 1, below.

As defined above and described herein, $R^1$ is hydrogen, deuterium, halogen, —CN, —OR, —SR, —S(O)R, —$S(O)_2R$, —$NR_2$, or an optionally substituted $C_{1-4}$ aliphatic.

In some embodiments, $R^1$ is hydrogen, deuterium, halogen, —CN, —OR, —SR, —S(O)R, —$S(O)_2R$, —$NR_2$, or an optionally substituted $C_{1-4}$ aliphatic.

In some embodiments, $R^1$ is selected from those depicted in Table 1, below.

As defined above and described herein, each of $R^2$, $R^{3b}$, and $R^{4a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^2$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^2$ is selected from those depicted in Table 1, below.

In some embodiments, $R^{3b}$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^{3b}$ is methyl.

In some embodiments, $R^{3b}$ is selected from those depicted in Table 1, below.

In some embodiments, $R^{4a}$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$.

In some embodiments, $R^{4a}$ is methyl.

In some embodiments, $R^{4a}$ is selected from those depicted in Table 1, below.

As defined above and described herein, $R^{5a}$ is hydrogen or $C_{1-6}$ aliphatic.

In some embodiments, $R^{5a}$ is t-butyl.

In some embodiments, $R^{5a}$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^6$ is an optionally substituted $C_{1-6}$ aliphatic group. In some embodiments, $R^6$ is an optionally substituted phenyl. In some embodiments, $R^6$ is an optionally substituted 4-7 membered saturated or partially unsaturated heterocyclic ring having 1-2 heteroatoms independently selected from nitrogen, oxygen, and sulfur. In some embodiments, $R^6$ is an optionally substituted 5-6 membered heteroaryl ring having 1-4 heteroatoms independently selected from nitrogen, oxygen, and sulfur.

In some embodiments, $R^6$ is selected from those depicted in Table 1, below.

As defined above and described herein, Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring $A^a$ is a fused 6-membered aryl containing 0-2 nitrogen atoms. In some embodiments Ring $A^a$ is a fused 5 to 7-membered partially saturated carbocyclyl. In some embodiments Ring $A^a$ is a fused 5 to 7-membered partially saturated heterocyclyl with 1-2 heteroatoms independently selected from nitrogen, oxygen or sulfur. In some embodiments Ring $A^a$ is a fused 5-membered heteroaryl with 1-3 heteroatoms independently selected from nitrogen, oxygen or sulfur.

In some embodiments, Ring $A^a$ is a fused phenyl.

In some embodiments, Ring $A^a$ is selected from those depicted in Table 1, below.

As defined above and described herein, Ring $B^a$ is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring $B^a$ is a 6-membered aryl containing 0-2 nitrogen atoms. In some embodiments, Ring $B^a$ is a 8-10 membered bicyclic heteroaryl having 1-5 heteroatoms independently selected from nitrogen, oxygen, or sulfur.

In some embodiments, Ring $B^a$ is

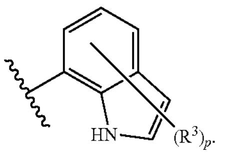

In some embodiments, Ring $B^a$ is selected from those depicted in Table 1, below.

As defined above and described herein, Ring $C^a$ is selected from 6-membered aryl containing 0-2 nitrogen atoms or a 5-membered heteroaryl with 1-3 heteroatoms independently selected from nitrogen, oxygen or sulfur.

In some embodiments, Ring $C^a$ is a 6-membered aryl containing 0-2 nitrogen atoms. In some embodiments, Ring $C^a$ is a 5-membered heteroaryl with 1-3 heteroatoms independently selected from nitrogen, oxygen or sulfur.

In some embodiments, Ring $C^a$ is

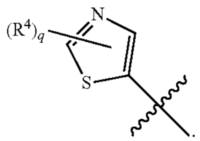

In some embodiments, Ring $C^a$ is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

In some embodiments, o is selected from those depicted in Table 1, below.

As defined above and described herein, o is 0, 1, 2, 3 or 4.

In some embodiments, o is 0. In some embodiments, o is 1. In some embodiments, o is 2. In some embodiments, o is 3. In some embodiments, o is 4.

In some embodiments, o is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In certain embodiments, the present invention provides a compound of formula I, wherein LBM is a VHL binding moiety thereby forming a compound of formula I-ddd:

I-ddd

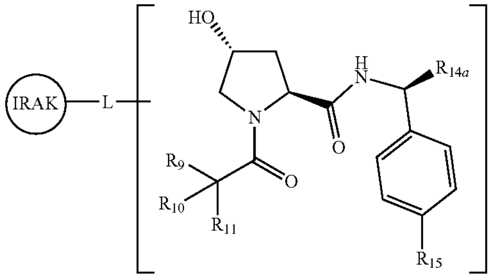

or a pharmaceutically acceptable salt thereof, wherein L and IRAK are as defined above and described in embodiments herein, and wherein each of the variables $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is a VHL binding moiety thereby forming a compound of formula I-eee-1 or I-eee-2:

I-eee-1

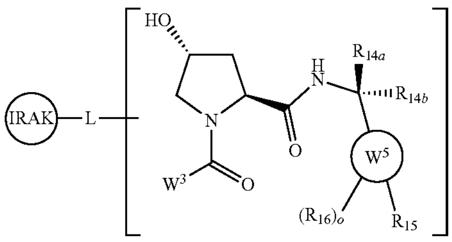

I-eee-2

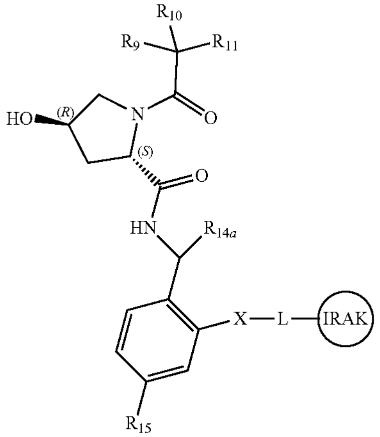

or a pharmaceutically acceptable salt thereof, wherein L and IRAK are as defined above and described in embodiments herein, and wherein each of the variables X, $W^3$, $W^5$, $R_9$, $R_{10}$, $R_{11}$, $R_{14a}$, $R_{14b}$, $R_{15}$, $R_{16}$, and o is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety thereby forming a compound of formula I-fff:

I-fff

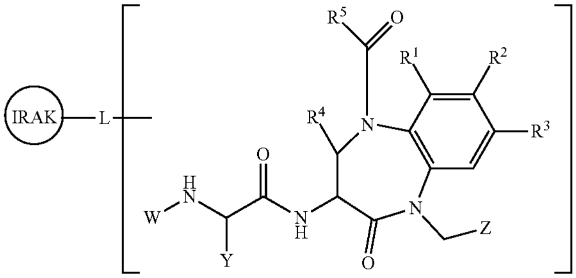

or a pharmaceutically acceptable salt thereof, wherein L and IRAK are as defined above and described in embodiments herein, and wherein each of the variables W, Y, Z, $R^1$, $R^2$, $R^3$, $R^4$, and $R^5$ is as described and defined in WO 2014/044622, US 2015/0225449. WO 2015/071393, and US 2016/0272596, the entirety of each of which is herein incorporated by reference.

In certain embodiments, the present invention provides a compound of formula I, wherein LBM is a MDM2 binding moiety thereby forming a compound of formula I-ggg:

I-ggg

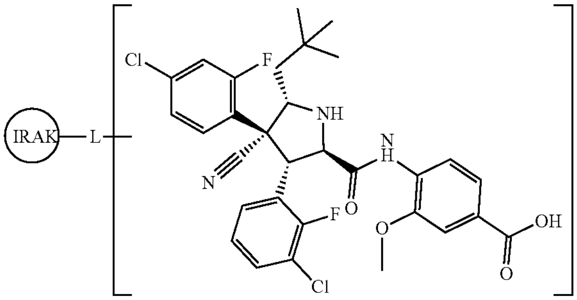

or a pharmaceutically acceptable salt thereof, wherein L and IRAK are as defined above and described in embodiments herein, as described and defined in Hines, J. et al., *Cancer Res*. (DOI: 10.1158/0008-5472.CAN-18-2918), the entirety of each of which is herein incorporated by reference.

In certain embodiments, the present invention provides a compound of formula I, wherein LBM is a DCAF16 binding moiety thereby forming a compound of formula I-hhh:

I-hhh

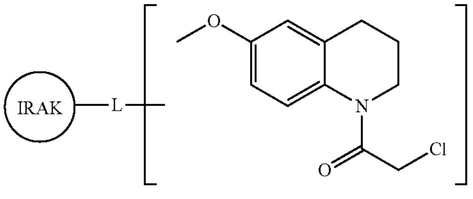

or a pharmaceutically acceptable salt thereof, wherein L and IRAK are as defined above and described in embodiments herein, as described and defined in Zhang, X. et al., *bioRxiv* (doi: https://doi.org/10.1101/443804), the entirety of each of which is herein incorporated by reference.

In certain embodiments, the present invention provides a compound of formula I, wherein LBM is a RNF114 binding moiety thereby forming a compound of formula I-iii:

I-iii

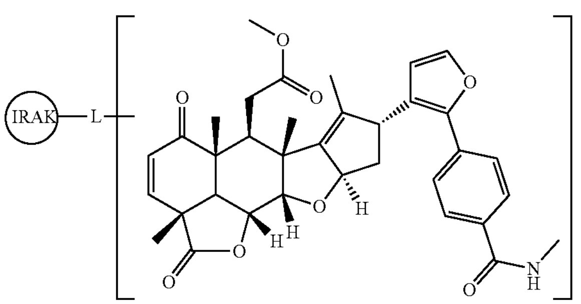

or a pharmaceutically acceptable salt thereof, wherein L and IRAK are as defined above and described in embodiments herein, as described and defined in Spradin, J. N. et al., *bioRxiv* (doi: https://doi.org/10.1101/436998), the entirety of each of which is herein incorporated by reference.

In certain embodiments, the present invention provides a compound of formula I, wherein LBM is a RNF4 binding moiety thereby forming a compound of formula I-jjj:

I-jjj

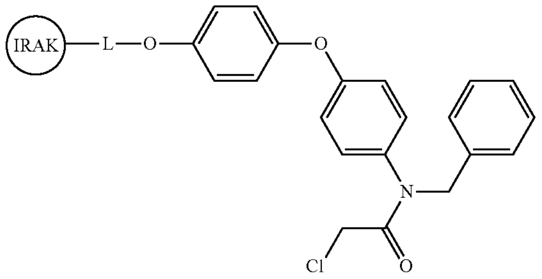

or a pharmaceutically acceptable salt thereof, wherein L and IRAK are as defined above and described in embodiments herein, as described and defined in Ward, C. C., et al., bioRxiv (doi: https://doi.org/10.1101/439125), the entirety of each of which is herein incorporated by reference.

In certain embodiments, the present invention provides a compound of formula I, wherein LBM is a VHL binding moiety thereby forming a compound of formula I-nnn-1 or I-nnn-2:

I-nnn-1

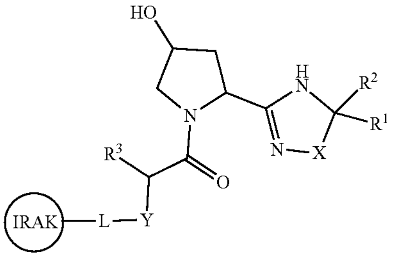

-continued

I-nnn-2

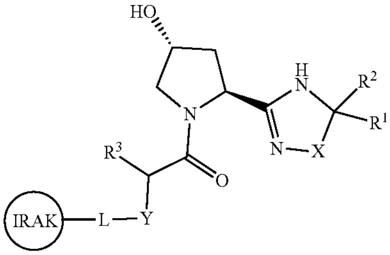

or a pharmaceutically acceptable salt thereof, wherein L and IRAK are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-ooo-1 or I-ooo-2:

I-ooo-1

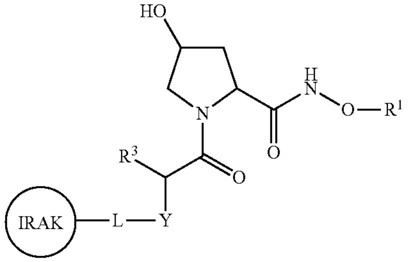

I-ooo-2

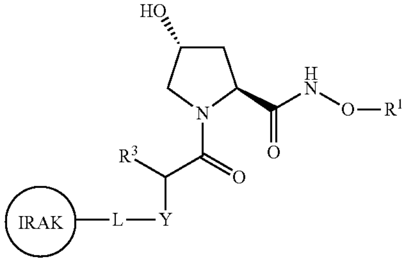

or a pharmaceutically acceptable salt thereof, wherein L and IRAK are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-ppp-1, I-ppp-2, I-ppp-3, or I-ppp-4:

I-ppp-1

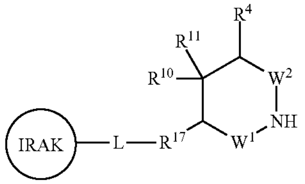

-continued

I-ppp-2

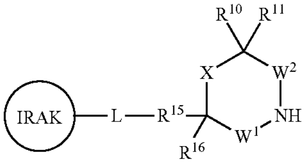

I-ppp-3

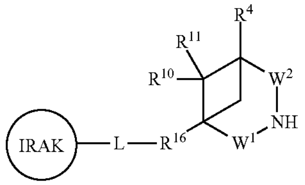

I-ppp-4

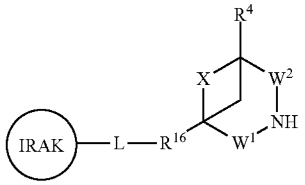

or a pharmaceutically acceptable salt thereof, wherein L and IRAK are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/099868 which is herein incorporated by reference in its entirety, and wherein

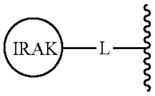

is attached to $R^{17}$ or $R^{16}$ at the site of attachment of $R^{12}$ as defined in WO 2018/237026, such that

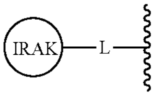

takes the lace of the $R^{12}$ substituent.

In some embodiments, LBM is

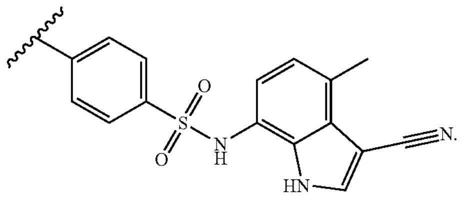 [SMILES: *c1ccc(S(=O)(=O)Nc2ccc(C)c3c(C#N)c[nH]c23)cc1]

In some embodiments, LBM is

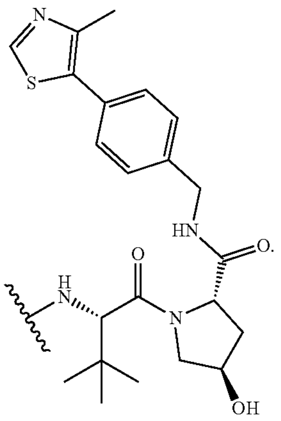 [SMILES: *N[C@H](C(=O)N1C[C@H](O)C[C@H]1C(=O)NCc1ccc(-c2scnc2C)cc1)C(C)(C)C]

In some embodiments, LBM is

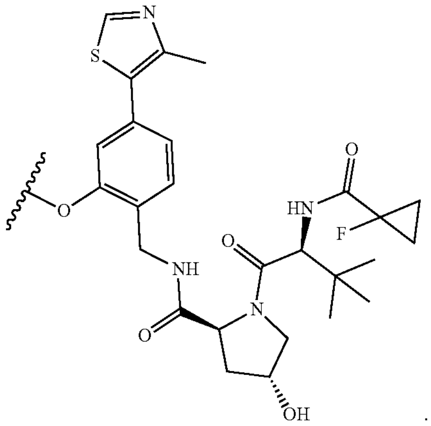 [SMILES: *Oc1cc(-c2scnc2C)ccc1CNC(=O)[C@@H]1C[C@@H](O)CN1C(=O)[C@@H](NC(=O)C1(F)CC1)C(C)(C)C]

In some embodiments, LBM is

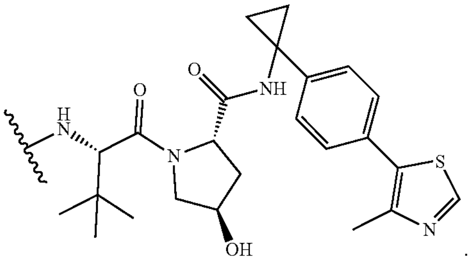 [SMILES: *N[C@H](C(=O)N1C[C@H](O)C[C@H]1C(=O)NC1(c2ccc(-c3scnc3C)cc2)CC1)C(C)(C)C]

In some embodiments, LBM is
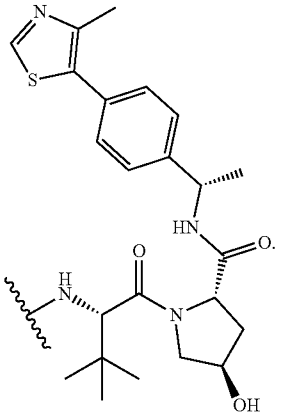 [SMILES: *N[C@H](C(=O)N1C[C@H](O)C[C@H]1C(=O)N[C@@H](C)c1ccc(-c2scnc2C)cc1)C(C)(C)C]
In some embodiments, LBM is
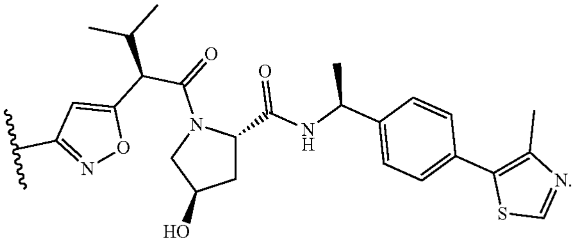 [SMILES: *c1cc([C@H](C(=O)N2C[C@H](O)C[C@H]2C(=O)N[C@@H](C)c2ccc(-c3scnc3C)cc2)C(C)C)on1]
In some embodiments, LBM is
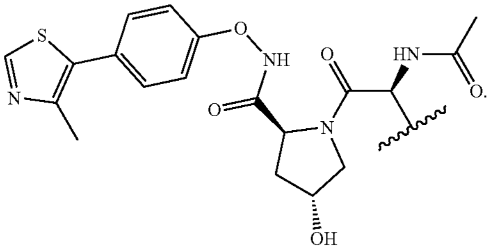 [SMILES: *[C@H](NC(C)=O)C(=O)N1C[C@H](O)C[C@H]1C(=O)NOc1ccc(-c2scnc2C)cc1]
In some embodiments, LBM is
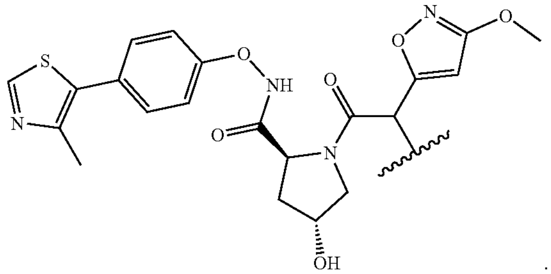 [SMILES: *C(C(=O)N1C[C@H](O)C[C@H]1C(=O)NOc1ccc(-c2scnc2C)cc1)c1cc(OC)no1]
In some embodiments, LBM is
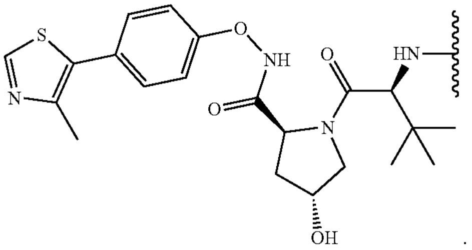 [SMILES: *N[C@H](C(=O)N1C[C@H](O)C[C@H]1C(=O)NOc1ccc(-c2scnc2C)cc1)C(C)(C)C]
In some embodiments, LBM is
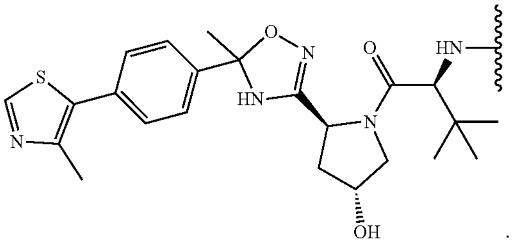 [SMILES: *N[C@H](C(=O)N1C[C@H](O)C[C@H]1C1=NOC(C)(c2ccc(-c3scnc3C)cc2)N1)C(C)(C)C]
In some embodiments, LBM is
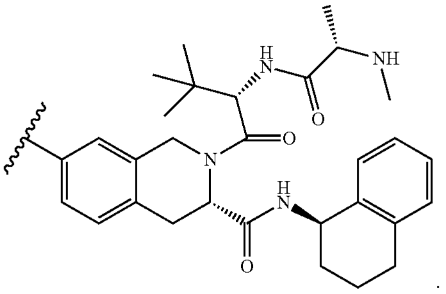 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
In some embodiments, LBM is
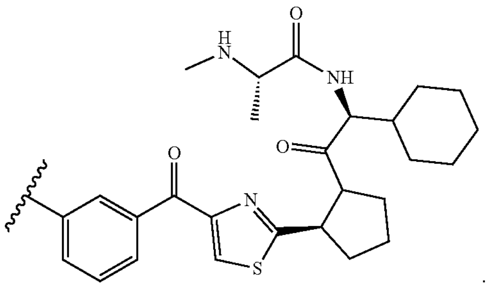 [SMILES: *c1cccc(C(=O)c2csc([C@@H]3CCCC3C(=O)[C@@H](NC(=O)[C@H](C)NC)C3CCCCC3)n2)c1]

In some embodiments, LBM is
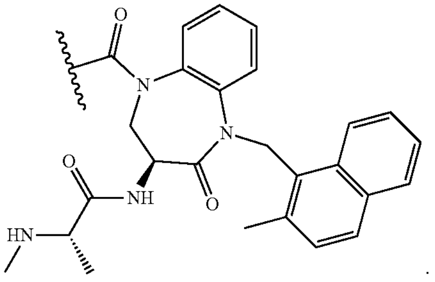 [SMILES: *C(=O)N1C[C@H](NC(=O)[C@H](C)NC)C(=O)N(Cc2c(C)ccc3ccccc23)c2ccccc21]
In some embodiments, LBM is
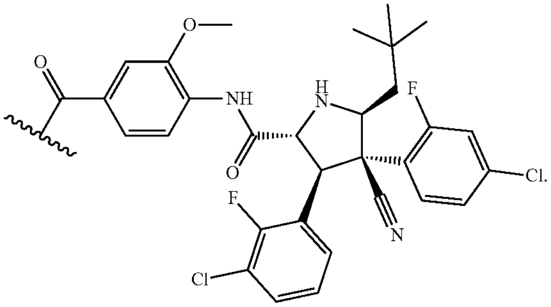 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
In some embodiments, LBM is
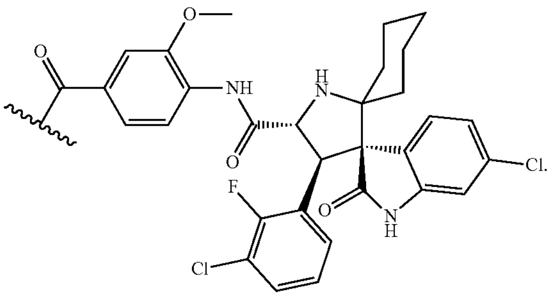 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)c(OC)c1]
In some embodiments, LBM is
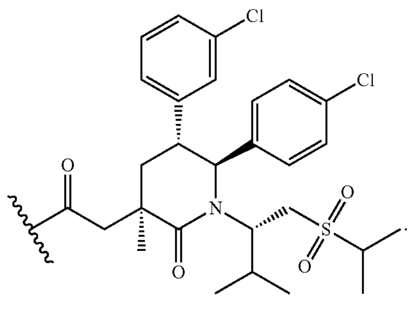 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]
In some embodiments LBM is
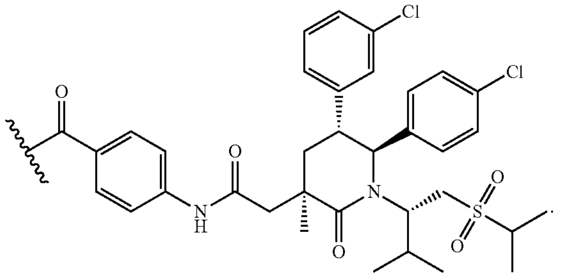 [SMILES: *C(=O)c1ccc(NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1]
In some embodiments, LBM is
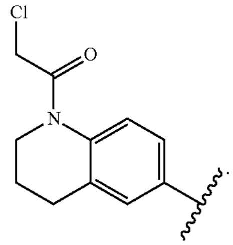 [SMILES: *c1ccc2c(c1)CCCN2C(=O)CCl]
In some embodiments, LBM is
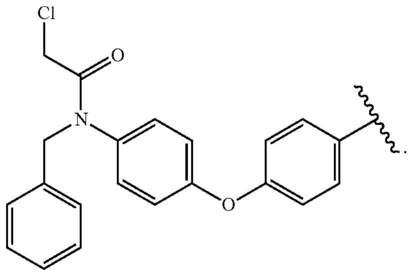 [SMILES: *c1ccc(Oc2ccc(N(Cc3ccccc3)C(=O)CCl)cc2)cc1]
In some embodiments, LBM is
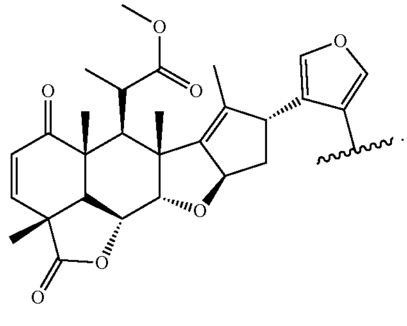

In some embodiments, LBM is
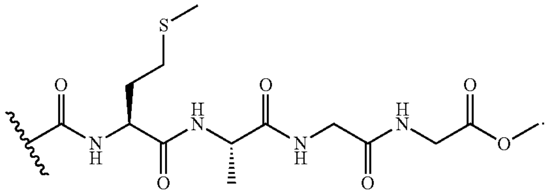 [SMILES: *C(=O)N[C@@H](CCSC)C(=O)N[C@@H](C)C(=O)NCC(=O)NCC(=O)OC]
In some embodiments, LBM is
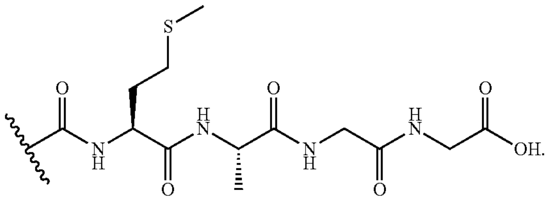 [SMILES: *C(=O)N[C@@H](CCSC)C(=O)N[C@@H](C)C(=O)NCC(=O)NCC(=O)O]
In some embodiments, LBM is
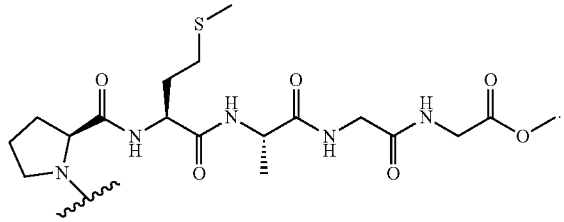 [SMILES: *N1CCC[C@H]1C(=O)N[C@@H](CCSC)C(=O)N[C@@H](C)C(=O)NCC(=O)NCC(=O)OC]
In some embodiments, LBM is
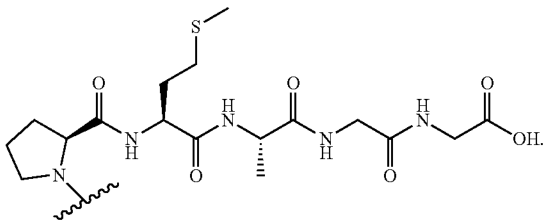 [SMILES: *N1CCC[C@H]1C(=O)N[C@@H](CCSC)C(=O)N[C@@H](C)C(=O)NCC(=O)NCC(=O)O]
In some embodiments, LBM is
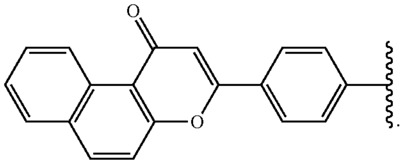 [SMILES: *c1ccc(-c2cc(=O)c3c(ccc4ccccc43)o2)cc1]
In some embodiments, LBM is
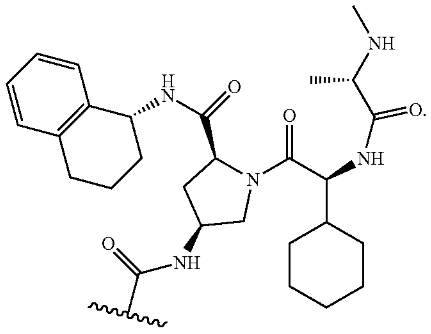 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]
In some embodiments, LBM is
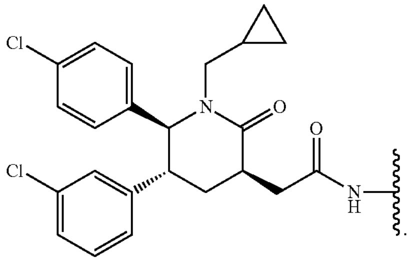 [SMILES: *NC(=O)C[C@H]1C[C@H](c2cccc(Cl)c2)[C@@H](c2ccc(Cl)cc2)N(CC2CC2)C1=O]
In some embodiments, LBM is
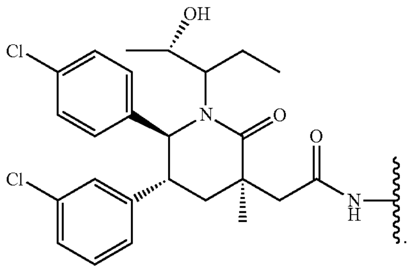 [SMILES: *NC(=O)C[C@@]1(C)C[C@H](c2cccc(Cl)c2)[C@@H](c2ccc(Cl)cc2)N(C(CC)[C@H](C)O)C1=O]
In some embodiments, LBM is
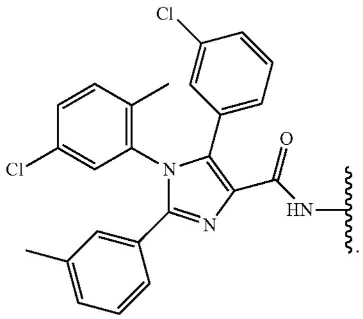 [SMILES: *NC(=O)c1nc(-c2cccc(C)c2)n(-c2cc(Cl)ccc2C)c1-c1cccc(Cl)c1]

In some embodiments, LBM is

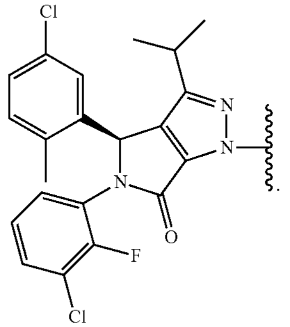 [SMILES: *n1nc(C(C)C)c2c1C(=O)N(c1cccc(Cl)c1F)[C@H]2c1cc(Cl)ccc1C]

In certain embodiments, the present invention provides a compound of formula I, wherein LBM is a CRBN E3 ubiquitin ligase binding moiety thereby forming a compound of formula I-qqq:

I-qqq

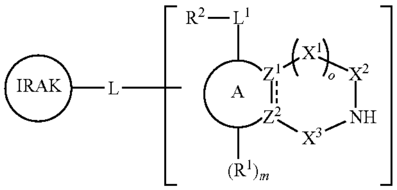

or a pharmaceutically acceptable salt thereof, wherein L and IRAK are as defined above and described in embodiments herein, wherein:

each $X^1$ is independently —$CH_2$—, —O—, —NR—, —$CF_2$—,

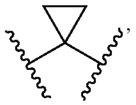 [SMILES: *C1(*)CC1]

—C(O)—, —C(S)—, or

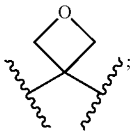

$X^2$ and $X^3$ are independently —$CH_2$—, —C(O)—, —C(S)— or

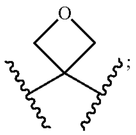 [SMILES: *C1(*)COC1]

$Z^1$ and $Z^2$ are independently a carbon atom or a nitrogen atom;

Ring A is a fused ring selected from benzo, a 4-6 membered saturated or partially unsaturated carbocyclic or heterocyclic ring having 1-3 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—;

each $R^1$ is independently selected from hydrogen, deuterium, $R^4$, halogen, —CN, —$NO_2$, —OR, —SR, —$NR_2$, —$S(O)_2R$, —$S(O)_2NR_2$, —S(O)R, —$CF_2R$, —$CR_2F$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —Si(OR)$R_2$, and —$SiR_3$; or two $R^1$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^2$ is selected from

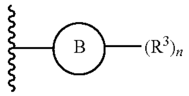

or hydrogen;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups;

each $R^3$ is independently selected from hydrogen, deuterium, $R^4$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, and —$SiR_3$;

each $R^4$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

is a single or double bond;

m is 0, 1, 2, 3 or 4;

n is 0, 1, 2, 3 or 4; and o is 0, 1, or 2.

As defined above and described herein each $X^1$ is independently a covalent bond, —$CH_2$—, —O—, —NR—, —$CF_2$—,

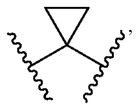 [SMILES: *C1(*)CC1]

—C(O)—, —C(S)—, or

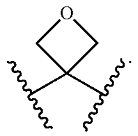 [SMILES: *C1(*)COC1]

In some embodiments, $X^1$ is a covalent bond. In some embodiments, $X^1$ is —$CH_2$—. In some embodiments, $X^1$ is —O—. In some embodiments, $X^1$ is —NR—. In some embodiments, $X^1$ is —$CF_2$—. In some embodiments, $X^1$ is

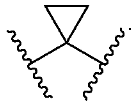 [SMILES: *C1(*)CC1]

In some embodiments, $X^1$ is —C(O)—. In some embodiments, $X^1$ is —C(S)—. In some embodiments, $X^1$ is

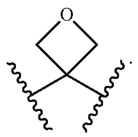 [SMILES: *C1(*)COC1]

In certain embodiments, $X^1$ is selected from those shown in the compounds of Table 1.

As defined above and described herein, $X^2$ and $X^3$ are independently —$CH_2$—, —C(O)—, —C(S)—, or

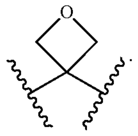 [SMILES: *C1(*)COC1]

In some embodiments, $X^2$ and $X^3$ are independently —$CH_2$—. In some embodiments, $X^2$ and $X^3$ are independently —C(O)—. In some embodiments, $X^2$ and $X^3$ are independently —C(S)—. In some embodiments, $X^2$ and $X^3$ are independently

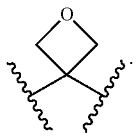 [SMILES: *C1(*)COC1]

In certain embodiments, $X^2$ and $X^3$ are independently selected from those shown in the compounds of Table 1.

As defined above and described herein, $X^4$ is a covalent bond, —$CH_2$—, —$CR_2$—, —O—, —NR—, $CF_2$—,

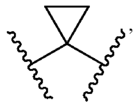 [SMILES: *C1(*)CC1]

—C(O)—, —C(S)—, or

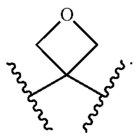 [SMILES: *C1(*)COC1]

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^2$ are independently a carbon atom.

In certain embodiments, $Z^1$ and $Z^2$ are independently selected from those shown in the compounds of Table 1.

As defined above and described herein, Ring A is fused ring selected from benzo or a 5-6 membered heteroaryl ring having 1-4 heteroatoms independently selected from nitrogen, oxygen, and sulfur.

In some embodiments, Ring A is benzo. In some embodiments, Ring A is a 5-6 membered heteroaryl ring having 1-4 heteroatoms independently selected from nitrogen, oxygen, and sulfur.

In some embodiments, Ring A is

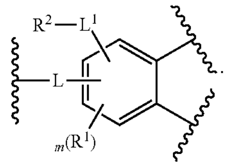

In some embodiments, Ring A is

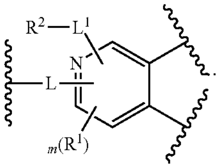

In some embodiments, Ring A is

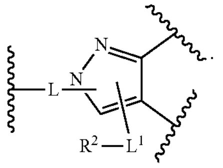

In some embodiments, Ring A is

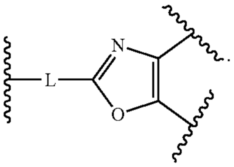

In certain embodiments, Ring A is selected from those shown in the compounds of Table 1.

As defined above and described herein, $L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, $—CR_2—$, —CRF—, $—CF_2—$, —NR—, or $—S(O)_2—$.

In some embodiments, $L^1$ is a covalent bond. In some embodiments, $L^1$ is a $C_{1-3}$ bivalent straight or branched saturated or unsaturated hydrocarbon chain wherein 1-2 methylene units of the chain are independently and optionally replaced with —O—, —S—, —C(O)—, —C(S)—, $—CR_2—$, —CRF—, $—CF_2—$, —NR—, or $—S(O)_2—$.

In some embodiments, $L^1$ is —C(O)—.

In certain embodiments, $L^1$ is selected from those shown in the compounds of Table 1.

As defined above and described herein, each $R^1$ is independently selected from hydrogen, deuterium, $R^4$, halogen, —CN, $—NO_2$, —OR, —SR, $—NR_2$, $—S(O)_2R$, $—S(O)_2NR_2$, —S(O)R, $—CF_2R$, $—CF_3$, $—CR_2(OR)$, $—CR_2(NR_2)$, —C(O)R, —C(O)OR, $—C(O)NR_2$, —C(O)N(R)OR, —OC(O)R, $—OC(O)NR_2$, $—C(S)NR_2$, —N(R)C(O)OR, —N(R)C(O)R, $—N(R)C(O)NR_2$, $—N(R)S(O)_2R$, $—OP(O)R_2$, $—OP(O)(OR)_2$, $—OP(O)(OR)NR_2$, $—OP(O)(NR_2)_2$, $—Si(OR)R_2$, and $—SiR_3$, or two $R^1$ groups are optionally taken together to form an optionally substituted 5-8 membered partially unsaturated or aryl fused ring having 0-2 heteroatoms independently selected from nitrogen, oxygen, or sulfur.

In some embodiments, $R^1$ is hydrogen. In some embodiments, $R^1$ is deuterium. In some embodiments, $R^1$ is $R^4$. In some embodiments, $R^1$ is halogen. In some embodiments, $R^1$ is —CN. In some embodiments, $R^1$ is $—NO_2$. In some embodiments, $R^1$ is —OR. In some embodiments, $R^1$ is —SR. In some embodiments, $R^1$ is $—NR_2$. In some embodiments, $R^1$ is $—S(O)_2R$. In some embodiments, $R^1$ is $—S(O)_2NR_2$. In some embodiments, $R^1$ is —S(O)R. In some embodiments, $R^1$ is $—CF_2R$. In some embodiments, $R^1$ is $—CF_3$. In some embodiments, $R^1$ is $—CR_2(OR)$. In some embodiments, $R^1$ is $—CR_2(NR_2)$. In some embodiments, $R^1$ is —C(O)R. In some embodiments, $R^1$ is —C(O)OR. In some embodiments, $R^1$ is $—C(O)NR_2$. In some embodiments, $R^1$ is —C(O)N(R)OR. In some embodiments, $R^1$ is —OC(O)R. In some embodiments, $R^1$ is $—OC(O)NR_2$. In some embodiments, $R^1$ is $—C(S)NR_2$. In some embodiments, $R^1$ is —N(R)C(O)OR. In some embodiments, $R^1$ is —N(R)C(O)R. In some embodiments, $R^1$ is $—N(R)C(O)NR_2$. In some embodiments, $R^1$ is $—N(R)S(O)_2R$. In some embodiments, $R^1$ is $—OP(O)R_2$. In some embodiments, $R^1$ is $—OP(O)(OR)_2$. In some embodiments, $R^1$ is $—OP(O)(OR)NR_2$. In some embodiments, $R^1$ is $—OP(O)(NR_2)_2$. In some embodiments, $R^1$ is $—Si(OR)R_2$. In some embodiments, $R^1$ is $—SiR_3$. In some embodiments, two $R^1$ groups are optionally taken together to form an optionally substituted 5-8 membered partially unsaturated or aryl fused ring having 0-2 heteroatoms independently selected from nitrogen, oxygen, or sulfur.

In some embodiments, $R^1$ is fluoro. In some embodiments, $R^1$ is bromo. In some embodiments, $R^1$ is methyl. In some embodiments, $R^1$ is —OH. In some embodiments, $R^1$ is $—NH_2$. In some embodiments, $R^1$ is $—NHCH_3$. In some embodiments, $R^1$ is $—N(CH_3)_2$. In some embodiments, $R^1$ is $—NHCH(CH_3)_2$. In some embodiments, $R^1$ is $—NHSO_2CH_3$. In some embodiments, $R^1$ is $—CH_2OH$. In some embodiments, $R^1$ is $—CH_2NH_2$. In some embodiments, $R^1$ is $—C(O)NH_2$. In some embodiments, $R^1$ is $—C(O)NHCH_3$. In some embodiments, $R^1$ is

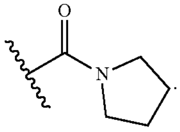 [SMILES: *C(=O)N1CCCC1]

In some embodiments, $R^1$ is

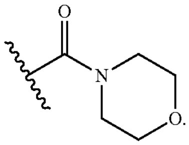 [SMILES: *C(=O)N1CCOCC1]

In some embodiments, $R^1$ is

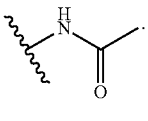

In some embodiments, $R^1$ is

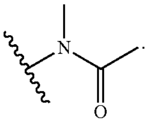 [SMILES: *N(C)C(C)=O]

In some embodiments, $R^1$ is

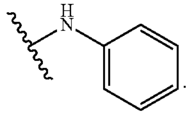

In some embodiments, $R^1$ is

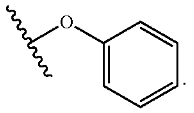 [SMILES: *Oc1ccccc1]

In some embodiments, $R^1$ is

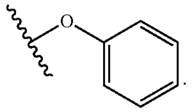

In some embodiments, $R^1$ is

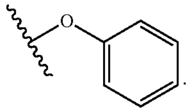

In some embodiments, $R^1$ is

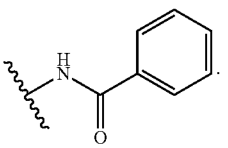 [SMILES: *NC(=O)c1ccccc1]

In some embodiments, $R^1$ is

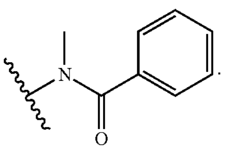 [SMILES: *N(C)C(=O)c1ccccc1]

In certain embodiments, each $R^1$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, $R^2$ is selected from

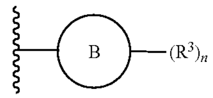

or hydrogen.

In some embodiment $R^2$ is

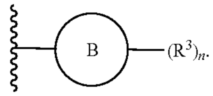

In some embodiments, $R^2$ is hydrogen.

In certain embodiments, $R^2$ is selected from those shown in the compounds of Table 1.

As defined above and described herein, Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups.

In some embodiments, Ring B is phenyl. In some embodiments, Ring B is a 4-10 membered saturated or partially unsaturated mono- or bicyclic carbocyclic or heterocyclic ring having 1-3 heteroatoms independently selected from nitrogen, oxygen, and sulfur In some embodiments, Ring B is a 5-6 membered heteroaryl ring having 1-4 heteroatoms independently selected from nitrogen, oxygen, and sulfur. In some embodiments, Ring B is further optionally substituted with 1-2 oxo groups.

In some embodiments, Ring B is

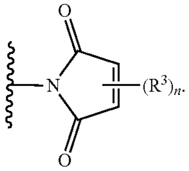

In some embodiments, Ring B is

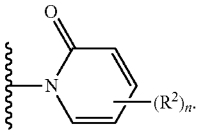

In some embodiments, Ring B is

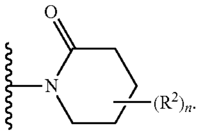

In some embodiments Ring B is

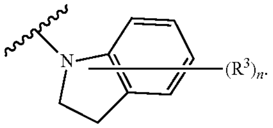

In some embodiments Ring B is

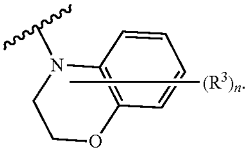

In some embodiments Ring B is

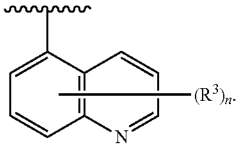

In some embodiments Ring B is

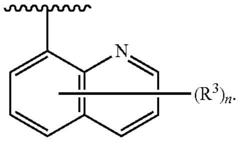

In some embodiments Ring B is

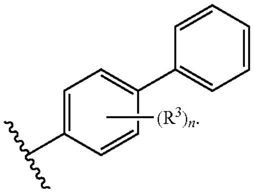

In some embodiments Ring B is

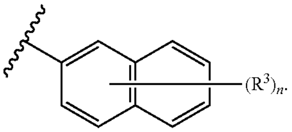

In some embodiments Ring B is

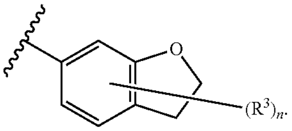

In some embodiments Ring B is

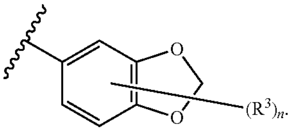

In some embodiments Ring B is

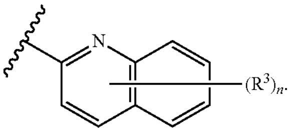

In some embodiments Ring B is

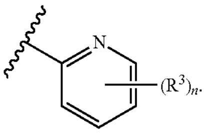

In some embodiments Ring B is

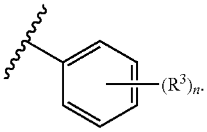

In certain embodiments, Ring B is selected from those shown in the compounds of Table 1.

As defined above and described herein, each $R^3$ is independently selected from hydrogen, deuterium, $R^4$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, and —$SiR_3$.

In some embodiments, $R^3$ is hydrogen. In some embodiments, $R^3$ is deuterium. In some embodiments, $R^3$ is $R^4$. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —SR. In some embodiments, $R^3$ is —$NR_2$. In some embodiments, $R^3$ is —$S(O)_2R$. In some embodiments, $R^3$ is —$S(O)_2NR_2$. In some embodiments, $R^3$ is —S(O)R. In some embodiments, $R^3$ is —$CF_2R$. In some embodiments, $R^3$ is —$CF_3$. In some embodiments, $R^3$ is —$CR_2(OR)$. In some embodiments, $R^3$ is —$CR_2(NR_2)$. In some embodiments, $R^3$ is —C(O)R. In some embodiments, $R^3$ is —C(O)OR. In some embodiments, $R^3$ is —$C(O)NR_2$. In some embodiments, $R^3$ is —C(O)N(R)OR. In some embodiments, $R^3$ is —OC(O)R. In some embodiments, $R^3$ is —$OC(O)NR_2$. In some embodiments, $R^3$ is —N(R)C(O)OR. In some embodiments, $R^3$ is —N(R)C(O)R. In some embodiments, $R^3$ is —$N(R)C(O)NR_2$. In some embodiments, $R^3$ is —$N(R)S(O)_2R$. In some embodiments, $R^3$ is —$OP(O)R_2$. In some embodiments, $R^3$ is —$OP(O)(OR)_2$. In some embodiments, $R^3$ is —$OP(O)(OR)NR_2$. In some embodiments, $R^3$ is —$OP(O)(NR_2)_2$. In some embodiments, $R^3$ is —$SiR_3$ In certain embodiments, $R^3$ is selected from those shown in the compounds of Table 1.

As defined above and described herein, each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^4$ is an optionally substituted $C_{1-6}$ aliphatic. In some embodiments, $R^4$ is an optionally substituted phenyl. In some embodiments, $R^4$ is an optionally substituted 4-7 membered saturated or partially unsaturated heterocyclic ring having 1-2 heteroatoms independently selected from nitrogen, oxygen, and sulfur. In some embodiments, $R^4$ is an optionally substituted 5-6 membered heteroaryl ring having 1-4 heteroatoms independently selected from nitrogen, oxygen, and sulfur.

In some embodiments, $R^4$ is

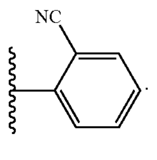 [SMILES: *c1ccccc1C#N]

In some embodiments, $R^4$ is

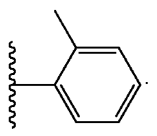 [SMILES: *c1ccccc1C]

In some embodiments, $R^4$ is

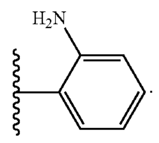 [SMILES: *c1ccccc1N]

In some embodiments, $R^4$ is

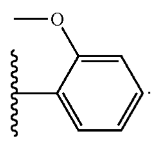 [SMILES: *c1ccccc1OC]

In some embodiments, $R^4$ is

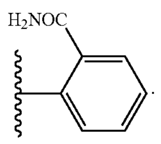

In some embodiments, $R^4$ is

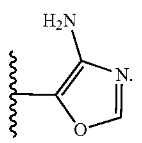

In some embodiments, $R^4$ is

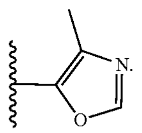 [SMILES: *c1ocnc1C]

In some embodiments, $R^4$ is

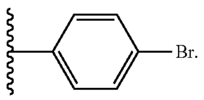 [SMILES: *c1ccc(Br)cc1]

In some embodiments, $R_4$ is

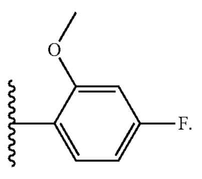 [SMILES: *c1ccc(F)cc1OC]

In some embodiments, $R^4$ is

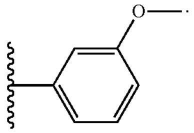 [SMILES: *c1cccc(OC)c1]

In some embodiments, $R^4$ is

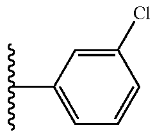 [SMILES: *c1cccc(Cl)c1]

In some embodiments, $R^4$ is

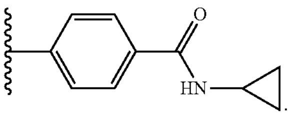 [SMILES: *c1ccc(C(=O)NC2CC2)cc1]

In some embodiments, $R^4$ is

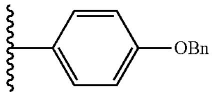 [SMILES: *c1ccc(OCc2ccccc2)cc1]

In some embodiments, $R^4$ is

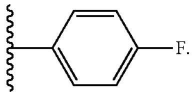 [SMILES: *c1ccc(F)cc1]

In some embodiments, $R^4$ is

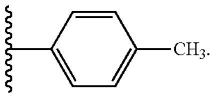 [SMILES: *c1ccc(C)cc1]

In some embodiments, $R^4$ is

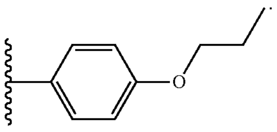 [SMILES: *c1ccc(OCCC)cc1]

In some embodiments, $R^4$ is

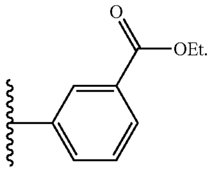 [SMILES: *c1cccc(C(=O)OCC)c1]

In some embodiments, $R^4$ is

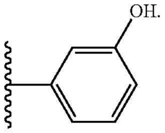 [SMILES: *c1cccc(O)c1]

In some embodiments, $R^4$ is

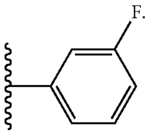

In some embodiments, $R^4$ is

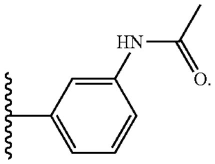 [SMILES: *c1cccc(NC(C)=O)c1]

In some embodiments, $R^4$ is

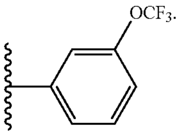 [SMILES: *c1cccc(OC(F)(F)F)c1]

In some embodiments, $R^4$ is

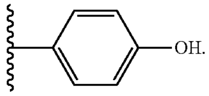 [SMILES: *c1ccc(O)cc1]

In some embodiments, $R^4$ is

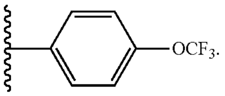 [SMILES: *c1ccc(OC(F)(F)F)cc1]

In some embodiments, $R^4$ is

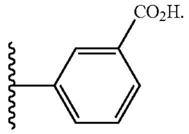 [SMILES: *c1cccc(C(=O)O)c1]

In some embodiments, $R^4$ is

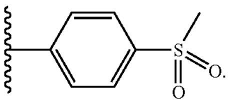 [SMILES: *c1ccc(S(C)(=O)=O)cc1]

In some embodiments, $R^4$ is

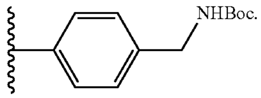 [SMILES: *c1ccc(CNC(=O)OC(C)(C)C)cc1]

In some embodiments, $R^4$ is

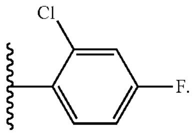 [SMILES: *c1ccc(F)cc1Cl]

In some embodiments, $R^4$ is

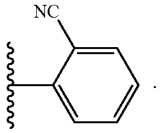

In some embodiments, $R^4$ is

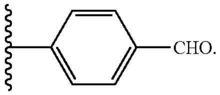 [SMILES: *c1ccc(C=O)cc1]

In some embodiments, $R^4$ is

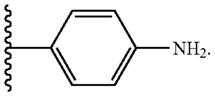

In some embodiments, $R^4$ is

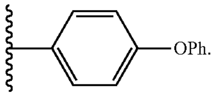

In some embodiments, $R^4$ is

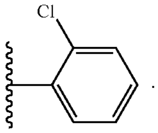 [SMILES: *c1ccccc1Cl]

In some embodiments, $R^4$ is

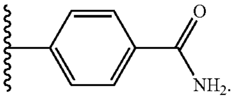

In some embodiments, $R^4$ is

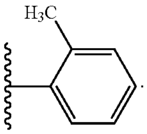

In some embodiments, $R^4$ is

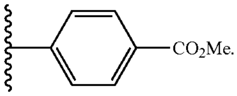 [SMILES: *c1ccc(C(=O)OC)cc1]

In some embodiments, $R^4$ is

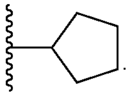

In some embodiments, $R^4$ is

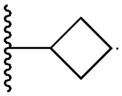 [SMILES: *C1CCC1]

In some embodiments, $R^4$ is

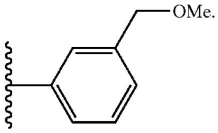 [SMILES: *c1cccc(COC)c1]

In some embodiments, $R^4$ is

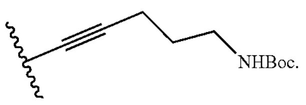 [SMILES: *C#CCCCNC(=O)OC(C)(C)C]

In certain embodiments, $R^4$ is selected from those shown in the compounds of Table 1.

As defined above and described herein, ---- is a single or double bond.

In some embodiments, ---- is a single bond. In some embodiments, ---- is a double bond.

In certain embodiments, ---- is selected from those shown in the compounds of Table 1.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In certain embodiments, m is selected from those shown in the compounds of Table 1.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In certain embodiments, n is selected from those shown in the compounds of Table 1.

As defined above and described herein, o is 0, 1, or 2.

In some embodiments, n is 0. In some embodiments, n is 1. In some embodiments, m is 2.

In certain embodiments, o is selected from those shown in the compounds of Table 1.

In some embodiments, the present invention provides a compound of formula I-qqq, wherein Ring A is benzo, o is 1, $X^1$ is —$CH_2$—, $X^2$ and $X^3$ are —C(O)—, and $Z^1$ and $Z^2$ are carbon atoms as shown, to provide a compound of formula I-qqq-1:

I-qqq-1

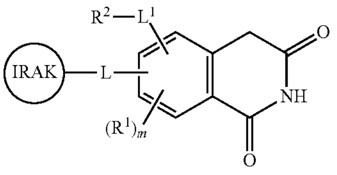

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is imidazolyl, o is 1, $X^1$ is —$CH_2$—, $X^2$ and $X^3$ are —C(O)—, and $Z^1$ and $Z^2$ are carbon atoms as shown, to provide a compound of formula I-qqq-2:

I-qqq-2

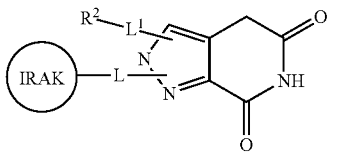

or a pharmaceutically acceptable salt thereof, wherein each of IRAK, L, $L^1$, and $R^2$ is as defined above and described in embodiments herein, both singly and in combination.

In some embodiments, the present invention provides a compound of formula I-qqq, wherein Ring A is imidazolyl, o is 1, $X^1$ is —$CH_2$—, $X^2$ and $X^3$ are —C(O)—, and $Z^1$ and $Z^2$ are carbon atoms as shown, to provide a compound of formula I-qqq-3:

I-qqq-3

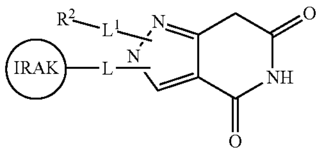

or a pharmaceutically acceptable salt thereof, wherein each of IRAK, L, $L^1$, and $R^2$ is as defined above and described in embodiments herein, both singly and in combination.

In some embodiments, the present invention provides a compound of formula I-qqq, wherein Ring A is oxazolyl, o is 1, $X^1$ is —$CH_2$—, $X^2$ and $X^3$ are —C(O)—, and $Z^1$ and $Z^2$ are carbon atoms as shown, to provide a compound of formula I-qqq-4:

I-qqq-4

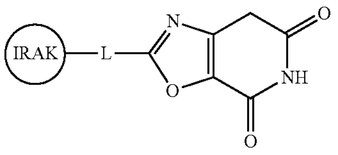

or a pharmaceutically acceptable salt thereof, wherein each of IRAK and L is as defined above and described in embodiments herein, both singly and in combination.

In some embodiments, the present invention provides a compound of formula I-qqq, wherein Ring A is benzo, o is 0, $X^1$ is a covalent bond, $X^2$ and $X^3$ are —C(O)—, and $Z^1$ and $Z^2$ are carbon atoms as shown, to provide a compound of formula I-qqq-5:

I-qqq-5

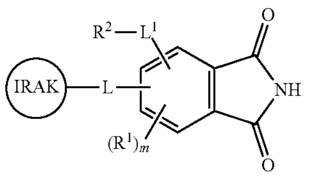

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$ is —O—, $X^2$ and $X^3$ are —C(O)—, and $Z^1$ and $Z^2$ are carbon atoms as shown, to provide a compound of formula I-qqq-6:

I-qqq-6

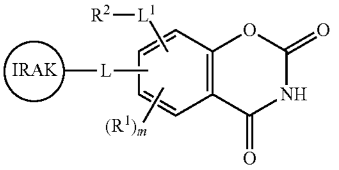

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$ is —NR—, $X^2$ and $X^3$ are —C(O)—, and $Z^1$ and $Z^2$ are carbon atoms as shown, to provide a compound of formula I-qqq-7:

I-qqq-7

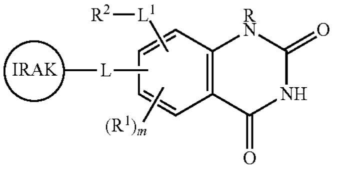

or a pharmaceutically acceptable salt thereof, wherein each of IRAK, L, $L^1$, R, $R^1$, $R^2$, and m is as defined above and described in embodiments herein, both singly and in combination.

In some embodiments, the present invention provides a compound of formula I-qqq, wherein Ring A is benzo, o is 1, $X^1$ is —$CF_2$—, $X^2$ and $X^3$ are —C(O)—, and $Z^1$ and $Z^2$ are carbon atoms as shown, to provide a compound of formula I-qqq-8:

I-qqq-8

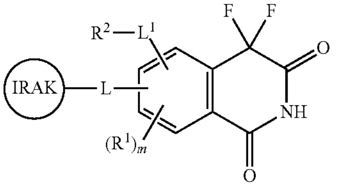

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$ is

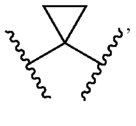 [SMILES: *C1(*)CC1]

$X^2$ and $X^3$ are —C(O)—, and $Z^1$ and $Z^2$ are carbon atoms as shown, to provide a compound of formula I-qqq-9:

I-qqq-9

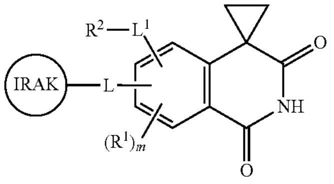

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is pyridyl, o is 1, $X^1$ is —$CH_2$—, $X^2$ and $X^3$ are —C(O)—, and $Z^1$ and $Z^2$ are carbon atoms as shown, to provide a compound of formula I-qqq-10:

I-qqq-10

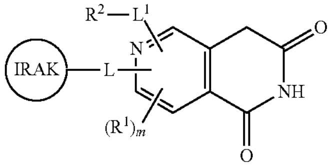

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is pyridyl, o is 1, $X^1$ is —$CH_2$—, $X^2$ and $X^3$ are —C(O)—, and $Z^1$ and $Z^2$ are carbon atoms as shown, to provide a compound of formula I-qqq-11:

I-qqq-11

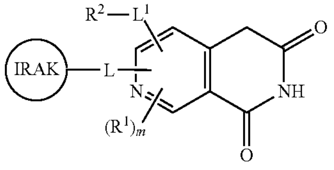

or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$, $X^2$ and $X^3$ are —C(O)—, and $Z^1$ and $Z^2$ are carbon atoms as shown, to provide a compound of formula I-qqq-12:

I-qqq-12

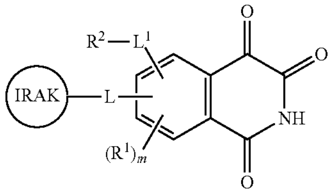

or a pharmaceutically acceptable salt thereof, wherein each of IRAK, L, $L^1$, $R^1$, $R^2$, and m is as defined above and described in embodiments herein, both singly and in combination.

In some embodiments, LBM is

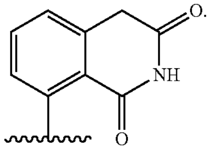 [SMILES: *c1cccc2c1C(=O)NC(=O)C2]

In some embodiments, LBM is

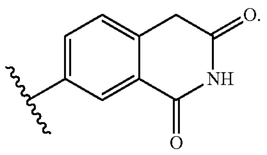 [SMILES: *c1ccc2c(c1)C(=O)NC(=O)C2]

In some embodiments, LBM is

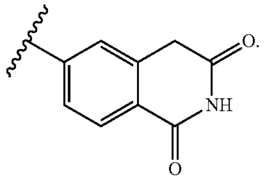 [SMILES: *c1ccc2c(c1)CC(=O)NC2=O]

In some embodiments, LBM is

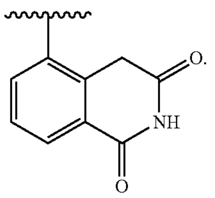 [SMILES: *c1cccc2c1CC(=O)NC2=O]

In some embodiments, LBM is

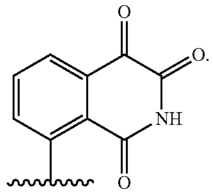 [SMILES: *c1cccc2c1C(=O)NC(=O)C2=O]

In some embodiments, LBM is

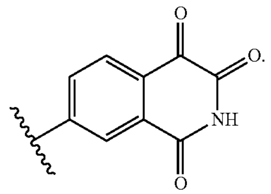 [SMILES: *c1ccc2c(c1)C(=O)NC(=O)C2=O]

In some embodiments, LBM is

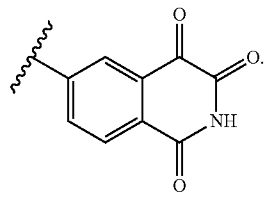 [SMILES: *c1ccc2c(c1)C(=O)C(=O)NC2=O]

In some embodiments, LBM is

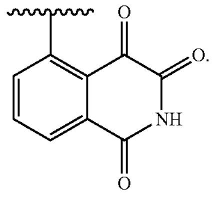 [SMILES: *c1cccc2c1C(=O)C(=O)NC2=O]

In some embodiments, LBM is selected from those in Table 1, below.

In certain embodiments, the present invention provides a compound of formula I, wherein LBM is a RPN13 binding moiety thereby forming a compound of formula I-rrr:

I-rrr

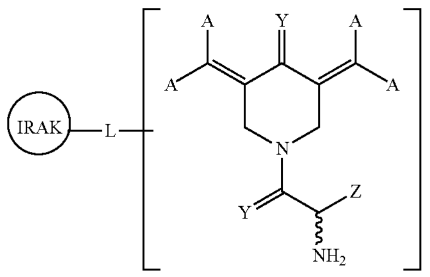

or a pharmaceutically acceptable salt thereof, wherein L and IRAK are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubr1 binding moiety as described in Shanmugasundaram, K. et al, J. Bio. Chem. 2019, doi: 10.1074/jbc.AC119.010790, the entirety of each of which is herein incorporated by reference, thereby forming a compound of formula I-sss-1 or I-sss-2:

I-sss-1

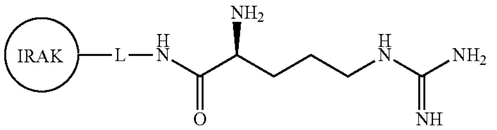

I-sss-2

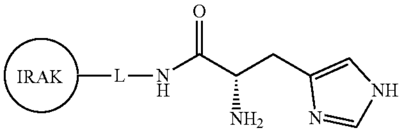

or a pharmaceutically acceptable salt thereof, wherein L and IRAK are as defined above and described in embodiments herein.

In certain embodiments, the present invention provides a compound of formula I, wherein LBM is a CRBN E3 ubiquitin ligase binding moiety thereby forming a compound of formula I-uuu-1, I-uuu-2, I-uuu-3 or I-uuu-4:

I-ttt-1

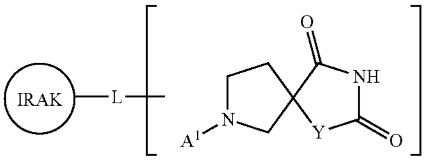

I-uuu-2

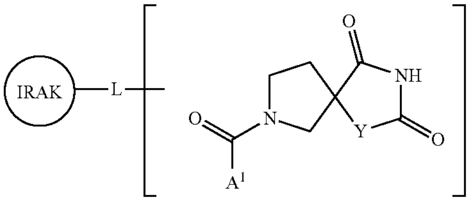

-continued

I-uuu-3

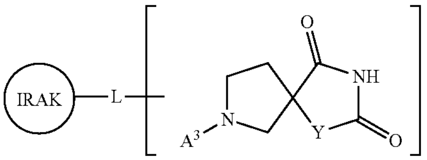

I-uuu-4

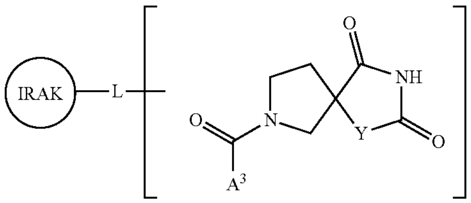

or a pharmaceutically acceptable salt thereof, wherein L and IRAK are as defined above and described in embodiments herein, and wherein each of the variables Y, $A^1$, and $A^3$ is as described and defined in WO 2019/236483, the entirety of each of which is herein incorporated by reference.

In certain embodiments, the present invention provides a compound of formula I, wherein LBM is human kelch-like ECH-associated protein 1 (KEAP1) thereby forming a compound of formula I-vvv:

I-vvv

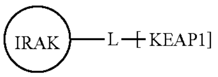

or a pharmaceutically acceptable salt thereof, wherein L and IRAK are as defined above and described in embodiments herein, both singly and in combination.

In certain embodiments, the present invention provides a compound of formula I, wherein LBM is KEAP1 binding moiety as recited in Lu et al., Euro. J. Med. Chem., 2018, 146:251-9, thereby forming a compound of formula I-www:

I-www

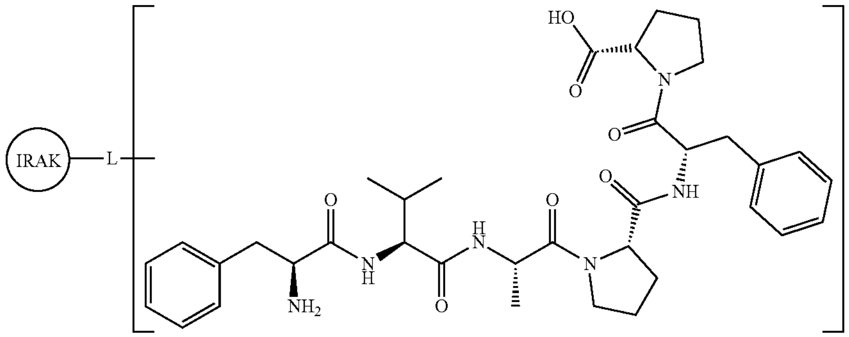

or a pharmaceutically acceptable salt thereof, wherein L and IRAK are as defined above and described in embodiments herein, both singly and in combination.

In certain embodiments, the present invention provides a compound of formula I, wherein LBM is KEAP1-NRF2 binding moiety thereby forming a compound of formula I-xxx or I-xxx-2:

I-xxx-1

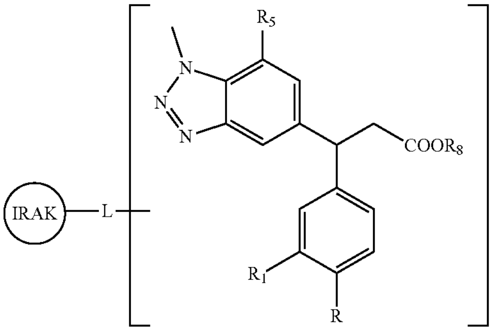

I-xxx-2

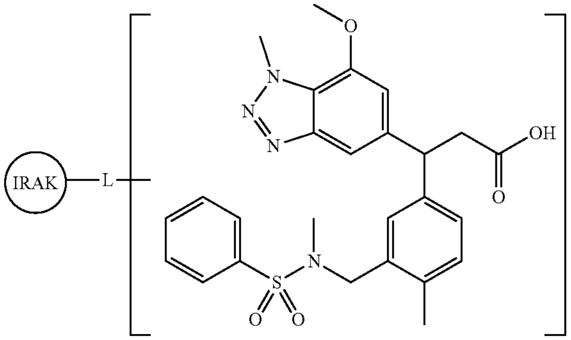

or a pharmaceutically acceptable salt thereof, wherein L and IRAK are as defined above and described in embodiments herein, and wherein each of the variables R, $R_1$, $R_5$, and $R_8$ is as described and defined in WO 2020/018788, the entirety of each of which is herein incorporated by reference.

In certain embodiments, the present invention provides a compound of formula I, wherein LBM is KEAP1-NRF2 binding moiety as recited in Tong et al., "Targeted Protein Degradation via a Covalent Reversible Degrader Based on Bardoxolone", ChemRxiv 2020, thereby forming a compound of formula I-yyy-1 or I-yyy-2:

I-yyy-1

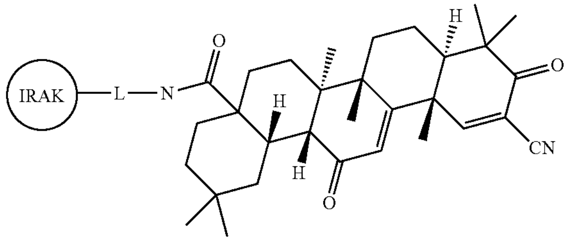

-continued

I-yyy-2

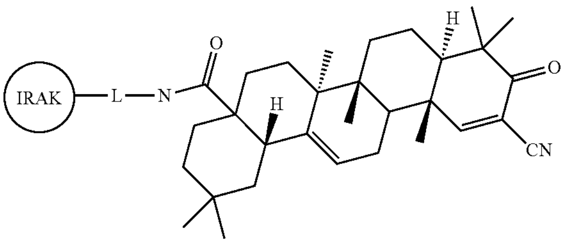

or a pharmaceutically acceptable salt thereof, wherein L and IRAK are as defined above and described in embodiments herein, both singly and in combination.

Lysine Mimetic

In some embodiments, DIM is LBM as described above and herein. In some embodiments, DIM is lysine mimetic. In some embodiments, the covalent attachment of ubiquitin to a member of the IRAK kinase family (i.e., IRAK-1, -2, -3, or -4) is achieved through the action of a lysine mimetic. In some embodiments, upon the binding of a compound of formula I to IRAK-1, the moiety that mimics a lysine undergoes ubiquitination thereby marking IRAK-1 for degradation via the Ubiquitin-Proteasome Pathway (UPP). In some embodiments, upon the binding of a compound of formula I to IRAK-2, the moiety that mimics a lysine undergoes ubiquitination thereby marking IRAK-2 for degradation via the Ubiquitin-Proteasome Pathway (UPP). In some embodiments, upon the binding of a compound of formula I to IRAK-3, the moiety that mimics a lysine undergoes ubiquitination thereby marking IRAK-3 for degradation via the Ubiquitin-Proteasome Pathway (UPP). In some embodiments, upon the binding of a compound of formula I to IRAK-4, the moiety that mimics a lysine undergoes ubiquitination thereby marking IRAK-4 for degradation via the Ubiquitin-Proteasome Pathway (UPP).

In some embodiments, DIM is

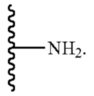

In some embodiments, DIM is

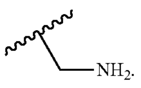

In some embodiments, DIM is

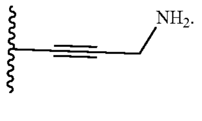 [SMILES: *C#CCN]

In some embodiments, DIM is selected from those depicted in Table 1, below.

In some embodiments, the present invention provides the compound of formula I wherein DIM is

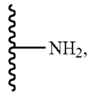

thereby forming a compound of formula I-kkk-1:

I-kkk-1

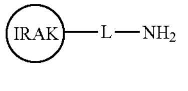

or a pharmaceutically acceptable salt thereof, wherein each of IRAK and L is as defined above and described in embodiments herein, both singly and in combination.

In some embodiments, the present invention provides the compound of formula I wherein DIM is

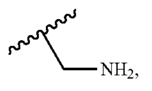

thereby forming a compound of formula I-kkk-2:

I-kkk-2

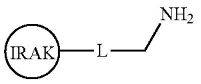

or a pharmaceutically acceptable salt thereof, wherein each of IRAK and L is as defined above and described in embodiments herein, both singly and in combination.

In some embodiments, the present invention provides the compound of formula I wherein DIM is

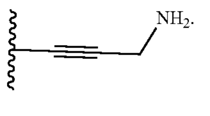 [SMILES: *C#CCN]

thereby forming a compound of formula I-kkk-3:

I-kkk-3

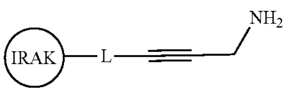

or a pharmaceutically acceptable salt thereof, wherein each of IRAK and L is as defined above and described in embodiments herein, both singly and in combination.

In certain embodiments, the present invention provides a compound of Formula I, wherein DIM is lysine mimetic

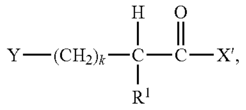

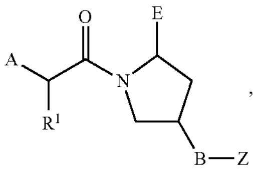

, or

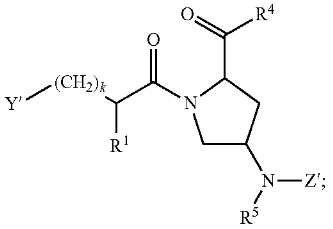

thereby forming a compound of formulae I-lll-1, I-lll-2, or I-III-3, respectively:

I-lll-1

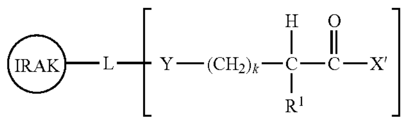

I-lll-2

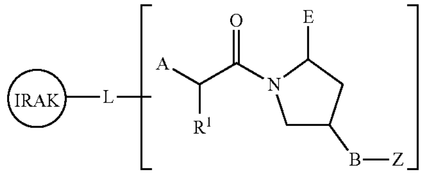

I-lll-3

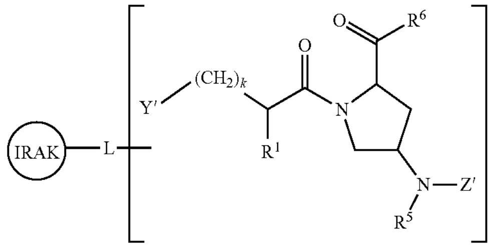

or a pharmaceutically acceptable salt thereof, wherein L and IRAK are as defined above and described in embodiments herein, and wherein each of the variables $R^1$, $R^4$, $R^5$, A, B, E, Y, Y', Z, Z', and k are as defined and described in U.S. Pat. No. 7,622,496, the entirety of each of which is herein incorporated by reference.

Hydrogen Atom

In some embodiments, DIM is a hydrogen atom. In some embodiments, the covalent attachment of ubiquitin to one or more members of the IRAK kinase family (i.e., IRAK-1, -2, -3, or -4) is achieved through a provided compound wherein DIM is a hydrogen atom. In some embodiments, upon the binding of a compound of formula I to IRAK-1, the DIM moiety being hydrogen effectuates ubiquitination thereby marking IRAK-1 for degradation via the Ubiquitin-Proteasome Pathway (UPP). In some embodiments, upon the binding of a compound of formula I to IRAK-2, the DIM moiety being hydrogen effectuates ubiquitination thereby marking IRAK-2 for degradation via the Ubiquitin-Proteasome Pathway (UPP). In some embodiments, upon the binding of a compound of formula I to IRAK-3, the DIM moiety being hydrogen effectuates ubiquitination thereby marking IRAK-3 for degradation via the Ubiquitin-Proteasome Pathway (UPP). In some embodiments, upon the binding of a compound of formula I to IRAK-4, the DIM moiety being hydrogen effectuates ubiquitination thereby marking IRAK-4 for degradation via the Ubiquitin-Proteasome Pathway (UPP).

In some embodiments, DIM is selected from those depicted in Table 1, below.

In some embodiments, the present invention provides the compound of formula I wherein DIM is a hydrogen atom, thereby forming a compound of formula I-mmm:

I-mmm

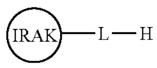

or a pharmaceutically acceptable salt thereof, wherein each of IRAK and L is as defined above and described in embodiments herein, both singly and in combination.

Linker (L)

As defined above and described herein, L is a bivalent moiety that connects IRAK to LBM or IRAK to DIM.

In some embodiments, L is a bivalent moiety that connects IRAK to LBM. In some embodiments, L is a bivalent moiety that connects IRAK to DIM. In some embodiments, L is a bivalent moiety that connects IRAK to a lysine mimetic.

In some embodiments, L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, —CRF—, —$CF_2$—, -Cy-, —O—, —N(R)—, —$Si(R)_2$—, —Si(OH)(R)—, —$Si(OH)_2$—, —P(O)(OR)—, —P(O)(R)—, —P(O)($NR_2$)—, —S—, —OC(O)—, —C(O)O—, —C(O)—, —S(O)—, —$S(O)_2$—, —N(R)$S(O)_2$—, —$S(O)_2$N(R)—, —N(R)C(O)—, —C(O)N(R)—, —OC(O)N(R)—, —N(R)C(O)O—,

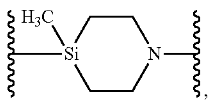,
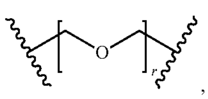,
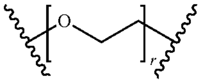,
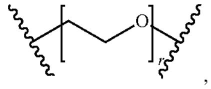,
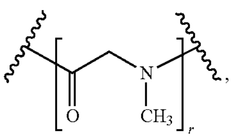, or
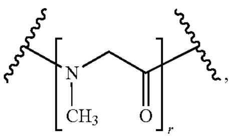, wherein: each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, and wherein r is 0, 1, 2, 3, 4, 5, 6, 7, 8, 9, or 10.

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-11 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-11 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

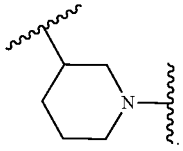 [SMILES: *C1CCCN(*)C1].

In some embodiments, -Cy- is

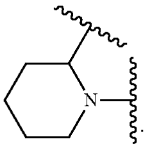 [SMILES: *C1CCCCN1*].

In some embodiments, -Cy- is

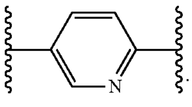 [SMILES: *c1ccc(*)nc1].

In some embodiments, -Cy- is
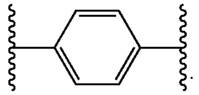 [SMILES: *c1ccc(*)cc1]
In some embodiments, -Cy- is
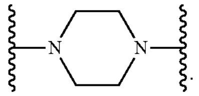 [SMILES: *N1CCN(*)CC1]
In some embodiments, -Cy- is
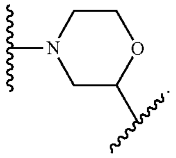
In some embodiments, -Cy- is
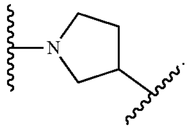
In some embodiments, -Cy- is
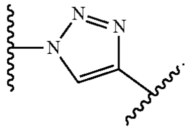
In some embodiments, -Cy- is
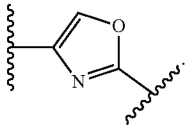
In some embodiments, -Cy- is
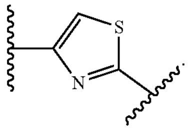
In some embodiments, -Cy- is
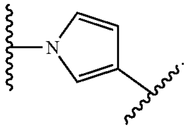
In some embodiments, -Cy- is
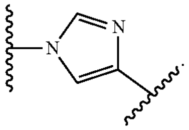
In some embodiments, -Cy- is
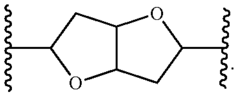 [SMILES: *C1CC2OC(*)CC2O1]
In some embodiments, -Cy- is
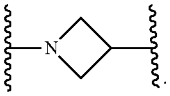 [SMILES: *C1CN(*)C1]
In some embodiments, -Cy- is
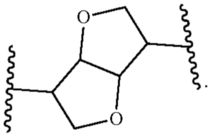 [SMILES: *C1COC2C(*)COC12]
In some embodiments, -Cy- is
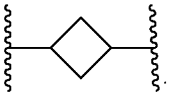 [SMILES: *C1CC(*)C1]
In some embodiments, -Cy- is
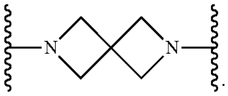 [SMILES: *N1CC2(C1)CN(*)C2]

In some embodiments, -Cy- is
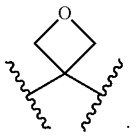 [SMILES: *C1(*)COC1]
In some embodiments, -Cy- is
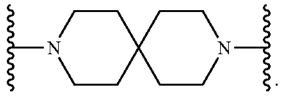
In some embodiments, -Cy- is
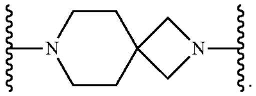 [SMILES: *N1CCC2(CC1)CN(*)C2]
In some embodiments, -Cy- is
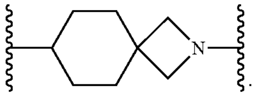
In some embodiments, -Cy- is
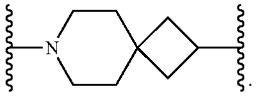 [SMILES: *C1CCC2(CC1)CC(*)C2]
In some embodiments, -Cy- is
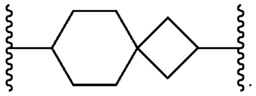
In some embodiments, -Cy- is
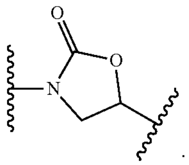 [SMILES: *C1CN(*)C(=O)O1]
In some embodiments, -Cy- is
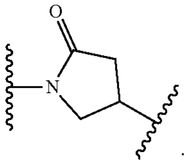 [SMILES: *C1CC(=O)N(*)C1]
In some embodiments, Cy- is
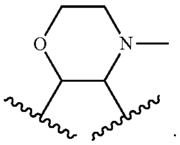 [SMILES: *C1OCCN(C)C1*]
In some embodiments, -Cy- is
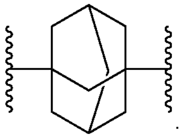 [SMILES: *C12CC3CC(C1)CC(*)(C3)C2]
In some embodiments, -Cy- is
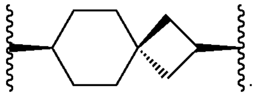
In some embodiments, -Cy- is
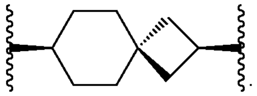
In some embodiments, -Cy- is
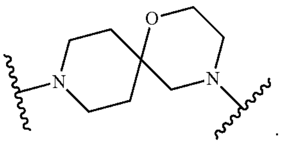 [SMILES: *N1CCC2(CC1)CN(*)CCO2]
In some embodiments, -Cy- is
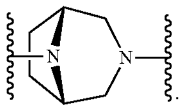 [SMILES: *N1C[C@H]2CC[C@@H](C1)N2*]

In some embodiments, -Cy- is

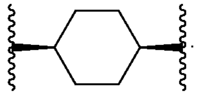 [SMILES: *[C@H]1CC[C@@H](*)CC1]

In some embodiments, Cy- is

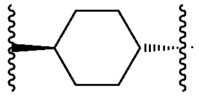

In some embodiments, -Cy- is

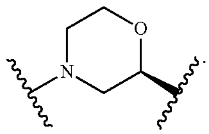 [SMILES: *[C@H]1CN(*)CCO1]

In some embodiments, Cy- is

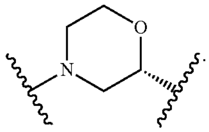 [SMILES: *[C@@H]1CN(*)CCO1]

In some embodiments, -Cy- is

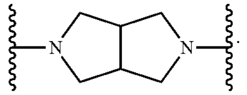 [SMILES: *N1CC2CN(*)CC2C1]

In some embodiments, -Cy- is

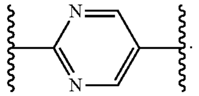 [SMILES: *c1cnc(*)nc1]

In some embodiments, -Cy- is

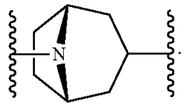 [SMILES: *C1C[C@H]2CC[C@@H](C1)N2*]

In some embodiments, -Cy- is selected from those depicted in Table 1, below.

In some embodiments, L is selected from those depicted in Table 1, below.

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 1, below.

In some embodiments, L is

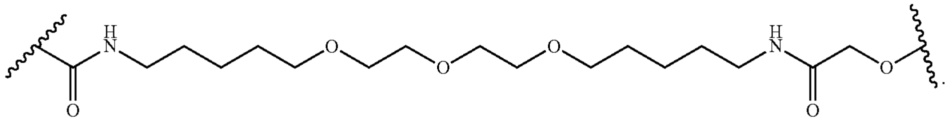 [SMILES: *OCC(=O)NCCCCCOCCOCCOCCCCCNC(*)=O]

In some embodiments, L is

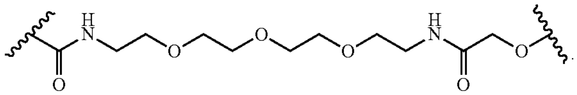 [SMILES: *OCC(=O)NCCOCCOCCOCCNC(*)=O]

In some embodiments, L is

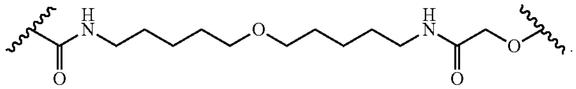 [SMILES: *OCC(=O)NCCCCCOCCCCCNC(*)=O]

In some embodiments, L is

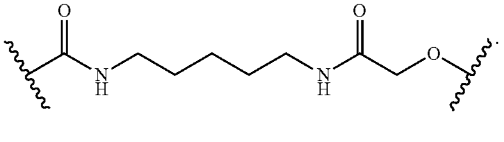 [SMILES: *OCC(=O)NCCCCCNC(*)=O]

In some embodiments, L is
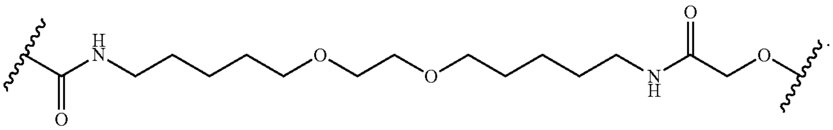 [SMILES: *OCC(=O)NCCCCCOCCOCCCCCNC(*)=O]
In some embodiments, L is
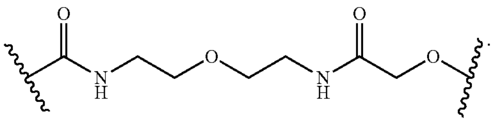 [SMILES: *OCC(=O)NCCOCCNC(*)=O]
In some embodiments, L is
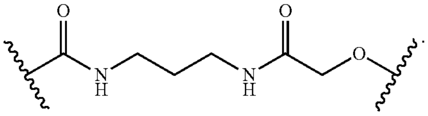 [SMILES: *OCC(=O)NCCCNC(*)=O]
In some embodiments, L is
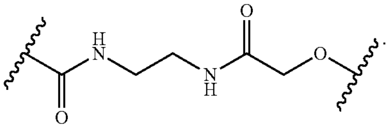 [SMILES: *OCC(=O)NCCNC(*)=O]
In some embodiments, L is
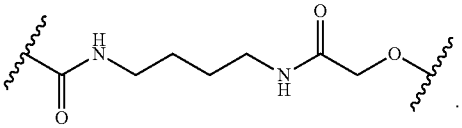 [SMILES: *OCC(=O)NCCCCNC(*)=O]
In some embodiments, L is
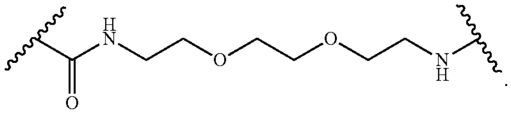 [SMILES: *NCCOCCOCCNC(*)=O]
In some embodiments, L is
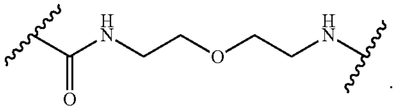 [SMILES: *NCCOCCNC(*)=O]
In some embodiments, L is
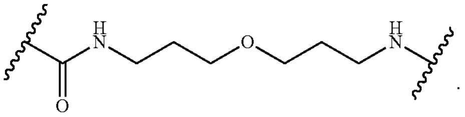 [SMILES: *NCCCOCCCNC(*)=O]
In some embodiments, L is
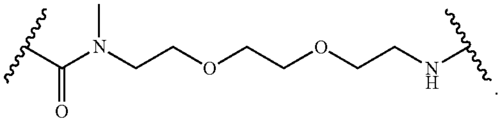 [SMILES: *NCCOCCOCCN(C)C(*)=O]
In some embodiments, L is
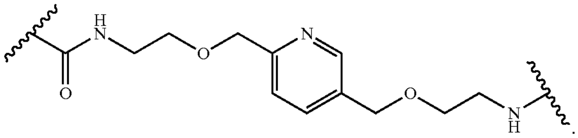 [SMILES: *NCCOCc1ccc(COCCNC(*)=O)nc1]
In some embodiments, L is
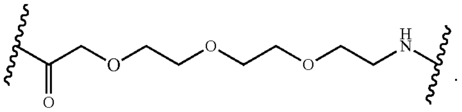 [SMILES: *NCCOCCOCCOCC(*)=O]
In some embodiments, L is
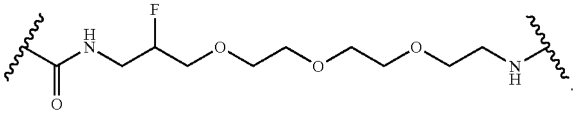 [SMILES: *NCCOCCOCCOCC(F)CNC(*)=O]

In some embodiments, L is
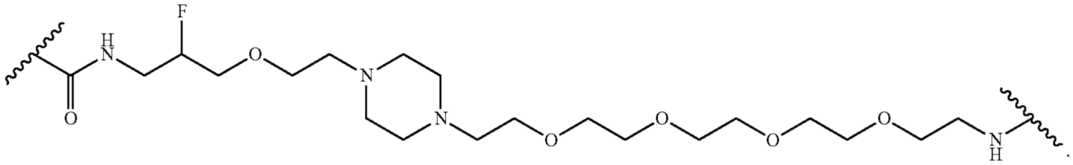 [SMILES: *NCCOCCOCCOCCOCCN1CCN(CCOCC(F)CNC(*)=O)CC1]
In some embodiments, L is
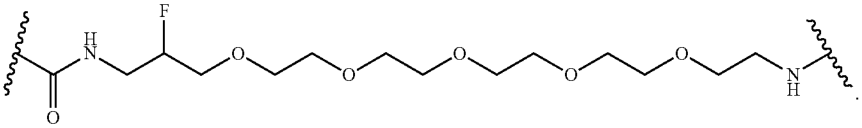 [SMILES: *NCCOCCOCCOCCOCCOCC(F)CNC(*)=O]
In some embodiments, L is
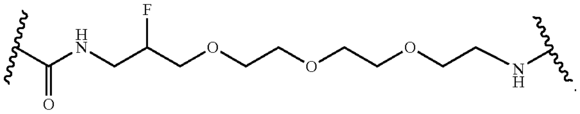 [SMILES: *NCCOCCOCCOCC(F)CNC(*)=O]
In some embodiments, L is
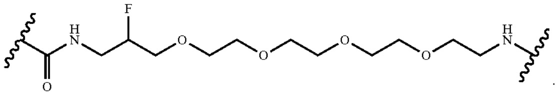 [SMILES: *NCCOCCOCCOCCOCC(F)CNC(*)=O]
In some embodiments, L is
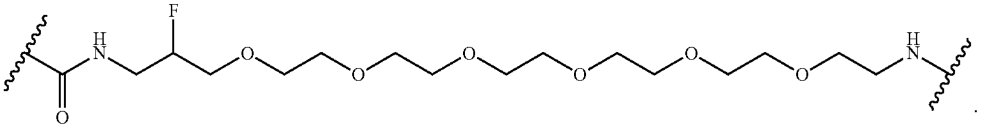 [SMILES: *NCCOCCOCCOCCOCCOCCOCC(F)CNC(*)=O]
In some embodiments, L is
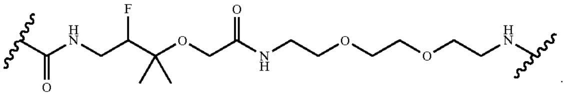 [SMILES: *NCCOCCOCCNC(=O)COC(C)(C)C(F)CNC(*)=O]
In some embodiments, L is
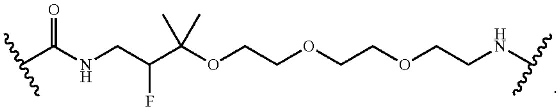 [SMILES: *NCCOCCOCCOC(C)(C)C(F)CNC(*)=O]
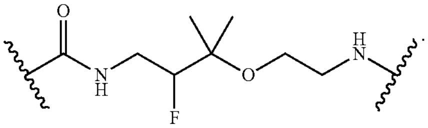 [SMILES: *NCCOC(C)(C)C(F)CNC(*)=O]

In some embodiments, L is
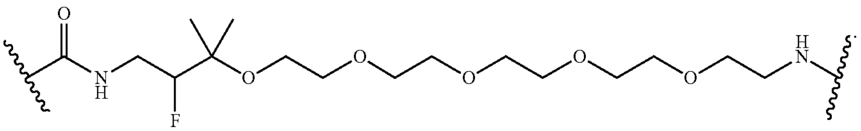 [SMILES: *NCCOCCOCCOCCOCCOC(C)(C)C(F)CNC(*)=O]
In some embodiments, L is
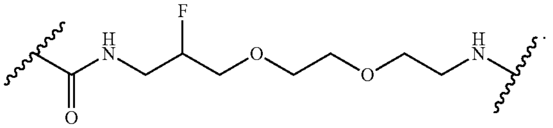 [SMILES: *NCCOCCOCC(F)CNC(*)=O]
In some embodiments, L is
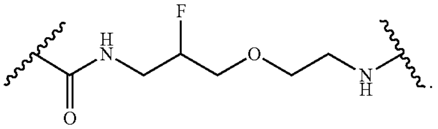 [SMILES: *NCCOCC(F)CNC(*)=O]
In some embodiments, L is
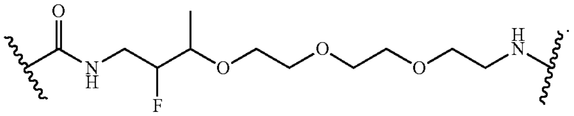 [SMILES: *NCCOCCOCCOC(C)C(F)CNC(*)=O]
In some embodiments, L is
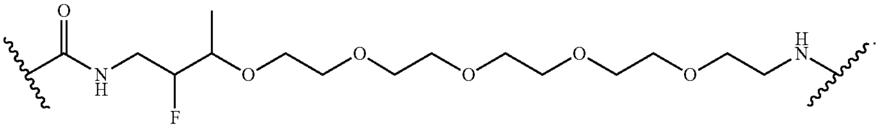 [SMILES: *NCCOCCOCCOCCOCCOC(C)C(F)CNC(*)=O]
In some embodiments, L is
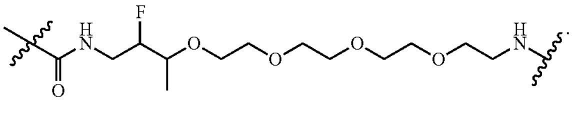 [SMILES: *NCCOCCOCCOCCOC(C)C(F)CNC(*)=O]
In some embodiments, L is
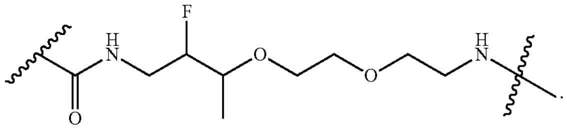 [SMILES: *NCCOCCOC(C)C(F)CNC(*)=O]
In some embodiments, L is
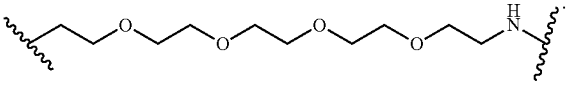 [SMILES: *CCOCCOCCOCCOCCN*]
In some embodiments, L is
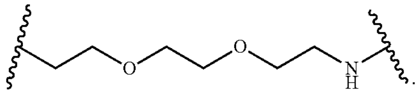 [SMILES: *CCOCCOCCN*]
In some embodiments, L is
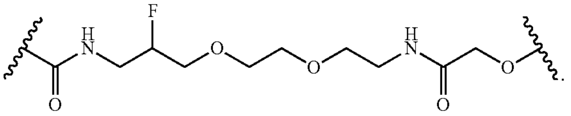 [SMILES: *OCC(=O)NCCOCCOCC(F)CNC(*)=O]
In some embodiments, L is
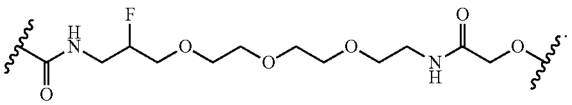 [SMILES: *OCC(=O)NCCOCCOCCOCC(F)CNC(*)=O]

In some embodiments, L is
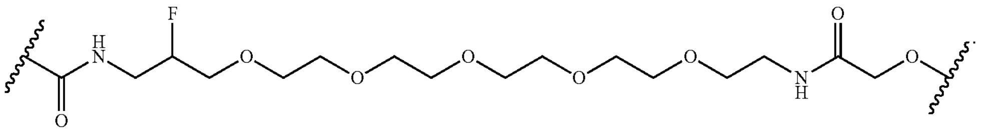 [SMILES: *OCC(=O)NCCOCCOCCOCCOCCOCC(F)CNC(*)=O]
In some embodiments, L is
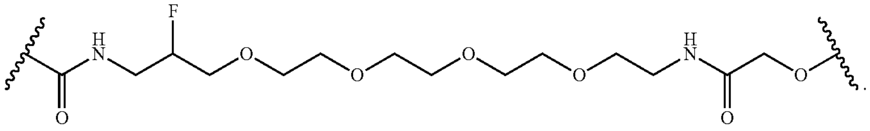 [SMILES: *OCC(=O)NCCOCCOCCOCCOCC(F)CNC(*)=O]
In some embodiments, L is
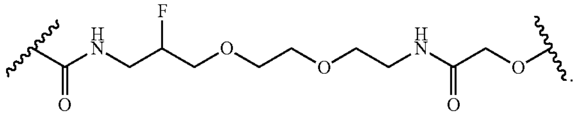 [SMILES: *OCC(=O)NCCOCCOCC(F)CNC(*)=O]
In some embodiments, L is
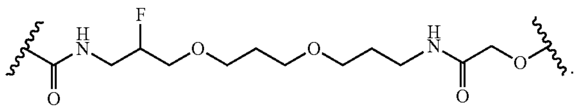 [SMILES: *OCC(=O)NCCCOCCCOCC(F)CNC(*)=O]
In some embodiments, L is
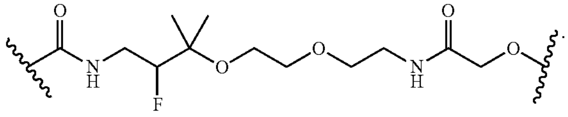 [SMILES: *OCC(=O)NCCOCCOC(C)(C)C(F)CNC(*)=O]
In some embodiments, L is
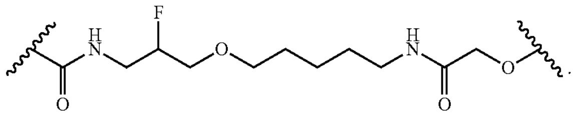 [SMILES: *OCC(=O)NCCCCCOCC(F)CNC(*)=O]
In some embodiments, L is
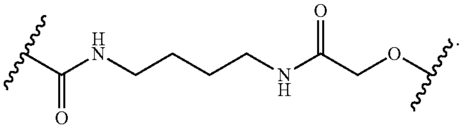 [SMILES: *OCC(=O)NCCCCNC(*)=O]
In some embodiments, L is
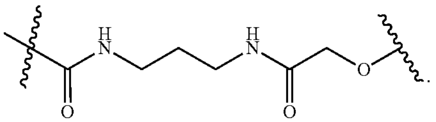 [SMILES: *OCC(=O)NCCCNC(*)=O]
In some embodiments, L is
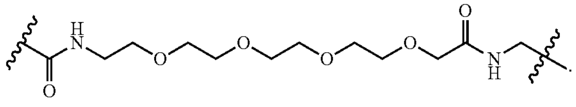
In some embodiments, L is
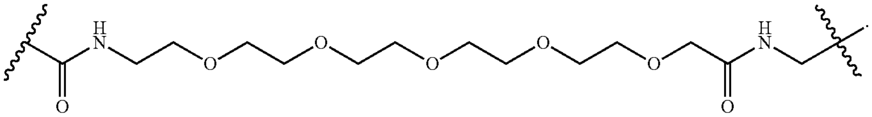
In some embodiments, L is
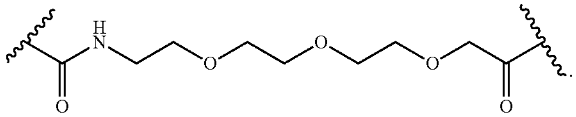 [SMILES: *C(=O)COCCOCCOCCNC(*)=O]

In some embodiments, L is

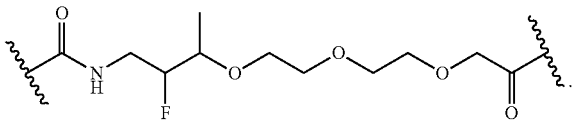 [SMILES: *C(=O)COCCOCCOC(C)C(F)CNC(*)=O]

In some embodiments, L is

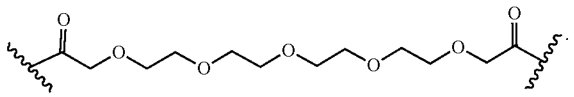 [SMILES: *C(=O)COCCOCCOCCOCCOCC(*)=O]

In some embodiments, L is

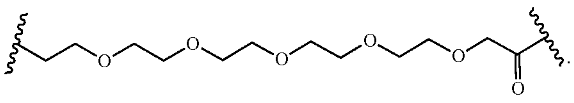 [SMILES: *CCOCCOCCOCCOCCOCC(*)=O]

In some embodiments, L is

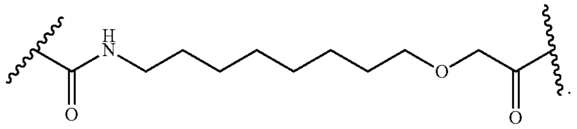 [SMILES: *C(=O)COCCCCCCCCNC(*)=O]

In some embodiments, L is

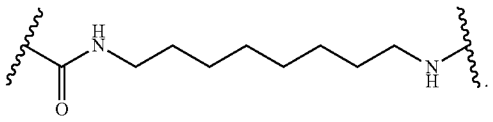 [SMILES: *NCCCCCCCCNC(*)=O]

In some embodiments, L is

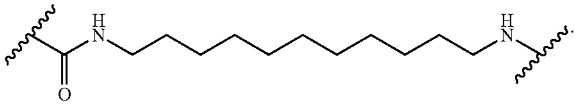 [SMILES: *NCCCCCCCCCCCNC(*)=O]

In some embodiments, L is

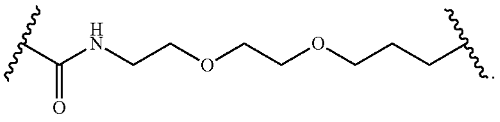 [SMILES: *CCCOCCOCCNC(*)=O]

In some embodiments, L is

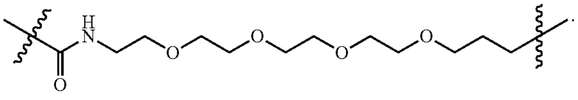 [SMILES: *CCCOCCOCCOCCOCCNC(*)=O]

In some embodiments, L is

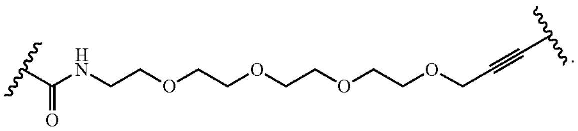 [SMILES: *C#CCOCCOCCOCCOCCNC(*)=O]

In some embodiments, L is

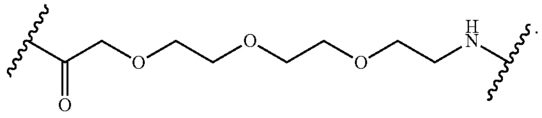 [SMILES: *NCCOCCOCCOCC(*)=O]

In some embodiments, L is

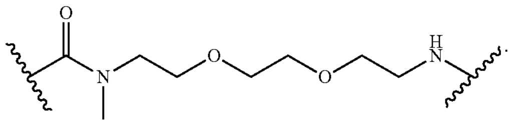 [SMILES: *NCCOCCOCCN(C)C(*)=O]

In some embodiments, L is

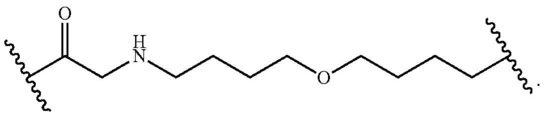 [SMILES: *CCCCOCCCCNCC(*)=O]

In some embodiments, L is

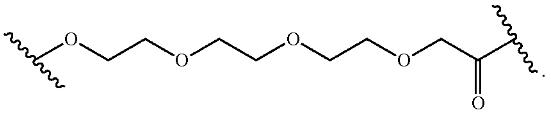 [SMILES: *OCCOCCOCCOCC(*)=O]

In some embodiments, L is

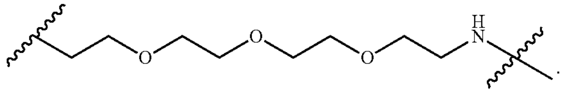 [SMILES: *CCOCCOCCOCCN*]

In some embodiments, L is

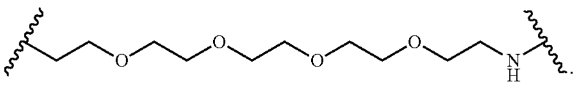 [SMILES: *CCOCCOCCOCCOCCN*]

In some embodiments, L is

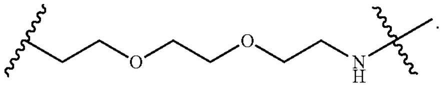 [SMILES: *CCOCCOCCN*]

In some embodiments, L is

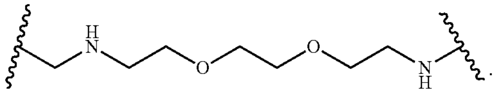 [SMILES: *CNCCOCCOCCN*]

In some embodiments, L is

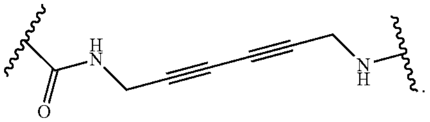 [SMILES: *NCC#CC#CCNC(*)=O]

In some embodiments, L is

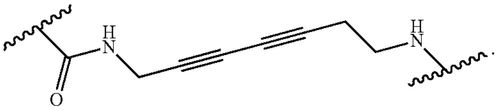 [SMILES: *NCCC#CC#CCNC(*)=O]

In some embodiments, L is

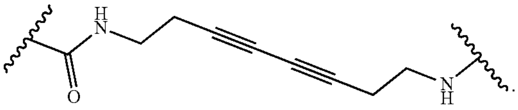 [SMILES: *NCCC#CC#CCCNC(*)=O]

In some embodiments, L is

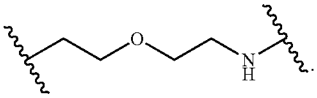 [SMILES: *CCOCCN*]

In some embodiments, L is

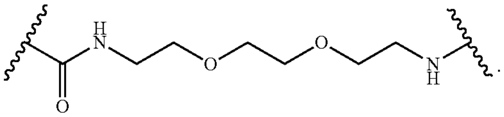 [SMILES: *NCCOCCOCCNC(*)=O]

In some embodiments, L is

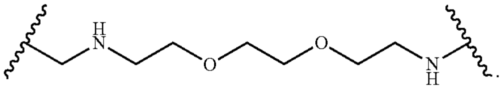 [SMILES: *CNCCOCCOCCN*]

In some embodiments, L is

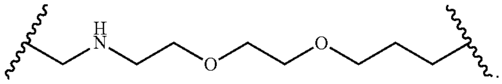 [SMILES: *CCCOCCOCCNC*]

In some embodiments, L is

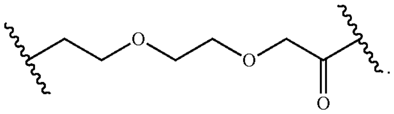 [SMILES: *CCOCCOCC(*)=O]

In some embodiments, L is

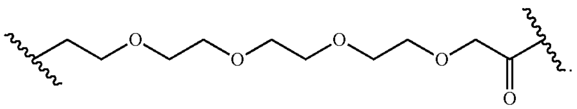 [SMILES: *CCOCCOCCOCCOCC(*)=O]

In some embodiments, L is

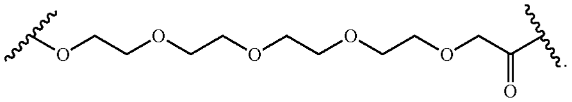 [SMILES: *OCCOCCOCCOCCOCC(*)=O]

In some embodiments, L is

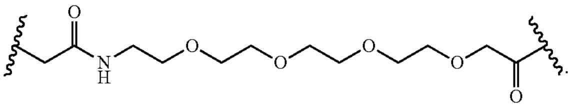 [SMILES: *CC(=O)NCCOCCOCCOCCOCC(*)=O]

In some embodiments, L is

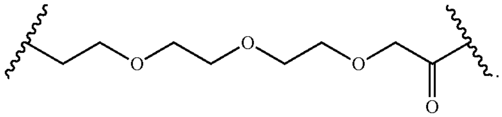 [SMILES: *CCOCCOCCOCC(*)=O]

In some embodiments, L is

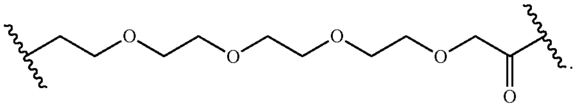 [SMILES: *CCOCCOCCOCCOCC(*)=O]

In some embodiments, L is

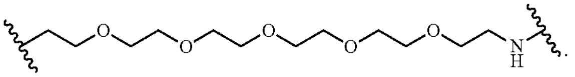 [SMILES: *CCOCCOCCOCCOCCOCCN*]

In some embodiments, L is

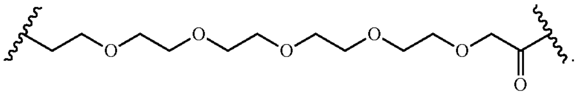 [SMILES: *CCOCCOCCOCCOCCOCC(*)=O]

In some embodiments, L is

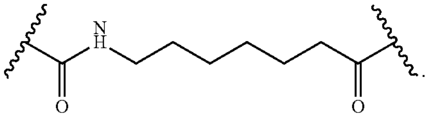 [SMILES: *C(=O)CCCCCCNC(*)=O]

In some embodiments, L is

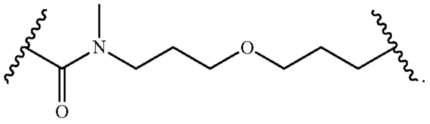 [SMILES: *CCCOCCCN(C)C(*)=O]

In some embodiments, L is

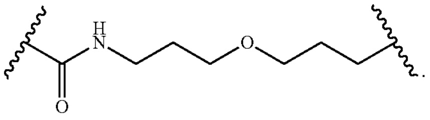 [SMILES: *CCCOCCCNC(*)=O]

In some embodiments, L is

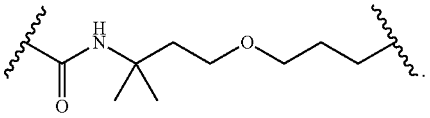 [SMILES: *CCCOCCC(C)(C)NC(*)=O]

In some embodiments, L is

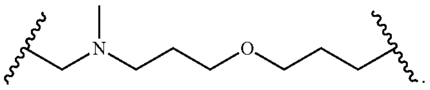 [SMILES: *CCCOCCCN(C)C*]

In some embodiments, L is

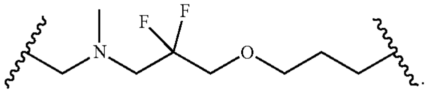 [SMILES: *CCCOCC(F)(F)CN(C)C*]

In some embodiments, L is

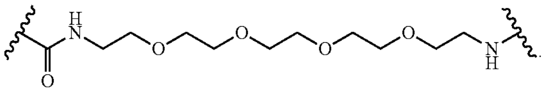 [SMILES: *NCCOCCOCCOCCOCCNC(*)=O]

In some embodiments, L is

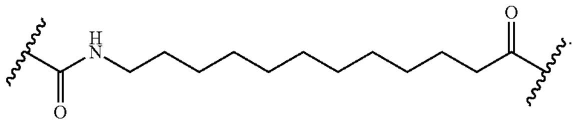 [SMILES: *C(=O)CCCCCCCCCCCNC(*)=O]

In some embodiments, L is

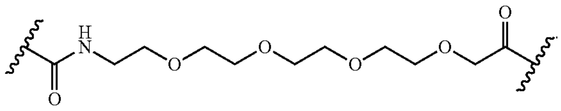 [SMILES: *C(=O)COCCOCCOCCOCCNC(*)=O]

In some embodiments, L is

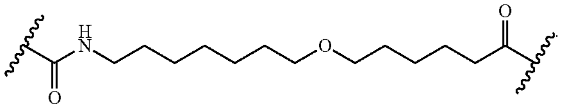 [SMILES: *C(=O)CCCCCOCCCCCCCNC(*)=O]

In some embodiments, L is

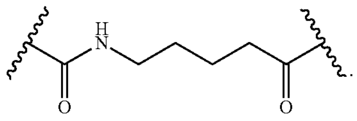 [SMILES: *C(=O)CCCCNC(*)=O]

In some embodiments, L is

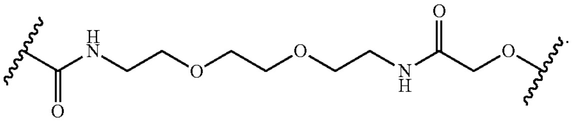 [SMILES: *OCC(=O)NCCOCCOCCNC(*)=O]

In some embodiments, L is

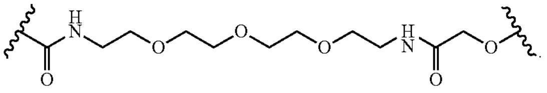 [SMILES: *OCC(=O)NCCOCCOCCOCCNC(*)=O]

In some embodiments, L is

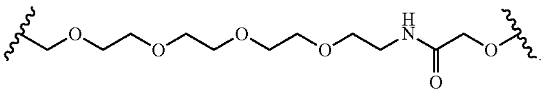 [SMILES: *COCCOCCOCCOCCNC(=O)CO*]

In some embodiments, L is

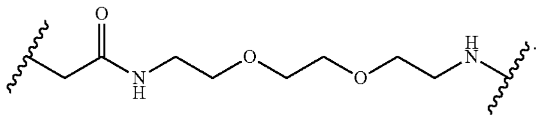 [SMILES: *CC(=O)NCCOCCOCCN*]

In some embodiments, L is

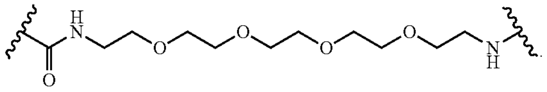 [SMILES: *NCCOCCOCCOCCOCCNC(*)=O]

In some embodiments, L is

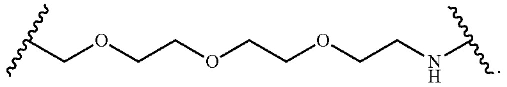 [SMILES: *COCCOCCOCCN*]

In some embodiments, L is

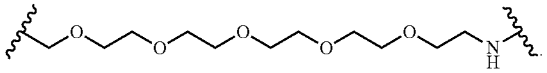 [SMILES: *COCCOCCOCCOCCOCCN*]

In some embodiments, L is

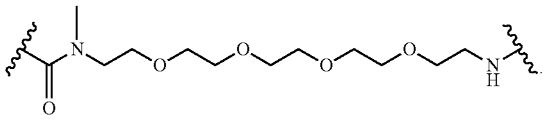 [SMILES: *NCCOCCOCCOCCOCCN(C)C(*)=O]

In some embodiments, L is

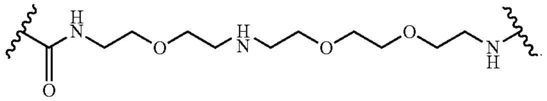 [SMILES: *NCCOCCOCCNCCOCCNC(*)=O]

In some embodiments, L is

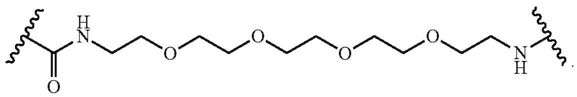 [SMILES: *NCCOCCOCCOCCOCCNC(*)=O]

In some embodiments, L is

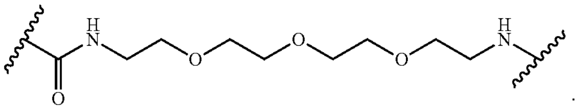 [SMILES: *NCCOCCOCCOCCNC(*)=O]

In some embodiments, L is

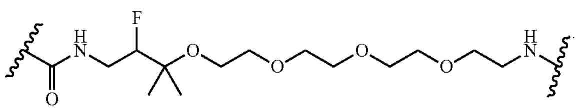 [SMILES: *NCCOCCOCCOCCOC(C)(C)C(F)CNC(*)=O]

In some embodiments, L is

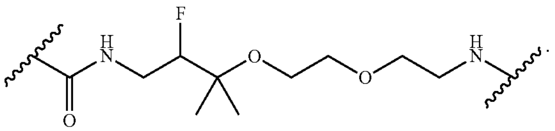 [SMILES: *NCCOCCOC(C)(C)C(F)CNC(*)=O]

In some embodiments, L is

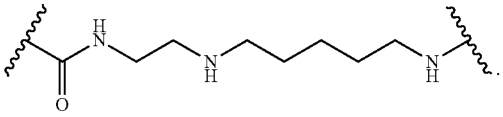 [SMILES: *NCCCCCNCCNC(*)=O]

In some embodiments, L is

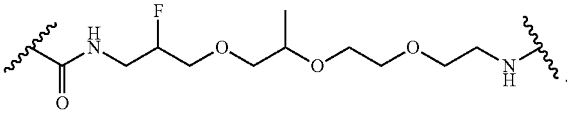 [SMILES: *NCCOCCOC(C)COCC(F)CNC(*)=O]

In some embodiments, L is

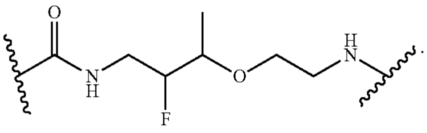 [SMILES: *NCCOC(C)C(F)CNC(*)=O]

In some embodiments, L is

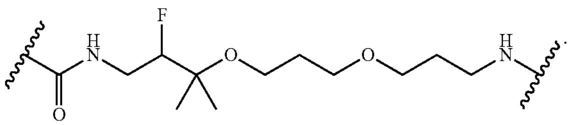 [SMILES: *NCCCOCCCOC(C)(C)C(F)CNC(*)=O]

In some embodiments, L is

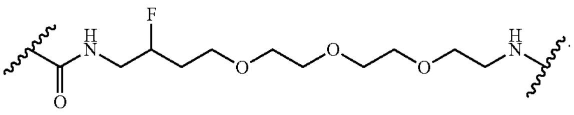 [SMILES: *NCCOCCOCCOCCC(F)CNC(*)=O]

In some embodiments, L is

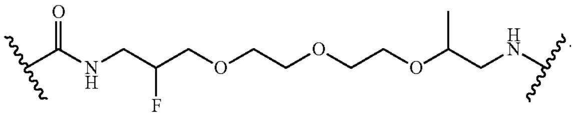 [SMILES: *NCC(C)OCCOCCOCC(F)CNC(*)=O]

In some embodiments, L is
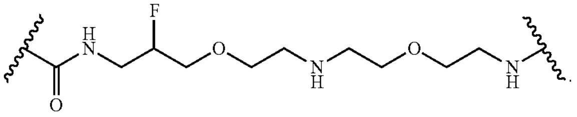 [SMILES: *NCCOCCNCCOCC(F)CNC(*)=O]
In some embodiments, L is
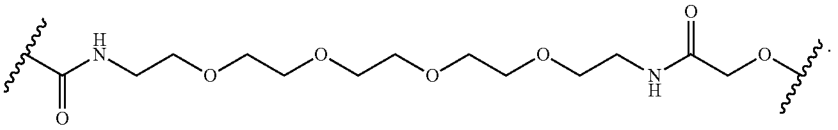 [SMILES: *OCC(=O)NCCOCCOCCOCCOCCNC(*)=O]
In some embodiments, L is
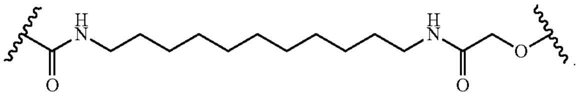 [SMILES: *OCC(=O)NCCCCCCCCCCCNC(*)=O]
In some embodiments, L is
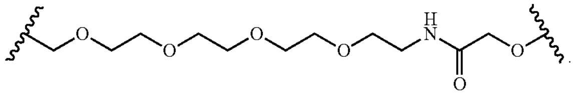 [SMILES: *COCCOCCOCCOCCNC(=O)CO*]
In some embodiments, L is
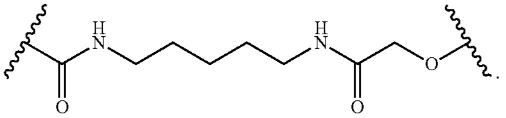 [SMILES: *OCC(=O)NCCCCCNC(*)=O]
In some embodiments, L is
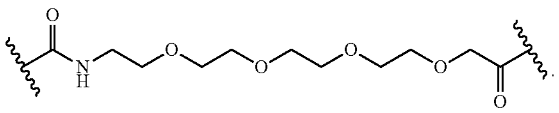 [SMILES: *C(=O)COCCOCCOCCOCCNC(*)=O]
In some embodiments, L is
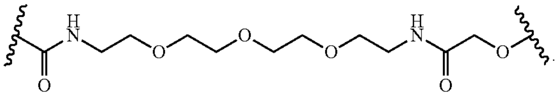 [SMILES: *OCC(=O)NCCOCCOCCOCCNC(*)=O]
In some embodiments, L is
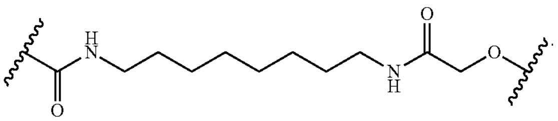 [SMILES: *OCC(=O)NCCCCCCCCNC(*)=O]
In some embodiments, L is
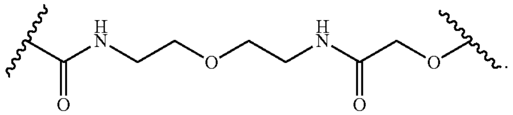 [SMILES: *OCC(=O)NCCOCCNC(*)=O]
In some embodiments, L is
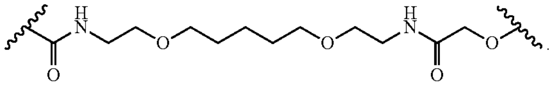 [SMILES: *OCC(=O)NCCOCCCCCOCCNC(*)=O]
In some embodiments, L is
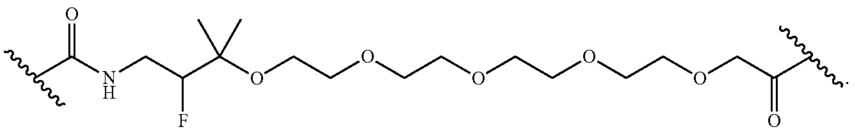 [SMILES: *C(=O)COCCOCCOCCOCCOC(C)(C)C(F)CNC(*)=O]

In some embodiments, L is
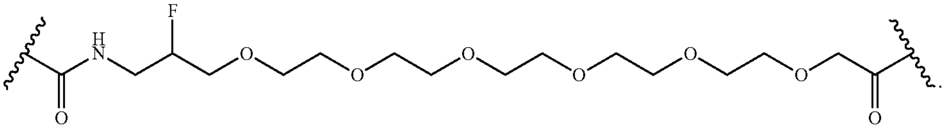 [SMILES: *C(=O)COCCOCCOCCOCCOCCOCC(F)CNC(*)=O]
In some embodiments, L is
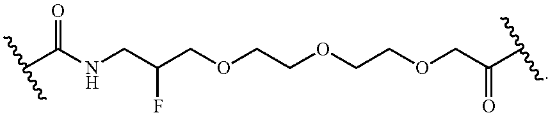 [SMILES: *C(=O)COCCOCCOCC(F)CNC(*)=O]
In some embodiments, L is
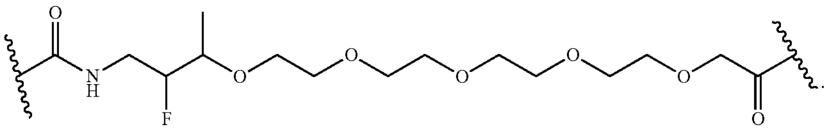 [SMILES: *C(=O)COCCOCCOCCOCCOC(C)C(F)CNC(*)=O]
n some embodiments, L is
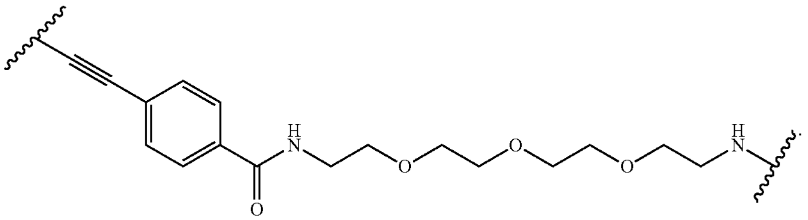 [SMILES: *C#Cc1ccc(C(=O)NCCOCCOCCOCCN*)cc1]
In some embodiments, L is
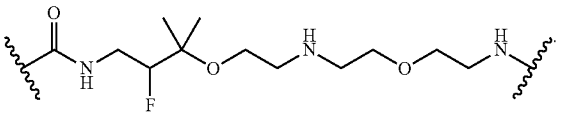 [SMILES: *NCCOCCNCCOC(C)(C)C(F)CNC(*)=O]
In some embodiments, L is
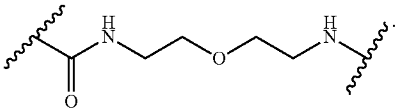 [SMILES: *NCCOCCNC(*)=O]
In some embodiments, L is
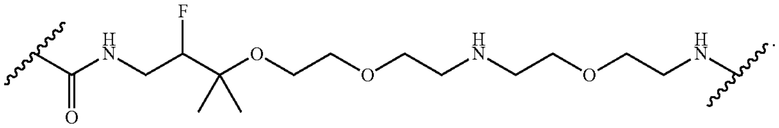 [SMILES: *NCCOCCNCCOCCOC(C)(C)C(F)CNC(*)=O]

In some embodiments, L is
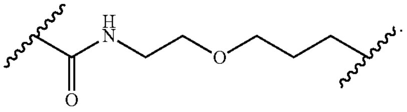 [SMILES: *CCCOCCNC(*)=O]
In some embodiments, L is
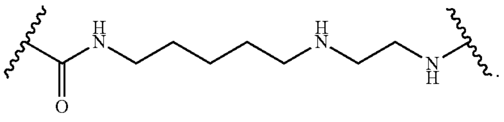 [SMILES: *NCCNCCCCCNC(*)=O]
In some embodiments, L is
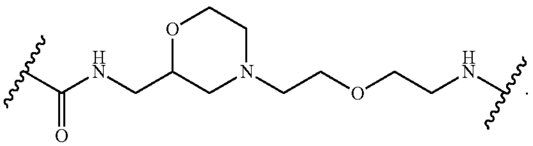 [SMILES: *NCCOCCN1CCOC(CNC(*)=O)C1]
In some embodiments, L is
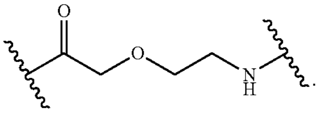 [SMILES: *NCCOCC(*)=O]
In some embodiments, L is
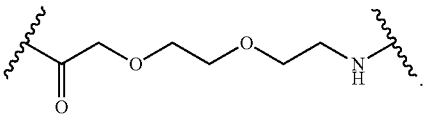 [SMILES: *NCCOCCOCC(*)=O]
In some embodiments, L is
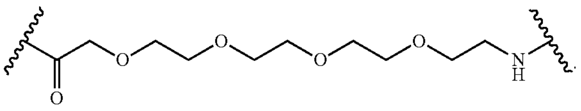 [SMILES: *NCCOCCOCCOCCOCC(*)=O]
In some embodiments, L is
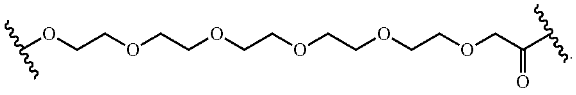 [SMILES: *OCCOCCOCCOCCOCCOCC(*)=O]
In some embodiments, L is
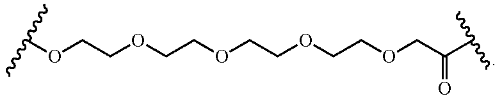 [SMILES: *OCCOCCOCCOCCOCC(*)=O]
In some embodiments, L is
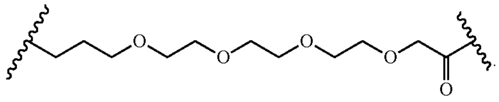
In some embodiments, L is
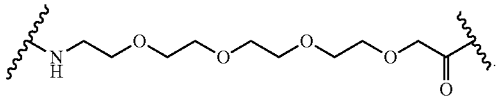 [SMILES: *NCCOCCOCCOCCOCC(*)=O]
In some embodiments, L is
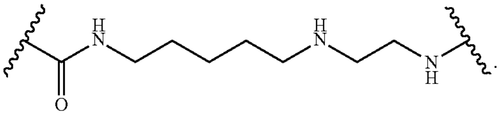 [SMILES: *NCCNCCCCCNC(*)=O]
In some embodiments, L is
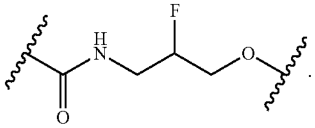 [SMILES: *OCC(F)CNC(*)=O]
In some embodiments, L is
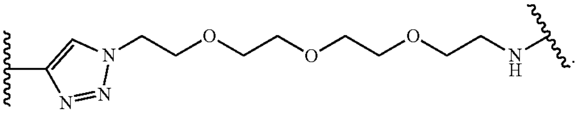 [SMILES: *NCCOCCOCCOCCn1cc(*)nn1]

In some embodiments, L is
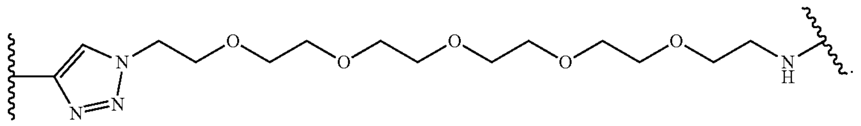 [SMILES: *NCCOCCOCCOCCOCCOCCn1cc(*)nn1]
In some embodiments, L is
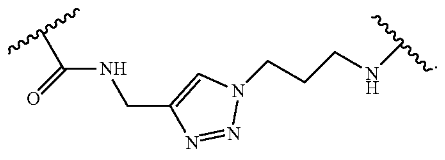 [SMILES: *NCCCn1cc(CNC(*)=O)nn1]
In some embodiments, L is
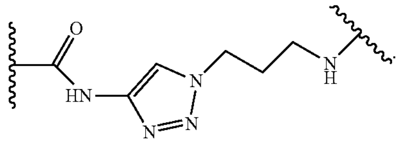 [SMILES: *NCCCn1cc(NC(*)=O)nn1]
In some embodiments, L is
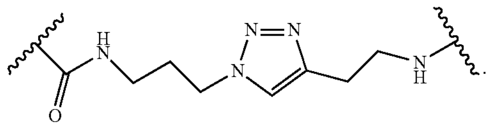 [SMILES: *NCCc1cn(CCCNC(*)=O)nn1]
In some embodiments, L is
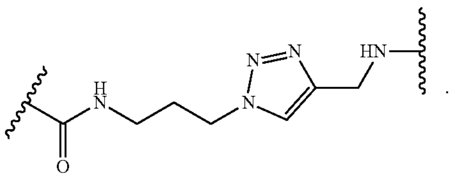 [SMILES: *NCc1cn(CCCNC(*)=O)nn1]
In some embodiments, L is
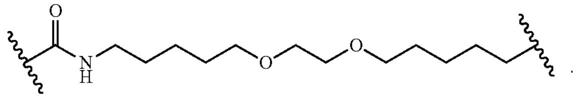 [SMILES: *CCCCCOCCOCCCCCNC(*)=O]
In some embodiments, L is
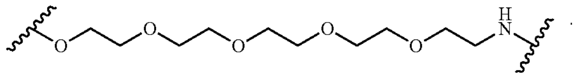 [SMILES: *NCCOCCOCCOCCOCCO*]
In some embodiments, L is
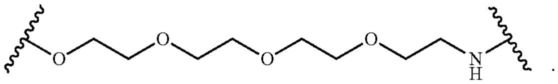 [SMILES: *NCCOCCOCCOCCO*]
In some embodiments, L is
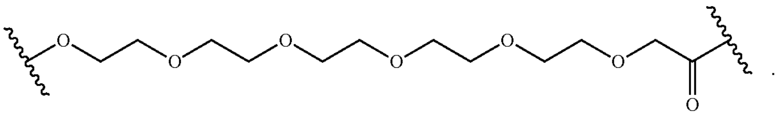 [SMILES: *OCCOCCOCCOCCOCCOCC(*)=O]
In some embodiments, L is
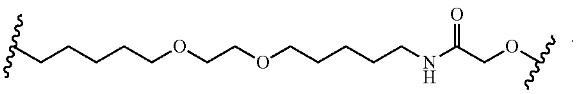 [SMILES: *CCCCCOCCOCCCCCNC(=O)CO*]
In some embodiments, L is
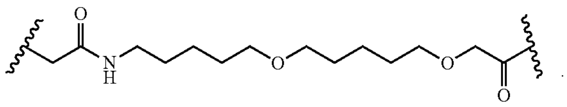 [SMILES: *CC(=O)NCCCCCOCCCCCOCC(*)=O]

In some embodiments, L is
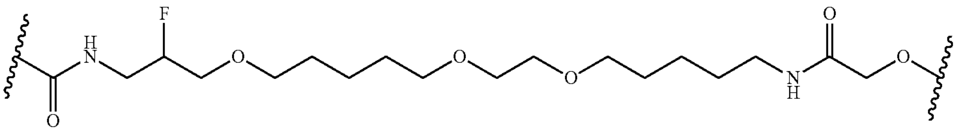
In some embodiments, L is
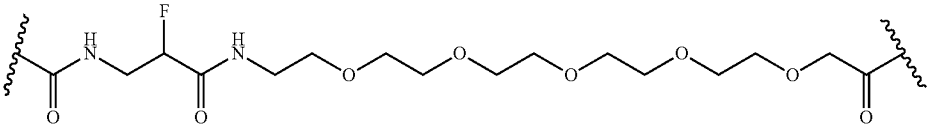
In some embodiments, L is
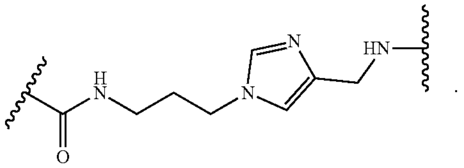 [SMILES: *NCc1cn(CCCNC(*)=O)cn1]
In some embodiments, L is
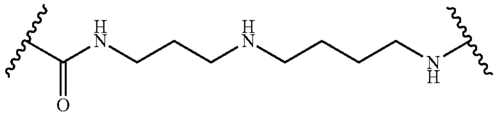
In some embodiments, L is
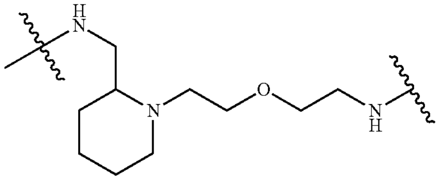
In some embodiments, L is
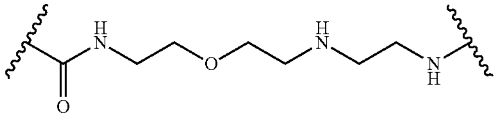
In some embodiments, L is
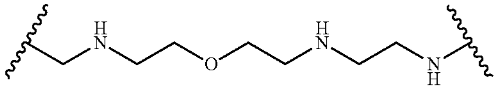
In some embodiment, L is
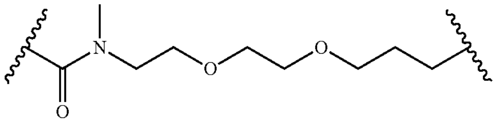
In some embodiment, L is
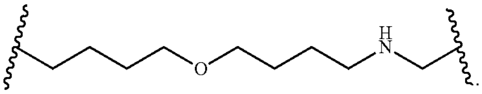 [SMILES: *CCCCOCCCCNC*]
In some embodiment, L is
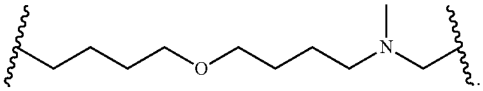 [SMILES: *CCCCOCCCCN(C)C*]
In some embodiments L is
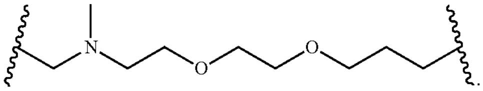 [SMILES: *CCCOCCOCCN(C)C*]
In some embodiments, L is
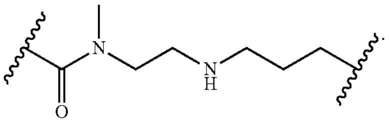 [SMILES: *CCCNCCN(C)C(*)=O]
In some embodiments, L is
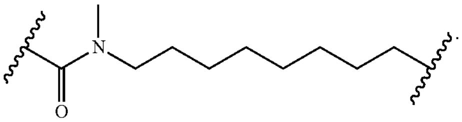 [SMILES: *CCCCCCCCN(C)C(*)=O]

In some embodiments, L is

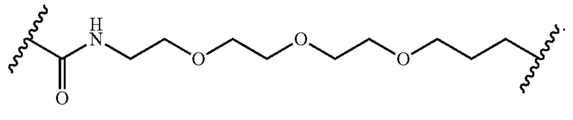 [SMILES: *CCCOCCOCCOCCNC(*)=O]

In some embodiments, L is

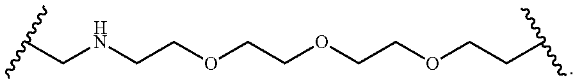 [SMILES: *CCOCCOCCOCCNC*]

In some embodiments, L is

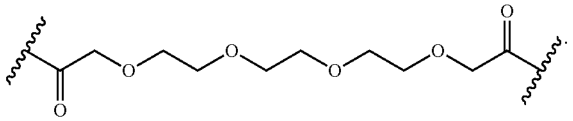 [SMILES: *C(=O)COCCOCCOCCOCC(*)=O]

In some embodiments, L is

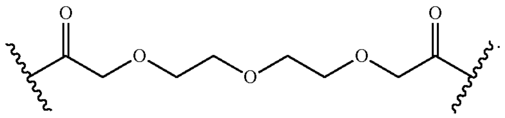 [SMILES: *C(=O)COCCOCCOCC(*)=O]

In In some embodiments, L is

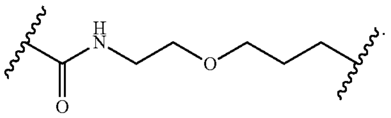 [SMILES: *CCCOCCNC(*)=O]

In some embodiments, L is

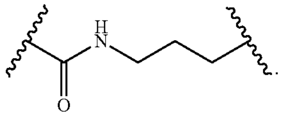 [SMILES: *CCCNC(*)=O]

In some embodiments, L is

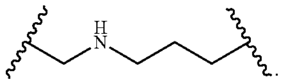 [SMILES: *CCCNC*]

In some embodiments, L is

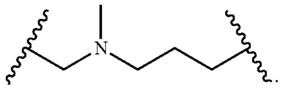 [SMILES: *CCCN(C)C*]

In some embodiments, L is

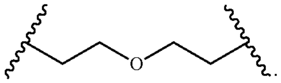 [SMILES: *CCOCC*]

In some embodiments, L is

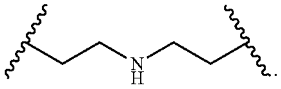 [SMILES: *CCNCC*]

In some embodiments, L is

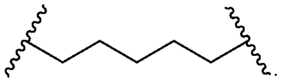 [SMILES: *CCCCC*]

In some embodiments, L is

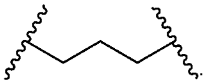 [SMILES: *CCC*]

In some embodiments, L is

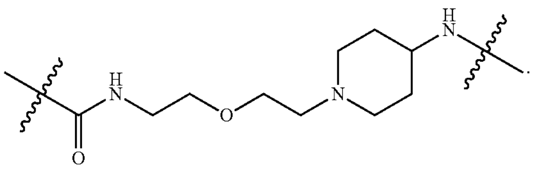 [SMILES: *NC1CCN(CCOCCNC(*)=O)CC1]

In some embodiments, L is

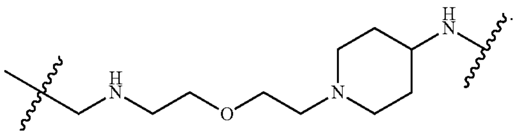 [SMILES: *CNCCOCCN1CCC(N*)CC1]

In some embodiments, L is

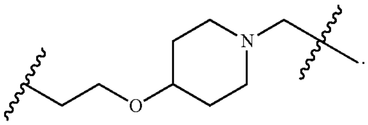 [SMILES: *CCOC1CCN(C*)CC1]

In some embodiments, L is
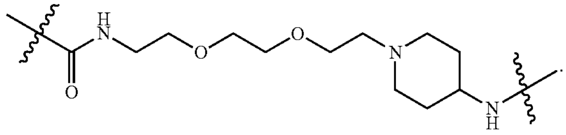 [SMILES: *NC1CCN(CCOCCOCCNC(*)=O)CC1]
In some embodiments, L is
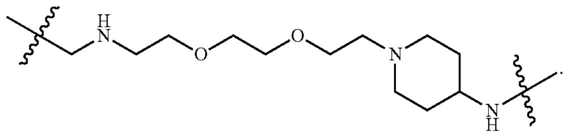 [SMILES: *CNCCOCCOCCN1CCC(N*)CC1]
In some embodiments, L is
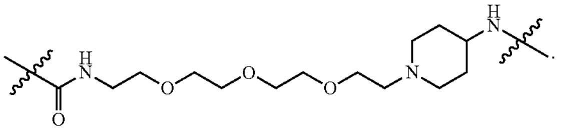 [SMILES: *NC1CCN(CCOCCOCCOCCNC(*)=O)CC1]
In some embodiments, L is
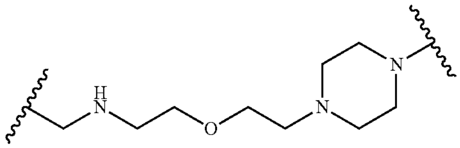
In some embodiments, L is
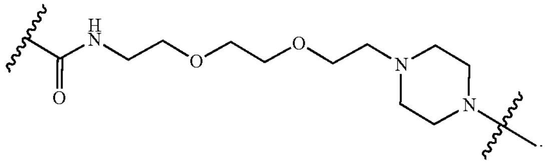
In some embodiments, L is
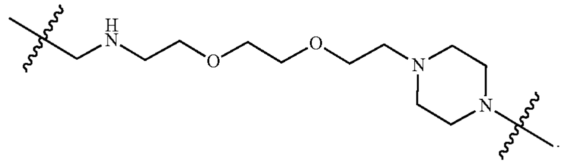
In some embodiments, L is
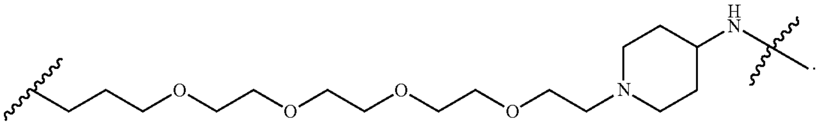 [SMILES: *CCCOCCOCCOCCOCCN1CCC(N*)CC1]
In some embodiments, L is
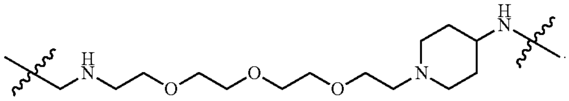 [SMILES: *CNCCOCCOCCOCCN1CCC(N*)CC1]
In some embodiments, L is
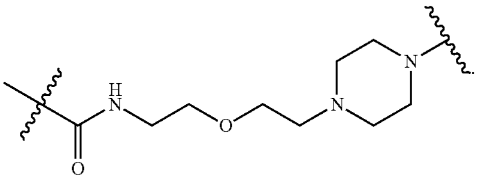 [SMILES: *C(=O)NCCOCCN1CCN(*)CC1]
In some embodiments, L is
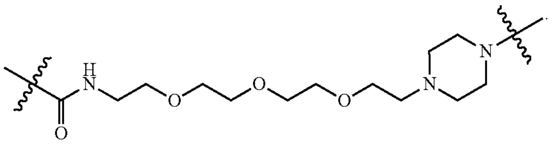 [SMILES: *C(=O)NCCOCCOCCOCCN1CCN(*)CC1]
In some embodiments, L is
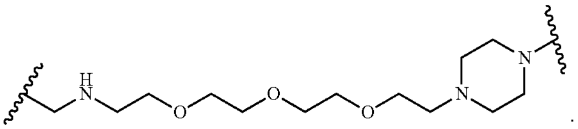 [SMILES: *CNCCOCCOCCOCCN1CCN(*)CC1]
In some embodiments, L is
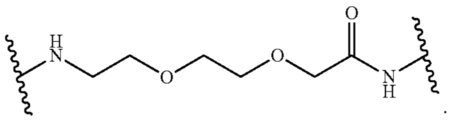 [SMILES: *NCCOCCOCC(=O)N*]

In some embodiments, L is
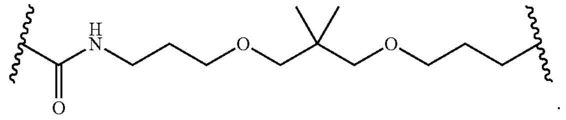 [SMILES: *CCCOCC(C)(C)COCCCNC(*)=O]
In some embodiments, L is
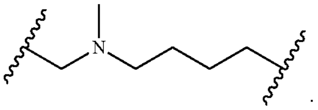
In some embodiments, L is
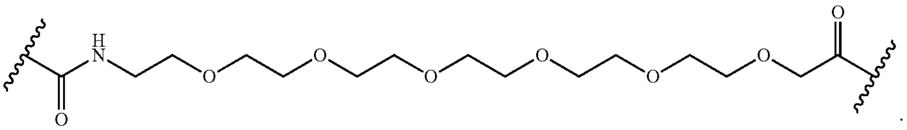 [SMILES: *C(=O)COCCOCCOCCOCCOCCOCCNC(*)=O]
In some embodiments, L is
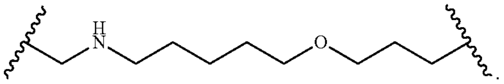 [SMILES: *CCCOCCCCCNC*]
In some embodiments Lis
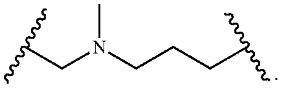
In some embodiments, L is
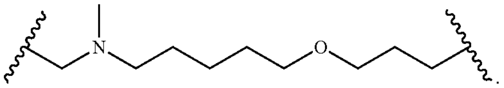 [SMILES: *CCCOCCCCCN(C)C*]
In some embodiments, L is
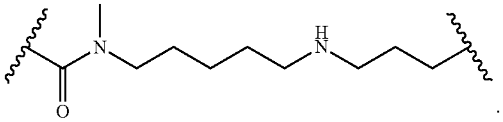 [SMILES: *CCCNCCCCCN(C)C(*)=O]
In some embodiments, L is
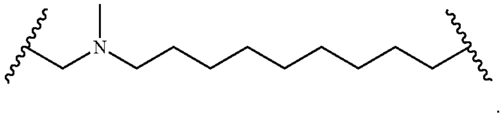 [SMILES: *CCCCCCCCCN(C)C*]
In some embodiments, L is
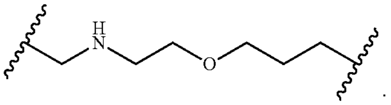
In some embodiments, L is
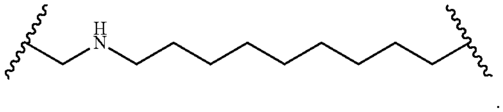 [SMILES: *CCCCCCCCCNC*]
In some embodiments, L is
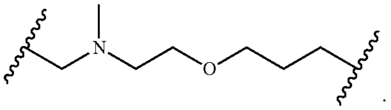
In some embodiments, L is
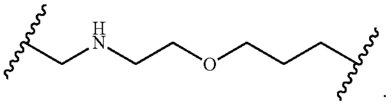 [SMILES: *CCCOCCNC*]
In some embodiments, L is
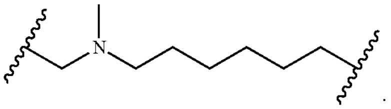
In some embodiments, L is
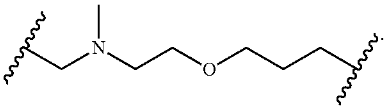 [SMILES: *CCCOCCN(C)C*]

In some embodiments, L is

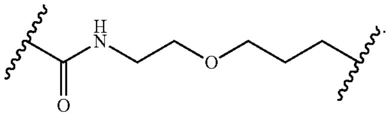 [SMILES: *CCCOCCNC(*)=O]

In some embodiments, L is

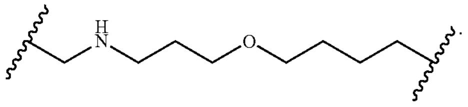 [SMILES: *CCCCOCCCNC*]

In some embodiments, L is

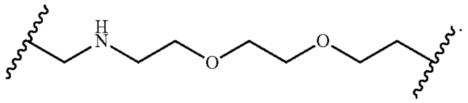 [SMILES: *CCOCCOCCNC*]

In some embodiments, L is

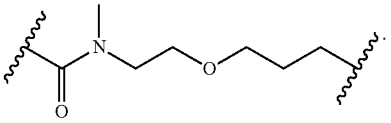 [SMILES: *CCCOCCN(C)C(*)=O]

In some embodiments, L is

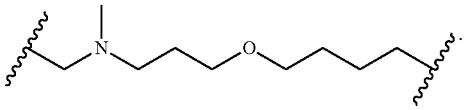 [SMILES: *CCCCOCCCN(C)C*]

In some embodiments, L is

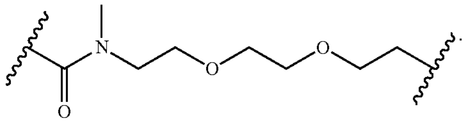 [SMILES: *CCOCCOCCN(C)C(*)=O]

In some embodiments, L is

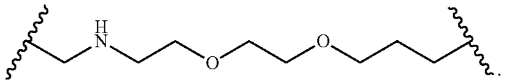 [SMILES: *CCCOCCOCCNC*]

In some embodiments, L is

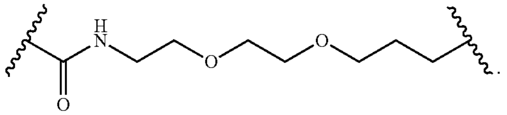 [SMILES: *CCCOCCOCCNC(*)=O]

In some embodiments, L is

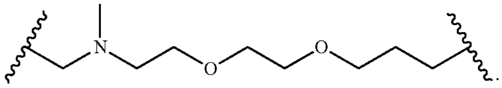 [SMILES: *CCCOCCOCCN(C)C*]

In some embodiments, L is

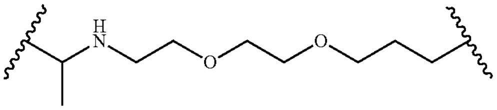 [SMILES: *CCCOCCOCCNC(*)C]

In some embodiments, L is

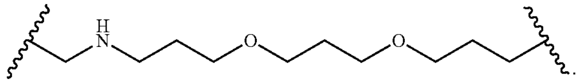 [SMILES: *CCCOCCCOCCCNC*]

In some embodiment, L is

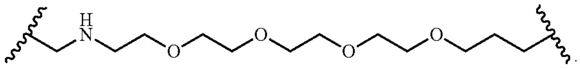 [SMILES: *CCCOCCOCCOCCOCCNC*]

In some embodiment, L is

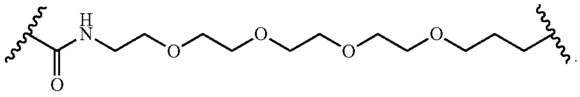 [SMILES: *CCCOCCOCCOCCOCCNC(*)=O]

In some embodiments, L is

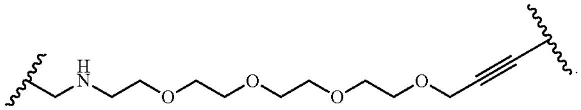 [SMILES: *C#CCOCCOCCOCCOCCNC*]

In some embodiments, L is

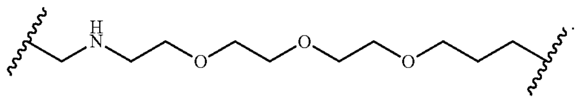 [SMILES: *CCCOCCOCCOCCNC*]

In some embodiments, L is

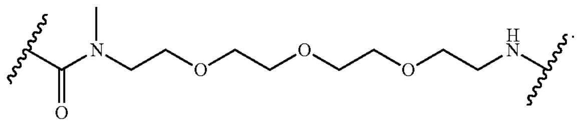 [SMILES: *NCCOCCOCCOCCN(C)C(*)=O]

In some embodiments, L is
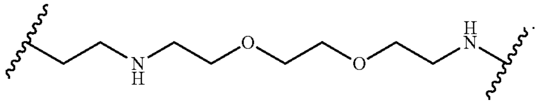 [SMILES: *CCNCCOCCOCCN*]
In some embodiments, L is
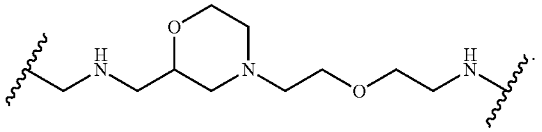 [SMILES: *CNCC1CN(CCOCCN*)CCO1]
In some embodiments, L is
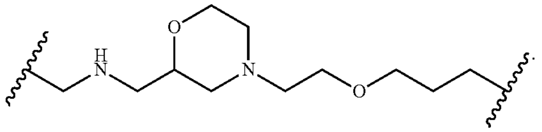 [SMILES: *CCCOCCN1CCOC(CNC*)C1]
In some embodiments, L is
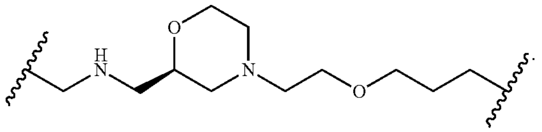 [SMILES: *CCCOCCN1CCO[C@H](CNC*)C1]
In some embodiments, L is
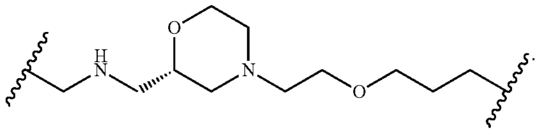
In some embodiments, L is
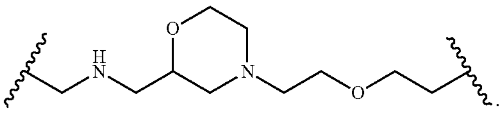 [SMILES: *CCOCCN1CCOC(CNC*)C1]
In some embodiments, L is
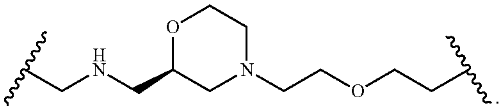 [SMILES: *CCOCCN1CCO[C@H](CNC*)C1]
In some embodiments, L is
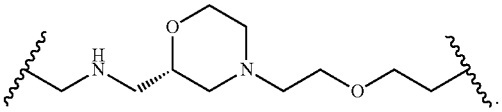
In some embodiments, L is
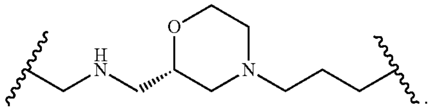
In some embodiments, L is
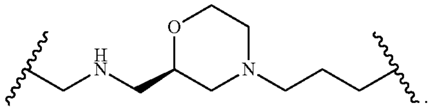
In some embodiments, L is
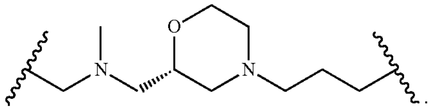 [SMILES: *CCCN1CCO[C@@H](CN(C)C*)C1]
In some embodiments, L is
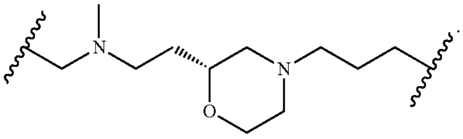 [SMILES: *CCCN1CCO[C@H](CCN(C)C*)C1]
In some embodiments L is
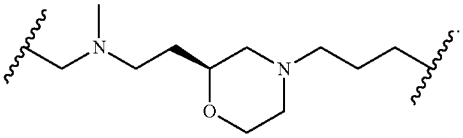 [SMILES: *CCCN1CCO[C@@H](CCN(C)C*)C1]
In some embodiments, L is
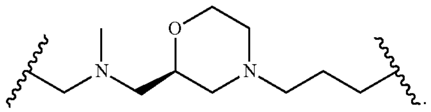 [SMILES: *CCCN1CCO[C@H](CN(C)C*)C1]

In some embodiments, L is
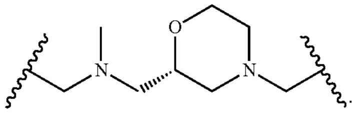 [SMILES: *CN(C)C[C@H]1CN(C*)CCO1]
In some embodiments, L is
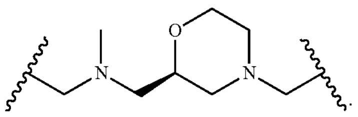 [SMILES: *CN(C)C[C@@H]1CN(C*)CCO1]
In some embodiments L is
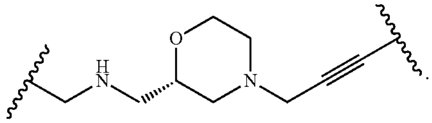 [SMILES: *C#CCN1CCO[C@@H](CNC*)C1]
In some embodiments, L is
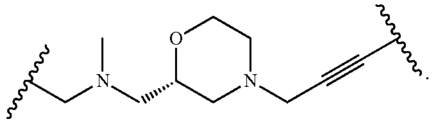 [SMILES: *C#CCN1CCO[C@@H](CN(C)C*)C1]
In some embodiments, L is
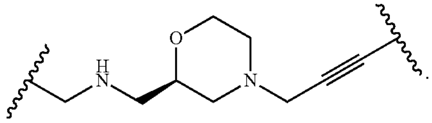 [SMILES: *C#CCN1CCO[C@H](CNC*)C1]
In some embodiments L is
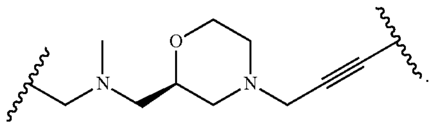 [SMILES: *C#CCN1CCO[C@H](CN(C)C*)C1]
In some embodiments, L is
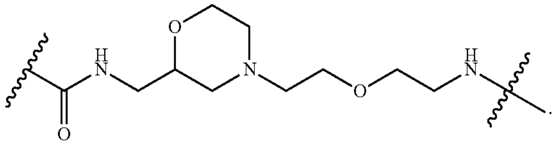 [SMILES: *NCCOCCN1CCOC(CNC(*)=O)C1]
In some embodiments, L is
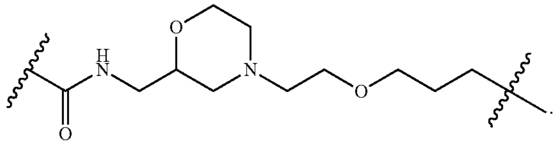 [SMILES: *CCCOCCN1CCOC(CNC(*)=O)C1]
In some embodiments, L is
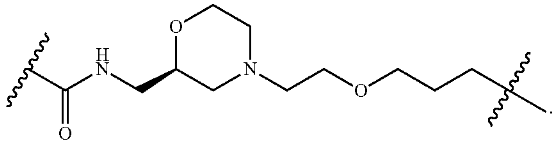 [SMILES: *CCCOCCN1CCO[C@H](CNC(*)=O)C1]
In some embodiments L is
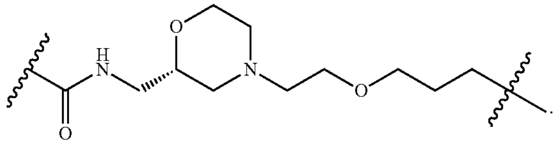 [SMILES: *CCCOCCN1CCO[C@@H](CNC(*)=O)C1]
In some embodiments, L is
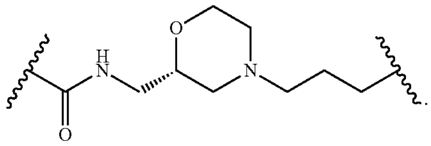 [SMILES: *CCCN1CCO[C@@H](CNC(*)=O)C1]
In some embodiments, L is
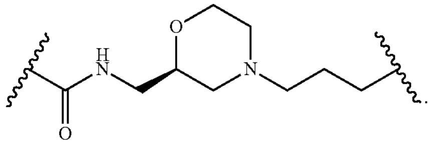 [SMILES: *CCCN1CCO[C@H](CNC(*)=O)C1]
In some embodiments, L is
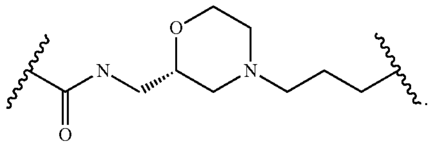 [SMILES: *CCCN1CCO[C@@H](CNC(*)=O)C1]
In some embodiments, L is
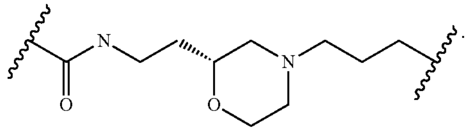 [SMILES: *CCCN1CCO[C@H](CCNC(*)=O)C1]

In some embodiments, L is
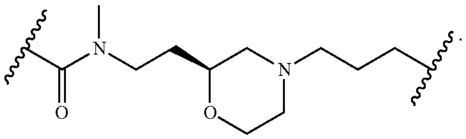 [SMILES: *CCCN1CCO[C@@H](CCN(C)C(*)=O)C1]
In some embodiments, L is
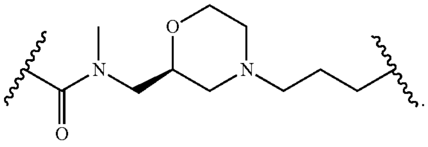 [SMILES: *CCCN1CCO[C@H](CN(C)C(*)=O)C1]
In some embodiments, L is
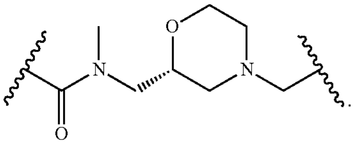 [SMILES: *CN1CCO[C@@H](CN(C)C(*)=O)C1]
In some embodiments, L is
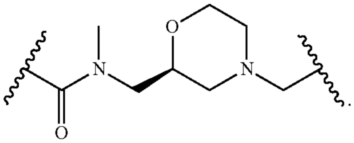 [SMILES: *CN1CCO[C@H](CN(C)C(*)=O)C1]
In some embodiments, L is
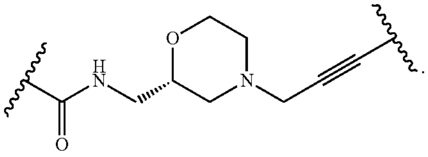 [SMILES: *C#CCN1CCO[C@@H](CNC(*)=O)C1]
In some embodiments, L is
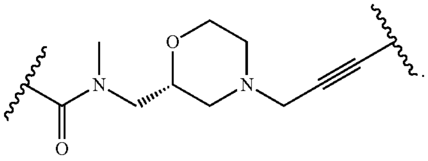 [SMILES: *C#CCN1CCO[C@@H](CN(C)C(*)=O)C1]
In some embodiments, L is
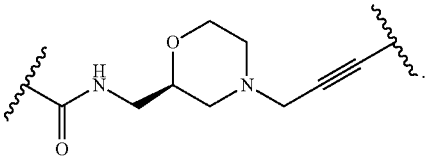 [SMILES: *C#CCN1CCO[C@H](CNC(*)=O)C1]
In some embodiments, L is
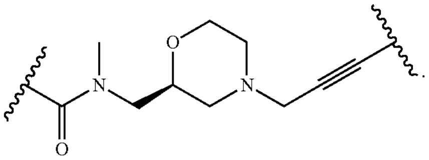 [SMILES: *C#CCN1CCO[C@H](CN(C)C(*)=O)C1]
In some embodiments, L is
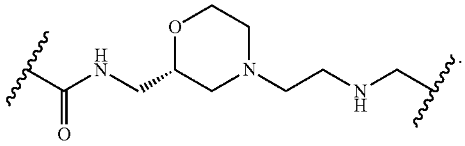 [SMILES: *CNCCN1CCO[C@@H](CNC(*)=O)C1]
In some embodiments, L is
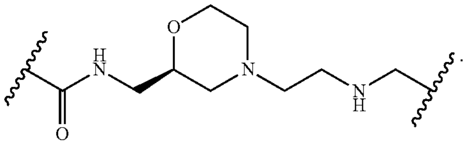 [SMILES: *CNCCN1CCO[C@H](CNC(*)=O)C1]
In some embodiments, L is
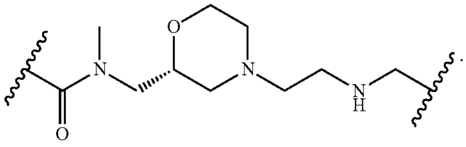 [SMILES: *CNCCN1CCO[C@@H](CN(C)C(*)=O)C1]
In some embodiments L is
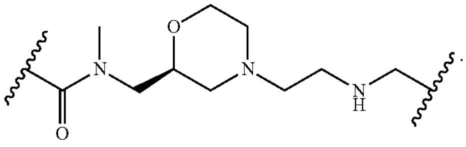 [SMILES: *CNCCN1CCO[C@H](CN(C)C(*)=O)C1]

In some embodiments, L is
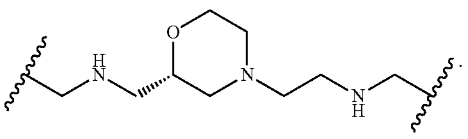 [SMILES: *CNCCN1CCO[C@@H](CNC*)C1]
In some embodiments, L is
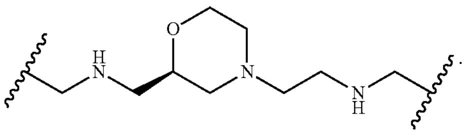 [SMILES: *CNCCN1CCO[C@H](CNC*)C1]
In some embodiments L is
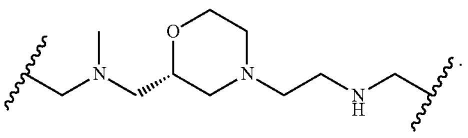 [SMILES: *CNCCN1CCO[C@@H](CN(C)C*)C1]
In some embodiments, L is
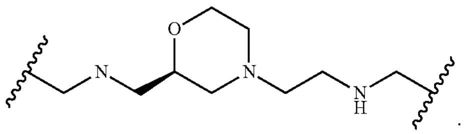 [SMILES: *CNCCN1CCO[C@H](CNC*)C1]
In some embodiments, L is
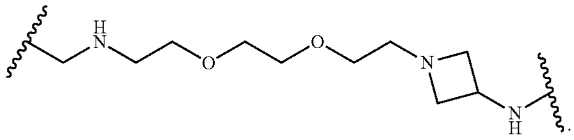 [SMILES: *CNCCOCCOCCN1CC(N*)C1]
In some embodiments, L is
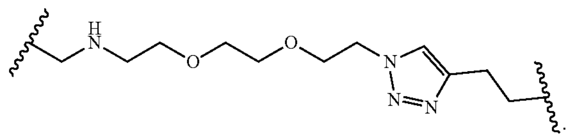 [SMILES: *CCc1cn(CCOCCOCCNC*)nn1]
In some embodiments, L is
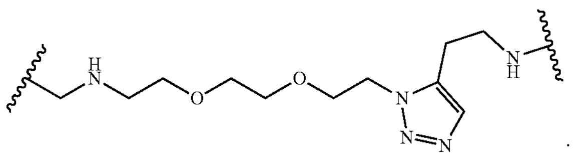 [SMILES: *CNCCOCCOCCn1nncc1CCN*]
In some embodiments, L is
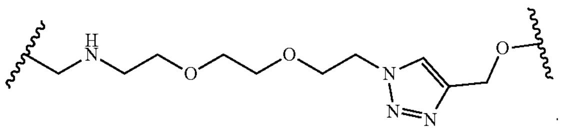 [SMILES: *CNCCOCCOCCn1cc(CO*)nn1]
In some embodiments, L is
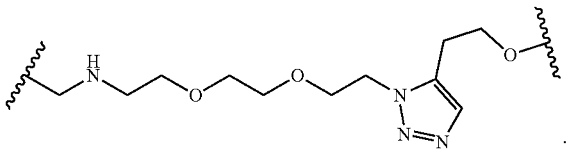 [SMILES: *CNCCOCCOCCn1nncc1CCO*]
In some embodiments, L is
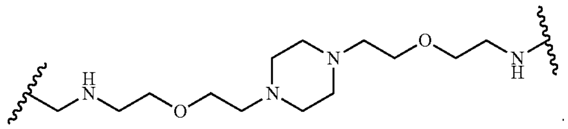 [SMILES: *CNCCOCCN1CCN(CCOCCN*)CC1]
In some embodiments, L is
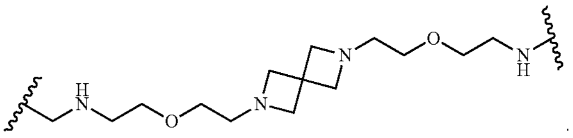 [SMILES: *CNCCOCCN1CC2(CN(CCOCCN*)C2)C1]
In some embodiments, L is
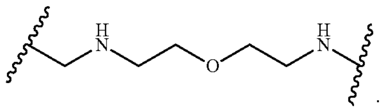 [SMILES: *CNCCOCCN*]
In some embodiments, L is
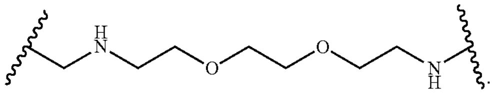 [SMILES: *CNCCOCCOCCN*]

In some embodiments L is
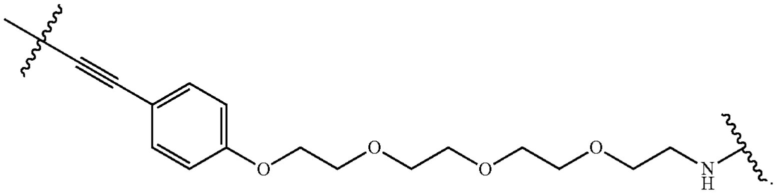 [SMILES: *C#Cc1ccc(OCCOCCOCCOCCN*)cc1]
In some embodiments, L is
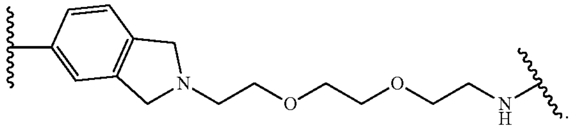 [SMILES: *NCCOCCOCCN1Cc2ccc(*)cc2C1]
In some embodiments, L is
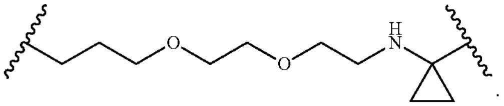 [SMILES: *CCCOCCOCCNC1(*)CC1]
In some embodiments, L is
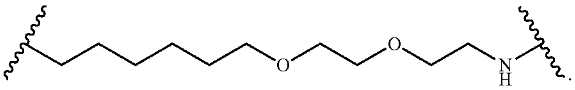 [SMILES: *CCCCCCOCCOCCN*]
In some embodiments, L is
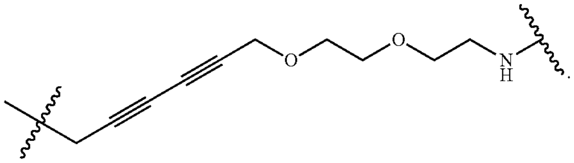 [SMILES: *CC#CC#CCOCCOCCN*]
In some embodiments, L is
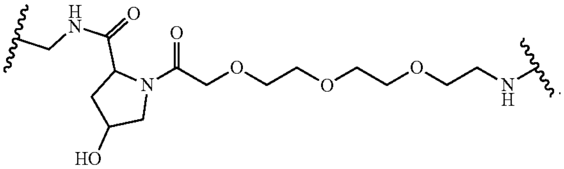 [SMILES: *CNC(=O)C1CC(O)CN1C(=O)COCCOCCOCCN*]
In some embodiments, L is
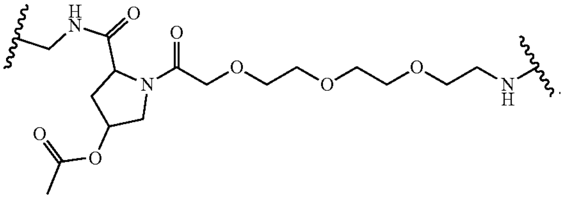 [SMILES: *CNC(=O)C1CC(OC(C)=O)CN1C(=O)COCCOCCOCCN*]
In some embodiments, L is
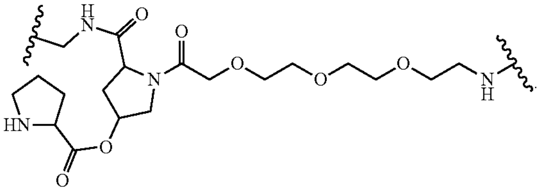 [SMILES: *CNC(=O)C1CC(OC(=O)C2CCCN2)CN1C(=O)COCCOCCOCCN*]
In some embodiments, L is
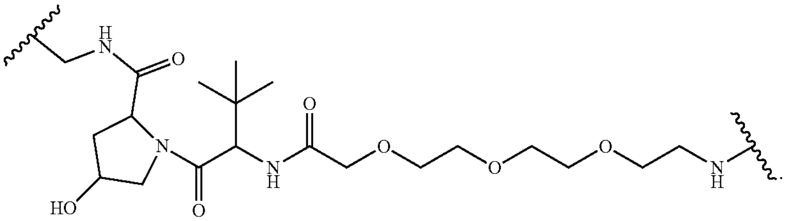 [SMILES: *CNC(=O)C1CC(O)CN1C(=O)C(NC(=O)COCCOCCOCCN*)C(C)(C)C]

In some embodiments, L is
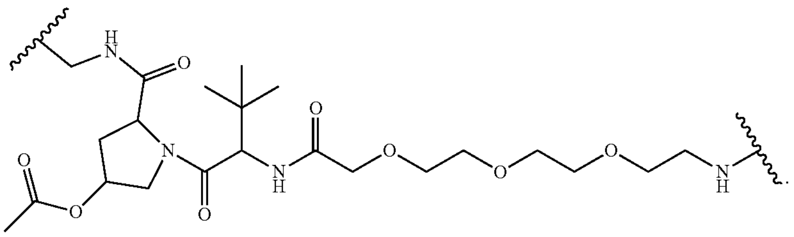 [SMILES: *CNC(=O)C1CC(OC(C)=O)CN1C(=O)C(NC(=O)COCCOCCOCCN*)C(C)(C)C]
In some embodiments, L is
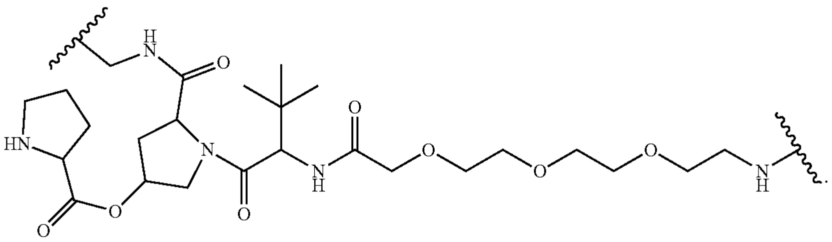 [SMILES: *CNC(=O)C1CC(OC(=O)C2CCCN2)CN1C(=O)C(NC(=O)COCCOCCOCCN*)C(C)(C)C]
In some embodiments, L is
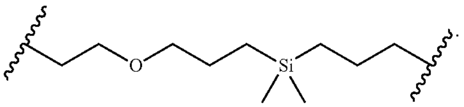 [SMILES: *CCC[Si](C)(C)CCCOCC*]
In some embodiments, L is
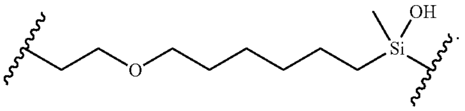
In some embodiments, L is
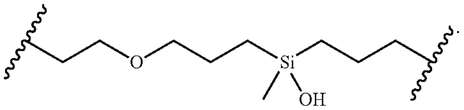 [SMILES: *CCC[Si](C)(O)CCCOCC*]
In some embodiments, L is
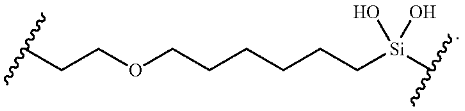
In some embodiments, L is
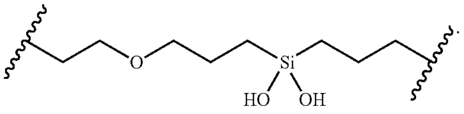 [SMILES: *CCC[Si](O)(O)CCCOCC*]
In some embodiments, L is
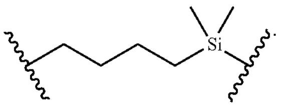
In some embodiments, L is
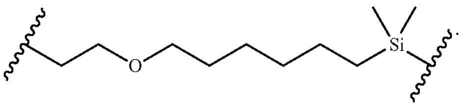 [SMILES: *CCOCCCCCC[Si](*)(C)C]
In some embodiments, L is
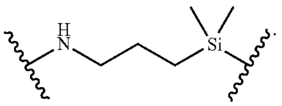 [SMILES: *NCCC[Si](*)(C)C]

In some embodiments, L is
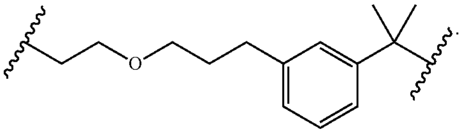 [SMILES: *CCOCCCc1cccc(C(*)(C)C)c1]
In some embodiments, L is
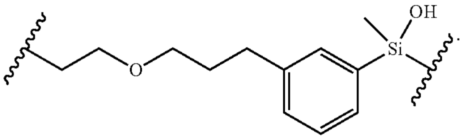 [SMILES: *CCOCCCc1cccc([Si](*)(C)O)c1]
In some embodiments, L is
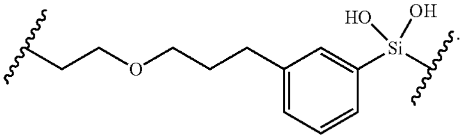 [SMILES: *CCOCCCc1cccc([Si](*)(O)O)c1]
In some embodiments, L is
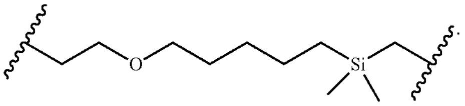 [SMILES: *CCOCCCCC[Si](C)(C)C*]
In some embodiments, L is
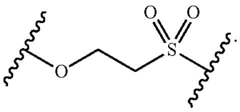 [SMILES: *OCCS(*)(=O)=O]
In some embodiments L is
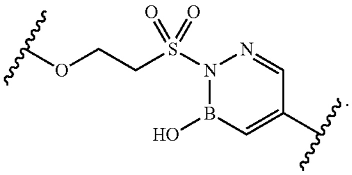 [SMILES: *OCCS(=O)(=O)N1N=CC(*)=CB1O]
In some embodiments, L is
In some embodiments, L is
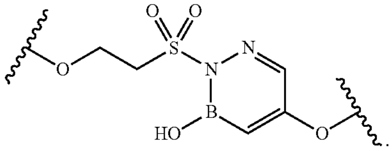 [SMILES: *OCCS(=O)(=O)N1N=CC(O*)=CB1O]
In some embodiments, L is
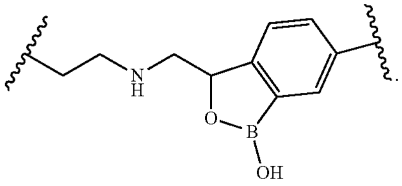 [SMILES: *CCNCC1OB(O)c2cc(*)ccc21]
In some embodiments, L is
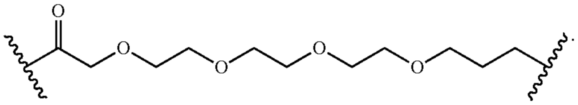 [SMILES: *CCCOCCOCCOCCOCC(*)=O]
In some embodiments, L is
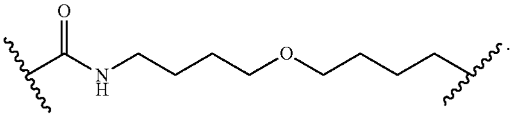 [SMILES: *CCCCOCCCCNC(*)=O]
In some embodiments, L is
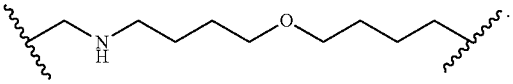 [SMILES: *CCCCOCCCCNC*]
In some embodiments, L is
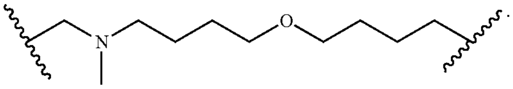 [SMILES: *CCCCOCCCCN(C)C*]
In some embodiments, L is
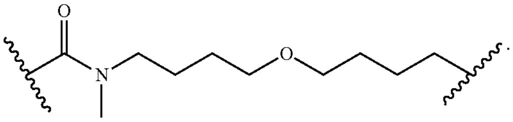 [SMILES: *CCCCOCCCCN(C)C(*)=O]

In some embodiments, L is

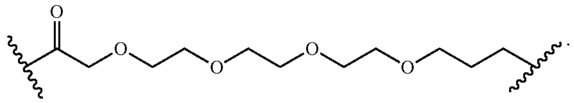 [SMILES: *CCCOCCOCCOCCOCC(*)=O]

In some embodiments, L is

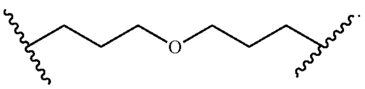 [SMILES: *CCCOCCC*]

In some embodiments, L is

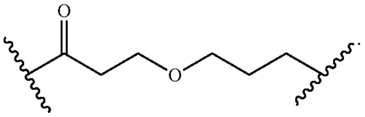 [SMILES: *CCCOCCC(*)=O]

In some embodiments, L is

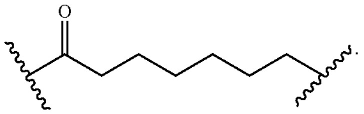 [SMILES: *CCCCCCC(*)=O]

In some embodiments, L is

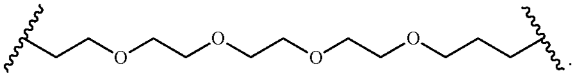 [SMILES: *CCCOCCOCCOCCOCC*]

In some embodiments, L is

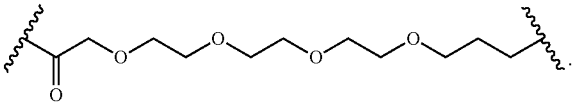 [SMILES: *CCCOCCOCCOCCOCC(*)=O]

In some embodiments, L is

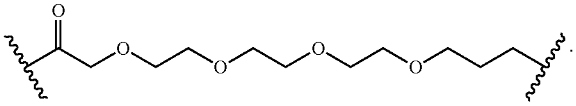 [SMILES: *CCCOCCOCCOCCOCC(*)=O]

In some embodiments, L is

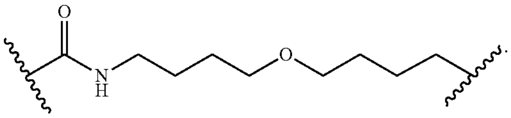 [SMILES: *CCCCOCCCCNC(*)=O]

In some embodiments, L is

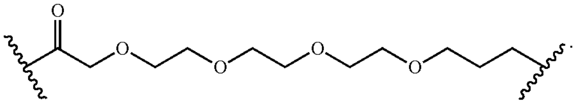 [SMILES: *CCCOCCOCCOCCOCC(*)=O]

In some embodiments, Lis

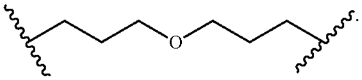 [SMILES: *CCCOCCC*]

In some embodiments, L is

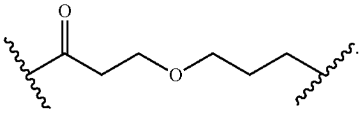 [SMILES: *CCCOCCC(*)=O]

In some embodiments, L is

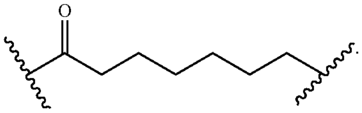 [SMILES: *CCCCCCC(*)=O]

In some embodiments, L is

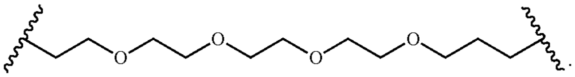 [SMILES: *CCCOCCOCCOCCOCC*]

In some embodiments, L is

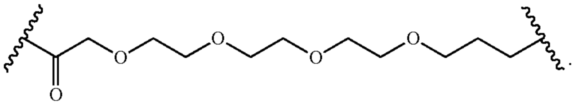 [SMILES: *CCCOCCOCCOCCOCC(*)=O]

In some embodiments, L is

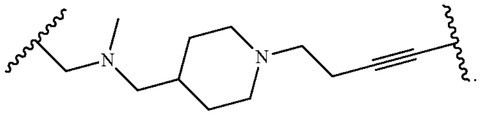 [SMILES: *C#CCCN1CCC(CN(C)C*)CC1]

In some embodiments, L is

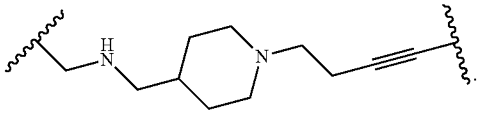

In some embodiments, L is
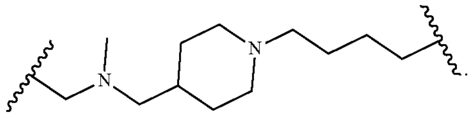 [SMILES: *CCCCN1CCC(CN(C)C*)CC1]
In some embodiments, L is
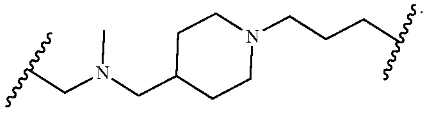 [SMILES: *CCCN1CCC(CN(C)C*)CC1]
In some embodiments, L is
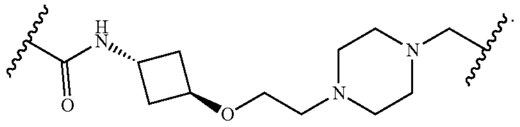 [SMILES: *CN1CCN(CCO[C@H]2C[C@H](NC(*)=O)C2)CC1]
In some embodiments, L is
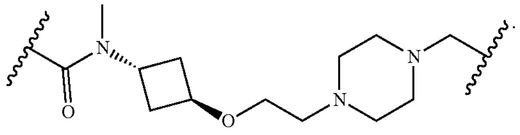 [SMILES: *CN1CCN(CCO[C@H]2C[C@H](N(C)C(*)=O)C2)CC1]
In some embodiments, L is
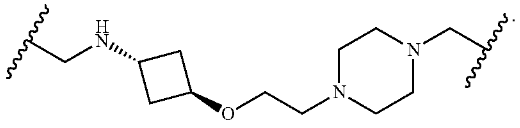 [SMILES: *CN[C@H]1C[C@H](OCCN2CCN(C*)CC2)C1]
In some embodiments, L is
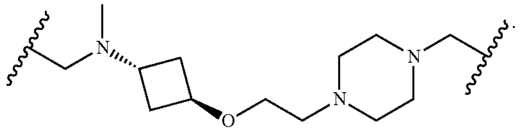 [SMILES: *CN1CCN(CCO[C@H]2C[C@H](N(C)C*)C2)CC1]
In some embodiments, L is
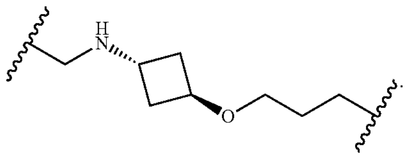 [SMILES: *CCCO[C@H]1C[C@H](NC*)C1]
In some embodiments, L is
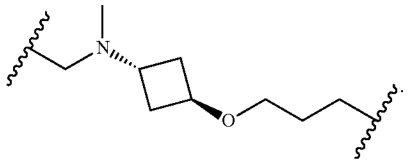 [SMILES: *CCCO[C@H]1C[C@H](N(C)C*)C1]
In some embodiments, L is
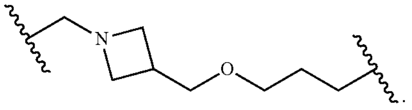 [SMILES: *CCCOCC1CN(C*)C1]
In some embodiments, L is
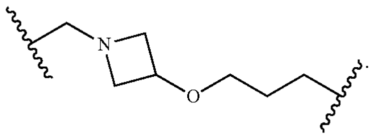 [SMILES: *CCCOC1CN(C*)C1]
In some embodiments, L is
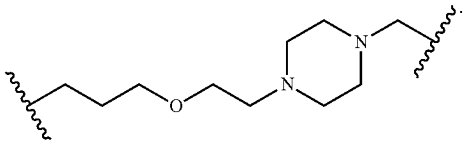 [SMILES: *CCCOCCN1CCN(C*)CC1]
In some embodiments, L is
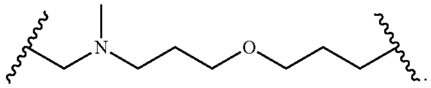 [SMILES: *CCCOCCCN(C)C*]
In some embodiments, L is
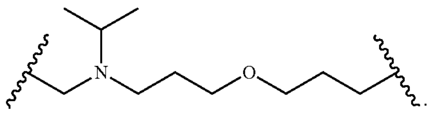 [SMILES: *CCCOCCCN(C*)C(C)C]
In some embodiments, L is
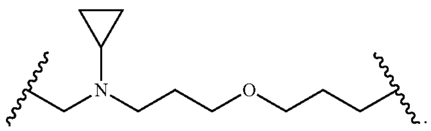 [SMILES: *CCCOCCCN(C*)C1CC1]

In some embodiments, L is
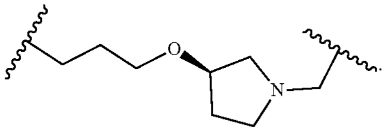 [SMILES: *CCCO[C@@H]1CCN(C*)C1]
In some embodiments, L is
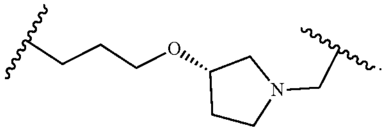 [SMILES: *CCCO[C@H]1CCN(C*)C1]
In some embodiments, L is
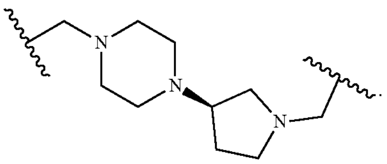 [SMILES: *CN1CCN([C@@H]2CCN(C*)C2)CC1]
In some embodiments, L is
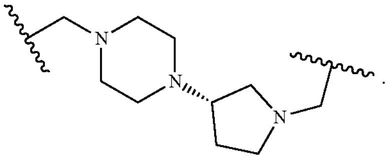 [SMILES: *CN1CCN([C@H]2CCN(C*)C2)CC1]
In some embodiments, L is
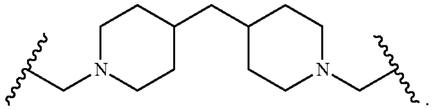 [SMILES: *CN1CCC(CC2CCN(C*)CC2)CC1]
In some embodiments, L is
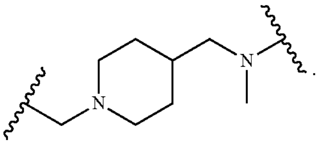 [SMILES: *CN1CCC(CN(*)C)CC1]
In some embodiments, L is
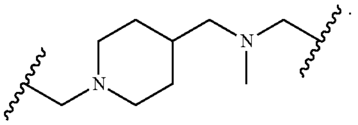 [SMILES: *CN(C)CC1CCN(C*)CC1]
In some embodiments, L is
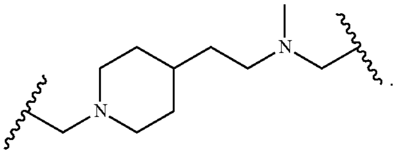 [SMILES: *CN(C)CCC1CCN(C*)CC1]
In some embodiments, L is
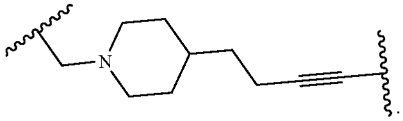 [SMILES: *C#CCCC1CCN(C*)CC1]
In some embodiments, L is
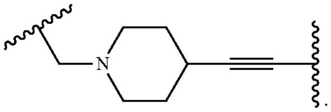 [SMILES: *C#CC1CCN(C*)CC1]
In some embodiments, L is
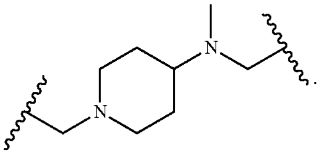 [SMILES: *CN1CCC(N(C)C*)CC1]
In some embodiments, L is
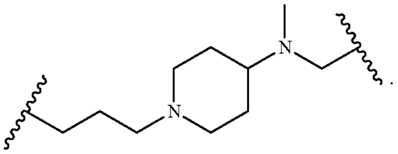 [SMILES: *CCCN1CCC(N(C)C*)CC1]
In some embodiments L is
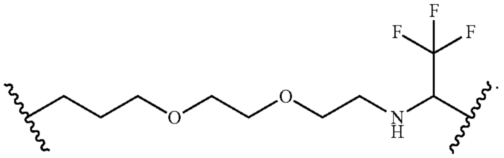 [SMILES: *CCCOCCOCCNC(*)C(F)(F)F]

In some embodiments, L is
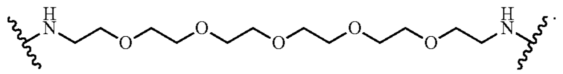 [SMILES: *NCCOCCOCCOCCOCCOCCN*]
In some embodiments, L is
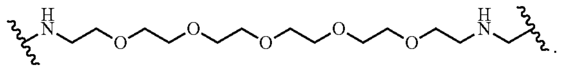 [SMILES: *CNCCOCCOCCOCCOCCOCCN*]
In some embodiments, L is
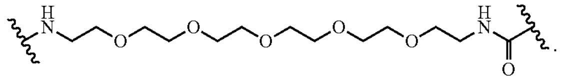 [SMILES: *NCCOCCOCCOCCOCCOCCNC(*)=O]
In some embodiments, L is
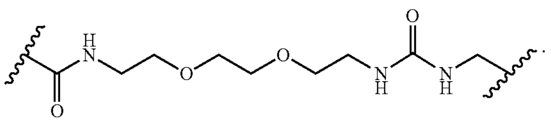 [SMILES: *CNC(=O)NCCOCCOCCNC(*)=O]
In some embodiments, L is
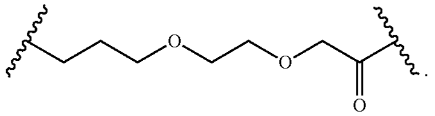 [SMILES: *CCCOCCOCC(*)=O]
In some embodiments, L is
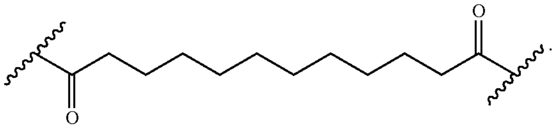 [SMILES: *C(=O)CCCCCCCCCCC(*)=O]
In some embodiments, L is
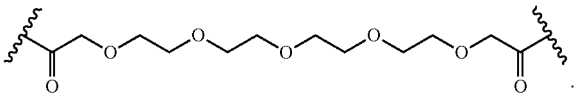 [SMILES: *C(=O)COCCOCCOCCOCCOCC(*)=O]
In some embodiments, L is
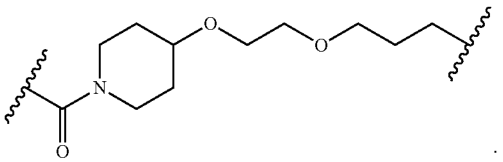 [SMILES: *CCCOCCOC1CCN(C(*)=O)CC1]
In some embodiments, L is
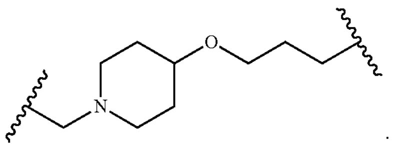 [SMILES: *CCCOC1CCN(C*)CC1]
In some embodiments, L is
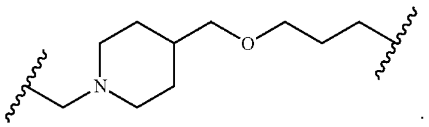 [SMILES: *CCCOCC1CCN(C*)CC1]
In some embodiments, L is
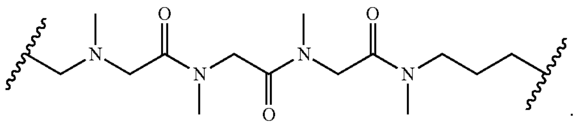 [SMILES: *CCCN(C)C(=O)CN(C)C(=O)CN(C)C(=O)CN(C)C*]
In some embodiments, L is
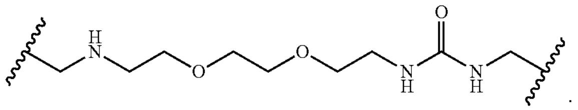 [SMILES: *CNCCOCCOCCNC(=O)NC*]
In some embodiment, L is
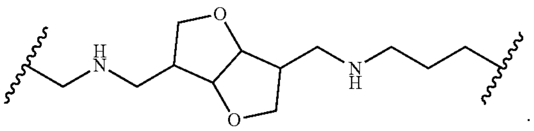 [SMILES: *CCCNCC1COC2C(CNC*)COC12]
In some embodiments, L is
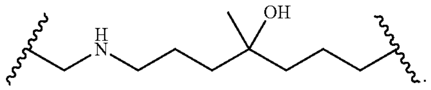 [SMILES: *CCCC(C)(O)CCCNC*]
In some embodiments, L is
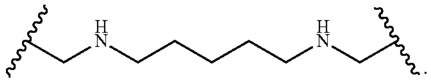 [SMILES: *CNCCCCCNC*]

In some embodiments, L is
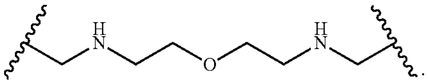 [SMILES: *CNCCOCCNC*]
In some embodiments L is
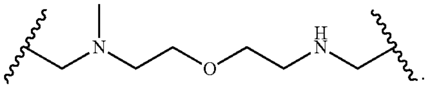 [SMILES: *CNCCOCCN(C)C*]
In some embodiments, L is
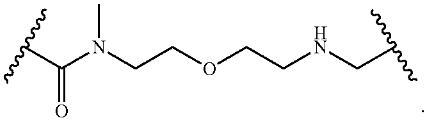 [SMILES: *CNCCOCCN(C)C(*)=O]
In some embodiments L is
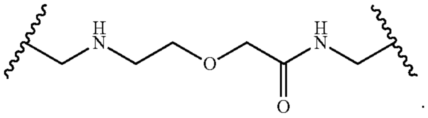 [SMILES: *CNCCOCC(=O)NC*]
In some embodiments, L is
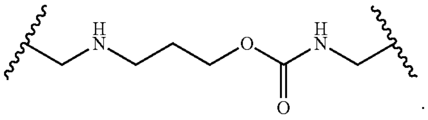 [SMILES: *CNCCCOC(=O)NC*]
In some embodiments, L is
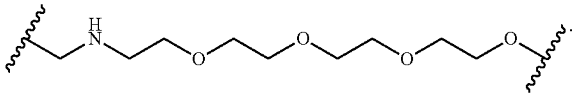 [SMILES: *CNCCOCCOCCOCCO*]
In some embodiments, L is
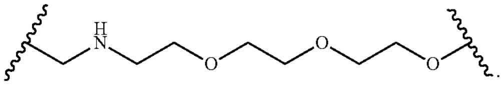 [SMILES: *CNCCOCCOCCO*]
In some embodiments, L is
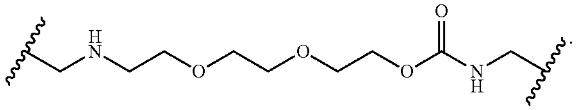 [SMILES: *CNCCOCCOCCOC(=O)NC*]
In some embodiments, L is
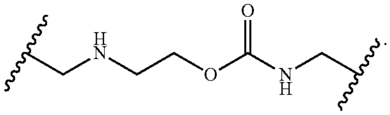 [SMILES: *CNCCOC(=O)NC*]
In some embodiments, L is
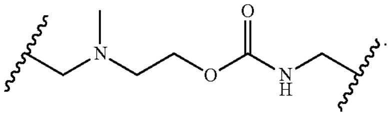 [SMILES: *CNC(=O)OCCN(C)C*]
In some embodiments, L is
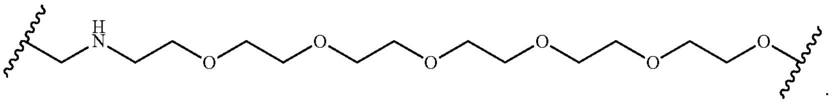
In some embodiments, L is
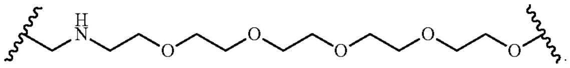
In some embodiments, L is
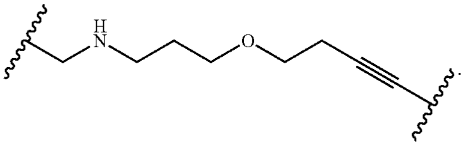 [SMILES: *C#CCCOCCCNC*]

In some embodiments, L is
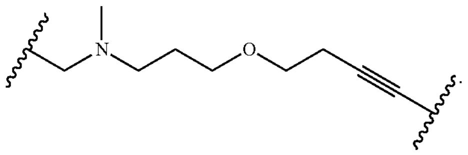 [SMILES: *C#CCCOCCCN(C)C*]
In some embodiments, L is
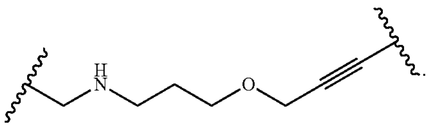 [SMILES: *C#CCOCCCNC*]
In some embodiments, L is
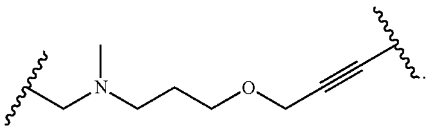 [SMILES: *C#CCOCCCN(C)C*]
In some embodiments, L is
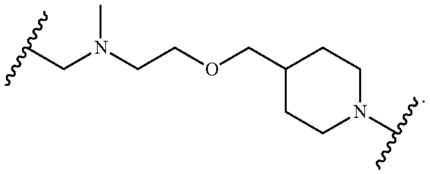 [SMILES: *CN(C)CCOCC1CCN(*)CC1]
In some embodiments, L is
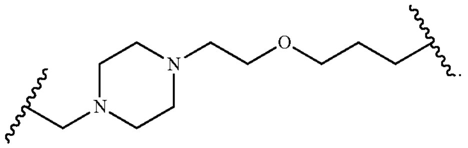 [SMILES: *CCCOCCN1CCN(C*)CC1]
In some embodiments, L is
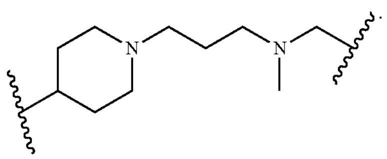 [SMILES: *CN(C)CCCN1CCC(*)CC1]
In some embodiments, L is
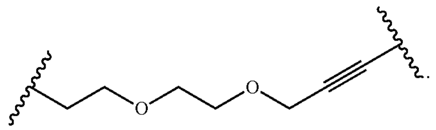 [SMILES: *C#CCOCCOCC*]
In some embodiments, L is
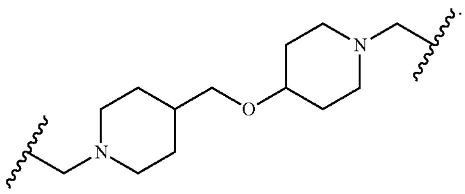 [SMILES: *CN1CCC(COC2CCN(C*)CC2)CC1]
In some embodiments, L is
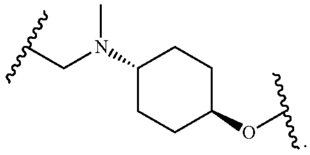 [SMILES: *CN(C)[C@H]1CC[C@H](O*)CC1]
In some embodiments, L is
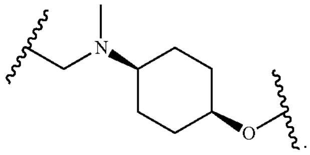 [SMILES: *CN(C)[C@H]1CC[C@@H](O*)CC1]
In some embodiments, L is
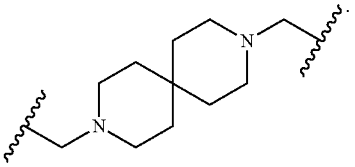 [SMILES: *CN1CCC2(CC1)CCN(C*)CC2]
In some embodiments, L is
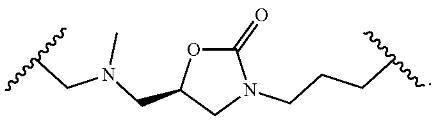 [SMILES: *CCCN1C[C@@H](CN(C)C*)OC1=O]

In some embodiments, L is
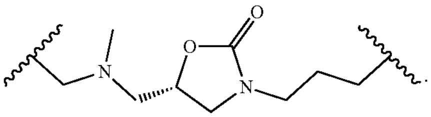 [SMILES: *CCCN1C[C@H](CN(C)C*)OC1=O]
In some embodiments, L is
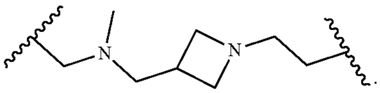 [SMILES: *CCN1CC(CN(C)C*)C1]
In some embodiments, L is
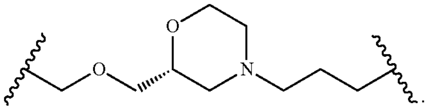 [SMILES: *CCCN1CCO[C@@H](COC*)C1]
In some embodiments, L is
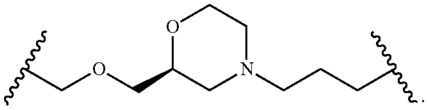
In some embodiments, L is
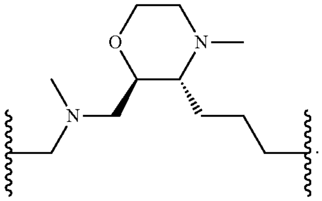 [SMILES: *CCC[C@@H]1[C@@H](CN(C)C*)OCCN1C]
In some embodiments, L is
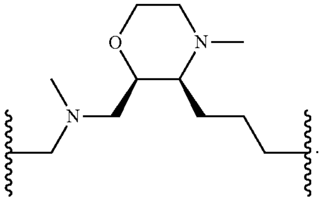 [SMILES: *CCC[C@H]1[C@@H](CN(C)C*)OCCN1C]
In some embodiments, L is
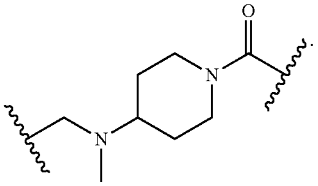 [SMILES: *CN(C)C1CCN(C(*)=O)CC1]
In some embodiments, L is
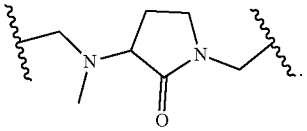 [SMILES: *CN1CCC(N(C)C*)C1=O]
In some embodiments, L is
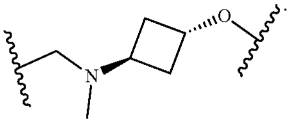 [SMILES: *CN(C)[C@H]1C[C@H](O*)C1]
In some embodiments, L is
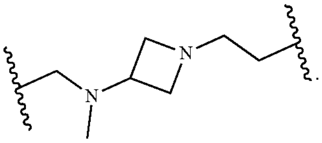 [SMILES: *CCN1CC(N(C)C*)C1]
In some embodiments L is
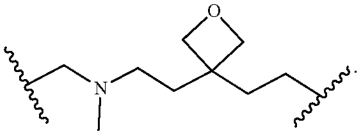 [SMILES: *CCC1(CCN(C)C*)COC1]
In some embodiments, L is
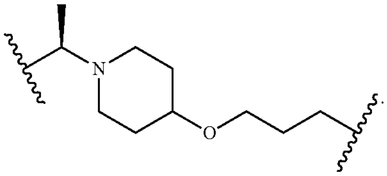 [SMILES: *CCCOC1CCN([C@@H](*)C)CC1]

In some embodiments, L is

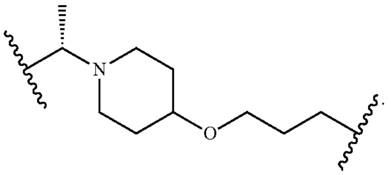 [SMILES: *CCCOC1CCN([C@H](*)C)CC1]

In some embodiments, L is

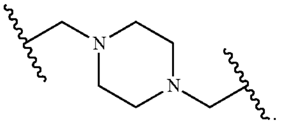 [SMILES: *CN1CCN(C*)CC1]

In some embodiments, L is

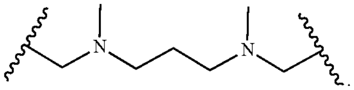 [SMILES: *CN(C)CCCN(C)C*]

In some embodiments L is

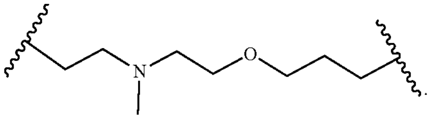 [SMILES: *CCCOCCN(C)CC*]

In some embodiments, L is

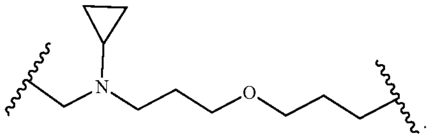 [SMILES: *CCCOCCCN(C*)C1CC1]

In some embodiments L is

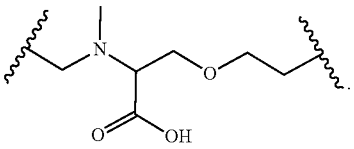 [SMILES: *CCOCC(C(=O)O)N(C)C*]

In some embodiments, L is

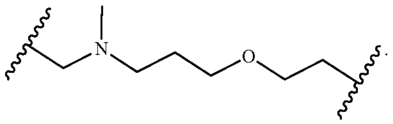 [SMILES: *CCOCCCN(C)C*]

In some embodiments, L is

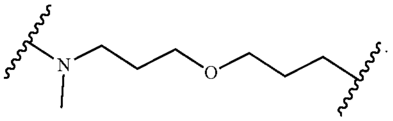 [SMILES: *CCCOCCCN(*)C]

In some embodiments, L is

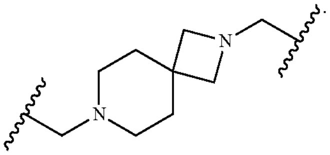 [SMILES: *CN1CCC2(CC1)CN(C*)C2]

In some embodiments, L is

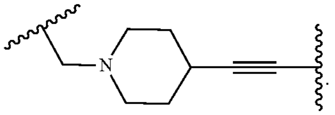 [SMILES: *C#CC1CCN(C*)CC1]

In some embodiments, L is

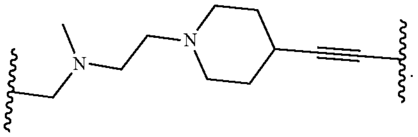 [SMILES: *C#CC1CCN(CCN(C)C*)CC1]

In some embodiments, L is

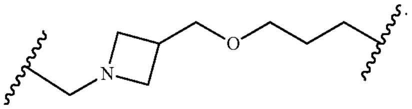 [SMILES: *CCCOCC1CN(C*)C1]

In some embodiments, L is a covalent bond. In some embodiments L is

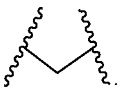 [SMILES: *C*]

In some embodiments, L is

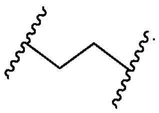 [SMILES: *CC*]

In some embodiments, L is

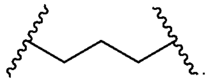 [SMILES: *CCC*]

In some embodiments, L is

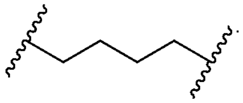 [SMILES: *CCCC*]

In some embodiments, L is

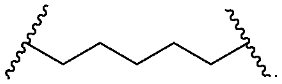 [SMILES: *CCCCC*]

In some embodiments, L is

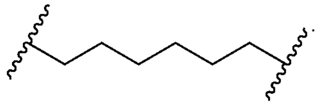 [SMILES: *CCCCCC*]

In some embodiments, L is

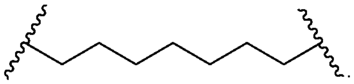 [SMILES: *CCCCCCC*]

In some embodiments, L is

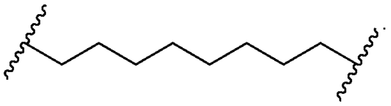 [SMILES: *CCCCCCCC*]

In some embodiments, L is

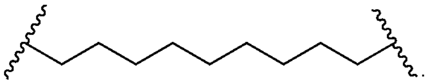 [SMILES: *CCCCCCCCC*]

In some embodiments, L is a covalent bond. In some embodiments, L is

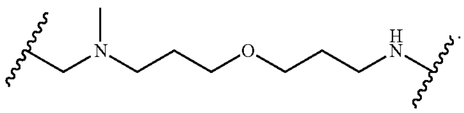 [SMILES: *CN(C)CCCOCCCN*]

In some embodiments, L is

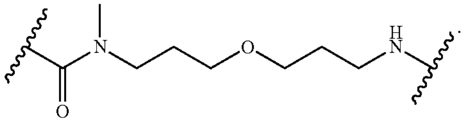 [SMILES: *NCCCOCCCN(C)C(*)=O]

In some embodiments, L is

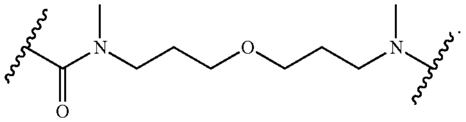 [SMILES: *C(=O)N(C)CCCOCCCN(*)C]

In some embodiments, L is

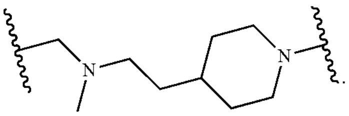 [SMILES: *CN(C)CCC1CCN(*)CC1]

In some embodiments, L is

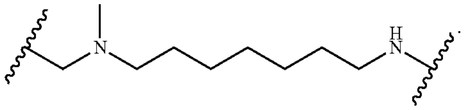 [SMILES: *CN(C)CCCCCCCN*]

In some embodiments, L is

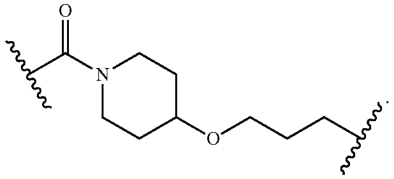 [SMILES: *CCCOC1CCN(C(*)=O)CC1]

In some embodiments, L is

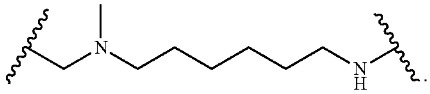 [SMILES: *CN(C)CCCCCCN*]

In some embodiments, L is

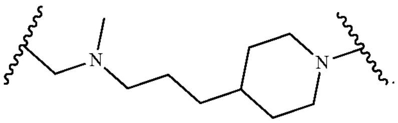 [SMILES: *CN(C)CCCC1CCN(*)CC1]

In some embodiments, L is
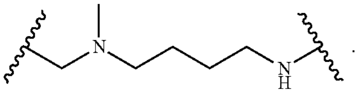 [SMILES: *CN(C)CCCCN*]
In some embodiments, L is
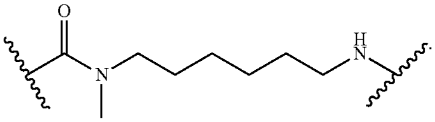 [SMILES: *NCCCCCCN(C)C(*)=O]
In some embodiments, L is
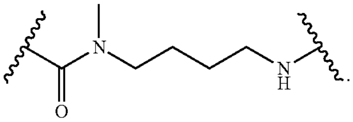 [SMILES: *NCCCCN(C)C(*)=O]
In some embodiments L is
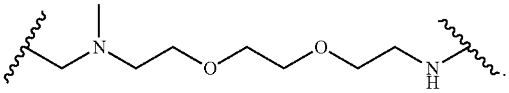 [SMILES: *CN(C)CCOCCOCCN*]
In some embodiments, L is
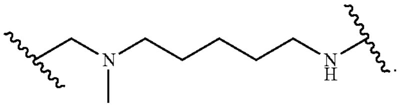 [SMILES: *CN(C)CCCCCN*]
In some embodiments, L is
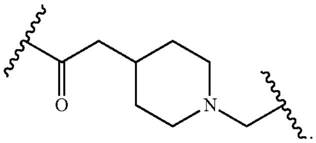 [SMILES: *CN1CCC(CC(*)=O)CC1]
In some embodiments, L is
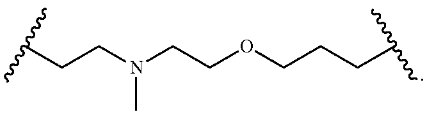 [SMILES: *CCCOCCN(C)CC*]
In some embodiments, L is
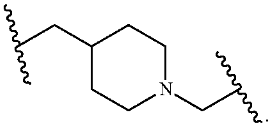 [SMILES: *CC1CCN(C*)CC1]
In some embodiments, L is
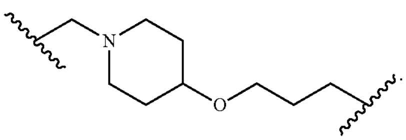 [SMILES: *CCCOC1CCN(C*)CC1]
In some embodiments, L is
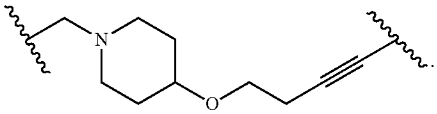 [SMILES: *C#CCCOC1CCN(C*)CC1]
In some embodiments, L is
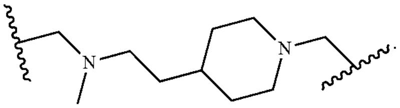 [SMILES: *CN(C)CCC1CCN(C*)CC1]
In some embodiments, L is
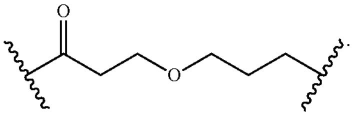 [SMILES: *CCCOCCC(*)=O]
In some embodiments, L is
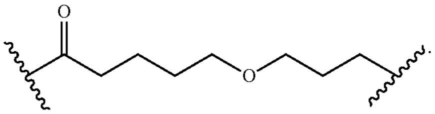 [SMILES: *CCCOCCCCC(*)=O]
In some embodiments, L is
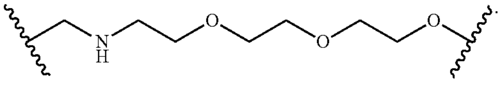 [SMILES: *CNCCOCCOCCO*]

In some embodiments L is
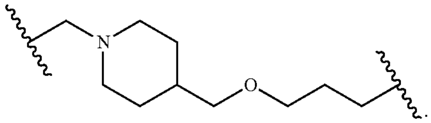 [SMILES: *CCCOCC1CCN(C*)CC1]
In some embodiments, L is
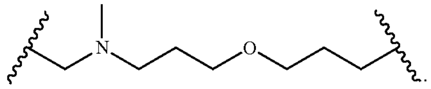 [SMILES: *CCCOCCCN(C)C*]
In some embodiments, L is
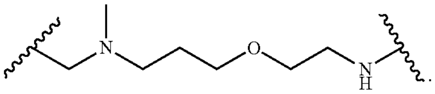 [SMILES: *CN(C)CCCOCCN*]
In some embodiments, L is
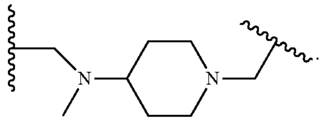 [SMILES: *CN1CCC(N(C)C*)CC1]
In some embodiments, L is
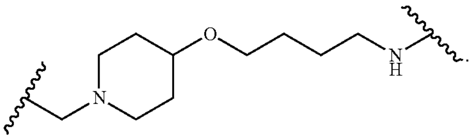 [SMILES: *CN1CCC(OCCCCN*)CC1]
In some embodiments, L is
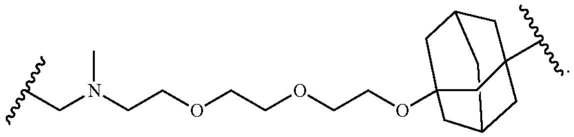 [SMILES: *CN(C)CCOCCOCCOC12CC3CC(CC(*)(C3)C1)C2]
In some embodiments, L is
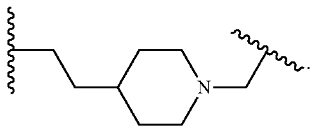 [SMILES: *CCC1CCN(C*)CC1]
In some embodiments, L is
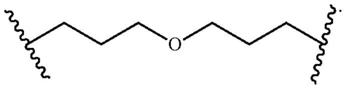 [SMILES: *CCCOCCC*]
In some embodiments, L is
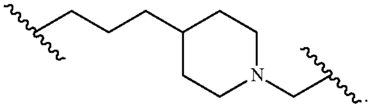 [SMILES: *CCCC1CCN(C*)CC1]
In some embodiments, L is
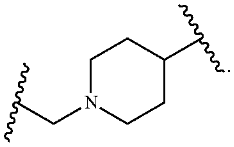 [SMILES: *CN1CCC(*)CC1]
In some embodiments, L is
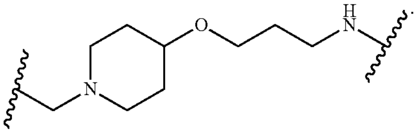 [SMILES: *CN1CCC(OCCCN*)CC1]
In some embodiments, L is
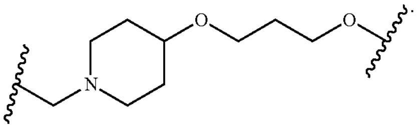 [SMILES: *CN1CCC(OCCCO*)CC1]
In some embodiments, L is
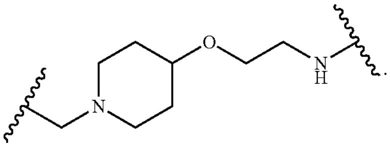 [SMILES: *CN1CCC(OCCN*)CC1]
In some embodiments, L is
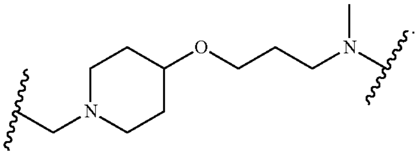 [SMILES: *CN1CCC(OCCCN(*)C)CC1]

In some embodiments, L is
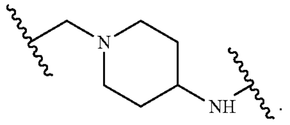 [SMILES: *CN1CCC(N*)CC1]
In some embodiments, L is
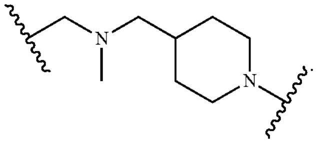 [SMILES: *CN(C)CC1CCN(*)CC1]
In some embodiments, L is
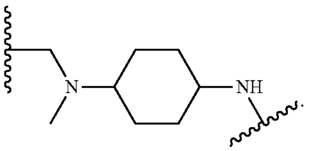 [SMILES: *CN(C)C1CCC(N*)CC1]
In some embodiments, L is
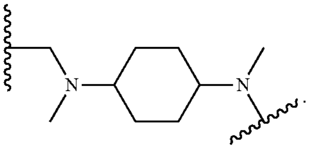 [SMILES: *CN(C)C1CCC(N(*)C)CC1]
In some embodiments, L is
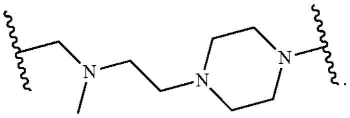 [SMILES: *CN(C)CCN1CCN(*)CC1]
In some embodiments, L is
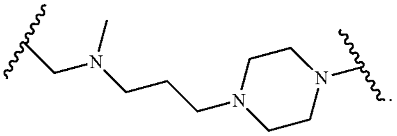 [SMILES: *CN(C)CCCN1CCN(*)CC1]
In some embodiments, L is
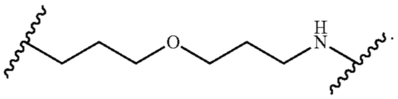 [SMILES: *CCCOCCCN*]
In some embodiments, L is
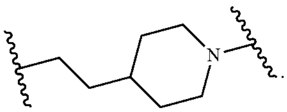 [SMILES: *CCC1CCN(*)CC1]
In some embodiments, L is
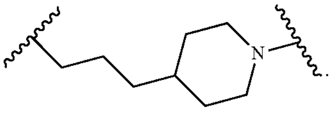 [SMILES: *CCCC1CCN(*)CC1]
In some embodiments, L is
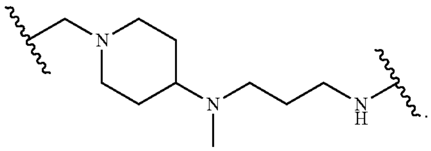 [SMILES: *CN1CCC(N(C)CCCN*)CC1]
In some embodiments, L is
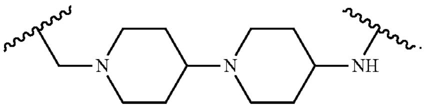 [SMILES: *CN1CCC(N2CCC(N*)CC2)CC1]
In some embodiments, L is
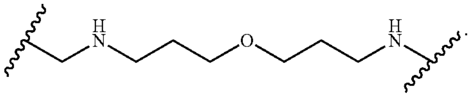 [SMILES: *CNCCCOCCCN*]
In some embodiments, L is
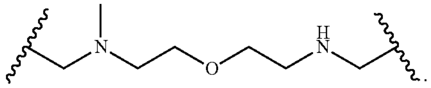 [SMILES: *CNCCOCCN(C)C*]
In some embodiments, L is
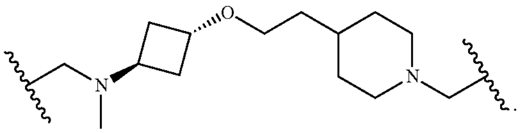 [SMILES: *CN1CCC(CCO[C@H]2C[C@H](N(C)C*)C2)CC1]

In some embodiments, L is
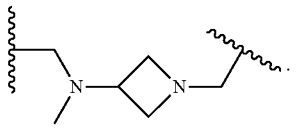 [SMILES: *CN1CC(N(C)C*)C1]
In some embodiments, L is
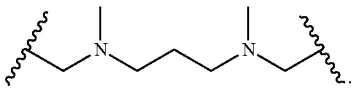 [SMILES: *CN(C)CCCN(C)C*]
In some embodiments, L is
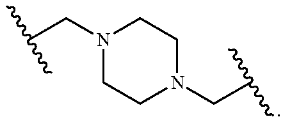 [SMILES: *CN1CCN(C*)CC1]
In some embodiments, L is
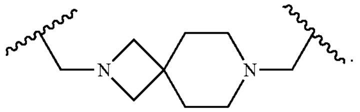 [SMILES: *CN1CCC2(CC1)CN(C*)C2]
In some embodiments, L is
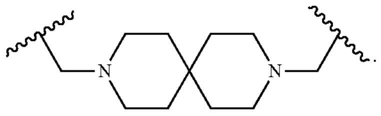 [SMILES: *CN1CCC2(CC1)CCN(C*)CC2]
In some embodiments, L is
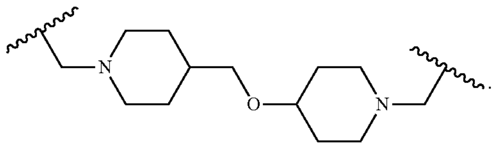 [SMILES: *CN1CCC(COC2CCN(C*)CC2)CC1]
In some embodiments, L is
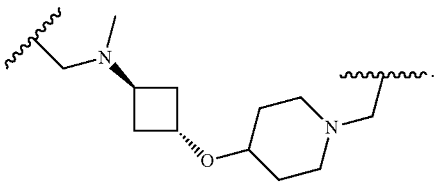 [SMILES: *CN1CCC(O[C@H]2C[C@H](N(C)C*)C2)CC1]
In some embodiments, L is
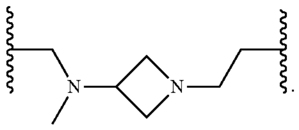 [SMILES: *CCN1CC(N(C)C*)C1]
In some embodiments, L is
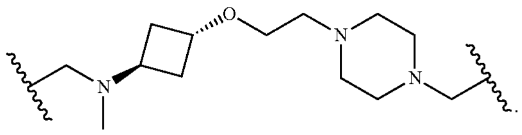
In some embodiments, L is
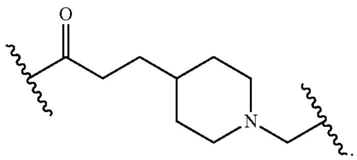 [SMILES: *CN1CCC(CCC(*)=O)CC1]
In some embodiments, L is
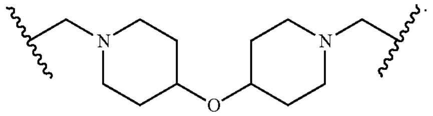 [SMILES: *CN1CCC(OC2CCN(C*)CC2)CC1]
In some embodiments, L is
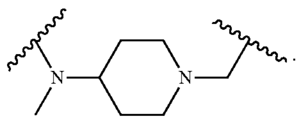 [SMILES: *CN1CCC(N(*)C)CC1]
In some embodiments, L is
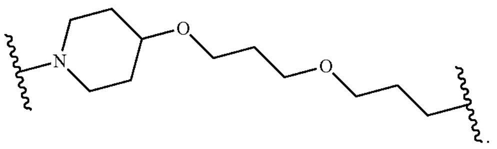 [SMILES: *CCCOCCCOC1CCN(*)CC1]
In some embodiments, L is
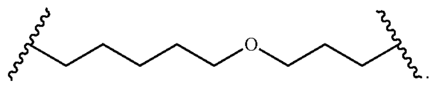 [SMILES: *CCCCCOCCC*]

In some embodiments, L is
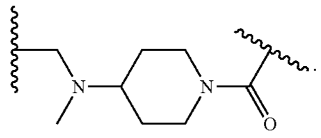 [SMILES: *CN(C)C1CCN(C(*)=O)CC1]
In some embodiments, L is
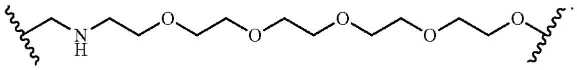 [SMILES: *CNCCOCCOCCOCCOCCO*]
In some embodiments, L is
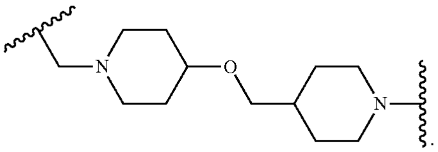 [SMILES: *CN1CCC(OCC2CCN(*)CC2)CC1]
In some embodiments, L is
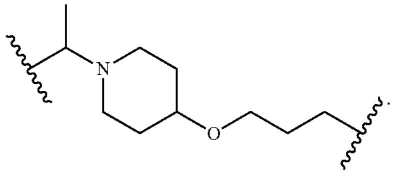 [SMILES: *CCCOC1CCN(C(*)C)CC1]
In some embodiments, L is
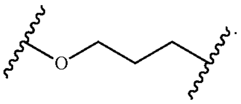 [SMILES: *CCCO*]
In some embodiments, L is
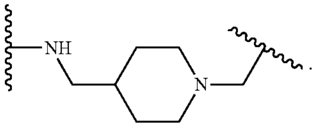 [SMILES: *CN1CCC(CN*)CC1]
In some embodiments, L is
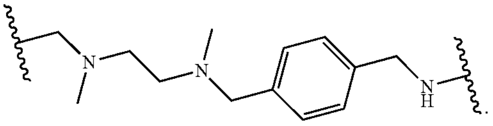 [SMILES: *CN(C)CCN(C)Cc1ccc(CN*)cc1]
In some embodiments, L is
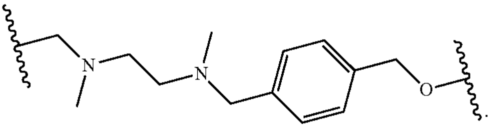 [SMILES: *CN(C)CCN(C)Cc1ccc(CO*)cc1]
In some embodiments, L is
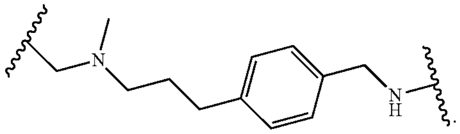 [SMILES: *CN(C)CCCc1ccc(CN*)cc1]
In some embodiments, L is
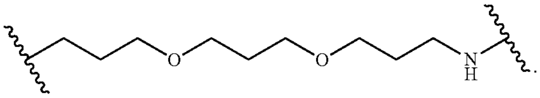 [SMILES: *CCCOCCCOCCCN*]
In some embodiments, L is
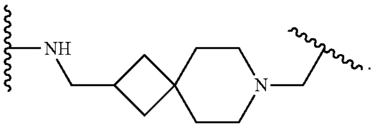 [SMILES: *CN1CCC2(CC1)CC(CN*)C2]
In some embodiments, L is
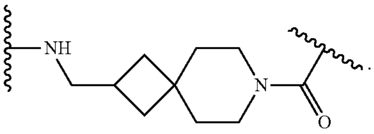 [SMILES: *NCC1CC2(CCN(C(*)=O)CC2)C1]
In some embodiments, L is
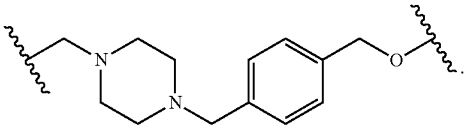 [SMILES: *CN1CCN(Cc2ccc(CO*)cc2)CC1]
In some embodiments, L is
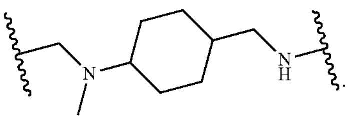 [SMILES: *CN(C)C1CCC(CN*)CC1]

In some embodiments, L is
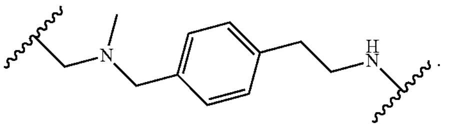 [SMILES: *CN(C)Cc1ccc(CCN*)cc1]
In some embodiments, L is
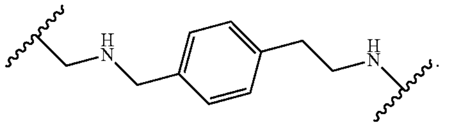 [SMILES: *CNCc1ccc(CCN*)cc1]
In some embodiments, L is
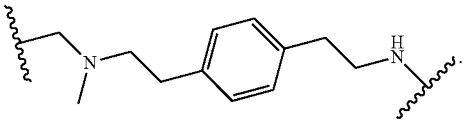 [SMILES: *CN(C)CCc1ccc(CCN*)cc1]
In some embodiments, L is
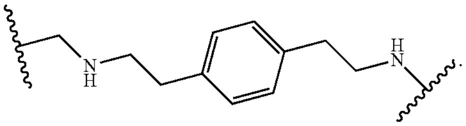 [SMILES: *CNCCc1ccc(CCN*)cc1]
In some embodiments L is
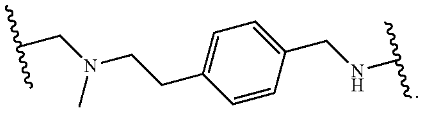 [SMILES: *CN(C)CCc1ccc(CN*)cc1]
In some embodiments, L is
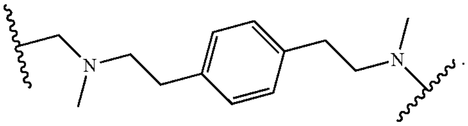 [SMILES: *CN(C)CCc1ccc(CCN(*)C)cc1]
In some embodiments, L is
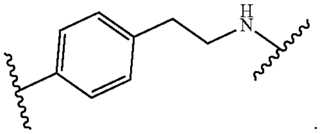 [SMILES: *NCCc1ccc(*)cc1]
In In some embodiments L is
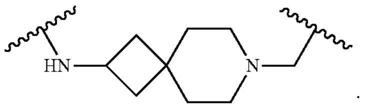 [SMILES: *CN1CCC2(CC1)CC(N*)C2]
In some In In some embodiments, L is
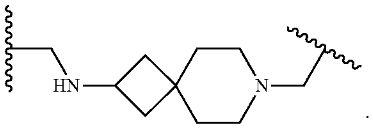 [SMILES: *CNC1CC2(CCN(C*)CC2)C1]
embodiments, L is
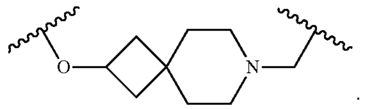 [SMILES: *CN1CCC2(CC1)CC(O*)C2]
In some embodiments, L is
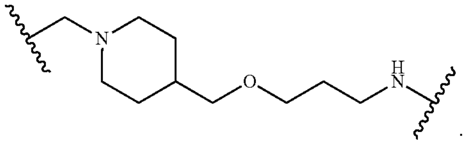 [SMILES: *CN1CCC(COCCCN*)CC1]
In some embodiments, L is
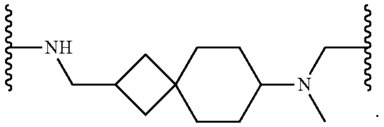 [SMILES: *CN(C)C1CCC2(CC1)CC(CN*)C2]
In some embodiments L is
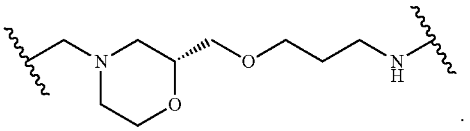 [SMILES: *CN1CCO[C@@H](COCCCN*)C1]
In some embodiments, L is
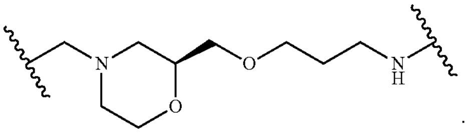 [SMILES: *CN1CCO[C@H](COCCCN*)C1]

In some embodiments, L is
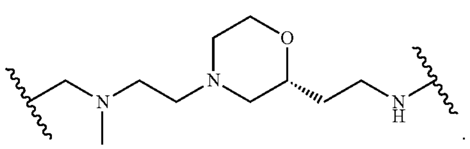 [SMILES: *CN(C)CCN1CCO[C@H](CCN*)C1]
In some embodiments, L is
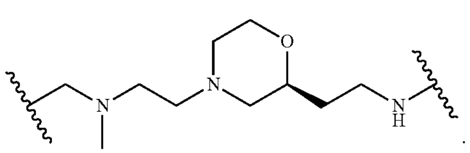 [SMILES: *CN(C)CCN1CCO[C@@H](CCN*)C1]
In some embodiments, L is
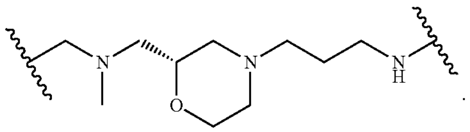 [SMILES: *CN(C)C[C@@H]1CN(CCCN*)CCO1]
In some embodiments, L is
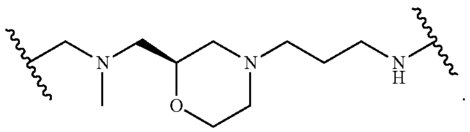 [SMILES: *CN(C)C[C@H]1CN(CCCN*)CCO1]
In some embodiments, L is
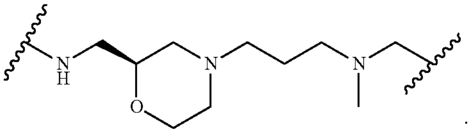 [SMILES: *CN(C)CCCN1CCO[C@@H](CN*)C1]
In some embodiments, L is
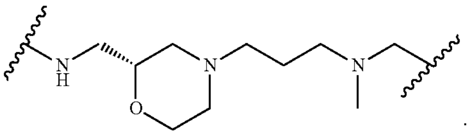 [SMILES: *CN(C)CCCN1CCO[C@H](CN*)C1]
In some embodiments, L is
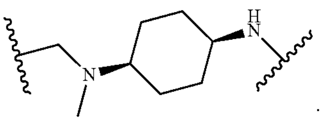 [SMILES: *CN(C)[C@H]1CC[C@@H](N*)CC1]
In some embodiments, L is
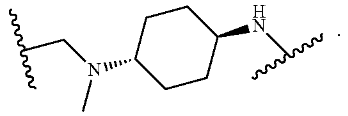 [SMILES: *CN(C)[C@H]1CC[C@H](N*)CC1]
In some embodiments, L is
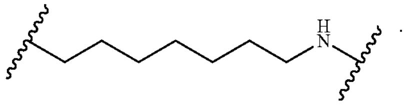 [SMILES: *CCCCCCCN*]
In some embodiments, L is
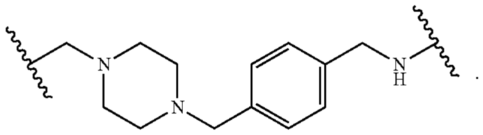 [SMILES: *CN1CCN(Cc2ccc(CN*)cc2)CC1]
In some embodiments, L is
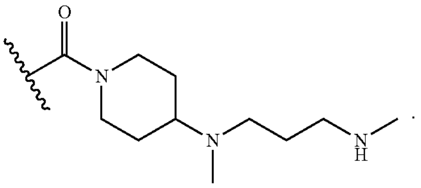 [SMILES: *C(=O)N1CCC(N(C)CCCNC)CC1]
In some embodiments, L is
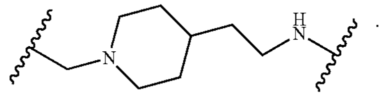 [SMILES: *CN1CCC(CCN*)CC1]
In some embodiments, L is
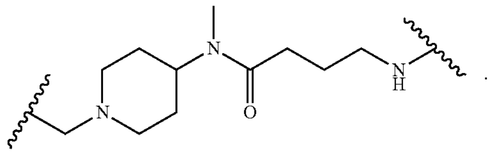 [SMILES: *CN1CCC(N(C)C(=O)CCCN*)CC1]
In some embodiments, L is
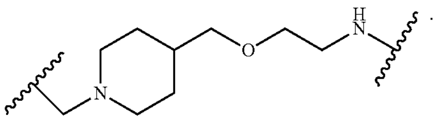 [SMILES: *CN1CCC(COCCN*)CC1]

In some embodiments, L is
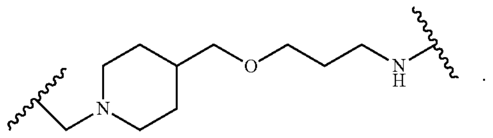 [SMILES: *CN1CCC(COCCCN*)CC1]
In some embodiments, L is
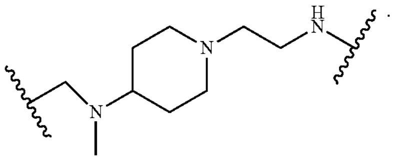 [SMILES: *CN(C)C1CCN(CCN*)CC1]
In some embodiments, L is
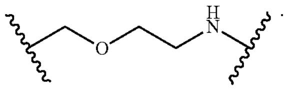 [SMILES: *COCCN*]
In some embodiments, L is
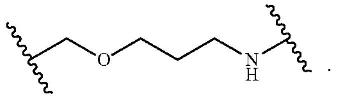 [SMILES: *COCCCN*]
In some embodiments, L is
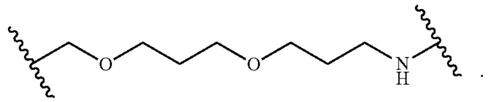 [SMILES: *COCCCOCCCN*]
In some embodiments, L is
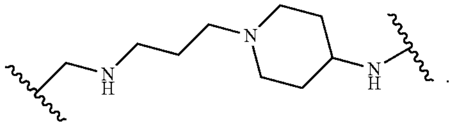 [SMILES: *CNCCCN1CCC(N*)CC1]
In some embodiments, L is
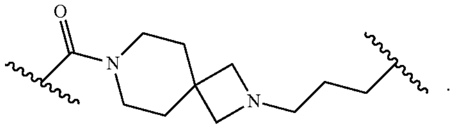 [SMILES: *CCCN1CC2(CCN(C(*)=O)CC2)C1]
In some embodiments, L is
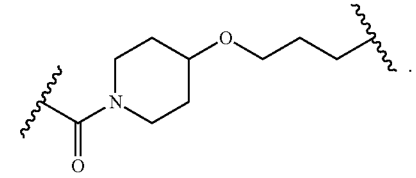 [SMILES: *CCCOC1CCN(C(*)=O)CC1]
In some embodiments, L is
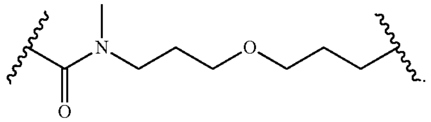 [SMILES: *CCCOCCCN(C)C(*)=O]
In some embodiments, L is
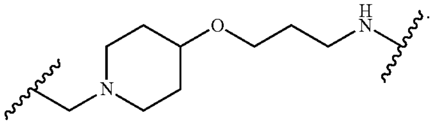 [SMILES: *CN1CCC(OCCCN*)CC1]
In some embodiments, L is
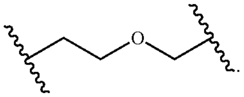 [SMILES: *CCOC*]
In some embodiments, L is
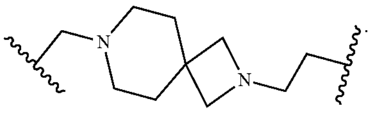 [SMILES: *CCN1CC2(CCN(C*)CC2)C1]
In some embodiments, L is
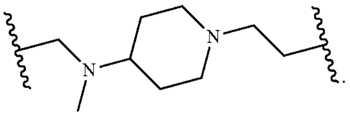 [SMILES: *CCN1CCC(N(C)C*)CC1]
In some embodiments, L is
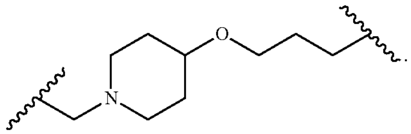 [SMILES: *CCCOC1CCN(C*)CC1]

In some embodiments L is
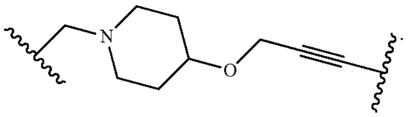 [SMILES: *C#CCOC1CCN(C*)CC1]
In some embodiments, L is
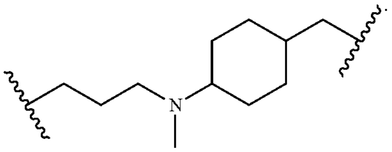 [SMILES: *CCCN(C)C1CCC(C*)CC1]
In some embodiments, L is
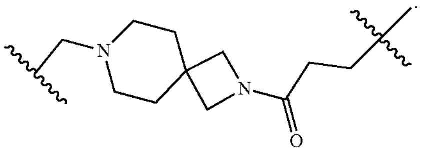 [SMILES: *CCC(=O)N1CC2(CCN(C*)CC2)C1]
In some embodiments, L is
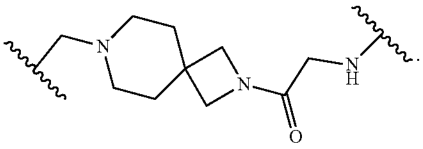 [SMILES: *CN1CCC2(CC1)CN(C(=O)CN*)C2]
In some embodiments, L is
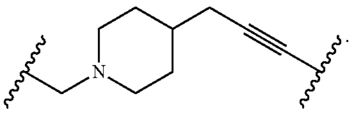
In some embodiments, L is
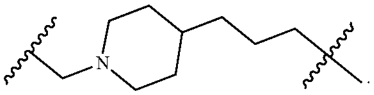 [SMILES: *CCCC1CCN(C*)CC1]
In some embodiments L is
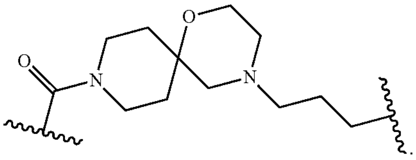 [SMILES: *CCCN1CCOC2(CCN(C(*)=O)CC2)C1]
In some embodiments, L is
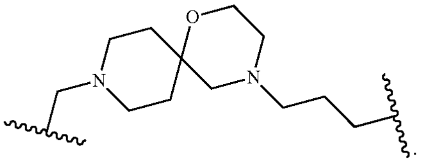 [SMILES: *CCCN1CCOC2(CCN(C*)CC2)C1]
In some embodiments, L is
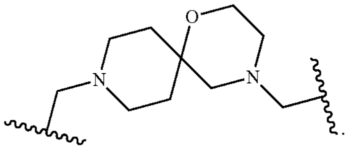 [SMILES: *CN1CCC2(CC1)CN(C*)CCO2]
In some embodiments, L is
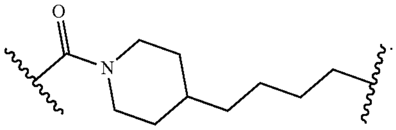 [SMILES: *CCCCC1CCN(C(*)=O)CC1]
In some embodiments, L is
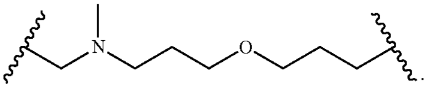 [SMILES: *CCCOCCCN(C)C*]
In some embodiments, L is
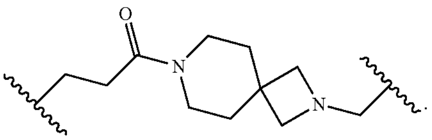 [SMILES: *CCC(=O)N1CCC2(CC1)CN(C*)C2]
In some embodiments L is
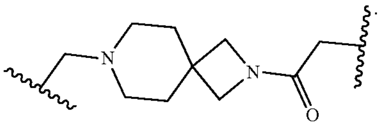 [SMILES: *CC(=O)N1CC2(CCN(C*)CC2)C1]
In some embodiments, L is
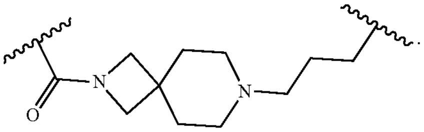 [SMILES: *CCCN1CCC2(CC1)CN(C(*)=O)C2]

In some embodiments, L is
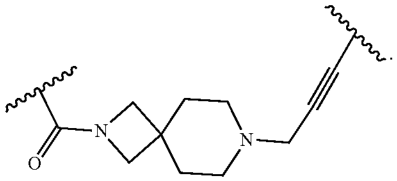 [SMILES: *C#CCN1CCC2(CC1)CN(C(*)=O)C2]
In some embodiments L is
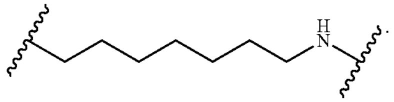 [SMILES: *CCCCCCCN*]
In some embodiments, L is
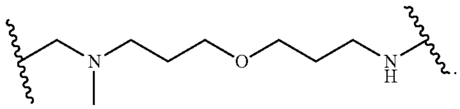 [SMILES: *CN(C)CCCOCCCN*]
In some embodiments L is
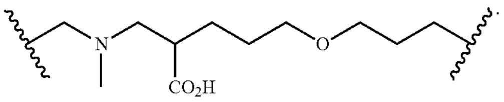
In some embodiments, L is
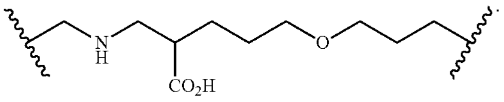
In some embodiments, L is
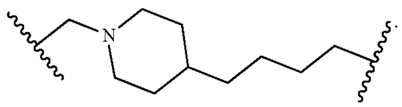 [SMILES: *CCCCC1CCN(C*)CC1]
In some embodiments, L is
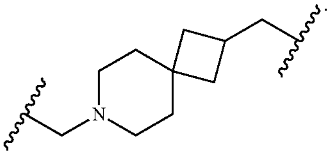 [SMILES: *CC1CC2(CCN(C*)CC2)C1]
In some embodiments, L is
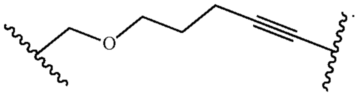 [SMILES: *C#CCCCOC*]
In some embodiments, L is
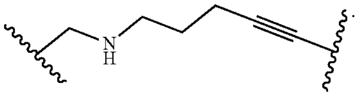 [SMILES: *C#CCCCNC*]
In some embodiments, L is
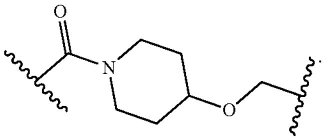 [SMILES: *COC1CCN(C(*)=O)CC1]
In some embodiments, L is
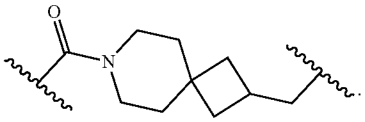 [SMILES: *CC1CC2(CCN(C(*)=O)CC2)C1]
In some embodiments, L is
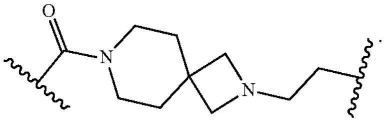 [SMILES: *CCN1CC2(CCN(C(*)=O)CC2)C1]
In some embodiments, L is
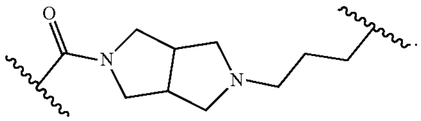 [SMILES: *CCCN1CC2CN(C(*)=O)CC2C1]
In some embodiments, L is
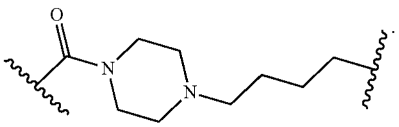 [SMILES: *CCCCN1CCN(C(*)=O)CC1]

In some embodiments, L is
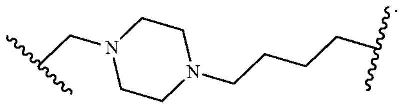 [SMILES: *CCCCN1CCN(C*)CC1]
In some embodiments, L is
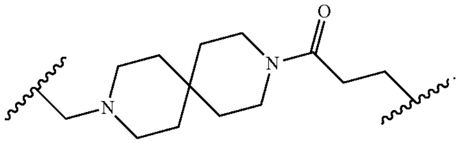 [SMILES: *CCC(=O)N1CCC2(CCN(C*)CC2)CC1]
In some embodiments, L is
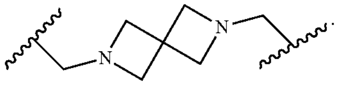 [SMILES: *CN1CC2(C1)CN(C*)C2]
In some embodiments, L is
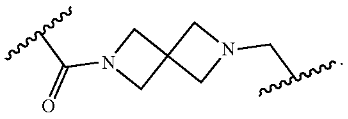 [SMILES: *CN1CC2(C1)CN(C(*)=O)C2]
In some embodiments, L is
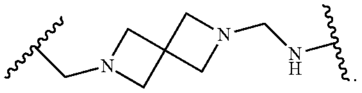 [SMILES: *CN1CC2(C1)CN(CN*)C2]
In some embodiments, L is
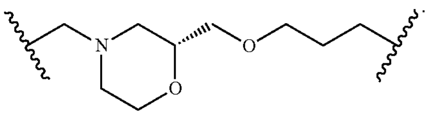 [SMILES: *CCCOC[C@H]1CN(C*)CCO1]
In some embodiments, L is
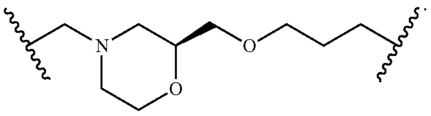 [SMILES: *CCCOC[C@@H]1CN(C*)CCO1]
In some embodiments, L is
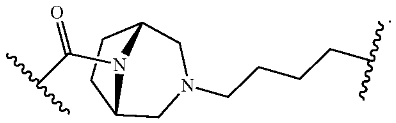 [SMILES: *CCCCN1C[C@H]2CC[C@@H](C1)N2C(*)=O]
In some embodiments, L is
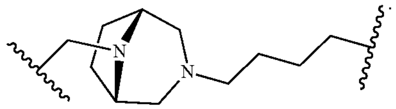 [SMILES: *CCCCN1C[C@H]2CC[C@@H](C1)N2C*]
In some embodiments, L is
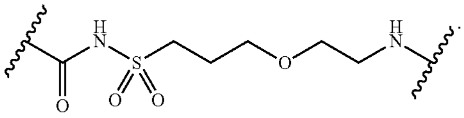 [SMILES: *NCCOCCCS(=O)(=O)NC(*)=O]
In some embodiments, L is
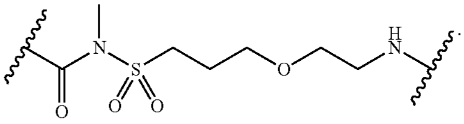 [SMILES: *NCCOCCCS(=O)(=O)N(C)C(*)=O]
In some embodiments, L is
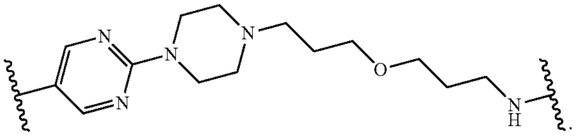 [SMILES: *NCCCOCCCN1CCN(c2ncc(*)cn2)CC1]
In some embodiments, L is
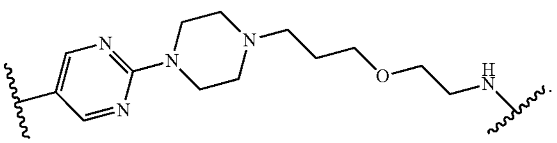 [SMILES: *NCCOCCCN1CCN(c2ncc(*)cn2)CC1]
In some embodiments, L is
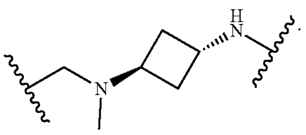 [SMILES: *CN(C)[C@H]1C[C@H](N*)C1]

In some embodiments, L is
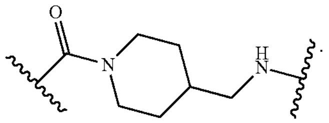 [SMILES: *NCC1CCN(C(*)=O)CC1]
In some embodiments, L is
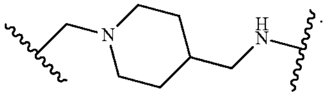 [SMILES: *CN1CCC(CN*)CC1]
In some embodiments, L is
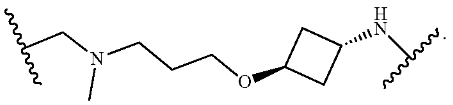 [SMILES: *CN(C)CCCO[C@H]1C[C@H](N*)C1]
In some embodiments, L is
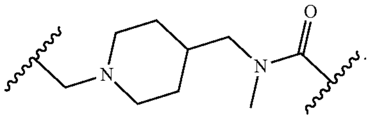 [SMILES: *CN1CCC(CN(C)C(*)=O)CC1]
In some embodiments, L is
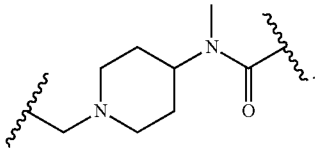 [SMILES: *CN1CCC(N(C)C(*)=O)CC1]
In some embodiments, L is
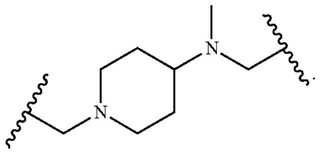 [SMILES: *CN1CCC(N(C)C*)CC1]
In some embodiments, L is
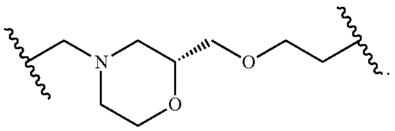 [SMILES: *CCOC[C@H]1CN(C*)CCO1]
In some embodiments, L is
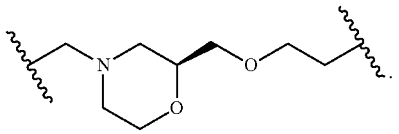 [SMILES: *CCOC[C@@H]1CN(C*)CCO1]
In some embodiments, L is
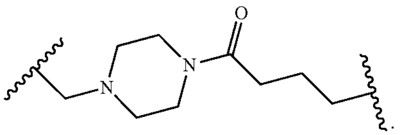 [SMILES: *CCCC(=O)N1CCN(C*)CC1]
In some embodiments, L is
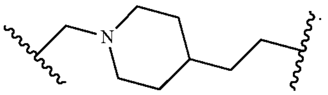 [SMILES: *CCC1CCN(C*)CC1]
In some embodiments, L is
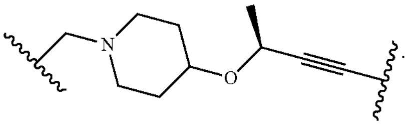 [SMILES: *C#C[C@H](C)OC1CCN(C*)CC1]
In some embodiments, L is
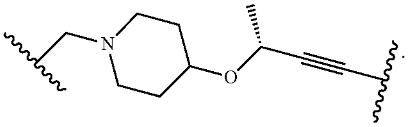 [SMILES: *C#C[C@@H](C)OC1CCN(C*)CC1]
In some embodiments, L is
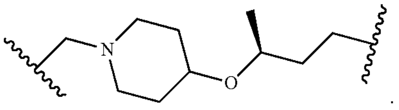 [SMILES: *CC[C@H](C)OC1CCN(C*)CC1]
In some embodiments, L is
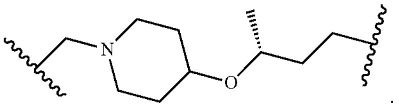 [SMILES: *CC[C@@H](C)OC1CCN(C*)CC1]

In some embodiments, L is
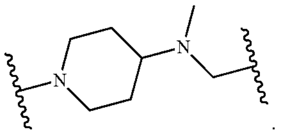 [SMILES: *CN(C)C1CCN(*)CC1]
In some embodiments L is
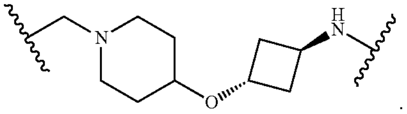 [SMILES: *CN1CCC(O[C@H]2C[C@H](N*)C2)CC1]
In some embodiments, L is
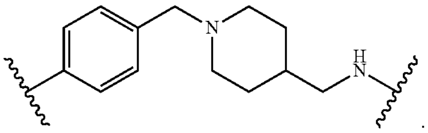 [SMILES: *NCC1CCN(Cc2ccc(*)cc2)CC1]
In some embodiments, L is
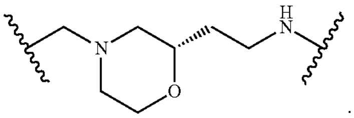 [SMILES: *CN1CCO[C@@H](CCN*)C1]
In some embodiments, L is
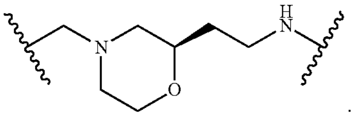 [SMILES: *CN1CCO[C@H](CCN*)C1]
In some embodiments, L is
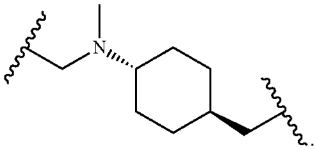 [SMILES: *CN(C)[C@H]1CC[C@H](C*)CC1]
In some embodiments, L is
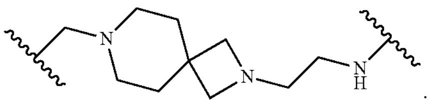 [SMILES: *CN1CCC2(CC1)CN(CCN*)C2]
In some embodiments, L is
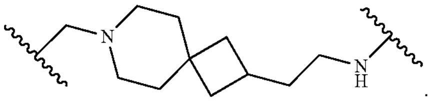 [SMILES: *CN1CCC2(CC1)CC(CCN*)C2]
In some embodiments, L is
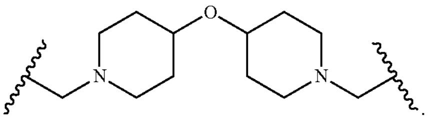 [SMILES: *CN1CCC(OC2CCN(C*)CC2)CC1]
In some embodiments, L is
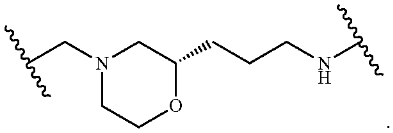 [SMILES: *CN1CCO[C@@H](CCCN*)C1]
In some embodiments, L is
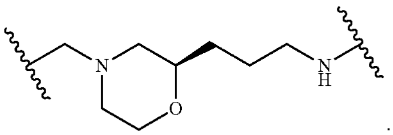 [SMILES: *CN1CCO[C@H](CCCN*)C1]
In some embodiments, L is
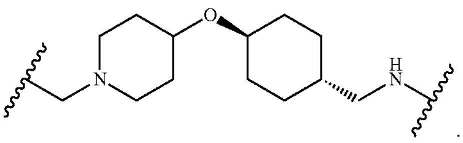 [SMILES: *CN1CCC(O[C@H]2CC[C@H](CN*)CC2)CC1]
In some embodiments, L is
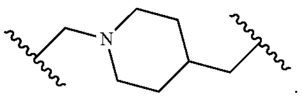 [SMILES: *CC1CCN(C*)CC1]
In some embodiments, L is
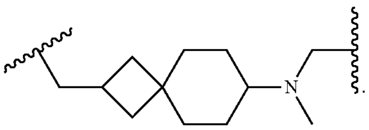 [SMILES: *CC1CC2(CCC(N(C)C*)CC2)C1]

In some embodiments, L is
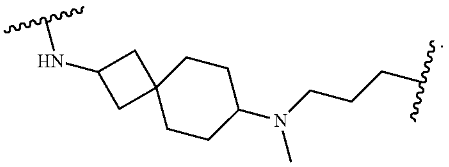 [SMILES: *CCCN(C)C1CCC2(CC1)CC(N*)C2]
In some embodiments, L is
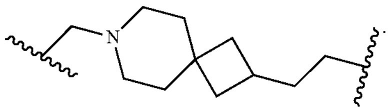 [SMILES: *CCC1CC2(CCN(C*)CC2)C1]
In some embodiments, L is
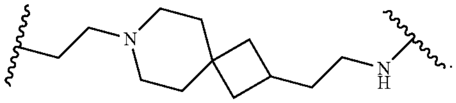 [SMILES: *CCN1CCC2(CC1)CC(CCN*)C2]
In some embodiments, L is
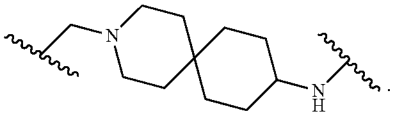 [SMILES: *CN1CCC2(CCC(N*)CC2)CC1]
In some embodiments, L is
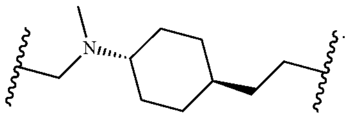 [SMILES: *CC[C@H]1CC[C@H](N(C)C*)CC1]
In some embodiments, L is
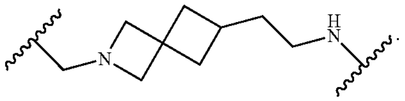 [SMILES: *CN1CC2(CC(CCN*)C2)C1]
In some embodiments, L is
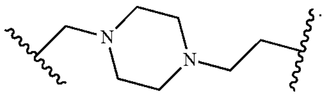 [SMILES: *CCN1CCN(C*)CC1]
In some embodiments, L is
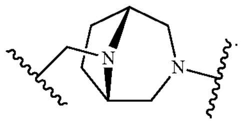 [SMILES: *CN1[C@@H]2CC[C@H]1CN(*)C2]
In some embodiments, L is
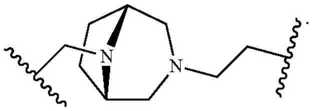 [SMILES: *CCN1C[C@H]2CC[C@@H](C1)N2C*]
In some embodiments, L is
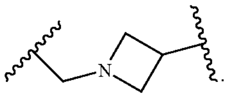 [SMILES: *CN1CC(*)C1]
In some embodiments, L is
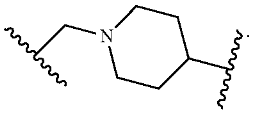 [SMILES: *CN1CCC(*)CC1]
In some embodiments, L is
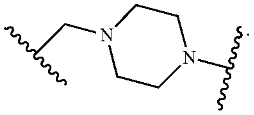 [SMILES: *CN1CCN(*)CC1]
In some embodiments, L is
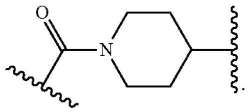 [SMILES: *C(=O)N1CCC(*)CC1]
In some embodiments, L is
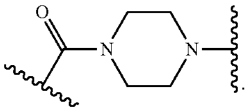 [SMILES: *C(=O)N1CCN(*)CC1]

In some embodiments, L is

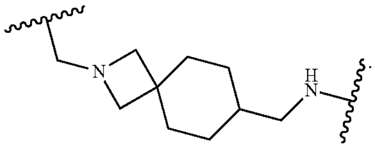 [SMILES: *CN1CC2(CCC(CN*)CC2)C1]

In some embodiments, L is

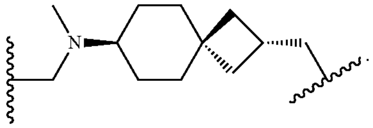

In some embodiments, L is

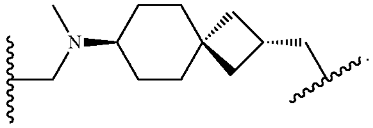

In some embodiments L is

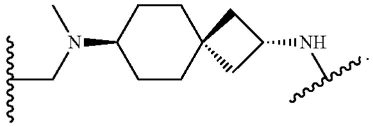

In some embodiments, L is

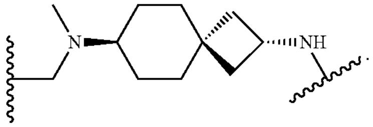

In some embodiments, L is

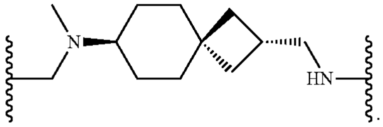

In some embodiments, L is

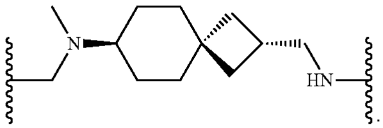

In some embodiments, L is

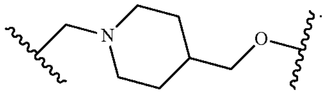 [SMILES: *CN1CCC(CO*)CC1]

In some embodiments, L is

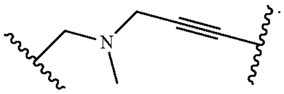 [SMILES: *C#CCN(C)C*]

In some embodiments, L is

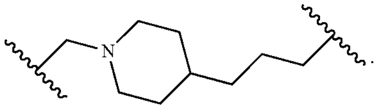 [SMILES: *CCCC1CCN(C*)CC1]

In some embodiments, L is

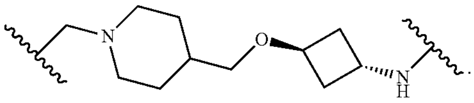 [SMILES: *CN1CCC(CO[C@H]2C[C@H](N*)C2)CC1]

In some embodiments, L is

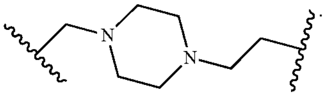 [SMILES: *CCN1CCN(C*)CC1]

In some embodiments, L is

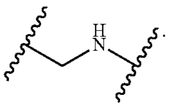 [SMILES: *CN*]

In some embodiments, L is

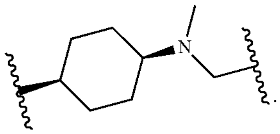 [SMILES: *CN(C)[C@H]1CC[C@@H](*)CC1]

In some embodiments, L is

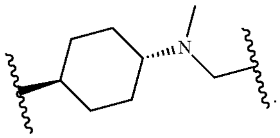 [SMILES: *CN(C)[C@H]1CC[C@H](*)CC1]

In some embodiments, L is
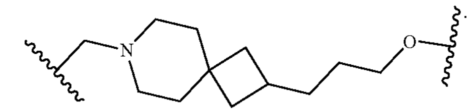 [SMILES: *CN1CCC2(CC1)CC(CCCO*)C2]
In some embodiments, L is
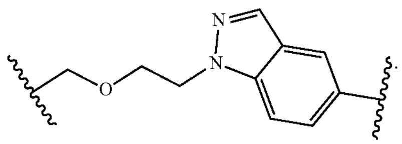 [SMILES: *COCCn1ncc2cc(*)ccc21]
In some embodiments, L is
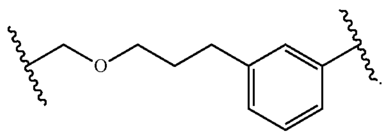 [SMILES: *COCCCc1cccc(*)c1]
In some embodiments, L is
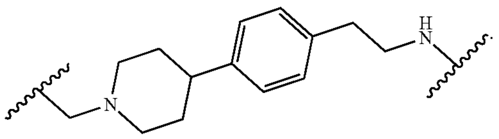 [SMILES: *CN1CCC(c2ccc(CCN*)cc2)CC1]
In some embodiments, L is
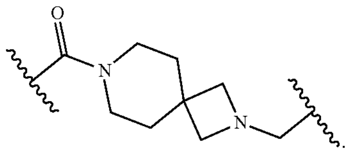 [SMILES: *CN1CC2(CCN(C(*)=O)CC2)C1]
In some embodiments, L is
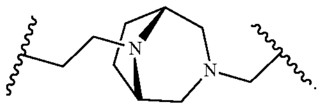
In some embodiments, L is
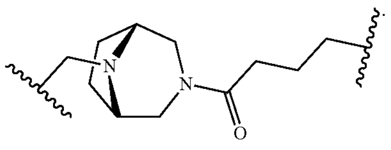
In some embodiments, L is
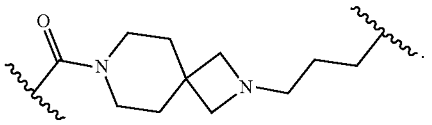 [SMILES: *CCCN1CC2(CCN(C(*)=O)CC2)C1]
In some embodiments, L is
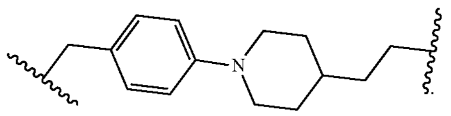 [SMILES: *CCC1CCN(c2ccc(C*)cc2)CC1]
In some embodiments, L is
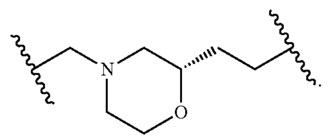 [SMILES: *CC[C@H]1CN(C*)CCO1]
In some embodiments, L is
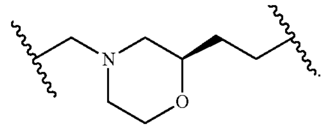 [SMILES: *CC[C@@H]1CN(C*)CCO1]
In some embodiments, L is
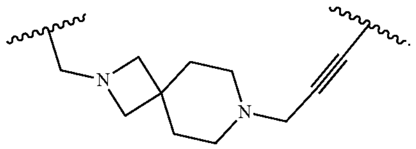 [SMILES: *C#CCN1CCC2(CC1)CN(C*)C2]
In some embodiments, L is
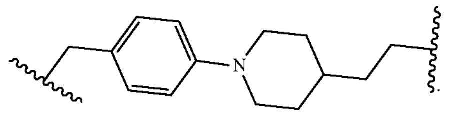 [SMILES: *CCC1CCN(c2ccc(C*)cc2)CC1]
In some embodiments, L is
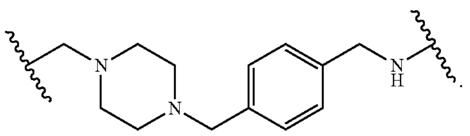 [SMILES: *CN1CCN(Cc2ccc(CN*)cc2)CC1]

In some embodiments, L is
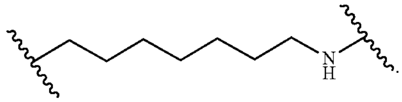 [SMILES: *CCCCCCCN*]
In some embodiments, L is
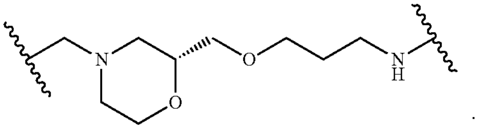 [SMILES: *CN1CCO[C@@H](COCCCN*)C1]
In some embodiments, L is
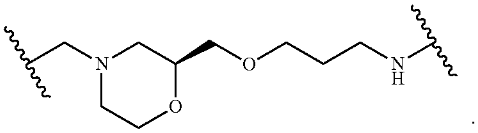 [SMILES: *CN1CCO[C@H](COCCCN*)C1]
In some embodiments, L is
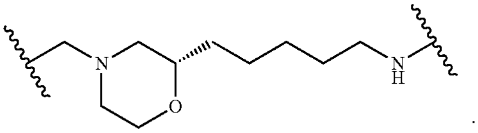 [SMILES: *CN1CCO[C@@H](CCCCCN*)C1]
In some embodiments, L is
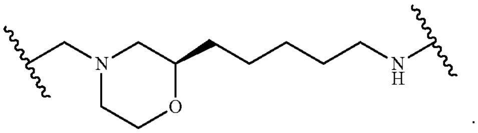 [SMILES: *CN1CCO[C@H](CCCCCN*)C1]
In some embodiments, L is
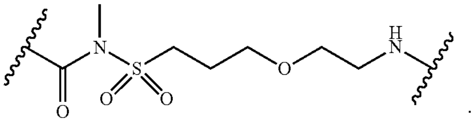 [SMILES: *NCCOCCCS(=O)(=O)N(C)C(*)=O]
In some embodiments, L is
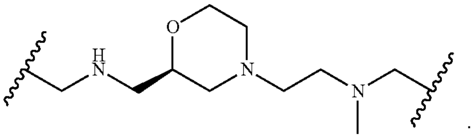 [SMILES: *CNC[C@@H]1CN(CCN(C)C*)CCO1]
In some embodiments L is
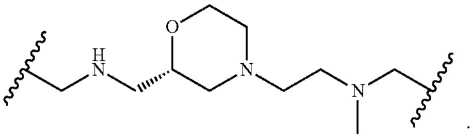 [SMILES: *CNC[C@H]1CN(CCN(C)C*)CCO1]
In some embodiments, L is
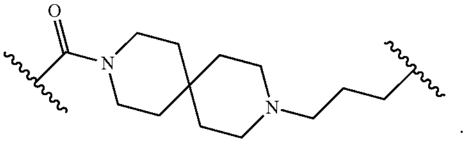 [SMILES: *CCCN1CCC2(CC1)CCN(C(*)=O)CC2]
In some embodiments, L is
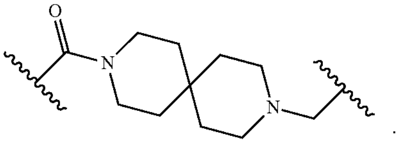 [SMILES: *CN1CCC2(CC1)CCN(C(*)=O)CC2]
In some embodiments, L is
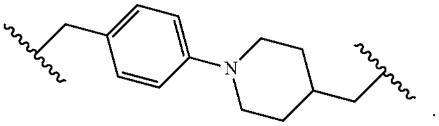 [SMILES: *Cc1ccc(N2CCC(C*)CC2)cc1]
In some embodiments, L is
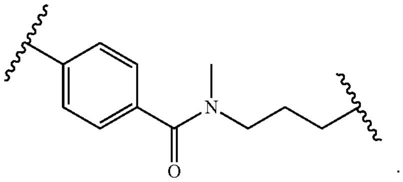 [SMILES: *CCCN(C)C(=O)c1ccc(*)cc1]
In some embodiments, L is
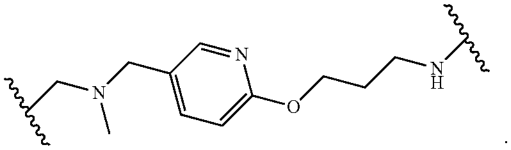 [SMILES: *CN(C)Cc1ccc(OCCCN*)nc1]

In some embodiments, L is
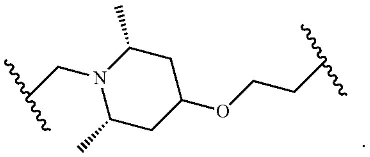 [SMILES: *CCOC1C[C@@H](C)N(C*)[C@@H](C)C1]
In some embodiments, L is
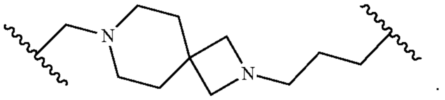 [SMILES: *CCCN1CC2(CCN(C*)CC2)C1]
In some embodiments, L is
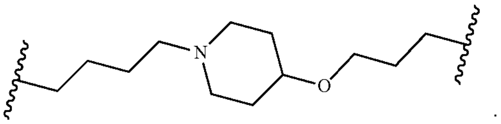 [SMILES: *CCCCN1CCC(OCCC*)CC1]
In some embodiments, L is
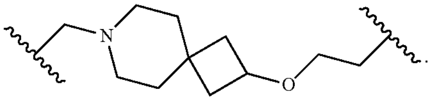 [SMILES: *CCOC1CC2(CCN(C*)CC2)C1]
In some embodiments, L is
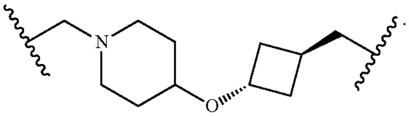 [SMILES: *CN1CCC(O[C@H]2C[C@H](C*)C2)CC1]
In some embodiments, L is
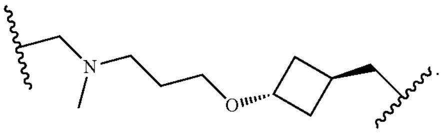 [SMILES: *CN(C)CCCO[C@H]1C[C@H](C*)C1]
In some embodiments, L is
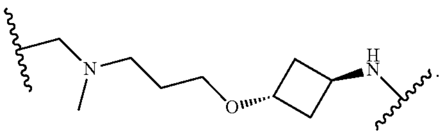 [SMILES: *CN(C)CCCO[C@H]1C[C@H](N*)C1]
In some embodiments, L is
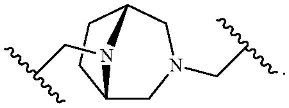 [SMILES: *CN1C[C@H]2CC[C@@H](C1)N2C*]
In some embodiments, L is
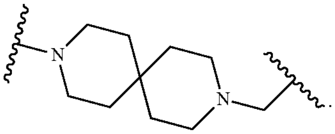 [SMILES: *CN1CCC2(CCN(*)CC2)CC1]
In some embodiments, L is
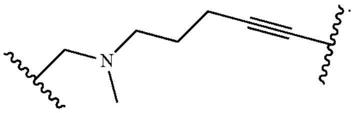 [SMILES: *C#CCCCN(C)C*]
In some embodiments, L is
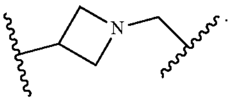 [SMILES: *CN1CC(*)C1]
In some embodiments, L is
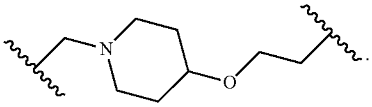 [SMILES: *CCOC1CCN(C*)CC1]
In some embodiments, L is
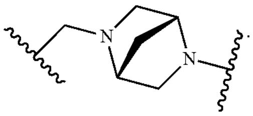 [SMILES: *CN1C[C@H]2C[C@@H]1CN2*]
In some embodiments, L is
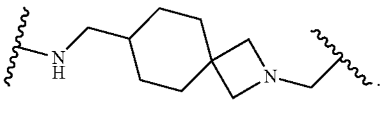 [SMILES: *CN1CC2(CCC(CN*)CC2)C1]

In some embodiments, L is

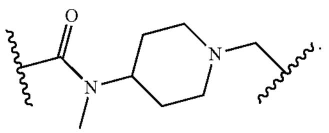 [SMILES: *CN1CCC(N(C)C(*)=O)CC1]

In some embodiments, L is

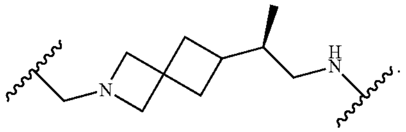 [SMILES: *CN1CC2(CC([C@@H](C)CN*)C2)C1]

In some embodiments, L is

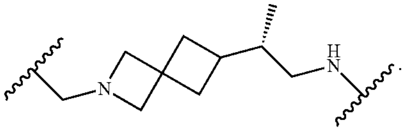 [SMILES: *CN1CC2(CC([C@H](C)CN*)C2)C1]

In some embodiments, L is

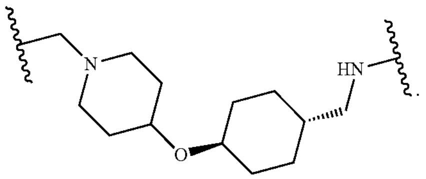 [SMILES: *CN1CCC(O[C@H]2CC[C@H](CN*)CC2)CC1]

In some embodiments, L is

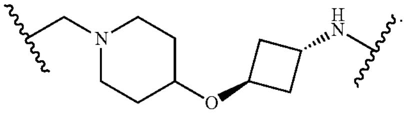 [SMILES: *CN1CCC(O[C@H]2C[C@H](N*)C2)CC1]

In some embodiments, L is

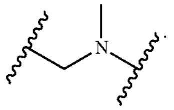 [SMILES: *CN(*)C]

In some embodiments, L is

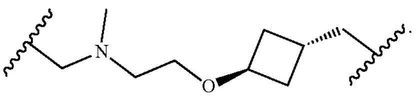 [SMILES: *CN(C)CCO[C@H]1C[C@H](C*)C1]

In some embodiments, L is

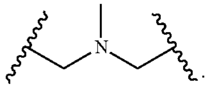 [SMILES: *CN(C)C*]

In some embodiments, L is

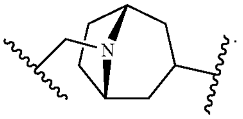 [SMILES: *CN1[C@@H]2CC[C@H]1CC(*)C2]

In some embodiments, L is

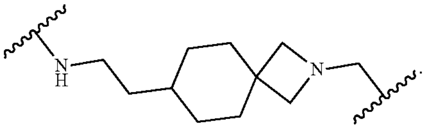 [SMILES: *CN1CC2(CCC(CCN*)CC2)C1]

In some embodiments, L is

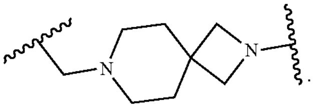 [SMILES: *CN1CCC2(CC1)CN(*)C2]

In some embodiments, L is

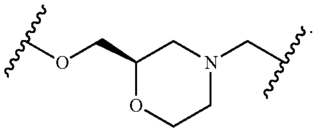 [SMILES: *CN1CCO[C@@H](CO*)C1]

In some embodiments, L is

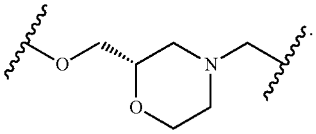 [SMILES: *CN1CCO[C@H](CO*)C1]

In some embodiments, L is selected from those depicted in Table 1, below.

Without limitation, the point of attachment of L to IRAK and DIM can be, for example when L is

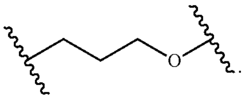 [SMILES: *CCCO*]

either

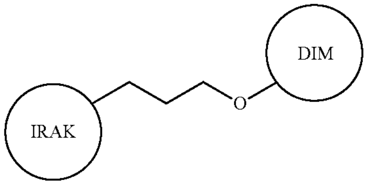

or

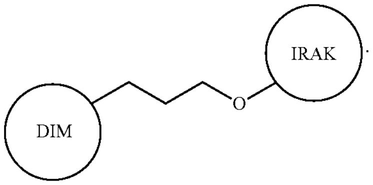

In some embodiments, a provided compound or pharmaceutically acceptable salt thereof, is selected from those wherein IRAK is

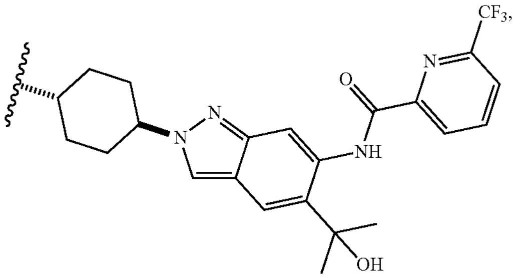

LBM is selected from any of those in Table A below, and L is selected from any of those in Table B below.

In some embodiments, a provided compound or pharmaceutically acceptable salt thereof, is selected from those wherein IRAK is

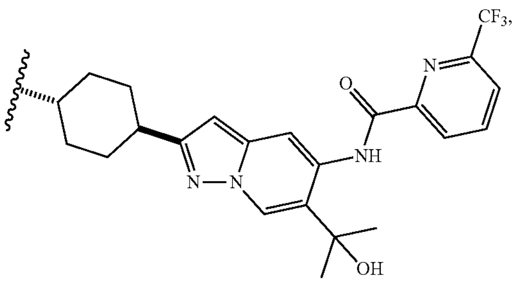

LBM is selected from any of those in Table A below, and L is selected from any of those in Table B below.

In some embodiments, a provided compound or pharmaceutically acceptable salt thereof, is selected from those wherein IRAK is

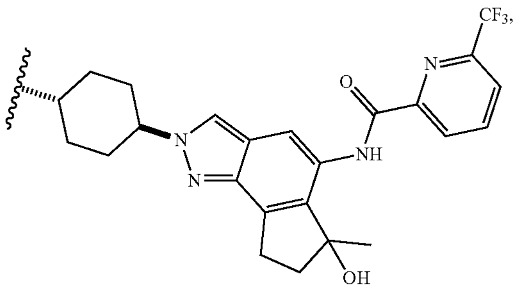

LBM is selected from any of those in Table A below, and L is selected from any of those in Table B below.

In some embodiments, a provided compound or pharmaceutically acceptable salt thereof, is selected from those wherein IRAK is

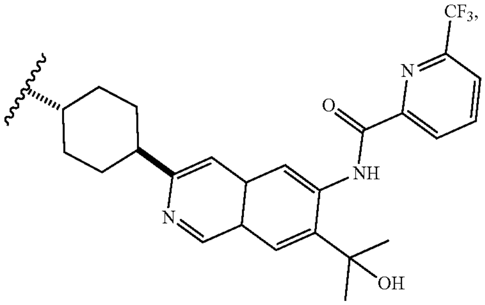

LBM is selected from any of those in Table A below, and L is selected from any of those in Table B below.

In some embodiments, a provided compound or pharmaceutically acceptable salt thereof, is selected from those wherein IRAK is

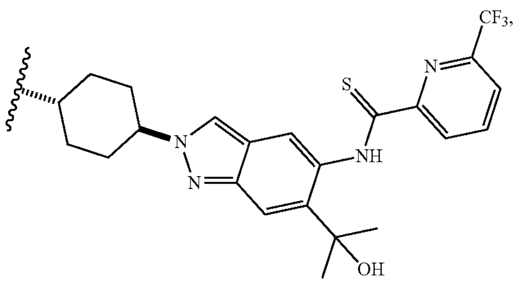

LBM is selected from any of those in Table A below, and L is selected from any of those in Table B below.

In some embodiments, a provided compound or pharmaceutically acceptable salt thereof, is selected from those wherein IRAK is

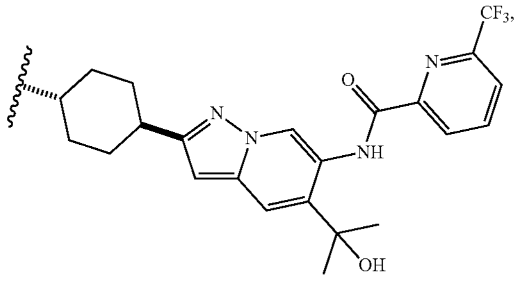

LBM is selected from any of those in Table A below, and L is selected from any of those in Table B below.

In some embodiments, a provided compound or pharmaceutically acceptable salt thereof, is selected from those wherein IRAK is

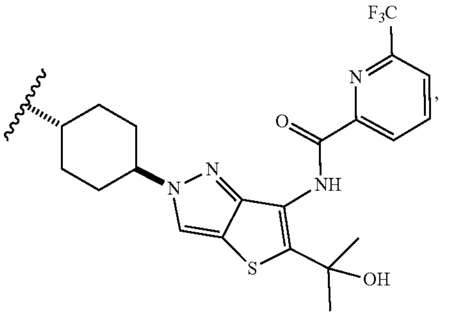

LBM is selected from any of those in Table A below, and L is selected from any of those in Table B below.

In some embodiments, a provided compound or pharmaceutically acceptable salt thereof, is selected from those wherein IRAK is

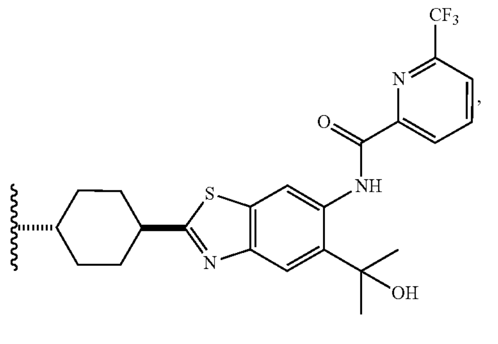

LBM is selected from any of those in Table A below, and L is selected from any of those in Table B below.

In some embodiments, a provided compound or pharmaceutically acceptable salt thereof, is selected from those wherein IRAK is

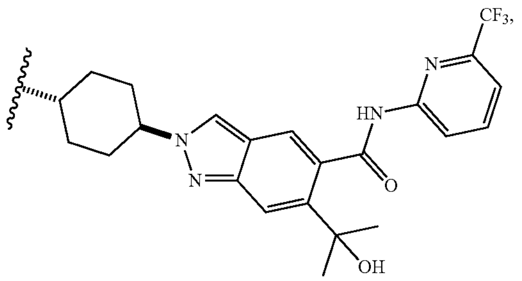

LBM is selected from any of those in Table A below, and L is selected from any of those in Table B below.

In some embodiments, a provided compound or pharmaceutically acceptable salt thereof, is selected from those wherein IRAK is

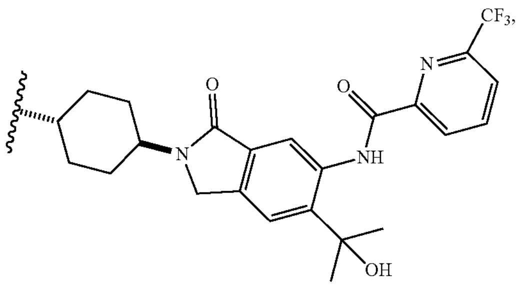

LBM is selected from any of those in Table A below, and L is selected from any of those in Table B below.

In some embodiments, a provided compound or pharmaceutically acceptable salt thereof, is selected from those wherein IRAK is

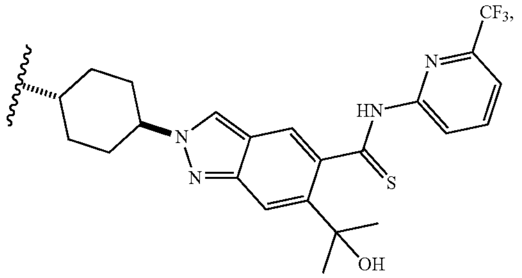

LBM is selected from any of those in Table A below, and L is selected from any of those in Table B below.

In some embodiments, a provided compound or pharmaceutically acceptable salt thereof, is selected from those wherein IRAK is

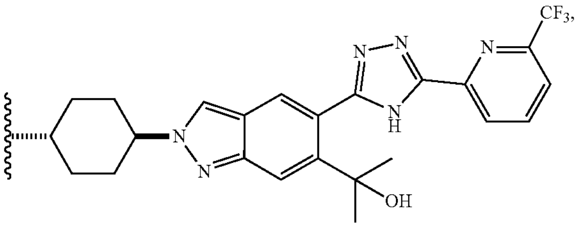

LBM is selected from any of those in Table A below, and L is selected from any of those in Table B below.

In some embodiments, a provided compound or pharmaceutically acceptable salt thereof, is selected from those wherein IRAK is

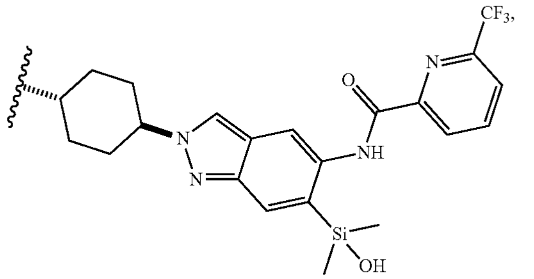

LBM is selected from any of those in Table A below, and L is selected from any of those in Table B below.

In some embodiments, a provided compound or pharmaceutically acceptable salt thereof, is selected from those wherein IRAK is

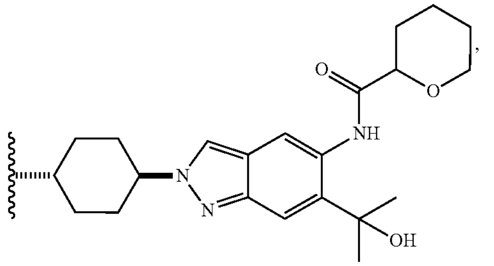

LBM is selected from any of those in Table A below, and L is selected from any of those in Table B below.

In some embodiments, a provided compound or pharmaceutically acceptable salt thereof, is selected from those wherein IRAK is

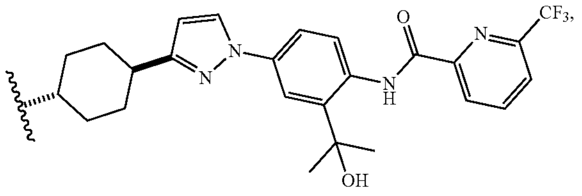 [SMILES: *[C@H]1CC[C@H](c2ccn(-c3ccc(NC(=O)c4cccc(C(F)(F)F)n4)c(C(C)(C)O)c3)n2)CC1]

LBM is selected from any of those in Table A below, and L is selected from any of those in Table B below.

In some embodiments, a provided compound or pharmaceutically acceptable salt thereof, is selected from those wherein IRAK is

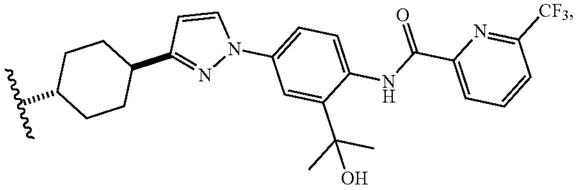 [SMILES: *[C@H]1CC[C@H](c2ccn(-c3ccc(NC(=O)c4cccc(C(F)(F)F)n4)c(C(C)(C)O)c3)n2)CC1]

LBM is selected from any of those in Table A below, and L is selected from any of those in Table B below.

In some embodiments, a provided compound or pharmaceutically acceptable salt thereof, is selected from those wherein IRAK is

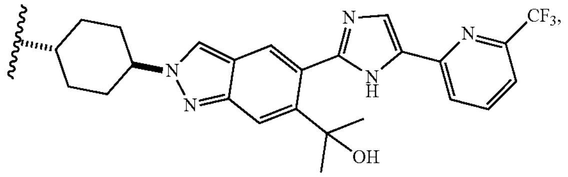

LBM is selected from any of those in Table A below, and L is selected from any of those in Table B below.

In some embodiments, a provided compound or pharmaceutically acceptable salt thereof, is selected from those wherein IRAK is

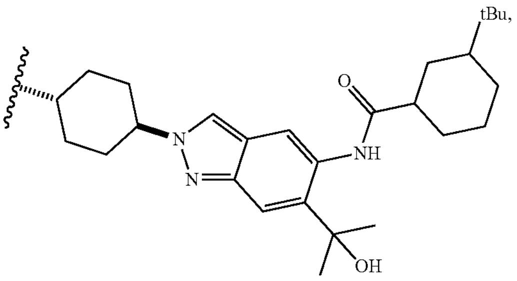

LBM is selected from any of those in Table A below, and L is selected from any of those in Table B below.

In some embodiments, a provided compound or pharmaceutically acceptable salt thereof, is selected from those wherein IRAK is

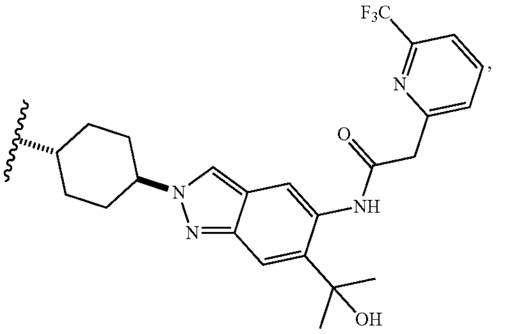

LBM is selected from any of those in Table A below, and L is selected from any of those in Table B below.

In some embodiments, a provided compound or pharmaceutically acceptable salt thereof, is selected from those wherein IRAK is

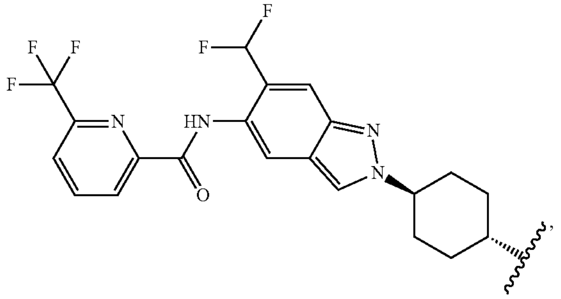 [SMILES: *[C@H]1CC[C@H](n2cc3cc(NC(=O)c4cccc(C(F)(F)F)n4)c(C(F)F)cc3n2)CC1]

LBM is selected from any of those in Table A below, and L is selected from any of those in Table B below.

In some embodiments, a provided compound or pharmaceutically acceptable salt thereof, is selected from those wherein IRAK is

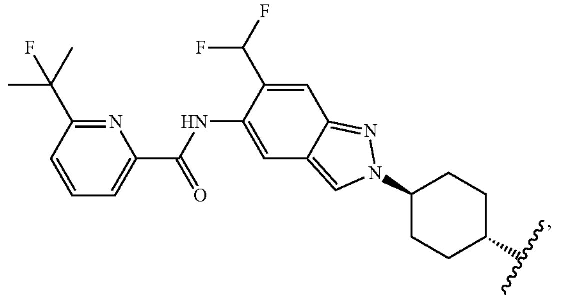 [SMILES: *[C@H]1CC[C@H](n2cc3cc(NC(=O)c4cccc(C(C)(C)F)n4)c(C(F)F)cc3n2)CC1]

LBM is selected from any of those in Table A below, and L is selected from any of those in Table B below.

In some embodiments, a provided compound or pharmaceutically acceptable salt thereof, is selected from those wherein IRAK is

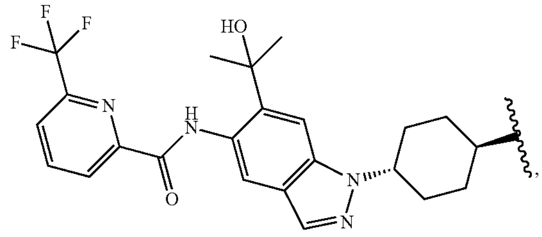 [SMILES: *[C@H]1CC[C@H](n2ncc3cc(NC(=O)c4cccc(C(F)(F)F)n4)c(C(C)(C)O)cc32)CC1]

LBM is selected from any of those in Table A below, and L is selected from any of those in Table B below.

In some embodiments, a provided compound or pharmaceutically acceptable salt thereof, is selected from those wherein IRAK is

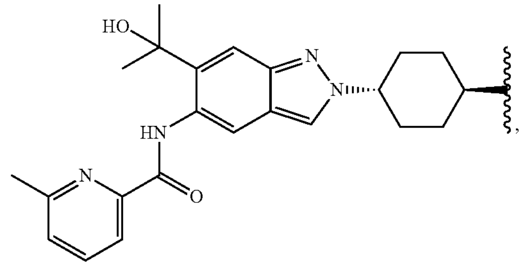 [SMILES: *[C@H]1CC[C@H](n2cc3cc(NC(=O)c4cccc(C)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

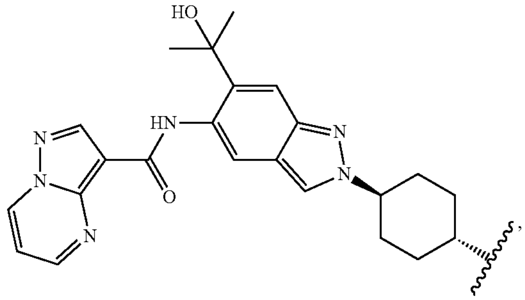 [SMILES: *[C@H]1CC[C@H](n2cc3cc(NC(=O)c4cnn5cccnc45)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

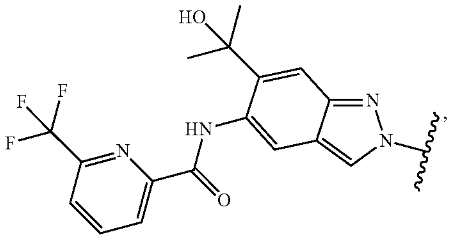 [SMILES: *n1cc2cc(NC(=O)c3cccc(C(F)(F)F)n3)c(C(C)(C)O)cc2n1]

LBM is selected from any of those in Table A below, and L is selected from any of those in Table B below.

In some embodiments, a provided compound or pharmaceutically acceptable salt thereof, is selected from those wherein IRAK is

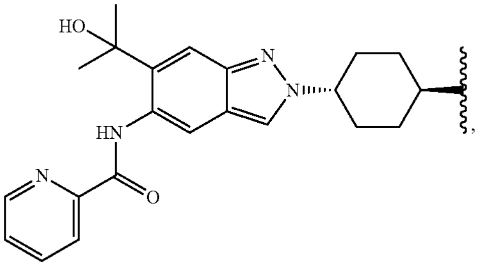 [SMILES: *[C@H]1CC[C@H](n2cc3cc(NC(=O)c4ccccn4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

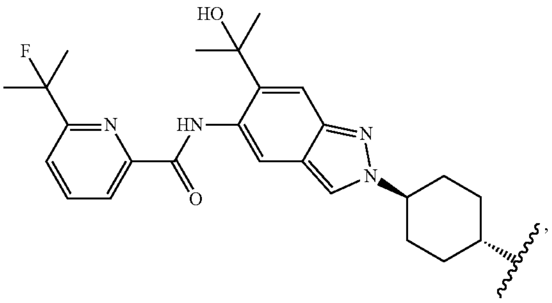 [SMILES: *[C@H]1CC[C@H](n2cc3cc(NC(=O)c4cccc(C(C)(C)F)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

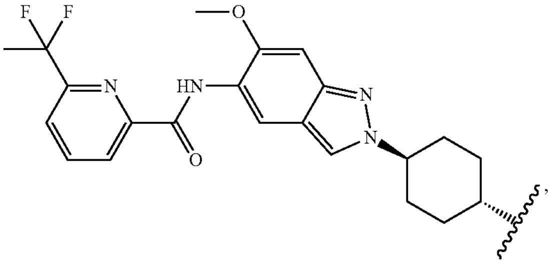 [SMILES: *[C@H]1CC[C@H](n2cc3cc(NC(=O)c4cccc(C(C)(F)F)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

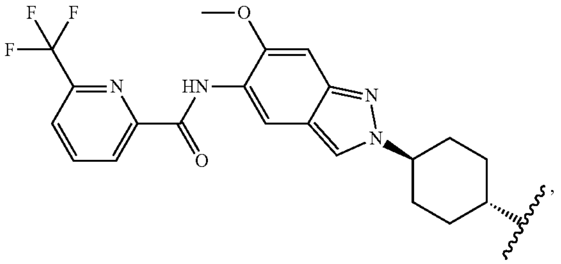 [SMILES: *[C@H]1CC[C@H](n2cc3cc(NC(=O)c4cccc(C(F)(F)F)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

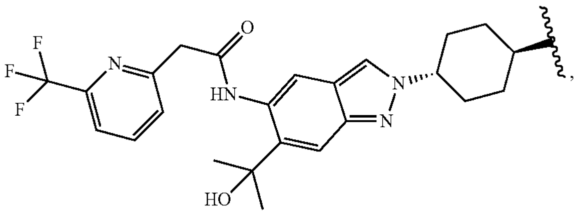 [SMILES: *[C@H]1CC[C@H](n2cc3cc(NC(=O)Cc4cccc(C(F)(F)F)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

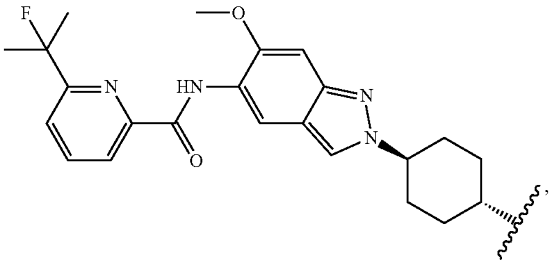 [SMILES: *[C@H]1CC[C@H](n2cc3cc(NC(=O)c4cccc(C(C)(C)F)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

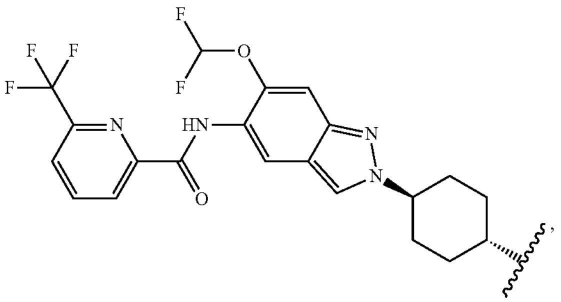 [SMILES: *[C@H]1CC[C@H](n2cc3cc(NC(=O)c4cccc(C(F)(F)F)n4)c(OC(F)F)cc3n2)CC1]

LBM is selected from any of those in Table A below, and L is selected from any of those in Table B below.

In some embodiments, a provided compound or pharmaceutically acceptable salt thereof, is selected from those wherein IRAK is

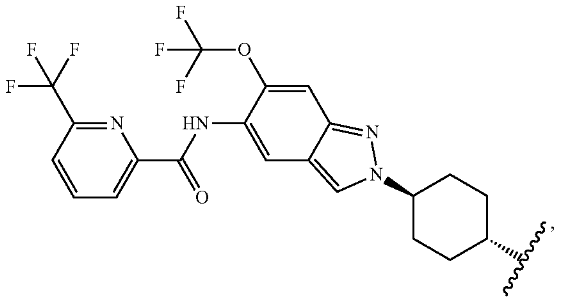 [SMILES: *[C@H]1CC[C@H](n2cc3cc(NC(=O)c4cccc(C(F)(F)F)n4)c(OC(F)(F)F)cc3n2)CC1]

LBM is selected from any of those in Table A below, and L is selected from any of those in Table B below.

In some embodiments, a provided compound or pharmaceutically acceptable salt thereof, is selected from those wherein IRAK is

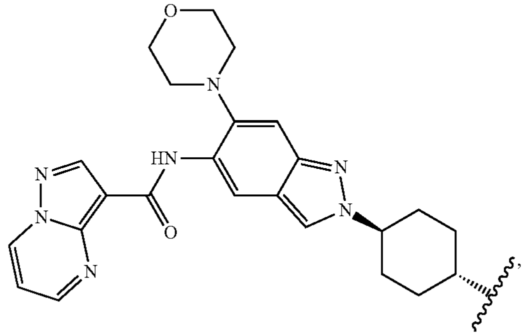

LBM is selected from any of those in Table A below, and L is selected from any of those in Table B below.

In some embodiments, a provided compound or pharmaceutically acceptable salt thereof, is selected from those wherein IRAK is

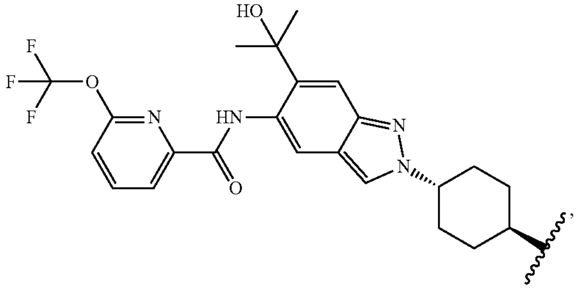 [SMILES: *[C@H]1CC[C@H](n2cc3cc(NC(=O)c4cccc(OC(F)(F)F)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

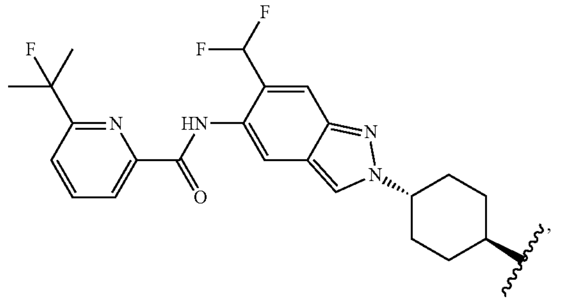 [SMILES: *[C@H]1CC[C@H](n2cc3cc(NC(=O)c4cccc(C(C)(C)F)n4)c(C(F)F)cc3n2)CC1]

LBM is selected from any of those in Table A below, and L is selected from any of those in Table B below.

In some embodiments, a provided compound or pharmaceutically acceptable salt thereof, is selected from those wherein IRAK is

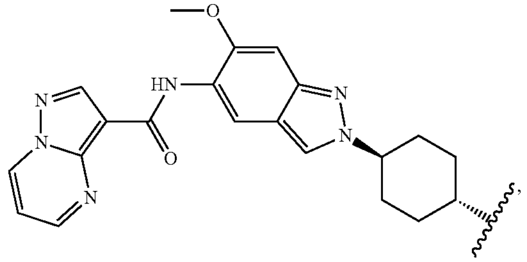 [SMILES: *[C@H]1CC[C@H](n2cc3cc(NC(=O)c4cnn5cccnc45)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

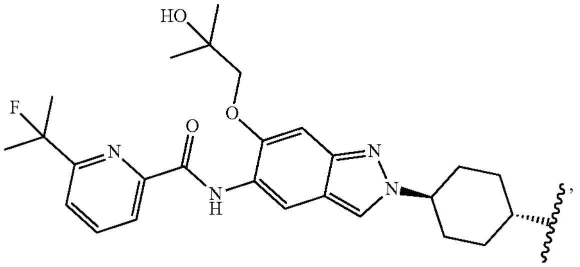 [SMILES: *[C@H]1CC[C@H](n2cc3cc(NC(=O)c4cccc(C(C)(C)F)n4)c(OCC(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

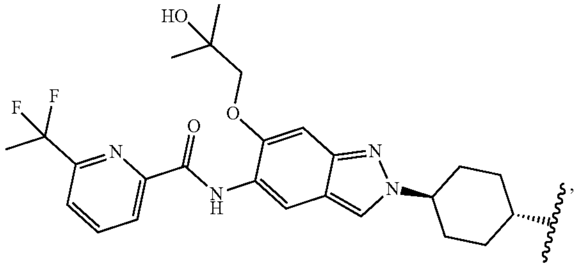

LBM is selected from any of those in Table A below, and L is selected from any of those in Table B below.

In some embodiments, a provided compound or pharmaceutically acceptable salt thereof, is selected from those wherein IRAK is

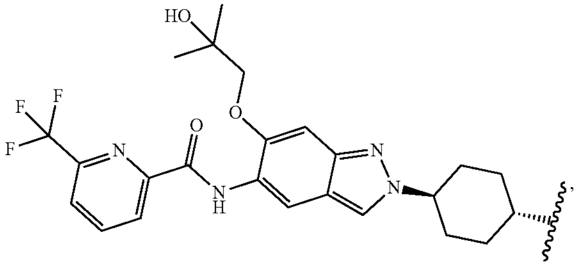 [SMILES: *[C@H]1CC[C@H](n2cc3cc(NC(=O)c4cccc(C(F)(F)F)n4)c(OCC(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

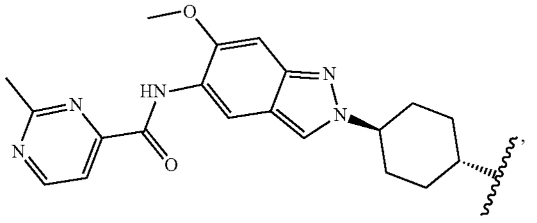 [SMILES: *[C@H]1CC[C@H](n2cc3cc(NC(=O)c4ccnc(C)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

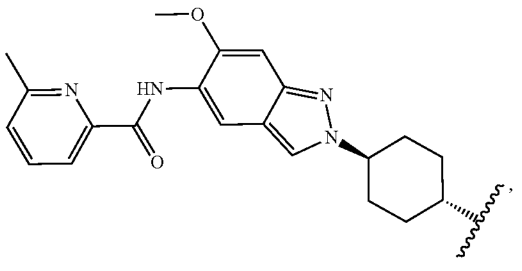 [SMILES: *[C@H]1CC[C@H](n2cc3cc(NC(=O)c4cccc(C)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

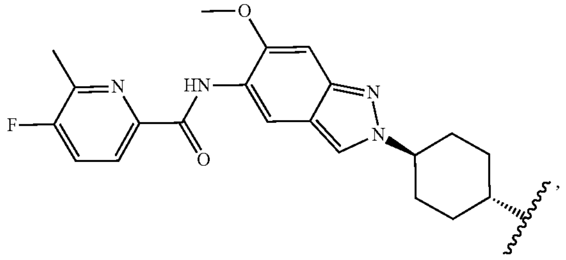 [SMILES: *[C@H]1CC[C@H](n2cc3cc(NC(=O)c4ccc(F)c(C)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

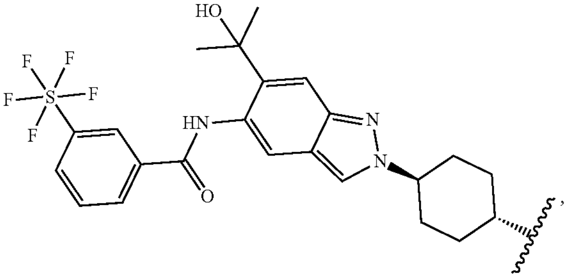 [SMILES: *[C@H]1CC[C@H](n2cc3cc(NC(=O)c4cccc(S(F)(F)(F)(F)F)c4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

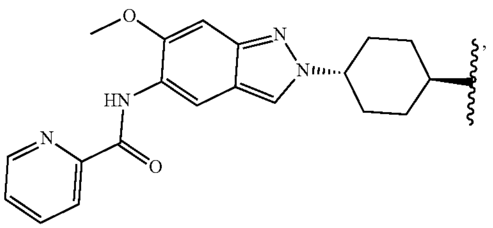 [SMILES: *[C@H]1CC[C@H](n2cc3cc(NC(=O)c4ccccn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

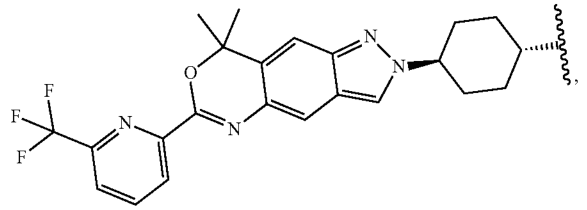 [SMILES: *[C@H]1CC[C@H](n2cc3cc4c(cc3n2)C(C)(C)OC(c2cccc(C(F)(F)F)n2)=N4)CC1]

LBM is selected from any of those in Table A below, and L is selected from any of those in Table B below.

In some embodiments, a provided compound or pharmaceutically acceptable salt thereof, is selected from those wherein IRAK is

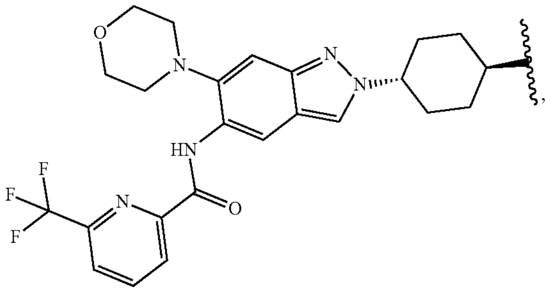 [SMILES: *[C@H]1CC[C@H](n2cc3cc(NC(=O)c4cccc(C(F)(F)F)n4)c(N4CCOCC4)cc3n2)CC1]

LBM is selected from any of those in Table A below, and L is selected from any of those in Table B below.

In some embodiments, a provided compound or pharmaceutically acceptable salt thereof, is selected from those wherein IRAK is

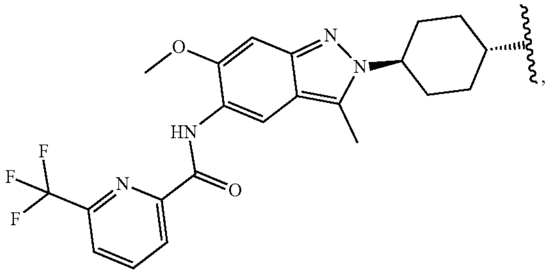 [SMILES: *[C@H]1CC[C@H](n2nc3cc(OC)c(NC(=O)c4cccc(C(F)(F)F)n4)cc3c2C)CC1]

LBM is selected from any of those in Table A below, and L is selected from any of those in Table B below.

In some embodiments, a provided compound or pharmaceutically acceptable salt thereof, is selected from those wherein IRAK is

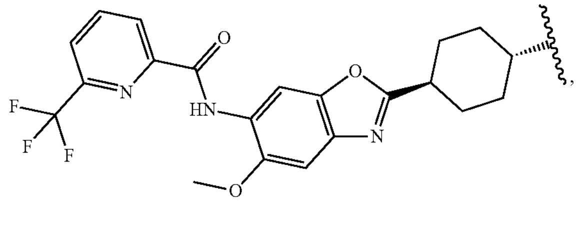 [SMILES: *[C@H]1CC[C@H](c2nc3cc(OC)c(NC(=O)c4cccc(C(F)(F)F)n4)cc3o2)CC1]

LBM is selected from any of those in Table A below, and L is selected from any of those in Table B below.

In some embodiments, a provided compound or pharmaceutically acceptable salt thereof, is selected from those wherein IRAK is

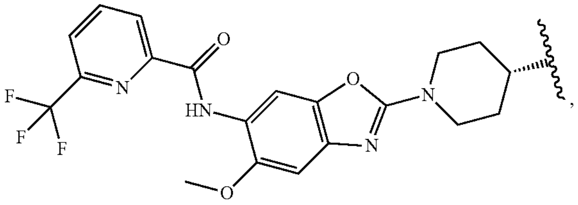

LBM is selected from any of those in Table A below, and L is selected from any of those in Table B below.

In some embodiments, a provided compound or pharmaceutically acceptable salt thereof, is selected from those wherein IRAK is

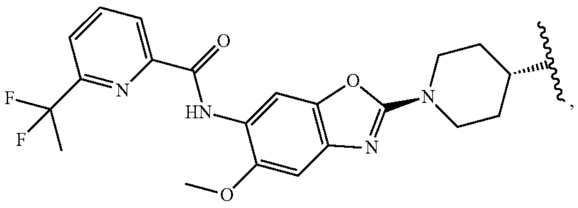

LBM is selected from any of those in Table A below, and L is selected from any of those in Table B below.

In some embodiments, a provided compound or pharmaceutically acceptable salt thereof, is selected from those wherein IRAK is

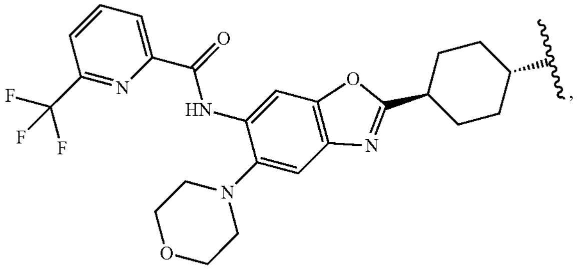 [SMILES: *[C@H]1CC[C@H](c2nc3cc(N4CCOCC4)c(NC(=O)c4cccc(C(F)(F)F)n4)cc3o2)CC1]

LBM is selected from any of those in Table A below, and L is selected from any of those in Table B below.

In some embodiments, a provided compound or pharmaceutically acceptable salt thereof, is selected from those wherein IRAK is

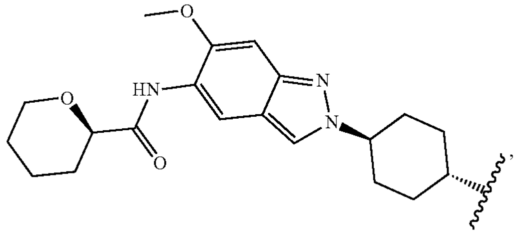 [SMILES: *[C@H]1CC[C@H](n2cc3cc(NC(=O)[C@H]4CCCCO4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

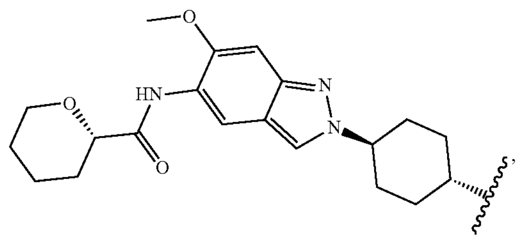 [SMILES: *[C@H]1CC[C@H](n2cc3cc(NC(=O)[C@@H]4CCCCO4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

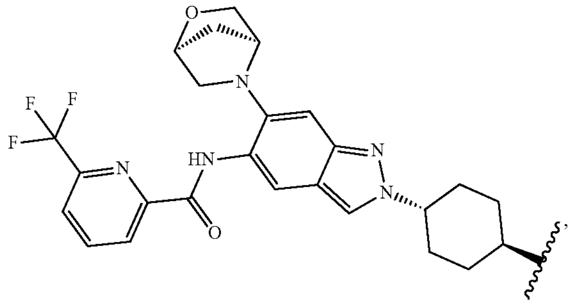 [SMILES: *[C@H]1CC[C@H](n2cc3cc(NC(=O)c4cccc(C(F)(F)F)n4)c(N4C[C@@H]5C[C@H]4CO5)cc3n2)CC1]

LBM is selected from any of those in Table A below, and L is selected from any of those in Table B below.

In some embodiments, a provided compound or pharmaceutically acceptable salt thereof, is selected from those wherein IRAK is

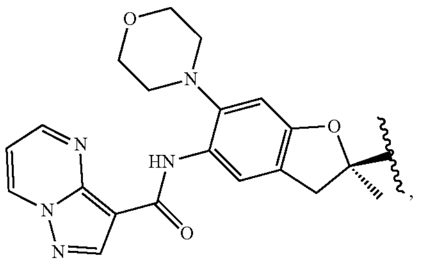 [SMILES: *[C@@]1(C)Cc2cc(NC(=O)c3cnn4cccnc34)c(N3CCOCC3)cc2O1]

LBM is selected from any of those in Table A below, and L is selected from any of those in Table B below.

In some embodiments, a provided compound or pharmaceutically acceptable salt thereof, is selected from those wherein IRAK is

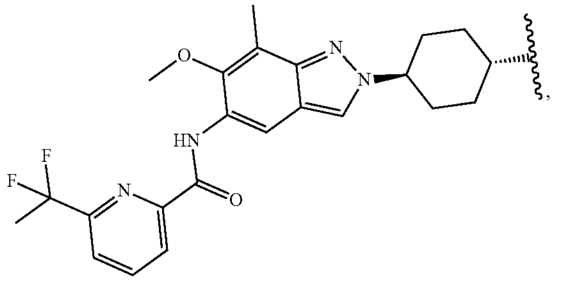 [SMILES: *[C@H]1CC[C@H](n2cc3cc(NC(=O)c4cccc(C(C)(F)F)n4)c(OC)c(C)c3n2)CC1]

LBM is selected from any of those in Table A below, and L is selected from any of those in Table B below.

In some embodiments, a provided compound or pharmaceutically acceptable salt thereof, is selected from those wherein IRAK is

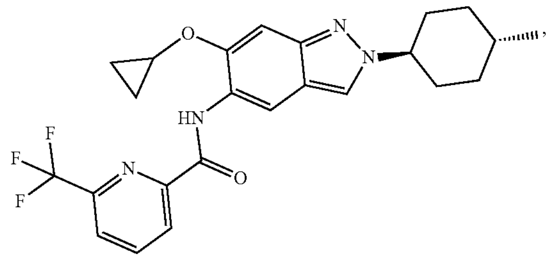 [SMILES: C[C@H]1CC[C@H](n2cc3cc(NC(=O)c4cccc(C(F)(F)F)n4)c(OC4CC4)cc3n2)CC1]

LBM is selected from any of those in Table A below, and L is selected from any of those in Table B below.

In some embodiments, a provided compound or pharmaceutically acceptable salt thereof, is selected from those wherein IRAK is

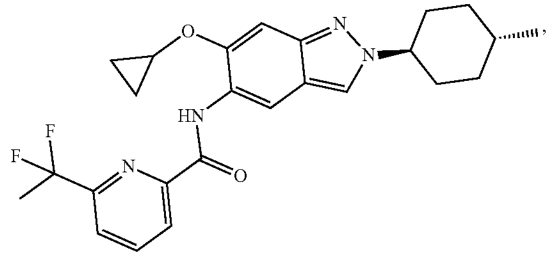 [SMILES: CC(F)(F)c1cccc(C(=O)Nc2cc3cn([C@H]4CC[C@H](C)CC4)nc3cc2OC2CC2)n1]

LBM is selected from any of those in Table A below, and L is selected from any of those in Table B below.

In some embodiments, a provided compound or pharmaceutically acceptable salt thereof, is selected from those wherein IRAK is

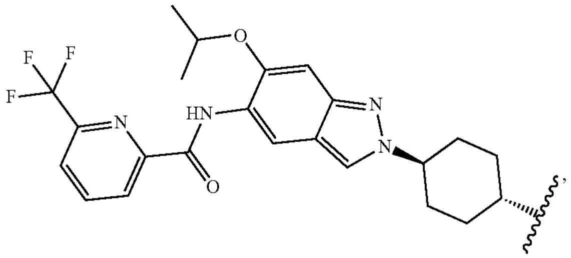 [SMILES: *[C@H]1CC[C@H](n2cc3cc(NC(=O)c4cccc(C(F)(F)F)n4)c(OC(C)C)cc3n2)CC1]

LBM is selected from any of those in Table A below, and L is selected from any of those in Table B below.

In some embodiments, a provided compound or pharmaceutically acceptable salt thereof, is selected from those wherein IRAK is

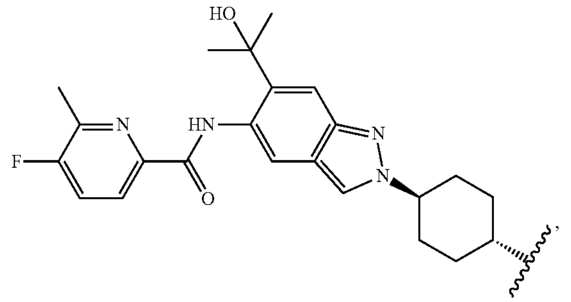

LBM is selected from any of those in Table A below, and L is selected from any of those in Table B below.

In some embodiments, a provided compound or pharmaceutically acceptable salt thereof, is selected from those wherein IRAK is

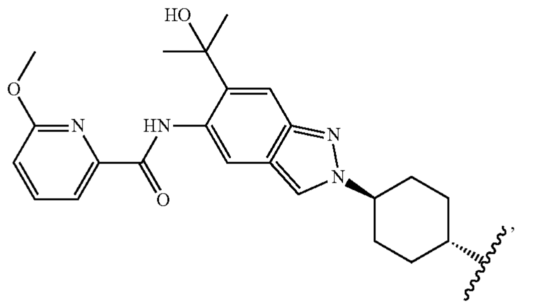

LBM is selected from any of those in Table A below, and L is selected from any of those in Table B below.

In some embodiments, a provided compound or pharmaceutically acceptable salt thereof, is selected from those wherein IRAK is

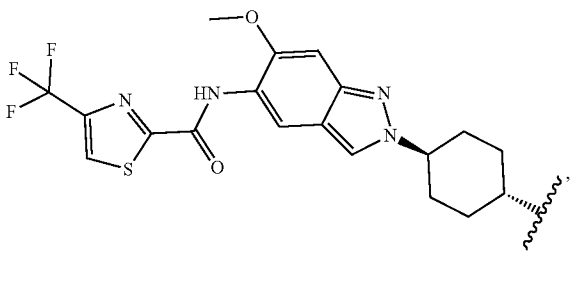 [SMILES: *[C@H]1CC[C@H](n2cc3cc(NC(=O)c4nc(C(F)(F)F)cs4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

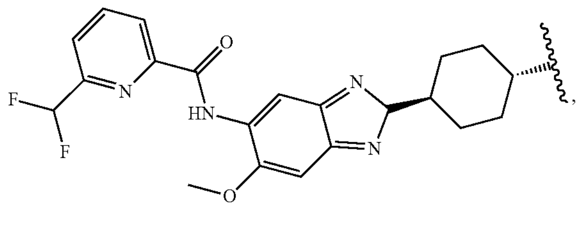 [SMILES: *[C@H]1CC[C@H](C2N=c3cc(NC(=O)c4cccc(C(F)F)n4)c(OC)cc3=N2)CC1]

LBM is selected from any of those in Table A below, and L is selected from any of those in Table B below.

In some embodiments, a provided compound or pharmaceutically acceptable salt thereof, is selected from those wherein IRAK is

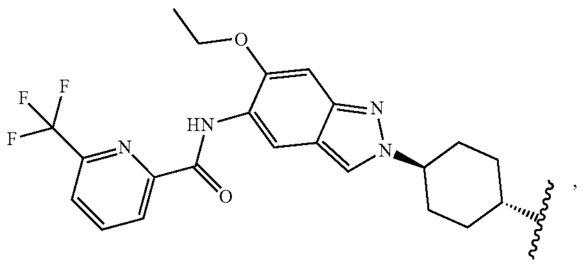 [SMILES: *[C@H]1CC[C@H](n2cc3cc(NC(=O)c4cccc(C(F)(F)F)n4)c(OCC)cc3n2)CC1]

LBM is selected from any of those in Table A below, and L is selected from any of those in Table B below.

In some embodiments, a provided compound or pharmaceutically acceptable salt thereof, is selected from those wherein IRAK is

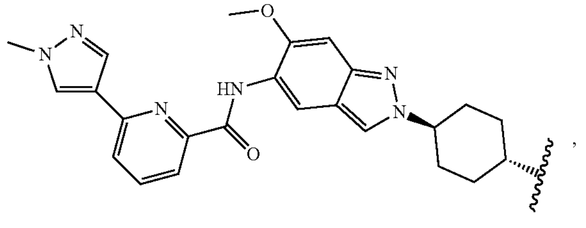 [SMILES: *[C@H]1CC[C@H](n2cc3cc(NC(=O)c4cccc(-c5cnn(C)c5)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

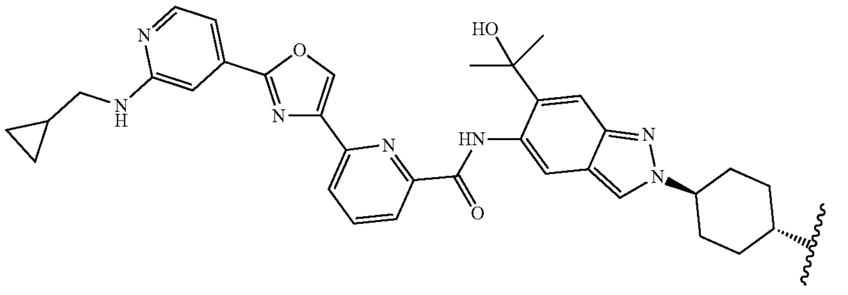
,

LBM is selected from any of those in Table A below, and L is selected from any of those in Table B below.

In some embodiments, a provided compound or pharmaceutically acceptable salt thereof, is selected from those wherein IRAK is

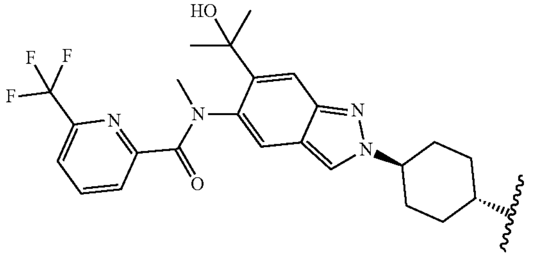
,

LBM is selected from any of those in Table A below, and L is selected from any of those in Table B below.

In some embodiments, a provided compound or pharmaceutically acceptable salt thereof, is selected from those wherein IRAK is

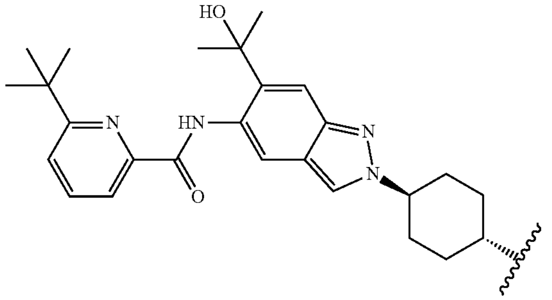
,

LBM is selected from any of those in Table A below, and L is selected from any of those in Table B below.

In some embodiments, a provided compound or pharmaceutically acceptable salt thereof, is selected from those wherein IRAK is

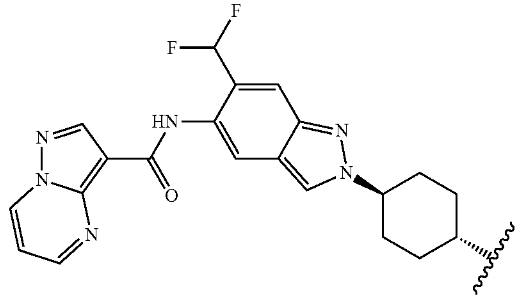
,

LBM is selected from any of those in Table A below, and L is selected from any of those in Table B below.

In some embodiments, a provided compound or pharmaceutically acceptable salt thereof, is selected from those wherein IRAK is

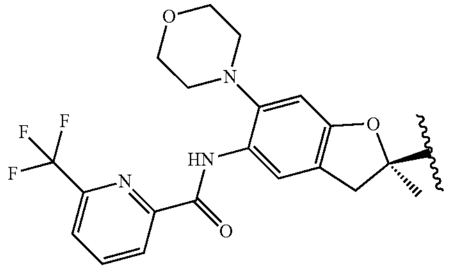
,

LBM is selected from any of those in Table A below, and L is selected from any of those in Table B below.

In some embodiments, a provided compound or pharmaceutically acceptable salt thereof, is selected from those wherein IRAK is

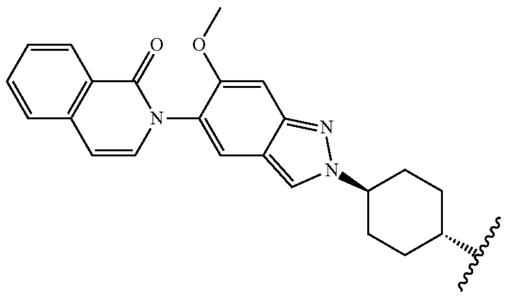
,

LBM is selected from any of those in Table A below, and L is selected from any of those in Table B below.

In some embodiments, a provided compound or pharmaceutically acceptable salt thereof, is selected from those wherein IRAK is

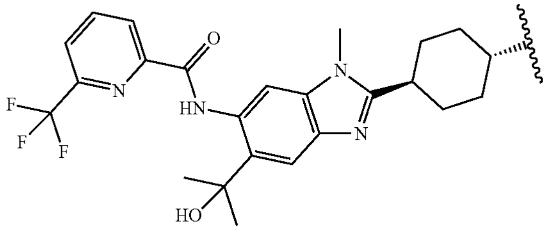
,

LBM is selected from any of those in Table A below, and L is selected from any of those in Table B below.

In some embodiments, a provided compound or pharmaceutically acceptable salt thereof, is selected from those wherein IRAK is

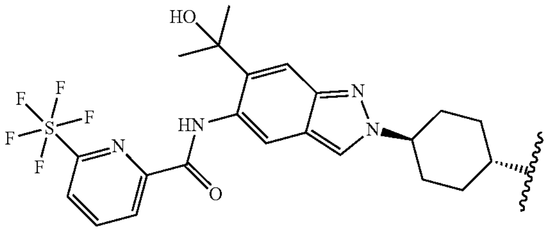
,

LBM is selected from any of those in Table A below, and L is selected from any of those in Table B below.

In some embodiments, a provided compound or pharmaceutically acceptable salt thereof, is selected from those wherein IRAK is

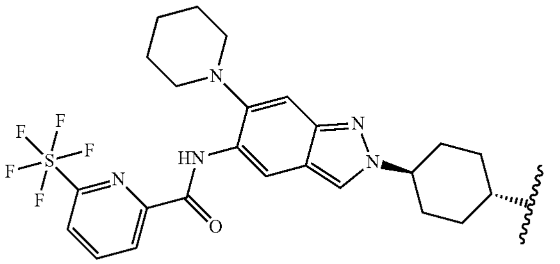
,

LBM is selected from any of those in Table A below, and L is selected from any of those in Table B below.

In some embodiments, a provided compound or pharmaceutically acceptable salt thereof, is selected from those wherein IRAK is

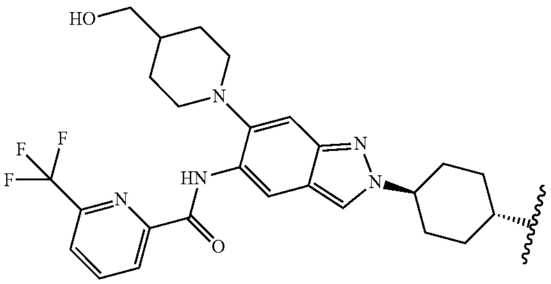
,

LBM is selected from any of those in Table A below, and L is selected from any of those in Table B below.

In some embodiments, a provided compound or pharmaceutically acceptable salt thereof, is selected from those wherein IRAK is

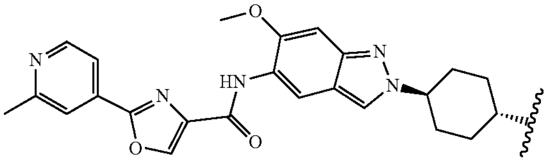
,

LBM is selected from any of those in Table A below, and L is selected from any of those in Table B below.

In some embodiments, a provided compound or pharmaceutically acceptable salt thereof, is selected from those wherein IRAK is

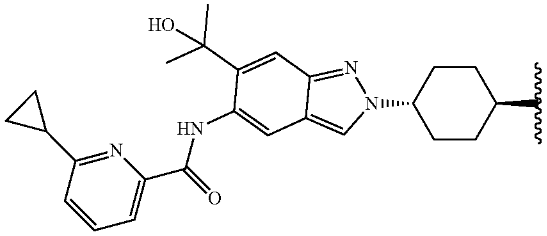
,

LBM is selected from any of those in Table A below, and L is selected from any of those in Table B below.

In some embodiments, a provided compound or pharmaceutically acceptable salt thereof, is selected from those wherein IRAK is

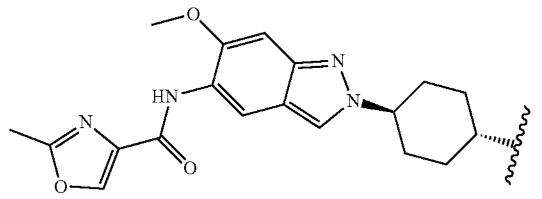
,

LBM is selected from any of those in Table A below, and L is selected from any of those in Table B below.

In some embodiments, a provided compound or pharmaceutically acceptable salt thereof, is selected from those wherein IRAK is

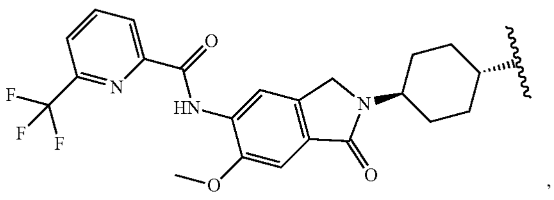 [SMILES: *[C@H]1CC[C@H](N2Cc3cc(NC(=O)c4cccc(C(F)(F)F)n4)c(OC)cc3C2=O)CC1]

,

LBM is selected from any of those in Table A below, and L is selected from any of those in Table B below.

In some embodiments, a provided compound or pharmaceutically acceptable salt thereof, is selected from those wherein IRAK is

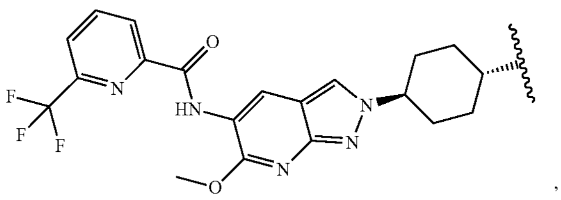 [SMILES: *[C@H]1CC[C@H](n2cc3cc(NC(=O)c4cccc(C(F)(F)F)n4)c(OC)nc3n2)CC1]

,

LBM is selected from any of those in Table A below, and L is selected from any of those in Table B below.

In some embodiments, a provided compound or pharmaceutically acceptable salt thereof, is selected from those wherein IRAK is

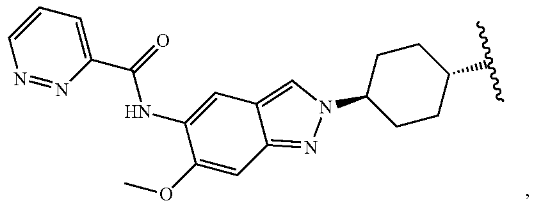 [SMILES: *[C@H]1CC[C@H](n2cc3cc(NC(=O)c4cccnn4)c(OC)cc3n2)CC1]

,

LBM is selected from any of those in Table A below, and L is selected from any of those in Table B below.

In some embodiments, a provided compound or pharmaceutically acceptable salt thereof, is selected from those wherein IRAK is

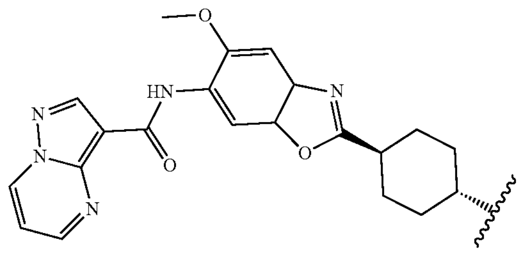

,

LBM is selected from any of those in Table A below, and L is selected from any of those in Table B below.

In some embodiments, a provided compound or pharmaceutically acceptable salt thereof, is selected from those wherein IRAK is

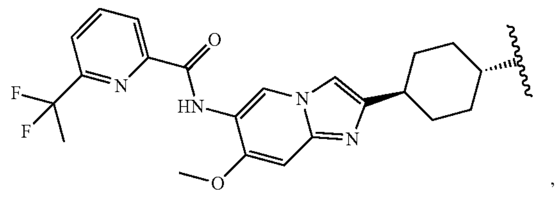 [SMILES: *[C@H]1CC[C@H](c2cn3cc(NC(=O)c4cccc(C(C)(F)F)n4)c(OC)cc3n2)CC1]

,

LBM is selected from any of those in Table A below, and L is selected from any of those in Table B below.

In some embodiments, a provided compound or pharmaceutically acceptable salt thereof, is selected from those wherein IRAK is

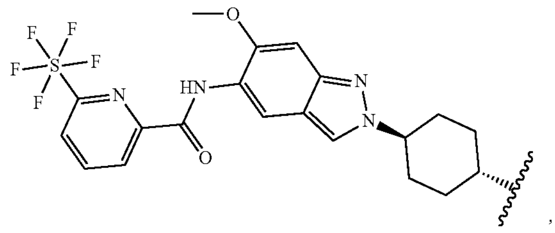 [SMILES: *[C@H]1CC[C@H](n2cc3cc(NC(=O)c4cccc(S(F)(F)(F)(F)F)n4)c(OC)cc3n2)CC1]

,

LBM is selected from any of those in Table A below, and L is selected from any of those in Table B below.

In some embodiments, a provided compound or pharmaceutically acceptable salt thereof, is selected from those wherein IRAK is

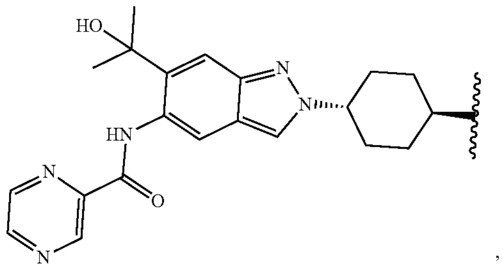 [SMILES: *[C@H]1CC[C@H](n2cc3cc(NC(=O)c4cnccn4)c(C(C)(C)O)cc3n2)CC1]

,

LBM is selected from any of those in Table A below, and L is selected from any of those in Table B below.

In some embodiments, a provided compound or pharmaceutically acceptable salt thereof, is selected from those wherein IRAK is

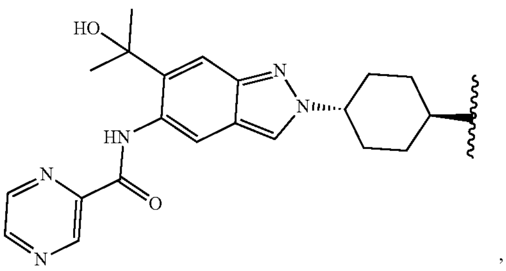 [SMILES: *[C@H]1CC[C@H](n2cc3cc(NC(=O)c4cnccn4)c(C(C)(C)O)cc3n2)CC1]

,

LBM is selected from any of those in Table A below, and L is selected from any of those in Table B below.

In some embodiments, a provided compound or pharmaceutically acceptable salt thereof, is selected from those wherein IRAK is

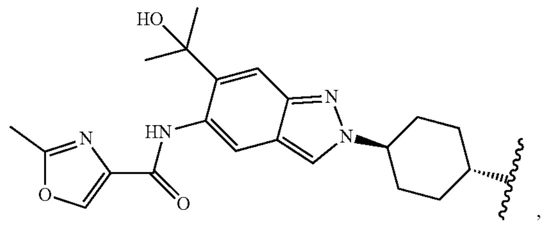 [SMILES: *[C@H]1CC[C@H](n2cc3cc(NC(=O)c4coc(C)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

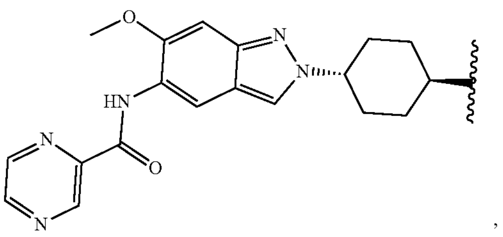 [SMILES: *[C@H]1CC[C@H](n2cc3cc(NC(=O)c4cnccn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

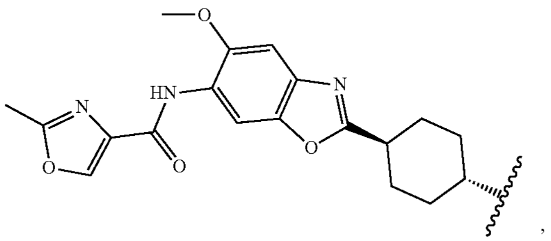 [SMILES: *[C@H]1CC[C@H](c2nc3cc(OC)c(NC(=O)c4coc(C)n4)cc3o2)CC1]

LBM is selected from any of those in Table A below, and L is selected from any of those in Table B below.

In some embodiments, a provided compound or pharmaceutically acceptable salt thereof, is selected from those wherein IRAK is

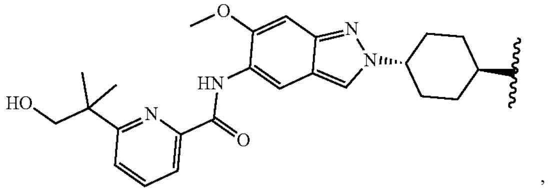 [SMILES: *[C@H]1CC[C@H](n2cc3cc(NC(=O)c4cccc(C(C)(C)CO)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

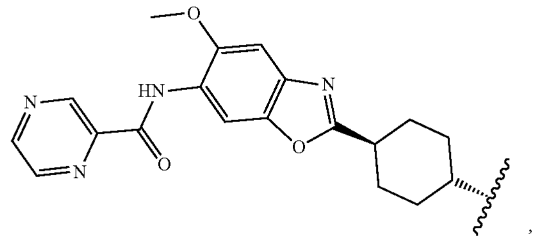

LBM is selected from any of those in Table A below, and L is selected from any of those in Table B below.

In some embodiments, a provided compound or pharmaceutically acceptable salt thereof, is selected from those wherein IRAK is

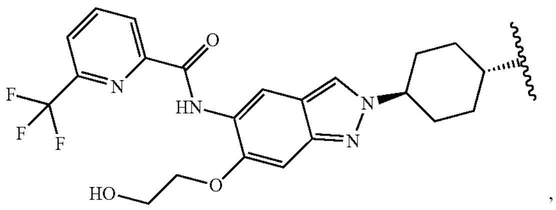 [SMILES: *[C@H]1CC[C@H](n2cc3cc(NC(=O)c4cccc(C(F)(F)F)n4)c(OCCO)cc3n2)CC1]

LBM is selected from any of those in Table A below, and L is selected from any of those in Table B below.

In some embodiments, a provided compound or pharmaceutically acceptable salt thereof, is selected from those wherein IRAK is

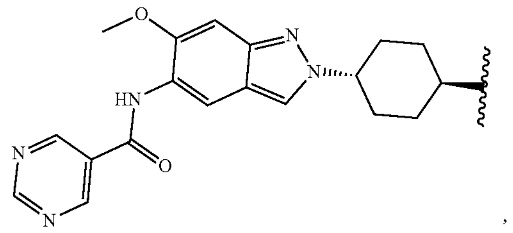 [SMILES: *[C@H]1CC[C@H](n2cc3cc(NC(=O)c4cncnc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

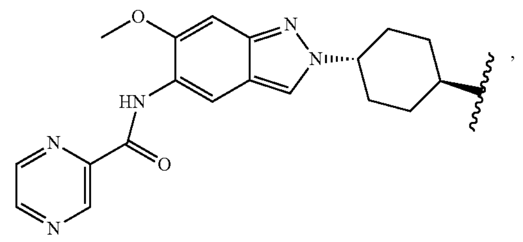 [SMILES: *[C@H]1CC[C@H](n2cc3cc(NC(=O)c4cnccn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

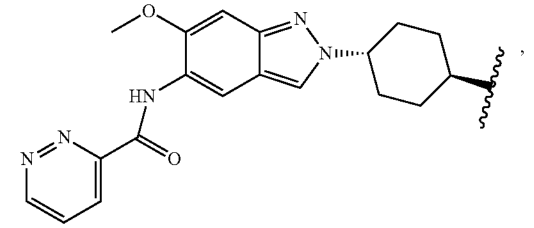 [SMILES: *[C@H]1CC[C@H](n2cc3cc(NC(=O)c4cccnn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

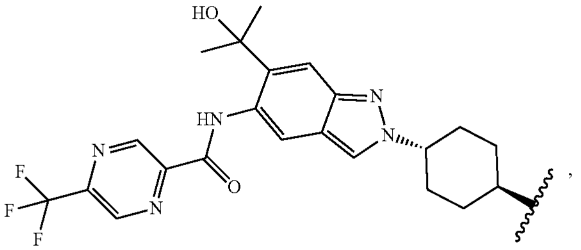 [SMILES: *[C@H]1CC[C@H](n2cc3cc(NC(=O)c4cnc(C(F)(F)F)cn4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

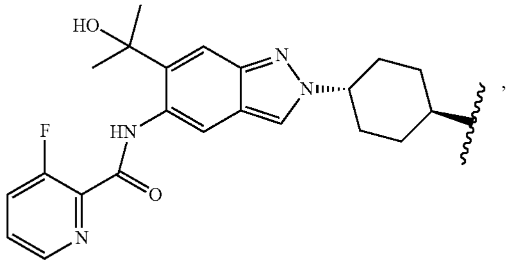 [SMILES: *[C@H]1CC[C@H](n2cc3cc(NC(=O)c4ncccc4F)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

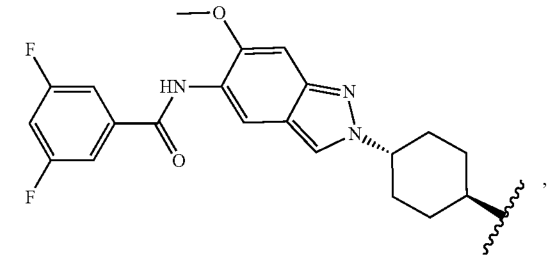 [SMILES: *[C@H]1CC[C@H](n2cc3cc(NC(=O)c4cc(F)cc(F)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

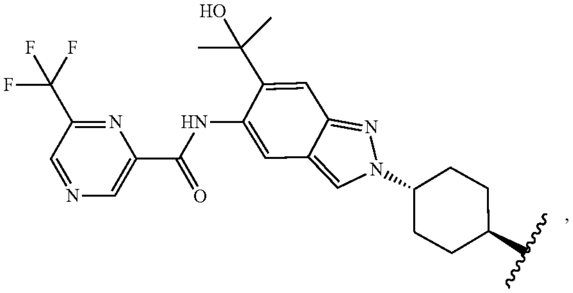 [SMILES: *[C@H]1CC[C@H](n2cc3cc(NC(=O)c4cncc(C(F)(F)F)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

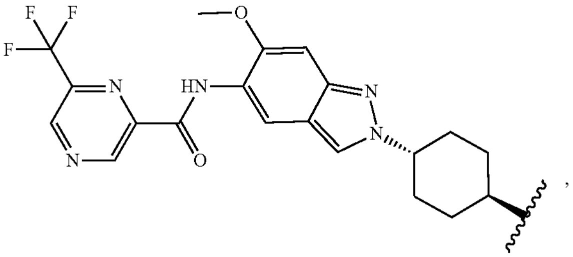 [SMILES: *[C@H]1CC[C@H](n2cc3cc(NC(=O)c4cncc(C(F)(F)F)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

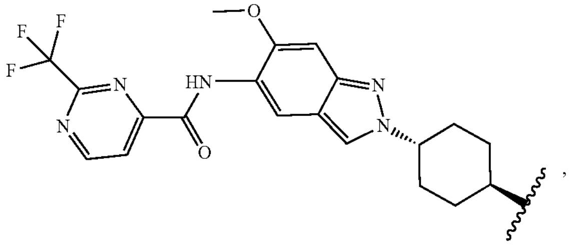

LBM is selected from any of those in Table A below, and L is selected from any of those in Table B below.

In some embodiments, a provided compound or pharmaceutically acceptable salt thereof, is selected from those wherein IRAK is

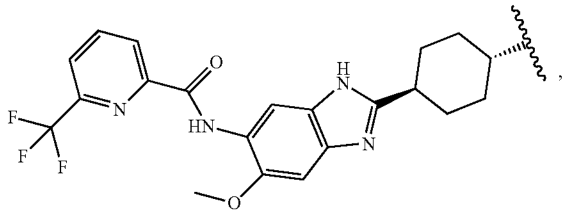 [SMILES: *[C@H]1CC[C@H](c2nc3cc(OC)c(NC(=O)c4cccc(C(F)(F)F)n4)cc3[nH]2)CC1]

LBM is selected from any of those in Table A below, and L is selected from any of those in Table B below.

In some embodiments, a provided compound or pharmaceutically acceptable salt thereof, is selected from those wherein IRAK is

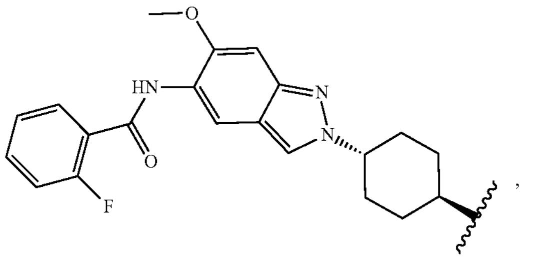 [SMILES: *[C@H]1CC[C@H](n2cc3cc(NC(=O)c4ccccc4F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

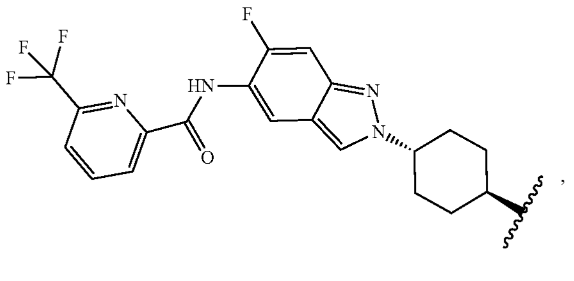 [SMILES: *[C@H]1CC[C@H](n2cc3cc(NC(=O)c4cccc(C(F)(F)F)n4)c(F)cc3n2)CC1]

LBM is selected from any of those in Table A below, and L is selected from any of those in Table B below.

In some embodiments, a provided compound or pharmaceutically acceptable salt thereof, is selected from those wherein IRAK is

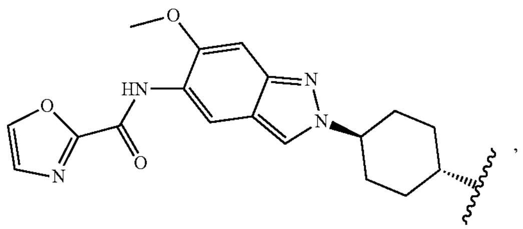 [SMILES: *[C@H]1CC[C@H](n2cc3cc(NC(=O)c4ncco4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

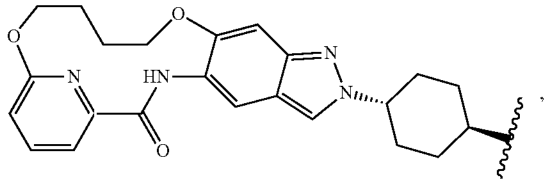 [SMILES: *[C@H]1CC[C@H](n2cc3cc(NC(C)=O)c(OCCCCOc4ccccn4)cc3n2)CC1]

LBM is selected from any of those in Table A below, and L is selected from any of those in Table B below.

In some embodiments, a provided compound or pharmaceutically acceptable salt thereof, is selected from those wherein IRAK is

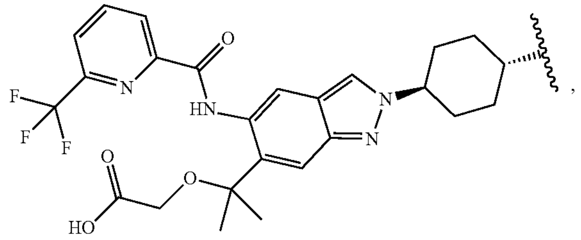 [SMILES: *[C@H]1CC[C@H](n2cc3cc(NC(=O)c4cccc(C(F)(F)F)n4)c(C(C)(C)OCC(=O)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

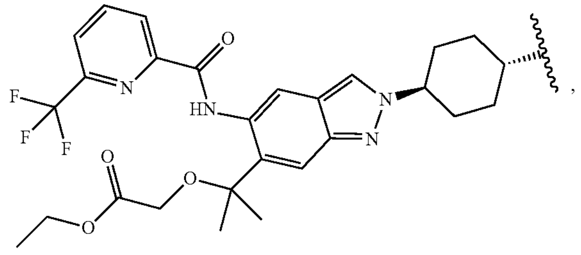 [SMILES: *[C@H]1CC[C@H](n2cc3cc(NC(=O)c4cccc(C(F)(F)F)n4)c(C(C)(C)OCC(=O)OCC)cc3n2)CC1]

LBM is selected from any of those in Table A below, and L is selected from any of those in Table B below.

In some embodiments, a provided compound or pharmaceutically acceptable salt thereof, is selected from those wherein IRAK is

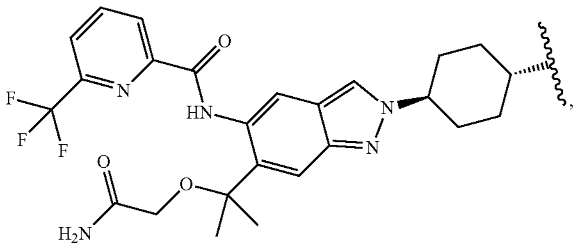 [SMILES: *[C@H]1CC[C@H](n2cc3cc(NC(=O)c4cccc(C(F)(F)F)n4)c(C(C)(C)OCC(N)=O)cc3n2)CC1]

LBM is selected from any of those in Table A below, and L is selected from any of those in Table B below.

In some embodiments, a provided compound or pharmaceutically acceptable salt thereof, is selected from those wherein IRAK is

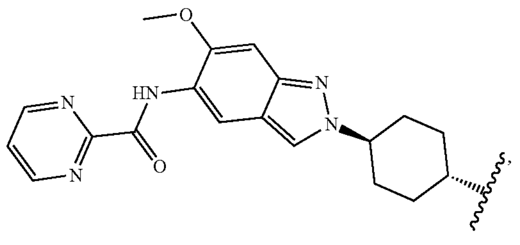 [SMILES: *[C@H]1CC[C@H](n2cc3cc(NC(=O)c4ncccn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

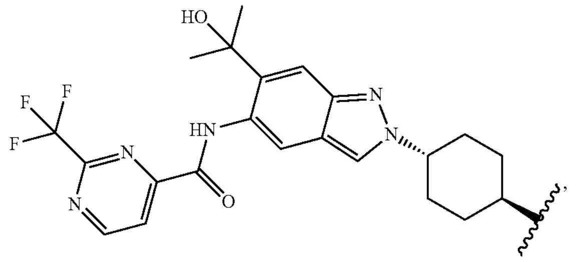 [SMILES: *[C@H]1CC[C@H](n2cc3cc(NC(=O)c4ccnc(C(F)(F)F)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

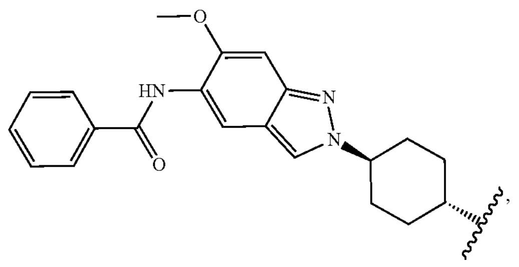 [SMILES: *[C@H]1CC[C@H](n2cc3cc(NC(=O)c4ccccc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

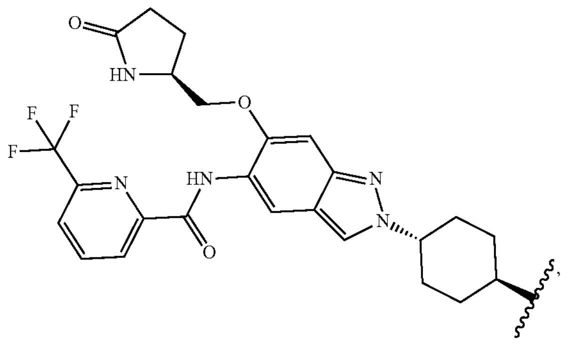 [SMILES: *[C@H]1CC[C@H](n2cc3cc(NC(=O)c4cccc(C(F)(F)F)n4)c(OC[C@@H]4CCC(=O)N4)cc3n2)CC1]

LBM is selected from any of those in Table A below, and L is selected from any of those in Table B below.

In some embodiments, a provided compound or pharmaceutically acceptable salt thereof, is selected from those wherein IRAK is

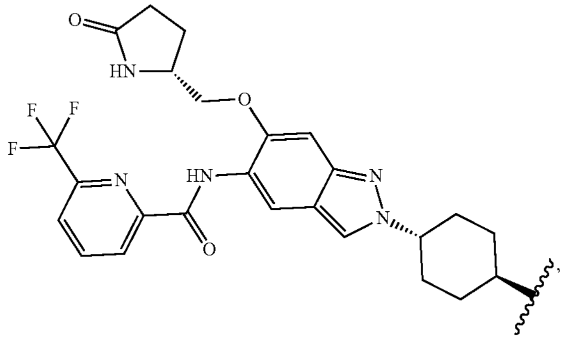 [SMILES: *[C@H]1CC[C@H](n2cc3cc(NC(=O)c4cccc(C(F)(F)F)n4)c(OC[C@H]4CCC(=O)N4)cc3n2)CC1]

LBM is selected from any of those in Table A below, and L is selected from any of those in Table B below.

In some embodiments, a provided compound or pharmaceutically acceptable salt thereof, is selected from those wherein IRAK is

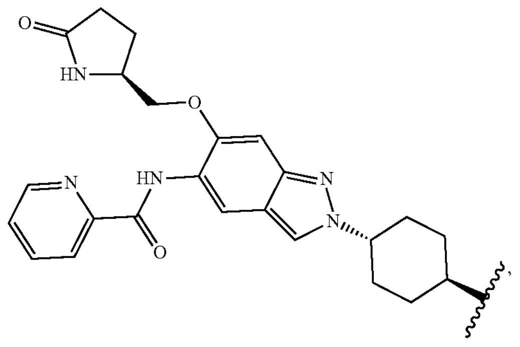 [SMILES: *[C@H]1CC[C@H](n2cc3cc(NC(=O)c4ccccn4)c(OC[C@@H]4CCC(=O)N4)cc3n2)CC1]

LBM is selected from any of those in Table A below, and L is selected from any of those in Table B below.

In some embodiments, a provided compound or pharmaceutically acceptable salt thereof, is selected from those wherein IRAK is

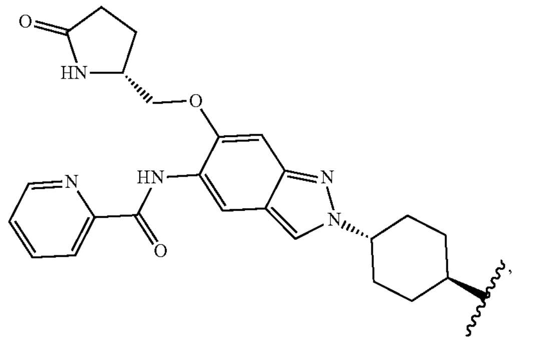 [SMILES: *[C@H]1CC[C@H](n2cc3cc(NC(=O)c4ccccn4)c(OC[C@H]4CCC(=O)N4)cc3n2)CC1]

LBM is selected from any of those in Table A below, and L is selected from any of those in Table B below.

In some embodiments, a provided compound or pharmaceutically acceptable salt thereof, is selected from those wherein IRAK is

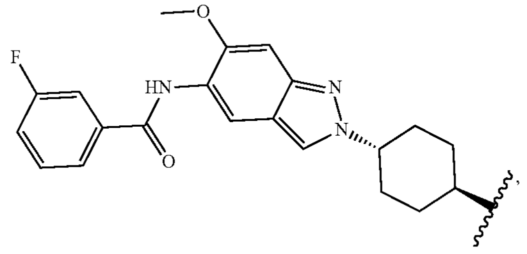 [SMILES: *[C@H]1CC[C@H](n2cc3cc(NC(=O)c4cccc(F)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is F

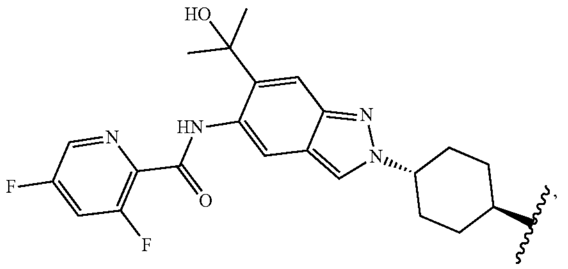 [SMILES: *[C@H]1CC[C@H](n2cc3cc(NC(=O)c4ncc(F)cc4F)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

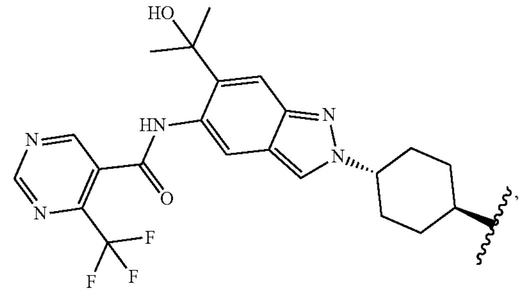 [SMILES: *[C@H]1CC[C@H](n2cc3cc(NC(=O)c4cncnc4C(F)(F)F)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

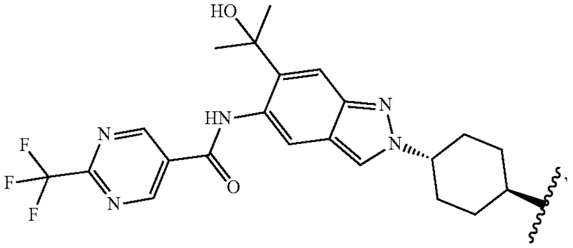 [SMILES: *[C@H]1CC[C@H](n2cc3cc(NC(=O)c4cnc(C(F)(F)F)nc4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

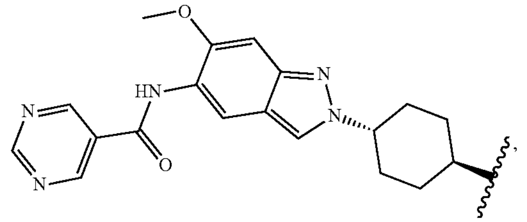 [SMILES: *[C@H]1CC[C@H](n2cc3cc(NC(=O)c4cncnc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

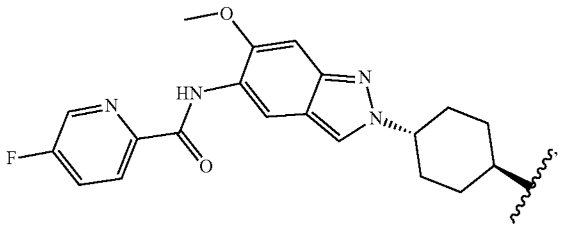 [SMILES: *[C@H]1CC[C@H](n2cc3cc(NC(=O)c4ccc(F)cn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

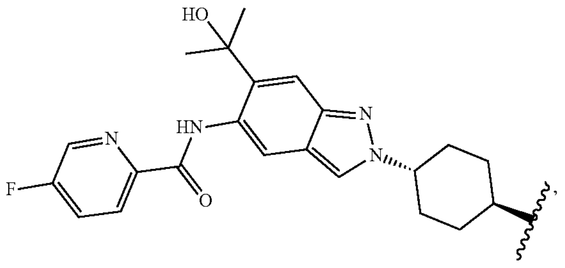 [SMILES: *[C@H]1CC[C@H](n2cc3cc(NC(=O)c4ccc(F)cn4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

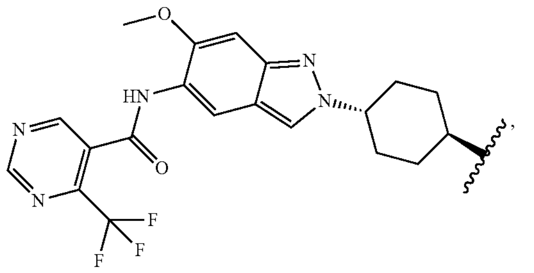 [SMILES: *[C@H]1CC[C@H](n2cc3cc(NC(=O)c4cncnc4C(F)(F)F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

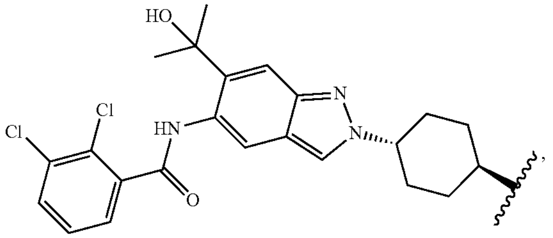 [SMILES: *[C@H]1CC[C@H](n2cc3cc(NC(=O)c4cccc(Cl)c4Cl)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

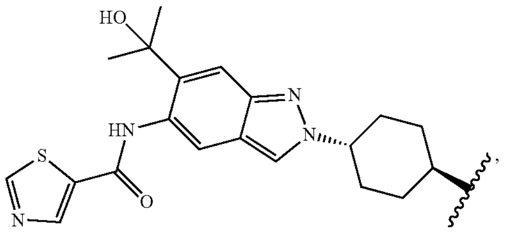 [SMILES: *[C@H]1CC[C@H](n2cc3cc(NC(=O)c4cncs4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

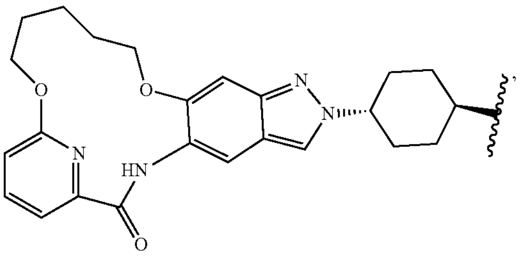 [SMILES: *[C@H]1CC[C@H](n2cc3cc(C)c(OCCCCCOc4cccc(C(N)=O)n4)cc3n2)CC1]

LBM is selected from any of those in Table A below, and L is selected from any of those in Table B below.

In some embodiments, a provided compound or pharmaceutically acceptable salt thereof, is selected from those wherein IRAK is

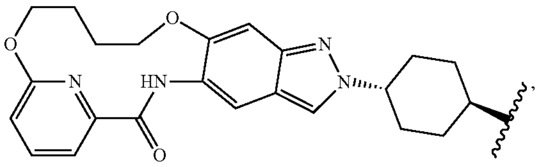 [SMILES: *[C@H]1CC[C@H](n2cc3cc4c(cc3n2)OCCCCOc2cccc(n2)C(=O)N4)CC1]

LBM is selected from any of those in Table A below, and L is selected from any of those in Table B below.

In some embodiments, a provided compound or pharmaceutically acceptable salt thereof, is selected from those wherein IRAK is

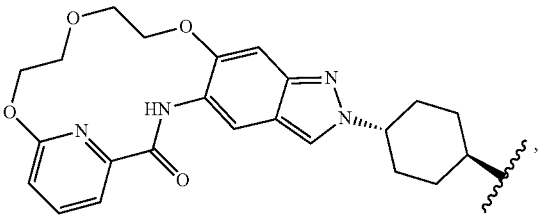 [SMILES: *[C@H]1CC[C@H](n2cc3cc4c(cc3n2)OCCOCCOc2cccc(n2)C(=O)N4)CC1]

LBM is selected from any of those in Table A below, and L is selected from any of those in Table B below.

In some embodiments, a provided compound or pharmaceutically acceptable salt thereof, is selected from those wherein IRAK is

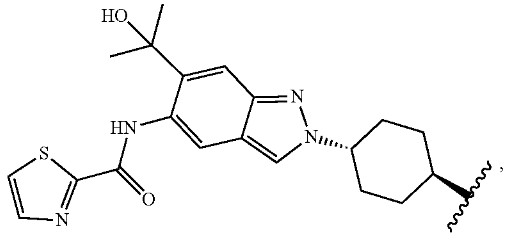 [SMILES: *[C@H]1CC[C@H](n2cc3cc(NC(=O)c4nccs4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

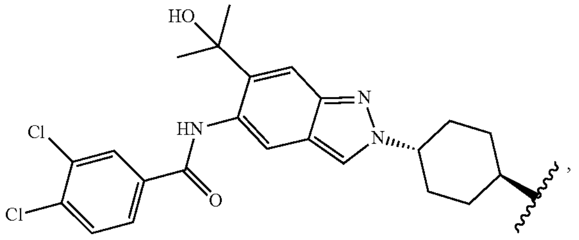 [SMILES: *[C@H]1CC[C@H](n2cc3cc(NC(=O)c4ccc(Cl)c(Cl)c4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

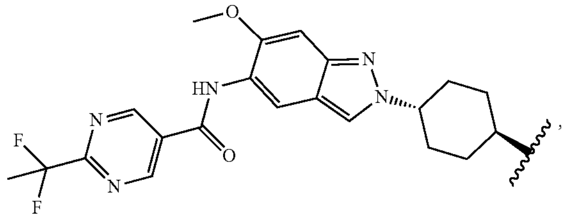 [SMILES: *[C@H]1CC[C@H](n2cc3cc(NC(=O)c4cnc(C(C)(F)F)nc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

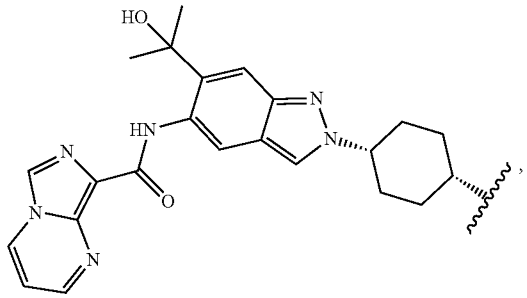 [SMILES: *[C@H]1CC[C@@H](n2cc3cc(NC(=O)c4ncn5cccnc45)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

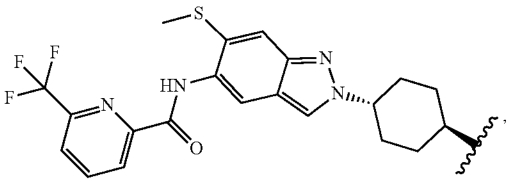 [SMILES: *[C@H]1CC[C@H](n2cc3cc(NC(=O)c4cccc(C(F)(F)F)n4)c(SC)cc3n2)CC1]

LBM is selected from any of those in Table A below, and L is selected from any of those in Table B below.

In some embodiments, a provided compound or pharmaceutically acceptable salt thereof, is selected from those wherein IRAK is

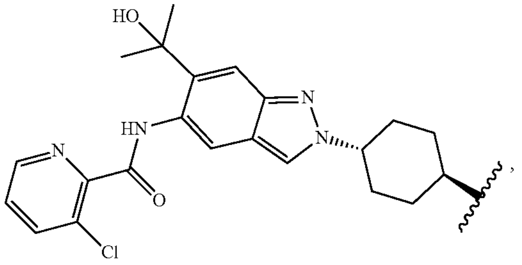 [SMILES: *[C@H]1CC[C@H](n2cc3cc(NC(=O)c4ncccc4Cl)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

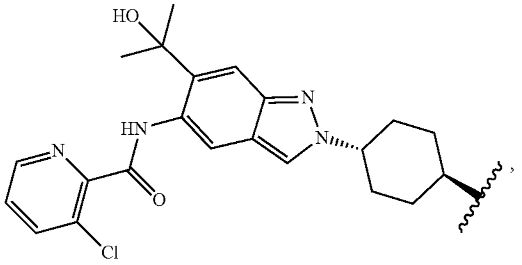 [SMILES: *[C@H]1CC[C@H](n2cc3cc(NC(=O)c4ncccc4Cl)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

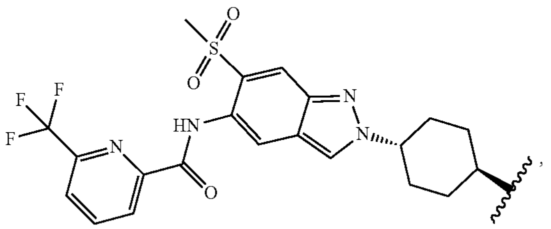 [SMILES: *[C@H]1CC[C@H](n2cc3cc(NC(=O)c4cccc(C(F)(F)F)n4)c(S(C)(=O)=O)cc3n2)CC1]

LBM is selected from any of those in Table A below, and L is selected from any of those in Table B below.

In some embodiments, a provided compound or pharmaceutically acceptable salt thereof, is selected from those wherein IRAK is

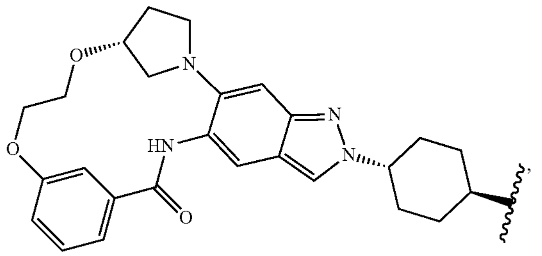 [SMILES: *[C@H]1CC[C@H](n2cc3cc4c(cc3n2)N2CC[C@H](C2)OCCOc2cccc(c2)C(=O)N4)CC1]

LBM is selected from any of those in Table A below, and L is selected from any of those in Table B below.

In some embodiments, a provided compound or pharmaceutically acceptable salt thereof, is selected from those wherein IRAK is

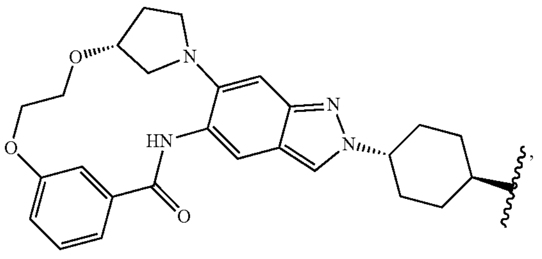 [SMILES: *[C@H]1CC[C@H](n2cc3cc4c(cc3n2)N2CC[C@H](C2)OCCOc2cccc(c2)C(=O)N4)CC1]

LBM is selected from any of those in Table A below, and L is selected from any of those in Table B below.

In some embodiments, a provided compound or pharmaceutically acceptable salt thereof, is selected from those wherein IRAK is

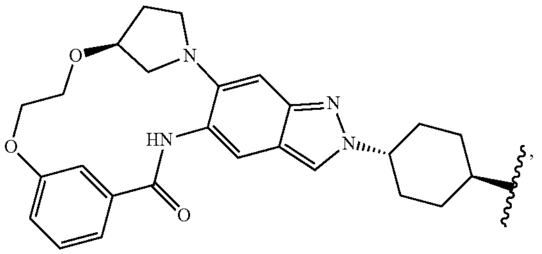 [SMILES: *[C@H]1CC[C@H](n2cc3cc4c(cc3n2)N2CC[C@@H](C2)OCCOc2cccc(c2)C(=O)N4)CC1]

LBM is selected from any of those in Table A below, and L is selected from any of those in Table B below.

In some embodiments, a provided compound or pharmaceutically acceptable salt thereof, is selected from those wherein IRAK is

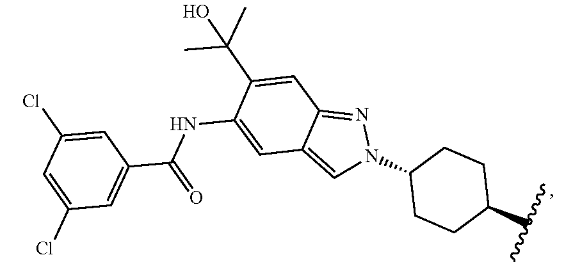 [SMILES: *[C@H]1CC[C@H](n2cc3cc(NC(=O)c4cc(Cl)cc(Cl)c4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

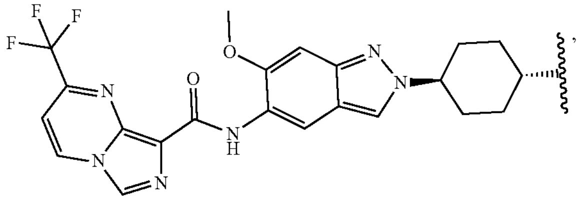 [SMILES: *[C@H]1CC[C@H](n2cc3cc(NC(=O)c4ncn5ccc(C(F)(F)F)nc45)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

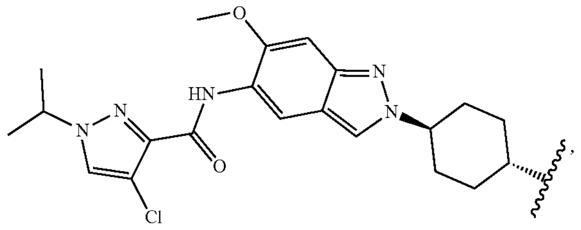 [SMILES: *[C@H]1CC[C@H](n2cc3cc(NC(=O)c4nn(C(C)C)cc4Cl)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

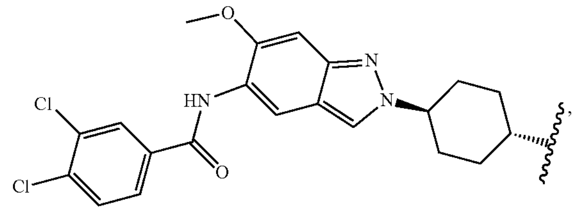 [SMILES: *[C@H]1CC[C@H](n2cc3cc(NC(=O)c4ccc(Cl)c(Cl)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

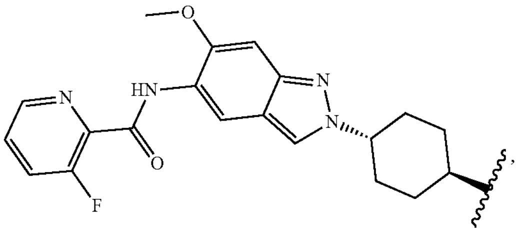 [SMILES: *[C@H]1CC[C@H](n2cc3cc(NC(=O)c4ncccc4F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

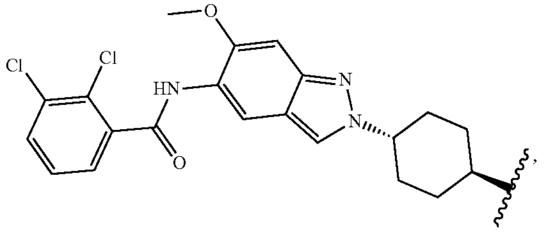 [SMILES: *[C@H]1CC[C@H](n2cc3cc(NC(=O)c4cccc(Cl)c4Cl)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

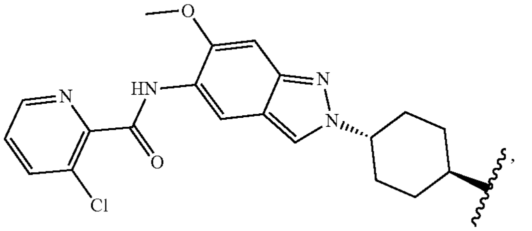 [SMILES: *[C@H]1CC[C@H](n2cc3cc(NC(=O)c4ncccc4Cl)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

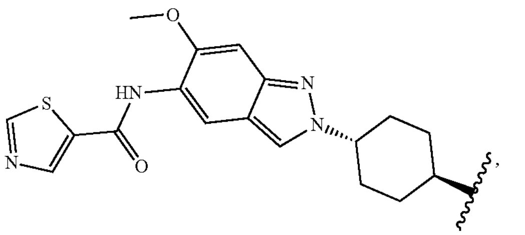 [SMILES: *[C@H]1CC[C@H](n2cc3cc(NC(=O)c4cncs4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

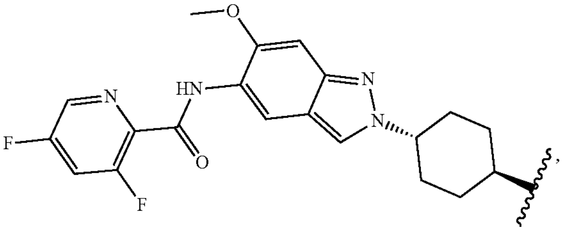 [SMILES: *[C@H]1CC[C@H](n2cc3cc(NC(=O)c4ncc(F)cc4F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

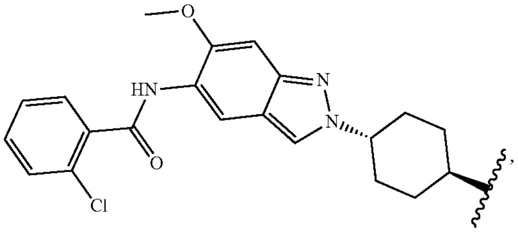 [SMILES: *[C@H]1CC[C@H](n2cc3cc(NC(=O)c4ccccc4Cl)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

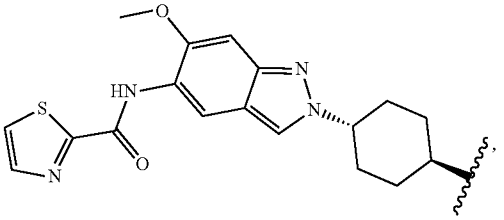 [SMILES: *[C@H]1CC[C@H](n2cc3cc(NC(=O)c4nccs4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

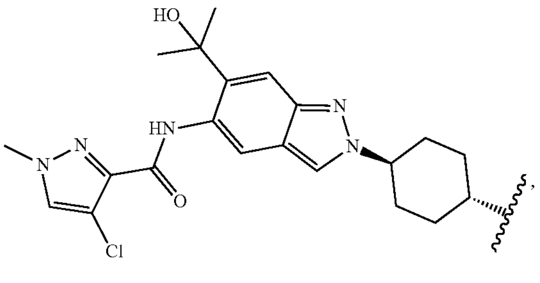 [SMILES: *[C@H]1CC[C@H](n2cc3cc(NC(=O)c4nn(C)cc4Cl)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

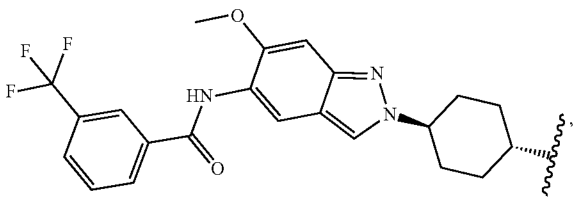 [SMILES: *[C@H]1CC[C@H](n2cc3cc(NC(=O)c4cccc(C(F)(F)F)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

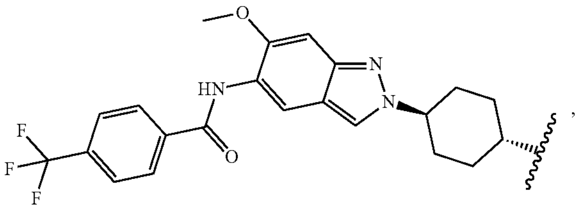 [SMILES: *[C@H]1CC[C@H](n2cc3cc(NC(=O)c4ccc(C(F)(F)F)cc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

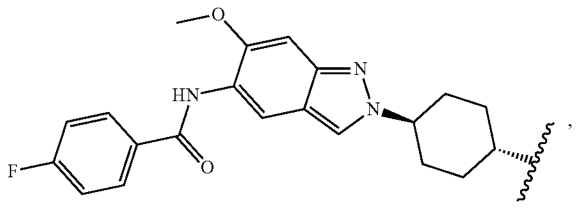 [SMILES: *[C@H]1CC[C@H](n2cc3cc(NC(=O)c4ccc(F)cc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

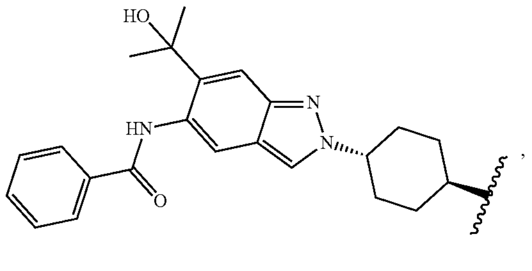 [SMILES: *[C@H]1CC[C@H](n2cc3cc(NC(=O)c4ccccc4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

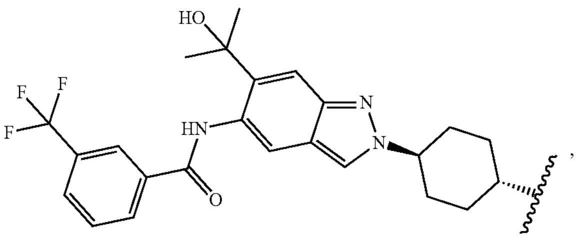 [SMILES: *[C@H]1CC[C@H](n2cc3cc(NC(=O)c4cccc(C(F)(F)F)c4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

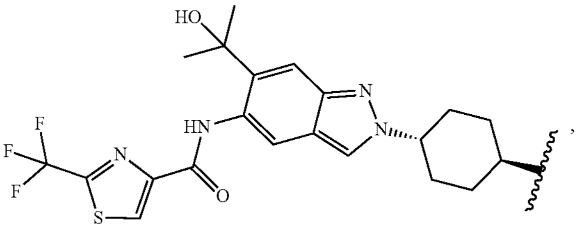 [SMILES: *[C@H]1CC[C@H](n2cc3cc(NC(=O)c4csc(C(F)(F)F)n4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

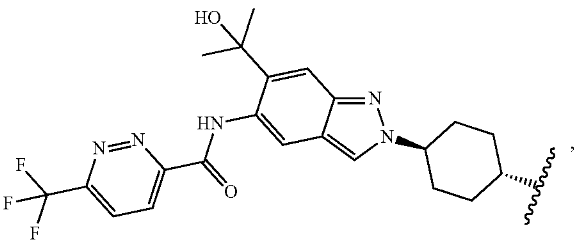 [SMILES: *[C@H]1CC[C@H](n2cc3cc(NC(=O)c4ccc(C(F)(F)F)nn4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

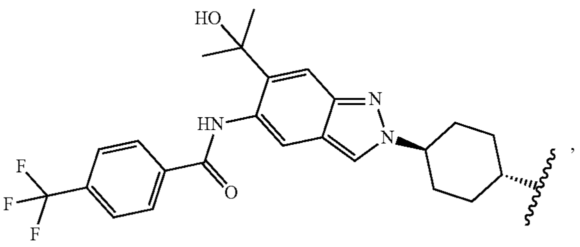 [SMILES: *[C@H]1CC[C@H](n2cc3cc(NC(=O)c4ccc(C(F)(F)F)cc4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

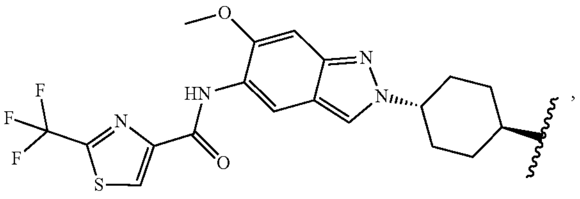 [SMILES: *[C@H]1CC[C@H](n2cc3cc(NC(=O)c4csc(C(F)(F)F)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

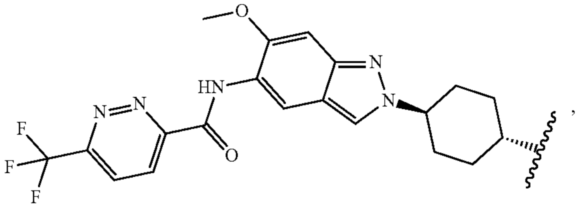 [SMILES: *[C@H]1CC[C@H](n2cc3cc(NC(=O)c4ccc(C(F)(F)F)nn4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

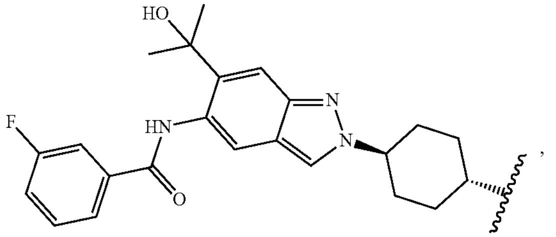 [SMILES: *[C@H]1CC[C@H](n2cc3cc(NC(=O)c4cccc(F)c4)c(C(C)(C)O)cc3n2)CC1]

LBM is selected from any of those in Table A below, and L is selected from any of those in Table B below.

In some embodiments, a provided compound or pharmaceutically acceptable salt thereof, is selected from those wherein IRAK is

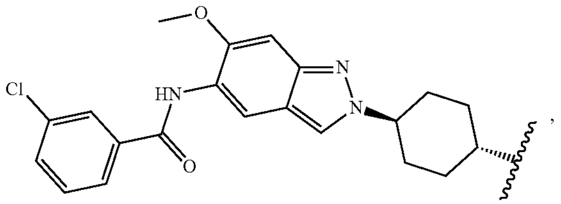 [SMILES: *[C@H]1CC[C@H](n2cc3cc(NC(=O)c4cccc(Cl)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

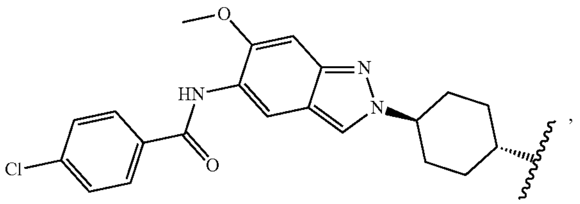 [SMILES: *[C@H]1CC[C@H](n2cc3cc(NC(=O)c4ccc(Cl)cc4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

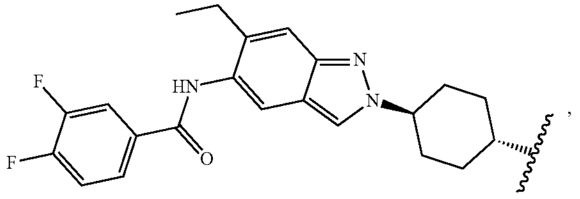 [SMILES: *[C@H]1CC[C@H](n2cc3cc(NC(=O)c4ccc(F)c(F)c4)c(CC)cc3n2)CC1]

LBM is selected from any of those in Table A below, and L is selected from any of those in Table B below.

In some embodiments, a provided compound or pharmaceutically acceptable salt thereof, is selected from those wherein IRAK is

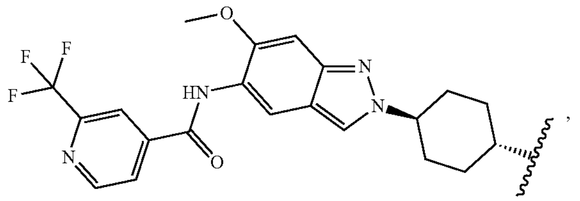 [SMILES: *[C@H]1CC[C@H](n2cc3cc(NC(=O)c4ccnc(C(F)(F)F)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

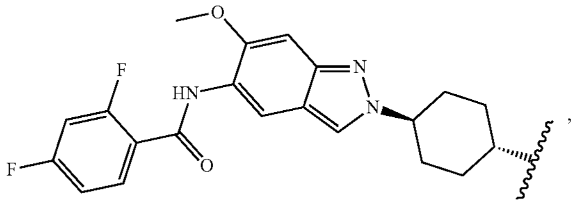 [SMILES: *[C@H]1CC[C@H](n2cc3cc(NC(=O)c4ccc(F)cc4F)c(OC)cc3n2)CC1]

In some embodiments, a provided compound or pharmaceutically acceptable salt thereof, is selected from those wherein IRAK is

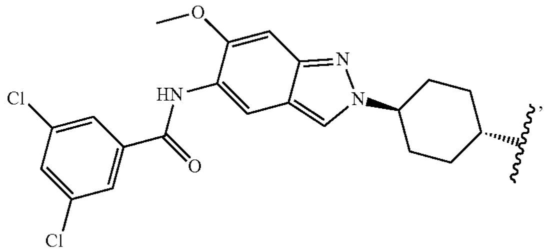 [SMILES: *[C@H]1CC[C@H](n2cc3cc(NC(=O)c4cc(Cl)cc(Cl)c4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

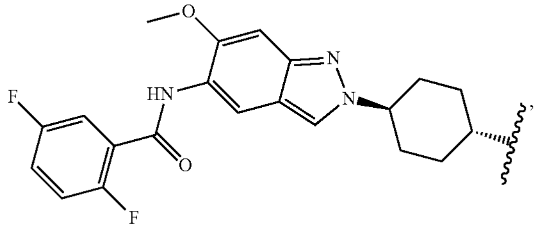 [SMILES: *[C@H]1CC[C@H](n2cc3cc(NC(=O)c4cc(F)ccc4F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

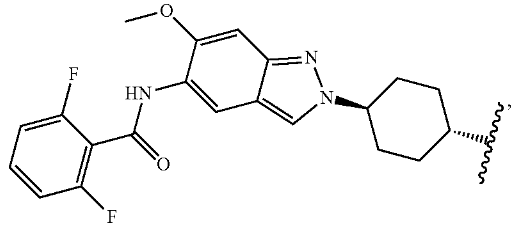 [SMILES: *[C@H]1CC[C@H](n2cc3cc(NC(=O)c4c(F)cccc4F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

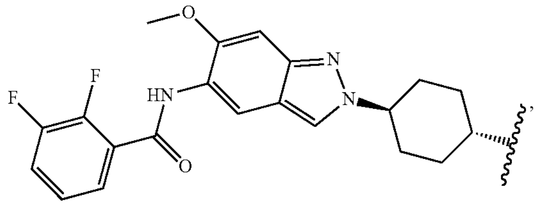 [SMILES: *[C@H]1CC[C@H](n2cc3cc(NC(=O)c4cccc(F)c4F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

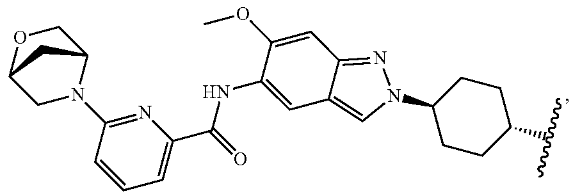 [SMILES: *[C@H]1CC[C@H](n2cc3cc(NC(=O)c4cccc(N5C[C@H]6C[C@@H]5CO6)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

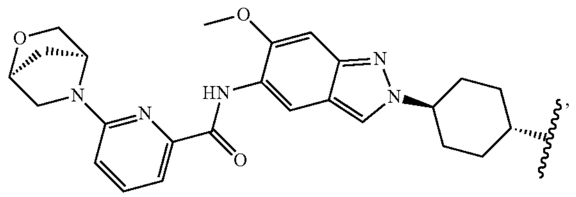 [SMILES: *[C@H]1CC[C@H](n2cc3cc(NC(=O)c4cccc(N5C[C@@H]6C[C@H]5CO6)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

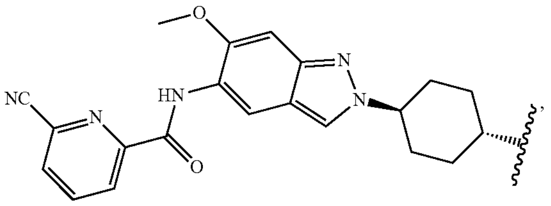 [SMILES: *[C@H]1CC[C@H](n2cc3cc(NC(=O)c4cccc(C#N)n4)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

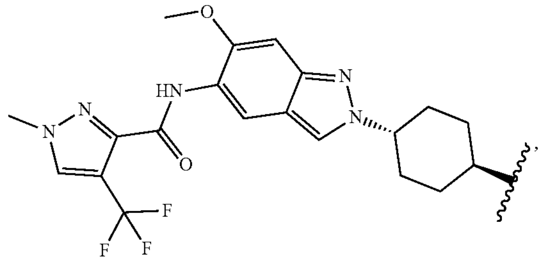 [SMILES: *[C@H]1CC[C@H](n2cc3cc(NC(=O)c4nn(C)cc4C(F)(F)F)c(OC)cc3n2)CC1]

LBM is selected from any of those in Table A below, and L is selected from any of those in Table B below.

In some embodiments, a provided compound or pharmaceutically acceptable salt thereof, is selected from those wherein IRAK is

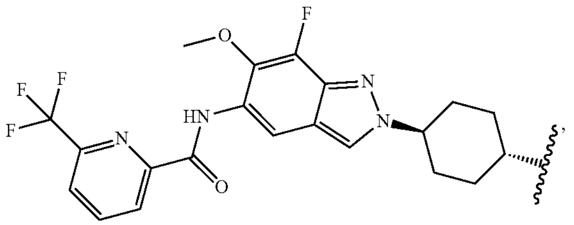 [SMILES: *[C@H]1CC[C@H](n2cc3cc(NC(=O)c4cccc(C(F)(F)F)n4)c(OC)c(F)c3n2)CC1]

LBM is selected from any of those in Table A below, and L is selected from any of those in Table B below.

In some embodiments, a provided compound or pharmaceutically acceptable salt thereof, is selected from those wherein IRAK is

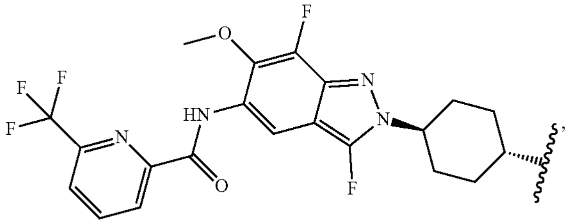 [SMILES: *[C@H]1CC[C@H](n2nc3c(F)c(OC)c(NC(=O)c4cccc(C(F)(F)F)n4)cc3c2F)CC1]

LBM is selected from any of those in Table A below, and L is selected from any of those in Table B below.

In some embodiments, a provided compound or pharmaceutically acceptable salt thereof, is selected from those wherein IRAK is

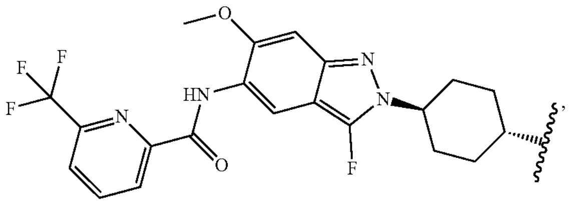 [SMILES: *[C@H]1CC[C@H](n2nc3cc(OC)c(NC(=O)c4cccc(C(F)(F)F)n4)cc3c2F)CC1]

LBM is selected from any of those in Table A below, and L is selected from any of those in Table B below.

In some embodiments, a provided compound or pharmaceutically acceptable salt thereof, is selected from those wherein IRAK is

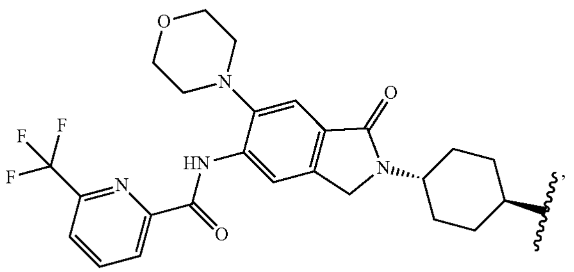 [SMILES: *[C@H]1CC[C@H](N2Cc3cc(NC(=O)c4cccc(C(F)(F)F)n4)c(N4CCOCC4)cc3C2=O)CC1]

LBM is selected from any of those in Table A below, and L is selected from any of those in Table B below.

In some embodiments, a provided compound or pharmaceutically acceptable salt thereof, is selected from those wherein IRAK is

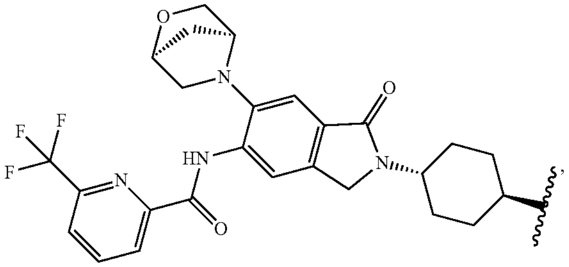 [SMILES: *[C@H]1CC[C@H](N2Cc3cc(NC(=O)c4cccc(C(F)(F)F)n4)c(N4C[C@@H]5C[C@H]4CO5)cc3C2=O)CC1]

LBM is selected from any of those in Table A below, and L is selected from any of those in Table B below.

In some embodiments, a provided compound or pharmaceutically acceptable salt thereof, is selected from those wherein IRAK is

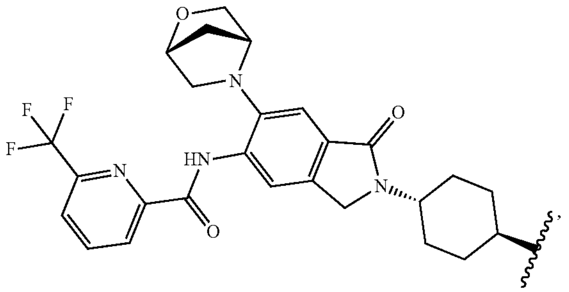 [SMILES: *[C@H]1CC[C@H](N2Cc3cc(NC(=O)c4cccc(C(F)(F)F)n4)c(N4C[C@H]5C[C@@H]4CO5)cc3C2=O)CC1]

LBM is selected from any of those in Table A below, and L is selected from any of those in Table B below.

In some embodiments, a provided compound or pharmaceutically acceptable salt thereof, is selected from those wherein TRAK is

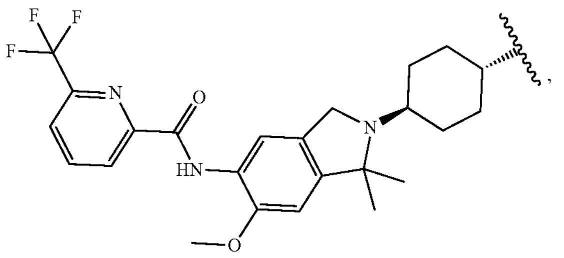 [SMILES: *[C@H]1CC[C@H](N2Cc3cc(NC(=O)c4cccc(C(F)(F)F)n4)c(OC)cc3C2(C)C)CC1]

LBM is selected from any of those in Table A below, and L is selected from any of those in Table B below.

TABLE A
| Exemplified E3 ligases (LBM) |
|---|
| 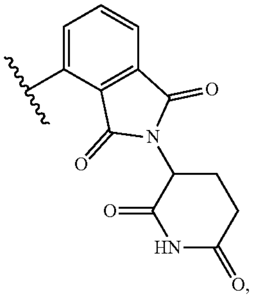 [SMILES: *c1cccc2c1C(=O)N(C1CCC(=O)NC1=O)C2=O] (a) |
| 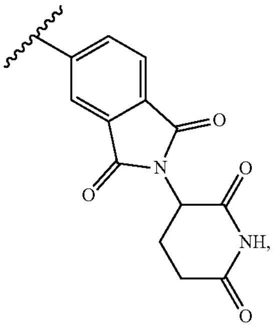 [SMILES: *c1ccc2c(c1)C(=O)N(C1CCC(=O)NC1=O)C2=O] (b) |
| 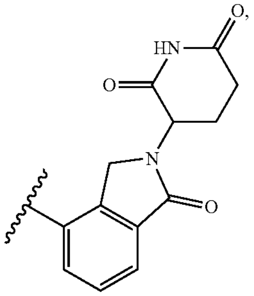 [SMILES: *c1cccc2c1CN(C1CCC(=O)NC1=O)C2=O] (c) |
| 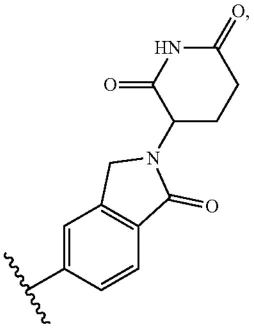 [SMILES: *c1ccc2c(c1)CN(C1CCC(=O)NC1=O)C2=O] (d) |
| 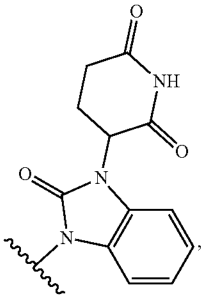 [SMILES: *n1c(=O)n(C2CCC(=O)NC2=O)c2ccccc21] (e) |

TABLE A-continued
| Exemplified E3 ligases (LBM) | |
|---|---|
| 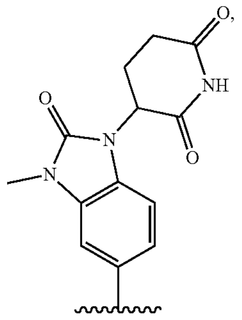 [SMILES: *c1ccc2c(c1)n(C)c(=O)n2C1CCC(=O)NC1=O] | (f) |
| 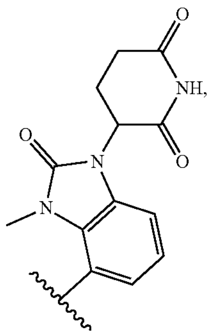 [SMILES: *c1cccc2c1n(C)c(=O)n2C1CCC(=O)NC1=O] | (g) |
| 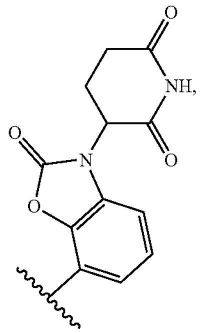 [SMILES: *c1cccc2c1oc(=O)n2C1CCC(=O)NC1=O] | (h) |
| 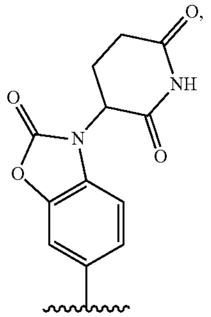 [SMILES: *c1ccc2c(c1)oc(=O)n2C1CCC(=O)NC1=O] | (i) |

TABLE A-continued
| Exemplified E3 ligases (LBM) | |
|---|---|
| 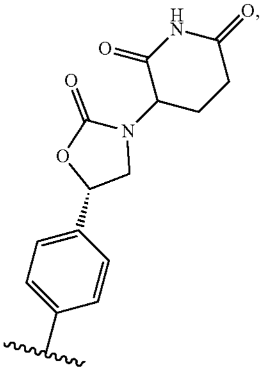 [SMILES: *c1ccc([C@H]2CN(C3CCC(=O)NC3=O)C(=O)O2)cc1] | (j) |
| 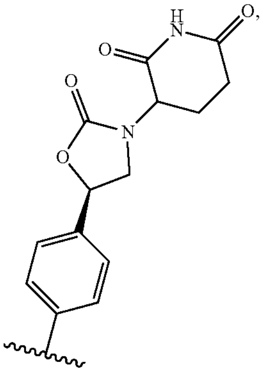 [SMILES: *c1ccc([C@@H]2CN(C3CCC(=O)NC3=O)C(=O)O2)cc1] | (k) |
| 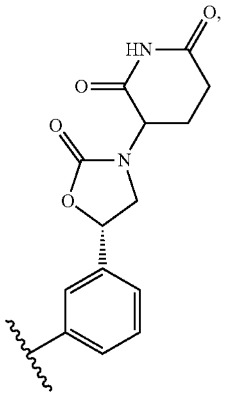 [SMILES: *c1cccc([C@H]2CN(C3CCC(=O)NC3=O)C(=O)O2)c1] | (l) |
| 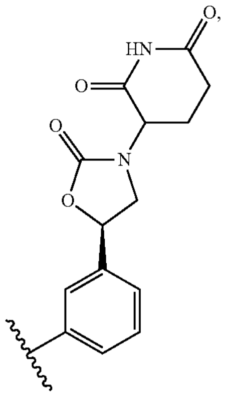 [SMILES: *c1cccc([C@@H]2CN(C3CCC(=O)NC3=O)C(=O)O2)c1] | (m) |

TABLE A-continued
| Exemplified E3 ligases (LBM) |
| --- |
| 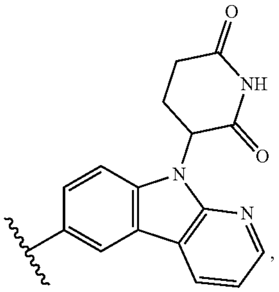 [SMILES: *c1ccc2c(c1)c1cccnc1n2C1CCC(=O)NC1=O] (n) |
| 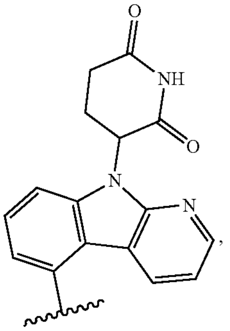 [SMILES: *c1cccc2c1c1cccnc1n2C1CCC(=O)NC1=O] (o) |
| 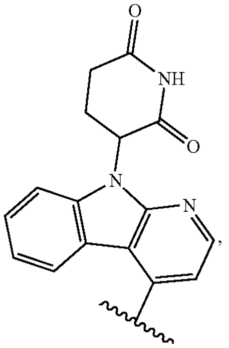 [SMILES: *c1ccnc2c1c1ccccc1n2C1CCC(=O)NC1=O] (p) |
| 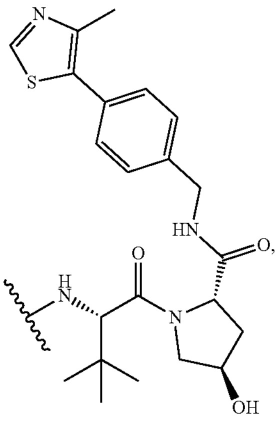 [SMILES: *N[C@H](C(=O)N1C[C@H](O)C[C@H]1C(=O)NCc1ccc(-c2scnc2C)cc1)C(C)(C)C] (q) |

TABLE A-continued
| Exemplified E3 ligases (LBM) |
| --- |
| (r) 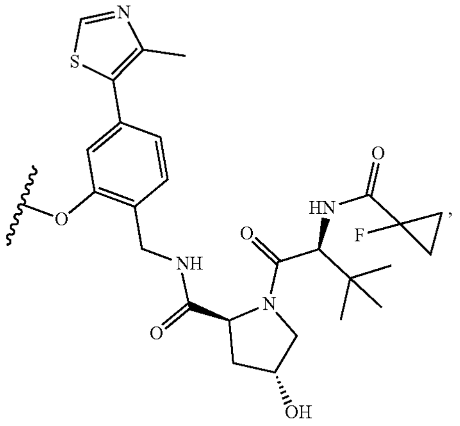 [SMILES: *Oc1cc(-c2scnc2C)ccc1CNC(=O)[C@@H]1C[C@@H](O)CN1C(=O)[C@@H](NC(=O)C1(F)CC1)C(C)(C)C] |
| (s) 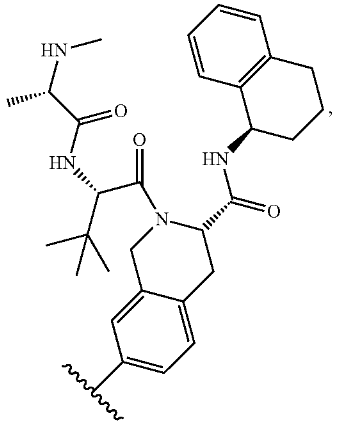 |
| (t) 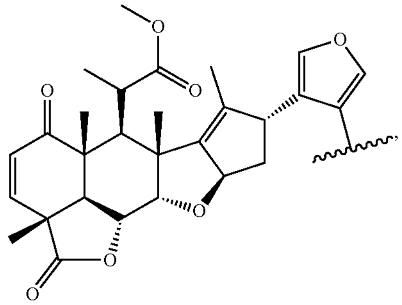 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45] |

TABLE A-continued
| Exemplified E3 ligases (LBM) |
| --- |
| 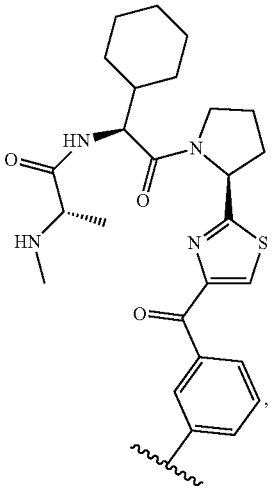 [SMILES: *c1cccc(C(=O)c2csc([C@@H]3CCCN3C(=O)[C@@H](NC(=O)[C@H](C)NC)C3CCCCC3)n2)c1] (u) |
| 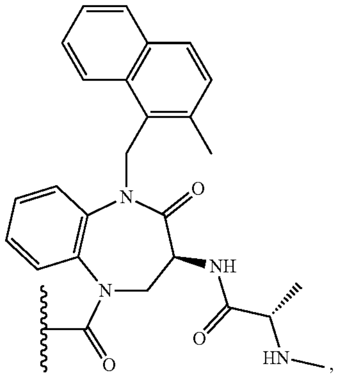 [SMILES: *C(=O)N1C[C@H](NC(=O)[C@H](C)NC)C(=O)N(Cc2c(C)ccc3ccccc23)c2ccccc21] (v) |
| 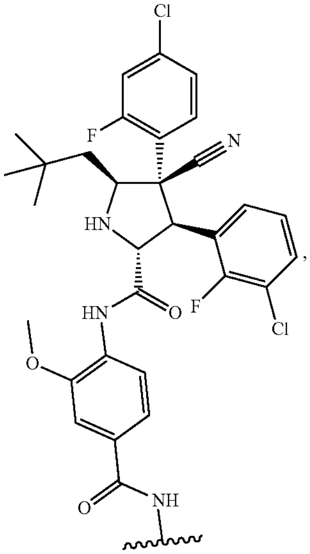 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1] (w) |

TABLE A-continued
| Exemplified E3 ligases (LBM) |
|---|
| 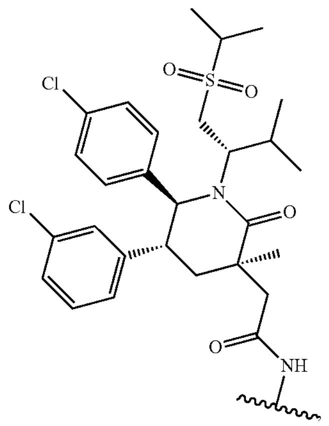 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O] (x) |
| 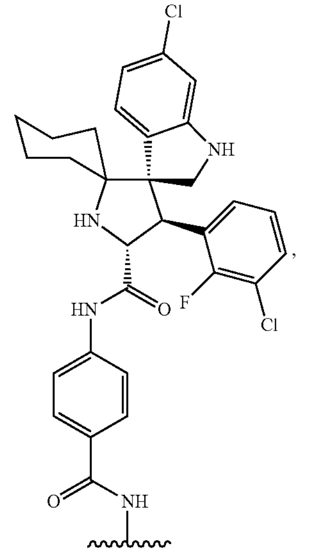 [SMILES: *NC(=O)c1ccc(NC(=O)[C@@H]2NC3(CCCCC3)[C@@]3(CNc4cc(Cl)ccc43)[C@H]2c2cccc(Cl)c2F)cc1] (y) |
| 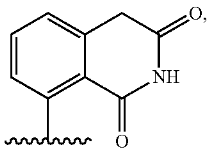 [SMILES: *c1cccc2c1C(=O)NC(=O)C2] (z) |
| 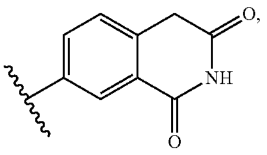 [SMILES: *c1ccc2c(c1)C(=O)NC(=O)C2] (aa) |
| 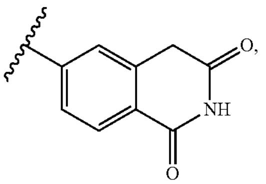 [SMILES: *c1ccc2c(c1)CC(=O)NC2=O] (bb) |

TABLE A-continued
| Exemplified E3 ligases (LBM) | |
|---|---|
| 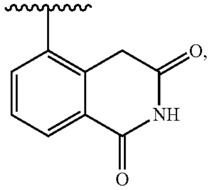 [SMILES: *c1cccc2c1CC(=O)NC2=O] | (cc) |
| 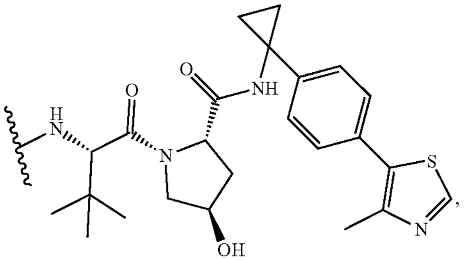 | (dd) |
| 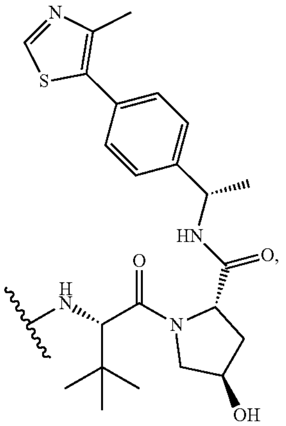 [SMILES: *N[C@H](C(=O)N1C[C@H](O)C[C@H]1C(=O)N[C@@H](C)c1ccc(-c2scnc2C)cc1)C(C)(C)C] | (ee) |
| 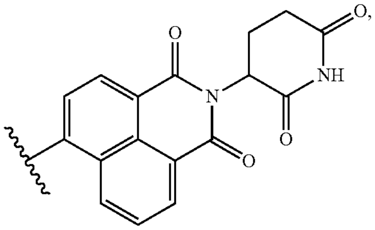 [SMILES: *c1ccc2c3c(cccc13)C(=O)N(C1CCC(=O)NC1=O)C2=O] | (ff) |
| 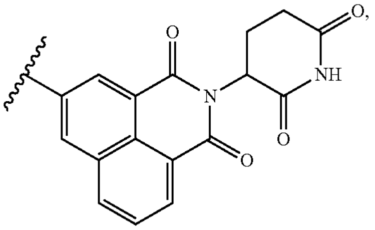 [SMILES: *c1cc2c3c(cccc3c1)C(=O)N(C1CCC(=O)NC1=O)C2=O] | (gg) |
| 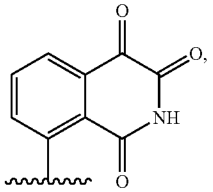 [SMILES: *c1cccc2c1C(=O)NC(=O)C2=O] | (hh) |

TABLE A-continued
| Exemplified E3 ligases (LBM) |
| --- |
| 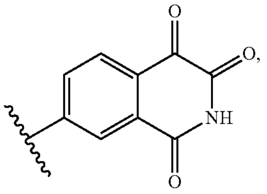 [SMILES: *c1ccc2c(c1)C(=O)NC(=O)C2=O] (ii) |
| 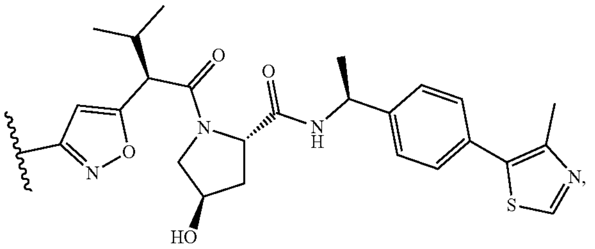 [SMILES: *c1cc([C@H](C(=O)N2C[C@H](O)C[C@H]2C(=O)N[C@@H](C)c2ccc(-c3scnc3C)cc2)C(C)C)on1] (jj) |
| 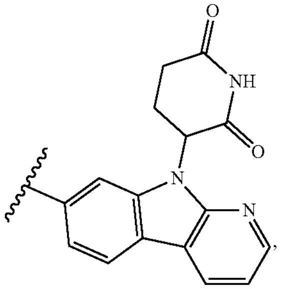 [SMILES: *c1ccc2c3cccnc3n(C3CCC(=O)NC3=O)c2c1] (kk) |
| 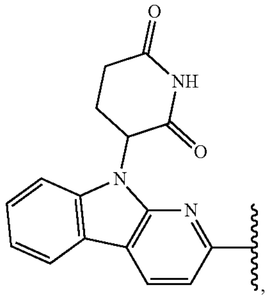 [SMILES: *c1ccc2c3ccccc3n(C3CCC(=O)NC3=O)c2n1] (ll) |
| 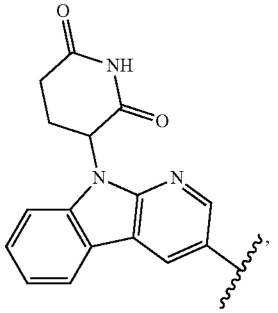 [SMILES: *c1cnc2c(c1)c1ccccc1n2C1CCC(=O)NC1=O] (mm) |

TABLE A-continued
| Exemplified E3 ligases (LBM) | |
|---|---|
| 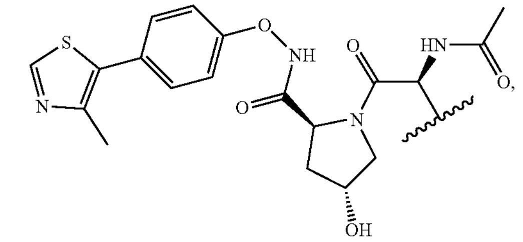 [SMILES: *[C@H](NC(C)=O)C(=O)N1C[C@H](O)C[C@H]1C(=O)NOc1ccc(-c2scnc2C)cc1] | (nn) |
| 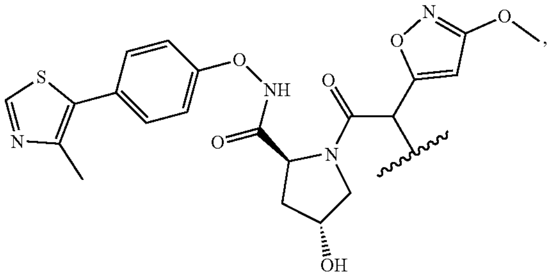 [SMILES: *C(C(=O)N1C[C@H](O)C[C@H]1C(=O)NOc1ccc(-c2scnc2C)cc1)c1cc(OC)no1] | (oo) |
| 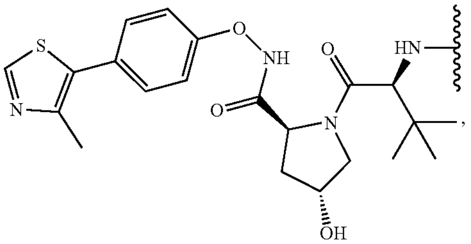 [SMILES: *N[C@H](C(=O)N1C[C@H](O)C[C@H]1C(=O)NOc1ccc(-c2scnc2C)cc1)C(C)(C)C] | (pp) |
| 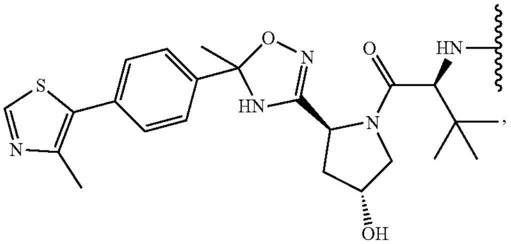 [SMILES: *N[C@H](C(=O)N1C[C@H](O)C[C@H]1C1=NOC(C)(c2ccc(-c3scnc3C)cc2)N1)C(C)(C)C] | (qq) |
| 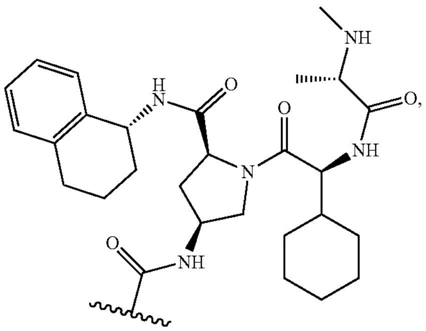 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1] | (rr) |

TABLE A-continued
| Exemplified E3 ligases (LBM) | |
|---|---|
| 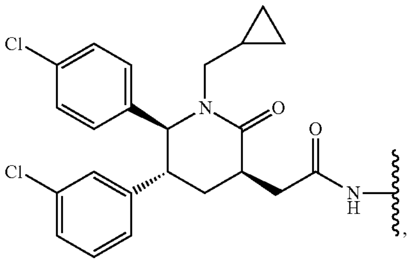 [SMILES: *NC(=O)C[C@H]1C[C@H](c2cccc(Cl)c2)[C@@H](c2ccc(Cl)cc2)N(CC2CC2)C1=O] | (ss) |
| 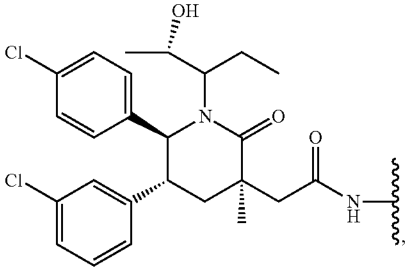 [SMILES: *NC(=O)C[C@@]1(C)C[C@H](c2cccc(Cl)c2)[C@@H](c2ccc(Cl)cc2)N(C(CC)[C@H](C)O)C1=O] | (tt) |
| 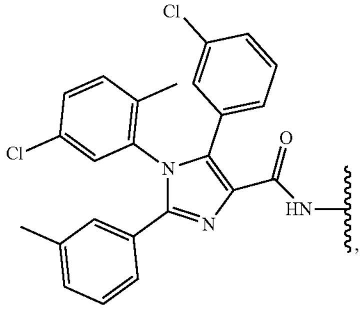 [SMILES: *NC(=O)c1nc(-c2cccc(C)c2)n(-c2cc(Cl)ccc2C)c1-c1cccc(Cl)c1] | (uu) |
| 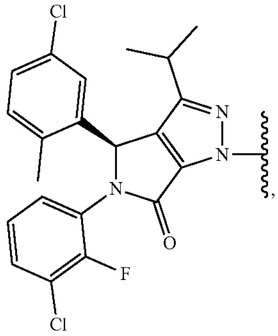 [SMILES: *n1nc(C(C)C)c2c1C(=O)N(c1cccc(Cl)c1F)[C@H]2c1cc(Cl)ccc1C] | (vv) |
| 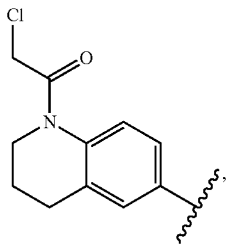 [SMILES: *c1ccc2c(c1)CCCN2C(=O)CCl] | (ww) |

TABLE A-continued
| Exemplified E3 ligases (LBM) |
| --- |
| 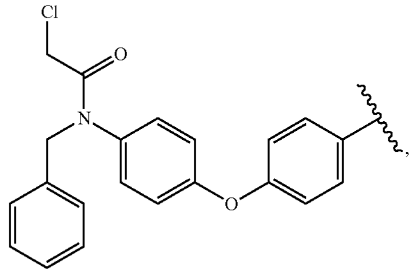 [SMILES: *c1ccc(Oc2ccc(N(Cc3ccccc3)C(=O)CCl)cc2)cc1] (xx) |
| 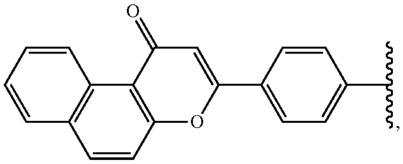 [SMILES: *c1ccc(-c2cc(=O)c3c(ccc4ccccc43)o2)cc1] (yy) |
| 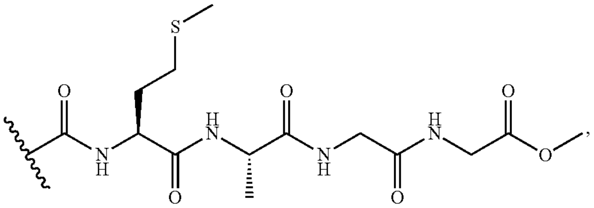 [SMILES: *C(=O)N[C@@H](CCSC)C(=O)N[C@@H](C)C(=O)NCC(=O)NCC(=O)OC] (zz) |
| 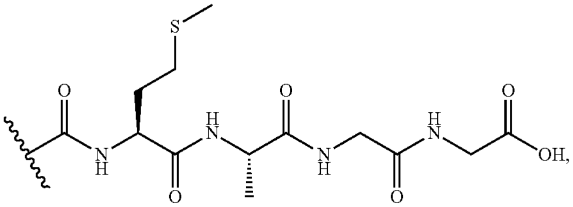 [SMILES: *C(=O)N[C@@H](CCSC)C(=O)N[C@@H](C)C(=O)NCC(=O)NCC(=O)O] (aaa) |
| 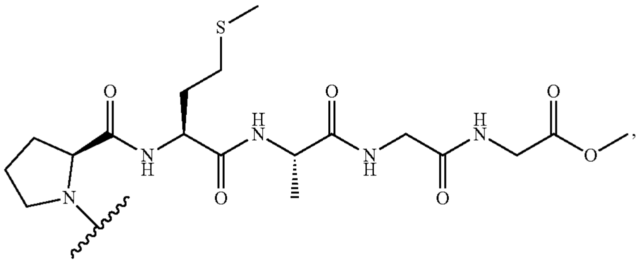 [SMILES: *N1CCC[C@H]1C(=O)N[C@@H](CCSC)C(=O)N[C@@H](C)C(=O)NCC(=O)NCC(=O)OC] (bbb) |
| 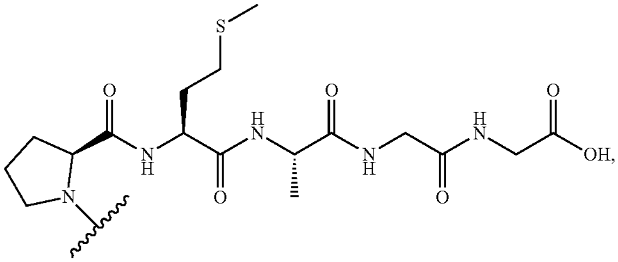 [SMILES: *N1CCC[C@H]1C(=O)N[C@@H](CCSC)C(=O)N[C@@H](C)C(=O)NCC(=O)NCC(=O)O] (ccc) |
| 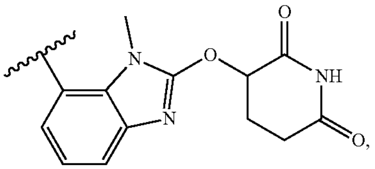 [SMILES: *c1cccc2nc(OC3CCC(=O)NC3=O)n(C)c12] (ddd) |

TABLE A-continued
| Exemplified E3 ligases (LBM) | |
|---|---|
| 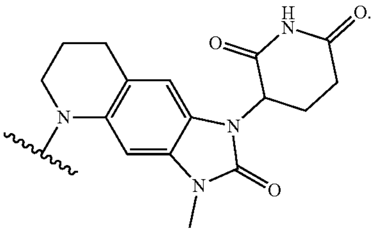 [SMILES: *N1CCCc2cc3c(cc21)n(C)c(=O)n3C1CCC(=O)NC1=O] | (eee) |
TABLE B
| Exemplified Linkers (L) | |
|---|---|
| 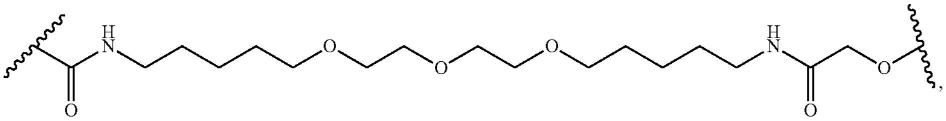 [SMILES: *OCC(=O)NCCCCCOCCOCCOCCCCCNC(*)=O] | (1) |
| 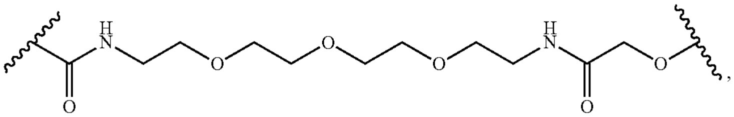 [SMILES: *OCC(=O)NCCOCCOCCOCCNC(*)=O] | (2) |
| 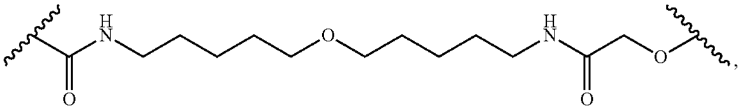 | (3) |
| 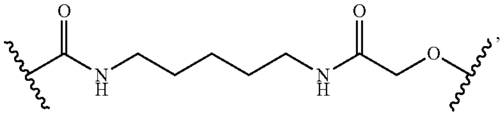 [SMILES: *OCC(=O)NCCCCCNC(*)=O] | (4) |
| 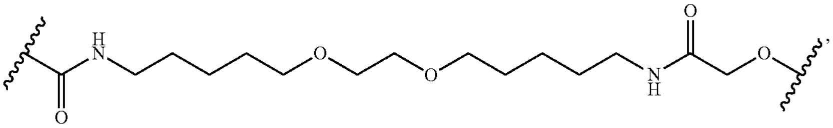 [SMILES: *OCC(=O)NCCCCCOCCOCCCCCNC(*)=O] | (5) |
| 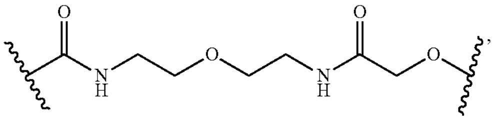 [SMILES: *OCC(=O)NCCOCCNC(*)=O] | (6) |
| 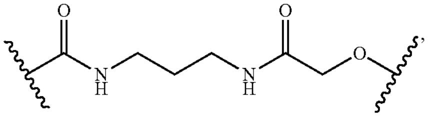 [SMILES: *OCC(=O)NCCCNC(*)=O] | (7) |
| 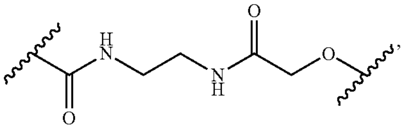 [SMILES: *OCC(=O)NCCNC(*)=O] | (8) |
| 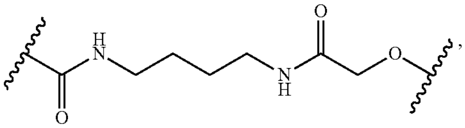 [SMILES: *OCC(=O)NCCCCNC(*)=O] | (9) |

TABLE B-continued
Exemplified Linkers (L)
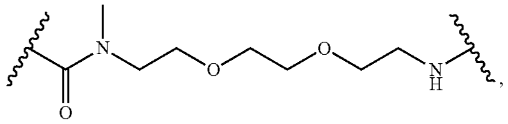 [SMILES: *NCCOCCOCCN(C)C(*)=O]
(10)
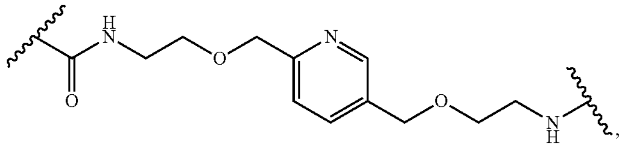 [SMILES: *NCCOCc1ccc(COCCNC(*)=O)nc1]
(11)
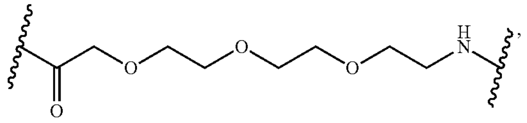 [SMILES: *NCCOCCOCCOCC(*)=O]
(12)
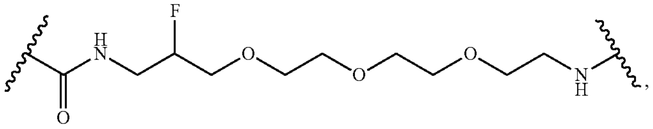 [SMILES: *NCCOCCOCCOCC(F)CNC(*)=O]
(13)
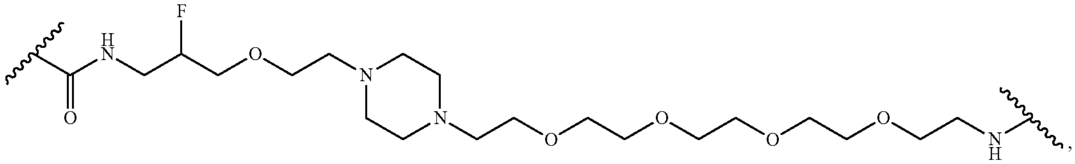 [SMILES: *NCCOCCOCCOCCOCCN1CCN(CCOCC(F)CNC(*)=O)CC1]
(14)
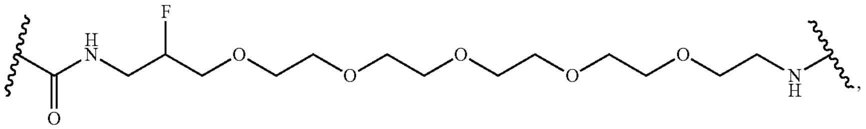 [SMILES: *NCCOCCOCCOCCOCCOCC(F)CNC(*)=O]
(15)
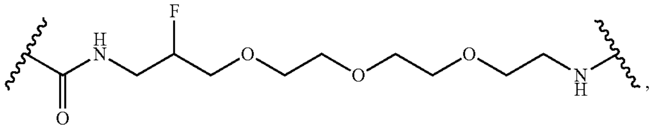 [SMILES: *NCCOCCOCCOCC(F)CNC(*)=O]
(16)
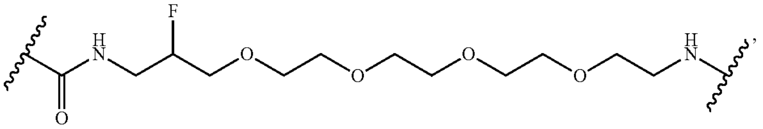 [SMILES: *NCCOCCOCCOCCOCC(F)CNC(*)=O]
(17)
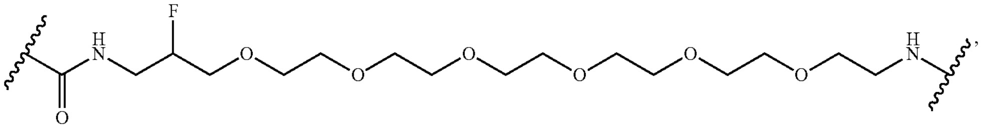 [SMILES: *NCCOCCOCCOCCOCCOCCOCC(F)CNC(*)=O]
(18)
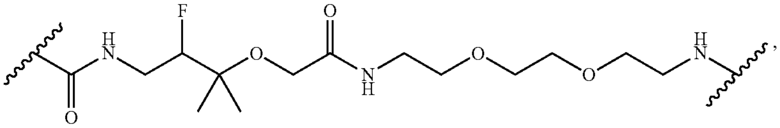 [SMILES: *NCCOCCOCCNC(=O)COC(C)(C)C(F)CNC(*)=O]
(19)

TABLE B-continued
| Exemplified Linkers (L) |
|---|
| 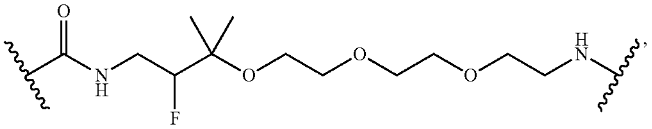 [SMILES: *NCCOCCOCCOC(C)(C)C(F)CNC(*)=O] (20) |
| 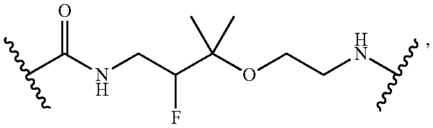 [SMILES: *NCCOC(C)(C)C(F)CNC(*)=O] (21) |
| 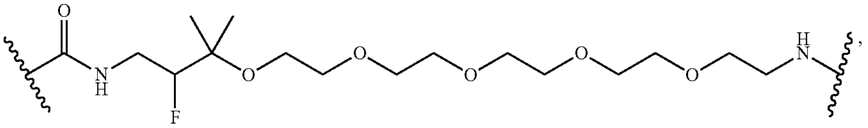 [SMILES: *NCCOCCOCCOCCOCCOC(C)(C)C(F)CNC(*)=O] (22) |
| 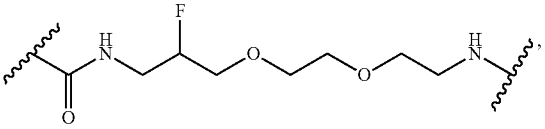 [SMILES: *NCCOCCOCC(F)CNC(*)=O] (23) |
| 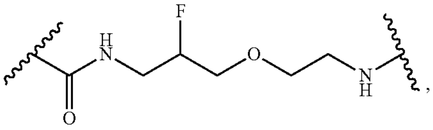 [SMILES: *NCCOCC(F)CNC(*)=O] (24) |
| 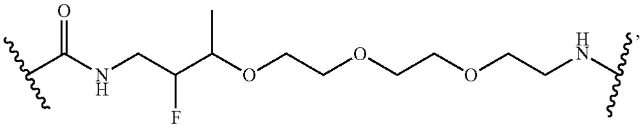 [SMILES: *NCCOCCOCCOC(C)C(F)CNC(*)=O] (25) |
| 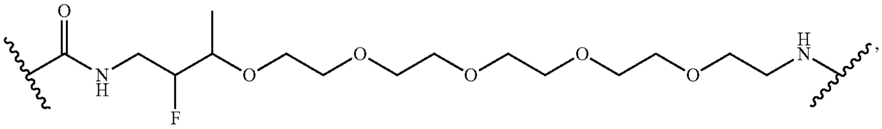 [SMILES: *NCCOCCOCCOCCOCCOC(C)C(F)CNC(*)=O] (26) |
| 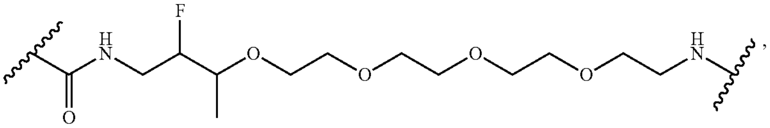 [SMILES: *NCCOCCOCCOCCOC(C)C(F)CNC(*)=O] (27) |
| 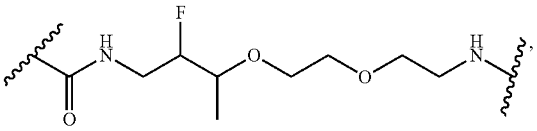 [SMILES: *NCCOCCOC(C)C(F)CNC(*)=O] (28) |
| 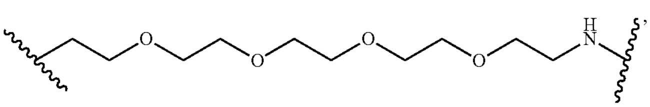 [SMILES: *CCOCCOCCOCCOCCN*] (29) |
| 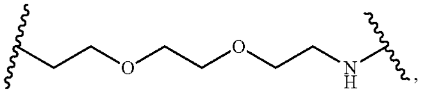 [SMILES: *CCOCCOCCN*] (30) |

TABLE B-continued
Exemplified Linkers (L)
(31)
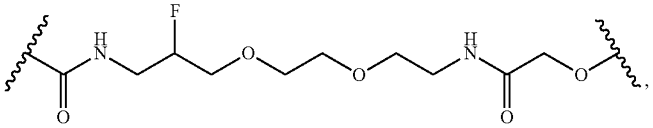 [SMILES: *OCC(=O)NCCOCCOCC(F)CNC(*)=O]
(32)
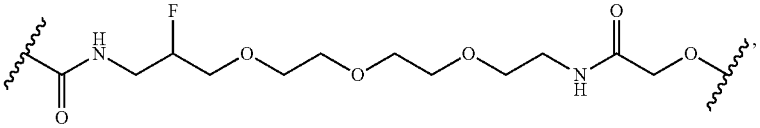 [SMILES: *OCC(=O)NCCOCCOCCOCC(F)CNC(*)=O]
(33)
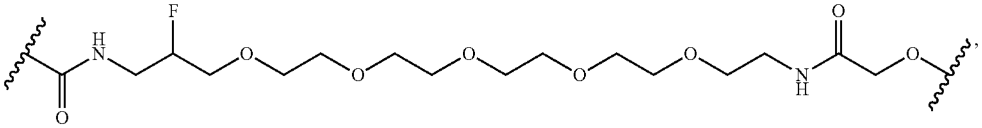 [SMILES: *OCC(=O)NCCOCCOCCOCCOCCOCC(F)CNC(*)=O]
(34)
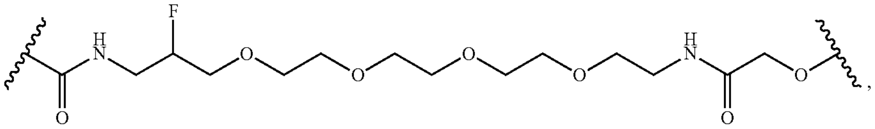 [SMILES: *OCC(=O)NCCOCCOCCOCCOCC(F)CNC(*)=O]
(35)
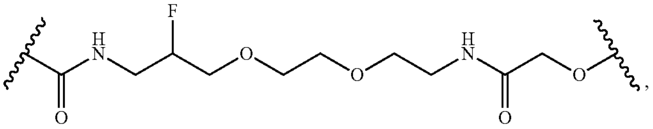 [SMILES: *OCC(=O)NCCOCCOCC(F)CNC(*)=O]
(36)
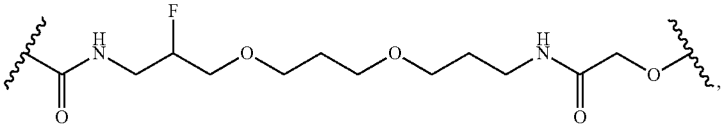 [SMILES: *OCC(=O)NCCCOCCCOCC(F)CNC(*)=O]
(37)
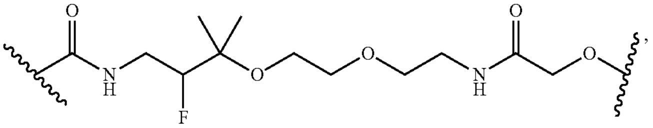 [SMILES: *OCC(=O)NCCOCCOC(C)(C)C(F)CNC(*)=O]
(38)
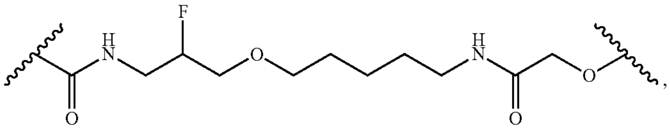 [SMILES: *OCC(=O)NCCCCCOCC(F)CNC(*)=O]
(39)
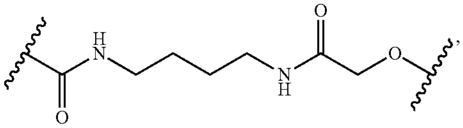 [SMILES: *OCC(=O)NCCCCNC(*)=O]
(40)
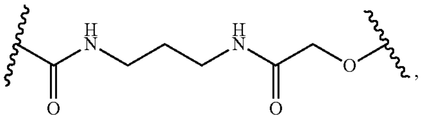 [SMILES: *OCC(=O)NCCCNC(*)=O]
(41)
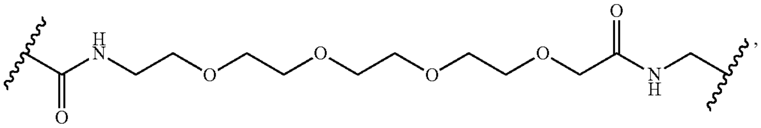 [SMILES: *CNC(=O)COCCOCCOCCOCCNC(*)=O]

TABLE B-continued
| Exemplified Linkers (L) |
|---|
| 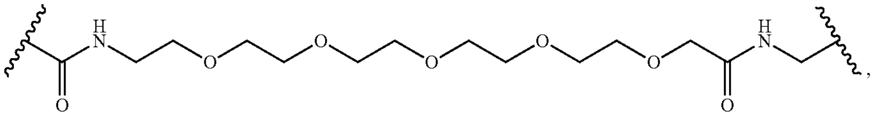 [SMILES: *CNC(=O)COCCOCCOCCOCCOCCNC(*)=O] (42) |
| 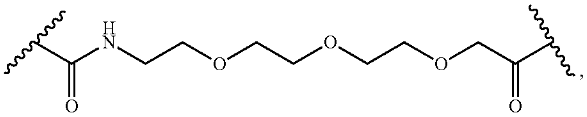 [SMILES: *C(=O)COCCOCCOCCNC(*)=O] (43) |
| 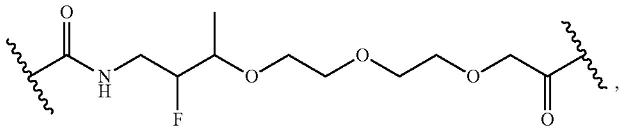 [SMILES: *C(=O)COCCOCCOC(C)C(F)CNC(*)=O] (44) |
| 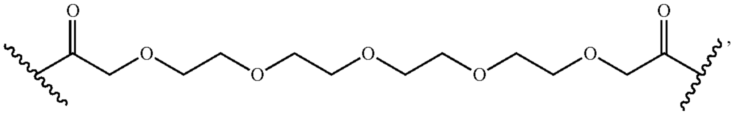 [SMILES: *C(=O)COCCOCCOCCOCCOCC(*)=O] (45) |
| 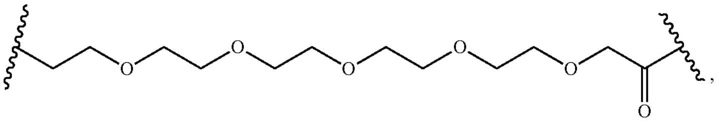 [SMILES: *CCOCCOCCOCCOCCOCC(*)=O] (46) |
| 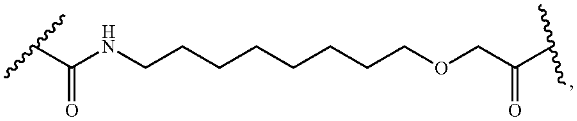 [SMILES: *C(=O)COCCCCCCCCNC(*)=O] (47) |
| 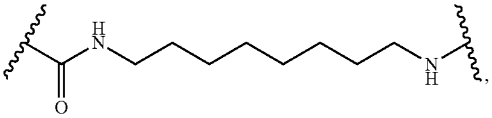 [SMILES: *NCCCCCCCCNC(*)=O] (49) |
| 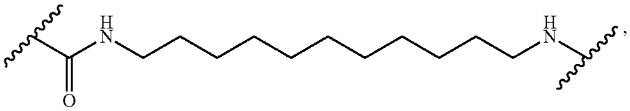 [SMILES: *NCCCCCCCCCCCNC(*)=O] (50) |
| 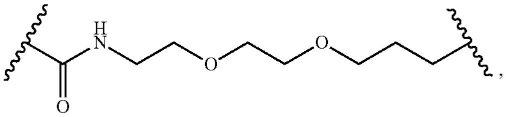 [SMILES: *CCCOCCOCCNC(*)=O] (51) |
| 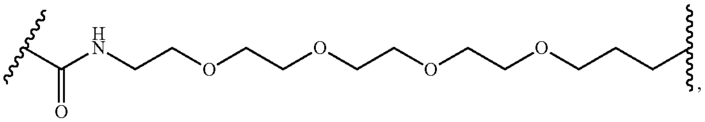 [SMILES: *CCCOCCOCCOCCOCCNC(*)=O] (52) |
| 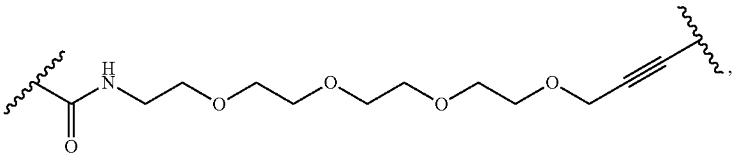 [SMILES: *C#CCOCCOCCOCCOCCNC(*)=O] (53) |

TABLE B-continued
Exemplified Linkers (L)
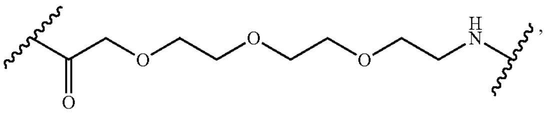 [SMILES: *NCCOCCOCCOCC(*)=O]
(54)
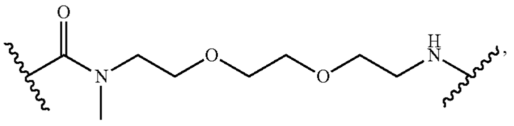 [SMILES: *NCCOCCOCCN(C)C(*)=O]
(55)
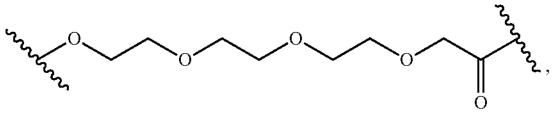 [SMILES: *OCCOCCOCCOCC(*)=O]
(56)
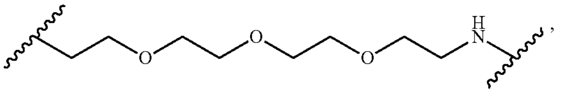 [SMILES: *CCOCCOCCOCCN*]
(57)
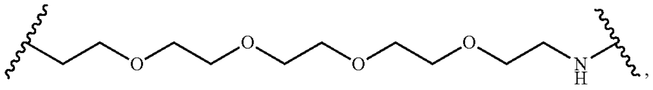 [SMILES: *CCOCCOCCOCCOCCN*]
(58)
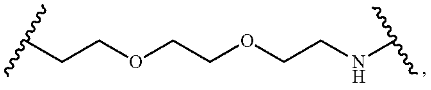 [SMILES: *CCOCCOCCN*]
(59)
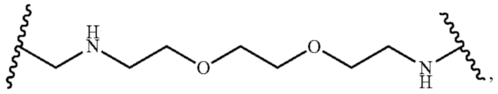 [SMILES: *CNCCOCCOCCN*]
(60)
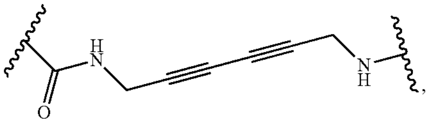 [SMILES: *NCC#CC#CCNC(*)=O]
(61)
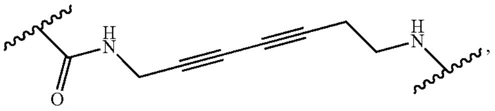 [SMILES: *NCCC#CC#CCNC(*)=O]
(62)
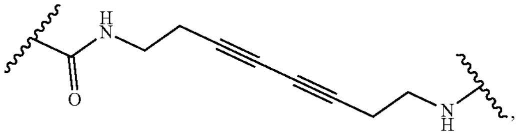 [SMILES: *NCCC#CC#CCCNC(*)=O]
(63)
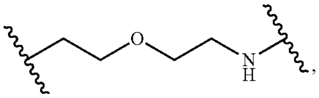 [SMILES: *CCOCCN*]
(64)
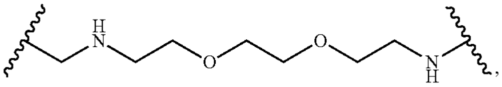
(65)
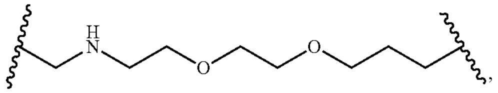 [SMILES: *CCCOCCOCCNC*]
(66)

TABLE B-continued
| Exemplified Linkers (L) | |
|---|---|
| 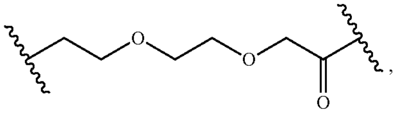 [SMILES: *CCOCCOCC(*)=O] | (67) |
| 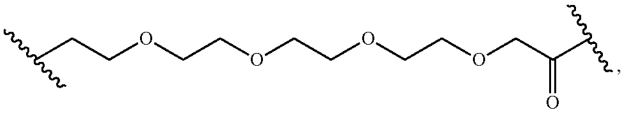 [SMILES: *CCOCCOCCOCCOCC(*)=O] | (68) |
| 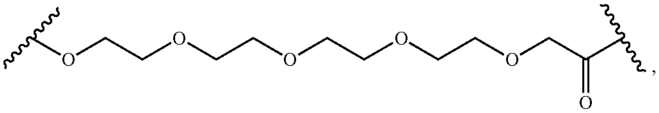 [SMILES: *OCCOCCOCCOCCOCC(*)=O] | (69) |
| 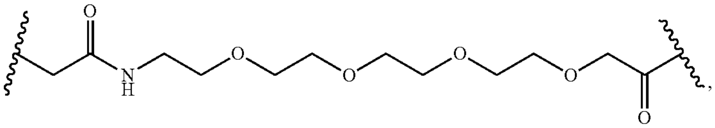 [SMILES: *CC(=O)NCCOCCOCCOCCOCC(*)=O] | (70) |
| 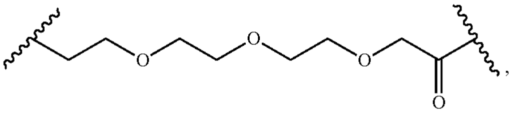 [SMILES: *CCOCCOCCOCC(*)=O] | (71) |
| 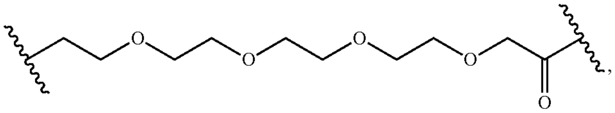 [SMILES: *CCOCCOCCOCCOCC(*)=O] | (72) |
| 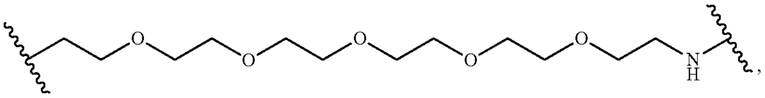 [SMILES: *CCOCCOCCOCCOCCOCCN*] | (73) |
| 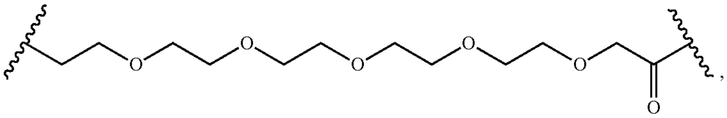 [SMILES: *CCOCCOCCOCCOCCOCC(*)=O] | (74) |
| 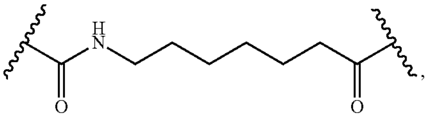 [SMILES: *C(=O)CCCCCCNC(*)=O] | (75) |
| 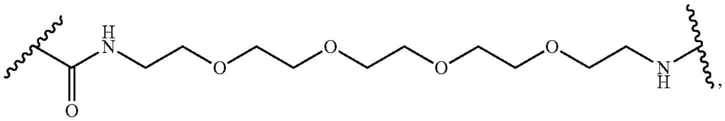 [SMILES: *NCCOCCOCCOCCOCCNC(*)=O] | (76) |
| 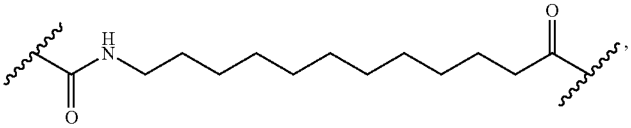 [SMILES: *C(=O)CCCCCCCCCCCNC(*)=O] | (77) |
| 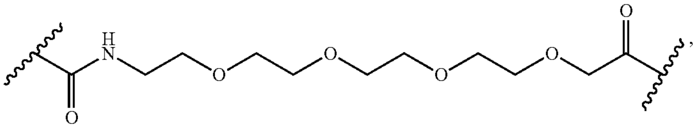 [SMILES: *C(=O)COCCOCCOCCOCCNC(*)=O] | (78) |

TABLE B-continued
| Exemplified Linkers (L) | |
|---|---|
| 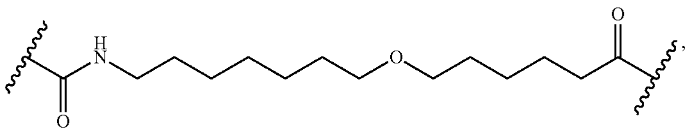 [SMILES: *C(=O)CCCCCOCCCCCCCNC(*)=O] | (79) |
| 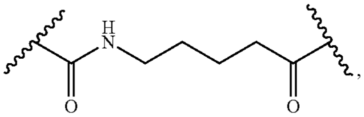 [SMILES: *C(=O)CCCCNC(*)=O] | (80) |
| 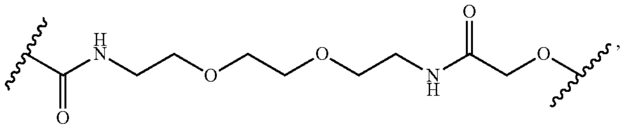 [SMILES: *OCC(=O)NCCOCCOCCNC(*)=O] | (81) |
| 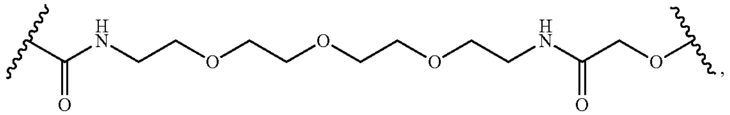 [SMILES: *OCC(=O)NCCOCCOCCOCCNC(*)=O] | (82) |
| 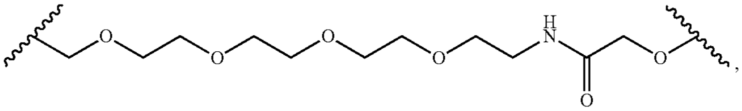 [SMILES: *COCCOCCOCCOCCNC(=O)CO*] | (83) |
| 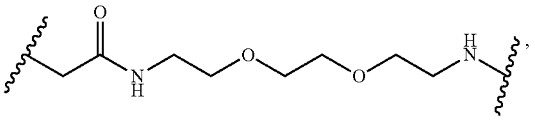 [SMILES: *CC(=O)NCCOCCOCCN*] | (84) |
| 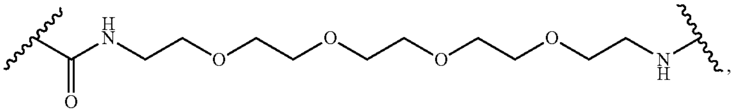 [SMILES: *NCCOCCOCCOCCOCCNC(*)=O] | (85) |
| 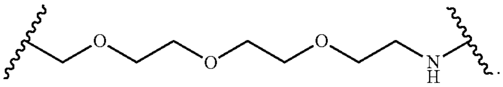 [SMILES: *COCCOCCOCCN*] | (86) |
| 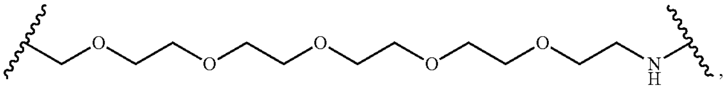 [SMILES: *COCCOCCOCCOCCOCCN*] | (87) |
| 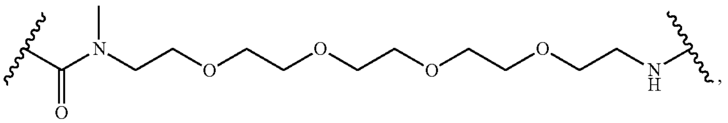 [SMILES: *NCCOCCOCCOCCOCCN(C)C(*)=O] | (88) |
| 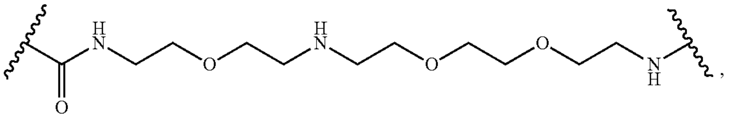 [SMILES: *NCCOCCOCCNCCOCCNC(*)=O] | (89) |
| 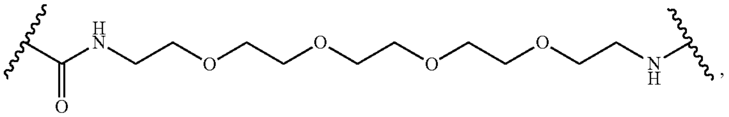 [SMILES: *NCCOCCOCCOCCOCCNC(*)=O] | (90) |

TABLE B-continued
Exemplified Linkers (L)
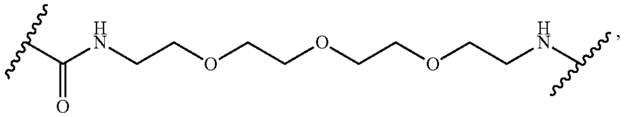 [SMILES: *NCCOCCOCCOCCNC(*)=O]
(91)
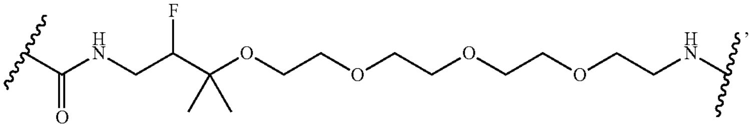 [SMILES: *NCCOCCOCCOCCOC(C)(C)C(F)CNC(*)=O]
(92)
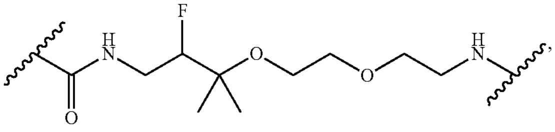 [SMILES: *NCCOCCOC(C)(C)C(F)CNC(*)=O]
(93)
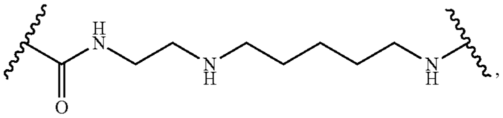 [SMILES: *NCCCCCNCCNC(*)=O]
(94)
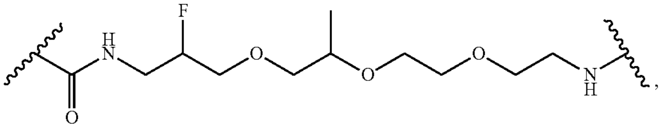 [SMILES: *NCCOCCOC(C)COCC(F)CNC(*)=O]
(95)
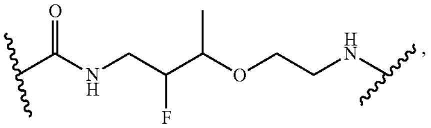 [SMILES: *NCCOC(C)C(F)CNC(*)=O]
(96)
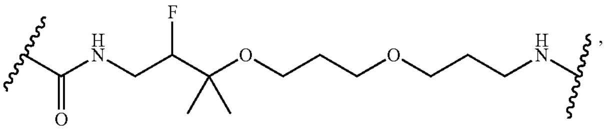 [SMILES: *NCCCOCCCOC(C)(C)C(F)CNC(*)=O]
(97)
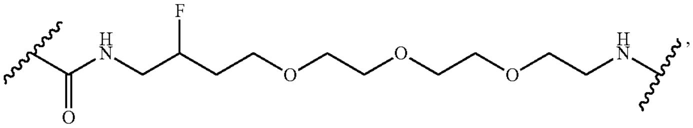 [SMILES: *NCCOCCOCCOCCC(F)CNC(*)=O]
(98)
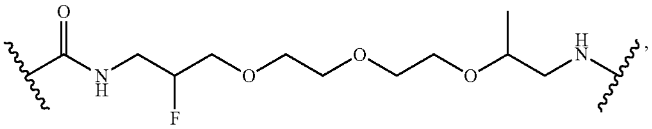 [SMILES: *NCC(C)OCCOCCOCC(F)CNC(*)=O]
(99)
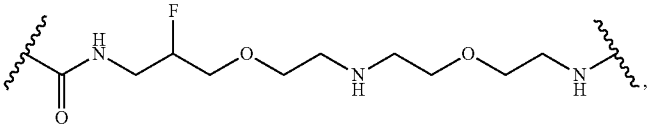 [SMILES: *NCCOCCNCCOCC(F)CNC(*)=O]
(100)
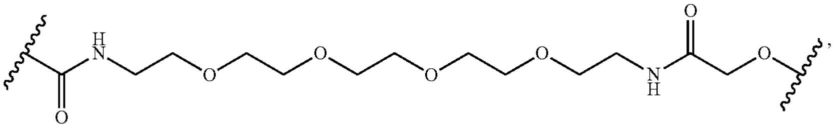 [SMILES: *OCC(=O)NCCOCCOCCOCCOCCNC(*)=O]
(101)

TABLE B-continued
Exemplified Linkers (L)
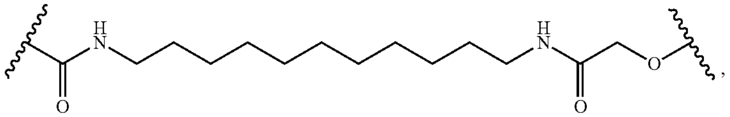 [SMILES: *OCC(=O)NCCCCCCCCCCCNC(*)=O]
(102)
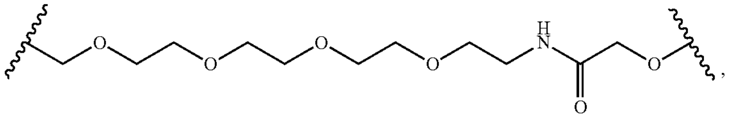 [SMILES: *COCCOCCOCCOCCNC(=O)CO*]
(103)
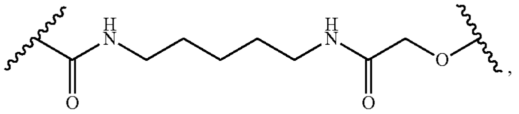 [SMILES: *OCC(=O)NCCCCCNC(*)=O]
(104)
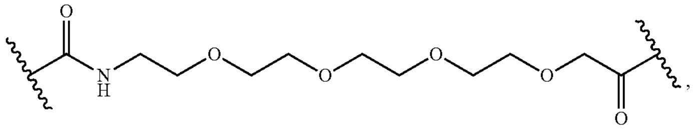 [SMILES: *C(=O)COCCOCCOCCOCCNC(*)=O]
(105)
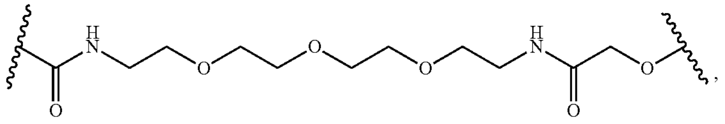 [SMILES: *OCC(=O)NCCOCCOCCOCCNC(*)=O]
(106)
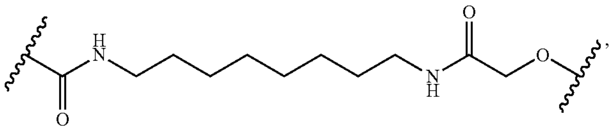 [SMILES: *OCC(=O)NCCCCCCCCNC(*)=O]
(107)
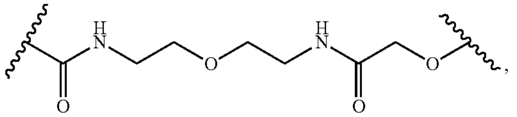 [SMILES: *OCC(=O)NCCOCCNC(*)=O]
(108)
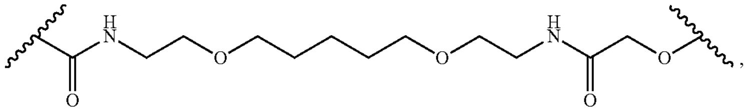 [SMILES: *OCC(=O)NCCOCCCCCOCCNC(*)=O]
(109)
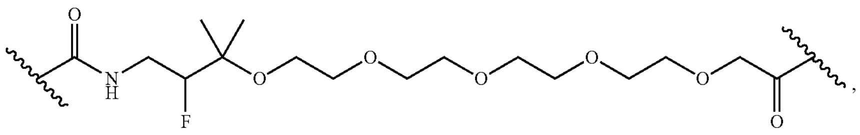 [SMILES: *C(=O)COCCOCCOCCOCCOC(C)(C)C(F)CNC(*)=O]
(110)
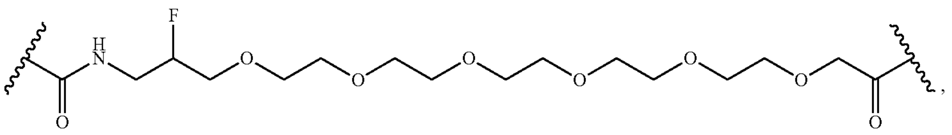 [SMILES: *C(=O)COCCOCCOCCOCCOCCOCC(F)CNC(*)=O]
(111)
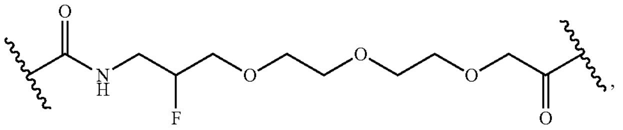 [SMILES: *C(=O)COCCOCCOCC(F)CNC(*)=O]
(112)

TABLE B-continued
Exemplified Linkers (L)
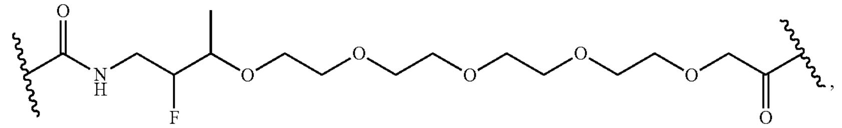 [SMILES: *C(=O)COCCOCCOCCOCCOC(C)C(F)CNC(*)=O]
(113)
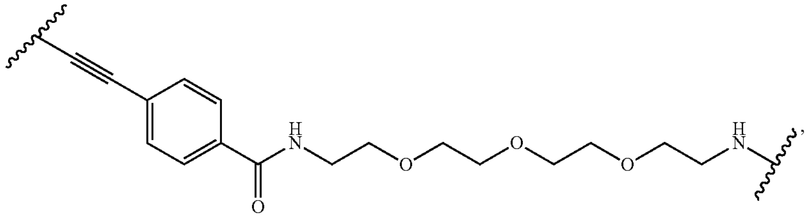 [SMILES: *C#Cc1ccc(C(=O)NCCOCCOCCOCCN*)cc1]
(114)
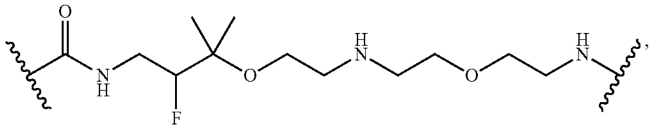 [SMILES: *NCCOCCNCCOC(C)(C)C(F)CNC(*)=O]
(115)
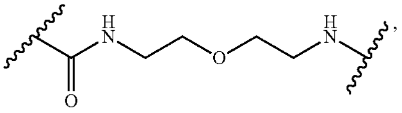 [SMILES: *NCCOCCNC(*)=O]
(116)
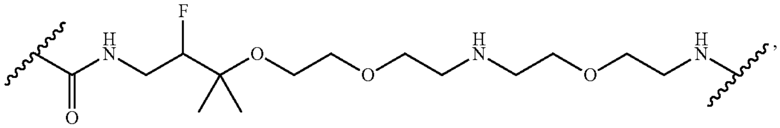 [SMILES: *NCCOCCNCCOCCOC(C)(C)C(F)CNC(*)=O]
(117)
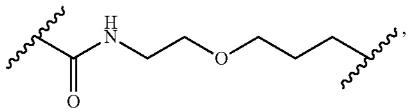 [SMILES: *CCCOCCNC(*)=O]
(118)
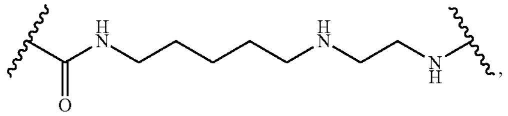 [SMILES: *NCCNCCCCCNC(*)=O]
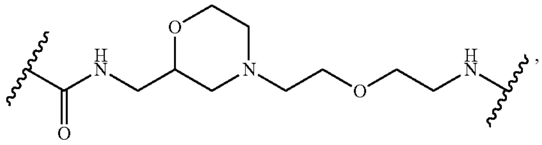 [SMILES: *NCCOCCN1CCOC(CNC(*)=O)C1]
(119)
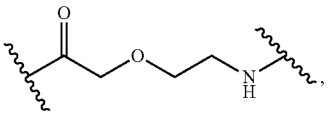 [SMILES: *NCCOCC(*)=O]
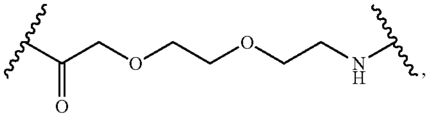 [SMILES: *NCCOCCOCC(*)=O]
(120)
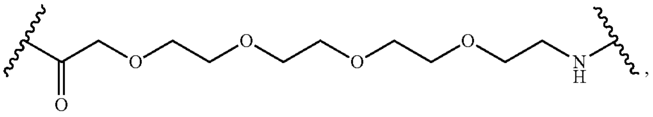 [SMILES: *NCCOCCOCCOCCOCC(*)=O]
(121)

TABLE B-continued
| Exemplified Linkers (L) |
|---|
(122)
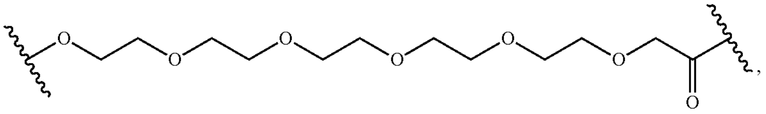 [SMILES: *OCCOCCOCCOCCOCCOCC(*)=O]
(123)
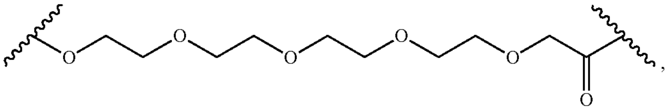 [SMILES: *OCCOCCOCCOCCOCC(*)=O]
(124)
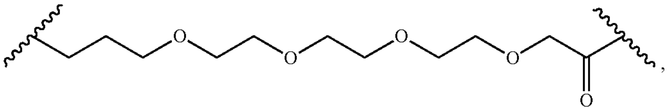 [SMILES: *CCCOCCOCCOCCOCC(*)=O]
(125)
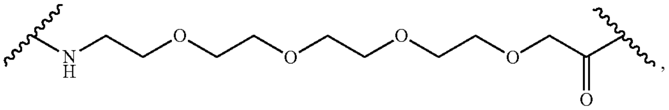 [SMILES: *NCCOCCOCCOCCOCC(*)=O]
(126)
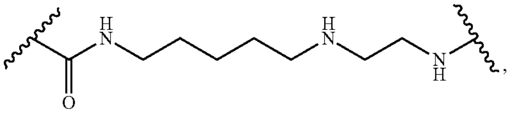 [SMILES: *NCCNCCCCCNC(*)=O]
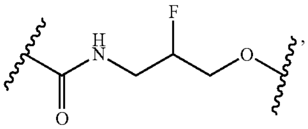 [SMILES: *OCC(F)CNC(*)=O]
(127)
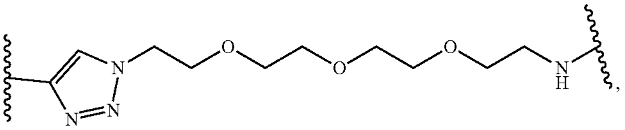 [SMILES: *NCCOCCOCCOCCn1cc(*)nn1]
(128)
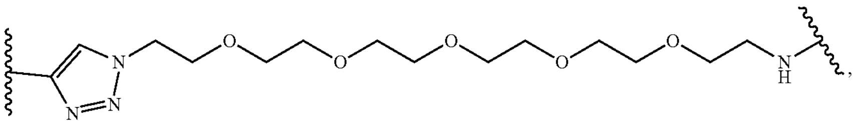 [SMILES: *NCCOCCOCCOCCOCCOCCn1cc(*)nn1]
(129)
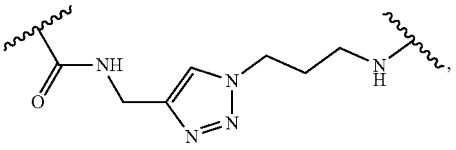 [SMILES: *NCCCn1cc(CNC(*)=O)nn1]
(130)
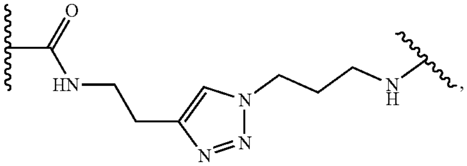 [SMILES: *NCCCn1cc(CCNC(*)=O)nn1]
(131)
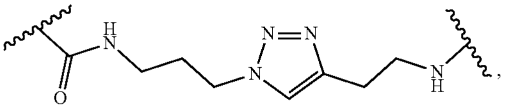 [SMILES: *NCCc1cn(CCCNC(*)=O)nn1]

TABLE B-continued
| Exemplified Linkers (L) |
|---|
| 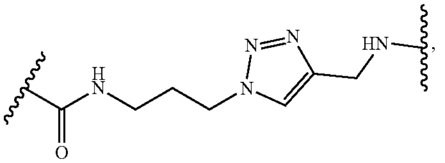 [SMILES: *NCc1cn(CCCNC(*)=O)nn1] (132) |
| 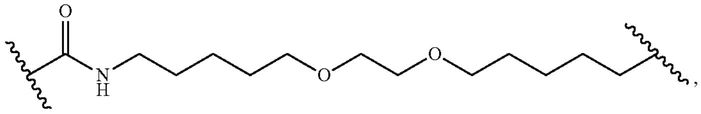 [SMILES: *CCCCCOCCOCCCCCNC(*)=O] (133) |
| 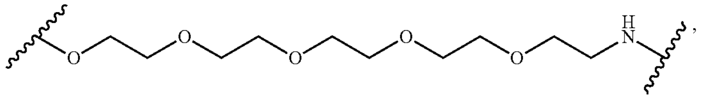 [SMILES: *NCCOCCOCCOCCOCCO*] (134) |
| 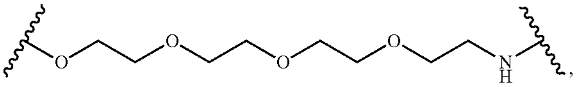 [SMILES: *NCCOCCOCCOCCO*] (135) |
| 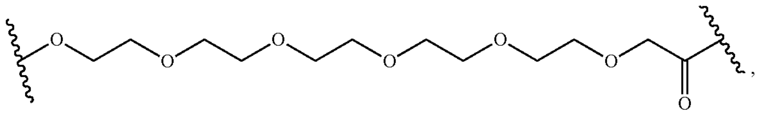 [SMILES: *OCCOCCOCCOCCOCCOCC(*)=O] (136) |
| 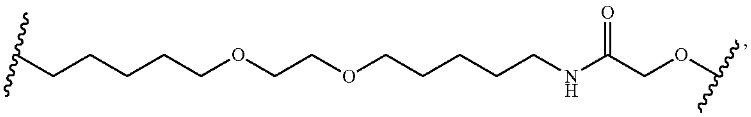 [SMILES: *CCCCCOCCOCCCCCNC(=O)CO*] (137) |
| 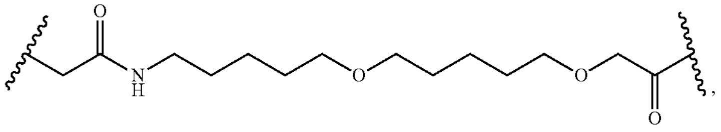 [SMILES: *CC(=O)NCCCCCOCCCCCOCC(*)=O] (138) |
| 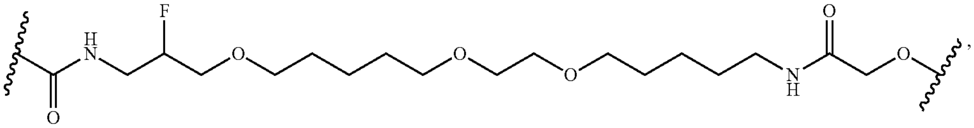 [SMILES: *OCC(=O)NCCCCCOCCOCCCCCOCC(F)CNC(*)=O] (139) |
| 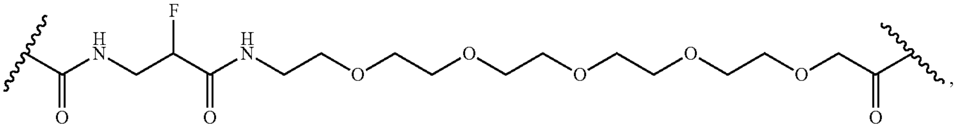 [SMILES: *C(=O)COCCOCCOCCOCCOCCNC(=O)C(F)CNC(*)=O] (140) |
| 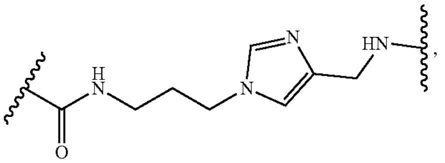 [SMILES: *NCc1cn(CCCNC(*)=O)cn1] (141) |
| 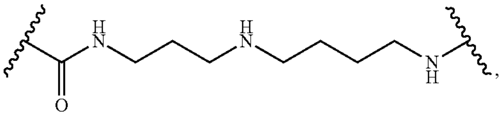 [SMILES: *NCCCCNCCCNC(*)=O] (142) |

TABLE B-continued
Exemplified Linkers (L)
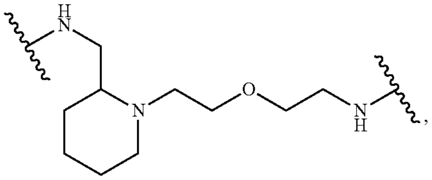 [SMILES: *NCCOCCN1CCCCC1CN*]
(143)
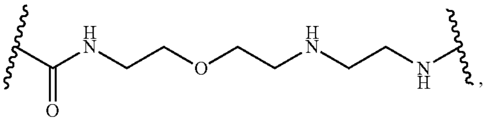 [SMILES: *NCCNCCOCCNC(*)=O]
(144)
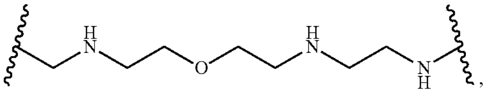 [SMILES: *CNCCOCCNCCN*]
(145)
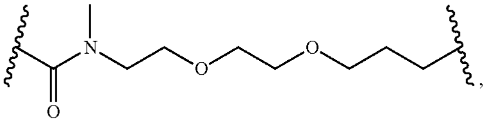 [SMILES: *CCCOCCOCCN(C)C(*)=O]
(146)
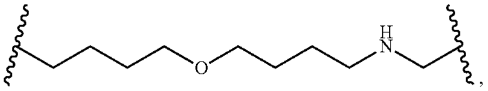 [SMILES: *CCCCOCCCCNC*]
(147)
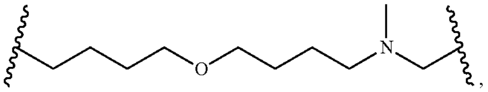 [SMILES: *CCCCOCCCCN(C)C*]
(148)
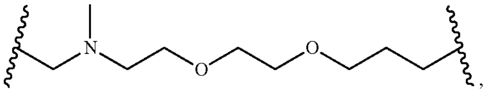 [SMILES: *CCCOCCOCCN(C)C*]
(149)
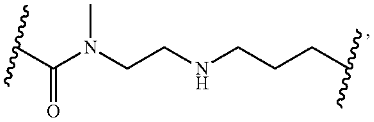 [SMILES: *CCCNCCN(C)C(*)=O]
(150)
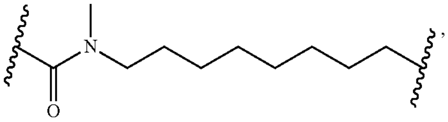 [SMILES: *CCCCCCCCN(C)C(*)=O]
(151)
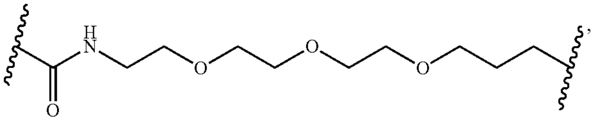 [SMILES: *CCCOCCOCCOCCNC(*)=O]
(152)
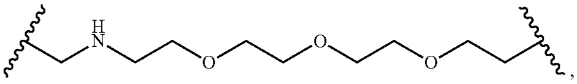 [SMILES: *CCOCCOCCOCCNC*]
(153)
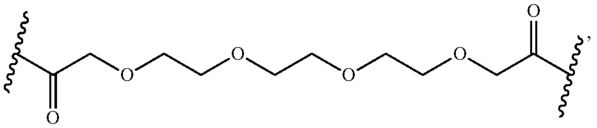 [SMILES: *C(=O)COCCOCCOCCOCC(*)=O]
(154)

TABLE B-continued
Exemplified Linkers (L)
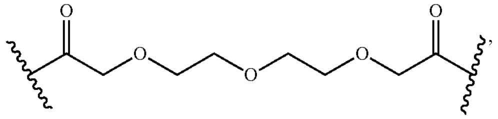 [SMILES: *C(=O)COCCOCCOCC(*)=O]
(155)
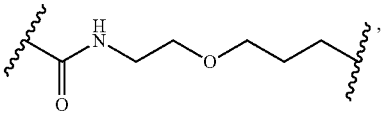 [SMILES: *CCCOCCNC(*)=O]
(156)
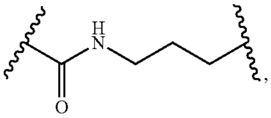 [SMILES: *CCCNC(*)=O]
(157)
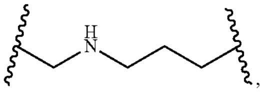 [SMILES: *CCCNC*]
(158)
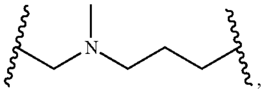
(159)
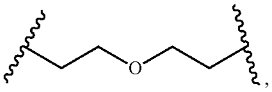 [SMILES: *CCOCC*]
(160)
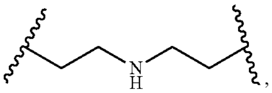 [SMILES: *CCNCC*]
(161)
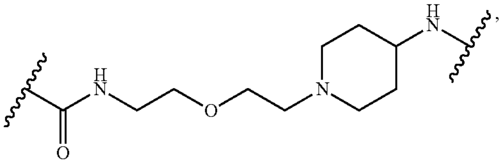 [SMILES: *NC1CCN(CCOCCNC(*)=O)CC1]
(162)
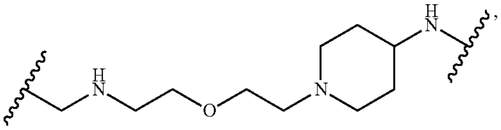 [SMILES: *CNCCOCCN1CCC(N*)CC1]
(163)
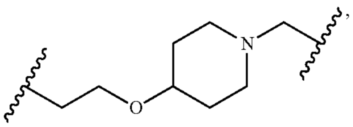 [SMILES: *CCOC1CCN(C*)CC1]
(164)
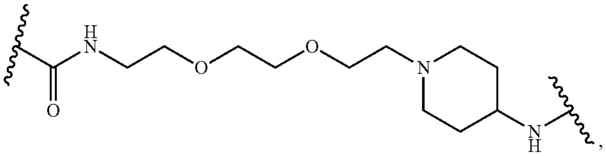 [SMILES: *NC1CCN(CCOCCOCCNC(*)=O)CC1]
(165)

TABLE B-continued
| Exemplified Linkers (L) |
|---|
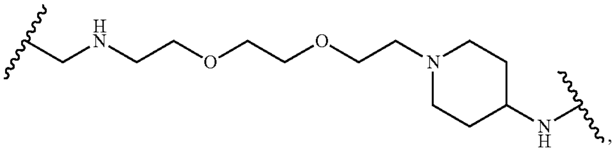 [SMILES: *CNCCOCCOCCN1CCC(N*)CC1]
(166)
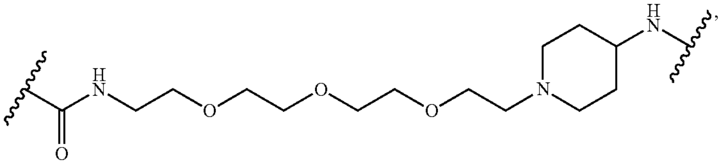 [SMILES: *NC1CCN(CCOCCOCCOCCNC(*)=O)CC1]
(167)
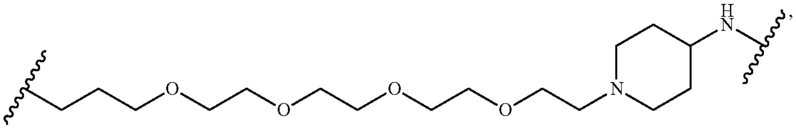 [SMILES: *CCCOCCOCCOCCOCCN1CCC(N*)CC1]
(168)
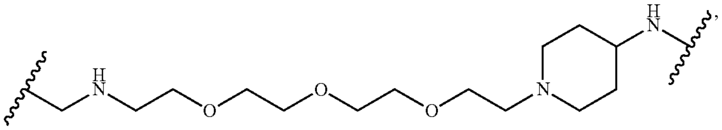 [SMILES: *CNCCOCCOCCOCCN1CCC(N*)CC1]
(169)
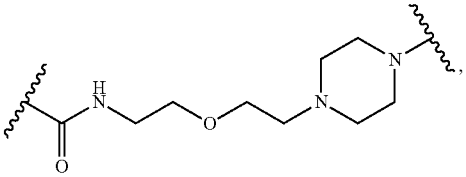 [SMILES: *C(=O)NCCOCCN1CCN(*)CC1]
(170)
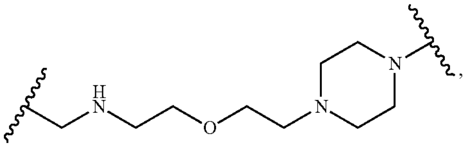 [SMILES: *CNCCOCCN1CCN(*)CC1]
(171)
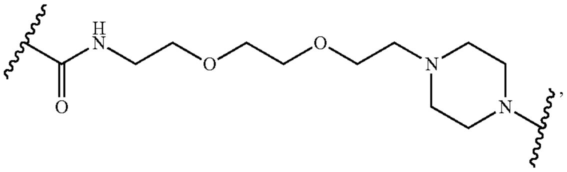 [SMILES: *C(=O)NCCOCCOCCN1CCN(*)CC1]
(172)
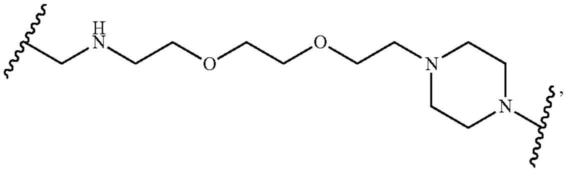 [SMILES: *CNCCOCCOCCN1CCN(*)CC1]
(173)
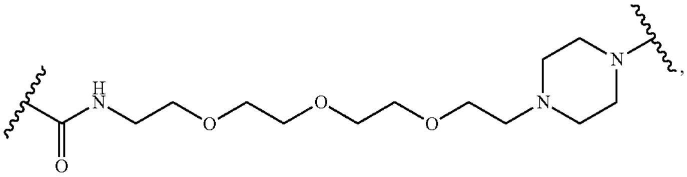 [SMILES: *C(=O)NCCOCCOCCOCCN1CCN(*)CC1]
(174)

TABLE B-continued
| Exemplified Linkers (L) |
|---|
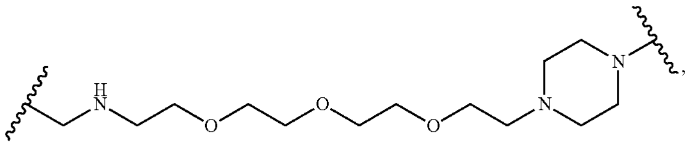 [SMILES: *CNCCOCCOCCOCCN1CCN(*)CC1]
(175)
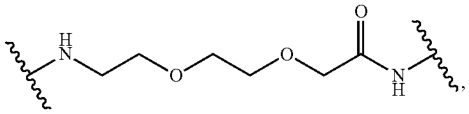 [SMILES: *NCCOCCOCC(=O)N*]
(176)
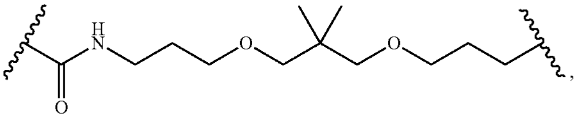 [SMILES: *CCCOCC(C)(C)COCCCNC(*)=O]
(177)
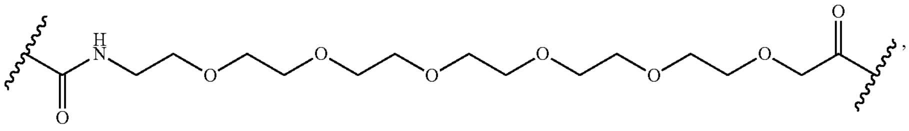 [SMILES: *C(=O)COCCOCCOCCOCCOCCOCCNC(*)=O]
(178)
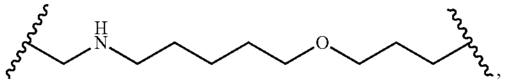 [SMILES: *CCCOCCCCCNC*]
(179)
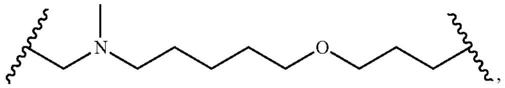 [SMILES: *CCCOCCCCCN(C)C*]
(180)
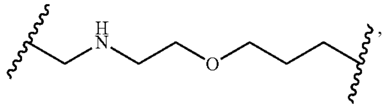 [SMILES: *CCCOCCNC*]
(181)
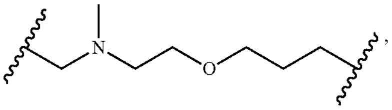 [SMILES: *CCCOCCN(C)C*]
(182)
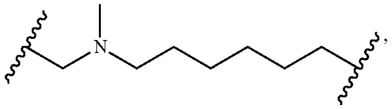 [SMILES: *CCCCCCN(C)C*]
(183)
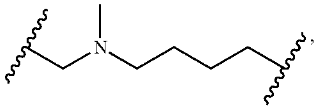 [SMILES: *CCCCN(C)C*]
(184)
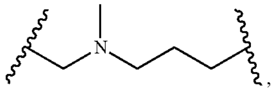
(185)
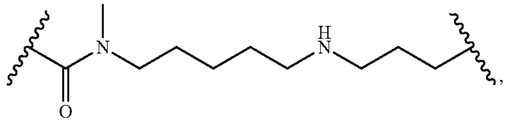 [SMILES: *CCCNCCCCCN(C)C(*)=O]
(186)

TABLE B-continued
| Exemplified Linkers (L) | |
|---|---|
| 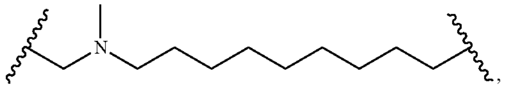 [SMILES: *CCCCCCCCCN(C)C*] | (187) |
| 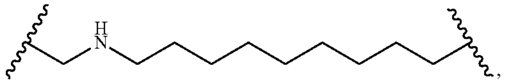 [SMILES: *CCCCCCCCCNC*] | (188) |
| 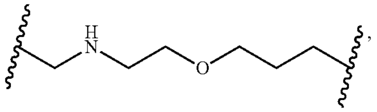 [SMILES: *CCCOCCNC*] | (189) |
| 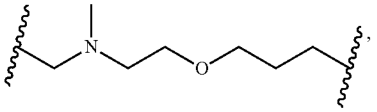 [SMILES: *CCCOCCN(C)C*] | (190) |
| 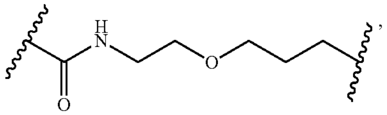 [SMILES: *CCCOCCNC(*)=O] | (191) |
| 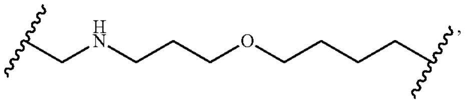 [SMILES: *CCCCOCCCNC*] | (192) |
| 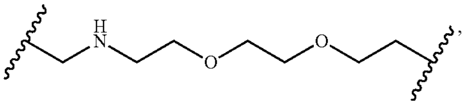 [SMILES: *CCOCCOCCNC*] | (193) |
| 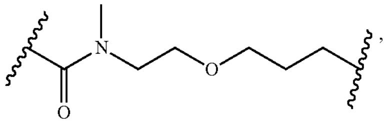 [SMILES: *CCCOCCN(C)C(*)=O] | (194) |
| 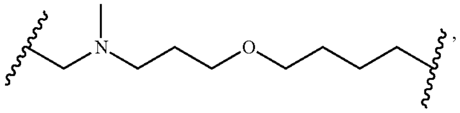 [SMILES: *CCCCOCCCN(C)C*] | (195) |
| 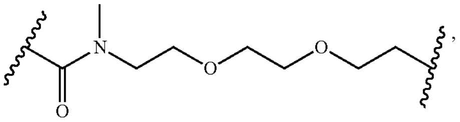 [SMILES: *CCOCCOCCN(C)C(*)=O] | (196) |
| 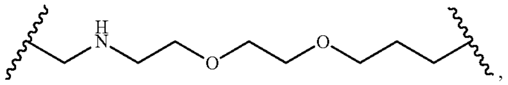 | (197) |
| 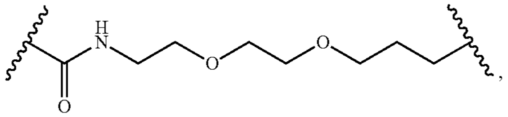 [SMILES: *CCCOCCOCCNC(*)=O] | (198) |
| 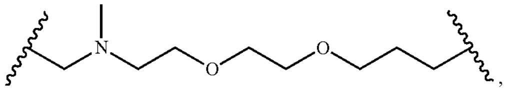 | (199) |

TABLE B-continued
Exemplified Linkers (L)
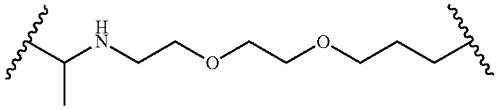,
(200)
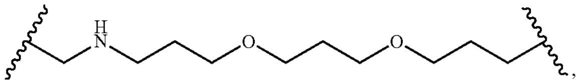 [SMILES: *CCCOCCCOCCCNC*],
(201)
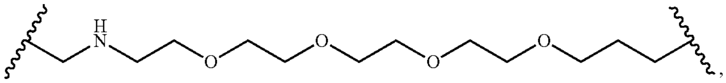 [SMILES: *CCCOCCOCCOCCOCCNC*],
(202)
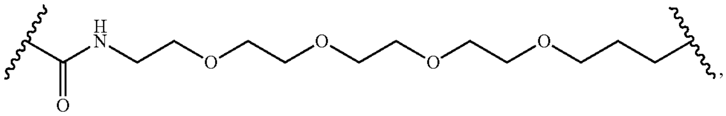 [SMILES: *CCCOCCOCCOCCOCCNC(*)=O],
(203)
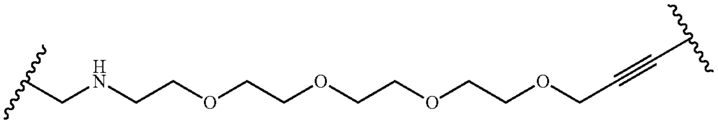,
(204)
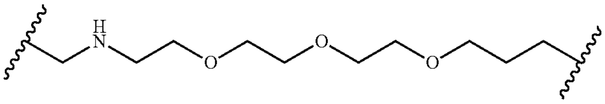,
(205)
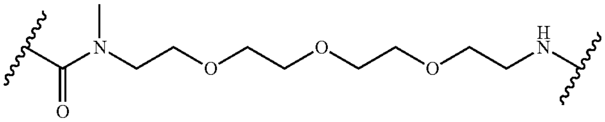,
(206)
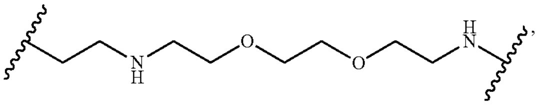 [SMILES: *CCNCCOCCOCCN*],
(207)
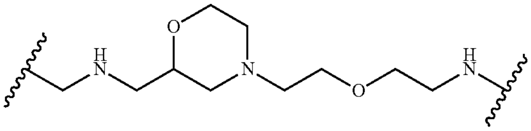,
(208)
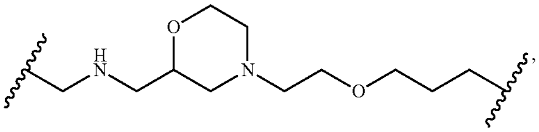 [SMILES: *CCCOCCN1CCOC(CNC*)C1],
(209)
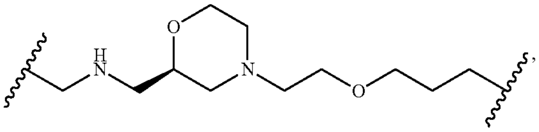 [SMILES: *CCCOCCN1CCO[C@H](CNC*)C1],
(210)
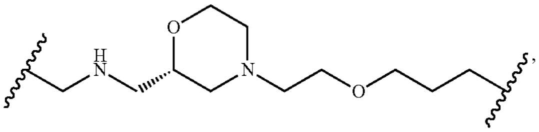 [SMILES: *CCCOCCN1CCO[C@@H](CNC*)C1],
(211)

TABLE B-continued
Exemplified Linkers (L)
(212)
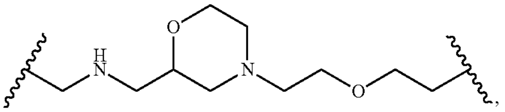 [SMILES: *CCOCCN1CCOC(CNC*)C1]
(213)
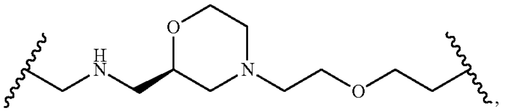 [SMILES: *CCOCCN1CCO[C@H](CNC*)C1]
(214)
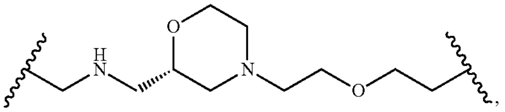 [SMILES: *CCOCCN1CCO[C@@H](CNC*)C1]
(215)
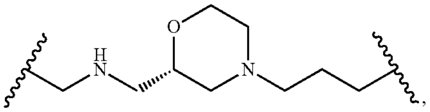 [SMILES: *CCCN1CCO[C@@H](CNC*)C1]
(216)
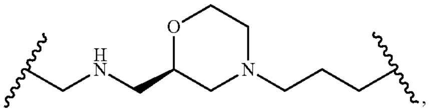 [SMILES: *CCCN1CCO[C@H](CNC*)C1]
(217)
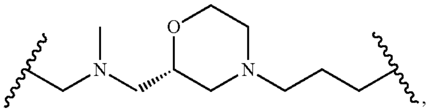 [SMILES: *CCCN1CCO[C@@H](CN(C)C*)C1]
(218)
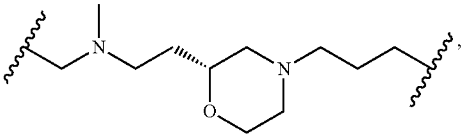 [SMILES: *CCCN1CCO[C@H](CCN(C)C*)C1]
(219)
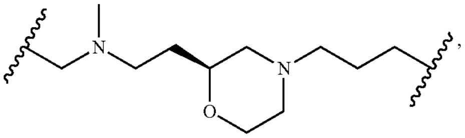 [SMILES: *CCCN1CCO[C@@H](CCN(C)C*)C1]
(220)
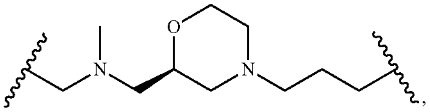 [SMILES: *CCCN1CCO[C@H](CN(C)C*)C1]
(221)
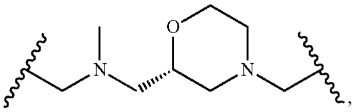 [SMILES: *CN(C)C[C@H]1CN(C*)CCO1]
(222)
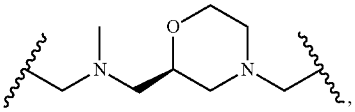 [SMILES: *CN(C)C[C@@H]1CN(C*)CCO1]
(223)
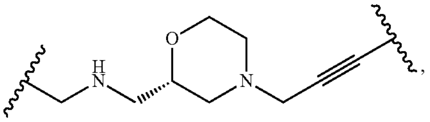 [SMILES: *C#CCN1CCO[C@@H](CNC*)C1]

TABLE B-continued
Exemplified Linkers (L)
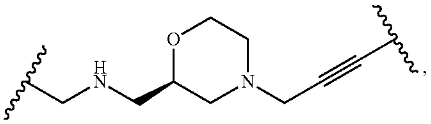 [SMILES: *C#CCN1CCO[C@H](CNC*)C1]
(224)
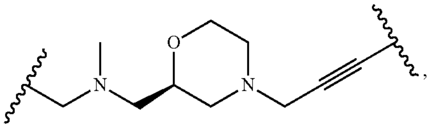 [SMILES: *C#CCN1CCO[C@H](CN(C)C*)C1]
(225)
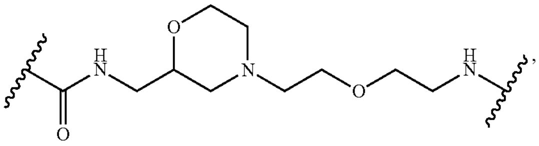 [SMILES: *NCCOCCN1CCOC(CNC(*)=O)C1]
(226)
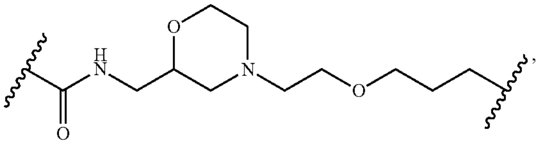 [SMILES: *CCCOCCN1CCOC(CNC(*)=O)C1]
(227)
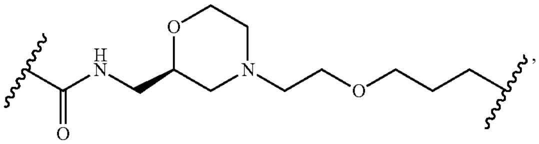 [SMILES: *CCCOCCN1CCO[C@H](CNC(*)=O)C1]
(228)
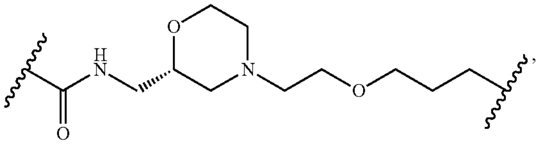 [SMILES: *CCCOCCN1CCO[C@@H](CNC(*)=O)C1]
(229)
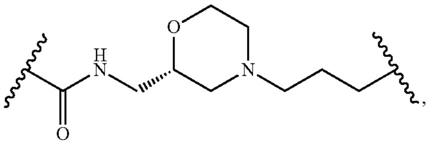 [SMILES: *CCCN1CCO[C@@H](CNC(*)=O)C1]
(230)
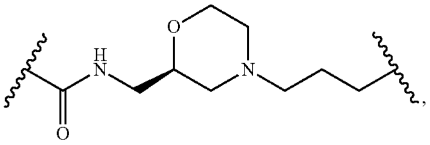 [SMILES: *CCCN1CCO[C@H](CNC(*)=O)C1]
(231)
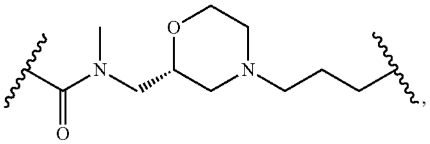 [SMILES: *CCCN1CCO[C@@H](CN(C)C(*)=O)C1]
(232)
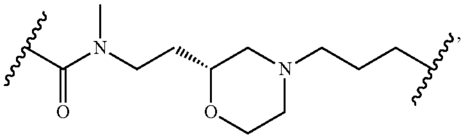 [SMILES: *CCCN1CCO[C@H](CCN(C)C(*)=O)C1]
(233)

TABLE B-continued
| Exemplified Linkers (L) |
|---|
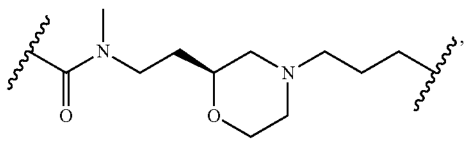 [SMILES: *CCCN1CCO[C@@H](CCN(C)C(*)=O)C1]
(234)
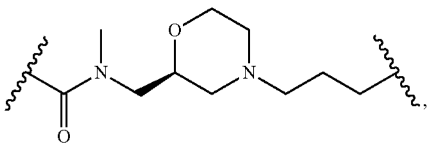 [SMILES: *CCCN1CCO[C@H](CN(C)C(*)=O)C1]
(235)
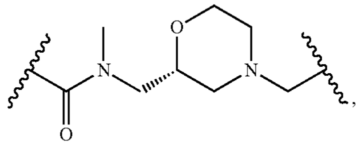 [SMILES: *CN1CCO[C@@H](CN(C)C(*)=O)C1]
(236)
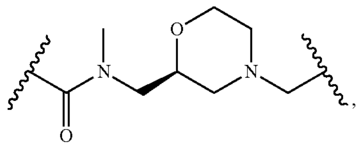 [SMILES: *CN1CCO[C@H](CN(C)C(*)=O)C1]
(237)
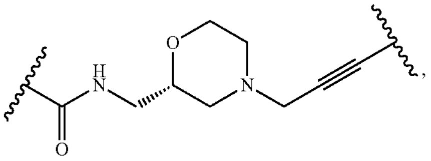 [SMILES: *C#CCN1CCO[C@@H](CNC(*)=O)C1]
(238)
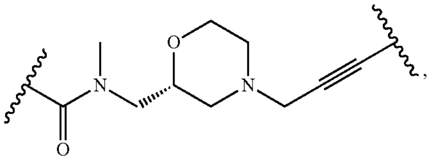 [SMILES: *C#CCN1CCO[C@@H](CN(C)C(*)=O)C1]
(239)
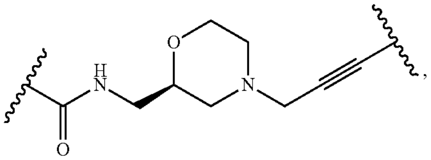 [SMILES: *C#CCN1CCO[C@H](CNC(*)=O)C1]
(240)
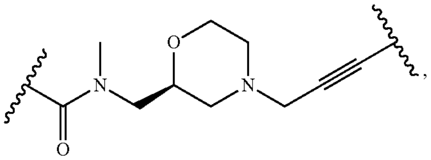 [SMILES: *C#CCN1CCO[C@H](CN(C)C(*)=O)C1]
(241)
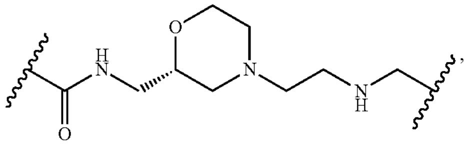 [SMILES: *CNCCN1CCO[C@@H](CNC(*)=O)C1]
(242)

TABLE B-continued
Exemplified Linkers (L)
(243)
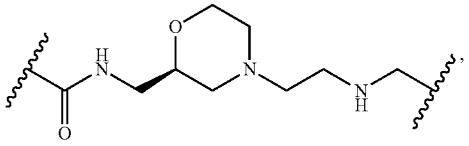 [SMILES: *CNCCN1CCO[C@H](CNC(*)=O)C1]
(244)
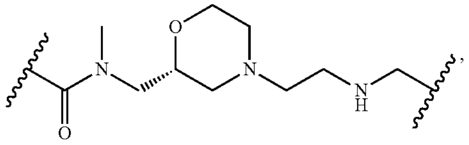 [SMILES: *CNCCN1CCO[C@@H](CN(C)C(*)=O)C1]
(245)
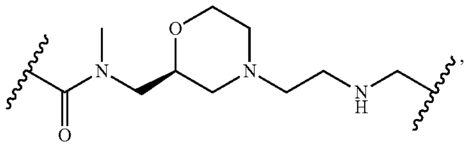 [SMILES: *CNCCN1CCO[C@H](CN(C)C(*)=O)C1]
(246)
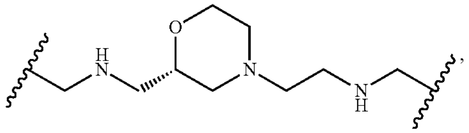 [SMILES: *CNCCN1CCO[C@@H](CNC*)C1]
(247)
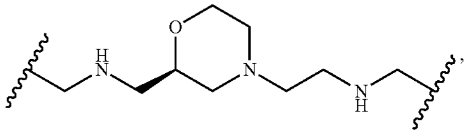 [SMILES: *CNCCN1CCO[C@H](CNC*)C1]
(248)
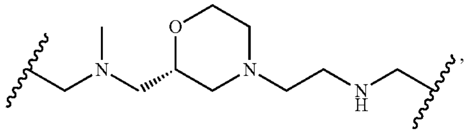 [SMILES: *CNCCN1CCO[C@@H](CN(C)C*)C1]
(249)
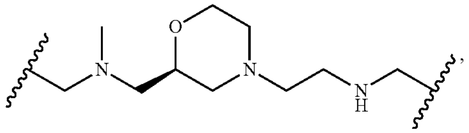 [SMILES: *CNCCN1CCO[C@H](CN(C)C*)C1]
(250)
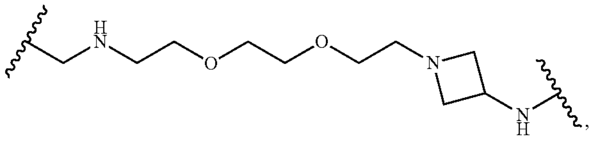 [SMILES: *CNCCOCCOCCN1CC(N*)C1]
(251)
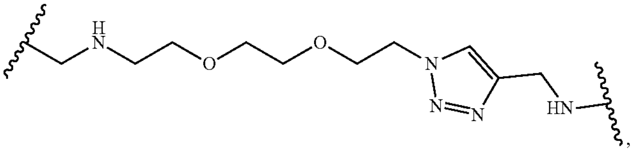 [SMILES: *CNCCOCCOCCn1cc(CN*)nn1]
(253)
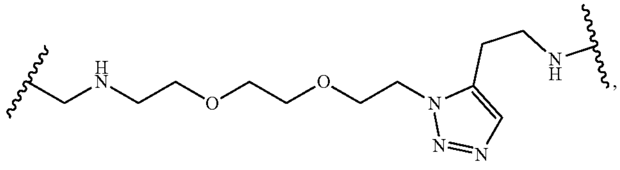 [SMILES: *CNCCOCCOCCn1nncc1CCN*]

TABLE B-continued
| Exemplified Linkers (L) |
| --- |
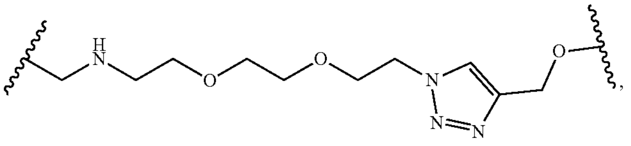 [SMILES: *CNCCOCCOCCn1cc(CO*)nn1]
(254)
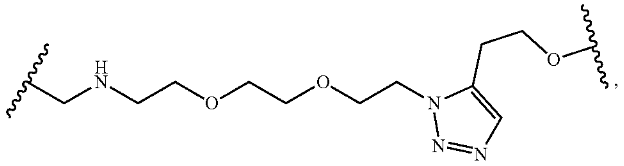 [SMILES: *CNCCOCCOCCn1nncc1CCO*]
(255)
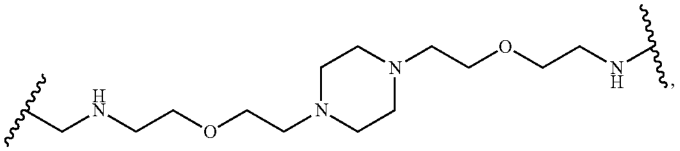 [SMILES: *CNCCOCCN1CCN(CCOCCN*)CC1]
(256)
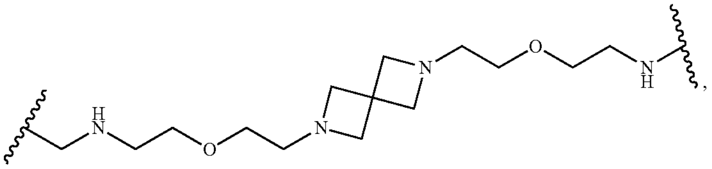 [SMILES: *CNCCOCCN1CC2(CN(CCOCCN*)C2)C1]
(257)
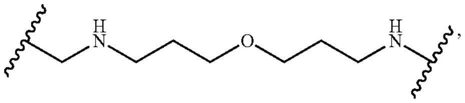 [SMILES: *CNCCCOCCCN*]
(258)
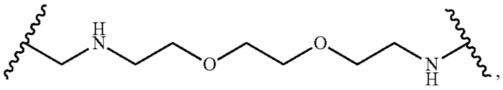 [SMILES: *CNCCOCCOCCN*]
(259)
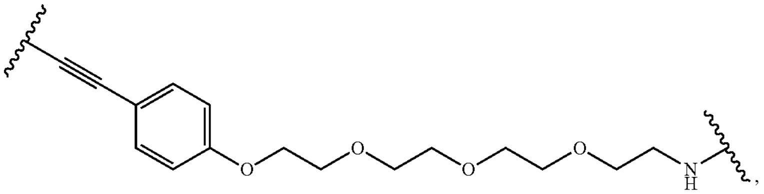 [SMILES: *C#Cc1ccc(OCCOCCOCCOCCN*)cc1]
(260)
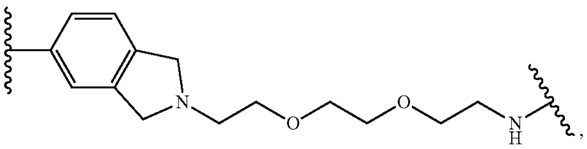 [SMILES: *NCCOCCOCCN1Cc2ccc(*)cc2C1]
(261)
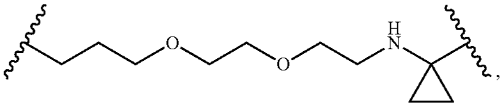 [SMILES: *CCCOCCOCCNC1(*)CC1]
(262)
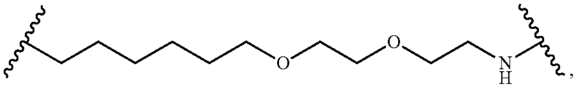 [SMILES: *CCCCCCOCCOCCN*]
(263)

TABLE B-continued
Exemplified Linkers (L)
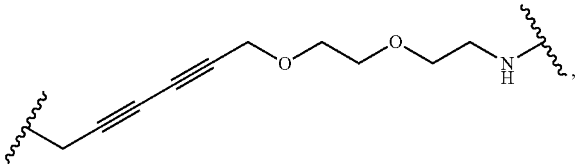 [SMILES: *CC#CC#CCOCCOCCN*]
(264)
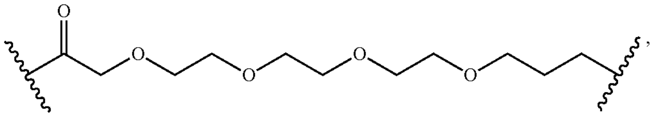 [SMILES: *CCCOCCOCCOCCOCC(*)=O]
(265)
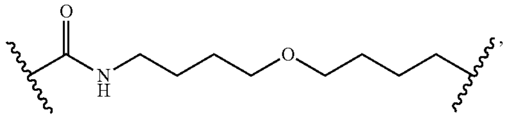 [SMILES: *CCCCOCCCCNC(*)=O]
(266)
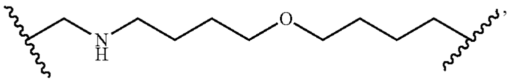 [SMILES: *CCCCOCCCCNC*]
(267)
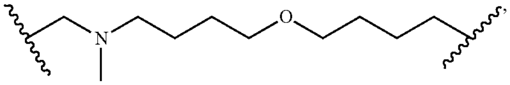 [SMILES: *CCCCOCCCCN(C)C*]
(268)
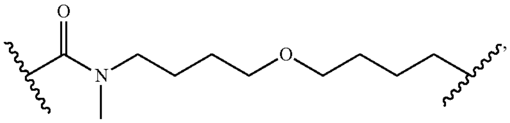 [SMILES: *CCCCOCCCCN(C)C(*)=O]
(269)
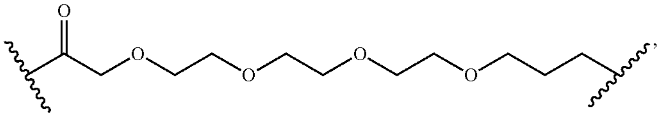 [SMILES: *CCCOCCOCCOCCOCC(*)=O]
(270)
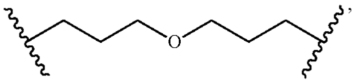 [SMILES: *CCCOCCC*]
(271)
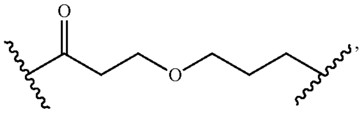 [SMILES: *CCCOCCC(*)=O]
(272)
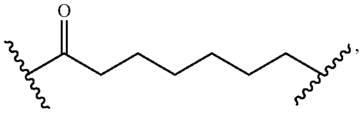 [SMILES: *CCCCCCC(*)=O]
(273)
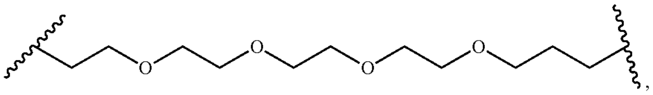 [SMILES: *CCCOCCOCCOCCOCC*]
(274)
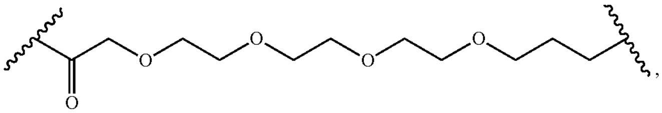 [SMILES: *CCCOCCOCCOCCOCC(*)=O]
(275)

TABLE B-continued
| Exemplified Linkers (L) | |
|---|---|
| 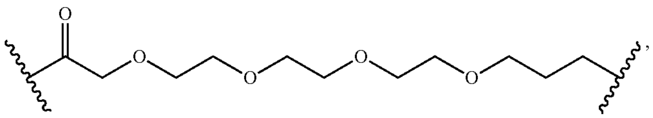 [SMILES: *CCCOCCOCCOCCOCC(*)=O] | (276) |
| 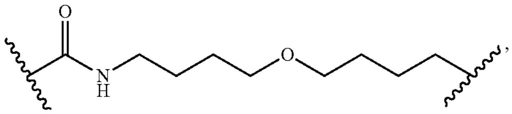 [SMILES: *CCCCOCCCCNC(*)=O] | (277) |
| 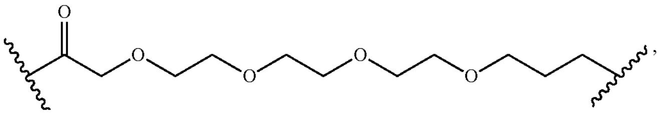 [SMILES: *CCCOCCOCCOCCOCC(*)=O] | (278) |
| 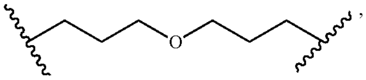 [SMILES: *CCCOCCC*] | (279) |
| 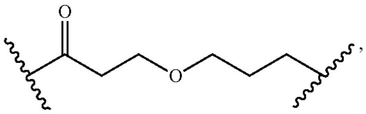 [SMILES: *CCCOCCC(*)=O] | (280) |
| 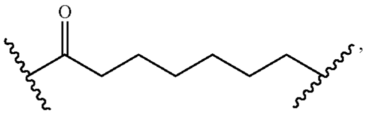 [SMILES: *CCCCCCC(*)=O] | (281) |
| 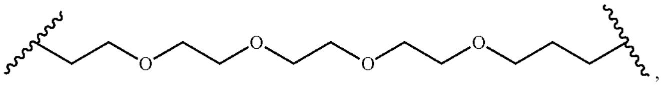 [SMILES: *CCCOCCOCCOCCOCC*] | (282) |
| 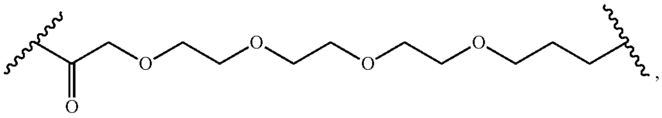 [SMILES: *CCCOCCOCCOCCOCC(*)=O] | (283) |
| 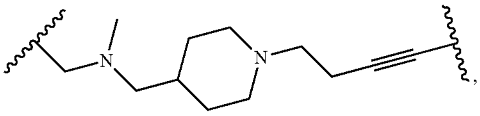 [SMILES: *C#CCCN1CCC(CN(C)C*)CC1] | (284) |
| 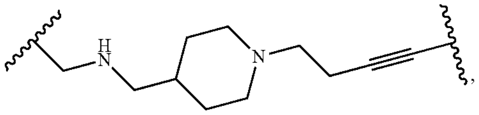 [SMILES: *C#CCCN1CCC(CNC*)CC1] | (285) |
| 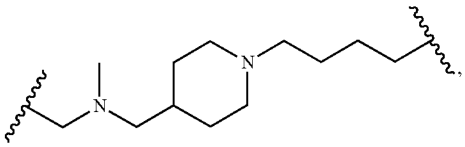 [SMILES: *CCCCN1CCC(CN(C)C*)CC1] | (286) |
| 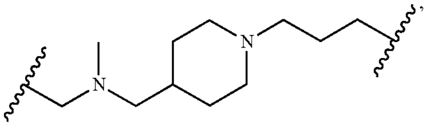 [SMILES: *CCCN1CCC(CN(C)C*)CC1] | (287) |

TABLE B-continued
Exemplified Linkers (L)
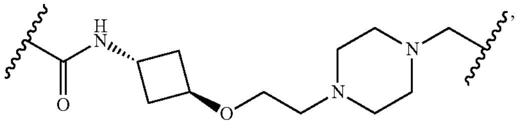 [SMILES: *CN1CCN(CCO[C@H]2C[C@H](NC(*)=O)C2)CC1]
(288)
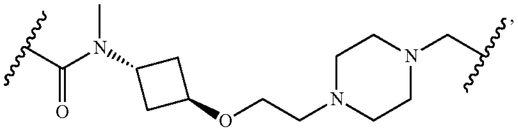 [SMILES: *CN1CCN(CCO[C@H]2C[C@H](N(C)C(*)=O)C2)CC1]
(289)
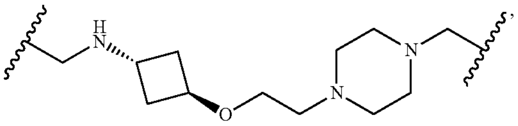 [SMILES: *CN[C@H]1C[C@H](OCCN2CCN(C*)CC2)C1]
(290)
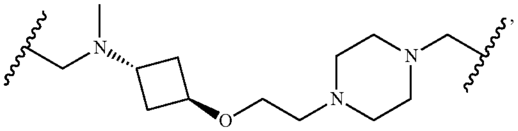 [SMILES: *CN1CCN(CCO[C@H]2C[C@H](N(C)C*)C2)CC1]
(291)
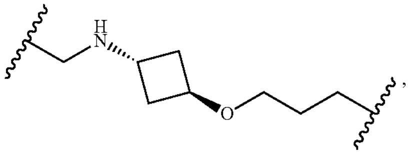 [SMILES: *CCCO[C@H]1C[C@H](NC*)C1]
(292)
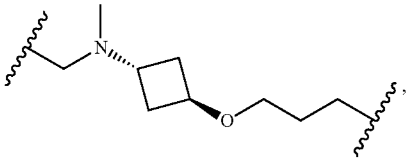 [SMILES: *CCCO[C@H]1C[C@H](N(C)C*)C1]
(293)
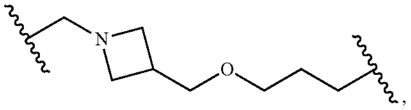 [SMILES: *CCCOCC1CN(C*)C1]
(294)
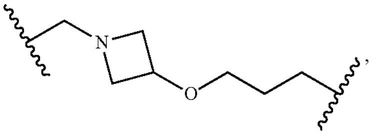 [SMILES: *CCCOC1CN(C*)C1]
(295)
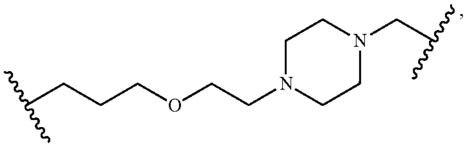 [SMILES: *CCCOCCN1CCN(C*)CC1]
(296)
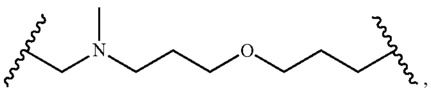
(297)
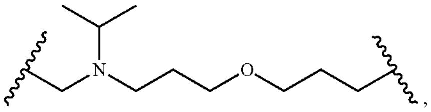
(298)

TABLE B-continued
Exemplified Linkers (L)
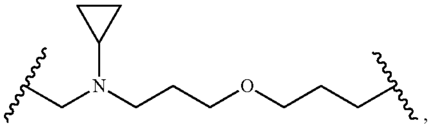 [SMILES: *CCCOCCCN(C*)C1CC1]
(299)
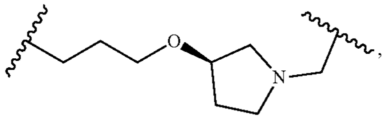 [SMILES: *CCCO[C@@H]1CCN(C*)C1]
(300)
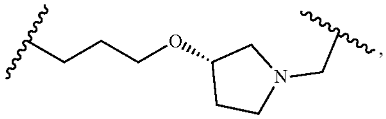 [SMILES: *CCCO[C@H]1CCN(C*)C1]
(301)
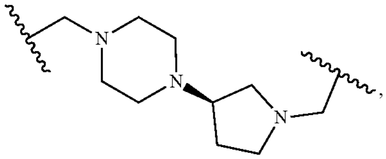 [SMILES: *CN1CCN([C@@H]2CCN(C*)C2)CC1]
(302)
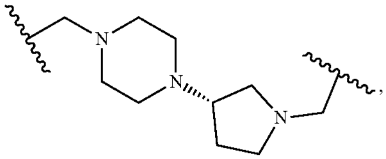 [SMILES: *CN1CCN([C@H]2CCN(C*)C2)CC1]
(303)
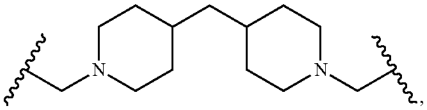 [SMILES: *CN1CCC(CC2CCN(C*)CC2)CC1]
(304)
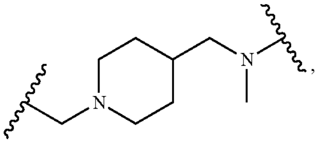 [SMILES: *CN1CCC(CN(*)C)CC1]
(305)
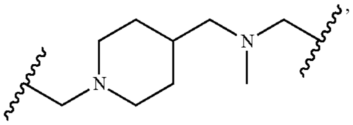 [SMILES: *CN(C)CC1CCN(C*)CC1]
(306)
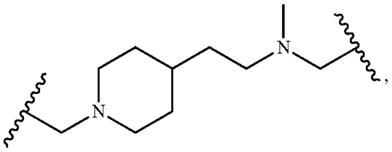 [SMILES: *CN(C)CCC1CCN(C*)CC1]
(307)
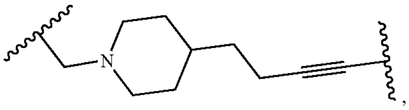 [SMILES: *C#CCCC1CCN(C*)CC1]
(308)

TABLE B-continued
| Exemplified Linkers (L) |
|---|
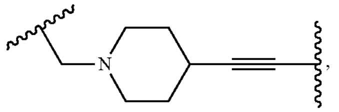 [SMILES: *C#CC1CCN(C*)CC1]
(309)
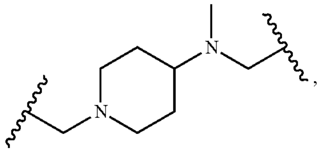 [SMILES: *CN1CCC(N(C)C*)CC1]
(310)
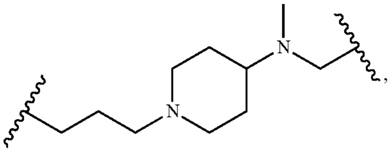 [SMILES: *CCCN1CCC(N(C)C*)CC1]
(311)
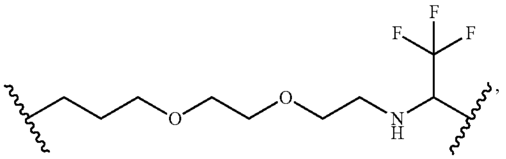 [SMILES: *CCCOCCOCCNC(*)C(F)(F)F]
(312)
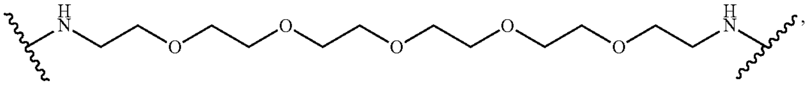 [SMILES: *NCCOCCOCCOCCOCCOCCN*]
(313)
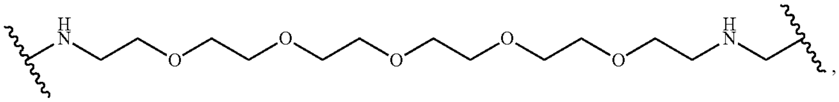 [SMILES: *CNCCOCCOCCOCCOCCOCCN*]
(314)
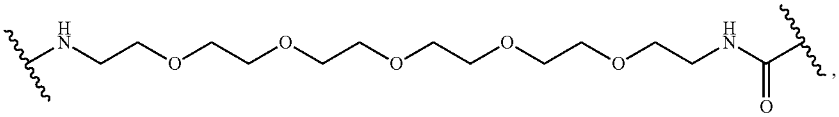 [SMILES: *NCCOCCOCCOCCOCCOCCNC(*)=O]
(315)
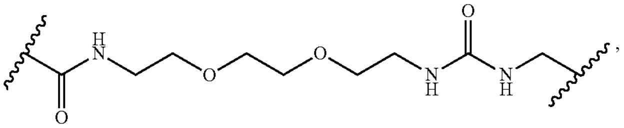 [SMILES: *CNC(=O)NCCOCCOCCNC(*)=O]
(316)
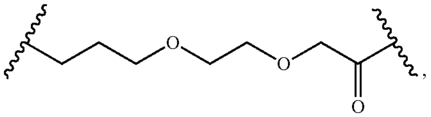 [SMILES: *CCCOCCOCC(*)=O]
(317)
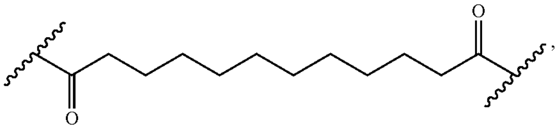 [SMILES: *C(=O)CCCCCCCCCCC(*)=O]
(318)
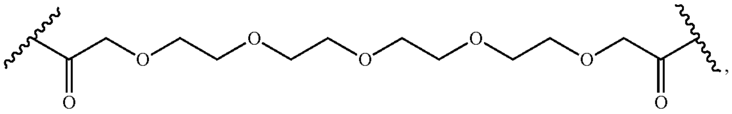 [SMILES: *C(=O)COCCOCCOCCOCCOCC(*)=O]
(319)

TABLE B-continued
| Exemplified Linkers (L) |
|---|
| 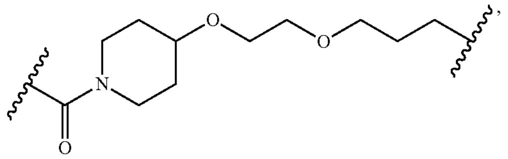 [SMILES: *CCCOCCOC1CCN(C(*)=O)CC1] (320) |
| 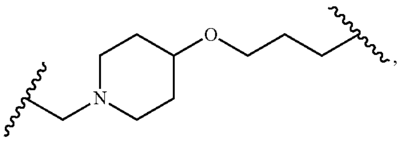 [SMILES: *CCCOC1CCN(C*)CC1] (321) |
| 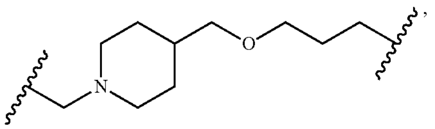 [SMILES: *CCCOCC1CCN(C*)CC1] (322) |
| 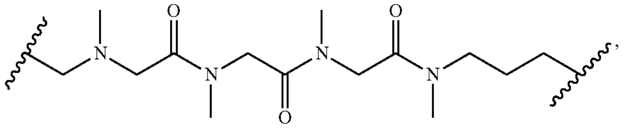 [SMILES: *CCCN(C)C(=O)CN(C)C(=O)CN(C)C(=O)CN(C)C*] (323) |
| 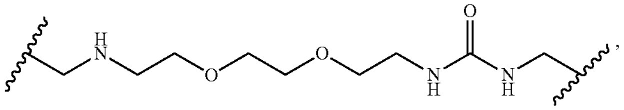 [SMILES: *CNCCOCCOCCNC(=O)NC*] (324) |
| 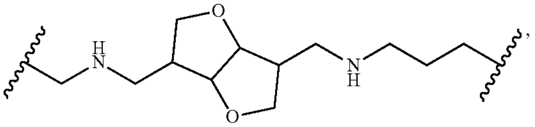 [SMILES: *CCCNCC1COC2C(CNC*)COC12] (325) |
| 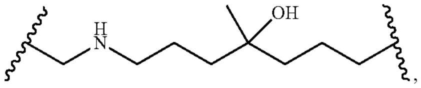 [SMILES: *CCCC(C)(O)CCCNC*] (326) |
| 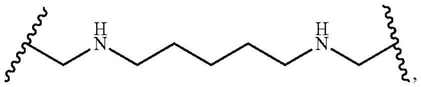 [SMILES: *CNCCCCCNC*] (327) |
| 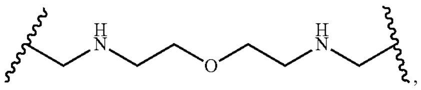 [SMILES: *CNCCOCCNC*] (328) |
| 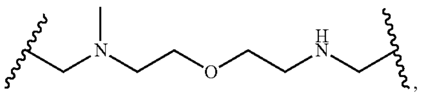 [SMILES: *CNCCOCCN(C)C*] (329) |
| 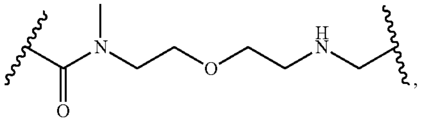 [SMILES: *CNCCOCCN(C)C(*)=O] (330) |
| 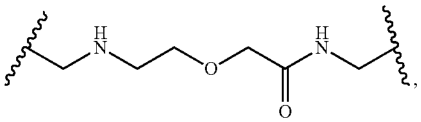 [SMILES: *CNCCOCC(=O)NC*] (331) |

TABLE B-continued
Exemplified Linkers (L)
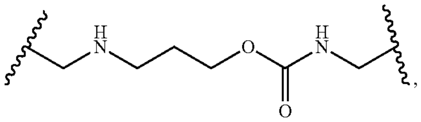 [SMILES: *CNCCCOC(=O)NC*]
(332)
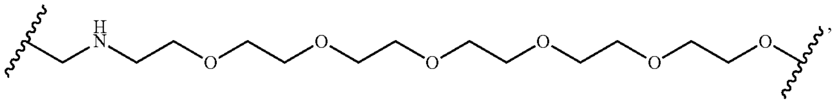 [SMILES: *CNCCOCCOCCOCCOCCOCCO*]
(333)
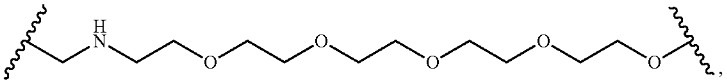 [SMILES: *CNCCOCCOCCOCCOCCO*]
(334)
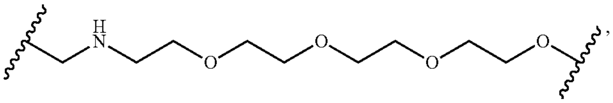 [SMILES: *CNCCOCCOCCOCCO*]
(335)
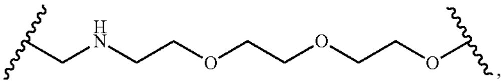 [SMILES: *CNCCOCCOCCO*]
(336)
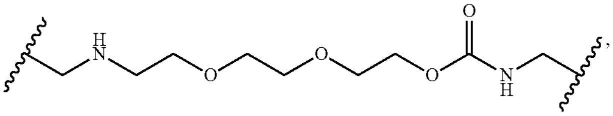 [SMILES: *CNCCOCCOCCOC(=O)NC*]
(337)
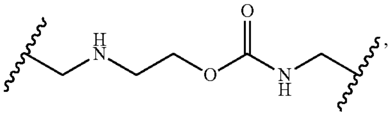 [SMILES: *CNCCOC(=O)NC*]
(338)
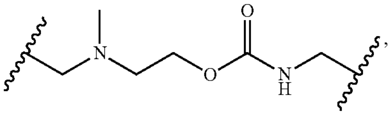 [SMILES: *CNC(=O)OCCN(C)C*]
(339)
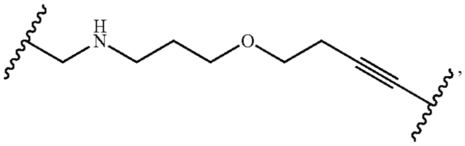 [SMILES: *C#CCCOCCCNC*]
(340)
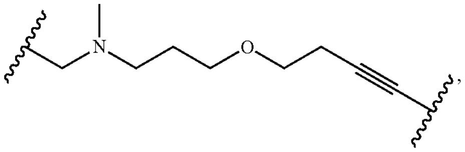 [SMILES: *C#CCCOCCCN(C)C*]
(341)
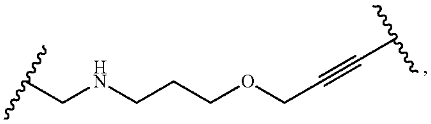 [SMILES: *C#CCOCCCNC*]
(342)
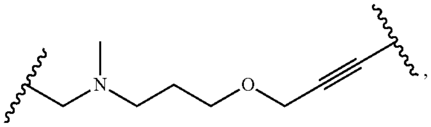 [SMILES: *C#CCOCCCN(C)C*]
(343)

TABLE B-continued
Exemplified Linkers (L)
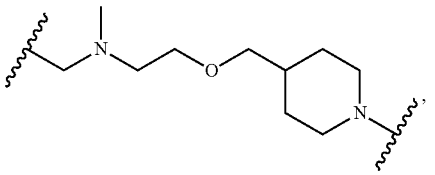 [SMILES: *CN(C)CCOCC1CCN(*)CC1]
(344)
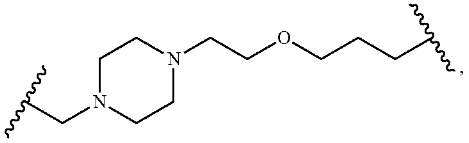 [SMILES: *CCCOCCN1CCN(C*)CC1]
(345)
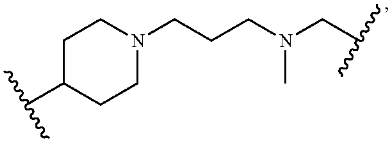 [SMILES: *CN(C)CCCN1CCC(*)CC1]
(346)
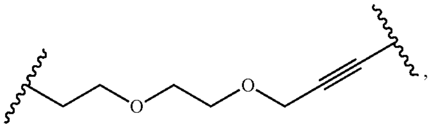 [SMILES: *C#CCOCCOCC*]
(347)
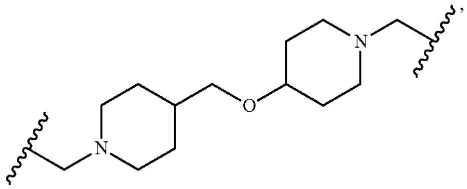 [SMILES: *CN1CCC(COC2CCN(C*)CC2)CC1]
(348)
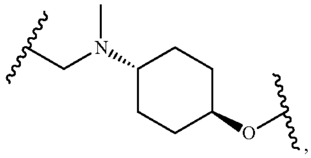 [SMILES: *CN(C)[C@H]1CC[C@H](O*)CC1]
(349)
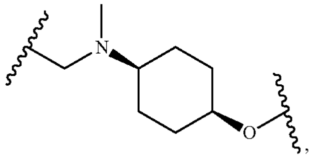 [SMILES: *CN(C)[C@H]1CC[C@@H](O*)CC1]
(350)
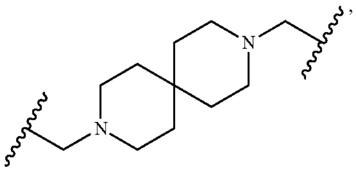 [SMILES: *CN1CCC2(CC1)CCN(C*)CC2]
(351)
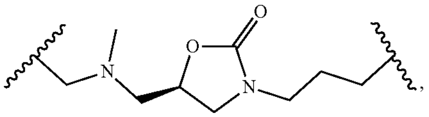 [SMILES: *CCCN1C[C@@H](CN(C)C*)OC1=O]
(352)

TABLE B-continued
| Exemplified Linkers (L) |
|---|
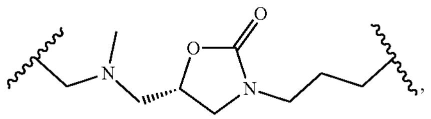 [SMILES: *CCCN1C[C@H](CN(C)C*)OC1=O]
(353)
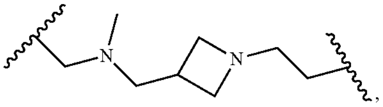 [SMILES: *CCN1CC(CN(C)C*)C1]
(354)
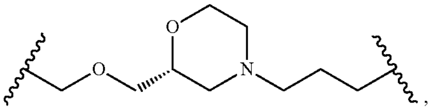 [SMILES: *CCCN1CCO[C@@H](COC*)C1]
(355)
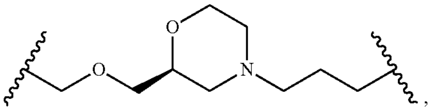 [SMILES: *CCCN1CCO[C@H](COC*)C1]
(356)
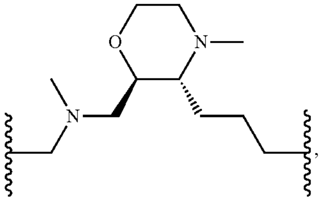 [SMILES: *CCC[C@@H]1[C@@H](CN(C)C*)OCCN1C]
(357)
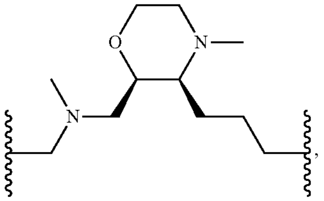 [SMILES: *CCC[C@H]1[C@@H](CN(C)C*)OCCN1C]
(358)
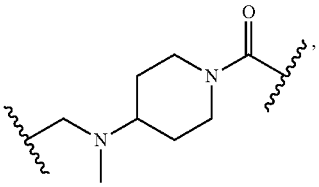 [SMILES: *CN(C)C1CCN(C(*)=O)CC1]
(359)
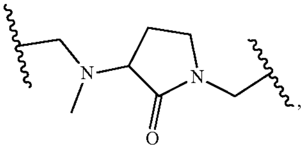 [SMILES: *CN1CCC(N(C)C*)C1=O]
(360)
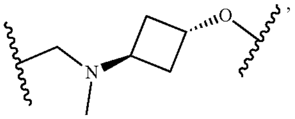 [SMILES: *CN(C)[C@H]1C[C@H](O*)C1]
(361)
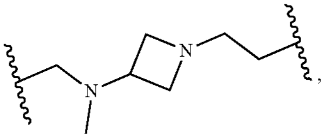 [SMILES: *CCN1CC(N(C)C*)C1]
(362)

TABLE B-continued
Exemplified Linkers (L)
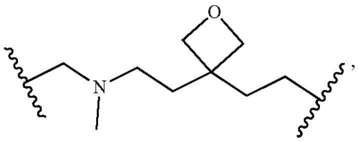 [SMILES: *CCC1(CCN(C)C*)COC1]
(363)
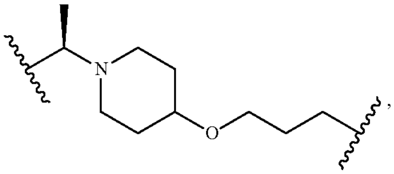 [SMILES: *CCCOC1CCN([C@@H](*)C)CC1]
(364)
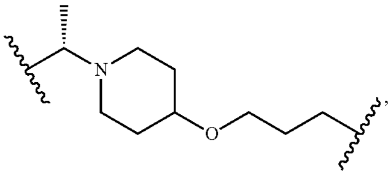 [SMILES: *CCCOC1CCN([C@H](*)C)CC1]
(365)
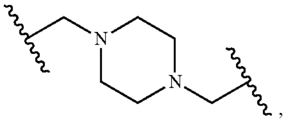 [SMILES: *CN1CCN(C*)CC1]
(366)
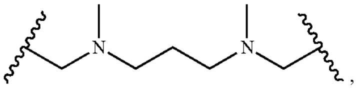 [SMILES: *CN(C)CCCN(C)C*]
(367)
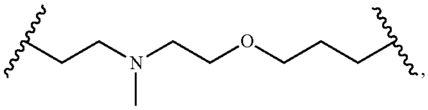 [SMILES: *CCCOCCN(C)CC*]
(368)
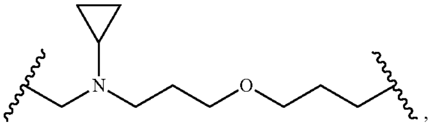 [SMILES: *CCCOCCCN(C*)C1CC1]
(369)
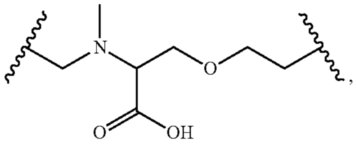 [SMILES: *CCOCC(C(=O)O)N(C)C*]
(370)
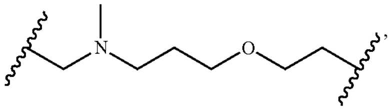 [SMILES: *CCOCCCN(C)C*]
(371)
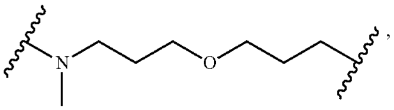 [SMILES: *CCCOCCCN(*)C]
(372)

TABLE B-continued
| Exemplified Linkers (L) |
|---|
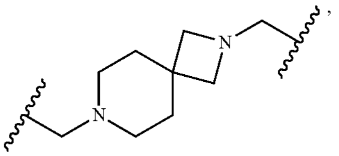 [SMILES: *CN1CCC2(CC1)CN(C*)C2]
(373)
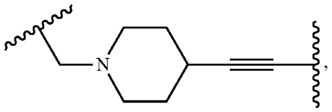 [SMILES: *C#CC1CCN(C*)CC1]
(374)
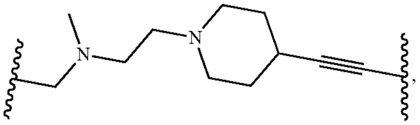 [SMILES: *C#CC1CCN(CCN(C)C*)CC1]
(375)
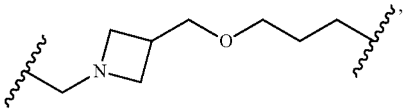 [SMILES: *CCCOCC1CN(C*)C1]
(376)
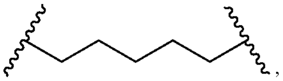 [SMILES: *CCCCC*]
(377)
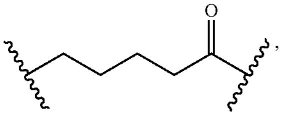 [SMILES: *CCCCC(*)=O]
(378)
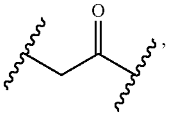 [SMILES: *CC(*)=O]
(379)
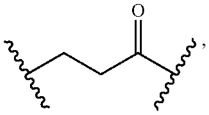 [SMILES: *CCC(*)=O]
(380)
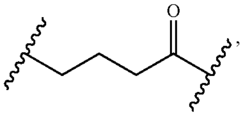 [SMILES: *CCCC(*)=O]
(381)
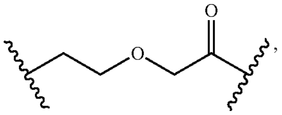 [SMILES: *CCOCC(*)=O]
(382)
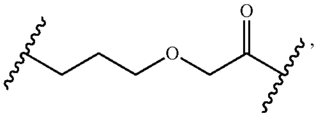 [SMILES: *CCCOCC(*)=O]
(383)
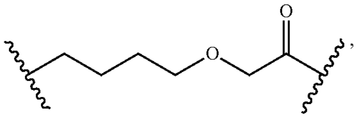 [SMILES: *CCCCOCC(*)=O]
(384)

TABLE B-continued
| Exemplified Linkers (L) |
|---|
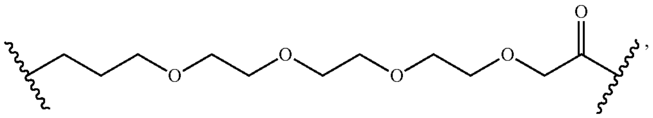 [SMILES: *CCCOCCOCCOCCOCC(*)=O]
(385)
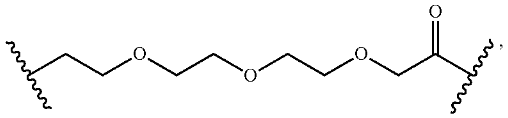 [SMILES: *CCOCCOCCOCC(*)=O]
(386)
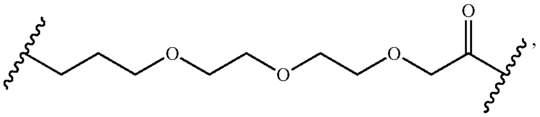 [SMILES: *CCCOCCOCCOCC(*)=O]
(387)
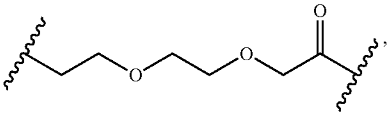 [SMILES: *CCOCCOCC(*)=O]
(388)
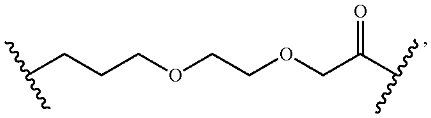 [SMILES: *CCCOCCOCC(*)=O]
(389)
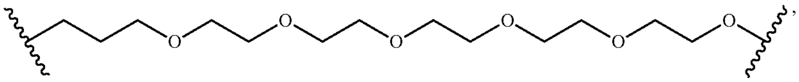 [SMILES: *CCCOCCOCCOCCOCCOCCO*]
(390)
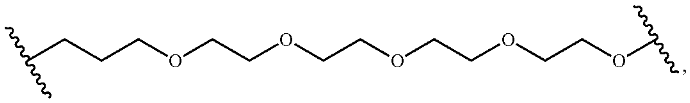 [SMILES: *CCCOCCOCCOCCOCCO*]
(391)
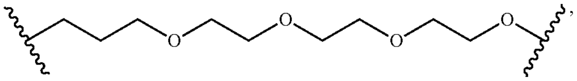 [SMILES: *CCCOCCOCCOCCO*]
(392)
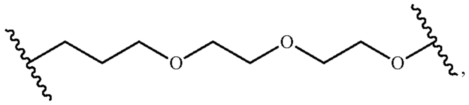 [SMILES: *CCCOCCOCCO*]
(393)
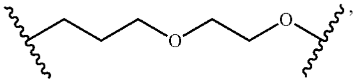 [SMILES: *CCCOCCO*]
(394)
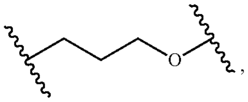 [SMILES: *CCCO*]
(395)
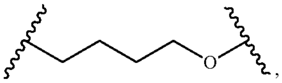 [SMILES: *CCCCO*]
(396)
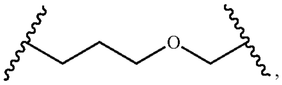 [SMILES: *CCCOC*]
(397)

TABLE B-continued
| Exemplified Linkers (L) | |
|---|---|
| 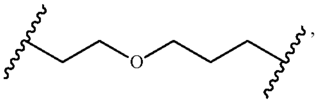 [SMILES: *CCCOCC*] | (398) |
| 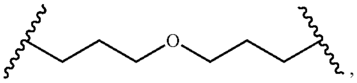 [SMILES: *CCCOCCC*] | (399) |
| 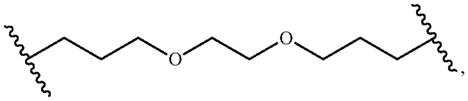 [SMILES: *CCCOCCOCCC*] | (400) |
| 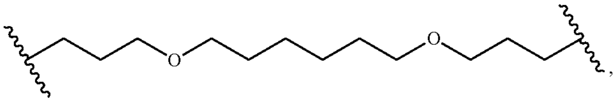 [SMILES: *CCCOCCCCCCOCCC*] | (401) |
| 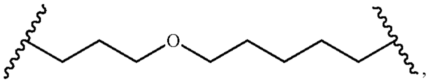 [SMILES: *CCCCCOCCC*] | (402) |
| 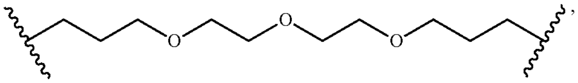 [SMILES: *CCCOCCOCCOCCC*] | (403) |
| 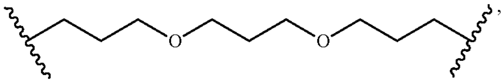 [SMILES: *CCCOCCCOCCC*] | (404) |
| 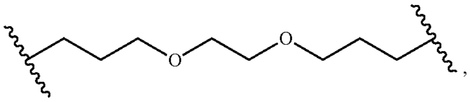 [SMILES: *CCCOCCOCCC*] | (405) |
| 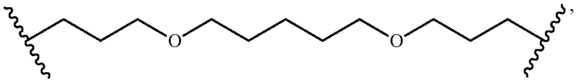 [SMILES: *CCCOCCCCCOCCC*] | (406) |
| 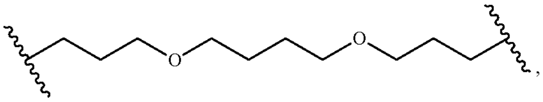 [SMILES: *CCCOCCCCOCCC*] | (407) |
| 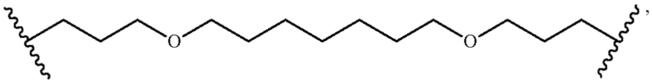 [SMILES: *CCCOCCCCCCCOCCC*] | (408) |
| 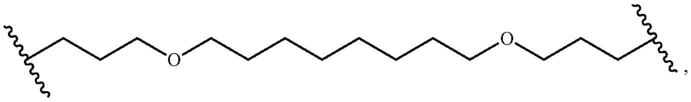 [SMILES: *CCCOCCCCCCCCOCCC*] | (409) |
| 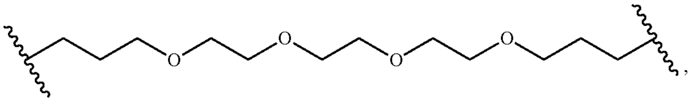 [SMILES: *CCCOCCOCCOCCOCCC*] | (410) |
| 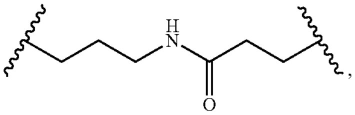 [SMILES: *CCCNC(=O)CC*] | (411) |

TABLE B-continued
Exemplified Linkers (L)
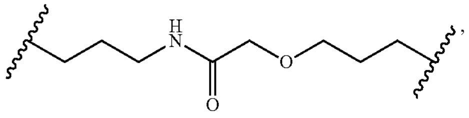 [SMILES: *CCCNC(=O)COCCC*]
(412)
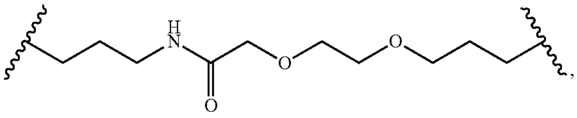 [SMILES: *CCCNC(=O)COCCOCCC*]
(413)
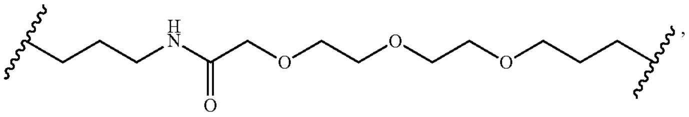 [SMILES: *CCCNC(=O)COCCOCCOCCC*]
(414)
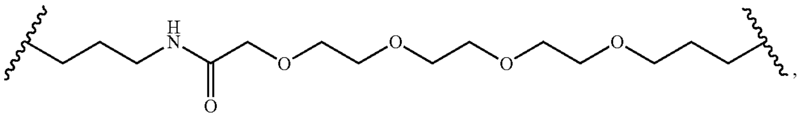 [SMILES: *CCCNC(=O)COCCOCCOCCOCCC*]
(415)
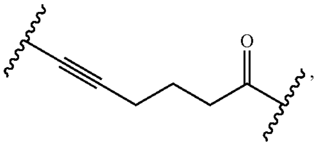 [SMILES: *C#CCCCC(*)=O]
(416)
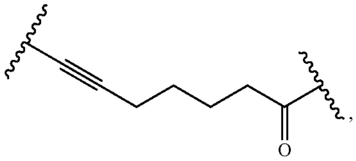 [SMILES: *C#CCCCCC(*)=O]
(417)
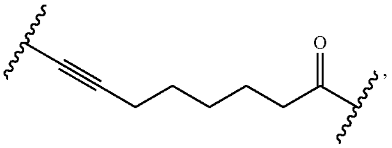 [SMILES: *C#CCCCCCC(*)=O]
(418)
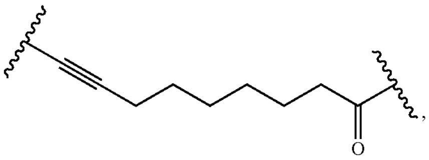 [SMILES: *C#CCCCCCCC(*)=O]
(419)
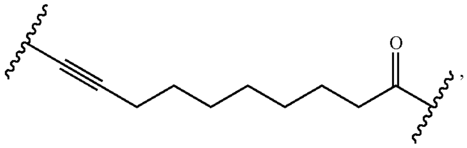 [SMILES: *C#CCCCCCCCC(*)=O]
(420)
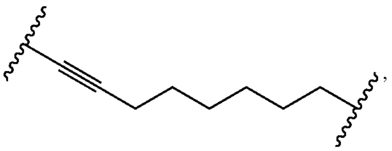 [SMILES: *C#CCCCCCC*]
(421)

TABLE B-continued
| Exemplified Linkers (L) |
| --- |
| 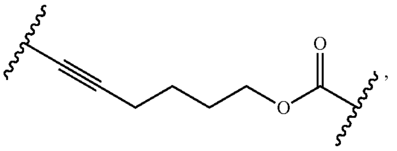 [SMILES: *C#CCCCCOC(*)=O] (422) |
| 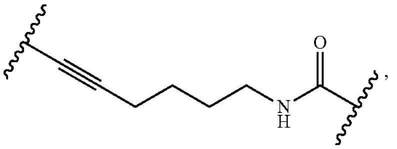 [SMILES: *C#CCCCCNC(*)=O] (423) |
| 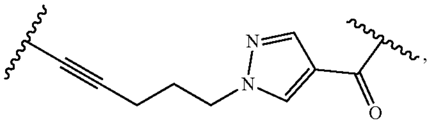 [SMILES: *C#CCCCn1cc(C(*)=O)cn1] (424) |
| 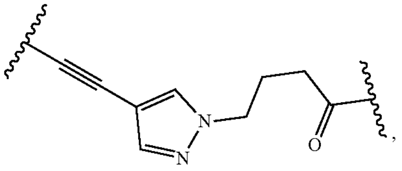 [SMILES: *C#Cc1cnn(CCCC(*)=O)c1] (425) |
| 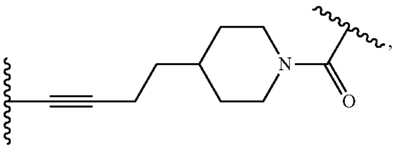 [SMILES: *C#CCCC1CCN(C(*)=O)CC1] (426) |
| 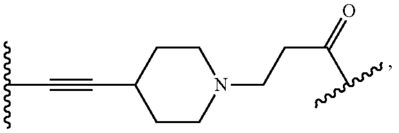 [SMILES: *C#CC1CCN(CCC(*)=O)CC1] (427) |
| 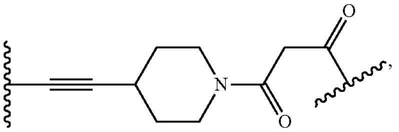 [SMILES: *C#CC1CCN(C(=O)CC(*)=O)CC1] (428) |
| 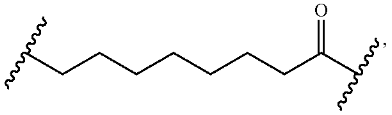 [SMILES: *CCCCCCCC(*)=O] (429) |
| 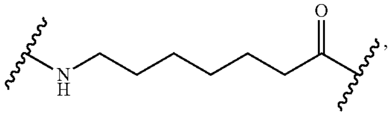 [SMILES: *NCCCCCCC(*)=O] (430) |
| 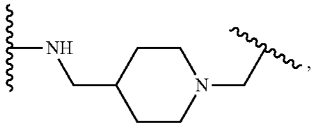 [SMILES: *CN1CCC(CN*)CC1] (431) |

TABLE B-continued
| Exemplified Linkers (L) |
| --- |
| 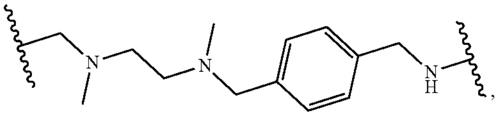 [SMILES: *CN(C)CCN(C)Cc1ccc(CN*)cc1] (432) |
| 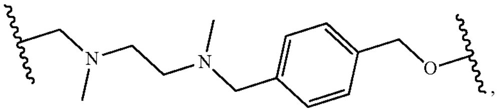 [SMILES: *CN(C)CCN(C)Cc1ccc(CO*)cc1] (433) |
| 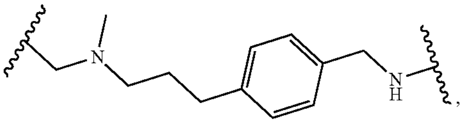 [SMILES: *CN(C)CCCc1ccc(CN*)cc1] (434) |
| 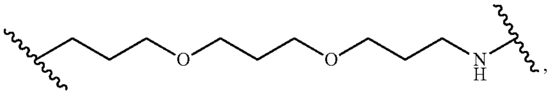 [SMILES: *CCCOCCCOCCCN*] (435) |
| 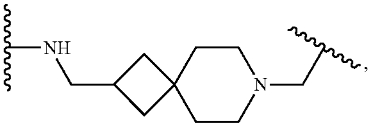 [SMILES: *CN1CCC2(CC1)CC(CN*)C2] (436) |
| 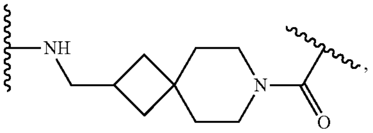 [SMILES: *NCC1CC2(CCN(C(*)=O)CC2)C1] (437) |
| 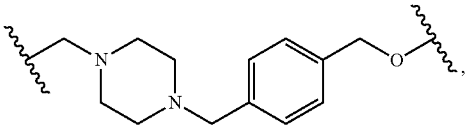 [SMILES: *CN1CCN(Cc2ccc(CO*)cc2)CC1] (438) |
| 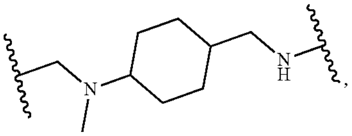 [SMILES: *CN(C)C1CCC(CN*)CC1] (438) |
| 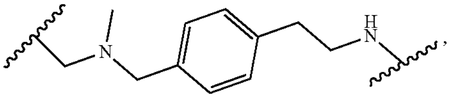 [SMILES: *CN(C)Cc1ccc(CCN*)cc1] (439) |
| 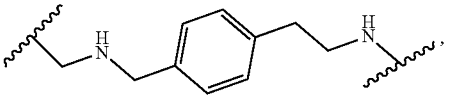 [SMILES: *CNCc1ccc(CCN*)cc1] (440) |
| 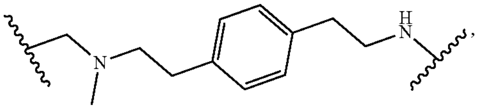 [SMILES: *CN(C)CCc1ccc(CCN*)cc1] (441) |
| 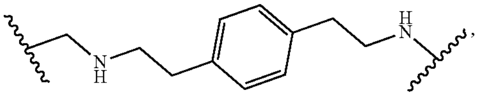 [SMILES: *CNCCc1ccc(CCN*)cc1] (442) |

TABLE B-continued
| Exemplified Linkers (L) | |
|---|---|
| 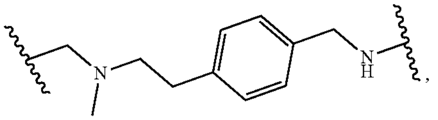 [SMILES: *CN(C)CCc1ccc(CN*)cc1] | (443) |
| 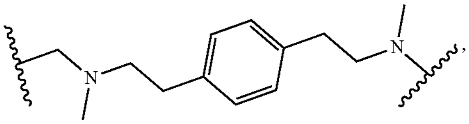 [SMILES: *CN(C)CCc1ccc(CCN(*)C)cc1] | (444) |
| 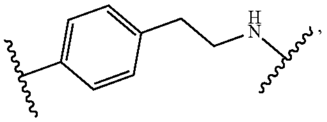 [SMILES: *NCCc1ccc(*)cc1] | (445) |
| 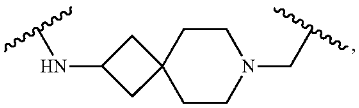 | (446) |
| 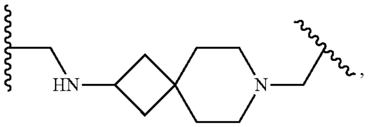 [SMILES: *CNC1CC2(CCN(C*)CC2)C1] | (447) |
| 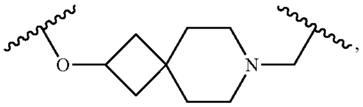 [SMILES: *CN1CCC2(CC1)CC(O*)C2] | (448) |
| 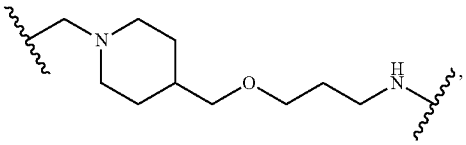 [SMILES: *CN1CCC(COCCCN*)CC1] | (449) |
| 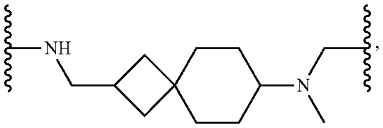 [SMILES: *CN(C)C1CCC2(CC1)CC(CN*)C2] | (450) |
| 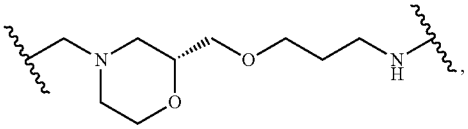 [SMILES: *CN1CCO[C@@H](COCCCN*)C1] | (451) |
| 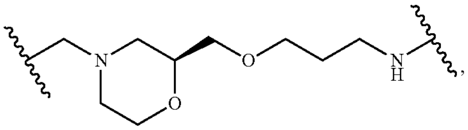 [SMILES: *CN1CCO[C@H](COCCCN*)C1] | (452) |
| 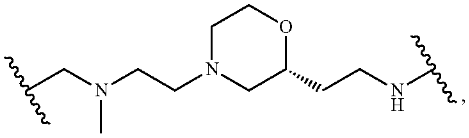 [SMILES: *CN(C)CCN1CCO[C@H](CCN*)C1] | (453) |

TABLE B-continued
Exemplified Linkers (L)
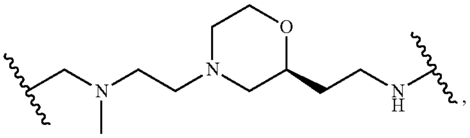 [SMILES: *CN(C)CCN1CCO[C@@H](CCN*)C1]
(454)
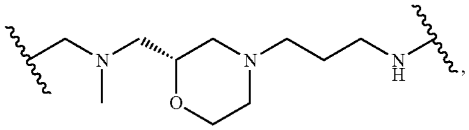 [SMILES: *CN(C)C[C@@H]1CN(CCCN*)CCO1]
(455)
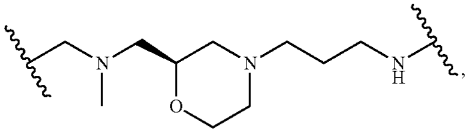 [SMILES: *CN(C)C[C@H]1CN(CCCN*)CCO1]
(456)
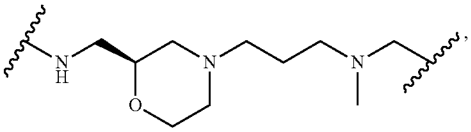 [SMILES: *CN(C)CCCN1CCO[C@@H](CN*)C1]
(457)
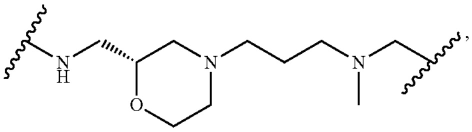
(458)
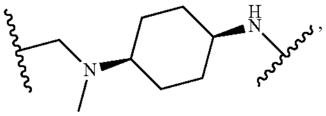 [SMILES: *CN(C)[C@H]1CC[C@@H](N*)CC1]
(459)
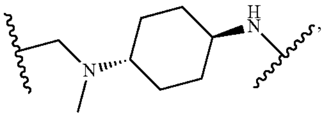 [SMILES: *CN(C)[C@H]1CC[C@H](N*)CC1]
(460)
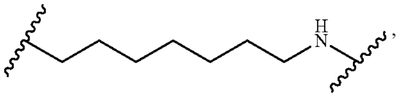 [SMILES: *CCCCCCCN*]
(461)
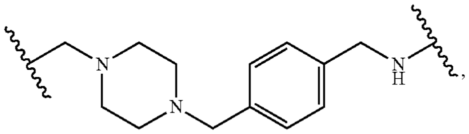 [SMILES: *CN1CCN(Cc2ccc(CN*)cc2)CC1]
(462)
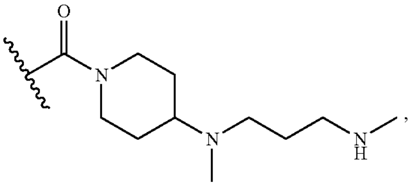 [SMILES: *C(=O)N1CCC(N(C)CCCNC)CC1]
(463)
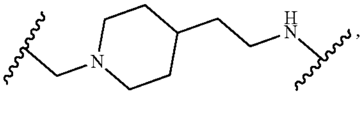 [SMILES: *CN1CCC(CCN*)CC1]
(464)

TABLE B-continued
| Exemplified Linkers (L) |
| --- |
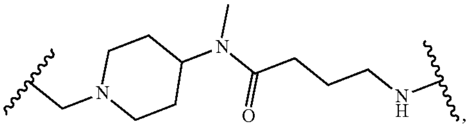 [SMILES: *CN1CCC(N(C)C(=O)CCCN*)CC1]
(465)
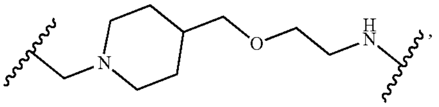 [SMILES: *CN1CCC(COCCN*)CC1]
(466)
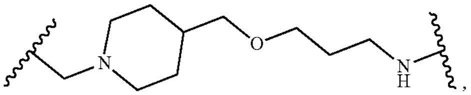 [SMILES: *CN1CCC(COCCCN*)CC1]
(467)
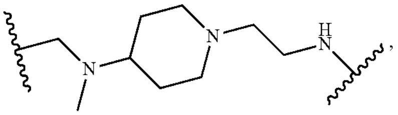 [SMILES: *CN(C)C1CCN(CCN*)CC1]
(468)
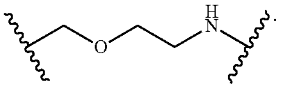 [SMILES: *COCCN*]
(469)
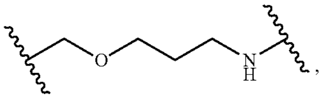 [SMILES: *COCCCN*]
(470)
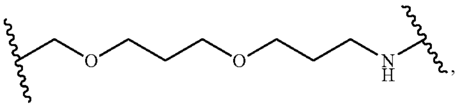 [SMILES: *COCCCOCCCN*]
(471)
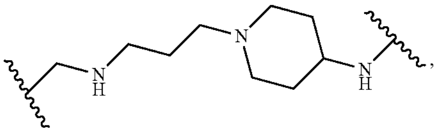 [SMILES: *CNCCCN1CCC(N*)CC1]
(472)
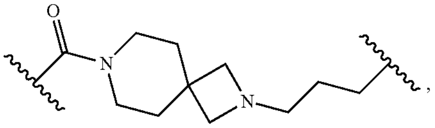 [SMILES: *CCCN1CC2(CCN(C(*)=O)CC2)C1]
(473)
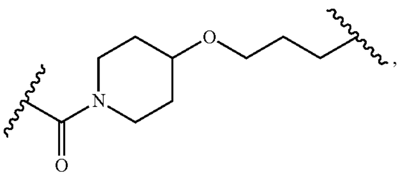 [SMILES: *CCCOC1CCN(C(*)=O)CC1]
(474)
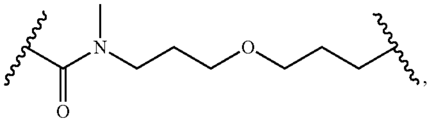 [SMILES: *CCCOCCCN(C)C(*)=O]
(475)

TABLE B-continued
| Exemplified Linkers (L) |
|---|
| 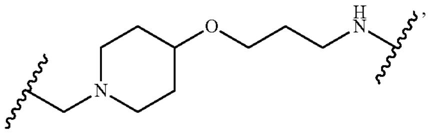 [SMILES: *CN1CCC(OCCCN*)CC1] (475) |
| 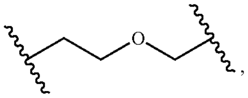 [SMILES: *CCOC*] (476) |
| 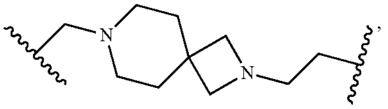 [SMILES: *CCN1CC2(CCN(C*)CC2)C1] (477) |
| 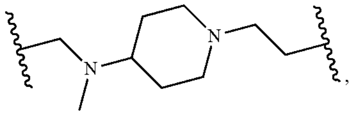 [SMILES: *CCN1CCC(N(C)C*)CC1] (478) |
| 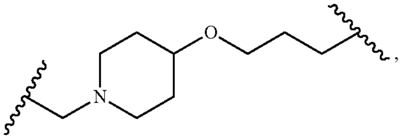 [SMILES: *CCCOC1CCN(C*)CC1] (479) |
| 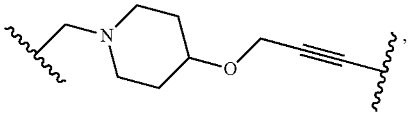 [SMILES: *C#CCOC1CCN(C*)CC1] (480) |
| 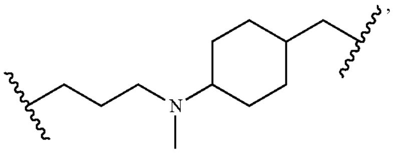 [SMILES: *CCCN(C)C1CCC(C*)CC1] (481) |
| 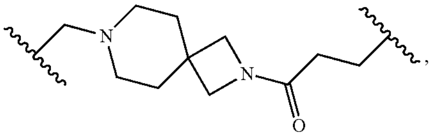 [SMILES: *CCC(=O)N1CC2(CCN(C*)CC2)C1] (482) |
| 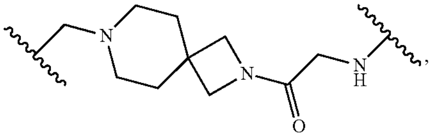 [SMILES: *CN1CCC2(CC1)CN(C(=O)CN*)C2] (483) |
| 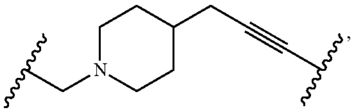 [SMILES: *C#CCC1CCN(C*)CC1] (484) |
| 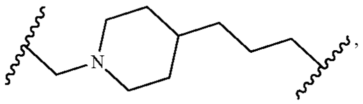 [SMILES: *CCCC1CCN(C*)CC1] (485) |

TABLE B-continued
| Exemplified Linkers (L) |
|---|
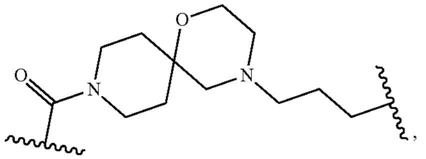 [SMILES: *CCCN1CCOC2(CCN(C(*)=O)CC2)C1]
(486)
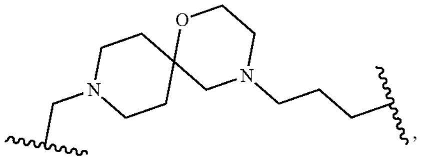 [SMILES: *CCCN1CCOC2(CCN(C*)CC2)C1]
(487)
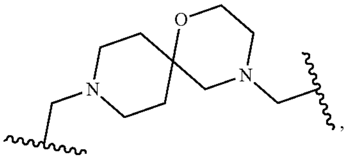 [SMILES: *CN1CCC2(CC1)CN(C*)CCO2]
(488)
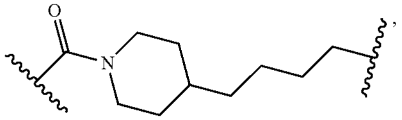
(489)
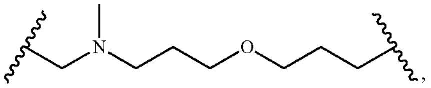 [SMILES: *CCCOCCCN(C)C*]
(490)
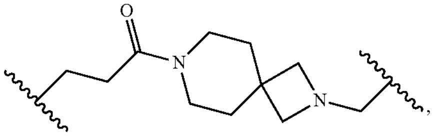 [SMILES: *CCC(=O)N1CCC2(CC1)CN(C*)C2]
(491)
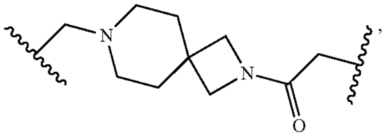 [SMILES: *CC(=O)N1CC2(CCN(C*)CC2)C1]
(492)
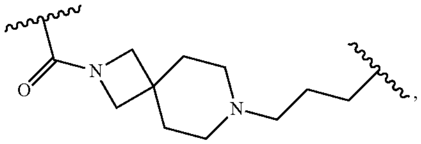 [SMILES: *CCCN1CCC2(CC1)CN(C(*)=O)C2]
(493)
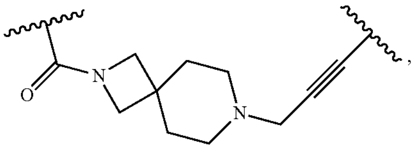 [SMILES: *C#CCN1CCC2(CC1)CN(C(*)=O)C2]
(494)
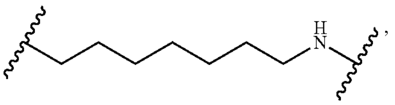 [SMILES: *CCCCCCCN*]
(495)

TABLE B-continued
Exemplified Linkers (L)
(496)
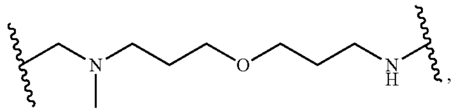 [SMILES: *CN(C)CCCOCCCN*]
(497)
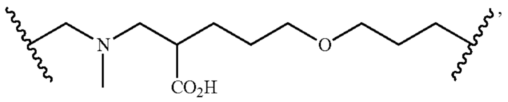 [SMILES: *CCCOCCCC(CN(C)C*)C(=O)O]
(498)
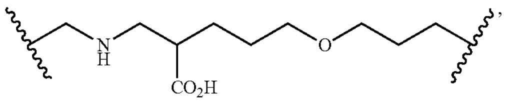 [SMILES: *CCCOCCCC(CNC*)C(=O)O]
(499)
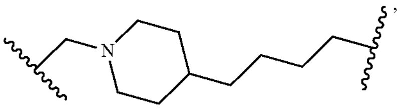 [SMILES: *CCCCC1CCN(C*)CC1]
(500)
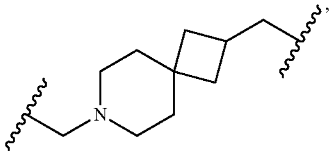 [SMILES: *CC1CC2(CCN(C*)CC2)C1]
(501)
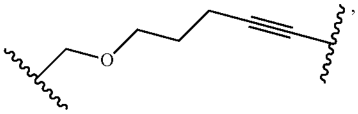 [SMILES: *C#CCCCOC*]
(502)
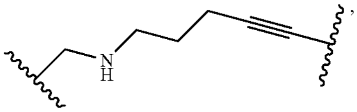 [SMILES: *C#CCCCNC*]
(503)
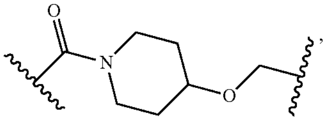 [SMILES: *COC1CCN(C(*)=O)CC1]
(504)
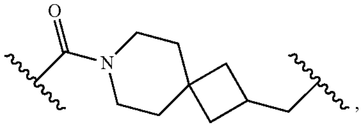 [SMILES: *CC1CC2(CCN(C(*)=O)CC2)C1]
(505)
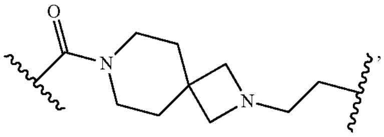 [SMILES: *CCN1CC2(CCN(C(*)=O)CC2)C1]
(506)
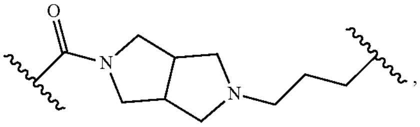 [SMILES: *CCCN1CC2CN(C(*)=O)CC2C1]

TABLE B-continued
Exemplified Linkers (L)
(507)
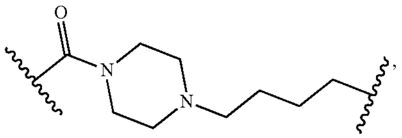 [SMILES: *CCCCN1CCN(C(*)=O)CC1]
(508)
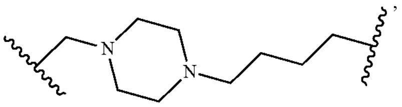 [SMILES: *CCCCN1CCN(C*)CC1]
(509)
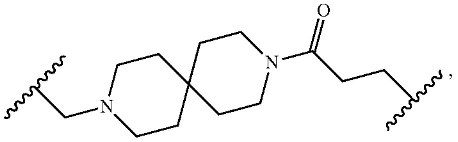 [SMILES: *CCC(=O)N1CCC2(CCN(C*)CC2)CC1]
(510)
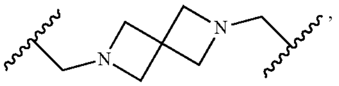 [SMILES: *CN1CC2(C1)CN(C*)C2]
(511)
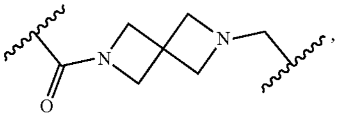 [SMILES: *CN1CC2(C1)CN(C(*)=O)C2]
(512)
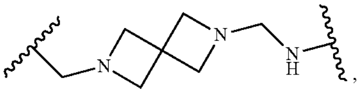 [SMILES: *CN1CC2(C1)CN(CN*)C2]
(513)
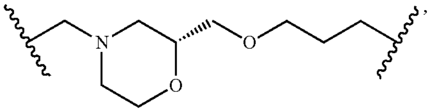 [SMILES: *CCCOC[C@H]1CN(C*)CCO1]
(514)
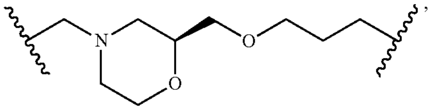 [SMILES: *CCCOC[C@@H]1CN(C*)CCO1]
(515)
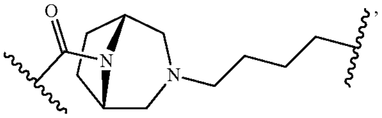 [SMILES: *CCCCN1C[C@H]2CC[C@@H](C1)N2C(*)=O]
(516)
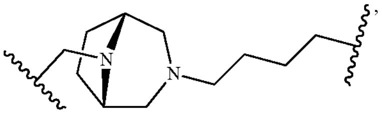 [SMILES: *CCCCN1C[C@H]2CC[C@@H](C1)N2C*]
(517)
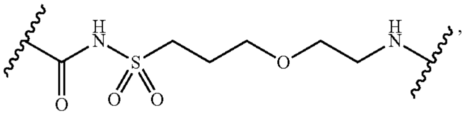 [SMILES: *NCCOCCCS(=O)(=O)NC(*)=O]
(518)
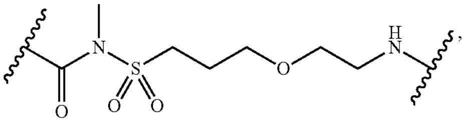 [SMILES: *NCCOCCCS(=O)(=O)N(C)C(*)=O]

TABLE B-continued
| Exemplified Linkers (L) |
|---|
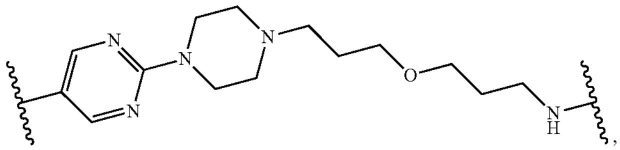 [SMILES: *NCCCOCCCN1CCN(c2ncc(*)cn2)CC1]
(519)
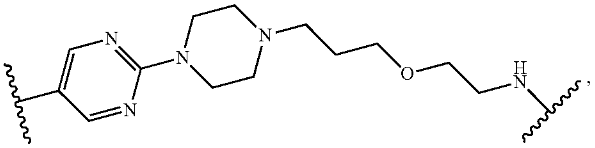 [SMILES: *NCCOCCCN1CCN(c2ncc(*)cn2)CC1]
(520)
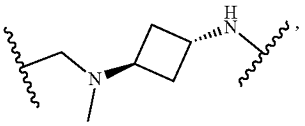 [SMILES: *CN(C)[C@H]1C[C@H](N*)C1]
(521)
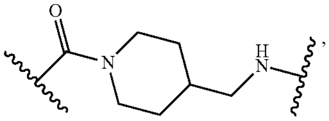 [SMILES: *NCC1CCN(C(*)=O)CC1]
(522)
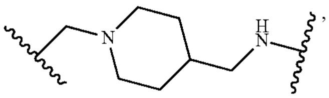 [SMILES: *CN1CCC(CN*)CC1]
(523)
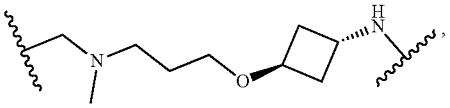 [SMILES: *CN(C)CCCO[C@H]1C[C@H](N*)C1]
(524)
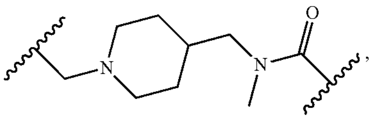 [SMILES: *CN1CCC(CN(C)C(*)=O)CC1]
(525)
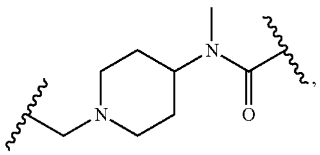 [SMILES: *CN1CCC(N(C)C(*)=O)CC1]
(526)
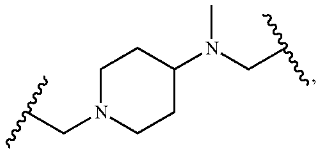 [SMILES: *CN1CCC(N(C)C*)CC1]
(527)
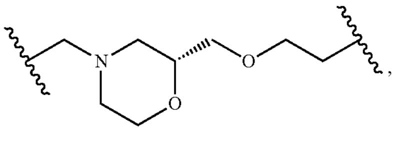 [SMILES: *CCOC[C@H]1CN(C*)CCO1]
(528)

TABLE B-continued
Exemplified Linkers (L)
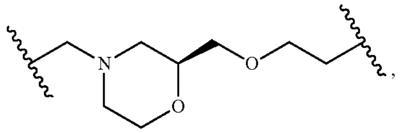 [SMILES: *CCOC[C@@H]1CN(C*)CCO1]
(529)
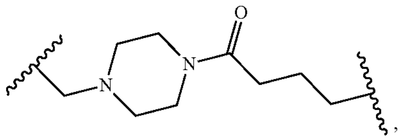 [SMILES: *CCCC(=O)N1CCN(C*)CC1]
(530)
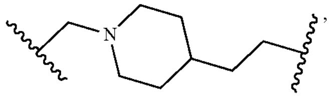 [SMILES: *CCC1CCN(C*)CC1]
(531)
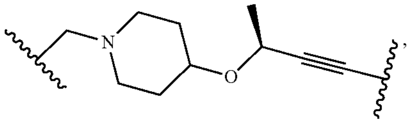 [SMILES: *C#C[C@H](C)OC1CCN(C*)CC1]
(532)
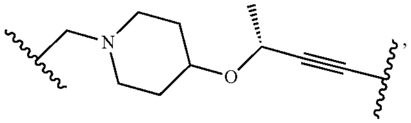 [SMILES: *C#C[C@@H](C)OC1CCN(C*)CC1]
(533)
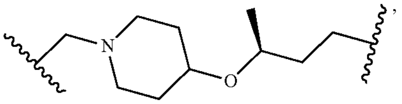 [SMILES: *CC[C@H](C)OC1CCN(C*)CC1]
(534)
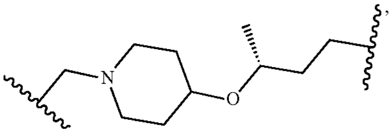 [SMILES: *CC[C@@H](C)OC1CCN(C*)CC1]
(535)
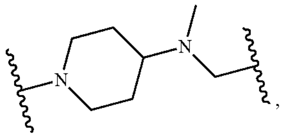 [SMILES: *CN(C)C1CCN(*)CC1]
(536)
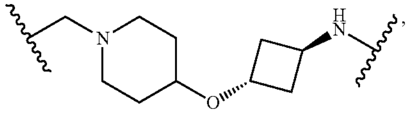 [SMILES: *CN1CCC(O[C@H]2C[C@H](N*)C2)CC1]
(537)
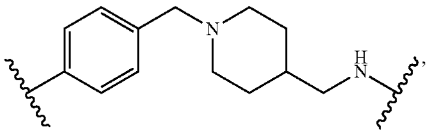 [SMILES: *NCC1CCN(Cc2ccc(*)cc2)CC1]
(538)
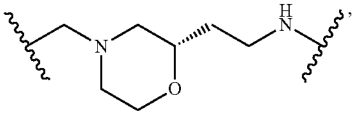 [SMILES: *CN1CCO[C@@H](CCN*)C1]
(539)

TABLE B-continued
| Exemplified Linkers (L) | |
|---|---|
| 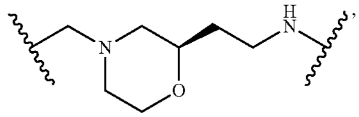 [SMILES: *CN1CCO[C@H](CCN*)C1] | (540) |
| 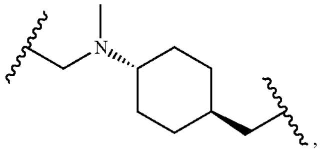 [SMILES: *CN(C)[C@H]1CC[C@H](C*)CC1] | (541) |
| 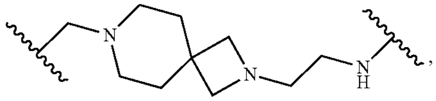 [SMILES: *CN1CCC2(CC1)CN(CCN*)C2] | (542) |
| 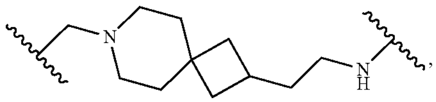 [SMILES: *CN1CCC2(CC1)CC(CCN*)C2] | (543) |
| 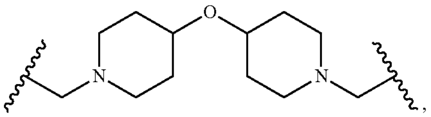 [SMILES: *CN1CCC(OC2CCN(C*)CC2)CC1] | (544) |
| 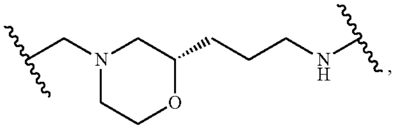 [SMILES: *CN1CCO[C@@H](CCCN*)C1] | (545) |
| 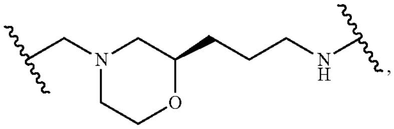 [SMILES: *CN1CCO[C@H](CCCN*)C1] | (546) |
| 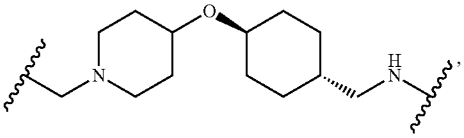 [SMILES: *CN1CCC(O[C@H]2CC[C@H](CN*)CC2)CC1] | (547) |
| 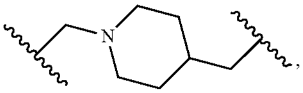 | (548) |
| 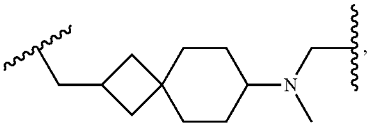 [SMILES: *CC1CC2(CCC(N(C)C*)CC2)C1] | (549) |
| 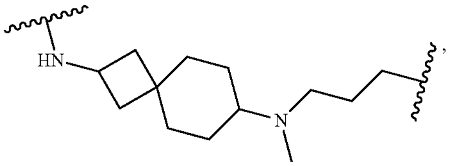 [SMILES: *CCCN(C)C1CCC2(CC1)CC(N*)C2] | (550) |

TABLE B-continued
Exemplified Linkers (L)
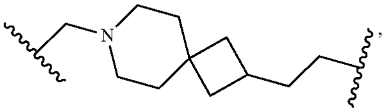 [SMILES: *CCC1CC2(CCN(C*)CC2)C1]
(551)
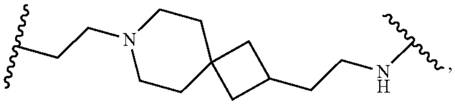 [SMILES: *CCN1CCC2(CC1)CC(CCN*)C2]
(552)
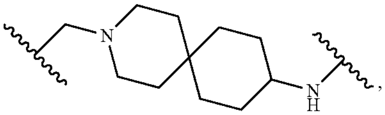 [SMILES: *CN1CCC2(CCC(N*)CC2)CC1]
(553)
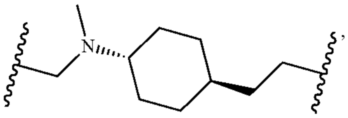 [SMILES: *CC[C@H]1CC[C@H](N(C)C*)CC1]
(554)
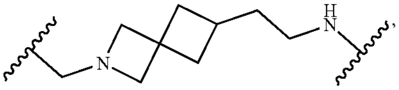 [SMILES: *CN1CC2(CC(CCN*)C2)C1]
(555)
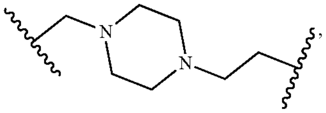 [SMILES: *CCN1CCN(C*)CC1]
(556)
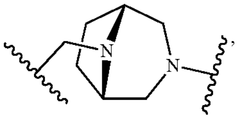 [SMILES: *CN1[C@@H]2CC[C@H]1CN(*)C2]
(557)
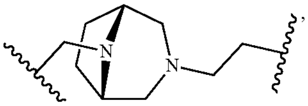 [SMILES: *CCN1C[C@H]2CC[C@@H](C1)N2C*]
(558)
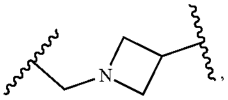 [SMILES: *CN1CC(*)C1]
(559)
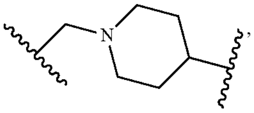 [SMILES: *CN1CCC(*)CC1]
(560)
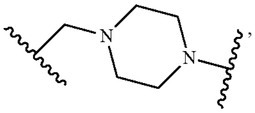 [SMILES: *CN1CCN(*)CC1]
(561)
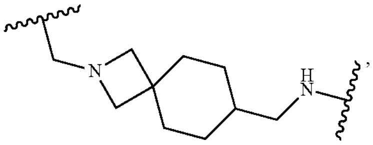 [SMILES: *CN1CC2(CCC(CN*)CC2)C1]
(562)

TABLE B-continued
Exemplified Linkers (L)
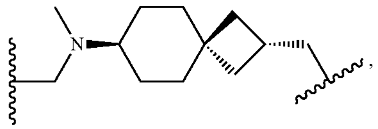
(563)
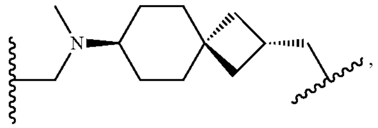
(564)
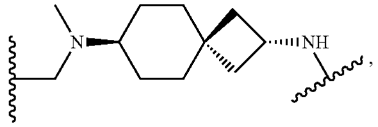
(565)
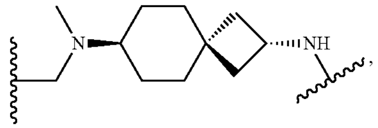
(566)
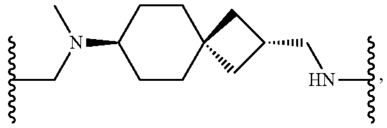
(567)
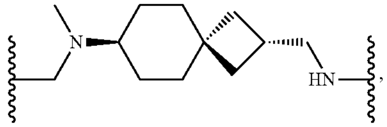
(568)
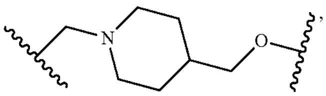 [SMILES: *CN1CCC(CO*)CC1]
(569)
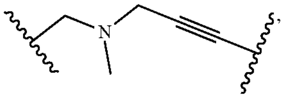 [SMILES: *C#CCN(C)C*]
(570)
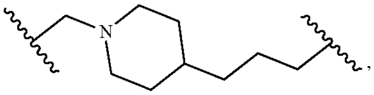 [SMILES: *CCCC1CCN(C*)CC1]
(571)
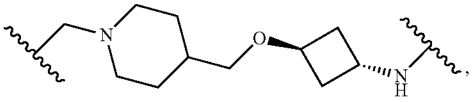 [SMILES: *CN1CCC(CO[C@H]2C[C@H](N*)C2)CC1]
(572)
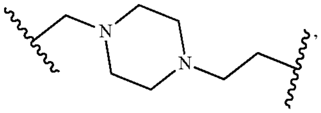 [SMILES: *CCN1CCN(C*)CC1]
(573)
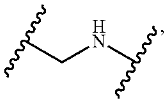 [SMILES: *CN*]
(574)

TABLE B-continued
Exemplified Linkers (L)
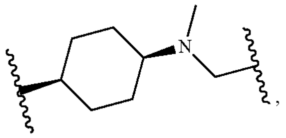 [SMILES: *CN(C)[C@H]1CC[C@@H](*)CC1]
(575)
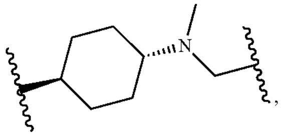 [SMILES: *CN(C)[C@H]1CC[C@H](*)CC1]
(576)
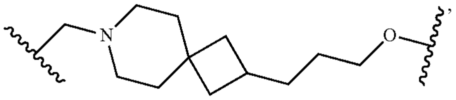 [SMILES: *CN1CCC2(CC1)CC(CCCO*)C2]
(577)
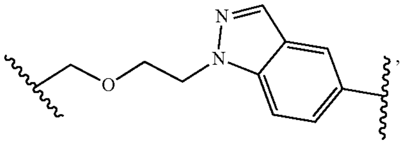 [SMILES: *COCCn1ncc2cc(*)ccc21]
(578)
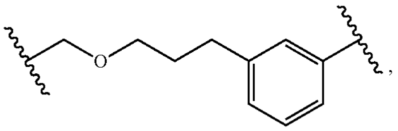 [SMILES: *COCCCc1cccc(*)c1]
(579)
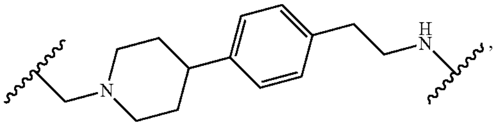 [SMILES: *CN1CCC(c2ccc(CCN*)cc2)CC1]
(580)
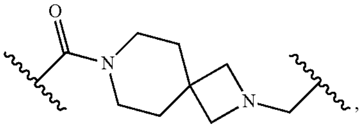 [SMILES: *CN1CC2(CCN(C(*)=O)CC2)C1]
(581)
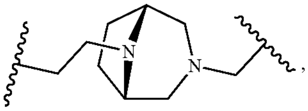 [SMILES: *CCN1[C@@H]2CC[C@H]1CN(C*)C2]
(582)
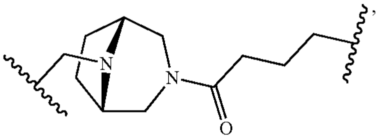 [SMILES: *CCCC(=O)N1C[C@H]2CC[C@@H](C1)N2C*]
(583)
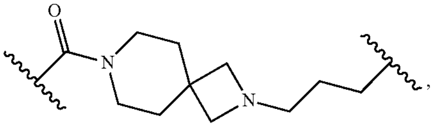 [SMILES: *CCCN1CC2(CCN(C(*)=O)CC2)C1]
(584)
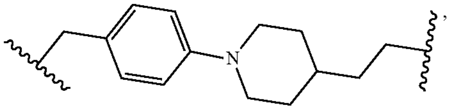 [SMILES: *CCC1CCN(c2ccc(C*)cc2)CC1]
(585)

TABLE B-continued
Exemplified Linkers (L)
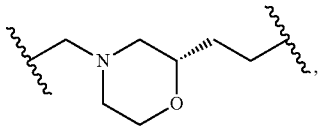 [SMILES: *CC[C@H]1CN(C*)CCO1]
(586)
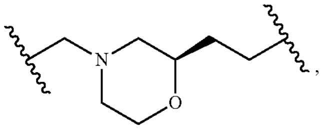 [SMILES: *CC[C@@H]1CN(C*)CCO1]
(587)
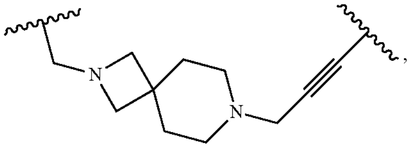 [SMILES: *C#CCN1CCC2(CC1)CN(C*)C2]
(588)
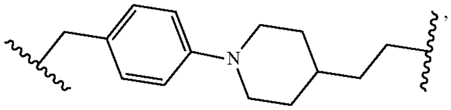 [SMILES: *CCC1CCN(c2ccc(C*)cc2)CC1]
(589)
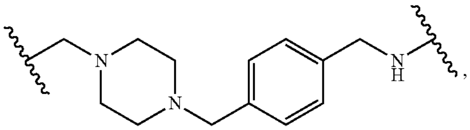 [SMILES: *CN1CCN(Cc2ccc(CN*)cc2)CC1]
(590)
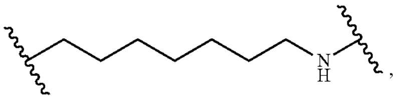 [SMILES: *CCCCCCCN*]
(591)
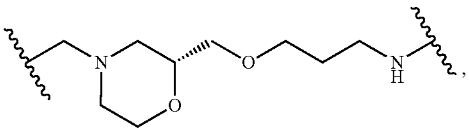 [SMILES: *CN1CCO[C@@H](COCCCN*)C1]
(592)
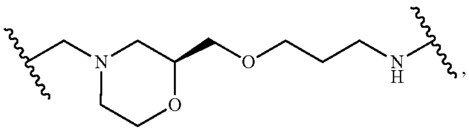 [SMILES: *CN1CCO[C@H](COCCCN*)C1]
(593)
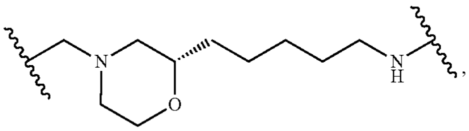 [SMILES: *CN1CCO[C@@H](CCCCCN*)C1]
(594)
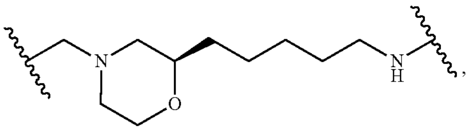 [SMILES: *CN1CCO[C@H](CCCCCN*)C1]
(595)
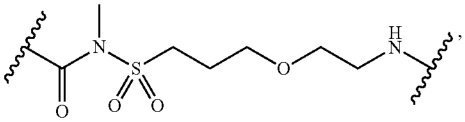 [SMILES: *NCCOCCCS(=O)(=O)N(C)C(*)=O]
(596)

TABLE B-continued
| Exemplified Linkers (L) |
|---|
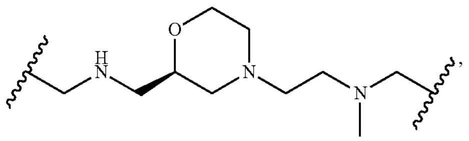 [SMILES: *CNC[C@@H]1CN(CCN(C)C*)CCO1]
(597)
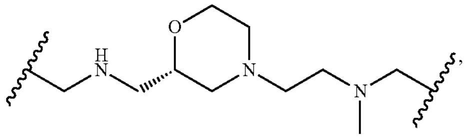 [SMILES: *CNC[C@H]1CN(CCN(C)C*)CCO1]
(598)
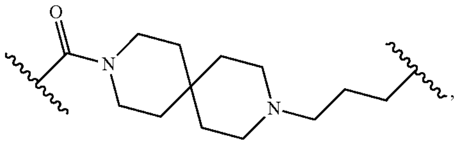 [SMILES: *CCCN1CCC2(CC1)CCN(C(*)=O)CC2]
(599)
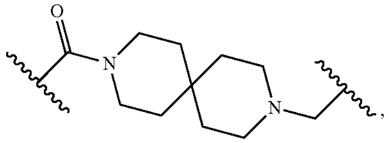 [SMILES: *CN1CCC2(CC1)CCN(C(*)=O)CC2]
(600)
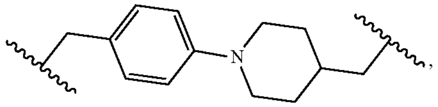 [SMILES: *Cc1ccc(N2CCC(C*)CC2)cc1]
(601)
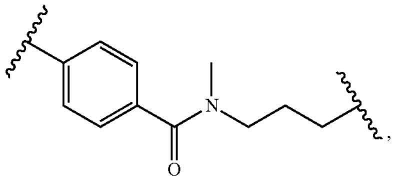 [SMILES: *CCCN(C)C(=O)c1ccc(*)cc1]
(602)
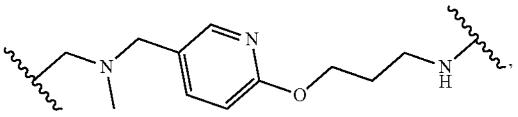 [SMILES: *CN(C)Cc1ccc(OCCCN*)nc1]
(603)
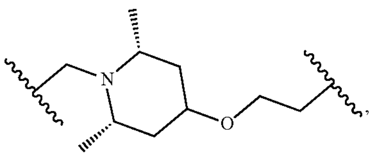 [SMILES: *CCOC1C[C@@H](C)N(C*)[C@@H](C)C1]
(604)
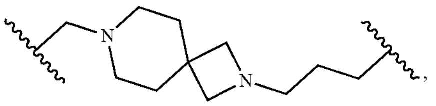 [SMILES: *CCCN1CC2(CCN(C*)CC2)C1]
(605)
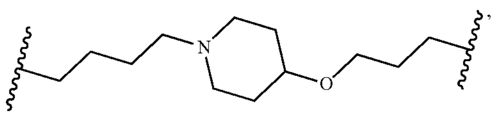 [SMILES: *CCCCN1CCC(OCCC*)CC1]
(606)
and TABLE B-continued
| Exemplified Linkers (L) |
| --- |
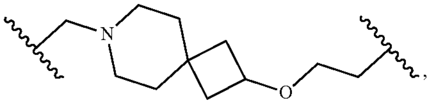 [SMILES: *CCOC1CC2(CCN(C*)CC2)C1]
(607)
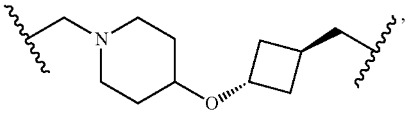 [SMILES: *CN1CCC(O[C@H]2C[C@H](C*)C2)CC1]
(608)
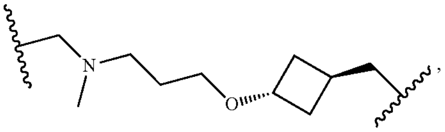 [SMILES: *CN(C)CCCO[C@H]1C[C@H](C*)C1]
(609)
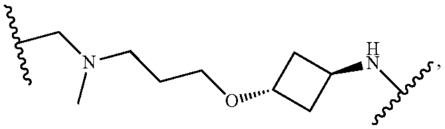 [SMILES: *CN(C)CCCO[C@H]1C[C@H](N*)C1]
(610)
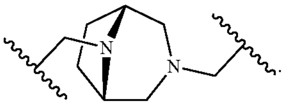 [SMILES: *CN1C[C@H]2CC[C@@H](C1)N2C*]
(611)
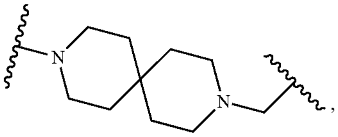 [SMILES: *CN1CCC2(CCN(*)CC2)CC1]
(612)
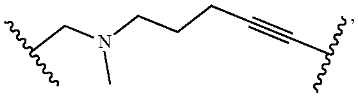 [SMILES: *C#CCCCN(C)C*]
(613)
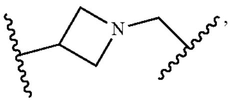 [SMILES: *CN1CC(*)C1]
(614)
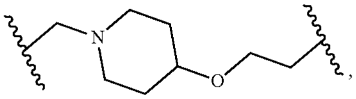 [SMILES: *CCOC1CCN(C*)CC1]
(615)
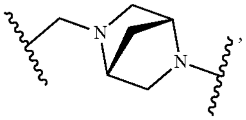 [SMILES: *CN1C[C@H]2C[C@@H]1CN2*]
(616)
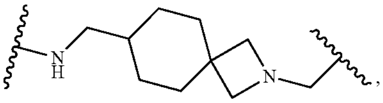 [SMILES: *CN1CC2(CCC(CN*)CC2)C1]
(617)
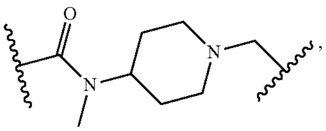 [SMILES: *CN1CCC(N(C)C(*)=O)CC1]
(618)

TABLE B-continued
| Exemplified Linkers (L) | |
|---|---|
| 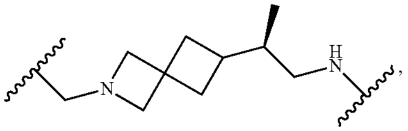 [SMILES: *CN1CC2(CC([C@@H](C)CN*)C2)C1] | (619) |
| 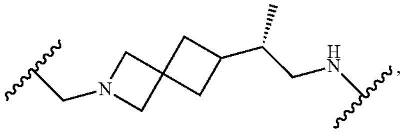 [SMILES: *CN1CC2(CC([C@H](C)CN*)C2)C1] | (620) |
| 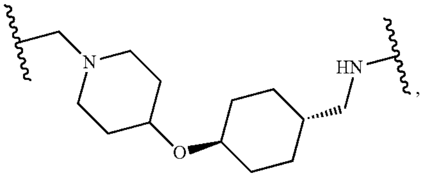 [SMILES: *CN1CCC(O[C@H]2CC[C@H](CN*)CC2)CC1] | (621) |
| 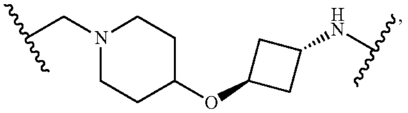 [SMILES: *CN1CCC(O[C@H]2C[C@H](N*)C2)CC1] | (622) |
| 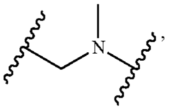 | (623) |
| 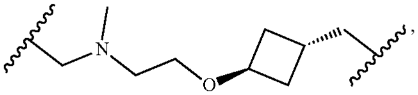 [SMILES: *CN(C)CCO[C@H]1C[C@H](C*)C1] | (624) |
| 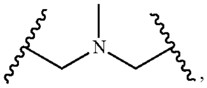 [SMILES: *CN(C)C*] | (625) |
| 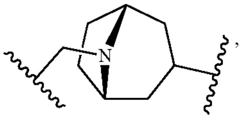 [SMILES: *CN1[C@@H]2CC[C@H]1CC(*)C2] | (626) |
| 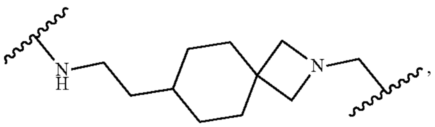 [SMILES: *CN1CC2(CCC(CCN*)CC2)C1] | (627) |
| 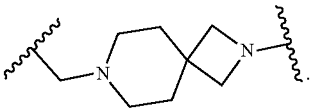 [SMILES: *CN1CCC2(CC1)CN(*)C2] | (628) |

In some embodiments, the present invention provides a compound having an TRAK binding moiety described and disclosed herein, a LBM set forth in Table A above, and a linker set forth in Table B above, or a pharmaceutically acceptable salt thereof.
Exemplary compounds of the invention are set forth in Table 1, below.
TABLE 1
| Exemplary Compounds | |
|---|---|
| I-# | Structure |
| I-1 | 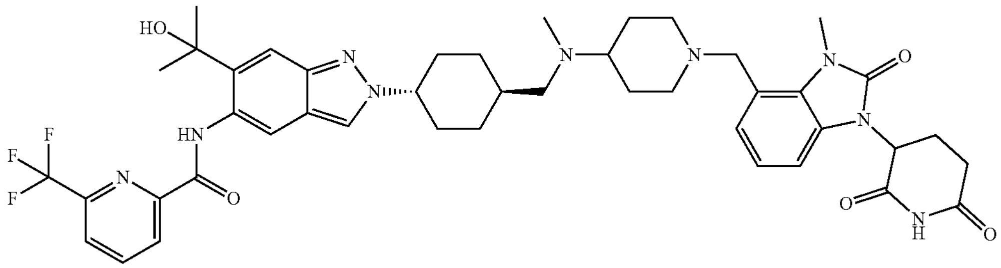 |
| I-2 | 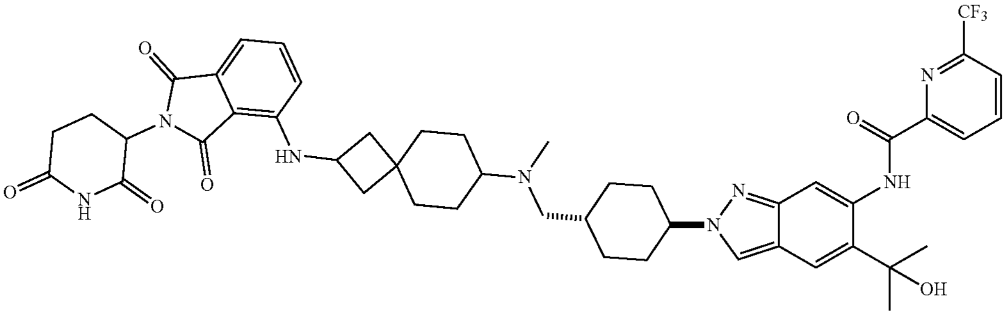 |
| I-3 | 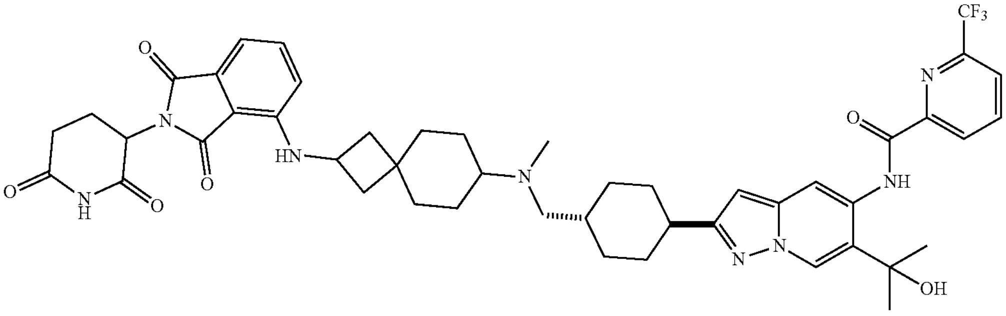 |
| I-4 | 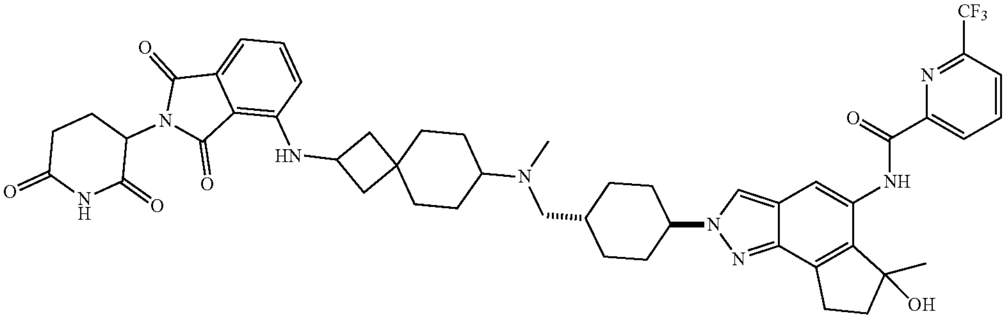 |

TABLE 1-continued
| Exemplary Compounds | |
|---|---|
| I-# | Structure |
| I-5 | 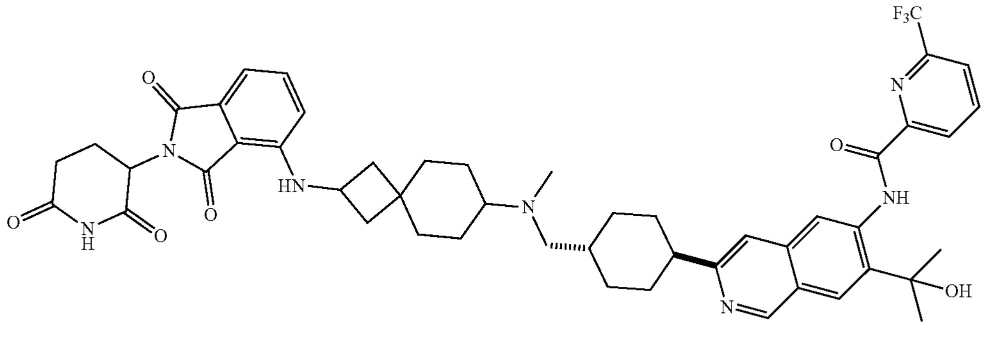 |
| I-6 | 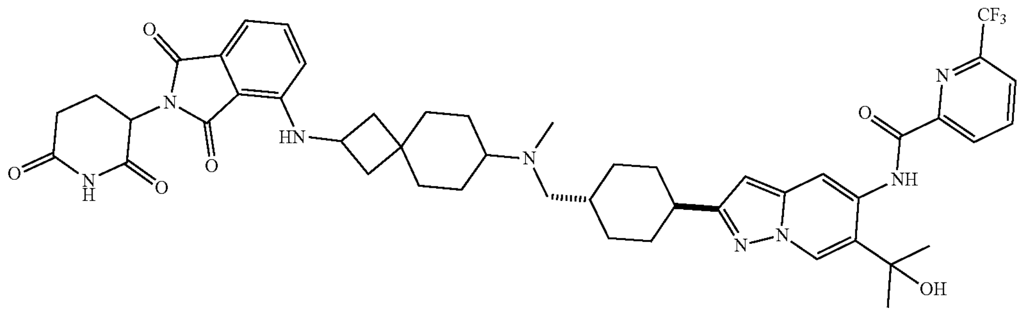 [SMILES: CN(C[C@H]1CC[C@H](c2cc3cc(NC(=O)c4cccc(C(F)(F)F)n4)c(C(C)(C)O)cn3n2)CC1)C1CCC2(CC1)CC(Nc1cccc3c1C(=O)N(C1CCC(=O)NC1=O)C3=O)C2] |
| I-7 | 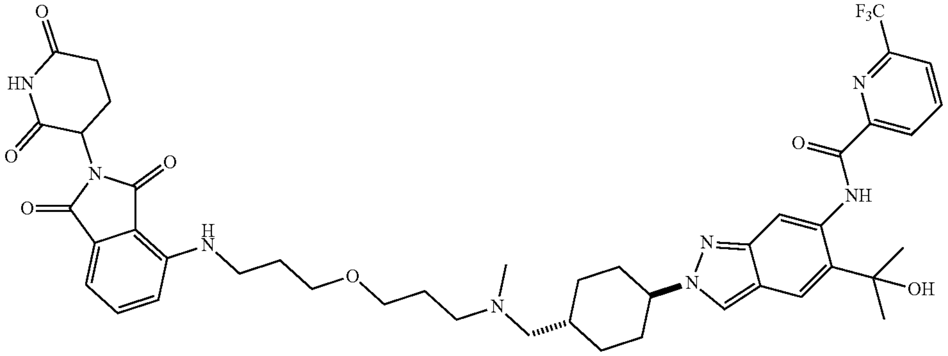 |
| I-8 | 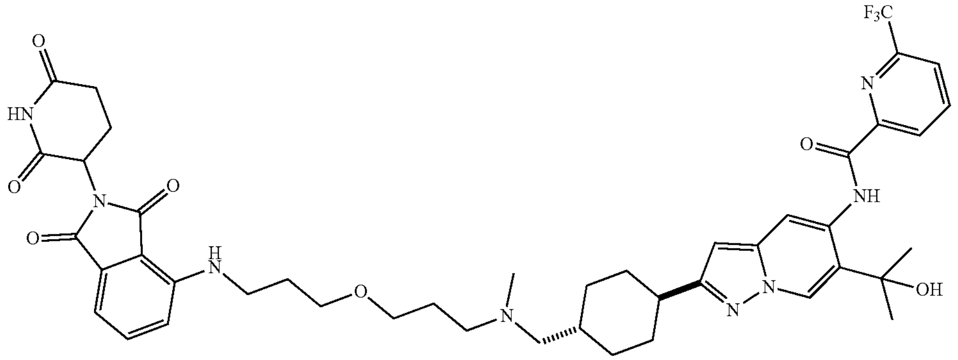 |

TABLE 1-continued
| Exemplary Compounds | |
|---|---|
| I-# | Structure |
| I-9 | 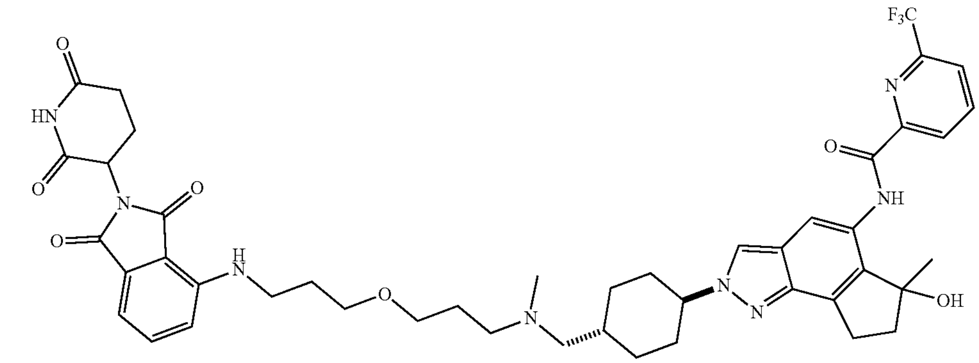 |
| I-10 | 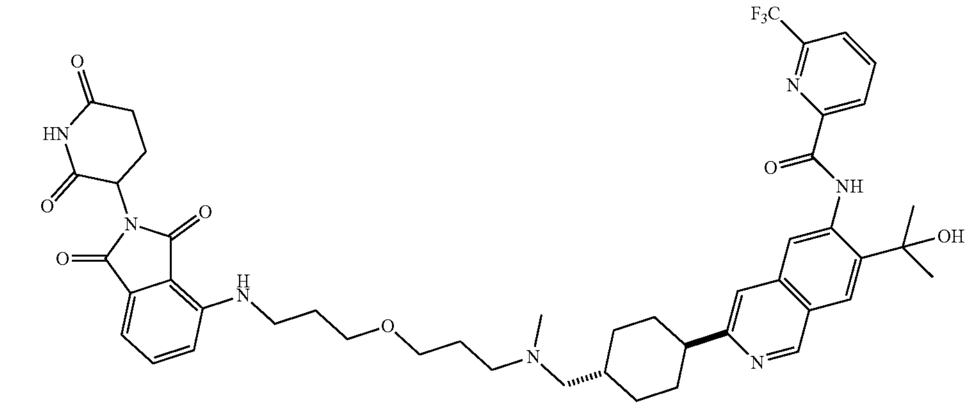 |
| I-11 | 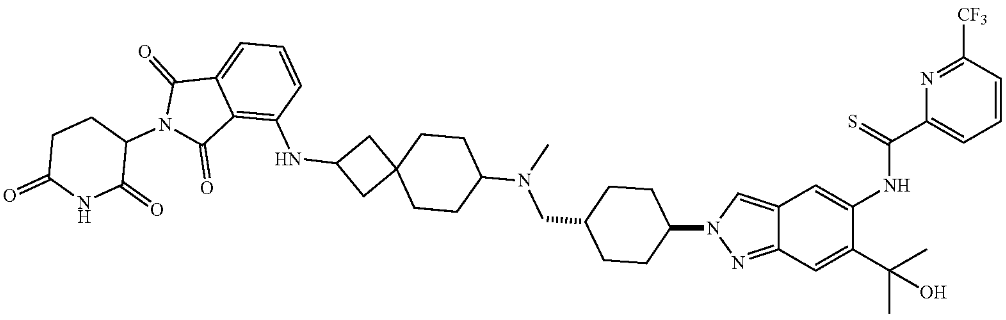 |
| I-12 | 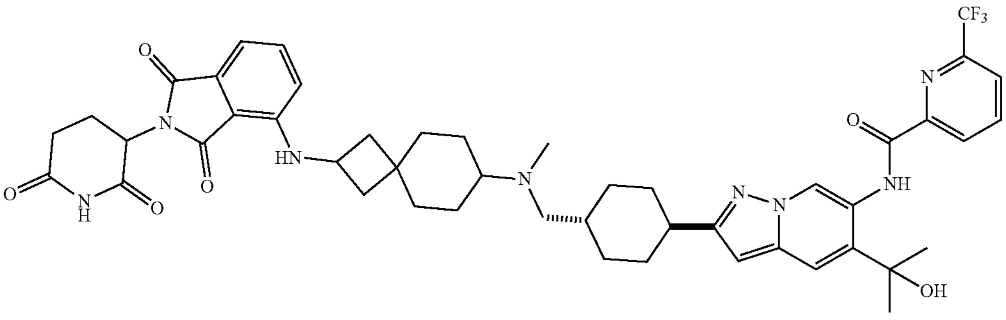 |

TABLE 1-continued
| Exemplary Compounds | |
|---|---|
| I-# | Structure |
| I-13 | 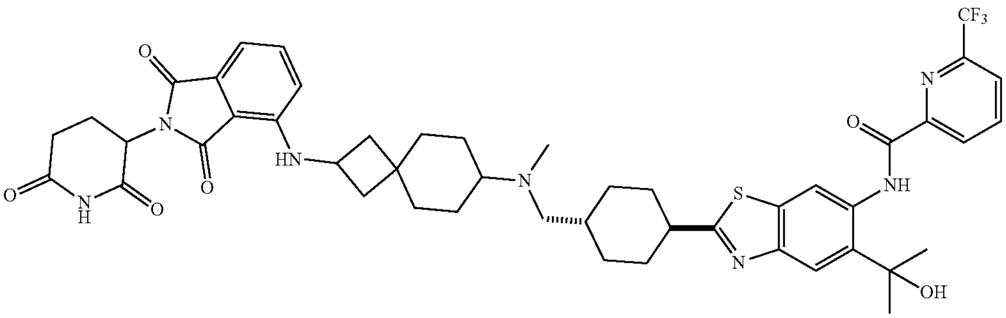 |
| I-14 | 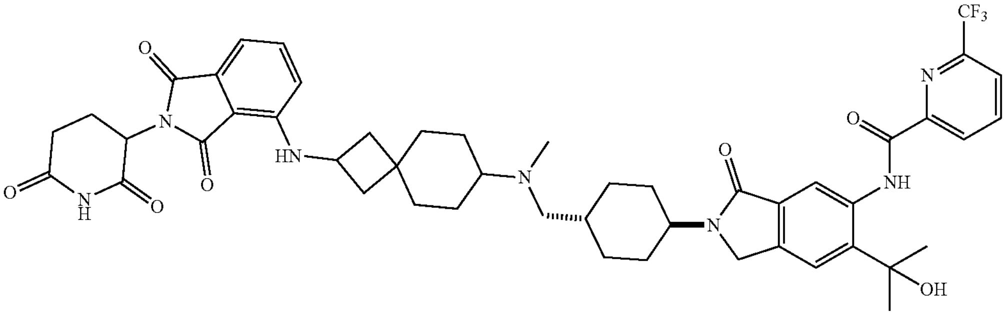 |
| I-15 | 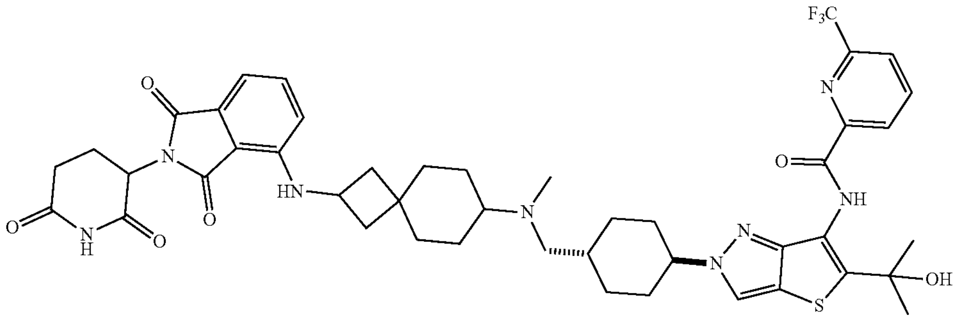 [SMILES: CN(C[C@H]1CC[C@H](n2cc3sc(C(C)(C)O)c(NC(=O)c4cccc(C(F)(F)F)n4)c3n2)CC1)C1CCC2(CC1)CC(Nc1cccc3c1C(=O)N(C1CCC(=O)NC1=O)C3=O)C2] |
| I-16 | 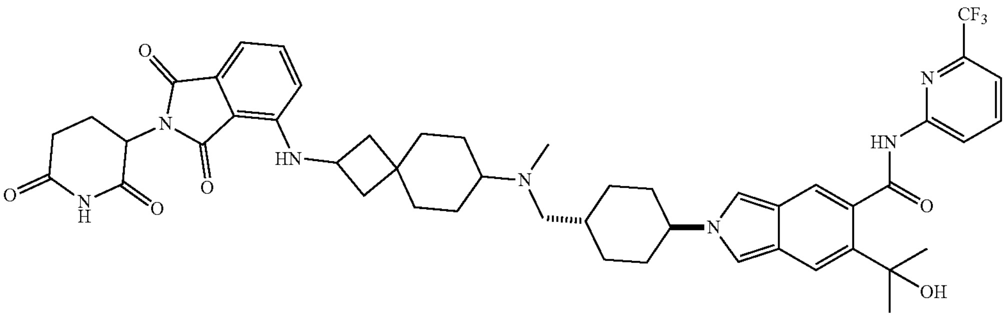 |

TABLE 1-continued
| Exemplary Compounds | |
|---|---|
| I-# | Structure |
| I-17 | 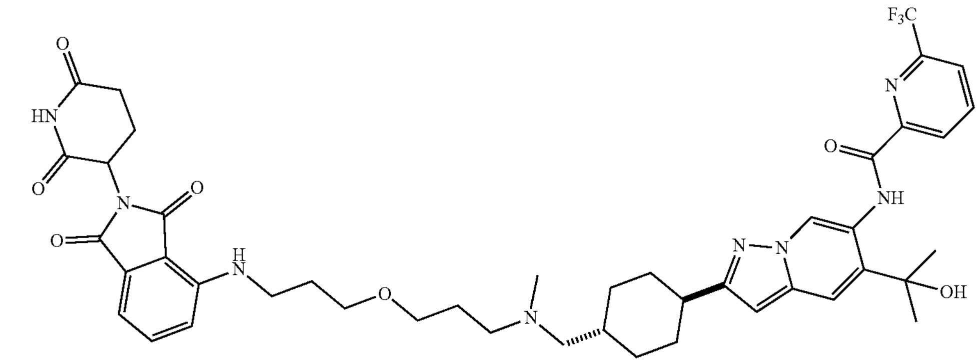 |
| I-18 | 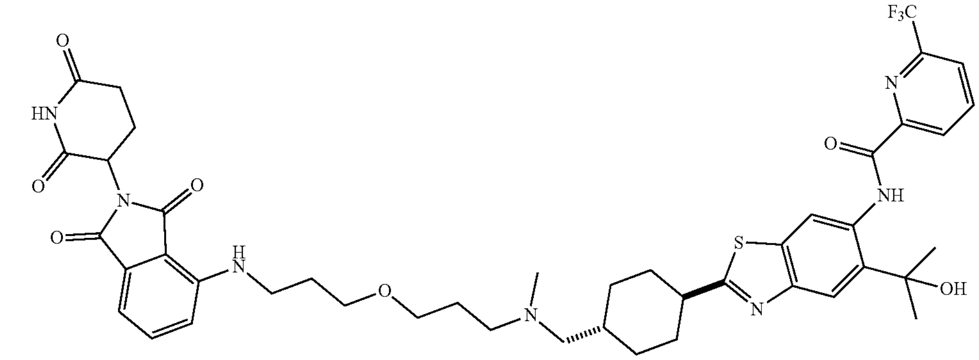 |
| I-19 | 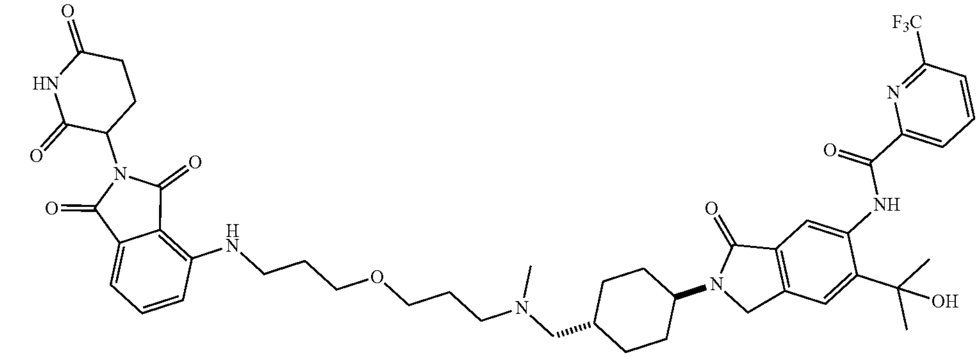 |
| I-20 | 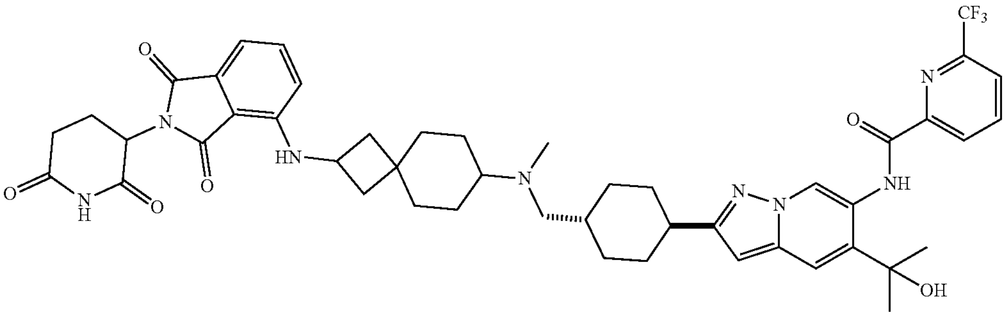 |

TABLE 1-continued
| Exemplary Compounds | |
|---|---|
| I-# | Structure |
| I-21 | 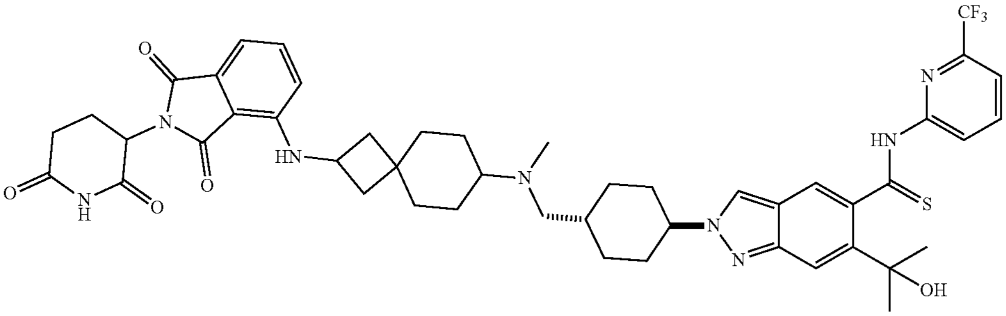 |
| I-22 | 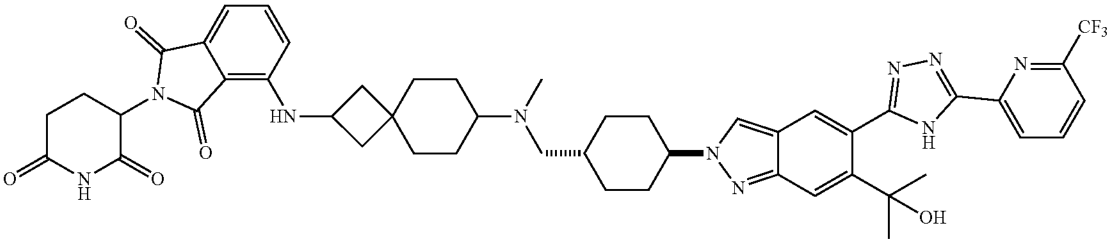 |
| I-23 | 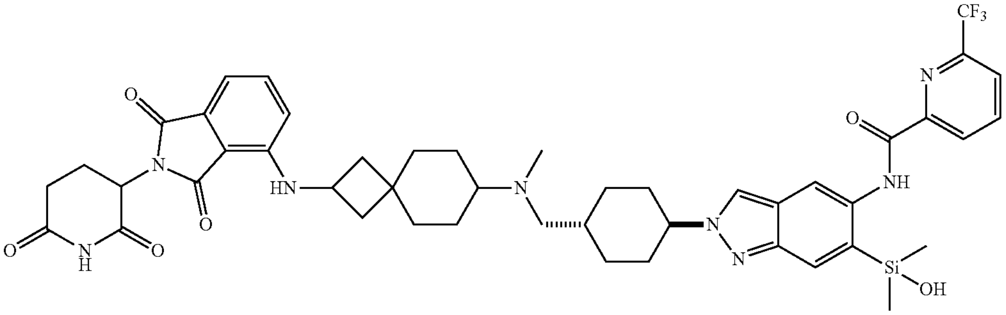 |
| I-24 | 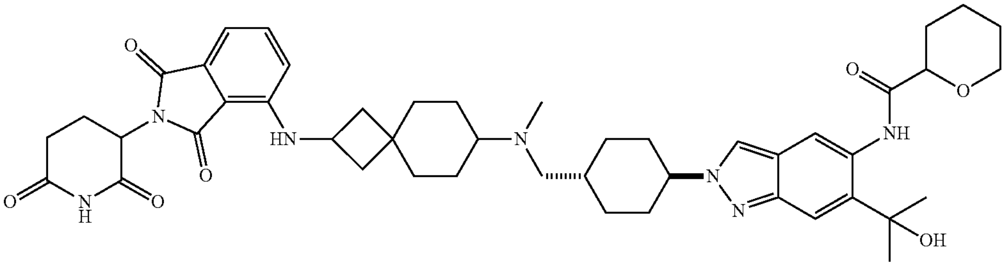 |
| I-25 | 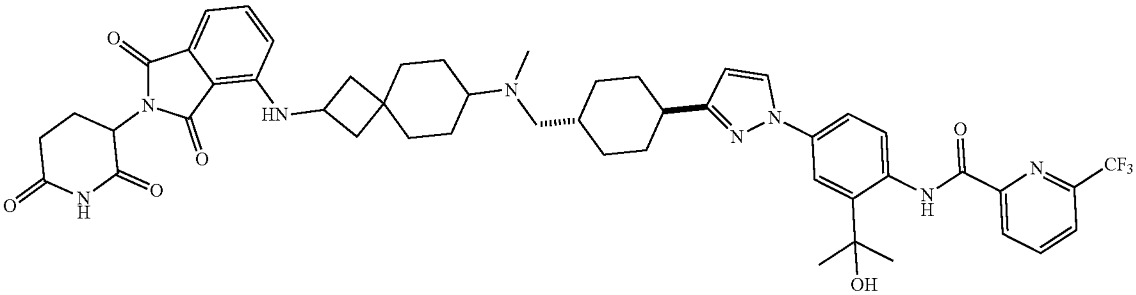 |

TABLE 1-continued
| Exemplary Compounds | |
|---|---|
| I-# | Structure |
| I-26 | 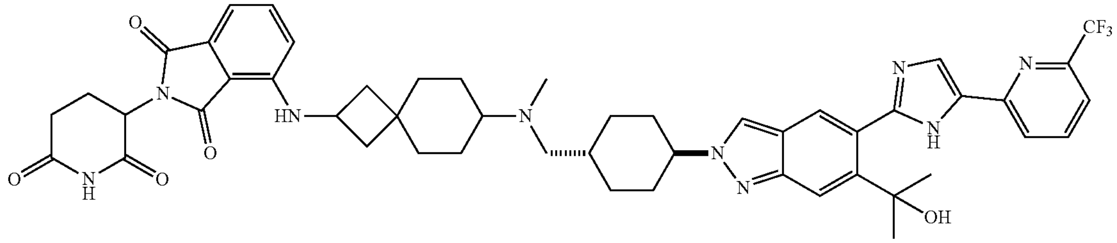 |
| I-27 | 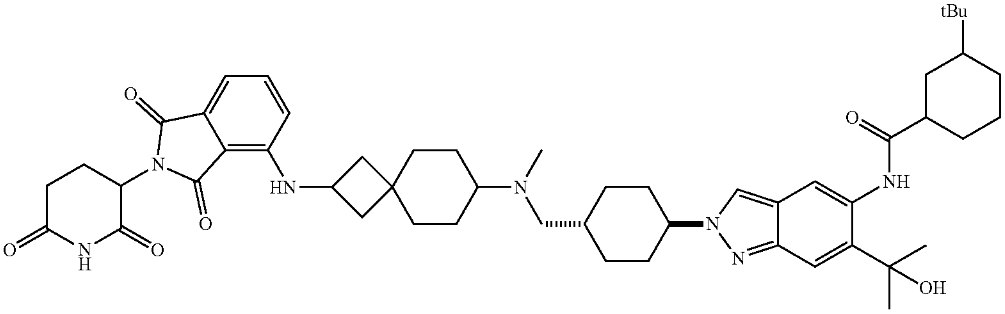 |
| I-28 | 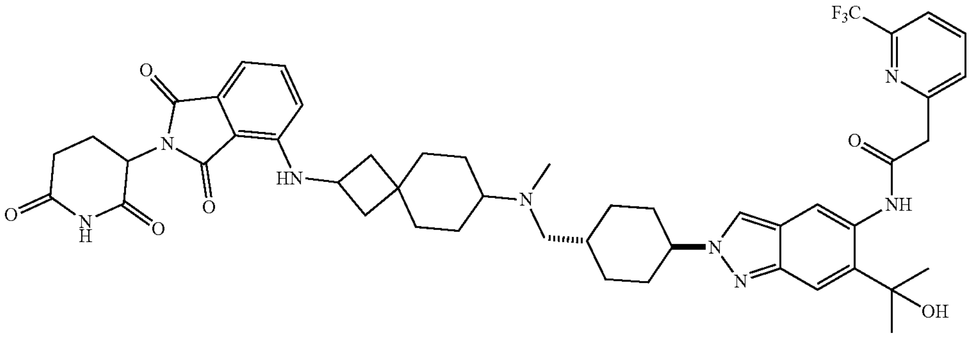 |
| I-29 | 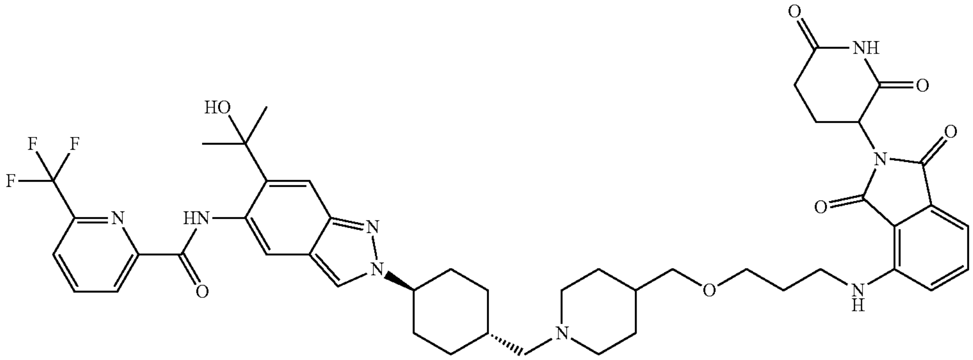 [SMILES: CC(C)(O)c1cc2nn([C@H]3CC[C@H](CN4CCC(COCCCNc5cccc6c5C(=O)N(C5CCC(=O)NC5=O)C6=O)CC4)CC3)cc2cc1NC(=O)c1cccc(C(F)(F)F)n1] |

TABLE 1-continued
| Exemplary Compounds | |
|---|---|
| I-# | Structure |
| I-31 | 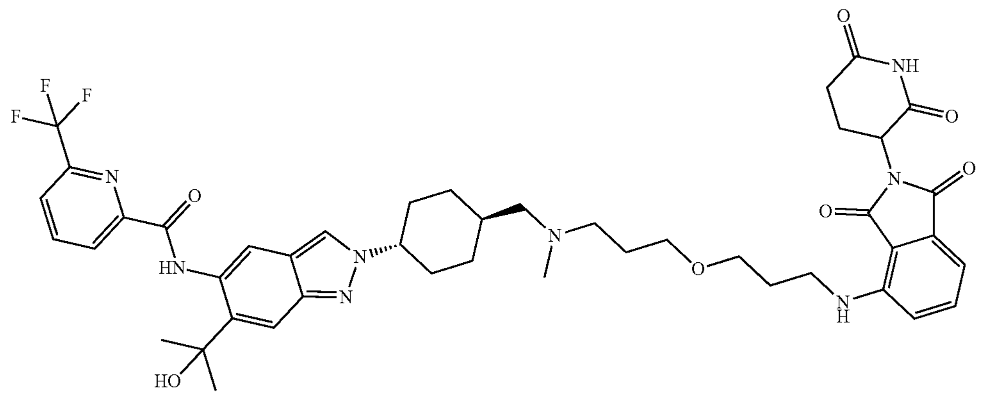 [SMILES: CN(CCCOCCCNc1cccc2c1C(=O)N(C1CCC(=O)NC1=O)C2=O)C[C@H]1CC[C@H](n2cc3cc(NC(=O)c4cccc(C(F)(F)F)n4)c(C(C)(C)O)cc3n2)CC1] |
| I-32 | 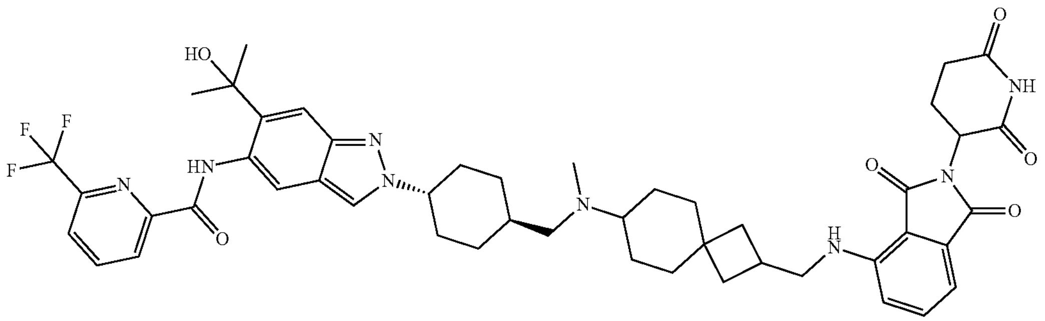 [SMILES: CN(C[C@H]1CC[C@H](n2cc3cc(NC(=O)c4cccc(C(F)(F)F)n4)c(C(C)(C)O)cc3n2)CC1)C1CCC2(CC1)CC(CNc1cccc3c1C(=O)N(C1CCC(=O)NC1=O)C3=O)C2] |
| I-33 | 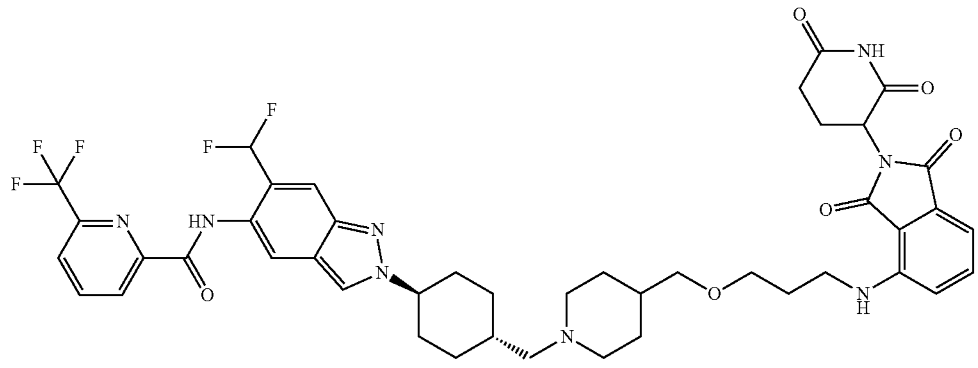 [SMILES: O=C1CCC(N2C(=O)c3cccc(NCCCOCC4CCN(C[C@H]5CC[C@H](n6cc7cc(NC(=O)c8cccc(C(F)(F)F)n8)c(C(F)F)cc7n6)CC5)CC4)c3C2=O)C(=O)N1] |
| I-34 | 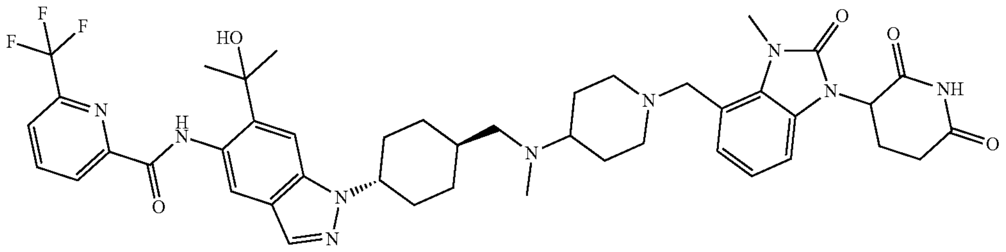 [SMILES: CN(C[C@H]1CC[C@H](n2ncc3cc(NC(=O)c4cccc(C(F)(F)F)n4)c(C(C)(C)O)cc32)CC1)C1CCN(Cc2cccc3c2n(C)c(=O)n3C2CCC(=O)NC2=O)CC1] |

TABLE 1-continued
| Exemplary Compounds | |
|---|---|
| I-# | Structure |
| I-35 | 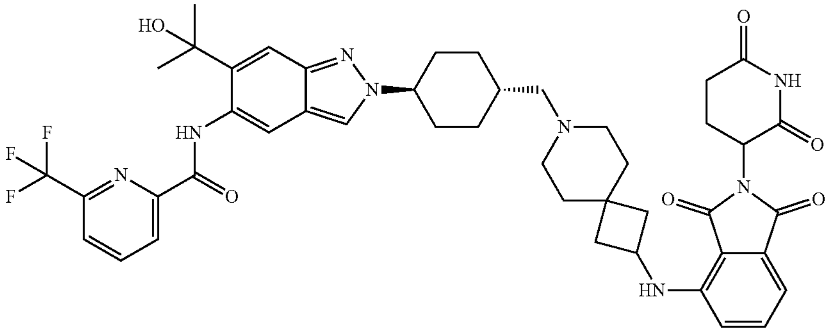 [SMILES: CC(C)(O)c1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cccc(C(F)(F)F)n1] |
| I-36 | 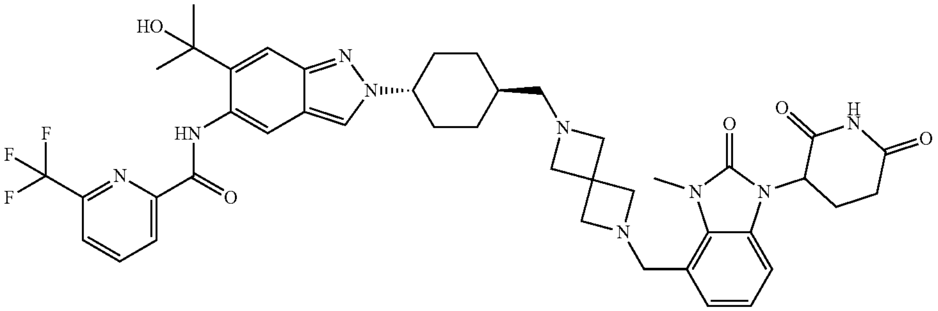 [SMILES: Cn1c(=O)n(C2CCC(=O)NC2=O)c2cccc(CN3CC4(C3)CN(C[C@H]3CC[C@H](n5cc6cc(NC(=O)c7cccc(C(F)(F)F)n7)c(C(C)(C)O)cc6n5)CC3)C4)c21] |
| I-37 | 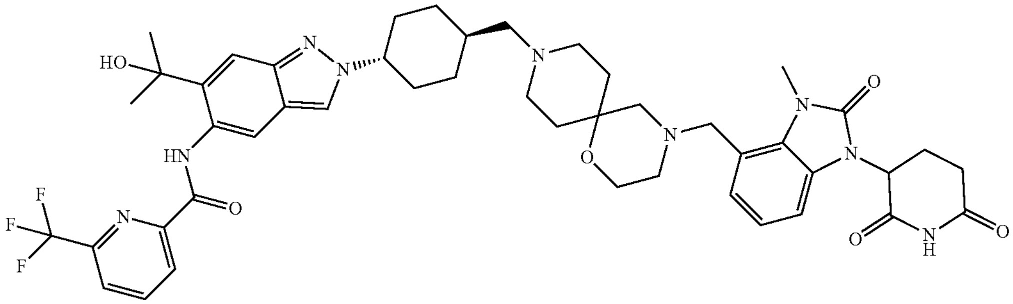 [SMILES: Cn1c(=O)n(C2CCC(=O)NC2=O)c2cccc(CN3CCOC4(CCN(C[C@H]5CC[C@H](n6cc7cc(NC(=O)c8cccc(C(F)(F)F)n8)c(C(C)(C)O)cc7n6)CC5)CC4)C3)c21] |
| I-38 | 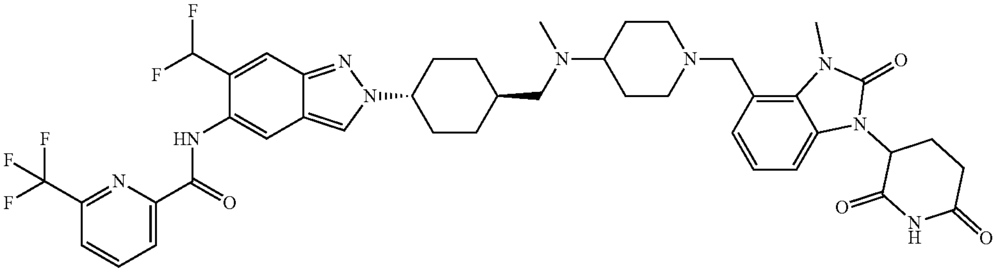 [SMILES: CN(C[C@H]1CC[C@H](n2cc3cc(NC(=O)c4cccc(C(F)(F)F)n4)c(C(F)F)cc3n2)CC1)C1CCN(Cc2cccc3c2n(C)c(=O)n3C2CCC(=O)NC2=O)CC1] |
| I-39 | 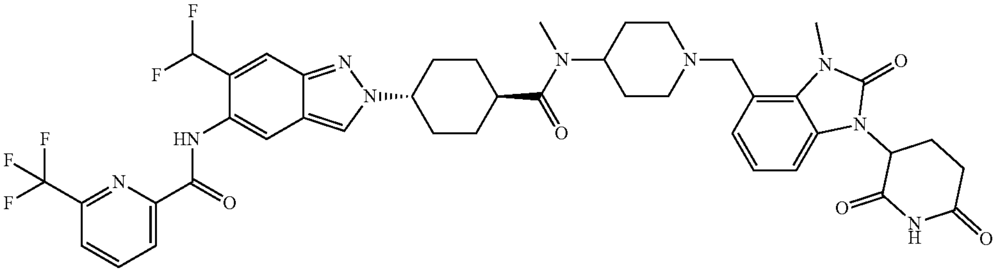 [SMILES: CN(C(=O)[C@H]1CC[C@H](n2cc3cc(NC(=O)c4cccc(C(F)(F)F)n4)c(C(F)F)cc3n2)CC1)C1CCN(Cc2cccc3c2n(C)c(=O)n3C2CCC(=O)NC2=O)CC1] |

TABLE 1-continued
| Exemplary Compounds | |
|---|---|
| I-# | Structure |
| I-40 | 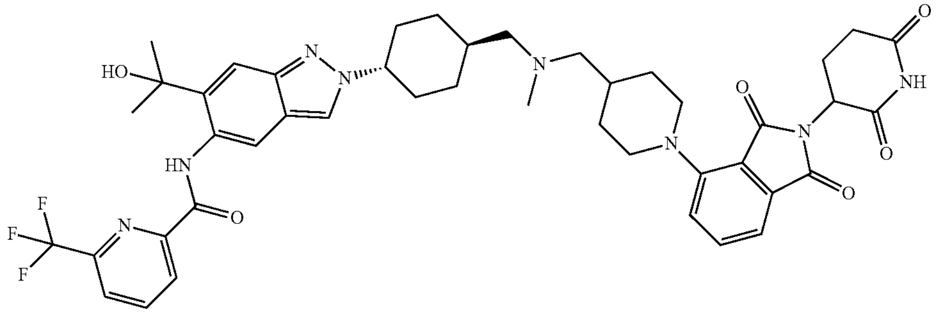 [SMILES: CN(CC1CCN(c2cccc3c2C(=O)N(C2CCC(=O)NC2=O)C3=O)CC1)C[C@H]1CC[C@H](n2cc3cc(NC(=O)c4cccc(C(F)(F)F)n4)c(C(C)(C)O)cc3n2)CC1] |
| I-41 | 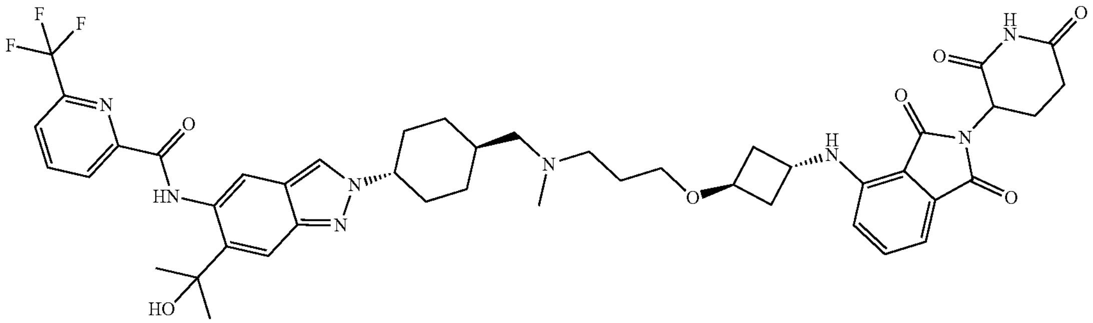 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)c4cccc(C(F)(F)F)n4)c(C(C)(C)O)cc3n2)CC1] |
| I-42 | 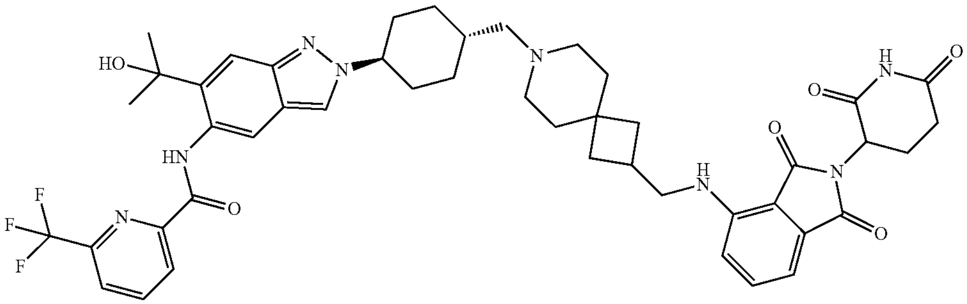 [SMILES: CC(C)(O)c1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(F)(F)F)n1] |
| I-43 | 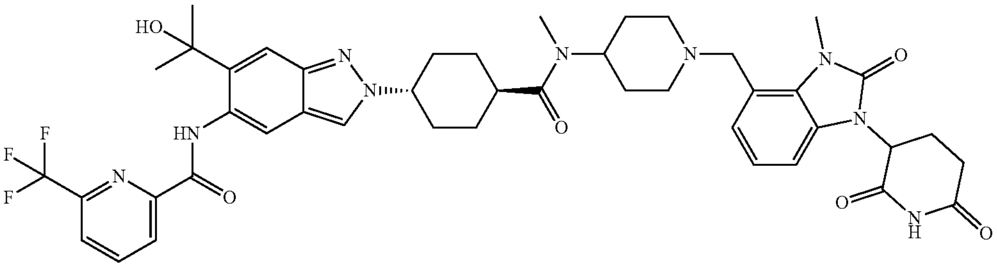 [SMILES: CN(C(=O)[C@H]1CC[C@H](n2cc3cc(NC(=O)c4cccc(C(F)(F)F)n4)c(C(C)(C)O)cc3n2)CC1)C1CCN(Cc2cccc3c2n(C)c(=O)n3C2CCC(=O)NC2=O)CC1] |
| I-44 | 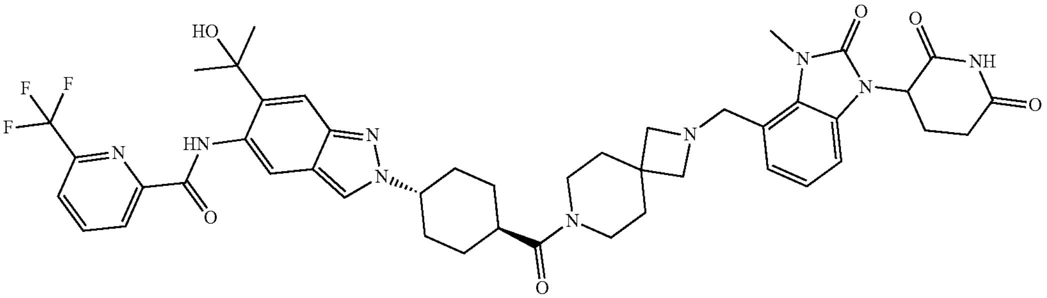 [SMILES: Cn1c(=O)n(C2CCC(=O)NC2=O)c2cccc(CN3CC4(CCN(C(=O)[C@H]5CC[C@H](n6cc7cc(NC(=O)c8cccc(C(F)(F)F)n8)c(C(C)(C)O)cc7n6)CC5)CC4)C3)c21] |

TABLE 1-continued
| Exemplary Compounds | |
|---|---|
| I-# | Structure |
| I-45 | 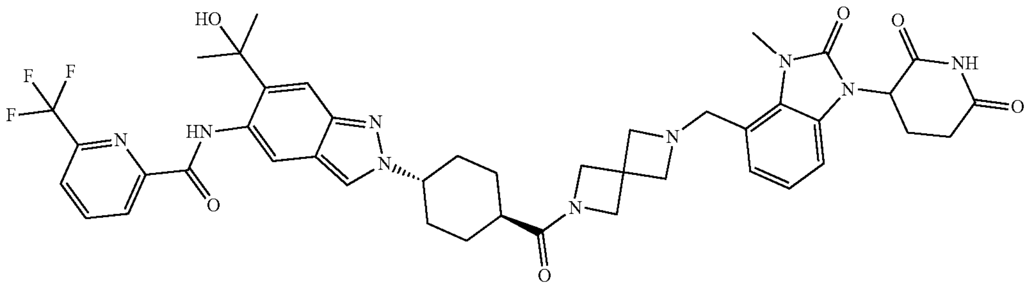 [SMILES: Cn1c(=O)n(C2CCC(=O)NC2=O)c2cccc(CN3CC4(C3)CN(C(=O)[C@H]3CC[C@H](n5cc6cc(NC(=O)c7cccc(C(F)(F)F)n7)c(C(C)(C)O)cc6n5)CC3)C4)c21] |
| I-46 | 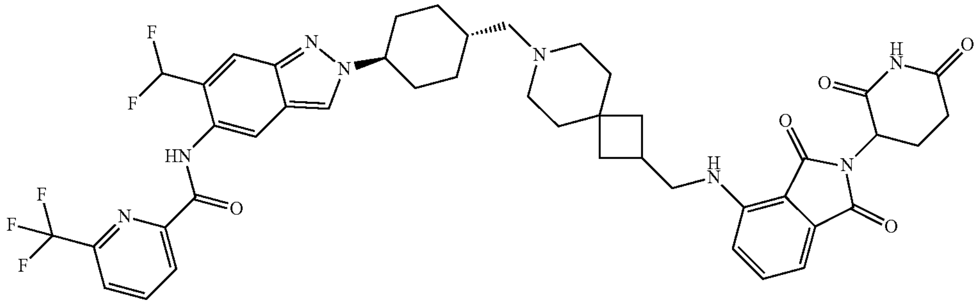 [SMILES: O=C1CCC(N2C(=O)c3cccc(NCC4CC5(CCN(C[C@H]6CC[C@H](n7cc8cc(NC(=O)c9cccc(C(F)(F)F)n9)c(C(F)F)cc8n7)CC6)CC5)C4)c3C2=O)C(=O)N1] |
| I-47 | 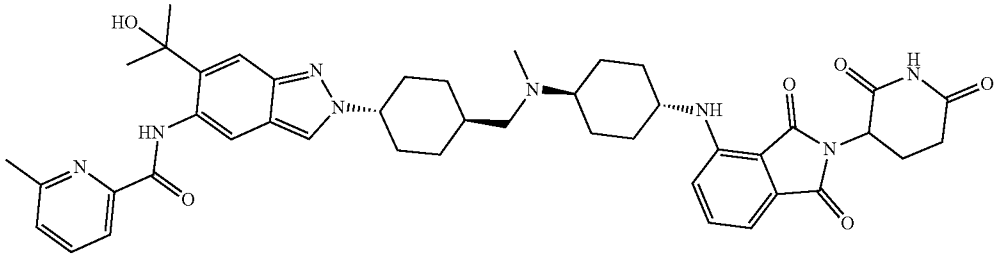 [SMILES: Cc1cccc(C(=O)Nc2cc3cn([C@H]4CC[C@H](CN(C)[C@H]5CC[C@H](Nc6cccc7c6C(=O)N(C6CCC(=O)NC6=O)C7=O)CC5)CC4)nc3cc2C(C)(C)O)n1] |
| I-48 | 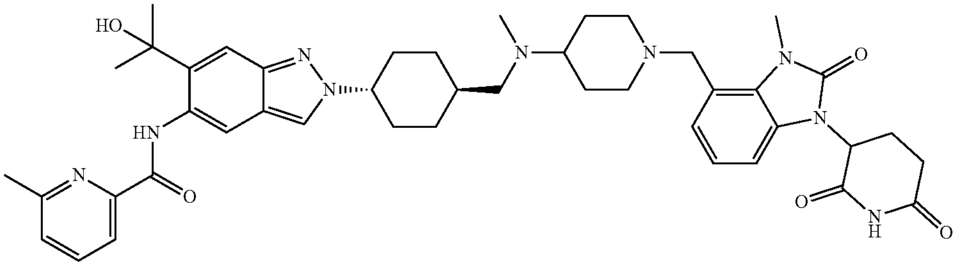 [SMILES: Cc1cccc(C(=O)Nc2cc3cn([C@H]4CC[C@H](CN(C)C5CCN(Cc6cccc7c6n(C)c(=O)n7C6CCC(=O)NC6=O)CC5)CC4)nc3cc2C(C)(C)O)n1] |
| I-49 | 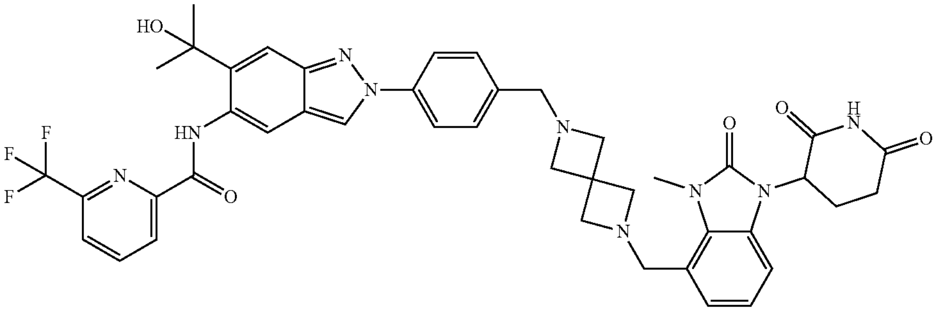 [SMILES: Cn1c(=O)n(C2CCC(=O)NC2=O)c2cccc(CN3CC4(CN(Cc5ccc(-n6cc7cc(NC(=O)c8cccc(C(F)(F)F)n8)c(C(C)(C)O)cc7n6)cc5)C4)C3)c21] |

TABLE 1-continued
| Exemplary Compounds | |
|---|---|
| I-# | Structure |
| I-50 | 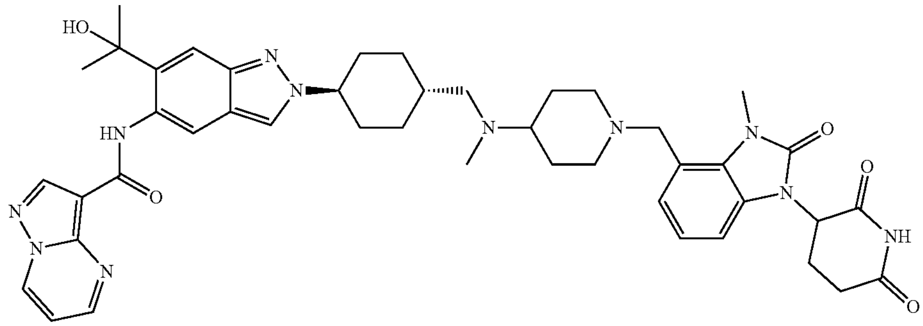 [SMILES: CN(C[C@H]1CC[C@H](n2cc3cc(NC(=O)c4cnn5cccnc45)c(C(C)(C)O)cc3n2)CC1)C1CCN(Cc2cccc3c2n(C)c(=O)n3C2CCC(=O)NC2=O)CC1] |
| I-51 | 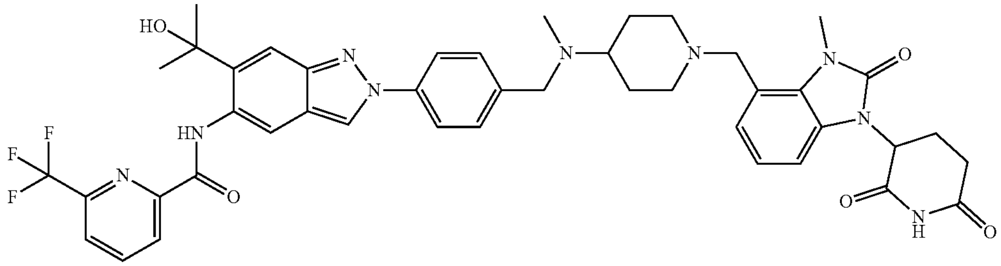 [SMILES: CN(Cc1ccc(-n2cc3cc(NC(=O)c4cccc(C(F)(F)F)n4)c(C(C)(C)O)cc3n2)cc1)C1CCN(Cc2cccc3c2n(C)c(=O)n3C2CCC(=O)NC2=O)CC1] |
| I-52 | 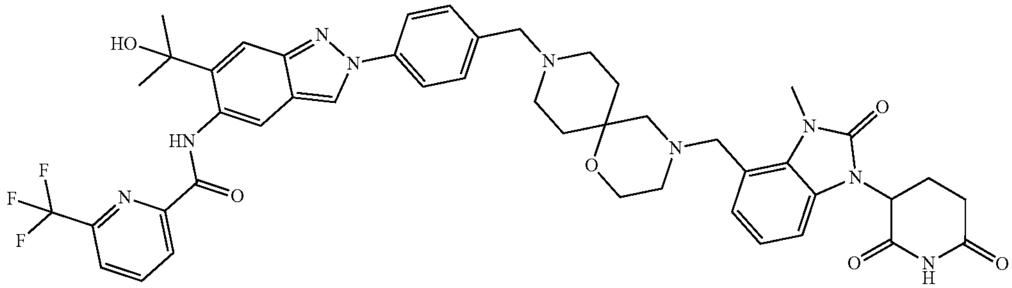 [SMILES: Cn1c(=O)n(C2CCC(=O)NC2=O)c2cccc(CN3CCOC4(CCN(Cc5ccc(-n6cc7cc(NC(=O)c8cccc(C(F)(F)F)n8)c(C(C)(C)O)cc7n6)cc5)CC4)C3)c21] |
| I-53 | 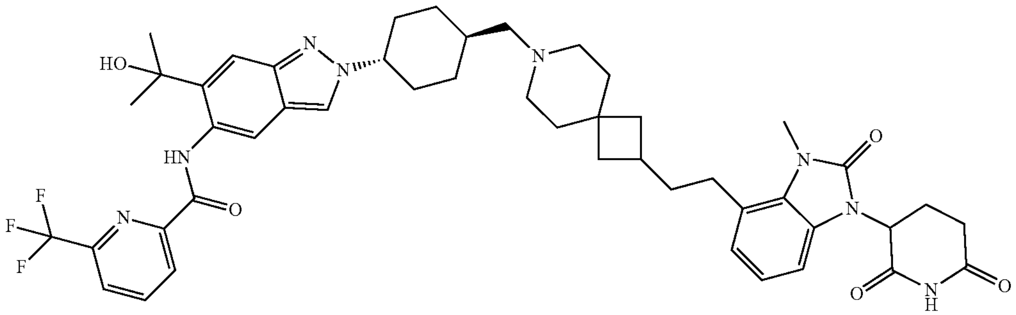 [SMILES: Cn1c(=O)n(C2CCC(=O)NC2=O)c2cccc(CCC3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-54 | 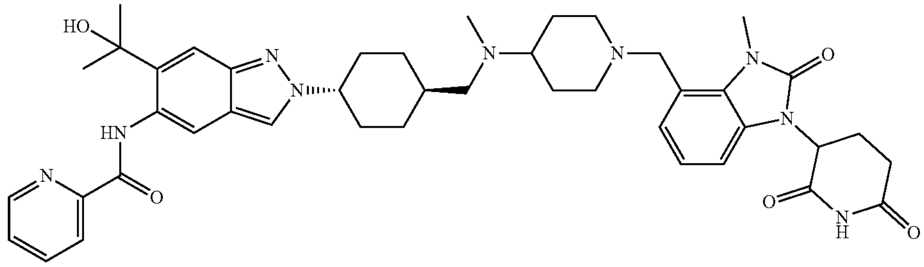 [SMILES: CN(C[C@H]1CC[C@H](n2cc3cc(NC(=O)c4ccccn4)c(C(C)(C)O)cc3n2)CC1)C1CCN(Cc2cccc3c2n(C)c(=O)n3C2CCC(=O)NC2=O)CC1] |

TABLE 1-continued
| Exemplary Compounds | |
|---|---|
| I-# | Structure |
| I-55 | 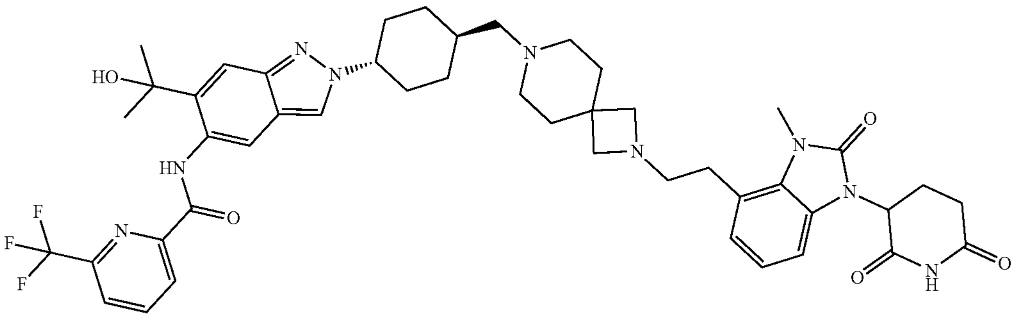 [SMILES: Cn1c(=O)n(C2CCC(=O)NC2=O)c2cccc(CCN3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-56 | 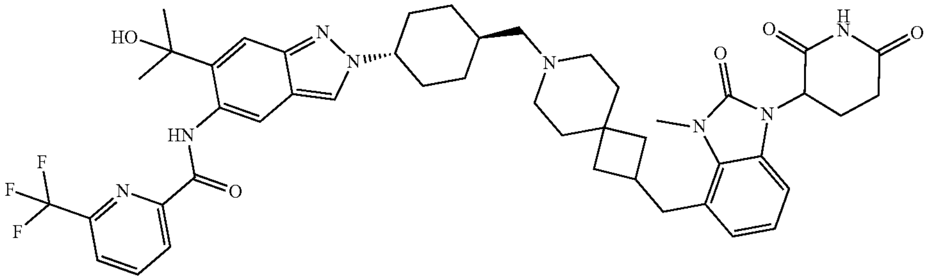 [SMILES: Cn1c(=O)n(C2CCC(=O)NC2=O)c2cccc(CC3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-57 | 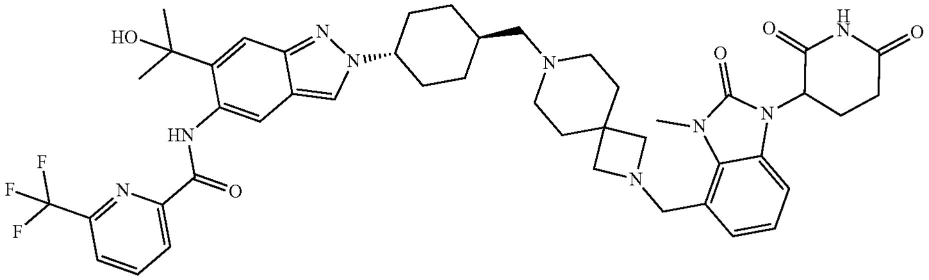 [SMILES: Cn1c(=O)n(C2CCC(=O)NC2=O)c2cccc(CN3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-58 | 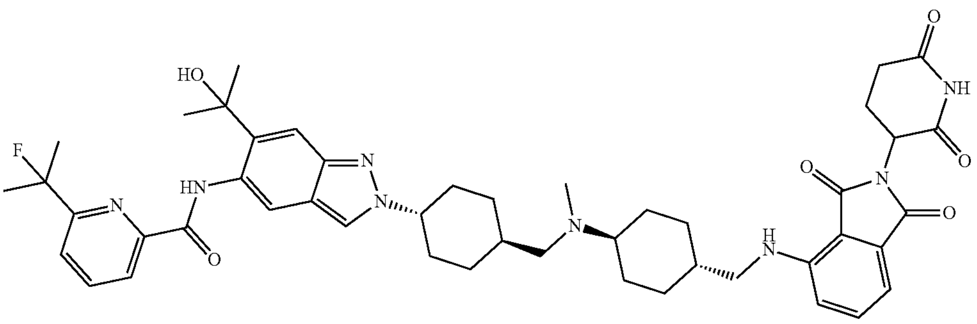 [SMILES: CN(C[C@H]1CC[C@H](n2cc3cc(NC(=O)c4cccc(C(C)(C)F)n4)c(C(C)(C)O)cc3n2)CC1)[C@H]1CC[C@H](CNc2cccc3c2C(=O)N(C2CCC(=O)NC2=O)C3=O)CC1] |

TABLE 1-continued
| Exemplary Compounds | |
|---|---|
| I-# | Structure |
| I-59 | 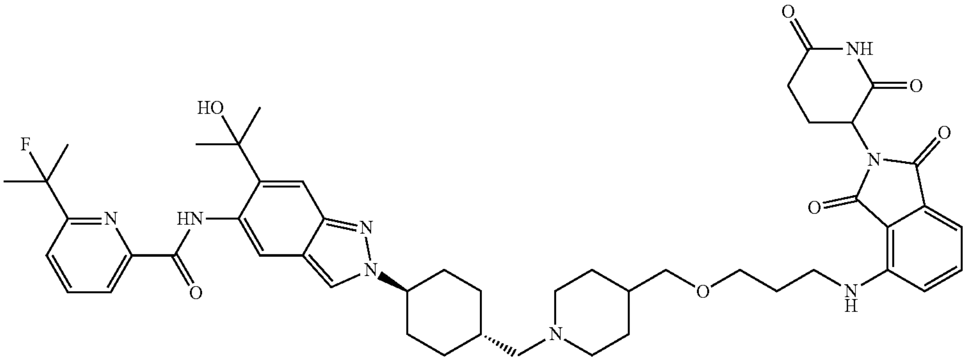 [SMILES: CC(C)(O)c1cc2nn([C@H]3CC[C@H](CN4CCC(COCCCNc5cccc6c5C(=O)N(C5CCC(=O)NC5=O)C6=O)CC4)CC3)cc2cc1NC(=O)c1cccc(C(C)(C)F)n1] |
| I-60 | 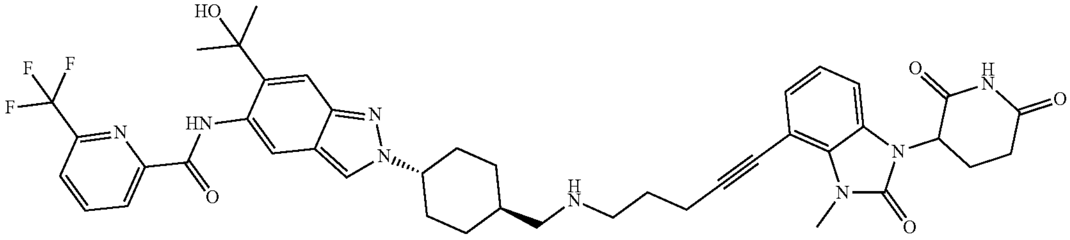 [SMILES: Cn1c(=O)n(C2CCC(=O)NC2=O)c2cccc(C#CCCCNC[C@H]3CC[C@H](n4cc5cc(NC(=O)c6cccc(C(F)(F)F)n6)c(C(C)(C)O)cc5n4)CC3)c21] |
| I-61 | 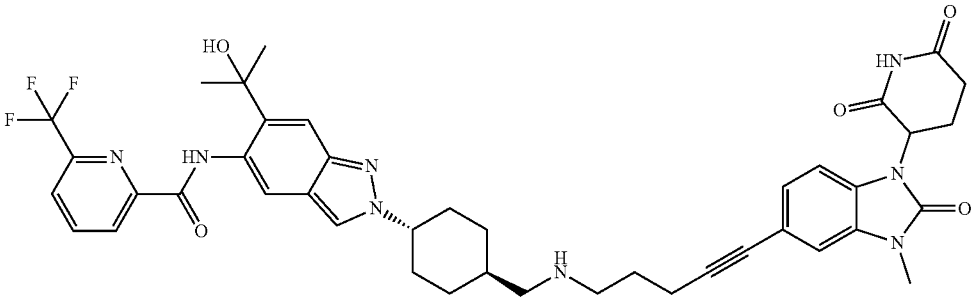 [SMILES: Cn1c(=O)n(C2CCC(=O)NC2=O)c2ccc(C#CCCCNC[C@H]3CC[C@H](n4cc5cc(NC(=O)c6cccc(C(F)(F)F)n6)c(C(C)(C)O)cc5n4)CC3)cc21] |
| I-62 | 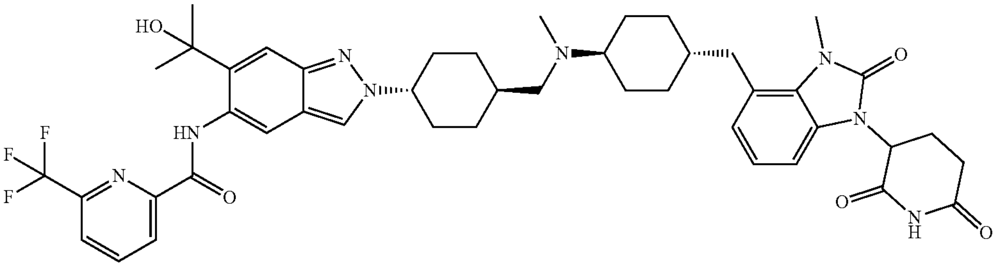 |
| I-63 | 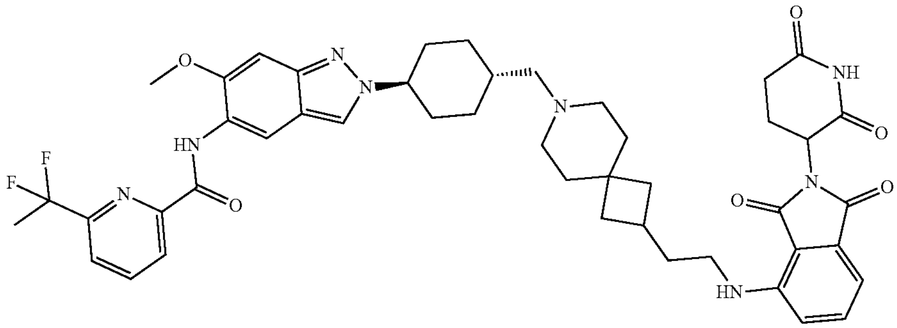 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cccc(C(C)(F)F)n1] |

TABLE 1-continued
| Exemplary Compounds | |
|---|---|
| I-# | Structure |
| I-64 | 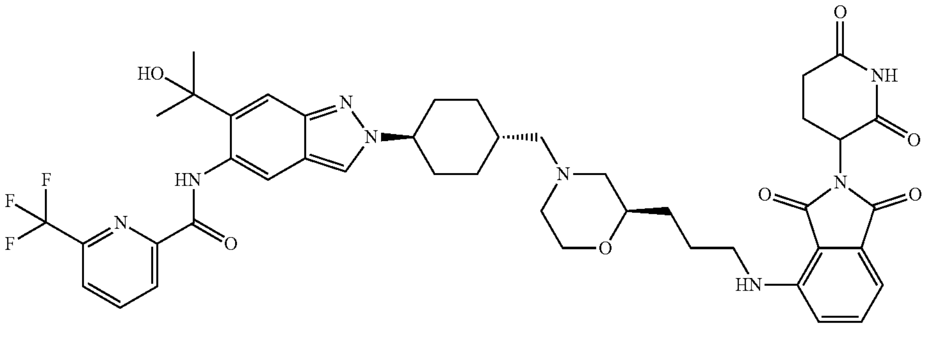 [SMILES: CC(C)(O)c1cc2nn([C@H]3CC[C@H](CN4CCO[C@H](CCCNc5cccc6c5C(=O)N(C5CCC(=O)NC5=O)C6=O)C4)CC3)cc2cc1NC(=O)c1cccc(C(F)(F)F)n1] |
| I-65 | 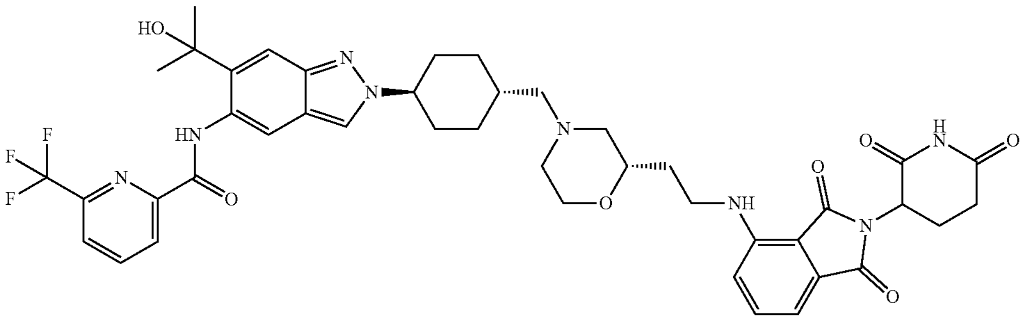 [SMILES: CC(C)(O)c1cc2nn([C@H]3CC[C@H](CN4CCO[C@@H](CCNc5cccc6c5C(=O)N(C5CCC(=O)NC5=O)C6=O)C4)CC3)cc2cc1NC(=O)c1cccc(C(F)(F)F)n1] |
| I-66 | 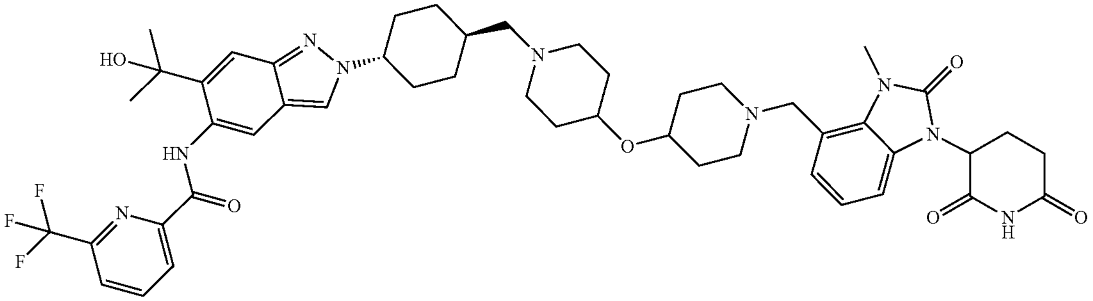 [SMILES: Cn1c(=O)n(C2CCC(=O)NC2=O)c2cccc(CN3CCC(OC4CCN(C[C@H]5CC[C@H](n6cc7cc(NC(=O)c8cccc(C(F)(F)F)n8)c(C(C)(C)O)cc7n6)CC5)CC4)CC3)c21] |
| I-67 | 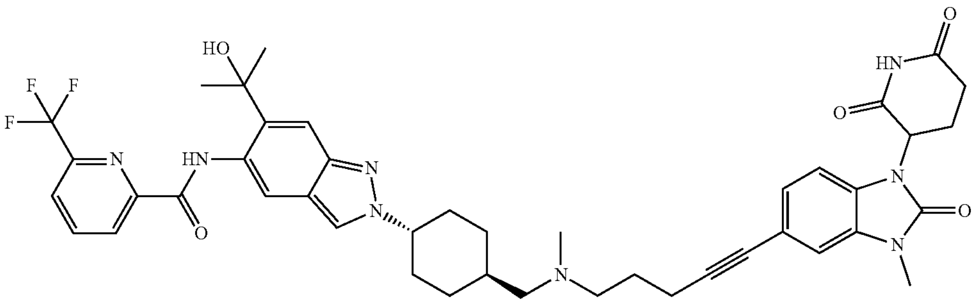 [SMILES: CN(CCCC#Cc1ccc2c(c1)n(C)c(=O)n2C1CCC(=O)NC1=O)C[C@H]1CC[C@H](n2cc3cc(NC(=O)c4cccc(C(F)(F)F)n4)c(C(C)(C)O)cc3n2)CC1] |

TABLE 1-continued
| Exemplary Compounds | |
|---|---|
| I-# | Structure |
| I-68 | 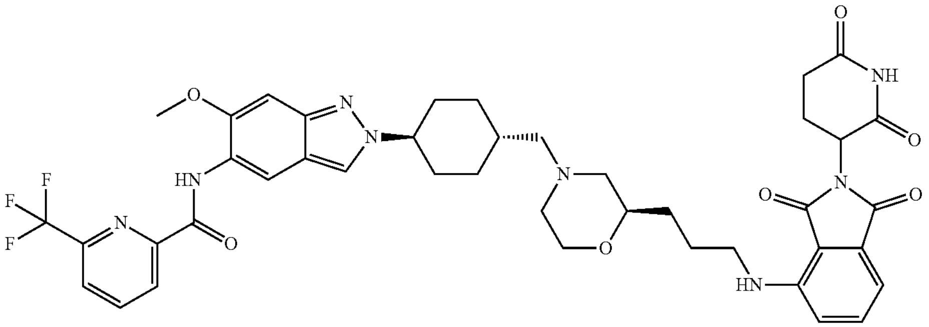 [SMILES: COc1cc2nn([C@H]3CC[C@H](CN4CCO[C@H](CCCNc5cccc6c5C(=O)N(C5CCC(=O)NC5=O)C6=O)C4)CC3)cc2cc1NC(=O)c1cccc(C(F)(F)F)n1] |
| I-69 | 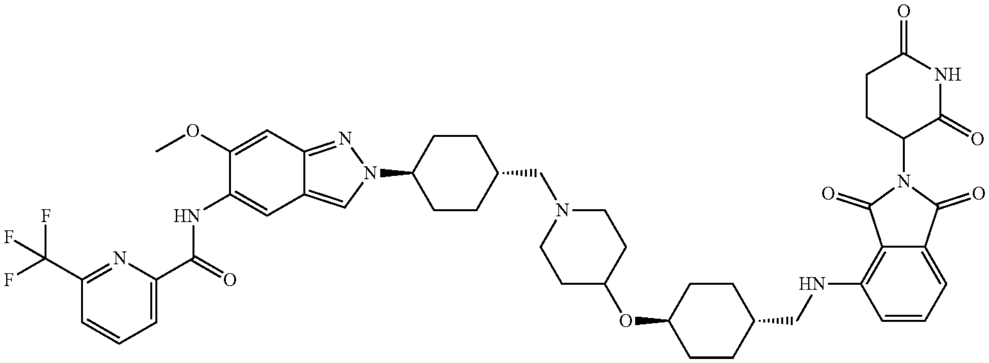 [SMILES: COc1cc2nn([C@H]3CC[C@H](CN4CCC(O[C@H]5CC[C@H](CNc6cccc7c6C(=O)N(C6CCC(=O)NC6=O)C7=O)CC5)CC4)CC3)cc2cc1NC(=O)c1cccc(C(F)(F)F)n1] |
| I-70 | 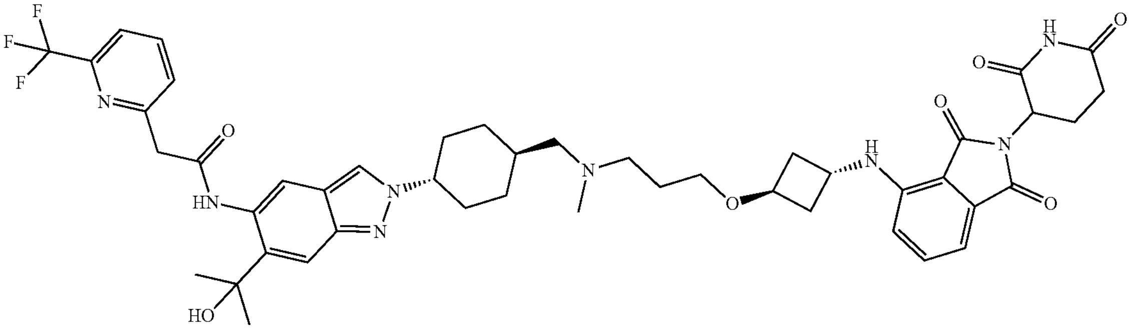 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)Cc4cccc(C(F)(F)F)n4)c(C(C)(C)O)cc3n2)CC1] |
| I-71 | 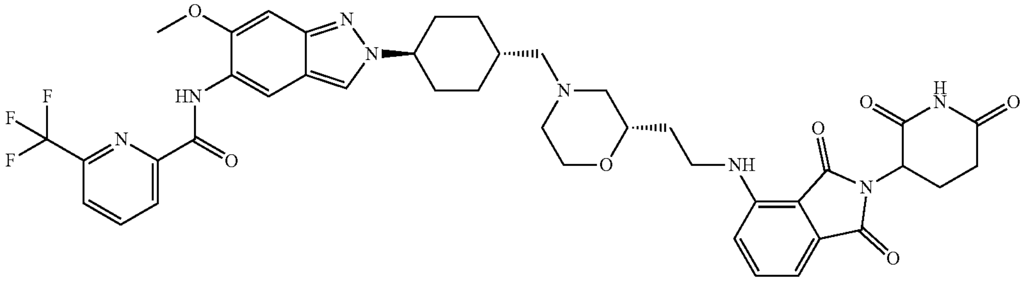 [SMILES: COc1cc2nn([C@H]3CC[C@H](CN4CCO[C@@H](CCNc5cccc6c5C(=O)N(C5CCC(=O)NC5=O)C6=O)C4)CC3)cc2cc1NC(=O)c1cccc(C(F)(F)F)n1] |

TABLE 1-continued
| Exemplary Compounds | |
|---|---|
| I-# | Structure |
| I-72 | 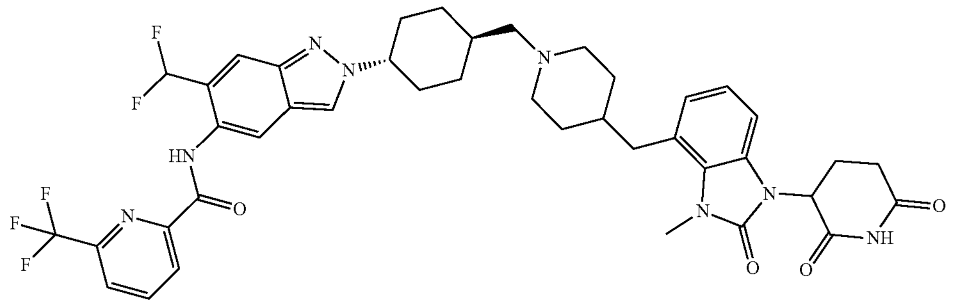 [SMILES: Cn1c(=O)n(C2CCC(=O)NC2=O)c2cccc(CC3CCN(C[C@H]4CC[C@H](n5cc6cc(NC(=O)c7cccc(C(F)(F)F)n7)c(C(F)F)cc6n5)CC4)CC3)c21] |
| I-73 | 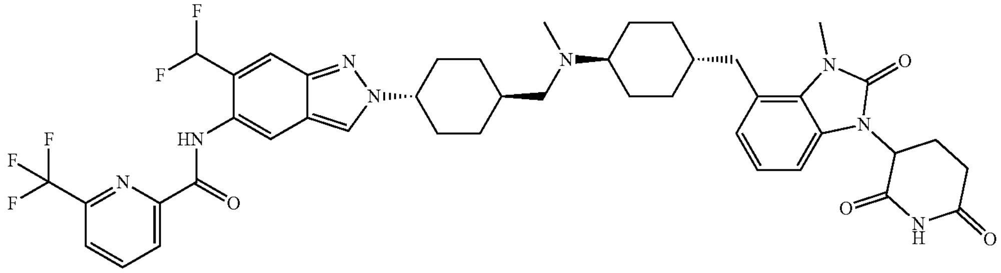 [SMILES: Cn1c(=O)n(C2CCC(=O)NC2=O)c2cccc(C[C@H]3CC[C@H](N(C)C[C@H]4CC[C@H](n5cc6cc(NC(=O)c7cccc(C(F)(F)F)n7)c(C(F)F)cc6n5)CC4)CC3)c21] |
| I-74 | 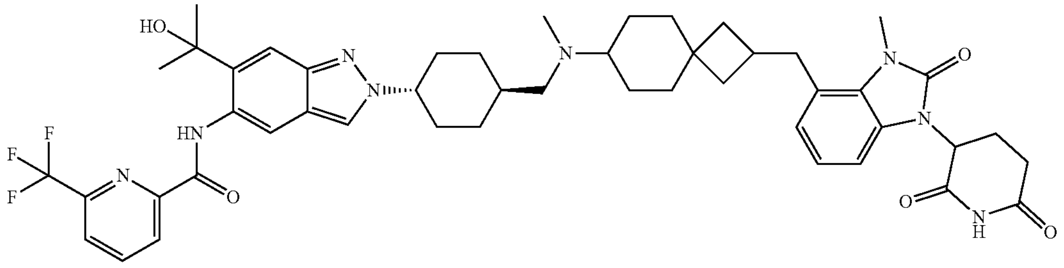 [SMILES: CN(C[C@H]1CC[C@H](n2cc3cc(NC(=O)c4cccc(C(F)(F)F)n4)c(C(C)(C)O)cc3n2)CC1)C1CCC2(CC1)CC(Cc1cccc3c1n(C)c(=O)n3C1CCC(=O)NC1=O)C2] |
| I-75 | 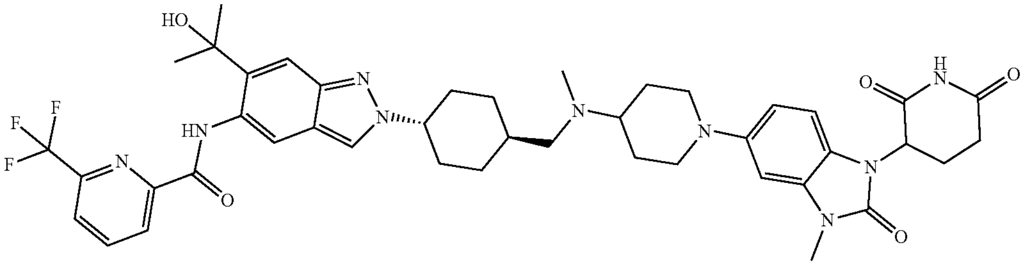 [SMILES: CN(C[C@H]1CC[C@H](n2cc3cc(NC(=O)c4cccc(C(F)(F)F)n4)c(C(C)(C)O)cc3n2)CC1)C1CCN(c2ccc3c(c2)n(C)c(=O)n3C2CCC(=O)NC2=O)CC1] |
| I-76 | 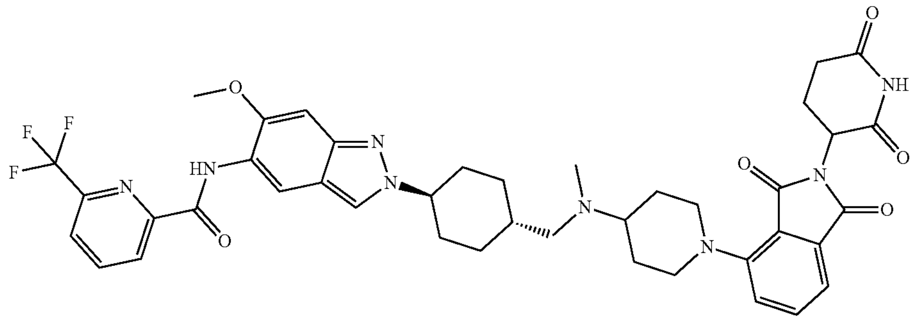 [SMILES: COc1cc2nn([C@H]3CC[C@H](CN(C)C4CCN(c5cccc6c5C(=O)N(C5CCC(=O)NC5=O)C6=O)CC4)CC3)cc2cc1NC(=O)c1cccc(C(F)(F)F)n1] |

TABLE 1-continued
| Exemplary Compounds | |
|---|---|
| I-# | Structure |
| I-77 | 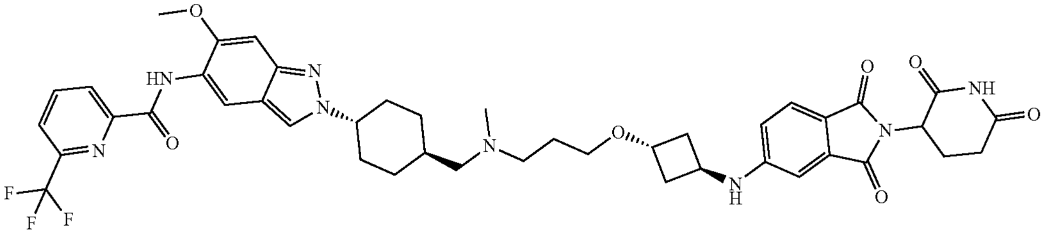 [SMILES: COc1cc2nn([C@H]3CC[C@H](CN(C)CCCO[C@H]4C[C@H](Nc5ccc6c(c5)C(=O)N(C5CCC(=O)NC5=O)C6=O)C4)CC3)cc2cc1NC(=O)c1cccc(C(F)(F)F)n1] |
| I-78 | 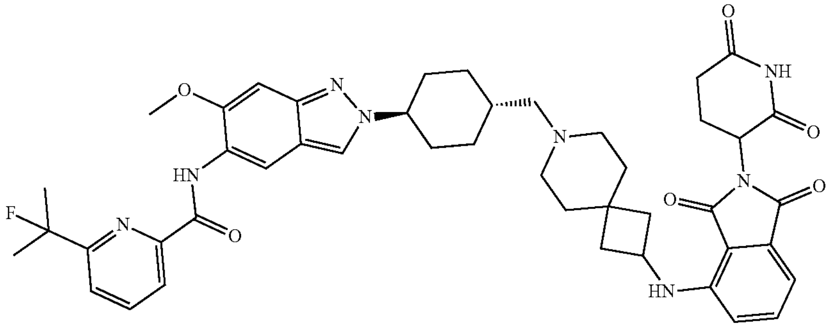 [SMILES: COc1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cccc(C(C)(C)F)n1] |
| I-79 | 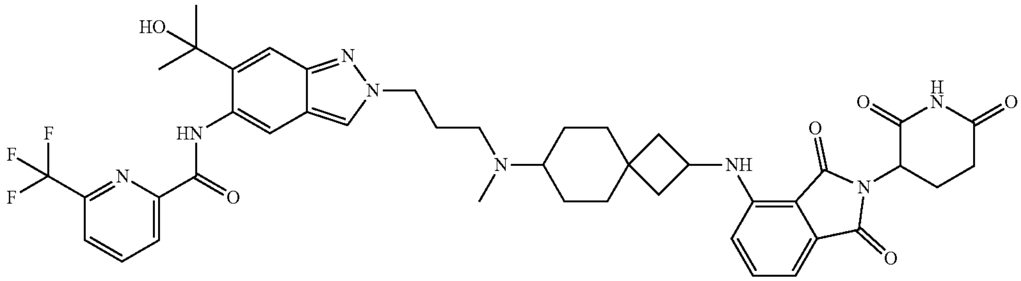 [SMILES: CN(CCCn1cc2cc(NC(=O)c3cccc(C(F)(F)F)n3)c(C(C)(C)O)cc2n1)C1CCC2(CC1)CC(Nc1cccc3c1C(=O)N(C1CCC(=O)NC1=O)C3=O)C2] |
| I-80 | 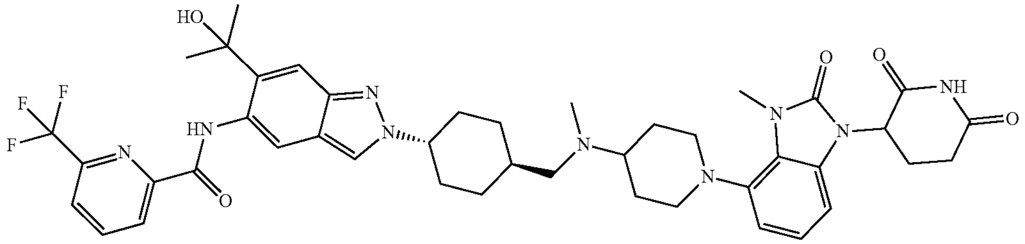 [SMILES: CN(C[C@H]1CC[C@H](n2cc3cc(NC(=O)c4cccc(C(F)(F)F)n4)c(C(C)(C)O)cc3n2)CC1)C1CCN(c2cccc3c2n(C)c(=O)n3C2CCC(=O)NC2=O)CC1] |
| I-81 | 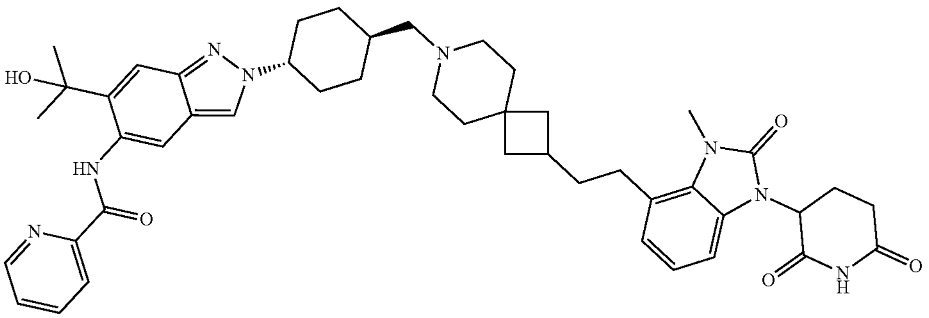 [SMILES: Cn1c(=O)n(C2CCC(=O)NC2=O)c2cccc(CCC3CC4(CCN(C[C@H]5CC[C@H](n6cc7cc(NC(=O)c8ccccn8)c(C(C)(C)O)cc7n6)CC5)CC4)C3)c21] |

TABLE 1-continued
| Exemplary Compounds | |
|---|---|
| I-# | Structure |
| I-82 | 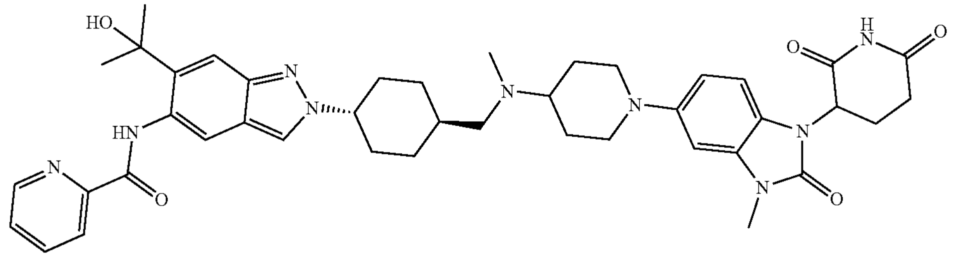 [SMILES: CN(C[C@H]1CC[C@H](n2cc3cc(NC(=O)c4ccccn4)c(C(C)(C)O)cc3n2)CC1)C1CCN(c2ccc3c(c2)n(C)c(=O)n3C2CCC(=O)NC2=O)CC1] |
| I-83 | 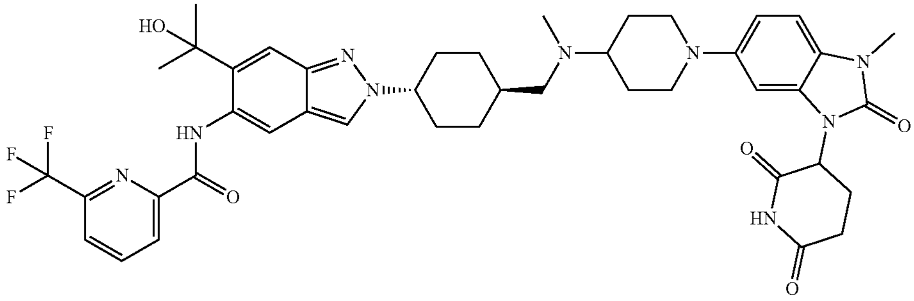 [SMILES: CN(C[C@H]1CC[C@H](n2cc3cc(NC(=O)c4cccc(C(F)(F)F)n4)c(C(C)(C)O)cc3n2)CC1)C1CCN(c2ccc3c(c2)n(C2CCC(=O)NC2=O)c(=O)n3C)CC1] |
| I-84 | 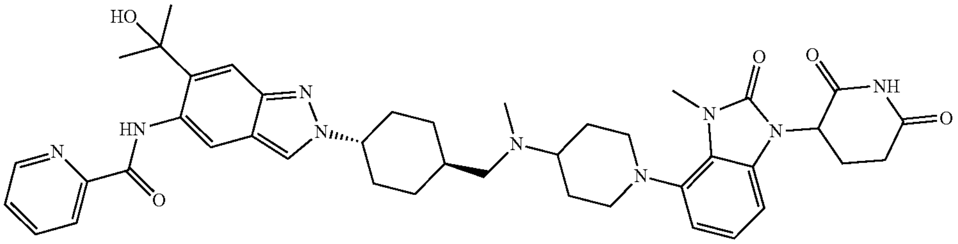 [SMILES: CN(C[C@H]1CC[C@H](n2cc3cc(NC(=O)c4ccccn4)c(C(C)(C)O)cc3n2)CC1)C1CCN(c2cccc3c2n(C)c(=O)n3C2CCC(=O)NC2=O)CC1] |
| I-85 | 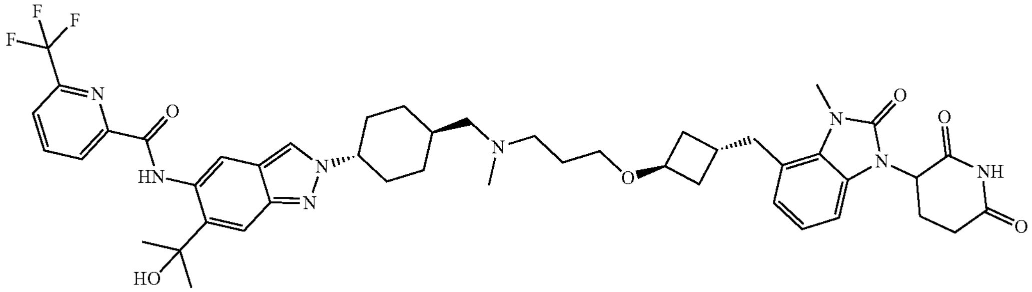 [SMILES: CN(CCCO[C@H]1C[C@H](Cc2cccc3c2n(C)c(=O)n3C2CCC(=O)NC2=O)C1)C[C@H]1CC[C@H](n2cc3cc(NC(=O)c4cccc(C(F)(F)F)n4)c(C(C)(C)O)cc3n2)CC1] |
| I-86 | 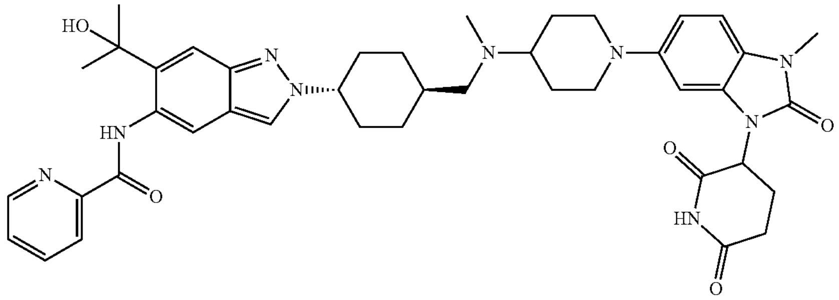 [SMILES: CN(C[C@H]1CC[C@H](n2cc3cc(NC(=O)c4ccccn4)c(C(C)(C)O)cc3n2)CC1)C1CCN(c2ccc3c(c2)n(C2CCC(=O)NC2=O)c(=O)n3C)CC1] |

TABLE 1-continued
| Exemplary Compounds | |
|---|---|
| I-# | Structure |
| I-87 | 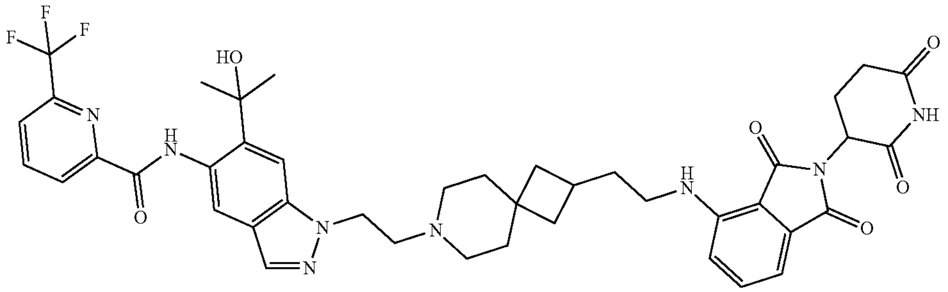 [SMILES: CC(C)(O)c1cc2c(cnn2CCN2CCC3(CC2)CC(CCNc2cccc4c2C(=O)N(C2CCC(=O)NC2=O)C4=O)C3)cc1NC(=O)c1cccc(C(F)(F)F)n1] |
| I-88 | 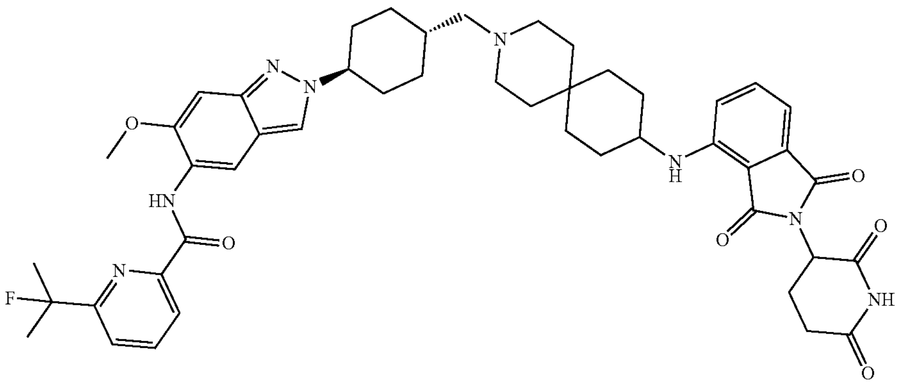 [SMILES: COc1cc2nn([C@H]3CC[C@H](CN4CCC5(CCC(Nc6cccc7c6C(=O)N(C6CCC(=O)NC6=O)C7=O)CC5)CC4)CC3)cc2cc1NC(=O)c1cccc(C(C)(C)F)n1] |
| I-89 | 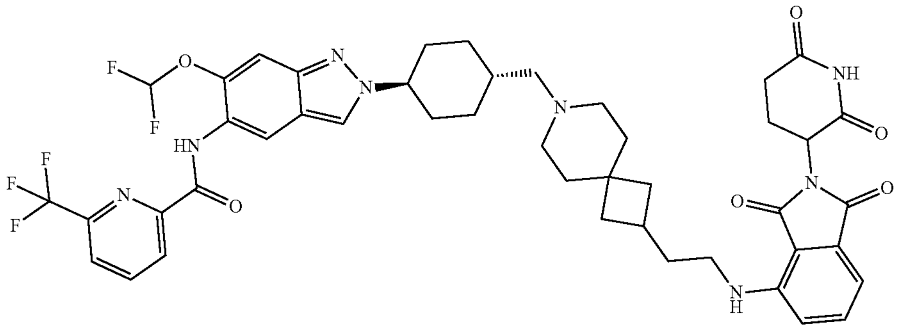 [SMILES: O=C1CCC(N2C(=O)c3cccc(NCCC4CC5(CCN(C[C@H]6CC[C@H](n7cc8cc(NC(=O)c9cccc(C(F)(F)F)n9)c(OC(F)F)cc8n7)CC6)CC5)C4)c3C2=O)C(=O)N1] |
| I-90 | 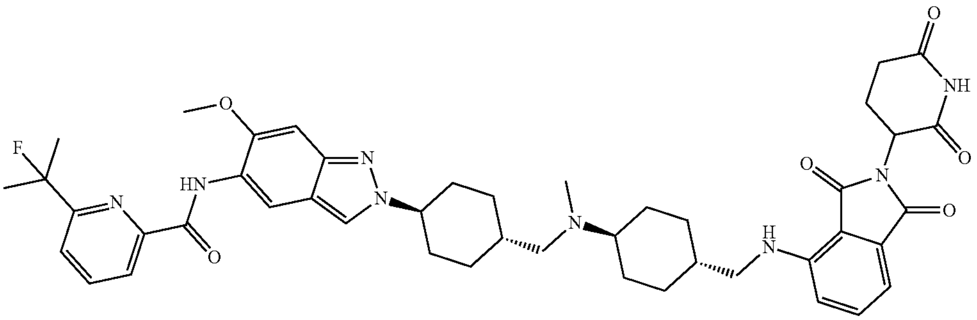 [SMILES: COc1cc2nn([C@H]3CC[C@H](CN(C)[C@H]4CC[C@H](CNc5cccc6c5C(=O)N(C5CCC(=O)NC5=O)C6=O)CC4)CC3)cc2cc1NC(=O)c1cccc(C(C)(C)F)n1] |

TABLE 1-continued
| Exemplary Compounds | |
|---|---|
| I-# | Structure |
| I-91 | 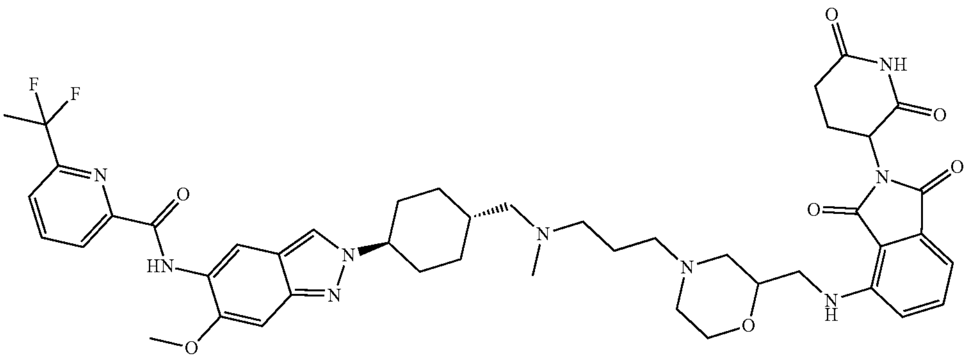 [SMILES: COc1cc2nn([C@H]3CC[C@H](CN(C)CCCN4CCOC(CNc5cccc6c5C(=O)N(C5CCC(=O)NC5=O)C6=O)C4)CC3)cc2cc1NC(=O)c1cccc(C(C)(F)F)n1] |
| I-92 | 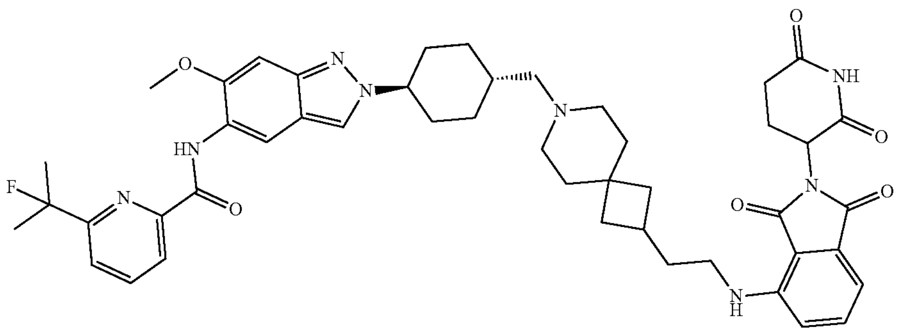 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cccc(C(C)(C)F)n1] |
| I-93 | 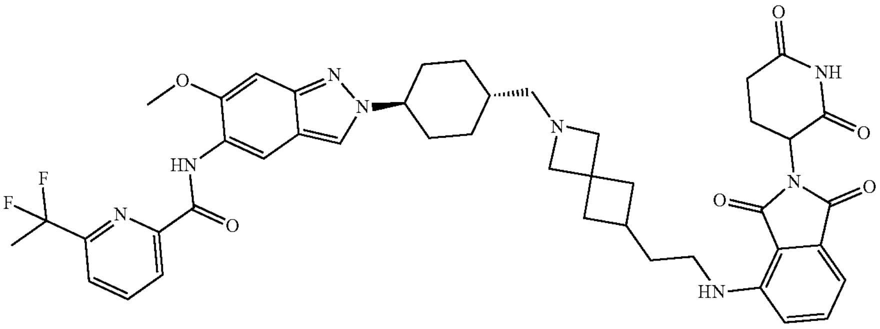 [SMILES: COc1cc2nn([C@H]3CC[C@H](CN4CC5(CC(CCNc6cccc7c6C(=O)N(C6CCC(=O)NC6=O)C7=O)C5)C4)CC3)cc2cc1NC(=O)c1cccc(C(C)(F)F)n1] |
| I-94 | 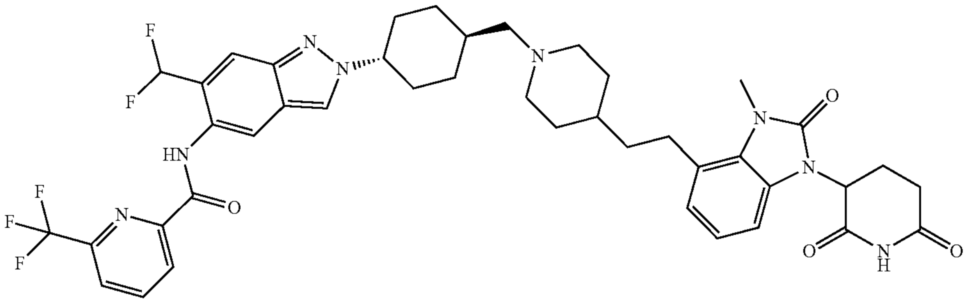 [SMILES: Cn1c(=O)n(C2CCC(=O)NC2=O)c2cccc(CCC3CCN(C[C@H]4CC[C@H](n5cc6cc(NC(=O)c7cccc(C(F)(F)F)n7)c(C(F)F)cc6n5)CC4)CC3)c21] |

TABLE 1-continued
| Exemplary Compounds | |
|---|---|
| I-# | Structure |
| I-95 | 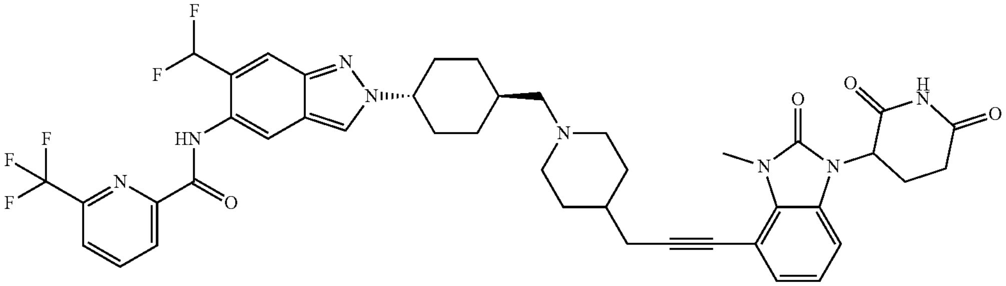 [SMILES: Cn1c(=O)n(C2CCC(=O)NC2=O)c2cccc(C#CCC3CCN(C[C@H]4CC[C@H](n5cc6cc(NC(=O)c7cccc(C(F)(F)F)n7)c(C(F)F)cc6n5)CC4)CC3)c21] |
| I-96 | 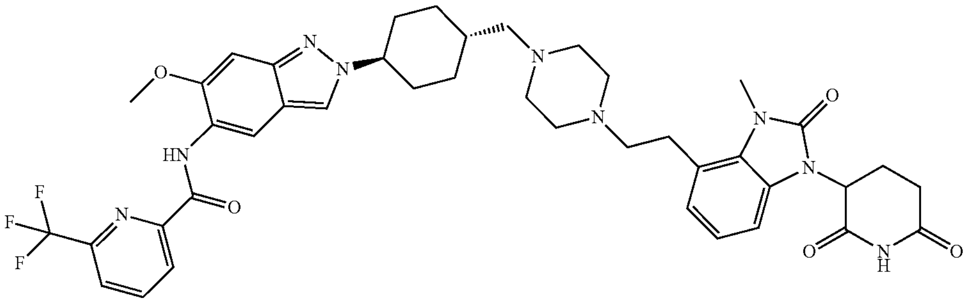 [SMILES: COc1cc2nn([C@H]3CC[C@H](CN4CCN(CCc5cccc6c5n(C)c(=O)n6C5CCC(=O)NC5=O)CC4)CC3)cc2cc1NC(=O)c1cccc(C(F)(F)F)n1] |
| I-97 | 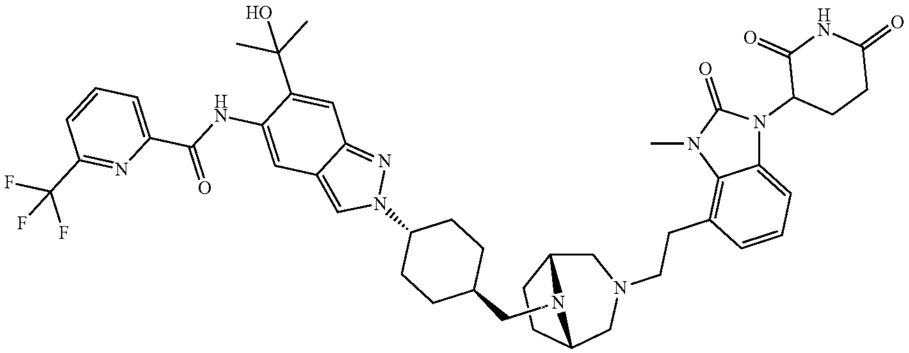 [SMILES: Cn1c(=O)n(C2CCC(=O)NC2=O)c2cccc(CCN3C[C@H]4CC[C@@H](C3)N4CC[C@H]3CC[C@H](n4cc5cc(NC(=O)c6cccc(C(F)(F)F)n6)c(C(C)(C)O)cc5n4)CC3)c21] |
| I-98 | 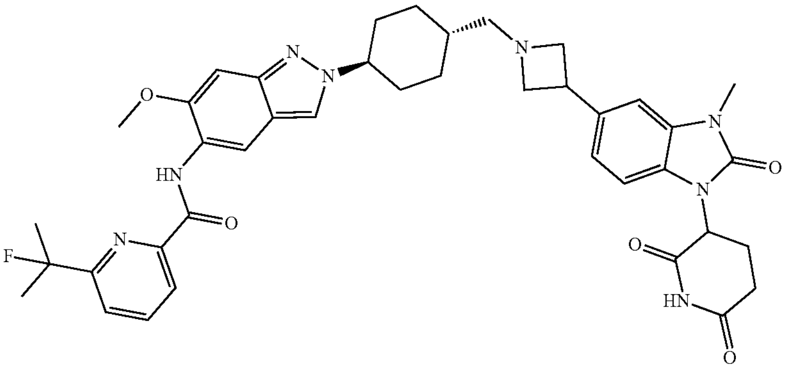 [SMILES: COc1cc2nn([C@H]3CC[C@H](CN4CC(c5ccc6c(c5)n(C)c(=O)n6C5CCC(=O)NC5=O)C4)CC3)cc2cc1NC(=O)c1cccc(C(C)(C)F)n1] |

TABLE 1-continued
| Exemplary Compounds | |
|---|---|
| I-# | Structure |
| I-99 | 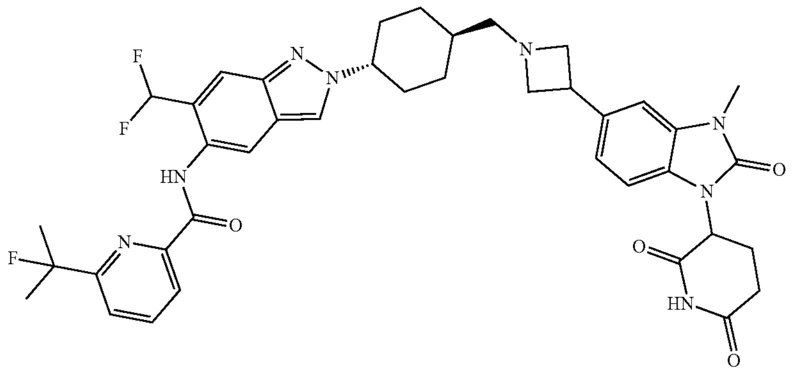 [SMILES: Cn1c(=O)n(C2CCC(=O)NC2=O)c2ccc(C3CN(C[C@H]4CC[C@H](n5cc6cc(NC(=O)c7cccc(C(C)(C)F)n7)c(C(F)F)cc6n5)CC4)C3)cc21] |
| I-100 | 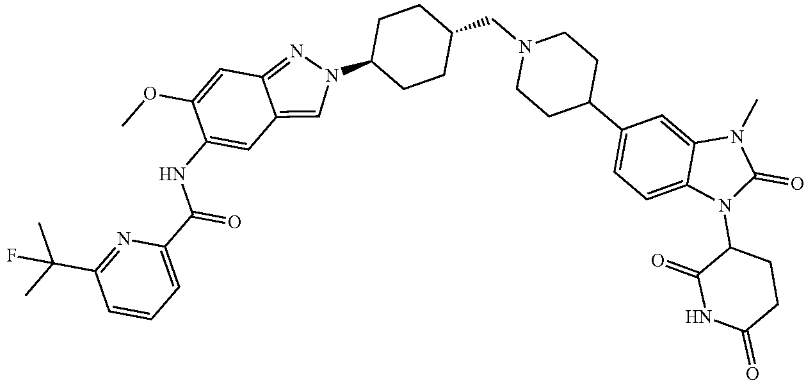 |
| I-101 | 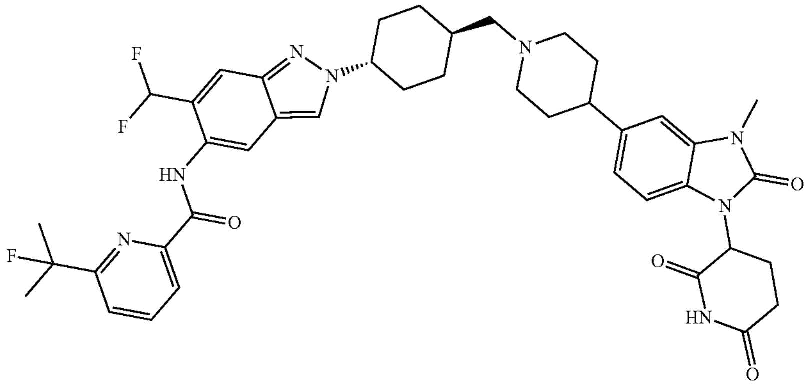 [SMILES: Cn1c(=O)n(C2CCC(=O)NC2=O)c2ccc(C3CCN(C[C@H]4CC[C@H](n5cc6cc(NC(=O)c7cccc(C(C)(C)F)n7)c(C(F)F)cc6n5)CC4)CC3)cc21] |
| I-102 | 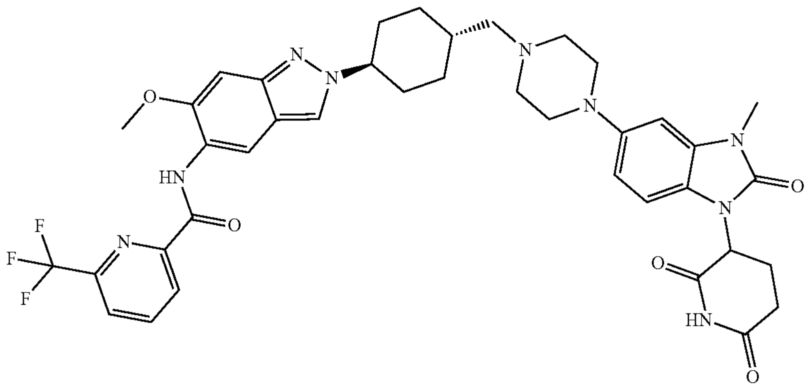 [SMILES: COc1cc2nn([C@H]3CC[C@H](CN4CCN(c5ccc6c(c5)n(C)c(=O)n6C5CCC(=O)NC5=O)CC4)CC3)cc2cc1NC(=O)c1cccc(C(F)(F)F)n1] |

TABLE 1-continued
| Exemplary Compounds | |
|---|---|
| I-# | Structure |
| I-103 | 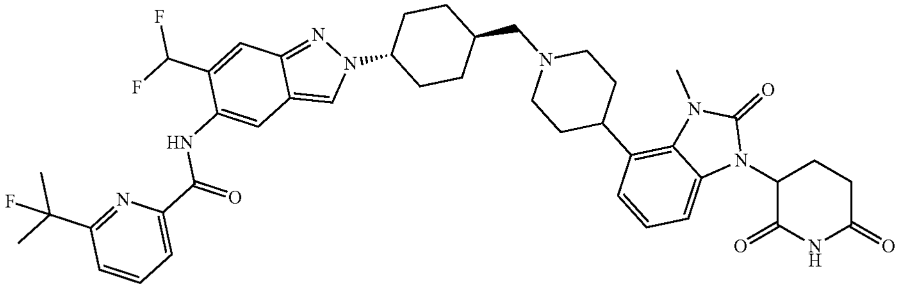 [SMILES: Cn1c(=O)n(C2CCC(=O)NC2=O)c2cccc(C3CCN(C[C@H]4CC[C@H](n5cc6cc(NC(=O)c7cccc(C(C)(C)F)n7)c(C(F)F)cc6n5)CC4)CC3)c21] |
| I-104 | 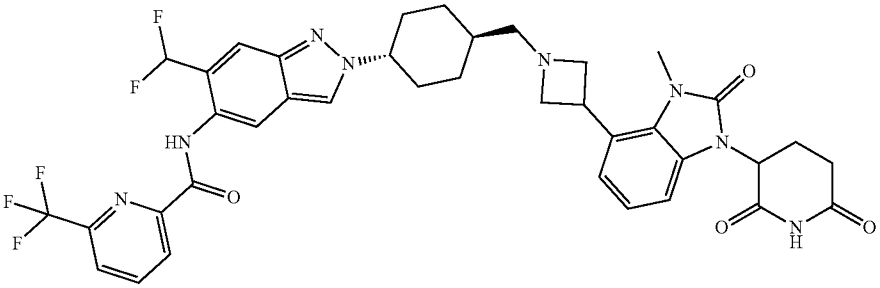 [SMILES: Cn1c(=O)n(C2CCC(=O)NC2=O)c2cccc(C3CN(C[C@H]4CC[C@H](n5cc6cc(NC(=O)c7cccc(C(F)(F)F)n7)c(C(F)F)cc6n5)CC4)C3)c21] |
| I-105 | 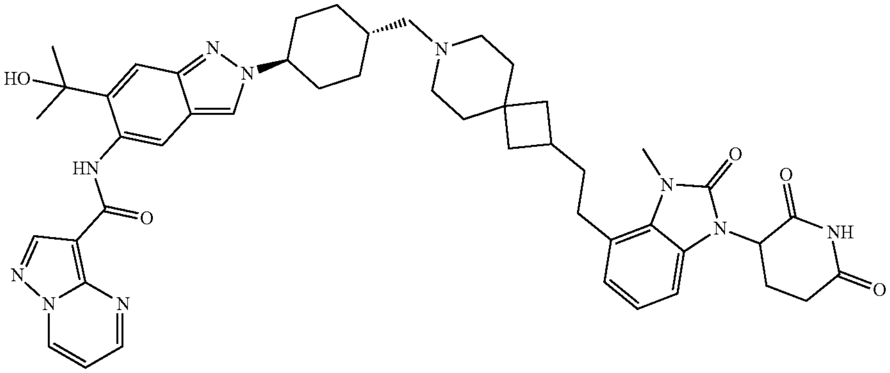 [SMILES: Cn1c(=O)n(C2CCC(=O)NC2=O)c2cccc(CCC3CC4(CCN(C[C@H]5CC[C@H](n6cc7cc(NC(=O)c8cnn9cccnc89)c(C(C)(C)O)cc7n6)CC5)CC4)C3)c21] |
| I-106 | 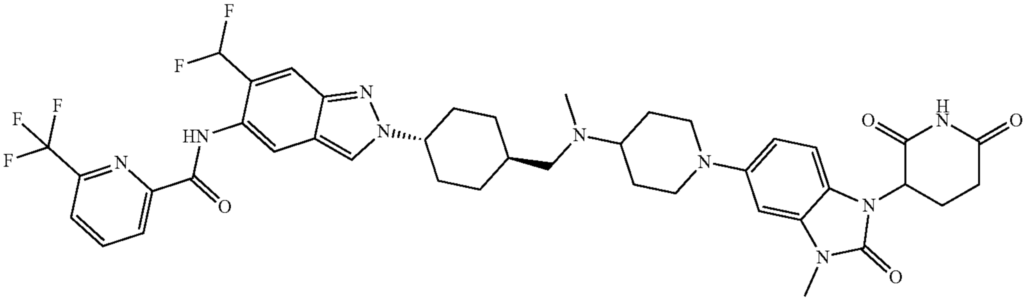 [SMILES: CN(C[C@H]1CC[C@H](n2cc3cc(NC(=O)c4cccc(C(F)(F)F)n4)c(C(F)F)cc3n2)CC1)C1CCN(c2ccc3c(c2)n(C)c(=O)n3C2CCC(=O)NC2=O)CC1] |
| I-107 | 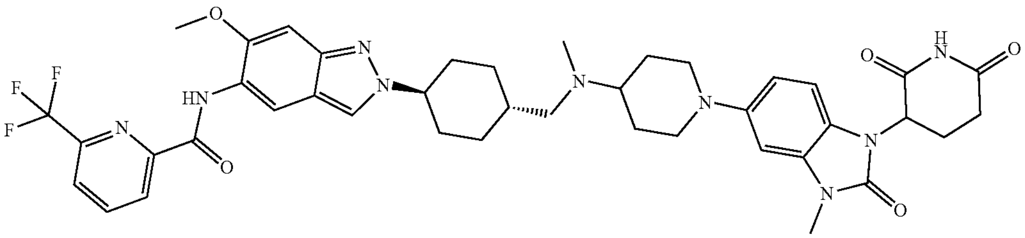 [SMILES: COc1cc2nn([C@H]3CC[C@H](CN(C)C4CCN(c5ccc6c(c5)n(C)c(=O)n6C5CCC(=O)NC5=O)CC4)CC3)cc2cc1NC(=O)c1cccc(C(F)(F)F)n1] |

TABLE 1-continued
| Exemplary Compounds | |
|---|---|
| I-# | Structure |
| I-108 | 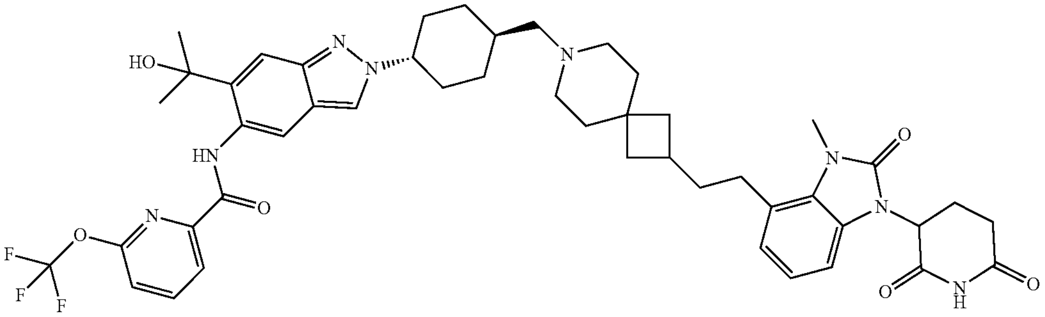 [SMILES: Cn1c(=O)n(C2CCC(=O)NC2=O)c2cccc(CCC3CC4(CCN(C[C@H]5CC[C@H](n6cc7cc(NC(=O)c8cccc(OC(F)(F)F)n8)c(C(C)(C)O)cc7n6)CC5)CC4)C3)c21] |
| I-109 | 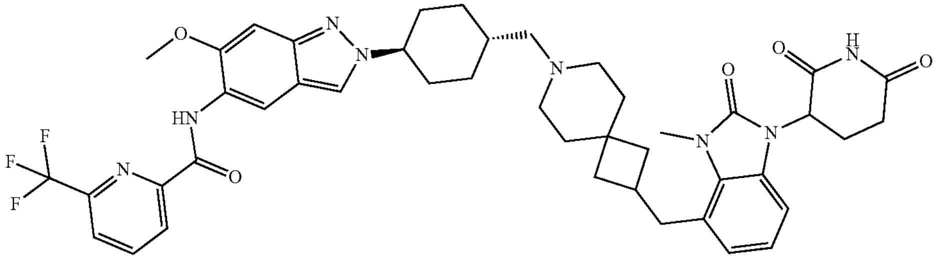 [SMILES: COc1cc2nn([C@H]3CC[C@H](CN4CCC5(CC4)CC(Cc4cccc6c4n(C)c(=O)n6C4CCC(=O)NC4=O)C5)CC3)cc2cc1NC(=O)c1cccc(C(F)(F)F)n1] |
| I-110 | 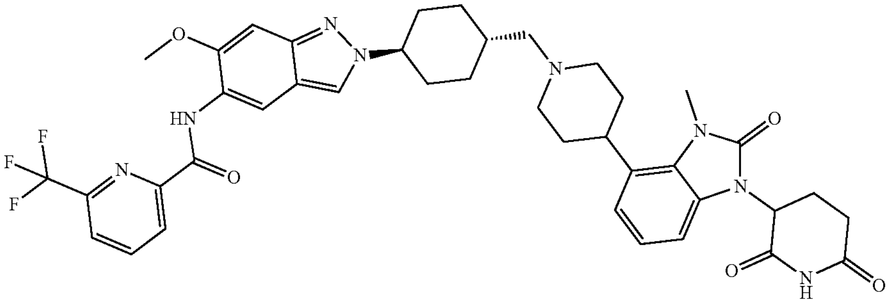 |
| I-111 | 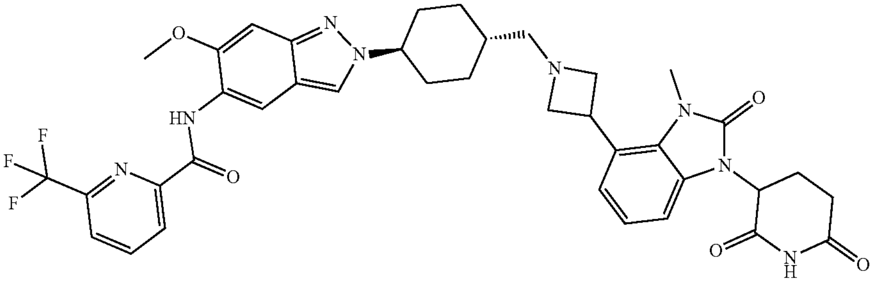 [SMILES: COc1cc2nn([C@H]3CC[C@H](CN4CC(c5cccc6c5n(C)c(=O)n6C5CCC(=O)NC5=O)C4)CC3)cc2cc1NC(=O)c1cccc(C(F)(F)F)n1] |
| I-112 | 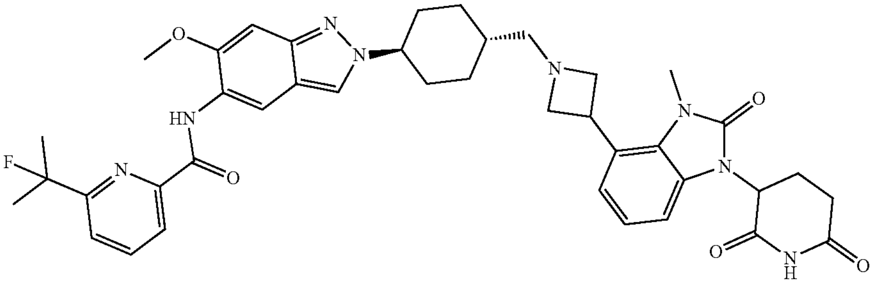 [SMILES: COc1cc2nn([C@H]3CC[C@H](CN4CC(c5cccc6c5n(C)c(=O)n6C5CCC(=O)NC5=O)C4)CC3)cc2cc1NC(=O)c1cccc(C(C)(C)F)n1] |

TABLE 1-continued
Exemplary Compounds
| I-# | Structure |
|---|---|
| I-113 | 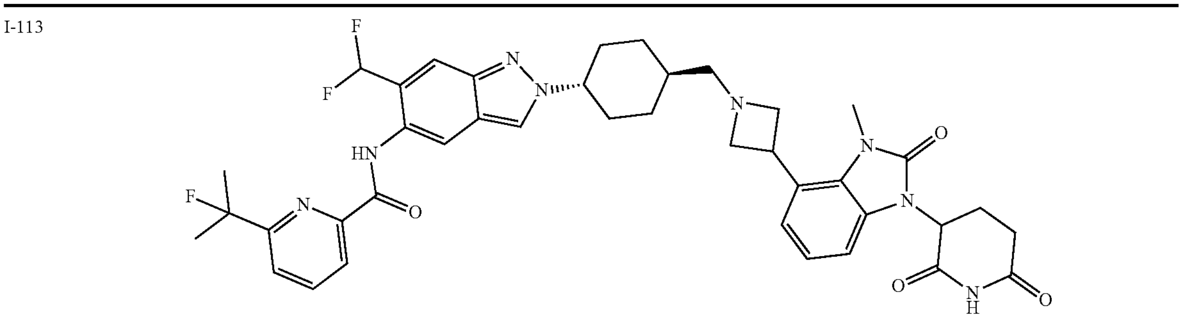 |
| I-114 | 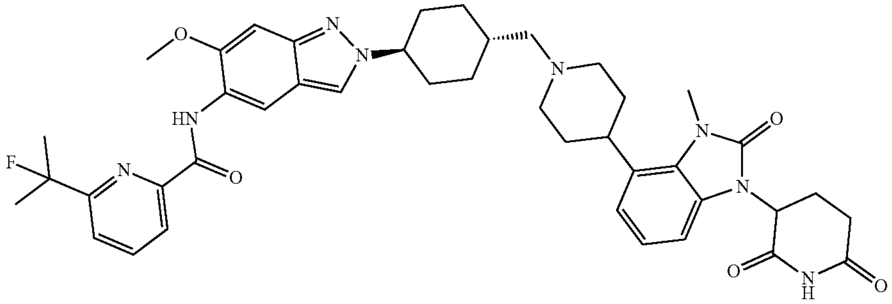 |
| I-115 | 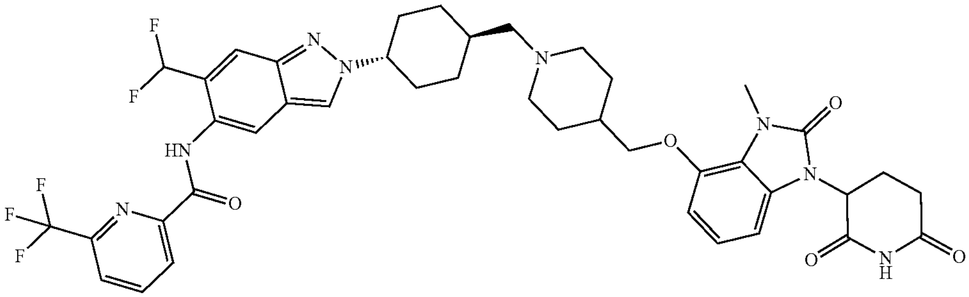 [SMILES: Cn1c(=O)n(C2CCC(=O)NC2=O)c2cccc(OCC3CCN(C[C@H]4CC[C@H](n5cc6cc(NC(=O)c7cccc(C(F)(F)F)n7)c(C(F)F)cc6n5)CC4)CC3)c21] |
| I-116 | 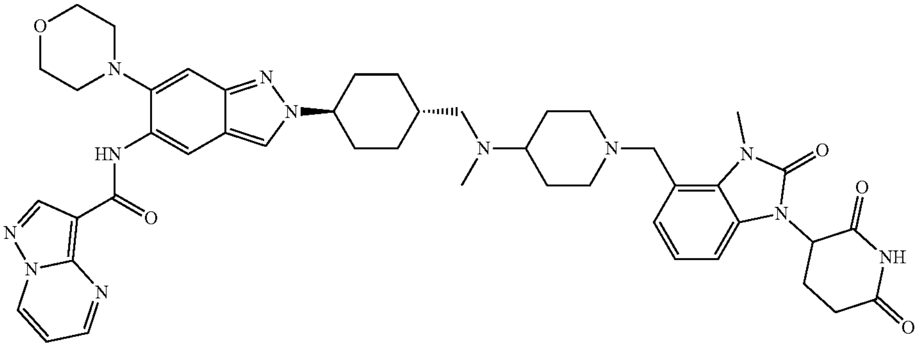 [SMILES: CN(C[C@H]1CC[C@H](n2cc3cc(NC(=O)c4cnn5cccnc45)c(N4CCOCC4)cc3n2)CC1)C1CCN(Cc2cccc3c2n(C)c(=O)n3C2CCC(=O)NC2=O)CC1] |
| I-117 | 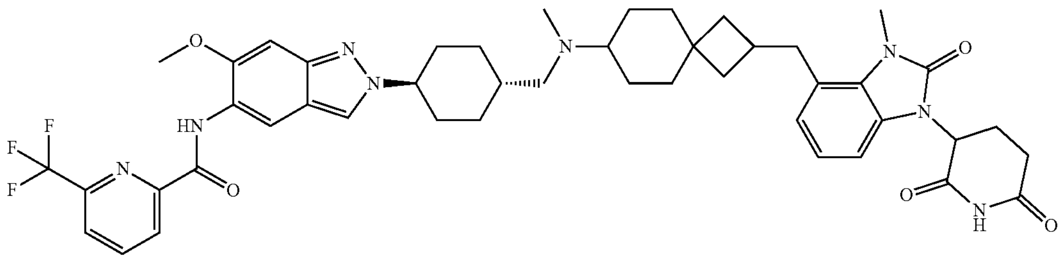 [SMILES: COc1cc2nn([C@H]3CC[C@H](CN(C)C4CCC5(CC4)CC(Cc4cccc6c4n(C)c(=O)n6C4CCC(=O)NC4=O)C5)CC3)cc2cc1NC(=O)c1cccc(C(F)(F)F)n1] |

TABLE 1-continued
| Exemplary Compounds | |
|---|---|
| I-# | Structure |
| I-118 | 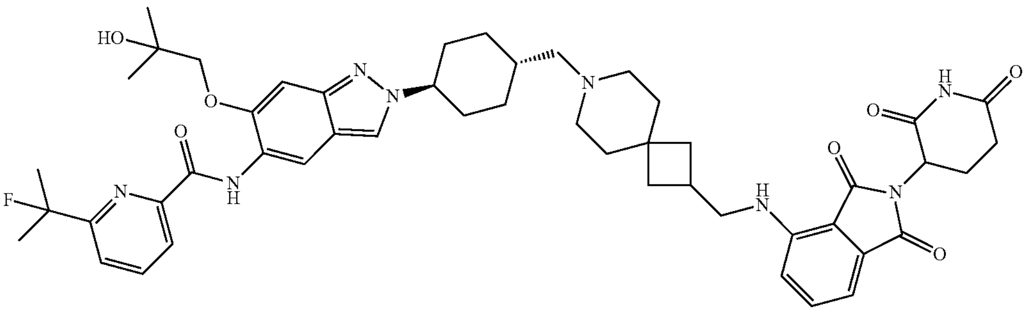 [SMILES: CC(C)(O)COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(C)(C)F)n1] |
| I-119 | 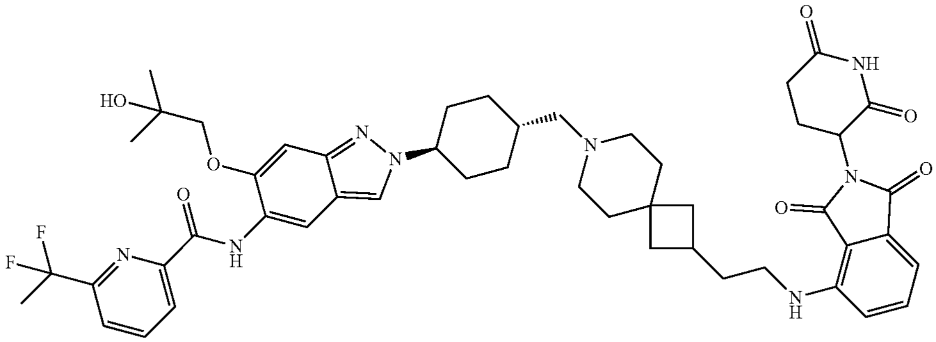 [SMILES: CC(C)(O)COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cccc(C(C)(F)F)n1] |
| I-120 | 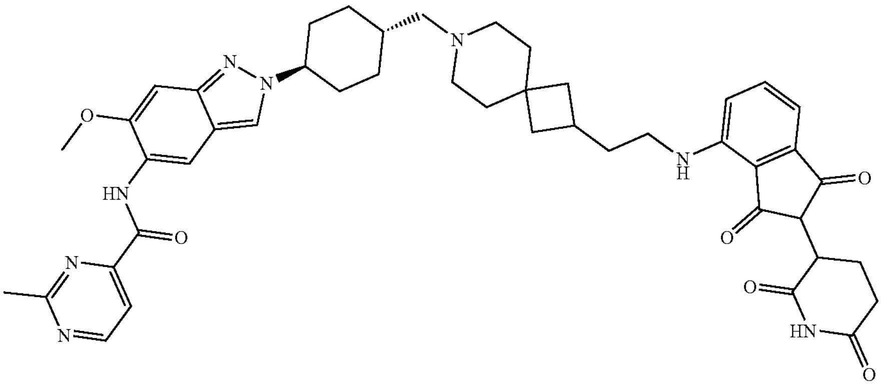 [SMILES: COc1cc2nn([C@H]3CC[C@H](CN4CCC5(CC4)CC(CCNc4cccc6c4C(=O)C(C4CCC(=O)NC4=O)C6=O)C5)CC3)cc2cc1NC(=O)c1ccnc(C)n1] |
| I-121 | 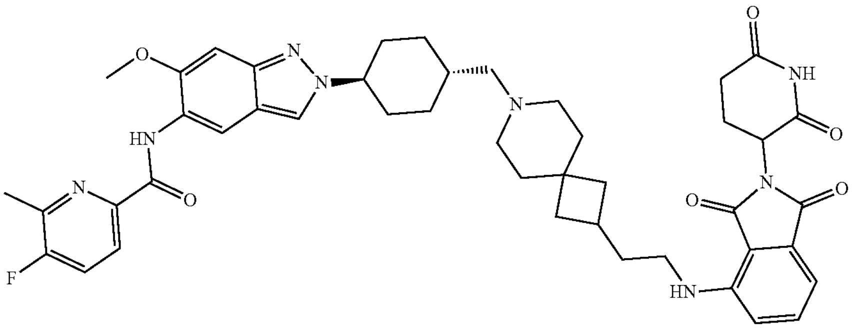 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1ccc(F)c(C)n1] |

TABLE 1-continued
| Exemplary Compounds | |
|---|---|
| I-# | Structure |
| I-122 | 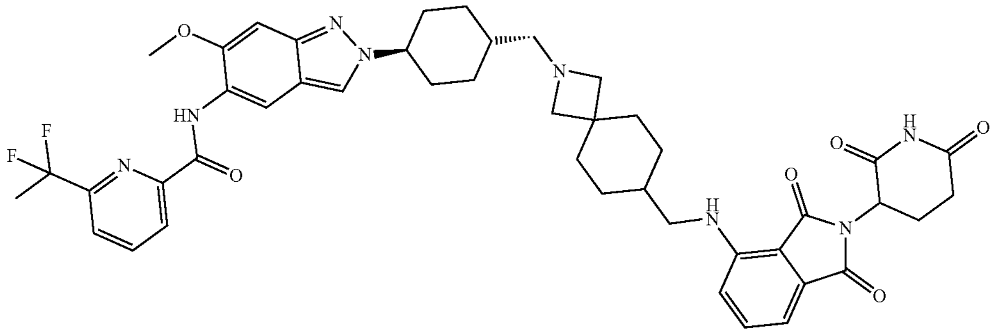 |
| I-123 | 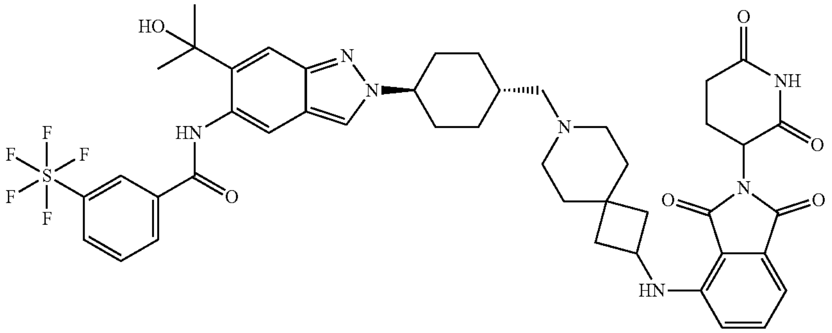 [SMILES: CC(C)(O)c1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cccc(S(F)(F)(F)(F)F)c1] |
| I-124 | 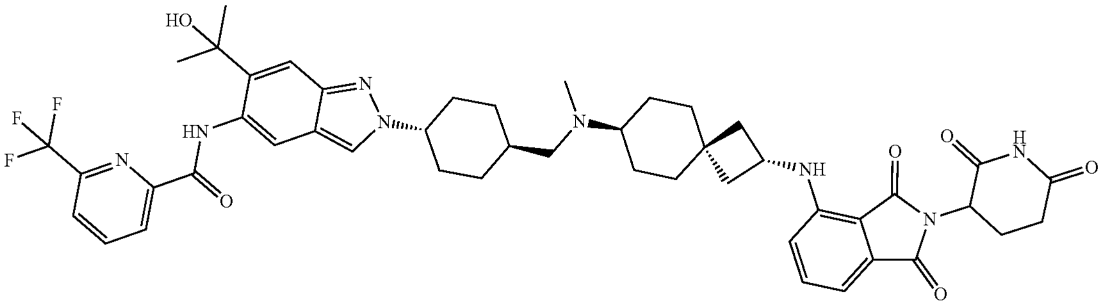 |
| I-125 | 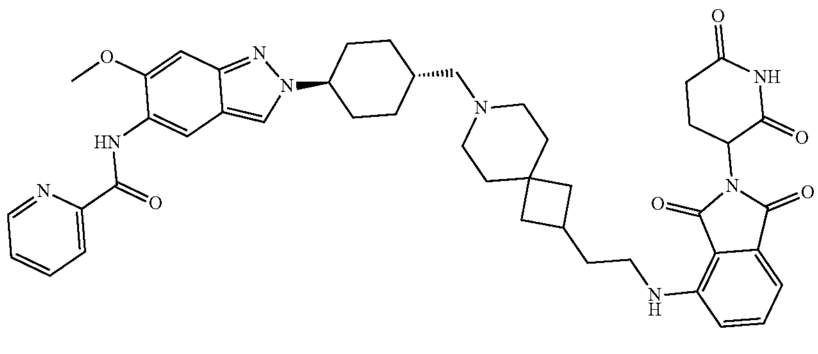 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1ccccn1] |

TABLE 1-continued
| Exemplary Compounds | |
|---|---|
| I-# | Structure |
| I-126 | 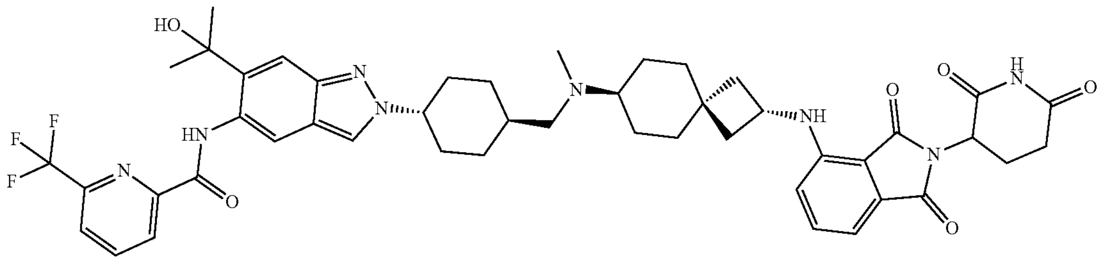 |
| I-127 | 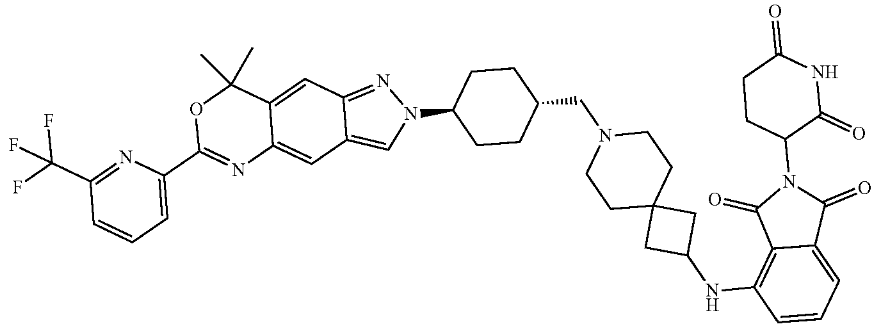 [SMILES: CC1(C)OC(c2cccc(C(F)(F)F)n2)=Nc2cc3cn([C@H]4CC[C@H](CN5CCC6(CC5)CC(Nc5cccc7c5C(=O)N(C5CCC(=O)NC5=O)C7=O)C6)CC4)nc3cc21] |
| I-128 | 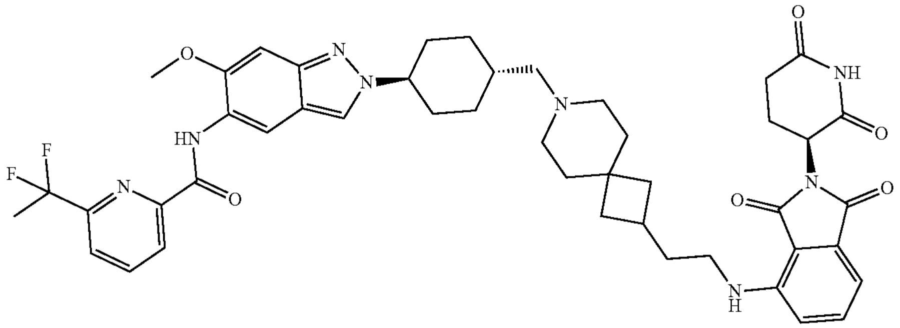 [SMILES: COc1cc2nn([C@H]3CC[C@H](CN4CCC5(CC4)CC(CCNc4cccc6c4C(=O)N([C@H]4CCC(=O)NC4=O)C6=O)C5)CC3)cc2cc1NC(=O)c1cccc(C(C)(F)F)n1] |
| I-129 | 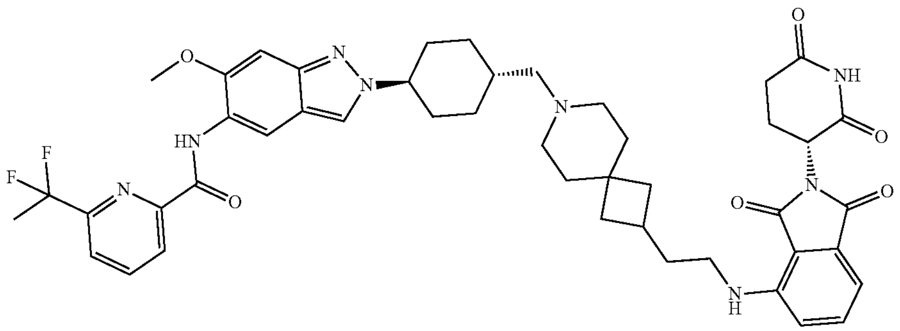 [SMILES: COc1cc2nn([C@H]3CC[C@H](CN4CCC5(CC4)CC(CCNc4cccc6c4C(=O)N([C@@H]4CCC(=O)NC4=O)C6=O)C5)CC3)cc2cc1NC(=O)c1cccc(C(C)(F)F)n1] |

TABLE 1-continued
| Exemplary Compounds | |
|---|---|
| I-# | Structure |
| I-130 | 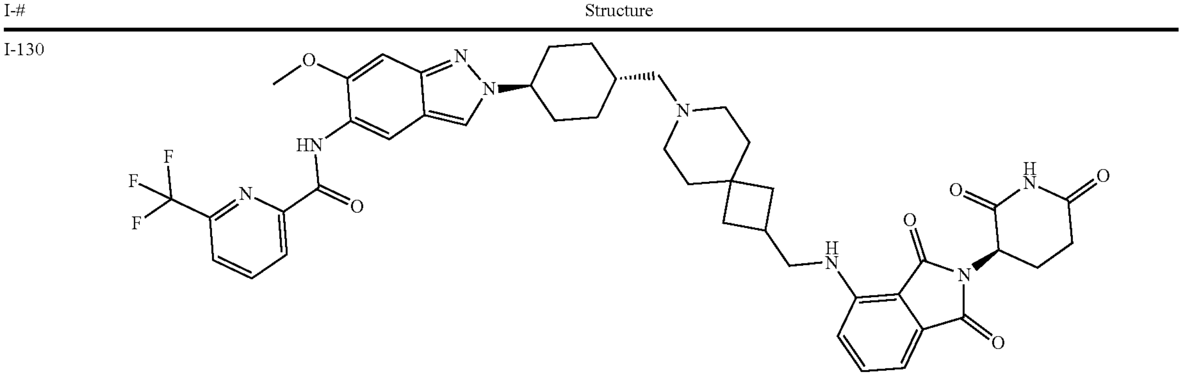 |
| I-131 | 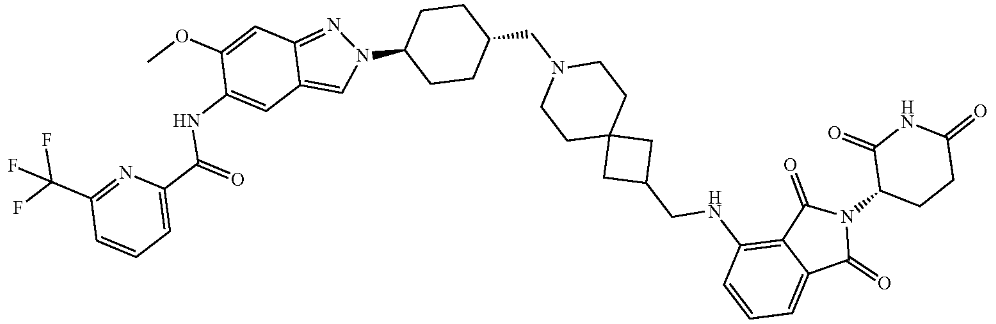 [SMILES: COc1cc2nn([C@H]3CC[C@H](CN4CCC5(CC4)CC(CNc4cccc6c4C(=O)N([C@H]4CCC(=O)NC4=O)C6=O)C5)CC3)cc2cc1NC(=O)c1cccc(C(F)(F)F)n1] |
| I-132 | 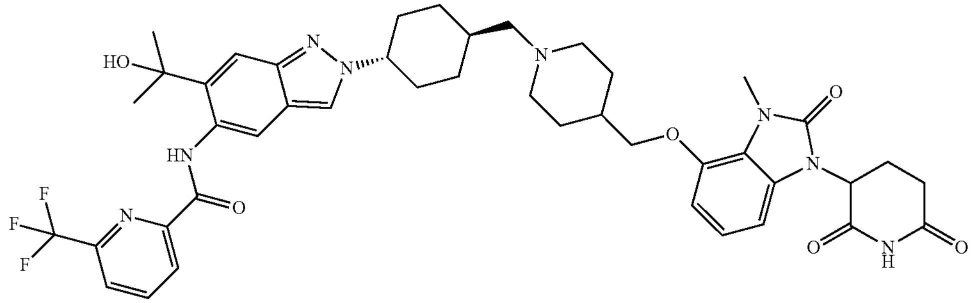 [SMILES: Cn1c(=O)n(C2CCC(=O)NC2=O)c2cccc(OCC3CCN(C[C@H]4CC[C@H](n5cc6cc(NC(=O)c7cccc(C(F)(F)F)n7)c(C(C)(C)O)cc6n5)CC4)CC3)c21] |
| I-133 | 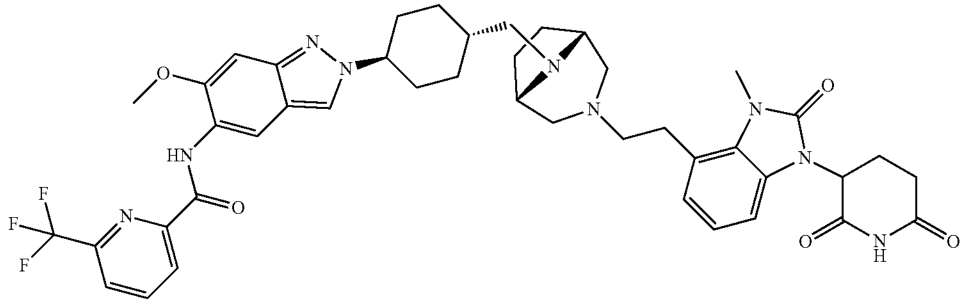 [SMILES: COc1cc2nn([C@H]3CC[C@H](CN4[C@@H]5CC[C@H]4CN(CCc4cccc6c4n(C)c(=O)n6C4CCC(=O)NC4=O)C5)CC3)cc2cc1NC(=O)c1cccc(C(F)(F)F)n1] |
| I-134 | 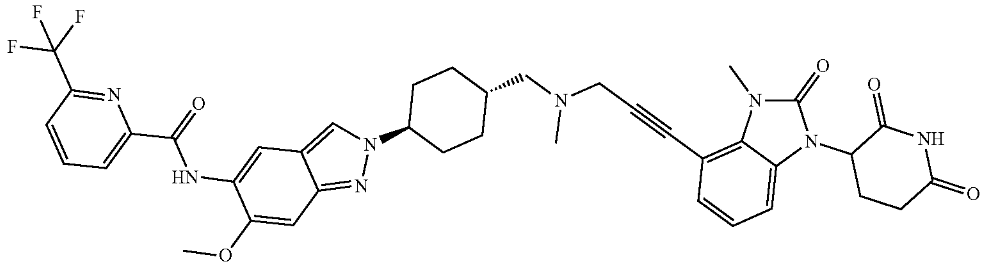 [SMILES: COc1cc2nn([C@H]3CC[C@H](CN(C)CC#Cc4cccc5c4n(C)c(=O)n5C4CCC(=O)NC4=O)CC3)cc2cc1NC(=O)c1cccc(C(F)(F)F)n1] |

TABLE 1-continued
| Exemplary Compounds | |
|---|---|
| I-# | Structure |
| I-135 | 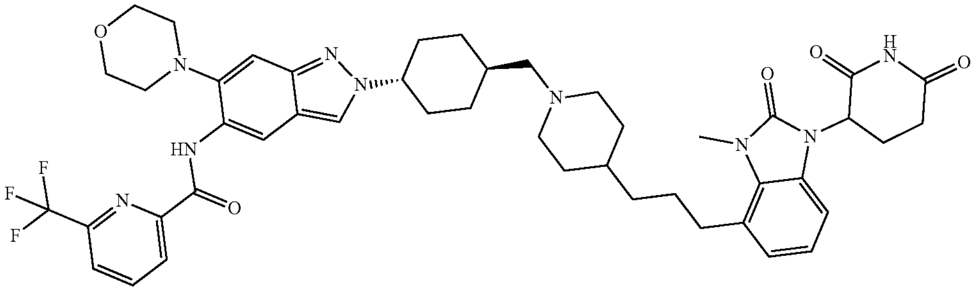 [SMILES: Cn1c(=O)n(C2CCC(=O)NC2=O)c2cccc(CCCC3CCN(C[C@H]4CC[C@H](n5cc6cc(NC(=O)c7cccc(C(F)(F)F)n7)c(N7CCOCC7)cc6n5)CC4)CC3)c21] |
| I-136 | 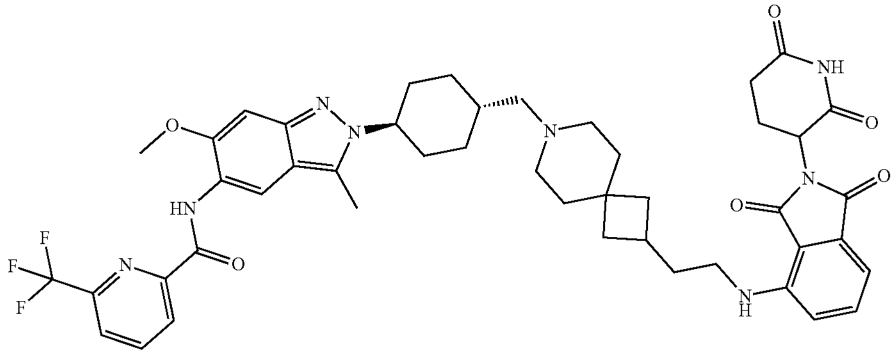 [SMILES: COc1cc2nn([C@H]3CC[C@H](CN4CCC5(CC4)CC(CCNc4cccc6c4C(=O)N(C4CCC(=O)NC4=O)C6=O)C5)CC3)c(C)c2cc1NC(=O)c1cccc(C(F)(F)F)n1] |
| I-137 | 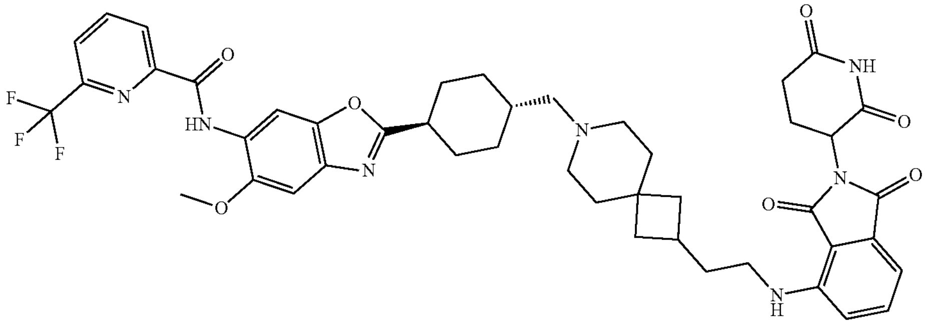 [SMILES: COc1cc2nc([C@H]3CC[C@H](CN4CCC5(CC4)CC(CCNc4cccc6c4C(=O)N(C4CCC(=O)NC4=O)C6=O)C5)CC3)oc2cc1NC(=O)c1cccc(C(F)(F)F)n1] |
| I-138 | 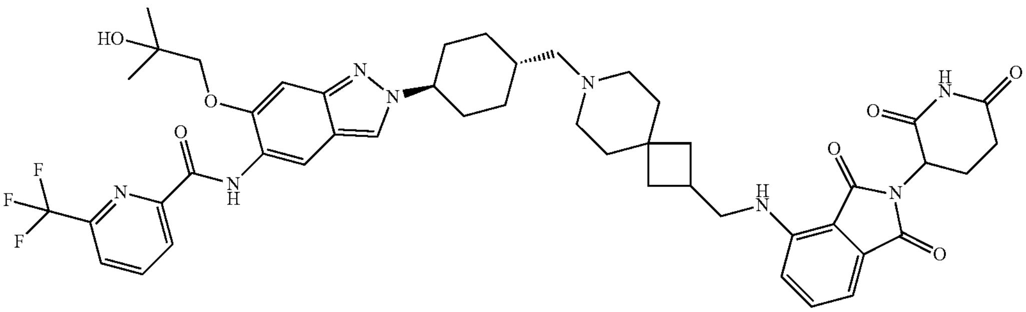 |

TABLE 1-continued
| Exemplary Compounds | |
|---|---|
| I-# | Structure |
| I-139 | 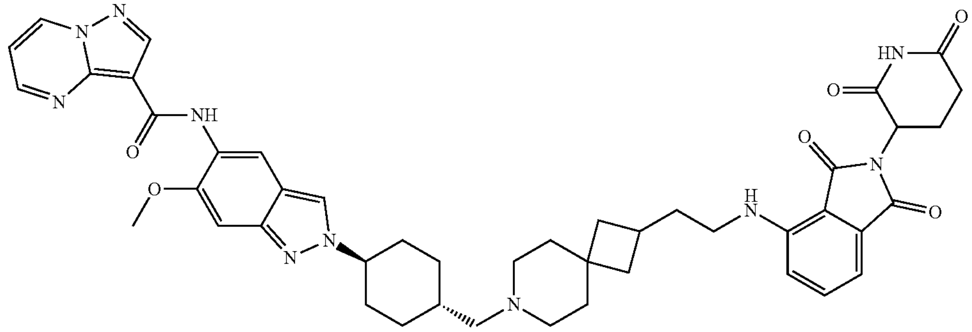 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cnn2cccnc12] |
| I-140 | 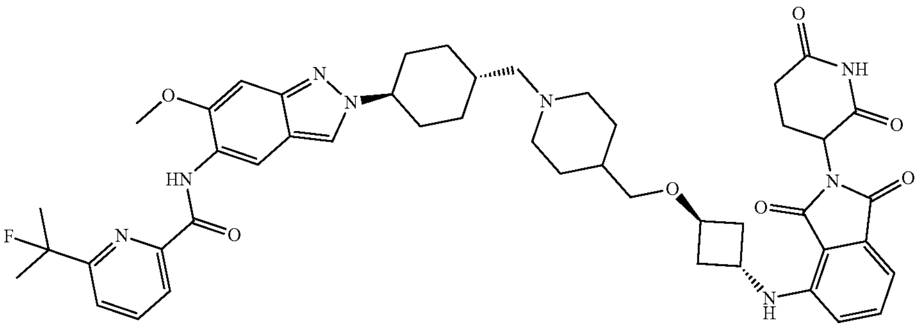 [SMILES: COc1cc2nn([C@H]3CC[C@H](CN4CCC(CO[C@H]5C[C@H](Nc6cccc7c6C(=O)N(C6CCC(=O)NC6=O)C7=O)C5)CC4)CC3)cc2cc1NC(=O)c1cccc(C(C)(C)F)n1] |
| I-141 | 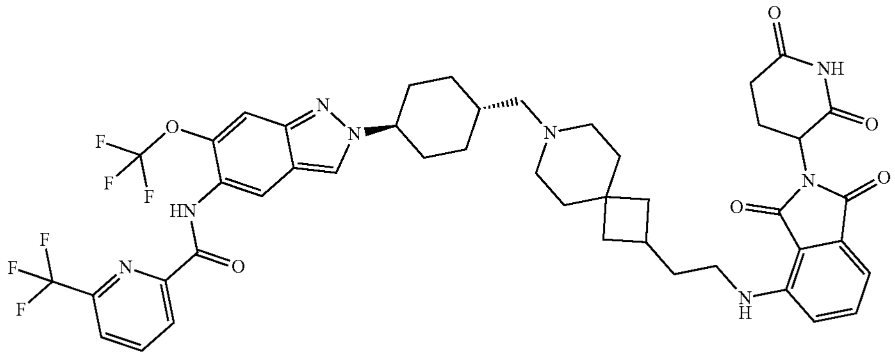 [SMILES: O=C1CCC(N2C(=O)c3cccc(NCCC4CC5(CCN(C[C@H]6CC[C@H](n7cc8cc(NC(=O)c9cccc(C(F)(F)F)n9)c(OC(F)(F)F)cc8n7)CC6)CC5)C4)c3C2=O)C(=O)N1] |
| I-142 | 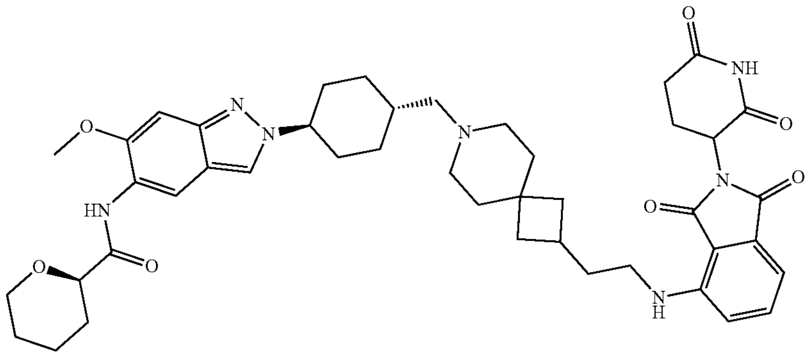 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)[C@H]1CCCCO1] |

TABLE 1-continued
| Exemplary Compounds | |
|---|---|
| I-# | Structure |
| I-143 | 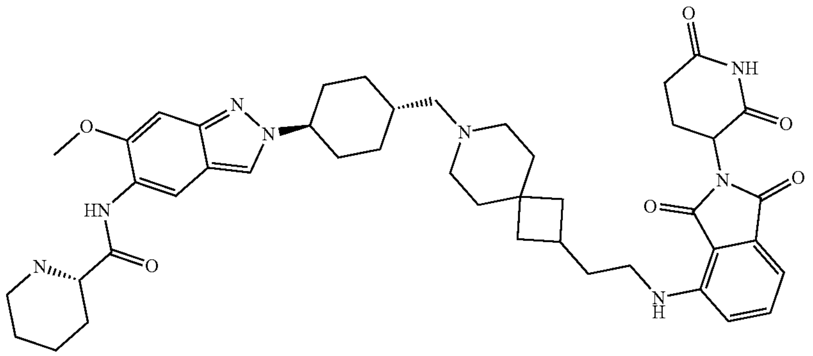 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)[C@@H]1CCCCN1] |
| I-144 | 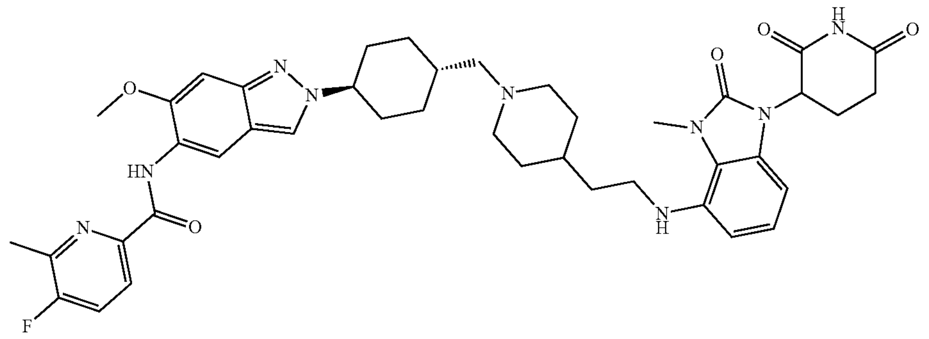 [SMILES: COc1cc2nn([C@H]3CC[C@H](CN4CCC(CCNc5cccc6c5n(C)c(=O)n6C5CCC(=O)NC5=O)CC4)CC3)cc2cc1NC(=O)c1ccc(F)c(C)n1] |
| I-145 | 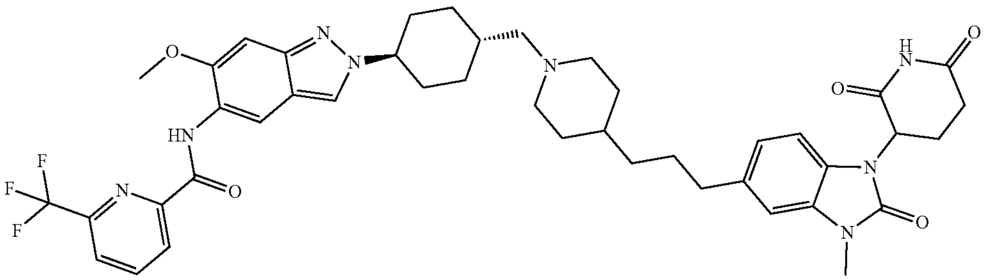 [SMILES: COc1cc2nn([C@H]3CC[C@H](CN4CCC(CCCc5ccc6c(c5)n(C)c(=O)n6C5CCC(=O)NC5=O)CC4)CC3)cc2cc1NC(=O)c1cccc(C(F)(F)F)n1] |
| I-146 | 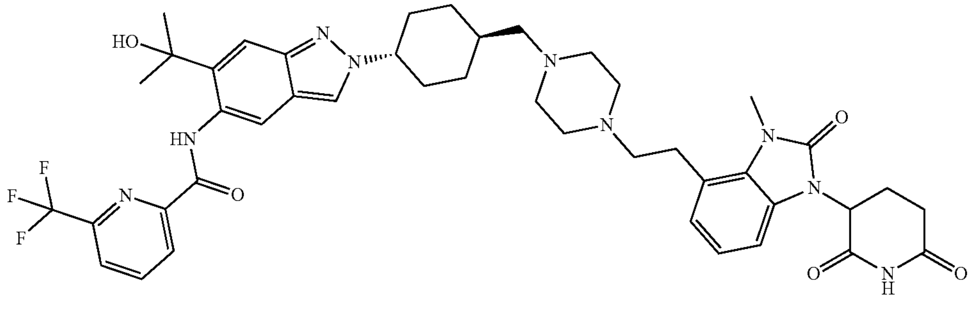 [SMILES: Cn1c(=O)n(C2CCC(=O)NC2=O)c2cccc(CCN3CCN(C[C@H]4CC[C@H](n5cc6cc(NC(=O)c7cccc(C(F)(F)F)n7)c(C(C)(C)O)cc6n5)CC4)CC3)c21] |
| I-147 | 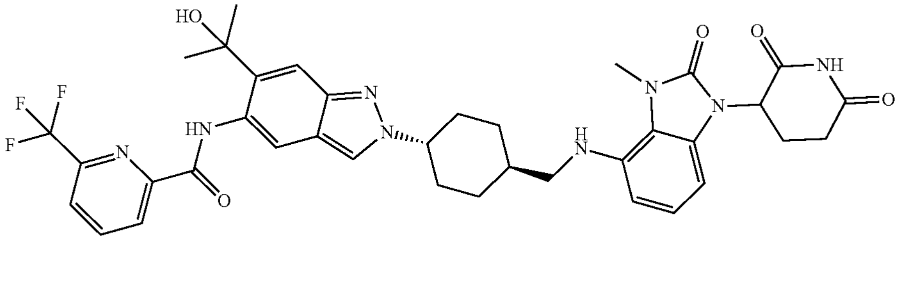 [SMILES: Cn1c(=O)n(C2CCC(=O)NC2=O)c2cccc(NC[C@H]3CC[C@H](n4cc5cc(NC(=O)c6cccc(C(F)(F)F)n6)c(C(C)(C)O)cc5n4)CC3)c21] |

TABLE 1-continued
| Exemplary Compounds | |
|---|---|
| I-# | Structure |
| I-148 | 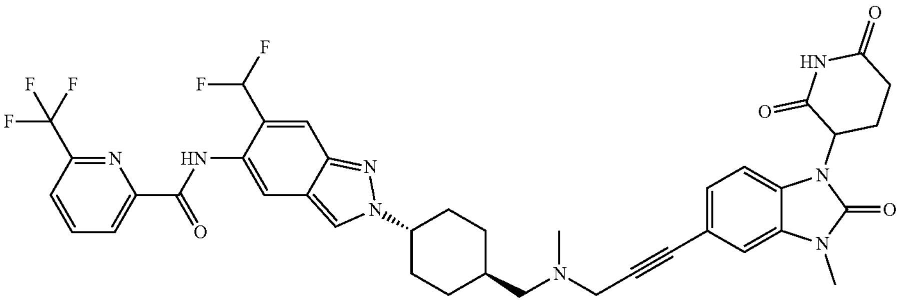 [SMILES: CN(CC#Cc1ccc2c(c1)n(C)c(=O)n2C1CCC(=O)NC1=O)C[C@H]1CC[C@H](n2cc3cc(NC(=O)c4cccc(C(F)(F)F)n4)c(C(F)F)cc3n2)CC1] |
| I-149 | 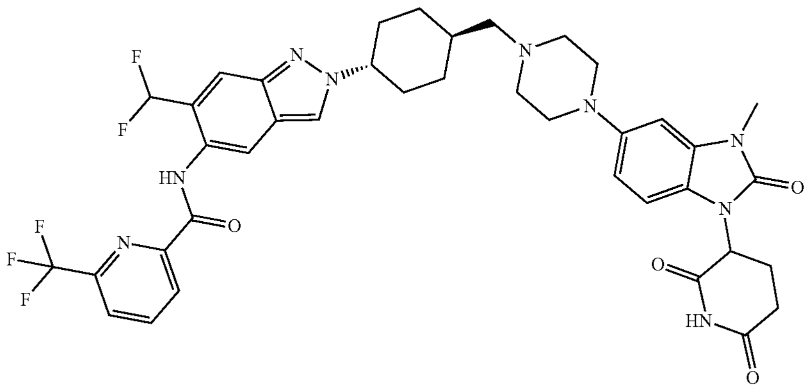 [SMILES: Cn1c(=O)n(C2CCC(=O)NC2=O)c2ccc(N3CCN(C[C@H]4CC[C@H](n5cc6cc(NC(=O)c7cccc(C(F)(F)F)n7)c(C(F)F)cc6n5)CC4)CC3)cc21] |
| I-150 | 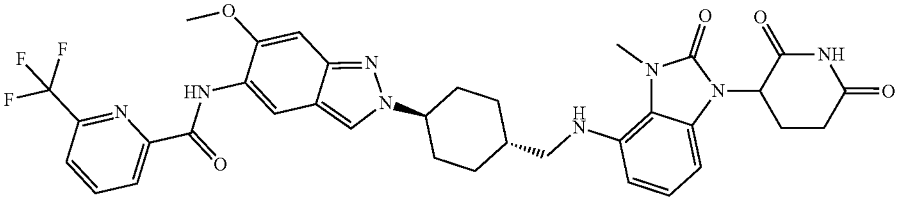 [SMILES: COc1cc2nn([C@H]3CC[C@H](CNc4cccc5c4n(C)c(=O)n5C4CCC(=O)NC4=O)CC3)cc2cc1NC(=O)c1cccc(C(F)(F)F)n1] |
| I-151 | 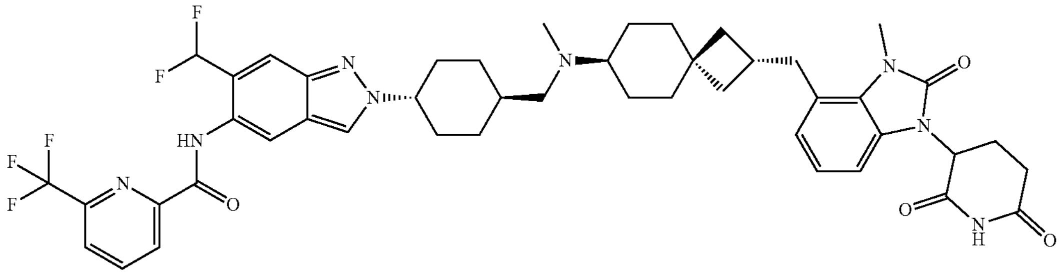 |
| I-152 | 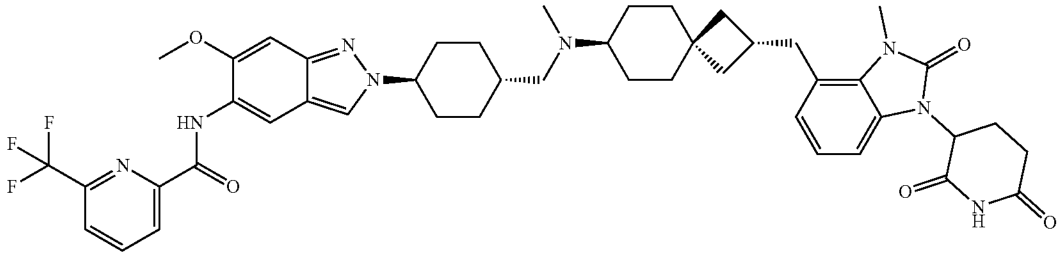 |

TABLE 1-continued
| Exemplary Compounds | |
|---|---|
| I-# | Structure |
| I-153 | 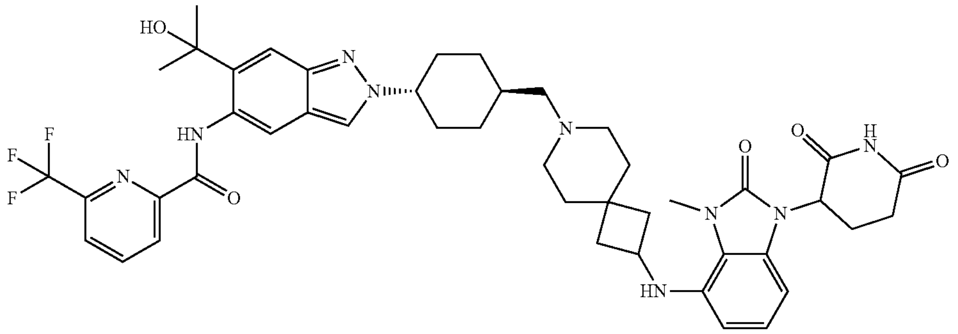 [SMILES: Cn1c(=O)n(C2CCC(=O)NC2=O)c2cccc(NC3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-154 | 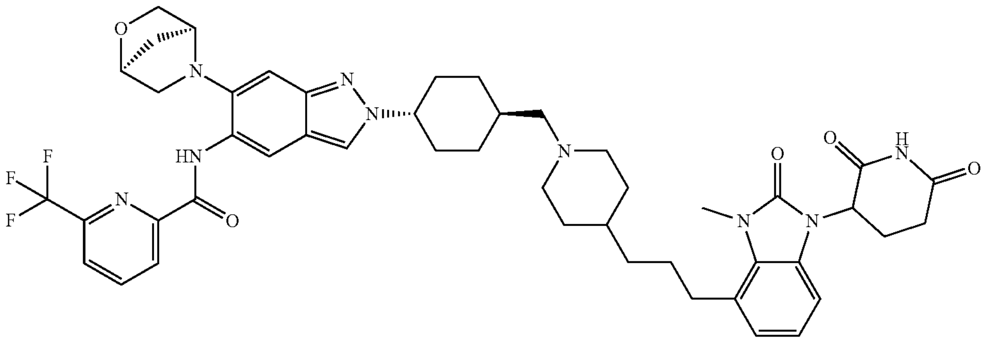 [SMILES: Cn1c(=O)n(C2CCC(=O)NC2=O)c2cccc(CCCC3CCN(C[C@H]4CC[C@H](n5cc6cc(NC(=O)c7cccc(C(F)(F)F)n7)c(N7C[C@@H]8C[C@H]7CO8)cc6n5)CC4)CC3)c21] |
| I-155 | 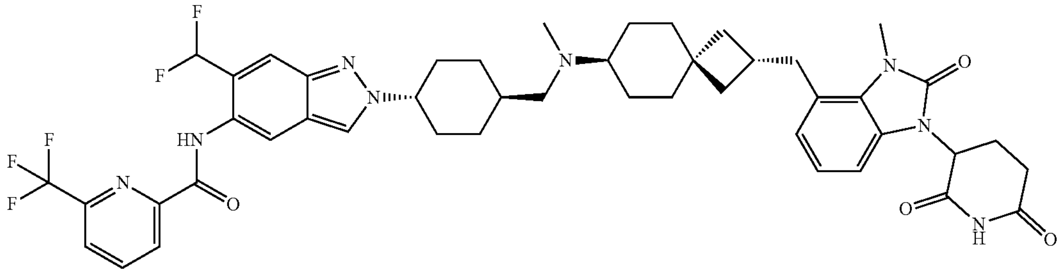 |
| I-156 | 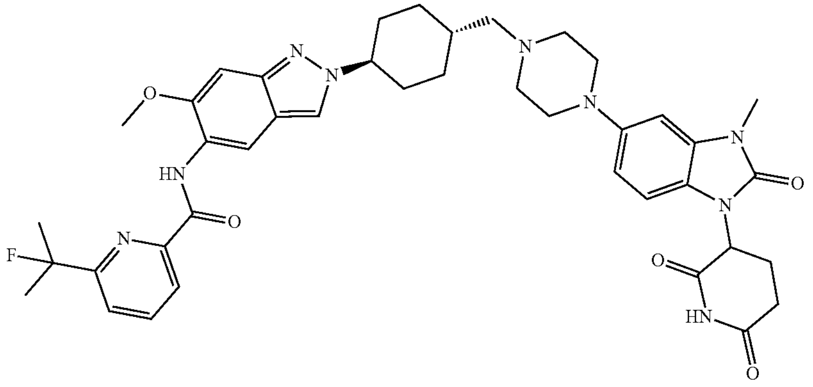 [SMILES: COc1cc2nn([C@H]3CC[C@H](CN4CCN(c5ccc6c(c5)n(C)c(=O)n6C5CCC(=O)NC5=O)CC4)CC3)cc2cc1NC(=O)c1cccc(C(C)(C)F)n1] |

TABLE 1-continued
| Exemplary Compounds | |
|---|---|
| I-# | Structure |
| I-157 | 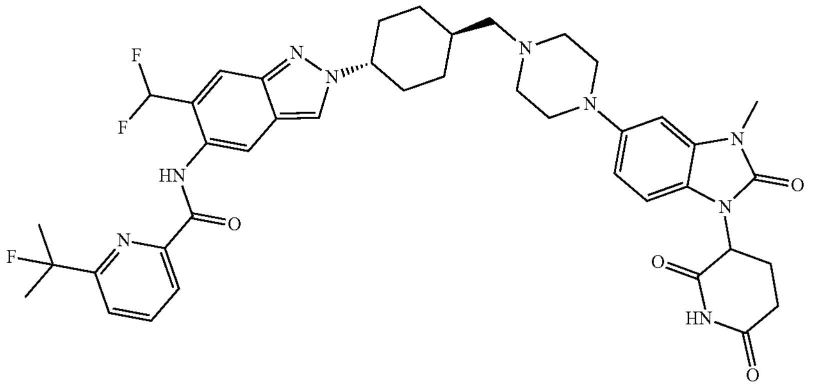 [SMILES: Cn1c(=O)n(C2CCC(=O)NC2=O)c2ccc(N3CCN(C[C@H]4CC[C@H](n5cc6cc(NC(=O)c7cccc(C(C)(C)F)n7)c(C(F)F)cc6n5)CC4)CC3)cc21] |
| I-158 | 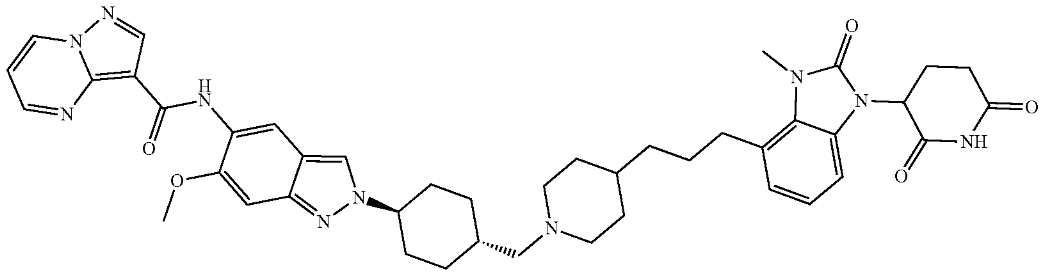 [SMILES: COc1cc2nn([C@H]3CC[C@H](CN4CCC(CCCc5cccc6c5n(C)c(=O)n6C5CCC(=O)NC5=O)CC4)CC3)cc2cc1NC(=O)c1cnn2cccnc12] |
| I-159 | 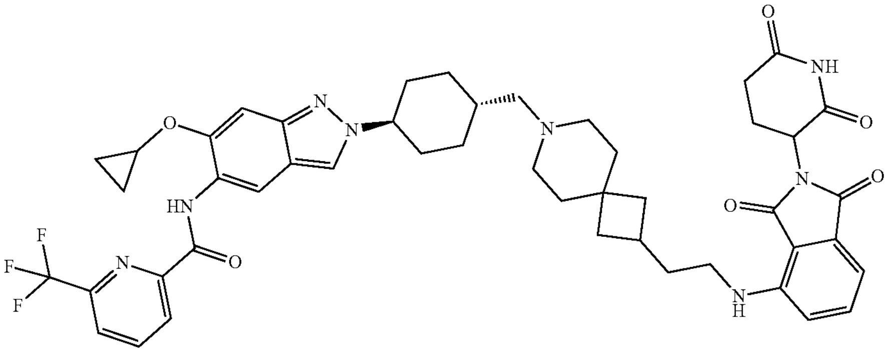 [SMILES: O=C1CCC(N2C(=O)c3cccc(NCCC4CC5(CCN(C[C@H]6CC[C@H](n7cc8cc(NC(=O)c9cccc(C(F)(F)F)n9)c(OC9CC9)cc8n7)CC6)CC5)C4)c3C2=O)C(=O)N1] |
| I-160 | 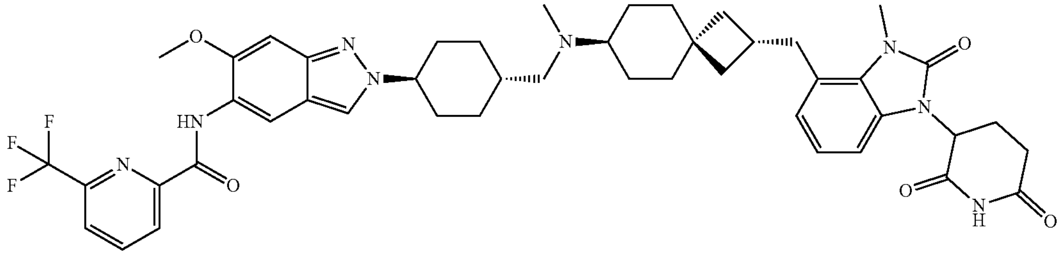 |

TABLE 1-continued
| Exemplary Compounds | |
|---|---|
| I-# | Structure |
| I-161 | 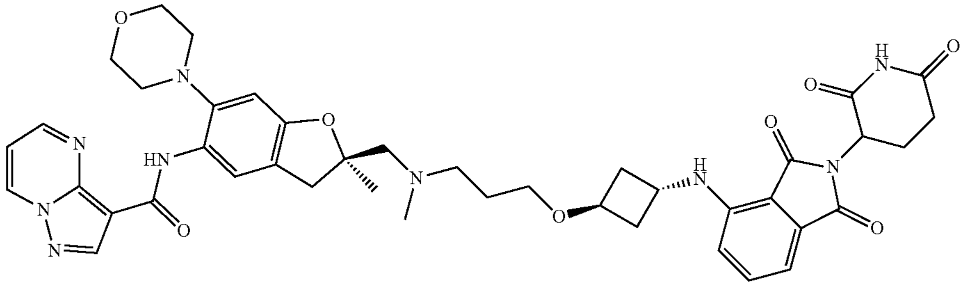 [SMILES: CN(CCCO[C@H]1C[C@H](Nc2cccc3c2C(=O)N(C2CCC(=O)NC2=O)C3=O)C1)C[C@@]1(C)Cc2cc(NC(=O)c3cnn4cccnc34)c(N3CCOCC3)cc2O1] |
| I-162 | 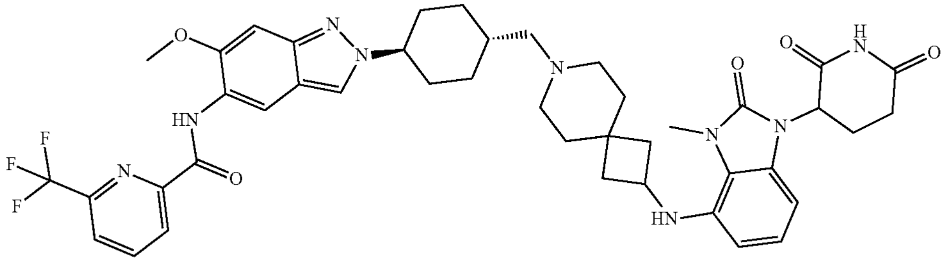 [SMILES: COc1cc2nn([C@H]3CC[C@H](CN4CCC5(CC4)CC(Nc4cccc6c4n(C)c(=O)n6C4CCC(=O)NC4=O)C5)CC3)cc2cc1NC(=O)c1cccc(C(F)(F)F)n1] |
| I-163 | 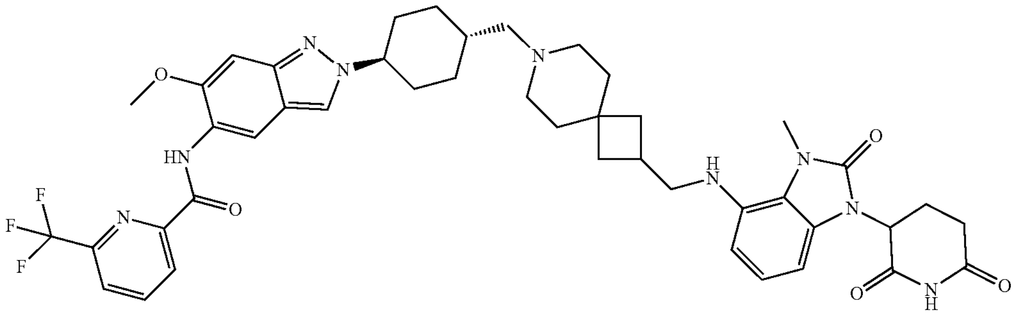 [SMILES: COc1cc2nn([C@H]3CC[C@H](CN4CCC5(CC4)CC(CNc4cccc6c4n(C)c(=O)n6C4CCC(=O)NC4=O)C5)CC3)cc2cc1NC(=O)c1cccc(C(F)(F)F)n1] |
| I-164 | 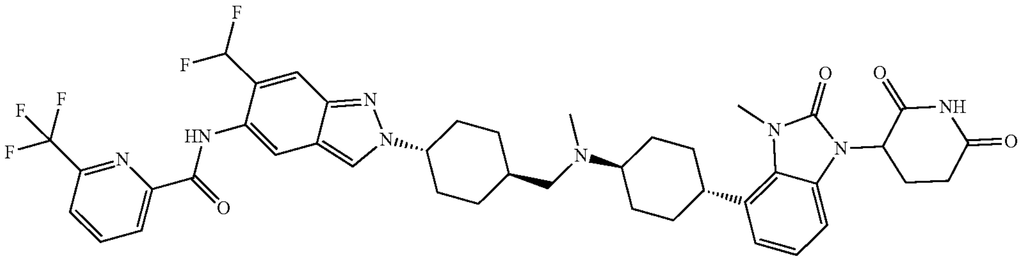 [SMILES: Cn1c(=O)n(C2CCC(=O)NC2=O)c2cccc([C@H]3CC[C@H](N(C)C[C@H]4CC[C@H](n5cc6cc(NC(=O)c7cccc(C(F)(F)F)n7)c(C(F)F)cc6n5)CC4)CC3)c21] |
| I-165 | 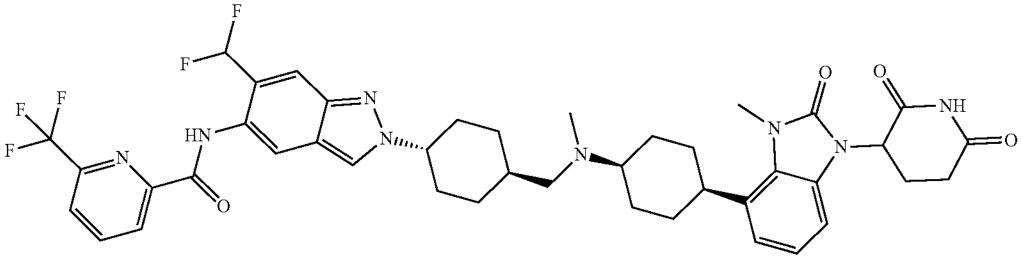 [SMILES: Cn1c(=O)n(C2CCC(=O)NC2=O)c2cccc([C@H]3CC[C@@H](N(C)C[C@H]4CC[C@H](n5cc6cc(NC(=O)c7cccc(C(F)(F)F)n7)c(C(F)F)cc6n5)CC4)CC3)c21] |

TABLE 1-continued
| Exemplary Compounds | |
|---|---|
| I-# | Structure |
| I-166 | 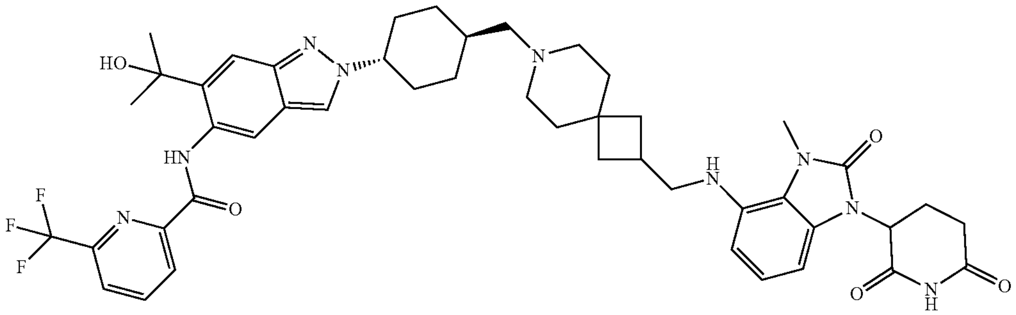 [SMILES: Cn1c(=O)n(C2CCC(=O)NC2=O)c2cccc(NCC3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-167 | 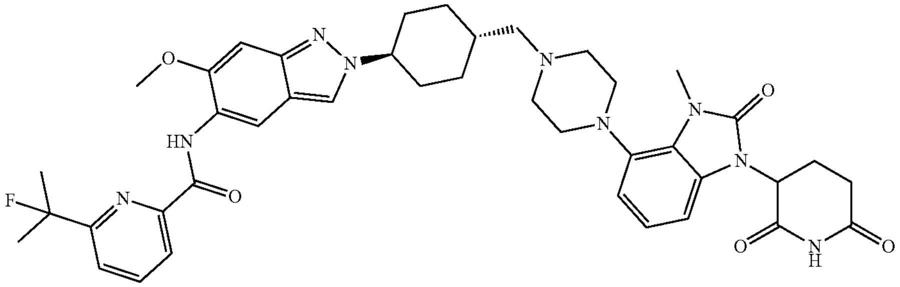 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1cccc(C(C)(C)F)n1] |
| I-168 | 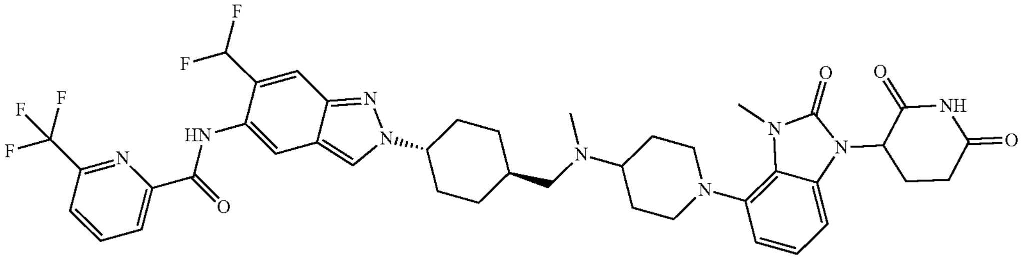 [SMILES: CN(C[C@H]1CC[C@H](n2cc3cc(NC(=O)c4cccc(C(F)(F)F)n4)c(C(F)F)cc3n2)CC1)C1CCN(c2cccc3c2n(C)c(=O)n3C2CCC(=O)NC2=O)CC1] |
| I-169 | 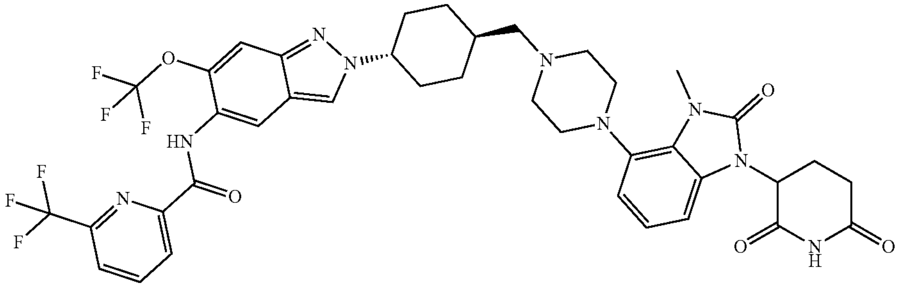 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(OC(F)(F)F)cc6n5)CC4)CC3)c21] |
| I-170 | 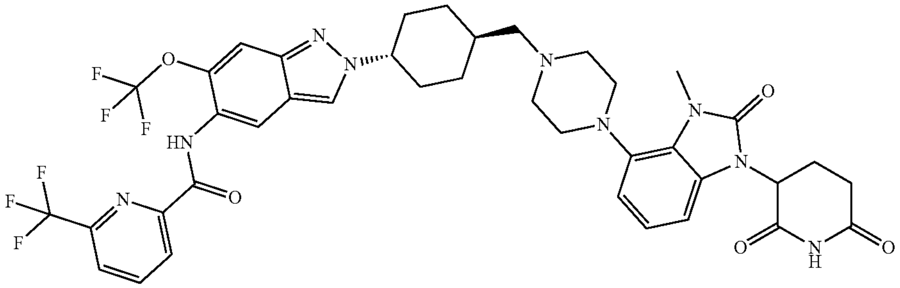 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(OC(F)(F)F)cc6n5)CC4)CC3)c21] |

TABLE 1-continued
| Exemplary Compounds | |
|---|---|
| I-# | Structure |
| I-171 | 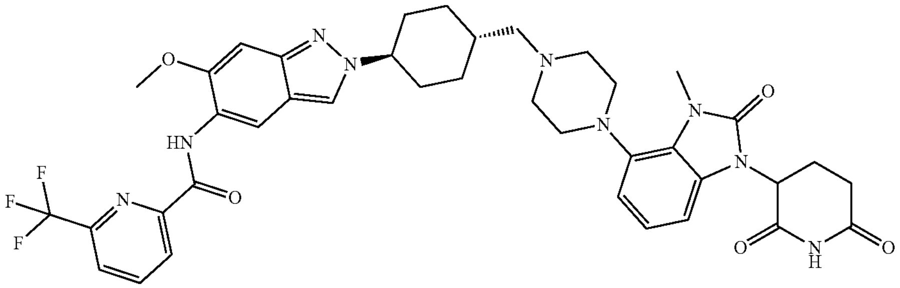 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |
| I-172 | 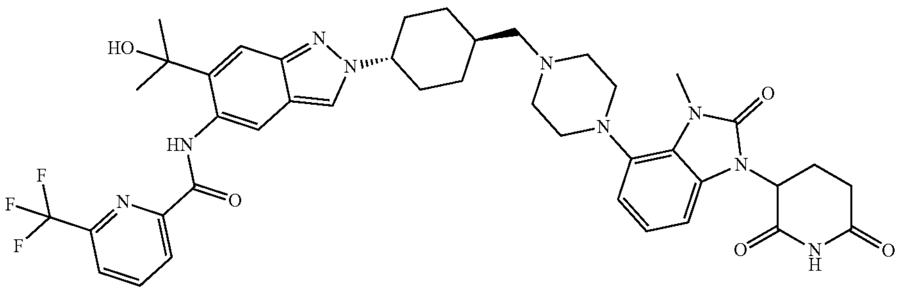 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(C(C)(C)O)cc6n5)CC4)CC3)c21] |
| I-173 | 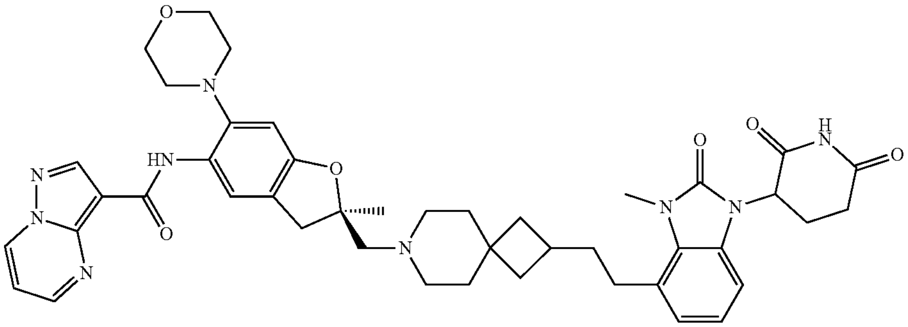 [SMILES: Cn1c(=O)n(C2CCC(=O)NC2=O)c2cccc(CCC3CC4(CCN(C[C@@]5(C)Cc6cc(NC(=O)c7cnn8cccnc78)c(N7CCOCC7)cc6O5)CC4)C3)c21] |
| I-174 | 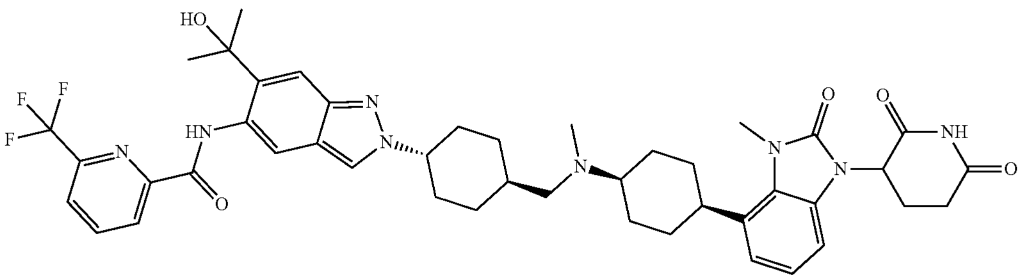 [SMILES: Cn1c(=O)n(C2CCC(=O)NC2=O)c2cccc([C@H]3CC[C@@H](N(C)C[C@H]4CC[C@H](n5cc6cc(NC(=O)c7cccc(C(F)(F)F)n7)c(C(C)(C)O)cc6n5)CC4)CC3)c21] |
| I-175 | 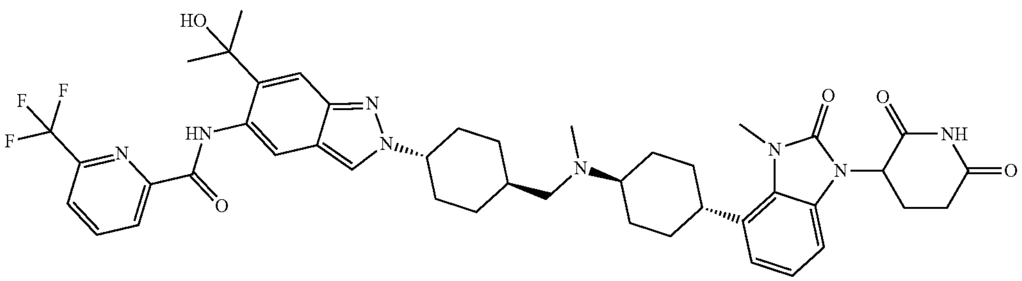 [SMILES: Cn1c(=O)n(C2CCC(=O)NC2=O)c2cccc([C@H]3CC[C@H](N(C)C[C@H]4CC[C@H](n5cc6cc(NC(=O)c7cccc(C(F)(F)F)n7)c(C(C)(C)O)cc6n5)CC4)CC3)c21] |

TABLE 1-continued
| Exemplary Compounds | |
|---|---|
| I-# | Structure |
| I-176 | 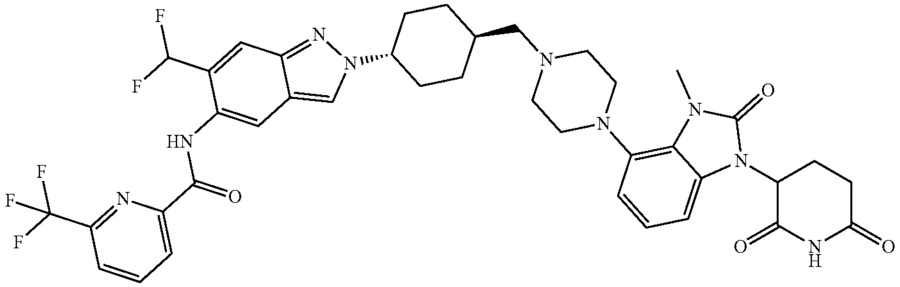 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(C(F)F)cc6n5)CC4)CC3)c21] |
| I-177 | 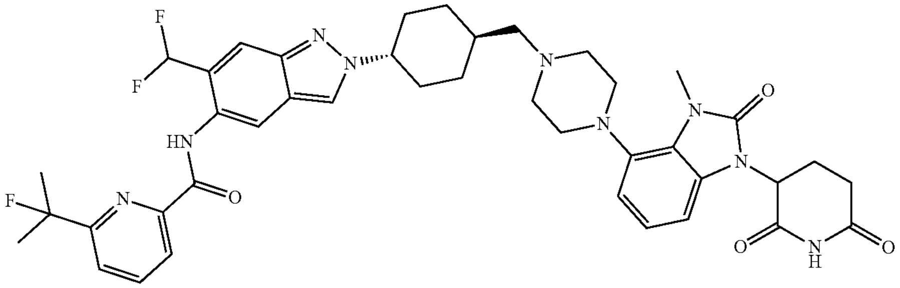 [SMILES: Cn1c(=O)n(C2CCC(=O)NC2=O)c2cccc(N3CCN(C[C@H]4CC[C@H](n5cc6cc(NC(=O)c7cccc(C(C)(C)F)n7)c(C(F)F)cc6n5)CC4)CC3)c21] |
| I-178 | 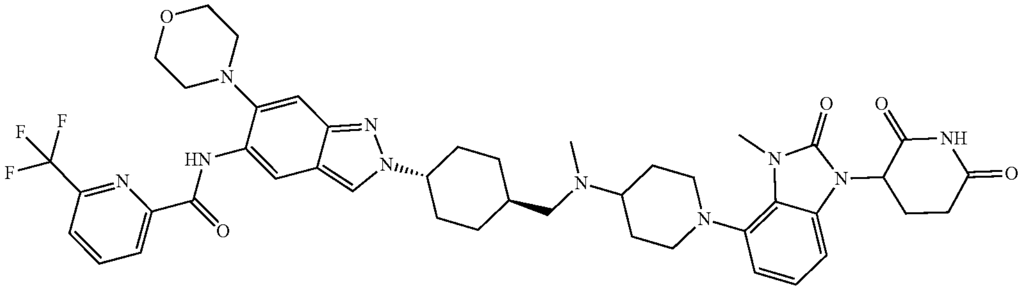 [SMILES: CN(C[C@H]1CC[C@H](n2cc3cc(NC(=O)c4cccc(C(F)(F)F)n4)c(N4CCOCC4)cc3n2)CC1)C1CCN(c2cccc3c2n(C)c(=O)n3C2CCC(=O)NC2=O)CC1] |
| I-179 | 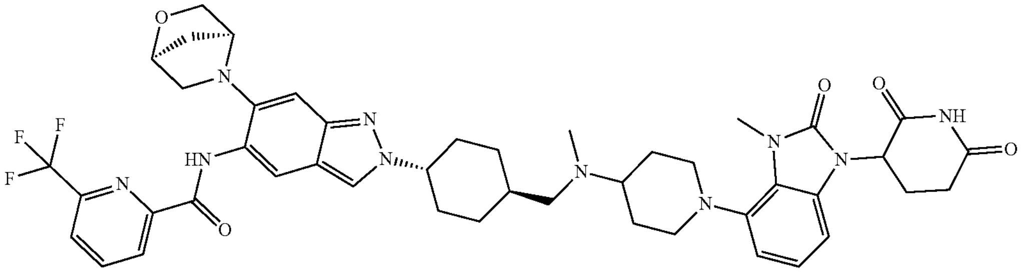 [SMILES: CN(C[C@H]1CC[C@H](n2cc3cc(NC(=O)c4cccc(C(F)(F)F)n4)c(N4C[C@@H]5C[C@H]4CO5)cc3n2)CC1)C1CCN(c2cccc3c2n(C)c(=O)n3C2CCC(=O)NC2=O)CC1] |
| I-180 | 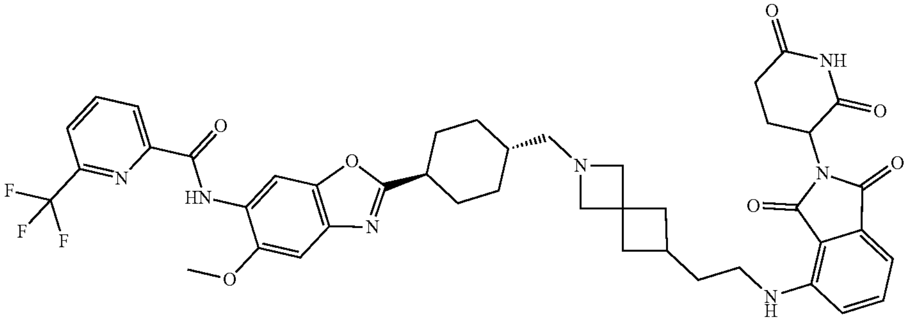 [SMILES: COc1cc2nc([C@H]3CC[C@H](CN4CC5(CC(CCNc6cccc7c6C(=O)N(C6CCC(=O)NC6=O)C7=O)C5)C4)CC3)oc2cc1NC(=O)c1cccc(C(F)(F)F)n1] |

TABLE 1-continued
| Exemplary Compounds | |
|---|---|
| I-# | Structure |
| I-181 | 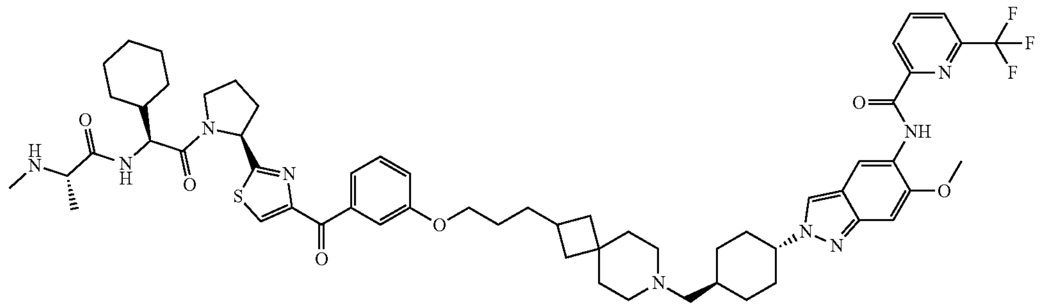 [SMILES: CN[C@@H](C)C(=O)N[C@H](C(=O)N1CCC[C@H]1c1nc(C(=O)c2cccc(OCCCC3CC4(CCN(C[C@H]5CC[C@H](n6cc7cc(NC(=O)c8cccc(C(F)(F)F)n8)c(OC)cc7n6)CC5)CC4)C3)c2)cs1)C1CCCCC1] |
| I-182 | 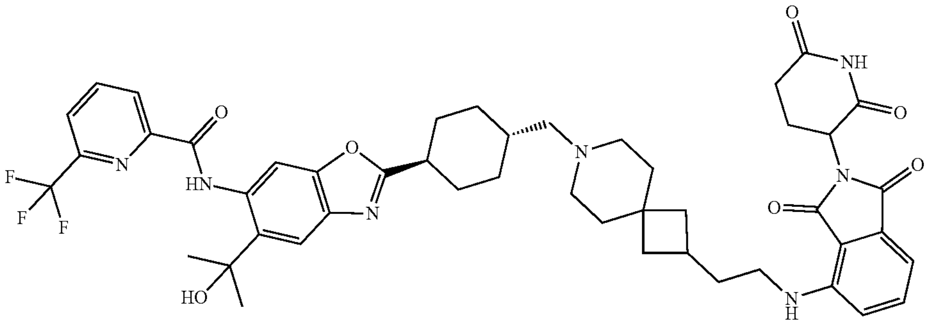 [SMILES: CC(C)(O)c1cc2nc([C@H]3CC[C@H](CN4CCC5(CC4)CC(CCNc4cccc6c4C(=O)N(C4CCC(=O)NC4=O)C6=O)C5)CC3)oc2cc1NC(=O)c1cccc(C(F)(F)F)n1] |
| I-183 | 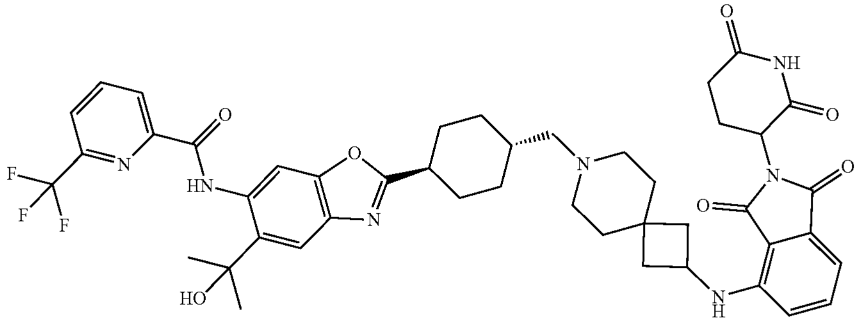 [SMILES: CC(C)(O)c1cc2nc([C@H]3CC[C@H](CN4CCC5(CC4)CC(Nc4cccc6c4C(=O)N(C4CCC(=O)NC4=O)C6=O)C5)CC3)oc2cc1NC(=O)c1cccc(C(F)(F)F)n1] |
| I-184 | 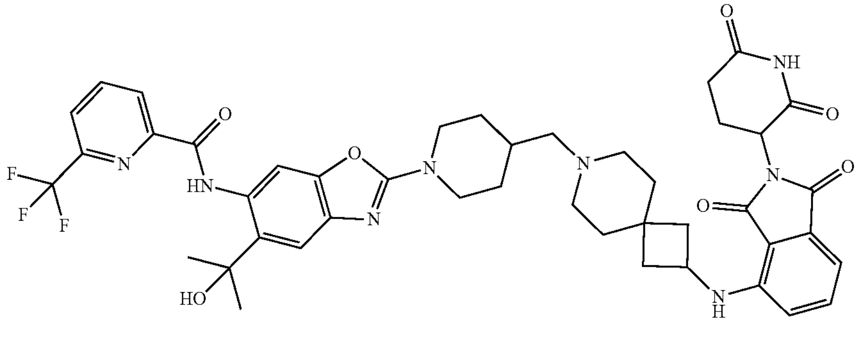 [SMILES: CC(C)(O)c1cc2nc(N3CCC(CN4CCC5(CC4)CC(Nc4cccc6c4C(=O)N(C4CCC(=O)NC4=O)C6=O)C5)CC3)oc2cc1NC(=O)c1cccc(C(F)(F)F)n1] |

TABLE 1-continued
| Exemplary Compounds | |
|---|---|
| I-# | Structure |
| I-185 | 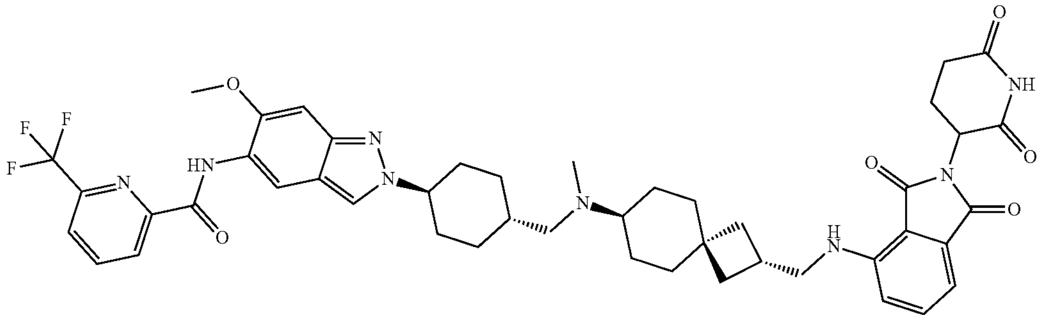 |
| I-186 | 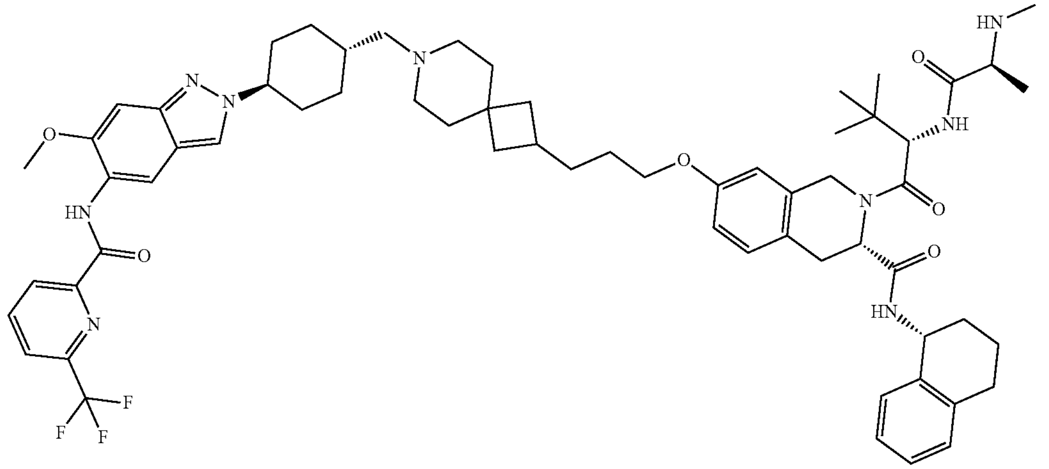 [SMILES: CN[C@@H](C)C(=O)N[C@H](C(=O)N1Cc2cc(OCCCC3CC4(CCN(C[C@H]5CC[C@H](n6cc7cc(NC(=O)c8cccc(C(F)(F)F)n8)c(OC)cc7n6)CC5)CC4)C3)ccc2C[C@H]1C(=O)N[C@@H]1CCCc2ccccc21)C(C)(C)C] |
| I-187 | 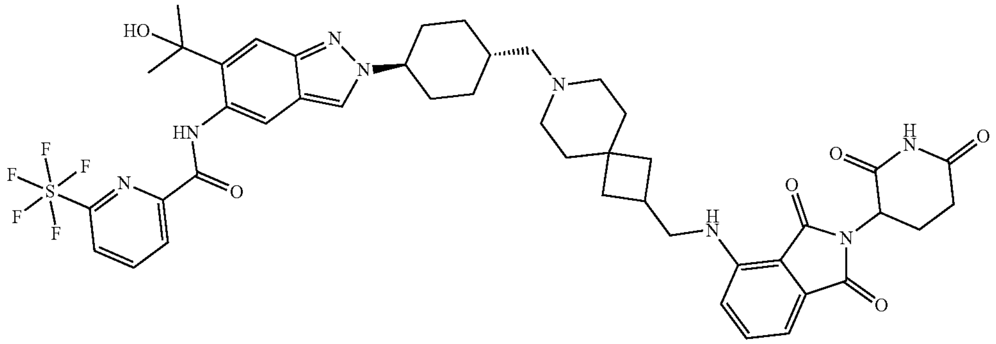 [SMILES: CC(C)(O)c1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(S(F)(F)(F)(F)F)n1] |
| I-188 | 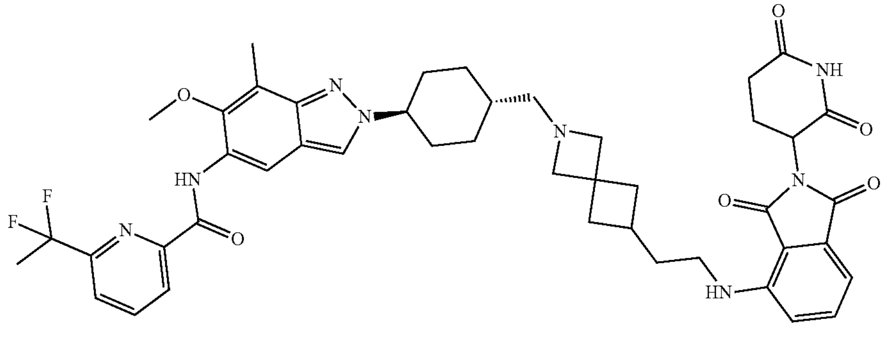 [SMILES: COc1c(NC(=O)c2cccc(C(C)(F)F)n2)cc2cn([C@H]3CC[C@H](CN4CC5(CC(CCNc6cccc7c6C(=O)N(C6CCC(=O)NC6=O)C7=O)C5)C4)CC3)nc2c1C] |

TABLE 1-continued
Exemplary Compounds
| I-# | Structure |
| --- | --- |
| I-189 | 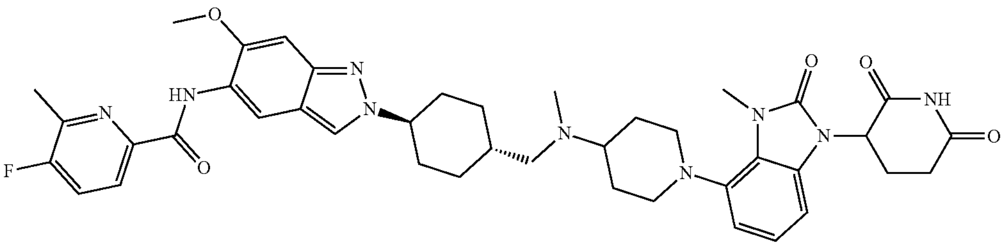 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(F)c(C)n1] |
| I-190 | 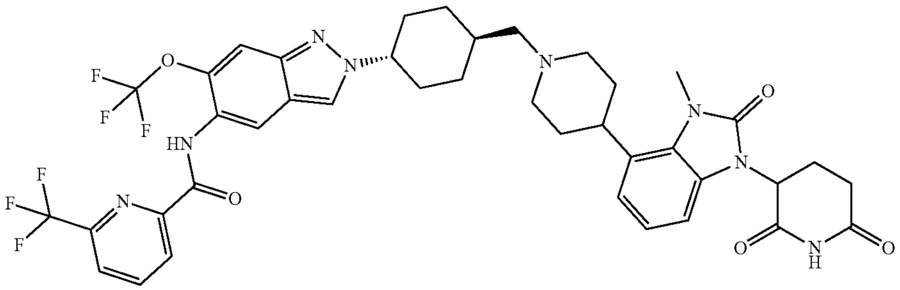 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(OC(F)(F)F)cc6n5)CC4)CC3)c21] |
| I-191 | 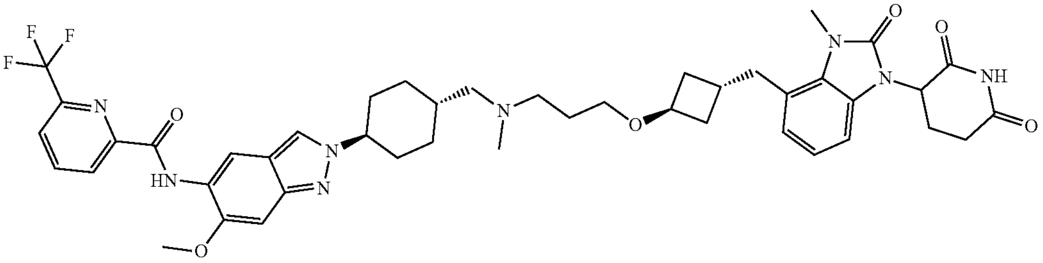 [SMILES: COc1cc2nn([C@H]3CC[C@H](CN(C)CCCO[C@H]4C[C@H](Cc5cccc6c5n(C)c(=O)n6C5CCC(=O)NC5=O)C4)CC3)cc2cc1NC(=O)c1cccc(C(F)(F)F)n1] |
| I-192 | 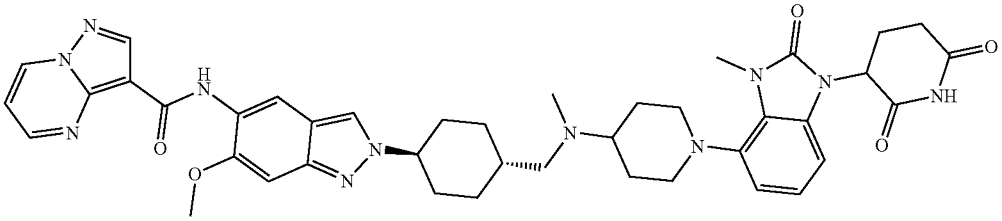 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cnn2cccnc12] |
| I-193 | 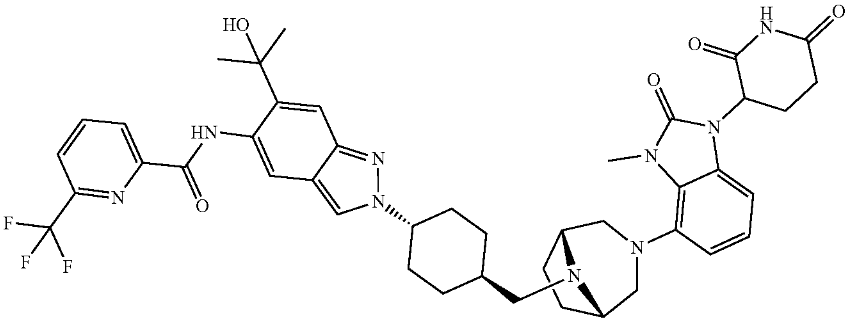 [SMILES: Cn1c(=O)n(C2CCC(=O)NC2=O)c2cccc(N3C[C@H]4CC[C@@H](C3)N4C[C@H]3CC[C@H](n4cc5cc(NC(=O)c6cccc(C(F)(F)F)n6)c(C(C)(C)O)cc5n4)CC3)c21] |

TABLE 1-continued
| Exemplary Compounds | |
|---|---|
| I-# | Structure |
| I-194 | 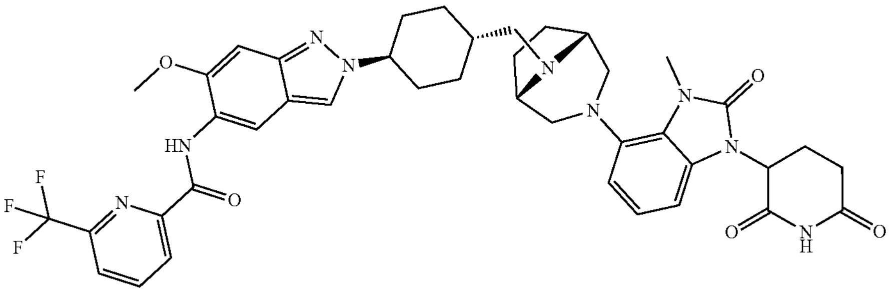 [SMILES: COc1cc2nn([C@H]3CC[C@H](CN4[C@@H]5CC[C@H]4CN(c4cccc6c4n(C)c(=O)n6C4CCC(=O)NC4=O)C5)CC3)cc2cc1NC(=O)c1cccc(C(F)(F)F)n1] |
| I-195 | 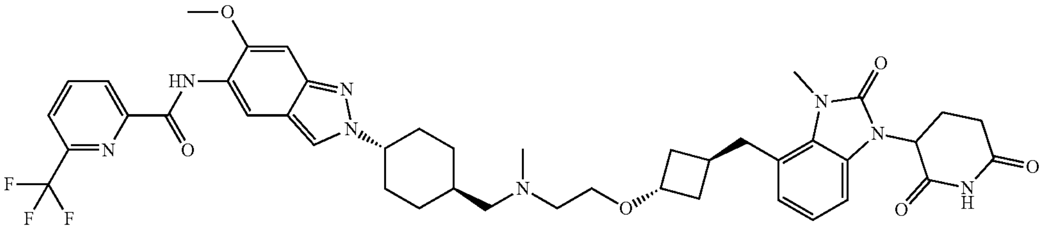 [SMILES: COc1cc2nn([C@H]3CC[C@H](CN(C)CCO[C@H]4C[C@H](Cc5cccc6c5n(C)c(=O)n6C5CCC(=O)NC5=O)C4)CC3)cc2cc1NC(=O)c1cccc(C(F)(F)F)n1] |
| I-196 | 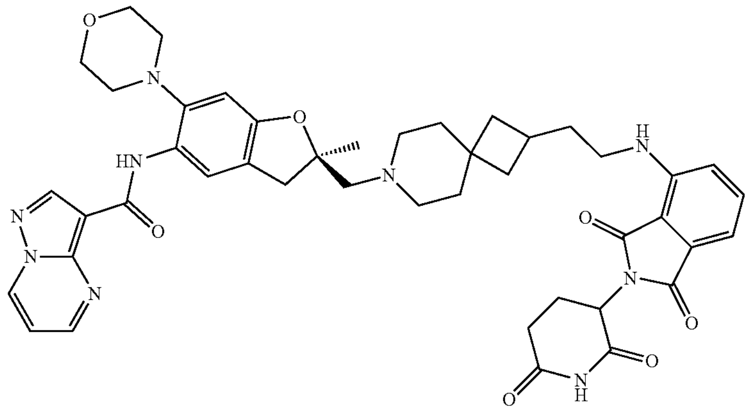 [SMILES: C[C@]1(CN2CCC3(CC2)CC(CCNc2cccc4c2C(=O)N(C2CCC(=O)NC2=O)C4=O)C3)Cc2cc(NC(=O)c3cnn4cccnc34)c(N3CCOCC3)cc2O1] |
| I-197 | 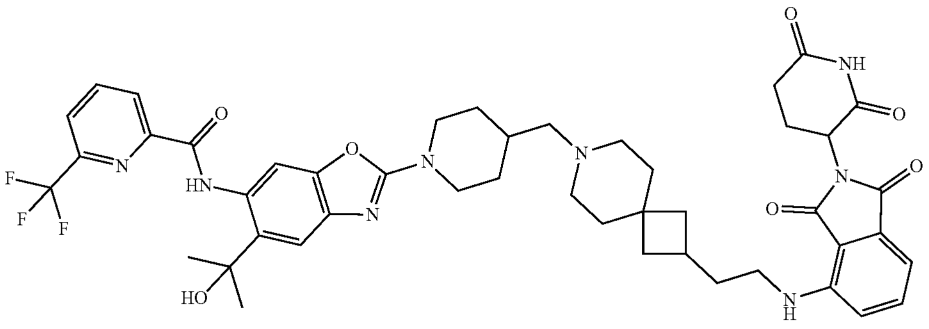 [SMILES: CC(C)(O)c1cc2nc(N3CCC(CN4CCC5(CC4)CC(CCNc4cccc6c4C(=O)N(C4CCC(=O)NC4=O)C6=O)C5)CC3)oc2cc1NC(=O)c1cccc(C(F)(F)F)n1] |

TABLE 1-continued
| Exemplary Compounds | |
|---|---|
| I-# | Structure |
| I-198 | 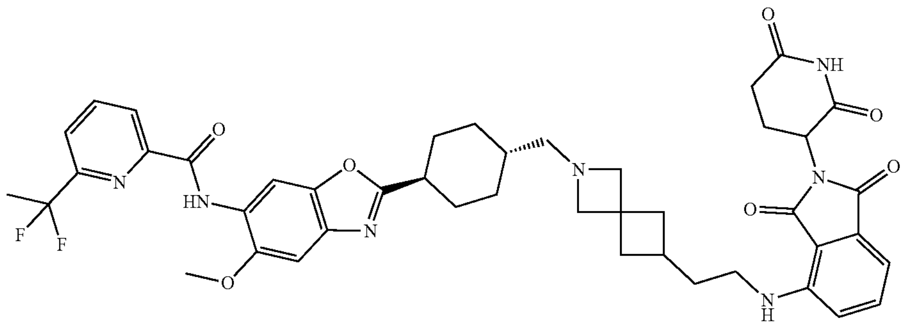 [SMILES: COc1cc2nc([C@H]3CC[C@H](CN4CC5(CC(CCNc6cccc7c6C(=O)N(C6CCC(=O)NC6=O)C7=O)C5)C4)CC3)oc2cc1NC(=O)c1cccc(C(C)(F)F)n1] |
| I-199 | 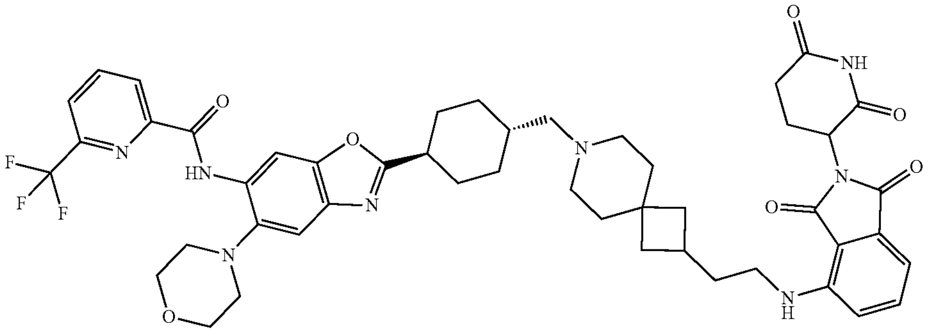 [SMILES: O=C1CCC(N2C(=O)c3cccc(NCCC4CC5(CCN(C[C@H]6CC[C@H](c7nc8cc(N9CCOCC9)c(NC(=O)c9cccc(C(F)(F)F)n9)cc8o7)CC6)CC5)C4)c3C2=O)C(=O)N1] |
| I-200 | 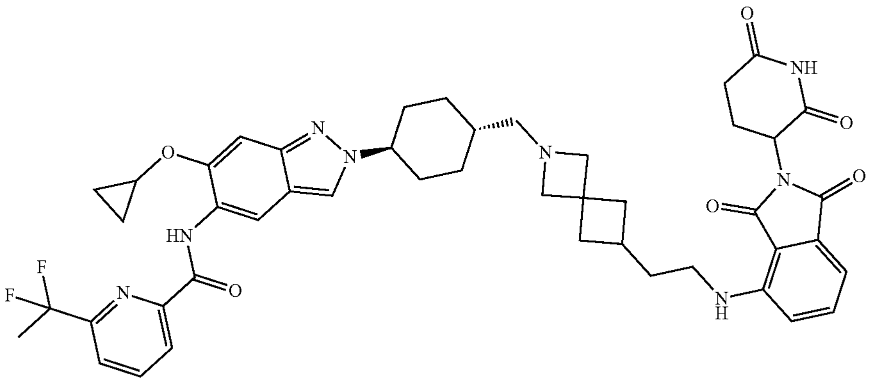 [SMILES: CC(F)(F)c1cccc(C(=O)Nc2cc3cn([C@H]4CC[C@H](CN5CC6(CC(CCNc7cccc8c7C(=O)N(C7CCC(=O)NC7=O)C8=O)C6)C5)CC4)nc3cc2OC2CC2)n1] |
| I-201 | 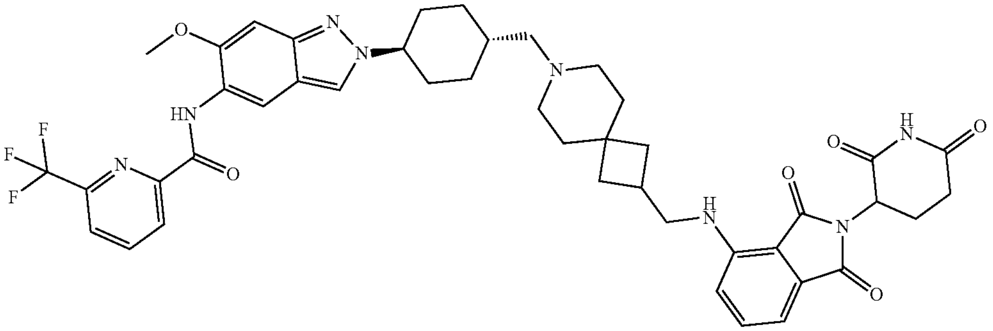 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(F)(F)F)n1] |

TABLE 1-continued
| Exemplary Compounds | |
|---|---|
| I-# | Structure |
| I-202 | 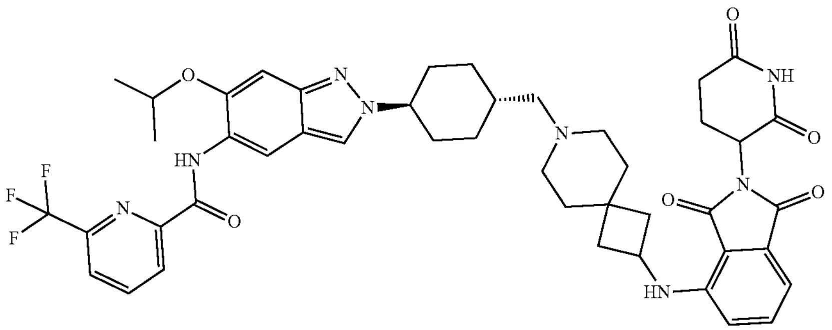 [SMILES: CC(C)Oc1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cccc(C(F)(F)F)n1] |
| I-203 | 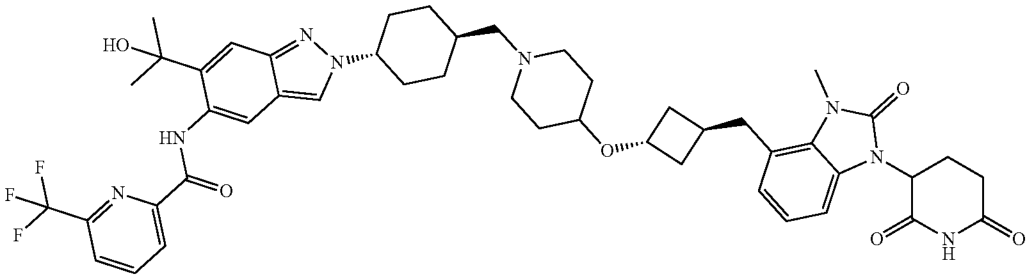 [SMILES: Cn1c(=O)n(C2CCC(=O)NC2=O)c2cccc(C[C@H]3C[C@H](OC4CCN(C[C@H]5CC[C@H](n6cc7cc(NC(=O)c8cccc(C(F)(F)F)n8)c(C(C)(C)O)cc7n6)CC5)CC4)C3)c21] |
| I-204 | 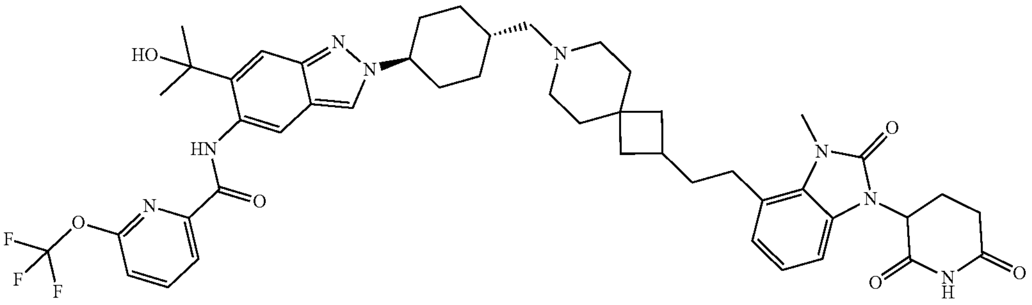 [SMILES: Cn1c(=O)n(C2CCC(=O)NC2=O)c2cccc(CCC3CC4(CCN(C[C@H]5CC[C@H](n6cc7cc(NC(=O)c8cccc(OC(F)(F)F)n8)c(C(C)(C)O)cc7n6)CC5)CC4)C3)c21] |
| I-205 | 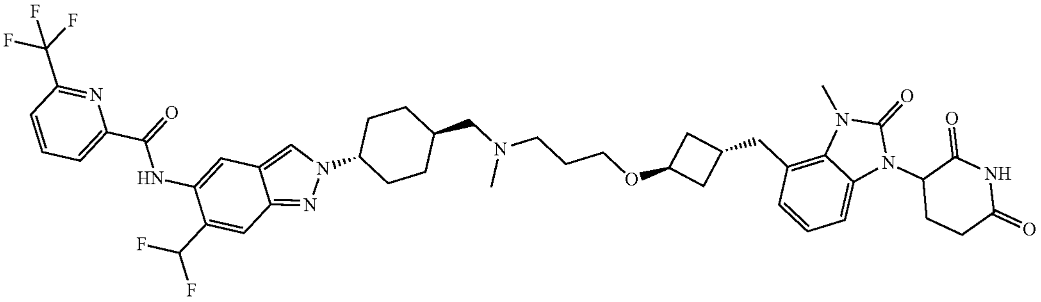 [SMILES: CN(CCCO[C@H]1C[C@H](Cc2cccc3c2n(C)c(=O)n3C2CCC(=O)NC2=O)C1)C[C@H]1CC[C@H](n2cc3cc(NC(=O)c4cccc(C(F)(F)F)n4)c(C(F)F)cc3n2)CC1] |

TABLE 1-continued
| Exemplary Compounds | |
|---|---|
| I-# | Structure |
| I-206 | 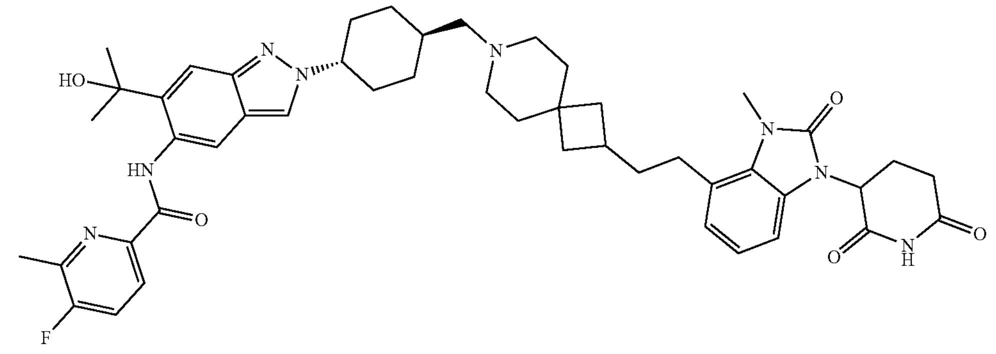 [SMILES: Cc1nc(C(=O)Nc2cc3cn([C@H]4CC[C@H](CN5CCC6(CC5)CC(CCc5cccc7c5n(C)c(=O)n7C5CCC(=O)NC5=O)C6)CC4)nc3cc2C(C)(C)O)ccc1F] |
| I-207 | 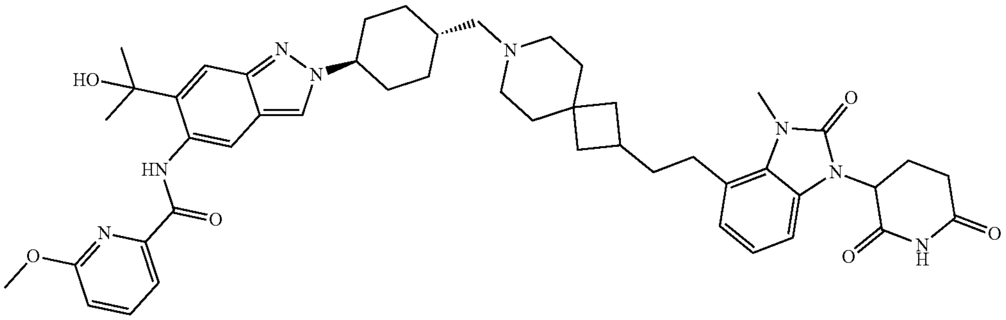 [SMILES: COc1cccc(C(=O)Nc2cc3cn([C@H]4CC[C@H](CN5CCC6(CC5)CC(CCc5cccc7c5n(C)c(=O)n7C5CCC(=O)NC5=O)C6)CC4)nc3cc2C(C)(C)O)n1] |
| I-208 | 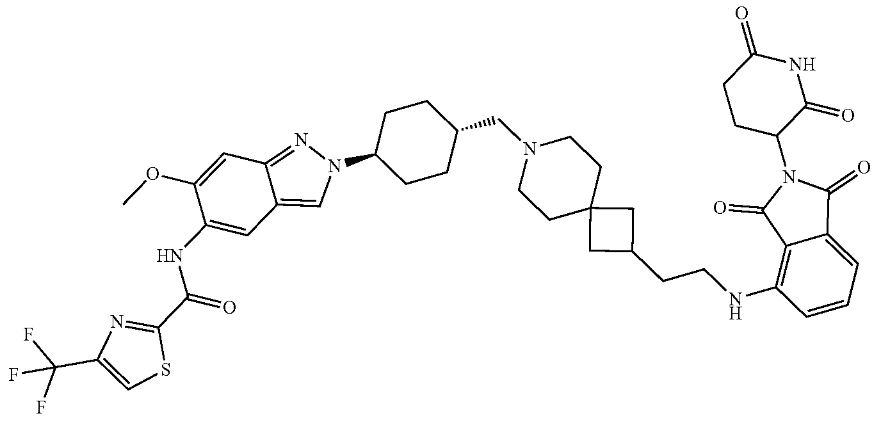 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1nc(C(F)(F)F)cs1] |
| I-209 | 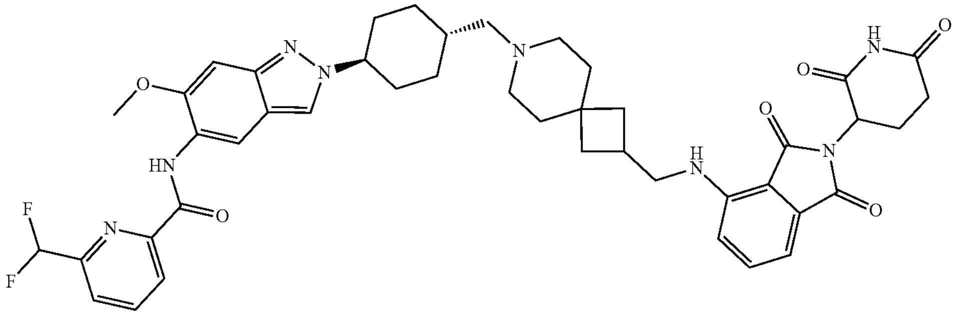 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(F)F)n1] |

TABLE 1-continued
| Exemplary Compounds | |
|---|---|
| I-# | Structure |
| I-210 | 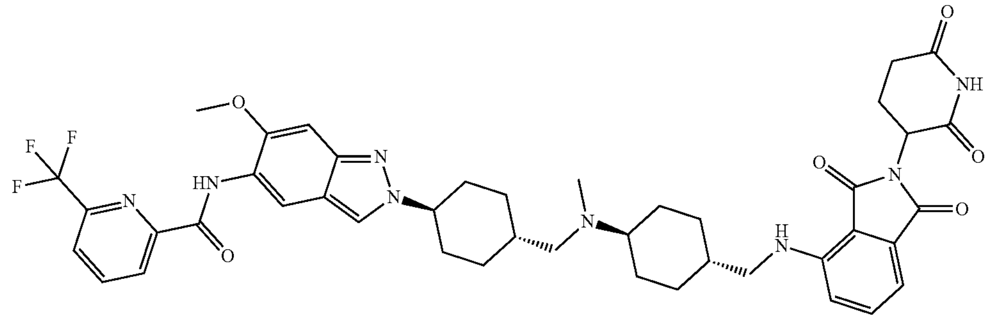 [SMILES: COc1cc2nn([C@H]3CC[C@H](CN(C)[C@H]4CC[C@H](CNc5cccc6c5C(=O)N(C5CCC(=O)NC5=O)C6=O)CC4)CC3)cc2cc1NC(=O)c1cccc(C(F)(F)F)n1] |
| I-211 | 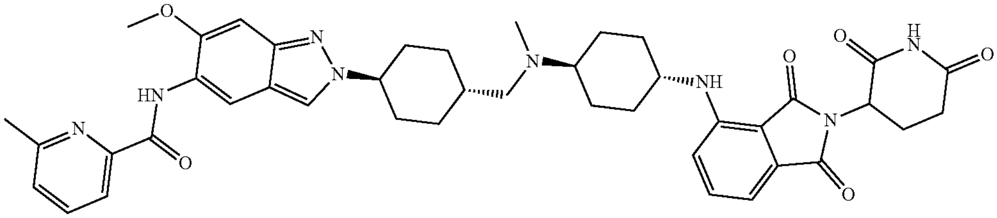 [SMILES: COc1cc2nn([C@H]3CC[C@H](CN(C)[C@H]4CC[C@H](Nc5cccc6c5C(=O)N(C5CCC(=O)NC5=O)C6=O)CC4)CC3)cc2cc1NC(=O)c1cccc(C)n1] |
| I-212 | 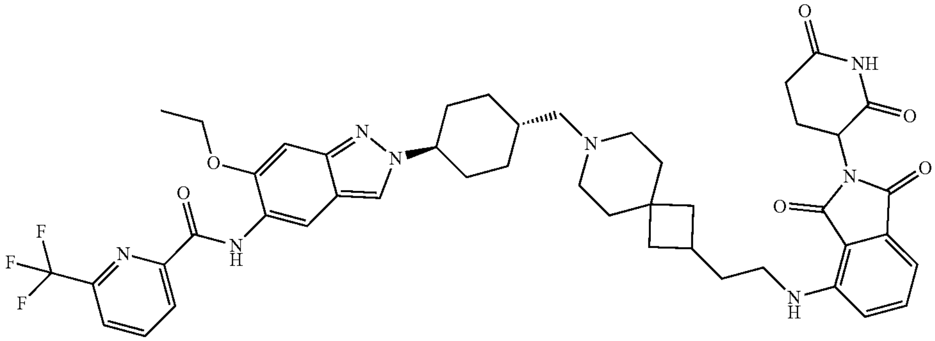 [SMILES: CCOc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cccc(C(F)(F)F)n1] |
| I-213 | 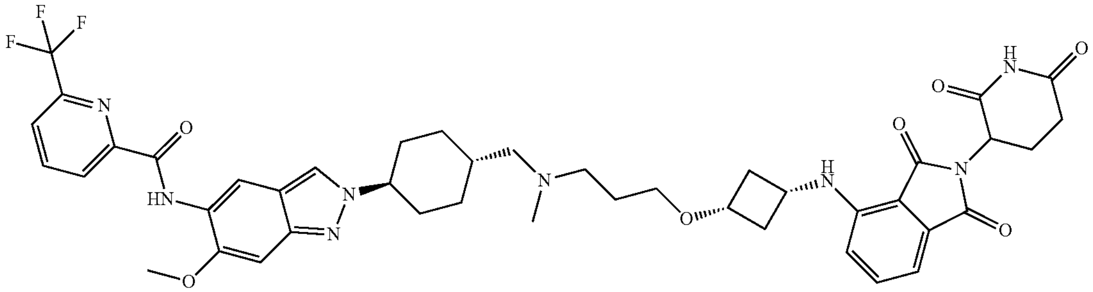 [SMILES: COc1cc2nn([C@H]3CC[C@H](CN(C)CCCO[C@H]4C[C@@H](Nc5cccc6c5C(=O)N(C5CCC(=O)NC5=O)C6=O)C4)CC3)cc2cc1NC(=O)c1cccc(C(F)(F)F)n1] |
| I-214 | 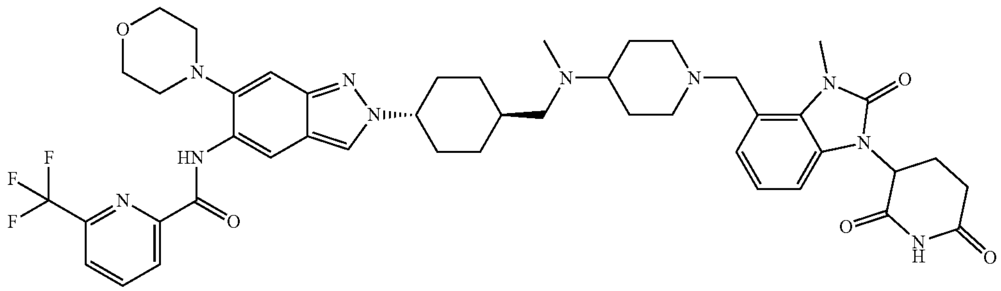 [SMILES: CN(C[C@H]1CC[C@H](n2cc3cc(NC(=O)c4cccc(C(F)(F)F)n4)c(N4CCOCC4)cc3n2)CC1)C1CCN(Cc2cccc3c2n(C)c(=O)n3C2CCC(=O)NC2=O)CC1] |

TABLE 1-continued
| Exemplary Compounds | |
|---|---|
| I-# | Structure |
| I-215 | 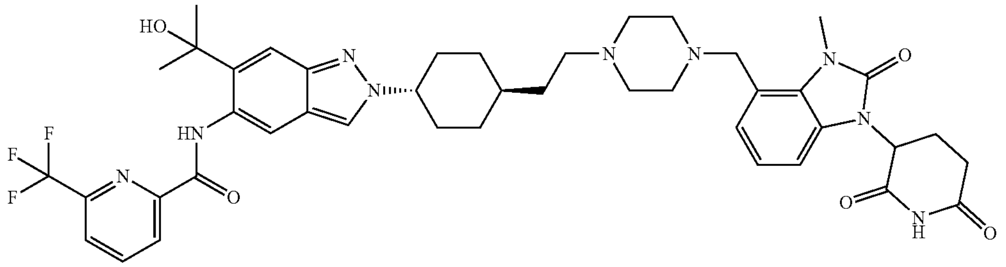 [SMILES: Cn1c(=O)n(C2CCC(=O)NC2=O)c2cccc(CN3CCN(CC[C@H]4CC[C@H](n5cc6cc(NC(=O)c7cccc(C(F)(F)F)n7)c(C(C)(C)O)cc6n5)CC4)CC3)c21] |
| I-216 | 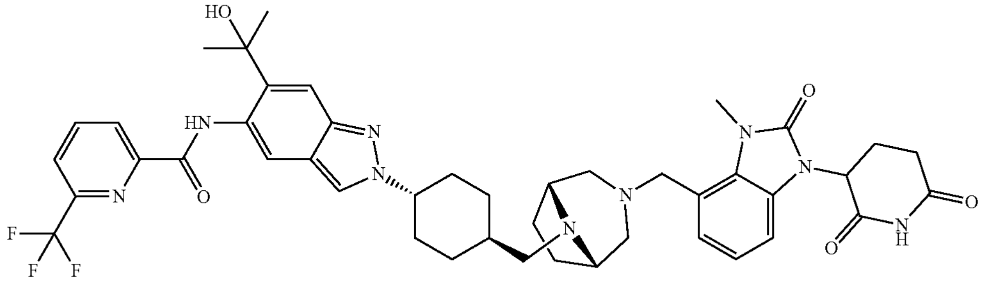 [SMILES: Cn1c(=O)n(C2CCC(=O)NC2=O)c2cccc(CN3C[C@H]4CC[C@@H](C3)N4C[C@H]3CC[C@H](n4cc5cc(NC(=O)c6cccc(C(F)(F)F)n6)c(C(C)(C)O)cc5n4)CC3)c21] |
| I-217 | 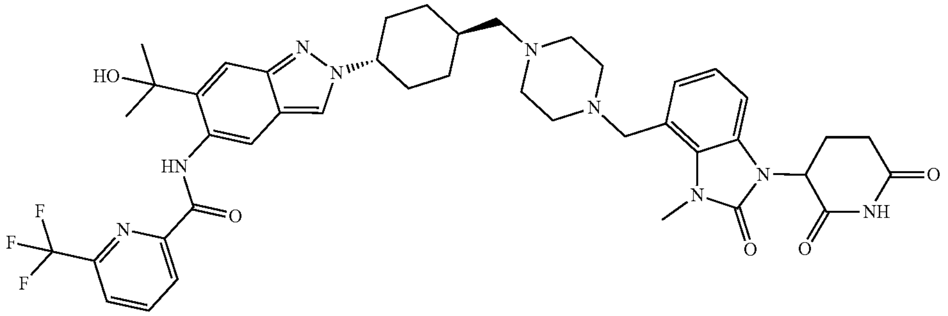 [SMILES: Cn1c(=O)n(C2CCC(=O)NC2=O)c2cccc(CN3CCN(C[C@H]4CC[C@H](n5cc6cc(NC(=O)c7cccc(C(F)(F)F)n7)c(C(C)(C)O)cc6n5)CC4)CC3)c21] |
| I-218 | 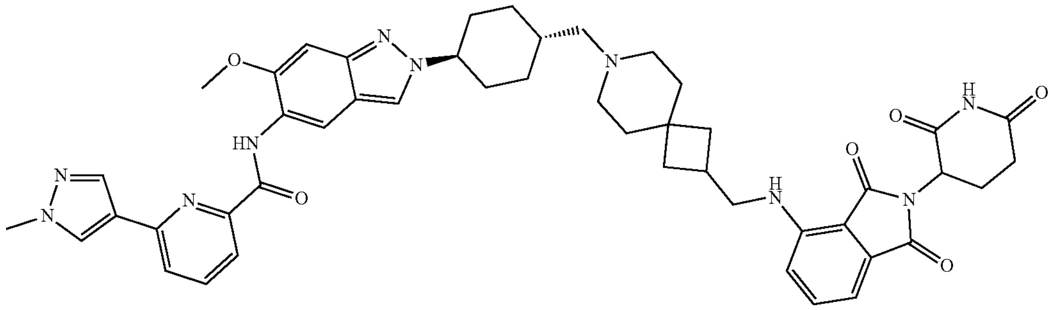 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(-c2cnn(C)c2)n1] |
| I-219 | 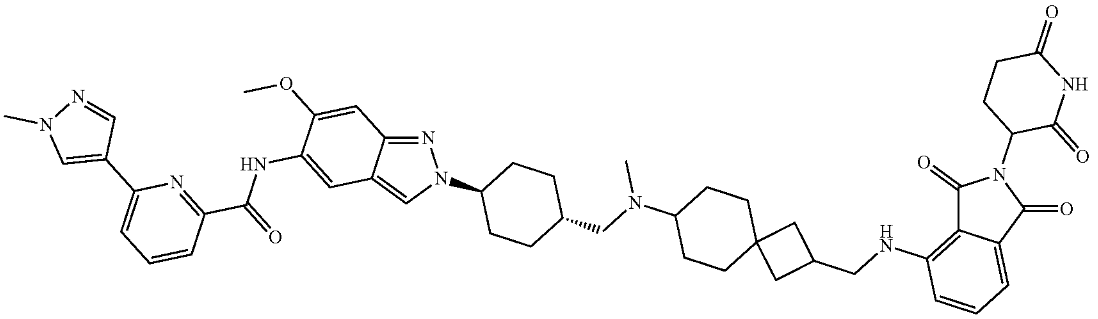 [SMILES: COc1cc2nn([C@H]3CC[C@H](CN(C)C4CCC5(CC4)CC(CNc4cccc6c4C(=O)N(C4CCC(=O)NC4=O)C6=O)C5)CC3)cc2cc1NC(=O)c1cccc(-c2cnn(C)c2)n1] |

TABLE 1-continued
| Exemplary Compounds | |
|---|---|
| I-# | Structure |
| I-220 | 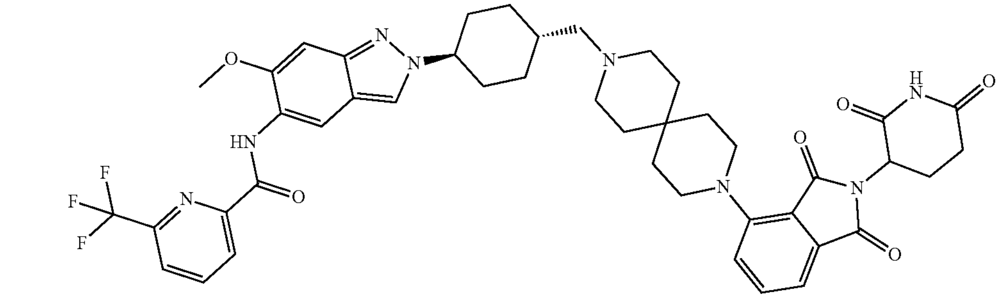 [SMILES: COc1cc2nn([C@H]3CC[C@H](CN4CCC5(CC4)CCN(c4cccc6c4C(=O)N(C4CCC(=O)NC4=O)C6=O)CC5)CC3)cc2cc1NC(=O)c1cccc(C(F)(F)F)n1] |
| I-221 | 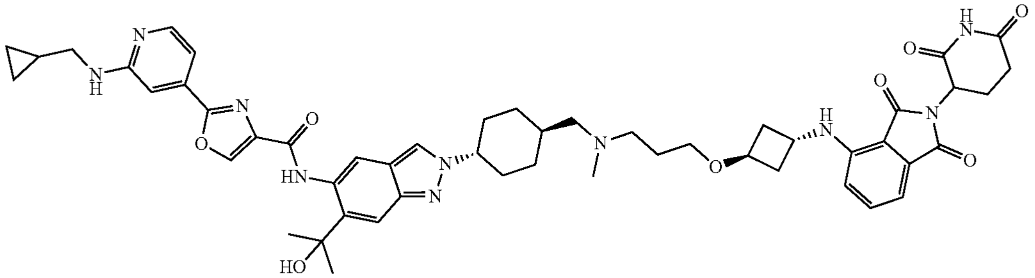 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)c4coc(-c5ccnc(NCC6CC6)c5)n4)c(C(C)(C)O)cc3n2)CC1] |
| I-222 | 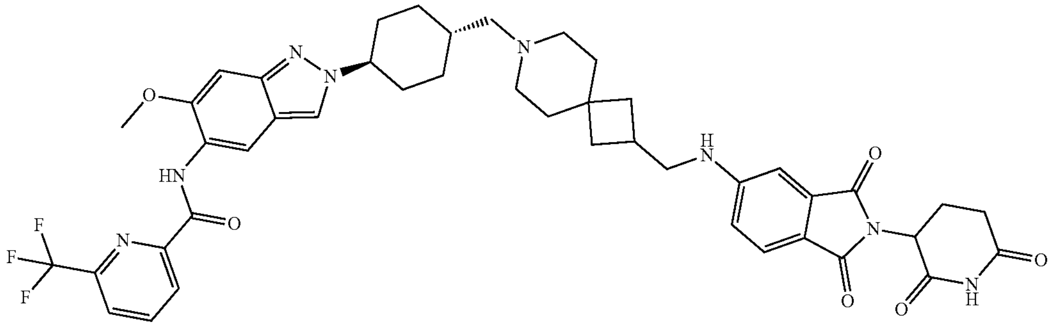 [SMILES: COc1cc2nn([C@H]3CC[C@H](CN4CCC5(CC4)CC(CNc4ccc6c(c4)C(=O)N(C4CCC(=O)NC4=O)C6=O)C5)CC3)cc2cc1NC(=O)c1cccc(C(F)(F)F)n1] |
| I-223 | 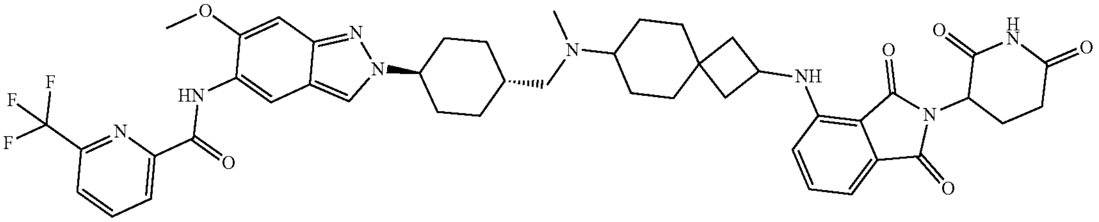 [SMILES: COc1cc2nn([C@H]3CC[C@H](CN(C)C4CCC5(CC4)CC(Nc4cccc6c4C(=O)N(C4CCC(=O)NC4=O)C6=O)C5)CC3)cc2cc1NC(=O)c1cccc(C(F)(F)F)n1] |
| I-224 | 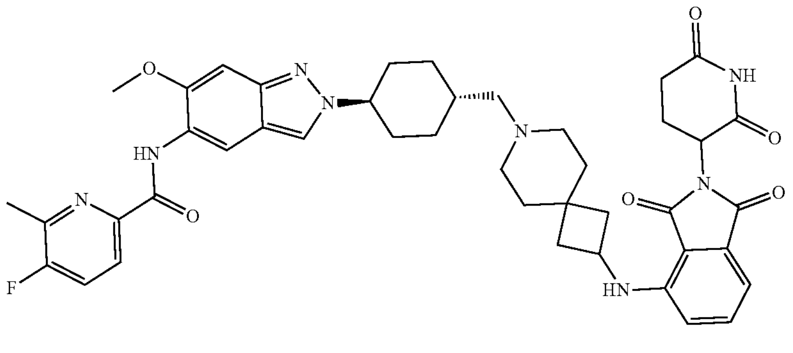 [SMILES: COc1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1ccc(F)c(C)n1] |

TABLE 1-continued
| Exemplary Compounds | |
|---|---|
| I-# | Structure |
| I-225 | 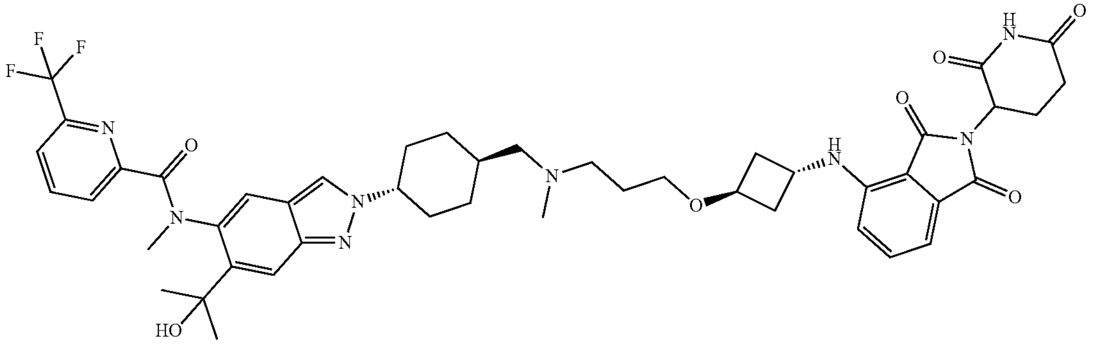 [SMILES: CN(CCCO[C@H]1C[C@H](Nc2cccc3c2C(=O)N(C2CCC(=O)NC2=O)C3=O)C1)C[C@H]1CC[C@H](n2cc3cc(N(C)C(=O)c4cccc(C(F)(F)F)n4)c(C(C)(C)O)cc3n2)CC1] |
| I-226 | 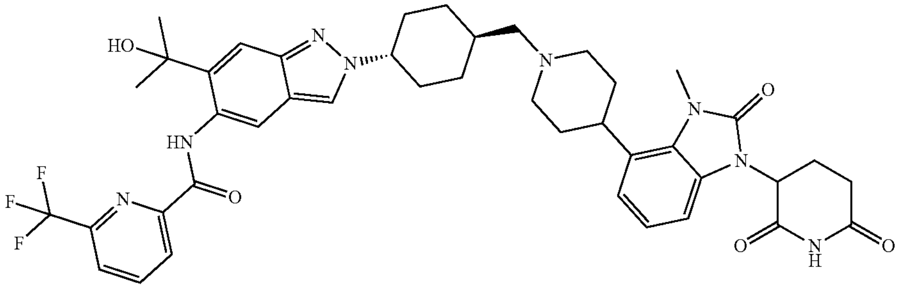 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(C)(C)O)cc6n5)CC4)CC3)c21] |
| I-227 | 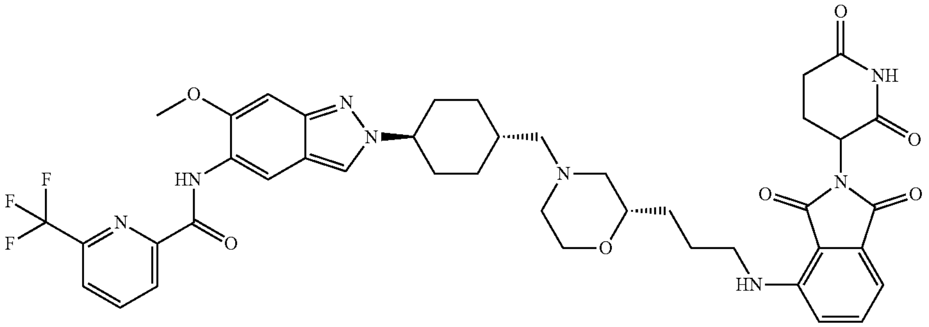 [SMILES: COc1cc2nn([C@H]3CC[C@H](CN4CCO[C@@H](CCCNc5cccc6c5C(=O)N(C5CCC(=O)NC5=O)C6=O)C4)CC3)cc2cc1NC(=O)c1cccc(C(F)(F)F)n1] |
| I-228 | 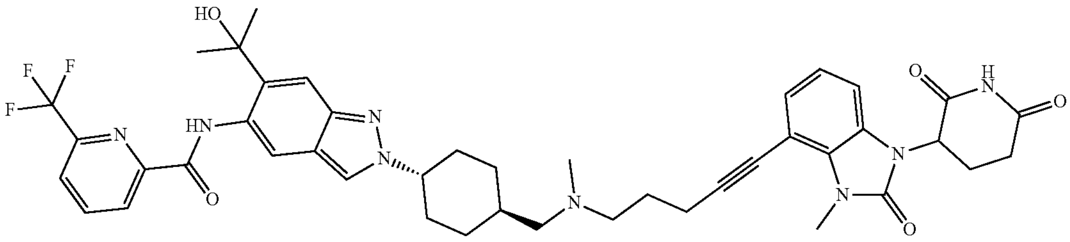 [SMILES: CN(CCCC#Cc1cccc2c1n(C)c(=O)n2C1CCC(=O)NC1=O)C[C@H]1CC[C@H](n2cc3cc(NC(=O)c4cccc(C(F)(F)F)n4)c(C(C)(C)O)cc3n2)CC1] |
| I-229 | 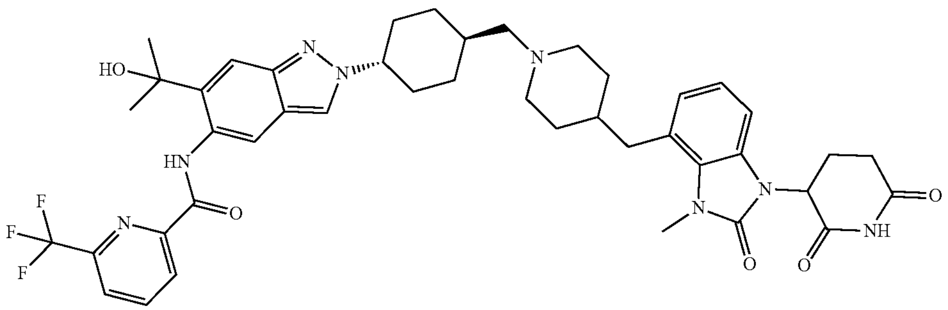 [SMILES: Cn1c(=O)n(C2CCC(=O)NC2=O)c2cccc(CC3CCN(C[C@H]4CC[C@H](n5cc6cc(NC(=O)c7cccc(C(F)(F)F)n7)c(C(C)(C)O)cc6n5)CC4)CC3)c21] |

TABLE 1-continued
| Exemplary Compounds | |
|---|---|
| I-# | Structure |
| I-230 | 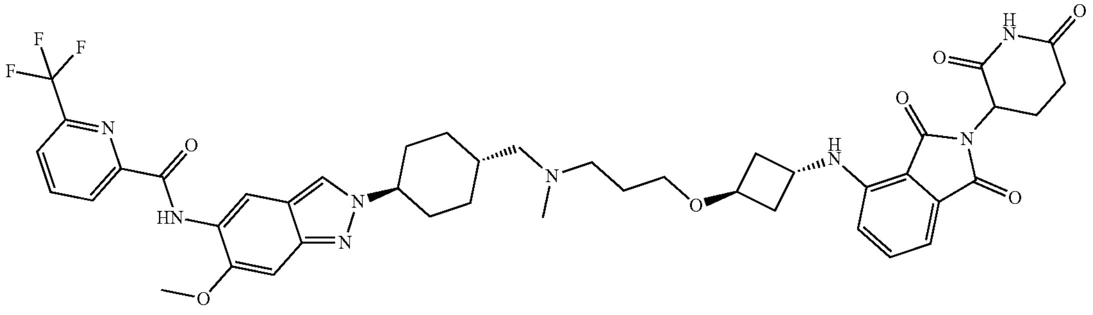 [SMILES: COc1cc2nn([C@H]3CC[C@H](CN(C)CCCO[C@H]4C[C@H](Nc5cccc6c5C(=O)N(C5CCC(=O)NC5=O)C6=O)C4)CC3)cc2cc1NC(=O)c1cccc(C(F)(F)F)n1] |
| I-231 | 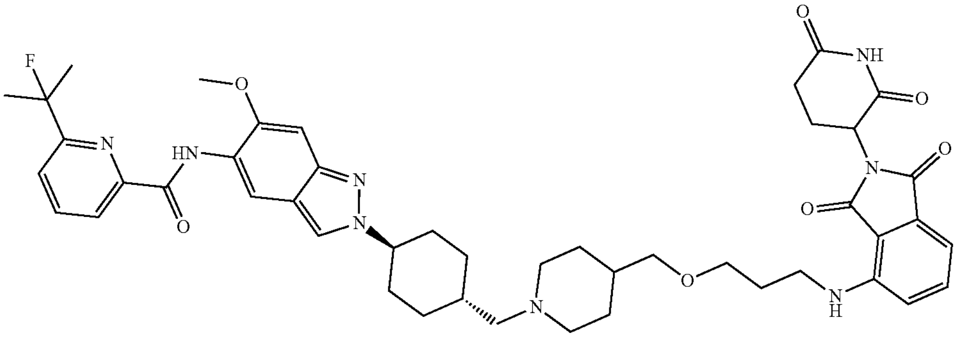 [SMILES: COc1cc2nn([C@H]3CC[C@H](CN4CCC(COCCCNc5cccc6c5C(=O)N(C5CCC(=O)NC5=O)C6=O)CC4)CC3)cc2cc1NC(=O)c1cccc(C(C)(C)F)n1] |
| I-232 | 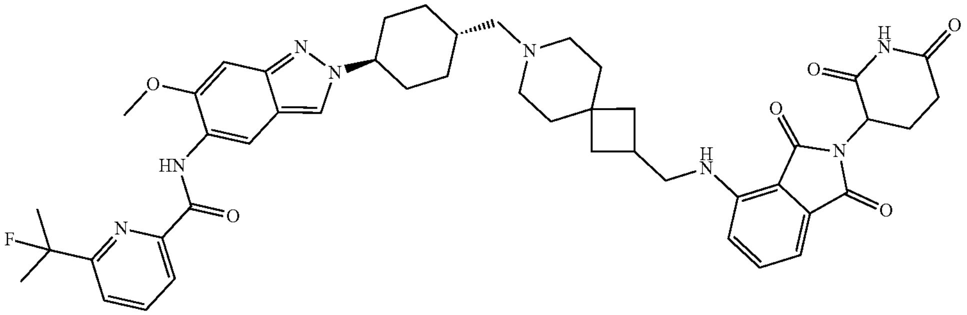 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(C)(C)F)n1] |
| I-233 | 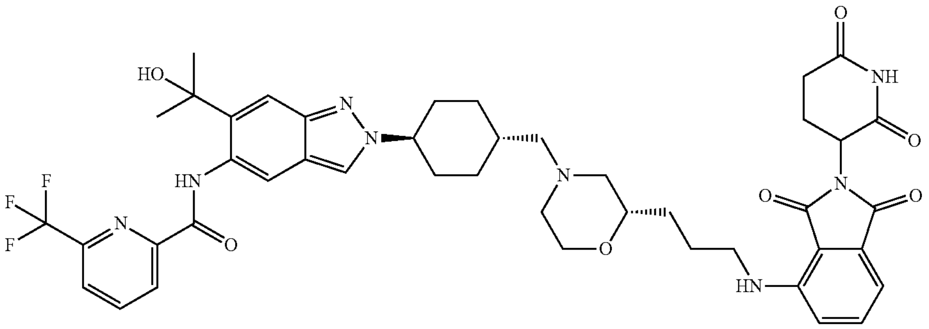 [SMILES: CC(C)(O)c1cc2nn([C@H]3CC[C@H](CN4CCO[C@@H](CCCNc5cccc6c5C(=O)N(C5CCC(=O)NC5=O)C6=O)C4)CC3)cc2cc1NC(=O)c1cccc(C(F)(F)F)n1] |

TABLE 1-continued
| Exemplary Compounds | |
|---|---|
| I-# | Structure |
| I-234 | 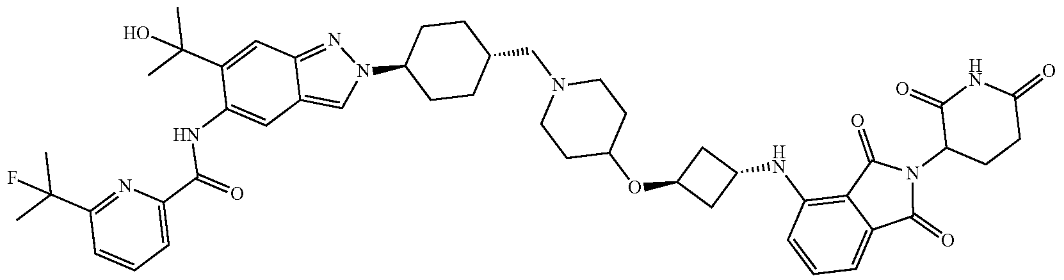 [SMILES: CC(C)(O)c1cc2nn([C@H]3CC[C@H](CN4CCC(O[C@H]5C[C@H](Nc6cccc7c6C(=O)N(C6CCC(=O)NC6=O)C7=O)C5)CC4)CC3)cc2cc1NC(=O)c1cccc(C(C)(C)F)n1] |
| I-235 | 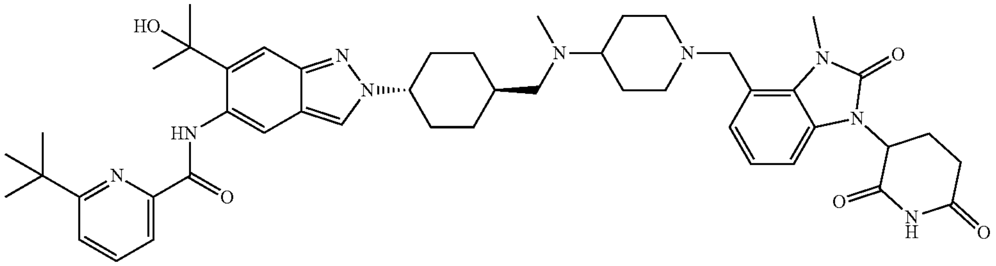 [SMILES: CN(C[C@H]1CC[C@H](n2cc3cc(NC(=O)c4cccc(C(C)(C)C)n4)c(C(C)(C)O)cc3n2)CC1)C1CCN(Cc2cccc3c2n(C)c(=O)n3C2CCC(=O)NC2=O)CC1] |
| I-236 | 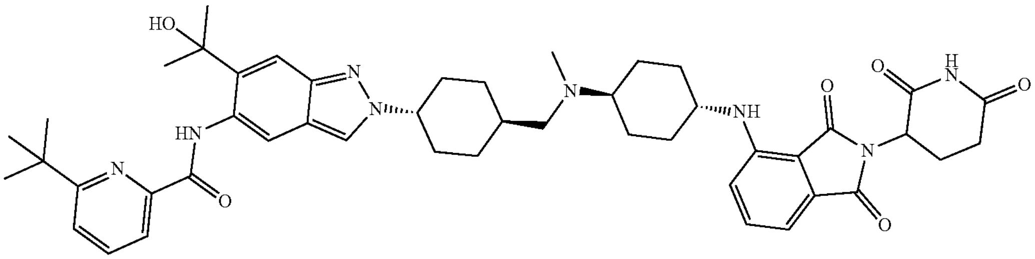 [SMILES: CN(C[C@H]1CC[C@H](n2cc3cc(NC(=O)c4cccc(C(C)(C)C)n4)c(C(C)(C)O)cc3n2)CC1)[C@H]1CC[C@H](Nc2cccc3c2C(=O)N(C2CCC(=O)NC2=O)C3=O)CC1] |
| I-237 | 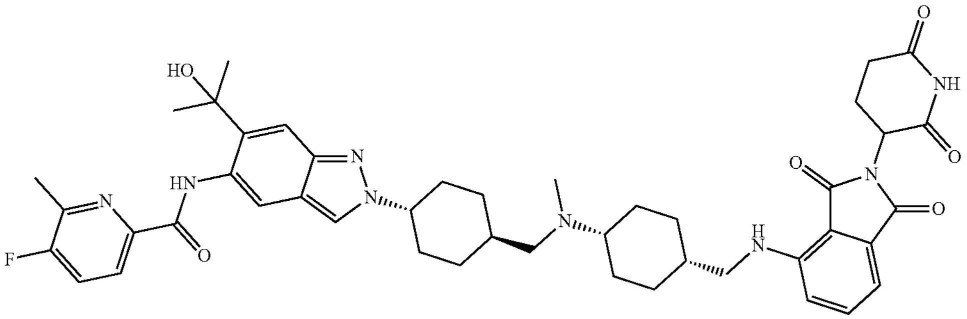 [SMILES: Cc1nc(C(=O)Nc2cc3cn([C@H]4CC[C@H](CN(C)[C@H]5CC[C@@H](CNc6cccc7c6C(=O)N(C6CCC(=O)NC6=O)C7=O)CC5)CC4)nc3cc2C(C)(C)O)ccc1F] |
| I-238 | 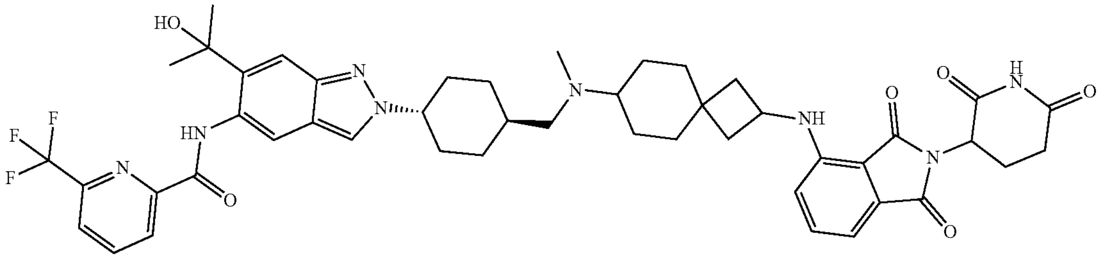 [SMILES: CN(C[C@H]1CC[C@H](n2cc3cc(NC(=O)c4cccc(C(F)(F)F)n4)c(C(C)(C)O)cc3n2)CC1)C1CCC2(CC1)CC(Nc1cccc3c1C(=O)N(C1CCC(=O)NC1=O)C3=O)C2] |

TABLE 1-continued
| Exemplary Compounds | |
|---|---|
| I-# | Structure |
| I-239 | 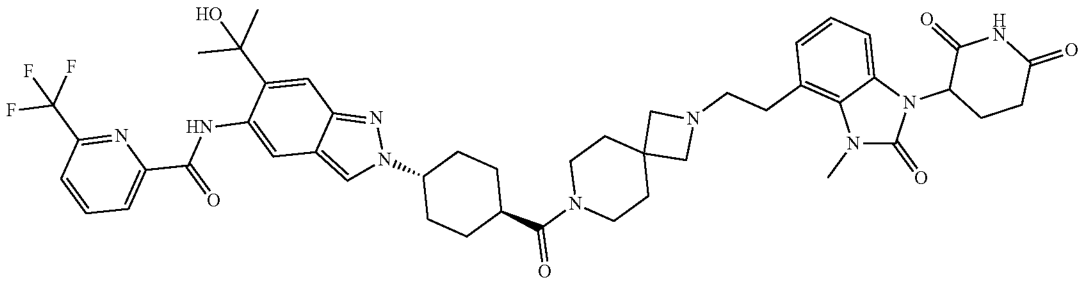 [SMILES: Cn1c(=O)n(C2CCC(=O)NC2=O)c2cccc(CCN3CC4(CCN(C(=O)[C@H]5CC[C@H](n6cc7cc(NC(=O)c8cccc(C(F)(F)F)n8)c(C(C)(C)O)cc7n6)CC5)CC4)C3)c21] |
| I-240 | 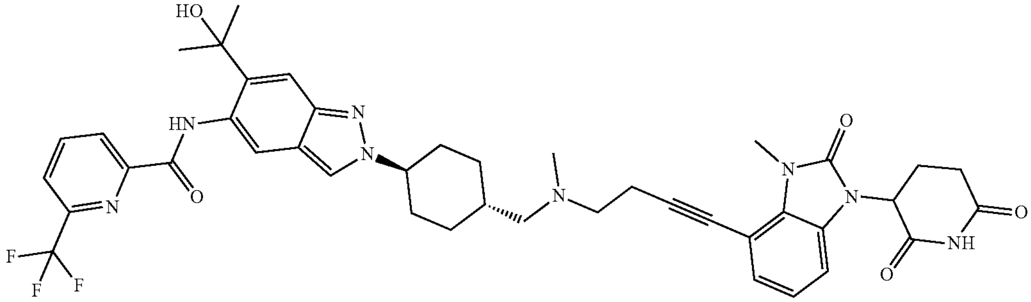 [SMILES: CN(CCC#Cc1cccc2c1n(C)c(=O)n2C1CCC(=O)NC1=O)C[C@H]1CC[C@H](n2cc3cc(NC(=O)c4cccc(C(F)(F)F)n4)c(C(C)(C)O)cc3n2)CC1] |
| I-241 | 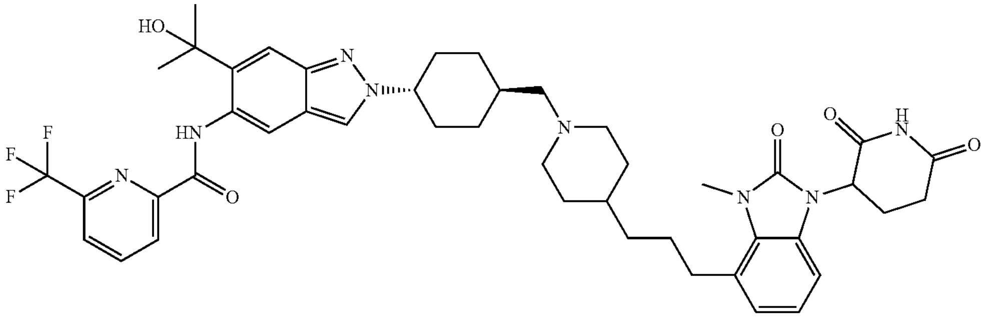 [SMILES: Cn1c(=O)n(C2CCC(=O)NC2=O)c2cccc(CCCC3CCN(C[C@H]4CC[C@H](n5cc6cc(NC(=O)c7cccc(C(F)(F)F)n7)c(C(C)(C)O)cc6n5)CC4)CC3)c21] |
| I-242 | 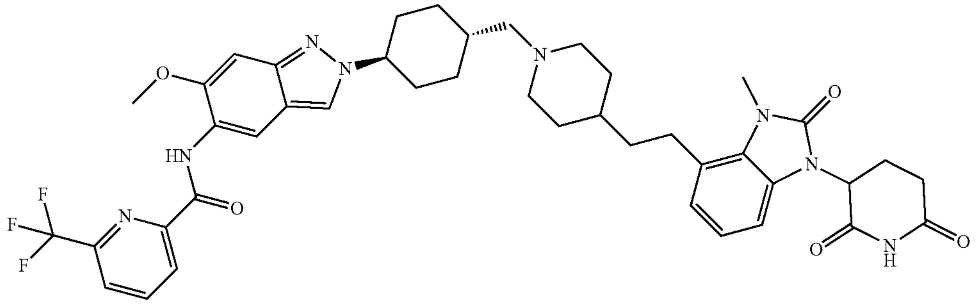 [SMILES: COc1cc2nn([C@H]3CC[C@H](CN4CCC(CCc5cccc6c5n(C)c(=O)n6C5CCC(=O)NC5=O)CC4)CC3)cc2cc1NC(=O)c1cccc(C(F)(F)F)n1] |
| I-243 | 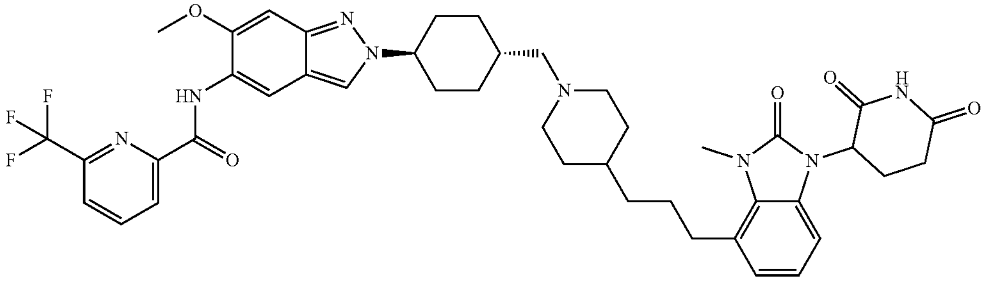 [SMILES: COc1cc2nn([C@H]3CC[C@H](CN4CCC(CCCc5cccc6c5n(C)c(=O)n6C5CCC(=O)NC5=O)CC4)CC3)cc2cc1NC(=O)c1cccc(C(F)(F)F)n1] |

TABLE 1-continued
| Exemplary Compounds | |
|---|---|
| I-# | Structure |
| I-244 | 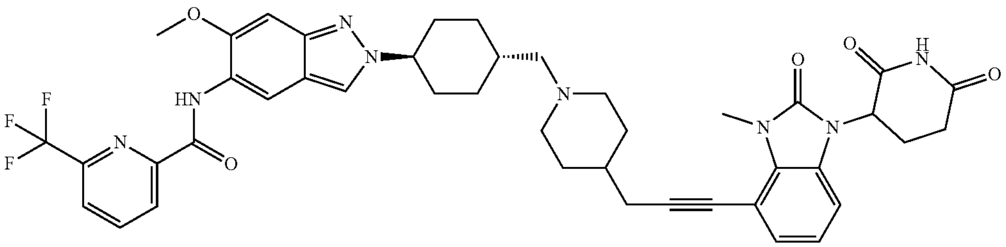 [SMILES: COc1cc2nn([C@H]3CC[C@H](CN4CCC(CC#Cc5cccc6c5n(C)c(=O)n6C5CCC(=O)NC5=O)CC4)CC3)cc2cc1NC(=O)c1cccc(C(F)(F)F)n1] |
| I-245 | 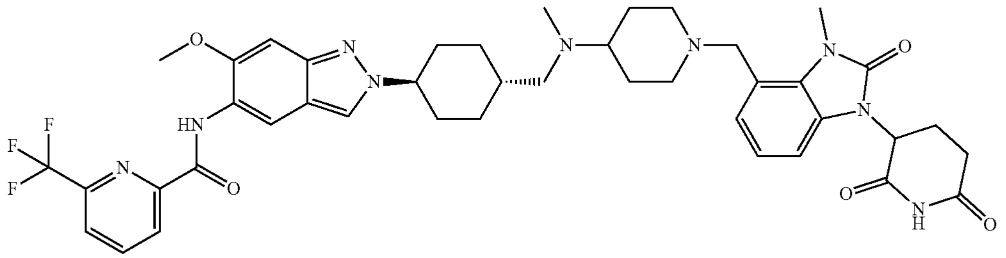 [SMILES: COc1cc2nn([C@H]3CC[C@H](CN(C)C4CCN(Cc5cccc6c5n(C)c(=O)n6C5CCC(=O)NC5=O)CC4)CC3)cc2cc1NC(=O)c1cccc(C(F)(F)F)n1] |
| I-246 | 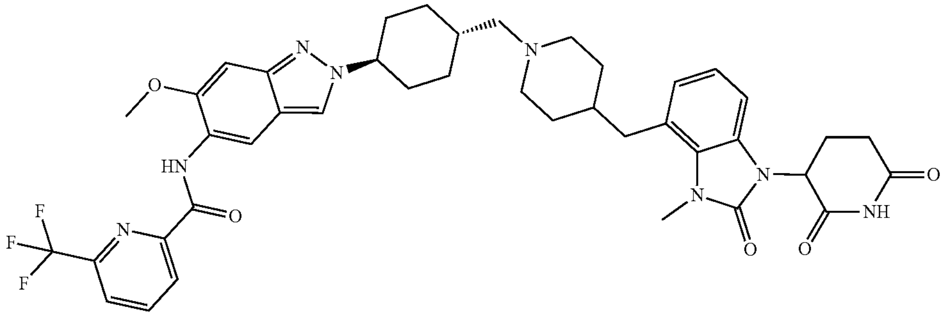 [SMILES: COc1cc2nn([C@H]3CC[C@H](CN4CCC(Cc5cccc6c5n(C)c(=O)n6C5CCC(=O)NC5=O)CC4)CC3)cc2cc1NC(=O)c1cccc(C(F)(F)F)n1] |
| I-247 | 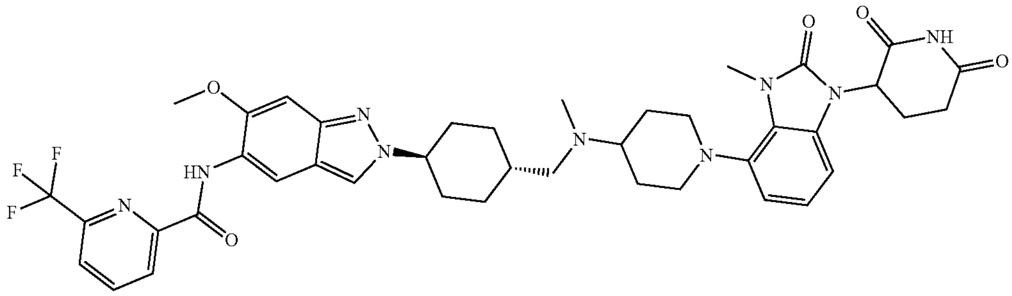 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(C(F)(F)F)n1] |
| I-248 | 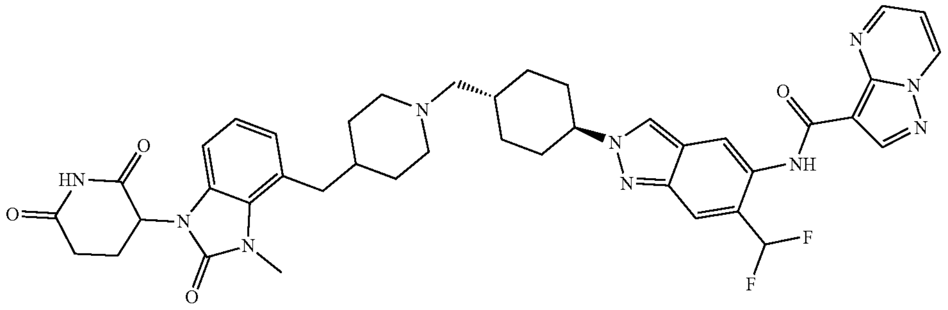 |

TABLE 1-continued
| Exemplary Compounds | |
|---|---|
| I-# | Structure |
| I-249 | 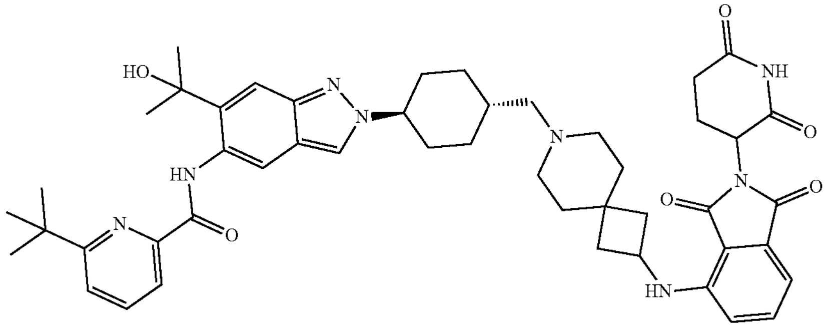 [SMILES: CC(C)(C)c1cccc(C(=O)Nc2cc3cn([C@H]4CC[C@H](CN5CCC6(CC5)CC(Nc5cccc7c5C(=O)N(C5CCC(=O)NC5=O)C7=O)C6)CC4)nc3cc2C(C)(C)O)n1] |
| I-250 | 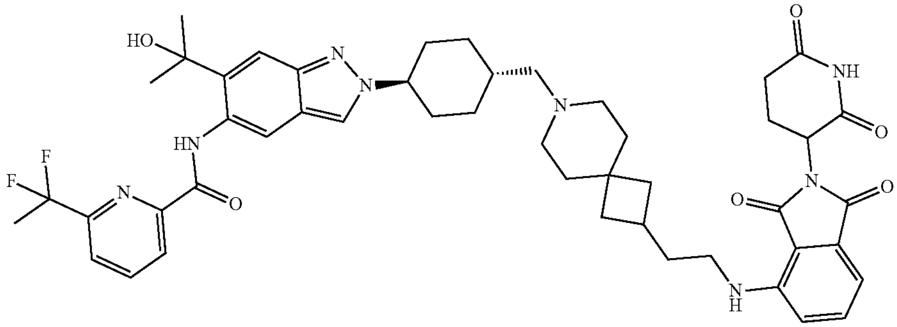 [SMILES: CC(C)(O)c1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cccc(C(C)(F)F)n1] |
| I-251 | 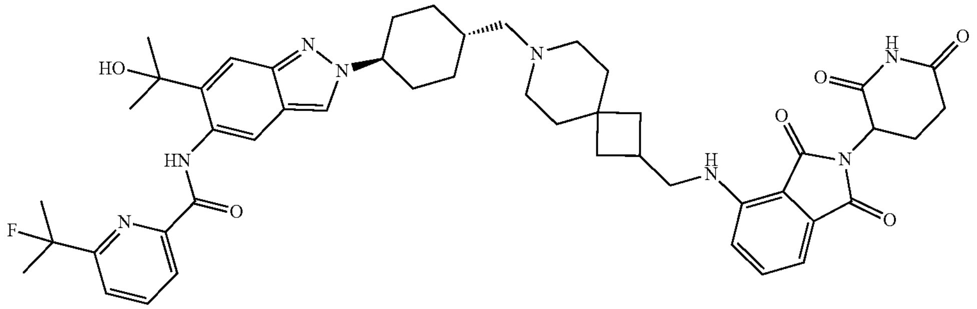 [SMILES: CC(C)(O)c1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1cccc(C(C)(C)F)n1] |
| I-252 | 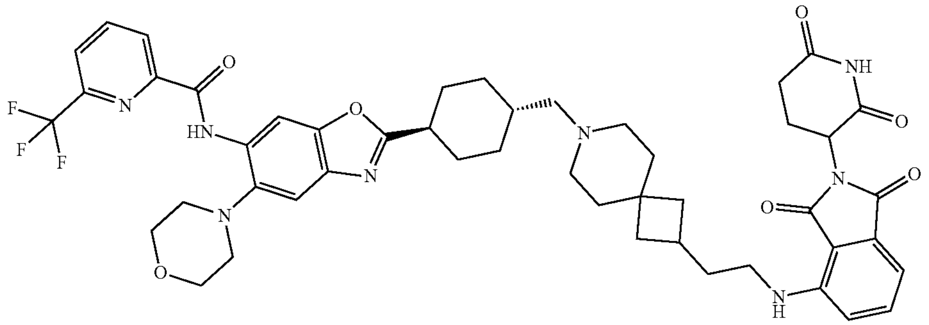 [SMILES: O=C1CCC(N2C(=O)c3cccc(NCCC4CC5(CCN(C[C@H]6CC[C@H](c7nc8cc(N9CCOCC9)c(NC(=O)c9cccc(C(F)(F)F)n9)cc8o7)CC6)CC5)C4)c3C2=O)C(=O)N1] |

TABLE 1-continued
| Exemplary Compounds | |
|---|---|
| I-# | Structure |
| I-254 | 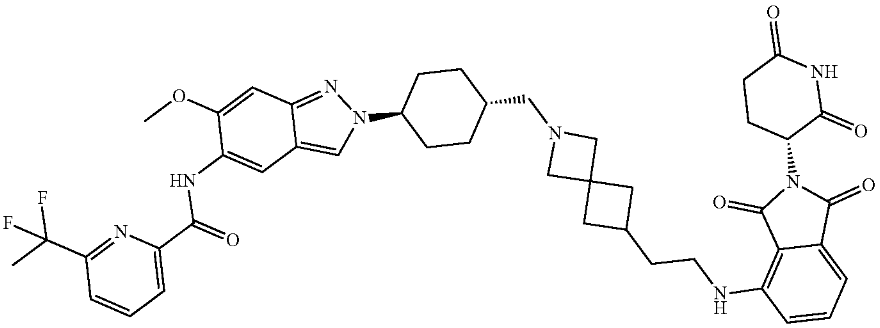 [SMILES: COc1cc2nn([C@H]3CC[C@H](CN4CC5(CC(CCNc6cccc7c6C(=O)N([C@@H]6CCC(=O)NC6=O)C7=O)C5)C4)CC3)cc2cc1NC(=O)c1cccc(C(C)(F)F)n1] |
| I-255 | 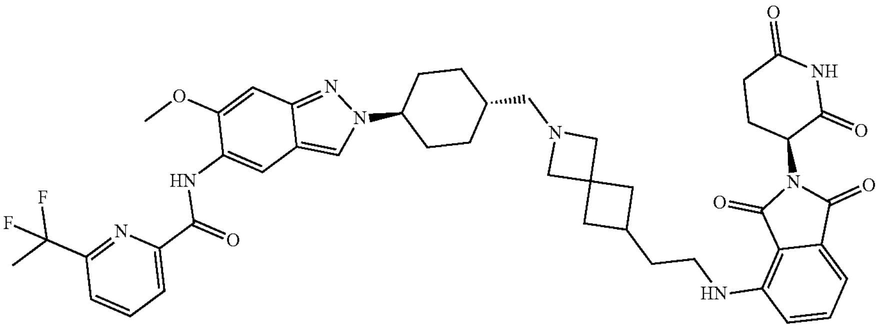 [SMILES: COc1cc2nn([C@H]3CC[C@H](CN4CC5(CC(CCNc6cccc7c6C(=O)N([C@H]6CCC(=O)NC6=O)C7=O)C5)C4)CC3)cc2cc1NC(=O)c1cccc(C(C)(F)F)n1] |
| I-256 | 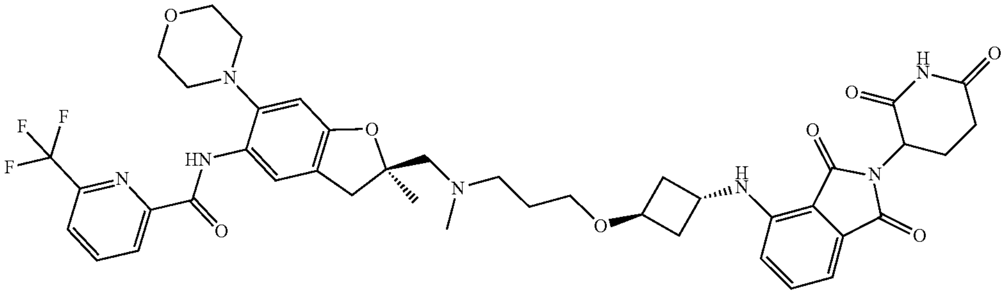 [SMILES: CN(CCCO[C@H]1C[C@H](Nc2cccc3c2C(=O)N(C2CCC(=O)NC2=O)C3=O)C1)C[C@@]1(C)Cc2cc(NC(=O)c3cccc(C(F)(F)F)n3)c(N3CCOCC3)cc2O1] |
| I-257 | 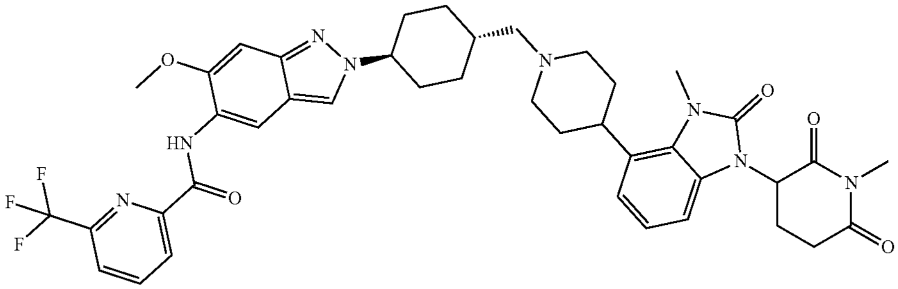 [SMILES: COc1cc2nn([C@H]3CC[C@H](CN4CCC(c5cccc6c5n(C)c(=O)n6C5CCC(=O)N(C)C5=O)CC4)CC3)cc2cc1NC(=O)c1cccc(C(F)(F)F)n1] |
| I-258 | 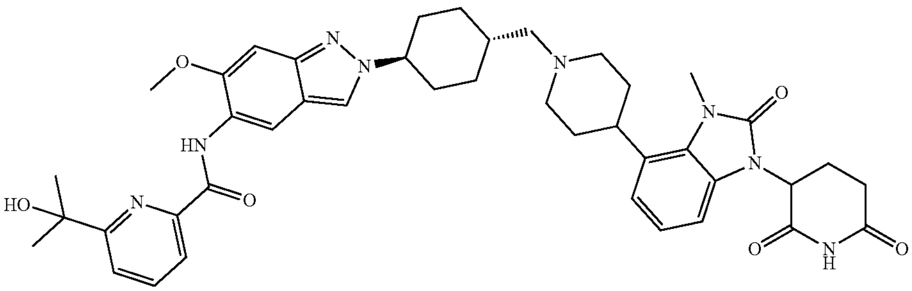 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cccc(C(C)(C)O)n1] |

TABLE 1-continued
| Exemplary Compounds | |
|---|---|
| I-# | Structure |
| I-259 | 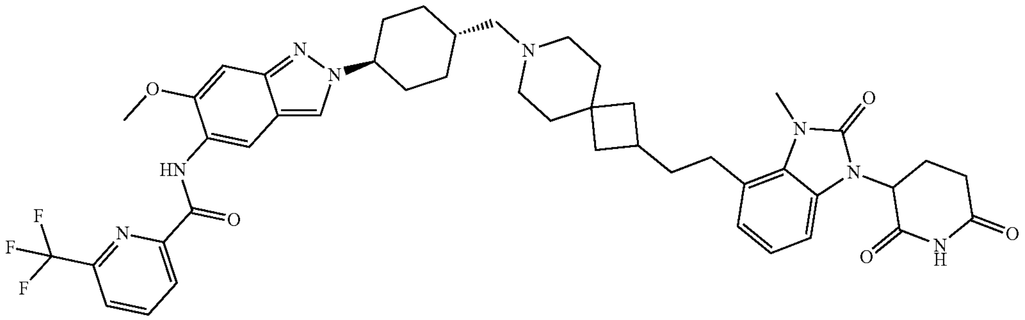 [SMILES: COc1cc2nn([C@H]3CC[C@H](CN4CCC5(CC4)CC(CCc4cccc6c4n(C)c(=O)n6C4CCC(=O)NC4=O)C5)CC3)cc2cc1NC(=O)c1cccc(C(F)(F)F)n1] |
| I-260 | 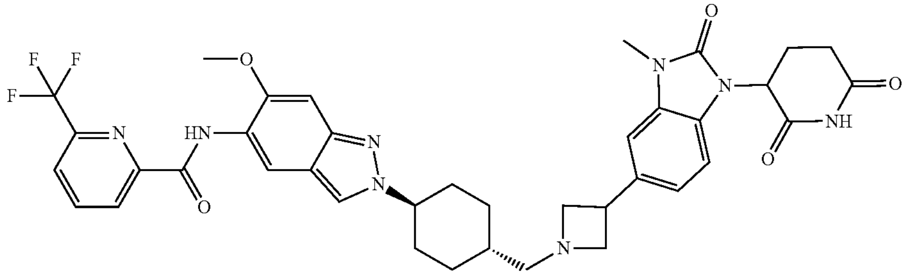 [SMILES: COc1cc2nn([C@H]3CC[C@H](CN4CC(c5ccc6c(c5)n(C)c(=O)n6C5CCC(=O)NC5=O)C4)CC3)cc2cc1NC(=O)c1cccc(C(F)(F)F)n1] |
| I-261 | 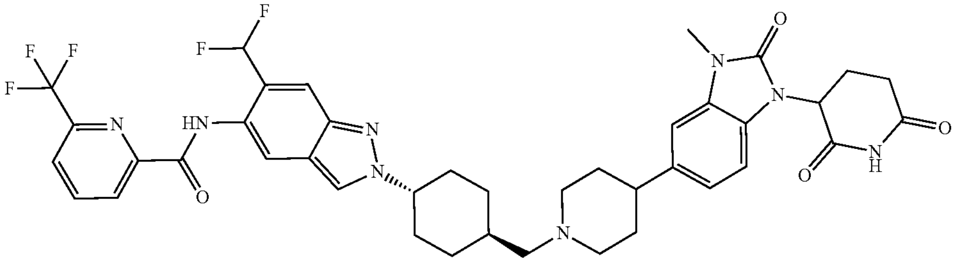 [SMILES: Cn1c(=O)n(C2CCC(=O)NC2=O)c2ccc(C3CCN(C[C@H]4CC[C@H](n5cc6cc(NC(=O)c7cccc(C(F)(F)F)n7)c(C(F)F)cc6n5)CC4)CC3)cc21] |
| I-262 | 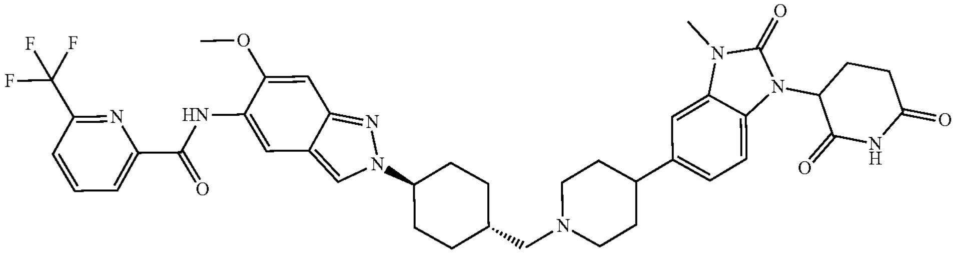 [SMILES: COc1cc2nn([C@H]3CC[C@H](CN4CCC(c5ccc6c(c5)n(C)c(=O)n6C5CCC(=O)NC5=O)CC4)CC3)cc2cc1NC(=O)c1cccc(C(F)(F)F)n1] |
| I-263 | 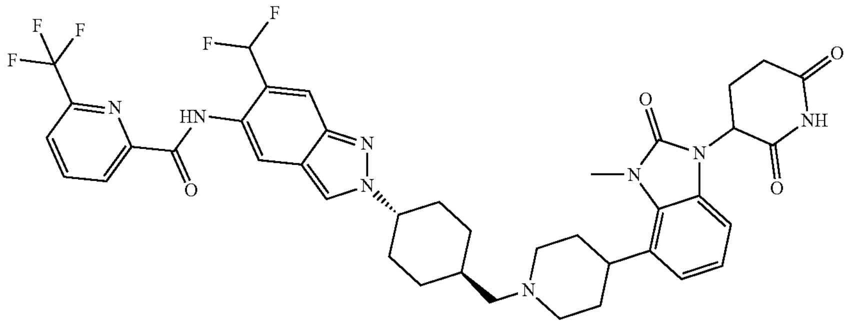 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(F)F)cc6n5)CC4)CC3)c21] |

TABLE 1-continued
| Exemplary Compounds | |
|---|---|
| I-# | Structure |
| I-264 | 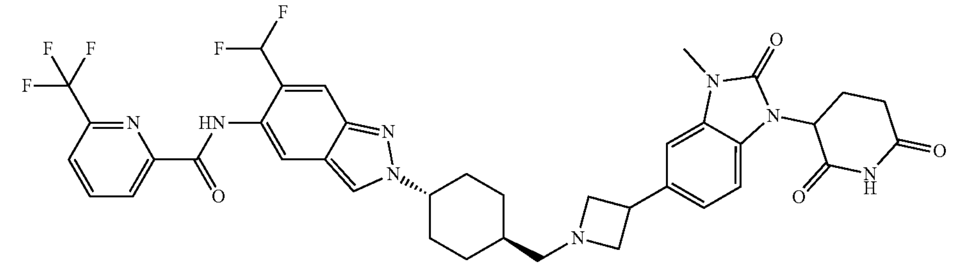 [SMILES: Cn1c(=O)n(C2CCC(=O)NC2=O)c2ccc(C3CN(C[C@H]4CC[C@H](n5cc6cc(NC(=O)c7cccc(C(F)(F)F)n7)c(C(F)F)cc6n5)CC4)C3)cc21] |
| I-265 | 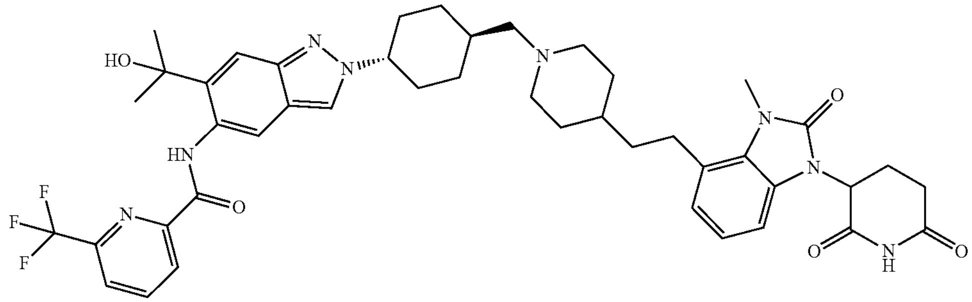 [SMILES: Cn1c(=O)n(C2CCC(=O)NC2=O)c2cccc(CCC3CCN(C[C@H]4CC[C@H](n5cc6cc(NC(=O)c7cccc(C(F)(F)F)n7)c(C(C)(C)O)cc6n5)CC4)CC3)c21] |
| I-266 | 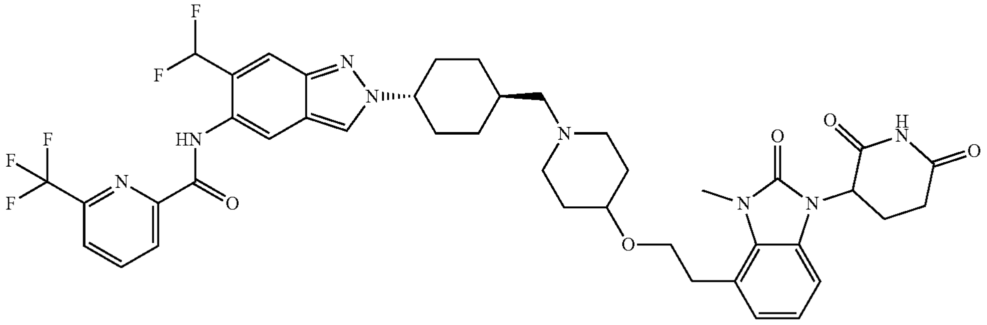 [SMILES: Cn1c(=O)n(C2CCC(=O)NC2=O)c2cccc(CCOC3CCN(C[C@H]4CC[C@H](n5cc6cc(NC(=O)c7cccc(C(F)(F)F)n7)c(C(F)F)cc6n5)CC4)CC3)c21] |
| I-267 | 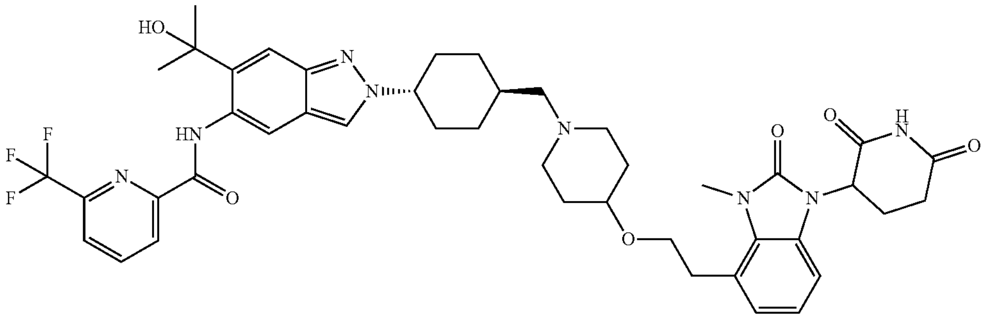 [SMILES: Cn1c(=O)n(C2CCC(=O)NC2=O)c2cccc(CCOC3CCN(C[C@H]4CC[C@H](n5cc6cc(NC(=O)c7cccc(C(F)(F)F)n7)c(C(C)(C)O)cc6n5)CC4)CC3)c21] |
| I-268 | 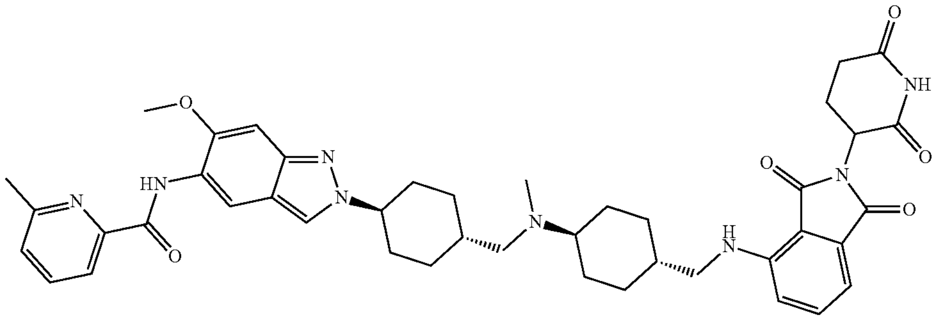 [SMILES: COc1cc2nn([C@H]3CC[C@H](CN(C)[C@H]4CC[C@H](CNc5cccc6c5C(=O)N(C5CCC(=O)NC5=O)C6=O)CC4)CC3)cc2cc1NC(=O)c1cccc(C)n1] |

TABLE 1-continued
| Exemplary Compounds | |
|---|---|
| I-# | Structure |
| I-269 | 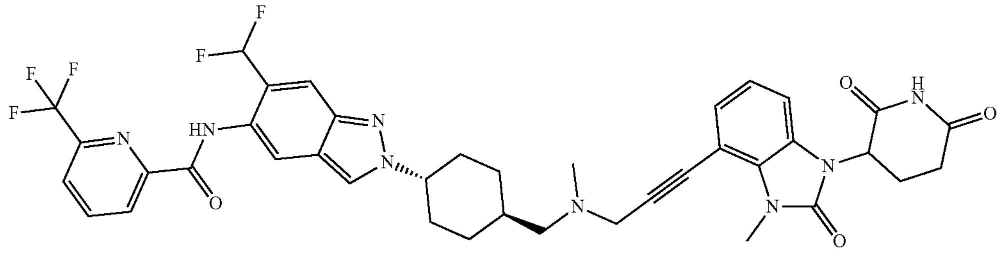 [SMILES: CN(CC#Cc1cccc2c1n(C)c(=O)n2C1CCC(=O)NC1=O)C[C@H]1CC[C@H](n2cc3cc(NC(=O)c4cccc(C(F)(F)F)n4)c(C(F)F)cc3n2)CC1] |
| I-270 | 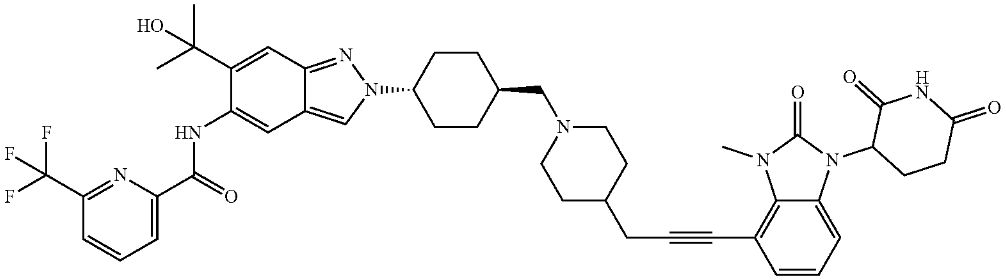 [SMILES: Cn1c(=O)n(C2CCC(=O)NC2=O)c2cccc(C#CCC3CCN(C[C@H]4CC[C@H](n5cc6cc(NC(=O)c7cccc(C(F)(F)F)n7)c(C(C)(C)O)cc6n5)CC4)CC3)c21] |
| I-271 | 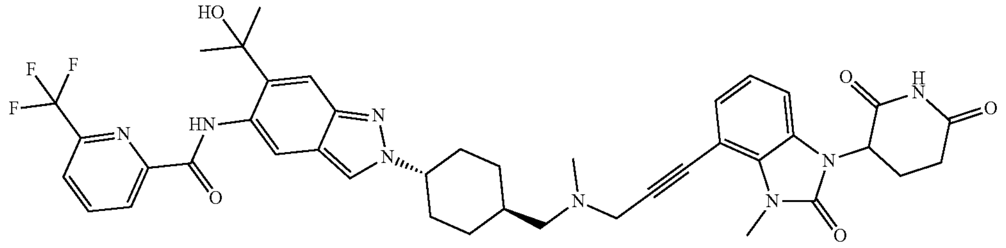 [SMILES: CN(CC#Cc1cccc2c1n(C)c(=O)n2C1CCC(=O)NC1=O)C[C@H]1CC[C@H](n2cc3cc(NC(=O)c4cccc(C(F)(F)F)n4)c(C(C)(C)O)cc3n2)CC1] |
| I-272 | 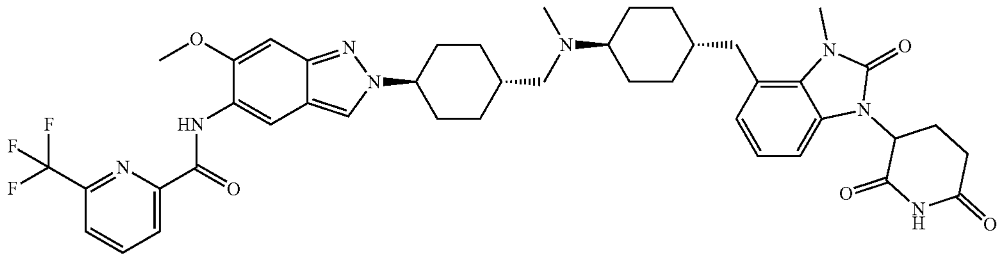 [SMILES: COc1cc2nn([C@H]3CC[C@H](CN(C)[C@H]4CC[C@H](Cc5cccc6c5n(C)c(=O)n6C5CCC(=O)NC5=O)CC4)CC3)cc2cc1NC(=O)c1cccc(C(F)(F)F)n1] |
| I-273 | 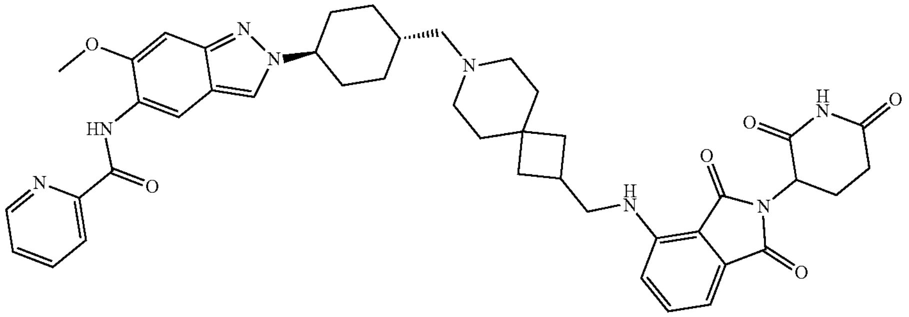 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1ccccn1] |

TABLE 1-continued
| Exemplary Compounds | |
|---|---|
| I-# | Structure |
| I-274 | 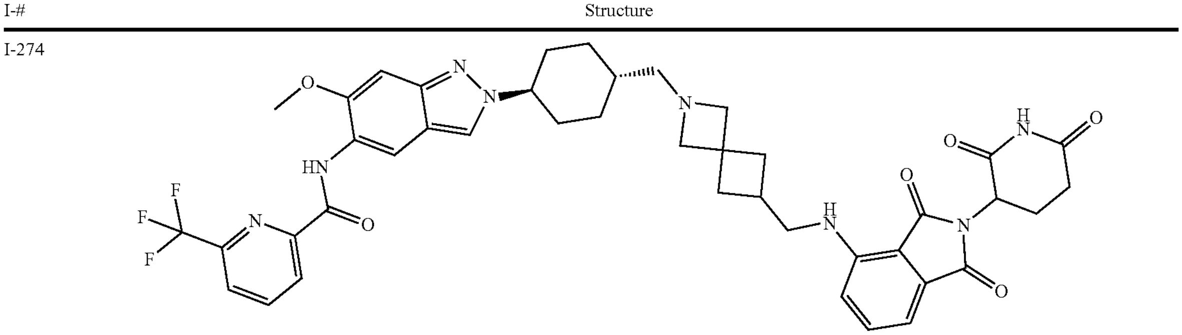 |
| I-275 | 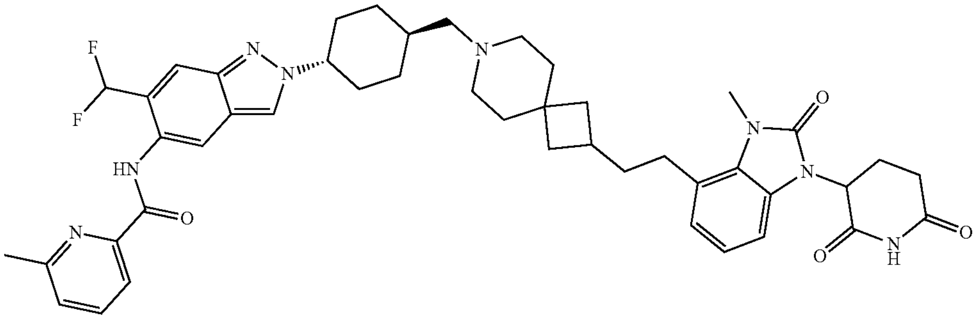 [SMILES: Cc1cccc(C(=O)Nc2cc3cn([C@H]4CC[C@H](CN5CCC6(CC5)CC(CCc5cccc7c5n(C)c(=O)n7C5CCC(=O)NC5=O)C6)CC4)nc3cc2C(F)F)n1] |
| I-276 | 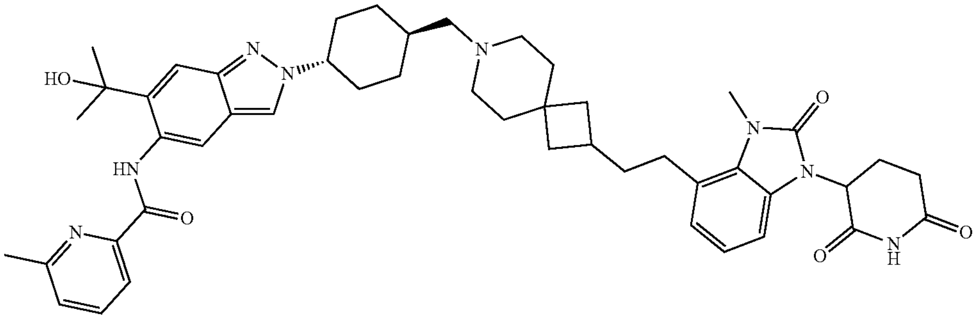 [SMILES: Cc1cccc(C(=O)Nc2cc3cn([C@H]4CC[C@H](CN5CCC6(CC5)CC(CCc5cccc7c5n(C)c(=O)n7C5CCC(=O)NC5=O)C6)CC4)nc3cc2C(C)(C)O)n1] |
| I-277 | 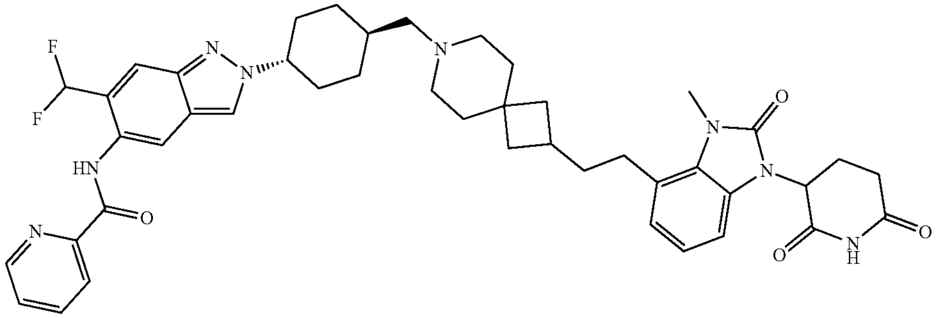 [SMILES: Cn1c(=O)n(C2CCC(=O)NC2=O)c2cccc(CCC3CC4(CCN(C[C@H]5CC[C@H](n6cc7cc(NC(=O)c8ccccn8)c(C(F)F)cc7n6)CC5)CC4)C3)c21] |
| I-278 | 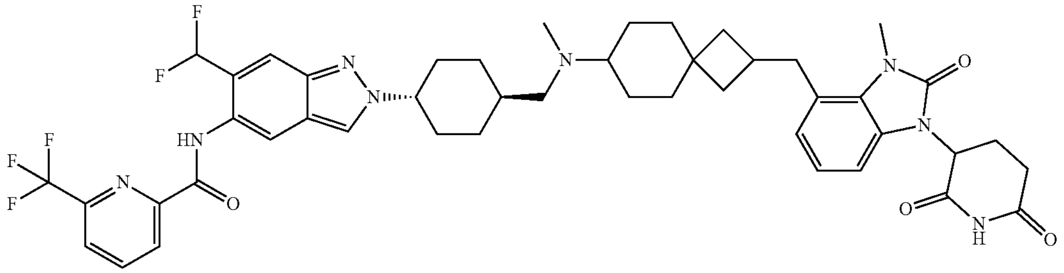 [SMILES: CN(C[C@H]1CC[C@H](n2cc3cc(NC(=O)c4cccc(C(F)(F)F)n4)c(C(F)F)cc3n2)CC1)C1CCC2(CC1)CC(Cc1cccc3c1n(C)c(=O)n3C1CCC(=O)NC1=O)C2] |

TABLE 1-continued
| Exemplary Compounds | |
|---|---|
| I-# | Structure |
| I-279 | 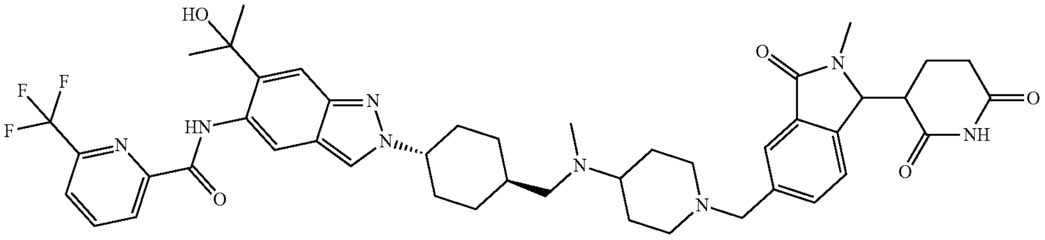 [SMILES: CN(C[C@H]1CC[C@H](n2cc3cc(NC(=O)c4cccc(C(F)(F)F)n4)c(C(C)(C)O)cc3n2)CC1)C1CCN(Cc2ccc3c(c2)C(=O)N(C)C3C2CCC(=O)NC2=O)CC1] |
| I-280 | 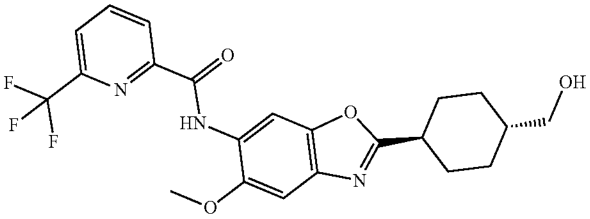 [SMILES: COc1cc2nc([C@H]3CC[C@H](CO)CC3)oc2cc1NC(=O)c1cccc(C(F)(F)F)n1] |
| I-281 | 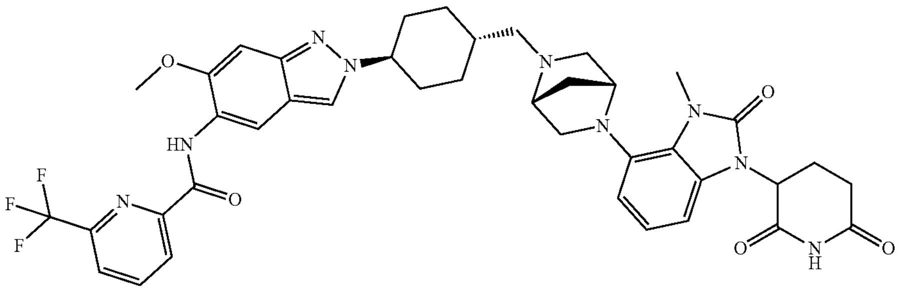 [SMILES: COc1cc2nn([C@H]3CC[C@H](CN4C[C@H]5C[C@@H]4CN5c4cccc5c4n(C)c(=O)n5C4CCC(=O)NC4=O)CC3)cc2cc1NC(=O)c1cccc(C(F)(F)F)n1] |
| I-282 | 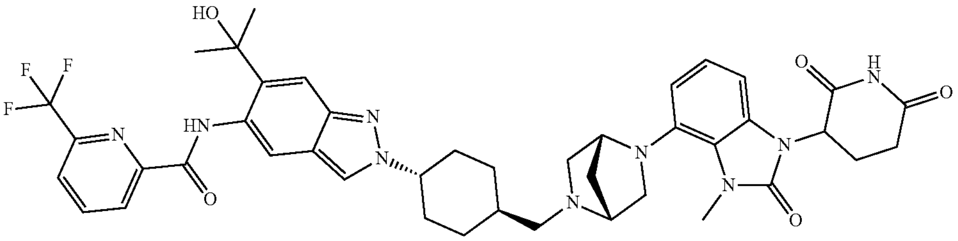 [SMILES: Cn1c(=O)n(C2CCC(=O)NC2=O)c2cccc(N3C[C@H]4C[C@@H]3CN4C[C@H]3CC[C@H](n4cc5cc(NC(=O)c6cccc(C(F)(F)F)n6)c(C(C)(C)O)cc5n4)CC3)c21] |
| I-283 | 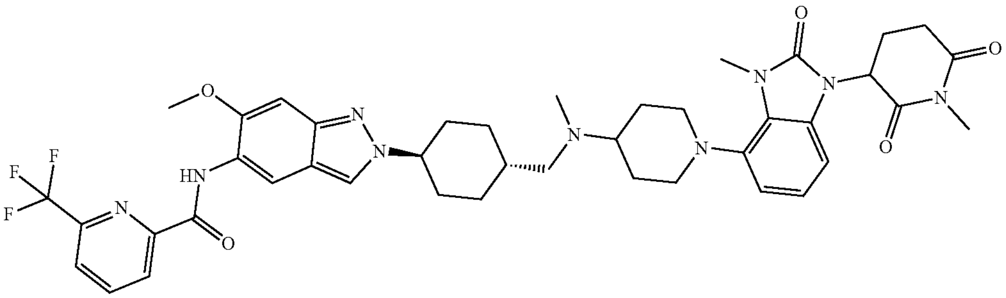 [SMILES: COc1cc2nn([C@H]3CC[C@H](CN(C)C4CCN(c5cccc6c5n(C)c(=O)n6C5CCC(=O)N(C)C5=O)CC4)CC3)cc2cc1NC(=O)c1cccc(C(F)(F)F)n1] |

TABLE 1-continued
| Exemplary Compounds | |
|---|---|
| I-# | Structure |
| I-284 | 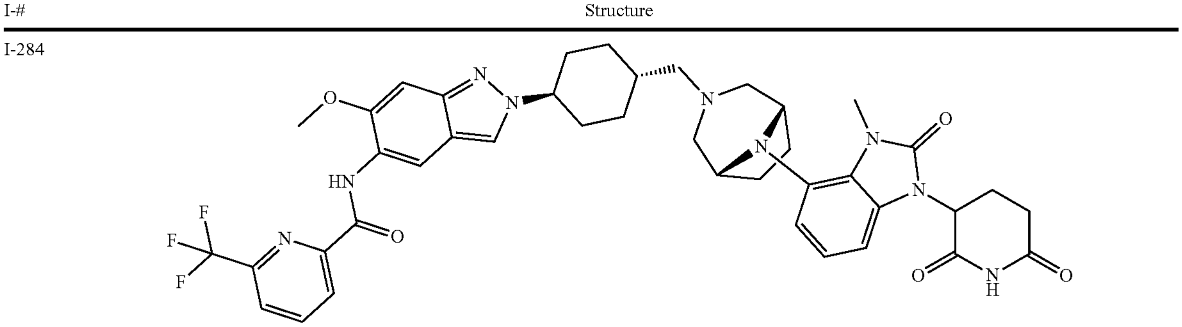 |
| I-285 | 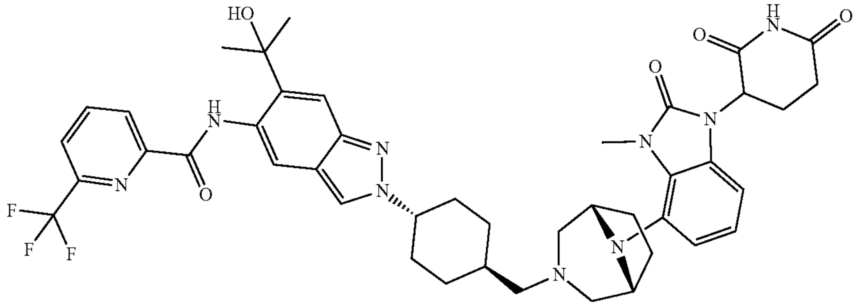 [SMILES: Cn1c(=O)n(C2CCC(=O)NC2=O)c2cccc(N3[C@@H]4CC[C@H]3CN(C[C@H]3CC[C@H](n5cc6cc(NC(=O)c7cccc(C(F)(F)F)n7)c(C(C)(C)O)cc6n5)CC3)C4)c21] |
| I-286 | 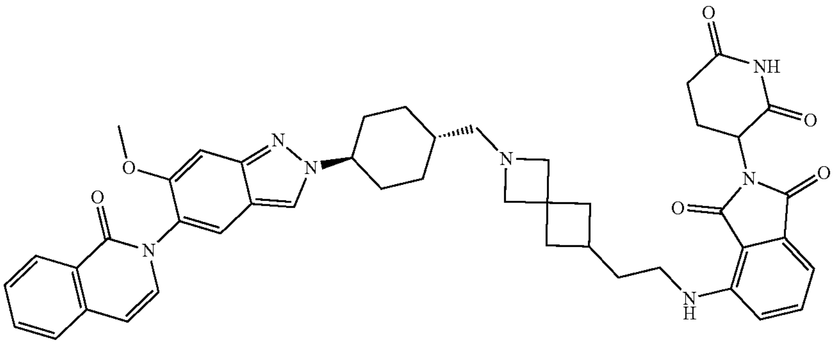 [SMILES: COc1cc2nn([C@H]3CC[C@H](CN4CC5(CC(CCNc6cccc7c6C(=O)N(C6CCC(=O)NC6=O)C7=O)C5)C4)CC3)cc2cc1-n1ccc2ccccc2c1=O] |
| I-287 | 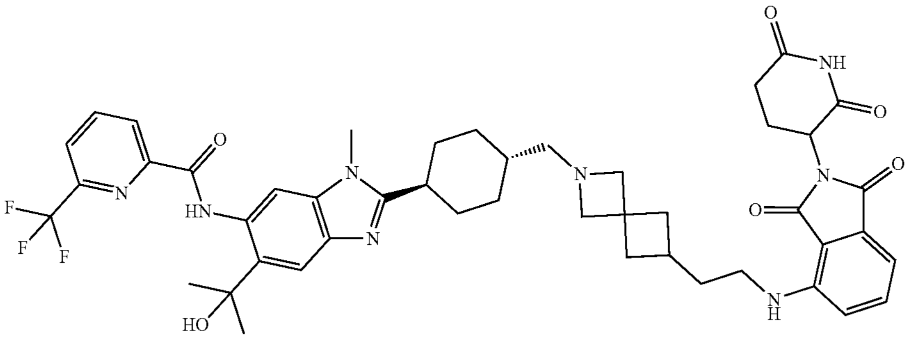 [SMILES: Cn1c2cc(NC(=O)c3cccc(C(F)(F)F)n3)c(C(C)(C)O)cc2nc1[C@H]1CC[C@H](CN2CC3(CC(CCNc4cccc5c4C(=O)N(C4CCC(=O)NC4=O)C5=O)C3)C2)CC1] |
| I-288 | 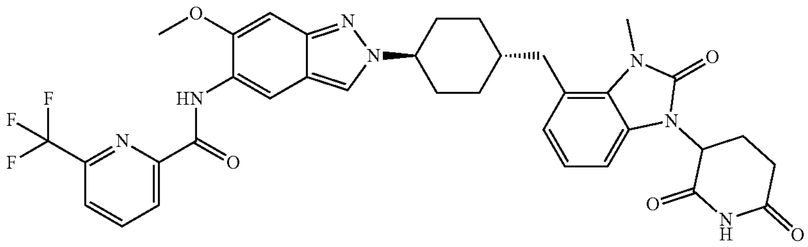 [SMILES: COc1cc2nn([C@H]3CC[C@H](Cc4cccc5c4n(C)c(=O)n5C4CCC(=O)NC4=O)CC3)cc2cc1NC(=O)c1cccc(C(F)(F)F)n1] |

TABLE 1-continued
| Exemplary Compounds | |
|---|---|
| I-# | Structure |
| I-289 | 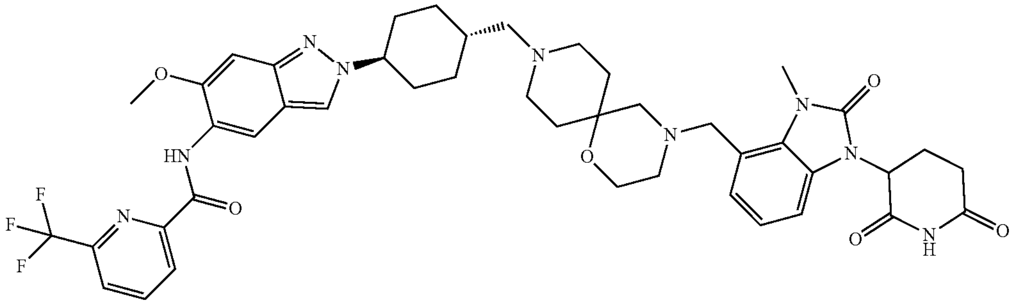 [SMILES: COc1cc2nn([C@H]3CC[C@H](CN4CCC5(CC4)CN(Cc4cccc6c4n(C)c(=O)n6C4CCC(=O)NC4=O)CCO5)CC3)cc2cc1NC(=O)c1cccc(C(F)(F)F)n1] |
| I-290 | 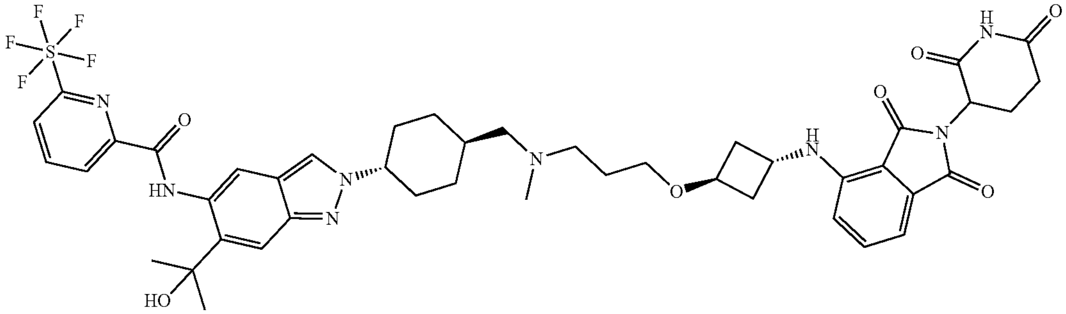 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)c4cccc(S(F)(F)(F)(F)F)n4)c(C(C)(C)O)cc3n2)CC1] |
| I-291 | 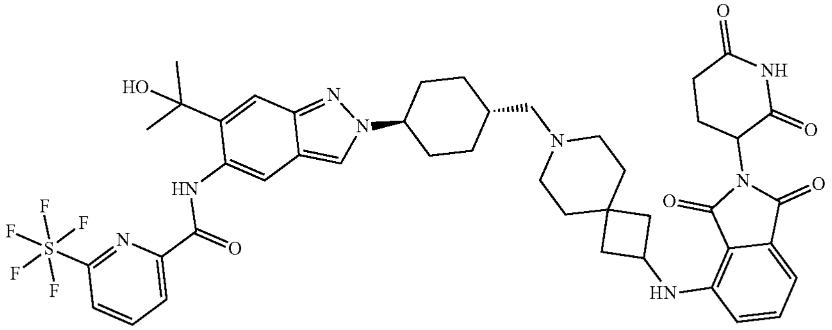 [SMILES: CC(C)(O)c1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cccc(S(F)(F)(F)(F)F)n1] |
| I-292 | 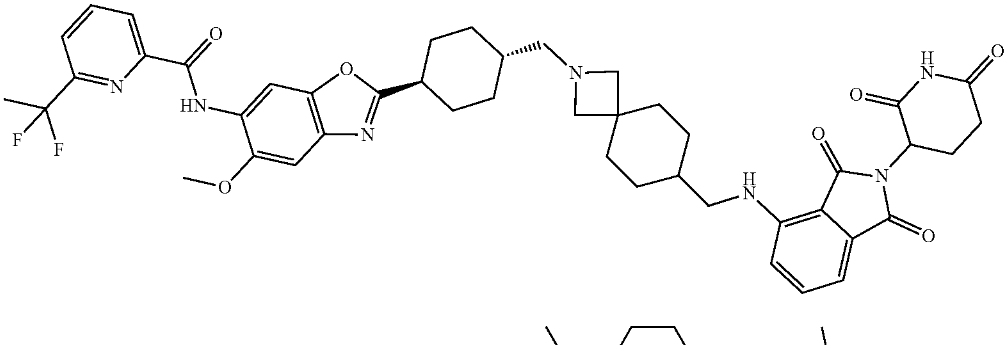 |
| I-293 | 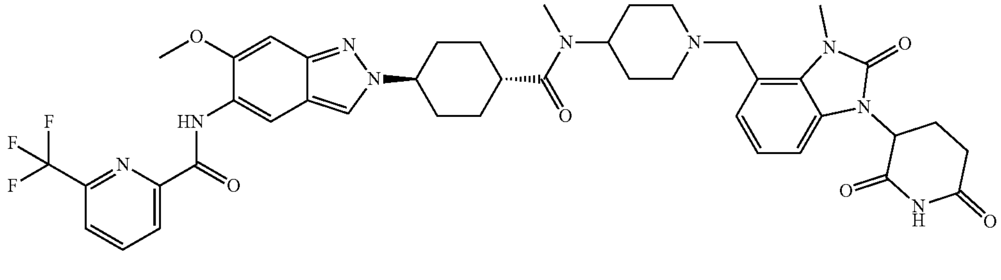 [SMILES: COc1cc2nn([C@H]3CC[C@H](C(=O)N(C)C4CCN(Cc5cccc6c5n(C)c(=O)n6C5CCC(=O)NC5=O)CC4)CC3)cc2cc1NC(=O)c1cccc(C(F)(F)F)n1] |

TABLE 1-continued
| Exemplary Compounds | |
|---|---|
| I-# | Structure |
| I-294 | 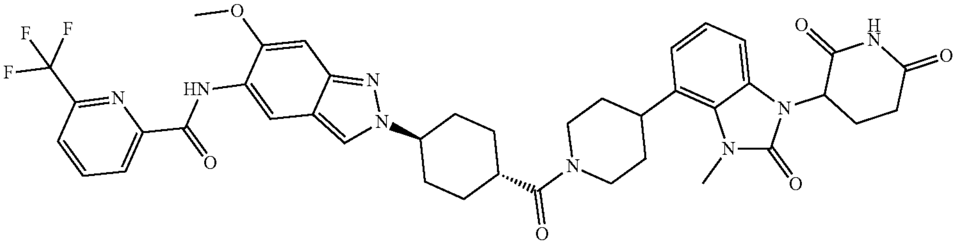 [SMILES: COc1cc2nn([C@H]3CC[C@H](C(=O)N4CCC(c5cccc6c5n(C)c(=O)n6C5CCC(=O)NC5=O)CC4)CC3)cc2cc1NC(=O)c1cccc(C(F)(F)F)n1] |
| I-295 | 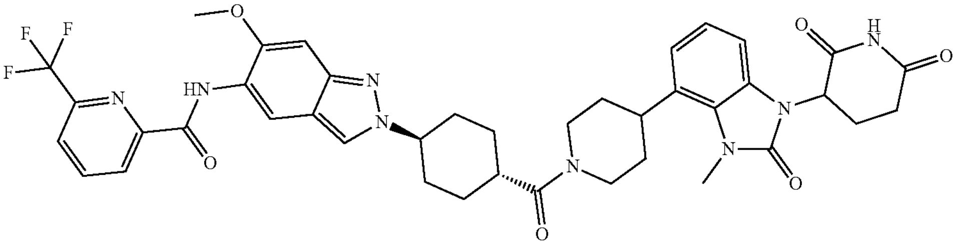 [SMILES: COc1cc2nn([C@H]3CC[C@H](C(=O)N4CCC(c5cccc6c5n(C)c(=O)n6C5CCC(=O)NC5=O)CC4)CC3)cc2cc1NC(=O)c1cccc(C(F)(F)F)n1] |
| I-296 | 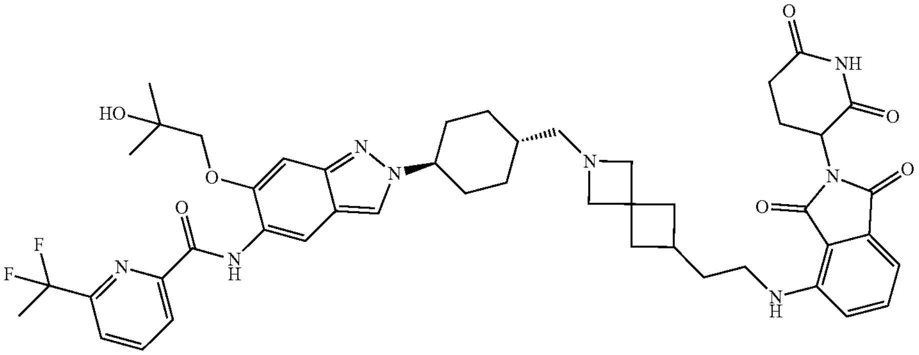 [SMILES: CC(C)(O)COc1cc2nn([C@H]3CC[C@H](CN4CC5(CC(CCNc6cccc7c6C(=O)N(C6CCC(=O)NC6=O)C7=O)C5)C4)CC3)cc2cc1NC(=O)c1cccc(C(C)(F)F)n1] |
| I-297 | 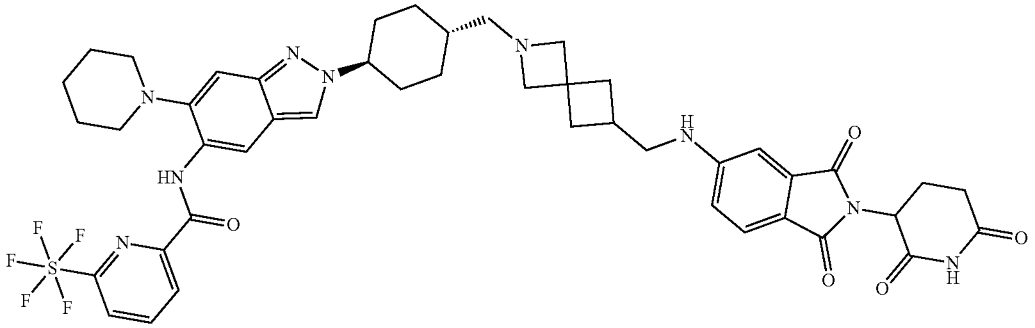 [SMILES: O=C1CCC(N2C(=O)c3ccc(NCC4CC5(C4)CN(C[C@H]4CC[C@H](n6cc7cc(NC(=O)c8cccc(S(F)(F)(F)(F)F)n8)c(N8CCCCC8)cc7n6)CC4)C5)cc3C2=O)C(=O)N1] |
| I-298 | 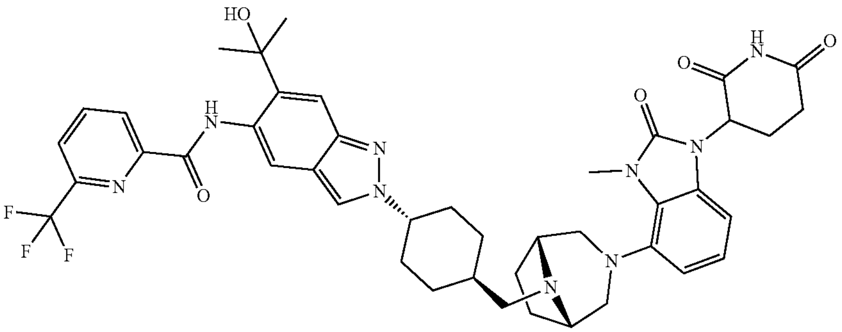 [SMILES: Cn1c(=O)n(C2CCC(=O)NC2=O)c2cccc(N3C[C@H]4CC[C@@H](C3)N4C[C@H]3CC[C@H](n4cc5cc(NC(=O)c6cccc(C(F)(F)F)n6)c(C(C)(C)O)cc5n4)CC3)c21] |

TABLE 1-continued
| Exemplary Compounds | |
|---|---|
| I-# | Structure |
| I-299 | 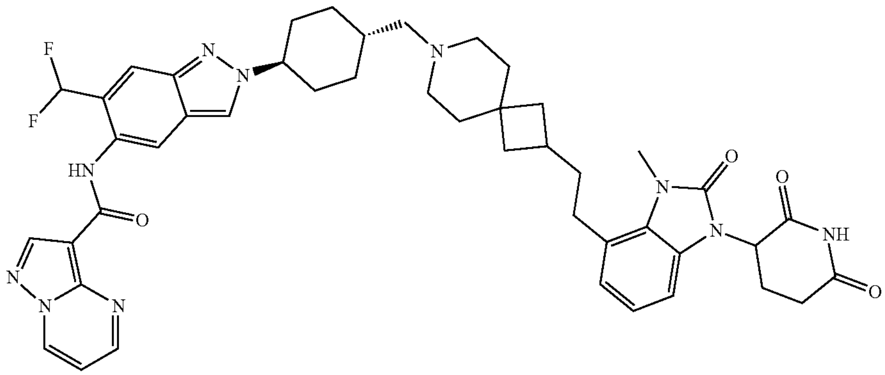 [SMILES: Cn1c(=O)n(C2CCC(=O)NC2=O)c2cccc(CCC3CC4(CCN(C[C@H]5CC[C@H](n6cc7cc(NC(=O)c8cnn9cccnc89)c(C(F)F)cc7n6)CC5)CC4)C3)c21] |
| I-300 | 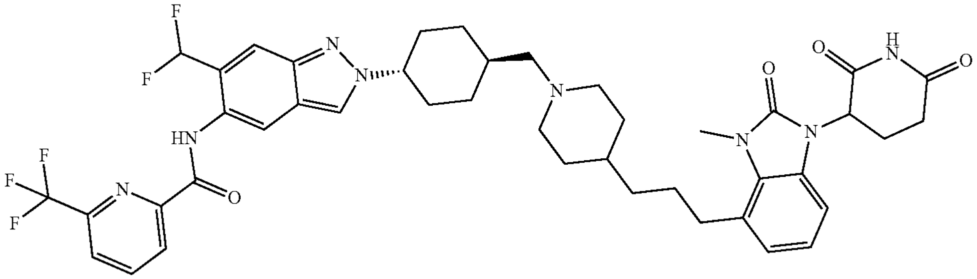 [SMILES: Cn1c(=O)n(C2CCC(=O)NC2=O)c2cccc(CCCC3CCN(C[C@H]4CC[C@H](n5cc6cc(NC(=O)c7cccc(C(F)(F)F)n7)c(C(F)F)cc6n5)CC4)CC3)c21] |
| I-301 | 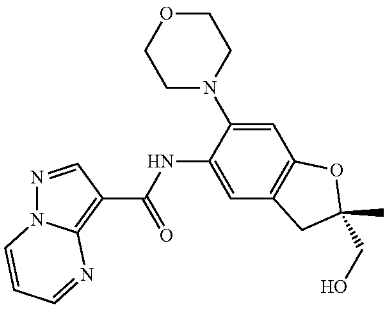 [SMILES: C[C@@]1(CO)Cc2cc(NC(=O)c3cnn4cccnc34)c(N3CCOCC3)cc2O1] |
| I-302 | 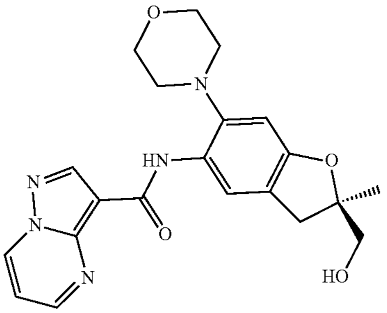 [SMILES: C[C@]1(CO)Cc2cc(NC(=O)c3cnn4cccnc34)c(N3CCOCC3)cc2O1] |

TABLE 1-continued
| Exemplary Compounds | |
|---|---|
| I-# | Structure |
| I-303 | 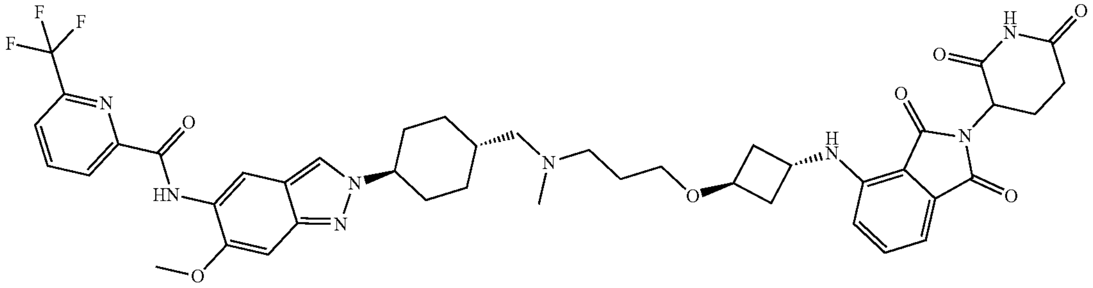 [SMILES: COc1cc2nn([C@H]3CC[C@H](CN(C)CCCO[C@H]4C[C@H](Nc5cccc6c5C(=O)N(C5CCC(=O)NC5=O)C6=O)C4)CC3)cc2cc1NC(=O)c1cccc(C(F)(F)F)n1] |
| I-304 | 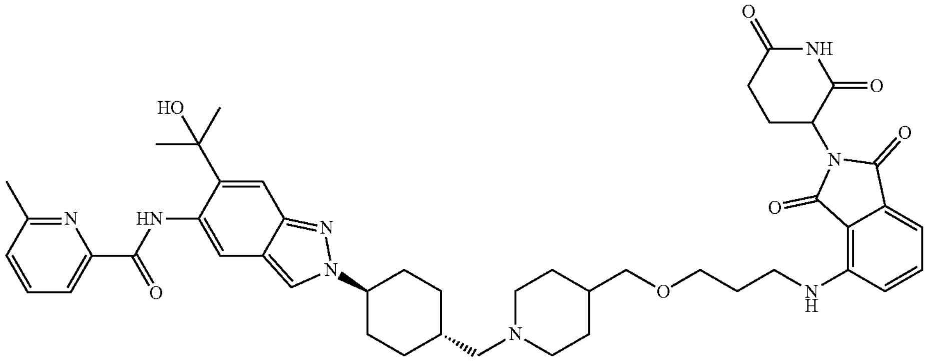 [SMILES: Cc1cccc(C(=O)Nc2cc3cn([C@H]4CC[C@H](CN5CCC(COCCCNc6cccc7c6C(=O)N(C6CCC(=O)NC6=O)C7=O)CC5)CC4)nc3cc2C(C)(C)O)n1] |
| I-305 | 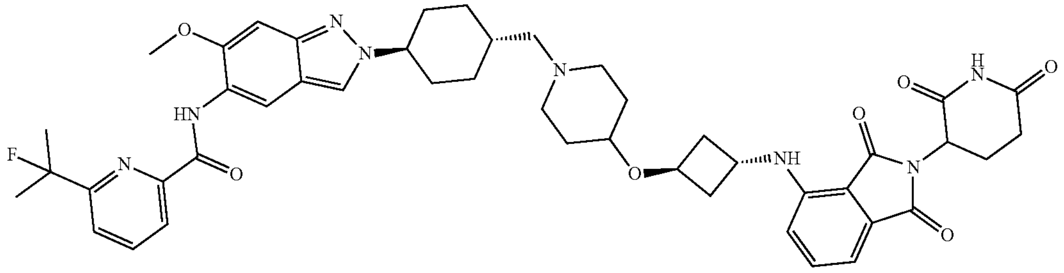 [SMILES: COc1cc2nn([C@H]3CC[C@H](CN4CCC(O[C@H]5C[C@H](Nc6cccc7c6C(=O)N(C6CCC(=O)NC6=O)C7=O)C5)CC4)CC3)cc2cc1NC(=O)c1cccc(C(C)(C)F)n1] |
| I-306 | 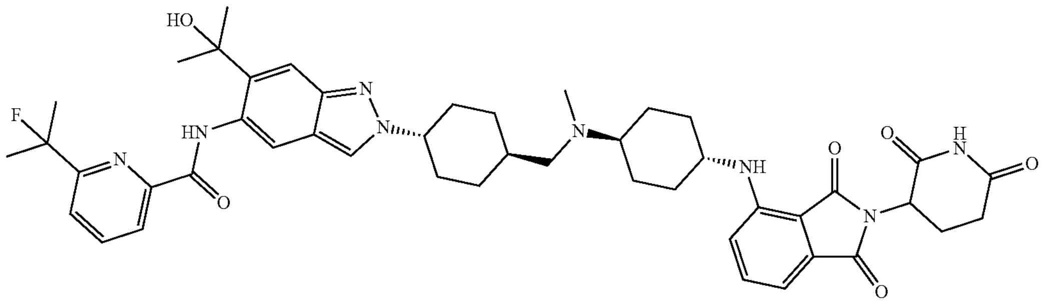 [SMILES: CN(C[C@H]1CC[C@H](n2cc3cc(NC(=O)c4cccc(C(C)(C)F)n4)c(C(C)(C)O)cc3n2)CC1)[C@H]1CC[C@H](Nc2cccc3c2C(=O)N(C2CCC(=O)NC2=O)C3=O)CC1] |
| I-307 | 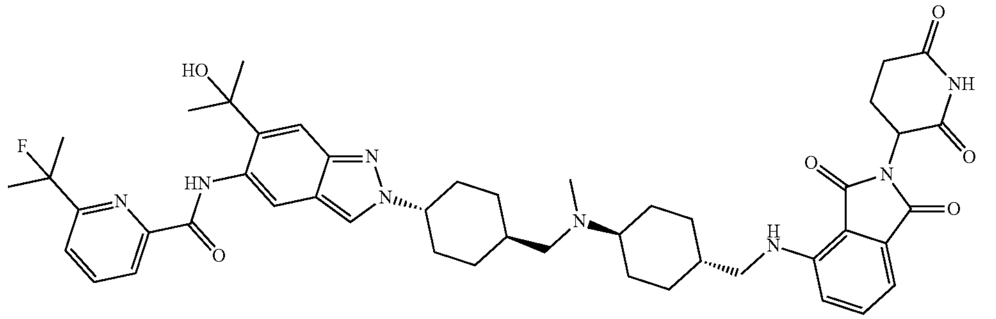 [SMILES: CN(C[C@H]1CC[C@H](n2cc3cc(NC(=O)c4cccc(C(C)(C)F)n4)c(C(C)(C)O)cc3n2)CC1)[C@H]1CC[C@H](CNc2cccc3c2C(=O)N(C2CCC(=O)NC2=O)C3=O)CC1] |

TABLE 1-continued
| Exemplary Compounds | |
|---|---|
| I-# | Structure |
| I-308 | 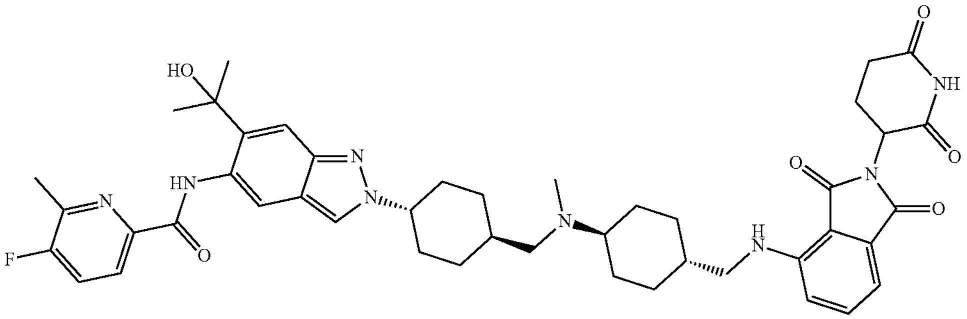 [SMILES: Cc1nc(C(=O)Nc2cc3cn([C@H]4CC[C@H](CN(C)[C@H]5CC[C@H](CNc6cccc7c6C(=O)N(C6CCC(=O)NC6=O)C7=O)CC5)CC4)nc3cc2C(C)(C)O)ccc1F] |
| I-309 | 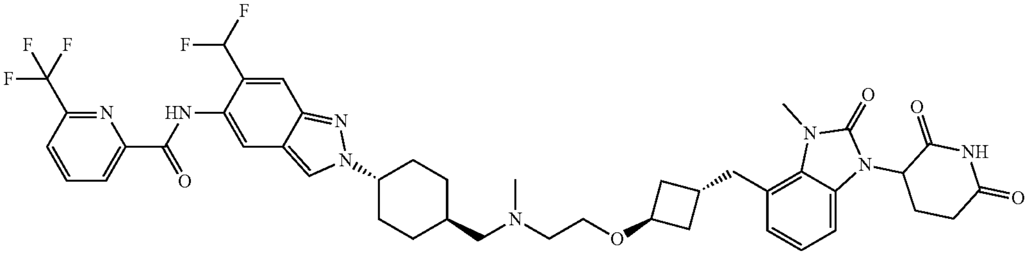 [SMILES: CN(CCO[C@H]1C[C@H](Cc2cccc3c2n(C)c(=O)n3C2CCC(=O)NC2=O)C1)C[C@H]1CC[C@H](n2cc3cc(NC(=O)c4cccc(C(F)(F)F)n4)c(C(F)F)cc3n2)CC1] |
| I-310 | 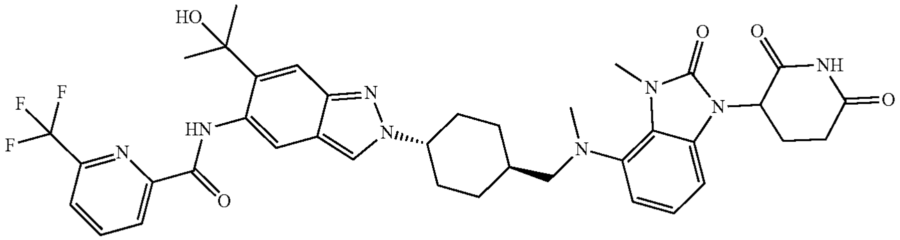 [SMILES: CN(C[C@H]1CC[C@H](n2cc3cc(NC(=O)c4cccc(C(F)(F)F)n4)c(C(C)(C)O)cc3n2)CC1)c1cccc2c1n(C)c(=O)n2C1CCC(=O)NC1=O] |
| I-311 | 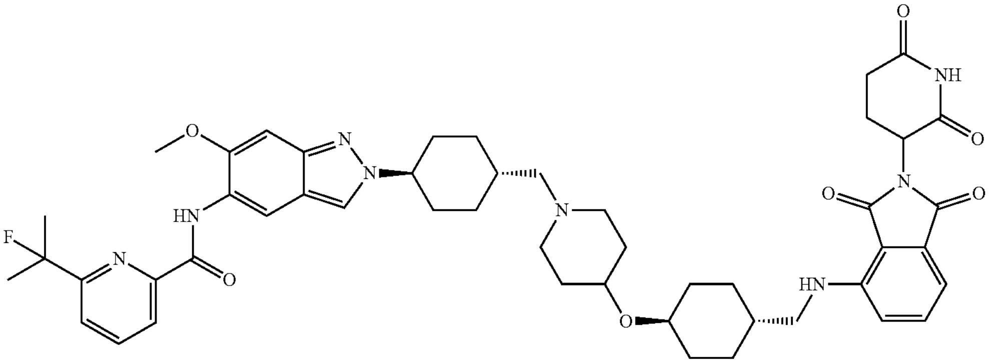 |
| I-312 | 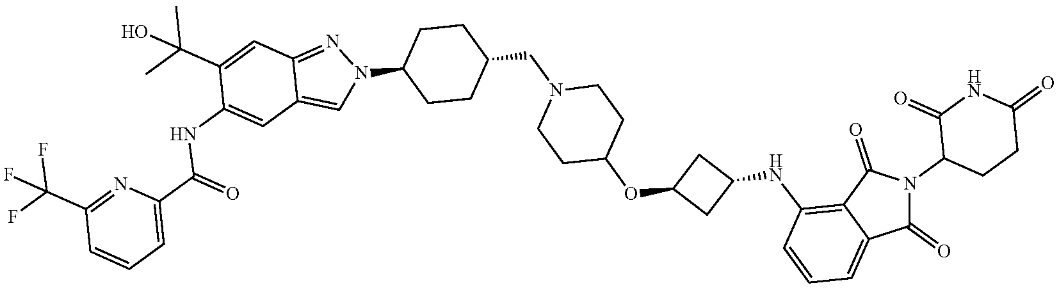 [SMILES: CC(C)(O)c1cc2nn([C@H]3CC[C@H](CN4CCC(O[C@H]5C[C@H](Nc6cccc7c6C(=O)N(C6CCC(=O)NC6=O)C7=O)C5)CC4)CC3)cc2cc1NC(=O)c1cccc(C(F)(F)F)n1] |

TABLE 1-continued
| Exemplary Compounds | |
|---|---|
| I-# | Structure |
| I-313 | 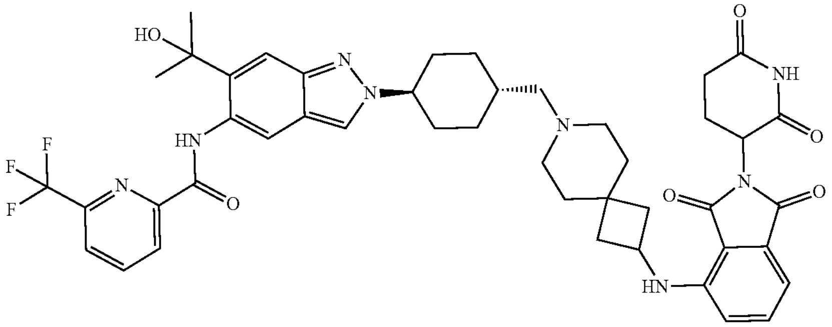 [SMILES: CC(C)(O)c1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cccc(C(F)(F)F)n1] |
| I-314 | 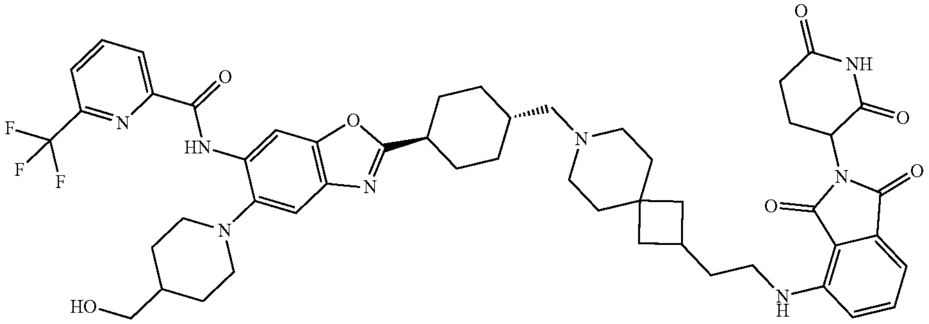 [SMILES: O=C1CCC(N2C(=O)c3cccc(NCCC4CC5(CCN(C[C@H]6CC[C@H](c7nc8cc(N9CCC(CO)CC9)c(NC(=O)c9cccc(C(F)(F)F)n9)cc8o7)CC6)CC5)C4)c3C2=O)C(=O)N1] |
| I-315 | 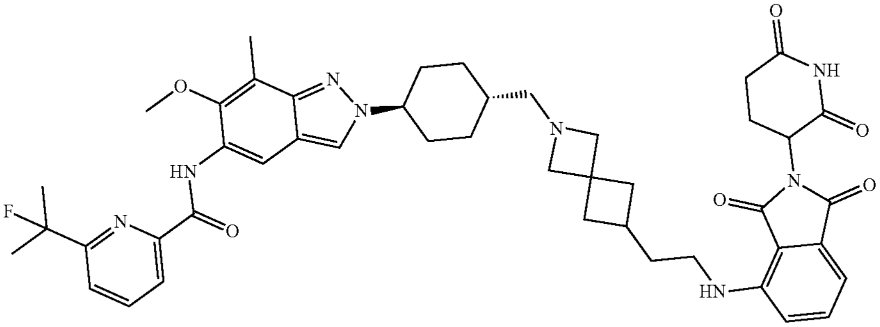 [SMILES: COc1c(NC(=O)c2cccc(C(C)(C)F)n2)cc2cn([C@H]3CC[C@H](CN4CC5(CC(CCNc6cccc7c6C(=O)N(C6CCC(=O)NC6=O)C7=O)C5)C4)CC3)nc2c1C] |
| I-316 | 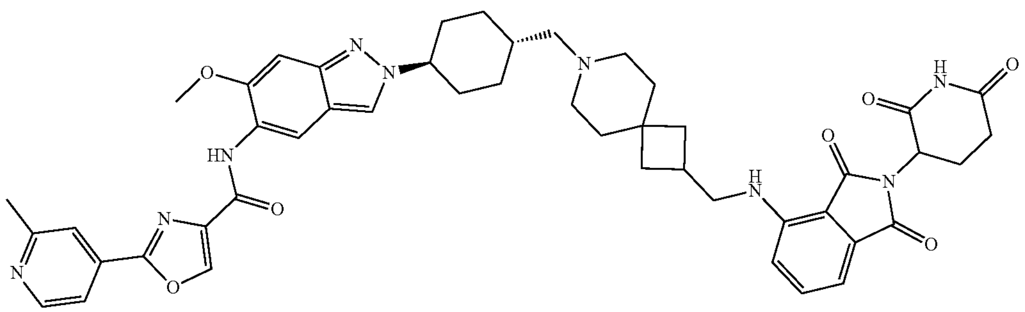 [SMILES: COc1cc2nn([C@H]3CC[C@H](CN4CCC5(CC4)CC(CNc4cccc6c4C(=O)N(C4CCC(=O)NC4=O)C6=O)C5)CC3)cc2cc1NC(=O)c1coc(-c2ccnc(C)c2)n1] |

TABLE 1-continued
| Exemplary Compounds | |
|---|---|
| I-# | Structure |
| I-317 | 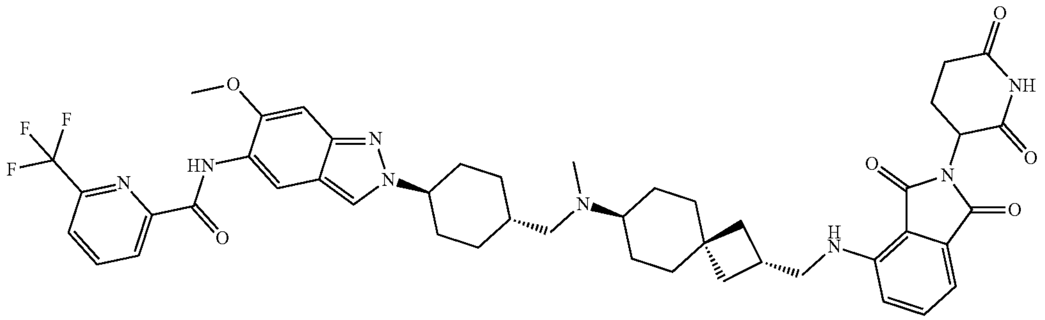 |
| I-318 | 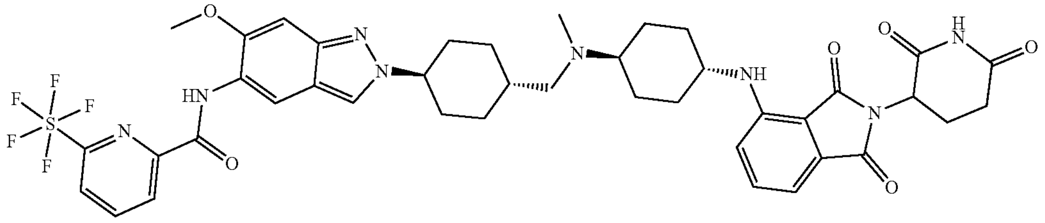 [SMILES: COc1cc2nn([C@H]3CC[C@H](CN(C)[C@H]4CC[C@H](Nc5cccc6c5C(=O)N(C5CCC(=O)NC5=O)C6=O)CC4)CC3)cc2cc1NC(=O)c1cccc(S(F)(F)(F)(F)F)n1] |
| I-319 | 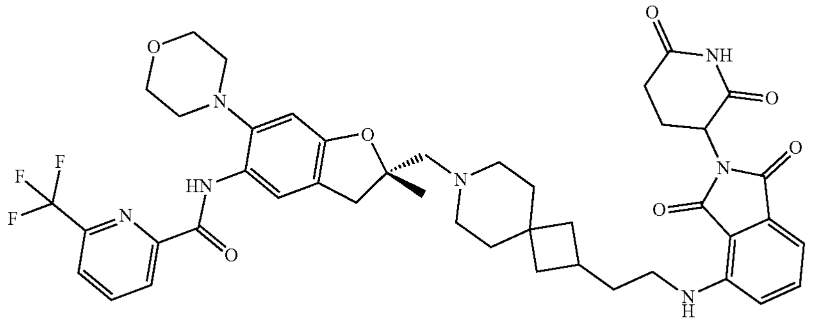 [SMILES: C[C@@]1(CN2CCC3(CC2)CC(CCNc2cccc4c2C(=O)N(C2CCC(=O)NC2=O)C4=O)C3)Cc2cc(NC(=O)c3cccc(C(F)(F)F)n3)c(N3CCOCC3)cc2O1] |
| I-320 | 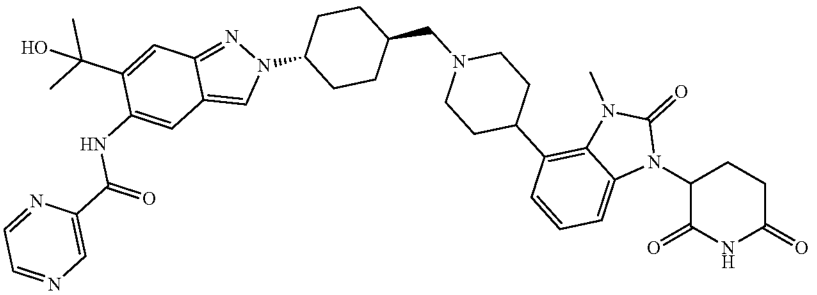 [SMILES: Cn1c(=O)n(C2CCC(=O)NC2=O)c2cccc(C3CCN(C[C@H]4CC[C@H](n5cc6cc(NC(=O)c7cnccn7)c(C(C)(C)O)cc6n5)CC4)CC3)c21] |
| I-321 | 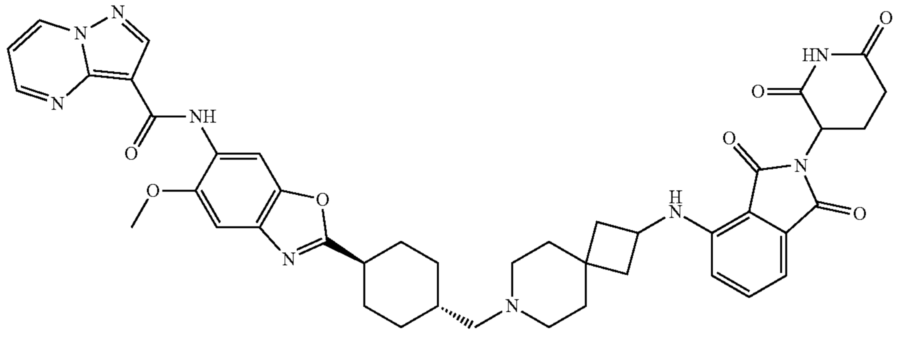 [SMILES: COc1cc2nc([C@H]3CC[C@H](CN4CCC5(CC4)CC(Nc4cccc6c4C(=O)N(C4CCC(=O)NC4=O)C6=O)C5)CC3)oc2cc1NC(=O)c1cnn2cccnc12] |

TABLE 1-continued
| Exemplary Compounds | |
|---|---|
| I-# | Structure |
| I-322 | 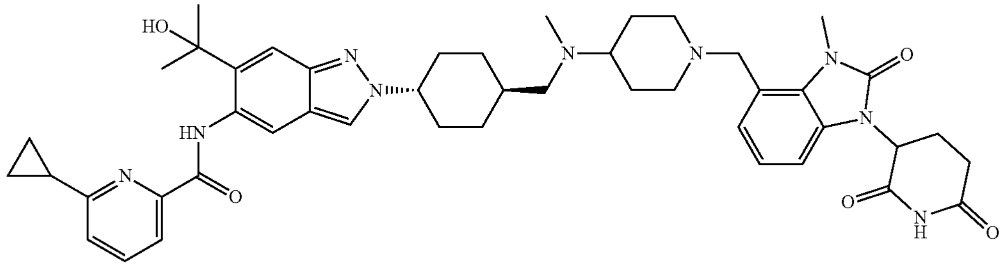 [SMILES: CN(C[C@H]1CC[C@H](n2cc3cc(NC(=O)c4cccc(C5CC5)n4)c(C(C)(C)O)cc3n2)CC1)C1CCN(Cc2cccc3c2n(C)c(=O)n3C2CCC(=O)NC2=O)CC1] |
| I-323 | 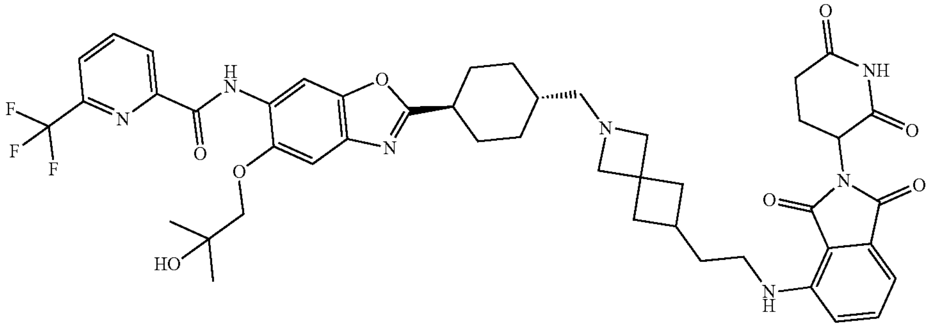 [SMILES: CC(C)(O)COc1cc2nc([C@H]3CC[C@H](CN4CC5(CC(CCNc6cccc7c6C(=O)N(C6CCC(=O)NC6=O)C7=O)C5)C4)CC3)oc2cc1NC(=O)c1cccc(C(F)(F)F)n1] |
| I-324 | 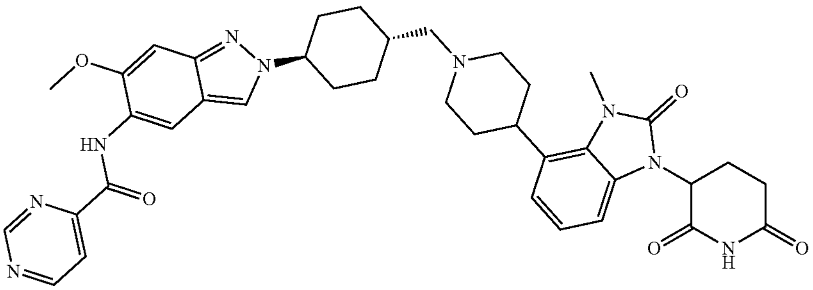 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1ccncn1] |
| I-325 | 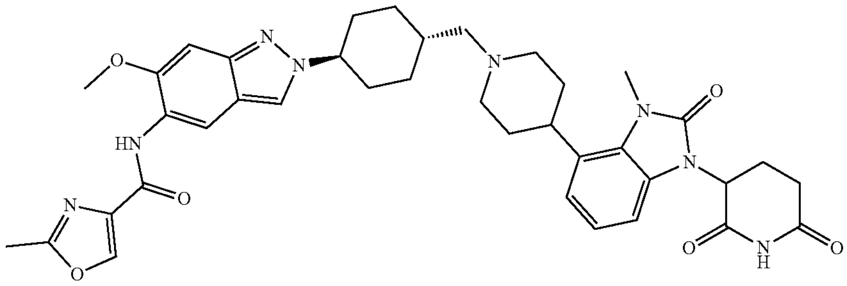 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1coc(C)n1] |
| I-326 | 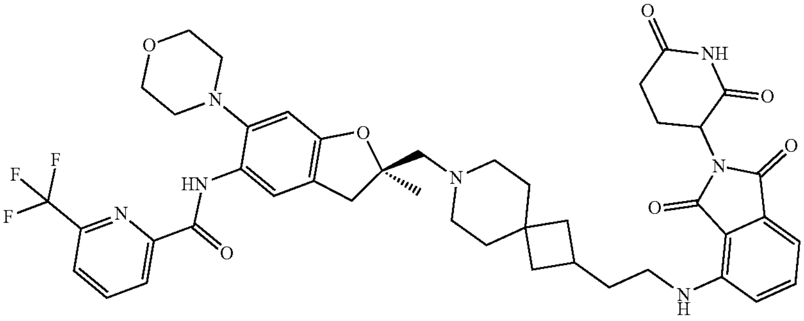 [SMILES: C[C@]1(CN2CCC3(CC2)CC(CCNc2cccc4c2C(=O)N(C2CCC(=O)NC2=O)C4=O)C3)Cc2cc(NC(=O)c3cccc(C(F)(F)F)n3)c(N3CCOCC3)cc2O1] |

TABLE 1-continued
| Exemplary Compounds | |
|---|---|
| I-# | Structure |
| I-327 | 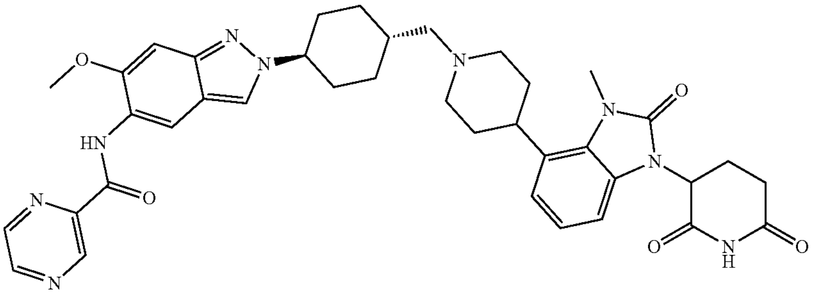 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cnccn1] |
| I-328 | 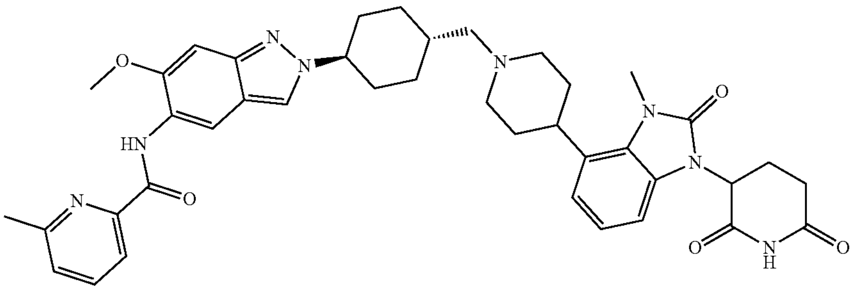 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cccc(C)n1] |
| I-329 | 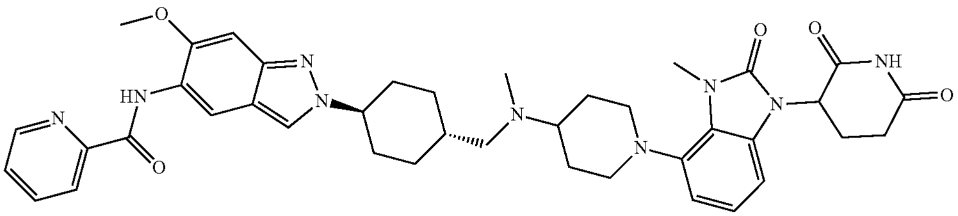 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccccn1] |
| I-330 | 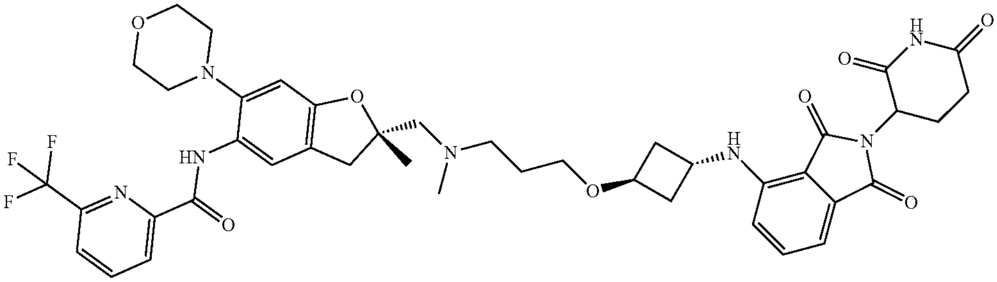 [SMILES: CN(CCCO[C@H]1C[C@H](Nc2cccc3c2C(=O)N(C2CCC(=O)NC2=O)C3=O)C1)C[C@]1(C)Cc2cc(NC(=O)c3cccc(C(F)(F)F)n3)c(N3CCOCC3)cc2O1] |
| I-331 | 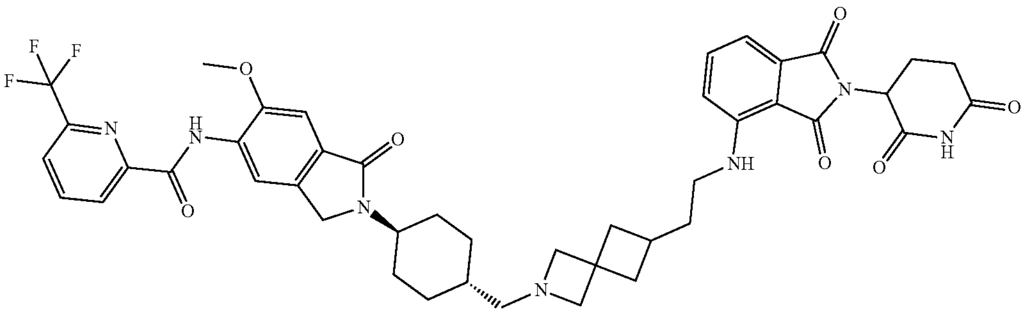 [SMILES: COc1cc2c(cc1NC(=O)c1cccc(C(F)(F)F)n1)CN([C@H]1CC[C@H](CN3CC4(CC(CCNc5cccc6c5C(=O)N(C5CCC(=O)NC5=O)C6=O)C4)C3)CC1)C2=O] |

TABLE 1-continued
| Exemplary Compounds | |
|---|---|
| I-# | Structure |
| I-332 | 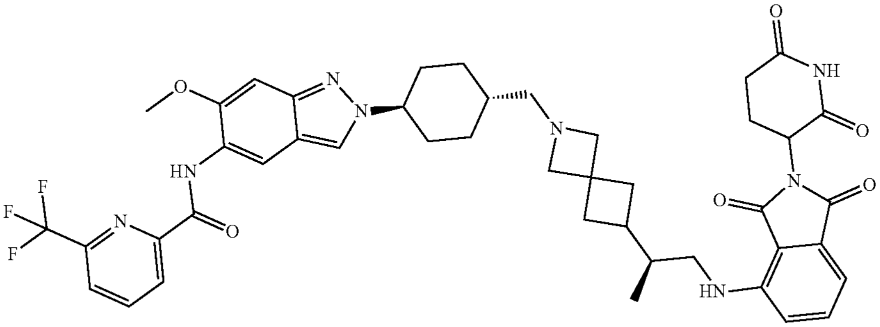 [SMILES: COc1cc2nn([C@H]3CC[C@H](CN4CC5(CC([C@H](C)CNc6cccc7c6C(=O)N(C6CCC(=O)NC6=O)C7=O)C5)C4)CC3)cc2cc1NC(=O)c1cccc(C(F)(F)F)n1] |
| I-333 | 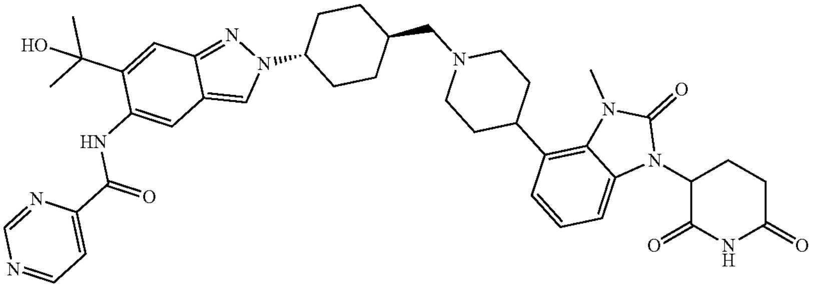 [SMILES: Cn1c(=O)n(C2CCC(=O)NC2=O)c2cccc(C3CCN(C[C@H]4CC[C@H](n5cc6cc(NC(=O)c7ccncn7)c(C(C)(C)O)cc6n5)CC4)CC3)c21] |
| I-334 | 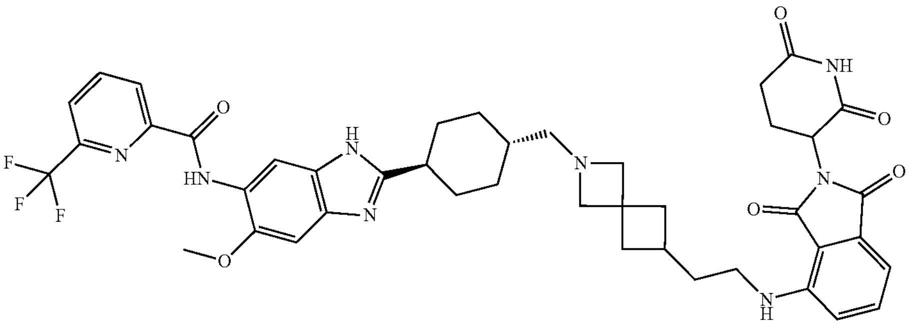 [SMILES: COc1cc2nc([C@H]3CC[C@H](CN4CC5(CC(CCNc6cccc7c6C(=O)N(C6CCC(=O)NC6=O)C7=O)C5)C4)CC3)[nH]c2cc1NC(=O)c1cccc(C(F)(F)F)n1] |
| I-335 | 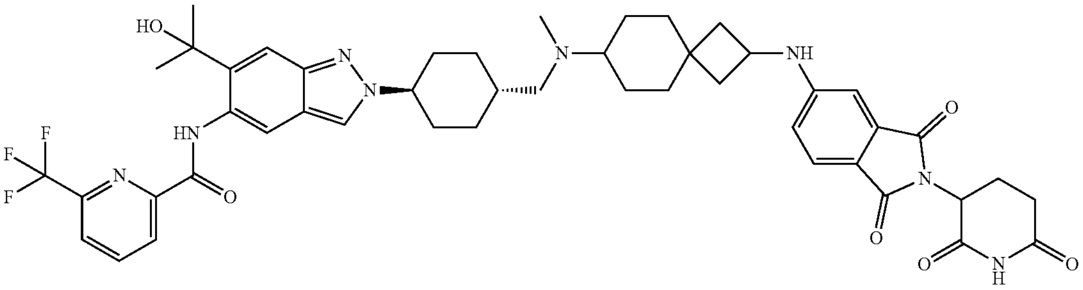 [SMILES: CN(C[C@H]1CC[C@H](n2cc3cc(NC(=O)c4cccc(C(F)(F)F)n4)c(C(C)(C)O)cc3n2)CC1)C1CCC2(CC1)CC(Nc1ccc3c(c1)C(=O)N(C1CCC(=O)NC1=O)C3=O)C2] |
| I-336 | 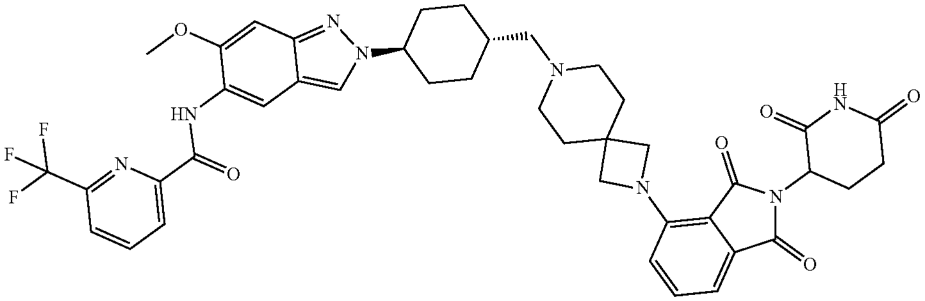 [SMILES: COc1cc2nn([C@H]3CC[C@H](CN4CCC5(CC4)CN(c4cccc6c4C(=O)N(C4CCC(=O)NC4=O)C6=O)C5)CC3)cc2cc1NC(=O)c1cccc(C(F)(F)F)n1] |

TABLE 1-continued
Exemplary Compounds
I-# Structure
I-337
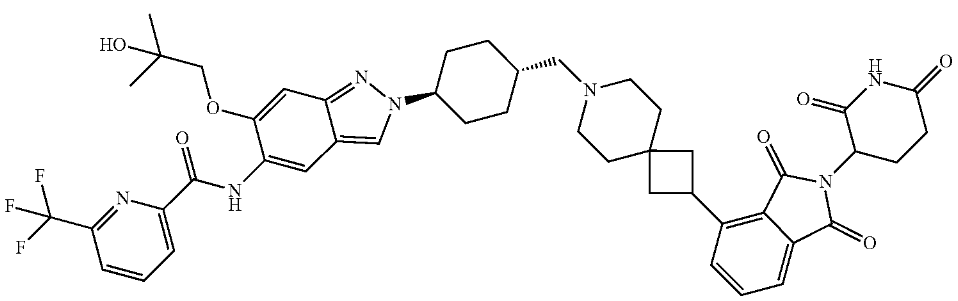 [SMILES: CC(C)(O)COc1cc2nn([C@H]3CC[C@H](CN4CCC5(CC4)CC(c4cccc6c4C(=O)N(C4CCC(=O)NC4=O)C6=O)C5)CC3)cc2cc1NC(=O)c1cccc(C(F)(F)F)n1]
I-338
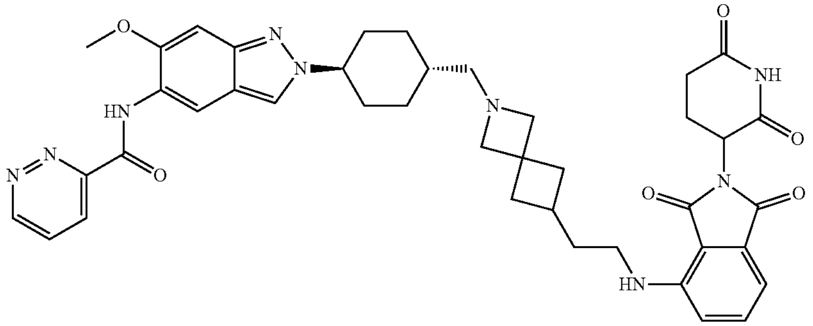 [SMILES: COc1cc2nn([C@H]3CC[C@H](CN4CC5(CC(CCNc6cccc7c6C(=O)N(C6CCC(=O)NC6=O)C7=O)C5)C4)CC3)cc2cc1NC(=O)c1cccnn1]
I-339
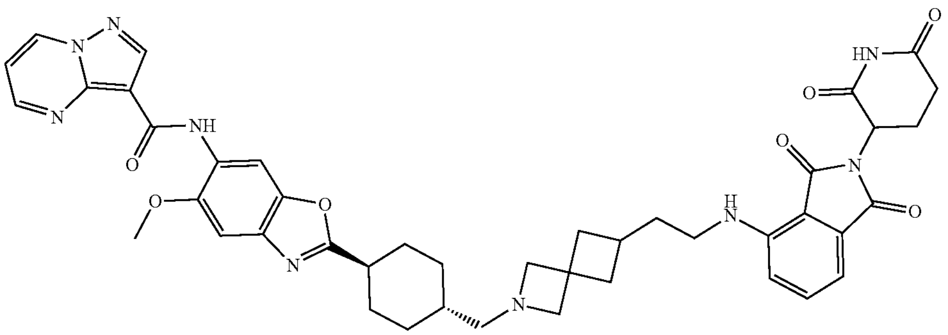 [SMILES: COc1cc2nc([C@H]3CC[C@H](CN4CC5(CC(CCNc6cccc7c6C(=O)N(C6CCC(=O)NC6=O)C7=O)C5)C4)CC3)oc2cc1NC(=O)c1cnn2cccnc12]
I-340
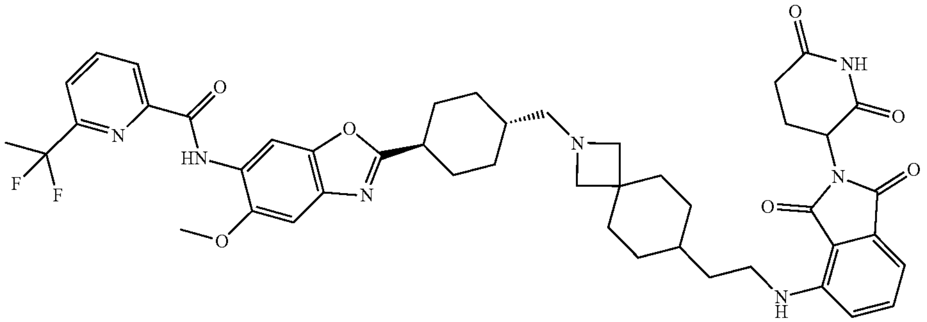 [SMILES: COc1cc2nc([C@H]3CC[C@H](CN4CC5(CCC(CCNc6cccc7c6C(=O)N(C6CCC(=O)NC6=O)C7=O)CC5)C4)CC3)oc2cc1NC(=O)c1cccc(C(C)(F)F)n1]

TABLE 1-continued
| Exemplary Compounds | |
|---|---|
| I-# | Structure |
| I-341 | 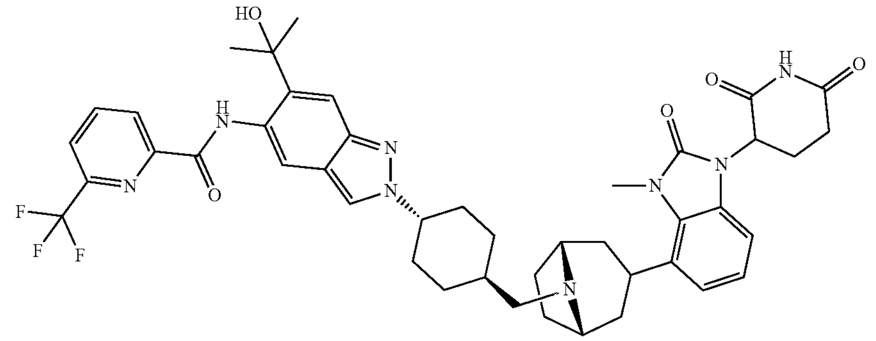 [SMILES: Cn1c(=O)n(C2CCC(=O)NC2=O)c2cccc(C3C[C@H]4CC[C@@H](C3)N4CC[C@H]3CC[C@H](n4cc5cc(NC(=O)c6cccc(C(F)(F)F)n6)c(C(C)(C)O)cc5n4)CC3)c21] |
| I-342 | 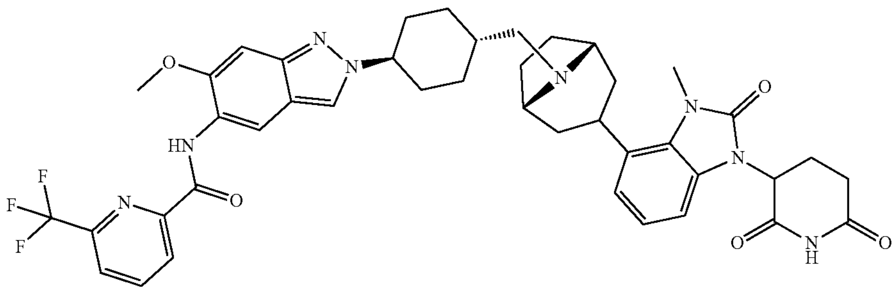 [SMILES: COc1cc2nn([C@H]3CC[C@H](CN4[C@@H]5CC[C@H]4CC(c4cccc6c4n(C)c(=O)n6C4CCC(=O)NC4=O)C5)CC3)cc2cc1NC(=O)c1cccc(C(F)(F)F)n1] |
| I-343 | 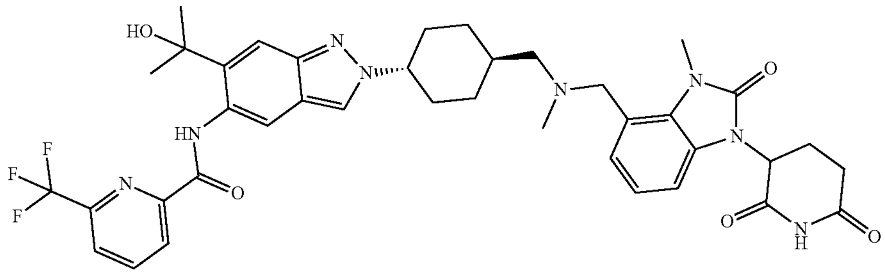 [SMILES: CN(Cc1cccc2c1n(C)c(=O)n2C1CCC(=O)NC1=O)C[C@H]1CC[C@H](n2cc3cc(NC(=O)c4cccc(C(F)(F)F)n4)c(C(C)(C)O)cc3n2)CC1] |
| I-344 | 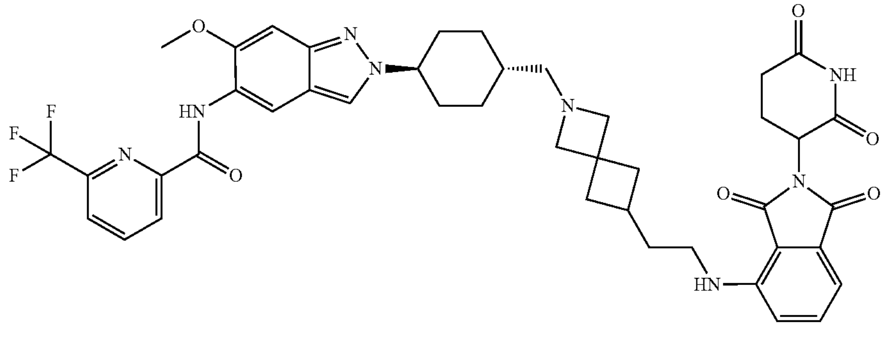 [SMILES: COc1cc2nn([C@H]3CC[C@H](CN4CC5(CC(CCNc6cccc7c6C(=O)N(C6CCC(=O)NC6=O)C7=O)C5)C4)CC3)cc2cc1NC(=O)c1cccc(C(F)(F)F)n1] |
| I-345 | 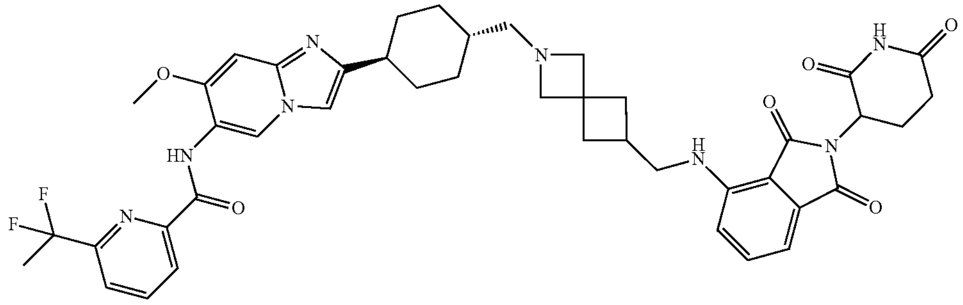 [SMILES: COc1cc2nc([C@H]3CC[C@H](CN4CC5(CC(CNc6cccc7c6C(=O)N(C6CCC(=O)NC6=O)C7=O)C5)C4)CC3)cn2cc1NC(=O)c1cccc(C(C)(F)F)n1] |

TABLE 1-continued
| Exemplary Compounds | |
|---|---|
| I-# | Structure |
| I-346 | 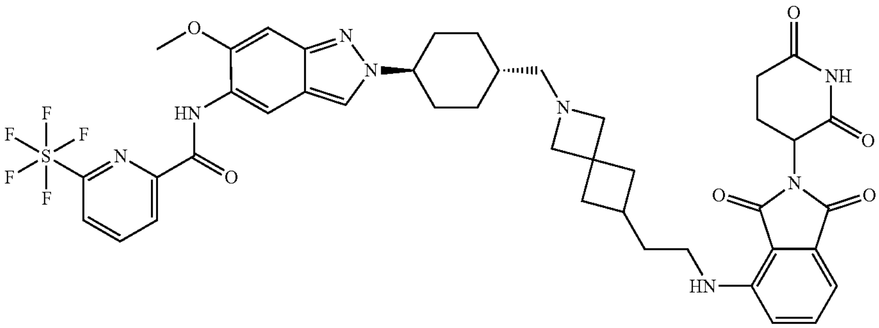 [SMILES: COc1cc2nn([C@H]3CC[C@H](CN4CC5(CC(CCNc6cccc7c6C(=O)N(C6CCC(=O)NC6=O)C7=O)C5)C4)CC3)cc2cc1NC(=O)c1cccc(S(F)(F)(F)(F)F)n1] |
| I-347 | 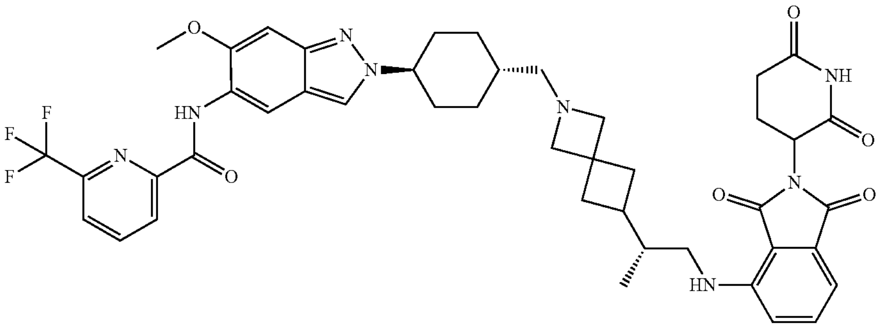 [SMILES: COc1cc2nn([C@H]3CC[C@H](CN4CC5(CC([C@@H](C)CNc6cccc7c6C(=O)N(C6CCC(=O)NC6=O)C7=O)C5)C4)CC3)cc2cc1NC(=O)c1cccc(C(F)(F)F)n1] |
| I-348 | 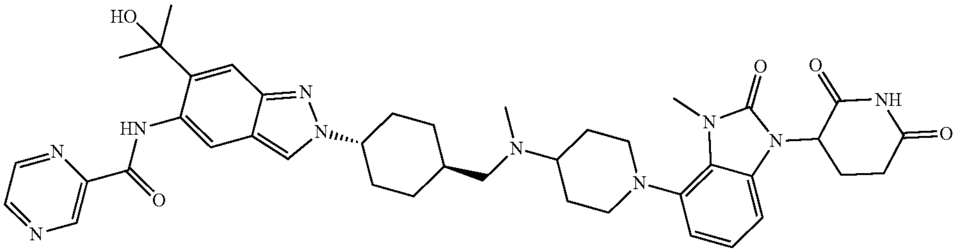 [SMILES: CN(C[C@H]1CC[C@H](n2cc3cc(NC(=O)c4cnccn4)c(C(C)(C)O)cc3n2)CC1)C1CCN(c2cccc3c2n(C)c(=O)n3C2CCC(=O)NC2=O)CC1] |
| I-349 | 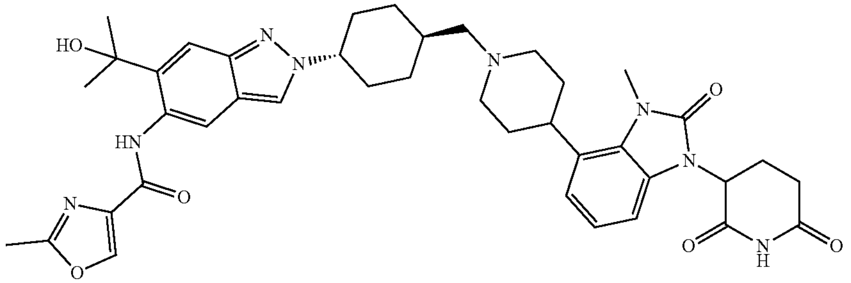 [SMILES: Cc1nc(C(=O)Nc2cc3cn([C@H]4CC[C@H](CN5CCC(c6cccc7c6n(C)c(=O)n7C6CCC(=O)NC6=O)CC5)CC4)nc3cc2C(C)(C)O)co1] |
| I-350 | 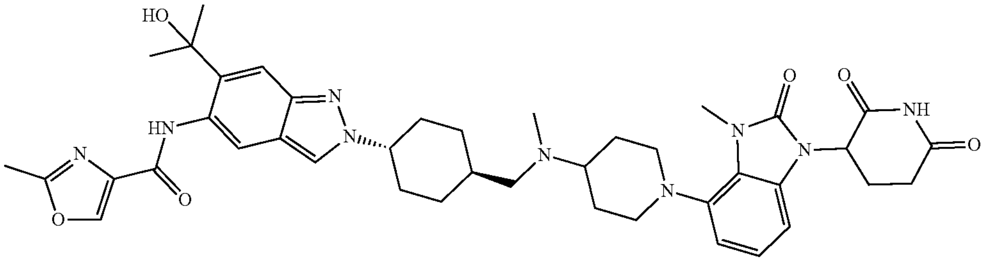 [SMILES: Cc1nc(C(=O)Nc2cc3cn([C@H]4CC[C@H](CN(C)C5CCN(c6cccc7c6n(C)c(=O)n7C6CCC(=O)NC6=O)CC5)CC4)nc3cc2C(C)(C)O)co1] |

TABLE 1-continued
| Exemplary Compounds | |
|---|---|
| I-# | Structure |
| I-351 | 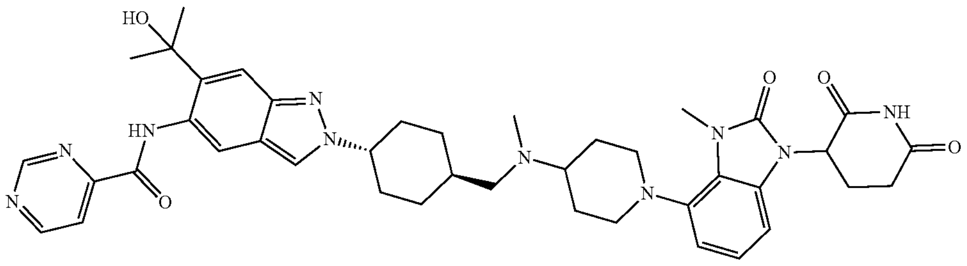 [SMILES: CN(C[C@H]1CC[C@H](n2cc3cc(NC(=O)c4ccncn4)c(C(C)(C)O)cc3n2)CC1)C1CCN(c2cccc3c2n(C)c(=O)n3C2CCC(=O)NC2=O)CC1] |
| I-352 | 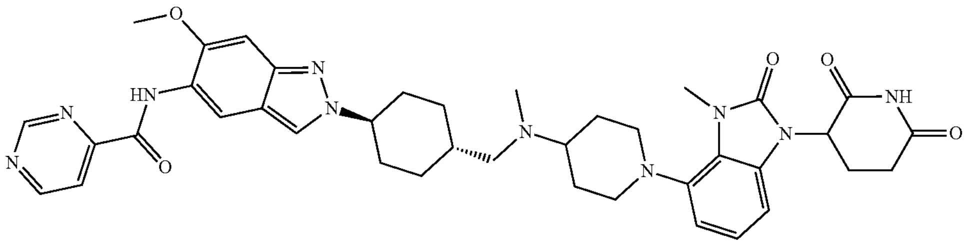 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccncn1] |
| I-353 | 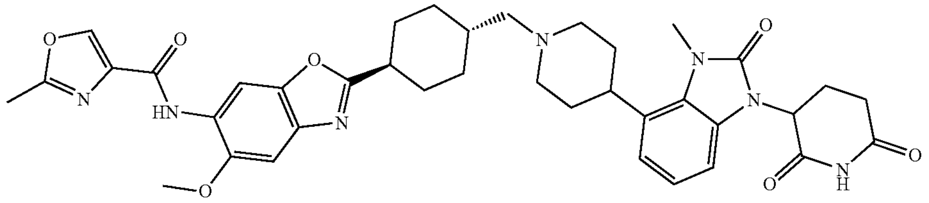 [SMILES: COc1cc2nc([C@H]3CC[C@H](CN4CCC(c5cccc6c5n(C)c(=O)n6C5CCC(=O)NC5=O)CC4)CC3)oc2cc1NC(=O)c1coc(C)n1] |
| I-354 | 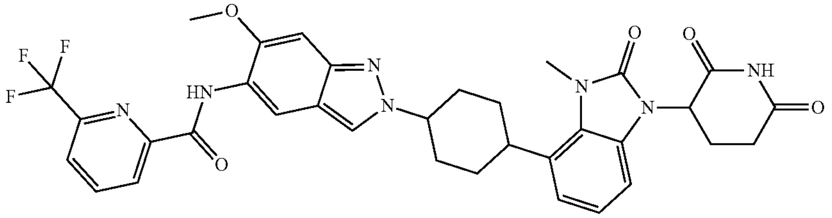 [SMILES: COc1cc2nn(C3CCC(c4cccc5c4n(C)c(=O)n5C4CCC(=O)NC4=O)CC3)cc2cc1NC(=O)c1cccc(C(F)(F)F)n1] |
| I-355 | 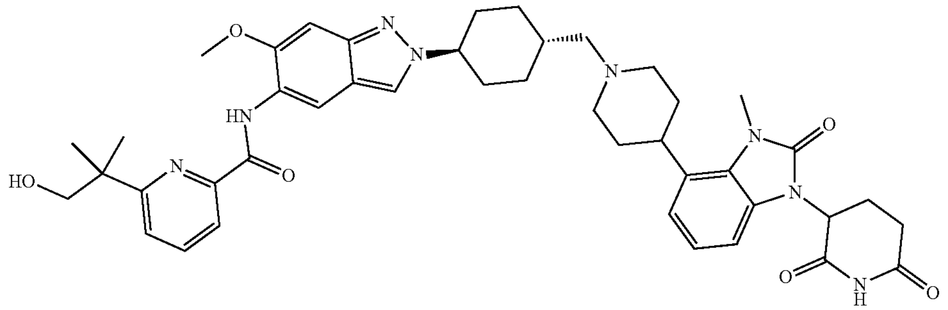 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cccc(C(C)(C)CO)n1] |
| I-356 | 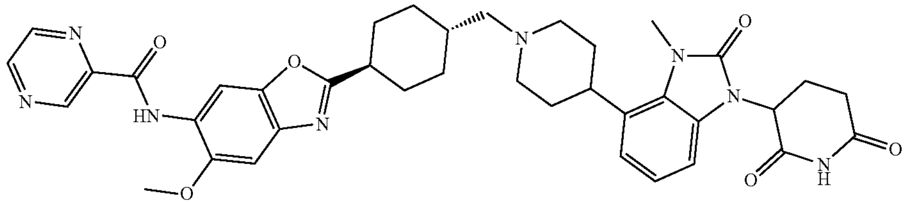 [SMILES: COc1cc2nc([C@H]3CC[C@H](CN4CCC(c5cccc6c5n(C)c(=O)n6C5CCC(=O)NC5=O)CC4)CC3)oc2cc1NC(=O)c1cnccn1] |

TABLE 1-continued
| Exemplary Compounds | |
|---|---|
| I-# | Structure |
| I-357 | 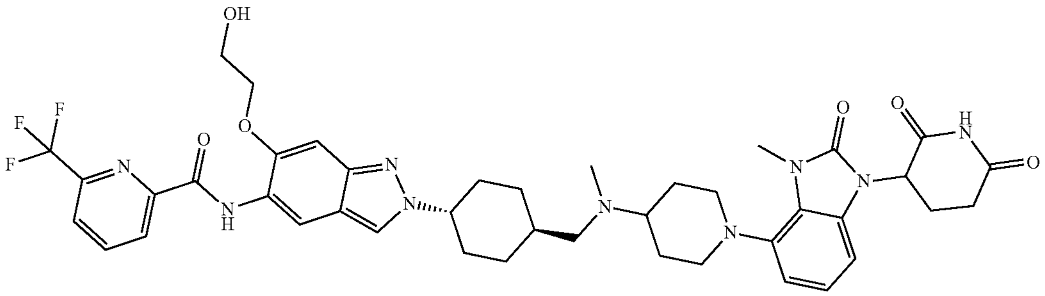 [SMILES: CN(C[C@H]1CC[C@H](n2cc3cc(NC(=O)c4cccc(C(F)(F)F)n4)c(OCCO)cc3n2)CC1)C1CCN(c2cccc3c2n(C)c(=O)n3C2CCC(=O)NC2=O)CC1] |
| I-358 | 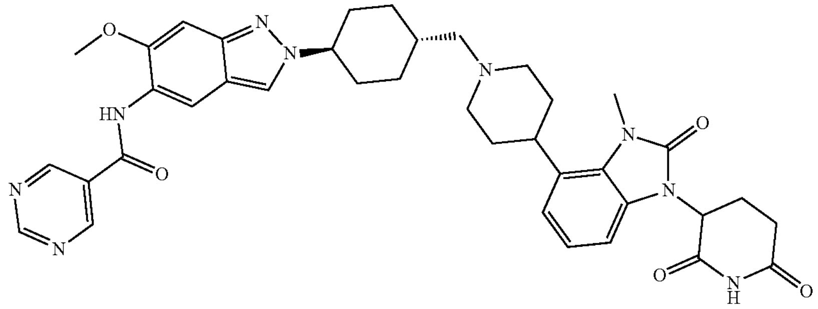 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncnc1] |
| I-359 | 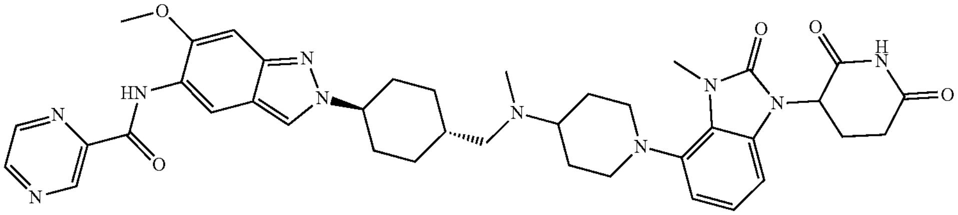 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cnccn1] |
| I-360 | 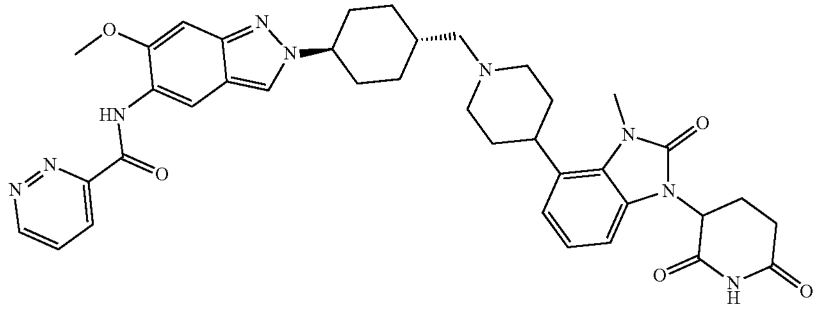 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cccnn1] |
| I-361 | 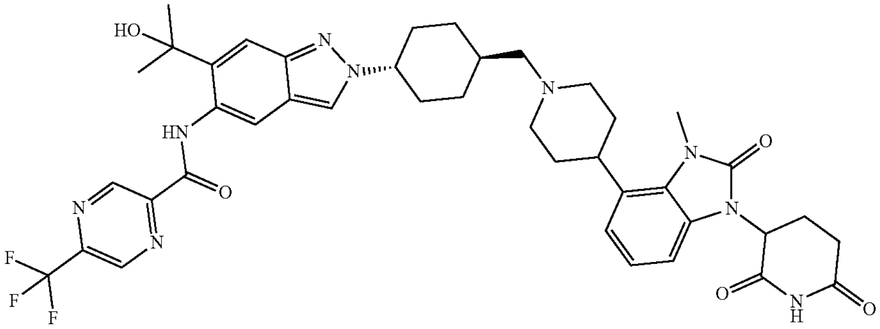 [SMILES: Cn1c(=O)n(C2CCC(=O)NC2=O)c2cccc(C3CCN(C[C@H]4CC[C@H](n5cc6cc(NC(=O)c7cnc(C(F)(F)F)cn7)c(C(C)(C)O)cc6n5)CC4)CC3)c21] |

TABLE 1-continued
| Exemplary Compounds | |
|---|---|
| I-# | Structure |
| I-362 | 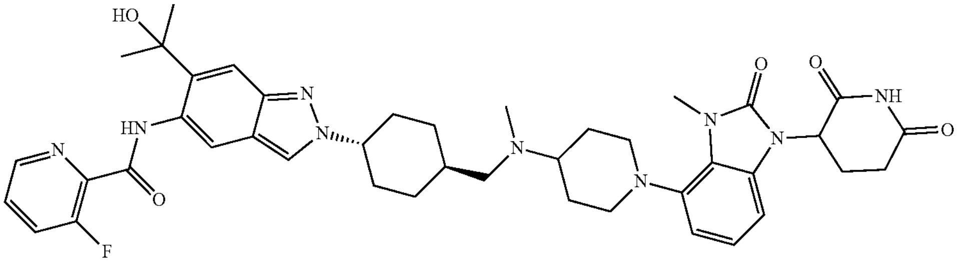 [SMILES: CN(C[C@H]1CC[C@H](n2cc3cc(NC(=O)c4ncccc4F)c(C(C)(C)O)cc3n2)CC1)C1CCN(c2cccc3c2n(C)c(=O)n3C2CCC(=O)NC2=O)CC1] |
| I-363 | 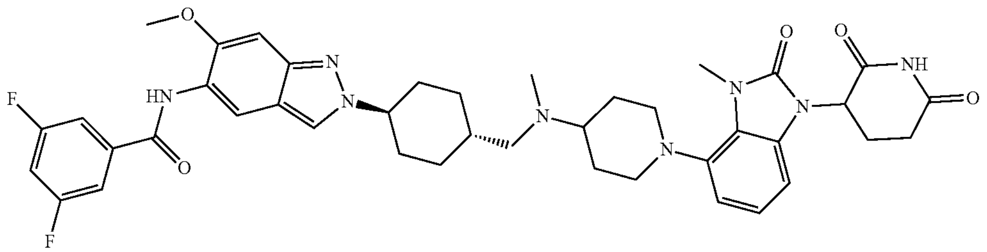 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cc(F)cc(F)c1] |
| I-364 | 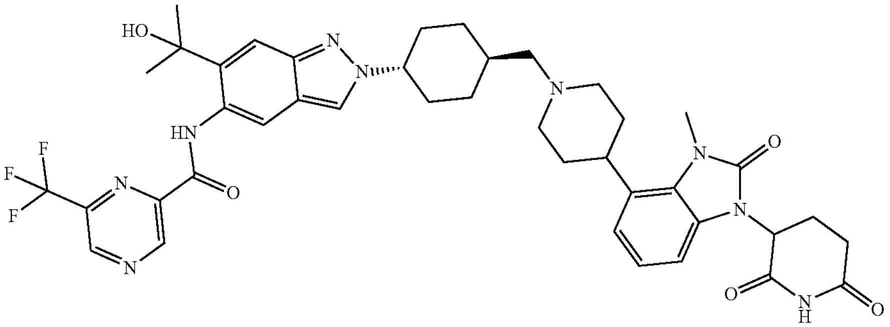 [SMILES: Cn1c(=O)n(C2CCC(=O)NC2=O)c2cccc(C3CCN(C[C@H]4CC[C@H](n5cc6cc(NC(=O)c7cncc(C(F)(F)F)n7)c(C(C)(C)O)cc6n5)CC4)CC3)c21] |
| I-365 | 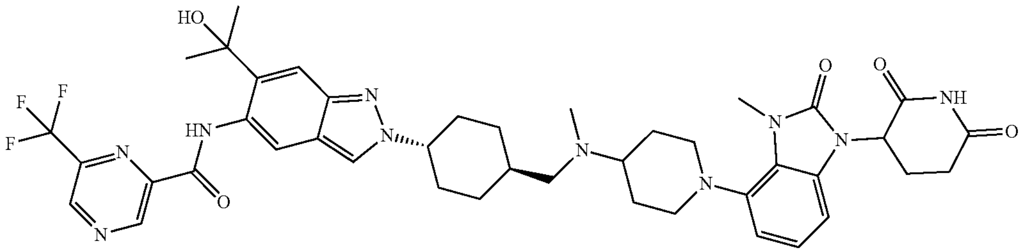 [SMILES: CN(C[C@H]1CC[C@H](n2cc3cc(NC(=O)c4cncc(C(F)(F)F)n4)c(C(C)(C)O)cc3n2)CC1)C1CCN(c2cccc3c2n(C)c(=O)n3C2CCC(=O)NC2=O)CC1] |
| I-366 | 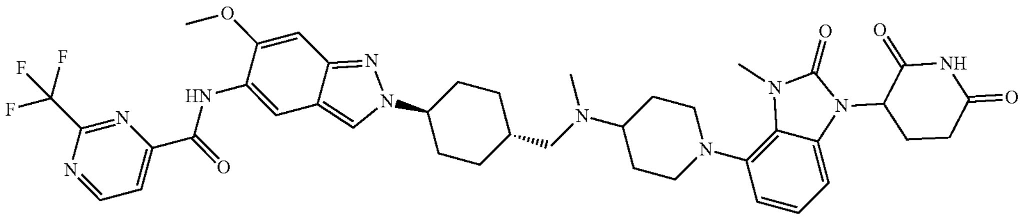 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccnc(C(F)(F)F)n1] |
| I-367 | 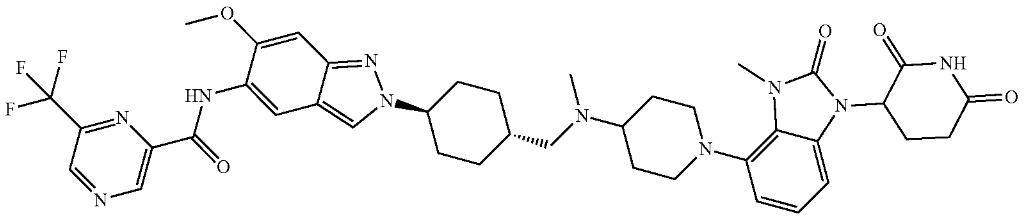 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncc(C(F)(F)F)n1] |

TABLE 1-continued
| Exemplary Compounds | |
| --- | --- |
| I-# | Structure |
| I-368 | 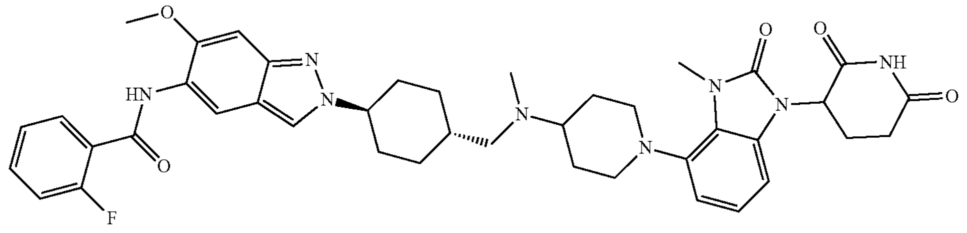 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccccc1F] |
| I-369 | 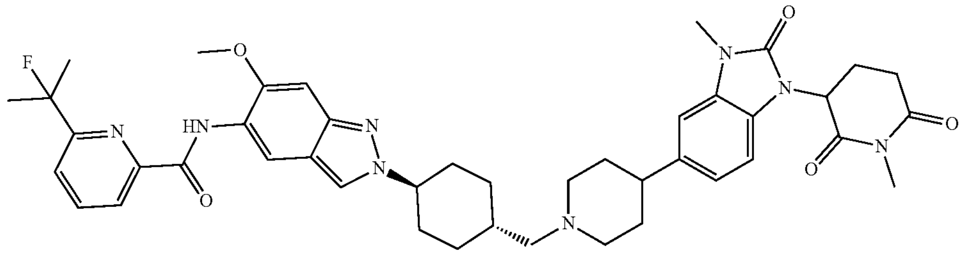 [SMILES: COc1cc2nn([C@H]3CC[C@H](CN4CCC(c5ccc6c(c5)n(C)c(=O)n6C5CCC(=O)N(C)C5=O)CC4)CC3)cc2cc1NC(=O)c1cccc(C(C)(C)F)n1] |
| I-370 | 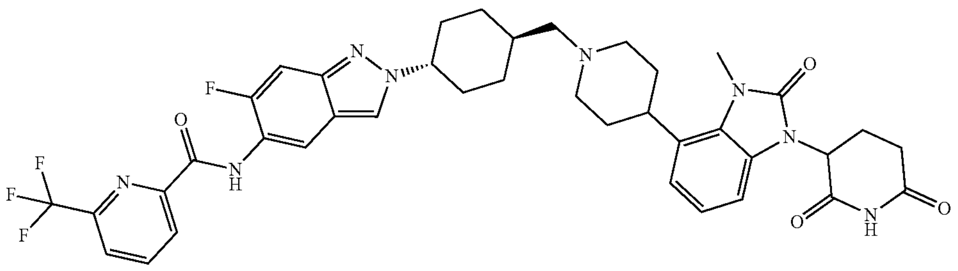 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(F)cc6n5)CC4)CC3)c21] |
| I-371 | 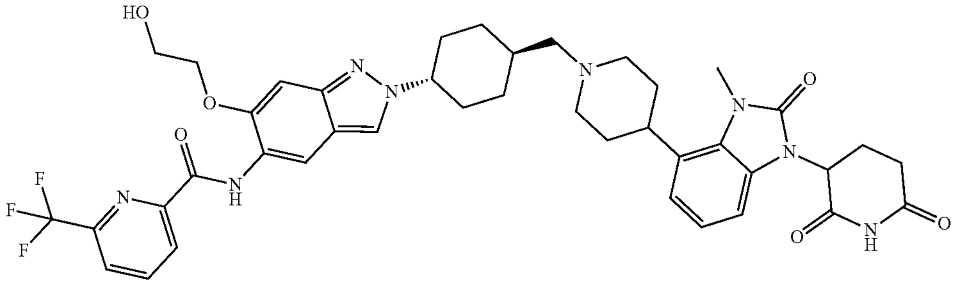 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(OCCO)cc6n5)CC4)CC3)c21] |
| I-372 | 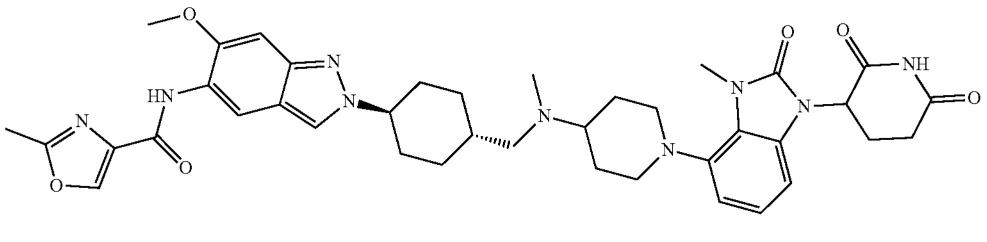 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1coc(C)n1] |

TABLE 1-continued
| Exemplary Compounds | |
|---|---|
| I-# | Structure |
| I-373 | 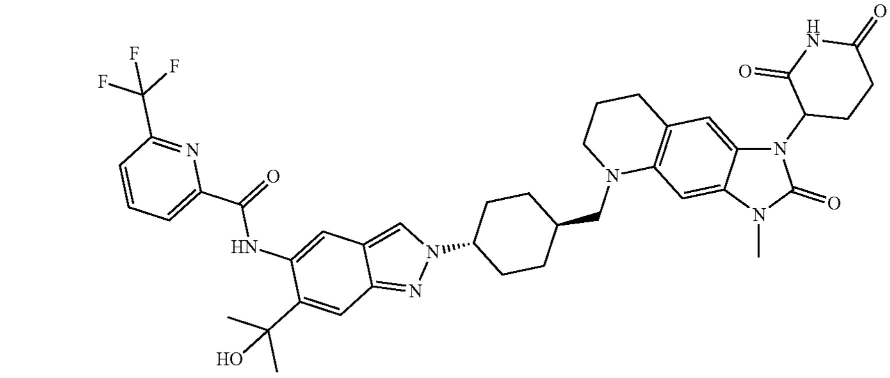 [SMILES: Cn1c(=O)n(C2CCC(=O)NC2=O)c2cc3c(cc21)N(C[C@H]1CC[C@H](n2cc4cc(NC(=O)c5cccc(C(F)(F)F)n5)c(C(C)(C)O)cc4n2)CC1)CCC3] |
| I-374 | 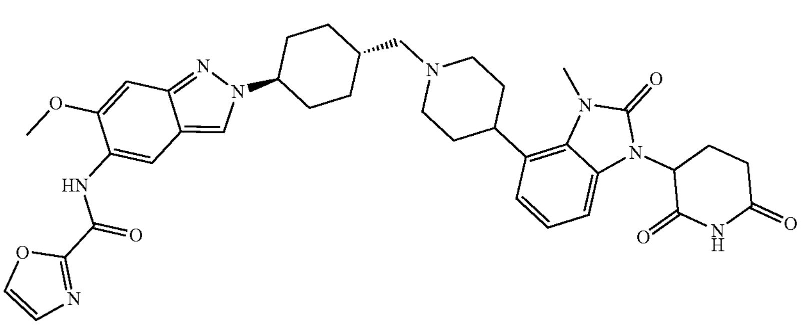 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1ncco1] |
| I-375 | 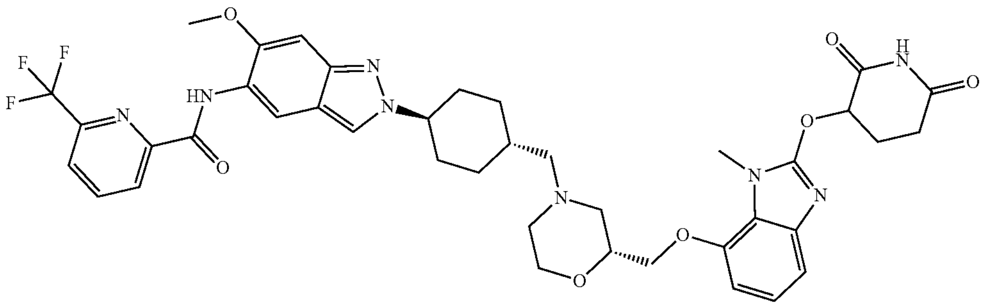 [SMILES: COc1cc2nn([C@H]3CC[C@H](CN4CCO[C@@H](COc5cccc6nc(OC7CCC(=O)NC7=O)n(C)c56)C4)CC3)cc2cc1NC(=O)c1cccc(C(F)(F)F)n1] |
| I-376 | 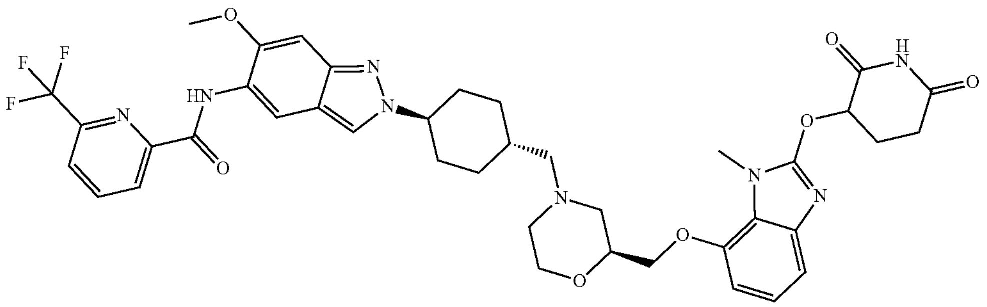 [SMILES: COc1cc2nn([C@H]3CC[C@H](CN4CCO[C@H](COc5cccc6nc(OC7CCC(=O)NC7=O)n(C)c56)C4)CC3)cc2cc1NC(=O)c1cccc(C(F)(F)F)n1] |

TABLE 1-continued
| Exemplary Compounds | |
|---|---|
| I-# | Structure |
| I-377 | 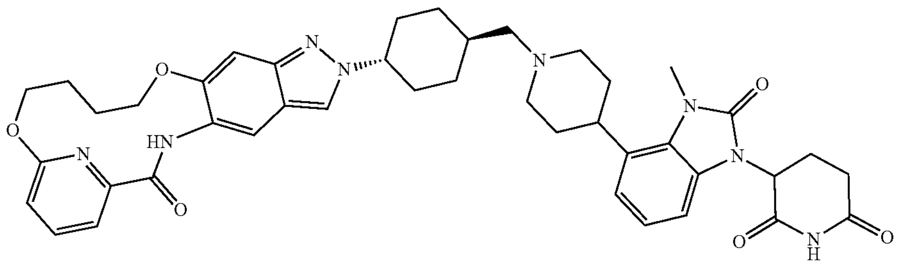 [SMILES: Cn1c(=O)n(C2CCC(=O)NC2=O)c2cccc(C3CCN(C[C@H]4CC[C@H](n5cc6cc7c(cc6n5)OCCCCOc5cccc(n5)C(=O)N7)CC4)CC3)c21] |
| I-378 | 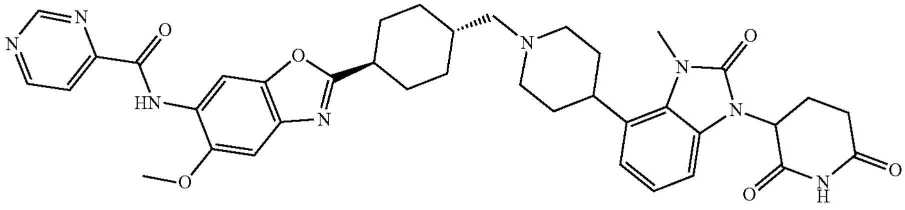 [SMILES: COc1cc2nc([C@H]3CC[C@H](CN4CCC(c5cccc6c5n(C)c(=O)n6C5CCC(=O)NC5=O)CC4)CC3)oc2cc1NC(=O)c1ccncn1] |
| I-379 | 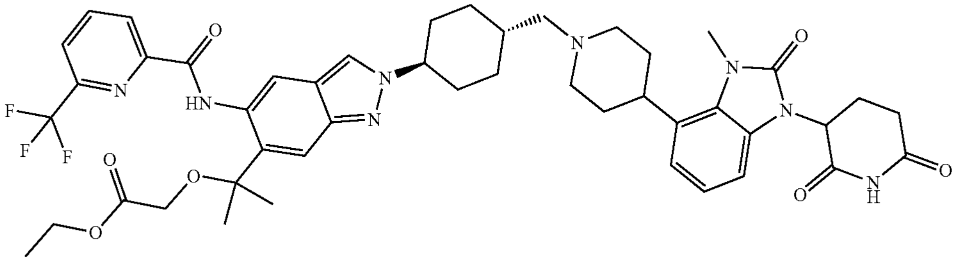 [SMILES: CCOC(=O)COC(C)(C)c1cc2nn([C@H]3CC[C@H](CN4CCC(c5cccc6c5n(C)c(=O)n6C5CCC(=O)NC5=O)CC4)CC3)cc2cc1NC(=O)c1cccc(C(F)(F)F)n1] |
| I-380 | 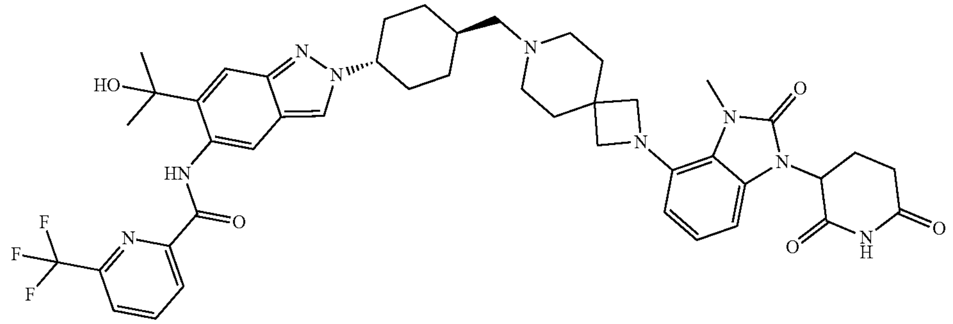 [SMILES: Cn1c(=O)n(C2CCC(=O)NC2=O)c2cccc(N3CC4(CCN(C[C@H]5CC[C@H](n6cc7cc(NC(=O)c8cccc(C(F)(F)F)n8)c(C(C)(C)O)cc7n6)CC5)CC4)C3)c21] |
| I-381 | 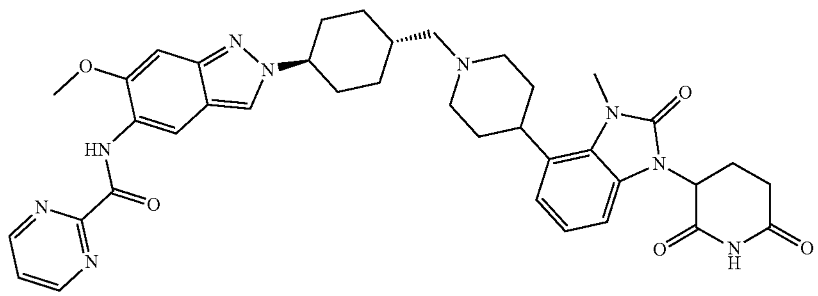 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1ncccn1] |

TABLE 1-continued
| Exemplary Compounds | |
|---|---|
| I-# | Structure |
| I-382 | 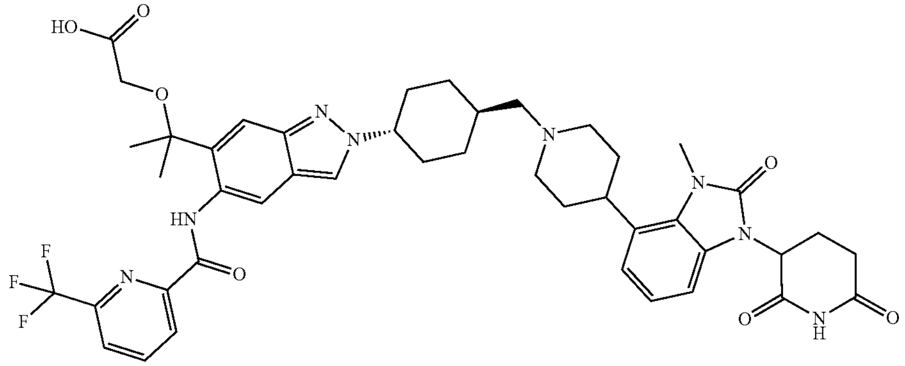 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(C)(C)OCC(=O)O)cc6n5)CC4)CC3)c21] |
| I-383 | 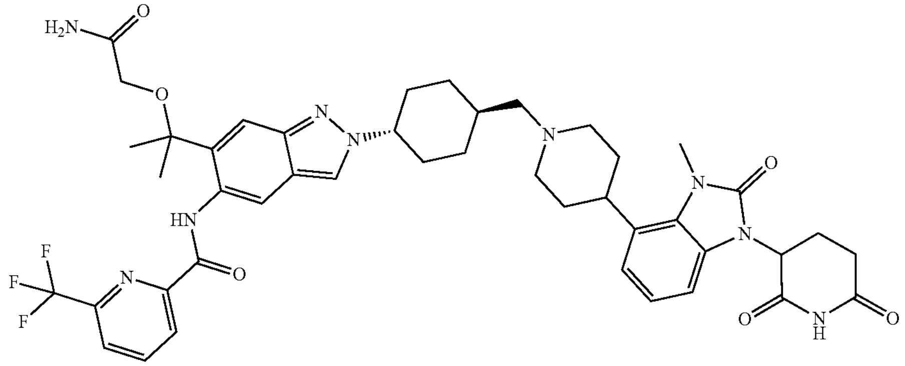 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(C)(C)OCC(N)=O)cc6n5)CC4)CC3)c21] |
| I-384 | 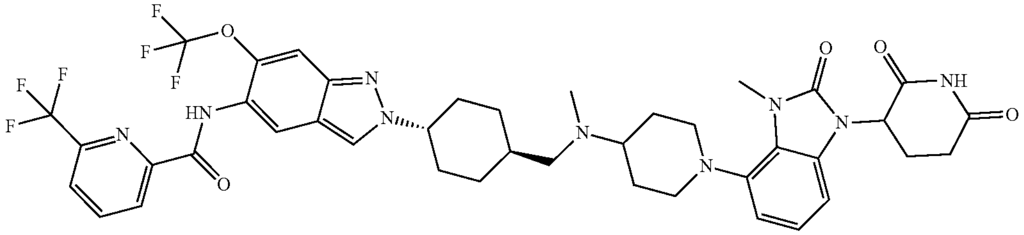 [SMILES: CN(C[C@H]1CC[C@H](n2cc3cc(NC(=O)c4cccc(C(F)(F)F)n4)c(OC(F)(F)F)cc3n2)CC1)C1CCN(c2cccc3c2n(C)c(=O)n3C2CCC(=O)NC2=O)CC1] |
| I-385 | 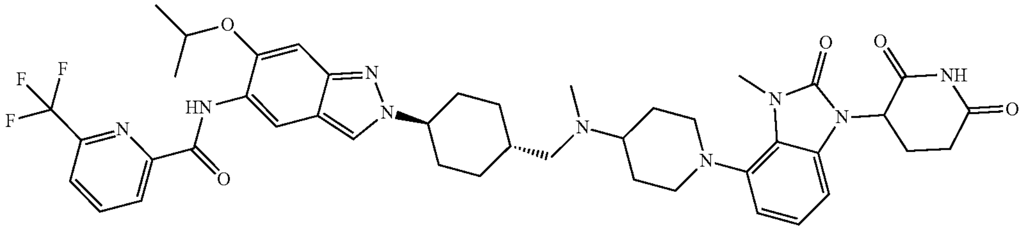 [SMILES: CC(C)Oc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(C(F)(F)F)n1] |
| I-386 | 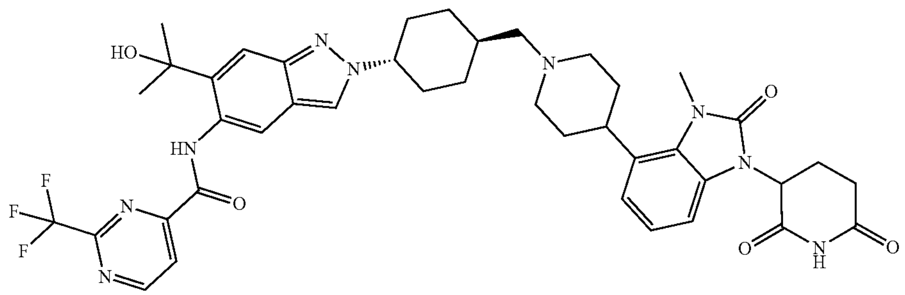 [SMILES: Cn1c(=O)n(C2CCC(=O)NC2=O)c2cccc(C3CCN(C[C@H]4CC[C@H](n5cc6cc(NC(=O)c7ccnc(C(F)(F)F)n7)c(C(C)(C)O)cc6n5)CC4)CC3)c21] |

TABLE 1-continued
| Exemplary Compounds | |
|---|---|
| I-# | Structure |
| I-387 | 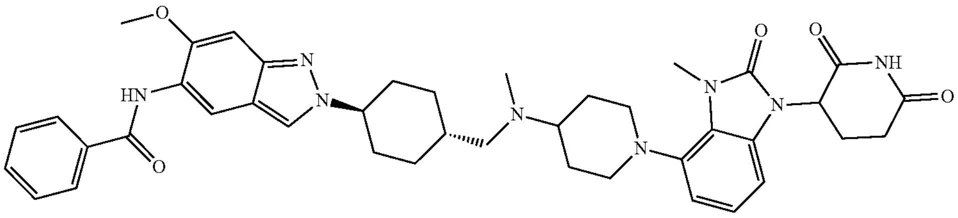 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccccc1] |
| I-388 | 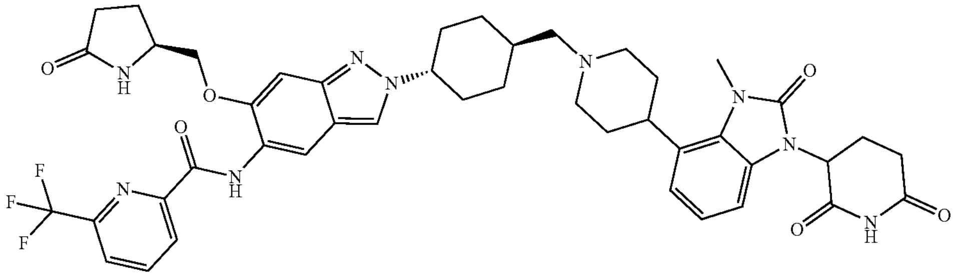 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(OC[C@@H]7CCC(=O)N7)cc6n5)CC4)CC3)c21] |
| I-389 | 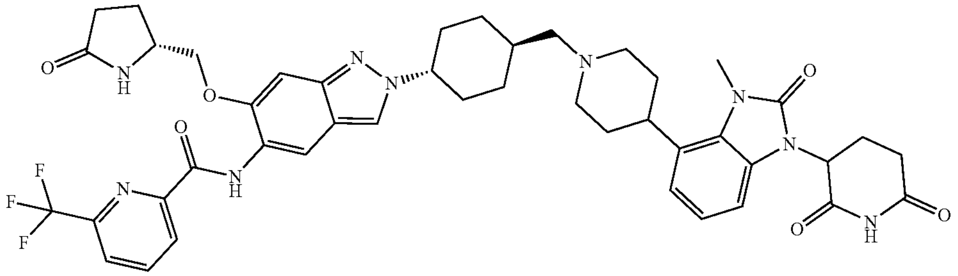 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(OC[C@H]7CCC(=O)N7)cc6n5)CC4)CC3)c21] |
| I-390 | 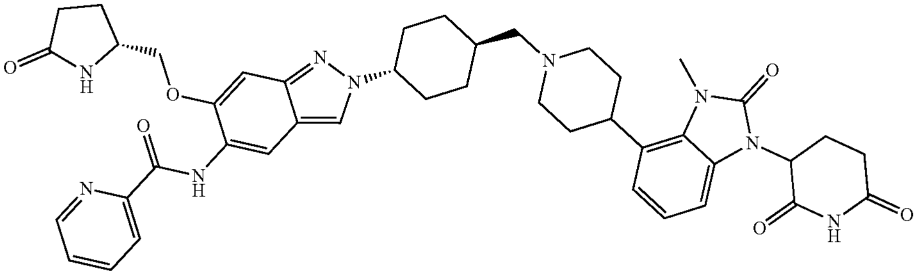 [SMILES: Cn1c(=O)n(C2CCC(=O)NC2=O)c2cccc(C3CCN(C[C@H]4CC[C@H](n5cc6cc(NC(=O)c7ccccn7)c(OC[C@H]7CCC(=O)N7)cc6n5)CC4)CC3)c21] |
| I-391 | 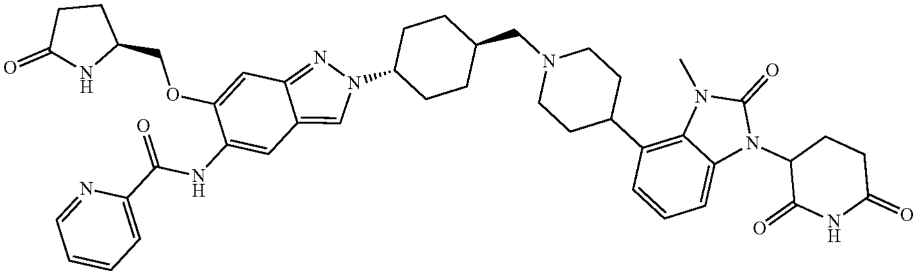 [SMILES: Cn1c(=O)n(C2CCC(=O)NC2=O)c2cccc(C3CCN(C[C@H]4CC[C@H](n5cc6cc(NC(=O)c7ccccn7)c(OC[C@@H]7CCC(=O)N7)cc6n5)CC4)CC3)c21] |
| I-392 | 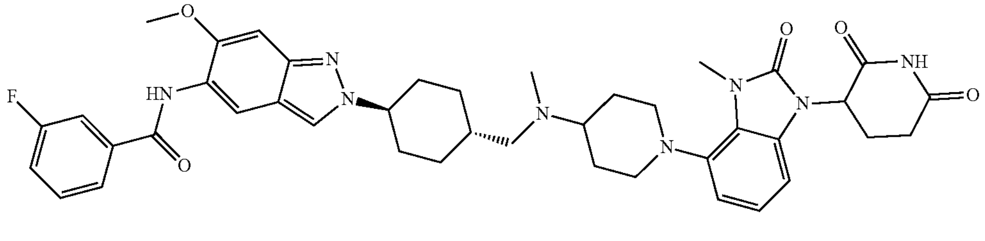 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(F)c1] |

TABLE 1-continued
| Exemplary Compounds | |
|---|---|
| I-# | Structure |
| I-393 | 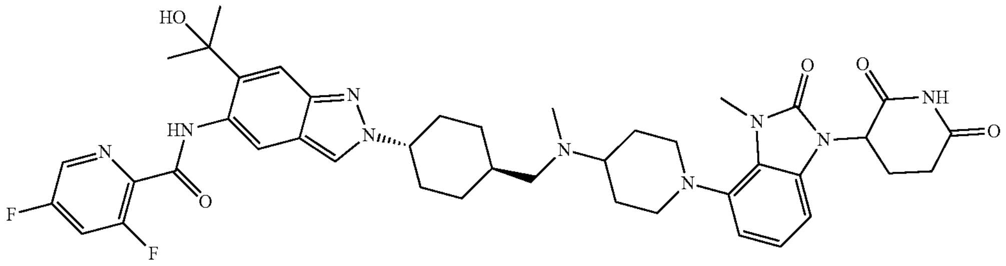 [SMILES: CN(C[C@H]1CC[C@H](n2cc3cc(NC(=O)c4ncc(F)cc4F)c(C(C)(C)O)cc3n2)CC1)C1CCN(c2cccc3c2n(C)c(=O)n3C2CCC(=O)NC2=O)CC1] |
| I-394 | 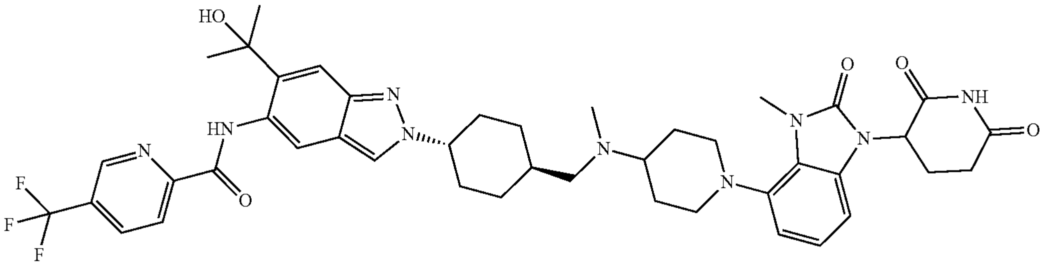 |
| I-395 | 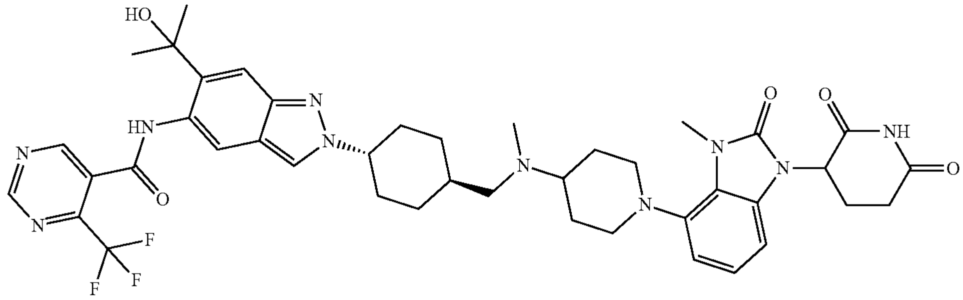 [SMILES: CN(C[C@H]1CC[C@H](n2cc3cc(NC(=O)c4cncnc4C(F)(F)F)c(C(C)(C)O)cc3n2)CC1)C1CCN(c2cccc3c2n(C)c(=O)n3C2CCC(=O)NC2=O)CC1] |
| I-396 | 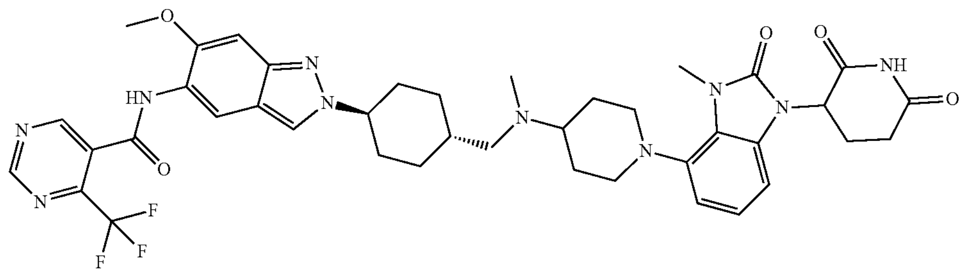 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncnc1C(F)(F)F] |
| I-397 | 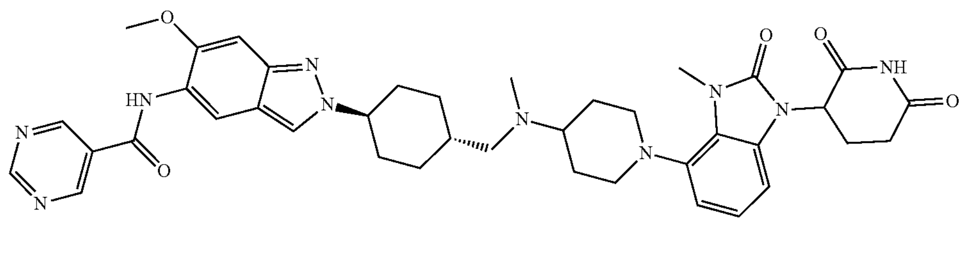 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncnc1] |

TABLE 1-continued
| Exemplary Compounds | |
|---|---|
| I-# | Structure |
| I-398 | 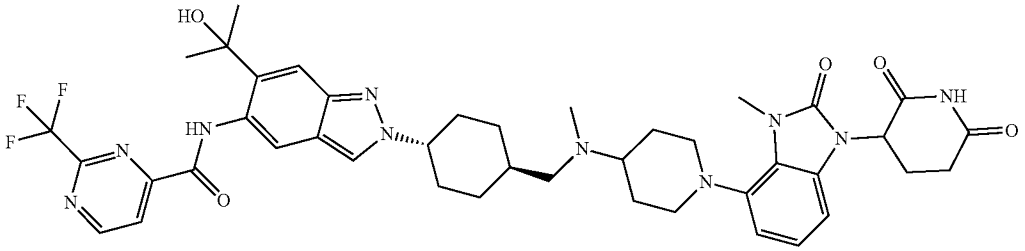 |
| I-399 | 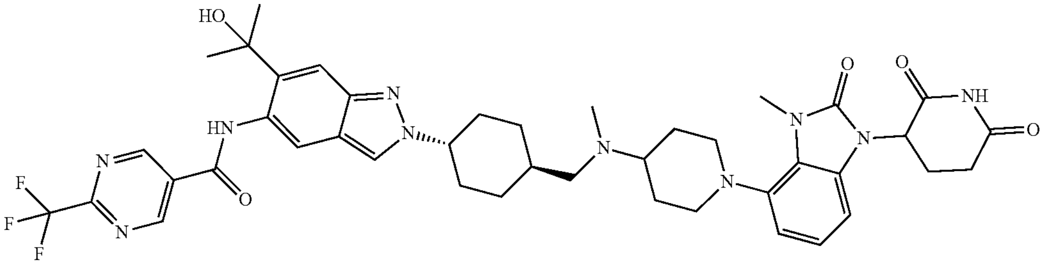 [SMILES: CN(C[C@H]1CC[C@H](n2cc3cc(NC(=O)c4cnc(C(F)(F)F)nc4)c(C(C)(C)O)cc3n2)CC1)C1CCN(c2cccc3c2n(C)c(=O)n3C2CCC(=O)NC2=O)CC1] |
| I-400 | 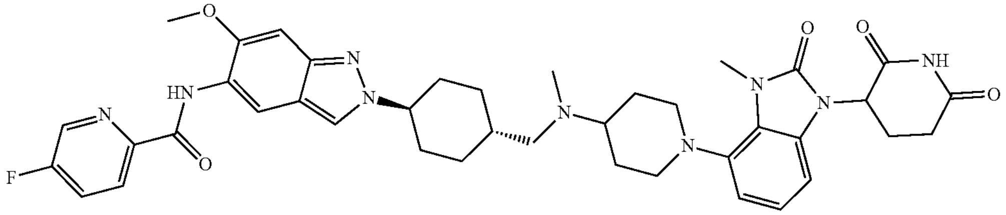 |
| I-401 | 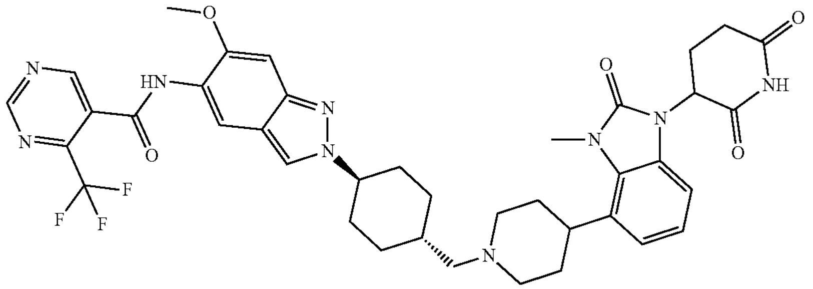 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncnc1C(F)(F)F] |
| I-402 | 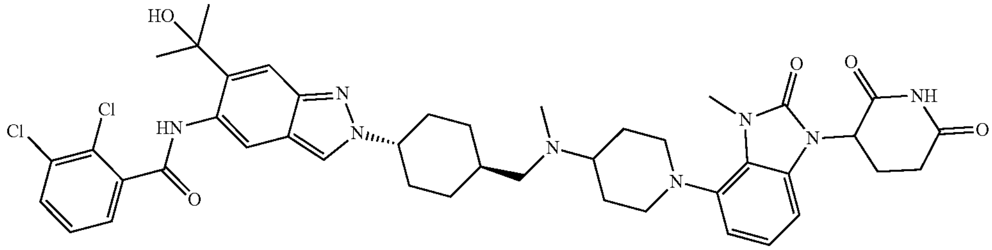 [SMILES: CN(C[C@H]1CC[C@H](n2cc3cc(NC(=O)c4cccc(Cl)c4Cl)c(C(C)(C)O)cc3n2)CC1)C1CCN(c2cccc3c2n(C)c(=O)n3C2CCC(=O)NC2=O)CC1] |
| I-403 | 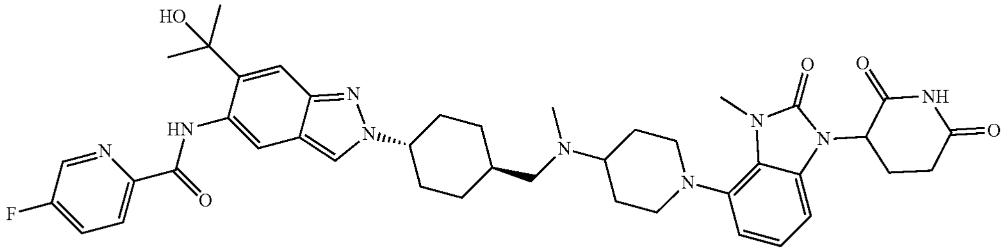 [SMILES: CN(C[C@H]1CC[C@H](n2cc3cc(NC(=O)c4ccc(F)cn4)c(C(C)(C)O)cc3n2)CC1)C1CCN(c2cccc3c2n(C)c(=O)n3C2CCC(=O)NC2=O)CC1] |

TABLE 1-continued
| Exemplary Compounds | |
|---|---|
| I-# | Structure |
| I-404 | 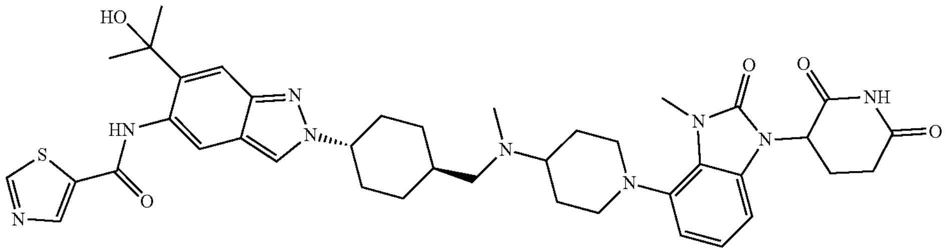 [SMILES: CN(C[C@H]1CC[C@H](n2cc3cc(NC(=O)c4cncs4)c(C(C)(C)O)cc3n2)CC1)C1CCN(c2cccc3c2n(C)c(=O)n3C2CCC(=O)NC2=O)CC1] |
| I-405 | 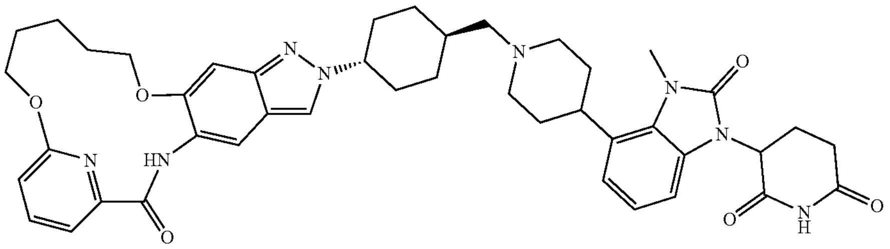 [SMILES: Cn1c(=O)n(C2CCC(=O)NC2=O)c2cccc(C3CCN(C[C@H]4CC[C@H](n5cc6cc7c(cc6n5)OCCCCCOc5cccc(n5)C(=O)N7)CC4)CC3)c21] |
| I-406 | 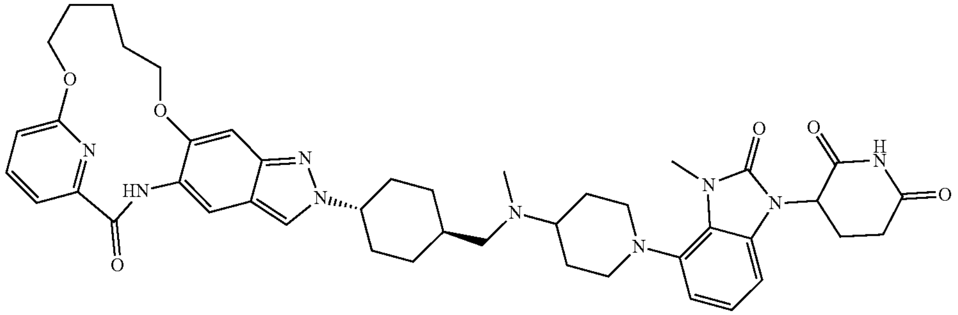 [SMILES: CN(C[C@H]1CC[C@H](n2cc3cc4c(cc3n2)OCCCCCOc2cccc(n2)C(=O)N4)CC1)C1CCN(c2cccc3c2n(C)c(=O)n3C2CCC(=O)NC2=O)CC1] |
| I-407 | 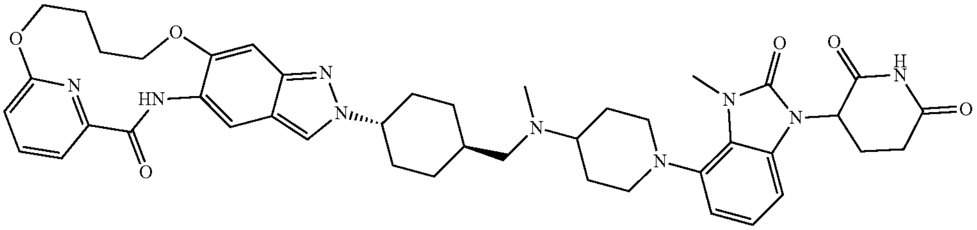 [SMILES: CN(C[C@H]1CC[C@H](n2cc3cc4c(cc3n2)OCCCCOc2cccc(n2)C(=O)N4)CC1)C1CCN(c2cccc3c2n(C)c(=O)n3C2CCC(=O)NC2=O)CC1] |
| I-408 | 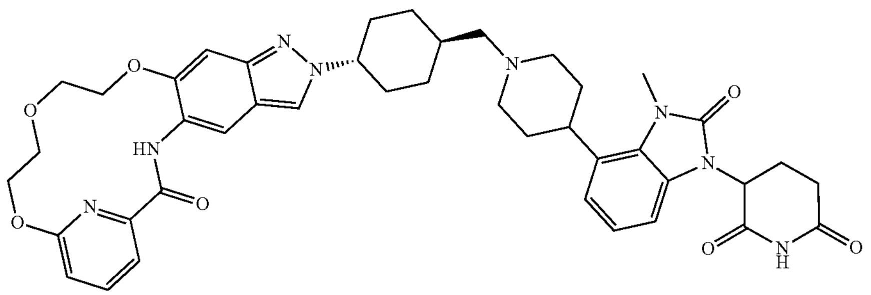 [SMILES: Cn1c(=O)n(C2CCC(=O)NC2=O)c2cccc(C3CCN(C[C@H]4CC[C@H](n5cc6cc7c(cc6n5)OCCOCCOc5cccc(n5)C(=O)N7)CC4)CC3)c21] |

TABLE 1-continued
| Exemplary Compounds | |
|---|---|
| I-# | Structure |
| I-409 | 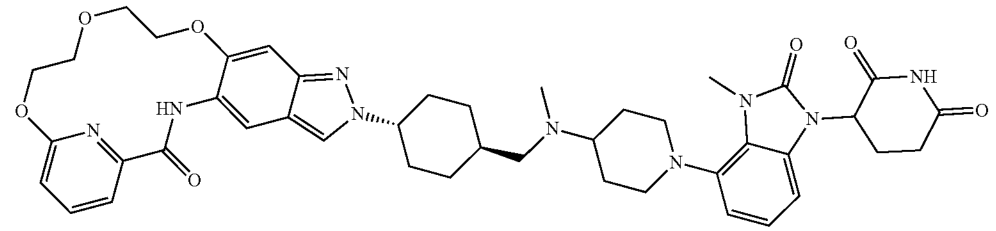 [SMILES: CN(C[C@H]1CC[C@H](n2cc3cc4c(cc3n2)OCCOCCOc2cccc(n2)C(=O)N4)CC1)C1CCN(c2cccc3c2n(C)c(=O)n3C2CCC(=O)NC2=O)CC1] |
| I-410 | 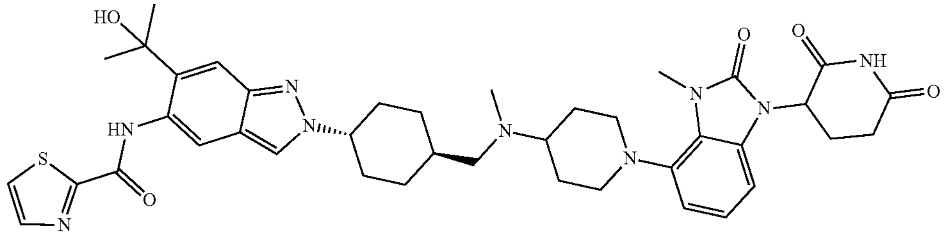 [SMILES: CN(C[C@H]1CC[C@H](n2cc3cc(NC(=O)c4nccs4)c(C(C)(C)O)cc3n2)CC1)C1CCN(c2cccc3c2n(C)c(=O)n3C2CCC(=O)NC2=O)CC1] |
| I-411 | 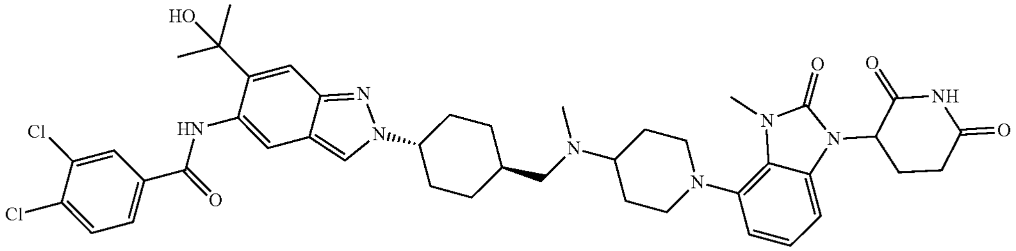 [SMILES: CN(C[C@H]1CC[C@H](n2cc3cc(NC(=O)c4ccc(Cl)c(Cl)c4)c(C(C)(C)O)cc3n2)CC1)C1CCN(c2cccc3c2n(C)c(=O)n3C2CCC(=O)NC2=O)CC1] |
| I-412 | 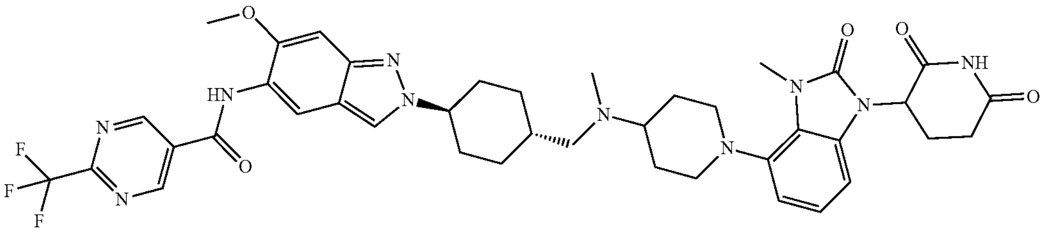 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cnc(C(F)(F)F)nc1] |
| I-413 | 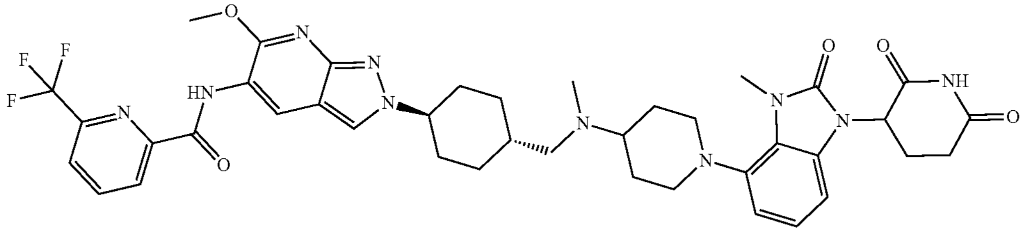 [SMILES: COc1nc2nn([C@H]3CC[C@H](CN(C)C4CCN(c5cccc6c5n(C)c(=O)n6C5CCC(=O)NC5=O)CC4)CC3)cc2cc1NC(=O)c1cccc(C(F)(F)F)n1] |
| I-414 | 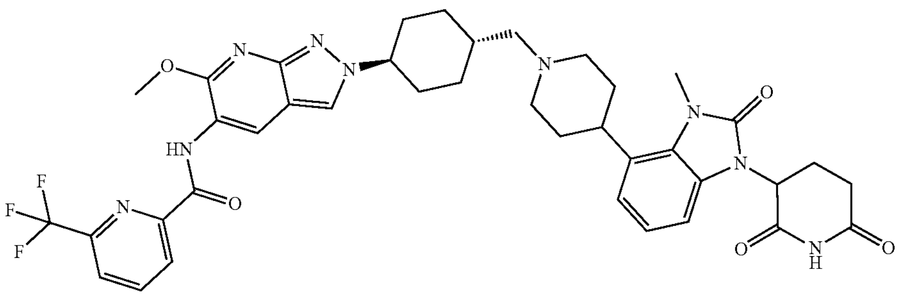 [SMILES: COc1nc2nn([C@H]3CC[C@H](CN4CCC(c5cccc6c5n(C)c(=O)n6C5CCC(=O)NC5=O)CC4)CC3)cc2cc1NC(=O)c1cccc(C(F)(F)F)n1] |

TABLE 1-continued
| Exemplary Compounds | |
|---|---|
| I-# | Structure |
| I-415 | 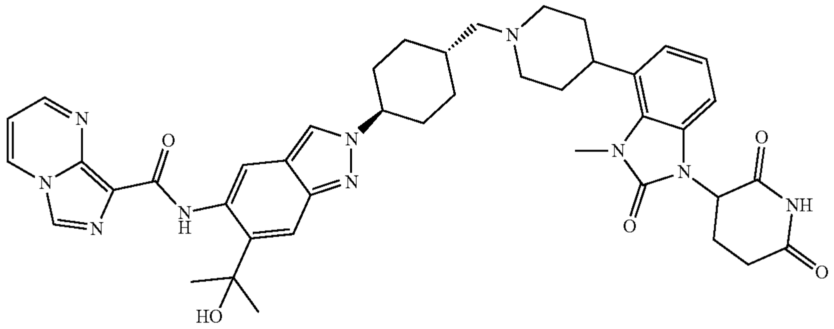 [SMILES: Cn1c(=O)n(C2CCC(=O)NC2=O)c2cccc(C3CCN(C[C@H]4CC[C@H](n5cc6cc(NC(=O)c7ncn8cccnc78)c(C(C)(C)O)cc6n5)CC4)CC3)c21] |
| I-416 | 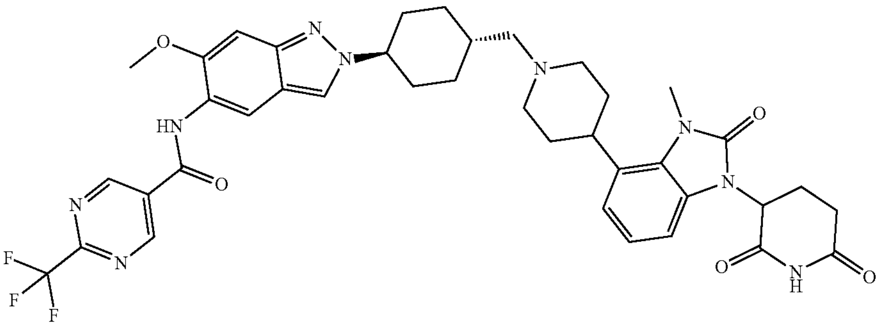 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cnc(C(F)(F)F)nc1] |
| I-417 | 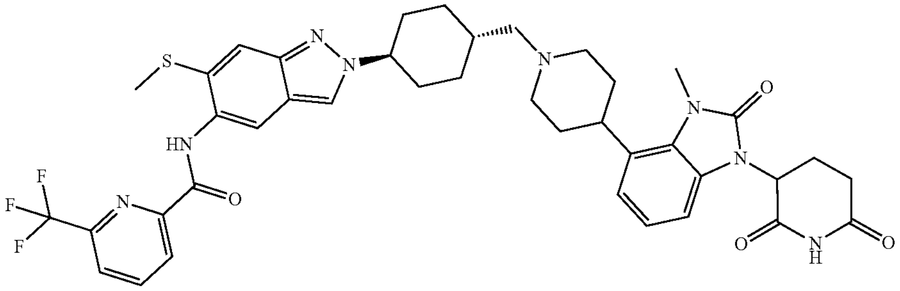 [SMILES: CSc1cc2nn([C@H]3CC[C@H](CN4CCC(c5cccc6c5n(C)c(=O)n6C5CCC(=O)NC5=O)CC4)CC3)cc2cc1NC(=O)c1cccc(C(F)(F)F)n1] |
| I-418 | 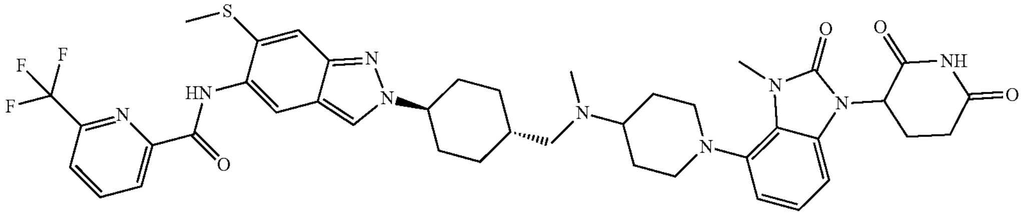 [SMILES: CSc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(C(F)(F)F)n1] |
| I-419 | 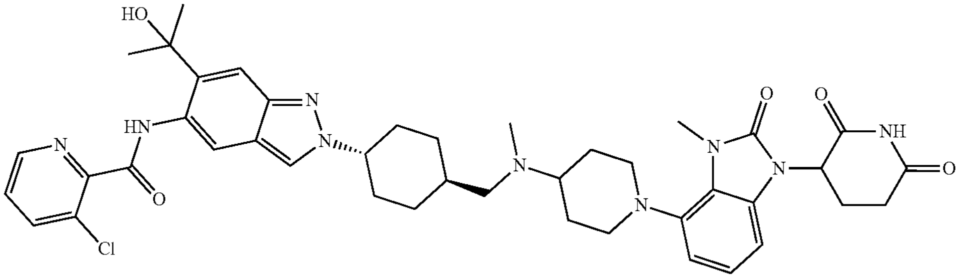 [SMILES: CN(C[C@H]1CC[C@H](n2cc3cc(NC(=O)c4ncccc4Cl)c(C(C)(C)O)cc3n2)CC1)C1CCN(c2cccc3c2n(C)c(=O)n3C2CCC(=O)NC2=O)CC1] |

TABLE 1-continued
| Exemplary Compounds | |
|---|---|
| I-# | Structure |
| I-420 | 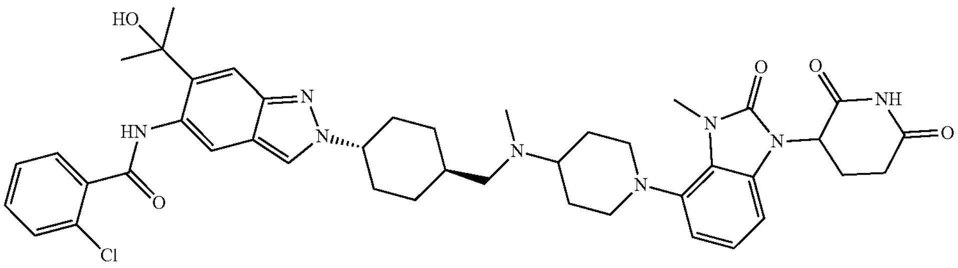 [SMILES: CN(C[C@H]1CC[C@H](n2cc3cc(NC(=O)c4ccccc4Cl)c(C(C)(C)O)cc3n2)CC1)C1CCN(c2cccc3c2n(C)c(=O)n3C2CCC(=O)NC2=O)CC1] |
| I-421 | 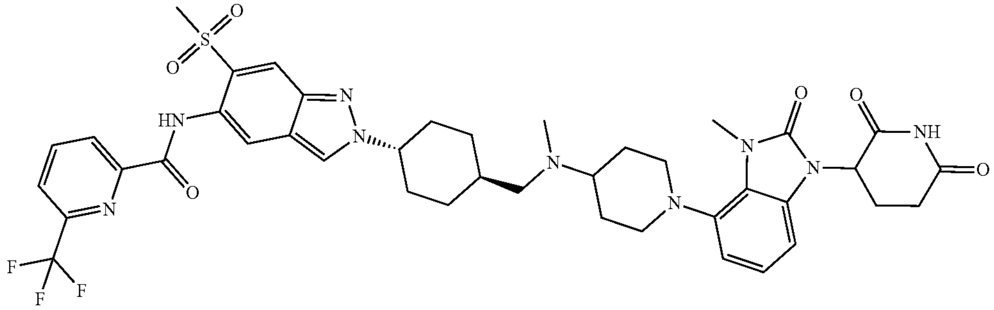 [SMILES: CN(C[C@H]1CC[C@H](n2cc3cc(NC(=O)c4cccc(C(F)(F)F)n4)c(S(C)(=O)=O)cc3n2)CC1)C1CCN(c2cccc3c2n(C)c(=O)n3C2CCC(=O)NC2=O)CC1] |
| I-422 | 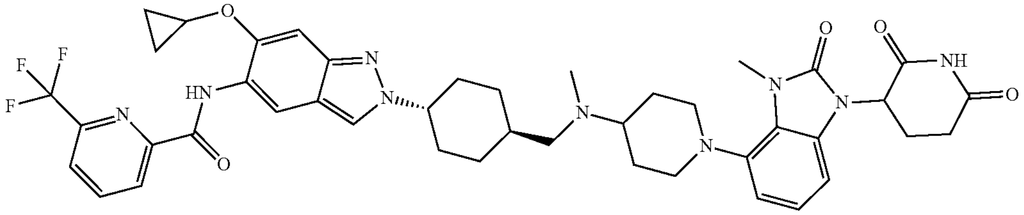 [SMILES: CN(C[C@H]1CC[C@H](n2cc3cc(NC(=O)c4cccc(C(F)(F)F)n4)c(OC4CC4)cc3n2)CC1)C1CCN(c2cccc3c2n(C)c(=O)n3C2CCC(=O)NC2=O)CC1] |
| I-423 | 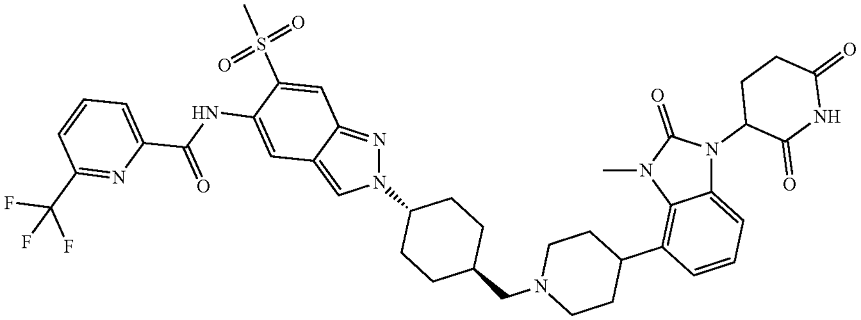 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(S(C)(=O)=O)cc6n5)CC4)CC3)c21] |
| I-424 | 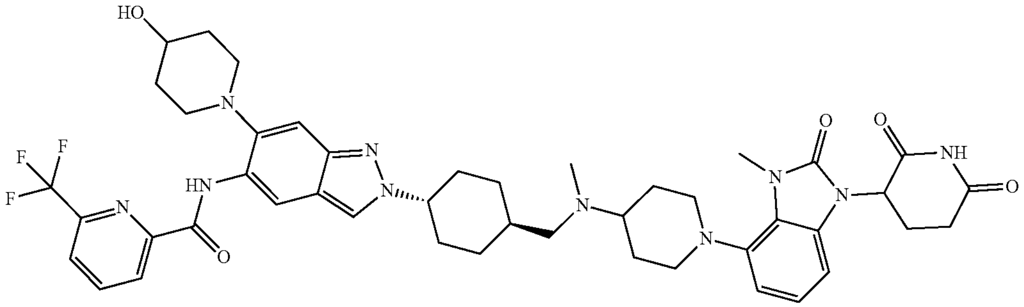 [SMILES: CN(C[C@H]1CC[C@H](n2cc3cc(NC(=O)c4cccc(C(F)(F)F)n4)c(N4CCC(O)CC4)cc3n2)CC1)C1CCN(c2cccc3c2n(C)c(=O)n3C2CCC(=O)NC2=O)CC1] |

TABLE 1-continued
| Exemplary Compounds | |
|---|---|
| I-# | Structure |
| I-425 | 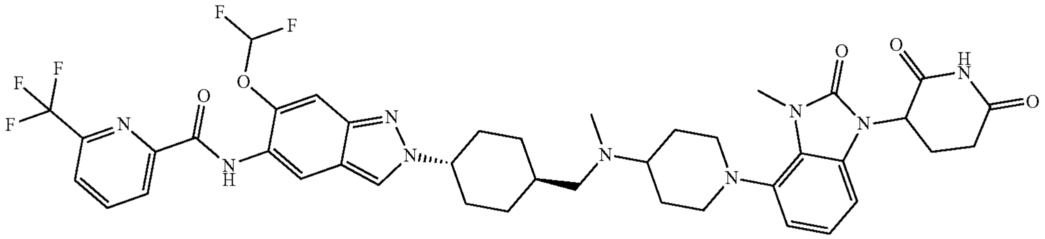 [SMILES: CN(C[C@H]1CC[C@H](n2cc3cc(NC(=O)c4cccc(C(F)(F)F)n4)c(OC(F)F)cc3n2)CC1)C1CCN(c2cccc3c2n(C)c(=O)n3C2CCC(=O)NC2=O)CC1] |
| I-426 | 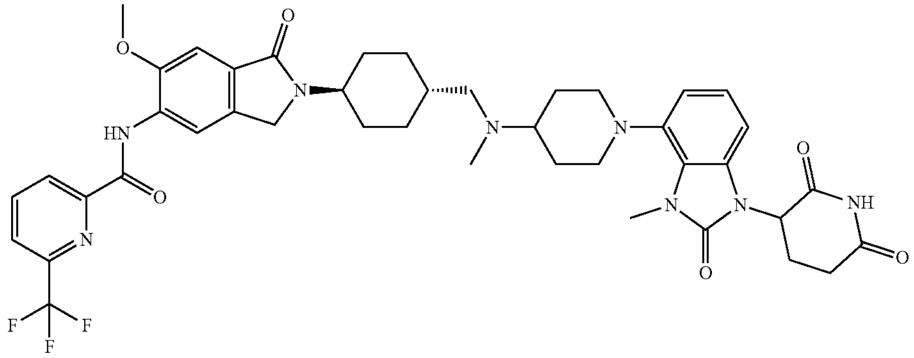 [SMILES: COc1cc2c(cc1NC(=O)c1cccc(C(F)(F)F)n1)CN([C@H]1CC[C@H](CN(C)C3CCN(c4cccc5c4n(C)c(=O)n5C4CCC(=O)NC4=O)CC3)CC1)C2=O] |
| I-427 | 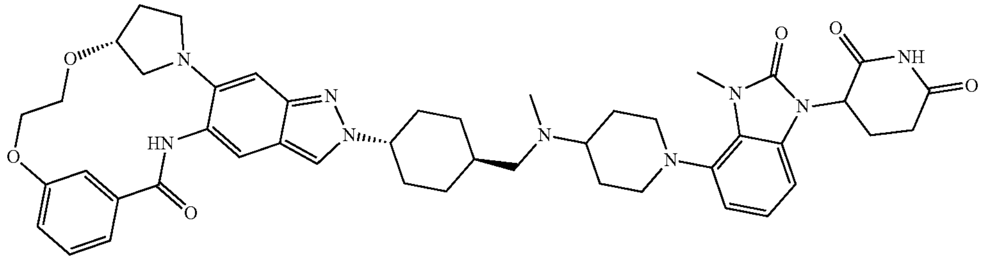 [SMILES: CN(C[C@H]1CC[C@H](n2cc3cc4c(cc3n2)N2CC[C@H](C2)OCCOc2cccc(c2)C(=O)N4)CC1)C1CCN(c2cccc3c2n(C)c(=O)n3C2CCC(=O)NC2=O)CC1] |
| I-428 | 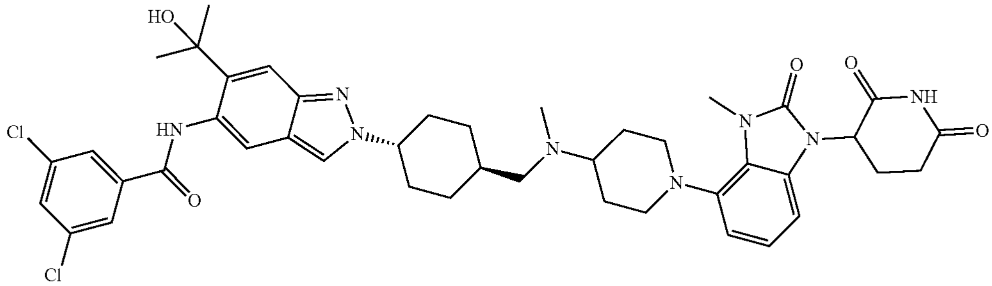 [SMILES: CN(C[C@H]1CC[C@H](n2cc3cc(NC(=O)c4cc(Cl)cc(Cl)c4)c(C(C)(C)O)cc3n2)CC1)C1CCN(c2cccc3c2n(C)c(=O)n3C2CCC(=O)NC2=O)CC1] |
| I-429 | 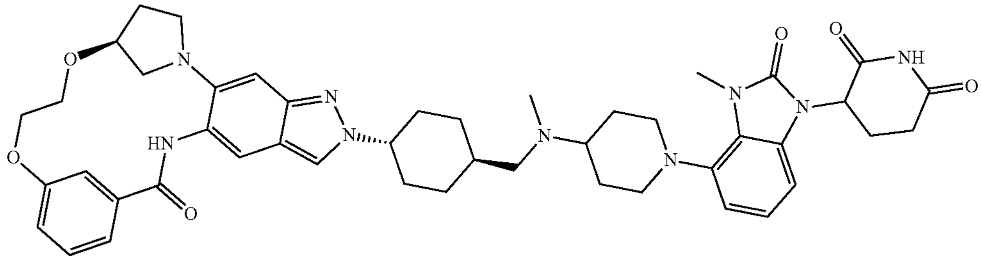 [SMILES: CN(C[C@H]1CC[C@H](n2cc3cc4c(cc3n2)N2CC[C@@H](C2)OCCOc2cccc(c2)C(=O)N4)CC1)C1CCN(c2cccc3c2n(C)c(=O)n3C2CCC(=O)NC2=O)CC1] |

TABLE 1-continued
| Exemplary Compounds | |
|---|---|
| I-# | Structure |
| I-430 | 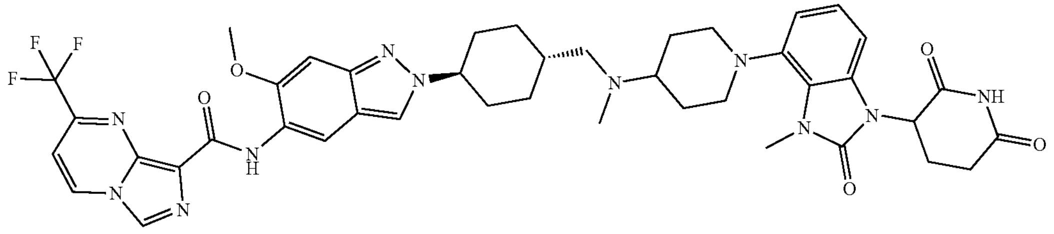 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ncn2ccc(C(F)(F)F)nc12] |
| I-431 | 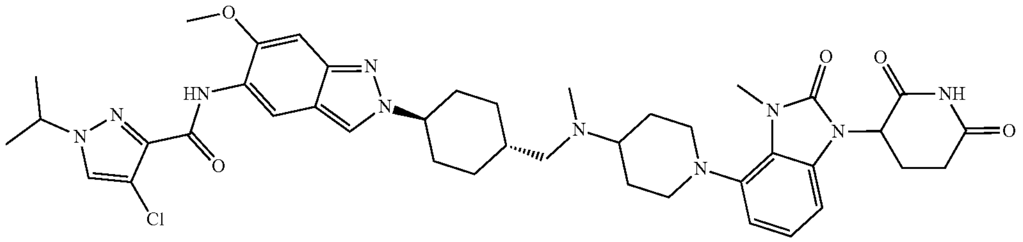 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1nn(C(C)C)cc1Cl] |
| I-432 | 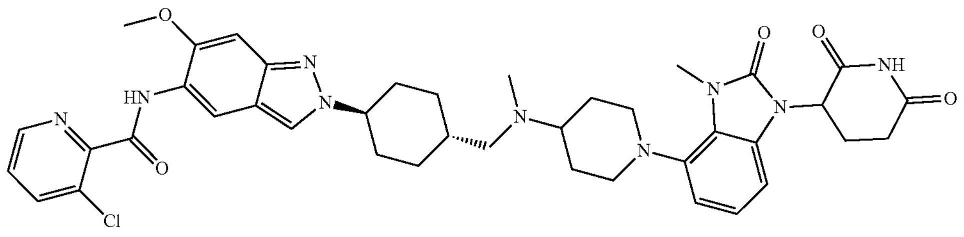 |
| I-433 | 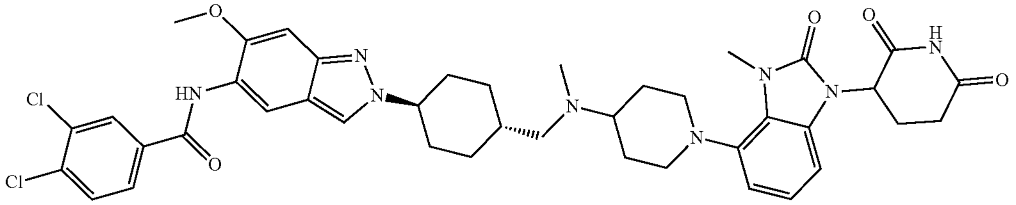 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(Cl)c(Cl)c1] |
| I-434 | 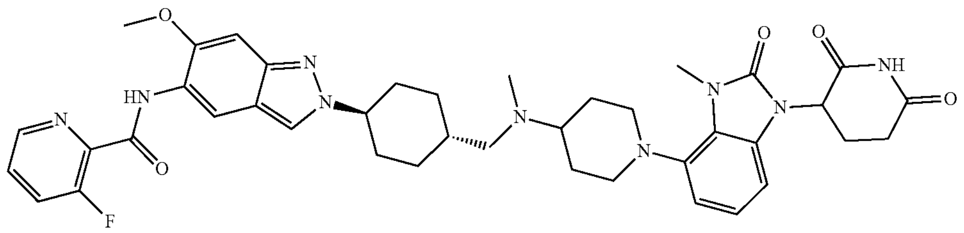 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ncccc1F] |
| I-435 | 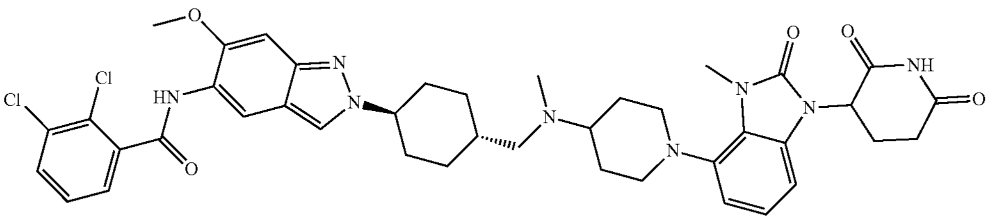 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(Cl)c1Cl] |

TABLE 1-continued
| Exemplary Compounds | |
|---|---|
| I-# | Structure |
| I-436 | 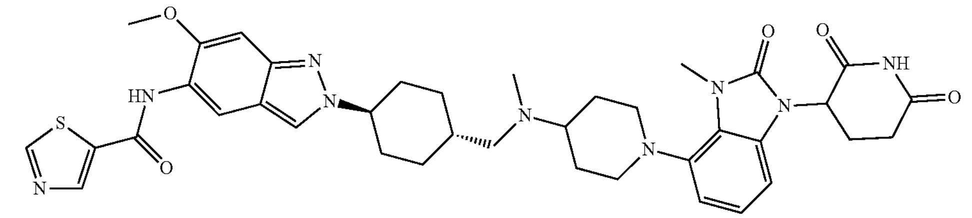 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncs1] |
| I-437 | 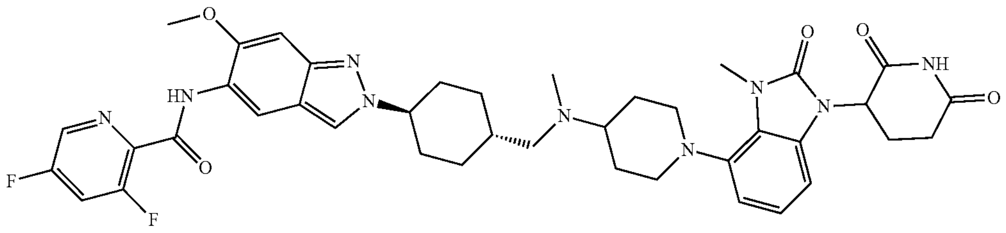 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ncc(F)cc1F] |
| I-438 | 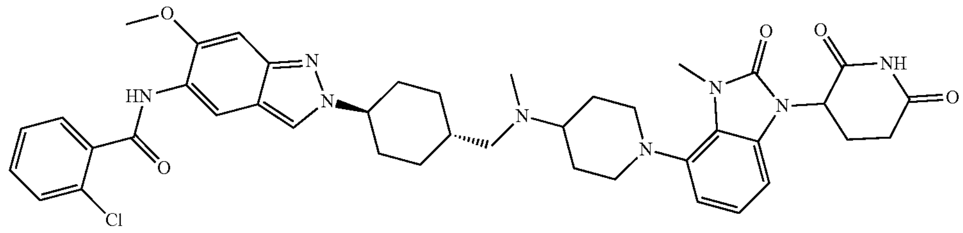 |
| I-439 | 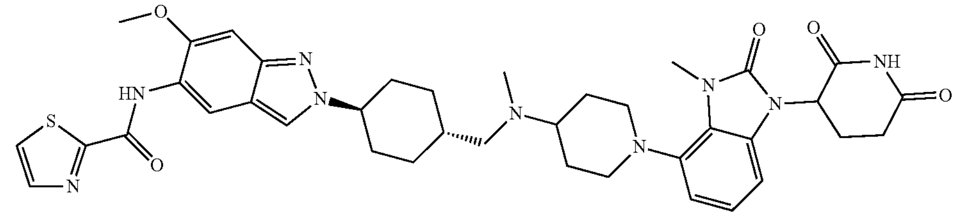 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1nccs1] |
| I-440 | 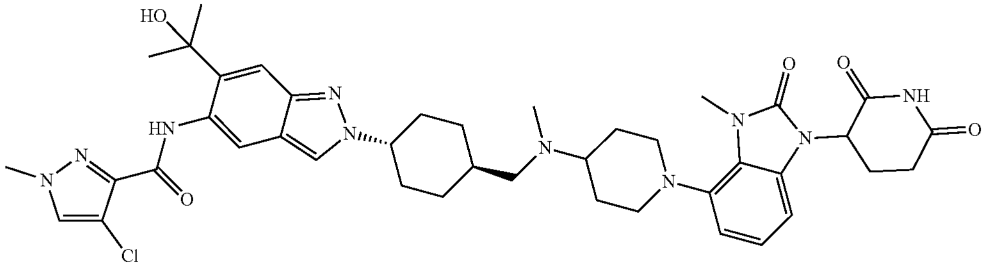 [SMILES: CN(C[C@H]1CC[C@H](n2cc3cc(NC(=O)c4nn(C)cc4Cl)c(C(C)(C)O)cc3n2)CC1)C1CCN(c2cccc3c2n(C)c(=O)n3C2CCC(=O)NC2=O)CC1] |
| I-441 | 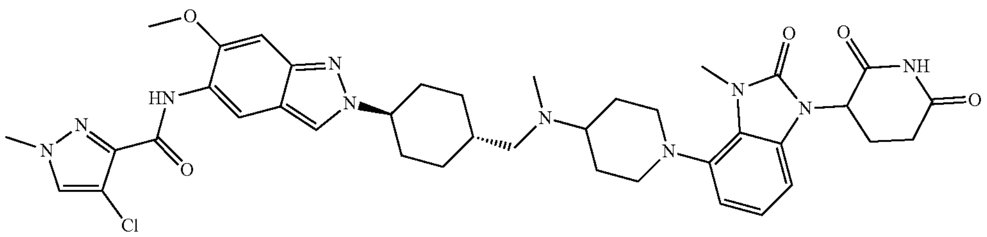 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1nn(C)cc1Cl] |

TABLE 1-continued
| Exemplary Compounds | |
|---|---|
| I-# | Structure |
| I-442 | 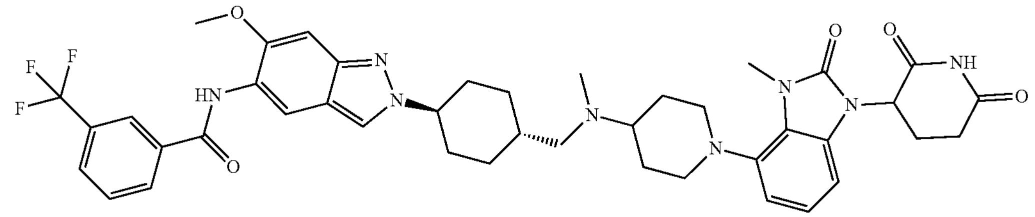 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(C(F)(F)F)c1] |
| I-443 | 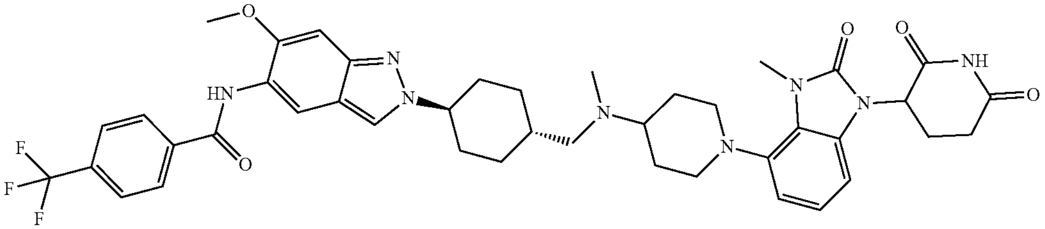 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(C(F)(F)F)cc1] |
| I-444 | 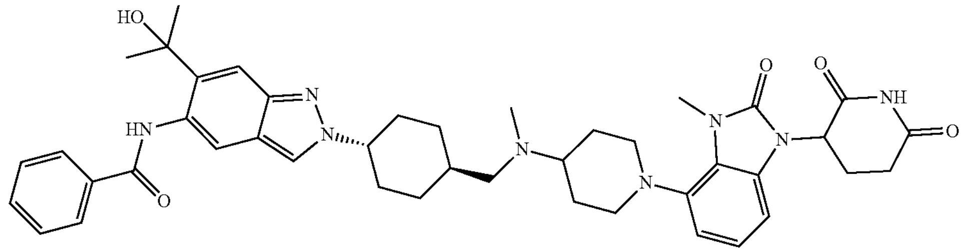 [SMILES: CN(C[C@H]1CC[C@H](n2cc3cc(NC(=O)c4ccccc4)c(C(C)(C)O)cc3n2)CC1)C1CCN(c2cccc3c2n(C)c(=O)n3C2CCC(=O)NC2=O)CC1] |
| I-445 | 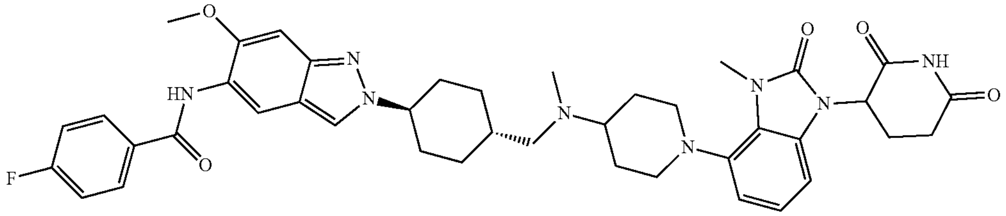 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(F)cc1] |
| I-446 | 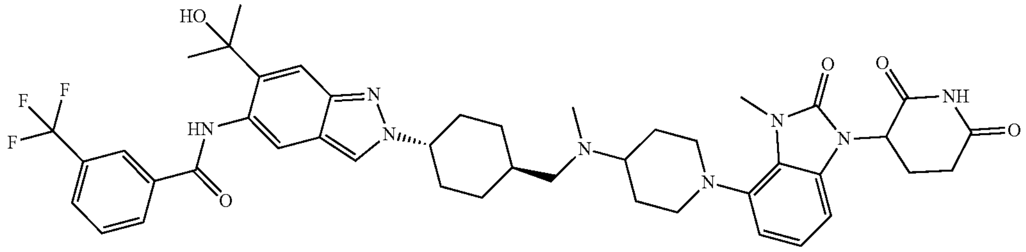 [SMILES: CN(C[C@H]1CC[C@H](n2cc3cc(NC(=O)c4cccc(C(F)(F)F)c4)c(C(C)(C)O)cc3n2)CC1)C1CCN(c2cccc3c2n(C)c(=O)n3C2CCC(=O)NC2=O)CC1] |
| I-447 | 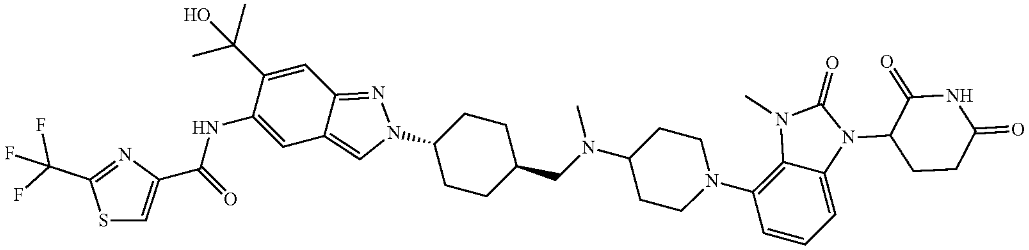 [SMILES: CN(C[C@H]1CC[C@H](n2cc3cc(NC(=O)c4csc(C(F)(F)F)n4)c(C(C)(C)O)cc3n2)CC1)C1CCN(c2cccc3c2n(C)c(=O)n3C2CCC(=O)NC2=O)CC1] |

TABLE 1-continued
| Exemplary Compounds | |
|---|---|
| I-# | Structure |
| I-448 | 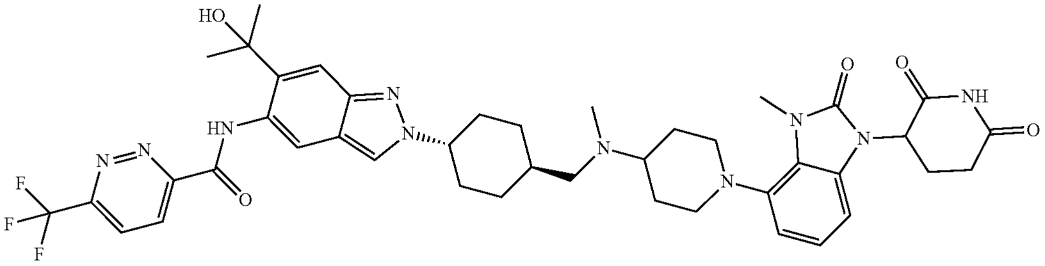 [SMILES: CN(C[C@H]1CC[C@H](n2cc3cc(NC(=O)c4ccc(C(F)(F)F)nn4)c(C(C)(C)O)cc3n2)CC1)C1CCN(c2cccc3c2n(C)c(=O)n3C2CCC(=O)NC2=O)CC1] |
| I-449 | 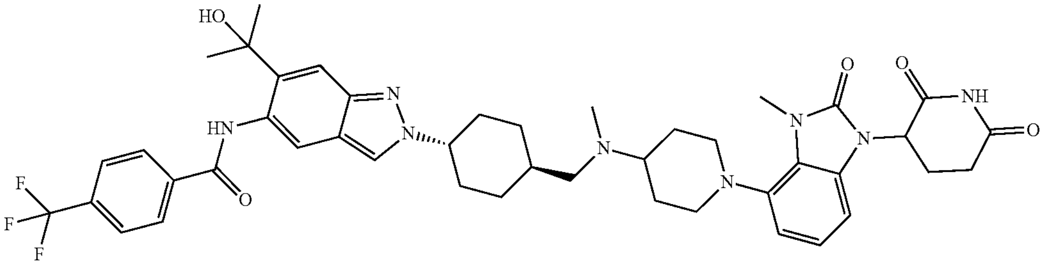 [SMILES: CN(C[C@H]1CC[C@H](n2cc3cc(NC(=O)c4ccc(C(F)(F)F)cc4)c(C(C)(C)O)cc3n2)CC1)C1CCN(c2cccc3c2n(C)c(=O)n3C2CCC(=O)NC2=O)CC1] |
| I-450 | 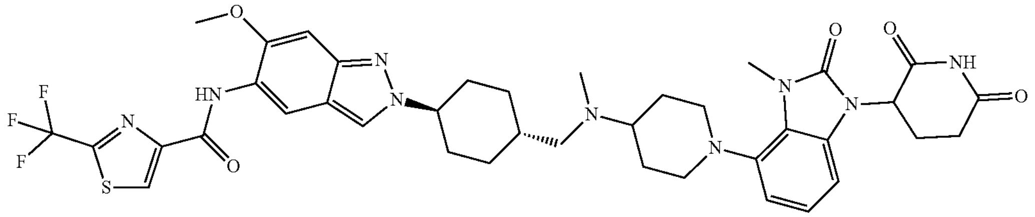 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1csc(C(F)(F)F)n1] |
| I-451 | 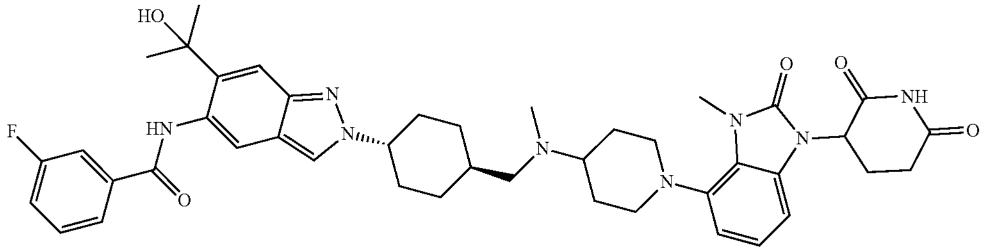 [SMILES: CN(C[C@H]1CC[C@H](n2cc3cc(NC(=O)c4cccc(F)c4)c(C(C)(C)O)cc3n2)CC1)C1CCN(c2cccc3c2n(C)c(=O)n3C2CCC(=O)NC2=O)CC1] |
| I-452 | 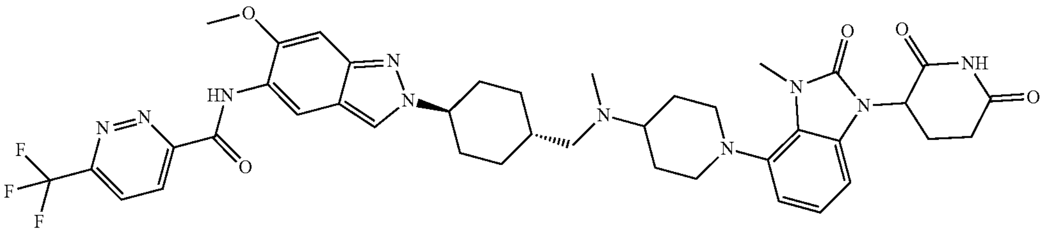 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(C(F)(F)F)nn1] |
| I-453 | 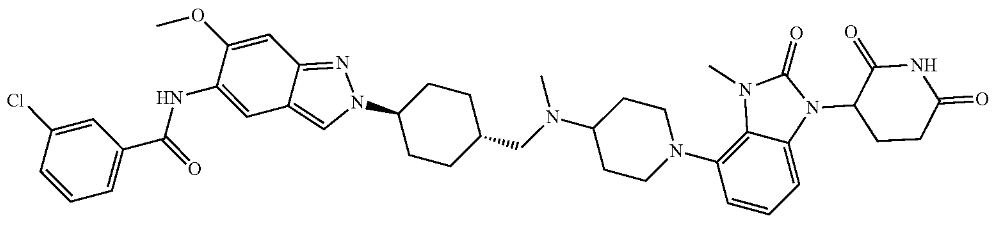 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(Cl)c1] |

TABLE 1-continued
| Exemplary Compounds | |
|---|---|
| I-# | Structure |
| I-454 | 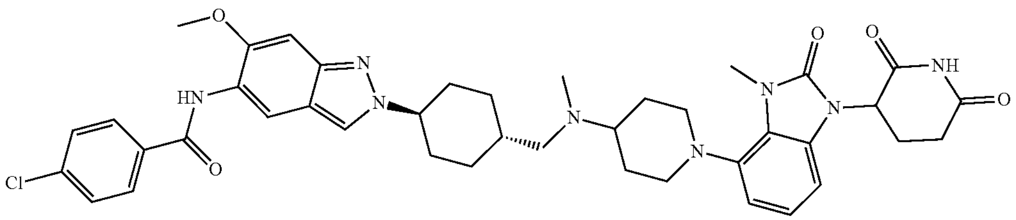 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(Cl)cc1] |
| I-455 | 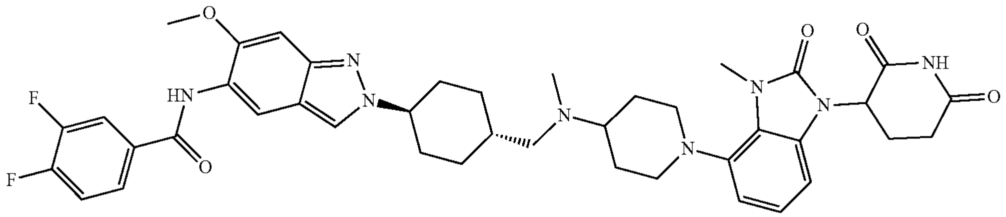 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(F)c(F)c1] |
| I-456 | 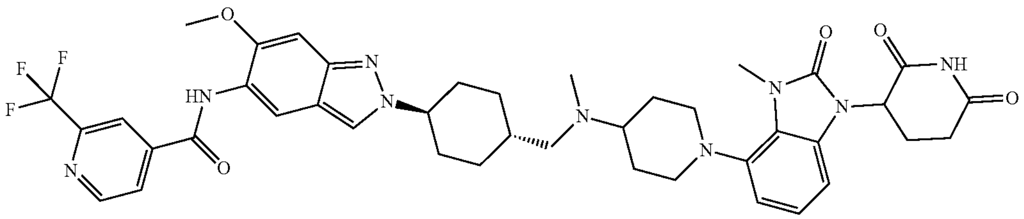 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccnc(C(F)(F)F)c1] |
| I-457 | 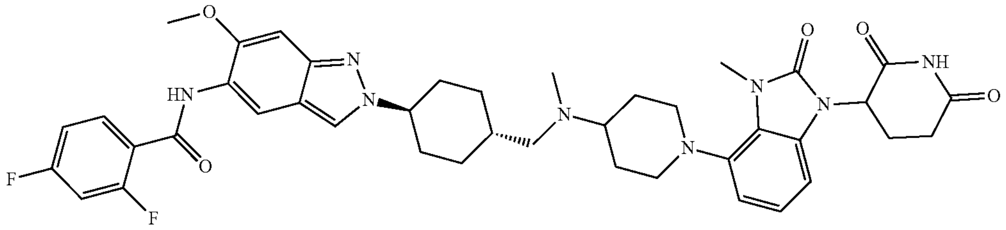 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(F)cc1F] |
| I-458 | 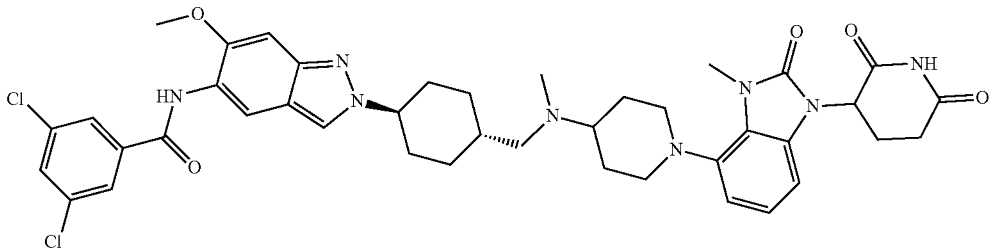 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cc(Cl)cc(Cl)c1] |
| I-459 | 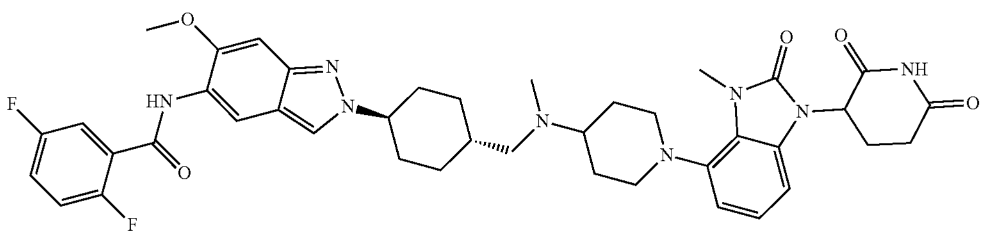 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cc(F)ccc1F] |

TABLE 1-continued
| Exemplary Compounds | |
|---|---|
| I-# | Structure |
| I-460 | 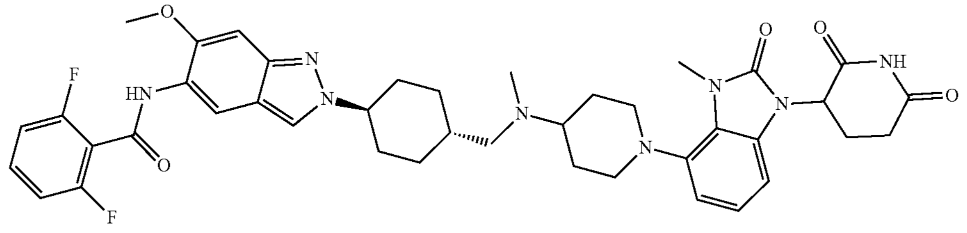 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1c(F)cccc1F] |
| I-461 | 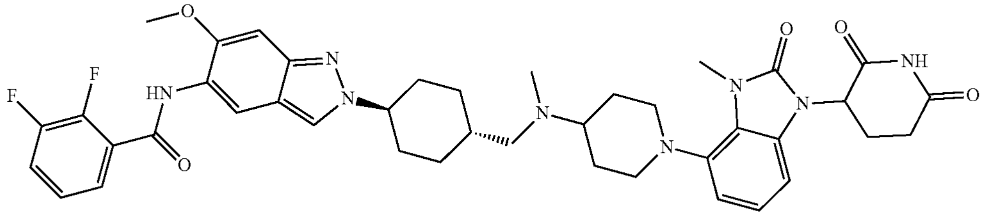 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(F)c1F] |
| I-462 | 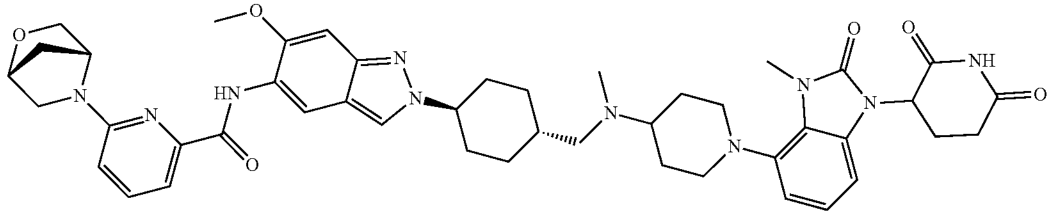 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(N2C[C@H]3C[C@@H]2CO3)n1] |
| I-463 | 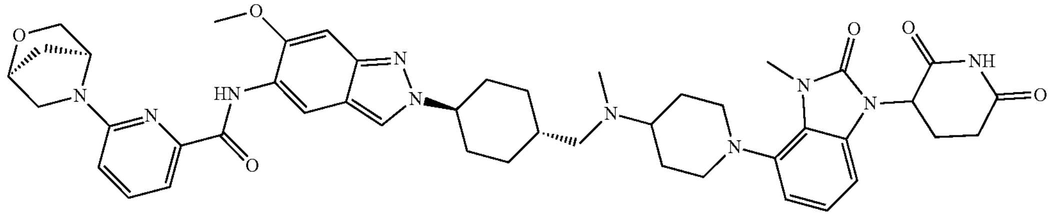 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(N2C[C@@H]3C[C@H]2CO3)n1] |
| I-464 | 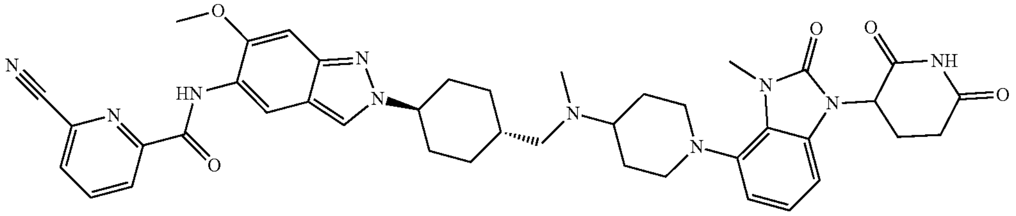 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(C#N)n1] |
| I-465 | 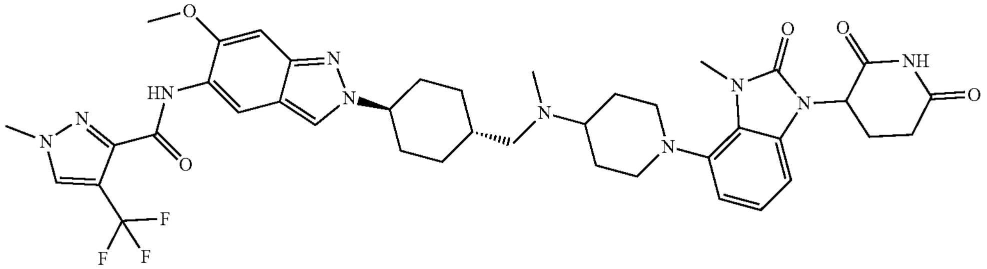 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1nn(C)cc1C(F)(F)F] |

TABLE 1-continued
Exemplary Compounds
| I-# | Structure |
|---|---|
| I-466 | 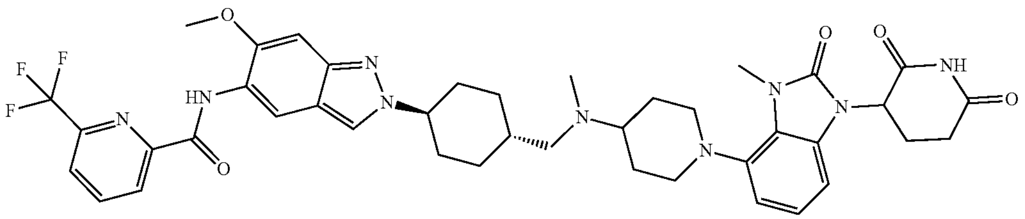 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cccc(C(F)(F)F)n1] |
| I-467 | 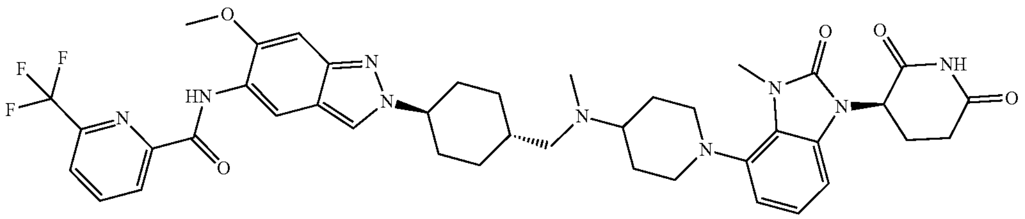 [SMILES: COc1cc2nn([C@H]3CC[C@H](CN(C)C4CCN(c5cccc6c5n(C)c(=O)n6[C@@H]5CCC(=O)NC5=O)CC4)CC3)cc2cc1NC(=O)c1cccc(C(F)(F)F)n1] |
| I-468 | 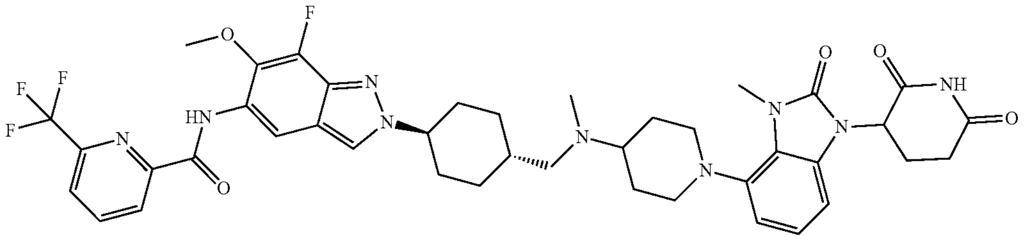 [SMILES: COc1c(NC(=O)c2cccc(C(F)(F)F)n2)cc2cn([C@H]3CC[C@H](CN(C)C4CCN(c5cccc6c5n(C)c(=O)n6C5CCC(=O)NC5=O)CC4)CC3)nc2c1F] |
| I-469 | 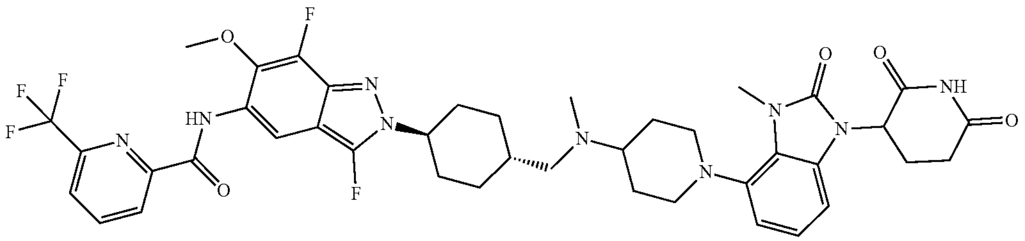 [SMILES: COc1c(NC(=O)c2cccc(C(F)(F)F)n2)cc2c(F)n([C@H]3CC[C@H](CN(C)C4CCN(c5cccc6c5n(C)c(=O)n6C5CCC(=O)NC5=O)CC4)CC3)nc2c1F] |
| I-470 | 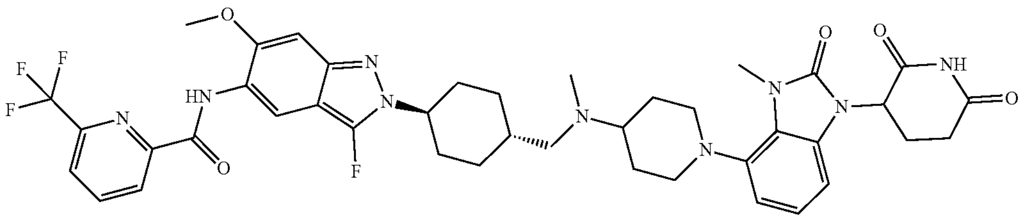 [SMILES: COc1cc2nn([C@H]3CC[C@H](CN(C)C4CCN(c5cccc6c5n(C)c(=O)n6C5CCC(=O)NC5=O)CC4)CC3)c(F)c2cc1NC(=O)c1cccc(C(F)(F)F)n1] |
| I-471 | 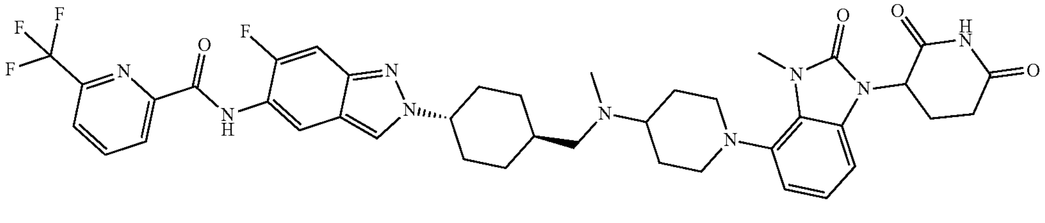 [SMILES: CN(C[C@H]1CC[C@H](n2cc3cc(NC(=O)c4cccc(C(F)(F)F)n4)c(F)cc3n2)CC1)C1CCN(c2cccc3c2n(C)c(=O)n3C2CCC(=O)NC2=O)CC1] |

TABLE 1-continued
| Exemplary Compounds | |
|---|---|
| I-# | Structure |
| I-472 | 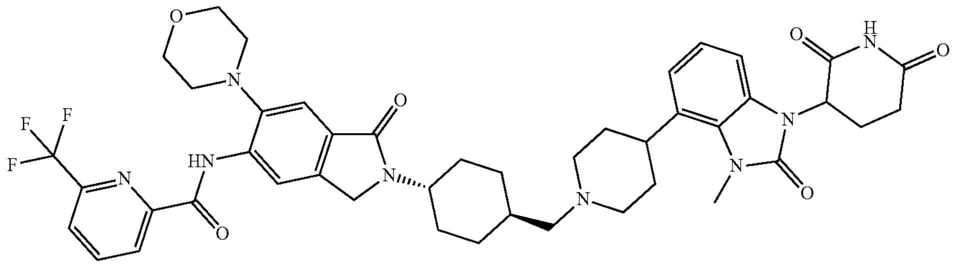 [SMILES: Cn1c(=O)n(C2CCC(=O)NC2=O)c2cccc(C3CCN(C[C@H]4CC[C@H](N5Cc6cc(NC(=O)c7cccc(C(F)(F)F)n7)c(N7CCOCC7)cc6C5=O)CC4)CC3)c21] |
| I-473 | 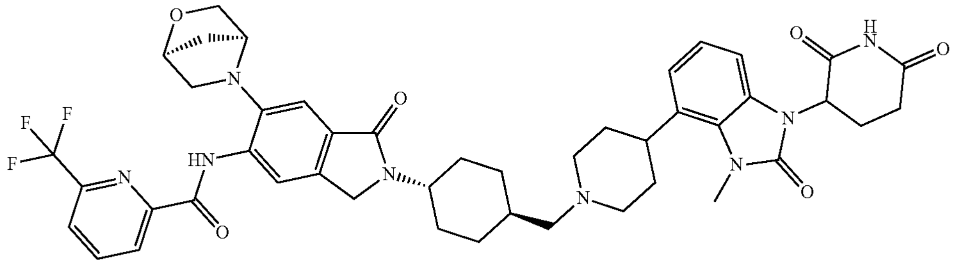 [SMILES: Cn1c(=O)n(C2CCC(=O)NC2=O)c2cccc(C3CCN(C[C@H]4CC[C@H](N5Cc6cc(NC(=O)c7cccc(C(F)(F)F)n7)c(N7C[C@@H]8C[C@H]7CO8)cc6C5=O)CC4)CC3)c21] |
| I-474 | 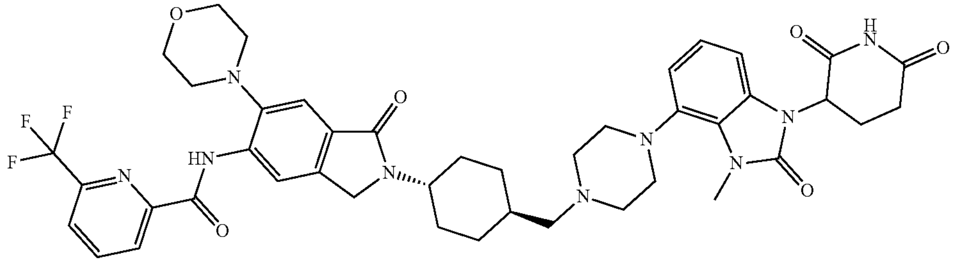 [SMILES: Cn1c(=O)n(C2CCC(=O)NC2=O)c2cccc(N3CCN(C[C@H]4CC[C@H](N5Cc6cc(NC(=O)c7cccc(C(F)(F)F)n7)c(N7CCOCC7)cc6C5=O)CC4)CC3)c21] |
| I-475 | 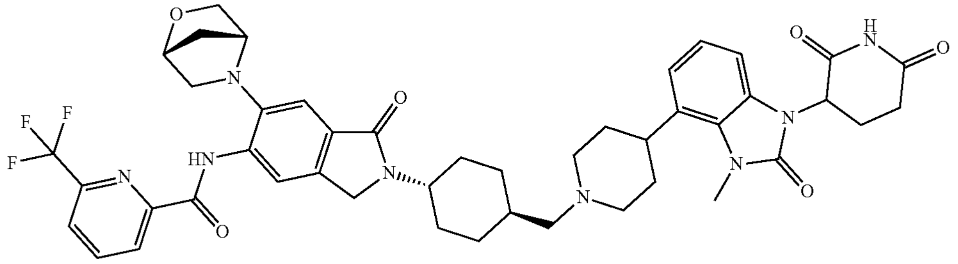 [SMILES: Cn1c(=O)n(C2CCC(=O)NC2=O)c2cccc(C3CCN(C[C@H]4CC[C@H](N5Cc6cc(NC(=O)c7cccc(C(F)(F)F)n7)c(N7C[C@H]8C[C@@H]7CO8)cc6C5=O)CC4)CC3)c21] |
| I-476 | 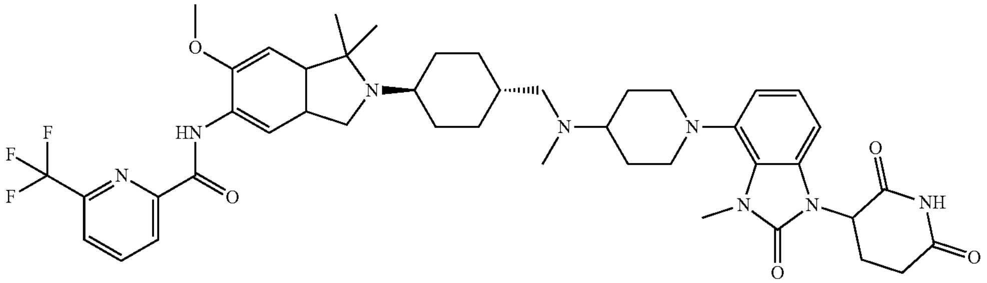 [SMILES: COC1=CC2C(C=C1NC(=O)c1cccc(C(F)(F)F)n1)CN([C@H]1CC[C@H](CN(C)C3CCN(c4cccc5c4n(C)c(=O)n5C4CCC(=O)NC4=O)CC3)CC1)C2(C)C] |

TABLE 1-continued
| Exemplary Compounds | |
|---|---|
| I-# | Structure |
| I-477 | 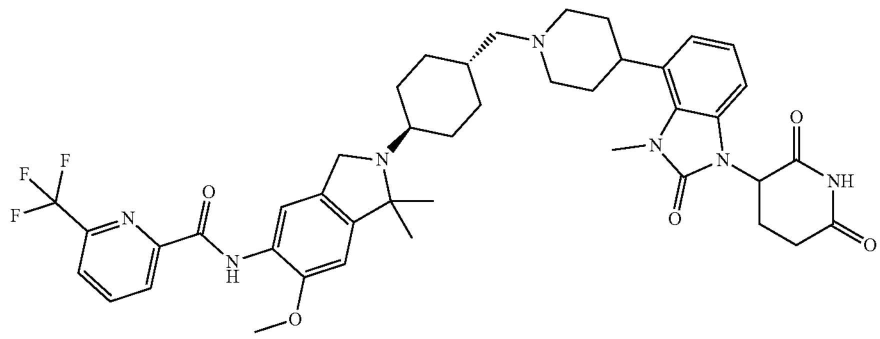 [SMILES: COc1cc2c(cc1NC(=O)c1cccc(C(F)(F)F)n1)CN([C@H]1CC[C@H](CN3CCC(c4cccc5c4n(C)c(=O)n5C4CCC(=O)NC4=O)CC3)CC1)C2(C)C] |
| I-478 | 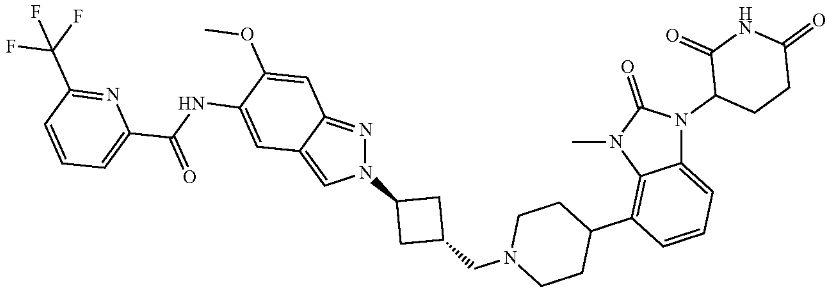 [SMILES: COc1cc2nn([C@H]3C[C@H](CN4CCC(c5cccc6c5n(C)c(=O)n6C5CCC(=O)NC5=O)CC4)C3)cc2cc1NC(=O)c1cccc(C(F)(F)F)n1] |
| I-479 | 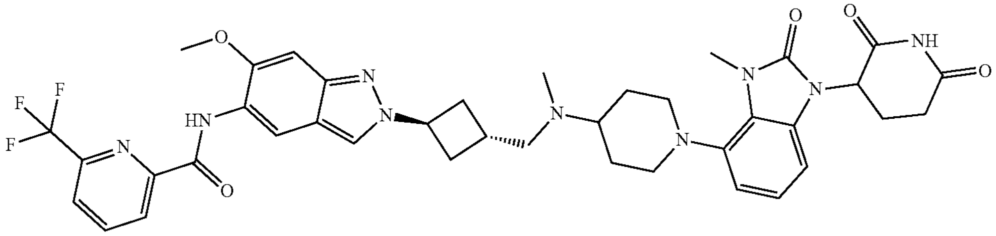 [SMILES: COc1cc2nn([C@H]3C[C@H](CN(C)C4CCN(c5cccc6c5n(C)c(=O)n6C5CCC(=O)NC5=O)CC4)C3)cc2cc1NC(=O)c1cccc(C(F)(F)F)n1] |
| I-480 | 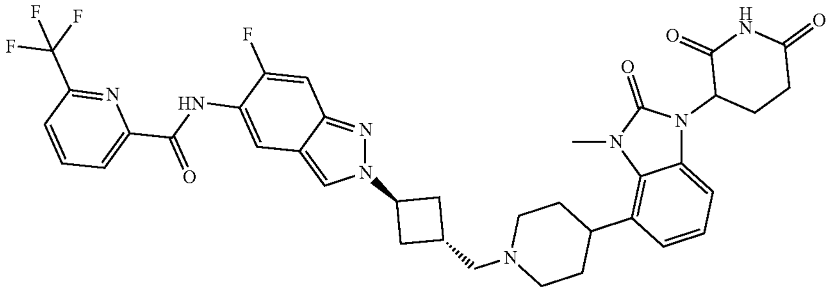 [SMILES: Cn1c(=O)n(C2CCC(=O)NC2=O)c2cccc(C3CCN(C[C@H]4C[C@H](n5cc6cc(NC(=O)c7cccc(C(F)(F)F)n7)c(F)cc6n5)C4)CC3)c21] |
| I-481 | 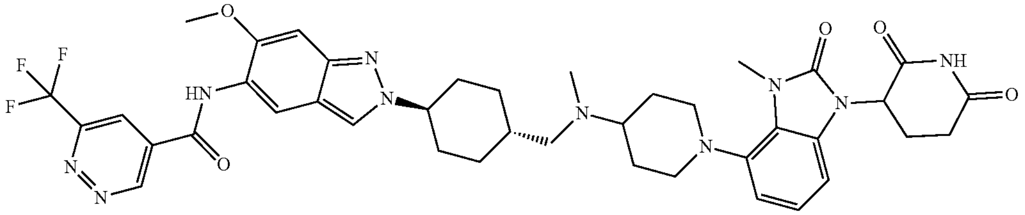 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cnnc(C(F)(F)F)c1] |

TABLE 1-continued
| Exemplary Compounds | |
|---|---|
| I-# | Structure |
| I-482 | 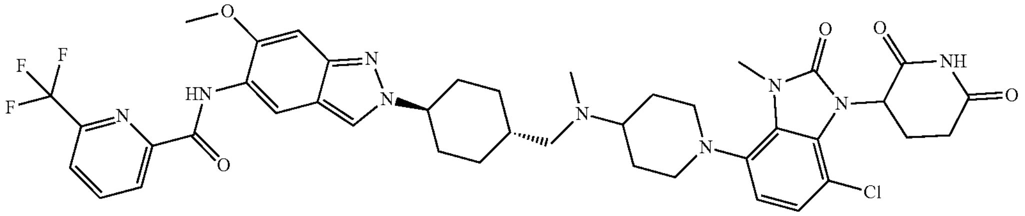 |
| I-483 | 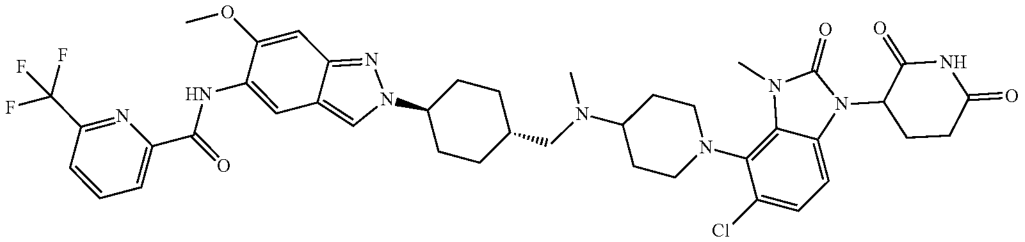 [SMILES: COc1cc2nn([C@H]3CC[C@H](CN(C)C4CCN(c5c(Cl)ccc6c5n(C)c(=O)n6C5CCC(=O)NC5=O)CC4)CC3)cc2cc1NC(=O)c1cccc(C(F)(F)F)n1] |
| I-484 | 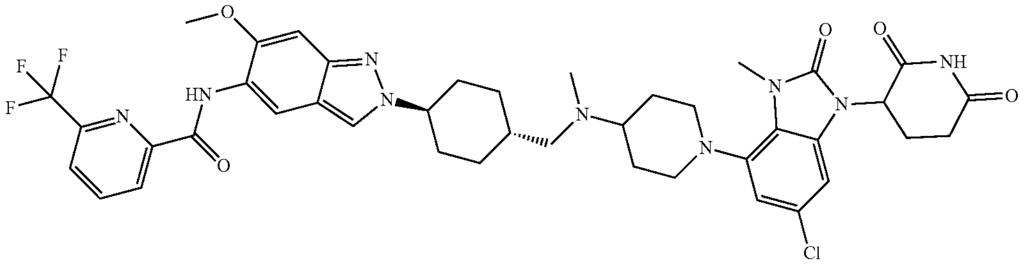 [SMILES: COc1cc2nn([C@H]3CC[C@H](CN(C)C4CCN(c5cc(Cl)cc6c5n(C)c(=O)n6C5CCC(=O)NC5=O)CC4)CC3)cc2cc1NC(=O)c1cccc(C(F)(F)F)n1] |
| I-485 | 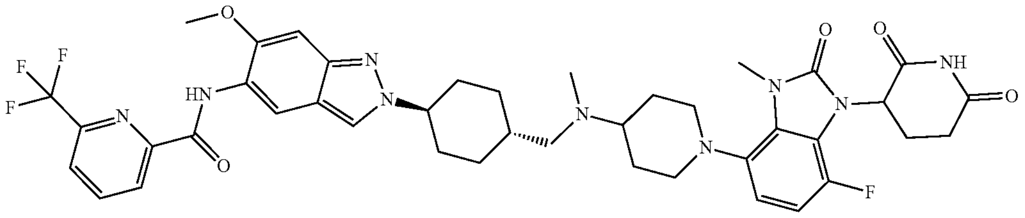 [SMILES: COc1cc2nn([C@H]3CC[C@H](CN(C)C4CCN(c5ccc(F)c6c5n(C)c(=O)n6C5CCC(=O)NC5=O)CC4)CC3)cc2cc1NC(=O)c1cccc(C(F)(F)F)n1] |
| I-486 | 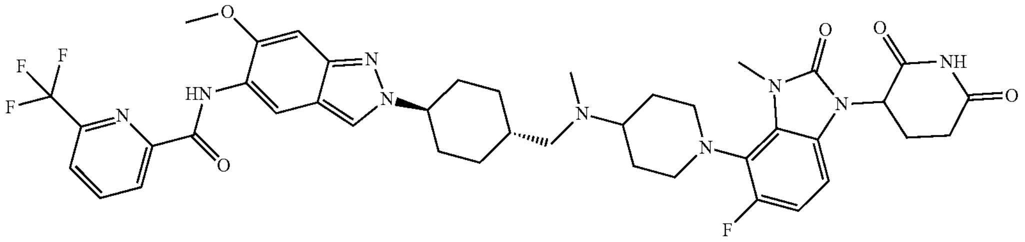 [SMILES: COc1cc2nn([C@H]3CC[C@H](CN(C)C4CCN(c5c(F)ccc6c5n(C)c(=O)n6C5CCC(=O)NC5=O)CC4)CC3)cc2cc1NC(=O)c1cccc(C(F)(F)F)n1] |
| I-487 | 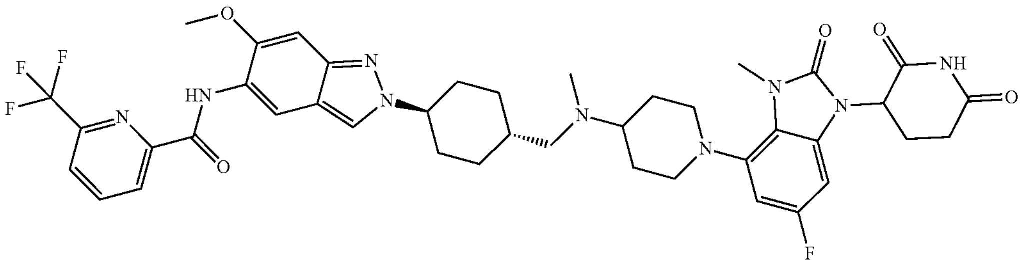 [SMILES: COc1cc2nn([C@H]3CC[C@H](CN(C)C4CCN(c5cc(F)cc6c5n(C)c(=O)n6C5CCC(=O)NC5=O)CC4)CC3)cc2cc1NC(=O)c1cccc(C(F)(F)F)n1] |

TABLE 1-continued

| Exemplary Compounds | |
|---|---|
| I-# | Structure |
| I-488 | 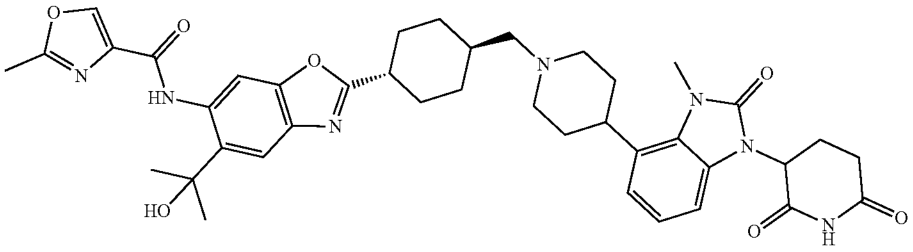 [SMILES: Cc1nc(C(=O)Nc2cc3oc([C@H]4CC[C@H](CN5CCC(c6cccc7c6n(C)c(=O)n7C6CCC(=O)NC6=O)CC5)CC4)nc3cc2C(C)(C)O)co1] |

In some embodiments, the present invention provides a compound set forth in Table 1, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $5^{th}$ Edition, John Wiley & Sons, 2001, *Comprehensive Organic Transformations*, R. C. Larock, $2^{nd}$ Edition, John Wiley & Sons, 1999, and *Protecting Groups in Organic Synthesis*, T. W. Greene and P. G. M. Wuts, $3^{rd}$ edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a provided compound is formed having a reactive DIM moiety (e.g., amine, alcohol, etc.), it is not shown but it is generally appreciated and well known by those having ordinary skill in the art that the reactivity of said reactive DIM moiety may be masked by employing a suitable protecting group that can thereafter be removed in situ or during a separate synthetic step.

In certain embodiments, compounds of the present invention are generally prepared according to Scheme 1 set forth below:

Scheme 1: Synthesis of Compounds of the Invention

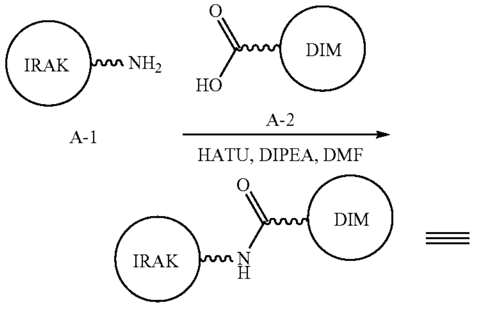

-continued

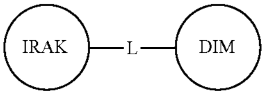

As depicted in Scheme 1, above, amine A-1 is coupled to acid A-2 using the coupling agent HATU in the presence of the base DIPEA in DMF to form a compound of the invention with a linker comprising an amide bond. The squiggly bond, , represents the portion of the linker between IRAK and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of the Invention

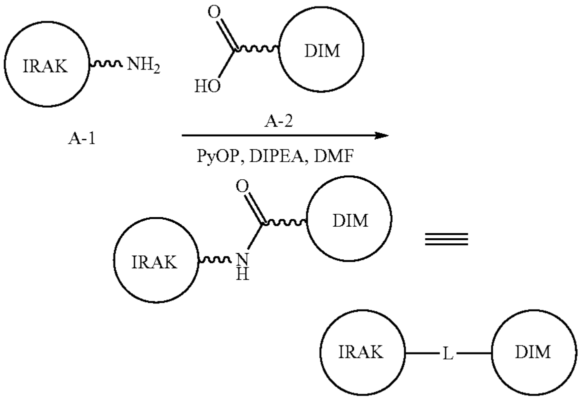

As depicted in Scheme 2, above, amine A-1 is coupled to acid A-2 using the coupling agent PyBOP in the presence of the base DIPEA in DMF to form a compound of the invention with a linker comprising an amide bond. The squiggly bond, , represents the portion of the linker between IRAK and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of the Invention

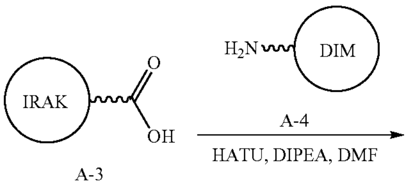

-continued

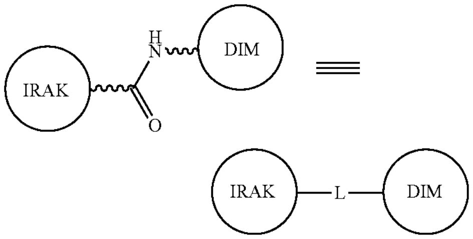

As depicted in Scheme 3, above, acid A-3 is coupled to amine A-4 using the coupling agent HATU in the presence of the base DIPEA in DMF to form a compound of the invention with a linker comprising an amide bond. The squiggly bond, , represents the portion of the linker between IRAK and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of the Invention

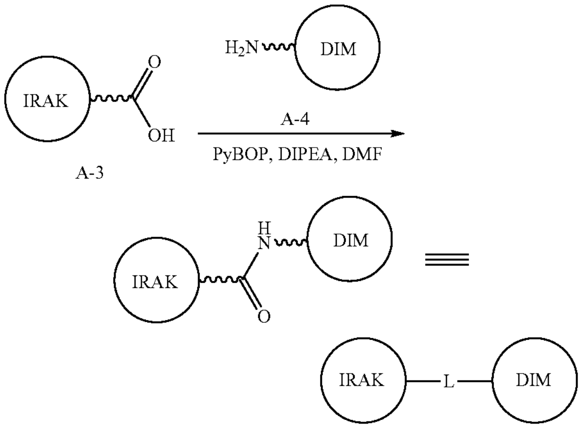

As depicted in Scheme 4, above, acid A-3 is coupled to amine A-4 using the coupling agent PyBOP in the presence of the base DIPEA in DMF to form a compound of the invention with a linker comprising an amide bond. The squiggly bond, represents the portion of the linker between IRAK and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of the Invention

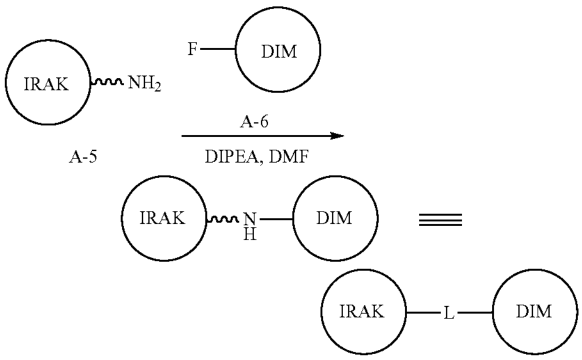

As depicted in Scheme 5, above, an $S_NAr$ displacement of fluoride A-6 by amine A-5 is effected in the presence of the base DIPEA in DMF to form a compound of the invention with a linker comprising a secondary amine. The squiggly bond, , represents the portion of the linker between IRAK and the terminal amino group of A-5.

In certain embodiments, compounds of the present invention are generally prepared according to Scheme 6 set forth below:

Scheme 6: Synthesis of Compounds of the Invention

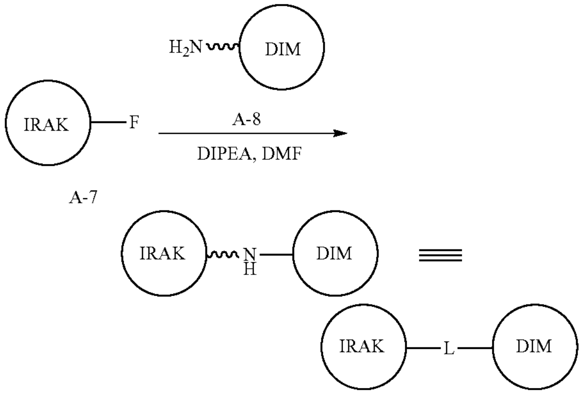

As depicted in Scheme 6, above, an $S_NAr$ displacement of fluoride A-7 by amine A-8 is effected in the presence of the base DIPEA in DMF to form a compound of the invention with a linker comprising a secondary amine. The squiggly bond, , represents the portion of the linker between DIM and the terminal amino group of A-8.

In certain embodiments, compounds of the present invention are generally prepared according to Scheme 7 set forth below:

Scheme 7: Synthesis of Compounds of the Invention

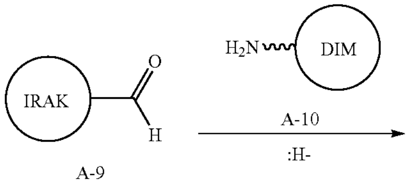

-continued

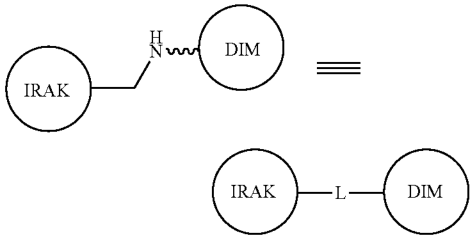

As depicted in Scheme 7, above, reductive alkylation of aldehyde A-9 by amine A-10 is effected in the presence of a mild hydride source (e.g., sodium cyanoborohydride or sodium triacetoxyborohydride) to form a provided compound with a linker comprising a secondary amine. The squiggly bond, , represents the portion of the linker between DIM and the terminal amino group of A-10.

In certain embodiments, compounds of the present invention are generally prepared according to Scheme 8 set forth below:

Scheme 8: Synthesis of Compounds of the Invention

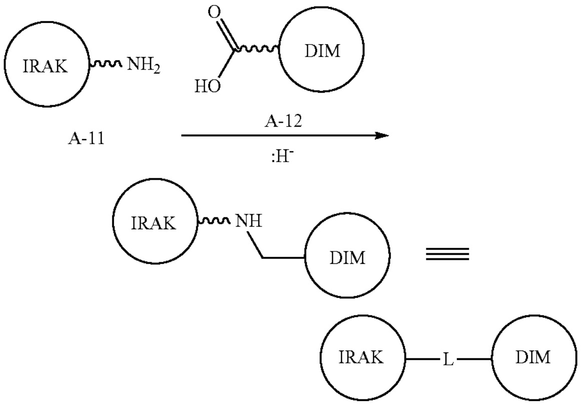

As depicted in Scheme 8, above, reductive alkylation of aldehyde A-12 by amine A-11 is effected in the presence of a mild hydride source (e.g., sodium cyanoborohydride or sodium triacetoxyborohydride) to form a provided compound with a linker comprising a secondary amine. The squiggly bond, , represents the portion of the linker between IRAK and the terminal amino group of A-11.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See for example, "March's Advanced Organic Chemistry", $5^{th}$ Ed., Ed.: Smith, M. B. and March, J., John Wiley & Sons, New York: 2001, the entirety of each of which is herein incorporated by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that it is effective to measurably degrade and/or inhibit an IRAK protein kinase, or a mutant thereof, in a biological sample or in a patient. In certain embodiments, the amount of compound in compositions of this invention is such that it is effective to measurably degrade and/or inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an IRAK protein kinase, or a mutant thereof.

As used herein, the term "degratorily active metabolite or residue thereof" means that a metabolite or residue thereof is also a degrader of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

Examples of kinases that are degraded and/or inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," PNAS 2002, 99(8), 5567-5572, Flannery et al., "The interleukin-1 receptor-associated kinases: Critical regulators of innate immune signaling" Biochem Pharm 2010, 80(12), 1981-1991 incorporated by reference in its entirety.

The activity of a compound utilized in this invention as a degrader and/or inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036; Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-KB," *Biochem*. J. 1999, 339, 227-231; Song et al., "The kinase activities of interleukin-e receptor associated kinase (IRAK)-1 and 4 are redundant in the control of inflammatory cytokine expression in human cells," Mol. Immunol. 2009, 46, 1458-1466, each of, the entirety of each of which is herein incorporated by reference. Detailed conditions for assaying a compound utilized in this invention as a degrader and/or inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1 α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine* (*Baltimore*), 2010, 89(6), 043-25; Li, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282(18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-KB," *Biochem. J.* 1999, 339, 227-231; Lin et al., "Helical assembly in the MyD88-IRAK4-IRAK2 complex in TLR/IL-1R signalling," *Nature* 2010, 465(17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," Nature 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of, the entirety of each of which is herein incorporated by reference. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204(10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets,* 12(7), pp: 883-903 (2008); Gearing, A. "Targeting toll-like receptors for drug development: a summary of commercial approaches," *Immunology and Cell Biology,* 85, pp: 490-494 (2007); Dinarello, C. "IL-1: Discoveries, controversies and future directions," *European Journal of Immunology,* 40, pp: 595-653 (2010), each of, the entirety of each of which is herein incorporated by reference. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wang et al., "IRAK-4 Inhibitors for Inflammation," *Curr. Topics in Med. Chem.* 2009, 9, 724-737, each of, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1β-Induced Interleukin 6 Production and the Myeloma Proliferative Component," *Mayo Clinic Proceedings,* 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr. Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology,* 22, pp: 246-251 (2010)), auto-inflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.,* 14, pp: 411-421 (2008)), inflammation (see, e.g., Dinarello, C. "Interleukin 1 and interleukin 18 as mediators of inflammation and the aging process," *The American Journal of Clinical Nutrition,* 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases,* 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomized, single-blind pilot study," *Annals of Rheumatic Diseases,* 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases,* 68, pp: 1602-1608 (2009)), neurological disorders, metabolic syndrome (see, e.g., Troseid, M. "The role of interleukin-18 in the metabolic syndrome," *Cardiovascular Diabetology,* 9:11, pp: 1-8 (2010)), immunodeficiency disorders such as AIDS and HIV (see, e.g., Iannello, A. et al., "Role of Interleukin-18 in the Development and Pathogenesis of *AIDS*," AIDS *Reviews,* 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53$^{rd}$ ASH Annual Meeting; Xu, et al., "A somatic variant in MYD88 (L256P) revealed by whole genome sequencing differentiates lymphoplasmacytic lymphoma from marginal zone lymphomas" 53$^{rd}$ ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53$^{rd}$ ASH Annual Meeting; Iriyama et al., "Clinical significance of genetic mutations of CD79B, CARD11, MYD88, and EZH2 genes in diffuse large B-cell lymphoma patients" 53$^{rd}$ ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit IRAK-1 only, IRAK-2-only, IRAK-4-only and/or IRAK1 and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma).

In some embodiments the proliferative disease which can be treated according to the methods of this invention is an MyD88 driven disorder. In some embodiments, the MyD88 driven disorder which can be treated according to the methods of this invention is selected from ABC DLBCL, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example anti-inflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil- related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus *foliaceus*, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, muscle wasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus *foliaceus*, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from systemic lupus erythematosus, multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the present invention provides a method of treating hidradenitis suppurativa in a patient in need thereof, comprising administering a compound of the present invention, or a pharmaceutically acceptable salt thereof.

In some embodiments, the present invention provides a method of treating atopic dermatitis in a patient in need thereof, comprising administering a compound of the present invention, or a pharmaceutically acceptable salt thereof.

In some embodiments, the present invention provides a method of treating rheumatoid arthritis in a patient in need thereof, comprising administering a compound of the present invention, or a pharmaceutically acceptable salt thereof.

In some embodiments, the present invention provides a method of treating solid and liquid tumors in a patient in need thereof, comprising administering a compound of the present invention, or a pharmaceutically acceptable salt thereof.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased Aβ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32(43), 15112-15123.

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Multiple Degradation

In some embodiments, the invention provides compounds that modulate targeted ubiquitination and degradation of one or more IRAK kinase. In some embodiments, a provided compound modulates targeted ubiquitination and degradation of one or more IRAK kinase and one or more additional protein. In some instances, a provided compound modulates targeted ubiquitination and degradation of IRAK4 and one, two, three, four, or five additional proteins.

In certain embodiments, the invention provides compounds that are triple degraders. In certain embodiments, the invention provides compounds that combine IRAK kinase degradation with IKZF1 and IKZF3 degradation. Some of the most commonly employed E3 ligase ligands are thalidomide and its derivatives, lenalidomide and pomalidomide, commonly referred to as IMiDs (immunomodulatory imide drugs). These agents are small-molecule ligands of cereblon (CRBN) (Ito et al. "Identification of a primary target of thalidomide teratogenicity" Science 2010, 327(5971):1345-1350), a substrate adaptor for the ubiquitously expressed cullin ring ligase 4 (CUL4)-RBX1-DDB1-CRBN (CUL4CRBN) E3 ligase. It has been shown that thalidomide interacts with CRBN to form a novel surface, resulting in interactions with neosubstrates such as Ikaros (IKZF1) and Aiolos (IKZF3) and their ubiquitination and subsequent proteasomal degradation (Krönke et al. "Lenalidomide causes selective degradation of IKZF1 and IKZF3 in multiple myeloma cells" Science 2014, 343(6168):301-305; and Lu et al. "The myeloma drug lenalidomide promotes the cereblon-dependent destruction of Ikaros proteins" Science, 2014; 343(6168):305-309). This activity alone has potent antitumor effects in some liquid malignancies, and lenalidomide (Reylimid®) is US Food and Drug Administration approved for the treatment of MCL, multiple myeloma, and myelodysplastic syndromes with deletion of chromosome 5q. Lenalidomide is also undergoing late-stage clinical trials for a number of lymphomas, including MCL and the activated B-cell subtype of diffuse large B-cell lymphoma (ABC DLBCL).

In some instances, degradation of IRAK4 alone is not sufficient to kill the MYD88 L265P mutant DLBCL cell line OCI-LY10 either in vitro or as a flank xenograft in vivo. Table 2 shows that IRAK4 binding moieties coupled to non-IMiD CRBN binders mediate effective knockdown of RAK4 but have little to no effect on the viability of MYD88 mutant ABC-DLBCL cell lines OCI-LY10 and SU-DHL-2 in vitro.

TABLE 2

IRAK4 degradation alone is insufficient to kill MYD88 mutant DLBCL cell lines in vitro

| | I-1 |
|---|---|
| IRAK4 Degradation in OCI-LY10, $DC_{50}$ (nM) | 4 |
| MYD88 Mutant Lines | |
| OCI-LY10 Viability, CTG $IC_{50}$ (nM) | >10,000 |
| SU-DHL2 Viability, CTG $IC_{50}$ (nM) | >10,000 |
| MYD88 WT Lines | |
| SU-DHL6 Viability, CTG $IC_{50}$ (nM) | 5,600 |
| U2932 Viability, CTG $IC_{50}$ (nM) | >10,000 |
| OCI-LY19 Viability, CTG $IC_{50}$ (nM) | >10,000 |

In some embodiments, a non-IMiD-based degraders effects IRAK degradation in MYD88 mutant ABC DLBCL cell line tumor xenografts but without causing regression. This is consistent with literature demonstrating no effect on growth of OCI-LY10 or other MYD88 mutant lines when the gene encoding TRAK4 is removed at the DNA level using CRISPR/Cas9 editing (Phelan et al. "A multiprotein supercomplex controlling oncogenic signaling in lymphoma" Nature, 2018, 7718:387-391).

It has been shown that activating MYD88 mutations increase production of beta-IFN, a pro-apoptotic cytokine, in ABC-DLBCL cells (Yang et al. "Exploiting synthetic lethality for the therapy of ABC diffuse large B cell lymphoma" Cancer Cell 2012, 21(6):723-737). The cells are rendered resistant to this effect by a concomitant MYD88-driven activation of NFkB signaling via IRF4 and SPIB transactivating CARD11 (Yang, Cancer Cell 2012). IMiDs are also known to increase the IFN response in MYD88 mutant ABC-DLBCL to levels sufficient to increase apoptosis (Yang, Cancer Cell 2012; and Hagner et al. "CC-122, a pleiotropic pathway modifier, mimics an interferon response and has antitumor activity in DLBCL" Blood 2015, 126: 779-789). This effect has been shown to synergize with inhibition of NFkB signaling to further drive DLBCL cell death (Yang, Cancer Cell 2012).

In some instances, the combination of an IMiD with a small molecule IRAK4 kinase inhibitor shows little to no additive effect on viability of the MYD88 mutant ABC DLBCL cell lines, such as OCI-LY10. In some embodiments, the combination of an IRAK4 inhibitor with IMiD is less active than an all-in-one IMiD-based IRAK4 degrader.

In certain embodiments, the combination of IRAK kinase degradation with IKZF1 and IKZF3 degradation in an all-in-one IMiD-based IRAK4 degrader shows potent, single agent activity versus MYD88 mutant ABC DLBCL cell lines in vitro and OCI-LY10 xenograft in vivo. In some embodiments, an all-in-one combination of an IMiD-based CRBN-binder and an IRAK4 binding moiety yields IRAK4 degraders that retain degradation of Ikaros (IKZF1) and other known IMiDs neosubstrates, while more strongly inducing an interferon response compared to pomalidomide alone. In some embodiments, IMiD-based IRAK4 degraders are potent at killing MYD88 mutant ABD-DLBCL cell lines in vitro, demonstrating increased activity versus that obtained from combining an IRAK4 inhibitor with IMiDs as single agents.

In certain embodiments, a provided compound comprising an IMiD-based E3 ligase degrades IRAK4, Ikaros, and Aiolos in MYD88 mutant ABC DLBCL cell line xenografts in vivo, and strongly induces a signature of interferon-driven proteins exemplified by IFIT1 (interferon-inducible transcript 1) and IFIT3 (interferon-inducible transcript 3). In some embodiments, a provided compound comprising an IMiD-based E3 ligase drives regression of tumor xenographs as a single agent.

In some embodiments, the provided compounds of present invention highlight a synergy obtained by combining IRAK4 degradation with IMiD induction of interferon response to drive single agent anti-tumor activity in MYD88 mutant DLBCL and possibly in other heme malignancies. In certain embodiments, a provided compound comprising an IMiD-based E3 ligase degrade IRAK4, Ikaros, and Aiolos acts synergistically. In some embodiments, a provided compound comprising an IRAK4 binder and an IMiD-based E3 ligase degrades IRAK4, Ikaros, and Aiolos with increased activity in comparison to a provided compound comprising the same IRAK4 binder and a non-IMiD-based E3 ligase and the same IMiD-based E3 ligase as a single agent.

In some embodiments, the present invention provides a method of treating MYD88-mutant Waldenstrom macroglobulinemia in a patient in need thereof, comprising administering a compound of the present invention, or a pharmaceutically acceptable salt thereof.

In some embodiments, the present invention provides a method of treating a AML, or a subset thereof, in a patient in need thereof, comprising administering a compound of the present invention, or a pharmaceutically acceptable salt thereof.

In some embodiments, the present invention provides a method of treating NSCLC in a patient in need thereof, comprising administering a compound of the present invention, or a pharmaceutically acceptable salt thereof.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound or a pharmaceutically acceptable salt thereof and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Reylimid®), or any combination(s) thereof.

In another embodiment, the present invention provides a method of treating gout comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound or a pharmaceutically acceptable salt thereof and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound or a pharmaceutically acceptable salt thereof and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a provided compound or a pharmaceutically acceptable salt thereof and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a provided compound or a pharmaceutically acceptable salt thereof and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound or a pharmaceutically acceptable salt thereof and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In some embodiments, the present invention provides a method of treating DLBCL comprising administering to a patient in need thereof a provided compound or a pharmaceutically acceptable salt thereof and a CHOP (cyclophosphamide, Hydrodaunorubicin®, Oncovin®, and prednisone or prednisolone) or R-CHOP (rituximab, cyclophosphamide, Hydrodaunorubicin®, Oncovin®, and prednisone or prednisolone) chemotherapy regimen.

In some embodiments, the present invention provides a method of treating DLBCL comprising administering to a patient in need thereof a provided compound or a pharmaceutically acceptable salt thereof and a rituximab/bendamustine chemotherapy regimen.

In some embodiments, the present invention provides a method of treating DLBCL comprising administering to a patient in need thereof a provided compound or a pharmaceutically acceptable salt thereof and a BTK inhibitor (e.g., ibrutinib).

In some embodiments, the present invention provides a method of treating DLBCL comprising administering to a patient in need thereof a provided compound or a pharmaceutically acceptable salt thereof and an anti-CD20 antibody (e.g., rituximab).

In some embodiments, the present invention provides a method of treating DLBCL comprising administering to a patient in need thereof a provided compound or a pharmaceutically acceptable salt thereof and an anti-CD79B ADC (e.g., polatuzumab).

In some embodiments, the present invention provides a method of treating DLBCL comprising administering to a patient in need thereof a provided compound or a pharmaceutically acceptable salt thereof and a BCL2 inhibitor (e.g., venetoclax).

In some embodiments, the present invention provides a method of treating DLBCL comprising administering to a patient in need thereof a provided compound or a pharmaceutically acceptable salt thereof and lenalidomide In some embodiments, the present invention provides a method of treating DLBCL comprising administering to a patient in need thereof a provided compound or a pharmaceutically acceptable salt thereof and a PI3K inhibitor (e.g., umbralisib).

In some embodiments, the present invention provides a method of treating a T-cell disease or deficiency describing herein comprising administering to a patient in need thereof a provided compound or a pharmaceutically acceptable salt thereof and a PI3K inhibitor (e.g., umbralisib).

In some embodiments, the present invention provides a method of treating DLBCL comprising administering to a patient in need thereof a provided compound or a pharmaceutically acceptable salt thereof and a proteasome inhibitor (e.g., bortezomib)

In some embodiments, the present invention provides a method of treating a T-cell disease or deficiency describing herein comprising administering to a patient in need thereof a provided compound or a pharmaceutically acceptable salt thereof and a protesome inhibitor (e.g., bortezomib).

In another embodiment, the present invention provides a method of treating multiple myeloma comprising administering to a patient in need thereof a provided compound or a pharmaceutically acceptable salt thereof and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Reylimid®).

In another embodiment, the present invention provides a method of treating Waldenstrom's macroglobulinemia comprising administering to a patient in need thereof a provided compound or a pharmaceutically acceptable salt thereof and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

In some embodiments, the present invention provides a method of treating Alzheimer's disease comprising administering to a patient in need thereof a provided compound or a pharmaceutically acceptable salt thereof and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound or a pharmaceutically acceptable salt thereof and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound or a pharmaceutically acceptable salt thereof and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degrading a protein kinase in a biological sample comprising the step of contacting said biological sample with a compound of this invention, or a composition comprising said compound.

According to another embodiment, the invention relates to a method of inhibiting or degrading IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition and/or degradation of a protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802, US 2010/0197686), navitoclax (and analogs thereof, see U.S. Pat. No. 7,390, 799), NH-1 (Shenayng Pharmaceutical University), obatoclax (and analogs thereof, see WO 2004/106328, US 2005/0014802), S—001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™) cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO 2008/039218, US 2008/0108636 and WO 2011/090760, US 2010/0249092, the entirety of each of which is herein incorporated by reference.

Further examples of SYK inhibitory compounds, and conditions treatable by such compounds in combination with compounds of this invention can be found in WO 2003/063794, US 2004/0029902, WO 2005/007623, US 2005/0075306, and WO 2006/078846, US 2006/0211657, the entirety of each of which is herein incorporated by reference.

Further examples of PI3K inhibitory compounds, and conditions treatable by such compounds in combination with compounds of this invention can be found in WO 2004/019973, US 2004/0106569, WO 2004/089925, US 2004/0242631, U.S. Pat. No. 8,138,347, WO 2002/088112, US 2004/0116421, WO 2007/084786, US 2010/0249126, WO 2007/129161, US 2008/0076768, WO 2006/122806, US 2008/0194579, WO 2005/113554, US 2008/0275067, and WO 2007/044729, US 2010/0087440, the entirety of each of which is herein incorporated by reference.

Further examples of JAK inhibitory compounds, and conditions treatable by such compounds in combination with compounds of this invention can be found in WO 2009/114512, US 2009/0233903, WO 2008/109943, US 2010/0197671, WO 2007/053452, US 2007/0191405, WO 2001/0142246, US 2001/0053782, and WO 2007/070514, US 2007/0135461, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin- 3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2- arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™), ); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]- amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12- 281 (*Asta Medica*), CDC-801 (Celgene), SeICID™ CC-10004 (Celgene), VM554/UM565 (*Vernalis*), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgGI, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MEDI4736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/053941, WO 2009/132238, US 2011/136796, WO 2011/056652, US 2012/277217, WO 2012/142237, US 2014/066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7- 1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgGI anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgGI Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALx-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgGI, acts by binding human CD47, and preventing it from delivering its “do not eat” signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STINGthat are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLx3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron -4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
$^n$BuOH: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium
hexafluorophosphate HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-methylmnorpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations were performed under reduced pressure, preferably between about 15 mm Hg and 100 mm Hg (=20-133 mbar). The structure of final products, intermediates and starting materials was confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention were either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions were carried out under nitrogen or argon unless otherwise stated.

Proton NMR ($^1H$ NMR) was conducted in deuterated solvent. In certain compounds disclosed herein, one or more $^1H$ shifts overlap with residual proteo solvent signals; these signals have not been reported in the experimental provided hereinafter.

TABLE 5

| Analytical instruments | |
|---|---|
| LCMS | Shimadzu UFLC MS: LCMS-2020<br>Agilent Technologies 1200 series MS: Agilent Technologies 6110<br>Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give $MH^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase are used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give $MH^+$] and equipped with Xbridge C18, 2.1X50 mm columns packed with 5 mm C18-coated silica or Kinetex EVO C18 2.1X30 mm columns packed with 5 mm C18-coated silica, eluting with 0.05 vol % $NH_3.H_2O$ in water (solvent A) and acetonitrile (solvent B).

HPLC Analytical Method: HPLC was carried out on X Bridge C18 150*4.6 mm, 5 micron. Column flow is 1.0 ml/min and mobile phase are used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19)mm, 5μ. Column flow was 16.0 ml/min. Mobile phase used was (A) 0.1% Formic Acid in Water and (B) Acetonitrile. Basic method used was (A) 5 mM ammonium bicarbonate and 0.1% $NH_3$ in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates 2-(2,6-Dioxopiperidin-3-yl)-4-fluoroisoindoline-1,3-dione (Intermediate R)

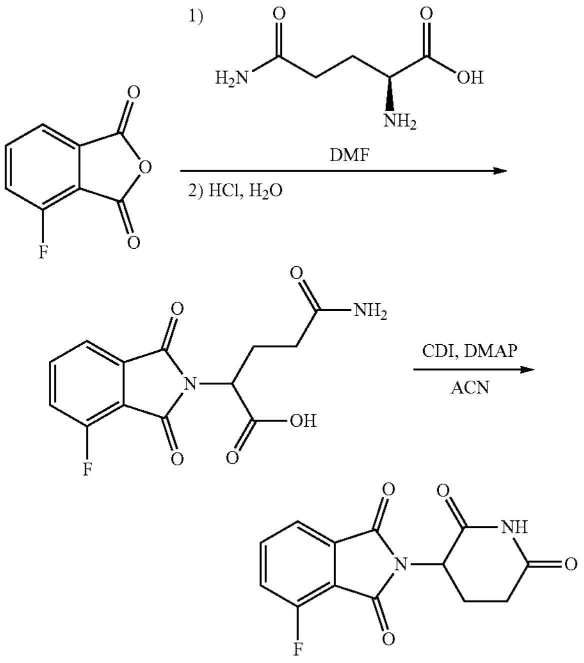

R

Step 1—5-amino-2-(4-fluoro-1,3-dioxoisoindolin-2-yl)-5-oxopentanoic acid

To a stirred solution of 4-fluoroisobenzofuran-1,3-dione (25 g, 150 mmol, CAS #652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4 N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS ($ESI^+$) m/z 295 $(M+H)^+$.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). $^1$H NMR (400 MHz, DMSO) δ ppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

Tert-butyl 4-(3-aminopropoxymethyl)piperidine-1-carboxylate (Intermediate AJG)

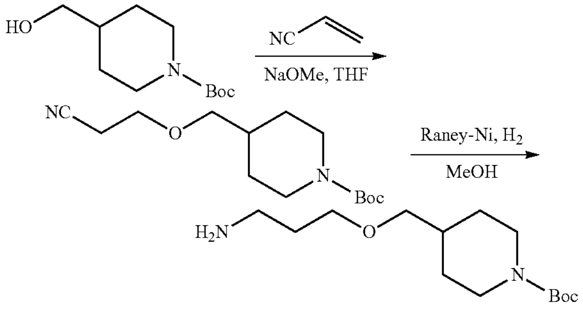

AJG

Step 1—Tert-butyl 4-(2-cyanoethoxymethyl)piperidine-1-carboxylate

To a mixture of tert-butyl 4-(hydroxymethyl)piperidine-1-carboxylate (10.0 g, 46.4 mmol, CAS #123855-51-6) and prop-2-enenitrile (4.93 g, 92.9 mmol) in THE (100 mL) was added NaOMe (250 mg, 4.64 mmol). The reaction mixture was stirred at 25° C. for 12 hours. On completion, the reaction mixture was diluted with water (100 mL) and extracted with EA (2×200 mL). The combined organic layers was dried over $Na_2SO_4$, filtered and concentrated in vacuo to give the title compound (8.20 g, 65% yield) as colorless oil. $^1$H NMR (400 MHz, $CDCl_3$) δ 4.19-4.04 (m, 2H), 3.64 (t, J=6.4 Hz, 2H), 3.33 (d, J=6.0 Hz, 2H), 2.78-2.63 (m, 2H), 2.59 (t, J=6.4 Hz, 2H), 1.81-1.73 (m, 1H), 1.73-1.68 (m, 2H), 1.45 (s, 9H), 1.21-1.09 (m, 2H).

Step 2—Tert-butyl 4-(3-aminopropoxymethyl)piperidine-1-carboxylate

To a mixture of tert-butyl 4-(2-cyanoethoxymethyl)piperidine-1-carboxylate (8.20 g, 30.5 mmol) in MeOH (80 mL) was added Raney-Ni (4.10 g, 47.8 mmol). The reaction mixture was stirred at 25° C. for 12 hours under $H_2$ (50 Psi).

On completion, the reaction mixture was filtered. The filtrate was concentrated in vacuo to give the title compound (8.00 g, 96% yield) as colorless oil. $^1$H NMR (400 MHz, $CDCl_3$) δ 4.09 (s, 2H), 3.51-3.44 (m, 2H), 3.25 (d, J=6.0 Hz, 2H), 2.79 (t, J=6.8 Hz, 2H), 2.74-2.60 (m, 2H), 1.77-1.65 (m, 5H), 1.45 (s, 9H), 1.42-1.27 (m, 2H), 1.20-1.05 (m, 2H).

2-(2,6-Dioxo-3-piperidyl)-4-[3-(4-piperidylmethoxy)propylamino]isoindoline-1,3-dione (Intermediate AJH)

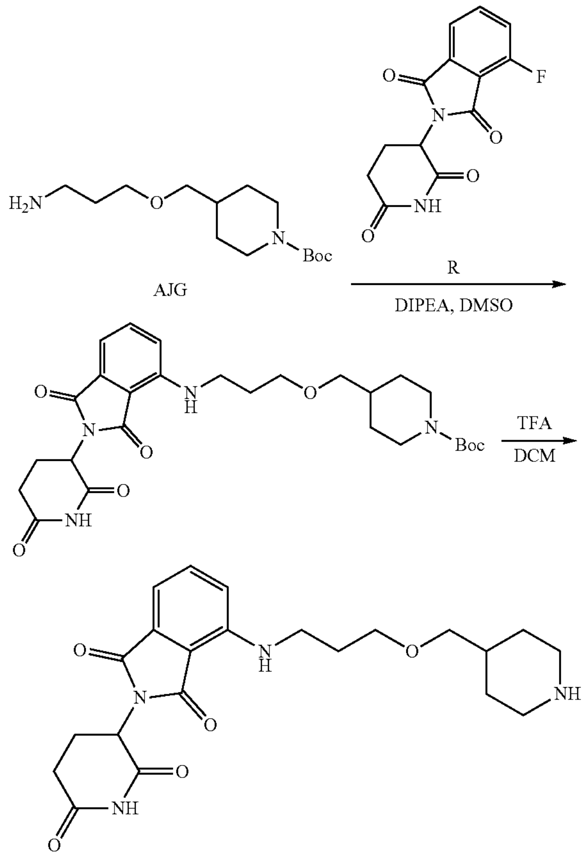

AJG

AJH

Step 1—Tert-butyl 4-[3-[[2-(2,6-dioxo-3-piperidyl)-1,3-dioxo-isoindolin-4-yl]amino]propoxymethyl]piperidine-1-carboxylate A mixture of 2-(2,6-dioxo-3-piperidyl)-4-fluoro-isoindoline-1,3-dione (300 mg, 1.09 mmol, Intermediate R), tert-butyl 4-(3-aminopropoxymethyl)piperidine-1-carboxylate (355 mg, 1.30 mmol, Intermediate AJG) and DIPEA (421 mg, 3.26 mmol) in DMSO (3 mL) was stirred at 130° C. for 2 hours. On completion, after cooled to 15° C., the reaction was quenched with water (0.2 mL). The mixture was concentrated in vacuo and the residue was purified by reversed phase flash (TFA condition) to give the title compound (200 mg, 35% yield) as light yellow solid. 1H NMR (400 MHz, DMSO-$d_6$) δ 11.09 (s, 1H), 7.63-7.54 (m, 1H), 7.09 (d, J=8.8 Hz, 1H), 7.02 (d, J=6.8 Hz, 1H), 6.66 (t, J=5.2 Hz, 1H), 5.07-5.02 (m, 1H), 3.98-3.86 (m, 2H), 3.45 (t, J=5.6 Hz, 2H), 3.41-3.35 (m, 3H), 3.22 (d, J=6.4 Hz, 2H), 2.95-2.83 (m, 1H), 2.62-2.53 (m, 3H), 2.06-1.98 (m, 1H), 1.82-1.81 (m, 2H), 1.74-1.60 (m, 3H), 1.38 (s, 9H), 1.06-0.94 (m, 2H).

Step 2—2-(2,6-Dioxo-3-piperidyl)-4-[3-(4-piperidylmethoxy)propylamino]isoindoline-1,3-dione To a solution of tert-butyl 4-[3-[[2-(2,6-dioxo-3-piperidyl)-1,3-dioxo-isoindolin-4-yl]amino]propoxymethyl]piperidine-1-carboxylate (60.0 mg, 113 umol) in DCM (2 mL) was added TFA (1 mL) at 15° C. The mixture was stirred at 15° C. for 2 hours. On completion, the mixture was concentrated in vacuo to give the title compound (60.0 mg, 97% yield, TFA salt) as light yellow oil. LC-MS (ESI$^+$) m/z 429.1 $(M+H)^+$.

Ethyl 4-(p-tolylsulfonyloxy)cyclohexanecarboxylate (Intermediate AGK)

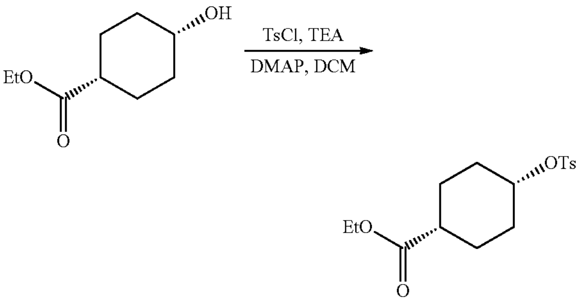

AGK

To a solution of ethyl 4-hydroxycyclohexanecarboxylate (10.0 g, 58.06 mmol, CAS #75877-66-6), DMAP (710 mg, 5.81 mmol) and TEA (17.6 g, 174 mmol) in DCM (150 mL) was added p-TsCl (22.1 g, 116 mmol) at 15° C. The mixture was stirred at 15° C. for 16 hours. On completion, the reaction was quenched with water (20 mL) and the mixture was partitioned. The organic layer was concentrated in vacuo. The residue was purified by column chromatography on silica gel to give the title compound (16.0 g, 84% yield) as white solid. $^1$H NMR (400 MHz, $CDCl_3$) δ 7.79 (d, J=8.2 Hz, 2H), 7.33 (d, J=7.9 Hz, 2H), 4.79-4.64 (m, 1H), 4.10 (q, J=7.2 Hz, 2H), 2.45 (s, 3H), 2.35-2.27 (m, 1H), 1.93-1.82 (m, 4H), 1.76-1.66 (m, 2H), 1.60-1.50 (m, 2H), 1.24 (t, J=7.2 Hz, 3H).

N-[6-(1-hydroxy-1-methyl-ethyl)-2H-indazol-5-yl]-6-(trifluoromethyl)pyridine-2-carboxamide (Intermediate TJ)

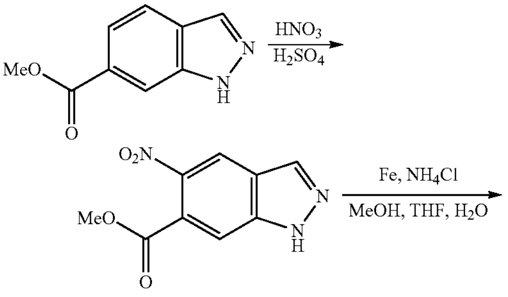

-continued

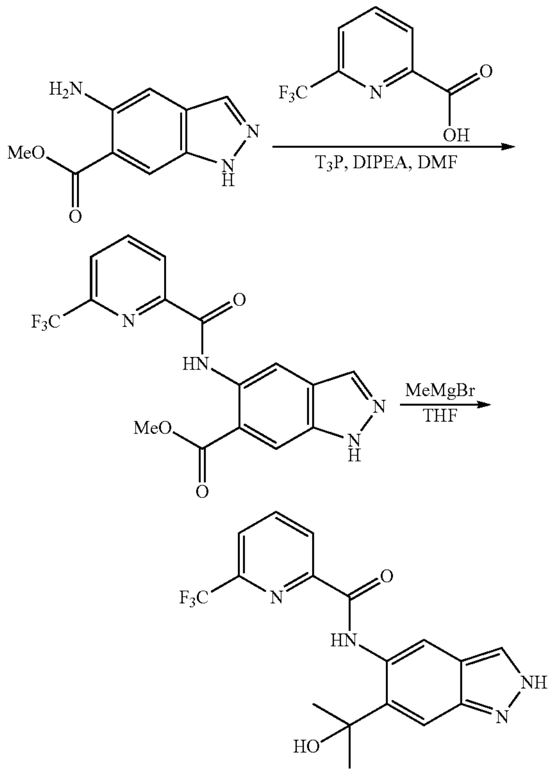

TJ

Step 1—Methyl 5-nitro-1H-indazole-6-carboxylate

To a solution of methyl 1H-indazole-6-carboxylate (10.0 g, 56.7 mmol) in $H_2SO_4$ (100 mL) was added a solution of $HNO_3$ (12.1 g, 125 mmol, 65% purity) in $H_2SO_4$ (20 mL) at −10-0° C. during 30 minutes. The mixture was stirred at −10-0° C. for 1 hour. On completion, the mixture was poured into ice/water (1.0 L) slowly. The mixture was filtered and the filter cake was washed with water (2×200 mL). Then the cake was collected and dried in vacuo to give the title compound (11.9 g, 94% yield) as yellow solid. $^1$H NMR (400 MHz, DMSO-$d_6$) δ 8.69 (s, 1H), 8.44 (s, 1H), 7.97 (s, 1H), 3.86 (s, 3H).

Step 2—Methyl 5-amino-1H-indazole-6-carboxylate

To a solution of methyl 5-nitro-1H-indazole-6-carboxylate (10.9 g, 49.2 mmol) in MeOH (100 mL) and THF (60 mL) was added a solution of $NH_4Cl$ (26.3 g, 492 mmol) in $H_2O$ (100 mL) at 25° C. Then Fe (13.7 g, 245 mmol) was added to the mixture in portions at 70° C., and the mixture was stirred at 70° C. for 1 hour. On completion, the mixture was filtered and the filter cake was washed with EA (200 mL). The filtrate was concentrated in vacuo. The residue was washed with water (100 mL), and extracted with EA (3×100 mL). The combined organic layer was washed with brine (100 mL), dried over $Na_2SO_4$, filtered and concentrated in vacuo to the title compound (7.30 g, 77% yield) as yellow solid. $^1$H NMR (400 MHz, DMSO-$d_6$) δ 12.82 (s, 1H), 7.99 (s, 1H), 7.85 (s, 1H), 6.99 (s, 1H), 6.00 (s, 2H), 3.85 (s, 3H).

Step 3—Methyl 5-[[6-(trifluoromethyl)pyridine-2-carbonyl]amino]-1H-indazole-6-carboxylate To a solution of methyl 5-amino-1H-indazole-6-carboxylate (7.20 g, 37.6 mmol), 6-(trifluoromethyl)pyridine-2-carboxylic acid (6.48 g, 33.9 mmol, CAS #131747-42-7) and DIPEA (7.35 g, 56.8 mmol) in THF (70 mL) was added $T_3P$ (47.9 g, 44.8 mL, 50 wt %) slowly at 0° C. Then the mixture was stirred at 0-5° C. for 2 hours. On completion, the reaction was quenched with cold water (0.1 mL). The mixture was diluted with water (280 mL), and stirred at 25° C. for 0.5 hour. The mixture was filtered and the filter cake was washed with water (30 mL). The filter cake was collected and dried in vacuo to give the title compound (12.3 g, 99% yield) as yellow solid. $^1$H NMR (400 MHz, DMSO-$d_6$) δ 12.58 (s, 1H), 9.15 (s, 1H), 8.47 (d, J=7.6 Hz, 1H), 8.39 (t, J=7.6 Hz, 1H), 8.30 (s, 1H), 8.25 (s, 1H), 8.20 (d, J=8.0 Hz, 1H), 3.97 (s, 3H).

Step 4—N-[6-(1-hydroxy-1-methyl-ethyl)-2H-indazol-5-yl]-6-(trifluoromethyl)pyridine-2- carboxamide To a solution of methyl 5-[[6-(trifluoromethyl)pyridine-2-carbonyl]amino]-1H-indazole-6-carboxylate (4.00 g, 10.9 mmol) in THF (40 mL) was added MeMgBr-$Et_2O$ solution (3.0 M, 29.3 mL) slowly at 0° C. The mixture was stirred at 0-25° C. for 16 hours. On completion, the reaction was quenched with sat.$NH_4Cl$ (40 mL) slowly at 0-10° C. The mixture was extracted with EA (3×40 mL). The combined organic layer was concentrated in vacuo. The residue was purified by reverse phase chromatography (FA condition) to give the title compound (1.50 g, 37% yield) as light yellow solid. $^1$H NMR (400 MHz, $CDCl_3$) δ 12.23 (s, 1H), 8.96 (s, 1H), 8.52 (d, J=7.6 Hz, 1H), 8.12 (t, J=7.6 Hz, 1H), 8.07 (s, 1H), 7.85 (d, J=7.6 Hz, 1H), 7.50 (s, 1H), 1.80 (s, 6H).

N-[2-(4-formylcyclohexyl)-6-(1-hydroxy-1-methyl-ethyl)indazol-5-yl]-6-(trifluoromethyl)pyridine-2-carboxamide (Intermediate AGL)

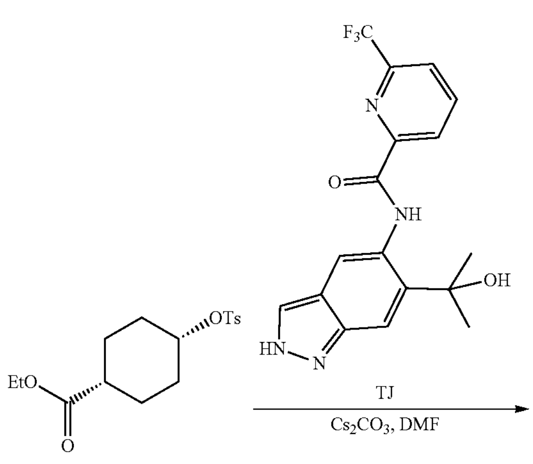

AGK

-continued

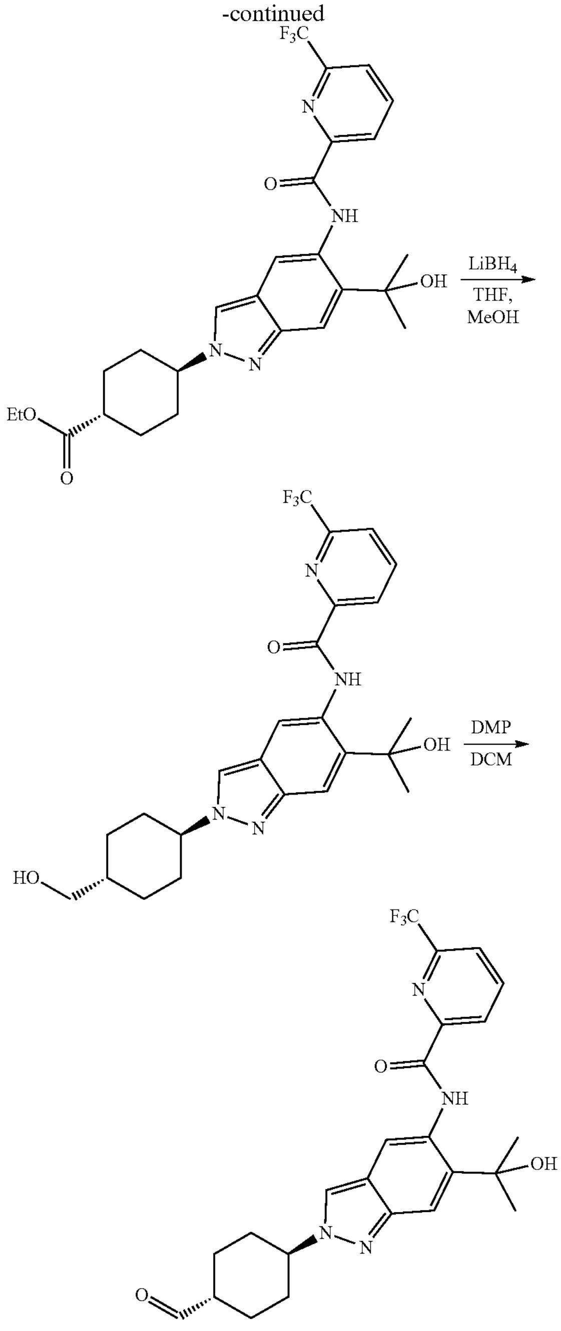

AGL

Step 1—Ethyl 4-[6-(1-hydroxy-1-methyl-ethyl)-5-[[6-(trifluoromethyl)pyridine-2-carbonyl]amino]indazol-2-yl]cyclohexanecarboxylate To a mixture of N-[6-(1-hydroxy-1-methyl-ethyl)-2H-indazol-5-yl]-6-(trifluoromethyl)pyridine-2- carboxamide (1.30 g, 3.57 mmol, Intermediate TJ), ethyl 4-(p-tolylsulfonyloxy)cyclohexane carboxylate (2.33 g, 7.14 mmol, Intermediate AGK) and $Cs_2CO_3$ (2.33 g, 7.14 mmol) in DMF (20 mL) was stirred at 80° C. for 16 hours. To the mixture was added ethyl 4-(p-tolylsulfonyloxy)cyclohexanecarboxylate (2.33 g, 7.14 mmol) and $Cs_2CO_3$ (2.33 g, 7.14 mmol) at 15° C. The mixture was stirred at 80° C. for 16 hours. On completion, after cooled to 15° C., the mixtures of two batches were combined, diluted with water (100 mL), and extracted with EA (3×60 mL). The organic layer was washed with brine (20 mL), dried over $Na_2SO_4$, filtered and concentrated in vacuo. The residue was purified by reverse phase flash and prep-HPLC (column: Phenomenex Synergi Max-RP 150*50 mm*10 um; mobile phase: [water (0.225% FA)-ACN]; B %: 52%-82%, 11 min) to give the title compound (530 mg, 14% yield) as white solid. $^1$H NMR (400 MHz, $CDCl_3$) δ 12.28 (s, 1H), 8.87 (s, 1H), 8.50 (d, J=7.6 Hz, 1H), 8.10 (t, J=8.0 Hz, 1H), 7.92 (s, 1H), 7.84 (d, J=7.6 Hz, 1H), 7.74 (s, 1H), 4.43-4.35 (m, 1H), 4.17 (q, J=7.2 Hz, 2H), 2.48-2.40 (m, 1H), 2.36-2.34 (m, 2H), 2.28-2.19 (m, 3H), 2.10-1.97 (m, 2H), 1.81 (s, 6H), 1.76-1.64 (m, 2H), 1.29 (t, J=7.2 Hz, 3H).

Step 2—N-[2-[4-(hydroxymethyl)cyclohexyl]-6-(1-hydroxy-1-methyl-ethyl)indazol-5-yl]-6-(trifluoro methyl)pyridine-2-carboxamide To a solution of ethyl 4-[6-(1-hydroxy-1-methyl-ethyl)-5-[[6-(trifluoromethyl)pyridine-2-carbonyl]amino]indazol-2-yl]cyclohexanecarboxylate (200 mg, 385 umol) in THF (3 mL) and MeOH (0.4 mL) was added $LiBH_4$ (21.0 mg, 964 umol) at 0° C. The mixture was stirred at 50° C. for 1 hour. On completion, the reaction was quenched with sat. aq. $NH_4Cl$ (5 mL). The mixture was diluted with water (40 mL), then extracted with EA (3×20 mL). The combined organic layer was washed with brine (10 mL), dried over $Na_2SO_4$, filtered and concentrated in vacuo to give the title compound (180 mg, 98% yield) as light yellow solid. $^1$H NMR (400 MHz, DMSO-$d_6$) δ 12.35 (s, 1H), 8.71 (s, 1H), 8.48-8.42 (m, 1H), 8.39-8.34 (m, 2H), 8.16 (d, J=7.6 Hz, 1H), 7.58 (s, 1H), 6.51 (s, 1H), 5.93 (s, 1H), 4.46-4.35 (m, 1H), 3.29 (s, 2H), 2.19-2.10 (m, 2H), 1.92-1.89 (m, 4H), 1.62 (s, 6H), 1.25-1.11 (m, 3H).

Step 3—N-[2-(4-formylcyclohexyl)-6-(1-hydroxy-1-methyl-ethyl)indazol-5-yl]-6-(trifluoromethyl)pyridine-2-carboxamide To a solution of N-[2-[4-(hydroxymethyl)cyclohexyl]-6-(1-hydroxy-1-methyl-ethyl)indazol-5-yl]-6- (trifluoromethyl)pyridine-2-carboxamide (50.0 mg, 104 umol) in DCM (5 mL) was added DMP (89.0 mg, 209 umol) at 0° C. The mixture was stirred at 0-10° C. for 6 hours. On completion, the reaction was quenched with sat. aq. $Na_2S_2O_3$ (5 mL), and extracted with DCM (2×10 mL). The combined organic layer was washed with sat. aq. $NaHCO_3$ (5 mL), dried over $Na_2SO_4$, filtered and concentrated in vacuo to give the title compound (49.0 mg, 98% yield) as light yellow solid. LC-MS ($ESI^+$) m/z 475.2 $(M+H)^+$.

1-(2,6-dioxo-3-piperidyl)-3-methyl-2-oxo-benzimidazole-4-carbaldehyde (Intermediate WW)

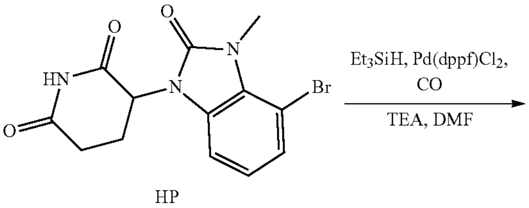

HP

-continued

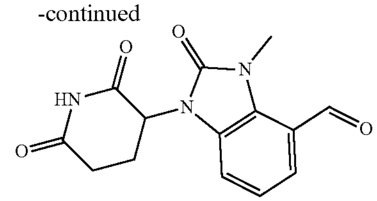

WW

To a solution of 3-(4-bromo-3-methyl-2-oxo-2,3-dihydro-1H-benzo[d]imidazol-1-yl)piperidine-2,6-dione (500 mg, 1.48 mmol, Intermediate HP) in DMF (20 mL) was added TEA (448 mg, 4.44 mmol), Pd(dppf)$Cl_2$ (162 mg, 221 umol) and $Et_3SiH$ (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS ($ESI^+$) m/z 288.0 $(M+H)^+$.

1-Methyl-3-[3-methyl-4-[[4-(methylamino)-1-piperidyl]methyl]-2-oxo-benzimidazol-1-yl]piperidine-2,6-dione (Intermediate AAM)

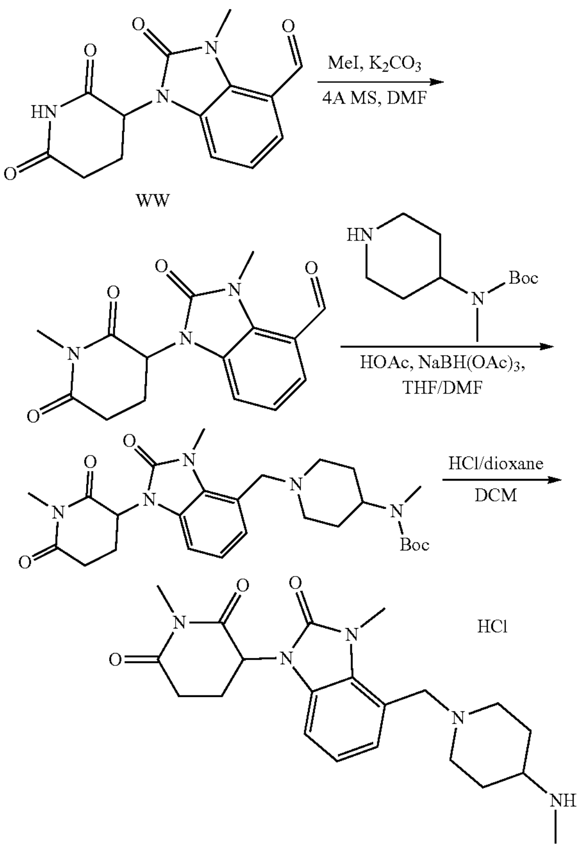

AAM

Step 1—3-Methyl-1-(1-methyl-2,6-dioxo-3-piperidyl)-2-oxo-benzimidazole-4-carbaldehyde To a solution of 1-(2,6-dioxo-3-piperidyl)-3-methyl-2-oxo-benzimidazole-4-carbaldehyde (150 mg, 522 umol, Intermediate WW), $K_2CO_3$ (108 mg, 783 umol), 4AMS (50 mg) in DMF (5 mL) was added MeI (111 mg, 783 umol, 48.7 uL). The reaction mixture was stirred at 15° C. for 12 hrs. On completion, the mixture was filtered and the filtrate was concentrated in vacuo to give a residue. The residue was purified by reverse phase (0.1% FA condition) to give the title compound (120 mg, 76% yield) as a white solid. $^1H$ NMR (400 MHz, DMSO-$d_6$) δ 10.40 (s, 1H), 7.61 (dd, J=0.8, 8.0 Hz, 1H), 7.46 (d, J=7.2 Hz, 1H), 7.20 (t, J=8.0 Hz, 1H), 5.53 (dd, J=5.4, 13.2 Hz, 1H), 3.68 (s, 3H), 3.04 (s, 3H), 3.01-2.93 (m, 1H), 2.84-2.72 (m, 2H), 2.11-2.03 (m, 1H); LC-MS ($ESI^+$) m/z 302.2 $(M+H)^+$.

Step 2—Tert-butyl N-methyl-N-[1-[[3-methyl-1-(1-methyl-2,6-dioxo-3-piperidyl)-2-oxo-benzimidazol-4-yl]methyl]-4-piperidyl]carbamate To a solution of 3-methyl-1-(1-methyl-2,6-dioxo-3-piperidyl)-2-oxo-benzimidazole-4-carbaldehyde (120 mg, 398 umol) and tert-butyl N-methyl-N-(4-piperidyl)carbamate (85.3 mg, 398 umol, CAS #108612-54-0) in THE (3 mL) was added HOAc (23.9 mg, 398 umol, 22.7 uL). The mixture was stirred at 20° C. for 30 minutes, then NaBH $(OAc)_3$ (168 mg, 796 umol) was added to the mixture. The reaction mixture was stirred at 20° C. for 16 hrs. On completion, the mixture was quenched by addition $H_2O$ (0.2 mL), then the mixture was concentrated in vacuo to give a residue. The residue was purified by reverse phase (0.1% FA condition) to give the title compound (160 mg, 80% yield) as a white solid. LC-MS ($ESI^+$) m/z 500.2 $(M+H)^+$.

Step 3—1-Methyl-3-[3-methyl-4-[[4-(methylamino)-1-piperidyl]methyl]-2-oxo-benzimidazol-1-yl]piperidine-2,6-dione To a solution of tert-butyl N-methyl-N-[1-[[3-methyl-1-(1-methyl-2,6-dioxo-3-piperidyl)-2-oxo- benzimidazol-4-yl]methyl]-4-piperidyl]carbamate (150 mg, 300 umol) in DCM (3 mL) was added HCl/dioxane (4 M, 3 mL). The reaction mixture was stirred at 20° C. for 2 hrs. On completion, the mixture was concentrated in vacuo to give the title compound (130 mg, 99% yield, HCl salt) as a white solid. LC-MS ($ESI^+$) m/z 400.2 $(M+H)^+$.

Benzyl N-[3-[3-(methylamino)propoxy]propyl]carbamate (Intermediate AEU)

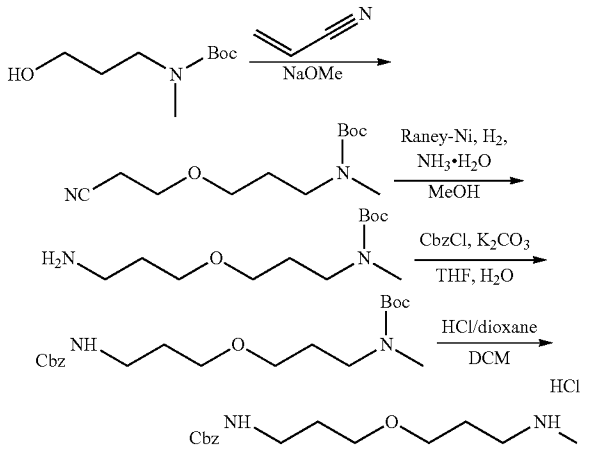

AEU

Step 1—Tert-butyl N-[3-(2-cyanoethoxy)propyl]-N-methyl-carbamate

To a mixture of NaOMe (5.71 mg, 106 umol) and tert-butyl N-(3-hydroxypropyl)-N-methyl-carbamate (2.00 g, 10.6 mmol, CAS #98642-44-5) in THF (20 mL) was added prop-2-enenitrile (1.12 g, 21.1 mmol). The reaction mixture was stirred at 20° C. for 12 hours. On completion, the mixture was concentrated in vacuo. The residue was diluted with water (40 mL), and extracted with EA (3×30 mL). The combined organic layers were washed with brine (50 mL), dried over $Na_2SO_4$, filtered and concentrated in vacuo to give the title compound (2.00 g, 78% yield) as light yellow oil. $^1H$ NMR (400 MHz, $CDCl_3$) δ 3.65 (t, J=6.4 Hz, 2H), 3.52 (t, J=6.4 Hz, 2H), 3.31 (t, J=6.8 Hz, 2H), 2.87 (s, 3H), 2.61 (t, J=6.4 Hz, 2H), 1.87-1.79 (m, 2H), 1.47 (s, 9H).

Step 2—Tert-butyl N-[3-(3-aminopropoxy)propyl]-N-methyl-carbamate

To a mixture of tert-butyl N-[3-(2-cyanoethoxy)propyl]-N-methyl-carbamate (2.00 g, 8.25 mmol) in MeOH (60 mL) was added Raney-Ni (1.00 g, 11.6 mmol) and $NH_3.H_2O$ (6.00 mL, 25% solution). The reaction mixture was stirred at 30° C. for 12 hours under $H_2$ (50 psi). On completion, the mixture was filtered with celite and concentrated in vacuo to give the title compound (1.80 g, 88% yield) as yellow oil. $^1H$ NMR (400 MHz, $CDCl_3$) δ 3.51 (t, J=6.4 Hz, 2H), 3.44 (t, J=6.4 Hz, 2H), 3.30 (s, 2H), 2.87 (s, 3H), 2.82 (t, J=6.8 Hz, 2H), 1.84-1.77 (m, 2H), 1.73 (t, J=6.4 Hz, 2H), 1.48 (s, 9H), 1.21-1.01 (m, 2H).

Step 3—Tert-butyl N-[3-[3-(benzyloxycarbonylamino)propoxy]propyl]-N-methyl-carbamate To a solution of tert-butyl N-[3-(3-aminopropoxy)propyl]-N-methyl-carbamate (1.00 g, 4.06 mmol) in THF (20 mL) and $H_2O$ (20 mL) was added $K_2CO_3$ (1.12 g, 8.12 mmol). Then CbzCl (762 mg, 4.47 mmol) was added at 0° C. The mixture was stirred at 0-15° C. for 2 hours. On completion, the mixture was diluted water (50 ml), then extracted with EA (3×50 mL). The combined organic layers were washed with brine (50 mL), dried over $Na_2SO_4$, filtered and concentrated in vacuo to give the title compound (1.50 g, 97% yield) as yellow oil. $^1H$ NMR (400 MHz, $CDCl_3$) δ 7.40-7.31 (m, 5H), 5.10 (s, 2H), 3.52-3.24 (m, 8H), 2.82 (s, 3H), 1.89-1.68 (m, 4H), 1.51-1.39 (m, 9H).

Step 4—Benzyl N-[3-[3-(methylamino)propoxy]propyl]carbamate

To a solution of tert-butyl N-[3-[3-(benzyloxycarbonylamino)propoxy]propyl]-N-methyl-carbamate (30.0 mg, 78.8 umol) in DCM (2 mL) was added HCl/dioxane (4 M, 3.00 mL). The mixture was stirred at 15° C. for 2 hours. On completion, the mixture was concentrated in vacuo to give the title compound (25.0 mg, 100% yield, HCl salt) as a white solid. LC-MS ($ESI^+$) m/z 281.1 $(M+H)^+$.

2-(2,6-Dioxo-3-piperidyl)-4-[3-[3-(methylamino)propoxy]propylamino]isoindoline-1,3-dione (Intermediate AMC)

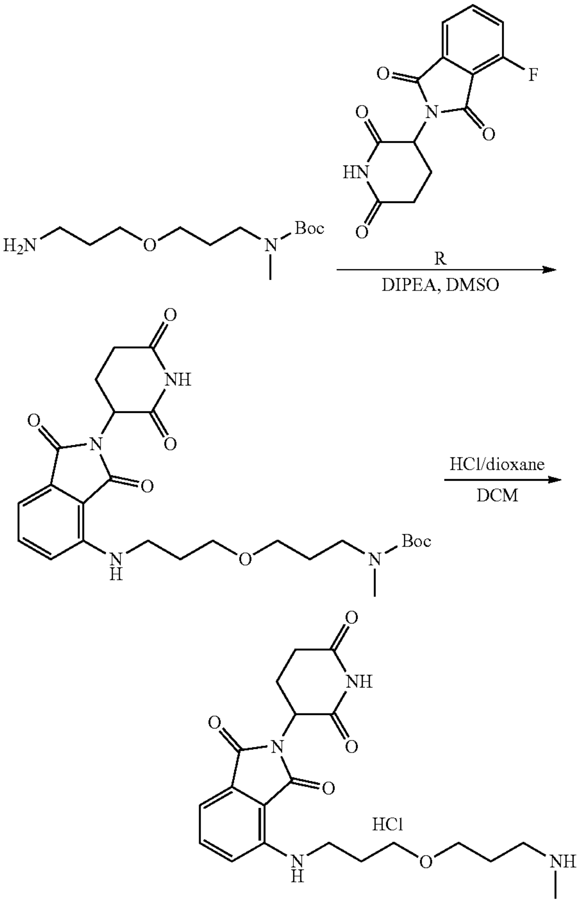

AMC

Step 1—Tert-butyl N-[3-[3-[[2-(2,6-dioxo-3-piperidyl)-1,3-dioxo-isoindolin-4-yl]amino]propoxy]propyl]-N-methyl-carbamate To a solution of tert-butyl N-[3-(3-aminopropoxy)propyl]-N-methyl-carbamate (130 mg, 527 umol, synthesized via Steps 1-2 on Intermediate AEU) and 2-(2,6-dioxo-3-piperidyl)-4-fluoro-isoindoline-1,3-dione (132 mg, 479 umol, Intermediate R) in DMSO (10 mL) was added DIPEA (18.7 mg, 144 umol) at 25° C. The reaction mixture was stirred at 130° C. for 2 hrs. On completion, the reaction mixture was concentrated in vacuo to give the residue. The residue was purified by reverse phase (0.1% FA condition) to give the title compound (160 mg, 66% yield) as a yellow solid. $^1H$ NMR (400 MHz, DMSO-$d_6$) δ 11.07 (s, 1H), 7.58 (dd, J=7.2, 8.0 Hz, 1H), 7.17-6.95 (m, 2H), 6.66 (t, J=6.0 Hz, 1H), 5.04 (dd, J=5.2, 12.8 Hz, 1H), 3.46 (t, J=6.0 Hz, 2H), 3.41-3.33 (m, 4H), 3.21 (t, J=6.8 Hz, 2H), 2.94-2.82 (m, 1H), 2.75 (s, 3H), 2.63-2.53 (m, 2H), 2.08-1.96 (m, 1H), 1.86-1.76 (m, 2H), 1.71-1.66 (m, 2H), 1.37 (s, 9H); LC-MS ($ESI^+$) m/z 503.4 $(M+H)^+$.

Step 2—2-(2,6-Dioxo-3-piperidyl)-4-[3-[3-(methylamino)propoxy]propylamino]isoindoline-1,3-dione To a solution of tert-butyl N-[3-[3-[[2-(2,6-dioxo-3-piperidyl)-1,3-dioxo-isoindolin-4-yl]amino]propoxy]propyl]-N-methyl-carbamate (140 mg, 278 umol) in DCM (5 mL) was added HCl/dioxane (4 M, 4 mL) at 25° C. The mixture was stirred at 25° C. for 2 hrs. On completion, the reaction mixture was concentrated in vacuo to give the title compound (120 mg, 98% yield, HCl salt) as a yellow solid. LC-MS (ESI$^+$) m/z 403.0 (M+H)$^+$.

Benzyl N-[2-(aminomethyl)spiro[3.5]nonan-7-yl]-N-methyl-carbamate (Intermediate ANJ)

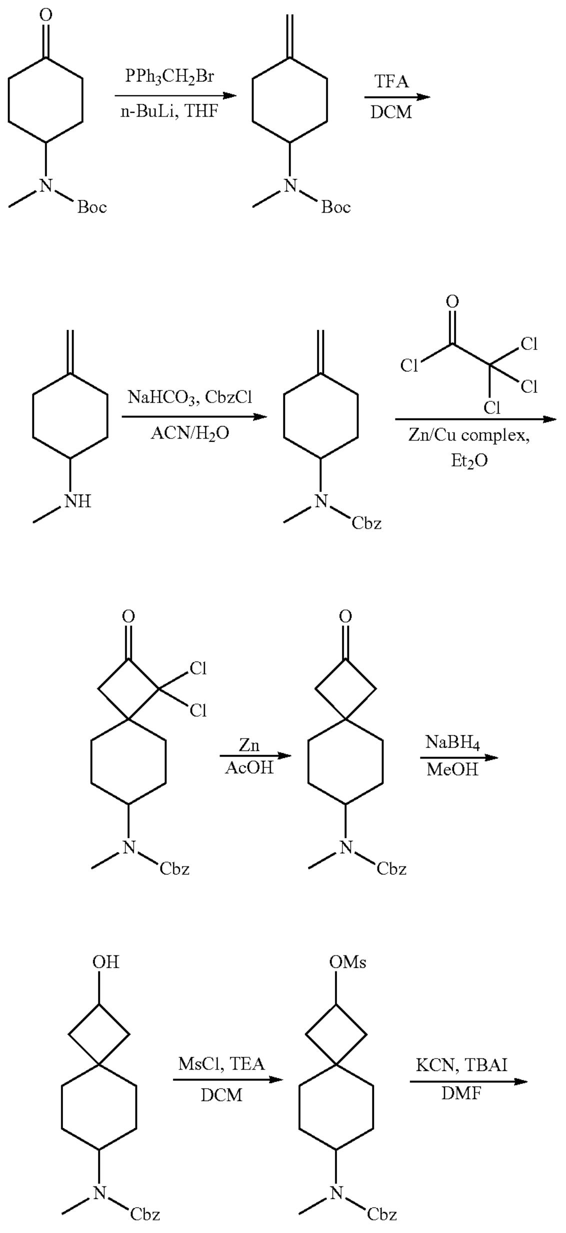

-continued

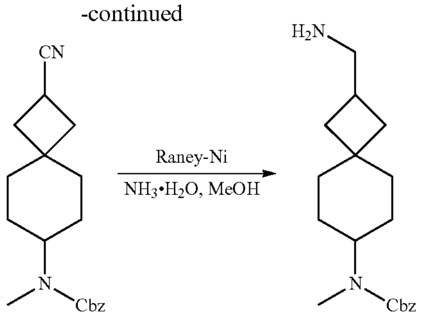

ANJ

Step 1—Tert-butyl N-methyl-N-(4-methylenecyclohexyl)carbamate

A solution of n-BuLi (2.5 M, 66.0 mL) was added to a mixture of methyltriphenylphosphonium bromide (58.9 g, 165 mmol) in tetrahydrofuran (200 mL) at −10° C. After stirring for 30 min at −10° C., the yellow suspension was cooled to −78° C. and a solution of tert-butyl N-methyl-N-(4-oxocyclohexyl)carbamate (25.0 g, 110 mmol, CAS #400899-84-5) in tetrahydrofuran (100 mL) was added. After stirring for 10 min at −78° C., the reaction mixture was warmed to 25° C. slowly and stirred for 3 hrs. On completion, the reaction mixture was quenched with saturated ammonium chloride (20 mL), then extracted with ethyl acetate (3×100 mL). The combined organic layers were washed with brine (100 mL), dried over anhydrous sodium sulfate, filtered and the filtrate was concentrated in vacuo. The residue was purified by column chromatography (Petroleum ether/Ethyl acetate=40/1) to give the title compound (23.7 g, 96% yield) as a white solid. $^1$H NMR (400 MHz, $CDCl_3$) δ 4.66 (s, 2H), 4.33-3.94 (m, 1H), 2.72 (s, 3H), 2.47-2.32 (m, 2H), 2.24-2.10 (m, 2H), 1.84-1.75 (m, 2H), 1.54-1.49 (m, 2H), 1.48 (m, 9H).

Step 2—N-methyl-4-methylene-cyclohexanamine

To a solution of tert-butyl N-methyl-N-(4-methylenecyclohexyl)carbamate (5.00 g, 22.2 mmol) in DCM (10 mL) was added tertfluoroacetic acid (7.70 g, 67.5 mmol, 5.00 mL). The reaction mixture was stirred at 20° C. for 2 hrs. On completion, the reaction mixture was concentrated in vacuo to give the title compound (5.31 g, 100% yield, TFA salt) as colorless oil. The product was unstable which was used for the next step without purification. $^1$H NMR (400 MHz, $CDCl_3$) δ 4.77 (s, 2H), 3.27-3.06 (m, 1H), 2.76-2.73 (m, 3H), 2.50-2.42 (m, 2H), 2.22-2.05 (m, 4H), 1.58-1.50 (m, 2H).

Step 3—Benzyl N-methyl-N-(4-methylenecyclohexyl)carbamate

To a solution of N-methyl-4-methylene-cyclohexanamine (5.31 g, 22.2 mmol, TFA salt) and $NaHCO_3$ (6.53 g, 77.7 mmol, 3.02 mL) in a mixed solvent of ACN (50 mL) and $H_2O$ (50 mL) was added CbzCl (5.68 g, 33.3 mmol, 4.73 mL). The reaction mixture was stirred at 25° C. for 12 hrs. On completion, the reaction mixture was concentrated in vacuo to remove ACN, and extracted with ethyl acetate (2×100 mL). The combined organic layer was washed with brine (20 mL), dried over anhydrous sodium sulfate, filtered and concentrated in vacuo. The residue was purified by silica gel chromatography (petroleum ether:ethyl acetate=50:1) to give the title compound (4.00 g, 68% yield) as a colorless oil. $^1$H NMR (400 MHz, $CDCl_3$) δ 7.42-7.28 (m, 5H), 5.15 (s, 2H), 4.66 (t, J=1.6 Hz, 2H), 4.33-4.01 (m, 1H), 2.79 (s, 3H), 2.37-2.34 (m, 2H), 2.18-2.15 (m, 2H), 1.87-1.73 (m, 2H), 1.57-1.48 (m, 2H). LC-MS ($ESI^+$) m/z 260.2 $(M+H)^+$.

Step 4—Benzyl N-(3,3-dichloro-2-oxo-spiro[3.5] nonan-7-yl)-N-methyl-carbamate

To a solution of benzyl N-methyl-N-(4-methylenecyclohexyl)carbamate (3.50 g, 13.5 mmol) in diethyl ether (70 mL) was added Zn/Cu complex (7 g). Then a mixture of 2,2,2-trichloroacetyl chloride (7.36 g, 40.5 mmol, 4.52 mL) in diethyl ether (140 mL) was added dropwise. The reaction mixture was stirred at 30° C. for 16 hrs. On completion, the reaction mixture was poured into saturated $NaHCO_3$ aqueous solution (100 mL) and filtered through a pad of Celite and the filtrate was collected. The organic layer was dried over anhydrous $Na_2SO_4$ and concentrated in vacuo to get a residue. The residue was purified by silica gel chromatography (petroleum ether/ethyl acetate=5/1) to give the title compound (3.80 g, 76% yield) as a white solid. H NMR (400 MHz, $CDCl_3$) δ 7.35-7.21 (m, 5H), 5.08 (s, 2H), 4.19-4.02 (m, 1H), 2.93 (s, 2H), 2.76 (s, 3H), 2.37-2.26 (m, 2H), 1.86-1.62 (m, 6H). LC-MS ($ESI^+$) m/z 370.0 $(M+H)^+$.

Step 5—Benzyl N-methyl-N-(2-oxospiro[3.5] nonan-7-yl)carbamate

To a solution of benzyl N-(3,3-dichloro-2-oxo-spiro[3.5] nonan-7-yl)-N-methyl-carbamate (3.30 g, 8.91 mmol) in acetic acid (10 mL) was added Zn (2.33 g, 35.6 mmol) at 15° C. The reaction mixture was stirred at 80° C. for 3 hrs. On completion, the reaction mixture was filtered and the filtrate was diluted with water (50 mL), then extracted with ethyl acetate (3×50 mL). The combined organic layers were washed saturated $NaHCO_3$ (30 mL) and brine (30 mL), dried over anhydrous sodium sulfate, filtered and concentrated in vacuo to give the title compound (2.40 g, 89% yield) as a gum oil. $^1$H NMR (400 MHz, $CDCl_3$) δ 7.46-7.28 (m, 5H), 5.15 (s, 2H), 4.20-3.84 (m, 1H), 2.90-2.68 (m, 7H), 1.86-1.68 (m, 6H), 1.55-1.42 (m, 2H); LC-MS ($ESI^+$) m/z 302.2 $(M+H)^+$.

Step 6—Benzyl N-(2-hydroxyspiro[3.5]nonan-7-yl)-N-methyl-carbamate

To a solution of benzyl N-methyl-N-(2-oxospiro[3.5] nonan-7-yl)carbamate (1.00 g, 3.32 mmol) in MeOH (10 mL) was added $NaBH_4$ (151 mg, 3.98 mmol) at 0° C., and the mixture was stirred at 25° C. for 1 h. On completion, the reaction mixture was quenched with water (5 mL). The mixture was concentrated in vacuo to remove methanol, then the solution was extracted with ethyl acetate (3×20 mL). The combined organic layers were washed with brine (10 mL), dried over anhydrous sodium sulfate, filtered and the filtrate was concentrated in vacuo to give the title compound (1.00 g, 99% yield) as a yellow oil. $^1$H NMR (400 MHz, $CDCl_3$) δ 7.44-7.28 (m, 5H), 5.14 (s, 2H), 4.28 (q, J=7.2 Hz, 1H), 4.05-3.75 (m, 1H), 2.79 (s, 3H), 2.40-2.27 (m, 1H), 2.22-2.11 (m, 1H), 1.71-1.64 (m, 3H), 1.62-1.51 (m, 4H), 1.48-1.46 (m, 3H); LC-MS ($ESI^+$) m z 304.1 $(M+H)^+$.

Step 7—[7-[Benzyloxycarbonyl(methyl)amino]spiro [3.5]nonan-2-yl]methanesulfonate To a solution of benzyl N-(2-hydroxyspiro[3.5]nonan-7-yl)-N-methyl-carbamate (1.00 g, 3.30 mmol) in DCM (20 mL) was added TEA (1.00 g, 9.89 mmol, 1.38 mL) and MsCl (566 mg, 4.94 mmol, 383 uL) at 0° C. . The reaction mixture was stirred at 20° C. for 3 hrs. On completion, the reaction mixture was quenched with water (10 mL). The organic layer was separated and washed with brine (50 mL), dried over anhydrous sodium sulfate, filtered and concentrated in vacuo to give the title compound (1.26 g, 100% yield) as yellow oil. $^1$H NMR (400 MHz, $CDCl_3$) δ 7.42-7.28 (m, 5H), 5.13 (s, 2H), 5.01-4.97 (m, 1H), 4.05-3.74 (m, 1H), 2.98 (s, 3H), 2.78 (s, 3H), 2.45 (m, 1H), 2.34-2.21 (m, 1H), 2.11-2.06 (m, 1H), 2.02-1.97 (m, 1H), 1.74-1.67 (m, 2H), 1.59-1.36 (m, 6H). LC-MS ($ESI^+$) m/z 382.1 $(M+H)^+$.

Step 8—Benzyl N-(2-cyanospiro[3.5]nonan-7-yl)-N-methyl-carbamate

To a solution of [7-[benzyloxycarbonyl(methyl)amino] spiro[3.5]nonan-2-yl]methanesulfonate (1.26 g, 3.30 mmol) in DMF (10 mL) was added KCN (430 mg, 6.61 mmol, 283 uL) and TBAI (122 mg, 330 umol). The reaction mixture was heated to 120° C. for 16 hrs. On completion, the reaction mixture was diluted with water (10 mL), and extracted with ethyl acetate (3×50 mL). The combined organic layers were wash with brine (30 mL), dried over anhydrous sodium sulfate, filtered and the filtrate was concentrated in vacuo. The residue was purified by silica gel chromatography (petroleum ether/ethyl acetate=4/1) to give the title compound (570 mg, 55% yield) as a yellow oil. $^1$H NMR (400 MHz, $CDCl_3$) δ 7.45-7.28 (m, 5H), 5.13 (s, 2H), 4.07-3.73 (m, 1H), 3.06-2.98 (m, 1H), 2.78 (s, 3H), 2.32-2.22 (m, 1H), 2.20-2.06 (m, 3H), 1.96-1.87 (m, 1H), 1.82-1.78 (m, 1H), 1.62-1.59 (m, 2H), 1.54-1.36 (m, 4H). LC-MS ($ESI^+$) m/z 313.1 $(M+H)^+$.

Step 9—Benzyl N-[2-(aminomethyl)spiro[3.5] nonan-7-yl]-N-methyl-carbamate

To a solution of benzyl N-(2-cyanospiro[3.5]nonan-7-yl)-N-methyl-carbamate (370 mg, 1.18 mmol) in MeOH (5 mL) was added Raney-Ni (101 mg, 1.18 mmol), $NH_3.H_2O$ (3.37 g, 31.7 mmol, 3.70 mL, 33% solution) under $N_2$. The suspension was degassed under vacuum and purged with $H_2$ several times. The mixture was stirred under $H_2$ (50 psi) at 25° C. for 4 hours. On completion, the reaction mixture was filtered and concentrated in vacuo to give the title compound (300 mg, 84% yield) as colorless oil. $^1$H NMR (400 MHz, $CDCl_3$) δ 7.47-7.29 (m, 5H), 5.15 (s, 2H), 4.89-4.50 (m, 2H), 4.04-3.78 (m, 1H), 2.79 (s, 3H), 2.69 (d, J=7.2 Hz, 2H), 2.28-2.20 (m, 1H), 2.02-1.73 (m, 6H), 1.48-1.31 (m, 6H); LC-MS ($ESI^+$) m/z 317.1 $(M+H)^+$.

2-(2,6-Dioxo-3-piperidyl)-4-[[7-(methylamino)spiro[3.5]nonan-2-yl]methylamino]isoindoline-1,3-dione (Intermediate ANK)

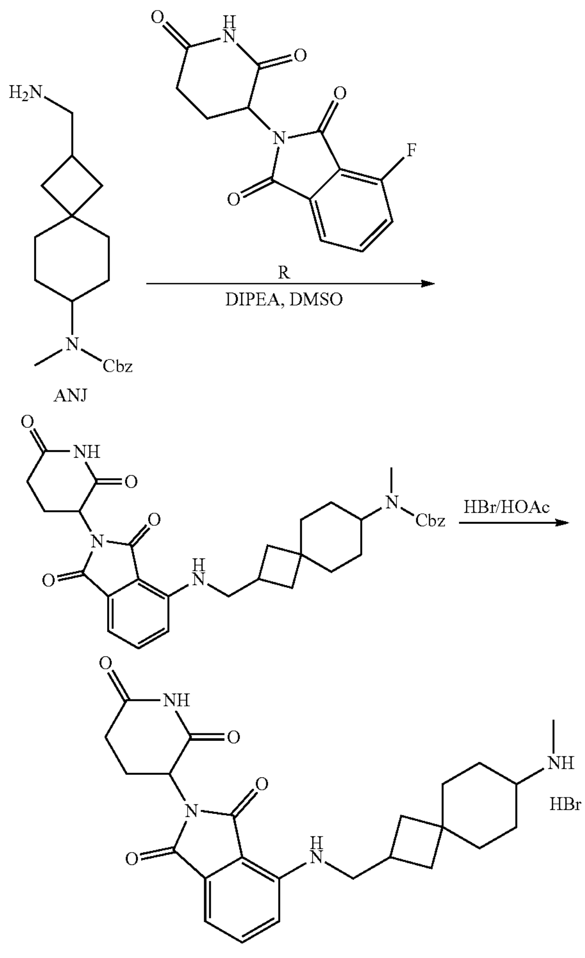

ANK

Step 1—Benzyl N-[2-[[[2-(2,6-dioxo-3-piperidyl)-1,3-dioxo-isoindolin-4-yl]amino]methyl]spiro[3.5]nonan-7-yl]-N-methyl-carbamate To a solution of benzyl N-[2-(aminomethyl)spiro[3.5]nonan-7-yl]-N-methyl-carbamate (300 mg, 948 umol, Intermediate ANJ) and 2-(2,6-dioxo-3-piperidyl)-4-fluoro-isoindoline-1,3-dione (262 mg, 948 umol, Intermediate R) in DMSO (5 mL) was added DIPEA (367 mg, 2.84 mmol). The reaction mixture was stirred at 90° C. for 3 hrs. On completion, the reaction mixture was acidified to pH=6 with formic acid (0.1 mL). The mixture was filtered and the filtrate was purified by reverse phase flash (0.1% FA condition) to give the title compound (100 mg, 18% yield) as a yellow solid. $^1H$ NMR (400 MHz, $CDCl_3$) δ 7.88 (s, 1H), 7.46-7.40 (m, 1H), 7.31-7.24 (m, 5H), 7.02 (d, J=7.2 Hz, 1H), 6.80 (d, J=8.8 Hz, 1H), 6.11 (t, J=5.2 Hz, 1H), 5.06 (s, 2H), 4.84 (dd, J=5.2, 12.8 Hz, 1H), 3.99-3.66 (m, 1H), 3.32-3.11 (m, 2H), 2.85-2.65 (m, 6H), 2.53-2.41 (m, 1H), 2.10-2.01 (m, 1H), 1.89-1.74 (m, 2H), 1.61-1.52 (m, 2H), 1.46-1.33 (m, 8H). LC-MS ($ESI^+$) m/z 573.1 $(M+H)^+$.

Step 2—2-(2,6-Dioxo-3-piperidyl)-4-[[7-(methylamino)spiro[3.5]nonan-2-yl]methylamino]isoindoline-1,3-dione A mixture of benzyl N-[2-[[[2-(2,6-dioxo-3-piperidyl)-1,3-dioxo-isoindolin-4-yl]amino]methyl]spiro[3.5]nonan-7-yl]-N-methyl-carbamate (50 mg, 87.3 umol) in HBr/HOAc (1 mL) was degassed and purged with $N_2$ for 3 times, and then the mixture was stirred at 25° C. for 12 hrs under $N_2$ atmosphere. On completion, the reaction mixture was concentrated in vacuo to give the title compound (45 mg, 99% yield, HBr salt) as a white solid. LC-MS ($ESI^+$) m/z 439.2 $(M+H)^+$.

N-[6-(difluoromethyl)-2-(4-formylcyclohexyl)indazol-5-yl]-6-(trifluoromethyl)pyridine-2-carboxamide (Intermediate ALU)

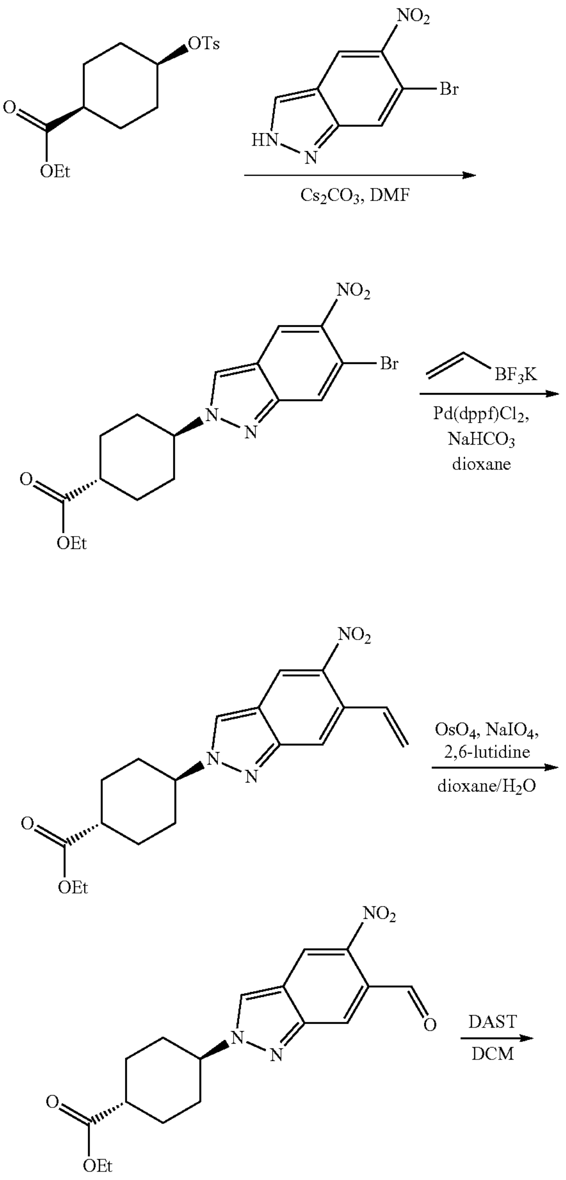

-continued

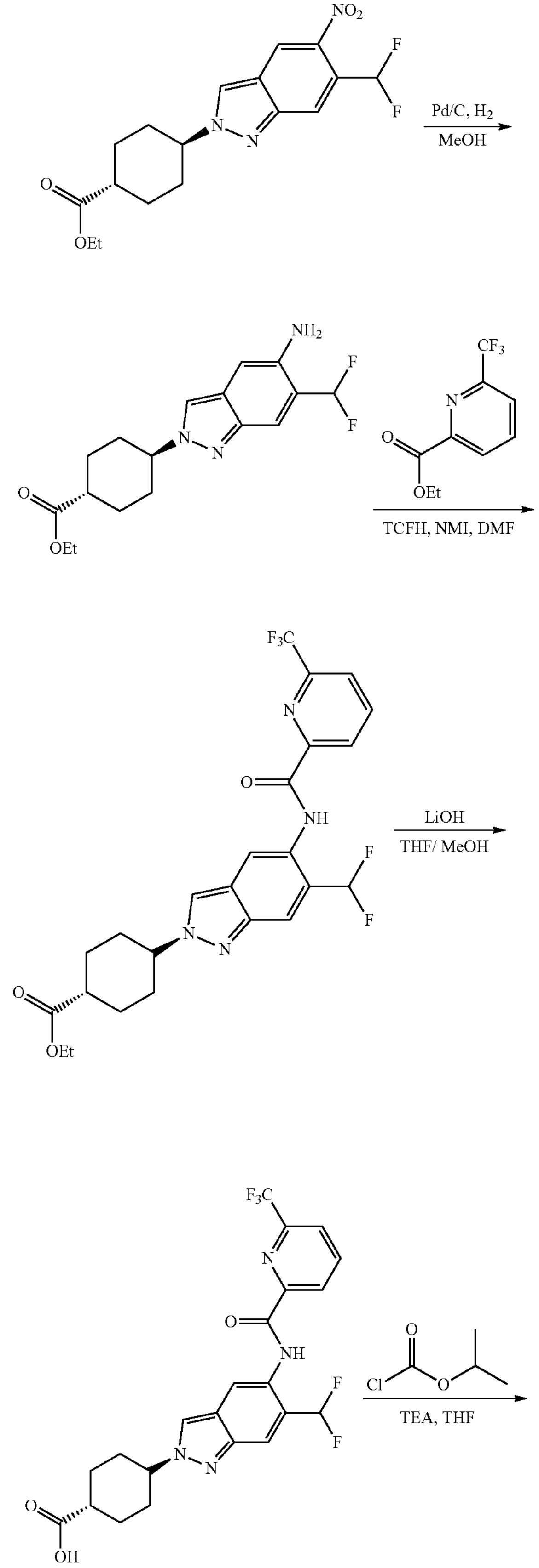

-continued

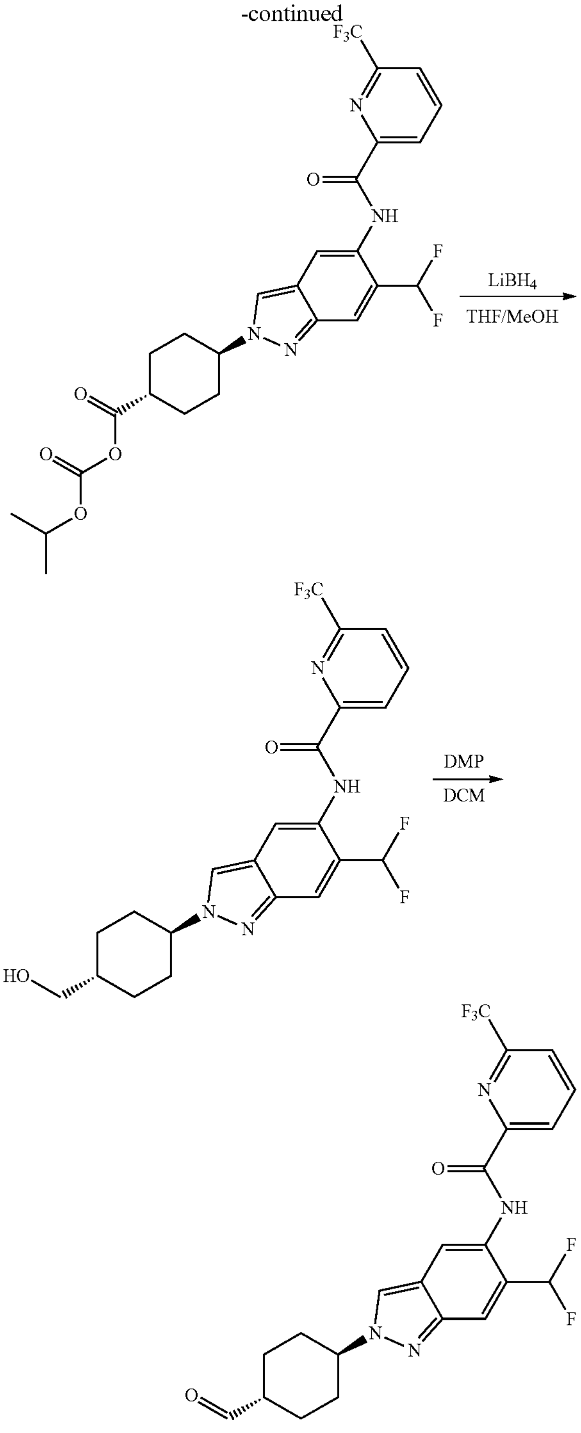

ALU

Step 1—Ethyl 4-(6-bromo-5-nitro-indazol-2-yl)cyclohexanecarboxylate

To a solution of 6-bromo-5-nitro-2H-indazole (8.30 g, 34.3 mmol, CAS #1351813-02-9) and ethyl 4-(p-tolylsulfonyloxy)cyclohexanecarboxylate (22.4 g, 68.6 mmol, Intermediate AGK) in DMF (100 mL) was added $Cs_2CO_3$ (22.4 g, 68.6 mmol). The mixture was stirred at 80° C. for 24 hrs. On completion, the reaction mixture was concentrated in vacuo to remove solvent. Then to the mixture was added 100 mL water and extracted with EA 150 mL (3×50 mL). The combined organic layers were washed with 100 mL brine, dried over $Na_2SO_4$, filtered and concentrated in vacuo to give a residue. The residue was purified by flash silica gel chromatography (PE:EA 2:1) and then the residue was purified by pre-HPLC (column: Phenomenex Synergi Max-RP 250*50 mm*10 um; mobile phase: [water (0.1% TFA)-ACN]; B %: 45ACN %-75ACN %, 29 min) to give the title compound (1.60 g, 40% yield) as yellow solid. $^1H$ NMR (400 MHz, DMSO-$d_6$) δ 8.60 (s, 1H), 8.45 (s, 1H), 8.34 (s, 1H), 4.91-4.71 (m, 1H), 4.08 (q, J=7.2 Hz, 2H), 2.47-2.40 (m, 1H), 2.10-1.89 (m, 6H), 1.74-1.55 (m, 2H), 1.20 (t, J=7.2 Hz, 3H).

Step 2—2-(2,6-Dioxo-3-piperidyl)-4-[[(2R)-morpholin-2-yl]methylamino]isoindoline-1,3-dione To a solution of ethyl 4-(6-bromo-5-nitro-indazol-2-yl) cyclohexanecarboxylate (1.60 g, 4.04 mmol) and potassium; trifluoro(vinyl)boranuide (1.62 g, 12.1 mmol) and potassium;trifluoro(vinyl)boranuide (1.62 g, 12.1 mmol) in dioxane (100 mL) was added Pd(dppf)$Cl_2$ (329 mg, 403 umol) and $NaHCO_3$ (2 M, 4.04 mL). The mixture was stirred at 90° C. for 6 hrs. On completion, the mixture was filtered with celite and concentrated in vacuo. The crude product was purified by flash silica gel chromatography (PE:EA 1:1) to give the title compound (1.39 g, 50% yield) as yellow solid. LC-MS ($ESI^+$) m/z 344.1 $(M+1)^+$.

Step 3—Ethyl 4-(6-formyl-5-nitro-indazol-2-yl) cyclohexanecarboxylate

A mixture of ethyl 4-(5-nitro-6-vinyl-indazol-2-yl)cyclohexanecarboxylate (1.39 g, 4.20 mmol), $NaIO_4$ (3.74 g, 17.4 mmol), $OsO_4$ (33.3 mg, 131 umol) and 2,6-dimethylpyridine (936 mg, 8.74 mmol, 1.02 mL) in a mixed solvents of dioxane (20 mL) and $H_2O$ (20 mL) was stirred at 0° C. for 1 hour. On completion, the mixture was added 10 mL $Na_2S_2O_4$ and extracted with DCM 150 mL (3×50 mL). The combined organic layers were washed with 100 mL brine, dried over $Na_2SO_4$, filtered and concentrated in vacuo to give the title compound (1.50 g, 80% yield) as yellow solid. LC-MS ($ESI^+$) m/z 346.0 $(M+1)^+$.

Step 4—Ehyl 4-[6-(difluoromethyl)-5-nitro-indazol-2-yl]cyclohexanecarboxylate

To a solution of ethyl 4-(6-formyl-5-nitro-indazol-2-yl) cyclohexanecarboxylate (1.50 g, 4.34 mmol) in DCM (80 mL) was added DAST (1.75 g, 10.8 mmol). The mixture was stirred at 0° C. for 2 hrs. On completion, to the mixture was added 2 mL $H_2O$ slowly at 0° C., then the solution was concentrated in vacuo. The crude product was purified by reverse phase HPLC (0.1% TFA condition) to give the title compound (900 mg, 56% yield) as yellow solid. $^1H$ NMR (400 MHz, DMSO-$d_6$) δ 8.87 (d, J=5.2 Hz, 2H), 8.07 (s, 1H), 7.73-7.37 (m, 1H), 4.71-4.66 (m, 1H), 4.09 (q, J=7.2 Hz, 2H), 2.24-2.15 (m, 2H), 2.13-1.92 (m, 4H), 1.61 (dq, J=3.1, 12.8 Hz, 2H), 1.20 (t, J=7.2 Hz, 3H); LC-MS ($ESI^+$) m/z 368.1 $(M+1)^+$.

Step 5—Ethyl 4-[5-amino-6-(difluoromethyl)indazol-2-yl]cyclohexanecarboxylate

To a solution of ethyl 4-[6-(difluoromethyl)-5-nitro-indazol-2-yl]cyclohexanecarboxylate (900 mg, 2.45 mmol) in THE (20 mL) was added Pd/C (500 mg, 10 wt %). The mixture was stirred at 15° C. for 2 hrs under $H_2$ (15 psi). On completion, the mixture was filtered through celite and concentrated in vacuo to give the title compound (800 mg, 96% yield) as yellow oil. $^1H$ NMR (400 MHz, DMSO-$d_6$) δ 8.07 (s, 1H), 7.65 (s, 1H), 7.23-6.91 (m, 1H), 6.84 (s, 1H), 4.78 (s, 2H), 4.48-4.32 (m, 1H), 3.62 (s, 3H), 2.48-2.40 (m, 1H), 2.17-2.02 (m, 4H), 1.99-1.86 (m, 2H), 1.64-1.50 (m, 2H).

Step 6—Ethyl 4-[6-(difluoromethyl)-5-[[6-(trifluoromethyl)pyridine-2-carbonyl]amino]indazol-2-yl] cyclohexanecarboxylate To a solution of 6-(trifluoromethyl)pyridine-2-carboxylic acid (679 mg, 3.56 mmol) and ethyl 4-[5-amino-6-(difluoromethyl)indazol-2-yl]cyclohexanecarboxylate (800 mg, 2.37 mmol) in DMF (20 mL) was added HATU (1.35 g, 3.56 mmol) and DIPEA (919 mg, 7.11 mmol). The mixture was stirred at 70° C. for 2 hrs. On completion, the mixture was added 0.5 mL water, the residue was purified by prep-HPLC (column: Phenomenex luna C18 250*50 mm*10 um; mobile phase: [water (0.1% TFA)-ACN]; B %: 68%-98%, 9 min) to give the title compound (750 mg, 59% yield) as light yellow solid. $^1H$ NMR (400 MHz, DMSO-$d_6$) δ 10.50 (s, 1H), 8.56 (s, 1H), 8.49 (s, 1H), 8.48-8.38 (m, 2H), 8.23 (dd, J=1.2, 7.6 Hz, 1H), 8.00 (s, 1H), 7.43-7.09 (m, 1H), 4.65-4.52 (m, 1H), 4.10 (q, J=7.2 Hz, 2H), 2.26-2.16 (m, 2H), 2.12-1.95 (m, 4H), 1.69-1.56 (m, 2H), 1.21 (t, J=7.2 Hz, 3H); LC-MS ($ESI^+$) m/z 511.1 $(M+1)^+$.

Step 7—Ethyl 4-[6-(difluoromethyl)-5-[[6-(trifluoromethyl)pyridine-2-carbonyl]amino]indazol -2-yl] cyclohexane carboxylic acid To a solution of ethyl 4-[6-(difluoromethyl)-5-[[6-(trifluoromethyl)pyridine-2-carbonyl]amino]indazol-2-yl]cyclohexanecarboxylate (300 mg, 587 umol) in THE (1 mL) and MeOH (0.1 mL) and $H_2O$ (1 mL) was added LiOH $H_2O$ (123 mg, 2.94 mmol). The mixture was stirred at 15° C. for 2 hrs. On completion, the mixture was concentrated in vacuo and M HCl was added to the mixture until the pH=5-6 then the mixture was filtered. The filtered cake was dried in vacuo to give the title compound (250 mg, 88% yield) as yellow solid. LC-MS ($ESI^+$) m/z 483.2 $(M+1)^+$.

Step 8—Isopropoxycarbonyl 4-[6-(difluoromethyl)-5-[[6-(trifluoromethyl)pyridine-2-carbonyl]amino] indazol-2-yl]cyclohexanecarboxylate To a solution of 4-[6-(difluoromethyl)-5-[[6-(trifluoromethyl)pyridine-2-carbonyl]amino]indazol-2-yl]cyclohexanecarboxylic acid (100 mg, 207 umol) in THF (1 mL) was added $Et_3N$ (83.9 mg, 829 umol) and isopropyl carbonochloridate (63.5 mg, 518 umol). The mixture was stirred at 0° C. for 2 hrs. On completion, the mixture was filtered and the cake was washed with THE (3×5 mL). The organic phase was concentrated in vacuo to give the title compound (100 mg, 85% yield) as yellow oil. LC-MS ($ESI^+$) m/z 569.0 $(M+1)^+$.

Step 9—N-[6-(difluoromethyl)-2-[4-(hydroxymethyl)cyclohexyl]indazol-5-yl]-6-(trifluoromethyl) pyridine-2-carboxamide To a solution of isopropoxycarbonyl 4-[6-(difluoromethyl)-5-[[6-(trifluoromethyl)pyridine-2-carbonyl]amino] indazol-2-yl]cyclohexanecarboxylate (100 mg, 175 umol) in THE (10 mL) and $H_2O$ (1 mL) was added $LiBH_4$ (23.0 mg, 1.06 mmol). The mixture was stirred at 0° C. for 2 hrs. The mixture was added 10 mL $NH_4Cl$ and extracted with EA (3×50 mL). The combined organic layers were washed with 50 mL brine, dried over $Na_2SO_4$, filtered and concentrated in vacuo to give the title compound (80.0 mg, 97% yield) as yellow solid. LC-MS ($ESI^+$) m/z 469.0 $(M+1)^+$.

Step 10—N-[6-(difluoromethyl)-2-(4-formylcyclohexyl)indazol-5-yl]-6-(trifluoromethyl)pyridine-2-carboxamide To a solution of N-[6-(difluoromethyl)-2-[4-(hydroxymethyl)cyclohexyl]indazol-5-yl]-6-(trifluoro methyl)pyridine-2-carboxamide (80.0 mg, 170 umol) in DCM (10 mL) was added DMP (108 mg, 256 umol). The mixture was stirred at 15° C. for 2 hrs. On completion, the mixture was added 10 mL sat. $Na_2S_2O_3$ and 10 mL sat. $NaHCO_3$ and extracted with DCM 150 mL (3×50 mL). The combined organic layers were washed with 100 mL brine, dried over $Na_2SO_4$, filtered and the organic phase was concentrated in vacuo to give the title compound (80.0 mg, 95% yield) as yellow solid. LC-MS ($ESI^+$) m/z 467.1 $(M+1)^+$.

Tert-butyl 2-(aminomethyl)-7-azaspiro[3.5]nonane-7-carboxylate (Intermediate AJZ)

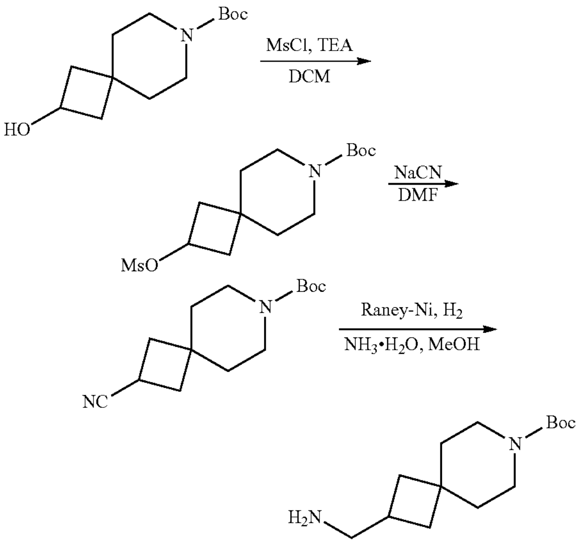

AJZ

Step 1—Tert-butyl 2-methylsulfonyloxy-7-azaspiro[3.5]nonane-7-carboxylate

To a solution of tert-butyl 2-hydroxy-7-azaspiro[3.5]nonane-7-carboxylate (2.00 g, 8.29 mmol, CAS #240401-28-9) and TEA (2.10 g, 20.7 mmol) in DCM (30 mL) was added MsCl (1.14 g, 9.95 mmol) dropwise at 0° C. Then the reaction mixture was stirred at 20° C. for 2 hrs. On completion, the mixture was quenched with water (50 mL), then extracted with DCM (2×50 mL). The organic layer was washed with citric acid (100 ml), brine (2×100 mL), dried with $Na_2SO_4$, filtered and the filtrate was concentrated in vacuo to give the title compound (2.60 g, 98% yield) as a yellowish oil. $^1H$ NMR (400 MHz, $CDCl_3$) δ 5.04 (t, J=7.2 Hz, 1H), 3.38-3.28 (m, 4H), 2.99 (s, 3H), 2.48-2.36 (m, 2H), 2.14-2.04 (m, 2H), 1.58-1.51 (m, 4H), 1.45 (s, 9H).

Step 2—Tert-butyl 2-cyano-7-azaspiro[3.5]nonane-7-carboxylate

To a solution of tert-butyl 2-methylsulfonyloxy-7-azaspiro[3.5]nonane-7-carboxylate (2.60 g, 8.14 mmol) in DMF (20 mL) was added NaCN (598 mg, 12.2 mmol). The reaction mixture was stirred at 120° C. for 3 days. On completion, the reaction mixture was cooled to 25° C., diluted with water (100 mL), then extracted with EA (2×100 mL). The organic layer was washed with brine (2×100 mL) and concentrated in vacuo. The residue was purified by silica gel chromatography to give the title compound (1.32 g, 65% yield) as a white solid. $^1H$ NMR (400 MHz, $CDCl_3$) δ 3.36-3.29 (m, 4H), 3.13-3.02 (m, 1H), 2.30-2.14 (m, 4H), 1.66-1.62 (m, 2H), 1.58-1.53 (m, 2H), 1.45 (s, 9H).

Step 3—Tert-butyl 2-(aminomethyl)-7-azaspiro[3.5]nonane-7-carboxylate

To a solution of tert-butyl 2-cyano-7-azaspiro[3.5]nonane-7-carboxylate (200 mg, 799 umol) and $NH_3.H_2O$ (0.2 mL) in MeOH (5 mL) was added Raney-Ni (30 mg). The reaction mixture was stirred at 20° C. for 16 hrs under $H_2$ (15 Psi) atmosphere. On completion, the mixture was filtered and the filtrate was concentrated in vacuo to give the title compound (200 mg, 98% yield) as a white solid. $^1H$ NMR (400 MHz, $CDCl_3$) δ 3.37-3.32 (m, 2H), 3.30-3.23 (m, 2H), 2.70 (d, J=7.2 Hz, 2H), 2.33-2.24 (m, 1H), 1.97-1.88 (m, 2H), 1.59-1.55 (m, 2H), 1.45 (s, 9H), 1.44-1.37 (m, 4H).

4-(7-azaspiro[3.5]nonan-2-ylmethylamino)-2-(2,6-dioxo-3-piperidyl)isoindoline-1,3-dione (Intermediate AJF)

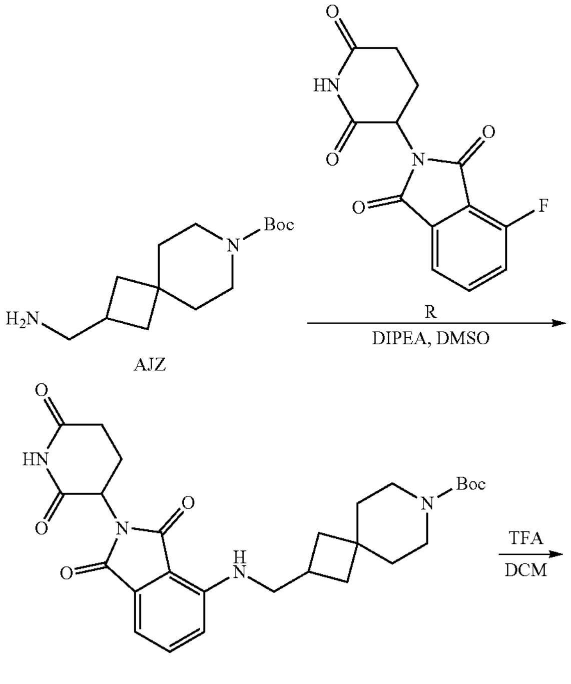

-continued

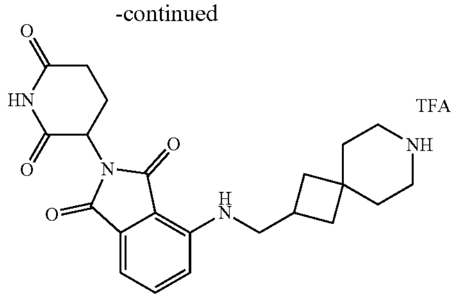

AJF

Step 1—Tert-butyl 2-[[[2-(2,6-dioxo-3-piperidyl)-1,3-dioxo-isoindolin-4-yl]amino]methyl]-7-azaspiro[3.5]nonane-7-carboxylate To a solution of tert-butyl 2-(aminomethyl)-7-azaspiro[3.5]nonane-7-carboxylate (200 mg, 786 umol, Intermediate AJZ) and 2-(2,6-dioxo-3-piperidyl)-4-fluoro-isoindoline-1,3-dione (228 mg, 825 umol, Intermediate R) in DMSO (3 mL) was added DIPEA (254 mg, 1.97 mmol). The reaction mixture was stirred at 125° C. for 3 hrs. On completion, the reaction mixture was diluted with water (50 mL), then extracted with EA (50 mL). The organic layer was concentrated in vacuo. The residue was purified by reverse phase (0.1% FA condition) to give the title compound (260 mg, 65% yield) as a yellow solid. LC-MS ($ESI^+$) m/z 511.3 $(M+H)^+$.

Step 2—4-(7-Azaspiro[3.5]nonan-2-ylmethylamino)-2-(2,6-dioxo-3-piperidyl)isoindoline-1,3-dione To a solution of tert-butyl 2-[[[2-(2,6-dioxo-3-piperidyl)-1,3-dioxo-isoindolin-4-yl]amino]methyl]-7- azaspiro[3.5]nonane-7-carboxylate (80.0 mg, 157 umol) in TFA (2 mL) was added DCM (2 mL). The reaction mixture was stirred at 20° C. for 2 hrs. On completion, the mixture was concentrated in vacuo to give the title compound (80 mg, 97% yield, TFA salt) as a yellow solid. LC-MS ($ESI^+$) m/z 411.2 $(M+H)^+$ 3-[3-Methyl-4-[[4-(methylamino)-1-piperidyl]methyl]-2-oxo-benzimidazol-1-yl]piperidine-2,6-dione (Intermediate WX)

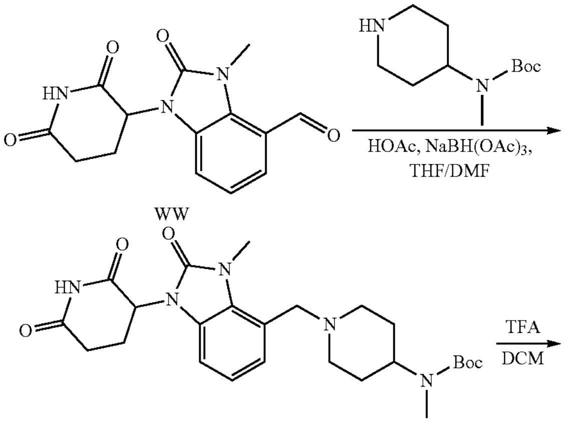

-continued

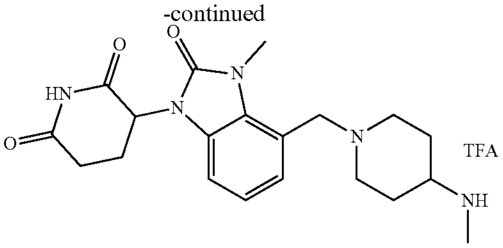

WX

Step 1—Tert-butyl N-[1-[[1-(2,6-dioxo-3-piperidyl)-3-methyl-2-oxo-benzimidazol-4-yl]methyl]-4- piperidyl]-N-methyl-carbamate To a solution of 1-(2,6-dioxo-3-piperidyl)-3-methyl-2-oxo-benzimidazole-4-carbaldehyde (160 mg, 556 umol, Intermediate WW) and tert-butyl N-methyl-N-(4-piperidyl) carbamate (119 mg, 556 umol) in a mixed solvents of THF (3 mL) and DMF (1.5 mL) was added AcOH until the pH=5-7. After the reaction mixture was stirred at 20° C. for 3 hours. $NaBH(OAc)_3$ (177 mg, 835 umol) was added to the reaction mixture. The mixture was stirred at 20° C. for 12 hours. On completion, the reaction mixture was quenched by water (3 drops) and filtered. The filtrate was concentrated in vacuo. The residue was purified by reverse phase (FA condition) to give the title compound (220 mg, 46% yield) as white solid. LC-MS ($ESI^+$) m/z 486.2 $(M+H)^+$.

Step 2—3-[3-Methyl-4-[[4-(methylamino)-1-piperidyl]methyl]-2-oxo-benzimidazol-1-yl]piperidine-2,6-dione To a solution of tert-butyl N-[1-[[1-(2,6-dioxo-3-piperidyl)-3-methyl-2-oxo-benzimidazol-4- yl]methyl]-4-piperidyl]-N-methyl-carbamate (200 mg, 235 umol) in DCM (3 mL) was added TFA (3 mL). The reaction mixture was stirred at 15° C. for 0.5 hour. On completion, the reaction mixture was concentrated in vacuo to give the title compound (220 mg, 100% yield, TFA salt) as yellow oil. LC-MS ($ESI^+$) m/z 386.2 $(M+H)^+$.

N-[1-(4-formylcyclohexyl)-6-(1-hydroxy-1-methyl-ethyl)indazol-5-yl]-6-(trifluoromethyl)pyridine-2-carboxamide (Intermediate ALT)

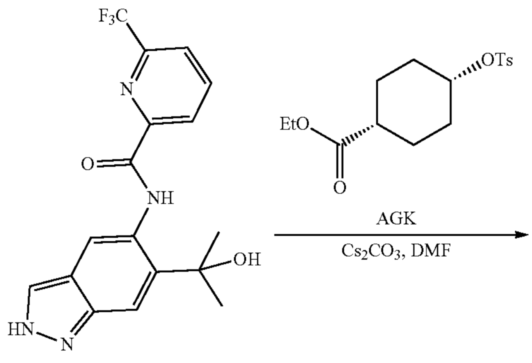

-continued

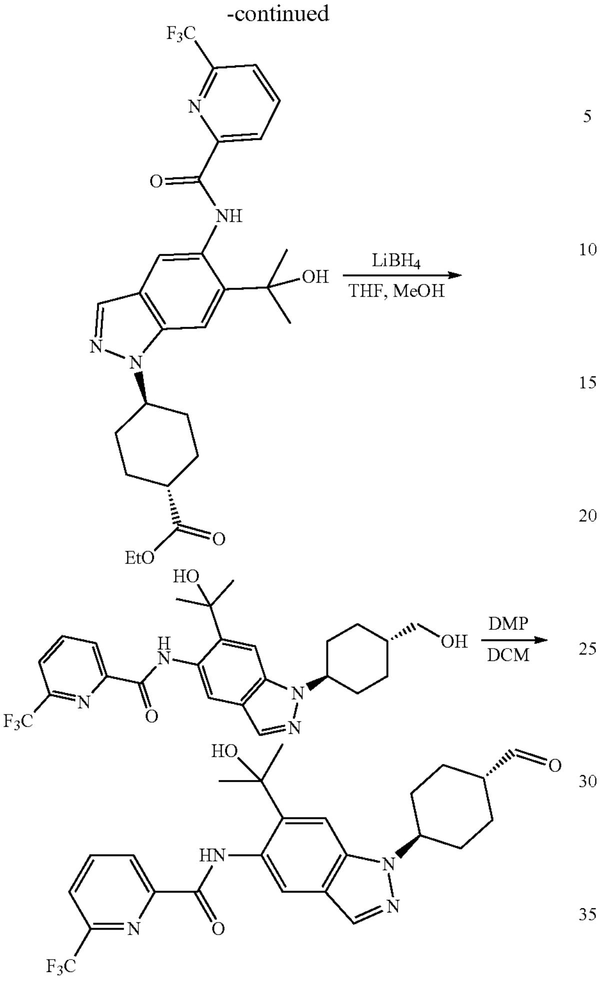

ALT

Step 1—Ethyl 4-[6-(1-hydroxy-1-methyl-ethyl)-5-[[6-(trifluoromethyl)pyridine-2-carbonyl]amino]indazol-1-yl]cyclohexanecarboxylate The reaction was performed in parallel for two batches: A mixture of N-[6-(1-hydroxy-1-methyl-ethyl)-2H-indazol-5-yl]-6-(trifluoromethyl)pyridine-2-carboxamide (1.30 g, 3.57 mmol, Intermediate TJ), ethyl 4-(p-tolylsulfonyloxy)cyclohexanecarboxylate (2.33 g, 7.14 mmol, Intermediate AGK) and $Cs_2CO_3$ (2.33 g, 7.14 mmol) in DMF (20 mL) was stirred at 80° C. for 16 hours. Then ethyl 4-(p-tolylsulfonyloxy)cyclohexanecarboxylate (2.33 g, 7.14 mmol) and $Cs_2CO_3$ (2.33 g, 7.14 mmol) was added to the mixture at 15° C., the mixture was stirred at 80° C. for 16 hours. On completion, the reaction mixture was cooled to 15° C., the mixtures of two batches were combined, diluted with water (100 mL), and extracted with EA (3×60 mL). The organic layer was washed with brine (20 mL), dried over $Na_2SO_4$, filtered and concentrated in vacuo to give a residue. The residue was purified by reverse phase flash and prep-HPLC (column: Phenomenex Synergi Max-RP 150*50 mm*10 um; mobile phase: [water (0.225% FA)-ACN]; B %: 52%-82%, 11 min) to give the title compound (1.80 g, 48% yield) as a yellow oil. $^1H$ NMR (400 MHz, $CDCl_3$) δ 8.91 (s, 1H), 8.50 (d, J=7.6 Hz, 1H), 8.10 (t, J=8.0 Hz, 1H), 7.92 (s, 1H), 7.84 (d, J=7.6 Hz, 1H), 7.74 (s, 1H), 4.43-4.35 (m, 1H), 4.17 (q, J=7.2 Hz, 2H), 2.48-2.40 (m, 1H), 2.36-2.34 (m, 2H), 2.28-1.97 (m, 5H), 1.81 (s, 6H), 1.76-1.64 (m, 2H), 1.29 (t, J=7.2 Hz, 3H).

Step 2—N-[1-[4-(hydroxymethyl)cyclohexyl]-6-(1-hydroxy-1-methyl-ethyl)indazol-5-yl]-6-(trifluoromethyl)pyridine-2-carboxamide To a solution of ethyl 4-[6-(1-hydroxy-1-methyl-ethyl)-5-[[6-(trifluoromethyl)pyridine-2-carbonyl]amino]indazol-1-yl]cyclohexanecarboxylate (200 mg, 385 umol) in THE (8 mL) and MeOH (1 mL) was added $LiBH_4$ (25 mg, 1.16 mmol) at 0° C. The reaction mixture was stirred at 0-10° C. for 2 hrs. On completion, the reaction mixture was quenched by addition $H_2O$ (1 mL), 15% aq NaOH (1 mL) and $H_2O$ (3 mL) at 0° C. The mixture was dried over by $Na_2SO_4$, filtered and concentrated in vacuo to give the title compound (230 mg, 93% yield, 75% purity) as yellow oil. $^1H$ NMR (400 MHz, DMSO-$d_6$) δ 12.35 (s, 1H), 8.74 (s, 1H), 8.46 (d, J=7.6 Hz, 1H), 8.37 (t, J=8.0 Hz, 1H), 8.16 (d, J=7.6 Hz, 1H), 8.03 (s, 1H), 7.65 (s, 1H), 5.98 (s, 1H), 4.72-4.60 (m, 1H), 4.49 (t, J=5.2 Hz, 1H), 3.32-3.26 (m, 2H), 1.97-1.84 (m, 7H), 1.65 (s, 6H), 1.54-1.43 (m, 2H).

Step 3—N-[i-(4-formylcyclohexyl)-6-(1-hydroxy-1-methyl-ethyl)indazol-5-yl]-6-(trifluoromethyl)pyridine-2-carboxamide To a solution of N-[1-[4-(hydroxymethyl)cyclohexyl]-6-(1-hydroxy-1-methyl-ethyl)indazol-5-yl]-6-(trifluoromethyl)pyridine-2-carboxamide (80.0 mg, 167 umol) in DCM (2 mL) was added DMP (85.4 mg, 201 umol) at 0° C. The reaction mixture was stirred at 25° C. for 2 hrs. On completion, the reaction mixture was quenched by addition sat. aq. $Na_2S_2O_3$ (10 mL) and $NaHCO_3$ (10 mL) and was extracted with DCM (3×10 mL). The combined organic layers were concentrated in vacuo to give the title compound (60.0 mg, 75% yield) as a white solid. LC-MS ($ESI^+$) m/z 475.4 $(M+H)^+$.

4-(7-Azaspiro[3.5]nonan-2-ylamino)-2-(2,6-dioxo-3-piperidyl)isoindoline-1,3-dione (Intermediate AML)

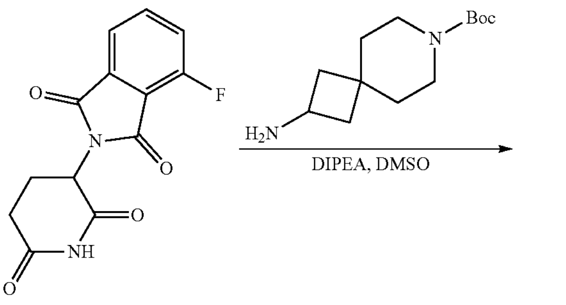

R

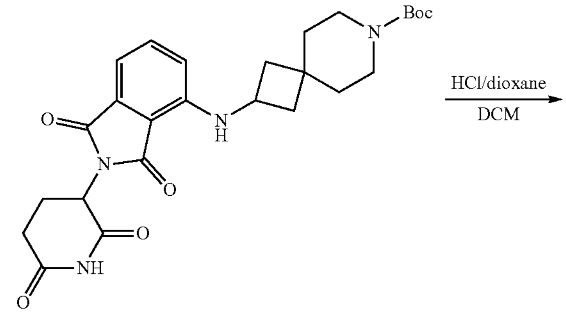

-continued

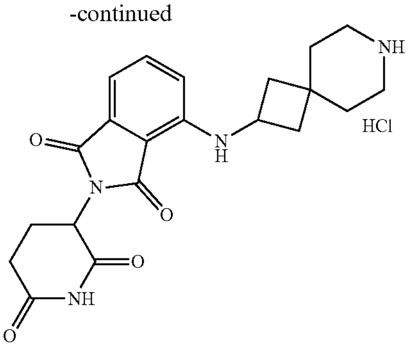

AML

Step 1—Tert-butyl 2-[[2-(2,6-dioxo-3-piperidyl)-1,3-dioxo-isoindolin-4-yl]amino]-7-azaspiro[3.5]nonane-7-carboxylate To a mixture of 2-(2,6-dioxo-3-piperidyl)-4-fluoro-isoindoline-1,3-dione (0.50 g, 1.81 mmol, Intermediate R) and tert-butyl 2-amino-7-azaspiro[3.5]nonane-7-carboxylate (478 mg, 1.99 mmol, CAS #1239319-82-4) in DMSO (10 mL) was added DIPEA (468 mg, 3.62 mmol). The mixture was stirred at 130° C. for 2 hours. On completion, the reaction mixture was poured into the water (30 mL), and extracted with EA (2×20 mL). The combined organic phase was washed with brine (2×30 mL), dried with anhydrous $Na_2SO_4$, filtered and concentrated in vacuo to give the title compound (0.80 g, 89% yield) as a yellow solid. $^1H$ NMR (400 MHz, $CDCl_3$) δ 8.33 (s, 1H), 7.48 (d, J=7.8 Hz, 1H), 7.11 (d, J=7.2 Hz, 1H), 6.74 (d, J=8.4 Hz, 1H), 6.31 (d, J=5.6 Hz, 1H), 4.95-4.89 (m, 1H), 4.08-3.99 (m, 1H), 3.42-3.35 (m, 2H), 3.33-3.26 (m, 2H), 2.93-2.84 (m, 1H), 2.83-2.71 (m, 2H), 2.48-2.35 (m, 2H), 2.17-2.09 (m, 1H), 1.78-1.71 (m, 2H), 1.65-1.60 (m, 2H), 1.58-1.52 (m, 2H), 1.45 (s, 9H).

Step 2—4-(7-Azaspiro[3.5]nonan-2-ylamino)-2-(2,6-dioxo-3-piperidyl)isoindoline-1,3-dione To a mixture of tert-butyl 2-[[2-(2,6-dioxo-3-piperidyl)-1,3-dioxo-isoindolin-4-yl]amino]-7-azaspiro[3.5]nonane-7-carboxylate (0.80 g, 1.61 mmol) in DCM (20 mL) was added HCl/dioxane (4 M, 1.21 mL). The reaction mixture was stirred at 20° C. for 0.5 hour. On completion, the reaction mixture was concentrated in vacuo to give the title compound (690 mg, 98% yield) as a yellow solid. LC-MS ($ESI^+$) m/z 397.2 $(M+H)^+$.

3-[4-(2,6-diazaspiro[3.3]heptan-2-ylmethyl)-3-methyl-2-oxo-benzimidazol- 1-yl]piperidine-2,6-dione (Intermediate AOE)

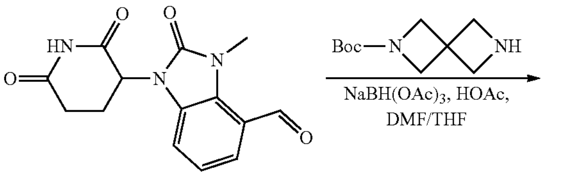

WW

-continued

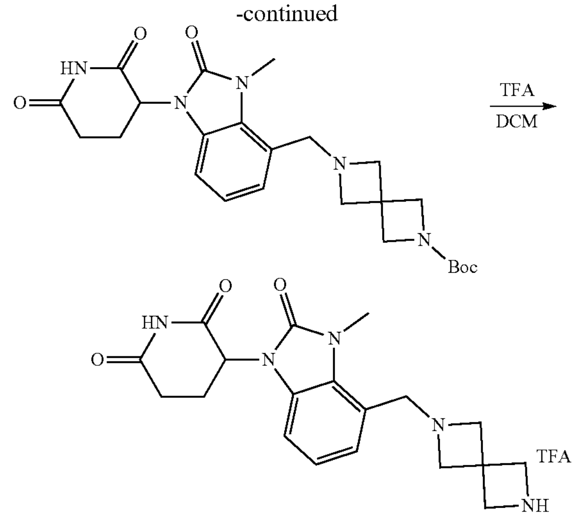

AOE

Step 1—Tert-butyl 6-[[1-(2,6-dioxo-3-piperidyl)-3-methyl-2-oxo-benzimidazol-4-yl]methyl]-2,6-diazaspiro[3.3]heptane-2-carboxylate To a mixture of tert-butyl 2,6-diazaspiro[3.3]heptane-2-carboxylate (600 mg, 3.03 mmol, CAS #1041026-70-3) in THE (10 mL)/DMF (2 mL) was added $NaBH(OAc)_3$ (769 mg, 3.63 mmol) and stirred at 25° C. for 15 min, then 1-(2,6-dioxo-3-piperidyl)-3-methyl-2-oxo-benzimidazole-4-carbaldehyde (869 mg, 3.03 mmol, Intermediate WW) was added and stirred at 25° C. for 10 min. Then HOAc (545 mg, 9.08 mmol) was added and stirred at 25° C. for 2 hrs. On completion, the mixture was concentrated in vacuo. The residue was purified by reverse phase (0.1% FA condition) to give the title compound (500 mg, 35% yield) as yellow solid. LC-MS ($ESI^+$) m/z 470.1 $(M+H)^+$.

Step 2—3-[4-(2,6-Diazaspiro[3.3]heptan-2-ylmethyl)-3-methyl-2-oxo-benzimidazol-1-yl]piperidine-2,6-dione To a solution of tert-butyl 6-[[1-(2,6-dioxo-3-piperidyl)-3-methyl-2-oxo-benzimidazol-4-yl]methyl]- 2,6-diazaspiro[3.3]heptane-2-carboxylate (80.0 mg, 170 umol) in DCM (2 mL) was added TFA (3.08 g, 27 mmol) and stirred at 25° C. for 15 mins. On completion, the mixture was concentrated in vacuo to give the title compound (70.0 mg, 84% yield, TFA salt) as yellow oil. LC-MS ($ESI^+$) m/z 370.2 $(M+H)^+$.

3-(4-(Hydroxymethyl)-3-methyl-2-oxo-2,3-dihydro-1H-benzo[d]imidazol-1-yl)piperidine-2,6-dione (Intermediate ANG)

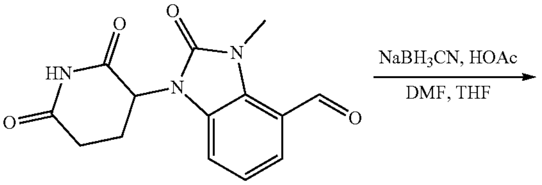

WW

-continued

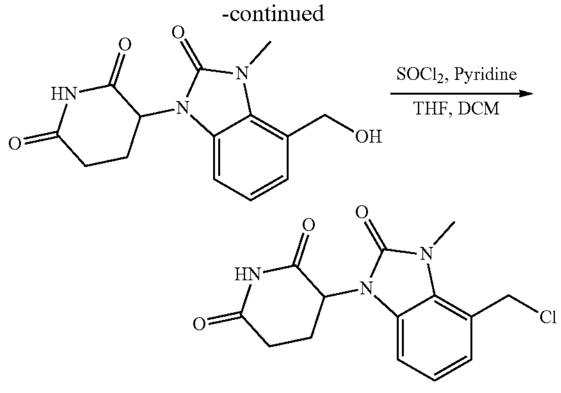

ANG

Step 1—3-(4-(Hydroxymethyl)-3-methyl-2-oxo-2,3-dihydro-1H-benzo[d]imidazol-1-yl)piperidine-2,6-dione To a solution of 1-(2,6-dioxo-3-piperidyl)-3-methyl-2-oxo-benzimidazole-4-carbaldehyde (7.00 g, 24.3 mmol, Intermediate WW) and HOAc (4.39 g, 73.1 mmol) in DMF (50 mL) and THF (50 mL) was added $NaBH_3CN$ (6.13 g, 97.4 mmol) at 60° C. portion-wise, then the mixture was stirred at 60° C. for 2 hours. On completion, the reaction was quenched with 5 mL of water and filtered and the filtrate was concentrated. The residue was purified by reverse phase (FA) to give the title compound (5.00 g, 70% yield) as a white solid. $^1H$ NMR (400 MHz, DMSO-$d_6$) δ 11.10 (s, 1H), 7.13-6.89 (m, 3H), 5.38 (d, J=5.4, 12.4 Hz, 1H), 4.74 (s, 2H), 3.62 (s, 3H), 2.95-2.86 (m, 1H), 2.78-2.60 (m, 2H), 2.10-1.95 (m, 1H).

Step 2—3-(4-(Hydroxymethyl)-3-methyl-2-oxo-2,3-dihydro-1H-benzo[d]imidazol-1-yl)piperidine-2,6-dione To a solution of 3-[4-(hydroxymethyl)-3-methyl-2-oxo-benzimidazol-1-yl]piperidine-2,6-dione (5.00 g, 17.2 mmol) and pyridine (273 mg, 3.46 mmol) in THF (30 mL) and DCM (30 mL) was added $SOCl_2$ (6.17 g, 51.8 mmol), then the mixture was stirred at 20° C. for 12 hrs. On completion, the reaction was concentrated to give the title compound (8.00 g, 90% yield) as a white solid. $^1H$ NMR (400 MHz, DMSO-$d_6$) δ 11.08 (s, 1H), 7.19-6.99 (m, 3H), 5.32 (dd, J=5.2, 12.4 Hz, 1H), 5.03 (s, 2H), 3.65 (s, 3H), 2.92-2.80 (m, 1H), 2.73-2.59 (m, 2H), 2.10-1.98 (m, 1H).

3-(4-(1-oxa-4,9-diazaspiro[5.5]undecan-4-ylmethyl)-3-methyl-2-oxo-2,3-dihydro-1H-benzo [d]imidazol-1-yl)piperidine-2,6-dione (Intermediate AMZ)

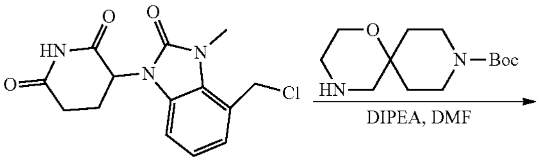

ANG

-continued

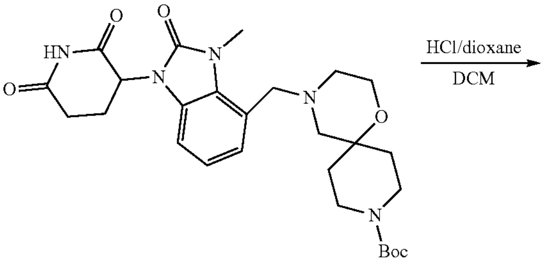

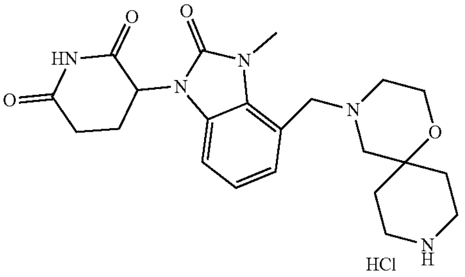

AMZ

Step 1—Tert-butyl 4-((1-(2,6-dioxopiperidin-3-yl)-3-methyl-2-oxo-2,3-dihydro-1H-benzo [d]imidazol-4-yl)methyl)-1-oxa-4,9-diazaspiro[5.5]undecane-9-carboxylate To a solution of 3-[4-(chloromethyl)-3-methyl-2-oxo-benzimidazol-1-yl]piperidine-2,6-dione (80.0 mg, 259 umol, Intermediate ANG) and tert-butyl 1-oxa-4,9-diazaspiro[5.5]undecane-9-carboxylate (66.6 mg, 259 umol) in DMF (1.0 mL) was added DIPEA (67.2 mg, 520 umol). The obtained mixture was heated to 80° C. with stirring for 2 hours. On completion, the reaction mixture was poured into 10 mL water, where a precipitate appeared. The solid was collected to give the title compound (100 mg, crude) as yellow solid. LC-MS (ESI$^+$) m/z 528.3 (M+H)$^+$.

Step 2—3-(4-(1-oxa-4,9-diazaspiro[5.5]undecan-4-ylmethyl)-3-methyl-2-oxo-2,3-dihydro-1H-benzo [d]imidazol-1-yl)piperidine-2,6-dione To a mixture of tert-butyl 4-[[1-(2,6-dioxo-3-piperidyl)-3-methyl-2-oxo-benzimidazol-4-yl]methyl]- 1-oxa-4,9-diazaspiro[5.5]undecane-9-carboxylate (50.0 mg, 94.7 umol) in DCM (3.0 mL) was added HCl/dioxane (4 M, 1 mL) and the mixture was stirred at 25° C. for 1 hour. On completion, the mixture was concentrated to give the title compound (40.0 mg, 90% yield, HCl salt) as white solid. LC-MS (ESI$^+$) m/z 428.2 (M+H)$^+$.

Ethyl 4-[6-(difluoromethyl)-5-[[6-(trifluoromethyl) pyridine-2-carbonyl]amino]indazol -2-yl]cyclohexane carboxylic acid (Intermediate ARO)

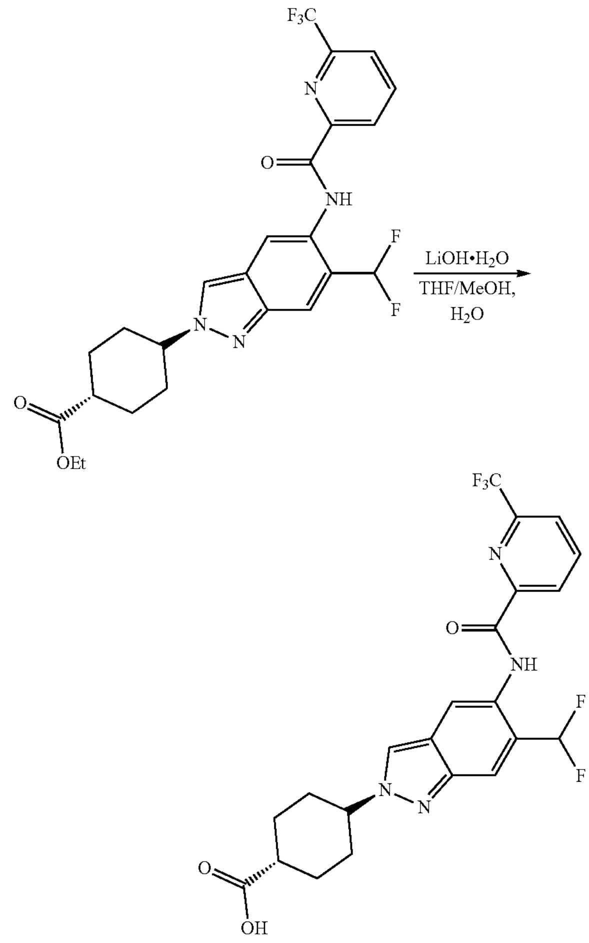

ARO

Ethyl 4-[6-(difluoromethyl)-5-[[6-(trifluoromethyl)pyridine-2-carbonyl]amino]indazol -2-yl]cyclohexane carboxylic acid was synthesized via Steps 1-7 of Intermediate ALU. LC-MS ($ESI^+$) m/z 483.2 $(M+1)^+$.

2-(2,6-Dioxo-3-piperidyl)-4-[4-(methylaminomethyl)-1-piperidyl]isoindoline-1,3-dione (Intermediate AGW)

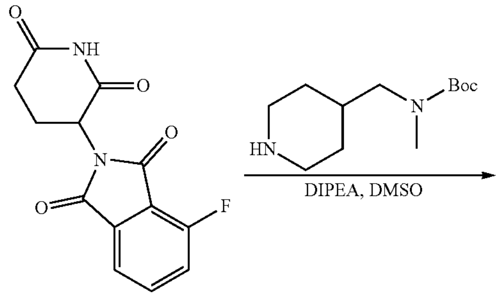

R

-continued

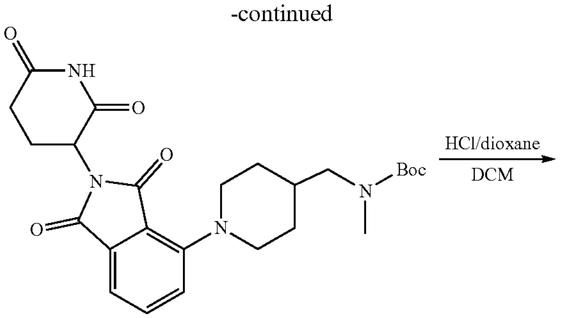

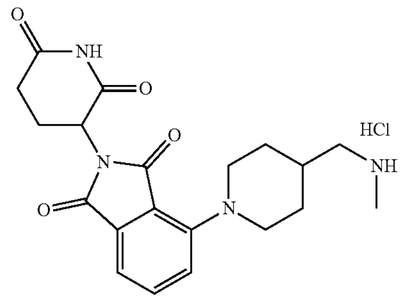

AGW

Step 1—Tert-butyl N-[[1-[2-(2,6-dioxo-3-piperidyl)-1,3-dioxo-isoindolin-4-yl]-4-piperidyl]methyl]-N—methyl-carbamate To a solution of 2-(2,6-dioxo-3-piperidyl)-4-fluoro-isoindoline-1,3-dione (302 mg, 1.09 mmol, Intermediate R) and tert-butyl N-methyl-N-(4-piperidylmethyl)carbamate (250 mg, 1.09 mmol, CAS #138022-04-5) in DMSO (12 mL) was added DIPEA (18.7 mg, 144 umol) at 25° C. The reaction mixture was stirred at 130° C. for 2 hrs. On completion, the reaction mixture was concentrated in vacuo to give a residue. The residue was purified by reverse phase (0.1% FA condition) to give the title compound (530 mg, 99% yield) as a yellow solid. $^1H$ NMR (400 MHz, DMSO-$d_6$) δ 11.07 (s, 1H), 7.68 (dd, J=7.2, 8.4 Hz, 1H), 7.36-7.28 (m, 2H), 5.09 (dd, J=5.2, 12.4 Hz, 1H), 3.70 (d, J=11.6 Hz, 2H), 3.12 (d, J=6.8 Hz, 2H), 2.92-2.78 (m, 6H), 2.63-2.52 (m, 2H), 2.07-1.97 (m, 1H), 1.86-1.73 (m, 1H), 1.67 (d, J=11.2 Hz, 2H), 1.40 (s, 9H), 1.39-1.30 (m, 2H); LC-MS ($ESI^+$) m/z 485.4 $(M+H)^+$.

Step 2—2-(2,6-Dioxo-3-piperidyl)-4-[4-(methylaminomethyl)-1-piperidyl]isoindoline-1,3-dione To a solution of tert-butyl N-[[1-[2-(2,6-dioxo-3-piperidyl)-1,3-dioxo-isoindolin-4-yl]-4-piperidyl]methyl]-N-methyl-carbamate (95.0 mg, 144 umol) in DCM (5 mL) was added HCl/dioxane (4 M, 3 mL). The mixture was stirred at 25° C. for 2 hrs. On completion, the reaction mixture was concentrated in vacuo to give the title compound (80.0 mg, 98% yield, HCl salt) as a yellow solid. LC-MS ($ESI^+$) m/z 385.1 $(M+H)^+$.

Benzyl N-[3-(3-aminocyclobutoxy)propyl]-N-methyl-carbamate (Intermediate AOY)

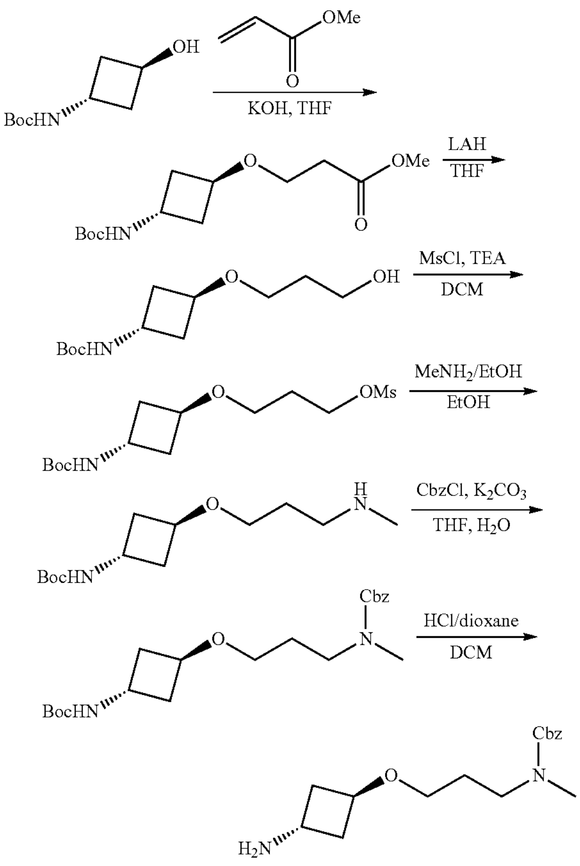

AOY

Step 1—Methyl 3-[3-(tert-butoxycarbonylamino) cyclobutoxy]propanoate

To a solution of tert-butyl N-(3-hydroxycyclobutyl)carbamate (2.50 g, 13.3 mmol, CAS #389890-42-0) and methyl prop-2-enoate (2.30 g, 26.7 mmol, CAS #96-33-3) in THF (25 mL) was added KOH (74.9 mg, 1.34 mmol). The reaction mixture was stirred at 20° C. for 16 hrs. On completion, the reaction mixture was diluted with water (80 mL) and extracted with EA (3×80 mL). The combined organic layers were washed with brine (2×50 mL), dried over $Na_2SO_4$, filtered and concentrated in vacuo. The residue was purified by silica gel chromatography (PE:EA=8:1) to give the title compound (1.80 g, 49% yield) as colorless oil. $^1H$ NMR (400 MHz, $CDCl_3$) δ 4.81-4.59 (m, 1H), 4.26-4.03 (m, 2H), 3.70 (s, 3H), 3.59 (t, J=6.4 Hz, 2H), 2.57 (t, J=6.4 Hz, 2H), 2.42-2.30 (m, 2H), 2.19-2.06 (m, 2H), 1.44 (s, 9H).

Step 2—Tert-butyl N-[3-(3-hydroxypropoxy)cyclobutyl]carbamate

To a solution of methyl 3-[3-(tert-butoxycarbonylamino) cyclobutoxy]propanoate (1.80 g, 6.59 mmol) in THE (20 mL) was added LAH (274 mg, 7.24 mmol). The reaction mixture was stirred at 0° C. for 1 hr. On completion, the reaction mixture was quenched by water (0.25 mL), added 15% NaOH (0.3 mL), water (0.8 mL), diluted with EA (50 mL), dried over $Na_2SO_4$, filtered and concentrated in vacuo to give the title compound (1.50 g, 92% yield) as yellow oil. $^1H$ NMR (400 MHz, $CDCl_3$) δ 4.70 (s, 1H), 4.54-4.41 (m, 1H), 4.27-4.14 (m, 1H), 4.12-4.04 (m, 1H), 3.81-3.74 (m, 2H), 3.50 (t, J=6.0 Hz, 2H), 2.37-2.30 (m, 2H), 2.24-2.14 (m, 2H), 1.86-1.80 (m, 2H), 1.44 (s, 9H).

Step 3—3-[3-(Tert-butoxycarbonylamino)cyclobutoxy]propyl methanesulfonate

To a solution of tert-butyl N-[3-(3-hydroxypropoxy)cyclobutyl]carbamate (1.50 g, 6.11 mmol) and TEA (928 mg, 9.17 mmol) in DCM (20 mL) was added MsC1 (840 mg, 7.34 mmol) at 0° C. The reaction mixture was stirred at 0° C. for 1 hr. On completion, the reaction mixture was diluted with water (20 mL) and extracted with DCM (3×40 mL). The combined organic layers were washed with brine (2×30 mL), dried over $Na_2SO_4$, filtered and concentrated in vacuo to give the title compound (1.90 g, crude) as yellow oil. $^1H$ NMR (400 MHz, $CDCl_3$) δ 5.23-5.11 (m, 1H), 4.79-4.66 (m, 1H), 4.34 (t, J=6.0 Hz, 2H), 4.09-4.04 (m, 1H), 3.42 (t, J=6.0 Hz, 2H), 3.02 (s, 3H), 2.51-2.26 (m, 4H), 2.00 (q, J=6.0 Hz, 2H), 1.44 (s, 9H).

Step 4—Tert-butyl N-[3-[3-(methylamino)propoxy] cyclobutyl]carbamate

A mixture of 3-[3-(tert-butoxycarbonylamino)cyclobutoxy]propyl methanesulfonate (1.90 g, 5.87 mmol) and $MeNH_2$/EtOH (5.87 mmol, 10 mL, 30% solution) was stirred at 70° C. for 12 hrs in a sealed tube (15 psi). On completion, the reaction mixture was concentrated in vacuo to give the title compound (1.80 g, crude) as yellow oil and used for next step directly. LC-MS ($ESI^+$) m/z 259.0 $(M+H)^+$.

Step 5—Benzyl N-[3-[3-(tert-butoxycarbonylamino) cyclobutoxy]propyl]-N-methyl-carbamate To a solution of tert-butyl N-[3-[3-(methylamino) propoxy]cyclobutyl]carbamate (1.80 g, 6.97 mmol) and $K_2CO_3$ (1.93 g, 13.9 mmol) in a mixed solvents of THF (15 mL) and water (5 mL) was added CbzCl (1.78 g, 10.4 mmol). The reaction mixture was stirred at 20° C. for 2 hrs. On completion, the reaction mixture was diluted with water (30 mL) and extracted with EA (3×50 mL). The combined organic layers were washed with brine (2×30 mL), dried over $Na_2SO_4$, filtered and concentrated in vacuo. The residue was purified by silica gel chromatography (PE:EA=5:1) to give the title compound (1.30 g, 41% yield) as yellow oil. $^1H$ NMR (400 MHz, $CDCl_3$) δ 7.39-7.29 (m, 5H), 5.13 (s, 2H), 4.79-4.58 (m, 1H), 4.32-4.14 (m, 1H), 4.07-3.92 (m, 1H), 3.42-3.21 (m, 4H), 2.94 (s, 3H), 2.39-2.23 (m, 2H), 2.14-2.05 (m, 2H), 1.87-1.72 (m, 2H), 1.45 (s, 9H).

Step 6—Benzyl N-[3-(3-aminocyclobutoxy)propyl]-N-methyl-carbamate

To a solution of benzyl N-[3-[3-(tert-butoxycarbonylamino)cyclobutoxy]propyl]-N-methyl-carbamate (1.60 g, 4.08 mmol) in DCM (20 mL) was added HCl/dioxane (4 M, 15 mL). The reaction mixture was stirred at 20° C. for 1 hour. On completion, the reaction mixture was concentrated in vacuo to give the title compound (1.30 g, 96% yield, HCl salt) as yellow semisolid. LC-MS (ESI$^+$) m/z 293.2 (M+H)$^+$.

2-(2,6-dioxo-3-piperidyl)-4-[[3-[3-(methylamino)propoxy]cyclobutyl]amino]isoindoline-1,3-dione (Intermediate AOQ)

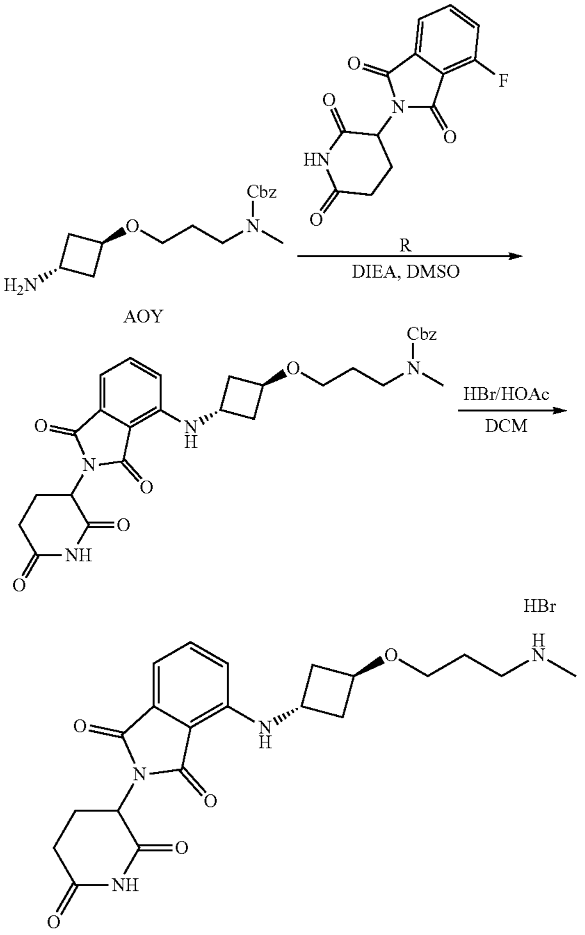

AOQ

Step 1—Benzyl N-[3-[3-[[2-(2,6-dioxo-3-piperidyl)-1,3-dioxo-isoindolin-4-yl]amino]cyclobutoxy]propyl]-N-methyl-carbamate To a solution of benzyl N-[3-(3-aminocyclobutoxy)propyl]-N-methyl-carbamate (1.30 g, 3.95 mmol, HCl salt, Intermediate AOY) and 2-(2,6-dioxo-3-piperidyl)-4-fluoro-isoindoline-1,3-dione (928 mg, 3.36 mmol, Intermediate R) in DMSO (15 mL) was added DIPEA (2.55 g, 19.7 mmol). The reaction mixture was stirred at 130° C. for 3 hrs. On completion, the reaction mixture was diluted with water (50 mL) and extracted with EA (3×70 mL). The combined organic layers were washed with brine (50 mL), dried over $Na_2SO_4$, filtered and concentrated in vacuo. The residue was purified by reverse phase (0.1% FA) to give the title compound (810 mg, 37% yield) as yellow solid. $^1$H NMR (400 MHz, $CDCl_3$) δ 8.02 (s, 1H), 7.54-7.47 (m, 1H), 7.42-7.28 (m, 5H), 7.14 (d, J=7.2 Hz, 1H), 6.80-6.64 (m, 1H), 6.36-6.22 (m, 1H), 5.14 (s, 2H), 4.99-4.87 (m, 1H), 4.24-4.05 (m, 2H), 3.47-3.28 (m, 4H), 2.95 (s, 3H), 2.93-2.84 (m, 1H), 2.84-2.70 (m, 2H), 2.57-2.35 (m, 2H), 2.28-2.09 (m, 3H), 1.90-1.74 (m, 2H).

Step 2—2-(2,6-Dioxo-3-piperidyl)-4-[[3-[3-(methylamino)propoxy]cyclobutyl]amino]isoindoline- 1,3-dione To a solution of benzyl N-[3-[3-[[2-(2,6-dioxo-3-piperidyl)-1,3-dioxo-isoindolin-4-yl]amino]cyclobutoxy]propyl]-N-methyl-carbamate (0.80 g, 1.46 mmol) in DCM (10 mL) was added HBr/AcOH (1.46 mmol, 10 mL, 30% solution). The reaction mixture was stirred at 20° C. for 1 hour. On completion, the reaction mixture was dried by nitrogen. The residue was diluted with ACN/$H_2O$=1/1 (100 mL) and lyophilizated to give the title compound (722 mg, 99% yield, HBr salt) as yellow solid. $^1$H NMR (400 MHz, DMSO-$d_6$) δ 11.09 (s, 1H), 8.32 (s, 2H), 7.60 (dd, J=7.2, 8.4 Hz, 1H), 7.09 (d, J=7.0 Hz, 1H), 6.91 (d, J=8.4 Hz, 1H), 6.68-6.25 (m, 1H), 5.06 (dd, J=5.6, 12.8 Hz, 1H), 4.22-4.11 (m, 2H), 3.38 (t, J=6.0 Hz, 2H), 3.04-2.80 (m, 3H), 2.63-2.55 (m, 4H), 2.54-2.52 (m, 1H), 2.44-2.33 (m, 2H), 2.29-2.18 (m, 2H), 2.12-1.97 (m, 1H), 1.90-1.76 (m, 2H).

2-(2,6-Dioxo-3-piperidyl)-4-[3-(4-piperidyloxy)propylamino]isoindoline-1,3-dione (Intermediate AFJ)

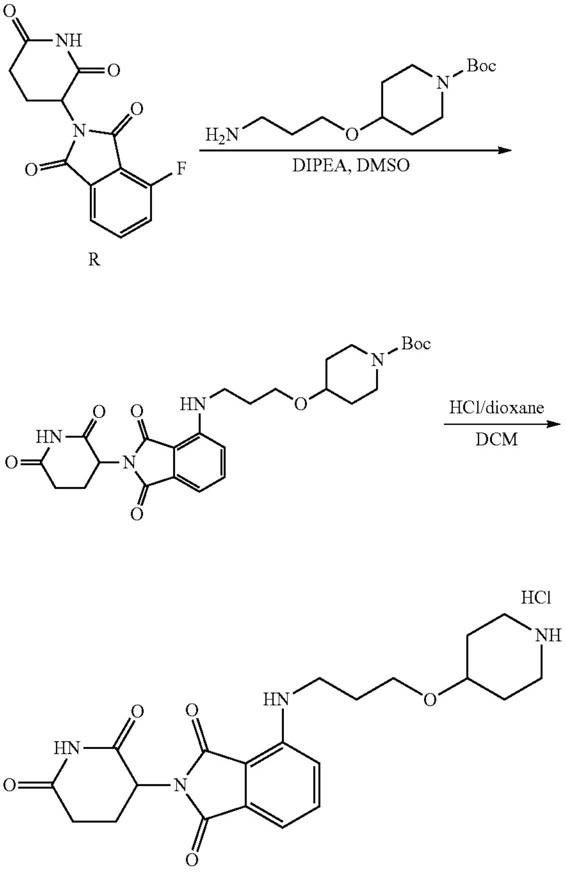

AFJ

Step 1—Tert-butyl 4-[3-[[2-(2,6-dioxo-3-piperidyl)-1,3-dioxo-isoindolin-4-yl]amino]propoxy]piperidine-1-carboxylate To a solution of 2-(2,6-dioxo-3-piperidyl)-4-fluoro-isoindoline-1,3-dione (230 mg, 832 umol, Intermediate R) and tert-butyl 4-(3-aminopropoxy)piperidine-1-carboxylate (322 mg, 1.25 mmol, CAS #771572-33-9) in DMSO (15 mL) was added DIPEA (18.7 mg, 144 umol) at 25° C. The reaction mixture was stirred at 130° C. for 2 hours. On completion, the reaction mixture was diluted with EA (30 mL), washed with $H_2O$ (3×10 mL), dried over by $Na_2SO_4$, filtered and concentrated in vacuo. The residue was purified by reverse phase (0.1% FA condition) to give the title compound (270 mg, 63% yield) as a yellow solid. $^1$H NMR (400 MHz, DMSO-$d_6$) δ 11.07 (s, 1H), 7.61-7.55 (m, 1H), 7.10 (d, J=8.4 Hz, 1H), 7.02 (d, J=6.8 Hz, 1H), 5.04 (dd, J=5.2, 13.2 Hz, 1H), 3.64-3.58 (m, 2H), 3.51 (t, J=6.0 Hz, 2H), 3.46-3.36 (m, 4H), 3.04-2.98 (m, 2H), 2.94-2.82 (m, 1H), 2.62-2.55 (m, 2H), 2.53-2.51 (m, 2H), 1.83-1.74 (m, 4H), 1.38 (s, 9H); LC-MS (ESI$^+$) m/z 415.2 (M-100)+.

Step 2—2-(2,6-Dioxo-3-piperidyl)-4-[3-(4-piperidyloxy)propylamino]isoindoline-1,3-dione To a solution of tert-butyl 4-[3-[[2-(2,6-dioxo-3-piperidyl)-1,3-dioxo-isoindolin-4-yl]amino]propoxy]piperidine-1-carboxylate (50.0 mg, 97.1 umol) in DCM (2 mL) was added HCl/dioxane (4 M, 2.50 mL). The mixture was stirred at 15° C. for 2 hours. On completion, the reaction mixture was concentrated in vacuo to give the title compound (40.0 mg, 91% yield, HCl salt) as a yellow solid. LC-MS (ESI$^+$) m/z 415.2 (M+H)$^+$.

4-[6-(1-hydroxy-1-methyl-ethyl)-5-[[6-(trifluoromethyl)pyridine-2-carbonyl]amino]indazol-2-yl]cyclohexanecarboxylic acid (Intermediate AMY)

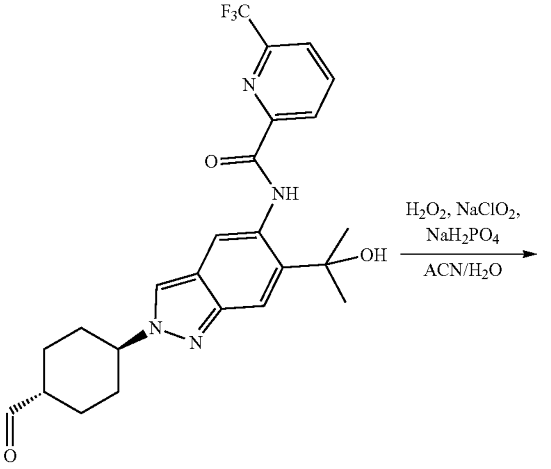

AGL

-continued

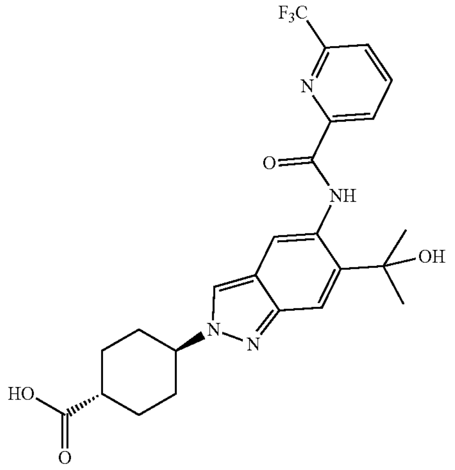

AMY

To a solution of N-[2-(4-formylcyclohexyl)-6-(1-hydroxy-1-methyl-ethyl)indazol-5-yl]-6-(trifluoro methyl) pyridine-2-carboxamide (200 mg, 421 umol, Intermediate AGL) and $NaH_2PO_4$ (252 mg, 2.11 mmol) in ACN (6 mL) was added $H_2O_2$ (95.5 mg, 843 umol, 81 uL, 30% solution) dropwise at 0° C. Then sodium chlorite (266 mg, 2.95 mmol) in $H_2O$ (3 mL) was added to the mixture at 0° C. The reaction mixture was stirred at 25° C. for 1 hour. On completion, the reaction mixture was diluted with ACN (20 mL) and the reaction was quenched with sat.$Na_2SO_3$ (20 mL) at 0° C. The reaction mixture was extracted with ACN (3×10 mL). The combined organic layers were concentrated in vacuo to give the title compound (200 mg, 96% yield) as a yellow solid. LC-MS (ESI$^+$) m/z 491.1 (M+1)$^+$.

3-[4-(2,7-Diazaspiro[3.5]nonan-2-ylmethyl)-3-methyl-2-oxo-benzimidazol-1-yl]piperidine-2,6-dione (Intermediate AGI)

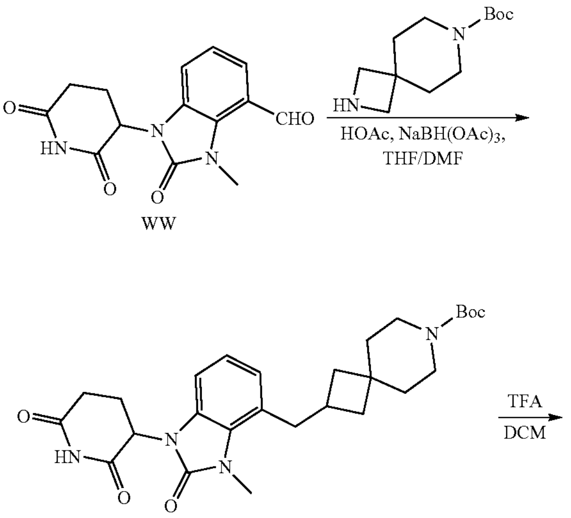

-continued

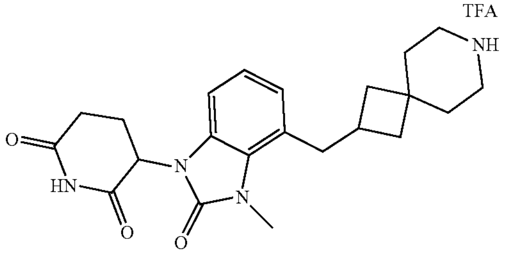

AGI

Step 1—Tert-butyl 2-[[1-(2,6-dioxo-3-piperidyl)-3-methyl-2-oxo-benzimidazol-4-yl]methyl]-2,7- diazaspiro[3.5]nonane-7-carboxylate To a mixture of tert-butyl 2,7-diazaspiro[3.5]nonane-7-carboxylate (330 mg, 1.46 mmol, CAS #896464-16-7) in THE (1 mL) and DMF (3 mL) was added 1-(2,6-dioxo-3-piperidyl)-3-methyl-2-oxo- benzimidazole-4-carbaldehyde (300 mg, 1.04 mmol, Intermediate WW) and HOAc (62.7 mg, 1.04 mmol, 59.7 uL). The mixture was stirred at 80° C. for 1 hour. Then $NaBH(OAc)_3$ (442 mg, 2.09 mmol) was added to the mixture and stirred at 40° C. for 48 hours. On completion, the reaction mixture was quenched with water (0.1 mL) and concentrated in vacuo. The residue was purified by prep-HPLC (column: Phenomenex Synergi C18 150*25*10 um; mobile phase: [water (0.05% HCl)-ACN]; B %: 16%-36%, 12 min) to give the title compound (25.0 mg, 4% yield) as light yellow solid. $^1H$ NMR (400 MHz, DMSO-$d_6$) δ 11.13 (s, 1H), 7.27-7.19 (m, 2H), 7.14-7.07 (m, 1H), 5.47-5.38 (m, 1H), 4.77 (d, J=5.6 Hz, 2H), 4.09-3.91 (m, 4H), 3.60 (s, 3H), 3.31-3.26 (m, 2H), 3.23 (s, 2H), 2.96-2.84 (m, 1H), 2.74-2.61 (m, 2H), 2.04-1.95 (m, 1H), 1.84-1.78 (m, 2H), 1.77-1.71 (m, 2H), 1.38 (s, 9H); LC-MS ($ESI^+$) m/z 498.4 $(M+H)^+$.

Step 2—3-[4-(2,7-Diazaspiro[3.5]nonan-2-ylmethyl)-3-methyl-2-oxo-benzimidazol-1-yl]piperidine -2,6-dione To a mixture of tert-butyl 2-[[1-(2,6-dioxo-3-piperidyl)-3-methyl-2-oxo-benzimidazol-4-yl]methyl]- 2,7-diazaspiro [3.5]nonane-7-carboxylate (25.0 mg, 50.2 umol) in DCM (3 mL) was added TFA (1.54 g, 13.5 mmol, 1 mL). The reaction mixture was stirred at 25° C. for 0.5 hour. On completion, the reaction mixture was concentrated in vacuo to give the title compound (25.0 mg, 97% yield, TFA) as red oil. LC-MS ($ESI^+$) m/z 398.3 $(M+H)^+$.

Tert-butyl N-(4-aminocyclohexyl)-N-methyl-carbamate (Intermediate AOZ)

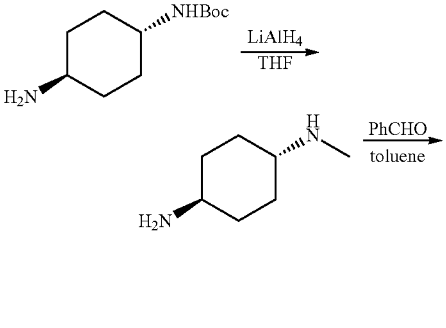

-continued

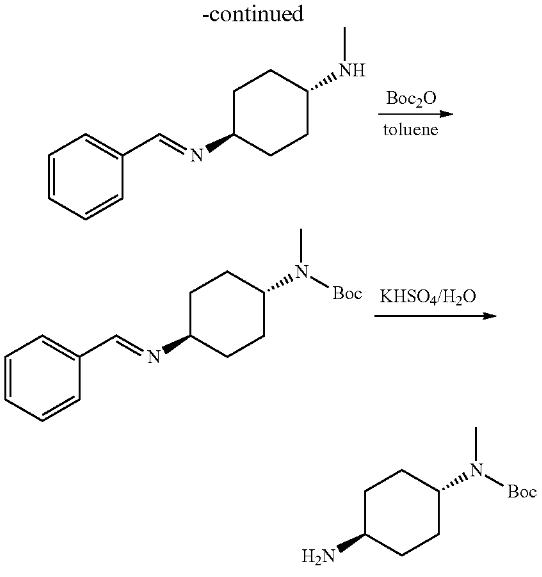

AOZ

Step 1—N4-methylcyclohexane-1,4-diamine

To a solution of tert-butyl N-(4-aminocyclohexyl)carbamate (15.0 g, 70.0 mmol, CAS #177906-48-8) in THE (100 mL) was added $LiAlH_4$ (13.3 g, 350 mmol) at 0° C. The mixture was stirred at 70° C. for 3 hours. On completion, the reaction was cooled to 20° C., then it was quenched with $H_2O$ (80 mL), filtered and the filtered cake was washed with EA (3×150 mL). The combined organic was dried over $Na_2SO_4$, filtered and concentrated in vacuo to give the title compound (6.90 g, 100% yield) as a yellow solid. $^1H$ NMR (400 MHz, DMSO-$d_6$) δ 2.48-2.41 (m, 1H), 2.27-2.21 (m, 3H), 2.13-2.10 (m, 1H), 1.85-1.65 (m, 4H), 1.06-0.87 (m, 4H).

Step 2—4-(Benzylideneamino)-N-methyl-cyclohexanamine

A solution of N4-methylcyclohexane-1,4-diamine (3.20 g, 20.0 mmol) and benzaldehyde (2.20 g, 21.0 mmol) in toluene (50 mL) was stirred at 120° C. for 16 hours. On completion, the reaction was concentrated in vacuo to give the title compound (4.00 g, 100% yield) as yellow oil. $^1H$ NMR (400 MHz, DMSO-$d_6$) δ 8.37 (s, 1H), 7.75-7.69 (m, 2H), 7.45-7.41 (m, 3H), 3.17 (br s, 1H), 2.30 (s, 4H), 1.98-1.91 (m, 2H), 1.71-1.63 (m, 2H), 1.60-1.47 (m, 2H), 1.16-1.05 (m, 2H).

Step 3—Tert-butyl N-[4-[(E)-benzylideneamino] cyclohexyl]-N-methyl-carbamate

To a solution of 4-[(E)-benzylideneamino]-N-methyl-cyclohexanamine (4.00 g, 18.5 mmol) in toluene (60 mL) was added $(Boc)_2O$ (4.80 g, 22.2 mmol, 5.1 mL). The mixture was stirred at 25° C. for 3 hours. On completion, the organic solvent was removed under vacuum to give the title compound (5.00 g, 90% yield) as yellow oil. $^1H$ NMR (400 MHz, DMSO-$d_6$) δ 8.42 (s, 1H), 7.81-7.73 (m, 2H), 7.52-7.46 (m, 3H), 4.02-3.71 (m, 1H), 3.24 (d, J=4.2 Hz, 1H), 2.74 (s, 3H), 1.83-1.74 (m, 2H), 1.73-1.62 (m, 6H), 1.46 (s, 9H).

Step 4—Tert-butyl N-(4-aminocyclohexyl)-N-methyl-carbamate

A solution of $KHSO_4$ (7.5 g, 55.3 mmol) in $H_2O$ (56 mL) was added to tert-butyl N-[4-[(E)-benzylideneamino]cyclohexyl]-N-methyl-carbamate (5 g, 15.8 mmol), and the reaction was stirred at 25° C. for 3 h. On completion, the reaction was extracted with MTBE (3×50 mL) and the aqueous phase was basified with NaOH (6 N) to pH=11, then it was extracted with DCM (5×50 mL). The organic phase was dried over $Na_2SO_4$, filtered and concentrated under vacuum to give the title compound (3.00 g, 90% yield) as colorless oil. LC-MS ($ESI^+$) m/z 229.7 $(M+H)^+$.

2-(2,6-dioxo-3-piperidyl)-4-[[4-(methylamino)cyclohexyl]amino]isoindoline-1,3-dione (Intermediate AOV)

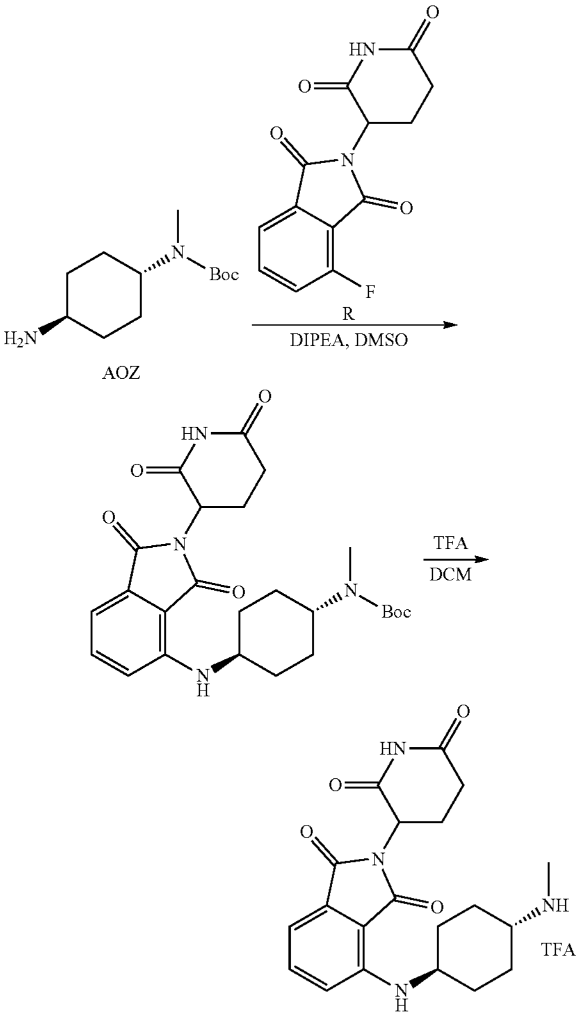

AOZ

AOV

Step 1—Tert-butyl N-[4-[[2-(2,6-dioxo-3-piperidyl)-1,3-dioxo-isoindolin-4-yl]amino]cyclohexyl]-N—methyl-carbamate To a solution of tert-butyl N-(4-aminocyclohexyl)-N-methyl-carbamate (3.00 g, 13.1 mmol, Intermediate AOZ) and 2-(2,6-dioxo-3-piperidyl)-4-fluoro-isoindoline-1,3-dione (3.60 g, 13.1 mmol, Intermediate R) in DMSO (30 mL) was added DIPEA (3.40 g, 26.3 mmol, 4.6 mL). The mixture was stirred at 130° C. for 2 hour. On completion, the crude product was purified by reversed-phase HPLC (0.1% FA condition) to give the title compound (3.40 g, 48% yield) as a yellow solid. LC-MS ($ESI^+$) m/z 485.5 $(M+H)^+$.

Step 2—2-(2,6-Dioxo-3-piperidyl)-4-[[4-(methylamino)cyclohexyl]amino]isoindoline-1,3-dione To a solution of tert-butyl N-[4-[[2-(2,6-dioxo-3-piperidyl)-1,3-dioxo-isoindolin-4-yl]amino]cyclohexyl]-N-methyl-carbamate (0.60 g, 1.2 mmol) in DCM (8 mL) was added TFA (6.20 g, 54.0 mmol, 4 mL). The mixture was stirred at 25° C. for 0.5 hour. On completion, the reaction mixture was concentrated in vacuo to give the title compound (1.00 g, 100% yield, TFA) as yellow oil. LC-MS ($ESI^+$) m/z 384.9 $(M+H)^+$.

N-[2-[4-(hydroxymethyl)cyclohexyl]-6-(1-hydroxy-1-methyl-ethyl)indazol-5-yl]-6-methyl- pyridine-2-carboxamide (Intermediate AOX)

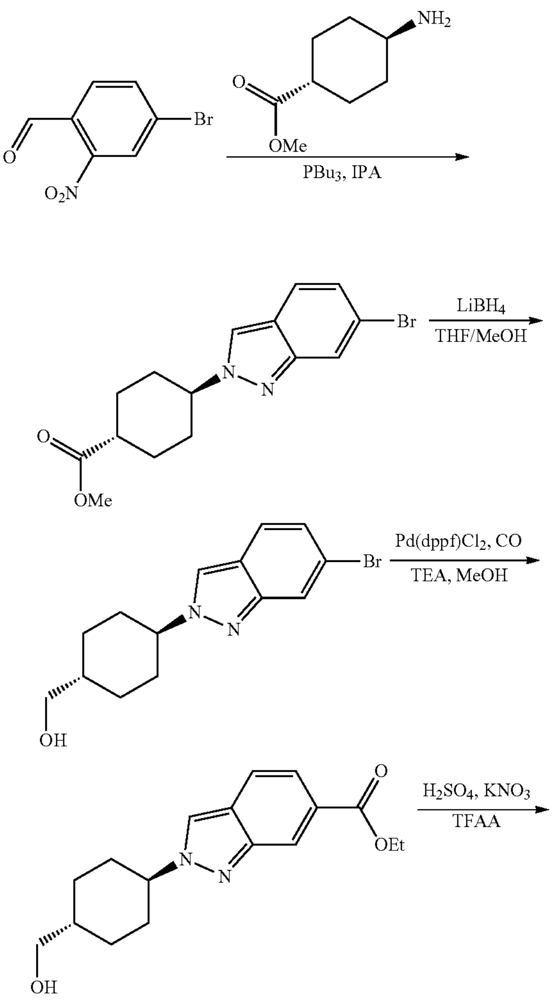

-continued

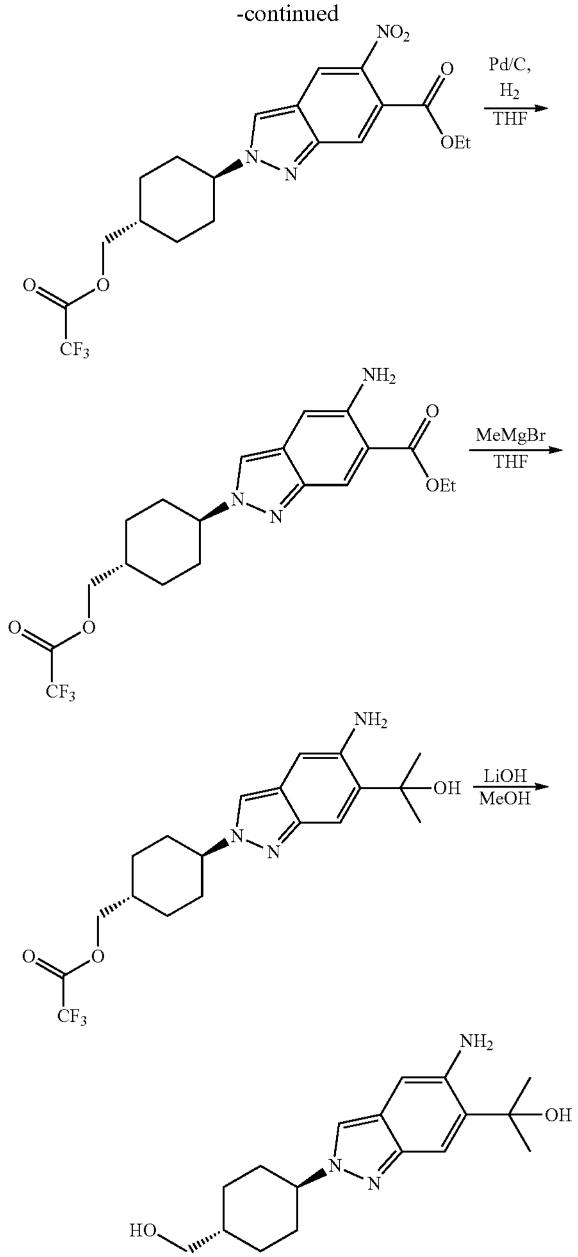

AOX

Step 1—(1r,4r)-Methyl 4-(6-bromo-2H-indazol-2-yl)cyclohexanecarboxylate

To a solution of 4-bromo-2-nitro-benzaldehyde (10.0 g, 43.5 mmol, CAS #62456-15-9) in IPA (100 mL) was added methyl 4-aminocyclohexanecarboxylate (6.83 g, 43.5 mmol, CAS #5551-12-2). The mixture was heated at 80° C. for 4 hrs under $N_2$. It was cooled to 25° C. Tributylphosphane (26.4 g, 130 mmol) was added and the reaction mixture was heated to 80° C. for 16 hrs. On completion, the reaction mixture was concentrated in vacuo to give a residue. The residue was purified by silica gel chromatography (PE: EA=10:1) to give the title compound (13.0 g, 87% yield) as a white solid. $^1H$ NMR (400 MHz, $CDCl_3$) δ 7.94 (d, J=0.8 Hz, 1H), 7.92-7.85 (m, 1H), 7.53 (d, J=8.8 Hz, 1H), 7.16 (dd, J=1.6, 8.8 Hz, 1H), 4.41 (tt, J=4.0, 12.0 Hz, 1H), 3.73 (s, 3H), 2.47 (tt, J=3.6, 12.4 Hz, 1H), 2.41-2.32 (m, 2H), 2.30-2.21 (m, 2H), 2.01 (dq, J=3.2, 12.8 Hz, 2H), 1.60-1.56 (m, 2H); LC-MS ($ESI^+$) m/z 339.0 $(M+H)^+$.

Step 2—((1r,4r)-4-(6-Bromo-2H-indazol-2-yl)cyclohexyl)methanol

To a solution of methyl 4-(6-bromoindazol-2-yl)cyclohexanecarboxylate (9.00 g, 26.7 mmol) in a mixed solvent of tertahydrofuran (90.0 mL) and methanol (11.0 mL) was added LiBH4 (1.74 g, 80.0 mmol) at 25° C. The reaction mixture was stirred at 60° C. for 3 hr. On completion, the reaction mixture was quenched with saturated $NH_4Cl$ (100 mL), then removed to terthydrofuran and methanol. The residue was extracted with dichloromethane (3×100 mL). The combined organic layers were washed with brine (50 mL), dried over anhydrous sodium sulfate, filtered and the filtrate was concentrated in vacuo to give the title compound (7.80 g, 95% yield) as a white solid. $^1H$ NMR (400 MHz, $CDCl_3$) δ 7.95 (s, 1H), 7.92-7.89 (m, 1H), 7.54 (d, J=8.8 Hz, 1H), 7.16 (dd, J=1.6, 8.8 Hz, 1H), 4.75 (s, 1H), 4.39 (tt, J=3.6, 12.0 Hz, 1H), 3.58 (d, J=6.4 Hz, 2H), 2.47-2.26 (m, 2H), 2.14-1.91 (m, 4H), 1.68-1.63 (m, 1H), 1.27 (dq, J=3.2, 12.8 Hz, 2H), LC-MS ($ESI^+$) m/z 311.2 $(M+H)^+$.

Step 3—Ethyl 2-((1r,4r)-4-(hydroxymethyl)cyclohexyl)-2H-indazole-6-carboxylate

To a stirring solution of [4-(6-bromoindazol-2-yl)cyclohexyl]methanol (7.30 g, 23.6 mmol) in EtOH (70.0 mL) in a steel bomb under inert atmosphere were added Pd(dppf)$Cl_2$ (1.73 g, 2.36 mmol), TEA (11.9 g, 118 mmol, 16.4 mL) and the mixture was heated to 80° C. under CO gas atmosphere (50 psi) and stirred for 12 hrs. On completion, the reaction mixture was filtered and concentrated in vacuo to give a residue. The residue was purified by silica gel chromatography (PE:EA=2:1) to give the title compound (6.70 g, 93% yield) as a white solid. LC-MS ($ESI^+$) m z 301.1 $(M+H)^+$.

Step 4—Ethyl 5-nitro-2-((1r,4r)-4-((2,2,2-trifluoroacetoxy)methyl)cyclohexyl)-2H-indazole-6- carboxylate To a solution of ethyl 2-[4-(hydroxymethyl)cyclohexyl] indazole-6-carboxylate (6.5 g, 21.5 mmol) in TFAA (22.6 g, 107 mmol, 15 mL). The reaction mixture was stirred at 20° C. for 2 hrs. After, $KNO_3$ (4.35 g, 43.0 mmol) in $H_2SO_4$ (60 mL) was added dropwise at −5° C. The reaction mixture was stirred at 20° C. for 1 hr. On completion, the reaction mixture was poured into cold water (10 mL) and extracted with EA (3×100 mL). The combined organic layers were washed with brine (2×100 mL), saturated $NaHCO_3$ (5×200 mL) until the pH=7, dried over $Na_2SO_4$, filtered and concentrated in vacuo to give the title compound (9.30 g, 97% yield) as a yellow solid. $^1H$ NMR (400 MHz, $CDCl_3$) δ 8.41 (s, 1H), 8.22 (d, J=0.6 Hz, 1H), 8.04 (s, 1H), 4.56-4.45 (m, 1H), 4.41 (q, J=7.2 Hz, 2H), 4.29 (d, J=6.4 Hz, 2H), 2.45-2.35 (m, 2H), 2.11-2.03 (m, 4H), 2.00-1.91 (m, 1H), 1.44-1.31 (m, 5H). LC-MS ($ESI^+$) m/z 444.1 $(M+H)^+$.

Step 5—Ethyl 5-amino-2-[4-[(2,2,2-trifluoroacetyl) oxymethyl]cyclohexyl]indazole-6-carboxylate To a solution of ethyl 5-nitro-2-[4-[(2,2,2-trifluoroacetyl) oxymethyl]cyclohexyl]indazole- 6-carboxylate (9.20 g, 20.7 mmol) in THE (150.0 mL) was added Pd/C (1.00 g, 10 wt %). The reaction mixture was stirred at 25° C. for 12 hrs under $H_2$ (15 Psi) atmosphere. On completion, the reaction mixture was filtered and the filtrate was concentrated in vacuo to give the title compound (8.30 g, 96% yield) as a yellow solid. LC-MS ($ESI^+$) m/z 414.2 $(M+H)^+$.

Step 6—[4-[5-Amino-6-(1-hydroxy-1-methyl-ethyl) indazol-2-yl]cyclohexyl]methyl 2,2,2- trifluoroacetate To a solution of ethyl 5-amino-2-[4-[(2,2,2-trifluoroacetyl)oxymethyl]cyclohexyl]indazole- 6-carboxylate (8.30 g, 20.1 mmol) in THE (80.0 mL) was added MeMgBr (3 M, 53.5 mL) dropwise at 0° C. Then the reaction mixture was stirred at 20° C. for 12 hrs. On completion, the reaction mixture was quenched with water (400 mL), and extracted with EA (2×300 mL). The organic layer was washed with brine (100 mL), and concentrated in vacuo. The residue was purified by silica gel chromatography (SiO2, PE:EA=3:1) to give the title compound (5.00 g, 62% yield) as a yellow solid. LC-MS ($ESI^+$) m/z 400.1 $(M+H)^+$.

Step 7—N-[2-[4-(hydroxymethyl)cyclohexyl]-6-(1-hydroxy-1-methyl-ethyl)indazol-5-yl]-6-methyl-pyridine-2-carboxamide To a solution of [4-[5-amino-6-(1-hydroxy-1-methyl-ethyl)indazol-2-yl]cyclohexyl]methyl 2,2,2-trifluoroacetate (2.60 g, 6.51 mmol) in a mixed solvent of THF (15.0 mL) and $H_2O$ (5.00 mL) was added $LiOH.H_2O$ (1.37 g, 32.5 mmol). The reaction mixture was stirred at 60° C. for 20 hrs. On completion, the residue was poured into water (5 mL) and stirred for 5 minutes, then the aqueous phase was extracted with ethyl acetate (50 mL×2). The combined organic phase was washed with brine (2×50 mL), dried with anhydrous $Na_2SO_4$, filtered and concentrated in vacuo. The residue was purified by silica gel chromatography (column height: 250 mm, diameter: 100 mm, 100-200 mesh silica gel, DCM/MeOH=25/1, Rf=0.41) to afford the compound (840 mg, 35% yield) as yellow solid. $^1H$ NMR (400 MHz, DMSO-$d_6$) δ 7.88 (s, 1H), 7.31 (s, 1H), 6.63 (s, 1H), 5.35-5.15 (m, 3H), 4.48 (t, J=5.2 Hz, 1H), 4.32-4.22 (m, 1H), 3.27 (t, J=5.6 Hz, 2H), 2.12-2.03 (m, 2H), 1.92-1.80 (m, 4H), 1.59 (s, 6H), 1.50-1.40 (m, 1H), 1.18-1.05 (m, 2H). LC-MS ($ESI^+$) m/z 304.1 $(M+H)^+$.

N-[2-(4-formylcyclohexyl)-6-(1-hydroxy-1-methyl-ethyl)indazol-5-yl]-6-methyl-pyridine-2-carboxamide (Intermediate APG)

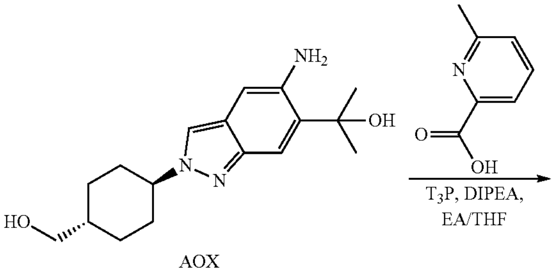

AOX

-continued

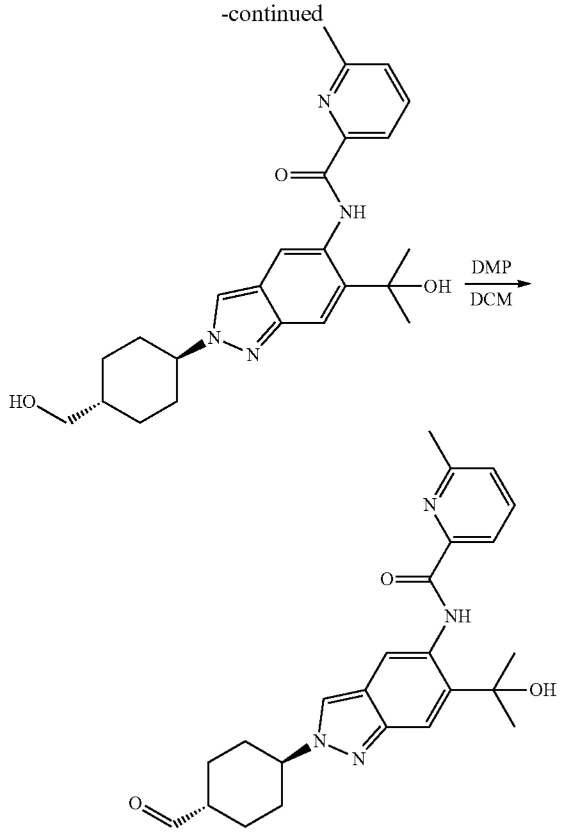

APG

Step 1—N-[2-[4-(hydroxymethyl)cyclohexyl]-6-(1-hydroxy-1-methyl-ethyl)indazol-5-yl]-6-methyl-pyridine-2-carboxamide To a solution of 2-[5-amino-2-[4-(hydroxymethyl)cyclohexyl]indazol-6-yl]propan-2-ol (300 mg, 988 umol, Intermediate AOX) and 6-methylpyridine-2-carboxylic acid (162 mg, 1.19 mmol, CAS #934-60-1) in a mixed solvent of EA (10.0 mL) and THE (10.0 mL) was added DIPEA (1.28 g, 9.89 mmol, 1.72 mL) and $T_3P$ (943 mg, 1.48 mmol, 50% solution). The reaction mixture was stirred at 25° C. for 3 hrs. On completion, the reaction mixture was quenched with water (10 mL), and extracted with ethyl acetate (3×80 mL). The combined organic layers were washed with brine (50 mL), dried over anhydrous sodium sulfate, filtered and concentrated in vacuo to give a residue. The crude product was purified by reversed phase (0.1% $NH_3.H_2O$ condition) to give the title compound (150 mg, 35% yield) as a yellow solid. $^1H$ NMR (400 MHz, $CDCl_3$) δ 12.01 (s, 1H), 8.73 (s, 1H), 8.03 (d, J=7.6 Hz, 1H), 7.81 (s, 1H), 7.69 (t, J=7.6 Hz, 1H), 7.65 (s, 1H), 7.22 (d, J=7.6 Hz, 1H), 4.39-4.19 (m, 1H), 3.56 (s, 1H), 3.46 (d, J=6.4 Hz, 2H), 2.56 (s, 3H), 2.40 (s, 1H), 2.30-2.18 (m, 2H), 1.91-1.83 (m, 2H), 1.72 (s, 6H), 1.60-1.49 (m, 3H), 1.22-1.07 (m, 2H).

Step 2—N-[2-(4-formylcyclohexyl)-6-(1-hydroxy-1-methyl-ethyl)indazol-5-yl]-6-methyl-pyridine-2-carboxamide To a solution of N-[2-[4-(hydroxymethyl)cyclohexyl]-6-(1-hydroxy-1-methyl-ethyl)indazol-5-yl]- 6-methyl-pyridine-2-carboxamide (150 mg, 355 umol) in DCM (3.00 mL) was added DMP (226 mg, 532 umol). The mixture was stirred at 20° C. for 3 hrs. On completion, the reaction mixture was quenched by addition saturated solution of $Na_2S_2O_3$(3 mL), and saturated solution of $NaHCO_3$ (1 mL), and extracted with DCM (3×3 mL). The combined organic layers was washed with brine (2×5 mL), dried over anhydrous $Na_2SO_4$, filtered and concentrated in vacuo to give the title compound (149 mg, 99% yield) as a yellow solid. LC-MS (ESI$^+$) m/z 422.3 (M+H)$^+$.

Methyl 5-amino-2-[4-(hydroxymethyl)phenyl]indazole-6-carboxylate (Intermediate APK)

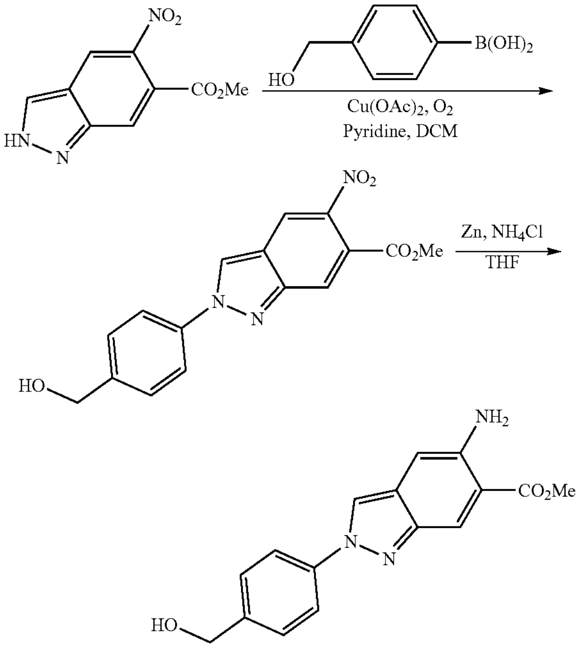

APK

Step 1—Methyl 2-[4-(hydroxymethyl)phenyl]-5-nitro-indazole-6-carboxylate

To a solution of methyl 5-nitro-2H-indazole-6-carboxylate (20.0 g, 90.4 mmol, synthesized via Steps 1 of Intermediate TJ) and [4-(hydroxymethyl)phenyl]boronic acid (16.4 g, 108 mmol, CAS #59016-53-2) in DCM (500 mL) was added $Cu(OAc)_2$ (19.7 g, 108 mmol) and pyridine (42.9 g, 542 mmol, 43.7 mL). The reaction mixture was stirred at 40° C. for 2 days under $O_2$ (15 psi). On completion, the reaction mixture was filtered. The filter cake was washed with DCM (2×20 mL) and water (3×100 mL). Then the solid was collected and dried in vacuo. The crude product was triturated with water (2×100 mL) to give the title compound (7.00 g, 23.6% yield) as an off-white solid, which was confirmed by NOE. $^1$H NMR (400 MHz, DMSO-$d_6$) δ 9.48 (s, 1H), 8.72 (s, 1H), 8.19 (s, 1H), 8.08 (d, J=8.0 Hz, 2H), 7.57 (d, J=8.0 Hz, 2H), 5.39 (t, J=4.0 Hz, 1H), 4.60 (d, J=4.0 Hz, 2H), 3.86 (s, 3H).

Step 2—Methyl 5-amino-2-[4-(hydroxymethyl)phenyl]indazole-6-carboxylate

To a solution of methyl 2-[4-(hydroxymethyl)phenyl]-5-nitro-indazole-6-carboxylate (2.00 g, 6.11 mmol) in THE (150 mL) was added Zn (2.00 g, 30.5 mmol) and $NH_4Cl$ (3.27 g, 61.1 mmol). The reaction mixture was stirred at 60° C. for 24 hours under $N_2$. On completion, the reaction mixture was filtered. The filter cake was diluted with THE (300 mL) and stirred at 60 C for 0.5 hour. Then the mixture was filtered. The filtrate was concentrated in vacuo to give the title compound (1.40 g, 77% yield) as a yellow solid. LC-MS (ESI$^+$) m/z 298.1 (M+1)$^+$.

N-[2-(4-formylphenyl)-6-(1-hydroxy-1-methyl-ethyl)indazol-5-yl]-6-(trifluoromethyl)pyridine-2-carboxamide (Intermediate APL)

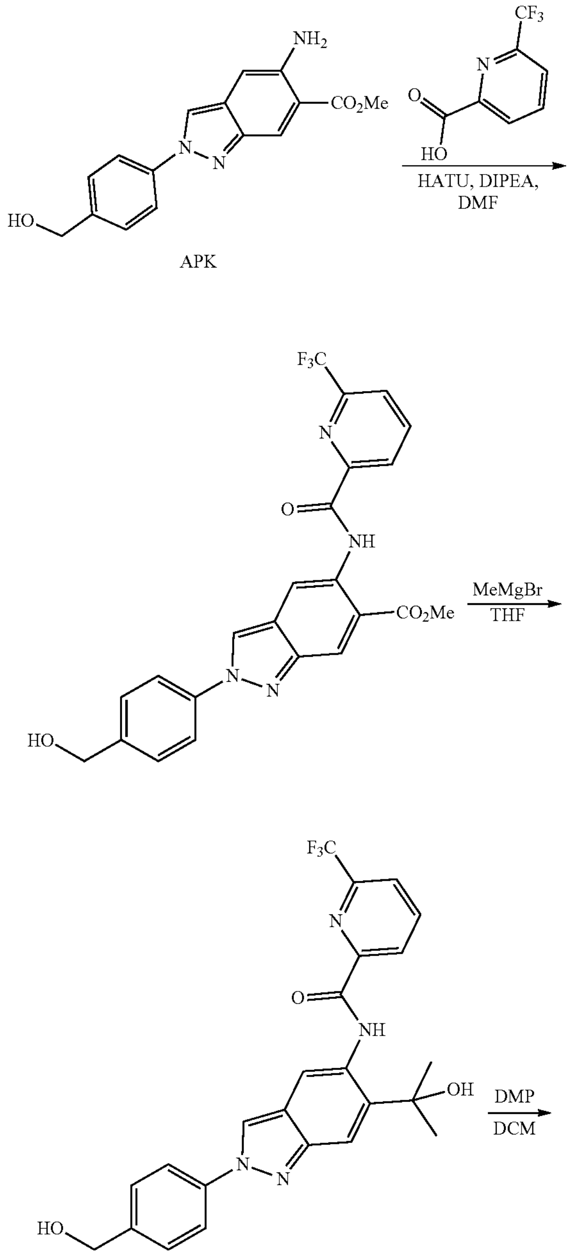

-continued

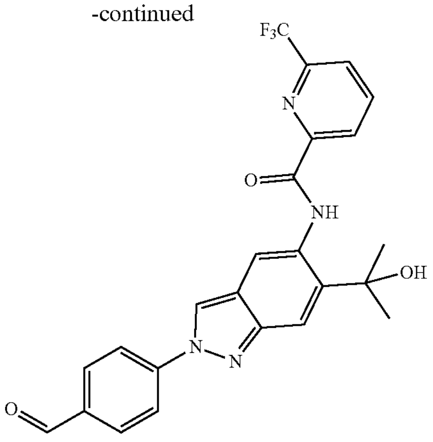

APL

Step 1—Methyl 2-[4-(hydroxymethyl)phenyl]-5-[[6-(trifluoromethyl)pyridine-2-carbonyl]amino]indazole-6-carboxylate To a solution of methyl 5-amino-2-[4-(hydroxymethyl) phenyl]indazole-6-carboxylate (1.00 g, 3.36 mmol, Intermediate APK) and 6-(trifluoromethyl)pyridine-2-carboxylic acid (642 mg, 3.36 mmol, CAS #131747-42-7) in DMF (5 mL) was added HATU (1.28 g, 3.36 mmol). The reaction mixture was stirred at 25° C. for 1 hour. Then DIPEA (217 mg, 1.68 mmol, 0.3 mL) was added and the reaction mixture was stirred at 25° C. for 1 hour. On completion, the reaction mixture was quenched with water (20 mL) and filtered. The filter cake was washed with water (2×10 mL) and dried in vacuo to give the title compound (1.30 g, 82% yield) as light yellow solid. LC-MS (ESI$^+$) m/z 471.1 (M+1)$^+$.

Step 2—N-[6-(1-hydroxy-1-methyl-ethyl)-2-[4-(hydroxymethyl)phenyl]indazol-5-yl]-6-(trifluoro methyl)pyridine-2-carboxamide To a solution of methyl 2-[4-(hydroxymethyl)phenyl]-5-[[6-(trifluoromethyl)pyridine-2-carbonyl]amino]indazole-6-carboxylate (800 mg, 1.70 mmol) in THE (50 mL) was added MeMgBr (3 M, 3.4 mL). The reaction mixture was stirred at 25° C. for 2 hours. On completion, the reaction mixture was poured into ice-water (200 mL) and extracted with EA (2×500 mL). The combined organic layers were washed with brine (2×300 mL), dried with anhydrous $Na_2SO_4$ and filtered. The filtrate was concentrated in vacuo. The residue was purified by reverse phase (0.1%, FA) to give the title compound (800 mg, 99% yield) as a light yellow solid. LC-MS (ESI$^+$) m/z 471.1 (M+1)$^+$.

Step 3—N-[2-(4-formylphenyl)-6-(1-hydroxy-1-methyl-ethyl)indazol-5-yl]-6-(trifluoromethyl)pyridine-2-carboxamide To a solution of N-[6-(1-hydroxy-1-methyl-ethyl)-2-[4-(hydroxymethyl)phenyl]indazol-5-yl]-6- (trifluoromethyl) pyridine-2-carboxamide (800 mg, 1.70 mmol) in THE (50 mL) was added DMP (721 mg, 1.70 mmol). The reaction mixture was stirred at 25° C. for 1 hour. On completion, the reaction mixture was diluted with EA (500 mL) and washed with sat. $NaHCO_3$ (2×100 mL) and sat. $Na_2S_2O_3$ (2×100 mL). The organic layer was dried with anhydrous $Na_2SO_4$ and filtered. The filtrate was concentrated in vacuo to give the title compound (280 mg, 32.6% yield) as a yellow solid. LC-MS (ESI$^+$) m/z 468.9 (M+1)$^+$.

Tert-butyl N-[2-(4-formylcyclohexyl)-6-(1-hydroxy-1-methyl-ethyl)indazol-5-yl]pyrazolo [1,5-a]pyrimidine-3-carboxamide (Intermediate APP)

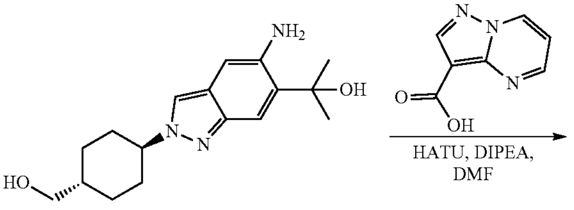

AOX

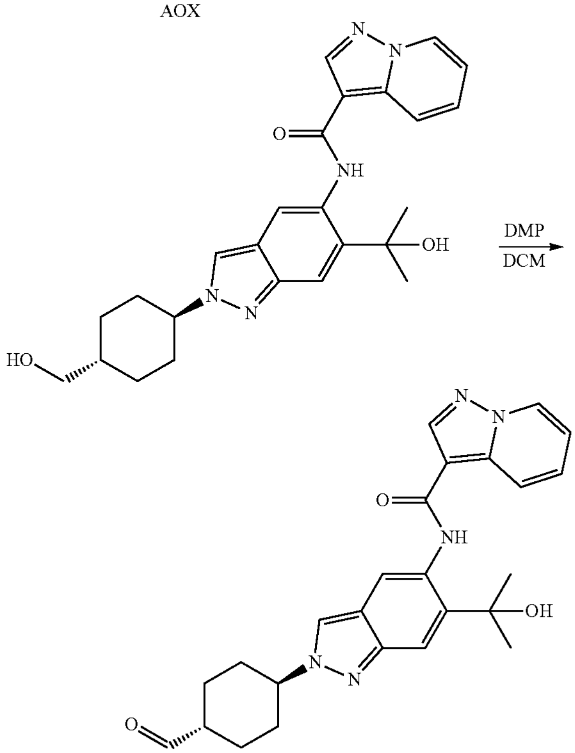

APP

Step 1—N-[2-[4-(hydroxymethyl)cyclohexyl]-6-(1-hydroxy-1-methyl-ethyl)indazol-5-yl]pyrazolo[1,5-a]pyrimidine-3-carboxamide To a solution of 2-[5-amino-2-[4-(hydroxymethyl)cyclohexyl]indazol-6-yl]propan-2-ol (120 mg, 329 umol, Intermediate AOX) and pyrazolo[1,5-a]pyrimidine-3-carboxylic acid (53.8 mg, 329 umol, CAS #25940-35-6) in DMF (3 mL) was added DIPEA (426 mg, 3.29 mmol) and HATU (163 mg, 428 umol). The reaction mixture was stirred at 25° C. for 2 hrs. On completion, the reaction mixture was filtered and concentrated in vacuo. The residue was purified by reverse phase flash (0.1% $NH_3.H_2O$) to give the title compound (80.0 mg, 51% yield) as white solid. $^1$H NMR (400 MHz, DMSO-$d_6$) δ 11.23 (s, 1H), 9.31 (dd, J=1.6, 7.2 Hz, 1H), 8.80 (dd, J=1.6, 4.4 Hz, 1H), 8.65 (s, 1H), 8.32 (d, J=5.2 Hz, 2H), 7.56 (s, 1H), 7.28 (dd, J=4.4, 7.2 Hz, 1H), 5.68 (s, 1H), 4.48 (t, J=5.2 Hz, 1H), 4.45-4.35 (m, 1H), 3.30-3.28 (m, 2H), 2.96 (s, 1H), 2.18-2.10 (m, 2H), 1.92-1.87 (m, 2H), 1.60 (s, 6H), 1.18-1.14 (m, 2H), 1.08-0.96 (m, 2H); LC-MS ($ESI^+$) m/z 471.3 $(M+Na)^+$.

Step 2—Tert-butyl N-[2-(4-formylcyclohexyl)-6-(1-hydroxy-1-methyl-ethyl)indazol-5-yl]pyrazolo [1,5-a]pyrimidine-3-carboxamide To a solution of N-[2-[4-(hydroxymethyl)cyclohexyl]-6-(1-hydroxy-1-methyl-ethyl)indazol-5-yl]pyrazolo[1,5-a]pyrimidine-3-carboxamide (80.0 mg, 166 umol) in DCM (2 mL) was added DMP (141 mg, 332 umol, 103 uL). The mixture was stirred at 25° C. for 1 hour. On completion, the mixture was quenched with sat. $Na_2S_2O_3$ (5 mL) and sat. $NaHCO_3$ (5 mL) and stirred for 10 minutes. The mixture was extracted with DCM (2×20 mL). The organic layer was washed with brine (2×10 mL), dried over $Na_2SO_4$, filtered and the filtrate was concentrated in vacuo to give the title compound (40.0 mg, 39% yield) as yellow solid. LC-MS ($ESI^+$) m/z 447.3 $(M+H)^+$.

Tert-butyl 2-(2-bromoethyl)-7-azaspiro[3.5]nonane-7-carboxylate (Intermediate AQG)

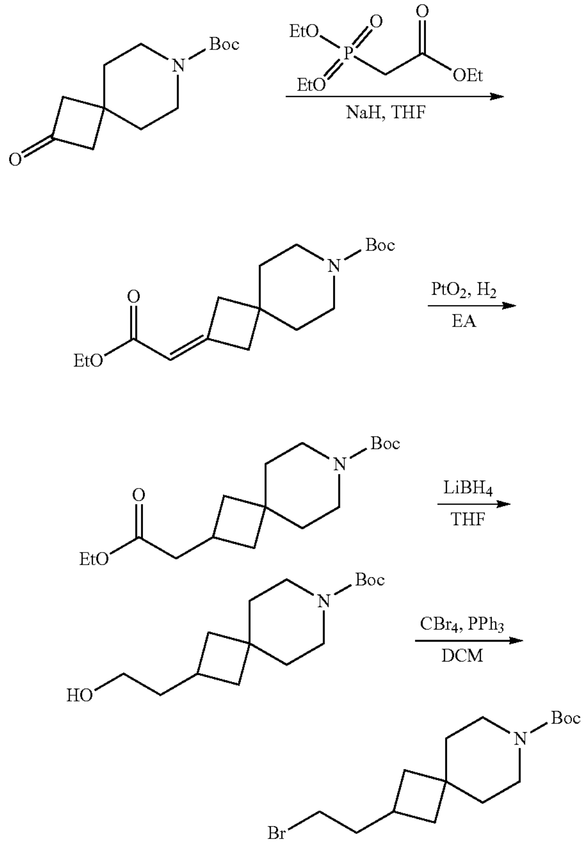

AQG

Step 1—Tert-butyl 2-(2-ethoxy-2-oxoethylidene)-7-azaspiro[3.5]nonane-7-carboxylate To a solution of methyl 2-diethoxyphosphorylacetate (2.64 g, 12.5 mmol) in DMF (30 mL) was added NaH (501 mg, 12.5 mmol, 60% dispersion in mineral oil) at 0° C. with stirring for 0.5 hour. Next was added a solution of tert-butyl 2-oxo-7-azaspiro[3.5]nonane-7-carboxylate (2.00 g, 8.36 mmol, CAS #203661-69-2) in DMF (10 mL). The mixture was warmed to 25° C. with stirring for 2 hours. On completion, the mixture was poured into 150 mL saturated ammonium chloride aqueous solution and extracted with ethyl acetate (50 mL×3). The combined organic layers were washed with brine (20 mL, dried over anhydrous sodium sulfate and concentrated in vacuo. The residue was purified by silica gel column chromatography [petroleum ether:ethyl acetate=10:1 to 3:1]. The title compound (2.00 g, 80% yield) was obtained as colorless oil. $^1H$ NMR (400 MHz, $CDCl_3$) δ 5.65-5.64 (m, 1H), 3.62 (s, 3H), 3.35-3.21 (m, 4H), 2.80 (s, 2H), 2.50 (s, 2H), 1.52-1.45 (m, 2H), 1.38 (m, 9H).

Step 2—Tert-butyl 2-(2-ethoxy-2-oxoethyl)-7-azaspiro[3.5]nonane-7-carboxylate

To a solution of tert-butyl 2-(2-methoxy-2-oxo-ethylidene)-7-azaspiro[3.5]nonane-7-carboxylate (1.8 g, 6.09 mmol) in EtOH (50 mL) was added $Pd(OH)_2/C$ (100 mg, 10% wt) and Pd/C (100 mg, 10% wt) under $N_2$. The suspension was degassed under vacuum and purged with $H_2$ several times. The mixture was stirred under $H_2$ (15 psi) at 25° C. for 16 hours. On completion, the reaction mixture was filtered and the filter was concentrated. The title compound (1.7 g, 80% purity) was obtained as colorless oil. $^1H$ NMR (400 MHz, $CDCl_3$) δ 3.58 (s, 3H), 3.32-3.24 (m, 2H), 3.22-3.14 (m, 2H), 2.57 (td, J=8.0, 16.0 Hz, 1H), 2.36 (d, J=7.8 Hz, 2H), 2.03-1.92 (m, 2H), 1.52-1.47 (m, 2H), 1.43-1.34 (m, 14H).

Step 3—Ttert-butyl 2-(2-hydroxyethyl)-7-azaspiro [3.5]nonane-7-carboxylate

To a solution of tert-butyl 2-(2-methoxy-2-oxo-ethyl)-7-azaspiro[3.5]nonane-7-carboxylate (1.70 g, 5.72 mmol) in THE (30 mL) was added $LiBH_4$ (373 mg, 17.1 mmol) and the mixture was stirred at 75° C. for 4 hours. On, completion, the mixture was cooled to rt and poured into 30 mL water and extracted with ethyl acetate (50 mL×3). The combined organic layers were washed with water, brine, dried over anhydrous sodium sulfate and concentrated in vacuo. The title compound (1.50 g, 97% yield) was obtained as colorless oil. $^1H$ NMR (400 MHz, $CDCl_3$) δ 3.57-3.45 (m, 2H), 3.31-3.23 (m, 2H), 3.22-3.15 (m, 2H), 2.27 (d, J=8.0, 16.0 Hz, 1H), 1.96-1.85 (m, 2H), 1.61 (q, J=6.8 Hz, 2H), 1.52-1.45 (m, 2H), 1.41-1.30 (m, 13H).

Step 4—Tert-butyl 2-(2-bromoethyl)-7-azaspiro[3.5] nonane-7-carboxylate

To a solution of tert-butyl 2-(2-hydroxyethyl)-7-azaspiro [3.5]nonane-7-carboxylate (1.50 g, 5.57 mmol) and $PPh_3$ (4.38 g, 16.7 mmol) in DCM (30 mL) was added $CBr_4$ (5.54 g, 16.7 mmol) at 0° C. and the mixture was stirred at 25° C. for 14 hours. On completion, the mixture was filtered and concentrated. The residue was purified by silica gel column chromatography [petroleum ether:ethyl acetate=100:1 to 3:1] and the title compound (1.50 g, 81% yield) was obtained as colorless oil. $^1H$ NMR (400 MHz, $CDCl_3$) δ 3.38-3.30 (m, 4H), 3.29-3.23 (m, 2H), 2.40 (J=8.0 Hz, 1H), 2.05-1.94 (m, 4H), 1.59-1.55 (m, 2H), 1.47-1.39 (m, 13H).

3-(4-Bromo-3-methyl-2-oxo-2,3-dihydro-1H-benzo[d]imidazol-1-yl)piperidine-2,6-dione (Intermediate HP)

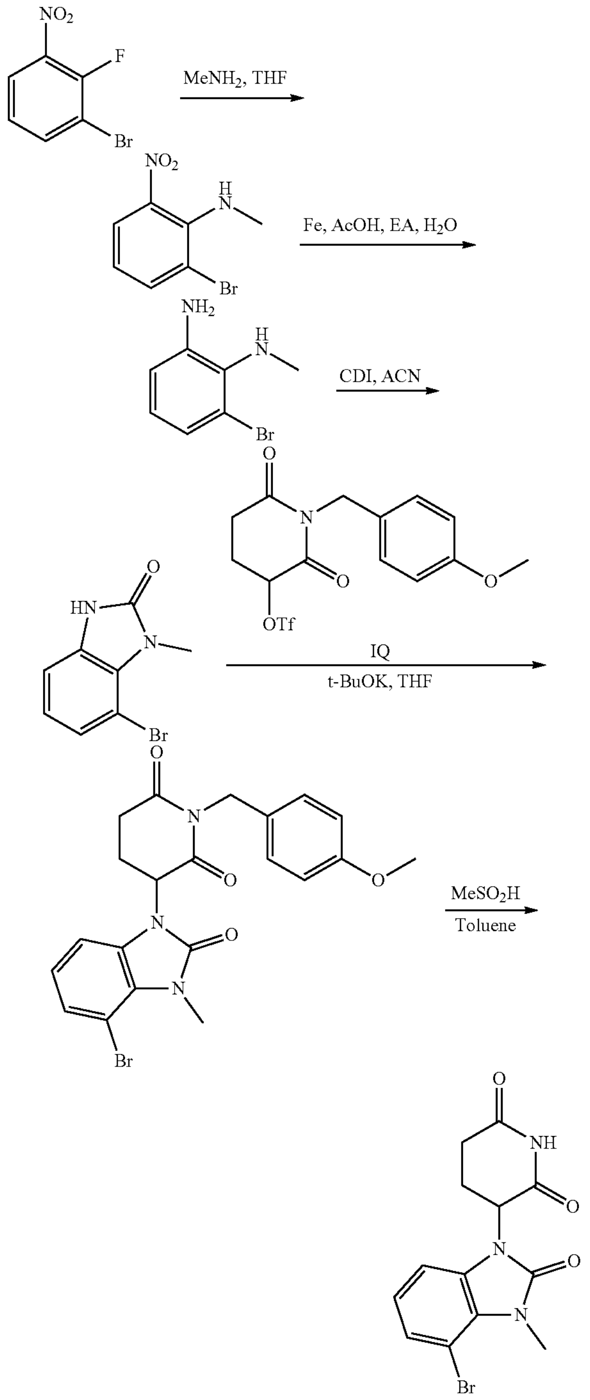

HP

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added $MeNH_2$ (2 M, 400 mL). The reaction mixture was stirred at 60° C. for 12 hours. On completion, the reaction mixture was poured into sat.$NaHCO_3$ (30 mL) and extracted with EA (3×200 mL). The combined organic layers were washed with brine (2×200 mL), dried with anhydrous $Na_2SO_4$, filtered and concentrated in vacuo to give the title compound (40.0 g, 95% yield) as red oil. LC-MS (ESI$^+$) m/z 230.9 $(M+H)^+$.

Step 2—3-Bromo-N2-methyl-benzene-1,2-diamine

To a mixture of 2-bromo-N-methyl-6-nitro-aniline (23.0 g, 99.5 mmol) in EA (300 mL) and $H_2O$ (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over $Na_2SO_4$, filtered and concentrated in vacuo to give the title compound (20.0 g, 99% yield) as red oil. $^1$H NMR (400 MHz, DMSO-$d_6$) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under $N_2$ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. $^1$H NMR (400 MHz, DMSO-$d_6$) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine- 2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl]trifluoromethanesulfonate (20.1 g, 52.8 mmol, Intermediate IQ) in a solution of THE (100 mL) was added dropwise. The resulting reaction mixture was stirred at 20° C. for 0.5 hr under $N_2$. On completion, the reaction mixture was quenched with saturated $NH_4Cl$ (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1$H NMR (400 MHz, $CDCl_3$) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine -2,6-dione (13.3 g, 29.0 mmol) in a mixed solvent of Tol. (80 mL) and methane sulfonic acid (40 mL) was degassed and purged with $N_2$ for 3 times, and then the mixture was stirred at 120° C. for 2 hrs under $N_2$ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1H$ NMR (400 MHz, DMSO-$d_6$) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

3-[4-[2-(7-azaspiro[3.5]nonan-2-yl)ethyl]-3-methyl-2-oxo-benzimidazol-1-yl]piperidine-2,6-dione (Intermediate APZ)

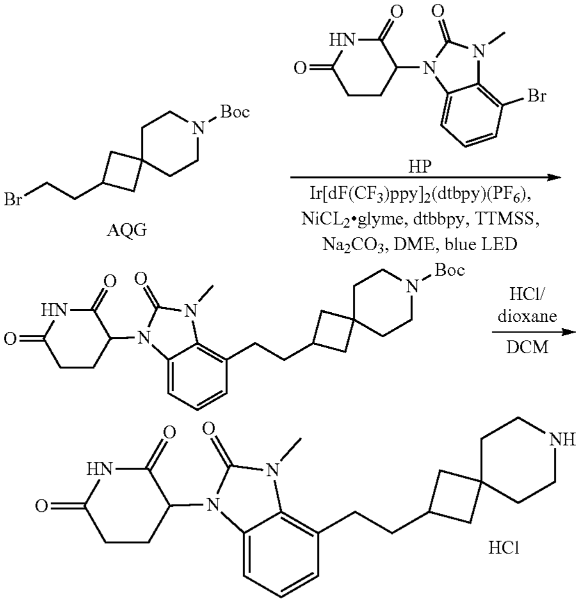

APZ

Step 1—Tert-butyl 2-(2-(1-(2,6-dioxopiperidin-3-yl)-3-methyl-2-oxo-2,3-dihydro-1H-benzo[d]imidazol-4-yl)ethyl)-7-azaspiro[3.5]nonane-7-carboxylate To an 40 mL vial equipped with a stir bar was added 3-(4-bromo-3-methyl-2-oxo-benzimidazol-1-yl)piperidine-2,6-dione (1.00 g, 2.96 mmol, Intermediate HP), tert-butyl 2-(2-bromoethyl)-7-azaspiro [3.5]nonane-7-carboxylate (1.08 g, 3.25 mmol, Intermediate AQG), bis[3,5-difluoro-2-[5-(trifluoromethyl)-2-pyridyl]phenyl]iridium(1+);4-tert-butyl-2-(4-tert-butyl-2-pyridyl)pyridine;hexafluorophosphate (33.1 mg, 29.5 umol), $NiCl_2$.dtbbpy (5.88 mg, 14.7 umol), TTMSS (735 mg, 2.96 mmol) and $Na_2CO_3$ (626 mg, 5.91 mmol) in DME (24 mL). The vial was sealed and placed under nitrogen was added. The reaction was stirred and irradiated with a 34 W blue LED lamp (7 cm away), with cooling fan to keep the reaction temperature at 25° C. for 4 hr. On completion, the mixture was filtered and concentrated. The residue was purified by prep-HPLC: reverse phase (condition: 0.1% FA). The title compound (400 mg, 26% yield) was obtained as red solid. LC-MS (ESI$^+$) m/z 455.2 (M+H-56)*.

Step 2—3-(4-(2-(7-azaspiro[3.5]nonan-2-yl)ethyl)-3-methyl-2-oxo-2,3-dihydro-1H-benzo[d]imidazol-1-yl)piperidine-2,6-dione To a solution of tert-butyl 2-[2-[1-(2,6-dioxo-3-piperidyl)-3-methyl-2-oxo-benzimidazol-4-yl]ethyl]-7-azaspiro[3.5]nonane-7-carboxylate (140 mg, 274 umol) in DCM (3 mL) was added HCl/dioxane (4 M, 1.08 mL) and the mixture was stirred at 25° C. for 1 hour. On completion, the mixture was concentrated. The title compound (110 mg, 89% yield, HCl) was obtained as white solid. LC-MS (ESI$^+$) m/z 411.0 (M+H)$^+$.

N-[2-(4-formylcyclohexyl)-6-(1-hydroxy-1-methyl-ethyl)indazol-5-yl]pyridine-2-carboxamide (Intermediate AOF)

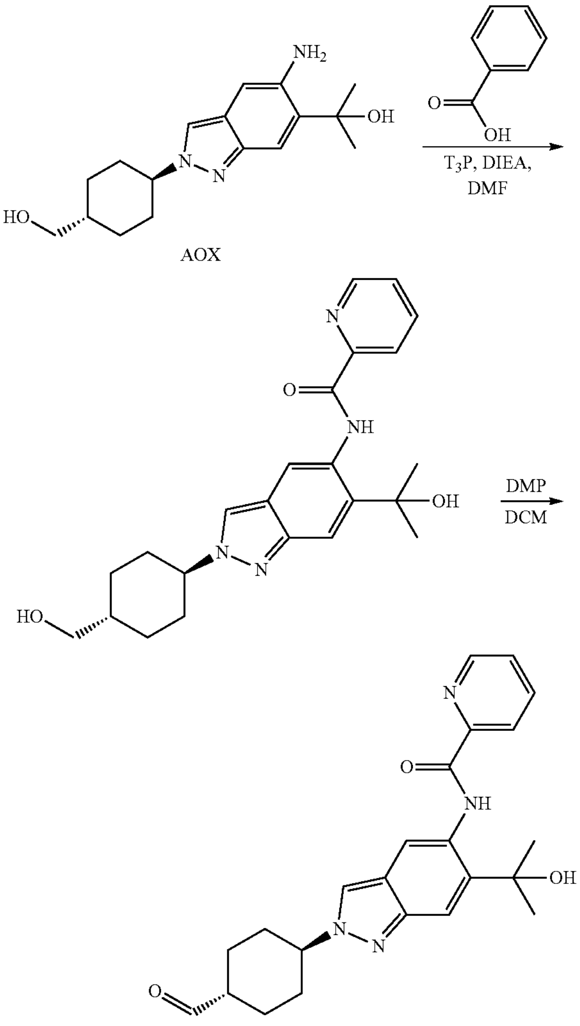

AOF

Step 1—N-[2-[4-(hydroxymethyl)cyclohexyl]-6-(1-hydroxy-1-methyl-ethyl)indazol-5-yl]pyridine-2-carboxamide To a solution of 2-[5-amino-2-[4-(hydroxymethyl)cyclohexyl]indazol-6-yl]propan-2-ol (160 mg, 369 umol, Intermediate AOX), pyridine-2-carboxylic acid (45.4 mg, 369 umol, CAS #98-98-6) in DMF (2 mL) was added DIPEA (143 mg, 1.11 mmol, 193 uL), 2,4,6-tripropyl-1,3,5,2,4,6-trioxatriphosphinane 2,4,6-trioxide (469 mg, 738 umol, 439 uL, 50% solution). The reaction mixture was stirred at 25° C. for 2 hrs. On completion, the reaction mixture was filtered and concentrated in vacuo. The crude product was purified by reversed-phase HPLC (0.1% $NH_3.H_2O$). to give the title compound (80.0 mg, 45% yield) as white solid. $^1H$ NMR (400 MHz, DMSO-$d_6$) δ 12.32 (s, 1H), 8.72-8.69 (m, 1H), 8.67 (s, 1H), 8.46-8.33 (m, 2H), 8.19 (d, J=7.6 Hz, 1H), 8.09-8.02 (m, 1H), 7.66-7.62 (m, 1H), 7.56 (s, 1H), 7.52-7.51 (m, 1H), 6.02 (s, 1H), 4.44-4.36 (m, 1H), 4.23 (d, J=6.4 Hz, 1H), 3.29 (d, J=6.4 Hz, 2H), 2.16-2.11 (m, 2H), 1.90 (d, J=10.8 Hz, 2H), 1.61 (s, 6H), 1.53-1.44 (m, 1H), 1.21-1.10 (m, 2H); LC-MS ($ESI^+$) m z 409.2 $(M+H)^+$.

Step 2—N-[2-(4-formylcyclohexyl)-6-(1-hydroxy-1-methyl-ethyl)indazol-5-yl]pyridine-2-carboxamide To a solution of N-[2-[4-(hydroxymethyl)cyclohexyl]-6-(1-hydroxy-1-methyl-ethyl)indazol-5-yl]pyridine -2-carboxamide (70.0 mg, 171 umol) in DCM (2 mL) was added DMP (87.2 mg, 206 umol, 63.6 uL). The mixture was stirred at 25° C. for 5 hours. On completion, the mixture was quenched with sat.$Na_2S_2O_3$ (2 mL) and sat.$NaHCO_3$ (2 mL), stirred for 10 minutes, then extracted with DCM (2×20 mL). The organic layer was washed with brine (2×10 mL), dried with $Na_2SO_4$, filtered and the filtrate was concentrated in vacuo to give the title compound (50.0 mg, 47% yield) as yellow solid. LC-MS ($ESI^+$) m/z 407.1 $(M+H)^+$.

Tert-butyl 2-(bromomethyl)-7-azaspiro[3.5]nonane-7-carboxylate (Intermediate AMR)

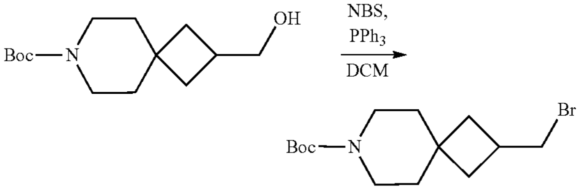

AMR

To a solution of tert-butyl 2-(hydroxymethyl)-7-azaspiro[3.5]nonane-7-carboxylate (1 g, 3.92 mmol) (CAS #1356476-27-1) in ACN (20 mL) was added NBS (1.39 g, 7.83 mmol) and $PPh_3$ (2.05 g, 7.83 mmol). The reaction mixture was stirred at 25° C. for 12 hrs under $N_2$. On completion, the reaction mixture was quenched with water (10 mL), and extracted with ethyl acetate (3×30 mL). The combined organic layers were washed with brine (10 mL), dried over anhydrous sodium sulfate, filtered and the filtrate was concentrated in vacuo. The residue was purified by silica gel chromatography (petroleum ether) to give the title compound (1.00 g, 80% yield) as a white solid. $^1H$ NMR (400 MHz, $CDCl_3$) δ 3.43 (d, J=7.2 Hz, 2H), 3.38-3.32 (m, 2H), 3.31-3.22 (m, 2H), 2.66 (td, J=8.0, 16.0 Hz, 1H), 2.06-1.94 (m, 2H), 1.61-1.46 (m, 6H), 1.45 (s, 9H).

3-(4-(7-Azaspiro[3.5]nonan-2-ylmethyl)-3-methyl-2-oxo-2,3-dihydro-1H-benzo[d]imidazol- 1-yl)piperidine-2,6-dione (Intermediate AMS)

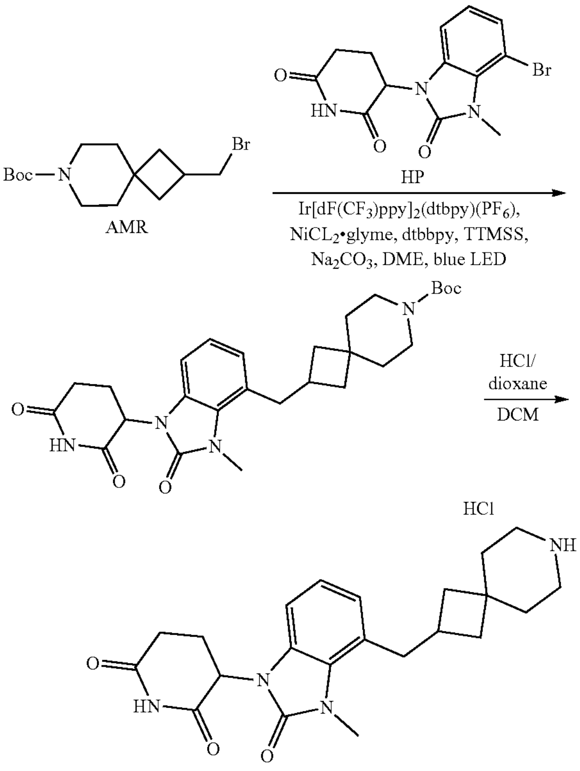

AMS

Step 1—Tert-butyl 2-[[1-(2,6-dioxo-3-piperidyl)-3-methyl-2-oxo-benzimidazol-4-yl]methyl]-7-azaspiro[3.5]nonane-7-carboxylate To an 8 mL vial equipped with a stir bar was added 3-(4-bromo-3-methyl-2-oxo-benzimidazol-1-yl)piperidine-2,6-dione (200 mg, 591 umol, Intermediate HP), tert-butyl 2-(bromomethyl)-7-azaspiro[3.5]nonane-7-carboxylate (245 mg, 769 umol, Intermediate AMR), bis[3,5-difluoro-2-[5-(trifluoromethyl)-2-pyridyl]phenyl]iridium(1+);4-tert-butyl-2-(4-tert-butyl-2-pyridyl)pyridine;hexafluorophosphate (6.64 mg, 5.91 umol), dichloronickel;1,2-dimethoxyethane (649 ug, 2.96 umol), 4-tert-butyl-2-(4-tert-butyl-2-pyridyl)pyridine (952 ug, 3.55 umol), bis (trimethylsilyl)silyltrimethyl-silane (147.0 mg, 591 umol, 182.47 uL) and $Na_2CO_3$ (125 mg, 1.18 mmol) in DME (6 mL). The vial was sealed and placed under nitrogen was added. The reaction was stirred and irradiated with a 34 W blue LED lamp (7 cm away), with cooling fan to keep the reaction temperature at 25° C. for 14 hrs. On completion, the reaction mixture was concentrated in vacuo. The residue was purified by reversed-phase HPLC (0.1% FA condition) to give the title compound (150 mg, 51% yield) as a white solid. $^1H$ NMR (400 MHz, $CDCl_3$) δ 8.24 (s, 1H), 7.02-6.94 (m, 1H), 6.85 (d, J=7.6 Hz, 1H), 6.67 (d, J=7.6 Hz, 1H), 5.26-5.16 (m, 1H), 3.66 (s, 3H), 3.39-3.24 (m, 4H), 3.05 (d, J=7.2 Hz, 2H), 3.00-2.68 (m, 3H), 2.57 (td, J=8.0, 16.0 Hz, 1H), 2.26-2.18 (m, 1H), 2.04-1.96 (m, 2H), 1.60-1.47 (m, 6H), 1.45 (s, 9H). LC-MS (ESI$^+$) m/z 497.2 $(M+H)^+$.

Step 2—3-(4-(7-Azaspiro[3.5]nonan-2-ylmethyl)-3-methyl-2-oxo-2,3-dihydro-1H-benzo[d]imidazol-1-yl)piperidine-2,6-dione To a solution of tert-butyl 2-[[1-(2,6-dioxo-3-piperidyl)-3-methyl-2-oxo-benzimidazol-4-yl]methyl]-7- azaspiro[3.5] nonane-7-carboxylate (80 mg, 161 umol) in DCM (5 mL) was added HCl/dioxane (4 M, 3 mL). The reaction mixture was stirred at 20° C. for 2 hrs. On completion, the reaction mixture was concentrated in vacuo to give the title compound (69.0 mg, 99% yield, HCl salt) as a white solid. LC-MS (ESI$^+$) m/z 397.1 $(M+H)^+$.

6-(1-Fluoro-1-methyl-ethyl)pyridine-2-carboxylic acid (Intermediate ARA)

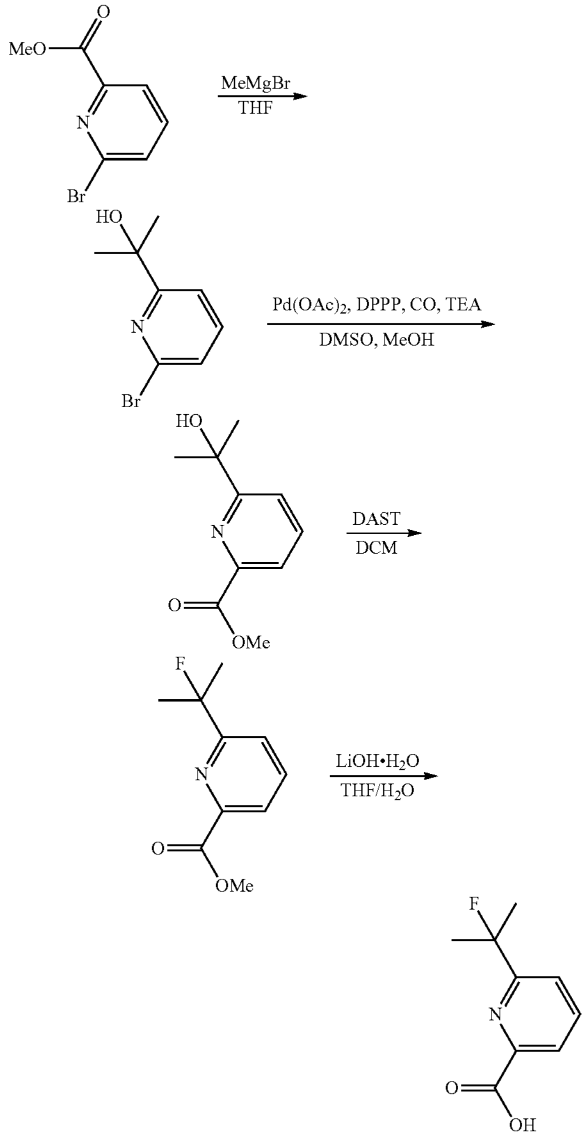

ARA

Step 1—2-(6-Bromo-2-pyridyl)propan-2-ol

To a solution of methyl 6-bromopyridine-2-carboxylate (2.00 g, 9.26 mmo, CAS #26218-75-7) in THE (40 mL) was added MeMgBr (1 M, 21.3 mL) at 0° C. under $N_2$. The mixture was stirred at 25° C. for 1 h. On completion, the reaction was quenched with HCl (1 N, 40 mL), then it was extracted with EA (3×20 mL). The organic layer was washed with sat. $NaHCO_3$ (3×15 mL) and brine (30 mL), dried over $Na_2SO_4$, filtered and concentrated under vacuum to afford the title compound (2.00 g, 90% yield) as a light yellow oil. $^1$H NMR (400 MHz, DMSO-$d_6$) δ 7.75-7.65 (m, 2H), 7.46 (dd, J=1.2, 7.6 Hz, 1H), 5.34 (s, 1H), 1.41 (s, 6H).

Step 2—Methyl 6-(1-hydroxy-1-methyl-ethyl)pyridine-2-carboxylate

To a solution of 2-(6-bromo-2-pyridyl)propan-2-ol (1.80 g, 8.33 mmol) in MeOH (20 mL) and DMSO (20 mL) were added $Pd(OAc)_2$ (131 mg, 583 umol), DPPP (240 mg, 583 umol) and TEA (1.96 g, 19.4 mmol, 2.7 mL). The mixture was degassed and purged with CO for 3 times, and was stirred at 25° C. for 30 min. Then the temperature was raised to 80° C. and the reaction mixture was stirred under CO at 40 psi for 16 hours. On completion, the reaction was filtered and the filtrate was diluted with EA (150 mL), washed with water (3×50 mL) and brine (80 mL), dried over $Na_2SO_4$, filtered and concentrated in vacuo. Then the crude was purified by silica gel column chromatography to afford the title compound (1.40 g, 77% yield) as colorless oil. LC-MS (ESI$^+$) m/z 196.0 $(M+H)^+$.

Step 3—Methyl 6-(1-fluoro-1-methyl-ethyl)pyridine-2-carboxylate

To a solution of methyl-6-(1-hydroxy-1-methyl-ethyl) pyridine-2-carboxylate (1.30 g, 6.0 mmol) in DCM (20 mL) was added DAST (1.20 g, 6.6 mmol, 90% solution) at 0° C. The mixture was stirred at 25° C. for 16 hours. On completion, the reaction was diluted with water (100 mL), extracted with DCM (3×30 mL), washed with brine (40 mL), dried over $Na_2SO_4$, filtered and concentrated in vacuo. Then the crude was purified by silica gel column chromatography to afford the title compound (1.10 g, 93% yield) as a yellow solid. $^1$H NMR (400 MHz, DMSO-$d_6$) δ 8.10-8.04 (m, 1H), 8.00 (d, J=7.8 Hz, 1H), 7.80 (d, J=7.8 Hz, 1H), 1.71 (s, 3H), 1.66 (s, 3 H); LC-MS (ESI$^+$) m/z 198.1 $(M+H)^+$.

Step 4—6-(1-Fluoro-1-methyl-ethyl)pyridine-2-carboxylic acid

To a solution of methyl 6-(1-fluoro-1-methyl-ethyl)pyridine-2-carboxylate (1.00 g, 5.07 mmol) in THF (20 mL) and $H_2O$ (10 mL) was added LiOH $H_2O$ (426 mg, 10.2 mmol) at 0° C. The mixture was stirred at 25° C. for 3 hours. On completion, the organic solvent was removed in vacuo and the crude product was purified by reversed-phase HPLC (0.1% TFA) to give the title compound (0.60 g, 58% yield) as a colorless solid. LC-MS (ESI$^+$) m/z 184.0 $(M+H)^+$.

2-[4-(Hydroxymethyl)cyclohexyl]4-methylbenzenesulfonate (Intermediate ARD)

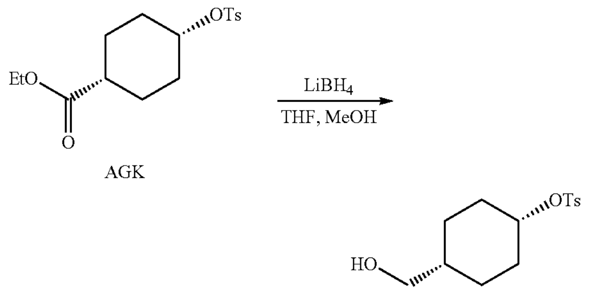

AGK

ARD

To a solution of ethyl 4-(p-tolylsulfonyloxy)cyclohexanecarboxylate (50.0 g, 153 mmol, Intermediate AGK) in a mixed solvent of THF (500 mL) and MeOH (60 mL) was added $LiBH_4$ (10.0 g, 460 mmol) in portions at 20-30° C. Then the reaction mixture was stirred at 40° C. for 1 hr. On completion, the mixture was quenched with water (500 mL), and extracted with EA (2×300 mL). The organic layer was washed with brine (300 mL), dried with $Na_2SO_4$, filtered and the filtrate was concentrated in vacuo to give the title compound (40 g, 92% yield) as a yellow solid. H NMR (400 MHz, $CDCl_3$) δ 7.82-7.76 (m, 2H), 7.33 (d, J=8.0 Hz, 2H), 4.80-4.75 (m, 1H), 3.46 (d, J=6.4 Hz, 2H), 2.45 (s, 3H), 1.93-1.86 (m, 2H), 1.62-1.52 (m, 3H), 1.50-1.41 (m, 3H), 1.40-1.30 (m, 2H).

Methyl 5-amino-2-[4-(hydroxymethyl)cyclohexyl] indazole-6-carboxylate (Intermediate ARE)

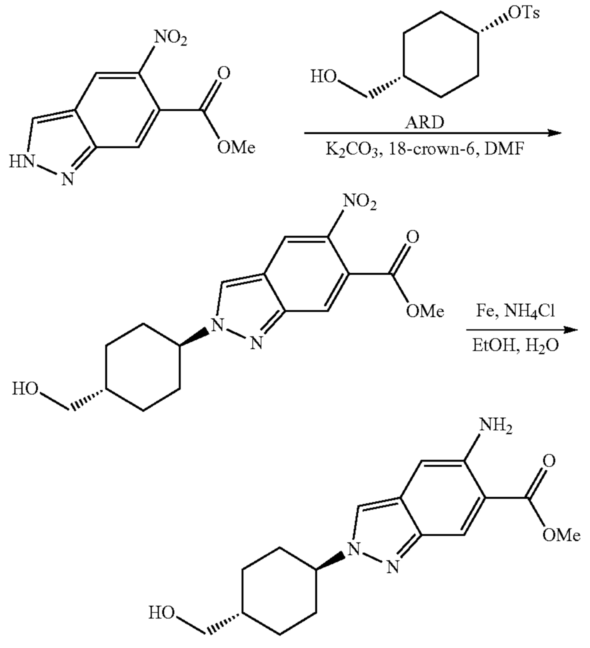

ARE

Step 1—Methyl 2-[4-(hydroxymethyl)cyclohexyl]-5-nitro-indazole-6-carboxylate

To a solution of methyl 5-nitro-2H-indazole-6-carboxylate (15.0 g, 67.8 mmol, synthesized via Steps 1 of Intermediate TJ) and [4-(hydroxymethyl)cyclohexyl]4-methylbenzenesulfonate (48.2 g, 169 mmol, Intermediate ARD) in DMF (300 mL) was added $K_2CO_3$ (23.4 g, 169 mmol), 18-crown-6 (1.79 g, 6.78 mmol) and 4 Å molecular sieves (2 g). The reaction mixture was stirred at 80° C. for 2 days. On completion, the mixture was concentrated in vacuo, then diluted with water (1 L), and extracted with EA (2×300 mL). The organic layer was washed with brine (200 mL), and concentrated in vacuo. The residue was purified by silica gel chromatography ($SiO_2$) to give the title compound (5.00 g, 22% yield) as a yellow solid. $^1H$ NMR (400 MHz, $CDCl_3$) δ 8.42 (s, 1H), 8.23 (d, J=0.6 Hz, 1H), 8.03 (s, 1H), 4.55-4.40 (m, H), 3.93 (s, 3H), 3.57 (t, J=5.2 Hz, 2H), 2.44-2.31 (m, 2H), 2.14-1.95 (m, 4H), 1.68-1.62 (m, 1H), 1.55 (t, J=4.8 Hz, 1H), 1.35-1.24 (m, 2H).

Step 2—Methyl 5-amino-2-[4-(hydroxymethyl)cyclohexyl]indazole-6-carboxylate

To a solution of methyl 2-[4-(hydroxymethyl)cyclohexyl]-5-nitro-indazole-6-carboxylate (4.94 g, 14.8 mmol) in a mixed solvent of EtOH (70 mL) and $H_2O$ (20 mL) was added Fe (8.28 g, 148 mmol) and $NH_4Cl$ (7.93 g, 148 mmol). The reaction mixture was stirred at 70° C. for 1 hr. On completion, the mixture was diluted with water (200 mL), and extracted with EA (2×200 mL). The organic layer was washed with brine (200 mL), dried with $Na_2SO_4$, filtered and the filtrate was concentrated in vacuo to give the title compound (3.60 g, 80% yield) as a yellow solid. LC-MS ($ESI^+$) m/z 304.1 $(M+H)^+$.

6-(1-fluoro-1-methyl-ethyl)-N-[2-(4-formylcyclohexyl)-6-(1-hydroxy -1-methyl-ethyl)indazol-5-yl] pyridine-2-carboxamide (Intermediate AQO)

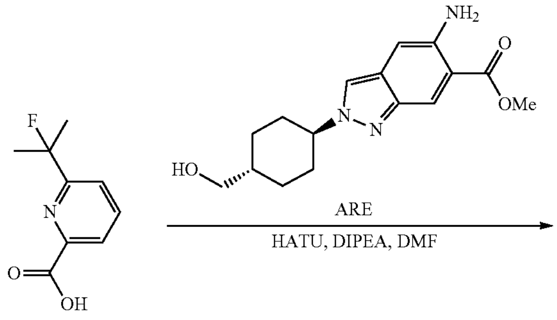

ARA

-continued

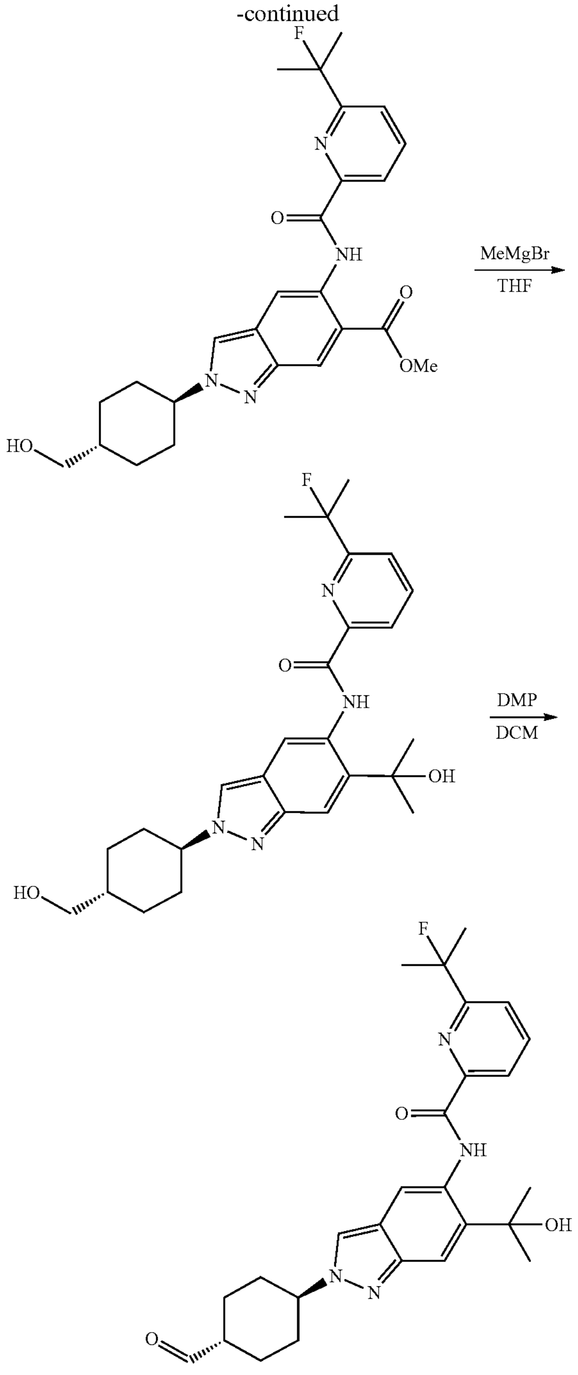

AQO

Step 1—Methyl 5-[[6-(1-fluoro-1-methyl-ethyl) pyridine-2-carbonyl]amino]-2-[4-(hydroxylmethyl) cyclohexyl]indazole-6-carboxylate To a solution of 6-(1-fluoro-1-methyl-ethyl)pyridine-2-carboxylic acid (0.50 g, 2.73 mmol, Intermediate ARA) and methyl 5-amino-2-[4-(hydroxymethyl)cyclohexyl]indazole-6-carboxylate (828 mg, 2.73 mmol, Intermediate ARE) in DMF (10 mL) was added DIPEA (706 mg, 5.46 mmol) and HATU (1.25 g, 3.28 mmol). The mixture was stirred at 25° C. for 16 hours. On completion, the reaction was diluted with EA (100 mL), washed with water (3x30 mL) and brine (40 mL), dried over $Na_2SO_4$, filtered and concentrated in vacuo to give a the residue. The residue was purified by silica gel column chromatography to give the title compound (0.70 g, 49% yield) as a yellow solid. LC-MS ($ESI^+$) m/z 469.2 $(M+H)^+$.

Step 2—6-(1-Fluoro-1-methyl-ethyl)-N-[2-[4-(hydroxymethyl)cyclohexyl]-6-(1-hydroxy-1-methyl-ethyl)indazol-5-yl]pyridine-2-carboxamide To a solution of methyl 5-[[6-(1-fluoro-1-methyl-ethyl) pyridine-2-carbonyl]amino]-2-[4-(hydroxyl methyl)cyclohexyl]indazole-6-carboxylate (0.60 g, 1.28 mmol) in THF (30 mL) was added MeMgBr (3 M, 4.27 mL) at 0° C. The mixture was stirred at 25° C. for 2 hours. On completion, the reaction was added to sat. $NaH_4Cl$ (100 mL), then it was extracted with EA (3x50 mL), washed with brine (50 mL), dried over $Na_2SO_4$, filtered and concentrated in vacuo to give the title compound (0.60 g, 79% yield) as a yellow solid. LC-MS ($ESI^+$) m/z 469.2 $(M+H)^+$.

Step 3—6-(1-Fluoro-1-methyl-ethyl)-N-[2-(4-formylcyclohexyl)-6-(1-hydroxy-1-methyl-ethyl)indazol-5-yl]pyridine-2-carboxamide To a solution of 6-(1-fluoro-1-methyl-ethyl)-N-[2-[4-(hydroxymethyl)cyclohexyl]-6-(1-hydroxyl-1-methyl-ethyl) indazol-5-yl]pyridine-2-carboxamide (0.50 g, 1.07 mmol) in DCM (20 mL) was added DMP (905 mg, 2.13 mmol) at 0° C. The mixture was stirred at 25° C. for 1 hour. On completion, the reaction was quenched with sat. $Na_2S_2O_3$ (100 mL), and extracted with EA (3x30 mL). Then the organic solvent was washed with sat.$NaHCO_3$ (50 mL) and brine (50 mL), dried over $Na_2SO_4$, filtered and concentrated in vacuo to give the title compound (0.48 g, 77% yield) as a light yellow solid.

Tert-butyl (2S)-2-(2-aminoethyl)morpholine-4-carboxylate (Intermediate AQX)

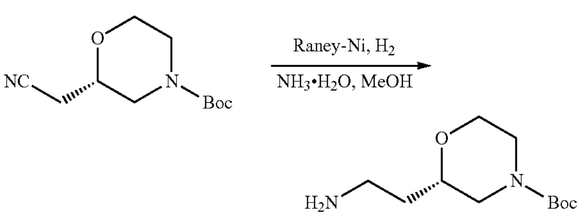

AQX

To a solution of tert-butyl (2S)-2-(cyanomethyl)morpholine-4-carboxylate (500 mg, 2.21 mmol, synthesized via Steps 1-2 of Intermediate ANS) in a mixture of $NH_3.H_2O$ (1.0 mL) and MeOH (10 mL) was added Raney-Ni (94.6 mg, 1.10 mmol) at 25° C. The reaction mixture was stirred at 25° C. for 3 hours under $H_2$ (50 Psi). On completion, the reaction mixture was filtered with celite to remove the Raney-Ni, and the filtrate was concentrated in vacuo to give the title compound (510 mg, 90% yield) as black oil. $^1$HNMR (400 MHz, DMSO-$d_6$) δ 3.84-3.64 (m, 3H), 3.41-3.31 (m, 4H), 2.88-2.73 (m, 2H), 2.59 (s, 2H), 1.55-1.43 (m, 2H), 1.40 (s, 9H).

2-(2,6-Dioxo-3-piperidyl)-4-[2-[(2S)-morpholin-2-yl]ethylamino]isoindoline-1,3-dione (Intermediate AOY)

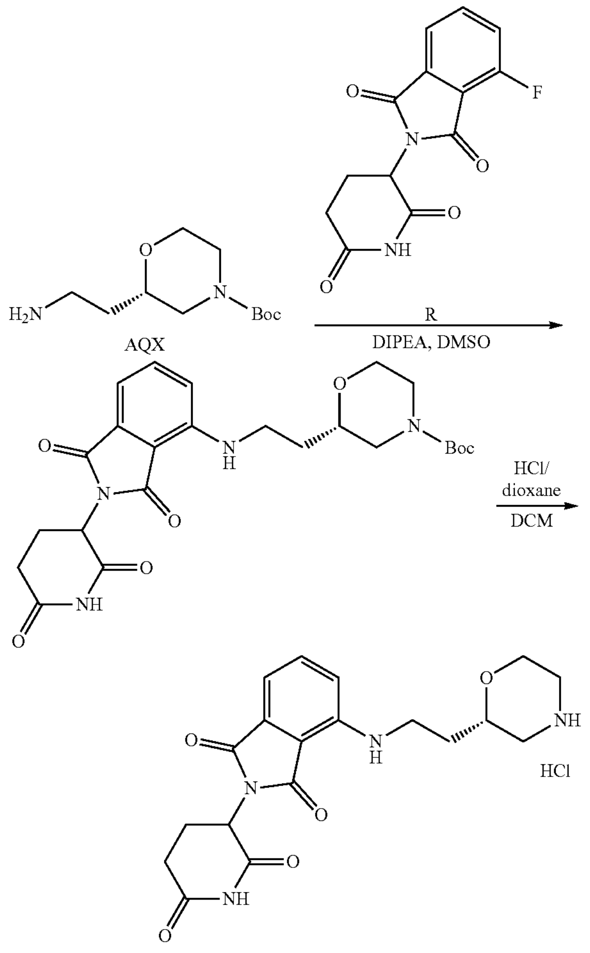

AQY

Step 1—Tert-butyl (2S)-2-[2-[[2-(2,6-dioxo-3-piperidyl)-1,3-dioxo-isoindolin-4-yl]amino]ethyl]morpholine-4-carboxylate To a solution of tert-butyl (2S)-2-(2-aminoethyl)morpholine-4-carboxylate (450 mg, 1.76 mmol, Intermediate AQX) and 2-(2,6-dioxo-3-piperidyl)-4-fluoro-isoindoline-1,3-dione (485 mg, 1.76 mmol, Intermediate R) in DMSO (15 mL) was added DIPEA (454 mg, 3.52 mmol) at 25° C. The reaction mixture was stirred at 130° C. for 3 hours. On completion, the reaction mixture was concentrated in vacuo. The residue was purified by reverse phase (0.1% FA condition) to give the title compound (610 mg, 71% yield) as a yellow solid. $^1H$ NMR (400 MHz, DMSO-$d_6$) δ 11.08 (s, 1H), 7.58 (dd, J=7.2, 8.4 Hz, 1H), 7.09 (d, J=8.8 Hz, 1H), 7.02 (d, J=6.8 Hz, 1H), 6.79-6.70 (m, 1H), 5.05 (dd, J=5.2, 12.8 Hz, 1H), 3.90-3.65 (m, 3H), 3.46-3.35 (m, 4H), 2.94-2.81 (m, 2H), 2.64-2.52 (m, 3H), 2.06-1.97 (m, 1H), 1.83-1.61 (m, 2H), 1.39 (s, 9H); LC-MS (ESI$^+$) m/z 386.9 (M+H-100)*.

Step 2—2-(2,6-dioxo-3-piperidyl)-4-[2-[(2S)-morpholin-2-yl]ethylamino]isoindoline-1,3-dione To a solution of tert-butyl (2S)-2-[2-[[2-(2,6-dioxo-3-piperidyl)-1,3-dioxo-isoindolin-4-yl]amino]ethyl]morpholine-4-carboxylate (110 mg, 226 umol) in DCM (6 mL) was added HCl/dioxane (4 M, 2.75 mL) at 25° C. The mixture was stirred at 25° C. for 1 hour. On completion, the reaction mixture was concentrated in vacuo to give the title compound (95.0 mg, 99% yield, HCl salt) as a yellow solid. LC-MS (ESI$^+$) m/z 387.2 (M+H)$^+$.

3-[3-Methyl-2-oxo-4-[[4-(4-piperidyloxy)-1-piperidyl]methyl]benzimidazol-1-yl]piperidine-2,6-dione (Intermediate ABA)

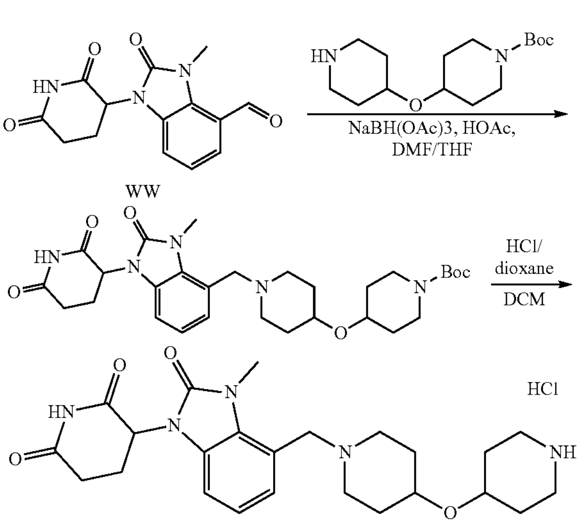

ABA

Step 1—Tert-butyl 4-[[1-[[1-(2,6-dioxo-3-piperidyl)-3-methyl-2-oxo-benzimidazol-4-yl]methyl]-4-piperidyl]oxy]piperidine-1-carboxylate To a solution of 1-(2,6-dioxo-3-piperidyl)-3-methyl-2-oxo-benzimidazole-4-carbaldehyde (200 mg, 696 umol, Intermediate WW), tertbutyl 4-(4-piperidyloxy)piperidine-1-carboxylate (218 mg, 766 umol, CAS #845305-83-1) in DMF (2.00 mL) and THE (2.00 mL) was added HOAc (83.6 mg, 1.39 mmol). The mixture was stirred at 80° C. for 0.5 hr. Then $NaBH(OAc)_3$ (295 mg, 1.39 mmol) was added, then the mixture was stirred at 20° C. for 16 hrs. On completion, the reaction was quenched by addition water (0.5 mL), and concentrated in vacuo to give a residue. The residue was purified by reverse phase (0.1% FA) to give the title compound (180 mg, 46% yield) as a yellow solid. LC-MS (ESI$^+$) m/z 556.3 (M+H)$^+$ Step 2—3-[3-Methyl-2-oxo-4-[[4-(4-piperidyloxy)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-4-yl]methyl]-4-piperidyl]oxy]piperidine-1-carboxylate (150 mg, 270 umol) in DCM (3.00 mL) was added HCl/dioxane (4 M, 3.00 mL), then the mixture was stirred at 20° C. for 1 hr. On completion, the reaction mixture was concentrated in vacuo to give a residue. The residue was purified by reverse phase (0.1% FA condition) to give the title compound (100 mg, 75% yield, HCl) as a white solid. $^1$H NMR (400 MHz, DMSO-$d_6$) δ 11.12 (s, 1H), 9.36-9.07 (m, 1H), 7.51-7.33 (m, 1H), 7.24 (s, 1H), 7.09 (s, 1H), 5.45 (dd, J=4.6, 12.0 Hz, 1H), 4.70-4.47 (m, 1H), 4.02-3.68 (m, 2H), 3.66 (s, 3H), 3.43-3.38 (m, 2H), 3.27-3.22 (m, 2H), 3.15-3.04 (m, 2H), 2.99-2.91 (m, 2H), 2.88 (d, J=5.8 Hz, 1H), 2.78-2.68 (m, 1H), 2.68-2.57 (m, 1H), 2.14-1.91 (m, 5H), 1.91-1.75 (m, 2H), 1.75-1.58 (m, 2H).

N-[2-(4-formylcyclohexyl)-6-(1-hydroxy-1-methyl-ethyl)indazol-5-yl]-2-[6-(trifluoromethyl)-2-pyridyl] acetamide (Intermediate AMI)

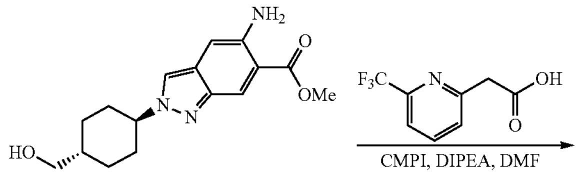

ARE

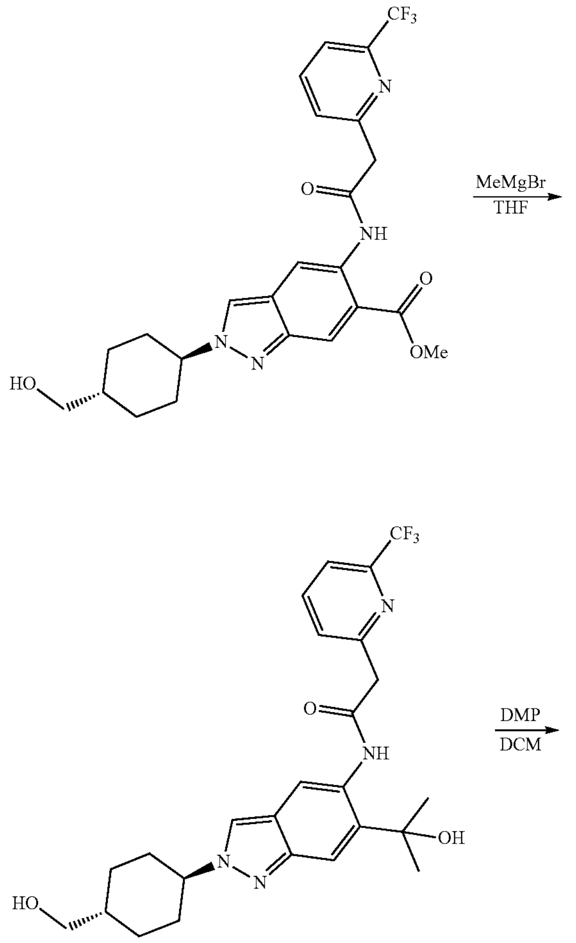

-continued

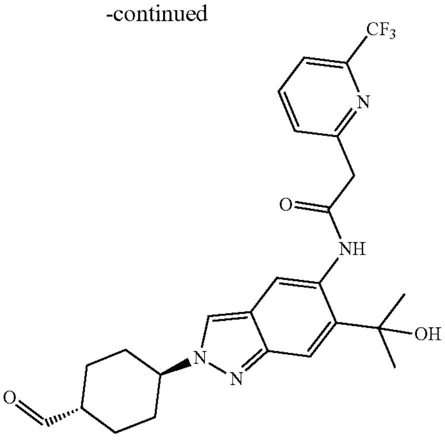

AMI

Step 1—Methyl 2-[4-(hydroxymethyl)cyclohexyl]-5-[[2-[6-(trifluoromethyl)-2-pyridyl]acetyl]amino] indazole-6-carboxylate To a solution of methyl 5-amino-2-[4-(hydroxymethyl) cyclohexyl]indazole-6-carboxylate (200 mg, 659 umol, Intermediate ARE) and 2-[6-(trifluoromethyl)-2-pyridyl] acetic acid (122 mg, 599 umol, CAS #1000565-32-1) in DMF (10 mL) was added DIPEA (232 mg, 1.80 mmol) and $T_3P$ (495 mg, 779 umol) at 25° C. . The reaction mixture was stirred at 25° C. for 3 hours. On completion, the reaction mixture was concentrated in vacuo. The residue was purified by reverse phase (FA condition) to give the title compound (200 mg, 68% yield) as a white solid. $^1$H NMR (400 MHz, DMSO-$d_6$) δ 10.46 (s, 1H), 8.48 (d, J=0.8 Hz, 1H), 8.28 (s, 1H), 8.23 (s, 1H), 8.14-8.06 (m, 1H), 7.87-7.74 (m, 2H), 4.54-4.45 (m, 2H), 4.02 (s, 2H), 3.78 (s, 3H), 3.30-3.27 (m, 2H), 2.19-2.11 (m, 2H), 1.95-1.85 (m, 4H), 1.53-1.43 (m, 1H), 1.22-1.08 (m, 2H); LC-MS (ESI$^+$) m/z 491.4 $(M+H)^+$.

Step 2—N-[2-[4-(hydroxymethyl)cyclohexyl]-6-(1-hydroxy-1-methyl-ethyl)indazol-5-yl]-2-[6- (trifluoromethyl)-2-pyridyl]acetamide To a solution of methyl 2-[4-(hydroxymethyl)cyclohexyl]-5-[[2-[6-(trifluoromethyl)-2-pyridyl]acetyl]amino] indazole-6-carboxylate (200 mg, 407 umol) in THE (15 mL) was added MeMgBr (3 M, 2.72 mL) at 25° C. The mixture was stirred at 0-25° C. for 12 hours. On completion, the reaction was quenched with sat. aq $NH_4Cl$ (30 mL) and extracted with EA 30 mL (3×10 mL). The combined organic layers were washed by brine (20 mL), dried over by $Na_2SO_4$, filtered and the filtrate was concentrated in vacuo. The residue was purified by column chromatography (($SiO_2$, petroleum ether/ethyl acetate=20:1 to 1:2) to give the title compound (80.0 mg, 28% yield) as a black oil. $^1$H NMR (400 MHz, $CDCl_3$-d) δ 10.20 (s, 1H), 8.49 (s, 1H), 7.85 (s, 2H), 7.66 (d, J=7.6 Hz, 2H), 7.61-7.57 (m, 2H), 4.36-4.29 (m, 1H), 4.03 (s, 2H), 3.54 (d, J=6.4 Hz, 2H), 2.27 (d, J=12.4 Hz, 4H), 2.02-1.90 (m, 6H), 1.61 (s, 6H).

Step 3—N-[2-(4-formylcyclohexyl)-6-(1-hydroxy-1-methyl-ethyl)indazol-5-yl]-2-[6-(trifluoromethyl)-2-pyridyl]acetamide To a solution of N-[2-[4-(hydroxymethyl)cyclohexyl]-6-(1-hydroxy-1-methyl-ethyl)indazol-5-yl]- 2-[6-(trifluoromethyl)-2-pyridyl]acetamide (80.0 mg, 114 umol) in DCM (2 mL) was added DMP (58.1 mg, 137 umol) at 0° C. The reaction mixture was stirred at 25° C. for 2 hours. On completion, the reaction was quenched with sat. aq. $Na_2S_2O_3$ (2 mL) and $NaHCO_3$ (2 mL). The mixture was extracted with DCM (3×10 mL). The combined organic layers were concentrated in vacuo. The residue was purified by prep-HPLC (column: UniSil 3-100 C18 Ultra (150*25 mm*3 um); mobile phase: [water(0.225% FA)-ACN]; B %: 35%-65%, 10 min) to give the title compound (25.0 mg, 44% yield) as a white solid. LC-MS (ESI$^+$) m/z 489.4 $(M+H)^+$.

Benzyl methyl(2-methylenespiro[3.5]nonan-7-yl) carbamate (Intermediate ARV)

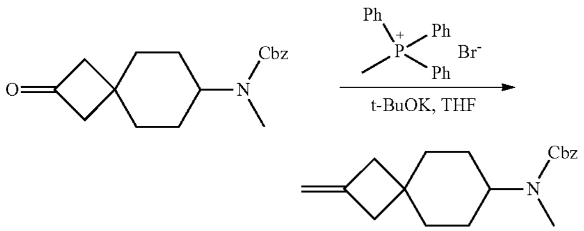

ARV

To a solution of methyl(triphenyl)phosphonium;bromide (1.69 g, 4.74 mmol) in THF (15 mL) was added t-BuOK (532 mg, 4.74 mmol) at 0° C., then the mixture was warmed to 40° C. and stirred for 3 hrs. Then benzyl N-methyl-N-(2-oxospiro[3.5]nonan-7-yl)carbamate (650 mg, 2.16 mmol, synthesized via Steps 1-5 of Intermediate ANJ) in THF (5 mL) was added at 0° C. and the mixture was warmed to 40° C. for 1 hr. On completion, the reaction was quenched with $NH_4Cl$ aqueous (10 mL). The aqueous was extracted with EA (3×20 mL). The combined organic layer was washed with brine, dried over $Na_2SO_4$ and concentrated in vacuo. The residue was purified by column chromatography (PE: EA=100:1) to give the title compound (400 mg, 62% yield) as a colorless oil. $^1H$ NMR (400 MHz, $CDCl_3$) δ 7.42-7.28 (m, 5H), 5.14 (s, 2H), 4.89-4.76 (m, 2H), 4.09-3.76 (m, 1H), 2.79 (s, 3H), 2.41-2.37 (m, 4H), 1.79-1.76 (m, 2H), 1.64-1.58 (m, 2H), 1.53-1.38 (m, 4H).

3-(3-Methyl-4-((7-(methylamino)spiro[3.5]nonan-2-yl)methyl)-2-oxo-2,3-dihydro-1H- benzo[d]imidazol-1-yl)piperidine-2,6-dione (Intermediate ARW)

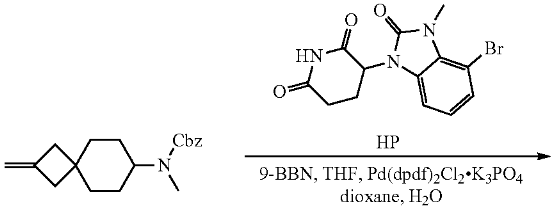

ARV

-continued

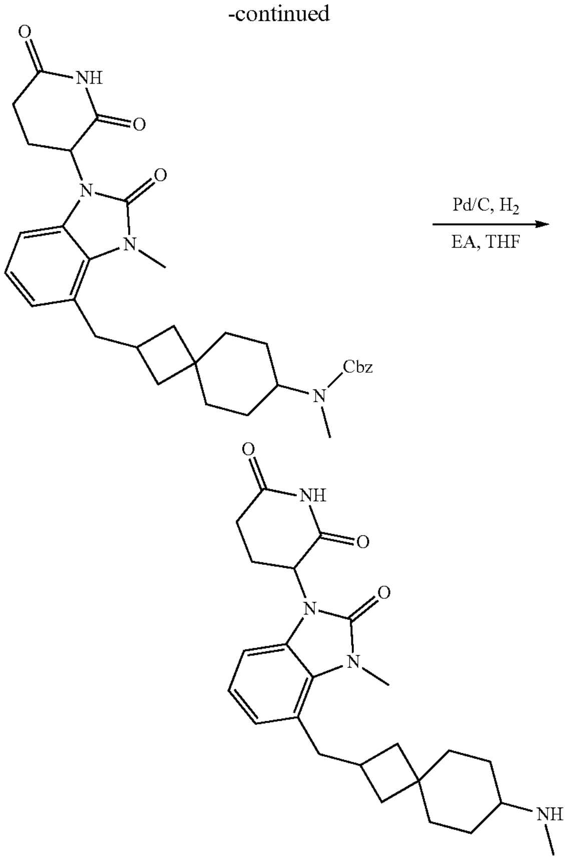

ARW

Step 1—Benzyl (2-((1-(2,6-dioxopiperidin-3-yl)-3-methyl-2-oxo-2,3-dihydro-1H-benzo[d]imidazol -4-yl)methyl)spiro[3.5]nonan-7-yl)(methyl)carbamate A mixture of benzyl N-methyl-N-(2-methylenespiro[3.5] nonan-7-yl)carbamate (1.30 g, 4.34 mmol, Intermediate ARV) and 9-BBN (0.5 M, 8.68 mL, CAS #280-64-8) in THF (10 mL) was stirred at 25° C. for 3 hrs. The above mixture was added to a mixture of 3-(4-bromo-3-methyl-2-oxo-benzimidazol-1-yl)piperidine -2,6-dione (2.20 g, 6.51 mmol, Intermediate HP), ditert-butyl(cyclopentyl)phosphane;dichloropalladium;iron (282 mg, 434 umol) and $K_3PO_4$ (2.30 g, 10.8 mmol) in a mixture of dioxane (20 mL) and $H_2O$ (2 mL). Then the mixture was stirred at 80° C. for 4 hrs under $N_2$ atmosphere. On completion, the reaction was filtered. The filtrate was purified by reverse phase (FA) to give the title compound (1.10 g, 45% yield) as a yellow solid. $^1H$ NMR (400 MHz, $CDCl_3$) δ=8.52 (s, 1H), 7.49-7.28 (m, 5H), 7.04-6.91 (m, 1H), 6.85 (d, J=7.6 Hz, 1H), 6.67 (d, J=7.6 Hz, 1H), 5.22 (dd, J=4.8, 12.0 Hz, 1H), 5.13 (s, 2H), 3.73-3.46 (m, 3H), 3.20-2.74 (m, 7H), 2.60-2.35 (m, 2H), 2.25-2.16 (m, 1H), 2.06-1.98 (m, 1H), 1.92-1.74 (m, 3H), 1.68-1.38 (m, 9H).

Step 2—3-(3-Methyl-4-((7-(methylamino)spiro[3.5] nonan-2-yl)methyl)-2-oxo-2,3-dihydro-1H- benzo[d] imidazol-1-yl)piperidine-2,6-dione To a solution of benzyl N-[2-[[1-(2,6-dioxo-3-piperidyl)-3-methyl-2-oxo-benzimidazol-4-yl]methyl]spiro[3.5]

nonan-7-yl]-N-methyl-carbamate (1.00 g, 1.79 mmol) in EA (10 mL) and THE (10 mL) was added Pd/C (200 mg, 10 wt %) under $N_2$ atmosphere. The suspension was degassed and purged with $H_2$ gas 3 times. The mixture was stirred at 25° C. for 4 hrs under $H_2$ (15 psi) atmosphere. On completion, the reaction was filtered. The filtrate was concentrated to give the title compound (700 mg, 92% yield, 90% purity) as a white solid. $^1$H NMR (400 MHz, $CDCl_3$) δ 7.00-6.92 (m, 1H), 6.85 (d, J=7.6 Hz, 1H), 6.66 (d, J=7.6 Hz, 1H), 5.30-5.15 (m, 1H), 3.66 (s, 3H), 3.02 (d, J=7.2 Hz, 1H), 2.97-2.90 (m, 2H), 2.83-2.74 (m, 2H), 2.58-2.45 (m, 1H), 2.41 (s, 3H), 2.32-2.18 (m, 2H), 2.04-1.97 (m, 1H), 1.93-1.67 (m, 4H), 1.63-1.42 (m, 4H), 1.40-1.28 (m, 2H), 1.20-1.02 (m, 2H).

3-[3-Methyl-4-[4-(methylamino)-1-piperidyl]-2-oxo-benzimidazol-1-yl]piperidine-2,6-dione (Intermediate AQK)

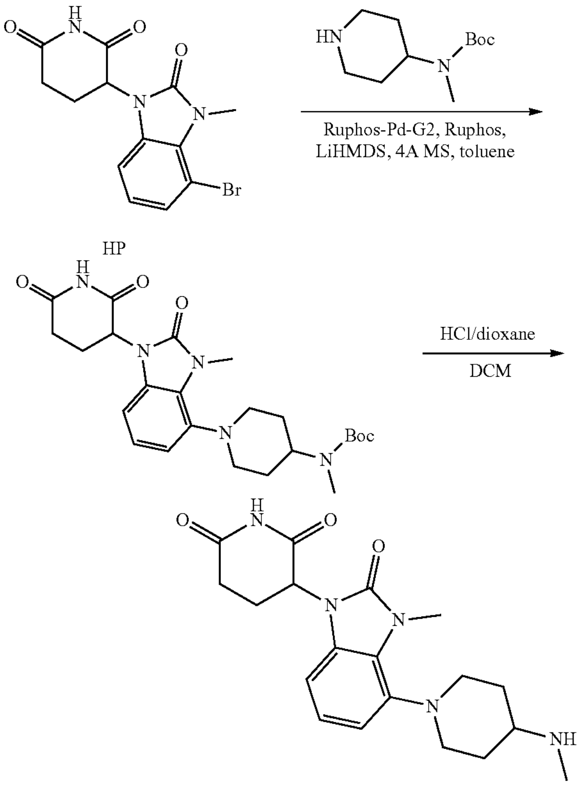

HP

AQK

Step 1—Tert-butyl N-[1-[1-(2,6-dioxo-3-piperidyl)-3-methyl-2-oxo-benzimidazol-4-yl]-4-piperidyl]-N-methyl-carbamate To a solution of 3-(4-bromo-3-methyl-2-oxo-benzimidazol-1-yl)piperidine-2,6-dione (500 mg, 1.48 mmol, Intermediate HP), tert-butyl N methyl-N-(4-piperidyl)carbamate (633 mg, 2.96 mmol, CAS #108612-54-0) and 4 Å molecular sieves (500 mg) in toluene (10 mL) was added [2-(2-aminophenyl)phenyl]-chloro-palladium;dicyclohexyl-[2-(2,6-diisopropoxyphenyl)phenyl]phosphane (229 mg, 295 umol), RuPhos (138 mg, 295 umol) and LiHMDS (1.00 M, 8.87 mL) under $N_2$ atmosphere. The mixture was stirred at 80° C. for 1 hr under $N_2$ atmosphere. On completion, the mixture was concentrated in vacuo. The residue was diluted with DMF (6 mL), filtered and the filtrate was acidified with FA until the pH=5. The filtrate was concentrated in vacuo. The residue was purified by reverse phase (0.1% FA) and silica gel column (PE:EA=1:1) to give the title compound (70 mg, 10% yield) as a yellow solid. $^1$H NMR (400 MHz, DMSO-$d_6$) δ 11.08 (s, 1H), 7.01-6.84 (m, 3H), 5.42-5.27 (m, 1H), 3.64 (s, 3H), 3.36-3.33 (m, 1H), 3.22-3.09 (m, 2H), 2.94-2.77 (m, 3H), 2.75 (s, 3H), 2.70-2.57 (m, 2H), 2.04-1.98 (m, 1H), 1.95-1.84 (m, 2H), 1.72-1.59 (m, 2H), 1.42 (s, 9H), LC-MS (ESI$^+$) m/z 472.2 (M+H)$^+$.

Step 2—3-[3-Methyl-4-[4-(methylamino)-1-piperidyl]-2-oxo-benzimidazol-1-yl]piperidine-2,6-dione To a solution of tert-butyl N-[1-[1-(2,6-dioxo-3-piperidyl)-3-methyl-2-oxo-benzimidazol-4-yl]-4-piperidyl]-N-methylcarbamate (70.0 mg, 148 umol) in DCM (3.00 mL) was added HCl/dioxane (4.00 M, 2.00 mL). The mixture was stirred at 25° C. for 0.5 hr. On completion, the mixture was concentrated in vacuo to give the title compound (60 mg, 99% yield, HCl salt) as a yellow solid. LC-MS (ESI$^+$) m/z 372.3 (M+H)$^+$.

Tert-butyl (3-((1r,3r)-3-(bromomethyl)cyclobutoxy) propyl)(methyl)carbamate (Intermediate ART)

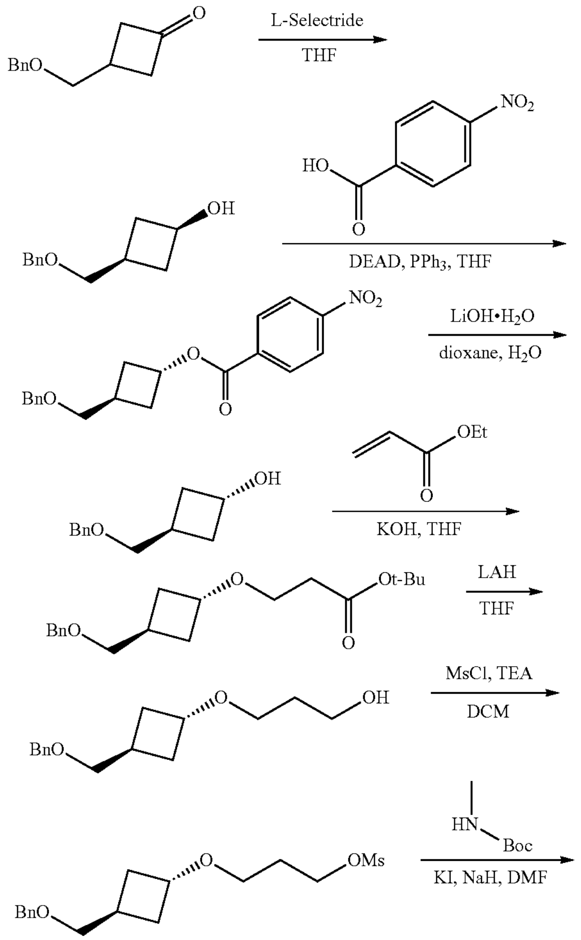

-continued

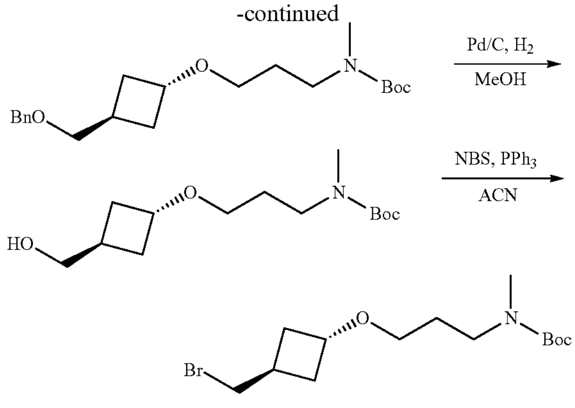

ART

Step 1—(1s,3s)-3-((Benzyloxy)methyl)cyclobutanol

To a solution of 3-(benzyloxymethyl)cyclobutanone (50.0 g, 263 mmol, CAS #172324-67-3) in tetrahydrofuran (400 mL) stirring at −70° C., was added dropwise a solution of L-Selectride (1 M, 526 mL), maintaining the reaction temperature below −65° C. The reaction mixture was allowed to warm to 25° C. for 18 hrs. On completion, the reaction was quenched with saturated sodium bicarbonate (150 mL) and extracted with ethyl acetate (3×150 mL). The combined organic layer was acidified with 2N HCl aqueous (150 mL), and stirred at 25° C. for 3 hrs. Then the organic layer was separated and washed with brine (40 mL), dried over anhydrous sodium sulfate, filtered and concentrated in vacuo. The residue was purified by column chromatography (petroleum ether/ethyl acetate=5/1) to give the title compound (46.0 g, 91% yield) as a colorless oil. $^1H$ NMR (400 MHz, $CDCl_3$) δ 7.42-7.28 (m, 5H), 4.52 (s, 2H), 4.39-4.27 (m, 1H), 3.45 (d, J=6.0 Hz, 2H), 2.54-2.41 (m, 2H), 2.16-2.05 (m, 1H), 1.56-1.47 (m, 3H).

Step 2—(1r,3r)-3-((Benzyloxy)methyl)cyclobutyl 4-nitrobenzoate

To a solution of (1s,3s)-3-((benzyloxy)methyl)cyclobutanol (30.0 g, 156 mmol), 4-nitrobenzoic acid (52.1 g, 312 mmol) and triphenylphosphine (85.9 g, 327 mmol) in tetrahydrofuran (300 mL) at 0° C. A solution of diisopropyl azodicarboxylate (66.2 g, 327 mmol) in tetrahydrofuran (100 mL) was added dropwise into the above mixture. The reaction mixture was stirred at 25° C. for 16 hrs. On completion, the reaction was quenched by addition water (5 mL), and then diluted with ethyl acetate (100 mL). The combined organic layers was washed with brine (20 mL), dried over anhydrous sodium sulfate, filtered and concentrated under reduced pressure to give a residue. The residue was purified by column chromatography (petroleum ether/ethyl acetate=20/1) to give the title compound (28.4 g, 53% yield) as a white solid. $^1H$ NMR (400 MHz, $CDCl_3$) δ 8.28-8.19 (m, 2H), 8.18-8.11 (m, 2H), 7.37-7.20 (m, 5H), 5.30-5.26 (m, 1H), 4.50 (s, 2H), 3.47 (d, J=6.8 Hz, 2H), 2.69-2.52 (m, 1H), 2.43-2.26 (m, 4H).

Step 3—(1r,3r)-3-((Benzyloxy)methyl)cyclobutanol

To a solution of (1r,3r)-3-((benzyloxy)methyl)cyclobutyl 4-nitrobenzoate (28.4 g, 83.2 mmol) in a mixed solvent of dioxane (100 mL) and water (50 mL) was added LiOH $H_2O$ (6.98 g, 166 mmol) at 25° C. The reaction mixture was stirred at 25° C. for 0.5 hr. On completion, the reaction was concentrated in vacuo and diluted with ethyl acetate (400 mL), filtered and the filtrate was washed with brine (2×60 mL). The organic layer was dried over anhydrous sodium sulfate, filtered and concentrated in vacuo to give the title compound (15.0 g, 94% yield) as colorless oil. $^1H$ NMR (400 MHz, $CDCl_3$) δ 7.53-7.27 (m, 5H), 4.53 (s, 2H), 4.41 (s, 1H), 3.47 (d, J=6.8 Hz, 2H), 2.60-2.40 (m, 1H), 2.27-2.16 (m, 2H), 2.13-2.02 (m, 2H), 1.75-1.71 (m, 1H).

Step 4—Tert-butyl 3-((1r,3r)-3-((benzyloxy)methyl)cyclobutoxy)propanoate

To a solution of (1r,3r)-3-((benzyloxy)methyl)cyclobutanol (3.00 g, 15.6 mmol) in tetrahydrofuran (40 mL) was added potassium hydroxide (101 mg, 1.56 mmol, 87%) and tert-butyl prop-2-enoate (6.00 g, 46.8 mmol, 6.79 mL). The reaction mixture was stirred at 25° C. for 12 hrs. On completion, the reaction was quenched with water (2 mL), and extracted with ethyl acetate (3×50 mL). The combined organic layers were washed with brine (50 mL), dried over anhydrous sodium sulfate, filtered and the filtrate was concentrated in vacuo. The residue was purified by column chromatography (Petroleum ether/Ethyl acetate=20/1) to give the title compound (4.70 g, 94% yield) as colorless oil. $^1H$ NMR (400 MHz, $CDCl_3$) δ 7.53-7.28 (m, 5H), 4.53 (s, 2H), 4.05 (t, J=6.8 Hz, 1H), 3.55 (t, J=6.8 Hz, 2H), 3.46 (d, J=6.8 Hz, 2H), 2.58-2.42 (m, 3H), 2.10 (t, J=6.8 Hz, 4H), 1.46 (s, 9H).

Step 5—3-((1r,3r)-3-((Benzyloxy)methyl)cyclobutoxy)propan-1-ol

To a solution of LAH (639 mg, 16.8 mmol) in tetrahydrofuran (50 mL) was added a solution of tert-butyl 3-((1r,3r)-3-((benzyloxy)methyl)cyclobutoxy)propanoate (4.50 g, 14.0 mmol) in tetrahydrofuran (20 mL) at 0° C. The reaction mixture was stirred at 20° C. for 1 hr. On completion, the reaction mixture was quenched with water (1 mL), and then was added anhydrous sodium sulfate into the mixture and filtered. The filtrate was concentrated in vacuo to give the title compound (3.52 g, 100% yield) as colorless oil. $^1H$ NMR (400 MHz, $CDCl_3$) δ 7.42-7.27 (m, 5H), 4.53 (s, 2H), 4.06-4.02 (m, 1H), 3.83-3.71 (m, 3H), 3.50 (t, J=5.6 Hz, 2H), 2.58-2.47 (m, 1H), 2.44 (t, J=5.6 Hz, 1H), 2.18-2.02 (m, 4H), 1.90-1.78 (m, 3H).

Step 6—3-((1r,3r)-3-((Benzyloxy)methyl)cyclobutoxy)propyl methanesulfonate

To a solution of 3-((1r,3r)-3-((benzyloxy)methyl)cyclobutoxy)propan-1-ol (3.60 g, 14.4 mmol) in dichloromethane (5 mL) was added triethylamine (4.37 g, 43.1 mmol, 6.00 mL) and methanesulfonyl chloride (2.47 g, 21.5 mmol, 1.67 mL) at 0° C. The reaction mixture was stirred at 25° C. for 0.5 hr. On completion, the reaction was quenched with water (5 mL), and extracted with dichloromethane (3×20 mL). The combined organic layers were washed with brine (2×20 mL), dried over anhydrous sodium sulfate, filtered and concentrated in vacuo to give the title compound (4.70 g, 100% yield) as colorless oil. $^1H$ NMR (400 MHz, $CDCl_3$) δ 7.44-7.28 (m, 5H), 4.53 (s, 2H), 4.34 (t, J=6.4 Hz, 2H), 4.03 (t, J=6.8 Hz, 1H), 3.47 (d, J=6.8 Hz, 2H), 3.41 (t, J=6.0 Hz, 2H), 3.01 (s, 3H), 2.60-2.42 (m, 1H), 2.14-2.04 (m, 4H), 2.02-1.98 (m, 2H).

Step 7—Tert-butyl (3-((1r,3r)-3-((benzyloxy)methyl)cyclobutoxy)propyl)(methyl)carbamate To a solution of tert-butyl N-methylcarbamate (2.82 g, 21.4 mmol) in N,N-dimethylformamide (3 mL) was added NaH (1.14 g, 28.6 mmol, 60% dispersion in mineral oil) at 0° C. for 0.5 hr. Then 3-((1r,3r)-3-((Benzyloxy)methyl)cyclobutoxy)propylmethanesulfonate (4.70 g, 14.3 mmol) and potassium iodide (237 mg, 1.43 mmol) was added into the above mixture. The reaction mixture was stirred at 25° C. for 12 hrs. On completion, the reaction mixture was quenched with water (2 mL), and extracted with ethyl acetate (3×150 mL). The combined organic layers were washed with brine (2×50 mL), dried over anhydrous sodium sulfate, filtered and the filtrate was concentrated in vacuo. The crude product was purified by silica gel chromatography (petroleum ether/ethyl acetate=20/1 to 10/1) to give the title compound (4.20 g, 80% yield) as a colorless oil. $^1$H NMR (400 MHz, $CDCl_3$) δ 7.43-7.27 (m, 5H), 4.53 (s, 2H), 4.02 (t, J=6.8 Hz, 1H), 3.47 (d, J=6.8 Hz, 2H), 3.40-3.17 (m, 4H), 2.85 (s, 3H), 2.56-2.41 (m, 1H), 2.09 (t, J=6.8 Hz, 4H), 1.77 (t, J=6.8 Hz, 2H), 1.46 (s, 9H). LC-MS (ESI$^+$) m/z 386.1 (M+23)*.

Step 8—Tert-butyl (3-((1r,3r)-3-(hydroxymethyl)cyclobutoxy)propyl)(methyl)carbamate To a solution of tert-butyl (3-((1r,3r)-3-((benzyloxy)methyl)cyclobutoxy)propyl)(methyl)carbamate (4.40 g, 12.1 mmol) in methanol (50 mL) was added Pd/C (1.00 g, 10% wt) under $N_2$ atmosphere. The suspension was degassed and purged with $H_2$ gas 6 times. The mixture was stirred under $H_2$ (50 Psi) at 50° C. for 16 hrs. On completion, the reaction was filtered and the filtrate was concentrated in vacuo to give the title compound (3.30 g, 100% yield) as colorless oil. $^1$H NMR (400 MHz, $CDCl_3$) δ 4.04-4.00 (m, 1H), 3.64 (d, J=6.8 Hz, 2H), 3.41-3.21 (m, 4H), 2.86 (s, 3H), 2.50-2.35 (m, 1H), 2.19-2.04 (m, 4H), 1.80-1.76 (m, 2H), 1.46 (s, 9H), 1.44-1.35 (m, 1H).

Step 9—Tert-butyl (3-((1r,3r)-3-(bromomethyl)cyclobutoxy)propyl)(methyl)carbamate To a solution of tert-butyl (3-((1r,3r)-3-(hydroxymethyl)cyclobutoxy)propyl)(methyl)carbamate (2.30 g, 8.41 mmol) in acetonitrile (20 mL) was added NBS (2.99 g, 16.8 mmol) and triphenylphosphine (4.41 g, 16.8 mmol). The reaction mixture was stirred at 25° C. for 12 hr under $N_2$. On completion, the mixture was quenched with water (10 mL), and extracted with ethyl acetate (3×30 mL). The combined organic layers were washed with brine (10 mL), dried over anhydrous sodium sulfate, filtered and the filtrate was concentrated in vacuo. The residue was purified by silica gel chromatography (petroleum ether/ethyl acetate=10/1) to give the title compound (650 mg, 23% yield) as colorless oil. $^1$H NMR (400 MHz, $CDCl_3$) δ 4.02-3.91 (m, 1H), 3.41-3.39 (m, 2H), 3.29-3.17 (m, 4H), 2.78 (s, 3H), 2.23-2.18 (m, 1H), 2.09-1.98 (m, 4H), 1.72-1.68 (m, 2H), 1.38 (s, 9H).

3-(3-Methyl-4-(((1r,3s)-3-(3-(methylamino)propoxy)cyclobutyl)methyl)-2-oxo-2,3-dihydro- 1H-benzo[d]imidazol-1-yl)piperidine-2,6-dione (Intermediate ARU)

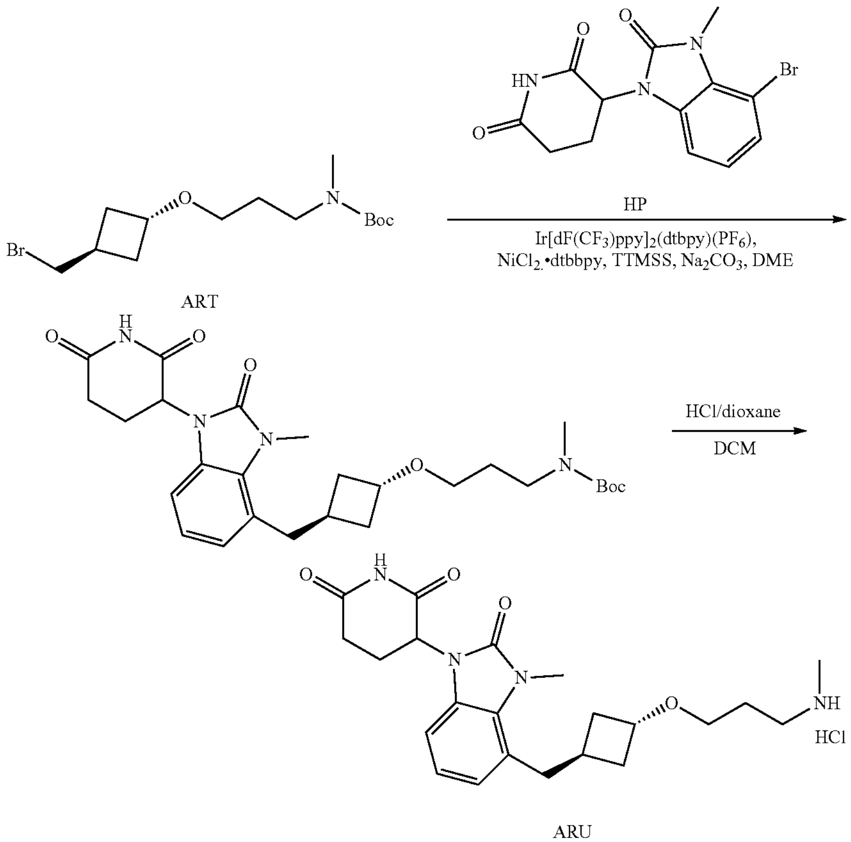

ARU

Step 1—Tert-butyl (3-((1s,3r)-3-((1-(2,6-dioxopiperidin-3-yl)-3-methyl-2-oxo-2,3-dihydro-1H- benzo[d]imidazol-4-yl)methyl)cyclobutoxy)propyl)(methyl)carbamate To an 8 mL vial equipped with a stir bar was added 3-(4-bromo-3-methyl-2-oxo-benzimidazol-1-yl)piperidine-2,6-dione (50.0 mg, 148 umol, Intermediate HP), tert-butyl (3-((1r,3r)-3-(bromomethyl)cyclobutoxy)propyl)(methyl) carbamate (59.6 mg, 177 umol, Intermediate ART), Ir[dF $(CF_3)ppy]_2(dtbpy)(PF_6)$ (1.66 mg, 1.48 umol), $NiCl_2$.dtbbpy (294 ug, 0.007 umol), TTMSS (36.7 mg, 148 umol), sodium carbonate (31.3 mg, 295 umol) in dimethyl ether (1.5 mL). The reaction mixture was stirred and irradiated with a 34 W blue LED lamp, with cooling fan to keep the reaction temperature at 25° C. for 14 hrs under nitrogen. On completion, the reaction mixture was filtered and the filtrate was concentrated in vacuo. The residue was purified by reversed-phase chromatography (acid condition: 0.1% FA) to give the title compound (66.0 mg, 84% yield) as a yellow solid. LC-MS ($ESI^+$) m/z 537.2 (M+Na)*.

Step 2—3-(3-Methyl-4-(((1r,3s)-3-(3-(methylamino)propoxy)cyclobutyl)methyl)-2-oxo-2,3-dihydro-1H-benzo[d]imidazol-1-yl)piperidine-2,6-dione To a solution of tert-butyl (3-((1s,3r)-3-((1-(2,6-dioxopiperidin-3-yl)-3-methyl-2-oxo-2,3-dihydro-1H- benzo[d]imidazol-4-yl)methyl)cyclobutoxy)propyl)(methyl)carbamate (60.0 mg, 116 umol) in dichloromethane (5 mL) was added HCl/dioxane (4 M, 2 mL). The reaction mixture was stirred at 25° C. for 0.5 hr. On completion, the reaction mixture was concentrated in vacuo to give the title compound (52.0 mg, 100% yield, HCl salt) as a white solid. LC-MS ($ESI^+$) m/z 415.1 $(M+H)^+$.

3-[3-Methyl-6-[4-(methylamino)-1-piperidyl]-2-oxo-benzimidazol-1-yl]piperidine-2,6-dione (Intermediate ASK)

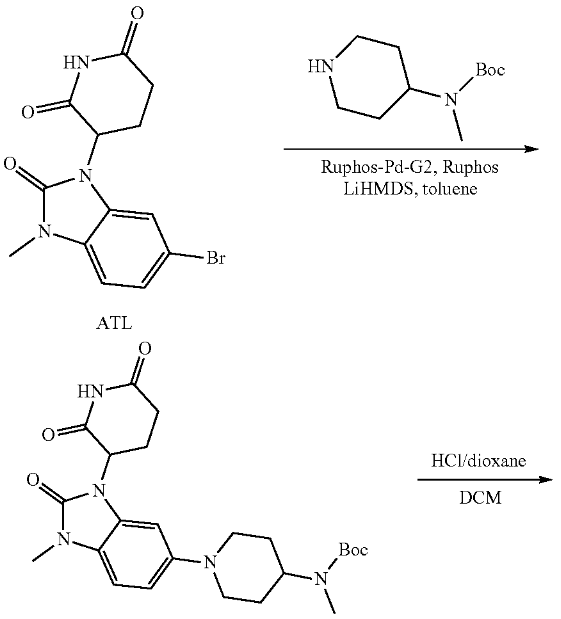

-continued

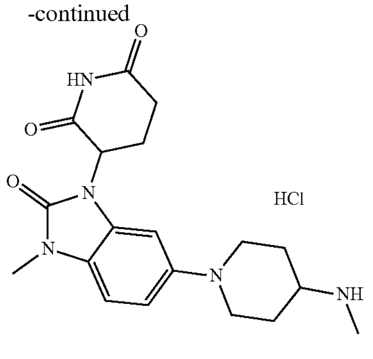

ASK

Tert-butyl N-[1-[3-(2, 6-dioxo-3-piperidyl)-1-methyl-2-oxo-benzimidazol-5-yl]-4-piperidyl]-N-methyl-carbamate A mixture of 3-(6-bromo-3-methyl-2-oxo-benzimidazol-1-yl)piperidine-2,6-dione (500 mg, 1.48 mmol, Intermediate ATL), tert-butyl N methyl-N-(4-piperidyl)carbamate (475 mg, 2.22 mmol), 4Δ molecular sieves (100 mg), LiHMDS (1 M, 8.87 mL), Ruphos (138 mg, 295 umol) and [2-(2-aminophenyl)phenyl]-chloro-palladium;dicyclohexyl-[2-(2,6-diisopropoxyphenyl)phenyl]phosphane (229 mg, 296 umol) in toluene (5 mL) was stirred at 80° C. for 1 hr under $N_2$ atmosphere. On completion, the reaction mixture was adjusted to pH 5 with FA, filtered and the filtrate was concentrated in vacuo. The residue was purified by reverse phase (0.1% FA) to give the title compound (300 mg, 43% yield) as a yellow solid. $^1H$ NMR (400 MHz, DMSO-$d_6$) δ 11.05 (s, 1H), 7.01 (d, J=8.4 Hz, 1H), 6.80 (s, 1H), 6.73-6.67 (m, 1H), 5.38-5.29 (m, 1H), 4.01-3.87 (m, 1H), 3.67-3.55 (m, 2H), 3.30-3.28 (m, 2H), 3.27 (s, 3H), 2.87-2.76 (m, 1H), 2.68-2.60 (m, 5H), 2.04-1.92 (m, 1H), 1.84-1.74 (m, 2H), 1.67-1.54 (m, 2H), 1.40 (s, 9H); LC-MS ($ESI^+$) m/z 472.2 $(M+H)^+$.

Step 2—3-[3-Methyl-6-[4-(methylamino)-1-piperidyl]-2-oxo-benzimidazol-1-yl]piperidine-2,6-dione To a solution of tert-butyl N-[1-[3-(2,6-dioxo-3-piperidyl)-1-methyl-2-oxo-benzimidazol-5-yl]-4- piperidyl]-N-methyl-carbamate (100 mg, 212 umol) in DCM (2 mL) was added HCl/dioxane (4 M, 10.0 mL). The mixture was stirred at 25° C. for 2 hours. On completion, the reaction mixture was concentrated in vacuo to give the title compound (86.0 mg, 99% yield, HCl salt) as a yellow solid. LC-MS ($ESI^+$) m/z 372.1 $(M+H)^+$.

N-[2-(4-formylcyclohexyl)-6-(1-hydroxy-1-methyl-ethyl)indazol-5-yl]pyridine-2-carboxamide (Intermediate ASM)

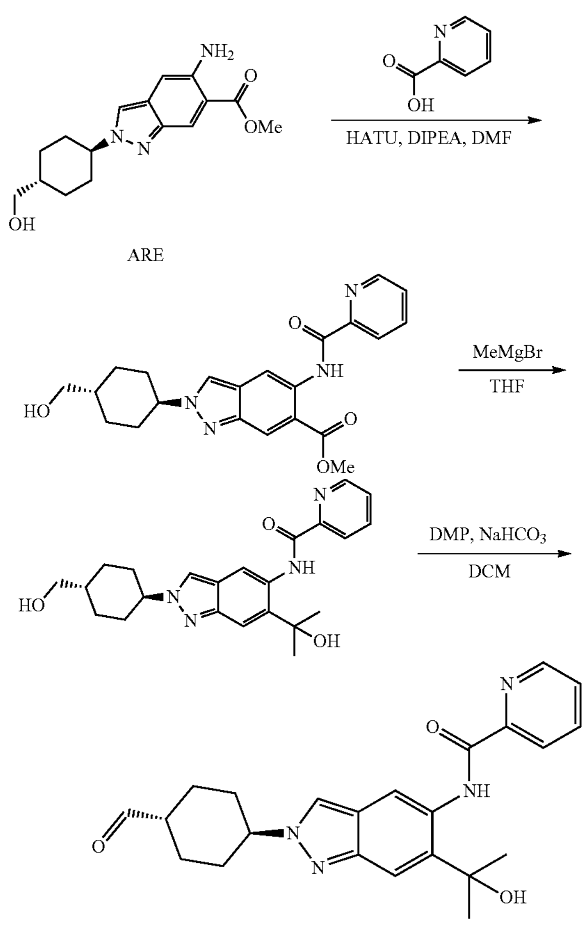

ASM

Step 1—Methyl 2-[4-(hydroxymethyl)cyclohexyl]-5-(pyridine-2-carbonylamino)indazole-6- carboxylate A mixture of pyridine-2-carboxylic acid (2.03 g, 16.4 mmol, CAS #636-80-6), methyl 5-amino-2-[4-(hydroxymethyl)cyclohexyl]indazole-6-carboxylate (5.00 g, 16.4 mmol, Intermediate ARE), HATU (8.15 g, 21.4 mmol) and DIPEA (6.39 g, 49.4 mmol) in DMF (30 mL) was stirred at 20° C. for 1 hr. On completion, the mixture was diluted with water (300 mL) and extracted with EA (3x100 mL). The organic layer was washed with brine (3x100 mL). The organic layer was dried over anhydrous sodium sulfate and filtered. The filtrated was concentrated in vacuo. The crude product was purified by reversed-phase HPLC (FA) to give the title compound (4.86 g, 72% yield) as a red solid. $^1$H NMR (400 MHz, DMSO-$d_6$) δ 12.64 (s, 1H), 9.09 (s, 1H), 8.78 (d, J=4.4 Hz, 1H), 8.56 (s, 1H), 8.47 (s, 1H), 8.20 (d, J=7.6 Hz, 1H), 8.08 (dt, J=1.6, 7.6 Hz, 1H), 7.71-7.65 (m, 1H), 4.58-4.44 (m, 2H), 3.97 (s, 3H), 3.29 (t, J=5.6 Hz, 2H), 2.22-2.13 (m, 2H), 1.98-1.86 (m, 4H), 1.58-1.42 (m, 1H), 1.26-1.07 (m, 2H).

Step 2—N-[2-[4-(hydroxymethyl)cyclohexyl]-6-(1-hydroxy-1-methyl-ethyl)indazol-5-yl]pyridine -2-carboxamide To a solution of methyl 2-[4-(hydroxymethyl)cyclohexyl]-5-(pyridine-2-carbonylamino)indazole-6- carboxylate (4.76 g, 11.6 mmol) in THE (200 mL) was added MeMgBr (3 M, 38.85 mL) at 0° C. The reaction mixture was stirred at 0° C. for 1 hr. The reaction mixture was stirred at 20° C. for 2 hrs. On completion, the mixture was diluted with water (500 mL) and extracted with EA (3x200 mL). The organic layer was washed with brine (3x200 mL), dried over anhydrous sodium sulfate and filtered. The filtrate was concentrated in vacuo and the residue was purified by silica gel chromatography (PE:EA=0:1) to give the title compound (2.82 g, 59% yield) as a yellow solid. $^1$H NMR (400 MHz, DMSO-$d_6$) δ 12.32 (s, 1H), 8.70 (d, J=4.0 Hz, 1H), 8.67 (s, 1H), 8.34 (s, 1H), 8.19 (d, J=7.6 Hz, 1H), 8.07-8.02 (m, 1H), 7.66-7.60 (m, 1H), 7.56 (s, 1H), 6.02 (s, 1H), 4.55-4.47 (m, 2H), 4.45-4.36 (m, 1H), 3.30-3.28 (m, 2H), 2.17-2.10 (m, 2H), 1.62 (s, 6H), 1.57-1.41 (m, 2H), 1.27-1.07 (m, 4H).

Step 3—N-[2-(4-formylcyclohexyl)-6-(1-hydroxy-1-methyl-ethyl)indazol-5-yl]pyridine-2-carboxamide To a mixture of N-[2-[4-(hydroxymethyl)cyclohexyl]-6-(1-hydroxy-1-methyl-ethyl)indazol-5-yl]pyridine-2-carboxamide (2.72 g, 6.66 mmol) and $NaHCO_3$ (2.80 g, 33.2 mmol) in DCM (50 mL) was added DMP (4.24 g, 9.99 mmol) at 0° C. The reaction mixture was stirred at 20° C. for 3 hrs. On completion, the reaction mixture was diluted with saturated $Na_2S_2O_3$ aqueous (50 mL) and saturated $NaHCO_3$ aqueous (50 mL). The mixture was stirred at 20° C. for 0.5 hr. The mixture was diluted with water (300 mL) and extracted with DCM (3x100 mL). The organic layer was washed with saturated $NaHCO_3$ aqueous (3x100 mL) and brine (3x100 mL). The organic layer was dried over anhydrous sodium sulfate and filtered. The filtrated was concentrated in vacuo. The residue was triturated with EA (50 mL) at 20° C. for 1 hr to give the title compound (2.00 g, 73% yield) as a yellow solid. $^1$H NMR (400 MHz, DMSO-$d_6$) δ 12.33 (s, 1H), 9.64 (s, 1H), 8.70 (d, J=4.4 Hz, 1H), 8.68 (s, 1H), 8.35 (s, 1H), 8.20 (d, J=7.6 Hz, 1H), 8.09-8.02 (m, 1H), 7.67-7.60 (m, 1H), 7.56 (s, 1H), 6.03 (s, 1H), 4.48-4.42 (m, 1H), 2.47-2.39 (m, 1H), 2.24-2.16 (m, 2H), 2.15-2.07 (m, 2H), 2.00-1.95 (m, 2H), 1.62 (s, 6H), 1.51-1.38 (m, 2H).

Tert-butyl (2R)-2-(3-aminopropyl)morpholine-4-carboxylate (Intermediate ASX)

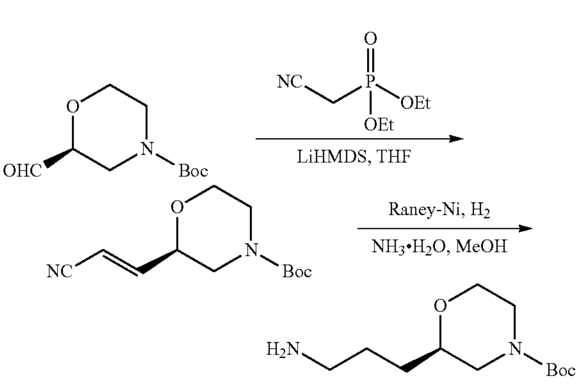

ASX

Step 1—Tert-butyl (2R)-2-[(E)-2-cyanovinyl]morpholine-4-carboxylate

To a mixture of 2-diethoxyphosphorylacetonitrile (987 mg, 5.58 mmol, 897 U1, CAS #2537-48-6) in THE (20 mL) was added LiHMDS (1 M, 6.69 mL) at −70° C. for 0.5 hour. Then tert-butyl (2S)-2-formylmorpholine-4-carboxylate (1.20 g, 5.58 mmol, synthesized via Step 1 of Intermediate ARZ) was added to the mixture at −70° C. The reaction mixture was stirred at -70° C. for 3 hours. The reaction mixture was quenched with $NH_4Cl$ (10 mL) and extracted with DCM (2×100 mL). The combined organic layers was dried over $Na_2SO_4$, filtered and concentrated in vacuo to give a residue. The residue was purified by column chromatography to give the title compound (0.50 g, 37% yield) as colorless oil. $^1H$ NMR (400 MHz, $CDCl_3$) δ 6.66-6.59 (m, 1H), 5.79-5.66 (m, 1H), 4.08-3.83 (m, 4H), 3.61-3.52 (m, 1H), 2.95 (s, 1H), 2.75-2.52 (m, 1H), 1.47 (s, 9H).

Step 2—Tert-butyl (2R)-2-(3-aminopropyl)morpholine-4-carboxylate

To a mixture of tert-butyl (2R)-2-[(E)-2-cyanovinyl]morpholine-4-carboxylate (450 mg, 1.89 mmol) in MeOH (20 mL) was added $NH_3.H_2O$ (455 mg, 3.25 mmol, 0.5 mL, 25% solution) and Raney-Ni (300 mg, 3.50 mmol). The reaction mixture was stirred at 25° C. for 12 hours under $H_2$ (50 psi) atmosphere. On completion, the reaction mixture was filtered and concentrated in vacuo to give the title compound (406 mg, 76% yield) as colourless oil.

2-(2,6-Dioxo-3-piperidyl)-4-[3-[(2R)-morpholin-2-yl]propylamino]isoindoline-1,3-dione (Intermediate ASY)

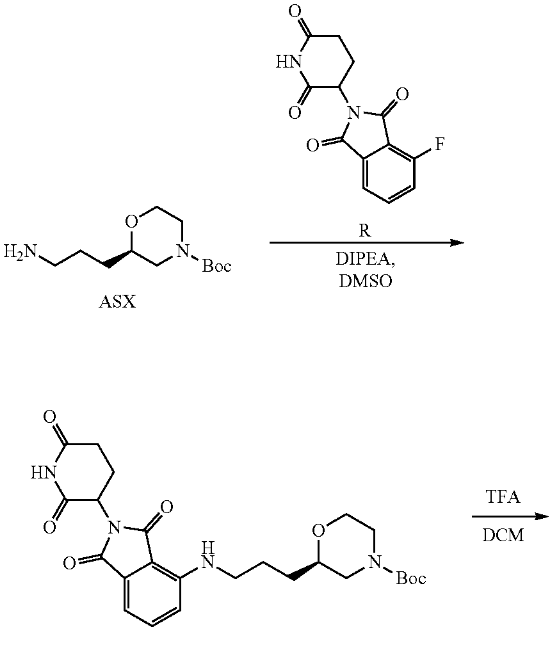

-continued

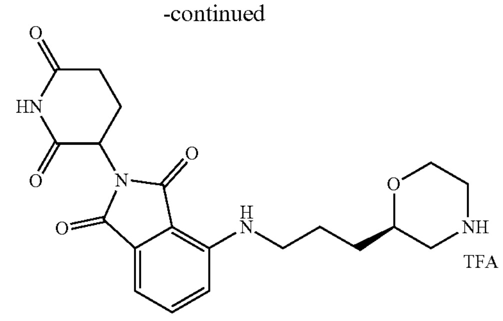

ASY

Step 1—Tert-butyl (2R)-2-[3-[[2-(2,6-dioxo-3-piperidyl)-1,3-dioxo-isoindolin-4-yl]amino]propyl]morpholine-4-carboxylate To a mixture of tert-butyl (2R)-2-(3-aminopropyl)morpholine-4-carboxylate (406 mg, 1.45 mmol, Intermediate ASX) and 2-(2,6-dioxo-3-piperidyl)-4-fluoro-isoindoline-1,3-dione (400 mg, 1.45 mmol, Intermediate R) in DMSO (8 mL) was added DIPEA (561 mg, 4.34 mmol, 756 uL). The reaction mixture was stirred at 130° C. for 2 hour. On completion, the reaction mixture was concentrated in vacuo. The residue was purified by reverse phase (0.1% FA condition) to give the title compound (440 mg, 60% yield) as yellow solid. $^1H$ NMR (400 MHz, DMSO-$d_6$) δ 11.08 (s, 1H), 7.61-7.53 (m, 1H), 7.09 (d, J=8.8 Hz, 1H), 7.02 (d, J=7.2 Hz, 1H), 6.58 (t, J=5.6 Hz, 1H), 5.08-5.01 (m, 1H), 3.81-3.66 (m, 3H), 3.38 (d, J=2.4 Hz, 1H), 3.32-3.25 (m, 4H), 2.94-2.74 (m, 2H), 2.63-2.53 (m, 2H), 2.08-1.97 (m, 1H), 1.73-1.53 (m, 2H), 1.50-1.43 (m, 2H), 1.39 (s, 9H); LC-MS ($ESI^+$) m/z 523.4 (M+Na)*.

Step 2—2-(2,6-Dioxo-3-piperidyl)-4-[3-[(2R)-morpholin-2-yl]propylamino]isoindoline-1,3-dione To a mixture of tert-butyl (2R)-2-[3-[[2-(2,6-dioxo-3-piperidyl)-1,3-dioxo-isoindolin-4-yl]amino]propyl]morpholine-4-carboxylate (150 mg, 299 umol) in DCM (1 mL) was added TFA (2.31 g, 20.2 mmol, 1.50 mL). The reaction mixture was stirred at 25° C. for 0.5 hour. On completion, the reaction mixture was concentrated in vacuo to give the title compound (154 mg, 99% yield, TFA) as red oil. LC-MS ($ESI^+$) m/z 401.2 $(M+H)^+$.

Tert-butyl 2-(2-aminoethyl)-7-azaspiro[3.5]nonane-7-carboxylate (Intermediate ATB)

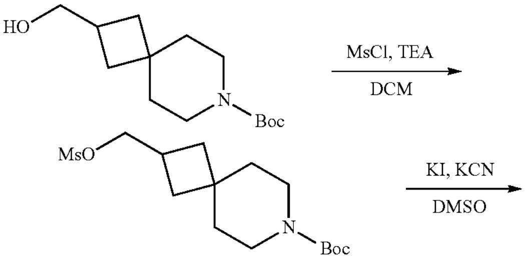

-continued

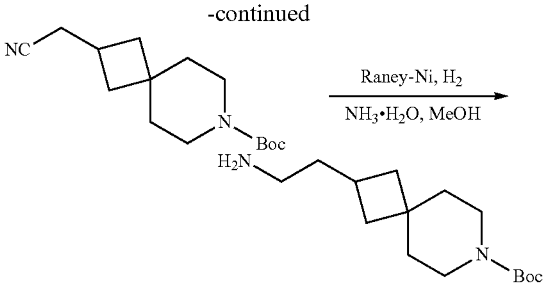

ATB

Step 1—Tert-butyl 2-(methylsulfonyloxyethyl)-7-azaspiro[3.5]nonane-7-carboxylate To a solution of tert-butyl 2-(hydroxymethyl)-7-azaspiro[3.5]nonane-7-carboxylate (1.00 g, 3.92 mmol, CAS #1356476-27-1) and TEA (594 mg, 5.87 mmol) in DCM (15 mL) was added MsCl (538 mg, 4.70 mmol) at 0° C. The reaction mixture was stirred at 0- 20° C. for 1 hr. On completion, the reaction mixture was diluted with water (30 mL) and extracted with DCM (3×40 mL). The combined organic layers were washed with brine (2×30 mL), dried over $Na_2SO_4$, filtered and concentrated in vacuo to give the title compound (1.20 g, 91% yield) as yellow oil. $^1$H NMR (400 MHz, $CDCl_3$) δ 4.20 (d, J=6.4 Hz, 2H), 3.41-3.32 (m, 2H), 3.30-3.23 (m, 2H), 3.02 (s, 3H), 2.75-2.62 (m, 1H), 2.03-1.93 (m, 2H), 1.66-1.61 (m, 2H), 1.61-1.59 (m, 1H), 1.58-1.56 (m, 1H), 1.50-1.47 (m, 2H), 1.45 (s, 9H).

Step 2—Tert-butyl 2-(cyanomethyl)-7-azaspiro[3.5]nonane-7-carboxylate

To a solution of tert-butyl 2-(methylsulfonyloxyethyl)-7-azaspiro[3.5]nonane-7-carboxylate (1.20 g, 3.60 mmol) and KI (896 mg, 5.40 mmol) in DMSO (15 mL) was added KCN (257 mg, 3.96 mmol,) at 25° C. The reaction mixture was stirred at 100° C. for 4 hrs. On completion, the reaction mixture was diluted with water (100 mL) and extracted with EA (3×60 mL). The combined organic layers were washed with brine (2×30 mL), dried over $Na_2SO_4$, filtered and concentrated in vacuo. The residue was purified by silica gel chromatography (PE:EA=10:1) to give the title compound (510 mg, 53% yield) as yellow solid. $^1$H NMR (400 MHz, $CDCl_3$) δ 3.43-3.33 (m, 2H), 3.31-3.22 (m, 2H), 2.70-2.52 (m, 1H), 2.45 (d, J=6.4 Hz, 2H), 2.14-1.99 (m, 2H), 1.68-1.58 (m, 4H), 1.54-1.48 (m, 2H), 1.46 (s, 9H).

Step 3—Tert-butyl 2-(2-aminoethyl)-7-azaspiro[3.5]nonane-7-carboxylate

To a solution of tert-butyl 2-(cyanomethyl)-7-azaspiro[3.5]nonane-7-carboxylate (0.50 g, 1.89 mmol) and $NH_3.H_2O$ (910 mg, 7.27 mmol, 28% solution) in MeOH (10 mL) was added Raney-Ni (32.4 mg, 378 umol). The reaction mixture was stirred at 20° C. for 3 hrs under hydrogen (50 psi). On completion, the reaction mixture was filtered and the filter cake was washed with methanol (50 mL). The combined organic phase was concentrated in vacuo to give the title compound (400 mg, 78% yield) as colorless oil. $^1$H NMR (400 MHz, DMSO-$d_6$) δ 3.25-3.23 (m, 2H), 3.17-3.14 (m, 2H), 2.42 (t, J=7.2 Hz, 2H), 2.30-2.17 (m, 1H), 1.93-1.84 (m, 2H), 1.49-1.41 (m, 4H), 1.37 (s, 9H), 1.36-1.28 (m, 4H).

4-[2-(7-Azaspiro[3.5]nonan-2-yl)ethylamino]-2-(2,6-dioxo-3-piperidyl)isoindoline-1,3-dione (Intermediate ATC)

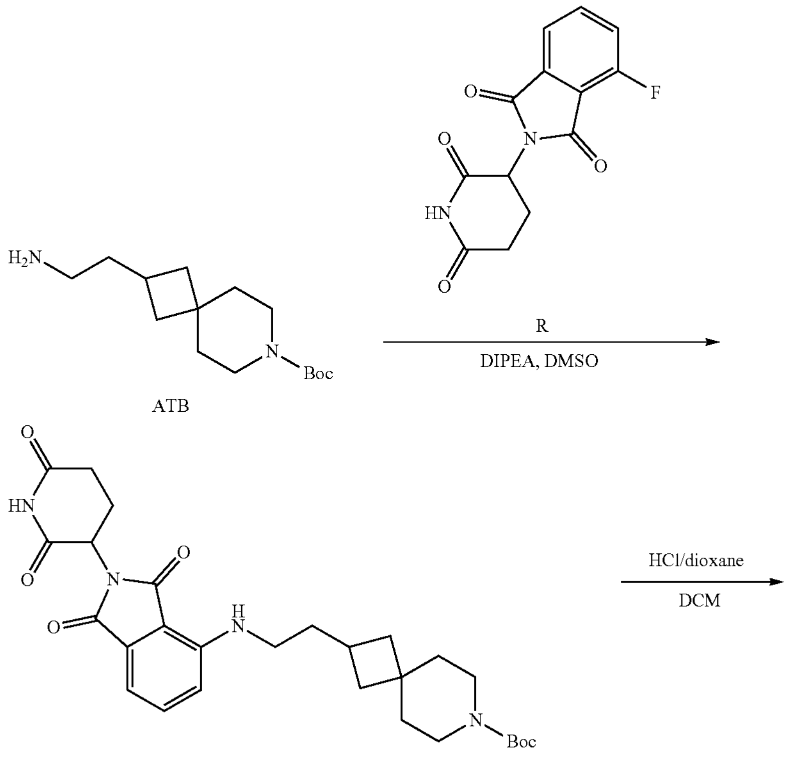

ATB

-continued

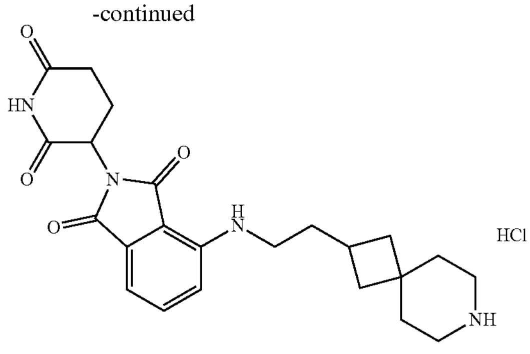

HCl

ATC

Step 1—Tert-butyl 2-[2-[[2-(2,6-dioxo-3-piperidyl)-1,3-dioxo-isoindolin-4-yl]amino]ethyl]-7-azaspiro[3.5]nonane-7-carboxylate To a solution of tert-butyl 2-(2-aminoethyl)-7-azaspiro[3.5]nonane-7-carboxylate (160 mg, 596 umol, Intermediate ATB) and 2-(2,6-dioxo-3-piperidyl)-4-fluoro-isoindoline-1,3-dione (181 mg, 655 umol, Intermediate R) in DMSO (3 mL) was added DIPEA (154 mg, 1.19 mmol). The reaction mixture was stirred at 130° C. for 2 hrs. On completion, the reaction mixture was diluted with water (10 mL) and extracted with EA (3x30 mL). The combined organic layers were washed with brine (20 mL), dried over $Na_2SO_4$, filtered and concentrated in vacuo. The residue was purified by reverse phase (0.1% FA) to give the title compound (200 mg, 63% yield) as yellow solid. $^1$H NMR (400 MHz, DMSO-$d_6$) δ 11.08 (s, 1H), 7.58 (dd, J=7.2, 8.4 Hz, 1H), 7.07 (d, J=8.4 Hz, 1H), 7.02 (d, J=6.8 Hz, 1H), 6.47 (t, J=5.6 Hz, 1H), 5.04 (dd, J=5.2, 12.8 Hz, 1H), 3.28-3.24 (m, 2H), 3.24-3.20 (m, 2H), 3.19-3.14 (m, 2H), 2.93-2.80 (m, 1H), 2.63-2.54 (m, 2H), 2.31-2.22 (m, 1H), 2.07-1.99 (m, 1H), 1.98-1.90 (m, 2H), 1.74-1.64 (m, 2H), 1.51-1.38 (m, 6H), 1.37 (s, 9H).

Step 2—4-[2-(7-Azaspiro[3.5]nonan-2-yl)ethyl-amino]-2-(2,6-dioxo-3-piperidyl)isoindoline-1,3-dione To a solution of tert-butyl 2-[2-[[2-(2,6-dioxo-3-piperidyl)-1,3-dioxo-isoindolin-4-yl]amino]ethyl]-7- azaspiro[3.5]nonane-7-carboxylate (50.0 mg, 95.3 umol) in DCM (1 mL) was added HCl/dioxane (4 M, 0.5 mL). The reaction mixture was stirred at 20° C. for 1 hr. On completion, the reaction mixture was concentrated in vacuo to give the title compound (43.0 mg, 97% yield, HCl salt) as yellow solid. LC-MS (ESI$^+$) m/z 425.3 (M+H)$^+$.

(4-Aminocyclohexyl)methanol (Intermediate ATD)

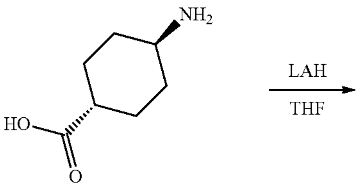

-continued

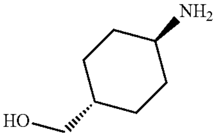

ATD

To a solution of LAH (26.5 g, 698 mmol) in THF (900 mL) was added 4-aminocyclohexanecarboxylic acid (50.0 g, 349 mmol, CAS #3685-25-4) dropwise at 0° C. The reaction mixture was stirred at 70° C. for 16 hrs. On completion, the reaction mixture was quenched by water (28 mL), then 10% NaOH aqueous (80 mL) and filtered. The filter cake was washed with DCM/THF=1/2 (5x800 mL). The combined organic layers were concentrated in vacuo to give the title compound (40.0 g, 88% yield) as light yellow solid. $^1$H NMR (400 MHz, DMSO-$d_6$) δ 4.33 (br s, 1H), 3.18 (d, J=6.4 Hz, 2H), 2.41 (tt, J=4.0, 10.4 Hz, 1H), 1.80-1.59 (m, 4H), 1.29-1.18 (m, 1H), 1.02-0.76 (m, 4H).

[4-(5-Amino-6-methoxy-indazol-2-yl)cyclohexyl]methanol (Intermediate ATE)

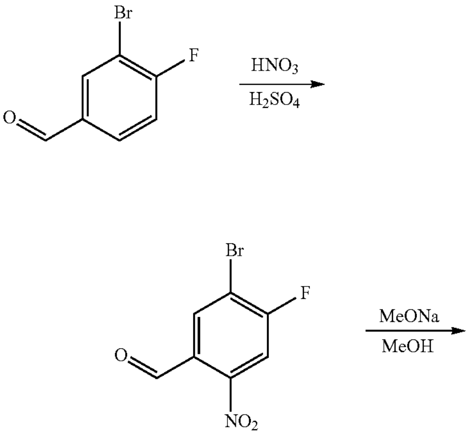

-continued

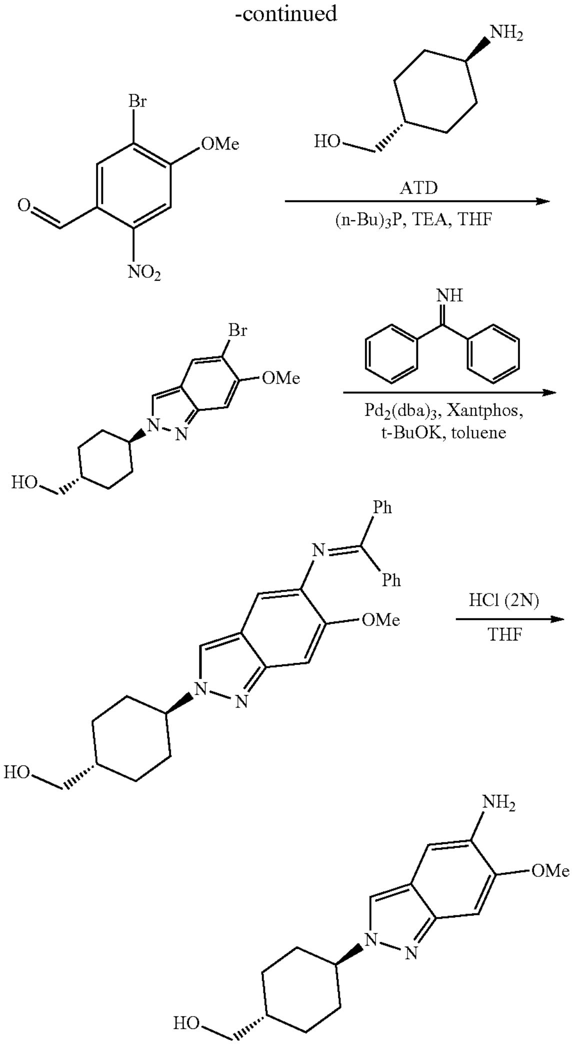

ATE

Step 1—5-Bromo-4-fluoro-2-nitro-benzaldehyde

To a solution of 3-bromo-4-fluoro-benzaldehyde (10.0 g, 49.2 mmol, CAS #77771-02-9) in $H_2SO_4$ (80 mL) was added $HNO_3$ (9.55 g, 98.5 mmol, 65% solution) dropwise at 0° C. The reaction mixture was stirred at 0- 20° C. for 12 hrs. On completion, the reaction mixture was poured into cold water (600 mL) and extracted with EA (3×200 mL). The combined organic layers were washed with brine (200 mL), dried over $Na_2SO_4$, filtered and concentrated in vacuo. The residue was purified by silica gel chromatography (PE: EA=200:1) to give the title compound (9.60 g, 78% yield) as yellow solid. $^1H$ NMR (400 MHz, DMSO-$d_6$) δ 10.14 (s, 1H), 8.31 (d, J=8.0 Hz, 1H), 8.26 (d, J=6.8 Hz, 1H).

Step 2—5-Bromo-4-methoxy-2-nitro-benzaldehyde

To a solution of 5-bromo-4-fluoro-2-nitro-benzaldehyde (4.00 g, 16.1 mmol) in MeOH (40 mL) was added NaOMe (1.31 g, 24.1 mmol) at 0° C. The reaction mixture was stirred at 0- 20° C. for 16 hrs. On completion, the reaction mixture was quenched by water (10 mL), diluted with water (60 mL) and filtered. The filter cake was dried in vacuo to give the title compound (2.10 g, 40% yield) as yellow solid. $^1H$ NMR (400 MHz, DMSO-$d_6$) δ 10.04 (s, 1H), 8.16 (s, 1H), 7.79 (s, 1H), 4.06 (s, 3H).

Step 3—[4-(5-Bromo-6-methoxy-indazol-2-yl)cyclohexyl]methanol

A mixture of 5-bromo-4-methoxy-2-nitro-benzaldehyde (1.90 g, 7.31 mmol) and (4-aminocyclohexyl) methanol (1.04 g, 8.04 mmol, Intermediate ATD) in IPA (20 mL) was stirred at 80° C. for 3 hrs. Then the solution was cooled to 25° C., and tributylphosphane (4.43 g, 21.9 mmol) was added and the reaction mixture was stirred at 80° C. for 16 hrs. On completion, the reaction mixture was concentrated in vacuo. The residue was purified by silica gel chromatography (PE:EA=1:1) to give the impure product. The impure product was triturated with PE (30 mL) to give the title compound (1.50 g, 60% yield) as white solid. $^1H$ NMR (400 MHz, DMSO-$d_6$) δ 8.27 (s, 1H), 7.95 (s, 1H), 7.10 (s, 1H), 4.47 (t, J=5.6 Hz, 1H), 4.42-4.31 (m, 1H), 3.86 (s, 3H), 3.28 (t, J=6.0 Hz, 2H), 2.17-2.04 (m, 2H), 1.95-1.79 (m, 4H), 1.54-1.39 (m, 1H), 1.21-1.05 (m, 2H).

Step 4—[4-[5-(Benzhydrylideneamino)-6-methoxy-indazol-2-yl]cyclohexyl]methanol

The reaction was performed in parallel two batches: A mixture of [4-(5-bromo-6-methoxy -indazol-2-yl)cyclohexyl]methanol (500 mg, 1.47 mmol), diphenylmethanimine (534 mg, 2.95 mmol), $Pd_2(dba)_3$ (134 mg, 147 umol), Xantphos (170 mg, 294 umol) and t-BuOK (496 mg, 4.42 mmol) in dioxane (10 mL) was stirred at 80° C. for 1 hr under nitrogen. On completion, the combined reaction mixture was quenched by methanol (1 mL), filtered and the filtrate was concentrated in vacuo. The residue was purified by silica gel chromatography (PE:EA=1:2) to give the title compound (600 mg, 11% yield) as yellow solid. LC-MS (ESI$^+$) m/z 440.2 (M+H)$^+$.

Step 5—[4-(5-Amino-6-methoxy-indazol-2-yl)cyclohexyl]methanol

To a solution of [4-[5-(benzhydrylideneamino)-6-methoxy-indazol-2-yl]cyclohexyl]methanol (650 mg, 1.48 mmol) in THE (3 mL) was added HCl/dioxane (2 M in water, 18.7 mL). The reaction mixture was stirred at 20° C. for 1 hr. On completion, the reaction mixture was concentrated in vacuo. The residue was purified by reverse phase (0.1% $NH_3.H_2O$) to give the title compound (180 mg, 33% yield) as yellow solid. LC-MS (ESI$^+$) m/z 276.1 (M+H)$^+$.

6-(1,1-Difluoroethyl)-N-[2-(4-formylcyclohexyl)-6-methoxy-indazol-5-yl]pyridine-2- carboxamide (Intermediate ATF)

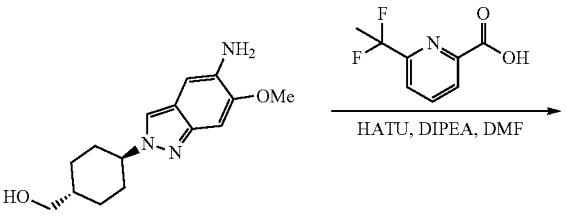

ATE

-continued

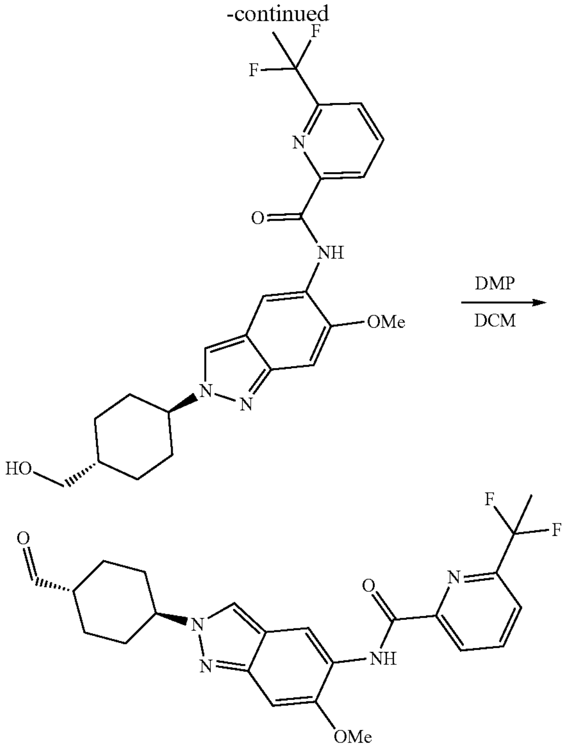

ATF

Step 1—6-(1,1-Difluoroethyl)-N-[2-[4-(hydroxymethyl)cyclohexyl]-6-methoxy-indazol-5-yl]pyridine-2-carboxamide To a solution of 6-(1,1-difluoroethyl)pyridine-2-carboxylic acid (80.8 mg, 432 umol, CAS #1211529-86-0), HATU (305 mg, 802 umol) and DIPEA (239 mg, 1.85 mmol) in DMF (3 mL) was added [4-(5-amino-6-methoxy -indazol-2-yl)cyclohexyl]methanol (170 mg, 617 umol, Intermediate ATE). The reaction mixture was stirred at 25° C. for 1 hr. On completion, the reaction mixture was quenched by water (0.1 mL) and concentrated in vacuo. The residue was purified by reverse phase (0.1% FA) to give the title compound (110 mg, 40% yield) as yellow solid. $^1$H NMR (400 MHz, DMSO-$d_6$) δ 10.67 (s, 1H), 8.67 (s, 1H), 8.40-8.26 (m, 3H), 8.01 (dd, J=2.0, 6.8 Hz, 1H), 7.16 (s, 1H), 4.49 (t, J=5.2 Hz, 1H), 4.41-4.29 (m, 1H), 3.99 (s, 3H), 3.31-3.27 (m, 2H), 2.23-2.10 (m, 3H), 1.97-1.80 (m, 4H), 1.56-1.39 (m, 1H), 1.31-1.03 (m, 4H).

Step 2—6-(1,1-Difluoroethyl)-N-[2-(4-formylcyclohexyl)-6-methoxy-indazol-5-yl]pyridine-2- carboxamide To a solution of 6-(1,1-difluoroethyl)-N-[2-[4-(hydroxymethyl)cyclohexyl]-6-methoxy-indazol-5- yl]pyridine-2-carboxamide (100 mg, 224 umol) in DCM (1 mL) was added DMP (114 mg, 269 umol). The reaction mixture was stirred at 20° C. for 1 hr. On completion, the reaction mixture was quenched by saturated Na$_2$S2SO$_3$ (1 mL), basified with saturated NaHCO$_3$ till pH=7~8 and extracted with DCM (3×20 mL). The combined organic layers were washed with brine (2×15 mL), dried over Na$_2$SO$_4$, filtered and concentrated in vacuo to give the title compound (90.0 mg, 90% yield) as yellow solid. $^1$H NMR (400 MHz, DMSO-$d_6$) δ 10.67 (s, 1H), 9.64 (s, 1H), 8.67 (s, 1H), 8.35-8.25 (m, 3H), 8.01 (dd, J=2.4, 6.8 Hz, 1H), 7.16 (s, 1H), 4.47-4.32 (m, 1H), 3.99 (s, 3H), 2.46-2.37 (m, 1H), 2.23-2.13 (m, 3H), 2.12-2.06 (m, 2H), 2.02-1.89 (m, 2H), 1.51-1.37 (m, 2H), 1.29-1.21 (m, 2H).

Tert-butyl 6-(2-aminoethyl)-2-azaspiro[3.3]heptane-2-carboxylate (Intermediate ATG)

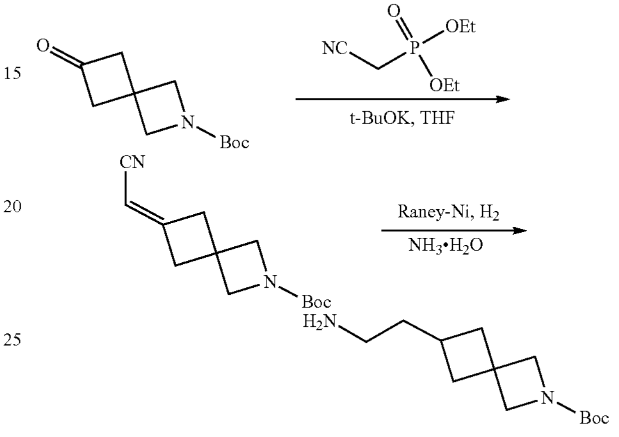

ATG

Step 1—Tert-butyl 6-(cyanomethylene)-2-azaspiro[3.3]heptane-2-carboxylate

To a solution of t-BuOK (3.98 g, 35.5 mmol,) in THE (35 mL) was added a solution of 2-diethoxyphosphorylacetonitrile (6.29 g, 35.5 mmol) in THE (70 mL) at 0° C. dropwise, and the reaction was stirred at 25° C. for 0.5 h. After, the mixture was cooled to 0° C. and a solution of tert-butyl 6-oxo-2-azaspiro[3.3]heptane-2-carboxylate (5.00 g, 23.7 mmol, CAS #1147557-97-8) in THE (35 mL) was added and the reaction was stirred at 25° C. for 16 hours. On completion, the reaction was quenched with water (10 mL) and the solvent was removed in vacuo to give a residue. The residue was purified by silica gel column chromatography (PE:EA from 5:1 to 1:1) to give the title compound (4.10 g, 66% yield) as a yellow oil. $^1$H NMR (400 MHz, DMSO-$d_6$) δ 5.55 (t, J=2.4 Hz, 1H), 3.91 (d, J=2.0 Hz, 4H), 3.17-3.01 (m, 4H), 1.37 (s, 9H).

Step 2—Tert-butyl 6-(2-aminoethyl)-2-azaspiro[3.3]heptane-2-carboxylate

To a solution of tert-butyl 6-(cyanomethylene)-2-azaspiro[3.3]heptane-2-carboxylate (4.10 g, 17.5 mmol) in MeOH (80 mL) and NH$_3$.H$_2$O (8 mL) was added Raney-Ni (1.50 g, 17.5 mmol). The mixture was degassed and purged with H$_2$ gas 3 times and then was stirred at 25° C. under H$_2$ at 50 psi for 3 hours. On completion, the reaction was filtered through celite, the filtered cake was washed with MeOH (3×5 mL) and the filtrate was concentrated in vacuo to give the title compound (3.10 g, 66% yield) as yellow oil. $^1$H NMR (400 MHz, DMSO-$d_6$) δ 3.82 (d, J=7.6 Hz, 4H), 2.47-2.00 (m, 5H), 1.79-1.67 (m, 2H), 1.46-1.38 (m, 2H), 1.36 (s, 9H).

4-[2-(2-Azaspiro[3.3]heptan-6-yl)ethylamino]-2-(2,6-dioxo-3-piperidyl)isoindoline-1,3-dione (Intermediate ATH)

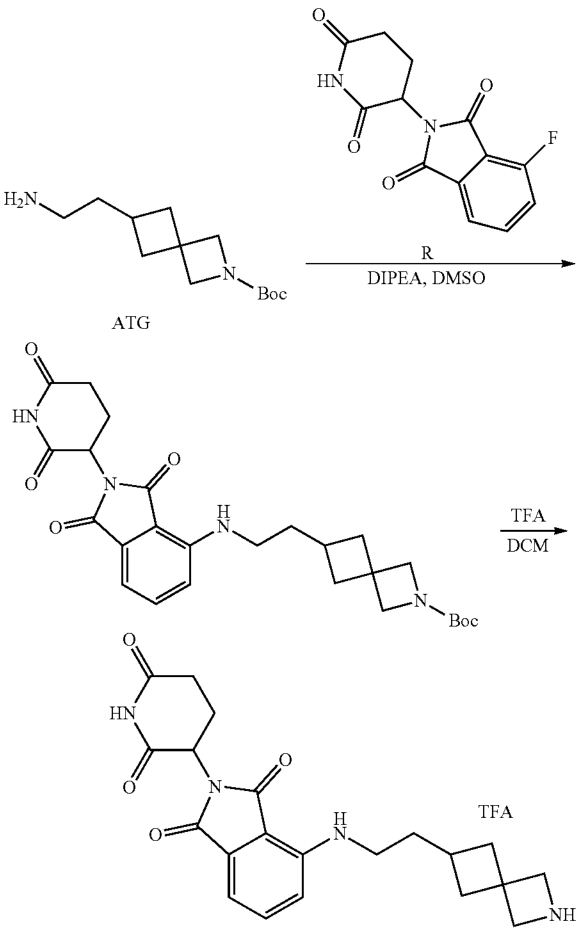

ATH

Step 1—Tert-butyl 6-[2-[[2-(2,6-dioxo-3-piperidyl)-1,3-dioxo-isoindolin-4-yl]amino]ethyl]-2-azaspiro[3.3]heptane-2-carboxylate To a solution of tert-butyl 6-(2-aminoethyl)-2-azaspiro[3.3]heptane-2-carboxylate (3.00 g, 12.5 mmol, Intermediate ATG) and 2-(2,6-dioxo-3-piperidyl)-4-fluoro-isoindoline-1,3-dione (3.79 g, 13.7 mmol, Intermediate R) in DMSO (30 mL) was added DIPEA (4.84 g, 37.5 mmol). The mixture was stirred at 130° C. for 1 hour. On completion, the reaction was diluted with EA (150 mL), washed with water (3×50 mL) and brine (100 mL), dried over $Na_2SO_4$, filtered and concentrated in vacuo to give a crude product which was purified by reversed phase (0.1% FA condition) to give the title compound (3.20 g, 46% yield) as a yellow solid. $^1H$ NMR (400 MHz, DMSO-$d_6$) δ 11.10 (s, 1H), 7.59 (dd, J=7.2, 8.4 Hz, 1H), 7.11-6.97 (m, 2H), 6.49 (t, J=5.6 Hz, 1H), 5.06 (dd, J=5.6, 12.8 Hz, 1H), 3.84 (s, 2H), 3.73 (s, 2H), 3.22 (q, J=6.4 Hz, 2H), 2.91-2.83 (m, 1H), 2.65-2.54 (m, 2H), 2.32-2.22 (m, 2H), 2.16 (t, J=7.6 Hz, 1H), 2.04 (d, J=2.4 Hz, 1H), 1.86-1.78 (m, 2H), 1.65 (q, J=7.2 Hz, 2H), 1.36 (s, 9H); LC-MS (ESI$^+$) m/z 497.3 (M+H)$^+$.

Step 2—4-[2-(2-Azaspiro[3.3]heptan-6-yl)ethylamino]-2-(2,6-dioxo-3-piperidyl)isoindoline-1,3-dione To a solution of tert-butyl 6-[2-[[2-(2,6-dioxo-3-piperidyl)-1,3-dioxo-isoindolin-4-yl]amino]ethyl]-2-azaspiro[3.3]heptane-2-carboxylate (0.30 g, 604 umol) in DCM (3 mL) was added TFA (2.31 g, 20.3 mmol). The mixture was stirred at 25° C. for 1 hour. On completion, the reaction was concentrated in vacuo to give the title compound (0.18 g, TFA, 58% yield) as a yellow solid. LC-MS (ESI$^+$) m/z 397.2 (M+H)$^+$.

6-(Trifluoromethyl)pyridine-2-carboxamide (Intermediate ATI)

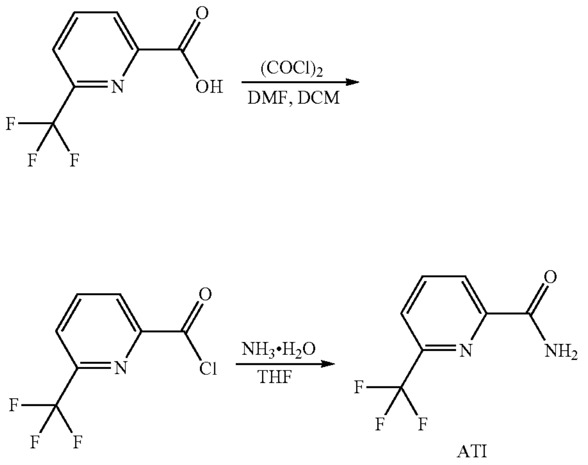

Step 1—6-(Trifluoromethyl)pyridine-2-carbonyl chloride

To a mixture of 6-(trifluoromethyl)pyridine-2-carboxylic acid (21.0 g, 109 mmol, CAS #131747-42-7) and DMF (401 mg, 5.49 mmol) in DCM (300 mL) was added $(COCl)_2$ (27.9 g, 219 mmol) at 0° C. The mixture was stirred at 25° C. for 1 hour. On completion, the reaction mixture was concentrated in vacuo to give the title compound (22 g, 95% yield) as light yellow oil.

Step 2—6-(Trifluoromethyl)pyridine-2-carboxamide

A solution of 6-(trifluoromethyl)pyridine-2-carbonyl chloride (21.5 g, 102 mmol) in THE (100 mL) was added $NH_3.H_2O$ (143 g, 1.03 mol, 158 mL, 25% solution) at 0° C. The mixture was stirred at 25° C. for 1 hour. On completion, the reaction mixture was concentrated in vacuo to remove THE and then filtered to give the filter cake as title product (19 g, 90% yield) as light yellow solid. $^1H$ NMR (400 MHz, DMSO-$d_6$) δ 8.35-8.24 (m, 2H), 8.08 (dd, J=1.6, 6.8 Hz, 1H), 8.05-7.78 (m, 2H); LC-MS (ESI$^+$) m/z 191.0 (M+H)$^+$.

N-[2-(4-formylcyclohexyl)-6-methoxy-indazol-5-yl]-6-(trifluoromethyl)pyridine-2- carboxamide (Intermediate ATJ)

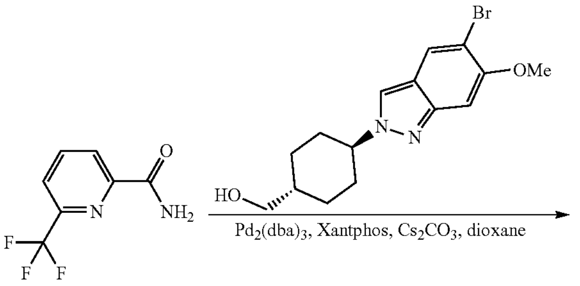

ATI

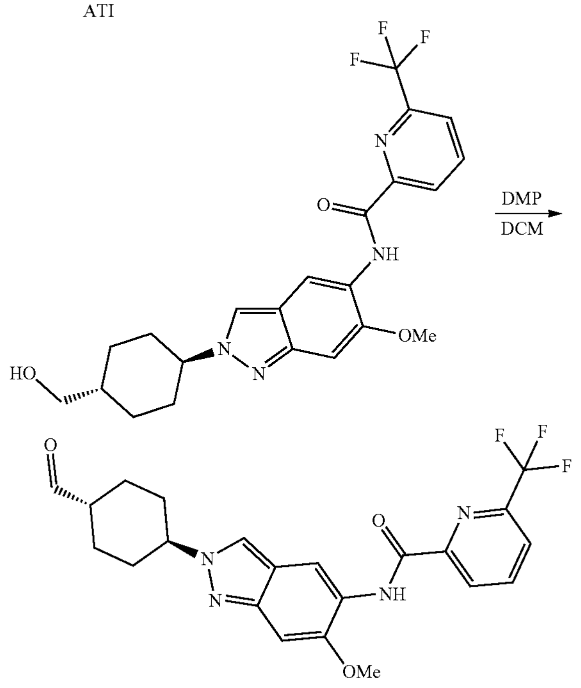

ATJ

Step 1—N-[2-[4-(hydroxymethyl)cyclohexyl]-6-methoxy-indazol-5-yl]-6-(trifluoromethyl)pyridine-2-carboxamide To a solution of [4-(5-bromo-6-methoxy-indazol-2-yl) cyclohexyl]methanol (6.50 g, 19.1 mmol, synthesized via Steps 1-3 of Intermediate ATE) in dioxane (150 mL) was added $Pd_2(dba)_3$ (1.75 g, 1.92 mmol), Xantphos (2.22 g, 3.83 mmol), $Cs_2CO_3$ (12.4 g, 38.3 mmol) and 6-(trifluoromethyl) pyridine-2-carboxamide (4.01 g, 21.0 mmol, Intermediate ATI). The mixture was stirred at 80° C. for 16 hours. On completion, the reaction was filtered and concentrated in vacuo to give a residue. The residue was diluted with DCM (150 mL), and washed with water (2×30 mL). The combined organic layers was dried over $Na_2SO_4$, filtered and concentrated in vacuo to give a residue. The residue was purified by column chromatography ($SiO_2$, PE/EA=1/1) to give the title compound (6.50 g, 75% yield) as gray solid. $^1$H NMR (400 MHz, DMSO-$d_6$) δ 10.48 (s, 1H), 8.67 (s, 1H), 8.50-8.41 (m, 1H), 8.41-8.33 (m, 1H), 8.31 (s, 1H), 8.19 (dd, J=0.8, 7.6 Hz, 1H), 7.14 (s, 1H), 4.77-4.26 (m, 2H), 4.04-3.92 (m, 1H), 3.97 (s, 2H), 3.29 (d, J=6.0 Hz, 2H), 2.22-2.06 (m, 2H), 1.96-1.79 (m, 4H), 1.55-1.40 (m, 1H), 1.25-1.03 (m, 2H); LC-MS (ESI$^+$) m/z 449.4 (M+H)$^+$.

Step 2—N-[2-(4-formylcyclohexyl)-6-methoxy-indazol-5-yl]-6-(trifluoromethyl)pyridine-2- carboxamide To a solution of N-[2-[4-(hydroxymethyl)cyclohexyl]-6-methoxy-indazol-5-yl]-6-(trifluoromethyl)pyridine-2-carboxamide (6.70 g, 14.9 mmol) in DCM (200 mL) was added DMP (7.60 g, 17.9 mmol). The mixture was stirred at 25° C. for 2 hours. On completion, the reaction mixture was diluted with DCM (100 mL) and quenched by saturated $Na_2S_2O_3$ (100 mL) and saturated $NaHCO_3$ (100 mL) at 0° C. The mixture was then stirred at 25° C. for 30 minutes. After, the organic layers was separated, then washed with saturated $NaHCO_3$ (100 mL) and saturated NaCl (100 mL). The organic layers dried over $Na_2SO_4$, filtered and concentrated in vacuo to give a residue. The residue was triturated with (EA/DCM=10/1) to give the title compound (6.6 g, 95% yield) as light yellow solid. $^1$H NMR (400 MHz, DMSO-$d_6$) δ 10.49 (s, 1H), 9.64 (s, 1H), 8.68 (s, 1H), 8.45 (d, J=8.0 Hz, 1H), 8.38 (t, J=8.0 Hz, 1H), 8.31 (s, 1H), 8.19 (d, J=7.6 Hz, 1H), 7.14 (s, 1H), 4.42-4.34 (m, 1H), 3.97 (s, 3H), 2.46-2.36 (m, 1H), 2.20 (dd, J=2.8, 12.4 Hz, 2H), 2.10 (d, J=11.6 Hz, 2H), 1.99-1.89 (m, 2H), 1.48-1.38 (m, 2H); LC-MS (ESI$^+$) m/z 447.2 (M+H)$^+$.

3-(3-Methyl-2-oxo-4-vinyl-benzimidazol-1-yl)piperidine-2,6-dione (Intermediate AAV)

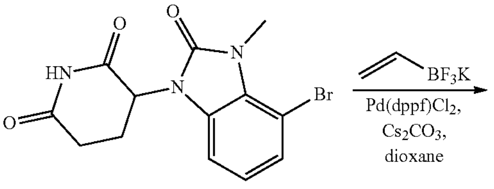

HP

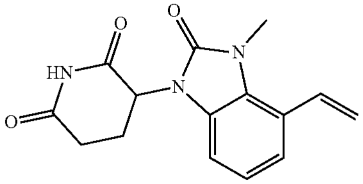

AAV

A mixture of 3-(4-bromo-3-methyl-2-oxo-benzimidazol-1-yl)piperidine-2,6-dione (10.0 g, 29.5 mmol, Intermediate HP), potassium;trifluoro(vinyl)boranuide (11.8 g, 88.7 mmol, CAS #13682-77-4), $Cs_2CO_3$ (2 M in water, 29.5 mL) and $Pd(dppf)Cl_2.CH_2Cl_2$ (1.69 g, 2.07 mmol) in dioxane (300 mL) was stirred at 90° C. for 2 hrs under nitrogen. On completion, the reaction mixture was filtered and the filtrated was concentrated in vacuo. The residue was purified by silica gel chromatography (petroleum ether:ethyl acetate=1:2) to give the title compound (5.70 g, 67% yield) as yellow solid. $^1$H NMR (400 MHz, DMSO-$d_6$) δ 11.10 (s, 1H), 7.40 (dd, J=10.8, 17.2 Hz, 1H), 7.18 (d, J=7.2 Hz, 1H), 7.10-6.98 (m, 2H), 5.72 (d, J=17.2 Hz, 1H), 5.47-5.31 (m, 2H), 3.54 (s, 3H), 2.96-2.82 (m, 1H), 2.79-2.57 (m, 2H), 2.06-1.94 (m, 1H).

[3-Methyl-4-[2-[3-(methylamino)azetidin-1-yl] ethyl]-2-oxo-benzimidazol-1-yl]piperidine-2,6-dione (Intermediate AAP)

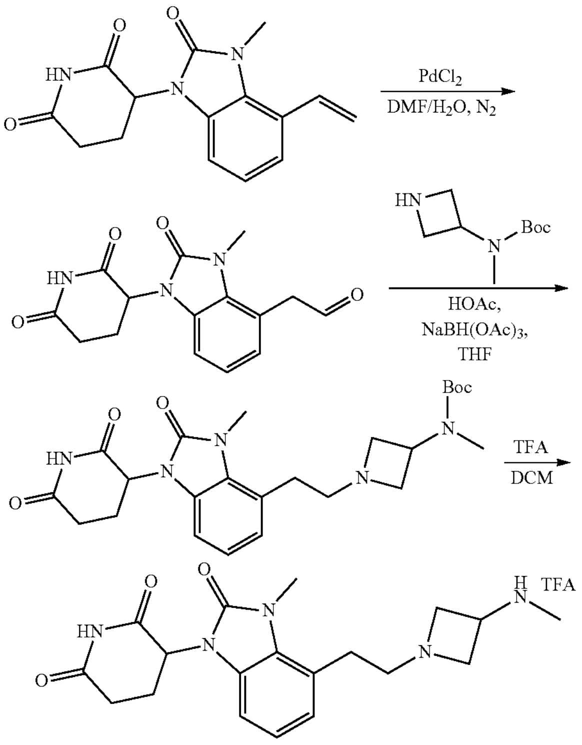

AAP

Step 1—2-[I-(2,6-Dioxo-3-piperidyl)-3-methyl-2-oxo-benzimidazol-4-yl]acetaldehyde To a solution of 3-(3-methyl-2-oxo-4-vinyl-benzimidazol-1-yl)piperidine-2,6-dione (1.00 g, 3.51 mmol, Intermediate AAV) in a mixed solvent of DMF (20 mL) and $H_2O$ (2 mL) was added $PdCl_2$ (1.24 g, 7.01 mmol, CAS #7647-10-1) at 25° C. under $N_2$. The mixture was stirred at 25° C. for 18 hours. On completion, the reaction mixture was concentrated under reduced pressure to remove solvent. The residue was diluted with water (20 mL) and extracted with EA (3×20 mL). The combined organic layers were dried over $Na_2SO_4$, filtered and concentrated in vacuo to give the title compound (260 mg, 24% yield) as black brown oil. LC-MS ($ESI^+$) m/z 301.9 $(M+H)^+$.

Step 2—Tert-butyl N-[1-[2-[1-(2,6-dioxo-3-piperidyl)-3-methyl-2-oxo-benzimidazol-4-yl]ethyl] azetidin-3-yl]-N-methyl-carbamate To a mixture of 2-[1-(2,6-dioxo-3-piperidyl)-3-methyl-2-oxo-benzimidazol-4-yl]acetaldehyde (200 mg, 663 umol) and tert-butyl N-(azetidin-3-yl)-N-methyl-carbamate (123 mg, 663 umol, CAS #577777-20-9) in THE (5 mL) was added HOAc (39.8 mg, 663 umol, 37.9 uL) at 25° C. The mixture was stirred at 25° C. for 0.5 hour. Then, NaBH $(OAc)_3$ (281 mg, 1.33 mmol) was added, and the mixture was stirred at 25° C. for another 3.5 hours. On completion, the reaction mixture was quenched by water (0.5 mL) at 25° C., and then concentrated in vacuo to give a residue. The residue was purified by reverse phase (0.1% FA condition) to give the title compound (260 mg, 83% yield, 51% purity) as light yellow oil. LC-MS ($ESI^+$) m/z 472.1 $(M+H)^+$.

Step 3—[3-Methyl-4-[2-[3-(methylamino)azetidin-1-yl]ethyl]-2-oxo-benzimidazol-1-yl]piperidine-2,6-dione To a solution of tert-butyl N-[1-[2-[1-(2,6-dioxo-3-piperidyl)-3-methyl-2-oxo-benzimidazol-4-yl]ethyl]azetidin-3-yl]-N-methyl-carbamate (110 mg, 233 umol) in DCM (5.5 mL) was added TFA (74.3 mmol, 5.50 mL) at 25° C. The mixture was stirred at 25° C. for 2 hours. On completion, the reaction mixture was concentrated in vacuo to give the title compound (80.0 mg, 70% yield, TFA salt) as yellow oil. LC-MS ($ESI^+$) m/z 372.1 $(M+H)^+$.

3-[4-[2-(2,7-Diazaspiro[3.5]nonan-2-yl)ethyl]-3-methyl-2-oxo-benzimidazol-1-yl]piperidine -2,6-dione (Intermediate ACV)

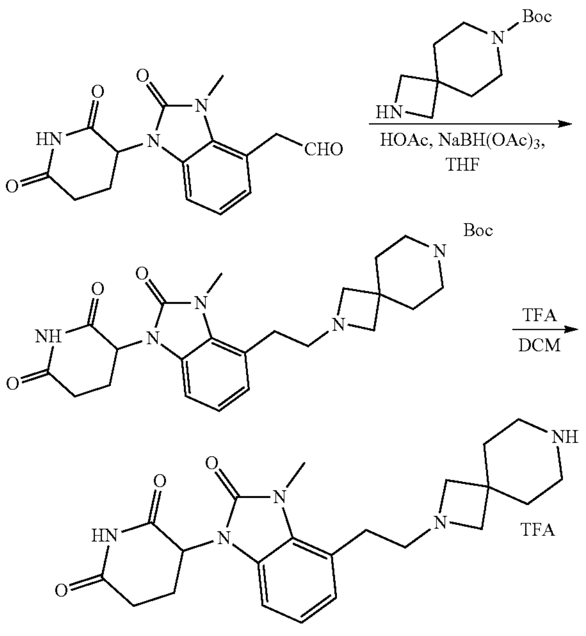

ACV

Step 1—Tert-butyl 2-[2-[1-(2,6-dioxo-3-piperidyl)-3-methyl-2-oxo-benzimidazol-4-yl]ethyl]-2,7- diazaspiro[3.5]nonane-7-carboxylate To a mixture of 2-[1-(2,6-dioxo-3-piperidyl)-3-methyl-2-oxo-benzimidazol-4-yl]acetaldehyde (200 mg, 663 umol, synthesized via Step 1 of Intermediate AAP) and tert-butyl 2,7-diazaspiro[3.5]nonane-7-carboxylate (187 mg, 663 umol, CAS #896464-16-7) in THE (5 mL) was added HOAc (39.8 mg, 663 umol) in one portion at 25° C. The mixture was stirred at 25° C. for 0.5 hour. Then $NaBH(OAc)_3$ (281 mg, 1.33 mmol) was added to the mixture. The mixture was stirred at 25° C. for 1.5 hours. On completion, the reaction mixture was quenched with water (0.5 mL) at 25° C., and then concentrated in vacuo to give a residue. The residue was purified by prep-HPLC (column: Shim-pack C18

150*25*10 um; mobile phase: [water (0.225% FA)-ACN]; B %: 6%-36%, 10 min) to give the title compound (35.0 mg, 10% yield) as a white solid. LC-MS ($ESI^+$) m/z 512.4 $(M+H)^+$.

Step 2—3-[4-[2-(2,7-Diazaspiro[3.5]nonan-2-yl) ethyl]-3-methyl-2-oxo-benzimidazol-1-yl]piperidine -2,6-dione To a mixture of tert-butyl 2-[2-[1-(2,6-dioxo-3-piperidyl)-3-methyl-2-oxo-benzimidazol-4-yl]ethyl]-2,7- diazaspiro [3.5]nonane-7-carboxylate (15.0 mg, 29.3 umol) in DCM (3 mL) was added TFA (3.00 mL) at 25° C. The mixture was stirred at 25° C. for 2 hours. On completion, the reaction mixture was concentrated in vacuo to give the title compound (15.0 mg, 97% yield, FA salt) as yellow solid. LC-MS ($ESI^+$) m/z 412.3 $(M+H)^+$.

3-[4-(5-aminopent-1-ynyl)-3-methyl-2-oxo-benzimidazol-1-yl]piperidine-2,6-dione (Intermediate AQJ)

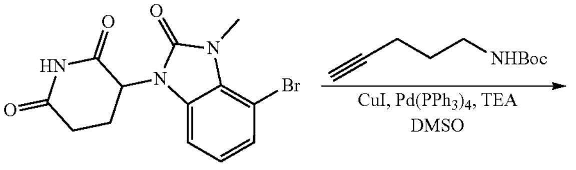

HP

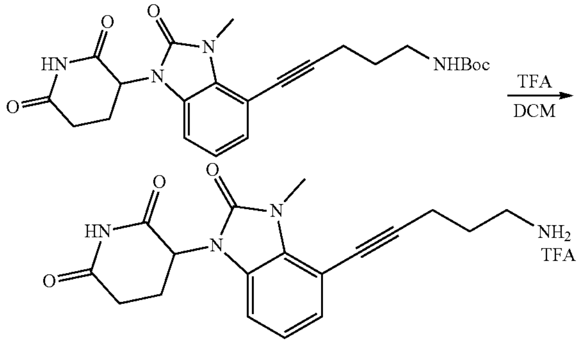

AQJ

Step 1—Tert-butyl N-[5-[1-(2,6-dioxopiperidin-3-yl)-3-methyl-2-oxo-1,3-benzodiazol-4-yl]pent-4-yn-1-yl]carbamate To a stirred mixture of 3-(4-bromo-3-methyl-2-oxo-1,3-benzodiazol-1-yl)piperidine-2,6-dione (10.00 g, 29.572 mmol, Intermediate HP) and tert-butyl N-(pent-4-yn-1-yl) carbamate (8.13 g, 44.358 mmol, CAS #151978-50-6) in DMSO (100.00 mL) was added TEA (50.00 mL) and CuI (0.56 g, 2.957 mmol) at rt. To the above mixture was added $Pd(PPh_3)_4$ (3.42 g, 2.957 mmol) at rt and the resulting mixture was stirred for 3 h at 80° C. under nitrogen atmosphere. After being cooled down to rt, the mixture was diluted with water (200 mL) and was extracted with EtOAc (4×200 mL). The combined organic layers were washed with brine (2×200 mL), dried over anhydrous $Na_2SO_4$ and filtered. The filtrate was concentrated under reduced pressure. The residue was purified by silica gel column chromatography with the following conditions (Mobile Phase: EtOAc) to afford the title compound (11 g, 84%) as a brown solid. $^1H$ NMR (400 MHz, Methanol-$d_4$) δ 7.15 (dd, J=7.5, 1.5 Hz, 1H), 7.10-7.01 (m, 2H), 5.34 (dd, J=12.2, 5.4 Hz, 1H), 3.78 (s, 3H), 3.23 (t, J=6.9 Hz, 2H), 3.01-2.75 (m, 3H), 2.54 (t, J=7.1 Hz, 2H), 2.19 (dp, J=10.3, 5.8, 5.2 Hz, 1H), 1.82 (p, J=7.0 Hz, 2H), 1.45 (s, 9H); LC/MS (ESI, m z): $[(M+18)]^+$=458.20.

Step 2—3-[4-(5-Aminopent-1-yn-1-yl)-3-methyl-2-oxo-1,3-benzodiazol-1-yl]piperidine-2,6-dione: trifluoroacetic acid To a solution of tert-butyl N-[5-[1-(2,6-dioxopiperidin-3-yl)-3-methyl-2-oxo-1,3-benzodiazol-4-yl]pent-4-yn-1-yl] carbamate (3.00 g, 6.810 mmol) in DCM (40.00 mL) was added TFA (10.00 mL) at 25° C. The mixture was stirred at 25° C. for 1 h. The resulting solution was concentrated under reduced pressure to afford the title compound (2 g, 86%) as a brown solid. $^1H$ NMR (400 MHz, Methanol-$d_4$) δ 7.13 (ddd, J=16.2, 7.9, 1.3 Hz, 2H), 7.04 (d, J=8.0 Hz, 1H), 5.35 (dd, J=12.2, 5.4 Hz, 1H), 3.77 (s, 3H), 3.13 (t, J=7.7 Hz, 2H), 2.99-2.75 (m, 3H), 2.68 (t, J=7.0 Hz, 2H), 2.23-2.13 (m, 1H), 2.02 (dd, J=14.7, 7.0 Hz, 2H); LC/MS (ESI, m z): $[(M+1)]^+$=341.10.

[1-[(4-Methoxyphenyl)methyl]-2,6-dioxo-3-piperidyl]trifluoromethanesulfonate (Intermediate IQ)

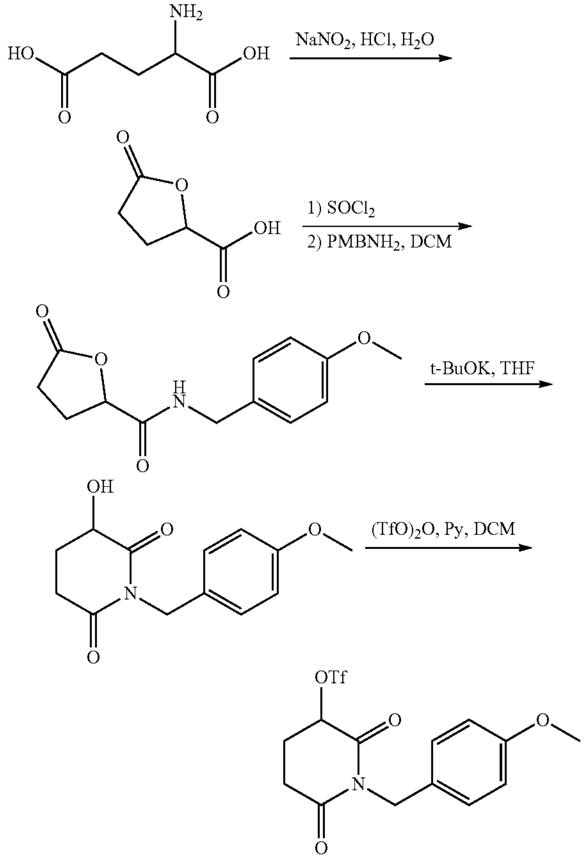

IQ

Step 1—5-Oxotetrahydrofuran-2-carboxylic acid

To a solution of 2-aminopentanedioic acid (210 g, 1.43 mol, CAS #617-65-2) in $H_2O$ (800 mL) and HCl (12 M, 210 mL) was added a solution of $NaNO_2$ (147 g, 2.13 mol) in $H_2O$ (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over $Na_2SO_4$, filtered and concentrated in vacuo to give the title compound (200 g, crude) as yellow oil. $^1H$ NMR (400 MHz, $CDCl_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added $SOCl_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under $N_2$. After that a solution of $Et_3N$ (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1H$ NMR (400 MHz, $CDCl_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS ($ESI^+$) m z 272.0 (M+Na)+.

Step 3—3-Hydroxy-1-[(4-methoxyphenyl)methyl] piperidine-2,6-dione

A solution of N-[(4-methoxyphenyl)methyl]-5-oxo-tetrahydrofuran-2-carboxamide (138 g, 553 mmol) in anhydrous THE (1500 mL) was cooled to −78° C. Then, t-BuOK (62.7 g, 559 mmol) in a solution of anhydrous THE (1000 mL) was added dropwise slowly at −78° C. under nitrogen atmosphere. The resulting reaction mixture was stirred at −40° C. for 1 hr. On completion, the reaction mixture was quenched with saturated $NH_4Cl$ solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1H$ NMR (400 MHz, $CDCl_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl)methyl]-2,6-dioxo-3-piperidyl]trifluoromethanesulfonate To a solution of 3-hydroxy-1-[(4-methoxyphenyl)methyl] piperidine-2, 6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under $N_2$. On completion, the mixture was concentrated in vacuo. The residue was purified by column chromatography on silica gel (PE:EA=20:1/8:1) to give the title compound (45.0 g, 68% yield) as light yellow gum. $^1H$ NMR (400 MHz, $CDCl_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

3-(5-bromo-3-methyl-2-oxo-benzimidazol-1-yl)piperidine-2,6-dione (Intermediate HN)

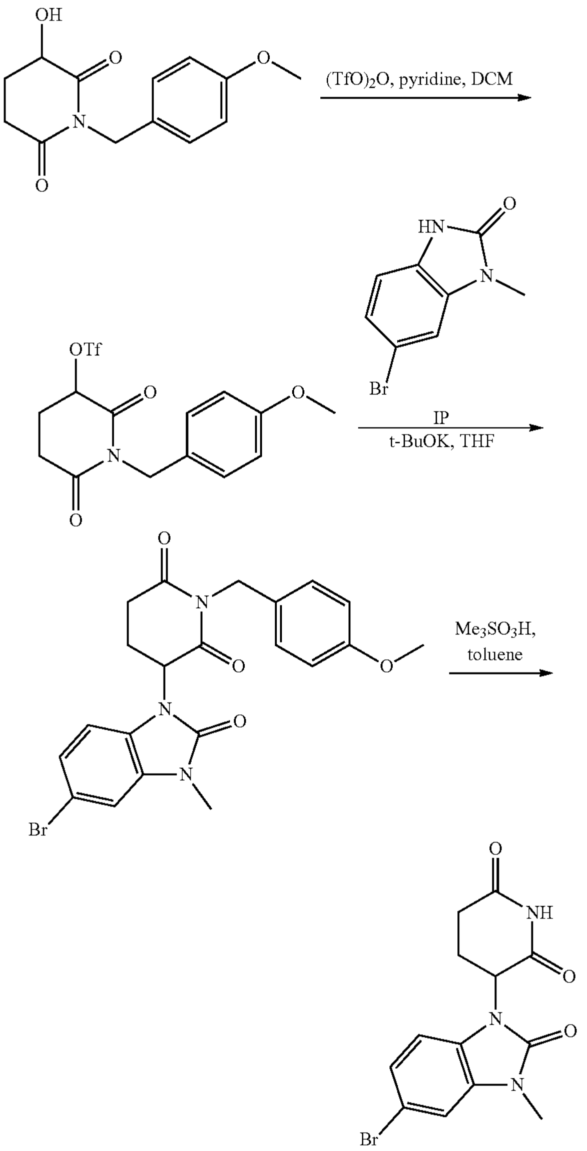

HN

Step 1—[1-[(4-Methoxyphenyl)methyl]-2,6-dioxo-3-piperidyl]trifluoromethanesulfonate To a solution of 3-hydroxy-1-[(4-methoxyphenyl)methyl] piperidine-2,6-dione (43.0 g, 173 mmol, Intermediate IQ) and pyridine (27.3 g, 345 mmol) in DCM (500 mL) was added trifluoromethylsulfonyl trifluoromethanesulfonate (73.0 g, 258.74 mmol) dropwise at 0° C. The mixture was stirred at 0-10° C. for 1.5 hours under $N_2$. On completion, the mixture was concentrated in vacuo. The residue was purified by column chromatography on silica gel to give the title compound (45.0 g, 68% yield) as light yellow gum. $^1$H NMR (400 MHz, $CDCl_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

Step 2—3-(5-Bromo-3-methyl-2-oxo-benzimidazol-1-yl)-1-[(4-methoxyphenyl)methyl]piperidine-2,6-dione To a solution of 5-bromo-3-methyl-1H-benzimidazol-2-one (4.90 g, 21.6 mmol, Intermediate IP) in THF (300 mL) was added t-BuOK (3.63 g, 32.3 mmol) at 0° C. The mixture was stirred at 0-10° C. for 1 hour under $N_2$. Then a solution of [1-[(4-methoxyphenyl)methyl]-2, 6-dioxo-3-piperidyl] trifluoromethanesulfonate (9.87 g, 25.9 mmol) in THE (100 mL) was added to the reaction mixture at 0-10° C. during 30 minutes. The mixture was stirred at 0-10° C. for 30 minutes under $N_2$. An additional solution of [1-[(4-methoxyphenyl) methyl]-2, 6-dioxo-3-piperidyl]trifluoromethanesulfonate (2.47 g, 6.47 mmol) in THE (20 mL) was added to the reaction mixture at 0-10° C. dropwise. The mixture was then stirred at 0-10° C. for another 30 minutes under $N_2$. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. $^1$H NMR (400 MHz, DMSO-$d_6$) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 3—3-(5-Bromo-3-methyl-2-oxo-benzimidazol-1-yl)piperidine-2,6-dione

To a mixture of 3-(5-bromo-3-methyl-2-oxo-benzimidazol-1-yl)-1-[(4-methoxyphenyl)methyl]piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over $Na_2SO_4$, filtered and concentrated in vacuo. The residue was triturated with EA (80 mL) and filtered. The filtrate cake was collected and dried in vacuo to give the title compound (4.20 g, 67% yield) as off-white solid. $^1$H NMR (400 MHz, DMSO-$d_6$) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

3-[5-(5-aminopent-1-ynyl)-3-methyl-2-oxo-benzimidazol-1-yl]piperidine-2,6-dione (Intermediate ATV)

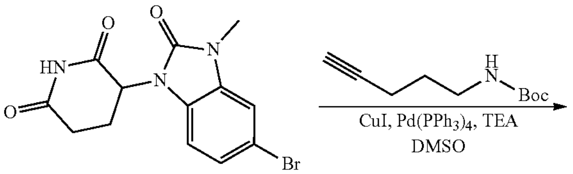

HN

-continued

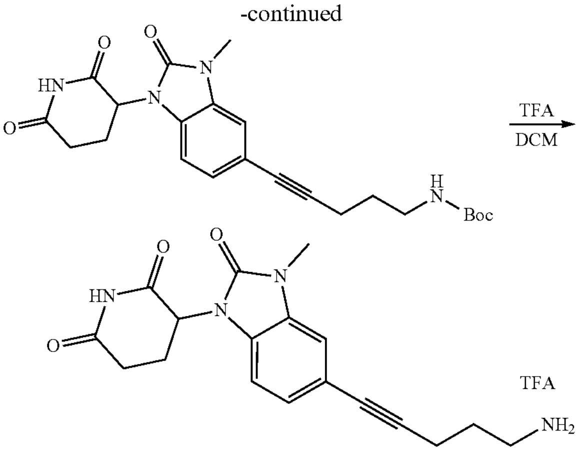

ATV

Step 1—Tert-butyl N-[5-[1-(2,6-dioxopiperidin-3-yl)-3-methyl-2-oxo-1,3-benzodiazol-5-yl]pent-4-yn-1-yl]carbamate To a stirred solution of 3-(5-bromo-3-methyl-2-oxo-1,3-benzodiazol-1-yl)piperidine-2,6-dione (3.80 g, 11.2 mmol, Intermediate HN) and tert-butyl N-(pent-4-yn-1-yl)carbamate (3.09 g, 16.8 mmol, CAS #151978-50-6) in DMSO (20.00 mL) and TEA (10.00 mL) were added $Pd(PPh_3)_4$ (1.30 g, 1.12 mmol) and CuI (0.21 g, 1.1 mmol) at room temperature under nitrogen atmosphere. The resulting mixture was stirred for overnight at 85° C. under nitrogen atmosphere. The resulting mixture was then cooled down to room temperature and concentrated under reduced pressure to remove TEA. The residue was diluted with water (100 mL) and extracted with EtOAc (5×200 mL). The combined organic layers were washed with brine (3×100 mL), and dried over anhydrous $Na_2SO_4$. After filtration, the filtrate was concentrated under reduced pressure. The residue was purified by silica gel column chromatography, eluted with petroleum ether/EtOAc (1:1) to afford the title compound (4 g, 81%) as a brown solid. $^1$H NMR (400 MHz, DMSO-$d_6$) δ 11.10 (s, 1H), 7.25 (s, 1H), 7.10 (s, 2H), 6.88 (s, 1H), 5.38 (dd, J=12.7, 5.3 Hz, 1H), 3.34 (s, 3H), 3.06 (q, J=6.7 Hz, 2H), 2.93-2.83 (m, 1H), 2.78-2.58 (m, 2H), 2.41 (t, J=7.1 Hz, 2H), 2.02 (dd, J=10.7, 5.7 Hz, 1H), 1.66 (p, J=7.1 Hz, 2H), 1.39 (s, 9H). LC/MS (ESI, m/z): [(M+1)]+=441.2.

Step 2—3-[5-(5-Aminopent-1-yn-1-yl)-3-methyl-2-oxo-1,3-benzodiazol-1-yl]piperidine-2,6-dione; trifluoroacetaldehyde To a stirred solution of tert-butyl N-[5-[1-(2,6-dioxopiperidin-3-yl)-3-methyl-2-oxo-1,3-benzodiazol-5-yl]pent-4-yn-1-yl]carbamate (4.90 g, 11.1 mmol) in DCM (50.00 mL) was added TFA (5.00 mL) dropwise at room temperature and the resulting mixture was stirred for 16 h at room temperature. The mixture was then concentrated under reduced pressure and the residue was triturated with ethyl ether (25 mL). After filtration, the filter cake was washed with ethyl ether (2×5 mL) and dried to give the title compound (4 g, crude) as a white solid. $^1$H NMR (400 MHz, Methanol-$d_4$) δ 7.21 (d, J=1.4 Hz, 1H), 7.17 (dd, J=8.2, 1.5 Hz, 1H), 7.07 (d, J=8.2 Hz, 1H), 5.34 (dd, J=12.6, 5.4 Hz, 1H), 3.41 (s, 3H), 3.14 (t, J=7.7 Hz, 2H), 2.93 (ddd, J=18.0, 14.2, 5.1 Hz, 1H), 2.87-2.71 (m, 2H), 2.60 (t, J=6.9 Hz, 2H), 2.23-2.11 (m, 1H), 1.97 (dq, J=9.7, 7.0 Hz, 2H). LC/MS (ESI, m z): [(M+1)]*=341.2.

Tert-butyl N-[4-(bromomethyl)cyclohexyl]-N-methyl-carbamate (Intermediate AVT)

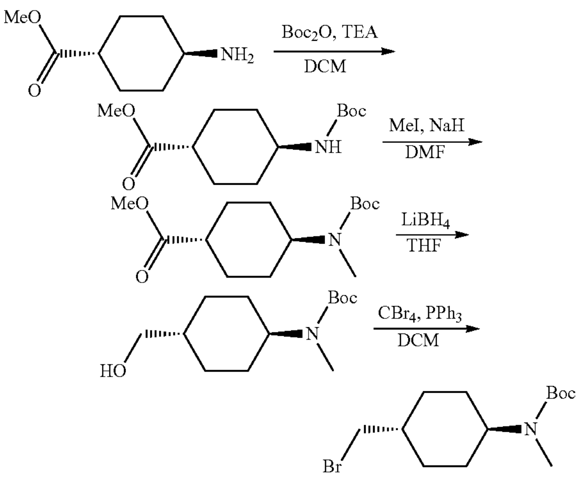

AVT

Step 1—Methyl 4-(tert-butoxycarbonylamino)cyclohexanecarboxylate

To a solution of methyl 4-aminocyclohexanecarboxylate (1.70 g, 10.8 mmol) in DCM (20 mL) was added TEA (2.41 g, 23.8 mmolL) and $Boc_2O$ (2.60 g, 11.9 mmol) at 0° C. and then the mixture was stirred at 25° C. for 12 hrs. On completion, the residue was added citric acid (8 g acid in 64 ml water) and extracted with EA (3×40 ml). The combined organic layers were washed with aqueous NaCl (3×30 mL), dried over anhydrous $Na_2SO_4$, filtered and concentrated under reduced pressure to give the title compound (3.0 g, 95% yield) as a gray solid. $^1H$ NMR (400 MHz, DMSO-$d_6$) δ 6.69 (d, J=7.6 Hz, 1H), 3.57 (s, 3H), 3.22-3.09 (m, 1H), 2.18 (tt, J=3.6, 12.0 Hz, 1H), 1.91-1.77 (m, 4H), 1.37 (s, 9H), 1.35-1.28 (m, 2H), 1.17-1.10 (m, 2H).

Step 2—Methyl 4-[tert-butoxycarbonyl(methyl) amino]cyclohexanecarboxylate

To a solution of methyl 4-(tert-butoxycarbonylamino) cyclohexanecarboxylate (3.00 g, 11.7 mmol) in DMF (100 mL) was added NaH (1.87 g, 46.6 mmol, 60% dispersion in mineral oil), the mixture was degassed and purged with $N_2$ for 3 times, and then stirred at 25° C. for 1 hr under $N_2$ atmosphere. MeI (16.6 g, 117 mmol, 7.26 mL) was added and the mixture was stirred at 25° C. for 17 hr under $N_2$ atmosphere. On completion, the mixture was adjusted pH to 7 with HCl (2 N). Then the mixture was added into 60 ml of water and extracted with EA (3×40 ml). The combined organic layers were washed with aqueous NaCl (3×40 mL), dried over anhydrous $Na_2SO_4$, filtered and concentrated under reduced pressure to give the title compound (3.4 g, crude) as yellow oil. $^1H$ NMR (400 MHz, DMSO-$d_6$) δ 3.82-3.63 (m, 1H), 3.58 (s, 3H), 2.65 (s, 3H), 2.25 (tt, J=3.6, 12.0 Hz, 1H), 1.98-1.92 (m, 2H), 1.60-1.54 (m, 2H), 1.53-1.45 (m, 2H), 1.45-1.41 (m, 1H), 1.39 (s, 9H), 1.33 (d, J=3.6 Hz, 1H).

Step 3—Tert-butyl N-[4-(hydroxymethyl)cyclohexyl]-N-methyl-carbamate

To a solution of methyl 4-[tert-butoxycarbonyl(methyl) amino]cyclohexanecarboxylate (3.4 g, 12.5 mmol) in THE (40 mL) was added $LiBH_4$ (1.09 g, 50.1 mmol) at 0° C. under $N_2$ atmosphere. The mixture was stirred at 80° C. for 3 hr. On completion, the reaction mixture was quenched by with $H_2O$ (60 mL) and extracted with EA (3×60 mL). The combined organic layers were washed with aqueous NaCl (3×40 mL), dried over anhydrous $Na_2SO_4$, filtered and concentrated under reduced pressure to give the title compound (3.00 g, 80% yield) as yellow oil. $^1H$ NMR (400 MHz, DMSO-$d_6$) δ 4.38 (s, 1H), 3.82-3.54 (m, 1H), 3.21-3.16 (m, 2H), 2.65 (s, 3H), 1.82-1.73 (m, 2H), 1.60-1.42 (m, 4H), 1.38 (s, 9H), 1.28-1.23 (m, 1H), 0.93 (dq, J=3.2, 12.4 Hz, 2H).

Step 4—Tert-butyl N-[4-(bromomethyl)cyclohexyl]-N-methyl-carbamate

A mixture of tert-butyl N-[4-(hydroxymethyl)cyclohexyl]-N-methyl-carbamate (3.00 g, 12.3 mmol), and $PPh_3$ (9.70 g, 40.0 mmol) in DCM (40 mL) was degassed and purged with $N_2$ for 3 times. Then the mixture was stirred at 0° C. and $CBr_4$ (12.3 g, 37.0 mmol) was added, and the mixture was stirred at 25° C. for 12 hr under $N_2$ atmosphere. On completion, the reaction mixture was filtered and concentrated under reduced pressure to give a residue. The residue was purified by column chromatography (PE: EA=20:1) to give the title compound (1.00 g, 27% yield) as yellow oil. $^1H$ NMR (400 MHz, DMSO-$d_6$) δ 3.84-3.59 (m, 1H), 3.42 (d, J=6.0 Hz, 2H), 2.64 (s, 3H), 1.87 (d, J=12.8 Hz, 2H), 1.61-1.45 (m, 5H), 1.38 (s, 9H), 1.14-1.04 (m, 2H).

3-[3-methyl-4-[[4-(methylamino)cyclohexyl] methyl]-2-oxo-benzimidazol-1-yl]piperidine- 2,6-dione (Intermediate AVU)

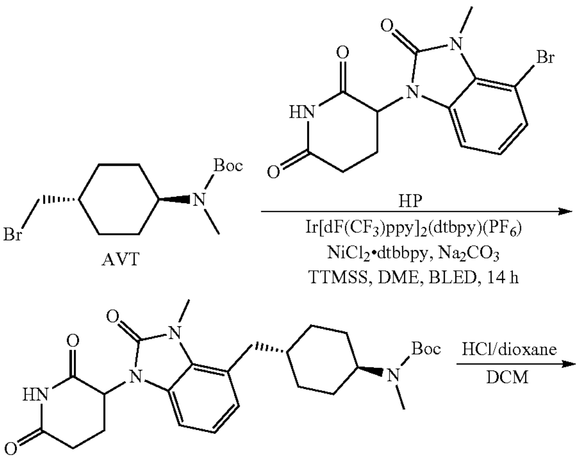

-continued

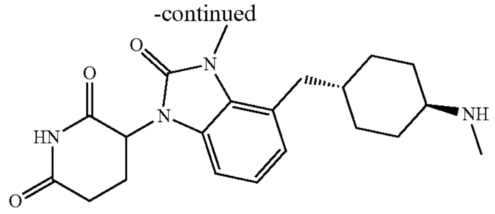

AVU

Step 1—Tert-butylN-[4-[[1-(2,6-dioxo-3-piperidyl)-3-methyl-2-oxo-benzimidazol-4-yl]methyl]cyclohexyl]-N-methyl-carbamate To an 40 mL vial equipped with a stir bar was added 3-(4-bromo-3-methyl-2-oxo-benzimidazol-1-yl)piperidine-2,6-dione (993 mg, 2.94 mmol, Intermediate HP), tert-butylN-[4-(bromomethyl)cyclohexyl]-N-methyl-carbamate (900 mg, 2.94 mmol, Intermediate AVT), 1r[dF(CF3)ppy]$_2$ (dtbpy)($PF_6$) (33.0 mg, 29.4 umol), $NiCl_2$-dtbbpy (5.85 mg, 14.7 umol), $Na_2CO_3$ (623 mg, 5.88 mmol), and TTMSS (731 mg, 2.94 mmol, 907 uL) in DME (20 mL). The vial was sealed and placed under nitrogen was added. The reaction was stirred and irradiated with a 34 W blue LED lamp (7 cm away), with cooling fan to keep the reaction temperature at 25° C. for 14 hr. On completion, the reaction mixture was filtered and concentrated under reduced pressure to give a residue. The crude product was purified by reversed-phase HPLC (0.1% FA condition, 65-70% $CH_3CN$,5 min) to give the title compound (150 mg, 10% yield) as a white solid. LC-MS ($ESI^+$) m/z 429.2 (M+H-56)*.

Step 2—3-[3-methyl-4-[[4-(methylamino)cyclohexyl]methyl]-2-oxo-benzimidazol-1-yl]piperidine-2,6-dione To a solution of tert-butylN-[4-[[1-(2,6-dioxo-3-piperidyl)-3-methyl-2-oxo-benzimidazol-4-yl]methyl]cyclohexyl]-N-methyl-carbamate (50 mg, 103 umol) in DCM (3.0 mL) was added HCl/dioxane (4 M, 1.0 mL). The mixture was stirred at 25° C. for 1 hr. On completion, the reaction mixture was concentrated under reduced pressure to give the title compound (40 mg, 90% yield, HCl salt) as a white solid.

4-[4-[[1-(2,6-Dioxo-3-piperidyl)-3-methyl-2-oxo-benzimidazol-4-yl]methyl]-1-piperidyl]benzaldehyde (Intermediate ATS) and [3-Methyl-2-oxo-4-(4-piperidylmethyl)benzimidazol-1-yl]piperidine-2,6-dione (Intermediate AVW)

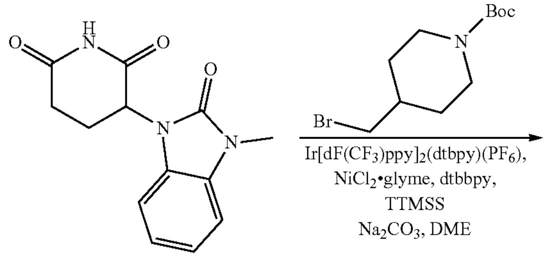

HP

-continued

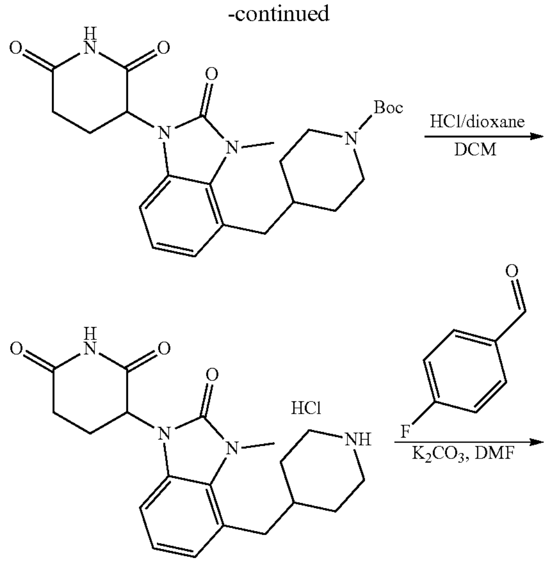

AVW

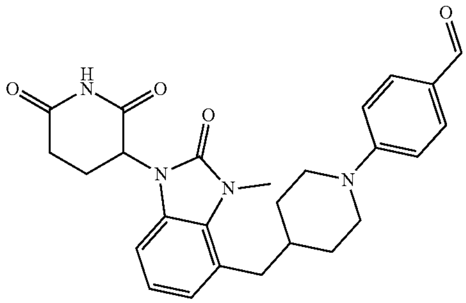

ATS

Step 1—Tert-butyl 4-[[1-(2,6-dioxo-3-piperidyl)-3-methyl-2-oxo-benzimidazol-4-yl]methyl]piperidine-1-carboxylate To an 40 mL vial equipped with a stir bar was added 3-(4-bromo-3-methyl-2-oxo-benzimidazol-1-yl) piperidine-2,6-dione (750 mg, 2.22 mmol, Intermediate HP), tert-butyl 4-(bromomethyl)piperidine-1-carboxylate (734 mg, 2.64 mmol, CAS #158407-06-6), 1r[dF(CF3)ppy]2(dtbpy)($PF_6$) (24.9 mg, 22.2 umol), $NiCl_2$.glyme (2.44 mg, 11.1 umol), dtbbpy (3.57 mg, 13.3 umol), TTMSS (552 mg, 2.22 mmol) and $Na_2CO_3$ (470 mg, 4.44 mmol) in DME (20 mL). The vial was sealed and placed under nitrogen was added. The reaction was stirred and irradiated with a 34 W blue LED lamp at 25° C. for 14 hr. On completion, the reaction mixture was filtered and the filtrate was concentrated in vacuo to give a residue. The residue was purified by reverse phase flash (0.1% TFA condition) to give the title compound (300 mg, 30% yield) as a white solid. $^1$H NMR (400 MHz, DMSO-$d_6$) δ=11.01 (s, 1H), 6.98-6.68 (m, 3H), 5.28 (dd, J=5.6, 12.4 Hz, 1H), 3.92-3.77 (m, 2H), 3.47 (s, 3H), 2.85-2.68 (m, 3H), 2.67-2.50 (m, 4H), 1.98-1.86 (m, 1H), 1.69-1.44 (m, 3H), 1.31 (s, 9H), 1.06-1.02 (m, 2H).

Step 2—[3-Methyl-2-oxo-4-(4-piperidylmethyl) benzimidazol-1-yl]piperidine-2,6-dione To a mixture of tert-butyl 4-[[1-(2,6-dioxo-3-piperidyl)-3-methyl-2-oxo-benzimidazol-4-yl]methyl]piperidine-1-carboxylate (100 mg, 219 umol) in DCM (2.0 mL) was added HCl/dioxane (4 M, 1.0 mL) in one portion at 25° C. under $N_2$. The reaction mixture was stirred at 25° C. for 30 min. On completion, the mixture was concentrated in vacuo to give the title compound (76.5 mg, 97% yield, HCl salt) as a white solid. LC-MS (ESI+) m/z 357.1 (M+H)+.

Step 3—4-[4-[[1-(2,6-dioxo-3-piperidyl)-3-methyl-2-oxo-benzimidazol-4-yl]methyl]-1-piperidyl]benzaldehyde A mixture of 3-[3-methyl-2-oxo-4-(4-piperidylmethyl) benzimidazol-1-yl]piperidine-2,6-dione (150 mg, 382 umol, HCl salt) in DMF (40 mL) was added $K_2CO_3$ (106 mg, 764 umol) and 4 Å molecular sieves (150 mg). The reaction mixture was stirred at 80° C. for 30 min. Then 4-fluorobenzaldehyde (71.1 mg, 573 umol) was added and stirred for 12 hours. On completion, the reaction mixture was filtered and the filtrate was concentrated in vacuo to give a residue. The residue was purified by reverse phase flash (FA condition) to give the title compound (100 mg, 57% yield) as white solid. $^1H$ NMR (400 MHz, DMSO-$d_6$) δ=11.10 (s, 1H), 9.69 (s, 1H), 7.69 (d, J=8.8 Hz, 2H), 7.06-6.94 (m, 4H), 6.85 (dd, J=1.6, 7.2 Hz, 1H), 5.38 (dd, J=5.6, 12.4 Hz, 1H), 4.02 (d, J=13.6 Hz, 2H), 3.58 (s, 3H), 2.97-2.81 (m, 5H), 2.78-2.59 (m, 2H), 2.07-1.95 (m, 1H), 1.84 (m, 1H), 1.71 (d, J=12.0 Hz, 2H), 1.40-1.23 (m, 2H). LC-MS (ESI+) m/z 461.2 (M+H)+.

3-[3-Methyl-5-[4-(methylamino)-1-piperidyl]-2-oxo-benzimidazol-1-yl]piperidine-2,6-dione (Intermediate AVX)

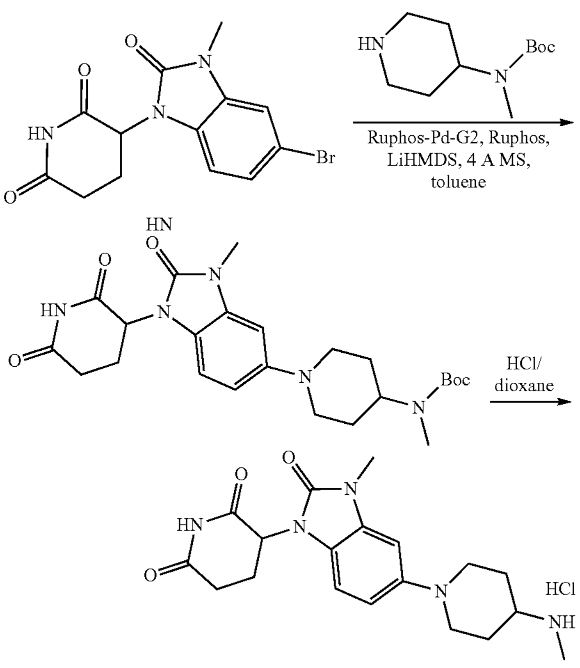

AVX

Step 1—Tert-butyl N-[1-[1-(2,6-dioxo-3-piperidyl)-3-methyl-2-oxo-benzimidazol-5-yl]-4-piperidyl]-N-methyl-carbamate A mixture of 3-(5-bromo-3-methyl-2-oxo-benzimidazol-1-yl)piperidine-2,6-dione (1.00 g, 2.96 mmol, Intermediate HN), tert-butyl N-methyl-N-(4-piperidyl)carbamate (951 mg, 4.44 mmol, CAS #108612-54-0), [2-(2-aminophenyl) phenyl]-chloro-palladium;dicyclohexyl-[2-(2,6-diisopropoxyphenyl)phenyl]phosphane (459 mg, 591 umol), RuPhos (276 mg, 591 umol), LiHMDS (1 M, 17.7 mL) and 4 Å molecular sieves (200 mg) in toluene (10 mL) was degassed and heated at 80° C. for 1 hr under $N_2$ atmosphere. On completion, the mixture was filtered and the filtrate was acidified with FA until the pH=5, then concentrated the mixture in vacuo. The residue was purified by reverse phase (FA) to give the title compound (610 mg, 44% yield) as a yellow solid. $^1H$ NMR (400 MHz, DMSO-$d_6$) δ 11.06 (s, 1H), 6.93 (d, J=8.8 Hz, 1H), 6.85 (d, J=2.0 Hz, 1H), 6.65 (dd, J=2.0, 8.8 Hz, 1H), 5.29 (dd, J=5.2, 12.8 Hz, 1H), 4.01-3.83 (m, 1H), 3.66 (d, J=12.0 Hz, 2H), 3.30 (s, 3H), 2.91-2.83 (m, 1H), 2.74-2.63 (m, 7H), 2.02-1.95 (m, 1H), 1.87-1.74 (m, 2H), 1.68-1.57 (m, 2H), 1.41 (s, 9H).

Step 2—3-[3-Methyl-5-[4-(methylamino)-1-piperidyl]-2-oxo-benzimidazol-1-yl]piperidine-2,6-dione To a solution of tert-butyl N-[1-[1-(2,6-dioxo-3-piperidyl)-3-methyl-2-oxo-benzimidazol-5-yl]-4- piperidyl]-N-methyl-carbamate (100 mg, 212 umol) in DCM (5 mL) was added HCl/dioxane (5 mL). The reaction mixture was stirred at 20° C. for 0.5 hr. On completion, the mixture was concentrated in vacuo to give the title compound (85.0 mg, 98% yield, HCl salt) as a yellow solid. LC-MS (ESI+) m/z 372.1 (M+H)+.

Tert-butyl ((1r,4r)-4-(aminomethyl)cyclohexyl) (methyl)carbamate (Intermediate AVY)

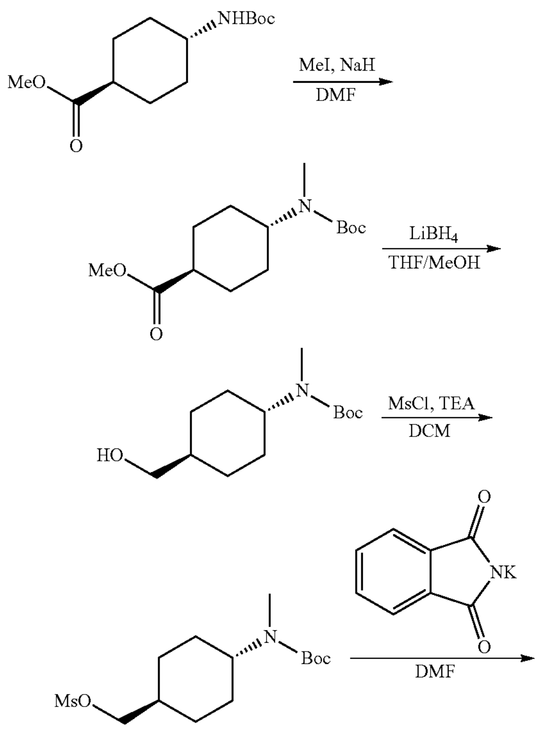

-continued

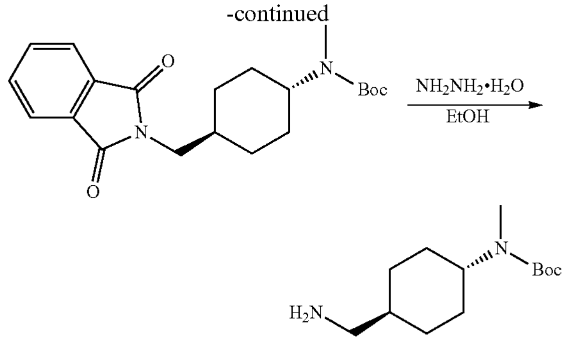

AVY

Step 1—(1R,4r)-methyl 4-((tert-butoxycarbonyl)(methyl)amino)cyclohexanecarboxylate To a solution of methyl 4-(tert-butoxycarbonylamino)cyclohexanecarboxylate (2.00 g, 7.77 mmol, CAS #146307-51-9) in DMF (20 mL) was added NaH (373 mg, 9.33 mmol, 60% dispersion in mineral oil) under 0° C. for 0.5 hr. Then $CH_3I$ (1.32 g, 9.33 mmol, 581 uL) was added to the reaction mixture and the mixture was stirred at 25° C. for 2 hrs. On completion, the reaction mixture was diluted with 100 mL $H_2O$ and extracted with EA (3×50 mL). The combined organic layers were washed with NaCl (50 mL×2), dried over $Na_2SO_4$, filtered and concentrated in vacuo to give a residue. The residue was purified by column chromatography to give the title compound (1.80 g, 85% yield) as yellow oil. $^1H$ NMR (400 MHz, DMSO-$d_6$) δ 3.61-3.54 (m, 3H), 3.17 (d, J=5.3 Hz, 1H), 2.65 (s, 3H), 2.31-2.15 (m, 1H), 2.01-1.88 (m, 2H), 1.62-1.31 (m, 13H).

Step 2—Tert-butyl ((1r,4r)-4-(hydroxymethyl)cyclohexyl)(methyl)carbamate

To a solution of methyl 4-[tert-butoxycarbonyl(methyl)amino]cyclohexanecarboxylate (800 mg, 2.95 mmol) in THE (12 mL) and MeOH (3 mL) was cooled to 0° C. and slowly added $LiBH_4$ (193 mg, 8.84 mmol) under $N_2$ atmosphere. After that, the reaction mixture was warmed to 50° C. and stirred for 2 hours. On completion, the reaction mixture was diluted with 100 mL $H_2O$ and extracted with EA 150 mL (50 mL×3). The combined organic layers were washed with NaCl 100 mL (50 mL×2), dried over $Na_2SO_4$, filtered and concentrated in vacuo to give the title compound (1.00 g, 70% purity, 97% yield) as a yellow solid. $^1H$ NMR (400 MHz, DMSO-$d_6$) δ 4.39 (t, J=5.2 Hz, 1H), 4.11-3.98 (m, 1H), 3.20 (t, J=5.6 Hz, 2H), 2.65 (s, 3H), 1.77 (d, J=11.2 Hz, 2H), 1.65-1.40 (m, 4H), 1.38 (s, 9H), 1.17 (t, J=7.2 Hz, 3H).

Step 3—((1R,4r)-4-((tert-butoxycarbonyl)(methyl)amino)cyclohexyl)methyl methanesulfonate To a solution of tert-butyl N-[4-(hydroxymethyl)cyclohexyl]-N-methyl-carbamate (0.90 g, 3.70 mmol) in DCM (10 mL) was added MsCl (847 mg, 7.40 mmol, 572 uL) and TEA (1.12 g, 11.10 mmol, 1.54 mL). The mixture was stirred at 0° C. for 2 hours. On completion, the reaction mixture was quenched by addition $H_2O$ 50 mL at 0° C., and then extracted with DCM (50 mL×3). The combined organic layers were washed with NaCl (50 mL×2), dried over $Na_2SO_4$, filtered and concentrated in vacuo to give the title compound (1.00 g, 84% yield) as a yellow oil. The crude product was used to the next step directly without further purification.

Step 4—Tert-butyl ((1r,4r)-4-((1,3-dioxoisoindolin-2-yl)methyl)cyclohexyl)(methyl)carbamate To a solution of [4-[tert-butoxycarbonyl(methyl)amino]cyclohexyl]methyl methanesulfonate (1.00 g, 3.11 mmol) in DMF (10 mL) was added (1,3-dioxoisoindolin-2-yl)potassium (1.15 g, 6.22 mmol). The mixture was stirred at 40° C. for 16 hrs. On completion, the reaction mixture was diluted with 100 mL $H_2O$ and extracted with EA (50 mL×3). The combined organic layers were washed with NaCl (50 mL×2), dried over $Na_2SO_4$, filtered and concentrated in vacuo to give a residue. The residue was purified by column chromatography to give the title compound (1.00 g, 84% purity, 72% yield) as a yellow solid. $^1H$ NMR (400 MHz, DMSO-$d_6$) δ 7.90-7.81 (m, 4H), 3.85-3.64 (m, 1H), 3.43 (d, J=7.2 Hz, 2H), 2.62 (s, 3H), 1.71 (d, J=13.2 Hz, 2H), 1.63 (dd, J=3.6, 7.6 Hz, 1H), 1.58-1.42 (m, 3H), 1.38 (s, 9H), 1.26-1.15 (m, 1H), 1.12-0.99 (m, 2H).

Step 5—Tert-butyl ((1r,4r)-4-(aminomethyl)cyclohexyl)(methyl)carbamate

To a solution of tert-butyl N-[4-[(1,3-dioxoisoindolin-2-yl)methyl]cyclohexyl]-N-methyl-carbamate (1.00 g, 2.26 mmol) in EtOH (10 mL) was added $NH_2NH_2.H_2O$ (266 mg, 4.51 mmol, 258 uL, 85% solution). The mixture was stirred at 60° C. for 2 hrs. On completion, the mixture was filtered and the filtrate was concentrated in vacuo to give the title compound (800 mg, 80% purity, 98% yield) as a yellow solid. $^1H$ NMR (400 MHz, DMSO-$d_6$) δ 4.16 (s, 2H), 3.44 (q, J=7.2 Hz, 1H), 2.66-2.62 (m, 3H), 2.42 (d, J=6.4 Hz, 2H), 1.92-1.68 (m, 2H), 1.54 (s, 2H), 1.46-1.39 (m, 2H), 1.38 (s, 9H), 1.27-1.16 (m, 1H), 0.98-0.84 (m, 2H).

2-(2,6-Dioxopiperidin-3-yl)-4-((((1r,4r)-4-(methylamino)cyclohexyl)methyl)amino) isoindoline-1,3-dione (Intermediate AVZ)

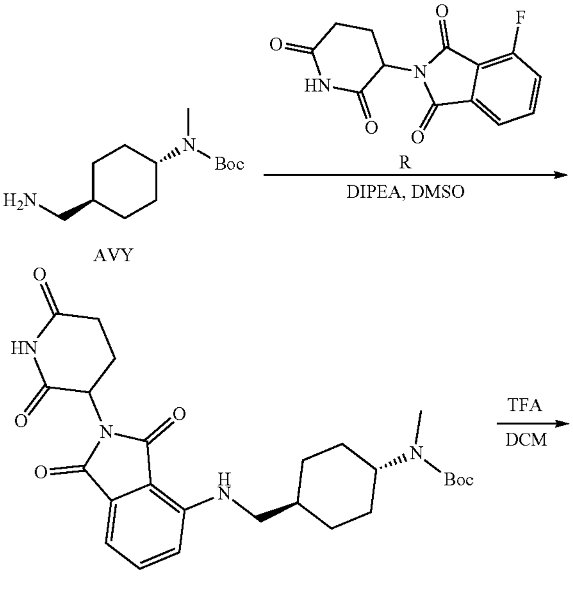

-continued

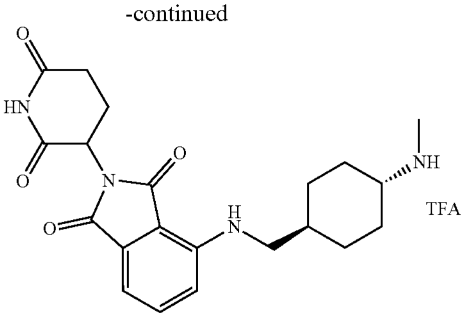

AVZ

Step 1—Tert-butyl ((1r,4r)-4-(((2-(2,6-dioxopiperidin-3-yl)-1,3-dioxoisoindolin-4-yl)amino)methyl)cyclohexyl)(methyl)carbamate To a solution of tert-butyl N-[4-(aminomethyl)cyclohexyl]-N-methyl-carbamate (750 mg, 3.09 mmol, Intermediate AVY) in DMSO (10 mL) was added 2-(2,6-dioxo-3-piperidyl)-4-fluoro-isoindoline-1,3-dione (1.71 g, 6.19 mmol, Intermediate R) and DIPEA (1.20 g, 9.28 mmol, 1.62 mL). The mixture was stirred at 130° C. for 0.5 hr. On completion, the reaction mixture was filtered and concentrated in vacuo to give a residue. The residue was purified by prep-HPLC (FA condition) to give the title compound (300 mg, 18% yield, 95% purity) as yellow oil. LC-MS (ESI$^+$) m/z 499.4 (M+H)$^+$.

Step 2—2-(2,6-Dioxopiperidin-3-yl)-4-((((1r,4r)-4-(methylamino)cyclohexyl)methyl)amino) isoindoline-1,3-dione To a solution of tert-butyl N-[4-[[[2-(2,6-dioxo-3-piperidyl)-1,3-dioxo-isoindolin-4-yl]amino]methyl]cyclohexyl]-N-methyl-carbamate (150 mg, 286 umol) in DCM (1 mL) was added TFA (0.5 mL). The mixture was stirred at 25° C. for 0.5 hr. On completion, the reaction mixture was concentrated in vacuo to give the title compound (150 mg, TFA, 96% yield) as yellow oil. LC-MS (ESI$^+$) m/z 399.4 (M+H)$^+$.

Tert-butyl 4-(((1r,4r)-4-(aminomethyl)cyclohexyl)oxy)piperidine-1-carboxylate (Intermediate AWA)

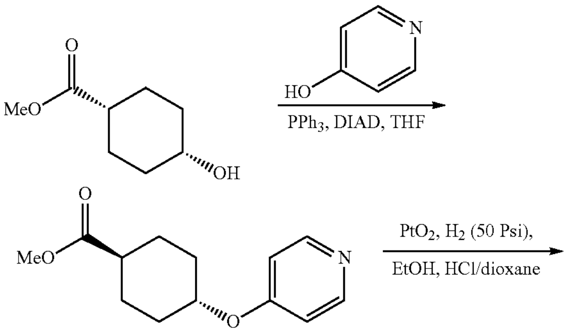

-continued

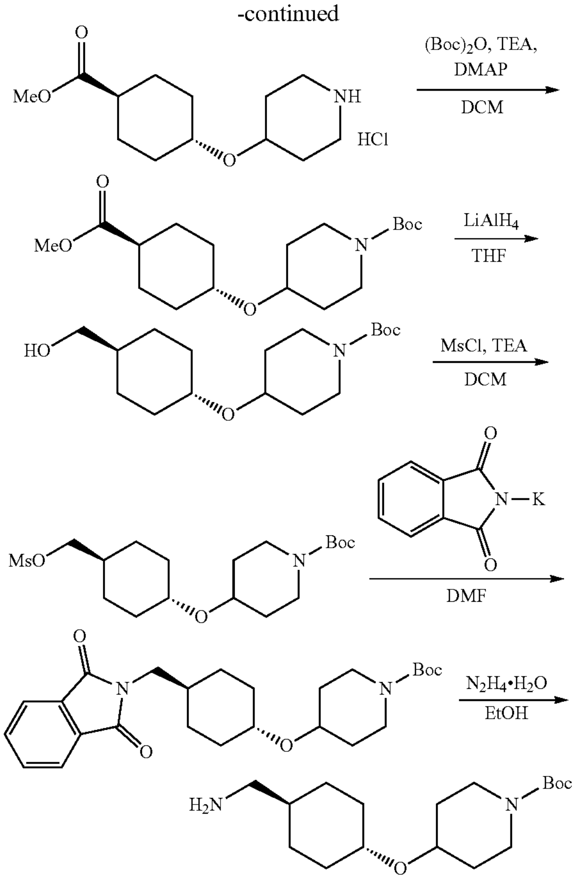

AWA

Step 1—(1R,4r)-Methyl 4-(pyridin-4-yloxy)cyclohexanecarboxylate

To a solution of methyl 4-hydroxycyclohexanecarboxylate (3.00 g, 19.0 mmol, CAS #3618-03-9), pyridin-4-ol (1.80 g, 19.0 mmol, CAS #626-64-2) and $PPh_3$ (7.46 g, 28.5 mmol) in THF (30 mL) was added DIAD (5.75 g, 28.5 mmol) at 0° C. The reaction mixture was stirred at 50° C. for 12 hours. On completion, the reaction mixture was concentrated in vacuo to give a residue. The residue was purified by reverse phase (0.1% $NH_3.H_2O$) to afford a crude product. Then, the crude product was further purified by prep-HPLC (column: Waters Xbridge C18 150*50 mm*10 um; mobile phase: [water (10 mM $NH_4HCO_3$)-ACN]; B %: 22%-52%, 11.5 min) to give the title compound (400 mg, 9% yield) as a white solid. $^1$H NMR (400 MHz, DMSO-$d_6$) δ 8.35 (d, J=4.0 Hz, 2H), 6.96 (d, J=4.4 Hz, 2H), 4.55-4.40 (m, 1H), 3.61 (s, 3H), 2.43-2.35 (m, 1H), 2.13-2.04 (m, 2H), 2.00-1.90 (m, 2H), 1.65-1.50 (m, 2H), 1.48-1.35 (m, 2H).

Step 2—(1R,4r)-Methyl 4-(piperidin-4-yloxy)cyclohexanecarboxylate hydrochloride

To a solution of methyl 4-(4-pyridyloxy)cyclohexanecarboxylate (350 mg, 1.49 mmol) in EtOH (20 mL) was added HCl/dioxane (4 M, 1.49 mL). The reaction mixture was stirred at 20° C. for 0.5 hour. Then $PtO_2$ (405 mg, 1.79 mmol) was added to the reaction mixture and the mixture was degassed and purged with $H_2$ for 3 times. The mixture was stirred under $H_2$ (50 Psi) at 40° C. for 15.5 hours. On completion, the reaction mixture was filtered and the filtrate was concentrated in vacuo to give the title compound (350 mg, 95% yield, HCl salt) as a white solid. $^1H$ NMR (400 MHz, DMSO-$d_6$) δ 9.10-8.80 (m, 2H), 3.74-3.65 (m, 1H), 3.61-3.55 (m, 3H), 3.17-3.04 (m, 2H), 3.02-2.85 (m, 3H), 1.95-1.82 (m, 5H), 1.75-1.50 (m, 4H), 1.43-1.30 (m, 2H), 1.20-1.10 (m, 2H).

Step 3—Tert-butyl 4-(((1r,4r)-4-(methoxycarbonyl) cyclohexyl)oxy)piperidine-1-carboxylate To a solution of methyl 4-(4-piperidyloxy)cyclohexanecarboxylate (350 mg, 1.26 mmol, HCl salt) in EtOH (20 mL) was added TEA (637 mg, 6.30 mmol), DMAP (308 mg, 2.52 mmol) and $Boc_2O$ (550 mg, 2.52 mmol). The reaction mixture was stirred at 20° C. for 12 hours. On completion, the reaction mixture was concentrated in vacuo to give a residue, which was diluted with water (20 mL) and extracted with EtOAc (3×20 mL). The combined organic layers were washed with water (2×20 mL) and brine (10 mL), dried over $Na_2SO_4$, filtered and concentrated in vacuo to give the title compound (430 mg, 99% yield) as a yellow solid. The crude product was used to the next step directly.

Step 4—Tert-butyl 4-(((1r,4r)-4-(hydroxymethyl) cyclohexyl)oxy)piperidine-1-carboxylate To a solution of tert-butyl 4-(4-methoxycarbonylcyclohexoxy)piperidine-1-carboxylate (430 mg, 1.26 mmol) in THF (20 mL) was added $LiAlH_4$ (57.4 mg, 1.51 mmol) at 0° C. and the mixture was stirred at 0° C. for 2 hours. On completion, the reaction mixture was quenched with water (0.4 mL) at 20° C., and then filtered and concentrated in vacuo to give a residue. The residue was purified by flash silica gel chromatography (ISCO®; 12 g SepaFlash® Silica Flash Column, Eluent of 10-80% Ethyl acetate/Petroleum ether gradient @ 30 mL/min) to afford the title compound (245 mg, 62% yield) as a white solid. $^1H$ NMR (400 MHz, $CDCl_3$) δ 4.73-4.63 (m, 2H), 3.77-3.67 (m, 2H), 3.55-3.45 (m, 1H), 3.38 (d, J=6.0 Hz, 2H), 3.28-3.18 (m, 1H), 3.01-2.91 (m, 2H), 1.96-1.88 (m, 2H), 1.82-1.74 (m, 2H), 1.45-1.35 (m, 12H), 1.25-1.13 (m, 2H), 0.98-0.85 (m, 2H).

Step 5—Tert-butyl 4-(((1r,4r)-4-(((methylsulfonyl) oxy)methyl)cyclohexyl)oxy)piperidine-1- carboxylate To a solution of tert-butyl 4-[4-(hydroxymethyl)cyclohexoxy]piperidine-1-carboxylate (230 mg, 734 umol) and TEA (149 mg, 1.47 mmol) in DCM (5.0 mL) was added MsCl (101 mg, 881 umol) at 0° C. The reaction mixture was stirred at 20° C. for 1 hour. On completion, the reaction mixture was diluted with water (10 mL) and extracted with DCM (3×10 mL). The combined organic layers were washed with water (2×10 mL) and brine (10 mL), dried over $Na_2SO_4$, filtered and concentrated in vacuo to afford the title product (245 mg, 85% yield) as a white solid. $^1H$ NMR (400 MHz, DMSO-$d_6$) δ 4.04 (d, J=6.4 Hz, 2H), 3.87-3.74 (m, 2H), 3.60-3.52 (m, 1H), 3.35-3.25 (m, 1H), 3.08-2.98 (m, 5H), 2.05-1.98 (m, 2H), 1.90-1.83 (m, 2H), 1.81-1.68 (m, 3H), 1.52-1.42 (m, 11H), 1.32-1.22 (m, 2H), 1.13-1.03 (m, 2H).

Step 6—Tert-butyl 4-(((1r,4r)-4-((1,3-dioxoisoindolin-2-yl)methyl)cyclohexyl)oxy)piperidine-1- carboxylate A mixture of tert-butyl 4-[4-(methylsulfonyloxyethyl)cyclohexoxy]piperidine-1-carboxylate (230 mg, 587 umol) and (1,3-dioxoisoindolin-2-yl)potassium (218 mg, 1.17 mmol, CAS #1074-82-4) in DMF (6.0 mL) was stirred at 100° C. for 12 hours. On completion, the reaction mixture was quenched with water (30 mL), and then filtered. The filter cake was dried in vacuo to afford the title product (210 mg, 81% yield) as a white solid. $^1H$ NMR (400 MHz, DMSO-$d_6$) δ 7.90-7.81 (m, 4H), 3.65-3.52 (m, 3H), 3.42 (d, J=6.8 Hz, 2H), 3.31-3.25 (m, 1H), 3.04-2.92 (m, 2H), 1.92-1.85 (m, 2H), 1.75-1.60 (m, 5H), 1.38 (s, 9H), 1.30-1.19 (m, 2H), 1.13-0.95 (m, 4H).

Step 7—Tert-butyl 4-(((1r,4r)-4-(aminomethyl)cyclohexyl)oxy)piperidine-1-carboxylate A mixed solution of tert-butyl 4-[4-[(1,3-dioxoisoindolin-2-yl)methyl]cyclohexoxy]piperidine -1-carboxylate (200 mg, 452 umol), $NH_2NH_2.H_2O$ (226 mg, 4.52 mmol) in EtOH (20 mL) was stirred at 80° C. for 1 hour. On completion, the reaction mixture was filtered and concentrated in vacuo to give a residue. The residue was diluted with DCM (20 mL), and then filtered. The filtrate was concentrated in vacuo to afford the title product (110 mg, 78% yield) as colorless oil. $^1H$ NMR (400 MHz, DMSO-$d_6$) δ 4.86 (s, 2H), 3.77-3.67 (m, 2H), 3.53-3.45 (m, 1H), 3.28-3.18 (m, 1H), 3.00-2.90 (m, 2H), 1.95-1.87 (m, 2H), 1.78-1.68 (m, 7H), 1.45-1.40 (m, 1H), 1.38 (s, 9H), 1.22-1.18 (m, 1H), 0.87-0.80 (m, 1H).

2-(2,6-Dioxopiperidin-3-yl)-4-((((1r,4r)-4-(piperidin-4-yloxy)cyclohexyl)methyl)amino) isoindoline-1,3-dione hydrochloride (Intermediate AWB)

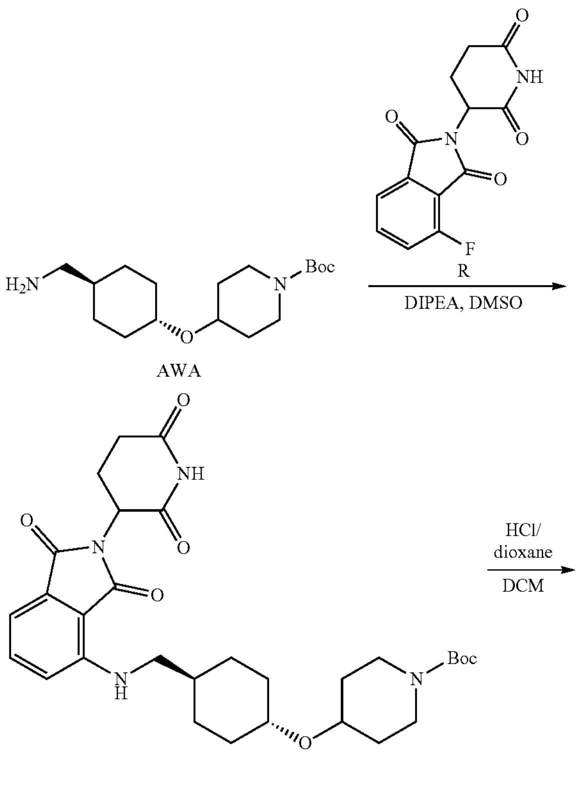

-continued

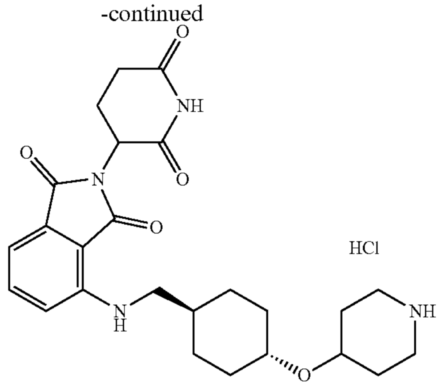

AWB 2-(2,6-Dioxo-3-piperidyl)-4-[4-(methylamino)-1-piperidyl]isoindoline-1,3-dione (Intermediate AWC)

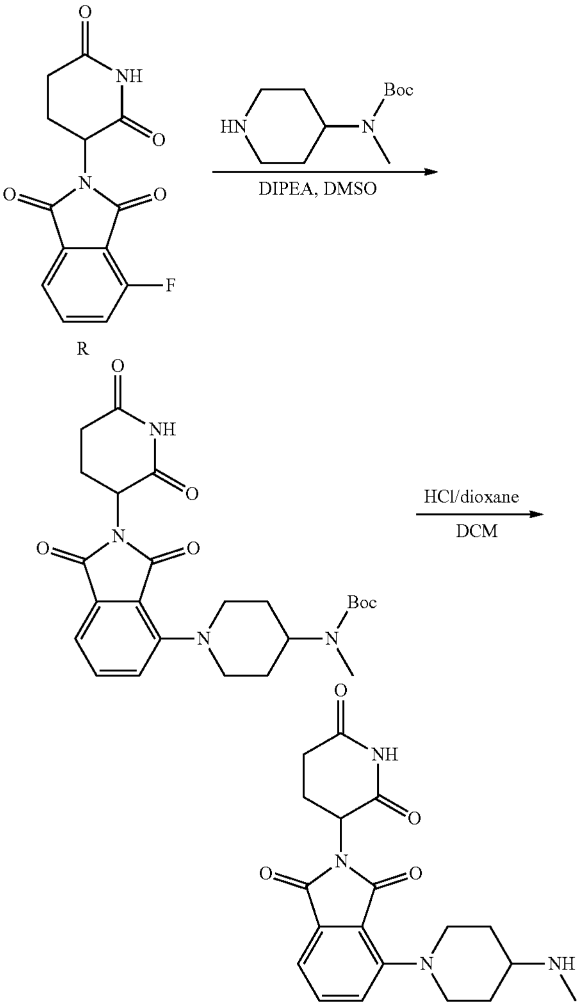

AWC

Step 1—Tert-butyl 4-(((r,4r)-4((2-(2,6-dioxopiperidin-3-yl)-1,3-dioxoisoindolin-4-yl)amino)methyl) cyclohexyl)oxy)piperidine-1l-carboxylate To a solution of 2-(2,6-di oxo-3-piperidyl)-4-fluoro-isoindoline- 1, 3-di one (90.0 mg, 326 umol, Intermediate R) and tert-butyl 4-[4-(aminomethyl)cyclohexoxy]piperidine-1l-carboxylate (102 mg, 326 umol, Intermediate AWA) in DMSO (1.0 mL) was added DIPEA (211 mg, 1.63 mmol). The reaction mixture was stirred at 130° C. for 2 hours. On completion, the reaction mixture was quenched with $H_2O$ (0.2 mL) and then concentrated in vacuo to give a residue. The residue was purified by prep-HPLC (FA condition: column: Phenomenex Synergi C18 150*25*10 um; mobile phase: [water (0.225% FA)-ACN]; B %: 51%-81%, 10 min) to afford the title compound (78.0 mg, 42% yield) as a yellow solid. $^1H$ NMR (400 MHz, DMSO-$d_6$) δ 11.09 (s, 1H), 7.58 (dd, J=8.4, 7.2 Hz, 1H), 7.12 (d, J=8.8 Hz, 1H), 7.02 (d, J=6.8 Hz, 1H), 6.61-6.53 (m, 1H), 5.05 (dd, J=12.8, 5.2 Hz, 1H), 3.67-3.54 (m, 3H), 3.17 (t, J=6.4 Hz, 2H), 3.05-2.83 (m, 3H), 2.63-2.55 (m, 2H), 2.07-1.99 (m, 3H), 1.97-1.90 (m, 2H), 1.82-1.68 (m, 4H), 1.59-1.49 (m, 1H), 1.39 (s, 9H), 1.33-1.23 (m, 2H), 1.15-1.10 (m, 4H).

Step 2—2-(2,6-Dioxopiperidin-3-yl)-4-((((1r,4r)-4-(piperidin-4-yloxy)cyclohexyl)methyl)amino) isoindoline-1,3-dione hydrochloride To a solution of tert-butyl 4-[4-[[[2-(2,6-dioxo-3-piperidyl)-1,3-dioxo-isoindolin-4-yl]amino]methyl]cyclohexoxy]piperidine-1-carboxylate (75.0 mg, 132 umol) in DCM (5.0 mL) was added HCl/dioxane (4 M, 1.0 mL). The reaction mixture was stirred at 20° C. for 0.2 hour. On completion, the reaction mixture was concentrated in vacuo to the title product (66.0 mg, 95% yield, HCl salt) as a green solid. LC-MS ($ESI^+$) m/z 468.1 $(M+H)^+$.

Step 1—Tert-butyl N-[1-[2-(2,6-dioxo-3-piperidyl)-1,3-dioxo-isoindolin-4-yl]-4-piperidyl]-N— methyl-carbamate To a solution of 2-(2,6-dioxo-3-piperidyl)-4-fluoro-isoindoline-1,3-dione (3.00 g, 10.8 mmol, Intermediate R) and tert-butyl N-methyl-N-(4-piperidyl)carbamate (2.12 g, 9.87 mmol, CAS #108612-54-0) in DMSO (30.0 mL) was added DIPEA (6.38 g, 49.3 mmol, 8.60 mL). The mixture was stirred at 130° C. for 3 hrs. On completion, the reaction mixture was diluted with $H_2O$ (200 mL), and extracted with EA (3×200 mL). The combined organic layers were washed with brine (3×300 mL), dried over $Na_2SO_4$, filtered and concentrated in vacuo to give a residue. The residue was purified by re-crystallization from $H_2O$ (20 mL) to give the title compound (4.40 g, 94% yield) as a yellow solid. $^1H$ NMR (400 MHz, DMSO-$d_6$) δ 11.09 (s, 1H), 7.69 (t, J=8.4 Hz, 1H), 7.42-7.26 (m, 2H), 5.10 (dd, J=5.2, 12.8 Hz, 1H), 4.12-3.86 (m, 1H), 3.76 (d, J=11.2 Hz, 2H), 2.98-2.81 (m, 3H), 2.71 (s, 3H), 2.64-2.53 (m, 2H), 2.09-1.99 (m, 1H), 1.97-1.82 (m, 2H), 1.66 (s, 2H), 1.41 (s, 9H). LC-MS (ESI$^+$) m/z 471.4 (M+H)$^+$.

Step 2—2-(2,6-Dioxo-3-piperidyl)-4-[4-(methylamino)-1-piperidyl]isoindoline-1,3-dione To a solution of tert-butyl N-[1-[2-(2,6-dioxo-3-piperidyl)-1,3-dioxo-isoindolin-4-yl]-4-piperidyl]- N-methyl-carbamate (70.0 mg, 148 umol) in DCM (1.00 mL) was added HCl/dioxane (4 M, 1.00 mL). The mixture was stirred at 20° C. for 1 hr. On completion, the reaction mixture was concentrated in vacuo to give the title compound (60.0 mg, 99% yield, HCl salt) as a yellow solid. LC-MS (ESI$^+$) m/z 371.4 (M+H)$^+$.

2-(2,6-Dioxo-3-piperidyl)-5-[[3-[3-(methylamino)propoxy]cyclobutyl]amino]isoindoline-1,3-dione (Intermediate AWD)

7.49-7.19 (m, 6H), 6.81 (s, 1H), 6.75 (d, J=7.6 Hz, 1H), 5.13-4.96 (m, 3H), 4.14-3.89 (m, 2H), 3.33-3.27 (m, 4H), 2.92-2.81 (m, 4H), 2.63-2.53 (m, 2H), 2.37-2.25 (m, 2H), 2.19-2.06 (m, 2H), 2.04-1.94 (m, 1H), 1.77-1.66 (m, 2H); LC-MS (ESI$^+$) m/z 549.2 (M+H)$^+$.

Step 2—2-(2,6-Dioxo-3-piperidyl)-5-[[3-[3-(methylamino)propoxy]cyclobutyl]amino]isoindoline-1,3-dione To a solution of benzyl N-[3-[3-[[2-(2,6-dioxo-3-piperidyl)-1,3-dioxo-isoindolin-5-yl]amino]cyclobutoxy]propyl]-N-methyl-carbamate (90.0 mg, 164 umol) in DCM (1 mL) was added HBr/HOAc (71.3 umol, 0.5 mL, 33% solution). The reaction mixture was stirred at 25° C. for 1 hr. On completion, the reaction mixture was concentrated in vacuo to give the title compound (80.0 mg, 98.4% yield, HBr salt) as a yellow solid. LC-MS (ESI$^+$) m/z 415.3 (M+H)$^+$.

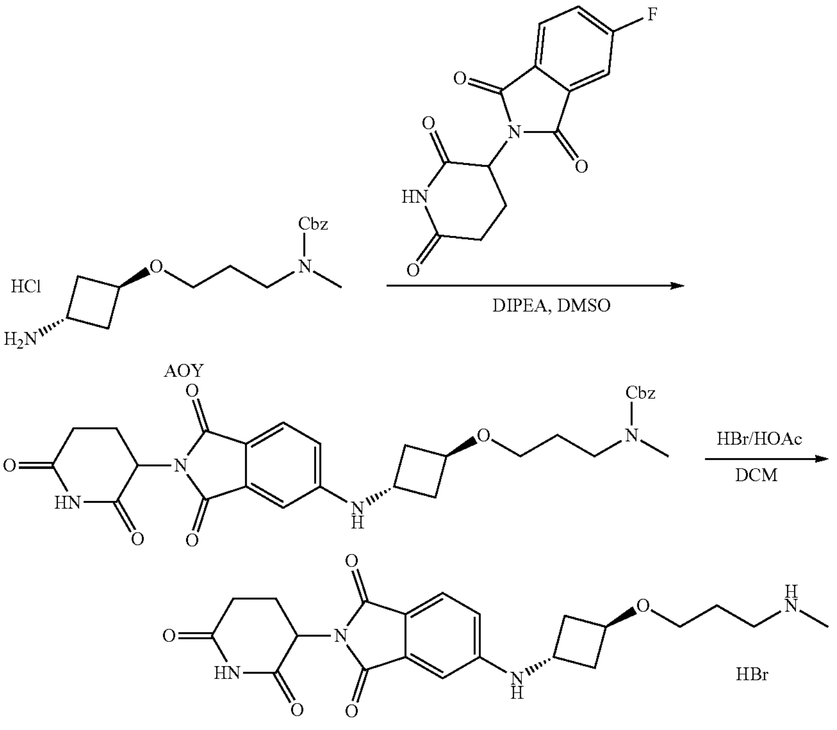

AWD

Step 1—Benzyl N-[3-[3-[[2-(2,6-dioxo-3-piperidyl)-1,3-dioxo-isoindolin-5-yl]amino]cyclobutoxy]propyl]-N-methyl-carbamate To a solution of benzyl N-[3-(3-aminocyclobutoxy)propyl]-N-methyl-carbamate (350 mg, 1.06 mmol, HCl, Intermediate AOY) and 2-(2,6-dioxo-3-piperidyl)-5-fluoro-isoindoline-1,3-dione (294 mg, 1.06 mmol, CAS #1160247-15-3) in DMSO (5 mL) was added DIPEA (550 mg, 4.26 mmol, 741 uL), and the reaction mixture was stirred at 130° C. for 3 hrs. On completion, the mixture was concentrated in vacuo to give a residue. The residue was purified by reverse phase (0.1% FA condition) to give the title compound (90 mg, 15.4% yield) as a yellow solid. 1H NMR (400 MHz, DMSO-$d_6$) δ 11.06 (s, 1H), 7.58 (d, J=8.4 Hz, 1H), 6-(2-Fluoropropan-2-yl)picolinamide (Intermediate AWE)

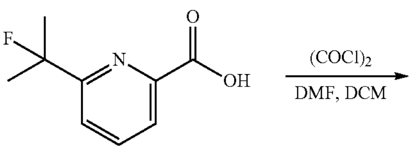

ARA

-continued

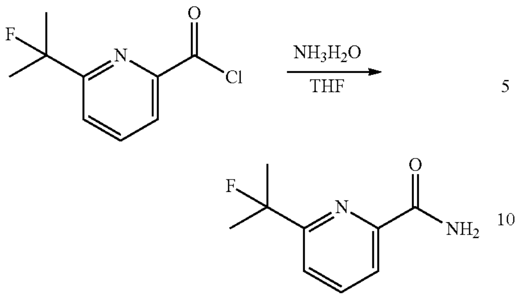

AWE

Step 1—6-(2-Fluoropropan-2-yl)picolinoyl chloride

To a solution of 6-(1-fluoro-1-methyl-ethyl)pyridine-2-carboxylic acid (300 mg, 1.64 mmol, Intermediate ARA) in DCM (3 mL) was added DMF (11.9 mg, 163 umol) and $(COCl)_2$ (415 mg, 3.28 mmol) at 0° C. The mixture was stirred at 25° C. for 0.5 hours. On completion, the reaction mixture concentrated under reduced pressure to afford the title compound (330 mg, 100% yield) as a brown solid. The crude product was used to the next step directly.

Step 2—6-(2-Fluoropropan-2-yl )picolinamide

A solution of 6-(1-fluoro-1-methyl-ethyl)pyridine-2-carbonyl chloride (330 mg, 1.64 mmol) in THF (3 mL) was added dropwise to $NH_3.H_2O$ (14.0 M, 1.17 mL). The mixture was stirred at 25° C. for 0.5 hours. On completion, the reaction mixture was diluted with $H_2O$ (20 mL) and extracted with EA (3x20 mL). The combined organic layers were washed with brine (20 mL), dried over $Na_2SO_4$, filtered and concentrated under reduced pressure to afford the title compound (237 mg, 62% purity, 79% yield) as a brown solid. LC-MS ($ESI^+$) m/z 183.2 $(M+H)^+$.

6-(2-Fluoropropan-2-yl)-N-(2-((1r,4r)-4-formylcyclohexyl)-6-methoxy-2H-indazol-5-yl) picolinamide (Intermediate AWF)

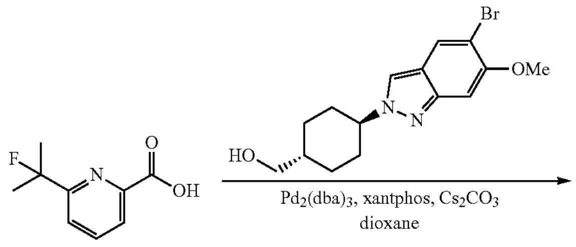

AWE

-continued

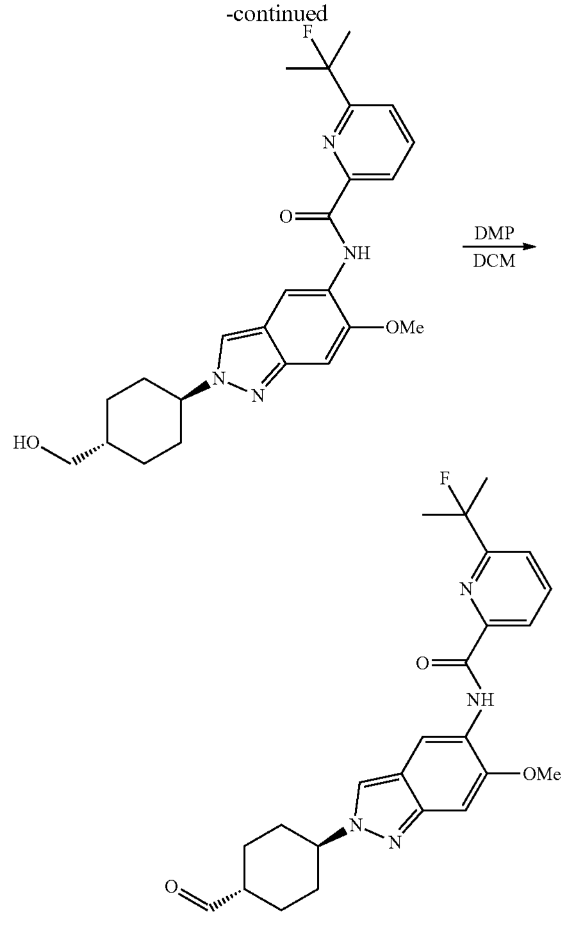

AWF

Step 1—6-(2-Fluoropropan-2-yl)-N-(2-((1r,4r)-4-(hydroxymethyl)cyclohexyl)-6-methoxy-2H-indazol-5-yl)picolinamide To a solution of [4-(5-bromo-6-methoxy-indazol-2-yl) cyclohexyl]methanol (300 mg, 884 mmol, synthesized via Steps 1-3 of Intermediate ATE) in dioxane (5 mL) was added $Pd_2(dba)_3$ (80.9 mg, 88.4 mmol), 6-(1-fluoro-1-methyl-ethyl)pyridine-2-carboxamide (193 mg, 1.06 umol, Intermediate AWE), $Cs_2CO_3$ (576 mg, 1.77 mmol) and Xantphos (102 mg, 176 mmol). The mixture was stirred at 80° C. for 12 hours. On completion, the reaction mixture was partitioned between $H_2O$ (20 mL) and EA (60 mL). The organic phase was separated, washed with brine (20 mL), dried over $Na_2SO_4$, filtered and concentrated under reduced pressure to give a residue. The residue was purified by column chromatography ($SiO_2$, DCM:MeOH=20:1) to give the title compound (390 mg, 80% yield, 80% purity) as an off-white solid. LC-MS ($ESI^+$) m/z 441.4 $(M+H)^+$.

Step 2—6-(2-Fluoropropan-2-yl)-N-(2-((1r,4r)-4-formylcyclohexyl)-6-methoxy-2H-indazol-5-yl) picolinamide To a solution of 6-(1-fluoro-1-methyl-ethyl)-N-[2-[4-(hydroxymethyl)cyclohexyl]-6-methoxy-indazol-5-yl]pyridine-2-carboxamide (390 mg, 885 umol) in DCM (4 mL) was added DMP (450 mg, 1.06 mmol). The mixture was stirred at 25° C. for 0.5 hours. On completion, the reaction mixture was quenched by addition $Na_2S_2O_3$ (10 mL) and $NaHCO_3$ (10 mL) at 0° C., and then diluted with $H_2O$ (20 mL) and extracted with DCM (3*20 mL). The combined organic layers were washed with brine (20 mL), dried over $Na_2SO_4$, filtered and concentrated under reduced pressure to give the title compound (390 mg, 80% yield, 80% purity) as a white solid. LC-MS ($ESI^+$) m/z 439.2 $(M+H)^+$.

N-(6-(2-hydroxypropan-2-yl)-2-(3-oxopropyl)-2H-indazol-5-yl)-6-(trifluoromethyl)picolinamide (Intermediate AWG)

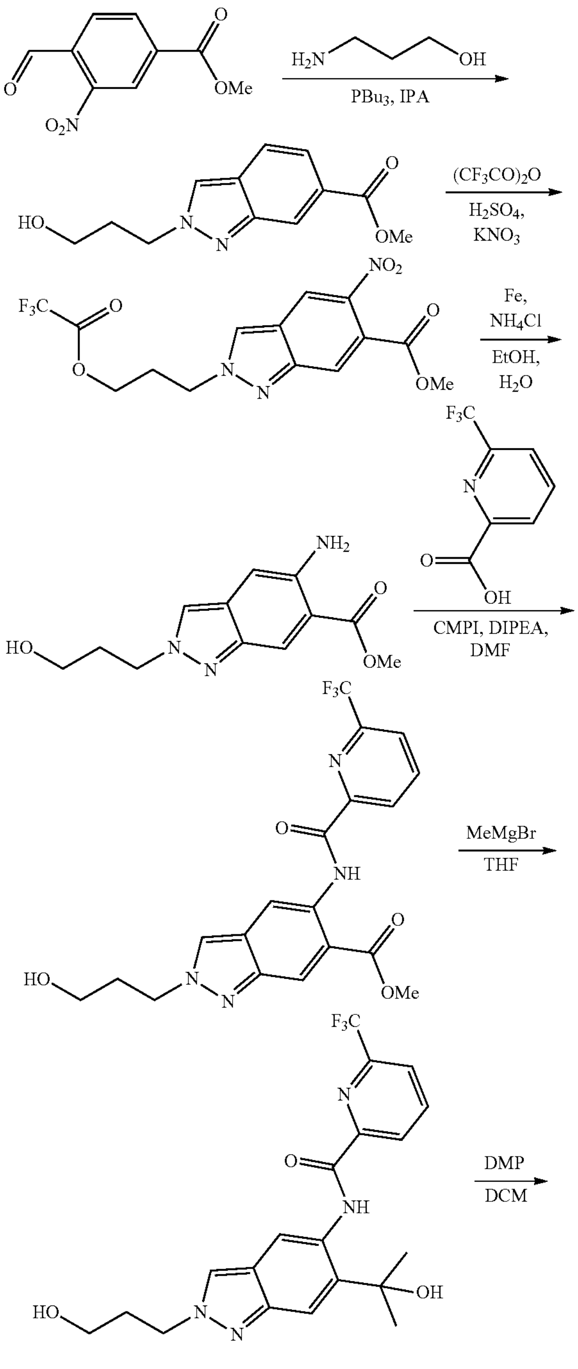

-continued

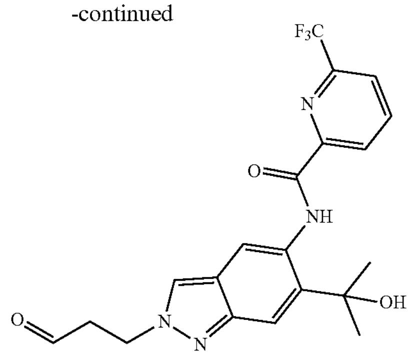

AWG

Step 1—Methyl 2-(3-hydroxypropyl)-2H-indazole-6-carboxylate

A mixture of methyl 4-formyl-3-nitro-benzoate (5.00 g, 23.9 mmol, CAS #153813-69-5) and 3-aminopropan-1-ol (1.98 g, 26.3 mmol, CAS #153-87-6) in IPA (50.0 mL) was stirred at 80° C. for 3 hours. After completed, the mixture was cooled to 25° C., tributylphosphane (14.5 g, 71.7 mmol) was added. The mixture and stirred at 80° C. for 12 hours. On completion, the reaction mixture was concentrated in vacuo to give a residue. The residue was purified by column chromatography ($SiO_2$, Petroleum ether/Ethyl acetate=100/1 to 1/1) to give the title compound (7.80 g, 78% yield) as brown oil. LC-MS ($ESI^+$) m/z 235.1 $(M+H)^+$.

Step 2—Methyl 5-nitro-2-(3-(2,2,2-trifluoroacetoxy)propyl)-2H-indazole-6-carboxylate A solution of methyl 2-(3-hydroxypropyl) indazole-6-carboxylate (6.80 g, 29.0 mmol) in TFAA (30.4 g, 145 mmol) at 25° C. was stirred for 2 hours. Then a solution of $KNO_3$ (6.21 g, 61.4 mmol) in $H_2SO_4$ (14.2 g, 145 mmol) was added dropwise to the above mixture at −5° C. The mixture was stirred at 25° C. for 1 hour. On completion, the reaction mixture was poured into ice-water (100 mL) and extracted with EA (3×100 mL). The combined organic phase was washed with brine (50 mL), dried over $Na_2SO_4$, filtered and concentrated in vacuo to give the residue. The residue was purified by column chromatography ($SiO_2$, Petroleum ether/Ethyl acetate=100/1 to 1/1) to give the title compound (5.30 g, 27% yield) as a yellow solid. $^1H$ NMR (400 MHz, $CDCl_3$) δ 8.42 (s, 1H), 8.23 (s, 1H), 8.04 (s, 1H), 4.64 (m, 2H), 4.40 (m, 2H), 3.94 (s, 3H), 2.55 (m, J=6.4 Hz, 2H); LC-MS ($ESI^+$) m/z 376.2 $(M+H)^+$.

Step 3—Methyl 5-amino-2-(3-hydroxypropyl)-2H-indazole-6-carboxylate

To a solution of methyl 5-nitro-2-[3-(2, 2, 2-trifluoroacetyl)oxypropyl]indazole-6-carboxylate (5.30 g, 14.1 mmol) in a mixed solvent of EtOH (60 mL) and $H_2O$ (20 mL) was added $NH_4Cl$ (3.78 g, 70.6 mmol) and Fe (3.94 g, 70.6 mmol). The mixture was stirred at 80° C. for 2 hours. On completion, the reaction mixture was concentrated in vacuo to give a residue. The residue was diluted with $H_2O$ (100 mL) and extracted with EA (3×100 mL). The combined organic layers were washed with brine (50 mL), dried over $Na_2SO_4$, filtered and concentrated in vacuo to give the title compound (3.30 g, 93% yield) as black brown oil. LC-MS ($ESI^+$) m/z 250.2 $(M+H)^+$.

Step 4—Methyl 2-(3-hydroxypropyl)-5-(6-(trifluoromethyl)picolinamido)-2H-indazole-6-carboxylate To a solution of methyl 5-amino-2-(3-hydroxypropyl) indazole-6-carboxylate (1.20 g, 4.81 mmol) and 6-(trifluoromethyl)pyridine-2-carboxylic acid (920 mg, 4.81 mmol, CAS #131747-42-7) in DMF (5 mL) was added CMPI (1.60 g, 6.26 mmol) and DIPEA (1.87 g, 14.4 mmol). The mixture was stirred at 25° C. for 0.5 hour. On completion, the reaction mixture was concentrated in vacuo to give a residue. The residue was diluted with $H_2O$ (50 mL) and extracted with EA (3×50 mL). The combined organic layers were washed with brine (50 mL), dried over $Na_2SO_4$, filtered and concentrated in vacuo to give a residue. The residue was purified by column chromatography ($SiO_2$, DCM:MeOH=100:1 to 20:1) to give the title compound (1.70 g, 61% yield) as a yellow solid. LC-MS ($ESI^+$) m/z 423.3 $(M+H)^+$.

Step 5—N-(6-(2-hydroxypropan-2-yl)-2-(3-hydroxypropyl)-2H-indazol-5-yl)-6-(trifluoromethyl) picolinamide To a solution of methyl 2-(3-hydroxypropyl)-5-[[6-(trifluoromethyl)pyridine-2-carbonyl]amino]indazole-6-carboxylate (1.60 g, 3.79 mmol) in THE (30 mL) was dropwise added MeMgBr (3.00 M, 12.6 mL). The mixture was stirred at 0° C. for 0.5 hour. On completion, the reaction mixture was quenched with sat. $NH_4Cl$ aqueous (100 mL) at 0° C., and then extracted with DCM (3×50 mL). The combined organic layers were washed with brine (50 mL), dried over $Na_2SO_4$, filtered and concentrated in vacuo to give a residue. The residue was purified by column chromatography ($SiO_2$, DCM:MeOH=100:1 to 10:1) to give the title compound (1.10 g, 68% yield) as a yellow solid. 1H NMR (400 MHz, $CDCl_3$) δ 12.22 (s, 1H), 8.77 (s, 1H), 8.42 (d, J=7.8 Hz, 1H), 8.03 (t, J=7.8 Hz, 1H), 7.84 (s, 1H), 7.76 (m, 1H), 7.61 (s, 1H), 4.51 (t, J=6.4 Hz, 2H), 3.58 (t, J=5.7 Hz, 2H), 2.50-2.28 (m, 1H), 2.12 (m, 2H), 1.72 (s, 6H); LC-MS ($ESI^+$) m/z 423.1 $(M+H)^+$.

Step 6—N-(6-(2-hydroxypropan-2-yl)-2-(3-oxopropyl)-2H-indazol-5-yl)-6-(trifluoromethyl)picolinamide To a solution of N-[6-(1-hydroxy-1-methyl-ethyl)-2-(3-hydroxypropyl)indazol-5-yl]-6-(trifluoro methyl)pyridine-2-carboxamide (200 mg, 473 umol) in DCM (5 mL) was added DMP (240 mg, 568 umol). The mixture was stirred at 25° C. for 0.5 hour. On completion, the reaction mixture was quenched with sat.$Na_2S_2O_3$ (20 mL) and sat. $NaHCO_3$ (20 mL) at 0° C., and then extracted with DCM (3×50 mL). The combined organic layers were washed with brine (50 mL), dried over $Na_2SO_4$, filtered and concentrated in vacuo to give the title compound (170 mg, 85% yield) as a yellow solid. LC-MS ($ESI^+$) m/z 421.4 $(M+H)^+$.

Tert-butyl (2-aminospiro[3.5]nonan-7-yl)(methyl) carbamate (Intermediate AWH)

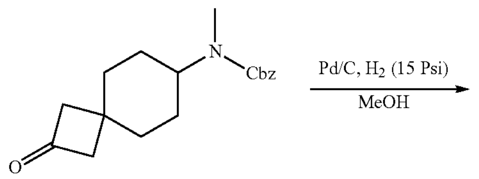

-continued

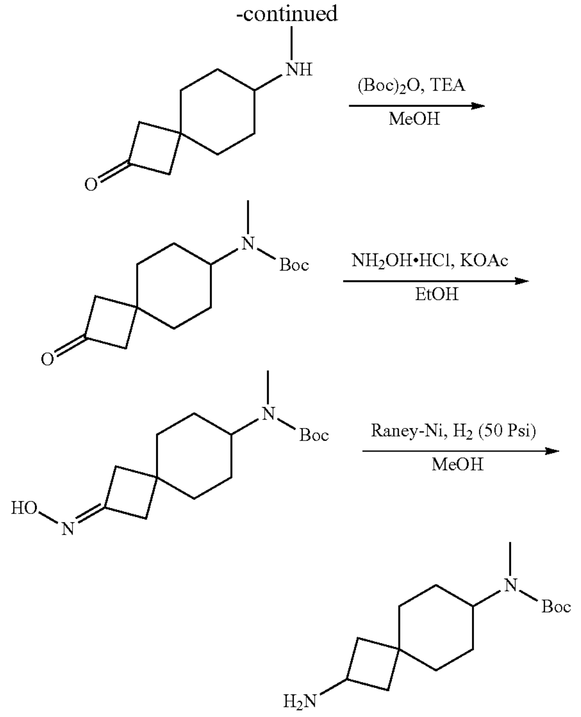

AWH

Step 1—7-(Methylamino)spiro[3.5]nonan-2-one

To a solution of benzyl N-methyl-N-(2-oxospiro[3.5] nonan-7-yl)carbamate (0.40 g, 1.33 mmol, synthesized via Steps 1-5 of Intermediate ANJ) in MeOH (10 mL) was added Pd/C (0.10 g, 10 wt %) under $N_2$ atmosphere. The suspension was degassed and purged with $H_2$ for 3 times. The mixture was stirred at 20° C. for 6 hours under $H_2$ (15 Psi). On completion, the reaction mixture was concentrated in vacuo to give the title compound (0.22 g, 100% yield) as colorless oil.

Step 2—Tert-butyl methyl(2-oxospiro[3.5]nonan-7-yl)carbamate

To a solution of 7-(methylamino)spiro[3.5]nonan-2-one (0.22 g, 1.32 mmol) in MeOH (5 mL) was added $(Boc)_2O$ (574 mg, 2.63 mmol), TEA (399 mg, 3.95 mmol). The reaction mixture was stirred at 40° C. for 12 hours. On completion, the reaction mixture was diluted with water (5 mL), and extracted with EtOAc (5 mL×3). The combined organic layers were washed with brine (5 mL×2), dried over $Na_2SO_4$, filtered and concentrated in vacuo to give the title compound (0.23 g, 65% yield) as a yellow oil. $^1$H NMR (400 MHz, $CDCl_3$) δ 4.01-3.74 (m, 1H), 2.72-2.68 (m, 4H), 2.67-2.63 (m, 3H), 1.70-1.60 (m, 6H), 1.41-1.37 (m, 11H).

Step 3—Tert-butyl (2-(hydroxyimino)spiro[3.5] nonan-7-yl)(methyl)carbamate

A mixture solution of tert-butyl N-methyl-N-(2-oxospiro [3.5]nonan-7-yl)carbamate (0.20 g, 748 umol), $NH_2OH$ HCl (260 mg, 3.74 mmol) and KOAc (367 mg, 3.74 mmol) in EtOH (5 mL) was stirred at 80° C. for 12 hrs. On completion, the reaction mixture was diluted with water (15 mL) and extracted with EtOAc (10 mL×3). The combined organic layers were washed with brine (10 mL×2), dried over $Na_2SO_4$, filtered and concentrated in vacuo to give the title compound (0.20 g, 94% yield) as a yellow solid.

Step 4—Tert-butyl (2-aminospiro[3.5]nonan-7-yl)(methyl)carbamate

To a solution of tert-butyl N-(2-hydroxyiminospiro[3.5]nonan-7-yl)-N-methyl-carbamate (0.20 g, 708 umol) in MeOH (10 mL) was added Raney-Ni (6.07 mg, 70.8 umol) under $N_2$ atmosphere. The suspension was degassed and purged with $H_2$ for 3 times. The mixture was stirred at 50° C. for 12 hours under $H_2$ (50 Psi). On completion, the reaction mixture was filtered and concentrated in vacuo to afford the title product (0.14 g, 73% yield) as yellow oil. $^1H$ NMR (400 MHz, $CDCl_3$) δ 4.90-4.50 (m, 4H), 3.95-3.65 (m, 1H), 2.75-2.48 (m, 4H), 2.20—1.50 (m, 10H), 1.45-1.25 (m, 12H).

2-(2,6-Dioxopiperidin-3-yl)-4-((7-(methylamino)spiro[3.5]nonan-2-yl)amino)isoindoline-1,3-dione (Intermediate AWI)

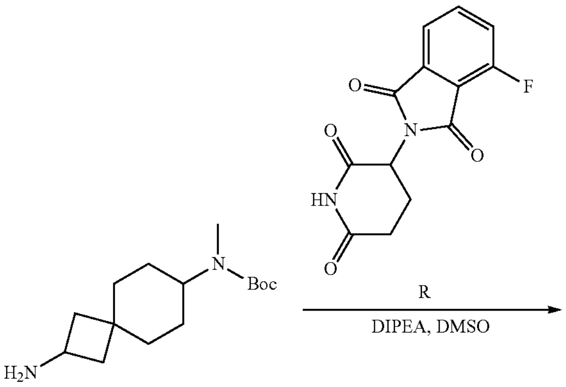

AWH

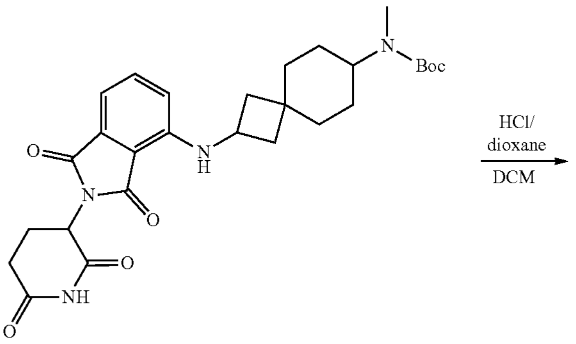

-continued

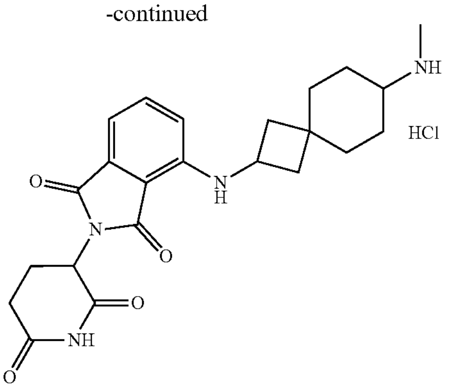

AWI

Step 1—Tert-butyl (2-((2-(2,6-dioxopiperidin-3-yl)-1,3-dioxoisoindolin-4-yl)amino)spiro[3.5]nonan-7-yl)(methyl)carbamate To a solution of 2-(2,6-dioxo-3-piperidyl)-4-fluoro-isoindoline-1,3-dione (50.0 mg, 181 umol, Intermediate R) and tert-butyl N-(2-aminospiro[3.5]nonan-7-yl)-N-methyl-carbamate (58.3 mg, 217 umol, Intermediate AWH) in DMSO (1 mL) was added DIPEA (117 mg, 905 umol). The reaction mixture was stirred at 130° C. for 2 hours. On completion, the reaction mixture was quenched by addition 0.5 N HCl to pH=5, and then filtered to afford a solution, which was purified by prep-HPLC (FA condition: column: Shim-pack C18 150*25*10 um; mobile phase: [water (0.225% FA)-ACN]; B %: 56%-86%, 10 min) to give the title product (38.0 mg, 39% yield) as a yellow solid. $^1H$ NMR (400 MHz, DMSO-d6) δ 8.00 (s, 1H), 7.50 (t, J=7.6 Hz, 1H), 7.13 (d, J=7.2 Hz, 1H), 6.77 (d, J=8.4 Hz, 1H), 6.32 (d, J=5.6 Hz, 1H), 4.97-4.91 (m, 1H), 4.05-3.97 (m, 1H), 2.95-2.67 (m, 6H), 2.54-2.44 (m, 1H), 2.36-2.37 (m, 1H), 2.20-2.13 (m, 1H), 1.91-1.84 (m, 1H), 1.80-1.60 (m, 5H), 1.55-1.35 (m, 13H).

Step 2—2-(2,6-Dioxopiperidin-3-yl)-4-((7-(methylamino)spiro[3.5]nonan-2-yl)amino)isoindoline-1,3-dione hydrochloride To a solution of tert-butyl N-[2-[[2-(2,6-dioxo-3-piperidyl)-1,3-dioxo-isoindolin-4-yl]amino]spiro[3.5]nonan-7-yl]-N-methyl-carbamate (35.0 mg, 66.7 umol) in DCM (3 mL) was added HCl/dioxane (4 M, 1 mL). The reaction mixture was stirred at 20° C. for 0.5 hour. On completion, the reaction mixture was concentrated in vacuo to afford the title product (30.0 mg, HCl salt, 100% yield) as a yellow solid.

2-hydroxyethyl 4-methylbenzenesulfonate (Intermediate AWJ)

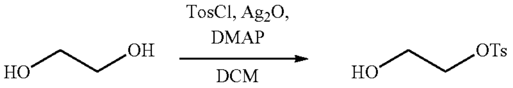

AWJ

To a solution of ethylene glycol (10.0 g, 161 mmol, CAS #107-21-1) in DCM (200 mL) was added DMAP (1.97 g, 16.1 mmol), $Ag_2O$ (44.8 g, 193 mmol) and TosCl (30.7 g, 161 mmol) at 0° C. The reaction mixture was stirred at 0-25° C. for 12 hours. On completion, the reaction mixture was filtered and the filtrate were diluted with $H_2O$ (150 mL) and was extracted with DCM (3×50 mL). The combined organic layers were washed with brine 60 mL (2×30 mL), dried over $Na_2SO_4$, filtered and was concentrated in vacuo. The residue was purified by column chromatography to give the title compound (16.0 g, 45% yield) as a colorless oil. $^1H$ NMR (400 MHz, $CDCl_3$) δ 7.81 (d, J=8.0 Hz, 2H), 7.36 (d, J=8.0 Hz, 2H), 4.15-4.12 (m, 2H), 3.85-3.78 (m, 2H), 2.45 (s, 3H), 2.31 (t, J=6.4 Hz, 1H).

N-[6-(1-hydroxy-1-methyl-ethyl)-1-(2-oxoethyl)indazol-5-yl]-6-(trifluoromethyl)pyridine-2-carboxamide (Intermediate AWK)

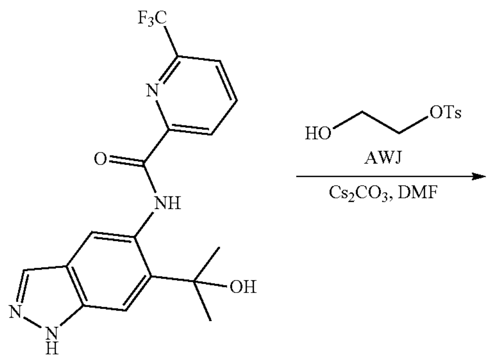

TJ

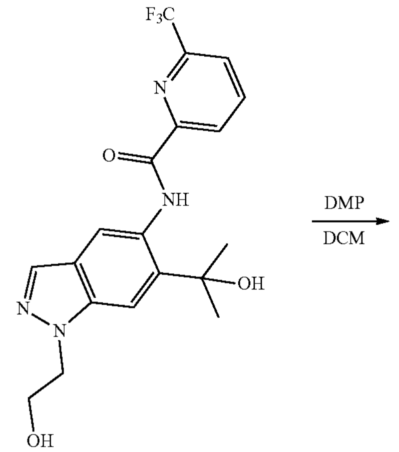

-continued

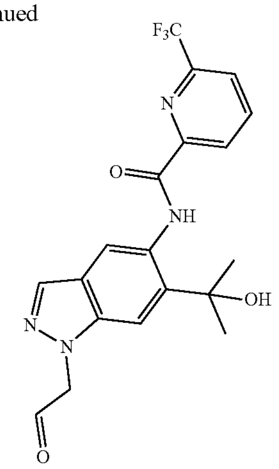

AWK

Step 1—N-[1-(2-hydroxyethyl)-6-(1-hydroxy-1-methyl-ethyl)indazol-5-yl]-6-(trifluoromethyl)pyridine-2-carboxamide To a solution of N-[6-(1-hydroxy-1-methyl-ethyl)-1H-indazol-5-yl]-6-(trifluoromethyl)pyridine -2-carboxamide (100 mg, 274 umol, Intermediate TJ) and 2-hydroxyethyl 4-methylbenzenesulfonate (118 mg, 548 umol, Intermediate AWJ) in DMF (3 mL) was added $Cs_2CO_3$ (268 mg, 823 umol) at 25° C. The reaction mixture was stirred at 80° C. for 12 hours. On completion, the reaction mixture was concentrated in vacuo. The residue was purified by prep-HPLC (column: Shim-pack C18 150*25*10 um; mobile phase: [water (0.225% FA)-ACN]; B %: 32%-52%, 10 min) to give the title compound (50.0 mg, 44% yield) as a white solid. $^1H$ NMR (400 MHz, DMSO-$d_6$) δ 12.35 (s, 1H), 8.75 (s, 1H), 8.46 (d, J=8.0 Hz, 1H), 8.37 (t, J=8.0 Hz, 1H), 8.16 (d, J=7.6 Hz, 1H), 8.04 (s, 1H), 7.63 (s, 1H), 6.01 (s, 1H), 4.86 (t, J=5.2 Hz, 1H), 4.45 (t, J=5.6 Hz, 2H), 3.86-3.73 (m, 2H), 1.64 (s, 6H); LC-MS ($ESI^+$) m/z 408.9 $(M+H)^+$.

Step 2—N-[6-(1-hydroxy-1-methyl-ethyl)-1-(2-oxoethyl)indazol-5-yl]-6-(trifluoromethyl)pyridine-2-carboxamide To a solution of N-[1-(2-hydroxyethyl)-6-(1-hydroxy-1-methyl-ethyl)indazol-5-yl]-6-(trifluoromethyl)pyridine-2-carboxamide (45.0 mg, 110 umol) in DCM (3 mL) and DMF (0.5 mL) was added DMP (70.1 mg, 165 umol) at 25° C., and the reaction mixture was stirred at 25° C. for 16 hours. On completion, the reaction mixture was quenched with sat. aq. $Na_2S_2O_3$ (2 mL) and sat. aq. $NaHCO_3$ (2 mL). The mixture was extracted with DCM (3×6 mL). The combined organic layers were concentrated in vacuo to give the title compound (40.0 mg, 89% yield) as brown oil. LC-MS ($ESI^+$) m/z 407.1 $(M+H)^+$.

Tert-butyl 9-amino-3-azaspiro[5.5]undecane-3-carboxylate (Intermediate AWL)

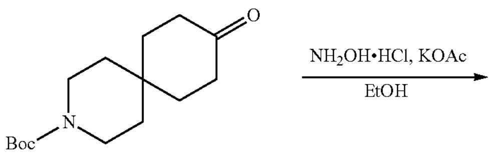

-continued

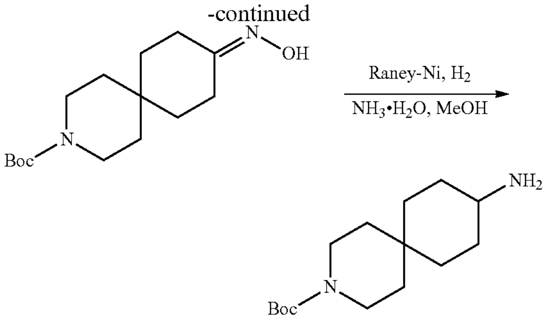

AWL

-continued

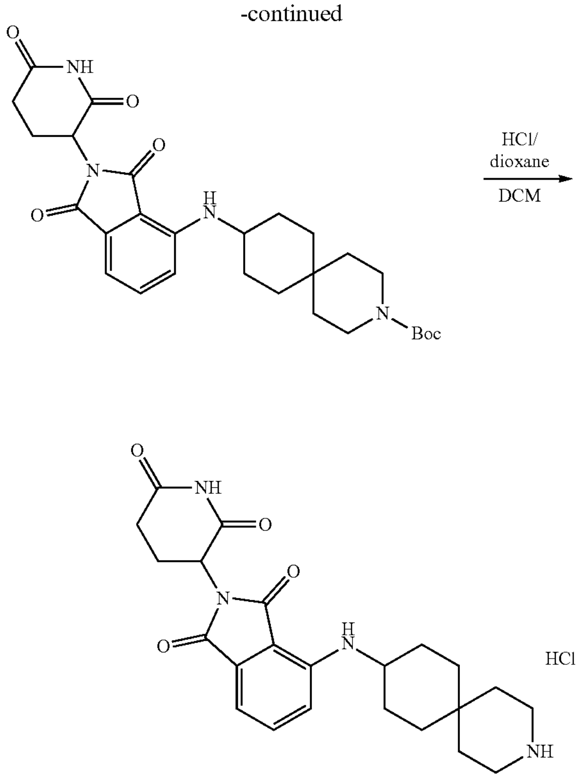

AWM

Step 1—Tert-butyl 9-hydroxyimino-3-azaspiro[5.5]undecane-3-carboxylate

To a solution of tert-butyl 9-oxo-3-azaspiro[5.5]undecane-3-carboxylate (1.00 g, 3.74 mmol, CAS #873924-08-4) in EtOH (15 mL) was added $NH_2OH$ HCl (389 mg, 5.61 mmol) and KOAc (550 mg, 5.61 mmol) at 25° C. The mixture was stirred at 80° C. for 3 hours. On completion, the mixture was concentrated in vacuo. The residue was purified by column chromatography to give the title compound (540 mg, 51% yield) as a white solid. $^1H$ NMR (400 MHz, $CDCl_3$) δ 3.44-3.37 (m, 4H), 2.59-2.46 (m, 2H), 2.30-2.19 (m, 2H), 1.65-1.48 (m, 8H), 1.47 (s, 9H).

Step 2—Tert-butyl 9-amino-3-azaspiro[5.5]undecane-3-carboxylate

To a solution of tert-butyl 9-hydroxyimino-3-azaspiro[5.5]undecane-3-carboxylate (540 mg, 1.91 mmol) in $NH_3.H_2O$ (1 mL) and MeOH (10 mL) was added Raney-Ni (300 mg, 3.50 mmol) at 25° C. The reaction mixture was stirred at 25° C. for 3 hours under $H_2$ (50 Psi). On completion, the mixture was filtered with celite and the filtrate was concentrated in vacuo to give the title compound (460 mg, 89% yield) as yellow oil. $^1H$ NMR (400 MHz, DMSO-$d_6$) δ 3.29-3.20 (m, 4H), 1.63-1.47 (m, 4H), 1.38 (s, 9H), 1.36-1.00 (m, 9H).

4-(3-Azaspiro[5.5]undecan-9-ylamino)-2-(2,6-dioxo-3-piperidyl)isoindoline-1,3-dione (Intermediate AWM)

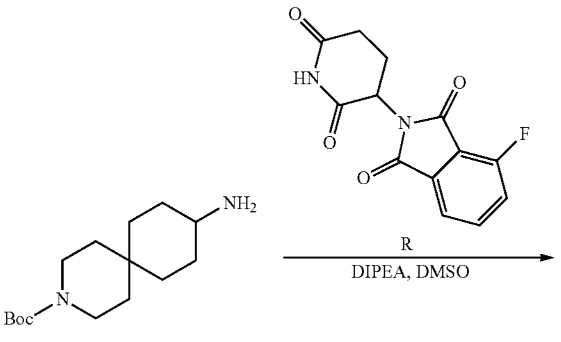

AWL

Step 1—Tert-butyl 9-[[2-(2,6-dioxo-3-piperidyl)-1,3-dioxo-isoindolin-4-yl]amino]-3-azaspiro[5.5]undecane-3-carboxylate To a solution of tert-butyl 9-amino-3-azaspiro[5.5]undecane-3-carboxylate (260 mg, 968 umol, Intermediate AWL) and 2-(2,6-dioxo-3-piperidyl)-4-fluoro-isoindoline-1,3-dione (294 mg, 1.07 mmol, Intermediate R) in DMSO (12 mL) was added DIPEA (250 mg, 1.94 mmol) at 25° C. The reaction mixture was stirred at 130° C. for 3 hours. The reaction mixture was then concentrated in vacuo. The residue was purified by reverse phase (0.1% FA condition) to give the title compound (300 mg, 59% yield) as yellow solid. $^1H$ NMR (400 MHz, DMSO-$d_6$) δ 11.09 (s, 1H), 7.57 (dd, J=7.2, 8.4 Hz, 1H), 7.14 (d, J=8.8 Hz, 1H), 7.02 (d, J=6.8 Hz, 1H), 6.30 (d, J=8.4 Hz, 1H), 5.05 (dd, J=5.6, 13.2 Hz, 1H), 3.60-3.50 (m, 1H), 3.33-3.25 (m, 4H), 2.96-2.80 (m, 1H), 2.07-1.97 (m, 1H), 1.83-1.72 (m, 2H), 1.64 (d, J=13.2 Hz, 2H), 1.52-1.42 (m, 4H), 1.39 (s, 9H), 1.31-1.22 (m, 4H); LC-MS ($ESI^+$) m/z 525.4 $(M+H)^+$.

Step 2—4-(3-Azaspiro[5.5]undecan-9-ylamino)-2-(2,6-dioxo-3-piperidyl)isoindoline-1,3-dione To a solution of tert-butyl 9-[[2-(2,6-dioxo-3-piperidyl)-1,3-dioxo-isoindolin-4-yl]amino]-3-azaspiro[5.5]undecane-3-carboxylate (150 mg, 285 umol) in DCM (4 mL) was added HCl/dioxane (4 M, 2 mL) at 25° C. The mixture was stirred at 25° C. for 1 hour. On completion, the reaction mixture was concentrated in vacuo to give the title compound (130 mg, 98% yield, HCl salt) as a yellow solid. LC-MS ($ESI^+$) m/z 425.3 $(M+H)^+$.

5-Bromo-4-hydroxy-2-nitro-benzaldehyde (Intermediate AWN)

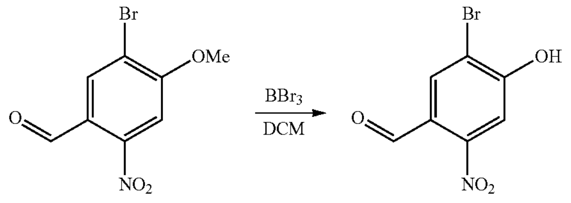

AWN

To a mixture of 5-bromo-4-methoxy-2-nitro-benzaldehyde (7.20 g, 27.6 mmol, synthesized via Steps 1-2 of Intermediate ATE) in DCM (100 mL) was added $BBr_3$ (20.8 g, 83.0 mmol). The reaction mixture was stirred at −70° C. to 25° C. for 12 hours. On completion, the reaction mixture was quenched with MeOH (10 mL) and concentrated in vacuo. The residue was triturated with DCM/PE=½, filtered and concentrated in vacuo to give to the title compound (4.70 g, 69% yield) as yellow solid. $^1H$ NMR (400 MHz, DMSO-$d_6$) δ 12.63-12.10 (m, 1H), 10.02 (s, 1H), 8.08 (s, 1H), 7.52 (s, 1H).

N-(6-(difluoromethoxy)-2-((1r,4r)-4-formylcyclohexyl)-2H-indazol-5-yl)-6-(trifluoro methyl) picolinamide (Intermediate AWO)

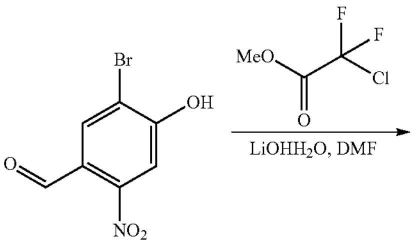

AWN

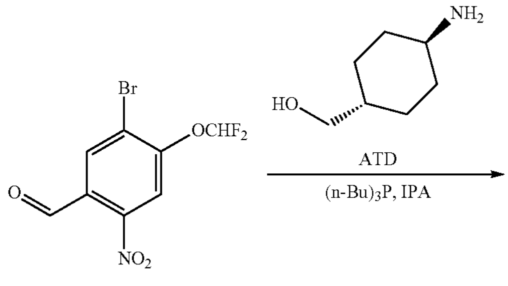

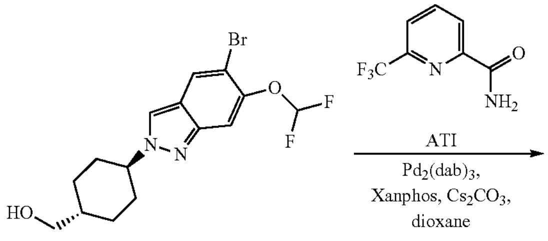

-continued

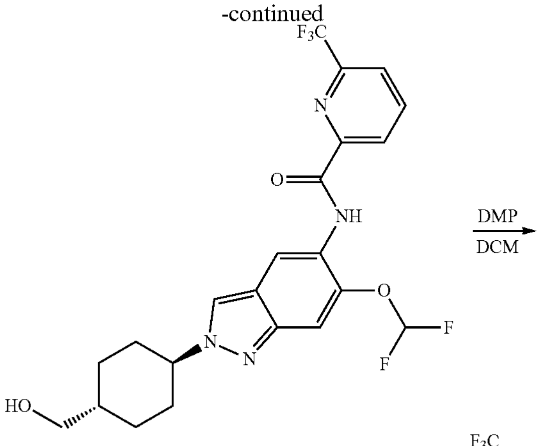

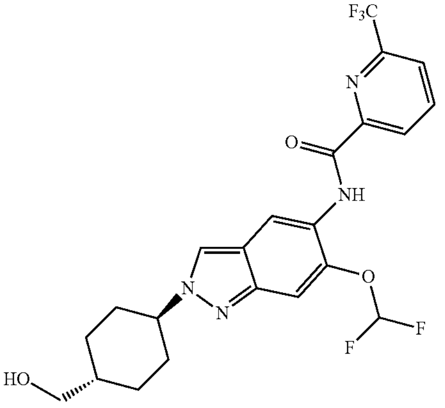

AWO

Step 1—5-Bromo-4-(difluoromethoxy)-2-nitrobenzaldehyde

To a solution of 5-bromo-4-hydroxy-2-nitro-benzaldehyde (1.00 g, 4.06 mmol, Intermediate AWN) and methyl 2-chloro-2, 2-difluoro-acetate (1.17 g, 8.13 mmol, CAS #1514-87-0) in DMF (10 mL) was added LiOH $H_2O$ (682 mg, 16.2 mmol). The mixture was stirred at 80° C. for 12 hours. On completion, the reaction mixture was quenched with $H_2O$ (50 mL) at 0° C. Then the mixture was extracted with EA (3*50 mL). The combined organic layers were washed with brine (50 mL), dried over $Na_2SO_4$, filtered and concentrated in vacuo to give a residue. The residue was purified by column chromatography ($SiO_2$, Petroleum ether/Ethyl acetate=100/1 to 5/1) to give the title compound (430 mg, 26% yield) as a brown oil. $^1H$ NMR (400 MHz, $CDCl_3$) δ 10.39 (s, 1H), 8.25 (s, 1H), 7.98 (s, 1H), 6.75 (t, J=142 Hz, 1H).

Step 2—((1R,4R)-4-(5-bromo-6-(difluoromethoxy)-2H-indazol-2-yl)cyclohexyl)methanol A solution of 5-bromo-4-(difluoromethoxy)-2-nitro-benzaldehyde (430 mg, 1.45 mmol) and (4-aminocyclohexyl) methanol (206 mg, 1.60 mmol, Intermediate ATD) in IPA (5 mL) was stirred at 80° C. for 3 hours. Then tributylphosphane (881 mg, 4.36 mmol) was added and the mixture was stirred at 80° C. for 12 hours. On completion, the mixture was concentrated in vacuo to give a residue. The residue was purified by column chromatography ($SiO_2$, Petroleum ether/

Ethyl acetate=100/1 to 10/1) to give the title compound (800 mg, 88% yield) as a brown oil. LC-MS ($ESI^+$) m/z 375.0 $(M+H)^+$.

Step 3—N-(6-(difluoromethoxy)-2-((1r,4r)-4-(hydroxymethyl)cyclohexyl)-2H-indazol-5-yl)-6-(trifluo romethyl)picolinamide To a solution of [4-[5-bromo-6-(difluoromethoxy)indazol-2-yl]cyclohexyl]methanol (700 mg, 1.87 mmol) and 6-(trifluoromethyl)pyridine-2-carboxamide (354 mg, 1.87 mmol, Intermediate ATI) in dioxane (7 mL) was added $Pd_2(dba)_3$ (170 mg, 186 umol), $Cs_2CO_3$ (1.22 g, 3.73 mmol) and Xantphos (215 mg, 373 umol). The mixture was stirred at 80° C. for 12 hours. On completion, the reaction mixture was filtered and concentrated in vacuo to give a residue. The residue was purified by column chromatography ($SiO_2$, DCM/MeOH=100/1 to 10/1) to give the title compound (0.90 g, 81% yield) as a brown oil. LC-MS ($ESI^+$) m/z 485.3 $(M+H)^+$.

Step 4—N-(6-(difluoromethoxy)-2-((1r,4r)-4-formylcyclohexyl)-2H-indazol-5-yl)-6-(trifluoro methyl) picolinamide To a solution of N-[6-(difluoromethoxy)-2-[4-(hydroxymethyl)cyclohexyl]indazol-5-yl]-6-(trifluoro methyl) pyridine-2-carboxamide (0.90 g, 1.86 mmol) in DCM (10 mL) was added DMP (788 mg, 1.86 mmol). The mixture was stirred at 25° C. for 0.5 hour. On completion, the reaction mixture was quenched with sat. $NaS_2O_3$ (20 mL) and sat. $NaHCO_3$ (20 mL) at 0° C. Then the mixture was diluted with $H_2O$ (20 mL) and extracted with DCM (3×50 mL). The combined organic layers were washed with brine (50 mL), dried over $Na_2SO_4$, filtered and concentrated in vacuo to give a residue. The residue was purified by column chromatography ($SiO_2$, DCM/MeOH=100/1 to 10/1) to give the title compound (0.50 g, 45% yield) as a yellow solid. LC-MS ($ESI^+$) m/z 483.3 $(M+H)^+$.

2-[1-(2, 6-Dioxo-3-piperidyl)-3-methyl-2-oxo-benzimidazol-4-yl]acetaldehyde (Intermediate AWP)

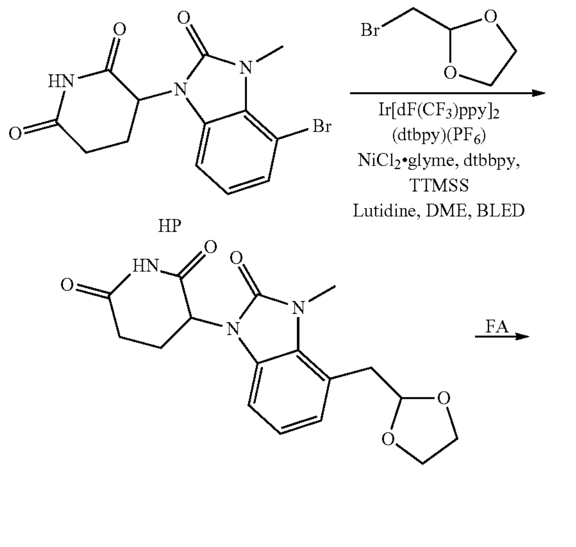

HP

-continued

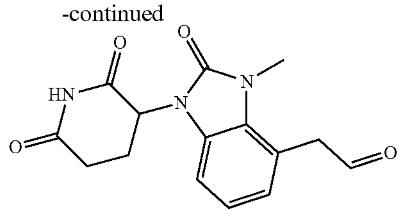

AWP

Step 1—3-[4-(1, 3-Dioxolan-2-ylmethyl)-3-methyl-2-oxo-benzimidazol-1-yl]piperidine-2,6-dione To an 40 mL vial equipped with a stir bar was added 3-(4-bromo-3-methyl-2-oxo-benzimidazol-1-yl)piperidine-2,6-dione (1.00 g, 2.96 mmol, Intermediate HP), 2-(bromomethyl)-1,3-dioxolane (741 mg, 4.44 mmol, 454 uL), $Ir[dF(CF_3)ppy]_2(dtbpy)(PF_6)$ (33.2 mg, 29.6 umol), $NiCl_2$.glyme (3.25 mg, 14.8 umol), dtbbpy (4.76 mg, 17.7 umol), TTMSS (882 mg, 3.55 mmol, 1.09 mL) and 2,6-dimethylpyridine (634 mg, 5.91 mmol, 689 uL) in DME (24 mL). The vial was sealed and placed under nitrogen was added. The reaction was stirred and irradiated with a 34 W blue LED lamp (7 cm away), with cooling fan to keep the reaction temperature at 25° C. for 14 hrs. On completion, the reaction mixture was filtered and concentrated in vacuo. The residue was purified by silica gel chromatography (column height: 250 mm, diameter: 100 mm, 100-200 mesh silica gel, petroleum ether/ethyl acetate=10/1 to 0/1) to give the title compound (340 mg, 26% yield) as yellow solid. LC-MS ($ESI^+$) m/z 346.5 $(M+H)^+$.

Step 2—2-[1-(2, 6-Dioxo-3-piperidyl)-3-methyl-2-oxo-benzimidazol-4-yl]acetaldehyde To a solution of 3-[4-(1, 3-dioxolan-2-ylmethyl)-3-methyl-2-oxo-benzimidazol-1-yl]piperidine- 2,6-dione (170 mg, 393 umol) in HCOOH (10 mL). The mixture was stirred at 25° C. for 1.5 hours. On completion, the reaction mixture was concentrated in vacuo to give the title compound (100 mg, 100% yield) as yellow solid. LC-MS ($ESI^+$) m/z 302.1 $(M+H)^+$.

3-[3-Methyl-2-oxo-4-(2-piperazin-1-ylethyl)benzimidazol-1-yl]piperidine-2,6-dione (Intermediate AWO)

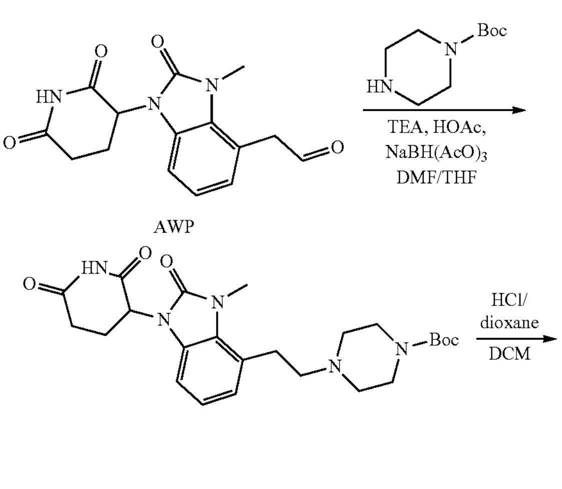

AWP

-continued

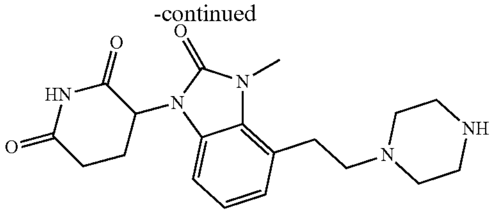

AWQ

Step 1—Tert-butyl 4-[2-[1-(2, 6-dioxo-3-piperidyl)-3-methyl-2-oxo-benzimidazol-4-yl]ethyl]piperazine-1-carboxylate To a solution of tert-butyl piperazine-1-carboxylate (73.9 mg, 331 umol, HCl, CAS #143238-38-4) in a mixed solvent of DMF (1 mL) and THE (2 mL) was added TEA (33.6 mg, 332 umol, 46.2 uL). The mixture was stirred at 0° C. for 10 mins. Subsequently, HOAc (39.9 mg, 664 umol, 37.9 uL) was added. The reaction mixture was adjust to pH 5-6, then 2-[1-(2,6-dioxo-3-piperidyl)-3-methyl-2-oxo- benzimidazol-4-yl]acetaldehyde (100 mg, 332 umol, Intermediate AWP) was added. Thirty minutes later, $NaBH(OAc)_3$ (91.5 mg, 431 umol) was added. The reaction mixture was stirred at 0° C. for 3 hrs. On completion, the reaction mixture was quenched with water (0.1 ml) and concentrated in vacuo. The crude product was purified by reversed-phase HPLC (0.1% FA condition) to give the title compound (150 mg, 84% yield) as white solid. LC-MS ($ESI^+$) m/z 472.2 $(M+H)^+$.

Step 2—3-[3-Methyl-2-oxo-4-(2-piperazin-1-yl-ethyl)benzimidazol-1-yl]piperidine-2,6-dione To a solution of tert-butyl 4-[2-[1-(2, 6-dioxo-3-piperidyl)-3-methyl-2-oxo-benzimidazol-4-yl]ethyl]piperazine-1-carboxylate (100 mg, 185 umol) in DCM (2 mL) was added HCl/dioxane (4 M, 53.0 uL). The mixture was stirred at 25° C. for 2 hours. On completion, the reaction mixture was filtered and concentrated in vacuo to give the title compound (75.0 mg, 99% yield, HCl) as white solid. LC-MS ($ESI^+$) m/z 372.2 $(M+H)^+$.

3-[4-[2-[(1R, 5S)-3, 8-Diazabicyclo[3.2.1]octan-3-yl]ethyl]-3-methyl-2-oxo-benzimidazol-1-yl]piperidine-2,6-dione (Intermediate AWR)

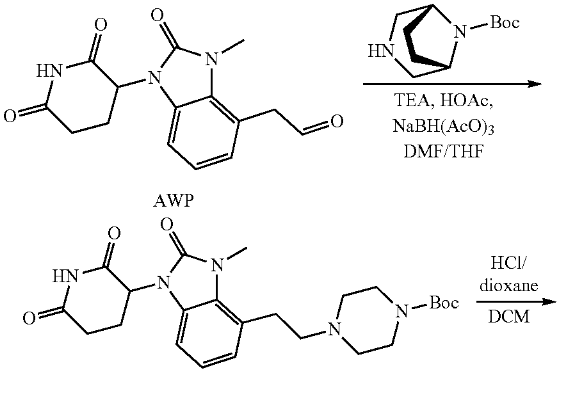

-continued

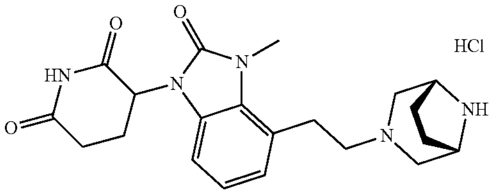

AWR

Step 1—Tert-butyl (1R, 5S)-3-[2-[1-(2, 6-dioxo-3-piperidyl)-3-methyl-2-oxo-benzimidazol-4-yl]ethyl]-3,8-diazabicyclo[3.2.1]octane-8-carboxylate To a solution of 2-[1-(2, 6-dioxo-3-piperidyl)-3-methyl-2-oxo-benzimidazol-4-yl]acetaldehyde(100 mg, 331 umol, Intermediate AWP) in a mixed solvent of DMF (1 mL) and THF (2 mL) was added TEA (33.6 mg, 332 umol, 46.2 uL), HOAc (39.8 mg, 664 umol, 37.9 uL). The reaction mixture was adjust to pH 5-6, then tert-butyl (1R, 5S)-3, 8-diazabicyclo[3.2.1]octane-8-carboxylate(70.5 mg, 332 umol, CAS #149771-44-8) was added. Thirty minutes later, NaBH $(OAc)_3$ (91.5 mg, 431 umol) was added. The reaction mixture was stirred at 0° C. for 20 hrs. On completion, the reaction mixture was quenched with water (0.1 ml) and concentrated in vacuo. The crude product was purified by reversed-phase HPLC (0.1% FA condition) to give the title compound (100 mg, 53% yield) as white solid. LC-MS ($ESI^+$) m/z 498.3 $(M+H)^+$.

Step 2—3-[4-[2-[(1R, 5S)-3, 8-Diazabicyclo[3.2.1] octan-3-yl]ethyl]-3-methyl-2-oxo-benzimidazol-1-yl]piperidine-2,6-dione To a solution of tert-butyl (1R, 5S)-3-[2-[1-(2, 6-dioxo-3-piperidyl)-3-methyl-2-oxo-benzimidazol-4-yl]ethyl]-3, 8-diazabicyclo[3.2.1]octane-8-carboxylate (100 mg, 177 umol) in DCM (2 mL) was added HCl/dioxane (4 M, 45.2 uL). The mixture was stirred at 25° C. for 2 hours. On completion, the reaction mixture was filtered and concentrated in vacuo to give the title compound (75.0 mg, 97% yield, HCl) as white solid. LC-MS ($ESI^+$) m/z 398.2 $(M+H)^+$.

3-(3-Methyl-2-oxo-5-piperazin-1-yl-benzimidazol-1-yl)piperidine-2,6-dione (Intermediate AWS)

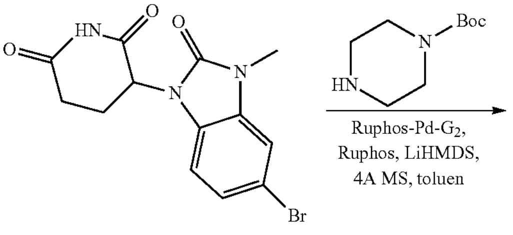

HN

-continued

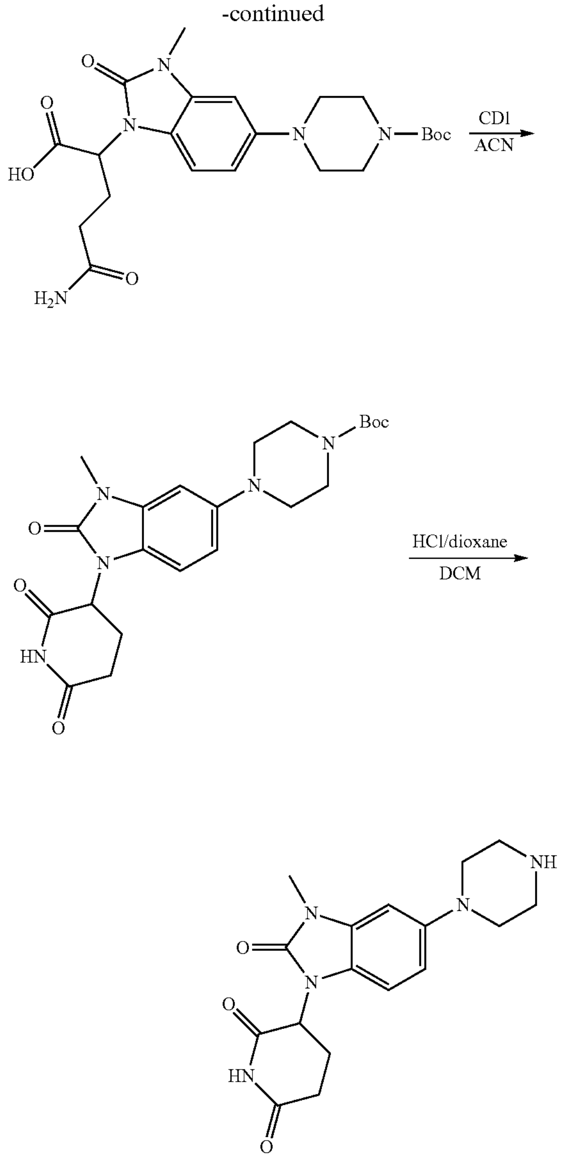

AWS

Step 1—5-Amino-4-[5-(4-tert-butoxycarbonylpiperazin-1-yl)-3-methyl-2-oxo-benzimidazol-1-yl]-5-oxo-pentanoic acid A mixture of 3-(5-bromo-3-methyl-2-oxo-benzimidazol-1-yl)piperidine-2,6-dione (1.00 g, 2.96 mmol, Intermediate HN), tert-butyl piperazine-1-carboxylate (826 mg, 4.44 mmol, CAS #143238-38-4), [2-(2-aminophenyl)phenyl]-chloro-palladium;dicyclohexyl-[2-(2,6-diisopropoxyphenyl)phenyl]phosphane (459 mg, 591 umol, CAS #1375325-68-0), RuPhos (276 mg, 591 umol), LiHMDS (1 M, 17.7 mL) and 4 Å molecular sieves (200 mg) in toluene (15 mL) was de-gassed and heated at 80° C. for 2 hrs under $N_2$ atmosphere. On completion, the mixture was acidified with FA to pH=3-5, filtered and the filtrate was concentrated in vacuo. The residue was purified by reverse phase (0.1% FA condition) to give the title compound (380 mg, 28% yield) as a yellow solid. LC-MS ($ESI^+$) m/z 462.2 $(M+H)^+$.

Step 2—Tert-butyl 4-[1-(2,6-dioxo-3-piperidyl)-3-methyl-2-oxo-benzimidazol-5-yl]piperazine-1- carboxylate To a solution of 5-amino-4-[5-(4-tert-butoxycarbonylpiperazin-1-yl)-3-methyl-2-oxo-benzimidazol -1-yl]-5-oxo-pentanoic acid (360 mg, 780 umol) in ACN (10 mL) was added CDI (253 mg, 1.56 mmol). The reaction mixture was stirred at 80° C. for 12 hrs. On completion, the mixture was concentrated in vacuo. The residue was purified by reverse phase (0.1% FA condition) to give the title compound (150 mg, 43% yield) as a yellow solid. LC-MS ($ESI^+$) m/z 444.4 $(M+H)^+$.

Step 3—3-(3-Methyl-2-oxo-5-piperazin-1-yl-benzimidazol-1-yl)piperidine-2,6-dione To a solution of tert-butyl 4-[1-(2,6-dioxo-3-piperidyl)-3-methyl-2-oxo-benzimidazol-5-yl]piperazine -1-carboxylate (70.0 mg, 158 umol) in DCM (5 mL) was added HCl/dioxane (5 mL). The reaction mixture was stirred at 20° C. for 1 hr. On completion, the mixture was concentrated in vacuo to give the title compound (59.0 mg, 98% yield, HCl salt) as a yellow solid. LC-MS ($ESI^+$) m/z 344.1 $(M+H)^+$.

N-[2-(4-formylcyclohexyl)-6-(1-hydroxy-1-methyl-ethyl)indazol-5-yl]pyrazolo[1,5-a] pyrimidine-3-carboxamide (Intermediate AWT)

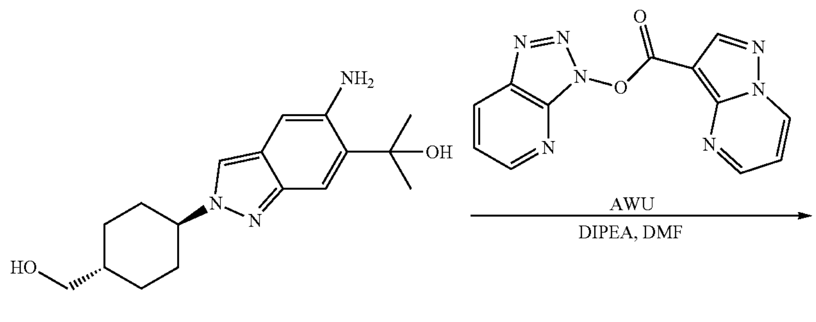

-continued

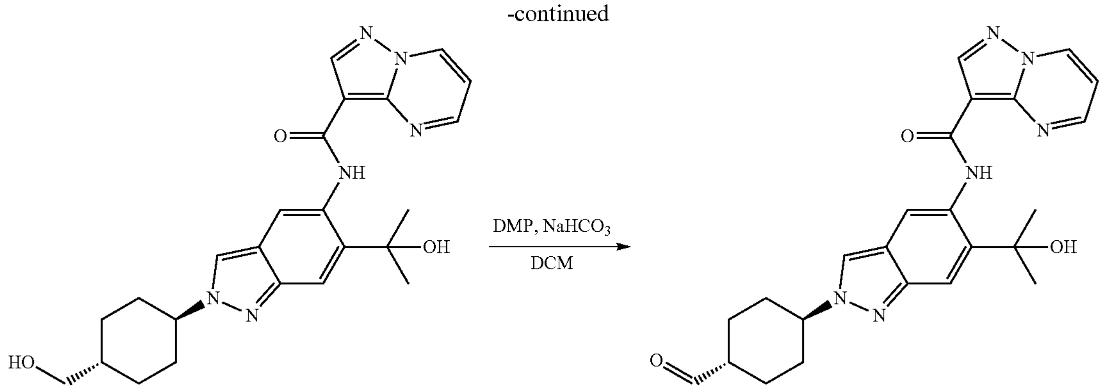

Step 1—N-[2-[4-(hydroxymethyl)cyclohexyl]-6-(1-hydroxy-1-methyl-ethyl)indazol-5-yl]pyrazolo [1,5-a]pyrimidine-3-carboxamide To a solution of 2-[5-amino-2-[4-(hydroxymethyl)cyclohexyl]indazol-6-yl]propan-2-ol (200 mg, 659 umol, Intermediate AOX) and triazolo[4,5-b]pyridin-3-ylpyrazolo[1,5-a]pyrimidine-3-carboxylate (370 mg, 1.32 mmol, Intermediate AWU) in DMF (2 mL) was added DIPEA (255 mg, 1.98 mmol, 344 uL). The mixture reaction was stirred at 25° C. for 24 hrs. On completion, the reaction mixture was filtered and concentrated in vacuo. The crude product was purified by reversed-phase HPLC (column: Phenomenex Synergi C18 150*25*10 um; mobile phase: [water (0.225% FA)-ACN]; B %: 16%-46%, 10 min) to give the title compound (180 mg, 43% yield) as yellow solid. $^{1}$H NMR (400 MHz, DMSO-$d_6$) δ 11.24 (s, 1H), 9.31 (dd, J=1.6, 7.2 Hz, 1H), 8.81 (dd, J=1.6, 4.4 Hz, 1H), 8.66 (s, 1H), 8.33 (d, J=3.2 Hz, 2H), 7.56 (s, 1H), 7.28 (dd, J=4.4, 7.2 Hz, 1H), 5.70 (s, 1H), 4.50 (t, J=5.2 Hz, 1H), 4.45-4.36 (m, 1H), 3.30-3.27 (m, 2H), 2.20-2.09 (m, 2H), 1.91 (d, J=10.4 Hz, 4H), 1.60 (s, 6H), 1.54-1.43 (m, 1H), 1.23-1.10 (m, 2H); LC-MS (ESI$^+$) m/z 449.3 $(M+H)^+$.

Step 2—N-[2-(4-formylcyclohexyl)-6-(1-hydroxy-1-methyl-ethyl)indazol-5-yl]pyrazolo[1,5-a] pyrimidine-3-carboxamide To a solution of N-[2-[4-(hydroxymethyl)cyclohexyl]-6-(1-hydroxy-1-methyl-ethyl)indazol-5-yl]pyrazolo[1,5-a]pyrimidine-3-carboxamide (170 mg, 270 umol) in DCM (3 mL) was added $NaHCO_3$ (114 mg, 1.35 mmol, 52.5 uL), DMP (149 mg, 351 umol, 109 uL) at 0° C. The reaction mixture was stirred at 25° C. for 24 hrs. On completion, the mixture was quenched with sat. $Na_2S_2O_3$ (2 mL) and sat. $NaHCO_3$ (2 mL), stirred for 10 minutes, then extracted with DCM (2×20 mL). The organic layer was washed with brine (2×10 mL), dried with $Na_2SO_4$, filtered and the filtrate was concentrated in vacuo to give the title compound (100 mg, 41% yield) as yellow solid. $^{1}$H NMR (400 MHz, DMSO-$d_6$) δ 9.34-9.27 (m, 1H), 8.88-8.75 (m, 1H), 8.65 (s, 1H), 8.40-8.24 (m, 2H), 8.03-7.93 (m, 1H), 7.75-7.67 (m, 1H), 7.55 (s, 1H), 7.28 (dd, J=4.4, 7.2 Hz, 1H), 4.45-4.34 (m, 1H), 2.15-2.10 (m, 2H), 1.88-1.82 (m, 2H), 1.78-1.67 (m, 4H), 1.60 (s, 6H), 1.35-1.27 (m, 2H); LC-MS (ESI$^+$) m/z 447.2 $(M+H)^+$.

3H-[1,2,3]triazolo[4,5-b]pyridin-3-ylpyrazolo[1,5-a] pyrimidine-3-carboxylate (Intermediate AWU)

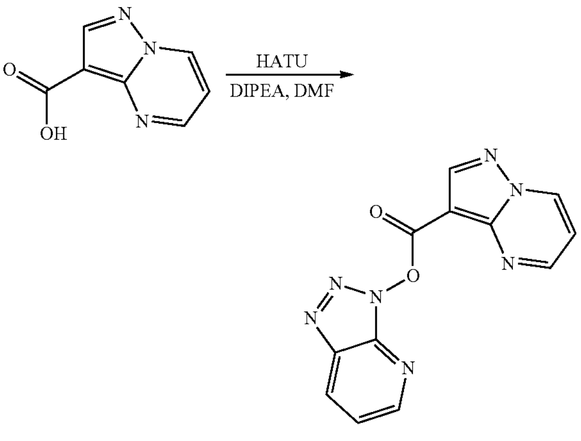

AWU

To a solution of pyrazolo[1,5-a]pyrimidine-3-carboxylic acid (2 g, 12.2 mmol, CAS #25940-35-6) in DMF (20 mL) was added HATU (5.13 g, 13.4 mmol) and DIPEA (1.58 g, 12.2 mmol, 2.14 mL). The reaction mixture was stirred at 25° C. for 1 hour. On completion, the reaction mixture was quenched with water (100 mL) and filtered. The filter cake was washed with water (2×40 mL) and dried in vacuo to give the title compound (1.70 g, 49% yield) as a light yellow solid. $^{1}$H NMR (400 MHz, DMSO-$d_6$) δ 9.51 (dd, J=1.6, 7.2 Hz, 1H), 9.14 (s, 1H), 9.02 (dd, J=1.6, 4.2 Hz, 1H), 8.84 (dd, J=1.2, 4.5 Hz, 1H), 8.76 (dd, J=1.2, 8.4 Hz, 1H), 7.67 (dd, J=4.2, 8.4 Hz, 1H), 7.52 (dd, J=4.2, 7.2 Hz, 1H).

Pyrazolo[1,5-a]pyrimidine-3-carboxamide (Intermediate AWV)

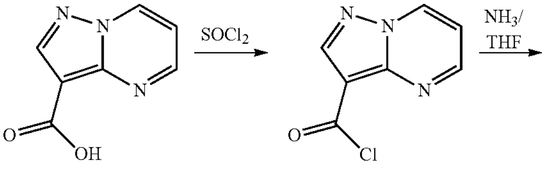

-continued

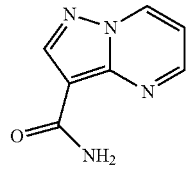

AWV

Step 1—Pyrazolo[1,5-a]pyrimidine-3-carbonyl chloride

A mixture of pyrazolo[1,5-a]pyrimidine-3-carboxylic acid (1.00 g, 6.13 mmol, CAS #25940-35-6) in $SOCl_2$ (32.8 g, 276 mmol, 20 mL) was heated at 100° C. for 2 h. On completion, the reaction mixture was concentrated in vacuo to give the title compound (1.00 g, 90% yield) as a yellow solid. $^1H$ NMR (400 MHz, DMSO-$d_6$) δ 9.30 (dd, J=1.6, 6.8 Hz, 1H), 8.85 (dd, J=1.6, 4.0 Hz, 1H), 8.66 (s, 1H), 7.31 (dd, J=4.0, 7.2 Hz, 1H), 3.83 (s, 3H).

Step 2—Pyrazolo[1,5-a]pyrimidine-3-carboxamide

A mixture of pyrazolo[1,5-a]pyrimidine-3-carbonyl chloride (500 mg, 2.75 mmol) in $NH_3$/THF (8.0 mL) was stirred at 25° C. for 5 hr. On completion, the reaction mixture was concentrated in vacuo to give the title compound (500 mg, 90% yield) as yellow solid. $^1H$ NMR (400 MHz, DMSO-$d_6$) δ 9.31 (dd, J=1.6, 7.2 Hz, 1H), 8.81 (dd, J=1.6, 4.0 Hz, 1H), 8.57 (s, 1H), 7.57-7.28 (m, 2H), 7.27 (dd, J=4.4, 7.2 Hz, 1H).

[4-(5-bromo-6-morpholino-indazol-2-yl)cyclohexyl]methanol (Intermediate AWW)

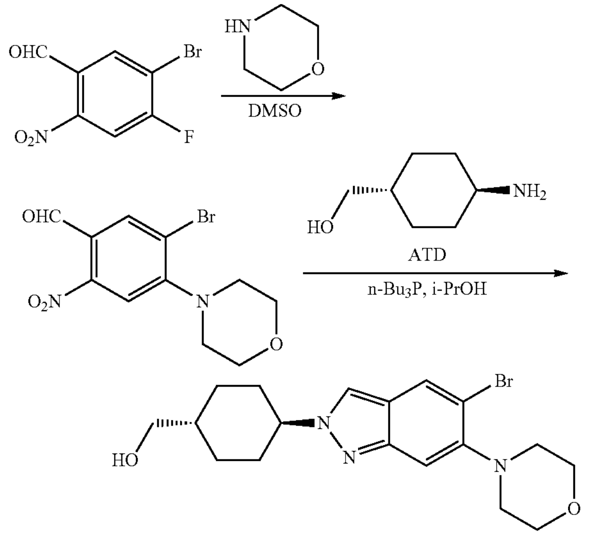

AWW

Step 1—5-bromo-4-morpholino-2-nitro-benzaldehyde

A solution of 5-bromo-4-fluoro-2-nitro-benzaldehyde (2.00 g, 8.06 mmol, synthesized via Step 1 of Intermediate ATE) in DMSO (25 mL) was added with morpholine (2.81 g, 32.3 mmol). The reaction mixture was stirred at 80° C. for 1 hours. On completion, the reaction mixture was then diluted in ethyl acetate (50 mL) and water (50 mL), then extracted with ethyl acetate (3×50 mL). The organic layer was dried over $Na_2SO_4$, filtered and concentrated in vacuo to afford the residue. The residue was purified by column chromatography (PE:EA=4:1) to give the title compound (1.50 g, 58% yield) as yellow solid. $^1H$ NMR (400 MHz, $CDCl_3$) δ 10.33 (s, 1H), 8.21 (s, 1H), 7.63 (s, 1H), 4.07-3.82 (m, 4H), 3.32-3.24 (m, 4H). LC-MS (ESI$^+$) m/z 314.9, 316.9 $(M+H)^+$.

Step 2—[4-(5-bromo-6-morpholino-indazol-2-yl)cyclohexyl]methanol

To a solution of 5-bromo-4-morpholino-2-nitro-benzaldehyde (1.50 g, 4.76 mmol) in IPA (50 mL) was added (4-aminocyclohexyl) methanol (738 mg, 5.71 mmol, Intermediate ATD). The mixture was heated at 80° C. for 4 hr under $N_2$. Then the reaction was cooled to 25° C., and tributylphosphine (2.89 g, 14.3 mmol) was added. The reaction mixture was heated to 80° C. for 16 hr. On completion, the reaction mixture was concentrated in vacuo to remove some IPA, and a solid was precipitated. The mixture was filtered and the filter cake was washed by petroleum ether to give the title compound (1.00 g, 53% yield) as yellow solid. $^1H$ NMR (400 MHz, $CDCl_3$) δ 7.93 (s, 1H), 7.86 (s, 1H), 7.32 (s, 1H), 4.39-4.32 (m, 1H), 4.02-3.86 (m, 4H), 3.58 (d, J=6.4 Hz, 2H), 3.10-3.09 (m, 4H), 2.51-2.22 (m, 2H), 2.15-1.89 (m, 4H), 1.78-1.64 (m, 2H), 1.34-1.25 (m, 2H).

N-[2-(4-formylcyclohexyl)-6-morpholino-indazol-5-yl]pyrazolo[1,5-a]pyrimidine-3-carboxamide (Intermediate AWX)

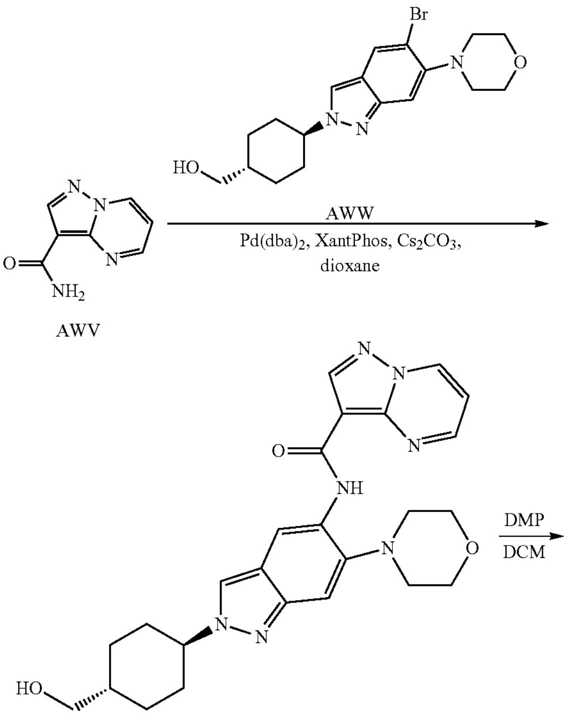

-continued

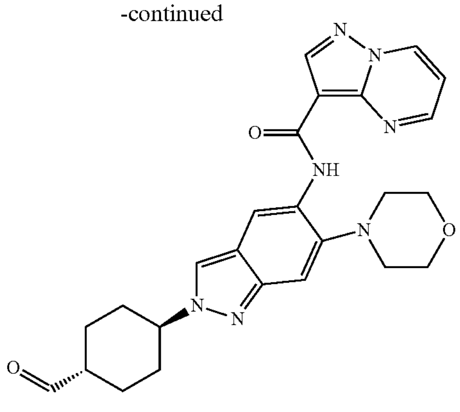

AWX

Step 1—N-[2-[4-(hydroxymethyl)cyclohexyl]-6-morpholino-indazol-5-yl]pyrazolo[1,5-a]pyrimidine-3-carboxamide To a solution of [4-(5-bromo-6-morpholino-indazol-2-yl) cyclohexyl]methanol (400 mg, 1.01 mmol, Intermediate AWW) in dioxane (6.0 mL) was added $Pd(dba)_2$ (58.3 mg, 101 umol), Xantphos (117 mg, 203 umol), $Cs_2CO_3$ (661 mg, 2.03 mmol) and pyrazolo[1,5-a]pyrimidine-3-carboxamide (329 mg, 2.03 mmol, Intermediate AWV). The mixture was stirred at 110° C. for 16 hr. On completion, the reaction mixture was filtered and the filtrate was concentrated in vacuo to give a residue. The residue was purified by reverse phase flash (0.1% FA condition) to give the title compound (100 mg, 19% yield) as white solid. $^1$H NMR (400 MHz, DMSO-$d_6$) δ 10.68 (s, 1H), 9.39 (dd, J=1.6, 7.2 Hz, 1H), 8.98 (dd, J=1.6, 4.4 Hz, 1H), 8.74 (d, J=11.2 Hz, 2H), 8.33 (s, 1H), 7.55-7.32 (m, 2H), 4.60-4.30 (m, 2H), 3.94-3.82 (m, 4H), 3.31-3.28 (m, 2H), 3.00-2.85 (m, 4H), 2.19-2.09 (m, 2H), 1.97-1.84 (m, 4H), 1.55-1.42 (m, 1H), 1.23-1.07 (m, 2H). LC-MS (ESI$^+$) m/z 476.2 $(M+H)^+$.

Step 2—N-[2-(4-formylcyclohexyl)-6-morpholino-indazol-5-yl]pyrazolo[1,5-a]pyrimidine-3-carboxamide To a mixture of N-[2-[4-(hydroxymethyl)cyclohexyl]-6-morpholino-indazol-5-yl]pyrazolo[1,5-a] pyrimidine-3-carboxamide (60.0 mg, 126 umol) in DCM (3.0 mL) was added DMP (80.3 mg, 189 umol) at 25° C. under $N_2$. The mixture was stirred at 25° C. for 1 hr. On completion, the reaction mixture was quenched with $Na_2S_2O_3$ (5.0 mL) and extracted with DCM (2×3.0 mL). The combined organic layer was washed with $NaHCO_3$ and brine (2×3.0 mL), dried with anhydrous $Na_2SO_4$, filtered and concentrated in vacuo to give the title compound (60.0 mg, 90% yield) as yellow solid. LC-MS (ESI$^+$) m/z 474.3 $(M+H)^+$.

5-Fluoro-6-methyl-pyridine-2-carboxamide (Intermediate AWY)

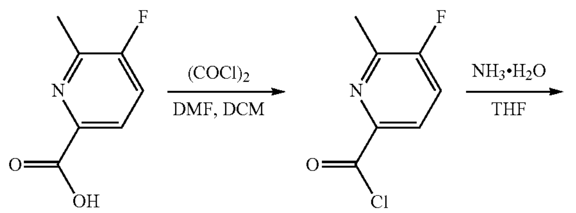

AWY

-continued

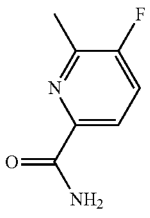

AWY

Step 1—5-Fluoro-6-methyl-pyridine-2-carbonyl chloride

To a solution of 5-fluoro-6-methyl-pyridine-2-carboxylic acid (1.00 g, 6.12 mmol, CAS #1005474-88-3) in DCM (12 mL) was added $(COCl)_2$ (1.55 g, 12.2 mmol) and DMF (44.7 mg, 612 umol) at 0° C. The mixture was stirred at 0—25° C. for 2 hours. On completion, the mixture was concentrated in vacuo to give the title compound (1.05 g, 98% yield) as a red solid.

Step 2—5-Fluoro-6-methyl-pyridine-2-carboxamide

A solution of 5-fluoro-6-methyl-pyridine-2-carbonyl chloride (1.05 g, 6.05 mmol) in THF (12 mL) was added to $NH_3.H_2O$ (7.07 g, 60.4 mmol, 30% solution) at 0° C. The mixture was stirred at 0-25° C. for 0.5 hour. On completion, the reaction mixture was diluted with $H_2O$ (15 mL) and extracted with EA (3×5 mL). The combined organic layers were washed by brine (20 mL), dried over $Na_2SO_4$, filtered and the filtrate was concentrated in vacuo to give the title compound (950 mg, 91% yield) as a white solid. $^1$H NMR (400 MHz, DMSO-$d_6$) δ 7.97 (s, 1H), 7.92 (dd, J=4.0, 8.4 Hz, 1H), 7.76 (t, J=9.2 Hz, 1H), 7.62 (s, 1H), 2.51 (s, 3H).

5-fluoro-N-[2-(4-formylcyclohexyl)-6-methoxy-indazol-5-yl]-6-methyl-pyridine-2- carboxamide (Intermediate AWZ)

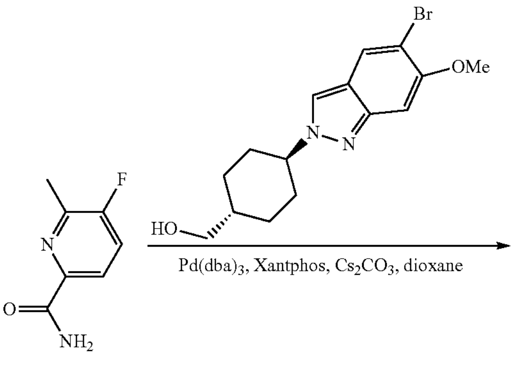

-continued

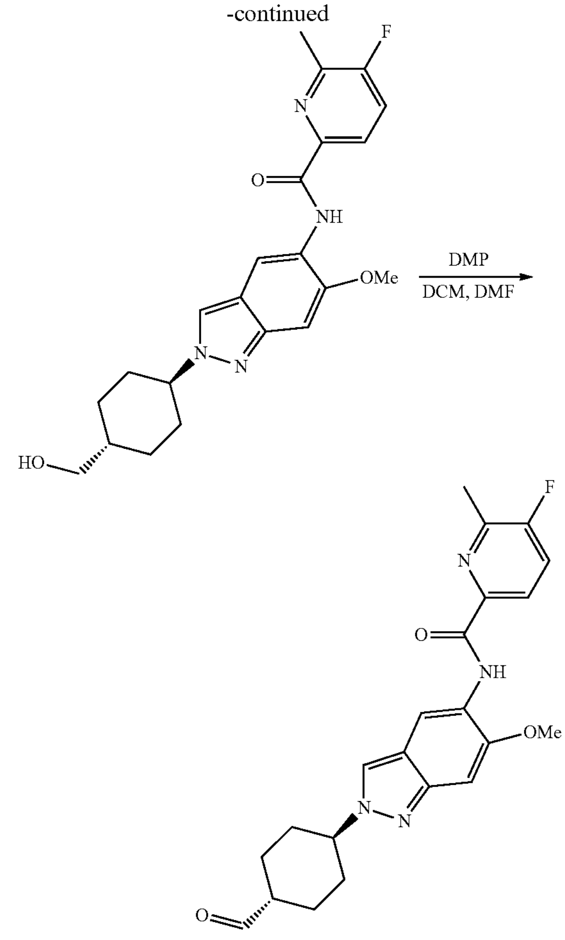

AWZ

Step 1—5-Fluoro-N-[2-[4-(hydroxymethyl)cyclohexyl]-6-methoxy-indazol-5-yl]-6-methyl-pyridine-2- carboxamide To a solution of 5-fluoro-6-methyl-pyridine-2-carboxamide (300 mg, 1.75 mmol, Intermediate AWY) and [4-(5-bromo-6-methoxy-indazol-2-yl)cyclohexyl]methanol (594 mg, 1.75 mmol, synthesized via Steps 1-3 of Intermediate ATE) in dioxane (15 mL) was added $Pd_2(dba)_3$ (160 mg, 175 umol), Xantphos (202 mg, 350 umol) and $Cs_2CO_3$ (1.14 g, 3.50 mmol) at 25° C. The reaction mixture was stirred at 80° C. for 12 hours under $N_2$. On completion, the reaction mixture was diluted with $H_2O$ (20 mL) and extracted with EA (3×6 mL). The combined organic layers were washed with brine 20 mL (2×10 mL), dried over $Na_2SO_4$, filtered and the filtrate was concentrated in vacuo. The residue was purified by reverse phase (0.1% FA condition) to give the title compound (160 mg, 13% yield, 60% purity) as a yellow solid. LC-MS (ESI$^+$) m/z 413.2 (M+H)$^+$.

Step 2—5-fluoro-N-[2-(4-formylcyclohexyl)-6-methoxy-indazol-5-yl]-6-methyl-pyridine-2- carboxamide To a solution of 5-fluoro-N-[2-[4-(hydroxymethyl)cyclohexyl]-6-methoxy-indazol-5-yl]-6-methyl- pyridine-2-carboxamide (110 mg, 160 umol) in DCM (2 mL) and DMF (0.5 mL) was added DMP (88.2 mg, 208 umol) at 25° C. The reaction mixture was stirred at 25° C. for 2 hours. On completion, the reaction was quenched with sat. aq. $Na_2S_2O_3$ (2 mL) and sat. aq. $NaHCO_3$ (2 mL). The mixture was extracted with DCM (3×10 mL). The combined organic layers were concentrated in vacuo to give the title compound (65.0 mg, 98% yield) as yellow oil. LC-MS (ESI$^+$) m/z 411.3 (M+H)$^+$.

Benzyl N-(2-aminospiro[3.5]nonan-7-yl)-N-methyl-carbamate (Intermediate AXA)

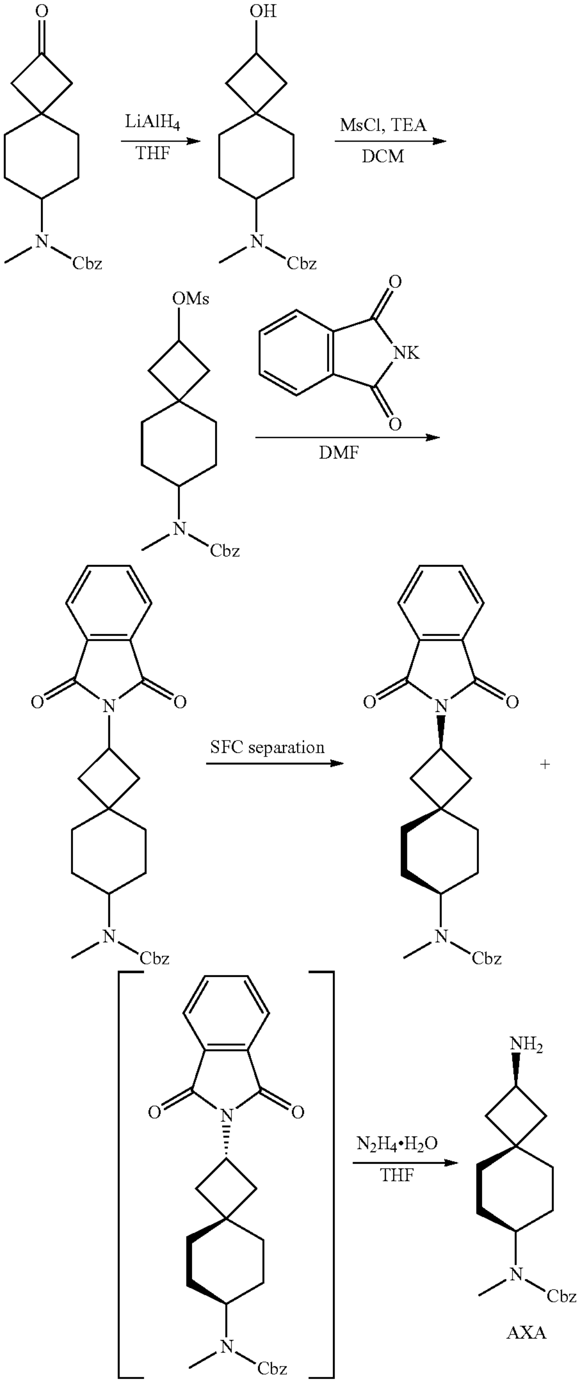

AXA

Step 1—Benzyl N-(2-hydroxyspiro[3.5]nonan-7-yl)-N-methyl-carbamate

To a solution of benzyl N-methyl-N-(2-oxospiro[3.5]nonan-7-yl)carbamate (1.00 g, 3.32 mmol, synthesized via Steps 1-5 of Intermediate ANJ) in THE (15 mL) was added $LiAlH_4$ (151 mg, 3.98 mmol) at 0° C. The mixture was stirred at 0° C. for 0.1 hr. On completion, the reaction mixture was quenched with water (0.5 mL) and NaOH (0.5 mL, 15%) at 0° C., then the mixture was stirred at 0° C. for 0.5 hr. Then the mixture was filtered and the filtrate was dried over $Na_2SO_4$, filtered and concentrated in vacuo to give the title compound (1.00 g, 95% yield) as colorless oil. $^1H$ NMR (400 MHz, $CDCl_3$) δ 7.44-7.29 (m, 5H), 5.13 (s, 2H), 4.34-4.23 (m, 1H), 3.95 (s, 1H), 3.75 (t, J=6.4 Hz, 1H), 2.79 (s, 3H), 2.38-2.27 (m, 1H), 2.17-2.11 (m, 1H), 1.87-1.84 (m, 1H), 1.77-1.69 (m, 2H), 1.61-1.42 (m, 7H).

Step 2—[7-[Benzyloxycarbonyl(methyl)amino]spiro[3.5]nonan-2-yl]methanesulfonate

To a solution of benzyl N-(2-hydroxyspiro[3.5]nonan-7-yl)-N-methyl-carbamate (1.00 g, 3.30 mmol) and TEA (1.00 g, 9.89 mmol) in DCM (20 mL) was added MsCl (566 mg, 4.94 mmol) at 0° C. The mixture was stirred at 30° C. for 0.5 hr. On completion, the mixture was quenched with water (20 mL), then washed with water (3×20 mL). The organic layer were dried over $Na_2SO_4$, filtered and concentrated in vacuo to give the title compound (1.20 g, 95% yield) as colorless oil. $^1H$ NMR (400 MHz, $CDCl_3$) δ 7.48-7.28 (m, 5H), 5.13 (s, 2H), 5.04-4.92 (m, 1H), 4.04-3.75 (m, 1H), 3.01-2.96 (s, 3H), 2.78 (s, 3H), 2.50-2.40 (m, 1H), 2.30-2.24 (m, 1H), 2.13-2.05 (m, 1H), 2.00 (dd, J=7.2, 12.0 Hz, 1H), 1.77-1.68 (m, 2H), 1.61-1.52 (m, 3H), 1.52-1.41 (m, 3H).

Step 3—Benzyl N-[2-(1,3-dioxoisoindolin-2-yl)spiro[3.5]nonan-7-yl]-N-methyl-carbamate To a solution of [7-[benzyloxycarbonyl(methyl)amino]spiro[3.5]nonan-2-yl]methanesulfonate (1.10 g, 2.88 mmol) in DMF (15 mL) was added (1,3-dioxoisoindolin-2-yl)potassium (801 mg, 4.33 mmol). The mixture was stirred at 100° C. for 16 hrs. On completion, the reaction mixture diluted with water (50 mL) and extracted with EA (3×20 mL). The combined organic layers were dried over $Na_2SO_4$, filtered and concentrated in vacuo to give a residue. On completion, the reaction mixture was purified by prep-HPLC (column: Phenomenex luna C18 150*40 mm*15 um; mobile phase: [water (0.225% FA)-ACN]) to give the title compound (0.35 g, 28% yield) as light yellow solid. $^1H$ NMR (400 MHz, $CDCl_3$) δ 7.88-7.76 (m, 2H), 7.75-7.66 (m, 2H), 7.44-7.28 (m, 5H), 5.15 (s, 2H), 4.78-4.69 (m, 1H), 4.11-3.72 (m, 1H), 2.79 (s, 3H), 2.73-2.65 (m, 1H), 2.59 (t, J=10.0 Hz, 1H), 2.31-2.17 (m, 1H), 2.12-1.99 (m, 2H), 1.98-1.87 (m, 1H), 1.64-1.35 (m, 6H); LC-MS ($ESI^+$) m/z 433.4 $(M+H)^+$.

Step 4—Benzyl ((2S,4s,7S)-2-(1,3-dioxoisoindolin-2-yl)spiro[3.5]nonan-7-yl)(methyl)carbamate and benzyl ((2R,4r,7R)-2-(1,3-dioxoisoindolin-2-yl)spiro[3.5]nonan-7-yl)(methyl)carbamate Benzyl N-[2-(1,3-dioxoisoindolin-2-yl)spiro[3.5]nonan-7-yl]-N-methyl-carbamate (0.30 g, 693 umol) was purified by SFC (column: DAICEL CHIRALPAK AD (250 mm*30 mm, 10 um); mobile phase: [0.1% $NH_3.H_2O$ EtOH];B %: 60%-60%, 4.4 min) to give to give two isomers. The first fraction was benzyl ((2S,4s,7S)-2-(1,3-dioxoisoindolin-2-yl)spiro[3.5]nonan-7-yl)(methyl)carbamate (120 mg, 38% yield, tR=1.50) isolated as yellow solid. $^1H$ NMR (400 MHz, $CDCl_3$) δ 7.75-7.73 (m, 2H), 7.67-7.58 (m, 2H), 7.35-7.19 (m, 5H), 5.07 (s, 2H), 4.70-4.61 (m, 1H), 4.04-3.71 (m, 1H), 2.72 (s, 3H), 2.62 (dd, J=9.6, 10.8 Hz, 1H), 2.51 (t, J=10.0 Hz, 1H), 2.24-2.11 (m, 1H), 2.03-1.92 (m, 2H), 1.88-1.84 (m, 1H), 1.72-1.31 (m, 6H); LC-MS ($ESI^+$) m/z 433.0 $(M+H)^+$. The second fraction was benzyl ((2R,4r,7R)-2-(1,3-dioxoisoindolin-2-yl)spiro[3.5]nonan-7-yl)(methyl)carbamate (120 mg, 38% yield, tR=1.89) isolated as yellow solid. $^1H$ NMR (400 MHz, $CDCl_3$) δ 7.79-7.70 (m, 2H), 7.68-7.59 (m, 2H), 7.36-7.20 (m, 5H), 5.07 (s, 2H), 4.70-4.61 (m, 1H), 4.02-3.73 (m, 1H), 2.72 (s, 3H), 2.62 (dd, J=9.6, 10.8 Hz, 1H), 2.51 (t, J=10.0 Hz, 1H), 2.22-2.11 (m, 1H), 2.05-1.92 (m, 2H), 1.88-1.84 (m, 1H), 1.67-1.32 (m, 6H); LC-MS ($ESI^+$) m/z 433.0 $(M+H)^+$.

Step 5—Benzyl N-(2-aminospiro[3.5]nonan-7-yl)-N-methyl-carbamate

To a solution of benzyl N-[2-(1,3-dioxoisoindolin-2-yl)spiro[3.5]nonan-7-yl]-N-methyl-carbamate (0.11 g, 254 umol) in EtOH (3 mL) was added $N_2H4H_2O$ (129 mg, 2.54 mmol, 98% purity). The mixture was stirred at 80° C. for 6 hrs. On completion, the reaction mixture was filtered to give the filtrate and concentrated in vacuo to give a residue. The residue was diluted with DCM (10 mL), filtered to give the filtrate and concentrated in vacuo to give the title compound (75.0 mg, 92% yield) as light yellow solid. $^1H$ NMR (400 MHz, $CDCl_3$) δ 7.45-7.28 (m, 5H), 5.13 (s, 2H), 4.06-3.74 (m, 1H), 3.44-3.36 (m, 1H), 2.78 (s, 3H), 2.34-2.23 (m, 1H), 2.11-2.05 (m, 1H), 1.76-1.68 (m, 1H), 1.63-1.36 (m, 9H); LC-MS ($ESI^+$) m/z 303.1 $(M+H)^+$.

2-(2,6-Dioxo-3-piperidyl)-4-[[7-(methylamino)spiro[3.5]nonan-2-yl]amino]isoindoline- 1,3-dione (Intermediate AXB)

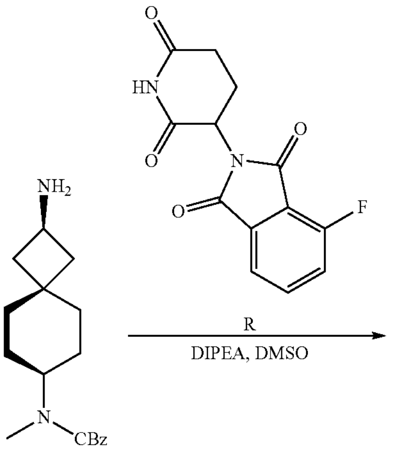

AXA

-continued

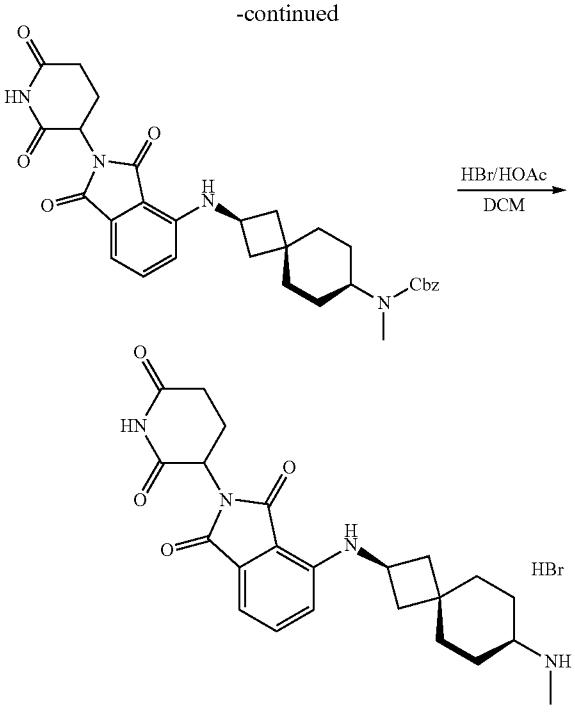

AXB

Step 1—Benzyl N-[2-[[2-(2,6-dioxo-3-piperidyl)-1, 3-dioxo-isoindolin-4-yl]amino]spiro[3.5]nonan-7-yl]-N-methyl-carbamate To a solution of benzyl N-(2-aminospiro[3.5]nonan-7-yl)-N-methyl-carbamate (70.0 mg, 231 umol, Intermediate AXA) and 2-(2,6-dioxo-3-piperidyl)-4-fluoro-isoindoline-1, 3-dione (83.1 mg, 300 umol, Intermediate R) in DMSO (2 mL) was added DIPEA (89.7 mg, 694 umol). The mixture was stirred at 130° C. for 3 hrs. On completion, the reaction mixture was diluted with water (8 mL) and extracted with EA (3x10 mL). The combined organic layers were dried over $Na_2SO_4$, filtered and concentrated in vacuo to give a residue. The residue was purified by reverse phase (FA condition) to give the title compound (65.0 mg, 50% yield) as yellow solid. $^1H$ NMR (400 MHz, $CDCl_3$) δ 8.14 (s, 1H), 7.48 (dd, J=7.2, 8.4 Hz, 1H), 7.43-7.28 (m, 5H), 7.11 (d, J=7.2 Hz, 1H), 6.74 (d, J=8.4 Hz, 1H), 6.30 (d, J=5.6 Hz, 1H), 5.14 (s, 2H), 4.98-4.88 (m, 1H), 4.11-3.78 (m, 2H), 2.95-2.68 (m, 6H), 2.46 (t, J=7.6 Hz, 1H), 2.32-2.27 (m, 1H), 2.19-2.10 (m, 1H), 1.90-1.82 (m, 1H), 1.79-1.65 (m, 4H), 1.59-1.39 (m, 5H); LC-MS ($ESI^+$) m/z 559.2 $(M+H)^+$.

Step 2—2-(2,6-Dioxo-3-piperidyl)-4-[[7-(methyl-amino)spiro[3.5]nonan-2-yl]amino]isoindoline- 1,3-dione To a solution of benzyl N-[2-[[2-(2,6-dioxo-3-piperidyl)-1,3-dioxo-isoindolin-4-yl]amino]spiro[3.5] nonan-7-yl]-N-methyl-carbamate (60.0 mg, 107 umol) in DCM (2 mL) was added HBr/HOAc (107 umol, 1 mL, 33% solution). The mixture was stirred at 25° C. for 2 hrs. On completion, the mixture was concentrated under $N_2$ flow to give the title compound (50.0 mg, 90% yield, HBr salt) as yellow solid. LC-MS ($ESI^+$) m/z 425.2 $(M+H)^+$.

N-(2-((1r,4r)-4-formylcyclohexyl)-6-methoxy-2H-indazol-5-yl)picolinamide (Intermediate AXC)

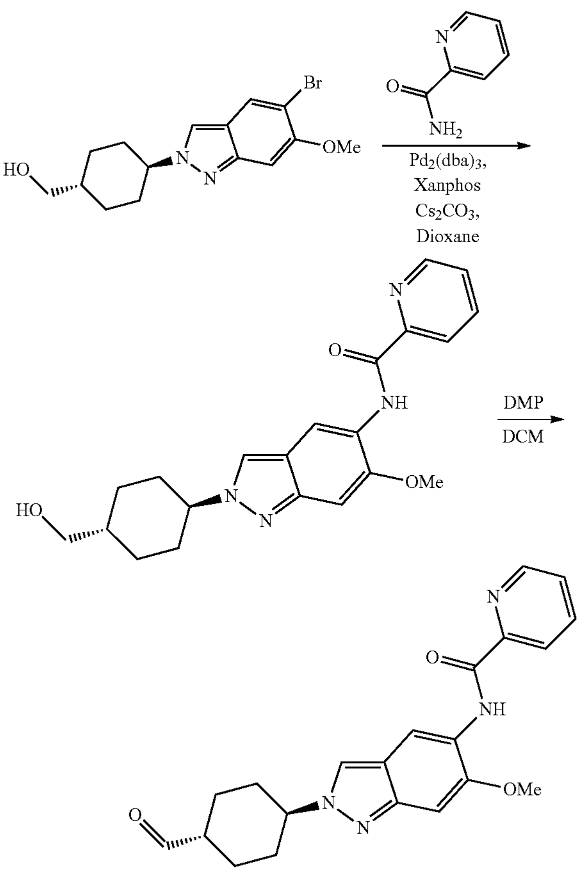

AXC

Step 1—N-(2-((1r,4r)-4-(hydroxymethyl)cyclo-hexyl)-6-methoxy-2H-indazol-5-yl)picolinamide A mixture of [4-(5-bromo-6-methoxy-indazol-2-yl)cyclo-hexyl]methanol (1.00 g, 2.95 mmol, synthesized via Steps 1-3 of Intermediate ATE), pyridine- 2-carboxamide (432 mg, 3.54 mmol, CAS #1452-77-3), $Pd_2(dba)_3$ (270 mg, 295 umol), Xantphos (341 mg, 590 umol, CAS #161265-03-8) and $Cs_2CO_3$ (1.92 g, 5.90 mmol) in the dioxane (15 mL) was stirred at 100° C. for 48 hours under $N_2$. On completion, the reaction mixture was filtered and concentrated in vacuo. The residue was purified by column chromatography ($SiO_2$, Petroleum ether/Ethyl acetate=5/1 to 1/3) to give the title compound (400 mg, 36% yield) as yellow solid. $^1H$ NMR (400 MHz, $CDCl_3$) δ 10.73 (s, 1H), 8.87 (s, 1H), 8.72-8.62 (m, 1H), 8.31 (d, J=7.6 Hz, 1H), 7.93-7.89 (m, 1H), 7.87 (s, 1H), 7.49-7.48 (m, 1H), 7.08 (s, 1H), 4.33 (tt, J=3.7, 11.9 Hz, 1H), 4.04 (s, 3H), 3.57 (t, J=5.2 Hz, 2H), 2.40-2.29 (m, 2H), 2.09-1.93 (m, 4H), 1.74-1.64 (m, 1H), 1.43 (s, 1H), 1.31-1.21 (m, 2H).

Step 2—N-(2-((1r,4r)-4-formylcyclohexyl)-6-methoxy-2H-indazol-5-yl)picolinamide

To a solution of N-[2-[4-(hydroxymethyl)cyclohexyl]-6-methoxy-indazol-5-yl]pyridine-2- carboxamide (150 mg, 394 umol) in the DCM (3 mL) was added DMP (201 mg, 473 umol). The mixture was stirred at 25° C. for 12 hours. On completion, the reaction mixture was quenched with sat. aq. $Na_2S_2O_3$ (5 mL), extracted with DCM (3×20 mL), and washed with sat. aq. $NaHCO_3$ (20 mL). The organic layer was dried over $Na_2SO_4$, filtered and concentrated in vacuo to give the title compound (145 mg, 97% yield) as yellow solid. $^1$H NMR (400 MHz, $CDCl_3$) δ 10.73 (s, 1H), 9.72 (d, J=0.8 Hz, 1H), 8.88 (s, 1H), 8.70-8.65 (m, 1H), 8.32-8.30 m, 1H), 7.91 (t, J=7.6 Hz, 1H), 7.87 (s, 1H), 7.49-7.48 (m, 1H), 7.08 (s, 1H), 4.37-4.30 (m, 1H), 4.04 (s, 3H), 2.46-2.36 (m, 3H), 2.30-2.22 (m, 2H), 2.12-2.00 (m, 2H), 1.56-1.53 (m, 2H).

3-[4-[2-[(1R, 5S)-3, 8-Diazabicyclo[3.2.1]octan-3-yl]ethyl]-3-methyl-2-oxo-benzimidazol-1- yl]piperidine-2,6-dione (Intermediate AXD)

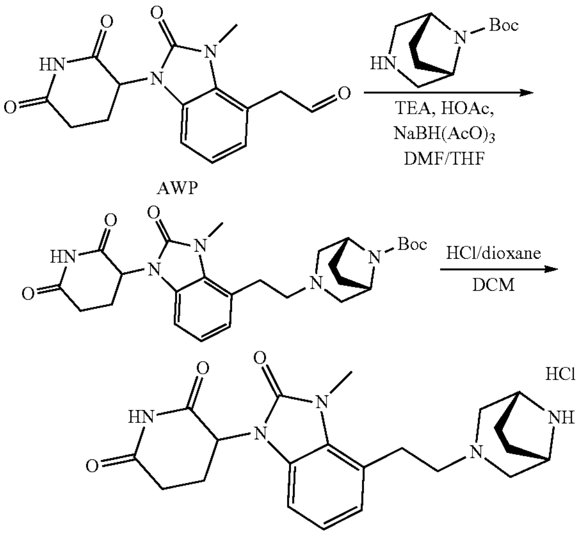

AWP

AXD

Step 1—Tert-butyl (1R, 5S)-3-[2-[1-(2, 6-dioxo-3-piperidyl)-3-methyl-2-oxo-benzimidazol-4-yl]ethyl]-3,8-diazabicyclo[3.2.1]octane-8-carboxylate To a solution of tert-butyl (1R,5S)-3,8-diazabicyclo [3.2.1]octane-8-carboxylate (28.2 mg, 133 umol, CAS #149771-44-8) in a mixed solvent of DMF (1 mL) and THE (2 mL) was added TEA (33.6 mg, 332 umol, 46.2 uL), HOAc (15.9 mg, 265 umol, 15.2 uL). The reaction mixture was adjust to pH 5-6, then 2-[1-(2, 6-dioxo-3-piperidyl)-3-methyl-2-oxo-benzimidazol-4-yl]acetaldehyde(40.0 mg, 133 umol, Intermediate AWP) was added. Thirty minutes later, $NaBH(OAc)_3$ (36.6 mg, 173 umol) was added. The reaction mixture was stirred at 0° C. for 20 hrs. On completion, the reaction mixture was quenched with water (0.1 ml) and concentrated in vacuo. The crude product was purified by reversed-phase HPLC (0.1% FA condition) to give the title compound (40.0 mg, 42% yield) as white solid. LC-MS (ESI$^+$) m/z 498.3 (M+H)$^+$.

Step 2—3-[4-[2-[(1R, 5S)-3, 8-Diazabicyclo[3.2.1] octan-3-yl]ethyl]-3-methyl-2-oxo-benzimidazol-1-yl]piperidine-2,6-dione To a solution of tert-butyl (1R, 5S)-3-[2-[1-(2, 6-dioxo-3-piperidyl)-3-methyl-2-oxo-benzimidazol-4-yl]ethyl]-3, 8-diazabicyclo[3.2.1]octane-8-carboxylate (40.0 mg, 55.3 umol) in DCM (2 mL) was added HCl/dioxane (4 M, 45.2 uL). The mixture was stirred at 25° C. for 2 hours. On completion, the reaction mixture was filtered and concentrated in vacuo to give the title compound (23.0 mg, 100% yield, HCl salt) as yellow solid. LC-MS (ESI$^+$) m/z 398.2 (M+H)$^+$.

[4-(5-Bromo-6-isopropoxy-indazol-2-yl)cyclohexyl] methanol (Intermediate AXE)

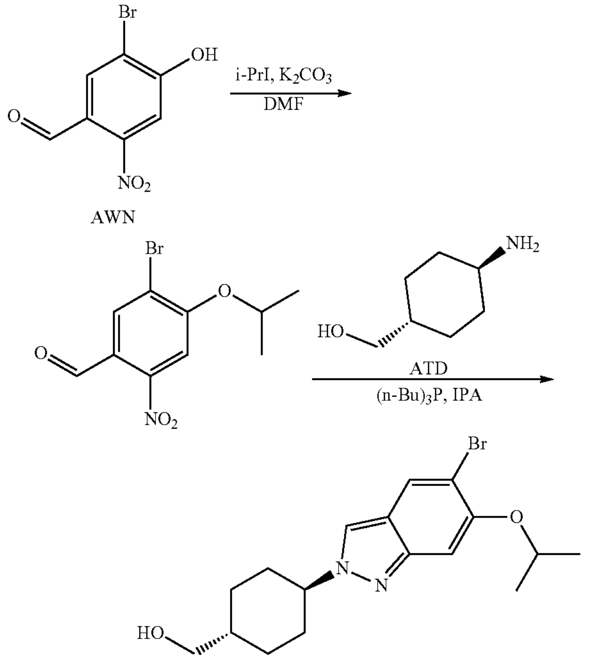

AWN

AXE

Step 1—5-Bromo-4-isopropoxy-2-nitro-benzaldehyde

To a mixture of 5-bromo-4-hydroxy-2-nitro-benzaldehyde (1.00 g, 4.06 mmol, Intermediate AWN) in DMF (15 mL) was added $K_2CO_3$ (1.12 g, 8.13 mmol) and 2-iodopropane (1.04 g, 6.10 mmol). The reaction mixture was stirred at 25° C. for 12 hours. On completion, the reaction mixture was filtered and diluted with water (20 mL) and extracted with EA (2×30 mL). The combined organic layers was dried over $Na_2SO_4$, filtered and concentrated in vacuo to give the title compound (700 mg, 59% yield) as yellow oil. $^1$H NMR (400 MHz, DMSO-$d_6$) δ 10.02 (s, 1H), 8.15 (s, 1H), 7.80 (s, 1H), 5.04-4.94 (m, 1H), 1.36 (d, J=6.0 Hz, 6H).

Step 2—[4-(5-Bromo-6-isopropoxy-indazol-2-yl) cyclohexyl]methanol

To a mixture of 5-bromo-4-isopropoxy-2-nitro-benzaldehyde (700 mg, 2.43 mmol) in IPA (10 mL) was added (4-aminocyclohexyl)methanol (345 mg, 2.67 mmol, Intermediate ATD). The mixture was stirred at 80° C. for 12 hours. When the mixture was cooled to 25° C., tributylphosphane (1.47 g, 7.29 mmol) was added. The reaction mixture was stirred at 80° C. for 3 hours. On completion, the residue was purified by column chromatography. Then the residue was triturated with PE (20 mL) to give the title compound (740 mg, 82% yield) as white solid. $^1$H NMR (400 MHz, DMSO-$d_6$) δ 8.26 (s, 1H), 7.95 (s, 1H), 7.12 (s, 1H), 4.73-4.64 (m, 1H), 4.48 (t, J=5.2 Hz, 1H), 4.41-4.31 (m, 1H), 3.28 (t, J=5.6 Hz, 2H), 2.16-2.06 (m, 2H), 1.94-1.79 (m, 4H), 1.53-1.40 (m, 1H), 1.32 (d, J=6.0 Hz, 6H), 1.20-1.06 (m, 2H).

N-[2-(4-formylcyclohexyl)-6-isopropoxy-indazol-5-yl]-6-(trifluoromethyl)pyridine-2- carboxamide (Intermediate AXF)

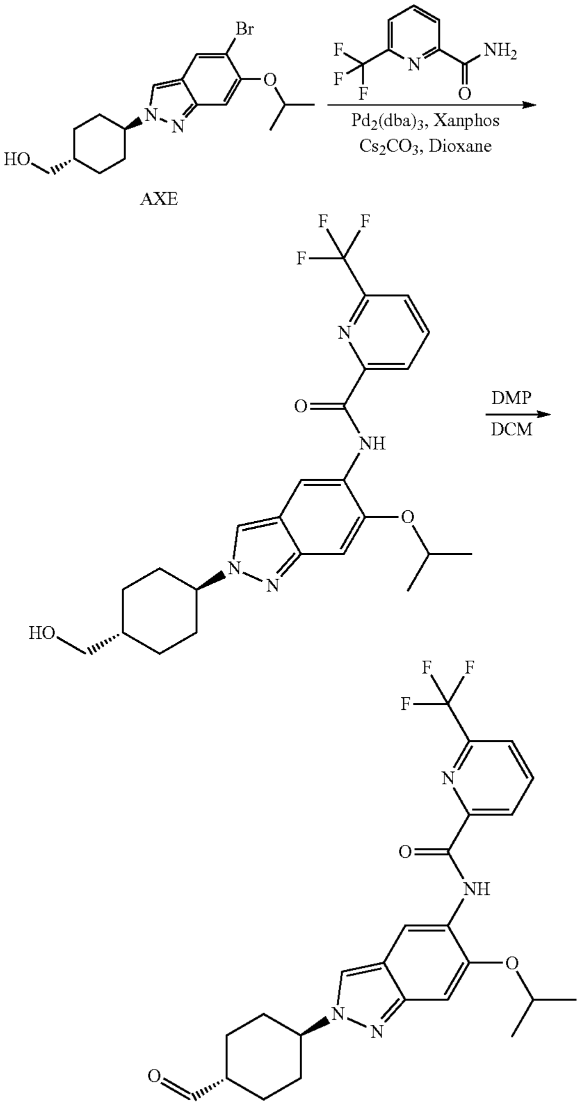

AXE

AXF

Step 1—N-[2-[4-(Hydroxymethyl)cyclohexyl]-6-isopropoxy-indazol-5-yl]-6-(trifluoromethyl)pyridine -2-carboxamide To a mixture of [4-(5-bromo-6-isopropoxy-indazol-2-yl) cyclohexyl]methanol (640 mg, 1.74 mmol, Intermediate AXE) in dioxane (10 mL) was added Pd$_2$(dba)$_3$ (159 mg, 174 umol), Xantphos (201 mg, 348 umol), $Cs_2CO_3$ (1.14 g, 3.49 mmol) and 6-(trifluoromethyl)pyridine-2-carboxamide (364 mg, 1.92 mmol, CAS #22245-84-7). The reaction mixture was stirred at 80° C. for 16 hours. On completion, the reaction mixture was filtered and concentrated in vacuo. The residue was diluted with water (30 mL) and extracted with DCM (2×30 mL). The combined organic layers were dried over $Na_2SO_4$, filtered and concentrated in vacuo. The residue was purified by column chromatography to give the title compound (700 mg, 84% yield) as white solid. $^1$H NMR (400 MHz, DMSO-$d_6$) δ 10.72 (s, 1H), 8.71 (s, 1H), 8.47-8.43 (m, 1H), 8.42-8.37 (m, 1H), 8.32 (s, 1H), 8.23-8.18 (m, 1H), 7.19 (s, 1H), 4.90-4.76 (m, 1H), 4.48 (t, J=5.2 Hz, 1H), 4.41-4.26 (m, 1H), 3.29 (t, J=5.6 Hz, 2H), 2.18-2.07 (m, 2H), 1.94-1.82 (m, 4H), 1.55-1.42 (m, 1H), 1.40 (d, J=6.0 Hz, 6H), 1.21-1.07 (m, 2H).

Step 2—N-[2-(4-formylcyclohexyl)-6-isopropoxy-indazol-5-yl]-6-(trifluoromethyl)pyridine-2- carboxamide To a mixture of N-[2-[4-(hydroxymethyl)cyclohexyl]-6-isopropoxy-indazol-5-yl]-6-(trifluoromethyl)pyridine-2-carboxamide (150 mg, 314 umol) in DCM (1 mL) was added DMP (160 mg, 377 umol). The reaction mixture was stirred at 25° C. for 1.5 hours. On completion, the reaction mixture was quenched with sat.aq.$Na_2S_2O_3$ (8 mL) and sat. aq. $NaHCO_3$ (8 mL) at 25° C. The mixture was extracted with DCM (2×50 mL). The combined organic phase was concentrated in vacuo to give the title compound (149 mg, 99% yield) as white solid. LC-MS (ESI$^+$) m/z 475.3 $(M+H)^+$.

Benzyl 4-[3-(bromomethyl)cyclobutoxy]piperidine-1-carboxylate (Intermediate AXG)

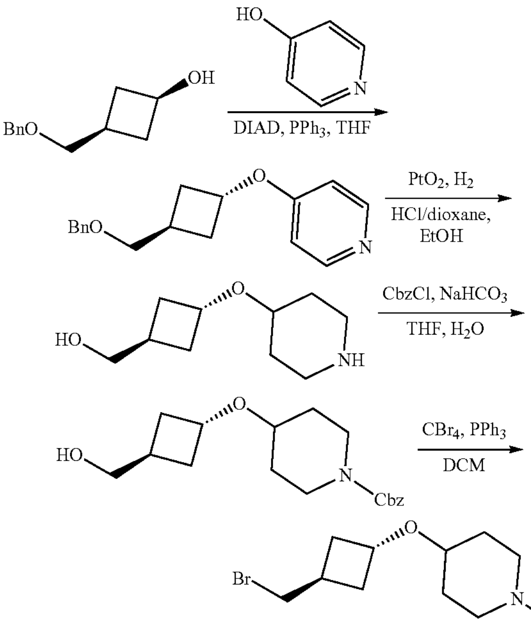

AXG

Step 1—4-[3-(Benzyloxymethyl)cyclobutoxy]pyridine

To a solution of 3-(benzyloxymethyl)cyclobutanol (5.50 g, 28.6 mmol, synthesized via Step 1 of Intermediate ART) and pyridin-4-ol (2.72 g, 28.6 mmol) in THF (10 mL) was added $PPh_3$ (11.3 g, 42.9 mmol) and DIAD (8.68 g, 42.9 mmol) at 0° C. The reaction mixture was stirred at 50° C. for 12 hrs under $N_2$. On completion, the reaction mixture was concentrated in vacuo. The residue was purified by column chromatography (PE:EA=2:1) to give the title compound (5.00 g, 65% yield) as a white solid. $^1$H NMR (400 MHz, DMSO-$d_6$) δ 8.46-8.31 (m, 2H), 7.56-7.19 (m, 5H), 6.90-6.76 (m, 2H), 4.88 (t, J=6.4 Hz, 1H), 4.53 (s, 2H), 3.53 (d, J=6.8 Hz, 2H), 2.62-2.53 (m, 1H), 2.35-2.31 (m, 2H), 2.24-2.11 (m, 2H).

Step 2—[3-(4-Piperidyloxy)cyclobutyl]methanol

To a solution of 4-[3-(benzyloxymethyl)cyclobutoxy]pyridine (4.00 g, 14.9 mmol) in EtOH (8.0 mL) was added $PtO_2$ (1.69 g, 7.43 mmol) and HCl/dioxane (4 M, 3.7 mL) at 25° C. The reaction mixture was stirred at 25° C. for 12 hrs under $H_2$ (50 Psi). On completion, the reaction mixture was filtered through celite and the filtrate was concentrated in vacuo to give the title compound (5.00 g, 90% yield, HCl salt) as a white solid. $^1$H NMR (400 MHz, DMSO-$d_6$) δ 9.31-8.52 (m, 2H), 4.13-4.09 (m, 1H), 3.41 (s, 1H), 3.40-3.27 (m, 2H), 3.20-2.79 (m, 4H), 2.23-2.07 (m, 1H), 2.06-1.76 (m, 4H), 1.72-1.60 (m, 3H), 1.59-1.53 (m, 1H).

Step 3—Benzyl 4-[3-(hydroxymethyl)cyclobutoxy]piperidine-1-carboxylate

To a solution of [3-(4-piperidyloxy)cyclobutyl]methanol (1.50 g, 8.10 mmol) in THF (20 mL) was added an aqueous solution of $Na_2CO_3$ (1.03 g, 9.72 mmol, 4.00 mL). Then CbzCl (1.38 g, 8.10 mmol) was added and the mixture was stirred for 2 hour at 25° C. On completion, the reaction mixture was concentrated in vacuo to give a residue. The residue was purified by reverse phase flash (0.1% FA condition) to give the title compound (250 mg, 8.31%) as colorless oil. $^1$H NMR (400 MHz, $CDCl_3$) δ 7.40-7.32 (m, 5H), 4.17 (q, J=7.2 Hz, 1H), 3.89-3.86 (m, 2H), 3.66 (d, J=7.2 Hz, 2H), 3.56-3.39 (m, 1H), 3.19-3.13 (m, 2H), 2.46-2.30 (m, 1H), 2.20-2.03 (m, 4H), 1.82-1.76 (m, 2H), 1.53-1.49 (m, 4H), 1.30-1.20 (m, 1H). LC-MS (ESI$^+$) m/z 320.1 (M+H)$^+$.

Step 4—Benzyl 4-[3-(bromomethyl)cyclobutoxy]piperidine-1-carboxylate

To a mixture of benzyl 4-[3-(hydroxymethyl)cyclobutoxy]piperidine-1-carboxylate (250 mg, 783 umol) and $PPh_3$ (616 mg, 2.35 mmol) in DCM (6.0 mL) was added $CBr_4$ (779 mg, 2.35 mmol) at 0° C. The reaction mixture was stirred at 25° C. for 12 hours. On completion, the reaction mixture was concentrated in vacuo to give the residue. The residue was purified by column chromatography (PE:EA=3:1) to give the title compound (200 mg, 65% yield) as colorless oil. $^1$H NMR (400 MHz, $CDCl_3$) δ 7.32-7.22 (m, 5H), 5.05 (s, 2H), 4.13-4.09 (m, 1H), 3.87-3.68 (m, 2H), 3.47-3.31 (m, 3H), 3.10-3.05 (m, 2H), 2.69-2.51 (m, 1H), 2.20-1.96 (m, 4H), 1.73-1.68 (m, 2H), 1.46-1.33 (m, 2H).

3-[3-Methyl-2-oxo-4-[[3-(4-piperidyloxy)cyclobutyl]methyl]benzimidazol-1-yl]piperidine -2,6-dione (Intermediate AXH)

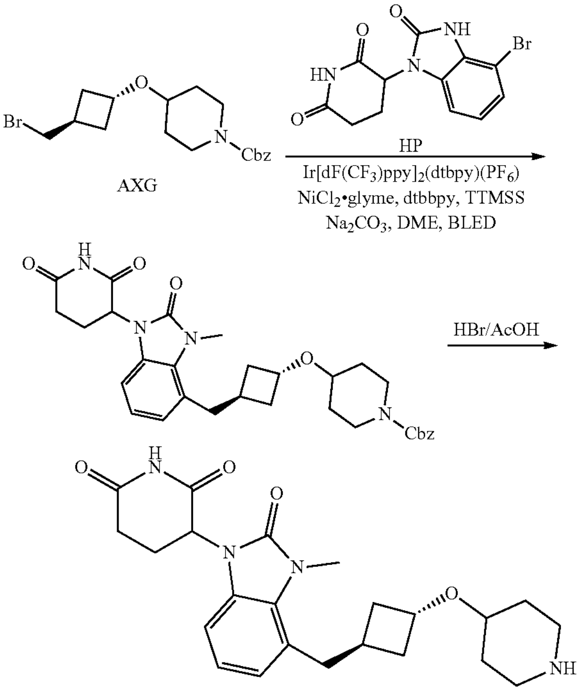

AXH

Step 1—Benzyl 4-[3-[[1-(2,6-dioxo-3-piperidyl)-3-methyl-2-oxo-benzimidazol-4-yl]methyl]cyclobutoxy]piperidine-1-carboxylate To an 40 mL vial equipped with a stir bar was added benzyl 4-[3-(bromomethyl)cyclobutoxy]piperidine-1-carboxylate (150 mg, 392 umol, Intermediate AXG), 3-(4-bromo-3-methyl-2-oxo-benzimidazol-1-yl) piperidine-2,6-dione (133 mg, 392 umol, Intermediate HP), Ir[dF($CF_3$)ppy]$_2$(dtbpy)($PF_6$) (4.40 mg, 3.92 umol), dichloronickel; 1,2-dimethoxyethane (431 ug, 1.96 umol), 4-tert-butyl-2-(4-tert-butyl-2-pyridyl)pyridine (631 ug, 2.35 umol), TTMSS (97.6 mg, 392 umol) and $Na_2CO_3$ (83.2 mg, 785 umol) in DME (6.0 mL). The reaction mixture was stirred and irradiated with a 34 W blue LED lamp at 25° C. for 14 hr. On completion, the reaction mixture was filtered and the filtrate was concentrated in vacuo to give a residue. The residue was purified by reverse phase flash (0.1% FA condition) to give the title compound (100 mg, 45.46% yield) as black brown solid. $^1$H NMR (400 MHz, $CDCl_3$) δ 8.12 (s, 1H), 7.39-7.32 (m, 5H), 7.08-6.96 (m, 1H), 6.86 (d, J=7.6 Hz, 1H), 6.70 (d, J=7.6 Hz, 1H), 5.32-5.19 (m, 2H), 5.14 (s, 1H), 4.29-4.25 (m, 1H), 3.98-3.79 (m, 2H), 3.68 (s, 3H), 3.54-3.39 (m, 1H), 3.24-3.05 (m, 4H), 3.01-2.70 (m, 3H), 2.53-2.51 (m, 1H), 2.33-2.00 (m, 5H), 1.93-1.77 (m, 2H), 1.55-1.45 (m, 2H).

Step 2—3-[3-Methyl-2-oxo-4-[[3-(4-piperidyloxy)cyclobutyl]methyl]benzimidazol-1-yl]piperidine -2,6-dione A mixture of benzyl4-[3-[[1-(2,6-dioxo-3-piperidyl)-3-methyl-2-oxo-benzimidazol-4-yl]methyl]cyclobutoxy]piperidine-1-carboxylate (70.0 mg, 125 umol) in HBr/AcOH (3.0 mL) was stirred at 25° C. for 2 hr under $N_2$ atmosphere. On completion, the reaction mixture was concentrated in vacuo to give the title compound (60.0 mg, 56% yield, HBr salt) as yellow solid. LC-MS (ESI+) m/z 427.2 $(M+H)^+$.

6-(Difluoromethoxy)-N-[2-(4-formylcyclohexyl)-6-(1-hydroxy-1-methyl-ethyl)indazol-5-yl]pyridine-2-carboxamide (Intermediate AXI)

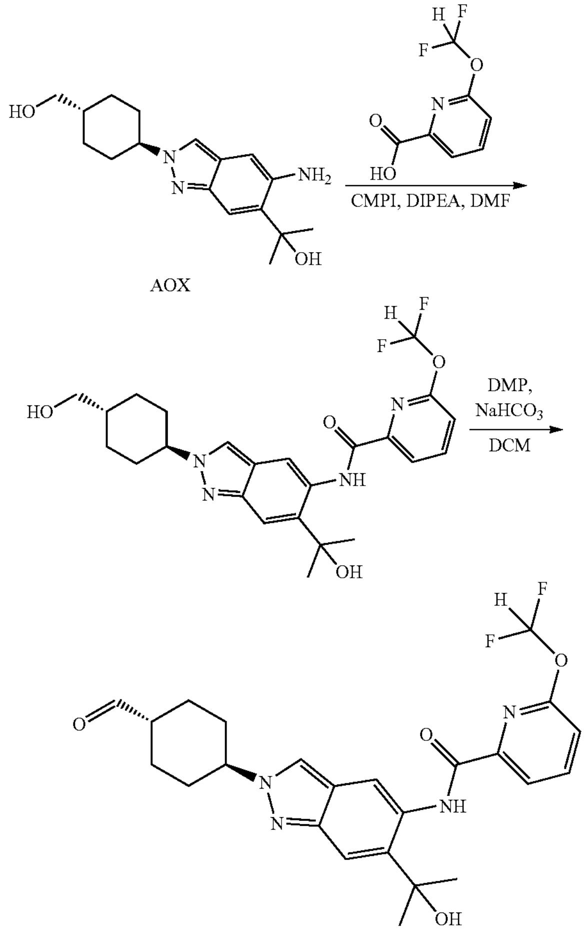

AOX
AXI

Step 1—6-(Difluoromethoxy)-N-[2-[4-(hydroxymethyl)cyclohexyl]-6-(1-hydroxy-1-methyl-ethyl)indazol-5-yl]pyridine-2-carboxamide To a solution of 2-[5-amino-2-[4-(hydroxymethyl)cyclohexyl]indazol-6-yl]propan-2-ol (360 mg, 1.07 mmol, Intermediate AOX) in DMF (2.00 mL) was added a mixture of 6-(difluoromethoxy)pyridine- 2-carboxylic acid (200 mg, 1.06 mmol, CAS #1522367-81-2), CMPI (324 mg, 1.27 mmol) and DIPEA (410 mg, 3.17 mmol, 552 uL) in DMF (1.00 mL). The mixture was stirred at 20° C. for 1 hr. On completion, the reaction mixture was concentrated in vacuo to give a residue, then diluted with water (20 mL) and extracted with EA (3×20 mL). The combined organic layers were washed with brine (2×40 mL), dried over $Na_2SO_4$. The filtrate was concentrated to give a residue. The residue was purified by reversed-phase (0.1% FA condition) to give the title compound (250 mg, 49% yield) as a yellow solid. $^1$H NMR (400 MHz, DMSO-$d_6$) δ 12.33 (s, 1H), 8.76 (s, 1H), 8.36 (s, 1H), 8.29-7.85 (m, 3H), 7.59 (s, 1H), 7.36 (d, J=7.8 Hz, 1H), 6.32 (s, 1H), 4.50 (s, 1H), 4.46-4.34 (m, 1H), 3.29-3.24 (m, 2H), 2.14 (d, J=8.4 Hz, 2H), 1.98-1.84 (m, 4H), 1.65 (s, 6H), 1.55-1.44 (m, 1H), 1.23-1.08 (m, 2H).

Step 2—6-(Difluoromethoxy)-N-[2-(4-formylcyclohexyl)-6-(1-hydroxy-1-methyl-ethyl)indazol-5-yl]pyridine-2-carboxamide To a solution of 6-(difluoromethoxy)-N-[2-[4-(hydroxymethyl)cyclohexyl]-6-(1-hydroxy-1-methyl- ethyl)indazol-5-yl]pyridine-2-carboxamide (100 mg, 210 umol) in DCM (8.00 mL) was added DMP (134 mg, 316 umol, 97.8 uL) and $NaHCO_3$ (88.5 mg, 1.05 mmol, 40.9 uL) at 0° C. The mixture was stirred at 20° C. for 2 hrs. On completion, the reaction mixture was quenched by addition saturated solution of $Na_2S_2O_3$ (4 mL), and saturated solution of $NaHCO_3$ (4 mL), then extracted with DCM (3×10 mL). The combined organic layers was washed with solution of $NaHCO_3$ (3×20 mL), then washed with brine (2×20 mL), dried over anhydrous $Na_2SO_4$, filtered and concentrated in vacuo to give the title compound (95.0 mg, 95% yield) as a yellow solid. $^1$H NMR (400 MHz, DMSO-$d_6$) δ 12.33 (s, 1H), 9.64 (s, 1H), 8.77 (s, 1H), 8.39-8.33 (m, 1H), 8.26-7.89 (m, 3H), 7.60 (s, 1H), 7.36 (d, J=8.0 Hz, 1H), 6.33 (s, 1H), 4.49-4.41 (m, 1H), 2.45-2.37 (m, 1H), 2.26-2.17 (m, 2H), 2.11 (d, J=11.2 Hz, 2H), 2.03-1.93 (m, 2H), 1.65 (s, 6H), 1.50-1.39 (m, 2H).

3-(3-methyl-4-(((1r,3s)-3-(3-(methylamino)propoxy) cyclobutyl)methyl)-2-oxo-2,3-dihydro- 1H-benzo[d] imidazol-1-yl)piperidine-2,6-dione (Intermediate AXJ)

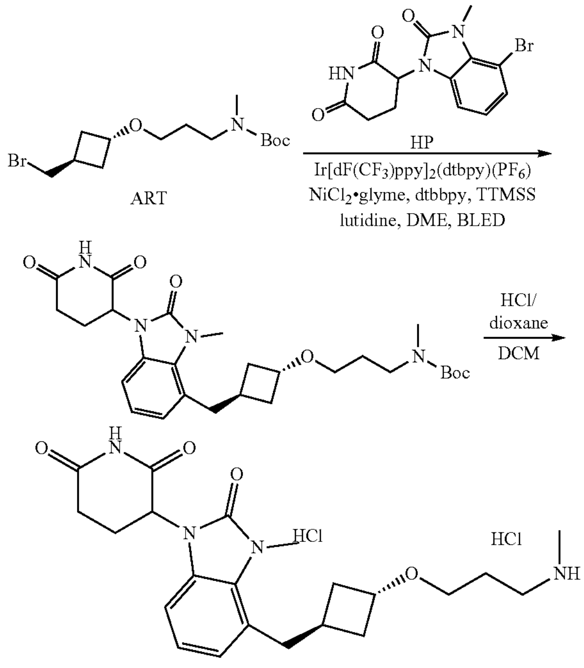

ART
AXJ

Step 1—Tert-butyl (3-((1s,3r)-3-((1-(2,6-dioxopiperidin-3-yl)-3-methyl-2-oxo-2,3-dihydro-1H- benzo[d]imidazol-4-yl)methyl)cyclobutoxy)propyl)(methyl)carbamate To an 40 mL vial equipped with a stir bar was added tert-butyl(3-((1r,3r)-3-(bromomethyl)cyclobutoxy)propyl)(methyl)carbamate (400 mg, 1.19 mmol, Intermediate ART), 3-(4-bromo-3-methyl-2-oxo-benzimidazol-1-yl)piperidine-2,6-dione (335 mg, 991 umol, Intermediate HP), bis[3,5-difluoro-2-[5- (trifluoromethyl)-2-pyridyl]phenyl]iridium(1+);4-tert-butyl-2-(4-tert-butyl-2-pyridyl)pyridine; hexafluorophosphate (11.1 mg, 9.91 umol, CAS #2173009-61-3), NiCl2.dtbbpy (1.97 mg, 4.96 umol), TTMSS (246 mg, 991 umol, 305 uL) and 2,6-dimethylpyridine (212 mg, 1.98 mmol, 230 uL) in DME (8.00 mL). The vial was sealed and placed under nitrogen was added. The reaction was stirred and irradiated with a 34 W blue LED lamp (7 cm away), with cooling fan to keep the reaction temperature at 25° C. for 14 hrs. On completion, the reaction mixture was filtered. The filtrate was concentrated in vacuo to give a residue. The residue was purified by reversed phase (0.1% FA condition) to give the title compound (60.0 mg, 11% yield) as a yellow solid. $^1$H NMR (400 MHz, DMSO-$d_6$) δ 11.15-10.99 (m, 1H), 7.00-6.92 (m, 2H), 6.83 (dd, J=2.4, 6.4 Hz, 1H), 5.35 (dd, J=5.4, 12.4 Hz, 1H), 4.16-4.08 (m, 1H), 3.54 (s, 3H), 3.24 (t, J=6.4 Hz, 2H), 3.19 (t, J=6.8 Hz, 2H), 3.07 (d, J=7.6 Hz, 2H), 2.93-2.84 (m, 1H), 2.75 (s, 3H), 2.72-2.67 (m, 1H), 2.64-2.58 (m, 1H), 2.56-2.53 (m, 1H), 2.07-1.95 (m, 5H), 1.71-1.61 (m, 2H), 1.37 (s, 9H).

Step 2—3-(3-methyl-4-(((1r,3s)-3-(3-(methylamino)propoxy)cyclobutyl)methyl)-2-oxo-2,3-dihydro-1H-benzo[d]imidazol-1-yl)piperidine-2,6-dione To a solution of tert-butyl (3-((1s,3r)-3-((1-(2,6-dioxopiperidin-3-yl)-3-methyl-2-oxo-2,3-dihydro- 1H-benzo[d]imidazol-4-yl)methyl)cyclobutoxy)propyl)(methyl)carbamate (60.0 mg, 116 umol) in DCM (4.00 mL) was added HCl/dioxane (4 M, 1.00 mL). The mixture was stirred at 20° C. for 1 hr. On completion, the reaction mixture was concentrated in vacuo to give the title compound (50.0 mg, 95% yield, HCl) as a yellow solid. LC-MS (ESI$^+$) m/z 415.2 $(M+H)^+$.

5-Fluoro-N-(2-((1r,4r)-4-formylcyclohexyl)-6-(2-hydroxypropan-2-yl)-2H-indazol-5-yl)-6- methylpicolinamide (Intermediate AXK)

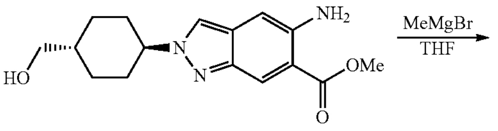

ARE

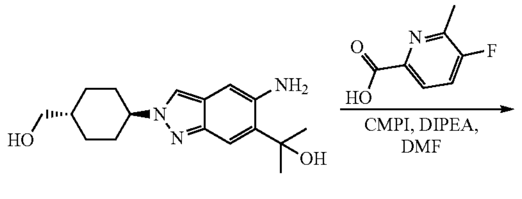

-continued

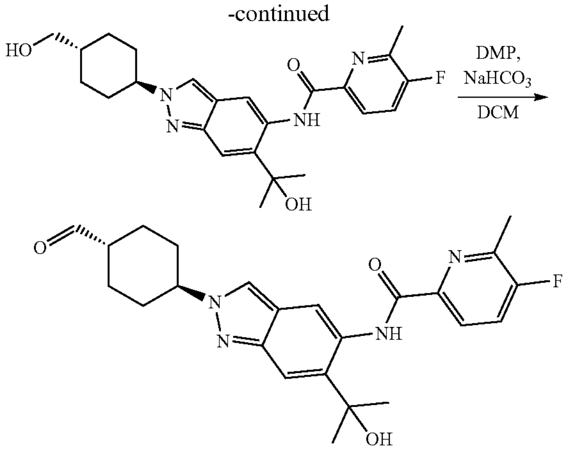

AXK

Step 1—2-(5-Amino-2-((1r,4r)-4-(hydroxymethyl)cyclohexyl)-2H-indazol-6-yl)propan-2-ol To a mixture of methyl methyl 5-amino-2-((1r,4r)-4-(hydroxymethyl)cyclohexyl)-2H-indazole- 6-carboxylate (7.00 g, 23.0 mmol, Intermediate ARE) in THE (50 mL) was added MeMgBr (3.00 M, 76.9 mL) at 0° C. under $N_2$. The mixture was stirred at 25° C. for 4 hours. On completion, the mixture was quenched with saturated aqueous $NH_4Cl$ (30 mL) at 0° C., and extracted with DCM (3×30 mL). The combined organic phase was dried over $Na_2SO_4$, filtered and the filtrate was concentrated in vacuo. The mixture was purified by reverse phase: (0.1% FA) to give the title compound (3.00 g, 42% yield) as yellow solid. $^1$H NMR (400 MHz, DMSO-$d_6$) δ 8.14 (s, 1H), 7.88 (s, 1H), 7.32 (s, 1H), 6.64 (s, 1H), 4.30-4.23 (m, 1H), 3.30-3.25 (m, 2H), 2.08-2.05 (m, 2H), 1.92-1.77 (m, 4H), 1.59 (s, 6H), 1.50-1.42 (m, 2H), 1.18-1.02 (m, 2H).

Step 2—5-Fluoro-N-(2-((1r,4r)-4-(hydroxymethyl)cyclohexyl)-6-(2-hydroxypropan-2-yl)-2H-indazol-5-yl)-6-methylpicolinamide To a solution of 2-(5-amino-2-((1r,4r)-4-(hydroxymethyl)cyclohexyl)-2H-indazol-6-yl)propan-2-ol (300 mg, 988 umol), 5-fluoro-6-methyl-pyridine-2-carboxylic acid (153 mg, 988 umol, CAS #1005474-88-3) in DMF (5.00 mL) was added CMPI (303 mg, 1.19 mmol) and DIPEA (383 mg, 2.97 mmol). The mixture was stirred at 25° C. for 1 hr. On completion, the mixture was quenched with $H_2O$ (0.5 mL) and concentrated in vacuo. The mixture was purified by reverse phase: (0.1% FA) to give the title compound (380 mg, 87% yield) as yellow solid. $^1$H NMR (400 MHz, DMSO-$d_6$) δ 12.37 (s, 1H), 8.69 (s, 1H), 8.35 (s, 1H), 8.10-8.03 (m, 1H), 7.90-7.80 (m, 1H), 7.57 (s, 1H), 5.98 (s, 1H), 4.54-4.47 (m, 1H), 4.46-4.35 (m, 1H), 3.31-3.27 (m, 2H), 2.59 (d, J=2.8 Hz, 3H), 2.19-2.10 (m, 2H), 1.98-1.83 (m, 4H), 1.64 (s, 6H), 1.54-1.40 (m, 1H), 1.24-1.06 (m, 2H), LC-MS (ESI$^+$) m/z 441.3 $(M+H)^+$.

Step 3—5-Fluoro-N-(2-((1r,4r)-4-formylcyclohexyl)-6-(2-hydroxypropan-2-yl)-2H-indazol-5-yl)-6- methylpicolinamide To a solution of 5-fluoro-N-(2-((1r,4r)-4-(hydroxymethyl)cyclohexyl)-6-(2-hydroxypropan-2-yl)- 2H-indazol-5-yl)-6-methylpicolinamide (80.0 mg, 181 umol) in DCM (3.00 mL) was added DMP (92.4 mg, 217 umol) and $NaHCO_3$ (76.2 mg, 908 umol). The mixture was stirred at 25° C. for 1 hr. On completion, the mixture was diluted with DCM (20 mL) then quenched with saturated $Na_2S_2O_3$ (15 mL) and washed with saturated $NaHCO_3$ (2×15 mL). The organic layer was dried over anhydrous $Na_2SO_4$, filtered and concentrated in vacuo to give the title compound (75 mg, 94% yield) as white solid. $^1H$ NMR (400 MHz, DMSO-$d_6$) δ 12.36 (s, 1H), 9.65 (s, 1H), 8.70 (s, 1H), 8.35 (s, 1H), 8.10-8.02 (m, 1H), 7.90-7.82 (m, 1H), 7.57 (s, 1H), 5.97 (s, 1H), 4.49-4.42 (m, 1H), 3.63-3.58 (m, 1H), 2.58 (d, J=2.8 Hz, 3H), 2.24-2.17 (m, 2H), 2.15-2.07 (m, 2H), 2.04-1.96 (m, 2H), 1.64 (s, 6H), 1.49-1.42 (m, 2H), LC-MS (ESI$^+$) m/z 439.3 (M+H)$^+$.

N-[2-(4-formylcyclohexyl)-6-(1-hydroxy-1-methyl-ethyl)indazol-5-yl]-6-methoxy-pyridine-2- carboxamide (Intermediate AXL)

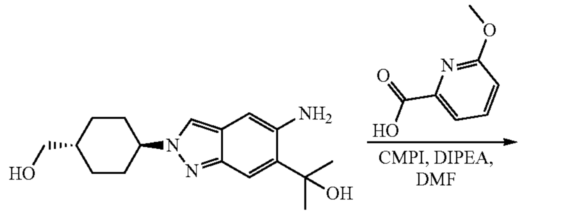

AOX

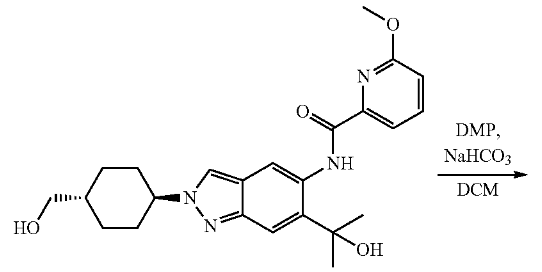

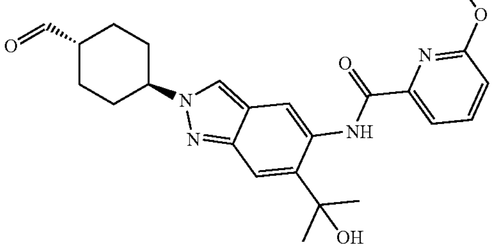

AXL

Step 1—N-[2-[4-(hydroxymethyl)cyclohexyl]-6-(1-hydroxy-1-methyl-ethyl)indazol-5-yl]-6-methoxy-pyridine-2-carboxamide To a solution of 2-[5-amino-2-[4-(hydroxymethyl)cyclohexyl]indazol-6-yl]propan-2-ol (300 mg, 988 umol, Intermediate AOX), 6-methoxypyridine-2-carboxylic acid (151 mg, 988 umol, CAS #26893-73-2) in DMF (5.00 mL) was added CMPI (303 mg, 1.19 mmol) and DIPEA (383 mg, 2.97 mmol). The mixture was stirred at 25° C. for 1 hr. On completion, the mixture was quenched with $H_2O$ (0.5 mL) and concentrated in vacuo. The mixture was purified by reverse phase: (0.1% FA) to give the title compound (380 mg, 87% yield) as yellow solid. $^1H$ NMR (400 MHz, DMSO-$d_6$) δ 12.29 (s, 1H), 8.77 (s, 1H), 8.35 (s, 1H), 8.02-7.86 (m, 1H), 7.78 (d, J=7.2 Hz, 1H), 7.58 (s, 1H), 7.07 (d, J=8.4 Hz, 1H), 6.01 (s, 1H), 4.51 (t, J=5.2 Hz, 1H), 4.46-4.36 (m, 1H), 4.04 (s, 3H), 3.32-3.28 (m, 2H), 2.21-2.08 (m, 2H), 1.99-1.82 (m, 4H), 1.65 (s, 6H), 1.56-1.41 (m, 1H), 1.25-1.08 (m, 2H), LC-MS (ESI$^+$) m/z 439.3 (M+H)$^+$.

Step 2—N-[2-(4-formylcyclohexyl)-6-(1-hydroxy-1-methyl-ethyl)indazol-5-yl]-6-methoxy-pyridine-2-carboxamide To a solution of N-[2-[4-(hydroxymethyl)cyclohexyl]-6-(1-hydroxy-1-methyl-ethyl)indazol-5-yl]-6- methoxy-pyridine-2-carboxamide (80.0 mg, 182 umol) in DCM (3.00 mL) was added DMP (92.8 mg, 218 umol) and $NaHCO_3$ (76.6 mg, 912 umol). The mixture was stirred at 25° C. for 1 hr. On completion, the mixture was diluted with DCM (20 mL) then quenched with saturated $Na_2S_2O_3$ (15 mL) and washed with saturated $NaHCO_3$ (2×15 mL). The organic layer was dried over anhydrous $Na_2SO_4$, filtered and concentrated in vacuo to give the title compound (70.0 mg, 87% yield) as white solid. $^1H$ NMR (400 MHz, DMSO-$d_6$) δ 12.29 (s, 1H), 9.66 (s, 1H), 8.78 (s, 1H), 8.36 (s, 1H), 7.99-7.90 (m, 1H), 7.78 (d, J=7.2 Hz, 1H), 7.59 (s, 1H), 7.07 (d, J=8.4 Hz, 1H), 6.01 (s, 1H), 4.54-4.43 (m, 1H), 4.05 (s, 3H), 3.66-3.56 (m, 1H), 2.26-2.18 (m, 2H), 2.16-2.08 (m, 2H), 2.05-1.94 (m, 2H), 1.65 (s, 6H), 1.53-1.42 (m, 2H), LC-MS (ESI$^+$) m/z 437.2 (M+H)$^+$.

4-(Trifluoromethyl)thiazole-2-carboxamide (Intermediate AXM)

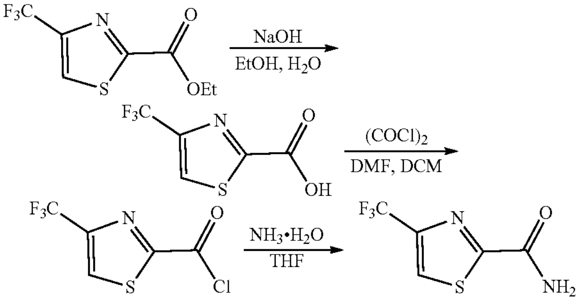

AXM

Step 1—4-(Trifluoromethyl)thiazole-2-carboxylic acid

To a solution of Ethyl 4-(trifluoromethyl)thiazole-2-carboxylate (2.00 g, 8.88 mmol, CAS #79247-86-2) in EtOH (50.0 mL) was added a solution of NaOH (1.20 g, 30.0 mmol) in $H_2O$ (30.0 mL). The mixture was stirred at 50° C. for 0.5 hour. On completion, the reaction was quenched with HCl (1 N, 30 mL), diluted with water (100 mL), and extracted with DCM (3×60 mL). The combined organic layer was dried over $Na_2SO_4$, filtered and concentrated in vacuo to give the title compound (1.3 g, 67% yield) as a white solid. LC-MS (ESI$^+$) m/z 198.0 (M+H)$^+$.

Step 2—4-(Trifluoromethyl)thiazole-2-carbonyl chloride

To a solution of 4-(trifluoromethyl)thiazole-2-carboxylic acid (1.30 g, 6.59 mmol) in DCM (30 mL) was added $(COCl)_2$ (1.26 g, 9.89 mmol) and DMF (48.2 mg, 660 umol) at 0° C. The mixture was stirred at 25° C. for 1 hour. On completion, the mixture was concentrated in vacuo to give the title compound (1.2 g, 72% yield) as yellow oil.

Step 3—4-(Trifluoromethyl)thiazole-2-carboxamide

To a solution of 4-(trifluoromethyl)thiazole-2-carbonyl chloride (1.20 g, 5.57 mmol) in THE (30 mL) was added $NH_3.H_2O$ (2.96 g, 27.8 mmol, 33% solution) at 0° C. The mixture was stirred at 25° C. for 1 hour. On completion, the mixture was concentrated in vacuo to give a residue. The crude product was purified by silica gel column chromatography (PE:EA from 10:1 to 1:1) to give the title compound (1.00 g, 82% yield) as a yellow solid.

N-[2-(4-formylcyclohexyl)-6-methoxy-indazol-5-yl]-4-(trifluoromethyl)thiazole-2-carboxamide (Intermediate AXN)

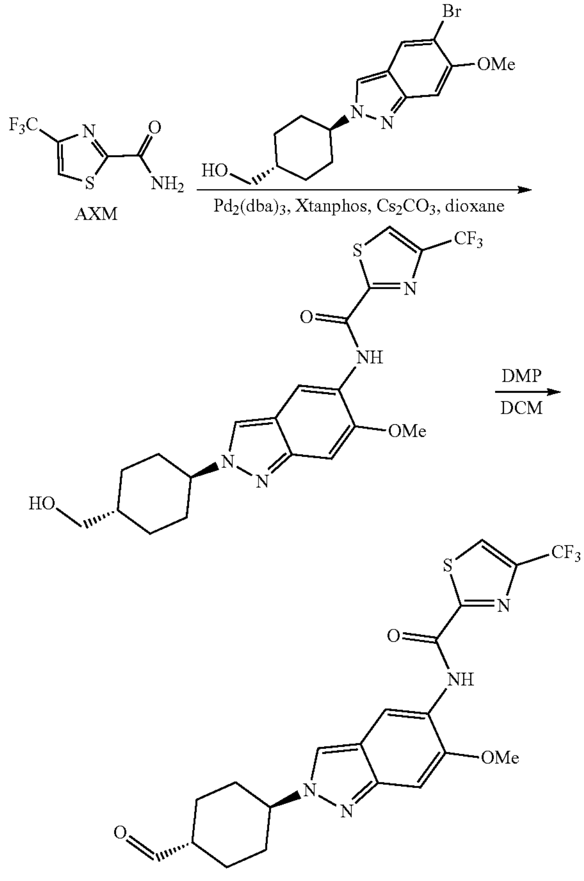

AXM

AXN

Step 1—N-[2-[4-(hydroxymethyl)cyclohexyl]-6-methoxy-indazol-5-yl]-4-(trifluoromethyl)thiazole-2-carboxamide To a solution of 4-(trifluoromethyl)thiazole-2-carboxamide (400 mg, 2.04 mmol, Intermediate AXM) and [4-(5-bromo-6-methoxy-indazol-2-yl)cyclohexyl]methanol (761 mg, 2.24 mmol, synthesized via Steps 1-3 of Intermediate ATE) in dioxane (10.0 mL) were added $Pd_2(dba)_3$ (187 mg, 203.9 umol), $Cs_2CO_3$ (1.33 g, 4.08 mmol) and Xantphos (118 mg, 204 umol). The mixture was degassed and purged with $N_2$ for 3 times and then it was stirred at 100° C. under $N_2$ for 16 hours. On completion, the mixture was concentrated in vacuo to give a residue. The residue was purified by silica gel column chromatography: (PE:EA from 5:1 to 0:1) to give the title compound (800 mg, 73% yield) as a yellow solid. LC-MS (ESI$^+$) m/z 455.3 $(M+H)^+$.

Step 2—N-[2-(4-formylcyclohexyl)-6-methoxy-indazol-5-yl]-4-(trifluoromethyl)thiazole-2-carboxamide To a solution of N-[2-[4-(hydroxymethyl)cyclohexyl]-6-methoxy-indazol-5-yl]-4-(trifluoromethyl)thiazole-2-carboxamide (400 mg, 880 umol) in DCM (8 mL) was added DMP (747 mg, 1.76 mmol). The mixture was stirred at 25° C. for 1 hour. On completion, the reaction was quenched with sat. $Na_2S_2O_3$ (30 mL), diluted with EA (100 mL), washed with sat.$NaHCO_3$ (2×50 mL) and brine (50 mL). The combined organic layer was dried over $Na_2SO_4$, filtered and concentrated in vacuo to give a residue. The residue was purified by silica gel column chromatography: (PE:EA from 5:1 to 1:2) to give the title compound (320 mg, 72% yield) as a yellow solid. LC-MS (ESI$^+$) m/z 453.1 $(M+H)^+$.

6-(Difluoromethyl)pyridine-2-carboxamide (Intermediate AXO)

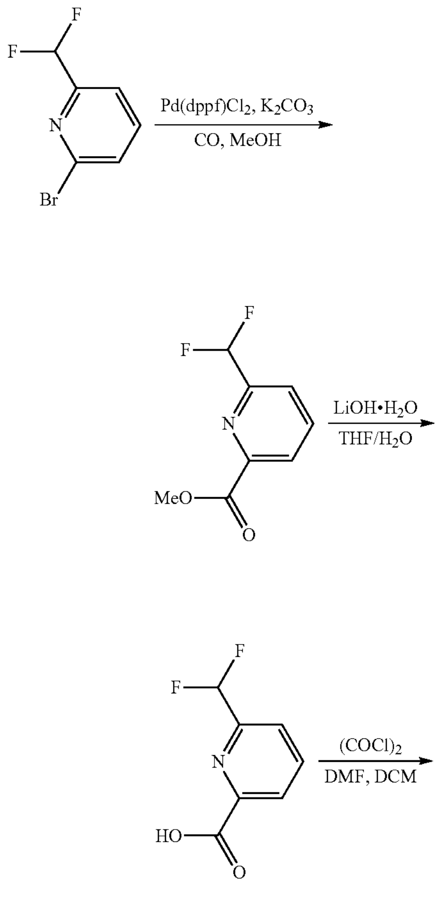

-continued

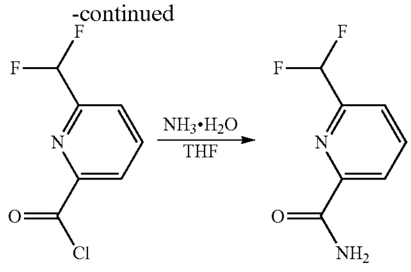

AXO

Step 1—Methyl 6-(difluoromethyl)pyridine-2-carboxylate

To a solution of 2-bromo-6-(difluoromethyl)pyridine (2.00 g, 9.62 mmol, CAS #872365-91-8) in MeOH (20 mL) and DMSO (20 mL) was added TEA (2.92 g, 28.8 mmol), $Pd(OAc)_2$ (215 mg, 961 umol) and DPPP (396 mg, 961 umol) at 25° C. The reaction mixture was stirred at 80° C. for 16 hours under CO (50 Psi). On completion, after cooled to 25° C., the mixture was diluted with $H_2O$ (60 mL) and extracted with EA (3×20 mL). The combined organic layers were washed by brine (20 mL), dried over by $Na_2SO_4$, filtered and the filtrate was concentrated in vacuo. The residue was purified by column chromatography to give the title compound (1.60 g, 88% yield) as colorless oil. $^1H$ NMR (400 MHz, $CDCl_3$) δ 8.22 (d, J=8.0 Hz, 1H), 8.01 (t, J=8.0 Hz, 1H), 7.83 (d, J=8.0 Hz, 1H), 6.74 (t, J=54.8 Hz, 1H), 4.01 (s, 3H); LC-MS ($ESI^+$) m/z 188.1 $(M+H)^+$.

Step 2—6-(Difluoromethyl)pyridine-2-carboxylic acid

To a solution of methyl 6-(difluoromethyl)pyridine-2-carboxylate (1.40 g, 7.48 mmol) in THF (24 mL) and $H_2O$ (12 mL) was added LiOH $H_2O$ (627 mg, 14.9 mmol) at 25° C. The reaction mixture was stirred at 25° C. for 2 hours. On completion, the mixture was concentrated in vacuo. The residue was purified by reverse phase (0.1% TFA condition) to give the title compound (1.50 g, 98% yield, 85% purity) as a white solid. LC-MS ($ESI^+$) m/z 174.2 $(M+H)^+$.

Step 3—6-(Difluoromethyl)pyridine-2-carbonyl chloride

To a solution of 6-(difluoromethyl)pyridine-2-carboxylic acid (330 mg, 1.81 mmol) in DCM (5 mL) was added $(COCl)_2$ (459 mg, 3.62 mmol) and DMF (13.2 mg, 181 umol) at 0° C. The mixture was stirred at 0-25° C. for 2 hours. On completion, the mixture was concentrated in vacuo to give the title compound (340 mg, 98% yield) as yellow oil.

Step 4—6-(Difluoromethyl)pyridine-2-carboxamide

A solution of 6-(difluoromethyl)pyridine-2-carbonyl chloride (340 mg, 1.77 mmol) in THF (5 mL) was added to $NH_3.H_2O$ (4.15 g, 35.5 mmol, 30% solution) at 0° C. The mixture was stirred at 0-25° C. for 1 hour. On completion, the reaction mixture was diluted with $H_2O$ (15 mL) and extracted with EA (3×5 mL). The combined organic layers were washed by brine (20 mL), dried over $Na_2SO_4$, filtered and the filtrate was concentrated in vacuo to give the title compound (180 mg, 58% yield) as a yellow solid. $^1H$ NMR (400 MHz, DMSO-$d_6$) δ 8.23-8.15 (m, 2H), 8.05 (s, 1H), 7.92-7.87 (m, 1H), 7.80 (s, 1H), 6.99 (t, J=54.8 Hz, 1H).

6-(Difluoromethyl)-N-[2-(4-formylcyclohexyl)-6-methoxy-indazol-5-yl]pyridine-2- carboxamide (Intermediate AXP)

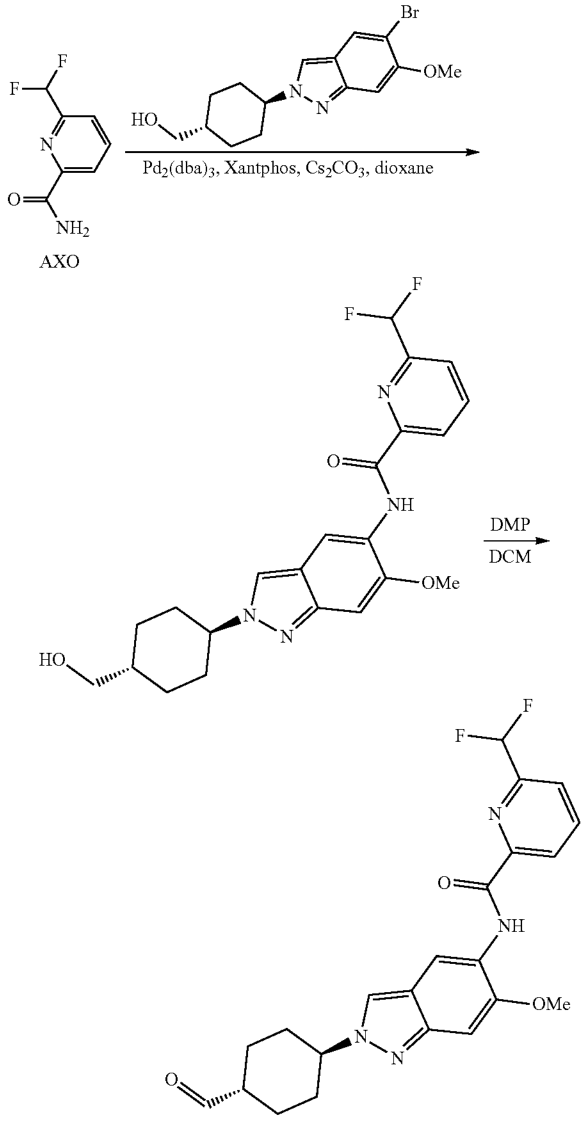

AXP

Step 1—6-(Difluoromethyl)-N-[2-[4-(hydroxymethyl)cyclohexyl]-6-methoxy-indazol-5-yl]pyridine-2- carboxamide To a solution of 6-(difluoromethyl)pyridine-2-carboxamide (180 mg, 1.05 mmol, Intermediate AXO) and [4-(5-bromo-6-methoxy-indazol-2-yl)cyclohexyl]methanol (461 mg, 1.36 mmol, synthesized via Steps 1-3 of Intermediate ATE) in dioxane (10 mL) was added $Pd_2(dba)_3$ (95.7 mg, 104 umol), Xantphos (121 mg, 209 umol) and $Cs_2CO_3$ (681 mg, 2.09 mmol) at 25° C., and the reaction mixture was stirred at 80° C. for 12 hours under $N_2$. On completion, the reaction mixture was diluted with $H_2O$ (20 mL) and extracted with EA (3×20 mL). The combined organic layers were washed with brine (2×10 mL), dried over by $Na_2SO_4$, filtered and the filtrate was concentrated in vacuo. The residue was purified by reverse phase (0.1% FA condition) to give the title compound (260 mg, 57% yield) as a white solid. $^1H$ NMR (400 MHz, DMSO-$d_6$) δ 10.55 (s, 1H), 8.68 (s, 1H), 8.39-8.25 (m, 3H), 7.99 (d, J=7.2 Hz, 1H), 7.32-6.96 (m, 2H), 4.49 (t, J=5.2 Hz, 1H), 4.43-4.28 (m, 1H), 3.99 (s, 3H), 3.31-3.27 (m, 2H), 2.19-2.08 (m, 2H), 1.98-1.82 (m, 4H), 1.53-1.42 (m, 1H), 1.23-1.07 (m, 2H); LC-MS (ESI$^+$) m/z 431.1 (M+H)$^+$.

Step 2—6-(Difluoromethyl)-N-[2-(4-formylcyclohexyl)-6-methoxy-indazol-5-yl]pyridine-2- carboxamide To a solution of 6-(difluoromethyl)-N-[2-[4-(hydroxymethyl)cyclohexyl]-6-methoxy-indazol-5-yl]pyridine-2-carboxamide (140 mg, 325 umol) in DCM (5 mL) was added DMP (179 mg, 422 umol) at 25° C. The reaction mixture was stirred at 25° C. for 2 hours. On completion, the reaction was quenched with sat. aq. $Na_2S_2O_3$ (2 mL) and sat. aq. $NaHCO_3$ (2 mL). The mixture was extracted with DCM (3×10 mL). The combined organic layers were concentrated in vacuo to give the title compound (130 mg, 93% yield) as colorless oil. LC-MS (ESI$^+$) m/z 429.2 (M+H)$^+$.

4-[6-Methoxy-5-[[6-(trifluoromethyl)pyridine-2-carbonyl]amino]indazol-2-yl]cyclohexane carboxylic acid (Intermediate AXQ)

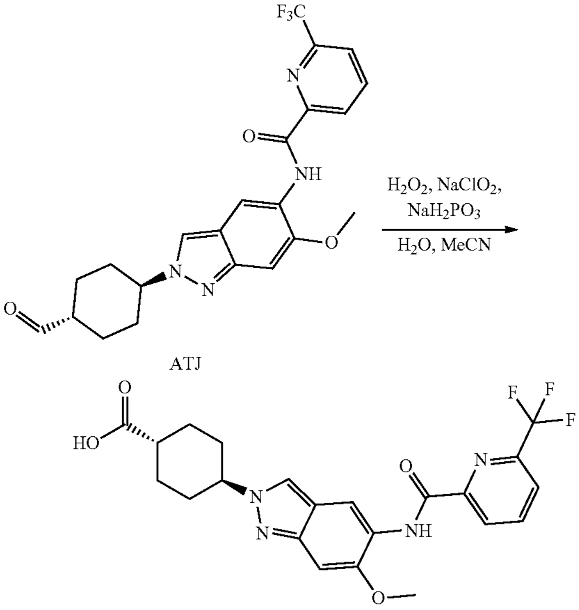

ATJ

AXQ

To a solution of N-[2-(4-formylcyclohexyl)-6-methoxy-indazol-5-yl]-6-(trifluoromethyl)pyridine-2-carboxamide (1.00 g, 2.24 mmol, Intermediate ATJ) and $NaH_2PO_4$ (1.34 g, 11.2 mmol) in ACN (20 mL) was added $H_2O_2$ (507 mg, 4.48 mmol, 30% solution) dropwise at 0° C. Then a solution of sodium chlorite (1.42 g, 15.6 mmol) in $H_2O$ (10 mL) was added and the reaction mixture was stirred at 0-25° C. for 1 hour. On completion, the reaction mixture was diluted with ACN (20 mL), quenched with $Na_2SO_3$ (10 mL) aqueous solution and filtered. The solid was dried in vacuo to give the title compound (800 mg, 80% yield) as brown solid. LC-MS (ESI$^+$) m/z 463.1 (M+H)$^+$.

6-Methylpyridine-2-carboxamide (Intermediate AXR)

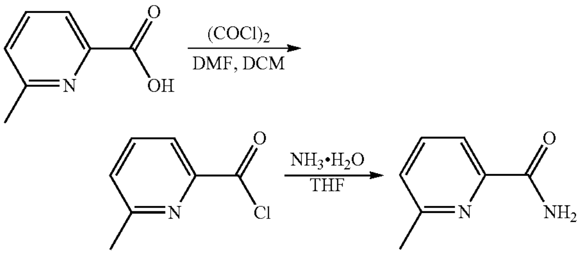

AXR

Step 1—6-Methylpyridine-2-carbonyl chloride

To a solution of 6-methylpyridine-2-carboxylic acid (1.00 g, 7.29 mmol, CAS #934-60-1) and $(COCl)_2$ (1.11 g, 8.75 mmol) in DCM (10 mL) was added DMF (53.3 mg, 729 umol) at 0° C. The reaction mixture was stirred at 0° C. for 2 hours. On completion, the reaction was concentrated in vacuo to give the title compound (1.10 g, 97% yield) as a white solid.

Step 2—6-Methylpyridine-2-carboxamide

A solution of 6-methylpyridine-2-carbonyl chloride (1.10 g, 7.07 mmol) in THE (5 mL) was added to $NH_3.H_2O$ (9.73 mL, 70.7 mmol, 28% solution) dropwise at 0° C. The reaction was stirred at 25° C. for 1 hour. On completion, the reaction mixture was diluted with $H_2O$ (20 mL), and extracted with EA (2×40 mL). The combined organic phase was dried over $Na_2SO_4$, and then concentrated in vacuo to give the title compound (560 mg, 58% yield) as a yellow solid. $^1H$ NMR (400 MHz, $CDCl_3$) δ 8.03-7.74 (m, 2H), 7.65 (t, J=7.6 Hz, 1H), 7.21 (d, J=7.6 Hz, 1H), 6.23 (s, 1H), 2.49 (s, 3H).

N-[2-(4-formylcyclohexyl)-6-methoxy-indazol-5-yl]-6-methyl-pyridine-2-carboxamide (Intermediate AXS)

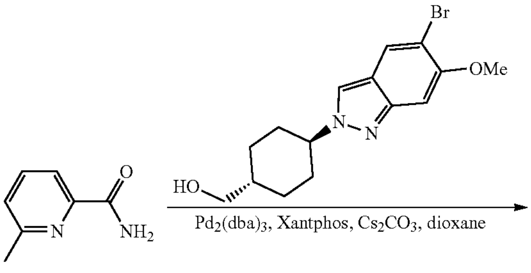

AXR

-continued

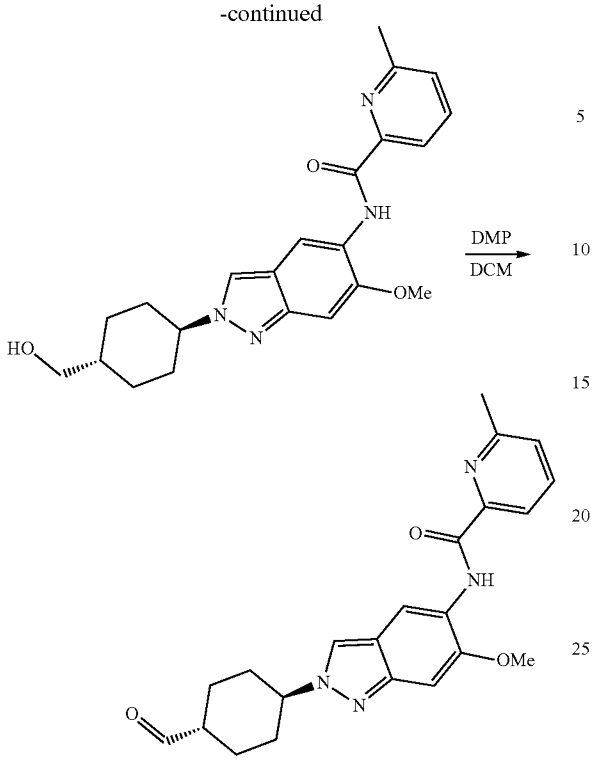

AXS

Step 1—N-[2-[4-(hydroxymethyl)cyclohexyl]-6-methoxy-indazol-5-yl]-6-methyl-pyridine-2- carboxamide To a solution of 6-methylpyridine-2-carboxamide (200 mg, 1.47 mmol, Intermediate AXR) and [4-(5-bromo-6-methoxy-indazol-2-yl)cyclohexyl]methanol (453 mg, 1.34 mmol, synthesized via Steps 1-3 of Intermediate ATE) in dioxane (5 mL) was addeed $Pd_2(dba)_3$ (122 mg, 133 umol), Xantphos (154 mg, 267 umol) and $Cs_2CO_3$ (870 mg, 2.67 mmol). The reaction mixture was stirred at 80° C. for 12 hours under $N_2$. On completion, the reaction mixture was filtered and the filtrate was concentrated in vacuo. The residue was purified by prep-HPLC (column: Phenomenex luna C18 150*40 mm*15 um; mobile phase: [water(0.225% FA)-ACN]; B %: 34%-64%, 9 min) to give the title compound (330 mg, 62% yield) as a yellow solid. $^1$H NMR (400 MHz, $CDCl_3$) δ 10.83 (s, 1H), 8.85 (s, 1H), 8.11 (d, J=7.6 Hz, 1H), 7.86 (s, 1H), 7.78 (t, J=7.6 Hz, 1H), 7.32 (d, J=7.2 Hz, 1H), 7.07 (s, 1H), 4.37-4.27 (m, 1H), 4.03 (s, 3H), 3.56 (d, J=6.4 Hz, 2H), 2.66 (s, 3H), 2.38-2.28 (m, 2H), 2.09-2.01 (m, 2H), 2.00-1.91 (m, 2H), 1.72-1.60 (m, 2H), 1.32-1.17 (m, 2H); LC-MS ($ESI^+$) m/z 395.1 $(M+H)^+$.

Step 2—N-[2-(4-formylcyclohexyl)-6-methoxy-indazol-5-yl]-6-methyl-pyridine-2-carboxamide To a solution of N-[2-[4-(hydroxymethyl)cyclohexyl]-6-methoxy-indazol-5-yl]-6-methyl- pyridine-2-carboxamide (100 mg, 253 umol) in DCM (4 mL) was added DMP (161 mg, 380 umol). The reaction mixture was stirred at 25° C. for 12 hours. On completion, the reaction mixture was quenched with $Na_2S_2O_3$ (15 mL) and extracted with DCM (2×30 mL). The combined organic phase was washed with sat. aq. $NaHCO_3$ (10 mL) and brine (2×15 mL), dried with anhydrous $Na_2SO_4$, filtered and concentrated in vacuo to give the title compound (95.0 mg, 95% yield) as a yellow solid. $^1$H NMR (400 MHz, DMSO-$d_6$) δ 10.70 (s, 1H), 9.64 (s, 1H), 8.70 (s, 1H), 8.30 (s, 1H), 8.01-7.94 (m, 2H), 7.55 (dd, J=1.2, 7.2 Hz, 1H), 7.13 (s, 1H), 4.45-4.33 (m, 1H), 4.00 (s, 3H), 2.62 (s, 3H), 2.47-2.36 (m, 1H), 2.29-2.15 (m, 2H), 2.14-2.06 (m, 2H), 2.01-1.89 (m, 2H), 1.51-1.37 (m, 2H).

[4-(5-Bromo-6-ethoxy-indazol-2-yl)cyclohexyl]methanol (Intermediate AXT)

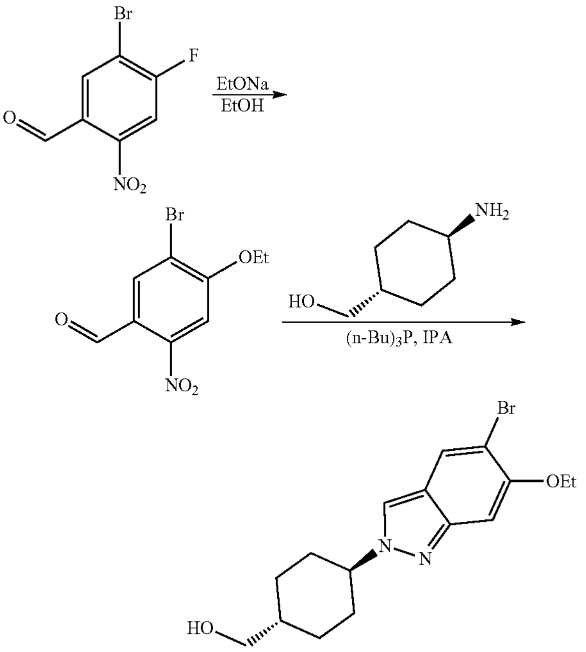

AXT

Step 1—5-Bromo-4-ethoxy-2-nitro-benzaldehyde

To a mixture of 5-bromo-4-fluoro-2-nitro-benzaldehyde (5.00 g, 20.1 mmol, synthesized via Step 1 of Intermediate ATE) in EtOH (40 mL) was added NaOEt (2.06 g, 30.2 mmol). The mixture was stirred at 25° C. for 12 hours. On completion, the mixture was concentrated in vacuo. Then water (30 mL) was added into the mixture. The aqueous phase was extracted with ethyl acetate (2×30 mL). The combined organic phase was washed with brine (2×30 mL), dried with anhydrous $Na_2SO_4$, filtered and concentrated in vacuo to give the residue. The residue was purified by column chromatography ($SiO_2$, PE:EA=50:1 to 10:1) to give the title compound (1.7 g, 30% yield) as a yellow solid. $^1$H NMR (400 MHz, DMSO-$d_6$) δ 10.04 (s, 1H), 8.17 (s, 1H), 7.77 (s, 1H), 4.35 (d, J=7.2 Hz, 2H), 1.41 (d, J=7.2 Hz, 3H).

Step 2—[4-(5-Bromo-6-ethoxy-indazol-2-yl)cyclohexyl]methanol

A solution of 5-bromo-4-ethoxy-2-nitro-benzaldehyde (500 mg, 1.82 mmol) and (4-aminocyclohexyl)methanol (259 mg, 2.01 mmol) in IPA (3 mL) was stirred at 80° C. for 12 hours. The mixture was cooled to 20° C. Then tributylphosphane (1.11 g, 5.47 mmol) was added into the mixture and stirred at 80° C. for 12 hours. On completion, the reaction mixture was cooled to 25° C. and concentrated in vacuo to give a residue. The residue was purified by column chromatography ($SiO_2$, PE/EA=3:1) to give the title compound (365 mg, 56% yield) as brown solid. LC-MS ($ESI^+$) m/z 353.0 $(M+H)^+$.

N-[6-ethoxy-2-(4-formylcyclohexyl)indazol-5-yl]-6-(trifluoromethyl)pyridine-2-carboxamide (Intermediate AXU)

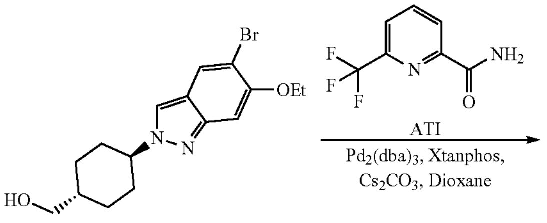

AXT

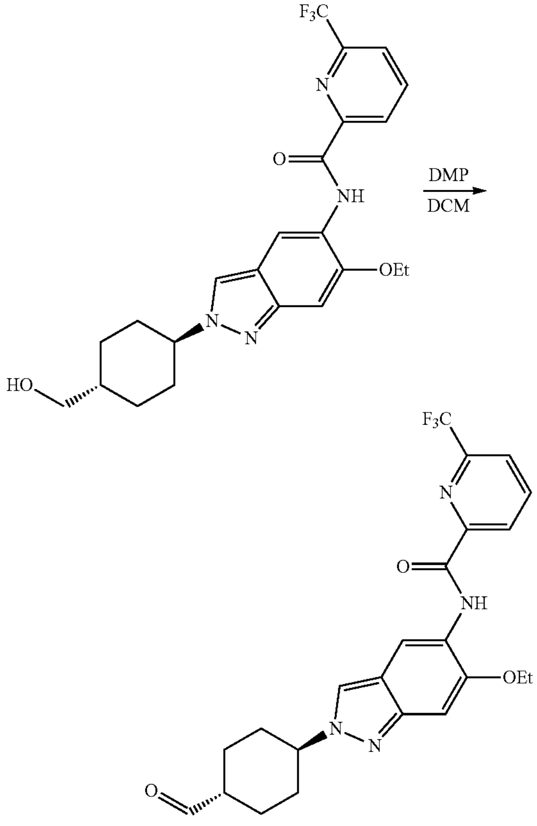

AXU

Step 1—N-[6-ethoxy-2-[4-(hydroxymethyl)cyclohexyl]indazol-5-yl]-6-(trifluoromethyl)pyridine-2-carboxamide To a solution of [4-(5-bromo-6-ethoxy-indazol-2-yl)cyclohexyl]methanol (350 mg, 990 umol, Intermediate AXT) in dioxane (15 mL) was added $Pd_2(dba)_3$ (90.7 mg, 99.0 umol), Xantphos (114 mg, 198 umol), $Cs_2CO_3$ (645 mg, 1.98 mmol) and 6-(trifluoromethyl)pyridine-2-carboxamide (207 mg, 1.09 mmol, Intermediate ATI). The mixture was stirred at 80° C. for 12 hours. On completion, the reaction was concentrated in vacuo to give a residue. The residue was purified by column chromatography ($SiO_2$, PE:EA=5:1 to 0:1) to give the title compound (165 mg, 36% yield) as a brown solid. $^1H$ NMR (400 MHz, $CDCl_3$) δ 10.93 (s, 1H), 8.84 (s, 1H), 8.51 (d, J=7.6 Hz, 1H), 8.14 (t, J=15.6 Hz, 1H), 7.90-7.88 (m, 1H), 7.07 (s, 1H), 4.35 (m, 1H), 4.21 (q, 2H), 3.59 (d, J=4.4 Hz, 2H), 2.40-2.32 (m, 2H), 2.12-1.94 (m, 4H), 1.75-1.62 (m, 4H), 1.46-1.39 (m, 1H), 1.36-1.19 (m, 3H).

Step 2—N-[6-ethoxy-2-(4-formylcyclohexyl)indazol-5-yl]-6-(trifluoromethyl)pyridine-2-carboxamide To a mixture of N-[6-ethoxy-2-[4-(hydroxymethyl)cyclohexyl]indazol-5-yl]-6-(trifluoromethyl)pyridine-2-carboxamide (114 mg, 246 umol) in DCM (10.0 mL) was added DMP (115 mg, 271 umol). The reaction mixture was stirred at 25° C. for 0.5 hour. On completion, the reaction mixture was poured into the water (80 mL), and extracted with DCM (2×60 mL). The combined organic phase was washed with brine (2×50 mL), dried with anhydrous $Na_2SO_4$, filtered and concentrated in vacuo to give the title compound (108 mg, 95% yield) as a brown solid. $^1H$ NMR (400 MHz, $CDCl_3$) δ 10.84 (s, 1H), 9.65 (s, 1H), 8.75 (s, 1H), 8.42 (d, J=7.6 Hz, 1H), 8.05 (d, J=8.0 Hz, 1H), 7.79 (s, 1H), 6.97 (s, 1H), 4.30-4.22 (m, 1H), 4.12 (d, J=6.8 Hz, 2H), 2.32 (d, J=11.6 Hz, 2H), 2.22-2.15 (m, 2H), 1.98 (d, J=16.0 Hz, 2H), 1.59 (s, 2H), 1.54 (t, J=6.8 Hz, 3H), 1.48-1.44 (m, 2H).

Benzyl N-[3-(3-aminocyclobutoxy)propyl]-N-methyl-carbamate (Intermediate AYJ)

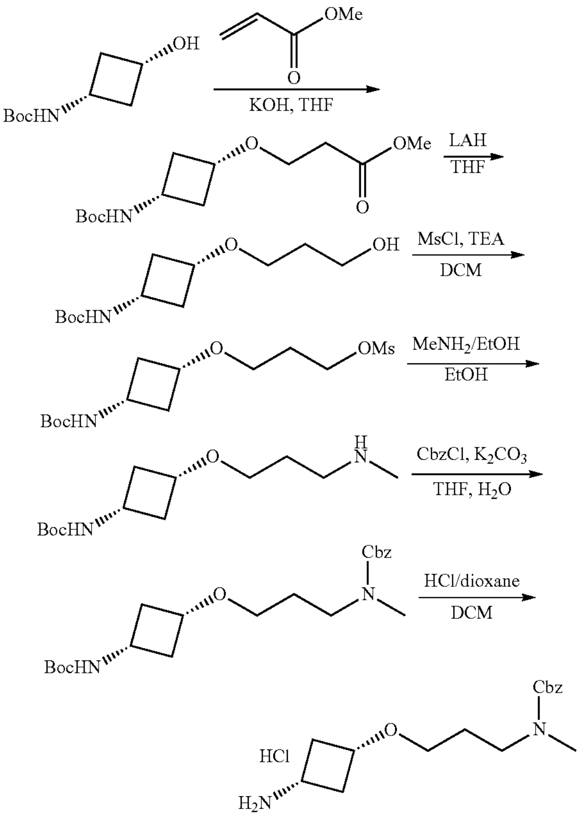

AYJ

Step 1—Methyl 3-[3-(tert-butoxycarbonylamino) cyclobutoxy]propanoate

To a mixture of tert-butyl N-(3-hydroxycyclobutyl)carbamate (2.60 g, 13.8 mmol, CAS #389890-43-1) and methyl prop-2-enoate (2.39 g, 27.7 mmol, CAS #96-33-3) in THF (30 mL) was added KOH (77.9 mg, 1.39 mmol). The reaction mixture was stirred at 25° C. for 12 hours. On completion, the reaction mixture was concentrated in vacuo. The residue was purified by column chromatography to give the title compound (1.89 g, 49% yield) as colourless oil. $^1$H NMR (400 MHz, $CDCl_3$) δ 4.80-4.54 (m, 1H), 3.82-3.71 (m, 1H), 3.69 (s, 3H), 3.68-3.63 (m, 1H), 3.59 (t, J=6.4 Hz, 2H), 2.70 (d, J=6.8 Hz, 2H), 2.55 (t, J=6.4 Hz, 2H), 1.79-1.71 (m, 2H), 1.42 (s, 9H).

Step 2—Tert-butyl N-[3-(3-hydroxypropoxy)cyclobutyl]carbamate

To a mixture of methyl 3-[3-(tert-butoxycarbonylamino) cyclobutoxy]propanoate (1.89 g, 6.91 mmol) in THF (30 mL) was added LAH (288 mg, 7.61 mmol) at 0° C. The reaction mixture was stirred at 0° C. for 2 hours. On completion, the reaction was quenched with water (0.05 mL) and 15% aq.NaOH (0.05 mL) at 0° C. and dried over $Na_2SO_4$. Then the mixture was filtered and the filtrate was concentrated in vacuo to give the title compound (1.69 g, 99% yield) as colorless oil. $^1$H NMR (400 MHz, $CDCl_3$) δ 4.73 (s, 1H), 3.76-3.73 (m, 2H), 3.69-3.62 (m, 1H), 3.49 (t, J=6.0 Hz, 2H), 2.77-2.68 (m, 2H), 2.57-2.18 (m, 1H), 1.84-1.73 (m, 4H), 1.42 (s, 9H).

Step 3—3-[3-(Tert-butoxycarbonylamino)cyclobutoxy]propyl methanesulfonate

To a mixture of tert-butyl N-[3-(3-hydroxypropoxy)cyclobutyl]carbamate (1.69 g, 6.89 mmol) and TEA (1.39 g, 13.7 mmol) in DCM (20 mL) was added MsCl (946 mg, 8.27 mmol). The reaction mixture was stirred at 25° C. for 1 hour. On completion, the reaction mixture was diluted with water (30 mL) and extracted with DCM (2×30 mL). The combined organic layer was dried over $Na_2SO_4$, filtered and concentrated in vacuo to give the title compound (2.20 g, 98% yield) as light yellow solid. $^1$H NMR (400 MHz, $CDCl_3$) δ 4.79-4.70 (m, 1H), 4.30 (t, J=6.4 Hz, 2H), 3.84-3.68 (m, 1H), 3.67-3.58 (m, 1H), 3.40 (t, J=6.0 Hz, 2H), 2.99 (s, 3H), 2.92-2.82 (m, 1H), 2.72-2.63 (m, 2H), 2.22-2.13 (m, 1H), 1.95-1.92 (m, 1H), 1.77-1.68 (m, 2H), 1.41 (s, 9H).

Step 4—Tert-butyl N-[3-[3-(methylamino)propoxy] cyclobutyl]carbamate

To a mixture of 3-[3-(tert-butoxycarbonylamino)cyclobutoxy]propyl methanesulfonate (2.20 g, 6.80 mmol) in EtOH (10 mL) was added $MeNH_2$ (10 mL, 20.4 mmol, 30% solution). The reaction mixture was stirred at 70° C. for 12 hours. On completion, the reaction mixture was concentrated in vacuo to give the title compound (1.70 g, 96% yield) as light yellow solid.

Step 5—Benzyl N-[3-[3-(tert-butoxycarbonylamino) cyclobutoxy]propyl]-N-methyl-carbamate To a mixture of tert-butyl N-[3-[3-(methylamino) propoxy]cyclobutyl]carbamate (1.70 g, 6.58 mmol) and $K_2CO_3$ (2.73 g, 19.7 mmol) in THE (20 mL) and $H_2O$ (7 mL) was added CbzCl (1.68 g, 9.87 mmol). The reaction mixture was stirred at 25° C. for 12 hours. On completion, the reaction mixture was diluted with water (30 mL) and extracted with EA (3×50 mL). The combined organic layer was dried over $Na_2SO_4$, filtered and concentrated in vacuo. The residue was purified by column chromatography to give the title compound (1.40 g, 54% yield) as colorless oil. $^1$H NMR (400 MHz, $CDCl_3$) δ 7.39-7.28 (m, 5H), 5.12 (s, 2H), 3.90-3.49 (m, 2H), 3.43-3.25 (m, 4H), 2.92 (s, 3H), 2.65 (s, 2H), 2.25-2.14 (m, 1H), 1.81-1.65 (m, 4H), 1.43 (s, 9H).

Step 6—Benzyl N-[3-(3-aminocyclobutoxy)propyl]-N-methyl-carbamate

To a mixture of benzyl N-[3-[3-(tert-butoxycarbonylamino)cyclobutoxy]propyl]-N-methyl-carbamate (1.20 g, 3.06 mmol) in DCM (10 mL) was added HCl/dioxane (4 M, 6 mL). The reaction mixture was stirred at 25° C. for 1 hour. On completion, the reaction mixture was concentrated in vacuo to give the title compound (1.00 g, 99% yield, HCl salt) as white solid.

2-(2,6-Dioxo-3-piperidyl)-4-[[3-[3-(methylamino) propoxy]cyclobutyl]amino]isoindoline-1,3-dione (Intermediate AYK)

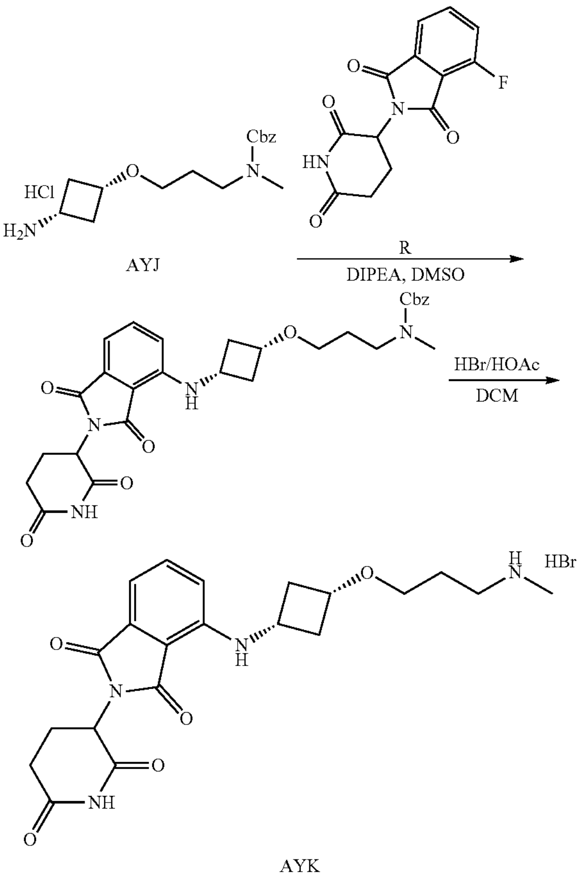

Step 1—Benzyl N-[3-[3-[[2-(2,6-dioxo-3-piperidyl)-1,3-dioxo-isoindolin-4-yl]amino]cyclobutoxy]propyl]-N-methyl-carbamate To a mixture of benzyl N-[3-(3-aminocyclobutoxy)propyl]-N-methyl-carbamate (1.00 g, 3.04 mmol, HCl salt, Intermediate AYJ) and 2-(2,6-dioxo-3-piperidyl)-4-fluoro-isoindoline-1,3-dione (840 mg, 3.04 mmol, Intermediate R) in DMSO (8 mL) was added DIPEA (786 mg, 6.08 mmol). The reaction mixture was stirred at 130° C. for 2 hours. On completion, the reaction mixture was concentrated in vacuo. The residue was purified by reverse phase (0.1% FA condition) to give the title compound (730 mg, 43% yield) as yellow solid. $^{1}$H NMR (400 MHz, DMSO-$d_4$) δ 11.10 (s, 1H), 7.63-7.56 (m, 1H), 7.39-7.27 (m, 5H), 7.07 (d, J=7.2 Hz, 1H), 7.01 (d, J=8.4 Hz, 1H), 6.42 (d, J=6.0 Hz, 1H), 5.09-5.03 (m, 3H), 3.70 (s, 2H), 3.31-3.25 (m, 4H), 2.95-2.81 (m, 4H), 2.75 (s, 2H), 2.63-2.52 (m, 2H), 2.07-1.94 (m, 1H), 1.80 (s, 2H), 1.74-1.60 (m, 2H); LC-MS (ESI$^+$) m/z 549.3 (M+H)$^+$.

Step 2—2-(2,6-Dioxo-3-piperidyl)-4-[[3-[3-(methylamino)propoxy]cyclobutyl]amino]isoindoline-1,3-dione To a mixture of benzyl N-[3-[3-[[2-(2,6-dioxo-3-piperidyl)-1,3-dioxo-isoindolin-4-yl]amino]cyclobutoxy]propyl]-N-methyl-carbamate (150 mg, 273 umol) in DCM (3 mL) was added HBr/HOAc (273 umol, 1 mL). The reaction mixture was stirred at 25° C. for 1 hour. On completion, the reaction mixture was concentrated in vacuo to give the title compound (135 mg, 99% yield, HBr salt) as yellow solid. LC-MS (ESI$^+$) m/z 415.3 (M+H)$^+$.

N-[2-(4-formylcyclohexyl)-6-morpholino-indazol-5-yl]-6-(trifluoromethyl)pyridine -2-carboxamide (Intermediate AYL)

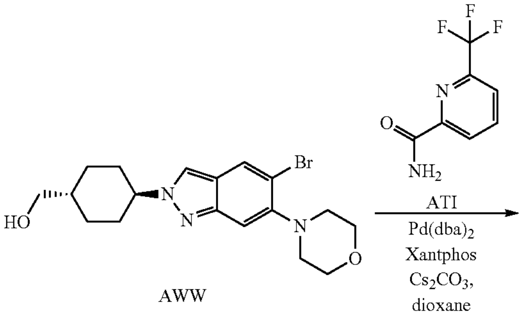

AWW

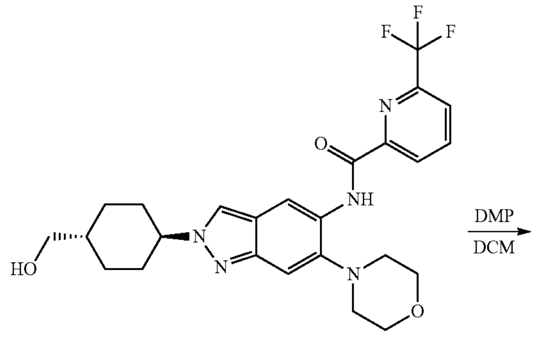

-continued

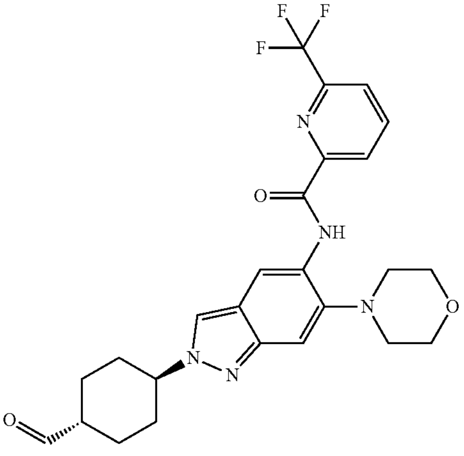

AYL

Step 1—N-[2-[4-(hydroxymethyl)cyclohexyl]-6-morpholino-indazol-5-yl]-6-(trifluoromethyl)pyridine-2-carboxamide To a solution of [4-(5-bromo-6-morpholino-indazol-2-yl)cyclohexyl]methanol (250 mg, 634 umol, Intermediate AWW) in dioxane (5.0 mL) was added Pd(dba)$_2$ (36.5 mg, 63.4 umol), Xantphos (73.4 mg, 127 umol), $Cs_2CO_3$ (413 mg, 1.27 mmol) and 6-(trifluoromethyl)pyridine-2-carboxamide (133 mg, 697 umol, Intermediate ATI). The mixture was stirred at 100° C. for 16 hours. On completion, the reaction mixture was filtered and concentrated in vacuo to give a residue. The residue was purified by reverse phase flash (0.1% FA condition) to give the title compound (100 mg, 31% yield) as a white solid. $^{1}$H NMR (400 MHz, $CDCl_3$) δ 11.25 (s, 1H), 8.93 (s, 1H), 8.57 (d, J=8.0 Hz, 1H), 8.16 (t, J=8.0 Hz, 1H), 8.00-7.85 (m, 2H), 7.54 (s, 1H), 4.38 (tt, J=3.6, 12.0 Hz, 1H), 4.10-3.95 (m, 4H), 3.59 (d, J=6.4 Hz, 2H), 3.18-2.97 (m, 4H), 2.44-2.27 (m, 2H), 2.14-1.90 (m, 5H), 1.53-1.39 (m, 1H), 1.35-1.19 (m, 2H). LC-MS (ESI$^+$) m/z 504.2 (M+H)$^+$.

Step 2—N-[2-(4-formylcyclohexyl)-6-morpholino-indazol-5-yl]-6-(trifluoromethyl)pyridine -2-carboxamide To a mixture of N-[2-[4-(hydroxymethyl)cyclohexyl]-6-morpholino-indazol-5-yl]-6-(trifluoromethyl)pyridine-2-carboxamide (100 mg, 200 umol) in DCM (3.0 mL) was added DMP (126 mg, 298 umol) at 25° C. under $N_2$. The mixture was stirred at 25° C. for 1 hr. On completion, the reaction mixture was quenched with $Na_2S_2O_3$ (6.0 mL) and extracted with DCM (2×5.0 mL). The combined organic layer was washed with $NaHCO_3$ aqueous and brine (2×5.0 mL), dried with anhydrous $Na_2SO_4$, filtered and concentrated in vacuo to give the title compound (100 mg, 96% yield) as white solid. LC-MS (ESI$^+$) m/z 502.2 (M+H)$^+$.

3-[3-Methyl-2-oxo-4-(piperazin-1-ylmethyl)benzimidazol-1-yl]piperidine-2,6-dione (Intermediate ARK)

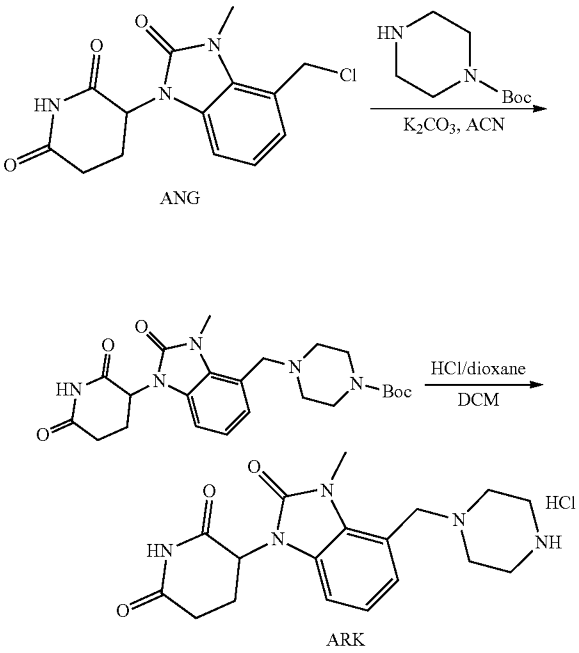

Step 1—Tert-butyl 4-[[1-(2,6-dioxo-3-piperidyl)-3-methyl-2-oxo-benzimidazol-4-yl]methyl]piperazine-1-carboxylate To a solution of 3-[4-(chloromethyl)-3-methyl-2-oxo-benzimidazol-1-yl]piperidine-2,6-dione (400 mg, 1.30 mmol, Intermediate ANG) and tert-butyl piperazine-1-carboxylate (200 mg, 1.07 mmol, CAS #143238-38-4) in ACN (5.00 mL) was added $K_2CO_3$ (297 mg, 2.15 mmol). The mixture was stirred at 80° C. for 3 hrs. On completion, the reaction mixture was filtered and concentrated in vacuo to give a residue. The residue was purified by reversed phase (0.1% FA condition) to give the title compound (430 mg, 87% yield) as a yellow solid. $^1$H NMR (400 MHz, $CDCl_3$) δ 8.57 (s, 1H), 7.02-6.95 (m, 1H), 6.95-6.89 (m, 1H), 6.81-6.75 (m, 1H), 5.27 (dd, J=5.2, 12.4 Hz, 1H), 3.80 (s, 3H), 3.75-3.67 (m, 2H), 3.47-3.35 (m, 4H), 2.99-2.90 (m, 1H), 2.90-2.80 (m, 1H), 2.80-2.68 (m, 1H), 2.55-2.35 (m, 4H), 2.29-2.17 (m, 1H), 1.46 (s, 9H).

Step 2—3-[3-Methyl-2-oxo-4-(piperazin-1-ylmethyl)benzimidazol-1-yl]piperidine-2,6-dione To a solution of tert-butyl 4-[[1-(2, 6-dioxo-3-piperidyl)-3-methyl-2-oxo-benzimidazol-4-yl]methyl]piperazine-1-carboxylate (60.0 mg, 131 umol) in DCM (5.00 mL) was added HCl/dioxane (4 M, 1.00 mL). The reaction mixture was stirred at 20° C. for 0.5 hr. On completion, the reaction mixture was concentrated in vacuo to give the title compound (50.0 mg, 96% yield, HCl salt) as a white solid. LC-MS (ESI$^+$) m/z 358.1 (M+H)$^+$.

N-(6-(2-hydroxypropan-2-yl)-2-((1r,4r)-4-(2-oxoethyl)cyclohexyl)-2H-indazol-5-yl)-6- (trifluoromethyl)picolinamide (Intermediate AYM)

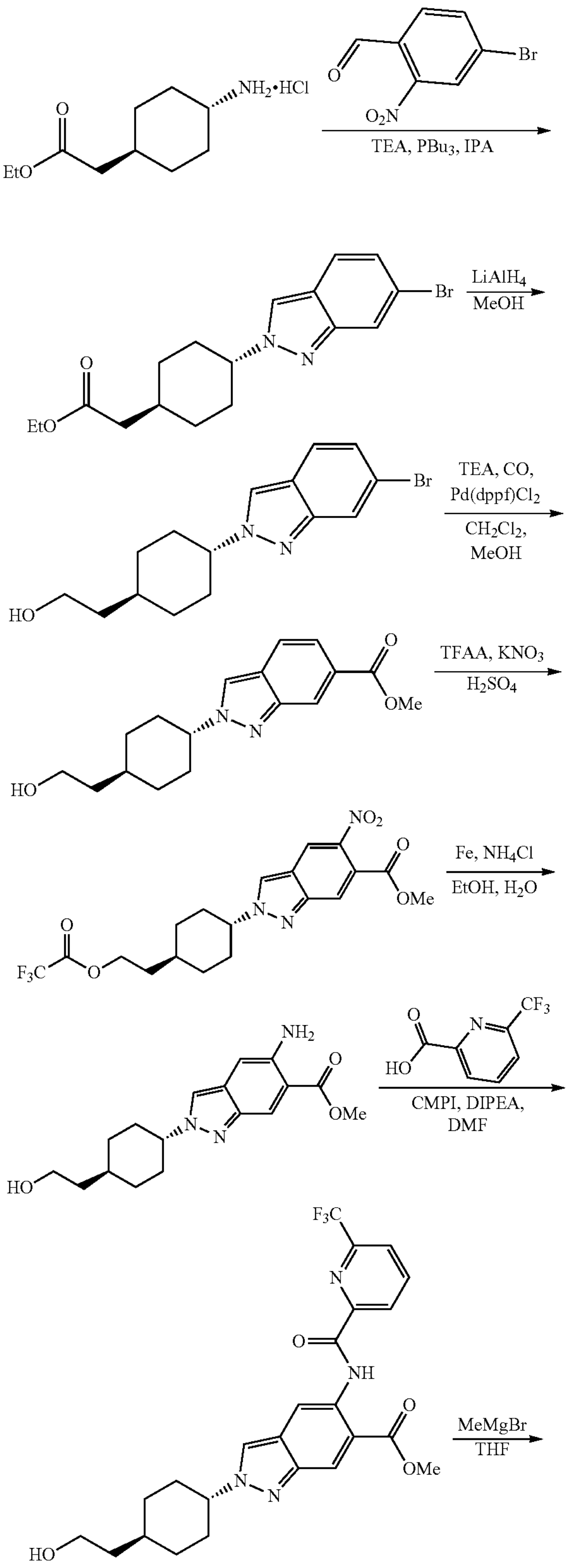

-continued

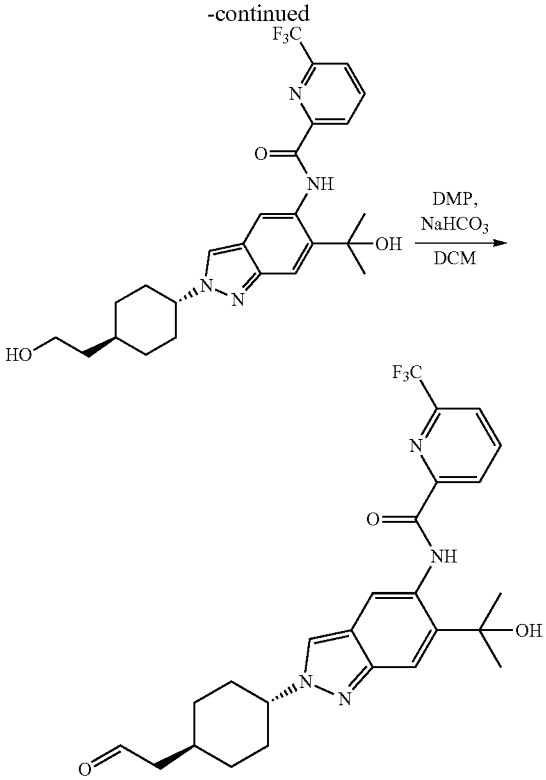

AYM

Step 1—Ethyl 2-((1r,4r)-4-(6-bromo-2H-indazol-2-yl)cyclohexyl)acetate

To a solution of ethyl 2-((1r,4r)-4-aminocyclohexyl)acetate hydrochloride (20.0 g, 90.2 mmol, CAS #76308-26-4) in IPA (240 mL) was added TEA (18.3 g, 180 mmol, 25.1 mL), mixture was stirred at 25° C. for 0.1 hr. Then 4-bromo-2-nitro-benzaldehyde (20.7 g, 90.2 mmol, CAS #5551-12-2) was added, and the mixture was stirred at 80° C. for 4 hrs under $N_2$. The mixture was cooled to 25° C., then tributylphosphane (54.7 g, 270 mmol) was added. The reaction mixture was stirred at 80° C. for 16 hrs. On completion, the reaction mixture was concentrated in vacuo to give a residue. The residue was diluted with water 100 mL and extracted with EA (4×150 mL). The combined organic layers were dried over $Na_2SO_4$, filtered and concentrated in vacuo to give a residue. The residue was purified by silica gel chromatography (PE:EA=20:1) to give the title compound (26.0 g, 78% yield) as yellow oil. $^1H$ NMR (400 MHz, $CDCl_3$) δ 7.92 (d, J=0.8 Hz, 1H), 7.89-7.86 (m, 1H), 7.55-7.48 (m, 1H), 7.14 (dd, J=1.6, 8.8 Hz, 1H), 4.44-4.29 (m, 1H), 4.16 (q, J=7.2 Hz, 2H), 2.37-2.24 (m, 4H), 2.04-1.88 (m, 5H), 1.29-1.26 (m, 5H). LC-MS ($ESI^+$) m/z 365.1 $(M+H)^+$.

Step 2—2-((1r,4r)-4-(6-Bromo-2H-indazol-2-yl)cyclohexyl)ethanol

To a solution of ethyl 2-((1r,4r)-4-(6-bromo-2H-indazol-2-yl)cyclohexyl)acetate (12.0 g, 32.8 mmol) in THE (240 mL) was added $LiAlH_4$ (1.50 g, 39.4 mmol) at 0° C., and the mixture was stirred at 0° C. for 0.5 hr. On completion, the reaction mixture was quenched with water (1.5 mL) and NaOH (4.5 mL, 15%) at 0° C., the mixture was stirred at 0° C. for 0.5 hr. After that, the mixture was filtered and the filtrate was dried over $Na_2SO_4$, filtered and concentrated in vacuo to give the title compound (10.5 g, 100% yield) as light yellow solid. $^1H$ NMR (400 MHz, DMSO-$d_6$) δ 8.44 (d, J=0.8 Hz, 1H), 7.90-7.81 (m, 1H), 7.66 (d, J=8.8 Hz, 1H), 7.11 (dd, J=1.6, 8.8 Hz, 1H), 4.52-4.34 (m, 2H), 3.54-3.40 (m, 2H), 2.10 (d, J=9.5 Hz, 2H), 1.95-1.78 (m, 4H), 1.58-1.42 (m, 1H), 1.41-1.33 (m, 2H), 1.22-1.05 (m, 2H). LC-MS ($ESI^+$) m/z 325.0 $(M+H)^+$.

Step 3—Methyl 2-((1r,4r)-4-(2-hydroxyethyl)cyclohexyl)-2H-indazole-6-carboxylate To a solution of 2-((1r,4r)-4-(6-bromo-2H-indazol-2-yl)cyclohexyl)ethanol (10.4 g, 32.2 mmol) in a mixed solvent of MeOH (150 mL) was added TEA (19.5 g, 193 mmol, 26.8 mL) and Pd(dppf)$Cl_2$.$CH_2Cl_2$ (2.63 g, 3.22 mmol). The suspension was degassed under vacuo and purged with CO three times. The mixture was stirred under CO (50 psi) at 80° C. for 16 hrs. On completion, the reaction mixture was concentrated in vacuo to give a residue. The residue was diluted with water (100 mL) and extracted with EA (3×150 mL), the combined organic layers was dried over $Na_2SO_4$, filtered and concentrated in vacuo to give a residue. The residue was purified by column chromatography (petroleum ether/ethyl acetate=10/1) to give the title compound (9.00 g, 92% yield) as light yellow solid. $^1H$ NMR (400 MHz, DMSO-$d_6$) δ 8.53 (d, J=0.8 Hz, 1H), 8.29 (d, J=0.8 Hz, 1H), 7.80 (dd, J=0.8, 8.8 Hz, 1H), 7.55 (dd, J=1.2, 8.8 Hz, 1H), 4.54-4.49 (m, 1H), 4.37 (t, J=5.2 Hz, 1H), 3.87 (s, 3H), 3.52-3.42 (m, 2H), 2.25-2.06 (m, 2H), 1.98-1.82 (m, 4H), 1.58-1.45 (m, 1H), 1.42-1.39 (m, 2H), 1.25-1.08 (m, 2H). LC-MS ($ESI^+$) m/z 303.2 $(M+H)^+$.

Step 4—Methyl 5-nitro-2-((1r,4r)-4-(2-(2,2,2-trifluoroacetoxy)ethyl)cyclohexyl)-2H-indazole-6- carboxylate A mixture of methyl 2-((1r,4r)-4-(2-hydroxyethyl)cyclohexyl)-2H-indazole-6-carboxylate (8.00 g, 26.5 mmol) in TFAA (80.0 mL) was stirred at 25° C. for 16 hrs. $H_2SO_4$ (12.9 g, 132 mmol, 7.05 mL) was added, then $KNO_3$ (5.35 g, 52.9 mmol) was added at 0° C. The mixture was stirred at 25° C. for 2 hrs. On completion, the reaction mixture was poured into ice water (50 mL). The mixture was extracted with ethyl acetate (3×100 mL). The organic phase was washed with solution of $NaHCO_3$ (2×80 mL), then washed with brine (2×200 mL). The organic phase was dried over anhydrous $Na_2SO_4$, filtered and concentrated in vacuo to give a residue. The residue was purified by column chromatography (petroleum ether/ethyl acetate=0/1) to give the title compound (0.90 g, 7.6% yield) as a yellow solid. $^1H$ NMR (400 MHz, DMSO-$d_6$) δ 8.86 (s, 1H), 8.68 (s, 1H), 8.06 (s, 1H), 4.68-4.55 (m, 1H), 4.47 (t, J=6.4 Hz, 2H), 3.84 (s, 3H), 2.21-2.11 (m, 2H), 1.97-1.85 (m, 4H), 1.75-1.65 (m, 2H), 1.60-1.45 (m, 1H), 1.29-1.16 (m, 2H).

Step 5—Methyl 5-amino-2-((1r,4r)-4-(2-hydroxyethyl)cyclohexyl)-2H-indazole-6-carboxylate To a solution of methyl 5-nitro-2-((1r,4r)-4-(2-(2,2,2-trifluoroacetoxy)ethyl)cyclohexyl)-2H- indazole-6-carboxylate (700 mg, 1.58 mmol) in EtOH (10.0 mL) and $H_2O$ (1.00 mL) was added Fe (440 mg, 7.89 mmol) and $NH_4Cl$ (422 mg, 7.89 mmol). The mixture was stirred at 60° C. for 1 hr. On completion, the reaction mixture was filtered and concentrated in vacuo to give the residue. The residue was diluted with $H_2O$ (10 mL) and extracted with ethyl acetate (3×10 mL). The organic phase was washed with brine (2×20 mL), dried over anhydrous $Na_2SO_4$, concentrated in vacuo to give the title compound (450 mg, 89% yield) as a yellow solid. $^1H$ NMR (400 MHz, DMSO-$d_6$) δ 8.19 (s, 1H), 8.05 (s, 1H), 6.80 (s, 1H), 5.78 (s, 2H), 4.49 (t, J=5.2 Hz, 1H), 4.40-4.31 (m, 1H), 3.83 (s, 3H), 3.48-3.44 (m, 2H), 2.12-2.03 (m, 2H), 1.90-1.79 (m, 4H), 1.53-1.44 (m, 1H), 1.40-1.35 (m, 2H), 1.16-1.08 (m, 2H).

Step 6—Methyl 2-((1r,4r)-4-(2-hydroxyethyl)cyclohexyl)-5-(6-(trifluoromethyl)picolinamido)-2H-indazole-6-carboxylate To a solution of methyl 5-amino-2-((1r,4r)-4-(2-hydroxyethyl)cyclohexyl)-2H-indazole-6-carboxylate (350 mg, 1.10 mmol) in DMF (2.00 mL) was added a mixture of 6-(trifluoromethyl)pyridine- 2-carboxylic acid (200 mg, 1.05 mmol, CAS #131747-42-7), CMPI (295 mg, 1.16 mmol) and DIPEA (407 mg, 3.15 mmol, 548 uL) in DMF (2 mL). The mixture was stirred at 20° C. for 1 hr. On completion, the reaction mixture was quenched by addition $H_2O$ (0.5 mL) and then concentrated in vacuo to give a residue. The residue was purified by reversed phase (0.1% FA condition) to give the title compound (350 mg, 67% yield) as a yellow solid. $^1H$ NMR (400 MHz, DMSO-$d_6$) δ 12.54 (s, 1H), 9.05 (s, 1H), 8.56 (s, 1H), 8.48-8.42 (m, 2H), 8.41-8.35 (m, 1H), 8.19 (d, J=7.8 Hz, 1H), 4.57-4.44 (m, 1H), 4.39 (t, J=4.8 Hz, 1H), 3.95 (s, 3H), 3.55-3.43 (m, 2H), 2.21-2.10 (m, 2H), 1.99-1.83 (m, 4H), 1.59-1.45 (m, 1H), 1.44-1.36 (m, 2H), 1.26-1.06 (m, 2H).

Step 7—N-(2-((1r,4r)-4-(2-hydroxyethyl)cyclohexyl)-6-(2-hydroxypropan-2-yl)-2H-indazol-5-yl)-6- (trifluoromethyl)picolinamide To a solution of methyl 2-((1r,4r)-4-(2-hydroxyethyl) cyclohexyl)-5-(6-(trifluoromethyl)picolinamido)- 2H-indazole-6-carboxylate (150 mg, 305 umol) in THE (5.00 mL) was added dropwise MeMgBr (3 M, 2.04 mL) at 0° C. under $N_2$ atmosphere. After addition, the mixture was stirred at this temperature for 0.5 hr, and then the resulting mixture was stirred at 20° C. for 3 hrs under $N_2$ atmosphere. On completion, the reaction mixture was poured into ice water (30 mL). The mixture was extracted with ethyl acetate (2×30 mL). The organic phase was washed with brine (2×40 mL), dried over anhydrous $Na_2SO_4$, concentrated in vacuo to give a residue. The residue was purified by column chromatography (DCM/MeOH=50/1) to give the title compound (110 mg, 73% yield) as a yellow solid. $^1H$ NMR (400 MHz, DMSO-$d_6$) δ 12.36 (s, 1H), 8.71 (s, 1H), 8.48-8.43 (m, 1H), 8.42-8.33 (m, 2H), 8.16 (d, J=7.6 Hz, 1H), 7.57 (s, 1H), 5.94 (s, 1H), 4.46-4.35 (m, 2H), 3.53-3.43 (m, 2H), 2.17-2.08 (m, 2H), 1.94-1.85 (m, 4H), 1.62 (s, 6H), 1.54-1.47 (m, 1H), 1.43-1.37 (m, 2H), 1.24-1.19 (m, 1H), 1.15-1.10 (m, 1H).

Step 8—N-(6-(2-hydroxypropan-2-yl)-2-((1r,4r)-4-(2-oxoethyl)cyclohexyl)-2H-indazol-5-yl)-6- (trifluoromethyl)picolinamide To a solution of N-(2-((1r,4r)-4-(2-hydroxyethyl)cyclohexyl)-6-(2-hydroxypropan-2-yl)-2H-indazol-5-yl)-6-(trifluoromethyl)picolinamide (80.0 mg, 163 umol) in DCM (6.00 mL) was added DMP (89.9 mg, 212 umol) and $NaHCO_3$ (41.1 mg, 489 umol) at 0° C. The mixture was stirred at 20° C. for 2 hrs. On completion, the reaction mixture was quenched by addition saturated solution of $Na_2S_2O_3$ (4 mL), and saturated solution of $NaHCO_3$ (4 mL), then extracted with DCM (3×10 mL). The combined organic layer was washed with solution of $NaHCO_3$ (2×20 mL), then washed with brine (2×20 mL). The organic layer was dried over anhydrous $Na_2SO_4$, filtered and concentrated in vacuo to give the title compound (77.0 mg, 96% yield) as a yellow solid. $^1H$ NMR (400 MHz, $CDCl_3$) δ 12.28 (s, 1H), 9.81 (t, J=2.0 Hz, 1H), 8.87 (s, 1H), 8.50 (d, J=8.0 Hz, 1H), 8.10 (t, J=8.0 Hz, 1H), 7.91 (s, 1H), 7.83 (dd, J=0.8, 8.0 Hz, 1H), 7.73 (s, 1H), 4.37 (tt, J=3.6, 11.8 Hz, 1H), 2.43 (dd, J=2.0, 6.8 Hz, 2H), 2.34-2.29 (m, 2H), 2.14-2.08 (m, 1H), 2.07-1.96 (m, 5H), 1.80 (s, 6H), 1.36-1.28 (m, 2H).

3-[4-[[(1R,5S)-3,8-diazabicyclo[3.2.1]octan-3-yl]methyl]-3-methyl-2-oxo-benzimidazol-1-yl]piperidine-2,6-dione (Intermediate ARN)

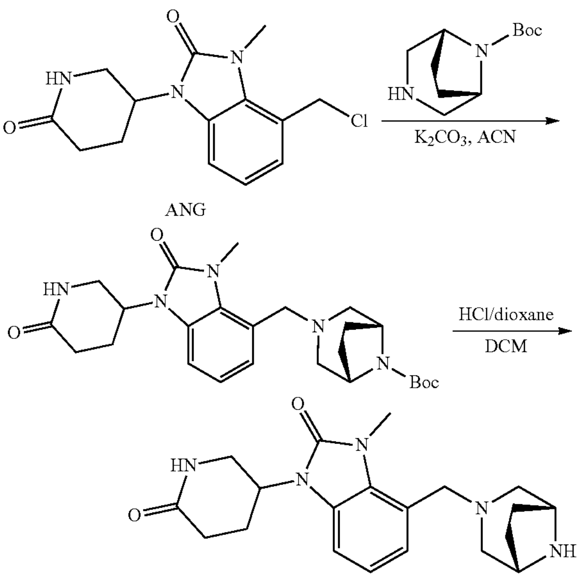

ANG
ARN

Step 1—Tert-butyl (1R,5S)-3-[[1-(2,6-dioxo-3-piperidyl)-3-methyl-2-oxo-benzimidazol-4-yl]methyl]-3,8-diazabicyclo[3.2.1]octane-8-carboxylate To a solution of 3-[4-(chloromethyl)-3-methyl-2-oxo-benzimidazol-1-yl]piperidine-2,6-dione (370 mg, 1.20 mmol, Intermediate ANG) and tert-butyl (1R,5S)-3,8-diazabicyclo[3.2.1]octane-8-carboxylate (200 mg, 942 umol, CAS #149771-44-8) in ACN (4.00 mL) was added $K_2CO_3$ (260 mg, 1.88 mmol). The reaction mixture was stirred at 80° C. for 3 hrs. On completion, the reaction mixture was filtered and the filtrate was concentrated in vacuo to give a residue. The residue was purified by reversed phase (0.1% FA condition) to give the title compound (380 mg, 83% yield) as a yellow solid. $^1H$ NMR (400 MHz, DMSO-$d_6$) δ 11.08 (s, 1H), 7.07 (d, J=7.6 Hz, 1H), 6.99-6.92 (m, 1H), 6.92-6.86 (m, 1H), 5.37 (dd, J=5.2, 12.4 Hz, 1H), 4.03 (s, 2H), 3.68 (s, 3H), 3.63 (s, 2H), 2.99-2.80 (m, 1H), 2.77-2.67 (m, 1H), 2.67-2.61 (m, 1H), 2.60-2.55 (m, 2H), 2.25-2.10 (m, 2H), 2.10-1.96 (m, 1H), 1.80-1.55 (m, 4H), 1.41 (s, 9H).

Step 2—3-[4-[[(1R,5S)-3,8-diazabicyclo[3.2.1]octan-3-yl]methyl]-3-methyl-2-oxo-benzimidazol-1-yl]piperidine-2,6-dione To a solution of tert-butyl (1R,5S)-3-[[1-(2,6-dioxo-3-piperidyl)-3-methyl-2-oxo-benzimidazol-4-yl]methyl]-3,8-diazabicyclo[3.2.1]octane-8-carboxylate (60.0 mg, 124 umol) in DCM (5.00 mL) was added HCl/dioxane (4 M, 6.00 mL). The mixture was stirred at 25° C. for 1 hr. On completion, the reaction mixture was concentrated in vacuo to give the title compound (50.0 mg, 95% yield, HCl) as a yellow solid. LC-MS (ESI$^+$) m/z 384.2 (M+H)$^+$.

6-(1-Methyl-1H-pyrazol-4-yl)picolinamide (Intermediate AYN)

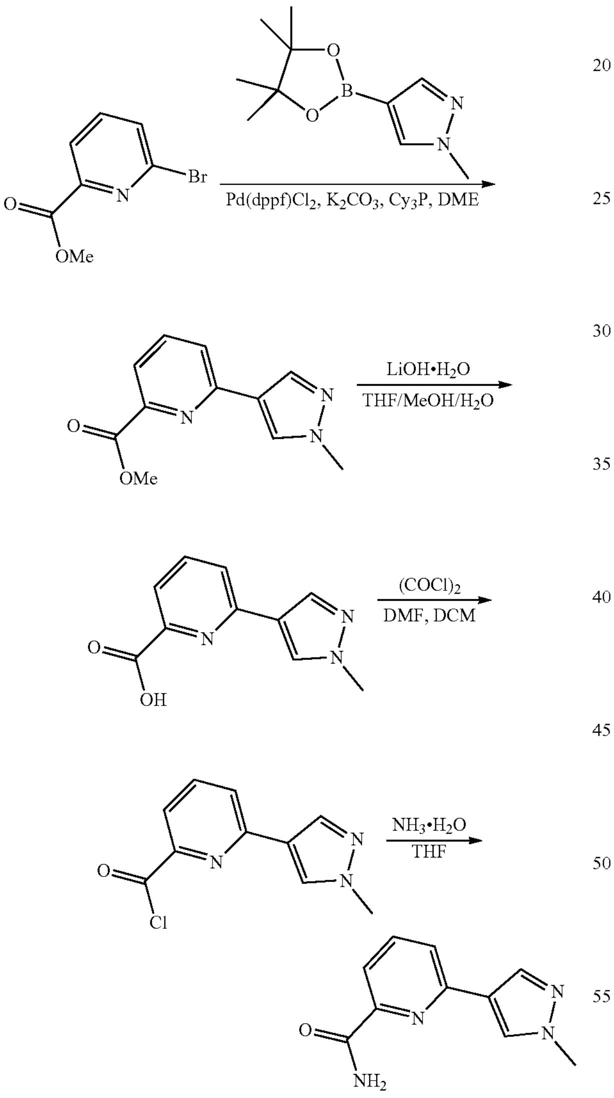

AYN

Step 1—Methyl 6-(1-methyl-1H-pyrazol-4-yl)picolinate

To a solution of methyl 6-bromopyridine-2-carboxylate (3.00 g, 13.8 mmol, CAS #26218-75-7) and 1-methyl-4-(4,4,5,5-tetramethyl-1,3,2-dioxaborolan-2-yl)pyrazole (3.47 g, 16.6 mmol, CAS #761446-44-0) in DME (30 mL) and $H_2O$ (3 mL) was added Pd(dppf)$Cl_2$ (1.02 g, 1.39 mmol) and $Na_2CO_3$ (4.42 g, 41.6 mmol). The mixture was stirred at 90° C. for 12 hours. On completion, the reaction mixture was partitioned between $H_2O$ (100 mL) and EA (100 mL). The organic phase was separated, washed with brine (50 mL), dried over $Na_2SO_4$, filtered and concentrated under reduced pressure to give a residue. The residue was purified by column chromatography ($SiO_2$, petroleum ether/ethyl acetate=100/1 to 1/1) to give the title compound (1.00 g, 51% purity, 33% yield) as a brown solid. LC-MS (ESI$^+$) m/z 218.1 (M+H)$^+$.

Step 2—6-(1-Methyl-1H-pyrazol-4-yl)picolinic acid

To a solution of methyl 6-(1-methylpyrazol-4-yl)pyridine-2-carboxylate (1.00 g, 4.60 mmol) in THF (8 mL) and MeOH (2 mL) was added a solution of LiOH $H_2O$ (579 mg, 13.8 mmol) in $H_2O$ (2 mL). The mixture was stirred at 25° C. for 2 hours. On completion, the reaction mixture was concentrated and then at 0° C. acidified with 2 M HCl aqueous to pH=3. Then the mixture was extracted with DCM (3*50 mL), dried over $Na_2SO_4$, filtered and concentrated to give the title compound (0.90 g, 63% purity, 96% yield) as a brown solid. LC-MS (ESI$^+$) m/z 204.2 (M+H)$^+$.

Step 3—6-(1-Methyl-1H-pyrazol-4-yl)picolinoyl chloride

To a solution of 6-(1-methylpyrazol-4-yl)pyridine-2-carboxylic acid (0.90 g, 4.43 mmol) in DCM (10 mL) was added DMF (32.3 mg, 442 umol) and dropwise $(COCl)_2$ (1.12 g, 8.86 mmol). The mixture was stirred at 25° C. for 0.5 hour. On completion, the reaction mixture was concentrated under reduced pressure to give the title compound (0.90 g, 43% purity, 91% yield) as a brown solid.

Step 4—6-(1-Methyl-1H-pyrazol-4-yl)picolinamide

A solution of 6-(1-methylpyrazol-4-yl)pyridine-2-carbonyl chloride (0.90 g, 4.06 mmol) in THF (5 mL) was added drop wise to $NH_3.H_2O$ (5.08 g, 40.6 mmol, 28% solution). The mixture was stirred at 25° C. for 0.5 hour. On completion, the reaction mixture was partitioned between brine (50 mL) and EA (100 mL). The organic phase was separated, washed with brine (50 mL), dried over $Na_2SO_4$, filtered and concentrated under reduced pressure to give the title compound (246 mg, 41% purity, 30% yield) as a brown solid. LC-MS (ESI$^+$) m/z 203.1 (M+H)$^+$.

N-(2-((1r,4r)-4-formylcyclohexyl)-6-methoxy-2H-indazol-5-yl)-6-(1-methyl-1H-pyrazol-4-yl)picolinamide (Intermediate AYO)

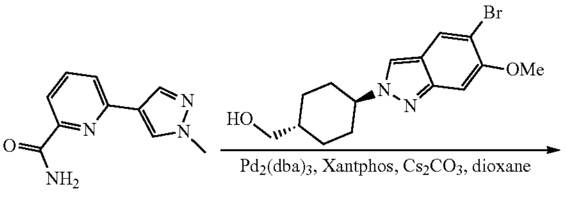

AYN

-continued

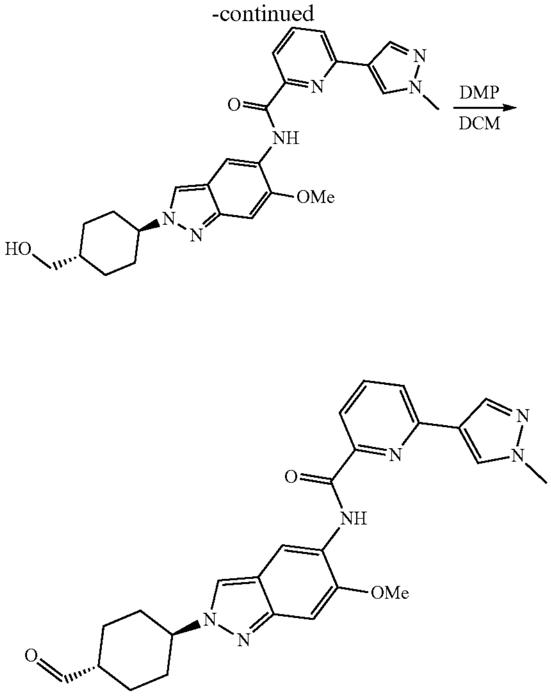

AYO

Step 1—N-(2-((1r,4r)-4-(hydroxymethyl)cyclohexyl)-6-methoxy-2H-indazol-5-yl)-6-(1-methyl-1H-pyrazol-4-yl)picolinamide To a solution of [4-(5-bromo-6-methoxy-indazol-2-yl)cyclohexyl]methanol (220 mg, 648 umol, synthesized via Steps 1-3 of Intermediate ATE) and 6-(1-methylpyrazol-4-yl)pyridine-2-carboxamide (196 mg, 972 umol, Intermediate AYN) in dioxane (1 mL) was added $Pd_2(dba)_3$ (59.3 mg, 64.8 umol), $Cs_2CO_3$ (422 mg, 1.30 mmol) and Xantphos (75.0 mg, 129 umol). The mixture was stirred at 80° C. for 12 hours. On completion, the reaction mixture was filtered and concentrated in vacuo to give a residue. The residue was purified by column chromatography ($SiO_2$, DCM: MeOH=100:1 to 10:1) to give the title compound (400 mg, 86% yield, 64% purity) as an off-white solid. LC-MS ($ESI^+$) m/z 461.4 $(M+H)^+$.

Step 2—N-(2-((1r,4r)-4-formylcyclohexyl)-6-methoxy-2H-indazol-5-yl)-6-(1-methyl-1H-pyrazol-4-yl) picolinamide To a solution of N-[2-[4-(hydroxymethyl)cyclohexyl]-6-methoxy-indazol-5-yl]-6-(1-methyl pyrazol -4-yl) pyridine-2-carboxamide (400 mg, 868 umol) in DCM (5 mL) was added DMP (442 mg, 1.04 mmol). The mixture was stirred at 25° C. for 0.5 hour. On completion, the reaction mixture was quenched by addition sat. $Na_2S_2O_3$ (20 mL) and sat. $NaHCO_3$ (20 mL) at 0° C., and then diluted with $H_2O$ (50 mL) and extracted with DCM (3x50 mL). The combined organic layers were washed with brine (50 mL), dried over $Na_2SO_4$, filtered and concentrated under reduced pressure to give the title compound (260 mg, 65% purity, 65% yield) as a gray solid. LC-MS ($ESI^+$) m/z 459.4 $(M+H)^+$.

4-(3,9-Diazaspiro[5.5]undecan-3-yl)-2-(2,6-dioxo-3-piperidyl)isoindoline-1,3-dione (Intermediate AYP)

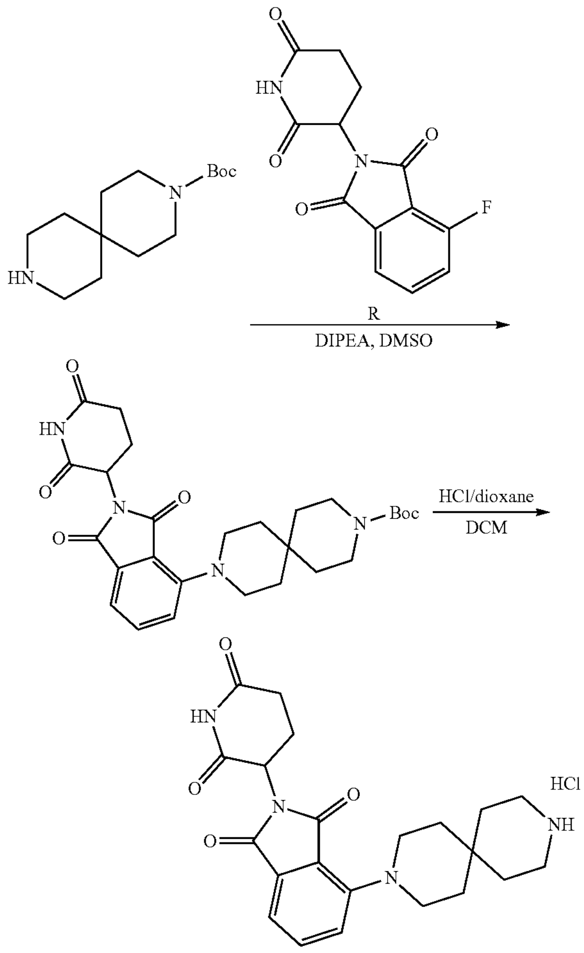

AYP

Step 1—Tert-butyl 9-[2-(2,6-dioxo-3-piperidyl)-1,3-dioxo-isoindolin-4-yl]-3,9-diazaspiro[5.5] undecane-3-carboxylate To a solution of tert-butyl 3,9-diazaspiro[5.5]undecane-3-carboxylate (900 mg, 3.54 mmol, CAS #173405-78-2) and 2-(2,6-dioxo-3-piperidyl)-4-fluoro-isoindoline-1,3-dione (782 mg, 2.83 mmol, Intermediate R) in DMSO (5 mL) was added to DIPEA (1.37 g, 10.6 mmol, 1.85 mL). The reaction mixture was stirred at 130° C. for 3 hrs. On completion, the reaction mixture was diluted with water (25 mL), and filtered to give the title compound (1.6 g, 88.6% yield) as a yellow solid. $^1H$ NMR (400 MHz, DMSO-$d_6$) δ 11.08 (s, 1H), 7.72-7.59 (m, 1H), 7.41-7.23 (m, 2H), 5.16-5.01 (m, 1H), 3.37-3.34 (m, 2H), 3.27 (s, 4H), 2.92-2.81 (m, 1H), 2.63-2.53 (m, 4H), 2.06-1.98 (m, 1H), 1.63 (s, 4H), 1.42 (d, J=5.6 Hz, 4H), 1.41-1.38 (m, 9H); LC-MS ($ESI^+$) m/z 511.3 $(M+H)^+$.

Step 2—4-(3,9-Diazaspiro[5.5]undecan-3-yl)-2-(2,6-dioxo-3-piperidyl)isoindoline-1,3-dione To a solution of tert-butyl 9-[2-(2,6-dioxo-3-piperidyl)-1,3-dioxo-isoindolin-4-yl]-3,9-diazaspiro[5.5]undecane-3-carboxylate (100.0 mg, 196 umol) in DCM (6 mL) was added to HCl/dioxane (4 M, 2 mL). The reaction mixture stirred at 25° C. for 1 hr. On completion, the mixture was concentrated in vacuo to give the title compound (85.0 mg, 97.1% yield, HCl salt) as a yellow solid. LC-MS (ESI$^+$) m/z 411.2 (M+H)$^+$.

2-[2-[tert-butoxycarbonyl(cyclopropylmethyl) amino]-4-pyridyl]oxazole-4-carboxylic acid (Intermediate OM)

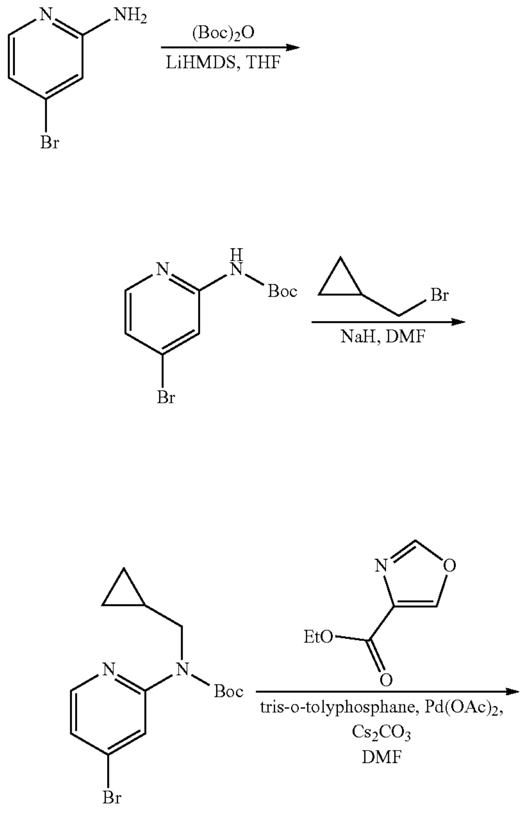

-continued

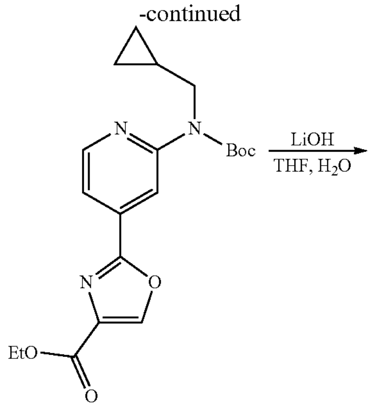

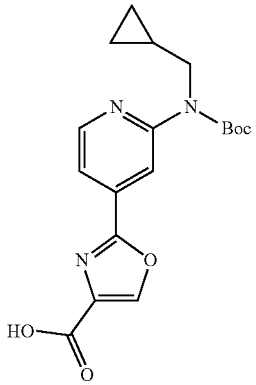

OM

2-[2-[tert-butoxycarbonyl(cyclopropylmethyl) amino]-4-pyridyl]oxazole-4-carboxylic acid was synthesized via Steps 1-4 of Intermediate DF 4-[4-[[2-[2-[Tert-butoxycarbonyl(cyclopropylmethyl)amino]-4-pyridyl]oxazole-4-carbonyl]amino]-3-carbamoyl-pyrazol-1-yl]benzoic acid (Intermediate DF)

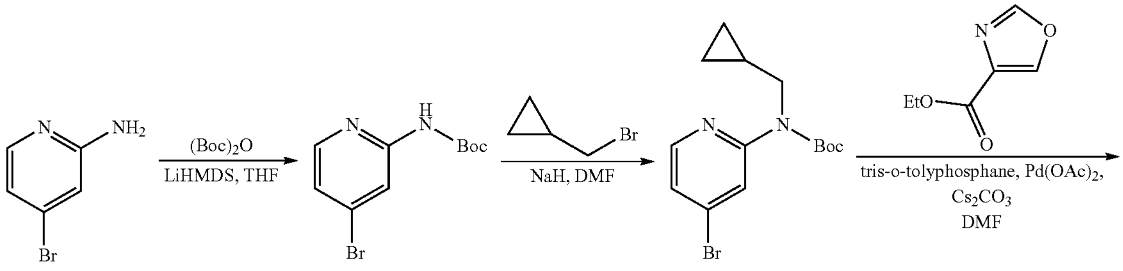

-continued

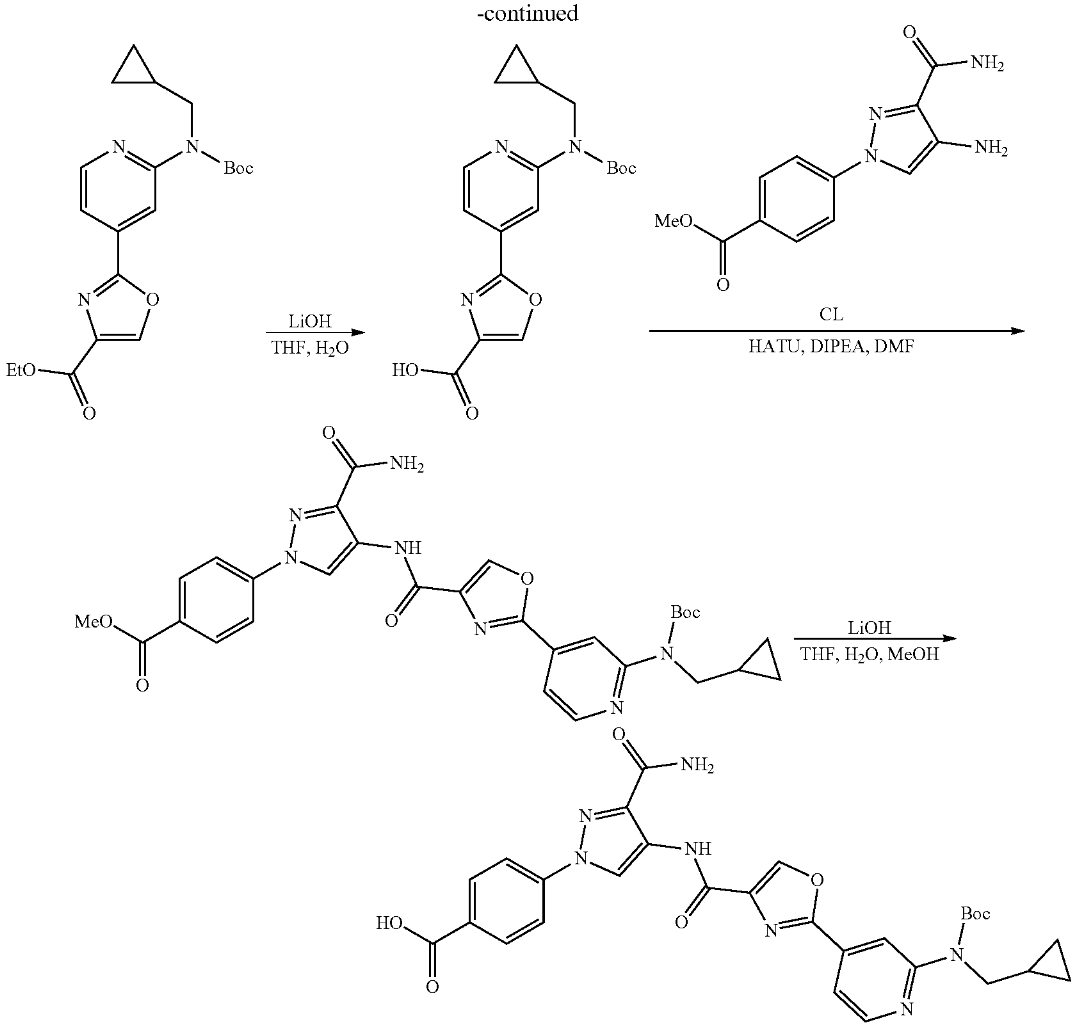

DF

Step 1—Tert-butyl N-(4-bromo-2-pyridyl)-N-(cyclopropylmethyl)carbamate

To a solution of tert-butyl N-(4-bromo-2-pyridyl)carbamate (5.0 g, 18.3 mmol, synthesized via Step 1 of Intermediate CM) in DMF (50 mL) was added NaH (1.10 g, 27.5 mmol) at 0° C. for 30 minutes. Then bromomethylcyclopropane (2.97 g, 22.0 mmol) was added into the mixture. The reaction mixture was stirred at rt for 17 h. On completion, the mixture was quenched with water (40 mL) and extracted with EA (2×50 mL). The organic phase was washed with brine (60 mL), dried over $Na_2SO_4$, and concentrated in vacuo. The residue was purified by silica gel chromatography to give the title compound (2.7 g, 45% yield) as a white solid. $^1$H NMR (400 MHz, $CDCl_3$) δ 8.18 (d, J=5.2 Hz, 1H), 7.98 (d, J=1.6 Hz, 1H), 7.17 (dd, J=1.6, 5.2 Hz, 1H), 3.88 (d, J=7.2 Hz, 2H), 1.55 (s, 9H), 1.22-1.15 (m, 1H), 0.47-0.40 (m, 2H), 0.28-0.23 (m, 2H).

Step 2—Ethyl 2-[2-[tert-butoxycarbonyl(cyclopropylmethyl)amino]-4-pyridyl]oxazole-4-carboxylate To a solution of ethyl oxazole-4-carboxylate (1.16 g, 8.25 mmol) and tert-butyl N-(4-bromo-2-pyridyl)-N-(cyclopropylmethyl)carbamate (2.7 g, 8.25 mmol) in DMF (30 mL) was added tris-o-tolylphosphane (502 mg, 1.65 mmol), $Pd(OAc)_2$ (185 mg, 825 umol) and $Cs_2CO_3$ (5.38 g, 16.5 mmol). The reaction mixture was stirred at 80° C. under nitrogen for 17 h. On completion, the mixture was diluted with water (50 mL) and extracted with EA (3×50 mL). The organic layer was washed with water (100 ml), dried over $Na_2SO_4$, and concentrated in vacuo. The residue was purified by silica gel chromatography to give the title compound (1.8 g, 56% yield) as a white oil. $^1$H NMR (400 MHz, $CDCl_3$) δ 8.50 (dd, J=1.6, 5.2 Hz, 1H), 8.38 (s, 1H), 8.35 (s, 1H), 7.71 (dd, J=1.6, 5.2 Hz, 1H), 4.46 (q, J=7.2 Hz, 2H), 3.93 (d, J=7.2 Hz, 2H), 1.57 (s, 9H), 1.44 (t, J=7.2 Hz, 3H), 1.24-1.16 (m, 1H), 0.46-0.40 (m, 2H), 0.28-0.24 (m, 2H).

Step 3—2-[2-Tert-butoxycarbonyl(cyclopropylmethyl)aminol-4-pyridyl]oxazole-4-carboxylic acid To a solution of ethyl 2-[2-[tert-butoxycarbonyl(cyclopropylmethyl)amino]-4-pyridyl]oxazole-4- carboxylate (0.5 g, 1.29 mmol) in a mixed solvent of THF (5 mL) and $H_2O$ (1 mL) was added LiOH (92.7 mg, 3.87 mmol). The reaction mixture was stirred at rt for 2 h. On completion, the mixture was acidified with 1N HCl solution until the pH=3-5, then extracted with EA (2×30 mL). The combined organic phase was dried over $Na_2SO_4$, filtered and concentrated in vacuo to give the title compound (460 mg, 99% yield) as a white solid. LC-MS ($ESI^+$) m/z 304.0 $(M-56)^+$.

Step 4—Methyl 4-[4-[[2-[2-[tert-butoxycarbonyl (cyclopropylmethyl)amino]-4-pyridyl]oxazole-4-carbonyl]amino]-3-carbamoyl-pyrazol-1-yl]benzoate To a solution of 2-[2-[tert-butoxycarbonyl(cyclopropylmethyl)amino]-4-pyridyl]oxazole-4-carboxylic acid (360 mg, 1.00 mmol) and methyl 4-(4-amino-3-carbamoyl-pyrazol-1-yl)benzoate (443 mg, 1.70 mmol, Intermediate CL) in DMF (5 mL) was added DIPEA (647 mg, 5.01 mmol) and HATU (457 mg, 1.20 mmol). The reaction mixture was stirred at rt for 0.5 hr. On completion, the mixture was diluted with water (40 mL) and extracted with EA (2×30 mL). The combined organic layer was washed with brine (40 mL) and concentrated in vacuo. The residue was purified by silica gel chromatography to give the title compound (190 mg, 32% yield) as a white solid. LC-MS ($ESI^+$) m/z 602.3 $(M+H)^+$.

Step 5—4-[4-[[2-[2-[Tert-butoxycarbonyl(cyclopropylmethyl)amino]-4-pyridyl]oxazole-4-carbonyl]amino]-3-carbamoyl-pyrazol-1-yl]benzoic acid To a solution of methyl 4-[4-[[2-[2-[tert-butoxycarbonyl (cyclopropylmethyl)amino]-4-pyridyl]oxazole -4-carbonyl] amino]-3-carbamoyl-pyrazol-1-yl]benzoate (190 mg, 316 umol) in a mixed solvent of THF (3 mL), MeOH (2 mL) and $H_2O$ (1 mL) was added LiOH (37.8 mg, 1.58 mmol). The reaction mixture was stirred at rt for 17 h. On completion, the mixture was acidified with 1N HCl solution until the pH=5-7, concentrated in vacuo to give the title compound (180 mg, 97% yield) as a yellow solid. LC-MS ($ESI^+$) m/z 588.3 $(M+H)^+$.

2-[2-(Cyclopropylmetinohylam)-4-pyridyl]oxazole-4-carboxylic acid (Intermediate AYQ)

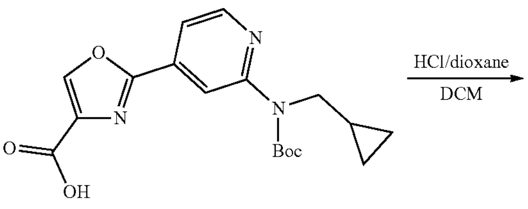

OM

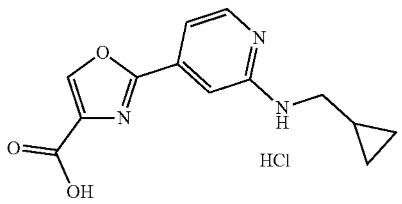

AYQ

To a solution of 2-[2-[tert-butoxycarbonyl(cyclopropylmethyl)amino]-4-pyridyl]oxazole-4-carboxylic acid (500 mg, 1.39 mmol, Intermediate OM) in DCM (16 mL) was added to HCl/dioxane (4 M, 10 mL), the mixture was stirred at 25° C. for 2 hours. On completion, the mixture was concentrated in vacuo to give the title compound (400 mg, 97.2% yield, HCl salt) as a yellow solid. LC-MS ($ESI^+$) m/z 260.1 $(M+H)^+$.

2-[2-(Cyclopropylmethylamino)-4-pyridyl]-N-[2-(4-formylcyclohexyl)-6-(1-hydroxy-1- methyl-ethyl) indazol-5-yl]oxazole-4-carboxamide (Intermediate AYR

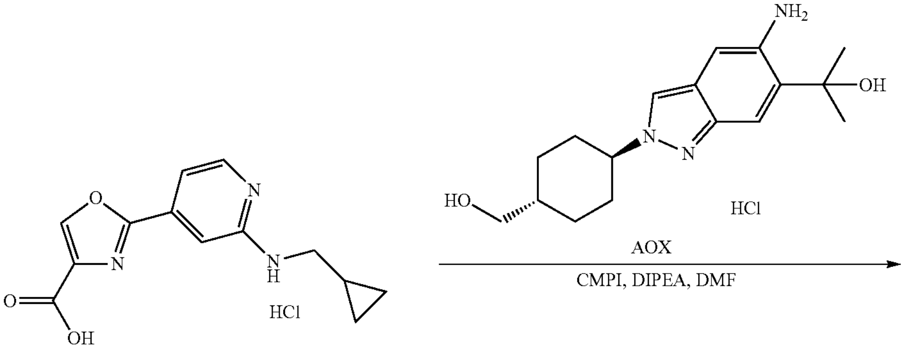

AYQ

-continued

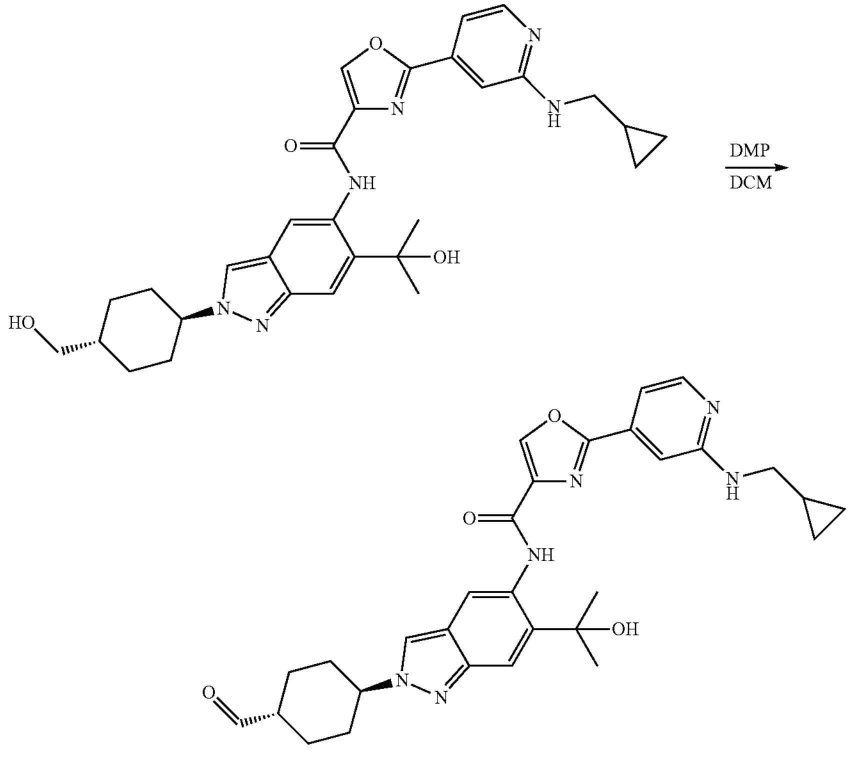

AYR

Step 1—2-[2-(Cyclopropylmethylamino)-4-pyridyl]-N-[2-[4-(hydroxymethyl)cyclohexyl]-6-(1- hydroxy-1-methyl-ethyl)indazol-5-yl]oxazole-4-carboxamide To a solution of 2-[2-(cyclopropylmethylamino)-4-pyridyl]oxazole-4-carboxylic acid (195 mg, 659 umol, HCl salt, Intermediate AYQ) and CMPI (219 mg, 857 umol) in DMF (5 mL) was added DIPEA (426 mg, 3.30 mmol, 574 uL), the mixture was stirred at 25° C. for 0.5 hour. Then 2-[(2S)-5-amino-2-[4-(hydroxylmethyl)cyclohexyl]indazol-6-yl]propan-2-ol (200 mg, 659 umol, Intermediate AOX) was added, the reaction mixture was stirred at 25° C. for 2 hours. On completion, the reaction mixture was diluted with water (40 mL), when a solid was precipitated out from the solution. The mixture was filtered and the filter cake was collected, and dried in vacuo to give the title compound (255 mg, 71.0% yield) as yellow solid. $^1$H NMR (400 MHz, DMSO-$d_6$) δ 11.80 (s, 1H), 8.88 (s, 1H), 8.61 (s, 1H), 8.35 (s, 1H), 8.16 (d, J=5.6 Hz, 1H), 7.57 (s, 1H), 7.09 (s, 1H), 6.14 (s, 1H), 4.57-4.37 (m, 3H), 3.31-3.29 (m, 7H), 2.07 (s, 3H), 1.65 (s, 6H), 1.46-1.33 (m, 1H), 1.27-1.06 (m, 4H), 0.46 (d, J=6.8 Hz, 2H), 0.23 d, J=4.0 Hz, 2H); LC-MS (ESI$^+$) m/z 545.5 (M+H)$^+$.

Step 2—2-[2-(Cyclopropylmethylamino)-4-pyridyl]-N-[2-(4-formylcyclohexyl)-6-(1-hydroxy-1- methyl-ethyl)indazol-5-yl]oxazole-4-carboxamide To a solution of 2-[2-(cyclopropylmethylamino)-4-pyridyl]-N-[2-[4-(hydroxymethyl)cyclohexyl]-6-(1-hydroxy-1-methyl-ethyl)indazol-5-yl]oxazole-4-carboxamide (200 mg, 367 umol) in DMF (5 mL) was added DMP (187 mg, 441 umol), and the reaction mixture was stirred at 25° C. for 1 hours. On completion, the reaction mixture was quenched with aq. $Na_2S_2O_3$ (10 mL) and extracted with DCM (2×30 mL). The combined organic phase was washed with aq. $NaHCO_3$ (10 mL) and brine (2×20 mL), dried with anhydrous $Na_2SO_4$, filtered and concentrated in vacuo to give residue. The residue was purified by reverse phase (0.1% FA condition) to give the title compound (100 mg, 50.2% yield) as a brown solid. $^1$H NMR (400 MHz, DMSO-$d_6$) δ 11.81 (s, 1H), 8.88 (s, 1H), 8.62-8.60 (m, 1H), 8.37-8.33 (m, 1H), 8.16 (d, J=5.6 Hz, 1H), 7.57 (s, 1H), 7.10-7.05 (m, 3H), 6.15 (s, 1H), 4.50-4.39 (m, 1H), 3.19 (t, J=6.0 Hz, 2H), 2.23-1.86 (m, 7H), 1.65 (s, 6H), 1.52-1.39 (m, 2H), 1.26-1.13 (m, 1H), 1.11-1.05 (m, 1H), 0.50-0.39 (m, 2H), 0.25-0.21 (m, 2H); LC-MS (ESI$^+$) m/z 543.2 (M+H)$^+$.

5-(7-Azaspiro[3.5]nonan-2-ylmethylamino)-2-(2,6-dioxo-3-piperidyl)isoindoline-1,3-dione (Intermediate AQZ)

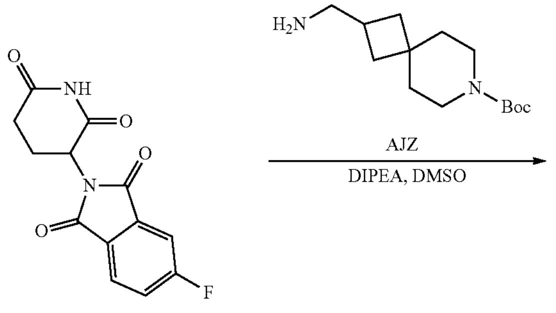

-continued

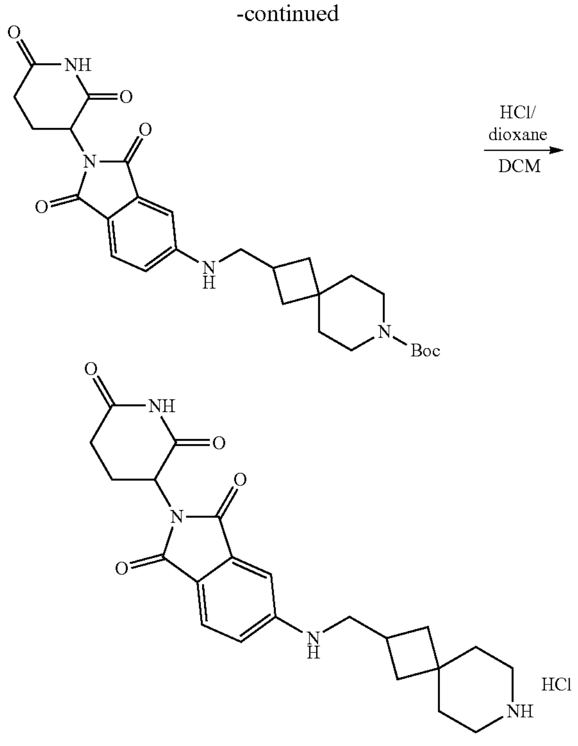

AQZ

Step 1—Tert-butyl 2-[[[2-(2,6-dioxo-3-piperidyl)-1,3-dioxo-isoindolin-5-yl]amino]methyl]-7-azaspiro[3.5]nonane-7-carboxylate To a solution of tert-butyl 2-(aminomethyl)-7-azaspiro[3.5]nonane-7-carboxylate (506 mg, 1.99 mmol, Intermediate AJZ) and 2-(2,6-dioxo-3-piperidyl)-5-fluoro-isoindoline-1,3-dione (500 mg, 1.81 mmol, CAS #1160247-15-3) in DMSO (6 mL) was added DIPEA (935 mg, 7.24 mmol, 1.26 mL), and the reaction mixture was stirred at 130° C. for 3 hrs. On completion, the mixture was concentrated in vacuo to give a residue. The residue was purified by reverse phase (0.1% FA condition) to give the title compound (430 mg, 46.5% yield) as a yellow solid. $^1$H NMR (400 MHz, DMSO-$d_6$) δ 11.05 (s, 1H), 7.54 (d, J=8.4 Hz, 1H), 7.12-7.03 (m, 1H), 6.94 (s, 1H), 6.84 (d, J=8.0 Hz, 1H), 5.02 (dd, J=5.2, 12.8 Hz, 1H), 3.37-3.30 (m, 2H), 3.28-3.24 (m, 2H), 3.22-3.17 (m, 3H), 2.95-2.80 (m, 1H), 2.64-2.53 (m, 2H), 2.03-1.96 (m, 1H), 1.92 (t, J=10.2 Hz, 2H), 1.54-1.46 (m, 4H), 1.43-1.40 (m, 2H), 1.37 (s, 9H); LC-MS (ESI$^+$) m/z 411.3 $(M+H-100)^+$.

Step 2—5-(7-Azaspiro[3.5]nonan-2-ylmethylamino)-2-(2,6-dioxo-3-piperidyl)isoindoline-1,3-dione To a solution of tert-butyl 2-[[[2-(2,6-dioxo-3-piperidyl)-1,3-dioxo-isoindolin-5-yl]amino]methyl]-7-azaspiro[3.5]nonane-7-carboxylate (430 mg, 842 umol) in DCM (4 mL) was added HCl/dioxane (4 M, 4 mL), and the reaction mixture was stirred at 25° C. for 2 hr. On completion, the reaction mixture was concentrated in vacuo to give the title compound (370 mg, 98% yield, HCl salt) as a yellow solid. LC-MS (ESI$^+$) m/z 411.2 $(M+H)^+$.

Methyl 2-[4-(hydroxymethyl)cyclohexyl]-5-(methylamino)indazole-6-carboxylate (Intermediate AYS)

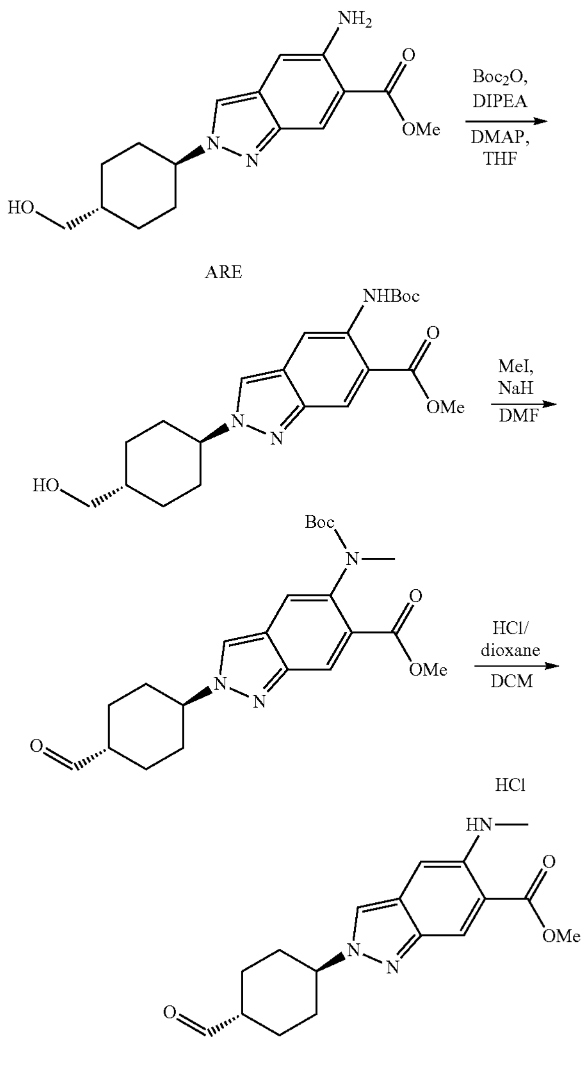

AYS

Step 1—Methyl 5-(tert-butoxycarbonylamino)-2-[4-(hydroxymethyl)cyclohexyl]indazole-6-carboxylate To a mixture of methyl 5-amino-2-[4-(hydroxymethyl)cyclohexyl]indazole-6-carboxylate (1.0 g, 3.30 mmol, Intermediate ARE) in DCM (4 mL) was added $Boc_2O$ (1.08 g, 4.94 mmol, 1.14 mL), DMAP (40.2 mg, 329 umol) and DIPEA (852 mg, 6.59 mmol). The mixture was stirred at 25° C. for 3 hours. On completion, the reaction mixture was quenched with water (15 mL) at 25° C. The mixture was extracted with DCM (3×20 mL). The combined organic layers were washed with brine (10 mL), dried over $Na_2SO_4$, filtered and concentrated in vacuo. The residue was purified by column chromatography ($SiO_2$, petroleum ether/ethyl acetate=15/1 to 10/1) to afford the title compound (400 mg, 30% yield) as yellow solid. LC-MS (ESI$^+$) m/z 404.2 $(M+H)^+$.

Step 2—Methyl 5-[tert-butoxycarbonyl(methyl] aminol-2-[4-(hydroxymethyl)cyclohexyl]indazole-6-carboxylate To a mixture of methyl 5-(tert-butoxycarbonylamino)-2-[4-(hydroxymethyl)cyclohexyl]indazole-6- carboxylate (400 mg, 991 umol) in DMF (2 mL) was added NaH (51.5 mg, 1.29 mmol, 60% dispersion in mineral oil) and MeI (168 mg, 1.19 mmol) at 25° C. The mixture was stirred at 25° C. for 3 hours. On completion, the reaction mixture was quenched with water (20 mL) at 25° C. and the mixture was extracted with DCM (3x20 mL). The combined organic layers were washed with brine (10 mL), dried over $Na_2SO_4$, filtered and concentrated in vacuo. The residue was purified by reverse phase (FA condition) to afford the title compound (400 mg, 96% yield) as a yellow solid. LC-MS (ESI$^+$) m/z 418.2 $(M+H)^+$.

Step 3—Methyl 2-[4-(hydroxymethyl)cyclohexyl]-5-(methylamino)indazole-6-carboxylate To a mixture of methyl 5-[tert-butoxycarbonyl(methyl) amino]-2-[4-(hydroxymethyl)cyclohexyl]indazole-6-carboxylate (400 mg, 958 umol) in DCM (10 mL) was added HCl/dioxane (4 M, 10 mL) at 25° C. The mixture was stirred at 25° C. for 2 hours. On completion, the reaction mixture was concentrated in vacuo to give the title compound (300 mg, 88% yield) as yellow solid. LC-MS (ESI$^+$) m/z 318.2 $(M+H)^+$.

N-[2-(4-formylcyclohexyl)-6-(1-hydroxy-1-methyl-ethyl)indazol-5-yl]-N-methyl-6-(trifluoro methyl) pyridine-2-carboxamide (Intermediate AYT)

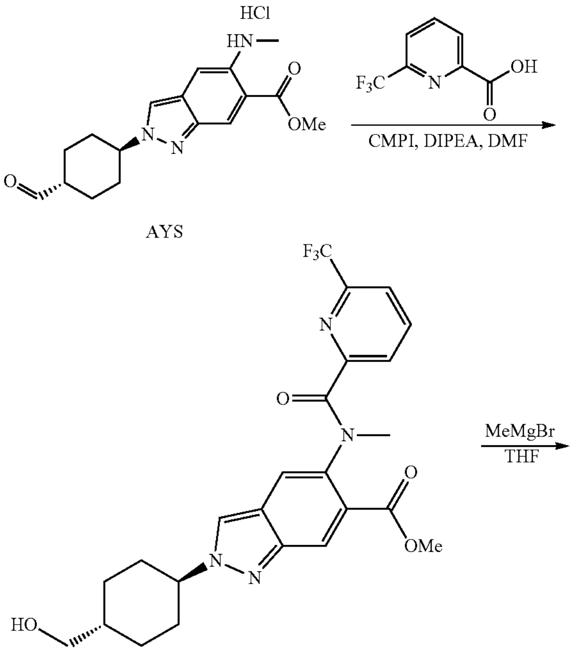

-continued

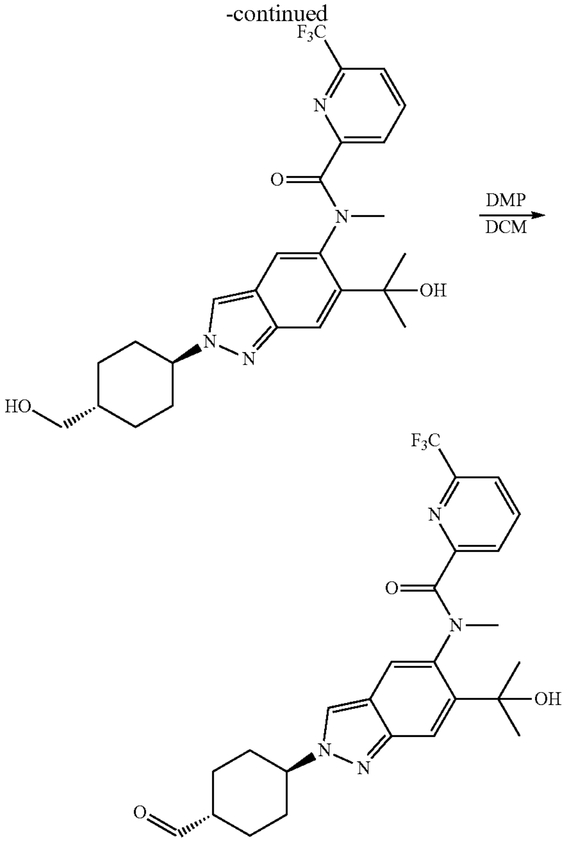

AYT

Step 1—Methyl 2-[4-(hydroxymethyl)cyclohexyl]-5-[methyl-[6-(trifluoromethyl)pyridine-2-carbonyl] amino]indazole-6-carboxylate To a mixture of 6-(trifluoromethyl)pyridine-2-carboxylic acid (156 mg, 819 umol, CAS #131747-42-7) in DMF (10 mL) was added CMPI (272 mg, 1.07 mmol) and DIPEA (529 mg, 4.10 mmol). The mixture was stirred at 25° C. for 1 hour. Then, methyl 2-[4-(hydroxymethyl)cyclohexyl]-5-(methyl amino)indazole-6-carboxylate (290 mg, 819 umol, HCl salt, Intermediate AYS) was added and the mixture was stirred at 25° C. for 4 hours. On completion, the reaction mixture was quenched with $H_2O$ (0.2 mL) at 25° C., and then concentrated in vacuo. The residue was purified by reverse phase (FA condition) to afford the title compound (390 mg, 97% yield) as yellow solid. $^1H$ NMR (400 MHz, DMSO-$d_6$) δ 8.46 (s, 1H), 8.07 (s, 1H), 8.00-7.92 (m, 1H), 7.74 (d, J=7.6 Hz, 1H), 7.70 (s, 1H), 7.65 (d, J=7.6 Hz, 1H), 4.53-4.40 (m, 2H), 3.81 (s, 3H), 3.35 (s, 3H), 3.29-3.25 (m, 2H), 2.13-2.04 (m, 2H), 1.92-1.82 (m, 4H), 1.54-1.40 (m, 1H), 1.20-1.09 (m, 2H); LC-MS (ESI$^+$) m/z 491.1 $(M+H)^+$.

Step 2—N-[2-[4-(hydroxymethyl)cyclohexyl]-6-(1-hydroxy-1-methyl-ethyl)indazol-5-yl]-N-methyl-6-(trifluoromethyl)pyridine-2-carboxamide To a mixture of methyl 2-[4-(hydroxymethyl)cyclohexyl]-5-[methyl-[6-(trifluoromethyl)pyridine-2- carbonyl] amino]indazole-6-carboxylate (140 mg, 285 umol) in THE (20 mL) was added MeMgBr (3 M, 2.38 mL) at 0° C. under $N_2$. The mixture was stirred at 25° C. for 16 hours. On completion, the reaction mixture was quenched by with sat. aq. $NH_4Cl$ (30 mL) at 0° C. The mixture was extracted with DCM (3×40 mL). The combined organic layers were washed with brine (20 mL), dried over $Na_2SO_4$, filtered and concentrated in vacuo. The residue was purified by prep-HPLC (column: Phenomenex Synergi C18 150*25*10 um; mobile phase: [water (0.225% FA)-ACN]; B %: 25%-55%, 10 min) to afford the title compound (25.0 mg, 18% yield) as yellow solid. $^1H$ NMR (400 MHz, DMSO-$d_6$) δ 8.47 (s, 1H), 8.31 (s, 1H), 8.19-8.11 (m, 1H), 8.00 (d, J=8.0 Hz, 1H), 7.89 (d, J=7.6 Hz, 1H), 7.66 (s, 1H), 4.56-4.46 (m, 1H), 3.29 (d, J=6.4 Hz, 3H), 2.65 (s, 3H), 2.13 (d, J=9.2 Hz, 2H), 1.98-1.84 (m, 5H), 1.55 (s, 6H), 1.23-1.08 (m, 2H); LC-MS ($ESI^+$) m/z 491.1 $(M+H)^+$.

Step 3—N-[2-(4-formylcyclohexyl)-6-(1-hydroxy-1-methyl-ethyl)indazol-5-yl]-N-methyl-6-(trifluoro methyl)pyridine-2-carboxamide To a mixture of N-[2-[4-(hydroxymethyl)cyclohexyl]-6-(1-hydroxy-1-methyl-ethyl)indazol-5-yl]-N— methyl-6-(trifluoromethyl)pyridine-2-carboxamide (25.0 mg, 50.9 umol) in DCM (3 mL) was added DMP (25.9 mg, 61.2 umol) and $NaHCO_3$ (21.4 mg, 254 umol) at 25° C. The mixture was stirred at 25° C. for 5 hours. On completion, the reaction mixture was quenched with sat. aq. $Na_2S_2O_3$ (10 mL) at 25° C. The mixture was extracted with DCM (3×20 mL). The combined organic layers dried over $Na_2SO_4$, filtered and concentrated in vacuo to give the title compound (10.0 mg, 40% yield) as yellow solid. LC-MS ($ESI^+$) m/z 489.2 $(M+H)^+$.

Tert-butyl(2S)-2-(3-aminopropyl)morpholine-4-carboxylate (Intermediate AYU)

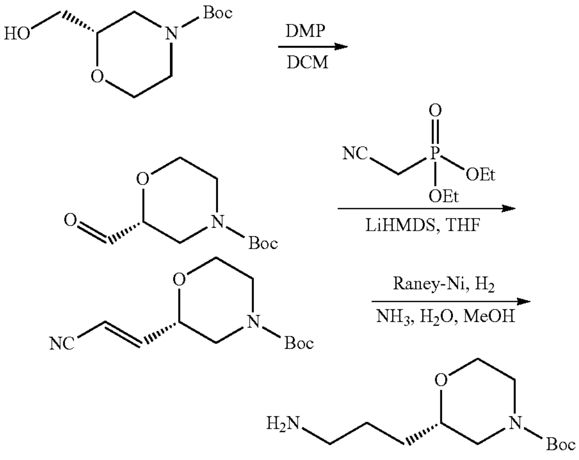

AYU

Step 1—Tert-butyl (2S)-2-formylmorpholine-4-carboxylate

To a mixture of tert-butyl (2S)-2-(hydroxymethyl)morpholine-4-carboxylate (3.00 g, 13.8 mmol, CAS #135065-76-8) in DCM (25 mL) was added DMP (7.03 g, 16.6 mmol) at 25° C. The mixture was stirred at 25° C. for 2 hours. On completion, the mixture was quenched with saturated aqueous $Na_2S_2O_3$ (10 mL) and $NaHCO_3$ (20 mL), then extracted with DCM (3×30 mL). The combined organic phase was dried over $Na_2SO_4$, filtered, and the filtrate was concentrated in vacuo to give the title compound (1.80 g, 45% yield) as white solid.

Step 2—Tert-butyl (2S)-2-[(E)-2-cyanovinyl]morpholine-4-carboxylate

To a solution of 2-diethoxyphosphorylacetonitrile (1.65 g, 9.29 mmol, 1.50 mL, CAS #2537-48-6) in THE (16 mL) was added LiHMDS (1.0 M, 11.2 mL). The mixture was stirred at −70° C. under $N_2$ atmosphere for 30 mins. Then, tert-butyl (2R)-2-formylmorpholine-4-carboxylate (2.0 g, 9.29 mmol) was added, and the reaction mixture was stirred at −70° C. for 4 hours. On completion, the reaction mixture was quenched with $NH_4Cl$ (20 ml) at −70° C., and extracted with EA (2×40 ml). The combined organic phase was dried over $Na_2SO_4$, filtered and concentrated in vacuo to give a residue. The residue was purified by column chromatography ($SiO_2$, petroleum ether/ethyl acetate=20/1) to give the title compound (1.4 g, 63% yield) as a yellow solid. $^1H$ NMR (400 MHz, $CDCl_3$) δ 6.65-6.59 (m, 1H), 5.75-5.71 (m, 1H), 4.07-4.02 (m, 2H), 3.94 (d, J=11.6 Hz, 1H), 3.90-3.87 (m, 1H), 3.61-3.54 (m, 1H), 2.95 (s, 1H), 2.61 (s, 1H), 1.48 (s, 9H).

Step 3—Tert-butyl (2S)-2-(3-aminopropyl)morpholine-4-carboxylate

To a solution of tert-butyl (2S)-2-[(E)-2-cyanovinyl]morpholine-4-carboxylate (1.4 g, 5.88 mmol) in MeOH (10 mL) was added $NH_3.H_2O$ (1.65 g, 11.8 mmol, 1.81 mL, 25% solution) and Raney-Ni (10.1 g, 11.8 mmol, 10 wt %). The mixture was purged with $H_2$ three times, and stirred at 25° C. under $H_2$ (50 Psi) for 12 hours. On completion, the reaction mixture was filtered and the filtrate was concentrated in vacuo to give the title compound (1.01 g, 70% yield,) as green oil.

2-(2,6-Dioxo-3-piperidyl)-4-[3-[(2S)-morpholin-2-yl]propylamino]isoindoline-1,3-dione (Intermediate AYV)

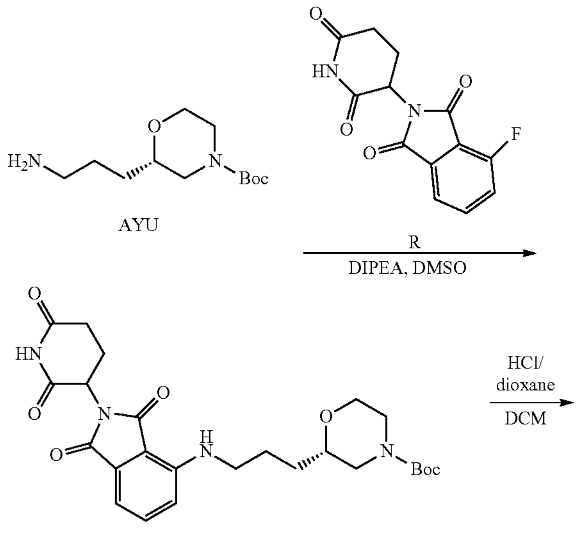

-continued

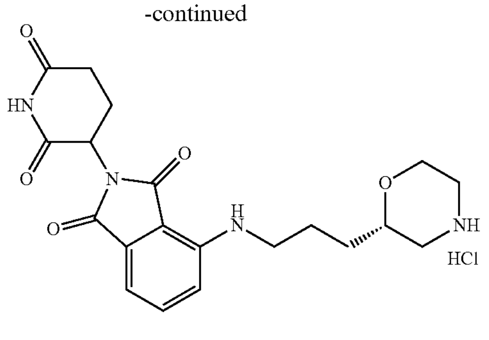

AYV

Step 1—Tert-butyl (2S)-2-[3-[[2-(2,6-dioxo-3-piperidyl)-1,3-dioxo-isoindolin-4-yl]amino]propyl]morpholine-4-carboxylate To a solution of tert-butyl (2S)-2-(3-aminopropyl)morpholine-4-carboxylate (530 mg, 2.17 mmol, Intermediate AYU) and 2-(2,6-dioxo-3-piperidyl)-4-fluoro-isoindoline-1,3-dione (599 mg, 2.17 mmol, Intermediate R) in DMSO (8 mL) was added DIPEA (280 mg, 2.17 mmol, 378 uL), and the reaction mixture was stirred at 130° C. for 3 hours. On completion, the reaction mixture quenched with $H_2O$ (0.5 mL), then concentrated in vacuo to give a residue. The residue was purified by reverse phase (0.1% FA condition) to give the title compound (450 mg, 41% yield) as a yellow solid. $^1H$ NMR (400 MHz, $CDCl_3$) δ 8.31 (s, 1H), 7.51-7.47 (m, 1H), 7.09 (d, J=6.8 Hz, 1H), 7.13-6.84 (m, 1H), 6.87 (d, J=8.8 Hz, 1H), 6.28 (s, 1H), 4.94-4.90 (m, 1H), 3.88 (d, J=10.0 Hz, 3H), 3.58-3.47 (m, 1H), 3.40-3.30 (m, 3H), 2.91-2.69 (m, 3H), 2.94 (s, 1H), 2.16-2.10 (m, 1H), 1.92-1.68 (m, 1H), 1.92-1.67 (m, 1H), 1.61-1.54 (m, 2H), 1.47 (s, 9H); LC-MS (ESI$^+$) m/z 401.1 (M -100+H)$^+$.

Step 2—2-(2,6-Dioxo-3-piperidyl)-4-[3-[(2S)-morpholin-2-yl]propylamino]isoindoline-1,3-dione To a solution of tert-butyl (2S)-2-[3-[[2-(2,6-dioxo-3-piperidyl)-1,3-dioxo-isoindolin-4-yl]amino]propyl]morpholine-4-carboxylate (100 mg, 200 umol) in DCM (4 mL) was added to HCl/dioxane (4 M, 45.0 uL) at 25° C. and the reaction was stirred at 25° C. for 3 hours. On completion, the mixture was concentrated in vacuo to give the title compound (87 mg, 99% yield, HCl salt) as a green solid. LC-MS (ESI$^+$) m/z 401.1 (M+H)$^+$.

Benzyl 4-(3-aminocyclobutoxy)piperidine-1-carboxylate (Intermediate ARB)

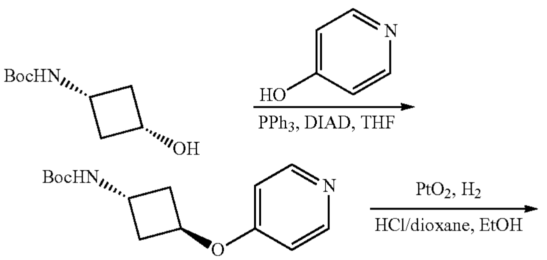

-continued

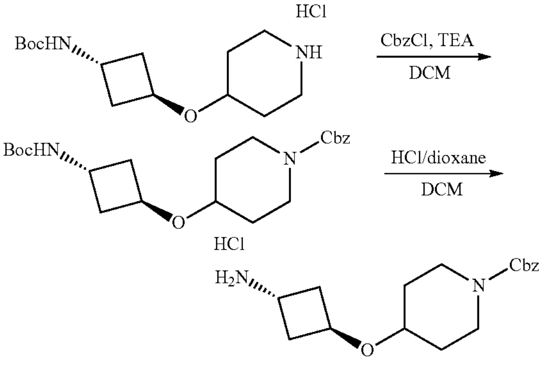

ARB

Step 1—Tert-butyl N-[3-(4-pyridyloxy)cyclobutyl]carbamate

To a mixture of tert-butyl N-(3-hydroxycyclobutyl)carbamate (500 mg, 2.67 mmol, CAS #154748-63-7) and pyridin-4-ol (253 mg, 2.67 mmol, CAS #626-64-2) in THF (2.0 mL) was added $PPh_3$ (1.05 g, 4.01 mmol). Then DIAD (810 mg, 4.01 mmol) was added into the mixture at 0° C. The mixture was stirred at 50° C. for 12 hours. On completion, the reaction was concentrated in vacuo to give a residue. The residue was purified by reverse phase (0.1% FA condition) to give the title compound (365 mg, 51% yield) as a white solid. $^1H$ NMR (400 MHz, DMSO-$d_6$) δ 8.37 (br s, 2H), 7.31 (d, J=6.8 Hz, 1H), 6.83 (d, J=4.8 Hz, 2H), 4.92-4.84 (m, 1H), 4.09 (d, J=6.8 Hz, 1H), 2.46-2.28 (m, 4H), 1.38 (s, 9H).

Step 2—Tert-butyl N-[3-(4-piperidyloxy)cyclobutyl]carbamate

To a mixture of tert-butyl N-[3-(4-pyridyloxy)cyclobutyl]carbamate (450 mg, 1.70 mmol) in THF (30 mL) was added $PtO_2$ (386 mg, 1.70 mmol) and HCl/dioxane (4 M, 851 uL) under $H_2$ (50 psi). The mixture was stirred at 25° C. for 12 hours. On completion, the mixture was filtered and concentrated in vacuo to give the title compound (425 mg, 92% yield) as a white solid. $^1H$ NMR (400 MHz, DMSO-$d_6$) δ 9.30-8.86 (m, 2H), 7.22-7.05 (m, 1H), 4.22-4.14 (m, 1H), 4.00-3.89 (m, 1H), 3.56-3.48 (m, 1H), 3.10 (s, 1H), 3.02-2.88 (m, 3H), 2.16-2.07 (m, 3H), 1.91 (d, J=13.6 Hz, 1H), 1.72-1.59 (m, 3H), 1.37 (d, J=1.1 Hz, 9H).

Step 3—Benzyl 4-[3-(tert-butoxycarbonylamino)cyclobutoxy]piperidine-1-carboxylate To a mixture of tert-butyl N-[3-(4-piperidyloxy)cyclobutyl]carbamate (345 mg, 1.28 mmol) in DCM (5 mL) was added TEA (387 mg, 3.83 mmol) and CbzCl (326 mg, 1.91 mmol). The mixture was stirred at 20° C. for 1 hour. On completion, the reaction mixture was concentrated to give the residue. The residue was purified by column chromatography ($SiO_2$, PE:EA=2:1) to give the title compound (430 mg, 83% yield) as brown oil. $^1H$ NMR (400 MHz, $CDCl_3$) δ 7.39-7.27 (m, 5H), 5.13 (s, 2H), 4.79-4.53 (m, 1H), 4.27-4.07 (m, 2H), 3.89-3.79 (m, 2H), 3.53-3.35 (m, 1H), 3.17 (d, J=26.4 Hz, 2H), 2.43-2.26 (m, 2H), 2.23-2.09 (m, 2H), 1.77 (s, 2H), 1.57-1.47 (m, 2H), 1.44 (s, 9H).

Step 4—Benzyl 4-(3-aminocyclobutoxy)piperidine-1-carboxylate

To a mixture of benzyl 4-[3-(tert-butoxycarbonylamino) cyclobutoxy]piperidine-1-carboxylate (420 mg, 1.04 mmol) in DCM (20 mL) was added HCl/dioxane (4 M, 778 uL). The reaction mixture was stirred at 20° C. for 0.5 hour. On completion, the mixture was concentrated in vacuo to give the title compound (353 mg, 99% yield, HCl salt) as a yellow solid. LC-MS ($ESI^+$) m/z 305.2 $(M+H)^+$.

2-(2,6-dioxo-3-piperidyl)-4-[[3-(4-piperidyloxy) cyclobutyl]amino]isoindoline-1,3-dione (Intermediate AQS)

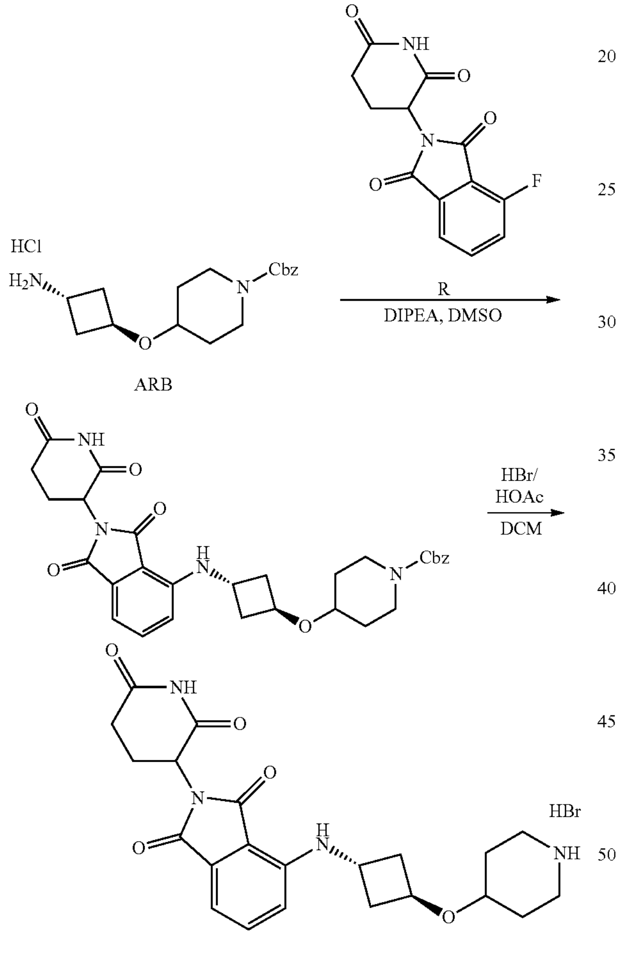

ARB

AQS

Step 1—Benzyl 4-[3-[[2-(2,6-dioxo-3-piperidyl)-1,3-dioxo-isoindolin-4-yl]amino]cyclobutoxy] piperidine-1-carboxylate To a mixture of 2-(2,6-dioxo-3-piperidyl)-4-fluoro-isoindoline-1,3-dione (259 mg, 938 umol, Intermediate R) and benzyl 4-(3-aminocyclobutoxy)piperidine-1-carboxylate (320 mg, 938 umol, HCl salt, Intermediate ARB) in DMSO (10 mL) was added DIPEA (243 mg, 1.88 mmol). The mixture was stirred at 130° C. for 2 hours. On completion, the mixture was poured into water (30 mL) and the aqueous phase was extracted with ethyl acetate (2×20 mL). The combined organic phase was washed with brine (2×30 mL), dried with anhydrous $Na_2SO_4$, filtered and concentrated in vacuo to give the residue. The residue was purified by reverse phase (0.1% FA condition) to give the title compound (220 mg, 41% yield) as a yellow solid. $^1H$ NMR (400 MHz, DMSO-$d_6$) δ 11.12 (s, 1H), 7.67-7.53 (m, 1H), 7.43-7.27 (m, 5H), 7.09 (d, J=7.2 Hz, 1H), 6.91 (d, J=8.4 Hz, 1H), 6.51 (d, J=5.6 Hz, 1H), 5.13-5.01 (m, 3H), 4.33 (d, J=6.0 Hz, 1H), 4.12 (d, J=4.4 Hz, 1H), 3.80-3.70 (m, 2H), 3.54-3.44 (m, 1H), 3.20-3.03 (m, 2H), 2.97-2.84 (m, 1H), 2.70-2.54 (m, 2H), 2.42-2.32 (m, 2H), 2.31-2.21 (m, 2H), 2.08-1.99 (m, 1H), 1.86-1.73 (m, 2H), 1.42-1.29 (m, 2H).

Step 2—2-(2,6-Dioxo-3-piperidyl)-4-[[3-(4-piperidyloxy)cyclobutyl]amino]isoindoline-1,3-dione To a mixture of benzyl 4-[3-[[2-(2,6-dioxo-3-piperidyl)-1,3-dioxo-isoindolin-4-yl]amino]cyclobutoxy]piperidine-1-carboxylate (40 mg, 71.3 umol) in DCM (5 mL) was added HBr/HOAc (19.2 mg, 71.3 umol, 12.9 uL). The mixture was stirred at 20° C. for 0.5 hour. On completion, the mixture was concentrated in vacuo to give the title compound (32.0 mg, 100% yield) as brown oil. LC-MS ($ESI^+$) m/z 427.3 $(M+H)^+$.

6-Tert-butylpyridine-2-carboxylic acid (Intermediate AYW)

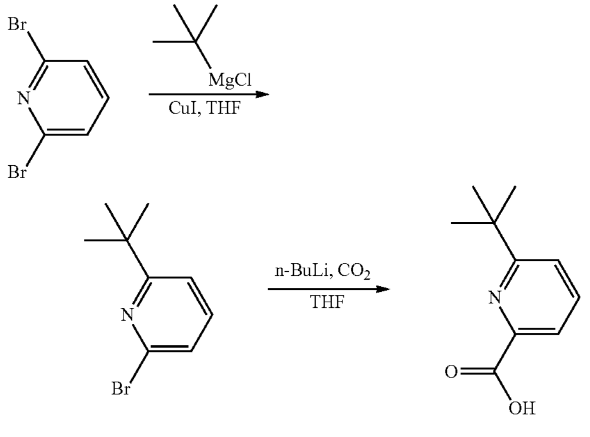

AYW

Step 1—2-Bromo-6-tert-butyl-pyridine

To a solution of 2,6-dibromopyridine (3.00 g, 12.6 mmol, CAS #626-05-1) in THE (30 mL) was added CuI (120 mg, 633 umol) followed by addition of tert-butyl(chloro)magnesium (1.7 M, 35.7 mL, CAS #677-22-5) at 0° C. The reaction mixture was stirred at 25° C. for 1 hr. On completion, the mixture was quenched by $NH_4Cl$ aqueous (100 mL), then extracted with EA (3×100 mL). The organic phase was separated and washed with water (100 mL), dried over $Na_2SO_4$ and filtered. The filtrate was concentrated in vacuo to give the title compound (2.1 g, 77% yield) as yellow oil. $^1H$ NMR (400 MHz, DMSO-$d_6$) δ 7.73-7.64 (m, 1H), 7.50-7.41 (m, 2H), 1.29 (s, 9H).

Step 2—6-Tert-butylpyridine-2-carboxylic acid

To a solution of 2-bromo-6-tert-butyl-pyridine (2 g, 9.34 mmol) in THE (12 mL) was added n-BuLi (2.5 M, 3.74 mL) at −78° C., then the mixture was stirred at −78° C. for 30 min. The reaction mixture was bubbling $CO_2$ (15 Psi) for 30 min at −78° C. and then warmed to 20° C. for 1 hrs. On completion, the reaction was diluted with 100 ml of water and washed with 20 ml of EA. Then the aqueous was adjusted pH to 2 and extracted with EA (3×30 mL). The extracted organic phase was concentrated in vacuo to give the title compound (530 mg, 29% yield) as brown oil. $^1$H NMR (400 MHz, $CDCl_3$) δ 8.09-8.01 (m, 1H), 7.90 (t, J=7.6 Hz, 1H), 7.72-7.61 (m, 1H), 1.41 (s, 9H).

6-Tert-butyl-N-[2-(4-formylcyclohexyl)-6-(1-hydroxy-1-methyl-ethyl)indazol-5-yl]pyridine- 2-carboxamide (Intermediate AYX)

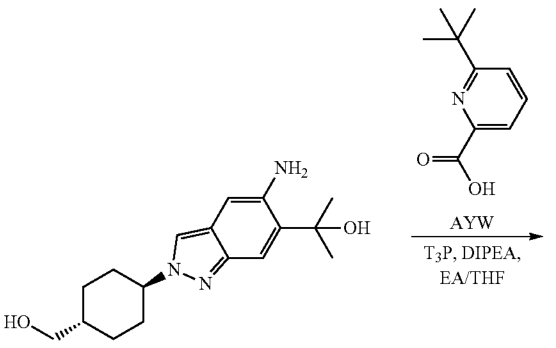

AOX

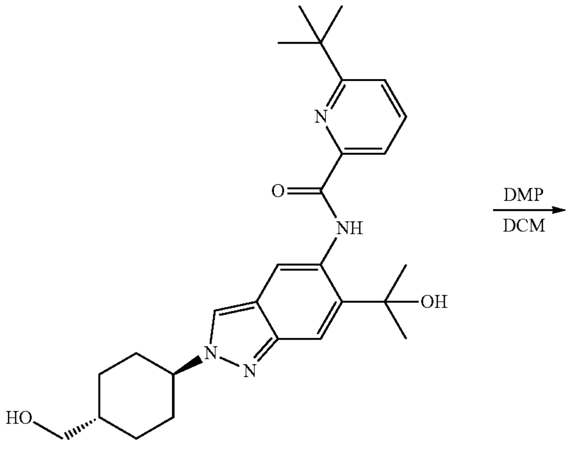

-continued

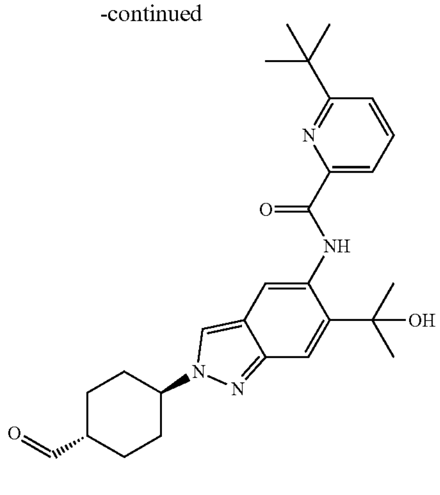

AYX

Step 1—6-Tert-butyl-N-[2-[4-(hydroxymethyl)cyclohexyl]-6-(1-hydroxy-1-methyl-ethyl)indazol-5-yl] pyridine-2-carboxamide To a mixture of 2-[5-amino-2-[4-(hydroxymethyl)cyclohexyl]indazol-6-yl]propan-2-ol (610 mg, 2.01 mmol, Intermediate AOX), 6-tert-butylpyridine-2-carboxylic acid (360 mg, 2.01 mmol, Intermediate AYW) and DIPEA (2.60 g, 20.1 mmol) in THE (10 mL) was add $T_3P$ (1.54 g, 2.41 mmol, 50% solution in EA) at 25° C. The reaction mixture stirred at 25° C. for 12 hours. On completion, the reaction mixture was quenched with water (1 mL), and concentrated in vacuo. The residue was purified by reversed-phase HPLC (0.1% FA condition) to give the title compound (300 mg, 32% yield) as a yellow solid. $^1$H NMR (400 MHz, DMSO-$d_6$) δ 12.34 (s, 1H), 8.77 (s, 1H), 8.35 (s, 1H), 8.10-7.89 (m, 2H), 7.74-7.44 (m, 2H), 5.92 (s, 1H), 4.59-4.24 (m, 2H), 3.30 (s, 2H), 2.13-2.09 (m, 2H), 2.01-1.81 (m, 4H), 1.65 (s, 6H), 1.55-1.46 (m, 1H), 1.43 (s, 9H), 1.23-1.09 (m, 2H).

Step 2—6-Tert-butyl-N-[2-(4-formylcyclohexyl)-6-(1-hydroxy-1-methyl-ethyl)indazol-5-yl]pyridine-2-carboxamide To a mixture of 6-tert-butyl-N-[2-[4-(hydroxymethyl)cyclohexyl]-6-(1-hydroxy-1-methyl-ethyl) indazol-5-yl]pyridine-2-carboxamide (230 mg, 495 umol) in DCM (7 mL) was added DMP (314 mg, 742 umol), and the mixture was stirred at 25° C. for 12 hours. On completion, the reaction mixture was quenched with saturated $Na_2SO_3$ aqueous (5 mL) and saturated $NaHCO_3$ (5 mL) aqueous was added. The mixture was extracted with DCM (2×10 mL). The organic phase was dried over anhydrous sodium sulfate. The organic phase concentrated in vacuo to give a residue. The residue was purified by reversed-phase HPLC (0.1% FA condition) to give the title compound (92 mg, 40% yield) as a yellow solid. $^1$H NMR (400 MHz, DMSO-$d_6$) δ 12.33 (s, 1H), 9.65 (s, 1H), 8.76 (s, 1H), 8.34 (s, 1H), 8.00-7.97 (m, 1H), 7.68-7.62 (m, 1H), 7.57 (s, 1H), 5.91 (s, 1H), 4.55-4.35 (m, 1H), 2.45-2.39 (m, 1H), 2.26-2.17 (m, 2H), 2.16-2.08 (m, 2H), 2.03-1.94 (m, 2H), 1.64 (s, 6H), 1.53-1.44 (m, 2H), 1.42 (s, 9H), 1.27-1.10 (m, 1H).

5-Fluoro-N-(2-((1r,4r)-4-formylcyclohexyl)-6-(2-hydroxypropan-2-yl)-2H-indazol-5-yl)-6-methylpicolinamide (Intermediate AYY)

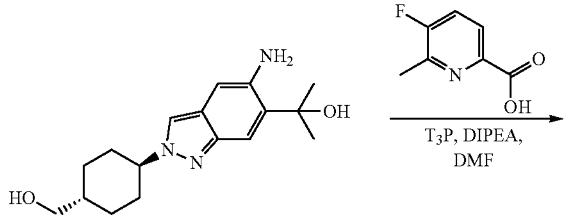

AOX

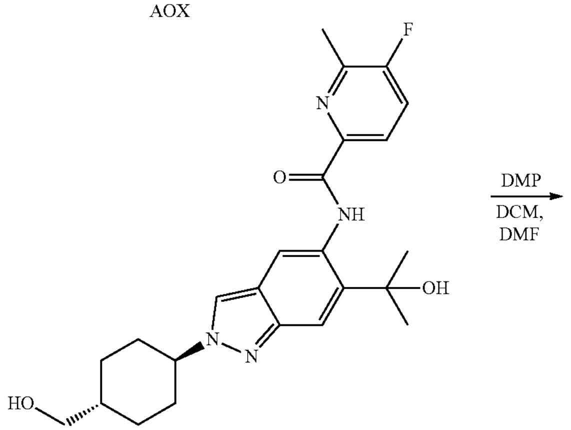

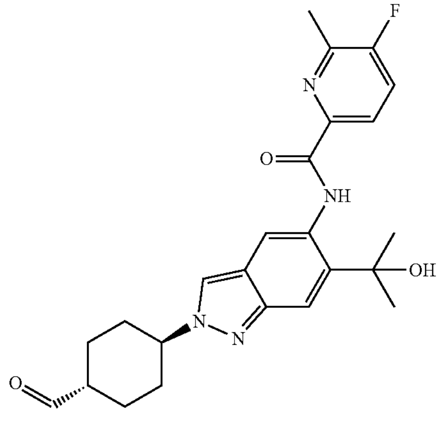

AYY

Step 1—5-Fluoro-N-(2-((1r,4r)-4-(hydroxymethyl)cyclohexyl)-6-(2-hydroxypropan-2-yl)-2H-indazol-5-yl)-6-methylpicolinamide To a solution of 2-[5-amino-2-[4-(hydroxymethyl)cyclohexyl]indazol-6-yl]propan-2-ol (200 mg, 659 umol, Intermediate AOX), 5-fluoro-6-methyl-pyridine-2-carboxylic acid (102 mg, 659 umol, CAS #1005474-88-3) in DMF (4.0 mL) was added $T_3P$ (839 mg, 1.32 mmol) and DIPEA (1.28 g, 9.89 mmol). The reaction mixture was stirred at 20° C. for 2 hours. On completion, the reaction mixture was diluted with water (30 mL) and extracted with EtOAc (3×20 mL). The combined organic layers were washed with water (2×20 mL) and brine (20 mL), dried over $Na_2SO_4$, filtered and concentrated in vacuo to give a residue. The residue was purified by prep-HPLC (FA condition: column: Waters Xbridge C18 150*50 mm*10 um; mobile phase: [water (10 mM $NH_4HCO_3$)-ACN]; B %: 25%-55%, 11.5 min) to give the title compound (128 mg, 44% yield, FA salt) as yellow solid. $^1H$ NMR (400 MHz, DMSO-$d_6$) δ 12.36 (s, 1H), 8.69 (s, 1H), 8.34 (s, 1H), 8.07 (dd, J=8.4, 4.0 Hz, 1H), 7.85 (t, J=8.8 Hz, 1H), 7.57 (s, 1H), 5.97 (s, 1H), 4.49 (t, J=5.2 Hz, 1H), 4.46-4.36 (m, 1H), 3.31-3.26 (m, 2H), 2.59 (d, J=2.8 Hz, 3H), 2.19-2.10 (m, 2H), 1.98-1.85 (m, 4H), 1.64 (s, 6H), 1.54-1.47 (m, 1H), 1.27-1.13 (m, 3H).

Step 2—5-Fluoro-N-(2-((1r,4r)-4-formylcyclohexyl)-6-(2-hydroxypropan-2-yl)-2H-indazol-5-yl)-6-methylpicolinamide To a solution of 5-fluoro-N-[2-[4-(hydroxymethyl)cyclohexyl]-6-(1-hydroxy-1-methyl-ethyl)indazol-5-yl]-6-methyl-pyridine-2-carboxamide (115 mg, 261 umol) in DCM (10 mL) and DMF (0.5 mL) was added DMP (554 mg, 1.31 mmol). The reaction mixture was stirred at 20° C. for 0.5 hour. On completion, the reaction mixture was quenched with sat. $Na_2S_2O_3$ aq. (10 mL) and sat. $NaHCO_3$ (10 mL), and then extracted with DCM (3×15 mL). The combined organic layers were washed with brine (20 mL), dried over $Na_2SO_4$, filtered and concentrated in vacuo to give the title compound (0.11 g, 96% yield) as a white solid. LC-MS ($ESI^+$) m/z 439.2 $(M+1)^+$.

Tert-butyl (1s,4s)-4-(aminomethyl)cyclohexyl)(methyl)carbamate (Intermediate AYZ)

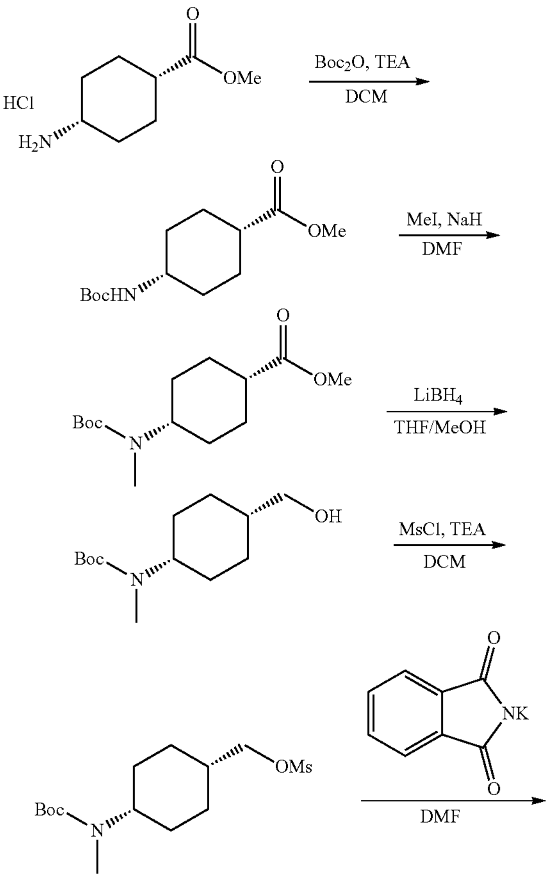

-continued

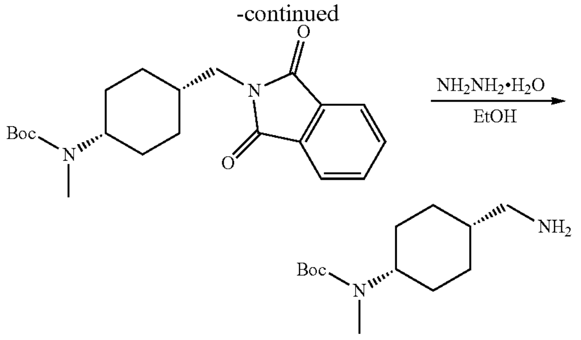

AYZ

Step 1—(1s,4s)-Methyl 4-((tert-butoxycarbonyl) amino)cyclohexanecarboxylate

To a solution of methyl 4-aminocyclohexanecarboxylate (3.00 g, 15.4 mmol, HCl salt, CAS #75143-07-6) in DCM (40 mL) was added TEA (1.73 g, 17.0 mmol) and $(Boc)_2O$ (3.72 g, 17.0 mmol) at 0° C. The mixture was stirred at 25° C. for 16 hours. On completion, the mixture was concentrated in vacuo. The crude was purified by silica gel column chromatography to give the title compound(2.30 g, 51% yield) as a colorless oil. $^1$H NMR (400 MHz, DMSO-$d_6$) δ 6.74 (d, J=6.4 Hz, 1H), 3.60 (s, 3H), 2.48 (m, 1H), 1.87-1.84 (m, 2H), 1.54-1.51 (m, 5H), 1.47-1.41 (m, 2H), 1.37 (s, 9H).

Step 2—(1s,4s)-Methyl 4-((tert-butoxycarbonyl) (methyl)amino)cyclohexanecarboxylate To a solution of methyl 4-(tert-butoxycarbonylamino) cyclohexanecarboxylate (2.00 g, 7.77 mmol) in DMF (20 mL) was added NaH (466 mg, 11.6 mmol, 60% dispersion in mineral oil) at 0° C. The mixture was stirred at 0° C. for 0.5 hour. Then $CH_3I$ (3.31 g, 23.3 mmol) was added and the mixture was stirred at 50° C. for 13.5 hours. On completion, the mixture was diluted with water (120 mL) and extracted with EA (3x30 mL), the organic layers were collected, dried over $Na_2SO_4$, filtered and concentrated to give the title compound (2.10 g, 99% yield) as a yellow oil. LC-MS (ESI$^+$) m/z 171.9 (M-Boc+H)$^+$.

Step 3—Tert-butyl ((1s,4s)-4-(hydroxymethyl)cyclohexyl)(methyl)carbamate

To a solution of methyl 4-[tert-butoxycarbonyl(methyl) amino]cyclohexanecarboxylate (1.50 g, 4.75 mmol) in THE (16 mL) and MeOH (4 mL) was added $LiBH_4$ (310 mg, 14.2 mmol) at 0° C. The mixture was stirred at 60° C. for 14 hours. On completion, the reaction was quenched with water (50 mL) and extracted with EA (3x30 mL). The organic layers were collected, dried over $Na_2SO_4$, filtered and concentrated to give the title compound (1.25 g, 92% yield) as a yellow oil. LC-MS (ESI$^+$) m/z 144.0 (M+H-100)$^+$.

Step 4—((1s,4s)-4-((Tert-butoxycarbonyl)(methyl) amino)cyclohexyl)methyl methanesulfonate To a solution of tert-butyl N-[4-(hydroxymethyl)cyclohexyl]-N-methyl-carbamate (1.25 g, 3.70 mmol) and TEA (1.12 g, 11.10 mmol) in DCM (15 mL) was added MsCl (847 mg, 7.40 mmol) at 0° C. The mixture was stirred at 20° C. for 1 hour. On completion, the mixture was diluted with brine (50 mL) and extracted with DCM (2x30 mL). The organic layers were collected, dried over $Na_2SO_4$, filtered and concentrated to give the title compound (1.70 g, 99% yield) as a yellow oil. LC-MS (ESI$^+$) m/z 221.9 (M+H-100)$^+$.

Step 5—Tert-butyl ((1s,4s)-4-((1,3-dioxoisoindolin-2-yl)methyl)cyclohexyl)(methyl)carbamate To a solution of [4-[tert-butoxycarbonyl(methyl)amino] cyclohexyl]methyl methanesulfonate (1.70 g, 5.29 mmol) in DMF (10 mL) was added (1,3-dioxoisoindolin-2-yl)potassium (1.96 g, 10.5 mmol, CAS #1074-82-4). The mixture was stirred at 100° C. for 14 hours. On completion, it was extracted with EA (3x50 mL) and the organic layers were collected, dried over $Na_2SO_4$, filtered and concentrated in vacuo. The residue was purified by Prep-HPLC(Neu: column: Waters Xbridge C18 150*50 mm*10 um; mobile phase: [water(10 mM NH4HCO3)-ACN];B %: 38%-68%, 11.5 min) to give the title product (1.00 g, 50% yield) as a yellow solid. $^1$H NMR (400 MHz, DMSO-$d_6$) δ 7.88-7.83 (m, 4H), 3.60-3.55 (m, 2H), 2.73-2.61 (m, 3H), 2.08 (s, 1H), 1.81-1.75 (m, 2H), 1.72-1.68 (m, 4H), 1.40-1.15 (m, 12H); LC-MS (ESI$^+$) m/z 273.2 (M+H-100)$^+$.

Step 6—Tert-butyl ((1s,4s)-4-(aminomethyl)cyclohexyl)(methyl)carbamate

To a solution of tert-butyl N-[4-[(1,3-dioxoisoindolin-2-yl)methyl]cyclohexyl]-N-methyl-carbamate (1.00 g, 2.68 mmol) in EtOH (15 mL) was added $NH_2NH_2.H_2O$ (474 mg, 8.05 mmol). The mixture was stirred at 60° C. for 2 hours. On completion, it was filtered and the filtrate was concentrated in vacuo. The residue was diluted with PE (30 mL), filtered and the filtrate was concentrated in vacuo to give the title compound (600 mg, 92% yield) as a yellow oil. LC-MS (ESI$^+$) m/z 243.3 (M+H)$^+$.

2-(2,6-Dioxopiperidin-3-yl)-4-((((1s,4s)-4-(methylamino)cyclohexyl)methyl)amino) isoindoline-1,3-dione (Intermediate AZA)

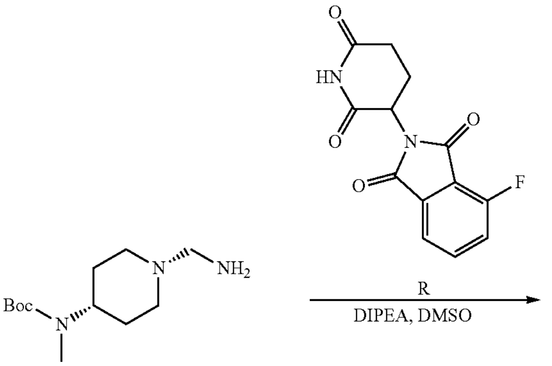

AYZ

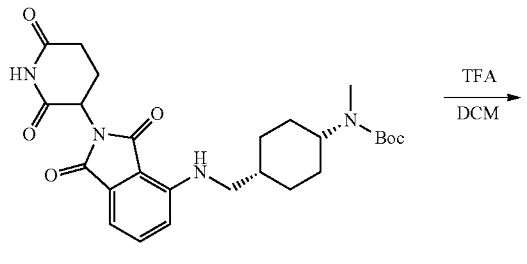

-continued

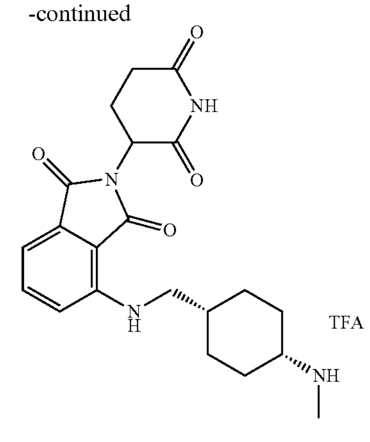

AZA

Step 1—Tert-butyl ((1s,4s)-4-(((2-(2,6-dioxopiperidin-3-yl)-1,3-dioxoisoindolin-4-yl)amino)methyl) cyclohexyl)(methyl)carbamate To a solution of tert-butyl N-[4-(aminomethyl)cyclohexyl]-N-methyl-carbamate (600 mg, 1.46 mmol, Intermediate AYZ) and 2-(2,6-dioxo-3-piperidyl)-4-fluoro-isoindoline-1,3-dione (605 mg, 2.19 mmol, Intermediate R) in DMSO (10 mL) was added DIPEA (377 mg, 2.92 mmol). The mixture was stirred at 130° C. for 0.5 hour. On completion, the mixture was concentrated in vacuo. The residue was purified by reverse-phase-flash (FA condition) to give the title product (450 mg, 61% yield) as a yellow solid. $^1$H NMR (400 MHz, DMSO-$d_6$) δ 11.08 (s, 1H), 7.60 (m, 1H), 7.15 (m, 1H), 7.02 (d, J=7.2 Hz, 1H), 6.62 (m, 1H), 5.05 (m, 1H), 3.70 (s, 1H), 3.45 (m, 3H), 2.85 (m, 1H), 2.70-2.50 (m, 6H), 2.00 (m, 2H), 1.70-1.50 (m, 6H), 1.39-1.34 (m, 10H). LC-MS (ESI$^+$) m/z 399.2 (M+H-100)$^+$.

Step 2—2-(2,6-Dioxopiperidin-3-yl)-4-((((1s,4s)-4-(methylamino)cyclohexyl)methyl)amino) isoindoline-1,3-dione A solution of tert-butyl N-[4-[[[2-(2,6-dioxo-3-piperidyl)-1,3-dioxo-isoindolin-4-yl]amino]methyl]cyclohexyl]-N-methyl-carbamate (450 mg, 902 umol) in TFA (1 mL) and DCM (4 mL) was stirred at 20° C. for 2 hours. On completion, the mixture was concentrated in vacuo to give the title compound (450 mg, 99% yield) as a yellow oil. LC-MS (ESI$^+$) m/z 399.2 (M+H)$^+$.

Tert-butyl but-3-yn-1-yl(methyl)carbamate (Intermediate AZB)

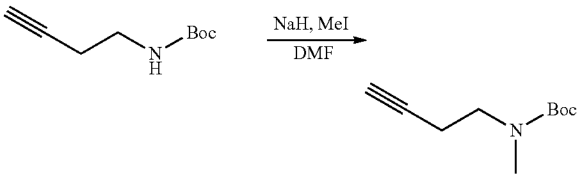

AZB

To a solution of tert-butyl N-but-3-ynylcarbamate (7 g, 41.4 mmol, CAS #149990-27-2) in THF (50 mL) was added NaH (1.99 g, 49.6 mmol, 60% dispersion in mineral oil) at 0° C. The mixture was stirred at 0° C. for 0.5 hr, then MeI (11.7 g, 82.7 mmol) was added and the mixture was stirred at 40° C. for 15.5 hrs. On completion, the reaction mixture was quenched by saturated ammonium chloride aqueous solution (250 mL) and extracted with ethyl acetate (3×200 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=100:1) to give the title compound (4.5 g, 59% yield) as colorless oil. $^1$H NMR (400 MHz, $CDCl_3$) δ 3.38 (m, 2H), 2.92 (s, 3H), 2.45-2.37 (m, 2H), 1.97 (t, J=2.8 Hz, 1H), 1.46 (s, 9H).

3-(3-Methyl-4-(4-(methylamino)but-1-yn- 1-yl)-2-oxo-2,3-dihydro- 1H-benzo[d]imidazol- 1- yl)piperidine-2,6-dione (Intermediate AZC)

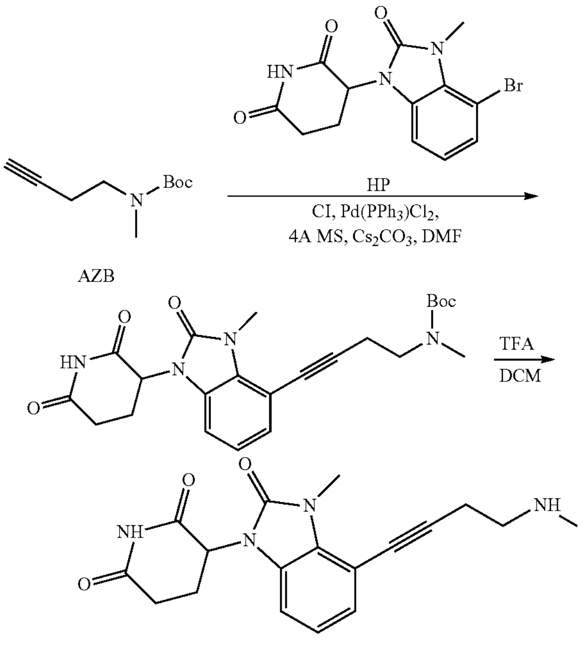

AZC

Step 1—Tert-butyl (4-(1-(2,6-dioxopiperidin-3-yl)-3- methyl-2-oxo-2,3-dihydro-1H- benzo[d]imidazol -4-yl)but-3-yn-1-yl)(methyl)carbamate To a solution of 3-(4-bromo-3-methyl-2-oxo-benzimidazol-1-yl)piperidine-2,6-dione (1.54 g, 4.55 mmol, Intermediate HP), $Cs_2CO_3$ (4.45 g, 13.7 mmol), CuI (86.6 mg, 455 umol), $Pd(PPh_3)_2Cl_2$ (319 mg, 455 umol) and 4 Å molecular sieves (500 mg) in DMF (10 mL) was degassed and purged with nitrogen for 3 times, then a solution of tert-butyl N-but-3-ynyl-N-methyl-carbamate (1 g, 5.46 mmol, Intermediate AZB) in DMF (5 mL) was added. The mixture was stirred at 80° C. for 3 hrs under nitrogen atmosphere. On completion, the reaction mixture was filtered and concentrated in vacuo to give a residue. The residue was purified by reversed-phase HPLC (FA condition) to give the title compound (1.40 g, 61% yield) as a green solid. $^1$H NMR (400 MHz, $CDCl_3$) δ 8.28 (s, 1H), 7.13 (d, J=8.0 Hz, 1H), 6.97 (t, J=8.0 Hz, 1H), 6.73 (d, J=7.6 Hz, 1H), 5.21 (dd, J=12.8, 5.6 Hz, 1H), 3.53-3.49 (m, 2H), 3.77 (s, 3H), 2.97 (s, 3H), 2.94-2.63 (m, 6H), 2.27-2.18 (m, 1H), 1.47 (s, 9H). LC-MS ($ESI^+$) m/z 341.1 $(M+H-Boc)^+$.

Step 2—3-(3-Methyl-4-(4-(methylamino)but-1-yn-1-yl)-2-oxo-2,3-dihydro- 1H-benzo[d]imidazol-1-yl)piperidine-2,6-dione To a solution of tert-butyl N-[4-[1-(2,6-dioxo-3-piperidyl)-3-methyl-2-oxo-benzimidazol-4-yl]but-3- ynyl]-N-methyl-carbamate (100 mg, 227 umol) in DCM (1 mL) was added TFA (0.1 mL). The mixture was stirred at 25° C. for 0.5 hr. On completion, the reaction mixture was concentrated in vacuo to give the title compound (100 mg, 96% yield) as yellow oil. LC-MS ($ESI^+$) m/z 341.3 $(M+H)^+$.

N-[2-(4-formylcyclohexyl)-6-(1-hydroxy-1-methyl-ethyl)indazol-5-yl]-3-(pentafluoro-sulfanyl)benzamide (Intermediate AZD)

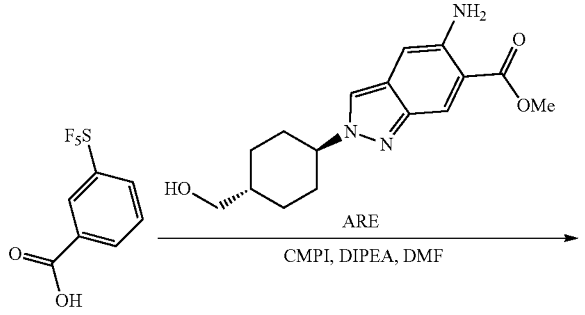

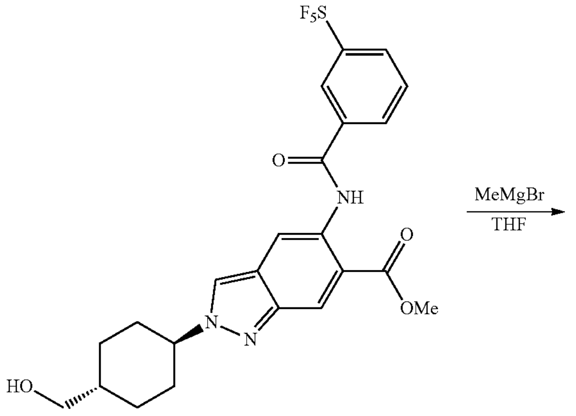

-continued

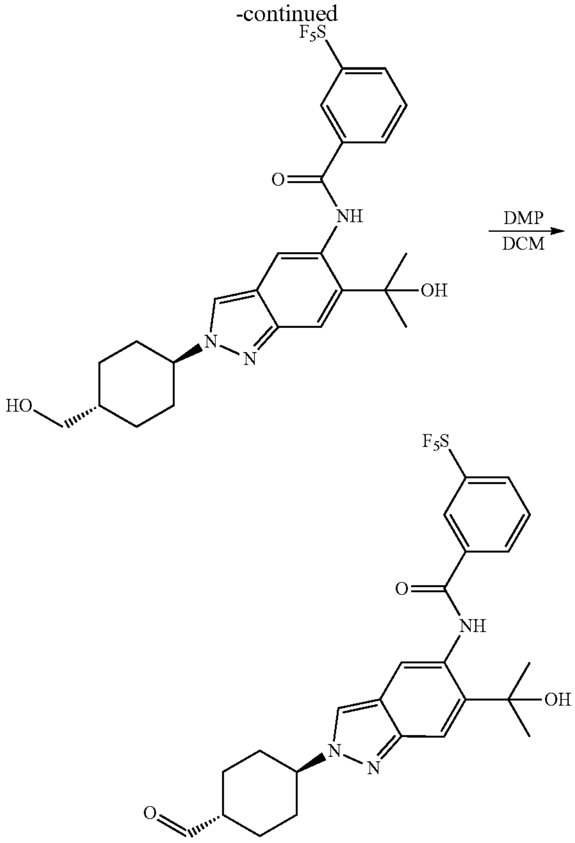

AZD

Step 1—Methyl 2-[4-(hydroxymethyl)cyclohexyl]-5-[[3-(pentafluoro-sulfanyl)benzoyl]amino]indazole-6-carboxylate To a mixture of 3-(pentafluoro-sulfanyl)benzoic acid (930 mg, 3.75 mmol, CAS #833-96-5) in DMF (20.0 mL) was added DIPEA (1.45 g, 11.2 mmol) and CMPI (1.15 g, 4.50 mmol). The mixture was stirred at 25° C. for 10 mims. Then, methyl 5-amino-2-[4-(hydroxymethyl)cyclohexyl]indazole-6- carboxylate (1.14 g, 3.75 mmol, Intermediate ARE) was added into the mixture. The reaction mixture was stirred at 25° C. for 1 hour. On completion, the reaction was poured into water (60 mL). The aqueous phase was extracted with ethyl acetate (3x30 mL). The combined organic phase was washed with brine (2x50 mL), dried with anhydrous $Na_2SO_4$, filtered and concentrated in vacuo to give a residue. The residue was triturated with PE:EA=5:1 (30 mL) at 25° C. to give the title compound (1.40 g, 70% yield) as a brown solid. $^1$H NMR (400 MHz, DMSO-$d_6$) δ 11.25 (s, 1H), 8.56 (s, 1H), 8.47 (s, 1H), 8.41 (s, 1H), 8.35 (s, 1H), 8.25 (d, J=8.0 Hz, 1H), 8.18 (dd, J=1.6, 1.6 Hz, 1H), 7.87 (t, J=8.0 Hz, 1H), 4.52 (t, J=5.2 Hz, 2H), 3.87 (s, 3H), 3.30 (t, J=5.6 Hz, 2H), 2.19 (d, J=9.2 Hz, 2H), 1.93 (d, J=10.4 Hz, 4H), 1.52-1.48 (m, 1H), 1.24-1.12 (m, 2H).

Step 2—N-[2-[4-(hydroxymethyl)cyclohexyl]-6-(1-hydroxy-1-methyl-ethyl)indazol-5-yl]-3- (pentafluoro-sulfanyl)benzamide To a mixture of methyl 2-[4-(hydroxymethyl)cyclohexyl]-5-[[3-(pentafluoro-sulfanyl)benzoyl]amino]indazole-6-carboxylate (500 mg, 937 umol) in THE (5.0 mL) was added MeMgBr (3 M, 3.12 mL) at 0° C. The mixture was stirred at 25° C. for 3 hours. On completion, the residue was poured into water (60 mL). The aqueous phase was extracted with ethyl acetate (3×30 mL). The combined organic phase was washed with brine (2×50 mL), dried with anhydrous $Na_2SO_4$, filtered and concentrated in vacuo to give a crude product. The crude product was triturated with PE:EA=5:1 (30 mL) at 25° C. to give the title compound (380 mg, 75% yield) as a brown solid $^1$H NMR (400 MHz, DMSO-$d_6$) δ 11.84 (s, 1H), 8.69-8.62 (m, 1H), 8.37 s, 2H), 8.22-8.13 (m, 2H), 7.86 (t, J=8.0 Hz, 1H), 7.60 (s, 1H), 6.62 (s, 1H), 4.50 (t, J=5.2 Hz, 1H), 4.41 (t, J=11.6 Hz, 1H), 2.22-2.10 (m, 2H), 1.90 (d, J=10.8 Hz, 4H), 1.65 (s, 6H), 1.55-1.43 (m, 2H), 1.22-1.12 (m, 3H).

Step 3—N-[2-(4-formylcyclohexyl)-6-(1-hydroxy-1-methyl-ethyl)indazol-5-yl]-3-(pentafluoro- sulfanyl) benzamide To a mixture of N-[2-[4-(hydroxymethyl)cyclohexyl]-6-(1-hydroxy-1-methyl-ethyl)indazol-5-yl]-3- (pentafluoro-sulfanyl)benzamide (380 mg, 712 umol) in DMF (5.0 mL) was added $NaHCO_3$ (299 mg, 3.56 mmol) and DMP (332 mg, 783 umol). The reaction mixture was stirred at 25° C. for 0.5 hour. On completion, the reaction mixture was poured into the water (80 mL), and extracted with DCM (2×60 mL). The combined organic phase was washed with brine (2×50 mL), dried with anhydrous $Na_2SO_4$, filtered and concentrated in vacuo to give the title compound (350 mg, 92% yield) as a brown solid. $^1$H NMR (400 MHz, DMSO-$d_6$) δ 11.85 (s, 1H), 9.66 (s, 1H), 8.67 (s, 1H), 8.38 (d, J=5.2 Hz, 2H), 8.19 (d, J=5.1 Hz, 2H), 7.87 (t, J=7.9 Hz, 1H), 7.61 (s, 1H), 6.63 (s, 1H), 4.52-4.40 (m, 1H), 2.25-2.09 (m, 5H), 2.00-1.94 (m, 2H), 1.66 (s, 6H), 1.50-1.43 (m, 2H).

Tert-butyl 4-prop-2-ynylpiperidine-1-carboxylate (Intermediate AKO)

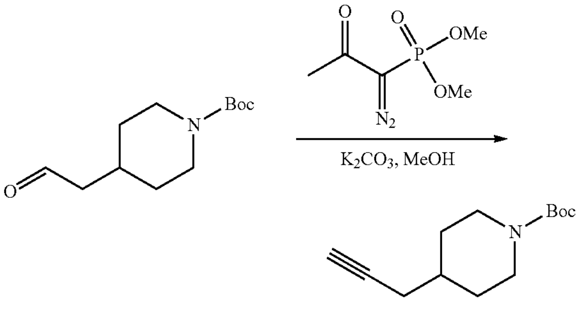

AKO

To a solution of tert-butyl 4-(2-oxoethyl)piperidine-1-carboxylate (500 mg, 2.20 mmol, CAS #142374-19-4), $K_2CO_3$ (912 mg, 6.60 mmol) in MeOH (15 mL) was added 1-diazo-1-dimethoxyphosphoryl-propan-2-one (507 mg, 2.64 mmol, CAS #90965-06-3) at 0° C. The mixture was stirred at 25° C. for 16 hours. On completion, the mixture was concentrated in vauco. The mixture was diluted with $H_2O$ (30 mL), then extracted with EA (3×20 mL). The organic layers were washed with brine (2×15 mL), dried over anhydrous $Na_2SO_4$, filtered and concentrated in vacuo to give the title compound (490 mg, 99% yield) as yellow oil. $^1$H NMR (400 MHz, $CDCl_3$) δ 4.25-4.03 (m, 2H), 2.78-2.65 (m, 2H), 2.22-2.13 (m, 2H), 2.00 (t, J=2.8 Hz, 1H), 1.85-1.72 (m, 2H), 1.72-1.60 (m, 1H), 1.48 (s, 9H), 1.30-1.15 (m, 2H).

3-[3-Methyl-2-oxo-4-[3-(4-piperidyl)propyl]benzimidazol-1-yl]piperidine-2,6-dione (Intermediate AKP)

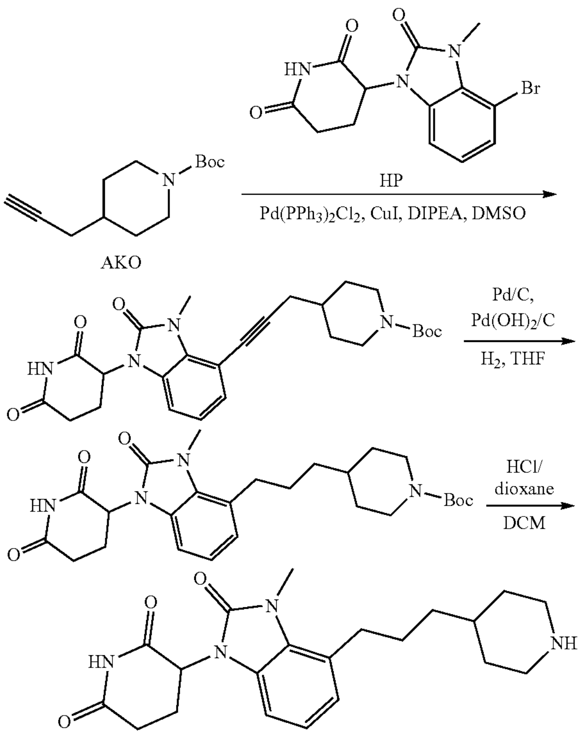

AKP

Step 1—Tert-butyl 4-[3-[1-(2,6-dioxo-3-piperidyl)-3-methyl-2-oxo-benzimidazol-4-yl]prop-2-ynyl] piperidine-1-carboxylate To a solution of tert-butyl 4-prop-2-ynylpiperidine-1-carboxylate (390 mg, 1.75 mmol, Intermediate AKO), 3-(4-bromo-3-methyl-2-oxobenzimidazol-1-yl)piperidine-2,6-dione (393 mg, 1.16 mmol, Intermediate HP) in DMSO (4 mL) was added $Pd(PPh_3)_2Cl_2$ (163 mg, 232 umol), CuI (44.3 mg, 232 umol) and DIPEA (752 mg, 5.82 mmol) under $N_2$. The mixture was stirred at 80° C. for 3 hours. On completion, the mixture was filtered and concentrated in vacuo. The mixture was purified by reverse phase: (0.1% FA) to give the title compound (450 mg, 80% yield) as yellow solid. $^1$H NMR (400 MHz, DMSO-$d_6$) δ 11.12 (s, 1H), 7.17-6.95 (m, 3H), 5.45-5.33 (m, 1H), 4.06-3.89 (m, 2H), 3.63 (s, 3H), 2.98-2.82 (m, 1H), 2.78-2.69 (m, 2H), 2.66-2.59 (m, 1H), 2.56-2.52 (m, 1H), 2.49-2.45 (m, 2H), 2.11-1.97 (m, 1H), 1.82-1.71 (m, 3H), 1.39 (s, 9H), 1.25-1.10 (m, 2H), LC-MS (ESI$^+$) m/z 503.3 (M+Na)$^+$.

Step 2—Tert-butyl 4-[3-[1-(2,6-dioxo-3-piperidyl)-3-methyl-2-oxo-benzimidazol-4-yl]propyl]piperidine-1-carboxylate To a solution of tert-butyl 4-[3-[1-(2,6-dioxo-3-piperidyl)-3-methyl-2-oxo-benzimidazol-4-yl]prop-2-ynyl]piperidine-1-carboxylate (500 mg, 1.04 mmol) in THE (50 mL) was added Pd/C (250 mg) and $Pd(OH)_2/C$ (250 mg). The mixture was stirred at 15° C. for 16 hours under $H_2$ (15 psi). On completion, the mixture was filtered and the filtrate was dried in vacuo to give the title compound (500 mg, 99% yield) as white solid. $^1H$ NMR (400 MHz, $CDCl_3$) δ 8.46 (s, 1H), 7.00 (s, 1H), 6.93-6.88 (m, 1H), 6.72-6.65 (m, 1H), 5.27-5.19 (m, 1H), 4.77 (s, 2H), 4.18-3.98 (m, 2H), 3.67 (s, 3H), 2.95-2.89 (m, 2H), 2.86-2.79 (m, 1H), 2.78-2.73 (m, 1H), 2.72-2.62 (m, 2H), 2.25-2.16 (m, 1H), 1.78-1.74 (m, 2H), 1.69-1.66 (m, 2H), 1.47 (s, 9H), 1.41-1.37 (m, 2H), 1.17-1.04 (m, 2H).

Step 3—3-[3-Methyl-2-oxo-4-[3-(4-piperidyl)propyl]benzimidazol-1-yl]piperidine-2,6-dione To a solution of tert-butyl 4-[3-[1-(2,6-dioxo-3-piperidyl)-3-methyl-2-oxo-benzimidazol-4-yl]propyl]piperidine-1-carboxylate (100 mg, 206 umol) in DCM (3.0 mL) was added HCl/dioxane (4.0 M, 2.0 mL). The mixture was stirred at 20° C. for 0.5 hour. On completion, the mixture was concentrated in vacuo to give the title compound (85.0 mg, 97% yield) as white solid. LC-MS ($ESI^+$) m/z 385.3 $(M+H)^+$.

6-(1,1-Difluoroethyl)-N-[2-(4-formylcyclohexyl)-6-(1-hydroxy-1-methyl-ethyl)indazol-5-yl]pyridine-2-carboxamide (Intermediate AZE)

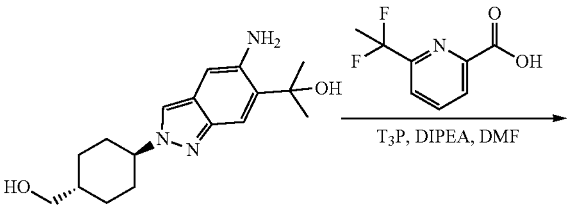

AOX

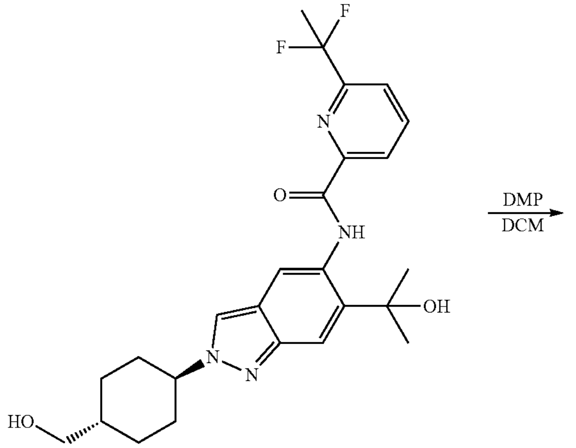

-continued

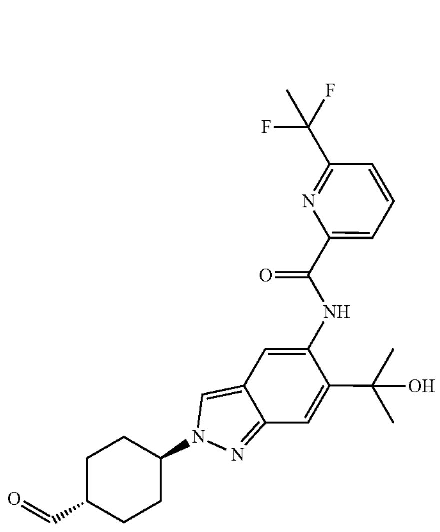

AZE

Step 1—6-(1,1-Difluoroethyl)-N-[2-[4-(hydroxymethyl)cyclohexyl]-6-(1-hydroxy-1-methyl-ethyl)indazol-5-yl]pyridine-2-carboxamide To a mixture of 2-[5-amino-2-[4-(hydroxymethyl)cyclohexyl]indazol-6-yl]propan-2-ol (120 mg, 395 umol, Intermediate AOX) and 6-(1,1-difluoroethyl)pyridine-2-carboxylic acid (81.4 mg, 435 umol, CAS #1211529-86-0) in DMF (6.0 mL) was added $T_3P$ (1.26 g, 1.98 mmol, 50% solution) and DIPEA (511 mg, 3.96 mmol) at 25° C. The mixture was stirred at 25° C. for 3 hours. On completion, the reaction mixture was quenched with water (0.5 mL) at 25° C., and concentrated in vacuo. The residue was purified by reverse phase (FA condition) to afford the title compound (100 mg, 54% yield) as a yellow solid. LC-MS ($ESI^+$) m/z 473.3 $(M+H)^+$.

Step 2—6-(1,1-Difluoroethyl)-N-[2-(4-formylcyclohexyl)-6-(1-hydroxy-1-methyl-ethyl)indazol-5-yl]pyridine-2-carboxamide To a mixture of 6-(1,1-difluoroethyl)-N-[2-[4-(hydroxymethyl)cyclohexyl]-6-(1-hydroxy-1-methyl- ethyl)indazol-5-yl]pyridine-2-carboxamide (80.0 mg, 169 umol) in DCM (5 mL) was added DMP (86.2 mg, 203 umol) at 25° C. The mixture was stirred at 25° C. for 2 hours. On completion, the mixture was quenched with sat. aq. $Na_2S_2O_3$ (2 mL) and sat. aq. $NaHCO_3$ (2 mL), and extracted with DCM (3x20 mL). The combined organic phase was dried over $Na_2SO_4$, filtered and the filtrate was concentrated in vacuo to give the title compound (70.0 mg, 87% yield). LC-MS ($ESI^+$) m/z 471.0 $(M+H)^+$.

3-[3-Methyl-2-oxo-4-[3-(4-piperidyl)prop-1-ynyl]benzimidazol-1-yl]piperidine-2,6-dione (Intermediate AZF)

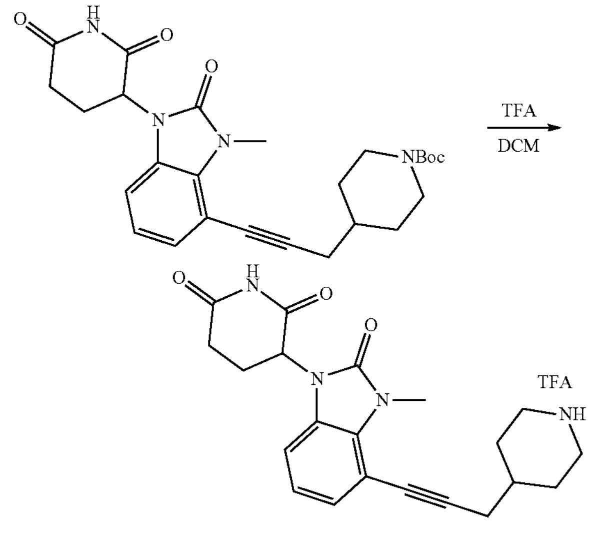

AZF

To a solution of tert-butyl 4-[3-[1-(2,6-dioxo-3-piperidyl)-3-methyl-2-oxo-benzimidazol-4-yl]prop-2- ynyl]piperidine-1-carboxylate (80 mg, 166.47 umol, synthesized via Step 1 of Intermediate AKP) in DCM (5.00 mL) was added TFA (770 mg, 6.75 mmol, 0.50 mL). The mixture was stirred at 20° C. for 1 hr. On completion, the reaction mixture was concentrated in vacuo to give the title compound (80.0 mg, 97% yield, TFA) as a yellow solid. LC-MS ($ESI^+$) m/z 381.1 $(M+H)^+$.

((1R,4R)-4-(5-amino-6-(difluoromethyl)-2H-indazol-2-yl)cyclohexyl)methanol (Intermediate AZG)

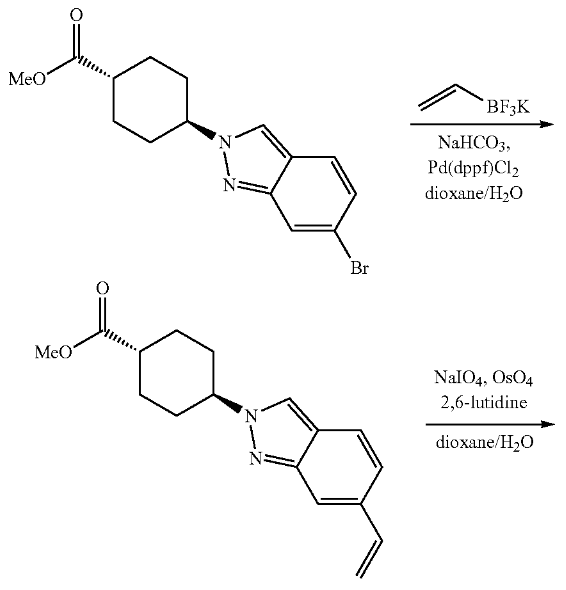

-continued

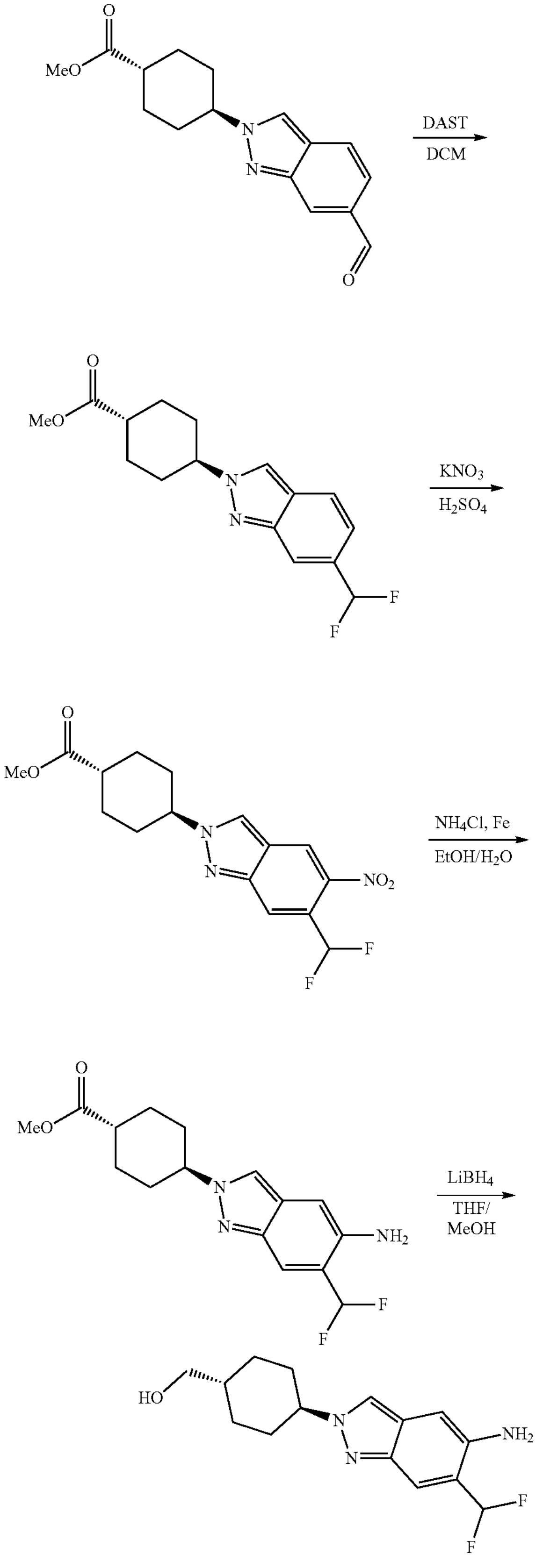

AZG

Step 1—(1R,4R)-methyl 4-(6-vinyl-2H-indazol-2-yl)cyclohexanecarboxylate

To a solution of methyl 4-(6-bromoindazol-2-yl)cyclohexanecarboxylate (6.00 g, 17.8 mmol, synthesized via Step 1 of Intermediate AOX), potassium hydride;trifluoro(vinyl) boron (7.15 g, 53.4 mmol) and $NaHCO_3$ (2.99 g, 35.6 mmol) in dioxane (120 mL) and $H_2O$ (12 mL) was added Pd(dppf)$Cl_2$ (651 mg, 890 umol). The mixture was degassed and purged with nitrogen for times, and then stirred at 90° C. for 16 hrs under nitrogen atmosphere. On completion, the reaction mixture was diluted with water (150 mL) and extracted with ethyl acetate (3×100 mL). The combined organic layers were washed with sodium chloride solution (150 mL), dried over anhydrous sodium sulfate, filtered and concentrated in vacuo to give a residue. The residue was purified by silica gel chromatography (petroleum ether:ethyl acetate=20:1 to 3:1) to give the title compound (4.60 g, 90% yield) as a white solid. $^1$H NMR (400 MHz, DMSO-$d_6$) δ 8.32 (s, 1H), 7.64 (d, J=8.8 Hz, 1H), 7.56 (s, 1H), 7.28 (dd, J=8.8, 1.2 Hz, 1H), 6.82 (dd, J=17.6, 11.2 Hz, 1H), 5.83 (d, J=17.6 Hz, 1H), 5.24 (d, J=11.2 Hz, 1H), 4.48 (m, 1H), 3.63 (s, 3H), 2.48-2.41 (m, 1H), 2.21-2.11 (m, 2H), 2.11-2.03 (m, 2H), 2.02-1.89 (m, 2H), 1.59 (m, 2H). LC-MS (ESI$^+$) m/z 285.4 (M+H)$^+$.

Step 2—(1R,4R)-methyl 4-(6-formyl-2H-indazol-2-yl)cyclohexanecarboxylate

To a solution of methyl 4-(6-vinylindazol-2-yl)cyclohexanecarboxylate (4.60 g, 16.2 mmol), 2,6-lutidine (3.47 g, 32.4 mmol) and $NaIO_4$ (13.8 g, 64.7 mmol) in dioxane (50 mL) was added a solution of $OsO_4$ (41.1 mg, 162 umol) in $H_2O$ (50 mL) at 0° C. The mixture was stirred at 25° C. for 1 hr. On completion, the reaction mixture was quenched by saturated sodium thiosulfate solution (150 mL) and extracted with ethyl acetate (3×200 mL). The combined organic layers were washed with sodium chloride solution (150 mL), dried over anhydrous sodium sulfate, filtered and concentrated in vacuo to give a residue. The residue was purified by silica gel chromatography (petroleum ether:ethyl acetate=3:1) to give the title compound (3.50 g, 76% yield) as a white solid. $^1$H NMR (400 MHz, DMSO-$d_6$) δ 10.05 (s, 1H), 8.55 (s, 1H), 8.33 (s, 1H), 7.84 (d, J=8.8 Hz, 1H), 7.47 (dd, J=8.8, 1.2 Hz, 1H), 4.69-4.55 (m, 1H), 3.64 (s, 3H), 2.49-2.43 (m, 1H), 2.26-2.15 (m, 2H), 2.12-1.95 (m, 4H), 1.62 (m, 2H). LC-MS (ESI$^+$) m/z 287.4 (M+H)$^+$.

Step 3—(1R,4R)-methyl 4-(6-(difluoromethyl)-2H-indazol-2-yl)cyclohexanecarboxylate To a solution of methyl 4-(6-formylindazol-2-yl)cyclohexanecarboxylate (2.00 g, 6.99 mmol) in DCM (5 mL) was added DAST (3.75 g, 21.0 mmol, 90% solution) dropwise at 0° C., then the mixture was warmed to 40° C. and stirred for 16 hrs. On completion, the reaction mixture was quenched with methanol (50 mL), and concentrated under reduced pressure to give a residue. The residue was diluted with water (100 mL) and extracted with ethyl acetate (3×50 mL). The combined organic layers were washed with sodium chloride solution (50 mL), dried over anhydrous sodium sulfate, filtered and concentrated in vacuo to give a residue. The residue was purified by silica gel chromatography (petroleum ether:ethyl acetate=5:1) to give the title compound (1.10 g, 31% yield) as a yellow solid. $^1$H NMR (400 MHz, DMSO-$d_6$) δ 8.49 (s, 1H), 7.89-7.78 (m, 2H), 7.22-7.14 (m, 1H), 7.11-6.90 (m, 1H), 4.55 (m, 1H), 3.63 (s, 3H), 2.49-2.40 (m, 1H), 2.22-2.13 (m, 2H), 2.12-2.04 (m, 2H), 2.04-1.92 (m, 2H), 1.60 (m, 2H). LC-MS (ESI$^+$) m/z 309.3 (M+H)$^+$.

Step 4—(1R,4R)-methyl 4-(6-(difluoromethyl)-5-nitro-2H-indazol-2-yl)cyclohexanecarboxylate To a solution of methyl 4-[6-(difluoromethyl)indazol-2-yl]cyclohexanecarboxylate (1.20 g, 3.89 mmol) in $H_2SO_4$ (5 mL) was added $KNO_3$ (787 mg, 7.78 mmol) at −10° C. Then the mixture was stirred at −10° C. for 1 hr. On completion, the reaction mixture was added into ice water and filtered. The filtrate was extracted with ethyl acetate (3×200 mL). The combined organic layers were washed with sodium chloride solution (250 mL), dried over anhydrous sodium sulfate, filtered and concentrated in vacuo to give the title compound (1.30 g, 94% yield) as a yellow solid. $^1$H NMR (400 MHz, DMSO-$d_6$) δ 8.87 (d, J=6.0 Hz, 2H), 8.07 (s, 1H), 7.69-7.37 (m, 1H), 4.69 (m, 1H), 3.63 (s, 3H), 2.49-2.43 (m, 1H), 2.19 (m, 2H), 2.13-1.98 (m, 4H), 1.61 (m, 2H). LC-MS (ESI$^+$) m/z 354.3 (M+H)$^+$.

Step 5—(1R,4R)-methyl 4-(5-amino-6-(difluoromethyl)-2H-indazol-2-yl)cyclohexanecarboxylate A solution of methyl 4-[6-(difluoromethyl)-5-nitro-indazol-2-yl]cyclohexanecarboxylate (1.30 g, 3.68 mmol), $NH_4Cl$ (1.97 g, 36.8 mmol) and Fe (2.05 g, 36.8 mmol) in EtOH (20 mL) and $H_2O$ (1 mL) was stirred at 80° C. for 16 hrs. On completion, the reaction mixture was filtered and the filtrate was concentrated in vacuo to give a residue. The residue was diluted with water (50 mL) and extracted with ethyl acetate (3×25 mL). The combined organic layers were washed with sodium chloride solution (25 mL), dried over anhydrous sodium sulfate, filtered and concentrated in vacuo to give the title compound (1.00 g, 84% yield) as a yellow solid. $^1$H NMR (400 MHz, DMSO-$d_6$) δ 8.07 (m, 1H), 7.66 (m, 1H), 7.23-6.91 (m, 1H), 6.84 (m, 1H), 4.79 (m, 2H), 4.42 (m, 1H), 3.62 (m, 3H), 2.46-2.39 (m, 1H), 2.16-2.03 (m, 4H), 1.98-1.87 (m, 2H), 1.64-1.52 (m, 2H). LC-MS (ESI$^+$) m/z 324.1 (M+H)$^+$.

Step 6—((1R,4R)-4-(5-amino-6-(difluoromethyl)-2H-indazol-2-yl)cyclohexyl)methanol To a solution of methyl 4-[5-amino-6-(difluoromethyl) indazol-2-yl]cyclohexanecarboxylate (600 mg, 1.86 mmol) in THE (4 mL) and MeOH (0.5 mL) was added $LiBH_4$ (121 mg, 5.57 mmol) at 0° C. The mixture was stirred at 25° C. for 0.5 hr then heated to 50° C. and stirred for 4 hrs. On completion, the reaction mixture was quenched with saturated ammonium chloride aqueous solution (20 mL) and the mixture was concentrated in vacuo. The residue was diluted in water (10 mL), and extracted with EA (3×10 mL). The organic phase was concentrated in vacuo to give the title compound (550 mg, 99% yield) as a yellow solid. $^1$H NMR (400 MHz, DMSO-$d_6$) δ 8.09 (s, 1H), 7.65 (s, 1H), 7.22-6.92 (m, 1H), 6.84 (s, 1H), 4.79 (m, 2H), 4.49 (t, J=5.2 Hz, 1H), 4.34 (m, 1H), 3.28 (t, J=5.6 Hz, 2H), 2.13-2.07 (m, 2H), 1.87 (m, 4H), 1.50-1.41 (m, 1H). LC-MS (ESI$^+$) m/z 296.1 (M+H)$^+$.

N-[6-(difluoromethyl)-2-(4-formylcyclohexyl)indazol-5-yl]pyrazolo[1,5-a]pyrimidine-3- carboxamide (Intermediate AZH)

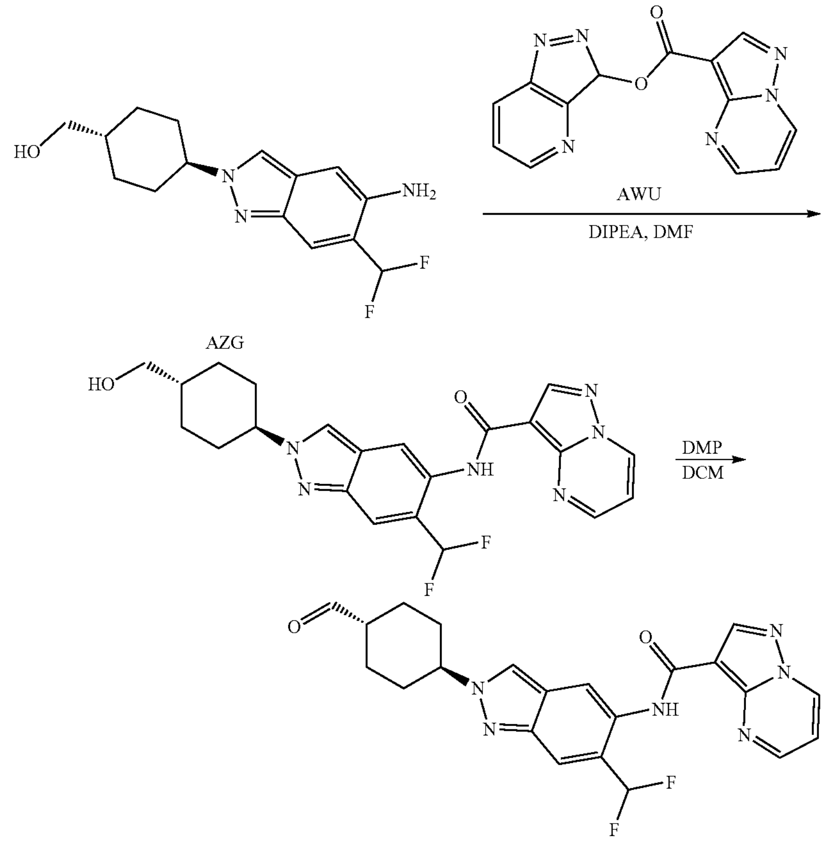

AZH

Step 1—N-[6-(difluoromethyl)-2-[4-(hydroxymethyl)]indazol-5-yl]pyrazolo[1,5-a]pyrimidine-3-carboxamide To a solution of [4-[5-amino-6-(difluoromethyl)indazol-2-yl]cyclohexyl]methanol (150 mg, 507 umol, Intermediate AZG) and in DMF (1 mL) was added triazolo[4,5-b]pyridin-3-ylpyrazolo[1,5-a] pyrimidine-3-carboxylate (214 mg, 761 umol, Intermediate AWU). The reaction mixture was stirred at 25° C. for 2 hours. Then the DIPEA (196 mg, 1.52 mmol, 265 uL) was added. The reaction mixture was stirred at 25° C. for 1 hour. On completion, the reaction was quenched with water (1 mL) and extracted with ethyl acetate (3x25 mL). The combined organic layers were washed with brine (2x20 mL), dried with anhydrous sodium sulfate and filtered. The filtrate was concentrated to give a residue. The residue was purified by silica chromatography ($SiO_2$, DCM/MeOH=40:1 to 10:1) to give the title compound (128 mg, 49% yield) as a yellow solid. LC-MS ($ESI^+$) m/z 441.2 $(M+H)^+$.

Step 2—N-[6-(difluoromethyl)-2-(4-formylcyclohexyl)indazol-5-yl]pyrazolo[1,5-a]pyrimidine-3-carboxamide To a solution of N-[6-(difluoromethyl)-2-[4-(hydroxymethyl)cyclohexyl]indazol-5-yl]pyrazolo[1,5- a]pyrimidine-3-carboxamide (125 mg, 283 umol) in THE (10 mL) was added DMP (144 mg, 340 umol, 105 uL). The reaction mixture was stirred at 25° C. for 1 hour. On completion, the mixture was quenched with $Na_2S_2O_3$ (5 mL) and extracted with ethyl acetate (3x25 mL). The combined organic layers were washed with $NaHCO_3$ (2x20 mL), dried over anhydrous sodium sulfate, filtered and concentrated in vacuo to give the title compound (119 mg, 61% yield) as yellow solid. LC-MS ($ESI^+$) m/z 439.4 $(M+H)^+$.

3-[3-methyl-2-oxo-4-[2-(4-piperidyl)ethyl]benzimidazol-1-yl]piperidine-2,6-dione (Intermediate APY)

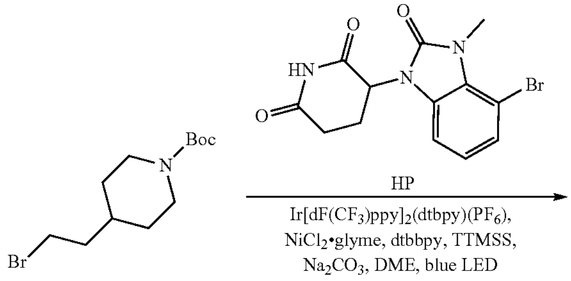

-continued

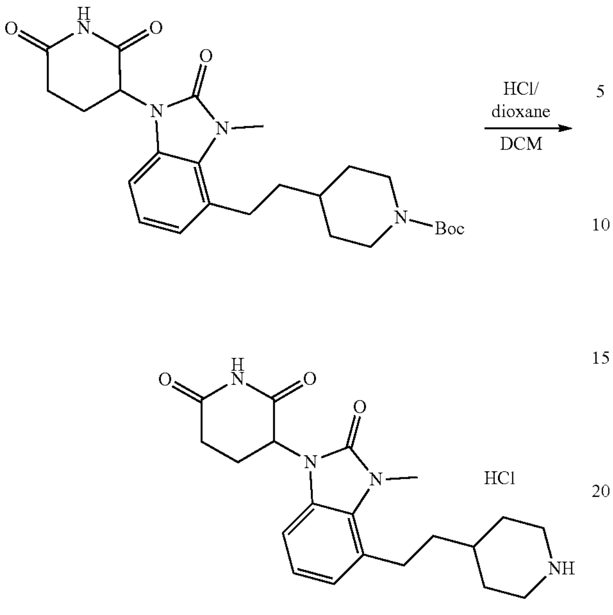

APY

Step 1—Tert-butyl4-[2-[1-(2,6-dioxo-3-piperidyl)-3-methyl-2-oxo-benzimidazol-4-yl]ethyl]piperidine-1-carboxylate To an 40 mL vial equipped with a stir bar was added 3-(4-bromo-3-methyl-2-oxo-benzimidazol-1-yl)piperidine-2,6-dione (868 mg, 2.57 mmol, Intermediate HP), tert-butyl 4-(2-bromoethyl) piperidine-1-carboxylate (900 mg, 3.08 mmol, CAS #169457-73-2), Ir[dF($CF_3$)ppy]$_2$(dtbpy)($PF_6$) (28.8 mg, 25.7 umol), NiCl2.glyme (2.82 mg, 12.8 umol), dtbbpy (4.13 mg, 15.4 umol), TTMSS (638 mg, 2.57 mmol, 792 uL) and $Na_2CO_3$ (544 mg, 5.13 mmol) in DME (20 mL). The reaction mixture was stirred and irradiated with a 34 W blue LED lamp at 25° C. for 14 hrs. On completion, the reaction mixture was filtered and the residue was concentrated in vacuo to give a residue. The crude product was purified by reverse phase flash (0.1% FA condition) to give the title compound (470 mg, 39% yield) as white solid. $^1$H NMR (400 MHz, DMSO-$d_6$) δ11.03 (br s, 1H), 6.98-6.92 (m, 2H), 6.90-6.83 (m, 1H), 5.35 (dd, J=5.2, 12.4 Hz, 1H), 3.96-3.92 (m, 2H), 3.55 (s, 3H), 2.95-2.83 (m, 3H), 2.75-2.57 (m, 4H), 2.03-1.95 (m, 1H), 1.74 (d, J=12.4 Hz, 2H), 1.53 (t, J=6.0 Hz, 3H), 1.39 (s, 9H), 1.13-0.99 (m, 2H); LC-MS (ESI$^+$) m/z 415.2 (M+H-56)$^+$.

Step 2—3-[3-Methyl-2-oxo-4-[2-(4-piperidyl)ethyl]benzimidazol-1-yl]piperidine-2,6-dione To a solution of tert-butyl4-[2-[1-(2,6-dioxo-3-piperidyl)-3-methyl-2-oxo-benzimidazol-4-yl]ethyl]piperidine-1-carboxylate (200 mg, 425 umol) in DCM (3.0 mL) was added HCl/dioxane (4 M, 1.0 mL). The reaction mixture was stirred at 25° C. for 1 hr. On completion, the reaction mixture was concentrated in vacuo to give the title compound (170 mg, 90% yield, HCl salt) as orange solid. LC-MS (ESI$^+$) m/z 371.2 (M+H)$^+$.

3-[5-(Azetidin-3-yl)-3-methyl-2-oxo-benzimidazol-1-yl]piperidine-2,6-dione (Intermediate AZI)

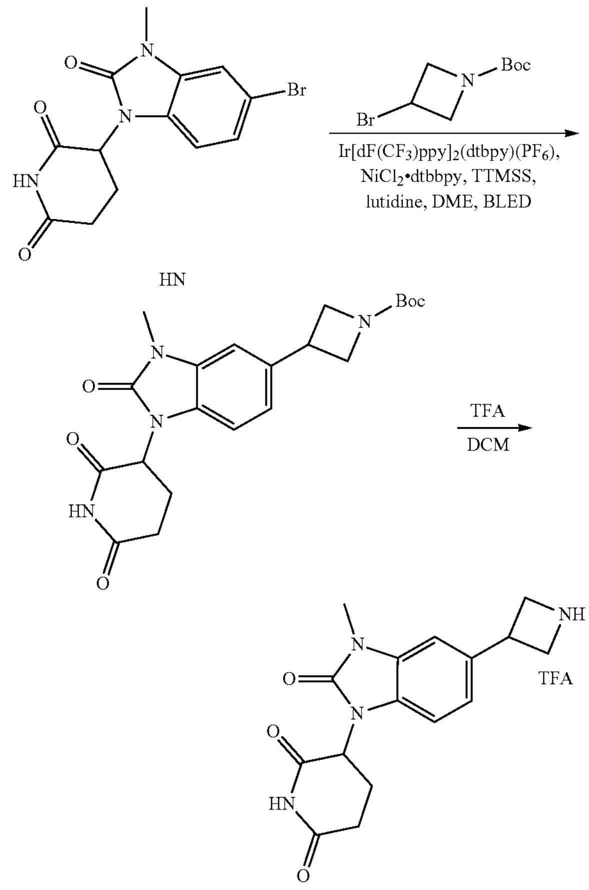

AZI

Step 1—Tert-butyl3-[1-(2,6-dioxo-3-piperidyl)-3-methyl-2-oxo-benzimidazol-5-yl]azetidine-1- carboxylate To an 40 mL vial equipped with a stir bar was added 3-(5-bromo-3-methyl-2-oxo-benzimidazol-1-yl)piperidine-2,6-dione (0.00 g, 2.96 mmol, Intermediate HN), tert-butyl 3-bromoazetidine-1-carboxylate (908 mg, 3.84 mmol, CAS #1064194-10-0), Ir[dF(CF3)ppy]2(dtbpy)($PF_6$) (33.2 mg, 29.57 umol), $NiCl_2$.dtbbpy (5.88 mg, 14.8 umol), TTMSS (735 mg, 2.96 mmol), 2,6-dimethylpyridine (634 mg, 5.91 mmol) in DME (24 mL). The reaction was stirred and irradiated with a 34 W blue LED lamp at 25° C. for 14 hr under nitrogen. On completion, the reaction mixture was filtered. The filtrate was concentrated in vacuo to give a residue. The crude product was purified by reverse phase flash (0.1% FA condition) to give the title compound (460 mg, 38% yield) as a white solid. $^1$H NMR (400 MHz, DMSO-$d_6$) δ 11.00 (s, 1H), 7.12 (d, J=1.2 Hz, 1H), 7.01-6.97 (m, 1H), 6.90 (dd, J=1.2, 8.0 Hz, 1H), 5.27 (dd, J=5.6, 12.8 Hz, 1H), 4.16 (s, 2H), 3.85-3.73 (m, 3H), 3.25 (s, 3H), 2.87-2.76 (m, 1H), 2.68-2.59 (m, 1H), 2.58-2.49 (m, 1H), 1.96-1.88 (m, 1H), 1.32 (s, 9H); LC-MS (ESI$^+$) m/z 415.2 (M+H)$^+$.

Step 2—3-[5-(Azetidin-3-yl)-3-methyl-2-oxo-benzimidazol-1-yl]piperidine-2,6-dione To a solution of tert-butyl 3-[1-(2,6-dioxo-3-piperidyl)-3-methyl-2-oxo-benzimidazol-5-yl]azetidine-1-carboxylate (100 mg, 241 umol) in DCM (3 mL) and TFA (1.0 mL). The mixture was stirred at 25° C. for 30 min. On completion, the reaction mixture was concentrated in vacuo to give the title compound (70 mg, 100% yield, TFA) as yellow oil. LC-MS (ESI$^+$) m/z 315.1 (M+H)$^+$.

N-[6-(difluoromethyl)-2-(4-formylcyclohexyl)indazol-5-yl]-6-(1-fluoro-1-methyl-ethyl)pyridine-2-carboxamide (Intermediate AZJ)

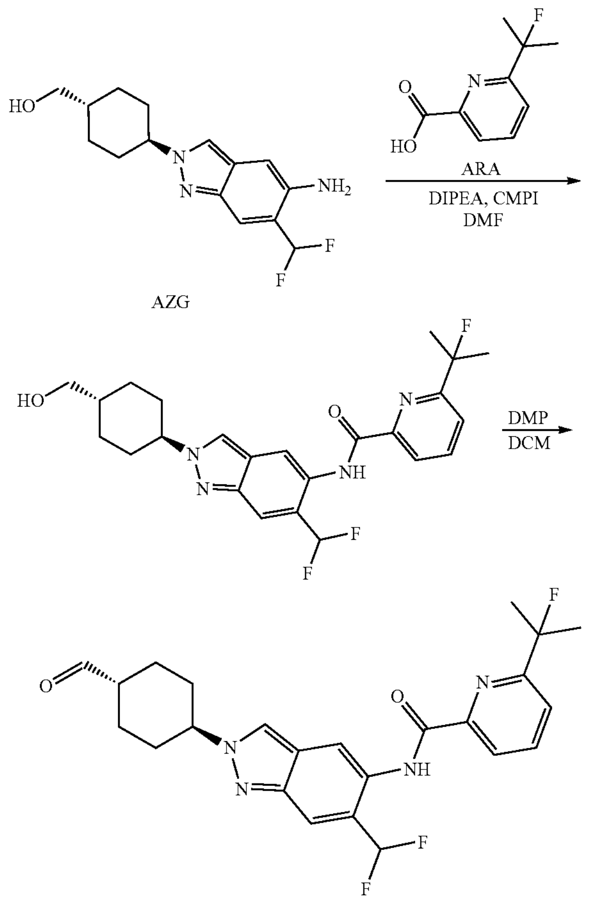

Step 1—N-[6-(difluoromethyl)-2-[4-(hydroxymethyl)cyclohexyl]indazol-5-yl]-6-(1-fluoro-1-methyl-ethyl)pyridine-2-carboxamide To a mixture of 6-(1-fluoro-1-methyl-ethyl)pyridine-2-carboxylic acid (600 mg, 3.28 mmol, Intermediate ARA), DIPEA (1.06 g, 8.20 mmol, 1.43 mL) in DMF (15 mL) was added CMPI (1.09 g, 4.26 mmol) at 25° C. The reaction mixture was stirred at 25° C. for 0.5 hour. Then the reaction mixture was added to a solution of [4-[5-amino-6-(difluoromethyl)indazol-2-yl]cyclohexyl]methanol (1.02 g, 3.44 mmol, Intermediate AZG) in DMF (15 mL). The reaction mixture stirred at 25° C. for 0.5 hour. On completion, the reaction mixture was quenched with water (15 ml), then the mixture was exacted with EA (3x50 ml). The organic layer was washed with saturated NaCl aqueous (100 ml) three times. The organic phase was dried over anhydrous sodium sulfate, and concentrated in vacuo to give the title compound (1.41 g, 93% yield) as a yellow solid. $^1$H NMR (400 MHz, DMSO-d$_6$) δ=10.69 (s, 1H), 8.66 (s, 1H), 8.57 (s, 1H), 8.17 (d, J=7.6 Hz, 1H), 8.16-8.10 (m, 1H), 8.01 (s, 1H), 7.85 (td, J=1.6, 7.2 Hz, 1H), 7.45-7.15 (m, 1H), 4.63-4.49 (m, 2H), 4.48 (br d, J=5.2 Hz, 1H), 3.30 (t, J=5.6 Hz, 2H), 2.18 (d, J=9.2 Hz, 2H), 1.80 (s, 3H), 1.74 (s, 3H), 1.60-1.36 (m, 2H), 1.32-1.18 (m, 2H), 1.18-1.04 (m, 2H). LC-MS (ESI$^+$) m/z 461.4 (M+1)$^+$.

Step 2—N-[6-(difluoromethyl)-2-(4-formylcyclohexyl)indazol-5-yl]-6-(1-fluoro-1-methyl- ethyl) pyridine-2-carboxamide To a solution of N-[6-(difluoromethyl)-2-[4-(hydroxymethyl)cyclohexyl]indazol-5-yl]-6-(1-fluoro-1- methyl-ethyl) pyridine-2-carboxamide (100 mg, 217 umol) in THF (5 mL) was added DMP (110 mg, 260 umol). The reaction mixture was stirred at 25° C. for 1 hour. On completion, the mixture was quenched with $Na_2S_2O_3$ (1 mL). The mixture was extracted with ethyl acetate (3x25 mL) and washed with sat. $NaHCO_3$ (25 mL). The combined organic phase was dried over anhydrous sodium sulfate and concentrated to give the title compound (100 mg, 83% yield) as a yellow solid. LC-MS (ESI$^+$) m/z 459.1 (M+1)$^+$.

3-(3-Methyl-2-oxo-4-(piperidin-4-yl)-2,3- dihydro-1H-benzo[d]imidazol-1-yl)piperidine-2,6-dione (Intermediate AZK)

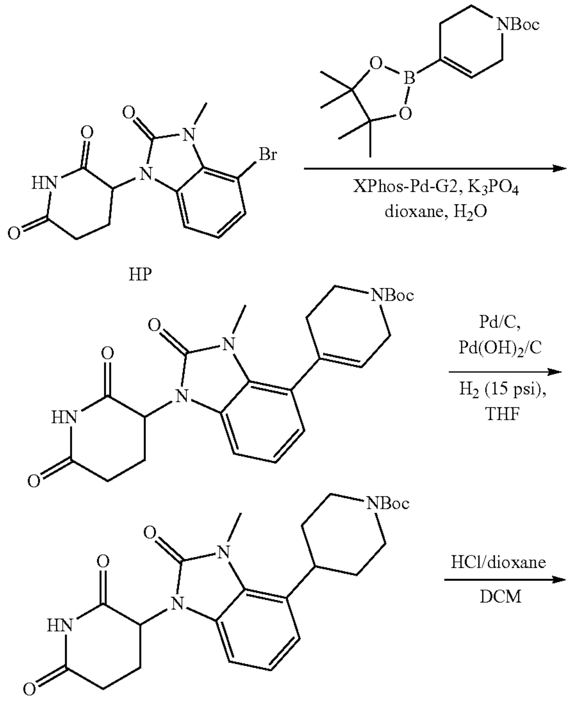

-continued

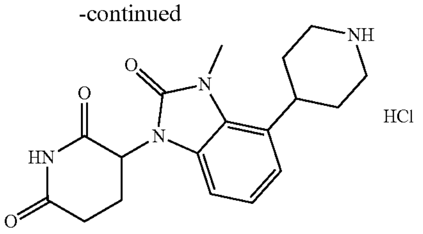

AZK

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1(2H)-carboxylate To a solution of 3-(4-bromo-3-methyl-2-oxo-benzimidazol-1-yl)piperidine-2,6-dione (9.00 g, 26.6 mmol, Intermediate HP), tert-butyl 4-(4,4,5,5-tetramethyl-1,3,2-dioxaborolan-2-yl)-3,6-dihydro-2H-pyridine-1-carboxylate (12.3 g, 39.9 mmol) and XPhos-Pd-G2 (2.09 g, 2.66 mmol) in dioxane (150 mL) and $H_2O$ (15 mL) was added $K_3PO_4$ (11.3 g, 53.2 mmol). The reaction mixture was stirred at 80° C. for 4 hours under $N_2$. On completion, the reaction mixture was filtered. The filtrate was dried with anhydrous $Na_2SO_4$ and filtered. The filtrate was concentrated in vacuo. The residue was triturated with sat. $NH_4Cl$ (2×50 mL), water (2×50 mL) and EA (2×50 mL) and filtered. The solid was dried in vacuo to give the title compound (8.00 g, 68% yield) as an off-white solid. LC-MS ($ESI^+$) m/z 441.1 $(M+H)^+$ Step 2—Tert-butyl 4-(1-(2,6-dioxopiperidin-3-yl)-3-methyl- 2-oxo-2,3-dihydro-1H- benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6- dihydro-2H-pyridine-1-carboxylate (8.00 g, 18.2 mmol) in DMF (20 mL) and THE (60 mL) was added $H_2$, Pd/C (1.00 g, 10 wt %) and $Pd(OH)_2$ (1.00 g, 3.56 mmol, 50 wt %). The mixture was degassed and purged with nitrogen 3 times, then degassed and purged with hydrogen 3 times. The mixture was stirred at 25° C. for 16 hrs under hydrogen (15 psi) atmosphere. On completion, the reaction mixture was filtered and the combined filtrates were concentrated in vacuo to give the title compound (5.60 g, 70% yield) as a white solid. $^1H$ NMR (400 MHz, DMSO-$d_6$) δ 11.10 (s, 1H), 7.06-6.92 (m, 3H), 5.38 (m, 1H), 4.18-3.96 (m, 2H), 3.60 (s, 3H), 3.48-3.39 (m, 1H), 2.97-2.81 (m, 3H), 2.76-2.61 (m, 2H), 2.05-1.94 (m, 1H), 1.81 (m, 2H), 1.65-1.50 (m, 2H), 1.47-1.40 (m, 9H). LC-MS ($ESI^+$) m/z 287.4 $(387.3)^+$.

Step 3—3-(3-Methyl-2-oxo-4-(piperidin-4-yl)-2,3-dihydro-1H-benzo[d]imidazol-1- yl)piperidine-2,6-dione To a solution of tert-butyl 4-[1-(2,6-dioxo-3-piperidyl)-3-methyl-2-oxo-benzimidazol-4- yl]piperidine -1-carboxylate (100 mg, 226 umol) in DCM (1 mL) was added HCl/dioxane (1 mL). The reaction mixture was stirred at 25° C. for 0.5 hr. On completion, the reaction mixture was concentrated in vacuo to give the title compound (85.0 mg, 99% yield) as a yellow solid. LC-MS ($ESI^+$) m/z 343.3 $(M+H)^+$.

3-[3-Methyl-2-oxo-5-(4-piperidyl)benzimidazol-1-yl]piperidine-2,6-dione (Intermediate AZL)

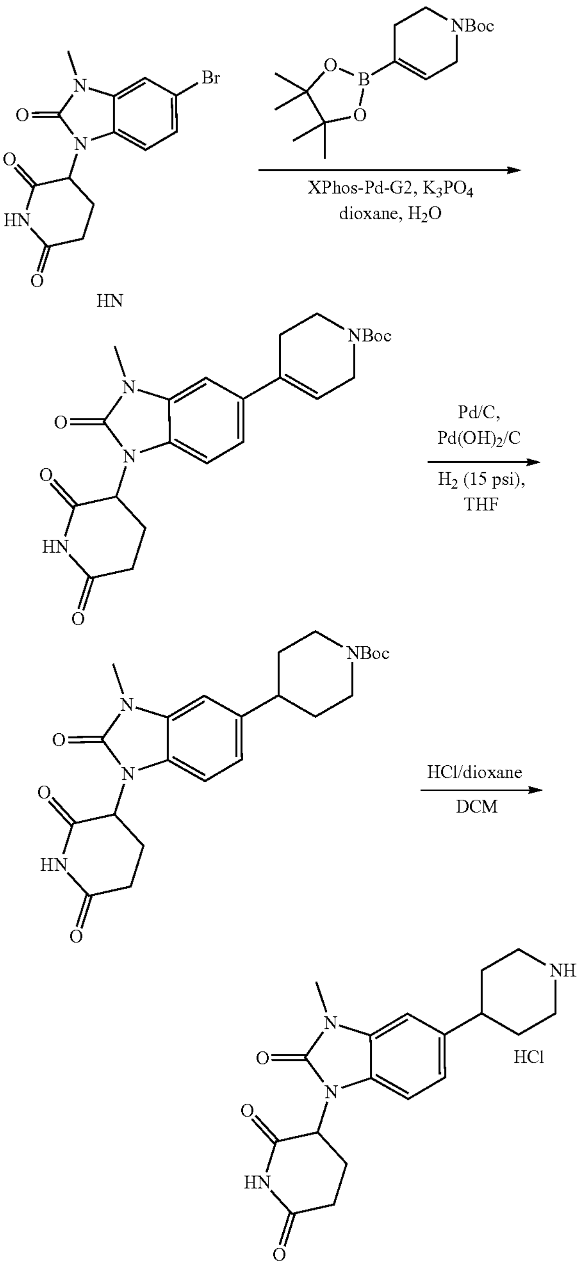

AZL

Step 1—Tert-butyl 4-[1-(2,6-dioxo-3-piperidyl)-3-methyl-2-oxo-benzimidazol-4-yl]-3,6-dihydro-2H -pyridine-1-carboxylate To a solution of 3-(5-bromo-3-methyl-2-oxo-benzimidazol-1-yl)piperidine-2,6-dione (5.00 g, 14.8 mmol, Intermediate HN), tert-butyl 4-(4,4,5,5-tetramethyl-1,3,2-dioxaborolan-2-yl)-3,6-dihydro-2H -pyridine-1-carboxylate (5.49 g, 17.7 mmol, CAS #286961-14-6), $K_3PO_4$(6.28 g, 29.6 mmol) and [2-(2-aminophenyl)phenyl]-chloro-palladium; dicyclohexyl-[3-(2,4,6-triisopropylphenyl)phenyl]phosphane (1.16 g, 1.48 mmol,) in dioxane (100 mL) and $H_2O$ (5.0 mL) was stirred at 80° C. for 4 hrs. On completion, the mixture filtered and the filtrate was concentrated in vacuo. The residue was purified by reversed phase flash (0.1% FA condition) to give the title compound (2.30 g, 53% yield) as white solid. $^1H$ NMR (400 MHz, DMSO-$d_6$) δ 11.09 (s, 1H), 7.27 (s, 1H), 7.14-7.04 (m, 2H), 6.11 (s, 1H), 5.36 (dd, J=12.8, 5.2 Hz, 1H), 4.01 (d, J=7.2 Hz, 2H), 3.55 (t, J=5.6 Hz, 2H), 3.35 (s, 3H), 2.95-2.83 (m, 1H), 2.73-2.59 (m, 2H), 2.06-1.95 (m, 2H), 1.46-1.39 (m, 9H), 1.17 (t, J=7.2 Hz, 1H). LC-MS (ESI$^+$) m/z 441.2 (M+H)$^+$.

Step 2—Tert-butyl 4-[i-(2,6-dioxo-3-piperidyl)-3-methyl-2-oxo-benzimidazol-5-yl]piperidine-1- carboxylate To a solution of tert-butyl 4-[1-(2,6-dioxo-3-piperidyl)-3-methyl-2-oxo-benzimidazol-5-yl]-3,6-dihydro-2H-pyridine-1-carboxylate (2.30 g, 5.22 mmol) in THE (150 mL) was added Pd/C (800 mg, 10 wt %) and $Pd(OH)_2$ (800 mg, 5.70 mmol) at 25° C. The reaction mixture was stirred at 60° C. for 16 hr under $H_2$ (15 psi). On completion, the reaction mixture was filtered with celite and the filtrate was concentrated in vacuo to give the title compound (2.30 g, 87% yield) as white solid. $^1H$ NMR (400 MHz, $CDCl_3$) δ 8.10 (s, 1H), 7.02-6.87 (m, 2H), 6.76 (d, J=8.0 Hz, 1H), 5.23 (dd, J=5.6, 12.6 Hz, 1H), 4.30-4.25 (m, 2H), 3.45 (s, 3H), 2.99-2.68 (m, 6H), 2.30-2.21 (m, 1H), 1.88-1.81 (m, 2H), 1.51 (s, 9H), 1.48-1.44 (m, 2H). LC-MS (ESI$^+$) m/z 465.2 (M+23)$^+$.

Step 3—3-[3-Methyl-2-oxo-5-(4-piperidyl)benzimidazol-1-yl]piperidine-2,6-dione

To a mixture of tert-butyl 4-[1-(2,6-dioxo-3-piperidyl)-3-methyl-2-oxo-benzimidazol-5-yl]piperidine -1-carboxylate (300 mg, 678 umol) in DCM (3.0 mL) was added HCl/dioxane (4 M, 170 uL) in one portion at 25° C. under $N_2$. The mixture was stirred at 25° C. for 30 min. On completion, the reaction mixture was concentrated in vacuo to give the title compound (250 mg, 91% yield, HCl salt) as white solid. LC-MS (ESI$^+$) m/z 343.1 (M+H)$^+$.

3-(4-(Azetidin-3-yl)-3-methyl-2-oxo-2,3-dihydro-1H-benzo[d]imidazol-1-yl)piperidine-2,6-dione (Intermediate AZM)

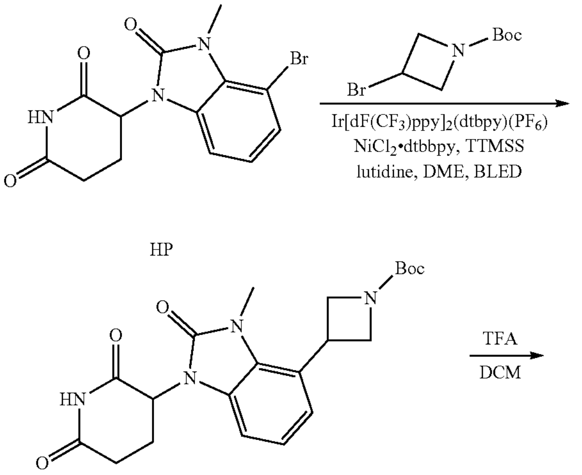

HP

-continued

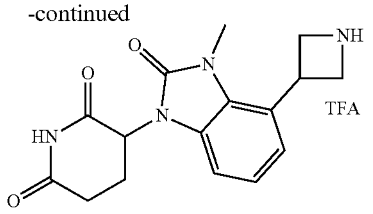

AZM

Step 1—Tert-butyl 3-(1-(2,6-dioxopiperidin-3-yl)-3-methyl-2-oxo-2,3-dihydro-1H-benzo[d]imidazol-4-yl)azetidine-1-carboxylate. (3) -Notebook- Page: EW18544-104

To an 40 mL vial equipped with a stir bar was added 3-(4-bromo-3-methyl-2-oxo-benzimidazol-1-yl)piperidine-2,6-dione (1.0 g, 2.96 mmol, Intermediate HP), tert-butyl 3-iodoazetidine-1-carboxylate (1.09 g, 3.84 mmol, CAS #254454-54-1), Ir[dF(CF3)ppy]2(dtbpy)(PF6) (33.1 mg, 29.5 umol), TTMSS (735 mg, 2.96 mmol), 2,6-dimethylpyridine (633 mg, 5.91 mmol) and $NiCl_2$ dtbbpy (5.88 mg, 14.7 umol) in DME (24 mL). The reaction was stirred and irradiated with a 34 W blue LED lamp at 25° C. for 14 hr. On completion, the mixture was filtered and the filtrate was concentrated in vacuo. The crude product was purified by reverse phase flash (0.1% FA condition) to give the title compound (900 mg, 71% yield) as white solid. $^1H$ NMR (400 MHz, DMSO-$d_6$) δ 11.10 (s, 1H), 7.24 (d, J=4.4 Hz, 1H), 7.14-7.00 (m, 2H), 5.42-5.34 (m, 1H), 4.56-4.46 (m, 1H), 4.29 (t, J=8.4 Hz, 2H), 3.97 (t, J=6.0 Hz, 2H), 3.51 (s, 3H), 2.96-2.81 (m, 1H), 2.78-2.59 (m, 2H), 2.06-1.95 (m, 1H), 1.42 (s, 9H).

Step 2—3-(4-(Azetidin-3-yl)-3-methyl-2-oxo-2,3-dihydro-1H-benzo[d]imidazol-1-yl)piperidine-2,6-dione To a solution of tert-butyl 3-[1-(2,6-dioxo-3-piperidyl)-3-methyl-2-oxo-benzimidazol-4-yl]azetidine-1- carboxylate (150 mg, 361 umol) in DCM (3.0 mL) was added TFA (1.54 g, 13.5 mmol). The mixture was stirred at 25° C. for 30 min. On completion, the reaction mixture was concentrated in vacuo to give the title compound (120 mg, 80% yield, TFA) as brown solid. LC-MS (ESI$^+$) m/z 315.2 (M+H)$^+$.

2-(2,6-dioxo-3-piperidyl)-4-[[(2R)-morpholin-2-yl]methylamino]isoindoline-1,3-dione (Intermediate ALB)

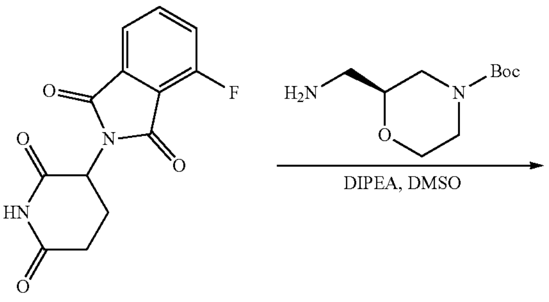

R

-continued

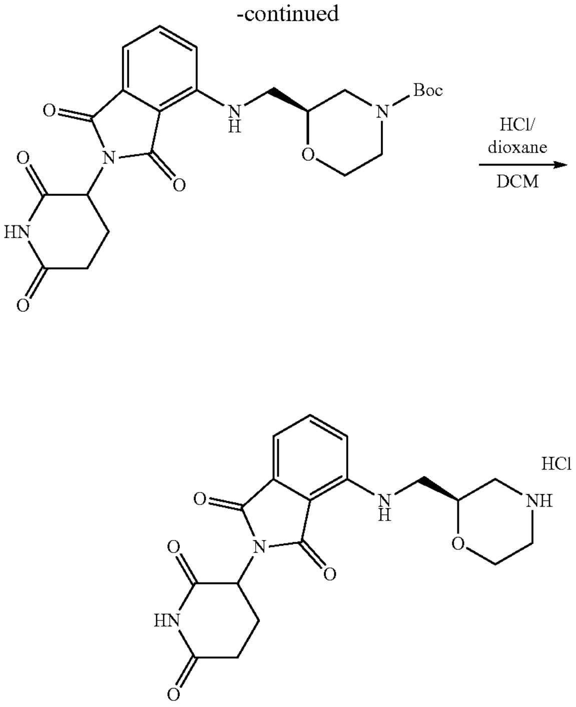

ALB

Step 1—Tert-butyl (2S)-2-[[[2-(2,6-dioxo-3-piperidyl)-1,3-dioxo-isoindolin-4-yl]amino]methyl] morpholine-4-carboxylate To a solution of 2-(2,6-dioxo-3-piperidyl)-4-fluoro-isoindoline-1,3-dione (210 mg, 762 umol, Intermediate R) and tert-butyl (2S)-2-(aminomethyl)morpholine-4-carboxylate (150 mg, 693 umol, CAS #879403-42-6) in DMSO (2.00 mL) was added DIPEA (448 mg, 3.47 mmol). The mixture was stirred at 90° C. for 3 hours. On completion, the reaction mixture was quenched with $H_2O$ (0.5 mL), and then concentrated in vacuo to give a residue. The residue was purified by reverse phase (0.1% FA condition) to give the title compound (100 mg, 30% yield) as a white solid. $^1H$ NMR (400 MHz, $CDCl_3$) δ 8.01 (s, 1H), 7.52 (dd, J=7.2, 8.4 Hz, 1H), 7.13 (d, J=6.8 Hz, 1H), 6.93 (d, J=8.5 Hz, 1H), 6.51 (t, J=5.6 Hz, 1H), 4.95-4.90 (m, 1H), 4.12-3.81 (m, 3H), 3.68-3.60 (m, 1H), 3.59-3.52 (m, 1H), 3.47-3.27 (m, 2H), 2.96-2.90 (m, 1H), 2.89-2.68 (m, 4H), 2.22-2.05 (m, 1H), 1.48 (s, 9H).

Step 2—2-(2,6-Dioxo-3-piperidyl)-4-[[(2R)-morpholin-2-yl]methylamino]isoindoline-1,3-dione To a solution of tert-butyl (2S)-2-[[[2-(2,6-dioxo-3-piperidyl)-1,3-dioxo-isoindolin-4-yl]amino]methyl]morpholine-4-carboxylate (100 mg, 211 umol) in DCM (1.00 mL) was added TFA (1.54 g, 13.5 mmol, 1.00 mL). The mixture was stirred at 20° C. for 1 hour. On completion, the reaction mixture was concentrated in vacuo to give the title compound (100 mg, 97% yield, TFA) as a yellow solid. LC-MS ($ESI^+$) m/z 373.5 $(M+H)^+$.

2-(2,6-Dioxo-3-piperidyl)-4-[[(2S)-4-[3-(methylamino)propyl]morpholin-2-yl]methylamino]isoindoline-1,3-dione (Intermediate ALC)

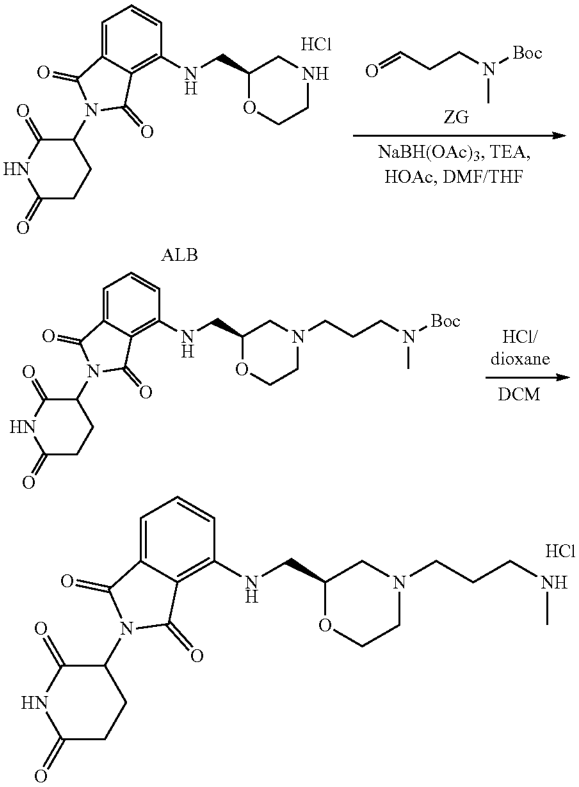

ALC

Step 1—Tert-butyl N-[3-[(2S)-2-[[[2-(2,6-dioxo-3-piperidyl)-1,3-dioxo-isoindolin-4-yl]amino]methyl] morpholin-4-yl]propyl]-N-methyl-carbamate To a solution of 2-(2,6-dioxo-3-piperidyl)-4-[[(2R)-morpholin-2-yl]methylamino]isoindoline-1,3-dione (100 mg, 205 umol, TFA salt, Intermediate ALB) in a mixed solvent of DMF (1.00 mL) and THF (1.00 mL) was added TEA (20.8 mg, 205 umol), the mixture was stirred at 20° C. for 10 minutes. Then, HOAc (24.7 mg, 411 umol) and tert-butyl N-methyl-N-(3-oxopropyl)carbamate (40.0 mg, 213 umol, Intermediate ZG) was added. The mixture was stirred at 20° C. for 0.5 hour. After that, $NaBH(OAc)_3$ (52.3 mg, 246 umol) was added, the mixture was stirred at 20° C. for 1 hour. On completion, the reaction mixture was quenched with $H_2O$ (0.5 mL), and then concentrated in vacuo to give a residue. The residue was purified by reverse phase (0.1% FA condition) to give the title compound (60.0 mg, 53% yield) as a yellow solid. $^1H$ NMR (400 MHz, $CDCl_3$) δ 8.19 (s, 1H), 7.55-7.48 (m, 1H), 7.14 (d, J=7.2 Hz, 1H), 6.93 (d, J=8.8 Hz, 1H), 6.48 (t, J=5.6 Hz, 1H), 4.99-4.88 (m, 1H), 4.03-3.90 (m, 2H), 3.89-3.79 (m, 1H), 3.48-3.41 (m, 2H), 3.36-3.33 (m, 2H), 3.27 (t, J=6.4 Hz, 2H), 2.94-2.87 (m, 1H), 2.84 (s, 3H), 2.82-2.70 (m, 2H), 2.68-2.52 (m, 2H), 2.49-2.19 (m, 2H), 2.18-2.10 (m, 1H), 1.95-1.74 (m, 2H), 1.46 (s, 9H).

Step 2—2-(2,6-Dioxo-3-piperidyl)-4-[[(2S)-4-[3-(methylamino)propyl]morpholin-2- yl]methylamino] isoindoline-1,3-dione To a solution of tert-butyl N-[3-[(2S)-2-[[[2-(2,6-dioxo-3-piperidyl)-1,3-dioxo-isoindolin-4-yl]amino]methyl]morpholin-4-yl]propyl]-N-methyl-carbamate (90.0 mg, 165 umol) in DCM (1.00 mL) was added HCl/dioxane (4 M, 1.00 mL). The mixture was stirred at 20° C. for 0.5 hour. On completion, the reaction mixture was concentrated in vacuo to give the title compound (79.0 mg, 99% yield, HCl salt) as a yellow solid. LC-MS ($ESI^+$) m/z 444.2 $(M+H)^+$.

4-Benzyloxy-3-methyl-1H-benzimidazol-2-one (Intermediate ARH)

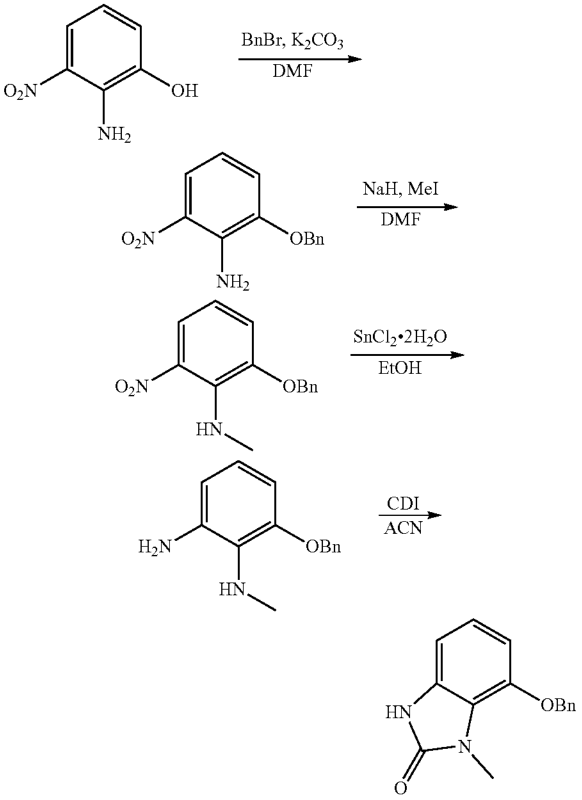

ARH

Step 1—2-Benzyloxy-6-nitro-aniline

To a solution of 2-amino-3-nitro-phenol (60.0 g, 389 mmol, CAS #2835-97-4) and $K_2CO_3$ (107 g, 778 mmol) in DMF (1000 mL) was added BnBr (79.9 g, 467 mmol) at −10° C. The reaction was then warmed to 25° C. and stirred for 18 hours. On completion, the reaction mixture was quenched by addition $H_2O$ (1000 mL), and extracted with ethyl acetate (3×5000 mL). The combined organic layers were washed with brine (3×500 mL) and dried over $Na_2SO_4$, filtered and concentrated in vacuo to give a crude product. The residue was purified by silica gel column chromatography (PE:EA=3:1) to give the title compound (95.0 g, 99% yield) as brown solid. $^1H$ NMR (400 MHz, $CDCl_3$) δ 7.77 (dd, J=1.2, 8.8 Hz, 1H), 7.49-7.36 (m, 5H), 7.04-6.95 (m, 1H), 6.61 (dd, J=7.6, 8.8 Hz, 1H), 6.48 (br s, 2H), 5.15 (s, 2H), LC-MS ($ESI^+$) m/z 245.6 $(M+H)^+$.

Step 2—2-Benzyloxy-N-methyl-6-nitro-aniline

To a solution of 2-benzyloxy-6-nitro-aniline (85.0 g, 348 mmol) in DMF (100 mL) was added NaH (13.9 g, 348 mmol, 60% dispersion in mineral oil) at 0° C. and stirred at 0° C. for 0.5 hr. Then MeI (49.4 g, 348 mmol, 21.6 mL) was added and the reaction mixture was stirred at 25° C. for 12 hrs. On completion, the reaction mixture was quenched by addition $H_2O$ (200 mL), and extracted with ethyl acetate (3×600 mL). The combined organic layers were washed with brine (3×100 mL) and dried over $Na_2SO_4$, filtered and concentrated in vacuo to give the title compound (100 g, 90% yield) as yellow oil. $^1H$ NMR (400 MHz, $CDCl_3$) δ 7.73 (dd, J=1.6, 8.8 Hz, 1H), 7.43-7.35 (m, 5H), 7.01-6.97 (m, 1H), 6.60 (dd, J=7.6, 8.8 Hz, 1H), 5.08 (s, 2H), 3.16 (s, 3H).

Step 3—3-Benzyloxy-N2-methyl-benzene-1,2-diamine

To a solution of 2-benzyloxy-N-methyl-6-nitro-aniline (75.0 g, 290 mmol) in EtOH (1500 mL) was added $SnCl_2.2H_2O$ (327 g, 1.45 mol). The reaction mixture was then exposed to ultrasonic radiation for approximately 30 minutes at 25° C. The reaction mixture was then basified with 1M KOH solution (5000 mL) and extracted with DCM (3×5000 mL). The combined organic layer was washed with brine (3×500 mL), dried over $NaSO_4$ and concentrated in vacuo. The residue was purified by silica gel column chromatography (PE:EA=3:1) to give the title compound (20.0 g, 30% yield) as yellow oil, $^1H$ NMR (400 MHz, $CDCl_3$) δ 7.48-7.32 (m, 5H), 6.84 (t, J=8.0 Hz, 1H), 6.49-6.38 (m, 2H), 5.07 (s, 2H), 3.91 (br s, 2H), 2.70 (s, 3H), LC-MS ($ESI^+$) m/z 229.7 $(M+H)^+$.

Step 4—4-Benzyloxy-3-methyl-1H-benzimidazol-2-one

To a solution of 3-benzyloxy-N2-methyl-benzene-1,2-diamine (20.0 g, 87.6 mmol) in ACN (600 mL) was added CDI (14.2 g, 87.6 mmol), and the reaction mixture was stirred at 25° C. for 16 hours. On completion, the reaction mixture was filtered and the solid was collected to give the title compound (17.0 g, 76% yield) as white solid. $^1H$ NMR (400 MHz, DMSO-$d_6$) δ 10.83 (s, 1H), 7.55-7.47 (m, 2H), 7.46-7.39 (m, 2H), 7.38-7.32 (m, 1H), 6.95-6.87 (m, 1H), 6.83-6.77 (m, 1H), 6.64 (dd, J=0.8, 7.6 Hz, 1H), 5.19 (s, 2H), 3.47 (s, 3H), LC-MS ($ESI^+$) m/z 255.0 $(M+H)^+$.

3-(4-Hydroxy-3-methyl-2-oxo-benzimidazol-1-yl) piperidine-2,6-dione (Intermediate ARI)

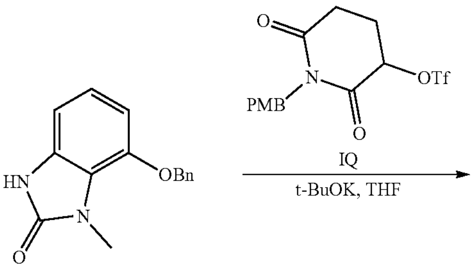

ARH

-continued

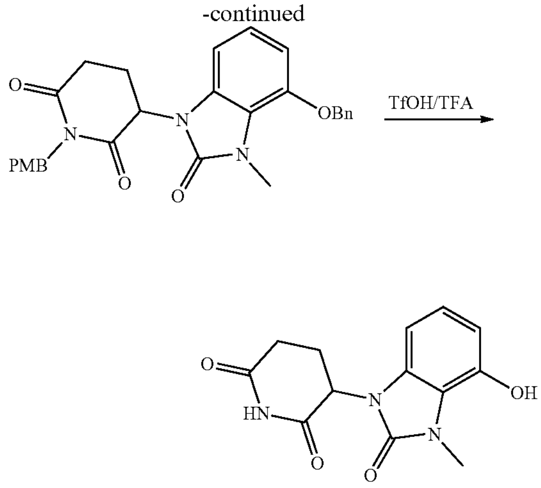

ARI

Step 1—3-(4-Benzyloxy-3-methyl-2-oxo-benzimidazol-1-yl)-1-[(4-methoxyphenyl)methyl]piperidine-2,6-dione To a mixture of 4-benzyloxy-3-methyl-1H-benzimidazol-2-one (2.00 g, 7.87 mmol, Intermediate ARH) in THE (60 mL) was added KOtBu (1.77 g, 15.7 mmol) at −10° C. for 0.5 hr under $N_2$. Then solution of [1-[(4-methoxyphenyl)methyl]-2,6-dioxo-3-piperidyl]trifluoromethanesulfonate (7.50 g, 19.6 mmol, Intermediate IQ) in THE (20 mL) was added dropwise and the mixture was stirred at −10° C. for 1 hour under $N_2$. On completion, the mixture was poured into saturated ammonium chloride aqueous solution (100 mL) and extracted with ethyl acetate (3×100 mL). The combined organic layers were washed with water, brine, dried over anhydrous sodium sulfate and concentrated in vacuo. The residue was purified by silica gel column chromatography (EA) to give the title compound (2.20 g, 57% yield) as blue solid. $^1$H NMR (400 MHz, DMSO-$d_6$) δ7.56-7.50 (m, 2H), 7.44-7.40 (m, 2H), 7.38-7.34 (m, 1H), 7.21 (d, J=8.8 Hz, 2H), 6.92-6.83 (m, 4H), 6.66 (dd, J=7.8, 13.6 Hz, 1H), 5.49 (dd, J=5.4, 12.8 Hz, 1H), 5.22 (s, 2H), 4.87-4.73 (m, 2H), 3.73 (s, 3H), 3.54 (s, 3H), 3.10-2.98 (m, 1H), 2.89-2.64 (m, 2H), 2.10-2.02 (m, 1H).

Step 2—3-(4-Hydroxy-3-methyl-2-oxo-benzimidazol-1-yl)piperidine-2,6-dione

To a mixture of 3-(4-benzyloxy-3-methyl-2-oxo-benzimidazol-1-yl)-1-[(4-methoxyphenyl)methyl]piperidine-2,6-dione (2.00 g, 4.12 mmol) in TFA (10.0 mL) was added TfOH (17.0 g, 113 mmol). The reaction mixture was heated to 60° C. and stirred for 1 hour. On completion, the mixture was concentrated in vacuo to remove TFA. The residue was poured into water (100 mL), neutralized with saturated $NaHCO_3$ aqueous solution until the pH=5, and concentrated in vacuo. The residue was purified by reverse phase: (0.1% FA) to give the title compound (500 mg, 43% yield) as off-white solid. $^1$H NMR (400 MHz, DMSO-$d_6$) δ 11.07 (s, 1H), 9.81 (s, 1H), 6.87-6.79 (m, 1H), 6.60-6.54 (m, 2H), 5.30 (dd, J=5.4, 12.8 Hz, 1H), 3.53 (s, 3H), 2.97-2.83 (m, 1H), 2.75-2.60 (m, 2H), 2.05-1.95 (m, 1H).

3-[3-Methyl-2-oxo-4-(4-piperidylmethoxy)benzimidazol-1-yl]piperidine-2,6-dione (Intermediate AZN)

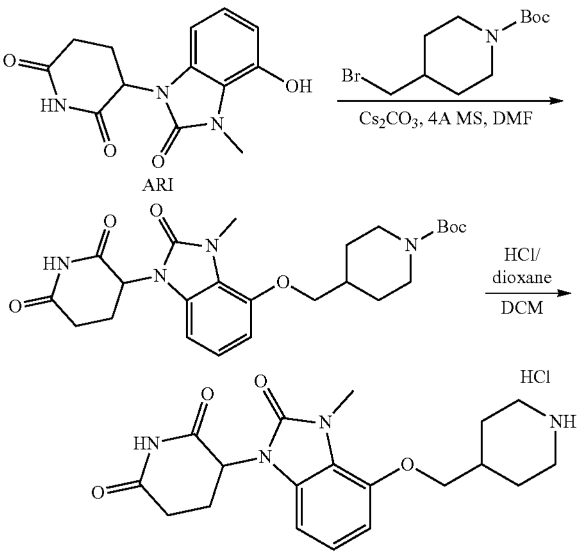

ARI

AZN

Step 1—Tert-butyl4-[[1-(2,6-dioxo-3-piperidyl)-3-methyl-2-oxo-benzimidazol-4-yl]oxymethyl]piperidine-1-carboxylate To a solution of 3-(4-hydroxy-3-methyl-2-oxo-benzimidazol-1-yl) piperidine-2,6-dione (500 mg, 1.82 mmol, Intermediate ARI), tert-butyl 4-(bromomethyl)piperidine-1-carboxylate (404 mg, 1.45 mmol, CAS #158407-04-6) in DMF (6.0 mL) was added $Cs_2CO_3$ (888 mg, 2.72 mmol) and 4 Å molecular sieves (500 mg). The mixture was stirred at 40° C. for 13 hrs. On completion, the reaction mixture was filtered and the filtrate was concentrated in vacuo to give a residue. The residue was purified by Prep-HPLC (FA condition;column: Phenomenex luna C18 150*40 mm*15 um;mobile phase: [water(0.225% FA)-ACN];B %: 28%-58%, 9 min) to give the title compound (60.0 mg, 6.0% yield) as red solid. $^1$H NMR (400 MHz, $CDCl_3$) δ 9.22 (s, 1H), 6.96-6.90 (m, 1H), 6.61 (d, J=8.4 Hz, 1H), 6.47 (d, J=7.6 Hz, 1H), 5.22 (dd, J=5.6, 12.4 Hz, 1H), 4.17 (s, 2H), 3.89 (d, J=6.4 Hz, 2H), 3.65 (s, 3H), 2.96-2.52 (m, 6H), 2.20-2.12 (m, 1H), 1.83-1.78 (m, 2H), 1.46 (s, 9H), 1.35-1.26 (m, 2H); LC-MS (ESI$^+$) m/z 417.1 (M+H-56)$^+$.

Step 2—3-[3-Methyl-2-oxo-4-(4-piperidylmethoxy)benzimidazol-1-yl]piperidine-2,6-dione To a solution of tert-butyl4-[[1-(2,6-dioxo-3-piperidyl)-3-methyl-2-oxo-benzimidazol-4-yl]oxymethyl]piperidine-1-carboxylate (60.0 mg, 114 umol) in DCM (3.0 mL) was added HCl/dioxane (4 M, 1.08 mL). The mixture was stirred at 25° C. for 1 hr. On completion, the reaction mixture was concentrated under reduced pressure to give the title compound (40.0 mg, 100% yield, HCl salt) as red solid. LC-MS (ESI$^+$) m/z 373.2 (M+H)$^+$.

Tert-butyl methyl (prop-2-yn-1-yl)carbamate (Intermediate AZO)

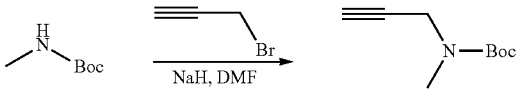

AZO

To a solution of tert-butyl N-methylcarbamate (10.0 g, 76.2 mmol, CAS #16066-84-5) in DMF (100 mL) was added NaH (3.66 g, 91.5 mmol) at 0° C. The reaction mixture was stirred at 25° C. for 0.5 h. Then 3-bromoprop-1-yne (13.6 g, 114 mmol, CAS #106-96-7) was added. The mixture was stirred at 25° C. for 2.5 hr. On completion, the reaction mixture was quenched by addition of $H_2O$ (50 mL) and extracted with dichloromethane (3×500 mL). The combined organic layers were washed with brine (3×100 mL) and dried over anhydrous $Na_2SO_4$, filtered and concentrated in vacuo. The residue was purified by column chromatography (Ethyl acetate) give the title compound (4.80 g, 37% yield) as colorless oil. $^1$H NMR (400 MHz, DMSO-d6) δ 3.98 (d, J=2.0 Hz, 2H), 3.19 (s, 1H), 2.80 (s, 3H), 1.40 (s, 9H).

3-(3-Methyl-4-(3-(methylamino)prop-1-yn-1-yl)-2-oxo-2,3-dihydro-1H-benzo[d]imidazol-1-yl)piperidine-2,6-dione (Intermediate AZP)

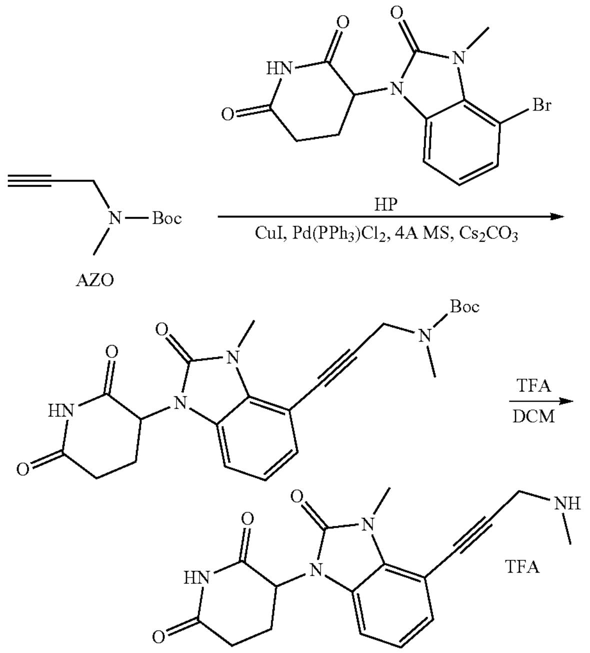

AZP

Step 1—Tert-butyl(3-(1-(2,6-dioxopiperidin-3-yl)-3-methyl-2-oxo-2,3-dihydro-1H-benzo[d]imidazol-4-yl)prop-2-yn-1-yl)(methyl)carbamate To a solution of tert-butyl N-methyl-N-prop-2-ynyl-carbamate (2.00 g, 11.8 mmol, Intermediate AZO), 3-(4-bromo-3-methyl-2-oxo-benzimidazol-1-yl)piperidine-2,6-dione (2.66 g, 7.88 mmol, Intermediate HP), CuI (150 mg, 787 umol), $Pd(PPh_3)_2Cl_2$ (553 mg, 787 umol), 4 Å molecular sieves (1.00 g, 7.88 mmol) and $Cs_2CO_3$ (10.2 g, 31.5 mmol) in DMF (50 mL). The mixture was stirred at 80° C. for 16 hr under $N_2$. On completion, the mixture was filtrated and the filtrate was concentrated in vacuo. The crude product was purified by reverse phase flash (0.1% FA condition) to give the title compound (600 mg, 16% yield) as yellow solid. $^1$H NMR (400 MHz, DMSO-d6) δ 11.12 (s, 1H), 7.23-6.90 (m, 3H), 5.44-5.35 (m, 1H), 4.29 (s, 2H), 3.61 (s, 3H), 3.54 (s, 1H), 2.89 (s, 2H), 2.95-2.80 (m, 1H), 2.77-2.59 (m, 2H), 2.07-1.96 (m, 1H), 1.42 (s, 9H).

Step 2—3-(3-Methyl-4-(3-(methylamino)prop-1-yn-1-yl)-2-oxo-2,3-dihydro-1H-benzo[d]imidazol-1-yl)piperidine-2,6-dione To a solution of tert-butylN-[3-[1-(2,6-dioxo-3-piperidyl)-3-methyl-2-oxo-benzimidazol-4-yl]prop-2- ynyl]-N-methyl-carbamate (100 mg, 234 umol) in DCM (10 mL) was added TFA (1.54 g, 13.5 mmol). The mixture was stirred at 25° C. for 20 min. On completion, the reaction mixture was concentrated in vacuo to give the title compound (750 mg, 95% yield, TFA salt) as yellow oil. LC-MS (ESI$^+$) m/z 349.2 $(M+23)^+$.

Methyl 4-chlorocarbonylcyclohexanecarboxylate (Intermediate AZQ)

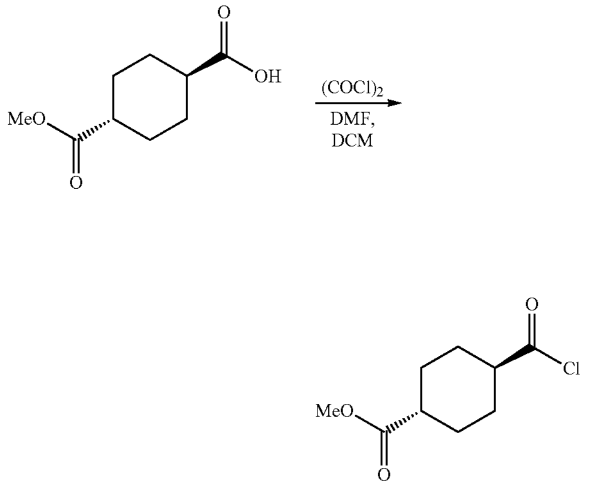

AZQ

To a solution of 4-methoxycarbonylcyclohexanecarboxylic acid (5.0 g, 26.8 mmol, CAS #1005474-88-3) in DCM (50.0 mL) was added $(COCl)_2$ (6.82 g, 53.7 mmol, 4.70 mL) and DMF (98.1 mg, 1.34 mmol, 103 uL) at 0° C. The reaction mixture was stirred at 0° C. for 2 hours. On completion, the reaction was concentrated in vacuo to give the title compound (5.0 g, 90% yield) as colorless oil.

[4-(6-Amino-5-methoxy-1,3-benzoxazol-2-yl)cyclohexyl]methanol (Intermediate AZR)

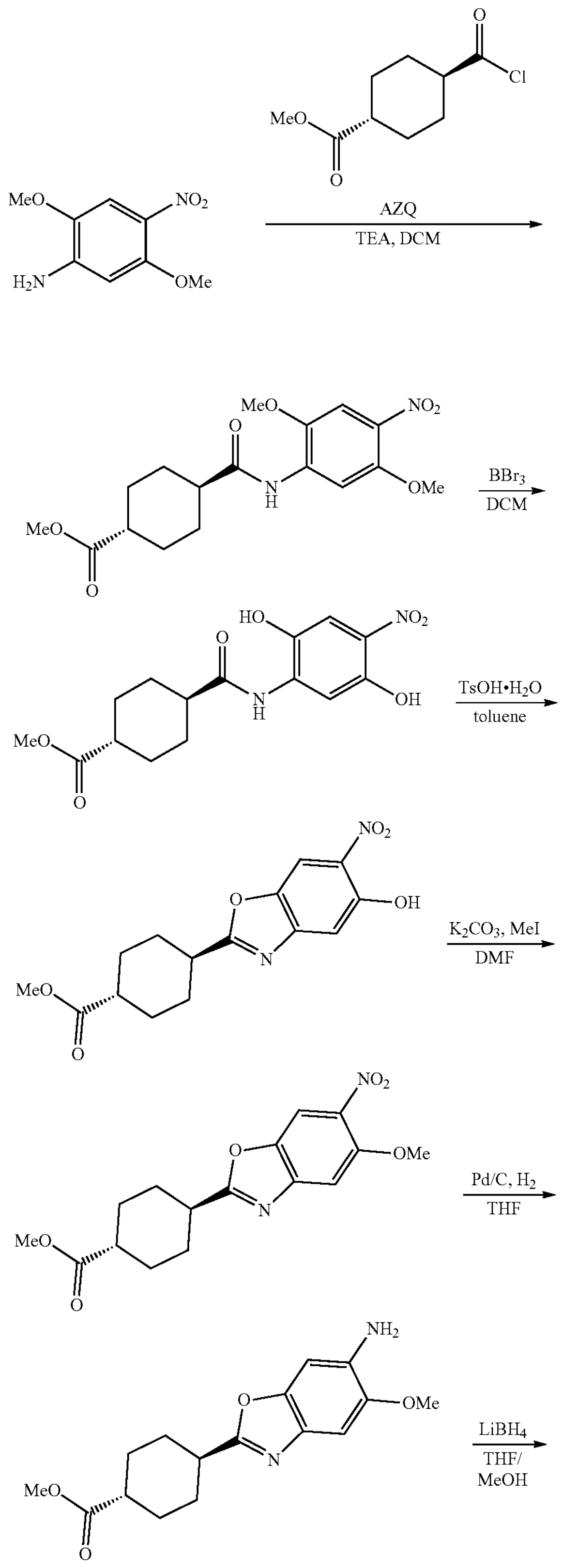

-continued

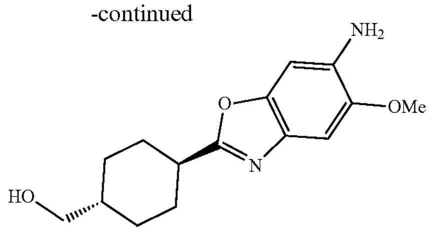

AZR

Step 1—Methyl 4-[(2,5-dimethoxy-4-nitro-phenyl) carbamoyl]cyclohexanecarboxylate To a solution of 2,5-dimethoxy-4-nitro-aniline (4.84 g, 24.4 mmol, CAS #6313-37-7) and TEA (7.42 g, 73.3 mmol, 10.2 mL) in DCM (50.0 mL) was added a solution of methyl 4-chlorocarbonyl cyclohexanecarboxylate (5.0 g, 24.4 mmol) in DCM (10 mL) at 0° C. The reaction mixture was stirred at 25° C. for 12 h. On completion, the reaction mixture was diluted with $H_2O$ (40 mL), and then extracted with DCM (2x60 mL). The combined organic phase was dried over $Na_2SO_4$, filtered and then concentrated in vacuo to give a residue, the residue was triturated with DCM (40 mL) and filtered to give the title compound (5.0 g, 55% yield) as a yellow solid. $^1H$ NMR (400 MHz, $CDCl_3$) δ 8.45 (s, 1H), 8.04 (s, 1H), 7.54 (s, 1H), 3.95 (s, 3H), 3.93 (s, 3H), 3.68 (s, 3H), 2.40-2.27 (m, 2H), 2.17-2.02 (m, 4H), 1.67-1.45 (m, 4H); LC-MS ($ESI^+$) m/z 367.1 $(M+1)^+$.

Step 2—Methyl 4-[(2,5-dihydroxy-4-nitro-phenyl) carbamoyl]cyclohexanecarboxylate To a solution of methyl 4-[(2,5-dimethoxy-4-nitro-phenyl)carbamoyl]cyclohexanecarboxylate (3.0 g, 8.19 mmol) in DCM (50 mL) was added $BBr_3$ (6.15 g, 24.5 mmol, 2.37 mL), and the reaction was stirred at −70° C. for 4 hour. On completion, the reaction was quenched with MeOH (15 mL), then diluted with $H_2O$ (40 mL), and extracted with DCM (3x80 mL). The combined organic layers were dried over $Na_2SO_4$, filtered and concentrated in vacuo to give a residue. The residue was triturated with DCM (50 mL) and filtered to afford the title compound (2.4 g, 86% yield) as a yellow solid. $^1H$ NMR (400 MHz, DMSO-$d_6$) δ 10.60-10.23 (m, 2H), 9.33 (s, 1H), 8.03 (s, 1H), 7.42 (s, 1H), 3.60 (s, 3H), 2.72-2.60 (m, 1H), 2.38-2.26 (m, 1H), 2.01-1.80 (m, 4H), 1.51-1.29 (m, 4H); LC-MS ($ESI^+$) m/z 339.1 $(M+1)^+$.

Step 3—Methyl 4-(5-hydroxy-6-nitro-1,3-benzoxazol-2-yl)cyclohexanecarboxylate

To a solution of methyl 4-[(2,5-dihydroxy-4-nitro-phenyl) carbamoyl]cyclohexanecarboxylate (1.9 g, 5.62 mmol) in toluene (50 mL) was added p-TsOH (386 mg, 2.25 mmol), the reaction mixture was stirred at 125° C. for 12 hours. On completion, the reaction mixture was concentrated in vacuo to give a residue, the residue was purified by reverse phase (0.1% FA condition) to give the title compound (1.3 g, 72% yield) as a yellow solid. LC-MS ($ESI^+$) m/z 321.0 $(M+1)^+$.

Step 4—Methyl 4-(5-methoxy-6-nitro-1,3-benzoxazol-2-yl)cyclohexanecarboxylate

To a solution of methyl 4-(5-hydroxy-6-nitro-1,3-benzoxazol-2-yl)cyclohexanecarboxylate (1.2 g, 3.75 mmol) and $K_2CO_3$ (1.04 g, 7.49 mmol) in DMF (20 mL) was added MeI (1.06 g, 7.49 mmol, 466 uL) at 0° C., and the reaction mixture was stirred at 25° C. for 3 hours. On completion, the mixture was filtered, and the filtrate was concentrated in vacuo to give a residue. The residue was purified by reverse phase (0.1% FA condition) to give the title compound (550 mg, 43% yield) as a yellow solid. $^1H$ NMR (400 MHz, DMSO-$d_6$) δ 8.35 (s, 1H), 7.66 (s, 1H), 3.94 (s, 3H), 3.62 (s, 3H), 3.11-2.98 (m, 1H), 2.46-2.36 (m, 1H), 2.25-2.13 (m, 2H), 2.06-1.96 (m, 2H), 1.70-1.45 (m, 4H); LC-MS (ESI$^+$) m/z 335.1 $(M+1)^+$.

Step 5—Methyl 4-(6-amino-5-methoxy-1,3-benzoxazol-2-yl)cyclohexanecarboxylate

To a solution of methyl 4-(5-methoxy-6-nitro-1,3-benzoxazol-2-yl)cyclohexanecarboxylate (550 mg, 1.65 mmol) in THE (10 mL) was added Pd/C (200 mg, 1.65 mmol, 10 wt %), and the reaction mixture was stirred at 25° C. under $H_2$ (15 psi) for 2 hours. On completion, the reaction mixture was filtered and the filtrate was concentrated in vacuo to give the title compound (500 mg, 99% yield) as a white solid. $^1H$ NMR (400 MHz, DMSO-$d_6$) δ 7.12 (s, 1H), 6.88 (s, 1H), 4.96 (s, 2H), 3.85 (s, 3H), 3.66 (s, 3H), 2.97-2.85 (m, 1H), 2.50-2.39 (m, 1H), 2.22-2.13 (m, 2H), 2.09-1.99 (m, 2H), 1.68-1.48 (m, 4H); LC-MS (ESI$^+$) m/z 305.1 $(M+1)^+$.

Step 6—[4-(6-Amino-5-methoxy-1,3-benzoxazol-2-yl)cyclohexyl]methanol

To a solution of methyl 4-(6-amino-5-methoxy-1,3-benzoxazol-2-yl)cyclohexanecarboxylate (500 mg, 1.64 mmol) in a mixed solvent of THF (10.0 mL) and MeOH (1.0 mL) was added $LiBH_4$ (107 mg, 4.93 mmol) at 25° C., and the reaction mixture was stirred at 50° C. for 3 hours. Then another batch of $LiBH_4$ (71 mg, 3.29 mmol) was added, and the reaction mixture was stirred at 50° C. for 2 hours. On completion, the reaction mixture was quenched with $H_2O$ (20 mL), then extracted with DCM (2×40 mL). The combined organic phase was dried over $Na_2SO_4$, filtered and the filtrate was concentrated in vacuo to give the title compound (280 mg, 62% yield) as a yellow solid. $^1H$ NMR (400 MHz, DMSO-$d_6$) δ 7.06 (s, 1H), 6.82 (s, 1H), 4.89 (s, 2H), 4.43 (t, J=5.2 Hz, 1H), 3.79 (s, 3H), 3.25 (t, J=5.6 Hz, 2H), 2.82-2.72 (m, 1H), 2.15-2.05 (m, 2H), 1.89-1.79 (m, 2H), 1.54-1.45 (m, 2H), 1.43-1.36 (m, 1H), 1.10-0.97 (m, 2H).

N-[2-(4-formylcyclohexyl)-5-methoxy-1,3-benzoxazol-6-yl]-6-(trifluoromethyl)pyridine-2- carboxamide (Intermediate AZS)

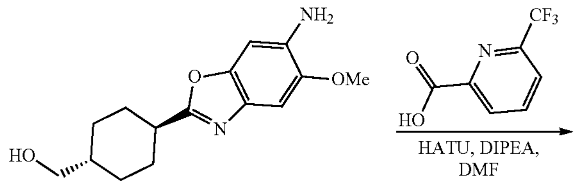

AZR

-continued

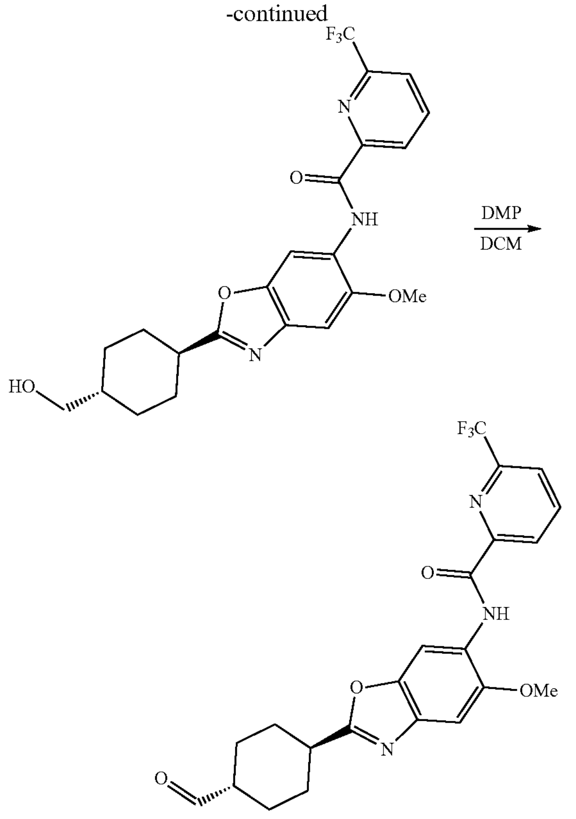

AZS

Step 1—N-[2-[4-(hydroxymethyl)cyclohexyl]-5-methoxy-1,3-benzoxazol-6-yl]-6-(trifluoromethyl) pyridine-2-carboxamide To a solution of 6-(trifluoromethyl)pyridine-2-carboxylic acid (193 mg, 1.01 mmol, CAS #131747-42-7) in DMF (8.0 mL) was added CMPI (310 mg, 1.22 mmol) and DIPEA (392 mg, 3.04 mmol, 529 uL), and the mixture was stirred at 25° C. for 30 mins. Then [4-(6-amino-5-methoxy-1,3-benzoxazol-2- yl)cyclohexyl]methanol (280 mg, 1.01 mmol, Intermediate AZR) was added, the reaction mixture was stirred at 25° C. for 1 hour. On completion, the reaction mixture was concentrated in vacuo to give a residue. The residue was purified by reverse phase (0.1% FA condition) to give the title compound (240 mg, 53% yield) as a white solid. LC-MS (ESI$^+$) m/z 450.2 $(M+1)^+$.

Step 2—N-[2-(4-formylcyclohexyl)-5-methoxy-1,3-benzoxazol-6-yl]-6-(trifluoromethyl)pyridine-2- carboxamide To a solution of N-[2-[4-(hydroxymethyl)cyclohexyl]-5-methoxy-1,3-benzoxazol-6-yl]-6- (trifluoromethyl)pyridine-2-carboxamide (120 mg, 267 umol) in DCM (3 mL) was added DMP (147 mg, 347 umol, 107 uL), and the reaction mixture was stirred at 25° C. for 2 hour. On completion, the reaction mixture was quenched with $Na_2S_2O_3$ (10 mL) and extracted with DCM (2×20 mL). The combined organic phase was washed with aq. $NaHCO_3$ (15 mL) and brine (2×15 mL), dried over $Na_2SO_4$, filtered and concentrated in vacuo to give the title compound (110 mg, 92% yield) as a yellow solid. $^1H$ NMR (400 MHz, DMSO-d$_6$) δ 10.49 (s, 1H), 9.62 (s, 1H), 8.67 (s, 1H), 8.48-8.43 (m, 1H), 8.43-8.37 (m, 1H), 8.22 (d, J=7.2 Hz, 1H), 7.48 (s, 1H), 3.98 (s, 3H), 3.02-2.90 (m, 1H), 2.44-2.34 (m, 1H), 2.27-2.17 (m, 2H), 2.10-2.01 (m, 2H), 1.73-1.59 (m, 2H), 1.46-1.32 (m, 2H); LC-MS (ESI$^+$) m/z 448.2 (M+1)$^+$.

1-[5-Bromo-2-[4-(hydroxymethyl)cyclohexyl]indazol-6-yl]oxy-2-methyl-propan-2-ol (Intermediate AZT)

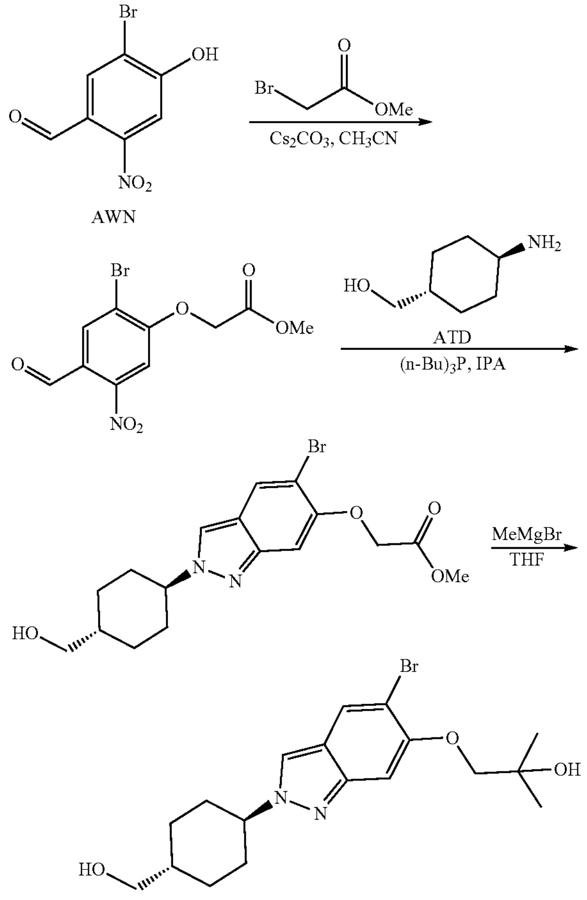

AZT

Step 1—Methyl 2-(2-bromo-4-formyl-5-nitro-phenoxy) acetate

To a solution of 5-bromo-4-hydroxy-2-nitro-benzaldehyde (1.00 g, 4.06 mmol, Intermediate AWN) and $K_2CO_3$ (841 mg, 6.09 mmol) in $CH_3CN$ (10 mL) was added methyl 2-bromoacetate (745 mg, 4.87 mmol, CAS #96-32-2). The reaction mixture was stirred at 25° C. for 12 hrs. On completion, the reaction mixture was filtered and the filtrate was concentrated in vacuo. The residue was purified by silica gel chromatography (PE:EA=20:1) to give the title compound (820 mg, 50% yield) as white solid. $^1$H NMR (400 MHz, $CDCl_3$) δ 10.35 (s, 1H), 8.25-8.24 (m, 1H), 7.45-7.43 (m, 1H), 4.92-4.90 (m, 2H), 3.87 (s, 3H).

Step 2—Methyl 2-[5-bromo-2-[4-(hydroxymethyl) cyclohexyl]indazol-6-yl]oxyacetate A mixture of methyl 2-(2-bromo-4-formyl-5-nitro-phenoxy)acetate (820 mg, 2.58 mmol) and (4-aminocyclohexyl) methanol (366 mg, 2.84 mmol, Intermediate ATD) in IPA (15 mL) was stirred at 80° C. for 3 hrs under $N_2$. Then tributylphosphane (1.04 g, 5.16 mmol, 1.27 mL) was added to the reaction mixture at 25° C. and the mixture was stirred at 80° C. for 13 hrs under $N_2$. On completion, the reaction mixture was concentrated in vacuo. The residue was purified by silica gel chromatography (PE:EA=2:1) to give the title compound (520 mg, 50% yield) as white solid. $^1$H NMR (400 MHz, DMSO-d$_6$) δ 8.30 (s, 1H), 7.99 (s, 1H), 7.04 (s, 1H), 4.93 (s, 2H), 4.48 (t, J=5.2 Hz, 1H), 4.37 (m, 1H), 3.72 (s, 3H), 3.28 (t, J=5.6 Hz, 2H), 2.14-2.06 (m, 2H), 1.93-1.82 (m, 4H), 1.52-1.40 (m, 1H), 1.20-1.06 (m, 2H).

Step 3—1-[5-Bromo-2-[4-(hydroxymethyl)cyclohexyl]indazol-6-yl]oxy-2-methyl-propan-2-ol To a solution of methyl 2-[5-bromo-2-[4-(hydroxymethyl)cyclohexyl]indazol-6-yl]oxyacetate (350 mg, 881 umol) in THF (5 mL) was added MeMgBr (525 mg, 4.41 mmoL) at 0° C. The reaction mixture was stirred at 0~10° C. for 2 hrs under $N_2$. On completion, the reaction mixture was quenched with sat. aq. $NH_4Cl$ (0.1 mL), diluted with water (10 mL) and extracted with EA (3×10 mL). The combined organic layers were washed with brine (2×10 mL), dried over $Na_2SO_4$, filtered and concentrated in vacuo. The residue was purified by silica gel chromatography (PE:EA=1:2) to give the title compound (300 mg, 83% yield) as white solid. $^1$H NMR (400 MHz, DMSO-d$_6$) δ 8.27 (s, 1H), 7.95 (s, 1H), 7.03 (s, 1H), 4.66 (s, 1H), 4.48 (t, J=5.2 Hz, 1H), 4.36 (m, 1H), 3.77 (s, 2H), 3.28 (t, J=5.6 Hz, 2H), 2.15-2.07 (m, 2H), 1.92-1.81 (m, 4H), 1.53-1.39 (m, 1H), 1.27 (s, 6H), 1.13 (m, 2H).

6-(1-Fluoro-1-methyl-ethyl)-N-[2-(4-formylcyclohexyl)-6-(2-hydroxy-2-methyl-propoxy) indaz 1-5-yl]pyridine-2-carboxamide (Intermediate AZU)

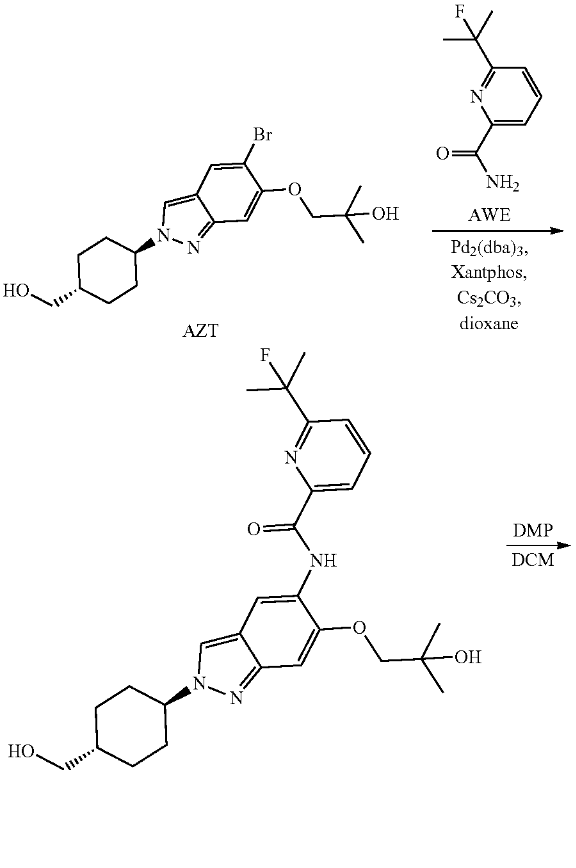

-continued

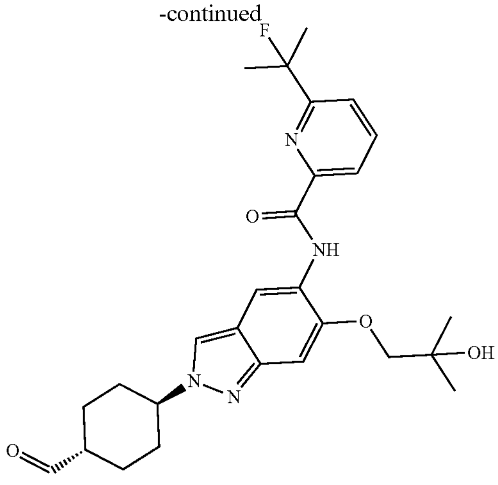

AZU

Step 1—6-(1-Fluoro-1-methyl-ethyl)-N-[2-[4-(hydroxymethyl)cyclohexyl]-6-(2-hydroxy-2-methyl-propoxy)indazol-5-yl]pyridine-2-carboxamide A mixture of 1-[5-bromo-2-[4-(hydroxymethyl)cyclohexyl]indazol-6-yl]oxy-2-methyl-propan-2-ol (300 mg, 755 umol, Intermediate AZT), 6-(1-fluoro-1-methyl-ethyl)pyridine-2-carboxamide (151 mg, 830 umol, Intermediate AWE), $Pd_2(dba)_3$ (69.1 mg, 75.5 umol), Xantphos (87.3 mg, 151 umol) and $Cs_2CO_3$ (492 mg, 1.51 mmol) in dioxane (5 mL) was stirred at 80° C. for 12 hrs under $N_2$. On completion, the reaction mixture was filtered and concentrated in vacuo. The residue was purified by reversed-phase (0.1% FA) to give the title compound (100 mg, 26% yield) as brown solid. $^1H$ NMR (400 MHz, DMSO-$d_6$) δ 10.33 (s, 1H), 8.77 (s, 1H), 8.32 (s, 1H), 8.18-8.12 (m, 2H), 7.81 (m, 1H), 7.10 (s, 1H), 4.73 (s, 1H), 4.49 (t, J=5.2 Hz, 1H), 4.39-4.30 (m, 1H), 3.91 (s, 2H), 3.29 (s, 1H), 3.29-3.27 (m, 1H), 2.19-2.10 (m, 2H), 1.93-1.85 (m, 4H), 1.81-1.78 (m, 3H), 1.76-1.72 (m, 3H), 1.52-1.44 (m, 1H), 1.34-1.30 (m, 6H), 1.19-1.10 (m, 2H).

Step 2—6-(1-Fluoro-1-methyl-ethyl)-N-[2-(4-formylcyclohexyl)-6-(2-hydroxy-2-methyl-propoxy) indaz 1-5-yl]pyridine-2-carboxamide To a solution of 6-(1-fluoro-1-methyl-ethyl)-N-[2-[4-(hydroxymethyl)cyclohexyl]-6-(2-hydroxy-2- methylpropoxy) indazol-5-yl]pyridine-2-carboxamide (100 mg, 200 umol) in DCM (1 mL) was added DMP (110 mg, 260 umol). The reaction mixture was stirred at 25° C. for 1 hr. On completion, the reaction mixture was quenched with Sat.aq.$Na_2S_2O_3$ (0.1 mL), then acidified with sat. aq. $NaHCO_3$ until the pH=7~ 8. The reaction mixture was diluted with water (10 mL) and extracted with DCM (3×10 mL). The combined organic layers were washed with brine (2×10 mL), dried over $Na_2SO_4$, filtered and concentrated in vacuo to give the title compound (90.0 mg, 90% yield) as brown solid. LC-MS (ESI$^+$) m/z 497.3 $(M+H)^+$.

6-(1,1-Difluoroethyl)-N-[2-(4-formylcyclohexyl)-6-(2-hydroxy-2-methyl-propoxy)indazol-5-yl]pyridine-2-carboxamide (Intermediate AZV)

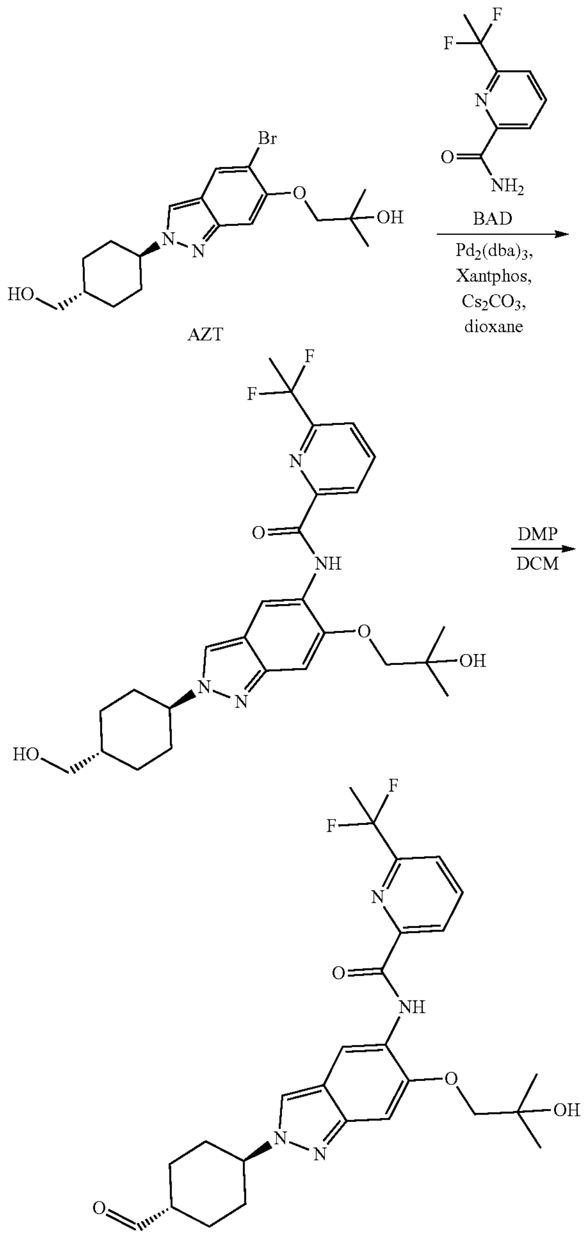

AZV

Step 1—6-(1,1-Difluoroethyl)-N-[2-[4-(hydroxymethyl)cyclohexyl]-6-(2-hydroxy-2-methyl-propoxy) indazol-5-yl]pyridine-2-carboxamide To a solution of 6-(1,1-difluoroethyl)pyridine-2-carboxamide (206 mg, 1.11 mmol, Intermediate BAD) and 1-[5-bromo-2-[4-(hydroxymethyl)cyclohexyl]indazol-6-yl]oxy-2-methyl-propan-2-ol (400 mg, 1.01 mmol, Intermediate AZT) in dioxane (8.0 mL) was added $Pd_2(dba)_3$ (92.2 mg, 100 umol), Xantphos (116 mg, 201 umol) and $Cs_2CO_3$ (656 mg, 2.01 mmol), the reaction mixture was stirred at 80° C.

for 12 hours. On completion, the reaction mixture was filtered and the filtrate was concentrated in vacuo to give a residue. The residue was purified by reverse phase (0.1% FA condition) to give the title compound (160 mg, 31% yield) as a white solid. $^1H$ NMR (400 MHz, DMSO-$d_6$) δ 10.39 (s, 1H), 8.77 (s, 1H), 8.36-8.32 (m, 1H), 8.32 (s, 1H), 8.30-8.24 (m, 1H), 7.96 (d, J=7.2 Hz, 1H), 7.09 (s, 1H), 4.74 (s, 1H), 4.49 (t, J=5.2 Hz, 1H), 4.41-4.28 (m, 1H), 3.90 (s, 2H), 3.29 (t, J=5.6 Hz, 2H), 2.19-2.04 (m, 5H), 1.95-1.80 (m, 4H), 1.56-1.40 (m, 1H), 1.33 (s, 6H), 1.20-1.06 (m, 2H); LC-MS (ESI$^+$) m/z 503.3 (M+1)$^+$.

Step 2—6-(1,1-Difluoroethyl)-N-[2-(4-formylcyclohexyl)-6-(2-hydroxy-2-methyl-propoxy)indazol-5-yl]pyridine-2-carboxamide To a solution of 6-(1,1-difluoroethyl)-N-[2-[4-(hydroxymethyl)cyclohexyl]-6-(2-hydroxy-2-methyl- propoxy) indazol-5-yl]pyridine-2-carboxamide (140 mg, 278 umol) in DCM (1.0 mL) was added DMP (153 mg, 362 umol), the reaction mixture was stirred at 25° C. for 2 hour. On completion, the reaction mixture was quenched with $Na_2S_2O_3$ (10 mL) and extracted with DCM (2×20 mL). The combined organic phase was washed with brine (2×15 mL), dried with anhydrous $Na_2SO_4$, filtered and concentrated in vacuo to give the title compound (130 mg, 93% yield) as a yellow solid. $^1H$ NMR (400 MHz, DMSO-$d_6$) δ 10.40 (s, 1H), 9.64 (s, 1H), 8.78 (s, 1H), 8.36-8.31 (m, 2H), 8.30-8.25 (m, 1H), 7.97 (dd, J=1.2, 7.6 Hz, 1H), 7.10 (s, 1H), 4.74 (s, 1H), 4.47-4.34 (m, 1H), 3.90 (s, 2H), 2.47-2.37 (m, 1H), 2.25-2.18 (m, 2H), 2.17-2.05 (m, 5H), 2.02-1.89 (m, 2H), 1.50-1.38 (m, 2H), 1.33 (s, 6H); LC-MS (ESI$^+$) m/z 501.3 (M+1)$^+$.

3-(6-Bromo-3-methyl-2-oxo-1,3-benzodiazol-1-yl) piperidine-2,6-dione (Intermediate ATL)

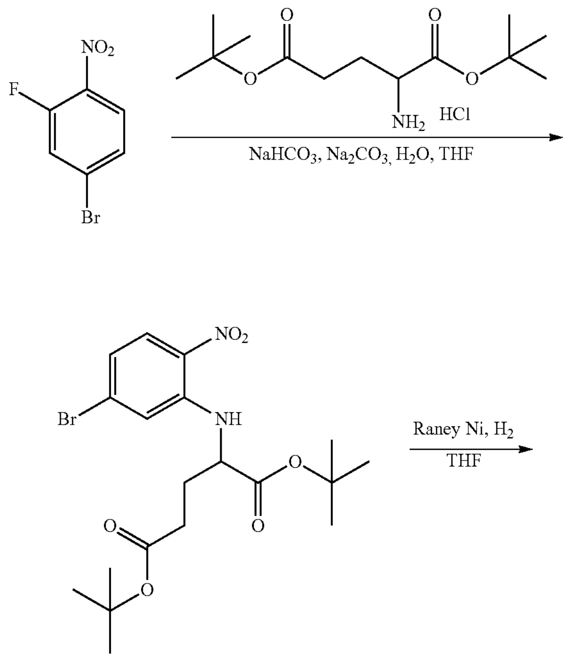

-continued

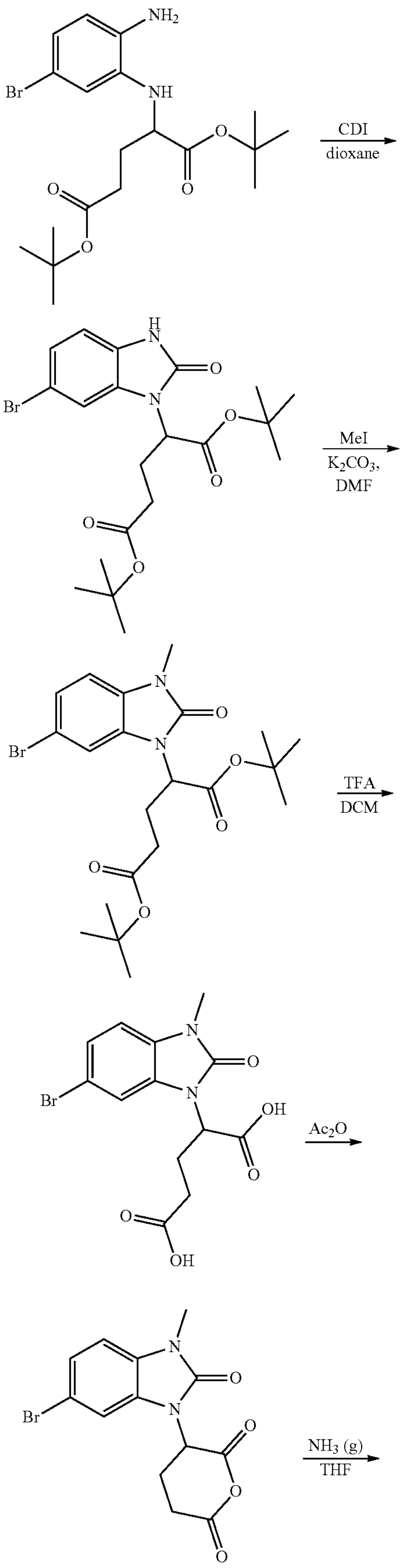

-continued

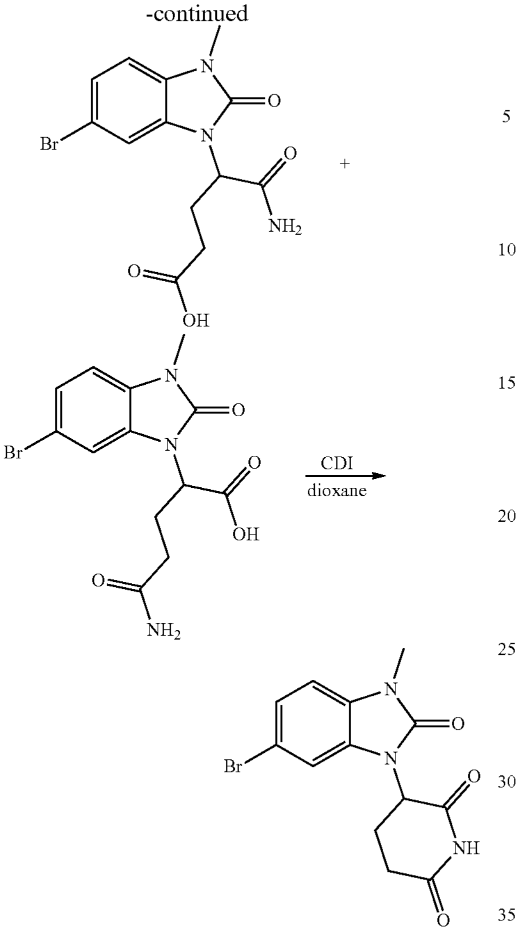

ATL

Step 1—1,5-Di-tert-butyl 2-[(5-bromo-2-nitrophenyl)amino]pentanedioate

A mixture of 4-bromo-2-fluoro-1-nitrobenzene (10.00 g, 45.45 mmol), $NaHCO_3$ (7.64 g, 90.9 mmol), $Na_2CO_3$ (14.45 g, 136.3 mmol) and 1,5-di-tert-butyl (2S)-2-aminopentanedioate hydrochloride (16.13 g, 54.54 mmol) in $H_2O$ (200.00 mL)/THF (200.00 mL) was stirred for overnight at 50° C. The mixture then cooled to room temperature and extracted with petroleum ether (2×200 mL). The combined organic phase was washed with HCl (1 M, 100 mL), brine (100 mL), dried with $Na_2SO_4$ and filtered. The filtrate was concentrated under reduced pressure. This resulted in the title compound (12 g, 57%) as an orange oil. Epimerization would occur under basic conditions. $^1H$ NMR (400 MHz, DMSO-$d_6$) δ 8.29 (d, J=7.6 Hz, 1H), 8.03 (d, J=9.1 Hz, 1H), 7.28 (d, J=2.0 Hz, 1H), 6.94 (dd, J=9.1, 2.0 Hz, 1H), 4.55 (q, J=6.5 Hz, 1H), 2.32 (td, J=7.3, 3.0 Hz, 2H), 2.08 (ddt, J=18.2, 14.2, 7.1 Hz, 2H), 1.45 (s, 9H), 1.36 (s, 9H); LC/MS (ESI, m/z): $[(M+1)]^+$=459.0, 461.0

Step 2—1,5-Di-tert-butyl 2-[(2-amino-5-bromophenyl)amino]pentanedioate

To a solution of 1,5-di-tert-butyl 2-[(5-bromo-2-nitrophenyl)amino]pentanedioate (69.00 g, 150.6 mmol) in THE (400.00 mL) was added Raney Ni (5.00 g) at room temperature under nitrogen atmosphere. The mixture was hydrogenated at room temperature under 30 psi of hydrogen pressure for 4 h. It was then filtered through a celite pad and concentrated under reduced pressure. This resulted in the title compound (64.48 g, 99%) as a light yellow solid: $^1H$ NMR (400 MHz, DMSO-$d_6$) δ 6.58 (dd, J=8.2, 2.1 Hz, 1H), 6.47 (d, J=8.2 Hz, 1H), 6.37 (d, J=2.2 Hz, 1H), 4.94 (d, J=8.8 Hz, 1H), 4.85 (s, 2H), 3.79 (td, J=8.4, 6.0 Hz, 1H), 2.41 (t, J=7.6 Hz, 2H), 1.93 (qt, J=13.6, 7.3 Hz, 2H), 1.41 (s, 18H); LC/MS (ESI, m/z): $[(M+1)]^+$=429.1, 431.1.

Step 3—1,5-Di-tert-butyl 2-(6-bromo-2-oxo-3H-1,3-benzodiazol-1-yl)pentanedioate

A solution of 1,5-di-tert-butyl 2-[(2-amino-5-bromophenyl)amino]pentanedioate (64.48 g, 150.1 mmol) and CDI (42.93 g, 300.3 mmol) in dioxane (1200.00 mL) was stirred for 4 h at 100° C. under nitrogen atmosphere. The mixture then cooled to room temperature and the resulting mixture was concentrated under reduced pressure. The residue was diluted with water (200 mL) and extracted with petroleum ether (3×200 mL). The combined organic layers were washed with brine (300 mL), and dried over anhydrous $Na_2SO_4$. After filtration, the filtrate was concentrated under reduced pressure. This resulted in the title compound (48 g, 70%) as a white powder. $^1H$ NMR (400 MHz, DMSO-$d_6$) δ 7.25 (d, J=1.9 Hz, 1H), 7.16 (dd, J=8.2, 1.9 Hz, 1H), 6.95 (d, J=8.3 Hz, 1H), 4.97 (dd, J=9.8, 5.5 Hz, 1H), 2.34-2.07 (m, 4H), 1.36 (s, 9H), 1.31 (s, 9H); LC/MS (ESI, m/z): [(M+1)]=455.1, 457.1.

Step 4—1,5-Di-tert-butyl 2-(6-bromo-3-methyl-2-oxo-1,3-benzodiazol-1-yl)pentanedioate To a stirred mixture of 1,5-di-tert-butyl 2-(6-bromo-2-oxo-3H-1,3-benzodiazol-1-yl)pentanedioate (48.00 g, 105.4 mmol) and $K_2CO_3$ (43.71 g, 316.2 mmol) in DMF (200.00 mL) was added methyl iodide (22.44 g, 158.1 mmol) dropwise at room temperature under air atmosphere and the resulting mixture was stirred for 2 h at rt. The mixture was the diluted with $H_2O$ (1200 mL) and petroleum ether (500 mL), where a lot of precipitate formed. The solids were filtered and dried under reduced pressure to give the title compound (40 g, 81%) as a white powder. $^1H$ NMR (400 MHz, DMSO-$d_6$) δ 7.33 (d, J=1.8 Hz, 1H), 7.26 (dd, J=8.3, 1.8 Hz, 1H), 7.15 (d, J=8.3 Hz, 1H), 5.03 (dd, J=8.6, 6.5 Hz, 1H), 3.32 (s, 3H), 2.41-2.24 (m, 2H), 2.24-2.07 (m, 2H), 1.36 (s, 9H), 1.31 (s, 9H); LC/MS (ESI, m/z): [(M+1)]+=469.1, 471.1.

Step 5—2-(6-Bromo-3-methyl-2-oxo-1,3-benzodiazol-1-yl)pentanedioic acid

To a stirred solution of 1,5-di-tert-butyl 2-(6-bromo-3-methyl-2-oxo-1,3-benzodiazol-1-yl)pentanedioate (32.00 g, 68.38 mmol) in DCM (150.00 mL) was added TFA (200.00 mL) dropwise at rt under air atmosphere and the resulting mixture was stirred for 3 h at rt. The solution was then concentrated under reduced pressure to give the title compound (23 g, 94%) as a white solid. $^1H$ NMR (400 MHz, DMSO-$d_6$) δ 7.35 (d, J=1.9 Hz, 1H), 7.26 (dd, J=8.3, 1.8 Hz, 1H), 7.15 (d, J=8.3 Hz, 1H), 5.07 (dd, J=10.0, 5.3 Hz, 1H), 3.32 (s, 3H), 2.45-2.28 (m, 2H), 2.28-2.05 (m, 2H); LC/MS (ESI, m/z): $[(M+1)]^+$=356.9, 358.9.

Step 6—3-(6-Bromo-3-methyl-2-oxo-1,3-benzodiazol-1-yl)oxane-2,6-dione

A solution 2-(6-bromo-3-methyl-2-oxo-1,3-benzodiazol-1-yl)pentanedioic acid (23.00 g, 64.61 mmol) in acetic anhydride (150.00 mL) was stirred for 4 h at 135° C. under nitrogen atmosphere. The solution was then cooled to rt. The precipitated solids were collected by filtration, washed with $Et_2O$ (3×100 mL) and dried under reduced pressure. This resulted in the title compound (21 g, 96%) as an off-white powder. $^1H$ NMR (400 MHz, DMSO-$d_6$) δ 7.62 (d, J=1.8 Hz, 1H), 7.30 (dd, J=8.3, 1.8 Hz, 1H), 7.19 (d, J=8.4 Hz, 1H), 5.72 (dd, J=13.2, 5.8 Hz, 1H), 3.33 (s, 3H), 3.15 (ddd, J=18.6, 13.0, 6.0 Hz, 1H), 2.95 (ddd, J=17.8, 4.9, 2.2 Hz, 1H), 2.85 (qd, J=12.9, 4.7 Hz, 1H), 2.03 (ddt, J=12.2, 6.0, 2.9 Hz, 1H); LC/MS (ESI, m/z): [(M+1)]=339.1, 341.1.

Step 7—2-(6-Bromo-3-methyl-2-oxo-1,3-benzodiazol-1-yl)-4-carbamoylbutanoic acid $NH_3$ (gas) was bubbled in a stirred solution of 3-(6-bromo-3-methyl-2-oxo-1,3-benzodiazol-1-yl)oxane-2,6-dione (21.00 g, 62.13 mmol) in THE (200.00 mL) at 0° C. for 30 min. Then the mixture was stirred at room temperature for 2 h. The mixture was then concentrated under reduced pressure to give 2-(6-bromo-3-methyl-2-oxo-1,3-benzodiazol-1-yl)-4-carbamoylbutanoic acid (20 g, 91%) as an off-white solid. LC/MS (ESI, m/z): $[(M+1)]^+$=355.9, 357.9.

Step 8—3-(6-Bromo-3-methyl-2-oxo-1,3-benzodiazol-1-yl)piperidine-2,6-dione

A stirred mixture of 2-(6-bromo-3-methyl-2-oxo-1,3-benzodiazol-1-yl)pentanedioic acid (20.00 g, 55.99 mmol) and CDI (18.16 g, 112.0 mmol) in 1,4-dioxane (400 mL) was stirred for 6 h at 100° C. The solution was then cooled to rt and concentrated under reduced pressure. The residue was triturated with $H_2O$ (300 mL) for 16 h. The resulting mixture was filtered. The filter cake was washed with water (3×300 mL) and dried under reduced pressure. This resulted in the title compound (16 g, 84%) as a white solid. $^1H$ NMR (400 MHz, DMSO-$d_6$) δ 11.11 (s, 1H), 7.43 (dd, J=26.3, 1.8 Hz, 1H), 7.27 (dd, J=8.3, 1.8 Hz, 1H), 7.16 (dd, J=8.4, 3.6 Hz, 1H), 5.39 (dd, J=12.7, 5.3 Hz, 1H), 3.33 (s, 3H), 2.97-2.70 (m, 2H), 2.63 (dd, J=16.4, 3.6 Hz, 1H), 2.05-1.90 (m, 1H); LC/MS (ESI, m/z): [(M+1)]=338.0, 340.0.

6-(1,1-Difluoroethyl)picolinamide (Intermediate BAD)

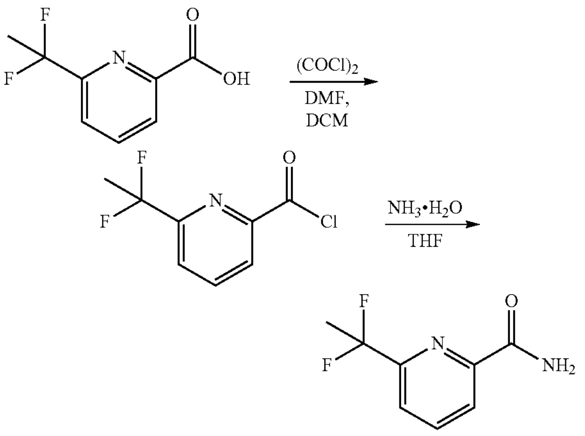

BAD

Step 1—6-(1,1-Difluoroethyl)picolinic acid

To a solution of methyl 6-(1, 1-difluoroethyl)pyridine-2-carboxylate (27.0 g, 134 mmol, CAS #1211529-86-0) in methanol (40 mL) and THE (80 mL) was added a solution of $LiOH.H_2O$ (11.2 g, 268 mmol) in $H_2O$ (20 mL). The mixture was stirred at 25° C. for 2 hours. On completion, the reaction mixture was concentrated in vacuo. The residue was acidified with 4 N aq.HCl till pH=3. The precipitated solid was filtered, collected and dried to give the title compound (22.0 g, 86% yield) as an off-white solid. $^1H$ NMR (400 MHz, DMSO-$d_6$) δ 14.26-12.46 (m, 1H), 8.22-8.10 (m, 2H), 7.96-7.86 (m, 1H), 2.03 (t, J=19.2 Hz, 3H).

Step 2—6-(1,1-Difluoroethyl)picolinoyl chloride

To a solution of 6-(1,1-difluoroethyl)pyridine-2-carboxylic acid (22.0 g, 117 mmol) in DCM (220 mL) and DMF (859 mg, 11.76 mmol) was added $(COCl)_2$ (29.8 g, 235.11 mmol) dropwise at 0° C. The mixture was stirred at 25° C. for 0.5 hour. On completion, the reaction mixture was concentrated in vacuo to give the title compound (24.0 g, 100% yield) as a yellow solid.

Step 3—6-(1,1-Difluoroethyl)picolinamide

A solution of 6-(1,1-difluoroethyl)pyridine-2-carbonyl chloride (24.0 g, 116 mmol) in THF (100 mL) was added to $NH_3.H_2O$ (146 g, 1.17 mol, 28% solution) dropwise at 0° C. The mixture was stirred at 25° C. for 0.5 hour. On completion, the residue was diluted with $H_2O$ (100 mL) and extracted with EA (3×200 mL). The combined organic layers were washed with brine (100 mL), dried over $Na_2SO_4$, filtered and concentrated in vacuo to give the title compound (18.0 g, 81% yield) as an off-white solid. $^1H$ NMR (400 MHz, DMSO-$d_6$) δ 8.26-8.10 (m, 3H), 7.90 (s, 1H), 7.78 (s, 1H), 2.12 (t, J=19.2 Hz, 3H).

Tert-butyl 2-methylpyrimidine-4-carboxamide (Intermediate BAE)

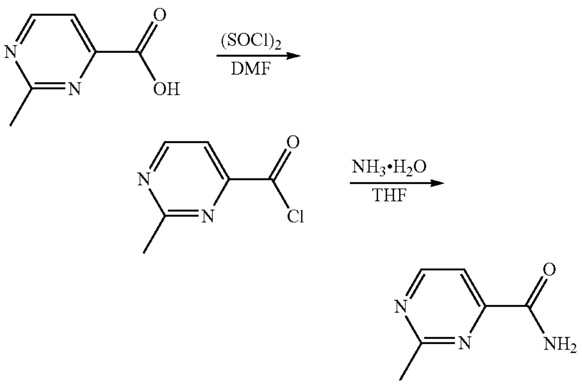

BAE

Step 1—Tert-butyl 2-methylpyrimidine-4-carbonyl chloride

To a solution of 2-methylpyrimidine-4-carboxylic acid (3.0 g, 21.7 mmol, CAS #13627-49-1) in $SOCl_2$ (5.0 mL) was added DMF (1 drop). The mixture was stirred at 80° C.

for 2 hours. On completion, the reaction mixture concentrated in vacuo to give the title compound (3.3 g, 99% yield) as yellow oil.

Step 2—Tert-butyl 2-methylpyrimidine-4-carboxamide

To a solution of 2-methylpyrimidine-4-carbonyl chloride (3.3 g, 19.2 mmol) in THF (5.0 mL) was added $NH_3.H_2O$ (24.0 g, 192 mmol, 26.4 mL, 28% solution). The mixture was stirred at 25° C. for 2 hours. On completion, the reaction mixture was concentrated in vacuo to give a residue. The residue was purified by column chromatography ($SiO_2$, petroleum ether/ethyl acetate=5/1 to 1/1) to give the title compound (1.5 g, 57% yield) as a yellow solid. LC-MS ($ESI^+$) m/z 138.1 $(M+H)^+$.

Tert-butyl 2- N-[2-(4-formylcyclohexyl)-6-methoxy-indazol-5-yl]-2-methyl-pyrimidine -4-carboxamide (Intermediate BAF)

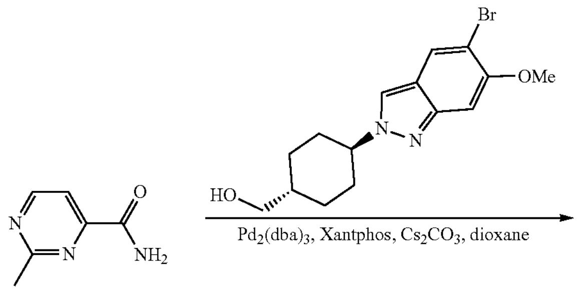

BAE

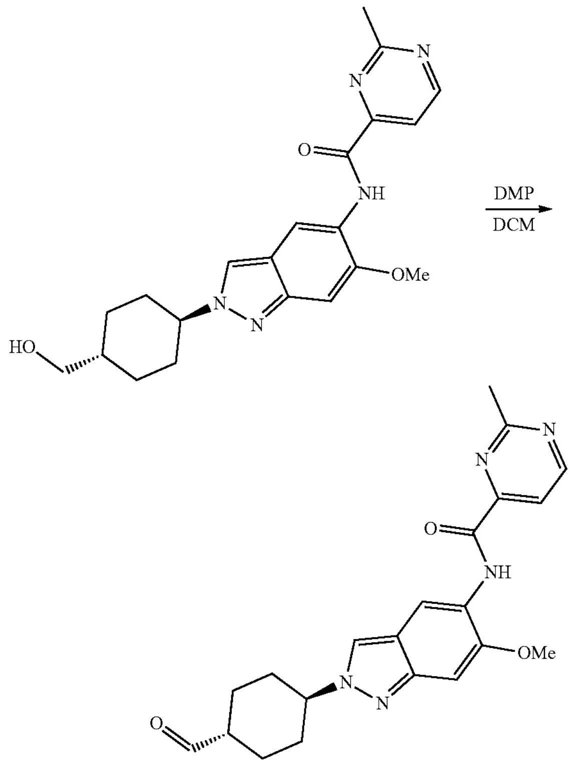

BAF

Step 1—Tert-butyl 2- N-[2-[4-(hydroxymethyl)cyclohexyl]-6-methoxy-indazol-5-yl]-2-methyl-pyrimidine-4-carboxamide To a mixture of 2-methylpyrimidine-4-carboxamide (550 mg, 4.01 mmol, Intermediate BAE) and [4-(5-bromo -6-methoxy-indazol-2-yl)cyclohexyl]methanol (1.36 g, 4.01 mmol, synthesized via Steps 1-3 of Intermediate ATE) in dioxane (8.0 mL) was added $Pd_2(dba)_3$ (367 mg, 401 umol), $Cs_2CO_3$ (2.61 g, 8.02 mmol) and Xantphos (232 mg, 401 umol) in one portion at 25° C. under $N_2$. The mixture was stirred at 80° C. under $N_2$ for 16 hours. On completion, the reaction mixture was quenched with water (10 mL) at 25° C., and then extracted with DCM (3×20 mL). The combined organic layers were dried over $Na_2SO_4$, filtered and the filtrate was concentrated in vacuo to give a residue. The residue was purified by column chromatography ($SiO_2$, petroleum ether/ethyl acetate=5/1 to 1/1) to give the title compound (200 mg, 12% yield) as a yellow solid. LC-MS ($ESI^+$) m/z 396.1 $(M+H)^+$.

Step 2—Tert-butyl 2- N-[2-(4-formylcyclohexyl)-6-methoxy-indazol-5-yl]-2-methyl- pyrimidine -4-carboxamide To a mixture of N-[2-[4-(hydroxymethyl)cyclohexyl]-6-methoxy-indazol -5-yl]-2-methyl- pyrimidine -4-carboxamide (160 mg, 405 umol) in DCM (3.0 mL) was added DMP (206 mg, 486 umol) at 25° C. The mixture was stirred at 25° C. for 2 hours. The reaction mixture was then quenched with saturated aq. $Na_2SO_3$ (10 mL) and aq. $NaHCO_3$ at 25° C., and then extracted with DCM (3×20 mL). The combined organic layers were dried over $Na_2SO_4$, filtered and concentrated in vacuo to give the title compound (150 mg, 94% yield) as a yellow solid. LC-MS ($ESI^+$) m/z 394.3 $(M+H)^+$.

Benzyl 4-[(3-aminocyclobutoxy)methyl]piperidine-1-carboxylate (Intermediate BAG)

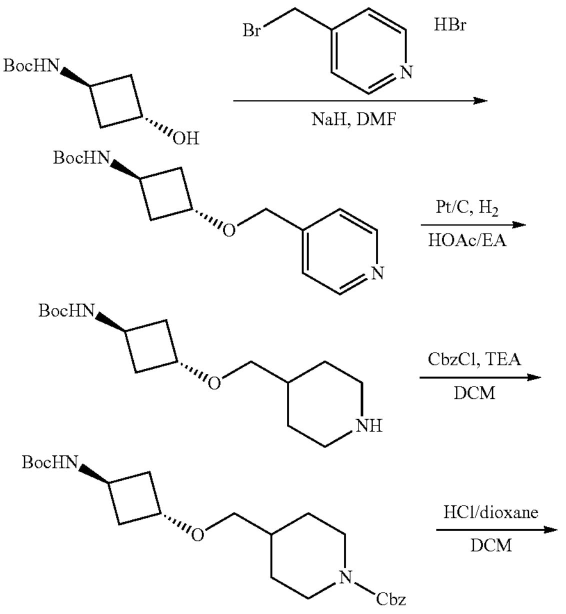

-continued

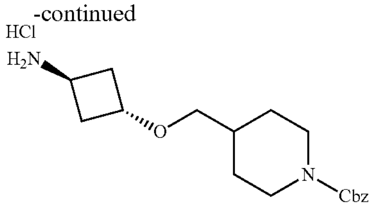

BAG

Step 1—Tert-butyl N-[3-(4-pyridylmethoxy)cyclobutyl]carbamate

To a mixture of 4-(bromomethyl)pyridine;hydrobromide (2.00 g, 7.91 mmol, CAS #73870-24-3) in TFH (40 mL) was added NaH (474 mg, 11.8 mmol, 60% dispersion in mineral oil) at 0° C. and stirred at 0.5 hour. Then tert-butyl N-(3-hydroxycyclobutyl)carbamate (1.78 g, 9.49 mmol, CAS #389890-42-0) was added into the mixture. The mixture was stirred at 20° C. for 3.5 hours. On completion, the reaction was quenched by water (0.5 mL) and concentrated in vacuo to give the residue. The residue was purified by reversed-phase HPLC (0.1% FA condition) title compound (1.50 g, 68% yield) as a white solid. $^1$H NMR (400 MHz, DMSO-$d_6$) δ 8.56-8.51 (m, 2H), 7.35-7.30 (m, 2H), 7.22-7.09 (m, 1H), 4.91 (d, J=5.2 Hz, 1H), 4.41 (s, 2H), 4.16-4.09 (m, 1H), 2.27-2.19 (m, 2H), 2.11-2.05 (m, 2H), 1.38 (s, 9H).

Step 2—Tert-butyl N-[3-(4-piperidylmethoxy)cyclobutyl]carbamate

To a mixture of tert-butyl N-[3-(4-pyridylmethoxy)cyclobutyl]carbamate (1.50 g, 5.39 mmol) in EA (20 mL) and HOAc (20 mL) was added Pt/C (1.13 g, 5 wt %) under $H_2$ (50 psi). The mixture was stirred at 25° C. for 12 hours. On completion, the mixture was filtered and concentrated to give the residue. The residue was purified by column chromatography ($SiO_2$, DCM:MeOH=10:1 to 3:1) to give the title compound (490 mg, 31% yield) as a white solid. $^1$H NMR (400 MHz, DMSO-$d_6$) δ 7.17 (d, J=6.8 Hz, 1H), 3.98-3.93 (m, 4H), 3.18 (s, 1H), 3.07 (d, J=5.6 Hz, 2H), 3.00 (d, J=12.0 Hz, 2H), 2.14-2.02 (m, 4H), 1.67-1.59 (m, 3H), 1.37 (s, 9H), 1.19-1.07 (m, 2H).

Step 3—Benzyl 4-[[3-(tert-butoxycarbonylamino)cyclobutoxy]methyl]piperidine-1-carboxylate To a mixture of tert-butyl N-[3-(4-piperidylmethoxy)cyclobutyl]carbamate (440 mg, 1.55 mmol) in DCM (3 mL) was added CbzCl (396 mg, 2.32 mmol) and TEA (313 mg, 3.09 mmol). The mixture was stirred at 20° C. for 1 hour. On completion, the reaction mixture was concentrated to give the residue. The residue was purified by column chromatography ($SiO_2$, PE:EA=2:1) to give the title compound (490 mg, 75% yield) as brown oil. $^1$H NMR (400 MHz, DMSO-$d_6$) δ 7.44-7.27 (m, 5H), 7.17 (d, J=7.2 Hz, 1H), 5.07 (s, 2H), 4.06-3.94 (m, 4H), 3.10 (d, J=6.0 Hz, 2H), 2.79 (d, J=2.4 Hz, 2H), 2.16-2.02 (m, 4H), 1.76-1.59 (m, 3H), 1.37 (s, 9H), 1.04-1.01 (m, 2H).

Step 4—Benzyl 4-[(3-aminocyclobutoxy)methyl]piperidine-1-carboxylate

To a mixture of benzyl 4-[[3-(tert-butoxycarbonylamino)cyclobutoxy]methyl]piperidine-1- carboxylate (340 mg, 812 umol) in DCM (5 mL) was added HCl/dioxane (4 M, 609 uL). The reaction mixture was stirred at 20° C. for 0.5 hour. On completion, the mixture was concentrated in vacuo to give the title compound (288 mg, 99% yield, HCl salt) as brown oil. LC-MS (ESI$^+$) m/z 319.4 (M+H)$^+$.

2-(2,6-Dioxo-3-piperidyl)-4-[[3-(4-piperidylmethoxy)cyclobutyl]amino]isoindoline-1,3-dione (Intermediate BAH)

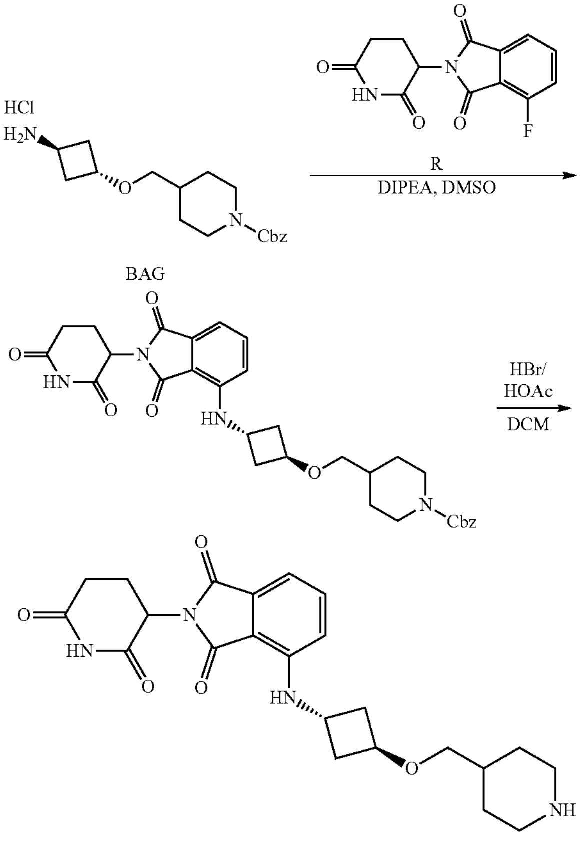

BAH

Step 1—Benzyl 4-[[3-[[2-(2,6-dioxo-3-piperidyl)-1,3-dioxo-isoindolin-4-yl]amino]cyclobutoxy] methyl]piperidine-1-carboxylate To a mixture of 2-(2,6-dioxo-3-piperidyl)-4-fluoro-isoindoline-1,3-dione (224 mg, 811 umol, Intermediate R) and benzyl 4-[(3-aminocyclobutoxy)methyl]piperidine-1-carboxylate (288 mg, 811 umol, HCl salt, Intermediate BAG) in DMSO (10 mL) was added DIPEA (209 mg, 1.62 mmol). The mixture was stirred at 130° C. for 2 hours. On completion, the mixture was poured into water (30 mL). The aqueous phase was extracted with ethyl acetate (2×20 mL). The combined organic phase was washed with brine (2×30 mL), dried with anhydrous $Na_2SO_4$, filtered and concentrated in vacuo to give the residue. The residue was purified by reversed-phase HPLC (0.1% FA condition) to give the title compound (286 mg, 61% yield) as a yellow solid. $^1$H NMR (400 MHz, DMSO-$d_6$) δ 11.11 (s, 1H), 7.60 (dd, J=7.2, 8.4 Hz, 1H), 7.40-7.32 (m, 5H), 7.09 (d, J=7.2 Hz, 1H), 6.92 (d, J=8.8 Hz, 1H), 6.50 (d, J=6.0 Hz, 1H), 5.10-5.03 (m, 3H), 4.21-4.09 (m, 2H), 4.02 (d, J=13.2 Hz, 2H), 3.17 (d, J=6.0 Hz, 2H), 2.96-2.74 (m, 3H), 2.67-2.54 (m, 2H), 2.37 (d, J=12.8 Hz, 2H), 2.28-2.19 (m, 2H), 2.08-1.99 (m, 1H), 1.78-1.64 (m, 3H), 1.16-1.02 (m, 2H).

Step 2—2-(2,6-Dioxo-3-piperidyl)-4-[[3-(4-piperidylmethoxy)cyclobutyl]amino]isoindoline-1,3-dione To a mixture of benzyl 4-[[3-[[2-(2,6-dioxo-3-piperidyl)-1,3-dioxo-isoindolin-4-yl]amino]cyclobutoxy]methyl]piperidine-1-carboxylate (103 mg, 179 umol) in DCM (5 mL) was added HBr (48.3 mg, 179 umol, 30% solution). The mixture was stirred at 20° C. for 0.5 hour. On completion, the mixture was concentrated in vacuo to give the title compound (78.0 mg, 98% yield) as brown oil. LC-MS (ESI$^+$) m/z 441.3 (M+H)$^+$.

3-(3-Methyl-2-oxo-4-piperazin-1-yl-benzimidazol-1-yl)piperidine-2,6-dione (Intermediate BAI)

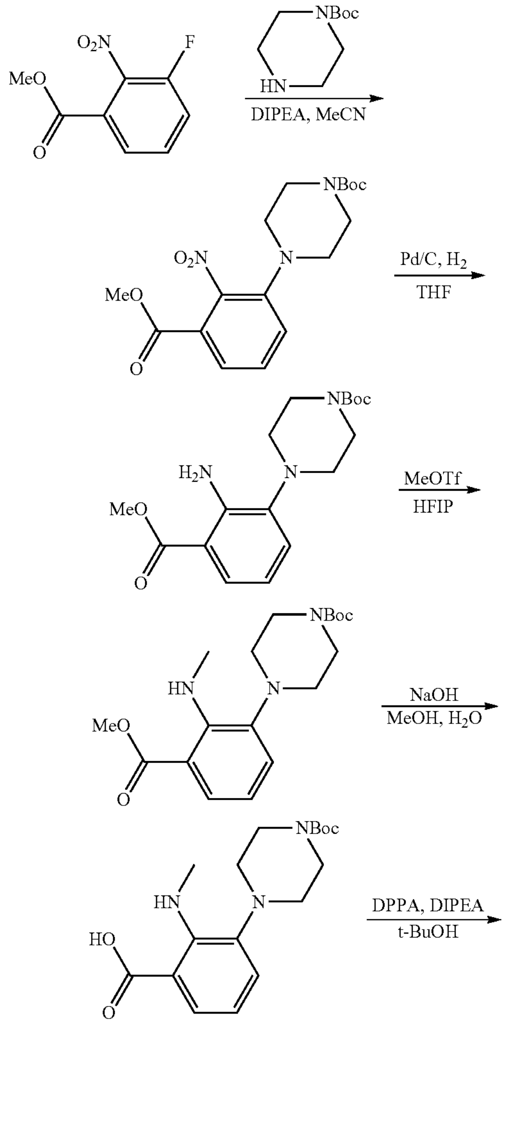

-continued

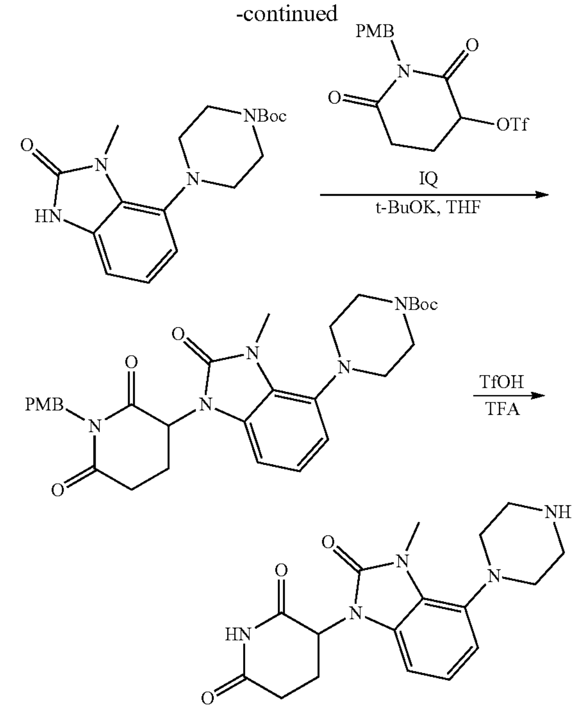

BAI

Step 1—Tert-butyl 4-(3-methoxycarbonyl-2-nitrophenyl)piperazine-1-carboxylate To a solution of methyl 3-fluoro-2-nitro-benzoate (10.0 g, 50.2 mmol, CAS #1214353-57-7) and tert-butyl piperazine-1-carboxylate (11.2 g, 60.3 mmol, CAS #143238-38-4) in ACN (100 mL) was added DIPEA (19.5 g, 151 mmol). The reaction mixture was stirred at 50° C. for 12 hrs. On completion, the mixture was concentrated in vacuo. The residue was dissolved in water (200 mL), then extracted with EA (2×200 mL). The organic layer was washed with brine (2×100 mL), dried with $Na_2SO_4$, filtered and the filtrate was concentrated in vacuo to give the title compound (18.3 g, 100% yield) as yellow oil. $^1$H NMR (400 MHz, DMSO-$d_6$) δ 7.86 (dd, J=1.2, 8.0 Hz, 1H), 7.82-7.79 (m, 1H), 7.74-7.68 (m, 1H), 3.83 (s, 3H), 3.40-3.35 (m, 4H), 2.88-2.84 (m, 4H), 1.41 (s, 9H).

Step 2—Tert-butyl 4-(2-amino-3-methoxycarbonylphenyl)piperazine-1-carboxylate To a solution of tert-butyl 4-(3-methoxycarbonyl-2-nitrophenyl)piperazine-1-carboxylate (17.0 g, 46.5 mmol) in THE (15 mL) was added Pd/C (2.00 g, 10 wt %). The reaction mixture was stirred at 20° C. for 12 hrs under $H_2$ (15 Psi) atmosphere. On completion, the mixture was filtered and the filtrate was concentrated in vacuo to give the title compound (15.2 g, 97% yield) as a yellow solid. $^1$H NMR (400 MHz, $CDCl_3$) δ 7.67 (dd, J=1.2, 8.0 Hz, 1H), 7.10 (dd, J=1.2, 7.6 Hz, 1H), 6.61 (t, J=7.6 Hz, 1H), 6.24 (br s, 2H), 4.28-3.95 (m, 2H), 3.87 (s, 3H), 3.16-2.84 (m, 4H), 2.80-2.55 (m, 2H), 1.49 (s, 9H).

Step 3—Tert-butyl 4-[3-methoxycarbonyl-2-(methylamino)phenyl]piperazine-1-carboxylate To a solution of tert-butyl 4-(2-amino-3-methoxycarbonyl-phenyl)piperazine-1-carboxylate (15.0 g, 44.7 mmol) in 1,1,1,3,3,3-hexafluoropropan-2-ol (40 mL) was added methyl trifluoromethanesulfonate (9.54 g, 58.1 mmol) at 0° C. The reaction mixture was stirred at 0° C. for 0.5 hr. On completion, the mixture was diluted with water (200 mL), then extracted with EA (2×200 mL). The organic layer was washed with brine (2×200 mL), dried with $Na_2SO_4$, filtered and the filtrate was concentrated in vacuo to give the title compound (15.0 g, 96% yield) as a yellow solid. $^1H$ NMR (400 MHz, DMSO-$d_6$) δ 8.16-7.90 (m, 1H), 7.46 (dd, J=1.2, 8.0 Hz, 1H), 7.23 (d, J=7.6 Hz, 1H), 6.77 (t, J=7.6 Hz, 1H), 3.80 (s, 3H), 3.55-3.45 (m, 4H), 2.87 (s, 3H), 2.80-2.74 (m, 4H), 1.42 (s, 9H).

Step 4—3-(4-Tert-butoxycarbonylpiperazin-1-yl)-2-(methylamino)benzoic acid

To a solution of tert-butyl 4-[3-methoxycarbonyl-2-(methylamino)phenyl]piperazine-1-carboxylate (14.0 g, 40.1 mmol) in a mixed solvent of $H_2O$ (20 mL) and MeOH (140 mL) was added NaOH (4.81 g, 120 mmol). The reaction mixture was stirred at 70° C. for 12 hrs. On completion, the mixture was concentrated in vacuo. The residue was diluted with water (200 mL), and extracted with EA (100 mL). The organic layer was discarded. The aqueous phase was acidified with HCl (1N) to pH=3-5, and extracted with EA (2×100 mL). The organic layer was washed with brine (200 mL), dried with $Na_2SO_4$, filtered and the filtrate was concentrated in vacuo. The residue was triturated with MeOH/H2O (1:10, 100 mL) and filtered. The filter cake was dried in vacuo to give the title compound (9.60 g, 71% yield) as a white solid. LC-MS (ESI$^+$) m/z 336.1 (M+H)$^+$.

Step 5—Tert-butyl 4-(3-methyl-2-oxo-1H-benzimidazol-4-yl)piperazine-1-carboxylate To a solution of 3-(4-tert-butoxycarbonylpiperazin-1-yl)-2-(methylamino)benzoic acid (9.60 g, 28.6 mmol) and DIPEA (11.1 g, 85.9 mmol) in t-BuOH (200 mL) was added DPPA (7.88 g, 28.6 mmol). The reaction mixture was stirred at 85° C. for 12 hrs. On completion, the mixture was concentrated in vacuo. The residue was diluted with water (200 mL), and extracted with EA (2×200 mL). The organic layer was washed with brine (200 mL) and concentrated in vacuo. The residue was purified by reverse phase (0.1% FA condition) to give the title compound (3.35 g, 35% yield) as a white solid. $^1H$ NMR (400 MHz, DMSO-$d_6$) δ 10.84 (s, 1H), 6.94-6.87 (m, 1H), 6.85-6.79 (m, 1H), 6.75 (dd, J=1.2, 7.6 Hz, 1H), 4.06-3.80 (m, 2H), 3.55 (s, 3H), 3.20-2.87 (m, 4H), 2.76-2.56 (m, 2H), 1.42 (s, 9H).

Step 6—Tert-butyl 4-[1-[1-[(4-methoxyphenyl)methyl]-2,6-dioxo-3-piperidyl]-3-methyl-2-oxo-benzimidazol-4-yl]piperazine-1-carboxylate To a solution of tert-butyl 4-(3-methyl-2-oxo-1H-benzimidazol-4-yl)piperazine-1-carboxylate (3.30 g, 9.93 mmol) in THE (50 mL) was added t-BuOK (1.67 g, 14.9 mmol) at 0° C. 1 hr later, and a solution of [1-[(4-methoxyphenyl)methyl]-2,6-dioxo-3-piperidyl]trifluoromethanesulfonate (4.54 g, 11.9 mmol, Intermediate IQ) in THF (20 mL) was added. The reaction mixture was stirred at 0° C. for 3 hrs. On completion, the mixture was acidified with FA to pH=3-5, diluted with water (300 mL), then extracted with EA (2×300 mL). The organic layer was washed with brine (200 mL) and concentrated in vacuo. The residue was purified by reverse phase flash (0.1% FA condition) to give the title compound (3.90 g, 70% yield) as a white solid. LC-MS (ESI$^+$) m/z 564.3 (M+H)$^+$.

Step 7—3-(3-Methyl-2-oxo-4-piperazin-1-yl-benzimidazol-1-yl)piperidine-2,6-dione To a solution of tert-butyl 4-[1-[1-[(4-methoxyphenyl)methyl]-2,6-dioxo-3-piperidyl]-3-methyl-2-oxo- benzimidazol-4-yl]piperazine-1-carboxylate (3.90 g, 6.92 mmol) in TFA (40 mL) was added TfOH (5 mL). The reaction mixture was stirred at 65° C. for 12 hrs. On completion, the mixture was concentrated in vacuo. The residue was purified by reverse phase flash (0.1% FA condition) to give the title compound (1.70 g, 63% yield, FA salt) as a blue solid. $^1H$ NMR (400 MHz, DMSO-$d_6$) δ 11.09 (s, 1H), 7.06-6.99 (m, 1H), 6.96-6.92 (m, 2H), 5.36 (dd, J=5.2, 12.4 Hz, 1H), 3.63 (s, 3H), 3.35-3.25 (m, 4H), 3.16-2.97 (m, 4H), 2.91-2.82 (m, 1H), 2.76-2.57 (m, 2H), 2.05-1.93 (m, 1H).

(2S)-Tetrahydropyran-2-carboxamide (Intermediate BAJ)

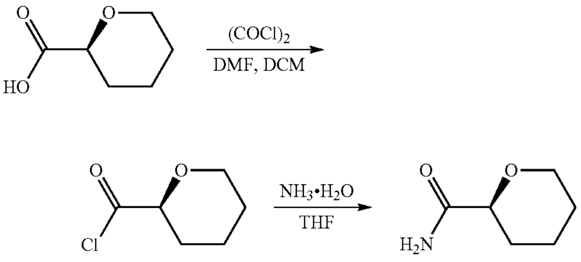

BAJ

Step 1—(2S)-Tetrahydropyran-2-carbonyl chloride

To a solution of (2S)-tetrahydropyran-2-carboxylic acid (500 mg, 3.84 mmol, CAS #105499-32-9) in DCM (10 mL) was added $(COCl)_2$ (975 mg, 7.68 mmol) and DMF (28.0 mg, 384 umol) at 0° C. The mixture was stirred at 0-25° C. for 2 hr. On completion, the mixture was concentrated in vacuo to give the title compound (570 mg, 99% yield) as colorless oil.

Step 2—(2S)-Tetrahydropyran-2-carboxamide

A solution of (2S)-tetrahydropyran-2-carbonyl chloride (570 mg, 3.84 mmol) in THF (10 mL) was added to $NH_3.H_2O$ (38.3 mmol, 4.93 mL, 30% solution) at 25° C. The mixture was stirred at 25° C. for 1 hour. On completion, the reaction mixture was diluted with $H_2O$ (15 mL) and extracted with EA (3×5 mL). The combined organic layers were washed with brine (10 mL), dried over $Na_2SO_4$, filtered and the filtrate was concentrated in vacuo to give the title compound (370 mg, 74% yield) as a white solid. 1H NMR (400 MHz, DMSO-d6) δ 7.23-6.79 (m, 2H), 3.97-3.87 (m, 1H), 3.63 (dd, J=2.4, 11.2 Hz, 1H), 3.45-3.37 (m, 1H), 1.90-1.74 (m, 2H), 1.52-1.41 (m, 3H), 1.35-1.22 (m, 1H).

2S)—N-[2-(4-formylcyclohexyl)-6-methoxy-indazol-5-yl]tetrahydropyran-2-carboxamide (Intermediate BAK)

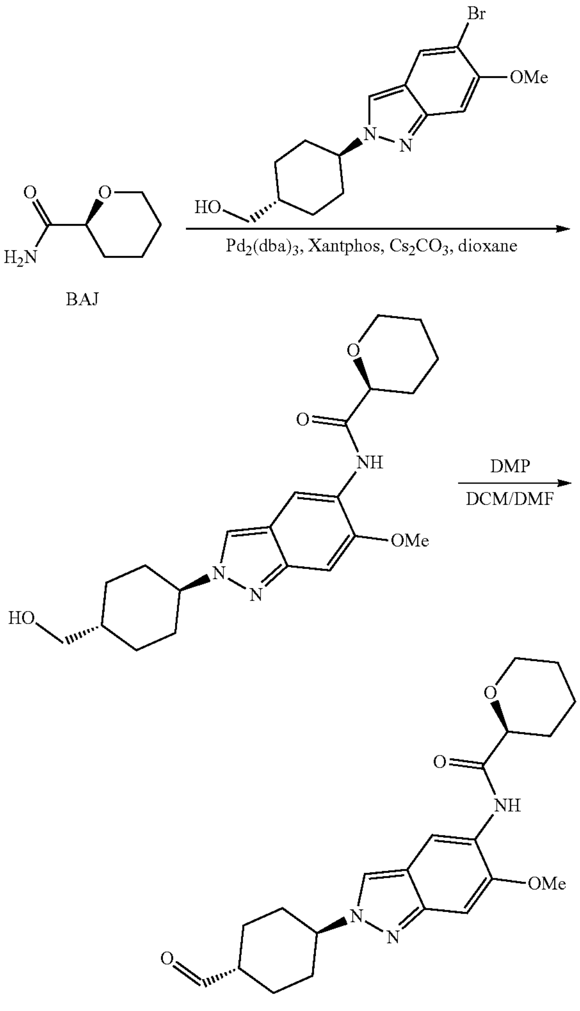

BAJ

BAK

Step 1—(2S)—N-[2-[4-(hydroxymethyl)cyclohexyl]-6-methoxy-indazol-5-yl]tetrahydropyran-2-carboxamide To a solution of (2S)-tetrahydropyran-2-carboxamide (178 mg, 1.39 mmol, Intermediate BAJ) and [4-(5-bromo-6-methoxy-indazol-2-yl)cyclohexyl]methanol (470 mg, 1.39 mmol, synthesized via Steps 1-3 of Intermediate ATE) in dioxane (12 mL) was added $Pd_2(dba)_3$ (126 mg, 138 umol), Xantphos (160 mg, 277 umol) and $Cs_2CO_3$ (902 mg, 2.77 mmol) at 25° C., the reaction mixture was stirred at 80° C. for 12 hours under nitrogen. On completion, the reaction mixture was filtered and the filtrate was concentrated in vacuo. The residue was purified by reverse phase (0.1% FA condition) to give the title compound (125 mg, 23% yield) as a yellow solid. 1H NMR (400 MHz, DMSO-d6) δ 8.96 (s, 1H), 8.47 (s, 1H), 8.25 (s, 1H), 7.07 (s, 1H), 4.49 (t, J=5.6 Hz, 1H), 4.39-4.27 (m, 1H), 4.08 (d, J=11.6 Hz, 1H), 3.95 (dd, J=2.4, 11.2 Hz, 1H), 3.90 (s, 3H), 3.59-3.50 (m, 1H), 3.31-3.26 (m, 2H), 2.11 (d, J=10.0 Hz, 2H), 2.06-1.99 (m, 1H), 1.92-1.80 (m, 5H), 1.57-1.36 (m, 5H), 1.21-1.05 (m, 2H); LC-MS ($ESI^+$) m/z 388.2 $(M+H)^+$.

Step 2—(2S)—N-[2-(4-formylcyclohexyl)-6-methoxy-indazol-5-yl]tetrahydropyran-2-carboxamide To a solution of (2S)—N-[2-[4-(hydroxymethyl)cyclohexyl]-6-methoxy-indazol-5-yl]tetrahydropyran -2-carboxamide (110 mg, 283 umol) in DCM (2 mL) and DMF (1 mL) was added DMP (156 mg, 369 umol) at 25° C. The reaction mixture was stirred at 25° C. for 2 hours. On completion, the reaction mixture was quenched with sat. aq. $Na_2S_2O_3$ (3 mL) and sat. aq. $NaHCO_3$ (3 mL) and extracted with DCM (3×15 mL). The combined organic layers were concentrated in vacuo to give the title compound (109 mg, 99% yield) as yellow oil. LC-MS ($ESI^+$) m/z 386.4 $(M+H)^+$.

3-[3-Methyl-2-oxo-4-(2-piperazin-1-ylethyl)benzimidazol-1-yl]piperidine-2,6-dione (Intermediate BAL)

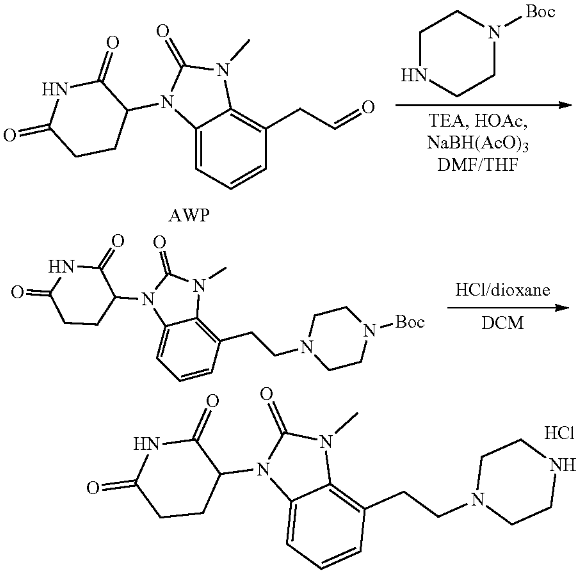

AWP

BAL

Step 1—Tert-butyl 4-[2-[1-(2, 6-dioxo-3-piperidyl)-3-methyl-2-oxo-benzimidazol-4-yl]ethyl]piperazine-1-carboxylate To a solution of tert-butyl piperazine-1-carboxylate (29.6 mg, 133 umol, HCl, CAS #143238-38-4) in a mixed solvent of DMF (1 mL) and THF (2 mL) was added TEA (13.4 mg, 133 umol, 18.5 uL), and HOAc (15.9 mg, 265 umol, 15.2 uL). The reaction mixture was adjust to pH 5-6, then 2-[1-(2, 6-dioxo-3-piperidyl)-3-methyl-2-oxo-benzimidazol-4-yl] acetaldehyde (40.0 mg, 133 umol, Intermediate AWP) was added. Thirty minutes later, $NaBH(OAc)_3$ (36.6 mg, 172 umol) was added and the reaction mixture was stirred at 0° C. for 3 hrs. On completion, the reaction mixture was quenched with water (0.1 ml) and concentrated in vacuo. The crude product was purified by reversed-phase HPLC (0.1% FA condition) to give the title compound (60.0 mg, 60% yield) as white solid. LC-MS (ESI+) m/z 472.3 $(M+H)^+$.

Step 2—3-[3-Methyl-2-oxo-4-(2-piperazin-1-yl-ethyl)benzimidazol-1-yl]piperidine-2,6-dione To a solution of tert-butyl 4-[2-[1-(2, 6-dioxo-3-piperidyl)-3-methyl-2-oxo-benzimidazol-4-yl]ethyl]piperazine-1-carboxylate (60.0 mg, 127 umol) in DCM (2 mL) was added HCl/dioxane (4 M, 53.0 uL). The mixture was stirred at 25° C. for 2 hours. On completion, the reaction mixture was filtered and concentrated in vacuo to give the title compound (45.0 mg, 66.4% yield, HCl) as yellow solid. LC-MS (ESI+) m/z 372.2 $(M+H)^+$.

3-[3-Methyl-4-[[7-(methylamino)spiro[3.5]nonan-2-yl]methyl]-2-oxo-benzimidazol-1-yl]piperidine-2,6-dione (Intermediate BAM) and 3-[3-Methyl-4-4[[7-(methylamino)spiro[3.5]nonan-2-yl]methyl]-2-oxo-benzimidazol-1- yl]piperidine-2,6-dione (Intermediate BAN)

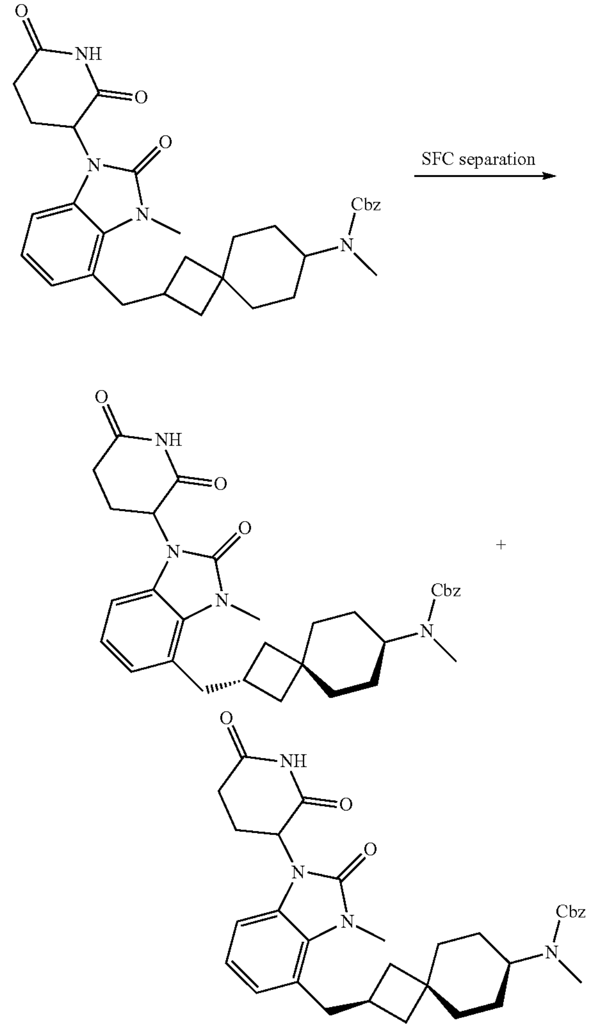

-continued

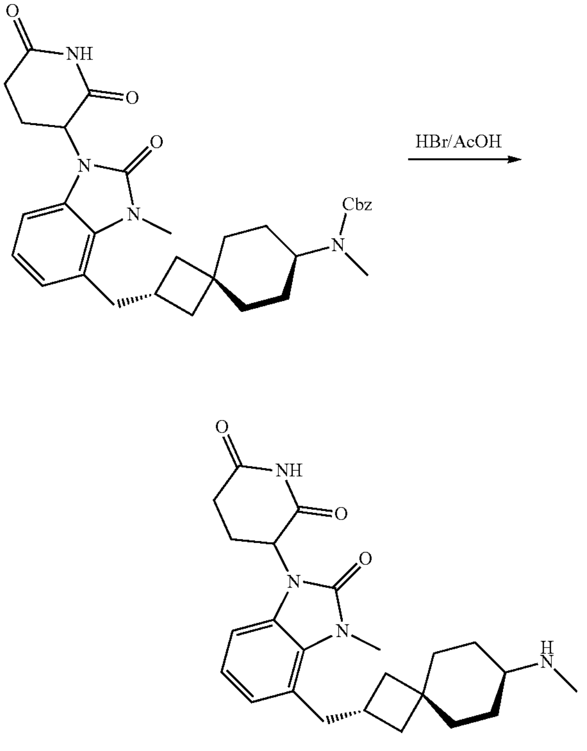

BAM

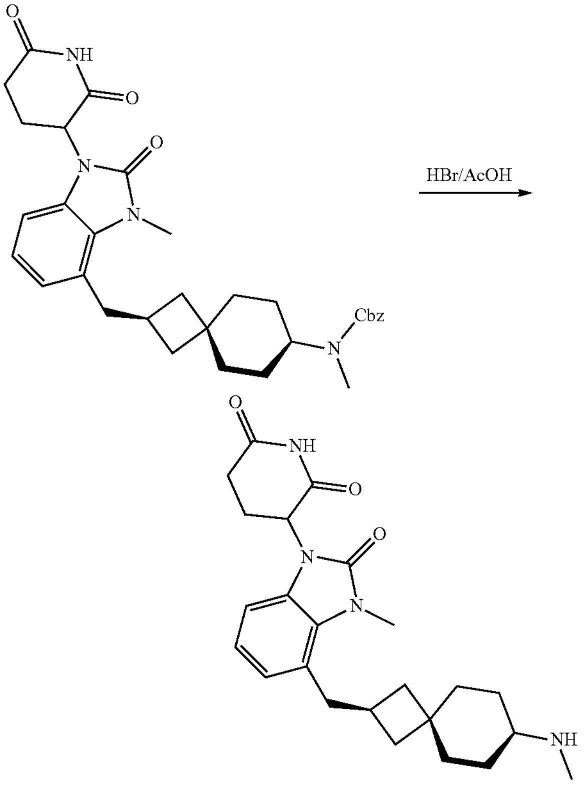

BAN

Step 1—Benzyl ((2R,4s,7R)-2-((1-(2,6-dioxopiperidin-3-yl)-3-methyl-2-oxo-2,3-dihydro-1H-benzo[d]imidazol-4-yl)methyl)spiro[3.5]nonan-7-yl)(methyl)carbamate and benzyl ((2S,4r,7S)-2-((1-(2,6-dioxopiperidin-3-yl)-3-methyl-2-oxo-2,3-dihydro-1H-benzo[d]imidazol-4-yl)methyl)spiro[3.5]nonan-7-yl)(methyl)carbamate Benzyl(2-((1-(2,6-dioxopiperidin-3-yl)-3-methyl-2-oxo-2,3-dihydro-1H-benzo[d]imidazol-4-yl)methyl)spiro[3.5]nonan-7-yl)(methyl)carbamate (1.90 g, 3.40 mmol, Intermediate ARW) was purified by SFC(column:REGIS(s,s) WHELK-O1(250 mm*50 mm,10 um);mobilephase:[Neu-ETOH];B %:50%-50%, 4.15 min; 651 minmin) and Prep-HPLC (column: Phenomenex luna C18 150*40 mm*15 um; mobilephase:[water (0.225% FA)-ACN];B %: 53%-83%, 9 min) to give the two isomers. The first fraction was benzyl ((2R,4s,7R)-2-((1-(2,6-dioxopiperidin-3-yl)-3-methyl-2-oxo-2,3-dihydro-1H-benzo [d]imidazol-4-yl)methyl)spiro[3.5]nonan-7-yl)(methyl)carbamate (350 mg, 18% yield, tR=2.44) isolated as a white solid. $^1$H NMR (400 MHz, $CDCl_3$) δ 8.29 (s, 1H), 7.46-7.27 (m, 5H), 7.01-6.93 (m, 1H), 6.85 (d, J=7.5 Hz, 1H), 6.67 (d, J=7.6 Hz, 1H), 5.25-5.17 (m, 1H), 5.13 (s, 2H), 4.02-3.74 (m, 1H), 3.66 (s, 3H), 3.11-2.72 (m, 8H), 2.61-2.45 (m, 1H), 2.25-2.17 (m, 1H), 2.07-1.98 (m, 1H), 1.93-1.80 (m, 2H), 1.68-1.41 (m, 9H); LC-MS ($ESI^+$) m/z 559.5 $(M+H)^+$. The second fraction was benzyl((2S,4r,7S)-2-((1-(2,6-dioxopiperidin-3-yl)-3-methyl -2-oxo-2,3-dihydro-1H-benzo[d]imidazol-4-yl)methyl)spiro[3.5]nonan-7-yl)(methyl)carbamate (360 mg, 18% yield, tR=3.02) as white solid. $^1$H NMR (400 MHz, $CDCl_3$) δ 8.16 (s, 1H), 7.41-7.28 (m, 5H), 7.01-6.93 (m, 1H), 6.85 (d, J=7.5 Hz, 1H), 6.67 (d, J=7.6 Hz, 1H), 5.24-5.17 (m, 1H), 5.16-5.09 (m, 2H), 4.05-3.74 (m, 1H), 3.66 (s, 3H), 3.12-2.90 (m, 3H), 2.90-2.69 (m, 5H), 2.63-2.46 (m, 1H), 2.29-2.18 (m, 1H), 2.07-1.98 (m, 1H), 1.94-1.80 (m, 2H), 1.60-1.30 (m, 9H); LC-MS ($ESI^+$) m/z 559.5 $(M+H)^+$.

Step 2—3-[3-Methyl-4-[[7-(methylamino)spiro[3.5]nonan-2-yl]methyl]-2-oxo-benzimidazol-1-yl]piperidine-2,6-dione A solution of benzyl N-[2-[[1-(2,6-dioxo-3-piperidyl)-3-methyl-2-oxo-benzimidazol-4-yl]methyl]spiro[3.5]nonan-7-yl]-N-methyl-carbamate (200 mg, 358 umol) in HBr/HOAc (15 mL, 33% solution) was stirred at 25° C. for 1 hr. On completion, the reaction mixture was concentrated in vacuo to give the title compound (200 mg, 80% purity, 88% yield, HBr salt) as a red solid. LC-MS ($ESI^+$) m/z 425.2 $(M+H)^+$.

Step 3—3-[3-Methyl-4-[[7-(methylamino)spiro[3.5]nonan-2-yl]methyl]-2-oxo-benzimidazol-1- yl]piperidine-2,6-dione To a solution of benzyl N-[2-[[1-(2,6-dioxo-3-piperidyl)-3-methyl-2-oxo-benzimidazol-4-yl]methyl]spiro[3.5]nonan-7-yl]-N-methyl-carbamate (100 mg, 179 umol) was added HBr/HOAc (2.5 mL, 46.0 mmol, 30% solution). The reaction mixture was stirred at 25° C. for 1 hr. On completion, the mixture was concentrated to give the title compound (70.0 mg, 40% yield) as yellow oil. LC-MS ($ESI^+$) m/z 425.5 $(M+H)^+$.

Tert-butyl 2-formyl-7-azaspiro[3.5]nonane-7-carboxylate (Intermediate BAO)

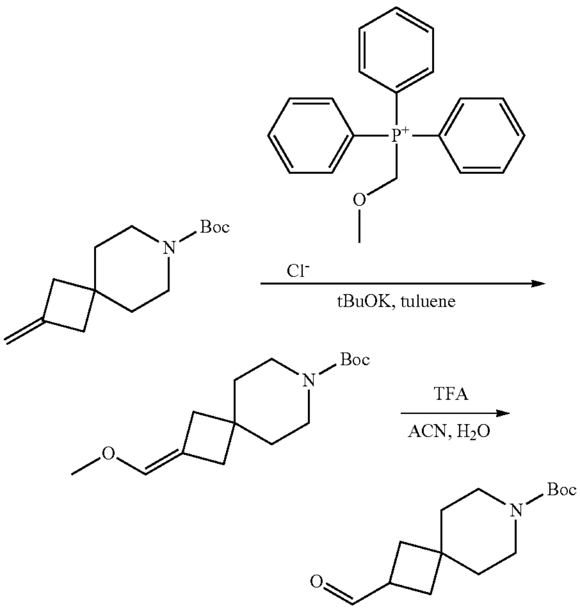

BAO

Step 1—Tert-butyl 2-(methoxymethylene)-7-azaspiro[3.5]nonane-7-carboxylate

Under argon atmosphere, to a suspension of methoxymethyl(triphenyl)phosphonium;chloride (9.31 g, 27.1 mmol, CAS #4009-98-7) in toluene (100 mL) was added tBuOK (3.05 g, 27.1 mmol) and the mixture was stirred at room temperature for 20 min. To this mixture was added a solution of tert-butyl 2-oxo-7-azaspiro[3.5]nonane-7-carboxylate (5.00 g, 20.8 mmol, CAS #1346556-73-7) in toluene (20 mL) and the mixture was stirred at 70° C. for 4 h. On completion, the mixture was washed by water (1000 mL) and extracted with EA (500 mL). The combined organic layer was dried over $Na_2SO_4$ and filtrated, and the filtrate was concentrated in vacuo. The residue was purified by column chromatography (petroleum ether:ethyl acetate=5:1) to give the title compound (5.59 g, 31% yield) as yellow oil. $^1$H NMR (400 MHz, DMSO-$d_6$) δ 5.99-5.82 (m, 1H), 3.46 (s, 3H), 3.27-3.16 (m, 4H), 2.31 (d, J=18.0 Hz, 4H), 1.49-1.41 (m, 4H), 1.38 (s, 9H).

Step 2—Tert-butyl 2-formyl-7-azaspiro[3.5]nonane-7-carboxylate

To a solution of tert-butyl 2-(methoxymethylene)-7-azaspiro[3.5]nonane-7-carboxylate (10.5 g, 39.2 mmol) in a mixed solution of ACN (100 mL) and $H_2O$ (25 mL) was added a solution of TFA (4.48 g, 39.2 mmol) in ACN (20 mL) and $H_2O$ (5 mL). The reaction mixture was stirred at 25° C. for 1 hr. On completion, the reaction mixture was exacted with EA (3×100 mL). The organic phase was dried over anhydrous sodium sulfate, then concentrated in vacuo. The residue was purified by silica gel chromatography (PE:EA=100:1 to 10:1) to give the title compound (8.2 g, 82% yield) as white liquid. $^1$H NMR (400 MHz, DMSO-$d_6$)

δ 9.68 (d, J=1.6 Hz, 1H), 3.28-3.24 (m, 2H), 3.22-3.18 (m, 2H), 3.17-3.03 (m, 1H), 1.96-1.94 (m, 2H), 1.92 (d, J=3.2 Hz, 2H), 1.55-1.51 (m, 2H), 1.39 (s, 9H), 1.36-1.32 (m, 2H).

3-(4-amino-3-methyl-2-oxo-benzimidazol-1-yl)piperidine-2,6-dione (Intermediate BAP)

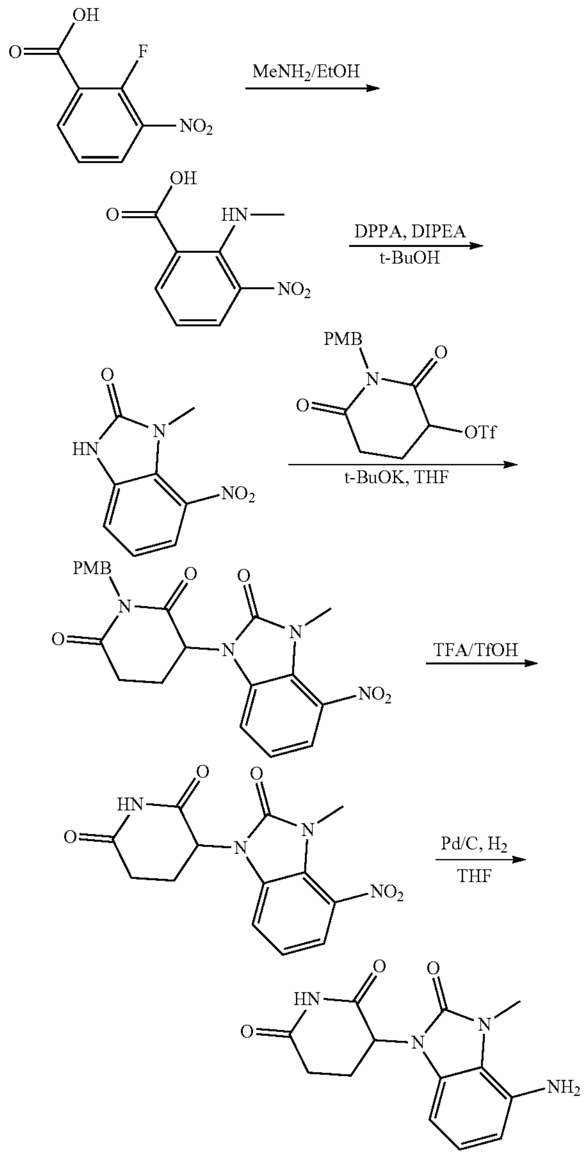

BAP

Step 1—2-(Methylamino)-3-nitro-benzoic acid

To a solution of $MeNH_2$/EtOH (54.0 mmol, 200 mL, 30% solution) was added 2-fluoro-3-nitro-benzoic acid (10.0 g, 54.0 mmol) in portions at 0° C. Then the reaction mixture was stirred at 20° C. for 2 hrs. On completion, the mixture was concentrated in vacuo. The residue was diluted with water (100 mL), acidified with citric acid to pH=3-5, stirred and filtered. The filter cake was dried in vacuo to give the title compound (9.60 g, 91% yield) as a yellow solid. $^1H$ NMR (400 MHz, DMSO-$d_6$) δ 13.41 (s, 1H), 8.62 (s, 1H), 8.04 (dd, J=1.6, 8.0 Hz, 1H), 7.97 (dd, J=1.6, 8.0 Hz, 1H), 6.72 (t, J=8.0 Hz, 1H), 2.70 (s, 3H).

Step 2—3-Methyl-4-nitro-1H-benzimidazol-2-one

To a solution of 2-(methylamino)-3-nitro-benzoic acid (8.60 g, 43.8 mmol) and DIPEA (17.0 g, 132 mmol) in t-BuOH (200 mL) was added DPPA (12.1 g, 43.8 mmol) dropwise at 0° C. Then the reaction mixture was stirred at 85° C. for 12 hours. On completion, the mixture was diluted with MeOH (100 mL), cooled to 10-20° C., filtered and the filter cake was dried in vacuo to give the title compound (6.80 g, 80% yield) as a yellow solid. $^1H$ NMR (400 MHz, DMSO-$d_6$) δ 11.61 (s, 1H), 7.58 (dd, J=0.8, 8.0 Hz, 1H), 7.30 (dd, J=0.8, 8.0 Hz, 1H), 7.18-7.07 (m, 1H), 3.34 (s, 3H).

Step 3—1-[(4-Methoxyphenyl)methyl]-3-(3-methyl-4-nitro-2-oxo-benzimidazol-1-yl)piperidine-2,6-dione To a solution of 3-methyl-4-nitro-1H-benzimidazol-2-one (7.20 g, 37.3 mmol) in THF (70 mL) was added t-BuOK (8.37 g, 74.6 mmol) at −10-0° C. One hour later, a solution of [1-[(4-methoxyphenyl)methyl]-2,6-dioxo-3-piperidyl]trifluoromethanesulfonate (21.3 g, 55.9 mmol, Intermediate IQ) in THE (50 mL) was added into the above mixture and the reaction mixture was stirred at 0-20° C. for 12 hrs. On completion, the mixture was acidified with FA to pH=3-5, diluted with water (300 mL), and extracted with EA (2×300 mL). The organic layer was washed with brine (200 mL), then concentrated in vacuo. The residue was purified by reverse phase (0.1% FA condition) to give the title compound (5.80 g, 37% yield) as a yellow solid. $^1H$ NMR (400 MHz, DMSO-$d_6$) δ 7.69 (dd, J=0.8, 8.0 Hz, 1H), 7.46 (d, J=8.0 Hz, 1H), 7.27-7.17 (m, 3H), 6.93-6.78 (m, 2H), 5.67 (dd, J=5.2, 12.8 Hz, 1H), 4.94-4.62 (m, 2H), 3.72 (s, 3H), 3.41 (s, 3H), 3.11-2.98 (m, 1H), 2.89-2.70 (m, 2H), 2.17-2.08 (m, 1H).

Step 4—3-(3-Methyl-4-nitro-2-oxo-benzimidazol-1-yl)piperidine-2,6-dione

To a solution of 1-[(4-methoxyphenyl)methyl]-3-(3-methyl-4-nitro-2-oxo-benzimidazol-1-yl) piperidine-2,6-dione (2.00 g, 4.71 mmol) in TFA (20 mL) was added TfOH (2 mL). The reaction mixture was stirred at 60° C. for 12 hours. On completion, the mixture was concentrated in vacuo. The residue was purified by reverse phase (0.1% FA condition) to give the title compound (900 mg, 63% yield) as a yellow solid. $^1H$ NMR (400 MHz, DMSO-$d_6$) δ 11.19 (s, 1H), 7.68 (dd, J=0.8, 8.0 Hz, 1H), 7.55 (d, J=8.0 Hz, 1H), 7.23 (t, J=8.0 Hz, 1H), 5.51 (dd, J=5.2, 12.8 Hz, 1H), 3.41 (s, 3H), 2.95-2.85 (m, 1H), 2.80-2.60 (m, 2H), 2.13-2.06 (m, 1H).

Step 5—3-(4-Amino-3-methyl-2-oxo-benzimidazol-1-yl)piperidine-2,6-dione

To a solution of 3-(3-methyl-4-nitro-2-oxo-benzimidazol-1-yl)piperidine-2,6-dione (850 mg, 2.79 mmol) in THE (50 mL) was added Pd/C (200 mg, 10% wt). The reaction mixture was stirred at 20° C. for 12 hrs under $H_2$ (15 Psi) atmosphere. On completion, the mixture was filtered and the filtrate was concentrated in vacuo to give the title compound (0.70 g, 91% yield) as a pink solid. LC-MS (ESI$^+$) m/z 275.1 $(M+H)^+$.

3-[4-(7-Azaspiro[3.5]nonan-2-ylmethylamino)-3-methyl-2-oxo-benzimidazol-1-yl]piperidine -2,6-dione (Intermediate BAO)

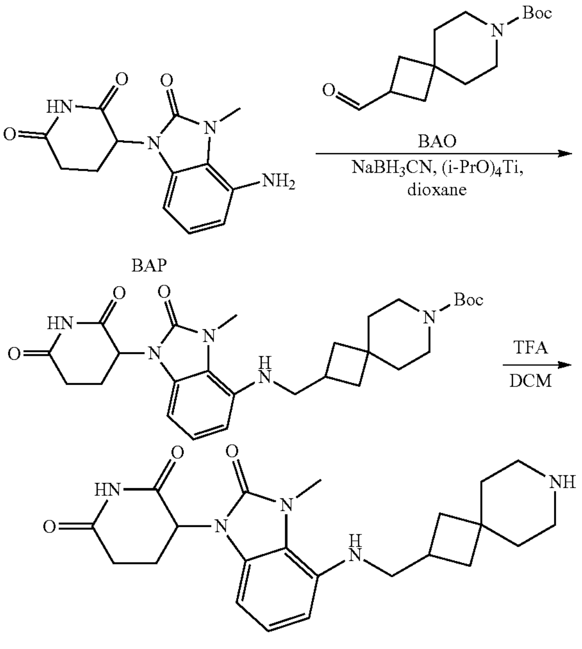

BAP

BAQ

Step 1—Tert-butyl 2-[[[1-(2,6-dioxo-3-piperidyl)-3-methyl-2-oxo-benzimidazol-4-yl]amino]methyl]-7-azaspiro[3.5]nonane-7-carboxylate To a mixture of 3-(4-amino-3-methyl-2-oxo-benzimidazol-1-yl)piperidine-2,6-dione (200 mg, 729 umol, Intermediate BAP) and tert-butyl 2-formyl-7-azaspiro[3.5]nonane-7-carboxylate (184 mg, 729 umol, Intermediate BAO) in dioxane (2 mL) was added tetraethoxytitanium (499 mg, 2.19 mmol). The reaction mixture was stirred at 80° C. for 17 hrs then cooled to 25° C. Then $NaBH_3CN$ (137 mg, 2.19 mmol) was added to the reaction mixture and stirred at 25° C. for 3 hr. On completion, the reaction mixture was filtered, the filtrate was concentrated in vacuo. The residue was purified by reversed-phase HPLC (0.1% FA condition) to give the title compound (160 mg, 42% yield) as a white solid. $^1H$ NMR (400 MHz, DMSO-$d_6$) δ 11.07 (s, 1H), 6.92-6.77 (m, 1H), 6.50 (d, J=7.6 Hz, 1H), 6.42 (d, J=8.4 Hz, 1H), 5.44-5.16 (m, 1H), 5.01-4.79 (m, 1H), 3.60 (s, 3H), 3.29-3.26 (m, 2H), 3.20-3.17 (m, 2H), 3.12-3.05 (m, 2H), 2.95-2.83 (m, 1H), 2.66-2.57 (m, 2H), 2.06-1.82 (m, 4H), 1.56-1.48 (m, 4H), 1.44-1.41 (m, 2H), 1.39 (s, 9H).

Step 2—3-[4-(7-Azaspiro[3.5]nonan-2-ylmethylamino)-3-methyl-2-oxo-benzimidazol-1-yl]piperidine -2,6-dione To a mixture of tert-butyl 2-[[[1-(2,6-dioxo-3-piperidyl)-3-methyl-2-oxo-benzimidazol-4-yl]amino]methyl]-7-azaspiro[3.5]nonane-7-carboxylate (70 mg, 136 umol) in DCM (3 mL) was added TFA (1 mL). The reaction mixture was stirred at 25° C. for 0.5 hr. On completion, the reaction mixture was concentrated in vacuo to give the title compound (65 mg, 90% yield, TFA salt) as yellow oil. LC-MS ($ESI^+$) m/z 412.4 $(M+H)^+$.

[4-[5-Bromo-6-[(1S,4S)-2-oxa-5-azabicyclo[2.2.1]heptan-5-yl]indazol-2-yl]cyclohexyl]methanol (Intermediate BAR)

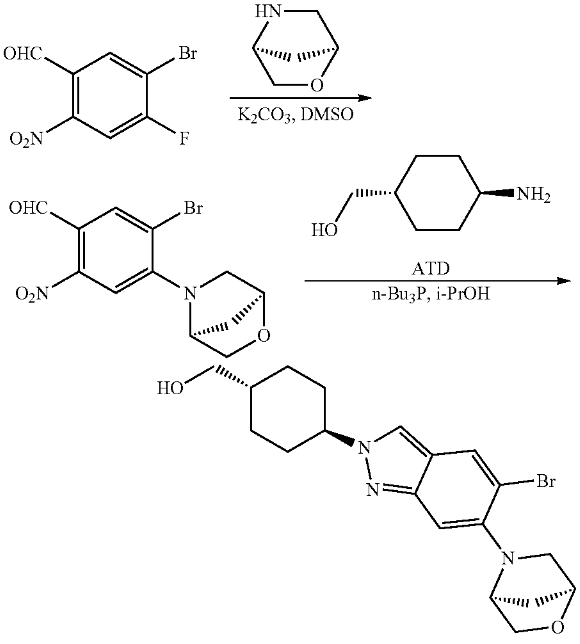

BAR

Step 1—[4-[5-Bromo-6-[(1S,4S)-2-oxa-5-azabicyclo[2.2.1]heptan-5-yl]indazol-2-yl]cyclohexyl]methanol To a solution of (1S,4S)-2-oxa-5-azabicyclo[2.2.1]heptane (4.00 g, 40.3 mmol, CAS #279-33-4), $K_2CO_3$ (5.57 g, 40.3 mmol) in DMSO (60 mL) was added with 5-bromo-4-fluoro-2-nitro-benzaldehyde (5.00 g, 20.2 mmol, synthesized via Step 1 of Intermediate ATE). The reaction mixture was stirred at 80° C. for 1 hours. On completion, the reaction mixture was diluted with EtOAc (50 mL) and extracted with EtOAc (3×50 mL). The combined organic layers were washed with saturated NaCl solution (3×50 mL), dried over $Na_2SO_4$, filtered and concentrated in vacuo to give the title compound (6.60 g, 91% yield) as a yellow solid. $^1H$ NMR (400 MHz, $CDCl_3$) δ 10.23 (s, 1H), 8.18 (s, 1H), 7.22 (s, 1H), 4.87-4.70 (m, 2H), 4.11-4.09 (m, 1H), 4.00 (dd, J=1.6, 8.0 Hz, 1H), 3.49 (d, J=10.0 Hz, 1H), 2.08 (s, 2H), 1.65 (s, 1H).

Step 2—[4-[5-Bromo-6-[(1S,4S)-2-oxa-5-azabicyclo[2.2.1]heptan-5-yl]indazol-2-yl]cyclohexyl]methanol To a solution of 5-bromo-2-nitro-4-[(1S,4S)-2-oxa-5-azabicyclo[2.2.1]heptan-5-yl]benzaldehyde (2.00 g, 6.11 mmol) in IPA (50 mL) was added (4-aminocyclohexyl)methanol (948 mg, 7.34 mmol, Intermediate ATD). The mixture was heated at 80° C. for 4 hr under $N_2$. Then the mixture was cooled to 25° C. and tributylphosphane (3.71 g, 18.3 mmol) was added. The reaction mixture was heated to 80° C. for 16 hr. On completion, the reaction mixture was concentrated in vacuo to give a residue. The residue was purified by reverse phase flash (0.1% FA condition) to give the title compound (4.00 g, 81% yield) as a yellow solid. $^1$H NMR (400 MHz, DMSO-$d_6$) δ 8.24 (s, 1H), 7.95 (s, 1H), 7.14 (s, 1H), 4.57 (s, 1H), 4.41-4.29 (m, 2H), 3.97 (d, J=7.6 Hz, 1H), 3.74 (dd, J=1.6, 7.6 Hz, 1H), 3.53 (dd, J=1.6, 9.6 Hz, 2H), 3.30-3.23 (m, 4H), 2.18-2.05 (m, 2H), 1.96-1.76 (m, 6H), 1.20-1.09 (m, 2H).

N-[2-(4-formylcyclohexyl)-6-[(1S,4S)-2-oxa-5-azabicyclo[2.2.1]heptan-5-yl]indazol-5-yl]-6-(trifluoromethyl)pyridine-2-carboxamide (Intermediate BAS)

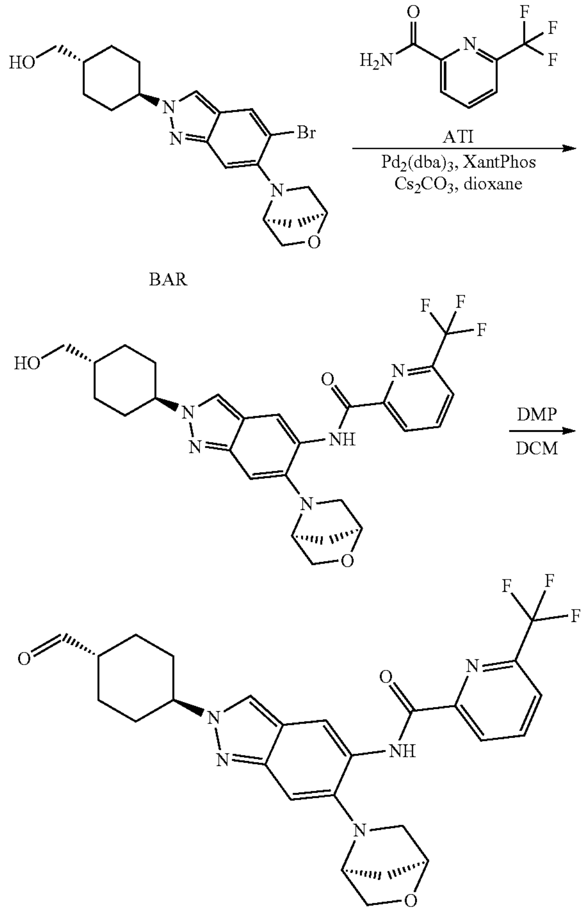

BAR

BAS

Step 1—N-[2-[4-(hydroxymethyl)cyclohexyl]-6-[(1S,4S)-2-oxa-5-azabicyclo[2.2.1]heptan-5-yl]indazol-5-yl]-6-(trifluoromethyl)pyridine-2-carboxamide To a solution of [4-[5-bromo-6-[(1S,4S)-2-oxa-5-azabicyclo[2.2.1]heptan-5-yl]indazol-2-yl]cyclohexyl]methanol (2.00 g, 4.92 mmol, Intermediate BAR) in dioxane (50 mL) was added $Pd_2(dba)_3$ (283 mg, 492 umol), Xantphos (570 mg, 984 umol), $Cs_2CO_3$ (3.21 g, 9.84 mmol) and 6-(trifluoromethyl)pyridine-2-carboxamide (1.40 g, 7.38 mmol, Intermediate ATI). The mixture was stirred at 110° C. for 16 hrs. On completion, the reaction mixture was filtered and the filtrate was concentrated in vacuo to give a residue. The residue was purified by reverse phase flash (0.1% FA condition) to give a residue. The residue was dissolved in solvent EtOAc, and the resulting suspension was stirred 30 min at 25° C., then the suspension was filtered and the filter cake was dried in vacuo to give the title compound (1.40 g, 55% yield). $^1$H NMR (400 MHz, DMSO-$d_6$) δ 10.69 (s, 1H), 8.68 (s, 1H), 8.54-8.38 (m, 2H), 8.34 (s, 1H), 8.22 (d, J=7.6 Hz, 1H), 7.40 (s, 1H), 4.62 (s, 1H), 4.54-4.27 (m, 2H), 4.12-3.94 (m, 2H), 3.67 (dd, J=1.6, 7.6 Hz, 1H), 3.43 (d, J=10.0 Hz, 1H), 3.32-3.23 (m, 4H), 2.17-2.07 (m, 3H), 1.92-1.80 (m, 4H), 1.47 (m, 1H), 1.26-1.06 (m, 2H).

Step 2—N-[2-(4-formylcyclohexyl)-6-[(1S,4S)-2-oxa-5-azabicyclo[2.2.1]heptan-5-yl]indazol-5-yl]-6-(trifluoromethyl)pyridine-2-carboxamide To a mixture of N-[2-[4-(hydroxymethyl)cyclohexyl]-6-[(1S,4S)-2-oxa-5-azabicyclo[2.2.1]heptan-5-yl]indazol-5-yl]-6-(trifluoromethyl)pyridine-2-carboxamide (201 mg, 390 umol) in DCM (5.0 mL) was added DMP (198 mg, 467 umol) at 0° C. under $N_2$. The mixture was stirred at 0° C. for 30 min. On completion, the mixture was quenched with saturated $Na_2S_2O_3$ (10 mL) and washed with saturated $NaHCO_3$ (2×10 mL). The organic layer was dried over anhydrous $Na_2SO_4$, filtered and concentrated in vacuo to give the title compound (200 mg, 94% yield) as yellow solid. LC-MS (ESI$^+$) m/z 514.2 (M+H)$^+$.

N-[2-(4-formylcyclohexyl)-6-methoxy-indazol-5-yl]pyrazolo[1,5-a]pyrimidine-3-carboxamide (Intermediate BAT)

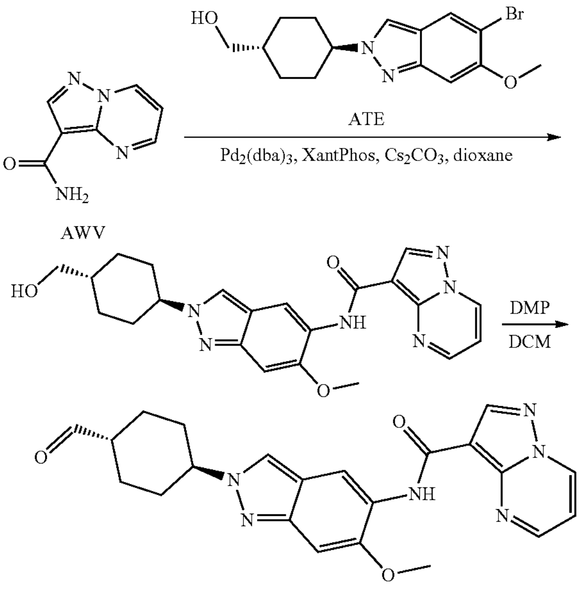

BAT

Step 1—N-[2-[4-(hydroxymethyl)cyclohexyl]-6-methoxy-indazol-5-yl]pyrazolo[1,5-a]pyrimidine-3-carboxamide A mixture of [4-(5-bromo-6-methoxy-indazol-2-yl)cyclohexyl]methanol (2.00 g, 5.90 mmol, synthesized via Steps 1-3 of Intermediate ATE), pyrazolo[1,5-a]pyrimidine-3-carboxamide (1.91 g, 11.8 mmol, Intermediate AWV), $Pd(dba)_2$ (339 mg, 590 umol), Xantphos (682 mg, 1.18 mmol) and $Cs_2CO_3$ (3.84 g, 11.8 mmol) in dioxane (20 mL) was stirred at 110° C. for 20 hr under $N_2$ atmosphere. On completion, the reaction mixture was filtered and concentrated in vacuo to give a residue. The crude product was purified by reverse phase flash (0.1% FA). The residue was purified by prep-TLC (EA:MeOH=10:1) to give the title compound (200 mg, 5% yield) as orange solid. LC-MS ($ESI^+$) m/z 421.0 $(M+H)^+$.

Step 2—N-[2-(4-formylcyclohexyl)-6-methoxy-indazol-5-yl]pyrazolo[1,5-a]pyrimidine-3- carboxamide To a solution of N-[2-[4-(hydroxymethyl)cyclohexyl]-6-methoxy-indazol-5-yl]pyrazolo[1,5-a] pyrimidine-3-carboxamide (200 mg, 476 umol) in DCM (4.0 mL) was added DMP (202 mg, 476 umol). The mixture was stirred at 0° C. for 30 min. Then the reaction mixture was stirred at 25° C. for 1.5 h. On completion, the reaction mixture was quenched with $Na_2S_2O_3$ and extracted with DCM (3×10 mL). The combined organic layer was washed with $NaHCO_3$, brine, dried with anhydrous $Na_2SO_4$, filtered and concentrated in vacuo to give the title compound (140 mg, 100% yield) as orange solid. LC-MS ($ESI^+$) m/z 419.2 $(M+H)^+$.

[4-[5-Bromo-6-(trifluoromethoxy)indazol-2-yl]cyclohexyl]methanol (Intermediate BAZ)

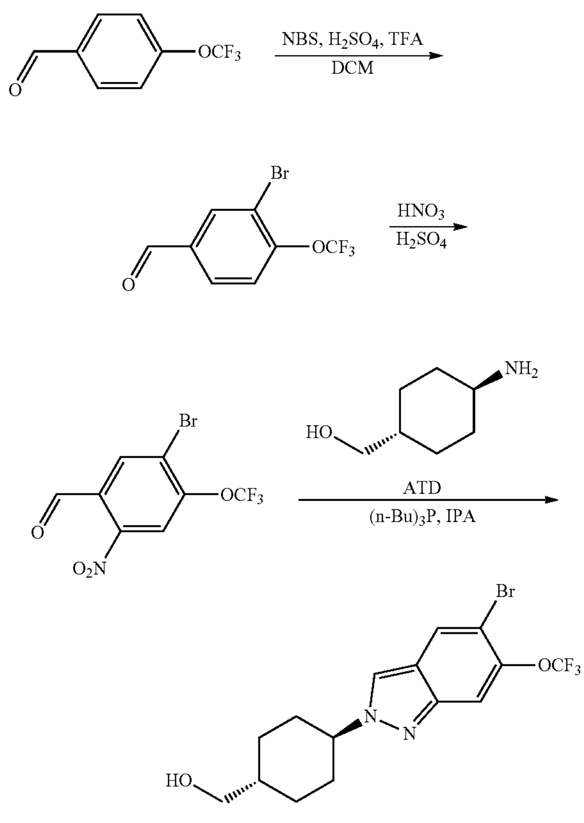

BAZ

Step 1—3-Bromo-4-(trifluoromethoxy)benzaldehyde

To a solution of 4-(trifluoromethoxy)benzaldehyde (20.4 g, 107 mmol, CAS #659-28-9) in a mixture of TFA (20 mL), DCM (20 mL) and $H_2SO_4$ (10 mL) was added NBS (38.2 g, 214 mmol) in portions over 1 hour at 25° C. The reaction mixture was stirred at 25° C. for 16 hours. Then NBS (19.1 g, 107 mmol) was added to the reaction mixture. The reaction mixture was stirred at 25° C. for 3 hours. On completion, the mixture was poured into ice water (500 mL) and extracted with DCM (2×200 mL). The organic layer was washed with saturated $NaHCO_3$ aqueous (2×100 mL), saturated $Na_2S_2O_3$ aqueous (2×100 mL) and brine (2×100 mL). The organic layer was dried over anhydrous sodium sulfate and filtered. The filtrated was concentrated in vacuo. The crude product was distilled in vacuum (60° C., 1 mm/Hg) to give the title compound (18.8 g, 65% yield, 62% starting material remained) as yellow liquid. $^1H$ NMR (400 MHz, $CDCl_3$) δ 9.97 (s, 1H), 8.18 (d, J=2.0 Hz, 1H), 7.89 (dd, J=2.0, 8.4 Hz, 1H), 7.48 (dd, J=1.6, 8.4 Hz, 1H).

Step 2—5-Bromo-2-nitro-4-(trifluoromethoxy)benzaldehyde

To a mixture of [3-bromo-4-(trifluoromethoxy)benzaldehyde (18.8 g, 69.8 mmol, 38% solution) and 4-(trifluoromethoxy)benzaldehyde] in $H_2SO_4$ (150 mL) was added $HNO_3$ (13.1 g, 139 mmol, 67% solution) at 0° C. The reaction mixture was stirred at 20° C. for 17 hours under nitrogen atmosphere. On completion, the mixture was poured into ice water (500 mL) and extracted with EA (2×200 mL). The organic layer was washed with saturated $NaHCO_3$ aqueous (2×200 mL) and brine (2×200 mL). The organic layer was dried over anhydrous sodium sulfate and filtered. The filtrated was concentrated in vacuo. The residue was purified by silica gel chromatography (PE:EA=100:1) to give the title compound (4.34 g, 19% yield) as yellow liquid. $^1H$ NMR (400 MHz, $CDCl_3$) δ 10.42 (s, 1H), 8.27 (s, 1H), 8.08 (d, J=1.2 Hz, 1H).

Step 3—[4-[5-Bromo-6-(trifluoromethoxy)indazol-2-yl]cyclohexyl]methanol

A mixture of 5-bromo-2-nitro-4-(trifluoromethoxy)benzaldehyde (4.34 g, 13.8 mmol) and (4-aminocyclohexyl) methanol (1.79 g, 13.8 mmol, Intermediate ATD) in IPA (40 mL) was stirred at 80° C. for 2 hrs under nitrogen atmosphere. Then the reaction mixture was cool to 20° C., and tributylphosphane (8.39 g, 41.4 mmol) was added. The reaction mixture was stirred at 80° C. for 2 hrs under nitrogen atmosphere. On completion, the reaction mixture was concentrated in vacuo. The residue was purified by silica gel chromatography (PE:EA=1:1) to give the title compound (10.1 g, 92% yield, 50% purity) as yellow oil. $^1H$ NMR (400 MHz, $CDCl_3$) δ 7.96 (s, 1H), 7.95 (s, 1H), 7.67 (s, 1H), 4.42-4.34 (m, 1H), 3.55 (d, J=6.0 Hz, 2H), 3.30-3.14 (m, 1H), 2.37-2.28 (m, 2H), 2.10-2.03 (m, 2H), 2.02-1.91 (m, 2H), 1.51-1.49 (m, 1H), 1.31-1.20 (m, 2H).

N-[2-(4-formylcyclohexyl)-6-(trifluoromethoxy)indazol-5-yl]-6-(trifluoromethyl)pyridine-2-carboxamide (Intermediate BBA)

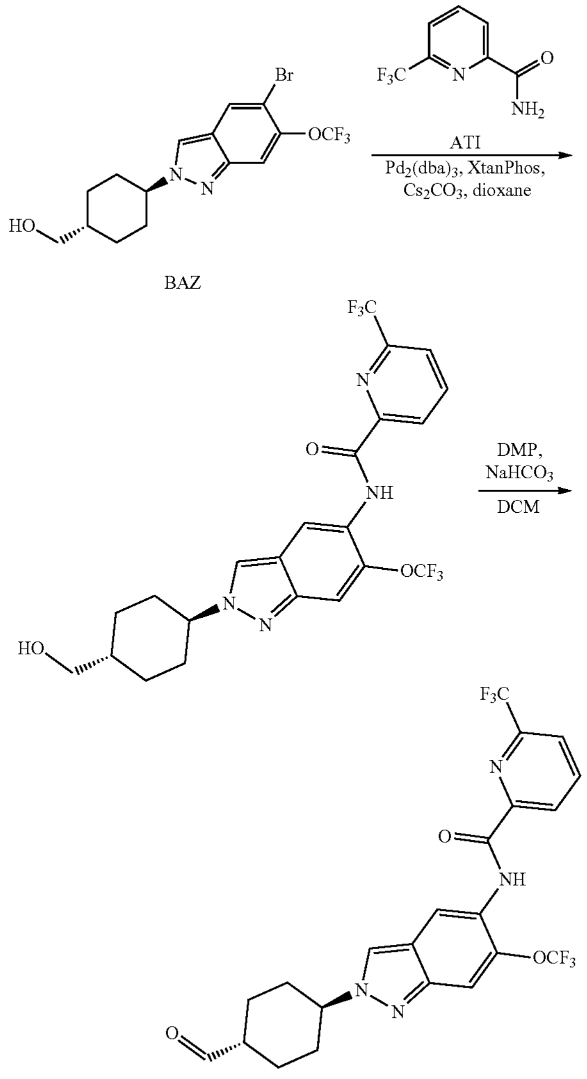

BAZ

BBA

Step 1—N-[2-[4-(hydroxymethyl)cyclohexyl]-6-(trifluoromethoxy)indazol-5-yl]-6- (trifluoromethyl) pyridine-2-carboxamide A mixture of [4-[5-bromo-6-(trifluoromethoxy)indazol-2-yl]cyclohexyl]methanol (5.00 g, 6.36 mmol, 50% purity, Intermediate BAZ), 6-(trifluoromethyl)pyridine-2-carboxamide (1.45 g, 7.63 mmol, Intermediate ATI), $Pd_2(dba)_3$ (582 mg, 635 umol), Xantphos (735 mg, 1.27 mmol) and $Cs_2CO_3$ (4.14 g, 12.7 mmol) in dioxane (50 mL) was stirred at 80° C. for 16 hours under nitrogen atmosphere. On completion, the reaction mixture was filtered and the filter cake was washed with EA (50 mL). The filtrate was concentrated in vacuo. The mixture was diluted with water (200 mL) and extracted with EA (3×100 mL). The organic layer was washed with brine (3×100 mL), dried over anhydrous sodium sulfate and filtered. The filtrate was concentrated in vacuo and the residue was purified by reverse phase flash (0.1% FA condition) to give an impure product. The impure product was triturated with EA (6 mL) at 25° C. for 30 min to give the title compound (1.44 g, 45% yield) as brown solid. $^1$H NMR (400 MHz, DMSO-$d_6$) δ 10.39 (s, 1H), 8.68 (s, 1H), 8.58 (s, 1H), 8.50-8.39 (m, 2H), 8.24 (dd, J=1.2, 7.6 Hz, 1H), 7.80 (s, 1H), 4.51 (t, J=5.2 Hz, 1H), 4.49-4.42 (m, 1H), 3.29 (t, J=5.6 Hz, 2H), 2.21-2.10 (m, 2H), 1.98-1.83 (m, 4H), 1.56-1.41 (m, 1H), 1.26-1.03 (m, 2H).

Step 2—N-[2-(4-formylcyclohexyl)-6-(trifluoromethoxy)indazol-5-yl]-6-(trifluoromethyl)pyridine-2-carboxamide To a mixture of N-[2-[4-(hydroxymethyl)cyclohexyl]-6-(trifluoromethoxy)indazol-5-yl]-6- (trifluoromethyl)pyridine-2-carboxamide (1.34 g, 2.67 mmol) and $NaHCO_3$ (1.12 g, 13.3 mmol) in DCM (50 mL) was added DMP (1.70 g, 4.00 mmol) at 0° C. The reaction mixture was stirred at 20° C. for 3 hrs. On completion, the reaction mixture was diluted with saturated $Na_2S_2O_3$ aqueous (5 mL) and saturated $NaHCO_3$ aqueous (5 mL). The mixture was stirred at 20° C. for 0.5 hr. The mixture was diluted with water (100 mL) and extracted with DCM (3×50 mL). The organic layer was washed with saturated $NaHCO_3$ aqueous (3×50 mL) and brine (3×50 mL). The organic layer was dried over anhydrous sodium sulfate and filtered, and the filtrate was concentrated in vacuo to give an impure product. The impure product was purified by reverse phase flash (0.1% FA condition) to give the title compound (960 mg, 71% yield) as yellow solid. $^1$H NMR (400 MHz, DMSO-$d_6$) δ 10.38 (s, 1H), 9.65 (s, 1H), 8.71-8.66 (m, 1H), 8.58 (s, 1H), 8.49-8.38 (m, 2H), 8.23 (d, J=7.6 Hz, 1H), 7.79 (s, 1H), 4.56-4.48 (m, 1H), 2.47-2.39 (m, 1H), 2.22-2.20 (m, 2H), 2.13-2.10 (m, 2H), 2.00-19.7 (m, 2H), 1.52-1.39 (m, 2H).

3-(Difluoromethyl)-4-nitro-1H-pyrazole (Intermediate HS)

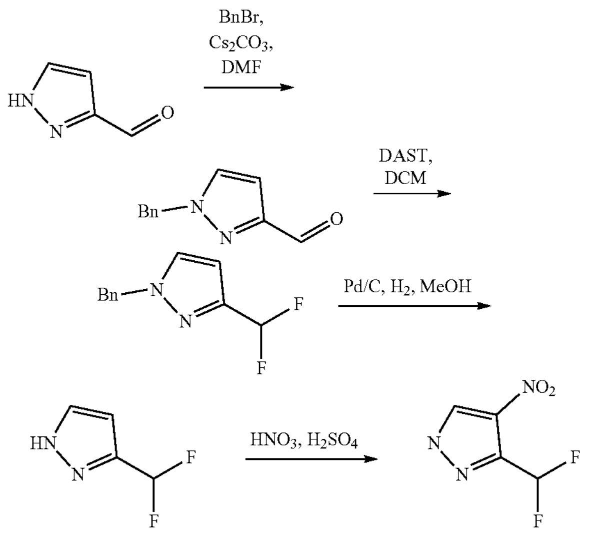

HS

Step 1—1-Benzyl-1H-pyrazole-3-carbaldehyde

To a solution of 1H-pyrazole-3-carbaldehyde (5.00 g, 52.0 mmol, CAS #: 3920-50-1) and BnBr (9.34 g, 54.6 mmol) in DMF (50 mL) was added $Cs_2CO_3$ (42.4 g, 130 mmol). The reaction mixture was stirred at 25° C. for 1 hour. On completion, the reaction mixture was diluted with water, extracted with ethyl acetate (3×100 mL). The combined organic layers was washed with brine (50 mL), dried over anhydrous sodium sulfate, filtered and concentrated in vacuo. The crude product was purified by silica gel chromatography (Petroleum ether:Ethyl acetate=20:1) to give the title compound (8.00 g, 83% yield) as a colorless oil. $^1H$ NMR (400 MHz, $CDCl_3$) δ 10.02 (s, 1H), 7.44 (d, J=2.4 Hz, 1H), 7.43-7.33 (m, 3H), 7.29-7.24 (m, 2H), 6.85 (d, J=2.4 Hz, 1H), 5.42 (s, 2H).

Step 2—1-Benzyl-3-(difluoromethyl)-1H-pyrazole

To a solution of 1-benzylpyrazole-3-carbaldehyde (5.00 g, 26.9 mmol) in DCM (30 mL) was added DAST (17.3 g, 107 mmol) at 0° C. The reaction mixture was stirred at 25° C. for 5 hours. On completion, the reaction mixture was quenched with methanol (30 mL) at 0° C. After, the mixture was concentrated in vacuo. The crude product was purified by silica gel chromatography (petroleum ether:ethyl acetate=20:1) to give the title compound (3.30 g, 59% yield) as a white solid. $^1H$ NMR (400 MHz, $CDCl_3$) δ 7.43-7.36 (m, 3H), 7.27-7.21 (m, 2H), 6.91-6.57 (m, 1H), 6.55-6.51 (m, 1H), 5.35 (s, 2H); LC-MS ($ESI^+$) m/z 209.1 $(M+H)^+$.

Step 3—3-(Difluoromethyl)-1H-pyrazole

To a solution of 1-benzyl-3-(difluoromethyl)pyrazole (1.00 g, 4.80 mmol) in methanol (20 mL) was added $Pd(OH)_2/C$ (0.1 g, 10% purity) under $N_2$ atmosphere. The suspension was degassed and purged with $H_2$ for 3 times. The mixture was stirred at 40° C. for 12 hrs under $H_2$ (50 Psi). On completion, the reaction mixture was filtered and concentrated in vacuo to give the title compound (470 mg, 83% yield) as colorless oil. $^1H$ NMR (400 MHz, DMSO-$d_6$) δ 13.16 (s, 1H), 7.85 (s, 1H), 7.14-6.82 (m, 1H), 6.52 (s, 1H).

Step 4—3-(Difluoromethyl)-4-nitro-1H-pyrazole

To a solution of 3-(difluoromethyl)-1H-pyrazole (470 mg, 3.98 mmol) in $H_2SO_4$ (5 mL) was carefully added a 65% solution of $HNO_3$ (965 mg, 9.95 mmol) dropwise at 0° C. After stirring for 10 minutes, the reaction mixture was heated to 115° C., and stirred for 12 hrs. On completion, the reaction mixture was cooled to 25° C. Then, the reaction mixture was poured onto the (100 mL) ice, extracted with ethyl acetate (3×50 mL). The combined organic layers was washed with brine (2×50 mL), dried over with anhydrous sodium sulfate, filtered and concentrated in vacuo to give the title compound (530 mg, 82% yield). $^1H$ NMR (400 MHz, DMSO-$d_6$) δ 14.41 (s, 1H), 9.04 (s, 1H), 7.50-7.17 (m, 1H), 7.50-7.17 (m, 1H).

Methyl 4-[4-amino-3-(difluoromethyl)pyrazol-1-yl] cyclohexanecarboxylate (Intermediate OS)

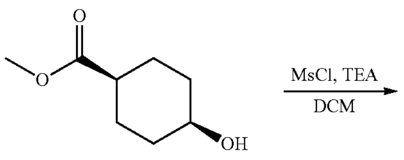

-continued

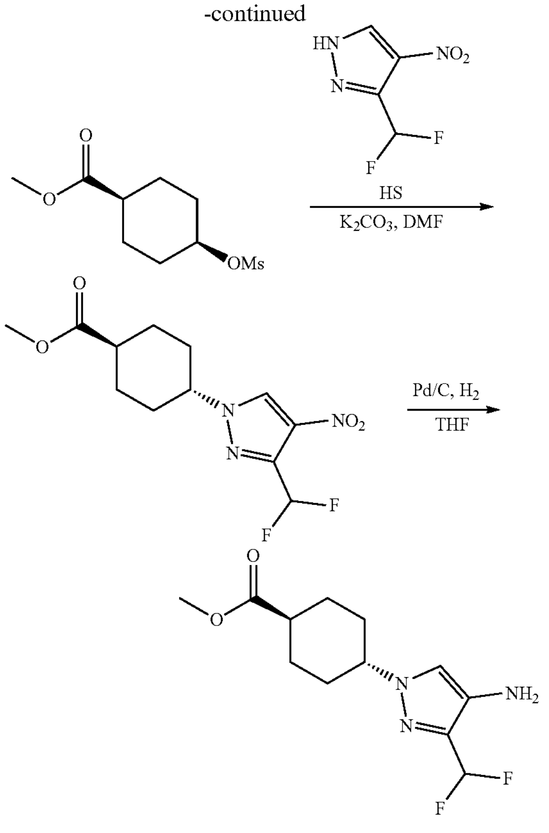

QS

Step 1—Methyl 4-methylsulfonyloxycyclohexanecarboxylate

To a mixture of methyl 4-hydroxycyclohexanecarboxylate (1.00 g, 6.32 mmol, CAS #3618-03-9) in DCM (10 mL) was added TEA (831 mg, 8.22 mmol) and MsCl (1.09 g, 9.48 mmol) at 0° C., the reaction mixture was stirred 0° C. for 2 hours. On completion, the mixture was poured into the ice-water (50 mL) and extracted with DCM (2×30 mL). The combined organic phase was washed with brine (2×50 mL), dried with anhydrous $Na_2SO_4$, filtered and concentrated in vacuo to give the title compound (1.20 g, 80% yield) as colorless oil. $^1H$ NMR (400 MHz, $CDCl_3$) δ 4.91 (t, J=2.8, 5.2 Hz, 1H), 3.69 (s, 3H), 3.02 (s, 3H), 2.41-2.39 (m, 1H), 2.09-1.99 (m, 2H), 1.97-1.86 (m, 2H), 1.80 (t, J=4.4, 9.2 Hz, 2H), 1.75-1.66 (m, 2H).

Step 2—Methyl 4-[3-(difluoromethyl)-4-nitro-pyrazol-1-yl]cyclohexanecarboxylate

To a mixture of 3-(difluoromethyl)-4-nitro-1H-pyrazole (555 mg, 3.40 mmol, Intermediate HS) and methyl 4-methyl sulfonyloxycyclohexanecarboxylate (1.20 g, 5.08 mmol) in DMF (30 mL) was added $K_2CO_3$ (2.11 g, 15.2 mmol). The reaction mixture was stirred at 80° C. for 12 hours. On completion, the mixture was poured into water (50 mL). The aqueous phase was extracted with ethyl acetate (2×30 mL). The combined organic phase was washed with brine (2×40 mL), dried with anhydrous $Na_2SO_4$, filtered and concentrated in vacuo. The residue was purified by column chromatography to give the title compound (480 mg, 25% yield) as brown oil. $^1H$ NMR (400 MHz, $CDCl_3$) δ 8.23 (s, 1H), 7.25-6.96 (m, 1H), 4.26-4.14 (m, 1H), 3.76-3.65 (m, 3H), 2.40 (t, J=3.6, 12.4 Hz, 1H), 2.36-2.17 (m, 4H), 1.83 (d, J=3.6, 12.8 Hz, 2H), 1.69-1.59 (m, 2H).

Step 3—Methyl 4-[4-amino-3-(difluoromethyl)pyrazol-1-yl]cyclohexanecarboxylate

To a mixture of methyl 4-[3-(difluoromethyl)-4-nitro-pyrazol-1-yl]cyclohexanecarboxylate (430 mg, 1.42 mmol) in THE (20 mL) was added Pd/C (100 mg, 10 wt %) under $N_2$. The suspension was degassed under vacuum and purged with $H_2$ gas three times. The mixture was stirred under $H_2$ (15 psi) at 25° C. for 12 hours. On completion, the mixture was filtered and the filtrate was concentrated in vacuo to give the title compound (350 mg, 90% yield) a brown solid. LC-MS (ESI+) m/z 274.1 (M+H)+.

[4-[4-Amino-3-(difluoromethyl)pyrazol-1-yl]cyclohexyl]methanol (Intermediate TD)

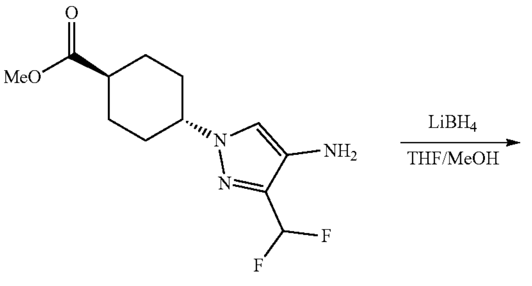

QS

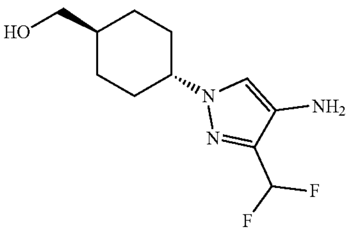

TD

To a mixture of methyl 4-[4-amino-3-(difluoromethyl) pyrazol-1-yl]cyclohexanecarboxylate (1.20 g, 4.39 mmol, Intermediate QS) in THE (80 mL) and MeOH (10 mL) was added $LiBH_4$ (191 mg, 8.78 mmol) at 0° C., then the mixture was stirred at 60° C. for 1 hour. On completion, the reaction mixture was poured into water (120 mL), and the aqueous phase was extracted with ethyl acetate (2×50 mL). The combined organic phase was washed with brine (2×40 mL), dried with anhydrous $Na_2SO_4$, filtered and concentrated in vacuo to give title compound (860 mg, 79% yield) as a brown solid. $^1$H NMR (400 MHz, $CDCl_3$-d) δ 7.02 (s, 1H), 6.82-6.53 (m, 1H), 3.94 (tt, J=4.0, 12.0 Hz, 1H), 3.50 (d, J=6.4 Hz, 2H), 2.21-2.12 (m, 3H), 2.01-1.92 (m, 3H), 1.69 (d, J=3.6, 12.4 Hz, 2H), 1.56 (tt, J=3.0, 6.4, 12.0 Hz, 2H), 1.20-1.08 (m, 2H). Absolute stereochemistry randomly assigned, compound is the trans isomer.

(R)-Tert-butyl 4-((4-aminobutan-2-yl)oxy)piperidine-1-carboxylate (Intermediate BBB)

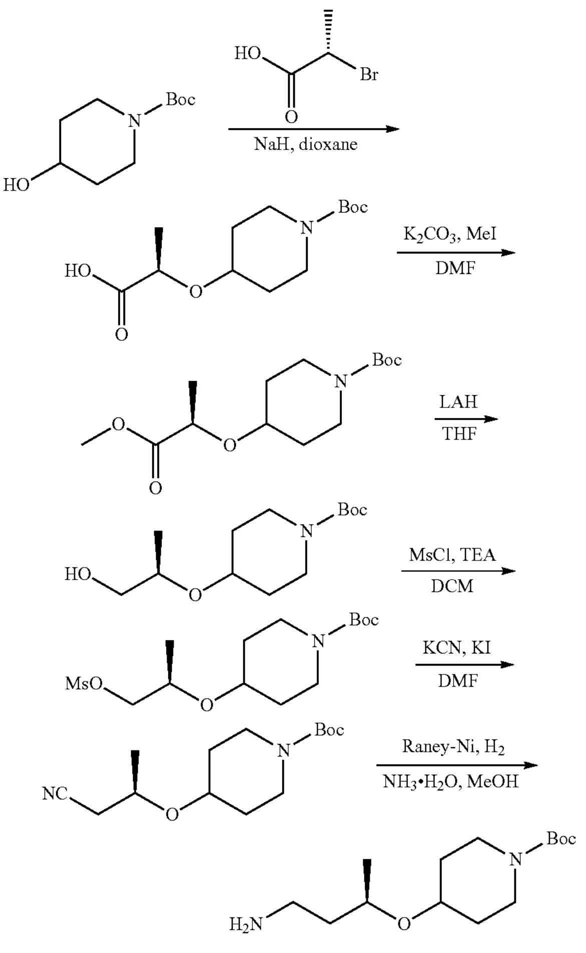

BBB

Step 1—(R)-2-((1-(Tert-butoxycarbonyl)piperidin-4-yl)oxy)propanoic acid

To a solution of NaH (26.2 g, 654 mmol) in dioxane (250 mL) was added tert-butyl 4-hydroxypiperidine-1-carboxylate (28.9 g, 144 mmol, CAS #109384-19-2) at 0° C., and the mixture was stirred at 0° C. for 0.5 hour. Then (2S)-2-bromopropanoic acid (20 g, 131 mmol, CAS #32644-15-8) was added, and the mixture was stirred at 25° C. for 16 hours. On completion, the mixture was quenched with water (1.5 L) and then extracted with EA (800 mL). The aqueous layer was acidified to pH=2, and then extracted with EA (2×500 mL). The combined organic layers were dried over $Na_2SO_4$, filtered and concentrated in vacuo to give a residue. The residue was left standing overnight where a solid precipitated from the solution. The solid was collected by filtering and washed with PE/MeOH (5/1, 20 mL) to give the title compound (21 g, 28% yield) as a yellow solid. $^1$H NMR (400 MHz, DMSO-$d_6$) δ 12.54 (s, 1H), 4.07 (m, 1H), 3.65 (m, 2H), 3.50 (s, 1H), 3.33 (s, 2H), 2.99 (s, 2H), 1.85 (m, 2H), 1.38 (s, 9H), 1.24 (m, 3H).

Step 2—(R)-Tert-butyl 4-((1-methoxy-1-oxopropan-2-yl)oxy)piperidine-1-carboxylate To a solution of (2R)-2-[(1-tert-butoxycarbonyl-4-piperidyl)oxy]propanoic acid (21.0 g, 76.8 mmol) in DMF (25.0 mL) was added $K_2CO_3$ (21.2 g, 154 mmol) and MeI (54.5 g, 384 mmol), and the mixture was stirred at 20° C. for 14 hours. On completion, the mixture was concentrated in vacuo to give a residue. The residue was then diluted with water (1.0 L), extracted with EA (3×200 mL), the combined organic phase was dried over $Na_2SO_4$, filtered and concentrated in vacuo to give the title product (21 g, 95% yield) as a yellow oil. $^1$H NMR (400 MHz, $CDC_3$) δ 4.13 (m, 1H), 3.74-3.52 (m, 5H), 3.50 (m, 1H), 3.10-3.03 (m, 2H), 1.82-1.80 (m, 2H), 1.58 (m, 2H), 1.49-1.45 (m, 9H), 1.44-1.38 (m, 3H).

Step 3—(R)-tert-butyl 4-((1-hydroxypropan-2-yl)oxy)piperidine-1-carboxylate

To a solution of $LiAlH_4$ (4.16 g, 110 mmol) in THF (100 mL) was dropwise added a solution of tert-butyl 4-[(1R)-2-methoxy-1-methyl-2-oxo-ethoxy]piperidine-1-carboxylate (21 g, 73.1 mmol) in THF (110 mL) at 0° C., and the reaction mixture was stirred at 0° C. for 1 hour. On completion, the mixture was quenched with NaOH (1N, 4.20 mL), and saturated aq. $Na_2SO_4$ (50 mL). After that, 200 mL of EA was added and the mixture was stirred at 25° C. for 0.15 hour. Then, the mixture was separated and the organic phase was collected, dried over $Na_2SO_4$ and concentrated in vacuo to give the title product (15.5 g, 82% yield) as yellow oil. $^1$H NMR (400 MHz, $CDCl_3$) δ 3.81-3.42 (m, 7H), 3.05-3.02 (m, 2H), 2.11 (m, 1H), 1.75 (s, 1H), 1.65 (m, 2H), 1.45 (s, 9H), 1.12-1.09 (m, 3H).

Step 4—(R)-Tert-butyl 4-((1-((methylsulfonyl)oxy)propan-2-yl)oxy)piperidine-1-carboxylate To a solution of tert-butyl 4-[(1R)-2-hydroxy-1-methyl-ethoxy]piperidine-1-carboxylate (3.0 g, 10.4 mmol) in DCM (30 mL) was added TEA (2.63 g, 26.0 mmol) and MsCl (1.79 g, 15.6 mmol) at 0° C., and the mixture was stirred at 0° C. for 1 hour. On completion, the mixture was diluted with brine (100 mL) and extracted with DCM (2×50 mL). The combined organic layers were collected, dried over $Na_2SO_4$, filtered and concentrated in vacuo to give the title product (3.51 g, 100% yield) as a yellow oil.

Step 5—(R)-Tert-butyl 4-((1-cyanopropan-2-yl)oxy)piperidine-1-carboxylate

To a solution of tert-butyl 4-[(1R)-1-methyl-2-methylsulfonyloxy-ethoxy]piperidine-1-carboxylate (3.51 g, 10.4 mmol) in DMF (30 mL) was added KI (3.45 g, 20.8 mmol) and KCN (1.02 g, 15.6 mmol) at 25° C. The mixture was stirred at 60° C. for 14 hours. On completion, the mixture was quenched with brine (100 mL), and extracted with EA (2×50 mL). The combined organic layers were collected, dried over $Na_2SO_4$, filtered and concentrated in vacuo to give a residue. The residue was purified by silica gel chromatography (PE/EA=10/1) to give the title product (1.0 g, 32% yield) as a yellow oil. $^1$H NMR (400 MHz, $CDCl_3$) δ 3.87 (m, 1H), 3.74-3.72 (m, 2H), 3.60 (m, 1H), 3.18-3.12 (m, 2H), 2.49-2.47 (m, 2H), 1.79-1.78 (m, 2H), 1.56-1.53 (m, 2H), 1.45 (s, 9H), 1.30-1.28 (m, 3H).

Step 6—(R)-Tert-butyl 4-((4-aminobutan-2-yl)oxy)piperidine-1-carboxylate

To a solution of tert-butyl 4-[(1R)-2-cyano-1-methyl-ethoxy]piperidine-1-carboxylate (500 mg, 1.68 mmol) in MeOH (10 mL) and $NH_3.H_2O$ (1.0 mL) was added Raney-Ni (143 mg, 1.68 mmol). The mixture was stirred under $H_2$ (40 psi) at 25° C. for 2 hours. On completion, the reaction mixture was filtered and the filtrate was concentrated in vacuo to give the title product (400 mg, 80% yield) as a yellow oil. $^1$H NMR (400 MHz, $CDCl_3$) δ 3.78-3.77 (m, 4H), 3.53-3.50 (m, 2H), 3.03-3.02 (m, 4H), 1.81-1.60 (m, 6H), 1.45 (s, 9H), 1.18 (s, 3H).

2-(2,6-Dioxopiperidin-3-yl)-4-(((R)-3-(piperidin-4-yloxy)butyl)amino)isoindoline-1,3-dione (Intermediate BBC)

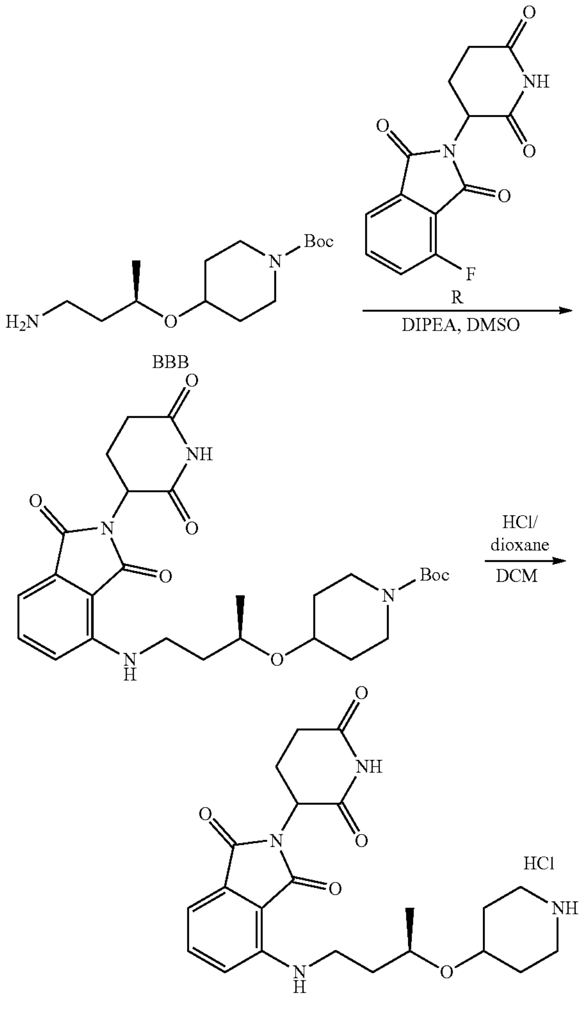

BBB

BBC

Step 1—Tert-butyl 4-(((2R)-4-((2-(2,6-dioxopiperidin-3-yl)-1,3-dioxoisoindolin-4-yl)amino)butan-2-yl)oxy)piperidine-1-carboxylate To a solution of 2-(2,6-dioxo-3-piperidyl)-4-fluoro-isoindoline-1,3-dione (400 mg, 1.45 mmol, Intermediate R) in DMSO (5.0 mL) was added DIPEA (374 mg, 2.90 mmol) and tert-butyl 4-[(1R)-3-amino-1-methyl-propoxy]piperidine-1-carboxylate (394 mg, 1.45 mmol, Intermediate BBB), and the mixture was stirred at 130° C. for 1 hour. On completion, the reaction was concentrated in vacuo to give a residue. The residue was purified by reverse phase (0.1% FA condition) to give the title product (380 mg, 49% yield) as a yellow solid. LC-MS (ESI$^+$) m/z 429.2 (M-100+H)$^+$.

Step 2—2-(2,6-Dioxopiperidin-3-yl)-4-(((R)-3-(piperidin-4-yloxy)butyl)amino)isoindoline-1,3-dione To a solution of tert-butyl 4-[(1R)-3-[[2- (2,6-dioxo-3-piperidyl)-1,3-dioxo-isoindolin-4-yl]amino]-1- methyl-propoxy] piperidine-1-carboxylate (380 mg, 718 umol) in DCM (2.0 mL) was added HCl/dioxane (1.0 mL) at 25° C. The mixture was stirred at 25° C. for 1 hour. On completion, the mixture was concentrated in vacuo to give the title product (340 mg, 71% yield, HCl salt) as a yellow solid. LC-MS (ESI$^+$) m/z 429.2 (M+H)$^+$.

3-(4-(7-Azaspiro[3.5]nonan-2-ylamino)-3-methyl-2-oxo-2,3-dihydro-1H-benzo[d]imidazol -1-yl)piperidine-2,6-dione (Intermediate BBD)

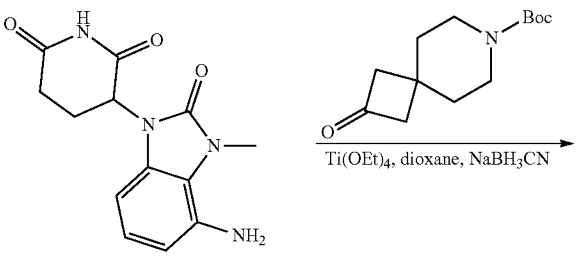

BAP

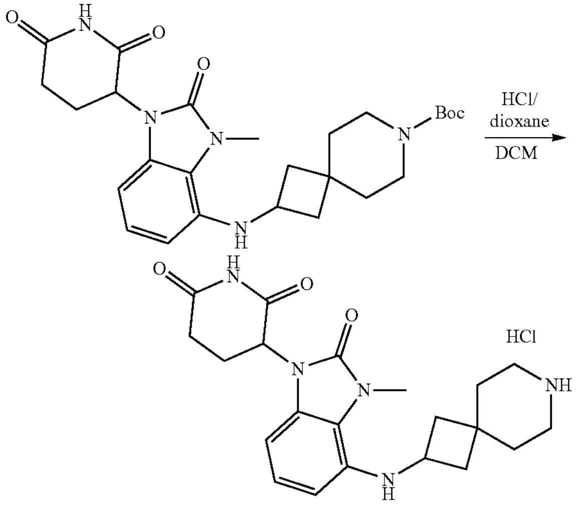

BBD

Step 1—Tert-butyl 2-[[1-(2,6-dioxo-3-piperidyl)-3-methyl-2-oxo-benzimidazol-4-yl]amino]-7- azaspiro [3.5]nonane-7-carboxylate To a mixture of 3-(4-amino-3-methyl-2-oxo-benzimidazol-1-yl)piperidine-2,6-dione (200 mg, 729 umol, Intermediate BAP) and tert-butyl 2-oxo-7-azaspiro[3.5]nonane-7-carboxylate (174 mg, 729 umol, CAS #203661-69-2) in dioxane (2 mL) was and tetraethoxytitanium (499 mg, 2.19 mmol). The reaction mixture stirred at 80° C. for 17 hrs. Then the mixture was cooled to 25° C. Then $NaBH_3CN$ (137 mg, 2.19 mmol) was added to the reaction mixture and the mixture was stirred at 25° C. for 3 hrs. On completion, the reaction mixture was filtered and the filtrate was concentrated in vacuo. The crude product was purified by reverse phase flash (0.1% FA condition) to give the title compound (100 mg, 27% yield) as white solid. $^1H$ NMR (400 MHz, DMSO-$d_6$) δ 11.07 (s, 1H), 6.85 (dd, J=7.6, 8.0 Hz, 1H), 6.53 (d, J=7.6 Hz, 1H), 6.30 (d, J=8.0 Hz, 1H), 5.29 (dd, J=5.2, 12.8 Hz, 1H), 5.21 (d, J=6.8 Hz, 1H), 3.91-3.75 (m, 1H), 3.62 (s, 3H), 3.31-3.26 (m, 2H), 3.22 (s, 2H), 2.93-2.83 (m, 1H), 2.71-2.59 (m, 2H), 2.32-2.28 (m, 2H), 2.02-1.93 (m, 1H), 1.73-1.66 (m, 2H), 1.56-1.54 (m, 2H), 1.51-1.48 (m, 2H), 1.40 (s, 9H); LC-MS (ESI$^+$) m/z 498.3 (M+H)$^+$.

Step 2—3-(4-(7-Azaspiro[3.5]nonan-2-ylamino)-3-methyl-2-oxo-2,3-dihydro-1H-benzo[d]imidazol -1-yl)piperidine-2,6-dione A solution of tert-butyl 2-[[1-(2,6-dioxo-3-piperidyl)-3-methyl-2-oxo-benzimidazol-4-yl]amino]-7- azaspiro[3.5] nonane-7-carboxylate (40.0 mg, 80.4 umol) and HCl/dioxane (4 M, 1 mL) in DCM (1 mL) was stirred at 25° C. for 1 hour. On completion, the reaction mixture was concentrated in vacuo to give the title compound (32.0 mg, 92% yield) as brown gum. LC-MS (ESI$^+$) m/z 398.2 (M+H)$^+$.

6-(Trifluoromethoxy)pyridine-2-carboxylic acid (Intermediate BBE)

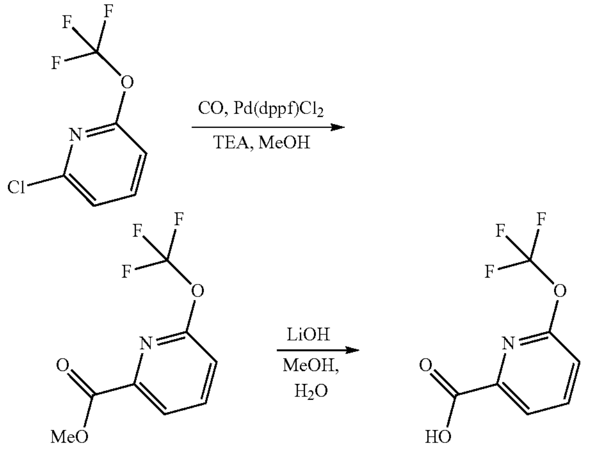

BBE

Step 1—Methyl 6-(trifluoromethoxy)pyridine-2-carboxylate

To a stirring solution of 2-chloro-6-(trifluoromethoxy) pyridine (4.90 g, 24.8 mmol, CAS #1221171-70-5) in MeOH (30 mL) in a steel bomb under inert atmosphere were added $Pd(dppf)Cl_2$ (1.81 g, 2.48 mmol) and TEA (25.1 g, 248.05 mmol) and the mixture was heated to 80° C. under CO gas atmosphere (50 psi) and stirred for 12 hrs. On completion, the reaction mixture was added filtered and concentrated in vacuo. The residue was purified by silica gel chromatography ($SiO_2$) to give the title compound (4.50 g, 82% yield) as a colorless oil. $^1$H NMR (400 MHz, $CDCl_3$) δ=8.08 (d, J=8.0 Hz, 1H), 7.96 (t, J=8.0 Hz, 1H), 7.26 (d, J=8.0 Hz, 1H), 4.00 (s, 3H).

Step 2—6-(Trifluoromethoxy)pyridine-2-carboxylic acid

To a solution of methyl 6-(trifluoromethoxy) pyridine-2-carboxylate (1.50 g, 6.78 mmol) in a mixed solvent of MeOH (20 mL) and $H_2O$ (20 mL) was added LiOH (487 mg, 20.4 mmol). The reaction mixture was stirred at 20° C. for 12 hrs. On completion, the mixture was acidified with 1 N HCl to pH=3-4, then extracted with EA (2×50 mL). The organic layer was washed with brine (20 mL), dried with $Na_2SO_4$, filtered and the filtrate was concentrated in vacuo to give the title compound (1.06 g, 75% yield) as white solid. $^1$H NMR (400 MHz, DMSO-$d_6$) δ 8.22-8.12 (m, 1H), 8.03 (d, J=7.6 Hz, 1H), 7.49 (d, J=8.0 Hz, 1H).

N-[2-(4-formylcyclohexyl)-6-(1-hydroxy-1-methyl-ethyl)indazol-5-yl]-6-(trifluoromethoxy)pyridine-2-carboxamide (Intermediate BBF)

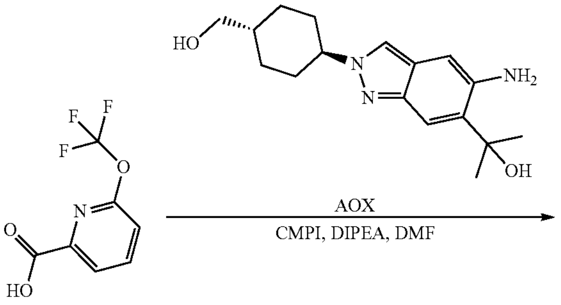

BBE

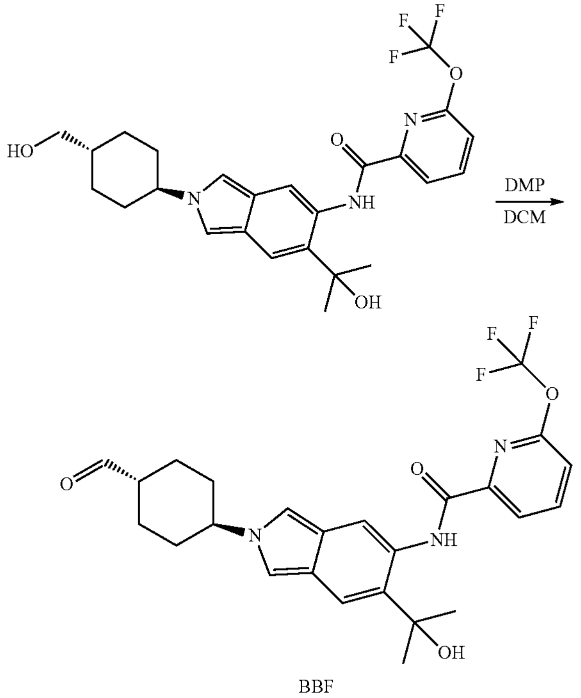

BBF

Step 1—N-[2-[4-(hydroxymethyl)cyclohexyl]-6-(1-hydroxy-1-methyl-ethyl)indazol-5-yl]-6- (trifluoromethoxy)pyridine-2- carboxamide To a solution of 6-(trifluoromethoxy) pyridine-2-carboxylic acid (400 mg, 1.93 mmol, Intermediate BBE), 2-[5-amino-2-[4-(hydroxymethyl)cyclohexyl]indazol-6-yl]propan-2-ol (557 mg, 1.83 mmol, Intermediate AOX) in DMF (15 mL) was added CMPI (543 mg, 2.12 mmol) and DIPEA (749 mg, 5.79 mmol). The mixture was stirred at 20° C. for 1 hr. On completion, the reaction mixture was quenched by addition $H_2O$ (70 mL), then extracted with EA (3×50 mL). The combined organic layers were washed with brine (2×40 mL), dried with $Na_2SO_4$, filtered and the filtrate was concentrated in vacuo to give the title compound (345 mg, 36% yield) as a white solid. $^1$H NMR (400 MHz, DMSO-$d_6$) δ 12.04 (s, 1H), 8.68 (s, 1H), 8.36 (s, 1H), 8.30-8.25 (m, 1H), 8.22-8.18 (m, 1H), 7.57-7.54 (m, 2H), 5.85 (s, 1H), 4.49 (t, J=5.2 Hz, 1H), 4.45-4.37 (m, 1H), 3.29 (t, J=5.6 Hz, 2H), 2.14 (d, J=8.8 Hz, 2H), 1.90 (d, J=10.8 Hz, 4H), 1.60 (s, 6H), 1.52-1.45 (m, 1H), 1.22-1.14 (m, 2H); LC-MS (ESI$^+$) m/z 493.4 (M+H)$^+$.

Step 2—N-[2-(4-formylcyclohexyl)-6-(1-hydroxy-1-methyl-ethyl)indazol-5-yl]-6-(trifluoromethoxy) pyridine-2-carboxamide To a solution of N-[2-[4-(hydroxymethyl)cyclohexyl]-6-(1-hydroxy-1-methyl-ethyl)indazol-5-yl]-6-(trifluoromethoxy)pyridine-2-carboxamide (150 mg, 305 umol) in DCM (2 mL) was added DMP (220 mg, 518 umol). The reaction mixture was stirred at 20° C. for 2 hrs. On completion, the mixture was quenched with $Na_2S_2O_3$ (15 mL) and $NaHCO_3$ (15 mL), then extracted with DCM (3×5 mL). The organic layer was washed with brine (3×5 mL), dried with $Na_2SO_4$, filtered and the filtrate was concentrated in vacuo to give a title compound (140 mg, 94% yield) as a white solid. LC-MS (ESI$^+$) m/z 491.4 (M+H)$^+$.

((1R,4R)-4-(5-bromo-6-cyclopropoxy-2H-indazol-2-yl)cyclohexyl)methanol (Intermediate BBG)

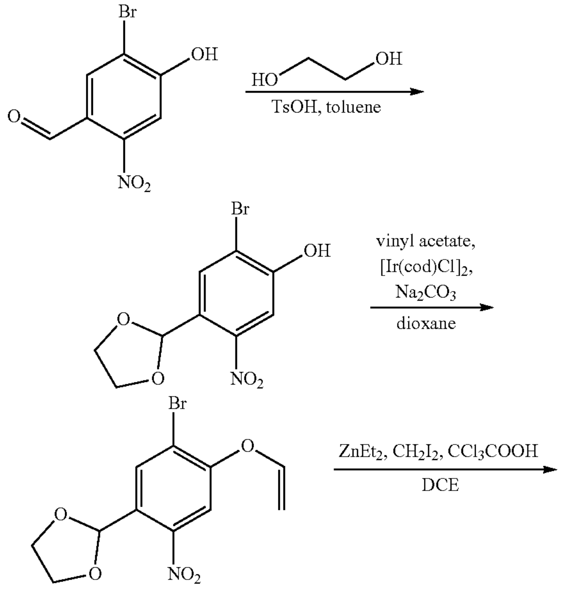

-continued

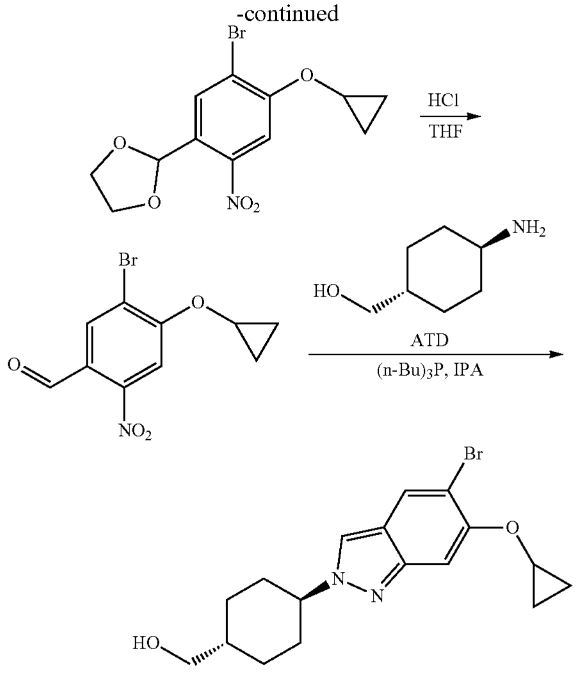

BBG

Step 1—2-Bromo-4-(1,3-dioxolan-2-yl)-5-nitrophenol

To a solution of 5-bromo-4-hydroxy-2-nitro-benzaldehyde (2.50 g, 10.2 mmol, Intermediate AWN) and ethylene glycol (9.46 g, 152 mmol) in toluene (20 mL) was added TsOH (262 mg, 1.52 mmol). The mixture was stirred at 130° C. for 5 hours. On completion, the reaction mixture was diluted with water(50 mL), and extracted with EA (2×50 mL). The organic layers were dried over $Na_2SO_4$, filtered and concentrated in vacuo. The residue was purified by silica gel chromatography(PE/EA=10/1 to 4/1) to give the title compound (2.80 g, 85% yield) as a yellow solid. $^1$H NMR (400 MHz, $CDCl_3$) δ 7.93 (s, 1H), 7.59 (s, 1H), 8.69 (s, 1H), 6.39 (s, 1H), 5.90 (s, 1H), 4.05 (m, 4H).

Step 2—2-(5-Bromo-2-nitro-4-(vinyloxy)phenyl)-1,3-dioxolane

To a solution of 2-bromo-4-(1,3-dioxolan-2-yl)-5-nitrophenol (2.50 g, 7.76 mmol) and vinyl acetate (10.0 g, 116 mmol) in dioxane (15 mL) was added $Na_2CO_3$ (1.64 g, 15.5 mmol) and chloroiridium;(1Z,5Z)-cycloocta-1,5-diene (1.04 g, 1.55 mmol). The mixture was stirred in sealed tube at 100° C. for 2 hours. On completion, the mixture was filtered. The filtrate was concentrated in vacuo. The residue was purified by silica gel chromatography (PE/EA=30/1) to give the title compound (1.00 g, 37% yield) as yellow solid. $^1$H NMR (400 MHz, $CDCl_3$-d) δ 8.04 (s, 1H), 7.59 (s, 1H), 6.64 (m, 1H), 6.44 (s, 1H), 5.01 (m, 1H), 4.76 (m, 1H), 4.07 (m, 4H); LC-MS (ESI$^+$) m/z 316.0, 317.9 (M+H)$^+$.

Step 3—2-(5-Bromo-4-cyclopropoxy-2-nitrophenyl)-1,3-dioxolane

A solution of 2,2,2-trichloroacetic acid (1.03 g, 6.33 mmol) in 1, 2-dichloroethane (5 mL) was added to a cooled solution of $ZnEt_2$ (1 M, 6.33 mL) in 1,2-dichloroethane (2 mL) at −50° C. The solution was warmed to −5° C. and stirred for 20 minutes. Diiodomethane (2.54 g, 9.49 mmol) was added to the reaction mixture dropwise. The mixture was stirred at −5° C. for another 10 minutes. To the mixture was added a solution of 2-(5-bromo-2-nitro-4-vinyloxy-phenyl)-1,3-dioxolane (200 mg, 632 umol) in 1, 2-dichloroethane (5 mL). It was then stirred at 25° C. for 13.5 hours. On completion, the reaction mixture was quenched with sat. aq. $NH_4Cl$ (50 mL), then extracted with EtOAc (3×20 mL). The combined organic layers were dried over $Na_2SO_4$ and concentrated in vacuo. The residue was purified by Prep-TLC (PE/EA=5/1) to give the title compound (150 mg, 72% yield) as yellow solid. $^1$H NMR (400 MHz, $CDCl_3$) δ 7.96 (s, 1H), 7.81 (s, 1H), 6.41 (s, 1H), 4.05 (m, 4H), 3.91 (m, 1H), 0.94 (m, 4H).

Step 4—5-Bromo-4-cyclopropoxy-2-nitrobenzaldehyde

To a solution of 2-[5-bromo-4-(cyclopropoxy)-2-nitro-phenyl]-1,3-dioxolane (150 mg, 409 umol) in THE (2 mL) was added HCl (4 M, 2 mL). The mixture was stirred at 30° C. for 14 hours. On completion, the mixture was extracted with EA (2×2 mL). The organic layers were dried over $Na_2SO_4$, filtered and concentrated in vacuo. The residue was purified by Prep-TLC(PE/EA=5/1) to give the title compound (80.0 mg, 61% yield) as yellow solid. LC-MS (ESI$^+$) m/z 286.0, 288.0 (M+H)$^+$.

Step 5—((1R,4R)-4-(5-bromo-6-cyclopropoxy-2H-indazol-2-yl)cyclohexyl)methanol A mixture of 5-bromo-4-(cyclopropoxy)-2-nitro-benzaldehyde (70.0 mg, 245 umol) and (4-aminocyclohexyl) methanol (35.0 mg, 269 umol, Intermediate ATD) in IPA (1.5 mL) was stirred at 80° C. for 2 hours. After the mixture was cooled to 25° C., tributylphosphane (149 mg, 734 umol) was added. The mixture was stirred at 80° C. for 2 hours. On completion, the mixture was concentrated in vacuo. The residue was purified by Prep-TLC (EA) to give the title compound (160 mg, 100% yield) as yellow oil. $^1$H NMR (400 MHz, $CDCl_3$) δ 7.83 (m, 2H), 7.44 (s, 1H), 4.34 (m, 1H), 3.83 (m, 1H), 3.55 (m, 2H), 2.33 (m, 2H), 2.02 (m, 2H), 1.69 (m, 4H), 1.57 (m, 4H), 0.88 (m, 4H); LC-MS (ESI$^+$) m/z 365.2 (M+H)$^+$.

N-(6-cyclopropoxy-2-((1r,4r)-4-formylcyclohexyl)-2H-indazol-5-yl)-6-(trifluoromethyl)picolinamide (Intermediate BBH)

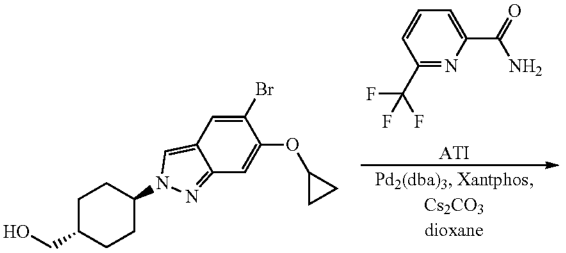

BBG

-continued

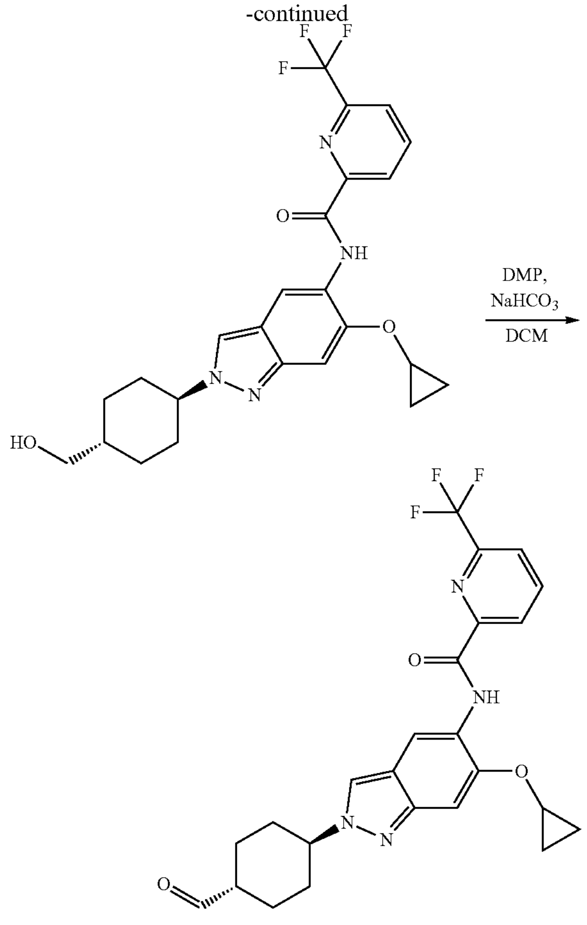

BBH

Step 1—N-(6-cyclopropoxy-2-((1r,4r)-4-(hydroxymethyl)cyclohexyl)-2H-indazol-5-yl)-6- (trifluoromethyl)picolinamide To a solution of [4-[5-bromo-6-(cyclopropoxy)indazol-2-yl]cyclohexyl]methanol (150 mg, 411 umol, Intermediate BBG) and 6-(trifluoromethyl)pyridine-2-carboxamide (117 mg, 616 umol, Intermediate ATI), Xantphos (47.5 mg, 82.1 umol) and $Cs_2CO_3$ (268 mg, 821 umol) in dioxane (2 mL) was added $Pd_2(dba)_3$ (37.6 mg, 41.0 umol). The mixture was stirred at 100° C. for 2 hours under $N_2$. On completion, the mixture was filtered and the filtrate was concentrated in vacuo. The residue was purified by Prep-TLC (EA) to give the title compound (150 mg, 75% yield) as yellow solid. $^1H$ NMR (400 MHz, MeOD) δ 10.72 (s, 1H), 8.97 (s, 1H), 8.72 (s, 1H), 8.48 (d, J=8.0 Hz, 1H), 8.35 (m, 1H), 8.08 (d, J=8.0 Hz, 1H), 7.49 (s, 1H), 4.63 (m, 1H), 4.21 (m, 1H), 3.47 (d, J=6.4 Hz, 2H), 2.36 (m, 2H), 2.10-1.99 (m, 4H), 1.78 (m, 2H), 1.55 (m, 2H), 1.02 (m, 4H). LC-MS (ESI$^+$) m/z 475.3 (M+H)$^+$.

Step 2—N-(6-cyclopropoxy-2-((1r,4r)-4-formylcyclohexyl)-2H-indazol-5-yl)-6-(trifluoromethyl) picolinamide A solution of N-[6-(cyclopropoxy)-2-[4-(hydroxymethyl) cyclohexyl]indazol-5-yl]-6-(trifluoromethyl)pyridine-2-carboxamide (80.0 mg, 164 umol), DMP (90.2 mg, 213 umol) and $NaHCO_3$ (68.7 mg, 818 umol) in DCM (5 mL) was stirred at 25° C. for 1 hour. On completion, the mixture was quenched with sat. aq. $Na_2S_2O_3$ (20 mL), washed with sat. aq. $NaHCO_3$ (20 mL), and extracted with EA (2×20 mL). The organic layers were dried over $Na_2SO_4$, filtered and concentrated in vacuo. The residue was purified by Prep-TLC (PE/EA=1/2) to give the title compound (55.0 mg, 70% yield) as yellow solid.LC-MS (ESI$^+$) m/z 473.2 (M+H)$^+$.

3-[4-(4-Aminocyclohexyl)-3-methyl-2-oxo-benzimidazol-1-yl]piperidine-2,6-dione (Intermediate BBO)

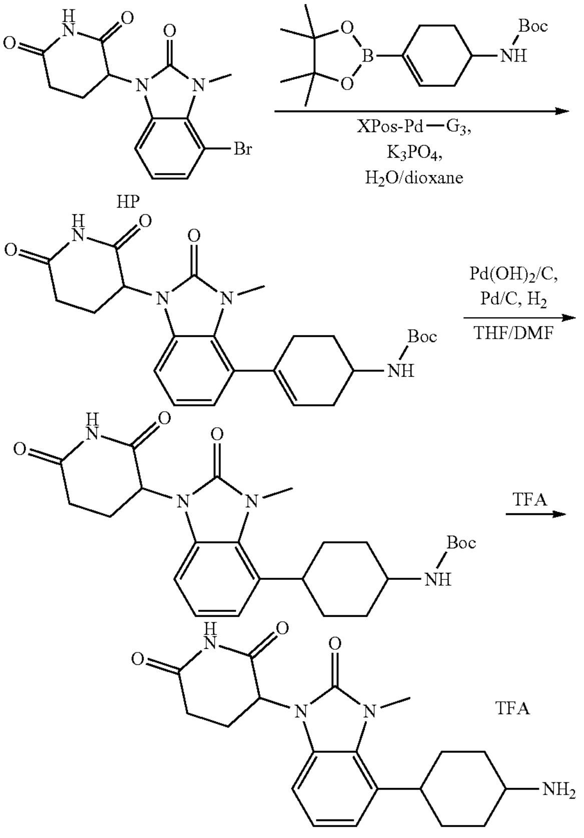

BBO

Step 1—Tert-butylN-[4-[1-(2,6-dioxo-3-piperidyl)-3-methyl-2-oxo-benzimidazol-4-yl]cyclohex-3-en-1-yl]carbamate A mixture of 3-(4-bromo-3-methyl-2-oxo-benzimidazol-1-yl)piperidine-2,6-dione (5.00 g, 14.8 mmol, Intermediate HP), tert-butyl N-[4-(4,4,5,5-tetramethyl-1,3,2-dioxaborolan-2-yl)cyclohex-3-en-1-yl]carbamate (5.26 g, 16.3 mmol, CAS #1251732-64-5), XPhos-Pd-$G_3$ (626 mg, 739 umol) and $K_3PO_4$ (6.28 g, 29.6 mmol) in dioxane (100 mL) and $H_2O$ (0.5 mL) was heated to 80° C. with stirring for 16 hours under $N_2$. On completion, the mixture was filtered and the filtrate was concentrated to give a residue. The residue was purified by prep-HPLC: reverse phase [ACN/(0.1% FA in water), 0% to 50%] to give the title compound (4.00 g, 60% yield) as off-white solid. LC-MS (ESI$^+$) m/z 455.2 (M+H)$^+$.

Step 2—Tert-butylN-[4-[1-(2,6-dioxo-3-piperidyl)-3-methyl-2-oxo-benzimidazol-4-yl]cyclohexyl]carbamate To a solution of tert-butyl N-[4-[1-(2,6-dioxo-3-piperidyl)-3-methyl-2-oxo-benzimidazol-4-yl]cyclohex-3-en-1-yl]carbamate (3.00 g, 6.60 mmol) in THE (500 mL) and DMF (40 mL) was added Pd/C (1.00 g, 6.60 mmol, 10 wt %), $Pd(OH)_2$ (1.50 g, 1.07 mmol, 10 wt %) under $N_2$ atmosphere. The suspension was degassed and purged with $H_2$ for three times. The mixture was stirred under $H_2$ (15 Psi) at 80° C. for 12 hr. On completion, the reaction mixture was filtered and the filtrate was concentrated in vacuo to give the title compound (2.20 g, 66% yield) as white solid. $^1H$ NMR (400 MHz, DMSO-$d_6$) δ 11.10 (s, 1H), 7.22-7.07 (m, 1H), 7.06-6.78 (m, 3H), 5.38 (dd, J=5.2, 12.4 Hz, 1H), 3.58 (s, 3H), 3.27-3.12 (m, 1H), 2.93-2.86 (m, 2H), 2.73-2.55 (m, 2H), 2.05-1.82 (m, 4H), 1.80-1.54 (m, 5H), 1.44-1.38 (m, 9H).

Step 3—3-[4-(4-Aminocyclohexyl)-3-methyl-2-oxo-benzimidazol-1-yl]piperidine-2,6-dione A solution of tert-butylN-[4-[1-(2,6-dioxo-3-piperidyl)-3-methyl-2-oxo-benzimidazol-4-yl]cyclohexyl]carbamate (1.00 g, 2.19 mmol) in TFA (10 mL) was stirred at 25° C. for 1 hr. The reaction mixture was concentrated in vacuo to give the title compound (780 mg, 100% yield, TFA salt) as blue oil. LC-MS ($ESI^+$) m/z 357.2 $(M+H)^+$.

(R)—N-(2-(iodomethyl)-2-methyl-6-morpholino-2,3-dihydrobenzofuran-5-yl)pyrazolo [1,5-a]pyrimidine-3-carboxamide (Intermediate BBP)

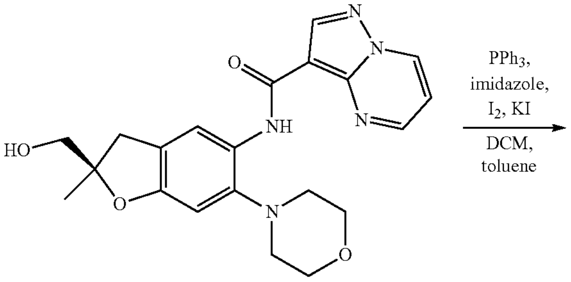

BCH

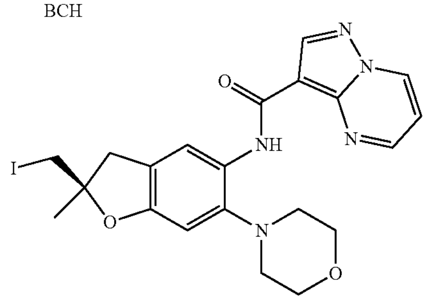

BBP

To a solution of $PPh_3$ (320 mg, 1.22 mmol) in DCM (2 mL) was added imidazole (83.1 mg, 1.22 mmol) and 12 (310 mg, 1.22 mmol) at 0° C. The mixture was stirred at 0° C. for 30 min and then was added to a solution of N-[(2R)-2-(hydroxymethyl)-2-methyl-6-morpholino-3H-benzofuran-5-yl]pyrazolo[1,5-a] pyrimidine-3-carboxamide (250 mg, 610 umol, Intermediate BCH) in toluene (15 mL) at 0° C. The mixture was stirred at 0° C. for 2 hrs. Then KI (507 mg, 3.05 mmol) was added and the mixture was stirred at 90° C. for 16 hrs. On completion, the reaction was concentrated. The residue was purified by Prep-HPLC(column: Phenomenex luna C18 150*40 mm*15 um;mobile phase: [water (0.225% FA)-ACN];B %: 45%-75%, 10 min) to give the title compound (200 mg, 62% yield) as a yellow solid. $^1H$ NMR (400 MHz, $CDCl_3$) δ 10.49 (s, 1H), 8.86 (dd, J=1.6, 7.2 Hz, 1H), 8.80 (s, 1H), 8.78 (dd, J=1.6, 4.0 Hz, 1H), 8.43 (s, 1H), 7.08 (dd, J=4.0, 7.2 Hz, 1H), 6.69 (s, 1H), 4.01-3.92 (m, 4H), 3.46 (s, 2H), 3.35 (d, J=16.0 Hz, 1H), 3.11 (d, J=16.0 Hz, 1H), 2.98-2.88 (m, 4H), 1.68 (s, 3H). LC-MS ($ESI^+$) m/z 520.0 $(M+H)^+$.

3-(7-azaspiro[3.5]nonan-2-yl)propan-1-ol (Intermediate BBQ)

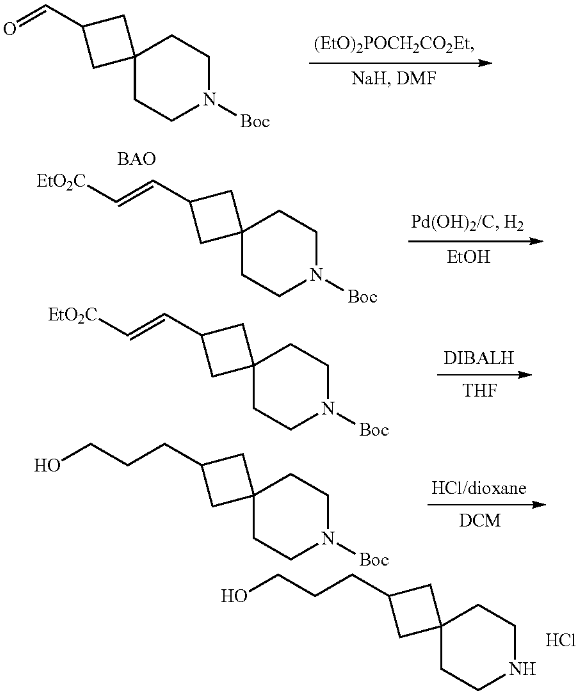

BBQ

Step 1—Tert-butyl 2-[(E)-3-ethoxy-3-oxo-prop-1-enyl]-7-azaspiro[3.5]nonane-7-carboxylate To a solution of ethyl 2-diethoxyphosphorylacetate (3.19 g, 14.2 mmol, 2.82 mL, CAS #30492-56-9) in DMF (20 mL) and THE (20 mL) was added NaH (568 mg, 14.2 mmol, 60% dispersion in mineral oil) at 0° C., the mixture was stirred at 0° C. for 30 min. Then a solution of tert-butyl 2-formyl-7-azaspiro[3.5]nonane-7-carboxylate (3 g, 11.8 mmol, Intermediate BAO) in a mixed solvent of DMF (20 mL) and THE (20 mL) was added to the mixture, and the reaction mixture was stirred at 25° C. for 3 hours. On completion, the reaction was quenched with $H_2O$ (50 mL), then extracted with EA/PE=2/1 (2×100 mL). The combined organic phase was dried over $Na_2SO_4$, filtered and the filtrate was concentrated in vacuo to give a residue. The residue was purified by column chromatography ($SiO_2$, PE/EA=50/1 to 10/1) to give the title compound (3.2 g, 83% yield) as colorless oil. $^1$H NMR (400 MHz, $CDCl_3$) δ 7.04 (dd, J=6.8, 15.6 Hz, 1H), 5.73 (dd, J=1.2, 15.6 Hz, 1H), 4.18 (q, J=7.2 Hz, 2H), 3.39-3.32 (m, 2H), 3.29-3.23 (m, 2H), 3.12-2.99 (m, 1H), 2.11-2.04 (m, 2H), 1.76-1.68 (m, 2H), 1.59 (t, J=5.6 Hz, 2H), 1.45-1.49 (m, 2H), 1.44 (s, 9H), 1.28 (t, J=7.2 Hz, 3H).

Step 2—Tert-butyl 2-(3-ethoxy-3-oxo-propyl)-7-azaspiro[3.5]nonane-7-carboxylate

To a solution of tert-butyl 2-[(E)-3-ethoxy-3-oxo-prop-1-enyl]-7-azaspiro[3.5]nonane-7-carboxylate (3.2 g, 9.89 mmol) in EtOH (30 mL) was added $Pd(OH)_2/C$ (500 mg, 10 wt %), and the reaction mixture was stirred at 25° C. under $H_2$ (15 psi) for 2 hour. On completion, the reaction mixture was filtered and the filtrate was concentrated in vacuo to give the title compound (3.0 g, 93% yield) as a white solid. $^1$H NMR (400 MHz, $CDCl_3$) δ 4.12 (q, J=7.2 Hz, 2H), 3.37-3.30 (m, 2H), 3.28-3.22 (m, 2H), 2.28-2.13 (m, 3H), 2.00-1.89 (m, 2H), 1.80-1.63 (m, 3H), 1.57-1.50 (m, 2H), 1.44 (s, 9H), 1.43-1.33 (m, 3H), 1.25 (t, J=7.2 Hz, 3H).

Step 3—Tert-butyl 2-(3-hydroxypropyl)-7-azaspiro[3.5]nonane-7-carboxylate

To a solution of tert-butyl 2-(3-ethoxy-3-oxo-propyl)-7-azaspiro[3.5]nonane-7-carboxylate (1.0 g, 3.07 mmol) in THF (30 mL) was added DIBAL-H (1 M, 7.68 mL) at 0° C., and the reaction mixture was stirred at 0° C. for 3 hour. On completion, the reaction mixture was quenched with sat. aq $NH_4Cl$ (20 mL), and then extracted with EA (2×40 mL). The combined organic phase was dried over $Na_2SO_4$, then filtered and the filtrate was concentrated in vacuo to give a residue. The residue was purified by column chromatography ($SiO_2$, PE/EA=10/1 to 4/1) to afford the title compound (520 mg, 59% yield) as colorless oil. $^1$H NMR (400 MHz, $CDCl_3$) δ 3.65-3.59 (m, 2H), 3.36-3.30 (m, 2H), 3.28-3.22 (m, 2H), 2.27-2.14 (m, 1H), 1.99-1.90 (m, 2H), 1.76-1.65 (m, 1H), 1.58-1.52 (m, 2H), 1.51-1.45 (m, 4H), 1.44 (s, 9H), 1.44-1.40 (m, 2H), 1.39-1.33 (m, 2H).

Step 4—3-(7-azaspiro[3.5]nonan-2-yl)propan-1-ol

To a solution of tert-butyl 2-(3-hydroxypropyl)-7-azaspiro[3.5]nonane-7-carboxylate (520 mg, 1.83 mmol) in DCM (5 mL) was added HCl/dioxane (4 M, 5 mL), and the reaction mixture was stirred at 25° C. for 2 hour. On completion, the reaction mixture was concentrated in vacuo to give the title compound (380 mg, 94% yield, HCl salt) as a white solid. $^1$H NMR (400 MHz, DMSO-$d_6$) δ 3.90-3.63 (m, 2H), 3.34 (t, J=6.4 Hz, 2H), 2.99-2.79 (m, 4H), 2.22-2.08 (m, 1H), 1.97-1.87 (m, 2H), 1.77-1.68 (m, 2H), 1.65-1.57 (m, 2H), 1.42-1.25 (m, 6H).

3-[7-[[4-[6-Methoxy-5-[[6-trifluoromethyl)pyridine-2-carbonyl]amino]indazol-2-yl]cyclohexyl]methyl]-7-azaspiro[3.5]nonan-2-yl]propyl methanesulfonate (Intermediate BBR)

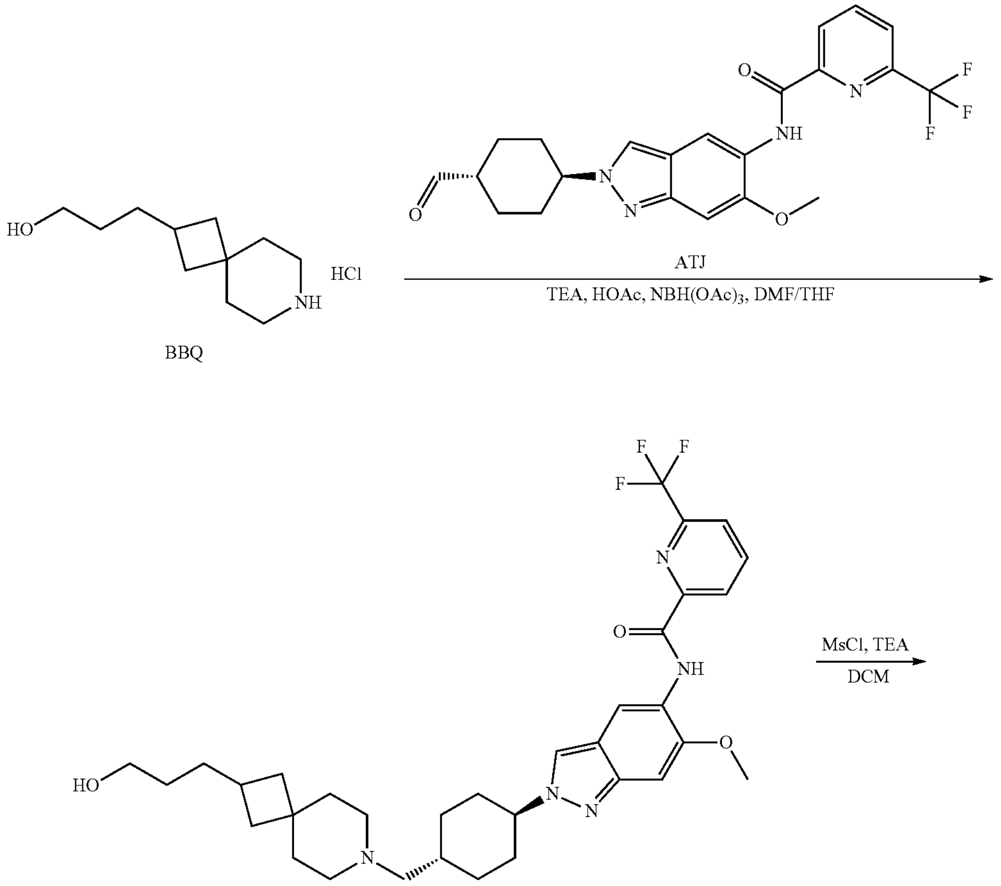

-continued

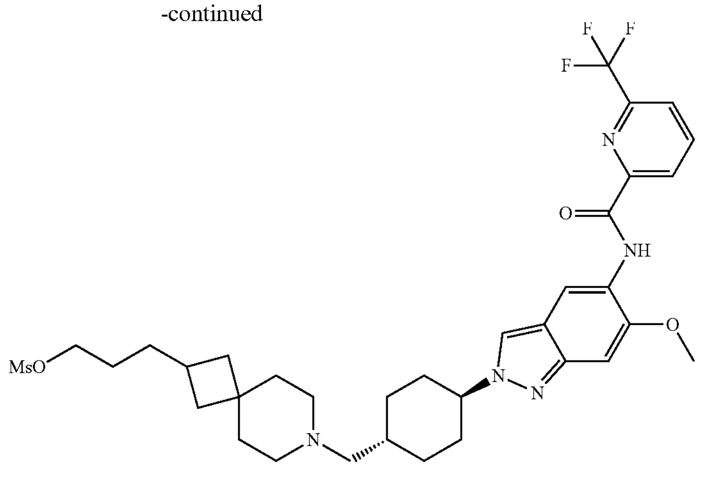

BBR

Step 1—N-[2-[4-[[2-(3-hydroxypropyl)-7-azaspiro[3.5]nonan-7-yl]methyl]cyclohexyl]-6-methoxy-indazol-5-yl]-6-(trifluoromethyl)pyridine-2-carboxamide To a solution of 3-(7-azaspiro[3.5]nonan-2-yl)propan-1-ol (360 mg, 1.64 mmol, HCl salt, Intermediate BBQ) in a mixed solvent of DMF (1.0 mL) and THE (1.0 mL) was added TEA (165 mg, 1.64 mmol, 228 uL), the reaction mixture was stirred at 0° C. for 10 min. Then N-[2-(4-formylcyclohexyl)-6-methoxy-indazol-5-yl]-6-(trifluoromethyl)pyridine-2-carboxamide (731 mg, 1.64 mmol, Intermediate ATJ) and HOAc (196 mg, 3.28 mmol, 187 uL) was added, and the mixture was stirred at 0° C. for 20 min. Next, $NaBH(OAc)_3$ (416 mg, 1.97 mmol) was added to the mixture, and the mixture was stirred at 0° C. for 1 hour. On completion, the mixture was quenched with $H_2O$ (0.5 mL), and then concentrated in vacuo to give a residue. The residue was purified by reverse phase (0.1% FA condition) to give the title compound (900 mg, 89% yield) as a yellow solid. $^1H$ NMR (400 MHz, DMSO-$d_6$) δ 10.49 (s, 1H), 8.68 (s, 1H), 8.48-8.42 (m, 1H), 8.42-8.35 (m, 1H), 8.30 (s, 1H), 8.21 (s, 1H), 7.14 (s, 1H), 4.36-4.29 (m, 1H), 3.97 (s, 3H), 3.91-3.81 (m, 1H), 3.34 (t, J=6.0 Hz, 2H), 2.45-1.98 (m, 9H), 1.96-1.70 (m, 6H), 1.69-1.50 (m, 3H), 1.45 (t, J=4.8 Hz, 2H), 1.40-1.18 (m, 6H), 1.13-0.97 (m, 2H); LC-MS ($ESI^+$) m/z 614.3 $(M+1)^+$.

Step 2—3-[7-[[4-[6-Methoxy-5-[[6-(trifluoromethyl)pyridine-2-carbonyl]amino]indazol-2-yl]cyclohexyl]methyl]-7-azaspiro[3.5]nonan-2-yl]propyl methanesulfonate To a solution of N-[2-[4-[[2-(3-hydroxypropyl)-7-azaspiro[3.5]nonan-7-yl]methyl]cyclohexyl]-6-methoxy-indazol-5-yl]-6-(trifluoromethyl)pyridine-2-carboxamide (200 mg, 325 umol) and MsCl (56.0 mg, 488 umol, 37.8 uL) in DCM (5.0 mL) was added TEA (98.9 mg, 977 umol, 136 uL) at 0° C., and the reaction mixture was stirred at 25° C. for 3 hours. On completion, the reaction mixture was quenched with $H_2O$ (20 mL), then extracted with DCM (2×40 mL). The organic phase was concentrated in vacuo to give the title compound (200 mg, 88% yield) as a white solid. LC-MS ($ESI^+$) m/z 692.1 $(M+1)^+$.

Benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (Intermediate OD)

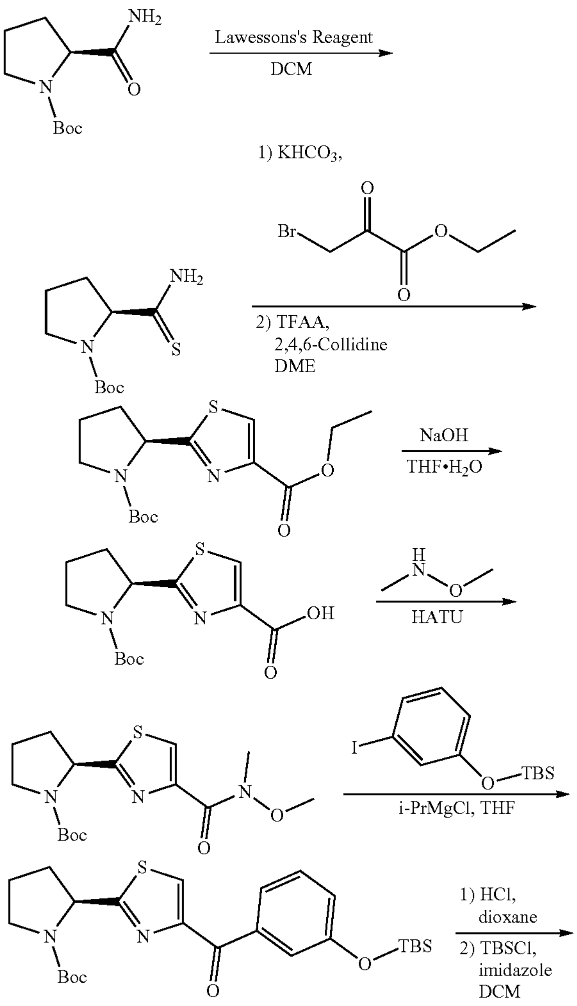

-continued

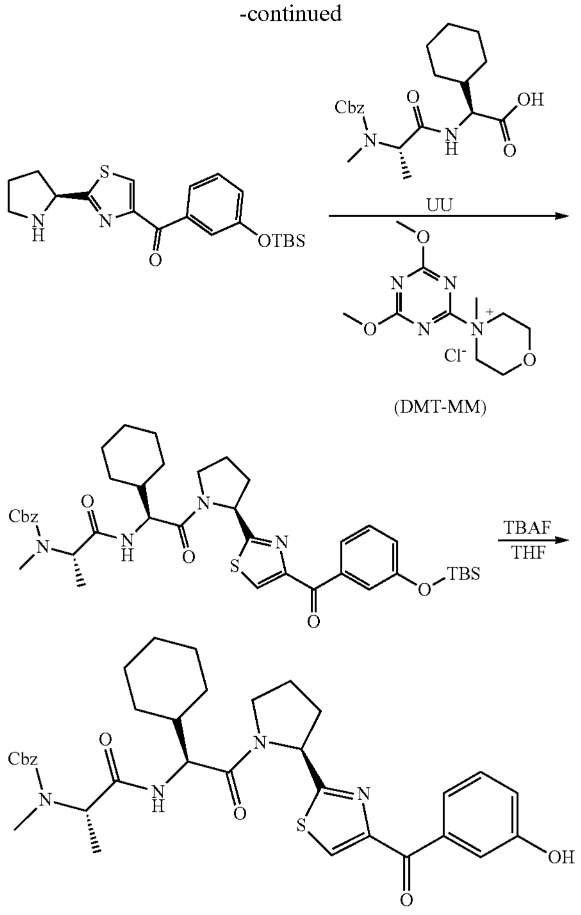

QD

Step 1—(S)-tert-butyl 2-carbamothioylpyrrolidine-1-carboxylate

To a stirred solution Boc-D-prolinamide (50.0 g, 234.0 mmol) in $CH_2CI_2$ (25 mL) at rt was added Lawesson's reagent (62.2 g, 140.0 mmol). The mixture was stirred overnight, then washed with $Na_2SO_4$. The oily residue was purified by column chromatography on silica gel, eluted with a 0-10 percent MeOH in $CH_2CI_2$ gradient, to afford the title compound (42 g, 78% yield) as a white solid. $^1H$ NMR (400 MHz, DMSO-$d_6$) δ 9.51 (s, 1H), 9.08 (m, 1H), 4.41 (dd, J=8.4, 3.3 Hz, 1H), 3.47-3.46 (m, 1H), 3.27 (s, 1H), 2.27-2.09 (m, 1H), 1.92-1.65 (m, 3H), 1.37 (m, 9H).

Step 2—ethyl (S)-2-(1-(tert-butoxycarbonyl)pyrrolidin-2-yl)thiazole-4-carboxylate Ethyl bromopyruvate (4.15 g, 21.3 mmol) was added dropwise via syringe to a mixture of (S)-tert-butyl 2-carbamothioylpyrrolidine-1-carboxylate (3.5 g, 15.2 mmol) and potassium bicarbonate (50.5 g, 504 mmol) in 35 mL of dimethoxyethane at 23c° C. The resulting mixture was stirred vigorously for 25 minutes, and then the mixture was cooled to 0° C. A mixture of trifluoroacetic anhydride (TFAA) (3.19 g, 15.2 mmol, 1 equiv.) and 2,4,6-collidine (2.94 g, 24.3 mmol, 1.6 equiv.) was then added dropwise via canula to the yellow mixture prepared above at 0° C. Following this addition, an additional three portions of neat TFAA (3.19 g, 15.2 mmol, 1 equiv.) and 2,4,6-collidine (2.94 g, 24.3 mmol, 1.6 equiv.) were prepared and added in sequence dropwise via canula to the yellow reaction mixture at 0° C. The resulting yellow mixture was stirred vigorously at 0° C. for 3 h. Then water (1,000 mL) was added and the solution was extracted with dichloromethane (2×50 mL). The organic phases were combined, washed with 0.5 N aqueous HCl (100 mL), washed with brine (100 mL), and dried over anhydrous sodium sulfate. The solution was filtered and concentrated to afford a light yellow solid. This solid was purified by flash column chromatography on silica gel (1:9 to 2:3 ethyl acetate:hexanes) providing a light yellow solid. This solid was triturated with ether (20 mL) to afford the title compound as a white solid (2.2 g, 44% yield). $^1H$ NMR (400 MHz, DMSO-$d_6$) δ 8.41 (d, J=9.8 Hz, 1H), 5.08 (d, J=7.3 Hz, 1H), 4.33-4.25 (m, 2H), 3.53-3.34 (m, 2H), 2.38-2.27 (m, 1H), 2.04-1.99 (m, 1H), 1.93-1.79 (m, 2H), 1.43 (s, 6H), 1.30 (t, J=7.1 Hz, 3H), 1.24 (s, 3H). LC/MS (ESI, m/z): [M+1]=327.3.

Step 3—(S)-2-(1-(tert-butoxycarbonyl)pyrrolidin-2-yl)thiazole-4-carboxylic acid

A solution of (S)-ethyl 2-(1-(tert-butoxycarbonyl)pyrrolidin-2-yl)thiazole-4-carboxylate (14.5 g, 44.5 mmol, 1 equiv.) in tetrahydrofuran (60 mL) was added to a solution of sodium hydroxide (5.33 g, 134.5 mmol, 3 equiv.) in water (40 mL) at 23° C. The resulting mixture was stirred vigorously at 23° C. for 3 h. Then the mixture was concentrated to 20 mL. The concentrated mixture was cooled to 0° C. and the pH was adjusted to 3 by the addition of concentrated HCl solution dropwise. A lot of white solid was formed and the solid was collected by filtration to provide the title compound as a white solid (10.4 g, 74% yield). LC/MS (ESI, m/z): [M+1]+=299.4.

Step 4—tert-butyl (S)-2-(4-(methoxy(methyl)carbamoyl)thiazol-2-yl)pyrrolidine-1-carboxylate (S)-2-(1-(tert-butoxycarbonyl)pyrrolidin-2-yl)thiazole-4-carboxylic acid (22.6 g, 75.8 mmol), O,N-dimethylhydroxylamine hydrochloride (11.9 g, 122.7 mmol), diisopropyl ethyl amine (45.0 mL, 243 mmol) and HATU (46.2 g, 122.0 mmol) in DMF (200 mL) were stirred at rt for 12 hours. The reaction mixture was quenched with water, and the layers were separated. The aqueous layer was extracted with EtOAc (100 mL×3), and the combined organic layers were dried, filtered and concentrated. The crude product was purified via column chromatography on silica gel, eluting with hexanes/ethyl acetate (1:1) to give the title compound as an oil (23.0 g, 89% yield). LC/MS (ESI, m/z): [M+1]+=342.2. $^1H$ NMR (400 MHz, DMSO-$d_6$) δ 8.11 (s, 1H), 5.08 (m, 1H), 3.72 (s, 3H), 3.52-3.35 (m, 2H), 3.29 (s, 3H), 2.32 (m, 1H), 2.06 (m, 1H), 1.96-1.77 (m, 2H), 1.50-1.20 (d, 9H).

Step 5—(S)-tert-butyl 2-(4-(3-((tert-butyldimethylsilyl)oxy)benzoyl)thiazol-2-yl)pyrrolidine-1-carboxylate To a solution of tert-butyl(3-iodophenoxy)dimethylsilane (6.9 g, 20.6 mmol) in THF (50 mL) was added isopropylmagnesium chloride solution (9.27 mL, 2.0 M in THF) dropwise at −10° C. under $N_2$. The reaction mixture was stirred at 0° C. for 30 min. Then this resulting mixture, which formed (3-((tert-butyldimethylsilyl)oxy)phenyl)magnesium iodide, was added dropwise via syringe to a solution of the weinreb amide tert-butyl (S)-2-(4-(methoxy(methyl)

carbamoyl)thiazol-2-yl)pyrrolidine-1-carboxylate (3.9 g, 11.4 mmol) in THE (10 mL) at 0° C. The mixture was stirred at 0° C. for 30 min then warmed up to rt and stirred for 4 h. The mixture was then cooled to −5° C. and quenched with saturated ammonium chloride solution (20 mL). The mixture was partitioned between water (30 mL) and ethyl acetate (100 mL). The organic phase was separated and the aqueous phase was further extracted with ethyl acetate (3×100 mL). The organic phases were combined, washed with brine (50 mL) and dried over anhydrous sodium sulfate. The dried solution was filtered and concentrated to give a light yellow oil. This oil was purified by flash column chromatography on silica gel (1:30 to 1:10 ethyl acetate: hexanes) providing the title compound as a colorless oil (5.13 g, 92.1%). $^1$H NMR (400 MHz, $CDCl_3$) δ 8.10 (s, 1H), 7.76 (d, J=7.7 Hz, 1H), 7.71-7.66 (m, 1H), 7.34 (t, J=7.9 Hz, 1H), 7.07 (d, J=7.0 Hz, 1H), 5.30-5.19 (m, 1H), 3.66-3.41 (m, 2H), 2.42-2.19 (m, 2H), 2.01-1.90 (m, 2H), 1.50 (s, 3H), 1.35 (s, 6H), 1.02-0.98 (m, 9H), 0.28-0.14 (m, 6H); LC/MS (ESI, m/z): [M+1]=489.5.

Step 6—(S)-(3-((tert-butyldimethylsilyl)oxy)phenyl)(2-(pyrrolidin-2-yl)thiazol-4-yl)methanone To a solution of (S)-tert-butyl 2-(4-(3-((tert-butyldimethylsilyl)oxy)benzoyl)thiazol-2-yl)pyrrolidine-1-carboxylate (12.0 g, 20.5 mmol) in 1,4-dioxane (60 mL) was added HCl-dioxane (40 mL) (4 M in dioxane) dropwise. The reaction mixture was stirred at rt for 3 h. The reaction mixture concentrated in vacuo and used directly without further purification to afford (S)-(3-hydroxyphenyl)(2-(pyrrolidin-2-yl)thiazol-4-yl)methanone HCl salt (8.0 g). To a solution of (S)-(3-hydroxyphenyl)(2-(pyrrolidin-2-yl)thiazol-4-yl)methanone HCl salt (8.00 g, 25.7 mmol) in DCM (80 mL) was added imidazole (5.2 g, 57.2 mmol) slowly at 0° C. Then TBSCI (3.89 g, 34.3 mmol, in 20 mL DCM) was added slowly at 0° C. The resulting mixture was stirred at rt for 130 min. The reaction mixture was quenched with water, extracted with ethyl acetate (3×100 mL), washed with brine (50 mL) and dried over anhydrous sodium sulfate. The solution was filtered, concentrated, and purified by flash column chromatography on silica gel (1:100 to 1:40 methanol/DCM) to give the title compound as a yellow oil (8.0 g, 84% yield). $^1$H NMR (400 MHz, DMSO-$d_6$) δ 8.38 (s, 1H), 7.71-7.64 (m, 2H), 7.43 (t, J=8.0 Hz, 1H), 7.14 (ddd, J=8.0, 2.4, 1.1 Hz, 1H), 4.51 (dd, J=8.3, 4.9 Hz, 1H), 3.56 (s, 1H), 3.00-2.89 (m, 2H), 2.27-2.10 (m, 1H), 1.75-1.70 (m, 1H), 1.77-1.65 (m, 2H), 0.97 (s, 9H), 0.22 (s, 6H).

Step 7—benzyl ((S)-1-(((S)-2-((S)-2-(4-(3-((tert-butyldimethylsilyl)oxy)benzoyl)thiazol-2-yl)pyrrolidin-1-yl)-1-cyclohexyl-2-oxoethyl)amino)-1-oxopropan-2-yl)(methyl)carbamate In a 250-mL round-bottom flask, was placed (S)-(3-((tert-butyldimethylsilyl)oxy)phenyl)(2-(pyrrolidin-2-yl)thiazol-4-yl)methanone (7.5 g, 19.3 mmol), (S)-2-((S)-2-(((benzyloxy)carbonyl)(methyl)amino)propanamido)-2-cyclohexylacetic acid (9.5 g, 25.1 mmol, Intermediate UU), and 4-methylmorpholine (3.90 g, 38.60 mmol) in EtOAc (100 mL) at 0° C. DMT-MM (6.94 g, 25.1 mmol) was then added and the resulting solution was stirred for h at 0° C. Then $H_2O$ (40 mL) was added, and the resulting solution was extracted with EtOAC (3×50 mL). The combined organic layers were washed with 50 mL of brine, dried over anhydrous sodium sulfate and concentrated under vacuum. The residue was applied onto a silica gel column eluting with ethyl acetate/petroleum ether (1:2) to give the title compound as a yellow solid. (7.3 g, 60% yield). $^1$H NMR (400 MHz, DMSO-$d_6$) δ 8.49 (s, 1H), 7.95 (d, J=39.4 Hz, 1H), 7.74-7.63 (m, 2H), 7.43 (t, J=7.9 Hz, 1H), 7.35-7.31 (m, 5H), 7.16 (dd, J=8.0, 2.5 Hz, 1H), 5.37 (dd, J=7.6, 2.2 Hz, 1H), 5.08-5.01 (m, 1H), 4.66 (d, J=6.6 Hz, 1H), 4.37 (t, J=7.5 Hz, 1H), 3.83-3.75 (m, 2H), 2.83 (s, 3H), 2.33-2.14 (m, 2H), 2.07-1.98 (m, 2H), 1.67-1.48 (m, 6H), 1.25 (s, 3H), 1.07-0.89 (m, 14H), 0.22 (s, 6H). LC/MS (ESI, m/z): [M+1]=747.6.

Step 8—benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate To a stirred solution of benzyl ((S)-1-(((S)-2-((S)-2-(4-(3-((tert-butyldimethylsilyl)oxy)benzoyl)thiazol-2-yl)pyrrolidin-1-yl)-1-cyclohexyl-2-oxoethyl)amino)-1-oxopropan-2-yl)(methyl)carbamate (5.0 g, 6.68 mmol) in THE (20 mL) was added TBAF (8.0 mL, 8.0 mmol) a rt. The reaction mixture was stirred at rt for 4 h. Then $H_2O$ (20 mL) was added and the mixture was extracted with EtOAc (50 mL×2). The combined organic layer was washed with brine, dried and concentrated in vacuo. The mixture was purified via column chromatography (DCM/EtOAc=5%-80%) to give the title compound (3.2 g, 76% yield) as a yellow solid. $^1$H NMR (400 MHz, MeOD-$d_4$) δ 8.26 (s, 1H), 7.59-7.53 (m, 1H), 7.51 (dd, J=2.3, 1.7 Hz, 1H), 7.37-7.28 (m, 6H), 7.05 (ddd, J=8.1, 2.6, 0.9 Hz, 1H), 5.50-5.39 (m, 1H), 5.13 (s, 2H), 4.69 (s, 1H), 4.54-4.38 (m, 1H), 4.02-3.93 (m, 1H), 3.90-3.86 (m, 1H), 2.94 (s, 3H), 2.23-2.10 (m, 4H), 1.72-1.56 (m, 6H), 1.37 (d, J=5.2 Hz, 3H), 1.16-0.88 (m, 5H); LC-MS ($ESI^+$): m/z 633.5 $(M+H)^+$.

(1R,4r)-4-((Benzyloxy)methyl)cyclohexanecarbonyl chloride (Intermediate BAU)

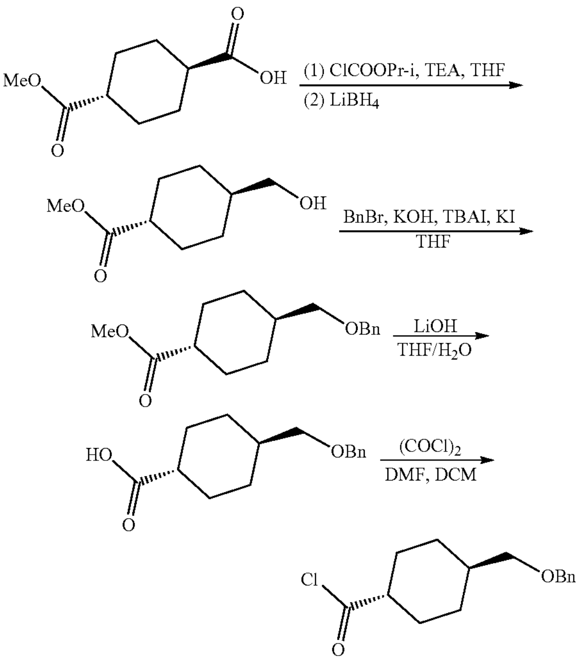

BAU

Step 1—(1R,4r)-Methyl 4-(hydroxymethyl)cyclohexanecarboxylate

To a solution of 4-methoxycarbonylcyclohexanecarboxylic acid (20.0 g, 107 mmol, CAS #15177-67-0) in the THF (200 mL) was added $Et_3N$ (21.7 g, 215 mmol, 29.9 mL) and isopropyl carbonochloridate (19.7 g, 161 mmol, 22.4 mL) at 0° C. The mixture was stirred at 25° C. for 1 hour. Then the mixture was filtered and the $LiBH_4$ (11.7 g, 537 mmol) was added in portion at 0° C. The mixture was stirred at 25° C. for 4 hours. On completion, the mixture was quenched by water (500 mL) and extracted with EA (3×1000 mL). The organic layers were dried over $Na_2SO_4$, filtered and concentrated in vacuo. The residue was purified by column chromatography to give the title compound (9.70 g, 52% yield) as colorless oil. $^1H$ NMR (400 MHz, $CDCl_3$) δ 3.67 (s, 3H), 3.47 (d, J=6.0 Hz, 2H), 2.26 (tt, J=3.6, 12.4 Hz, 1H), 2.06-1.99 (m, 2H), 1.88 (dd, J=3.2, 13.6 Hz, 2H), 1.56-1.39 (m, 3H), 1.07-0.93 (m, 2H).

Step 2—(1R,4r)-Methyl 4-((benzyloxy)methyl)cyclohexanecarboxylate

To a solution of methyl 4-(hydroxymethyl)cyclohexanecarboxylate (9.70 g, 56.3 mmol) in the THF (100 mL) was added KOH (4.74 g, 84.5 mmol), TBAI (4.16 g, 11.3 mmol), KI (1.87 g, 11.3 mmol) and BnBr (14.5 g, 84.5 mmol, 10.0 mL). The mixture was stirred at 25° C. for 12 hours. On completion, the reaction mixture was filtered and concentrated in vacuo. The residue was purified by column chromatography to give the title compound (11.0 g, 74% yield) as colorless oil. $^1H$ NMR (400 MHz, $CDCl_3$) δ 7.39-7.27 (m, 5H), 4.50 (s, 2H), 3.67 (s, 3H), 3.29 (d, J=6.4 Hz, 2H), 2.25 (tt, J=3.6, 12.4 Hz, 1H), 2.04-1.98 (m, 2H), 1.91 (br dd, J=3.6, 13.6 Hz, 2H), 1.71-1.61 (m, 1H), 1.45-1.42 (m, 2H), 1.08-0.94 (m, 2H).

Step 3—(1R,4r)-4-((benzyloxy)methyl)cyclohexanecarboxylic acid

To a solution of methyl 4-(benzyloxymethyl)cyclohexanecarboxylate (11.0 g, 41.9 mmol) in the THEF (100 mL), MeOH (20 mL) and $H_2O$ (20 mL) was added LiOH (5.02 g, 210 mmol). The mixture was stirred at 25° C. for 12 hours. On completion, the reaction mixture was concentrated in vacuo. The residue was diluted with water (100 mL) and washed with PE (200 mL). The water phase was acidifed by HCl (aq, 1M) to pH=4. Then the mixture was extracted with DCM (3×200 mL). The organic layer was dried over $Na_2SO_4$, filtered and concentrated in vacuo to give the title compound (10.1 g, 97% yield) as colorless oil. $^1H$ NMR (400 MHz, $CDCl_3$) δ 7.41-7.26 (m, 5H), 4.50 (s, 2H), 3.30 (d, J=6.4 Hz, 2H), 2.28 (tt, J=3.6, 12.4 Hz, 1H), 2.05 (dd, J=2.8, 13.6 Hz, 2H), 1.92 (dd, J=2.8, 13.6 Hz, 2H), 1.65-1.62 (m, 1H), 1.46 (dq, J=3.6, 12.8 Hz, 2H), 1.11-0.95 (m, 2H).

Step 4—(1R,4r)-4-((Benzyloxy)methyl)cyclohexanecarbonyl chloride

To a solution of 4-(benzyloxymethyl)cyclohexanecarboxylic acid (10.0 g, 40.3 mmol) in the DCM (100 mL) was added DMF (294 mg, 4.03 mmol) and $(COCl)_2$ (7.67 g, 60.4 mmol, 5.29 mL) in portion at 0° C. The mixture was stirred at 0° C. for 2 hrs. On completion, the reaction mixture was concentrated in vacuo to give the title compound (10.7 g, 99% yield) as yellow oil.

Methyl 6-bromo-2-((1r,4r)-4-(hydroxymethyl)cyclohexyl)benzo[d]oxazole-5-carboxylate (Intermediate BBS)

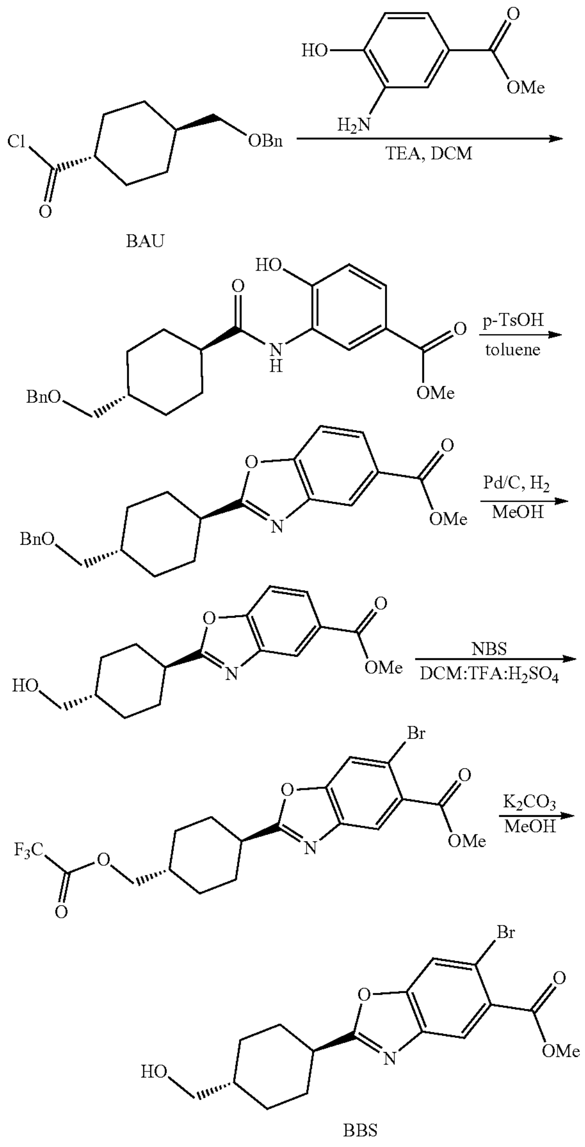

Step 1—Methyl 3-((1r,4r)-4-((benzyloxy)methyl)cyclohexanecarboxamido)-4-hydroxybenzoate To a solution of methyl 3-amino-4-hydroxy-benzoate (7.38 g, 44.1 mmol, CAS #536-25-4) and $Et_3N$ (12.2 g, 120 mmol) in the DCM (100 mL) was added 4-(benzyloxymethyl)cyclohexanecarbonyl chloride (10.7 g, 40.1 mmol, Intermediate BAU) slowly at 0° C. The mixture was stirred at 25° C. for 12 hrs. On completion, the reaction mixture was diluted with DCM (200 mL) and washed with water (3×200 mL). The organic layer was dried over $Na_2SO_4$, filtered and concentrated in vacuo. The residue was purified by trituration (PE:EA=5:1) to give the title compound (13.0 g, 82% yield) as white solid. $^1H$ NMR (400 MHz, $CDCl_3$) δ 7.80 (dd, J=2.0, 8.4 Hz, 1H), 7.71 (d, J=1.6 Hz, 1H), 7.64 (s, 1H), 7.39-7.28 (m, 5H), 7.03 (d, J=8.4 Hz, 1H), 4.52 (s, 2H), 3.88 (s, 3H), 3.33 (d, J=6.4 Hz, 2H), 2.36 (tt, J=3.2, 12.0 Hz, 1H), 2.11-1.95 (m, 4H), 1.77-1.67 (m, 1H), 1.61 (dq, J=3.2, 12.8 Hz, 2H), 1.10 (dq, J=3.6, 12.8 Hz, 2H).

Step 2—Methyl 2-((1r,4r)-4-((benzyloxy)methyl) cyclohexyl)benzo[d]oxazole-5-carboxylate A mixture of methyl 3-[[4-(benzyloxymethyl)cyclohexanecarbonyl]amino]-4-hydroxy-benzoate (13.0 g, 32.7 mmol) and TsOH (2.25 g, 13.1 mmol) in the toluene (150 mL) was refluxed at 130° C. for 12 hrs. On completion, the reaction mixture was concentrated in vacuo and the residue was purified by column chromatography ($SiO_2$, PE:EA=10:1 to 5:1) to give the title compound (12.0 g, 97% yield) as white solid. $^1H$ NMR (400 MHz, $CDCl_3$) δ 8.37 (d, J=1.6 Hz, 1H), 8.06 (dd, J=1.6, 8.4 Hz, 1H), 7.51 (d, J=8.4 Hz, 1H), 7.41-7.27 (m, 5H), 4.54 (s, 2H), 3.96 (s, 3H), 3.36 (d, J=6.4 Hz, 2H), 2.93 (tt, J=3.2, 12.0 Hz, 1H), 2.34-2.23 (m, 2H), 2.08-1.99 (m, 2H), 1.95-1.84 (m, 1H), 1.78-1.66 (m, 2H), 1.25-1.12 (m, 2H).

Step 3—Methyl 2-((1r,4r)-4-(hydroxymethyl)cyclohexyl)benzo[d]oxazole-5-carboxylate To a solution of methyl 2-[4-(benzyloxymethyl)cyclohexyl]-1,3-benzoxazole-5-carboxylate (5.30 g, 14.0 mmol) in the MeOH (10 mL) was added Pd/C (100 mg, 10 wt %). The mixture was stirred at 25° C. for 4 hrs under $H_2$ (15 Psi). On completion, the reaction mixture was filtered and concentrated in vacuo and purified by column chromatography ($SiO_2$, Petroleum ether/Ethyl acetate=5/1 to 2/1) to give the title compound (3.50 g, 87% yield) as white solid. $^1H$ NMR (400 MHz, $CDCl_3$) δ 8.38 (d, J=1.2 Hz, 1H), 8.07 (dd, J=1.6, 8.4 Hz, 1H), 7.52 (d, J=8.4 Hz, 1H), 3.96 (s, 3H), 3.55 (t, J=5.6 Hz, 2H), 2.94 (tt, J=3.6, 12.2 Hz, 1H), 2.36-2.26 (m, 2H), 2.01 (dd, J=3.2, 13.2 Hz, 2H), 1.74 (dq, J=3.2, 12.8 Hz, 2H), 1.68-1.60 (m, 1H), 1.35 (t, J=5.6 Hz, 1H), 1.25-1.12 (m, 2H).

Step 4—Methyl 6-bromo-2-((1r,4r)-4-((2,2,2-trifluoroacetoxy)methyl)cyclohexyl)benzo[d]oxazole-5-carboxylate To a solution of methyl 2-[4-(hydroxymethyl)cyclohexyl]-1,3-benzoxazole-5-carboxylate (1.00 g, 3.46 mmol) in the DCM (6 mL), TFA (6 mL) and $H_2SO_4$ (3 mL) was added NBS (738 mg, 4.15 mmol). The mixture was stirred at 45° C. for 12 hr. On completion, the reaction mixture was concentrated in vacuo to give the title compound (1.5 g, 93% yield) as yellow oil. LC-MS ($ESI^+$) m/z 463.9 $(M+H)^+$.

Step 5—Methyl 6-bromo-2-((1r,4r)-4-(hydroxymethyl)cyclohexyl)benzo[d]oxazole-5-carboxylate To a solution of methyl 6-bromo-2-[4-[(2,2,2-trifluoroacetyl)oxymethyl]cyclohexyl]-1,3-benzoxazole -5-carboxylate (1.20 g, 2.58 mmol) in the MeOH (6 mL) was added $K_2CO_3$ (1.07 g, 7.75 mmol). The mixture was stirred at 25° C. for 1 hour. On completion, the reaction mixture was filtered and concentrated in vacuo and the residue was purified by reversed phase (TFA, 0.1%) to give the title compound (300 mg, 31% yield) as yellow solid. $^1H$ NMR (400 MHz, $CDCl_3$) δ 8.12 (s, 1H), 7.80 (s, 1H), 3.97 (s, 3H), 3.55 (d, J=6.2 Hz, 2H), 2.92 (tt, J=3.6, 12.4 Hz, 1H), 2.29 (dd, J=3.2, 13.2 Hz, 2H), 2.05-1.96 (m, 2H), 1.77-1.66 (m, 2H), 1.65-1.62 (m, 1H), 1.23-1.12 (m, 2H).

N-(2-((1r,4r)-4-formylcyclohexyl)-5-(2-hydroxypropan-2-yl)benzo[d]oxazol-6-yl)-6- (trifluoromethyl) picolinamide (Intermediate BBT)

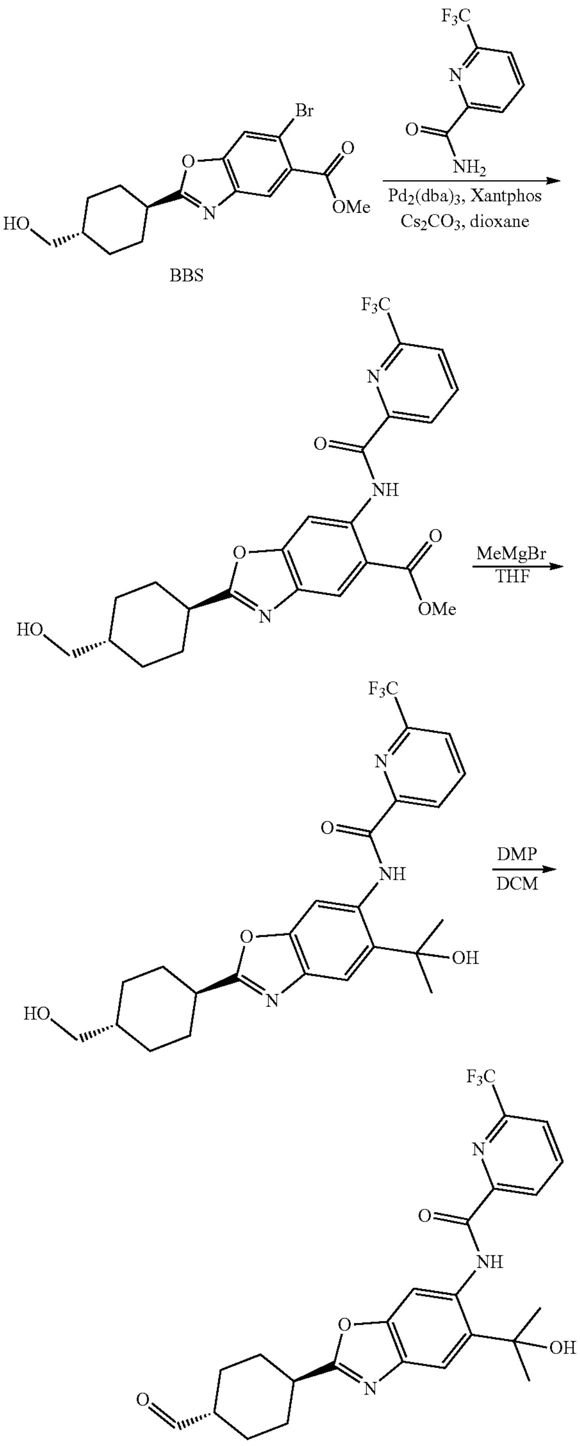

BBS

BBT

Step 1—Methyl 2-((1r,4r)-4-(hydroxymethyl)cyclohexyl)-6-(6-(trifluoromethyl)picolinamido) benzo[d]oxazole-5-carboxylate A mixture of methyl 6-bromo-2-[4-(hydroxymethyl)cyclohexyl]-1,3-benzoxazole-5-carboxylate (200 mg, 543 umol, Intermediate BBS), 6-(trifluoromethyl)pyridine-2-carboxamide (124 mg, 652 umol), Xantphos (31.4 mg, 54.3 umol), $Pd_2(dba)_3$ (49.7 mg, 54.3 umol) and $Cs_2CO_3$ (354 mg, 1.09 mmol) in the dioxane (2 mL) was stirred at 100° C. for 4 hrs under $N_2$. On completion, the reaction mixture was concentrated in vacuo and purified by column chromatography ($SiO_2$, Petroleum ether/Ethyl acetate=5/1 to 2/1) to give the title compound (100 mg, 39% yield) as yellow solid. $^1H$ NMR (400 MHz, $CDCl_3$) δ 13.21 (s, 1H), 9.18 (s, 1H), 8.52 (d, J=7.6 Hz, 1H), 8.45 (s, 1H), 8.14 (t, J=7.6 Hz, 1H), 7.91 (d, J=7.6 Hz, 1H), 4.05 (s, 3H), 3.56 (br d, J=6.0 Hz, 2H), 2.94 (tt, J=3.6, 12.4 Hz, 1H), 2.35-2.28 (m, 2H), 2.02 (dd, J=2.8, 13.2 Hz, 2H), 1.74 (J=3.6, 13.0 Hz, 2H), 1.38-1.31 (m, 1H), 1.24-1.13 (m, 2H).

Step 2—N-(2-((1r,4r)-4-(hydroxymethyl)cyclohexyl)-5-(2-hydroxypropan-2-yl)benzo[d]oxazol-6-yl)-6-(trifluoromethyl)picolinamide To a solution of methyl 2-[4-(hydroxymethyl)cyclohexyl]-6-[[6-(trifluoromethyl)pyridine-2-carbonyl]amino]-1,3-benzoxazole-5-carboxylate (100 mg, 210 umol) in the THF (2 mL) was added MeMgBr (3 M, 698 uL) at 0° C. The mixture was stirred at 0° C. for 5 hrs. On completion, the mixture was poured into saturated $NH_4Cl$ (10 mL) and extracted with EA (2×30 mL). The organic layer was dried over $Na_2SO_4$, filtered and concentrated in vacuo. The residue was purified by column chromatography ($SiO_2$, Petroleum ether/Ethyl acetate=3/1 to 1/1) to give the title compound (80.0 mg, 80% yield) as yellow solid. $^1H$ NMR (400 MHz, $CDCl_3$) δ 12.44 (s, 1H), 8.84 (s, 1H), 8.52 (d, J=7.6 Hz, 1H), 8.13 (t, J=7.6 Hz, 1H), 7.87 (d, J=7.6 Hz, 1H), 7.68 (s, 1H), 3.55 (t, J=5.6 Hz, 2H), 2.92 (tt, J=3.6, 12.2 Hz, 1H), 2.31 (d, J=10.8 Hz, 2H), 2.21 (s, 1H), 2.04-1.96 (m, 2H), 1.79 (s, 6H), 1.72 (dd, J=3.2, 12.8 Hz, 2H), 1.66-1.62 (m, 1H), 1.36 (t, J=5.6 Hz, 1H), 1.18 (dq, J=3.2, 12.8 Hz, 2H).

Step 3—N-(2-((1r,4r)-4-formylcyclohexyl)-5-(2-hydroxypropan-2-yl)benzo[d]oxazol-6-yl)-6- (trifluoromethyl)picolinamide To a solution of N-[2-[4-(hydroxymethyl)cyclohexyl]-5-(1-hydroxy-1-methyl-ethyl)-1,3-benzoxazol-6-yl]-6-(trifluoromethyl)pyridine-2-carboxamide (80.0 mg, 168 umol) in the DCM (2 mL) was added DMP (92.4 mg, 218 umol) at 0° C. The mixture was stirred at 25° C. for 1 hour. On completion, the reaction mixture was poured into saturated $Na_2SO_3$ (aq, 2 mL) and $NaHCO_3$ (aq, 2 mL). The mixture was stirred for 10 minutes, then the mixture was extracted with DCM (20 mL). The organic layer was dried over $Na_2SO_4$, filtered and concentrated in vacuo to give the title compound (70.0 mg, 88% yield) as yellow solid. LC-MS ($ESI^+$) m/z 476.2 $(M+H)^+$.

(S)-7-Hydroxy-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide (Intermediate MH)

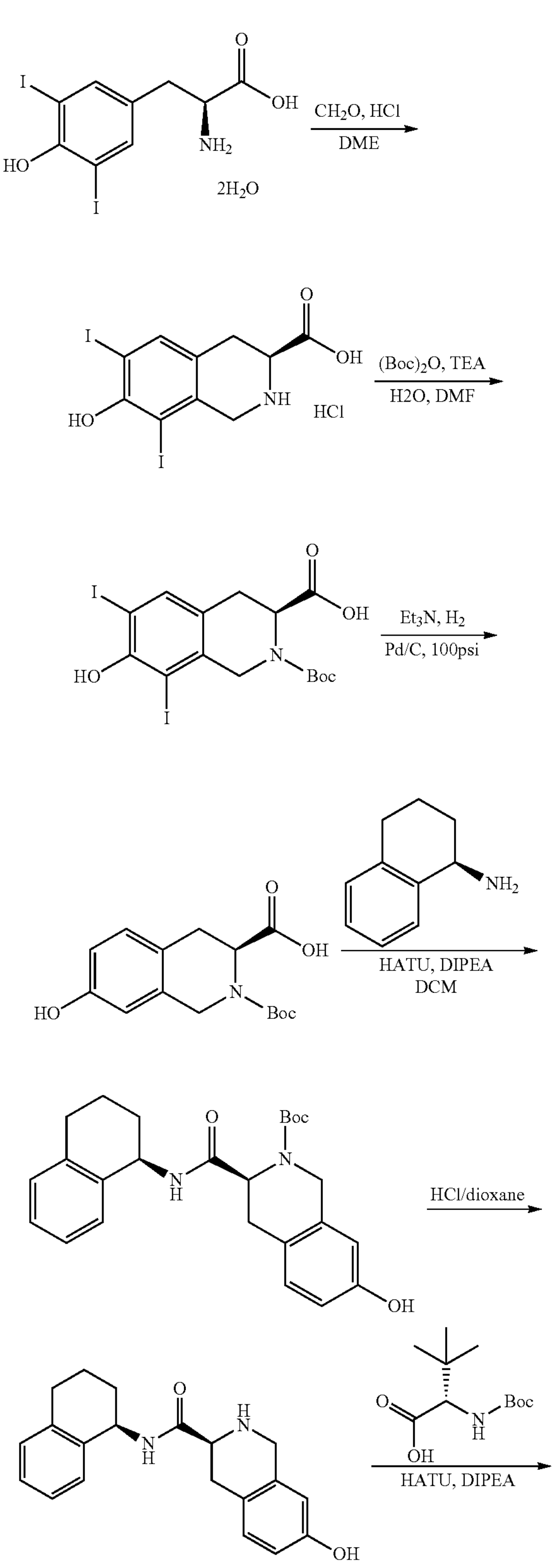

-continued

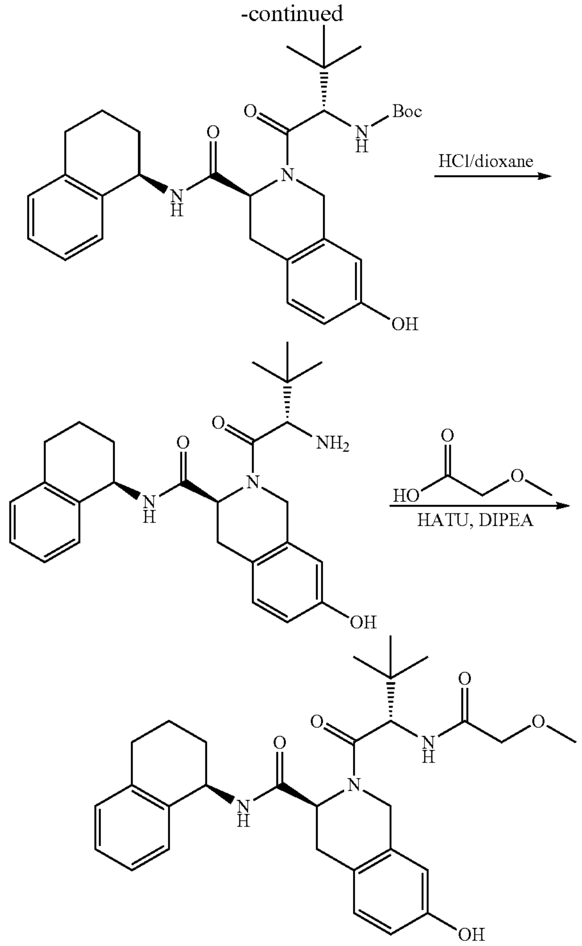

MH

Step 1—(S)-7-hydroxy-6,8-diiodo-1,2,3,4-tetrahydroisoquinoline-3-carboxylic acid hydrochloride To concentrate HCl (780 mL) was added (S)-2-amino-3-(4-hydroxy-3,5-diiodophenyl)propanoic acid (65 g, 150 mmol, CAS #18835-59-1), $CH_2O$ (37% in $H_2O$) and DME (65 mL). The mixture was heated to 72° C. slowly, and then stirred overnight. To the mixture was added another 20 mL of $CH_2O$ (37% in $H_2O$), and the reaction was stirred for another 4 h at 72° C. The mixture was cooled to 0° C. and filtered. The filter cake was washed with DME (50 mL) give (S)-7-hydroxy-6,8-diiodo-1,2,3,4-tetrahydroisoquinoline-3-carboxylic acid hydrochloride HCl salt (32 g, 72% yield) as a yellow solid. $^1H$ NMR (400 MHz, DMSO-$d_6$) δ 9.89 (s, 1H), 9.69 (s, 1H), 7.73 (s, 1H), 4.34-4.30 (dd, J=4.8 Hz, J=11.2 Hz, 1H), 4.14-4.00 (dd, J=16.4 Hz, J=40 Hz, 2H), 3.24-3.18 (m, 1H), 3.09-3.02 (m, 1H). LC-MS (ESI$^+$): m/z 482.5 $(M+H)^+$.

Step 2—(S)-2-(tert-butoxycarbonyl)-7-hydroxy-6,8-diiodo-1,2,3,4-tetrahydroisoquinoline-3-carboxylic acid A mixture of (S)-7-hydroxy-6,8-diiodo-1,2,3,4-tetrahydroisoquinoline-3-carboxylic acid hydrochloride (20 g, 41.6 mmol0, $(Boc)_2O$ (13.6 g, 62.4 mmol), TEA (16.8 g, 166 mmol), $H_2O$ (40 mL) and DMF (300 mL) was stirred overnight at rt. To the mixture was added $H_2O$ (200 mL), and the solution was washed with EA (200 mL). The aqueous layer adjusted with 1 N HCl to pH<7, then extracted with EA (300 mL). The organic layer was washed with brine (100 mL), dried over $Na_2SO_4$, filtered, concentrated, and purified by column to give (S)-2-(tert-butoxycarbonyl)-7-hydroxy-6,8-diiodo-1,2,3,4-tetrahydroisoquinoline-3-carboxylic acid (15.5 g, 68% yield) as a yellow solid. $^1H$ NMR (400 MHz, DMSO-$d_6$) δ 12.77 (s, 1H), 9.46 (s, 1H), 7.64 (s, 1H), 4.83-4.67 (m, 1H), 4.49-4.39 (m, 1H), 4.21-4.17 (d, J=16.8 Hz, 1H), 3.05-3.04 (d, J=4 Hz, 2H), 1.47-1.40 (d, J=24.4 Hz, 9H).

Step 3: (S)-2-(tert-butoxycarbonyl)-7-hydroxy-1,2,3,4-tetrahydroisoquinoline-3-carboxylic acid A mixture of (S)-2-(tert-butoxycarbonyl)-7-hydroxy-6,8-diiodo-1,2,3,4-tetrahydroisoquinoline-3-carboxylic acid (7 g, 12.8 mmol), Pd/C (10 wt %, 1.4 g), TEA (2.9 g, 28.3 mmol) and MeOH (100 mL) was stirred for overnight at rt under $N_2$. The mixture was filtered to remove Pd/C, concentrated to dry, then $H_2O$ (100 mL) was added and the mixture was washed with EA (100 mL). The aqueous layer was adjusted with 1N HCl to pH<7, then extracted with EA (300 mL). The organic layer was dried over $Na_2SO_4$, filtered and concentrated to give (S)-2-(tert-butoxycarbonyl)-7-hydroxy-1,2,3,4-tetrahydroisoquinoline-3-carboxylic acid (3 g, 80% yield) as a yellow solid. $^1H$ NMR (400 MHz, DMSO-$d_6$) δ 12.58 (s, 1H), 9.26 (s, 1H), 6.97 (t, J=8.4 Hz, 1H), 6.58-6.52 (m, 2H), 4.83-4.25 (m, 3H), 3.01-2.96 (m, 2H), 1.45-1.39 (d, J=26.4 Hz, 9H). LC-MS (ESI$^+$): m/z 294.4 $(M+H)^+$.

Step 4—(S)-tert-butyl7-hydroxy-3-(((R)-1,2,3,4-tetrahydronaphthalen-1-yl)carbamoyl)-3,4-dihy droisoquinoline-2(1H)-carboxylate To a mixture of (S)-2-(tert-butoxycarbonyl)-7-hydroxy-1,2,3,4-tetrahydroisoquinoline -3- carboxylic acid (32 g, 109 mmol) and (R)-1,2,3,4-tetrahydronaphthalen-1-amine (19.3 g, 131 mmol, CAS #23357-46-2) in DMF (150 mL) was added HATU (54 g, 142 mmol) and DIPEA (42 g, 328 mmol), and the mixture was stirred at rt for 15 min. The solution was then poured into water(1500 mL) and extracted with EtOAc (200 mL×2). The combined organic layer was washed with brine (500 mL×3), dried over $Na_2SO_4$, filtered, concentrated in vacuo and purified via column chromatography (Petroleum ether/EtOAc=4/1) to give the title compound (40.2 g, 86.9% yield) as a white solid. LC-MS (ESI$^+$): m/z 423.1 $(M+H)^+$

Step 5—(S)-7-hydroxy-N—((R)-1,2,3,4-tetrahydronaphthalen-1-yl)-1,2,3,4-tetrahydroisoquino line -3-carboxamide hydrochloride To a mixture of (S)-tert-butyl7-hydroxy-3-(((R)-1,2,3,4-tetrahydronaphthalen-1-yl) carbamoyl)-3,4-dihy droisoquinoline-2(1H)-carboxylate (44 g, 104 mmol) in THE (300 mL) was added 4N HCl in dioxane(300 mL), and the mixture was stirred at rt overnight. The solution was concentrated under reduced pressure to give the crude product, which was recrystallized by EA to give the title compound (33.3 g, 82.0% yield) as a white solid. LC-MS (ESI$^+$): m/z 323.1 $(M+H)^+$.

Step 6—tert-butyl ((S)-1-((S)-7-hydroxy-3-(((R)-1,2,3,4-tetrahydronaphthalen-1-yl) carbamoyl)-3,4-dihydroisoquinolin-2(1H)-yl)-3,3-dimethyl-1-oxobutan-2-yl)carbamate To a mixture of (S)-7-hydroxy-N—((R)-1,2,3,4-tetrahydronaphthalen-1-yl)-1,2,3,4-tetrahydroisoquinoline-3-carboxamidehydrochloride(33.3 g, 92.8 mmol) and (S)-2-((tert-butoxy carbonyl)amino)-3,3-dimethylbutanoic acid (22.5, 97.4 mmol, CAS #62963-35-9) in DMF (400 mL) was added HATU (42.3 g, 111.3 mmol) and DIPEA (48 g, 371 mmol), and the mixture was stirred at rt for 1.5 h. The solution was then poured into water (2500 mL) and the mixture was extracted with EtOAc (200 mL×2). The combined organic layer was washed with brine (500 mL×3), dried over $Na_2SO_4$, filtered, concentrated in vacuo and purified via column chromatography (Petroleum ether/EtOAc=2/1) to give the title compound (21.5 g, 43.9% yield) as a white solid. LC-MS ($ESI^+$): m/z 536.2 $(M+H)^+$.

Step 7—(S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide hydrochloride To a mixture of tert-butyl ((S)-1-((S)-7-hydroxy-3-(((R)-1,2,3,4-tetrahydronaphthalen-1-yl) carbamoyl)-3,4-dihydroisoquinolin-2(1H)-yl)-3,3-dimethyl-1-oxobutan-2-yl) carbamate (21.5 g, 40 mmol) in THE (200 mL) was added 4N HCl in dioxane(200 mL), and the mixture was stirred at rt overnight. The solution was then poured into aq.$NaHCO_3$ (1000 mL), and the mixture was extracted with EtOAc (200 mL×2). The combined organic layer was washed with brine (500 mL×3), dried over $Na_2SO_4$, filtered, and concentrated in vacuo to give the title compound as the HCl salt (17 g, 97% yield) as a white solid. LC-MS ($ESI^+$): m/z 436.1 $(M+H)^+$.

Step 8—(S)-7-hydroxy-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide To a mixture of (S)-2-((S)-2-amino-3,3-dimethylbutanoyl)-7-hydroxy-N— ((R)-1,2,3,4- tetrahy dronaphthalen-1-yl)-1,2,3,4-tetrahydroisoquinoline-3-carboxamide hydrochloride (14.4 g, 33 mmol) and 2-methoxyacetic acid (2.97 g, 131 mmol) in DMF (120 mL) was added HATU (15 g, 39.6 mmol) and DIPEA (6.4 g, 49.5 mmol), and the mixture was stirred at rt for 1 h. The solution was then poured into water (1500 mL), and the mixture was extracted with EtOAc (200 mL×2). The combined organic layer was washed with brine (500 mL×3), dried over $Na_2SO_4$, filtered, concentrated in vacuo and purified via column chromatography (Petroleum ether/EtOAc=1/1) to give the title compound (14 g, 83.8% yield) as a white solid. LC-MS ($ESI^+$): m/z 508.2 $(M+H)^+$.

Benzyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (Intermediate PE)

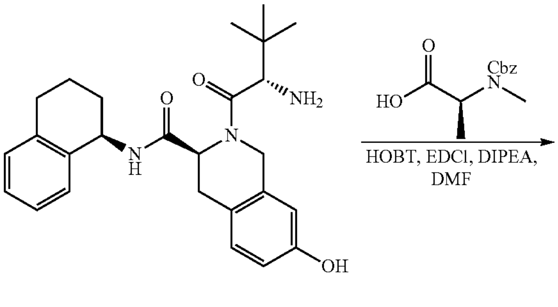

-continued

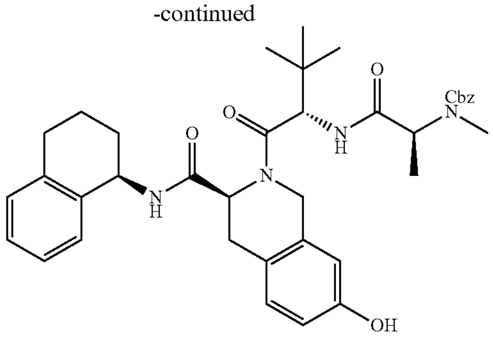

PE

To a solution of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide (13.45 g, 30.92 mmol, synthesized via Steps 1-7 of Intermediate MH), (S)-2-(((benzyloxy)carbonyl)(methyl)amino)propanoic acid (7.70 g, 32.47 mmol, CAS #21691-41-8) in DMF (150 mL) was added HOBT (4.59 g, 34.01 mmoL), EDCI (6.53 g, 34.01 mmoL), and DIPEA (9.97 g, 77.30 mmoL) at rt. The reaction mixture was stirred at r.t. for 4 h. The mixture was then concentrated under reduce pressure. Then the mixture was poured into $H_2O$ (200 mL), extracted with EA (3×100 mL), and the combined organic layers were dried over anhydrous $Na_2SO_4$. The solid was filtered and the filtrate was concentrated under reduced pressure. The crude product was purified by silica gel chromatography eluted with DCM/MEOH=10:1 to give the title compound (13.7 g, 63% yield) as a white solid. LC/MS (ESI, m/z): $[M+1]^+$ =655.4.

5-Fluoro-6-methylpicolinamide (Intermediate BBU)

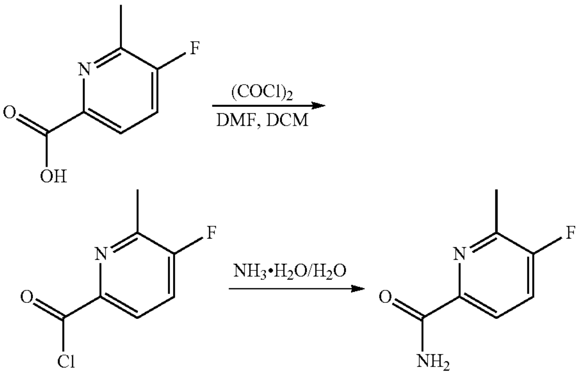

BBU

Step 1—5-Fluoro-6-methylpicolinoyl chloride

To a solution of 5-fluoro-6-methyl-pyridine-2-carboxylic acid (1.00 g, 6.45 mmol, CAS #1005474-88-3) in DCM (10 mL) was added $(COCl)_2$ (1.64 g, 12.9 mmol) and DMF (47.1 mg, 644 umol) at 0° C. The reaction mixture was stirred at 25° C. for 16 hrs. On completion, the reaction mixture was concentrated to give the title compound (1.00 g, 89% yield) as a red solid.

Step 2—5-Fluoro-6-methylpicolinamide

To a solution of 5-fluoro-6-methyl-pyridine-2-carbonyl chloride (1.00 g, 5.76 mmol) in THE (5 mL) was added into $NH_3.H_2O$ (33.3 mL, 30% solution) at 0° C. The reaction mixture was stirred at 25° C. for 10 min. On completion, the reaction mixture was extracted with ethyl acetate (3×20 mL). The combined organic layers were dried over anhydrous sodium sulfate, filtered and concentrated to give the title compound (850 mg, 96% yield) as a brown solid. $^1H$ NMR (400 MHz, DMSO-$d_6$) δ 7.91 (m, 1H), 7.86 (dd, J=8.4, 4.0 Hz, 1H), 7.70 (t, J=8.8 Hz, 1H), 7.57 (m, 1H), 2.45 (s, 3H).

5-Fluoro-N-(2-((1r,4r)-4-formylcyclohexyl)-6-methoxy-2H-indazol-5-yl)-6-methylpicolinamide (Intermediate BBV)

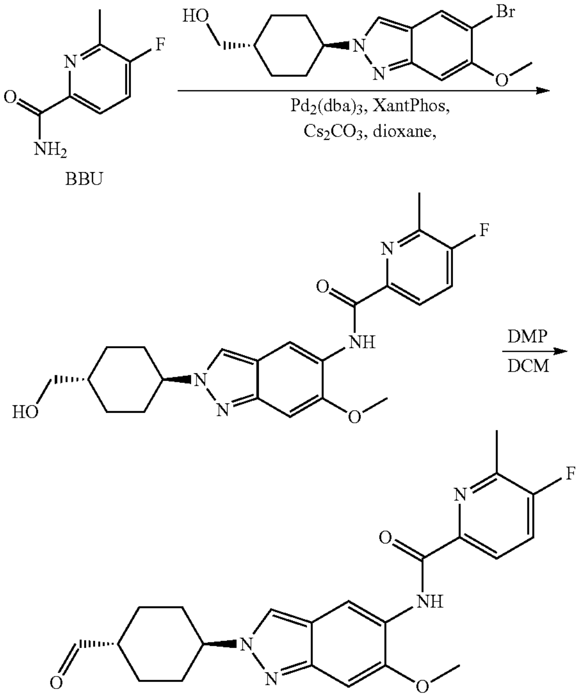

BBU

BBV

Step 1—5-Fluoro-N-(2-((1r,4r)-4-(hydroxymethyl) cyclohexyl)-6-methoxy-2H-indazol-5-yl)-6-methylpicolinamide A solution of ((1r,4r)-4-(5-bromo-6-methoxy-2H-indazol-2-yl)cyclohexyl)methanol (1.72 g, 5.06 mmol, synthesized via Steps 1-3 of Intermediate ATE), 5-fluoro-6-methyl-pyridine-2-carboxamide (650 mg, 4.22 mmol, Intermediate BBU), $Cs_2CO_3$ (2.75 g, 8.43 mmol), $Pd_2(dba)_3$ (386 mg, 421 umol) and Xantphos (488 mg, 843 umol) in dioxane (50 mL) was stirred under nitrogen atmosphere at 80° C. for 16 hrs. On completion, the mixture was quenched with water (250 mL) and extracted with ethyl acetate (3×350 mL). The combined organic phase was dried over anhydrous sodium sulfate, filtered and concentrated to give a residue. The residue was triturated with EA (30 mL) at 30° C. for 5 min to give the title compound (940 mg, 54% yield) as a brown solid. LC-MS ($ESI^+$) m/z 413.4 $(M+H)^+$. $^1H$ NMR (400 MHz, DMSO-$d_6$) δ 10.51 (s, 1H), 8.66 (s, 1H), 8.31 (s, 1H), 8.08 (d, J=8.4 Hz, 1H), 7.89 (t, J=8.8 Hz, 1H), 7.14 (s, 1H), 4.51 (t, J=5.2 Hz, 1H), 4.34 (t, J=11.2 Hz, 1H), 4.00 (s, 3H), 3.32-3.27 (m, 2H), 2.59 (d, J=2.8 Hz, 3H), 2.14 (d, J=10.0 Hz, 2H), 1.95-1.81 (m, 4H), 1.53-1.42 (m, 1H), 1.22-1.07 (m, 2H).

Step 2—5-Fluoro-N-(2-((1r,4r)-4-formylcyclohexyl)-6-methoxy-2H-indazol-5-yl)-6- methylpicolinamide A solution of 5-fluoro-N-(2-((1r,4r)-4-(hydroxymethyl) cyclohexyl)-6-methoxy-2H-indazol-5-yl)-6-methylpicolinamide (400 mg, 969 umol) and DMP (493 mg, 1.16 mmol q) in DCM (10 mL) was stirred at −5° C. for 1 hr. On completion, the reaction mixture was quenched with saturated solution of sodium thiosulfate (10 mL), then the mixture was diluted with water (100 mL) and extracted with DCM (3×300 mL). The combined organic phase was washed with sodium bicarbonate solution, dried over anhydrous sodium sulfate, filtered and concentrated to give a residue. The residue was triturated with EA (50 mL) at 30° C. for 5 min to give the title compound (350 mg, 87% yield) as a brown solid. LC-MS ($ESI^+$) m/z 411.4 $(M+H)^+$. $^1H$ NMR (400 MHz, DMSO-$d_6$) δ 10.51 (s, 1H), 9.65 (s, 1H), 8.67 (s, 1H), 8.31 (s, 1H), 8.09 (d, J=3.6, 8.4 Hz, 1H), 7.89 (t, J=8.8 Hz, 1H), 7.14 (s, 1H), 4.39 (t, J=11.6 Hz, 1H), 4.00 (s, 3H), 2.59 (d, J=2.8 Hz, 3H), 2.47-2.37 (m, 1H), 2.25-2.07 (m, 4H), 2.00-1.92 (m, 2H), 1.45 (d, J=13.2 Hz, 2H).

3-[4-[(1R,5S)-3,8-Diazabicyclo[3.2.1]octan-3-yl]-3-methyl-2-oxo-benzimidazol-1-yl]piperidine-2,6-dione (Intermediate BBW)

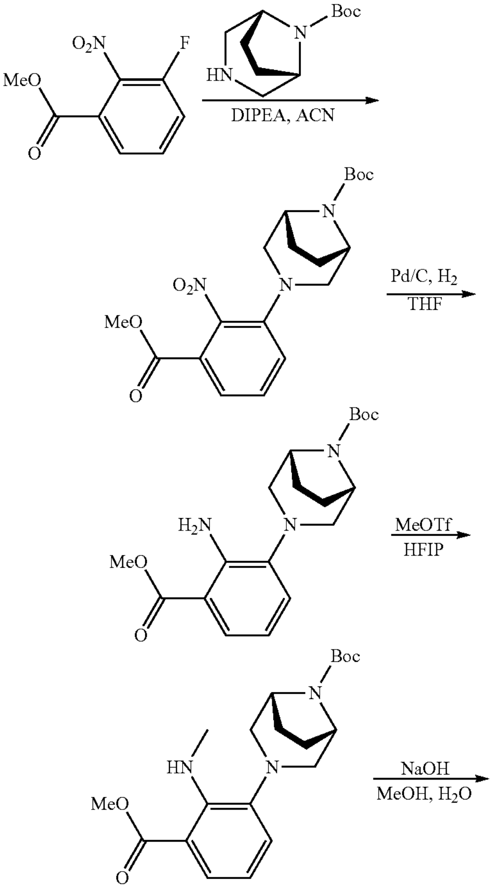

-continued

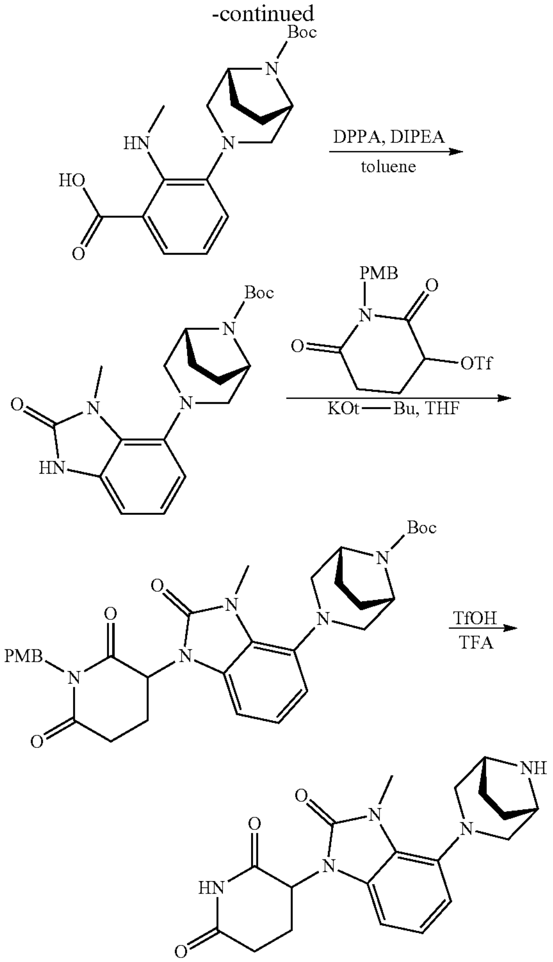

BBW

Step 1—Tert-butyl (1R,5S)-3-(3-methoxycarbonyl-2-nitro-phenyl)-3,8-diazabicyclo[3.2.1]octane-8-carboxylate To a solution of methyl 3-fluoro-2-nitro-benzoate (2.14 g, 10.7 mmol) in ACN (50 mL) was added tert-butyl (1R, 5S)-3,8-diazabicyclo[3.2.1]octane-8-carboxylate (2.50 g, 11.7 mmol). Then DIPEA (2.77 g, 21.4 mmol) was added and the reaction mixture was stirred at 70° C. for 16 hrs. On completion, the mixture was poured into water (100 mL). The mixture was filtered and the filtered cake was collected to give the title compound (2.50 g, 55% yield) as an off-white solid. LC-MS (ESI$^+$) m/z 392.2 (M+H)$^+$.

Step 2—Tert-butyl (1R,5S)-3-(2-amino-3-methoxycarbonyl-phenyl)-3,8-diazabicyclo[3.2.1]octane-8-carboxylate To a solution of tert-butyl(1R,5S)-3-(3-methoxycarbonyl-2-nitro-phenyl)-3,8-diazabicyclo[3.2.1] octane-8-carboxylate (2.50 g, 6.39 mmol) in THE (25 mL) was added Pd/C (10.0 g, 5 wt %). The reaction mixture was stirred at 25° C. for 16 hrs under $H_2$ (15 Psi) atmosphere. On completion, the reaction mixture was filtered and the filtrate was concentrated to give the title compound (2.00 g, 79% yield) as an off-white solid. LC-MS (ESI$^+$) m/z 362.2 (M+H)$^+$.

Step 3—Tert-butyl(1R,5S)-3-[3-methoxycarbonyl-2-(methylamino)phenyl]-3,8-diazabicyclo[3.2.1] octane-8-carboxylate To a solution of tert-butyl (1R,5S)-3-(2-amino-3-methoxycarbonyl-phenyl)-3,8-diazabicyclo[3.2.1] octane-8-carboxylate (2.00 g, 5.53 mmol) in 1,1,1,3,3,3-hexafluoro-propan-2-ol (20 mL) was added MeOTf (998 mg, 6.09 mmol). The reaction mixture was stirred at 25° C. for 2 hrs. On completion, the mixture was quenched with $NaHCO_3$ (20 mL) and extracted with ethyl acetate (3x25 mL). The combined organic phase was dried over anhydrous sodium sulfate and concentrated to give a residue. The residue was purified by reversed-phase HPLC (0.1% FA condition) to give the title compound (1.80 g, 73% yield) as yellow oil. $^1H$ NMR (400 MHz, DMSO-$d_6$) δ 8.07-8.02 (m, 1H), 7.41-7.36 (m, 1H), 7.23-7.16 (m, 1H), 6.78-7.68 (m, 1H), 5.20-5.10 (m, 1H), 4.23-4.10 (m, 2H), 3.84-3.79 (m, 3H), 2.89-2.73 (m, 7H), 1.99-1.85 (m, 4H), 1.45-1.43 (m, 8H). LC-MS (ESI$^+$) m/z 376.4 (M+1)$^+$.

Step 4—3-[(1R,5S)-8-Tert-butoxycarbonyl-3,8-diazabicyclo[3.2.1]octan-3-yl]-2-(methylamino) benzoic acid To a solution of tert-butyl (1R, 5S)-3-[3-methoxycarbonyl-2-(methylamino)phenyl]-3,8-diazabicyclo [3.2.1]octane-8-carboxylate (1.80 g, 4.79 mmol) in MeOH (15 mL) was added $H_2O$ (3 mL) and NaOH (575 mg, 14.3 mmol). The reaction mixture was stirred at 60° C. for 2 hrs. On completion, the solvent was concentrated to remove MeOH, the residue was diluting with water (20 ml), then adjusted pH to around 5 with HCl (2 N). Then the mixture was extracted with ethyl acetate (3x25 mL), the combined organic phase was dried over anhydrous sodium sulfate, filtered and concentrated to give the title compound (1.80 g, 99% yield) as an off-white solid. $^1H$ NMR (400 MHz, DMSO-$d_6$) δ 7.51-7.49 (m, 1H), 7.24-7.18 (m, 1H), 6.81-6.75 (m, 1H), 4.21-4.14 (m, 2H), 2.99-2.93 (m, 2H), 2.89 (s, 3H), 2.78-2.73 (m, 2H), 2.03-1.82 (m, 5H), 1.51-1.36 (m, 10H), LC-MS (ESI$^+$) m/z 362.1 (M+1)$^+$.

Step 5—Tert-butyl (1R,5S)-3-(3-methyl-2-oxo-1H-benzimidazol-4-yl)-3,8-diazabicyclo[3.2.1]octane-8-carboxylate To a solution of 3-[(1R,5S)-8-tert-butoxycarbonyl-3,8-diazabicyclo[3.2.1]octan-3-yl]-2- (methylamino)benzoic acid (1.80 g, 4.98 mmol) in toluene (20 mL) was added DPPA (1.37 g, 4.98 mmol) and DIPEA (1.93 g, 14.9 mmol). The reaction mixture was stirred at 85° C. for 16 hrs. On completion, the mixture was quenched with water (2 mL) and concentrated to give a residue. The residue was purified by reversed-phase HPLC (0.1% $NH_3.H_2O$ condition) to give the title compound (1.10 g, 61% yield) as a brown solid. $^1H$ NMR (400 MHz, DMSO-$d_6$) δ 10.87 (s, 1H), 6.97-6.89 (m, 2H), 6.81-6.79 (m, 1H), 4.25-4.18 (m, 2H), 3.68-3.64 (m, 3H), 2.98-2.92 (m, 2H), 2.89-2.83 (m, 2H), 2.03-1.99 (m, 2H), 1.91-1.87 (m, 2H), 1.47-1.43 (m, 9H), LC-MS (ESI$^+$) m/z 359.2 (M+1)$^+$.

Step 6—Tert-butyl(1R,5S)-3-[1-[1-[(4-methoxyphenyl)methyl]-2,6-dioxo-3-piperidyl]-3-methyl-2-oxo-benzimidazol-4-yl]-3,8-diazabicyclo[3.2.1]octane-8-carboxylate To a solution of tert-butyl (1R,5S)-3-(3-methyl-2-oxo-1H-benzimidazol-4-yl)-3,8-diazabicyclo[3.2.1] octane-8-carboxylate (1.00 g, 2.79 mmol) in THE (10 mL) was added t-BuOK (469 mg, 4.18 mmol). The reaction mixture was stirred at 0° C. for 30 min. Then [1-[(4-methoxyphenyl) methyl]-2,6-dioxo-3- piperidyl]trifluoromethanesulfonate (1.60 g, 4.18 mmol) was added. The reaction mixture was stirred at 0° C. for 2 hrs. On completion, the mixture was quenched with water (2 mL) and extracted with ethyl acetate (3×25 mL). The combined organic phase was dried over anhydrous sodium sulfate, filtered and concentrated to give a residue. The residue was purified by reversed-phase HPLC (0.1% FA condition) to give the title compound (1.00 g, 39% yield) as a brown solid. $^1$H NMR (400 MHz, DMSO-$d_6$) δ 7.21 (d, J=8.8 Hz, 2H), 7.03-6.92 (m, 2H), 6.88-6.81 (m, 3H), 5.51 (dd, J=5.2, 12.8 Hz, 1H), 4.90-4.65 (m, 2H), 4.19 (s, 2H), 3.72 (s, 3H), 3.71 (s, 3H), 3.09-2.66 (m, 7H), 2.06-1.95 (m, 3H), 1.88 (d, J=3.2 Hz, 2H), 1.50-1.40 (m, 9H).

Step 7—3-[4-[(1R,5S)-3,8-Diazabicyclo[3.2.1]octan-3-yl]-3-methyl-2-oxo-benzimidazol-1-yl]piperidine-2,6-dione To a solution of tert-butyl (1R,5S)-3-[1-[1-[(4-methoxyphenyl)methyl]-2,6-dioxo-3-piperidyl]-3-methyl-2-oxo-benzimidazol-4-yl]-3,8-diazabicyclo[3.2.1]octane-8-carboxylate (1.00 g, 1.70 mmol) in TFA (10 mL) was added TfOH (1 mL). The reaction mixture was stirred at 25° C. for 16 hrs. On completion, the mixture was quenched with water (2 mL) and extracted with ethyl acetate (3×25 mL). The combined organic phase was dried over anhydrous sodium sulfate, filtered and concentrated to give a residue. The residue was purified by reversed-phase HPLC (0.1% FA condition) to give the title compound (500 mg, 31% yield) as a blue solid. $^1$H NMR (400 MHz, DMSO-$d_6$) δ 11.11 (d, J=1.2 Hz, 1H), 8.28 (s, 1H), 7.09-7.06 (m, 2H), 6.99 (dd, J=3.2, 5.6 Hz, 1H), 5.38 (dd, J=5.2, 12.4 Hz, 1H), 4.03 (s, 2H), 3.70 (s, 3H), 3.25 (s, 1H), 3.01 (d, J=10.0 Hz, 2H), 2.93-2.85 (m, 1H), 2.73-2.64 (m, 1H), 2.14 (d, J=8.0 Hz, 2H), 2.08 (s, 2H), 2.00-1.94 (m, 3H).

Tert-butyl N-[2-[3-(bromomethyl)cyclobutoxy]ethyl]-N-methyl-carbamate (Intermediate BBX)

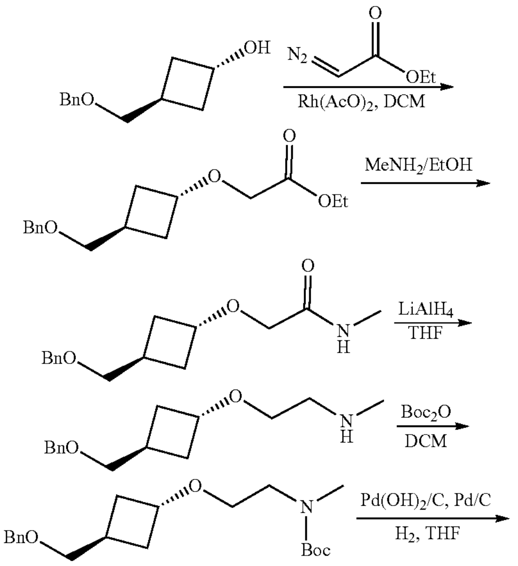

-continued

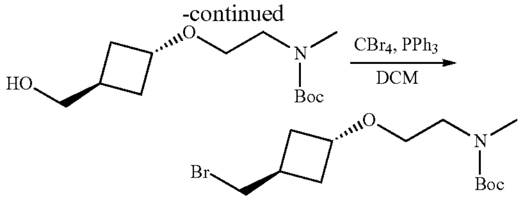

BBX

Step 1—Ethyl 2-[3-(benzyloxymethyl)cyclobutoxy]acetate

To a solution of 3-(benzyloxymethyl)cyclobutanol (4.00 g, 20.8 mmol, synthesized via Step 1 of Intermediate ART) and $Rh(OAc)_2$ (184 mg, 832 umol) in DCM (100 mL) was added a solution of ethyl 2-diazoacetate (4.75 g, 41.6 mmol, CAS #623-74-4) in DCM (40 mL) dropwise at 20° C. Then the reaction mixture was stirred at 20° C. for 12 hrs. On completion, the mixture was quenched with water (100 mL), then extracted with DCM (2×50 mL). The organic layer was washed with brine (100 mL), concentrated in vacuo. The residue was purified by silica gel chromatography ($SiO_2$) to give the title compound (5.79 g, 86% yield) as yellowish oil. $^1$H NMR (400 MHz, $CDCl_3$) δ 7.38-7.28 (m, 5H), 4.53 (s, 2H), 4.25-4.17 (m, 2H), 3.97 (s, 2H), 3.46 (d, J=6.8 Hz, 2H), 2.52-2.48 (m, 1H), 2.22-2.13 (m, 3H), 1.36-1.29 (m, 3H).

Step 2—2-[3-(Benzyloxymethyl)cyclobutoxy]-N-methyl-acetamide

A solution of ethyl 2-[3-(benzyloxymethyl)cyclobutoxy] acetate (5.00 g, 18.0 mmol) in $MeNH_2$/EtOH (40 mL) was added into a tube. Then the reaction mixture was stirred at 80° C. for 12 hrs. On completion, the mixture was concentrated in vacuo. The residue was purified by silica gel chromatography ($SiO_2$) to give the title compound (4.73 g, 85% yield) as yellowish oil. $^1$H NMR (400 MHz, $CDCl_3$) δ 7.40-7.27 (m, 5H), 6.57 (s, 1H), 4.53 (s, 2H), 4.17-4.03 (m, 1H), 3.83 (s, 2H), 3.46 (d, J=6.4 Hz, 2H), 2.86 (d, J=5.2 Hz, 3H), 2.61-2.43 (m, 1H), 2.17-2.09 (m, 4H).

Step 3—2-[3-(Benzyloxymethyl)cyclobutoxy]-N-methyl-ethanamine

To a solution of 2-[3-(benzyloxymethyl)cyclobutoxy]-N-methyl-acetamide (4.00 g, 15.2 mmol,) in THE (50 mL) was added $LiAlH_4$ (865 mg, 22.8 mmol,) at 0° C. Then the reaction mixture was stirred at 60° C. for 12 hrs. On completion, the mixture was quenched with water (870 mL) and 15% aqueous NaOH (2.50 mL), dried with $Na_2SO_4$, stirred and filtered. The filtrate was concentrated in vacuo to give the title compound (3.79 g, 92% yield) as yellow oil. $^1$H NMR (400 MHz, $CDCl_3$) δ 7.38-7.27 (m, 5H), 4.53 (s, 2H), 4.05 (t, J=6.8 Hz, 1H), 3.50-3.39 (m, 4H), 2.73 (t, J=5.2 Hz, 2H), 2.56-2.47 (m, 1H), 2.45 (s, 3H), 2.10 (t, J=6.8 Hz, 4H).

Step 4—Tert-butyl N-[2-[3-(benzyloxymethyl)cyclobutoxy]ethyl]-N-methyl-carbamate To a solution of 2-[3-(benzyloxymethyl)cyclobutoxy]-N-methyl-ethanamine (3.50 g, 14.0 mmol,) and $Boc_2O$ (3.37 g, 15.4 mmol) in DCM (40 mL) was added TEA (2.13 g, 21.1 mmol). The reaction mixture was stirred at 20° C. for 12 hrs. On completion, the mixture was concentrated in vacuo. The residue was purified by silica gel chromatography ($SiO_2$) to give the title compound (4.40 g, 90% yield) as colorless oil. $^1H$ NMR (400 MHz, $CDCl_3$) δ 7.34-7.20 (m, 5H), 4.46 (s, 2H), 3.96 (m, 1H), 3.39 (d, J=6.8 Hz, 2H), 3.37-3.23 (m, 4H), 2.84 (s, 3H), 2.50-2.33 (m, 1H), 2.06-1.95 (m, 4H), 1.38 (s, 9H).

Step 5—Tert-butyl N-[2-[3-(hydroxymethyl)cyclobutoxy]ethyl]-N-methyl-carbamate

To a solution of tert-butyl N-[2-[3-(benzyloxymethyl) cyclobutoxy]ethyl]-N-methyl-carbamate (3.80 g, 10.9 mmol) in THE (50 mL) was added $Pd(OH)_2/C$ (0.50 g, 20 wt %) and Pd/C (0.50 g, 10 wt %). The reaction mixture was stirred at 50° C. for 12 hrs under $H_2$ (50 psi) atmosphere. On completion, the mixture was filtered and the filtrate was concentrated in vacuo to give a title compound (2.71 g, 96% yield) as yellowish oil. $^1H$ NMR (400 MHz, DMSO-$d_6$) δ 4.54 (t, J=4.8 Hz, 1H), 3.99 (m, 1H), 3.40-3.33 (m, 4H), 3.29-3.23 (m, 2H), 2.79 (s, 3H), 2.20 (m, 1H), 2.02-1.94 (m, 2H), 1.92-1.82 (m, 2H), 1.39 (s, 9H).

Step 6—Tert-butyl N-[2-[3-(bromomethyl)cyclobutoxy]ethyl]-N-methyl-carbamate

A mixture of tert-butyl N-[2-[3-(hydroxymethyl)cyclobutoxy]ethyl]-N-methyl-carbamate (2.70 g, 10.4 mmol), $PPh_3$ (5.46 g, 20.8 mmol) in DCM (40 mL) was added $CBr_4$ (6.91 g, 20.8 mmol) at 0° C. The reaction mixture was stirred at 20° C. for 12 hrs. On completion, the mixture was concentrated in vacuo. The residue was purified by silica gel chromatography ($SiO_2$) to give the title compound (2.17 g, 65% yield) as yellow oil. $^1H$ NMR (400 MHz, DMSO-$d_6$) δ 4.11-4.02 (m, 1H), 3.61 (d, J=8.0 Hz, 2H), 3.38-3.33 (m, 2H), 3.30-3.25 (m, 2H), 2.92-2.76 (m, 4H), 2.00 (t, J=6.4 Hz, 4H), 1.38 (s, 9H).

3-[3-Methyl-4-[[3-[2-(methylamino)ethoxy]cyclobutyl]methyl]-2-oxo-benzimidazol-1-yl]piperidine-2,6-dione (Intermediate BBY)

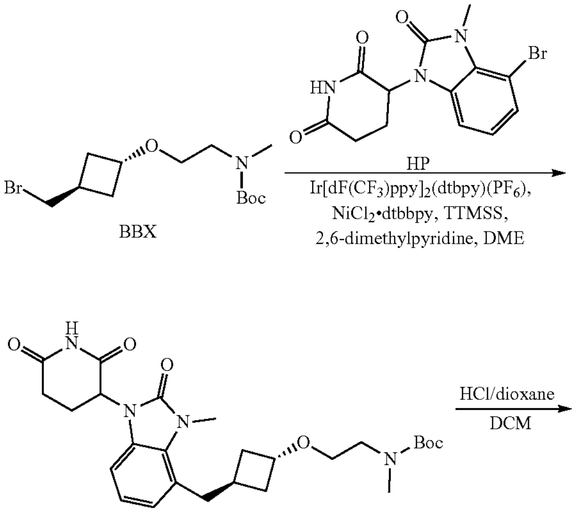

BBX

-continued

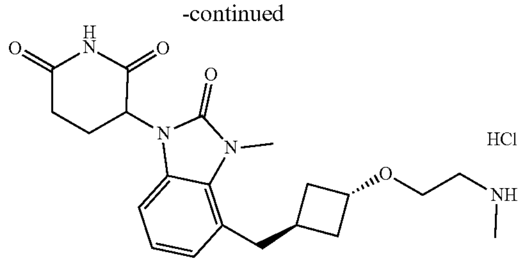

BBY

Step 1—Tert-butyl N-[2-[3-[[1-(2,6-dioxo-3-piperidyl)-3-methyl-2-oxo-benzimidazol-4-yl]methyl] cyclobutoxy]ethyl]-N-methylcarbamate To an 40 mL vial equipped with a stir bar was added photocatalyst, 3-(4-bromo-3-methyl-2-oxo-benzimidazol-1-yl)piperidine-2,6-dione (400 mg, 1.18 mmol, Intermediate HP), tert-butyl N-[2-[3-(bromomethyl)cyclobutoxy]ethyl]-N-methyl-carbamate (496 mg, 1.54 mmol Intermediate BBX), $Ir[dF(CF_3)ppy]_2$ (dtbpy)($PF_6$) (13.3 mg, 11.83 umol), $NiCl_2$.dtbbpy (2.35 mg, 5.91 umol), TTMSS (294 mg, 1.18 mmol,), 2,6-dimethylpyridine (253 mg, 2.37 mmol) in DME (10 mL). The vial was sealed and placed under nitrogen was added. The reaction was stirred and irradiated with a 34 W blue LED lamp (7 cm away), with cooling fan to keep the reaction temperature at 25° C. for 14 hrs. On completion, the reaction mixture was concentrated under reduced pressure. The residue was purified by reversed-phase HPLC (0.1% FA condition) to give a title compound (170 mg, 57% yield) as a white solid. $^1H$ NMR (400 MHz, DMSO-$d_6$) δ 11.24-10.91 (m, 1H), 7.04-6.91 (m, 2H), 6.88-6.79 (m, 1H), 5.41-5.32 (m, 1H), 4.22-4.10 (m, 1H), 3.54 (s, 3H), 3.35 (s, 2H), 3.29-3.25 (m, 2H), 3.06 (d, J=7.6 Hz, 2H), 2.94-2.85 (m, 1H), 2.84-2.75 (m, 3H), 2.74-2.52 (m, 3H), 2.09-1.90 (m, 5H), 1.38 (s, 9H).

Step 2—3-[3-Methyl-4-[[3-[2-(methylamino)ethoxy] cyclobutyl]methyl]-2-oxo-benzimidazol-1-yl]piperidine-2,6-dione To a solution of tert-butyl N-[2-[3-[[1-(2,6-dioxo-3-piperidyl)-3-methyl-2-oxo-benzimidazol-4-yl]methyl]cyclobutoxy]ethyl]-Nmethyl-carbamate (170 mg, 340 umol) in DCM (3 mL) was added HCl/dioxane (3 mL). The reaction mixture was stirred at 20° C. for 1 hr. On completion, the reaction mixture was concentrated under reduced pressure to give the title compound (140 mg, 94% yield, HCl salt) as a white solid. LC-MS ($ESI^+$) m/z 401.4 $(M+H)^+$ 6-(1,1-Difluoroethyl)-N-[2-(4-formylcyclohexyl)-5-methoxy-1,3-benzoxazol-6-yl]pyridine-2- carboxamide (Intermediate BBZ)

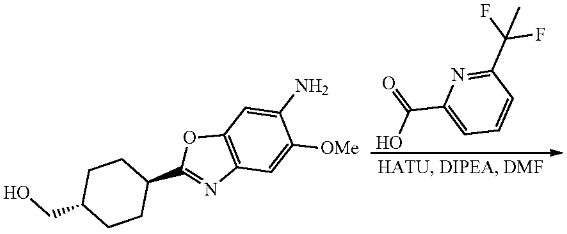

AZR

-continued

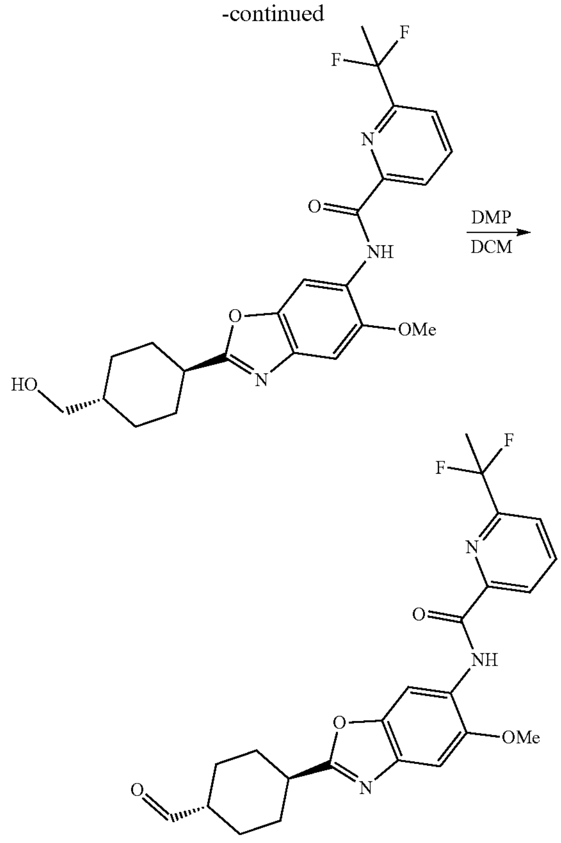

BBZ

Step 1—6-(1,1-Difluoroethyl)-N-[2-[4-(hydroxymethyl)cyclohexyl]-5-methoxy-1,3-benzoxazol-6-yl] pyridine-2-carboxamide To a solution of 6-(1,1-difluoroethyl)pyridine-2-carboxylic acid (237 mg, 1.27 mmol, CAS #1211529-86-0) in DMF (1 mL) was added DIPEA (491 mg, 3.80 mmol, 661 uL) and 2-chloro-1- methyl-pyridin-1-ium;iodide (388.31 mg, 1.52 mmol). The mixture was stirred at 25° C. for 30 minutes, then [4-(6-amino-5-methoxy-1,3-benzoxazol-2-yl) cyclohexyl]methanol (350 mg, 1.27 mmol, Intermediate AZR) was added, the reaction mixture was stirred at 25° C. for 1 hour. On completion, the reaction mixture was concentrated in vacuo to give a residue. The residue was purified by reverse phase (0.1% FA condition) to give the title compound (185 mg, 32.8% yield) as a white solid. LC-MS ($ESI^+$) m/z 446.2 $(M+1)^+$.

Step 2—6-(1,1-Difluoroethyl)-N-[2-(4-formylcyclohexyl)-5-methoxy-1,3-benzoxazol-6-yl]pyridine-2-carboxamide To a solution of 6-(1,1-difluoroethyl)-N-[2-[4-(hydroxymethyl)cyclohexyl]-5-methoxy-1,3- benzoxazol-6-yl] pyridine-2-carboxamide (180 mg, 404 umol) in DCM (5 mL) was added DMP (222 mg, 525 umol, 162 uL). The reaction mixture was stirred at 25° C. for 1 hr. On completion, the reaction mixture was quenched with $Na_2S_2O_3$ (10 mL) and extracted with DCM (2×20 mL). The combined organic phase was washed with $NaHCO_3$ and brine (2×15 mL), with anhydrous $Na_2SO_4$, filtered and concentrated in vacuo to give the title compound (175 mg, 97.6% yield) as a yellow solid. LC-MS ($ESI^+$) m/z 444.1 $(M+1)^+$.

[4-(6-Amino-5-morpholino-1,3-benzoxazol-2-yl) cyclohexyl]methanol (Intermediate BCA)

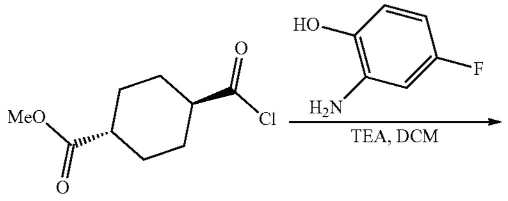

AZQ

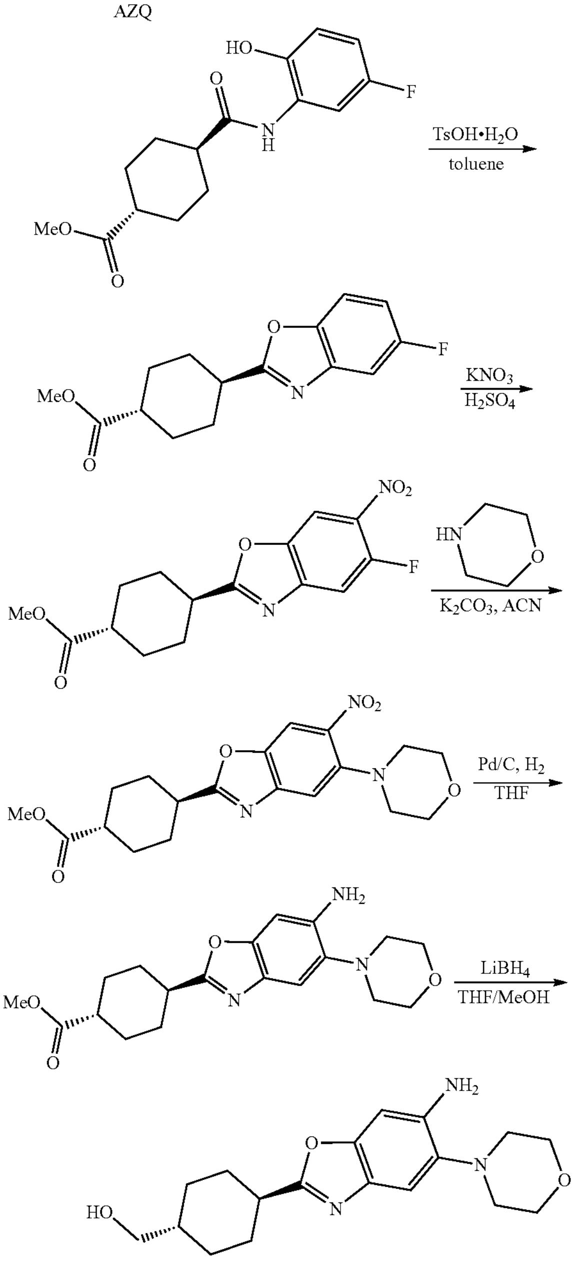

BCA

Step 1—4-[(5-Fluoro-2-hydroxy-phenyl)carbamoyl] cyclohexanecarboxylate

To a mixture of 2-amino-4-fluoro-phenol (1.24 g, 9.77 mmol, CAS #388-95-3) and TEA (2.97 g, 29.3 mmol, 4.08 mL in DCM (20 mL) was added methyl 4-chlorocarbonyl-cyclohexanecarboxylate (2.00 g, 9.77 mmol, Intermediate AZQ) at 0° C. The reaction mixture was stirred at 25° C. for 12 hours. On completion, the reaction mixture was concentrated in vacuo. The residue was purified by column chromatography to give the title compound methyl (1.90 g, 65% yield) as light yellow solid. $^1$H NMR (400 MHz, DMSO-$d_6$) δ 9.11 (s, 1H), 7.81-7.72 (m, 1H), 6.85-6.78 (m, 1H), 6.76-6.68 (m, 1H), 3.59 (s, 3H), 2.59-2.51 (m, 1H), 2.35-2.27 (m, 1H), 1.98-1.92 (m, 2H), 1.89-1.82 (m, 2H), 1.49-1.33 (m, 5H).

Step 2—Methyl 4-(5-fluoro-1,3-benzoxazol-2-yl) cyclohexanecarboxylate

To a mixture of methyl 4-[(5-fluoro-2-hydroxy-phenyl) carbamoyl]cyclohexanecarboxylate (1.90 g, 6.43 mmol) in Tol. (40 mL) was added TsOH.$H_2O$ (489 mg, 2.57 mmol). The reaction mixture was stirred at 125° C. for 12 hours. On completion, the reaction mixture was concentrated in vacuo to give the title compound (1.70 g, 95% yield) as white solid. $^1$H NMR (400 MHz, DMSO-$d_6$) δ 7.72-7.67 (m, 1H), 7.60-7.54 (m, 1H), 7.23-7.18 (m, 1H), 3.61 (s, 3H), 3.05-2.93 (m, 1H), 2.45-2.35 (m, 1H), 2.21-2.14 (m, 2H), 2.06-1.97 (m, 2H), 1.65-1.47 (m, 4H).

Step 3—Methyl 4-(5-fluoro-6-nitro-1,3-benzoxazol-2-yl)cyclohexanecarboxylate

To a mixture of methyl 4-(5-fluoro-1,3-benzoxazol-2-yl) cyclohexanecarboxylate (1.40 g, 5.05 mmol) in $H_2SO_4$ (10 mL) was added $KNO_3$ (1.53 g, 15.1 mmol) at 0° C. The reaction mixture was stirred at 0° C. for 5 hours. The reaction mixture was quenched with ice water (50 mL), where white solid formed and was filtered to give the title compound (1.40 g, 86% yield) as white solid. $^1$H NMR (400 MHz, DMSO-$d_6$) δ 8.66-8.62 (m, 1H), 8.03-7.98 (m, 1H), 3.13-3.03 (m, 1H), 2.35-2.25 (m, 1H), 2.24-2.16 (m, 2H), 2.07-1.98 (m, 2H), 1.70-1.58 (m, 2H), 1.57-1.44 (m, 2H).

Step 4—Methyl 4-(5-morpholino-6-nitro-1,3-benzoxazol-2-yl)cyclohexanecarboxylate To a mixture of methyl 4-(5-fluoro-6-nitro-1,3-benzoxazol-2-yl)cyclohexanecarboxylate (1.10 g, 3.41 mmol) and morpholine (594 mg, 6.83 mmol, 600 uL, CAS #110-91-8) in ACN (10 mL) was added $K_2CO_3$ (943 mg, 6.83 mmol). The reaction mixture was stirred at 60° C. for 12 hours. On completion, the reaction mixture was diluted with water (30 mL) and extracted with EA (2×50 mL). The combined organic layers were dried over $Na_2SO_4$, filtered and concentrated in vacuo to give a residue. The residue was purified by column chromatography to give the title compound (500 mg, 37% yield) as light yellow solid. $^1$H NMR (400 MHz, DMSO-$d_6$) δ 8.30 (s, 1H), 7.78 (s, 1H), 3.70-3.67 (m, 4H), 3.62 (s, 3H), 3.09-3.00 (m, 1H), 2.95 (d, J=4.4 Hz, 4H), 2.46-2.37 (m, 1H), 2.23-2.13 (m, 2H), 2.05-1.99 (m, 2H), 1.69-1.47 (m, 4H).

Step 5—Methyl 4-(6-amino-5-morpholino-1,3-benzoxazol-2-yl)cyclohexanecarboxylate To a mixture of methyl 4-(5-morpholino-6-nitro-1,3-benzoxazol-2-yl)cyclohexanecarboxylate (400 mg, 1.03 mmol) in THE (10 mL) was added Pd/C (300 mg, 10 wt %). The reaction mixture was stirred at 25° C. for 3 hours under $H_2$ (15 Psi) atmosphere. On completion, the reaction mixture was filtered and concentrated in vacuo to give the title compound (350 mg, 94% yield) as light yellow solid. $^1$H NMR (400 MHz, DMSO-$d_6$) δ 7.19 (s, 1H), 6.86 (s, 1H), 3.79-3.72 (m, 4H), 3.61 (s, 3H), 2.89-2.81 (m, 1H), 2.80-2.75 (m, 4H), 2.43-2.34 (m, 1H), 2.15-2.08 (m, 2H), 2.03-1.95 (m, 2H), 1.62-1.43 (m, 4H).

Step 6—[4-(6-Amino-5-morpholino-1,3-benzoxazol-2-yl)cyclohexyl]methanol

To a mixture of methyl 4-(6-amino-5-morpholino-1,3-benzoxazol-2-yl)cyclohexanecarboxylate (440 mg, 1.22 mmol) in THF (10 mL) and MeOH (1 mL) was added $LiBH_4$ (79.9 mg, 3.67 mmol) at 25° C. The reaction mixture was stirred at 50° C. for 7 hours. On completion, the reaction mixture was quenched with $NH_4Cl$ (10 mL). The reaction mixture was diluted with water (10 mL) and extracted with EA (2×20 mL). The combined organic layers were dried over $Na_2SO_4$, filtered and concentrated in vacuo to give the title compound (390 mg, 96% yield) as brown solid. LC-MS (ESI$^+$) m/z 332.2 $(M+H)^+$.

N-[2-(4-formylcyclohexyl)-5-morpholino-1,3-benzoxazol-6-yl]-6-(trifluoromethyl)pyridine -2-carboxamide (Intermediate BCB)

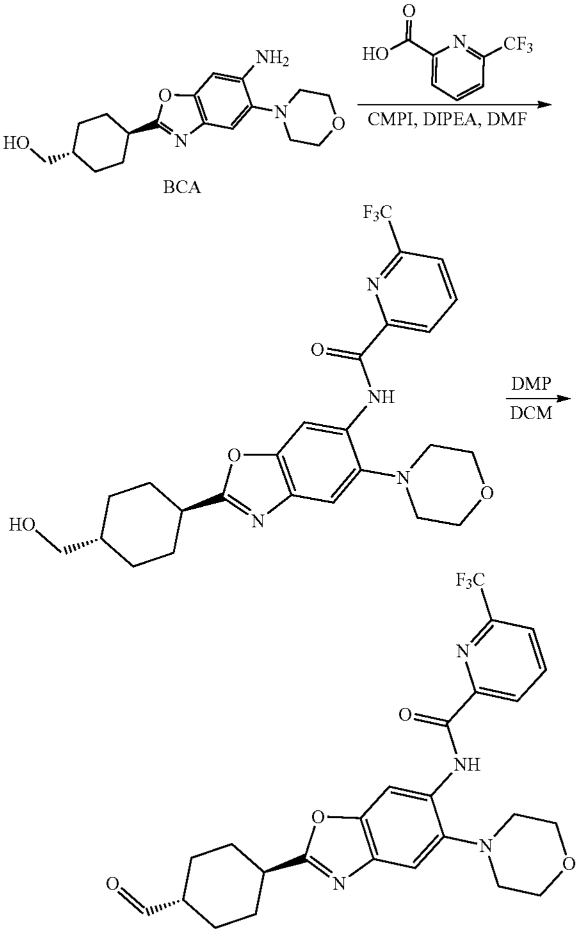

BCB

Step 1—N-[2-[4-(hydroxymethyl)cyclohexyl]-5-morpholino-1,3-benzoxazol-6-yl]-6-(trifluoromethyl)pyridine-2-carboxamide To a mixture of 6-(trifluoromethyl)pyridine-2-carboxylic acid (196 mg, 1.03 mmol, CAS #131747-42-7), CMPI (314 mg, 1.23 mmol) and DIPEA (265 mg, 2.05 mmol, 357 uL) in DMF (1 mL) was added [4-(6-amino-5-morpholino-1,3-benzoxazol-2-yl)cyclohexyl]methanol (340 mg, 1.03 mmol, Intermediate BCA). The reaction mixture was stirred at 25° C. for 1 hour. On completion, the reaction mixture was quenched with water (0.05 mL) and concentrated in vacuo. The residue was purified by reverse phase (0.1% FA condition) to give the title compound (190 mg, 36% yield) as brown solid. $^1$H NMR (400 MHz, DMSO-$d_6$) δ 11.31-11.23 (m, 1H), 8.75-8.73 (m, 1H), 8.50-8.47 (m, 1H), 8.41 (t, J=7.6 Hz, 1H), 8.23 (d, J=7.6 Hz, 1H), 7.79-7.74 (m, 1H), 3.85 (s, 4H), 3.32-3.27 (m, 2H), 3.25-3.22 (m, 1H), 2.90 (d, J=3.2 Hz, 5H), 2.19-2.14 (m, 2H), 1.91-1.82 (m, 2H), 1.59-1.50 (m, 2H), 1.14-1.01 (m, 2H); LC-MS (ESI$^+$) m/z 505.3 $(M+H)^+$.

Step 2—N-[2-(4-formylcyclohexyl)-5-morpholino-1,3-benzoxazol-6-yl]-6-(trifluoromethyl)pyridine-2-carboxamide To a mixture of N-[2-[4-(hydroxymethyl)cyclohexyl]-5-morpholino-1,3-benzoxazol-6-yl]-6- (trifluoromethyl)pyridine-2-carboxamide (140 mg, 277 umol) in DCM (5 mL) was added DMP (141 mg, 333 umol, 103 uL) at 0° C. The reaction mixture was stirred at 25° C. for 4 hours. On completion, the reaction mixture was quenched by saturated $Na_2S_2O_3$ (3 mL) and saturated $NaHCO_3$ (3 mL) at 25° C., and then stirred for 30 minutes. The mixture was extracted with DCM (2×20 mL). Then the organic layers were separated and concentrated in vacuo to give the title compound (131 mg, 93% yield) as white solid. LC-MS (ESI$^+$) m/z 503.3 $(M+H)^+$.

N-(6-cyclopropoxy-2-((1r,4r)-4-formylcyclohexyl)-2H-indazol-5-yl)-6-(1,1-difluoroethyl) picolinamide (Intermediate BCC)

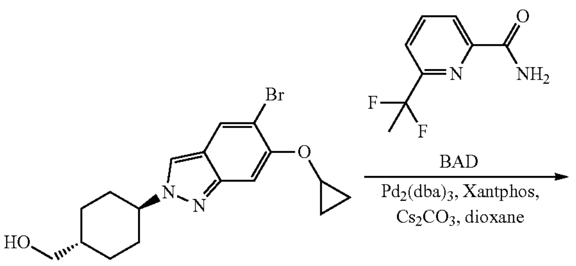

BBG

-continued

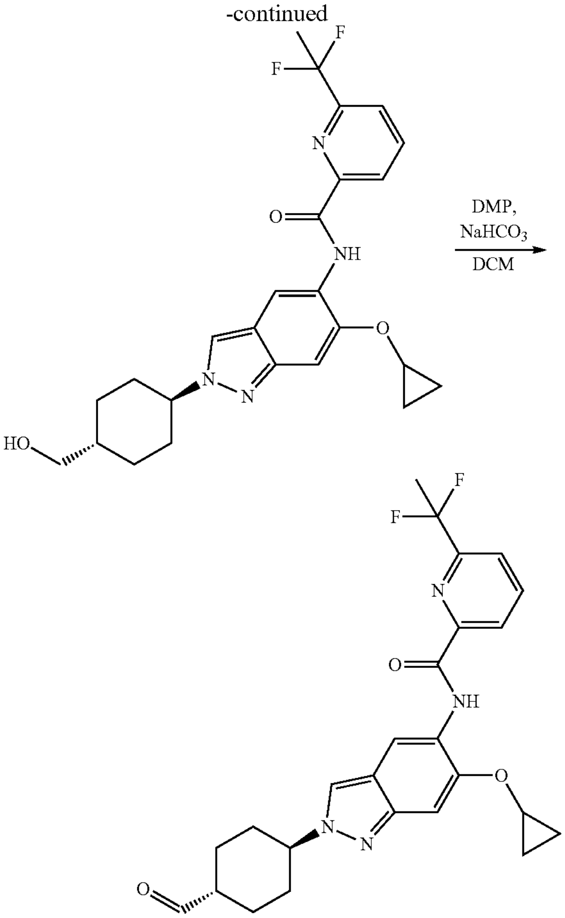

BCC

Step 1—N-(6-cyclopropoxy-2-((1r,4r)-4- (hydroxymethyl)cyclohexyl)-2H-indazol-5-yl)-6-(1,1-difluoroethyl)picolinamide To a solution of [4-[5-bromo-6-(cyclopropoxy)indazol-2-yl]cyclohexyl]methanol (200 mg, 548 umol, Intermediate BBG) and 6-(1,1-difluoroethyl)pyridine-2-carboxamide (151 mg, 821 umol, Intermediate BAD), Xantphos (63.4 mg, 110 umol) and $Cs_2CO_3$ (357 mg, 1.10 mmol) in dioxane (5 mL) was added $Pd_2(dba)_3$ (50.1 mg, 54.8 umol), it was stirred at 100° C. for 2 hours under $N_2$. On completion, the reaction mixture was filtered and the filtrate was concentrated in vacuo to give the residue. The residue was purified by prep-TLC (PE/EA=0/1) to give the title product (240 mg, 89.4% yield, 96% purity) as a yellow solid. $^1$H NMR (400 MHz, $CD_3OD$) δ 10.71 (s, 1H), 8.74 (s, 1H), 8.30 (d, J=7.6 Hz, 1H), 8.21 (m, 2H), 8.18 (d, J=6.0 Hz, 1H), 7.39 (s, 1H), 4.39 (m, 1H), 4.06 (m, 1H), 3.46 (d, J=6.0 Hz, 2H), 2.25-1.97 (m, 11H), 1.28 (m, 1H), 0.98 (m, 1H), 0.88-0.87 (m, 4H); LC-MS (ESI$^+$) m/z 471.3 $(M+H)^+$.

Step 2—N-(6-cyclopropoxy-2-((1r,4r)-4-formylcyclohexyl)-2H-indazol-5-yl)-6-(1,1-difluoroethyl) picolinamide To a mixture of N-[6-(cyclopropoxy)-2-[4-(hydroxymethyl)cyclohexyl]indazol-5-yl]-6-(trifluoro methyl)pyridine-2-carboxamide (240 mg, 506 umol) in DCM (10 mL) was added DMP (279 mg, 658 umol) and $NaHCO_3$ (212 mg, 2.53 mmol). The mixture was stirred at 25° C. for 1 hour. On completion, it was quenched with $Na_2S_2O_3$ (aq., 20 mL), washed with $NaHCO_3$ (aq., 20 mL), then extracted with EA (2×20 mL). The organic layers were dried with $Na_2SO_4$, filtered and concentrated in vacuo to give the residue. The residue was washed with a solution of (PE/EA=10/1, 30 mL) to give the title product (200 mg, 80% yield, 96% purity) as a yellow solid. LC-MS (ESI$^+$) m/z 469.2 (M+H)$^+$.

1-Methyl-3-[3-methyl-2-oxo-4-(4-piperidyl)benzimidazol-1-yl]piperidine-2,6-dione (Intermediate BCD)

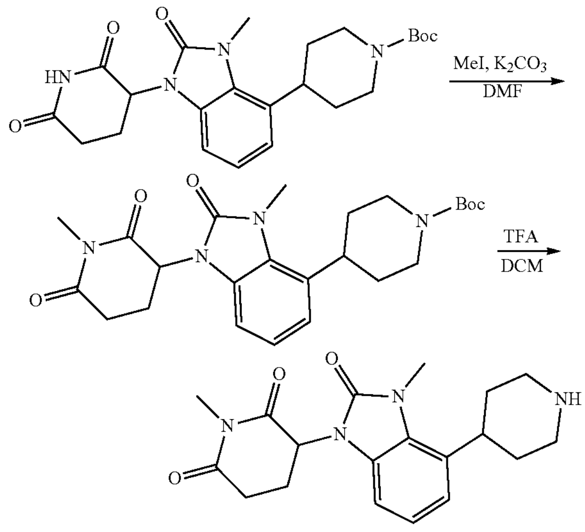

BCD

Step 1—Tert-butyl 4-[3-methyl-1-(1-methyl-2,6-dioxo-3-piperidyl)-2-oxo-benzimidazol-4- yl]piperidine-1-carboxylate To a solution of tert-butyl 4-[1-(2,6-dioxo-3-piperidyl)-3-methyl-2-oxo-benzimidazol-4-yl]piperidine-1-carboxylate (300 mg, 677 umol, synthesized via Steps 1-2 of Intermediate AZK) in DMF (4 mL) was added $K_2CO_3$ (93.7 mg, 677 umol). The reaction mixture was stirred at 0° C. for 15 min. Then MeI (192 mg, 1.36 mmol) was added and the reaction mixture was stirred at 25° C. for 4 hrs. On completion, the mixture was quenched with water (1 mL) and extracted with ethyl acetate (3×25 mL). The combined organic phase was dried over anhydrous sodium sulfate, filtered and concentrated to give a residue. The residue was triturated with $NH_4Cl$ (20 mL) at 25° C. for 15 min to give the title compound (250 mg, 80% yield) as an off-white solid. $^1H$ NMR (400 MHz, DMSO-$d_6$) δ 7.22 (s, 2H), 6.99 (s, 1H), 4.22-3.96 (m, 2H), 3.63-3.59 (m, 3H), 3.48-3.38 (m, 1H), 3.03 (s, 3H), 2.99-2.91 (m, 2H), 2.89 (s, 1H), 2.83-2.64 (m, 3H), 2.06-1.94 (m, 1H), 1.82 (d, J=12.4 Hz, 2H), 1.66-1.50 (m, 2H), 1.43 (s, 9H), LC-MS (ESI$^+$) m/z 401.3 (M+1)$^+$.

Step 2—1-Methyl-3-[3-methyl-2-oxo-4-(4-piperidyl)benzimidazol-1-yl]piperidine-2,6-dione To a solution of tert-butyl 4-[3-methyl-1-(1-methyl-2,6-dioxo-3-piperidyl)-2-oxo-benzimidazol-4-yl]piperidine-1-carboxylate (250 mg, 547 umol) in DCM (3 mL) was added TFA (1 mL). The reaction mixture was stirred at 25° C. for 1 hr. On completion, the mixture was concentrated to give the title compound (100 mg, 38% yield, TFA) as brown oil. LC-MS (ESI$^+$) m/z 357.1 (M+1)$^+$.

6-(2-Hydroxypropan-2-yl)picolinamide (Intermediate BCE)

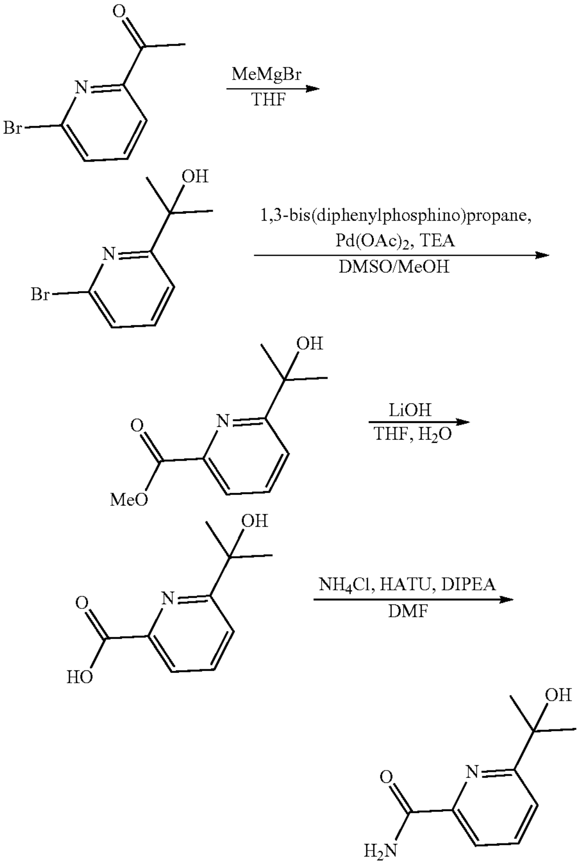

BCE

Step 1—2-(6-Bromopyridin-2-yl)propan-2-ol

A mixture of 1-(6-bromo-2-pyridyl)ethanone (2.00 g, 10.00 mmol, CAS #49669-13-8) in THF (40 mL) was added MeMgBr (3 M, 4.00 mL) at 0° C. The reaction mixture was stirred at 25° C. for 16 hrs. On completion, the mixture was poured into water (20 mL) and extracted with EA (3×15 mL). The combined organic layer was dried over $Na_2SO_4$, filtrated and the filtrate was concentrated in vacuo. The residue was purified by column chromatography ($SiO_2$, Petroleum ether:Ethyl acetate=10:1) to give the title compound (2.00 g, 92% yield) as yellow oil. $^1H$ NMR (400 MHz, DMSO-$d_6$) δ 7.74-7.70 (m, 1H), 7.68-7.65 (m, 1H), 7.46 (d, J=7.6 Hz, 1H), 5.32 (s, 1H), 1.41 (s, 6H).

Step 2—Methyl 6-(2-hydroxypropan-2-yl)picolinate

A solution of 2-(6-bromo-2-pyridyl)propan-2-ol (2.00 g, 9.26 mmol), TEA (2.81 g, 27.7 mmol), 1,3- bis(diphenylphosphino)propane (267 mg, 647 umol) and $Pd(OAc)_2$ (145 mg, 647 umol) in MeOH (15 mL) and DMSO (15 mL) was stirred at 80° C. for 16 hrs under CO (50 psi) atmosphere. On completion, the solid was removed by filtration, the filtrate was concentrated under reduced pressure to give a residue. The residue was purified by Prep-HPLC (column: C18 180 g; mobile phase: [water (0.1% FA)-ACN]; B %: 0%-30%, 15 min) to give the title compound (1.10 g, 5.63 mmol, 60% yield) as a brown solid. $^1$H NMR (400 MHz, DMSO-d6) δ=7.99-7.94 (m, 1H), 7.92-7.88 (m, 2H), 3.88 (s, 3H), 1.46 (s, 6H). LC-MS (ESI$^+$) m/z 196.2 (M+H)$^+$.

Step 3—6-(2-Hydroxypropan-2-yl)picolinic acid

A solution of methyl 6-(1-hydroxy-1-methyl-ethyl)pyridine-2-carboxylate (800 mg, 4.10 mmol) and LiOH $H_2O$ (343 mg, 8.20 mmol) in THE (6 mL) and $H_2O$ (2 mL) was stirred at 60° C. for 12 hrs. On completion, the solid was removed by filtration, and the filtrate was concentrated under reduced pressure to give a residue. The residue was purified by Prep-HPLC (column: C18 180 g; mobile phase: [water (0.1% FA)-ACN]; B %: 0%-20%, 15 min) to give the title compound (700 mg, 94% yield) as a yellow solid. $^1$H NMR (400 MHz, DMSO-$d_6$) δ 7.99-7.92 (m, 1H), 7.92-7.87 (m, 1H), 7.83 (d, J=7.6 Hz, 1H), 5.90-5.18 (m, 1H), 1.48 (s, 6H). LC-MS (ESI$^+$) m/z 182.1 (M+H)$^+$.

Step 4—6-(2-Hydroxypropan-2-yl)picolinamide

A solution of 6-(1-hydroxy-1-methyl-ethyl)pyridine-2-carboxylic acid (900 mg, 4.97 mmol), HATU (1.89 g, 4.97 mmol), $NH_4Cl$ (5.31 g, 99.3 mmol) and DIPEA (1.93 g, 14.90 mmol) in DMF (20 mL) was stirred at 25° C. for 16 hrs. On completion, the solid was removed by filtration, the filtrate was concentrated under reduced pressure to give a residue. The residue was purified by Prep-HPLC (column: C18 180 g; mobile phase: [water (0.1% FA)-ACN]; B %: 0%-20%, 15 min) to give the title compound (600 mg, 67% yield) as a brown solid. $^1$H NMR (400 MHz, DMSO-$d_6$) δ 8.30 (s, 1H), 7.96-7.90 (m, 1H), 7.89-7.84 (m, 1H), 7.76 (d, J=7.6 Hz, 1H), 7.59 (s, 1H), 5.39 (s, 1H), 1.47 (s, 6H). LC-MS (ESI$^+$) m/z 181.1 (M+H)$^+$.

N-(2-((1r,4r)-4-Formylcyclohexyl)-6-methoxy-2H-indazol-5-yl)-6-(2-hydroxypropan-2- yl)picolinamide (Intermediate BCF)

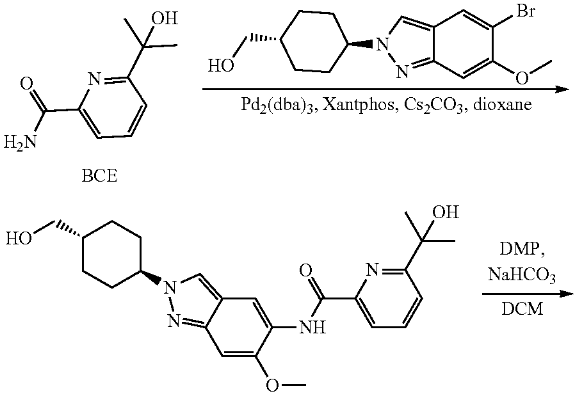

BCE

-continued

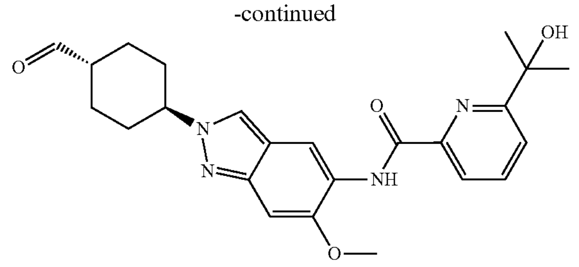

BCF

Step 1—N-(2-((1r,4r)-4-(Hydroxymethyl)cyclohexyl)-6-methoxy-2H-indazol-5-yl)-6-(2- hydroxypropan-2-yl)picolinamide A solution of 6-(1-hydroxy-1-methyl-ethyl)pyridine-2-carboxamide (300 mg, 1.66 mmol, Intermediate BCE), ((1r,4r)-4-(5-bromo-6-methoxy-2H-indazol-2-yl)cyclohexyl)methanol (564 mg, 1.66 mmol, synthesized via Steps 1-3 of Intermediate ATF), $Pd_2(dba)_3$ (76.2 mg, 83.2 umol), Xantphos (96.3 mg, 166 umol) and $Cs_2CO_3$ (1.08 g, 3.33 mmol) in dioxane (10 mL) was stirred at 80° C. for 16 hrs under $N_2$ atmosphere. On completion, the reaction mixture was filtered and the filtrate was concentrated under reduced pressure to give a residue. The residue was slurried in DCM, the precipitate was filtered and the filtrate was concentrated in vacuo to give a solid. The solid was slurried in EA, the precipitate was collected by filtration to give the title compound (450 mg, 61% yield) as a yellow solid. $^1$H NMR (400 MHz, DMSO-$d_6$) δ 10.92 (s, 1H), 8.67 (s, 1H), 8.31 (s, 1H), 8.11-8.04 (m, 1H), 8.04-7.99 (m, 1H), 7.94 (d, J=7.6 Hz, 1H), 7.15 (s, 1H), 4.51 (t, J=5.2 Hz, 1H), 4.35 (d, J=11.6 Hz, 1H), 3.99 (s, 3H), 3.57 (s, 1H), 3.30 (t, J=5.6 Hz, 2H), 2.17-2.11 (m, 2H), 1.93-1.86 (m, 4H), 1.57 (s, 6H), 1.51-1.44 (m, 1H), 1.19-1.11 (m, 2H). LC-MS (ESI$^+$) m/z 439.4 (M+H)$^+$.

Step 2—N-(2-((1r,4r)-4-Formylcyclohexyl)-6-methoxy-2H-indazol-5-yl)-6-(2-hydroxypropan-2-yl)picolinamide To a solution of N-(2-((1r,4r)-4-(hydroxymethyl)cyclohexyl)-6-methoxy-2H-indazol-5-yl)-6-(2- hydroxypropan-2-yl)picolinamide (400 mg, 912 umol) and $NaHCO_3$ (383 mg, 4.56 mmol) in DCM (10 mL) was added DMP (386 mg, 912 umol) and the mixture was stirred at 25° C. for 1 hr. On completion, the reaction mixture was filtered and the filtrate was concentrated under reduced pressure to give a residue. The residue was diluted with water (30 mL) and extracted with ethyl acetate (3×30 mL). The combined organic layers were washed with sodium chloride solution (30 mL), dried over anhydrous sodium sulfate, filtered and concentrated under reduced pressure to give a residue. The residue was triturated with DCM to give the title compound (240 mg, 60% yield) as a brown solid. $^1$H NMR (400 MHz, DMSO-$d_6$) δ 10.93 (s, 1H), 9.65 (s, 1H), 8.68 (s, 1H), 8.32 (s, 1H), 8.11-8.05 (m, 1H), 8.04-8.00 (m, 1H), 7.94 (d, J=7.6 Hz, 1H), 7.15 (s, 1H), 5.47 (s, 1H), 4.40 (d, J=11.6 Hz, 1H), 3.99 (s, 3H), 2.21 (d, J=10.0 Hz, 2H), 2.11 (d, J=11.2 Hz, 2H), 1.96 (d, J=12.4 Hz, 2H), 1.58 (s, 6H), 1.52-1.39 (m, 3H). LC-MS (ESI$^+$) m/z 437.2 (M+H)$^+$.

(5-Amino-2-methyl-6-morpholino-2,3-dihydrobenzofuran-2-yl)methanol (Intermediate BCG)

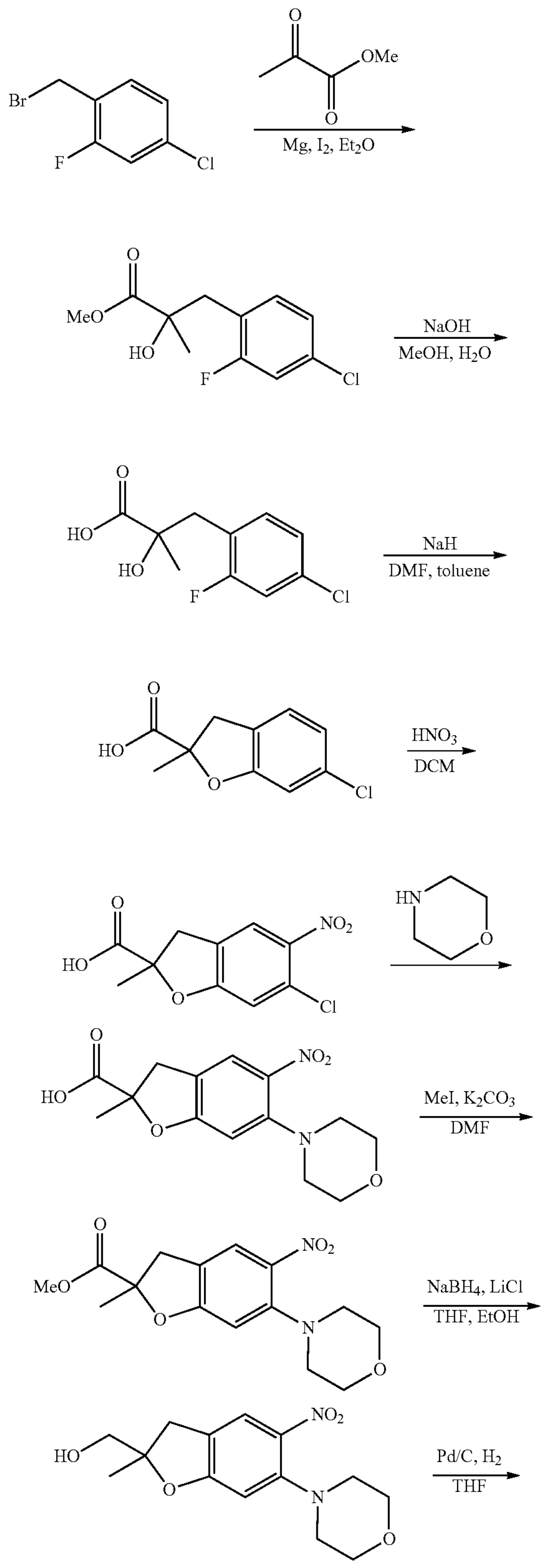

-continued

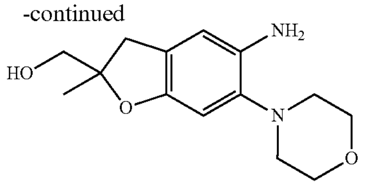

BCG

Step 1—Methyl 3-(4-chloro-2-fluorophenyl)-2-hydroxy-2-methylpropanoate

To a solution of Mg (13.60 g, 559 mmol) and $I_2$ (1.00 g, 3.94 mmol) in diethyl ether (500 mL) at 40° C. was added 1-(bromomethyl)-4-chloro-2-fluoro-benzene (50.0 g, 223 mmol, CAS #71916-82-0) dropwise. The reaction mixture was stirred for 30 min at 25° C. Then the solution was added to a solution of methyl 2-oxopropanoate (23.0 g, 225 mmol, 20.3 mL, CAS #600-22-6) in diethyl ether (500 mL) at −78° C. and stirred for 30 min followed by warming to 25° C. for 2 hours. On completion, saturated ammonium chloride solution and ethyl acetate (1000 mL) was added. The organic phase was separated and dried over sodium sulfate. After concentration, the residue was purified by silica gel chromatography to give the title compound (20.0 g, 28% yield) as yellow oil. $^1H$ NMR (400 MHz, $CDCl_3$) δ 7.25-7.18 (m, 1H), 7.12-7.01 (m, 2H), 3.78 (s, 3H), 3.16-3.06 (m, 2H), 2.94 (d, J=13.6 Hz, 1H), 1.49 (s, 3H).

Step 2—3-(4-Chloro-2-fluorophenyl)-2-hydroxy-2-methylpropanoic acid

To a solution of methyl 3-(4-chloro-2-fluoro-phenyl)-2-hydroxy-2-methyl-propanoate (10.0 g, 40.5 mmol) in THF (80 mL) and $H_2O$ (20 mL) was added NaOH (4.86 g, 121 mmol), then the mixture was stirred at 20° C. for 12 hours. On completion, the reaction mixture was concentrated in vacuo to remove the organic solvent. The aqueous layer was adjusted pH to 5 with 1 N HCl, then extracted with EA (3×30 ml). The combined organic layers were washed with brine, dried with $Na_2SO_4$ and filtered. The filtrate was concentrated in vacuo to give title compound (9.50 g, 100% yield) as a yellow solid. $^1H$ NMR (400 MHz, $CDCl_3$) δ 7.27-7.20 (m, 1H), 7.13-7.05 (m, 2H), 3.20-2.97 (m, 2H), 1.53 (s, 3H).

Step 3—6-Chloro-2-methyl-2,3-dihydrobenzofuran-2-carboxylic acid

To a solution of 3-(4-chloro-2-fluoro-phenyl)-2-hydroxy-2-methyl-propanoic acid (9.50 g, 40.8 mmol) in toluene (120 mL) and dmf (30 mL) was added NaH (3.59 g, 89.8 mmol, 60% dispersion in mineral oil) at 20° C., then the mixture was warmed to 110° C. and stirred for 2 hrs. On completion, the reaction mixture was diluted with 150 ml of water and adjusted pH to 5 with 2M HCl and extracted with EA (3×100 mL). The combined organic layers were washed with brine, dried over $Na_2SO_4$ and concentrated in vacuo to give the title compound (7.00 g, 100% yield) as a yellow solid. $^1H$ NMR (400 MHz, $CDCl_3$) δ 7.07-7.03 (m, 1H), 6.89-6.84 (m, 2H), 3.60 (d, J=16.4 Hz, 1H), 3.13 (dd, J=0.8, 16.0 Hz, 1H), 1.74 (s, 3H).

Step 4—6-Chloro-2-methyl-5-nitro-2,3-dihydrobenzofuran-2-carboxylic acid

To a solution of 6-chloro-2-methyl-3H-benzofuran-2-carboxylic acid (7.00 g, 32.9 mmol) in DCM (70 mL) was added $HNO_3$ (21.0 g, 333 mmol), then the mixture was stirred at 20° C. for 1 hour. On completion, the reaction mixture was diluted with 100 mL of water and the organic phase was washed with brine, dried over $Na_2SO_4$ and concentrated in vacuo to give title compound (4.00 g, 100% yield) as a yellow solid. $^1H$ NMR (400 MHz, $CDCl_3$) δ 7.84 (s, 1H), 6.99 (s, 1H), 3.69 (dd, J=0.8, 16.4 Hz, 1H), 3.23 (dd, J=1.2, 16.4 Hz, 1H), 1.80 (s, 3H).

Step 5—2-Methyl-6-morpholino-5-nitro-2,3-dihydrobenzofuran-2-carboxylic acid

A mixture of 6-chloro-2-methyl-5-nitro-3H-benzofuran-2-carboxylic acid (1.00 g, 3.88 mmol) in morpholine (4.95 g, 56.8 mmol, 5 mL) was stirred at 120° C. for 12 hours. On completion, water and ethyl acetate (50 mL) were added. The organic phase was separated and dried over sodium sulfate and concentrated in vacuo. The residue was triturated with 3 mL of EA to give the title compound (900 mg, 75% yield) as a yellow solid.

Step 6—Methyl 2-methyl-6-morpholino-5-nitro-2,3-dihydrobenzofuran-2-carboxylate

To a solution of 2-methyl-6-morpholino-5-nitro-3H-benzofuran-2-carboxylic acid (900 mg, 2.92 mmol) and $K_2CO_3$ (806 mg, 5.84 mmol) in DMF (7 mL) was added MeI (828 mg, 5.84 mmol), then the mixture was stirred at 20° C. for 12 hours. On completion, the mixture was quenched with 100 mL water and extracted with EtOAc (3x30 mL). The organic phase was separated, dried over sodium sulfate and concentration in vacuo. The residue was purified by column chromatography to give the title compound (700 mg, 74% yield) as yellow oil. $^1H$ NMR (400 MHz, $CDCl_3$) δ 7.84 (s, 1H), 6.59 (s, 1H), 3.89-3.84 (m, 4H), 3.81 (s, 3H), 3.60 (dd, J=0.8, 16.0 Hz, 1H), 3.13 (dd, J=1.2, 16.0 Hz, 1H), 3.06-3.01 (m, 4H), 1.74 (s, 3H).

Step 7—(2-Methyl-6-morpholino-5-nitro-2,3-dihydrobenzofuran-2-yl)methanol

To a mixture of methyl 2-methyl-6-morpholino-5-nitro-3H-benzofuran-2-carboxylate (700 mg, 2.17 mmol) in THE (4 mL) and EtOH (1 mL) was added $NaBH_4$ (246 mg, 6.52 mmol) followed by LiCl (276 mg, 6.52 mmol) at 0° C. The mixture was stirred at 25° C. for 3 hours. On completion, the mixture was quenched with saturated ammonium chloride and extracted with DCM. The organic phase was dried over sodium sulfate and concentrated in vacuo to give title compound (600 mg, 94% yield) as yellow oil. $^1H$ NMR (400 MHz, $CDCl_3$) δ 7.86 (s, 1H), 6.48 (s, 1H), 3.90-3.83 (m, 4H), 3.79-3.60 (m, 2H), 3.27 (dd, J=1.2, 15.6 Hz, 1H), 3.06-3.00 (m, 4H), 2.90 (dd, J=1.2, 15.6 Hz, 1H), 1.84 (t, J=6.0 Hz, 1H), 1.48 (s, 3H).

Step 8—(5-Amino-2-methyl-6-morpholino-2,3-dihydrobenzofuran-2-yl)methanol

To a solution of (2-methyl-6-morpholino-5-nitro-3H-benzofuran-2-yl)methanol (600 mg, 2.04 mmol) in THF (30 mL) was added Pd/C (50 mg, 10 wt %). The reaction mixture was stirred at 25° C. for 2 hours under $H_2$ (15 psi). On completion, the reaction mixture was diluted with THE (50 mL) and filtered. The organic layer was concentrated in vacuo to give the title compound (538 mg, 99% yield) as a light yellow solid. LC-MS (ESI$^+$) m/z 265.1 $(M+1)^+$.

(R)—N-(2-(hydroxymethyl)-2-methyl-6-morpholino-2,3-dihydrobenzofuran-5-yl)pyrazolo [1,5-a]pyrimidine-3-carboxamide (Intermediate BCH) and (S)—N-(2-(hydroxymethyl)-2-methyl-6- morpholino-2,3-dihydrobenzofuran-5-yl)pyrazolo[1,5-a] pyrimidine-3-carboxamide (Intermediate BCI)

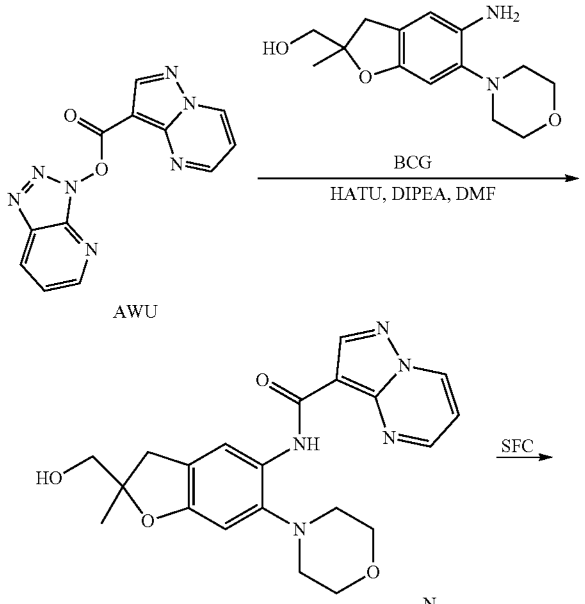

AWU

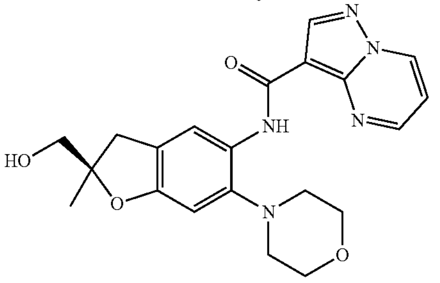

BCH

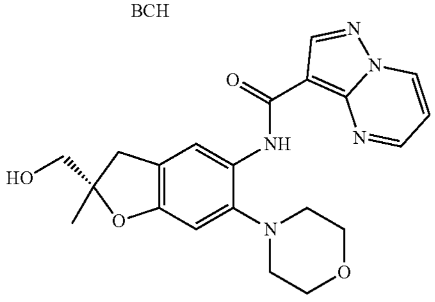

BCI

Step 1—N-(2-(hydroxymethyl)-2-methyl-6-morpholino-2,3-dihydrobenzofuran-5-yl)pyrazolo [1,5-a]pyrimidine-3-carboxamide To a solution of (5-amino-2-methyl-6-morpholino-3H-benzofuran-2-yl)methanol (530 mg, 2.01 mmol, Intermediate BCG) in DMF (1 mL) was added triazolo[4,5-b]pyridin-3-yl pyrazolo[1,5-a]pyrimidine-3-carboxylate (507 mg, 1.80 mmol, Intermediate AWU). The reaction mixture was stirred at 25° C. for 1 hour. Then DIPEA (3.89 g, 30.1 mmol) was added and the reaction mixture was stirred at 25° C. for 0.5 hour. On completion, the reaction mixture was quenched with water (50 mL) and filtered. The filter cake was washed with water (2×10 mL) and dried in vacuo to give the title compound (670 mg, 78% yield) as an off-white solid. LC-MS (ESI$^+$) m/z 410.1 (M+1)$^+$.

Step 2—(R)—N-(2-(hydroxymethyl)-2-methyl-6-morpholino-2,3-dihydrobenzofuran-5-yl)pyrazolo[1,5-a]pyrimidine-3-carboxamide and (S)—N-(2-(hydroxymethyl)-2-methyl-6- morpholino-2,3-dihydrobenzofuran-5-yl)pyrazolo[1,5-a]pyrimidine-3-carboxamide Compound N-[2-(hydroxymethyl)-2-methyl-6-morpholino-3H-benzofuran-5-yl]pyrazolo[1,5-a] pyrimidine-3-carboxamide (670 mg, 1.64 mmol) was separated with SFC (column: DAICEL CHIRALCEL OJ (250 mm*30 mm, 10 um); mobile phase: [0.1% $NH_3H_2O$ MEOH]; B %: 35%-35%, 3.4 min; 110 min) to give (R)—N-(2-(hydroxymethyl)-2-methyl-6-morpholino-2,3-dihydrobenzofuran-5-yl) pyrazolo [1,5-a]pyrimidine-3-carboxamide (339 mg, 50% yield, ee value=100%): $^1$H NMR (400 MHz, DMSO-$d_6$) δ 10.43 (s, 1H), 9.37 (dd, J=1.6, 7.2 Hz, 1H), 8.94 (dd, J=1.6, 4.2 Hz, 1H), 8.67 (s, 1H), 8.29 (s, 1H), 7.34 (dd, J=4.2, 7.2 Hz, 1H), 6.70 (s, 1H), 5.04 (t, J=5.6 Hz, 1H), 3.87-3.80 (m, 4H), 3.47-3.37 (m, 2H), 3.24-3.15 (m, 1H), 2.86-2.77 (m, 5H), 1.34 (s, 3H); LC-MS (ESI$^+$) m/z 410.2 (M+1)* and (S)—N-(2-(hydroxymethyl)-2-methyl-6- morpholino-2,3-dihydrobenzofuran-5-yl)pyrazolo[1,5-a]pyrimidine-3-carboxamide (325 mg, 48% yield, 100% purity, ee value=100%) as a light yellow solid: $^1$H NMR (400 MHz, DMSO-$d_6$) δ 10.43 (s, 1H), 9.36 (dd, J=1.6, 7.2 Hz, 1H), 8.94 (dd, J=1.6, 4.2 Hz, 1H), 8.67 (s, 1H), 8.29 (s, 1H), 7.34 (dd, J=4.2, 7.2 Hz, 1H), 6.70 (s, 1H), 5.04 (t, J=5.6 Hz, 1H), 3.87-3.79 (m, 4H), 3.48-3.38 (m, 2H), 3.23-3.16 (m, 1H), 2.86-2.77 (m, 5H), 1.34 (s, 3H), LC-MS (ESI$^+$) m/z 410.2 (M+1)$^+$. Stereochemistry arbitrarily assigned.

Benzyl N-(2-aminospiro[3.5]nonan-7-yl)-N-methyl-carbamate (Intermediate BCX)

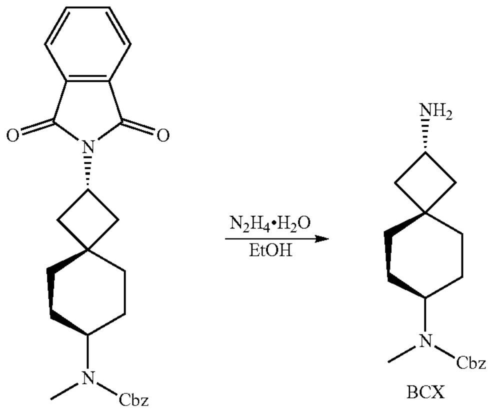

BCX

To a solution of benzyl N-[2-(1,3-dioxoisoindolin-2-yl) spiro[3.5]nonan-7-yl]-N-methyl-carbamate (130 mg, 300 umol, synthesized via Steps 1-4 of Intermediate AXA) in EtOH (2 mL) was added N2H4.H2O (45.1 mg, 901 umol). The reaction mixture was stirred at 80° C. for 2 hours. On completion, the reaction mixture was filtered and the filtrate was concentrated in vacuo. The residue was dissolved in DCM (30 mL) and filtered. The filtrate was concentrated in vacuo to give the title compound (60.0 mg, 66% yield) as yellow oil. $^1$H NMR (400 MHz, $CDCl_3$) δ 7.40-7.28 (m, 5H), 5.14 (s, 2H), 4.05-3.78 (m, 1H), 3.43-3.35 (m, 1H), 2.79 (s, 3H), 2.33-2.21 (m, 1H), 2.15-2.00 (m, 1H), 1.78-1.73 (m, 1H), 1.62-1.55 (m, 2H), 1.54-1.42 (m, 5H), 1.37-1.21 (m, 4H).

2-(2,6-Dioxo-3-piperidyl)-4-[[7-(methylamino)spiro[3.5]nonan-2-yl]amino]isoindoline-1,3-dione (Intermediate BCY)

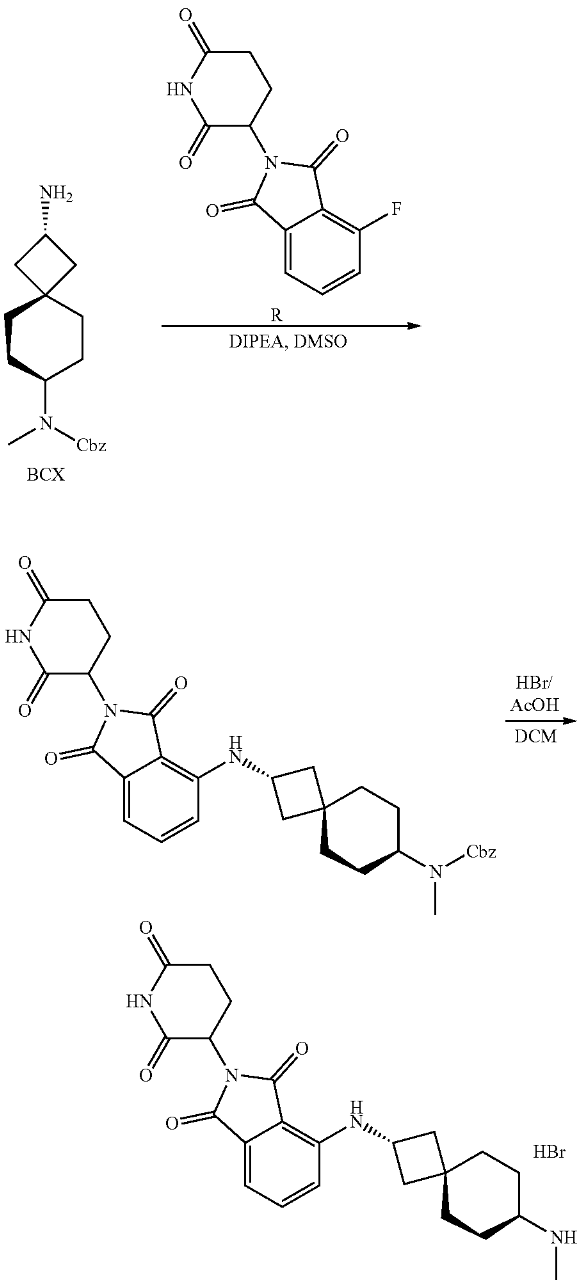

BCX

BCY

Step 1—Benzyl N-[2-[[2-(2,6-dioxo-3-piperidyl)-1,3-dioxo-isoindolin-4-yl]amino]spiro[3.5]nonan-7-yl]-N-methyl-carbamate To a solution of benzyl N-(2-aminospiro[3.5]nonan-7-yl)-N-methyl-carbamate (60.0 mg, 198 umol, Intermediate BCX) and 2-(2,6-dioxo-3-piperidyl)-4-fluoro-isoindoline-1,3-dione (54.8 mg, 198 umol, Intermediate R) in DMSO (1.5 mL) was added DIPEA (51.2 mg, 396 umol). The reaction mixture was stirred at 130° C. for 2 hours. On completion, the reaction mixture was diluted with water (6 mL) and extracted with EA (3×15 mL). The combined organic layers were washed with brine (2×10 mL), dried over $Na_2SO_4$, filtered and concentrated in vacuo. The residue was purified by reverse phase (0.1% FA) to give the title compound (55.0 mg, 49% yield) as yellow solid. $^1$H NMR (400 MHz, $CDCl_3$) δ 8.01 (s, 1H), 7.48 (dd, J=7.2, 8.4 Hz, 1H), 7.40-7.29 (m, 5H), 7.12 (d, J=7.2 Hz, 1H), 6.74 (d, J=8.4 Hz, 1H), 6.30 (d, J=5.6 Hz, 1H), 5.14 (s, 2H), 5.00-4.85 (m, 1H), 4.09-3.73 (m, 2H), 2.96-2.68 (m, 6H), 2.53-2.41 (m, 1H), 2.35-2.25 (m, 1H), 2.20-2.10 (m, 1H), 1.94-1.81 (m, 1H), 1.79-1.62 (m, 4H), 1.56-1.39 (m, 5H).

Step 2—2-(2,6-Dioxo-3-piperidyl)-4-[[7-(methylamino)spiro[3.5]nonan-2-yl]amino]isoindoline-1,3-dione To a solution of benzyl N-[2-[[2-(2,6-dioxo-3-piperidyl)-1,3-dioxo-isoindolin-4-yl]amino]spiro [3.5] nonan-7-yl]-N-methyl-carbamate (55.0 mg, 98.4 umol) in DCM (1 mL) was added HBr/AcOH (1 mL, 33% solution). The reaction mixture was stirred at 20° C. for 1 hour. On completion, the reaction mixture was concentrated in vacuo to give the title compound (45.0 mg, 90% yield, HBr salt) as yellow solid. LC-MS (ESI$^+$) m/z 425.2.

[4-(5-Bromo-6-methoxy-3-methyl-indazol-2-yl)cyclohexyl]methanol (Intermediate BCZ)

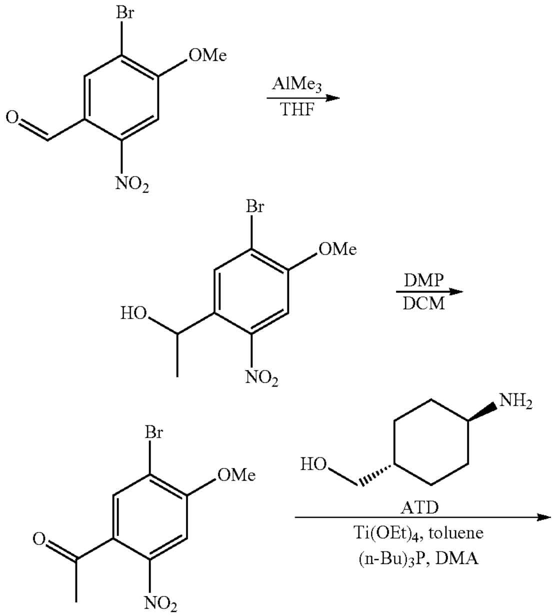

-continued

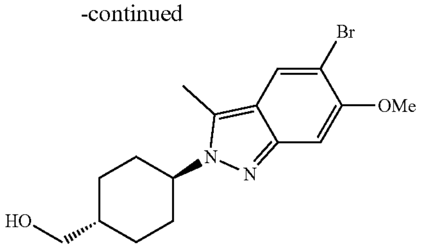

BCZ

Step 1—1-(5-Bromo-4-methoxy-2-nitro-phenyl)ethanol

To a solution of 5-bromo-4-methoxy-2-nitro-benzaldehyde (1.00 g, 3.85 mmol, synthesized via Steps 1-2 of Intermediate ATE) in DCM (40 mL) was added 2.0 M $Al(CH_3)_3$ toluene solution (2.31 mL, 4.62 mmol) at 0° C. The mixture was stirred at 0° C. for 1 hour. On completion, the reaction was quenched with 1.0 M aq. HCl (5 mL) slowly at 0° C. The mixture was partitioned. The organic layer was washed with brine (10 mL), dried over $Na_2SO_4$, filtered and concentrated in vacuo. The residue was purified by column chromatography on silica gel (PE:EA=20:1-5:1) to give the title compound (1.00 g, 94% yield) as light yellow solid. $^1$H NMR (400 MHz, $CDCl_3$) δ 8.04 (s, 1H), 7.45 (s, 1H), 5.41 (q, J=6.4 Hz, 1H), 3.98 (s, 3H), 2.30 (s, 1H), 1.55 (d, J=6.4 Hz, 3H).

Step 2—1-(5-Bromo-4-methoxy-2-nitro-phenyl)ethanone

To a solution of 1-(5-bromo-4-methoxy-2-nitro-phenyl)ethanol (950 mg, 3.44 mmol) in DCM (20 mL) was added Dess-Martin (2.19 g, 5.16 mmol) at 0° C. The mixture was stirred at 25° C. for 16 hours. On completion, the reaction was quenched with sat. aq. $Na_2S_2O_3$ (10 mL). The mixture was partitioned and the aqueous phase was extracted with DCM (2×10 mL). The combined organic layer was washed with sat. aq. $NaHCO_3$ (10 mL) and brine (10 mL), dried over $Na_2SO_4$, filtered and concentrated in vacuo. The residue was purified by column chromatography on silica gel (PE: EA=20:1-5:1) to give the title compound (940 mg, 99% yield) as white solid. $^1$H NMR (400 MHz, $CDCl_3$) δ 7.68 (s, 1H), 7.50 (s, 1H), 4.03 (s, 3H), 2.52 (s, 3H).

Step 3—[4-(5-Bromo-6-methoxy-3-methyl-indazol-2-yl)cyclohexyl]methanol

A mixture of 1-(5-bromo-4-methoxy-2-nitro-phenyl)ethanone (840 mg, 3.06 mmol), (4-aminocyclohexyl)methanol (402 mg, 3.11 mmol, Intermediate ATD) and $Ti(OEt)_4$ (1.40 g, 6.14 mmol) in toluene (10 mL) was stirred at 80° C. for 16 hours under $N_2$. The mixture was concentrated in vacuo. Then, tributylphosphane (1.87 g, 9.26 mmol) and DMA (3 mL) was added to the reaction mixture at 25° C. The mixture was stirred at 130° C. for 16 hours under $N_2$. After cooled to 25° C., the mixture was with water (50 mL), extracted with EA (3×20 mL). The combined organic layer was washed with brine (10 mL), dried over $Na_2SO_4$, filtered and concentrated in vacuo. The residue was purified by reverse phase flash (FA condiction) and column chromatography on silica gel (PE:EA:DCM=10:1:1-2:1:1) to give the title compound (550 mg, 50% yield) as light yellow oil. $^1$H NMR (400 MHz, $CDCl_3$) δ 7.76 (s, 1H), 7.02 (s, 1H), 4.25-4.19

(m, 1H), 3.92 (s, 3H), 3.56 (d, J=6.0 Hz, 2H), 2.55 (s, 3H), 2.26-2.14 (m, 2H), 1.58-1.52 (m, 5H), 1.26-1.18 (m, 2H).

N-[2-(4-formylcyclohexyl)-6-methoxy-3-methyl-indazol-5-yl]-6-(trifluoromethyl)pyridine -2-carboxamide (Intermediate BDA)

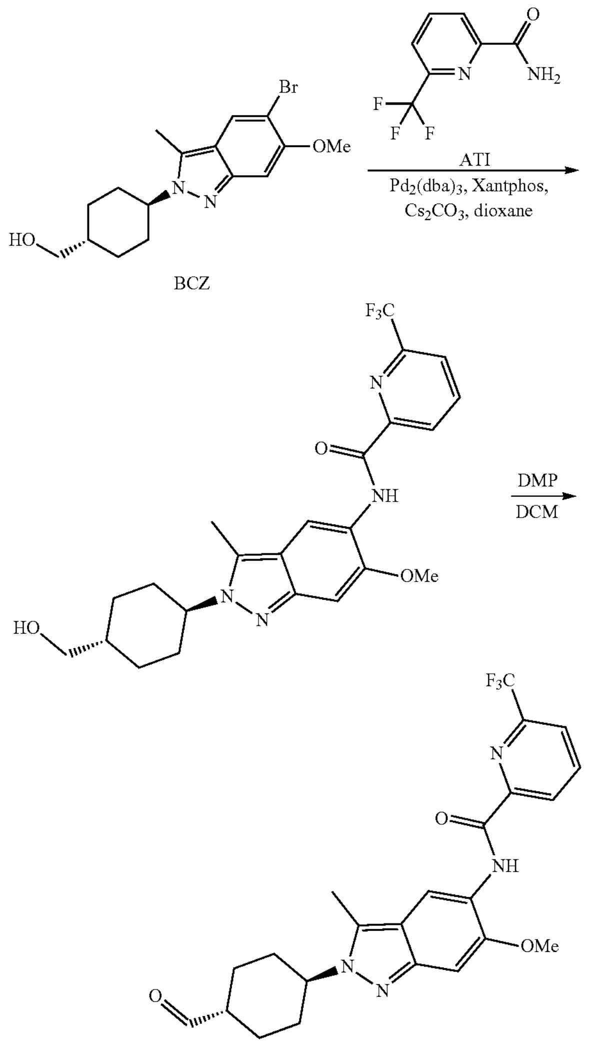

BCZ

BDA

Step 1—N-[2-[4-(hydroxymethyl)cyclohexyl]-6-methoxy-3-methyl-indazol-5-yl]-6-(trifluoromethyl) pyridine-2-carboxamide A mixture of [4-(5-bromo-6-methoxy-3-methyl-indazol-2-yl)cyclohexyl]methanol (500 mg, 1.42 mmol, Intermediate BCZ), 6-(trifluoromethyl)pyridine-2-carboxamide (270 mg, 1.42 mmol, Intermediate ATI), $Pd_2(dba)_3$ (130 mg, 141 umol), Xantphos (164 mg, 283 umol) and $Cs_2CO_3$ (930 mg, 2.85 mmol,) in dioxane (10 mL) was stirred at 80° C. for 16 hours under $N_2$. On completion, after cooled to 25° C., the mixture was filtered, and the cake was washed with THE (10 mL). The filtrate and washing were combined and concentrated in vacuo. The residue was purified by reversed phase flash (FA condition) to give the title compound (220 mg, 33% yield) as light yellow solid. $^1$H NMR (400 MHz, $CDCl_3$) δ 10.71 (s, 1H), 8.74 (s, 1H), 8.49 (d, J=8.0 Hz, 1H), 8.13 (t, J=8.0 Hz, 1H), 7.91-7.82 (m, 1H), 7.05 (s, 1H), 4.28-4.21 (m, 1H), 4.02 (s, 3H), 3.57 (d, J=6.0 Hz, 2H), 2.61 (s, 3H), 2.27-2.15 (m, 2H), 2.09-2.03 (m, 4H), 1.31-1.16 (m, 3H).

Step 2—N-[2-(4-formylcyclohexyl)-6-methoxy-3-methyl-indazol-5-yl]-6-(trifluoromethyl)pyridine -2-carboxamide To a solution of N-[2-[4-(hydroxymethyl)cyclohexyl]-6-methoxy-3-methyl-indazol-5-yl]-6-(trifluoro methyl)pyridine-2-carboxamide (190 mg, 410 umol) in DCM (5 mL) was added Dess-Martin (266 mg, 627 umol) at 0° C. The mixture was stirred at 25° C. for 1 hour. On completion, the reaction mixture was diluted with DCM (10 mL), quenched with sat. aq. $Na_2S_2O_3$ (5 mL). The mixture was partitioned and the aqueous phase was extracted with DCM (2×5 mL). The combined organic layer was washed with sat.aq-.$NaHCO_3$ (5 mL) and brine (5 mL), dried over $Na_2SO_4$, filtered and concentrated in vacuo to give the title compound (189 mg, 99% yield) as light yellow solid. LC-MS (ESI$^+$) m/z 461.1 $(M+H)^+$.

(2R)-Tetrahydropyran-2-carboxamide (Intermediate BDB)

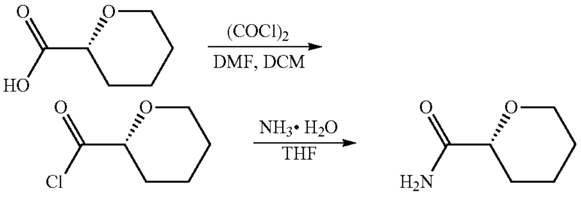

BDB

Step 1—(2R)-Tetrahydropyran-2-carbonyl chloride

To a solution of (2R)-tetrahydropyran-2-carboxylic acid (500 mg, 3.84 mmol, CAS #105499-34-1) and DMF (28.0 mg, 384 umol) in DCM (10 mL) was added $(COCl)_2$ (975 mg, 7.68 mmol) at 0° C. The reaction mixture was stirred at 0° C. for 2 hours. On completion, the reaction was concentrated in vacuo to give the title compound (560 mg, 98% yield) as colorless oil.

Step 2—(2R)-Tetrahydropyran-2-carboxamide

To a solution of $NH_3.H_2O$ (10.0 mL, 77.8 mmol, 30% solution) was added a solution of (2R)-tetrahydropyran-2-carbonyl chloride (560 mg, 3.77 mmol) inTHF (5 mL) dropwise at 0° C. The reaction was stirred at 25° C. for 30 minutes. On completion, the reaction mixture was diluted with $H_2O$ (20 mL), and extracted with EA (2×40 mL). The organic phase was dried over $Na_2SO_4$, and concentrated in vacuo to give the title compound (340 mg, 70% yield) as a white solid. $^1$H NMR (400 MHz, $CDCl_3$) δ 6.50 (s, 1H), 5.66 (s, 1H), 4.08-4.00 (m, 1H), 3.79 (dd, J=2.4, 11.2 Hz, 1H), 3.53-3.44 (m, 1H), 2.15-2.06 (m, 1H), 1.96-1.85 (m, 1H), 1.62-1.51 (m, 3H), 1.49-1.37 (m, 1H).

(2R)—N-[2-(4-formylcyclohexyl)-6-methoxy-indazol-5-yl]tetrahydropyran-2-carboxamide (Intermediate BDC)

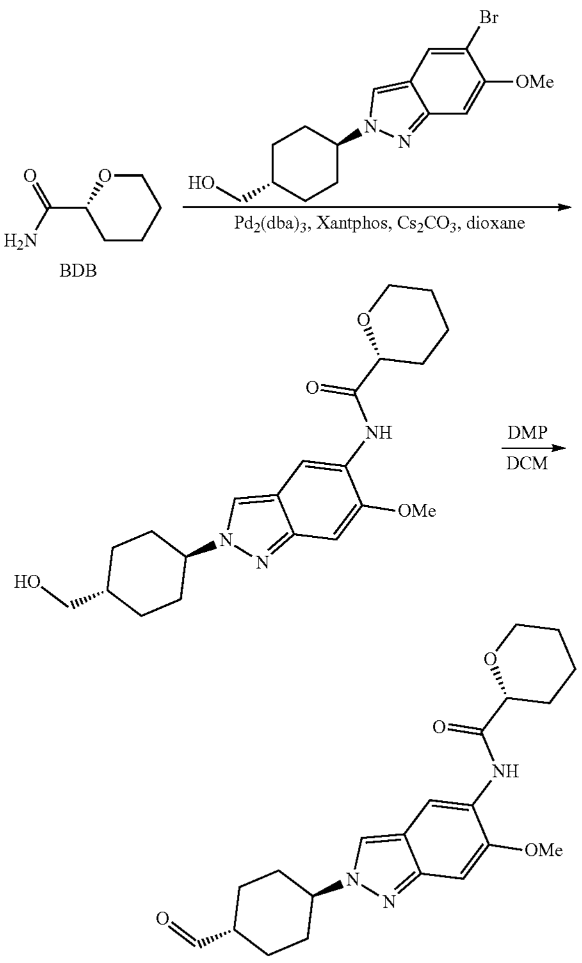

BDB

BDC

Step 1—(2R)—N-[2-[4-(hydroxymethyl)cyclohexyl]-6-methoxy-indazol-5-yl]tetrahydropyran-2-carboxamide To a solution of (2R)-tetrahydropyran-2-carboxamide (290 mg, 2.25 mmol, Intermediate BDB) and [4-(5-bromo-6-methoxy-indazol-2-yl)cyclohexyl]methanol (692 mg, 2.04 mmol, synthesized via Steps 1-3 of Intermediate ATE) in dioxane (15 mL) was added $Cs_2CO_3$ (1.33 g, 4.08 mmol), Xantphos (236 mg, 408 umol) and Pd$_2$(dba)$_3$ (186 mg, 204 umol). The reaction mixture was stirred at 80° C. for 12 hours. On completion, the reaction mixture was filtered and the filtrate was concentrated in vacuo. The residue was purified by reverse phase (0.1% FA condition) to give the title compound (200 mg, 25% yield) as a yellow solid. $^1$H NMR (400 MHz, DMSO-d$_6$) δ 8.96 (s, 1H), 8.47 (s, 1H), 8.24 (s, 1H), 7.07 (s, 1H), 4.48 (s, 1H), 4.38-4.27 (m, 1H), 4.12-4.03 (m, 1H), 3.95 (dd, J=2.4, 11.6 Hz, 1H), 3.90 (s, 3H), 3.60-3.50 (m, 1H), 3.30-3.26 (m, 2H), 2.14-1.99 (m, 3H), 1.95-1.79 (m, 5H), 1.59-1.50 (m, 3H), 1.49-1.31 (m, 2H), 1.21-1.05 (m, 2H); LC-MS (ESI$^+$) m/z 388.3 (M+H)$^+$.

Step 2—(2R)—N-[2-(4-formylcyclohexyl)-6-methoxy-indazol-5-yl]tetrahydropyran-2-carboxamide To a solution of (2R)—N-[2-[4-(hydroxymethyl)cyclohexyl]-6-methoxy-indazol-5-yl]tetrahydropyran -2-carboxamide (90.0 mg, 232 umol) in DCM (5 mL) was added DMP (128 mg, 301 umol). The reaction mixture was stirred at 25° C. for 2 hours. On completion, the reaction mixture was quenched with sat. aq. $Na_2S_2O_3$ (15 mL) and extracted with DCM (2×30 mL). The combined organic phase was washed with $NaHCO_3$ and brine (2×15 mL), dried with anhydrous $Na_2SO_4$, filtered and concentrated in vacuo to give the title compound (85.0 mg, 95% yield) as a yellow solid. $^1$H NMR (400 MHz, DMSO-d$_6$) δ 9.63 (s, 1H), 8.97 (s, 1H), 8.48 (s, 1H), 8.25 (s, 1H), 7.07 (s, 1H), 4.42-4.31 (m, 1H), 4.12-4.04 (m, 1H), 3.95 (dd, J=2.4, 11.6 Hz, 1H), 3.90 (s, 3H), 3.60-3.50 (m, 1H), 3.30 (s, 1H), 2.45-2.36 (m, 1H), 2.23-1.78 (m, 9H), 1.56-1.52 (m, 2H), 1.48-1.40 (m, 2H).

2-(((((2S,4s,7S)-7-((tert-butoxycarbonyl)(methyl)amino)spiro[3.5]nonan-2-yl)methyl)-12-azaneyl)carbonyl)benzoic acid (Intermediate BDD) and 2-(((((2R,4r,7R)-7-((tert-butoxycarbonyl)(methyl)amino)spiro[3.5]nonan-2-yl)methyl)-12-azaneyl)carbonyl)benzoic acid (Intermediate BDE)

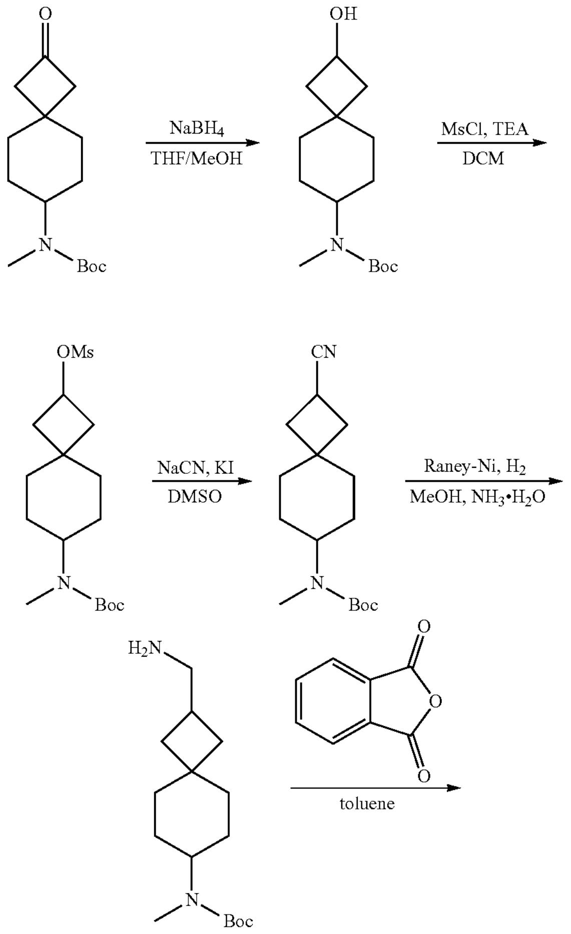

-continued

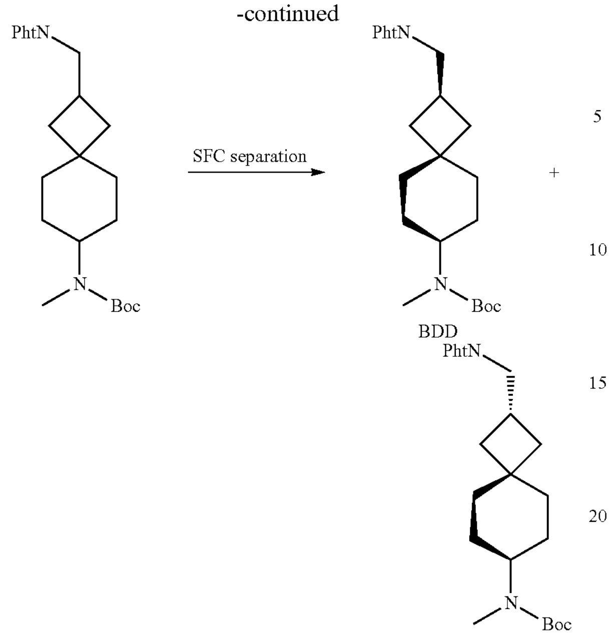

BDD

BDE

Step 1—Tert-butyl N-(2-hydroxyspiro[3.5]nonan-7-yl)-N-methyl-carbamate

To a solution of tert-butyl N-methyl-N-(2-oxospiro[3.5]nonan-7-yl)carbamate (12.0 g, 44.8 mmol, synthesized via Steps 1-2 of Intermediate AWH) in a mixed solvents of THF (100 mL) and MeOH (30 mL) was added $NaBH_4$ (1.87 g, 49.3 mmol) at 0° C. The reaction mixture was stirred at 0° C. for 1 hour. On completion, the reaction mixture was quenched with sat. aq. $NH_4Cl$ (30 mL), diluted with water (100 mL) and extracted with EA (3×200 mL). The combined organic layers were washed with brine (2×60 mL), dried over $Na_2SO_4$, filtered and concentrated in vacuo to give the title compound (11.5 g, 95% yield) as yellow oil. $^1H$ NMR (400 MHz, $CDCl_3$) δ 4.38-4.20 (m, 1H), 4.03-3.52 (m, 1H), 2.70 (s, 3H), 2.39-2.25 (m, 1H), 2.20-2.08 (m, 1H), 1.74-1.62 (m, 4H), 1.61-1.49 (m, 4H), 1.49-1.38 (m, 12H).

Step 2—[7-[Tert-butoxycarbonyl(methyl)amino]spiro[3.5]nonan-2-yl]methanesulfonate To a solution of tert-butyl N-(2-hydroxyspiro[3.5]nonan-7-yl)-N-methyl-carbamate (15.5 g, 57.5 mmol) and TEA (8.73 g, 86.3 mmol) in DCM (150 mL) was added MsCl (7.91 g, 69.0 mmol) at 0° C. The reaction mixture was stirred at 0-20° C. for 1 hour. On completion, the reaction mixture was diluted with water (100 mL) and extracted with DCM (3×100 mL). The combined organic layers were washed with brine (2×60 mL), dried over $Na_2SO_4$, filtered and concentrated in vacuo to give the title compound (19.0 g, 95% yield) as yellow oil. $^1H$ NMR (400 MHz, $CDCl_3$) δ 5.03-4.96 (m, 1H), 4.00-3.59 (m, 1H), 2.98 (s, 3H), 2.70 (s, 3H), 2.53-2.40 (m, 1H), 2.33-2.21 (m, 1H), 2.17-1.93 (m, 2H), 1.75-1.66 (m, 2H), 1.61-1.47 (m, 4H), 1.46 (s, 9H), 1.44-1.34 (m, 2H).

Step 3—Tert-butyl N-(2-cyanospiro[3.5]nonan-7-yl)-N-methyl-carbamate

To a solution of [7-[tert-butoxycarbonyl(methyl)amino]spiro[3.5]nonan-2-yl]methanesulfonate (19.0 g, 54.6 mmol) and KI (13.6 g, 82.0 mmol) in DMSO (200 mL) was added NaCN (4.02 g, 82.0 mmol) at 25° C. The reaction mixture was stirred at 100° C. for 48 hours. On completion, the reaction mixture was poured into water (400 mL), and extracted with EA (3×180 mL). The combined organic layers were washed with brine (2×100 mL), dried over $Na_2SO_4$, filtered and concentrated in vacuo. The residue was purified by silica gel chromatography (PE:EA=20:1) to give the title compound (9.90 g, 65% yield) as white solid. $^1H$ NMR (400 MHz, $CDCl_3$) δ 4.05-3.51 (m, 1H), 3.04-2.97 (m, 1H), 2.69 (s, 3H), 2.31-2.21 (m, 1H), 2.17-2.07 (m, 3H), 1.94-1.84 (m, 1H), 1.82-1.72 (m, 1H), 1.60-1.50 (m, 2H), 1.50-1.46 (m, 1H), 1.45 (s, 9H), 1.44-1.34 (m, 3H).

Step 4—Tert-butyl N-[2-(aminomethyl)spiro[3.5]nonan-7-yl]-N-methyl-carbamate

To a solution of tert-butyl N-(2-cyanospiro[3.5]nonan-7-yl)-N-methyl-carbamate (10.5 g, 37.7 mmol) and $NH_3.H_2O$ (36.4 g, 259 mmol, 40 mL) in MeOH (100 mL) was added Raney-Ni (969 mg, 11.3 mmol). The reaction mixture was stirred at 25° C. for 16 hours under $H_2$ (50 psi). On completion, the reaction mixture was filtered and the filtrate was concentrated in vacuo to give the title compound (10.1 g, 94% yield) as yellow oil. $^1H$ NMR (400 MHz, DMSO-$d_6$) δ 3.88-3.56 (m, 1H), 2.62 (s, 3H), 2.55-2.51 (m, 2H), 2.26-2.04 (m, 1H), 1.95-1.74 (m, 2H), 1.72-1.63 (m, 1H), 1.62-1.40 (m, 4H), 1.38 (s, 9H), 1.37-1.22 (m, 5H).

Step 5—Tert-butyl N-[2-[(1,3-dioxoisoindolin-2-yl)methyl]spiro[3.5]nonan-7-yl]-N-methyl- carbamate A mixture of tert-butyl N-[2-(aminomethyl)spiro[3.5]nonan-7-yl]-N-methyl-carbamate (9.80 g, 34.7 mmol) and isobenzofuran-1,3-dione (6.17 g, 41.6 mmol, CAS #85-44-9) in toluene (100 mL) was stirred at 110° C. for 12 hours. On completion, the reaction mixture was concentrated in vacuo. The residue was purified by silica gel chromatography (PE:EA=20:1) to give the title compound (11.6 g, 80% yield) as white solid. $^1H$ NMR (400 MHz, $CDCl_3$) δ 7.84 (dd, J=3.2, 5.6 Hz, 2H), 7.72 (dd, J=3.2, 5.6 Hz, 2H), 3.98-3.53 (m, 3H), 2.73-2.57 (m, 4H), 2.00-1.89 (m, 1H), 1.85-1.75 (m, 2H), 1.73-1.64 (m, 1H), 1.64-1.59 (m, 1H), 1.59-1.46 (m, 4H), 1.45 (s, 9H), 1.43-1.34 (m, 3H).

Step 6—2-(((((2S,4s,7S)-7-((tert-butoxycarbonyl)(methyl)amino)spiro[3.5]nonan-2-yl)methyl)-12-azaneyl)carbonyl)benzoic acid and 2-(((((2R,4r,7R)-7-((tert-butoxycarbonyl)(methyl)amino)spiro[3.5]nonan-2-yl)methyl)-12-azaneyl)carbonyl)benzoic acid The racemate tert-butyl N-[2-[(1,3-dioxoisoindolin-2-yl)methyl]spiro[3.5]nonan-7-yl]-N-methyl- carbamate was separated by SFC ((column: DAICEL CHIRALCEL OJ-H (250 mm*30 mm, Sum); mobile phase: [0.1% $NH_3.H_2O$ ETOH]) to give the two title compounds. The first peak -(((((2S,4s,7S)-7-((tert-butoxycarbonyl)(methyl)amino)spiro[3.5]nonan-2-yl)methyl)-12-azaneyl)carbonyl)benzoic acid (4.80 g, 96% yield, 99.1% ee) was obtained as colorless gum. $^1H$ NMR (400 MHz, $CDCl_3$) δ 7.84 (dd, J=3.2, 5.6 Hz, 2H), 7.72 (dd, J=3.2, 5.6 Hz, 2H), 3.97-3.62 (m, 3H), 2.75-2.57 (m, 4H), 2.00-1.90 (m, 1H), 1.86-1.74 (m, 2H), 1.72-1.64 (m, 1H), 1.63-1.54 (m, 2H), 1.54-1.46 (m, 3H), 1.45 (s, 9H), 1.43-1.33 (m, 3H); LC-MS ($ESI^+$) m/z 357.2 $(M+H-56)^+$. The second peak 2-(((((2R,4r,7R)-7-((tert-butoxycarbonyl)(methyl)amino)spiro[3.5]nonan-2-yl)

methyl)-12-azaneyl)carbonyl)benzoic acid (4.90 g, 97% yield, 96.4% ee) was obtained as colorless gum. $^1H$ NMR (400 MHz, $CDCl_3$) δ 7.85 (dd, J=3.2, 5.6 Hz, 2H), 7.72 (dd, J=3.2, 5.6 Hz, 2H), 3.94-3.62 (m, 3H), 2.76-2.55 (m, 4H), 2.01-1.90 (m, 1H), 1.86-1.74 (m, 2H), 1.72-1.65 (m, 1H), 1.64-1.59 (m, 1H), 1.55-1.47 (m, 3H), 1.45 (s, 9H), 1.44-1.32 (m, 4H); LC-MS ($ESI^+$) m/z 357.2 $(M+H-56)^+$. The stereoisomers were assigned arbitrarily.

Tert-butyl N-[2-(aminomethyl)spiro[3.5]nonan-7-yl]-N-methyl-carbamate (Intermediate BDF)

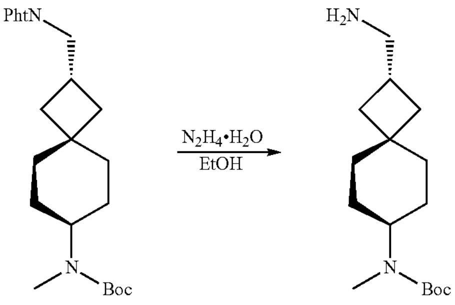

BDE BDF

To a solution of tert-butyl N-[2-[(1,3-dioxoisoindolin-2-yl)methyl]spiro[3.5]nonan-7-yl]-N-methyl -carbamate (383 mg, 929 umol, Intermediate BDE) in EtOH (6 mL) was added $N_2H4.H_2O$ (232 mg, 4.65 mmol). The reaction mixture was stirred at 80° C. for 2 hours. On completion, the reaction mixture was concentrated in vacuo. The residue was diluted with DCM (40 mL) and filtered. The filtrate was concentrated in vacuo to give the title compound (230 mg, 87% yield) as yellow oil. $^1H$ NMR (400 MHz, DMSO-$d_6$) δ 3.83-3.47 (m, 1H), 2.62 (s, 3H), 2.52-2.50 (m, 2H), 2.14 (td, J=7.6, 15.6 Hz, 1H), 1.93-1.73 (m, 2H), 1.72-1.62 (m, 1H), 1.61-1.53 (m, 1H), 1.52-1.45 (m, 1H), 1.43-1.39 (m, 2H), 1.38 (s, 9H), 1.36-1.32 (m, 2H), 1.32-1.22 (m, 3H).

2-(2,6-Dioxo-3-piperidyl)-4-[[7-(methylamino)spiro[3.5]nonan-2-yl]methylamino]isoindoline-1,3-dione (Intermediate BDG)

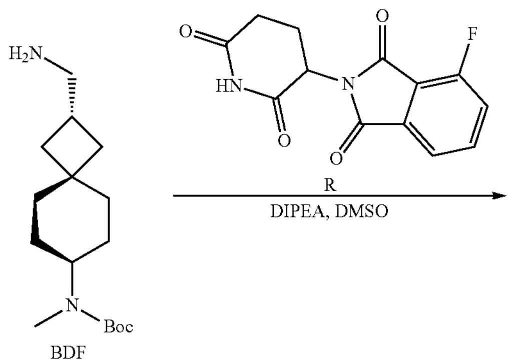

BDF

-continued

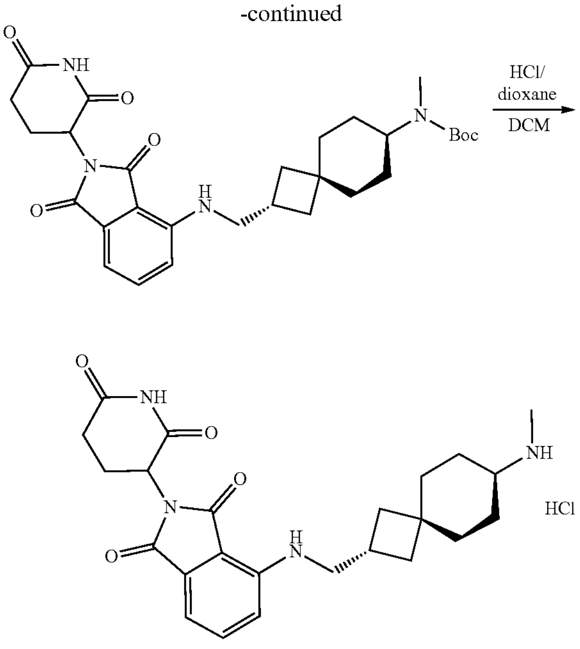

BDG

Step 1—Tert-butyl N-[2-[[[2-(2,6-dioxo-3-piperidyl)-1,3-dioxo-isoindolin-4-yl]amino]methyl]spiro[3.5]nonan-7-yl]-N-methyl-carbamate To a solution of tert-butyl N-[2-(aminomethyl)spiro[3.5]nonan-7-yl]-N-methyl-carbamate (230 mg, 814 umol, Intermediate BDF) and 2-(2,6-dioxo-3-piperidyl)-4-fluoro-isoindoline-1,3-dione (224 mg, 814 umol, Intermediate R) in DMSO (3 mL) was added DIPEA (210 mg, 1.63 mmol). The reaction mixture was stirred at 130° C. for 3 hours. On completion, the reaction mixture was diluted with water (15 mL) and extracted with EA (3x20 mL). The combined organic layers were washed with brine (2x15 mL), dried over $Na_2SO_4$, filtered and concentrated in vacuo. The residue was purified by reverse phase (0.1% FA) to give the title compound (280 mg, 63% yield) as yellow solid. $^1H$ NMR (400 MHz, $CDCl_3$) δ 8.09 (s, 1H), 7.49 (dd, J=7.2, 8.4 Hz, 1H), 7.10 (d, J=7.2 Hz, 1H), 6.88 (d, J=8.8 Hz, 1H), 6.19 (t, J=5.2 Hz, 1H), 4.92 (dd, J=5.2, 12.0 Hz, 1H), 4.03-3.58 (m, 1H), 3.37-3.13 (m, 2H), 2.96-2.84 (m, 1H), 2.84-2.72 (m, 2H), 2.70 (s, 3H), 2.61-2.49 (m, 1H), 2.18-2.03 (m, 2H), 1.95-1.82 (m, 2H), 1.68-1.60 (m, 1H), 1.57-1.52 (m, 2H), 1.52-1.48 (m, 2H), 1.46 (s, 9H), 1.45-1.36 (m, 4H).

Step 2—2-(2,6-Dioxo-3-piperidyl)-4-[[7-(methylamino)spiro[3.5]nonan-2-yl]methylamino]isoindoline-1,3-dione To a solution of tert-butyl N-[2-[[[2-(2,6-dioxo-3-piperidyl)-1,3-dioxo-isoindolin-4-yl]amino]methyl]spiro[3.5]nonan-7-yl]-N-methyl-carbamate (280 mg, 519 umol) in DCM (4 mL) was added HCl/dioxane (4 M, 4 mL). The reaction mixture was stirred at 20° C. for 0.5 hour. On completion, the reaction mixture was concentrated in vacuo to give the title compound (240 mg, 97% yield, HCl salt) as yellow solid. LC-MS ($ESI^+$) m/z 439.4 $(M+H)^+$.

6-(Pentafluoro-sulfanyl)pyridine-2-carboxylic acid (Intermediate BDH)

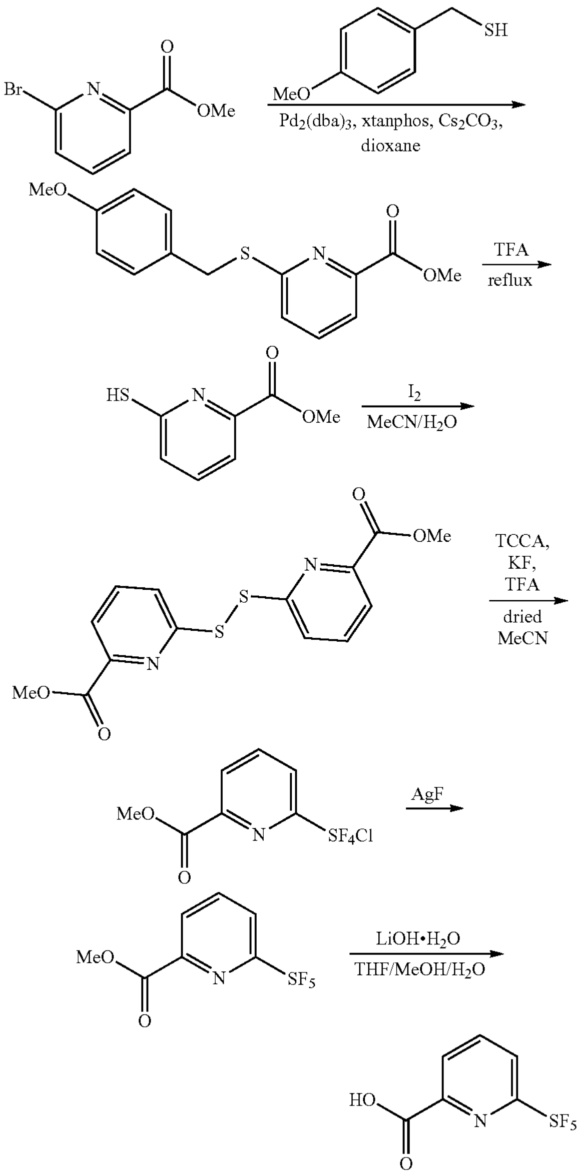

BDH

Step 1—Methyl 6-((4-methoxybenzyl)thio)picolinate

To a solution of (4-methoxyphenyl)methanethiol (7.14 g, 46.2 mmol, CAS #6258-60-2) and methyl 6-bromopyridine-2-carboxylate (10.0 g, 46.2 mmol, CAS #26218-75-7) in dioxane (100 mL) was added $Pd_2(dba)_3$ (2.12 g, 2.31 mmol), Xantphos (2.68 g, 4.63 mmol) and DIPEA (11.9 g, 92.5 mmol). The mixture was stirred at 110° C. for 2 hours. On completion, the reaction mixture was filtered and concentrated in vacuo. The residue was purified by column chromatography ($SiO_2$, Petroleum ether/Ethyl acetate=100/1 to 10/1) to give the title compound (13.0 g, 89% yield) as a brown oil. $^1H$ NMR (400 MHz, $CDCl_3$) δ 7.79 (dd, J=0.8, 7.6 Hz, 1H), 7.58 (t, J=7.6 Hz, 1H), 7.42 (d, J=8.8 Hz, 2H), 7.31-7.27 (m, 1H), 6.86-6.79 (m, 2H), 4.45 (s, 2H), 4.01 (s, 3H), 3.78 (s, 3H); LC-MS ($ESI^+$) m/z 290.1 $(M+H)^+$.

Step 2—Methyl 6-mercaptopicolinate

A solution of methyl 6-[(4-methoxyphenyl)methylsulfanyl]pyridine-2-carboxylate (13.0 g, 44.9 mmol) in TFA (65 mL) was stirred at 85° C. for 12 hours. On completion, the reaction mixture was concentrated in vacuo. The residue was diluted with EA (30 mL) and stirred at 25° C. for 30 minutes. Then the mixture was filtered. The filter cake was collected and dried in vacuo to give the title compound (6.10 g, 77% yield) as a yellow solid. LC-MS ($ESI^+$) m/z 170.2 $(M+H)^+$.

Step 3—Dimethyl 6,6'-disulfanediyldipicolinate

To a solution of methyl 6-sulfanylpyridine-2-carboxylate (6.00 g, 35.4 mmol) in MeCN (80 mL) and $H_2O$ (16 mL) was added $I_2$ (4.50 g, 17.7 mmol). The mixture was stirred at 25° C. for 2 hours. On completion, the reaction mixture was quenched with 1% aq. $Na_2S_2O_3$ (200 mL) at 25° C., and filtered. The cake was washed with $H_2O$ (3×50 mL). The filter cake was dissolved in EA (200 mL), washed with 1% aq.$Na_2S_2O_3$ aqueous (50 mL) and brine (3×50 mL). The organic layer was concentrated in vacuo to give the title compound (3.00 g, 24% yield) as a yellow solid. $^1H$ NMR (400 MHz, DMSO-$d_6$) δ 8.04-7.98 (m, 2H), 7.95-7.89 (m, 4H), 3.88 (s, 6H); LC-MS ($ESI^+$) m/z 337.0 $(M+H)^+$.

Step 4—Methyl 6-[chloro(tetrafluoro)-sulfanyl]pyridine-2-carboxylate

To a mixture of methyl 6-[(6-methoxycarbonyl-2-pyridyl)disulfanyl]pyridine-2-carboxylate (2.00 g, 5.95 mmol) in MeCN (40.0 mL) was added dried KF (11.0 g, 190 mmol), 1,3,5-trichloro-1,3,5- triazinane-2,4,6-trione (24.8 g, 107 mmol) in glove box under $N_2$. Then, a solution of TFA (13.6 mg, 118 umol) in MeCN (1.0 mL) was added. The mixture was stirred at 25° C. under $N_2$ for 18 hours. On completion, the reaction mixture was filtered quickly, and the filtrate was concentrated in vacuo to give the title compound (1.30 g, 80% yield) as white solid. The crude product was very sensitive to moisture and used to the next step directly. $^{19}F$ NMR (376 MHz, CDCN) δ 123.63.

Step 5—Methyl 6-(pentafluoro-sulfanyl)pyridine-2-carboxylate

A mixture of methyl 6-[chloro(tetrafluoro)-sulfanyl]pyridine-2-carboxylate (2.50 g, 8.94 mmol) and AgF (3.40 g, 26.8 mmol) was stirred at 85° C. under $N_2$ for 48 hours. On completion, the mixture was quenched with $H_2O$ (10 mL) and then extracted with DCM (3×20 mL). The combined organic phase was dried over $Na_2SO_4$, filtered and the filtrate was concentrated in vacuo. The residue was purified by column chromatography ($SiO_2$, Petroleum ether/Ethyl acetate=30/1 to 10/1) to give crude product. The crude product was re-purified by reverse phase (FA condition) to give the title compound (100 mg, 4% yield) as yellow solid. $^1H$ NMR (400 MHz, $CDCl_3$) δ 8.32 (d, J=7.6 Hz, 1H), 8.10 (t, J=8.0 Hz, 1H), 7.95 (d, J=8.0 Hz, 1H), 4.04 (s, 3H); $^{19}F$ NMR (376 MHz, $CDCl_3$) δ 77.97-76.19 (m, 1F), 52.65 (s, 2F), 52.25 (s, 2F); LC-MS ($ESI^+$) m/z 264.0 $(M+H)^+$.

Step 6—6-(Pentafluoro-sulfanyl)pyridine-2-carboxylic acid

To a mixture of methyl 6-(pentafluoro-sulfanyl)pyridine-2-carboxylate (90.0 mg, 341 umol) in a mixed solvent of THE (3 mL) and $H_2O$ (1 mL) was added LiOH $H_2O$ (43.0 mg, 1.03 mmol) at 25° C. The mixture was stirred at 25° C. for 1 hour. On completion, the mixture was concentrated in vacuo. The residue was made acidic to pH=3 with 1.0 M aq. HCl, then extracted with DCM (3×10 mL). The combined organic phase was dried over $Na_2SO_4$, filtered and the filtrate was concentrated in vacuo to give the title compound (70.0 mg, 82% yield) as yellow solid. LC-MS (ESI$^+$) m/z 250.0 (M+H)$^+$.

N-[2-(4-formylcyclohexyl)-6-(1-hydroxy-1-methyl-ethyl)indazol-5-yl]-6-(pentafluoro- sulfanyl)pyridine-2-carboxamide (Intermediate BDI)

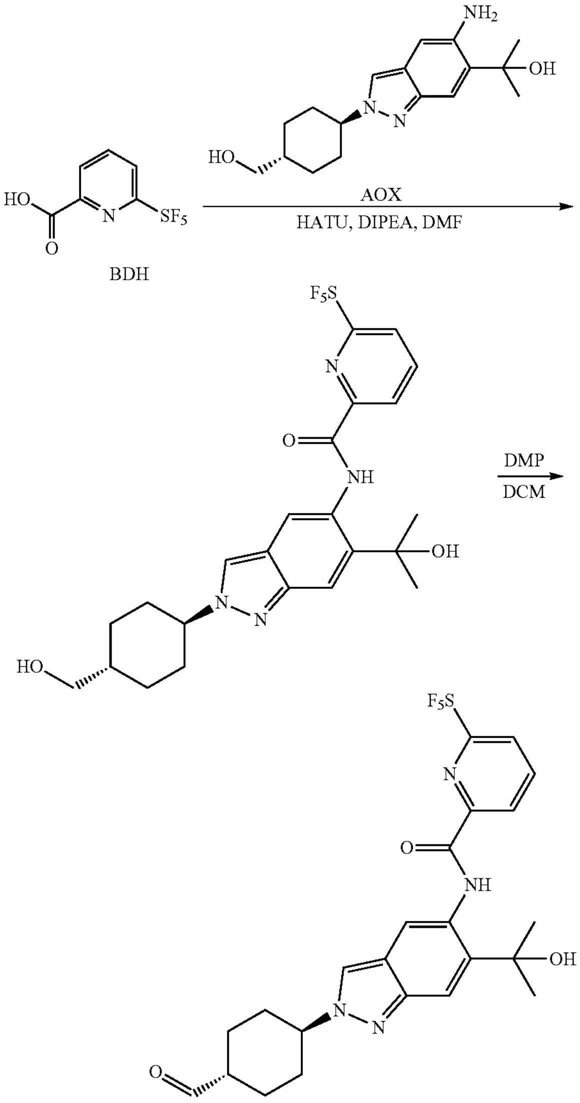

BDH

BDI

Step 1—N-[2-[4-(hydroxymethyl)cyclohexyl]-6-(1-hydroxy-1-methyl-ethyl)indazol-5-yl]-6- (pentafluoro-sulfanyl)pyridine-2-carboxamide To a mixture of 6-(pentafluoro-sulfanyl)pyridine-2-carboxylic acid (50.0 mg, 200 umol, Intermediate BDH) in DMF (4 mL) was added CMPI (66.6 mg, 260 umol) and DIPEA (77.8 mg, 602 umo). The mixture was stirred at 25° C. for 5 minutes. 2-[5-amino-2-[4-(hydroxymethyl)cyclohexyl]indazol-6-yl]propan-2-ol (60.8 mg, 200 umol, Intermediate AOX) was then added and the mixture was stirred at 25° C. for 1.5 hours. On completion, the reaction mixture was quenched with $H_2O$ (0.2 mL) at 25° C. The mixture was concentrated in vacuo and the residue was purified by reverse phase (FA condition) to afford the title compound (50.0 mg, 46% yield) as yellow solid. $^1$H NMR (400 MHz, DMSO-$d_6$) δ 12.32 (s, 1H), 8.74 (s, 1H), 8.49-8.41 (m, 2H), 8.37 (s, 1H), 8.29-8.24 (m, 1H), 7.58 (s, 1H), 5.91 (s, 1H), 4.49 (t, J=4.8 Hz, 1H), 4.46-4.36 (m, 1H), 3.30 (s, 2H), 2.19-2.09 (m, 2H), 1.96-1.83 (m, 4H), 1.62 (s, 6H), 1.55-1.42 (m, 1H), 1.23-1.08 (m, 2H). LC-MS (ESI$^+$) m/z 535.1 (M+H)$^+$.

Step 2—N-[2-(4-formylcyclohexyl)-6-(1-hydroxy-1-methyl-ethyl)indazol-5-yl]-6-(pentafluoro- sulfanyl) pyridine-2-carboxamide To a mixture of N-[2-[4-(hydroxymethyl)cyclohexyl]-6-(1-hydroxy-1-methyl-ethyl)indazol-5-yl]-6- (pentafluoro-sulfanyl)pyridine-2-carboxamide (45 mg, 84.2 umol) in DCM (1.0 mL) was added DMP (49.9 mg, 117 umol) at 25° C. The mixture was stirred at 25° C. for 2 hours. On completion, the reaction mixture was quenched with saturated $Na_2SO_3$ (10.0 mL) and $NaHCO_3$ (10.0 mL) at 25° C., and then extracted with DCM (3×20 mL). The combined organic layer was washed with brine (10 mL), dried over $Na_2SO_4$, filtered and concentrated in vacuo to give the title compound (45.0 mg, 99% yield) as yellow solid. LC-MS (ESI$^+$) m/z 533.1 (M+H)$^+$.

((1R, 4R)-4-(5-bromo-6-methoxy-7-methyl-2H-indazol-2-yl)cyclohexyl)methanol (Intermediate BDJ)

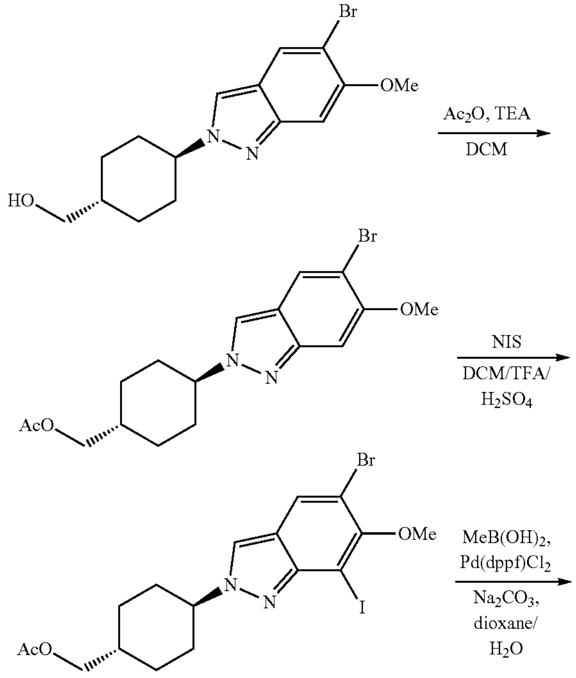

-continued

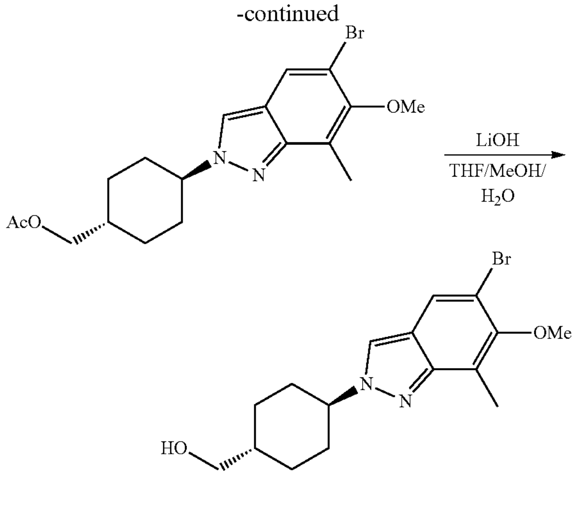

Step 1—((1R, 4R)-4-(5-Bromo-6-methoxy-2H-indazol-2-yl)cyclohexyl)methyl acetate

To a solution of [4-(5-bromo-6-methoxy-indazol-2-yl) cyclohexyl]methanol (2.00 g, 5.90 mmol, synthesized via Steps 1-3 of Intermediate ATE) in DCM (20 mL) was added TEA (1.79 g, 17.6 mmol) and $Ac_2O$ (1.20 g, 11.7 mmol) at 0° C. The mixture was stirred at 25° C. for 12 hours. On completion, the reaction mixture was quenched with $H_2O$ (100 mL) at 25° C. and extracted with DCM (3×50 mL). The combined organic layers were washed with brine (50 mL), dried over $Na_2SO_4$, filtered and concentrated in vacuo. The residue was purified by column chromatography ($SiO_2$, Petroleum ether/Ethyl acetate=100/1 to 1/1) to give the title compound (2.00 g, 86% yield) as an off-white solid. $^1H$ NMR (400 MHz, $CDCl_3$) δ 7.86 (s, 1H), 7.82 (s, 1H), 7.05 (s, 1H), 4.32 (m, 1H), 3.98 (d, J=6.4 Hz, 2H), 3.94 (s, 3H), 2.37-2.28 (m, 2H), 2.09 (s, 3H), 2.06-1.89 (m, 4H), 1.82 (m, 1H), 1.35-1.19 (m, 2H); LC-MS ($ESI^+$) m/z 381.0 $(M+H)^+$.

Step 2—((1R, 4R)-4-(5-Bromo-7-iodo-6-methoxy-2H-indazol-2-yl)cyclohexyl)methyl acetate To a solution of [4-(5-bromo-6-methoxy-indazol-2-yl) cyclohexyl]methyl acetate (1.00 g, 2.62 mmol) in DCM (5 mL) and TFA (5 mL) and $H_2SO_4$ (2.5 mL) was added NIS (590 mg, 2.62 mmol). The mixture was stirred at 25° C. for 0.5 hour. On completion, the reaction mixture was quenched with sat. aq. $NaHCO_3$ (50 mL) at 0° C., and then diluted with $H_2O$ (50 mL) and extracted with DCM (3×50 mL). The combined organic layers were washed with brine (50 mL), dried over $Na_2SO_4$, filtered and concentrated in vacuo. The residue was purified by column chromatography ($SiO_2$, Petroleum ether/Ethyl acetate=100/1 to 1/1) to give the title compound (1.00 g, 74% yield) as a brown oil. $^1H$ NMR (400 MHz, $CDCl_3$) δ 8.04 (s, 1H), 7.85 (s, 1H), 4.56-4.44 (m, 1H), 3.98 (d, J=6.4 Hz, 2H), 3.93 (s, 3H), 2.42-2.34 (m, 2H), 2.09 (s, 3H), 2.06-1.97 (m, 2H), 1.94-1.78 (m, 3H), 1.35-1.21 (m, 2H); LC-MS ($ESI^+$) m/z 508.9 $(M+H)^+$.

Step 3—((1R, 4R)-4-(5-Bromo-6-methoxy-7-methyl-2H-indazol-2-yl)cyclohexyl)methyl acetate To a solution of [4-(5-bromo-7-iodo-6-methoxy-indazol-2-yl)cyclohexyl]methyl acetate (800 mg, 1.58 mmol) in dioxane (8 mL) and $H_2O$ (0.8 mL) was added $MeB(OH)_2$ (94.4 mg, 1.58 mmol), $Na_2CO_3$ (501 mg, 4.73 mmol) and $Pd(dppf)Cl_2.CH_2Cl_2$ (128 mg, 157 umol). The mixture was stirred at 100° C. for 6 hours. On completion, the reaction mixture was filtered and concentrated in vacuo. The residue was purified by column chromatography ($SiO_2$, PE/EA=100/1 to 3/1) to give the title compound (120 mg, 15% yield) as a white solid. LC-MS ($ESI^+$) m/z 397.0 $(M+H)^+$.

Step 4—((1R, 4R)-4-(5-bromo-6-methoxy-7-methyl-2H-indazol-2-yl)cyclohexyl)methanol To a solution of [4-(5-bromo-6-methoxy-7-methyl-indazol-2-yl)cyclohexyl]methyl acetate (120 mg, 239 umol) in THE (1 mL) and MeOH (1 mL) and $H_2O$ (0.5 mL) was added LiOH $H_2O$ (50.3 mg, 1.20 mmol). The mixture was stirred at 25° C. for 0.5 hour. On completion, the reaction mixture was partitioned between $H_2O$ (50 mL) and EA (50 mL). The organic phase was separated, washed with brine (50 mL), dried over $Na_2SO_4$, filtered and concentrated in vacuo to give the title compound (120 mg, 100% yield) as an off-white solid. LC-MS ($ESI^+$) m/z 355.2 $(M+H)^+$.

6-(1,1-Difluoroethyl)-N-(2-((1R, 4R)-4-formylcyclohexyl)-6-methoxy-7-methyl-2H-indazol -5-yl)picolinamide (Intermediate BDK)

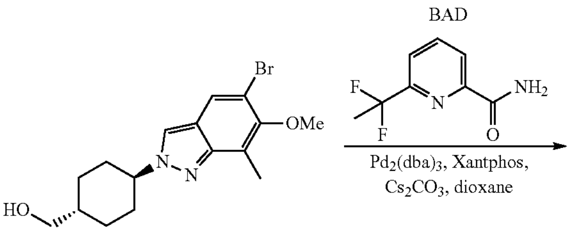

BDJ

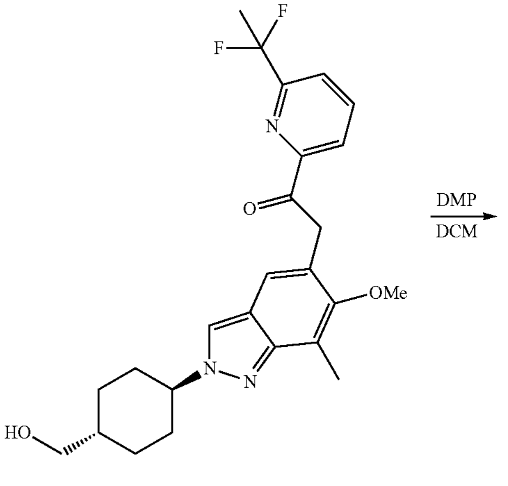

-continued

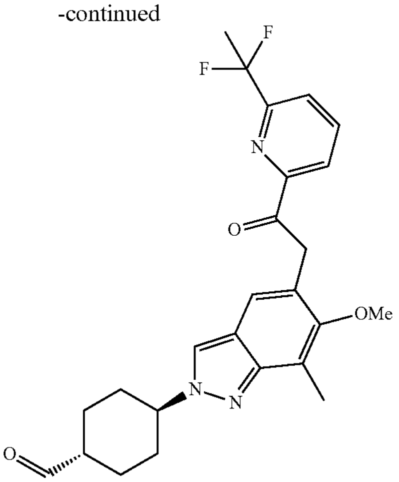

BDK

Step 1—6-(1,1-Difluoroethyl)-N-(2-((1R, 4R)-4-(hydroxymethyl)cyclohexyl)-6-methoxy-7-methyl-2H -indazol-5-yl)picolinamide To a solution of [4-(5-bromo-6-methoxy-7-methyl-indazol-2-yl)cyclohexyl]methanol (120 mg, 339 umol, Intermediate BDJ) and 6-(1,1-difluoroethyl)pyridine-2-carboxamide (69.5 mg, 373 umol, Intermediate BAD) in dioxane (2 mL) was added $Pd_2(dba)_3$ (31.1 mg, 33.9 umol), $Cs_2CO_3$ (221 mg, 679 umol) and Xantphos (39.3 mg, 67.9 umol). The mixture was stirred at 80° C. for 12 hours. On completion, the reaction mixture was filtered and concentrated in vacuo. The residue was purified by prep-TLC ($SiO_2$, PE:EA=1:1) to give the title compound (70.0 mg, 44% yield) as a white solid. LC-MS ($ESI^+$) m/z 459.3 $(M+H)^+$.

Step 2—6-(1,1-Difluoroethyl)-N-(2-((1R, 4R)-4-formylcyclohexyl)-6-methoxy-7-methyl-2H-indazol-5-yl)picolinamide To a solution of 6-(1, 1-difluoroethyl)-N-[2-[4-(hydroxymethyl)cyclohexyl]-6-methoxy-7-methyl- indazol-5-yl]pyridine-2-carboxamide (70.0 mg, 152 umol) in DCM (1 mL) was added DMP (84.1 mg, 198 umol) at 0° C. The mixture was stirred at 25° C. for 0.5 hour. On completion, the reaction was quenched with sat .aq. $Na_2SO_3$ (20 mL) and sat. aq. $NaHCO_3$ (20 mL) at 0° C. The mixture was diluted with $H_2O$ (20 mL) and extracted with DCM (3×50 mL). The combined organic layers were washed with brine (50 mL), dried over $Na_2SO_4$, filtered and concentrated in vacuo to give the title compound (69.0 mg, 44% yield) as a white solid. LC-MS ($ESI^+$) m/z 457.3 $(M+H)^+$.

Methyl 2-methylsulfanyl-1,3-benzoxazole-5-carboxylate (Intermediate BDL)

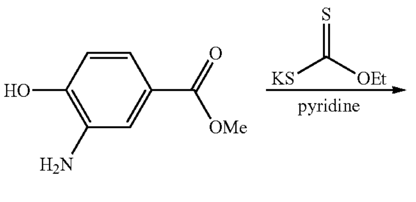

-continued

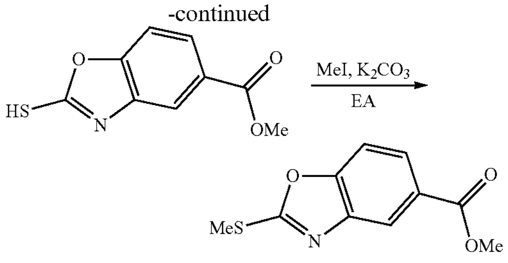

BDL

Step 1—Methyl 2-sulfanyl-1,3-benzoxazole-5-carboxylate

A mixture of methyl 3-amino-4-hydroxy-benzoate (5.00 g, 29.9 mmol) and ethoxycarbothioylsulfanyl potassium (7.19 g, 44.8 mmol, CAS #140-89-6) in the pyridine (50 mL) was stirred at 110° C. for 18 hours. On completion, the mixture was concentrated in vacuo. The residue was diluted with water (100 mL) and made acidic to pH=7 with 1.0 M aq. HCl. The mixture was filtered and the cake was diluted with EA (50 mL), dried over $Na_2SO_4$, filtered and concentrated in vacuo to give the title compound (4.20 g, 67% yield). $^1H$ NMR (400 MHz, DMSO-$d_6$) δ 7.88 (dd, J=1.6, 8.4 Hz, 1H), 7.68 (d, J=1.2 Hz, 1H), 7.62 (d, J=8.4 Hz, 1H), 3.87 (s, 3H).

Step 2—Methyl 2-methylsulfanyl-1,3-benzoxazole-5-carboxylate

To a solution of methyl 2-sulfanyl-1,3-benzoxazole-5-carboxylate (2.00 g, 9.56 mmol) in EtOAc (20 mL) was added $K_2CO_3$ (1.98 g, 14.3 mmol) and MeI (4.07 g, 28.6 mmol). The mixture was stirred at 25° C. for 12 hours. On completion, the mixture was diluted with EA (100 mL) and washed with water (50 mL). The organic layer was dried over $Na_2SO_4$, filtered and concentrated in vacuo to give the title compound (2.10 g, 98% yield) as gray solid. $^1H$ NMR (400 MHz, $CDCl_3$) δ 8.30 (d, J=1.2 Hz, 1H), 8.02 (dd, J=1.6, 8.4 Hz, 1H), 7.47 (d, J=8.4 Hz, 1H), 3.96 (s, 3H), 2.79 (s, 3H).

Methyl 6-bromo-2-[4-(hydroxymethyl)-1-piperidyl]-1,3-benzoxazole-5-carboxylate (Intermediate BDM)

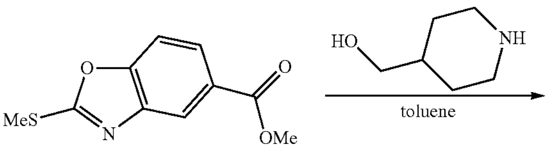

BDL

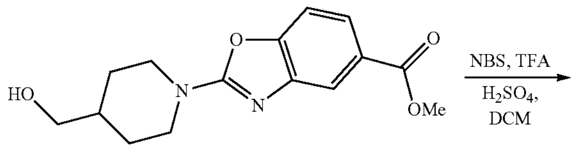

-continued

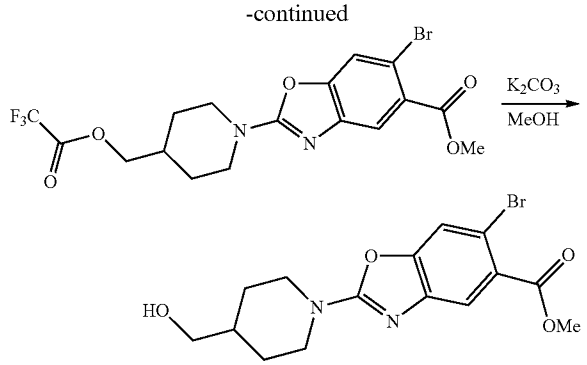

BDM

Step 1—Methyl 2-[4-(hydroxymethyl)-1-piperidyl]-1,3-benzoxazole-5-carboxylate

To a solution of methyl 2-methylsulfanyl-1,3-benzoxazole-5-carboxylate (2.10 g, 9.41 mmol, Intermediate BDL) in toluene (30 mL) was added 4-piperidylmethanol (5.42 g, 47.0 mmol, CAS #6457-49-4). The mixture was stirred at 120° C. for 6 hours. On completion, the mixture was concentrated in vacuo. The residue was diluted with EA (100 mL) and washed with water (2×100 mL). The organic layer was dried over $Na_2SO_4$, filtered and concentrated in vacuo. The residue was purified by reversed phase (FA condition) to give the title compound (2.30 g, 84% yield) as yellow solid. $^1$H NMR (400 MHz, $CDCl_3$) δ 8.00 (d, J=1.2 Hz, 1H), 7.79 (dd, J=1.6, 8.4 Hz, 1H), 7.25 (s, 1H), 4.36 (d, J=13.2 Hz, 2H), 3.92 (s, 3H), 3.56 (d, J=6.4 Hz, 2H), 3.15-3.08 (m, 2H), 1.92-1.88 (m, 2H), 1.80-1.74 (m, 1H), 1.42-1.32 (m, 2H).

Step 2—Methyl 6-bromo-2-[4-[(2,2,2-trifluoroacetyl)oxymethyl]-1-piperidyl]-1,3-benzoxazole-5-carboxylate To a solution of methyl 2-[4-(hydroxymethyl)-1-piperidyl]-1,3-benzoxazole-5-carboxylate (2.15 g, 7.41 mmol) in DCM (8 mL), TFA (8 mL) and $H_2SO_4$ (4 mL) was added NBS (1.71 g, 9.63 mmol) at 0° C. The mixture was stirred at 25° C. for 1 hour. On completion, the mixture was poured into sat. aq. $K_2CO_3$ (100 mL) slowly at 0-5° C., extracted with DCM (3×100 mL). The combine organic layer was washed with brine (50 mL), dried over $Na_2SO_4$, filtered and concentrated in vacuo to give the title compound (3.20 g, 92% yield) as light yellow gum. LC-MS (ESI$^+$) m/z 465.0, 467.0 (M+H)$^+$.

Step 3—Methyl 6-bromo-2-[4-(hydroxymethyl)-1-piperidyl]-1,3-benzoxazole-5-carboxylate A mixture of methyl 6-bromo-2-[4-[(2,2,2-trifluoroacetyl)oxymethyl]-1-piperidyl]-1,3-benzoxazole -5-carboxylate (3.20 g, 6.88 mmol) and $K_2CO_3$ (2.88 g, 20.8 mmol) in MeOH (30 mL) was stirred at 25° C. for 1 hour. On completion, the mixture was concentrated in vacuo. The residue was diluted with EA (100 mL), washed with brine (20 mL), dried over $Na_2SO_4$, filtered and concentrated in vacuo. The residue was purified by reversed phase flash (FA condition) to give the title compound (2.00 g, 78% yield) as light yellow gum. $^1$H NMR (400 MHz, $CDCl_3$) δ 7.75 (s, 1H), 7.51 (s, 1H), 4.40-4.28 (m, 2H), 3.93 (s, 3H), 3.57 (d, J=4.4 Hz, 2H), 3.16-3.08 (m, 2H), 1.92-1.89 (m, 2H), 1.85-1.75 (m, 1H), 1.51 (m, 1H), 1.40-1.32 (m, 2H).

N-[2-(4-formyl-1-piperidyl)-5-(1-hydroxy-1-methylethyl)-1,3-benzoxazol-6-yl]-6-(trifluoro methyl)pyridine-2-carboxamide (Intermediate BDN)

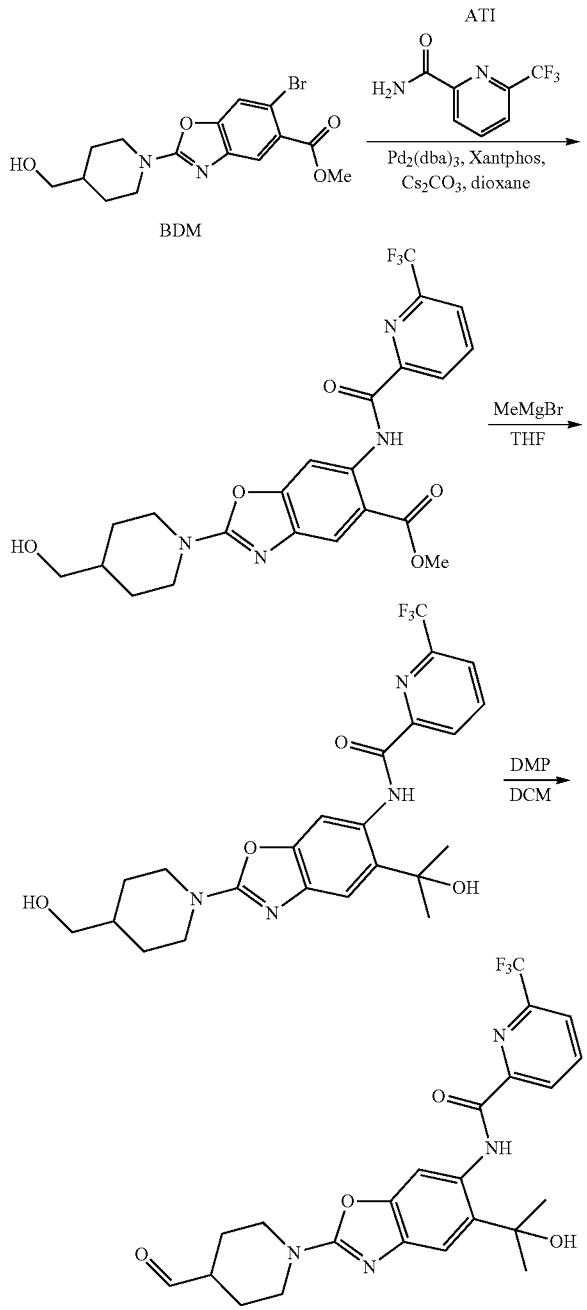

Step 1—Methyl 2-[4-(hydroxymethyl)-1-piperidyl]-6-[[6-(trifluoromethyl)pyridine-2-carbonyl]amino]-1,3-benzoxazole-5-carboxylate A mixture of methyl 6-bromo-2-[4-(hydroxymethyl)-1-piperidyl]-1,3-benzoxazole-5-carboxylate (1.90 g, 5.15 mmol, Intermediate BDM), 6-(trifluoromethyl)pyridine-2-carboxamide (1.14 g, 6.00 mmol, Intermediate ATI), $Pd_2(dba)_3$ (472 mg, 515 umol), Xantphos (596 mg, 1.03 mmol) and $Cs_2CO_3$ (3.36 g, 10.3 mmol) in dioxane (40 mL) was stirred at 80° C. for 16 hours under $N_2$. On completion, the mixture was filtered, and the cake was washed with DCM (50 mL). The filtrate and washing were combined and concentrated in vacuo. The residue was purified by reverse phase flash (FA condition) to give the title compound (1.70 g, 45% yield) as light yellow solid. LC-MS ($ESI^+$) m/z 479.2 $(M+H)^+$ Step 2—N-[5-(1-hydroxy-1-methyl-ethyl)-2-[4-(hydroxymethyl)-1-piperidyl]-1,3-benzoxazol-6-yl]-6-(trifluoromethyl)pyridine-2-carboxamide To a solution of methyl 2-[4-(hydroxymethyl)-1-piperidyl]-6-[[6-(trifluoromethyl)pyridine-2-carbonyl]amino]-1,3-benzoxazole-5-carboxylate (1.70 g, 2.33 mmol) in THE (30 mL) was added 3.0 M MeMgBr in THE solution (7.8 mL, 23.4 mmol) at 0° C. The mixture was stirred at 25° C. for 4 hours. On completion, the reaction was quenched with sat. aq. $NH_4Cl$ (10 mL). The mixture was diluted with water (80 mL), and extracted with EA (3×50 mL). The combined organic layer was washed with brine (20 mL), dried over $Na_2SO_4$, filtered and concentrated in vacuo. The residue was purified by column chromatography on silica gel to give the title compound (550 mg, 49% yield) as light yellow solid. $^1H$ NMR (400 MHz, DMSO-$d_6$) δ 12.43 (s, 1H), 8.46 (s, 1H), 8.44 (d, J=7.6 Hz, 1H), 8.39-8.33 (m, 1H), 8.15 (d, J=7.2 Hz, 1H), 7.26 (s, 1H), 5.93 (s, 1H), 4.57 (t, J=5.2 Hz, 1H), 4.14 (d, J=13.2 Hz, 2H), 3.28 (t, J=5.6 Hz, 2H), 3.14-3.02 (m, 2H), 1.79-1.73 (m, 2H), 1.56 (s, 6H), 1.24-1.11 (m, 3H).

Step 3—N-[2-(4-formyl-1-piperidyl)-5-(1-hydroxy-1-methyl-ethyl)-1,3-benzoxazol-6-yl]-6-(trifluoro methyl)pyridine-2-carboxamide To a solution of N-[5-(1-hydroxy-1-methyl-ethyl)-2-[4-(hydroxymethyl)-1-piperidyl]-1,3-benzoxazol- 6-yl]-6-(trifluoromethyl)pyridine-2-carboxamide (120 mg, 250 umol) in DCM (3 mL) was added Dess-Martin (139 mg, 327 umol) at 0° C. The mixture was stirred at 25° C. for 1 hour. On completion, the reaction was quenched with sat. aq. $Na_2S_2O_3$ (10 mL). The mixture was partitioned and the aqueous phase was extracted with DCM (2×10 mL). The combined organic layer was washed with sat. aq. $NaHCO_3$ (10 mL) and brine (10 mL), dried over $Na_2SO_4$, filtered and concentrated in vacuo to give the title compound (119 mg, 99% yield) as light yellow solid. LC-MS ($ESI^+$) m/z 477.2 $(M+H)^+$.

(R)—N-(2-(hydroxymethyl)-2-methyl-6-morpholino-2,3-dihydrobenzofuran-5-yl)-6- (trifluoromethyl)picolinamide (Intermediate BDO) and (S)—N-(2-(hydroxymethyl)-2-methyl-6-morpholino-2,3-dihydro benzofuran-5-yl)-6-(trifluoro methyl) picolinamide (Intermediate BDP)

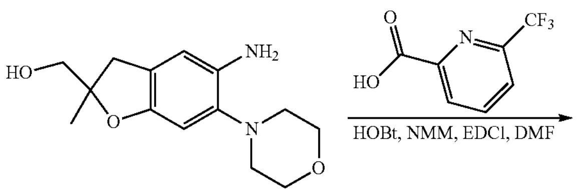

BCG

-continued

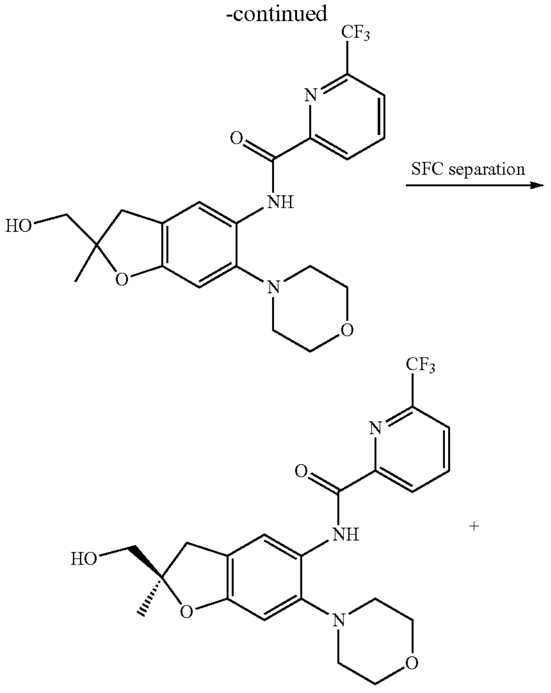

BDO

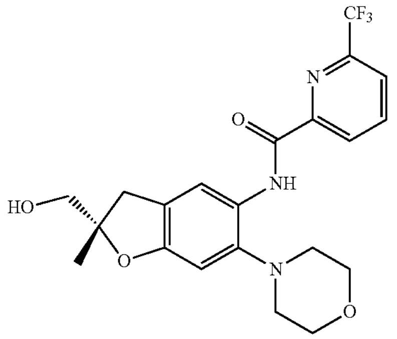

BDP

Step 1—N-(2-(hydroxymethyl)-2-methyl-6-morpholino-2,3-dihydrobenzofuran-5-yl)-6-(trifluoro methyl)picolinamide A solution of 6-(trifluoromethyl)pyridine-2-carboxylic acid (350 mg, 1.83 mmol, CAS #131747-42-7), 4-methylmorpholine (556 mg, 5.49 mmol), HOBt (247 mg, 1.83 mmol), EDCI (702 mg, 3.66 mmol) in DMF (5.0 mL) was stirred at 25° C. under $N_2$ for 0.5 hour. Then a solution of (5-amino-2- methyl-6-morpholino-3H-benzofuran-2-yl) methanol (460 mg, 1.74 mmol, Intermediate BCG) in DMF (5.0 mL) was added, and the mixture was stirred at 25° C. for 1.5 hours. Upon completion, the mixture was diluted with water (100 mL) and then extracted with EA (2×50 mL). The combined organic layers were dried over $Na_2SO_4$, filtered and concentrated in vacuo to give a residue. The residue was purified by silica gel chromatography (PE/EA=2/1 to 1/1) to give the title product (500 mg, 5% yield) as a yellow solid. $^1H$ NMR (400 MHz, $CDCl_3$) δ 10.97 (s, 1H), 8.51-8.464 (m, 2H), 8.14 (m, 1H), 7.87 (d, J=8.0 Hz, 1H), 6.69 (s, 1H), 3.96-3.94 (m, 4H), 3.69-3.66 (m, 2H), 3.29 (m, 1H), 2.97 (m, 1H), 2.93-2.88 (m, 4H), 1.92 (m, 1H), 1.47 (s, 3H). LC-MS ($ESI^+$) m/z 438.2 $(M+H)^+$.

Step 2—(R)—N-(2-(hydroxymethyl)-2-methyl-6-morpholino-2,3-dihydrobenzofuran-5-yl)-6- (trifluoromethyl)picolinamide and (S)—N-(2-(hydroxymethyl)-2-methyl-6-morpholino-2,3-dihydro benzofuran-5-yl)-6-(trifluoro methyl)picolinamide N-[2-(hydroxymethyl)-2-methyl-6-morpholino-3H-benzofuran-5-yl]-6-(trifluoromethyl)pyridine-2- carboxamide (1.0 g, 2.29 mmol) was separated by SFC (Base: column: DAICEL CHIRALCEL OJ-H (250 mm*30 mm, 5 um) to give peak 1 (100% ee) and peak 2. Then, the peak 1 was re-purified by prep-HPLC (mobile phase: [0.1% $NH_3H_2O$ IPA]; B %: 25%-25%, 6.6 min; 90 min) to afford the title compound (R)—N-(2-(hydroxymethyl)-2-methyl-6-morpholino-2,3-dihydrobenzofuran-5-yl)-6- (trifluoromethyl) picolinamide (450 mg, 35% yield, 100% ee) as a yellow solid. The peak 2 was re-purified by prep-HPLC (mobile phase: [0.1% $NH_3H_2O$ IPA]; B %: 25%-25%, 6.6 min; 90 min) to afford the title compound (S)—N-(2-(hydroxymethyl)-2-methyl-6-morpholino-2,3-dihydro benzofuran-5-yl)-6-(trifluoro methyl)picolinamide (450 mg, 35% yield) as a yellow solid. LC-MS ($ESI^+$) m/z 438.2 $(M+H)^+$. Stereochemistry was assigned arbitrarily.

(S)—N-(2-(iodomethyl)-2-methyl-6-morpholino-2,3-dihydrobenzofuran-5-yl)-6-(trifluor omethyl)picolinamide (Intermediate BDQ)

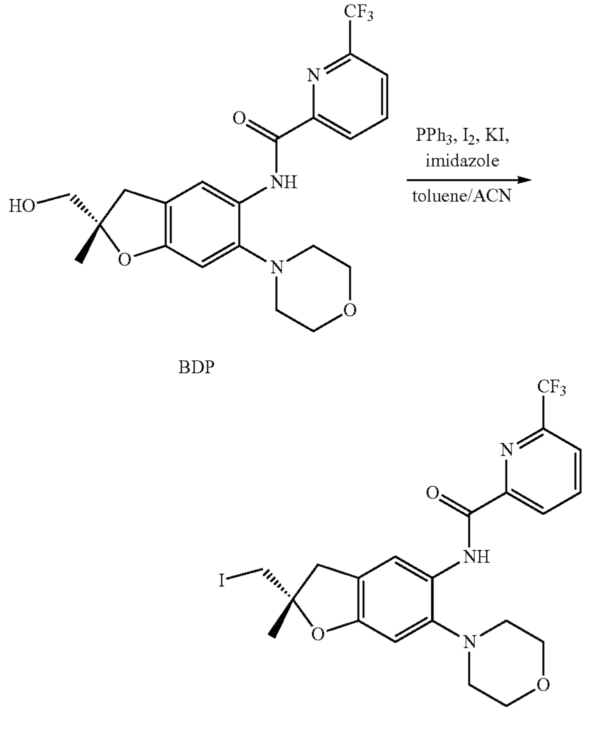

BDP

BDQ

A solution of $PPh_3$ (353 mg, 1.34 mmol), $I_2$ (341 mg, 1.34 mmol) and imidazole (91.5 mg, 1.34 mmol) in ACN (1.0 mL) was stirred at 0° C. for 0.5 hour. Then a solution of KI (335 mg, 2.02 mmol) and N-[(2S)-2-(hydroxymethyl)-2-methyl-6-morpholino-3H-benzofuran-5-yl]-6-(trifluoromethyl)pyridine-2-carboxamide (300 mg, 672 umol, Intermediate BDP) in toluene (4.0 mL) and ACN (1.0 mL) was added, and the mixture was stirred at 90° C. for 2 hours. On completion, the reaction mixture was filtered and concentrated in vacuo to give a residue. The residue was purified by silica gel chromatography (PE/EA=10/1) to give the title product (320 mg, 87% yield) as a yellow solid $^1H$ NMR (400 MHz, $CDCl_3$) δ 10.96 (s, 1H), 8.52-8.45 (m, 2H), 8.15 (m, 1H), 7.88 (m, 1H), 6.71 (s, 1H), 3.96 (m, 4H), 3.46 (m, 2H), 3.38 (m, 1H), 3.13 (m, 1H), 2.90 (m, 4H), 1.68 (s, 3H). LC-MS ($ESI^+$) m/z 548.1 $(M+H)^+$.

Tert-butyl 4-(2-bromoethoxy)piperidine-1-carboxylate (Intermediate BDR)

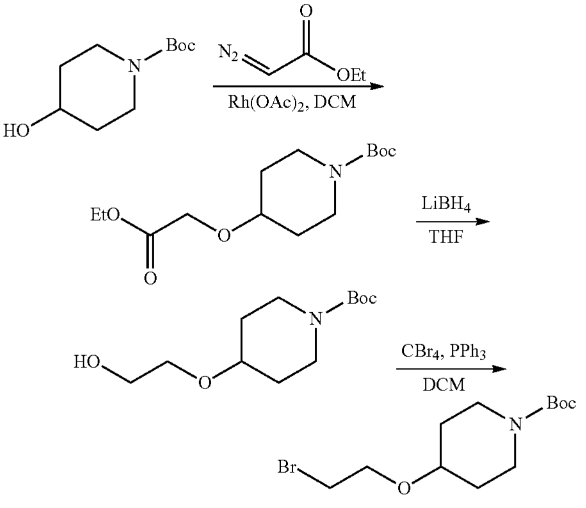

BDR

Step 1—Tert-butyl 4-(2-ethoxy-2-oxo-ethoxy)piperidine-1-carboxylate

To a solution of tert-butyl 4-hydroxypiperidine-1-carboxylate (5.00 g, 24.8 mmol, CAS #109384-19-2) in DCM (50 mL) was added $Rh(OAc)_2$ (54.9 mg, 248 umol) at 0° C. Then ethyl 2-diazoacetate (8.50 g, 74.5 mmol, 7.8 mL) was added and stirred 25° C. for 12 hr. On completion, the reaction mixture was filtered and the filtrate was concentrated in vacuo to give a residue. The residue was diluted with water (70 mL) and extracted with EA (3×60 mL). The combined organic layers were washed with brine (3×40 mL), dried over anhydrous $Na_2SO_4$, filtered and concentrated in vacuo to give a residue. The residue was purified by column chromatography (Petroleum ether/Ethyl acetate=5/1) to give the title compound (4.00 g, 56% yield) as a yellow oil. $^1H$ NMR (400 MHz, DMSO-$d_6$) δ 4.14-4.10 (m, 4H), 3.66-3.59 (m, 2H), 3.55-3.51 (m, 1H), 3.00 (t, J=9.6 Hz, 2H), 1.83-1.75 (m, 2H), 1.39 (s, 9H), 1.36-1.29 (m, 2H), 1.21-1.18 (m, 3H).

Step 2—Tert-butyl 4-(2-hydroxyethoxy)piperidine-1-carboxylate

A mixture of tert-butyl 4-(2-ethoxy-2-oxo-ethoxy)piperidine-1-carboxylate (4.00 g, 13.9 mmol) in THE (40 mL) was degassed and purged with $N_2$ for 3 times, and then the mixture was stirred at 0° C. and $LiBH_4$ (909 mg, 41.8 mmol)

was added at 0° C. Then the reaction mixture was stirred at 80° C. for 2 hr under $N_2$ atmosphere. On completion, the reaction mixture was quenched by water (60 mL) and extracted with EA (3×50 mL). The combined organic layers were washed with brine (3×30 mL), dried over anhydrous $Na_2SO_4$, filtered and concentrated in vacuo to give the title compound (2.20 g, 90% yield) as white oil. $^1$H NMR (400 MHz, DMSO-$d_6$) δ 4.55 (t, J=5.6 Hz, 1H), 3.66-3.60 (m, 2H), 3.50-3.42 (m, 5H), 3.00 (t, J=9.6 Hz, 2H), 1.81-1.73 (m, 2H), 1.39 (s, 9H), 1.37-1.30 (m, 2H).

Step 3—Tert-butyl 4-(2-bromoethoxy)piperidine-1-carboxylate

To a solution of tert-butyl 4-(2-hydroxyethoxy) piperidine-1-carboxylate (2.20 g, 8.97 mmol), $PPh_3$ (7.06 g, 26.9 mmol) in DCM (30 mL) was added $CBr_4$ (8.92 g, 26.9 mmol) at 0° C. The mixture was stirred at 25° C. for 12 hr. On completion, the reaction mixture was filtered and the filtrate was concentrated in vacuo to give a residue. The residue was purified by column chromatography (petroleum ether/ethyl acetate=20/1) to give the title compound (1.40 g, 46% yield) as a yellow oil. $^1$H NMR (400 MHz, DMSO-$d_6$) δ 3.77-3.72 (m, 2H), 3.64-3.52 (m, 5H), 3.04 (s, 2H), 1.82-1.73 (m, 2H), 1.40 (s, 9H), 1.37-1.30 (m, 2H).

3-[3-Methyl-2-oxo-4-[2-(4-piperidyloxy)ethyl]benzimidazol-1-yl]piperidine-2,6-dione (Intermediate BDS)

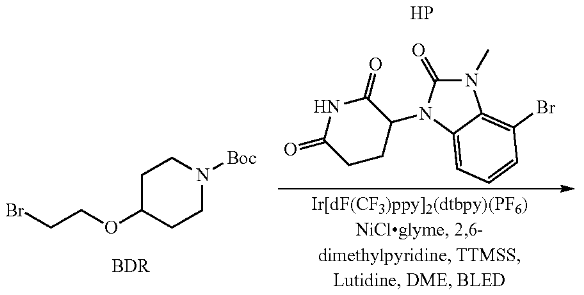

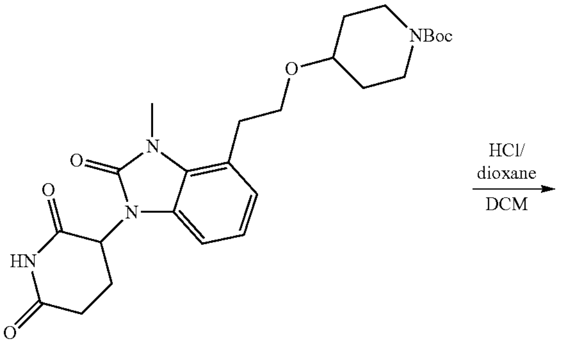

-continued

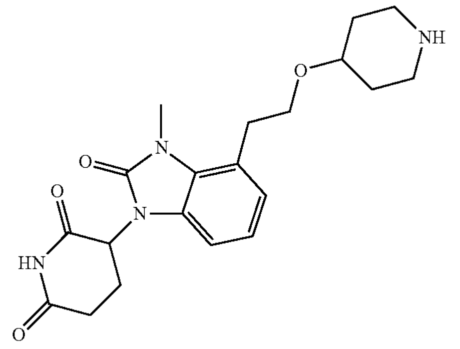

BDS

Step 1—Tert-butyl4-[2-[1-(2,6-dioxo-3-piperidyl)-3-methyl-2-oxo-benzimidazol-4-yl]ethoxy] piperidine-1-carboxylate To an 40 mL vial equipped with a stir bar was added 3-(4-bromo-3-methyl-2-oxo-benzimidazol-1-yl)piperidine-2,6-dione (1.28 g, 3.79 mmol, Intermediate HP), tert-butyl 4-(2-bromoethoxy)piperidine-1-carboxylate (1.40 g, 4.54 mmol, Intermediate BDR), $Ir[dF(CF_3)ppy]_2(dtbpy)(PF_6)$ (42.4 mg, 37.8 umol), $NiCl_2$.glyme (4.16 mg, 18.9 umol), TTMSS (941 mg, 3.79 mmol, 1.17 mL), 2,6-dimethylpyridine (811 mg, 7.57 mmol, 882 uL) in DME (20 mL). The reaction was stirred and irradiated with a 34 W blue LED lamp, and the reaction mixture was stirred at 25° C. for 14 hr under $N_2$. On completion, the reaction mixture was filtered and the filtrate was concentrated in vacuo to give a residue. The crude product was purified by reverse phase flash (0.1% FA condition) to give the title compound (800 mg, 34% yield) as a white solid. $^1$H NMR (400 MHz, DMSO-$d_6$) δ 11.10 (s, 1H), 7.02-6.91 (m, 3H), 5.38 (dd, J=5.2, 12.4 Hz, 1H), 3.68 (t, J=6.4 Hz, 2H), 3.59 (s, 3H), 3.48-3.44 (m, 2H), 3.36 (s, 2H), 3.15 (t, J=6.4 Hz, 2H), 3.01 (s, 1H), 2.76-2.60 (m, 2H), 2.06-1.91 (m, 1H), 1.74 (d, J=10.8 Hz, 2H), 1.39 (s, 9H), 1.33-1.27 (m, 2H), 1.11 (t, J=7.2 Hz, 1H).

Step 2—3-[3-Methyl-2-oxo-4-[2-(4-piperidyloxy)ethyl]benzimidazol-1-yl]piperidine-2,6-dione To a solution of tert-butyl 4-[2-[1-(2,6-dioxo-3-piperidyl)-3-methyl-2-oxo-benzimidazol-4-yl]ethoxy]piperidine-1-carboxylate (80.0 mg, 164 umol) in DCM (3.0 mL) was added HCl/dioxane (4 M, 1.0 mL). The mixture was stirred at 25° C. for 40 min. On completion, the reaction mixture was concentrated in vacuo to give the title compound (60 mg, 100% yield, HCl salt) as a white solid. LC-MS ($ESI^+$) m/z 387.3 $(M+H)^+$.

Tert-butyl N-[2-(4-formylcyclohexyl)-6-methoxy-indazol-5-yl]pyridine-2-carboxamide (Intermediate BDT)

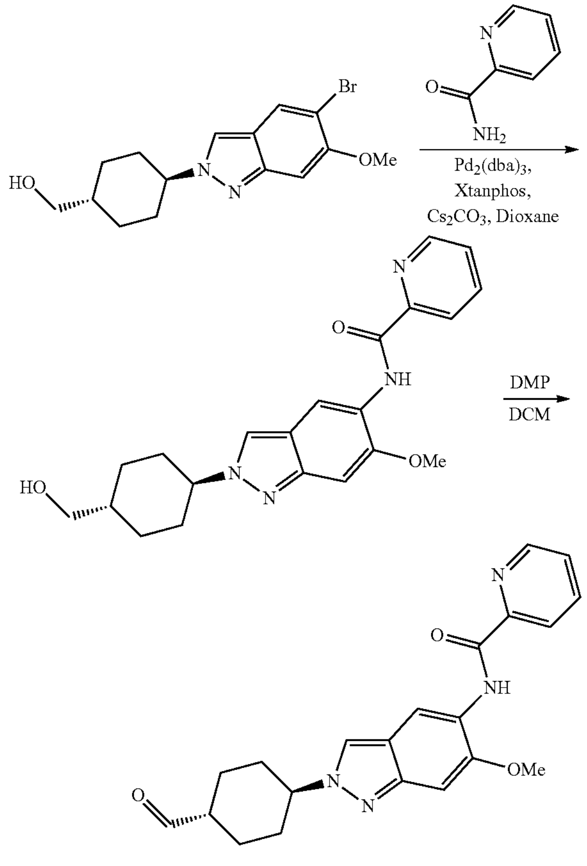

BDT

Step 1—Tert-butyl 4-[[4-nitro-2-(trifluoromethyl) phenyl]methyl]piperazine-1-carboxylate To a mixture of [4-(5-bromo-6-methoxy-indazol-2-yl)cyclohexyl]methanol (500 mg, 1.47 mmol, synthesized via Steps 1-3 of Intermediate ATE) and pyridine-2-carboxamide (360 mg, 2.95 mmol, CAS #1452-77-3) in dioxane (8.0 mL) was added $Pd_2(dba)_3$ (135 mg, 147 umol), $Cs_2CO_3$ (960 mg, 2.95 mmol) and Xantphos (171 mg, 295 umol) at 25° C. under $N_2$. The mixture was stirred at 110° C. under $N_2$ for 16 hours. On completion, the reaction mixture was quenched with water (10.0 mL) at 25° C., and then extracted with DCM (3x20 mL). The combined organic layers were dried over $Na_2SO_4$, filtered and concentrated in vacuo to give a residue. The residue was purified by column chromatography ($SiO_2$, petroleum ether/ethyl acetate=5/1 to 1/1) to give the title compound (68 mg, 12% yield) as a white solid. LC-MS ($ESI^+$) m/z 381.1 $(M+H)^+$.

Step 2—Tert-butyl N-[2-(4-formylcyclohexyl)-6-methoxy-indazol-5-yl]pyridine-2-carboxamide To a mixture of N-[2-[4-(hydroxymethyl)cyclohexyl]-6-methoxy-indazol-5-yl]pyridine-2-carboxamide (68.0 mg, 179 umol) in DCM (3.0 mL) was added DMP (91.0 mg, 215 umol) at 25° C. The mixture was stirred at 25° C. for 2 hours. On completion, the reaction mixture was quenched with water (10 mL) at 25° C., and then extracted with DCM (3x20 mL). The combined organic layers were dried over $Na_2SO_4$, filtered and concentrated in vacuo to give the title compound (56 mg, 83% yield) as a yellow solid. LC-MS ($ESI^+$) m/z 379.3 $(M+H)^+$.

Tert-butyl 6-(aminomethyl)-2-azaspiro[3.3]heptane-2-carboxylate (Intermediate APA)

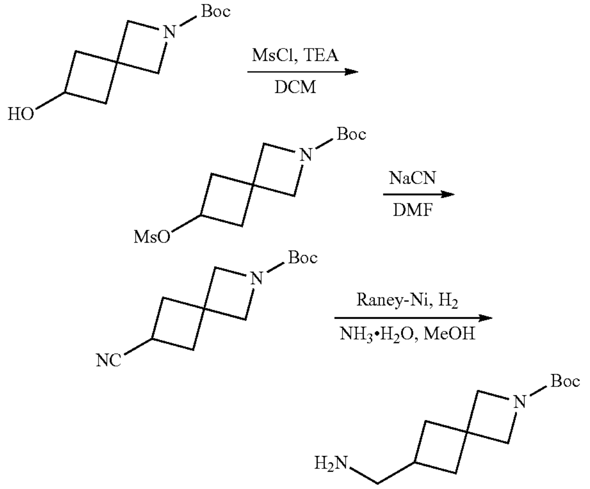

APA

Step 1—Tert-butyl 6-((methylsulfonyl)oxy)-2-azaspiro[3.3]heptane-2-carboxylate

To a solution of tert-butyl 6-hydroxy-2-azaspiro[3.3]heptane-2-carboxylate (2.5 g, 11.7 mmol, CAS #1147557-97-8) in the DCM (20 mL) was added MsCl (2.01 g, 17.6 mmol) and TEA (3.56 g, 35.2 mmol, 4.89 mL) at 0° C. The resulting mixture was stirred at 25° C. for 2 hours. On completion, the reaction mixture was quenched with water (20 mL) and extracted with EA (100 mL). The organic layer was dried over $Na_2SO_4$, filtered and concentrated in vacuo to give the title compound (3.2 g, 94% yield) as yellow solid. $^1H$ NMR (400 MHz, $CDCl_3$) δ 4.89 (q, J=7.2 Hz, 1H), 3.92 (d, J=1.8 Hz, 4H), 2.98 (s, 3H), 2.72-2.65 (m, 2H), 2.51-2.42 (m, 2H), 1.42 (s, 9H).

Step 2—Tert-butyl 6-cyano-2-azaspiro[3.3]heptane-2-carboxylate

To a solution of tert-butyl 6-methylsulfonyloxy-2-azaspiro[3.3]heptane-2-carboxylate (3.2 g, 11.0 mmol) in the DMF (30 mL) was added NaCN (2.15 g, 43.9 mmol). The mixture was stirred at 100° C. for 18 hours. On completion, the reaction mixture was poured into water (200 mL) and extracted with EA (2x200 mL). The organic layer was washed with brine (200 mL) and dried over $Na_2SO_4$, filtered and concentrated in vacuo. The residue was purified by column chromatography ($SiO_2$, PE:EA=10:1 to 5:1) to give the title compound (1.6 g, 66% yield) as white solid. $^1H$ NMR (400 MHz, $CDCl_3$) δ 3.94 (d, J=4.4 Hz, 4H), 3.00 (q, J=8.3 Hz, 1H), 2.67-2.52 (m, 4H), 1.43 (s, 9H).

Step 3—Tert-butyl 6-(aminomethyl)-2-azaspiro[3.3]heptane-2-carboxylate

To a solution of tert-butyl 6-cyano-2-azaspiro[3.3]heptane-2-carboxylate (0.8 g, 3.60 mmol) in the MeOH (5.0 mL) was added Raney-Ni (200 mg) and $NH_3.H_2O$ (1.01 g, 7.20 mmol). The reaction mixture was stirred at 25° C. for 4 hours under $H_2$ (50 Psi). On completion, the reaction mixture was filtered and concentrated in vacuo to give the title compound (800 mg, 98% yield) as colorless oil. $^1H$ NMR (400 MHz, $CDCl_3$) δ 3.92 (s, 2H), 3.81 (s, 2H), 2.65 (d, J=7.0 Hz, 2H), 2.30-2.22 (m, 2H), 2.22-2.11 (m, 1H), 1.85-1.77 (m, 2H), 1.43 (s, 9H).

4-((2-Azaspiro[3.3]heptan-6-ylmethyl)amino)-2-(2,6-dioxopiperidin-3-yl)isoindoline-1,3-dione (Intermediate APB)

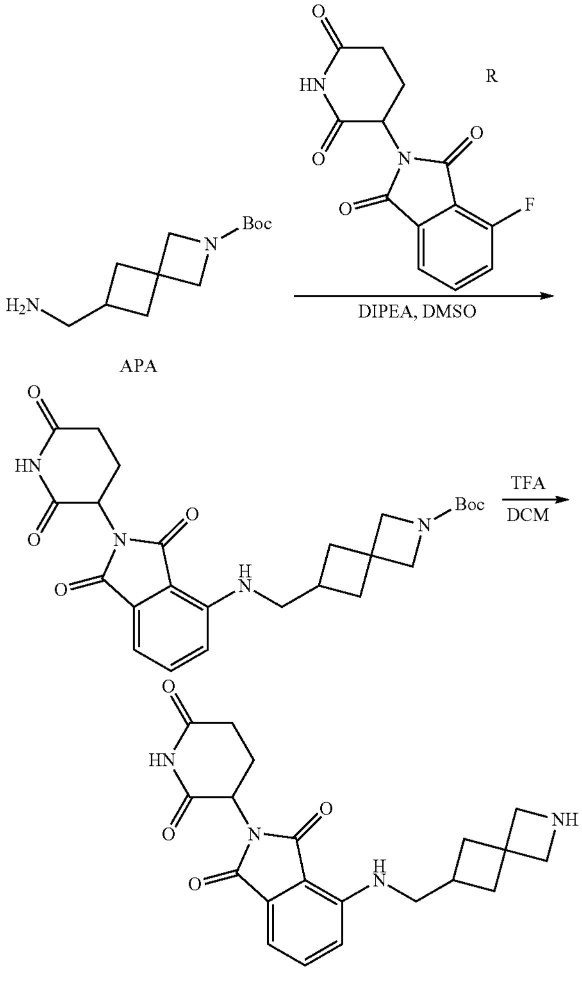

Step 1—Tert-butyl 6-(((2-(2,6-dioxopiperidin-3-yl)-1,3-dioxoisoindolin-4-yl)amino)methyl)-2- azaspiro[3.3]heptane-2-carboxylate To a solution of tert-butyl 6-(aminomethyl)-2-azaspiro[3.3]heptane-2-carboxylate (100 mg, 442 umol, Intermediate APA) and 2-(2,6-dioxo-3-piperidyl)-4-fluoro-isoindoline-1,3-dione (147 mg, 530 umol, Intermediate R) in the DMSO (2 mL) was added DIPEA (171 mg, 1.33 mmol, 231 uL). The mixture was stirred at 130° C. for 1 hour. On completion, the reaction mixture was filtered and the filtrate was concentrated in vacuo to give a residue. The residue was purified by reversed phase (FA condition) to give the title compound (140 mg, 66% yield) as yellow solid. $^1H$ NMR (400 MHz, $CDCl_3$) δ 7.90 (br s, 1H), 7.43 (dd, J=7.3, 8.4 Hz, 1H), 7.04 (d, J=7.0 Hz, 1H), 6.79 (d, J=8.5 Hz, 1H), 6.11 (t, J=5.4 Hz, 1H), 4.89-4.80 (m, 1H), 3.88 (s, 2H), 3.78 (s, 2H), 3.22-3.13 (m, 2H), 2.89-2.60 (m, 3H), 2.47-2.36 (m, 1H), 2.33-2.23 (m, 2H), 2.13-2.01 (m, 1H), 1.93-1.83 (m, 2H), 1.36 (s, 9H), 0.84-0.75 (m, 2H). LC-MS (ESI$^+$) m/z 483.3 $(M+H)^+$.

Step 2—4-((2-Azaspiro[3.3]heptan-6-ylmethyl)amino)-2-(2,6-dioxopiperidin-3-yl)isoindoline-1,3-dione To a solution of tert-butyl 6-[[[2-(2,6-dioxo-3-piperidyl)-1,3-dioxo-isoindolin-4-yl]amino]methyl]-2- azaspiro[3.3]heptane-2-carboxylate (70 mg, 145 umol) in the DCM (2 mL) was added TFA (1 mL). The mixture was stirred at 25° C. for 1 hour. On completion, the reaction mixture was concentrated in vacuo to give the title compound (55 mg, 99% yield) as yellow solid. LC-MS (ESI$^+$) m/z 383.2 $(M+H)^+$.

N-(6-(difluoromethyl)-2-((1r,4r)-4-formylcyclohexyl)-2H-indazol-5-yl)-6-methylpicolinamide (Intermediate BDU)

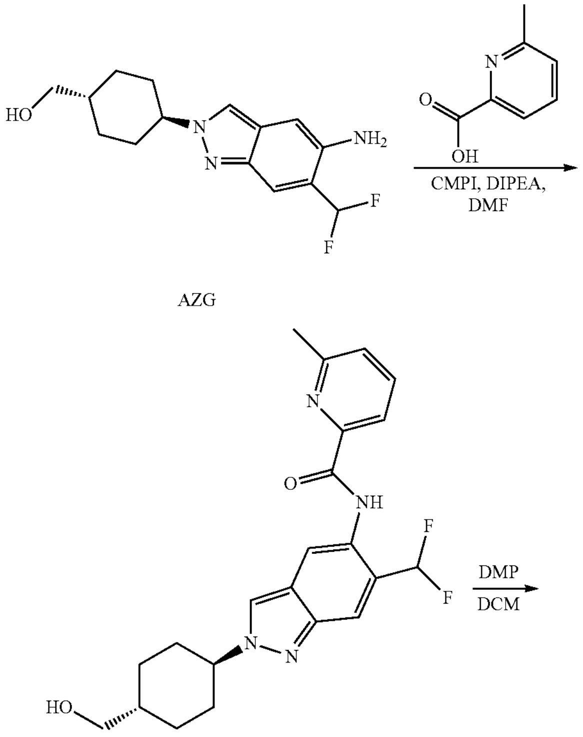

-continued

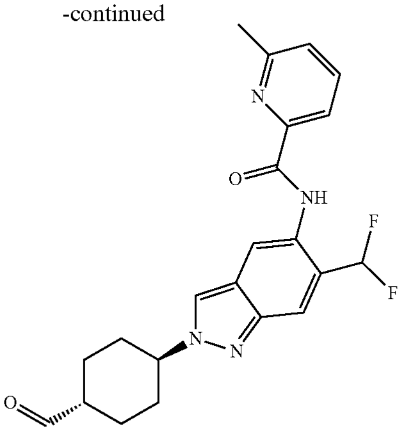

BDU

Step 1—N-(6-(difluoromethyl)-2- ((1r,4r)-4-(hydroxymethyl)cyclohexyl)- 2H-indazol-5-yl)-6-methylpicolinamide To a solution of [4-[5-amino-6-(difluoromethyl)indazol-2-yl]cyclohexyl]methanol (100 mg, 339 umol, Intermediate AZG), DIPEA (131 mg, 1.02 mmol) and CMPI (104 mg, 40 umol) in DMF (1 mL) was stirred at 25° C. for 0.5 hr. Then the mixture was added into a solution of 6-methylpyridine-2-carboxylic acid (55.7 mg, 406 umol, CAS #937-60-1) in DMF (1 mL). The mixture was stirred at 25° C. for 1.5 hrs. On completion, the reaction mixture was diluted with water (15 mL) and extracted with ethyl acetate (3×10 mL). The combined organic layers were washed with sodium chloride solution (15 mL), dried over anhydrous sodium sulfate, filtered and concentrated in vacuo to give a residue. The residue was purified by silica gel chromatography (petroleum ether:ethyl acetate=1:2) to give the title compound (100 mg, 67% yield) as a white solid. $^1$H NMR (400 MHz, DMSO-$d_6$) δ 10.66 (s, 1H), 8.52 (d, J=16.4 Hz, 2H), 8.02-7.92 (m, 3H), 7.58-7.53 (m, 1H), 7.39-7.06 (m, 1H), 4.54-4.44 (m, 2H), 3.32-3.27 (m, 3H), 2.60 (s, 3H), 2.17 (m, 2H), 1.96-1.87 (m, 4H), 1.23-1.11 (m, 2H). LC-MS (ESI$^+$) m/z 415.3 (M+H)$^+$.

Step 2—N-(6-(difluoromethyl)-2-((1r,4r)-4-formylcyclohexyl)-2H-indazol-5-yl)-6-methylpicolinamide To a solution of N-[6-(difluoromethyl)-2-[4- (hydroxymethyl)cyclohexyl]indazol-5- yl]-6- methyl- pyridine-2-carboxamide (100 mg, 241 umol) in DCM (2 mL) was added DMP (143 mg, 338 umol) at 0° C. The mixture was stirred at 25° C. for 2 hrs. On completion, the reaction mixture was quenched by saturated sodium thiosulfate solution (10 mL), then adjusted to pH to 7-8 with sodium bicarbonate saturated solution and extracted with dichloromethane (3×15 mL). The combined organic layers were washed with sodium chloride solution (5 mL), dried over anhydrous sodium sulfate, filtered and concentrated in vacuo to give a residue. The residue was triturated with ethyl acetate to give the title compound (40.0 mg, 38% yield) as a white solid. LC-MS (ESI$^+$) m/z 413.3 (M+H)$^+$.

N-(6-(Difluoromethyl)-2-((1r,4r)-4-formylcyclohexyl)-2H-indazol-5-yl)picolinamide (Intermediate BDV)

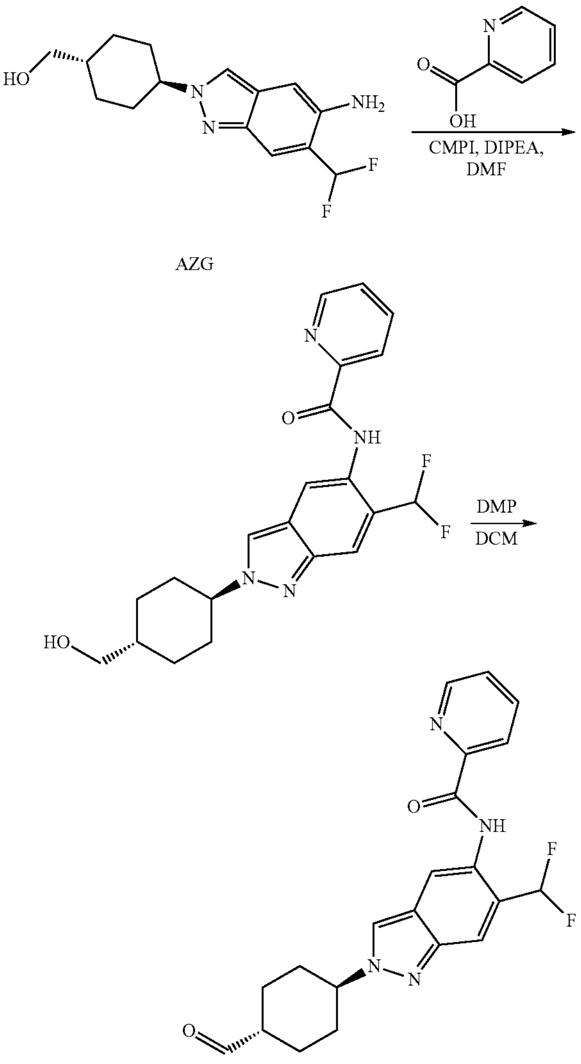

BDV

Step 1—N-(6-(Difluoromethyl)-2-((1r,4r)-4-(hydroxymethyl)cyclohexyl)-2H-indazol-5-yl) picolinamide A solution of pyridine-2-carboxylic acid (62.5 mg, 507 umol, CAS #636-80-6), CMPI (155 mg, 609 umol) and DIPEA (197 mg, 1.52 mmol) in DMF (3 mL) was stirred at 25° C. for 0.5 hr, then the reaction mixture was added to a solution of [4-[5-amino-6-(difluoromethyl)indazol-2-yl]cyclohexyl]methanol (150 mg, 507 umol, Intermediate AZG) in DMF (2 mL) and the reaction mixture was stirred at 25° C. for 2 hrs. On completion, the mixture was quenched with water (20 mL) and extracted with ethyl acetate (3×30 mL). The combined organic phase was dried over anhydrous sodium sulfate, filtered and concentrated to give a residue. The residue was purified by silica gel chromatography (PE:EA=1:1) to give the title compound (200 mg, 94% yield) as a white solid. $^1$H NMR (400 MHz, DMSO-$d_6$) δ 10.59 (s, 1H), 8.76 (d, J=4.4 Hz, 1H), 8.56 (s, 1H), 8.41 (s, 1H), 8.24-8.16 (m, 1H), 8.13-8.09 (m, 1H), 7.97 (s, 1H), 7.75-7.68 (m, 1H), 7.40-7.08 (m, 1H), 4.56-4.45 (m, 2H), 3.32-3.29 (m, 2H), 2.18 (d, J=9.2 Hz, 2H), 1.96-1.86 (m, 4H), 1.53-1.48 (m, 1H), 1.22-1.13 (m, 2H).

Step 2—N-(6-(Difluoromethyl)-2-((1r,4r)-4-formylcyclohexyl)-2H-indazol-5-yl)picolinamide To a solution of N-[6-(difluoromethyl)-2-[4-(hydroxymethyl)cyclohexyl]indazol-5-yl]pyridine-2- carboxamide (200 mg, 499 umol) in DCM (5 mL) was added DMP (211 mg, 499 umol) at 0° C., then the mixture was stirred at 25° C. for 2 hrs. On completion, the reaction mixture was diluted with water (50 mL) and extracted with ethyl acetate (3×50 mL). The combined organic phase was washed with sodium bicarbonate aqueous, dried over anhydrous sodium sulfate, filtered and concentrated to give a residue. The residue was triturated with EA (10 mL) at 25° C. for 5 min to give the title compound (110 mg, 54% yield) as a yellow solid. $^1$H NMR (400 MHz, DMSO-$d_6$) δ 10.59 (s, 1H), 9.66 (s, 1H), 8.76 (d, J=4.8 Hz, 1H), 8.56 (s, 1H), 8.42 (s, 1H), 8.20 (d, J=7.6 Hz, 1H), 8.11 (dt, J=1.6, 7.6 Hz, 1H), 7.98 (s, 1H), 7.73-7.69 (m, 1H), 7.41-7.10 (m, 1H), 4.57-4.53 (m, 1H), 2.47-2.41 (m, 1H), 2.27-2.22 (m, 2H), 2.13 (d, J=11.6 Hz, 2H), 2.06-1.97 (m, 2H), 1.49-1.45 (m, 2H).

1-(2,6-Dioxo-3-piperidyl)-3-methyl-2-oxo-benzimidazole-5-carbaldehyde (Intermediate SK)

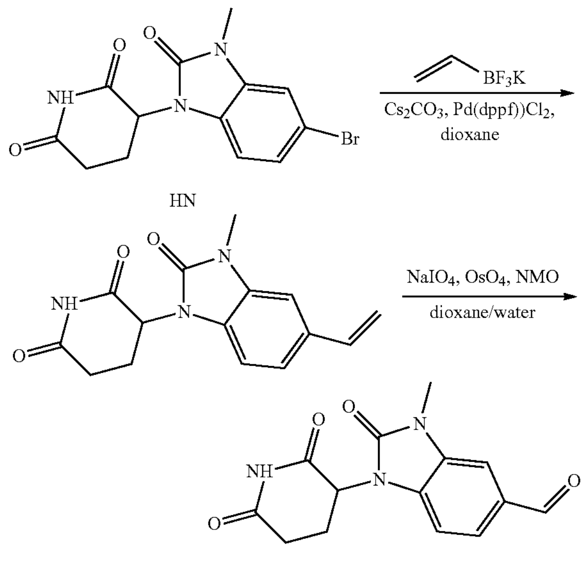

HN

SK

Step 1—3-(3-Methyl-2-oxo-5-vinyl-benzimidazol-1-yl)piperidine-2,6-dione

A mixture of 3-(5-bromo-3-methyl-2-oxo-benzimidazol-1-yl)piperidine-2,6-dione (3.00 g, 8.87 mmol, Intermediate HN), potassium hydride, trifluoro (vinyl)boron (3.57 g, 26.6 mmol), $Cs_2CO_3$ (2 M solution, 8.87 mL), Pd(dppf)C12 $CH_2Cl_2$ (724 mg, 887 umol) and in dioxane (30 mL) was degassed and purged with $N_2$ for 3 times, and then the mixture was stirred at 80° C. for 3 hours under $N_2$ atmosphere. On completion, the reaction mixture was concentrated in vacuo to give a residue. The residue was purified by reverse phase (TFA condition) to give the title compound (1.60 g, 58% yield) as a yellow solid. LC-MS (ESI$^+$) m/z 286.0 (M+H)$^+$.

Step 2—1-(2,6-Dioxo-3-piperidyl)-3-methyl-2-oxobenzimidazole-5-carbaldehyde

To a solution of 3-(3-methyl-2-oxo-5-vinyl-benzimidazol-1-yl)piperidine-2,6-dione (0.30 g, 1.05 mmol) in a mixed solvent of dioxane (20 mL) and $H_2O$ (2 mL) was added $NaIO_4$ (449 mg, 2.10 mmol), $OsO_4$ (267 mg, 1.00 mmol) and NMO (61.0 mg, 525 umol). The mixture was stirred at 25° C. for 0.5 hr. On completion, the residue was diluted with water (10 mL) and extracted with ethyl acetate (2×20 mL). The combined organic layers were washed with brine (20 mL), dried over $Na_2SO_4$, filtered and concentrated in vacuo to give a residue. The residue was purified by prep-HPLC (TFA condition) to give the title compound (0.1 g, 32% yield) as a gray solid. LC-MS (ESI$^+$) m/z 288.0 (M+H)$^+$.

3-(3-Methyl-5-((4-(methylamino)piperidin-1-yl)methyl)-2-oxo-2,3-dihydro-1H-benzo[d] imidazol-1-yl)piperidine-2,6-dione (Intermediate BDW)

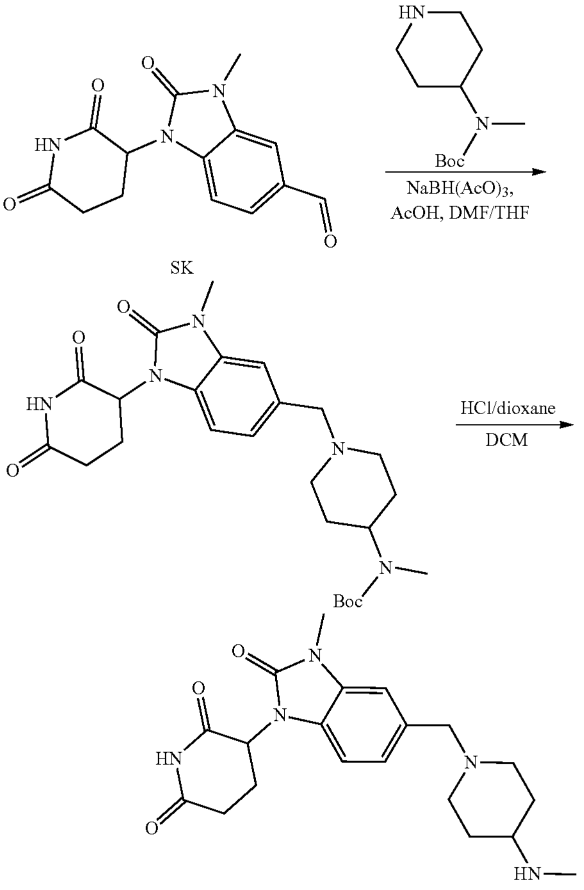

SK

BDW

Step 1—Tert-butyl (1-((1-(2,6-dioxopiperidin-3-yl)-3-methyl-2-oxo-2,3-dihydro-1H-benzo[d]imidazol-5-yl)methyl)piperidin-4-yl)(methyl)carbamate To a solution of 1-(2,6-dioxo-3-piperidyl)-3-methyl-2-oxo-benzimidazole-5-carbaldehyde (100 mg, 348 umol, Intermediate SK) and tert-butyl N-methyl-N-(4-piperidyl) carbamate (74.6 mg, 348 umol) in DMF (2 mL) and THE (8 mL) was added AcOH (20.9 mg, 348 umol), and then $NaBH(OAc)_3$ (148 mg, 696 umol) was added portion-wise. The mixture was stirred at 25° C. for 48 hrs. On completion, the reaction mixture was concentrated under reduced pressure to give a residue. The residue was purified by Prep-HPLC (column: Phenomenex Synergi C18 150*25*10 um;mobile phase: [water(0.225% FA)-ACN];B %: 6%-26%, 10 min) to give the title compound (20.0 mg, 10% yield) as a yellow solid. $^1H$ NMR (400 MHz, DMSO-$d_6$) δ 11.09 (s, 1H), 7.11-7.02 (m, 1H), 6.95 (t, J=7.6 Hz, 1H), 6.91-6.83 (m, 1H), 3.71-3.61 (m, 3H), 3.48 (m, 3H), 2.93-2.83 (m, 3H), 2.77-2.62 (m, 5H), 2.08-1.92 (m, 3H), 1.71-1.42 (m, 4H).

Step 2—3-(3-Methyl-5-((4-(methylamino)piperidin-1-yl)methyl)-2-oxo-2,3-dihydro-1H- benzo[d] imidazol-1-yl)piperidine-2,6-dione To a solution of tert-butyl N-[1-[[1-(2,6-dioxo-3-piperidyl)-3-methyl-2-oxo-benzimidazol-5-yl]methyl]-4-piperidyl]-N-methyl-carbamate (20.0 mg, 41.2 umol) in DCM (1 mL) was added HCl/dioxane (1 mL). The mixture was stirred at 25° C. for 0.5 hr. On completion, the reaction mixture was concentrated under reduced pressure to give the title compound (30.0 mg, 99% yield, HCl salt) as a yellow solid. LC-MS ($ESI^+$) m/z 386.2 $(M+H)^+$.

N-[(2R)-2-(iodomethyl)-2-methyl-6-morpholino-3H-benzofuran-5-yl]-6-(trifluoromethyl)pyridine-2-carboxamide (Intermediate BDX)

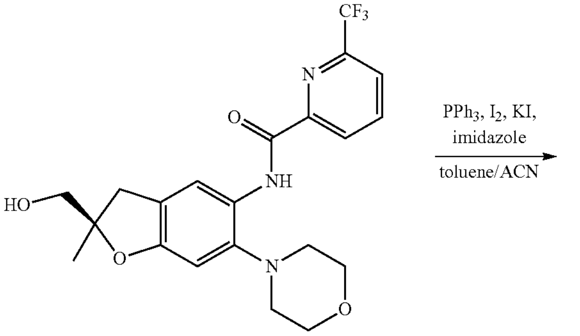

BDO

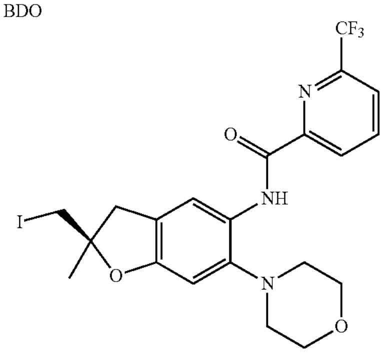

BDX

To a solution of $PPh_3$ (539 mg, 2.06 mmol) in ACN (2 mL) was added imidazole (140 mg, 2.06 mmol) and $I_2$ (522 mg, 2.06 mmol) at 0° C. The mixture was stirred at 0° C. for 30 min and then N-[(2R)-2-(hydroxymethyl)-2-methyl-6-morpholino-3H-benzofuran-5-yl]-6-(trifluoromethyl)pyridine-2-carboxamide (450 mg, 1.03 mmol, Intermediate BDO) and toluene (8 mL) was added at 0° C. The mixture was stirred at 0° C. for 2 hrs. KI (853 mg, 5.14 mmol) was added and the mixture was stirred at 90° C. for 16 hrs. On completion, the reaction mixture was filtered. The filtrate was concentrated in vacuo and the residue was purified by column chromatography (silica gel, PE:EA=10:1) to give the title compound (300 mg, 53% yield) as a yellow solid. $^1H$ NMR (400 MHz, $CDCl_3$) δ 10.96 (s, 1H), 8.51 (d, J=7.6 Hz, 1H), 8.46 (s, 1H), 8.13 (t, J=7.6 Hz, 1H), 7.88 (dd, J=0.8, 7.6 Hz, 1H), 6.71 (s, 1H), 3.99-3.92 (m, 4H), 3.46 (s, 2H), 3.36 (d, J=16.4 Hz, 1H), 3.11 (d, J=16.4 Hz, 1H), 2.95-2.85 (m, 4H), 1.69 (s, 3H).

3-(4-((1R,4R)-2,5-diazabicyclo[2.2.1]heptan-2-yl)-3-methyl-2-oxo-2,3-dihydro-1H- benzo[d]imidazol-1-yl)piperidine-2,6-dione (Intermediate BDY)

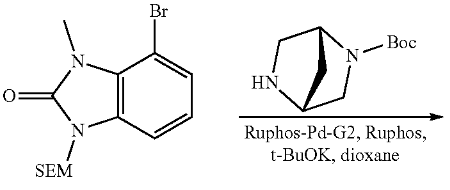

BED

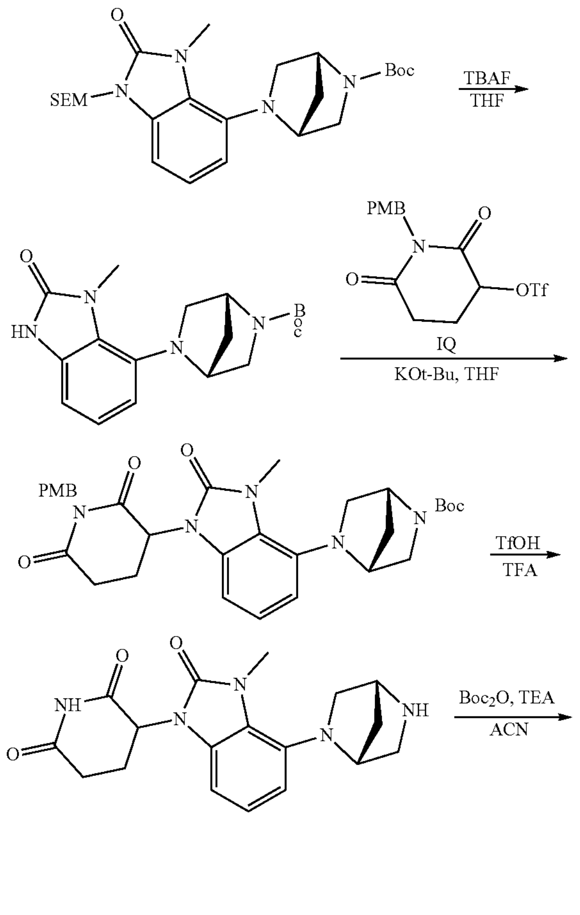

-continued

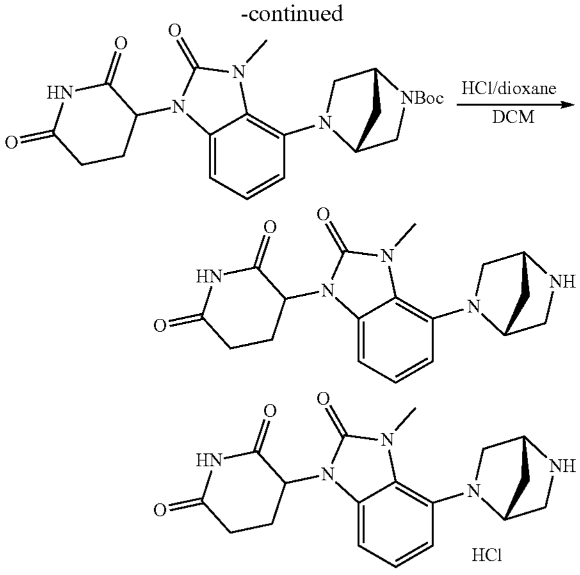

BDY

Step 1—(1R,4R)-tert-butyl 5-(3-methyl-2-oxo-1-((2-(trimethylsilyl)ethoxy)methyl)- 2,3-dihydro-1H -benzo[d]imidazol-4-yl)-2,5-diazabicyclo[2.2.1]heptane-2-carboxylate To a solution of 4-bromo-3-methyl-1-(2-trimethylsilylethoxymethyl)benzimidazol-2-one (3.00 g, 8.40 mmol, Intermediate BED), tert-butyl (1R,4R)-2,5-diazabicyclo[2.2.1]heptane-2-carboxylate (1.66 g, 8.40 mmol, CAS #134003-84-2) and t-BuOK (1.88 g, 16.8 mmol) in dioxane (40 mL) was added RuPhos (196 mg, 420 umol) and [2-(2-aminophenyl)phenyl]-chloro-palladium;dicyclohexyl-[2-(2,6-diisopropoxyphenyl)phenyl]phosphane (326 mg, 420 umol). The reaction mixture was degassed and purged with nitrogen for 3 times, and then the mixture was stirred at 80° C. for 2 hrs under nitrogen atmosphere. On completion, the reaction mixture was filtered and the combined filtrate was concentrated in vacuo to give a residue. The residue was purified by silica gel chromatography (petroleum ether:ethyl acetate=3:1) to give the title compound (2.86 g, 71% yield) as yellow oil. $^{1}$H NMR (400 MHz, DMSO-$d_6$) δ 7.05-6.90 (m, 2H), 6.81 (d, J=8.0 Hz, 1H), 5.21 (s, 2H), 4.37 (m, 1H), 3.90 (m, 1H), 3.58 (s, 3H), 3.53 (t, J=8.0 Hz, 2H), 3.44-3.35 (m, 1H), 3.31-3.16 (m, 2H), 3.15-3.06 (m, 1H), 2.04 (m, 1H), 1.88 (m, 1H), 1.43 (m, 9H), 0.88-0.76 (m, 2H), −0.03−0.13 (m, 9H). LC-MS (ESI$^+$) m/z 475.3 (M+H)$^+$.

Step 2—(1R,4R)-tert-butyl 5-(3-methyl-2-oxo-2,3-dihydro-1H-benzo[d]imidazol-4-yl)-2,5- diazabicyclo[2.2.1]heptanes-2-carboxylate A solution of tert-butyl (1R,4R)-5-[3-methyl-2-oxo-1-(2-trimethylsilylethoxymethyl)benzimidazol- 4-yl]-2,5-diazabicyclo[2.2.1]heptane-2-carboxylate (2.76 g, 5.81 mmol) in TBAF (40 mL, 1 M) was stirred at 80° C. for 16 hrs. On completion, the reaction mixture was diluted with water (80 mL) and extracted with ethyl acetate (3×25 mL). The combined organic layers were washed with sodium chloride solution (50 mL), dried over anhydrous sodium sulfate, filtered and concentrated in vacuo to give a residue. The residue was purified by silica gel chromatography (petroleum ether:ethyl acetate=1:2) to give the title compound (1.60 g, 79% yield) as a yellow solid. 1H NMR (400 MHz, $CDCl_3$) δ 10.34 (m, 1H), 7.03-6.94 (m, 1H), 6.88 (m, 1H), 6.81 (d, J=8.0 Hz, 1H), 4.66-4.41 (m, 1H), 3.85 (m, 1H), 3.73 (s, 3H), 3.66-3.53 (m, 1H), 3.48 (m, 1H), 3.30-3.12 (m, 2H), 2.17-2.07 (m, 1H), 1.95 (m, 1H), 1.51 (m, 9H). LC-MS (ESI$^+$) m/z 345.4 (M+H)$^+$.

Step 3—(1R,4R)-tert-butyl 5-(1-(1-(4-methoxybenzyl)-2,6-dioxopiperidin-3-yl)-3-methyl-2-oxo-2,3-dihydro-1H-benzo[d]imidazol-4-yl)-2,5-diazabicyclo[2.2.1]heptane-2-carboxylate To a solution of tert-butyl (1R,4R)-5-(3-methyl-2-oxo-1H-benzimidazol-4-yl)-2,5-diazabicyclo[2.2.1]heptanes-2-carboxylate (1.30 g, 3.77 mmol) in THE (30 mL) was added tBuOK (635 mg, 5.66 mmol) at 0° C. and stirred for 0.5 hr. Then the mixture was added [1-[(4-methoxyphenyl)methyl]-2,6-dioxo-3-piperidyl]trifluoromethanesulfonate (2.16 g, 5.66 mmol, Intermediate IQ) in batch at 0° C. and stirred at 25° C. for 2 hrs. On completion, the reaction mixture was poured into saturated ammonium chloride aqueous solution (50 mL) at 0° C. and extracted with ethyl acetate (3×25 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=1:1) and reversed-phase HPLC (FA condition) to give the title compound (1.50 g, 69% yield) as a blue solid. $^{1}$H NMR (400 MHz, $CDCl_3$) δ 7.37 (dd, J=8.8, 2.0 Hz, 2H), 6.90-6.77 (m, 4H), 6.27 (m, 1H), 5.34-5.08 (m, 1H), 5.03-4.87 (m, 2H), 4.61-4.43 (m, 1H), 3.86-3.76 (m, 4H), 3.72 (s, 3H), 3.63-3.40 (m, 2H), 3.29-3.13 (m, 2H), 3.05-2.95 (m, 1H), 2.89-2.76 (m, 1H), 2.68-2.51 (m, 1H), 2.21-2.07 (m, 3H), 1.96 (m, 1H), 1.51 (m, 9H). LC-MS (ESI$^+$) m/z 576.2 (M+H)$^+$.

Step 4—3-(4-((1R,4R)-2,5-diazabicyclo[2.2.1]heptan-2-yl)-3-methyl-2-oxo-2,3-dihydro-1H- benzo[d]imidazol-1-yl)piperidine-2,6-dione A solution of tert-butyl (1R,4R)-5-[1-[1-[(4-methoxyphenyl)methyl]-2,6-dioxo-3-piperidyl]-3- methyl-2-oxo-benzimidazol-4-yl]-2,5-diazabicyclo[2.2.1]heptane-2-carboxylate (800 mg, 1.39 mmol) in TfOH (1 mL) and TFA (10 mL) was stirred at 60° C. for 16 hrs. On completion, the reaction mixture was concentrated in vacuo to give the title compound (652 mg, 70% yield) as green oil. LC-MS (ESI$^+$) m/z 356.1 (M+H)$^+$.

Step 5—(1R,4R)-tert-butyl 5-(1-(2,6-dioxopiperidin-3-yl)-3-methyl-2-oxo-2,3-dihydro-1H- benzo[d]imidazol-4-yl)-2,5-diazabicyclo[2.2.1]heptane-2-carboxylate To a solution of 3-[4-[(1R,4R)-2,5-diazabicyclo[2.2.1]heptan-2-yl]-3-methyl-2-oxo-benzimidazol-1- yl]piperidine-2,6-dione (610 mg, 1.30 mmol, TFA) in ACN (5 mL) was added TEA (394 mg, 3.90 mmol) and $(Boc)_2O$ (340 mg, 1.56 mmol). The mixture was stirred at 25° C. for 2 hrs. On completion, the reaction mixture was concentrated in vacuo to give a residue. The residue was diluted with saturated ammonium chloride aqueous solution (25 mL) and extracted with ethyl acetate (3×15 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=1:5) to give the title compound (580 mg, 90% yield) as a green solid. $^1$H NMR (400 MHz, $CDCl_3$) δ 8.25 (m, 1H), 7.05-6.94 (m, 1H), 6.85 (d, J=8.0 Hz, 1H), 6.57 (d, J=7.6 Hz, 1H), 5.29-5.15 (m, 1H), 4.63-4.43 (m, 1H), 3.90-3.79 (m, 1H), 3.73 (s, 3H), 3.58 (m, 1H), 3.47 (m, 1H), 3.31-3.13 (m, 2H), 2.98-2.65 (m, 3H), 2.29-2.16 (m, 1H), 2.11 (m, 1H), 1.97 (m, 1H), 1.51 (m, 9H). LC-MS ($ESI^+$) m/z 456.3 $(M+H)^+$.

Step 6—3-(4-((1R,4R)-2,5-diazabicyclo[2.2.1]heptan-2-yl)-3-methyl-2-oxo-2,3-dihydro-1H- benzo[d]imidazol-1-yl)piperidine-2,6-dione A solution of tert-butyl (1R,4R)-5-[1-(2,6-dioxo-3-piperidyl)-3-methyl-2-oxo-benzimidazol-4- yl]-2,5-diazabicyclo[2.2.1]heptane-2-carboxylate (100 mg, 220 umol) in HCl/dioxane (1 mL) and DCM was stirred at 25° C. for 0.5 hr. On completion, the reaction mixture was concentrated in vacuo to give the title compound (86 mg, 99% yield) as a yellow solid. LC-MS ($ESI^+$) m/z 356.4 $(M+H)^+$.

3-[4-[(1S,5R)-3,8-Diazabicyclo[3.2.1]octan-8-yl]-3-methyl-2-oxo-benzimidazol-1- yl]piperidine-2,6-dione (Intermediate BDZ)

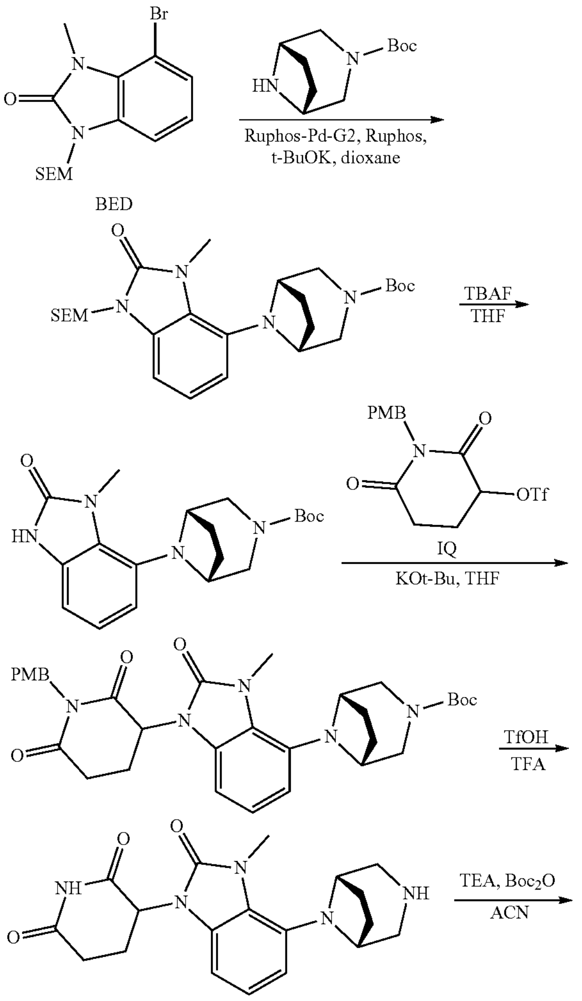

-continued

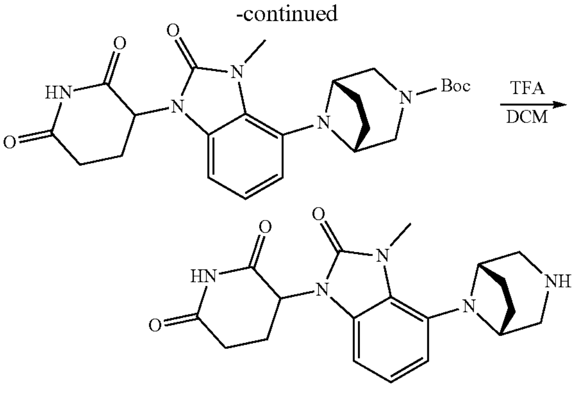

BDZ

Step 1—Tert-butyl (1S,5R)-8-[3-methyl-2-oxo-1-(2-trimethylsilylethoxymethyl)benzimidazol-4-yl]-3,8-diazabicyclo[3.2.1]octane-3-carboxylate To a solution of 4-bromo-3-methyl-1-(2-trimethylsilylethoxymethyl)benzimidazol-2-one (3 g, 8.40 mmol, Intermediate BED) in dioxane (30 mL) was added tert-butyl (1S,5R)-3,8-diazabicyclo[3.2.1] octane-3-carboxylate (1.78 g, 8.40 mmol), t-BuOK (1.88 g, 16.7 mmol), RuPhos (195 mg, 419 umol) and [2-(2-aminophenyl)phenyl]-chloro-palladium;dicyclohexyl-[2-(2,6-diisopropoxyphenyl)phenyl] phosphane (326 mg, 419 umol). The reaction mixture was degassed and purged with nitrogen for 3 times, and then the mixture was stirred at 80° C. for 2 hrs under nitrogen atmosphere. On completion, the mixture was quenched with water and extracted with ethyl acetate (3x25 mL). The combined organic phase was dried over anhydrous sodium sulfate, filtered and concentrated to give a residue. The residue was purified by column chromatography (petroleum ether:ethyl acetate=1:2) to give the title compound (2.5 g, 61% yield) as an off-white solid. $^1$H NMR (400 MHz, DMSO-$d_6$) δ 7.03-6.96 (m, 2H), 6.77 (d, J=7.2 Hz, 1H), 5.28 (s, 2H), 3.90-3.71 (m, 7H), 3.65-3.58 (m, 2H), 3.38-3.31 (m, 2H), 3.21 (d, J=11.2 Hz, 1H), 2.02-1.87 (m, 2H), 1.68 (d, J=8.0 Hz, 2H), 1.49 (s, 8H), 0.96-0.84 (m, 2H), 0.00 (s, 9H), LC-MS ($ESI^+$) m/z 489.3 $(M+H)^+$.

Step 2—Tert-butyl (1S,5R)-8-(3-methyl-2-oxo-1H-benzimidazol-4-yl)-3,8-diazabicyclo[3.2.1]octane-3-carboxylate A solution of tert-butyl (1S,5R)-8-[3-methyl-2-oxo-1-(2-trimethylsilylethoxymethyl)benzimidazol -4-yl]-3,8-diazabicyclo[3.2.1]octane-3-carboxylate (2.5 g, 5.12 mmol) in TBAF (1 M, 50 mL) was stirred at 80° C. for 12 hrs. On completion, the mixture was quenched with water and extracted with ethyl acetate (3x25 mL). The combined organic phase was dried over anhydrous sodium sulfate, filtered and concentrated to give a residue. The residue was purified by column chromatography (petroleum ether:ethyl acetate=1:2) to give the title compound (1.60 g, 87% yield) as a yellow solid. $^1$H NMR (400 MHz, DMSO-$d_6$) δ 10.81 (s, 1H), 6.88-6.80 (m, 1H), 6.67 (dd, J=0.8, 7.6 Hz, 1H), 6.60 (d, J=8.0 Hz, 1H), 3.84-3.67 (m, 4H), 3.61 (s, 3H), 3.31-3.23 (m, 1H), 3.13 (d, J=11.6 Hz, 1H), 1.92-1.82 (m, 2H), 1.66-1.56 (m, 2H), 1.47-1.37 (m, 9H). LC-MS ($ESI^+$) m/z 359.1 $(M+H)^+$.

Step 3—Ttert-butyl (1S,5R)-8-[1-[1-[(4-methoxyphenyl)methyl]-2,6-dioxo-3-piperidyl]-3-methyl-2-oxo-benzimidazol-4-yl]-3,8-diazabicyclo[3.2.1]octane-3-carboxylate To a solution of tert-butyl (1S,5R)-8-(3-methyl-2-oxo-1H-benzimidazol-4-yl)-3,8-diazabicyclo[3.2.1] octane-3-carboxylate (1.57 g, 4.38 mmol) in THE (20 mL) was added t-BuOK (737 mg, 6.57 mmol). The reaction mixture was stirred at 0° C. for 1 hr. Then [1-[(4-methoxyphenyl) methyl]-2,6- dioxo-3-piperidyl]trifluoromethanesulfonate (2.51 g, 6.57 mmol, Intermediate IQ) was added. The reaction mixture was stirred at 0° C. for 3 hrs. On completion, the mixture was quenched with water and extracted with ethyl acetate (3×25 mL). The combined organic phase was dried over anhydrous sodium sulfate, filtered and concentrated to give a residue. The residue was purified by reversed-phase HPLC (0.1% FA condition) to give the title compound (1.4 g, 52% yield) as an off-white solid. $^1$H NMR (400 MHz, DMSO-$d_6$) δ 7.22 (d, J=8.8 Hz, 2H), 6.88-6.84 (m, 2H), 6.69 (d, J=8.2 Hz, 2H), 5.50 (dd, J=5.6, 12.8 Hz, 1H), 4.90-4.69 (m, 2H), 4.08-4.00 (m, 1H), 3.79 (d, J=10.8 Hz, 3H), 3.73 (s, 3H), 3.69 (s, 3H), 3.21-2.98 (m, 2H), 2.87-2.64 (m, 2H), 2.10-1.96 (m, 2H), 1.90 (dd, J=2.4, 7.6 Hz, 2H), 1.69-1.54 (m, 2H), 1.43 (s, 9H), 1.18 (t, J=7.2 Hz, 1H), LC-MS (ESI$^+$) m/z 590.1 (M+H)$^+$.

Step 4—3-[4-[(1S,5R)-3,8-Diazabicyclo[3.2.1]octan-8-yl]-3-methyl-2-oxo-benzimidazol-1-yl]piperidine-2,6-dione A solution of tert-butyl (1S,5R)-8-[1-[1-[(4-methoxyphenyl)methyl]-2,6-dioxo-3-piperidyl]-3- methyl-2-oxo-benzimidazol-4-yl]-3,8-diazabicyclo[3.2.1]octane-3-carboxylate (750 mg, 1.27 mmol) in TFA (10 mL) was added TfOH (1 mL) was stirred at 60° C. for 12 hrs. On completion, the mixture was concentrated to give the title compound (450 mg, 73% yield, TFA) as black brown oil. LC-MS (ESI$^+$) m/z 370.4 (M+H)$^+$.

Step 5—Tert-butyl (1S,5R)-8-[1-(2,6-dioxo-3-piperidyl)-3-methyl-2-oxo-benzimidazol-4-yl]-3,8-diazabicyclo[3.2.1]octane-3-carboxylate To a solution of 3-[4-[(1S,5R)-3,8-diazabicyclo[3.2.1] octan-8-yl]-3-methyl-2-oxo-benzimidazol-1- yl]piperidine-2,6-dione (400 mg, 827 umol, TFA) in ACN (5 mL) was added TEA (83.7 mg, 827 umol). The reaction mixture was stirred at 25° C. for 15 min. Then the tert-butoxycarbonyl tert-butyl carbonate (216 mg, 992 umol) was added. The reaction mixture was stirred at 25° C. for 2 hrs. On completion, the mixture was extracted with EA (3×25 mL). The combined organic phase was dried over anhydrous sodium sulfate, filtered and concentrated to give a residue. The residue was purified by column chromatography (Petroleum ether: Ethyl acetate=1:3) to give the title compound (308 mg, 77% yield) as a yellow solid. $^1$H NMR (400 MHz, DMSO-$d_6$) δ 11.14 (s, 1H), 7.00-6.93 (m, 1H), 6.88 (d, J=8.0 Hz, 1H), 6.74 (d, J=8.4 Hz, 1H), 5.40 (dd, J=5.2, 12.4 Hz, 1H), 3.88-3.78 (m, 4H), 3.74 (s, 3H), 3.37-3.30 (m, 1H), 3.20 (d, J=11.2 Hz, 1H), 2.98-2.89 (m, 1H), 2.81-2.64 (m, 2H), 1.99-1.93 (m, 2H), 1.68 (d, J=8.4 Hz, 2H), 1.48 (s, 10H). LC-MS (ESI$^+$) m/z 470.1 (M+H)$^+$.

Step 6—3-[4-[(1S,5R)-3,8-Diazabicyclo[3.2.1]octan-8-yl]-3-methyl-2-oxo-benzimidazol-1- yl]piperidine-2,6-dione To a solution of tert-butyl (1S,5R)-8-[1-(2,6-dioxo-3-piperidyl)-3-methyl-2-oxo-benzimidazol-4-yl]-3,8-diazabicyclo[3.2.1]octane-3-carboxylate (100 mg, 212 umol) in DCM (1 mL) was added TFA (1 mL). The reaction mixture was stirred at 25° C. for 1 hr. On completion, the mixture was concentrated to give the title compound (75 mg, 95% yield) as brown oil. LC-MS (ESI$^+$) m/z 370.1 (M+H)$^+$.

Methyl 6-bromo-2-((1r,4r)-4-(hydroxymethyl)cyclohexyl)-1- methyl-1H-benzo[d]imidazole- 5-carboxylate (Intermediate BEA)

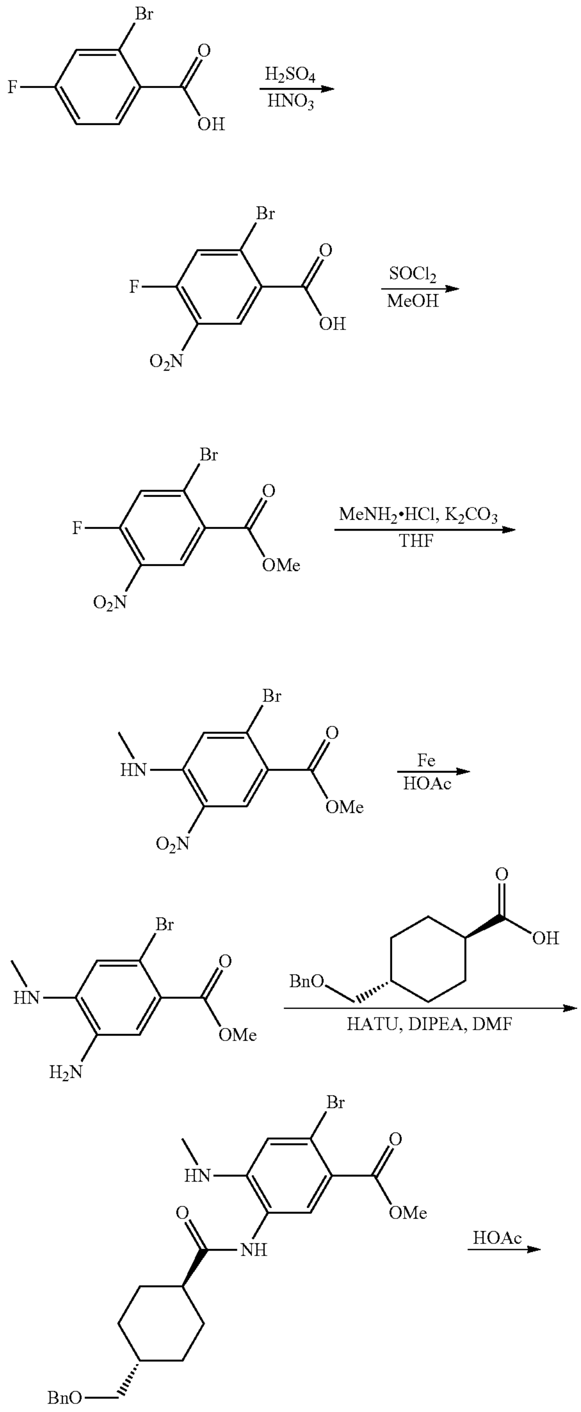

-continued

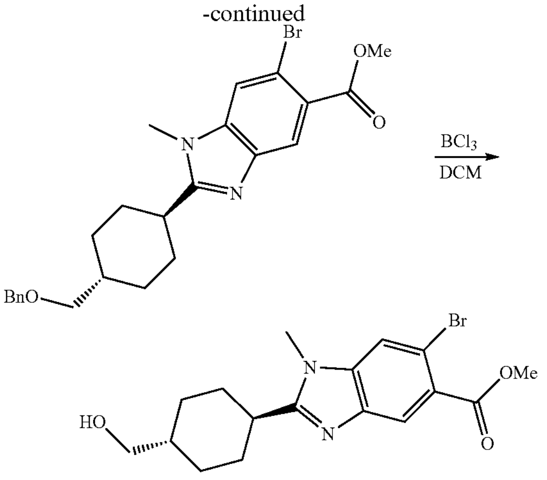

BEA

Step 1—2-Bromo-4-fluoro-5-nitrobenzoic acid

To a mixture of 2-bromo-4-fluoro-benzoic acid (25.0 g, 114 mmol) in $H_2SO_4$ (100 mL) was added $HNO_3$ (8.63 g, 137 mmol, CAS #1006-41-3) slowly at −5° C. The reaction mixture stirred at 0° C. for 2 hrs. On completion, the reaction mixture was poured into ice-water (1 L) slowly and the mixture was filtered. The filter cake was dried in vacuo to give the title compound (27.0 g, 90% yield) as a light yellow solid. $^1H$ NMR (400 MHz, $CDCl_3$) δ 8.72-8.70 (d, J=2.0 Hz, 1H), 7.66-7.64 (d, J=2.0 Hz, 1H).

Step 2—Methyl 2-bromo-4-fluoro-5-nitrobenzoate

To a mixture of 2-bromo-4-fluoro-5-nitro-benzoic acid (27.0 g, 102 mmol) in MeOH (120 mL) was added $SOCl_2$ (60.8 g, 511 mmol) at 0° C. The reaction mixture was warmed to 25° C. and stirred for 24 hrs. On completion, the reaction mixture was concentrated in vacuo. The residue was diluted in water (300 mL, 0° C.). The mixture was extracted with EA (3×300 ml) and the organic phase was concentrated in vacuo. The residue was triturated with PE (50 ml) and EA (1 ml) at 25° C. for 2 hrs to give the title compound (25.5 g, 90% yield) as a light yellow solid. $^1H$ NMR (400 MHz, $CDCl_3$) δ 8.56 (d, J=7.6 Hz, 1H), 7.61 (d, J=10.0 Hz, 1H), 3.92 (s, 3H).

Step 3—Methyl 2-bromo-4-(methylamino)-5-nitrobenzoate

To a solution of methyl 2-bromo-4-fluoro-5-nitro-benzoate (25.0 g, 90.0 mmol) in $MeNH_2$ (2 M, 250 mL) was added MeOH (10 mL) and the mixture was stirred at 25° C. for 2 hrs. On completion, the reaction mixture was concentrated in vacuo. The residue was purified by silica gel chromatography (petroleum ether:ethyl acetate=3:1) to give the title compound (25.0 g, 96% yield) as a yellow solid. $^1H$ NMR (400 MHz, DMSO-$d_6$) δ 8.58 (s, 1H), 8.54 (m, 1H), 7.26 (s, 1H), 3.81 (s, 3H), 2.99 (d, J=4.8 Hz, 3H). LC-MS ($ESI^+$) m/z 291.2 $(M+H)^+$.

Step 4—Methyl 5-amino-2-bromo-4-(methylamino)benzoate

To a solution of methyl 2-bromo-4-(methylamino)-5-nitro-benzoate (25.0 g, 86.5 mmol) in AcOH (300 mL) was added Fe (24.2 g, 432 mmol) at 60° C. portion-wise. The reaction mixture was stirred at 60° C. for 3 hrs. On completion, the reaction mixture was filtered and the filtrate was concentrated in vacuo to give a residue. The residue was purified by silica gel chromatography (petroleum ether:ethyl acetate=1:1) to give the title compound (15.6 g, 68% yield) as a yellow solid. $^1H$ NMR (400 MHz, DMSO-$d_6$) δ 7.15 (s, 1H), 6.52 (s, 1H), 5.60 (m, 1H), 4.84 (s, 2H), 3.78-3.68 (m, 3H), 2.76 (d, J=4.8 Hz, 3H). LC-MS ($ESI^+$) m/z 259.3 $(M+H)^+$.

Step 5—Methyl 5-((1r,4r)-4-((benzyloxy)methyl) cyclohexanecarboxamido)-2-bromo-4- (methylamino)benzoate To a solution of 4-(benzyloxymethyl)cyclohexanecarboxylic acid (2.00 g, 8.05 mmol, synthesized via Steps 1-3 of Intermediate BAU) and methyl 5-amino-2-bromo-4-(methylamino)benzoate (2.30 g, 8.86 mmol) in DMF (30 mL) was added HATU (4.59 g, 12.1 mmol) and DIPEA (3.12 g, 24.2 mmol). The reaction mixture was stirred at 25° C. for 16 hrs. On completion, the reaction mixture was diluted with water (50 mL) and extracted with ethyl acetate (3×25 mL). The combined organic layers were washed with sodium chloride solution (50 mL), dried over anhydrous sodium sulfate, filtered and concentrated in vacuo to give a residue. The residue was purified by silica gel chromatography (petroleum ether:ethyl acetate=1:1) to give the title compound (3.40 g, 85% yield) as a pink solid. $^1H$ NMR (400 MHz, DMSO-$d_6$) δ 8.97 (s, 1H), 7.77 (s, 1H), 7.45-7.21 (m, 5H), 6.78 (s, 1H), 5.99 (m, 1H), 4.45 (s, 2H), 3.85-3.66 (m, 3H), 3.27 (d, J=6.4 Hz, 2H), 2.77 (d, J=4.8 Hz, 3H), 2.37-2.25 (m, 1H), 1.94-1.75 (m, 4H), 1.65-1.51 (m, 1H), 1.49-1.32 (m, 2H), 0.99 (m, 2H). LC-MS ($ESI^+$) m/z 491.2 $(M+H)^+$.

Step 6—Methyl 2-((1r,4r)-4-((benzyloxy)methyl) cyclohexyl)-6-bromo-1-methyl-1H-benzo[d] imidazole-5-carboxylate A solution of methyl 5-[[4-(benzyloxymethyl)cyclohexanecarbonyl]amino]-2-bromo-4-(methylamino) benzoate (3.40 g, 6.95 mmol) in AcOH (50 mL) was stirred at 80° C. for 16 hrs. On completion, the reaction mixture was concentrated in vacuo to give the title compound (3.20 mg, 98% yield) as brown oil. $^1H$ NMR (400 MHz, $CDCl_3$) δ 8.26 (s, 1H), 7.59 (s, 1H), 7.38-7.29 (m, 4H), 4.54 (s, 2H), 3.94 (s, 3H), 3.74 (s, 3H), 3.37 (d, J=6.0 Hz, 2H), 2.84-2.76 (m, 2H), 2.05 (m, 4H), 1.91-1.79 (m, 3H), 1.22 (m, 2H). LC-MS ($ESI^+$) m/z 473.2 $(M+H)^+$.

Step 7—Methyl 6-bromo-2-((1r,4r)-4-(hydroxymethyl)cyclohexyl)-1- methyl-1H-benzo[d]imidazole-5-carboxylate To a solution of methyl 2-[4-(benzyloxymethyl)cyclohexyl]-6-bromo-1- methyl-benzimidazole-5- carboxylate (3.20 g, 6.79 mmol) in DCM (30 mL) was added $BCl_3$ (27.0 g, 231 mmol) at 0° C., and the mixture was stirred at 25° C. for 2 hrs. On completion, the reaction mixture was diluted with water (50 mL) and extracted with ethyl acetate (3×25 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=1:1) to give the title compound (1.60 mg, 60% yield) as brown oil. $^1H$ NMR (400 MHz, $CDCl_3$) δ 8.22 (s, 1H), 7.58 (s, 1H), 3.93 (s, 3H), 3.73

(s, 3H), 3.54 (d, J=6.0 Hz, 2H), 2.80 (m, 1H), 2.04 (m, 4H), 1.93-1.80 (m, 3H), 1.66 (m, 1H), 1.18 (m, 2H). LC-MS ($ESI^+$) m/z 383.2 $(M+H)^+$.

N-(2-((1r,4r)-4-formylcyclohexyl)-5-(2-hydroxypropan-2-yl)-1-methyl-1H-benzo[d] imidazol-6-yl)-6-(trifluoromethyl)picolinamide (Intermediate BEB)

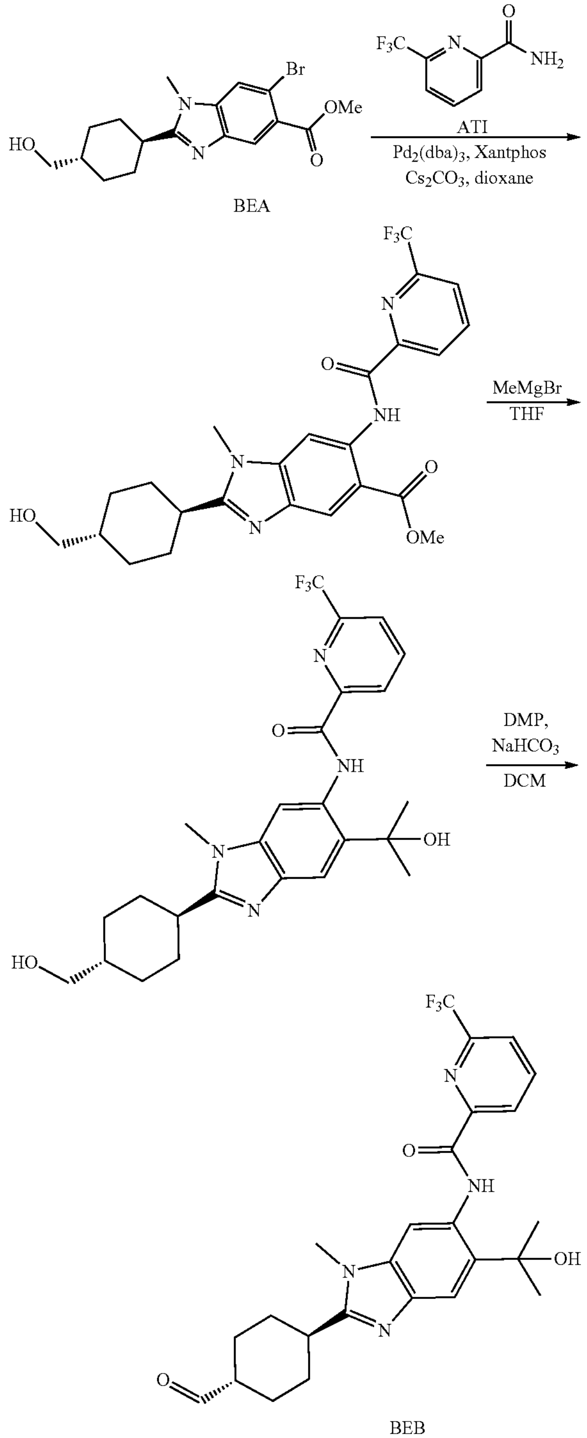

Step 1—Methyl 2-((1r,4r)-4-(hydroxymethyl)cyclohexyl)-1-methyl-6-(6-(trifluoromethyl)picolinamido)-1H-benzo[d]imidazole-5-carboxylate To a solution of methyl 6-bromo-2-[4-(hydroxymethyl) cyclohexyl]-1-methyl-benzimidazole-5- carboxylate (1.60 g, 4.20 mmol, Intermediate BEA), 6-(trifluoromethyl)pyridine-2-carboxamide (878 mg, 4.62 mmol, Intermediate ATI) and $Cs_2CO_3$ (2.73 g, 8.39 mmol) in dioxane (20 mL) was added $Pd_2(dba)_3$ (192 mg, 210 umol) and Xantphos (243 mg, 420 umol). The reaction mixture was degassed and purged with nitrogen for 3 times, and then the mixture was stirred at 80° C. for 16 hrs under nitrogen atmosphere. On completion, the reaction mixture was filtered and the filter cake was triturated with EA (50 mL) at 25° C. for 10 min to give the title compound (1.10 g, 53% yield) as a yellow solid. $^1H$ NMR (400 MHz, $CDCl_3$) δ 13.27 (s, 1H), 9.01 (s, 1H), 8.54 (s, 1H), 8.49 (s, 1H), 8.13 (t, J=7.6 Hz, 1H), 7.92-7.84 (m, 1H), 4.03 (s, 3H), 3.80 (s, 3H), 3.71 (s, 1H), 3.56 (d, J=6.0 Hz, 2H), 2.84 (m, 1H), 2.11 (m, 2H), 2.02 (m, 1H), 1.92-1.81 (m, 2H), 1.76-1.57 (m, 2H), 1.26-1.13 (m, 2H). LC-MS ($ESI^+$) m/z 491.3 $(M+H)^+$.

Step 2—N-(2-((1r,4r)-4-(hydroxymethyl)cyclohexyl)-5-(2-hydroxypropan-2-yl)-1-methyl-1H-benzo[d]imidazol-6-yl)-6-(trifluoromethyl)picolinamide To a solution of methyl 2-[4-(hydroxymethyl)cyclohexyl]-1-methyl-6-[[6-(trifluoromethyl)pyridine- 2- carbonyl]amino]benzimidazole-5-carboxylate (200 mg, 408 umol) in THF (10 mL) was added MeMgBr (3 M, 1.36 mL) at 0° C. The mixture was stirred at 25° C. for 16 hrs. On completion, the reaction mixture was poured into saturated ammonium chloride aqueous solution (10 mL) at 0° C. and extracted with ethyl acetate (3×5 mL). The combined organic layers were washed with sodium chloride solution (5 mL), dried over anhydrous sodium sulfate, filtered and concentrated in vacuo to give a residue. The residue was triturated with EA (5 mL) at 25° C. for 10 min to give the title compound (100 mg, 49% yield) as a white solid. $^1H$ NMR (400 MHz, DMSO-$d_6$) δ 12.48 (s, 1H), 8.59-8.48 (m, 1H), 8.48-8.43 (m, 1H), 8.41-8.33 (m, 1H), 8.17 (d, J=7.6 Hz, 1H), 7.54 (s, 1H), 5.87 (s, 1H), 4.45 (t, J=5.2 Hz, 1H), 3.74 (s, 3H), 3.28 (t, J=5.6 Hz, 2H), 2.98-2.85 (m, 1H), 1.99-1.93 (m, 2H), 1.86 (m, 2H), 1.66-1.56 (m, 8H), 1.49-1.40 (m, 1H), 1.16-1.04 (m, 2H). LC-MS ($ESI^+$) m/z 491.3 $(M+H)^+$.

Step 3—N-(2-((1r,4r)-4-formylcyclohexyl)-5-(2-hydroxypropan-2-yl)-1-methyl-1H-benzo[d] imidazol-6-yl)-6-(trifluoromethyl)picolinamide To a solution of N-[2-[4-(hydroxymethyl)cyclohexyl]-6-(1-hydroxy-1-methyl-ethyl)-3-methyl- benzimidazol-5-yl]-6-(trifluoromethyl)pyridine-2-carboxamide (70.0 mg, 143 umol) and $NaHCO_3$ (60.0 mg, 714 umol) in DCM (1 mL) was added DMP (72.6 mg, 171 umol) at 0° C. The mixture was stirred at 25° C. for 3 hrs. On completion, the reaction mixture was concentrated in vacuo to give a residue. The residue was triturated with EA (5 mL) at 25° C. for 10 min to give the title compound (50.0 mg, 61% yield) as a yellow solid. $^1H$ NMR (400 MHz, $CDCl_3$) δ 12.49 (s, 1H), 9.72 (s, 1H), 8.73 (s, 1H), 8.49 (d, J=7.6 Hz, 1H), 8.12 (t, J=7.6 Hz, 1H), 7.85 (d, J=7.6 Hz, 1H), 7.80 (s, 1H), 3.87-3.70 (m, 3H), 2.93-2.77 (m, 1H), 2.75-2.52 (m, 1H), 2.43 (m, 1H), 2.30-

2.09 (m, 4H), 2.01-1.87 (m, 2H), 1.80 (s, 5H), 1.55-1.38 (m, 2H). LC-MS ($ESI^+$) m/z 489.3 $(M+H)^+$.

N-[2-[4-(bromomethyl)cyclohexyl]-6-methoxy-indazol-5-yl]-6-(trifluoromethyl)pyridine-2- carboxamide (Intermediate BEC)

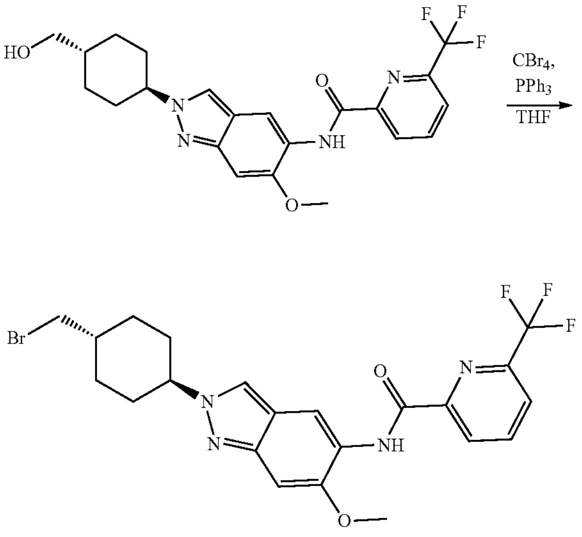

BEC

To a mixture of N-[2-[4-(hydroxymethyl)cyclohexyl]-6-methoxy-indazol-5-yl]-6-(trifluoromethyl)pyridine-2-carboxamide (1.15 g, 2.56 mmol, synthesized via Step 1 of Intermediate ATJ) in THE (10 mL) was added $PPh_3$ (807 mg, 3.08 mmol), $CBr_4$ (1.02 g, 3.08 mmol) at 0° C. The reaction mixture was stirred at 0° C. for 0.5 hr, then the reaction mixture warm to 25° C. and stirred for 12 hr. On completion, the mixture was quenched with water (1 mL) and extracted with ethyl acetate (3×25 mL). The combined organic phase was dried over anhydrous sodium sulfate, filtered and concentrated to give a residue. The residue was purified by reversed-phase flash(0.1% FA condition) to give the title compound (470 mg, 34% yield) as a yellow solid. $^1H$ NMR (400 MHz, DMSO-$d_6$) δ 10.50 (s, 1H), 8.69 (s, 1H), 8.49-8.44 (m, 1H), 8.43-8.37 (m, 1H), 8.33 (s, 1H), 8.21 (dd, J=0.8, 7.6 Hz, 1H), 7.16 (s, 1H), 4.42-4.32 (m, 1H), 3.98 (s, 3H), 3.51-3.48 (m, 2H), 2.19-2.12 (m, 2H), 2.01-1.83 (m, 4H), 1.70-1.63 (m, 1H), 1.39-1.22 (m, 2H). LC-MS ($ESI^+$) m/z 512.9 $(M+H)^+$.

Tert-butyl 7-(aminomethyl)-2-azaspiro[3.5]nonane-2-carboxylate (Intermediate AUJ)

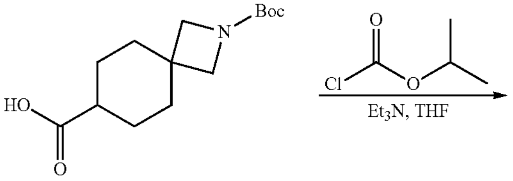

-continued

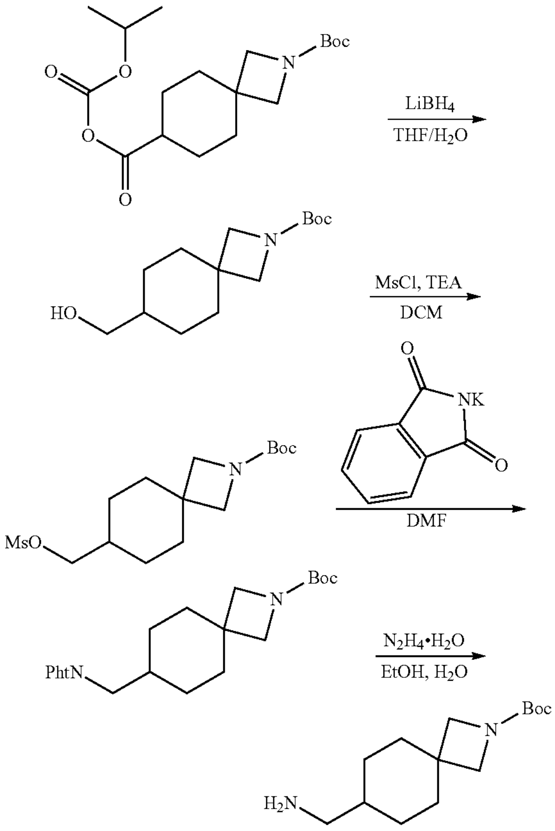

AUJ

Step 1—2-Tert-butyl 7-isopropoxycarbonyl 2-azaspiro[3.5]nonane-2,7-dicarboxylate To a solution of 2-tert-butoxycarbonyl-2-azaspiro[3.5]nonane-7-carboxylic acid (840 mg, 3.12 mmol, CAS #1363381-18-3) in THF (10.0 mL) was added $Et_3N$ (1.26 g, 12.5 mmol) and isopropyl carbonochloridate (573 mg, 4.68 mmol). The mixture was stirred at 0° C. for 2 hours. On completion, the mixture was filtered and the filter cake was washed with THF (30 mL). The filtrate was concentrated in vacuo to give the title compound (1.10 g, 99% yield) as yellow oil.

Step 2—Tert-butyl 7-(hydroxymethyl)-2-azaspiro[3.5]nonane-2-carboxylate

To a solution of tert-butyl-isopropoxycarbonyl 2-azaspiro[3.5]nonane-2,7-dicarboxylate (1.10 g, 3.09 mmol) in a mixed solvent of THF (20 mL) and $H_2O$ (1 mL) was added $LiBH_4$ (404 mg, 18.5 mmol). The mixture was stirred at 0° C. for 2 hours. On completion, the reaction mixture was quenched with water (5.0 mL) at 0° C., and then extracted with (3×20 mL). The combined organic layers were washed with brine (50 mL), dried over $Na_2SO_4$, filtered and concentrated in vacuo to give the title compound (800 mg, 80% yield) as colorless oil. $^1H$ NMR (400 MHz, $CDCl_3$) δ 3.57 (s, 2H), 3.54 (s, 2H), 3.42 (d, J=6.4 Hz, 2H), 1.89 (d, J=13.4 Hz, 2H), 1.76-1.67 (m, 3H), 1.45-1.39 (m, 12H), 1.01-0.89 (m, 2H).

Step 3—Tert-butyl 7-(methylsulfonyloxymethyl)-2-azaspiro[3.5]nonane-2-carboxylate To a solution of tert-butyl 7-(hydroxymethyl)-2-azaspiro[3.5]nonane-2-carboxylate (800 mg, 3.13 mmol) in DCM (10 mL) was added $Et_3N$ (951 mg, 9.40 mmol). Then MsCl (43.0 mg, 3.76 mmol) was added to the mixture. The mixture was stirred at 0° C. for 2 hours. On completion, the mixture was concentrated in vacuo to give a residue. The residue was diluted with water (50 mL) and extracted with EA (3×60 mL). The combined organic layers were washed with brine (100 mL), dried over $Na_2SO_4$, filtered and concentrated in vacuo to give the title compound (1.00 g, 95% yield) as yellow oil. $^1H$ NMR (400 MHz, $CDCl_3$) δ 4.04 (d, J=6.0 Hz, 2H), 3.60 (d, J=11.6 Hz, 4H), 3.02 (s, 3H), 1.95 (d, J=13.6 Hz, 2H), 1.82-1.72 (m, 3H), 1.46 (s, 10H), 1.11-1.02 (m, 2H).

Step 4—Tert-butyl 7-[(1,3-dioxoisoindolin-2-yl)methyl]-2-azaspiro[3.5]nonane-2-carboxylate To a solution of tert-butyl 7-(methylsulfonyloxymethyl)-2-azaspiro[3.5]nonane-2-carboxylate (1.00 g, 3.00 mmol) in DMF (10 mL) was added (1,3-dioxoisoindolin-2-yl)potassium (833 mg, 4.50 mmol, CAS #1074-82-4). The mixture was stirred at 80° C. for 2 hours. On completion, the mixture was diluted with water (50 mL) and extracted with EA (3×50 mL). The combined organic layers were washed with brine (100 mL), dried over $Na_2SO_4$, filtered and concentrated in vacuo to give a residue. The residue was triturated with PE/EA (3:1) and the filtered cake was collected and dried in vacuo to give the title compound (200 mg, 17% yield) as white solid. $^1H$ NMR (400 MHz, $CDCl_3$) δ 7.81-7.76 (m, 2H), 7.70-7.62 (m, 2H), 3.53 (s, 2H), 3.48-3.44 (m, 3H), 1.82 (d, J=13.2 Hz, 2H), 1.72-1.68 (m, 1H), 1.62-1.55 (m, 3H), 1.36 (s, 9H), 1.33-1.26 (m, 2H), 1.04-0.90 (m, 2H).

Step 5—Tert-butyl 7-(aminomethyl)-2-azaspiro[3.5]nonane-2-carboxylate

To a solution of tert-butyl 7-[(1,3-dioxoisoindolin-2-yl)methyl]-2-azaspiro[3.5]nonane-2-carboxylate (200 mg, 520 umol) in EtOH (5.0 mL) was added $NH_2NH_2.H_2O$ (130 mg, 2.60 mmol). The mixture was stirred at 80° C. for 2 hours. On completion, the mixture was concentrated in vacuo to give a residue. The residue was washed with DCM (3×50 mL) then filtered, and the organic phase was concentrated in vacuo to give the title compound (100 mg, 75% yield) as colorless oil.

4-(2-Azaspiro[3.5]nonan-7-ylmethylamino)-2-(2,6-dioxo-3-piperidyl) isoindoline-1,3-dione (Intermediate AUK)

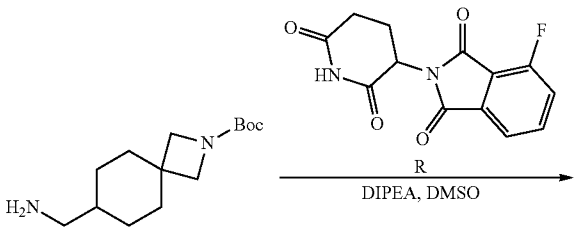

AUJ

-continued

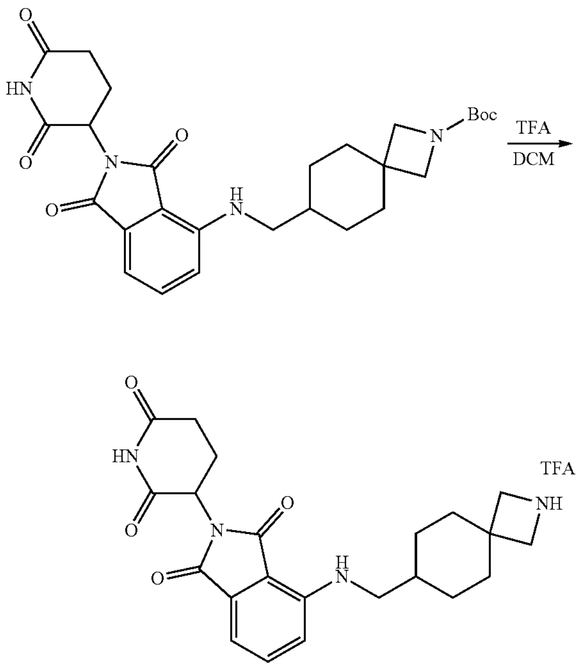

AUK

Step 1—Tert-butyl 7-[[[2-(2,6-dioxo-3-piperidyl)-1,3-dioxo-isoindolin-4-yl]amino]methyl]-2- azaspiro[3.5]nonane-2-carboxylate To a solution of tert-butyl 7-(aminomethyl)-2-azaspiro[3.5]nonane-2-carboxylate (100 mg, 393 umol, Intermediate AUJ) and 2-(2,6-dioxo-3-piperidyl)-4-fluoro-isoindoline-1,3-dione (108 mg, 393 umol, Intermediate R) in DMSO (2 mL) was added DIPEA (50.8 mg, 393 umol). The mixture was stirred at 130° C. for 2 hours. On completion, the mixture was quenched with $H_2O$ (0.2 mL) and concentrated in vacuo to give a residue. The residue was purified by reverse phase (0.1% FA condition) to give the title compound (90.0 mg, 44% yield) as yellow solid. $^1H$ NMR (400 MHz, DMSO-$d_6$) δ 11.19-10.96 (m, 1H), 7.57-7.53 (m, 1H), 7.10 (d, J=8.8 Hz, 1H), 6.99 (d, J=6.8 Hz, 1H), 6.55 (t, J=6.2 Hz, 1H), 5.05-5.00 (m, 1H), 3.52-3.41 (m, 4H), 3.13 (t, J=6.4 Hz, 2H), 2.93-2.80 (m, 1H), 2.61-2.51 (m, 2H), 2.06-1.96 (m, 1H), 1.84-1.76 (m, 2H), 1.68-1.59 (m, 2H), 1.40-1.33 (m, 12H), 1.04-0.92 (m, 2H); LC-MS ($ESI^+$) m/z 511.1 $(M+1)^+$.

Step 2—4-(2-Azaspiro[3.5]nonan-7-ylmethylamino)-2-(2,6-dioxo-3-piperidyl) isoindoline-1,3-dione To a solution of tert-butyl 7-[[[2-(2,6-dioxo-3-piperidyl)-1,3-dioxo-isoindolin-4-yl]amino]methyl]-2- azaspiro[3.5]nonane-2-carboxylate (80.0 mg, 156 umol) in DCM (3 mL) was added TFA (1.54 g, 13.5 mmol). The mixture was stirred at 15° C. for 2 hours. On completion, the mixture was concentrated in vacuo to give the title compound (64.0 mg, 99.51% yield) as yellow oil. LC-MS ($ESI^+$) m/z 411.3 $(M+1)^+$.

4-Bromo-3-methyl-1-(2-trimethylsilylethoxymethyl) benzimidazol-2-one (Intermediate BED)

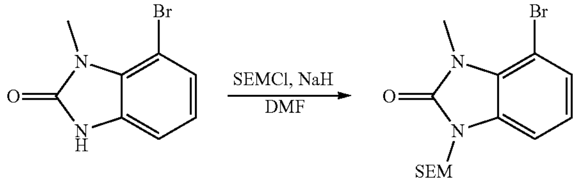

BED

To a mixture of 4-bromo-3-methyl-1H-benzimidazol-2-one (50.0 g, 220 mmol, synthesized via Steps 1-3 of Intermediate HP) in DMF (500 mL) was added NaH (13.2 g, 330 mmol, 60% dispersion in mineral oil) at 0° C. The reaction mixture was stirred for 30 minutes. Then SEMCl (44.0 g, 264 mmol) was added dropwise at 0° C. and the reaction mixture was stirred for 16 hours. On completion, the mixture was poured into water (500 mL). The mixture was extracted with DCM (3×200 mL) and the combined organic layer was dried over by $Na_2SO_4$. The mixture was filtrated and the filtrate was concentrated in vacuo. The residue was purified by column chromatography (petroleum ether/ethyl acetate=20/1) to give the title compound (60.0 g, 76% yield) as yellow oil. $^1H$ NMR (400 MHz, DMSO-$d_6$) δ 7.34-7.21 (m, 2H), 7.01-6.97 (m, 1H), 5.24 (s, 2H), 3.61 (s, 3H), 3.55-3.51 (m, 2H), 0.85-0.81 (m, 2H), 0.07 (s, 9H).

5-(2-Azaspiro[3.3]heptan-6-ylmethylamino)-2-(2,6-dioxo-3-piperidyl)isoindoline-1,3-dione (Intermediate BEE)

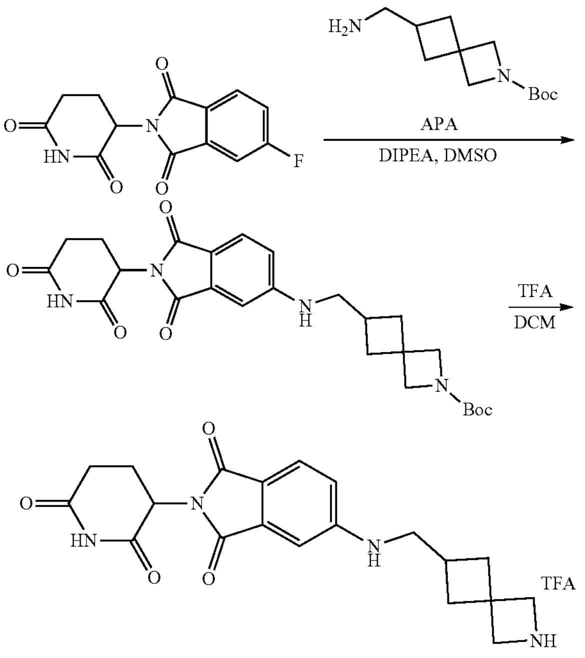

BEE

Step 1—Tert-butyl 6-[[[2-(2,6-dioxo-3-piperidyl)-1,3-dioxo-isoindolin-5-yl]amino]methyl]-2- azaspiro [3.3]heptanes-2-carboxylate To a solution of 2-(2,6-dioxo-3-piperidyl)-5-fluoro-isoindoline-1,3-dione (219 mg, 795 umol, CAS #1160247-15-3) and tert-butyl 6-(aminomethyl)-2-azaspiro[3.3]heptane-2-carboxylate (150 mg, 662 umol, Intermediate APA) in DMSO (3 mL) was added DIPEA (171 mg, 1.33 mmol) at 25° C. The reaction mixture was stirred at 130° C. for 3 hours. On completion, the reaction mixture was concentrated in vacuo. The residue was purified by reverse phase (0.1% FA condition) to give the title compound (160 mg, 50% yield) as a yellow solid. $^1H$ NMR (400 MHz, DMSO-$d_6$) δ 11.05 (s, 1H), 7.55 (d, J=8.4 Hz, 1H), 7.09 (t, J=5.6 Hz, 1H), 6.94 (d, J=1.6 Hz, 1H), 6.84 (dd, J=2.0, 8.4 Hz, 1H), 5.02 (dd, J=5.6, 13.2 Hz, 1H), 3.88-3.72 (m, 4H), 3.30 (s, 2H), 3.15 (t, J=6.0 Hz, 2H), 2.92-2.82 (m, 1H), 2.44-2.35 (m, 1H), 2.30-2.21 (m, 2H), 2.03-1.95 (m, 1H), 1.94-1.85 (m, 2H), 1.35 (s, 9H).

Step 2—5-(2-Azaspiro[3.3]heptan-6-ylmethylamino)-2-(2,6-dioxo-3-piperidyl)isoindoline-1,3-dione To a solution of tert-butyl 6-[[[2-(2,6-dioxo-3-piperidyl)-1,3-dioxo-isoindolin-5-yl]amino]methyl]-2- azaspiro[3.3] heptane-2-carboxylate (70.0 mg, 145 umol) in DCM (2 mL) was added TFA (1.67 mL) at 25° C. The mixture was stirred at 25° C. for 1 hour. On completion, the mixture was concentrated in vacuo to give the title compound (70.0 mg, 97% yield, TFA salt) as yellow oil. LC-MS (ESI$^+$) m/z 383.3 (M+H)$^+$.

[4-[5-Amino-6-(1-piperidyl)indazol-2-yl]cyclohexyl] methanol (Intermediate BEF)

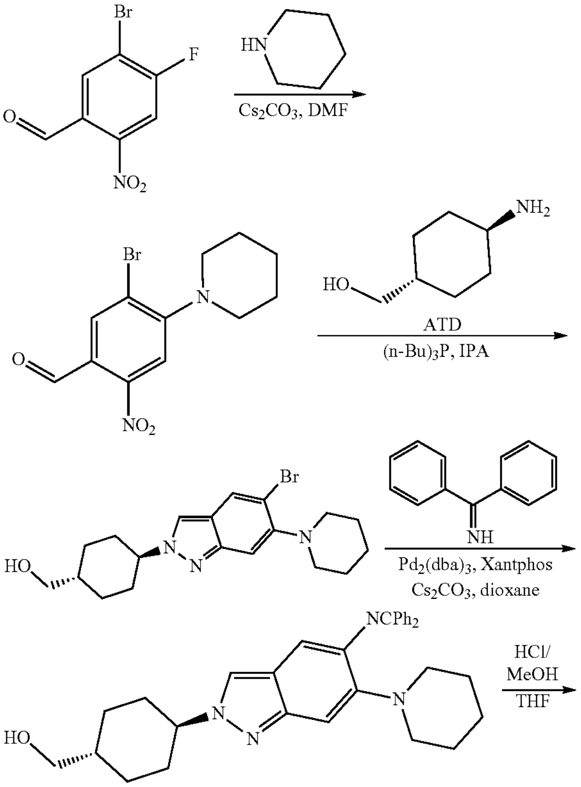

-continued

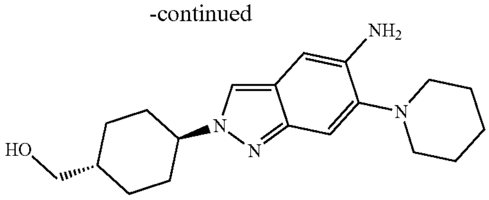

BEF

Step 1—5-Bromo-2-nitro-4-(1-piperidyl)benzaldehyde

To a solution of 5-bromo-4-fluoro-2-nitro-benzaldehyde (1.50 g, 6.05 mmol, synthesized via Step 1 of Intermediate ATE) and piperidine (1.54 g, 18.1 mmol, CAS #110-89-4) in DMSO (20 mL) was added $Cs_2CO_3$ (5.91 g, 18.1 mmol) at 25° C. The reaction mixture was stirred at 80° C. for 3 hours. On completion, the mixture was concentrated in vacuo. The residue was purified by reverse phase (0.1% FA condition) to give the title compound (1.40 g, 73% yield) as yellow solid. LC-MS ($ESI^+$) m/z 315.1 $(M+H)^+$.

Step 2—[4-[5-Bromo-6-(1-piperidyl)indazol-2-yl]cyclohexyl]methanol

To a solution of 5-bromo-2-nitro-4-(1-piperidyl)benzaldehyde (1.30 g, 4.15 mmol) and (4-aminocyclohexyl)methanol (590 mg, 4.57 mmol, Intermediate ATD) in IPA (20 mL) was stirred at 80° C. for 3 hours. Then tributylphosphane (12.4 mmol, 3.07 mL) was added to above mixture at 25° C., then the reaction mixture was stirred at 80° C. for 12 hours. On completion, the reaction mixture was concentrated in vacuo. The residue was purified by column chromatography ($SiO_2$, petroleum ether/ethyl acetate=10/1 to 1/1) to give the title compound (2.10 g, 96% yield) as a yellow solid. $^1H$ NMR (400 MHz, DMSO-$d_6$) δ 8.27 (s, 1H), 7.96 (s, 1H), 7.20 (s, 1H), 4.49 (t, J=5.2 Hz, 1H), 4.42-4.31 (m, 1H), 3.28 (t, J=5.6 Hz, 2H), 2.89 (s, 3H), 2.15-2.03 (m, 2H), 1.93-1.81 (m, 4H), 1.74-1.65 (m, 4H), 1.60-1.56 (m, 4H), 1.40-1.38 (m, 2H); LC-MS ($ESI^+$) m/z 391.9 $(M+H)^+$.

Step 3—[4-[5-(Benzhydrvlideneamino)-6-(1-piperidyl)indazol-2-yl]cyclohexyl]methanol To a solution of diphenylmethanimine (346 mg, 1.91 mmol, CAS #1013-88-3) and [4-[5-bromo-6-(1-piperidyl)indazol-2-yl]cyclohexyl]methanol (500 mg, 955 umol) in toluene (8 mL) was added $Pd_2(dba)_3$ (87.5 mg, 95.5 umol), BINAP (119 mg, 191 umol) and t-BuONa (275 mg, 2.87 mmol) at 25° C. The reaction mixture was stirred at 80° C. for 12 hours under $N_2$. On completion, the reaction mixture was filtered and the filtrate was concentrated in vacuo. The residue was purified by reverse phase (0.1% $NH_3.H_2O$ condition) to give the title compound (230 mg, 19% yield) as a yellow solid. LC-MS ($ESI^+$) m/z 493.4 $(M+H)^+$.

Step 4—[4-[5-Amino-6-(1-piperidyl)indazol-2-yl]cyclohexyl]methanol

To a solution of [4-[5-(benzhydrylideneamino)-6-(1-piperidyl)indazol-2-yl]cyclohexyl]methanol (200 mg, 405 umol) in THF (5 mL) was added HCl/MeOH (4 M, 3 mL) at 25° C. The mixture was stirred at 25° C. for 1 hour. On completion, the reaction mixture was concentrated in vacuo.

The residue was purified by reverse phase (0.1% FA condition) to give the title compound (80.0 mg, 60% yield) as a brown solid. $^1H$ NMR (400 MHz, DMSO-$d_6$) δ 7.94 (s, 1H), 7.05 (s, 1H), 6.94-6.75 (m, 1H), 6.09-5.32 (m, 1H), 4.47 (s, 1H), 4.30-4.20 (m, 1H), 3.27 (d, J=6.0 Hz, 2H), 2.81 (s, 4H), 2.11-2.02 (m, 2H), 1.90-1.77 (m, 4H), 1.74-1.65 (m, 4H), 1.59-1.41 (m, 3H), 1.18-1.05 (m, 2H); LC-MS ($ESI^+$) m/z 329.2 $(M+H)^+$.

N-[2-(4-formylcyclohexyl)-6-(1-piperidyl)indazol-5-yl]-6-(pentafluoro-sulfanyl)pyridine-2-carboxamide (Intermediate BEG)

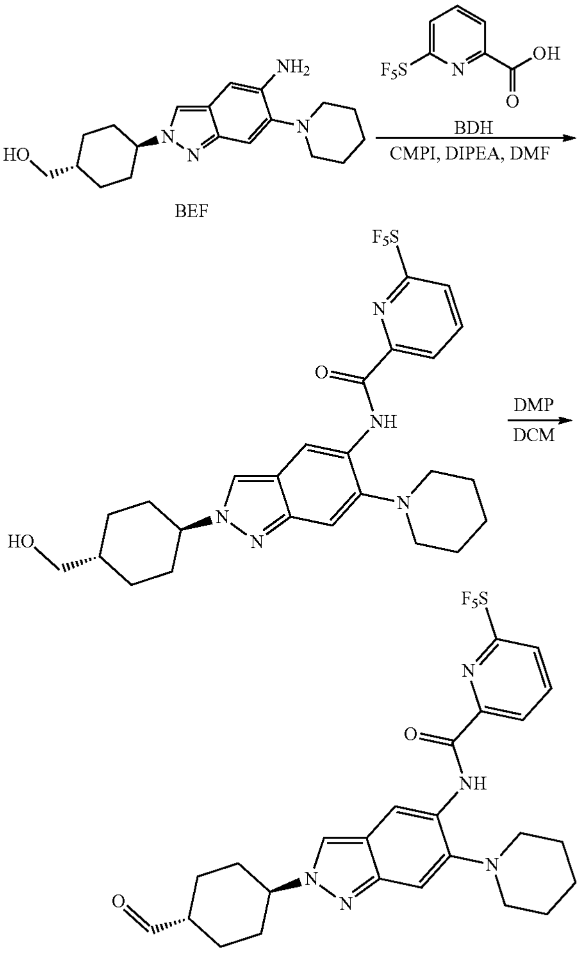

BEG

Step 1—N-[2-[4-(hydroxymethyl)cyclohexyl]-6-(1-piperidyl)indazol-5-yl]-6-(pentafluoro-sulfanyl)pyridine-2-carboxamide To a solution of 6-(pentafluoro-sulfanyl)pyridine-2-carboxylic acid (50.0 mg, 200 umol, Intermediate BDH) in DMF (3 mL) was added CMPI (66.6 mg, 260 umol) and DIPEA (77.8 mg, 602 umol) at 25° C. The mixture was stirred for 30 minutes. Then, [4-[5-amino-6-(1-piperidyl)indazol-2- yl]cyclohexyl]methanol (65.9 mg, 200 umol, Intermediate BEF) was added to above mixture at 25° C. The reaction mixture was stirred at 25° C. for 1.5 hours. On completion, the reaction mixture was concentrated in vacuo. The residue was purified by reverse phase (0.1% FA condition) to give the title compound (70.0 mg, 62% yield) as a white solid. $^1$H NMR (400 MHz, DMSO-$d_6$) δ 10.85 (s, 1H), 8.78 (s, 1H), 8.55-8.51 (m, 1H), 8.50-8.45 (m, 1H), 8.37 (s, 1H), 8.34 (dd, J=1.2, 8.0 Hz, 1H), 7.46 (s, 1H), 4.49 (t, J=4.8 Hz, 1H), 4.43-4.33 (m, 1H), 3.30 (s, 2H), 2.84 (s, 4H), 2.18-2.07 (m, 2H), 1.95-1.84 (m, 4H), 1.80-1.73 (m, 4H), 1.65-1.53 (m, 2H), 1.52-1.43 (m, 1H), 1.23-1.08 (m, 2H); LC-MS (ESI$^+$) m/z 560.2 (M+H)$^+$.

Step 2—N-[2-(4-formylcyclohexyl)-6-(1-piperidyl)indazol-5-yl]-6-(pentafluoro-sulfanyl)pyridine-2-carboxamide To a solution of N-[2-[4-(hydroxymethyl)cyclohexyl]-6-(1-piperidyl)indazol-5-yl]-6- (pentafluoro-sulfanyl)pyridine-2-carboxamide (70.0 mg, 125 umol) in DCM (1.5 mL) was added DMP (79.5 mg, 187 umol) at 25° C. The reaction mixture was stirred at 25° C. for 2 hours. On completion, the reaction mixture was quenched with sat. aq. $Na_2S_2O_3$ (3 mL) and sat. aq. $NaHCO_3$ (3 mL), then extracted with DCM (3×5 mL). The combined organic layers were washed with brine (2×2 mL), dried over by $Na_2SO_4$, filtered and concentrated in vacuo to give the title compound (65.0 mg, 93% yield) as a brown solid. LC-MS (ESI$^+$) m/z 558.3 (M+H)$^+$.

[4-[6-Amino-5-[4-[[tert-butyl(dimethyl)silyl]oxymethyl]-1-piperidyl]-1,3-benzoxazol-2-yl]cyclohexyl]methanol (Intermediate BEH)

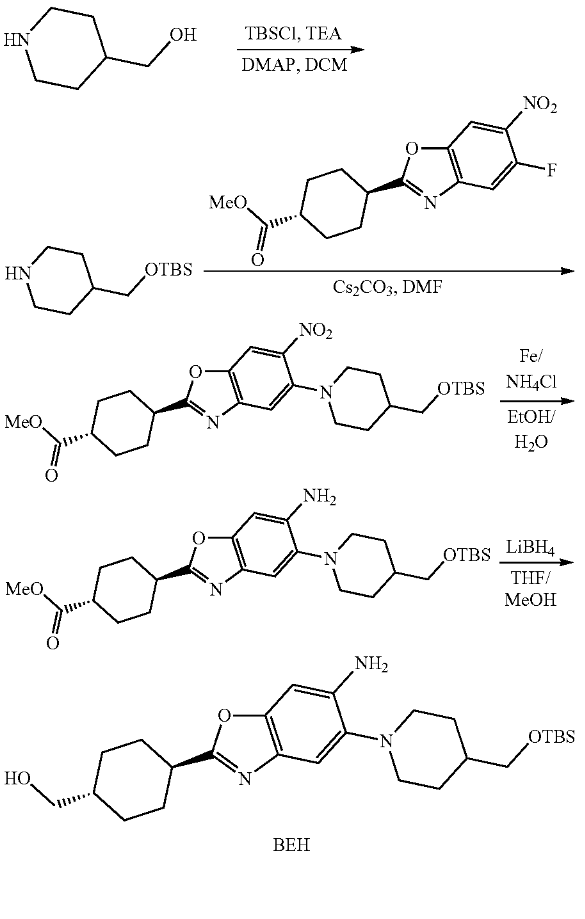

BEH

Step 1—Tert-butyl-dimethyl-(4-piperidylmethoxy)silane

To a solution of 4-piperidylmethanol (4 g, 34.7 mmol, CAS #6457-49-4), tert-butyl-chloro-dimethyl-silane (5.76 g, 38.2 mmol) and DMAP (424 mg, 3.47 mmol) in DCM (50 mL) was added TEA (4.25 g, 41.9 mmol, 5.84 mL) at 0° C. The reaction mixture was stirred at 0° C. for 2 hours. On completion, the reaction mixture was diluted with water (50 mL) and extracted with EA (3×50 mL). The combined organic layers were washed with brine (2×50 mL), dried over $Na_2SO_4$, filtered and concentrated in vacuo to give the title compound (6.40 g, 80% yield) as white solid. $^1$H NMR (400 MHz, $CDCl_3$) δ 3.54-3.45 (m, 4H), 2.85 (m, 2H), 1.93 (d, J=12.8 Hz, 2H), 1.79-1.54 (m, 3H), 0.88 (s, 9H), 0.04 (s, 6H).

Step 2—Methyl 4-[5-[4-[[tert-butyl(dimethyl)silyl]oxymethyl]-1-piperidyl]-6-nitro-1,3-benzoxazol-2-yl]cyclohexanecarboxylate A mixture of methyl 4-(5-fluoro-6-nitro-1,3-benzoxazol-2-yl)cyclohexanecarboxylate (1.00 g, 3.10 mmol, synthesized via Steps 1-3 of Intermediate BCA), tert-butyl-dimethyl-(4-piperidylmethoxy)silane (854 mg, 3.72 mmol) and $Cs_2CO_3$ (2.02 g, 6.21 mmol) in DMF (10 mL) was stirred at 25° C. for 12 hrs. On completion, the reaction mixture was diluted with water (50 mL), then extracted with EA (3×50 mL). The combined organic layers were washed with brine (2×50 mL), dried over $Na_2SO_4$, filtered and concentrated in vacuo. On completion, the residue was purified by silica gel chromatography (PE:EA=10:1) to give the title compound (0.90 g, 49% yield) as yellow solid. $^1$H NMR (400 MHz, $CDCl_3$) δ 7.92 (s, 1H), 7.46 (s, 1H), 3.70 (s, 3H), 3.49 (d, J=6.6 Hz, 2H), 3.24 (d, J=12.0 Hz, 2H), 2.95 (m, 1H), 2.80-2.74 (m, 2H), 2.42-2.36 (m, 1H), 2.34-2.27 (m, 2H), 2.18 (dd, J=3.2, 13.2 Hz, 2H), 1.84-1.77 (m, 2H), 1.72-1.60 (m, 4H), 1.47-1.37 (m, 2H), 0.90 (s, 9H), 0.06 (s, 6H).

Step 3—Methyl 4-[6-amino-5-[4-[[tert-butyl(dimethyl)silyl]oxymethyl]-1-piperidyl]-1,3-benzoxazol-2-yl]cyclohexanecarboxylate A mixture of methyl 4-[5-[4-[[tert-butyl(dimethyl)silyl]oxymethyl]-1-piperidyl]-6-nitro-1,3-benzoxazol- 2-yl]cyclohexanecarboxylate (1.10 g, 2.07 mmol), $NH_4Cl$ (1.11 g, 20.6 mmol) in EtOH (10 mL) and $H_2O$ (10 mL) was stirred at 80° C., then Fe (577 mg, 10.3 mmol) was added. The reaction mixture was stirred at 80° C. for 4 hours. On completion, the reaction mixture was filtered. The filtrate was diluted with water (50 ml), then extracted with EA (3×50 mL). The combined organic layers were washed with brine (2×50 mL), dried over $Na_2SO_4$, filtered and concentrated in vacuo to give the title compound (0.95 g, 82% yield) as brown solid, $^1$H NMR (400 MHz, $CDCl_3$) δ 7.28-7.26 (m, 1H), 7.23 (s, 1H), 6.79 (s, 1H), 4.32-4.01 (m, 2H), 3.66 (s, 3H), 3.48 (d, J=6.4 Hz, 2H), 3.06 (d, J=11.2 Hz, 2H), 2.81 (tt, J=3.6, 11.6 Hz, 1H), 2.57 (t, J=11.2 Hz, 2H), 2.38-2.32 (m, 1H), 2.23 (dd, J=2.0, 13.6 Hz, 2H), 2.13-2.08 (m, 2H), 1.80 (d, J=11.6 Hz, 2H), 1.60 (d, J=10.4 Hz, 4H), 1.39-1.28 (m, 2H), 0.88 (s, 9H), 0.03 (s, 6H).

Step 4—[4-[6-Amino-5-[4-[[tert-butyl(dimethyl)silyl]oxymethyl]-1-piperidyl]-1,3-benzoxazol-2-yl]cyclohexyl]methanol To a solution of methyl 4-[6-amino-5-[4-[[tert-butyl(dimethyl)silyl]oxymethyl]-1-piperidyl]-1,3-benzoxazo 1-2-yl]cyclohexanecarboxylate (900 mg, 1.61 mmol) in a mixed solution of MeOH (1 mL) and THE (8 mL) was added $LiBH_4$ (105 mg, 4.84 mmol,) at 0° C. The reaction mixture was stirred at 25° C. for 4 hrs. On completion, the reaction mixture was quenched with sat. eq. $NH_4Cl$ (1 ml). The reaction mixture was diluted with water (50 mL), and extracted with EA (2×50 mL). The combined organic layers was washed with brine (2×50 mL), dried over $Na_2SO_4$, filtered and concentrated in vacuo. The residue was purified by silica gel chromatography (PE:EA=2:1) to give the title compound (350 mg, 45% yield) as obtained as red solid. $^1H$ NMR (400 MHz, $CDCl_3$) δ 7.32 (s, 1H), 6.84 (s, 1H), 3.53 (dd, J=3.6, 6.4 Hz, 4H), 3.11 (d, J=11.6 Hz, 2H), 2.82 (m, 1H), 2.62 (t, J=10.8 Hz, 2H), 2.31-2.19 (m, 2H), 2.01-1.93 (m, 2H), 1.85 (d, J=10.8 Hz, 2H), 1.74-1.52 (m, 6H), 1.43-1.32 (m, 2H), 1.20-1.08 (m, 2H), 0.93-0.91 (m, 9H), 0.09-0.06 (m, 6H).

N-[5-[4-[[tert-butyl(dimethyl)silyl]oxymethyl]-1-piperidyl]-2-(4-formylcyclohexyl)-1,3- benzoxazol-6-yl]-6-(trifluoromethyl)pyridine-2-carboxamide (Intermediate BEI)

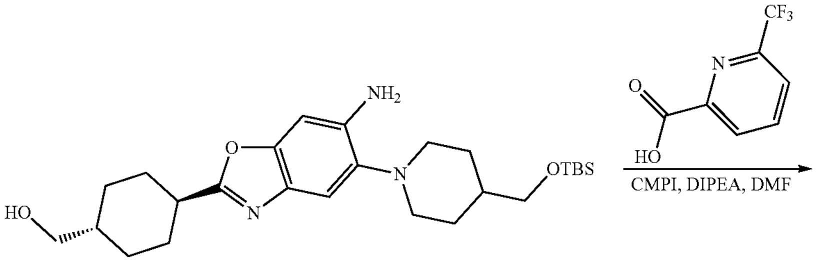

BEH

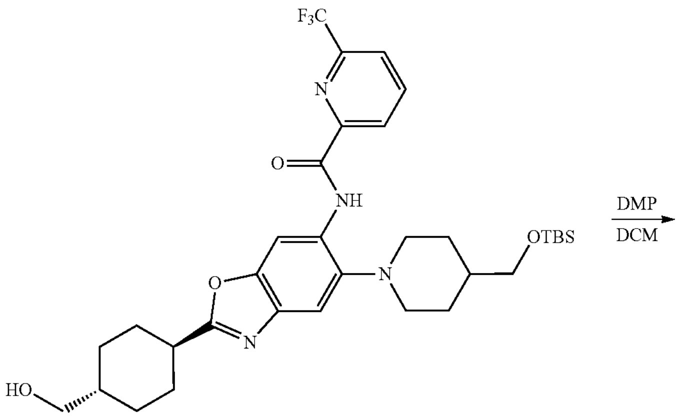

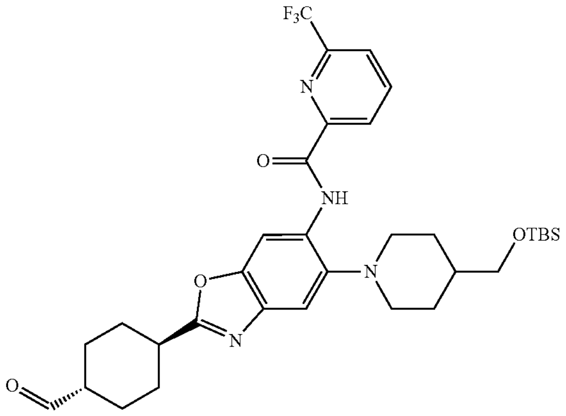

BEI

Step 1—N-[5-[4-[[tert-butyl(dimethyl)silyl]oxymethyl]-1-piperidyl]-2-[4-(hydroxymethyl)cyclohexyl]-1,3-benzoxazol-6-yl]-6-(trifluoromethyl)pyridine-2-carboxamide To a solution of [4-[6-amino-5-[4-[[tert-butyl(dimethyl)silyl]oxymethyl]-1-piperidyl]-1,3-benzoxazol-2-yl]cyclohexyl]methanol (330 mg, 696 umol, Intermediate BEH) and DIPEA (180 mg, 1.39 mmol, 242 uL) in DMF (1 mL) was added 6-(trifluoromethyl)pyridine-2-carboxylic acid (133 mg, 696 umol, CAS #131747-42-7) and CMPI (213 mg, 835 umol) in DMF (1 mL). The reaction mixture was stirred at 25° C. for 2 hrs. On completion, the reaction mixture was diluted with water (10 mL), then extracted with EA (3×10 mL). The combined organic layers were washed with brine (2×10 mL), dried over $Na_2SO_4$, filtered and concentrated in vacuo. The residue was purified by silica gel chromatography (PE:EA=2:1) to give the title compound (320 mg, 71% yield) as obtained brown solid. $^1H$ NMR (400 MHz, DMSO-$d_6$) δ 11.25 (s, 1H), 8.75 (s, 1H), 8.52-8.48 (m, 1H), 8.41 (t, J=7.6 Hz, 1H), 8.24-8.19 (m, 1H), 7.68 (s, 1H), 4.45 (t, J=5.2 Hz, 1H), 3.53 (d, J=6.8 Hz, 2H), 3.27 (t, J=5.8 Hz, 2H), 2.98-2.84 (m, 3H), 2.78 (t, J=10.8 Hz, 2H), 2.20-2.11 (m, 2H), 1.86 (d, J=12.8 Hz, 3H), 1.81-1.79 (m, 1H), 1.68-1.49 (m, 3H), 1.47-1.35 (m, 3H), 1.07 (m, 2H), 0.89 (s, 9H), 0.07 (s, 6H).

Step 2—N-[5-[4-[[tert-butyl(dimethyl)silyl]oxymethyl]-1-piperidyl]-2-(4-formylcyclohexyl)-1,3- benzoxazol-6-yl]-6-(trifluoromethyl)pyridine-2-carboxamide To a solution of N-[5-[4-[[tert-butyl(dimethyl)silyl]oxymethyl]-1-piperidyl]-2-[4-(hydroxymethyl)cyclohexyl]-1,3-benzoxazol-6-yl]-6-(trifluoromethyl)pyridine-2-carboxamide (60.0 mg, 92.7 umol) in DCM (0.5 mL) was added DMP (51.1 mg, 120 umol). The reaction mixture was stirred at 25° C. for 2 hours. On completion, the reaction mixture was quenched by sat. aq. $Na_2S_2O_3$ (1 mL), then acidified by sat.aq. $NaHCO_3$ until the pH=7~8. The reaction mixture was diluted with water (10 mL) and extracted with DCM (3×10 mL). The combined organic layers were washed with brine (2×10 mL), dried over $Na_2SO_4$, filtered and concentrated in vacuo to the title compound (48.0 mg, 80% yield) as brown solid. $^1H$ NMR (400 MHz, $CDCl_3$) δ 11.30 (s, 1H), 9.61 (d, J=0.8 Hz, 1H), 8.78 (s, 1H), 8.45 (d, J=7.6 Hz, 1H), 8.04 (t, J=7.6 Hz, 1H), 7.79 (dd, J=0.8, 7.6 Hz, 1H), 7.46 (s, 1H), 3.48 (d, J=6.8 Hz, 2H), 2.96 (d, J=11.2 Hz, 2H), 2.84 (m, 1H), 2.66 (t, J=10.8 Hz, 2H), 2.32-2.21 (m, 3H), 2.15-2.06 (m, 2H), 1.81 (m, 2H), 1.73-1.55 (m, 3H), 1.45-1.32 (m, 4H), 1.16 (m, 1H), 0.83 (s, 9H), 0.00 (s, 6H).

6-(2-Fluoropropan-2-yl)-N-(2-((1R,4R)-4-formylcyclohexyl)-6-methoxy-7-methyl-2H-inda zol-5-yl) picolinamide (Intermediate BEJ)

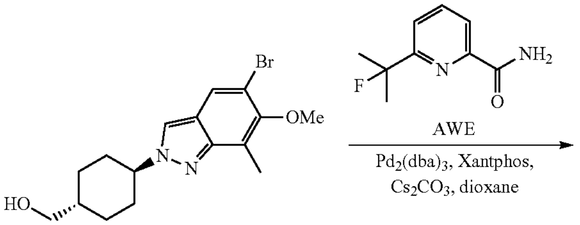

BDJ

-continued

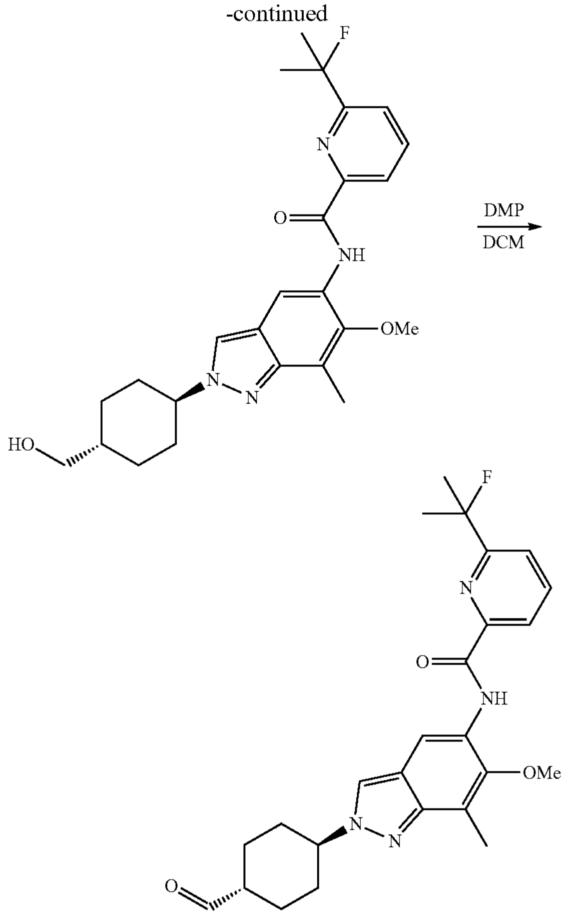

BEJ

Step 1—6-(2-Fluoropropan-2-yl)-N-(2-((1R, 4R)-4-(hydroxymethyl)cyclohexyl)-6-methoxy-7-methyl -2H-indazol-5-yl)picolinamide To a solution of [4-(5-bromo-6-methoxy-7-methyl-indazol-2-yl)cyclohexyl]methanol (150 mg, 424 umol, Intermediate BDJ) and 6-(1-fluoro-1-methyl-ethyl)pyridine-2-carboxamide (85.1 mg, 467 umol, Intermediate AWE) in dioxane (1.5 mL) was added $Pd_2(dba)_3$ (38.8 mg, 42.4 umol), $Cs_2CO_3$ (276 mg, 849 umol) and Xantphos (49.1 mg, 84.9 umol). The mixture was stirred at 80° C. for 12 hours. On completion, the reaction mixture was filtered and concentrated in vacuo to give a residue. The residue was purified by prep-TLC ($SiO_2$, PE:EA=1:1) to give the title compound (180 mg, 88% yield) as an off-white solid. LC-MS ($ESI^+$) m/z 455.3 $(M+H)^+$.

Step 2—6-(2-Fluoropropan-2-yl)-N-(2-((1R,4R)-4-formylcyclohexyl)-6-methoxy-7-methyl-2H-inda zol-5-yl)picolinamide To a solution of 6-(1-fluoro-1-methyl-ethyl)-N-[2-[4-(hydroxymethyl)cyclohexyl]-6-methoxy-7- methyl-indazol-5-yl]pyridine-2-carboxamide (180 mg, 396 umol) in DCM (2.0 mL) was added DMP (218 mg, 514 umol) at 0° C. Then the mixture was stirred at 25° C. for 0.5 hour. On completion, the reaction mixture was quenched with sat. $Na_2SO_3$ (20 mL) and sat. $NaHCO_3$ (20 mL) at 0° C., and then diluted with $H_2O$ (20 mL), and the mixture was extracted with DCM (3×50 mL). The combined organic layers were washed with brine (50 mL), dried over $Na_2SO_4$, filtered and concentrated in vacuo to give the title compound (170 mg, 94% yield) as an off-white solid. LC-MS ($ESI^+$) m/z 453.4 $(M+H)^+$.

2-(2-Methyl-4-pyridyl)oxazole-4-carboxylic acid (Intermediate MO)

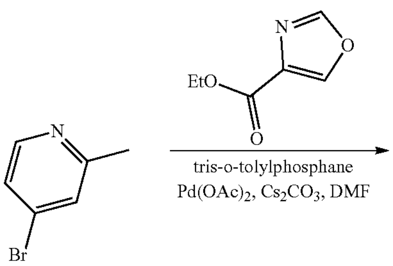

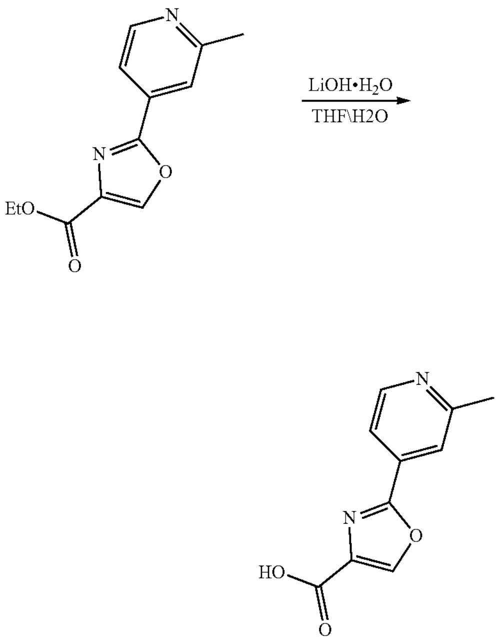

MO

Step 1—Ethyl 2-(2-methylpyridin-4-yl)oxazole-4-carboxylate

To a solution of 4-bromo-2-methyl-pyridine (1.50 g, 8.72 mmol, from CAS #22282-99-1) and ethyl oxazole-4-carboxylate (1.23 g, 8.72 mmol, from CAS #170487-38-4) in DMF (40 mL) was added tris-o-tolylphosphane (531 mg, 1.74 mmol), $Pd(OAc)_2$ (196 mg, 872 umol) and $Cs_2CO_3$ (5.68 g, 17.4 mmol). The reaction mixture was stirred at 70° C. for 12 hours under nitrogen. On completion, the reaction mixture was filtered and concentrated. The residue was purified by silica gel column chromatography to give the title compound (1.10 g, 44% yield) as a yellow solid. $^1H$ NMR (400 MHz, $CDCl_3$) δ 8.65 (d, J=5.2 Hz, 1H), 8.31-8.36 (m, 1H), 7.86 (s, 1H), 7.75 (d, J=5.2 Hz, 1H), 4.44 (q, J=7.2 Hz, 2H), 2.64 (s, 3H), 1.41 (t, J=7.2 Hz, 3H); LC-MS ($ESI^+$) m/z 233.1 $(M+H)^+$.

Step 2—2-(2-Methyl-4-pyridyl)oxazole-4-carboxylic acid

To a solution of ethyl 2-(2-methyl-4-pyridyl)oxazole-4-carboxylate (1.10 g, 4.74 mmol) in THE (20 mL) was added $LiOH.H_2O$ (795 mg, 19.0 mmol) in $H_2O$ (4 mL). The reaction mixture was stirred at rt for 12 hours. On completion, the reaction mixture was filtered and the filter cake was dissolved in water (20 mL). The solution was acidified to pH=4 and filtered. The filter cake was washed with water (2×5 mL) and dried in vacuo. The residue was purified by prep-HPLC to give the title compound (600 mg, 52% yield) as a white solid.

2-(2-Methyl-4-pyridyl)oxazole-4-carboxamide (Intermediate BEK)

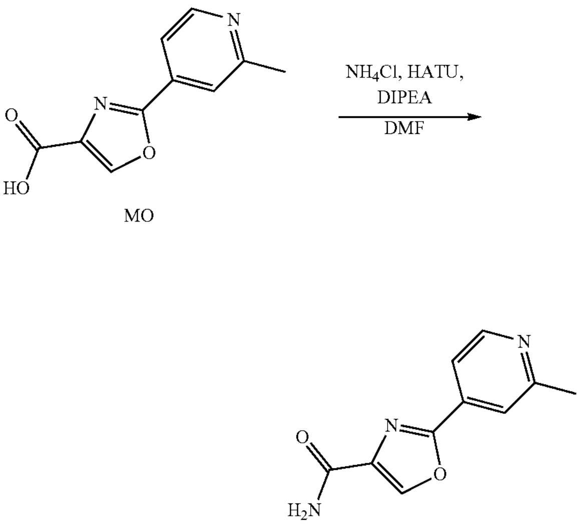

MO

BEK

To a solution of 2-(2-methyl-4-pyridyl)oxazole-4-carboxylic acid (500 mg, 2.45 mmol, Intermediate MO), $NH_4Cl$ (785 mg, 14.6 mmol) and HATU (1.21 g, 3.18 mmol) in DMF (10 mL) was added DIPEA (3.16 g, 24.4 mmol). The reaction mixture was stirred at 25° C. for 1 hour. On completion, the reaction mixture was diluted with water (100 mL) and extracted with EA (3×100 mL). The combined organic layers were dried over $Na_2SO_4$, filtered and concentrated in vacuo to give a residue. The residue was purified by silica gel chromatography (PE:EA=1:1) to give the title compound (0.33 g, 66% yield) as white solid. $^1H$ NMR (400 MHz, DMSO-$d_6$) δ 8.80-8.77 (m, 1H), 8.66 (d, J=5.2 Hz, 1H), 7.81 (s, 1H), 7.78 (s, 1H), 7.74-7.71 (m, 1H), 7.63 (s, 1H), 2.57 (s, 3H).

N-[2-(4-formylcyclohexyl)-6-methoxy-indazol-5-yl]-2-(2-methyl-4-pyridyl)oxazole-4-carboxamide (Intermediate BED)

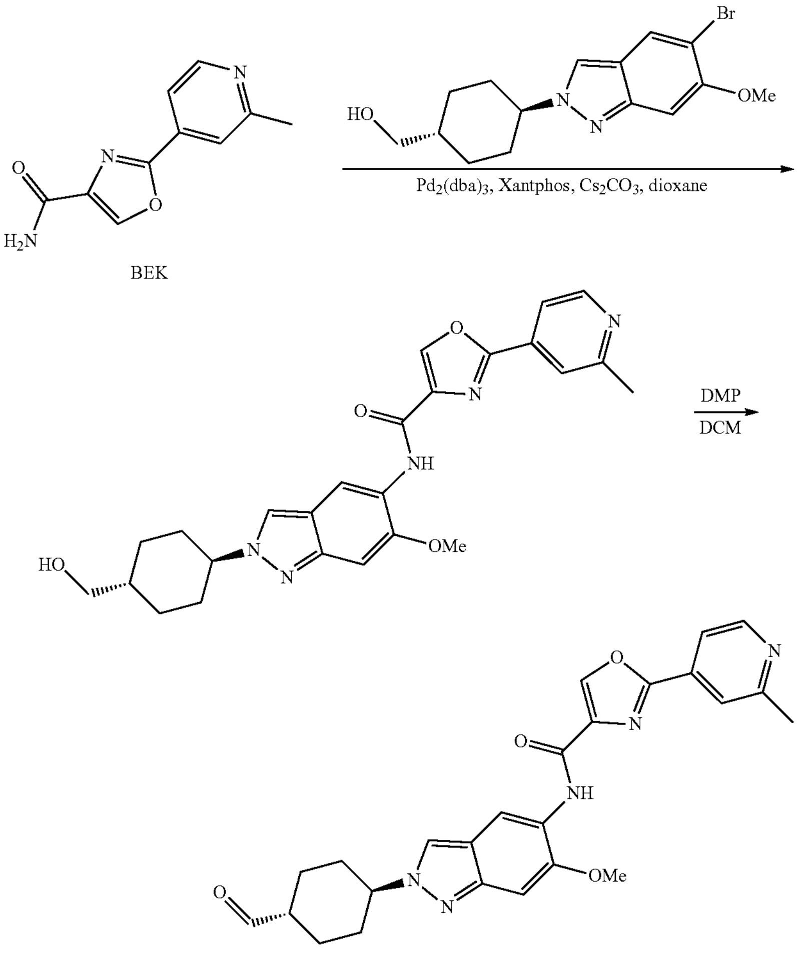

BEK

BEL

Step 1—N-[2-[4-(hydroxymethyl)cyclohexyl]-6-methoxy-indazol-5-yl]-2-(2-methyl-4-pyridyl)oxazole-4-carboxamide A mixture of [4-(5-bromo-6-methoxy-indazol-2-yl)cyclohexyl]methanol (300 mg, 884 umol, synthesized via Steps 1-3 of Intermediate ATE), 2-(2-methyl-4-pyridyl)oxazole-4-carboxamide (233 mg, 1.15 mmol, Intermediate BEK), $Pd_2(dba)_3$ (80.9 mg, 88.4 umol), Xantphos (102 mg, 176 umol) and $Cs_2CO_3$ (576 mg, 1.77 mmol) in dioxane (8 mL) was stirred at 80° C. for 12 hours under $N_2$. On completion, the reaction mixture was diluted with water (100 ml) and extracted with EA (3×100 mL). The combined organic layers were washed with brine (2×50 mL), dried over $Na_2SO_4$, filtered and concentrated in vacuo. The crude product was purified by reversed-phase (0.1% FA) to give the title compound (30.0 mg, 7% yield) as white solid. $^1H$ NMR (400 MHz, DMSO-$d_6$) δ 9.52 (s, 1H), 9.06-9.01 (m, 1H), 8.71-8.67 (m, 1H), 8.57-8.51 (m, 1H), 8.32 (s, 1H), 7.89-7.83 (m, 1H), 7.82-7.76 (m, 1H), 7.18-7.11 (m, 1H), 4.52-4.46 (m, 1H), 4.03-3.99 (m, 3H), 3.26 (s, 2H), 2.61 (s, 3H), 2.13 (d, J=12.0 Hz, 2H), 1.94-1.83 (m, 4H), 1.53-1.41 (m, 1H), 1.54-1.40 (m, 1H).

Step 2—N-[2-(4-formylcyclohexyl)-6-methoxy-indazol-5-yl]-2-(2-methyl-4-pyridyl)oxazole-4-carbox amide To a mixture of N-[2-[4-(hydroxymethyl)cyclohexyl]-6-methoxy-indazol-5-yl]-2-(2-methyl-4-pyridyl) oxazole-4-carboxamide (40.0 mg, 86.6 umol) in DCM (1 mL) was added DMP (47.7 mg, 112 umol). The reaction mixture was stirred at 25° C. for 3 hours. On completion, the reaction mixture was quenched with sat. aq. $Na_2S_2O_3$ (0.1 mL), then acidified with sat. aq. $NaHCO_3$ until the pH=7~ 8. The reaction mixture was diluted with water (10 mL) and extracted with DCM (3×10 mL). The combined organic layers were dried over $Na_2SO_4$, filtered and concentrated in vacuo to give the title compound (38.0 mg, 95% yield) as brown solid. $^1H$ NMR (400 MHz, DMSO-$d_6$) δ 9.65-9.63 (m, 1H), 9.54-9.51 (m, 1H), 9.05 (s, 1H), 8.70 (d, J=5.2 Hz, 1H), 8.55 (s, 1H), 8.33 (s, 1H), 7.87 (s, 1H), 7.80 (d, J=5.2 Hz, 1H), 7.15 (s, 1H), 4.44-4.35 (m, 1H), 4.02 (s, 3H), 2.61 (s, 3H), 2.25-2.04 (m, 5H), 1.99-1.91 (m, 2H), 1.45 (m, 2H).

2-(((((2S,4s,7S)-7-((tert-butoxycarbonyl)(methyl)amino)spiro[3.5]nonan-2-yl)methyl)-12-azaneyl)carbonyl)benzoic acid (Intermediate BCO) and 2-(((((2R,4r,7R)-7-((tert-butoxycarbonyl)(methyl)amino)spiro[3.5]nonan-2-yl)methyl)-12-azaneyl)carbonyl)benzoic acid (Intermediate BCP)

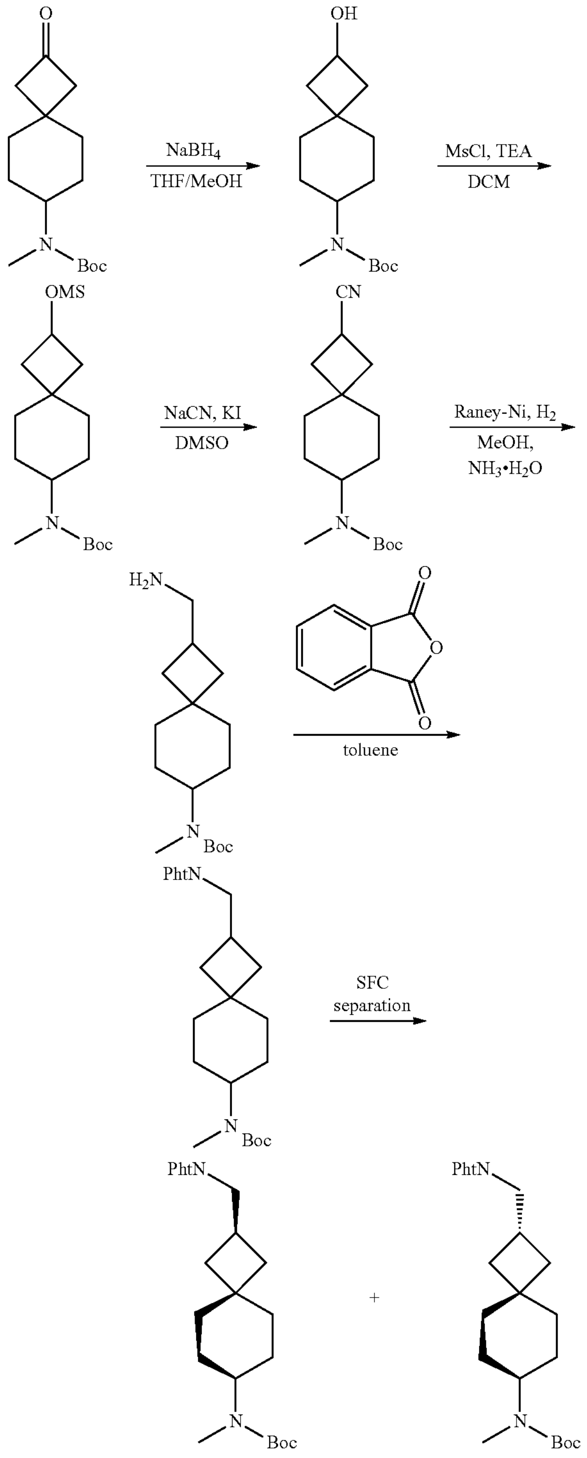

BCO BCP

Step 1—Tert-butyl N-(2-hydroxyspiro[3.5]nonan-7-yl)-N-methyl-carbamate

To a solution of tert-butyl N-methyl-N-(2-oxospiro[3.5]nonan-7-yl)carbamate (12.0 g, 44.8 mmol, synthesized via Steps 1-5 of Intermediate ANJ) in a mixed solvents of THF (100 mL) and MeOH (30 mL) was added $NaBH_4$ (1.87 g, 49.3 mmol) at 0° C. The reaction mixture was stirred at 0° C. for 1 hour. On completion, the reaction mixture was quenched with sat. aq. $NH_4Cl$ (30 mL), diluted with water (100 mL) and extracted with EA (3×200 mL). The combined organic layers were washed with brine (2×60 mL), dried over $Na_2SO_4$, filtered and concentrated in vacuo to give the title compound (11.5 g, 95% yield) as yellow oil. $^1H$ NMR (400 MHz, $CDCl_3$) δ 4.38-4.20 (m, 1H), 4.03-3.52 (m, 1H), 2.70 (s, 3H), 2.39-2.25 (m, 1H), 2.20-2.08 (m, 1H), 1.74-1.62 (m, 4H), 1.61-1.49 (m, 4H), 1.49-1.38 (m, 12H).

Step 2—[7-[Tert-butoxycarbonyl(methyl)amino]spiro[3.5]nonan-2-yl]methanesulfonate To a solution of tert-butyl N-(2-hydroxyspiro[3.5]nonan-7-yl)-N-methyl-carbamate (15.5 g, 57.5 mmol) and TEA (8.73 g, 86.3 mmol) in DCM (150 mL) was added MsCl (7.91 g, 69.0 mmol) at 0° C. The reaction mixture was stirred at 0-20° C. for 1 hour. On completion, the reaction mixture was diluted with water (100 mL) and extracted with DCM (3×100 mL). The combined organic layers were washed with brine (2×60 mL), dried over $Na_2SO_4$, filtered and concentrated in vacuo to give the title compound (19.0 g, 95% yield) as yellow oil. $^1H$ NMR (400 MHz, $CDCl_3$) δ 5.03-4.96 (m, 1H), 4.00-3.59 (m, 1H), 2.98 (s, 3H), 2.70 (s, 3H), 2.53-2.40 (m, 1H), 2.33-2.21 (m, 1H), 2.17-1.93 (m, 2H), 1.75-1.66 (m, 2H), 1.61-1.47 (m, 4H), 1.46 (s, 9H), 1.44-1.34 (m, 2H).

Step 3—Tert-butyl N-(2-cyanospiro[3.5]nonan-7-yl)-N-methyl-carbamate

To a solution of [7-[tert-butoxycarbonyl(methyl)amino]spiro[3.5]nonan-2-yl]methanesulfonate (19.0 g, 54.6 mmol) and KI (13.6 g, 82.0 mmol) in DMSO (200 mL) was added NaCN (4.02 g, 82.0 mmol) at 25° C. The reaction mixture was stirred at 100° C. for 48 hours. On completion, the reaction mixture was poured into water (400 mL), and extracted with EA (3×180 mL). The combined organic layers were washed with brine (2×100 mL), dried over $Na_2SO_4$, filtered and concentrated in vacuo. The residue was purified by silica gel chromatography (PE:EA=20:1) to give the title compound (9.90 g, 65% yield) as white solid. $^1H$ NMR (400 MHz, $CDCl_3$) δ 4.05-3.51 (m, 1H), 3.04-2.97 (m, 1H), 2.69 (s, 3H), 2.31-2.21 (m, 1H), 2.17-2.07 (m, 3H), 1.94-1.84 (m, 1H), 1.82-1.72 (m, 1H), 1.60-1.50 (m, 2H), 1.50-1.46 (m, 1H), 1.45 (s, 9H), 1.44-1.34 (m, 3H).

Step 4—Tert-butyl N-[2-(aminomethyl)spiro[3.5]nonan-7-yl]-N-methyl-carbamate

To a solution of tert-butyl N-(2-cyanospiro[3.5]nonan-7-yl)-N-methyl-carbamate (10.5 g, 37.7 mmol) and $NH_3.H_2O$ (36.4 g, 259 mmol, 40 mL) in MeOH (100 mL) was added Raney-Ni (969 mg, 11.3 mmol). The reaction mixture was stirred at 25° C. for 16 hours under $H_2$ (50 psi). On completion, the reaction mixture was filtered and the filtrate was concentrated in vacuo to give the title compound (10.1 g, 94% yield) as yellow oil. $^1H$ NMR (400 MHz, DMSO-$d_6$) δ 3.88-3.56 (m, 1H), 2.62 (s, 3H), 2.55-2.51 (m, 2H), 2.26-2.04 (m, 1H), 1.95-1.74 (m, 2H), 1.72-1.63 (m, 1H), 1.62-1.40 (m, 4H), 1.38 (s, 9H), 1.37-1.22 (m, 5H).

Step 5—Tert-butyl N-[2-[(1,3-dioxoisoindolin-2-yl) methyl]spiro[3.5]nonan-7-yl]-N-methyl- carbamate A mixture of tert-butyl N-[2-(aminomethyl)spiro[3.5] nonan-7-yl]-N-methyl-carbamate (9.80 g, 34.7 mmol) and isobenzofuran-1,3-dione (6.17 g, 41.6 mmol, CAS #85-44-9) in toluene (100 mL) was stirred at 110° C. for 12 hours. On completion, the reaction mixture was concentrated in vacuo. The residue was purified by silica gel chromatography (PE:EA=20:1) to give the title compound (11.6 g, 80% yield) as white solid. $^1$H NMR (400 MHz, $CDCl_3$) δ 7.84 (dd, J=3.2, 5.6 Hz, 2H), 7.72 (dd, J=3.2, 5.6 Hz, 2H), 3.98-3.53 (m, 3H), 2.73-2.57 (m, 4H), 2.00-1.89 (m, 1H), 1.85-1.75 (m, 2H), 1.73-1.64 (m, 1H), 1.64-1.59 (m, 1H), 1.59-1.46 (m, 4H), 1.45 (s, 9H), 1.43-1.34 (m, 3H).

Step 6—2-(((((2S,4s,7S)-7-((tert-butoxycarbonyl) (methyl)amino)spiro[3.5]nonan-2-yl)methyl)-12-azaneyl)carbonyl)benzoic acid (Intermediate BCO) and 2-(((((2R,4r,7R)-7-((tert-butoxycarbonyl) (methyl)amino)spiro[3.5]nonan-2-yl)methyl)-12-azaneyl)carbonyl)benzoic acid Racemic tert-butyl N-[2-[(1,3-dioxoisoindolin-2-yl) methyl]spiro[3.5]nonan-7-yl]-N-methyl- carbamate was separated by SFC ((column: DAICEL CHIRALCEL OJ-H (250 mm*30 mm, Sum); mobile phase: [0.1% $NH_3.H_2O$ ETOH]) to give the two title compound. The first peak 2-(((((2S,4s,7S)-7-((tert-butoxycarbonyl)(methyl)amino) spiro[3.5]nonan-2-yl)methyl)-12-azaneyl)carbonyl)benzoic acid (4.80 g, 96% yield, 99% ee) was obtained as colorless gum. $^1$H NMR (400 MHz, $CDCl_3$) δ 7.84 (dd, J=3.2, 5.6 Hz, 2H), 7.72 (dd, J=3.2, 5.6 Hz, 2H), 3.97-3.62 (m, 3H), 2.75-2.57 (m, 4H), 2.00-1.90 (m, 1H), 1.86-1.74 (m, 2H), 1.72-1.64 (m, 1H), 1.63-1.54 (m, 2H), 1.54-1.46 (m, 3H), 1.45 (s, 9H), 1.43-1.33 (m, 3H); LC-MS ($ESI^+$) m/z 357.2 $(M+H-56)^+$. The second peak 2-(((((2R,4r,7R)-7-((tert-butoxycarbonyl)(methyl)amino)spiro[3.5]nonan-2-yl)methyl)-12-azaneyl)carbonyl)benzoic acid (4.90 g, 97% yield, 96.4% ee) was obtained as colorless gum. $^1$H NMR (400 MHz, $CDCl_3$) δ 7.85 (dd, J=3.2, 5.6 Hz, 2H), 7.72 (dd, J=3.2, 5.6 Hz, 2H), 3.94-3.62 (m, 3H), 2.76-2.55 (m, 4H), 2.01-1.90 (m, 1H), 1.86-1.74 (m, 2H), 1.72-1.65 (m, 1H), 1.64-1.59 (m, 1H), 1.55-1.47 (m, 3H), 1.45 (s, 9H), 1.44-1.32 (m, 4H); LC-MS ($ESI^+$) m/z 357.2 $(M+H-56)^+$. Stereochemistry was assigned arbitrarily.

Tert-butyl N-[2-(aminomethyl)spiro[3.5]nonan-7-yl]-N-methyl-carbamate (Intermediate BCQ)

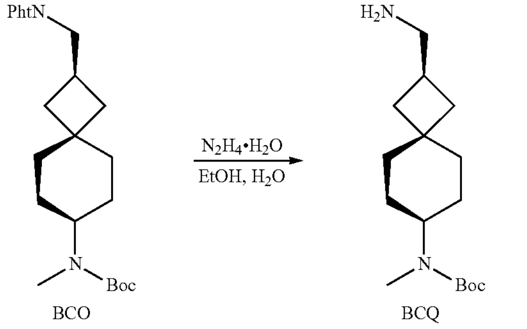

To a solution of tert-butyl N-[2-[(1,3-dioxoisoindolin-2-yl)methyl]spiro[3.5]nonan-7-yl]-N-methyl- carbamate (450 mg, 1.09 mmol, Intermediate BCO) in EtOH (4 mL) was added $N_2H4H_2O$ (222 mg, 4.36 mmol). The reaction mixture was stirred at 80° C. for 2 hours. On completion, the reaction mixture was concentrated in vacuo. The residue was diluted with DCM (100 mL) and filtered in vacuo. The filtrate was concentrated in vacuo to give the title compound (290 mg, 94% yield) as colorless oil. $^1$H NMR (400 MHz, $CDCl_3$) δ 2.69 (s, 3H), 2.67 (s, 1H), 2.23 (m, 1H), 1.95 (m, 1H), 1.88-1.74 (m, 2H), 1.64-1.46 (m, 4H), 1.45 (s, 9H), 1.44-1.23 (m, 8H).

2-(2,6-Dioxo-3-piperidyl)-4-[[7-(methylamino)spiro [3.5]nonan-2-yl]methylamino]isoindoli ne-1,3-dione (Intermediate BCR)

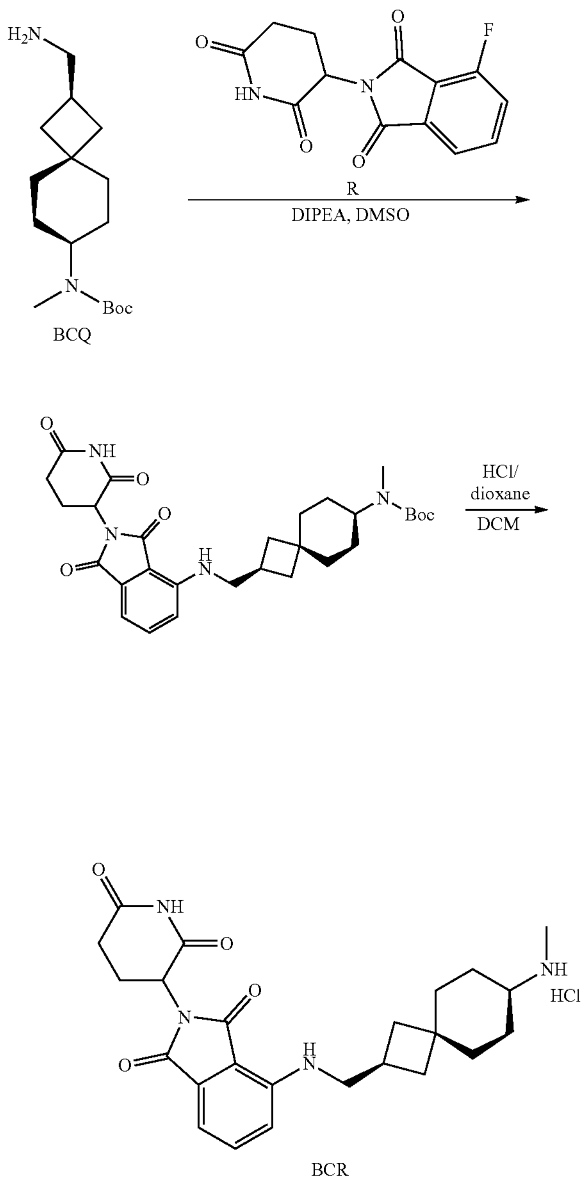

Step 1—Tert-butyl N-[2-[[[2-(2,6-dioxo-3-piperidyl)-1,3-dioxo-isoindolin-4-yl]amino]methyl] spiro [3.5]nonan-7-yl]-N-methyl-carbamate To a solution of 2-(2,6-dioxo-3-piperidyl)-4-fluoro-isoindoline-1,3-dione (283 mg, 1.03 mmol, Intermediate R) and tert-butyl N-[2-(aminomethyl)spiro[3.5]nonan-7-yl]-N-methyl-carbamate (290 mg, 1.03 mmol, Intermediate BCQ) in DMSO (3 mL) was added DIPEA (663 mg, 5.13 mmol). The reaction mixture was stirred at 130° C. for 3 hours. On completion, the reaction mixture was filtered and the filtrate was purified by reversed-phase (0.1% FA) to give the title compound (300 mg, 52% yield) as yellow solid. $^1H$ NMR (400 MHz, $CDCl_3$) δ 8.03-7.97 (m, 1H), 7.50 (dd, J=7.2, 8.4 Hz, 1H), 7.10 (d, J=7.2 Hz, 1H), 6.88 (d, J=8.4 Hz, 1H), 6.19 (t, J=5.2 Hz, 1H), 4.96-4.89 (m, 1H), 4.02-3.59 (m, 1H), 3.35-3.20 (m, 2H), 2.92-2.84 (m, 1H), 2.84-2.79 (m, 1H), 2.78-2.74 (m, 1H), 2.70 (s, 3H), 2.55 (m, 1H), 2.18-2.04 (m, 2H), 1.94-1.83 (m, 2H), 1.66-1.62 (m, 1H), 1.58 (d, m, 2H), 1.56-1.52 (m, 2H), 1.46 (s, 9H), 1.45-1.35 (m, 3H).

Step 2—2-(2,6-Dioxo-3-piperidyl)-4-[[7-(methylamino)spiro[3.5]nonan-2-yl]methylamino]isoindoline-1,3-dione To a solution of tert-butyl N-[2-[[[2-(2,6-dioxo-3-piperidyl)-1,3-dioxo-isoindolin-4-yl]amino]methyl]spiro [3.5] nonan-7-yl]-Nmethyl-carbamate (290 mg, 538 umol) in DCM (2.5 mL) was added HCl/dioxane (4 M, 2.5 mL). The reaction mixture was stirred at 25° C. for 2 hours. On completion, the reaction mixture was concentrated in vacuo to give the title compound (200 mg, 78% yield, HCl) as yellow solid. LCMS ($ESI^+$) m/z 439.2 $(M+H)^+$.

N-[2-(4-formylcyclohexyl)-6-methoxy-indazol-5-yl]-6-(pentafluoro-sulfanyl)pyridine-2- carboxamide (Intermediate BEM)

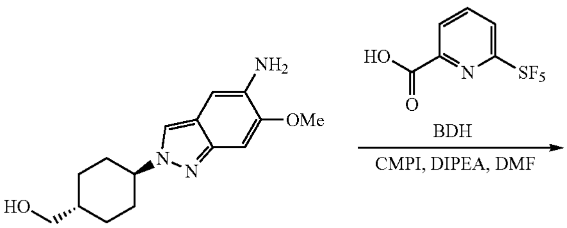

ATE

-continued

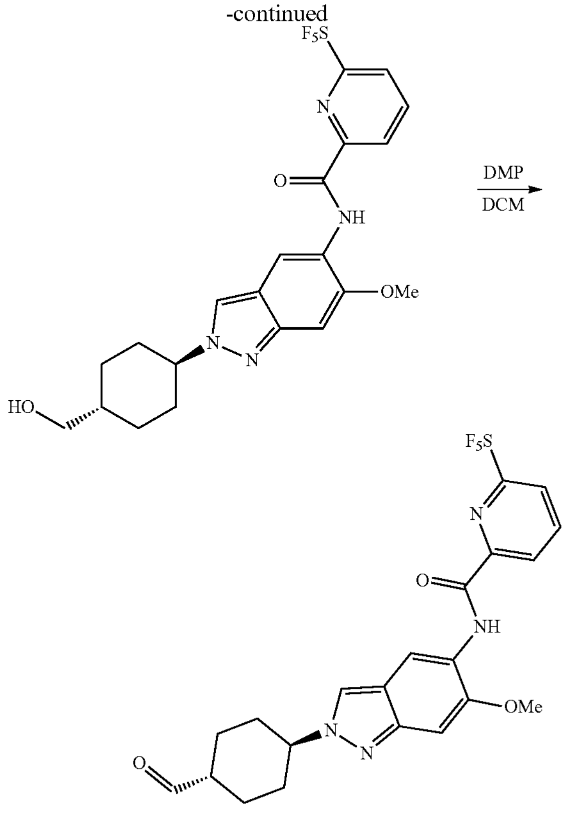

BEM

Step 1—N-[2-[4-(hydroxymethyl)cyclohexyl]-6-methoxy-indazol-5-yl]-6-(pentafluoro-sulfanyl)pyridine-2-carboxamide To a solution of [4-(5-amino-6-methoxy-indazol-2-yl)cyclohexyl]methanol (50.0 mg, 181 umol, Intermediate ATE) and 6-(pentafluoro-sulfanyl)pyridine-2-carboxylic acid (45.2 mg, 181 umol, Intermediate BDH) in DMF (1 mL) was added CMPI (60.3 mg, 236 umol) and DIPEA (70.4 mg, 544 umol). The mixture was stirred at 25° C. for 0.5 hour. On completion, the reaction mixture was diluted with $H_2O$ (50 mL) and DCM (50 mL), and partitioned. The organic phase was washed with brine (50 mL), dried over $Na_2SO_4$, filtered and concentrated in vacuo to give the title compound (90.0 mg, 97% yield) as an off-white solid. LC-MS ($ESI^+$) m/z 507.3 $(M+H)^+$.

Step 2—N-[2-(4-formylcyclohexyl)-6-methoxy-indazol-5-yl]-6-(pentafluoro-sulfanyl)pyridine-2-carboxamide To a solution of N-[2-[4-(hydroxymethyl)cyclohexyl]-6-methoxy-indazol-5-yl]-6-(pentafluoro- sulfanyl)pyridine-2-carboxamide (90.0 mg, 177 umol) in DCM (1 mL) was added DMP (97.9 mg, 231 umol) at 0° C. The mixture was stirred at 25° C. for 0.5 hour. On completion, the reaction mixture was quenched with addition sat. aq. $NaS_2O_3$ (20 mL) and sat. aq. $NaHCO_3$ (20 mL) at 0° C. Then mixture was extracted with DCM (3×50 mL). The combined organic layer was washed with brine (50 mL), dried over $Na_2SO_4$, filtered and concentrated in vacuo. The residue was purified by prep-TLC ($SiO_2$, PE:EA=1:1) to give the title compound (68.0 mg, 75% yield) as an off-white solid. LC-MS ($ESI^+$) m/z 505.2 $(M+H)^+$.

N-(2-((1r,4r)-4-formylcyclohexyl)-6-(2-hydroxypropan-2-yl)-2H-indazol-5-yl)pyrazine-2-carboxamide (Intermediate BEN)

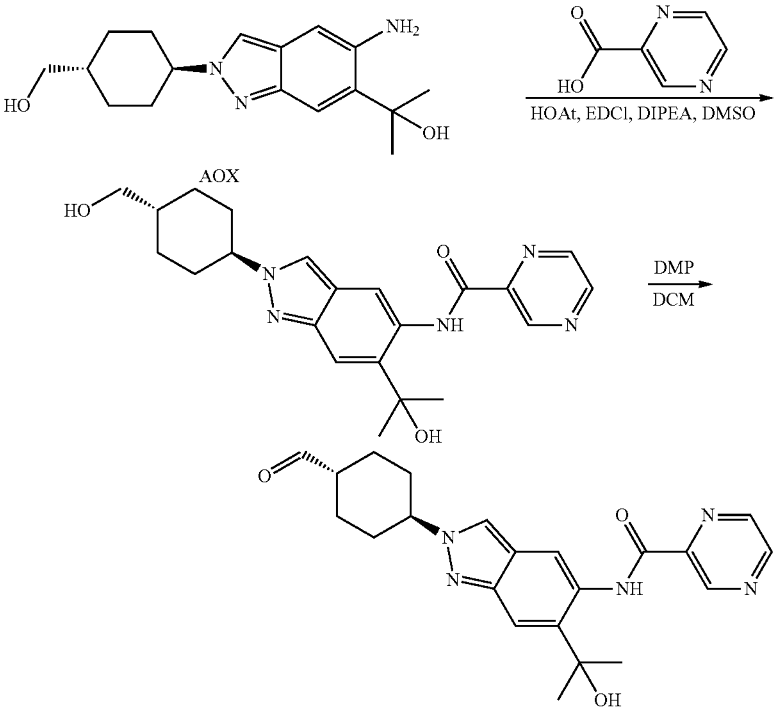

AOX

BEN

Step 1—N-(2-((1r,4r)-4-(hydroxymethyl)cyclohexyl)-6-(2-hydroxypropan-2-yl)-2H-indazol-5-yl) pyrazine-2-carboxamide A mixture of 2-[5-amino-2-[4-(hydroxymethyl)cyclohexyl]indazol-6-yl]propan-2-ol (0.40 g, 1.32 mmol, Intermediate AOX), pyrazine-2-carboxylic acid (245 mg, 1.98 mmol, CAS #98-97-5), HOAt (269 mg, 1.98 mmol), EDCI (379 mg, 1.98 mmol) and DIPEA (852 mg, 6.59 mmol) in DMSO (5 mL) was stirred at 20° C. for 1 h. On completion, the reaction mixture was concentrated in vacuo to give a residue. The residue was purified by reverse phase flash (0.1% FA) to give the title compound (0.28 g, 52% yield) as a white solid. LC-MS ($ESI^+$) m/z 410.1 $(M+H)^+$. $^1H$ NMR (400 MHz, DMSO-$d_6$) δ 9.35 (d, J=1.2 Hz, 1H), 8.92 (d, J=2.4 Hz, 1H), 8.83-8.76 (m, 1H), 8.70 (s, 1H), 8.37 (s, 1H), 7.58 (s, 1H), 6.15 (s, 1H), 4.49 (t, J=5.2 Hz, 1H), 4.45-4.36 (m, 1H), 3.89 (s, 1H), 3.31-3.27 (m, 2H), 2.14 (d, J=9.2 Hz, 2H), 1.92-1.89 (m, 4H), 1.62 (s, 6H), 1.56-1.41 (m, 1H), 1.24-1.09 (m, 2H).

Step 2—N-(2-((1r,4r)-4-formylcyclohexyl)-6-(2-hydroxypropan-2-yl)-2H-indazol-5-yl)pyrazine-2-carboxamide To a solution of N-[2-[4-(hydroxymethyl)cyclohexyl]-6-(1-hydroxy-1-methyl-ethyl)indazol-5-yl]pyrazine-2-carboxamide (0.27 g, 659 umol) in DCM (30 mL) was added DMP (447 mg, 1.05 mmol) at 0° C. The reaction mixture was stirred at 0-20° C. for 12 h. On completion, the reaction mixture was quenched by addition sat. $Na_2S_2O_3$ aq. (20 mL) and sat. $NaHCO_3$ (52 mL) was added. The reaction mixture was extracted with DCM (3×13 mL). The combined organic layers were washed with brine (2×50 mL), dried over $Na_2SO_4$, filtered and concentrated in vacuo to give the title compound (0.26 g, 90% yield) as a light yellow oil. LC-MS ($ESI^+$) m/z 408.1 $(M+H)^+$. $^1H$ NMR (400 MHz, DMSO-$d_6$) δ 12.36 (s, 1H), 9.65 (s, 1H), 9.35 (s, 1H), 8.92 (d, J=2.4 Hz, 1H), 8.79 (s, 1H), 8.71 (s, 1H), 8.38 (s, 1H), 7.58 (s, 1H), 6.15 (s, 1H), 4.49-4.44 (m, 1H), 2.44-2.41 (m, 1H), 2.28-2.06 (m, 4H), 2.01-1.97 (m, 2H), 1.60 (s, 6H), 1.47-1.43 (m, 2H).

N-[2-(4-formylcyclohexyl)-5-methoxy-1,3-benzoxazol-6-yl]pyrazolo[1,5-a]pyrimidine-3-carboxamide (Intermediate BEO)

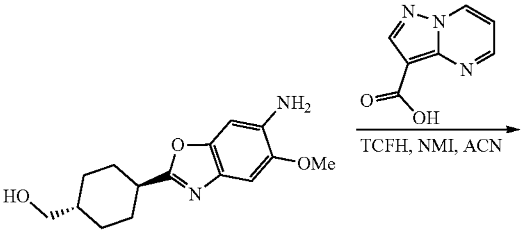

AZR

-continued

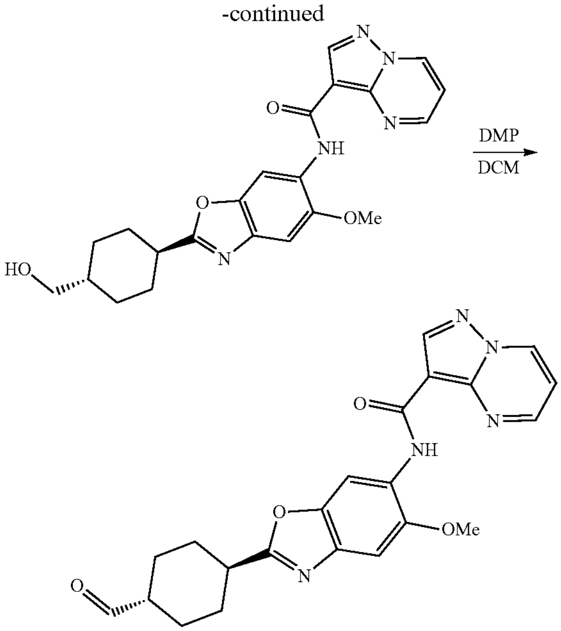

BEO

Step 1—N-[2-[4-(hydroxymethyl)cyclohexyl]-5-methoxy-1,3-benzoxazol-6-yl]pyrazolo[1,5-a]pyrimidine-3-carboxamide To a solution of pyrazolo[1,5-a]pyrimidine-3-carboxylic acid (180 mg, 1.10 mmol, CAS #25940-35-6), 1-methylimidazole (317 mg, 3.86 mmol) and [chloro(dimethylamino)methylene]-dimethyl-ammonium;hexafluorophosphate (371 mg, 1.32 mmol) in ACN (15 mL) was added [4-(6-amino-5-methoxy-1,3-benzoxazol-2-yl)cyclohexyl]methanol (304 mg, 1.10 mmol, Intermediate AZR). The mixture was stirred at 15° C. for 1.5 hrs. On completion, the reaction mixture was quenched with water (0.3 mL) and filtered to give the title compound (330 mg, 71% yield) as yellow solid. $^1$H NMR (400 MHz, DMSO-$d_6$) δ 10.59 (s, 1H), 9.38 (dd, J=1.2, 6.8 Hz, 1H), 8.95 (dd, J=1.2, 4.0 Hz, 1H), 8.74-8.68 (m, 2H), 7.42-7.39 (m, 1H), 7.35 (dd, J=4.4, 7.2 Hz, 1H), 4.46 (t, J=5.2 Hz, 1H), 4.02 (s, 3H), 3.26 (t, J=6.0 Hz, 2H), 2.87 (tt, J=3.6, 12.0 Hz, 1H), 2.22-2.11 (m, 2H), 1.86 (d, J=10.8 Hz, 2H), 1.60-1.50 (m, 2H), 1.44-1.39 (m, 1H), 1.11-1.01 (m, 2H).

Step 2—N-[2-(4-formylcyclohexyl)-5-methoxy-1,3-benzoxazol-6-yl]pyrazolo[1,5-a]pyrimidine-3-carboxamide To a solution of N-[2-[4-(hydroxymethyl)cyclohexyl]-5-methoxy-1,3-benzoxazol-6-yl]pyrazolo[1,5-a] pyrimidine-3-carboxamide (160 mg, 379 umol) in DCM (5 mL) was added DMP (193 mg, 455 umol). The mixture was stirred at 25° C. for 1 hr. On completion, the reaction mixture was diluted with DCM (30 mL), then quenched with saturated $Na_2S_2O_3$ (10 mL) and saturated $NaHCO_3$ (10 mL) at 0° C. The mixture was stirred at 25° C. for 30 minutes. After that, the organic layers were separated and washed with saturated $NaHCO_3$ (10 mL) and saturated NaCl (20 mL). The organic layer was then dried over $Na_2SO_4$, filtered and concentrated in vacuo to give the title compound (140 mg, 90% yield) as yellow solid. $^1$H NMR (400 MHz, DMSO-$d_6$) δ 10.60 (s, 1H), 9.62 (s, 1H), 9.38 (dd, J=1.6, 7.2 Hz, 1H), 8.95 (dd, J=1.6, 4.4 Hz, 1H), 8.73 (d, J=4.8 Hz, 2H), 7.42 (s, 1H), 7.35 (dd, J=4.2, 7.2 Hz, 1H), 4.03 (s, 3H), 2.94 (tt, J=3.6, 11.6 Hz, 1H), 2.44-2.31 (m, 1H), 2.27-2.16 (m, 2H), 2.07-2.01 (m, 2H), 1.65 (dq, J=3.2, 12.4 Hz, 2H), 1.39 (dq, J=3.2, 12.4 Hz, 2H).

3-[3-Methyl-2-oxo-5-[3-(4-piperidyl)propyl]benzimidazol-1-yl]piperidine-2,6-dione (Intermediate BEP)

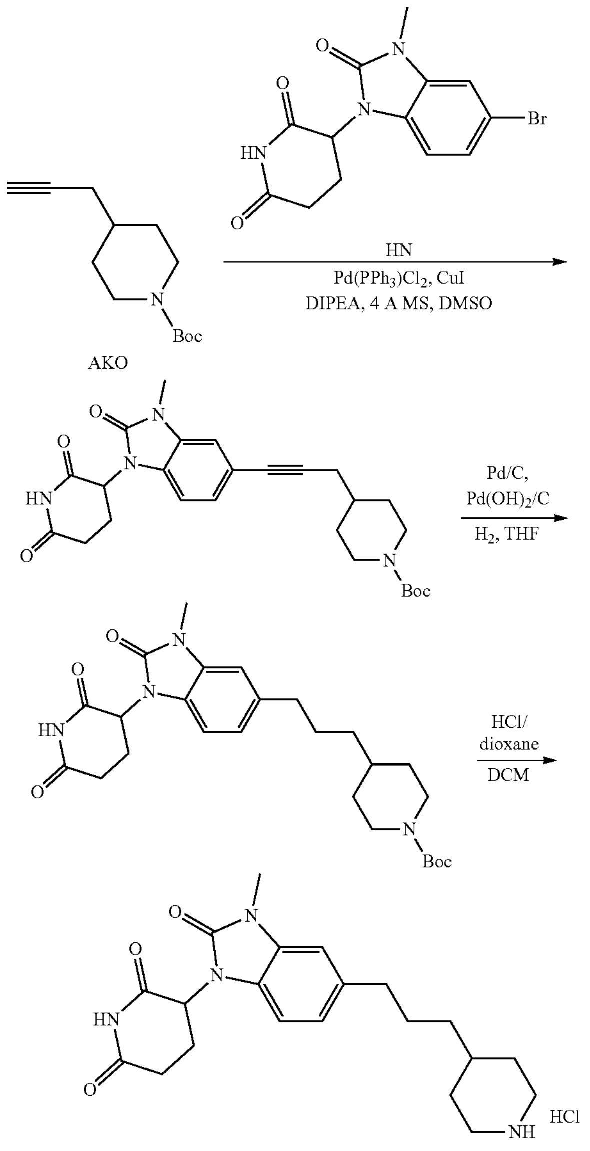

BEP

Step 1—Tert-butyl 4-[3-[1-(2,6-dioxo-3-piperidyl)-3-methyl-2-oxo-benzimidazol-5-yl]prop-2-ynyl]piperidine-1-carboxylate A mixture of 3-(5-bromo-3-methyl-2-oxo-benzimidazol-1-yl)piperidine-2,6-dione (1.00 g, 2.96 mmol, Intermediate HN), tert-butyl 4-prop-2-ynylpiperidine-1-carboxylate (990 mg, 4.44 mmol, Intermediate AKO), $Pd(PPh_3)_2Cl_2$ (415 mg, 591 umol), CuI (112 mg, 591 umol), DIPEA (1.91 g, 14.7 mmol, 2.58 mL) and 4 Å molecular sieves (200 mg, 2.96 mmol) in DMSO (10.0 mL) was degassed and purged with $N_2$ for 3 times, and then the mixture was stirred at 80° C. for 3 hrs under $N_2$ atmosphere. On completion, the reaction mixture was filtered and the filtrate was concentrated in vacuo to give a residue. The residue was purified by reversed phase (0.1% FA condition) to give the title compound (600 mg, 42% yield) as a yellow solid. $^1H$ NMR (400 MHz, $CDCl_3$) δ 8.17 (s, 1H), 7.14 (dd, J=1.6, 8.0 Hz, 1H), 7.06 (d, J=1.2 Hz, 1H), 6.73 (d, J=8.0 Hz, 1H), 5.19 (dd, J=5.2, 12.8 Hz, 1H), 4.27-4.00 (m, 2H), 3.43 (s, 3H), 3.00-2.90 (m, 1H), 2.89-2.78 (m, 1H), 2.78-2.66 (m, 3H), 2.38 (d, J=6.8 Hz, 2H), 2.29-2.20 (m, 1H), 1.82 (d, J=13.2 Hz, 2H), 1.77-1.71 (m, 1H), 1.47 (s, 9H), 1.34-1.23 (m, 2H).

Step 2—Tert-butyl 4-[3-[1-(2,6-dioxo-3-piperidyl)-3-methyl-2-oxo-benzimidazol-5-yl]propyl]piperidine-1-carboxylate To a solution of tert-butyl 4-[3-[1-(2,6-dioxo-3-piperidyl)-3-methyl-2-oxo-benzimidazol-5-yl]prop-2- ynyl]piperidine-1-carboxylate (150 mg, 312 umol) in THE (10.0 mL) was added $Pd(OH)_2/C$ (100 mg, 20% wt) and Pd/C (100 mg, 10% wt) under $N_2$ atmosphere. The suspension was degassed and purged with $H_2$ gas 3 times. The mixture was stirred under $H_2$ (15 psi) at 20° C. for 16 hrs. On completion, the reaction mixture was filtered and concentrated in vacuo to give the title compound (150 mg, 99% yield) as a white solid. $^1H$ NMR (400 MHz, $CDCl_3$) δ 8.32 (s, 1H), 6.88 (dd, J=1.6, 8.0 Hz, 1H), 6.84 (s, 1H), 6.72 (d, J=8.0 Hz, 1H), 5.22 (dd, J=5.2, 12.8 Hz, 1H), 4.07 (s, 2H), 3.43 (s, 3H), 2.97-2.89 (m, 1H), 2.88-2.78 (m, 1H), 2.77-2.67 (m, 2H), 2.66-2.62 (m, 3H), 2.27-2.19 (m, 1H), 1.69-1.65 (m, 2H), 1.64-1.60 (m, 2H), 1.45 (s, 9H), 1.42-1.34 (m, 1H), 1.32-1.26 (m, 2H), 1.13-1.02 (m, 2H).

Step 3—3-[3-Methyl-2-oxo-5-[3-(4-piperidyl)propyl]benzimidazol-1-yl]piperidine-2,6-dione To a solution of tert-butyl 4-[3-[1-(2,6-dioxo-3-piperidyl)-3-methyl-2-oxo-benzimidazol-5-yl]propyl]piperidine-1-carboxylate (150 mg, 309 umol) in DCM (5 mL) was added HCl/dioxane (4 M, 3 mL). The mixture was stirred at 25° C. for 1 hr. On completion, the reaction mixture was concentrated in vacuo to give the title compound (130 mg, 99% yield, HCl) as a white solid. LC-MS ($ESI^+$) m/z 385.2 $(M+H)^+$.

3-(3-Methyl-5-(3-(methylamino)prop-1-yn-1-yl)-2-oxo-2,3-dihydro-1H-benzo[d]imidazol-1- yl)piperidine-2,6-dione (Intermediate BEQ)

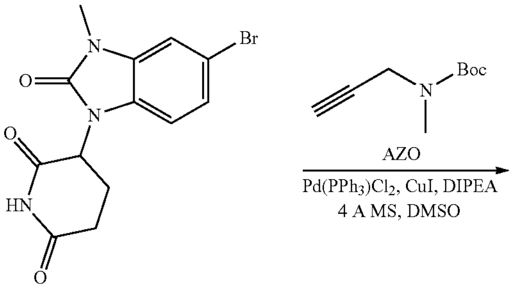

HN

-continued

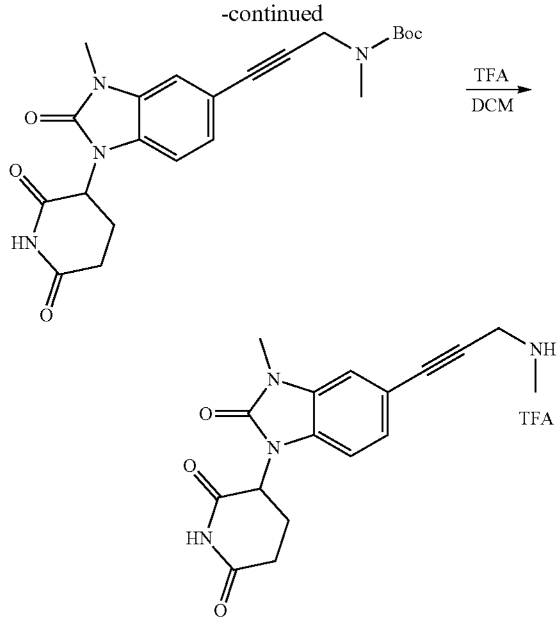

BEQ

Step 1—Tert-butyl (3-(1-(2,6-dioxopiperidin-3-yl)-3-methyl-2-oxo-2,3-dihydro-1H-benzo[d]imidazol-5-yl)prop-2-yn-1-yl)(methyl)carbamate A mixture of tert-butyl N-methyl-N-prop-2-ynyl-carbamate (1.00 g, 5.91 mmol, Intermediate AZO), 3-(5-bromo-3-methyl-2-oxo-2,3-dihydro-1H-benzo[d]imidazol-1-yl)piperidine-2,6-dione (1.54 g, 4.55 mmol, Intermediate HN), $Pd(PPh_3)_2Cl_2$ (638 mg, 909 umol), CuI (173 mg, 909 umol), DIPEA (2.94 g, 22.7 mmol, 3.96 mL) and 4 Å molecular sieves (500 mg, 4.55 mmol) in DMSO (15.0 mL) was degassed and purged with $N_2$ for 3 times, and then the mixture was stirred at 80° C. for 3 hrs under $N_2$ atmosphere. On completion, the reaction mixture was filtered and the filtrate was concentrated in vacuo to give a residue. The residue was purified by reversed phase (0.1% FA condition) to give the title compound (400 mg, 20% yield) as a yellow solid. $^1H$ NMR (400 MHz, $CDCl_3$) δ 8.62-8.16 (m, 1H), 7.20-7.14 (m, 1H), 7.09 (s, 1H), 6.75 (d, J=8.0 Hz, 1H), 5.20 (dd, J=5.2, 12.8 Hz, 1H), 4.27 (s, 2H), 3.42 (s, 3H), 2.98 (s, 3H), 2.96-2.90 (m, 1H), 2.88-2.77 (m, 1H), 2.77-2.65 (m, 1H), 2.26-2.02 (m, 1H), 1.49 (s, 9H).

Step 2—3-(3-Methyl-5-(3-(methylamino)prop-1-yn-1-yl)-2-oxo-2,3-dihydro-1H-benzo[d]imidazol-1-yl)piperidine-2,6-dione To a solution of tert-butyl (3-(1-(2,6-dioxopiperidin-3-yl)-3-methyl-2-oxo-2,3-dihydro-1H-benzo[d] imidazol-5-yl) prop-2-yn-1-yl)(methyl)carbamate (150 mg, 351 umol) in DCM (5.00 mL) was added TFA (770 mg, 6.75 mmol, 0.5 mL). On completion, the reaction mixture was concentrated in vacuo to give the title compound (90.0 mg, 58% yield, TFA) as a yellow solid. LC-MS ($ESI^+$) m/z 345.0 $(M+H_2O+H)^+$.

6-Cyclopropylpyridine-2-carboxylic acid (Intermediate BER)

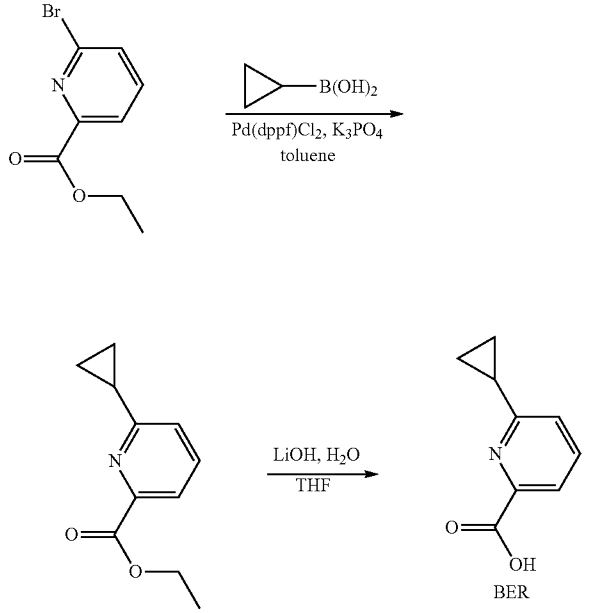

Step 1—6-Cyclopropylpyridine-2-carboxylic acid

To a solution of ethyl 6-bromopyridine-2-carboxylate (CAS #21190-88-5, 4.00 g, 17.3 mmol) in toluene (35 mL) was added cyclopropylboronic acid (3.73 g, 43.4 mmol), $K_3PO_4$ (7.38 g, 34.7 mmol) and Pd(dppf)$Cl_2$ (636 mg, 869 umol). Then the mixture was stirred at 100° C. for 8 hrs. On completion, the reaction mixture was filtered through celite, and washed with DCM (20 mL). The filtrate was concentrated in vacuo and he residue was purified by flash silica gel chromatography (PE/EA=3/1) to give the title compound (1.60 g, 48% yield) as yellow oil. LC-MS ($ESI^+$) m/z 192.0 $(M+H)^+$; $^1H$ NMR (400 MHz, DMSO-$d_6$) δ 7.86-7.72 (m, 2H), 7.47 (d, J=7.2 Hz, 1H), 4.31 (q, J=7.2 Hz, 2H), 2.24-2.09 (m, 1H), 1.31 (t, J=7.2 Hz, 3H), 1.04-0.87 (m, 4H).

Step 2—6-Cyclopropylpyridine-2-carboxylic acid

To a solution of ethyl 6-cyclopropylpyridine-2-carboxylate (1.6 g, 8.37 mmol) and LiOH (601 mg, 25.1 mmol) in $H_2O$ (10 mL) and THE (20 mL) was stirred at 25° C. for 16 hrs. On completion, the mixture was extracted with EA (20 mL) and the organic layer was discarded. The aqueous phase was acidified by HCl aqueous (5N) until the pH=6, and extracted by EA (3×20 mL). The combined organic layers were dried over by $Na_2SO_4$, filtered and concentrated in vacuo to give the title compound (1.10 g, 80% yield) as yellow solid. LC-MS ($ESI^+$) m/z 164.1 $(M+H)^+$, $^1H$ NMR (400 MHz, DMSO-$d_6$) δ 8.10-7.98 (m, 1H), 7.90 (dd, J=7.6, 0.8 Hz, 1H), 7.55 (dd, J=8.0, 0.8 Hz, 1H), 2.45-2.34 (m, 1H), 1.20-0.95 (m, 4H).

6-Cyclopropyl-N-[2-(4-formylcyclohexyl)-6-(1-hydroxy-1-methyl-ethyl)indazol-5-yl]pyridine-2-carboxamide (Intermediate BES)

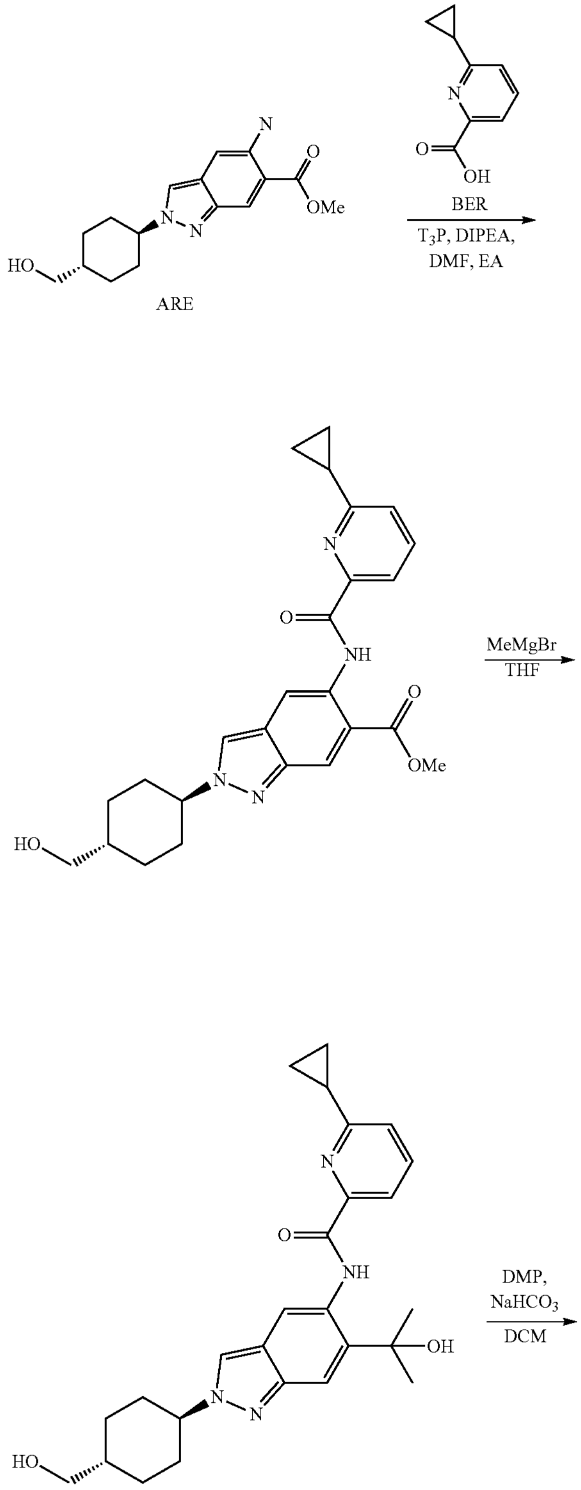

-continued

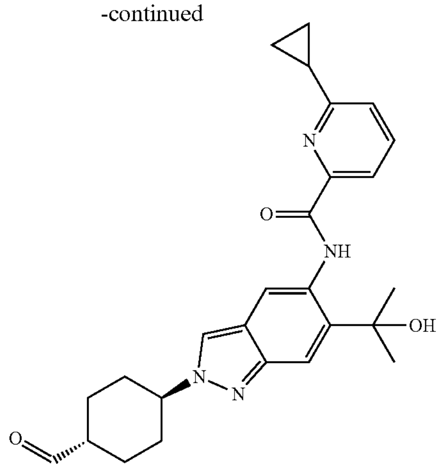

BES

Step 1—6-Cyclopropyl-N-[2-(4-formylcyclohexyl)-6-(1-hydroxy-1-methyl-ethyl)indazol-5-yl]pyridine-2-carboxamide To a solution of 6-cyclopropylpyridine-2-carboxylic acid (161 mg, 988 umol, Intermediate BER) in DMF (6 mL) was added DIEA (1.28 g, 9.89 mmol) and methyl 5-amino-2-[4-(hydroxymethyl)cyclohexyl]indazole-6-carboxylate (299 mg, 988 umol, Intermediate ARE). The reaction mixture was stirred at 25° C. for 10 min. Then $T_3P$ (755 mg, 1.19 mmol, 50% solution in EA) was added and the mixture was stirred at 25° C. for 16 hrs. On completion, the mixture was quenched by water (1 mL) and purified by reverse phase flash (0.1% FA condition) to give the title compound (260 mg, 58% yield) as brown solid. $^1H$ NMR (400 MHz, DMSO-$d_6$) δ 12.54 (s, 1H), 9.06 (s, 1H), 8.53 (s, 1H), 8.43 (s, 1H), 7.94-7.86 (m, 2H), 7.60 (dd, J=6.4, 2.4 Hz, 1H), 4.59-4.40 (m, 2H), 3.96 (s, 3H), 3.29 (t, J=5.2 Hz, 2H), 2.27-2.12 (m, 3H), 1.97-1.84 (m, 4H), 1.52-1.47 (m, 1H), 1.35-1.30 (m, 2H), 1.21-1.11 (m, 2H), 1.09-1.02 (m, 2H).LC-MS ($ESI^+$) m/z 449.3 $(M+H)^+$.

Step 2—6-Cyclopropyl-N-[2-[4-(hydroxymethyl) cyclohexyl]-6-(1-hydroxy-1-methyl-ethyl) indazol-5-yl]pyridine-2-carboxamide To a mixture of methyl 5-[(6-cyclopropylpyridine-2-carbonyl)amino]-2-[4-(hydroxymethyl)cyclohexyl]indazole-6-carboxylate (140 mg, 312 umol) in THE (10 mL) was added MeMgBr (3 M, 1.04 mL) at 0° C. then the mixture was stirred at 25° C. for 16 hrs. On completion, the mixture was quenched by $NH_4Cl$ aqueous and extracted by EA (3×20 mL), then the combined organic layers was dried over by $Na_2SO_4$ and filtered. The filtrate was concentrated in vacuo to give the title compound (103 mg, 73% yield) as yellow solid. LC-MS ($ESI^+$) m/z 471.2 $(M+23)^+$.

Step 3—6-Cyclopropyl-N-[2-(4-formylcyclohexyl)-6-(1-hydroxy-1-methyl-ethyl)indazol-5-yl]pyridine-2-carboxamide To a solution of 6-cyclopropyl-N-[2-[4-(hydroxymethyl) cyclohexyl]-6-(1-hydroxy-1-methyl-ethyl) indazol-5-yl] pyridine-2-carboxamide (90.0 mg, 200 umol), and $NaHCO_3$ (168 mg, 2.01 mmol) in DCM (1 mL) was added DMP (85.1 mg, 200 umol). The reaction mixture was stirred at 25° C. for 1 hr. Then DMP (42.5 mg, 100 umol) was added and stirred at 25° C. for 4 hrs. On completion, the mixture was quenched by $Na_2S_2O_3$ aqueous (5 mL) and extracted by EA (3×10 mL). The combined organic layer was dried over by $Na_2SO_4$ and filtered and the filtrate was concentrated in vacuo. The residue was purified by column chromatography (petroleum ether/ethyl acetate=1/1) to give the title compound (55 mg, 61% yield) as yellow solid. LC-MS ($ESI^+$) m/z 429.2 $(M-17)^+$.

Methyl 4-[6-amino-5-[tert-butyl(dimethyl)silyl]oxy-1,3-benzoxazol-2-yl]cyclohexane carboxylate (Intermediate BET)

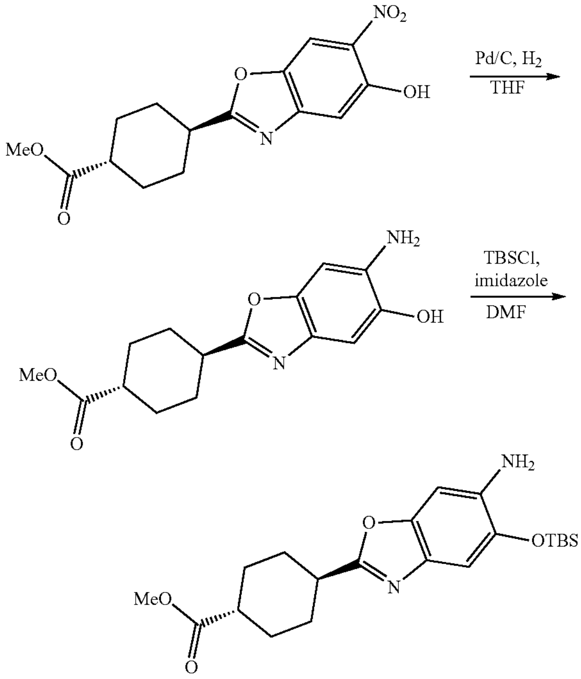

BET

Step 1—Methyl 4-(6-amino-5-hydroxy-1,3-benzoxazol-2-yl)cyclohexanecarboxylate

A mixture of methyl 4-(5-hydroxy-6-nitro-1,3-benzoxazol-2-yl)cyclohexanecarboxylate (890 mg, 2.78 mmol, synthesized via Steps 1-3 of Intermediate AZR) and Pd/C (400 mg, 10 wt %) in THE (20 mL) was stirred at 25° C. under $H_2$ (15 psi) for 1 hour. On completion, the mixture was filtered, and the cake was washed with THE (20 mL). The filtrate and washing were combined and concentrated in vacuo give a residue. The residue was purified by column chromatography on silica gel (PE:EA=20:1-1:2) to give the title compound (680 mg, 84% yield) as light yellow solid. $^1H$ NMR (400 MHz, DMSO-$d_6$) δ 9.19 (s, 1H), 6.85 (s, 1H), 6.77 (s, 1H), 4.73 (s, 2H), 3.61 (s, 3H), 2.83-2.81 (m, 1H), 2.39-2.37 (m, 1H), 2.16-2.08 (m, 2H), 2.03-1.94 (m, 2H), 1.62-1.45 (m, 4H).

Step 2—Methyl 4-[6-amino-5-[tert-butyl(dimethyl) silyl]oxy-1,3-benzoxazol-2-yl]cyclohexane carboxylate To a solution of methyl 4-(6-amino-5-hydroxy-1,3-benzoxazol-2-yl)cyclohexanecarboxylate (630 mg, 2.17 mmol)

and imidazole (296 mg, 4.35 mmol) in DMF (10 mL) was added TBSCl (491 mg, 3.26 mmol) at 0° C. The mixture was stirred at 25° C. for 2 hours. On completion, the mixture was diluted with water (100 mL), then extracted with EA (3×50 mL). The combine organic layer was washed with brine (30 mL), dried over $Na_2SO_4$, filtered and concentrated in vacuo. The residue was purified by column chromatography on silica gel (PE:EA=100:1-5:1) to give the title compound (740 mg, 84% yield) as light yellow solid. $^1H$ NMR (400 MHz, DMSO-$d_6$) δ 6.91 (s, 1H), 6.87 (s, 1H), 4.72 (s, 2H), 3.61 (s, 3H), 2.85-2.83 (m, 1H), 2.43-2.35 (m, 1H), 2.18-2.07 (m, 2H), 2.04-1.95 (m, 2H), 1.63-1.41 (m, 4H), 0.98 (s, 9H), 0.21 (s, 6H).

N-[2-(4-formylcyclohexyl)-5-(2-hydroxy-2-methyl-propoxy)-1,3-benzoxazol-6-yl]-6-(trifluoromethyl)pyridine-2-carboxamide (Intermediate BEU)

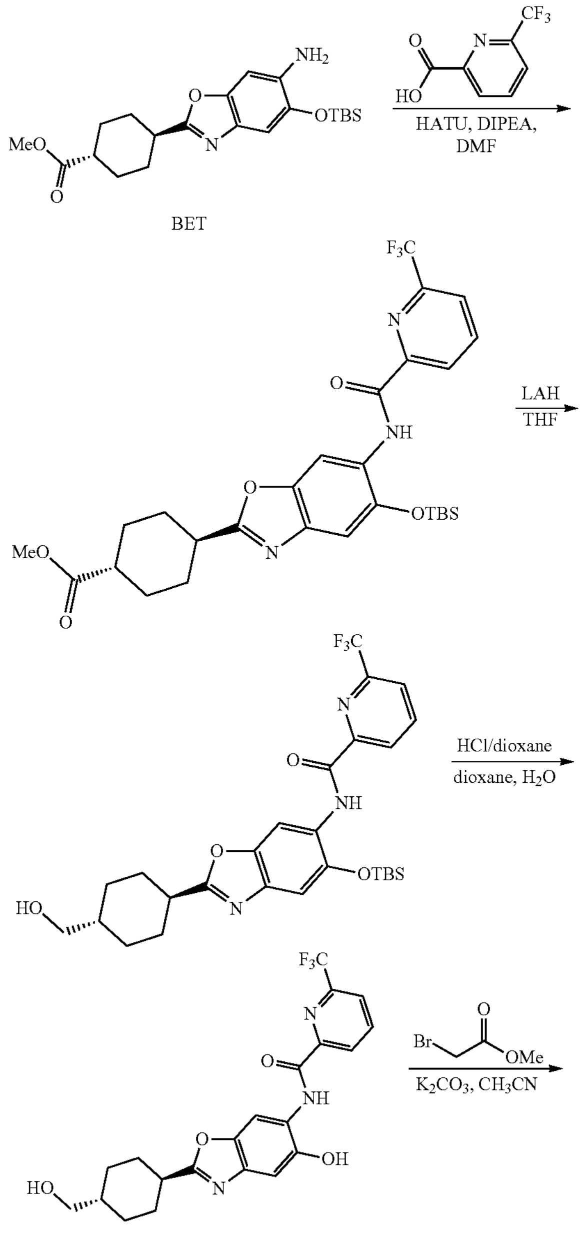

BET

-continued

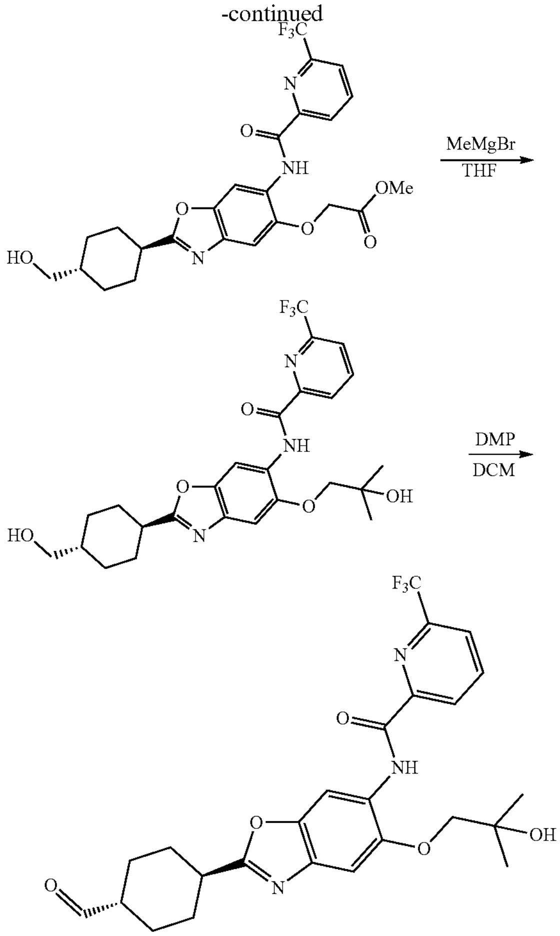

BEU

Step 1—Methyl 4-[5-[tert-butyl(dimethyl)silyl]oxy-6-[[6-(trifluoromethyl)pyridine-2-carbonyl]amino]-1,3-benzoxazol-2-yl]cyclohexanecarboxylate To a solution of methyl 4-[6-amino-5-[tert-butyl(dimethyl)silyl]oxy-1,3-benzoxazol-2-yl]cyclohexanecarboxylate (690 mg, 1.71 mmol, Intermediate BET), 6-(trifluoromethyl)pyridine-2-carboxylic acid (326 mg, 1.71 mmol, CAS #131747-42-7) and DIPEA (662 mg, 5.12 mmol) in DMF (1.0 mL) was added HATU (973 mg, 2.56 mmol) at 25° C. The mixture was stirred at 25° C. for 0.5 hour. On completion, the reaction was quenched with water (0.2 mL) and the mixture was concentrated in vacuo. The residue was purified by reverse phase (FA condition) to give the title compound (660 mg, 66% yield) as light yellow solid. $^1H$ NMR (400 MHz, DMSO-$d_6$) δ 10.17 (s, 1H), 8.76-8.67 (m, 1H), 8.51 (d, J=8.0 Hz, 1H), 8.41 (t, J=8.0 Hz, 1H), 8.22 (d, J=8.0 Hz, 1H), 7.30-7.25 (m, 1H), 3.66-3.58 (m, 3H), 3.04-2.91 (m, 1H), 2.45-2.35 (m, 1H), 2.21-2.17 (m, 2H), 2.08-1.97 (m, 2H), 1.79-1.45 (m, 4H), 0.97 (s, 9H), 0.40-0.29 (m, 6H).

Step 2—N-[5-[tert-butyl(dimethyl)silyl]oxy-2-[4-(hydroxymethyl)cyclohexyl]-1,3-benzoxazol-6-yl]-6-(trifluoromethyl)pyridine-2-carboxamide To a solution of methyl 4-[5-[tert-butyl(dimethyl)silyl]oxy-6-[[6-(trifluoromethyl)pyridine-2-carbonyl]amino]-1,3-benzoxazol-2-yl]cyclohexanecarboxylate (640 mg, 1.11 mmol) in THE (10 mL) was added LAH (85.0 mg, 2.24 mmol) at 0° C. and the mixture was stirred at 0° C. for 0.5 hour. On completion, the reaction was quenched with water (0.1 mL) slowly at 0-20° C. Then, to the mixture was added 15% aq. NaOH (0.1 mL) and water (0.3 mL). The mixture was filtered and the filtrate was concentrated in vacuo to give the title compound (608 mg, 99% yield) as light yellow solid. LC-MS (ESI$^+$) m/z 550.3 (M+H)$^+$.

Step 3—N-[5-hydroxy-2-[4-(hydroxymethyl)cyclohexyl]-1,3-benzoxazol-6-yl]-6-(trifluoromethyl)pyridine-2-carboxamide To a solution of N-[5-[tert-butyl(dimethyl)silyl]oxy-2-[4-(hydroxymethyl)cyclohexyl]-1,3-benzoxazol-6-yl]-6-(trifluoromethyl)pyridine-2-carboxamide (608 mg, 1.11 mmol) in dioxane (10.0 mL) and water (5.0 mL) was added HCl/dioxane (4.0 M, 10 mL) at 25° C. The mixture was stirred at 65° C. for 3 hours. On completion, after cooled to 25° C., and the mixture was basified to pH=8 with sat. aq. $NaHCO_3$, and then extracted with EA (3×50 mL). The combined organic layer was washed with brine (30 mL), dried over $Na_2SO_4$, filtered and concentrated in vacuo to give the title compound (480 mg, 99% yield) as light yellow solid. LC-MS (ESI$^+$) m/z 436.2 (M+H)$^+$.

Step 4—Methyl 2-[[2-[4-(hydroxymethyl)cyclohexyl]-6-[[6-(trifluoromethyl)pyridine-2-carbonyl]amino]-1,3-benzoxazol-5-yl]oxy]acetate A mixture of N-[5-hydroxy-2-[4-(hydroxymethyl)cyclohexyl]-1,3-benzoxazol-6-yl]-6-(trifluoro methyl)pyridine-2-carboxamide (480 mg, 1.10 mmol), methyl 2-bromoacetate (192 mg, 1.26 mmol) and $K_2CO_3$ (320 mg, 2.32 mmol) in DMF (5.0 mL) was stirred at 25° C. for 1 hour. On completion, the mixture was filtered, and the cake was washed with THE (5.0 mL). The filtrate and washing were combined and concentrated in vacuo to give a residue. The residue was purified by reverse phase (0.1% FA condition) to give the title compound (300 mg, 53% yield) as light yellow solid. $^1$H NMR (400 MHz, $CDCl_3$) δ 10.80 (s, 1H), 8.86 (s, 1H), 8.52 (d, J=8.0 Hz, 1H), 8.14 (t, J=7.6 Hz, 1H), 7.89 (dd, J=0.8, 7.6 Hz, 1H), 7.21-7.17 (m, 1H), 4.82 (s, 2H), 3.84 (s, 3H), 3.54 (s, 2H), 2.95-2.87 (m, 1H), 2.37-2.23 (m, 2H), 2.02-1.98 (m, 2H), 1.76-1.69 (m, 2H), 1.65-1.60 (m, 1H), 1.24-1.11 (m, 2H).

Step 5—N-[2-[4-(hydroxymethyl)cyclohexyl]-5-(2-hydroxy-2-methyl-propoxy)-1,3-benzoxazol-6-yl]-6-(trifluoromethyl)pyridine-2-carboxamide To a solution of methyl 2-[[2-[4-(hydroxymethyl)cyclohexyl]-6-[[6-(trifluoromethyl)pyridine-2-carbonyl]amino]-1,3-benzoxazol-5-yl]oxy]acetate (250 mg, 492 umol) in THE (10 mL) was added MeMgBr (3.0 M, 0.85 mL) at 0° C. The mixture was stirred at 0° C. for 2 hours. On completion, the reaction was quenched with sat. aq. $NH_4Cl$ (10 mL). The mixture was diluted with water (20 mL), then extracted with EA (3×20 mL). The combined organic layer was washed with brine (10 mL), dried over $Na_2SO_4$, filtered and concentrated in vacuo to give the title compound (250 mg, 99% yield) as light yellow solid. LC-MS (ESI$^+$) m/z 508.2 (M+H)$^+$.

Step 6—N-[2-(4-formylcyclohexyl)-5-(2-hydroxy-2-methyl-propoxy)-1,3-benzoxazol-6-yl]-6-(trifluoromethyl)pyridine-2-carboxamide To a solution of N-[2-[4-(hydroxymethyl)cyclohexyl]-5-(2-hydroxy-2-methyl-propoxy)-1,3-benzoxazol-6-yl]-6-(trifluoromethyl)pyridine-2-carboxamide (250 mg, 492 umol) in DCM (5.0 mL) was added DMP (272 mg, 641 umol) at 0° C. The mixture was stirred at 25° C. for 1 hour. On completion, the reaction was quenched with sat. aq. $Na_2S_2O_3$ (5 mL). The mixture was partitioned and the aqueous phase was extracted with DCM (2×10 mL). The combined organic layer was washed with sat. aq. $NaHCO_3$ (5.0 mL) and brine (5.0 mL), dried over $Na_2SO_4$, filtered and concentrated in vacuo. The residue was purified by reverse phase (0.1% FA condition) to give the title compound (160 mg, 64% yield) as light yellow solid. LC-MS (ESI$^+$) m/z 506.2 (M+H)$^+$.

Pyrimidine-4-carboxamide (Intermediate BEV)

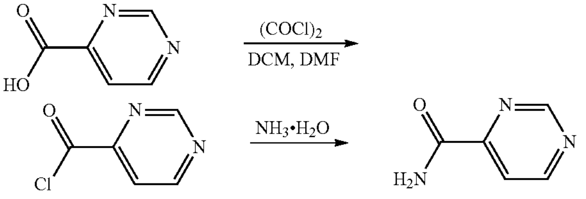

BEV

Step 1—Pyrimidine-4-carbonyl chloride

To a solution of pyrimidine-4-carboxylic acid (800 mg, 6.45 mmol, CAS #31462-59-6) in DCM (8.00 mL) was added $(COCl)_2$ (1.64 g, 12.8 mmol) and DMF (47.1 mg, 644 umol) at 0° C. and the mixture was stirred at 0° C. for 2 hrs. On completion, the mixture was concentrated in vacuo to give the title compound (918 mg, 99% yield) as black solid. LC-MS (ESI$^+$) m/z 139.1 (M+1)*(quenched by MeOH).

Step 2—Pyrimidine-4-carboxamide

A mixture of $NH_3.H_2O$ (8.06 g, 64.4 mmol, 28% solution) was added a solution of pyrimidine-4-carbonylchloride (918 mg, 6.44 mmol) in THE (10 mL) dropwise at 0° C. The mixture was stirred at 0° C. for 0.5 hr. On completion, the mixture was concentrated in vacuo. Then diluted with $H_2O$ (30 mL), and extracted with EA (8×40 mL). The organic layers were dried over anhydrous $Na_2SO_4$, filtered and concentrated in vacuo to give the title compound (460 mg, 58% yield) as yellow solid. $^1$H NMR (400 MHz, DMSO-$d_6$) δ 9.37 (d, J=1.2 Hz, 1H), 9.11 (d, J=5.2 Hz, 1H), 8.40 (s, 1H), 8.07 (dd, J=1.2, 5.2 Hz, 1H), 8.02 (s, 1H), LC-MS (ESI$^+$) m/z 124.1 (M+H)$^+$.

N-[2-(4-formylcyclohexyl)-6-methoxy-indazol-5-yl]pyrimidine-4-carboxamide (Intermediate BEW)

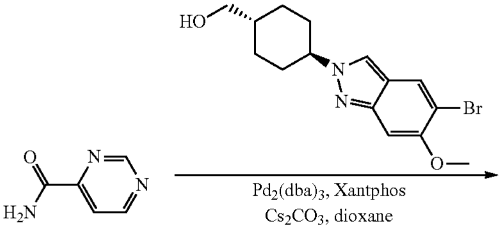

BEV

-continued

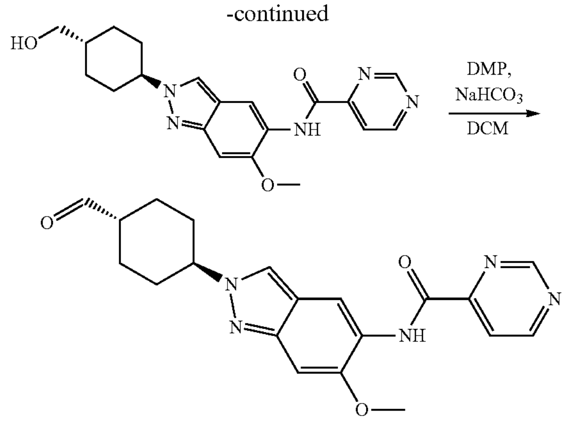

BEW

Step 1—N-[2-[4-(hydroxymethyl)cyclohexyl]-6-methoxy-indazol-5-yl]pyrimidine-4-carboxamide To a solution of pyrimidine-4-carboxamide (217 mg, 1.77 mmol, Intermediate BEV), [4-(5-bromo-6-methoxy-indazol-2-yl)cyclohexyl]methanol (500 mg, 1.47 mmol, synthesized via Steps 1-3 of Intermediate ATE) in dioxane (8.00 mL) was added $Pd_2(dba)_3$ (134 mg, 147 umol), Xantphos (170 mg, 294 umol) and $Cs_2CO_3$ (960 mg, 2.95 mmol). The mixture was stirred at 80° C. for 160 hrs under $N_2$. On completion, the mixture was filtered and the filtrate was concentrated in vacuo. The mixture was purified by reverse phase (0.1% TFA) to give the title compound (100 mg, 17% yield) as yellow solid. $^1$H NMR (400 MHz, DMSO-$d_6$) δ 10.53 (s, 1H), 9.44 (d, J=1.2 Hz, 1H), 9.17 (d, J=5.2 Hz, 1H), 8.71 (s, 1H), 8.36 (s, 1H), 8.19 (dd, J=1.2, 5.2 Hz, 1H), 7.18 (s, 1H), 4.45-4.30 (m, 1H), 4.00 (s, 3H), 3.32-3.26 (m, 2H), 2.17-2.10 (m, 2H), 1.98-1.72 (m, 5H), 1.55-1.41 (m, 1H), 1.19-1.08 (m, 2H).

Step 2—N-[2-(4-formylcyclohexyl)-6-methoxy-indazol-5-yl]pyrimidine-4-carboxamide To a solution of N-[2-[4-(hydroxymethyl)cyclohexyl]-6-methoxy-indazol-5-yl]pyrimidine-4- carboxamide (90.0 mg, 235 umol) in DCM (3.00 mL) was added DMP (120 mg, 283 umol) and $NaHCO_3$ (99.1 mg, 1.18 mmol) and the mixture was stirred at 25° C. for 1 hr. On completion, the mixture was diluted with DCM (20 mL) and quenched with saturated $Na_2S_2O_3$ (30 mL) and washed with saturated $NaHCO_3$ (2×30 mL). The organic layer was dried over anhydrous $Na_2SO_4$, filtered and concentrated in vacuo to give the title compound (70.0 mg, 78% yield) as yellow solid. $^1$H NMR (400 MHz, DMSO-$d_6$) δ 10.53 (s, 1H), 9.65 (s, 1H), 9.44 (d, J=1.2 Hz, 1H), 9.17 (d, J=5.2 Hz, 1H), 8.72 (s, 1H), 8.36 (s, 1H), 8.19 (dd, J=1.2, 5.2 Hz, 1H), 7.18 (s, 1H), 4.50-4.32 (m, 1H), 4.01 (s, 3H), 2.47-2.40 (m, 1H), 2.25-2.16 (m, 2H), 2.15-2.05 (m, 2H), 2.03-1.93 (m, 2H), 1.50-1.40 (m, 2H).

2-Methyloxazole-4-carboxamide (Intermediate BEX)

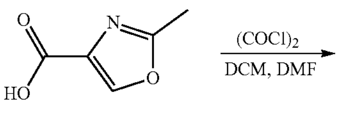

-continued

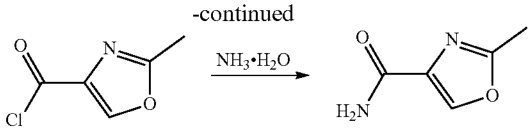

BEX

Step 1—2-Methyloxazole-4-carbonyl chloride

To a solution of 2-methyloxazole-4-carboxylic acid (2.00 g, 15.7 mmol, CAS #23062-17-1) and DMF (11.5 mg, 157 umol) in DCM (20 mL) was added $(COCl)_2$ (4.99 g, 39.3 mmol, 3.44 mL) at 0° C. The mixture was stirred at 20° C. for 4 hrs. On completion, the reaction mixture was concentrated in vacuo to give the title compound (2.00 g, 87% yield) as a yellow solid. $^1$H NMR (400 MHz, $CDCl_3$) δ 8.34 (s, 1H), 2.54 (s, 3H).

Step 2—2-Methyloxazole-4-carboxamide

To a solution of $NH_3.H_2O$ (9.63 g, 68.7 mmol, 10.5 mL, 25% solution) was added a solution of 2-methyloxazole-4-carbonyl chloride (2.00 g, 13.7 mmol) in THF (5 mL) at 0° C. The mixture was stirred at 20° C. for 0.5 hr. On completion, the reaction mixture was concentrated in vacuo to remove THF. Then the mixture was filtered, the filter cake was washed with water and dried in vacuo to give the title compound (1.30 g, 75% yield) as a white solid. $^1$H NMR (400 MHz, DMSO-$d_6$) δ 8.41 (s, 1H), 7.63-7.34 (m, 2H), 2.44 (s, 3H), LC-MS (ESI$^+$) m/z 128.1 (M+H)$^+$.

N-[2-(4-formylcyclohexyl)-6-methoxy-indazol-5-yl]-2-methyl-oxazole-4-carboxamide (Intermediate BEY)

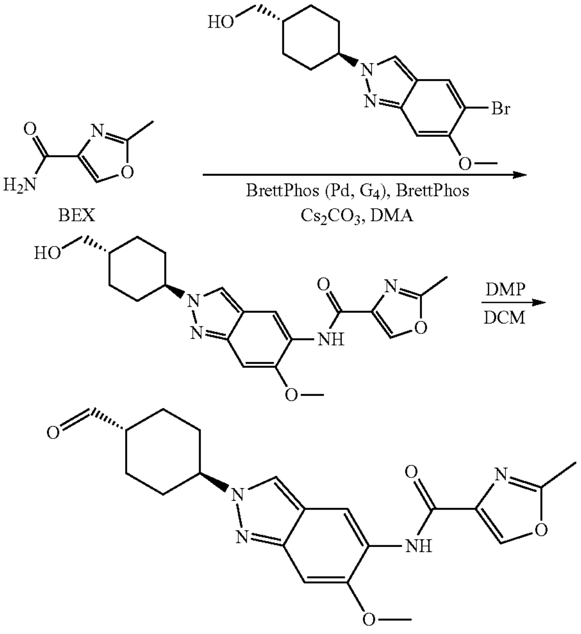

BEX

BEY

Step 1—N-[2-[4-(hydroxymethyl)cyclohexyl]-6-methoxy-indazol-5-yl]-2-methyl-oxazole-4- carboxamide A mixture of 2-methyloxazole-4-carboxamide (70.0 mg, 555 umol, Intermediate BEX), [4-(5-bromo-6-methoxy-indazol-2-yl)cyclohexyl]methanol (226 mg, 666 umol, synthesized via Steps 1-3 of Intermediate ATE), BrettPhos (Pd, G4) (51.1 mg, 55.5 umol), BrettPhos (29.8 mg, 55.5 umol) and $Cs_2CO_3$ (362 mg, 1.11 mmol) in DMA (6.00 mL) was stirred at 100° C. for 16 hours under nitrogen atmosphere. On completion, the reaction mixture was filtered and the filtrate was concentrated in vacuo to give a residue. The residue was purified by reverse phase (0.1% TFA condition) to give the title compound (190 mg, 89% yield) as a yellow solid. $^1H$ NMR (400 MHz, DMSO-$d_6$) δ 9.45 (s, 1H), 8.74 (s, 1H), 8.17 (s, 1H), 7.85 (s, 1H), 7.06 (s, 1H), 4.35-4.27 (m, 1H), 4.01 (s, 3H), 3.56 (d, J=6.4 Hz, 2H), 2.54 (s, 3H), 2.36-2.28 (m, 2H), 2.09-2.02 (m, 2H), 2.01-1.91 (m, 2H), 1.70-1.63 (m, 2H), 1.26-1.20 (m, 2H). LC-MS (ESI$^+$) m/z 385.2 $(M+H)^+$.

Step 2—N-[2-(4-formylcyclohexyl)-6-methoxy-indazol-5-yl]-2-methyl-oxazole-4-carboxamide To a solution of N-[2-[4-(hydroxymethyl)cyclohexyl]-6-methoxy-indazol-5-yl]-2-methyl-oxazole-4- carboxamide (100 mg, 260 umol) in DCM (5.00 mL) was added DMP (132 mg, 312 umol) at 0° C. The reaction mixture was stirred at 20° C. for 1 hr. On completion, the reaction mixture was quenched by addition saturated solution of $Na_2S_2O_3$ (5 mL), and saturated solution of $NaHCO_3$ (4 mL), then extracted with DCM (3x10 mL). The combined organic layer was washed with brine (2x20 mL), dried over anhydrous $Na_2SO_4$, filtered and concentrated in vacuo to give the title compound (89.0 mg, 89% yield) as a yellow solid. $^1H$ NMR (400 MHz, $CDCl_3$) δ 9.72 (s, 1H), 9.45 (s, 1H), 8.75 (s, 1H), 8.17 (s, 1H), 7.85 (s, 1H), 7.05 (s, 1H), 4.36-4.28 (m, 1H), 4.02 (s, 3H), 2.54 (s, 3H), 2.45-2.35 (m, 3H), 2.30-2.22 (m, 2H), 2.10-1.99 (m, 2H), 1.58-1.48 (m, 2H).

Pyrazine-2-carboxamide (Intermediate BEZ)

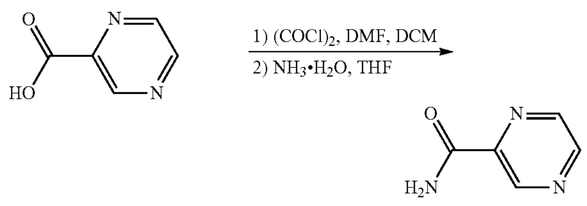

BEZ

To a solution of pyrazine-2-carboxylic acid (CAS #98-97-5, 2.00 g, 16.1 mmol) and DMF (11.7 mg, 161 umol) in DCM (20 mL) was added $(COCl)_2$ (6.14 g, 48.3 mmol) at 0° C. and stirred at 25° C. for 1.5 hrs. The mixture was concentrated in vacuo, the residue was dissolved in THF (20 mL) and added to $NH_3.H_2O$ (1.88 g, 16.1 mmol, 30% solution) at 0° C. The mixture was stirred at 25° C. for 10 min. On completion, the mixture was poured into water and extracted by EA (8x100 mL). The combined organic layer was dried over $Na_2SO_4$ and filtered. The filtrate was concentrated in vacuo to give the title compound (1.50 g, 75% yield) as yellow oil. $^1H$ NMR (400 MHz, DMSO-$d_6$) δ 9.18 (d, J=1.6 Hz, 1H), 8.85 (d, J=2.4 Hz, 1H), 8.71 (dd, J=2.4, 1.6 Hz, 1H), 8.25 (br s, 1H), 7.86 (br s, 1H).

N-[2-(4-formylcyclohexyl)-6-methoxy-indazol-5-yl] pyrazine-2-carboxamide (Intermediate BFA)

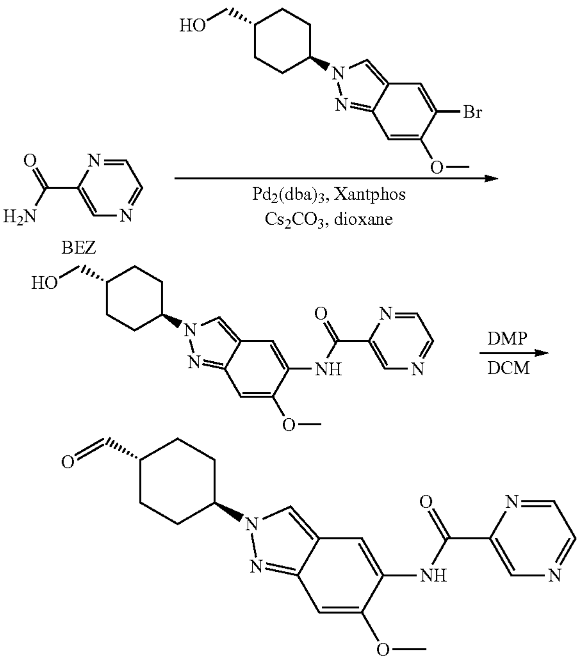

BFA

Step 1—N-[2-[4-(hydroxymethyl)cyclohexyl]-6-methoxy-indazol-5-yl]pyrazine-2-carboxamide A mixture of pyrazine-2-carboxamide (139 mg, 1.13 mmol, Intermediate BEZ), [4-(5-bromo-6-methoxy-indazol-2-yl)cyclohexyl]methanol (350 mg, 1.03 mmol, synthesized via Steps 1-3 of Intermediate ATE), $Pd_2(dba)_3$ (94.4 mg, 103 umol), Xantphos (119 mg, 206 umol) and $Cs_2CO_3$ (672 mg, 2.06 mmol) in dioxane (1 mL) was stirred at 110° C. for 16 hrs. On completion, The mixture was filtered and the filtrate was concentrated in vacuo. The residue was purified by column chromatography (ethyl acetate) to give the title compound (120 mg, 30% yield) as yellow solid. $^1H$ NMR (400 MHz, DMSO-$d_6$) δ 10.33 (s, 1H), 9.35 (d, J=1.2 Hz, 1H), 8.96 (d, J=2.4 Hz, 1H), 8.83 (s, 1H), 8.69 (s, 1H), 8.33 (s, 1H), 7.16 (s, 1H), 4.39-4.31 (m, 1H), 3.98 (s, 3H), 3.30-3.27 (m, 2H), 2.15-2.13 (m, 2H), 1.89-1.82 (m, 4H), 1.53-1.42 (m, 1H), 1.20-1.10 (m, 2H), 0.10-0.19 (m, 1H).

Step 2—N-[2-(4-formylcyclohexyl)-6-methoxy-indazol-5-yl]pyrazine-2-carboxamide

To a solution of N-[2-[4-(hydroxymethyl)cyclohexyl]-6-methoxy-indazol-5-yl]pyrazine-2-carboxamide (90.0 mg, 235 umol) in DCM (1 mL) was added DMP (120 mg, 283 umol) at 0° C. and stirred at 25° C. for 1.5 hr. On completion, the mixture was quenched by $Na_2S_2O_3$ and extracted by DCM (3x10 mL). The combined organic layer was dried over by $Na_2SO_4$. The mixture was filtered and the filtrate was concentrated in vacuo. The residue was purified by Prep-TLC (EA) to give the title compound (50.0 mg, 42% yield) as yellow oil. LC-MS (ESI$^+$) m/z 380.2 $(M+H)^+$.

N-[2-(4-formylcyclohexyl)-6-methoxy-1-oxo-isoindolin-5-yl]-6-(trifluoromethyl)pyridine-2-carboxamide (Intermediate BFB)
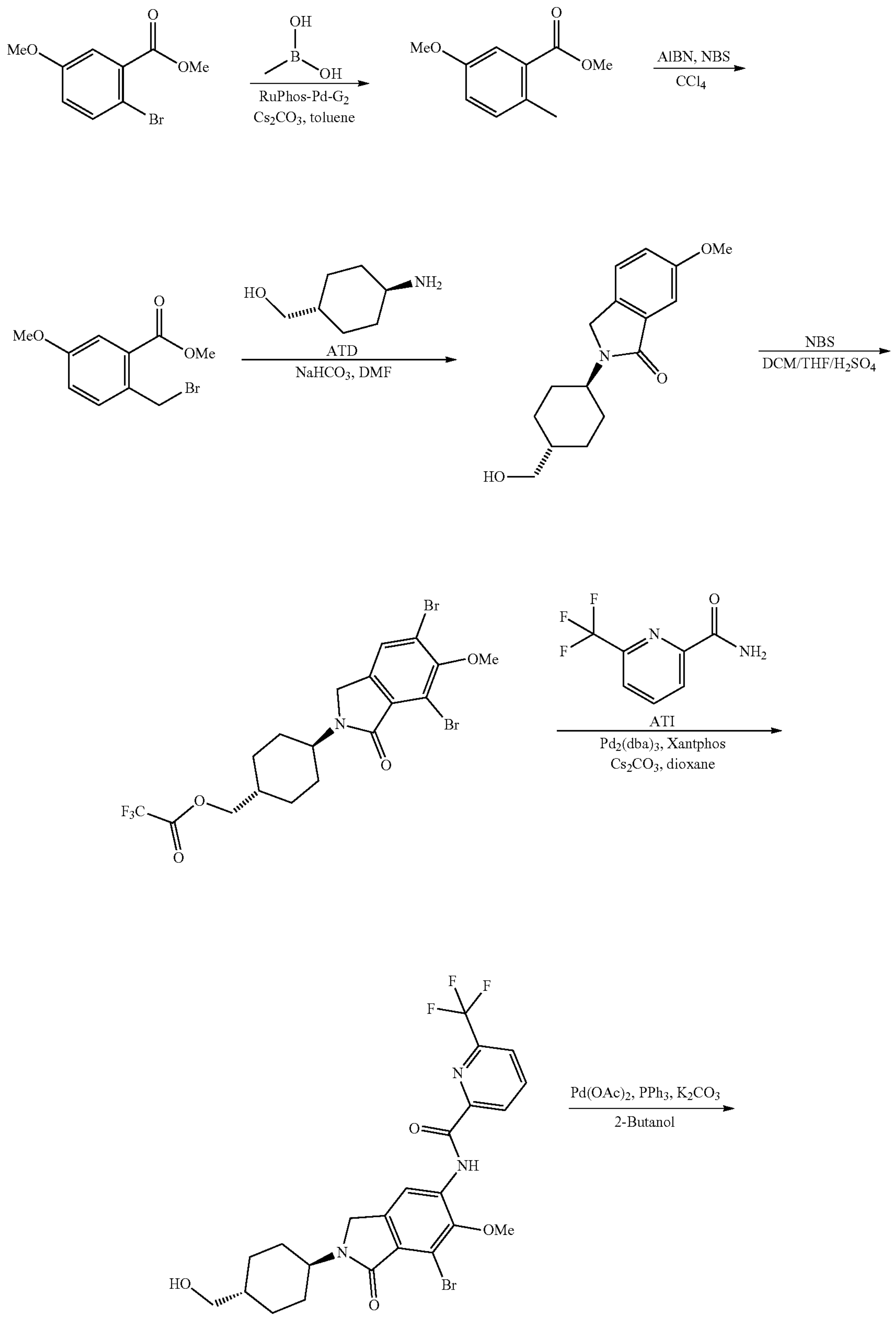

-continued

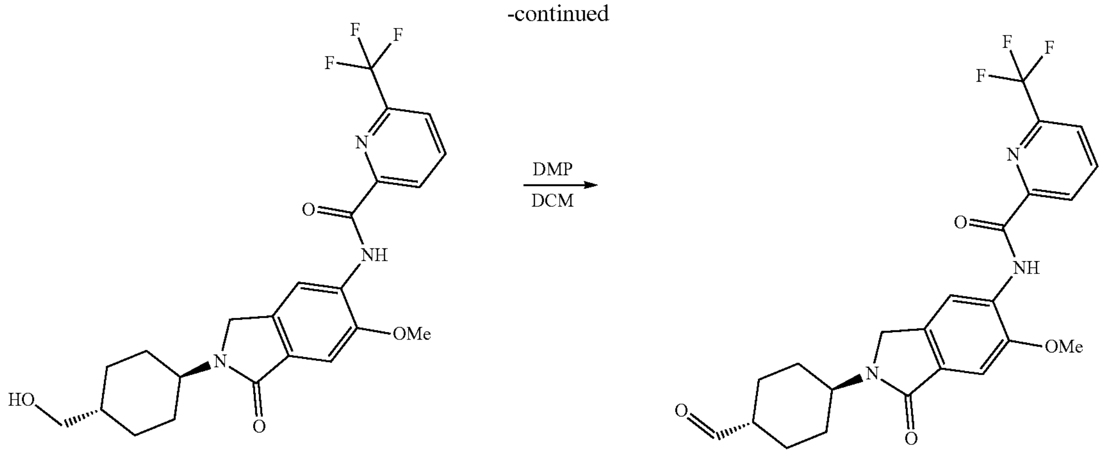

BFB

Step 1—Methyl 5-methoxy-2-methyl-benzoate

A mixture of methyl 2-bromo-5-methoxy-benzoate (5.00 g, 20.4 mmol, CAS #35450-36-3), methylboronic acid (24.4 g, 408 mmol, CAS #13061-96-6), [2-(2-aminophenyl)phenyl]-chloro-palladium;dicyclohexyl-[2-(2,6-diisopropoxyphenyl)phenyl]phosphane (1.58 g, 2.04 mmol) and $Cs_2CO_3$ (19.9 g, 61.2 mmol) in toluene (100 mL) was stirred at 115° C. for 16 hours. On completion, after cooled to 25° C., the mixture was diluted with water (100 mL), and extracted with EA (3×50 mL). The combined organic layer was washed with brine (30 mL), dried over $Na_2SO_4$, filtered and concentrated in vacuo to give a residue. The residue was purified by column chromatography on silica gel (PE:EA=100:1-50:1) to give the title compound (3.50 g, 95% yield) as light yellow oil. $^1H$ NMR (400 MHz, $CDCl_3$) δ 7.45 (d, J=2.8 Hz, 1H), 7.15 (d, J=8.4 Hz, 1H), 6.97 (dd, J=2.8, 8 .4 Hz, 1H), 3.90 (s, 3H), 3.83 (s, 3H), 2.53 (s, 3H).

Step 2—Methyl 2-(bromomethyl)-5-methoxy-benzoate

A mixture of methyl 5-methoxy-2-methyl-benzoate (3.10 g, 17.2 mmol), NBS (3.07 g, 17.2 mmol) and AIBN (283 mg, 1.72 mmol) in $CCl_4$ (30 mL) was stirred at 80° C. for 16 hours. On completion, after cooled to 25° C., the mixture was filtered through a pad of silica gel, and the cake was washed with a mixed solution (PE:EA=10:1) (100 mL). The filtrate and washing were combined and concentrated in vacuo to give the title compound (4.40 g, 98% yield) as light yellow oil. $^1H$ NMR (400 MHz, $CDCl_3$) δ 7.49 (d, J=2.8 Hz, 1H), 7.38 (d, J=8.4 Hz, 1H), 7.03 (dd, J=2.8, 8.4 Hz, 1H), 4.94 (s, 2H), 3.96 (s, 3H), 3.86 (s, 3H).

Step 3—2-[4-(hydroxymethyl)cyclohexyl]-6-methoxy-isoindolin-1-one

To a mixture of (4-aminocyclohexyl)methanol (4.19 g, 32.4 mmol, Intermediate ATD) and $NaHCO_3$ (2.73 g, 32.5 mmol) in DMF (60 mL) was added methyl 2-(bromomethyl)-5-methoxy-benzoate (4.20 g, 16.2 mmol) at 25° C. The mixture was stirred at 25° C. for 3 hours. On completion, the mixture was diluted with water (300 mL), and extracted with EA (3×100 mL). The combined organic layer was washed with brine (50 mL), dried over $Na_2SO_4$, filtered and concentrated in vacuo to give a residue. The residue was purified by column chromatography on silica gel (PE:EA=20:1-3:1) to give the title compound (2.90 g, 64% yield) as light yellow solid. $^1H$ NMR (400 MHz, $CDCl_3$) δ 7.36-7.30 (m, 2H), 7.08 (dd, J=2.4, 8.4 Hz, 1H), 4.29 (s, 2H), 4.27-4.19 (m, 1H), 3.86 (s, 3H), 3.51 (d, J=6.4 Hz, 2H), 1.95 (d, J=10.8 Hz, 4H), 1.62-1.46 (m, 3H), 1.28-1.12 (m, 2H).

Step 4—[4-(5,7-dibromo-6-methoxy-1-oxo-isoindolin-2-yl)cyclohexyl]methyl 2,2,2-trifluoroacetate To a solution of 2-[4-(hydroxymethyl)cyclohexyl]-6-methoxy-isoindolin-1-one (2.30 g, 8.35 mmol) in a mixed solvents of TFA (8.0 mL), DCM (8.0 mL) and $H_2SO_4$ (4.0 mL) was added NBS (2.97 g, 16.7 mmol) at 0° C. The mixture was stirred at 25° C. for 5 hours. On completion, the mixture was diluted with ice/water (100 mL), and basified to pH=8 with sat. aq. $K_2CO_3$, then extracted with DCM (3×100 mL). The combined organic layer was washed with brine (80 mL), dried over $Na_2SO_4$, filtered and concentrated in vacuo to give the title compound (4.00 g, 90% yield) as light yellow solid. LC-MS ($ESI^+$) m/z 530.0 $(M+H)^+$.

Step 5—N-[7-bromo-2-[4-(hydroxymethyl)cyclohexyl]-6-methoxy-1-oxo-isoindolin-5-yl]-6-(trifluoromethyl)pyridine-2-carboxamide A mixture of [4-(5,7-dibromo-6-methoxy-1-oxo-isoindolin-2-yl)cyclohexyl]methyl 2,2,2- trifluoroacetate (700 mg, 1.32 mmol), 6-(trifluoromethyl)pyridine-2-carboxamide (277 mg, 1.46 mmol, Intermediate ATI), $Pd_2(dba)_3$ (121 mg, 132 umol), Xantphos (154 mg, 266 umol) and $Cs_2CO_3$ (863 mg, 2.65 mmol) in dioxane (15 mL) was stirred at 80° C. for 16 hours under $N_2$. On completion, after cooled to 25° C., the mixture was filtered, and the cake was washed with DCM (50 mL). The filtrate and washing were combined and concentrated in vacuo to give a residue. The residue was purified by reverse phase (FA condition) and column chromatography on silica gel (DCM:EA=10:1-3:1) to give the title compound (180 mg, 25% yield) as light yellow solid. $^1H$ NMR (400 MHz, $CDCl_3$) δ 10.82 (s, 1H), 8.70 (s, 1H), 8.50

(d, J=7.6 Hz, 1H), 8.18 (t, J=8.0 Hz, 1H), 7.93 (d, J=7.6 Hz, 1H), 4.32 (s, 2H), 4.29-4.19 (m, 1H), 4.04 (s, 3H), 3.53 (d, J=6.4 Hz, 2H), 1.96 (d, J=11.6 Hz, 4H), 1.54 (s, 3H), 1.41-1.31 (m, 1H), 1.27-1.17 (m, 2H).

Step 6—N-[2-[4-(hydroxymethyl)cyclohexyl]-6-methoxy-1-oxo-isoindolin-5-yl]-6-(trifluoromethyl)pyridine-2-carboxamide A mixture of N-[7-bromo-2-[4-(hydroxymethyl)cyclohexyl]-6-methoxy-1-oxo-isoindolin-5-yl]-6-(trifluoromethyl)pyridine-2-carboxamide (165 mg, 304 umol), $Pd(OAc)_2$ (9.30 mg, 41.4 umol), $PPh_3$ (16.5 mg, 62.9 umol) and $K_2CO_3$ (84.0 mg, 608 umol) in 2-butanol (6.0 mL) was stirred at 100° C. for 3 hours under $N_2$. On completion, after cooled to 25° C., the mixture was filtered, and the cake was washed with THE (30 mL). The filtrate and washing were combined and concentrated in vacuo. The residue was purified by reverse phase (FA condition) to give the title compound (130 mg, 92% yield) as light yellow solid. $^1H$ NMR (400 MHz, $CDCl_3$) δ 10.76 (s, 1H), 8.74 (s, 1H), 8.50 (d, J=8.0 Hz, 1H), 8.15 (t, J=8.0 Hz, 1H), 7.94-7.86 (m, 1H), 7.41 (s, 1H), 4.35 (s, 2H), 4.30-4.20 (m, 1H), 4.05 (s, 3H), 3.53 (d, J=5.2 Hz, 2H), 3.50 (s, 1H), 1.97 (d, J=11.6 Hz, 4H), 1.64-1.58 (m, 2H), 1.35 (s, 1H), 1.28-1.18 (m, 2H).

Step 7—N-[2-(4-formylcyclohexyl)-6-methoxy-1-oxo-isoindolin-5-yl]-6-(trifluoromethyl)pyridine-2-carboxamide To a solution of N-[2-[4-(hydroxymethyl)cyclohexyl]-6-methoxy-1-oxo-isoindolin-5-yl]-6-(trifluoromethyl)pyridine-2-carboxamide (120 mg, 258 umol) in DCM (5.0 mL) was added DMP (165 mg, 389 umol) at 0° C. The mixture was stirred at 25° C. for 2 hours. On completion, the reaction was quenched with sat. aq. $Na_2S_2O_3$ (3 mL). The mixture was partitioned and the aqueous phase was extracted with DCM (2×10 mL). The combined organic layer was washed with sat. aq. $NaHCO_3$ (3.0 mL) and brine (5.0 mL), dried over $Na_2SO_4$, filtered and concentrated in vacuo to give the title compound (118 mg, 98% yield) as light yellow solid. LC-MS ($ESI^+$) m/z 462.3 $(M+H)^+$.

N-[2-(4-formylcyclohexyl)-6-(1-hydroxy-1-methyl-ethyl)indazol-5-yl]pyrimidine-4-carboxamide (Intermediate BFC)

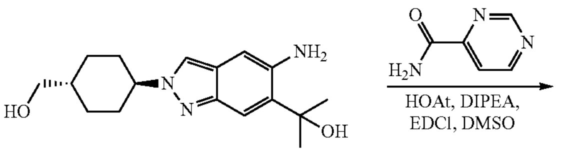

AOX

-continued

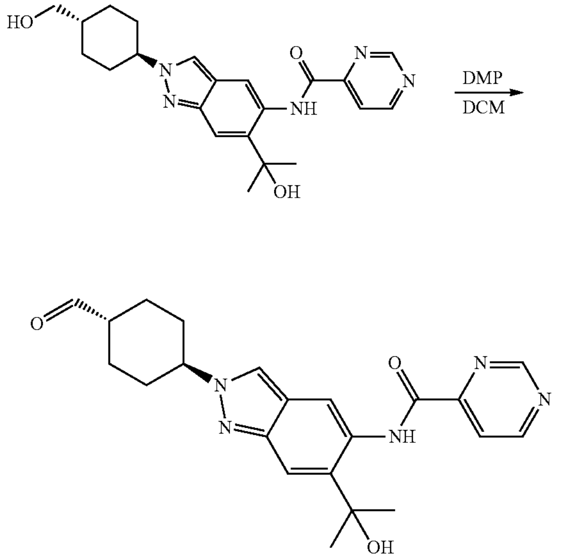

BFC

Step 1—N-[2-[4-(hydroxymethyl)cyclohexyl]-6-(1-hydroxy-1-methyl-ethyl)indazol-5-yl]pyrimidine-4-carboxamide To a solution of 2-[5-amino-2-[4-(hydroxymethyl)cyclohexyl]indazol-6-yl]propan-2-ol (500 mg, 1.65 mmol, Intermediate AOX) and pyrimidine-4-carboxylic acid (CAS #31462-59-6, 204 mg, 1.65 mmol) in DMSO (5 mL) was added DIPEA (1.06 g, 8.24 mmol), HOAt (291 mg, 2.14 mmol) and EDCI (410 mg, 2.14 mmol). The mixture was stirred at 25° C. for 3 hours. On completion, the reaction mixture was filtered and the filtrate was concentrated in vacuo. The residue was purified by reverse phase flash (0.1% FA) to give the title compound (390 mg, 39% yield, FA salt) as a yellow solid. LC-MS ($ESI^+$) m/z 410.1 $(M+H)^+$.

Step 2—N-[2-(4-formylcyclohexyl)-6-(1-hydroxy-1-methyl-ethyl)indazol-5-yl]pyrimidine-4-carboxamide To a solution of N-[2-[4-(hydroxymethyl)cyclohexyl]-6-(1-hydroxy-1-methyl-ethyl)indazol-5-yl]pyrimidine-4-carboxamide (370 mg, 617 umol) in DCM (10 mL) was added DMP (392 mg, 926 umol) at 0° C. The mixture was stirred at 25° C. for 1 hour. On completion, the reaction mixture was quenched by addition saturated $NaHCO_3$ (5 mL) and $Na_2S_2O_3$ (5 mL), and then diluted with $H_2O$ (10 mL) and extracted with DCM (2×100 mL). The combined organic layers were washed with brine (50 mL), dried over $Na_2SO_4$, filtered and concentrated in vacuo to give the title compound (380 mg, 95% yield) as a yellow solid. LC-MS ($ESI^+$) m/z 408.1 $(M+H)^+$.

N-[2-(4-formylcyclohexyl)-6-methoxy-3H-benzimidazol-5-yl]-6-(trifluoromethyl)pyridine-2- carboxamide (Intermediate BFD)
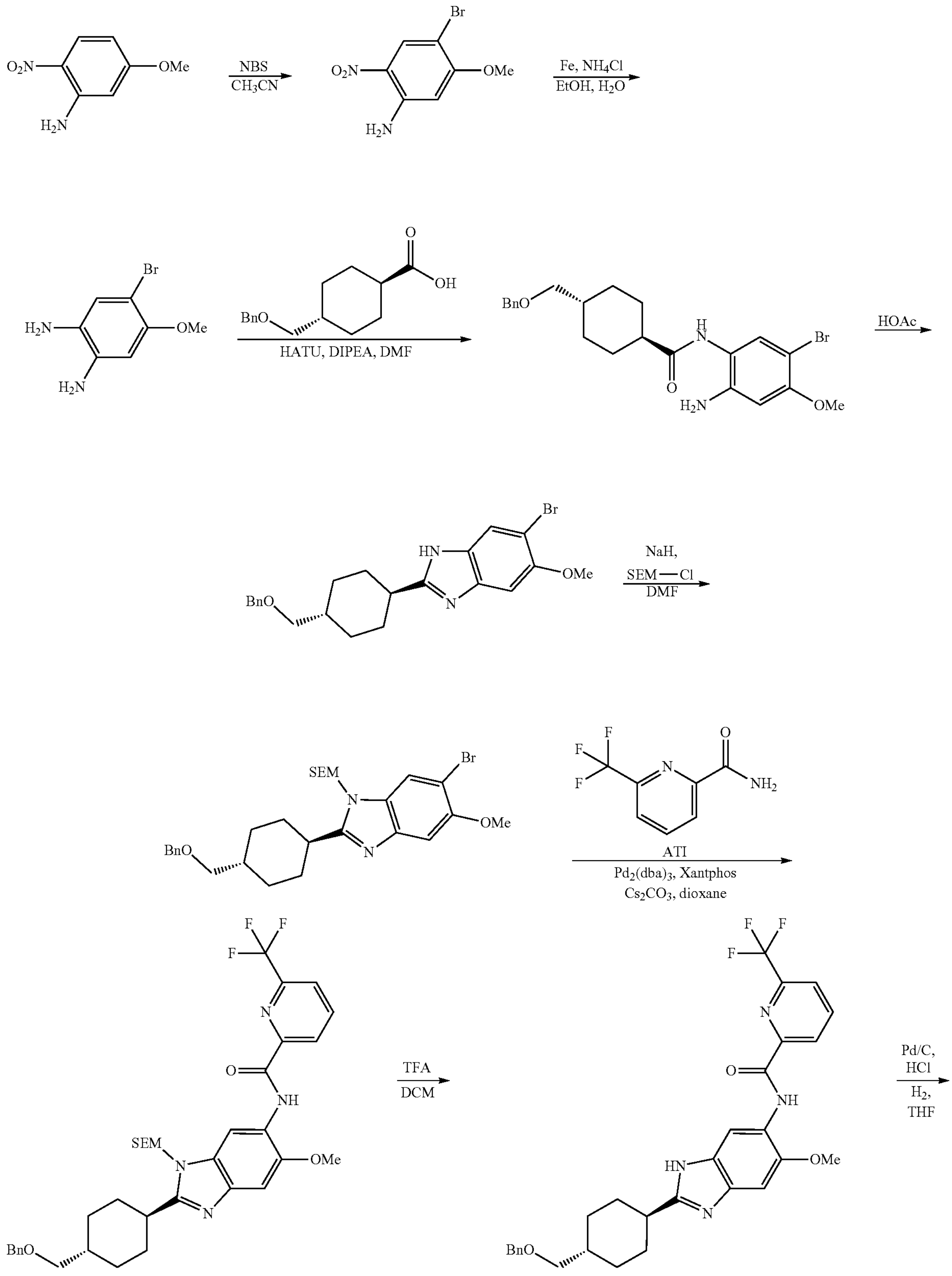

-continued

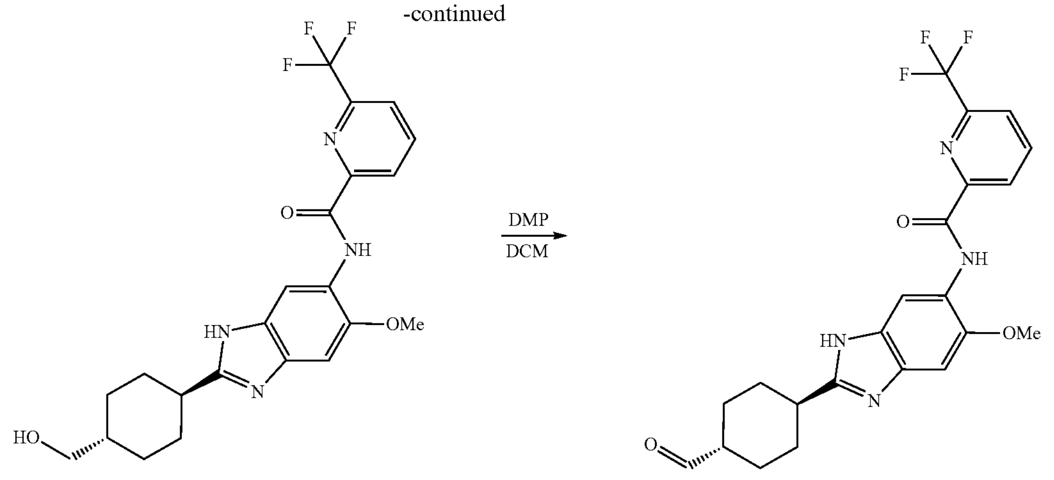

BFD

Step 1—4-Bromo-5-methoxy-2-nitro-aniline

To a solution of 5-methoxy-2-nitro-aniline (11.0 g, 65.4 mmol, CAS #16133-49-6) in ACN (150 mL) was added NBS (12.8 g, 71.9 mmol) at 25° C. The mixture was stirred at 25° C. for 3 hours. On completion, the mixture was quenched with sat. aq. $Na_2SO_3$ (300 mL) and $H_2O$ (500 mL) at 25° C. A solid was precipitated out from the solution, and the solid was washed with $H_2O$ (200 mL) and filtered. The filter cake was dissolved in EA (500 mL), dried over by $Na_2SO_4$, filtered and the filtrate was concentrated in vacuo to give the title compound (16.0 g, 89% yield) as a yellow solid.

Step 2—4-Bromo-5-methoxy-benzene-1,2-diamine

To a solution of 4-bromo-5-methoxy-2-nitro-aniline (16.0 g, 58.2 mmol) in a mixed solvent of EtOH (160 mL), THE (80 mL) and $H_2O$ (80 mL) was added $NH_4Cl$ (31.1 g, 582 mmol) at 25° C. Then Fe (16.2 g, 291 mmol) was added to the above mixture at 70° C. The reaction mixture was stirred at 80° C. for 12 hours. On completion, the reaction mixture was filtered through celite and the filtrate was concentrated in vacuo to give a residue. The residue was diluted with $H_2O$ (600 mL) and extracted with EA (3×200 mL). The combined organic layers were washed with brine (2×150 mL), dried over $Na_2SO_4$, filtered and the filtrate was concentrated in vacuo to give the title compound (10.5 g, 82% yield) as a black solid. $^1$H NMR (400 MHz, DMSO-$d_6$) δ 6.67 (s, 1H), 6.35 (s, 1H), 4.56 (s, 4H), 3.64 (s, 3H).

Step 3—N-(2-amino-5-bromo-4-methoxy-phenyl)-4-(benzyloxymethyl)cyclohexanecarboxamide To a solution of 4-(benzyloxymethyl)cyclohexanecarboxylic acid (6.29 g, 25.3 mmol, synthesized via Steps 1-3 of Intermediate BAU) and 4-bromo-5-methoxy-benzene-1,2-diamine (5.50 g, 25.3 mmol) in DMF (60 mL) was added DIPEA (6.55 g, 50.6 mmol, 8.83 mL) and HATU (11.5 g, 30.4 mmol) at 25° C. The reaction mixture was stirred at 25° C. for 2 hours. On completion, the reaction mixture was diluted with $H_2O$ (300 mL) and extracted with EA (3×100 mL). The combined organic layers were washed with brine (2×100 mL), dried over by $Na_2SO_4$, filtered and concentrated in vacuo to give a residue The residue was purified by column chromatography ($SiO_2$, petroleum ether/ethyl acetate=10/1 to 1/1) to give the title compound (3.40 g, 29% yield) as a brown solid. LC-MS (ESI$^+$) m/z 449.1 $(M+1)^+$.

Step 4—2-[4-(Benzyloxymethyl)cyclohexyl]-6-bromo-5-methoxy-1H-benzimidazole

A solution of N-(2-amino-5-bromo-4-methoxy-phenyl)-4-(benzyloxymethyl)cyclohexanecarboxamide (1.00 g, 2.24 mmol) in HOAc (15 mL) was stirred at 80° C. for 15 hours. On completion, the reaction mixture was concentrated in vacuo to give a residue. The residue was diluted with $H_2O$ (60 mL) and extracted with EA (3×20 mL). The combined organic layers were washed with sat. aq. $NaHCO_3$ (2×20 mL), dried over $Na_2SO_4$, filtered and the filtrate was concentrated in vacuo to give a residue. The residue was purified by column chromatography ($SiO_2$, petroleum ether/ethyl acetate=10/1 to 2/1) to give the title compound (800 mg, 66% yield) as a white solid. LC-MS (ESI$^+$) m/z 431.1 $(M+H)^+$.

Step 5—2-[[2-[4-(benzyloxymethyl)cyclohexyl]-6-bromo-5-methoxy-benzimidazol-1-yl]methoxy]ethyl-trimethyl-silane To a solution of 2-[4-(benzyloxymethyl)cyclohexyl]-6-bromo-5-methoxy-1H-benzimidazole (3.00 g, 5.59 mmol) in DMF (35 mL) was added NaH (290 mg, 7.27 mmol, 60% dispersion in mineral oil) at 0° C. and the mixture was stirred at 0-25° C. for 0.5 hour. Then SEM-Cl (1.40 g, 8.38 mmol, 1.48 mL) was added to above mixture, and the reaction mixture was stirred at 25° C. for 1.5 hours. On completion, the reaction mixture was quenched with sat. aq. $NH_4Cl$ (5 mL), and then diluted with $H_2O$ (60 mL) and extracted with EA (3×20 mL). The combined organic layers were washed with brine (2×20 mL), dried over $Na_2SO_4$, filtered and the filtrate was concentrated in vacuo to give a residue. The residue was purified by column chromatography ($SiO_2$, petroleum ether/ethyl acetate=1/0 to 5/1) to give the title compound (2.40 g, 76% yield) as yellow oil. LC-MS (ESI$^+$) m/z 559.3 $(M+H)^+$.

Step 6—N-[2-[4-(benzyloxymethyl)cyclohexyl]-6-methoxy-3-(2-trimethylsilylethoxymethyl) benzimidazol-5-yl]-6-(trifluoromethyl)pyridine-2-carboxamide To a solution of 2-[[2-[4-(benzyloxymethyl)cyclohexyl]-6-bromo-5-methoxy-benzimidazol-1- yl]methoxy]ethyl-trimethyl-silane (1.00 g, 1.79 mmol) and 6-(trifluoromethyl) pyridine-2-carboxamide (373 mg, 1.97 mmol, Intermediate ATI) in dioxane (10 mL) was added Xantphos (206 mg, 357 umol), $Cs_2CO_3$ (1.16 g, 3.57 mmol) and $Pd_2(dba)_3$ (163 mg, 178 umol) at 25° C., then the reaction mixture was stirred at 100° C. under $N_2$ for 36 hours. On completion, the reaction mixture was filtered and the filtrate was concentrated in vacuo to give a residue. The residue was purified by column chromatography ($SiO_2$, petroleum ether/ethyl acetate=10/1 to 1/1) to give the title compound (900 mg, 75% yield) as yellow oil. $^1H$ NMR (400 MHz, DMSO-$d_6$) δ 10.50 (s, 1H), 8.67 (s, 1H), 8.49-8.39 (m, 2H), 8.22 (d, J=7.6 Hz, 1H), 7.40-7.29 (m, 6H), 5.56 (s, 2H), 4.48 (s, 2H), 3.96 (s, 3H), 3.57 (t, J=8.0 Hz, 2H), 3.31 (s, 2H), 3.02-2.92 (m, 1H), 1.94 (s, 2H), 1.87 (d, J=10.8 Hz, 2H), 1.74-1.62 (m, 3H), 1.25-1.12 (m, 4H), -0.08 (s, 9H); LC-MS (ESI+) m/z 669.3 $(M+H)^+$.

Step 7—N-[2-[4-(benzyloxymethyl)cyclohexyl]-6-methoxy-3H-benzimidazol-5-yl]-6-(trifluoromethyl) pyridine-2-carboxamide To a solution of N-[2-[4-(benzyloxymethyl)cyclohexyl]-6-methoxy-3-(2-trimethylsilylethoxymethyl) benzimidazol-5-yl]-6-(trifluoromethyl)pyridine-2-carboxamide (600 mg, 897 umol) in DCM (3.0 mL) was added TFA (40.5 mmol, 3.0 mL) at 25° C. The mixture was stirred at 25° C. for 1 hour. On completion, the reaction mixture was concentrated in vacuo to give a residue. The residue was purified by reverse phase (0.1% FA condition) to give the title compound (350 mg, 72% yield) as a white solid. $^1H$ NMR (400 MHz, DMSO-$d_6$) δ 10.47 (s, 1H), 8.62 (s, 1H), 8.49-8.44 (m, 1H), 8.43-8.36 (m, 1H), 8.21 (d, J=7.6 Hz, 1H), 7.41-7.21 (m, 6H), 4.48 (s, 2H), 3.97 (s, 3H), 3.31 (d, J=6.0 Hz, 2H), 2.88-2.77 (m, 1H), 2.14-2.03 (m, 2H), 1.94-1.84 (m, 2H), 1.72-1.54 (m, 3H), 1.21-1.05 (m, 2H); LC-MS (ESI+) m/z 539.1 $(M+H)^+$.

Step 8—N-[2-[4-(hydroxymethyl)cyclohexyl]-6-methoxy-3H-benzimidazol-5-yl]-6- (trifluoromethyl) pyridine-2-carboxamide To a solution of N-[2-[4-(benzyloxymethyl)cyclohexyl]-6-methoxy-3H-benzimidazol-5-yl]-6- (trifluoromethyl)pyridine-2-carboxamide (250 mg, 464 umol) in THF (2.0 mL) was added Pd/C (200 mg, 464 umol, 10 wt %) and HCl (1.0 M, 464 uL) at 25° C. The mixture was stirred at 25° C. under $H_2$ (15 Psi) for 1 hour. On completion, the reaction mixture was filtered through celite and the filtrate was concentrated in vacuo to give the title compound (170 mg, 81% yield) as yellow oil. $^1H$ NMR (400 MHz, DMSO-$d_6$) δ 12.04 (s, 1H), 10.58-10.33 (m, 1H), 8.56 (s, 1H), 8.50-8.45 (m, 1H), 8.43-8.37 (m, 1H), 8.21 (d, J=8.0 Hz, 1H), 7.34-7.04 (m, 1H), 4.43 (t, J=5.2 Hz, 1H), 3.95 (s, 3H), 3.60 (t, J=6.4 Hz, 2H), 2.78-2.71 (m, 1H), 2.07 (d, J=11.2 Hz, 2H), 1.87 (d, J=10.8 Hz, 2H), 1.77-1.75 (m, 1H), 1.63-1.53 (m, 2H), 1.11-1.02 (m, 2H); LC-MS (ESI+) m/z 449.2 $(M+H)^+$.

Step 9—N-[2-(4-formylcyclohexyl)-6-methoxy-3H-benzimidazol-5-yl]-6-(trifluoromethyl)pyridine-2-carboxamide To a solution of N-[2-[4-(hydroxymethyl)cyclohexyl]-6-methoxy-3H-benzimidazol-5-yl]-6- (trifluoro methyl)pyridine-2-carboxamide (140 mg, 312 umol) in DCM (3.0 mL) was added DMP (172 mg, 405 umol) at 25° C. The reaction mixture was stirred at 25° C. for 2 hours. On completion, the reaction mixture was quenched with sat. aq. $Na_2S_2O_3$ (3 mL) and $NaHCO_3$ (3 mL), and then diluted with $H_2O$ (15 mL) and then extracted with DCM (3×5 mL). The combined organic layers were washed with brine (2×5 mL), dried over $Na_2SO_4$, filtered and concentrated in vacuo to give the title compound (130 mg, 93% yield) as a white solid. LC-MS (ESI+) m/z 447.2 $(M+H)^+$.

Tert-butyl 6-[(1R)-2-(1,3-dioxoisoindolin-2-yl)-1-methyl-ethyl]-2-azaspiro[3.3]heptane-2- carboxylate (Intermediate BFE) and tert-butyl 6-[(1S)-2-(1,3-dioxoisoindolin-2-yl)-1-methyl-ethyl]-2-azaspiro [3.3] heptanes-2-carboxylate (Intermediate BFF)

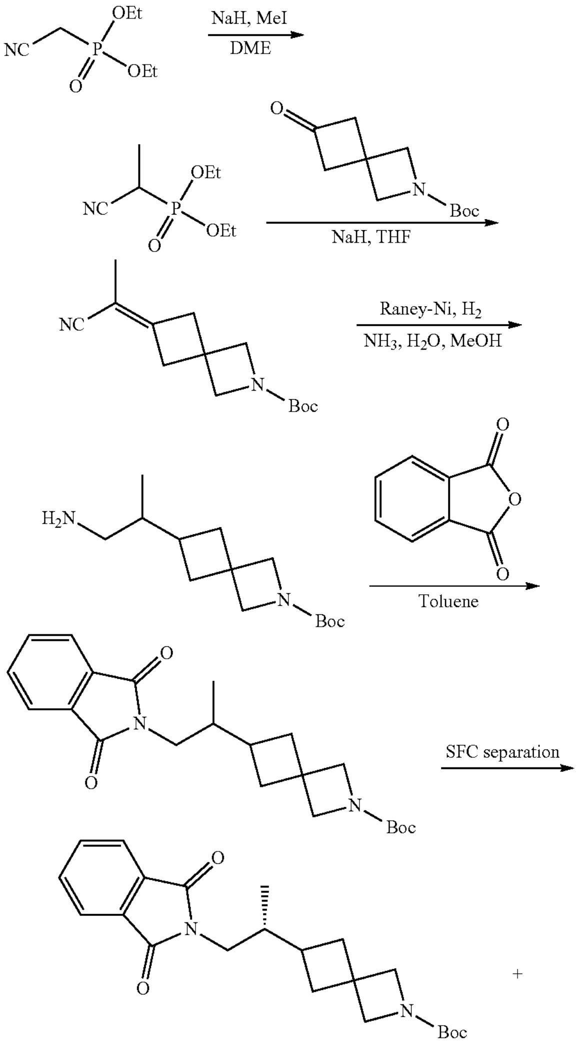

BFE

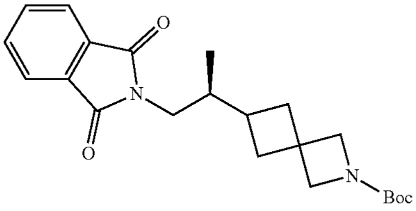

BFF

Step 1—2-Diethoxyphosphorylpropanenitrile

To a mixture of 2-diethoxyphosphorylacetonitrile (10.0 g, 56.45 mmol, CAS #2537-48-6) in DMF (100 mL) was added NaH (2.71 g, 67.7 mmol, 60% dispersion in mineral oil) at 0° C. and the mixture was stirred for 1 hour. Then $CH_3I$ (9.62 g, 67.7 mmol) was added dropwise into the mixture. The mixture was stirred at 20° C. for 2 hours. On completion, the mixture was poured into the water (300 mL). The aqueous phase was extracted with ethyl acetate (2×200 mL). The combined organic phase was washed with brine (2×200 mL), dried with anhydrous $Na_2SO_4$, filtered and concentrated in vacuo to give the residue. The residue was purified by column chromatography ($SiO_2$, petroleum ether/ethyl acetate=3:1 to 0:1) to give the title compound (7.20 g, 66% yield) as a yellow solid. $^1H$ NMR (400 MHz, $CDCl_3$) δ 4.29-4.19 (m, 4H), 3.05-2.82 (m, 1H), 1.57-1.51 (m, 3H), 1.41-1.34 (m, 6H).

Step 2—Tert-butyl 6-(1-cyanoethylidene)-2-azaspiro [3.3]heptane-2-carboxylate

To a mixture of 2-diethoxyphosphorylpropanenitrile (7.20 g, 37.7 mmol) in THE (80 mL) was added NaH (1.81 g, 45.2 mmol, 60% dispersion in mineral oil) at 0° C. and the mixture was stirred for 1 hour. Then tert-butyl 6-oxo-2-azaspiro[3.3]heptane-2-carboxylate (9.55 g, 45.2 mmol, CAS #1147557-97-8) was added into the mixture and the mixture was stirred at 20° C. for 2 hours. On completion, the residue was poured into water (150 mL) and the aqueous phase was extracted with ethyl acetate (2×80 mL). The combined organic phase was washed with brine (2×80 mL), dried with anhydrous $Na_2SO_4$, filtered and concentrated in vacuo to give the residue. The residue was purified by column chromatography ($SiO_2$, petroleum ether/ethyl acetate=3:1 to 0:1) to give the title compound (4.50 g, 48% yield) as a white solid. $^1H$ NMR (400 MHz, $CDCl_3$) δ 3.94-3.87 (m, 4H), 3.00 (d, J=1.6 Hz, 2H), 2.87 (s, 2H), 1.72-1.66 (m, 3H), 1.37 (s, 9H).

Step 3—Tert-butyl 6-(2-amino-1-methyl-ethyl)-2-azaspiro[3.3]heptane-2-carboxylate To a mixture of tert-butyl 6-(1-cyanoethylidene)-2-azaspiro[3.3]heptane-2-carboxylate (3.20 g, 12.9 mmol) in MeOH (50 mL) and $NH_3.H_2O$ (5 mL) was added Raney-Ni (1.10 g, 12.89 mmol) under $H_2$ (50 psi) and the mixture was stirred at 30° C. for 12 hours. On completion, the mixture was filtered and concentrated in vacuo to give the title compound (2.70 g, 82% yield) as a white solid. $^1H$ NMR (400 MHz, $CDCl_3$) δ 3.85 (s, 2H), 3.69 (s, 2H), 2.81-2.20 (m, 2H), 2.14 (d, J=8.0 Hz, 2H), 1.87-1.69 (m, 3H), 1.36 (s, 9H), 1.30-1.18 (m, 2H), 1.08 (d, J=15.2 Hz, 1H), 0.74 (d, J=6.4 Hz, 3H).

Step 4—Tert-butyl 6-[2-(1,3-dioxoisoindolin-2-yl)-1-methyl-ethyl]-2-azaspiro[3.3]heptane-2- carboxylate A solution of isobenzofuran-1,3-dione (1.89 g, 12.7 mmol) and tert-butyl 6-(2-amino-1-methyl-ethyl)-2-azaspiro[3.3]heptane-2-carboxylate (2.70 g, 10.6 mmol) in toluene (50 mL) was stirred at 110° C. for 12 hours. On completion, the mixture was concentrated in vacuo to give the residue. The residue was purified by column chromatography ($SiO_2$, PE:EA=10:1 to 3:1) to give the title compound (3.60 g, 77% yield) as a white solid. $^1H$ NMR (400 MHz, $CDCl_3$) δ 7.86 (dd, J=2.8, 5.2 Hz, 2H), 7.74 (dd, J=3.2, 5.2 Hz, 2H), 3.93 (s, 2H), 3.75 (s, 2H), 3.59-3.42 (m, 2H), 2.30-2.14 (m, 2H), 2.00-1.83 (m, 4H), 1.43 (s, 9H), 0.82 (d, J=6.4 Hz, 3H).

Step 5—Tert-butyl 6-[(1R)-2-(1,3-dioxoisoindolin-2-yl)-1-methyl-ethyl]-2-azaspiro[3.3]heptane-2- carboxylate and tert-butyl 6-[(1S)-2-(1,3-dioxoisoindolin-2-yl)-1-methyl-ethyl]-2-azaspiro [3.3]heptanes-2-carboxylate Tert-butyl 6-[2-(1,3-dioxoisoindolin-2-yl)-1-methyl-ethyl]-2-azaspiro[3.3]heptane-2- carboxylate (3.50 g, 9.10 mmol) was separated by SFC. The residue was purified by SFC (column: daicel chiralcel od (250 mm*30 mm, 10 um); mobile phase: [0.1% NH3H2O.MEOH]; B %: %-%, 0 min; 0 min min) and (column: daicel chiralcel ad (250 mm*30 mm,10 um); mobile phase: [0.1% $NH_3H_2O$ ETOH]; B %: 25%-25%, 5.4 min; 130 minmin) to give tert-butyl 6-[(1R)-2-(1,3-dioxoisoindolin-2-yl)-1-methyl-ethyl]-2-azaspiro [3.3]heptane-2- carboxylate (1.20 g, 34% yield) and tert-butyl 6-[(1S)-2-(1,3-dioxoisoindolin-2-yl)-1-methyl-ethyl]-2-azaspiro [3.3] heptanes-2-carboxylate (1.20 g, 34% yield) as a white solid. Absolute stereochemistry of the enantiomers were assigned arbitrarily.

Tert-butyl 6-[(1R)-2-amino-1-methyl-ethyl]-2-azaspiro[3.3]heptane-2-carboxylate (Intermediate BFG)

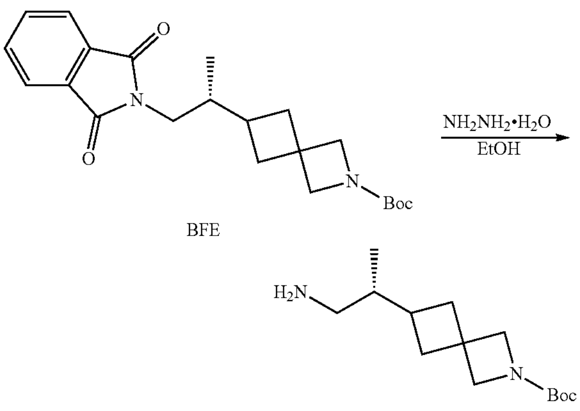

BFE

BFG

To a mixture of tert-butyl 6-[(1R)-2-(1,3-dioxoisoindolin-2-yl)-1-methyl-ethyl]-2-azaspiro[3.3]heptane -2-carboxylate (600 mg, 1.56 mmol, Intermediate BFE) in EtOH (20 mL) was added $N_2H4.H_2O$ (208 mg, 3.12 mmol, 75% solution). The mixture was stirred at 80° C. for 2 hours. On completion, the mixture was cooled to 20° C. and filtered. The mother liquor was concentrated in vacuo. Then the DCM was added the residue and the mixture was stirred at 10 minutes. The mixture was filtered and the mother liquor was concentrated in vacuo to give the title compound (305 mg, 76% yield) as a white solid. $^1H$ NMR (400 MHz, $CDCl_3$) δ 3.94 (s, 2H), 3.78 (s, 2H), 2.65 (dd, J=4.4, 12.4 Hz, 1H), 2.36 (dd, J=7.2, 12.4 Hz, 1H), 2.25-2.19 (m, 2H), 1.94-1.78 (m, 3H), 1.44 (s, 9H), 1.39-1.30 (m, 3H), 0.83 (d, J=6.8 Hz, 3H).

Tert-butyl 6-[(1S)-2-amino-1-methyl-ethyl]-2-azaspiro[3.3]heptane-2-carboxylate (Intermediate BFH)

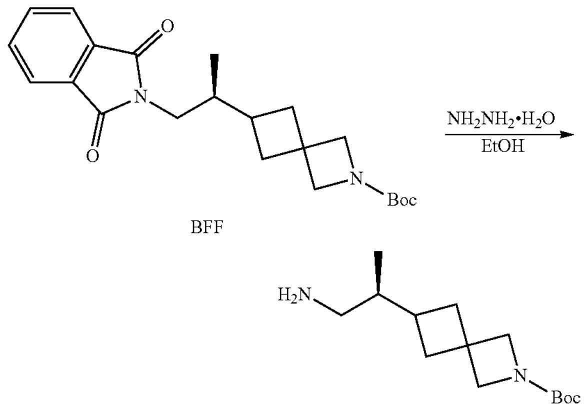

BFF

BFH

To a mixture of tert-butyl 6-[(1S)-2-(1,3-dioxoisoindolin-2-yl)-1-methyl-ethyl]-2-azaspiro[3.3]heptane -2-carboxylate (500 mg, 1.30 mmol, Intermediate BFF) in EtOH (10 mL) was added $N_2H4H_2O$ (132 mg, 26 uL, 98% solution). The reaction mixture was stirred at 80° C. for 12 hour. On completion, the reaction mixture was concentrated in vacuo. Then residue was diluted with DCM (20 mL) and filtered. The filtrate was concentrated in vacuo to give the title compound (300 mg, 90% yield) as light yellow oil. $^1H$ NMR (400 MHz, $CDCl_3$) δ 3.92 (s, 2H), 3.76 (s, 2H), 2.67-2.61 (m, 1H), 2.40-2.31 (m, 1H), 2.25-2.16 (m, 2H), 1.93-1.75 (m, 3H), 1.43 (s, 9H), 1.40-1.26 (m, 3H), 0.81 (d, J=6.6 Hz, 3H).

4-[[(2R)-2-(2-azaspiro[3.3]heptan-6-yl)propyl]amino]-2-(2,6-dioxo-3-piperidyl)isoindoline- 1,3-dione (Intermediate BFI)

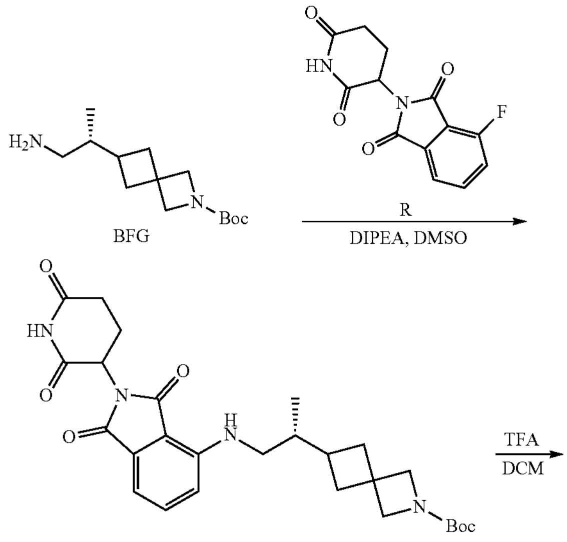

BFG

-continued

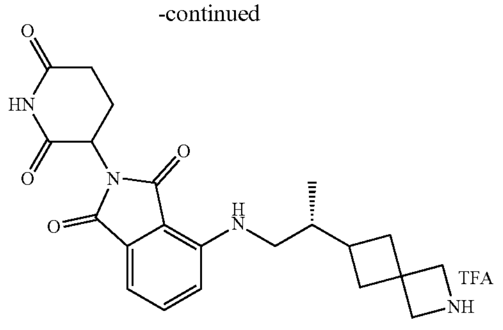

BFI

Step 1—Tert-butyl 6-[(1R)-2-[[2-(2,6-dioxo-3-piperidyl)-1,3-dioxo-isoindolin-4-yl]amino]-1-methyl-ethyl]-2-azaspiro[3.3]heptane-2-carboxylate To a mixture of 2-(2,6-dioxo-3-piperidyl)-4-fluoro-isoindoline-1,3-dione (326 mg, 1.18 mmol, Intermediate R) and tert-butyl 6-[(1R)-2-amino-1-methyl-ethyl]-2-azaspiro[3.3]heptane-2-carboxylate (300 mg, 1.18 mmol, Intermediate BFG) in DMSO (10 mL) was added DIPEA (304.85 mg, 2.36 mmol, 410.85 uL). The mixture was stirred at 130° C. for 2 hours. On completion, the residue was poured into water (30 mL) and the aqueous phase was extracted with ethyl acetate (2×20 mL). The combined organic phase was washed with brine (2×30 mL), dried with anhydrous $Na_2SO_4$, filtered and concentrated in vacuo to give the residue. The residue was purified by reverse phase to give the title compound (425 mg, 70% yield) as a yellow solid. $^1H$ NMR (400 MHz, $CDCl_3$) δ 8.07 (s, 1H), 7.50 (dd, J=7.2, 8.4 Hz, 1H), 7.10 (d, J=6.8 Hz, 1H), 6.86 (d, J=8.4 Hz, 1H), 6.26 (t, J=5.2 Hz, 1H), 4.92 (dd, J=5.2, 12.0 Hz, 1H), 3.98-3.92 (m, 2H), 3.79 (s, 2H), 3.23-3.12 (m, 1H), 3.00 (dd, J=6.4, 13.2 Hz, 1H), 2.94-2.87 (m, 1H), 2.85-2.69 (m, 2H), 2.37-2.22 (m, 2H), 2.19-2.11 (m, 1H), 1.98-1.85 (m, 2H), 1.68 (dd, J=7.2, 14.8 Hz, 2H), 1.43 (s, 9H), 0.92 (d, J=6.8 Hz, 3H).

Step 2—4-[[(2R)-2-(2-azaspiro[3.3]heptan-6-yl)propyl]amino]-2-(2,6-dioxo-3-piperidyl)isoindoline-1,3-dione To a mixture of tert-butyl 6-[(1R)-2-[[2-(2,6-dioxo-3-piperidyl)-1,3-dioxo-isoindolin-4-yl]amino]-1-methyl-ethyl]-2-azaspiro[3.3]heptane-2-carboxylate (150 mg, 294 umol) in DCM (5 mL) was added TFA (67.0 mg, 587 umol) and the mixture was stirred at 20° C. for 0.5 hour. On completion, the mixture was concentrated in vacuo to give the title compound (134 mg, 99% yield) as brown oil. LC-MS ($ESI^+$) m/z 411.2 $(M+H)^+$.

4-[[(2S)-2-(2-azaspiro[3.3]heptan-6-yl)propyl]amino]-2-(2,6-dioxo-3-piperidyl)isoindoline -1,3-dione (Intermediate BFJ)

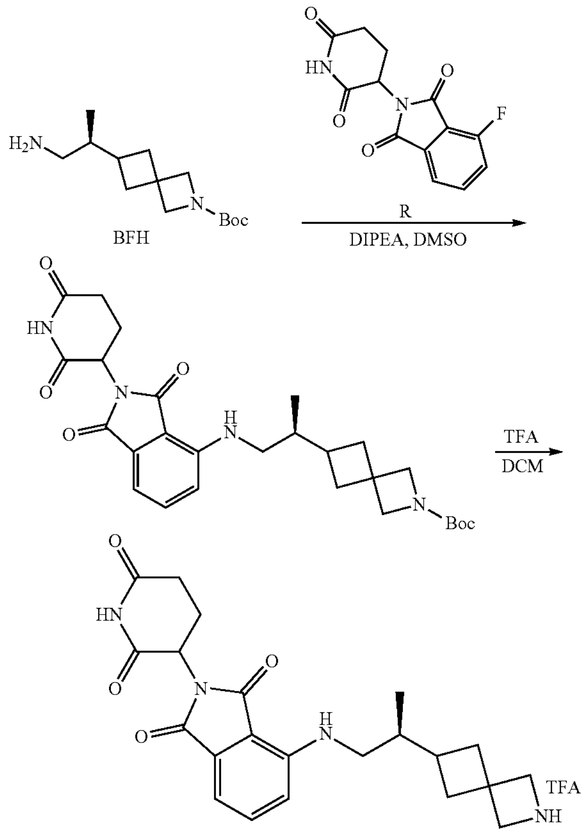

BFJ

Step 1—Tert-butyl 6-[(1S)-2-[[2-(2,6-dioxo-3-piperidyl)-1,3-dioxo-isoindolin-4-yl]amino]-1-methyl-ethyl]-2-azaspiro[3.3]heptane-2-carboxylate To a mixture of tert-butyl 6-[(1S)-2-amino-1-methyl-ethyl]-2-azaspiro[3.3]heptane-2-carboxylate (300 mg, 1.18 mmol, Intermediate BFH) and 2-(2,6-dioxo-3-piperidyl)-4-fluoro-isoindoline-1,3-dione (325 mg, 1.18 mmol, Intermediate R) in DMSO (3.0 mL) was added DIPEA (457 mg, 3.54 mmol, 616 uL). The reaction mixture was stirred at 130° C. for 2 hours. On completion, the reaction mixture was concentrated in vacuo to give a residue. The residue was purified by reverse phase (0.1% FA condition) to give the title compound (480 mg, 79% yield) as yellow solid. $^1H$ NMR (400 MHz, DMSO-$d_6$) δ11.09 (s, 1H), 7.65-7.38 (m, 1H), 7.13-6.94 (m, 2H), 6.47 (t, J=6.0 Hz, 1H), 5.09-5.02 (m, 1H), 3.84 (s, 2H), 3.68 (s, 2H), 3.23-3.13 (m, 1H), 3.09-2.98 (m, 1H), 2.94-2.81 (m, 1H), 2.63-2.52 (m, 2H), 2.26-2.15 (m, 2H), 2.06-1.98 (m, 1H), 1.96-1.87 (m, 2H), 1.86-1.76 (m, 1H), 1.70-1.59 (m, 1H), 1.35 (s, 9H), 0.80 (d, J=6.4 Hz, 3H).

Step 2—4-[[(2S)-2-(2-azaspiro[3.3]heptan-6-yl)propyl]amino]-2-(2,6-dioxo-3-piperidyl)isoindoline -1,3-dione To a mixture of tert-butyl 6-[(1S)-2-[[2-(2,6-dioxo-3-piperidyl)-1,3-dioxo-isoindolin-4-yl]amino]-1-methyl-ethyl]-2-azaspiro[3.3]heptane-2-carboxylate (120 mg, 235 umol) in DCM (2.0 mL) was added TFA (1.85 g, 16.2 mmol, 1.20 mL). The reaction mixture was stirred at 25° C. for 0.5 hour. On completion, the reaction mixture was concentrated in vacuo to give title compound (120 mg, 97% yield, TFA salt) as red oil. LC-MS (ESI$^+$) m/z 411.2 (M+H)$^+$.

N-[2-(4-formylcyclohexyl)-6-(2-hydroxy-2-methyl-propoxy)indazol-5-yl]-6-(trifluoromethyl)pyridine-2-carboxamide (Intermediate BFK)

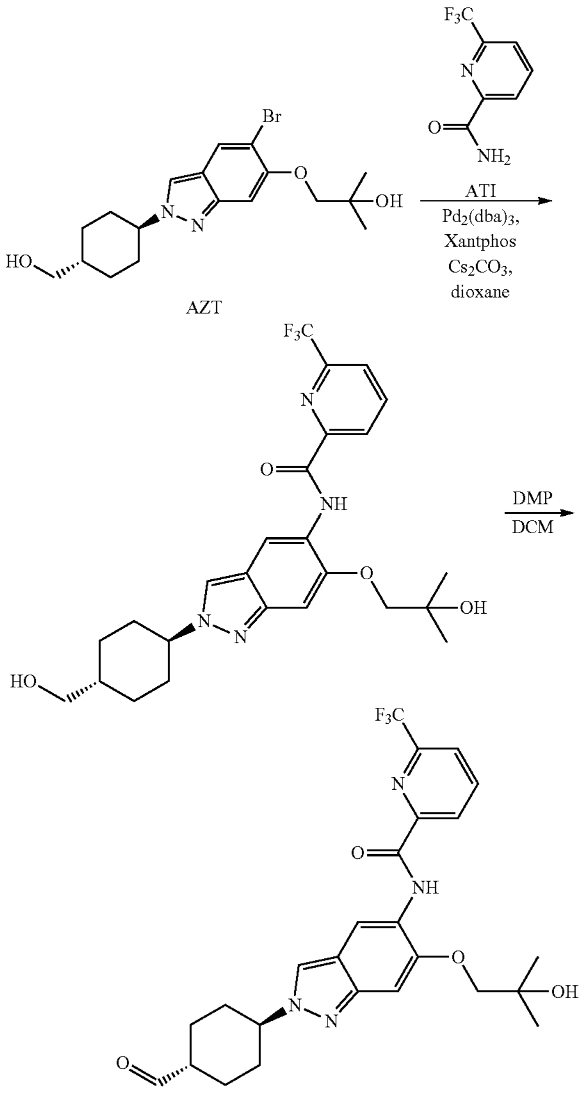

BFK

Step 1—N-[2-[4-(hydroxymethyl)cyclohexyl]-6-(2-hydroxy-2-methyl-propoxy)indazol-5-yl]-6- (trifluoromethyl)pyridine-2-carboxamide To a solution of 1-[5-bromo-2-[4-(hydroxymethyl)cyclohexyl]indazol-6-yl]oxy-2-methyl-propan-2-ol (150 mg, 378 umol, Intermediate AZT) and 6-(trifluoromethyl)pyridine-2-carboxamide (71.8 mg, 378 umol, Intermediate ATI) in dioxane (10 mL) was added $Pd_2(dba)_3$ (34.6 mg, 37.8 umol), $Cs_2CO_3$ (246 mg, 755 umol) and Xantphos (43.7 mg, 75.5 umol). The mixture was degassed and purged with $N_2$ for 3 times and then stirred at 100° C. for 4 hours. On completion, the reaction was diluted with EA (100 mL), washed with water (3×30 mL) and brine (50 mL), dried over $Na_2SO_4$, filtered and concentrated in vacuo to give a residue. The residue was purified by reversed-phase HPLC (0.1% TFA condition) to afford the title compound (80.0 mg, 38% yield) as yellow oil. LC-MS (ESI$^+$) m/z 507.1 (M+H)$^+$.

Step 2—N-[2-(4-formylcyclohexyl)-6-(2-hydroxy-2-methyl-propoxy)indazol-5-yl]-6-(trifluoromethyl) pyridine-2-carboxamide To a solution of N-[2-[4-(hydroxymethyl)cyclohexyl]-6-(2-hydroxy-2-methyl-propoxy)indazol-5-yl]-6-(trifluoromethyl)pyridine-2-carboxamide (80.0 mg, 158 umol) in DCM (2.0 mL) was added DMP (134 mg, 316 umol) and the mixture was stirred at 25° C. for 1 hour. On completion, the reaction was diluted with EA (40 mL), washed with sat. $Na_2S_2O_3$ (20 mL), and sat. $NaHCO_3$ (20 mL). The organic layer was washed with brine (20 mL), dried over $Na_2SO_4$, filtered and concentrated in vacuo to give the title compound (80.0 mg, 80% yield) as a light yellow solid. LC-MS (ESI$^+$) m/z 505.1 (M+H)$^+$.

1-Methyl-3-[3-methyl-4-[4-(methylamino)-1-piperidyl]-2-oxo-benzimidazol-1-yl]piperidine -2,6-dione (Intermediate BFL)

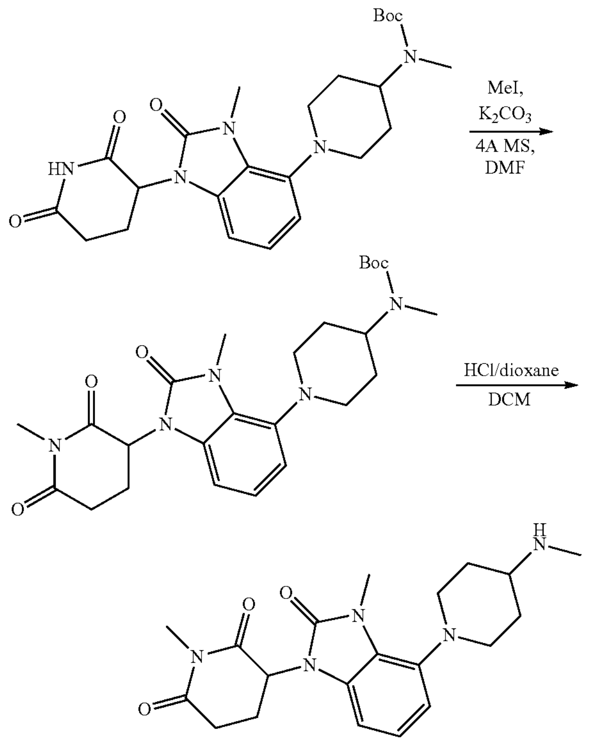

BFL

Step 1—Tert-butyl N-methyl-N-[1-[3-methyl-1-(1-methyl-2,6-dioxo-3-piperidyl)-2-oxo- benzimidazol-4-yl]-4-piperidyl]carbamate To a solution of tert-butyl N-[1-[1-(2, 6-dioxo-3-piperidyl)-3-methyl-2-oxo-benzimidazol-4-yl]-4- piperidyl]-N-methyl-carbamate (353 mg, 742 umol, synthesized via Step 1 of Intermediate AQK) in DMF (5 mL) was added 4 Å molecular sieves (30.0 mg), $K_2CO_3$ (113 mg, 816 umol) at 25° C. The reaction mixture was stirred for 10 minutes. Then MeI (158 mg, 1.11 mmol, 69.3 uL) was added at 0° C. and the mixture was stirred at 25° C. for 16 hours. On completion, the reaction mixture was filtered and the filtrate was adjusted to pH 4-5 with FA. The residue was poured into ice-water (10 mL) and stirred for 2 min. The aqueous phase was then extracted with ethyl acetate (2×10 mL). The combined organic layer was washed with brine (2×20 mL), dried with anhydrous $Na_2SO_4$, filtered and concentrated in vacuo. The residue was purified by silica gel chromatography (ethyl acetate) to give the title compound (240 mg, 66% yield) as yellow solid. LC-MS (ESI$^+$) m/z 486.2 (M+H)$^+$.

Step 2—1-Methyl-3-[3-methyl-4-[4-(methylamino)-1-piperidyl]-2-oxo-benzimidazol-1-yl]piperidine -2,6-dione To a solution of tert-butyl N-methyl-N-[1-[3-methyl-1-(1-methyl-2,6-dioxo-3-piperidyl)-2-oxo- benzimidazol-4-yl]-4-piperidyl]carbamate (100 mg, 206 umol) in DCM (3 mL) was added HCl/dioxane (4 M, 3 mL) and the mixture was stirred at 25° C. for 2 hours. On completion, the reaction mixture was concentrated in vacuo to give the title compound (86.0 mg, 99% yield, HCl salt) as brown solid. LC-MS (ESI$^+$) m/z 386.1 (M+H)$^+$.

4-[6-Methoxy-5-(1-oxo-2-isoquinolyl)indazol-2-yl] cyclohexanecarbaldehyde (Intermediate BFM)

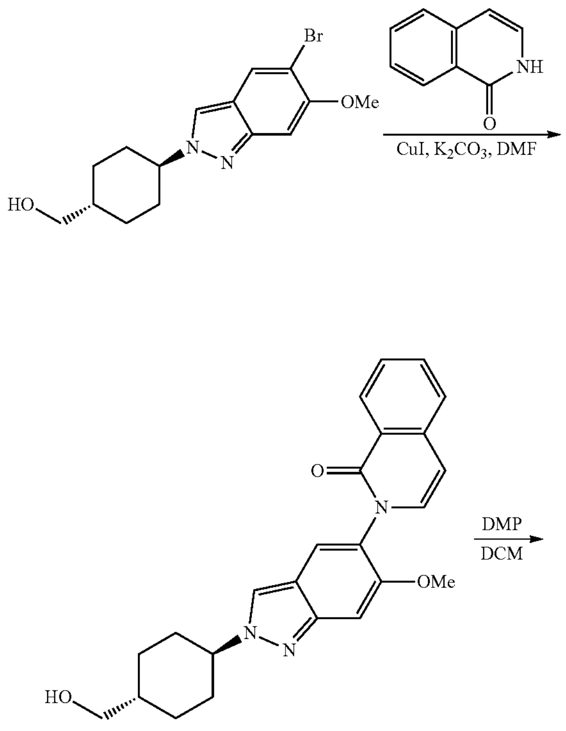

-continued

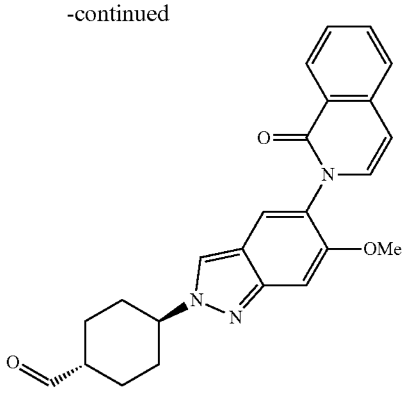

BFM

Step 1—2-[2-[4-(Hydroxymethyl)cyclohexyl]-6-methoxy-indazol-5-yl]isoquinolin-1-one To a solution of [4-(5-bromo-6-methoxy-indazol-2-yl)cyclohexyl]methanol (800 mg, 2.36 mmol, synthesized via Steps 1-3 of Intermediate ATE) and 2H-isoquinolin-1-one (410 mg, 2.83 mmol, CAS #491-30-5) in DMF (10 mL) was added CuI (224 mg, 1.18 mmol) and $K_2CO_3$ (651 mg, 4.72 mmol). The mixture was stirred at 130° C. for 72 hrs. On completion, the reaction mixture was filter and concentrated in vacuo to give a residue. The residue was diluted with DCM (60 mL) and washed with water (2×10 mL), the combined organic layers was dried over $Na_2SO_4$, filtered and concentrated in vacuo to give a residue. The residue was purified by reverse phase (FA condition) to give the title compound (0.35 g, 36% yield) as yellow solid. $^1H$ NMR (400 MHz, DMSO-$d_6$) δ 8.38 (s, 1H), 8.27-8.16 (m, 1H), 7.76-7.68 (m, 3H), 7.60-7.47 (m, 1H), 7.29 (d, J=7.2 Hz, 1H), 7.15 (s, 1H), 6.65 (d, J=7.2 Hz, 1H), 4.50 (t, J=5.2 Hz, 1H), 4.46-4.35 (m, 1H), 3.82-3.69 (m, 3H), 3.31-3.21 (m, 2H), 2.20-2.07 (m, 2H), 1.99-1.78 (m, 4H), 1.54-1.45 (m 1H), 1.25-1.07 (m, 2H).

Step 2—4-[6-Methoxy-5-(1-oxo-2-isoquinolyl)indazol-2-yl]cyclohexanecarbaldehyde

To a solution of 2-[2-[4-(hydroxymethyl)cyclohexyl]-6-methoxy-indazol-5-yl]isoquinolin-1-one (120 mg, 297 umol) in DCM (2 mL) was added DMP (151 mg, 356 umol) and the mixture was stirred at 25° C. for 1 hour. On completion, the reaction mixture was diluted with DCM (30 mL), then quenched by saturated $Na_2S_2O_3$ (10 mL) and saturated $NaHCO_3$ (10 mL) at 0° C., then stirred for 30 minutes. After that, the organic layer was separated and washed with saturated $NaHCO_3$ (10 mL) and saturated NaCl (10 mL). The organic layers dried over $Na_2SO_4$, filtered and concentrated in vacuo to give the title compound (115 mg, 90% yield) as light yellow solid. $^1H$ NMR (400 MHz, DMSO-$d_6$) δ 9.65 (s, 1H), 8.39 (s, 1H), 8.22 (d, J=8.0 Hz, 1H), 7.80-7.66 (m, 3H), 7.58-7.46 (m, 1H), 7.29 (d, J=7.2 Hz, 1H), 7.15 (s, 1H), 6.69-6.58 (m, 1H), 6.50-6.42 (m, 1H), 3.83-3.65 (m, 3H), 2.47-2.37 (m, 1H), 2.22-2.18 (m, 2H), 2.13-2.10 (m, 2H), 2.05-1.90 (m, 2H), 1.53-1.39 (m, 2H).

2-(2,6-dioxo-3-piperidyl)-5-fluoro-isoindoline-1,3-dione (Intermediate HX)

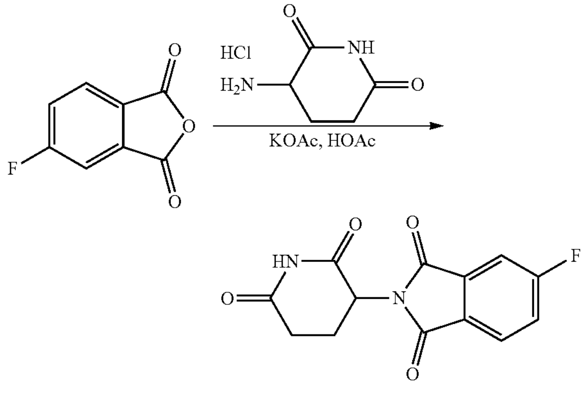

HX

To a mixture of 3-aminopiperidine-2,6-dione (10.8 g, 65.8 mmol, HCl) and KOAc (18.2 g, 185 mmol) in HOAc (160 mL) was added 5-fluoroisobenzofuran-1,3-dione (9.95 g, 59.9 mmol, CAS #319-03-9). Then the mixture was stirred at 90° C. for 16 hours. On completion, the reaction mixture was cooled to 25° C. and diluted with water (600 mL), and then stirred at 0° C. for 0.5 hour then filtered. The filter cake was dried in vacuo to give the title compound (14.0 g, 84% yield) as black brown solid. $^1H$ NMR (400 MHz, DMSO-$d_6$) δ 11.15 (s, 1H), 8.01 (dd, J=4.4, 8.0 Hz, 1H), 7.84 (dd, J=2.4, 7.6 Hz, 1H), 7.76-7.67 (m, 1H), 5.17 (dd, J=5.6, 12.8 Hz, 1H), 2.97-2.83 (m, 1H), 2.65-2.51 (m, 2H), 2.13-2.03 (m, 1H).

2-(2,6-Dioxo-3-piperidyl)-5-[[7-(methylamino)spiro[3.5]nonan-2-yl]amino]isoindoline-1,3-dione (Intermediate BFU)

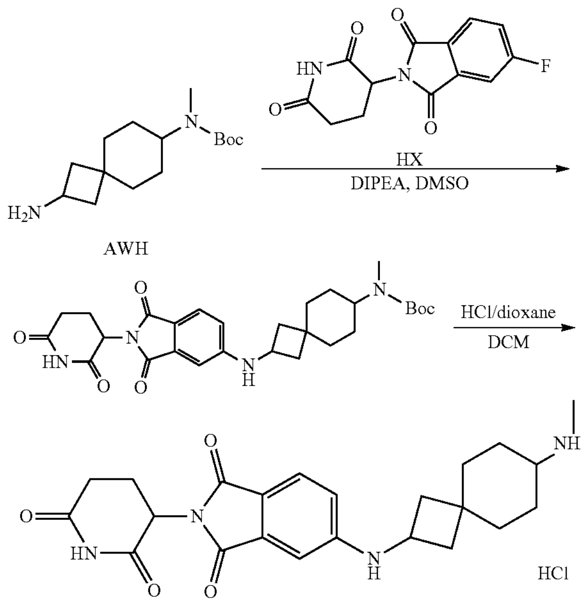

BFU

Step 1—Tert-butyl N-[2-[[2-(2,6-dioxo-3-piperidyl)-1,3-dioxo-isoindolin-5-yl]amino]spiro[3.5]nonan-7-yl]-N-methyl-carbamate To a solution of tert-butyl N-(2-aminospiro[3.5]nonan-7-yl)-N-methyl-carbamate (750 mg, 2.79 mmol, Intermediate AWH) and 2-(2,6-dioxo-3-piperidyl)-5-fluoro-isoindoline-1,3-dione (694 mg, 2.51 mmol, Intermediate HX) in DMSO (10 mL) was added DIPEA (1.11 g, 8.61 mmol) at 25° C. The mixture was stirred at 130° C. for 16 hours. The mixture was concentrated in vacuo. On completion, the crude product was purified by reverse phase (FA condition) to give the title compound (0.68 g, 46% yield) as light yellow solid. $^1H$ NMR (400 MHz, DMSO-$d_6$) δ 11.05 (s, 1H), 7.56 (d, J=8.4 Hz, 1H), 7.35 (d, J=6.0 Hz, 1H), 6.86 (s, 1H), 6.78 (br d, J=9.2 Hz, 1H), 5.02 (dd, J=5.2, 13.0 Hz, 1H), 4.01-3.94 (m, 1H), 2.92-2.82 (m, 1H), 2.64 (s, 3H), 2.59 (br d, J=2.4 Hz, 1H), 2.43 (br d, J=2.0 Hz, 2H), 2.24-2.16 (m, 2H), 2.02-1.96 (m, 1H), 1.90 (br dd, J=2.0, 10.0 Hz, 1H), 1.69-1.63 (m, 2H), 1.58-1.51 (m, 2H), 1.39 (s, 14H).

Step 2—2-(2,6-Dioxo-3-piperidyl)-5-[[7-(methylamino)spiro[3.5]nonan-2-yl]amino]isoindoline-1,3-dione To a solution of tert-butyl N-[2-[[2-(2,6-dioxo-3-piperidyl)-1,3-dioxo-isoindolin-5-yl]amino]spiro [3.5]nonan-7-yl]-N-methyl-carbamate (80.0 mg, 152 umol) in DCM (4.0 mL) was added HCl/dioxane (4 M, 1.91 mL) at 25° C. The mixture was stirred at 25° C. for 1 hour. On completion, the mixture was concentrated in vacuo to give the title compound (63 mg, 89% yield, HCl salt) as light white solid. LC-MS (ESI$^+$) m/z 425.2 (M+H)$^+$.

2-(2,7-diazaspiro[3.5]nonan-2-yl)-2-(2,6-dioxo-3-piperidyl)isoindoline-1,3-dione (Intermediate BFV)

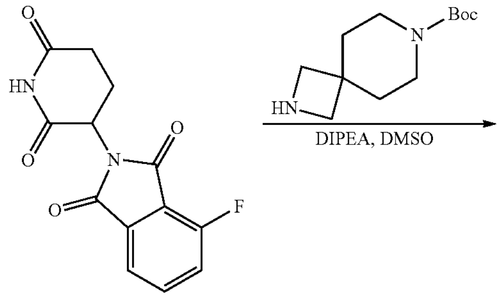

R

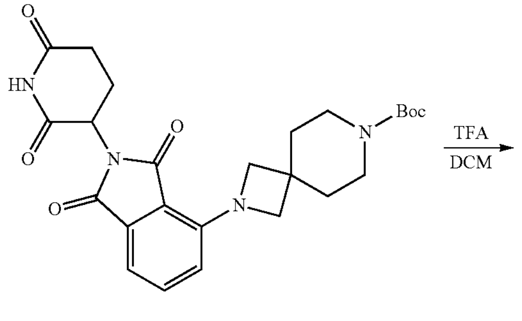

-continued

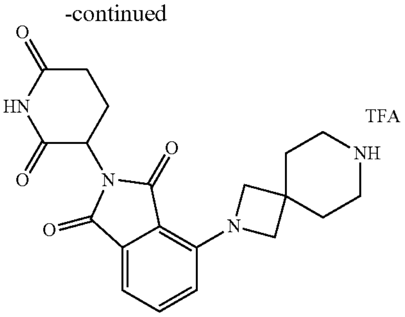

BFV

Step 1—Tert-butyl 2-[2-(2,6-dioxo-3-piperidyl)-1,3-dioxo-isoindolin-4-yl]-2,7-diazaspiro[3.5]nonane-7-carboxylate To a solution of 2-(2,6-dioxo-3-piperidyl)-4-fluoro-isoindoline-1, 3-dione (500 mg, 1.8 mmol, Intermediate R) and tert-butyl 2, 7-diazaspiro[3.5]nonane-7-carboxylate (409 mg, 1.8 mmol, CAS #896464-16-7) in DMSO (8.0 mL) was added DIPEA (701 mg, 5.4 mmol) at 25° C. The mixture was stirred at 130° C. for 2 hours. On completion, the reaction mixture was concentrated in vacuo. The residue was purified by reverse phase (FA condition) to give the title compound (677 mg, 77% yield) as green solid. $^1H$ NMR (400 MHz, DMSO-$d_6$) δ 11.06 (s, 1H), 7.56 (dd, J=7.2, 8.4 Hz, 1H), 7.11 (d, J=7.2 Hz, 1H), 6.77 (d, J=8.4 Hz, 1H), 5.04 (dd, J=5.6, 12.7 Hz, 1H), 3.94 (s, 4H), 2.93-2.80 (m, 1H), 2.65-2.52 (m, 2H), 2.48-2.42 (m, 1H), 2.02-1.94 (m, 1H), 1.73-1.65 (m, 4H), 1.46-1.33 (m, 11H), 1.25-1.03 (m, 1H); LC-MS (ESI+) m/z 383.1 (M+H)$^+$.

Step 2—(2,7-diazaspiro[3.5]nonan-2-yl)-2-(2,6-dioxo-3-piperidyl)isoindoline-1,3-dione To a solution of tert-butyl 2-[2-(2,6-dioxo-3-piperidyl)-1, 3-dioxo-isoindolin-4-yl]-2,7-diazaspiro[3.5] nonane-7-carboxylate (80.0 mg, 165 umol) in DCM (2.0 mL) was added TFA (2.0 mL, 27.0 mmol) at 25° C. The mixture was stirred at 25° C. for 1 hour. On completion, the mixture was concentrated in vacuo to give the compound (80.0 mg, 97% yield, TFA salt) as light yellow solid. LC-MS (ESI$^+$) m/z 383.1 (M+H)$^+$.

Pyridazine-3-carboxamide (Intermediate BFW)

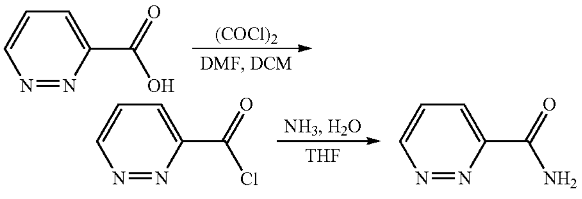

BFW

Step 1—Pyridazine-3-carbonyl chloride

To a mixture of pyridazine-3-carboxylic acid (2.0 g, 16.1 mmol, from CAS #2164-61-6) and DMF (58.9 mg, 805 umol,) in DCM (30.0 mL) was added $(COCl)_2$ (4.1 g, 32.2 mmol) at 0° C. The mixture was stirred at 25° C. for 1 hour. On the completion, the mixture was concentrated in vacuo to give the title compound (2.2 g, 96% yield) as green solid.

Step 2—Pyridazine-3-carboxamide $NH_3.H_2O$ (21.6 g, 154 mmol, 25% solution) was added to a solution of pyridazine-3-carbonyl chloride (2.2 g, 15.4 mmol) in THE (30.0 mL), the mixture was stirred at 25° C. for 1 hour. On completion, the mixture was concentrated in vacuo to give a residue. The residue was diluted in $H_2O$ (100 mL) and extracted with DCM/MeOH=20:1 (6×150 mL). The combined organic layers were washed with brine (20.0 mL), dried over $Na_2SO_4$, filtered and concentrated in vacuo to give the crude product. The crude product was purified by column chromatography on silica gel (PE:EA:DCM=5:1:0.1-1:1:0.2) to give the title compound (1.1 g, 58% yield) as white solid. $^1H$ NMR (400 MHz, DMSO-$d_6$) δ 9.40 (dd, J=1.6, 5.0 Hz, 1H), 8.59 (s, 1H), 8.20 (dd, J=1.6, 8.4 Hz, 1H), 7.99-7.86 (m, 2H).

N-[2-(4-formylcyclohexyl)-6-methoxy-indazol-5-yl] pyridazine-3-carboxamide (Intermediate BFX)

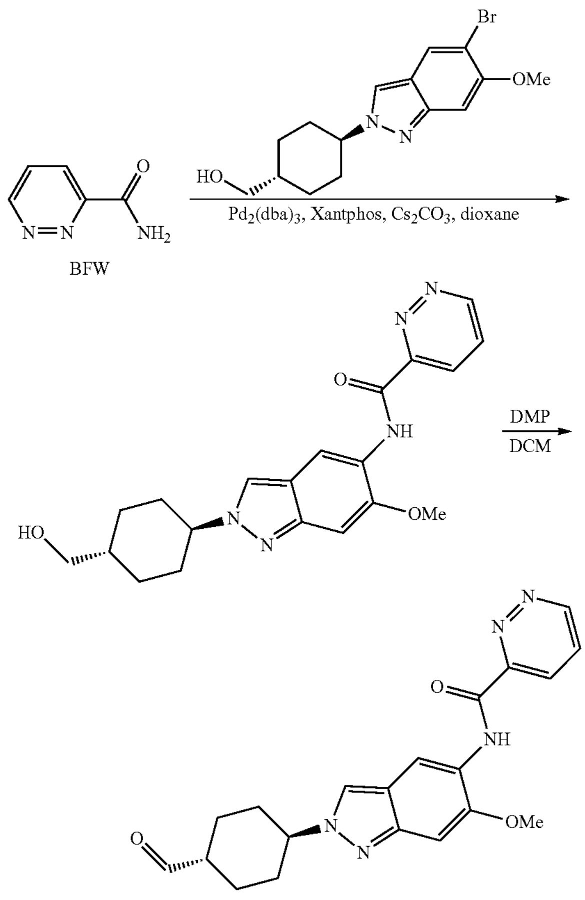

BFW

BFX

Step 1—N-[2-[4-(hydroxymethyl)cyclohexyl]-6-methoxy-indazol-5-yl]pyridazine-3-carboxamide A mixture of pyridazine-3-carboxamide (400 mg, 3.3 mmol, Intermediate BFW), [4-(5-bromo-6-methoxy- indazol-2-yl) cyclohexyl]methanol (1.10 g, 3.25 mmol, synthesized via Steps 1-3 of Intermediate ATE), Xantphos (1.1 g, 2.0 mmol), $Cs_2CO_3$ (2.1 g, 6.5 mmol) and $Pd_2(dba)_3$ (892 mg, 974 umol) in dioxane (15.0 mL) was stirred at 80° C. for 50 hours under $N_2$. On completion, the mixture was filtered and the cake was washed with DCM (100 mL). The filtrate and washing were combined and concentrated in vacuo to give a crude product. The crude product was purified by reverse phase (FA condition) to give the title compound (657 mg, 53% yield) as yellow solid. LC-MS (ESI$^+$) m/z 382.1 $(M+H)^+$.

Step 2—N-[2-(4-formylcyclohexyl)-6-methoxy-indazol-5-yl]pyridazine-3-carboxamide To a solution of N-[2-[4-(hydroxymethyl)cyclohexyl]-6-methoxy-indazol-5-yl]pyridazine-3- carboxamide (550 mg, 1.4 mmol) in DCM (9.0 mL) was added DMP (917 mg, 2.2 mmol) at 0° C., then the mixture was stirred at 25° C. for 1 hour. On completion, the reaction mixture was quenched with $Na_2S_2O_3$ (1.0 mL) and $NaHCO_3$ (3.0 mL). The mixture was then diluted with water (30 mL), then extracted with DCM (3×80 mL). The combined organic layers were dried over $Na_2SO_4$, filtered and concentrated in vacuo to give the title compound (546 mg, 99% yield) as light yellow solid. $^1H$ NMR (400 MHz, DMSO-$d_6$) δ 10.67 (s, 1H), 9.64 (s, 1H), 9.48 (dd, J=1.6, 5.2 Hz, 1H), 8.70 (s, 1H), 8.38 (dd, J=1.6, 8.6 Hz, 1H), 8.35 (s, 1H), 8.01 (dd, J=5.2, 8.4 Hz, 1H), 7.17 (s, 1H), 4.40 (tt, J=3.6, 11.8 Hz, 1H), 4.01 (s, 3H), 2.46-2.38 (m, 1H), 2.25-2.17 (m, 2H), 2.15-2.06 (m, 2H), 1.98-1.89 (m, 2H), 1.45 (dq, J=3.2, 13.0 Hz, 2H).

Tert-butyl 7-(2-aminoethyl)-2-azaspiro[3.5]nonane-2-carboxylate (Intermediate BFY)

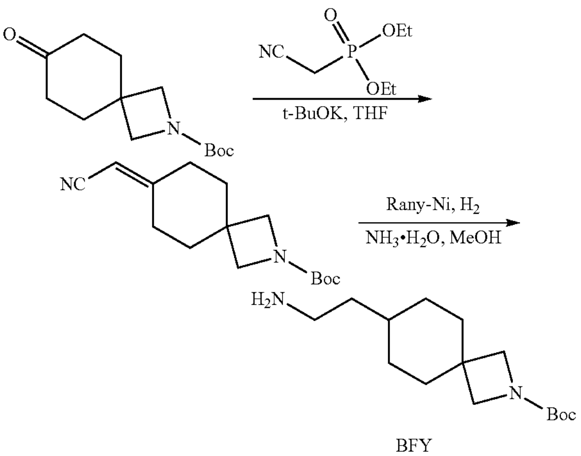

BFY

Step 1—Tert-butyl 7-(cyanomethylene)-2-azaspiro [3.5]nonane-2-carboxylate

To a solution of 2-diethoxyphosphorylacetonitrile (166 mg, 940 umol, CAS #2537-48-6) in THE (2 mL) was added t-BuOK (105 mg, 940 umol) at 0° C. Then tert-butyl 7-oxo-2-azaspiro[3.5]nonane-2- carboxylate (150 mg, 626 umol, CAS #1363381-22-9) was added to above mixture and the reaction mixture was stirred at 25° C. for 2 hours. On completion, the reaction mixture was diluted with $H_2O$ (5 mL), and extracted with EA (3×5 mL). The combined organic layer was washed with brine (2×5 mL), dried over by $Na_2SO_4$, filtered and concentrated in vacuo. The residue was purified by column chromatography ($SiO_2$, petroleum ether/ethyl acetate=10/1 to 5/1) to give the title compound (150 mg, 91% yield) as a white solid. $^1H$ NMR (400 MHz, DMSO-$d_6$) δ 5.44 (s, 1H), 3.57 (s, 4H), 2.39 (t, J=6.0 Hz, 2H), 2.25 (t, J=6.0 Hz, 2H), 1.81-1.66 (m, 4H), 1.38 (s, 9H).

Step 2—Tert-butyl 7-(2-aminoethyl)-2-azaspiro[3.5] nonane-2-carboxylate

To a solution of tert-butyl 7-(cyanomethylene)-2-azaspiro [3.5]nonane-2-carboxylate (150 mg, 571 umol) in $NH_3.H_2O$ (0.4 mL) and MeOH (4 mL) was added Raney-Ni (97.9 mg, 1.14 mmol) at 25° C. The reaction mixture was stirred at 25° C. for 3 hours under $H_2$ (50 psi). On completion, the mixture was filtered with celite and the filtrate was concentrated in vacuo to give the title compound (110 mg, 71% yield) as colorless oil.

4-[2-(2-Azaspiro[3.5]nonan-7-yl)ethylamino]-2-(2,6-dioxo-3-piperidyl)isoindoline-1,3-dione (Intermediate BFZ)

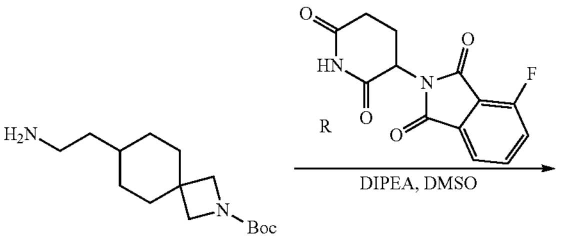

BFY

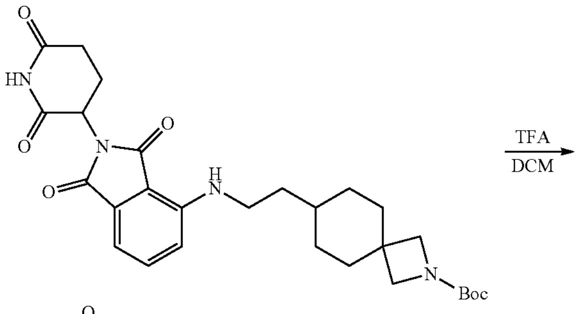

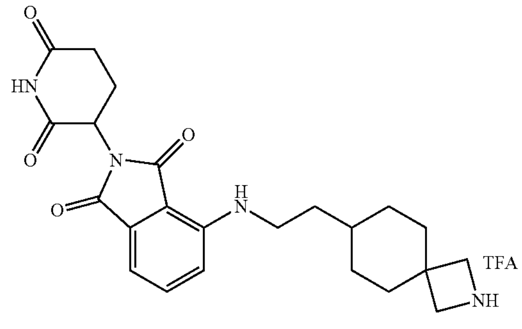

BFZ

Step 1—Tert-butyl 7-[2-[[2-(2,6-dioxo-3-piperidyl)-1,3-dioxo-isoindolin-4-yl]amino]ethyl]-2- azaspiro [3.5]nonane-2-carboxylate To a solution of tert-butyl 7-(2-aminoethyl)-2-azaspiro [3.5]nonane-2-carboxylate (110 mg, 409 umol, Intermediate BFY) and 2-(2,6-dioxo-3-piperidyl)-4-fluoro-isoindoline-1,3-dione (135 mg, 491 umol, Intermediate R) in DMSO (2 mL) was added DIPEA (105 mg, 819 umol) at 25° C. The reaction mixture was stirred at 130° C. for 3 hours. On completion, the reaction mixture was concentrated in vacuo. The residue was purified by reverse phase (0.1% FA condition) to give the title compound (120 mg, 55% yield) as a yellow solid. $^1H$ NMR (400 MHz, DMSO-$d_6$) δ 11.09 (s, 1H), 7.58 (dd, J=7.6, 8.4 Hz, 1H), 7.08 (d, J=8.8 Hz, 1H), 7.02 (d, J=6.8 Hz, 1H), 6.49 (t, J=5.6 Hz, 1H), 5.04 (dd, J=5.2, 12.8 Hz, 1H), 3.53-3.40 (m, 4H), 3.29 (s, 2H), 2.94-2.83 (m, 1H), 2.61-2.56 (m, 2H), 2.06-1.99 (m, 1H), 1.79 (d, J=12.4 Hz, 2H), 1.69-1.62 (m, 2H), 1.52-1.43 (m, 3H), 1.40 (s, 1H), 1.37 (s, 9H), 1.35-1.32 (m, 1H), 1.03-0.88 (m, 2H); LC-MS (ESI$^+$) m/z 525.1 $(M+H)^+$.

Step 2—4-[2-(2-Azaspiro[3.5]nonan-7-yl)ethylamino]-2-(2,6-dioxo-3-piperidyl)isoindoline-1,3-dione To a solution of tert-butyl 7-[2-[[2-(2,6-dioxo-3-piperidyl)-1,3-dioxo-isoindolin-4-yl]amino]ethyl]-2- azaspiro [3.5]nonane-2-carboxylate (110 mg, 209 umol) in DCM (4 mL) was added TFA (2 mL) at 25° C. The mixture was stirred at 25° C. for 1 hour. On completion, the reaction mixture was concentrated in vacuo to give the title compound (110 mg, 97% yield, TFA salt) as yellow oil. LC-MS (ESI$^+$) m/z 425.2 $(M+H)^+$.

3-[4-[(1R,5S)-8-Azabicyclo[3.2.1]octan-3-yl]-3-methyl-2-oxo-benzimidazol-1-yl]piperidine- 2,6-dione (Intermediate BGA)

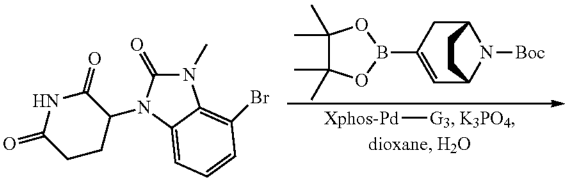

HP

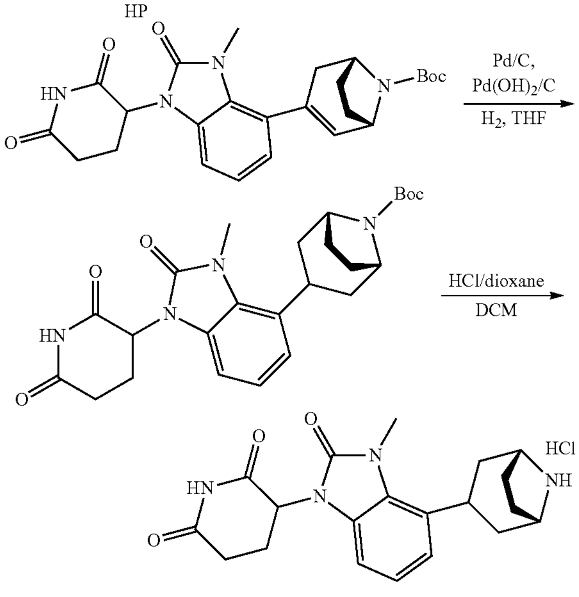

BGA

Step 1—Tert-butyl (1R,5S)-3-[1-(2, 6-dioxo-3-piperidyl)-3-methyl-2-oxo-benzimidazol-4-yl]-8-azabicyclo[3.2.1]oct-3-ene-8-carboxylate A solution of 3-(4-bromo-3-methyl-2-oxo-benzimidazol-1-yl)piperidine-2,6-dione (800 mg, 2.37 mmol, Intermediate HP), tert-butyl (1R,5S)-3-(4,4,5,5-tetramethyl-1,3,2-dioxaborolan-2-yl)-8- azabicyclo[3.2.1]oct-3-ene-8-carboxylate (CAS #900503-08-4, 952 mg, 2.84 mmol), Xphos-Pd-G3 (200 mg, 236 umol) and $K_3PO_4$ (1.00 g, 4.73 mmol) in a mixed solvent of dioxane (12 mL) and $H_2O$ (1.2 mL) was stirred at 80° C. for 4 hrs. On completion, the reaction mixture was filtered and the residue was concentrated in vacuo. The residue was quenched with water (10 mL) and the aqueous phase was extracted with ethyl acetate (3×20 mL). The combined organic layer was washed with brine (3×20 mL), dried with anhydrous $Na_2SO_4$, filtered and concentrated in vacuo. The crude product was purified by reverse phase flash (0.1% FA condition) to give the title compound (740 mg, 67% yield) as white solid. $^1H$ NMR (400 MHz, DMSO-$d_6$) δ 11.10 (s, 1H), 7.09-6.94 (m, 2H), 6.76 (d, J=5.6 Hz, 1H), 6.03 (d, J=4.8 Hz, 1H), 5.38 (dd, J=5.6, 12.4 Hz, 1H), 4.37 (s, 1H), 4.32-4.20 (m, 1H), 3.31 (s, 3H), 2.97-2.83 (m, 2H), 2.73-2.60 (m, 2H), 2.26-2.13 (m, 2H), 1.99 (s, 3H), 1.88-1.78 (m, 1H), 1.42 (s, 9H); LC-MS ($ESI^+$) m/z 467.2 $(M+H)^+$.

Step 2—Tert-butyl (1R,5S)-3-[1-(2, 6-dioxo-3-piperidyl)-3-methyl-2-oxo-benzimidazol-4-yl]-8- azabicyclo[3.2.1]octane-8-carboxylate To a solution of tert-butyl (1R,5S)-3-[1-(2,6-dioxo-3-piperidyl)-3-methyl-2-oxo-benzimidazol-4-yl]-8-azabicyclo[3.2.1]oct-3-ene-8-carboxylate (740 mg, 1.58 mmol) in THF (8 mL) was added Pd/C (80.0 mg, 1.59 mmol, 10% wt), $Pd(OH)_2/C$ (80.0 mg, 1.59 mmol, 10% wt) under $N_2$ atmosphere. The suspension was stirred at 25° C. for 20 hours under $H_2$ (15 psi). On completion, the reaction mixture was filtered and the filtrate was concentrated in vacuo to give the title compound (680 mg, 91% yield) as white solid. LC-MS ($ESI^+$) m/z 469.2 $(M+H)^+$.

Step 3—3-[4-[(1R,5S)-8-Azabicyclo[3.2.1]octan-3-yl]-3-methyl-2-oxo-benzimidazol-1-yl]piperidine-2,6-dione To a solution of tert-butyl (1R, 5S)-3-[1-(2, 6-dioxo-3-piperidyl)-3-methyl-2-oxo-benzimidazol-4-yl]-8-azabicyclo[3.2.1]octane-8-carboxylate (110 mg, 231 umol) in DCM (3 mL) was added HCl/dioxane (4 M, 3 mL). The mixture was stirred at 25° C. for 2 hours. On completion, the reaction mixture was filtered and the filtrate was concentrated in vacuo to give the title compound (92.0 mg, 98% yield, HCl salt) as white solid. LC-MS ($ESI^+$) m/z 369.1 $(M+H)^+$.

3-[3-Methyl-4-(methylaminomethyl)-2-oxo-benzimidazol-1-yl]piperidine-2,6-dione (Intermediate BGB)

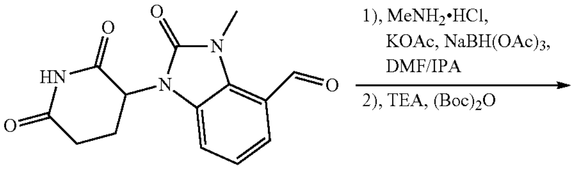

WW

-continued

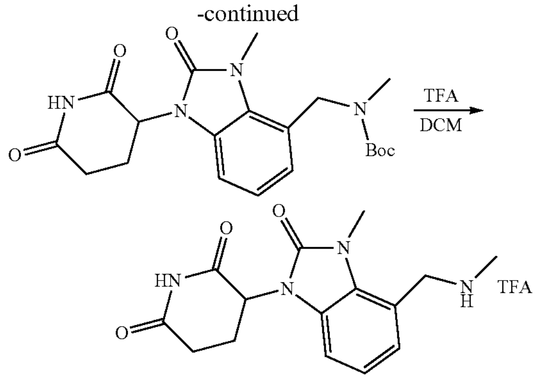

BGB

Step 1—Tert-butyl N-[[1-(2,6-dioxo-3-piperidyl)-3-methyl-2-oxo-benzimidazol-4-yl]methyl]-N—methyl-carbamate To a solution of 1-(2,6-dioxo-3-piperidyl)-3-methyl-2-oxo-benzimidazole-4-carbaldehyde (0.2 g, 696 umol, Intermediate WW), TEA (176 mg, 1.74 mmol) and methanamine; hydrochloride (117 mg, 1.74 mmol) in a mixed solvent of IPA (20 mL) and DMF (2 mL) was added AcOH (41.8 mg, 696 umol). Thirty minutes later, $NaBH(OAc)_3$ (295 mg, 1.39 mmol) was added into the above mixture and the reaction mixture was stirred at 20° C. for 12 hrs. Then $Boc_2O$ (760 mg, 3.48 mmol) and TEA (211 mg, 2.09 mmol) was added and the reaction mixture was stirred at 20° C. for 2 hrs. On completion, the mixture was quenched with water (50 mL), then extracted with EA (2×50 mL). The organic layer was concentrated in vacuo and the residue was purified by reverse phase (0.1% FA condition) to give the title compound (120 mg, 43% yield) as a white solid. $^1H$ NMR (400 MHz, DMSO-$d_6$) δ 11.10 (s, 1H), 7.08-7.00 (m, 2H), 6.76 (dd, J=2.0, 6.8 Hz, 1H), 5.38 (dd, J=5.2, 12.4 Hz, 1H), 4.83 (s, 2H), 3.55 (s, 3H), 2.94-2.83 (m, 1H), 2.79 (s, 3H), 2.77-2.62 (m, 2H), 2.04-1.96 (m, 1H), 1.40 (s, 9H).

Step 2—3-[3-Methyl-4-(methylaminomethyl)-2-oxo-benzimidazol-1-yl]piperidine-2,6-dione To a solution of tert-butyl N-[[1-(2,6-dioxo-3-piperidyl)-3-methyl-2-oxo-benzimidazol-4-yl]methyl]-N-methyl-carbamate (60.0 mg, 149 umol) in DCM (5 mL) was added TFA (5 mL). The reaction mixture was stirred at 20° C. for 0.5 hr. On completion, the mixture was concentrated in vacuo to give the title compound (60.0 mg, 97% yield, TFA salt) as yellow oil. LC-MS ($ESI^+$) m/z 272.1 $(M-30)^+$.

(1R, 4R)-Methyl 4-(2-bromoacetyl)cyclohexanecarboxylate (Intermediate BGC)

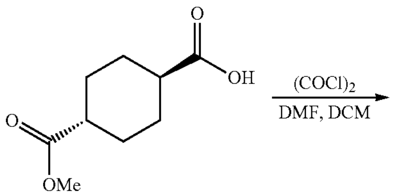

-continued

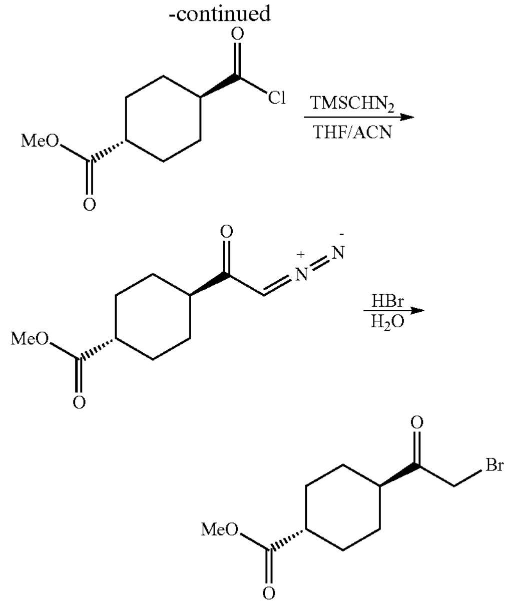

BGC

Step 1—(1R, 4R)-methyl 4-(chlorocarbonyl)cyclohexanecarboxylate

To a solution of 4-methoxycarbonylcyclohexanecarboxylic acid (1.00 g, 5.37 mmol, CAS #15177-67-0) in DCM (10 mL) was added DMF (39.2 mg, 537 umol) and dropwise $(COCl)_2$ (1.50 g, 11.8 mmol) at 25° C. The mixture was stirred at 45° C. for 1 hour. On completion, the reaction mixture was concentrated in vacuo to give the title compound (1.10 g, 100% yield) as brown oil. After adding methanol, LC-MS ($ESI^+$) m/z 201.2 $(M+H)^+$.

Step 2—(1R, 4R)-Methyl 4-(2-diazoacetyl)cyclohexanecarboxylate

To a solution of methyl 4-chlorocarbonylcyclohexanecarboxylate (1.10 g, 5.38 mmol) in a mixed solvent of THE (5.0 mL) and ACN (5.0 mL) was added dropwise $TMSCHN_2$ (2.0 M, 3.23 mL, 6.45 mmol) at 0° C. The mixture was stirred at 0° C. for 1 hour and then at 25° C. for another 1 hour. On completion, the reaction mixture was concentrated in vacuo to give the title compound (1.10 g, 100% yield) as brown oil. After adding methanol, LC-MS ($ESI^+$) m/z 201.2 $(M+H)^+$.

Step 3—(1R, 4R)-Methyl 4-(2-bromoacetyl)cyclohexanecarboxylate

To a solution of 2-(4-methoxycarbonylcyclohexyl)-2-oxo-ethanediazonium (1.10 g, 5.21 mmol) in a mixed solvent of THF (3.0 mL) and MeCN (3.0 mL) was added dropwise HBr (1.14 g, 6.77 mmol, 48% solution). The mixture was stirred at 0° C. for 15 min. On completion, the reaction mixture was partitioned between sat. $NaHCO_3$ (50 mL) and EA (50 mL). The organic phase was separated, washed with brine (50 mL), dried over $Na_2SO_4$, filtered and concentrated in vacuo to give a residue. The residue was purified by column chromatography ($SiO_2$, petroleum ether/ethyl acetate=100/1 to 10/1) to give the title compound (0.60 g, 23% yield) as an off-white solid. $^1H$ NMR (400 MHz, $CDCl_3$) δ 4.17 (s, 1H), 3.97 (s, 1H), 3.68 (s, 3H), 2.82-2.60 (m, 1H), 2.37-2.23 (m, 1H), 2.18-1.92 (m, 4H), 1.56-1.38 (m, 4H); LC-MS ($ESI^+$) m/z 263.2 $(M+H)^+$.

(1R, 4R)-Methyl 4-(6-bromo-7-methoxyimidazo[1,2-a]pyridin-2-yl)cyclohexanecarboxylate (Intermediate BGD)

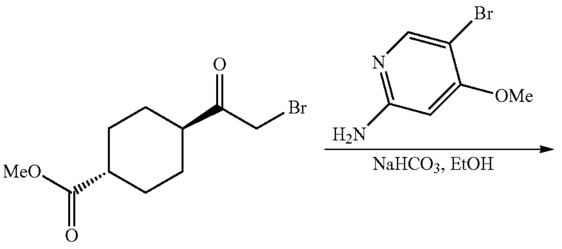

BGC

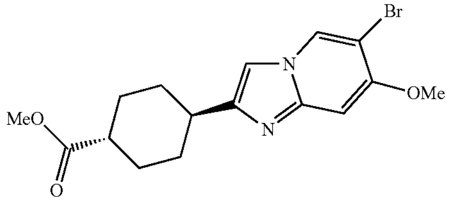

BGD

Step 1—(1R, 4R)-Methyl 4-(6-bromo-7-methoxyimidazo[1,2-a]pyridin-2-yl)cyclohexanecarboxylate To a solution of methyl 4-(2-bromoacetyl)cyclohexanecarboxylate (500 mg, 1.90 mmol, Intermediate BGC) and 5-bromo-4-methoxy-pyridin-2-amine (385 mg, 1.90 mmol, CAS #1232431-11-6) in EtOH (10 mL) was added $NaHCO_3$ (319 mg, 3.80 mmol). The mixture was stirred at 90° C. for 12 hours. On completion, the reaction mixture was concentrated in vacuo to give a residue. The residue was purified by column chromatography ($SiO_2$, DCM/MeOH=100/1 to 20/1) to give the title compound (500 mg, 63% yield) as an off-white solid. LC-MS ($ESI^+$) m/z 369.2 $(M+H)^+$. The structure of the compound was confirmed by HMBP and HSQC spectrum.

6-(1,1-Difluoroethyl)-N-(2-((1R,4R)-4-formylcyclohexyl)-7-methoxyimidazo [1,2-a] pyridine -6-yl) picolinamide (Intermediate BGE)

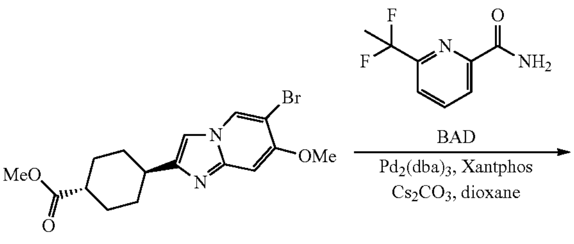

BGD

-continued

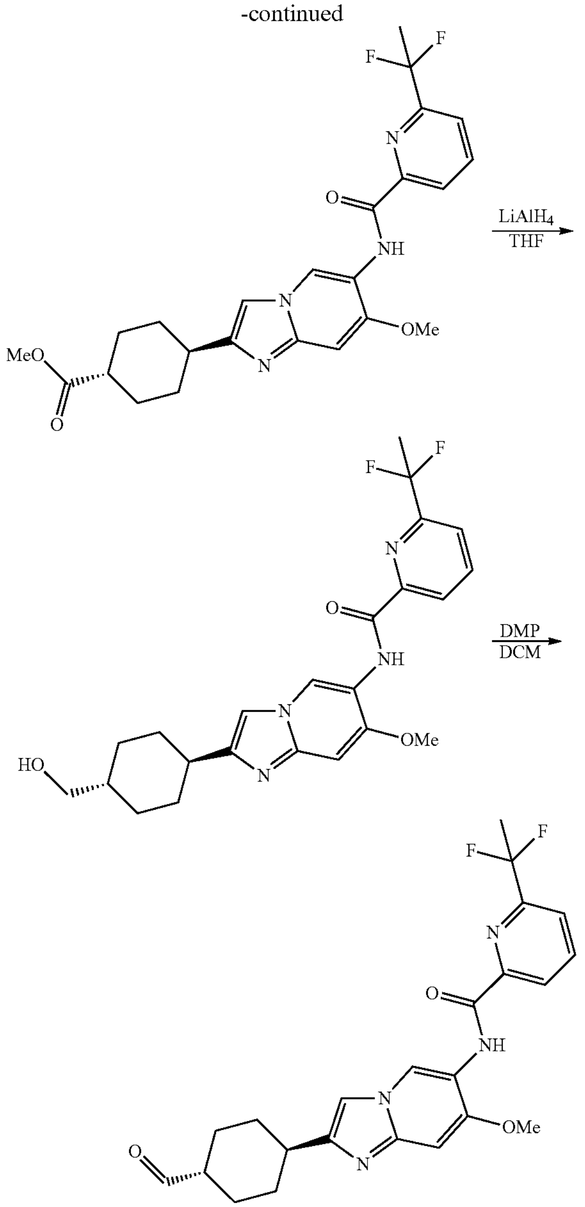

BGE

Step 1—(1R,4R)-Methyl 4-(6-(6-(1,1-difluoroethyl) picolinamido)-7-methoxyimidazo[1,2-a]pyridine -2-yl)cyclohexanecarboxylate To a solution of methyl 4-(6-bromo-7-methoxy-imidazo [1,2-a]pyridin-2-yl)cyclohexanecarboxylate (500 mg, 1.36 mmol, Intermediate BGD) and 6-(1,1-difluoroethyl)pyridine-2-carboxamide (253 mg, 1.36 mmol, Intermediate BAD) in dioxane (7.0 mL) was added $Pd_2(dba)_3$ (124 mg, 136 umol), $Cs_2CO_3$ (887 mg, 2.72 mmol) and Xantphos (157 mg, 272 umol). The mixture was stirred at 80° C. under nitrogen atmosphere for 12 hours. On completion, the reaction mixture was filtered and the filtrate was concentrated in vacuo to give a residue. The residue was purified by column chromatography ($SiO_2$, DCM/MeOH=100/1 to 20/1) to give the title compound (250 mg, 23% yield) as an off-white solid. LC-MS ($ESI^+$) m/z 473.4 $(M+H)^+$.

Step 2—6-(1,1-Difluoroethyl)-N-(2-((1r,4r)-4-(hydroxymethyl)cyclohexyl)-7-methoxyimidazo[1,2-a] pyridin-6-yl)picolinamide To a solution of methyl 4-[6-[[6-(1, 1-difluoroethyl)pyridine-2-carbonyl]amino]-7-methoxy-imidazo [1,2-a]pyridin-2-yl]cyclohexanecarboxylate (200 mg, 423 umol) in THE (4.0 mL) was added $LiAlH_4$ (32.1 mg, 846 umol) at 0° C. and the mixture was stirred at 0° C. for 0.5 hour. On completion, the reaction mixture was quenched with $H_2O$ (0.1 mL) at 0° C. and then diluted with THF (10 mL) and dried over $Na_2SO_4$, filtered and concentrated in vacuo to give a residue. The residue was purified by prep-TLC ($SiO_2$, DCM:MeOH=20:1) to give the title compound (180 mg, 95% yield) as a light brown solid. LC-MS ($ESI^+$) m/z 445.4 $(M+H)^+$.

Step 3—6-(1,1-Difluoroethyl)-N-(2-((1R,4R)-4-formylcyclohexyl)-7-methoxyimidazo[1,2-a]pyridine -6-yl)picolinamide To a solution of 6-(1, 1-difluoroethyl)-N-[2-[4-(hydroxymethyl)cyclohexyl]-7-methoxy-imidazo[1,2-a] pyridin-6-yl]pyridine-2-carboxamide (180 mg, 404 umol) in DCM (2.0 mL) was added DMP (223 mg, 526 umol) at 0° C. The mixture was stirred at 25° C. for 1 hour. On completion, the reaction mixture was quenched with sat. $Na_2SO_3$ (20 mL) and sat. $NaHCO_3$ (20 mL) at 0° C. And then the mixture was diluted with $H_2O$ (10 mL) and extracted with DCM (3×50 mL). The combined organic layers were washed with brine (50 mL), dried over $Na_2SO_4$, filtered and concentrated in vacuo to give a residue. The residue was purified by prep-TLC ($SiO_2$, DCM:MeOH=20: 1) to give the title compound (115 mg, 51% yield) as a light brown solid. LC-MS ($ESI^+$) m/z 443.3 $(M+H)^+$.

N-(2-((1r,4r)-4-formylcyclohexyl)-6-(2-hydroxypropan-2-yl)-2H-indazol-5-yl)-2-methyloxazole-4-carboxamide (Intermediate BGF)

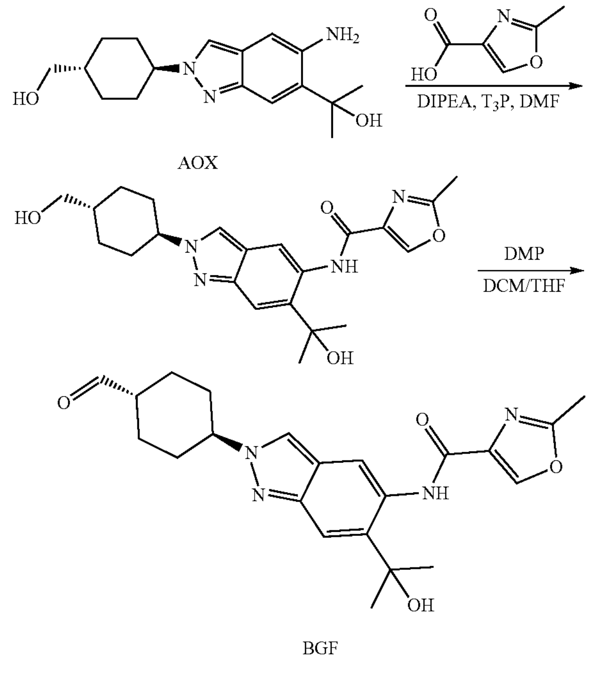

AOX

BGF

Step 1—N-(2-((1r,4r)-4-(hydroxymethyl)cyclohexyl)-6-(2-hydroxypropan-2-yl)-2H-indazol-5-yl)-2-methyloxazole-4-carboxamide To a solution of 2-[5-amino-2-[4-(hydroxymethyl)cyclohexyl]indazol-6-yl]propan-2-ol (200 mg, 659 umol, Intermediate AOX), 2-methyloxazole-4-carboxylic acid (CAS #23062-17-1, 83.7 mg, 659 umol) in DMF (2 mL) was added DIPEA (1.28 g, 9.89 mmol) and $T_3P$ (838 mg, 1.32 mmol, 50% solution) and the mixture was stirred at 20° C. for 12 hours. On completion, the reaction mixture was quenched with $H_2O$ (0.5 mL). The mixture was purified by reverse phase flash (0.1% FA) to give the title compound (200 mg, 63% yield) as a yellow solid. LC-MS ($ESI^+$) m/z 413.2 $(M+H)^+$.

Step 2—N-(2-((1r,4r)-4-formylcyclohexyl)-6-(2-hydroxypropan-2-yl)-2H-indazol-5-yl)-2- methyloxazole-4-carboxamide To a solution of N-[2-[4-(hydroxymethyl)cyclohexyl]-6-(1-hydroxy-1-methyl-ethyl)indazol-5-yl]-2-methyl-oxazole-4-carboxamide (180 mg, 436 umol) in DCM (9 mL) and THF (9 mL) was added DMP (222 mg, 523 umol) at 0° C. The mixture was stirred at 0-25° C. for 1 hour. On completion, the reaction mixture was quenched with $H_2O$ (10 mL) at 25° C. and extracted with EA (3×10 mL). The combined organic layers were washed with brine (2×10 mL), dried over $Na_2SO_4$ and filtered. The filtrate was concentrated in vacuo to give the title compound (175 mg, 95% yield) as a brown solid. LC-MS ($ESI^+$) m/z 411.4 $(M+H)^+$.

N-[2-(4-formylcyclohexyl)-5-methoxy-1,3-benzoxazol-6-yl]-2-methyl-oxazole-4-carboxamide (Intermediate BGG)

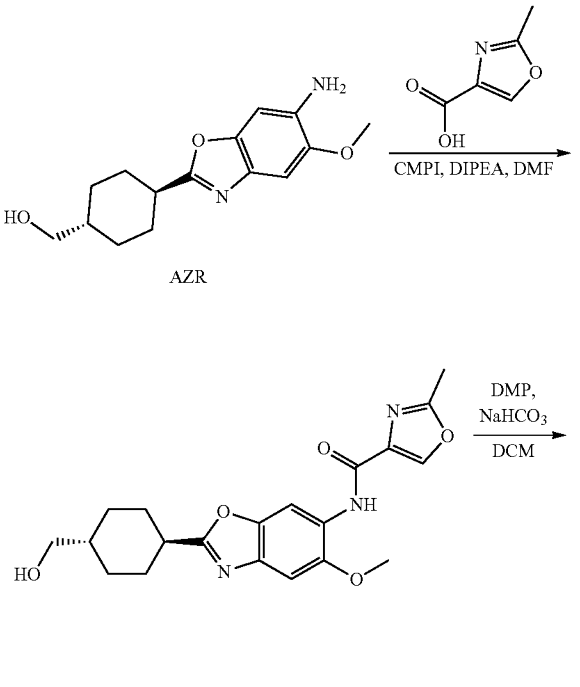

AZR

-continued

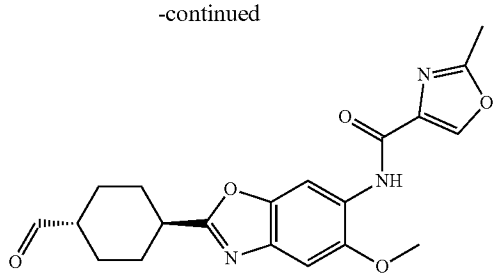

BGG

Step 1—N-[2-[4-(hydroxymethyl)cyclohexyl]-5-methoxy-1,3-benzoxazol-6-yl]-2-methyl-oxazole-4-carboxamide A mixture of 2-methyloxazole-4-carboxylic acid (96.5 mg, 759 umol, CAS #23062-17-1), CMPI (240 mg, 940 umol) and DIPEA (294 mg, 2.28 mmol) in DMF (2 mL) was stirred at ° C. for 0.5 hr. Then a mixture of [4-(6-amino-5-methoxy-1,3-benzoxazol-2-yl)cyclohexyl]methanol (200 mg, 724 umol, Intermediate AZR) in DMF (2 mL) was added at 20° C. The reaction mixture was stirred at 20° C. for 1 hrs. On completion, the reaction mixture was quenched with water (1 mL). The mixture was diluted with water (50 mL) and extracted with EA (3×30 mL). The organic layer was washed with brine (3×40 mL), then dried over anhydrous sodium sulfate and filtered. The filtrate was concentrated in vacuo and the residue was purified by silica gel chromatography (PE:EA=1:5) to give the title compound (180 mg, 64% yield) as yellow solid. $^1H$ NMR (400 MHz, DMSO-$d_6$) δ 9.38 (s, 1H), 8.71 (s, 1H), 8.56 (s, 1H), 7.45 (s, 1H), 3.97 (s, 3H), 3.41 (br s, 1H), 3.26 (d, J=6.4 Hz, 2H), 2.93-2.83 (m, 1H), 2.52 (s, 3H), 2.22-2.10 (m, 2H), 1.90-1.81 (m, 2H), 1.62-1.49 (m, 2H), 1.48-1.36 (m, 1H), 1.13-1.00 (m, 2H).

Step 2—N-[2-(4-formylcyclohexyl)-5-methoxy-1,3-benzoxazol-6-yl]-2-methyl-oxazole-4- carboxamide To a mixture of N-[2-[4-(hydroxymethyl)cyclohexyl]-5-methoxy-1,3-benzoxazol-6-yl]-2-methyl- oxazole-4-carboxamide (150 mg, 389 umol) and $NaHCO_3$ (163 mg, 1.95 mmol, 75.6 uL) in DCM (10 mL) was added DMP (247 mg, 584 umol, 181 uL) at 0° C. The reaction mixture was stirred at 20° C. for 2 hrs. On completion, the reaction mixture was diluted with saturated $Na_2S_2O_3$ aq. (5 mL) and saturated $NaHCO_3$ aq. (5 mL). The mixture was diluted with water (50 mL) and extracted with DCM (3×30 mL). The organic layer was washed with saturated $NaHCO_3$ aqueous (2×50 mL) and brine (3×50 mL). The organic layer was then dried over anhydrous sodium sulfate and filtered. The filtrate was concentrated in vacuo and the crude product was purified by reverse phase flash (0.1% FA condition) to give the title compound (80.0 mg, 53% yield) as yellow solid. $^1H$ NMR (400 MHz, DMSO-$d_6$) δ 9.62 (s, 1H), 9.38 (s, 1H), 8.71 (s, 1H), 8.60-8.53 (m, 1H), 7.46 (s, 1H), 3.97 (s, 3H), 3.00-2.90 (m, 1H), 2.52 (s, 3H), 2.43-2.34 (m, 1H), 2.27-2.17 (m, 2H), 2.10-2.00 (m, 2H), 1.71-1.58 (m, 2H), 1.45-1.32 (m, 2H).

6-[2-[Tert-butyl(dimethyl)silyl]oxy-1,1-dimethyl-ethyl]pyridine-2-carboxamide (Intermediate BGH)

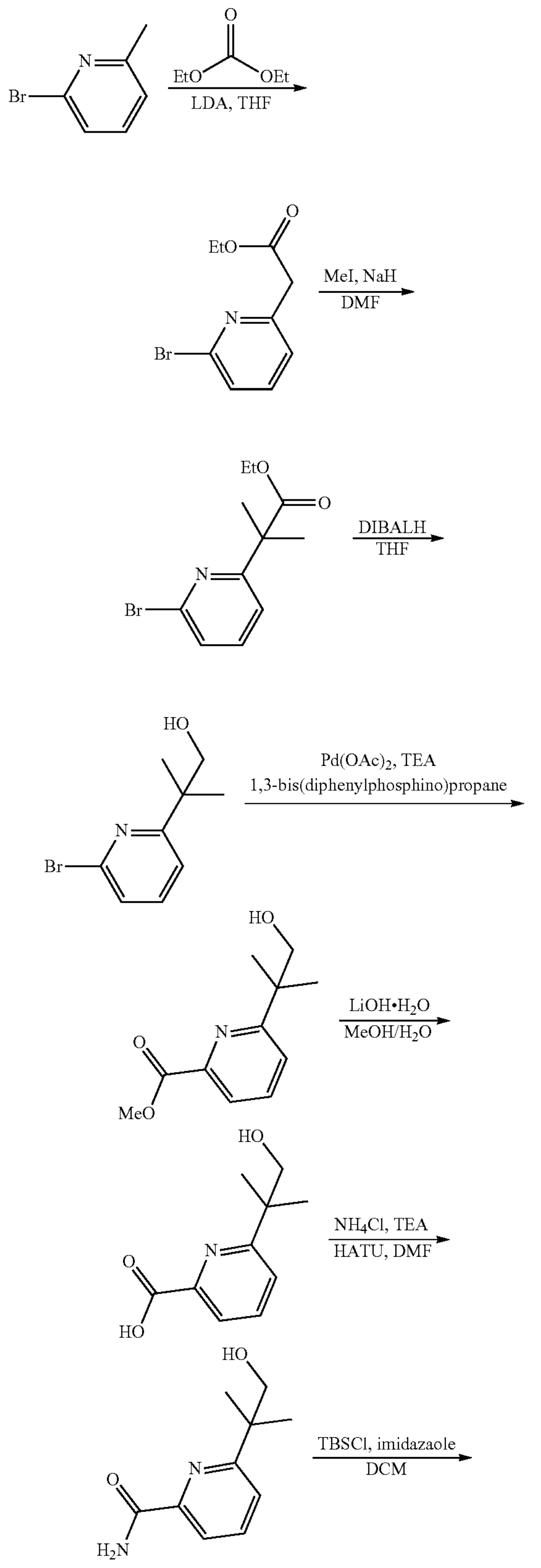

-continued

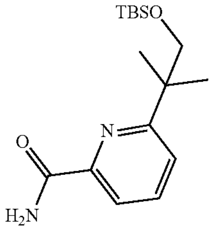

BGH

Step 1—Ethyl 2-(6-bromo-2-pyridyl)acetate

A solution of LDA (2.00 M, 21.8 mL) in THF (50.0 mL) and cooled to −78° C. Then 2-bromo-6-methyl-pyridine (5.00 g, 29.0 mmol, CAS #5315-25-3) was added to above solution at −78° C. and the mixture was stirred at −78° C. for 30 min. Then diethyl carbonate (4.46 g, 37.7 mmol, CAS #105-58-8) was added dropwise and the mixture was stirred at −78° C. for 1 hr. On completion, the mixture was quenched with sat. $NH_4Cl$ (100 mL), then extracted with EA (3×50 mL). The organic layers were washed with brine (2×50 mL), dried over anhydrous $Na_2SO_4$, filtered and concentrated in vacuo. The mixture was purified with silica gel column (PE:EA=15:1) to give the title compound (2.50 g, 35% yield) as yellow oil. $^1H$ NMR (400 MHz, $CDCl_3$) δ 7.57-7.48 (m, 1H), 7.40 (d, J=7.6 Hz, 1H), 7.29 (d, J=7.6 Hz, 1H), 4.19 (q, J=7.2 Hz, 2H), 3.83 (s, 2H), 1.27 (t, J=7.2 Hz, 3H), LC-MS ($ESI^+$) m/z 246.0 $(M+H)^+$.

Step 2—Ethyl 2-(6-bromo-2-pyridyl)-2-methyl-propanoate

To a solution of ethyl 2-(6-bromo-2-pyridyl) acetate (5.00 g, 20.4 mmol) in DMF (50 mL) was added NaH (2.05 g, 51.2 mmol, 60% dispersion in mineral oil) at 0° C. The mixture was stirred at 0° C. for 0.5 hr. Then $CH_3I$ (14.5 g, 102 mmol) was added, the mixture was stirred at 20° C. for 4 hrs. On completion, the mixture quenched with $H_2O$ (250 mL) and extracted with EA (3×50 mL). The organic layers were washed with brine (2×50 mL), dried over anhydrous $Na_2SO_4$, filtered and concentrated in vacuo. The mixture was purified by reverse phase (0.1% FA) to give the title compound (4.60 g, 82% yield) as yellow oil. $^1H$ NMR (400 MHz, $CDCl_3$) δ 7.52-7.46 (m, 1H), 7.34 (d, J=7.6 Hz, 1H), 7.23 (d, J=7.6 Hz, 1H), 4.16 (q, J=7.2 Hz, 2H), 1.59 (s, 6H), 1.21 (t, J=7.2 Hz, 3H), LC-MS ($ESI^+$) m/z 274.0 $(M+H)^+$.

Step 3—2-(6-Bromo-2-pyridyl)-2-methyl-propan-1-ol

To a solution of ethyl 2-(6-bromo-2-pyridyl)-2-methyl-propanoate (1.50 g, 5.51 mmol) in toluene (15 mL) was added diisobutylalumane (1.00 M, 13.7 mL) at −78° C., and the mixture was stirred at −78° C. for 0.5 hr. On completion, the mixture was diluted with toluene (50 mL) and quenched with saturated $NH_4Cl$ (30 mL). The organic layer was washed with saturated $NaHCO_3$ (2×30 mL), brine (2×30 mL), dried over anhydrous $Na_2SO_4$, filtered and concentrated in vacuo to give the title compound (1.12 g, 88% yield) as yellow oil, $^1H$ NMR (400 MHz, DMSO-$d_6$) δ 7.70-7.63 (m, 1H), 7.44-7.40 (m, 2H), 4.68 (t, J=5.6 Hz, 1H), 3.51 (d, J=5.6 Hz, 2H), 1.22 (s, 6H).

Step 4—Methyl 6-(2-hydroxy-1,1-dimethyl-ethyl) pyridine-2-carboxylate

To a solution of 2-(6-bromo-2-pyridyl)-2-methyl-propan-1-ol (900 mg, 3.91 mmol) in MeOH (5.00 mL) and DMSO (5.00 mL) was added TEA (791 mg, 7.82 mmol), $Pd(OAc)_2$ (61.4 mg, 273 umo) and 1,3-bis(diphenylphosphino)propane (112 mg, 273 umol). The mixture was stirred at 80° C. for 16 hrs under CO (50 psi). On completion, the mixture was concentrated in vacuo. The residue was purified by reverse phase: (0.1% FA) to give the title compound (780 mg, 95% yield) as yellow oil. $^1H$ NMR (400 MHz, $CDCl_3$) δ 7.99 (dd, J=1.2, 8.0 Hz, 1H), 7.84 (t, J=8.0 Hz, 1H), 7.52 (dd, J=1.2, 8.0 Hz, 1H), 5.40-5.25 (m, 1H), 4.00 (s, 3H), 3.81 (d, J=6.4 Hz, 2H), 1.37 (s, 6H), LC-MS ($ESI^+$) m/z 210.2 $(M+H)^+$.

Step 5—6-(2-Hydroxy-1,1-dimethyl-ethyl)pyridine-2-carboxylic acid

To a solution of methyl 6-(2-hydroxy-1,1-dimethyl-ethyl) pyridine-2-carboxylate (760 mg, 3.63 mmol) in MeOH (8 mL) and $H_2O$ (2 mL) was added LiOH $H_2O$ (762 mg, 18.1 mmol) and the mixture was stirred at 60° C. for 3 hrs. On completion, the mixture was adjusted to pH=6 with 1N HCl and concentrated in vacuo. The mixture was purified by reverse phase (0.1% FA) to give the title compound (550 mg, 77% yield) as yellow solid. $^1H$ NMR (400 MHz, DMSO-$d_6$) δ 7.95-7.89 (m, 1H), 7.89-7.85 (m, 1H), 7.70-7.62 (m, 1H), 5.21 (s, 1H), 4.13 (s, 1H), 3.59 (s, 2H), 1.28 (s, 6H), LC-MS ($ESI^+$) m/z 196.1 $(M+H)^+$.

Step 6—6-(2-Hydroxy-1,1-dimethyl-ethyl)pyridine-2-carboxamide

To a solution of 6-(2-hydroxy-1,1-dimethyl-ethyl)pyridine-2-carboxylic acid (550 mg, 2.82 mmol), $NH_4Cl$ (3.01 g, 56.3 mmol) in DMF (10.0 mL) was added TEA (855 mg, 8.45 mmol) and HATU (1.61 g, 4.23 mmol), and the mixture was stirred at 20° C. for 1 hr. On completion, the mixture was quenched with $H_2O$ (5 mL) and concentrated in vacuo. The mixture was purified by reverse phase: (0.1% FA) to give the title compound (420 mg, 76% yield) as yellow solid. $^1H$ NMR (400 MHz, $CDCl_3$) δ 8.00 (dd, J=1.2, 8.0 Hz, 1H), 7.78 (t, J=8.0 Hz, 1H), 7.60 (s, 1H), 7.48 (dd, J=1.2, 8.0 Hz, 1H), 5.70 (s, 1H), 3.76 (s, 2H), 2.45 (s, 1H), 1.31 (s, 6H), LC-MS ($ESI^+$) m/z 195.2 $(M+H)^+$.

Step 7—6-[2-[Tert-butyl(dimethyl)silyl]oxy-1,1-dimethyl-ethyl]pyridine-2-carboxamide To a solution of 6-(2-hydroxy-1,1-dimethyl-ethyl)pyridine-2-carboxamide (370 mg, 1.90 mmol) in DCM (8.00 mL) was added TBSCI (344 mg, 2.29 mmol) and imidazole (259 mg, 3.81 mmol), and the mixture was stirred at 25° C. for 16 hrs. On completion, the mixture was diluted with DCM (30 mL) and washed with $H_2O$ (2×15 mL). The organic layer was dried over anhydrous $Na_2SO_4$, filtered and concentrated in vacuo. The mixture was purified by silica gel column (PE:EA=5:1) to give the title compound (500 mg, 85% yield) as yellow oil. $^1H$ NMR (400 MHz, DMSO-$d_6$) δ 8.02 (dd, J=0.8, 7.6 Hz, 1H), 7.91 (s, 1H), 7.77 (t, J=7.6 Hz, 1H), 7.52 (dd, J=0.8, 7.6 Hz, 1H), 5.56 (s, 1H), 3.69 (s, 2H), 1.37 (s, 6H), 0.78 (s, 9H), -0.10 (s, 6H), LC-MS ($ESI^+$) m/z 309.2 $(M+H)^+$.

6-[2-[Tert-butyl(dimethyl)silyl]oxy-1,1-dimethyl-ethyl]-N-[2-(4-formylcyclohexyl)-6-methoxy-indazol-5-yl]pyridine-2-carboxamide (Intermediate BGI)

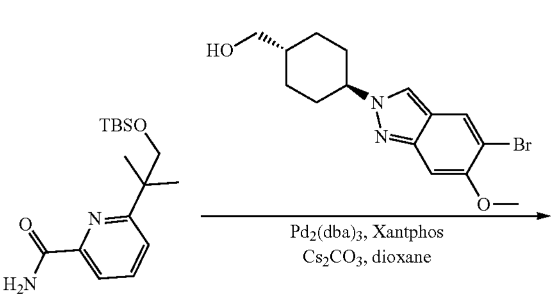

BGH

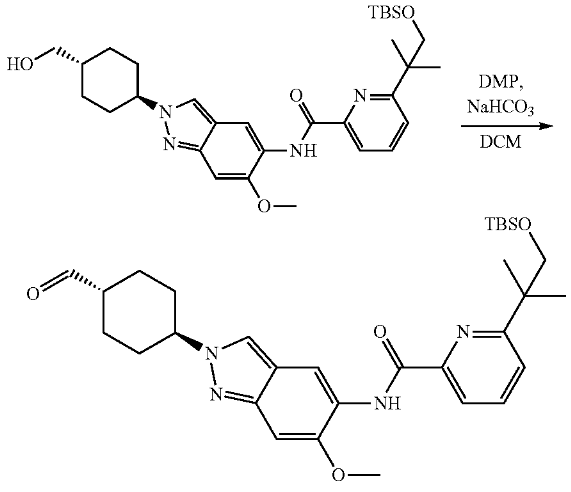

BGI

Step 1—6-[2-[Tert-butyl(dimethyl)silyl]oxy-1,1-dimethyl-ethyl]-N-[2-[4-(hydroxymethyl)cyclohexyl]-6-methoxy-indazol-5-yl]pyridine-2-carboxamide To a solution of 6-[2-[tert-butyl(dimethyl)silyl]oxy-1,1-dimethyl-ethyl]pyridine-2-carboxamide (300 mg, 972 umol, Intermediate BGH), [4-(5-bromo-6-methoxy-indazol-2-yl) cyclohexyl]methanol (300 mg, 884 umol, synthesized via Steps 1-3 of Intermediate ATE) in dioxane (6.00 mL) was added $Pd_2(dba)_3$ (80.9 mg, 88.4 umol), Xantphos (102 mg, 176 umol) and $Cs_2CO_3$ (576 mg, 1.77 mmol). The mixture was stirred at 80° C. for 16 hrs under $N_2$. On completion, the mixture was filtered and concentrated in vacuo. The mixture was purified by silica gel column (EA) to give the title compound (270 mg, 53% yield) as yellow solid. $^1H$ NMR (400 MHz, DMSO-$d_6$) δ 10.98 (s, 1H), 8.68 (s, 1H), 8.31 (s, 1H), 8.04-7.96 (m, 2H), 7.69 (dd, J=1.6, 6.8 Hz, 1H), 7.14 (s, 1H), 4.50-4.20 (m, 2H), 3.98 (s, 3H), 3.78 (s, 2H), 3.30-3.27 (m, 2H), 2.17-2.07 (m, 2H), 1.95-1.84 (m, 4H), 1.55-1.44 (m, 1H), 1.40 (s, 6H), 1.23-1.09 (m, 2H), 0.71 (s, 9H), -0.14 (s, 6H), LC-MS ($ESI^+$) m/z 567.2 $(M+H)^+$.

Step 2—6-[2-[Tert-butyl(dimethyl)silyl]oxy-1,1-dimethyl-ethyl]-N-[2-(4-formylcyclohexyl)-6-methoxy-indazol-5-yl]pyridine-2-carboxamide To a solution of 6-[2-[tert-butyl(dimethyl)silyl]oxy-1,1-dimethyl-ethyl]-N-[2-[4-(hydroxymethyl)cyclohexyl]-6-methoxyindazol-5-yl]pyridine-2-carboxamide (270 mg, 476 umol) in DCM (4.00 mL) was added DMP (303 mg, 714 umol) and $NaHCO_3$ (200 mg, 2.38 mmol) and the mixture was stirred at 25° C. for 1 hr. On completion, the mixture was diluted with DCM (30 mL) and quenched with sat. $Na_2S_2O_3$ (30 mL) and washed with sat. $NaHCO_3$ (2×30 mL). The organic layer was dried over anhydrous $Na_2SO_4$, filtered and concentrated in vacuo to give the title compound (255 mg, 94% yield) as yellow solid. $^1$H NMR (400 MHz, DMSO-$d_6$) δ 10.99 (s, 1H), 9.65 (s, 1H), 8.69 (s, 1H), 8.32 (s, 1H), 8.05-7.97 (m, 2H), 7.72-7.68 (m, 1H), 7.15 (s, 1H), 4.49-4.32 (m, 1H), 4.00 (s, 3H), 3.79 (s, 2H), 2.47-2.37 (m, 1H), 2.25-2.15 (m, 2H), 2.15-2.05 (m, 2H), 2.03-1.90 (m, 2H), 1.52-1.43 (m, 2H), 1.41 (s, 6H), 0.72 (s, 9H), -0.13 (s, 6H), LC-MS (ESI$^+$) m/z 565.4 (M+H)$^+$.

N-(2-((1r,4r)-4-formylcyclohexyl)-5-methoxybenzo[d]oxazol-6-yl)pyrazine-2-carboxamide (Intermediate BGJ)

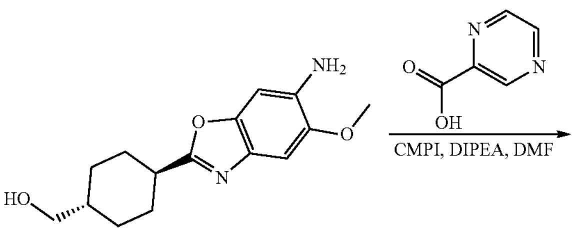

AZR

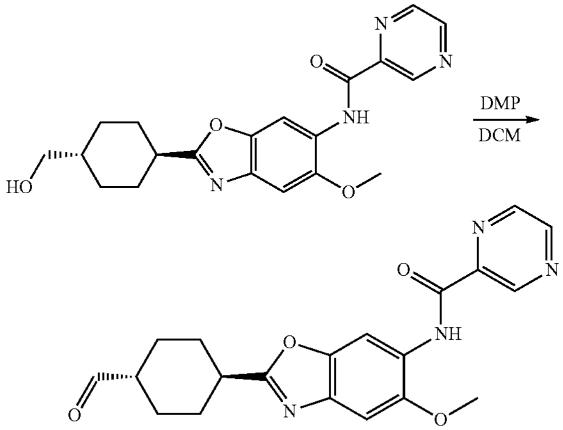

BGJ

Step 1—N-(2-((1r,4r)-4-(hydroxymethyl)cyclohexyl)-5-methoxybenzo[d]oxazol-6-yl)pyrazine-2-carboxamide A solution of pyrazine-2-carboxylic acid (67.4 mg, 543 umol, CAS #98-97-5,) and CMPI (166 mg, 651 umol), DIPEA (210 mg, 1.63 mmol) in DMF (1 mL) was stirred for 10 mins and then added to the solution of [4-(6-amino-5-methoxy-1,3-benzoxazol-2-yl)cyclohexyl]methanol (150 mg, 543 umol, Intermediate AZR) in DMF (1 mL). Then the mixture was stirred at 25° C. for 20 mins. On completion, the mixture was purified by reversed phase flash (0.1% FA condition) to give the title compound (200 mg, 95% yield, FA salt) as a white solid. LC-MS (ESI$^+$) m/z 383.3 (M+H)$^+$.

Step 2—N-(2-((1r,4r)-4-formylcyclohexyl)-5-methoxybenzo[d]oxazol-6-yl)pyrazine-2-carboxamide To a solution of N-[2-[4-(hydroxymethyl)cyclohexyl]-5-methoxy-1,3-benzoxazol-6-yl]pyrazine-2-carboxamide (200 mg, 523 umol) in DCM (2 mL) and THF (1 mL) was added DMP (333 mg, 784 umol) at 0° C. Then the mixture was stirred at 25° C. for 1 hr. On completion, saturated $Na_2S_2O_3$ aq. (3 mL) was added to the solution and the mixture was extracted with DCM (3×30 mL). The combined organic phase was dried over $Na_2SO_4$, filtered and concentrated in vacuo to give the title compound (180 mg, 90% yield) as yellow solid. LC-MS (ESI$^+$) m/z 381.3 (M+H)$^+$.

Pyrimidine-5-carboxamide (Intermediate BGK)

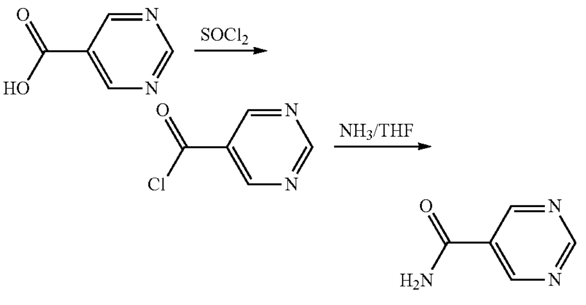

BGK

Step 1—Pyrimidine-5-carbonyl chloride

A solution of pyrimidine-5-carboxylic acid (500 mg, 4.03 mmol, CAS #4595-61-3) in $SOCl_2$ (10 mL) was stirred at 110° C. for 1 hour. On completion, the reaction mixture was concentrated in vacuo to give the title compound (500 mg, 87% yield) as a brown solid, which was used for next step directly.

Step 2—Pyrimidine-5-carboxamide

To a solution of pyrimidine-5-carbonyl chloride (500 mg, 3.51 mmol) in THE (5 mL) was added saturated $NH_3$/THF at 0° C. The mixture was stirred at 25° C. for 0.5 hour. On completion, the reaction mixture was concentrated in vacuo to give the title compound (383 mg, 88% yield) as a brown solid. $^1$H NMR (400 MHz, DMSO-$d_6$) δ 9.30 (s, 1H), 9.21 (s, 2H), 8.50 (br s, 1H), 7.70 (br s, 1H).

N-[2-(4-formylcyclohexyl)-6-methoxy-indazol-5-yl]pyrimidine-5-carboxamide (Intermediate BGL)

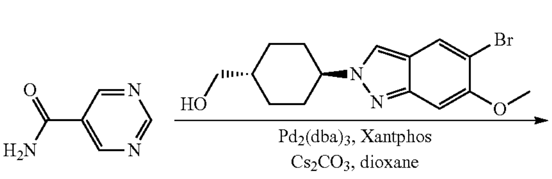

BGK

-continued

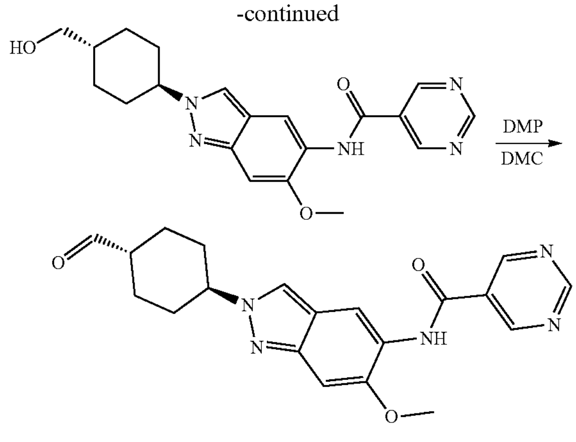

BGL

Step 1—N-[2-[4-(hydroxymethyl)cyclohexyl]-6-methoxy-indazol-5-yl]pyrimidine-5-carboxamide A mixture of pyrimidine-5-carboxamide (152 mg, 1.24 mmol), [4-(5-bromo-6-methoxy-indazol-2-yl)cyclohexyl] methanol (300 mg, 884 umol, synthesized via Steps 1-3 of Intermediate ATE), $Pd_2(dba)_3$ (81.0 mg, 88.4 umol), Xantphos (102 mg, 176 umol) and $Cs_2CO_3$ (576 mg, 1.77 mmol) in dioxane (6 mL) was stirred at 80° C. for 12 hours under $N_2$ atmosphere. On completion, the reaction mixture was filtered and the filtrate was dried in vacuo to give a residue. The crude product was purified by reverse phase flash (0.1% FA condition) to give the title compound (100 mg, 21% yield) as a brown solid. LC-MS ($ESI^+$) m/z 382.1 $(M+H)^+$.

Step 2—N-[2-(4-formylcyclohexyl)-6-methoxy-indazol-5-yl]pyrimidine-5-carboxamide To a solution of N-[2-[4-(hydroxymethyl)cyclohexyl]-6-methoxy-indazol-5-yl]pyrimidine- 5-carboxamide (100 mg, 262 umol) in DCM (5 mL) was added DMP (144 mg, 340 umol). The mixture was stirred at 0-25° C. for 1 hour. On completion, the reaction mixture was quenched by addition saturated $NaHCO_3$ (1 mL) and $Na_2S_2O_3$ (1 mL) aqueous. The mixture was diluted with $H_2O$ (5 mL) and extracted with DCM (2×50 mL). The combined organic layers were washed with brine (30 mL), dried over $Na_2SO_4$, filtered and concentrated in vacuo to give the title compound (100 mg, 38% yield) as a brown solid. LC-MS ($ESI^+$) m/z 380.1 $(M+H)^+$.

Pyridazine-3-carboxamide (Intermediate BGM)

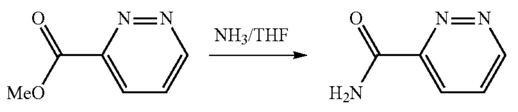

BGM

A solution of methyl pyridazine-3-carboxylate (2.00 g, 14.4 mmol, CAS #34253-02-6) in saturated $NH_3$/THF (50 mL) was stirred at 50° C. for 12 hours. On completion, the reaction mixture was concentrated in vacuo to give the title compound (1.60 g, 80% yield) as a yellow solid, $^1H$ NMR (400 MHz, DMSO-$d_6$) δ 9.40-9.39 (m, 1H), 8.58 (br s, 1H), 8.21-8.19 (m, 1H), 7.91-7.88 (m, 2H).

N-(2-((1r,4r)-4-formylcyclohexyl)-6-methoxy-2H-indazol-5-yl)pyridazine-3-carboxamide (Intermediate BGN)

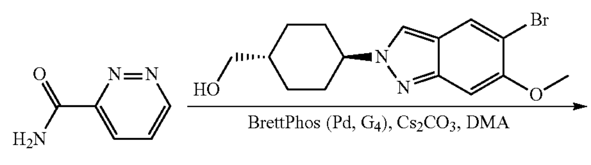

BGM

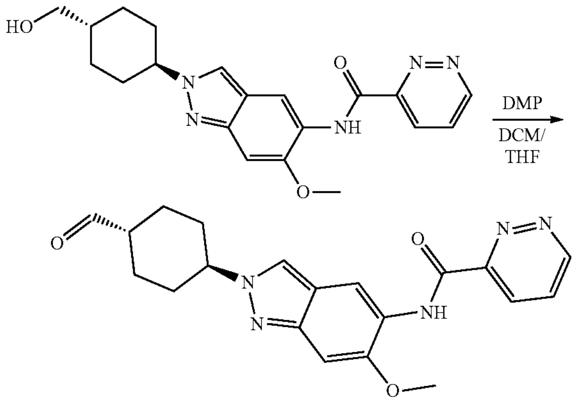

BGN

Step 1—N-(2-((1r,4r)-4-(hydroxymethyl)cyclohexyl)-6-methoxy-2H-indazol-5-yl)pyridazine-3-carboxamide A mixture of [4-(5-bromo-6-methoxy-indazol-2-yl)cyclohexyl]methanol (500 mg, 1.47 mmol, synthesized via Steps 1-3 of Intermediate ATE), pyridazine-3-carboxamide (199 mg, 1.62 mmol, Intermediate BGM), $Cs_2CO_3$ (960 mg, 2.95 mmol), BrettPhos (Pd, G4) (67.8 mg, 73.7 umol) in DMA (5 mL) was stirred at 120° C. for 12 hours under $N_2$ atmosphere. On completion, the reaction mixture was quenched by addition $H_2O$ (0.5 mL) at 25° C., and then purified by reverse phase flash (0.1% FA condition) to give the title compound (60.0 mg, 8% yield) as a yellow solid. LC-MS ($ESI^+$) m/z 382.3 $(M+H)^+$.

Step 2—N-(2-((1r,4r)-4-formylcyclohexyl)-6-methoxy-2H-indazol-5-yl)pyridazine-3-carboxamide To a solution of N-[2-[4-(hydroxymethyl)cyclohexyl]-6-methoxy-indazol-5-yl]pyridazine-3- carboxamide (60.0 mg, 157 umol) in DCM (1 mL) and THE (1 mL) was added DMP (80.0 mg, 188 umol) at 0° C. The mixture was stirred at 25° C. for 1 hour. On completion, the reaction mixture was quenched by addition $Na_2S_2O_3$ (5 mL) at 25° C. and adjusted to pH=8 with $NaHCO_3$ aqueous. The mixture was extracted with DCM (3×5 mL). The combined organic layers were washed with brine (5 mL), dried over $Na_2SO_4$, filtered and concentrated in vacuo to give the title compound (50.0 mg, 83% yield) as a yellow solid. LC-MS ($ESI^+$) m/z 380.3 $(M+H)^+$.

N-[2-(4-formylcyclohexyl)-6-(1-hydroxy-1-methyl-ethyl)indazol-5-yl]-5-(trifluoromethyl) pyrazine-2-carboxamide (Intermediate BGO)

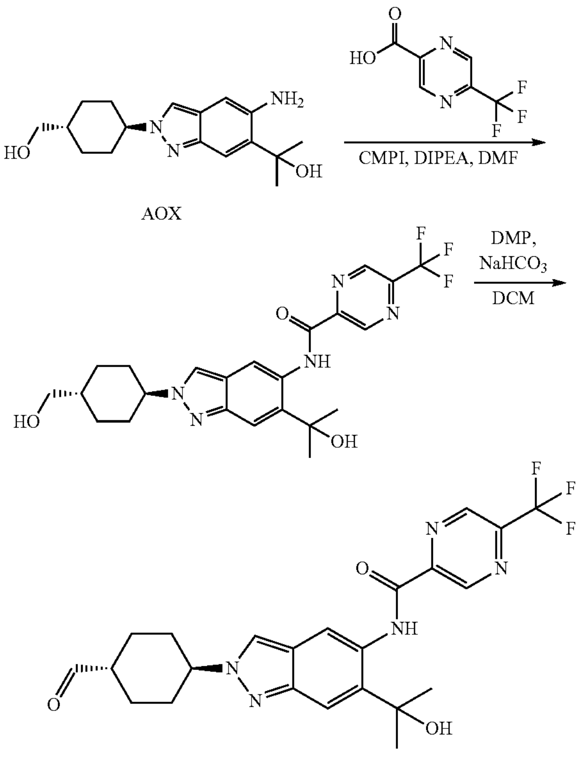

AOX

BGO

Step 1—N-[2-[4-(hydroxymethyl)cyclohexyl]-6-(1-hydroxy-1-methyl-ethyl)indazol-5-yl]-5- (trifluoromethyl)pyrazine-2-carboxamide To a solution of 2-[5-amino-2-[4-(hydroxymethyl)cyclohexyl]indazol-6-yl]propan-2-ol (50.0 mg, 165 umol, Intermediate AOX) and 5-(trifluoromethyl)pyrazine-2-carboxylic acid (28.5 mg, 148 umol, CAS #1060814-50-7) in DMF (1 mL) was added DIPEA (63.9 mg, 494 umol) and CMPI (50.5 mg, 198 umol). The reaction mixture was stirred at 20° C. for 0.5 hr. On completion, the mixture was quenched with water (0.1 mL), concentrated in vacuo. The residue was purified by reverse phase (0.1% FA condition) to give the title compound (50.0 mg, 64% yield) as a yellow solid. $^1H$ NMR (400 MHz, DMSO-$d_6$) δ 12.48 (s, 1H), 9.51 (s, 1H), 9.30 (s, 1H), 8.73 (s, 1H), 8.40 (s, 1H), 7.59 (s, 1H), 6.21 (s, 1H), 4.49 (t, J=5.2 Hz, 1H), 4.46-4.34 (m, 1H), 3.29-3.25 (m, 2H), 2.19-2.09 (m, 2H), 1.95-1.85 (m, 4H), 1.62 (s, 6H), 1.53-1.43 (m, 1H), 1.26-1.06 (m, 2H).

Step 2—N-[2-(4-formylcyclohexyl)-6-(1-hydroxy-1-methyl-ethyl)indazol-5-yl]-5-(trifluoromethyl) pyrazine-2-carboxamide To a solution of N-[2-[4-(hydroxymethyl)cyclohexyl]-6-(1-hydroxy-1-methyl-ethyl)indazol-5- yl]-5-(trifluoromethyl)pyrazine-2-carboxamide (70.0 mg, 147 umol) and $NaHCO_3$ (61.6 mg, 733 umol) in DCM (5 mL) was added DMP (93.3 mg, 220 umol). The reaction mixture was stirred at 20° C. for 2 hrs. On completion, the mixture was quenched with sat. $Na_2S_2O_3$ (20 mL) and $NaHCO_3$ (20 mL), stirred for 10 min, then extracted with DCM (2×30 mL). The organic layer was washed with brine (50 mL), dried over anhydrous $Na_2SO_4$, filtered and the filtrate was concentrated in vacuo to give the title compound (60.0 mg, 86% yield) as a yellow solid. LC-MS ($ESI^+$) m/z 476.3 $(M+H)^+$ 3-Fluoro-N-[2-(4-formylcyclohexyl)-6-(1-hydroxy-1-methyl-ethyl)indazol-5-yl]pyridine-2-carboxamide (Intermediate BGP)

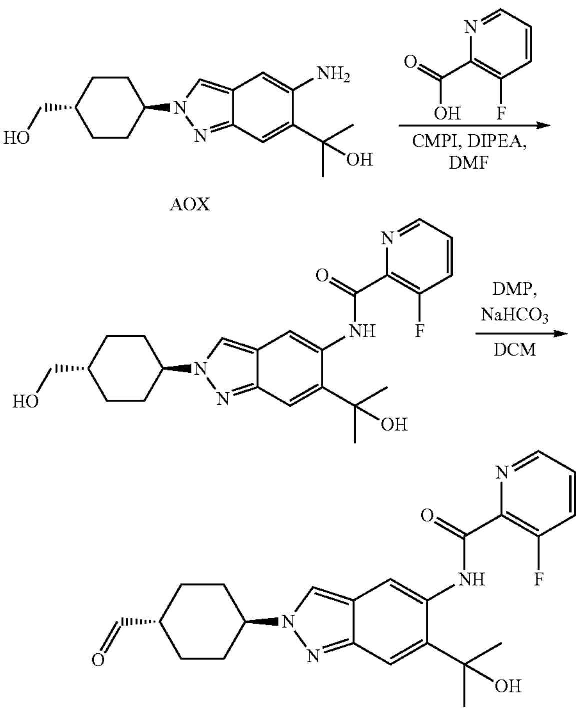

AOX

BGP

Step 1—3-Fluoro-N-[2-[4-(hydroxymethyl)cyclohexyl]-6-(1-hydroxy-1-methyl-ethyl)indazol-5-yl] pyridine-2-carboxamide To a solution of 3-fluoropyridine-2-carboxylic acid (69.7 mg, 494 umol, CAS #152126-31-3) in DMF (4.00 mL) was added CMPI (151 mg, 593 umol) and DIPEA (191 mg, 1.48 mmol). The mixture was stirred at 15° C. for 10 min. Then 2-[5-amino-2-[4-(hydroxymethyl)cyclohexyl]Indazol-6-yl] propan-2-ol (150 mg, 494 umol, Intermediate AOX) was added, the mixture was stirred at 15° C. for 50 min. On completion, the mixture was diluted with $H_2O$ (30 mL), and extracted with EA (3×15 mL). The combined organic layers were washed with brine (2×20 mL), dried over anhydrous $Na_2SO_4$, filtered and the filtrate was concentrated in vacuo to give the title compound (200 mg, 94% yield) as yellow solid. $^1H$ NMR (400 MHz, DMSO-$d_6$) δ 12.12 (s, 1H), 8.63 (s, 1H), 8.58-8.51 (m, 1H), 8.34 (s, 1H), 8.00-7.90 (m, 1H), 7.78-7.67 (m, 1H), 7.56 (s, 1H), 6.03 (s, 1H), 4.53-4.46 (m, 1H), 4.46-4.35 (m, 1H), 3.31-3.25 (m, 2H), 2.20-2.10 (m, 2H), 1.97-1.82 (m, 4H), 1.62 (s, 6H), 1.53-1.39 (m, 1H), 1.21-1.13 (m, 2H), LC-MS ($ESI^+$) m/z 427.3 $(M+H)^+$.

Step 2—3-Fluoro-N-[2-(4-formylcyclohexyl)-6-(1-hydroxy-1-methyl-ethyl)indazol-5-yl]pyridine-2-carboxamide To a solution of 3-fluoro-N-[2-[4-(hydroxymethyl)cyclohexyl]-6-(1-hydroxy-1-methyl-ethyl) indazol-5-yl]pyridine-2-carboxamide (100 mg, 234 umol) in DCM (3.00 mL) was added DMP (149 mg, 351 umol) and $NaHCO_3$ (98.4 mg, 1.17 mmol). The mixture was stirred at 15° C. for 0.5 hr. On completion, the mixture was quenched with DCM (20 mL), and quenched with saturated $Na_2S_2O_3$ (10 mL) and washed with saturated $NaHCO_3$ (3x20 mL). The organic layer was dried over anhydrous $Na_2SO_4$, filtered and concentrated in vacuo to give the title compound (95.0 mg, 95% yield) as yellow solid. $^1$H NMR (400 MHz, DMSO-$d_6$) δ 12.12 (s, 1H), 9.65 (s, 1H), 8.64 (s, 1H), 8.57-8.52 (m, 1H), 8.35 (s, 1H), 7.97-7.90 (m, 1H), 7.76-7.70 (m, 1H), 7.56 (s, 1H), 6.04 (s, 1H), 4.58-4.39 (m, 1H), 2.47-2.38 (m, 1H), 2.24-2.17 (m, 2H), 2.15-2.07 (m, 2H), 2.05-1.92 (m, 2H), 1.62 (s, 6H), 1.53-1.38 (m, 2H), LC-MS (ESI$^+$) m/z 425.1 (M+H)$^+$.

3,5-Difluoro-N-[2-(4-formylcyclohexyl)-6-methoxy-indazol-5-yl]benzamide (Intermediate BGO)

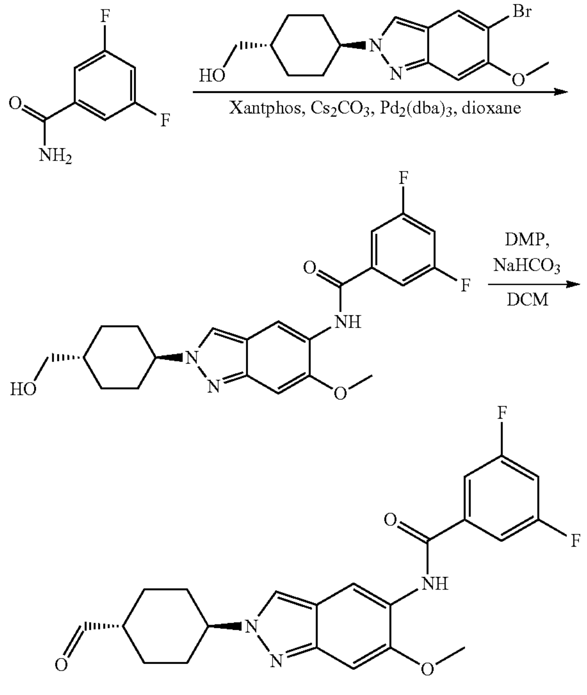

BGQ

Step 1—3,5-Difluoro-N-[2-[4-(hydroxymethyl)cyclohexyl]-6-methoxy-indazol-5-yl]benzamide A mixture of [4-(5-bromo-6-methoxy-indazol-2-yl)cyclohexyl]methanol (300 mg, 884 umol, synthesized via Steps 1-3 of Intermediate ATE), 3,5-difluorobenzamide (208 mg, 1.33 mmol, CAS #132980-99-5), $Pd_2(dba)_3$ (80.9 mg, 88.4 umol), $Cs_2CO_3$ (576 mg, 1.77 mmol) and Xantphos (102 mg, 177 umol) in dioxane (4 mL) was de-gassed and heated at 100° C. for 12 hrs. On completion, the mixture was filtered and the filtrate was concentrated in vacuo. The residue was purified by reverse phase (0.1% FA condition) to give the title compound (150 mg, 41% yield) as a yellow solid. $^1$H NMR (400 MHz, DMSO-$d_6$) δ 9.64 (s, 1H), 8.30 (s, 1H), 7.98 (s, 1H), 7.68 (d, J=6.4 Hz, 2H), 7.55-7.47 (m, 1H), 7.08 (s, 1H), 4.55-4.45 (m, 1H), 4.41-4.31 (m, 1H), 3.86 (s, 3H), 3.30-3.26 (m, 2H), 2.20-2.10 (m, 2H), 1.96-1.85 (m, 4H), 1.54-1.41 (m, 1H), 1.22-1.07 (m, 2H).

Step 2—3,5-Difluoro-N-[2-(4-formylcyclohexyl)-6-methoxy-indazol-5-yl]benzamide

To a solution of 3,5-difluoro-N-[2-[4-(hydroxymethyl) cyclohexyl]-6-methoxy-indazol-5-yl]benzamide (75.0 mg, 181 umol) and $NaHCO_3$ (75.8 mg, 903 umol) in DCM (10 mL) was added DMP (115 mg, 271 umol). The reaction mixture was stirred at 20° C. for 2 hrs. On completion, the mixture was quenched with sat. $Na_2S_2O_3$ (20 mL) and $NaHCO_3$ (20 mL), stirred for 10 min, then extracted with DCM (2x30 mL). The organic layer was washed with brine (50 mL), dried in $Na_2SO_4$, filtered and the filtrate was concentrated in vacuo. The residue was purified by reverse phase (0.1% FA condition) to give the title compound (50.0 mg, 67% yield) as a yellow solid. LC-MS (ESI$^+$) m/z 414.2 (M+H)$^+$.

6-(Trifluoromethyl)pyrazine-2-carboxylic acid (Intermediate BGR)

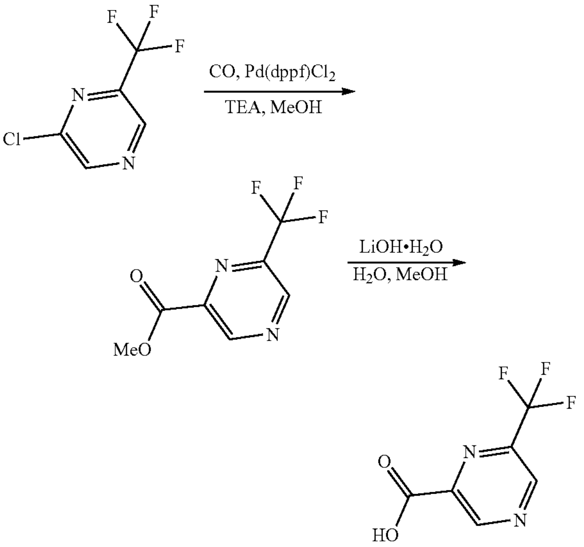

BGR

Step 1—Methyl 6-(trifluoromethyl)pyrazine-2-carboxylate

A solution of 2-chloro-6-(trifluoromethyl)pyrazine (1.90 g, 10.4 mmol), $Pd(dppf)Cl_2$ (762 mg, 1.04 mmol) and TEA (10.5 g, 104 mmol) in MeOH (50 mL) was stirred at 70° C. for 12 hrs under CO (50 Psi) atmosphere. On completion, the mixture was concentrated in vacuo. The residue was purified by silica gel chromatography ($SiO_2$) to give the title compound (1.90 g, 89% yield) as colorless oil. $^1$H NMR (400 MHz, $CDCl_3$) δ 9.52 (s, 1H), 9.15 (s, 1H), 4.08 (s, 3H).

Step 2—6-(Trifluoromethyl)pyrazine-2-carboxylic acid

To a solution of methyl 6-(trifluoromethyl)pyrazine-2-carboxylate (300 mg, 1.46 mmol) in a mixed solvent of $H_2O$ (1 mL) and MeOH (5 mL) was added LiOH $H_2O$ (183 mg, 4.37 mmol). The reaction mixture was stirred at 20° C. for 1 hr. On completion, the mixture was acidified with 1N HCl to pH=3-4, then dried in vacuo to give the title compound (260 mg, 93% yield) as a white solid. $^1$H NMR (400 MHz, DMSO-$d_6$) δ 9.38 (s, 1H), 9.24 (s, 1H).

N-[2-(4-formylcyclohexyl)-6-(1-hydroxy-1-methyl-ethyl)indazol-5-yl]-6-(trifluoromethyl) pyrazine-2-carboxamide (Intermediate BGS)

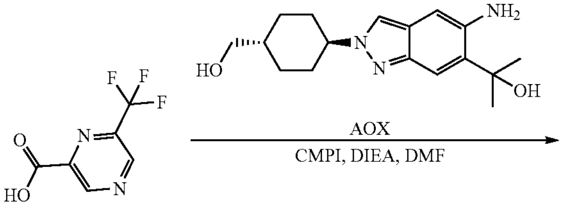

BGR

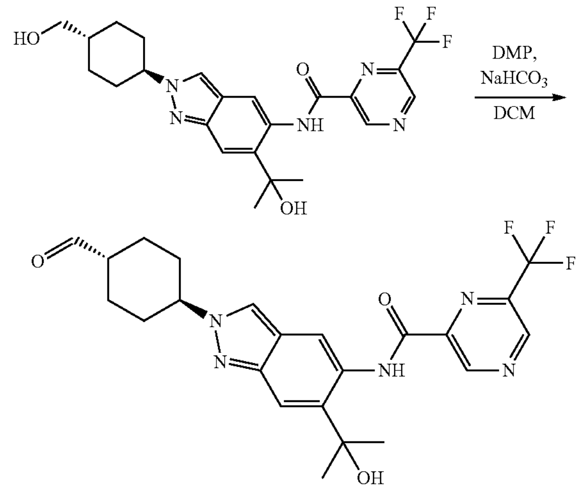

BGS

Step 1—N-[2-[4-(hydroxymethyl)cyclohexyl]-6-(1-hydroxy-1-methyl-ethyl)indazol-5-yl]-6- (trifluoromethyl)pyrazine-2-carboxamide To a solution of 6-(trifluoromethyl)pyrazine-2-carboxylic acid (85.5 mg, 445 umol, Intermediate BGR) and 2-[5-amino-2-[4-(hydroxymethyl)cyclohexyl]indazol-6-yl]propan-2-ol (150 mg, 494 umol, Intermediate AOX) in DMF (2 mL) was added CMPI (151 mg, 593 umol) and DIPEA (192 mg, 1.48 mmol). The reaction mixture was stirred at 20° C. for 0.5 hr. On completion, the mixture was quenched with water (0.1 mL), concentrated in vacuo. The residue was purified by reverse phase (0.1% FA condition) to give the title compound (140 mg, 59% yield) as a yellow solid. $^1$HNMR (400 MHz, DMSO-$d_6$) δ 12.41 (s, 1H), 9.62 (s, 1H), 9.45 (s, 1H), 8.73 (s, 1H), 8.39 (s, 1H), 7.59 (s, 1H), 6.09 (s, 1H), 4.50 (t, J=5.6 Hz, 1H), 4.47-4.36 (m, 1H), 3.29 (t, J=5.6 Hz, 2H), 2.20-2.10 (m, 2H), 1.97-1.84 (m, 4H), 1.62 (s, 6H), 1.54-1.41 (m, 1H), 1.22-1.09 (m, 2H).

Step 2—N-[2-(4-formylcyclohexyl)-6-(1-hydroxy-1-methyl-ethyl)indazol-5-yl]-6-(trifluoromethyl) pyrazine-2-carboxamide To a solution of N-[2-[4-(hydroxymethyl)cyclohexyl]-6-(1-hydroxy-1-methyl-ethyl)indazol-5-yl]-6- (trifluoromethyl)pyrazine-2-carboxamide (140 mg, 293 umol) and $NaHCO_3$ (98.5 mg, 1.17 mmol) in DCM (10 mL) was added DMP (187 mg, 440 umol). Then the reaction mixture was stirred at 20° C. for 2 hrs. On completion, the mixture was quenched with sat. $Na_2S_2O_3$ (20 mL) and $NaHCO_3$ (20 mL), stirred for 10 min, then extracted with DCM (2×30 mL). The organic layer was washed with brine (50 mL), dried in $Na_2SO_4$, filtered and the filtrate was concentrated in vacuo to give the title compound (100 mg, 72% yield) as a yellow solid. LC-MS (ESI$^+$) m/z 476.2 (M+H)$^+$.

Tert-butyl N-[2-(4-formylcyclohexyl)-6-methoxy-indazol-5-yl]carbamate (Intermediate BGT)

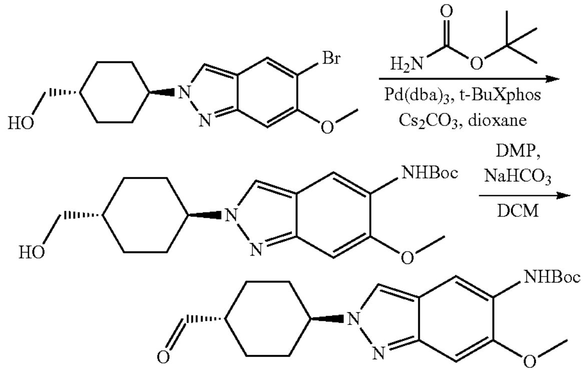

BGT

Step 1—Tert-butyl N-[2-[4-(hydroxymethyl)cyclohexyl]-6-methoxy-indazol-5-yl]carbamate A mixture of [4-(5-bromo-6-methoxy-indazol-2-yl)cyclohexyl]methanol (8.00 g, 23.6 mmol, synthesized via Steps 1-3 of Intermediate ATE), tert-butyl carbamate (4.14 g, 35.4 mmol), $Pd_2(dba)_3$ (2.16 g, 2.36 mmol), t-Bu Xphos (2.00 g, 4.72 mmol) and $Cs_2CO_3$ (15.4 g, 47.2 mmol) in dioxane (150 mL) was de-gassed and heated at 90° C. for 12 hrs. On completion, the mixture was concentrated in vacuo. The residue was purified by silica gel chromatography ($SiO_2$) and then re-purified by reverse phase (0.1% FA condition) to give the title compound (5.00 mg, 57% yield) as a white solid. LC-MS (ESI$^+$) m/z 376.1 (M+H)$^+$.

Step 2—Tert-butyl N-[2-(4-formylcyclohexyl)-6-methoxy-indazol-5-yl]carbamate

To a mixture of tert-butyl N-[2-[4-(hydroxymethyl)cyclohexyl]-6-methoxy-indazol-5-yl]carbamate (800 mg, 2.13 mmol) and $NaHCO_3$ (716 mg, 8.52 mmol) in DCM (20 mL) was added DMP (1.36 g, 3.20 mmol). The reaction mixture was stirred at 20° C. for 2 hrs. On completion, the mixture was quenched with sat. $Na_2S_2O_3$ (50 mL) and $NaHCO_3$ (50 mL), stirred for 10 min, then extracted with DCM (2×50 mL). The organic layer was washed with brine (80 mL), dried in $Na_2SO_4$, filtered and the filtrate was concentrated in vacuo to give the title compound (700 mg, 88% yield) as a yellow solid. LC-MS (ESI$^+$) m/z 374.2 (M+H)$^+$.

3-[4-[4-[[4-(5-Amino-6-methoxy-indazol-2-yl)cyclohexyl]methyl-methyl-amino]-1-piperidyl]-3-methyl-2-oxo-benzimidazol-1-yl]piperidine-2,6-dione (Intermediate BGU)

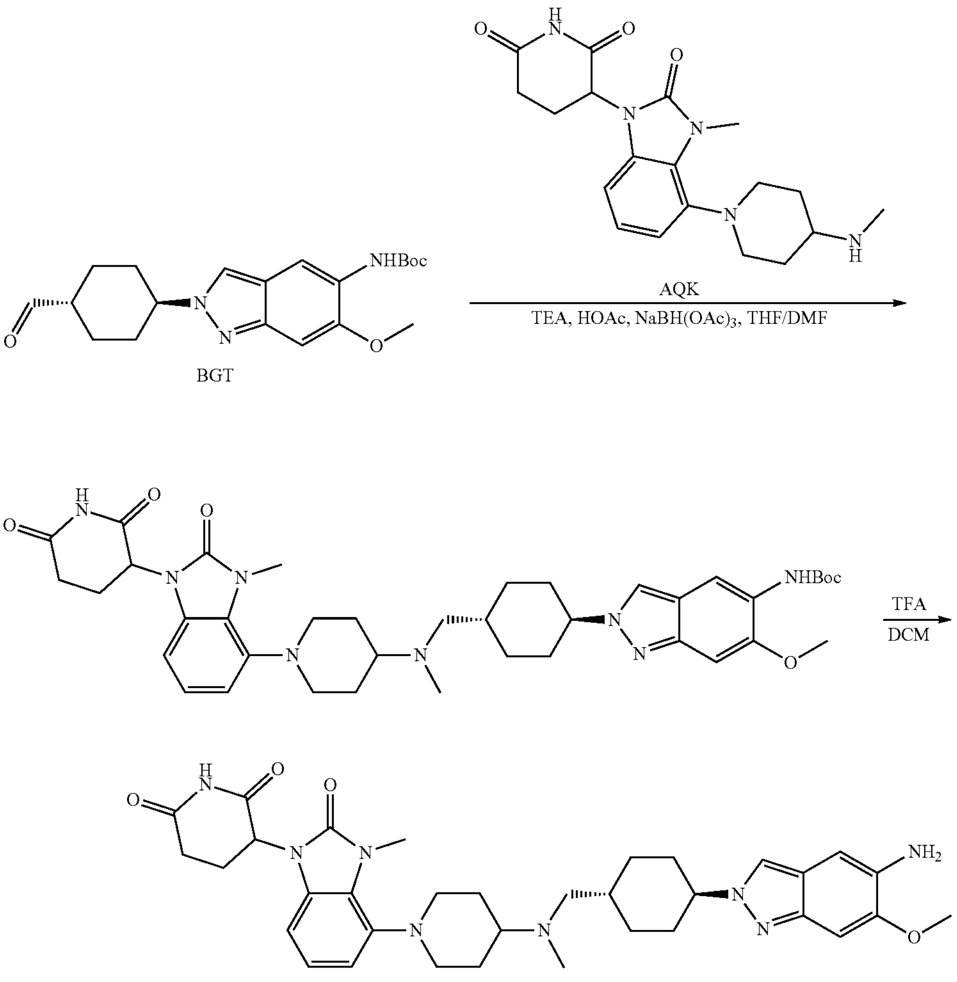

BGT

BGU

Step 1—Tert-butyl N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-methoxy-indazol-5-yl]carbamate To a solution of 3-[3-methyl-4-[4-(methylamino)-1-piperidyl]-2-oxo-benzimidazol-1-yl]piperidine-2,6-dione (873 mg, 2.14 mmol, HCl salt, Intermediate AQK) in a mixed solvent of DMF (10 mL) and THE (50 mL) was added KOAc (315 mg, 3.21 mmol). Then the mixture was cooled to 0° C. and tert-butyl N-[2-(4-formylcyclohexyl)-6-methoxy-indazol-5-yl]carbamate (800 mg, 2.14 mmol, Intermediate BGT) was added. Thirty minutes later, NaBH $(OAc)_3$ (907 mg, 4.28 mmol) was added into the above mixture and the reaction mixture was stirred at 0° C. for 3 hrs. On completion, the mixture was quenched with water (5 mL), concentrated in vacuo. The residue was purified by reverse phase (0.1% FA condition) to give the title compound (1.00 g, 64% yield) as a yellow solid. $^1$H NMR (400 MHz, DMSO-$d_6$) δ 11.08 (s, 1H), 8.17 (s, 1H), 7.89 (s, 1H), 7.75 (s, 1H), 7.08-6.77 (m, 4H), 5.34 (dd, J=5.2, 12.8 Hz, 1H), 4.40-4.24 (m, 1H), 3.84 (s, 3H), 3.63 (s, 3H), 3.16-3.12 (m, 2H), 2.96-2.81 (m, 1H), 2.76-2.57 (m, 4H), 2.47-2.39 (m, 1H), 2.28-2.26 (m, 2H), 2.24 (s, 3H), 2.15-2.06 (s, 2H), 1.99-1.74 (m, 7H), 1.72-1.51 (m, 3H), 1.45 (s, 9H), 1.14-1.01 (m, 2H).

Step 2—3-[4-[4-[[4-(5-Amino-6-methoxy-indazol-2-yl)cyclohexyl]methyl-methyl-amino]-1-piperidyl]-3-methyl-2-oxo-benzimidazol-1-yl]piperidine-2,6-dione To a solution of tert-butyl N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-methoxy-indazol-5-yl] carbamate (60.0 mg, 82.3 umol) in TFA (2 mL) was added DCM (2 mL). The reaction mixture was stirred at 20° C. for 0.5 hr. On completion, the mixture was concentrated in vacuo to give the title compound (60.0 mg, 98% yield, TFA salt) as a yellow solid. LC-MS (ESI$^+$) m/z 629.4 $(M+H)^+$ Ethyl 2-[1-[5-amino-2-[4-(hydroxymethyl)cyclohexyl]indazol-6-yl]-1-methyl-ethoxy]acetate (Intermediate BIN)

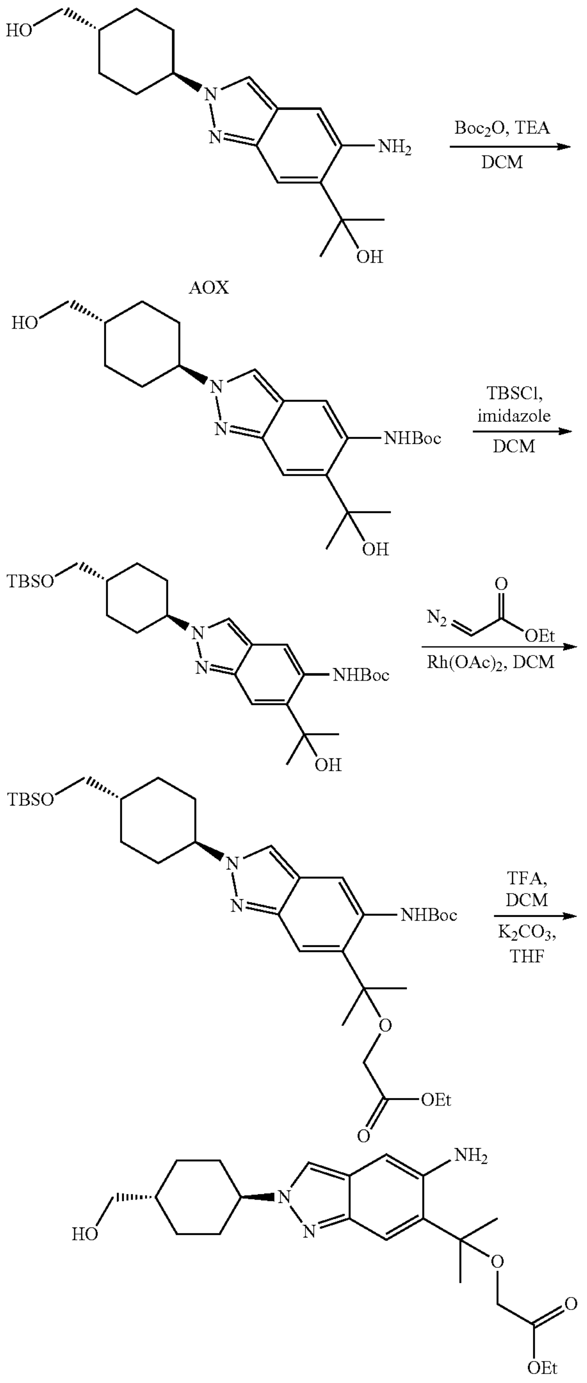

AOX

BIN

Step 1—Tert-butyl N-[2-[4-(hydroxymethyl)cyclohexyl]-6-(1-hydroxy-1-methyl-ethyl)indazol-5-yl]carbamate A solution of 2-[5-amino-2-[4-(hydroxymethyl)cyclohexyl]indazol-6-yl]propan-2-ol (5.00 g, 16.5 mmol, Intermediate AOX), $(Boc)_2O$ (7.19 g, 33.0 mmol) and TEA (3.34 g, 33.0 mmol) in DCM (100 mL) was stirred at 25° C. for 12 hrs. On completion, the reaction mixture was filtered and the filtrate was concentrated in vacuo. The residue was diluted with water (200 mL) and extracted with ethyl acetate (3×200 mL). The combined organic layer was washed with brine (100 mL), dried over anhydrous sodium sulfate, filtered and concentrated in vacuo. The crude product was triturated with EA (20 mL), stirred and filtered. The filter cake was dried in vacuo to give the title compound (6.20 mg, 93% yield) as a gray solid. 1H NMR (400 MHz, DMSO-$d_6$) δ 9.64 (s, 1H), 8.24 (s, 1H), 8.07 (s, 1H), 7.49 (s, 1H), 6.04 (s, 1H), 4.49 (t, J=5.2 Hz, 1H), 4.42-4.33 (m, 1H), 3.29 (t, J=5.6 Hz, 2H), 2.16-2.07 (m, 2H), 1.95-1.85 (m, 4H), 1.60 (s, 6H), 1.48 (s, 9H), 1.34-0.97 (m, 3H).

Step 2—Tert-butyl N-[2-[4-[[tert-butyl(dimethyl)silyl]oxymethyl]cyclohexyl]-6-(1-hydroxy-1-methyl-ethyl)indazol-5-yl]carbamate To a solution of tert-butyl N-[2-[4-(hydroxymethyl)cyclohexyl]-6-(1-hydroxy-1-methyl-ethyl)indazol -5-yl]carbamate (3.00 g, 7.43 mmol) and imidazole (1.01 g, 14.9 mmol) in DCM (40 mL) was added TBSCI (1.23 g, 8.18 mmol). The reaction mixture was stirred at 20° C. for 12 hrs. On completion, the mixture was quenched with water (100 mL), separated and the organic layer was concentrated in vacuo. The residue was purified by reverse phase (0.1% FA condition) to give the title compound (3.20 g, 83% yield) as a yellow solid. LC-MS ($ESI^+$) m/z 518.4 $(M+H)^+$.

Step 3—Ethyl 2-[1-[5-(tert-butoxycarbonylamino)-2-[4-[[tert-butyl(dimethyl)silyl]oxymethyl]cyclohexyl]indazol-6-yl]-1-methyl-ethoxy]acetate To a solution of tert-butyl N-[2-[4-[[tert-butyl(dimethyl)silyl]oxymethyl]cyclohexyl]-6-(1-hydroxy-1- methyl-ethyl)indazol-5-yl]carbamate (3.20 g, 6.18 mmol) and $Rh_2(OAc)_4$ (273 mg, 618 umol) in DCM (50 mL) was added a solution of ethyl 2-diazoacetate (14.1 g, 124 mmol) in DCM (50 mL) dropwise. Then the reaction mixture was stirred at 20° C. for 3 days. On completion, the mixture was washed with water (200 mL) and brine (2×200 mL). The organic layer was concentrated in vacuo and the residue was purified by silica gel chromatography ($SiO_2$) to give the title compound (700 mg, 19% yield) as green oil. $^1H$ NMR (400 MHz, $CDCl_3$) δ 8.67 (s, 1H), 8.17 (s, 1H), 7.83 (s, 1H), 7.64 (s, 1H), 4.41-4.32 (m, 1H), 4.13 (q, J=7.2 Hz, 2H), 3.88 (s, 2H), 3.49 (d, J=6.0 Hz, 2H), 2.34-2.21 (m, 2H), 2.03-1.88 (m, 4H), 1.73 (s, 6H), 1.54 (s, 9H), 1.35-1.28 (m, 5H), 0.92 (s, 9H), 0.08-0.05 (m, 6H).

Step 4—Ethyl 2-[1-[5-amino-2-[4-(hydroxymethyl)cyclohexyl]indazol-6-yl]-1-methyl-ethoxy]acetate To a solution of ethyl 2-[1-[5-(tert-butoxycarbonylamino)-2-[4-[[tert-butyl(dimethyl)silyl]oxymethyl]cyclohexyl]indazol-6-yl]-1-methyl-ethoxy]acetate (360 mg, 596 umol) in TFA (2 mL) was added DCM (5 mL). The reaction mixture was stirred at 20° C. for 0.5 hr. Then the mixture was concentrated in vacuo. The residue was then dissolved in THE (5 mL) and then $K_2CO_3$ (247 mg, 1.79 mmol) was added. The reaction mixture was stirred at 20° C. for 2 hrs. On completion, the mixture was diluted with water (30 mL), and extracted with EA (2×50 mL). The organic layer was washed with brine (50 mL), dried in $Na_2SO_4$, filtered and the filtrate was concentrated in vacuo to give the title compound (220 mg, 95% yield) as yellow oil. LC-MS ($ESI^+$) m/z 390.3 $(M+H)^+$.

Ethyl 2-[1-[2-(4-formylcyclohexyl)-5-[[6-(trifluoromethyl)pyridine-2-carbonyl]amino]indazol-6-yl]-1-methyl-ethoxy]acetate (Intermediate BIO)

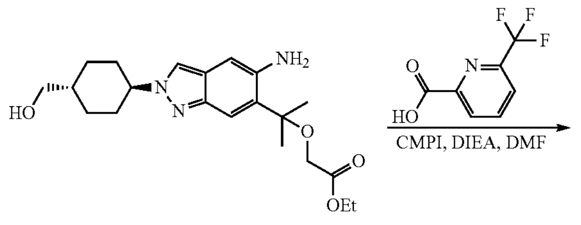

BIN

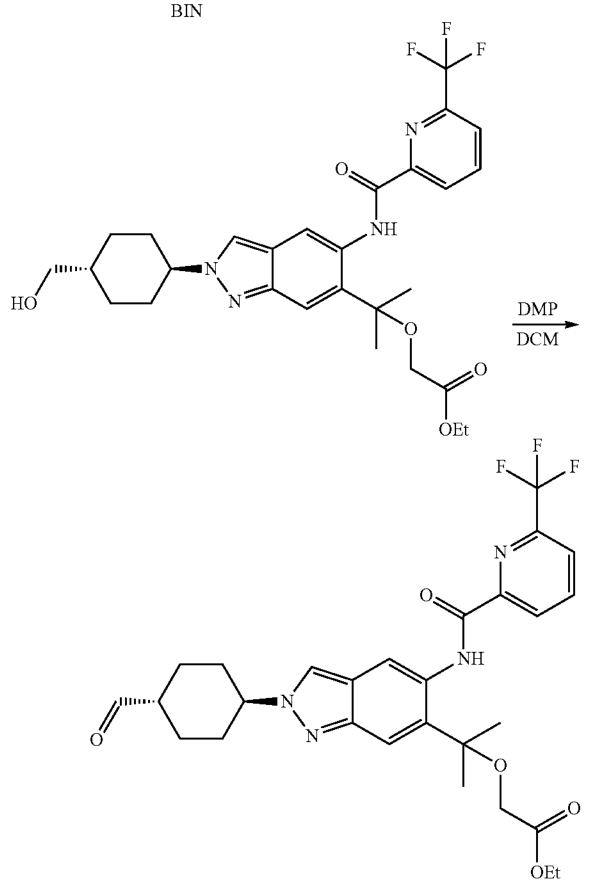

BIO

Step 1—Ethyl 2-[1-[2-[4-(hydroxymethyl)cyclohexyl]-5-[[6-(trifluoromethyl)pyridine-2-carbonyl]amino]indazol-6-yl]-1-methyl-ethoxy]acetate To a solution of 6-(trifluoromethyl)pyridine-2-carboxylic acid (92.7 mg, 485 umol, CAS #131747-42-7), CMPI (165 mg, 647 umol) and DIEA (209 mg, 1.62 mmol) in DMF (5 mL) was added ethyl 2-[1-[5-amino-2-[4-(hydroxymethyl)cyclohexyl]indazol-6-yl]-1-methyl-ethoxy]acetate (210 mg, 539 umol, Intermediate BIN). Then the reaction mixture was stirred at 20° C. for 0.5 hr. On completion, the mixture was quenched with water (0.1 mL), then concentrated in vacuo. The residue was purified by reverse phase (0.1% FA condition) to give the title compound (160 mg, 53% yield) as a yellow solid. $^1H$ NMR (400 MHz, DMSO-$d_6$) δ 11.61 (s, 1H), 8.77 (s, 1H), 8.47-8.33 (m, 3H), 8.15 (dd, J=0.8, 7.6 Hz, 1H), 7.65 (s, 1H), 4.51-4.45 (m, 1H), 4.45-4.38 (m, 1H), 4.23-4.04 (m, 2H), 3.94 (s, 2H), 3.90 (q, J=7.2 Hz, 2H), 2.21-2.05 (m, 2H), 1.98-1.83 (m, 4H), 1.70 (s, 6H), 1.53-1.40 (m, 1H), 1.22-1.18 (m, 2H), 0.97 (t, J=7.2 Hz, 3H).

Step 2—Ethyl 2-[1-[2-(4-formylcyclohexyl)-5-[[6-(trifluoromethyl)pyridine-2-carbonyl]amino]indazol-6-yl]-1-methyl-ethoxy]acetate To a solution of ethyl 2-[1-[2-[4-(hydroxymethyl)cyclohexyl]-5-[[6-(trifluoromethyl)pyridine-2- carbonyl]amino]indazol-6-yl]-1-methyl-ethoxy]acetate (40.0 mg, 71.1 umol) in DCM (1 mL) was added DMP (36.2 mg, 85.3 umol). Then the reaction mixture was stirred at 20° C. for 2 hrs. On completion, the mixture was quenched with sat. $Na_2S_2O_3$ (20 mL) and $NaHCO_3$ (20 mL), stirred for 10 min, then extracted with DCM (2×30 mL). The organic layer was washed with brine (50 mL), dried in $Na_2SO_4$, filtered and the filtrate was concentrated in vacuo to give the title compound (35.0 mg, 88% yield) as yellow oil. LC-MS ($ESI^+$) m/z 561.3 $(M+H)^+$.

3-[4-(2,7-Diazaspiro[3.5]nonan-2-yl)-3-methyl-2-oxo-benzimidazol-1-yl]piperidine-2,6-dione (Intermediate BIL)

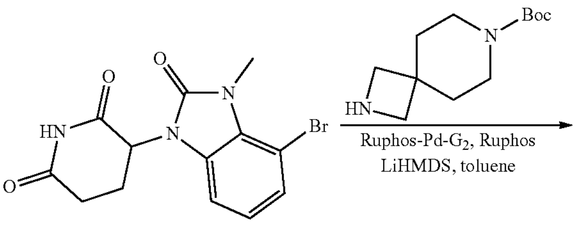

HP

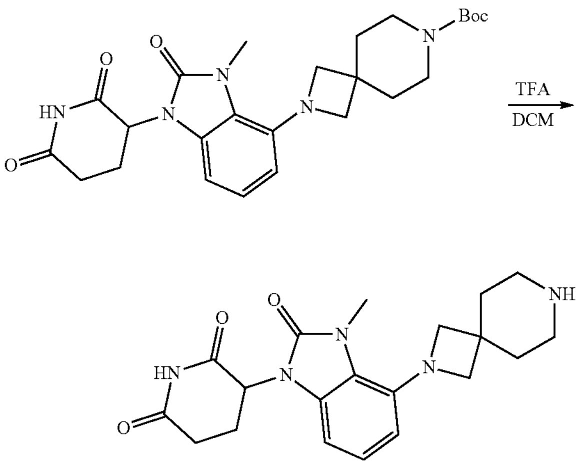

BIL

Step 1—Tert-butyl 2-[1-(2,6-dioxo-3-piperidyl)-3-methyl-2-oxo-benzimidazol-4-yl]-2,7-diazaspiro [3.5] nonane-7-carboxylate To a solution of 3-(4-bromo-3-methyl-2-oxo-benzimidazol-1-yl)piperidine-2,6-dione (500 mg, 1.48 mmol, Intermediate HP), tert-butyl2,7-diazaspiro[3.5]nonane-7-carboxylate (501 mg, 2.22 mmol, CAS #896464-16-7) and 4 Å molecular sieve (500 mg) in toluene (10.0 mL) was added [2-(2-aminophenyl)phenyl]-chloro-palladium;dicyclohexyl-[2-(2,6-diisopropoxyphenyl)phenyl]phosphane (229 mg, 295 umol), RuPhos (138 mg, 295 umol) and LiHMDS (1.00 M, 7.39 mL) under $N_2$. The mixture was stirred at 80° C. for 6 hrs under $N_2$. On completion, the mixture was adjust to pH=6 with FA. The mixture was then filtered and concentrated in vacuo. The mixture was diluted with $H_2O$ (30 mL) and extracted with EA (3x30 mL). The organic layers were washed with brine (2x20 mL), dried over anhydrous $Na_2SO_4$, filtered and concentrated in vacuo. The mixture was purified by reverse phase (0.1% FA) to give the title compound (300 mg, 41% yield) as yellow solid. $^1H$ NMR (400 MHz, $CDCl_3$) δ 8.26 (s, 1H), 6.99 (t, J=8.0 Hz, 1H), 6.70 (d, J=8.0 Hz, 1H), 6.47 (d, J=8.0 Hz, 1H), 5.25-5.10 (m, 1H), 3.72 (s, 3H), 3.66-3.60 (m, 4H), 3.45-3.38 (m, 4H), 2.98-2.89 (m, 1H), 2.88-2.78 (m, 1H), 2.77-2.66 (m, 1H), 2.28-2.17 (m, 1H), 1.85-1.79 (m, 4H), 1.48 (s, 9H); LC-MS ($ESI^+$) m/z 484.1 $(M+H)^+$.

Step 2—3-[4-(2,7-Diazaspiro[3.5]nonan-2-yl)-3-methyl-2-oxo-benzimidazol-1-yl]piperidine-2,6-dione To a solution of tert-butyl 2-[1-(2,6-dioxo-3-piperidyl)-3-methyl-2-oxo-benzimidazol-4-yl]-2,7- diazaspiro[3.5] nonane-7-carboxylate (100 mg, 206 umol) in DCM (3.00 mL) was added TFA (770 mg, 6.75 mmol). The mixture was stirred at 15° C. for 0.5 hr. On completion, the mixture was concentrated in vacuo to give the title compound (100 mg, 97% yield, TFA) as yellow oil. LC-MS ($ESI^+$) m/z 384.2 $(M+H)^+$ N-[6-[1-(2-amino-2-oxo-ethoxy)-1-methyl-ethyl]-2-(4-formylcyclohexyl)indazol-5-yl]-6- (trifluoromethyl)pyridine-2-carboxamide (Intermediate BIP)

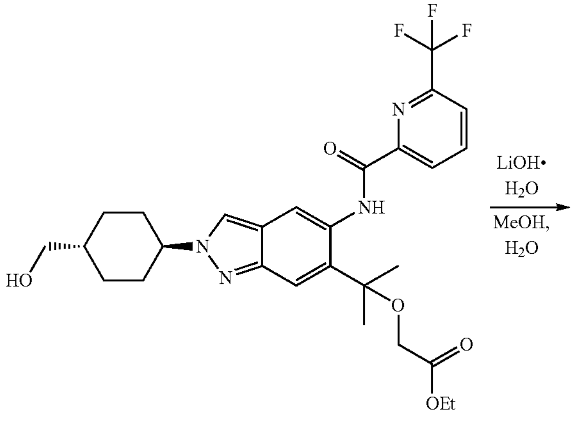

-continued

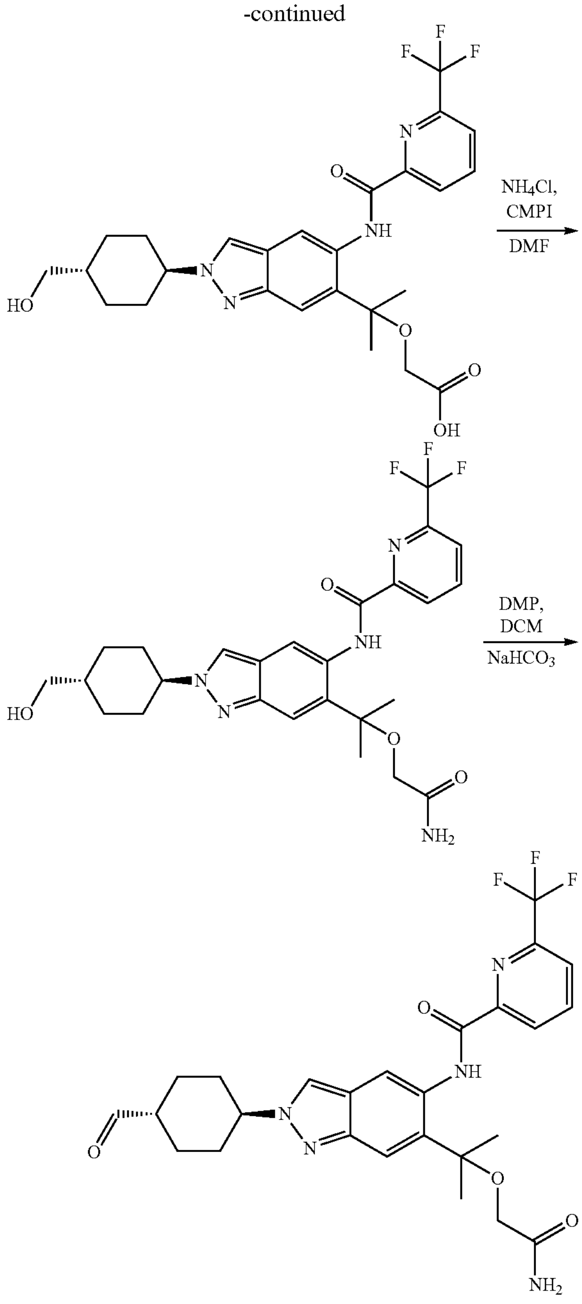

BIP

Step 1—2-[1-[2-[4-(hydroxymethyl)cyclohexyl]-5-[[6-(trifluoromethyl)pyridine-2-carbonyl]amino] indazol-6-yl]-1-methyl-ethoxy]acetic acid To a solution of ethyl 2-[1-[2-[4-(hydroxymethyl)cyclohexyl]-5-[[6-(trifluoromethyl)pyridine-2- carbonyl]amino] indazol-6-yl]-1-methyl-ethoxy]acetate (100 mg, 178 umol, synthesized via Step 1 of Intermediate BIO) in a mixed solvent of THF (1 mL), MeOH (0.2 mL) and $H_2O$ (0.2 mL) was added LiOH $H_2O$ (29.8 mg, 711 umol). Then the reaction mixture was stirred at 20° C. for 12 hrs. On completion, the mixture was acidified with 1N HCl to pH=3-4, then concentrated in vacuo. The residue was purified by reverse phase (0.1% FA condition) to give the title compound (90.0 mg, 95% yield) as a yellow solid. LC-MS ($ESI^+$) m/z 535.2 $(M+H)^+$.

Step 2—N-[6-[1-(2-amino-2-oxo-ethoxy)-1-methyl-ethyl]-2-[4-(hydroxymethyl)cyclohexyl]indazol-5-yl]-6-(trifluoromethyl)pyridine-2-carboxamide To a solution of 2-[1-[2-[4-(hydroxymethyl)cyclohexyl]-5-[[6-(trifluoromethyl)pyridine-2-carbonyl]amino]indazol-6-yl]-1-methyl-ethoxy]acetic acid (40.0 mg, 74.8 umol), DIEA (29.0 mg, 224 umol) and $NH_4Cl$ (80.1 mg, 1.50 mmol) in DMF (1 mL) was added CMPI (22.9 mg, 89.8 umol). The reaction mixture was stirred at 20° C. for 0.5 hr. On completion, the mixture was quenched with water (0.05 mL), and concentrated in vacuo. The residue was purified by reverse phase (0.1% FA condition) to give the title compound (35.0 mg, 88% yield) as a yellow solid. $^1H$ NMR (400 MHz, DMSO-$d_6$) δ 11.53 (s, 1H), 8.87 (s, 1H), 8.49-8.45 (m, 1H), 8.43 (s, 1H), 8.42-8.36 (m, 1H), 8.19 (d, J=7.2 Hz, 1H), 7.66 (s, 1H), 7.35 (s, 1H), 6.82 (s, 1H), 4.53-4.37 (m, 2H), 3.61 (s, 2H), 3.28 (s, 2H), 2.17-2.10 (m, 2H), 1.97-1.85 (m, 4H), 1.75 (s, 6H), 1.55-1.41 (m, 1H), 1.22-1.08 (m, 2H).

Step 3—N-[6-[1-(2-amino-2-oxo-ethoxy)-1-methyl-ethyl]-2-(4-formylcyclohexyl)indazol-5-yl]-6- (trifluoromethyl)pyridine-2-carboxamide To a solution of N-[6-[1-(2-amino-2-oxo-ethoxy)-1-methyl-ethyl]-2-[4-(hydroxymethyl)cyclohexyl]indazol-5-yl]-6-(trifluoromethyl)pyridine-2-carboxamide (30.0 mg, 56.2 umol) and $NaHCO_3$ (9.45 mg, 112 umol) in DCM (5 mL) was added DMP (35.8 mg, 84.3 umol). Then the reaction mixture was stirred at 20° C. for 6 hrs. On completion, the mixture was quenched with sat. $Na_2S_2O_3$ (20 mL) and $NaHCO_3$ (20 mL), then stirred for 10 min, and extracted with DCM (2×30 mL). The organic layer was washed with brine (50 mL), dried in $Na_2SO_4$, filtered and the filtrate was concentrated in vacuo to give the title compound (29.0 mg, 97% yield, FA salt) as yellow oil. LC-MS ($ESI^+$) m/z 554.3 $(M+Na)^+$.

2-[1-[2-(4-Formylcyclohexyl)-5-[[6-(trifluoromethyl)pyridine-2-carbonyl]amino]indazol-6- yl]-1-methyl-ethoxy]acetic acid (Intermediate BIO)

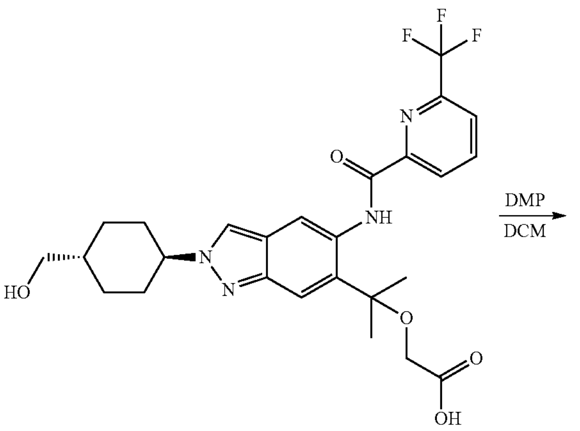

-continued

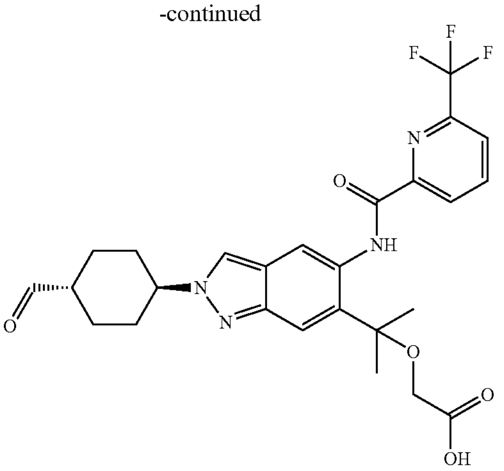

BIQ

To a solution of 2-[1-[2-[4-(hydroxymethyl)cyclohexyl]-5-[[6-(trifluoromethyl)pyridine-2-carbonyl]amino]indazol-6-yl]-1-methyl-ethoxy]acetic acid (60.0 mg, 112 umol, synthesized via Step 1 of Intermediate BIP) in DCM (1 mL) was added DMP (71.4 mg, 168 umol). Then the reaction mixture was stirred at 20° C. for 2 hrs. On completion, the mixture was quenched with sat. $Na_2S_2O_3$ (20 mL) and $NaHCO_3$ (20 mL), then stirred for 10 min, and extracted with DCM (2×30 mL). The organic layer was washed with brine (50 mL), dried over $Na_2SO_4$, filtered and the filtrate was concentrated in vacuo. The residue was purified by reverse phase (0.1% FA condition) to give the title compound (45.0 mg, 75% yield) as a yellow solid. LC-MS ($ESI^+$) m/z 533.2 $(M+H)^+$.

2-(Trifluoromethyl)pyrimidine-4-carboxylic acid (Intermediate BIR)

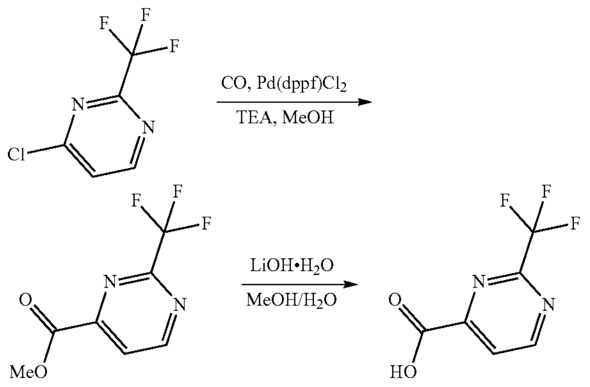

BIR

Step 1—Methyl 2-(trifluoromethyl)pyrimidine-4-carboxylate

To a solution of 4-chloro-2-(trifluoromethyl)pyrimidine (100 mg, 547 umol, CAS #1514-96-1) in MeOH (3 mL) was added $Pd(dppf)Cl_2$ (40.1 mg, 54.8 umol) and TEA (166 mg, 1.64 mmol, 228 uL) under $N_2$ atmosphere. The suspension was degassed and purged with CO for 3 times. The mixture was stirred under CO (50 Psi.) at 80° C. for 16 hrs. On completion, the reaction mixture was filtered and the filtrate concentrated in vacuo to give a residue. The residue was purified by column chromatography ($SiO_2$, petroleum ether/ethyl acetate=0/1 to 10/1, PE:EA=5:1, Rf=0.24) to give the title compound (100 mg, 88% yield) as a white solid. $^1H$ NMR (400 MHz, $CDC_3$-d) δ 9.17 (d, J=5.2 Hz, 1H), 8.20 (d, J=4.8 Hz, 1H), 4.08 (s, 3H).

Step 2—2-(Trifluoromethyl)pyrimidine-4-carboxylic acid

To a solution of methyl 2-(trifluoromethyl)pyrimidine-4-carboxylate (70.0 mg, 339 umol) in MeOH (4.00 mL) and $H_2O$ (0.40 mL) was added LiOH $H_2O$ (42.7 mg, 1.02 mmol). The mixture was stirred at 20° C. for 2 hrs. On completion, the reaction mixture was concentrated in vacuo to remove MeOH, then acid by addition 1 N HCl until the pH=3-4, then extracted with EA (3×5 mL). The combined organic layer was washed with brine (2×10 mL), dried over anhydrous $Na_2SO_4$, filtered and concentrated in vacuo to give the title compound (45.0 mg, 68% yield) as a white solid. H NMR (400 MHz, DMSO-$d_6$) δ 9.29 (d, J=5.2 Hz, 1H), 8.26 (d, J=4.8 Hz, 1H).

N-[2-(4-formylcyclohexyl)-6-(1-hydroxy-1-methyl-ethyl)indazol-5-yl]-2-(trifluoromethyl) pyrimidine-4-carboxamide (Intermediate BIS)

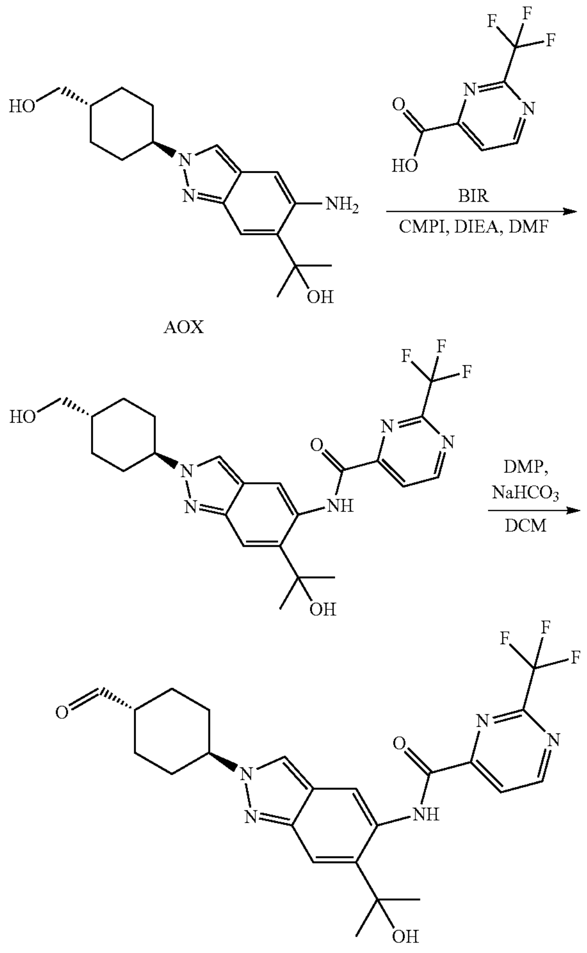

AOX

BIS

Step 1—N-[2-[4-(hydroxymethyl)cyclohexyl]-6-(1-hydroxy-1-methyl-ethyl)indazol-5-yl]-2-(trifluoro methyl)pyrimidine-4-carboxamide To a solution of 2-(trifluoromethyl)pyrimidine-4-carboxylic acid (45.0 mg, 234 umol, Intermediate BIR) and 2-[5-amino-2-[4-(hydroxymethyl)cyclohexyl]indazol-6-yl]propan-2-ol (71.07 mg, 234 umol, Intermediate AOX) in DMF (1.00 mL) was added CMPI (71.8 mg, 281 umol) and DIEA (90.8 mg, 702 umol, 122 uL). The mixture was stirred at 20° C. for 16 hrs. On completion, the reaction mixture was concentrated in vacuo to give the residue. The residue was purified by reversed phase (0.1% FA condition) to give the title compound (650 mg, 58.11% yield) as a white solid. $^1H$ NMR (400 MHz, $CDCl_3$-d) δ12.47-12.36 (m, 1H), 9.17 (d, J=4.8 Hz, 1H), 8.89 (s, 1H), 8.41 (d, J=5.2 Hz, 1H), 7.95 (s, 1H), 7.76 (s, 1H), 4.47-4.31 (m, 1H), 3.61-3.54 (m, 2H), 2.40-2.29 (m, 2H), 2.22 (s, 1H), 2.09-1.99 (m, 4H), 1.81 (s, 6H), 1.72-1.66 (m, 1H), 1.33-1.27 (m, 2H); LC-MS ($ESI^+$) m/z 478.2 $(M+H)^+$.

Step 2—N-[2-(4-formylcyclohexyl)-6-(1-hydroxy-1-methyl-ethyl)indazol-5-yl]-2-(trifluoromethyl) pyrimidine-4-carboxamide To a solution of N-[2-[4-(hydroxymethyl)cyclohexyl]-6-(1-hydroxy-1-methyl-ethyl)indazol-5-yl]-2- (trifluoromethyl)pyrimidine-4-carboxamide (65.0 mg, 136 umol) in DCM (6.00 mL) was added DMP (69.3 mg, 163 umol) and $NaHCO_3$ (34.3 mg, 408 umol) at 0° C. The mixture was stirred at 20° C. for 16 hrs. On completion, the reaction mixture was quenched by addition saturated solution of $Na_2S_2O_3$ (1 mL), and saturated solution of $NaHCO_3$ (2 mL), then extracted with DCM (3×10 mL). The combined organic layer was washed with brine (2×20 mL), dried over anhydrous $Na_2SO_4$, filtered and concentrated in vacuo to give the title compound (60.0 mg, 92% yield) as a yellow solid. $^1H$ NMR (400 MHz, DMSO-$d_6$) δ 12.61-12.53 (m, 1H), 9.65 (s, 1H), 9.36 (d, J=5.2 Hz, 1H), 8.75 (s, 1H), 8.43 (d, J=4.8 Hz, 1H), 8.40 (s, 1H), 7.59 (s, 1H), 6.11-6.05 (m, 1H), 4.46 (tt, J=4.0, 11.6 Hz, 1H), 2.46-2.39 (m, 1H), 2.21 (dd, J=2.8, 12.4 Hz, 2H), 2.15-2.07 (m, 2H), 1.98 (dq, J=3.6, 12.4 Hz, 2H), 1.63 (s, 6H), 1.52-1.40 (m, 2H). LC-MS ($ESI^+$) m/z 476.2 $(M+H)^+$.

3-Fluoro-N-[2-(4-formylcyclohexyl)-6-methoxy-indazol-5-yl]benzamide (Intermediate BIT)

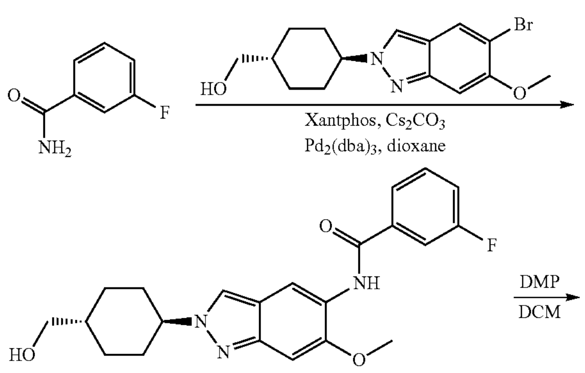

-continued

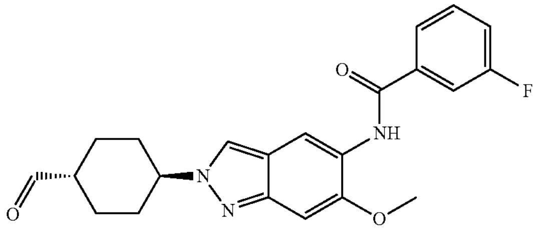

BIT

Step 1—3-Fluoro-N-[2-[4-(hydroxymethyl)cyclohexyl]-6-methoxy-indazol-5-yl]benzamide A mixture of 3-fluorobenzamide (148 mg, 1.06 mmol, CAS #455-37-8), [4-(5-bromo-6-methoxy-indazol-2-yl)cyclohexyl]methanol (300 mg, 884 umol, synthesized via Steps 1-3 of Intermediate ATE), $Pd_2(dba)_3$ (80.9 mg, 88.4 umol), $Cs_2CO_3$ (576 mg, 1.77 mmol) and Xantphos (102 mg, 177 umol) in dioxane (4 mL) was de-gassed and heated at 90° C. for 12 hrs. On completion, the mixture was filtered and the filtrate was concentrated in vacuo. The residue was purified by reverse phase (0.1% FA condition) to give the title compound (240 mg, 68% yield) as a yellow solid. $^1H$ NMR (400 MHz, DMSO-$d_6$) δ 9.51 (s, 1H), 8.29 (s, 1H), 8.05 (s, 1H), 7.87-7.72 (m, 2H), 7.61-7.55 (m, 1H), 7.47-7.40 (m, 1H), 7.07 (s, 1H), 4.60-4.41 (m, 1H), 4.40-4.32 (m, 1H), 3.87 (s, 3H), 3.29 (d, J=6.0 Hz, 2H), 2.20-2.06 (m, 2H), 1.95-1.85 (m, 4H), 1.55-1.40 (m, 1H), 1.22-1.08 (m, 2H).

Step 2—3-Fluoro-N-[2-(4-formylcyclohexyl)-6-methoxy-indazol-5-yl]benzamide

To a solution of 3-fluoro-N-[2-[4-(hydroxymethyl)cyclohexyl]-6-methoxy-indazol-5-yl]benzamide (70.0 mg, 176 umol) in DCM (2 mL) was added DMP (112 mg, 264 umol). The reaction mixture was stirred at 20° C. for 2 hrs. On completion, the mixture was quenched with sat. $Na_2S_2O_3$ (20 mL) and $NaHCO_3$ (20 mL), and stirred for 10 min, then extracted with DCM (2×30 mL). The organic layer was washed with brine (50 mL), dried in $Na_2SO_4$, filtered and the filtrate was concentrated in vacuo to give the title compound (40.0 mg, 57% yield) as a yellow solid. LC-MS (ESI$^+$) m/z 396.2 (M+H)$^+$.

3,5-Difluoro-N-[2-(4-formylcyclohexyl)-6-(1-hydroxy-1-methyl-ethyl)indazol-5-yl]pyridine- 2-carboxamide (Intermediate BIU)

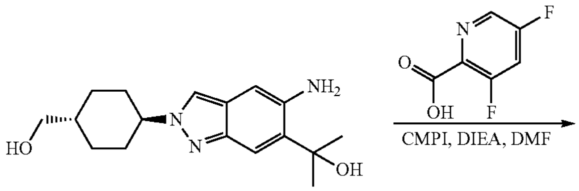

AOX

-continued

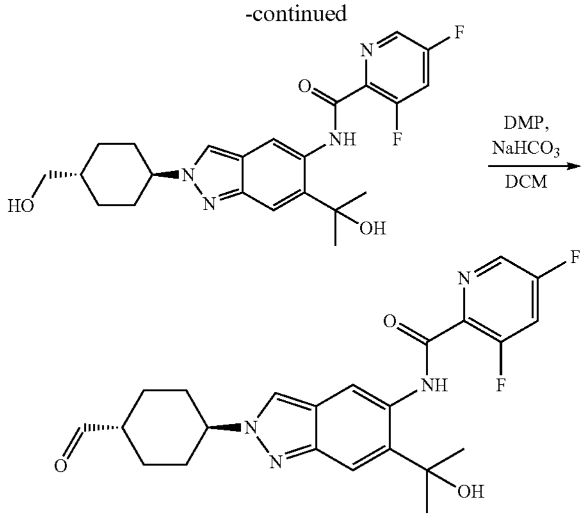

BIU

Step 1—3,5-Difluoro-N-[2-[4-(hydroxymethyl)cyclohexyl]-6-(1-hydroxy-1-methyl-ethyl)indazol-5-yl]pyridine-2-carboxamide To a solution of 3,5-difluoropyridine-2-carboxylic acid (78.6 mg, 494 umol, CAS #745784-04-7) in DMF (4.00 mL) was added CMPI (151 mg, 593 umol) and DIEA (191 mg, 1.48 mmol). The mixture was stirred at 15° C. for 10 min. Then 2-[5-amino-2-[4-(hydroxymethyl)cyclohexyl]indazol-6-yl]propan-2-ol (150 mg, 494 umol, Intermediate AOX) was added, and the mixture was stirred at 15° C. for 50 min. On completion, the mixture was diluted with $H_2O$ (30 mL), and extracted with EA (3×15 mL). The organic layers were washed with brine (2×20 mL), dried over anhydrous $Na_2SO_4$, filtered and concentrated in vacuo to give the title compound (215 mg, 97% yield) as yellow solid. $^1H$ NMR (400 MHz, DMSO-$d_6$) δ 12.05 (s, 1H), 8.65-8.56 (m, 2H), 8.35 (s, 1H), 8.20-8.10 (m, 1H), 7.56 (s, 1H), 6.06 (s, 1H), 4.49 (t, J=5.2 Hz, 1H), 4.45-4.35 (m, 1H), 3.31-3.25 (m, 2H), 2.19-2.08 (m, 2H), 1.95-1.81 (m, 4H), 1.61 (s, 6H), 1.54-1.41 (m, 1H), 1.18-1.13 (m, 2H), LC-MS (ESI$^+$) m/z 445.3 (M+H)$^+$.

Step 2—3,5-Difluoro-N-[2-(4-formylcyclohexyl)-6-(1-hydroxy-1-methyl-ethyl)indazol-5-yl]pyridine-2-carboxamide To a solution of 3,5-difluoro-N-[2-[4-(hydroxymethyl)cyclohexyl]-6-(1-hydroxy-1-methyl-ethyl) indazol-5-yl]pyridine-2-carboxamide (100 mg, 224 umol) in DCM (3.00 mL) was added DMP (143 mg, 337 umol) and $NaHCO_3$ (94.5 mg, 1.12 mmol). The mixture was stirred at 15° C. for 0.5 hr. On completion, the mixture was quenched with DCM (20 mL), quenched with saturated $Na_2S_2O_3$ (10 mL) and washed with saturated $NaHCO_3$ (3×20 mL). The organic layer was dried over anhydrous $Na_2SO_4$, filtered and concentrated in vacuo to give the title compound (80.0 mg, 80% yield) as yellow solid. $^1H$ NMR (400 MHz, DMSO-$d_6$) δ 12.06 (s, 1H), 9.65 (s, 1H), 8.66-8.57 (m, 2H), 8.35 (s, 1H), 8.20-8.10 (m, 1H), 7.56 (s, 1H), 6.07 (s, 1H), 4.64-4.36 (m, 1H), 2.46-2.37 (m, 1H), 2.25-2.15 (m, 2H), 2.14-2.07 (m, 2H), 2.03-1.94 (m, 2H), 1.61 (s, 6H), 1.50-1.38 (m, 2H); LC-MS (ESI$^+$) m/z 443.1 (M+H)$^+$.

N-[2-(4-formylcyclohexyl)-6-(1-hydroxy-1-methyl-ethyl)indazol-5-yl]thiazole-5-carboxamide (Intermediate BIV)

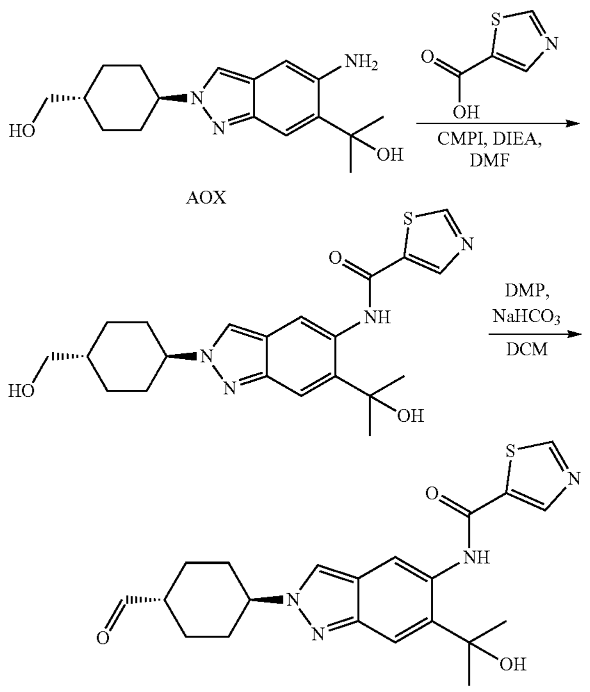

AOX

BIV

Step 1—N-[2-[4-(hydroxymethyl)cyclohexyl]-6-(1-hydroxy-1-methyl-ethyl)indazol-5-yl]thiazole-5-carboxamide A mixture of 2-[5-amino-2-[4-(hydroxymethyl)cyclohexyl]indazol-6-yl]propan-2-ol (100 mg, 330 umol, Intermediate AOX), thiazole-5-carboxylic acid (42.6 mg, 330 umol, CAS #14527-41-4), CMPI (101 mg, 396 umol), DIEA (128 mg, 989 umol) in DMF (1 mL) was degassed and purged with $N_2$ for 3 times, and then the mixture was stirred at 25° C. for 1 hour under $N_2$ atmosphere. On completion, the reaction mixture was diluted with $H_2O$ (5 mL) and EA (30 mL). The organic phase was separated, washed with brine (10 mL), dried over $Na_2SO_4$, filtered and concentrated in vacuo to give the title compound (95.0 mg, 69% yield) as a brown solid. LC-MS ($ESI^+$) m/z 415.1 $(M+H)^+$.

Step 2—N-[2-(4-formylcyclohexyl)-6-(1-hydroxy-1-methyl-ethyl)indazol-5-yl]thiazole-5- carboxamide To a solution of N-[2-[4-(hydroxymethyl)cyclohexyl]-6-(1-hydroxy-1-methyl-ethyl)indazol-5-yl]thiazole-5-carboxamide (130 mg, 314 umol) in DCM (3 mL) was added $NaHCO_3$ (132 mg, 1.57 mmol) and DMP (200 mg, 470 umol) at 0° C. The mixture was stirred at 0-25° C. for 2 hours. The reaction mixture was quenched by addition $Na_2S_2O_3$ (1 mL) and $NaHCO_3$ (1 mL) until the pH=8 at 25° C. The mixture was diluted with $H_2O$ (5 mL) and extracted with DCM 20 mL (2×10 mL). The combined organic layers were dried over $Na_2SO_4$, filtered and concentrated in vacuo to give the title compound (81.0 mg, 63% yield) as a brown solid. LC-MS ($ESI^+$) m/z 413.2 $(M+H)^+$.

N-[2-(4-formylcyclohexyl)-6-methoxyindazol-5-yl]-2-(trifluoromethyl) pyrimidine-5-carboxamide (Intermediate BIW)

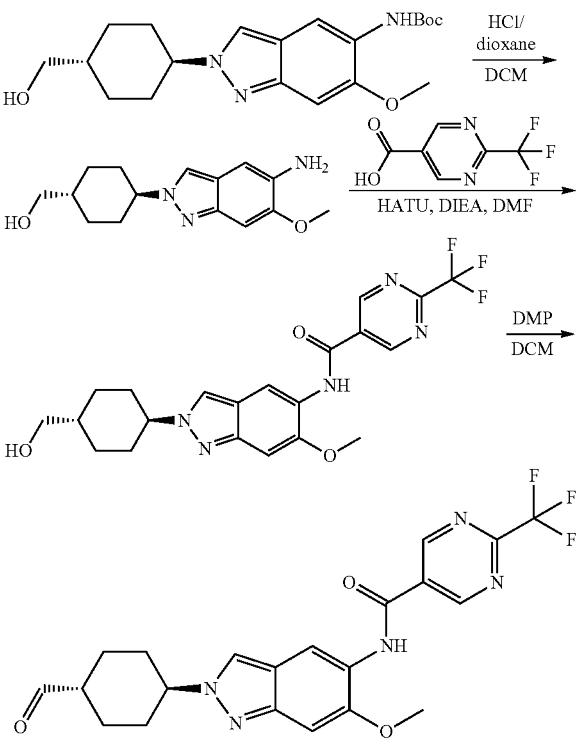

BIW

Step 1—[4-(5-Amino-6-methoxy-indazol-2-yl)cyclohexyl]methanol

To a solution of tert-butyl N-[2-[4-(hydroxymethyl)cyclohexyl]-6-methoxy-indazol-5-yl]carbamate (300 mg, 799 umol, synthesized via Step 1 of Intermediate BGT) in DCM (5.00 mL) was added HCl/dioxane (4 M, 2.00 mL). The mixture was stirred at 20° C. for 1 hr. On completion, the reaction mixture was concentrated in vacuo to give the residue. The residue was triturated with EA (3 mL) at 20° C. for 20 minutes to give the title compound (240 mg, 96% yield, HCl) as a yellow solid. $^1H$ NMR (400 MHz, DMSO-$d_6$) δ 10.48-9.93 (m, 2H), 8.45 (s, 1H), 7.89 (s, 1H), 7.19 (s, 1H), 4.45-4.34 (m, 1H), 3.91 (s, 3H), 3.27 (d, J=6.0 Hz, 2H), 2.19-2.05 (m, 2H), 1.96-1.80 (m, 4H), 1.53-1.38 (m, 1H), 1.21-1.07 (m, 2H). LC-MS ($ESI^+$) m/z 276.2 $(M+H)^+$.

Step 2—N-[2-[4-(hydroxymethyl)cyclohexyl]-6-methoxy-indazol-5-yl]-2-(trifluoromethyl)pyrimidine- 5-carboxamide To a solution of [4-(5-amino-6-methoxy-indazol-2-yl)cyclohexyl]methanol (214 mg, 687 umol, HCl) and 2-(trifluoromethyl)pyrimidine-5-carboxylic acid (120 mg, 625 umol, CAS #306960-74-7) in DMF (3.00 mL) was added HATU (285 mg, 749 umol) and DIEA (323 mg, 2.50 mmol, 435 uL). The mixture was stirred at 20° C. for 1 hr. On completion, the reaction mixture was quenched by addition $H_2O$ (10 mL), and extracted with DCM (3×10 mL). The combined organic layer was washed with brine (3×30 mL), dried over anhydrous $Na_2SO_4$, filtered and concentrated in vacuo to give a residue. The residue was purified by reversed-phase (0.1% FA condition) to give the title compound (140 mg, 49% yield) as a yellow solid. $^1H$ NMR (400 MHz, DMSO-$d_6$) δ 10.12 (s, 1H), 9.47 (s, 2H), 8.33 (s, 1H), 8.15 (s, 1H), 7.10 (s, 1H), 4.50 (t, J=5.2 Hz, 1H), 4.43-4.30 (m, 1H), 3.88 (s, 3H), 3.29 (t, J=5.2 Hz, 2H), 2.19-2.10 (m, 2H), 1.95-1.82 (m, 4H), 1.54-1.41 (m, 1H), 1.21-1.08 (m, 2H). LC-MS ($ESI^+$) m/z 450.3 $(M+H)^+$.

Step 3—N-[2-(4-formylcyclohexyl)-6-methoxy-indazol-5-yl]-2-(trifluoromethyl)pyrimidine-5- carboxamide To a solution of N-[2-[4-(hydroxymethyl)cyclohexyl]-6-methoxy-indazol-5-yl]-2-(trifluoromethyl) pyrimidine-5-carboxamide (100 mg, 222 umol) in DCM (10 mL) was added DMP (120 mg, 282 umol). The mixture was stirred at 20° C. for 1 hr. On completion, the reaction mixture was quenched by addition saturated solution of $Na_2S_2O_3$ (8 mL), and saturated solution of $NaHCO_3$ (20 mL), then extracted with DCM (2×30 mL). The combined organic layer was washed with brine (2×60 mL), dried over anhydrous $Na_2SO_4$, filtered and concentrated in vacuo to give the title compound (99.0 mg, 99% yield) as a yellow solid. $^1H$ NMR (400 MHz, DMSO-$d_6$) δ 10.13 (s, 1H), 9.64 (s, 1H), 9.47 (s, 2H), 8.33 (s, 1H), 8.16 (s, 1H), 7.10 (s, 1H), 4.47-4.34 (m, 1H), 3.88 (s, 3H), 2.47-2.37 (m, 1H), 2.26-2.05 (m, 4H), 2.03-1.90 (m, 2H), 1.52-1.38 (m, 2H). LC-MS ($ESI^+$) m/z 448.1 $(M+H)^+$.

((1r,4r)-4-(5-Bromo-6-methoxy-2H-pyrazolo[3,4-b]pyridin-2-yl)cyclohexyl)methanol (Intermediate BIX)

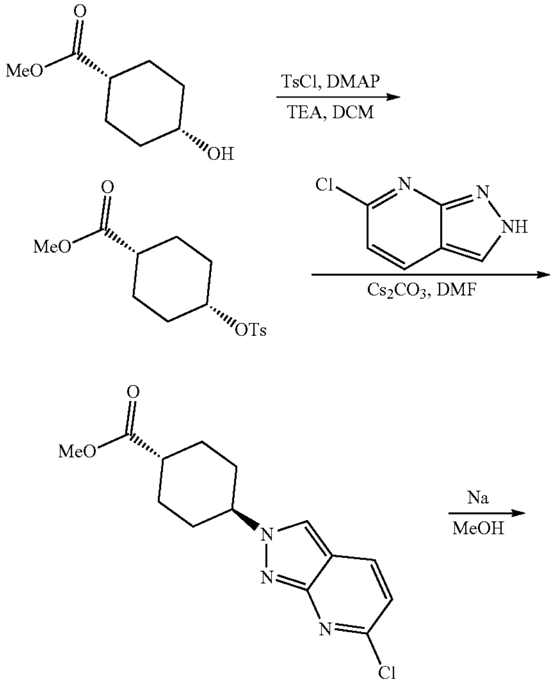

-continued

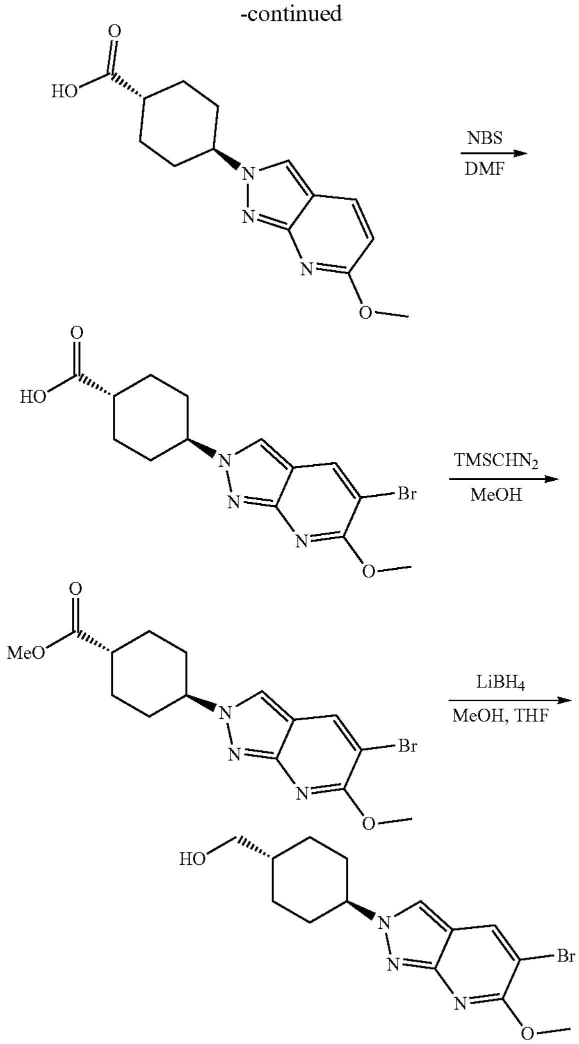

BIX

Step 1—2- Methyl 4-(p-tolylsulfonyloxy)cyclohexanecarboxylate

To a solution of methyl 4-hydroxycyclohexanecarboxylate (6.00 g, 37.9 mmol), DMAP (463 mg, 3.79 mmol) and TEA (11.5 g, 113 mmol) in DCM (120 mL) was added TosCl (14.4 g, 75.8 mmol) at 20° C. The reaction mixture was stirred at 20° C. for 2 days. On completion, the mixture was quenched with water (100 mL). The organic layer was washed with brine (400 mL) and concentrated in vacuo. The residue was purified by silica gel chromatography (PE: EA=8:1) to give the title compound (10.2 g, 86% yield) obtained as yellow solid.

Step 2—(1r,4r)-Methyl 4-(6-chloro-2H-pyrazolo[3,4-b]pyridin-2-yl)cyclohexanecarboxylate A mixture of methyl 4-(p-tolylsulfonyloxy)cyclohexanecarboxylate (10.2 g, 32.6 mmol), 6-chloro-2H-pyrazolo[3,4-b]pyridine (4.18 g, 27.2 mmol, CAS #63725-51-9), $Cs_2CO_3$ (26.6 g, 81.6 mmol) in DMF (150 mL) was degassed and purged with $N_2$ for three times. The mixture was stirred at 80° C. for 12 hours under $N_2$. On completion, the reaction mixture was diluted with EA (500 mL) and filtered. The filtrate was washed with water (2×150 mL) and brine (2×100 mL). The organic phase was dried with anhydrous $Na_2SO_4$ and filtered. The filtrate was concentrated in vacuo. The residue was purified by silica column (PE/EA=10/1 to 3/1) to give the title compound (1.00 g, 10% yield) as yellow oil. $^1$H NMR (400 MHz, $CDCl_3$) δ 7.97-7.94 (m, 2H), 7.02 (d, J=8.4 Hz, 1H), 4.43-4.35 (m, 1H), 2.35-2.31 (m, 1H), 2.28-2.24 (m, 2H), 2.24-2.20 (m, 2H), 2.08-2.03 (m, 2H), 1.71-1.68 (m, 2H).

Step 3—(1r,4r)-4-(6-Methoxy-2H-pyrazolo[3,4-b]pyridin-2-yl)cyclohexanecarboxylic acid To a solution of MeOH (17 mL) was added sodium (332 mg, 14.4 mmol) at 25° C. The methyl 4-(6-chloropyrazolo[3,4-b]pyridin-2-yl)cyclohexanecarboxylate (850 mg, 2.89 mmol) in MeOH (34 mL) was added slowly at 0° C. The mixture was stirred 70° C. for 12 hours. On completion, the reaction mixture was concentrated in vacuo to remove MeOH, acidified with aq. HCl (4 M) to pH=7 and concentrated in vacuo to give a residue. The residue was purified by column chromatography (ethyl acetate) to give the title compound (100 mg, 8% yield) as a yellow solid. $^1$H NMR (400 MHz, DMSO-$d_6$) δ 8.29 (s, 1H), 7.99 (d, J=8.8 Hz, 1H), 6.58-6.54 (m, 1H), 4.39-4.32 (m, 1H), 3.87 (s, 3H), 2.25-2.19 (m, 1H), 2.15-2.03 (m, 4H), 1.94-1.84 (m, 2H), 1.54-1.51 (m, 2H).

Step 4—(1r,4r)-4-(5-Bromo-6-methoxy-2H-pyrazolo[3,4-b]pyridin-2-yl)cyclohexanecarboxylic acid To a solution of 4-(6-methoxypyrazolo[3,4-b]pyridin-2-yl)cyclohexanecarboxylic acid (700 mg, 1.27 mmol) in DMF (10 mL) was added NBS (158 mg, 889 umol) at 0° C. The mixture was stirred at 0° C. for 2 hours. On completion, the reaction mixture was quenched with water (2 mL) at 0° C., diluted with EA (10 mL) and extracted with EA (2×25 mL). The combined organic layers were washed with brine (20 mL), dried with anhydrous $Na_2SO_4$ and filtered. The filtrate was concentrated in vacuo to give a residue. The residue was purified by reversed phase HPLC (0.1% FA condition) to give the title compound (130 mg, 28% yield) as a brown solid $^1$H NMR (400 MHz, DMSO-$d_6$) δ 8.43 (s, 1H), 8.30 (s, 1H), 4.46-4.35 (m, 1H), 3.96 (s, 3H), 2.60-2.51 (m, 1H), 2.11-2.03 (m, 4H), 1.94-1.90 (m, 2H), 1.56-1.54 (m, 2H), LC-MS (ESI$^+$) m/z 354.0 (M+H)$^+$.

Step 5—(1r,4r)-Methyl 4-(5-romo-6-methoxy-2H-pyrazolo[3,4-b]pyridin-2-yl)cyclohexane carboxylate To a solution of 4-(5-bromo-6-methoxy-pyrazolo[3,4-b]pyridin-2-yl)cyclohexanecarboxylic acid (100 mg, 282 umol) in MeOH (1 mL) was added diazomethyl(trimethyl)silane (2 M, 2.12 mL) dropwise. The reaction mixture was stirred at 25° C. for 1 hour. On completion, the reaction was quenched with AcOH (2 mL) and concentrated in vacuo. The residue was purified by silica column (PE/EA=2/1) to give the title compound (100 mg, 96% yield) as a light yellow solid. LC-MS (ESI$^+$) m/z 368.0 (M+H)$^+$.

Step 6—((1r,4r)-4-(5-Bromo-6-methoxy-2H-pyrazolo[3,4-b]pyridin-2-yl)cyclohexyl)methanol To a solution of methyl 4-(5-bromo-6-methoxy-pyrazolo[3,4-b]pyridin-2-yl)cyclohexanecarboxylate (90.0 mg, 244 umol) in MeOH (0.2 mL) and THE (1.6 mL) was added $LiBH_4$ (26.6 mg, 1.22 mmol) in portions at 0° C. The reaction mixture was stirred at 25° C. for 2 hours. On completion, the reaction was quenched with water (20 mL) and extracted with EA (2×40 mL). The organic layers were washed with brine (2×20 mL), dried with anhydrous $Na_2SO_4$ and concentrated in vacuo to give the title compound (80.0 mg, 96% yield) as a light yellow solid. LC-MS (ESI$^+$) m/z 340.0 (M+H)$^+$.

N-(2-((1r,4r)-4-Formylcyclohexyl)-6-methoxy-2H-pyrazolo[3,4-b]pyridin-5-yl)-6- (trifluoromethyl)picolinamide (Intermediate BIY)

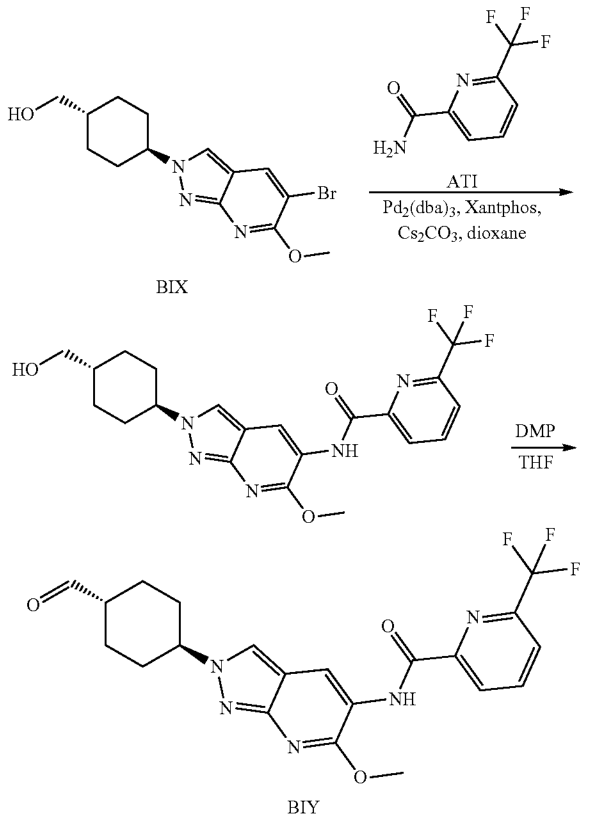

Step 1—N-(2-((1r,4r)-4-(hydroxymethyl)cyclohexyl)-6-methoxy-2H-pyrazolo[3,4-b]pyridin-5-yl)-6- (trifluoromethyl)picolinamide To a solution of [4-(5-bromo-6-methoxy-pyrazolo[3,4-b]pyridin-2-yl)cyclohexyl]methanol (55.0 mg, 161 umol, Intermediate BIX) and 6-(trifluoromethyl)pyridine-2-carboxamide (36.8 mg, 194 umol, Intermediate ATI) in dioxane (1 mL) was added $Pd_2(dba)_3$ (14.8 mg, 16.1 umol), Xantphos (18.7 mg, 32.3 umol) and $Cs_2CO_3$ (105 mg, 323 umol). The reaction mixture was stirred at 80° C. for 12 hours under $N_2$. On completion, the reaction mixture was diluted with THE (20 mL) and filtered. The filtrate was concentrated in vacuo, and he residue was purified by silica column (EA) to give the title compound (60.0 mg, 82% yield) as a white solid. LC-MS (ESI$^+$) m/z 450.2 (M+H)$^+$.

Step 2—N-(2-((1r,4r)-4-Formylcyclohexyl)-6-methoxy-2H-pyrazolo[3,4-b]pyridin-5-yl)-6- (trifluoromethyl)picolinamide To a solution of N-[2-[4-(hydroxymethyl)cyclohexyl]-6-methoxy-pyrazolo[3,4-b]pyridin-5- yl]-6-(trifluoromethyl) pyridine-2-carboxamide (55.0 mg, 122 umol) in THE (2 mL) was added DMP (62.2 mg, 146 umol). The reaction mixture was stirred at 25° C. for 1 hour. On completion, the reaction mixture was diluted with THE (20 mL) and EA (30 mL) and washed with sat. $Na_2S_2O_3$ (20 mL) and brine (2×20 mL). The organic layer was concentrated in vacuo to give the title compound (50.0 mg, 91% yield) as off-white solid. LC-MS ($ESI^+$) m/z 448.1 $(M+H)^+$.

N-[2-(4-formylcyclohexyl)-6-methylsulfanyl-indazol-5-yl]-6-(trifluoromethyl)pyridine- 2-carboxamide (Intermediate BIZ)

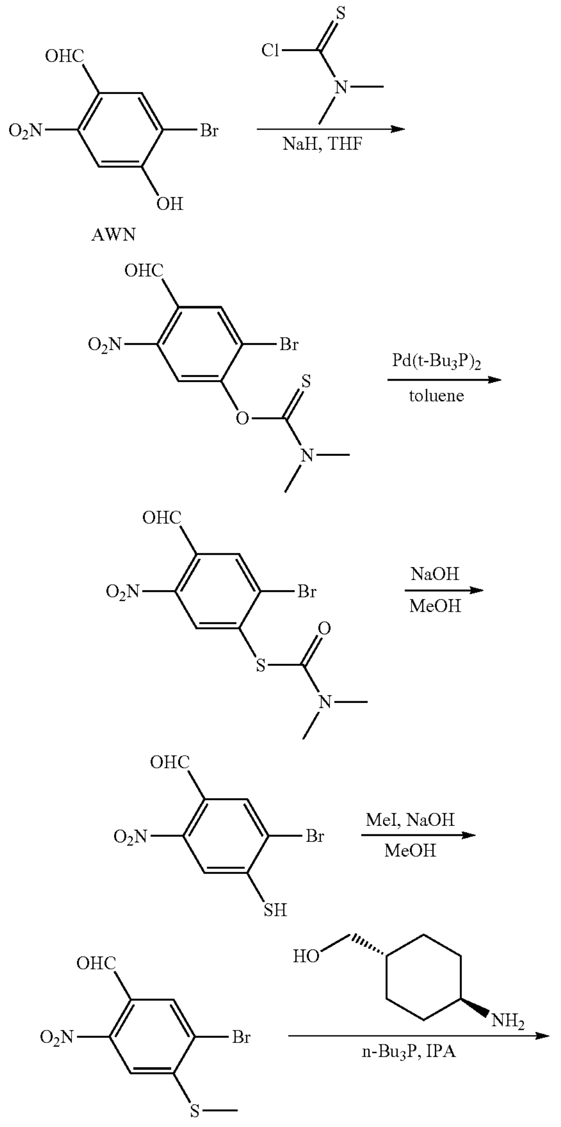

-continued

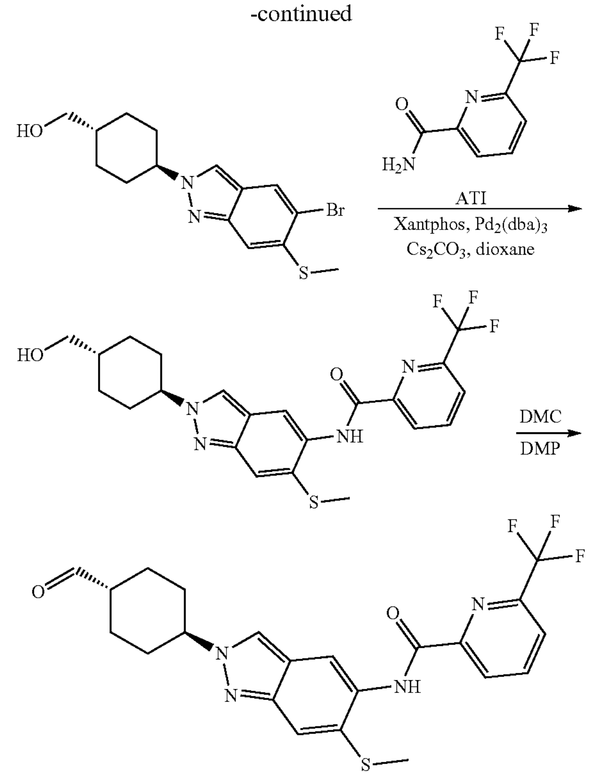

BIZ

Step 1—O-(2-bromo-4-formyl-5-nitro-phenyl) N,N-dimethylcarbamothioate

To a solution of 5-bromo-4-hydroxy-2-nitro-benzaldehyde (5.00 g, 20.3 mmol, Intermediate AWN) in THE (250 mL) was added NaH (894 mg, 22.3 mmol, 60% dispersion in mineral oil) at 0° C. for 0.5 hour. Then the mixture was stirred at 25° C. for 1 hour. Then N,Ndimethylcarbamothioylchloride (3.01 g, 24.4 mmol, CAS #16420-13-6) in THE (100 mL) was added at 0° C. Then the mixture was stirred 25° C. for 12 hours. On completion, the reaction mixture was diluted in $H_2O$ (100 mL) and EA (300 mL). The organic phase was separated, washed with brine (100 mL), dried over $Na_2SO_4$, filtered and concentrated. The residue was purified by column chromatography (petroleum ether/ethyl acetate=10/1 to 0/1) to give the title compound (13.0 g, 64% yield) as a yellow solid. $^1H$ NMR (400 MHz, $CDCl_3$) δ 10.43 (s, 1H), 8.21 (s, 1H), 7.98 (s, 1H), 3.50 (s, 3H), 3.46 (s, 3H).

Step 2—S-(2-bromo-4-formyl-5-nitro-phenyl) N,N-dimethylcarbamothioate

A mixture of O-(2-bromo-4-formyl-5-nitro-phenyl) N,N-dimethylcarbamothioate (13 g, 39.0 mmol), $Pd(t-Bu_3P)_2$ (399 mg, 780 umol) in toluene (200 mL) was degassed and purged with $N_2$ for 3 times, and then the mixture was stirred at 120° C. for 24 hours under $N_2$ atmosphere. On completion, the reaction mixture was concentrated under reduced pressure to remove toluene. The residue was diluted with $H_2O$ (200 mL) and extracted with DCM (400 mL×2). The combined organic layers were washed with brine (200 mL), dried over $Na_2SO_4$, filtered and concentrated under reduced pressure to give a residue. The residue was triturated with EA (20 mL) to give the title compound (7.00 g, 53% yield) as a yellow solid. $^1$HNMR (400 MHz, $CDCl_3$) δ 10.42 (s, 1H), 8.47 (s, 1H), 8.18 (s, 1H), 3.17 (s, 3H), 3.09 (s, 3H).

Step 3—5-Bromo-2-nitro-4-sulfanyl-benzaldehyde

A mixture of S-(2-bromo-4-formyl-5-nitro-phenyl) N,N-dimethylcarbamothioate (2.00 g, 6.00 mmol), NaOH (480 mg, 12.0 mmol) in MeOH (80 mL) was degassed and purged with $N_2$ for 3 times, and then the mixture was stirred at 25° C. for 12 hours under $N_2$ atmosphere. On completion, the reaction mixture was quenched by addition HCl (1M) and adjusted to pH=5-6 at 25° C., and then filtered. The filter cake was dried in vacuo to give the title compound (1.50 g, 90% yield) as a brown solid.

Step 4—5-Bromo-4-methylsulfanyl-2-nitro-benzaldehyde

To a solution of 5-bromo-2-nitro-4-sulfanyl-benzaldehyde (1.5 g, 5.72 mmol), NaOH (458 mg, 11.5 mmol) in MeOH (80 mL) was stirred for 0.5 hr. Then iodomethane (4.06 g, 28.6 mmol) was added at 25° C. and the mixture was stirred at 25° C. for 3 hours. On completion, the reaction mixture was quenched by addition HCl (1 M) to adjust the pH=7-8 at 0° C., and then the reaction mixture was concentrated under reduced pressure to remove MeOH. The residue was diluted with $H_2O$ (20 mL) and extracted with EA (2×200 mL). The combined organic layers were washed with brine (100 mL), dried over $Na_2SO_4$, filtered and concentrated in vacuo to give a residue. The residue was purified by column chromatography (petroleum ether/ethyl acetate=10/1 to 1/1) to give the title compound (1.50 g, 94% yield) as a yellow solid. $^1$HNMR (400 MHz, $CDCl_3$) δ 10.34 (s, 1H), 8.12 (s, 1H), 7.74 (s, 1H), 2.62 (s, 3H).

Step 5—[4-(5-Bromo-6-methylsulfanyl-indazol-2-yl)cyclohexyl]methanol

A mixture of 5-bromo-4-methylsulfanyl-2-nitro-benzaldehyde (1.30 g, 4.71 mmol) and (4-aminocyclohexyl) methanol (608 mg, 4.71 mmol, CAS #1467-84-1) in IPA (45 mL) was stirred at 80° C. for 16 hours under $N_2$. The mixture was cooled to 25° C. and tributylphosphane (2.86 g, 14.1 mmol) was added. The reaction mixture was stirred at 80° C. for 6 hours. On completion, the reaction mixture was partitioned between $H_2O$ (100 mL) and EA (400 mL). The organic phase was separated, washed with brine (100 mL), dried over $Na_2SO_4$, filtered and concentrated in vacuo. The residue was purified by column chromatography (petroleum ether/ethyl acetate=10/1 to 1/1) to give the title compound (1.10 g, 65% yield) as a yellow solid. $^1$H NMR (400 MHz, $CDCl_3$) δ 7.85 (d, J=6.8 Hz, 2H), 7.39 (s, 1H), 4.36-430 (m, 1H), 3.54 (s, 2H), 2.50 (s, 3H), 2.30 (d, J=10.8 Hz, 2H), 2.05-1.94 (m, 4H), 1.67-1.65 (m, 1H), 1.44-1.43 (m, 1H), 1.28-1.19 (m, 2H); LC-MS ($ESI^+$) m/z 357.0 $(M+H)^+$.

Step 6—N-[2-[4-(hydroxymethyl)cyclohexyl]-6-methylsulfanyl-indazol-5-yl]-6-(trifluoromethyl) pyridine-2-carboxamide A mixture of [4-(5-bromo-6-methylsulfanyl-indazol-2-yl) cyclohexyl]methanol (1.00 g, 2.81 mmol), 6-(trifluoromethyl)pyridine-2-carboxamide (535 mg, 2.81 mmol, Intermediate ATI), $Cs_2CO_3$ (1.83 g, 5.63 mmol), Xantphos (326 mg, 563 umol) and $Pd_2(dba)_3$ (258 mg, 281 umol) in dioxane (15 mL) was degassed and purged with $N_2$ for 3 times, and then the mixture was stirred at 95° C. for 24 hours under $N_2$ atmosphere. The reaction mixture was filtered and concentrated under reduced pressure to give a residue. The residue was purified by column chromatography (petroleum ether/ethyl acetate=20/1 to 1/1) to give the title compound (700 mg, 46% yield) as a brown solid. $^1$H NMR (400 MHz, $CDCl_3$) δ 11.04 (s, 1H), 8.76 (s, 1H), 8.43 (d, J=8.0 Hz, 1H), 8.06 (t, J=8.0 Hz, 1H), 7.88 (d, J=7.2 Hz, 2H), 7.81 (d, J=7.2 Hz, 1H), 4.35-4.27 (m, 1H), 3.49 (d, J=6.0 Hz, 2H), 2.42 (s, 3H), 2.29-2.25 (m, 2H), 2.00-1.90 (m, 4H), 1.65-1.56 (m, 2H), 1.24-1.14 (m, 2H).

Step 7—N-[2-(4-formylcyclohexyl)-6-methylsulfanyl-indazol-5-yl]-6-(trifluoromethyl)pyridine- 2-carboxamide To a solution of N-[2-[4-(hydroxymethyl)cyclohexyl]-6-methylsulfanyl-indazol-5-yl]-6-(trifluoromethyl)pyridine-2-carboxamide (120 mg, 258 umol) in DCM (2 mL) was added DMP (142 mg, 336 umol) at 0° C. The mixture was stirred at 0-25° C. for 1 hour. On completion, the reaction mixture was quenched by addition of $Na_2S_2O_3$ (1 mL). Then $NaHCO_3$ (1 mL) was added until the pH=8 at 25° C. The mixture was next diluted with $H_2O$ (5 mL) and extracted with DCM (2×10 mL). The combined organic layers were dried over $Na_2SO_4$, filtered and concentrated in vacuo to give the title compound (100 mg, 84% yield) as a yellow solid. LC-MS (ESI+) m/z 463.2 $(M+H)^+$.

3-Chloro-N-[2-(4-formylcyclohexyl)-6-(1-hydroxy-1-methyl-ethyl)indazol-5-yl]pyridine-2- carboxamide (Intermediate BJA)

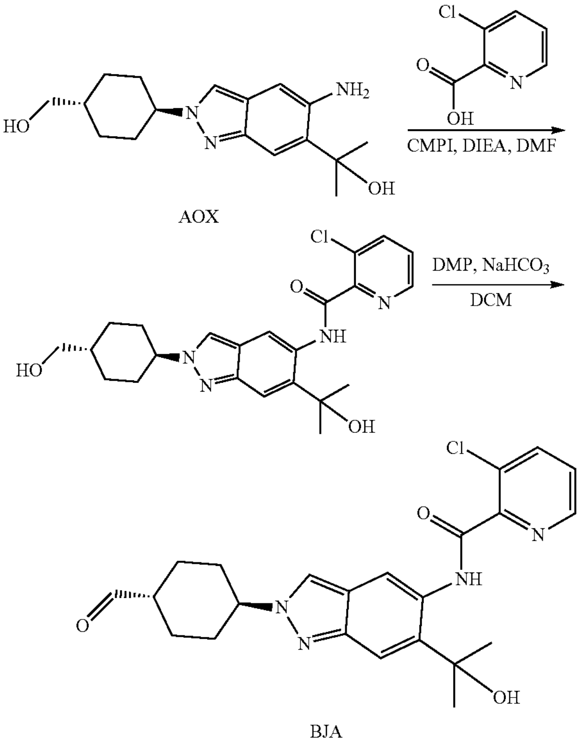

AOX

BJA

Step 1—3-Chloro-N-[2-[4-(hydroxymethyl)cyclohexyl]-6-(1-hydroxy-1-methyl-ethyl) indazol-5-yl] pyridine-2-carboxamide A mixture of 2-[5-amino-2-[4-(hydroxymethyl)cyclohexyl]indazol-6-yl]propan-2-ol (100 mg, 330 umol, Intermediate AOX), 3-chloropyridine-2-carboxylic acid (CAS #57266-69-0, 51.9 mg, 330 umol), CMPI (101 mg, 396 umol), DIEA (127 mg, 988 umol) in DMF (1 mL) was degassed and purged with $N_2$ for 3 times, and then the mixture was stirred at 25° C. for 1 hour under $N_2$ atmosphere. On completion, the reaction mixture was diluted with $H_2O$ (5 mL) and EA (20 mL). The organic phase was separated, washed with brine (10 mL), dried over $Na_2SO_4$, filtered and concentrated in vacuo to give the title compound (130 mg, 8900 yield) as a yellow solid. LC-MS ($ESI^+$) m/z 443.2 $(M+H)^+$.

Step 2—3-Chloro-N-[2-(4-formylcyclohexyl)-6-(1-hydroxy-1-methyl-ethyl) indazol-5-yl]pyridine-2-carboxamide To a solution of 3-chloro-N-[2-[4-(hydroxymethyl)cyclohexyl]-6-(1-hydroxy-1-methyl-ethyl)indazol -5-yl]pyridine-2-carboxamide (130 mg, 294 umol) in DCM (2 mL) was added DMP (162 mg, 382 umol) and $NaHCO_3$ (123 mg, 1.47 mmol). The mixture was stirred at 0-25° C. for 2 hours. The reaction mixture was quenched by addition of $Na_2S_2O_3$ (1 mL), then $NaHCO_3$ (1 mL) was added until pH=8 at 25° C. Then the mixture was diluted with $H_2O$ (5 mL) and extracted with DCM 20 mL (2×10 mL). The combined organic layers were dried over $Na_2SO_4$, filtered and concentrated in vacuo to give the title compound (120 mg, 92% yield) as a yellow solid. LC-MS ($ESI^+$) m/z 441.2 $(M+H)^+$.

N-[2-(4-formylcyclohexyl)-6-methylsulfonyl- indazol-5-yl]-6-(trifluoromethyl)pyridine-2-carboxamide (Intermediate BJB)

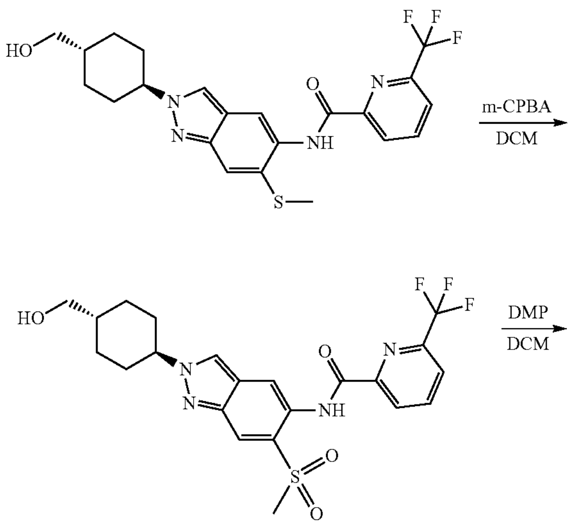

-continued

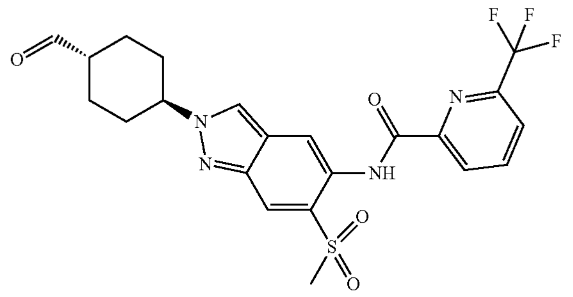

BJB

Step 1—N-[2-[4-(hydroxymethyl)cyclohexyl]-6-methylsulfonyl-indazol-5-yl]-6-(trifluoromethyl) pyridine-2-carboxamide To a solution of N-[2-[4-(hydroxymethyl)cyclohexyl]-6-methylsulfanyl-indazol-5-yl]-6-(trifluoromethyl)pyridine-2-carboxamide (400 mg, 861 umol, synthesized via Steps 1-6 of Intermediate BIZ) in DCM (15 mL) was added m-CPBA (928 mg, 4.31 mmol, 80% solution) at 0° C. The mixture was then stirred at 25° C. for 12 hours. On completion, the reaction mixture was concentrated in vacuo to give a residue. The residue was purified by column chromatography (petroleum ether/ethyl acetate=10/1 to 3/1) to give the title compound (300 mg, 56% yield) as a yellow solid. LC-MS (ESI+) m/z 497.1 $(M+H)^+$.

Step 2—N-[2-(4-formylcyclohexyl)-6-methylsulfonyl-indazol-5-yl]-6-(trifluoromethyl)pyridine-2-carboxamide To a solution of N-[2-[4-(hydroxymethyl)cyclohexyl]-6-methylsulfonyl-indazol-5-yl]-6- (trifluoromethyl)pyridine-2-carboxamide (70.0 mg, 140 umol) in DCM (2 mL) was added DMP (77.7 mg, 183 umol). The mixture was stirred at 0-25° C. for 1 hour. The reaction mixture was quenched by addition saturated $NaHCO_3$ (1 mL) and $Na_2S_2O_3$ (1 mL), and then diluted with $H_2O$ (5 mL) and extracted with DCM (2×25 mL). The combined organic layers were washed with brine (10 mL), dried over $Na_2SO_4$, filtered and concentrated in vacuo to give the title compound (60.0 mg, 86% yield) as a yellow solid. LC-MS (ESI+) m/z 495.1 $(M+H)^+$.

[4-[5-Bromo-6-[4-[tert-butyl(dimethyl)silyl]oxy-1-piperidyl]indazol-2-yl]cyclohexyl]methanol (Intermediate BJC)

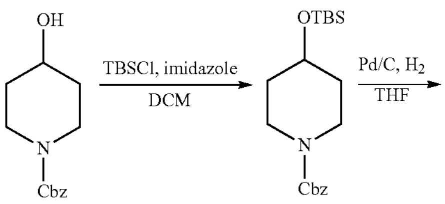

-continued

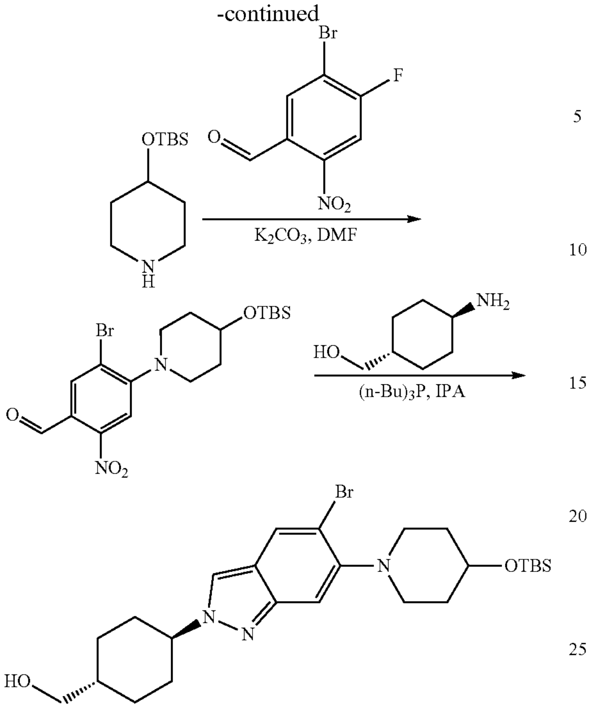

BJC

Step 1—Benzyl 4-[tert-butyl(dimethyl)silyl]oxypiperidine-1-carboxylate

To a solution of benzyl 4-hydroxypiperidine-1-carboxylate (10.0 g, 42.5 mmol, CAS #95798-23-5) in DCM (100 mL) was added TBSCl (7.69 g, 51.0 mmol) and imidazole (8.68 g, 127 mmol). The mixture was stirred at 15° C. for 16 hrs. On completion, the mixture was washed with $H_2O$ (3×150 mL), and brine (3×100 mL). The organic layer was dried over anhydrous $Na_2SO_4$, filtered and concentrated in vacuo to give the title compound (14.8 g, 99% yield) as colorless oil. $^1H$ NMR (400 MHz, $CDCl_3$) δ 7.45-7.27 (m, 5H), 5.13 (s, 2H), 3.93-3.85 (m, 1H), 3.76-3.61 (m, 2H), 3.50-3.30 (m, 2H), 1.80-1.63 (m, 2H), 1.57-1.42 (m, 2H), 0.89 (s, 9H), 0.06 (s, 6H).

Step 2—Tert-butyl-dimethyl-(4-piperidyloxy)silane

To a solution of benzyl 4-[tert-butyl(dimethyl)silyl]oxypiperidine-1-carboxylate (12.8 g, 36.6 mmol) in THF (130 mL) was added Pd/C (1.28 g, 10 wt %). The mixture was stirred at 15° C. for 16 hrs under $H_2$ (15 psi). On completion, the mixture was filtered and concentrated in vacuo to give the title compound (7.8 g, 98% yield) as black oil. $^1H$ NMR (400 MHz, $CDCl_3$) δ 3.80-3.66 (m, 1H), 3.11-3.01 (m, 2H), 2.65-2.55 (m, 2H), 1.85-1.71 (m, 2H), 1.47-1.38 (m, 2H), 0.89 (s, 9H), 0.05 (s, 6H).

Step 3—5-Bromo-4-[4-[tert-butyl(dimethyl)silyl]oxy-1-piperidyl]-2-nitro-benzaldehyde To a solution of tert-butyl-dimethyl-(4-piperidyloxy)silane (3.82 g, 17.7 mmol), 5-bromo-4-fluoro-2-nitrobenzaldehyde (4.00 g, 16.1 mmol, CAS #213382-45-7) in DMF (70.0 mL) was added $K_2CO_3$ (6.69 g, 48.3 mmol). The mixture was stirred at 80° C. for 16 hrs. On completion, the mixture was quenched with $H_2O$ (400 mL) and extracted with EA (3×100 mL). The organic layers were washed with brine (3×80 mL) and dried over anhydrous $Na_2SO_4$, filtered and concentrated in vacuo. The mixture was purified by silica gel column (PE:EA=100:1) to give the title compound (2.5 g, 34% yield) as yellow solid, $^1H$ NMR (400 MHz, $CDCl_3$) δ 10.29 (s, 1H), 8.18 (s, 1H), 7.60 (s, 1H), 4.04-3.97 (m, 1H), 3.45-3.35 (m, 2H), 3.19-3.09 (m, 2H), 2.05-1.93 (m, 2H), 1.81-1.74 (m, 2H), 0.92 (s, 9H), 0.10 (s, 6H), LC-MS ($ESI^+$) m/z 445.2 $(M+H)^+$.

Step 4—[4-[5-Bromo-6-[4-[tert-butyl(dimethyl)silyl]oxy-1-piperidyl]indazol-2-yl]cyclohexyl]methanol To a solution of 5-bromo-4-[4-[tert-butyl(dimethyl)silyl]oxy-1-piperidyl]-2-nitro-benzaldehyde (1.40 g, 3.16 mmol) in IPA (14 mL) was added (4-aminocyclohexyl)methanol (407 mg, 3.16 mmol, CAS #1467-84-1). The mixture was stirred at 80° C. for 16 hrs. Then tributylphosphane (1.92 g, 9.47 mmol) was added and the mixture was stirred at 80° C. for 16 hrs. On completion, the mixture was concentrated in vacuo. The mixture was purified by reverse phase (0.1% FA) to give the title compound (920 mg, 55% yield) as yellow solid. $^1H$ NMR (400 MHz, DMSO-$d_6$) δ 8.27 (s, 1H), 7.96 (s, 1H), 7.21 (s, 1H), 4.52-4.45 (m, 1H), 4.43-4.32 (m, 1H), 3.95-3.80 (m, 1H), 3.30-3.25 (m, 2H), 3.19-3.07 (m, 2H), 2.80-2.70 (m, 2H), 2.14-2.05 (m, 2H), 1.95-1.82 (m, 6H), 1.70-1.57 (m, 2H), 1.50-1.40 (m, 1H), 1.20-1.04 (m, 2H), 0.89 (s, 9H), 0.08 (s, 6H); LC-MS ($ESI^+$) m/z 522.2 $(M+H)^+$.

N-[6-[4-[tert-butyl(dimethyl)silyl]oxy-1-piperidyl]-2-(4-formylcyclohexyl)indazol-5-yl]-6- (trifluoromethyl)pyridine-2-carboxamide (Intermediate BJD)

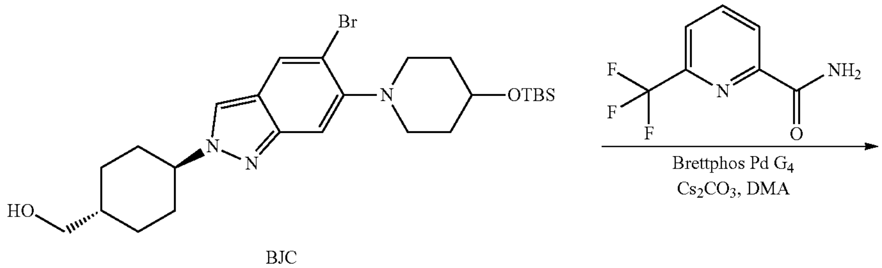

BJC

-continued

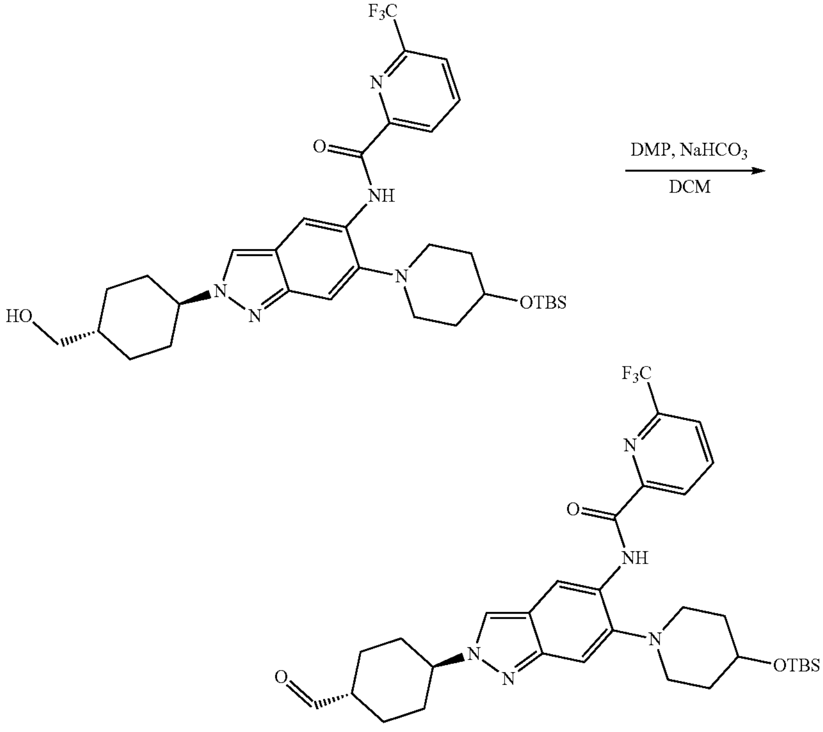

BJD

Step 1—N-[6-[4-[tert-butyl(dimethyl)silyl]oxy-1-piperidyl]-2-[4-(hydroxymethyl)cyclohexyl]indazol-5-yl]-6-(trifluoromethyl)pyridine-2-carboxamide To a solution of [4-[5-bromo-6-[4-[tert-butyl(dimethyl)silyl]oxy-1-piperidyl]indazol-2-yl]cyclohexyl]methanol (50 mg, 95.6 umol, Intermediate BJC), 6-(trifluoromethyl)pyridine-2-carboxamide (21.8 mg, 114 umol, CAS #22245-84-7) in DMA (1.00 mL) was added $Cs_2CO_3$ (62.3 mg, 191 umol), BrettPhos (Pd, $G_4$) (8.81 mg, 9.57 umol). The mixture was stirred at 100° C. for 16 hrs under $N_2$. On completion, the mixture was filtered and concentrated in vacuo. The mixture was purified by prep-HPLC (reverse phase: 0.1% FA) to give the title compound (45.0 mg, 37% yield) as yellow solid. $^1$H NMR (400 MHz, DMSO-$d_6$) δ 11.10 (s, 1H), 8.77 (s, 1H), 8.51-8.48 (m, 1H), 8.44-8.38 (m, 1H), 8.37 (s, 1H), 8.23-8.17 (m, 1H), 7.43 (s, 1H), 4.50 (t, J=5.2 Hz, 1H), 4.45-4.32 (m, 1H), 3.99-3.83 (m, 1H), 3.31-3.28 (m, 2H), 3.07-2.99 (m, 2H), 2.86-2.75 (m, 2H), 2.20-2.09 (m, 2H), 2.01-1.87 (m, 6H), 1.85-1.75 (m, 2H), 1.52-1.44 (m, 1H), 1.22-1.12 (m, 2H), 0.92 (s, 9H), 0.09 (s, 6H); LC-MS (ESI$^+$) m/z 632.5 $(M+H)^+$.

Step 2—N-[6-[4-[tert-butyl(dimethyl)silyl]oxy-1-piperidyl]-2-(4-formylcyclohexyl)indazol-5-yl]-6-(trifluoromethyl)pyridine-2-carboxamide To a solution of N-[6-[4-[tert-butyl(dimethyl)silyl]oxy-1-piperidyl]-2-[4-(hydroxymethyl)cyclohexyl]indazol-5-yl]-6-(trifluoromethyl)pyridine-2-carboxamide (35.0 mg, 55.4 umol) in DCM (2.00 mL) was added DMP (35.2 mg, 83.1 umol) and $NaHCO_3$ (23.2 mg, 276 umol). The mixture was stirred at 15° C. for 0.5 hr. On completion, the mixture was diluted with DCM (20 mL) and quenched with saturated $Na_2S_2O_3$ (10 mL) and washed with saturated $NaHCO_3$ (2×10 mL). The organic layer was dried over anhydrous $Na_2SO_4$, filtered and concentrated in vacuo to give the title compound (33 mg, 94% yield) as yellow solid. LC-MS (ESI$^+$) m/z 630.3 $(M+H)^+$.

6-[(1S,4S)-2-oxa-5-azabicyclo[2.2.1]heptan-5-yl]pyridine-2-carboxylic acid (Intermediate BJE)

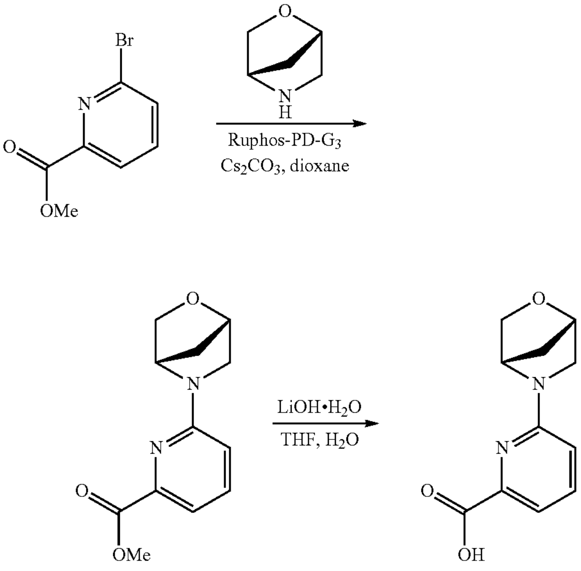

BJE

Step 1—Methyl 6-[(1S,4S)-2-oxa-5-azabicyclo[2.2.1]heptan-5-yl]pyridine-2-carboxylate To a solution of methyl 6-bromopyridine-2-carboxylate (200 mg, 925 umol) in dioxane (4 mL) was added (1S,4S)-2-oxa-5-azabicyclo[2.2.1]heptane (91.7 mg, 925 umol), $Cs_2CO_3$ (603 mg, 1.85 mmol) and RuPhos Pd G3 (77.4 mg, 92.2 umol). The reaction mixture was stirred at 80° C. for 12 hrs. On completion, the mixture was diluted with water (50 mL) and extracted with ethyl acetate (3x25 mL). The combined organic phase was dried over anhydrous sodium sulfate, filtered and concentrated to give a residue. The residue was purified by column chromatography (petroleum ether/ethyl acetate=5:1 to 1:1) to give the title compound (160 mg, 73% yield) as yellow oil. $^1H$ NMR (400 MHz, DMSO-$d_6$) δ 7.65 (t, J=8.4 Hz, 1H), 7.25 (d, J=8.4 Hz, 1H), 6.76 (d, J=8.4 Hz, 1H), 4.91 (s, 1H), 4.67 (s, 1H), 3.83 (s, 3H), 3.80-3.78 (m, 1H), 3.63-3.61 (m, 1H), 3.47-3.44 (m, 1H), 3.29-3.26 (m, 1H), 1.91-1.84 (m, 2H).

Step 2—6-[(1S,4S)-2-oxa-5-azabicyclo[2.2.1]heptan-5-yl]pyridine-2-carboxylic acid To a solution of methyl 6-[(1S,4S)-2-oxa-5-azabicyclo[2.2.1]heptan-5-yl]pyridine-2-carboxylate (150 mg, 640 umol) in THF (2 mL) and $H_2O$ (2 mL) was added $LiOH.H_2O$ (53.7 mg, 1.28 mmol). The reaction mixture was stirred at 25° C. for 2 hrs. On completion, the mixture was adjusted to pH=6.0 with 1N HCl aqueous and concentrated in vacuo to give the title compound (100 mg, 454.08 umol, 71% yield) as obtained as yellow oil. $^1H$ NMR (400 MHz, DMSO-$d_6$) δ 7.65 (t, J=8.4 Hz, 1H), 7.25 (d, J=8.4 Hz, 1H), 6.75 (d, J=8.4 Hz, 1H), 5.04 (s, 1H), 4.67 (s, 1H), 3.79-3.77 (m, 1H), 3.63-3.61 (m, 1H), 3.47-3.44 (m, 1H), 3.29-3.26 (m, 1H), 1.91-1.84 (m, 2H).

Methyl 2-((1r,4r)-4-((benzyloxy)methyl)cyclohexyl)-6-bromobenzo[d]oxazole-5-carboxylate (Intermediate BJK)

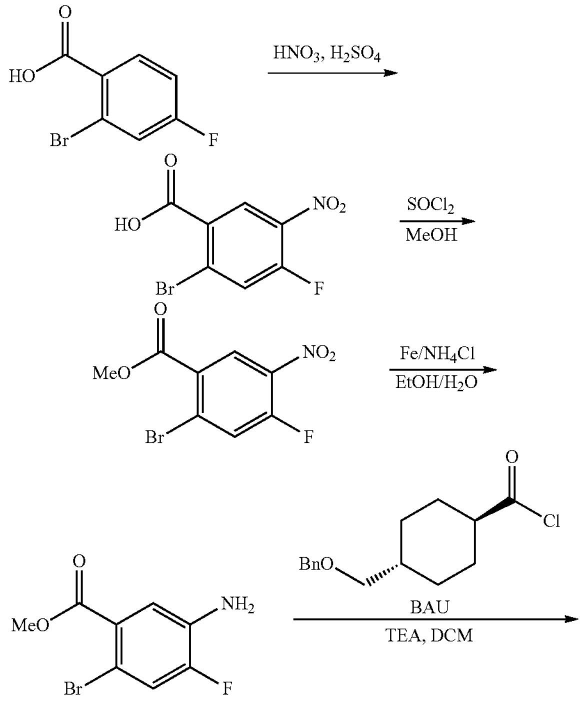

-continued

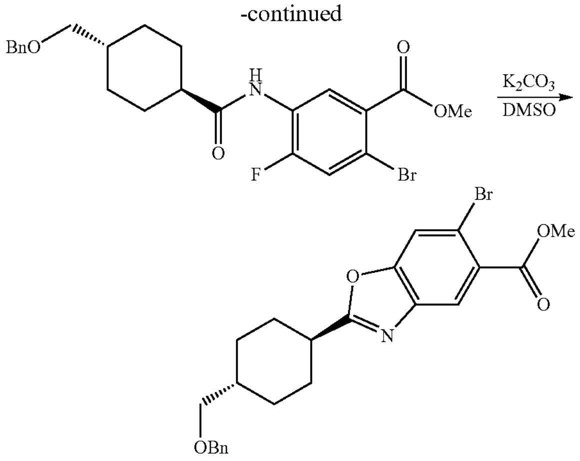

BJK

Step 1—2-Bromo-4-fluoro-5-nitrobenzoic acid

To a solution of 2-bromo-4-fluoro-benzoic acid (15.0 g, 68.4 mmol, CAS #1006-41-3) in $H_2SO_4$ (120 g, 1.23 mol) was added dropwise $HNO_3$ (8.63 g, 136 mmol) at 0° C. The mixture was stirred at 0° C. for 1 hour. On completion, the reaction mixture was poured into ice water slowly 0° C., and then diluted with $H_2O$ (300 mL) and extracted with EA (3x200 mL). The combined organic layers were washed with brine (100 mL), dried over $Na_2SO_4$, filtered and concentrated under reduced pressure to give the title compound (17.4 g, 96% yield) as an off-white solid. $^1H$ NMR (400 MHz, DMSO-$d_6$) δ 14.00 (s, 1H), 8.49 (d, J=8.0 Hz, 1H), 8.15 (d, J=10.8 Hz, 1H).

Step 2—Methyl 2-bromo-4-fluoro-5-nitrobenzoate

To a solution of 2-bromo-4-fluoro-5-nitro-benzoic acid (17.0 g, 64.3 mmol) in MeOH (170 mL) was added dropwise $SOC_2$ (11.4 g, 96.6 mmol) at 0° C. and stirred for 0.5 hour. The mixture was stirred at 60° C. for 11.5 hour. On completion, the reaction mixture was concentrated under reduced pressure to remove solvent. The residue was diluted with sat. $NaHCO_3$ (100 mL) and extracted with EA (3x100 mL). The combined organic layers were washed with brine (100 mL), dried over $Na_2SO_4$, filtered and concentrated under reduced pressure to give the title compound (16.0 g, 89% yield) as an off-white solid. $^1H$ NMR (400 MHz, $CDCl_3$) δ 8.64 (d, J=8.0 Hz, 1H), 7.69 (d, J=10.0 Hz, 1H), 4.01-3.96 (s, 3H).

Step 3—Methyl 5-amino-2-bromo-4-fluorobenzoate

To a solution of methyl 2-bromo-4-fluoro-5-nitro-benzoate (16.0 g, 57.5 mmol) in EtOH (90 mL) and $H_2O$ (30 mL) was added Fe (16.0 g, 287 mmol) and $NH_4Cl$ (15.3 g, 287 mmol) and the mixture was stirred at 80° C. for 2 hours. On completion, the reaction mixture was diluted with EA (200 mL) and $H_2O$ (100 mL), filtered and extracted with EA (3x50 mL). The combined organic layers were washed with brine (50 mL), dried over $Na_2SO_4$, filtered and concentrated under reduced pressure to give a residue. The residue was purified by column chromatography ($SiO_2$, petroleum ether/ethyl acetate=10/1 to 1/1) to give the title compound (8.60 g, 56% yield) was obtained as an off-white solid. LC-MS ($ESI^+$) m/z 250.1 $(M+H)^+$. $^1H$ NMR (400 MHz, $CDCl_3$) δ 7.26-7.16 (m, 2H), 3.83 (s, 3H), 3.81-3.71 (m, 2H).

Step 4—Methyl 5-((1r,4r)-4-((benzyloxy)methyl) cyclohexanecarboxamido)-2-bromo-4- fluorobenzoate To a solution of methyl 5-amino-2-bromo-4-fluoro-benzoate (1.60 g, 6.45 mmol) in DCM (30 mL) was added TEA (1.31 g, 12.9 mmol) and dropwise 4-(benzyloxymethyl) cyclohexanecarbonyl chloride (2.24 g, 8.39 mmol, Intermediate BAU) at 0° C. The mixture was stirred at 25° C. for 1 hour. On completion, the reaction mixture was partitioned between $H_2O$ (50 mL) and DCM (100 mL). The organic phase was separated, washed with brine (50 mL), dried over $Na_2SO_4$, filtered and concentrated under reduced pressure to give a residue. The residue was purified by column chromatography ($SiO_2$, petroleum ether/ethyl acetate=20/1 to 10/1) to give the title compound (1.40 g, 40% yield) as an off-white solid. LC-MS (ESI$^+$) m/z 478.3 (M+H)$^+$. $^1$H NMR (400 MHz, $CDCl_3$) δ 8.86 (d, J=8.4 Hz, 1H), 7.34 (d, J=10.4 Hz, 1H), 7.30-7.16 (m, 5H), 4.43 (s, 2H), 3.83 (s, 3H), 3.24 (d, J=6.0 Hz, 2H), 2.25-2.11 (m, 1H), 2.03-1.81 (m, 4H), 1.70-1.45 (m, 3H), 1.09-0.91 (m, 2H).

Step 5—Methyl 2-((1r,4r)-4-((benzyloxy)methyl) cyclohexyl)-6-bromobenzo[d]oxazole-5-carboxylate To a solution of methyl 5-[[4-(benzyloxymethyl)cyclohexanecarbonyl]amino]-2-bromo-4-fluoro- benzoate (1.60 g, 3.34 mmol) in DMSO (8 mL) was added $K_2CO_3$ (924 mg, 6.69 mmol). The mixture was stirred at 130° C. for 1 hour. On completion, the reaction mixture was partitioned between DCM (100 mL) and $H_2O$ (100 mL). The organic phase was separated, washed with brine (50 mL), dried over $Na_2SO_4$, filtered and concentrated under reduced pressure to give a residue. The residue was purified by column chromatography ($SiO_2$, petroleum ether/ethyl acetate=100/1 to 5/1) to give the title compound (510 mg, 1.09 mmol, 32% yield) as an off-white solid. LC-MS (ESI$^+$) m/z 460.0 (M+H)$^+$. 1H NMR (400 MHz, $CDCl_3$) δ 8.12 (s, 1H), 7.80 (s, 1H), 7.40-7.28 (m, 5H), 4.53 (s, 2H), 3.96 (s, 3H), 3.36 (d, J=6.4 Hz, 2H), 2.91 (tt, J=3.6, 12.2 Hz, 1H), 2.31-2.21 (m, 2H), 2.03 (br dd, J=3.6, 13.6 Hz, 2H), 1.82-1.63 (m, 3H), 1.23-1.11 (m, 2H).

N-(2-((1r,4r)-4-formylcyclohexyl)-5-(2-hydroxypropan-2-yl)benzo[d]oxazol-6-yl)-2-methyl oxazole-4-carboxamide (Intermediate BJL)

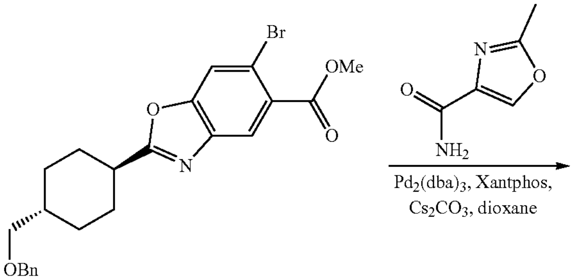

BJK

-continued

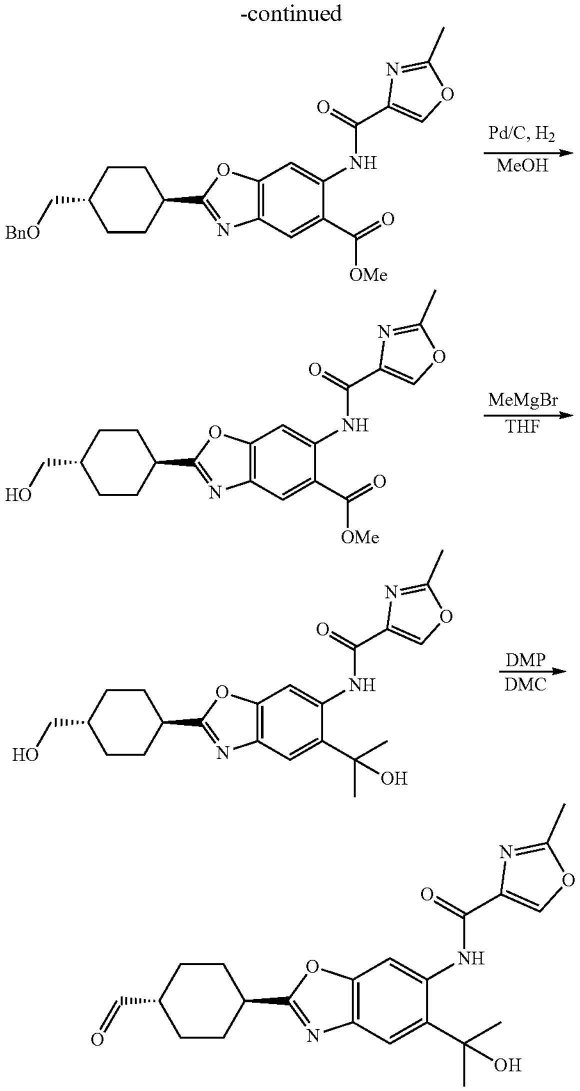

BJL

Step 1—methyl 2-((1r,4r)-4-((benzyloxy)methyl) cyclohexyl)-6-(2-methyloxazole-4-carbox amido) benzo[d]oxazole-5-carboxylate To a solution of methyl 2-[4-(benzyloxymethyl)cyclohexyl]-6-bromo-1,3-benzoxazole-5-carboxylate (180 mg, 392 umol, Intermediate BJK) and 2-methyloxazole-4-carboxamide (54.4 mg, 431 umol, CAS #100959-91-9) in dioxane (2 mL) was added $Pd_2(dba)_3$ (35.9 mg, 39.2 umol), $Cs_2CO_3$ (255 mg, 785 umol) and Xantphos (45.4 mg, 78.5 umol). The mixture was stirred at 80° C. for 12 hours. On completion, the reaction mixture was filtered and concentrated under reduced pressure to give a residue. The residue was purified by column chromatography ($SiO_2$, PE/EA=100/1 to 3/1) to give the title compound (180 mg, 328 umol, 83% yield) as an off-white solid. LC-MS (ESI$^+$) m/z 504.3 (M+H)$^+$. $^1$H NMR (400 MHz, $CDCl_3$) δ 12.43 (s, 1H), 9.12 (s, 1H), 8.42 (s, 1H), 8.22 (s, 1H), 7.42-7.28 (m, 5H), 4.54 (s, 2H), 4.03 (s, 3H), 3.36 (d, J=6.4 Hz, 2H), 2.91 (tt, J=3.6, 12.4 Hz, 1H), 2.59 (s, 3H), 2.34-2.23 (m, 2H), 2.07-1.97 (m, 2H), 1.82-1.64 (m, 3H), 1.24-1.08 (m, 2H).

Step 2—Methyl 2-((1r,4r)-4-(hydroxymethyl)cyclohexyl)-6-(2-methyloxazole-4-carboxamido) benzo[d]oxazole-5-carboxylate To a solution of methyl 2-[4-(benzyloxymethyl)cyclohexyl]-6-[(2-methyloxazole-4-carbonyl) amino]-1,3-benzoxazole-5-carboxylate (140 mg, 278 umol) in MeOH (5 mL) was added Pd/C (50.0 mg, 10% wt) at 25° C. The mixture was stirred at 25° C. for 12 hours under hydrogen (50 Psi). On completion, the reaction mixture was filtered and concentrated under reduced pressure to give the title compound (86.0 mg, 74% yield) as an off-white solid. LC-MS (ESI$^+$) m/z 414.1 (M+H)$^+$. $^1$H NMR (400 MHz, $CDCl_3$) δ 12.43 (s, 1H), 9.12 (s, 1H), 8.43 (s, 1H), 8.23 (s, 1H), 4.03 (s, 3H), 3.55 (d, J=6.4 Hz, 2H), 2.93 (tt, J=3.6, 12.8 Hz, 1H), 2.59 (s, 3H), 2.36-2.26 (m, 2H), 2.05-1.97 (m, 2H), 1.73 (dq, J=3.6, 12.8 Hz, 2H), 1.66-1.47 (m, 1H), 1.24-1.10 (m, 2H).

Step 3—N-(2-((1r,4r)-4-(hydroxymethyl)cyclohexyl)-5-(2-hydroxypropan-2-yl)benzo[d] oxazol-6-yl)-2-methyloxazole-4-carboxamide To a solution of methyl 2-[4-(hydroxymethyl)cyclohexyl]-6-[(2-methyloxazole-4-carbonyl) amino]-1,3-benzoxazole-5-carboxylate (80.0 mg, 193 umol) in THF (2 mL) was added MeMgBr (3 M, 645 uL) at 0° C. The mixture was stirred at 0° C. for 1 hour. On completion, the reaction mixture was quenched by addition sat. $NH_4Cl$ (50 mL) at 0° C., and then diluted with $H_2O$ (50 mL) and extracted with DCM (3×50 mL). The combined organic layers were washed with brine (50 mL), dried over $Na_2SO_4$, filtered and concentrated under reduced pressure to give a residue. The crude product was purified by reversed-phase HPLC (column: Phenomenex Synergi C18 150*25*10 um; mobile phase: [water(0.225% FA)-ACN]; B %: 22%-52%, 10 min) to give the title compound (80.0 mg, 100% yield) as an off-white solid. LC-MS (ESI$^+$) m/z 414.2 (M+H)$^+$.

Step 4—N-(2-((1r,4r)-4-formylcyclohexyl)-5-(2-hydroxypropan-2-yl)benzo[d]oxazol-6-yl)-2-methyl oxazole-4-carboxamide To a solution of N-[2-[4-(hydroxymethyl)cyclohexyl]-5-(1-hydroxy-1-methyl-ethyl)-1,3-benz oxazol-6-yl]-2-methyl-oxazole-4-carboxamide (80.0 mg, 193 umol) in DCM (1 mL) was added DMP (123 mg, 290 umol) at 0° C. The mixture was stirred at 25° C. for 0.5 hours. On completion, the reaction mixture was quenched with sat. $NaHSO_3$ (20 mL) and sat. $NaHCO_3$ (20 mL) at 0° C., and then diluted with $H_2O$ (50 mL) and extracted with DCM (3×50 mL). The combined organic layers were washed with brine (50 mL), dried over $Na_2SO_4$, filtered and concentrated under reduced pressure to give a residue. The residue was purified by column chromatography ($SiO_2$, DCM/MeOH=20/1) to give the title compound (45.0 mg, 55% yield) was obtained as an off-white solid. LC-MS (ESI$^+$) m/z 412.3 (M+H)$^+$.

1-Methyl-3-[3-methyl-2-oxo-5-(4-piperidyl)benzimidazol-1-yl]piperidine-2,6-dione (Intermediate BKO)

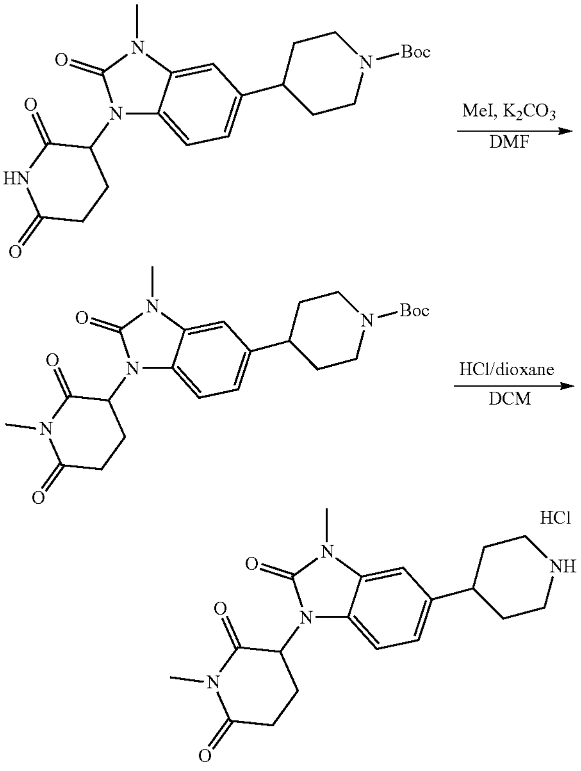

BKO

Step 1—Tert-butyl 4-[3-methyl-1-(1-methyl-2,6-dioxo-3-piperidyl)-2-oxo-benzimidazol-5-yl]piperidine-1-carboxylate To a solution of tert-butyl 4-[1-(2,6-dioxo-3-piperidyl)-3-methyl-2-oxo-benzimidazol-5-yl]piperidine -1-carboxylate (300 mg, 678 umol, synthesized via Steps 1-2 of Intermediate AZL), $K_2CO_3$ (187 mg, 1.36 mmol) in DMF (4 mL) was added MeI (289 mg, 2.03 mmol) at 25° C., and the reaction mixture was stirred at 25° C. for 2.5 hours. On completion, the reaction was quenched with water (0.1 mL) and the mixture was filtered and the cake was washed with DCM (15 mL). The filtrate and washing were combined and concentrated in vacuo. The residue was purified by reverse phase flash (FA condition) to give the title compound (240 mg, 77% yield, FA salt). $^1$H NMR (400 MHz, DMSO-$d_6$) δ 7.11 (d, J=1.2 Hz, 1H), 7.01 (d, J=8.0 Hz, 1H), 6.90 (dd, J=1.2, 8.0 Hz, 1H), 5.40 (dd, J=5.6, 13.1 Hz, 1H), 4.09 (d, J=12.0 Hz, 2H), 3.33 (s, 3H), 3.03 (s, 3H), 3.00-2.92 (m, 1H), 2.79 (d, J=2.4 Hz, 1H), 2.74 (s, 1H), 2.71-2.67 (m, 1H), 2.53-2.51 (m, 2H), 2.04-1.95 (m, 1H), 1.75 (d, J=12.0 Hz, 2H), 1.56-1.54 (m, 2H), 1.42 (s, 9H).

Step 2—1-Methyl-3-[3-methyl-2-oxo-5-(4-piperidyl)benzimidazol-1-yl]piperidine-2,6-dione To a solution of tert-butyl 4-[3-methyl-1-(1-methyl-2,6-dioxo-3-piperidyl)-2-oxo-benzimidazol-5-yl]piperidine-1-carboxylate (150 mg, 328 umol) in DCM (5 mL) was added HCl/dioxane (4 M, 2 mL) at 25° C. and the mixture was stirred at 25° C. for 1 hour. On completion, the mixture was concentrated in vacuo to give the title compound (120 mg, 92% yield, HCl salt) as white solid. LC-MS ($ESI^+$) m/z 357.2 $(M+H)^+$.

((1R,4r)-4-(5-bromo-6-fluoro-2H-indazol-2-yl)cyclohexyl)methanol (Intermediate BKP)

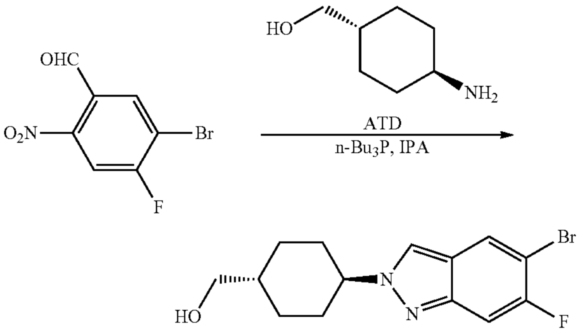

BKP

A mixture of 5-bromo-4-fluoro-2-nitro-benzaldehyde (500 mg, 2.02 mmol, synthesized via Step 1 of Intermediate ATE) and ((1r,4r)-4-aminocyclohexyl)methanol (286 mg, 2.22 mmol, Intermediate ATD) in IPA (6.00 mL) was stirred at 80° C. for 4 hrs under $N_2$. It was cooled to 25° C., then tributylphosphine (1.22 g, 6.05 mmol, 1.49 mL) was added. Then the reaction mixture was stirred at 80° C. for 16 hrs. On completion, the reaction mixture was concentrated in vacuo to give a residue. The residue was diluted with $H_2O$ (10 mL) and extracted with EA (3×10 mL). The combined organic layers were washed with brine (2×20 mL), dried over anhydrous $Na_2SO_4$ then filtered. The filtrate was concentrated in vacuo to give a residue. The residue was purified by column chromatography ($SiO_2$, petroleum ether/ethyl acetate=1/1) to give the title compound (500 mg, 75% yield) as a yellow solid. $^1H$ NMR (400 MHz, $CDCl_3$) δ 7.91 (s, 1H), 7.87 (d, J=6.8 Hz, 1H), 7.39 (d, J=9.6 Hz, 1H), 4.40-432 (m, 1H), 3.55 (d, J=6.4 Hz, 2H), 2.37-2.28 (m, 2H), 2.11-2.02 (m, 2H), 2.00-1.89 (m, 2H), 1.46-1.20 (m, 4H). LC-MS ($ESI^+$) m/z 327.0 $(M+H)^+$.

N-(6-fluoro-2-((1r,4r)-4-formylcyclohexyl)-2H-indazol-5-yl)-6-(trifluoromethyl) picolinamide (Intermediate BKQ)

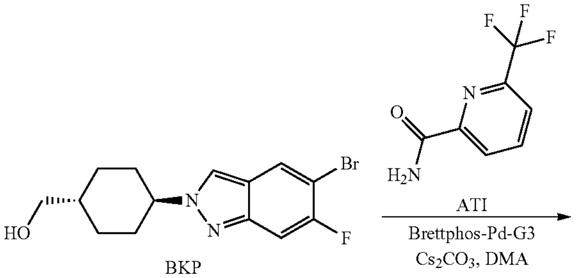

BKP

-continued

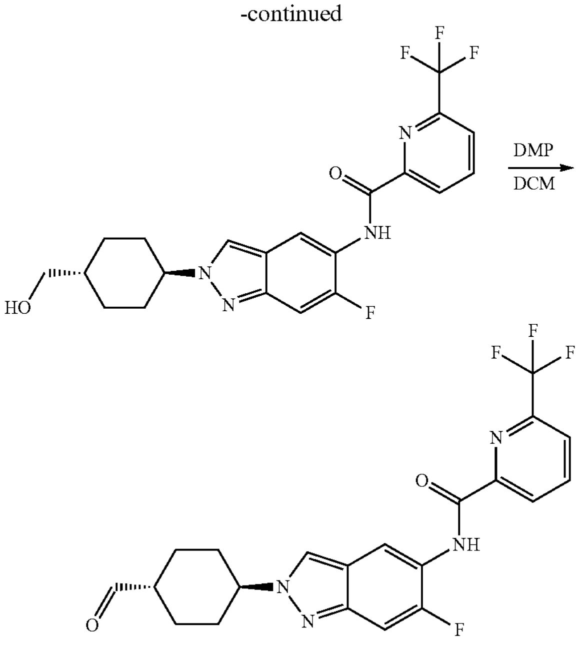

BKQ

Step 1—N-(6-fluoro-2-((1r,4r)-4-(hydroxymethyl) cyclohexyl)-2H-indazol-5-yl)-6-(trifluoromethyl) picolinamide A mixture of ((1r,4r)-4-(5-bromo-6-fluoro-2H-indazol-2-yl)cyclohexyl)methanol (400 mg, 1.22 mmol, Intermediate BKP), 6-(trifluoromethyl)pyridine-2-carboxamide (255 mg, 1.34 mmol, Intermediate ATI), BrettPhos Pd G3 (55.4 mg, 61.1 umol) and $Cs_2CO_3$ (1.19 g, 3.67 mmol) in DMA (6 mL) was degassed and purged with $N_2$ for 3 times. The mixture was stirred at 100° C. for 2 hrs under $N_2$ atmosphere. On completion, the reaction mixture was filtered and the filtrate was concentrated in vacuo to give a residue. The residue was diluted with $H_2O$ (50 mL) and extracted with EA (2×50 mL). The combined organic layers were washed with brine (2×60 mL), dried over anhydrous $Na_2SO_4$, filtered and concentrated in vacuo to give a residue. The residue was purified by reverse-phase (0.1% FA condition) to give the crude product. The crude product was triturated with PE (5 mL) at 25° C. for 0.5 hr to give the title compound (190 mg, 35% yield) as a yellow solid. $^1H$ NMR (400 MHz, $CDCl_3$) δ 10.24 (d, J=2.8 Hz, 1H), 8.82 (d, J=7.6 Hz, 1H), 8.51 (d, J=7.6 Hz, 1H), 8.15 (t, J=8.0 Hz, 1H), 7.97 (s, 1H), 7.90 (d, J=7.6 Hz, 1H), 7.44 (d, J=11.6 Hz, 1H), 4.42-4.34 (m, 1H), 3.57 (d, J=6.0 Hz, 2H), 2.42-2.30 (m, 2H), 2.12-1.93 (m, 4H), 1.72-1.65 (m, 1H), 1.33-1.21 (m, 2H). LC-MS ($ESI^+$) m/z 437.2 $(M+H)^+$.

Step 2—N-(6-fluoro-2-((1r,4r)-4-formylcyclohexyl)-2H-indazol-5-yl)-6-(trifluoromethyl) picolinamide To a solution of N-(6-fluoro-2-((1r,4r)-4-(hydroxymethyl) cyclohexyl)-2H-indazol-5-yl)-6- (trifluoromethyl)picolinamide (160 mg, 366 umol) in DCM (3.00 mL) was added DMP (202 mg, 476 umol) at 0° C. The reaction mixture was stirred at 20° C. for 1 hr. On completion, the reaction mixture was quenched by addition saturated solution of $Na_2S_2O_3$ (5 mL), and saturated solution of $NaHCO_3$ (4 mL), then extracted with DCM (3×10 mL). The combined organic layers were washed with brine (2×20 mL). The organic was dried over anhydrous $Na_2SO_4$, filtered and concentrated in vacuo to give the title compound (140 mg, 88% yield) as a yellow solid. $^1H$ NMR (400 MHz, $CDCl_3$) δ 10.24 (d, J=3.2 Hz, 1H), 9.73 (s, 1H), 8.82 (d, J=7.8 Hz, 1H), 8.51 (d, J=7.6 Hz, 1H), 8.15 (t, J=8.0 Hz, 1H), 7.97 (s, 1H), 7.92-7.87 (m, 1H), 7.44 (d, J=11.6 Hz, 1H), 4.42-4.34 (m, 1H), 2.47-2.37 (m, 3H), 2.32-2.26 (m, 2H), 2.12-2.01 (m, 2H), 1.60-1.50 (m, 2H). LC-MS ($ESI^+$) m/z 435.1 $(M+H)^+$.

[4-[5-Bromo-6-[2-[tert-butyl(dimethyl)silyl]oxy-ethoxy]indazol- 2-yl]cyclohexyl]methanol (Intermediate BKR)

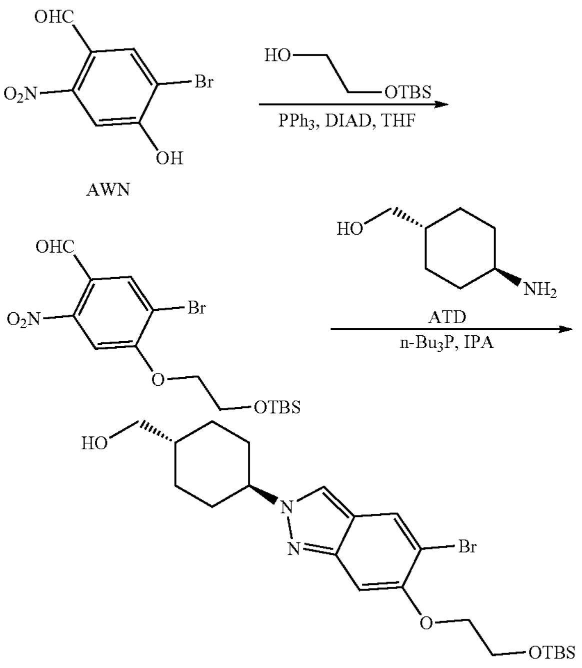

AWN

BKR

Step 1—5-Bromo-4-[2-[tert-butyl(dimethyl)silyl]oxyethoxy]-2-nitro-benzaldehyde

To a solution of 5-bromo-4-hydroxy-2-nitro-benzaldehyde (2.00 g, 8.13 mmol, Intermediate AWN), 2-[tert-butyl(dimethyl)silyl]oxyethanol (2.15 g, 12.2 mmol, CAS #102229-10-7) and $PPh_3$ (3.20 g, 12.1 mmol) in THE (20 mL) was added DIAD (3.29 g, 16.2 mmol) at 0° C. The mixture was stirred at 20° C. for 16 hrs. On completion, the reaction mixture was quenched by water (10 mL) and the mixture was concentrated in vacuo to remove the THF. The residue was diluted with water (100 mL) and extracted with EA (3×50 mL). The organic layer was washed with brine (2×50 mL), dried over anhydrous sodium sulfate and filtered. The filtrated was concentrated in vacuo and the residue was purified by silica gel chromatography (PE:EA=0:1 to 100:1) to give the title compound (2.11 g, 64% yield) as yellow solid. $^1H$ NMR (400 MHz, $CDCl_3$) δ 10.33 (s, 1H), 8.22 (s, 1H), 7.65 (s, 1H), 4.36-4.29 (m, 2H), 4.11-4.04 (m, 2H), 0.89 (s, 9H), 0.11 (s, 6H).

Step 2—[4-[5-Bromo-6-[2-[tert-butyl(dimethyl)silyl]oxyethoxy]indazol-2-yl]cyclohexyl]methanol A mixture of 5-bromo-4-[2-[tert-butyl(dimethyl)silyl]oxyethoxy]-2-nitro-benzaldehyde (2.11 g, 4.17 mmol) and (4-aminocyclohexyl)methanol (539 mg, 4.17 mmol, Intermediate ATD) in IPA (20 mL) was stirred at 80° C. for 16 hrs under nitrogen atmosphere. After reactant was consumed completely, then tributylphosphane (2.53 g, 12.5 mmol) was added to the reaction mixture. The reaction mixture was stirred at 80° C. for 5 hrs under nitrogen atmosphere. On completion, the reaction mixture was concentrated in vacuo. The residue was purified by silica gel chromatography (PE:EA=10:1 to 1:1). The crude product was purified by reversed-phase HPLC (0.1% FA condition) to give the title compound (730 mg, 37% yield) as yellow solid. $^1H$ NMR (400 MHz, $CDCl_3$) δ 7.85 (s, 1H), 7.82 (d, J=0.8 Hz, 1H), 7.05 (s, 1H), 4.32 (tt, J=3.6, 12.0 Hz, 1H), 4.16-4.11 (m, 2H), 4.10-4.05 (m, 2H), 3.56 (d, J=6.4 Hz, 2H), 2.36-2.27 (m, 2H), 2.09-2.01 (m, 3H), 1.99-1.90 (m, 2H), 1.72-1.60 (m, 1H), 1.30-1.21 (m, 2H), 0.93 (s, 9H), 0.14 (s, 6H).

N-[6-[2-[tert-butyl(dimethyl)silyl]oxyethoxy]-2-(4-formylcyclohexyl)indazol-5-yl]-6- (trifluoromethyl) pyridine-2-carboxamide (Intermediate BKS)

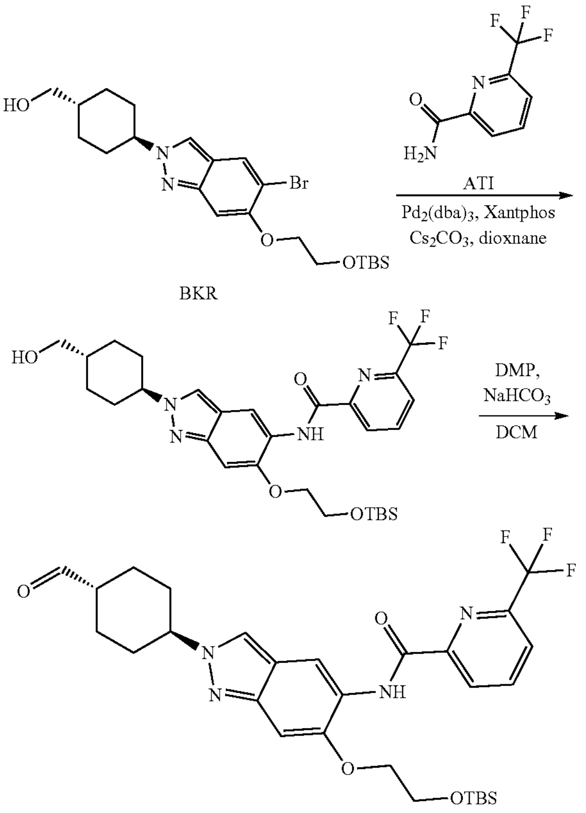

BKR

BKS

Step 1—N-[6-[2-[tert-butyl(dimethyl)silyl]oxy-ethoxy]-2-[4-(hydroxymethyl)cyclohexyl]indazol-5-yl]-6-(trifluoromethyl)pyridine-2-carboxamide A mixture of [4-[5-bromo-6-[2-[tert-butyl(dimethyl)silyl]oxyethoxy]indazol-2-yl]cyclohexyl]methanol (630 mg, 1.30 mmol, Intermediate BKR), 6-(trifluoromethyl)pyridine-2-carboxamide (297 mg, 1.56 mmol, Intermediate ATI), $Pd_2(dba)_3$ (119 mg, 130 umol), Xantphos (150 mg, 260 umol) and $Cs_2CO_3$ (849 mg, 2.61 mmol) in dioxane (15 mL) was stirred at 80° C. for 16 hours under nitrogen atmosphere. On completion, the reaction mixture was filtered and the filtrated was concentrated in vacuo. The residue was purified by reversed-phase HPLC (0.1% FA condition) to give the title compound (520 mg, 67% yield) as yellow solid. $^1$H NMR (400 MHz, DMSO-$d_6$) δ 10.57 (s, 1H), 8.68 (s, 1H), 8.49-8.43 (m, 1H), 8.43-8.37 (m, 1H), 8.33 (s, 1H), 8.24-8.17 (m, 1H), 7.19 (s, 1H), 4.49 (t, J=5.2 Hz, 1H), 4.42-4.31 (m, 1H), 4.26 (t, J=5.2 Hz, 2H), 4.05 (t, J=5.2 Hz, 2H), 3.29-3.26 (m, 2H), 2.19-2.08 (m, 2H), 1.95-1.80 (m, 4H), 1.55-1.37 (m, 1H), 1.24-1.06 (m, 2H), 0.78 (s, 9H), 0.04-0.04 (m, 6H).

Step 2—N-[6-[2-[tert-butyl(dimethyl)silyl]oxy-ethoxy]-2-(4-formylcyclohexyl)indazol-5-yl]-6- (trifluoromethyl)pyridine-2-carboxamide To a mixture of N-[6-[2-[tert-butyl(dimethyl)silyl]oxy-ethoxy]-2-[4-(hydroxymethyl)cyclohexyl]indazol-5-yl]-6-(trifluoromethyl)pyridine-2-carboxamide (500 mg, 843.56 umol) and $NaHCO_3$ (354 mg, 4.22 mmol) in DCM (10 mL) was added DMP (536 mg, 1.27 mmol) at 0° C. The reaction mixture was stirred at 20° C. for 1 hr. On completion, the reaction mixture was diluted with saturated $Na_2S_2O_3$ aqueous (5 mL) and saturated $NaHCO_3$ aqueous (5 mL). The mixture was stirred at 20° C. for 0.5 hr. The mixture was diluted with water (50 mL) and extracted with DCM (3×30 mL). The organic layer was washed with saturated $NaHCO_3$ aqueous (2×50 mL) and brine (3×50 mL). The organic layer was dried over anhydrous sodium sulfate and filtered. The filtrated was concentrated in vacuo to give the title compound (490 mg, 98% yield) as yellow solid. $^1$H NMR (400 MHz, DMSO-$d_6$) δ 10.57 (s, 1H), 9.64 (s, 1H), 8.69 (s, 1H), 8.49-8.44 (m, 1H), 8.43-8.37 (m, 1H), 8.34 (s, 1H), 8.21 (d, J=7.6 Hz, 1H), 7.19 (s, 1H), 4.47-4.34 (m, 1H), 4.26 (t, J=5.2 Hz, 2H), 4.11-4.00 (m, 2H), 2.43-2.38 (m, 1H), 2.24-2.16 (m, 2H), 2.15-2.06 (m, 2H), 2.03-1.89 (m, 2H), 1.51-1.38 (m, 2H), 0.79 (s, 9H), 0.00 (s, 6H).

3-(3-Methyl-2-oxo-5,6,7,8-tetrahydroimidazo[4,5-g]quinolin-1-yl)piperidine-2,6-dione (Intermediate BKT)

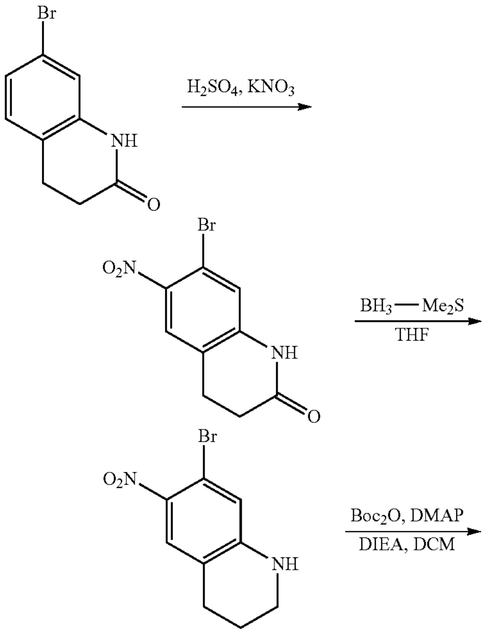

-continued

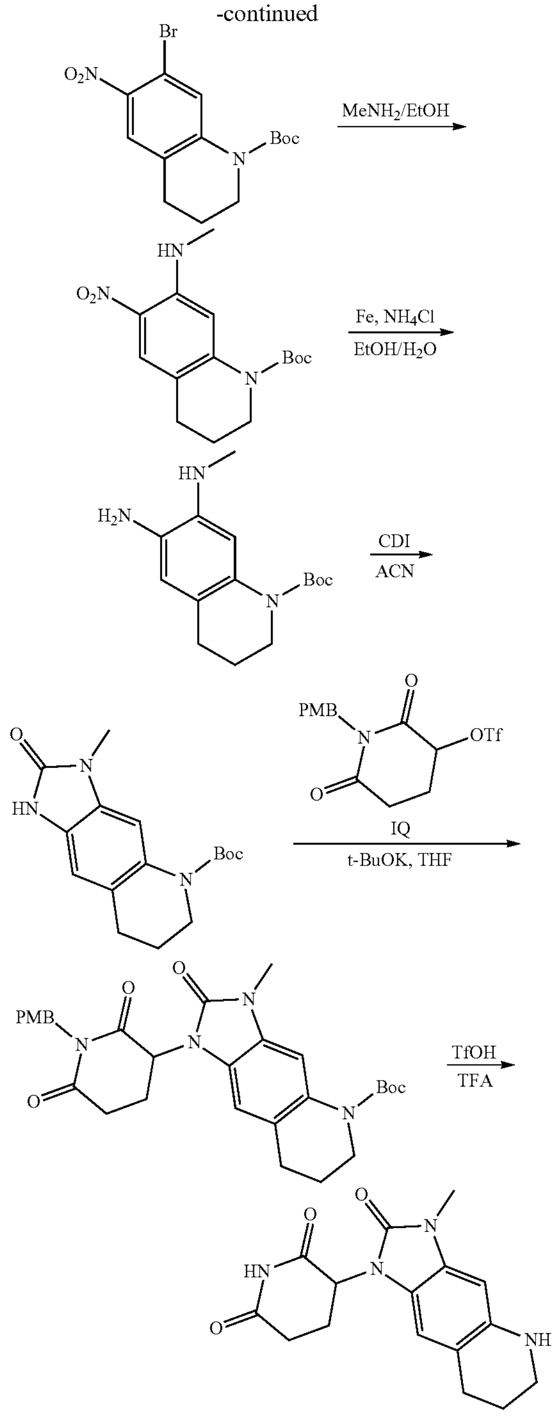

BKT

Step 1—7-Bromo-6-nitro-3,4-dihydro-1H-quinolin-2-one

To a mixture of 7-bromo-3,4-dihydro-1H-quinolin-2-one (5.00 g, 22.1 mmol, CAS #14548-51-7) in $H_2SO_4$ (140 mL) was added $KNO_3$ (2.68 g, 26.5 mmol) at 25° C. for portions and then the mixture was stirred at 0° C. to 25° C. for 2 hours. On completion, the mixture was poured into 500 mL ice-water and extracted with ethyl acetate (3×100 mL). The combined organic layers were washed with $NaHCO_3$ aqueous solution, water, brine, dried over anhydrous sodium sulfate, filtered and concentrated in vacuo to give the title compound (3.00 g, 50% yield) as a yellow solid. LC-MS ($ESI^+$) m/z 272.9 $(M+H)^+$.

Step 2—7-Bromo-6-nitro-1,2,3,4-tetrahydroquinoline

To a mixture of 7-bromo-6-nitro-3,4-dihydro-1H-quinolin-2-one (3.00 g, 11.1 mmol) in THE (100 mL) was added $BH_3$-$Me_2S$ (10 M, 3.32 mL) at 0° C., and the reaction mixture was heated to 70° C. with stirring for 16 hours under $N_2$. On completion, the mixture was quenched with MeOH (5.0 mL) carefully, and then concentrated in vacuo. The residue was dissolved in EA (100 mL), washed with water, brine, dried over anhydrous sodium sulfate and concentrated in vacuo to give the title compound (2.50 g, 88% yield) as a yellow solid. $^1H$ NMR (400 MHz, DMSO-$d_6$) δ 7.81 (s, 1H), 7.46 (s, 1H), 6.79 (s, 1H), 3.28-3.26 (m, 2H), 2.75-2.66 (m, 2H), 1.81-1.75 (m, 2H).

Step 3—Ttert-butyl 7-bromo-6-nitro-3,4-dihydro-2H-quinoline-1-carboxylate

To a mixture of 7-bromo-6-nitro-1,2,3,4-tetrahydroquinoline (2.50 g, 9.72 mmol), $(Boc)_2O$ (4.24 g, 19.5 mmol, 4.47 mL) in DCM (100 mL) was added DMAP (237 mg, 1.94 mmol) and DIEA (3.77 g, 29.2 mmol, 5.08 mL), and the mixture was stirred at 25° C. for 16 hours. On completion, the mixture was poured into saturated ammonium chloride aqueous solution (50 mL) and extracted with dichloromethane (3×50 mL). The combined organic layers were washed with water, brine, dried over anhydrous sodium sulfate and concentrated in vacuo to give residue. The residue was purified by silica gel column chromatography (petroleum ether:ethyl acetate=3:1) to give the title compound (2.00 g, 55% yield) as a yellow solid. $^1H$ NMR (400 MHz, DMSO-$d_6$) δ 8.22 (s, 1H), 7.93 (s, 1H), 3.69 (t, J=6.0 Hz, 2H), 2.78 (t, J=6.0 Hz, 2H), 1.89-1.82 (m, 2H), 1.51 (m, 9H).

Step 4—Tert-butyl 7-(methylamino)-6-nitro-3,4-dihydro-2H-quinoline-1-carboxylate A mixture of tert-butyl 7-bromo-6-nitro-3,4-dihydro-2H-quinoline-1-carboxylate (2.00 g, 5.60 mmol) in $MeNH_2$ (8.0 mL, 30% solution in EtOH) was stirred at 100° C. for 12 h in a autoclave. On completion, the mixture was concentrated in vacuo. The residue was diluted with DCM (30 mL), and saturated $NaHCO_3$ solution was added until the pH=9. The mixture was extracted with DCM (3×30 mL), and the organic layer was dried over $Na_2SO_4$, filtered and concentrated in vacuo to give the residue. The residue was purified by reverse phase flash (0.1% FA condition)] to give the title compound (500 mg, 29% yield) as yellow solid. LC-MS ($ESI^+$) m/z 308.1 $(M+H)^+$.

Step 5—Tert-butyl 6-amino-7-(methylamino)-3,4-dihydro-2H-quinoline-1-carboxylate To a solution of tert-butyl 7-(methylamino)-6-nitro-3,4-dihydro-2H-quinoline-1-carboxylate (300 mg, 976 umol) in EtOH (3.00 mL) and $H_2O$ (3.00 mL) was added Fe (164 mg, 2.93 mmol) and $NH_4Cl$ (522 mg, 9.76 mmol) at 25° C., then the reaction mixture was stirred at 60° C. for 1 hrs. On completion, the reaction mixture was filtered and the filtrate was concentrated in vacuo to give the title compound (350 mg, 90% yield) as black brown solid. LC-MS ($ESI^+$) m/z 278.2 $(M+H)^+$.

Step 6—Tert-butyl 3-methyl-2-oxo-1,6,7,8-tetrahydroimidazo[4,5-g]quinoline-5-carboxylate To a solution of tert-butyl 6-amino-7-(methylamino)-3,4-dihydro-2H-quinoline-1-carboxylate (300 mg, 1.08 mmol) in ACN (5.00 mL) was added CDI (210 mg, 1.30 mmol), and the mixture was stirred at 25° C. for 12 hours. On completion, the reaction mixture was concentrated in vacuo to give a residue. The residue was purified by reverse phase flash (0.1% FA condition) to give the title compound (150 mg, 46% yield) as black brown solid. $^1H$ NMR (400 MHz, DMSO-$d_6$) δ 10.66 (s, 1H), 7.20 (s, 1H), 6.70 (s, 1H), 3.65-3.55 (m, 2H), 3.22 (s, 3H), 2.71 (t, J=6.4 Hz, 2H), 1.87-1.77 (m, 2H), 1.47 (s, 9H).

Step 7—Tert-butyl 1-[1-[(4-methoxyphenyl)methyl]-2,6-dioxo-3-piperidyl]-3-methyl-2-oxo-7,8-dihydro-6H-imidazo[4,5-g]quinoline-5-carboxylate To a mixture of tert-butyl 3-methyl-2-oxo-1,6,7,8-tetrahydroimidazo[4,5-g]quinoline-5-carboxylate (130 mg, 428 umol) in THE (2.00 mL) was added t-BuOK (144 mg, 1.29 mmol) at −10° C. under $N_2$. The reaction mixture was stirred for 0.5 hr. Then solution of [1-[(4-methoxyphenyl)methyl]-2,6-dioxo-3-piperidyl]trifluoromethanesulfonate (490 mg, 1.29 mmol, Intermediate IQ) in THF (2.00 mL) was added dropwise and the mixture was stirred at −10° C. for 1 hour under $N_2$. On completion, the reaction mixture was concentrated in vacuo to give a residue. The residue was purified by reverse phase flash (0.1% FA condition) to give the title compound (200 mg, 87% yield) as brown gum solid. $^1H$ NMR (400 MHz, $CDCl_3$) δ 7.43-7.36 (m, 3H), 6.89-6.79 (m, 3H), 5.22 (dd, J=5.6, 13.2 Hz, 1H), 5.04-4.94 (m, 2H), 3.81 (s, 3H), 3.73-3.59 (m, 2H), 3.42 (s, 3H), 3.11-2.97 (m, 1H), 2.92-2.80 (m, 1H), 2.63-2.50 (m, 3H), 2.25-2.16 (m, 1H), 1.97-1.84 (m, 2H), 1.56 (s, 9H).

Step 8—3-(3-Methyl-2-oxo-5,6,7,8-tetrahydroimidazo[4,5-g]quinolin-1-yl)piperidine-2,6-dione A mixture of tert-butyl1-[1-[(4-methoxyphenyl)methyl]-2,6-dioxo-3-piperidyl]-3-methyl-2-oxo-7,8-dihydro-6H-imidazo[4,5-g]quinoline-5-carboxylate (150 mg, 281 umol) in TfOH (0.2 mL) and TFA (1.0 mL) was stirred at 60° C. for 12 hr under $N_2$ atmosphere. On completion, the reaction mixture was concentrated in vacuo to give a residue. The residue was adjusted pH=5-6 by added $NaHCO_3$ dropwise, and then the mixture was filtered to give residue. The residue was purified by Prep-HPLC (column: Shim-pack C18 150*25*10 um; mobile phase: [water (0.225% FA)-ACN]; B %: 1%-20%, 10 min) to give the title compound (29.4 mg, 32% yield, FA salt)$^1H$ NMR (400 MHz, DMSO-$d_6$) δ 11.01 (s, 1H), 6.60 (s, 1H), 6.23 (s, 1H), 5.53-5.30 (m, 1H), 5.21 (dd, J=5.2, 12.8 Hz, 1H), 3.20 (s, 3H), 3.18-3.12 (m, 2H), 2.98-2.80 (m, 1H), 2.76-2.57 (m, 4H), 2.00-1.88 (m, 1H), 1.78-1.75 (m, 2H). LC-MS ($ESI^+$) m/z 315.4 $(M+H)^+$.

N-[2-(4-formylcyclohexyl)-6-methoxy-indazol-5-yl]oxazole-2-carboxamide (Intermediate BKW)

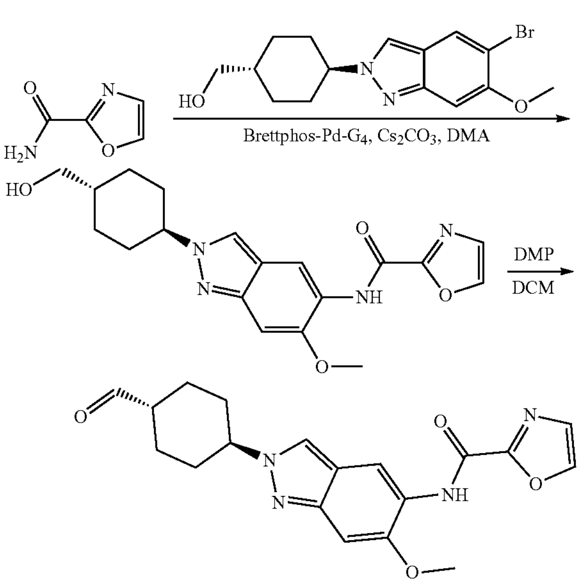

BKW

Step 1—N-[2-[4-(hydroxymethyl)cyclohexyl]-6-methoxy-indazol-5-yl]oxazole-2-carboxamide A mixture of [4-(5-bromo-6-methoxy-indazol-2-yl)cyclohexyl]methanol (300 mg, 884 umol, synthesized via Steps 1-3 of Intermediate ATE), oxazole-2-carboxamide (99.1 mg, 884 umol, CAS #884539-45-1), $Cs_2CO_3$ (576 mg, 1.77 mmol) and BrettPhos (Pd, G4) (40.7 mg, 44.2 umol) in DMA (10.0 mL) was stirred at 100° C. for 64 hrs. On completion, the reaction mixture was filtered. The filtrated was concentrated in vacuo to give the residue. The residue was purified by reversed phase (0.1% FA condition) to give the title compound (280 mg, 85% yield) as yellow solid. $^1$H NMR (400 MHz, $CDCl_3$) δ 9.62 (s, 1H), 8.75 (s, 1H), 7.89 (s, 1H), 7.86 (s, 1H), 7.32 (s, 1H), 7.08 (s, 1H), 4.42-4.28 (m, 1H), 4.02 (s, 3H), 3.57 (d, J=6.4 Hz, 2H), 2.40-2.27 (m, 2H), 2.10-2.02 (m, 2H), 2.01-1.90 (m, 2H), 1.74-1.61 (m, 1H), 1.33-1.18 (m, 2H).

Step 2—N-[2-(4-formylcyclohexyl)-6-methoxy-indazol-5-yl]oxazole-2-carboxamide

To a mixture of N-[2-[4-(hydroxymethyl)cyclohexyl]-6-methoxy-indazol-5-yl]oxazole-2-carboxamide (250 mg, 674 umol) and $NaHCO_3$ (283 mg, 3.37 mmol) in DCM (10.0 mL) was added DMP (429 mg, 1.01 mmol) at 0° C., then the mixture was stirred at 20° C. for 2 hrs. On completion, the reaction mixture was quenched with saturated $Na_2S_2O_3$ aqueous (5 mL) and saturated $NaHCO_3$ aqueous (5 mL). The mixture was stirred at 20° C. for 0.5 hr. The mixture was diluted with water (50 mL) and extracted with DCM (3×30 mL). The organic layer was washed with saturated $NaHCO_3$ aqueous (2×50 mL) and brine (3×50 mL). The organic layer was dried over anhydrous sodium sulfate and filtered. The filtrate was concentrated in vacuo to give the title compound (240 mg, 96% yield) as yellow solid. $^1$H NMR (400 MHz, DMSO-$d_6$) δ 9.64 (s, 2H), 8.44 (d, J=8.8 Hz, 2H), 8.33 (s, 1H), 7.55 (s, 1H), 7.14 (s, 1H), 4.40 (tt, J=3.6, 11.6 Hz, 1H), 3.96 (s, 3H), 2.45-2.37 (m, 1H), 2.23-2.16 (m, 2H), 2.15-2.05 (m, 2H), 1.99-1.88 (m, 2H), 1.51-1.37 (m, 2H).

Tert-butyl (2R)-2-(methylsulfonyloxymethyl)morpholine-4-carboxylate (Intermediate BKX)

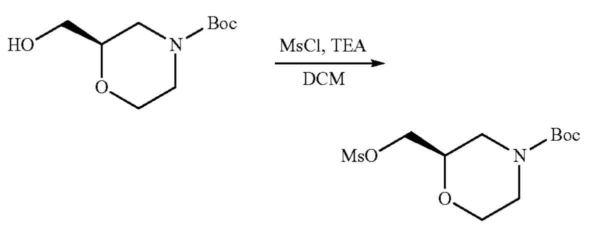

BKX

To a solution of tert-butyl (2R)-2-(hydroxymethyl)morpholine-4-carboxylate (5.00 g, 23.0 mmol, CAS #135065-71-3) in DCM (50 mL) was added $Et_3N$ (5.82 g, 57.5 mmol, 8.01 mL), MsCl (3.95 g, 34.5 mmol, 2.67 mL) at 0° C. Then the mixture was stirred at 0° C. for 3 hours. On completion, the reaction mixture was filtered and concentrated in vacuo. The mixture was cooled to 25° C. and concentrated in reduced pressure at 25° C. The residue was poured into ice-water (20 mL) and stirred for 3 min. The aqueous phase was extracted with DCM (3×20 mL). The combined organic phase was washed with citric acid (2×20 mL), washed with brine (2×20 mL), dried with anhydrous $Na_2SO_4$, filtered and concentrated in vacuo. The residue was purified by silica gel chromatography (petroleum ether/ethyl acetate=20/1) to give the title compound (6.79 g, 99% yield) as yellow oil. $^1$H NMR (400 MHz, DMSO-$d_6$) δ 4.29-4.23 (m, 1H), 4.22-4.15 (m, 1H), 3.91-3.76 (m, 2H), 3.70 (d, J=13.2 Hz, 1H), 3.65-3.58 (m, 1H), 3.43-3.39 (m, 1H), 3.19 (s, 3H), 2.95-2.80 (m, 1H), 2.78-2.57 (m, 1H), 1.41 (s, 9H).

3-((1-Methyl-7-((R)-morpholin-2-ylmethoxy)-1H-benzo[d]imidazol-2-yl)oxy)piperidine-2,6-dione (Intermediate BKY)

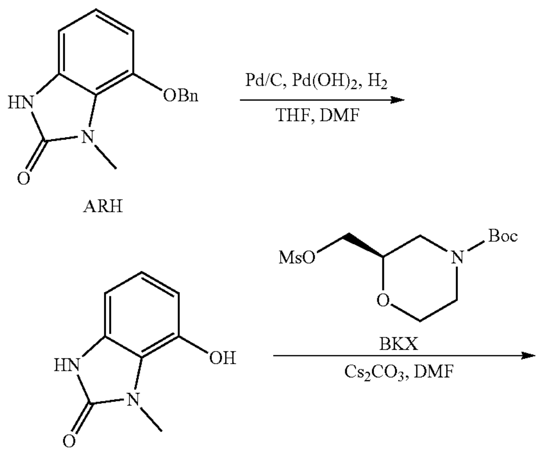

-continued

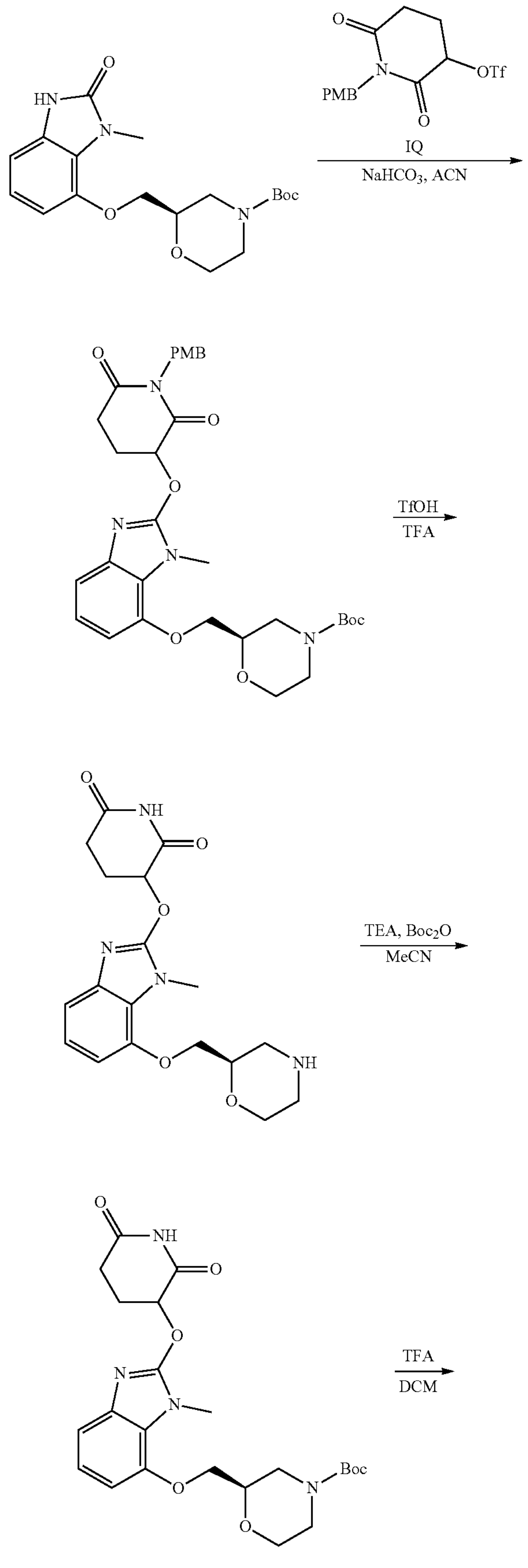

-continued

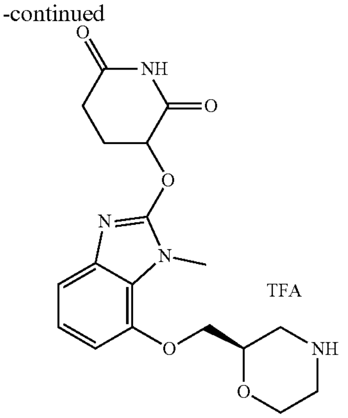

BKY

Step 1—4-Hydroxy-3-methyl-1H-benzimidazol-2-one

To a solution of 4-benzyloxy-3-methyl-1H-benzimidazol-2-one (7.00 g, 27.5 mmol, Intermediate ARH) in THF (500 mL) and DMF (10 mL) was added Pd/C (0.5 g, 10 wt %) and $Pd(OH)_2$/C (0.5 g, 10 wt %) under $N_2$. The suspension was degassed under vacuum and purged with $H_2$ several times. The mixture was stirred under $H_2$ (15 psi) at 25° C. for 16 hours. On completion, the mixture was filtered and concentrated to give the title compound (4.50 g, 99% yield) as off white solid. $^1$H NMR (400 MHz, DMSO-$d_6$) δ 10.66 (s, 1H), 9.61 (s, 1H), 6.77-6.73 (m, 1H), 6.50-6.44 (m, 2H), 3.46 (s, 1H).

Step 2—Tert-butyl (2R)-2-[(3-methyl-2-oxo-1H-benzimidazol-4-yl)oxymethyl]morpholine-4- carboxylate To a mixture of 4-hydroxy-3-methyl-1H-benzimidazol-2-one (800 mg, 4.87 mmol) and 4 Å molecular sieves (100 mg) in DMF (8 mL) was added $Cs_2CO_3$ (1.75 g, 5.36 mmol) and tert-butyl (2R)-2-(methylsulfonyloxymethyl)morpholine-4-carboxylate (1.51 g, 5.12 mmol, Intermediate BKX). The mixture was stirred at 60° C. for 16 hours. On completion, the reaction mixture was filtered and concentrated in vacuo. The crude product was purified by reverse phase flash (0.1% FA condition) to give the title compound (620 mg, 33% yield) as yellow solid. $^1$H NMR (400 MHz, DMSO-$d_6$) δ 10.83 (s, 1H), 6.93-6.86 (m, 1H), 6.69 (d, J=8.4 Hz, 1H), 6.63 (d, J=7.6 Hz, 1H), 4.15-4.03 (m, 2H), 3.97 (d, J=12.8 Hz, 1H), 3.87 (d, J=11.6 Hz, 1H), 3.78-3.70 (m, 2H), 3.47 (d, J=2.4 Hz, 3H), 3.30 (s, 1H), 2.94-2.82 (m, 2H), 1.41 (s, 9H).

Step 3—(2R)-tert-butyl 2-(((2-((1-(4-methoxybenzyl)-2,6-dioxopiperidin-3-yl)oxy)-1-methyl-1H-benzo[d]imidazol-7-yl)oxy)methyl)morpholine-4-carboxylate To a solution of tert-butyl (2R)-2-[(3-methyl-2-oxo-1H-benzimidazol-4-yl)oxymethyl]morpholine-4- carboxylate (620 mg, 1.63 mmol), [1-[(4-methoxyphenyl)methyl]-2,6-dioxo-3-piperidyl]trifluoromethanesulfonate (744 mg, 1.95 mmol, Intermediate IQ) in ACN (10 mL). Then $NaHCO_3$ (342 mg, 4.07 mmol, 158 uL) was added. The mixture was stirred at 80° C. for 2 hours. On completion, the reaction mixture was filtered and concentrated in vacuo. The aqueous phase was extracted with ethyl acetate (3×20 mL). The combined organic phase was washed with brine (3×20 mL), dried with anhydrous $Na_2SO_4$, filtered and concentrated in vacuo. The crude product was purified by reverse phase flash (0.1% FA condition) to give the title compound (690 mg, 71% yield) as yellow solid. $^1H$ NMR (400 MHz, DMSO-$d_6$) δ 7.19 (d, J=8.4 Hz, 2H), 7.03-6.97 (m, 2H), 6.85 (d, J=8.4 Hz, 2H), 6.78-6.71 (m, 1H), 6.06-5.94 (m, 1H), 4.74 (s, 2H), 4.14-4.06 (m, 1H), 3.99 (d, J=13.2 Hz, 1H), 3.88 (d, J=10.4 Hz, 1H), 3.77 (s, 3H), 3.71 (s, 3H), 3.51-3.44 (m, 1H), 3.31-3.27 (m, 2H), 3.10-2.78 (m, 5H), 2.41-2.35 (m, 2H), 1.40 (s, 9H); LC-MS (ESI$^+$) m/z 595.1 (M+H)$^+$.

Step 4—3-((1-methyl-7-((R)-morpholin-2-yl-methoxy)-1H-benzo[d]imidazol-2-yl)oxy)piperidine-2.6- dione To a solution of (2R)-tert-butyl 2-(((2-((1-(4-methoxy-benzyl)-2,6-dioxopiperidin-3-yl)oxy)-1- methyl-1H-benzo [d]imidazol-7-yl)oxy)methyl)morpholine-4-carboxylate (690 mg, 1.16 mmol) in TFA (8 mL) was added TfOH (1 mL). The mixture was stirred at 65° C. for 20 hrs. On completion, the reaction mixture was filtered and concentrated in vacuo to give the title compound (430 mg, 99% yield) as brown solid. LC-MS (ESI$^+$) m/z 375.1 (M+H)$^+$.

Step 5—(2R)-tert-butyl 2-(((2-((2,6-dioxopiperidin-3-yl)oxy)-1-methyl-1H-benzo[d]imidazol-7-yl)oxy) methyl)morpholine-4-carboxylate To a solution of 3-((1-methyl-7-((R)-morpholin-2-yl-methoxy)-1H-benzo[d]imidazol-2-yl)oxy) piperidine-2,6-dione (400 mg, 1.07 mmol) in ACN (4 mL) was added TEA (1.38 g, 13.6 mmol, 1.90 mL), $Boc_2O$ (349 mg, 1.60 mmol, 368 uL). The mixture was stirred at 25° C. for 2 hours. On completion, the reaction mixture was concentrated in vacuo. The residue was poured into ice-water (10 mL) and stirred for 3 min, then the aqueous phase was extracted with ethyl acetate (2×10 mL). The combined organic phase was washed with brine (2×10 mL), dried with anhydrous $Na_2SO_4$, filtered and concentrated in vacuo. The crude product was purified by reverse phase flash (0.1% FA condition), then further purified by Prep-HPLC (column: Welch Ultimate XB-CN 250*70*10 um; mobile phase: [n-Heptane-IPA (0.1% TEA)]; B %: 25%-65%, 10 min.) to give the title compound (120 mg, 23% yield) as yellow solid. $^1H$ NMR (400 MHz, DMSO-$d_6$) δ 11.02 (s, 1H), 7.03-6.98 (m, 2H), 6.77-6.71 (m, 1H), 5.86 (dd, J=6.8, 10.8 Hz, 1H), 4.19-1.14 (m, 1H), 4.13-4.06 (m, 1H), 3.90-3.85 (m, 1H), 3.77 (s, 5H), 3.62-3.57 (m, 2H), 3.47 (dt, J=2.4, 11.6 Hz, 2H), 2.37-2.31 (m, 2H), 1.80-1.70 (m, 2H), 1.40 (s, 9H); LC-MS (ESI$^+$) m/z 475.1 (M+H)$^+$.

Step 6—3-((1-Methyl-7-((R)-morpholin-2-yl-methoxy)-1H-benzo[d]imidazol-2-yl)oxy)piperidine-2,6-dione To a solution of (2R)-tert-butyl 2-(((2-((2,6-dioxopiperi-din-3-yl)oxy)-1-methyl-1H-benzo[d]imidazol-7-yl)oxy) methyl)morpholine-4-carboxylate (110 mg, 228 umol) in DCM (3 mL) was added TFA (2 mL). The mixture was stirred at 25° C. for 2 hours. On completion, the reaction mixture was concentrated in vacuo to give the title compound (100 mg, 89% yield, TFA) as yellow solid. LC-MS (ESI$^+$) m/z 375.1 (M+H)$^+$.

Tert-butyl (2S)-2-(methylsulfonyloxymethyl)morpholine-4-carboxylate (Intermediate BKZ)

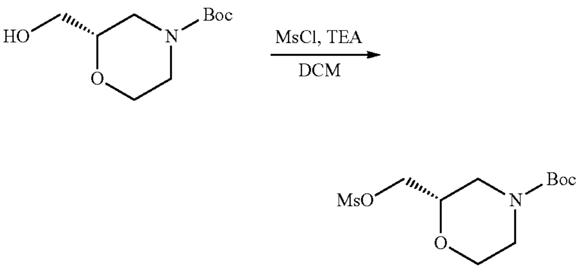

BKZ

To a mixture of tert-butyl (2S)-2-(hydroxymethyl)morpholine-4-carboxylate (5.00 g, 23.0 mmol, CAS #135065-76-8) and TEA (6.99 g, 69.0 mmol) in DCM (40 mL) was added MsCl (3.95 g, 34.5 mmol) at 0° C. The reaction mixture was stirred at 20° C. for 1 hr. On completion, the mixture was diluted with water (200 mL) and extracted with DCM (3×50 mL). The organic layer was washed with citric acid aqueous (50 mL), saturated $NaHCO_3$ aqueous (50 mL) and brine (3×50 mL). The organic layer was dried over anhydrous sodium sulfate and filtered. The filtrated was concentrated in vacuo to give the mixed compound (6.70 g, 98% yield) as yellow oil. $^1H$ NMR (400 MHz, $CDCl_3$) δ 4.24 (d, J=4.8 Hz, 2H), 4.05-3.79 (m, 3H), 3.76-3.65 (m, 1H), 3.55 (dt, J=2.8, 11.6 Hz, 1H), 3.07 (s, 3H), 3.03-2.89 (m, 1H), 2.86-2.68 (m, 1H), 1.47 (s, 9H).

3-[1-Methyl-7-[[(2S)-morpholin-2-yl]methoxy]benzimidazol-2-yl]oxypiperidine-2,6-dione (Intermediate BLA)

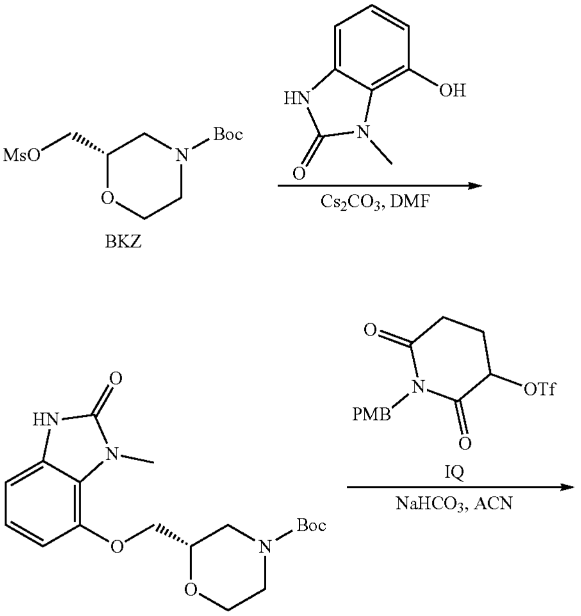

-continued

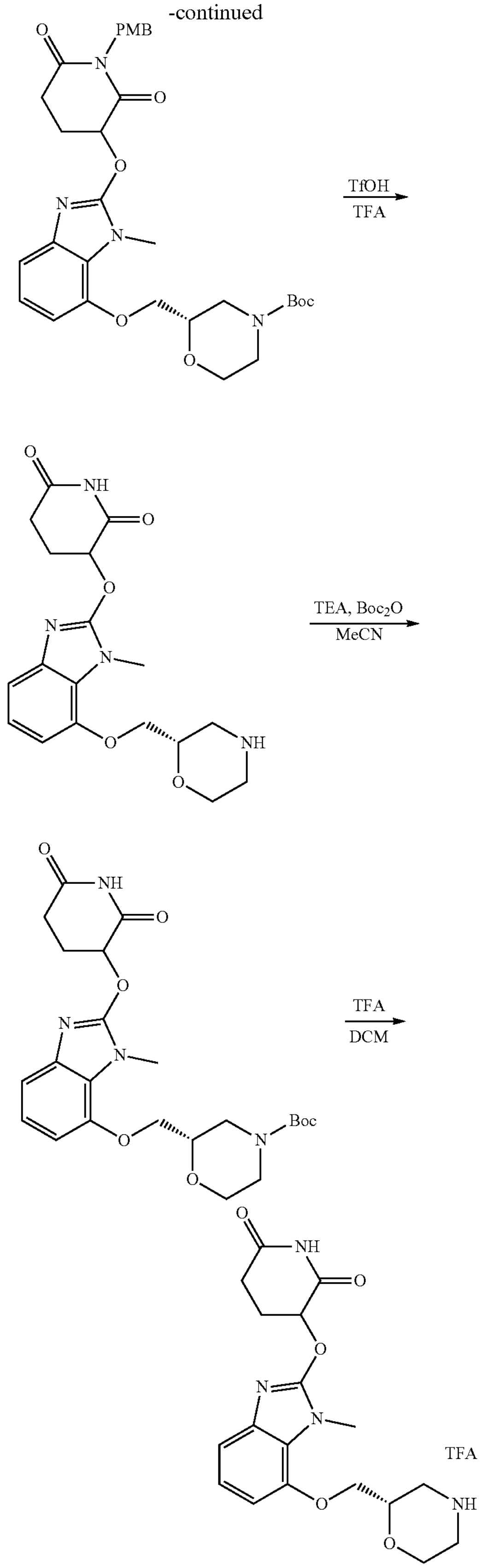

BLA

Step 1—Tert-butyl (2S)-2-[(3-methyl-2-oxo-1H-benzimidazol-4-yl)oxymethyl]morpholine-4- carboxylate To a mixture of 4-hydroxy-3-methyl-1H-benzimidazol-2-one (830 mg, 5.06 mmol, synthesized via Step 1 of Intermediate BKY), tert-butyl (2S)-2-(methylsulfonyloxymethyl)morpholine-4-carboxylate (1.57 g, 5.31 mmol, Intermediate BKZ) and 4 Å molecular sieves (80 mg) in DMF (10 mL) was added $Cs_2CO_3$ (1.73 g, 5.31 mmol). The reaction mixture was then stirred at 60° C. for 16 hrs. On completion, the reaction mixture was filtered and the filtrate was concentrated in vacuo. The residue was purified by reversed-phase HPLC (0.1% FA condition) to give the title compound (970 mg, 52% yield) as yellow solid. $^1H$ NMR (400 MHz, $CDCl_3$) δ 9.80 (s, 1H), 7.00-6.93 (m, 1H), 6.77 (d, J=7.6 Hz, 1H), 6.62 (d, J=8.4 Hz, 1H), 4.21-4.08 (m, 2H), 4.08-4.00 (m, 1H), 3.99-3.88 (m, 2H), 3.88-3.80 (m, 1H), 3.68 (s, 3H), 3.65-3.57 (m, 1H), 3.05-2.81 (m, 2H), 1.49-1.47 (m, 9H).

Step 2—Tert-butyl (2S)-2-[[2-[[1-[(4-methoxyphenyl)methyl]-2,6-dioxo-3-piperidyl]oxy]-3-methyl-benzimidazol-4-yl]oxymethyl]morpholine-4-carboxylate A mixture of tert-butyl (2S)-2-[(3-methyl-2-oxo-1H-benzimidazol-4-yl)oxymethyl]morpholine-4- carboxylate (870 mg, 2.39 mmol), [1-[(4-methoxyphenyl)methyl]-2,6-dioxo-3-piperidyl]trifluoromethanesulfonate (1.10 g, 2.87 mmol, Intermediate IQ) and $NaHCO_3$ (402 mg, 4.79 mmol) in ACN (15 mL) was stirred at 80° C. for 16 hours under nitrogen atmosphere. On completion, the reaction mixture was filtered and the filtrated was concentrated in vacuo. The residue was purified by reversed-phase HPLC (0.1% FA condition) to give the title compound (1.10 g, 77% yield) as gray solid. $^1H$ NMR (400 MHz, $CDCl_3$) δ 7.39-7.30 (m, 2H), 7.17-7.11 (m, 1H), 7.09-7.01 (m, 1H), 6.86-6.77 (m, 2H), 6.64 (d, J=8.0 Hz, 1H), 5.87 (dd, J=5.2, 12.4 Hz, 1H), 4.94-4.84 (m, 2H), 4.22-4.16 (m, 1H), 4.16-4.03 (m, 2H), 4.01-3.90 (m, 2H), 3.87 (s, 3H), 3.86-3.82 (m, 1H), 3.79 (s, 3H), 3.66-3.57 (m, 1H), 3.08-2.93 (m, 2H), 2.92-2.76 (m, 2H), 2.57-2.45 (m, 1H), 2.37-2.23 (m, 1H), 1.49 (s, 9H).

Step 3—3-[1-Methyl-7-[[(2S)-morpholin-2-yl]methoxy]benzimidazol-2-yl]oxypiperidine-2,6-dione To a mixture of tert-butyl (2S)-2-[[2-[[1-[(4-methoxyphenyl)methyl]-2,6-dioxo-3-piperidyl]oxy]-3- methyl-benzimidazol-4-yl]oxymethyl]morpholine-4-carboxylate (500 mg, 840 umol) in TFA (8 mL) was added TfOH (1.70 g, 11.3 mmol, 1.00 mL). The reaction mixture was stirred at 60° C. for 16 hr. On completion, the reaction mixture was concentrated in vacuo to give the title compound (410 mg, 99% yield, TFA salt) as yellow oil. LC-MS (ESI+) m/z 375.2 $(M+H)^+$.

Step 4—Tert-butyl (2S)-2-[[2-[(2,6-dioxo-3-piperidyl)oxy]-3-methyl-benzimidazol-4-yl]oxymethyl]morpholine-4-carboxylate To a mixture of 3-[1-methyl-7-[[(2S)-morpholin-2-yl]methoxy]benzimidazol-2-yl]oxypiperidine-2,6- dione (410 mg, 839 umol, TFA) in ACN (10 mL) was added TEA (84.9 mg, 839 umol) until pH=8. Then $Boc_2O$ (219 mg, 1.01 mmol) was added to the mixture. The reaction mixture was stirred at 20° C. for 2 hrs. On completion, the reaction mixture was concentrated in vacuo. The crude product was purified by reversed-phase HPLC (0.1% FA condition). The residue was purified by silica gel chromatography (PE: EA=2:1 to 1:1) to give the title compound (210 mg, 52% yield) as gray solid. $^1$H NMR (400 MHz, $CDCl_3$) δ 8.06 (s, 1H), 7.19-7.12 (m, 1H), 7.10-7.03 (m, 1H), 6.65 (d, J=8.0 Hz, 1H), 5.91 (dd, J=5.2, 12.0 Hz, 1H), 4.22-4.17 (m, 1H), 4.13-4.02 (m, 2H), 4.01-3.90 (m, 2H), 3.88 (s, 3H), 3.87-3.81 (m, 1H), 3.65-3.57 (m, 1H), 3.06-2.95 (m, 1H), 2.95-2.75 (m, 3H), 2.66-2.54 (m, 1H), 2.44-2.30 (m, 1H), 1.48 (s, 9H).

Step 5—3-[1-Methyl-7-[[(2S)-morpholin-2-yl]methoxy]benzimidazol-2-yl]oxypiperidine-2,6-dione To a mixture of tert-butyl (2S)-2-[[2-[(2,6-dioxo-3-piperidyl)oxy]-3-methyl-benzimidazol-4-yl]oxymethyl]morpholine-4-carboxylate (80.0 mg, 168 umol) in DCM (4 mL) was added TFA (3.08 g, 27.0 mmol, 2.00 mL). The mixture was stirred at 20° C. for 1 hr. On completion, the reaction mixture was concentrated in vacuo to give the title compound (82.3 mg, 99% yield, TFA salt) as yellow oil. LC-MS (ESI+) m/z 375.2 (M+H)$^+$.

N-[2-(4-formylcyclohexyl)-5-methoxy-1,3-benzoxazol-6-yl]pyrimidine-4-carboxamide (Intermediate BLB)

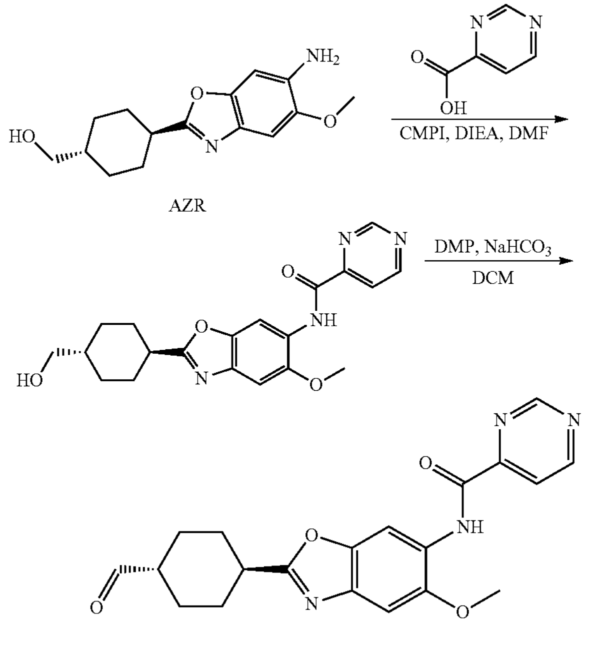

BLB

Step 1—N-[2-[4-(hydroxymethyl)cyclohexyl]-5-methoxy-1,3-benzoxazol-6-yl]pyrimidine-4- carboxamide A mixture of pyrimidine-4-carboxylic acid (70.7 mg, 569 umol, CAS #31462-59-6), CMPI (180 mg, 706 umol) and DIPEA (140 mg, 1.09 mmol) in DMF (2 mL) was stirred at 20° C. for 0.5 hr. The resulting mixture was added to a mixture of [4-(6-amino-5-methoxy-1,3-benzoxazol-2-yl)cyclohexyl]methanol (150 mg, 543 umol, Intermediate AZR) in DMF (2 mL) at 20° C., and the reaction mixture was stirred at 20° C. for 1 hr. On completion, the reaction mixture was quenched by water (1 mL). The mixture was diluted with water (50 mL) and extracted with EA (3×30 mL). The organic layer was washed with brine (3×40 mL), dried over anhydrous sodium sulfate and filtered. The filtrated was concentrated in vacuo and the residue was purified by silica gel chromatography (PE:EA=2:1 to 1:5) to give the title compound (160 mg, 77% yield) as yellow solid. $^1$H NMR (400 MHz, DMSO-$d_6$) δ 10.54 (s, 1H), 9.45 (d, J=1.6 Hz, 1H), 9.18 (d, J=5.2 Hz, 1H), 8.68 (s, 1H), 8.19 (dd, J=1.6, 5.2 Hz, 1H), 7.50 (s, 1H), 4.00 (s, 3H), 3.41 (s, 1H), 3.27 (d, J=6.4 Hz, 2H), 2.95-2.85 (m, 1H), 2.23-2.12 (m, 2H), 1.96-1.80 (m, 2H), 1.63-1.50 (m, 2H), 1.48-1.37 (m, 1H), 1.14-1.02 (m, 2H).

Step 2—N-[2-(4-formylcyclohexyl)-5-methoxy-1,3-benzoxazol-6-yl]pyrimidine-4-carboxamide To a mixture of N-[2-[4-(hydroxymethyl)cyclohexyl]-5-methoxy-1,3-benzoxazol-6-yl]pyrimidine- 4-carboxamide (130 mg, 339 umol) and $NaHCO_3$ (143 mg, 1.70 mmol) in DCM (10 mL) was added DMP (216 mg, 509 umol) at 0° C. Then the reaction mixture was stirred at 20° C. for 2 hrs. On completion, the reaction mixture was diluted with saturated $Na_2S_2O_3$ aqueous (5 mL) and saturated $NaHCO_3$ aqueous (5 mL), then the mixture was stirred at 20° C. for 0.5 hr. Next the mixture was diluted with water (50 mL) and extracted with DCM (3×30 mL). The organic layer was washed with saturated $NaHCO_3$ aqueous (2×50 mL) and brine (3×50 mL), dried over anhydrous sodium sulfate and filtered. The filtrated was concentrated in vacuo and the crude product was purified by reversed-phase HPLC (0.1% FA condition) to give the title compound (80.0 mg, 61% yield) as yellow solid. $^1$H NMR (400 MHz, DMSO-$d_6$) δ 10.53 (s, 1H), 9.62 (s, 1H), 9.44 (d, J=1.6 Hz, 1H), 9.17 (d, J=5.2 Hz, 1H), 8.68 (s, 1H), 8.19 (dd, J=1.2, 5.2 Hz, 1H), 7.50 (s, 1H), 4.01 (s, 3H), 3.02-2.91 (m, 1H), 2.44-2.34 (m, 1H), 2.28-2.18 (m, 2H), 2.10-2.00 (m, 2H), 1.72-1.59 (m, 2H), 1.45-1.33 (m, 2H).

Pyrimidine-2-carboxamide (Intermediate BLC)

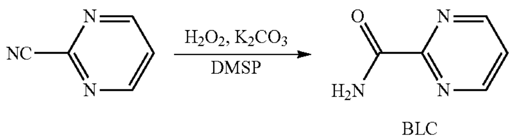

BLC

To a solution of pyrimidine-2-carbonitrile (1.00 g, 9.52 mmol, CAS #14080-23-0) in DMSO (20 mL) was added $K_2CO_3$ (3.95 g, 28.5 mmol). Then $H_2O_2$ (5.39 g, 47.6 mmol, 4.57 mL, 30% purity) was added dropwise. The mixture was stirred at 25° C. for 1 hr. On completion, the reaction mixture was quenched by addition saturated solution of $Na_2SO_3$ (5 mL), then diluted with $H_2O$ (50 mL) and extracted with EA (3×100 mL). The combined organic layer was dried over anhydrous $Na_2SO_4$, filtered and concentrated in vacuo to give a residue. The residue was purified by column chromatography ($SiO_2$) the title compound (0.40 g, 34% yield) as a yellow solid. $^1$H NMR (400 MHz, DMSO- $d_6$) δ 8.94 (d, J=4.8 Hz, 2H), 8.19 (s, 1H), 7.80 (s, 1H), 7.66 (t, J=4.8 Hz, 1H). LC-MS ($ESI^+$) m/z 124.1 $(M+H)^+$.

N-[2-(4-formylcyclohexyl)-6-methoxy-indazol-5-yl]pyrimidine-2-carboxamide (Intermediate BLD)

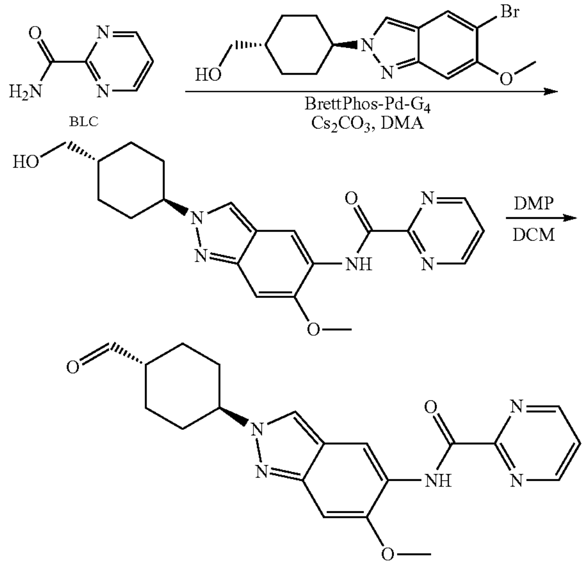

BLD

Step 1—N-[2-[4-(hydroxymethyl)cyclohexyl]-6-methoxy-indazol-5-yl]pyrimidine-2-carboxamide A mixture of pyrimidine-2-carboxamide (200 mg, 1.62 mmol, Intermediate BLC), [4-(5-bromo-6-methoxy-indazol-2-yl)cyclohexyl]methanol (367 mg, 1.08 mmol, synthesized via Steps 1-3 of Intermediate ATE), $Cs_2CO_3$ (705 mg, 2.17 mmol) and BrettPhos (Pd, G4) (49.8 mg, 54.2 umol) in DMA (5.00 mL) was degassed and purged with $N_2$ for 3 times, and then the mixture was stirred at 100° C. for 48 hrs under $N_2$ atmosphere. On completion, the reaction mixture was filtered and the filtrate was concentrated in vacuo to give a residue. The residue was purified by reversed phase (0.1% FA condition) to give the crude product. The crude product was re-purified by prep-TLC ($SiO_2$) to give the title compound (30.0 mg, 7.2% yield) as a yellow solid. $^1H$ NMR (400 MHz, DMSO-$d_6$) δ 10.58 (s, 1H), 9.07 (d, J=4.8 Hz, 2H), 8.73 (s, 1H), 8.34 (s, 1H), 7.77 (t, J=4.8 Hz, 1H), 7.15 (s, 1H), 4.50 (t, J=5.2 Hz, 1H), 4.41-4.29 (m, 1H), 3.98 (s, 3H), 3.29 (t, J=5.6 Hz, 2H), 2.17-2.10 (m, 2H), 1.91 (s, 2H), 1.89-1.81 (m, 2H), 1.54-1.40 (m, 1H), 1.19-1.08 (m, 2H). LC-MS ($ESI^+$) m/z 382.3 $(M+H)^+$.

Step 2—N-[2-(4-formylcyclohexyl)-6-methoxy-indazol-5-yl]pyrimidine-2-carboxamide To a solution of N-[2-[4-(hydroxymethyl)cyclohexyl]-6-methoxy-indazol-5-yl]pyrimidine-2- carboxamide (30.0 mg, 78.65 umol) in DCM (6.00 mL) was added DMP (40.0 mg, 94.4 umol) at 0° C., then the mixture was stirred at 20° C. for 1 hr. On completion, the reaction mixture was quenched by addition saturated solution of $Na_2S_2O_3$ (1 mL), and saturated solution of $NaHCO_3$ (2 mL), then extracted with DCM (3x10 mL). The combined organic layer was washed with brine (2x20 mL), dried over anhydrous $Na_2SO_4$, filtered and concentrated in vacuo to give the title compound (25.0 mg, 83% yield) as a yellow solid. LC-MS ($ESI^+$) m/z 380.3 $(M+H)^+$.

N-[2-(4-formylcyclohexyl)-6-methoxy-indazol-5-yl]benzamide (Intermediate BLE)

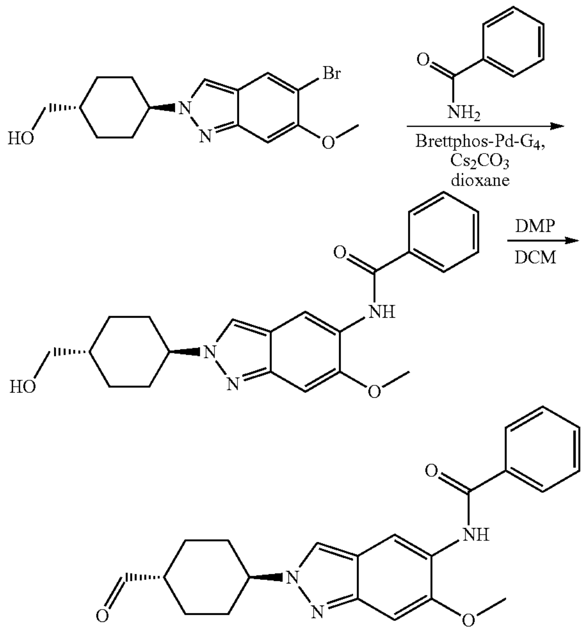

BLE

Step 1—N-[2-[4-(hydroxymethyl)cyclohexyl]-6-methoxy-indazol-5-yl]benzamide

To a solution of benzamide (53.6 mg, 442 umol, CAS #27208-38-4), [4-(5-bromo-6-methoxy-indazol-2-yl)cyclohexyl]methanol (150 mg, 442 umol, synthesized via Steps 1-3 of Intermediate ATE) in dioxane (4 mL) was added $Cs_2CO_3$ (288 mg, 884 umol), BrettPhos (Pd, G4) (36.6 mg, 39.8 umol) under $N_2$. The reaction mixture was stirred at 85° C. for 16 hrs. On completion, the reaction mixture was filtered and concentrated in vacuo to give a residue. The crude product was purified by reverse phase HPLC (0.1% FA condition) to give the title compound (130 mg, 73% yield) as yellow solid. $^1H$ NMR (400 MHz, DMSO-$d_6$) δ 9.36 (s, 1H), 8.29 (s, 1H), 8.14 (s, 1H), 7.97 (d, J=7.2 Hz, 2H), 7.62-7.50 (m, 3H), 7.08 (s, 1H), 4.48 (t, J=5.2 Hz, 1H), 4.41-4.30 (m, 1H), 3.89 (s, 3H), 3.29 (t, J=5.6 Hz, 2H), 2.19-2.09 (m, 2H), 1.96-1.81 (m, 4H), 1.53-1.42 (m, 1H), 1.21-1.08 (m, 2H); LC-MS ($ESI^+$) m/z 380.2 $(M+H)^+$.

Step 2—N-[2-(4-formylcyclohexyl)-6-methoxy-indazol-5-yl]benzamide

To a solution of N-[2-[4-(hydroxymethyl)cyclohexyl]-6-methoxy-indazol-5-yl]benzamide (120 mg, 296 umol) in DCM (2 mL) was added DMP (163 mg, 385 umol, 119 uL) at 0° C. under $N_2$. The reaction mixture was stirred at 25° C. for 6 hrs. On completion, the reaction mixture was quenched with $Na_2S_2O_3$ (10 mL), and then diluted with $H_2O$ (2×10 mL) and extracted with DCM (3×10 mL). The combined organic layers were washed with $NaHCO_3$ (2×10 mL), then organic layers were washed with NaCl (2×10 mL ), dried over $Na_2SO_4$, filtered and concentrated in vacuo to give a residue to give the title compound (110 mg, 77% yield) as yellow solid. $^1$H NMR (400 MHz, DMSO-$d_6$) δ 9.64 (s, 1H), 9.36 (s, 1H), 8.29 (s, 1H), 8.15 (s, 1H), 7.97 (d, J=7.2 Hz, 2H), 7.62-7.51 (m, 3H), 7.08 (s, 1H), 4.46-4.34 (m, 1H), 3.89 (s, 3H), 2.47-2.38 (m, 1H), 2.24-2.16 (m, 2H), 2.11 (d, J=11.2 Hz, 2H), 2.02-1.91 (m, 2H), 1.51-1.37 (m, 2H); LC-MS (ESI$^+$) m/z 378.2 (M+H)$^+$.

(S)-(5-oxo-1-((2-(trimethylsilyl)ethoxy)methyl)pyrrolidin-2-yl)methyl4-methylbenzenesulfonate (Intermediate BLF)

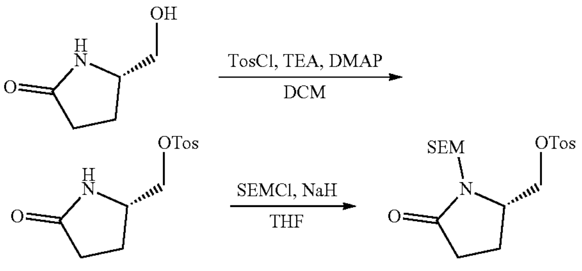

BLF

Step 1—(S)-(5-oxopyrrolidin-2-yl)methyl 4-methylbenzenesulfonate

To a solution of (5S)-5-(hydroxymethyl)pyrrolidin-2-one (CAS #17342-08-4, 19.4 g, 168 mmol), 4-methylbenzenesulfonyl chloride (35.4 g, 185 mmol), DMAP (4.13 g, 33.7 mmol) in DCM (360 mL) was added TEA (17.0 g, 168 mmol) at 0° C. The mixture was stirred at 0-25° C. for 12 hours. On completion, the reaction mixture was quenched by addition $H_2O$ (100 mL) at 25° C., and then diluted with DCM (100 mL) and extracted with DCM (100 mL×3). The combined organic layers were dried over $Na_2SO_4$, filtered, and concentrated in vacuo. The residue was purified by column chromatography (petroleum ether/ethyl acetate=10/1 to 0/1) to give the title compound (21.0 g, 45% yield) as a yellow solid. LC-MS (ESI$^+$) m/z 270.1 (M+H)$^+$.

Step 2—(S)-(5-oxo-1-((2-(trimethylsilyl)ethoxy)methyl)pyrrolidin-2-yl)methyl4-methylbenzenesulfonate To a solution of [(2S)-5-oxopyrrolidin-2-yl]methyl 4-methylbenzenesulfonate (10.0 g, 37.1 mmol), 2-(chloromethoxy)ethyl-trimethyl-silane (6.19 g, 37.1 mmol) in THF (300 mL) was added NaH (1.49 g, 37.1 mmol, 60% dispersion in mineral oil) at 0° C. The mixture was then stirred at 0° C. for 3 hours. On completion, the reaction mixture was quenched by addition $H_2O$ (100 mL) at 0° C., and then diluted with EA (100 mL) and extracted with EA (3×100 mL). The combined organic layers were washed with brine (100 mL×2), dried over $Na_2SO_4$, filtered, concentrated in vacuo. The residue was purified by column chromatography (petroleum ether/ethyl acetate=10/1 to 0/1) to give the title compound (4 g, 26% yield) as a colorless oil. LC-MS (ESI$^+$) m/z 422.3 (M+Na)$^+$.

(S)-5-(((5-bromo-2-((1r,4S)-4-(hydroxymethyl)cyclohexyl)-2H-indazol-6-yl)oxy)methyl)-1-((2-(trimethylsilyl)ethoxy)methyl)pyrrolidin-2-one (Intermediate BLG)

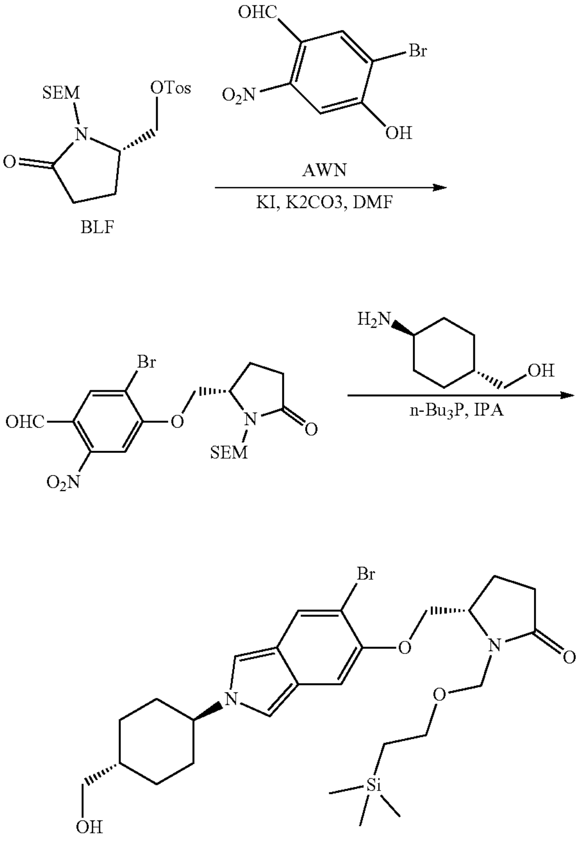

BLG

Step 1—(S)-5-bromo-2-nitro-4-((5-oxo-1-((2-(trimethylsilyl)ethoxy)methyl)pyrrolidin-2-yl)methoxy) benzaldehyde To a solution of [(2S)-5-oxo-1-(2-trimethylsilylethoxymethyl)pyrrolidin-2-yl]methyl 4-methylbenzenesulfonate (4.00 g, 10.0 mmol, Intermediate BLF), 5-bromo-4-hydroxy-2-nitro-benzaldehyde (2.46 g, 10.0 mmol, Intermediate AWN) in DMF (90 mL) was added KI (1.66 g, 10.0 mmol) and $K_2CO_3$ (1.38 g, 10.0 mmol). The mixture was stirred at 80° C. for 12 hours. On completion, the reaction mixture was quenched by addition $H_2O$ (40 mL) at 25° C., and then diluted with EA (40 mL) and extracted with EA (3×40 mL). The combined organic layers were washed with brine (2×30 mL), dried over $Na_2SO_4$, filtered, concentrated in vacuo and purified by column chromatography (petroleum ether/ethyl acetate=10/1 to 0/1) to give the title compound (1.50 g, 28% yield) as a yellow oil. LC-MS (ESI$^+$) m/z 497.0 (M+23)$^+$.

Step 2—(S)-5-(((5-bromo-2-((1r,4S)-4-(hydroxymethyl)cyclohexyl)-2H-indazol-6-yl)oxy)methyl)-1-((2-(trimethylsilyl)ethoxy)methyl)pyrrolidin-2-one A mixture of 5-bromo-2-nitro-4-[[(2S)-5-oxo-1-(2-trimethylsilylethoxymethyl)pyrrolidin-2-yl]methoxy]benzaldehyde (1.50 g, 3.17 mmol), (4-aminocyclohexyl)methanol (CAS #1467-84-1, 409 mg, 3.17 mmol) in IPA (15 mL) was degassed and purged with $N_2$ for 3 times, and then the mixture was stirred at 80° C. for 16 hr under $N_2$ atmosphere. Next, tributylphosphane (1.92 g, 9.51 mmol) was added to the mixture at 25° C. Then the mixture was stirred at 80° C. for 6 hours under $N_2$ atmosphere. On completion, the reaction mixture was concentrated in vacuo. The residue was purified by reverse phase flash (0.1% FA condition) to give the title compound (1.10 g, 62% yield) as a brown oil. LC-MS (ESI+) m/z 574.4 $(M+23)^+$.

N-[2-(4-formylcyclohexyl)-6-[[(2S)-5-oxo-1-(2-trimethylsilylethoxymethyl)pyrrolidin-2-yl]methoxy]indazol-5-yl]pyridine-2-carboxamide (Intermediate BLH)

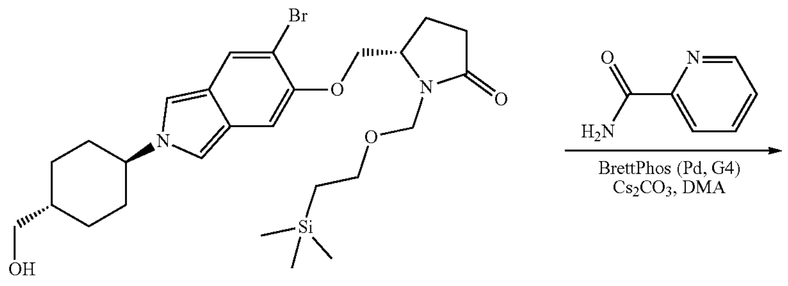

BLG

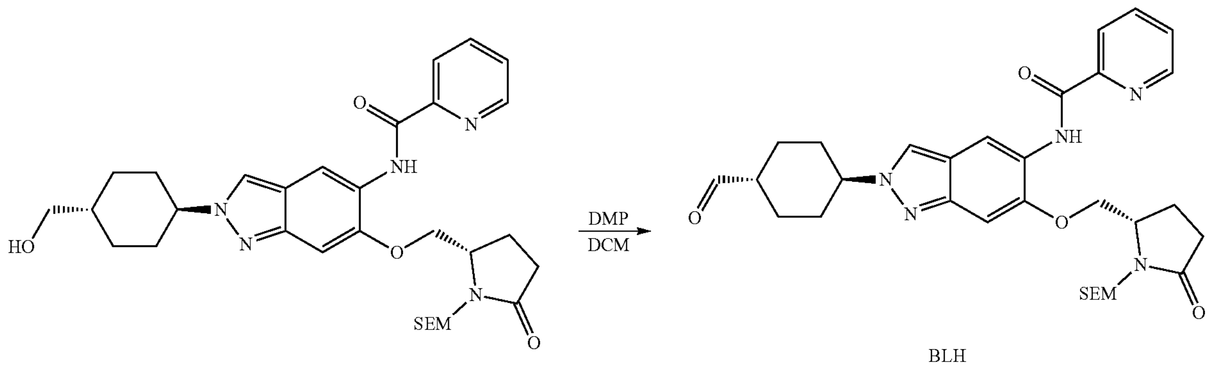

BLH

Step 1—N-(2-((1r,4S)-4-(hydroxymethyl)cyclohexyl)-6-(((S)-5-oxo-1-((2-(trimethylsilyl)ethoxy)methyl)pyrrolidin-2-yl)methoxy)-2H-indazol-5-yl)picolinamide A mixture of (5S)-5-[[5-bromo-2-[4-(hydroxymethyl)cyclohexyl]indazol-6-yl]oxymethyl]-1-(2-trimethylsilylethoxymethyl)pyrrolidin-2-one (0.50 g, 904 umol, Intermediate BLG), pyridine-2-carboxamide (110 mg, 904 umol), $Cs_2CO_3$ (589 mg, 1.81 mmol), BrettPhos (Pd, G4) (41.6 mg, 45.2 umol) in DMA (10 mL) was degassed and purged with $N_2$ for 3 times, and then the mixture was stirred at 100° C. for 12 hours under $N_2$ atmosphere. On completion, the reaction mixture was quenched by addition $H_2O$ (1 mL) at 25° C. The residue was purified by reverse phase flash (0.1% FA condition) to give the title compound (105 mg, 17% yield) as a brown solid. LC-MS (ESI+) m/z 594.4 $(M+H)^+$.

Step 2—N-[2-(4-formylcyclohexyl)-6-[[(2S)-5-oxo-1-(2-trimethylsilylethoxymethyl)pyrrolidin-2-yl]methoxy]indazol-5-yl]pyridine-2-carboxamide To a solution of N-[2-[4-(hydroxymethyl)cyclohexyl]-6-[[(2S)-5-oxo-1-(2-trimethylsilylethoxymethyl)pyrrolidin-2-yl]methoxy]indazol-5-yl]pyridine-2-carboxamide (350 mg, 589 umol) in DCM (10 mL) was added DMP (375 mg, 884 umol) at 0° C. The mixture was stirred at 25° C. for 1 hr. The reaction mixture was quenched by addition $Na_2S_2O_3$ (5 mL) and $NaHCO_3$ (5 mL) adjusted to the pH=8 at 25° C. Then the mixture was diluted with DCM (5 mL) and extracted with DCM 15 mL (3x5 mL). The combined organic layers were dried over $Na_2SO_4$, filtered and concentrated under reduced pressure to give a residue. The residue was purified by prep-TLC (petroleum ether/ethyl acetate=1/1) to give the title compound (50.0 mg, 13% yield) as a brown solid. LC-MS $(ESI^+)$ m/z 592.4 $(M+H)^+$.

N-[2-(4-formylcyclohexyl)-6-[[(2S)-5-oxo-1-(2-trimethylsilylethoxymethyl)-pyrrolidin-2-yl]methoxy]indazol-5-yl]-6-(trifluoromethyl)pyridine-2-carboxamide (Intermediate BLI

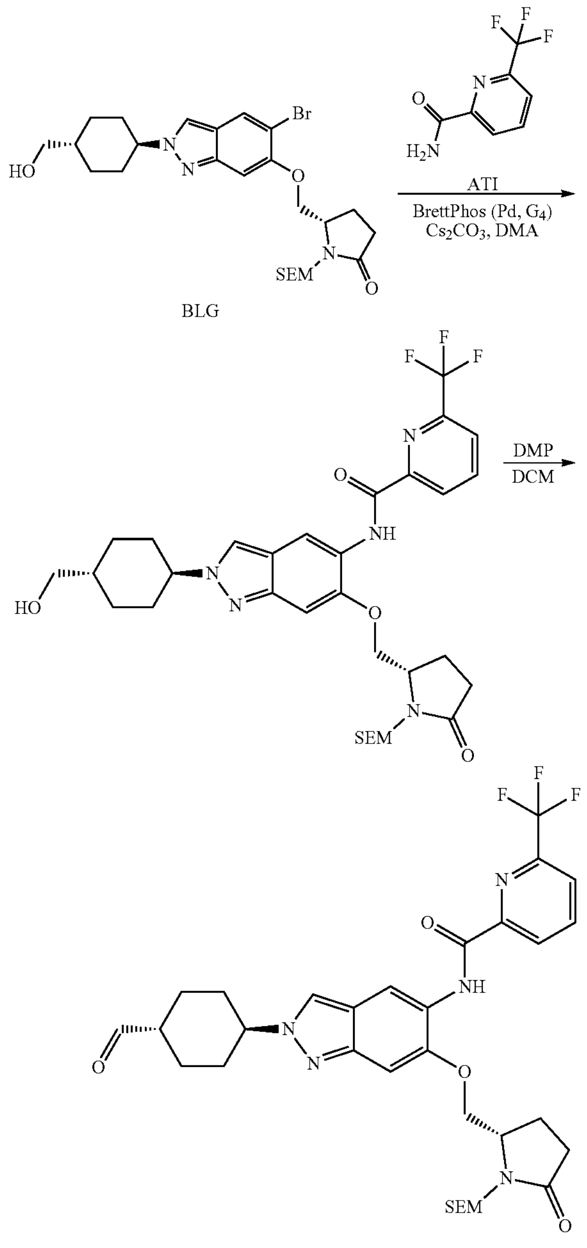

BLG

BLI

Step 1—N-(2-((1r,4S)-4-(hydroxymethyl)cyclohexyl)-6-(((S)-5-oxo-1-((2-(trimethylsilyl)ethoxy)methyl)pyrrolidin-2-yl)methoxy)-2H-indazol-5-yl)-6-(trifluoromethyl)picolinamide A mixture of (5S)-5-[[5-bromo-2-[4-(hydroxymethyl)cyclohexyl]indazol-6-yl]oxymethyl]-1-(2-trimethylsilylethoxymethyl)pyrrolidin-2-one (0.50 g, 904 umol, Intermediate BLG), 6-(trifluoromethyl)pyridine-2-carboxamide (172 mg, 904 umol, Intermediate ATI), $Cs_2CO_3$ (589 mg, 1.81 mmol), BrettPhos (Pd, G4) (41.6 mg, 45.2 umol) in DMA (1 mL) was degassed and purged with $N_2$ for 3 times, and then the mixture was stirred at 100° C. for 12 hours under $N_2$ atmosphere. On completion, the reaction mixture was quenched by addition $H_2O$ (0.5 mL) at 25° C., and then concentrated in vacuo. The residue was purified by reverse phase flash (0.1% FA condition) to give the title compound (300 mg, 46% yield) as a solid. LC-MS (ESI+) m/z 662.3 $(M+H)^+$.

Step 2—N-[2-(4-formylcyclohexyl)-6-[[(2S)-5-oxo-1-(2-trimethylsilylethoxymethyl)pyrrolidin-2-yl]methoxy]indazol-5-yl]-6-(trifluoromethyl)pyridine-2-carboxamide To a solution of N-[2-[4-(hydroxymethyl)cyclohexyl]-6-[[(2S)-5-oxo-1-(2-trimethylsilylethoxymethyl) pyrrolidin-2-yl]methoxy]indazol-5-yl]-6-(trifluoromethyl)pyridine-2-carboxamide (300 mg, 453 umol) in DCM (6 mL) was added DMP (231 mg, 544 umol) at 0° C. The mixture was stirred at 25° C. for 1 hour. The reaction mixture was quenched by addition $Na_2S_2O_3$ (5 mL) and $NaHCO_3$ (5 mL) adjusted the pH=8 at 25° C., and then diluted with DCM (5 mL) and extracted with DCM (3×5 mL). The combined organic layers were dried over $Na_2SO_4$, filtered and concentrated under reduced pressure to give the title compound (240 mg, 80% yield) as a yellow solid. LC-MS (ESI+) m/z 660.4 $(M+H)^+$.

(S) [(2R)-5-oxo-1-(2-trimethylsilylethoxymethyl)pyrrolidin-2-yl]methyl4-methylbenzenesulfonate (Intermediate BLJ)

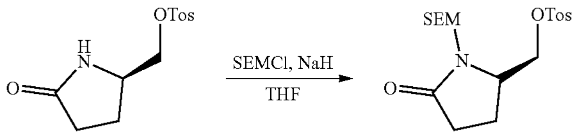

BLJ

To a solution of [(2R)-5-oxopyrrolidin-2-yl]methyl 4-methylbenzenesulfonate (5.80 g, 21.5 mmol, CAS #128899-31-0) and 2-(chloromethoxy)ethyl-trimethyl-silane (4.67 g, 28.0 mmol) in THF (150 mL) was added NaH (1.12 g, 28.0 mmol, 60% dispersion in mineral oil) at 0° C. The mixture was stirred at 0-25° C. for 12 hours. On completion, the reaction mixture was quenched by addition $H_2O$ (100 mL) at 0° C., and then diluted with EA (100 mL) and extracted with EA (3×100 mL). The combined organic layers were washed with brine (2×50 mL), dried over $Na_2SO_4$, filtered and concentrated under reduced pressure to give a residue, which was purified by column chromatography (petroleum ether/ethyl acetate=10/1 to 1/1) to give the title compound (3.00 g, 34% yield) obtained as a yellow oil. $^1H$ NMR (400 MHz, $CDCl_3$) δ 7.78 (d, J=8.4 Hz, 2H), 7.36 (d, J=8.4 Hz, 2H), 4.71 (d, J=10.8 Hz, 1H), 4.50 (d, J=10.8 Hz, 1H), 4.14 (d, J=4.0 Hz, 2H), 3.92-3.89 (m, 1H), 3.46-3.42 (m, 2H), 2.51-2.46 (m, 4H), 2.28-2.16 (m, 1H), 2.21-2.13 (m, 1H), 1.96-1.88 (m, 1H), 0.87-0.83 (m, 2H), -0.01 (s, 9H).

(5R)-5-[[5-bromo-2-[4-(hydroxymethyl)cyclohexyl] indazol-6-yl]oxymethyl]-1-(2- trimethylsilylethoxymethyl)pyrrolidin-2-one (Intermediate BLK)

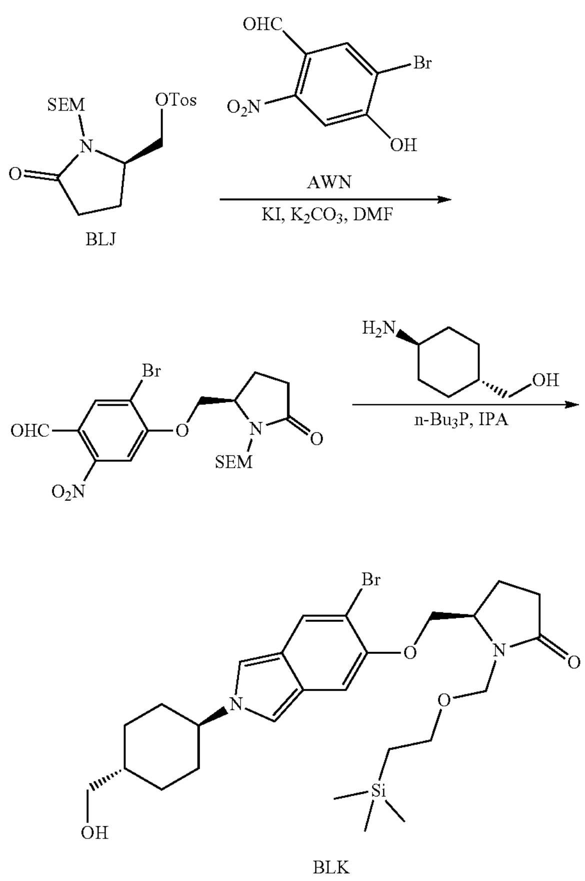

Step 1—5-Bromo-2-nitro-4-[[(2R)-5-oxo-1-(2-trimethylsilylethoxymethyl)pyrrolidin-2-yl]methoxy] benzaldehyde A mixture of [(2R)-5-oxo-1-(2-trimethylsilylethoxymethyl)pyrrolidin-2-yl]methyl4- methylbenzenesulfonate (2.90 g, 7.26 mmol, Intermediate BLK), 5-bromo-4-hydroxy-2-nitro-benzaldehyde (1.79 g, 7.26 mmol, Intermediate AWN), $K_2CO_3$ (3.01 g, 21.8 mmol) and KI (1.20 g, 7.26 mmol) in DMF (50 mL) was degassed and purged with $N_2$ for 3 times, and then the mixture was stirred at 80° C. for 12 hours under $N_2$ atmosphere. On completion, the reaction mixture was partitioned between $H_2O$ (50 mL) and EA (300 mL). The organic phase was separated, washed with brine (100 mL), dried over $Na_2SO_4$, filtered and concentrated under reduced pressure to give a residue. The residue was purified by column chromatography (petroleum ether/ethyl acetate=10/1 to 0/1) to give the title compound (1.00 g, 29% yield) as a yellow oil. $^1$H NMR (400 MHz, DMSO-$d_6$) δ10.05 (s, 1H), 8.19 (s, 1H), 7.81 (s, 1H), 4.81 (d, J=10.8 Hz, 1H), 4.65 (d, J=10.8 Hz, 1H), 4.55 (d, J=8.8 Hz, 1H), 4.36-4.32 (m, 1H), 4.14-4.12 (m, 1H), 3.37-3.33 (m, 2H), 2.73 (s, 2H), 2.26-2.22 (m, 1H), 2.02-1.99 (m, 1H), 0.70-0.62 (m, 1H), 0.54-0.46 (m, 1H), -0.12 (s, 9H).

Step 2—(5R)-5-[[5-bromo-2-[4-(hydroxymethyl) cyclohexyl]indazol-6-yl]oxymethyl]-1-(2- trimethylsilylethoxymethyl)pyrrolidin-2-one A mixture of 5-bromo-2-nitro-4-[[(2R)-5-oxo-1-(2-trimethylsilylethoxymethyl)pyrrolidin-2-yl]methoxy] benzaldehyde (500 mg, 1.06 mmol) and (4-aminocyclohexyl)methanol (136 mg, 1.06 mmol) in IPA (10 mL) was stirred at 80° C. for 16 hours under $N_2$. The reaction was cooled to 25° C. and tributylphosphane (CAS #1467-84-1, 641 mg, 3.17 mmol) was added. Then the reaction mixture was stirred at 80° C. for 6 hours. On completion, the reaction mixture was filtered and concentrated and purified by reverse phase flash (0.1% FA condition) to give the title compound (200 mg, 30% yield, FA salt) as a yellow solid. LC-MS (ESI$^+$) m/z 554.2 (M+H)$^+$.

N-[2-(4-formylcyclohexyl)-6-[[(2R)-5-oxo-1-(2-trimethylsilylethoxymethyl)pyrrolidin- 2-yl] methoxy]indazol-5-yl]pyridine-2-carboxamide (Intermediate BLL)

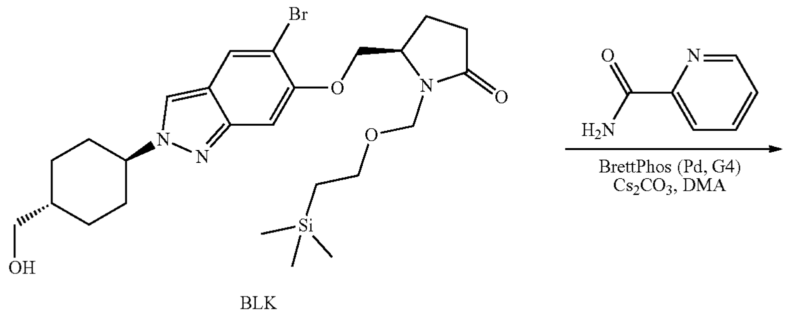

-continued

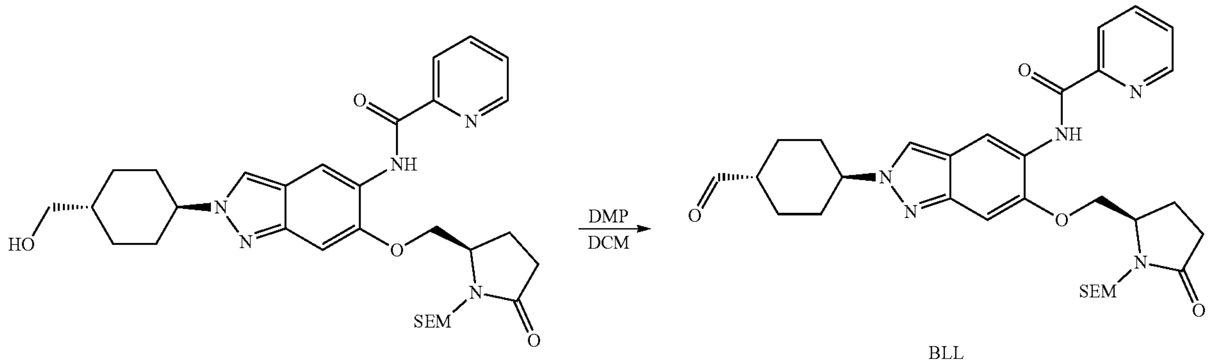

BLL

Step 1—(R)-5-(((5-bromo-2-((1r,4S)-4-(hydroxymethyl)cyclohexyl)-2H-indazol-6-yl)oxy)methyl)-1-((2-(trimethylsilyl)ethoxy)methyl)pyrrolidin-2-one A mixture of (5R)-5-[[5-bromo-2-[4-(hydroxymethyl)cyclohexyl]indazol-6-yl]oxymethyl]-1-(2- trimethylsilylethoxymethyl)pyrrolidin-2-one (150 mg, 271 umol, Intermediate BLK), pyridine-2-carboxamide (CAS #1452-77-3, 39.8 mg, 326 umol), BrettPhos (Pd, G4) (12.5 mg, 13.6 umol), $Cs_2CO_3$ (177 mg, 543 umol) in DMA (3 mL) was degassed and purged with $N_2$ for 3 times, and then the mixture was stirred at 100° C. for 12 hours under $N_2$ atmosphere. On completion, the reaction mixture was filtered and concentrated under reduced pressure to give a residue. The residue was purified by reverse phase flash (0.1% FA condition) to give the title compound (100 mg, 28% yield, FA salt) as a brown solid. LC-MS (ESI+) m/z 594.5 $(M+H)^+$.

Step 2—N-[2-(4-formylcyclohexyl)-6-[[(2R)-5-oxo-1-(2-trimethylsilylethoxymethyl)pyrrolidin- 2-yl]methoxy]indazol-5-yl]pyridine-2-carboxamide To a solution of N-[2-[4-(hydroxymethyl)cyclohexyl]-6-[[(2R)-5-oxo-1-(2-trimethylsilylethoxymethyl) pyrrolidin-2-yl]methoxy]indazol-5-yl]pyridine-2-carboxamide (100 mg, 84.2 umol) in DCM (5 mL) was added DMP (53.6 mg, 126 umol) at 0° C. Then the mixture was stirred at 25° C. for 1 hour. On completion, the reaction mixture was quenched by addition saturated $NaHCO_3$ (1 mL) and $Na_2S_2O_3$ (1 mL), and then diluted with $H_2O$ (2 mL) and extracted with DCM 50 mL (2×25 mL). The combined organic layers were washed with brine (30 mL), dried over $Na_2SO_4$, filtered and concentrated under reduced pressure to give a residue, and which was purified by prep-TLC (petroleum ether/ethyl acetate=0/1) to give the title compound (20.0 mg, 34% yield) as a yellow solid. LC-MS (ESI+) m/z 592.3 $(M+H)^+$.

N-[2-(4-formylcyclohexyl)-6-[[(2R)-5-oxo-1-(2-trimethylsilylethoxymethyl)-pyrrolidin-2-yl]methoxy]indazol-5-yl]-6-(trifluoromethyl)pyridine-2-carboxamide (Intermediate BLM)

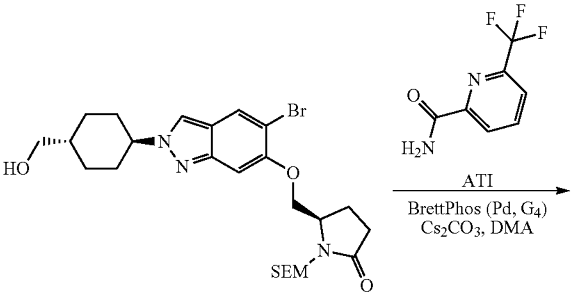

BLK

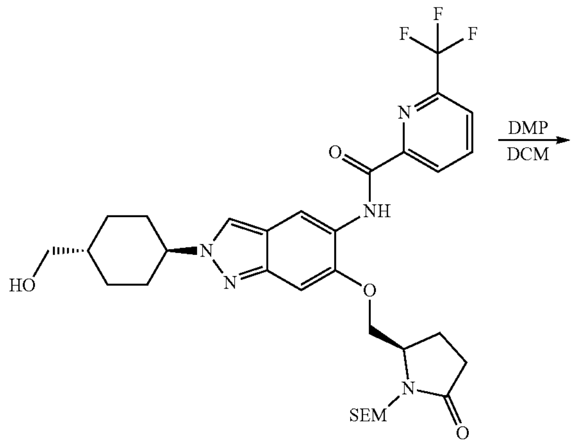

-continued

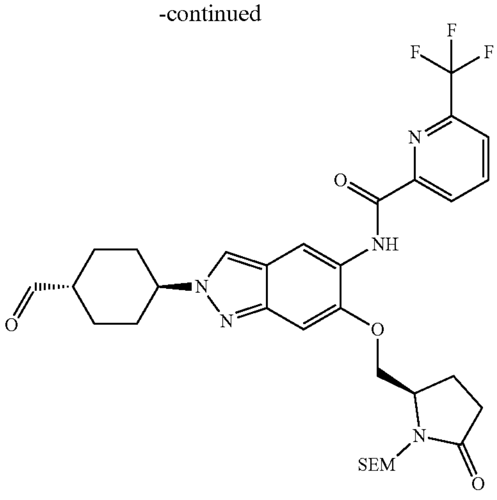

BLM

Step 1—N-[2-[4-(hydroxymethyl)cyclohexyl]-6-[[(2R)-5-oxo-1-(2-trimethylsilylethoxymethyl) pyrrolidin-2-yl]methoxy]indazol-5-yl]-6-(trifluoromethyl)pyridine-2-carboxamide A mixture of (5R)-5-[[5-bromo-2-[4-(hydroxymethyl)cyclohexyl]indazol-6-yl]oxymethyl]-1-(2-trimethylsilylethoxymethyl)pyrrolidin-2-one (160 mg, 289.55 umol, Intermediate BLK), 6-(trifluoromethyl)pyridine-2-carboxamide (55.1 mg, 289 umol, Intermediate ATI), $Cs_2CO_3$ (189 mg, 579 umol), BrettPhos (Pd, G4) (13.3 mg, 14.5 umol) in DMA (3 mL) was degassed and purged with $N_2$ for 3 times, and then the mixture was stirred at 100° C. for 12 hours under $N_2$ atmosphere. On completion, the reaction mixture was filtered and the filtrate was concentrated under reduced pressure to give a residue. The crude product was purified by reverse phase flash (0.1% FA condition) to give the title compound (95.0 mg, 45% yield, FA salt) as a yellow solid. LC-MS (ESI+) m/z 662.5 $(M+H)^+$.

Step 2—N-[2-(4-formylcyclohexyl)-6-[[(2R)-5-oxo-1-(2-trimethylsilylethoxymethyl)pyrrolidin-2-yl]methoxy]indazol-5-yl]-6-(trifluoromethyl)pyridine-2-carboxamide To a solution of N-[2-[4-(hydroxymethyl)cyclohexyl]-6-[[(2R)-5-oxo-1-(2-trimethylsilylethoxymethyl) pyrrolidin-2-yl]methoxy]indazol-5-yl]-6-(trifluoromethyl)pyridine-2-carboxamide (95.0 mg, 134 umol, FA) in DCM (5 mL) was added DMP (85.4 mg, 201 umol) at 0° C. The mixture was stirred at 25° C. for 1 hour. Then the reaction mixture was quenched by addition saturated $NaHCO_3$ (3 mL) and $Na_2S_2O_3$ (3 mL), and then diluted with $H_2O$ (5 mL) and extracted with DCM 100 mL (2×50 mL). The combined organic layers were washed with brine (30 mL), dried over $Na_2SO_4$, filtered and concentrated under reduced pressure to give the title compound (80.0 mg, 66% yield) as a yellow solid. LC-MS (ESI+) m/z 660.2 $(M+H)^+$.

N-(2-((1r,4r)-4-Formylcyclohexyl)-6-(2-hydroxypropan-2-yl)-2H-indazol-5-yl)-5-(trifluoromethyl)picolinamide (Intermediate BLN)

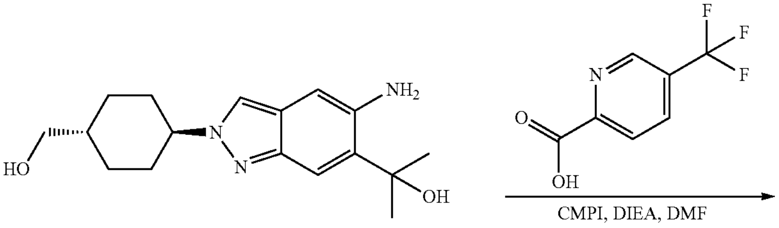

AOX

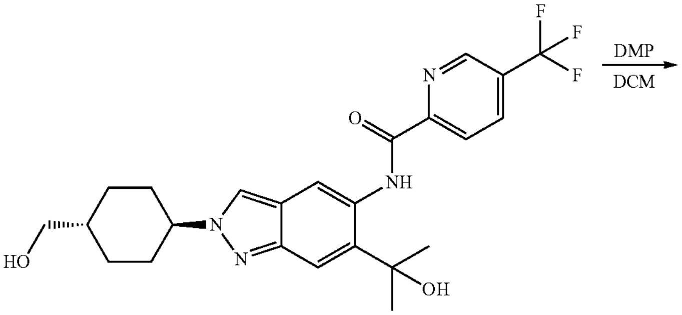

-continued

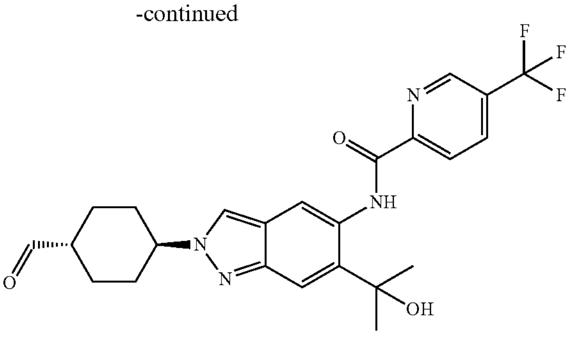

BLN

Step 1—N-(2-((1r,4r)-4-(Hydroxymethyl)cyclohexyl)-6-(2-hydroxypropan-2-yl)-2H-indazol-5-yl)-5- (trifluoromethyl)picolinamide To a solution of 2-[5-amino-2-[4-(hydroxymethyl)cyclohexyl]indazol-6-yl]propan-2-ol (50 mg, 165 umol, Intermediate AOX) and 5-(trifluoromethyl)pyridine-2-carboxylic acid (31.5 mg, 165 umol, CAS #80194-69-0) in the DMF (1.0 mL) was added CMPI (54.7 mg, 214 umol) and DIEA (63.9 mg, 494 umol). The mixture was stirred at 25° C. for 1 hour. On completion, the mixture was diluted with EA (20 mL) and washed with water (3x20 mL). The mixture was dried over $Na_2SO_4$, filtered and concentrated in vacuo to give the title compound (75 mg, 95% yield) as yellow solid. $^1$H NMR (400 MHz, $CDCl_3$) δ 12.11 (s, 1H), 8.99-8.96 (m, 1H), 8.84 (s, 1H), 8.47 (d, J=8.2 Hz, 1H), 8.15 (dd, J=1.7, 8.2 Hz, 1H), 7.93 (s, 1H), 7.75 (s, 1H), 4.38 (tt, J=3.6, 11.8 Hz, 1H), 3.57 (t, J=5.6 Hz, 2H), 2.34-2.31 (m, 2H), 2.05-2.03 (m, 2H), 2.03-1.94 (m, 2H), 1.80 (s, 6H), 1.73-1.62 (m, 1H), 1.40 (t, J=5.4 Hz, 1H), 1.29-1.25 (m, 2H).

Step 2—N-(2-((1r,4r)-4-Formylcyclohexyl)-6-(2-hydroxypropan-2-yl)-2H-indazol-5-yl)-5- (trifluoromethyl)picolinamide To a solution of N-[2-[4-(hydroxymethyl)cyclohexyl]-6-(1-hydroxy-1-methyl-ethyl)indazol-5-yl]-5- (trifluoromethyl)pyridine-2-carboxamide (75 mg, 157 umol) in the DCM (2.0 mL) was added DMP (80.1 mg, 189 umol). The mixture was stirred at 25° C. for 1 hour. On completion, the reaction mixture was quenched with saturated $Na_2S_2O_3$ (aq, 5 mL) and $NaHCO_3$ (aq, 5 mL), then the mixture was extracted with DCM (2x20 mL). The organic layer was dried over $Na_2SO_4$, filtered and concentrated in vacuo to give the title compound (74 mg, 99% yield) as yellow solid. $^1$H NMR (400 MHz, $CDCl_3$) δ 12.15 (s, 1H), 9.71 (d, J=0.8 Hz, 1H), 8.97-8.92 (m, 1H), 8.83 (s, 1H), 8.43 (d, J=8.2 Hz, 1H), 8.12 (dd, J=1.6, 8.2 Hz, 1H), 7.92 (s, 1H), 7.72 (s, 1H), 4.36 (tt, J=3.8, 11.8 Hz, 1H), 2.45-2.34 (m, 3H), 2.28-2.20 (m, 2H), 2.11-2.00 (m, 2H), 1.79 (s, 6H), 1.52 (dq, J=3.6, 13.1 Hz, 2H).

N-(2-((1r,4r)-4-formylcyclohexyl)-6-(2-hydroxypropan-2-yl)-2H-indazol-5-yl)-4-(trifluoromethyl)pyrimidine-5-carboxamide (Intermediate BLO)

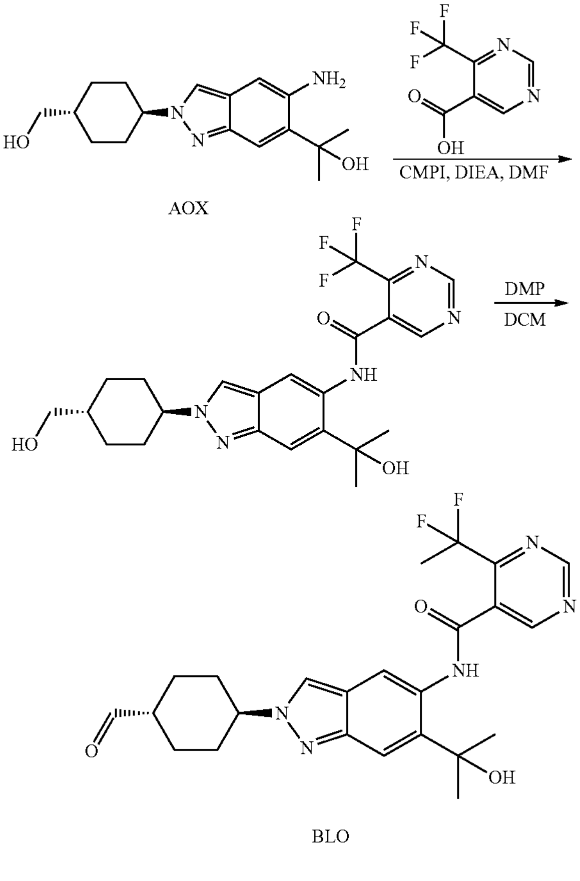

Step 1—N-(2-((1r,4r)-4-(hydroxymethyl)cyclohexyl)-6-(2-hydroxypropan-2-yl)-2H-indazol-5-yl)-4- (trifluoromethyl)pyrimidine- 5-carboxamide To a solution of 2-[5-amino-2-[4-(hydroxymethyl)cyclohexyl]indazol-6-yl]propan-2-ol (50 mg, 164 umol, Intermediate AOX) and 4-(trifluoromethyl)pyrimidine-5-carboxylic acid (31.6 mg, 164 umol, CAS #220880-12-6) in the DMF (1 mL) was added CMPI (54.7 mg, 214 umol) and DIEA (63.9 mg, 494 umol). The mixture was stirred at 25° C. for 1 hr. On completion, the mixture was diluted with EA (30 mL) and washed with water (3x30 mL). The organic layer was dried over $Na_2SO_4$, filtered and concentrated in vacuo to give the title compound (75.0 mg, 95% yield) as yellow solid. $^1H$ NMR (400 MHz, $CDCl_3$) δ 10.66 (s, 1H), 9.46 (s, 1H), 9.12 (s, 1H), 8.70 (s, 1H), 7.95 (s, 1H), 7.70 (s, 1H), 4.41-4.32 (m, 1H), 3.56 (d, J=6.4 Hz, 2H), 2.31 (d, J=11.6 Hz, 2H), 2.05-1.92 (m, 4H), 1.75 (s, 6H), 1.68-1.60 (m, 1H), 1.26-1.19 (m, 2H).

Step 2—N-(2-((1r,4r)-4-formylcyclohexyl)-6-(2-hydroxypropan-2-yl)-2H-indazol-5-yl)-4- (trifluoromethyl)pyrimidine-5-carboxamide To a solution of N-[2-[4-(hydroxymethyl)cyclohexyl]-6-(1-hydroxy-1-methyl-ethyl)indazol-5-yl]-4- (trifluoromethyl)pyrimidine-5-carboxamide (75.0 mg, 157 umol) in the DCM (2 mL) was added DMP (80.0 mg, 188 umol). The mixture was stirred at 25° C. for 1 hr. On completion, the reaction mixture was quenched with saturated $Na_2S_2O_3$ (aq, 5 mL) and $NaHCO_3$ (aq, 5 mL). The mixture was then extracted with DCM (2x20 mL). The organic layer was dried over $Na_2SO_4$, filtered and concentrated in vacuo to give the title compound (72 mg, 96% yield) as yellow solid. LC-MS ($ESI^+$) m/z 476.1 $(M+H)^+$.

N-(2-((1r,4r)-4-formylcyclohexyl)-6-methoxy-2H-indazol-5-yl)-4-(trifluoromethyl) pyrimidine-5-carboxamide (Intermediate BLP)

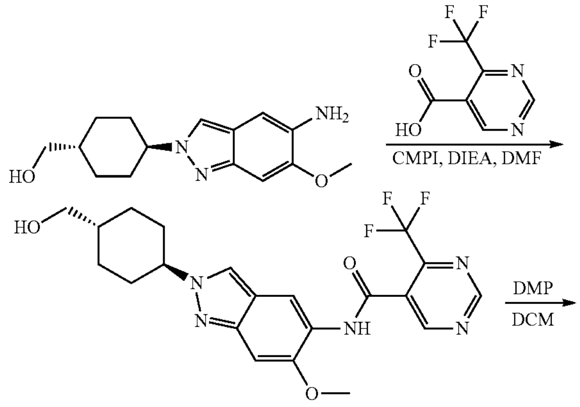

-continued

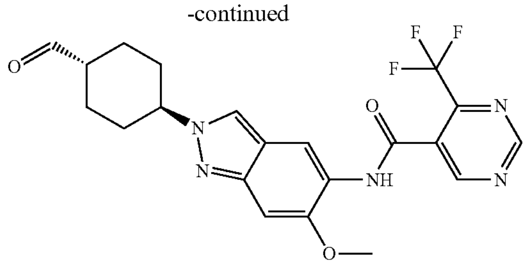

BLP

Step 1—N-(2-((1r,4r)-4-(hydroxymethyl)cyclohexyl)-6-methoxy-2H-indazol-5-yl)-4-(trifluoromethyl) pyrimidine-5-carboxamide To a solution of [4-(5-amino-6-methoxy-indazol-2-yl)cyclohexyl]methanol (120 mg, 385 umol, HCl salt, Intermediate ATE) and 4-(trifluoromethyl)pyrimidine-5-carboxylic acid (73.9 mg, 385 umol, CAS #220880-12-6) in the DMF (2.0 mL) was added CMPI (118 mg, 462 umol) and DIEA (149 mg, 1.15 mmol). The mixture was stirred at 25° C. for 1 hour. On completion, the mixture was diluted with EA (30 mL) and washed with water (3x30 mL). The organic layer was dried over $Na_2SO_4$, filtered and concentrated in vacuo to give the title compound (80 mg, 46% yield) as yellow solid. $^1H$ NMR (400 MHz, $CDCl_3$) δ 9.47 (s, 1H), 9.19 (s, 1H), 8.74 (s, 1H), 8.33 (s, 1H), 7.90 (s, 1H), 7.08 (s, 1H), 4.39-4.30 (m, 1H), 3.94 (s, 3H), 3.57 (d, J=6.2 Hz, 2H), 2.34 (d, J=12.2 Hz, 2H), 2.10-1.92 (m, 5H), 1.72-1.58 (m, 1H), 1.33-1.20 (m, 3H).

Step 2—N-(2-((1r,4r)-4-formylcyclohexyl)-6-methoxy-2H-indazol-5-yl)-4-(trifluoromethyl) pyrimidine-5-carboxamide To a solution of N-[2-[4-(hydroxymethyl)cyclohexyl]-6-methoxy-indazol-5-yl]-4-(trifluoromethyl) pyrimidine-5-carboxamide (80 mg, 178 umol) in the DCM (1.0 mL) was added DMP (90.6 mg, 214 umol). The mixture was stirred at 25° C. for 1 hour. On completion, the reaction mixture was quenched with saturated $Na_2S_2O_3$ (aq, 5.0 mL) and $NaHCO_3$ (aq, 5.0 mL), then the mixture was extracted with DCM (2x20 mL). The organic layer was dried over $Na_2SO_4$, filtered and concentrated in vacuo to give the title compound (79 mg, 99% yield) as yellow solid. LC-MS ($ESI^+$) m/z 448.2 $(M+H)^+$.

N-[2-(4-formylcyclohexyl)-6-(1-hydroxy-1-methyl-ethyl)indazol-5-yl]-2-(trifluoromethyl) pyrimidine-5-carboxamide (Intermediate BLQ)

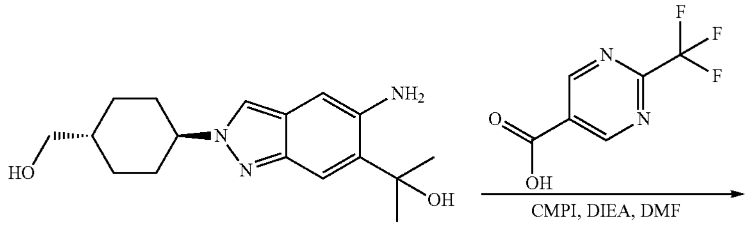

AOX

-continued

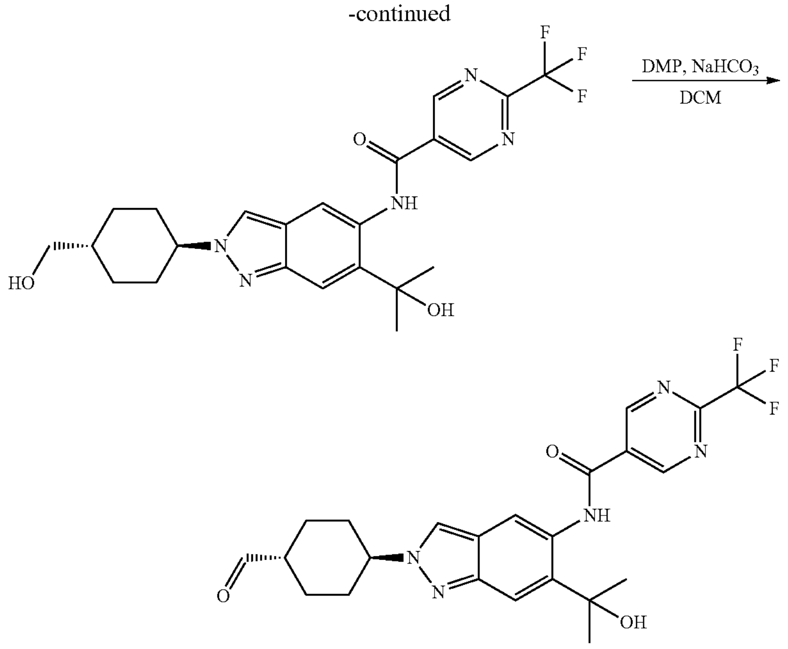

BLQ

Step 1—N-[2-[4-(hydroxymethyl)cyclohexyl]-6-(1-hydroxy-1-methyl-ethyl)indazol-5-yl]-2- (trifluoromethyl)pyrimidine-5-carboxamide To a solution of 2-[5-amino-2-[4-(hydroxymethyl)cyclohexyl]indazol-6-yl]propan-2-ol (78.9 mg, 260 umol, Intermediate AOX) and 2-(trifluoromethyl)pyrimidine-5-carboxylic acid (50.0 mg, 260 umol, CAS #306960-74-7) in DMF (1 mL) was added CMPI (79.8 mg, 312 umol) and DIEA (101 mg, 780 umol, 136 uL). The mixture was stirred at 20° C. for 1 hr. On completion, the reaction mixture was concentrated in vacuo to give the residue. The residue was purified by reversed phase (0.1% FA condition) to give the compound (65.0 mg, 52% yield) as a yellow solid. $^1$H NMR (400 MHz, DMSO-$d_6$) δ 12.26-11.63 (m, 1H), 9.43 (s, 2H), 8.64 (s, 1H), 8.40 (s, 1H), 7.62 (s, 1H), 6.64 (d, J=0.8 Hz, 1H), 4.50 (t, J=5.2 Hz, 1H), 4.47-4.36 (m, 1H), 3.31-3.27 (m, 2H), 2.14 (d, J=9.6 Hz, 2H), 1.97-1.84 (m, 4H), 1.66 (s, 6H), 1.50-1.46 (m, 1H), 1.22-1.08 (m, 2H). LC-MS (ESI$^+$) m/z 478.2 (M+H)$^+$.

Step 2—N-[2-(4-formylcyclohexyl)-6-(1-hydroxy-1-methyl-ethyl)indazol-5-yl]-2-(trifluoromethyl) pyrimidine-5-carboxamide To a solution of N-[2-[4-(hydroxymethyl)cyclohexyl]-6-(1-hydroxy-1-methyl-ethyl)indazol-5-yl]-2-(trifluoromethyl)pyrimidine-5-carboxamide (65.0 mg, 136 umol) in DCM (6.00 mL) was added DMP (69.3 mg, 163.4 umol) and $NaHCO_3$ (34.3 mg, 408 umol) at 0° C. The mixture was stirred at 20° C. for 16 hrs. On completion, the reaction mixture was quenched by addition saturated solution of $Na_2S_2O_3$ (1 mL), and saturated solution of $NaHCO_3$ (2 mL), then extracted with DCM (3×20 mL). The combined organic layer was washed with brine (2×50 mL), dried over anhydrous $Na_2SO_4$, filtered and concentrated in vacuo to give the title compound (60.0 mg, 92% yield) as a yellow solid. $^1$H NMR (400 MHz, DMSO-$d_6$) δ 11.97 (s, 1H), 9.64 (s, 1H), 9.43 (s, 2H), 8.64 (s, 1H), 8.40 (s, 1H), 7.62 (s, 1H), 6.64 (s, 1H), 4.49-4.42 (m, 1H), 2.44-2.37 (m, 1H), 2.24-2.16 (m, 2H), 2.15-2.06 (m, 2H), 2.03-1.93 (m, 2H), 1.66 (s, 6H), 1.52-1.40 (m, 2H).

5-Fluoro-N-[2-(4-formylcyclohexyl)-6-methoxy-indazol-5-yl]pyridine-2-carboxamide (Intermediate BLR)

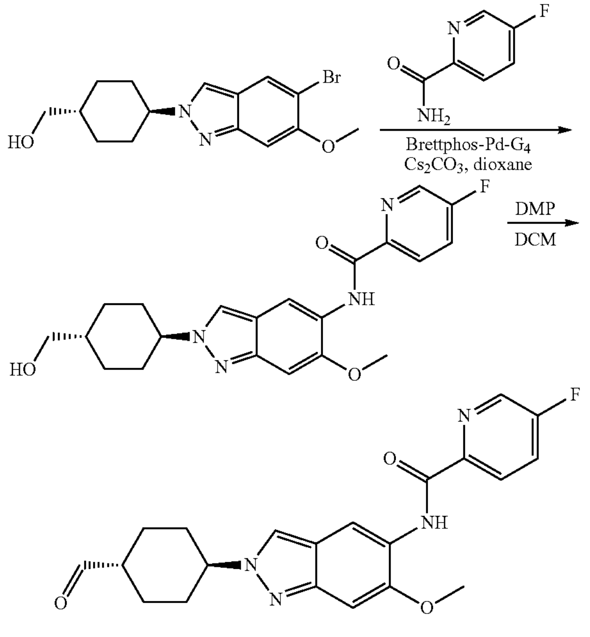

BLR

Step 1—5-Fluoro-N-[2-[4-(hydroxymethyl)cyclohexyl]-6-methoxy-indazol-5-yl]pyridine-2- carboxamide To a solution of 5-fluoropyridine-2-carboxamide (80.0 mg, 570 umol, CAS #499796-71-3), [4-(5-bromo-6-methoxy-indazol-2-yl)cyclohexyl]methanol (203 mg, 599 umol, synthesized via Steps 1-3 of Intermediate ATE) in dioxane (15 mL) was added BrettPhos (Pd, G4) (52.5 mg, 57.1 umol), and $Cs_2CO_3$ (372 mg, 1.14 mmol) under $N_2$. The reaction mixture was stirred at 85° C. for 26 hours. On completion, the reaction mixture was filtered and the filter cake was washed with DCM (3×20 mL), then the filtrate was concentrated in vacuo. The crude product was purified by reverse phase flash (0.1% FA condition) to give the title compound (140 mg, 61% yield) as a light yellow solid. LCMS (ESI+) m/z 399.2 $(M+H)^+$. $^1H$ NMR (400 MHz, DMSO-$d_6$) δ 10.41 (s, 1H), 8.78 (s, 1H), 8.69 (s, 1H), 8.32 (s, 1H), 8.28 (dd, J=4.4, 8.4 Hz, 1H), 8.06-7.96 (m, 1H), 7.16 (s, 1H), 4.49 (t, J=5.2 Hz, 1H), 4.42-4.30 (m, 1H), 3.99 (s, 3H), 3.31-3.27 (m, 2H), 2.14-2.13 (m, 2H), 1.98-1.81 (m, 4H), 1.56-1.42 (m, 1H), 1.24-1.07 (m, 2H).

Step 2—5-Fluoro-N-[2-(4-formylcyclohexyl)-6-methoxy-indazol-5-yl]pyridine-2-carboxamide A mixture of 5-fluoro-N-[2-[4-(hydroxymethyl)cyclohexyl]-6-methoxy-indazol-5-yl]pyridine-2- carboxamide (130 mg, 326 umol) in DCM (15 mL) was added DMP (179 mg, 424 umol) at 0° C. The mixture was stirred at 25° C. for 5 hours under $N_2$ atmosphere. On completion, the reaction mixture was quenched by water (10 mL) and $NaHCO_3$ aqueous was added until the pH=7. The mixture was then extracted with DCM (3×10 mL), dried over $Na_2SO_4$, filtered and concentrated in vacuo to give the title compound (110 mg, 85% yield) as a light yellow solid. LCMS (ESI+) m/z 397.2 $(M+H)^+$. $^1H$ NMR (400 MHz, DMSO-$d_6$) δ 10.41 (s, 1H), 9.65 (s, 1H), 8.78 (d, J=2.8 Hz, 1H), 8.70 (s, 1H), 8.33 (s, 1H), 8.28 (dd, J=4.8, 8.8 Hz, 1H), 8.11-8.05 (m, 1H), 7.16 (s, 1H), 4.45-4.33 (m, 1H), 3.99 (s, 3H), 2.47-2.38 (m, 1H), 2.24-2.16 (m, 2H), 2.15-2.07 (m, 2H), 2.04-1.90 (m, 2H), 1.54-1.38 (m, 2H).

2,3-dichloro-N-(2-((1r,4r)-4-formylcyclohexyl)-6-(2-hydroxypropan-2-yl)-2H -indazol-5-yl)benzamide (Intermediate BLS)

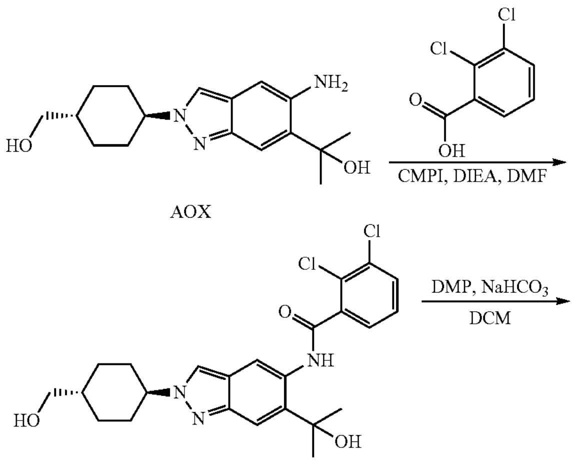

-continued

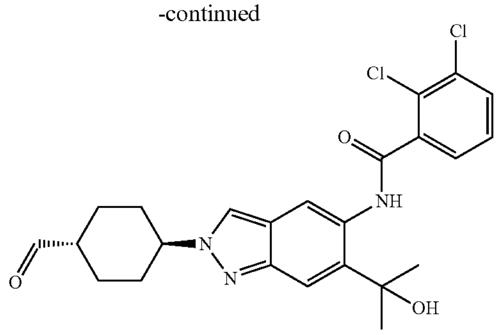

BLS

Step 1—2,3-dichloro-N-(2-((1r,4r)-4-(hydroxymethyl)cyclohexyl)-6-(2-hydroxypropan-2-yl)-2H- indazol-5-yl)benzamide To a solution of 2-[5-amino-2-[4-(hydroxymethyl)cyclohexyl]indazol-6-yl]propan-2-ol (150 mg, 494 umol, Intermediate AOX) and 2,3-dichlorobenzoic acid (94.4 mg, 494 umol, CAS #50-45-3) in DMF (1.5 mL) was added DIEA (191 mg, 1.48 mmol) and CMPI (126 mg, 494 umol). The mixture was stirred at 25° C. for 0.5 hour. On completion, the reaction mixture was partitioned between DCM (100 mL) and $H_2O$ (50 mL). The organic phase was separated, washed with brine (50 mL), dried over $Na_2SO_4$, filtered and concentrated in vacuo to give a residue. The residue was purified by column chromatography ($SiO_2$, DCM/MeOH=100/1 to 10/1) to give the title compound (230 mg, 97% yield) as a white solid. $^1H$ NMR (400 MHz, DMSO-$d_6$) δ 11.11 (s, 1H), 8.57 (s, 1H), 8.36 (s, 1H), 7.78 (dd, J=1.6, 8.0 Hz, 1H), 7.62-7.58 (m, 1H), 7.55 (s, 1H), 7.53-7.48 (m, 1H), 6.19 (s, 1H), 4.48 (t, J=5.4 Hz, 1H), 4.45-4.35 (m, 1H), 3.28 (t, J=5.8 Hz, 2H), 2.13 (m, 2H), 1.95-1.82 (m, 4H), 1.58 (s, 6H), 1.47 (m, 1H), 1.15 (m, 2H); LC-MS $(ESI^+)$ m/z 476.1 $(M+H)^+$.

Step 2—2,3-dichloro-N-(2-((1r,4r)-4-formylcyclohexyl)-6-(2-hydroxypropan-2-yl)-2H -indazol- 5-yl) benzamide To a solution of 2,3-dichloro-N-[2-[4-(hydroxymethyl) cyclohexyl]-6-(1-hydroxy-1-methyl-ethyl) indazol-5-yl] benzamide (50.0 mg, 104 umol) in DCM (1.0 mL) was added DMP (66.7 mg, 157 umol). The mixture was stirred at 25° C. for 0.5 hour. On completion, the reaction mixture was quenched with sat. $NaHSO_3$ (30 mL) and sat. $NaHCO_3$ (30 mL) at 0° C., and then diluted with $H_2O$ (50 mL) and extracted with DCM (3×50 mL). The combined organic layers were washed with brine (3×50 mL), dried over $Na_2SO_4$, filtered and concentrated under reduced pressure to give a residue. The residue was purified by column chromatography ($SiO_2$, petroleum ether/ethyl acetate=100/1 to 3/1) to give the title compound (49.0 mg, 99% yield) as a white solid $^1H$ NMR (400 MHz, $CDCl_3$) δ 10.41 (s, 1H), 9.73 (s, 1H), 8.78 (s, 1H), 7.93 (s, 1H), 7.68 (s, 1H), 7.56 (dd, J=1.4, 8.0 Hz, 1H), 7.50 (dd, J=1.5, 7.7 Hz, 1H), 7.30 (t, J=8.0 Hz, 1H), 4.38 (tt, J=3.8, 11.9 Hz, 1H), 2.47-2.34 (m, 3H), 2.30-2.19 (m, 2H), 2.14-2.01 (m, 2H), 1.76 (s, 6H), 1.63-1.46 (m, 2H); LC-MS $(ESI^+)$ m/z 474.2 $(M+H)^+$.

5-Fluoro-N-[2-(4-formylcyclohexyl)-6-(1-hydroxy-1-methyl-ethyl)indazol-5-yl]pyridine-2- carboxamide (Intermediate BLT)

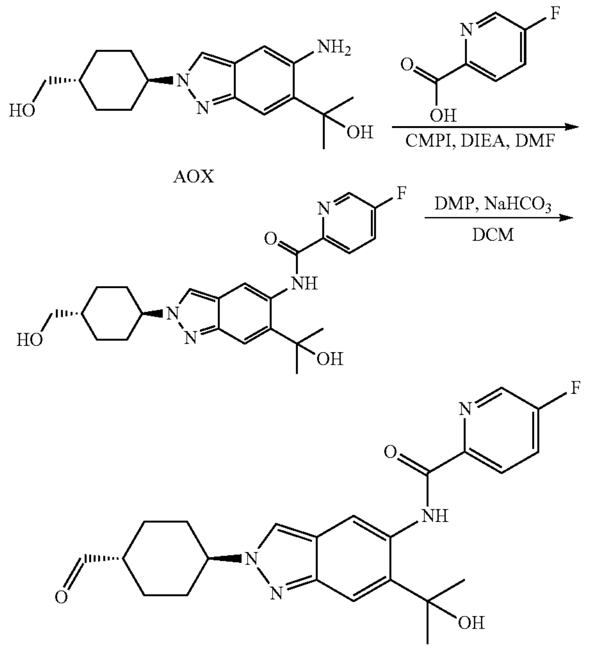

AOX

BLT

Step 1—5-Fluoro-N-[2-[4-(hydroxymethyl)cyclohexyl]-6-(1-hydroxy-1-methyl-ethyl)indazol-5-yl] pyridine-2-carboxamide To a mixture of 5-fluoropyridine-2-carboxylic acid (100 mg, 708 umol, CAS #107504-08-5) and CMPI (235 mg, 921 umol) in DMF (5 mL) was added DIEA (274 mg, 2.13 mmol). The mixture was stirred at 25° C. for 0.5 hr. Then a solution of 2-[5-amino-2-[4-(hydroxymethyl)cyclohexyl]indazol-6-yl]propan-2-ol (215 mg, 708 umol, Intermediate AOX) in DMF (1 mL) was added to the mixture. The reaction mixture was stirred at 25° C. for 15.5 hrs. On completion, the reaction mixture was concentrated in vacuo. The crude product was purified by reversed-phase HPLC (0.1% FA condition) to give the title compound (330 mg, 99% yield) as yellow solid. $^1$H NMR (400 MHz, $CDCl_3$) δ 12.25 (s, 1H), 8.68 (d, J=2.8 Hz, 1H), 8.65 (s, 1H), 8.35 (s, 1H), 8.27 (dd, J=4.8, 8.8 Hz, 1H), 7.97 (dt, J=2.8, 8.8 Hz, 1H), 7.55 (s, 1H), 6.07 (s, 1H), 4.52 (t, J=5.2 Hz, 1H), 4.46-4.35 (m, 1H), 3.29 (t, J=5.6 Hz, 2H), 2.18-2.09 (m, 2H), 1.96-1.83 (m, 4H), 1.61 (s, 6H), 1.53-1.42 (m, 1H), 1.20-1.13 (m, 2H).

Step 2—5-Fluoro-N-[2-(4-formylcyclohexyl)-6-(1-hydroxy-1-methyl-ethyl)indazol-5-yl]pyridine-2-carboxamide To a mixture of 5-fluoro-N-[2-[4-(hydroxymethyl)cyclohexyl]-6-(1-hydroxy-1-methyl-ethyl)indazol -5-yl]pyridine-2-carboxamide (280 mg, 656 umol) and $NaHCO_3$ (275 mg, 3.28 mmol) in DCM (10 mL) was added DMP (417 mg, 984 umol) at 0° C. The reaction mixture was stirred at 25° C. for 2 hrs. On completion, the reaction mixture was diluted with saturated $Na_2S_2O_3$ aqueous (10 mL) and saturated $NaHCO_3$ aqueous (10 mL). The mixture was stirred at 20° C. for 0.5 hr, then the mixture was diluted with water (100 mL) and extracted with DCM (3×50 mL). The organic layer was washed with saturated $NaHCO_3$ aqueous (2×100 mL) and brine (2×100 mL). The organic layer was dried over anhydrous sodium sulfate and filtered, then the filtrate was concentrated in vacuo. The crude product was purified by silica gel chromatography (PE:EA=1:0 to 1:1) and Prep-TLC (PE:EA=0:1) to give the title compound (70.0 mg, 25% yield) as yellow solid. $^1$H NMR (400 MHz, DMSO-$d_6$) δ 12.26 (s, 1H), 9.65 (s, 1H), 8.69 (d, J=2.8 Hz, 1H), 8.66 (s, 1H), 8.35 (s, 1H), 8.27 (dd, J=4.8, 8.8 Hz, 1H), 7.97 (dt, J=2.8, 8.8 Hz, 1H), 7.56 (s, 1H), 6.06 (s, 1H), 4.45 (tt, J=3.6, 11.6 Hz, 1H), 2.45-2.38 (m, 1H), 2.25-2.17 (m, 2H), 2.15-2.08 (m, 2H), 2.03-1.93 (m, 2H), 1.61 (s, 6H), 1.51-1.39 (m, 2H).

N-(2-((1r,4r)-4-formylcyclohexyl)-6-(2-hydroxypropan-2-yl)-2H-indazol-5-yl)thiazole-2- carboxamide (Intermediate BLU)

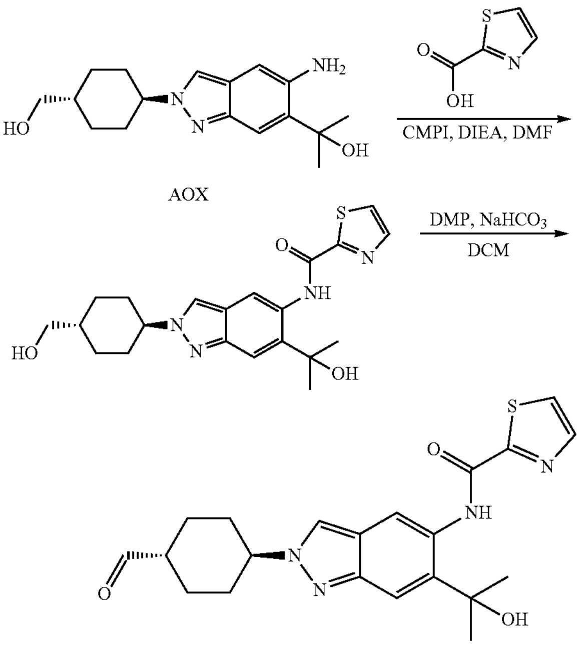

AOX

BLU

Step 1—N-(2-((1r,4r)-4-(Hydroxymethyl)cyclohexyl)-6-(2-hydroxypropan-2-yl)-2H-indazol-5-yl) thiazole-2-carboxamide To a solution of 2-[5-amino-2-[4-(hydroxymethyl)cyclohexyl]indazol-6-yl]propan-2-ol (150 mg, 494 umol, Intermediate AOX) and thiazole-2-carboxylic acid (63.8 mg, 494 umol, CAS #14190-59-1) in DMF (1.5 mL) was added CMPI (126 mg, 494 umol) and DIEA (191 mg, 1.48 mmol). The mixture was stirred at 25° C. for 0.5 hour. On completion, the reaction mixture was partitioned between DCM (100 mL) and $H_2O$ (100 mL). The organic phase was separated, washed with brine (3×50 mL), dried over $Na_2SO_4$, filtered and concentrated in vacuo to give a residue. The residue was purified by prep-TLC ($SiO_2$, DCM: MeOH=20:1) to give the title compound (190 mg, 91% yield) as an off-white solid. 1H NMR (400 MHz, CDCl3) δ 11.67 (s, 1H), 8.73 (s, 1H), 7.96 (d, J=3.2 Hz, 1H), 7.90 (s, 1H), 7.69 (s, 1H), 7.58 (d, J=3.2 Hz, 1H), 4.34 (tt, J=3.6, 11.8 Hz, 1H), 3.54 (d, J=6.2 Hz, 2H), 2.34-2.25 (m, 2H), 2.06-1.88 (m, 4H), 1.80 (s, 6H), 1.68-1.57 (m, 2H), 1.27-1.14 (m, 2H); LC-MS (ESI+) m/z 415.2 $(M+H)^+$.

Step 2—N-(2-((1r,4r)-4-formylcyclohexyl)-6-(2-hydroxypropan-2-yl)-2H-indazol-5-yl)thiazole-2-carboxamide To a solution of N-[2-[4-(hydroxymethyl)cyclohexyl]-6-(1-hydroxy-1-methyl-ethyl)indazol-5-yl]thiazole-2-carboxamide (116 mg, 279 umol) in DCM (3.0 mL) was added DMP (178 mg, 419 umol). The mixture was stirred at 25° C. for 0.5 hour. On completion, the reaction mixture was quenched with sat. $NaHSO_3$ (20 mL) and sat. $NaHCO_3$ (20 mL) at 0° C., and then diluted with $H_2O$ (20 mL) and extracted with DCM (3×50 mL). The combined organic layers were washed with brine (3×50 mL), dried over $Na_2SO_4$, filtered and concentrated in vacuo to give the title compound (115 mg, 99% yield) as an off-white solid. 1H NMR (400 MHz, CDCl3) δ 11.64 (s, 1H), 9.73 (d, J=0.6 Hz, 1H), 8.76 (s, 1H), 7.98 (d, J=3.2 Hz, 1H), 7.92 (s, 1H), 7.71 (s, 1H), 7.60 (d, J=3.2 Hz, 1H), 4.37 (tt, J=3.8, 11.9 Hz, 1H), 2.52-2.35 (m, 3H), 2.30-2.21 (m, 2H), 2.14-2.00 (m, 2H), 1.81 (s, 6H), 1.68-1.44 (m, 2H); LC-MS (ESI+) m/z 413.2 $(M+H)^+$.

3,4-Dichloro-N-[2-(4-formylcyclohexyl)-6-(1-hydroxy-1-methyl-ethyl)indazol-5-yl]benzamide (Intermediate BLV)

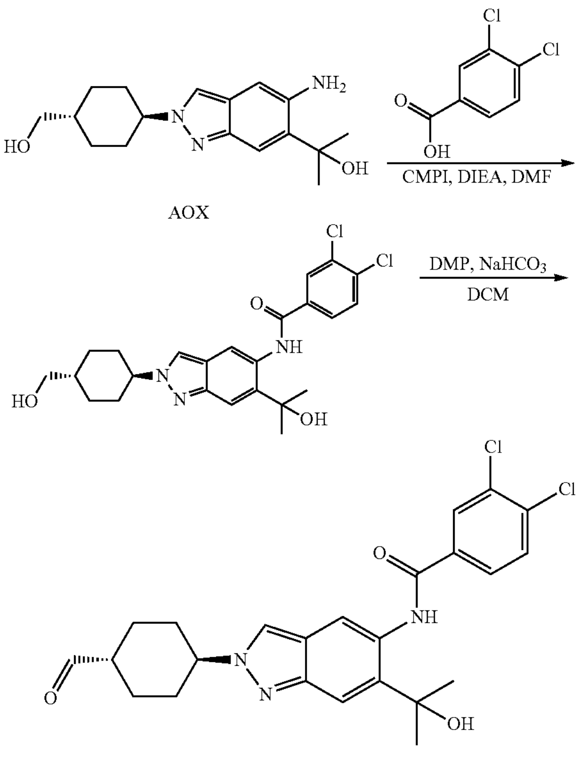

AOX

BLV

Step 1—3,4-Dichloro-N-[2-[4-(hydroxymethyl)cyclohexyl]-6-(1-hydroxy-1-methyl-ethyl)indazol-5-yl]benzamide To a solution of 2-[5-amino-2-[4-(hydroxymethyl)cyclohexyl]indazol-6-yl]propan-2-ol (180 mg, 593 umol, Intermediate AOX) in DMF (3 mL) was added 3,4-dichlorobenzoic acid (113 mg, 593 umol, CAS #51-44-5) and CMPI (181 mg, 711 umol). The reaction mixture was stirred at 25° C. for 15 min. Then DIEA (1.78 mmol, 310.02 uL) was added and the reaction mixture was stirred at 25° C. for 4 hours. On completion, the mixture was concentrated in vacuo to give a residue. The crude product was triturated with $H_2O$ (10 mL) at 25° C. for 15 min to give the title compound (120 mg, 42% yield) as a yellow solid. LCMS $(ESI^+)$ m/z 476.3 $(M+H)^+$. $^1H$ NMR (400 MHz, DMSO-$d_6$) δ 11.73 (s, 1H), 8.64 (s, 1H), 8.36 (s, 1H), 8.11-8.04 (m, 1H), 7.87 (s, 1H), 7.62-7.57 (m, 1H), 6.76-6.48 (m, 1H), 4.45-4.36 (m, 1H), 2.89 (s, 1H), 2.73 (s, 1H), 2.19-2.08 (m, 2H), 2.00-1.83 (m, 5H), 1.65 (s, 6H), 1.47 (d, J=9.2 Hz, 1H), 1.24-1.06 (m, 3H).

Step 2—3,4-Dichloro-N-[2-(4-formylcyclohexyl)-6-(1-hydroxy-1-methyl-ethyl)indazol-5- yl]benzamide To a solution of 3,4-dichloro-N-[2-[4-(hydroxymethyl) cyclohexyl]-6-(1-hydroxy-1-methyl-ethyl) indazol-5-yl] benzamide (120 mg, 251 umol) in DCM (2 mL) was added DMP (128 mg, 302 umol). The reaction mixture was stirred at 25° C. for 2 hours. On completion, the mixture was quenched with $Na_2S_2O_3$ (2 mL) and extracted with ethyl acetate (3×25 mL). Then the combined organic layers were dried over anhydrous sodium sulfate, filtered and concentrated in vacuo to give the title compound (115 mg, 96% yield) as a off-white solid. LCMS (ESI+) m/z 474.1 $(M+H)^+$.

Imidazo[1,5-a]pyrimidine-8-carboxylic acid (Intermediate BLW)

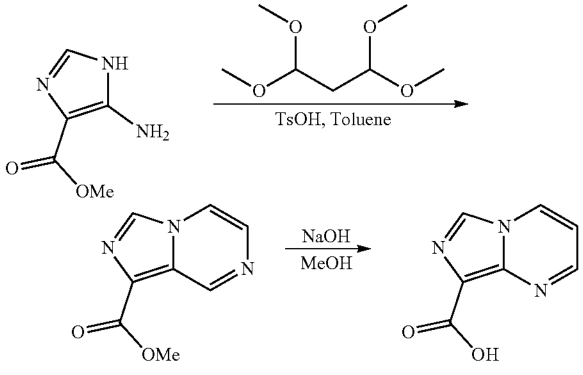

BLW

Step 1—Methyl imidazo[1,5-a]pyrimidine-8-carboxylate

To a solution of methyl 5-amino-1H-imidazole-4-carboxylate (500 mg, 3.54 mmol) (CAS #: 4919-00-0), 1,1,3,3-tetramethoxypropane (697 mg, 4.25 mmol) in toluene (30 mL) was added TsOH (61.0 mg, 354 umol). The mixture was heated to 110° C. and remove ethanol by Dean-Stark trap for 4 days. After that, 1,1,3,3-tetramethoxypropane (581 mg, 3.54 mmol) was charged into the reaction mixture and stirred for 2 days. On completion, the reaction mixture was concentrated in vacuo. The residue was purified by silica gel chromatography (DCM:MeOH=40:1) to give the title compound (180 mg, 28% yield) as a yellow solid. $^1$H NMR (400 MHz, DMSO-$d_6$) δ 8.90 (dd, J=1.6, 7.2 Hz, 1H), 8.58 (dd, J=1.6, 3.6 Hz, 1H), 8.43 (s, 1H), 7.04 (dd, J=3.6, 7.2 Hz, 1H), 3.82 (s, 3H), LC-MS (ESI$^+$) m/z 200.1 (M+Na)$^+$.

Step 2—Imidazo[1,5-a]pyrimidine-8-carboxylic acid

To a solution of methyl imidazo[1,5-a]pyrimidine-8-carboxylate (186 mg, 1.05 mmol) in MeOH (5 mL) was added a aqueous NaOH (1 M, 2.50 mL). The reaction mixture was stirred at 50° C. for 12 hrs. On completion, the reaction mixture was acidified with HCl (1N) 2.5 mL and concentrated in vacuo to remove methanol, and then the residue was concentrated further in vacuo to give the title compound (170 mg, 99% yield). $^1$H NMR (400 MHz, DMSO-$d_6$) δ 8.89 (dd, J=1.6, 7.2 Hz, 1H), 8.50 (dd, J=1.6, 3.6 Hz, 1H), 8.40 (s, 1H), 6.98 (dd, J=3.6, 7.2 Hz, 1H), LC-MS (ESI$^+$) m/z 146.1 (M-OH)$^+$ N-[2-(4-formylcyclohexyl)-6-(1-hydroxy-1-methyl-ethyl)indazol-5-yl]imidazo[1,5-a] pyrimidine-8-carboxamide (Intermediate BLX)

Step 1—N-[2-[4-(hydroxymethyl)cyclohexyl]-6-(1-hydroxy-1-methyl-ethyl)indazol-5-yl]imidazo [1,5-a]pyrimidine-8-carboxamide To a solution of imidazo[1,5-a]pyrimidine-8-carboxylic acid (80 mg, 490 umol, Intermediate BLW) and 2-[5-amino-2-[4-(hydroxymethyl)cyclohexyl]indazol-6-yl]propan-2-ol (148 mg, 490 umol, Intermediate AOX) in DMF (3 mL) was added DIEA (127 mg, 980 umol) and CMPI (150 mg, 588 umol). The reaction mixture was stirred at 20° C. for 1 hr. On completion, the reaction mixture was quenched with water (0.5 mL), then the residue was concentrated in vacuo. The crude product was purified by reversed phase flash (0.1% FA condition) to give impure product. The impure product was re-purified by Prep-HPLC (column: Shim-pack C18 150*25*10 um;mobile phase: [water(0.225% FA)-ACN];B %: 18%-38%, 10 min) to give the title compound (10.0 mg, 4.5% yield) as a yellow solid. $^1$H NMR (400 MHz, DMSO-$d_6$) δ 11.62 (s, 1H), 8.87 (dd, J=1.6, 7.2 Hz, 1H), 8.59 (s, 1H), 8.53 (dd, J=1.6, 3.6 Hz, 1H), 8.45 (s, 1H), 8.33 (s, 1H), 7.54 (s, 1H), 7.02-6.98 (m, 1H), 5.93 (s, 1H), 4.40-4.39 (m, 1H), 3.30-3.28 (m, 2H), 2.15-2.11 (m, 2H), 1.93-1.89 (m, 4H), 1.63 (s, 6H), 1.56-1.43 (m, 2H), 1.19-1.14 (m, 2H). LC-MS (ESI$^+$) m/z 431.2 (M-OH)$^+$.

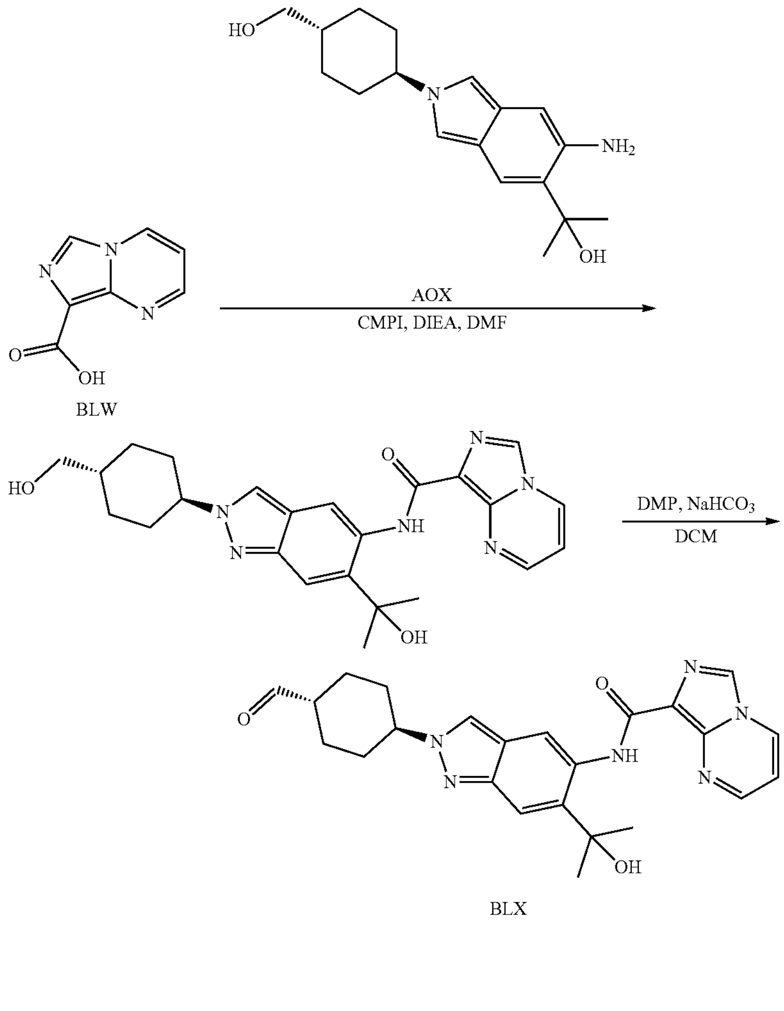

BLW

BLX

Step 2—N-[2-(4-formylcyclohexyl)-6-(1-hydroxy-1-methyl-ethyl)indazol-5-yl]imidazo[1,5-a] pyrimidine-8-carboxamide To a solution of N-[2-[4-(hydroxymethyl)cyclohexyl]-6-(1-hydroxy-1-methyl-ethyl)indazol-5-yl]imidazo[1,5-a]pyrimidine-8-carboxamide (10 mg, 22.3 umol) in DCM (8 mL) was added $NaHCO_3$ (6.74 mg, 80.2 umol) and DMP (11.3 mg, 26.7 umol). The reaction mixture was stirred at 20° C. for 12 hrs. On completion, the reaction mixture was quenched with saturated $Na_2S_2O_3$ (2 mL), and extracted with DCM (30 mL×3). The combined organic layers were washed with saturated $NaHCO_3$ (10 mL), dried over anhydrous sodium sulfate, filtered and concentrated in vacuo. The residue was purified by reversed phase flash (0.1% FA condition) to give the title compound (9.9 mg, 99% yield) as a yellow solid. LC-MS ($ESI^+$) m/z 429.2 $(M-OH)^+$.

4-Chloro-1-methyl-pyrazole-3-carboxylic acid (Intermediate BLY)

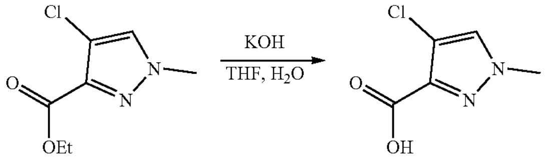

BLY

To a mixture of ethyl 4-chloro-1-methyl-pyrazole-3-carboxylate (200 mg, 1.06 mmol, CAS #942853-19-2) in THF (10 mL) was added a solution of KOH (118 mg, 2.12 mmol) in $H_2O$ (5 mL) at 40° C. and the reaction mixture was stirred at 40° C. for 16 hrs. On completion, the reaction mixture was concentrated in vacuo. The mixture was diluted with water (100 mL) and extracted with EA (3×30 mL). The organic layer was discarded. The aqueous phase was acidified with 1N HCl until the pH=3. The mixture was extracted with EA (3×50 mL), then the organic layer was washed with brine (3×50 mL). The organic layer was dried over anhydrous sodium sulfate and filtered. The filtrated was concentrated in vacuo to give the title compound (140 mg, 82% yield) as white solid. $^1H$ NMR (400 MHz, DMSO-$d_6$) δ 13.47-12.40 (m, 1H), 8.06 (s, 1H), 3.87 (s, 3H)

Tert-butyl N-[2-(4-formylcyclohexyl)-6-(1-hydroxy-1-methyl-ethyl)indazol-5-yl]carbamate (Intermediate BLZ)

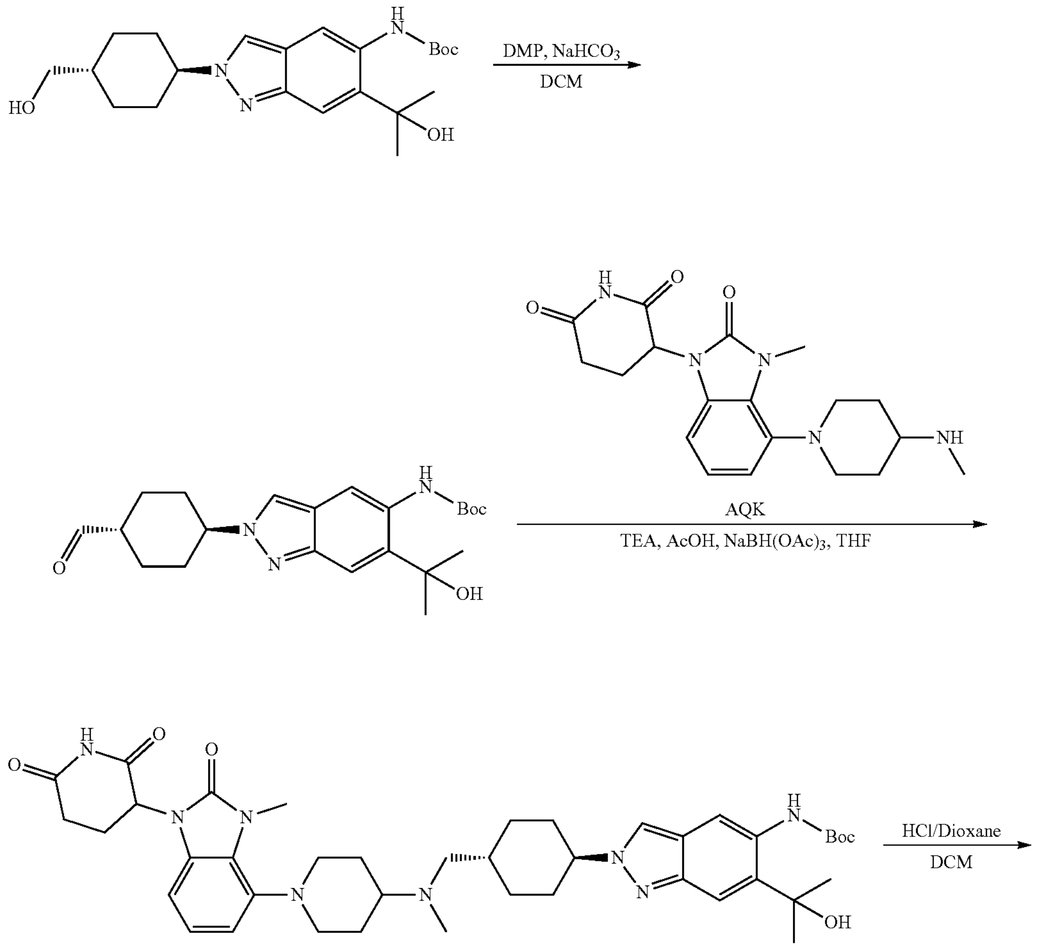

-continued

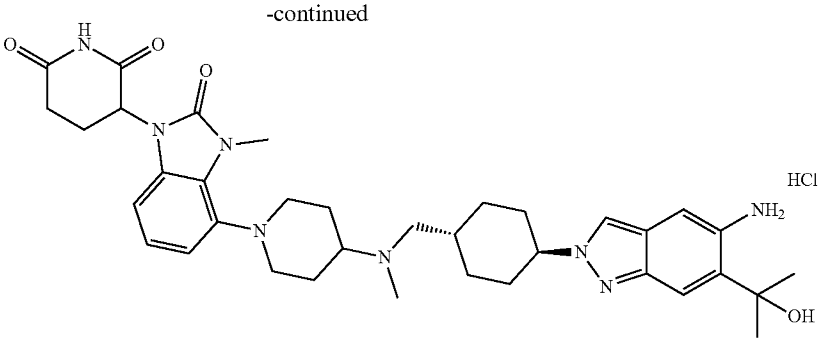

BLZ

Step 1—Tert-butyl N-[2-(4-formylcyclohexyl)-6-(1-hydroxy-1-methyl-ethyl)indazol-5-yl]carbamate To a solution of tert-butyl N-[2-[4-(hydroxymethyl)cyclohexyl]-6-(1-hydroxy-1-methyl-ethyl) indazol-5-yl]carbamate (2.00 g, 4.96 mmol, synthesized via Step 1 of Intermediate BIN) in THE (100 mL) was added $NaHCO_3$ (1.67 g, 19.8 mmol) and DMP (2.73 g, 6.44 mmol, 1.99 mL). The reaction mixture was stirred at 25° C. for 1.5 hours. On completion, the reaction mixture was diluted with EA (500 mL) and washed with sat. $Na_2SO_3$ (50 mL) and brine (2×40 mL). The organic layer was concentrated in vacuo and the residue was purified by reversed phase flash (0.1% FA) to give the title compound (1.00 g, 50% yield) as a yellow solid. $^1H$ NMR (400 MHz, $CDCl_3$) δ 9.71 (s, 1H), 8.95 (s, 1H), 8.22 (s, 1H), 7.61 (s, 1H), 7.64 (s, 1H), 4.38-4.30 (m, 1H), 2.43-2.37 (m, 3H), 2.34-2.23 (m, 2H), 2.07-2.03 (m, 2H), 1.75 (s, 6H), 1.54-1.50 (m, 11H).

Step 2—Tert-butyl N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-(1-hydroxy-1-methyl-ethyl)indazol-5-yl]carbamate To a a solution of 3-[3-methyl-4-[4-(methylamino)-1-piperidyl]-2-oxo-benzimidazol-1-yl]piperidine-2,6-dione (406 mg, 996 umol, Intermediate AQK) in THE (25 mL) was added TEA (201 mg, 1.99 mmol). The reaction mixture was stirred at 25° C. for 15 minutes. Then tert-butyl N-[2-(4-formylcyclohexyl)-6-(1-hydroxy-1-methyl-ethyl)indazol-5-yl]carbamate (400 mg, 996 umol) and AcOH (59.8 mg, 996 umol) was added. The reaction mixture was stirred at −10° C. for 15 minutes. Then $NaBH(OAc)_3$ (422 mg, 1.99 mmol) was added in four parts for 1 hour at −10° C. Then the reaction mixture was stirred at −10° C. for 0.5 hour. On completion, the reaction was diluted with EA (300 mL) and washed with water (2×50 mL). The organic layers were concentrated in vacuo. The residue was purified by reversed phase flash (0.1% FA) to give the title compound (250 mg, 33% yield) as a white solid. LCMS (ESI+) m/z 757.5 (M+H)+. $^1H$ NMR (400 MHz, DMSO-$d_6$) δ 11.08 (s, 1H), 9.63 (s, 1H), 8.23 (s, 1H), 8.06 (s, 1H), 7.47 (s, 1H), 6.99-6.86 (m, 3H), 6.04-6.03 (m, 1H), 5.37-5.32 (m, 1H), 4.42-4.38 (m, 1H), 3.64 (s, 3H), 3.14-3.18 (m, 2H), 2.89-2.87 (m, 1H), 2.70-2.66 (m, 4H), 2.36-2.34 (m, 3H), 2.33 (s, 3H), 2.18-2.10 (m, 2H), 1.95-1.80 (m, 8H), 1.70-1.57 (m, 2H), 1.57 (s, 6H), 1.47 (s, 9H), 1.20-1.10 (m, 2H).

Step 3—3-[4-[4-[[4-[5-Amino-6-(1-hydroxy-1-methyl-ethyl)indazol-2-yl]cyclohexyl]methyl-methyl- amino]-1-piperidyl]-3-methyl-2-oxo-benzimidazol-1-yl]piperidine-2,6-dione To a solution of tert-butyl N-[2-[4-[[[1-[1-(2,6-dioxo-3-piperidyl)-3-methyl-2-oxo-benzimidazol-4- yl]-4-piperidyl]-methyl-amino]methyl]cyclohexyl]-6-(1-hydroxy-1-methyl-ethyl)indazol-5-yl]carbamate (60 mg, 79.2 umol) in DCM (8.5 mL) was added HCl/dioxane (4 M, 0.5 mL). The reaction mixture was stirred at −10° C. for 1 hour. On completion, the mixture was concentrated in vacuo to the title compound (50 mg, 90% yield, HCl) as brown oil. LCMS (ESI$^+$) m/z 639.5 (M-18)$^+$.

2-Chloro-N-[2-(4-formylcyclohexyl)-6-(1-hydroxy-1-methyl-ethyl)indazol-5-yl]benzamide (Intermediate BMA)

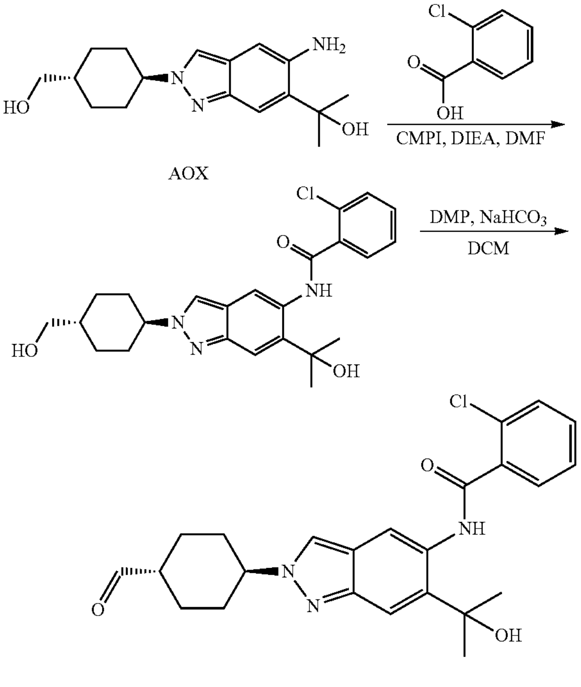

AOX

BMA

Step 1—2-chloro-N-[2-[4-(Hydroxymethyl)cyclohexyl]-6-(1-hydroxy-1-methyl-ethyl)indazol-5-yl]benzamide To a solution of 2-[5-amino-2-[4-(hydroxymethyl)cyclohexyl]indazol-6-yl]propan-2-ol (180 mg, 593 umol, Intermediate AOX) in DMF (3 mL) was added 2-chlorobenzoic acid (92.8 mg, 593 umol, CAS #118-91-2) and CMPI (181 mg, 711 umol). The reaction mixture was stirred at 25° C. for 15 min. Next, DIEA (1.78 mmol, 310 uL) was added and the reaction mixture was stirred at 25° C. for 2 hours. On completion, the mixture was concentrated in vacuo to give a residue. The crude product was purified by reverse phase flash (0.1% FA condition) to give the title compound (120 mg, 45% yield) as a light yellow solid. LCMS (ESI+) m/z 442.2 (M+H)+. $^{1}$H NMR (400 MHz, DMSO-$d_6$) δ 11.08 (s, 1H), 8.61 (s, 1H), 8.37 (s, 1H), 7.65-7.62 (m, 1H), 7.61-7.58 (m, 1H), 7.56 (s, 1H), 7.54-7.48 (m, 2H), 6.20 (s, 1H), 4.54-4.37 (m, 2H), 3.32-3.27 (m, 3H), 2.14 (d, J=8.8 Hz, 2H), 1.97-1.87 (m, 4H), 1.60 (s, 6H), 1.24-1.09 (m, 2H).

Step 2—2-Chloro-N-[2-(4-formylcyclohexyl)-6-(1-hydroxy-1-methyl-ethyl)indazol-5-yl]benzamide To a solution of 2-chloro-N-[2-[4-(hydroxymethyl)cyclohexyl]-6-(1-hydroxy-1-methyl-ethyl)indazol-5-yl]benzamide (120 mg, 271 umol) in DCM (2 mL) was added DMP (352 umol, 109 uL) and $NaHCO_3$ (91.2 mg, 1.09 mmol). The reaction mixture was stirred at 25° C. for 48 hours. On completion, the mixture was quenched with $Na_2S_2O_3$ (0.5 mL) and extracted with ethyl acetate (3×25 mL). The combined organic layers were dried over anhydrous sodium sulfate, filtered and concentrated in vacuo to give the title compound (100 mg, 83% yield) as an off-white solid. LCMS (ESI+) m/z 440.2 $(M+H)^+$.

2-(Trifluoromethyl)imidazo[1,5-a]pyrimidine-8-carboxylic acid (Intermediate BMB)

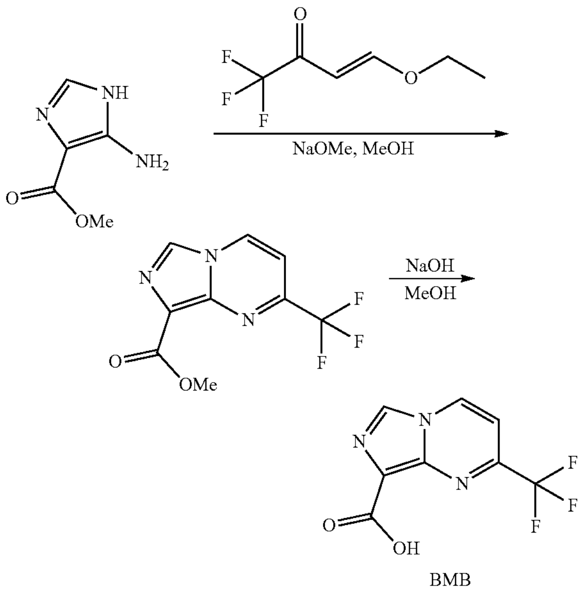

BMB

Step 1—Methyl 2-(trifluoromethyl)imidazo[1,5-a]pyrimidine-8-carboxylate

To a solution of methyl 5-amino-1H-imidazole-4-carboxylate (1 g, 7.09 mmol), 4-ethoxy-1,1,1-trifluoro-but-3-en-2-one (1.19 g, 7.09 mmol) in MeOH (20 mL) was added NaOMe (383 mg, 7.09 mmol), then the mixture was stirred at 25° C. for 1 hr. Next, the mixture was heated to 60° C. for 12 hrs. On completion, the reaction mixture was concentrated in vacuo. The residue was purified by silica gel chromatography (DCM:MeOH=50:1) to give the title compound (800 mg, 46% yield) as a yellow solid. $^{1}$H NMR (400 MHz, DMSO-$d_6$) δ 9.19 (d, J=7.2 Hz, 1H), 8.67 (s, 1H), 7.46 (d, J=7.2 Hz, 1H), 3.87 (s, 3H), LC-MS (ESI$^+$) m/z 246.0 $(M+H)^+$.

Step 2—2-(Trifluoromethyl)imidazo[1,5-a]pyrimidine-8-carboxylic acid

To a solution of methyl 2-(trifluoromethyl)imidazo[1,5-a]pyrimidine-8-carboxylate (300 mg, 1.22 mmol) in MeOH (20 mL) was added an aqueous NaOH (1 M, 1.84 mL). The reaction mixture was stirred at 50° C. for 1 hr. On completion, the reaction mixture was acidified with HCl (1 N) 2.5 mL, then concentrated in vacuo removed to methanol. The crude product was purified by reversed-phase HPLC (0.1% HCl condition) to give the title compound (200 mg, 70% yield). LC-MS (ESI$^+$) m/z 214.0 $(M-OH)^+$.

6-[(1R,4R)-2-oxa-5-azabicyclo[2.2.1]heptan-5-yl]pyridine-2-carboxylic acid (Intermediate BMC)

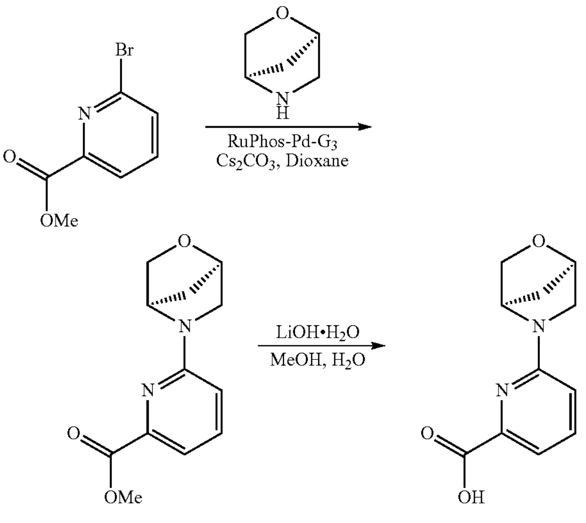

BMC

Step 1—Methyl 6-[(1R,4R)-2-oxa-5-azabicyclo[2.2.1]heptan-5-yl]pyridine-2-carboxylate To a solution of methyl 6-bromopyridine-2-carboxylate (200 mg, 925 umol, CAS #26218-75-7), and (1R,4R)-2-oxa-5-azabicyclo[2.2.1]heptane (91.8 mg, 925 umol, CAS #661470-56-0) in dioxane (8 mL) was added $Cs_2CO_3$ (603 mg, 1.85 mmol), and RuPhos Pd G3 (77.43 mg, 92.6 umol) at 25° C. The mixture was stirred at 80° C. under $N_2$ (15 psi) for 16 hours. On completion, the mixture was filtered and the filter cake was washed with EA (30 mL) and concentrated in vacuo to give the crude product. The crude product was purified by reversed phase flash (0.1% FA condition) to give the title compound (158 mg, 60% yield, FA salt) $^1$H NMR (400 MHz, DMSO-$d_6$) δ 7.65 (dd, J=7.2, 8.4 Hz, 1H), 7.26 (d, J=7.2 Hz, 1H), 6.77 (d, J=8.4 Hz, 1H), 4.91 (s, 1H), 4.66 (s, 1H), 3.82 (s, 3H), 3.79 (dd, J=1.2, 7.2 Hz, 1H), 3.62 (d, J=7.2 Hz, 1H), 3.45 (dd, J=1.2, 10.1 Hz, 1H), 3.27 (d, J=10.0 Hz, 1H), 1.93-1.79 (m, 2H); LC-MS (ESI$^+$) m/z 235.2 (M+H)$^+$.

Step 2—6-[(1R,4R)-2-oxa-5-azabicyclo[2.2.1]heptan-5-yl]pyridine-2-carboxylic acid To a solution of methyl 6-[(1R,4R)-2-oxa-5-azabicyclo[2.2.1]heptan-5-yl]pyridine-2-carboxylate (120 mg, 512 umol) in THF (0.5 mL), and $H_2O$ (0.5 mL) was added $LiOH.H_2O$ (43 mg, 1.02 mmol) at 25° C. The mixture was stirred at 25° C. for 1 hour. On completion, the mixture was poured into water (25 mL) and concentrated in vacuo to remove THF. The aqueous phase was washed with EA (30 mL×3), and the organic layer was discarded. The aqueous phase was acidified with 1 N HCl to pH=4 and extracted with DCM (5×25 mL). The combined organic layer was washed with brine (10 mL), dried over $Na_2SO_4$, filtered and concentrated in vacuo to give the title compound as light yellow solid (110 mg, 97% yield). $^1$H NMR (400 MHz, DMSO-$d_6$) δ 7.73-7.59 (m, 1H), 7.32-7.20 (m, 1H), 6.81-6.66 (m, 1H), 5.04 (s, 1H), 4.93 (dd, J=5.6, 13.9 Hz, 1H), 4.66 (s, 1H), 4.54-4.30 (m, 1H), 3.77 (d, J=8.0 Hz, 1H), 3.47-3.37 (m, 2H), 3.27 (d, J=10.0 Hz, 1H), 1.95-1.75 (m, 1H); LC-MS (ESI$^+$) m/z 221.2 (M+H)$^+$.

3,5-Dichloro-N-[2-(4-formylcyclohexyl)-6-(1-hydroxy-1-methyl-ethyl)indazol-5-yl]benzamide (Intermediate BMD)

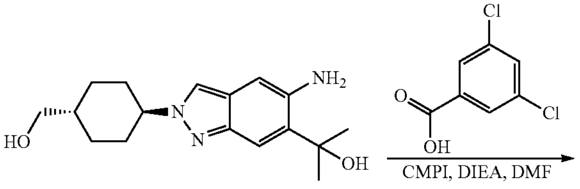

AOX

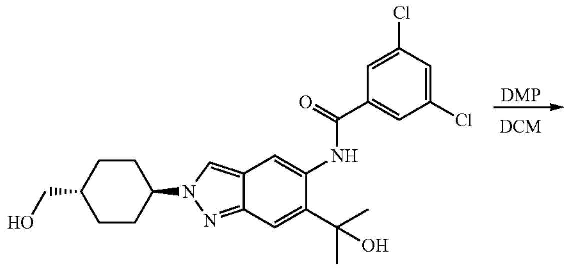

-continued

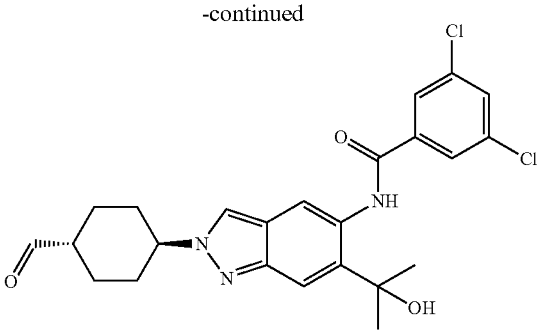

BMD

Step 1—3,5-Dichloro-N-[2-[4-(hydroxymethyl)cyclohexyl]-6-(1-hydroxy-1-methyl-ethyl)indazol-5-yl]benzamide To a solution of 2-[5-amino-2-[4-(hydroxymethyl)cyclohexyl]indazol-6-yl]propan-2-ol (73.0 mg, 240 umol, TFA salt, Intermediate AOX) and 3,5-dichlorobenzoic acid (46.0 mg, 240 umol, CAS #51-36-5) in DMF (2.5 mL) was added DIEA (93.3 mg, 722 umol), CMPI (73.8 mg, 289 umol) at 25° C. The mixture was stirred at 25° C. for 1 hour. The mixture was concentrated in vacuo. The residue was purified by reverse phase flash (FA condition) to give the title compound (110 mg, 86% yield, FA salt) as white solid. $^1$H NMR (400 MHz, DMSO-$d_6$) δ 11.73 (s, 1H), 8.62 (s, 1H), 8.36 (s, 1H), 7.95-7.89 (m, 1H), 7.85 (d, J=1.6 Hz, 2H), 7.59 (s, 1H), 6.64 (s, 1H), 4.55-4.32 (m, 2H), 3.30 (d, J=4.8 Hz, 2H), 2.18-2.07 (m, 2H), 1.89 (d, J=10.8 Hz, 4H), 1.64 (s, 6H), 1.48-1.46 (m, 1H), 1.23-1.07 (m, 2H); LC-MS (ESI$^+$) m/z 476.1 (M+H)$^+$.

Step 2—3,5-Dichloro-N-[2-(4-formylcyclohexyl)-6-(1-hydroxy-1-methyl-ethyl)indazol-5-yl]benzamide To a solution of 3,5-dichloro-N-[2-[4-(hydroxymethyl)cyclohexyl]-6-(1-hydroxy-1-methyl-ethyl) indazol-5-yl]benzamide (100 mg, 191 umol, FA salt) in DCM (5 mL) was added DMP (106 mg, 249 umol) at 25° C. The mixture was stirred at 25° C. for 1 hour. On completion, the reaction was quenched with $Na_2S_2O_3$ (4 mL). The mixture was diluted with water (10 mL), then extracted with DCM (3×40 mL). The combined organic layer was dried over $Na_2SO_4$, filtered and concentrated in vacuo to give the product (90.0 mg, 99% yield) as light yellow solid. $^1$H NMR (400 MHz, DMSO-$d_6$) δ 11.73 (s, 1H), 9.64 (s, 1H), 8.62 (s, 1H), 8.37 (s, 1H), 7.91 (t, J=1.6 Hz, 1H), 7.85 (d, J=1.6 Hz, 2H), 7.59 (s, 1H), 6.64 (s, 1H), 4.53-4.38 (m, 1H), 2.44-2.38 (m, 1H), 2.25-2.16 (m, 2H), 2.11 (d, J=12.0 Hz, 2H), 2.02-1.92 (m, 2H), 1.64 (s, 6H), 1.45 (dq, J=3.2, 12.8 Hz, 2H); LC-MS (ESI$^+$) m/z 474.2 (M+H)$^+$.

1-Methyl-4-(trifluoromethyl)pyrazole-3-carboxylic acid (Intermediate BME)

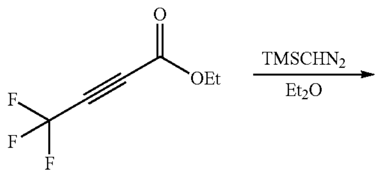

-continued

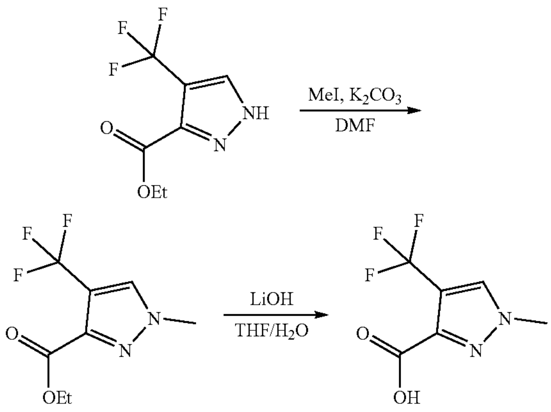

BME

Step 1—Ethyl 4-(trifluoromethyl)-1H-pyrazole-3-carboxylate

To a solution of ethyl 4,4,4-trifluorobut-2-ynoate (2 g, 12.0 mmol, CAS #79424-03-6) in THE (30 mL) was added $TMSCHN_2$ (2 M, 7.20 mL) dropwise at 0° C. under $N_2$, then the reaction mixture was stirred at 20° C. for 2 hrs. On completion, the reaction mixture was concentrated in vacuo to give a residue. The residue was purified by reverse phase (0.1% FA condition) to give the title compound (1.5 g, 60% yield) as a white solid. 1H NMR (400 MHz, DMSO-$d_6$) δ 14.12 (s, 1H), 8.49 (s, 1H), 4.31 (q, J=7.2 Hz, 2H), 1.29 (t, J=7.2 Hz, 3H); LC-MS (ESI$^+$) m/z 209.0 $(M+1)^+$.

Step 2—Ethyl 1-methyl-4-(trifluoromethyl)pyrazole-3-carboxylate

To a solution of ethyl 4-(trifluoromethyl)-1H-pyrazole-3-carboxylate (300 mg, 1.44 mmol) and $K_2CO_3$ (298 mg, 2.16 mmol) in DMF (5 mL) was added MeI (409 mg, 2.88 mmol, 179 uL) at 0° C., then the reaction mixture was stirred at 12 hrs. On completion, the reaction mixture was filtered and the filtrate was concentrated in vacuo to give a residue. The residue was purified by reverse phase (0.1% FA condition) to give the title compound (60 mg, 18% yield) as a white solid. $^1$H NMR (400 MHz, DMSO-$d_6$) δ 8.47 (s, 1H), 4.30 (q, J=7.2 Hz, 2H), 3.95 (s, 3H), 1.28 (t, J=7.2 Hz, 3H).

Step 3—1-Methyl-4-(trifluoromethyl)pyrazole-3-carboxylic acid

To a solution of ethyl 1-methyl-4-(trifluoromethyl)pyrazole-3-carboxylate (60 mg, 270 umol) in THE (2 mL), MeOH (0.5 mL) and $H_2O$ (0.5 mL) was added LiOH (12.9 mg, 540 umol), then the reaction mixture was stirred at 15° C. for 3 hrs. On completion, the mixture was concentrated in vacuo and then diluted with $H_2O$ (10 mL). Then the mixture was adjusted with 1N HCl until the pH 5. Then the mixture was extracted with EA (3x20 mL), the organic phase was dried with $Na_2SO_4$, then concentrated in vacuo to give the title compound (45.0 mg, 85% yield) as a white solid. LC-MS (ESI$^+$) m/z 195.0 $(M+H)^+$.

4-Chloro-1-isopropyl-pyrazole-3-carboxylic acid (Intermediate BMF)

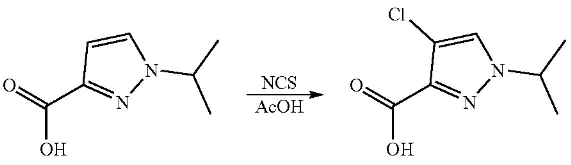

BMF

To a mixture of 1-isopropylpyrazole-3-carboxylic acid (400 mg, 2.59 mmol, CAS #942631-65-4) in AcOH (10 mL) was added NCS (363 mg, 2.72 mmol). The reaction mixture was stirred at 70° C. for 16 hrs under nitrogen atmosphere. On completion, the reaction mixture was concentrated in vacuo. The crude product was purified by reverse phase (0.1% HCl condition) to give the title compound (450 mg, 91% yield) as yellow solid. $^1$H NMR (400 MHz, DMSO-$d_6$) δ 12.88 (s, 1H), 8.17 (s, 1H), 4.59-4.46 (m, 1H), 1.41 (d, J=6.6 Hz, 6H).

(1S,4r)-4-((13S)-4-oxo-22H-6,9-dioxa-3-aza-2(6,5)-indazola-1(1,3)-pyrrolidina-5(1.3)-benzenacyclononaphane-22-yl)cyclohexane-1-carbaldehyde (Intermediate BMG)

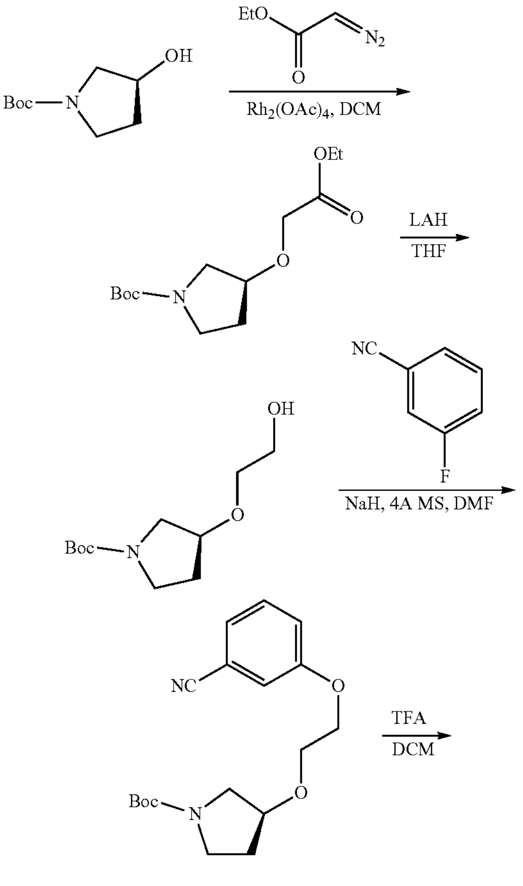

-continued

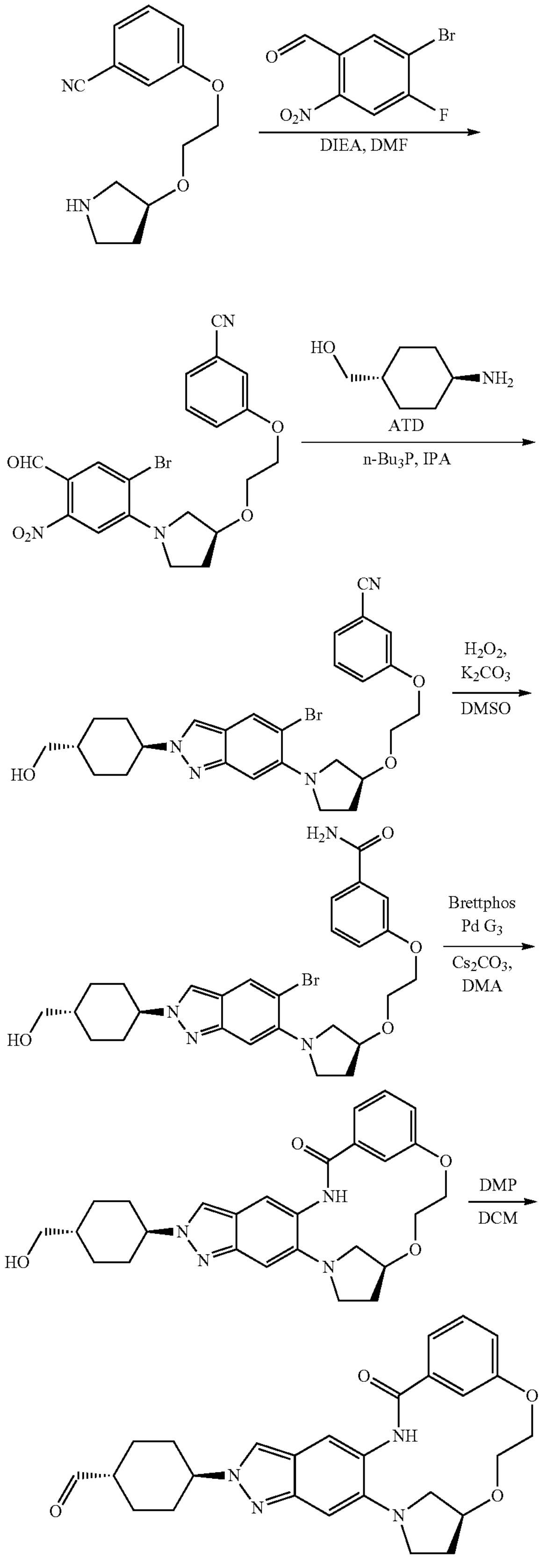

BMG

Step 1—(S)-Tert-butyl 3-(2-ethoxy-2-oxoethoxy) pyrrolidine-1-carboxylate

To a solution of tert-butyl (3S)-3-hydroxypyrrolidine-1-carboxylate (5.00 g, 26.7 mmol, CAS #101469-92-5) in DCM (100 mL) was added $Rh_2(OAc)_4$ (236 mg, 1.07 mmol, CAS #15956-28-2) and ethyl 2-diazoacetate (6.09 g, 53.4 mmol, CAS #623-73-4) was added dropwise. The mixture was stirred at 25° C. for 12 hours. On completion, the reaction mixture was diluted with $H_2O$ (100 mL), and partitioned. The organic phase was separated, washed with brine (50 mL), dried over $Na_2SO_4$, filtered and concentrated under reduced pressure to give a residue. The residue was purified by column chromatography ($SiO_2$, petroleum ether/ethyl acetate=50:1 to 3:1) to give the title compound (5.20 g, 68% yield) as colorless oil. $^1H$ NMR (400 MHz, $CDCl_3$) δ 4.25-4.20 (m, 2H), 4.17-4.13 (m, 1H), 4.11-3.99 (m, 2H), 3.57-3.34 (m, 4H), 2.13-1.87 (m, 2H), 1.45 (s, 9H), 1.28 (t, J=7.2 Hz, 3H).

Step 2—(S)-Tert-butyl 3-(2-hydroxyethoxy)pyrrolidine-1-carboxylate

To a suspension of LAH (717 mg, 18.9 mmol) in THE (50 mL) was added dropwise a solution of tert-butyl (3S)-3-(2-ethoxy-2-oxo-ethoxy)pyrrolidine-1-carboxylate (4.70 g, 17.2 mmol) in THE (50 mL) at 0° C. The mixture was stirred at 0° C. for 0.5 hour. On completion, the reaction mixture was quenched with $H_2O$ (0.8 mL) slowly, then 15% aq.NaOH (1.6 mL) and more $H_2O$ (0.8 mL) at 0° C. was added. The mixture was then diluted with additonal $H_2O$ (100 mL) and extracted with EA (3×100 mL). The combined organic layers were washed with brine (50 mL), dried over $Na_2SO_4$, filtered and concentrated in vacuo. The residue was purified by column chromatography ($SiO_2$, petroleum ether/ethyl acetate=10:1 to 1:1) to give the title compound (2.10 g, 52% yield) as brown oil. $^1H$ NMR (400 MHz, $CDCl_3$) δ 4.12-4.04 (m, 1H), 3.74-3.72 (m, 2H), 3.59-3.52 (m, 2H), 3.49-3.35 (m, 4H), 2.06-1.88 (m, 3H), 1.46 (s, 9H).

Step 3—(S)-Tert-butyl 3-(2-(3-cyanophenoxy) ethoxy)pyrrolidine-1-carboxylate

To a solution of tert-butyl (3S)-3-(2-hydroxyethoxy)pyrrolidine-1-carboxylate (7.30 g, 31.5 mmol) in DMF (70 mL) was added NaH (1.89 g, 47.3 mmol, 60% dispersion in mineral oil) at 0° C. and the mixture was stirred at 25° C. for 0.5 hour. Then 3-fluorobenzonitrile (3.82 g, 31.5 mmol, CAS #403-54-3) was added and the mixture was stirred at 25° C. for 11.5 hours. On completion, the reaction mixture was quenched with $H_2O$ (100 mL) at 0° C., diluted with $H_2O$ (100 mL) and extracted with EA (3×100 mL). The combined organic layers were washed with brine (50 mL), dried over $Na_2SO_4$, filtered and concentrated in vacuo. The residue was purified by column chromatography ($SiO_2$, petroleum ether/ethyl acetate=5:1 to 1:1) to give the title compound (7.40 g, 69% yield) as brown oil. $^1H$ NMR (400 MHz, $CDCl_3$) δ 7.42-7.35 (m, 1H), 7.30-7.24 (m, 1H), 7.20-7.14 (m, 2H), 4.15-4.13 (m, 3H), 3.88-3.77 (m, 2H), 3.56-3.35 (m, 4H), 2.10-1.91 (m, 2H), 1.47 (s, 9H).

Step 4—(S)-3-(2-(Pyrrolidin-3-yloxy)ethoxy)benzonitrile

To a solution of tert-butyl (3S)-3-[2-(3-cyanophenoxy) ethoxy]pyrrolidine-1-carboxylate (7.40 g, 22.2 mmol) in DCM (70 mL) was added TFA (20 mL). The mixture was stirred at 25° C. for 0.5 hour. On completion, the reaction mixture was concentrated in vacuo to give the title compound (7.70 g, 99% yield, TFA salt) as brown oil. LC-MS ($ESI^+$) m/z 233.1 $(M+H)^+$.

Step 5—(S)-3-(2-((1-(2-Bromo-4-formyl-5-nitrophenyl)pyrrolidin-3-yl)oxy)ethoxy)benzonitrile To a solution of 3-[2-[(3S)-pyrrolidin-3-yl]oxyethoxy] benzonitrile (7.70 g, 22.2 mmol, TFA salt) in DMF (80 mL) was added DIEA (8.62 g, 66.7 mmol) and 5-bromo-4-fluoro-2-nitro-benzaldehyde (4.96 g, 20.0 mmol, CAS #213382-45-7, synthesized via Step 1 of Intermediate ATE). The mixture was stirred at 25° C. for 12 hours. On completion, the reaction mixture was diluted with $H_2O$ (500 mL), and extracted with EA (3×200 mL). The organic phase was washed with brine (100 mL), dried over $Na_2SO_4$, filtered and concentrated in vacuo. The residue was purified by column chromatography ($SiO_2$, petroleum ether/ethyl acetate=50:1 to 1:1) to give the title compound (8.00 g, 74% yield) as brown oil. $^1H$ NMR (400 MHz, $CDCl_3$) δ 10.19 (s, 1H), 8.16 (s, 1H), 7.39-7.33 (m, 1H), 7.26-7.23 (m, 1H), 7.21 (s, 1H), 7.17-7.10 (m, 2H), 4.34-4.28 (m, 1H), 4.16-4.12 (m, 2H), 4.07-4.05 (m, 1H), 3.93-3.77 (m, 3H), 3.74-3.72 (m, 1H), 3.64-3.62 (m, 1H), 2.33-2.22 (m, 1H), 2.15-2.05 (m, 1H).

Step 6—3-(2-(((S)-1-(5-Bromo-2-((1r,4S)-4-(hydroxymethyl)cyclohexyl)-2H-inda zol-6-yl pyrrolidin -3-yl)oxy)ethoxy)benzonitrile A solution of 3-[2-[(3S)-1-(2-bromo-4-formyl-5-nitrophenyl)pyrrolidin-3-yl]oxyethoxy]benzonitrile (4.00 g, 8.69 mmol) and (4-aminocyclohexyl)methanol (1.12 g, 8.69 mmol, Intermediate ATD) in IPA (40 mL) was stirred at 80° C. for 3 hours. Then tributylphosphane (5.27 g, 26.0 mmol) was added and the resulting mixture was stirred at 80° C. for 9 hours. On completion, the reaction mixture was filtered and concentrated in vacuo. The residue was purified by column chromatography ($SiO_2$, petroleum ether/ethyl acetate=1:1 to 1:2) to give the title compound (4.80 g, 99% yield) as brown oil. $^1H$ NMR (400 MHz, $CDCl_3$) δ 7.87 (s, 1H), 7.80 (s, 1H), 7.38-7.32 (m, 1H), 7.25-7.21 (m, 2H), 7.19-7.13 (m, 2H), 4.40-4.25 (m, 2H), 4.15 (t, J=4.8 Hz, 2H), 3.94-3.77 (m, 2H), 3.63-3.61 (m, 1H), 3.55-3.54 (m, 2H), 3.44-3.26 (m, 3H), 2.37-2.20 (m, 3H), 2.10-2.00 (m, 3H), 1.99-1.89 (m, 2H), 1.31-1.17 (m, 2H); LC-MS ($ESI^+$) m/z 539.3 $(M+H)^+$.

Step 7—3-(2-(((S)-1-(5-Bromo-2-((1r,4S)-4-(hydroxymethyl)cyclohexyl)-2H-indazol-6-yl) pyrrolidin -3-yl)oxy)ethoxy)benzamide To a solution of 3-[2-[(3S)-1-[5-bromo-2-[4-(hydroxymethyl)cyclohexyl]indazol-6-yl]pyrrolidin-3-yl]oxyethoxy] benzonitrile (1.00 g, 1.85 mmol) in DMSO (10 mL) was added $H_2O_2$ (840 mg, 7.41 mmol, 30% solution) and $K_2CO_3$ (128 mg, 926 umol) at 0° C. The mixture was stirred at 25° C. for 1 hour. On completion, the reaction mixture was quenched with sat. aq. $NaHSO_3$ (50 mL) at 0° C., and then diluted with $H_2O$ (50 mL) and extracted with EA (3×50 mL). The combined organic layers were washed with brine (50 mL), dried over $Na_2SO_4$, filtered and concentrated in vacuo. The residue was purified by column chromatography ($SiO_2$, DCM/MeOH=100:1 to 10:1) to give the title compound (900 mg, 86% yield) as brown oil. $^1H$ NMR (400 MHz, $CDCl_3$) δ 7.87 (s, 1H), 7.80 (s, 1H), 7.44-7.40 (m, 1H), 7.37-7.32 (m, 2H), 7.22 (s, 1H), 7.10 (td, J=2.4, 6.8 Hz, 1H), 6.25-6.06 (m, 1H), 5.75-5.55 (m, 1H), 4.37-4.27 (m, 2H), 4.20 (m, 2H), 3.86 (m, 2H), 3.63 (m, 1H), 3.56 (m, 2H), 3.44-3.26 (m, 3H), 2.35-2.20 (m, 3H), 2.02 (m, 1H), 1.99-1.90 (m, 2H), 1.27 (m, 5H); LC-MS ($ESI^+$) m/z 559.1 $(M+H)^+$.

Step 8—(13S)-22-((1r,4S)-4-(hydroxymethyl)cyclohexyl)-22H-6,9-dioxa-3-aza-2(6,5)-indazola-1(1,3)-pyrrolidina-5(1,3)-benzenacyclononaphan-4-one A mixture of 3-[2-[(3S)-1-[5-bromo-2-[4-(hydroxymethyl)cyclohexyl]indazol-6-yl]pyrrolidin-3-yl]oxyethoxy] benzamide (560 mg, 1.00 mmol), $Cs_2CO_3$ (672 mg, 2.06 mmol), and BrettPhos Pd G3 (137 mg, 151 umol) in DMA (10 mL) was stirred at 90° C. for 16 hours under $N_2$. On completion, after cooled to 25° C., the mixture was filtered, and the cake was washed with EA (10 mL). The filtrate and washing were combined and concentrated in vacuo. The residue was purified by reversed phase flash (FA condition) to give the desired compound (160 mg, 33% yield) as light yellow solid. $^1H$ NMR (400 MHz, DMSO-$d_6$) δ 10.04 (s, 1H), 8.60 (s, 1H), 8.42 (s, 1H), 8.33 (s, 1H), 7.55 (d, J=7.6 Hz, 1H), 7.51 (s, 1H), 7.40 (t, J=8.0 Hz, 1H), 7.12-7.09 (m, 1H), 4.53-4.32 (m, 4H), 4.21-4.18 (m, 1H), 3.92-3.84 (m, 1H), 3.80-3.72 (m, 1H), 3.39-3.37 (m, 1H), 3.20-3.14 (m, 1H), 2.60-2.56 (m, 1H), 2.31-2.21 (m, 1H), 2.14-2.02 (m, 3H), 1.93-1.84 (m, 4H), 1.61-1.55 (m, 1H), 1.48-1.33 (m, 3H), 1.20-1.08 (m, 2H).

Step 9—(1S,4r)-4-((13S)-4-oxo-22H-6,9-dioxa-3-aza-2(6,5)-indazola-1(1,3)-pyrrolidina-5(1,3)-benzenacyclononaphane-22-yl)cyclohexane-1-carbaldehyde To a solution of (13S)-22-((1r,4S)-4-(hydroxymethyl)cyclohexyl)-22H-6,9-dioxa-3-aza-2(6,5)-indazola-1(1,3)-pyrrolidina-5(1,3)-benzenacyclononaphan-4-one (70.0 mg, 146 umol) in DCM (2 mL) was added Dess-Martin (93.6 mg, 220 umol) at 0° C. The mixture was stirred at 15° C. for 1 hour. On completion, the reaction was quenched with sat. aq. $Na_2S_2O_3$ (2 mL) and sat. aq. $NaHCO_3$ (2 mL). The aqueous phase was extracted with DCM (3×10 mL). The combined organic layer was washed with brine (5 mL), dried over $Na_2SO_4$, filtered and concentrated in vacuo to give the title compound (69.0 mg, 98% yield) as light yellow solid. LC-MS ($ESI^+$) m/z 475.3 $(M+H)^+$.

4(1R,4r)-4-((13R)-4-oxo-22H-6,9-dioxa-3-aza-2(6,5)-indazola-1(1,3)-pyrrolidina-5(1.3)-benzenacyclononaphane-22-yl)cyclohexane-1-carbaldehyde (Intermediate BMH)

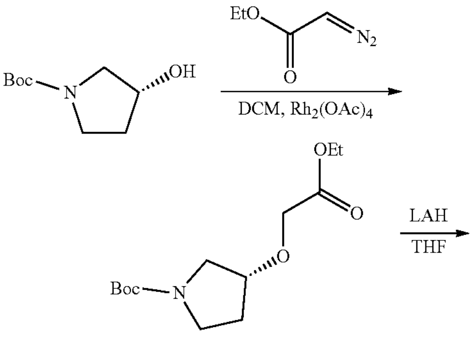

-continued

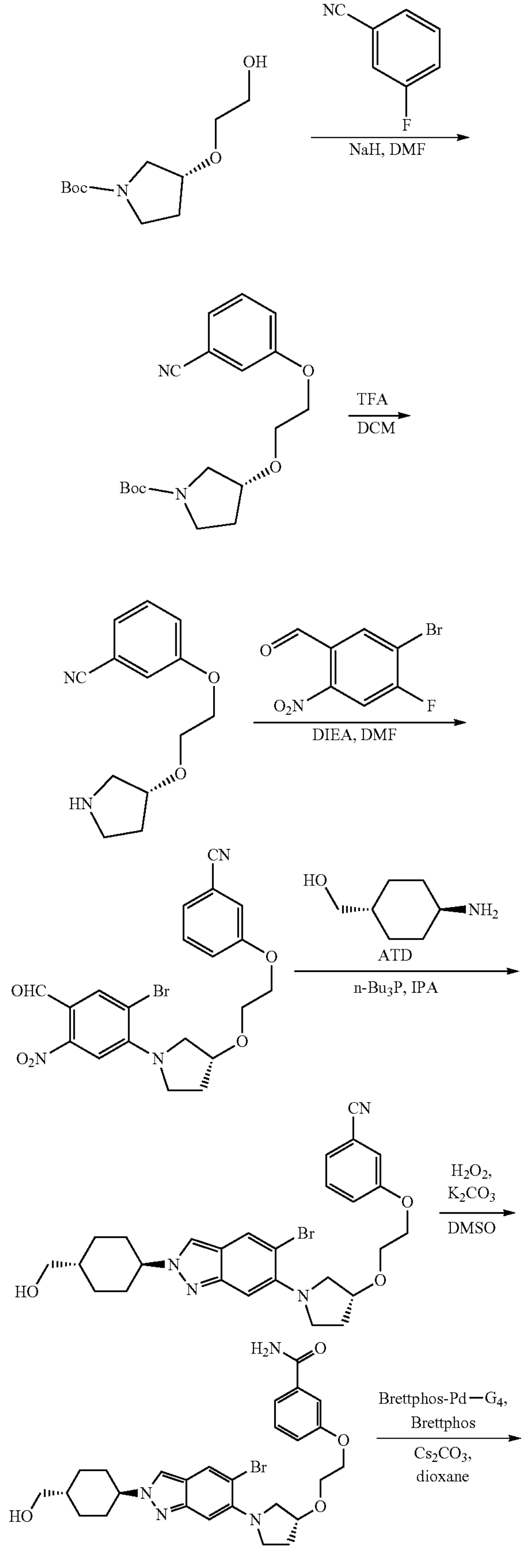

-continued

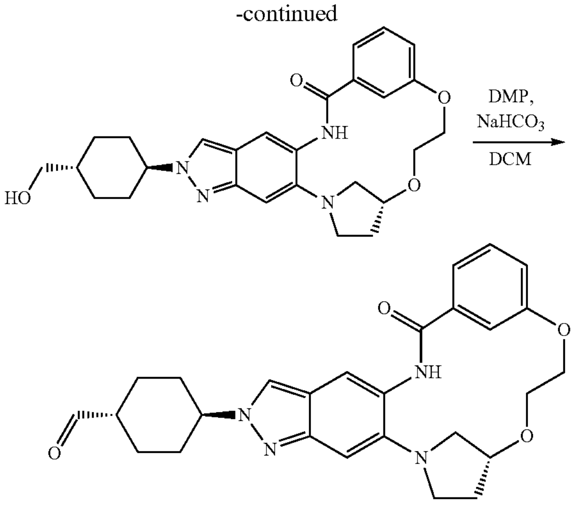

BMH

Step 1—Tert-butyl (3R)-3-(2-ethoxy-2-oxo-ethoxy) pyrrolidine-1-carboxylate

To a solution of tert-butyl (3R)-3-hydroxypyrrolidine-1-carboxylate (10.0 g, 53.4 mmol, CAS #109431-87-0) and $Rh_2(OAc)_4$ (472 mg, 1.07 mmol) in DCM (200 mL) was added a solution of ethyl 2-diazoacetate (12.2 g, 107 mmol) in DCM (100 mL) dropwise. Then the reaction mixture was stirred at 20° C. for 12 hrs. On completion, the mixture was diluted with water (200 mL), and extracted with DCM (2×100 mL). The organic layer was washed with brine (2×100 mL), then concentrated in vacuo. The residue was purified by silica gel chromatography ($SiO_2$) to give the title compound (12.1 g, 83% yield) as yellowish oil. $^1H$ NMR (400 MHz, $CDCl_3$) δ 4.28-4.08 (m, 5H), 3.54-3.46 (m, 4H), 2.12-2.04 (m, 1H), 1.99-1.88 (m, 1H), 1.45 (s, 9H), 1.29 (t, J=7.2 Hz, 3H).

Step 2—Tert-butyl (3R)-3-(2-hydroxyethoxy)pyrrolidine-1-carboxylate

To a solution of tert-butyl (3R)-3-(2-ethoxy-2-oxo-ethoxy)pyrrolidine-1-carboxylate (12.0 g, 43.9 mmol) in THF (100 mL) was added $LiAlH_4$ (2.00 g, 52.7 mmol) at 0° C. Then the reaction mixture was stirred at 0° C. for 1 hr. On completion, the mixture was quenched with water (2 mL), a solution of NaOH (15% wt, 6 mL), and more water (2 mL). Then the mixture was stirred and dried over $Na_2SO_4$, filtered and the filtrate was concentrated in vacuo to give the title compound (8.70 g, 86% yield) as a yellowish solid. $^1H$ NMR (400 MHz, $CDCl_3$) δ 4.08 (d, J=3.6 Hz, 1H), 3.73 (t, J=4.4 Hz, 2H), 3.60-3.35 (m, 6H), 2.14-1.89 (m, 3H), 1.46 (s, 9H).

Step 3—Tert-butyl (3R)-3-[2-(3-cyanophenoxy) ethoxy]pyrrolidine-1-carboxylate

To a solution of tert-butyl (3R)-3-(2-hydroxyethoxy)pyrrolidine-1-carboxylate (8.60 g, 37.2 mmol) in DMF (150 mL) was added NaH (2.23 g, 55.8 mmol, 60% dispersion in mineral oil) at 0° C. Thirty minutes later, 3-fluorobenzonitrile (4.95 g, 40.9 mmol, CAS #403-54-3) was added and the reaction mixture was stirred at 20° C. for 12 hrs. On completion, the mixture was quenched with water (700 mL), and extracted with EA (2×300 mL). The organic layer was concentrated in vacuo. The residue was purified by silica gel chromatography ($SiO_2$) to give the title compound (7.7 g, 62% yield) as yellow oil. $^1H$ NMR (400 MHz, $CDCl_3$) δ 7.41-7.35 (m, 1H), 7.29-7.24 (m, 1H), 7.19-7.14 (m, 2H), 4.14 (t, J=4.8 Hz, 3H), 3.85-3.77 (m, 2H), 3.56-3.33 (m, 4H), 2.08-1.89 (m, 2H), 1.47 (s, 9H).

Step 4—3-[2-[(3R)-pyrrolidin-3-yl]oxyethoxy]benzonitrile

To a solution of tert-butyl (3R)-3-[2-(3-cyanophenoxy) ethoxy]pyrrolidine-1-carboxylate (7.70 g, 23.2 mmol) in DCM (100 mL) was added TFA (50 mL). The reaction mixture was stirred at 20° C. for 0.5 hr. On completion, the mixture was concentrated in vacuo to give the title compound (8.00 g, 100% yield, TFA salt) as yellow oil. LC-MS ($ESI^+$) m/z 233.1 $(M+H)^+$.

Step 5—3-[2-[(3R)-1-(2-bromo-4-formyl-5-nitro-phenyl)pyrrolidin-3-yl]oxyethoxy]benzonitrile To a solution of 3-[2-[(3R)-pyrrolidin-3-yl]oxyethoxy] benzonitrile (8.00 g, 23.1 mmol, TFA salt) and 5-bromo-4-fluoro-2-nitro-benzaldehyde (6.30 g, 25.4 mmol, synthesized via Step 1 of Intermediate ATE) in DMF (80 mL) was added DIEA (11.9 g, 92.4 mmol). Then the reaction mixture was stirred at 60° C. for 12 hrs. On completion, the mixture was diluted with water (600 mL), and extracted with EA (2×300 mL). The combined organic layers were washed with brine (300 mL), then concentrated in vacuo. The residue was purified by silica gel chromatography ($SiO_2$) to give the title compound (10.0 g, 94% yield) as red gum. $^1H$ NMR (400 MHz, $CDCl_3$) δ 10.18 (s, 1H), 8.14 (s, 1H), 7.38-7.33 (m, 1H), 7.26-7.22 (m, 1H), 7.20 (s, 1H), 7.15-7.09 (m, 2H), 4.35-4.28 (m, 1H), 4.16-4.11 (m, 2H), 4.06 (dd, J=4.8, 11.2 Hz, 1H), 3.92-3.70 (m, 4H), 3.67-3.58 (m, 1H), 2.31-2.22 (m, 1H), 2.13-2.06 (m, 1H).

Step 6—3-[2-[(3R)-1-[5-bromo-2-[4-(hydroxymethyl)cyclohexyl]indazol-6-yl]pyrrolidin-3-yl]oxyethoxy]benzonitrile A solution of 3-[2-[(3R)-1-(2-bromo-4-formyl-5-nitro-phenyl)pyrrolidin-3-yl]oxyethoxy]benzonitrile (5.00 g, 10.9 mmol) and (4-aminocyclohexyl)methanol (2.11 g, 16.3 mmol, CAS #1467-84-1, Intermediate ATD) in IPA (60 mL) was stirred at 80° C. for 12 hrs. Then tributylphosphane (6.59 g, 32.6 mmol) was added and the reaction mixture was stirred at 80° C. for 12 hrs. On completion, the mixture was concentrated in vacuo. The residue was diluted with EA (300 mL) and washed with brine (2×200 mL). The organic layer was dried with anhydrous $Na_2SO_4$, filtered and the filtrate was concentrated in vacuo to give the title compound (5.00 g, 85% yield) as yellow oil. LC-MS ($ESI^+$) m/z 539.2 $(M+H)^+$.

Step 7—3-[2-[(3R)-1-[5-bromo-2-[4-(hydroxymethyl)cyclohexyl]indazol-6-yl]pyrrolidin-3-yl]oxyethoxy]benzamide To a solution of 3-[2-[(3R)-1-[5-bromo-2-[4-(hydroxymethyl)cyclohexyl]indazol-6-yl]pyrrolidin-3-yl]oxyethoxy] benzonitrile (0.8 g, 1.48 mmol) and $K_2CO_3$ (102 mg, 741 umol) in DMSO (10 mL) was added $H_2O_2$ (673 mg, 5.93 mmol, 30% solution). Then the reaction mixture was stirred at 20° C. for 2 hrs. On completion, the mixture was quenched with sat. $Na_2S_2O_3$ (10 mL), diluted with water (50 mL), and extracted with EA (100 mL). The organic layer was washed with brine (100 mL), concentrated in vacuo. The residue was purified by reverse phase (0.1% FA condition) to give the title compound (0.8 g, 97% yield) as yellow oil. LC-MS ($ESI^+$) m/z 557.2 $(M+H)^+$.

Step 8—(13R)-22-((1r,4R)-4-(hydroxymethyl)cyclohexyl)-22H-6,9-dioxa-3-aza-2(6.5)-indazola-1(1.3)-pyrrolidina-5(1.3)-benzenacyclononaphan-4-one A mixture of 3-[2-[(3R)-1-[5-bromo-2-[4-(hydroxymethyl)cyclohexyl]indazol-6-yl]pyrrolidin-3-yl]oxyethoxy] benzamide (0.3 g, 538 umol), Brettphos (28.9 mg, 53.8 umol), $Cs_2CO_3$ (351 mg, 1.08 mmol) and BrettPhos-Pd-$G_4$ (49.5 mg, 53.8 umol) in dioxane (10 mL) was de-gassed and heated at 60° C. for 16 hrs under $N_2$. On completion, the mixture was filtered and the filtrate was concentrated in vacuo. The residue was purified by prep-HPLC (column: Phenomenex Synergi C18 150*25 mm*10 um; mobile phase: [water (0.225% FA)-ACN]; B %: 38%-68%, 10 min) to give the title compound (80.0 mg, 31% yield) as a yellow solid. $^1H$ NMR (400 MHz, DMSO-$d_6$) δ 10.04 (s, 1H), 8.60 (s, 1H), 8.42 (s, 1H), 8.32 (s, 1H), 7.55 (d, J=8.0 Hz, 1H), 7.51 (s, 1H), 7.40 (t, J=8.0 Hz, 1H), 7.10 (dd, J=1.2, 8.0 Hz, 1H), 4.49 (s, 1H), 4.43-4.33 (m, 3H), 4.25-4.15 (m, 1H), 3.91-3.84 (m, 1H), 3.79-3.71 (m, 2H), 3.40-3.30 (m, 1H), 3.29-3.09 (m, 4H), 2.65-2.50 (m, 1H), 2.32-2.20 (m, 1H), 2.18-2.00 (m, 3H), 1.96-1.85 (m, 4H), 1.28-1.08 (m, 2H).

Step 9—(1R,4r)-4-((13R)-4-oxo-22H-6,9-dioxa-3-aza-2(6,5)-indazola-1(1,3)-pyrrolidina-5(1,3)-benzenacyclononaphane-22-yl)cyclohexane-1-carbaldehyde To a solution of (13R)-22-((1r,4R)-4-(hydroxymethyl) cyclohexyl)-22H-6,9-dioxa-3-aza-2(6,5)-indazola-1(1,3)-pyrrolidina-5(1,3)-benzenacyclononaphan-4-one (60.0 mg, 126 umol) and $NaHCO_3$ (31.7 mg, 378 umol) in DCM (5 mL) was added DMP (64.1 mg, 151 umol). Then the reaction mixture was stirred at 20° C. for 2 hrs. On completion, the mixture was quenched with sat. $Na_2S_2O_3$ (20 mL) and then washed with sat. $NaHCO_3$ (20 mL), stirred for 10 min, and extracted with DCM (2×30 mL). The organic layer was washed with brine (50 mL), dried in $Na_2SO_4$, filtered and the filtrate was concentrated in vacuo to give the title compound (59 mg, 99% yield) as a yellow solid. LC-MS ($ESI^+$) m/z 475.2 $(M+H)^+$.

N-(2-((1r,4r)-4-formylcyclohexyl)-6-methoxy-1-oxoisoindolin-5-yl)-6-(trifluoromethyl)picolinamide (Intermediate BMI)

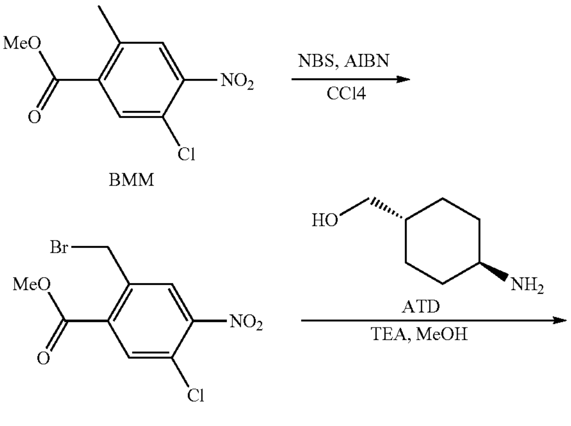

-continued

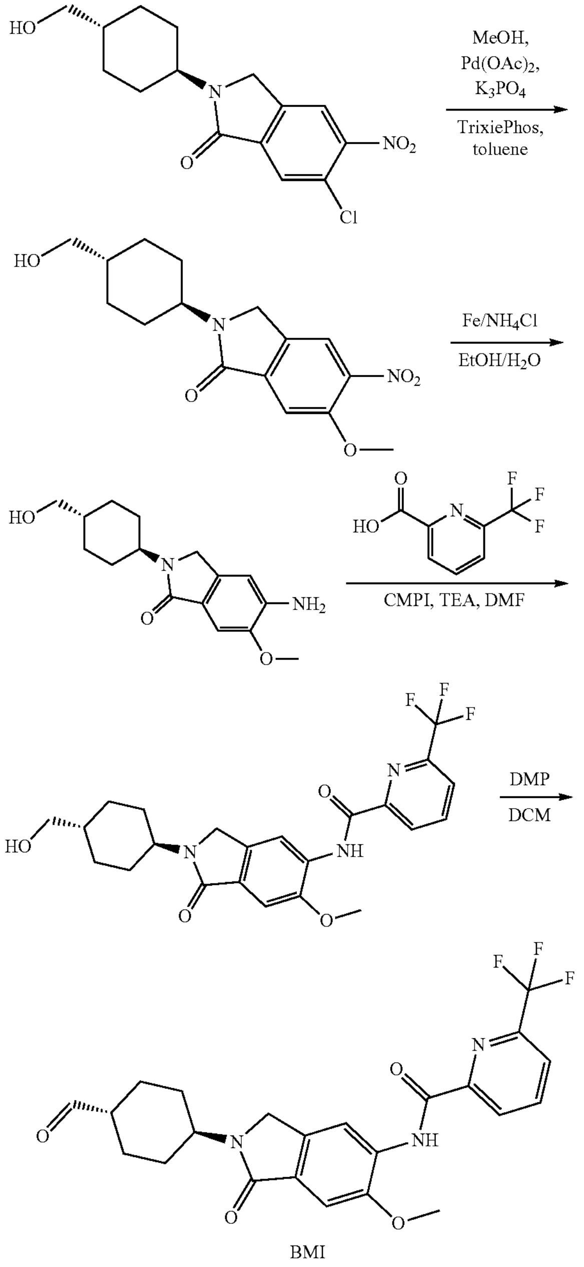

Step 1—Methyl 2-(bromomethyl)-5-chloro-4-nitrobenzoate

To a solution of methyl 5-chloro-2-methyl-4-nitro-benzoate (3.1 g, 13.5 mmol, Intermediate BMM) in ACN (60 mL) was added NBS (2.88 g, 16.2 mmol) and AIBN (111 mg, 675 umol). The mixture was stirred at 70° C. for 16 hours under $N_2$. On completion, the reaction mixture was concentrated in vacuo and the residue was diluted with EA (100 mL) and washed with brine (2×100 mL). The organic layer was dried over $Na_2SO_4$, filtered and concentrated in vacuo to give the title compound (4.0 g, 96% yield) as yellow solid. $^1H$ NMR (400 MHz, $CDCl_3$) δ 8.15 (s, 1H), 7.99 (s, 1H), 4.92 (s, 2H), 4.01 (s, 3H).

Step 2—6-Chloro-2-((1r,4r)-4-(hydroxymethyl)cyclohexyl)-5-nitroisoindolin-1-one To a solution of methyl 2-(bromomethyl)-5-chloro-4-nitro-benzoate (4.0 g, 13.0 mmol) and (4-aminocyclohexyl) methanol (2.01 g, 15.6 mmol, Intermediate ATD) in MeOH (40 mL) was added TEA (2.62 g, 25.9 mmol, 3.61 mL) and the mixture was stirred at 80° C. for 16 hours under $N_2$. On completion, the reaction mixture was concentrated in vacuo. The residue was purified by column chromatography ($SiO_2$, PE:EA=5:1 to 1:2) to give the title compound (2.86 g, 68% yield) as yellow solid. $^1H$ NMR (400 MHz, $CDCl_3$) δ 8.01 (s, 1H), 7.91 (s, 1H), 4.44 (s, 2H), 4.25 (tt, J=3.6, 12.1 Hz, 1H), 3.53 (d, J=6.2 Hz, 2H), 2.01-1.93 (m, 4H), 1.62-1.55 (m, 2H), 1.55-1.49 (m, 1H), 1.46 (s, 1H), 1.28-1.17 (m, 2H).

Step 3—2-((1r,4r)-4-(Hydroxymethyl)cyclohexyl)-6-methoxy-5-nitroisoindolin-1-one To a solution of 6-chloro-2-[4-(hydroxymethyl)cyclo-hexyl]-5-nitro-isoindolin-1-one (1.0 g, 3.08 mmol) in MeOH (1.97 g, 61.6 mmol, 2.49 mL) and toluene (10 mL) was added $K_3PO_4$ (1.31 g, 6.16 mmol), $Pd(OAc)_2$ (69.1 mg, 308 umol) and ditert-butyl-[1-(1-naphthyl)-2-naphthyl] phosphane (245 mg, 616 umol), and the mixture was stirred at 80° C. for 16 hours under $N_2$. On completion, the reaction mixture was concentrated in vacuo and purified by column chromatography ($SiO_2$, PE/EA=10/1 to 1/10) to give the title compound (500 mg, 51% yield) as yellow solid. $^1H$ NMR (400 MHz, $CDCl_3$) δ 7.86 (s, 1H), 7.55 (s, 1H), 4.37 (s, 2H), 4.31-4.21 (m, 1H), 4.02 (s, 3H), 3.53 (d, J=1.8 Hz, 2H), 1.97 (d, J=11.0 Hz, 4H), 1.61-1.49 (m, 3H), 1.44 (s, 1H), 1.29-1.17 (m, 2H).

Step 4—5-Amino-2-((1r,4r)-4-(hydroxymethyl)cyclohexyl)-6-methoxyisoindolin-1-one To a solution of 2-[4-(hydroxymethyl)cyclohexyl]-6-methoxy-5-nitro-isoindolin-1-one (500 mg, 1.56 mmol) in the EtOH (6.0 mL) and $H_2O$ (2.0 mL) was added Fe (436 mg, 7.80 mmol) and $NH_4Cl$ (417 mg, 7.80 mmol). The mixture was stirred at 80° C. for 4 hours. On completion, the reaction mixture was filtered and concentrated in vacuo. The residue was diluted with DCM (100 mL) and MeOH (1.0 mL, then the mixture was washed with water (100 mL). The organic layer was dried over $Na_2SO_4$, filtered and concentrated in vacuo to give the title compound (400 mg, 88% yield) as yellow solid. $^1H$ NMR (400 MHz, DMSO-$d_6$) δ 6.98 (s, 1H), 6.72 (s, 1H), 5.36 (s, 2H), 4.43 (s, 1H), 4.19 (s, 2H), 3.90 (t, J=11.8 Hz, 1H), 3.81 (s, 3H), 3.24 (t, J=5.2 Hz, 2H), 1.82 (d, J=12.4 Hz, 2H), 1.71 (d, J=11.2 Hz, 2H), 1.50 (q, J=11.8 Hz, 2H), 1.38-1.29 (m, 1H), 1.03 (q, J=12.0 Hz, 2H).

Step 5—N-(2-((1r,4r)-4-(hydroxymethyl)cyclohexyl)-6-methoxy-1-oxoisoindolin-5-yl)-6- (trifluoromethyl)picolinamide To a solution of 5-amino-2-[4-(hydroxymethyl)cyclo-hexyl]-6-methoxy-isoindolin-1-one (100 mg, 344 umol) and 6-(trifluoromethyl)pyridine-2-carboxylic acid (65.8 mg, 344 umol) in the DMF (2 mL) was added CMPI (106 mg, 413 umol) and DIEA (133 mg, 1.03 mmol, 180 uL). The mixture was stirred at 25° C. for 1 hr. On completion, the reaction mixture was diluted with EA (20 mL) and washed with water (3×20 mL). The organic layer was dried over $Na_2SO_4$, filtered and concentrated in vacuo to give the title compound (155 mg, 97% yield) as yellow solid. $^1$H NMR (400 MHz, $CDCl_3$) δ 10.76 (s, 1H), 8.74 (s, 1H), 8.50 (d, J=7.8 Hz, 1H), 8.15 (t, J=7.8 Hz, 1H), 7.90 (d, J=7.6 Hz, 1H), 7.41 (s, 1H), 4.34 (s, 2H), 4.25 (t, J=11.6 Hz, 1H), 4.05 (s, 3H), 3.53 (d, J=6.4 Hz, 2H), 1.97 (d, J=11.0 Hz, 4H), 1.62-1.54 (m, 3H), 1.29-1.24 (m, 2H).

Step 6—N-(2-((1r,4r)-4-formylcyclohexyl)-6-methoxy-1-oxoisoindolin-5-yl)-6-(trifluoromethyl) picolinamide To a solution of N-[2-[4-(hydroxymethyl)cyclohexyl]-6-methoxy-1-oxo-isoindolin-5-yl]-6- (trifluoromethyl)pyridine-2-carboxamide (155 mg, 334 umol) in the DCM (3 mL) was added DMP (170 mg, 401 umol) and the mixture was stirred at 25° C. for 1 hr. On completion, the reaction mixture was quenched by $Na_2S_2O_3$ (aq, 5 mL) and $NaHCO_3$ (aq, 5 mL), then the mixture was extracted with DCM (2×20 mL). The organic layer was dried over $Na_2SO_4$, filtered and concentrated in vacuo and purified by column chromatography (SiO2, PE/EA=10/1 to 1/1) to give the title compound (150 mg, 87% yield) as yellow solid. LC-MS (ESI$^+$) m/z 462.2 $(M+H)^+$.

(1R,4R)-4-(3-oxo-12H-5,8,11-trioxa-2-aza-1(5,6)-indazola-4(2,6)-pyridinacycloundecaphane-12-yl) cyclohexane-1-carbaldehyde (Intermediate BMJ)

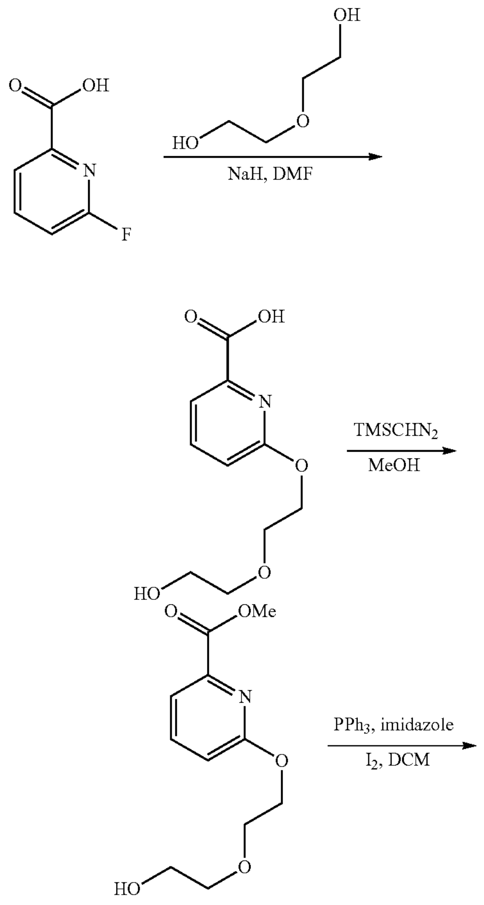

-continued

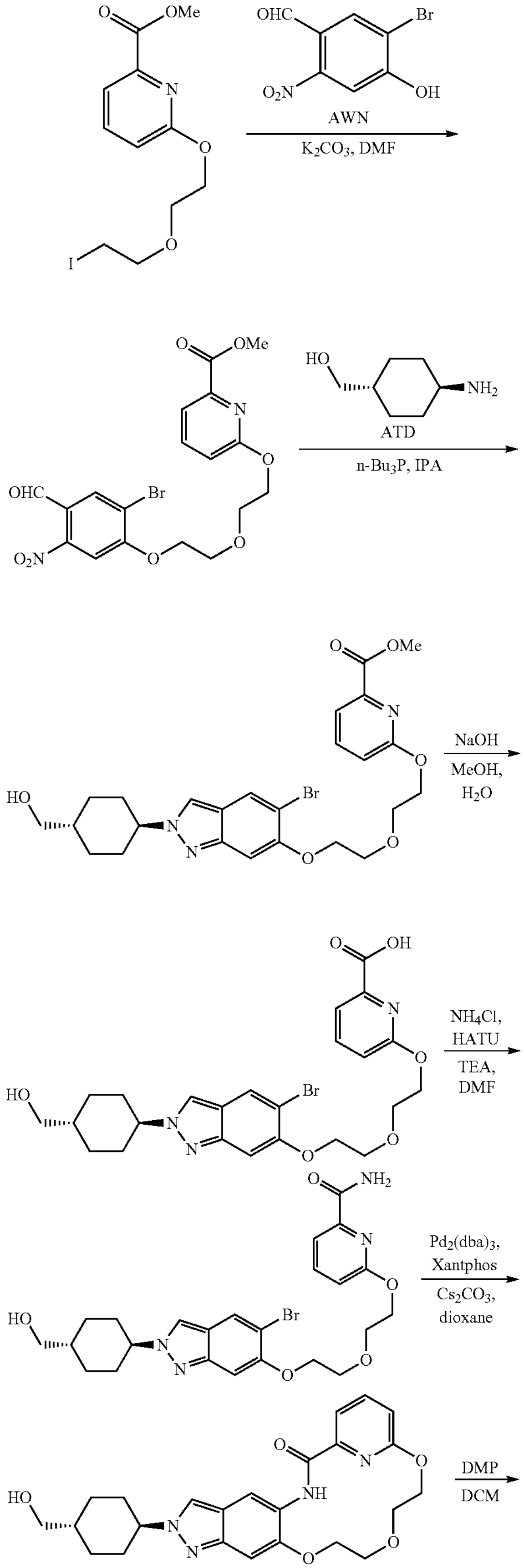

-continued

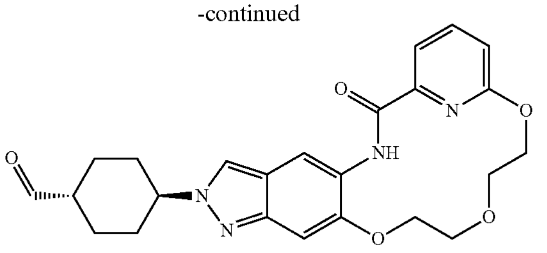

BMJ

Step 1—6-[2-(2-Hydroxyethoxy)ethoxy]pyridine-2-carboxylic acid

To a solution of 2-(2-hydroxyethoxy)ethanol (11.2 g, 106 mmol, CAS #111-46-6) in DMF (30 mL) was added NaH (1.36 g, 34.0 mmol, 60% dispersion in mineral oil) at 0° C. The mixture was stirred at 0° C. for 0.5 hr. Then 6-fluoropyridine-2-carboxylic acid (3.00 g, 21.2 mmol, CAS #402-69-7) was added, and the mixture was stirred at 60° C. for 3 hrs. On completion, the mixture was quenched with $H_2O$ (10 mL) and concentrated in vacuo. The mixture was purified by prep-HPLC (reverse phase: 0.1% FA) to give the title compound (2.70 g, 55% yield) as yellow solid. $^1H$ NMR (400 MHz, DMSO-$d_6$) δ 14.11-12.08 (m, 1H), 7.92-7.80 (m, 1H), 7.65 (d, J=7.2 Hz, 1H), 7.06 (d, J=8.4 Hz, 1H), 4.51-4.39 (m, 2H), 3.81-3.70 (m, 2H), 3.55-3.41 (m, 4H).

Step 2—Methyl 6-[2-(2-hydroxyethoxy)ethoxy]pyridine-2-carboxylate

To a solution of 6-[2-(2-hydroxyethoxy)ethoxy]pyridine-2-carboxylic acid (2.20 g, 9.68 mmol) in MeOH (22 mL) was added $TMSCHN_2$ (2 M, 7.26 mL). The mixture was stirred at 20° C. for 16 hrs. On completion, the mixture was quenched with HOAc (3 mL) and concentrated in vacuo. The mixture was diluted with $H_2O$ (50 mL) and extracted with EA (3×40 mL). Then the organic layers were washed with brine (2×50 mL) and dried over anhydrous $Na_2SO_4$, filtered and concentrated in vacuo. The mixture was purified by prep-HPLC (reverse phase: 0.1% FA) to give the title compound (2.00 g, 85% yield) as yellow oil. $^1H$ NMR (400 MHz, DMSO-$d_6$) δ 7.92-7.86 (m, 1H), 7.69 (dd, J=0.8, 7.2 Hz, 1H), 7.11 (dd, J=0.8, 8.4 Hz, 1H), 4.65-4.60 (m, 1H), 4.49-4.37 (m, 2H), 3.87 (s, 3H), 3.81-3.73 (m, 2H), 3.55-3.46 (m, 4H).

Step 3—Methyl 6-[2-(2-iodoethoxy)ethoxy]pyridine-2-carboxylate

To a mixture of methyl 6-[2-(2-hydroxyethoxy)ethoxy] pyridine-2-carboxylate (1.00 g, 4.15 mmol), $PPh_3$ (1.30 g, 4.97 mmol) and imidazole (338 mg, 4.97 mmol) in DCM (20 mL) was added $I_2$ (1.26 g, 4.97 mmol). The reaction mixture was stirred at 25° C. for 2 hrs. On completion, the reaction mixture was diluted with water (150 mL) and extracted with DCM (3×50 mL). The organic layer was washed with brine (3×100 mL), dried over anhydrous sodium sulfate and filtered. The filtrated was concentrated in vacuo and the residue was purified by silica gel chromatography (PE:EA=1:0 to 25:1) to give the title compound (1.16 g, 79% yield) as white solid. $^1H$ NMR (400 MHz, DMSO-$d_6$) δ 7.89 (dd, J=7.2, 8.4 Hz, 1H), 7.68 (d, J=7.2 Hz, 1H), 7.10 (d, J=8.4 Hz, 1H), 4.47-4.41 (m, 2H), 3.86 (s, 3H), 3.83-3.78 (m, 2H), 3.73 (t, J=6.4 Hz, 2H), 3.36-3.32 (m, 2H).

Step 4—Methyl 6-[2-[2-(2-bromo-4-formyl-5-nitrophenoxy)ethoxy]ethoxy]pyridine-2-carboxylate To a mixture of 5-bromo-4-hydroxy-2-nitro-benzaldehyde (812 mg, 3.30 mmol, Intermediate AWN) and $K_2CO_3$ (913 mg, 6.61 mmol) in DMF (15 mL) was added methyl 6-[2-(2-iodoethoxy)ethoxy] pyridine-2-carboxylate (1.16 g, 3.30 mmol). The reaction mixture was stirred at 60° C. for 24 hrs. Then $K_2CO_3$ (456 mg, 3.30 mmol) was added. The reaction mixture was stirred at 60° C. for 32 hrs. On completion, the reaction mixture was filtered, then the filtrated was concentrated in vacuo. The crude product was purified by reversed-phase HPLC (0.1% FA condition) to give the title compound (860 mg, 55% yield) as yellow oil. $^1H$ NMR (400 MHz, DMSO-$d_6$) δ 10.03 (s, 1H), 8.13 (s, 1H), 7.88-7.81 (m, 2H), 7.65 (d, J=7.2 Hz, 1H), 7.04 (d, J=8.4 Hz, 1H), 4.48-4.42 (m, 4H), 3.91-3.86 (m, 4H), 3.85 (s, 3H).

Step 5—Methyl 6-[2-[2-[5-bromo-2-[4-(hydroxymethyl)cyclohexyl]indazol-6-yl]oxyethoxy]ethoxy]pyridine-2-carboxylate A mixture of methyl 6-[2-[2-(2-bromo-4-formyl-5-nitrophenoxy)ethoxy]ethoxy]pyridine-2- carboxylate (860 mg, 1.83 mmol) and (4-aminocyclohexyl)methanol (236 mg, 1.83 mmol, Intermediate ATD, CAS #1467-84-1) in IPA (20 mL) was stirred at 80° C. for 3 hrs under nitrogen atmosphere. After reactant was consumed completely, tributylphosphane (1.11 g, 5.50 mmol) was added to the reaction mixture. The reaction mixture was stirred at 80° C. for 16 hrs under nitrogen atmosphere. On completion, the reaction mixture was concentrated in vacuo to give the title compound (1.00 g, 99% yield) as yellow oil. LC-MS (ESI+) m/z 550.2 $(M+H)^+$.

Step 6—6-[2-[2-[5-Bromo-2-[4-(hydroxymethyl)cyclohexyl]indazol-6-yl]oxyethoxy]ethoxy]pyridine-2-carboxylic acid To a mixture of methyl 6-[2-[2-[5-bromo-2-[4-(hydroxymethyl)cyclohexyl]indazol-6-yl]oxyethoxy] ethoxy] pyridine-2-carboxylate (1.00 g, 1.82 mmol) in a mixed solution of MeOH (20 mL) and $H_2O$ (2 mL) was added NaOH (145 mg, 3.65 mmol). The reaction mixture was stirred at 60° C. for 2 hrs. On completion, the reaction mixture was concentrated in vacuo, and the mixture was diluted with water (100 mL) and extracted with DCM (3×30 mL). The aqueous phase was acidified with 1N HCl until the pH=3. The mixture was extracted with EA (3×50 mL) and the organic layer was washed with brine (3×50 mL). The organic layer was dried over anhydrous sodium sulfate and filtered. The filtrated was concentrated in vacuo to give the title compound (600 mg, 61% yield) as yellow solid. $^1H$ NMR (400 MHz, DMSO-$d_6$) δ 8.27 (s, 1H), 7.94 (s, 1H), 7.84 (dd, J=7.2, 8.4 Hz, 1H), 7.66-7.62 (m, 1H), 7.12 (s, 1H), 7.07-7.02 (m, 1H), 4.57-4.43 (m, 3H), 4.42-4.32 (m, 1H), 4.23-4.15 (m, 2H), 3.94-3.86 (m, 4H), 3.29-3.26 (m, 2H), 2.16-2.07 (m, 2H), 1.94-1.80 (m, 4H), 1.33-1.28 (m, 1H), 1.17-1.07 (m, 2H).

Step 7—6-[2-[2-[5-Bromo-2-[4-(hydroxymethyl)cyclohexyl]indazol-6-yl]oxyethoxy]ethoxy]pyridine-2-carboxamide To a mixture of 6-[2-[2-[5-bromo-2-[4-(hydroxymethyl)cyclohexyl]indazol-6-yl]oxyethoxy]ethoxy] pyridine-2-carboxylic acid (590 mg, 1.10 mmol), $NH_4Cl$ (1.18 g, 22.0 mmol) and TEA (335 mg, 3.31 mmol) in DMF (1 mL) was added HATU (629 mg, 1.66 mmol). The reaction mixture was stirred at 25° C. for 1 hr. On completion, the mixture was diluted with water (100 mL) and extracted with EA (3×50 mL). The organic layer was washed with brine (3×100 mL), then the organic layer was dried over anhydrous sodium sulfate and filtered. The filtrated was concentrated in vacuo to give the title compound (580 mg, 98% yield) as yellow solid. $^1H$ NMR (400 MHz, DMSO-$d_6$) δ 8.27 (s, 1H), 8.02 (s, 1H), 7.95 (s, 1H), 7.87-7.80 (m, 1H), 7.62-7.58 (m, 2H), 7.12 (s, 1H), 7.02-6.98 (m, 1H), 4.58-4.54 (m, 2H), 4.48 (t, J=5.2 Hz, 1H), 4.41-4.32 (m, 1H), 4.22-4.16 (m, 2H), 3.92-3.88 (m, 4H), 3.28 (t, J=5.6 Hz, 2H), 2.15-2.06 (m, 2H), 1.91-1.79 (m, 4H), 1.34-1.30 (m, 1H), 1.18-1.08 (m, 2H).

Step 8—12-((1R,4R)-4-(hydroxymethyl)cyclohexyl)-12H-5,8,11-trioxa-2-aza-1(5,6)-indazola-4(2,6)-pyridinacycloundecaphan-3-one A mixture of 6-[2-[2-[5-bromo-2-[4-(hydroxymethyl)cyclohexyl]indazol-6-yl]oxyethoxy]ethoxy] pyridine-2-carboxamide (340 mg, 637 umol), $Cs_2CO_3$ (415 mg, 1.27 mmol) and BrettPhos (Pd, $G_4$) (58.6 mg, 63.7 umol) in DMA (30 mL) was stirred at 80° C. for 16 hrs. On completion, the reaction mixture was diluted with water (150 mL) and extracted with EA (3×80 mL). The organic layer was washed with brine (3×100 mL), dried over anhydrous sodium sulfate and filtered. The filtrated was concentrated in vacuo and the residue was purified by reversed-phase HPLC (0.1% FA condition) to give the title compound (170 mg, 58% yield) as yellow solid. $^1H$ NMR (400 MHz, DMSO-$d_6$) δ 11.00 (s, 1H), 8.57 (s, 1H), 8.32 (s, 1H), 8.02-7.94 (m, 1H), 7.74 (d, J=7.2 Hz, 1H), 7.18 (s, 1H), 7.11 (d, J=8.4 Hz, 1H), 4.57 (t, J=6.8 Hz, 2H), 4.49 (s, 1H), 4.41-4.30 (m, 1H), 4.27-4.19 (m, 2H), 4.07 (t, J=6.8 Hz, 2H), 3.97-3.89 (m, 2H), 3.30-3.27 (m, 2H), 2.20-2.10 (m, 2H), 1.95-1.79 (m, 4H), 1.52-1.41 (m, 1H), 1.20-1.07 (m, 2H).

Step 9—(1R,4R)-4-(3-oxo-12H-5,8,11-trioxa-2-aza-1(5,6)-indazola-4(2,6)-pyridinacycloundecaphane-12-yl)cyclohexane-1-carbaldehyde To a mixture of 12-((1R,4R)-4-(hydroxymethyl)cyclohexyl)-12H-5,8,11-trioxa-2-aza-1(5,6)-indazola-4(2,6)-pyridinacycloundecaphan-3-one (160 mg, 353 umol) and $NaHCO_3$ (148 mg, 1.77 mmol) in DCM (10 mL) was added DMP (224 mg, 530 umol) at 0° C. The reaction mixture was stirred at 25° C. for 1 hr. On completion, the reaction mixture was diluted with saturated $Na_2S_2O_3$ aqueous (5 mL) and saturated $NaHCO_3$ aqueous (5 mL), and the mixture was stirred at 20° C. for 0.5 hr. The mixture was then diluted with water (150 mL) and extracted with DCM (3×60 mL). The organic layer was washed with saturated $NaHCO_3$ aqueous (2×100 mL) and brine (3×100 mL). The organic layer was dried over anhydrous sodium sulfate and filtered. The filtrated was concentrated in vacuo to give the title compound (150 mg, 94% yield) as yellow solid. $^1H$ NMR (400 MHz, DMSO-$d_6$) δ 11.00 (s, 1H), 9.64 (s, 1H), 8.58 (s, 1H), 8.33 (s, 1H), 8.01-7.95 (m, 1H), 7.74 (d, J=6.8 Hz, 1H), 7.18 (s, 1H), 7.11 (d, J=8.4 Hz, 1H), 4.57 (t, J=6.8 Hz, 2H), 4.39 (tt, J=4.0, 11.6 Hz, 1H), 4.28-4.18 (m, 2H), 4.07 (t, J=6.8 Hz, 2H), 3.97-3.84 (m, 2H), 2.46-2.37 (m, 1H), 2.24-2.16 (m, 2H), 2.15-2.05 (m, 2H), 2.00-1.90 (m, 2H), 1.50-1.38 (m, 2H).

(1R,4R)-4-(3-oxo-12H-5,10-dioxa-2-aza-1(5,6)-indazola-4(2,6)-pyridinacyclodecaphane-12-yl)cyclohexane-1-carbaldehyde (Intermediate BMK)

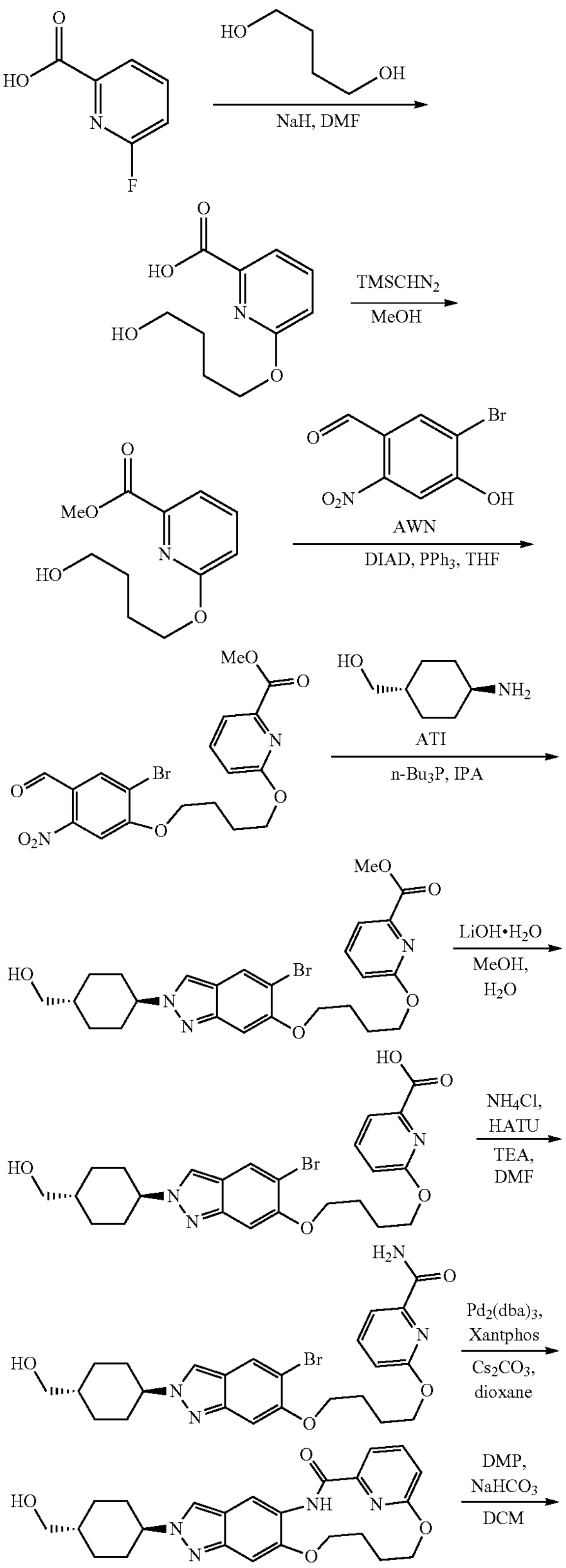

-continued

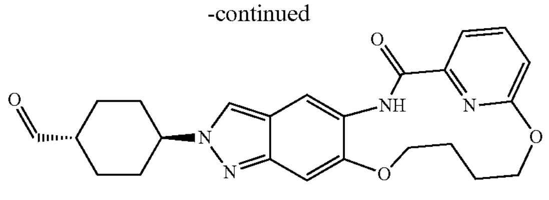

BMK

Step 1—6-(4-Hydroxybutoxy)pyridine-2-carboxylic acid

To a solution of butane-1,4-diol (4.15 g, 46.0 mmol, CAS #110-63-4) in DMF (40 mL) was added NaH (589 mg, 14.7 mmol, 60% dispersion in mineral oil) at 0° C. The mixture was stirred at 0° C. for 0.5 hr. Then 6-fluoropyridine-2-carboxylic acid (1.30 g, 9.21 mmol, CAS #402-69-7) was added to above solution and the mixture was stirred at 25° C. for 2 hrs. On completion, the mixture was quenched with $H_2O$ (200 mL) and adjusted to pH=3 with 1N HCl. The mixture was then extracted with EA (5×40 mL), the organic layers were dried over anhydrous $Na_2SO_4$, filtered and concentrated in vacuo. The mixture was purified by reverse phase (0.1% FA) to give the title compound (740 mg, 38% yield) as yellow oil. $^1$H NMR (400 MHz, DMSO-$d_6$) δ 13.0 (s, 1H), 7.90-7.80 (m, 1H), 7.68-7.60 (m, 1H), 7.07-6.99 (m, 1H), 4.45 (s, 1H), 4.36-4.29 (m, 2H), 3.55-3.40 (m, 2H), 1.82-1.71 (m, 2H), 1.61-1.50 (m, 2H), LC-MS (ESI$^+$) m/z 234.1 (M+Na)$^+$.

Step 2—Methyl 6-(4-hydroxybutoxy)pyridine-2-carboxylate

To a solution of 6-(4-hydroxybutoxy)pyridine-2-carboxylic acid (720 mg, 3.41 mmol) in MeOH (10 mL) was added $TMSCHN_2$ (2.00 M, 2.56 mL). The mixture was stirred at 20° C. for 16 hrs. On completion, the mixture was quenched with HOAc (1 mL) and concentrated in vacuo. The mixture was purified by silica gel column (PE:EA=5:1) to give the title compound (640 mg, 83% yield) as yellow oil. $^1$H NMR (400 MHz, $CDCl_3$) δ 7.75-7.63 (m, 2H), 6.99-6.88 (m, 1H), 4.47 (t, J=6.4 Hz, 2H), 3.98 (s, 3H), 3.77 (t, J=6.4 Hz, 2H), 1.95-1.88 (m, 2H), 1.80-1.72 (m, 2H), LC-MS (ESI$^+$) m/z 226.2 (M+H)$^+$.

Step 3—Methyl 6-[4-(2-bromo-4-formyl-5-nitrophenoxy)butoxy]pyridine-2-carboxylate To a solution of 5-bromo-4-hydroxy-2-nitro-benzaldehyde (364 mg, 1.48 mmol, Intermediate AWN), methyl 6-(4-hydroxybutoxy) pyridine-2-carboxylate (500 mg, 2.22 mmol) and $PPh_3$ (582 mg, 2.22 mmol) in THF (10 mL) was added DIAD (598 mg, 2.96 mmol) at 0° C. dropwise. The mixture was stirred at 20° C. for 16 hrs under $N_2$. On completion, the mixture was quenched with $H_2O$ (40 mL), and extracted with EA (2×30 mL). The organic layer were dried over anhydrous $Na_2SO_4$, filtered and concentrated in vacuo. The mixture was purified by reverse phase (0.1% FA) to give the title compound (400 mg, 59% yield) as yellow oil. $^1$H NMR (400 MHz, DMSO-$d_6$) δ 10.04 (s, 1H), 8.17 (s, 1H), 7.93-7.83 (m, 1H), 7.81 (s, 1H), 7.70-7.65 (m, 1H), 7.10-7.03 (m, 1H), 4.55-4.18 (m, 4H), 3.86 (s, 3H), 2.00-1.90 (m, 4H), LC-MS (ESI$^+$) m/z 453.0 (M+H)$^+$.

Step 4—Methyl 6-[4-[5-bromo-2-[4-(hydroxymethyl)cyclohexyl]indazol-6-yl]oxybutoxy]pyridine-2-carboxylate To a solution of methyl 6-[4-(2-bromo-4-formyl-5-nitrophenoxy)butoxy]pyridine-2-carboxylate (400 mg, 882 umol) in IPA (4.00 mL) was added (4-aminocyclohexyl) methanol (114 mg, 882 umol, Intermediate ATD) and the mixture was stirred at 80° C. for 16 hrs. Then tributylphosphane (535 mg, 2.65 mmol) was added and the mixture was stirred at 80° C. for 12 hrs. On completion, the mixture was concentrated in vacuo and the mixture was purified by reverse phase (0.1% FA) to give the title compound (400 mg, 85% yield) as yellow solid. $^1$H NMR (400 MHz, DMSO-$d_6$) δ 8.27 (s, 1H), 7.95 (s, 1H), 7.90-7.84 (m, 1H), 7.70-7.64 (m, 1H), 7.14-7.06 (m, 2H), 4.50 (s, 1H), 4.44-4.39 (m, 2H), 4.39-4.32 (m, 1H), 4.18-4.07 (m, 2H), 3.86 (s, 3H), 3.30-3.27 (m, 2H), 2.17-2.06 (m, 2H), 2.01-1.95 (m, 3H), 1.91-1.79 (m, 4H), 1.51-1.29 (m, 2H), 1.24-1.10 (m, 2H), LC-MS (ESI$^+$) m/z 534.2 (M+H)$^+$.

Step 5—6-[4-[5-Bromo-2-[4-(hydroxymethyl)cyclohexyl]indazol-6-yl]oxybutoxy]pyridine-2- carboxylic acid To a solution of methyl 6-[4-[5-bromo-2-[4-(hydroxymethyl)cyclohexyl]indazol-6-yl]oxybutoxy] pyridine-2-carboxylate (450 mg, 845 umol) in MeOH (5.00 mL) and $H_2O$ (1.00 mL) was added LiOH $H_2O$ (177 mg, 4.23 mmol) and the mixture was stirred at 60° C. for 2 hrs. On completion, the mixture was diluted with $H_2O$ (20 mL) and concentrated in vacuo. The mixture was extracted with EA (2×15 mL), and the aqueous phase was adjusted to pH=4 with 1N HCl. Then the mixture was extracted with EA (3×15 mL), and the organic layers were washed with brine (2×20 mL), dried over anhydrous $Na_2SO_4$, filtered and concentrated in vacuo to give the title compound (400 mg, 91% yield) as yellow solid. $^1$H NMR (400 MHz, DMSO-$d_6$) δ 13.0 (s, 1H), 8.27 (s, 1H), 7.95 (s, 1H), 7.90-7.80 (m, 1H), 7.70-7.60 (m, 1H), 7.11 (s, 1H), 7.08-7.03 (m, 1H), 4.52-4.47 (m, 1H), 4.46-4.40 (m, 2H), 4.40-4.31 (m, 1H), 4.17-4.10 (m, 2H), 3.30-3.27 (m, 2H), 2.19-2.07 (m, 2H), 1.98-1.84 (m, 8H), 1.56-1.39 (m, 1H), 1.17-1.06 (m, 2H), LC-MS (ESI$^+$) m/z 520.2 (M+H)$^+$.

Step 6—6-[4-[5-Bromo-2-[4-(hydroxymethyl)cyclohexyl]indazol-6-yl]oxybutoxy]pyridine-2-carboxamide To a solution of 6-[4-[5-bromo-2-[4-(hydroxymethyl)cyclohexyl]indazol-6-yl]oxybutoxy] pyridine-2-carboxylic acid (350 mg, 675 umol), $NH_4Cl$ (722 mg, 13.5 mmol) in DMF (7.00 mL) was added TEA (204 mg, 2.03 mmol) and HATU (385 mg, 1.01 mmol). The mixture was stirred at 20° C. for 1 hr. On completion, the mixture was diluted with $H_2O$ (50 mL), and extracted with EA (3×30 mL). The organic layers were washed with brine (2×30 mL), dried over anhydrous $Na_2SO_4$, filtered and concentrated in vacuo to give the title compound (340 mg, 97% yield) as yellow solid. $^1$H NMR (400 MHz, DMSO-$d_6$) δ 8.27 (s, 1H), 8.01-7.94 (m, 2H), 7.90-7.80 (m, 1H), 7.65-7.59 (m, 2H), 7.11 (s, 1H), 7.03-6.95 (m, 1H), 4.53-4.44 (m, 3H), 4.43-4.31 (m, 1H), 4.22-4.07 (m, 2H), 3.30-3.26 (m, 2H), 2.19-2.04 (m, 2H), 1.99-1.78 (m, 8H), 1.57-1.38 (m, 1H), 1.21-1.03 (m, 2H), LC-MS (ESI$^+$) m/z 519.2 (M+H)$^+$.

Step 7—12-((1R,4R)-4-(hydroxymethyl)cyclohexyl)-12H-5,10-dioxa-2-aza-1(5,6)-indazola-4(2,6)-pyridinacyclodecaphan-3-one To a solution of 6-[4-[5-bromo-2-[4-(hydroxymethyl)cyclohexyl]indazol-6-yl]oxybutoxy] pyridine-2-carboxamide (150 mg, 289 umol) in dioxane (16.0 mL) was added $Pd_2(dba)_3$ (26.5 mg, 28.9 umol), Xantphos (33.5 mg, 57.9 umol) and $Cs_2CO_3$ (188 mg, 579 umol). The mixture was stirred at 80° C. for 16 hrs under $N_2$. On completion, the mixture was filtered and concentrated in vacuo. The mixture was purified by prep-TLC (EA) to give the title compound (70 mg, 55% yield) as yellow solid. LC-MS ($ESI^+$) m/z 437.2 $(M+H)^+$.

Step 8—(1R,4R)-4-(3-oxo-12H-5,10-dioxa-2-aza-1(5,6)-indazola-4(2,6)-pyridinacyclodecaphane-12-yl)cyclohexane-1-carbaldehyde To a solution of 12-((1r,4r)-4-(hydroxymethyl)cyclohexyl)-12H-5,10-dioxa-2-aza-1(5,6)-indazola-4(2,6)-pyridinacyclodecaphan-3-one (60.0 mg, 137 umol) in DCM (2.00 mL) was added DMP (87.4 mg, 206 umol) and $NaHCO_3$ (57.7 mg, 687 umol). The mixture was stirred at 25° C. for 0.5 hr. On completion, the mixture was diluted with DCM (20 mL), quenched with saturated $Na_2S_2O_3$ (15 mL) and washed with saturated $NaHCO_3$ (2×15 mL), The organic layer was dried over anhydrous $Na_2SO_4$, filtered and concentrated in vacuo to give the title compound (59.0 mg, 98% yield) as yellow solid. LC-MS ($ESI^+$) m/z 435.4 $(M+H)^+$.

(1R,4R)-4-(3-oxo-12H-5,11-dioxa-2-aza-1(5,6)-indazola-4(2,6)-pyridinacycloundecaphane-12-yl)cyclohexane-1-carbaldehyde (Intermediate BML)

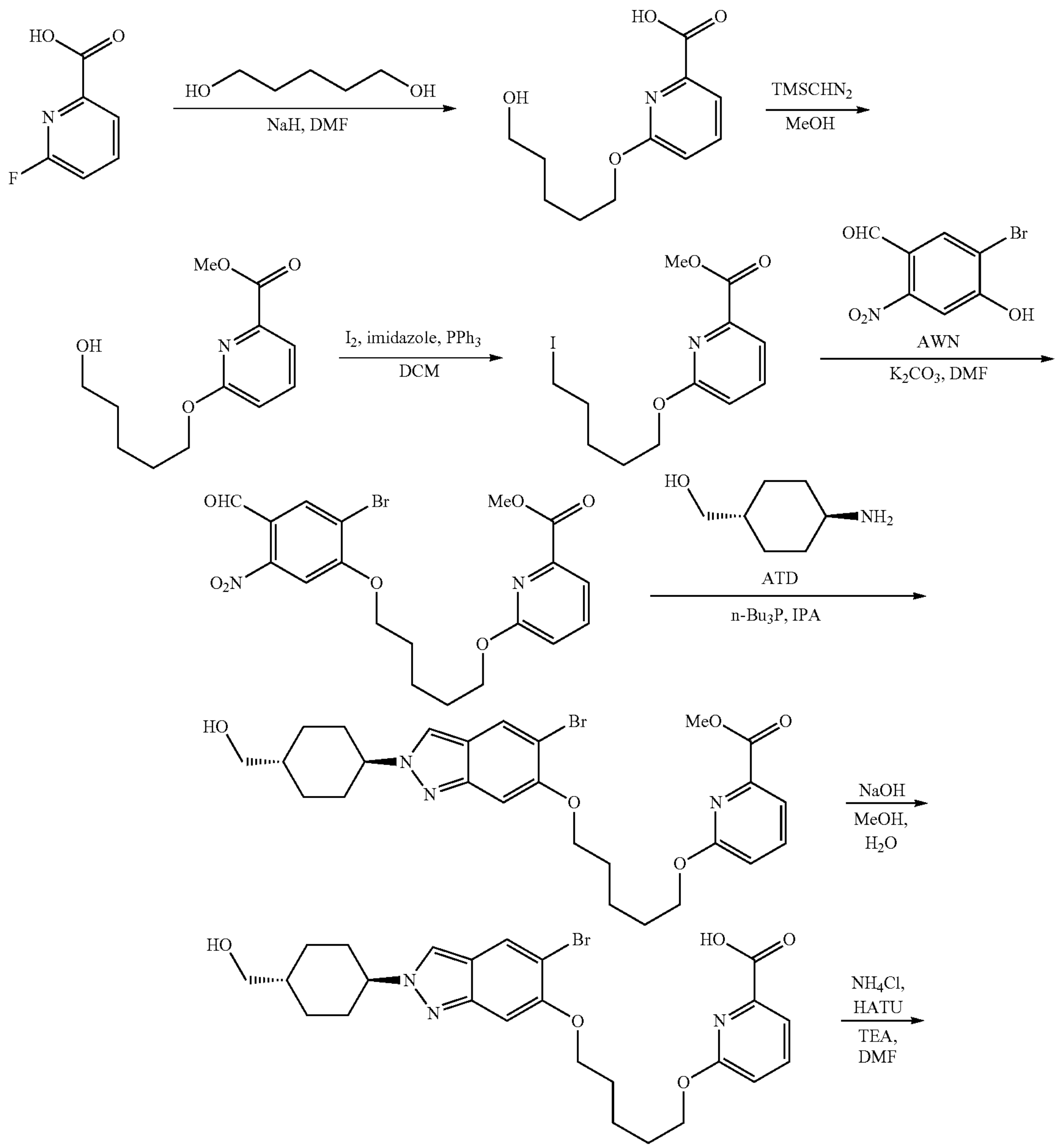

-continued

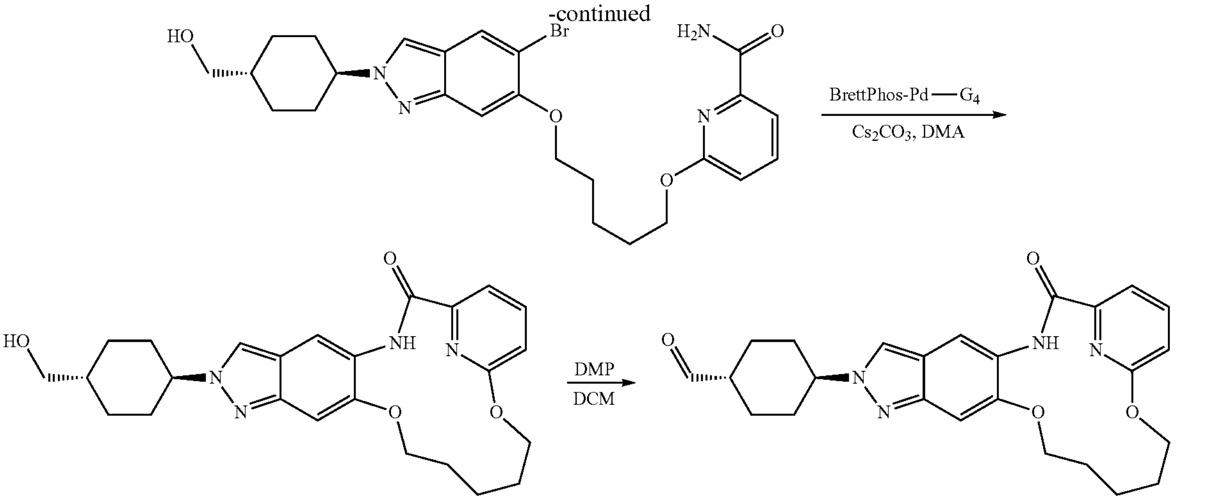

BML

Step 1—6-(5-Hydroxypentoxy)pyridine-2-carboxylic acid

To a solution of pentane-1, 5-diol (18.5 g, 177 mmol, 18.6 mL, CAS #111-29-5) in DMF (30.0 mL) was added NaH (2.83 g, 70.9 mmol, 60% dispersion in mineral oil) at 0° C. The mixture was stirred at 0° C. for thirty minutes. Next, 6-Fluoropyridine-2-carboxylic acid (5.00 g, 35.4 mmol, CAS #402-69-7) was added, and the mixture was stirred at 60° C. for 16 hrs. On completion, the reaction mixture was quenched by addition $H_2O$ (5 mL) and concentrated in vacuo to give a residue. The residue was purified by reversed-phase (0.1% FA condition) to give the compound (5.00 g, 62% yield) as a yellow solid. $^1$H NMR (400 MHz, $CDCl_3$-d) 6 7.85-7.78 (m, 2H), 7.03 (dd, J=2.0, 7.2 Hz, 1H), 4.36 (t, J=6.4 Hz, 2H), 3.71 (t, J=6.4 Hz, 2H), 1.93-1.81 (m, 2H), 1.73-1.62 (m, 2H), 1.62-1.51 (m, 2H).

Step 2—Methyl 6-(5-hydroxypentoxy)pyridine-2-carboxylate

To a solution of 6-(5-hydroxypentoxy)pyridine-2-carboxylic acid (5.00 g, 22.2 mmol) in MeOH (50.0 mL) was added $TMSCHN_2$ (2 M, 16.6 mL) at 0° C. The mixture was stirred at 20° C. for 16 hrs. On completion, the reaction mixture was quenched by addition HOAc (7 mL) by dripping slowly, and then concentrated in vacuo to remove MeOH. The mixture was diluted with $H_2O$ (50 mL) and extracted with EA (3×50 mL). The combined organic layers were washed with brine (2×100 mL), dried over $Na_2SO_4$, filtered and concentrated in vacuo to give a residue. The residue was purified by column chromatography ($SiO_2$, petroleum ether/ethyl acetate=10/1 to 5/1, PE:EA=2:1, Rf=0.26) to give the title compound (4.20 g, 79% yield) as a yellow oil. $^1$H NMR (400 MHz, $CDCl_3$-d) δ 7.72-7.65 (m, 2H), 6.95-6.88 (m, 1H), 4.41 (t, J=6.5 Hz, 2H), 3.96 (s, 3H), 3.69 (t, J=6.4 Hz, 2H), 1.88-1.78 (m, 2H), 1.73-1.63 (m, 2H), 1.61-1.54 (m, 3H).

Step 3—Methyl 6-(5-iodopentoxy)pyridine-2-carboxylate

To a solution of methyl 6-(5-hydroxypentoxy)pyridine-2-carboxylate (4.20 g, 17.6 mmol) in DCM (50.0 mL) was added $PPh_3$ (5.52 g, 21.1 mmol), imidazole (1.43 g, 21.1 mmol) and $I_2$ (5.35 g, 21.1 mmol, 4.24 mL). The mixture was stirred at 25° C. for 1 hr. On completion, the reaction mixture was diluted with $H_2O$ (3 mL) and extracted with DCM (2×50 mL). The combined organic layer was washed with brine (2×100 mL), dried over anhydrous $Na_2SO_4$, filtered and concentrated in vacuo to give a residue. The residue was purified by column chromatography ($SiO_2$, petroleum ether/ethyl acetate=0/1 to 10/1, PE:EA=10:1, Rf=0.32) to give the title compound (5.90 g, 96% yield) as a yellow oil. $^1$H NMR (400 MHz, $CDCl_3$-d) 6 7.73-7.66 (m, 2H), 6.92 (dd, J=2.4, 7.2 Hz, 1H), 4.41 (t, J=6.4 Hz, 2H), 3.97 (s, 3H), 3.23 (t, J=7.2 Hz, 2H), 1.96-1.89 (m, 2H), 1.87-1.78 (m, 2H), 1.64-1.58 (m, 2H).

Step 4—Methyl 6-[5-(2-Bromo-4-formyl-5-nitro-phenoxy)pentoxy]pyridine-2-carboxylate To a solution of methyl 6-(5-iodopentoxy)pyridine-2-carboxylate (1.40 g, 4.01 mmol) and 5-bromo-4-hydroxy-2-nitrobenzaldehyde (986 mg, 4.01 mmol, Intermediate AWN) in DMF (20.0 mL) was added $K_2CO_3$ (1.66 g, 12.03 mmol). The mixture was stirred at 60° C. for 16 hrs. On completion, the reaction mixture was filtered, and the filtrate was acidified with FA (2 mL), then concentrated in vacuo to give the residue. The residue was purified by reversed-phase (0.1% FA condition) to give the title compound (1.30 g, 69% yield) as a brown solid. $^1$H NMR (400 MHz, DMSO-$d_6$) δ 10.03 (s, 1H), 8.14 (s, 1H), 7.85 (t, J=7.8 Hz, 1H), 7.78 (s, 1H), 7.64 (d, J=7.2 Hz, 1H), 7.04 (d, J=8.4 Hz, 1H), 4.32 (q, J=6.4 Hz, 4H), 3.85 (s, 3H), 1.91-1.78 (m, 4H), 1.66-1.55 (m, 2H). LC-MS ($ESI^+$) m/z 467.0 $(M+H)^+$.

Step 5—Methyl 6-[5-[5-bromo-2-[4-(hydroxymethyl)cyclohexyl]indazol-6-yl]oxypentoxy]pyridine-2-carboxylate A mixture of methyl 6-[5-(2-bromo-4-formyl-5-nitro-phenoxy)pentoxy]pyridine-2-carboxylate (1.30 g, 2.78 mmol) and (4-aminocyclohexyl)methanol (395 mg, 3.06 mmol, Intermediate ATD) in IPA (30.0 mL) was stirred at 80° C. for 16 hrs under $N_2$. It was cooled to 25° C., then tributylphosphane (1.69 g, 8.35 mmol, 2.06 mL) was added. The reaction mixture was stirred at 80° C. for 16 hrs. On completion, the reaction mixture was concentrated in vacuo to give the residue. The residue was purified by column chromatography ($SiO_2$, petroleum ether/ethyl acetate=1/1 to 0/1, PE:EA=0:1, Rf=0.35) to give the title compound methyl (1.50 g, 98% yield) as a white solid. LC-MS ($ESI^+$) m/z 548.1 $(M+H)^+$.

Step 6—6-[5-[5-Bromo-2-[4-(hydroxymethyl)cyclohexyl]indazol-6-yl]oxypentoxy]pyridine-2- carboxylic acid To a solution of methyl 6-[5-[5-bromo-2-[4-(hydroxymethyl)cyclohexyl]indazol-6-yl]oxypentoxy] pyridine-2-carboxylate (1.50 g, 2.74 mmol) in MeOH (15.0 mL) and $H_2O$ (3.00 mL) was added LiOH $H_2O$ (576 mg, 13.7 mmol). The mixture was stirred at 60° C. for 2 hrs. On completion, the reaction mixture was concentrated in vacuo to remove MeOH, and then diluted with $H_2O$ (50 mL) and extracted with EA (2×50 mL). The combined organic layers were discarded. The combined water layers were acidified with 1 N HCl until the pH=3 and extracted with EA (3×50 mL). The combined organic layers were washed with brine (2×100 mL), dried over anhydrous $Na_2SO_4$, filtered and concentrated in vacuo to give the title compound (1.02 g, 69% yield) as an off-white solid. $^1H$ NMR (400 MHz, DMSO-$d_6$) δ 13.51-12.42 (m, 1H), 8.25 (s, 1H), 7.94 (s, 1H), 7.84 (dd, J=7.6, 8.4 Hz, 1H), 7.63 (d, J=7.2 Hz, 1H), 7.09 (s, 1H), 7.02 (d, J=7.7 Hz, 1H), 4.58-4.42 (m, 1H), 4.41-4.31 (m, 3H), 4.07 (t, J=6.2 Hz, 2H), 3.28 (br d, J=6.2 Hz, 2H), 2.16-2.07 (m, 2H), 1.92-1.78 (m, 8H), 1.68-1.58 (m, 2H), 1.52-1.40 (m, 1H), 1.17-1.07 (m, 2H). LC-MS ($ESI^+$) m/z 534.2 $(M+H)^+$.

Step 7—6-[5-[5-Bromo-2-[4-(hydroxymethyl)cyclohexyl]indazol-6-yl]oxypentoxy]pyridine-2- carboxamide To a solution of 6-[5-[5-bromo-2-[4-(hydroxymethyl)cyclohexyl]indazol-6-yl]oxypentoxy]pyridine-2-carboxylic acid (1.02 g, 1.92 mmol) and $NH_4Cl$ (2.05 g, 38.3 mmol) in DMF (10.0 mL) was added TEA (581 mg, 5.75 mmol, 800 uL) and HATU (1.09 g, 2.87 mmol). The mixture was stirred at 20° C. for 1 hr. On completion, the reaction mixture was diluted with $H_2O$ (60 mL) and extracted with EA (4×60 mL). The combined organic layers were washed with brine (2×100 mL), dried over anhydrous $Na_2SO_4$, filtered and concentrated in vacuo to give a residue. The residue was triturated with EA (5 mL) at 80° C. for 30 mins to give the title compound (1.00 g, 98% yield) as an off-white solid. $^1H$ NMR (400 MHz, DMSO-$d_6$) δ 8.26 (s, 1H), 7.97 (s, 1H), 7.94 (s, 1H), 7.83 (dd, J=7.6, 8.0 Hz, 1H), 7.67-7.55 (m, 2H), 7.52 (dd, J=4.4, 8.4 Hz, 1H), 7.09 (s, 1H), 6.97 (d, J=8.4 Hz, 1H), 4.41 (t, J=6.4 Hz, 2H), 4.38-4.31 (m, 1H), 4.07 (t, J=6.4 Hz, 2H), 3.28 (d, J=6.2 Hz, 2H), 2.16-2.07 (m, 2H), 1.92-1.78 (m, 8H), 1.69-1.60 (m, 2H), 1.51-1.39 (m, 1H), 1.19-1.07 (m, 2H). LC-MS ($ESI^+$) m/z 531.2 $(M+H)^+$.

Step 8—12-((1R,4R)-4-(hydroxymethyl)cyclohexyl)-12H-5,11-dioxa-2-aza-1(5,6)-indazola-4(2,6)-pyridinacycloundecaphan-3-one A mixture of 6-[5-[5-bromo-2-[4-(hydroxymethyl)cyclohexyl]indazol-6-yl]oxypentoxy]pyridine- 2-carboxamide (300 mg, 564 umol), $Cs_2CO_3$ (367 mg, 1.13 mmol) and BrettPhos (Pd, G4) (51.9 mg, 56.5 umol) in DMA (60.0 mL) was degassed and purged with $N_2$ for 3 times, and then the mixture was stirred at 80° C. for 16 hrs under $N_2$ atmosphere. On completion, the reaction mixture was filtered and the filtrate was concentrated in vacuo to give a residue. The residue was purified by reversed phase (0.1% FA condition) to give the title compound (100 mg, 39% yield) as a yellow solid. $^1H$ NMR (400 MHz, DMSO-$d_6$) δ. 11.15 (s, 1H), 8.57 (s, 1H), 8.28 (s, 1H), 7.94 (t, J=7.8 Hz, 1H), 7.67 (d, J=7.2 Hz, 1H), 7.13-6.98 (m, 2H), 4.49-4.40 (m, 2H), 4.33 (t, J=11.2 Hz, 1H), 4.19 (s, 2H), 3.28 (d, J=6.0 Hz, 2H), 2.27-2.08 (m, 4H), 1.95-1.81 (m, 6H), 1.76-1.70 (m, 2H), 1.46 (d, J=6.0 Hz, 1H), 1.19-1.08 (m, 2H). LC-MS ($ESI^+$) m/z 451.2 $(M+H)^+$.

Step 9—(1R,4R)-4-(3-oxo-12H-5,11-dioxa-2-aza-1(5,6)-indazola-4(2,6)-pyridinacycloundecaphane-12-yl)cyclohexane-1-carbaldehyde To a solution of 12-((1r,4r)-4-(hydroxymethyl)cyclohexyl)-12H-5,11-dioxa-2-aza-1(5,6)-indazola-4(2,6)-pyridinacycloundecaphan-3-one (80.0 mg, 177 umol) in DCM (5.00 mL) was added DMP (97.9 mg, 231 umol, 71.5 uL) and the mixture was stirred at 20° C. for 2 hrs. On completion, the reaction mixture was quenched by addition saturated solution of $Na_2S_2O_3$ (3 mL), and saturated solution of $NaHCO_3$ (5 mL), then extracted with DCM (3×20 mL). The combined organic layer was washed with brine (2×50 mL), dried over anhydrous $Na_2SO_4$, filtered and concentrated in vacuo to give the title compound (79.0 mg, 99% yield) as a yellow solid. $^1H$ NMR (400 MHz, DMSO-$d_6$) δ 11.15 (s, 1H), 9.64 (s, 1H), 8.58 (s, 1H), 8.29 (s, 1H), 7.95 (t, J=7.8 Hz, 1H), 7.68 (d, J=7.2 Hz, 1H), 7.14-7.02 (m, 2H), 4.56-4.43 (m, 2H), 4.41-4.32 (m, 1H), 4.26-4.15 (m, 2H), 2.44-2.37 (m, 1H), 2.26-2.16 (m Hz, 4H), 2.10 (d, J=12.4 Hz, 2H), 1.98-1.88 (m, 4H), 1.79-1.70 (m, 2H), 1.49-1.39 (m, 2H).LC-MS ($ESI^+$) m/z 449.3 $(M+H)^+$.

Methyl 5-chloro-2-methyl-4-nitrobenzoate (Intermediate BMM)

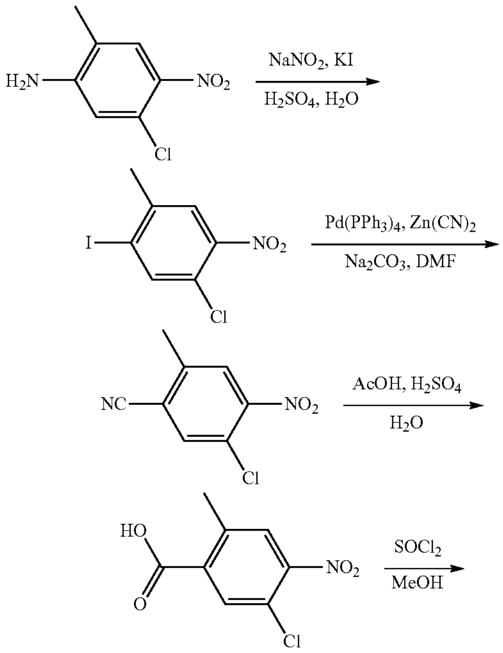

-continued

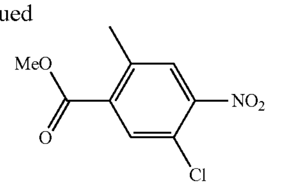

BMM

Step 1—1-Chloro-5-iodo-4-methyl-2-nitrobenzene

To a mixture of 5-chloro-2-methyl-4-nitro-aniline (10 g, 53.6 mmol, CAS #13852-51-2) in $H_2SO_4$ (3 M, 100 mL) was added dropwise a solution of $NaNO_2$ (3.70 g, 53.6 mmol) in $H_2O$ (10 mL) over 1 hr at 0° C. Then a solution of KI (10.7 g, 64.3 mmol) in $H_2O$ (10 mL) was added. The reaction mixture was stirred at 0° C. for 1 hr and allowed to warm to 25° C. for 1 hr. On completion, the reaction mixture was diluted with water (500 mL) and extracted with EA (3x200 mL). The organic layer was washed with saturated $NaHCO_3$ (aq., 2x500 mL) and brine (3x300 mL). The organic layer was dried over $Na_2SO_4$, filtered and concentrated in vacuo. The residue was purified by silica gel chromatography (PE:EA=1:0 to 100:1) to give the title compound (12.2 g, 76% yield) as yellow solid. $^1H$ NMR (400 MHz, DMSO-$d_6$) δ 8.24 (s, 1H), 8.04 (s, 1H), 2.43 (s, 3H).

Step 2—5-Chloro-2-methyl-4-nitrobenzonitrile

To a mixture of 1-chloro-5-iodo-4-methyl-2-nitro-benzene (11.6 g, 39.2 mmol), $Pd(PPh_3)_4$(4.53 g, 3.92 mmol) and $Na_2CO_3$ (8.31 g, 78.4 mmol) in DMF (80 mL) was added $Zn(CN)_2$ (2.76 g, 23.5 mmol, 1.49 mL). The reaction mixture was stirred at 50° C. for 24 hrs under $N_2$. On completion, the reaction mixture was diluted with water (500 mL) and extracted with EA (3x300 mL). The organic layer was washed with brine (3x300 mL), dried over $Na_2SO_4$, filtered and concentrated in vacuo. The residue was purified by silica gel chromatography (PE:EA=1:0 to 80:1) to give the title compound (6.30 g, 82% yield) as yellow solid. $^1H$ NMR (400 MHz, $CDCl_3$) δ 7.82-7.79 (m, 2H), 2.64 (s, 3H).

Step 3—5-Chloro-2-methyl-4-nitrobenzoic acid

A mixture of 5-chloro-2-methyl-4-nitro-benzonitrile (2.20 g, 11.2 mmol) in a mixed of AcOH (20 mL), $H_2O$ (20 mL) and $H_2SO_4$ (20 mL) was stirred at 120° C. for 16 hrs. On completion, the reaction mixture was diluted with water (40 mL) and filtered. The filtrate cake was dried in vacuo to give the title compound (2.20 g, 91% yield) as off-white solid. $^1H$ NMR (400 MHz, $CDCl_3$) δ 8.23 (s, 1H), 7.76 (s, 1H), 2.71 (s, 3H).

Step 4—Methyl 5-chloro-2-methyl-4-nitrobenzoate

To a mixture of 5-chloro-2-methyl-4-nitro-benzoic acid (2.20 g, 10.2 mmol) in MeOH (40 mL) was dropwise $SOCl_2$ (1.82 g, 15.3 mmol, 1.11 mL) at 0° C. The reaction mixture was stirred at 70° C. for 16 hrs under $N_2$. On completion, the reaction mixture was concentrated in vacuo and the residue was diluted with EA (100 mL) and washed with brine (3x100 mL). The organic layer was dried over $Na_2SO_4$, filtered and concentrated in vacuo to give the title compound (2.30 g, 98% yield) as off-white solid. $^1H$ NMR (400 MHz, $CDCl_3$) δ 8.08 (s, 1H), 7.74 (s, 1H), 3.96 (s, 3H), 2.64 (s, 3H).

N-[7-fluoro-2-(4-formylcyclohexyl)-6-methoxy-indazol-5-yl]-6-(trifluoromethyl)pyridine-2-carboxamide (Intermediate BNX)

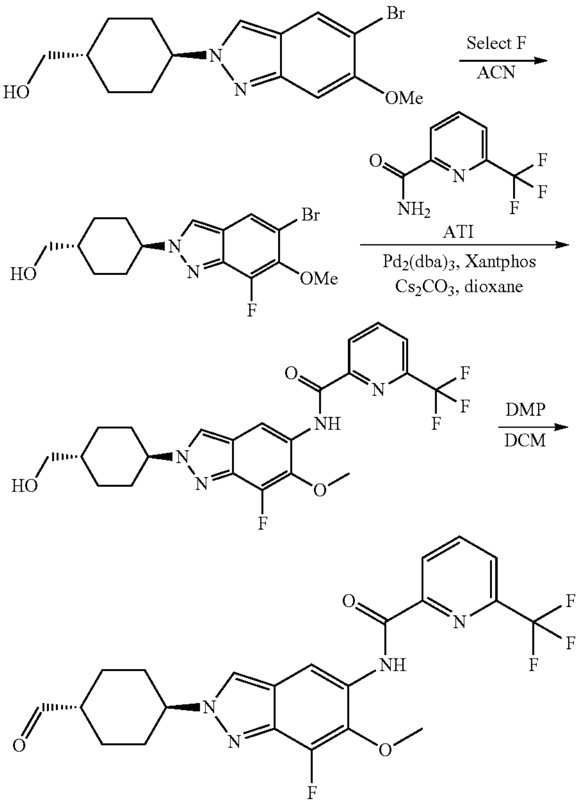

BNX

Step 1—[4-(5-Bromo-7-fluoro-6-methoxy-indazol-2-yl)cyclohexyl]methanol

To a solution of [4-(5-bromo-6-methoxy-indazol-2-yl) cyclohexyl]methanol (5.00 g, 14.7 mmol, synthesized via Steps 1-3 of Intermediate ATE) in ACN (50 mL) was added Select F (6.27 g, 17.7 mmol) and the reaction mixture was stirred at 20° C. for 12 hrs. On completion, the mixture was concentrated in vacuo to give the residue. The residue was purified by reverse phase (0.1% FA condition) to give the title compound (1.70 g, 32% yield) as a yellow solid. LC-MS ($ESI^+$) m/z 357.0 $(M+H)^+$.

Step 2—N-[7-fluoro-2-[4-(hydroxymethyl)cyclohexyl]-6-methoxy-indazol-5-yl]-6-(trifluoromethyl) pyridine-2-carboxamide A mixture of [4-(5-bromo-7-fluoro-6-methoxy-indazol-2-yl)cyclohexyl]methanol (300 mg, 839 umol), 6-(trifluoromethyl)pyridine-2-carboxamide (239.50 mg, 1.26 mmol, Intermediate ATI), Xantphos (97.2 mg, 168 umol), $Pd_2(dba)_3$ (76.9 mg, 84.0 umol) and $Cs_2CO_3$ (547 mg, 1.68 mmol) in dioxane (6 mL) was de-gassed and heated at 90°

C. for 12 hrs. On completion, the mixture was filtered and the filtrate was concentrated in vacuo to give the residue. The residue was purified by reverse phase (0.1% FA condition) to give the title compound (200 mg, 51% yield) as yellow solid. LC-MS (ESI+) m/z 467.1 $(M+H)^+$.

Step 3—N-[7-fluoro-2-(4-formylcyclohexyl)-6-methoxy-indazol-5-yl]-6-(trifluoromethyl)pyridine-2- carboxamide To a mixture of N-[7-fluoro-2-[4-(hydroxymethyl)cyclohexyl]-6-methoxy-indazol-5-yl]-6-(trifluoro methyl)pyridine-2-carboxamide (100 mg, 214 umol) in DCM (3 mL) was added DMP (100 mg, 236 umol) at 0° C. The mixture was then stirred at 20° C. for 0.5 hour. On completion, the mixture was poured into the water (30 mL) and the aqueous phase was extracted with ethyl acetate (2×20 mL). The combined organic phase was washed with brine (2×20 mL), dried with anhydrous $Na_2SO_4$, filtered and concentrated in vacuo to give the title compound (95.0 mg, 95% yield) as a brown solid. $^1H$ NMR (400 MHz, $CDCl_3$) δ 10.74 (s, 1H), 9.75 (s, 1H), 8.63 (d, J=0.8 Hz, 1H), 8.51 (d, J=8.0 Hz, 1H), 8.16 (d, J=8.0 Hz, 1H), 7.96 (d, J=2.8 Hz, 1H), 7.93-7.88 (m, 1H), 4.44-4.40 (m, 1H), 4.26-4.18 (m, 3H), 2.48-2.37 (m, 3H), 2.34-2.24 (m, 2H), 2.10-2.07 (m, 2H), 1.63-1.57 (m, 2H).

N-[3,7-difluoro-2-(4-formylcyclohexyl)-6-methoxy-indazol-5-yl]-6-(trifluoromethyl)pyridine-2-carboxamide (Intermediate BNY)

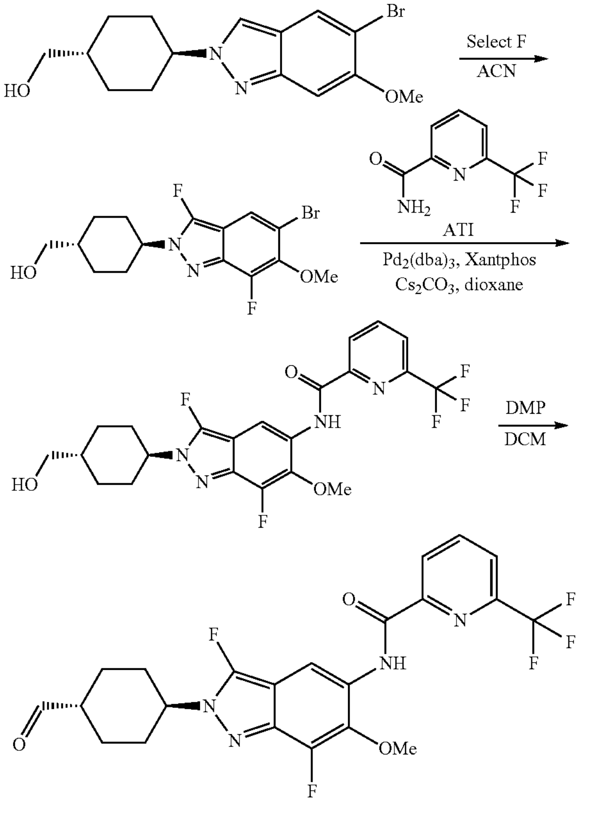

BNY

Step 1—[4-(5-Bromo-3,7-difluoro-6-methoxy-indazol-2-yl)cyclohexyl]methanol

To a solution of [4-(5-bromo-6-methoxy-indazol-2-yl)cyclohexyl]methanol (5.00 g, 14.7 mmol, synthesized via Steps 1-3 of Intermediate ATE) in ACN (50 mL) was added Select F (6.27 g, 17.6 mmol, CAS #140681-55-6). The reaction mixture was stirred at 20° C. for 12 hours. On completion, the mixture was concentrated in vacuo. The residue was purified by reverse phase (0.1% FA) to give the title compound (600 mg, 10% yield) as a yellow solid. LCMS (ESI+) m/z 375.0 $(M+H)^+$.

Step 2—N-[3,7-difluoro-2-[4-(hydroxymethyl)cyclohexyl]-6-methoxy-indazol-5-yl]-6-(trifluoro methyl)pyridine-2-carboxamide To a solution of [4-(5-bromo-3,7-difluoro-6-methoxy-indazol-2-yl)cyclohexyl]methanol (200 mg, 533 umol), 6-(trifluoromethyl)pyridine-2-carboxamide (101 mg, 533 umol, Intermediate ATI) in dioxane (3 mL) was added $Cs_2CO_3$ (347 mg, 1.07 mmol), BrettPhos Pd G3 (48.3 mg, 53.3 umol) at 25° C. Then the mixture was stirred at 80° C. for 16 hours under $N_2$. On completion, the reaction mixture was filtered and concentrated in vacuo to give a residue. The residue was purified by silica gel chromatography (PE: EA=2:1) to give the title compound (160 mg, 61% yield) as white solid. $^1H$ NMR (400 MHz, $CDCl_3$) δ 10.61 (s, 1H), 8.46-8.37 (m, 2H), 8.07 (t, J=8.0 Hz, 1H), 7.85-7.77 (m, 1H), 4.39-4.28 (m, 1H), 4.12 (d, J=2.4 Hz, 3H), 3.48 (d, J=6.4 Hz, 2H), 2.18-2.03 (m, 4H), 2.01-1.94 (m, 2H), 1.61 (m, 1H), 1.21-1.12 (m, 2H).

Step 3—N-[3,7-difluoro-2-(4-formylcyclohexyl)-6-methoxy-indazol-5-yl]-6-(trifluoromethyl)pyridine -2-carboxamide A mixture of N-[3,7-difluoro-2-[4-(hydroxymethyl)cyclohexyl]-6-methoxy-indazol-5-yl]-6-(trifluoromethyl)pyridine-2-carboxamide (120 mg, 247 umol) and DMP (136 mg, 322 umol) in DCM (3 mL) was stirred at 25° C. for 3 hours. On completion, the reaction mixture was quenched with sat. aq. $Na_2S_2O_3$ (1 mL), then sat. aq. $NaHCO_3$ was added until the pH=7~8, then the mixture was extracted with ethyl acetate (3×10 mL). The combined organic layer was washed with brine (2×10 mL), dried over $Na_2SO_4$, filtered and concentrated in vacuo to give the title compound (110 mg, 92% yield) as yellow solid. $^1H$ NMR (400 MHz, $CDCl_3$) δ 10.62 (s, 1H), 9.65 (s, 1H), 8.45-8.37 (m, 2H), 8.07 (t, J=7.6 Hz, 1H), 7.81 (d, J=7.6 Hz, 1H), 4.41-4.27 (m, 1H), 4.13 (d, J=2.4 Hz, 3H), 2.41-2.28 (m, 1H), 2.22-2.12 (m, 6H), 1.48-1.40 (m, 2H).

N-[3-fluoro-2-(4-formylcyclohexyl)-6-methoxy-indazol-5-yl]-6-(trifluoromethyl)pyridine-2-carboxamide (Intermediate BNZ)

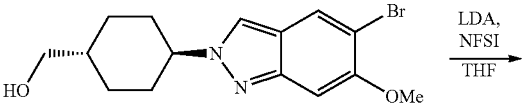

-continued

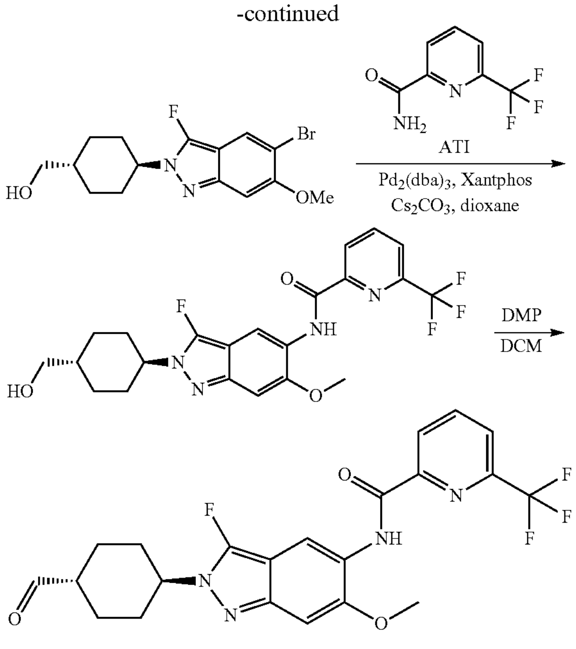

BNZ

Step 1—[4-(5-Bromo-3-fluoro-6-methoxy-indazol-2-yl)cyclohexyl]methanol

To a mixture of [4-(5-bromo-6-methoxy-indazol-2-yl)cyclohexyl]methanol (3.00 g, 8.84 mmol, synthesized via Steps 1-3 of Intermediate ATE) in THE (30 mL) was added LDA (2 M, 13.3 mL) at −78° C. The mixture was then warmed to 20° C. and stirred for 1.0 hour. NFSI (5.58 g, 17.7 mmol) was then added and the mixture was stirred at 20° C. for 2 hours. On completion, the mixture was poured into the water (30 mL) and extracted with ethyl acetate (2×20 mL). The combined organic phases were washed with brine (2×30 mL), dried over anhydrous $Na_2SO_4$, filtered and concentrated in vacuo to give a residue. The residue was purified by reverse phase (0.1% FA condition) to give the title compound (520 mg, 16% yield) as brown oil. $^1H$ NMR (400 MHz, $CDCl_3$) δ 7.74 (s, 1H), 6.85 (d, J=1.6 Hz, 1H), 4.39-4.29 (m, 1H), 3.91 (s, 3H), 3.55 (d, J=6.0 Hz, 2H), 2.16-2.08 (m, 4H), 2.06-1.99 (m, 2H), 1.67-1.62 (m, 2H), 1.32-1.16 (m, 2H).

Step 2—N-[3-fluoro-2-[4-(hydroxymethyl)cyclohexyl]-6-methoxy-indazol-5-yl]-6-(trifluoromethyl)pyridine-2-carboxamide A mixture of [4-(5-bromo-3-fluoro-6-methoxy-indazol-2-yl)cyclohexyl]methanol (100 mg, 279 umol), 6-(trifluoromethyl)pyridine-2-carboxamide (58.5 mg, 307 umol, Intermediate ATI), Xantphos (32.4 mg, 55.9 umol), $Pd_2(dba)_3$ (25.6 mg, 828 umol) and $Cs_2CO_3$ (182 mg, 560 umol)) in dioxane (3.0 mL) was de-gassed and heated at 100° C. for 12 hours under $N_2$. On completion, the mixture was filtered and the filtrate was concentrated in vacuo to give a residue. The residue was purified by reverse phase (0.1% FA condition) to give the title compound (105 mg, 80% yield) as brown solid. $^1H$ NMR (400 MHz, $CDCl_3$) δ 10.68 (s, 1H), 8.70 (s, 1H), 8.50 (d, J=7.6 Hz, 1H), 8.13 (d, J=7.6 Hz, 1H), 7.87 (d, J=7.6 Hz, 1H), 6.90 (d, J=1.2 Hz, 1H), 4.41-4.30 (m, 1H), 4.01 (s, 3H), 3.56 (d, J=6.0 Hz, 2H), 2.18-2.10 (m, 4H), 2.08-2.02 (m, 2H), 1.75-1.61 (m, 2H), 1.30-1.22 (m, 2H).

Step 3—N-[3-fluoro-2-(4-formylcyclohexyl)-6-methoxy-indazol-5-yl]-6-(trifluoromethyl)pyridine-2-carboxamide To a mixture of N-[3-fluoro-2-[4-(hydroxymethyl)cyclohexyl]-6-methoxy-indazol-5-yl]-6-(trifluoro methyl)pyridine-2-carboxamide (100 mg, 182 umol) in DCM (3.0 mL) was added DMP (92.7 mg, 219 umol) at 0° C. The mixture was then stirred at 20° C. for 0.5 hour. On completion, the mixture was poured into the water (30 mL) and the aqueous phase was extracted with ethyl acetate (2×20 mL). The combined organic phase was washed with brine (2×20 mL), dried with anhydrous $Na_2SO_4$, filtered and concentrated in vacuo to give the title compound (95.0 mg, 95% yield) as a brown solid. $^1H$ NMR (400 MHz, $CDCl_3$) δ 10.69 (s, 1H), 9.72 (d, J=0.7 Hz, 1H), 8.71 (s, 1H), 8.50 (d, J=7.8 Hz, 1H), 8.13 (t, J=7.8 Hz, 1H), 7.90-7.85 (m, 1H), 6.89 (d, J=1.6 Hz, 1H), 4.40-4.32 (m, 1H), 4.02 (s, 3H), 2.46-2.36 (m, 1H), 2.31-2.11 (m, 6H), 1.52 (dd, J=4.2, 12.8 Hz, 2H).

N-[2-(4-formylcyclohexyl)-6-morpholino-1-oxo-isoindolin-5-yl]-6-(trifluoromethyl)pyridine-2-carboxamide (Intermediate BOA)

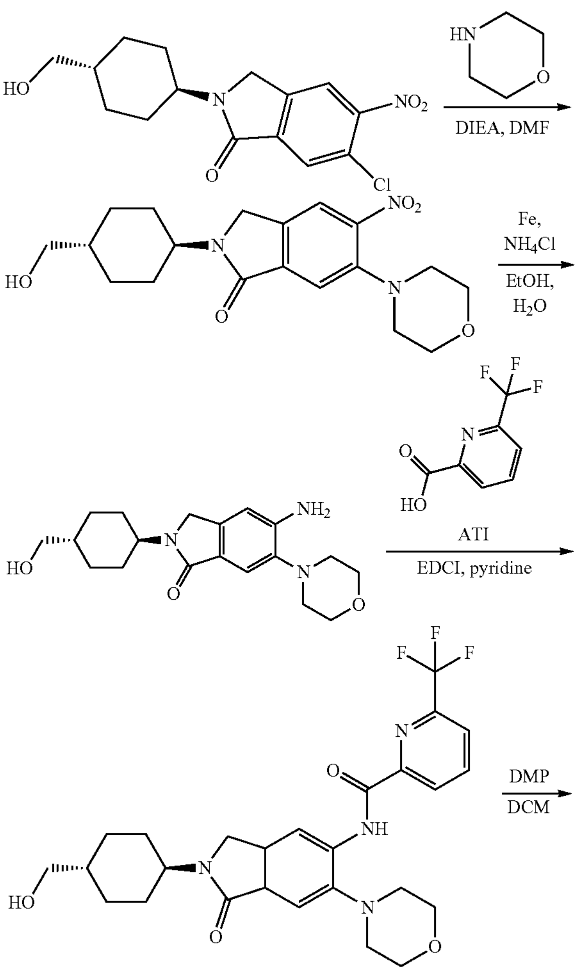

-continued

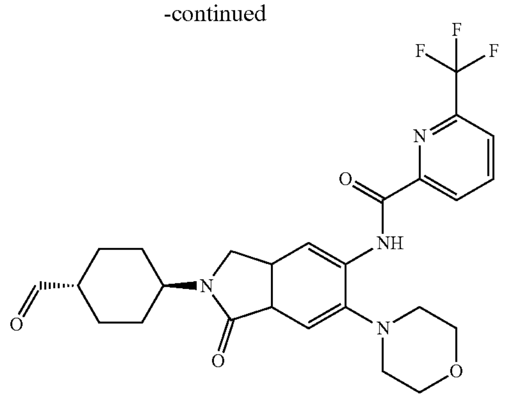

BOA

Step 1—2-[4-(Hydroxymethyl)cyclohexyl]-6-morpholino-5-nitro-isoindolin-1-one

To a solution of 6-chloro-2-[4-(hydroxymethyl)cyclohexyl]-5-nitro-isoindolin-1-one (300 mg, 923 umol, synthesized via Steps 1-2 of Intermediate BMI) and morpholine (104 mg, 1.20 mmol) in DMSO (4 mL) was added DIEA (238 mg, 1.85 mmol) at 25° C. The reaction mixture was stirred at 80° C. for 12 hours. On completion, the reaction mixture was concentrated in vacuo. The residue was purified by reverse phase (0.1% FA condition) to give the title compound (240 mg, 69% yield) as a yellow solid. LC-MS (ESI+) m/z 375.9 (M+H)+.

Step 2—5-Amino-2-[4-(hydroxymethyl)cyclohexyl]-6-morpholino-isoindolin-1-one

To a solution of 2-[4-(hydroxymethyl)cyclohexyl]-6-morpholino-5-nitro-isoindolin-1-one (140 mg, 372 umol) in $H_2O$ (2.5 mL), EtOH (2.5 mL) and THE (0.5 mL) was added $NH_4Cl$ (199 mg, 3.73 mmol) at 25° C. Then Fe (104 mg, 1.86 mmol) was added to the above mixture at 70° C., and the reaction mixture was stirred at 80° C. for 2 hours. On completion, the reaction mixture was filtered with celite and the filtrate was concentrated in vacuo. The residue was diluted with $H_2O$ (30 mL) and extracted with EA (3×10 mL). The combined organic layers were washed with brine (2×15 mL), dried over $Na_2SO_4$, filtered and concentrated in vacuo. The residue was purified by reverse phase (0.1% FA condition) to give the title compound (30.0 mg, 23% yield) as a white solid. LC-MS (ESI+) m/z 346.2 (M+H)+.

Step 3—N-[2-[4-(hydroxymethyl)cyclohexyl]-6-morpholino-1-oxo-isoindolin-5-yl]-6-(trifluoro methy)pyridine-2-carboxamide To a solution of 5-amino-2-[4-(hydroxymethyl)cyclohexyl]-6-morpholino-isoindolin-1-one (30.0 mg, 86.8 umol) and 6-(trifluoromethyl)pyridine-2-carboxylic acid (19.9 mg, 104 umol, Intermediate ATI) in pyridine (0.6 mL) was added EDCI (24.9 mg, 130 umol) and the reaction mixture was stirred at 25° C. for 12 hours. On completion, the reaction mixture was concentrated in vacuo. The residue was purified by reverse phase (0.1% FA condition) to give the title compound (20.0 mg, 44% yield) as a white solid. LC-MS (ESI+) m/z 519.2 (M+H)+.

Step 4—N-[2-(4-formylcyclohexyl)-6-morpholino-1-oxo-isoindolin-5-yl]-6-(trifluoromethyl)pyridine-2-carboxamide To a solution of N-[2-[4-(hydroxymethyl)cyclohexyl]-6-morpholino-1-oxo-isoindolin-5-yl]-6-(trifluoromethyl) pyridine-2-carboxamide (15.0 mg, 28.9 umol) in DCM (1 mL) was added DMP (15.9 mg, 37.6 umol) and the reaction mixture was stirred at 25° C. for 1 hour. On completion, the reaction mixture was quenched with sat. aq. $Na_2S_2O_3$ (1 mL) and sat. aq. $NaHCO_3$ (1 mL) and diluted with $H_2O$ (15 mL) and were extracted with DCM (3×5 mL). The combined organic layers were washed with brine 10 mL (2×5 mL), dried over $Na_2SO_4$, filtered and concentrated in vacuo to give the title compound (14.0 mg, 93% yield) as a white solid. LC-MS (ESI+) m/z 517.2 (M+H)+.

N-[2-(4-formylcyclohexyl)-6-[(1S,4S)-2-oxa-5-azabicyclo[2.2.1]heptan-5-yl]-1-oxo- isoindolin-5-yl]-6-(trifluoromethyl)pyridine-2-carboxamide (Intermediate BOB)

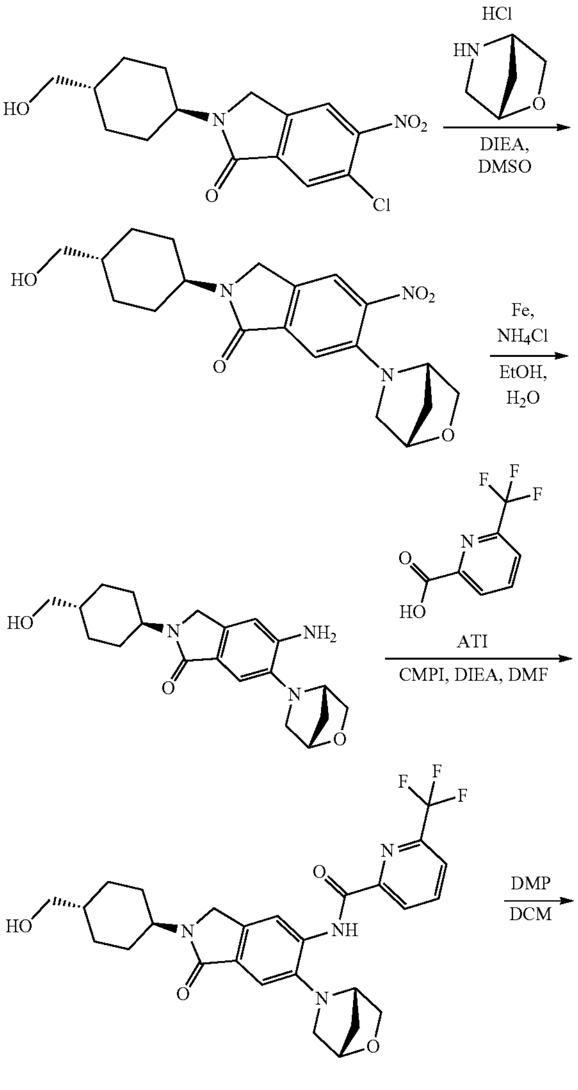

-continued

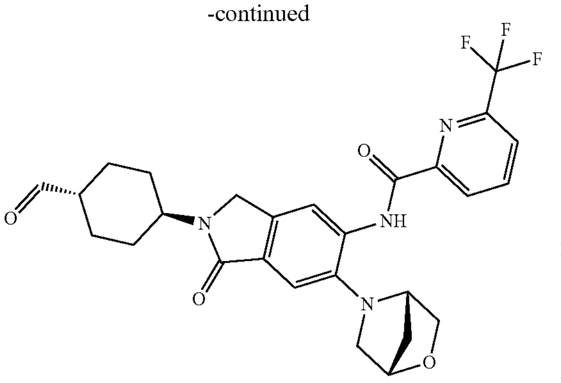

BOB

Step 1—2-[4-(Hydroxymethyl)cyclohexyl]-5-nitro-6-[(1S,4S)-2-oxa-5-azabicyclo[2.2.1]heptan-5-yl]isoindolin-1-one To a solution of 6-chloro-2-[4-(hydroxymethyl)cyclohexyl]-5-nitro-isoindolin-1-one (220 mg, 677 umol, synthesized via Steps 1-2 of Intermediate BMI) and (1S,4S)-2-oxa-5-azabicyclo[2.2.1]heptane (137.78 mg, 1.02 mmol, HCl salt, CAS #31560-06-2) in DMSO (3 mL) was added DIEA (175 mg, 1.35 mmol) at 25° C. The reaction mixture was then stirred at 80° C. for 36 hrs. On completion, the reaction mixture was concentrated in vacuo. The residue was purified by prep-HPLC (column: Phenomenex luna C18 150*25 mm*10 um; mobile phase: [water (0.2250% FA)-ACN]; B %: 22%-52%, 10 min) to give the title compound (45.0 mg, 17% yield) as a yellow solid. $^1H$ NMR (400 MHz, DMSO-$d_6$) δ 7.97 (s, 1H), 7.30 (s, 1H), 4.39 (s, 2H), 4.02-3.92 (m, 1H), 3.83-3.79 (m, 1H), 3.77-3.74 (m, 1H), 3.45 (d, J=10.0 Hz, 2H), 3.24 (d, J=5.6 Hz, 2H), 2.40 (d, J=10.0 Hz, 1H), 1.99-1.88 (m, 3H), 1.87-1.72 (m, 5H), 1.61-1.49 (m, 2H), 1.42-1.31 (m, 1H), 1.12-1.00 (in, 2H); LC-MS (ESI+) m/z 388.1 $(M+H)^+$.

Step 2—5-Amino-2-[4-(hydroxymethyl)cyclohexyl]-6-[(1S,4S)-2-oxa-5-azabicyclo[2.2.1]heptan-5-yl]isoindolin-1-one To a solution of 2-[4-(hydroxymethyl)cyclohexyl]-5-nitro-6-[(1S,4S)-2-oxa-5-azabicyclo[2.2.1]heptan -5-yl]isoindolin-1-one (45.0 mg, 116 umol) in THF (0.1 mL), EtOH (0.5 mL) and $H_2O$ (0.5 mL) was added $NH_4Cl$ (62.1 mg, 1.16 mmol) and Fe (32.4 mg, 580 umol) at 70° C. The reaction mixture was then stirred at 80° C. for 2 hrs. On completion, the reaction mixture was filtered with celite and the filtrate was concentrated in vacuo to give a residue. The residue was diluted with 30 mL $H_2O$ and extracted with EA (3×10 mL). The combined organic layers were washed with brine (2×15 mL), dried over by $Na_2SO_4$, filtered and concentrated in vacuo to give the title compound (35.0 mg, 84% yield) as a yellow solid. LC-MS (ESI+) m/z 358.1 $(M+H)^+$.

Step 3—N-[2-[4-(hydroxymethyl)cyclohexyl]-6-[(1S,4S)-2-oxa-5-azabicyclo[2.2.1]heptan-5-yl]-1-oxo-isoindolin-5-yl]-6-(trifluoromethyl)pyridine-2-carboxamide To a solution of 5-amino-2-[4-(hydroxymethyl)cyclohexyl]-6-[(1S,4S)-2-oxa-5-azabicyclo[2.2.1] heptan-5-yl] isoindolin-1-one (35.0 mg, 97.9 umol) and 6-(trifluoromethyl)pyridine -2-carboxylic acid (18.71 mg, 97.9 umol, Intermediate ATI) in DMF (3 mL) was added DIEA (25.3 mg, 195 umol) and CMPI (40.0 mg, 156 umol) and the reaction mixture was stirred at 25° C. for 1 hr. On completion, the reaction mixture was concentrated in vacuo. The residue was purified by reverse phase (0.1% FA condition) to give the title compound (17.0 mg, 32% yield) as a white solid. LC-MS (ESI+) m/z 531.4 $(M+H)^+$.

Step 4—N-[2-(4-formylcyclohexyl)-6-[(1S,4S)-2-oxa-5-azabicyclo[2.2.1]heptan-5-yl]-1-oxo- isoindolin-5-yl]-6-(trifluoromethyl)pyridine-2-carboxamide To a solution of N-[2-[4-(hydroxymethyl)cyclohexyl]-6-[(1S,4S)-2-oxa-5-azabicyclo[2.2.1]heptan-5- yl]-1-oxo-isoindolin-5-yl]-6-(trifluoromethyl)pyridine-2-carboxamide (17.0 mg, 32.0 umol) in DCM (1 mL) was added DMP (21.7 mg, 51.2 umol) and the reaction mixture was stirred at 25° C. for 1 hrs. On completion, the reaction mixture was quenched with 1 mL sat.aq. $Na_2S_2O_3$ and 1 mL $NaHCO_3$, and then the solution was diluted with 15 mL $H_2O$ and extracted with DCM (3×5 mL). The combined organic layers were washed with brine 10 mL (2×5 mL), dried over by $Na_2SO_4$, filtered and concentrated in vacuo to give the title compound (8.00 mg, 47% yield) as a white solid. LC-MS (ESI+) m/z 529.1 $(M+H)^+$.

N-[2-(4-formylcyclohexyl)-6-[(1R,4R)-2-oxa-5-azabicyclo[2.2.1]heptan-5-yl]-1-oxo- isoindolin-5-yl]-6-(trifluoromethyl)pyridine-2-carboxamide (Intermediate BOC)

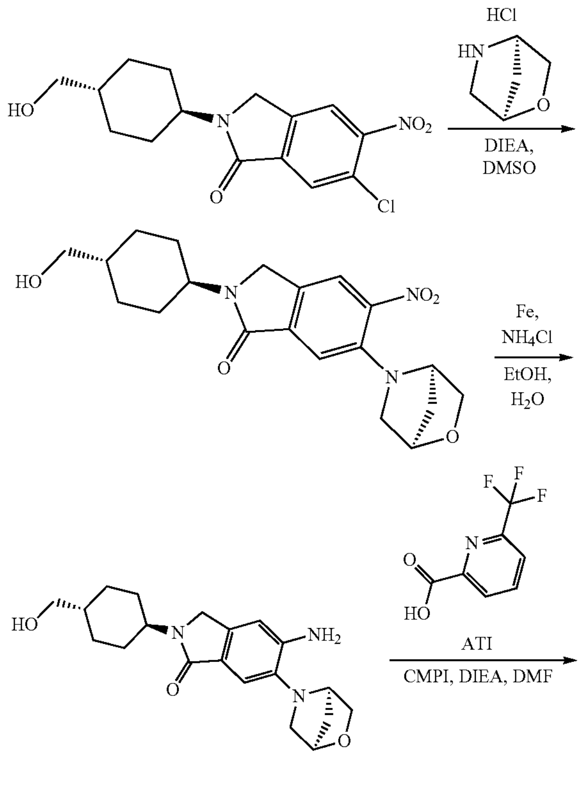

-continued

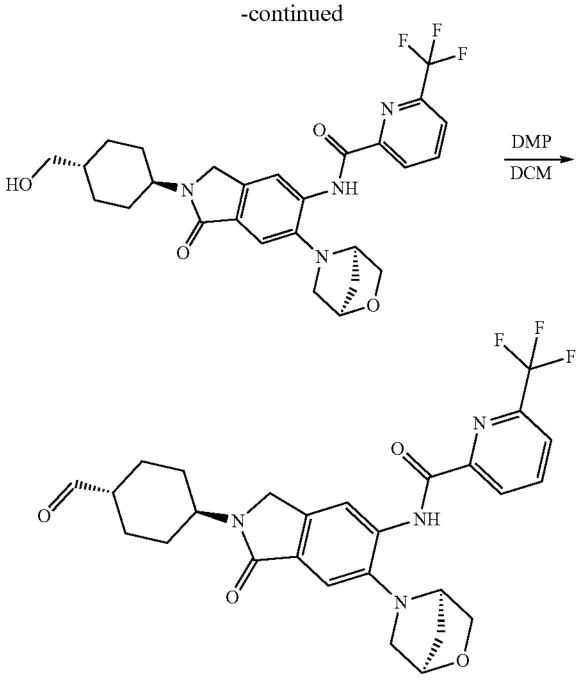

BOC

Step 1—2-[4-(Hydroxymethyl)cyclohexyl]-5-nitro-6-[(1R,4R)-2-oxa-5-azabicyclo[2.2.1] heptan-5-yl] isoindolin-1-one To a solution of 6-chloro-2-[4-(hydroxymethyl)cyclohexyl]-5-nitro-isoindolin-1-one (220 mg, 677 umol, synthesized via Steps 1-2 of Intermediate BMI) and (1R,4R)-2-oxa-5-azabicyclo[2.2.1]heptane (183 mg, 1.35 mmol, HCl salt, CAS #279-33-4) in DMSO (4 mL) was added DIEA (262 mg, 2.03 mmol) at 25° C. The reaction mixture was then stirred at 80° C. for 36 hrs. On completion, the reaction mixture was concentrated in vacuo. The residue was purified by reverse phase (0.1% FA condition) to give the title compound (55.0 mg, 20% yield) as a yellow solid. LC-MS (ESI+) m/z 388.4 $(M+H)^+$.

Step 2—5-Amino-2-[4-(hydroxymethyl)cyclohexyl]-6-[(1R,4R)-2-oxa-5-azabicyclo[2.2.1]heptan-5- yl]isoindolin-1-one To a solution of 2-[4-(hydroxymethyl)cyclohexyl]-5-nitro-6-[(1R,4R)-2-oxa-5-azabicyclo[2.2.1] heptan-5-yl]isoindolin-1-one (55.0 mg, 141 umol) in EtOH (1 mL), THE (0.2 mL) and $H_2O$ (1 mL) was added $NH_4Cl$ (75.9 mg, 1.42 mmol) and Fe (39.6 mg, 709 umol) at 70° C. Then the reaction mixture was stirred at 80° C. for 1 hr. On completion, the reaction mixture was filtered through celite and the filtrate was concentrated in vacuo to give a residue. The residue was diluted with 30 mL $H_2O$ and extracted with EA (3x10 mL). The combined organic layers were washed with brine (2x15 mL), dried over by $Na_2SO_4$, filtered and concentrated in vacuo to give the title compound (35.0 mg, 68% yield) as a yellow solid. LC-MS (ESI+) m/z 357.9 $(M+H)^+$.

Step 3—N-[2-[4-(hydroxymethyl)cyclohexyl]-6-[(1R,4R)-2-oxa-5-azabicyclo[2.2.1]heptan-5-yl]-1-oxo-isoindolin-5-yl]-6-(trifluoromethyl)pyridine-2-carboxamide To a solution of 5-amino-2-[4-(hydroxymethyl)cyclohexyl]-6-[(1R,4R)-2-oxa-5-azabicyclo[2.2.1] heptan-5-yl] isoindolin-1-one (35.0 mg, 97.9 umol) and 6-(trifluoromethyl)pyridine-2- carboxylic acid (18.7 mg, 97.9 umol, Intermediate ATI) in DMF (1 mL) was added DIEA (25.3 mg, 195 umol) and CMPI (40.0 mg, 156 umol). The mixture was stirred at 25° C. for 1 hr. On completion, the reaction mixture was concentrated in vacuo. The residue was purified by reverse phase (0.1% FA condition) to give the title compound (26.0 mg, 50% yield) as a white solid. LC-MS (ESI+) m/z 531.4 $(M+H)^+$.

Step 4—N-[2-(4-formylcyclohexyl)-6-[(1R,4R)-2-oxa-5-azabicyclo[2.2.1]heptan-5-yl]-1-oxo- isoindolin-5-yl]-6-(trifluoromethyl)pyridine-2-carboxamide To a solution of N-[2-[4-(hydroxymethyl)cyclohexyl]-6-[(1R,4R)-2-oxa-5-azabicyclo[2.2.1]heptan-5- yl]-1-oxo-isoindolin-5-yl]-6-(trifluoromethyl)pyridine-2-carboxamide (26.0 mg, 49.0 umol) in DCM (1 mL) was added DMP (33.2 mg, 78.4 umol) and the reaction mixture was stirred at 25° C. for 1 hr. On completion, the reaction mixture was quenched with 1 mL sat. aq. $Na_2S_2O_3$ and 1 mL $NaHCO_3$, and then the solution was diluted with 15 mL $H_2O$ and extracted with DCM (3x5 mL). The combined organic layers were washed with brine 10 mL (2x5 mL), dried over by $Na_2SO_4$, filtered and concentrated in vacuo to give the title compound (20.0 mg, 77% yield) as a white solid. LC-MS (ESI+) m/z 529.2 $(M+H)^+$.

2-[4-[[Tert-butyl(dimethyl)silyl]oxymethyl]cyclohexyl]-6-methoxy-1,1-dimethyl-isoindolin-5-amine (Intermediate BOD)

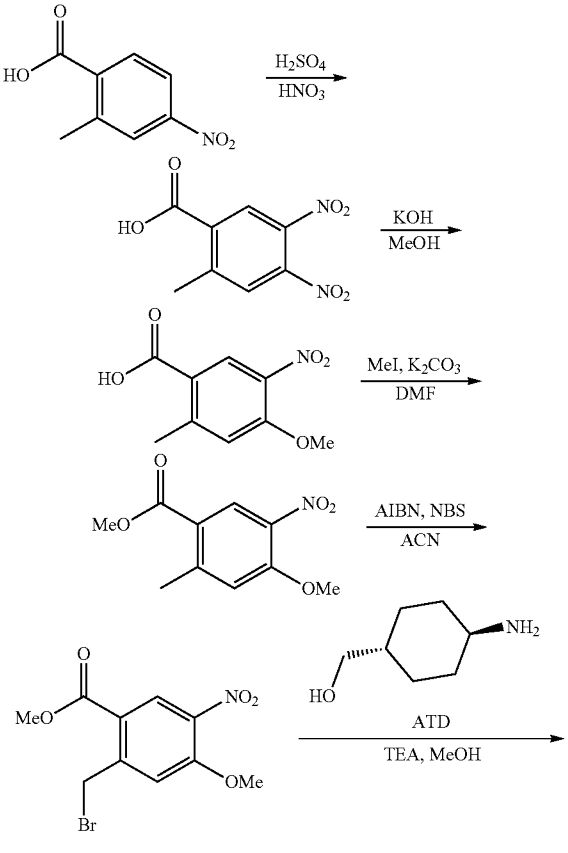

-continued

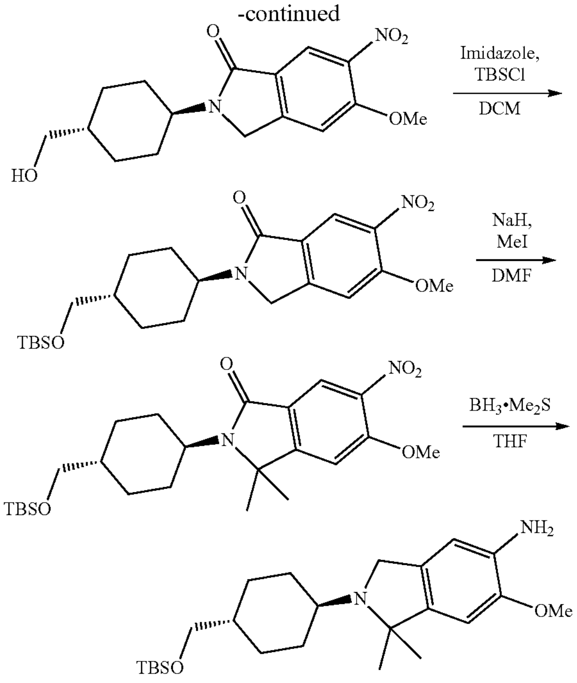

BOD

Step 1—2-Methyl-4,5-dinitro-benzoic acid

To $H_2SO_4$ (50 mL) was added $HNO_3$ (70.0 g, 722 mmol, 50 mL, 65% solution) dropwise at 0° C. and the mixture was allowed to stirred at 0° C. for 10 mins. Then 2-methyl-4-nitro-benzoic acid (10.0 g, 55.2 mmol, CAS #1975-51-5) was added dropwise at 0° C. and the reaction mixture was stirred at 0- 20° C. for 16 hrs. On completion, the reaction mixture was poured into ice water (500 mL) and filtered. The filter cake was dried in vacuo to give the title compound (9.60 g, 46.14% yield, 60% purity) as yellow solid. $^1H$ NMR (400 MHz, DMSO-$d_6$) δ 14.60-12.71 (m, 1H), 8.50 (s, 1H), 8.22 (s, 1H), 2.67 (s, 3H).

Step 2—4-Methoxy-2-methyl-5-nitro-benzoic acid

To a solution of KOH (7.15 g, 127 mmol) in MeOH (100 mL) was added 2-methyl-4,5-dinitro-benzoic acid (9.60 g, 25.4 mmol, 60% purity) and the reaction mixture was stirred at 70° C. for 2 hrs. On completion, the reaction mixture was concentrated in vacuo. The residue was diluted with water (30 mL), then acidified with HCl (2N in water) until the pH=4. The mixture was extracted with EA (3×100 mL), and the combined organic layers were washed with brine (2×80 mL), dried over $Na_2SO_4$, filtered and concentrated in vacuo to give the title compound (8.50 g, 79% yield, 50% purity) as yellow solid. $^1H$ NMR (400 MHz, DMSO-$d_6$) δ 8.36 (s, 1H), 7.31 (s, 1H), 3.98 (s, 3H), 2.63 (s, 3H).

Step 3—Methyl 4-methoxy-2-methyl-5-nitro-benzoate

To a solution of 4-methoxy-2-methyl-5-nitro-benzoic acid (8.50 g, 40.2 mmol, crude) and $K_2CO_3$ (11.1 g, 80.5 mmol) in DMF (60 mL) was added MeI (11.4 g, 80.5 mmol). The reaction mixture was stirred at 20° C. for 2 hrs. On completion, the reaction mixture was filtered and the filtrate was diluted with water (100 mL) and extracted with EA (3×100 mL). The combined organic layers were washed with brine (2×80 mL), dried over $Na_2SO_4$, filtered and concentrated in vacuo. The residue was purified by silica gel chromatography (PE:EA=20:1) to give the title compound (3.20 g, 35% yield) as yellow solid. $^1H$ NMR (400 MHz, $CDCl_3$) δ 8.57 (s, 1H), 6.92 (s, 1H), 4.02 (s, 3H), 3.91 (s, 3H), 2.72 (s, 3H).

Step 4—Methyl 2-(bromomethyl)-4-methoxy-5-nitro-benzoate

To a solution of methyl 4-methoxy-2-methyl-5-nitro-benzoate (2.60 g, 11.5 mmol) and NBS (2.47 g, 13.8 mmol) in ACN (30 mL) was added AIBN (379 mg, 2.31 mmol). The reaction mixture was stirred at 80° C. for 16 hrs. On completion, the reaction mixture was concentrated in vacuo. The residue was diluted with water (30 mL) and extracted with EA (3×60 mL). The combined organic layers were washed with brine (2×50 mL), dried over $Na_2SO_4$, filtered and concentrated in vacuo to give the title compound (3.60 g, 51% yield, 50% purity) as yellow solid. $^1H$ NMR (400 MHz, $CDCl_3$) δ 8.55 (s, 1H), 7.19 (s, 1H), 5.00 (s, 2H), 4.05 (s, 3H), 3.94 (s, 3H).

Step 5—2-[4-(Hydroxymethyl)cyclohexyl]-5-methoxy-6-nitro-isoindolin-1-one

To a solution of methyl 2-(bromomethyl)-4-methoxy-5-nitro-benzoate (3.50 g, 5.75 mmol, 50% purity) and TEA (698 mg, 6.91 mmol) in MeOH (35 mL) was added (4-aminocyclohexyl)methanol (892 mg, 6.91 mmol, Intermediate ATD). The reaction mixture was stirred at 70° C. for 12 hrs. On completion, the reaction mixture was concentrated in vacuo. The residue was purified by silica gel chromatography (PE:EA=1:2) to give the title compound (1.30 g, 70% yield) as yellow solid. $^1H$ NMR (400 MHz, DMSO-$d_6$) δ 8.08 (s, 1H), 7.59 (s, 1H), 4.51 (s, 2H), 4.47-4.40 (m, 1H), 3.99 (s, 3H), 3.97-3.89 (m, 1H), 3.24 (t, J=5.2 Hz, 2H), 1.86-1.74 (m, 4H), 1.65-1.50 (m, 2H), 1.46-1.33 (m, 1H), 1.15-0.96 (m, 2H).

Step 6—2-[4-[[Tert-butyl(dimethyl)silyl]oxymethyl]cyclohexyl]-5-methoxy-6-nitro-isoindolin-1-one To a solution of 2-[4-(hydroxymethyl)cyclohexyl]-5-methoxy-6-nitro-isoindolin-1-one (1.20 g, 3.75 mmol) and imidazole (382 mg, 5.62 mmol) in DCM (20 mL) was added TBSCI (677 mg, 4.50 mmol) at 20° C. The reaction mixture was stirred at 20° C. for 12 hrs. On completion, the reaction mixture was poured into water (20 mL) and extracted with DCM (3×35 mL). The combined organic layers were washed with brine (2×20 mL), dried over $Na_2SO_4$, filtered and concentrated in vacuo. The residue was purified by silica gel chromatography (PE:EA=5:1) to give the title compound (1.30 g, 79% yield) as light yellow solid. $^1H$ NMR (400 MHz, $CDCl_3$) δ 8.25 (s, 1H), 7.14 (s, 1H), 4.39 (s, 2H), 4.21-4.20 (m, 1H), 4.02 (s, 3H), 3.45 (d, J=6.4 Hz, 2H), 2.00-1.84 (m, 4H), 1.59-1.42 (m, 3H), 1.29-1.11 (m, 2H), 0.91 (s, 9H), 0.06 (s, 6H).

Step 7—2-[4-[[Tert-butyl(dimethyl)silyl]oxymethyl]cyclohexyl]-5-methoxy-3,3-dimethyl-6-nitro- isoindolin-1-one To a solution of 2-[4-[[tert-butyl(dimethyl)silyl]oxymethyl]cyclohexyl]-5-methoxy-6-nitro- isoindolin-1-one (1.10 g, 2.53 mmol) in DMF (20 mL) at 0° C. was added NaH (253 mg, 6.33 mmol, 60% dispersion in mineral oil). After 15 min, MeI (1.44 g, 10.1 mmol) was added and the reaction mixture was stirred at 0° C. for 1 hr. On completion, the reaction mixture was poured into water (50 mL) and extracted with EA (3x60 mL). The combined organic layers were washed with brine (2x50 mL), dried over $Na_2SO_4$, filtered and concentrated in vacuo. The residue was purified by silica gel chromatography (PE:EA=15:1) to give the title compound (560 mg, 47% yield) as red solid. $^1$H NMR (400 MHz, $CDCl_3$) δ 8.17 (s, 1H), 6.97 (s, 1H), 4.03 (s, 3H), 3.45 (d, J=6.4 Hz, 2H), 3.20-3.06 (m, 1H), 2.58 (dd, J=3.6, 12.4 Hz, 2H), 1.97-1.86 (m, 2H), 1.73-1.61 (m, 3H), 1.51 (s, 6H), 1.11-0.97 (m, 2H), 0.92-0.90 (m, 9H), 0.06 (s, 6H).

Step 8—2-[4-[[Tert-butyl(dimethyl)silyl]oxymethyl] cyclohexyl]-6-methoxy-1,1-dimethyl-isoindolin-5-amine To a solution of 2-[4-[[tert-butyl(dimethyl)silyl]oxymethyl]cyclohexyl]-5-methoxy-3,3-dimethyl-6- nitro-isoindolin-1-one (300 mg, 648 umol) in THE (6 mL) was added $BH_3$-$Me_2S$ (10 M, 324 uL) at 20° C. The reaction mixture was then stirred at 70° C. for 24 hrs. On completion, the reaction mixture was quenched by MeOH (3 mL) and concentrated in vacuo. The residue was purified by reverse phase (0.1% FA) to give the title compound (110 mg, 36% yield, FA salt) as yellow solid. LC-MS (ESI$^+$) m/z 419.3 $(M+H)^+$.

N-[2-(4-formylcyclohexyl)-6-methoxy-1,1-dimethyl-isoindolin-5-yl]-6-(trifluoromethyl)pyridine-2-carboxamide (Intermediate BOE)

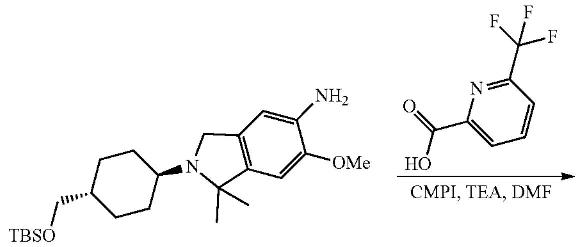

BOD

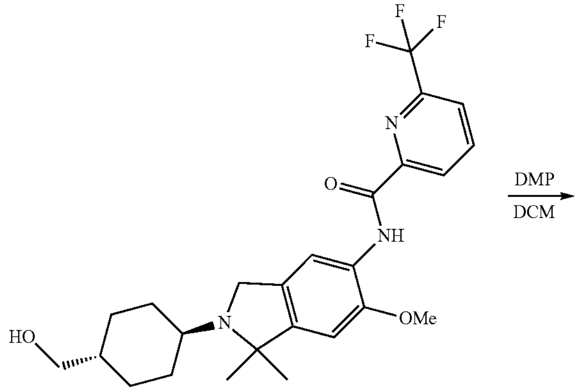

-continued

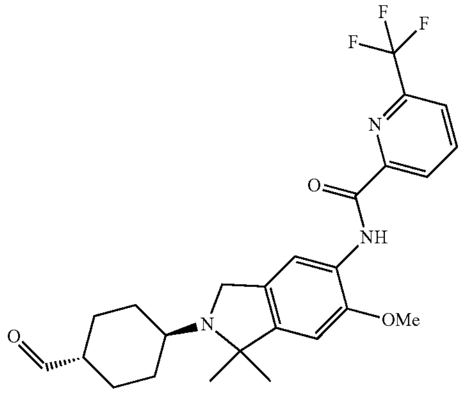

BOE

Step 1—N-[2-[4-(hydroxymethyl)cyclohexyl]-6-methoxy-1,1-dimethyl-isoindolin-5-yl]-6-(trifluoro methyl)pyridine-2-carboxamide To a solution of 2-[4-[[tert-butyl(dimethyl)silyl]oxymethyl]cyclohexyl]-6-methoxy-1,1-dimethyl- isoindolin-5-amine (100 mg, 215 umol, FA salt, Intermediate BOD), 6-(trifluoromethyl)pyridine-2-carboxylic acid (41.1 mg, 215 umol) and DIEA (55.6 mg, 430 umol) in DMF (3 mL) was added CMPI (65.9 mg, 258 umol). The reaction mixture was stirred at 20° C. for 1 hour. On completion, the reaction mixture was quenched with water (0.2 mL). The solution was purified by reverse phase (0.1% FA) and the fraction was concentrated in vacuo to give the title compound (65.0 mg, 57% yield, FA salt) as yellow solid. $^1$H NMR (400 MHz, $CDCl_3$) δ 10.55 (s, 1H), 8.52 (s, 1H), 8.48 (d, J=7.6 Hz, 1H), 8.14 (t, J=7.6 Hz, 1H), 7.89 (d, J=7.6 Hz, 1H), 6.68 (s, 1H), 4.60 (s, 2H), 4.00 (s, 3H), 3.48 (d, J=6.0 Hz, 2H), 3.42-3.30 (m, 1H), 2.31-2.10 (m, 2H), 2.07-1.92 (m, 4H), 1.85 (s, 6H), 1.67-1.53 (m, 1H), 1.21-1.03 (m, 2H).

Step 2—N-[2-(4-formylcyclohexyl)-6-methoxy-1,1-dimethyl-isoindolin-5-yl]-6-(trifluoromethyl)pyridine-2-carboxamide To a solution of N-[2-[4-(hydroxymethyl)cyclohexyl]-6-methoxy-1,1-dimethyl-isoindolin-5-yl]-6- (trifluoromethyl) pyridine-2-carboxamide (65.0 mg, 124 umol, FA salt) in DCM (1.5 mL) was added DMP (63.1 mg, 148 umol). The reaction mixture was stirred at 25° C. for 1 hr. On completion, the reaction mixture was quenched by saturated $Na_2S2SO_3$ (2 mL), basified with saturated $NaHCO_3$ until the pH=8 and extracted with DCM (3x15 mL). The combined organic layers were washed with brine (2x10 mL), dried over $Na_2SO_4$, filtered and concentrated in vacuo to give the title compound (50.0 mg, 72% yield) as yellow solid. LC-MS (ESI$^+$) m/z 476.0 $(M+H)^+$.

Example 1 (Method 1). Synthesis of N-[2-[4-[4-[1-(2,6-dioxo-3-piperidyl)-3-methyl-2-oxo-benzimidazol-4-yl]piperidine-1-carbonyl]cyclohexyl]-6-methoxy-indazol-5-yl]-6-(trifluoromethyl)pyridine-2-carboxamide (I-295)

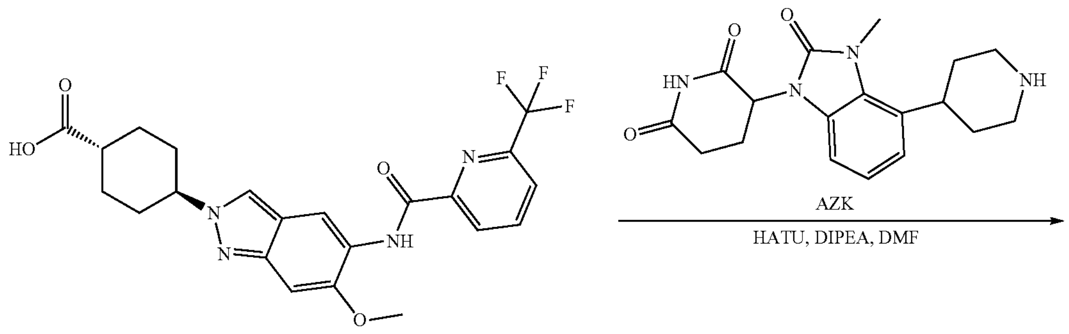

AXQ

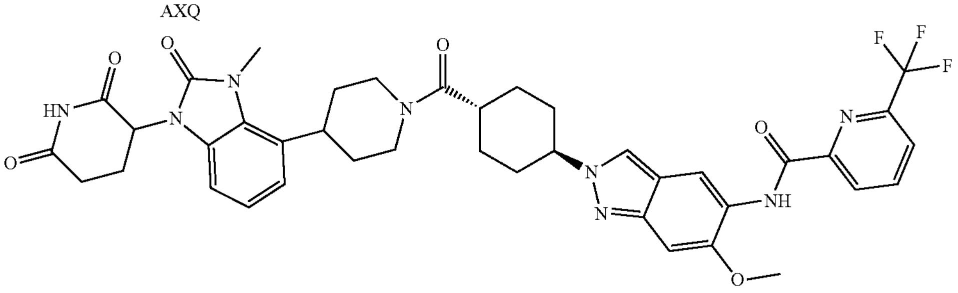

I-295

To a solution of 4-[6-methoxy-5-[[6-(trifluoromethyl)pyridine-2-carbonyl]amino]indazol-2-yl]cyclohexanecarboxylic acid (150 mg, 227 umol, Intermediate AXQ), 3-[3-methyl-2-oxo-4-(4-piperidyl)benzimidazol-1-yl]piperidine-2,6-dione (86.0 mg, 227 umol, HCl, Intermediate AZK) in DMF (3.0 mL) was added DIPEA (88.0 mg, 681 umol) and HATU (130 mg, 341 umol). The reaction mixture was stirred at 25° C. for 1 hr. On completion, the reaction mixture was quenched by $H_2O$ (0.2 mL) and filtered. The filtrate was concentrated in vacuo to give a residue. The residue was purified by Prep-HPLC (column: Phenomenex Synergi C18 150*25*10 um;mobile phase: [water(0.225% FA)-ACN];B %: 42%-72%, 10 min) to give the title compound (109 mg, 61% yield) as off-white solid. $^1H$ NMR (400 MHz, DMSO-$d_6$) δ 11.10 (s, 1H), 10.51 (s, 1H), 8.70 (s, 1H), 8.51-8.38 (m, 2H), 8.33 (s, 1H), 8.24-8.19 (m, 1H), 7.15 (s, 1H), 7.05-6.95 (m, 3H), 5.39 (dd, J=5.2, 12.4 Hz, 1H), 4.62 (d, J=12.4 Hz, 1H), 4.51-4.39 (m, 1H), 4.18 (d, J=10.4 Hz, 1H), 3.99 (s, 3H), 3.64 (s, 3H), 3.55 (t, J=11.6 Hz, 1H), 3.26 (t, J=12.0 Hz, 1H), 2.96-2.78 (m, 2H), 2.77-2.59 (m, 3H), 2.17 (s, 2H), 2.02 (t, J=12.0 Hz, 3H), 1.97-1.84 (m, 4H), 1.77-1.62 (m, 3H), 1.61-1.50 (m, 1H); LC-MS ($ESI^+$) m/z 787.3 $(M+H)^+$.

TABLE 6

Compounds synthesized via Method 1 with the coupling of various intermediate amines and acids.

| I-# | Intermediate Amine | Intermediate Acid | LCMS (ES+) m/z $(M + H)^+$ | $^1$HNMR (400 MHz, DMSO-$d_6$) δ |
|---|---|---|---|---|
| I-43 | WX | AMY | 858.2 | 12.36 (s, 1H), 11.11 (s, 1H), 8.74-8.69 (m, 1H), 8.47-8.43 (m, 1H), 8.39-8.33 (m, 2H), 8.18-8.14 (m, 1H), 7.56 (s, 1H), 7.12-6.86 (m, 3H), 5.97-5.92 (m, 1H), 5.38 (dd, J = 5.2, 12.4 Hz, 1H), 4.54-4.44 (m, 1H), 3.83-3.79 (m, 1H), 3.72-3.63 (m, 5H), 2.88 (s, 4H), 2.80-2.64 (m, 4H), 2.22-1.98 (m, 7H), 1.88-1.75 (m, 3H), 1.71-1.38 (m, 12H) |
| I-44 | AGI | AMY | 870.6 | 12.35 (s, 1H), 11.10 (s, 1H), 8.71 (s, 1H), 8.47-8.42 (m, 1H), 8.39-8.31 (m, 2H), 8.16 (d, J = 8.0 Hz, 1H), 7.56 (s, 1H), 7.08-6.91 (m, 3H), 5.94 (s, 1H), 5.37 (dd, J = 4.0, 12.0 Hz, 1H), 4.52-4.42 (m, 1H), 3.81 (s, 2H), 3.67 (S, 3H), 3.49-3.45 (m, 1H), 3.00 (s, 4H), 2.93-2.84 (m, 1H), 2.77-2.62 (m, 4H), 2.19-1.93 (m, 6H), 1.88-1.56 (m, 15H) |
| I-239 | ACV | AMY | 884.5 | 12.35 (s, 1H), 11.09 (s, 1H), 8.71 (s, 1H), 8.47-8.42 (m, 1H), 8.40-8.36 (m, 1H), 8.34 (s, 1H), 8.16 (dd, J = 0.8, 7.6 Hz, 1H), 7.56 (s, 1H), 6.98-6.95 (m, 1H), |

TABLE 6-continued

Compounds synthesized via Method 1 with the coupling of various intermediate amines and acids.

| I-# | Intermediate Amine | Intermediate Acid | LCMS (ES+) m/z (M + H)+ | $^1$HNMR (400 MHz, DMSO-$d_6$) δ |
|---|---|---|---|---|
| | | | | 6.91-6.78 (m, 1H), 5.94 (s, 1H), 5.36 (dd, J = 5.2, 12.0 Hz, 1H), 4.55-4.41 (m, 1H), 3.58 (s, 3H), 3.05-2.97 (m, 5H), 2.96-2.81 (m, 4H), 2.78-2.73 (m, 1H), 2.73-2.69 (m, 2H), 2.66-2.56 (m, 2H), 2.19-1.96 (m, 6H), 1.86-1.65 (m, 6H), 1.65-1.55 (m, 10H) |
| I-292 | WX | AXQ | 830.3 | 10.83 (s, 1H), 10.45 (s, 1H), 8.67 (s, 1H), 8.49-8.36 (m, 2H), 8.27 (s, 1H), 8.16 (d, J = 7.6 Hz, 1H), 7.30-6.90 (m, 4H), 5.44-5.31 (m, 1H), 4.46-4.44 (m, 2H), 4.01 (s, 4H), 3.69-3.67 (m, 5H), 2.93-2.87 (m, 4H), 2.76-2.70 (m, 4H), 2.22-2.20 (dd, J = 3.2, 12.8 Hz, 3H), 2.13-1.99 (m, 4H), 1.94-1.82 (m, 3H), 1.80-1.59 (m, 5H) |
| I-295 | BAI | AXQ | 788.3 | 11.29-10.89 (m, 1H), 10.51 (s, 1H), 8.71 (s, 1H), 8.50-8.45 (m, 1H), 8.44-8.38 (m, 1H), 8.34 (s, 1H), 8.23 (dd, J = 0.8, 7.6 Hz, 1H), 7.16 (s, 1H), 7.05-6.89 (m, 3H), 5.38 (dd, J = 5.6, 12.8 Hz, 1H), 4.59-4.34 (m, 2H), 4.20-4.04 (m, 1H), 4.00 (s, 3H), 3.68 (s, 3H), 3.48-3.33 (m, 2H), 3.20-3.02 (m, 2H), 2.97-2.77 (m, 4H), 2.74-2.69 (m, 1H), 2.66-2.59 (m, 1H), 2.22-2.14 (m, 2H), 2.09-1.98 (m, 3H), 1.92 (m, 2H), 1.76-1.60 (m, 2H) |
| I-368 | BGU | 2-fluorobenzoic acid (CAS# 445-29-4) | 751.5 | 11.10 (s, 1H), 9.48 (d, J = 10.0 Hz, 1H), 8.51 (s, 1H), 8.31 (s, 1H), 7.93 (t, J = 7.2 Hz, 1H), 7.66-7.62 (m, 1H), 7.43-7.37 (m, 2H), 7.09 (s, 1H), 7.02-6.98 (m, 1H), 6.94-6.89 (m, 2H), 5.38-5.34 (m, 1H), 4.45-4.33 (m, 1H), 3.93 (s, 3H), 3.65 (s, 3H), 3.22 (d, J = 10.0 Hz, 2H), 2.95-2.85 (m, 2H), 2.82-2.71 (m, 4H), 2.65-2.60 (m, 2H), 2.52 (s, 3H), 2.21-2.19 (m, 2H), 2.01-1.90 (m, 7H), 1.88-1.76 (m, 3H), 1.25-1.19 (m, 2H) |

Variations in reaction time for Method 1 were as follows: the reaction was run anywhere from 0.5-12 h. The reaction temperature was run anywhere from −15° C. to 60° C. If the product of Step 1 was not a precipitate, a standard work up with water and extraction with ethyl acetate was used to isolate the product. The final products were isolated under standard purification techniques including reverse HPLC, silica gel chromatography, and prep-TLC with appropriate solvent conditions.

Example 2 (Method 2). Synthesis of 6-(1,1-Difluoroethyl)-N-[2-[4-[[2-[2-[[2-(2,6-dioxo-3-piperidyl)-1,3-dioxo-isoindolin-4- yl]amino]ethyl]-7-azaspiro[3.5]nonan-7-yl]methyl]cyclohexyl]-6-methoxy-indazol-5-yl]pyridine-2-carboxamide (I-63)

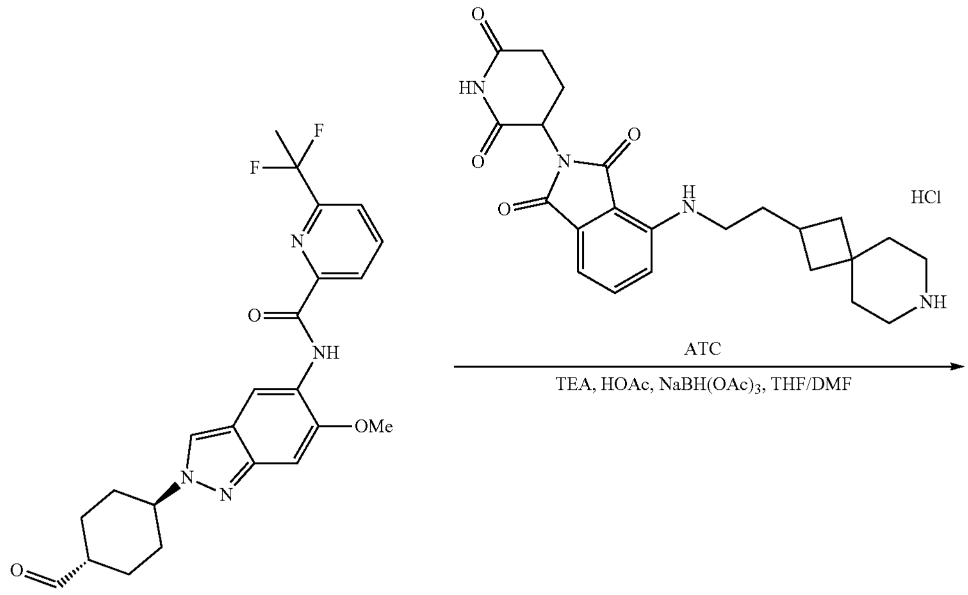

ATF

-continued

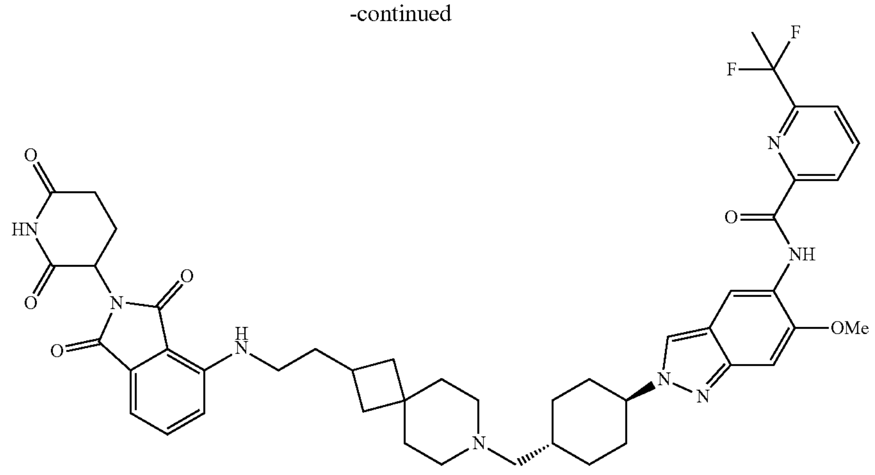

I-63

To a solution of 4-[2-(7-azaspiro[3.5]nonan-2-yl)ethylamino]-2-(2,6-dioxo-3-piperidyl)isoindoline-1,3-dione (43.0 mg, 93.2 umol, HCl salt, Intermediate ATC) in a mixed solvent of THE (1 mL) and DMF (0.5 mL) was added TEA until the pH=7~8, then the mixture was acidified with AcOH until the pH=6~7. Next, 6-(1,1- difluoroethyl)-N-[2-(4-formylcyclohexyl)-6-methoxy-indazol-5-yl]pyridine-2-carboxamide (41.2 mg, 93.2 umol, Intermediate ATF) was added at 0° C. After the reaction mixture was stirred at 0° C. for 0.5 hr, $NaBH(OAc)_3$ (39.5 mg, 186 umol) was added. The reaction mixture was stirred at 0- 25)C for 2 hrs. On completion, the reaction mixture was quenched with water (0.1 mL), filtered and concentrated in vacuo. The residue was purified by Prep-HPLC (column: Shim-pack C18 150*25*10 um; mobile phase: [water (0.225% FA)-ACN]) to give the title compound (37.8 mg, 45% yield, FA salt) as yellow solid. LC-MS ($ESI^+$) m/z 851.5 $(M+H)^+$. $^1H$ NM/R (400 MHz, DMSO-$d_6$) δ 11.10 (s, 1H), 10.67 (s, 1H), 8.66 (s, 1H), 8.33-8.26 (m, 3H), 8.04-7.98 (m, 1H), 7.58 (t, J=8.0 Hz, 1H), 7.14 (s, 1H), 7.09-7.04 (i, 1H), 7.02 (d, J 7.2 Hz, 1H), 6.48 (t, J 5.2 Hz, 1H), 5.05 (dd, J=5.2, 12.8 Hz, 1H), 4.39-4.28 (s, 1H), 3.99 (s, 3H), 3.23-3.19 (m, 2H), 2.93-2.82 (m, 1H), 2.63-2.53 (m, 2H), 2.32-2.23 (i, 3H), 2.23-2.05 (i, 9H), 2.05-1.98 (m, 1H), 1.96-1.80 (m, 6H), 1.74-1.64 (m, 2H), 1.62-1.52 (br s, 3H), 1.50-1.44 (m, 2H), 1.43-1.33 (m, 2H), 1.16-0.99 (m, 2H).

TABLE 7

Compounds synthesized via Method 2 with the reductive amination of various intermediate amines and aldehydes.

| I-# | Intermediate Amine | Intermediate Aldehyde | LCMS (ES+) m/z $(M + H)^+$ | $^1$HNMR (400 MHz, DMSO-$d_6$) δ |
|---|---|---|---|---|
| I-1 | AAM | AGL | 858.5 | 12.36 (s, 1H), 8.72 (s, 1H), 8.48-8.42 (m, 1H), 8.39-8.34 (m, 2H), 8.16 (d, J = 8.4 Hz, 1H), 7.55 (s, 1H), 7.37-6.84 (m, 3H), 6.01-5.90 (m, 1H), 5.54-5.43 (m, 1H), 4.51-4.40 (m, 1H), 3.65 (s, 3H), 3.43-3.42 (m, 2H), 3.04 (s, 3H), 3.03-2.91 (m, 3H), 2.84-2.70 (m, 5H), 2.54-2.52 (m, 4H), 2.23-2.13 (m, 3H), 2.10-1.82 (m, 10H), 1.62 (s, 6H), 1.35-1.21 (m, 2H) |
| I-29 | AJH | AGL | 887.5 | 12.36 (s, 1H), 11.10 (s, 1H), 8.71 (s, 1H), 8.48-8.43 (m, 1H), 8.40-8.33 (m, 2H), 8.16 (d, J = 8.4 Hz, 1H), 7.62-7.55 (m, 2H), 7.10 (d, J = 8.6 Hz, 1H), 7.03 (d, J = 7.2 Hz, 1H), 6.67 (t, J = 6.0 Hz, 1H), 5.94 (s, 1H), 5.08-5.03 (m, 1H), 4.49-4.38 (m, 1H), 3.48 (t, J = 5.2 Hz, 2H), 3.41-3.37 (m, 3H), 3.25-3.24 (m, 2H), 2.95-2.80 (m, 2H), 2.62-2.55 (m, 5H), 2.18-2.09 (m, 2H), 2.08-1.88 (m, 6H), 1.85-1.65 (m, 6H), 1.62 (s, 6H), 1.38-1.09 (m, 4H) |
| I-31 | AMC | AGL | 861.3 | 12.37 (s, 1H), 11.10 (s, 1H), 8.72 (s, 1H), 8.48-8.43 (m, 1H), 8.41-8.31 (m, 2H), 8.21-8.16 (m, 1H), 7.61-7.56 (m, 2H), 7.11 (d, J = 8.8 Hz, 1H), 7.03 (d, J = 6.8 Hz, 1H), 6.68 (t, J = 5.6 Hz, 1H), 5.97 (s, 1H), 5.05 (dd, J = 12.8, 5.4 Hz, 1H), 4.45-4.43 (m, 1H), 3.50-3.40 (m, 5H), 2.93-2.83 (m, 1H) 2.62-2.52 (m, 2H), 2.38-2.33 (m, 2H), 2.16-2.10 (m, 6H), 2.05-1.97 (m, 1H), 1.95-1.80 (m, 6H), 1.70-1.65 (m, 2H), 1.64-1.52 (m, 7H), 1.14-1.03 (m, 2H) |
| I-32 | ANK | AGL | 897.4 | 11.10 (s, 1H), 8.71 (s, 1H), 8.50-8.33 (m, 3H), 8.18-8.15 (m, 1H), 7.64-7.53 (m, 2H), 7.15-7.01 (m, 2H), 6.47 (t, J = 5.2 Hz, 1H), 5.95 (s, 1H), 5.06 (dd, J = 5.2, 12.8 Hz, 1H), 4.46-4.36 (m, 1H), 2.94-2.83 (m, 2H), |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 2.64-2.57 (m, 2H), 2.25-2.23 (m, 2H), 2.20 (s, 3H), 2.16-2.10 (m, 2H), 2.07-2.01 (m, 1H), 1.98-1.75 (m, 8H), 1.68-1.67 (m, 1H), 1.65-1.62 (m, 6H), 1.60-1.42 (m, 6H), 1.33-1.00 (m, 7H) |
| I-33 | AJH | ALU | 879.2 | 11.08 (s, 1H), 10.48 (s, 1H), 8.55 (s, 1H), 8.48 (s, 1H), 8.47-8.38 (m, 2H), 8.22 (dd, J = 7.6 Hz, 1H), 7.98 (s, 1H), 7.58 (dd, J = 8.4 Hz, 1H), 7.40-7.07 (m, 2H), 7.03 (d, J = 6.8 Hz, 1H), 6.67 (t, J = 3.2 Hz, 1H), 5.08-5.03 (m, 1H), 4.58-4.43 (m, 1H), 3.48-3.45 (m, 2H), 3.41-3.37 (m, 3H), 3.22 (br d, J = 6.8 Hz, 2H), 2.94-2.80 (m, 4H), 2.21-2.12 (m, 4H), 2.07-1.82 (m, 9H), 1.70-1.54 (m, 4H), 1.23-1.06 (m, 4H) |
| I-34 | WX | ALT | 844.3 | 12.34 (s, 1H), 11.10 (s, 1H), 8.74 (s, 1H), 8.51-8.42 (m, 1H), 8.37 (t, J = 8.0 Hz, 1H), 8.16 (d, J = 7.6 Hz, 1H), 8.03 (s, 1H), 7.62 (s, 1H), 7.07 (d, J = 7.6 Hz, 1H), 6.96 (t, J = 7.6 Hz, 1H), 6.87 (d, J = 7.6 Hz, 1H), 5.98 (s, 1H), 5.38 (dd, J = 5.6, 12.4 Hz, 1H), 4.70-4.57 (m, 1H), 3.68 (s, 3H), 3.62 (s, 2H), 2.88 (d, J = 10.4 Hz, 3H), 2.77-2.68 (m, 1H), 2.65-2.58 (m, 1H), 2.52 (s, 2H), 2.44-2.36 (m, 1H), 2.24 (d, J = 6.0 Hz, 2H), 2.20 (s, 3H), 2.06-1.87 (m, 9H), 1.64 (s, 6H), 1.57-1.47 (m, 1H), 1.46-1.33 (m, 2H), 1.22-1.08 (m, 2H) |
| I-35 | AML | AGL | 855.5 | 12.36 (s, 1H), 11.10 (s, 1H), 8.71 (s, 1H), 8.47-8.42 (m, 1H), 8.39-8.33 (m, 2H), 8.17-8.13 (m, 1H), 7.64-7.53 (m, 2H), 7.06 (d, J = 7.2 Hz, 1H), 7.00 (d, J = 8.4 Hz, 1H), 6.45 (d, J = 6.4 Hz, 1H), 5.94 (s, 1H), 5.06 (dd, J = 5.2, 12.8 Hz, 1H), 4.47-4.35 (m, 1H), 4.17-4.06 (m, 1H), 2.94-2.83 (m, 1H), 2.63-2.52 (m, 2H), 2.48-2.44 (m, 1H), 2.39-2.20 (m, 6H), 2.17-2.09 (m, 4H), 2.06-1.99 (m, 1H), 1.97-1.85 (m, 4H), 1.72-1.64 (m, 4H), 1.62 (s, 6H), 1.58-1.54 (m, 2H), 1.18-1.03 (m, 2H) |
| I-36 | AOE | AGL | 828.5 | 12.36 (s, 1H), 11.10 (s, 1H), 8.70 (s, 1H), 8.47-8.43 (m, 1H), 8.40-8.32 (m, 2H), 8.23-8.14 (m, 1H), 7.57 (s, 1H), 7.05 (d, J = 7.6 Hz, 1H), 6.99-6.88 (m, 2H), 5.94 (s, 1H), 5.36 (dd, J = 12.0, 5.2 Hz, 1H), 4.50-4.26 (m, 1H), 3.74 (d, J = 1.6 Hz, 2H), 3.63 (s, 3H), 3.22 (s, 9H), 2.97-2.82 (m, 1H), 2.74-2.60 (m, 2H), 2.25 (d, J = 6.4 Hz, 2H), 2.10 (d, J = 9.2 Hz, 2H), 2.05-1.96 (m, 1H), 1.92-1.81 (m, 4H), 1.62 (s, 6H), 1.42-1.27 (m, 1H), 1.16-1.03 (m, 2H) |
| I-37 | AMZ | ALT | 886.5 | 12.36 (s, 1H), 11.10 (s, 1H), 8.71 (s, 1H), 8.48-8.42 (m, 1H), 8.40-8.32 (m, 2H), 8.16 (d, J = 7.6 Hz, 1H), 7.57 (s, 1H), 7.08 (d, J = 7.6 Hz, 1H), 6.97 (t, J = 7.6 Hz, 1H), 6.89 (d, J = 7.3 Hz, 1H), 5.94 (s, 1H), 5.38 (dd, J = 5.2, 12.4 Hz, 1H), 4.46-4.34 (m, 1H), 3.68 (s, 3H), 3.62-3.54 (m, 4H), 2.93-2.85 (m, 1H), 2.78-2.69 (m, 1H), 2.64-2.60 (m, 1H), 2.40-2.34 (m, 2H), 2.32-2.19 (m, 6H), 2.12 (d, J = 7.2 Hz, 4H), 2.05-1.98 (m, 1H), 1.96-1.75 (m, 6H), 1.61 (s, 6H), 1.54-1.41 (m, 2H), 1.16-1.01 (m, 2H) |
| I-38 | WX | ALU | 836.5 | 11.10 (s, 1H), 10.49 (s, 1H), 8.55 (s, 1H), 8.48 (s, 1H), 8.47-8.43 (m, 1H), 8.43-8.37 (m, 1H), 8.24-8.19 (m, 1H), 7.98 (s, 1H), 7.39-7.10 (m, 1H), 7.07 (d, J = 7.6 Hz, 1H), 6.96 (t, J = 7.6 Hz, 1H), 6.87 (d, J = 7.6 Hz, 1H), 5.38 (dd, J = 5.6, 12.4 Hz, 1H), 4.57-4.38 (m, 1H), 3.68 (s, 3H), 3.62 (s, 2H), 2.95-2.83 (m, 3H), 2.79-2.61 (m, 2H), 2.42-2.36 (m, 1H), 2.31-2.25 (m, 2H), 2.22 (s, 3H), 2.18-2.12 (m, 2H), 2.04-1.84 (m, 7H), 1.70-1.61 (m, 2H), 1.60-1.49 (m, 1H), 1.48-1.34 (m, 2H), 1.16-1.03 (m, 2H) |
| I-39 | WX | ARO | 850.2 | 11.20-11.08 (m, 1H), 10.49 (s, 1H), 8.58-8.54 (m, 1H), 8.51-8.38 (m, 3H), 8.23 (d, J = 7.6 Hz, 1H), 7.99 (s, 1H), 7.42-6.87 (m, 4H), 5.52-5.35 (m, 1H), 4.67-4.57 (m, 2H), 3.73-3.62 (m, 4H), 3.58-3.51 (m, 1H), 3.17 (s, 1H), 2.90 (s, 4H), 2.53-2.52 (m, 5H), 2.25-2.15 ( m, 2H), 2.09 (s, 2H), 2.08-1.99 (m, 3H), 1.92-1.79 (m, 3H), 1.77-1.56 (m, 4H) |
| I-40 | AGW | AGL | 843.5 | 12.36 (s, 1H), 11.08 (s, 1H), 8.71 (s, 1H), 8.48-8.42 (m, 1H), 8.40-8.31 (m, 2H), 8.16 (d, J = 7.6 Hz, 1H), 7.71-7.63 (m, 1H), 7.57 (s, 1H), 7.38-7.27 (m, 2H), 5.94 (s, 1H), 5.09 (dd, J = 5.6, 12.8 Hz, 1H), 4.50-4.35 |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | (m, 1H), 3.78-3.59 (m, 2H), 2.97-2.79 (m, 3H), 2.63-2.53 (m, 2H), 2.24-1.80 (m, 16H), 1.76-1.63 (m, 2H), 1.62 (s, 6H), 1.39-1.25 (m, 2H), 1.18-1.05 (m, 2H) |
| I-41 | AOQ | AGL | 873.4 | 12.36 (s, 1H), 11.09 (s, 1H), 8.71 (s, 1H), 8.48-8.42 (m, 1H), 8.40-8.32 (m, 2H), 8.20-8.10 (m, 1H), 7.63-7.53 (m, 2H), 7.07 (d, J = 7.2 Hz, 1H), 6.91 (d, J = 8.4 Hz, 1H), 6.51 (d, J = 6.0 Hz, 1H), 5.94 (s, 1H), 5.05 (dd, J = 5.6, 12.8 Hz, 1H), 4.48-4.37 (m, 1H), 4.22-4.09 (m, 2H), 3.38-3.37 (m, 2H), 2.95-2.81 (m, 1H), 2.62-2.52 (m, 2H), 2.48-2.44 (m, 2H), 2.43-2.35 (m, 2H), 2.31-2.19 (m, 7H), 2.18-2.10 (m, 2H), 2.06-1.99 (m, 1H), 1.99-1.85 (m, 4H), 1.75-1.67 (m, 2H), 1.67-1.63 (m, 1H), 1.61 (s, 6H), 1.22-1.03 (m, 2H) |
| I-42 | AFJ | AGL | 869.6 | 12.36 (s, 1H), 11.11 (s, 1H), 8.71 (s, 1H), 8.48-8.30 (m, 3H), 8.21-8.12 (m, 1H), 7.63-7.52 (m, 2H), 7.11 (d, J = 8.4 Hz, 1H), 7.03 (d, J = 6.8 Hz, 1H), 6.48 (t, J = 5.6 Hz, 1H), 5.95 (s, 1H), 5.05 (dd, J = 5.2, 12.8 Hz, 1H), 4.46-4.34 (m, 1H), 3.32-3.31 (m, 2H), 2.95-2.80 (m, 1H), 2.63-2.54 (m, 3H), 2.53-2.52 (m, 2H), 2.32-2.20 (m, 3H), 2.17-2.08 (m, 4H), 2.07-1.99 (m, 1H), 1.97-1.81 (m, 6H), 1.61 (s, 6H), 1.60-1.55 (m, 2H), 1.54-1.46 (m, 4H), 1.20-1.00 (m, 2H) |
| I-43 | WX | AMY | 858.2 | 12.36 (s, 1H), 11.11 (s, 1H), 8.74-8.69 (m, 1H), 8.47-8.43 (m, 1H), 8.39-8.33 (m, 2H), 8.18-8.14 (m, 1H), 7.56 (s, 1H), 7.12-6.86 (m, 3H), 5.97-5.92 (m, 1H), 5.38 (dd, J = 5.2, 12.4 Hz, 1H), 4.54-4.44 (m, 1H), 3.83-3.79 (m, 1H), 3.72-3.63 (m, 5H), 2.88 (s, 4H), 2.80-2.64 (m, 4H), 2.22-1.98 (m, 7H), 1.88-1.75 (m, 3H), 1.71-1.38 (m, 12H) |
| I-44 | AGI | AMY | 870.6 | 12.35 (s, 1H), 11.10 (s, 1H), 8.71 (s, 1H), 8.47-8.42 (m, 1H), 8.39-8.31 (m, 2H), 8.16 (d, J = 8.0 Hz, 1H), 7.56 (s, 1H), 7.08-6.91 (m, 3H), 5.94 (s, 1H), 5.37 (dd, J = 4.0, 12.0 Hz, 1H), 4.52-4.42 (m, 1H), 3.81 (s, 2H), 3.67 (S, 3H), 3.49-3.45 (m, 1H), 3.00 (s, 4H), 2.93-2.84 (m, 1H), 2.77-2.62 (m, 4H), 2.19-1.93 (m, 6H), 1.88-1.56 (m, 15H) |
| I-46 | AJF | ALU | 861.2 | 11.20-10.95 (m, 1H), 10.62-10.37 (m, 1H), 8.55 (s, 1H), 8.48 (s, 1H), 8.47-8.44 (m, 1H), 8.43-8.38 (m, 1H), 8.22 (dd, J = 0.8, 7.6 Hz, 1H), 7.98 (s, 1H), 7.58 (dd, J = 7.6, 8.4 Hz, 1H), 7.43-7.07 (m, 2H), 7.02 (d, J = 7.2 Hz, 1H), 6.46 (t, J = 5.2 Hz, 1H), 5.04 (dd, J = 5.6, 12.8 Hz, 1H), 4.56-4.42 (m, 1H), 2.94-2.80 (m, 1H), 2.63-2.53 (m, 2H), 2.30-2.12 (m, 7H), 2.11-2.00 (m, 4H), 1.98-1.82 (m, 7H), 1.67-1.54 (m, 3H), 1.50 (t, J = 9.2 Hz, 4H), 1.17-1.02 (m, 2H) |
| I-47 | AOV | APG | 789.6 | 12.39 (s, 1H), 11.09 (s, 1H), 8.71 (s, 1H), 8.34 (s, 1H), 8.00-7.88 (m, 2H), 7.63-7.55 (m, 2H), 7.50 (dd, J = 0.8, 7.2 Hz, 1H), 7.19 (d, J = 8.8 Hz, 1H), 7.05 (d, J = 6.8 Hz, 1H), 6.17 (d, J = 8.4 Hz, 1H), 5.90 (s, 1H), 5.06 (dd, J = 5.2, 12.8 Hz, 1H), 4.43 (br s, 1H), 3.58-3.49 (m, 1H), 2.94-2.83 (m, 1H), 2.61 (s, 3H), 2.30 (br s, 3H), 2.20-1.89 (m, 10H), 1.82 (br d, J = 10.4 Hz, 2H), 1.64 (s, 6H), 1.53-1.43 (m, 2H), 1.39-1.29 (m, 2H), 1.19-1.08 (m, 2H) |
| I-48 | WX | APG | 790.6 | 12.38 (s, 1H), 11.38-10.82 (m, 1H), 8.69 (s, 1H), 8.32 (s, 1H), 7.98-7.89 (m, 2H), 7.55 (s, 1H), 7.52-7.45 (m, 1H), 7.07 (d, J = 7.6 Hz, 1H), 6.96 (t, J = 7.8 Hz, 1H), 6.87 (d, J = 7.2 Hz, 1H), 5.89 (s, 1H), 5.38 (dd, J = 5.2, 12.4 Hz, 1H), 4.48-4.31 (m, 1H), 3.68 (s, 3H), 3.62 (s, 2H), 2.96-2.81 (m, 3H), 2.77-2.67 (m, 1H), 2.66-2.60 (m, 1H), 2.60 (s, 3H), 2.31-2.26 (m, 1H), 2.21 (d, J = 6.8 Hz, 2H), 2.17 (s, 3H), 2.12 (d, J = 10.8 Hz, 2H), 2.03-1.84 (m, 8H), 1.67-1.64 (m, 1H), 1.63 (s, 6H), 1.54-1.46 (m, 1H), 1.44-1.32 (m, 2H), 1.12-1.00 (m, 2H) |
| I-46 | AOE | APL | 822.5 | 12.45 (s, 1H), 11.08 (s, 1H), 9.04 (s, 1H), 8.82 (s, 1H), 8.49-8.44 (m, 1H), 8.38 (t, J = 8.0 Hz, 1H), 8.17 (d, J = 7.6 Hz, 1H), 7.99 (d, J = 8.8 Hz, 2H), 7.69 (s, 1H), 7.43 (d, J = 8.8 Hz, 2H), 7.09-6.81 (m, 3H), 6.04 (s, 1H), 5.36 (dd, J = 12.4, 5.2 Hz, 1H), 3.82-3.68 (m, 2H), 3.62 (s, 3H), 3.57 (s, 2H), 3.24 (s, 8H), 2.96-2.81 (m, 1H), 2.76-2.58 (m, 2H), 2.07-1.94 (m, 1H), 1.66 (s, 6H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-47 | WX | APP | 816.6 | 11.22 (s, 1H), 9.30 (dd, J = 1.6, 7.2 Hz, 1H), 8.80 (dd, J = 1.6, 4.4 Hz, 1H), 8.64 (s, 1H), 8.31 (d, J = 8.8 Hz, 2H), 7.54 (s, 1H), 7.29-7.25 (m, 1H), 7.09-7.03 (m, 1H), 6.95 (t, J = 7.6 Hz, 1H), 6.87 (d, J = 8.4 Hz, 1H), 5.68 (s, 1H), 5.42-5.32 (m, 1H), 4.44-4.33 (m, 1H), 3.68 (s, 3H), 3.61 (s, 2H), 2.87 (d, J = 10.8 Hz, 3H), 2.60-2.55 (m, 2H), 2.21 (d, J = 6.4 Hz, 2H), 2.17 (s, 3H), 2.15-2.08 (m, 3H), 2.05-1.86 (m, 8H), 1.59 (s, 8H), 1.54-1.46 (m, 1H), 1.44-1.33 (m, 2H), 1.15-1.00 (m, 2H) |
| I-48 | WX | APL | 838.4 | 12.45 (s, 1H), 11.09-11.06 (m, 1H), 9.04 (s, 1H), 8.82 (s, 1H), 8.47 (d, J = 8.0 Hz, 1H), 8.38 (t, J = 8.0 Hz, 1H), 8.17 (d, J = 8.0 Hz, 1H), 8.02-7.98 (m, 2H), 7.69 (s, 1H), 7.52-7.46 (m, 2H), 7.07 (d, J = 8.0 Hz, 1H), 6.96 (t, J = 8.0 Hz, 1H), 6.87 (d, J = 8.0 Hz, 1H), 6.04 (s, 1H), 5.37 (dd, J = 5.2, 12.4 Hz, 1H), 3.68 (s, 3H), 3.64-3.59 (m, 4H), 2.97-2.87 (m, 3H), 2.76-2.62 (m, 2H), 2.13 (s, 3H), 2.03-1.96 (m, 3H), 1.79-1.71 (m, 2H), 1.65 (s, 6H), 1.56-1.44 (m, 2H) |
| I-49 | AMZ | APL | 880.5 | 12.45 (s, 1H), 11.19-10.99 (m, 1H), 9.04 (s, 1H), 8.82 (s, 1H), 8.49-8.44 (m, 1H), 8.17 (d, J = 7.8 Hz, 1H), 8.00 (d, J = 8.4 Hz, 2H), 7.69 (s, 1H), 7.47 (d, J = 8.4 Hz, 2H), 7.08 (d, J = 7.6 Hz, 1H), 6.96 (t, J = 7.6 Hz, 1H), 6.90-6.86 (m, 1H), 6.11-5.98 (m, 1H), 5.37 (dd, J = 5.2, 12.4 Hz, 1H), 3.67 (s, 3H), 3.60-3.49 (m, 7H), 2.93-2.59 (m, 4H), 2.42-2.36 (m, 2H), 2.33-2.27 (m, 5H), 2.03-1.97 (m, 1H), 1.88-1.76 (m, 2H), 1.66 (s, 6H), 1.53-1.45 (m, 2H) |
| I-50 | APZ | AGL | 869.5 | 12.36 (s, 1H), 11.09 (s, 1H), 8.72 (s, 1H), 8.48-8.43 (m, 1H), 8.42-8.34 (m, 2H), 8.16 (d, J = 7.6 Hz, 1H), 7.58 (s, 1H), 6.96 (d, J = 4.8 Hz, 2H), 6.88-6.82 (m, 1H), 5.94 (s, 1H), 5.37 (dd, J = 5.2, 12.4 Hz, 1H), 4.47-4.36 (m, 1H), 3.56 (s, 3H), 2.96-2.73 (m, 4H), 2.69-2.58 (m, 2H), 2.32-2.16 (m, 5H), 2.17-2.08 (m, 4H), 2.01-1.86 (m, 7H), 1.76-1.68 (m, 2H), 1.63 (s, 6H), 1.57 (s, 2H), 1.49 (t, J = 5.2 Hz, 2H), 1.43-1.34 (m, 2H), 1.17-1.03 (m, 2H) |
| I-51 | WX | AOF | 776.6 | 12.32 (s, 1H), 11.09 (s, 1H), 8.70 (d, J = 4.4 Hz, 1H), 8.67 (s, 1H), 8.35-8.19 (m, 2H), 8.06 (t, J = 1.6, 7.6 Hz, 1H), 7.64-7.61(m, 1H), 7.56-7.04 (m, 2H), 6.96 (t, J = 7.6 Hz, 1H), 6.87 (d, J = 7.2 Hz, 1H), 6.01 (s, 1H), 5.38 (dd, J = 5.6, 12.8 Hz, 1H), 4.44-4.34 (m, 1H), 3.68 (s, 3H), 3.62 (s, 2H), 2.92-2.84 (m, 3H), 2.79-2.69 (m, 1H), 2.22 (d, J = 6.8 Hz, 2H), 2.18 (s, 3H), 2.15-2.07 (m, 3H), 2.06-1.83 (m, 8H), 1.68-1.59 (m, 8H), 1.55-1.47 (m, 1H), 1.45-1.34 (m, 2H), 1.13-1.01 (m, 2H) |
| I-52 | ACV | AGL | 870.6 | 12.36 (s, 1H), 11.08 (s, 1H), 8.71 (s, 1H), 8.48-8.41 (m, 1H), 8.39-8.35 (m, 1H), 8.34 (s, 1H), 8.15 (dd, J = 0.8, 8.0 Hz, 1H), 7.57 (s, 1H), 7.02-6.85 (m, 3H), 6.11-5.77 (m, 1H), 5.36 (dd, J = 5.4, 12.4 Hz, 1H), 4.50-4.38 (m, 1H), 3.57 (s, 3H), 3.37-3.22 (m, 2H), 3.05 (s, 4H), 2.95-2.89 (m, 2H), 2.88-2.80 (m, 1H), 2.79-2.73 (m, 2H), 2.73-2.60 (m, 2H), 2.27 (s, 3H), 2.17-2.06 (m, 4H), 2.02-1.97 (m, 1H), 1.96-1.81 (m, 4H), 1.68 (s, 4H), 1.62 (s, 6H), 1.18-1.00 (m, 2H) |
| I-53 | AMS | AGL | 855.6 | 12.35 (s, 1H), 11.08 (s, 1H), 8.71 (s, 1H), 8.47-8.42 (m, 1H), 8.39-8.31 (m, 2H), 8.15 (dd, J = 0.7, 7.8 Hz, 1H), 7.56 (s, 1H), 7.01-6.90 (m, 2H), 6.83 (dd, J = 2.1, 6.8 Hz, 1H), 5.93 (s, 1H), 5.35 (dd, J = 5.3, 12.6 Hz, 1H), 4.48-4.29 (m, 1H), 3.54 (s, 3H), 3.03 (d, J = 7.3 Hz, 2H), 2.96-2.83 (m, 1H), 2.76-2.66 (m, 1H), 2.66-2.58 (m, 1H), 2.58-2.52 (m, 1H), 2.31-2.10 (m, 5H), 2.08 (d, J = 7.3 Hz, 2H), 2.02-1.96 (m, 1H), 1.96-1.81 (m, 6H), 1.62 (s, 6H), 1.56 (s, 2H), 1.53-1.44 (m, 4H), 1.17-0.99 (m, 2H) |
| I-54 | AGI | AGL | 856.6 | 12.35 (s, 1H), 11.09 (s, 1H), 8.71 (s, 1H), 8.47-8.42 (m, 1H), 8.39-8.32 (m, 2H), 8.15 (dd, J = 0.8, 7.6 Hz, 1H), 7.56 (s, 1H), 7.08-7.02 (m, 1H), 6.98-6.89 (m, 2H), 5.92 (s, 1H), 5.36 (dd, J = 5.2, 12.8 Hz, 1H), 4.48-4.33 (m, 1H), 3.80 (s, 2H), 3.65 (s, 4H), 2.94 (s, 3H), 2.92-2.82 (m, 2H), 2.75-2.58 (m, 2H), 2.53-2.51 (m, |

TABLE 7-continued

| Compounds synthesized via Method 2 with the reductive amination of various intermediate amines and aldehydes. | | | | |
|---|---|---|---|---|
| I-# | Intermediate Amine | Intermediate Aldehyde | LCMS (ES+) m/z $(M + H)^+$ | $^1$HNMR (400 MHz, DMSO-$d_6$) δ |
| | | | | 1H), 2.36-2.20 (m, 4H), 2.18-2.07 (m, 4H), 2.04-1.98 (m, 1H), 1.96-1.83 (m, 4H), 1.68 (s, 3H), 1.61 (s, 6H), 1.17-1.00 (m, 2H) |
| I-55 | AVZ | AQO | 849.6 | 12.45 (s, 1H), 11.11 (s, 1H), 9.32 (s, 1H), 8.81 (s, 1H), 8.36 (s, 1H), 8.14-8.09 (m, 2H), 7.80-7.74 (m, 1H), 7.62-7.55 (m, 2H), 7.15 (d, J = 8.8 Hz, 1H), 7.05 (d, J = 7.2 Hz, 1H), 6.70-6.61 (m, 1H), 6.19-5.90 (m, 1H), 5.07 (dd, J = 5.6, 12.8 Hz, 1H), 4.50-4.40 (m, 1H), 3.23 (s, 3H), 3.15-3.05 (m, 1H), 2.96-2.83 (m, 2H), 2.75 (d, J = 4.8 Hz, 3H), 2.65-2.53 (m, 2H), 2.16 (d, J = 10.0 Hz, 4H), 2.07-2.02 (m, 2H), 1.99-1.84 (m, 6H), 1.82 (s, 3H), 1.78-1.72 (m, 4H), 1.65 (s, 6H), 1.56-1.47 (m, 2H), 1.32-1.11 (m, 4H) |
| I-56 | AJH | AQO | 879.1 | 12.44 (s, 1H), 11.09 (s, 1H), 8.79 (s, 1H), 8.34 (s, 1H), 8.27 (br s, 1H), 8.14-8.07 (m, 2H), 7.76 (td, J = 2.0, 3.6 Hz, 1H), 7.62-7.54 (m, 2H), 7.15-6.99 (m, 2H), 6.67 (s, 1H), 6.04 (s, 1H), 5.04 (s, 1H), 4.40 (s, 1H), 3.46 (t, J = 5.6 Hz, 3H), 3.22 (d, J = 6.4 Hz, 2H), 2.95-2.77 (m, 3H), 2.64-2.53 (m, 2H), 2.18-2.08 (m, 4H), 2.06-2.00 (m, 1H), 1.96-1.79 (m, UH), 1.75 (s, 3H), 1.69-1.49 (m, 11H), 1.20-1.03 (m, 4H) |
| I-57 | AQJ | AGL | 799.5 | 12.36 (s, 1H), 11.53-10.69 (m, 1H), 8.71 (s, 1H), 8.48-8.42 (m, 1H), 8.41-8.21 (m, 3H), 8.16 (dd, J = 0.8. 7.6 Hz, 1H), 7.57 (s, 1H), 7.12 (d, J = 7.6 Hz, 1H), 7.09-7.05 (m, 1H), 7.03-6.97 (m, 1H), 6.05-5.82 (m, 1H), 5.38 (dd, J = 5.2, 12.4 Hz, 1H), 4.48-4.34 (m, 1H), 3.66 (s, 3H), 2.94-2.86 (m, 1H), 2.85-2.70 (m, 3H), 2.66-2.62 (m, 1H), 2.60-2.53 (m, 4H), 2.18-2.09 (m, 2H), 2.04-1.83 (m, 5H), 1.82-1.74 (m, 2H), 1.62 (s, 6H), 1.59-1.50 (m, 1H), 1.26-1.10 (m, 2H) |
| I-58 | ATV | AGL | 799.2 | 12.38 (s, 1H), 11.30-10.95 (m, 1H), 8.73 (s, 1H), 8.49-8.44 (m, 1H), 8.41-8.34 (m, 2H), 8.20-8.15 (m, 1H), 7.58 (s, 1H), 7.26 (s, 1H), 7.13 (s, 2H), 5.97 (s, 1H), 5.39 (dd, J = 5.6, 12.8 Hz, 1H), 4.52-4.41 (m, 1H), 3.51-3.38 (m, 4H), 3.01 (t, J = 7.2 Hz, 2H), 2.93-2.79 (m, 3H), 2.76-2.61 (m, 2H), 2.56 (t, J = 6.8 Hz, 2H), 2.18 (d, J = 11.6 Hz, 2H), 2.06-1.85 (m, 7H), 1.79-1.71 (m, 1H), 1.63 (s, 6H), 1.31-1.19 (m, 2H) |
| I-59 | AVU | AGL | 843.5 | 12.36 (s, 1H), 11.10 (s, 1H), 8.71 (s, 1H), 8.47-8.42 (m, 1H), 8.41-8.33 (m, 2H), 8.15 (d, J = 7.6 Hz, 1H), 7.56 (s, 1H), 7.01-6.91 (m, 2H), 6.83-6.77 (m, 1H), 6.12-5.71 (m, 1H), 5.37 (dd, J = 5.6, 12.4 Hz, 1H), 4.39 (t, J = 11.2 Hz, 1H), 3.54 (s, 3H), 2.95-2.85 (m, 1H), 2.80-2.60 (m, 4H), 2.49-2.40 (m, 2H), 2.35-2.27 (m, 2H), 2.23 (s, 3H), 2.12 (d, J = 10.4 Hz, 2H), 2.02-1.84 (m, 5H), 1.75 (d, J = 8.0 Hz, 4H), 1.61 (s, 6H), 1.55-1.41 (m, 2H), 1.30-1.16 (m, 2H), 1.13-0.99 (m, 4H) |
| I-60 | AJF | ALU | 861.2 | 11.20-10.95 (m, 1H), 10.62-10.37 (m, 1H), 8.55 (s, 1H), 8.48 (s, 1H), 8.47-8.44 (m, 1H), 8.43-8.38 (m, 1H), 8.22 (dd, J = 0.8, 7.6 Hz, 1H), 7.98 (s, 1H), 7.58 (dd, J = 7.6, 8.4 Hz, 1H), 7.43-7.07 (m, 2H), 7.02 (d, J = 7.2 Hz, 1H), 6.46 (t, J = 5.2 Hz, 1H), 5.04 (dd, J = 5.6, 12.8 Hz, 1H), 4.56-4.42 (m, 1H), 2.94-2.80 (m, 1H), 2.63-2.53 (m, 2H), 2.30-2.12 (m, 7H), 2.11-2.00 (m, 4H), 1.98-1.82 (m, 7H), 1.67-1.54 (m, 3H), 1.50 (t, J = 9.2 Hz, 4H), 1.17-1.02 (m, 2H) |
| I-61 | AOV | APG | 789.6 | 12.39 (s, 1H), 11.09 (s, 1H), 8.71 (s, 1H), 8.34 (s, 1H), 8.00-7.88 (m, 2H), 7.63-7.55 (m, 2H), 7.50 (dd, J = 0.8, 7.2 Hz, 1H), 7.19 (d, J = 8.8 Hz, 1H), 7.05 (d, J = 6.8 Hz, 1H), 6.17 (d, J = 8.4 Hz, 1H), 5.90 (s, 1H), 5.06 (dd, J = 5.2, 12.8 Hz, 1H), 4.43 (br s, 1H), 3.58-3.49 (m, 1H), 2.94-2.83 (m, 1H), 2.61 (s, 3H), 2.30 (br s, 3H), 2.20-1.89 (m, 10H), 1.82 (br d, J = 10.4 Hz, 2H), 1.64 (s, 6H), 1.53-1.43 (m, 2H), 1.39-1.29 (m, 2H), 1.19-1.08 (m, 2H) |
| I-62 | WX | APG | 790.6 | 12.38 (s, 1H), 11.38-10.82 (m, 1H), 8.69 (s, 1H), 8.32 (s, 1H), 7.98-7.89 (m, 2H), 7.55 (s, 1H), 7.52-7.45 (m, 1H), 7.07 (d, J = 7.6 Hz, 1H), 6.96 (t, J = 7.8 Hz, 1H), 6.87 (d, J = 7.2 Hz, 1H), 5.89 (s, 1H), 5.38 (dd, J = 5.2, 12.4 Hz, 1H), 4.48-4.31 (m, 1H), 3.68 (s, 3H), 3.62 (s, 2H), 2.96-2.81 (m, 3H), 2.77-2.67 (m, 1H), 2.66-2.60 (m, 1H), 2.60 (s, 3H), 2.31-2.26 (m, 1H), |

TABLE 7-continued

| Compounds synthesized via Method 2 with the reductive amination of various intermediate amines and aldehydes. | | | | |
|---|---|---|---|---|
| I-# | Intermediate Amine | Intermediate Aldehyde | LCMS (ES+) m/z $(M + H)^+$ | $^1$HNMR (400 MHz, DMSO-$d_6$) δ |
| | | | | 2.21 (d, J = 6.8 Hz, 2H), 2.17 (s, 3H), 2.12 (d, J = 10.8 Hz, 2H), 2.03-1.84 (m, 8H), 1.67-1.64 (m, 1H), 1.63 (s, 6H), 1.54-1.46 (m, 1H), 1.44-1.32 (m, 2H), 1.12-1.00 (m, 2H) |
| I-64 | ASY | AGL | 859.5 | 12.36 (s, 1H), 11.10 (s, 1H), 8.71 (s, 1H), 8.48-8.00 (m, 4H), 7.63-7.52 (m, 2H), 7.10 (d, J = 8.8 Hz, 1H), 7.02 (d, J = 7.2 Hz, 1H), 6.59 (d, J = 4.4 Hz, 1H), 5.94 (s, 1H), 5.09-5.01 (m, 1H), 4.41 (t, J = 11.6 Hz, 1H), 3.77 (d, J = 10.8 Hz, 1H), 3.55-3.33 (m, 6H), 2.93-2.81 (m, 1H), 2.77-2.55 (m, 4H), 2.19-1.83 (m, 9H), 1.73-1.64 (m, 3H), 1.62 (s, 6H), 1.51-1.39 (m, 2H), 1.18-1.00 (m, 2H) |
| I-65 | AQY | AGL | 845.2 | 12.36 (s, 1H), 11.09 (s, 1H), 8.71 (s, 1H), 8.47-8.42 (m, 1H), 8.39-8.32 (m, 2H), 8.19-8.13 (m, 1H), 7.63-7.55 (m, 2H), 7.13-6.99 (m, 2H), 6.76-6.71 (m, 1H), 5.94 (s, 1H), 5.05 (dd, J = 5.2, 12.8 Hz, 1H), 4.48-4.34 (m, 1H), 3.83 (d, J = 9.6 Hz, 1H), 3.57-3.47 (m, 2H), 3.44-3.36 (m, 2H), 2.94-2.83 (m, 1H), 2.81-2.72 (m, 1H), 2.63-2.52 (m, 3H), 2.18-2.08 (m, 4H), 2.06-1.98 (m, 2H), 1.97-1.87 (m, 4H), 1.81-1.65 (m, 4H), 1.61 (s, 6H), 1.17-1.05 (m, 2H) |
| I-66 | ABA | AGL | 914.5 | 12.37 (s, 1H), 11.11 (s, 1H), 8.72 (s, 1H), 8.49-8.43 (m, 1H), 8.41-8.33 (m, 2H), 8.16 (s, 1H), 7.58 (s, 1H), 7.07 (d, J = 7.6 Hz, 1H), 6.96 (t, J = 7.6 Hz, 1H), 6.88 (d, J = 7.2 Hz, 1H), 5.95 (d, J = 6.4 Hz, 1H), 5.38 (d, J = 12.4 Hz, 1H), 4.42 (t, J = 11.2 Hz, 1H), 3.68 (s, 4H), 3.62 (s, 3H), 2.94-2.87 (m, 1H), 2.79-2.63 (m, 6H), 2.24-1.71 (m, 18H), 1.62 (s, 6H), 1.50-1.31 (m, 4H), 1.17-1.02 (m, 2H) |
| I-68 | ASY | ATJ | 831.5 | 11.10 (s, 1H), 10.50 (s, 1H), 8.69 (s, 1H), 8.49-8.37 (m, 2H), 8.32 (s, 1H), 8.22 (d, J = 7.6 Hz, 1H), 7.59 (t, J = 7.6 Hz, 1H), 7.18-7.00 (m, 3H), 6.63-6.54 (m, 1H), 5.09-5.02 (m, 1H), 4.48-4.28 (m, 1H), 3.98 (s, 4H), 3.86-3.63 (m, 2H), 3.62-3.42 (m, 2H), 3.10-2.96 (m, 1H), 2.94-2.83 (m, 2H), 2.82-2.70 (m, 1H), 2.64-2.54 (m, 2H), 2.21-1.82 (m, 10H), 1.77-1.58 (m, 3H), 1.56-1.43 (m, 2H), 1.33-1.05 (m, 2H) |
| I-69 | AWB | ATJ | 899.5 | 11.10 (s, 1H), 10.50 (s, 1H), 8.69 (s, 1H), 8.48-8.44 (m, 1H), 8.43-8.38 (m, 1H), 8.32 (s, 1H), 8.24-8.19 (m, 1H), 7.61-7.53 (m, 1H), 7.14 (s, 1H), 7.11 (d, J = 8.4 Hz, 1H), 7.02 (d, J = 7.2 Hz, 1H), 6.58 (t, J = 6.0 Hz, 1H), 5.08-5.02 (m, 1H), 4.45-4.32 (m, 1H), 3.98 (s, 3H), 3.73-3.52 (m, 1H), 3.17 (t, J = 6.4 Hz, 3H), 3.13-2.96 (m, 2H), 2.95-2.83 (m, 2H), 2.80-2.69 (m, 1H), 2.64-2.53 (m, 2H), 2.15 (d, J = 9.6 Hz, 2H), 2.07-1.50 (m, 16H), 1.26-0.96 (m, 7H) |
| I-70 | AOQ | AMI | 887.3 | 11.17-10.98 (m, 1H), 10.53 (s, 1H), 8.34 (s, 1H), 8.26 (s, 1H), 8.14-8.05 (m, 1H), 7.79 (dd, J = 7.6, 18.4 Hz, 2H), 7.61-7.54 (m, 1H), 7.47 (s, 1H), 7.07 (d, J = 7.2 Hz, 1H), 6.91 (d, J = 8.4 Hz, 1H), 6.50 (d, J = 5.6 Hz, 1H), 5.97-5.88 (m, 1H), 5.05 (dd, J = 5.6, 12.8 Hz, 1H), 4.44-4.31 (m, 1H), 4.20-4.06 (m, 2H), 3.97 (s, 2H), 3.36-3.34 (m, 2H), 2.95-2.79 (m, 1H), 2.62-2.52 (m, 3H), 2.42-2.32 (m, 5H), 2.27-2.20 (m, 2H), 2.13 (s, 3H), 2.12-1.98 (m, 4H), 1.96-1.84 (m, 4H), 1.68-1.61 (m, 2H), 1.49 (s, 6H), 1.15-1.02 (m, 2H) |
| I-71 | AQY | ATJ | 817.2 | 11.09 (s, 1H), 10.50 (s, 1H), 8.68 (s, 1H), 8.50-8.37 (m, 2H), 8.31 (s, 1H), 8.21 (dd, J = 0.8, 7.6 Hz, 1H), 7.59 (dd, J = 7.2, 8.4 Hz, 1H), 7.15 (s, 1H), 7.10 (d, J = 8.8 Hz, 1H), 7.02 (d, J = 7.2 Hz, 1H), 6.79-6.70 (m, 1H), 5.05 (dd, J = 5.2, 12.8 Hz, 1H), 4.42-4.31 (m, 1H), 3.98 (s, 3H), 3.82 (d, J = 10.8 Hz, 1H), 3.55-3.47 (m, 2H), 3.42-3.38 (m, 2H), 2.95-2.82 (m, 1H), 2.76 (d, J = 10.8 Hz, 1H), 2.68-2.63 (m, 1H), 2.62-2.52 (m, 2H), 2.18-2.09 (m, 4H), 2.05-1.83 (m, 6H), 1.80-1.60 (m, 4H), 1.18-1.04 (m, 2H) |
| I-72 | AVW | ALU | 807.3 | 11.11 (s, 1H), 10.50 (s, 1H), 8.61-8.37 (m, 4H), 8.22 (d, J = 0.8 Hz, 1H), 7.99 (s, 1H), 7.46-7.07 (m, 1H), 7.04-6.77 (m, 3H), 5.38 (dd, J = 5.6, 12.4 Hz, 1H), 4.59-4.44 (m, 1H), 3.55 (s, 3H), 2.92-2.80 (m, 5H), 2.78-2.69 (m, 1H), 2.65-2.57 (m, 2H), 2.26-1.75 (m, 10H), 1.68-1.57 (m, 3H), 1.54-1.44 (m, 1H), 1.37-1.25 (m, 2H), 1.18-1.04 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | 1HNMR (400 MHz, DMSO-$d_6$) δ |
|---|---|---|---|---|
| I-73 | AVU | ALU | 835.5 | 11.10 (s, 1H), 10.49 (s, 1H), 8.55 (s, 1H), 8.50-8.43 (m, 2H), 8.43-8.37 (m, 1H), 8.22 (dd, J = 0.8, 7.6 Hz, 1H), 7.98 (s, 1H), 7.39-7.09 (m, 1H), 7.00-6.92 (m, 2H), 6.80 (dd, J = 1.2, 7.2 Hz, 1H), 5.37 (dd, J = 5.6, 12.4 Hz, 1H), 4.55-4.43 (m, 1H), 3.54 (s, 3H), 2.94-2.84 (m, 1H), 2.78-2.60 (m, 4H), 2.44-2.36 (m, 1H), 2.26 (d, J = 6.4 Hz, 2H), 2.20 (s, 3H), 2.14 (d, J = 92 Hz, 2H), 2.02-1.86 (m, 5H), 1.73 (t, J = 11.2 Hz, 4H), 1.56-1.40 (m, 2H), 1.27-1.16 (m, 2H), 1.12-1.00 (m, 4H) |
| I-74 | ARW | AGL | 883.6 | 12.36 (s, 1H), 11.09 (s, 1H), 8.71 (s, 1H), 8.49-8.41 (m, 1H), 8.39-8.31 (m, 2H), 8.15 (d, J = 7.6 Hz, 1H), 7.56 (s, 1H), 7.01-6.90 (m, 2H), 6.87-6.79 (m, 1H), 6.09-5.76 (m, 1H), 5.36 (dd, J = 5.2, 12.4 Hz, 1H), 4.46-4.33 (m, 1H), 3.54 (s, 3H), 3.09-2.83 (m, 3H), 2.73-2.58 (m, 2H), 2.24 (d, J = 6.8 Hz, 2H), 2.19 (s, 3H), 2.12 (d, J = 10.4 Hz, 2H), 2.03-1.74 (m, 9H), 1.61 (s, 6H), 1.57-1.47 (m, 4H), 1.46-1.39 (m, 1H), 1.33-1.14 (m, 4H), 1.13-1.00 (m, 2H) |
| I-75 | AVX | AGL | 830.5 | 12.36 (s, 1H), 11.06 (s, 1H), 8.71 (s, 1H), 8.48-8.42 (m, 1H), 8.40-8.30 (m, 2H), 8.16 (dd, J = 0.8, 7.6 Hz, 1H), 7.57 (s, 1H), 6.93 (d, J = 8.8 Hz, 1H), 6.83 (d, J = 2.0 Hz, 1H), 6.64 (dd, J = 2.0, 8.8 Hz, 1H), 5.94 (s, 1H), 5.29 (dd, J = 5.2, 12.8 Hz, 1H), 4.50-4.36 (m, 1H), 3.70-3.62 (m, 2H), 3.31 (s, 3H), 2.94-2.83 (m, 1H), 2.70-2.58 (m, 4H), 2.46-2.41 (m, 1H), 2.29 (d, J = 6.8 Hz, 2H), 2.24 (s, 3H), 2.18-2.10 (m, 2H), 2.02-1.86 (m, 5H), 1.82-1.71 (m, 2H), 1.62 (s, 6H), 1.60-1.52 (m, 3H), 1.21-1.00 (m, 2H) |
| I-76 | AWC | ATJ | 801.4 | 11.15-11.05 (m, 1H), 10.50 (s, 1H), 8.68 (s, 1H), 8.48-8.43 (m, 1H), 8.43-8.37 (m, 1H), 8.33 (s, 1H), 8.23-8.17 (m, 1H), 7.70-7.66 (m, 1H), 7.40-7.27 (m, 2H), 7.15 (s, 1H), 5.10 (dd, J = 5.2, 12.8 Hz, 1H), 4.42-4.30 (m, 1H), 3.98 (s, 3H), 3.75 (d, J = 11.2 Hz, 2H), 2.94-2.83 (m, 3H), 2.65-2.55 (m, 2H), 2.47-2.38 (m, 1H), 2.29 (d, J = 6.8 Hz, 2H), 2.25 (s, 3H), 2.14 (m, 2H), 2.07-2.00 (m, 1H), 1.99-1.86 (m, 4H), 1.83-1.74 (m, 2H), 1.70-1.60 (m, 2H), 1.58-1.46 (m Hz, 1H), 1.24-1.01 (m, 2H) |
| I-77 | AWD | ATJ | 845.1 | 11.05 (s, 1H), 10.50 (s, 1H), 8.68 (s, 1H), 8.49-8.44 (m, 1H), 8.43-8.37 (m, 1H), 8.32 (s, 1H), 8.22 (dd, J = 1.2, 8.0 Hz, 1H), 7.58 (d, J = 8.4 Hz, 1H), 7.44 (d, J = 5.6 Hz, 1H), 7.14 (s, 1H), 6.82 (s, 1H), 6.76 (d, J = 8.0 Hz, 1H), 5.02 (dd, J = 5.2, 12.8 Hz, 1H), 4.41-4.32 (m, 1H), 4.16-4.08(m, 1H), 4.06-3.99 (m, 1H), 3.97 (s, 3H), 2.92-2.81 (m, 1H), 2.61-2.53 (m, 2H), 2.45-2.40 (m, 2H), 2.39-2.31 (m, 3H), 2.25-2.11 (m, 9H), 2.06-1.80 (m, 6H), 1.71-1.64 (m, 2H), 1.62-1.53(m, 1H), 021.16-1.06 (m, 2H) |
| I-78 | AML | AWF | 819.4 | 11.10 (s, 1H), 10.79 (s, 1H), 8.66 (s, 1H), 8.30 (s, 1H), 8.26 (s, 1H), 8.19-8.09 (m, 2H), 7.87-7.82 (m, 1H), 7.58 (m, 1H), 7.14 (s, 1H), 7.06 (d, J = 7.1 Hz, 1H), 7.00 (d, J = 8.7 Hz, 1H), 6.44 (d, J = 6.6 Hz, 1H), 5.06 (m, 1H), 4.40-4.29 (m, 1H), 4.18-4.07 (m, 1H), 3.99 (s, 3H), 2.95-2.81 (m, 1H), 2.69-2.65 (m, 1H), 2.69-2.59 (m, 2H), 2.38-2.28 (m, 4H), 2.26-2.19 (m, 2H), 2.16-2.08 (m, 4H), 2.06-1.98 (m, 1H), 1.96-1.84 (m, 4H), 1.82 (s, 3H), 1.76 (s, 3H), 1.72-1.49 (m, 7H), 1.08 (q, J = 11.9 Hz, 2H) |
| I-79 | AWI | AWG | 829.4 | 12.36 (s, 1H), 11.10 (s, 1H), 8.72 (s, 1H), 8.47-8.42 (m, 1H), 8.36 (t, J = 8.0 Hz, 1H), 8.32 (s, 1H), 8.21 (s, 1H), 8.16 (d, J = 7.8 Hz, 1H), 7.61-7.52 (m, 2H), 7.05 (d, J = 7.2 Hz, 1H), 6.98 (d, J = 8.6 Hz, 1H), 6.42 (d, J = 6.4 Hz, 1H), 5.95 (s, 1H), 5.05 (m, 1H), 4.41 (m, 2H), 4.13-4.00 (m, 1H), 2.96-2.79 (m, 1H), 2.70-2.55 (m, 1H), 2.45-2.35 (m, 3H), 2.34-2.25 (m, 1H), 2.23-2.13 (m, 4H), 2.09-1.96 (m, 3H), 1.85 (m, 1H), 1.74-1.46 (m, 12H), 1.39-1.11 (m, 4H) |
| I-80 | AQK | AGL | 852.5 (M + Na) | 12.37 (s, 1H), 11.10 (s, 1H), 8.72 (s, 1H), 8.49-8.42 (m, 1H), 8.40-8.33 (m, 2H), 8.19-8.13 (m, 1H), 7.58 (s, 1H), 7.02-6.84 (m, 3H), 5.95 (s, 1H), 5.42-5.29 (m, 1H), 4.49-4.38 (m, 1H), 3.65 (s, 3H), 3.18-3.13 (m, 2H), 2.95-2.84 (m, 1H), 2.79-2.68 (m, 3H), 2.66-2.57 (m, 1H), 2.35-2.30 (m, 2H), 2.27 (s, 3H), 2.19- |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 2.11 (m, 2H), 2.02-1.87 (m, 5H), 1.85-1.76 (m, 2H), 1.75-1.50 (m, 10H), 1.19-1.05 (m, 2H) |
| I-81 | APZ | ASM | 801.5 | 12.33 (s, 1H), 11.09 (s, 1H), 8.70 (dd, J = 1.2, 4.4 Hz, 1H), 8.68 (s, 1H), 8.33 (s, 1H), 8.19 (s, 1H), 8.06 (dt, J = 1.6, 7.6 Hz, 1H), 7.64 (ddd, J = 1.2, 4.8, 7.6 Hz, 1H), 7.55 (s, 1H), 6.95 (d, J = 4.8 Hz, 2H), 6.87-6.81 (m, 1H), 6.14-5.90 (m, 1H), 5.36 (dd, J = 5.2, 12.8 Hz, 1H), 4.45-4.35 (m, 1H), 3.55 (s, 3H), 2.93-2.60 (m, 5H), 2.39-2.21 (m, 5H), 2.19-2.10 (m, 4H), 2.08-1.77 (m, 8H), 1.74-1.67 (m, 2H), 1.61 (s, 6H), 1.58 (d, J = 4.8 Hz, 2H), 1.50 (t, J = 5.2 Hz, 2H), 1.42-1.35 (m, 2H), 1.15-1.04 (m, 2H) |
| I-82 | AVX | ASM | 744.5 (M-17)+ | 12.33 (s, 1H), 11.07 (s, 1H), 8.70 (d, J = 4.4 Hz, 1H), 8.68 (s, 1H), 8.34 (s, 1H), 8.19 (d, J = 8.0 Hz, 1H), 8.10-8.03 (m, 1H), 7.67-7.60 (m, 1H), 7.55 (s, 1H), 6.93 (d, J = 8.8 Hz, 1H), 6.83 (d, J = 1.6 Hz, 1H), 6.64 (dd, J = 1.6, 8.8 Hz, 1H), 5.97 (s, 1H), 5.29 (dd, J = 5.2, 12.8 Hz, 1H), 4.50-4.33 (m, 1H), 3.68-3.62 (m, 3H), 3.31 (s, 3H), 2.93-2.84 (m, 1H), 2.71-2.58 (m, 4H), 2.55-2.52 (m, 2H), 2.46-2.40 (m, 1H), 2.28 (d, J = 6.8 Hz, 2H), 2.18-2.10 (m, 2H), 2.03-1.87 (m, 5H), 1.81-1.73 (m, 2H), 1.61 (s, 6H), 1.60-1.49 (m, 3H), 1.17-1.03 (m, 2H) |
| I-83 | ASK | AGL | 830.6 | 12.36 (s, 1H), 11.06 (s, 1H), 8.71 (s, 1H), 8.49-8.41 (m, 1H), 8.39-8.33 (m, 2H), 8.19-8.12 (m, 1H), 7.57 (s, 1H), 7.00 (d, J = 8.4 Hz, 1H), 6.80 (s, 1H), 6.69 (d, J = 8.8 Hz, 1H), 5.94 (s, 1H), 5.34 (dd, J = 5.2, 12.4 Hz, 1H), 4.48-4.37 (m, 1H), 3.68-3.54 (m, 3H), 3.28 (s, 3H), 2.68-2.59 (m, 5H), 2.30 (d, J = 6.8 Hz, 2H), 2.25 (s, 3H), 2.18-2.11 (m, 2H), 2.01-1.88 (m, 5H), 1.78 (d, J = 10.4 Hz, 2H), 1.65-1.53 (m, 9H), 1.17-1.03 (m, 2H) |
| I-84 | AQK | ASM | 744.5 (M-17)+ | 12.33 (s, 1H), 11.09 (s, 1H), 8.70 (dd, J = 1.2, 4.4 Hz, 1H), 8.68 (s, 1H), 8.35 (s, 1H), 8.19 (d, J = 7.6 Hz, 1H), 8.06 (dt, J = 1.6.7.6 Hz, 1H), 7.67-7.61 (m, 1H), 7.56 (s, 1H), 7.00-6.95 (m, 1H), 6.93-6.89 (m, 1H), 6.89-6.84 (m, 1H), 6.16-5.85 (m, 1H), 5.41-5.29 (m, 1H), 4.52-4.34 (m, 1H), 3.64 (s, 3H), 3.16 (d, J = 11.2 Hz, 2H), 2.93-2.84 (m, 1H), 2.75-2.69 (m, 2H), 2.65-2.57 (m, 1H), 2.46-2.41 (m, 1H), 2.30 (d, J = 6.4 Hz, 2H), 2.26 (s, 3H), 2.19-2.10 (m, 2H), 2.05-1.75 (m, 8H), 1.73-1.63 (m, 2H), 1.62 (s, 6H), 1.58-1.51 (m, 1H), 1.20-1.03 (m, 2H) |
| I-85 | ARU | AGL | 873.6 | 12.37 (s, 1H), 11.09 (s, 1H), 8.72 (s, 1H), 8.53-8.32 (m, 3H), 8.17 (d, J = 8.0 Hz, 1H), 7.58 (s, 1H), 7.02-6.90 (m, 2H), 6.85 (dd, J = 2.0, 6.8 Hz, 1H), 5.95 (s, 1H), 5.36 (dd, J = 5.2, 12.8 Hz, 1H), 4.51-4.36 (m, 1H), 4.16-4.12 (m, 1H), 3.55 (s, 3H), 3.33-3.30 (m, 2H), 3.08 (d, J = 8.0 Hz 2H), 2.94-2.83 (m, 1H), 2.77-2.68 (m, 1H), 2.66-2.58 (m, 1H), 2.46-2.44 (m, 1H), 2.35 (t, J = 6.8 Hz, 2H), 2.20-2.10 (m, 7H), 2.07-1.85 (m, 9H), 1.70-1.53 (m, 9H), 1.17-1.02 (m, 2H) |
| I-86 | ASK | ASM | 762.5 | 12.33 (s, 1H), 11.07 (s, 1H), 8.73-8.69 (m, 1H), 8.67 (s, 1H), 8.34 (s, 1H), 8.19 (d, J = 8.0 Hz, 1H), 8.06 (dt, J = 2.0, 8.0 Hz, 1H), 7.68-7.60 (m, 1H), 7.55 (s, 1H), 7.00 (d, J = 8.4 Hz, 1H), 6.80 (s, 1H), 6.69 (dd, J = 2.0, 8.4 Hz, 1H), 6.03 (s, 1H), 5.40-5.24 (m, 1H), 4.49-4.35 (m, 1H), 3.63-3.56 (m, 2H), 3.28 (s, 3H), 2.93-2.73 (m, 2H), 2.64-2.57 (m, 2H), 2.44-2.36 (m, 2H), 2.28 (d, J = 6.8 Hz, 2H), 2.23 (s, 3H), 2.18-2.10 (m, 2H), 2.00-1.87 (m, 5H), 1.81-1.72 (m, 2H), 1.61 (s, 9H), 1.15-1.03 (m, 2H) |
| I-87 | ATC | AWK | 815.2 | 12.37 (s, 1H), 11.22-10.93 (m, 1H), 8.74 (s, 1H), 8.51-8.41 (m, 1H), 8.36 (s, 1H), 8.16 (d, J = 7.6 Hz, 1H), 8.03 (s, 1H), 7.65-7.50 (m, 2H), 7.09-6.93 (m, 2H), 6.46 (t, J = 6.0 Hz, 1H), 6.02 (s, 1H), 5.04 (dd, J = 5.2, 12.8 Hz, 1H), 4.50 (t, J = 6.4 Hz, 2H), 3.22-3.17 (m, 4H), 2.94-2.81 (m, 2H), 2.61-2.56 (m, 2H), 2.30-2.17 (m, 4H), 2.05-1.97 (m, 1H), 1.87 (t, J = 10.0 Hz, 2H), 1.71-1.62 (m, 8H), 1.47 (s, 2H), 1.41-1.31 (m, 4H) |
| I-88 | AWM | AWF | 847.3 | 11.10 (s, 1H), 10.79 (s, 1H), 8.67 (s, 1H), 8.31 (s, 1H), 8.18-8.12 (m, 2H), 7.85 (d, J = 7.6 Hz, 1H), 7.57 (t, J = 8.4 Hz, 1H), 7.14 (t, J = 4.8 Hz, 2H), 7.02 (d, J = 7.2 |

TABLE 7-continued

| Compounds synthesized via Method 2 with the reductive amination of various intermediate amines and aldehydes. | | | | |
|---|---|---|---|---|
| I-# | Intermediate Amine | Intermediate Aldehyde | LCMS (ES+) m/z (M + H)+ | $^1$HNMR (400 MHz, DMSO-$d_6$) δ |
| | | | | Hz, 1H), 6.31 (d, J = 8.4 Hz, 1H), 5.05 (dd, J = 5.2, 12.8 Hz, 1H), 4.35 (t, J = 11.6 Hz, 1H), 3.99 (s, 3H), 3.60-3.51 (m, 2H), 2.94-2.83 (m, 1H), 2.63-2.52 (m, 3H), 2.39 (s, 4H), 2.26-2.10 (m, 4H), 2.07-1.98 (m, 1H), 1.96-1.85 (m, 4H), 1.82 (s, 3H), 1.76 (s, 3H), 1.68-1.52 (m, 5H), 1.50-1.36 (m, 4H), 1.26 (t, J = 12.0 Hz, 2H), 1.17-1.02 (m, 2H) |
| I-89 | ATC | AWO | 891.6 | 11.08 (s, 1H), 10.43 (s, 1H), 8.71 (s, 1H), 8.50-8.33 (m, 3H), 8.22 (m, 1H), 8.18 (s, 1H), 7.60 (s, 1H), 7.58-7.55 (m, 1H), 7.50 (s, 1H), 7.37 (s, 1H), 7.19 (s, 1H), 7.06 (d, J = 8.8 Hz, 1H), 7.01 (d, J = 7.0 Hz, 1H), 6.47 (t, J = 5.8 Hz, 1H), 5.01-5.01 (m, 1H), 4.47-4.37 (m, 1H), 3.24-3.16 (m, 2H), 2.94-2.81 (m, 1H), 2.68-2.58 (m, 1H), 2.54 (m, 1H), 2.34-2.17 (m, 5H), 2.16-2.07 (m, 4H), 2.06-1.98 (m, 1H), 1.94-1.83 (m, 6H), 1.72-1.64 (m, 2H), 1.63-1.58 (m, 1H), 1.55 (m, 2H), 1.46 (m, 2H), 1.42-1.34 (m, 2H), 1.15-0.99 (m, 2H) |
| I-90 | AVZ | AWF | 821.7 | 11.10 (s, 1H), 10.79 (s, 1H), 8.66 (s, 1H), 8.31 (s, 1H), 8.21-8.08 (m, 3H), 7.85 (d, J = 7.6 Hz, 1H), 7.62-7.51 (m, 1H), 7.16-7.09 (m, 2H), 7.02 (d, J = 7.2 Hz, 1H), 6.59 (m, 1H), 5.05 (m, 1H), 4.40-4.30 (m, 1H), 3.99 (s, 3H), 3.18 (m, 2H), 2.91-2.82 (m, 1H), 2.69-2.65 (m, 1H), 2.63-2.56 (m, 2H), 2.42-2.37 (m, 1H), 2.34-2.27 (m, 4H), 2.17-2.10 (m, 2H), 2.07-2.00 (m, 1H), 1.97-1.89 (m, 3H), 1.88-1.78 (m, 8H), 1.76 (s, 3H), 1.59-1.52 (m, 2H), 1.31-1.23 (m, 2H), 1.16-0.97 (m, 4H) |
| I-91 | ALC | ATF | 870.7 | 11.24 (s, 1H), 10.81 (s, 1H), 8.81 (s, 1H), 8.48-8.40 (m, 3H), 8.33 (s, 1H), 8.16 (dd, J = 1.8, 6.4 Hz, 1H), 7.71 (t, J = 7.8 Hz, 1H), 7.32-7.24 (m, 2H), 7.16 (d, J = 6.8 Hz, 1H), 6.76 (t, J = 4.8 Hz, 1H), 5.19 (dd, J = 5.4, 12.8 Hz, 1H), 4.55-4.42 (m, 1H), 3.97 (d, J = 10.6 Hz, 1H), 3.83-3.74 (m, 2H), 3.70-3.65 (m, 2H), 3.07-2.94 (m, 3H), 2.85-2.78 (m, 2H), 2.76-2.70 (m, 2H), 2.51-2.42 (m, 5H), 2.34-2.26 (m, 9H), 2.16 (d, J = 11.2 Hz, 2H), 2.10-2.02 (m, 3H), 2.01-1.94 (m, 2H), 1.79-1.66 (m, 3H), 1.30-1.15 (m, 2H) |
| I-92 | ATC | AWF | 847.4 | 11.11-11.06 (m, 1H), 10.79 (s, 1H), 8.66 (s, 1H), 8.31-8.28 (m, 1H), 8.19-8.10 (m, 2H), 7.85 (d, J = 7.6 Hz, 1H), 7.58 (m, 1H), 7.14 (s, 1H), 7.07 (d, J = 8.4 Hz, 1H), 7.02 (d, J = 6.8 Hz, 1H), 6.47 (t, J = 5.6 Hz, 1H), 5.05 (dd, J = 5.2, 12.8 Hz, 1H), 4.38-4.30 (m, 1H), 4.00-3.97 (m, 3H), 3.22 (m, 2H), 2.92-2.84 (m, 1H), 2.63-2.59 (m, 1H), 2.64-2.59 (m, 1H), 2.55 (m, 3H), 2.29-2.20 (m, 3H), 2.16-2.09 (m, 4H), 2.02 (m, 1H), 1.95-1.85 (m, 6H), 1.82 (s, 3H), 1.76 (s, 3H), 1.72-1.66 (m, 2H), 1.57 (m, 2H), 1.48 (m, 2H), 1.39 (m, 2H), 1.13-1.02 (m, 2H) |
| I-93 | ATH | ATF | 823.4 | 11.11 (s, 1H), 10.68 (s, 1H), 9.62-9.45 (m, 1H), 8.70-8.66 (m, 1H), 8.38-8.29 (m, 3H), 8.03 (dd, J = 2.8, 6.0 Hz, 1H), 7.63-7.57 (m, 1H), 7.07 (dd, J = 7.6, 16.8 Hz, 3H), 6.48 (t, J = 5.2 Hz, 1H), 5.06 (dd, J = 5.6, 12.4 Hz, 1H), 4.54-4.22 (m, 2H), 4.17-4.04 (m, 2H), 4.00 (s, 4H), 3.28-3.15 (m, 3H), 2.95-2.83 (m, 1H), 2.65-2.55 (m, 2H), 2.30-2.1 (m, 7H), 2.0.8-1.80 (m, 8H), 1.72-1.50 (m, 4H), 1.28-1.14 (m, 2H) |
| I-94 | APY | ALU | 821.4 | 11.09 (s, 1H), 10.50-10.47 (m, 1H), 8.58-8.53 (m, 1H), 8.49-8.44 (m, 2H), 8.43-8.38 (m, 1H), 8.24-8.21 (m, 1H), 7.99 (s, 1H), 7.29 (s, 1H), 6.96 (d, J = 4.8 Hz, 2H), 6.89-6.84 (m, 1H), 5.40-5.32 (m, 1H), 4.58-4.46 (m, 1H), 3.56 (s, 3H), 2.93-2.83 (m, 6H), 2.15 (d, J = 6.8 Hz, 4H), 1.99-1.84 (m, 8H), 1.78-1.72 (m, 2H), 1.55-1.49 (m, 2H), 1.38-1.09 (m, 6H) |
| I-95 | AZF | ALU | 831.4 | 11.11 (s, 1H), 10.49 (s, 1H), 8.55 (s, 1H), 8.50-8.38 (m, 3H), 8.24-8.21 (m, 1H), 8.01-7.96 (m, 1H), 7.39-7.22 (m, 1H), 7.13-7.05 (m, 2H), 7.02-6.96 (m, 1H), 5.43-5.32 (m, 1H), 4.58-4.46 (m, 1H), 3.64 (s, 3H), 2.97-2.58 (m, 6H), 2.21-2.09 (m, 4H), 2.06-1.84 (m, 8H), 1.80-1.73 (m, 2H), 1.69-1.50 (m, 2H), 1.40-1.28 (m, 2H), 1.18-1.04 (m, 2H) |
| I-96 | AWQ | ATJ | 802.5 | 11.09 (s, 1H), 10.50 (s, 1H), 8.68 (s, 1H), 8.49-8.43 (m, 1H), 8.43-8.37 (m, 1H), 8.32 (s, 1H), 8.22 (d, J = 6.8 Hz, 1H), 7.16 (s, 1H), 7.00-6.93 (m, 2H), 6.93-6.86 (m, 1H), 5.41-5.32 (m, 1H), 4.41-4.31 (m, 1H), |

TABLE 7-continued

Compounds synthesized via Method 2 with the reductive amination of various intermediate amines and aldehydes.

| I-# | Intermediate Amine | Intermediate Aldehyde | LCMS (ES+) m/z $(M + H)^+$ | $^1$HNMR (400 MHz, DMSO-$d_6$) δ |
|---|---|---|---|---|
| | | | | 3.98 (s, 3H), 3.58 (s, 3H), 3.09-3.02 (m, 2H), 2.87 (m, 1H), 2.73-2.62 (m, 3H), 2.61-2.53 (m, 6H), 2.44-2.34 (m, 3H), 2.19-2.09 (m, 4H), 2.03-1.83 (m, 5H), 1.69-1.53 (m, 1H), 1.17-1.02 (m, 2H) |
| I-97 | AWR | AGL | 856.4 | 12.36 (s, 1H), 11.09 (s, 1H), 8.71 (s, 1H), 8.48-8.41 (m, 1H), 8.40-8.31 (m, 2H), 8.16 (dd, J = 0.8, 7.6 Hz, 1H), 7.57 (s, 1H), 7.02-6.87 (m, 3H), 6.00-5.86 (m, 1H), 5.36 (dd, J = 5.6, 12.8 Hz, 1H), 4.47-4.36 (m, 1H), 3.57 (s, 3H), 3.13-3.08 (m, 2H), 3.05-2.98 (m, 2H), 2.92-2.84 (m, 1H), 2.69-2.64 (m, 3H), 2.60-2.54 (m, 2H), 2.32-2.28 (m, 2H), 2.22-2.11 (m, 4H), 2.10-1.82 (m, 6H), 1.82-1.72 (m, 2H), 1.73-1.65 (m, 2H), 1.62 (s, 6H), 1.54-1.44 (m, 1H), 1.21-1.05 (m, 2H) |
| I-98 | AZI | AWF | 737.4 | 11.11 (s, 1H), 10.80 (s, 1H), 8.70-8.66 (m, 1H), 8.32 (s, 1H), 8.20-8.16 (m, 1H), 8.15-8.11 (m, 1H), 7.88-7.83 (m, 1H), 7.24 (s, 1H), 7.17-7.13 (m, 1H), 7.12-7.02 (m, 2H), 5.37 (dd, J = 5.6, 12.8 Hz, 1H), 4.44-4.30 (m, 1H), 4.00 (s, 3H), 3.97-3.94 (m, 1H), 3.87-3.80 (m, 1H), 3.58-3.51 (m, 3H), 3.37 (s, 3H), 2.96-2.86 (m, 1H), 2.78-2.58 (m, 4H), 2.16 (d, J = 11.2 Hz, 2H), 2.06-1.86 (m, 5H), 1.83 (s, 3H), 1.77 (s, 3H), 1.61-1.49 (m, 1H), 1.28-1.11 (m, 2H) |
| I-99 | AZI | AZJ | 757.4 | 11.10 (s, 1H), 10.69 (s, 1H), 8.66 (s, 1H), 8.56 (s, 1H), 8.19-8.13 (m, 2H), 8.00 (s, 1H), 7.86-7.83 (m, 1H), 7.44-7.16 (m, 2H), 7.10-7.02 (m, 2H), 5.37 (dd, J = 5.2, 12.8 Hz, 1H), 4.57-4.47 (m, 1H), 3.86-3.81 (m, 2H), 3.77-3.73 (m, 2H), 3.37 (s, 3H), 2.96-2.87 (m, 1H), 2.81-2.58 (m, 3H), 2.56 (d, J = 6.4 Hz, 2H), 2.18 (d, J = 10.0 Hz, 2H), 2.04-1.89 (m, 5H), 1.80 (s, 3H), 1.74 (s, 3H), 1.51 ( d, J = 7.2 Hz, 1H), 1.21 (q, J = 11.6 Hz, 2H) |
| I-100 | AZL | AWF | 765.4 | 11.07 (s, 1H), 10.80 (s, 1H), 8.68 (s, 1H), 8.42-8.28 (m, 1H), 8.20-8.14 (m, 2H), 7.93-7.80 (m, 1H), 7.14 (d, J = 15.6 Hz, 2H), 7.05-6.90 (m, 2H), 5.35 (dd, J = 5.2, 12.8 Hz, 1H), 4.49-4.30 (m, 1H), 4.00 (s, 3H), 3.35 (s, 3H), 3.05 (d, J = 8.4 Hz, 2H), 2.91 (s, 1H), 2.78-2.69 (m, 1H), 2.65-2.61 (m, 2H), 2.32-2.25 (m, 2H), 2.20-2.09 (m, 4H), 2.03-1.95 (m, 3H), 1.94-1.86 (m, 2H), 1.83 (s, 3H), 1.78 (s, 8H), 1.20-1.09 (m, 2H) |
| I-101 | AZL | AZJ | 785.3 | 11.09 (s, 1H), 10.69 (s, 1H), 8.74-8.45 (m, 2H), 8.21-8.12 (m, 2H), 8.01 (s, 1H), 7.85 (dd, J = 1.6, 7.6 Hz, 1H), 7.50-7.15 (m, 1H), 7.14-6.87 (m, 3H), 5.35 (dd, J = 5.2, 12.8 Hz, 1H), 4.63-4.44 (m, 1H), 3.35 (s, 3H), 3.09-2.98 (m, 2H), 2.97-2.86 (m, 1H), 2.77-2.69 (m, 1H), 2.66-2.54 (m, 3H), 2.31-2.16 (m, 4H), 2.12-2.07 (m, 1H), 2.07-1.88 (m, 6H), 1.80-1.77 (m, 6H), 1.76-1.58 (m, 4H), 1.29-1.05 (m, 2H) |
| I-102 | AWS | ATJ | 774.4 | 11.06 (s, 1H), 10.50 (s, 1H), 8.69 (s, 1H), 8.49-8.36 (m, 2H), 8.34 (s, 1H), 8.23-8.20 (m, 1H), 7.16 (s, 1H), 6.94 (d, J = 8.4 Hz, 1H), 6.85 (d, J = 2.0 Hz, 1H), 6.63 (dd, J = 2.0, 8.4 Hz, 1H), 5.29 (dd, J = 5.2, 12.8 Hz, 1H), 4.43-4.34 (m, 1H), 3.98 (s, 3H), 3.31 (s, 3H), 3.14-3.06 (m, 4H), 2.95-2.83 (m, 1H), 2.70-2.55 (m, 5H), 2.23-2.21 (m, 2H), 2.18-2.12 (m, 2H), 2.05-1.75 (m, 6H), 1.72-1.57 (m, 1H), 1.23-1.03 (m, 2H) |
| I-103 | AZK | AZJ | 785.5 | 11.12-11.06 (m, 1H), 10.68 (s, 1H), 8.66 (s, 1H), 8.56 (s, 1H), 8.21-8.17 (m, 1H), 8.15-8.12 (m, 1H), 8.00 (s, 1H), 7.86-7.81 (m, 1H), 7.44-7.15 (m, 1H), 7.05-6.95 (m, 3H), 5.42-5.32 (m, 1H), 4.59-4.46 (m, 1H), 3.59 (s, 3H), 3.03-2.83 (m, 4H), 2.72-2.58 (m, 3H), 2.26-1.89 (m, 12H), 1.81-1.72 (m, 9H), 1.22-1.09 (m, 2H) |
| I-104 | AZM | ALU | 765.2 | 11.10 (s, 1H), 10.49 (s, 1H), 8.57 (s, 1H), 8.52-8.35 (m, 3H), 8.22 (dd, J = 1.2, 7.6 Hz, 1H), 7.99 (s, 1H), 7.39-7.13 (m, 2H), 7.13-7.06 (m, 2H), 5.39 (dd, J = 5.6, 12.4 Hz, 1H), 4.66-4.45 (m, 2H), 4.09 (d, J = 1.2 Hz, 2H), 3.93-3.67 (m, 2H), 3.54 (s, 3H), 2.96-2.74 (m, 3H), 2.74-2.61 (m, 2H), 2.19 ( d, J = 8.8 Hz, 2H), 2.05-1.89 (m, 5H), 1.68-1.60 (m, 1H), 1.36-1.09 (m, 2H) |
| I-105 | APZ | AWT | 841.6 | 11.23 (s, 1H), 11.10 (s, 1H), 9.31 (d, J = 7.2 Hz, 1H), 8.87-8.73 (m, 1H), 8.65 (d, J = 1.2 Hz, 1H), 8.32 (d, J = 9.6 Hz, 2H), 7.55 (s, 1H), 7.30-7.26 (m, 1H), 7.04-6.78 (m, 3H), 5.69 (s, 1H), 5.42-5.29 (m, 1H), 4.46- |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 4.35 (m, 1H), 3.55 (s, 3H), 2.91-2.84 (m, 2H), 2.82-2.78 (m, 2H), 2.73-2.62 (m, 5H), 2.20-2.08 (m, 5H), 2.02-1.85 (m, 9H), 1.75-1.66 (m, 3H), 1.60 (s, 6H), 1.53-1.47 (s, 2H), 1.39 (t, J = 9.2 Hz, 2H), 1.17-1.03 (m, 2H) |
| I-106 | ASK | ALU | 822.5 | 11.06 (s, 1H), 10.49 (s, 1H), 8.56 (s, 1H), 8.51-8.36 (m, 3H), 8.22 (d, J = 8.4 Hz, 1H), 7.99 (s, 1H), 7.40-7.08 (m, 1H), 6.93 (d, J = 8.4 Hz, 1H), 6.83 (d, J = 2.4 Hz, 1H), 6.64 (dd, J = 2.4, 8.4 Hz, 1H), 5.29 (dd, J = 5.2, 12.8 Hz, 1H), 4.57-4.46 (m, 1H), 3.65 (d, J = 11.6 Hz, 2H), 3.31 (s, 3H), 2.97-2.82 (m, 2H), 2.66-2.61 (m, 3H), 2.32-2.28 (m, 1H), 2.25 (s, 3H), 2.23-2.11 (m, 3H), 2.06-1.86 (m, 6H), 1.84-1.72 (m, 2H), 1.66-1.54 (m, 3H), 1.18-1.05 (m, 2H) |
| I-107 | ASK | ATJ | 802.5 | 11.06 (s, 1H), 10.50 (s, 1H), 8.69 (s, 1H), 8.51-8.37 (m, 2H), 8.25-8.14 (m, 2H), 7.16 (s, 1H), 6.93 (d, J = 8.4 Hz, 1H), 6.83 (s, 1H), 6.64 (d, J = 8.4 Hz, 1H), 5.34-5.21 (m, 1H), 4.42-4.32 (m, 1H), 3.98 (s, 3H), 3.65 (d, J = 12.4 Hz, 2H), 3.31 (s, 3H), 2.94-2.84 (m, 2H), 2.68-2.63 (m, 3H), 2.29 (d, J = 6.8 Hz, 2H), 2.25 (s, 3H), 2.17-2.12 (m, 2H), 2.01-1.85 (m, 6H), 1.79-1.77 (m, 2H), 1.63-1.51 (m, 3H), 1.16-1.04 (m, 2H) |
| I-108 | APZ | BBF | 885.5 | 12.03 (s, 1H), 11.08 (s, 1H), 8.67 (s, 1H), 8.33 (s, 1H), 8.29-8.23 (m, 1H), 8.20-8.18 (m, 1H), 7.57-7.50 (m, 2H), 6.99-6.90 (m, 2H), 6.86-6.80 (m, 1H), 5.99-5.71 (m, 1H), 5.39-5.30 (m, 1H), 4.44-4.35 (m, 1H), 3.54 (s, 3H), 2.93-2.84 (m, 1H), 2.82-2.75 (m, 2H), 2.74-2.51 (m, 4H), 2.38-2.22 (m, 4H), 2.19-2.08 (m, 4H), 2.01-1.95 (m, 1H), 1.94-1.82 (m, 6H), 1.74-1.64 (m, 2H), 1.59 (s, 6H), 1.57 (s, 2H), 1.49 (t, J = 5.2 Hz, 2H), 1.44-1.33 (m, 2H), 1.17-1.00 (m, 2H) |
| I-109 | AMS | ATJ | 827.5 | 11.10 (s, 1H), 10.51 (s, 1H), 8.69 (s, 1H), 8.49-8.38 (m, 2H), 8.33 (s, 1H), 8.25-8.20 (m, 1H), 7.16 (s, 1H), 7.00-6.92 (m, 2H), 6.87-6.81 (m, 1H), 5.44-5.30 (m, 1H), 4.44-4.27 (m, 1H), 3.99 (s, 3H), 3.55 (s, 3H), 3.06-3.01 (m, 2H), 2.95-2.87 (m, 1H), 2.77-2.68 (m, 1H), 2.67-2.53 (m, 3H), 2.33-2.20 (m, 3H), 2.18-2.09 (m, 4H), 2.06-1.98 (m, 1H), 1.96-1.83 (m, 6H), 1.68-1.55 (m, 3H), 1.55-1.44 (m, 4H), 1.15-1.00 (m, 2H) |
| I-110 | AZK | ATJ | 773.4 | 11.09 (s, 1H), 10.51 (s, 1H), 8.74 (s, 1H), 8.54 (s, 1H), 8.49-8.36 (m, 2H), 8.21 (dd, J = 7.6, 1.2 Hz, 1H), 8.15 (s, 1H), 7.18 (s, 1H), 7.14-6.96 (m, 3H), 5.40 (m, 1H), 4.53 (m, 2H), 4.01 (s, 3H), 3.74-3.47 (m, 6H), 3.29-3.10 (m, 2H), 3.06-2.84 (m, 3H), 2.78-2.67 (m, 1H), 2.65-2.58 (m, 1H), 2.43-2.37 (m, 1H), 2.25-2.08 (m, 4H), 2.08-1.87 (m, 6H), 1.38-1.20 (m, 2H) |
| I-111 | AZM | ATJ | 745.3 | 11.11 (s, 1H), 10.51 (s, 1H), 8.70 (s, 1H), 8.48-8.39 (m, 2H), 8.35 (s, 1H), 8.23 (dd, J = 1.2, 7.6 Hz, 1H), 7.29 (d, J = 7.6 Hz, 1H), 7.18-7.05 (m, 3H), 5.39 (dd, J = 5.2, 12.4 Hz, 1H), 4.56-4.34 (m, 2H), 3.99 (s, 3H), 3.55 (s, 3H), 2.95-2.77 (m, 2H), 2.74-2.60 (m, 3H), 2.53 (s, 4H), 2.21-2.12 (m, 2H), 2.03-1.85 (m, 5H), 1.68-1.56 (m, 1H), 1.31-1.11 (m, 2H) |
| I-112 | AZM | AWF | 737.4 | 11.11 (s, 1H), 10.80 (s, 1H), 8.72-8.65 (m, 1H), 8.33 (s, 1H), 8.20-8.11 (m, 2H), 7.90-7.82 (m, 1H), 7.30 (d, J = 7.2 Hz, 1H), 7.17-7.04 (m, 3H), 5.40 (dd, J = 5.2, 12.4 Hz, 1H), 4.57-4.33 (m, 2H), 4.20-3.95 (m, 5H), 3.55 (s, 3H), 2.97-2.82 (m, 2H), 2.81-2.59 (m, 3H), 2.53 (s, 2H), 2.17 (d, J = 10.4 Hz, 2H), 2.05-1.86 (m, 5H), 1.83 (s, 3H), 1.77 (s, 3H), 1.68-1.58 (m, 1H), 1.33-1.13 (m, 2H) |
| I-113 | AZM | AZJ | 757.4 | 11.10 (s, 1H), 10.68 (s, 1H), 8.66 (s, 1H), 8.56 (s, 1H), 8.16-8.12 (m, 2H), 7.99 (s, 1H), 7.86-7.82 (m, 1H), 7.32-7.12 (m, 2H), 7.12-7.00 (m, 2H), 5.38 (dd, J = 5.2, 12.4 Hz, 1H), 4.57-4.46 (m, 1H), 4.44-3.82 (m, 2H), 3.53 (s, 3H), 2.96-2.53 (m, 3H), 2.52-2.50 (m, 4H), 2.24-2.13 (m, 2H), 2.02-1.88 (m, 6H), 1.79 (s, 3H), 1.73 (s, 3H), 1.62-1.46 (m, 1H), 1.28-1.12 (m, 2H) |
| I-114 | AZK | AWF | 765.4 | 11.10 (s, 1H), 10.80 (s, 1H), 8.68 (s, 1H), 8.33 (s, 1H), 8.17 (d, J = 7.6 Hz, 1H), 8.15-8.09 (m, 1H), 7.86 (d, J = 7.2 Hz, 1H), 7.16 (s, 1H), 7.09-6.91 (m, 3H), 5.45-5.33 (m, 1H), 4.44-4.33 (m, 1H), 4.00 (s, 3H), 3.60 (s, 3H), 3.26-3.21 (m, 2H), 3.00 (m, 2H), 2.94-2.85 (m, |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 1H), 2.72-2.63 (m, 2H), 2.63-2.57 (m, 1H), 2.23 (d, J = 6.8 Hz, 2H), 2.20-2.14(m, 2H), 2.13-2.05 (m, 2H), 2.04-1.98 (m, 2H), 1.97 (s, 1H), 1.92 (d, J = 12.8 Hz, 2H), 1.83 (s, 3H), 1.82-1.79 (m, 2H), 1.78 (s, 3H), 1.70-1.60 (m, 1H), 1.21-1.09 (m, 2H) |
| I-115 | AZN | ALU | 823.3 | 11.09 (s, 1H), 10.49 (s, 1H), 8.56 (s, 1H), 8.52-8.37 (m, 3H), 8.25-8.20 (m, 1H), 7.99 (s, 1H), 7.25 (s, 1H), 6.99-6.94 (m, 1H), 6.77 (dd, J = 4.4, 8.0 Hz, 2H), 5.34 (dd, J = 5.6, 12.8 Hz, 1H), 4.59-4.49 (m, 1H), 3.99 (d, J = 4.8 Hz, 2H), 3.55 (s, 3H), 2.96-2.81 (m, 2H), 2.77-2.56 (m, 5H), 2.23-2.15 (m, 2H), 2.05-1.82 (m, 9H), 1.73-1.54 (m, 2H), 1.25 (s, 2H), 1.20-1.13 (m, 2H) |
| I-116 | WX | AWX | 843.5 | 11.11 (s, 1H), 10.67 (s, 1H), 9.39 (dd, J = 1.6, 7.2 Hz, 1H), 8.98 (dd, J = 1.6, 4.4 Hz, 1H), 8.74 (d, J = 10.4 Hz, 2H), 8.32 (s, 1H), 7.53-7.26 (m, 2H), 7.19-6.71 (m, 3H), 5.49-5.26 (m, 1H), 4.48-4.27 (m, 1H), 3.97-3.80 (m, 4H), 3.71-3.61 (m, 5H), 2.98-2.83 (m, 7H), 2.79-2.69 (m, 1H), 2.67-2.59 (m, 1H), 2.35 (d, J = 1.2 Hz, 1H), 2.25 (d, J = 6.4 Hz, 2H), 2.20 (s, 3H), 2.12 (d, J = 9.6 Hz, 2H), 2.06-1.81 (m, 7H), 1.74-1.58 (m, 2H), 1.54-1.34 (m, 3H), 1.17-0.95 (m, 2H) |
| I-117 | ARW | ATJ | 855.1 | 11.09 (s, 1H), 10.50 (s, 1H), 8.69 (s, 1H), 8.50-8.44 (m, 1H), 8.44-8.37 (m, 1H), 8.33 (s, 1H), 8.22 (d, J = 8.00 Hz, 1H), 7.14 (s, 1H), 7.02-6.90 (m, 2H), 6.88-6.76 (m, 1H), 5.45-5.28 (m, 1H), 4.44-4.29 (m, 1H), 3.98 (s, 3H), 3.55 (s, 3H), 3.14-2.95 (m, 2H), 2.93-2.83 (m, 16.4 Hz, 1H), 2.76-2.70 (m, 1H), 2.65-2.58 (m, 2H), 2.57-2.54 (m, 1H), 2.53-2.51 (m, 3H), 2.47-2.39 (m, 2H), 2.14 (d, J = 11.6 Hz, 2H), 2.04-1.85 (m, 7H), 1.83-1.77 (m, 1H), 1.75-1.60 (m, 4H), 1.57-1.50 (m, 1H), 1.48-1.41 (m, 1H), 1.41-1.21 (m, 4H), 1.20-1.08 (m, 2H) |
| I-118 | AJF | AZU | 891.3 | 11.10 (s, 1H), 10.33 (s, 1H), 8.78 (s, 1H), 8.32-8.29 (m, 1H), 8.18-8.12 (m, 2H), 7.81 (d, J = 6.8 Hz, 1H), 7.64-7.52 (m, 1H), 7.18-6.96 (m, 3H), 6.49 (s, 1H), 5.05 (dd, J = 5.6, 12.8 Hz, 1H), 4.74 (s, 1H), 4.37 (s, 1H), 3.91 (s, 2H), 3.39-3.35 (m, 2H), 2.93-2.84 (m, 2H), 2.61 (m, 1H), 2.56 (m, 2H), 2.53 (m, 2H), 2.49-2.44 (m, 2H), 2.14 (d, J = 10.0 Hz, 2H), 2.09-1.84 (m, 8H), 1.83-1.71 (m, 9H), 1.70-1.62 (m, 2H), 1.58-1.53 (m, 2H), 1.32 (s, 6H), 1.21-1.15 (m, 2H) |
| I-119 | ATC | AZV | 909.5 | 11.09 (s, 1H), 10.39 (s, 1H), 8.77 (s, 1H), 8.36-8.23 (m, 3H), 7.97 (dd, J = 1.2, 7.6 Hz, 1H), 7.58 (dd, J = 7.2, 8.4 Hz, 1H), 7.11-6.99 (m, 3H), 6.47 (t, J = 6.0 Hz, 1H), 5.05 (dd, J = 5.2, 12.8 Hz, 1H), 4.89-4.57 (m, 1H), 4.40-4.27 (m, 1H), 3.90 (s, 2H), 3.25-3.17 (m, 2H), 2.94-2.83 (m, 1H), 2.63-2.52 (m, 2H), 2.31-2.18 (m, 4H), 2.17-1.97 (m, 9H), 1.95-1.81 (m, 6H), 1.73-1.65 (m, 2H), 1.64-1.53 (m, 3H), 1.47 (t, J = 5.2 Hz, 2H), 1.42-1.35 (m, 2H), 1.33 (s, 6H), 1.14-1.01 (m, 2H) |
| I-120 | ATC | BAF | 802.2 | 11.09 (s, 1H), 10.59 (s, 1H), 9.04 (d, J = 5.0 Hz, 1H), 8.67 (s, 1H), 8.32 (s, 1H), 8.25 (s, 1H), 7.96 (d, J = 5.0 Hz, 1H), 7.58 (dd, J = 7.2, 8.4 Hz, 1H), 7.15 (s, 1H), 7.07 (d, J = 8.6 Hz, 1H), 7.02 (d, J = 7.0 Hz, 1H), 6.50-6.45 (m, 1H), 5.05 (dd, J = 5.6, 12.9 Hz, 1H), 4.40-4.29 (m, 1H), 4.00 (s, 3H), 3.25-3.15 (m, 3H), 2.94-2.82 (m, 1H), 2.78 (s, 3H), 2.63-2.52 (m, 2H), 2.16-1.98 (m, 12H), 1.95-1.80 (m, 6H), 1.74-1.34 (m, 6H), 1.47-1.45 (m, 2H), 1.41-1.36 (m, 2H), 1.14-1.00 (m, 2H) |
| I-121 | ATC | AWZ | 819.3 | 11.09 (s, 1H), 10.51 (s, 1H), 8.66 (s, 1H), 8.29 (s, 1H), 8.08 (dd, J = 3.6, 8.0 Hz, 1H), 7.89 (t, J = 9.2 Hz, 1H), 7.63-7.54 (m, 1H), 7.12 (s, 1H), 7.07 (d, J = 8.8 Hz, 1H), 7.02 (d, J = 7.2 Hz, 1H), 6.47 (t, J = 5.2 Hz, 1H), 5.05 (dd, J = 5.2, 12.8 Hz, 1H), 4.39-4.29 (m, 1H), 3.99 (s, 3H), 3.22-3.18 (m, 2H), 2.91-2.83 (m, 1H), 2.61 (s, 1H), 2.59 (d, J = 3.2 Hz, 3H), 2.55-2.53 (m, 1H), 2.32-2.18 (m, 4H), 2.17-1.97 (m, 6H), 1.95-1.80 (m, 6H), 1.73-1.66 (m, 2H), 1.57 (s, 3H), 1.48 (t, J = 5.6 Hz, 2H), 1.44-1.35 (m, 2H), 1.16-0.99 (m, 2H) |
| I-122 | AUK | ATF | 837.2 | 11.14-11.05 (tn, 1H), 10.66 (s, 1H), 8.66 (s, 1H), 8.37-8.26 (m, 3H), 8.22-8.18 (m, 1H), 8.01 (dd, J = 2.4, 6.4 Hz, 1H), 7.56 (dd, J = 7.2, 8.4 Hz, 1H), 7.17-7.13 |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | (m, 1H), 7.10 (d, J = 8.4 Hz, 1H), 7.01 (d, J = 6.8 Hz, 1H), 6.60-6.53 (m, 1H), 5.04 (dd, J = 5.6, 12.8 Hz, 1H), 4.41-4.27 (m, 1H), 3.98 (s, 3H), 3.16-3.10 (m, 4H), 2.93-2.82 (m, 2H), 2.63-2.55 (m, 2H), 2.42-2.37 (m, 2H), 2.15-2.02 (m, 5H), 1.92-1.81 (m, 6H), 1.69-1.59 (m, 3H), 1.54-1.49 (m, 1H), 1.41-1.28 (m, 3H), 1.18-0.94 (m, 5H) |
| I-123 | AML | AZD | 912.4 | 11.85 (s, 1H), 11.11 (s, 1H), 8.67 (s, 1H), 8.37 (s, 2H), 8.20-8.16 (m, 2H), 7.87 (t, J = 8.0 Hz, 1H), 7.62-7.56 (m, 2H), 7.07 (d, J = 7.2 Hz, 1H), 7.01 (d, J = 8.8 Hz, 1H), 6.73-6.53 (m, 1H), 6.46 (d, J = 6.7 Hz, 1H), 5.07 (d, J = 5.2, 12.8 Hz, 1H), 4.49-4.36 (m, 1H), 4.18-4.09 (m, 1H), 2.95-2.84 (m, 1H), 2.64-2.54 (m, 2H), 2.40-2.29 (m, 4H), 2.29-2.20 (m, 2H), 2.13 (d, J = 6.8 Hz, 4H), 2.08-2.00 (m, 1H), 1.99-1.84 (m, 4H), 1.74-1.66 (m, 5H), 1.66 (s, 6H), 1.57 (d, J = 4.8 Hz, 2H), 1.17-1.03 (m, 2H) |
| I-124 | AXB | AGL | 883.4 | 11.10 (s, 1H), 10.50 (s, 1H), 9.94 (s, 1H), 8.69 (s, 1H), 8.52-8.36 (m, 2H), 8.33 (s, 1H), 8.25-8.16 (m, 1H), 7.58 (dd, J = 7.2, 8.4 Hz, 1H), 7.19-7.08 (m, 2H), 7.03 (d, J = 7.2 Hz, 1H), 6.51 (s, 1H), 5.05 (dd, J = 5.2, 12.2 Hz, 1H), 4.42-4.36 (m, 1H), 3.98 (s, 3H), 3.43-3.25 (m, 4H), 3.02-2.74 (m, 5H), 2.64-2.52 (m, 3H), 2.14 (d, J = 10.0 Hz, 2H), 2.09-1.99 (m, 4H), 1.99-1.83 (m, 7H), 1.72 (d, J = 13.2 Hz, 1H), 1.67-1.50 (m, 2H), 1.33-1.16 (m, 2H) |
| I-125 | ATC | AXC | 787.2 | 11.10 (s, 1H), 10.60 (s, 1H), 8.78-8.74 (m, 1H), 8.73 (s, 1H), 8.31 (s, 1H), 8.21 (d, J = 7.6 Hz, 1H), 8.12-8.10 (m, 1H), 7.71-7.69 (m, 1H), 7.61-7.59 (m, 1H), 7.15 (s, 1H), 7.08 (d, J = 8.8 Hz, 1H), 7.03 (d, J = 7.2 Hz, 1H), 6.49 (t, J = 6.0 Hz, 1H), 5.09-5.04 (m, 1H), 4.40-4.31 (m, 1H), 4.00 (s, 3H), 3.23-3.20 (m, 2H), 2.95-2.85 (m, 1H), 2.64-2.55 (m, 2H), 2.32-2.22 (m, 4H), 2.16-2.00 (m, 6H), 1.96-1.86 (m, 6H), 1.73-1.67 (m, 2H), 1.65-1.60 (m, 1H), 1.60-1.55 (m, 2H), 1.49 (m, 2H), 1.42-1.38 (m, 2H), 1.15-1.04 (m, 2H) |
| I-126 | BCY | AGL | 883.4 | 12.36 (s, 1H), 11.10 (s, 1H), 8.71 (s, 1H), 8.47-8.42 (m, 1H), 8.39-8.33 (m, 2H), 8.16 (d, J = 8.4 Hz, 1H), 7.63-7.51 (m, 2H), 7.09-6.95 (m, 2H), 6.43 (d, J = 6.0 Hz, 1H), 5.94 (s, 1H), 5.06 (dd, J = 5.2, 12.8 Hz, 1H), 4.49-4.34 (m, 1H), 4.17-4.00 (m, 1H), 2.98-2.80 (m, 1H), 2.64-2.54 (m, 2H), 2.44-2.38 (m, 1H), 2.30-2.10 (m, 9H), 2.08-1.99 (m, 1H), 1.98-1.82 (m, 5H), 1.75-1.66 (m, 2H), 1.65-1.44 (m, 10H), 1.42-1.27 (m, 3H), 1.26-0.99 (m, 3H) |
| I-132 | AZN | AGL | 831.4 | 12.36 (s, 1H), 11.09 (s, 1H), 8.72 (s, 1H), 8.47-8.43 (m, 1H), 8.39-8.33 (m, 2H), 8.16 (d, J = 7.2 Hz, 1H), 7.57 (s, 1H), 6.99-6.92 (m, 1H), 6.76 (dd, J = 3.2, 8.0 Hz, 2H), 5.94 (s, 1H), 5.34 (dd, J = 5.6, 12.8 Hz, 1H), 4.47-4.38 (m, 1H), 3.95 (d, J = 5.6 Hz, 2H), 3.55 (s, 3H), 3.02 (d, J = 10.4 Hz, 2H), 2.93-2.85 (m, 1H), 2.73-2.59 (m, 2H), 2.35-2.27 (m, 2H), 2.14 (d, J = 10.4 Hz, 4H), 2.03-1.93 (m, 4H), 1.91-1.78 (m, 4H), 1.73-1.66 (m, 1H), 1.62 (s, 6H), 1.49-1.38 (m, 2H), 1.20-1.08 (m, 2H) |
| I-133 | AXD | ATJ | 828.4 | 11.09 (s, 1H), 10.55-10.44 (m, 1H), 8.69 (s, 1H), 8.49-8.36 (m, 2H), 8.33 (s, 1H), 8.21 (d, J = 7.6 Hz, 1H), 7.15 (s, 1H), 7.03-6.86 (m, 3H), 5.41-5.31 (m, 1H), 4.41-4.35 (m, 1H), 3.98 (s, 3H), 3.58 (s, 3H), 3.09-3.03 (m, 4H), 2.84-2.77 (m, 4H), 2.67-2.63 (m, 4H), 2.20-2.11 (m, 3H), 2.05-1.88 (m, 8H), 1.86-1.79 (m, 2H), 1.75-1.66 (m, 1H), 1.29-1.10 (m, 3H) |
| I-134 | AZP | ATJ | 757.3 | 11.14 (s, 1H), 10.51 (s, 1H), 8.70 (s, 1H), 8.48-8.41 (m, 2H), 8.41-8.21 (m, 2H), 7.24-7.16 (m, 3H), 7.06 (d, J = 8.0 Hz, 1H), 5.42 (dd, J = 5.2, 12.8 Hz, 1H), 4.50-4.41 (m, 1H), 3.99 (s, 3H), 3.69 (s, 3H), 3.35-3.32 (m, 5H), 3.01-2.90 (m, 1H), 2.89-2.62 (m, 3H), 2.52-2.40 (m, 1H), 2.16 (d, J = 10.4 Hz, 2H), 2.17-1.92 (m, 5H), 1.82-1.63(m, 1H), 1.29-1.15 (m, 2H) |
| I-135 | AKP | AYL | 870.5 | 11.10 (s, 2H), 8.79 (s, 1H), 8.56-8.47 (m, 1H), 8.46-8.35 (m, 2H), 8.24 (d, J = 7.6 Hz, 1H), 7.52 (s, 1H), 7.03-6.83 (m, 3H), 5.37 (dd, J = 5.6, 12.4 Hz, 1H), 4.47-4.33 (m, 1H), 3.87 (d, J = 4.8 Hz, 4H), 3.56 (s, |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^{1}$HNMR (400 MHz, DMSO-$d_6$) δ |
|---|---|---|---|---|
| | | | | 3H), 3.00-2.83 (m, 9H), 2.78-2.69 (m, 1H), 2.67-2.59 (m, 1H), 2.26 (d, J = 6.0 Hz, 2H), 2.18-2.09 (m, 2H), 2.08-1.78 (m, 7H), 1.75-1.55 (m, 5H), 1.39-1.26 (m, 3H), 1.26-1.05 (m, 4H) |
| I-136 | ATC | BDA | 869.4 | 11.09 (s, 1H), 10.47 (s, 1H), 8.59 (s, 1H), 8.48-8.43 (m, 1H), 8.43-8.37 (m, 1H), 8.22 (d, J = 1.2 Hz, 1H), 7.58 (dd, J = 7.2, 8.4 Hz, 1H), 7.09-7.04 (m, 2H), 7.02 (d, J = 7.2 Hz, 1H), 6.47 (t, J = 6.0 Hz, 1H), 5.05 (dd, J = 5.6, 12.8 Hz, 1H), 4.42-4.30 (m, 1H), 3.96 (s, 3H), 3.22 (d, J = 6.4 Hz, 2H), 2.90-2.86 (m, 1H), 2.61 (m, 1H), 2.57 (s, 3H), 2.55-2.52 (m, 2H), 2.32-2.16 (m, 4H), 2.11 (m, 2H), 2.05-1.86 (m, 9H), 1.69-1.68 (m, 2H), 1.56 (s, 3H), 1.48-1.47 (m, 2H), 1.43-1.34 (m, 2H), 1.17-1.03 (m, 2H) |
| I-137 | ATC | AZS | 856.5 | 11.10 (s, 1H), 10.50 (s, 1H), 8.67 (s, 1H), 8.49-8.44 (m, 1H), 8.44-8.38 (m, 1H), 8.25-8.21 (m, 1H), 7.58 (dd, J = 7.2, 8.4 Hz, 1H), 7.48 (s, 1H), 7.09-6.98 (m, 2H), 6.47 (t, J = 5.6 Hz, 1H), 5.05 (dd, J = 5.2, 12.8 Hz, 1H), 3.98 (s, 3H), 3.23-3.18 (m, 2H), 2.94-2.82 (m, 2H), 2.63-2.52 (m, 2H), 2.38-2.19 (m, 5H), 2.18-2.10 (m, 4H), 2.06-1.99 (m, 1H), 1.95-1.82 (m, 4H), 1.68 (q, J = 6.8 Hz, 2H), 1.63-1.50 (m, 5H), 1.47 (t, J = 5.2 Hz, 2H), 1.43-1.35 (m, 2H), 1.10-0.92 (m, 2H) |
| I-138 | AJF | BFK | 899.2 | 11.23-10.96 (m, 1H), 10.40 (s, 1H), 8.79 (s, 1H), 8.52-8.47 (m, 1H), 8.40 (t, J = 7.6 Hz, 1H), 8.32 (s, 1H), 8.25-8.15 (m, 2H), 7.58 (dd, J = 7.2, 8.4 Hz, 1H), 7.19-6.92 (m, 3H), 6.47 (t, J = 5.6 Hz, 1H), 5.06 (dd, J = 5.6, 12.8 Hz, 1H), 4.42-4.27 (m, 1H), 3.88 (s, 3H), 3.33 (t, J = 6.4 Hz, 2H), 2.95-2.82 (m, 1H), 2.71-2.54 (m, 1H), 2.35-1.99 (m, 10H), 1.96-1.77 (m, 7H), 1.68-1.44 (m, 8H), 1.35 (s, 7H), 1.15-0.98 (m, 3H) |
| I-139 | ATC | BAT | 827.5 | 11.15-10.98 (m, 1H), 10.53 (s, 1H), 9.38 (dd, J = 1.2, 6.8 Hz, 1H), 8.95 (dd, J = 1.2, 4.0 Hz, 1H), 8.69 (d, J = 12.0 Hz, 2H), 8.26 (s, 1H), 7.58 (t, J = 7.6 Hz, 1H), 7.35 (dd, J = 4.4, 6.8 Hz, 1H), 7.12-6.97 (m, 3H), 6.47 (t, J = 6.0 Hz, 1H), 5.05 (dd, J = 5.6, 12.8 Hz, 1H), 4.39-4.25 (m, 1H), 4.02 (s, 3H), 3.22 (q, J = 6.8 Hz, 2H), 2.94-2.81 (m, 1H), 2.63-2.56 (m, 1H), 2.28-1.99 (m, 10H), 1.95-1.81 (m, 6H), 1.68 (q, J = 7.2 Hz, 2H), 1.62-1.34 (m, 8H), 1.14-1.00 (m, 2H) |
| I-140 | BAH | AWF | 863.4 | 11.10 (s, 1H), 10.79 (s, 1H), 8.67 (s, 1H), 8.30 (s, 1H), 8.21-8.08 (m, 2H), 7.88-7.82 (m, 1H), 7.64-7.57 (m, 1H), 7.14 (s, 1H), 7.08 (d, J = 6.8 Hz, 1H), 6.91 (d, J = 8.4 Hz, 1H), 6.50 (d, J = 6.0 Hz, 1H), 5.06 (dd, J = 5.2, 12.8 Hz, 1H), 4.41-4.29 (m, 1H), 4.20-4.07 (m, 2H), 3.99 (s, 3H), 3.16 (d, J = 6.0 Hz, 3H), 2.98-2.87 (m, 3H), 2.64-2.52 (m, 2H), 2.41-2.32 (m, 2H), 2.28-2.18 (m, 4H), 2.17-2.10 (m, 2H), 2.08-1.96 (m, 3H), 1.95-1.86 (m, 3H), 1.82 (s, 3H), 1.76 (s, 3H), 1.68 (d, J = 11.2 Hz, 3H), 1.59-1.48 (m, 1H), 1.31-1.19 (m, 2H), 1.17-1.03 (m, 2H) |
| I-141 | ATC | BBA | 909.5 | 11.09 (s, 1H), 10.38 (s, 1H), 8.68 (s, 1H), 8.56 (s, 1H), 8.50-8.37 (m, 2H), 8.23 (dd, J = 1.2, 7.6 Hz, 1H), 7.79 (s, 1H), 7.58 (dd, J = 7.2, 8.4 Hz, 1H), 7.06 (d, J = 8.8 Hz, 1H), 7.02 (d, J = 7.2 Hz, 1H), 6.47 (t, J = 6.0 Hz, 1H), 5.05 (dd, J = 5.2, 12.8 Hz, 1H), 4.54-4.41 (m, 1H), 3.22-3.17 (m, 2H), 2.93-2.81 (m, 1H), 2.63-2.51 (m, 3H), 2.32-2.18 (m, 4H), 2.17-2.07 (m, 4H), 2.06-1.99 (m, 1H), 1.97-1.82 (m, 6H), 1.70-1.65 (m, 2H), 1.64-1.51 (m, 3H), 1.46 (t, J = 5.2 Hz, 2H), 1.40-1.35 (m, 2H), 1.16-0.99 (m, 2H) |
| I-142 | ATC | BDC | 794.5 | 11.09 (s, 1H), 8.96 (s, 1H), 8.47 (s, 1H), 8.23 (s, 1H), 7.58 (dd, J = 7.2, 8.4 Hz, 1H), 7.09-7.04 (m, 2H), 7.02 (d, J = 7.2 Hz, 1H), 6.47 (t, J = 5.6 Hz, 1H), 5.05 (dd, J = 5.2, 13.2 Hz, 1H), 4.38-4.26 (m, 1H), 4.12-4.03 (m, 1H), 3.94 (dd, J = 2.4, 11.2 Hz, 1H), 3.90 (s, 3H), 3.56-3.53 (m, 1H), 3.24-3.18 (m, 2H), 2.93-2.83 (m, 1H), 2.63-2.53 (m, 2H), 2.31-1.99 (m, 11H), 1.94-1.79 (m, 7H), 1.72-1.65 (m, 2H), 1.64-1.50 (m, 6H), 1.46 (t, J = 5.2 Hz, 2H), 1.43-1.34 (m, 3H), 1.13-0.99 (m, 2H) |
| I-143 | ATC | BAK | 794.3 | 11.09 (s, 1H), 8.96 (s, 1H), 8.47 (s, 1H), 8.23 (s, 1H), 7.62-7.54 (m, 1H), 7.08-7.00 (m, 3H), 6.47 (t, J = 5.6 |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | Hz, 1H), 5.05 (dd, J = 5.6, 12.8 Hz, 1H), 4.39-4.27 (m, 1H), 4.07 (d, J = 12.0 Hz, 1H), 3.95 (dd, J = 2.4, 11.2 Hz, 1H), 3.90 (s, 3H), 3.56-3.53 (m, 1H), 3.24-3.20 (m, 2H), 2.93-2.84 (m, 1H), 2.30-2.19 (m, 4H), 2.14-1.98 (m, 7H), 1.97-1.78 (m, 8H), 1.73-1.65 (m, 2H), 1.61-1.35 (m, 12H), 1.13-1.00 (m, 2H) |
| I-144 | AKP | AWZ | 779.5 | 11.09 (s, 1H), 10.51 (s, 1H), 8.66 (s, 1H), 8.29 (s, 1H), 8.11-8.05 (m, 1H), 7.89 (t, J = 8.8 Hz, 1H), 7.13 (s, 1H), 6.96 (d, J = 4.8 Hz, 2H), 6.90-6.84 (m, 1H), 5.36 (dd, J = 5.2, 13.2 Hz, 1H), 4.40-4.29 (m, 1H), 3.99 (s, 3H), 3.54 (s, 3H), 2.90-2.79 (m, 5H), 2.76-2.68 (m, 1H), 2.67-2.61 (m, 1H), 2.59 (d, J = 2.8 Hz, 3H), 2.14-2.07 (m, 4H), 2.02-1.96 (m, 1H), 1.95-1.90 (m, 2H), 1.88-1.79 (m, 4H), 1.67-1.57 (m, 5H), 1.37-1.30 (m, 2H), 1.27-1.20 (m, 1H), 1.17-1.05 (m, 4H) |
| I-145 | BEP | ATJ | 815.2 | 11.09 (s, 1H), 10.50 (s, 1H), 8.68 (s, 1H), 8.49-8.43 (m, 1H), 8.43-8.37 (m, 1H), 8.32 (s, 1H), 8.21 (dd, J = 0.8, 7.6 Hz, 1H), 8.17 (s, 1H), 7.15 (s, 1H), 7.03 (s, 1H), 6.99 (d, J = 8.0 Hz, 1H), 6.86 (dd, J = 1.2, 8.0 Hz, 1H), 5.33 (dd, J = 5.2, 12.8 Hz, 1H), 4.39-4.31 (m, 1H), 3.98 (s, 3H), 3.32 (s, 3H), 2.94-2.87 (m, 1H), 2.88-2.85 (m, 2H), 2.76-2.67 (m, 1H), 2.66-2.61 (m, 1H), 2.60-2.56 (m, 2H), 2.19 (d, J = 6.8 Hz, 2H), 2.15-2.08 (m, 2H), 2.03-1.97 (m, 1H), 1.96-1.87 (m, 5H), 1.87-1.81 (m, 1H), 1.67-1.57 (m, 5H), 1.28-1.20 (m, 3H), 1.18-1.04 (m, 4H) |
| I-146 | BAL | AGL | 830.6 | 12.45-12.32 (m, 1H), 8.71 (s, 1H), 8.50-8.32 (m, 3H), 8.23-8.12 (m, 1H), 7.64-7.55 (m, 1H), 7.06-6.86 (m, 3H), 6.05-5.84 (m, 1H), 5.39-5.33 (m, 1H), 4.46-4.38 (m, 2H), 3.58 (s, 3H), 3.11-3.00 (m, 6H), 2.42-2.40 (m, 2H), 2.20-2.09 (m, 6H), 2.04-1.83 (m, 8H), 1.70-1.55 (m, 8H), 1.21-1.02 (m, 3H) |
| I-147 | BAP | AGL | 733.4 | 12.37 (s, 1H), 11.01 (s, 1H), 8.72 (s, 1H), 8.49-8.33 (m, 3H), 8.17 (d, J = 8.0 Hz, 1H), 7.58 (s, 1H), 6.97-6.84 (m, 1H), 6.58-6.39 (m, 2H), 6.10-5.73 (m, 1H), 5.36-5.22 (m, 1H), 5.12 (d, J = 4.4 Hz, 1H), 4.58-4.36 (m, 1H), 3.66 (s, 3H), 3.05-2.98 (m, 2H), 2.92-2.85 (m, 1H), 2.73-2.65 (m, 2H), 2.25-2.16 (m, 2H), 2.06-1.87 (m, 5H), 1.83-1.75 (m, 1H), 1.63 (s, 6H), 1.34-1.22 (m, 2H) |
| I-148 | BEQ | ALU | 777.2 | 11.10 (s, 1H), 10.49 (s, 1H), 8.56 (s, 1H), 8.51-8.37 (m, 3H), 8.22 (d, J = 6.8 Hz, 1H), 7.98 (s, 1H), 7.39-7.19 (m, 2H), 7.17-7.09 (m, 2H), 5.45-5.33 (m, 1H), 4.59-4.46 (m, 1H), 3.54 (s, 3H), 2.93-2.84 (m, 1H), 2.77-2.59 (m, 3H), 2.30 (s, 5H), 2.16 (s, 2H), 2.07-1.91 (m, 6H), 1.62 (d, J = 7.2 Hz, 1H), 1.21-1.09 (m, 2H) |
| I-149 | AWS | ALU | 794.4 | 11.06 (s, 1H), 10.49 (s, 1H), 8.57 (s, 1H), 8.52-8.44 (m, 2H), 8.43-8.38 (m, 1H), 8.24-8.21 (m, 1H), 7.99 (s, 1H), 7.39-7.09 (m, 1H), 6.94 (d, J = 8.4 Hz, 1H), 6.85 (d, J = 2.0 Hz, 1H), 6.67-6.60 (m, 1H), 5.33-5.25 (m, 1H), 4.58-4.48 (m, 1H), 3.31 (s, 3H), 3.11 (s, 4H), 2.95-2.83 (m, 1H), 2.72-2.54 (m, 6H), 2.25-2.17 (m, 4H), 2.03-1.97 (m, 4H), 1.95 (s, 1H), 1.76-1.67 (m, 1H), 1.22-1.11 (m, 2H) |
| I-150[a] | BAP | ATJ | 705.4 | 11.03 (s, 1H), 10.50 (s, 1H), 8.68 (s, 1H), 8.49-8.44 (m, 1H), 8.43-8.38 (m, 1H), 8.35 (s, 1H), 8.22 (d, J = 7.6 Hz, 1H), 7.16 (s, 1H), 6.92-6.85 (m, 1H), 6.51-6.48 (m, 2H), 5.29 (dd, J = 5.2, 12.4 Hz, 1H), 5.11 (t, J = 5.2 Hz, 1H), 4.47-4.36 (m, 1H), 3.98 (s, 3H), 3.65 (s, 3H), 3.00 (t, J = 5.6 Hz, 2H), 2.95-2.82 (m, 1H), 2.70-2.61 (m, 2H), 2.22-2.14 (m, 2H), 2.10-2.03 (m, 2H), 2.00-1.87 (m, 3H), 1.80-1.69 (m, 1H), 1.35-1.23 (m, 2H) |
| I-151 | BAN | ALU | 875.7 | 11.09 (s, 1H), 10.49 (s, 1H), 8.55 (s, 1H), 8.52-8.36 (m, 3H), 8.22 (d, J = 7.6 Hz, 1H), 7.98 (s, 1H), 7.41-7.07 (m, 1H), 7.02-6.90 (m, 2H), 6.84 (d, J = 6.8 Hz, 1H), 5.36 (dd, J = 5.2, 12.0 Hz, 1H), 4.57-4.42 (m, 1H), 3.54 (s, 3H), 3.06-2.97 (m, 2H), 2.94-2.84 (m, 1H), 2.79-2.62 (m, 2H), 2.33 (s, 2H), 2.26 (s, 3H), 2.16 (d, J = 9.2 Hz, 2H), 2.05-1.73 (m, 9H), 1.70-1.37 (m, 7H), 1.35-1.05 (m, 6H) |
| I-152 | BAN | ATJ | 855.7 | 11.09 (s, 1H), 10.50 (s, 1H), 8.68 (s, 1H), 8.48-8.36 (m, 2H), 8.32 (s, 1H), 8.21 (dd, J = 0.8, 7.6 Hz, 1H), |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | 1HNMR (400 MHz, DMSO-$d_6$) δ |
|---|---|---|---|---|
| | | | | 7.14 (s, 1H), 7.02-6.91 (m, 2H), 6.83 (dd, J = 2.0, 6.8 Hz, 1H), 5.36 (dd, J = 5.2, 12.4 Hz, 1H), 4.52-4.21 (m, 1H), 3.97 (s, 3H), 3.54 (s, 3H), 3.09-2.98 (m, 2H), 2.94-2.84 (m, 1H), 2.76-2.62 (m, 2H), 2.27 (d, J = 6.0 Hz, 2H), 2.21 (s, 3H), 2.12 (d, J = 10.4 Hz, 2H), 2.05-1.72 (m, 9H), 1.68-1.37 (m, 7H), 1.33-1.02 (m, 6H) |
| I-153 | BBD | AGL | 856.1 | 12.36 (s, 1H), 11.06 (s, 1H), 8.71 (s, 1H), 8.49-8.42 (m, 1H), 8.40-8.32 (m, 2H), 8.16 (d, J = 7.6 Hz, 1H), 7.57 (s, 1H), 6.84 (t, J = 8.0 Hz, 1H), 6.52 (m, 1H), 6.29 (d, J = 8.0 Hz, 1H), 5.94 (s, 1H), 5.28 (m, 1H), 5.17 (m, 1H), 4.41 (m, 1H), 3.84-3.76 (m, 1H), 3.62 (s, 3H), 2.92-2.82 (m, 1H), 2.75-2.60 (m, 2H), 2.52 (m, 2H), 2.31-2.21 (m, 4H), 2.12 (m, 4H), 2.01-1.86 (m, 5H), 1.70-1.56 (m, 13H), 1.10 (m, 2H) |
| I-154 | AKP | BAS | 882.4 | 11.09 (s, 1H), 10.69 (s, 1H), 8.68 (s, 1H), 8.53-8.38 (m, 2H), 8.33 (s, 1H), 8.25-8.19 (m, 1H), 7.39 (s, 1H), 7.02-6.78 (m, 3H), 5.37 (dd, J = 5.2, 12.4 Hz, 1H), 4.62 (s, 1H), 4.45-4.30 (m, 1H), 4.10-3.96 (m, 2H), 3.67 (d, J = 6.4 Hz, 1H), 3.55 (s, 3H), 3.43 (d, J = 10.0 Hz, 2H), 3.25 (d, J = 8.8 Hz, 2H), 2.91-2.83 (m, 4H), 2.77-2.69 (m, 1H), 2.66-2.59 (m, 1H), 2.14 (dd, J = 7.6, 17.6 Hz, 4H), 2.05-1.79 (m, 8H), 1.70-1.54 (m, 5H), 1.40-1.23 (m, 3H), 1.22-1.00 (m, 4H) |
| I-155 | BAM | ALU | 875.2 | 11.09 (s, 1H), 10.49 (s, 1H), 8.55 (s, 1H), 8.52-8.47 (m, 1H), 8.47-8.44 (m, 1H), 8.43-8.37 (m, 1H), 8.22 (dd, J = 1.2, 7.6 Hz, 1H), 7.98 (s, 1H), 7.40-7.08 (m, 1H), 7.00-6.91 (m, 2H), 6.87-6.79 (m, 1H), 5.41-5.30 (m, 1H), 4.56-4.43 (m, 1H), 3.55 (s, 3H), 3.08-2.95 (m, 2H), 2.94-2.82 (m, 1H), 2.75-2.59 (m, 2H), 2.54-2.51 (m, 2H), 2.33-2.27 (m, 2H), 2.23 (s, 3H), 2.19-2.10 (m, 2H), 2.03-1.74 (m, 8H), 1.69-1.38 (m, 6H), 1.35-1.04 (m, 6H) |
| I-156 | AWS | AWF | 766.5 | 11.18-10.91 (m, 1H), 10.85-10.68 (m, 1H), 8.67 (s, 1H), 8.32 (s, 1H), 8.21-8.04 (m, 2H), 7.85 (d, J = 7.2 Hz, 1H), 7.14 (s, 1H), 6.94 (d, J = 7.6 Hz, 1H), 6.85 (s, 1H), 6.63 (d, J = 8.4 Hz, 1H), 5.34-5.22 (m, 1H), 4.43-4.31 (m, 1H), 3.99 (s, 3H), 3.31-3.30 (tn, 3H), 3.10 (s, 4H), 2.91-2.85 (m, 1H), 2.66 (m, 2H), 2.58 (m, 4H), 2.22 (d, J = 6.4 Hz, 2H), 2.15 (d, J = 7.6 Hz, 2H), 2.02-1.90 (m, 5H), 1.82 (s, 3H), 1.76 (s, 3H), 1.70-1.60 (m, 1H), 1.21-1.06 (m, 2H) |
| I-157 | AWS | AZJ | 786.5 | 11.17-10.93 (m, 1H), 10.68 (s, 1H), 8.66 (s, 1H), 8.56 (s, 1H), 8.20-8.11 (m, 2H), 8.00 (s, 1H), 7.84 (d, J = 7.2 Hz, 1H), 7.45-7.14 (m, 1H), 6.95 (d, J = 8.8 Hz, 1H), 6.85 (d, J = 1.6 Hz, 1H), 6.64 (dd, J = 2.0, 8.8 Hz, 1H), 5.35-5.23 (m, 1H), 4.58-4.47 (m, 1H), 3.31 (d, J = 2.4 Hz, 3H), 3.14-3.08 (m, 4H), 2.93-2.86 (m, 1H), 2.74-2.66 (m, 2H), 2.54-2.52 (m, 4H), 2.23 (d, J = 7.2 Hz, 2H), 2.21-2.14 (m, 2H), 2.02-1.93 (m, 5H), 1.80 (s, 3H), 1.74 (s, 3H), 1.72-1.64 (m, 1H), 1.22-1.09 (m, 2H) |
| I-158 | AKP | BAT | 787.5 | 11.10 (s, 1H), 10.54 (s, 1H), 9.38 (dd, J = 1.6, 7.2 Hz, 1H), 8.96 (dd, J = 1.6, 4.0 Hz, 1H), 8.70 (d, J = 9.6 Hz, 2H), 8.27 (s, 1H), 7.38-7.32 (m, 1H), 7.10 (s, 1H), 6.96 (d, J = 5.2 Hz, 2H), 6.87 (dd, J = 3.6, 5.2 Hz, 1H), 5.37 (dd, J = 5.2, 12.4 Hz, 1H), 4.38-4.29 (m, 1H), 4.03 (s, 3H), 3.55 (s, 3H), 2.91-2.81 (m, 5H), 2.77-2.68 (m, 1H), 2.66-2.59 (m, 1H), 2.17-2.09 (m, 4H), 2.04-1.97 (m, 1H), 1.94-1.83 (m, 6H), 1.68-1.57 (m, 5H), 1.37-1.24 (m, 3H), 1.20-1.05 (m, 4H) |
| I-159 | ATC | BBH | 881.0 | 11.09 (s, 1H), 10.50 (s, 1H), 8.67(s, 1H), 8.43 (m, 3H), 8.33 (m, 1H), 8.17 (s, 1H), 7.60 (m, 1H), 7.39 (s, 1H), 7.08 (m, 2H), 5.07 (m, 1H), 4.38 (m, 1H), 4.14 (tn, 1H), 2.88 (m, 2H), 2.28-2.09 (m, 11H), 1.91-1.89 (m, 6H), 1.69-1.47 (m, 11H), 1.09 (m, 2H), 0.94 (m, 2H), 0.92 (m, 2H), 0.76 (m, 2H) |
| I-160 | BAM | ATJ | 855.5 | 11.10 (s, 1H), 10.51 (s, 1H), 8.69 (s, 1H), 8.50-8.44 (m, 1H), 8.44-8.38 (m, 1H), 8.33 (s, 1H), 8.22 (d, J = 7.6 Hz, 1H), 7.15 (s, 1H), 7.00-6.93 (m, 2H), 6.87-6.83 (m, 1H), 5.42-5.33 (m, 1H), 4.41-4.31 (m, 1H), 3.99 (s, 3H), 3.56 (s, 3H), 3.10-2.99 (m, 2H), 2.92-2.83 (m, 1H), 2.78-2.64 (m, 2H), 2.56-2.53 (m, 1H), 2.41 (s, 2H), 2.35-2.29 (m, 3H), 2.14 (d, J = 10.8 Hz, |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 2H), 2.07-1.82 (m, 8H), 1.81-1.75 (m, 1H), 1.71-1.57 (m, 4H), 1.56-1.51 (m, 1H), 1.44 (t, J = 9.6 Hz, 1H), 1.38-1.20 (m, 4H), 1.18-1.08 (m, 2H) |
| I-162 | BBD | ATJ | 828.7 | 11.07 (s, 1H), 10.51 (s, 1H), 8.69 (s, 1H), 8.49-8.45 (m, 1H), 8.44-8.38 (m, 1H), 8.33 (s, 1H), 8.28-8.19 (m, 2H), 7.16 (s, 1H), 6.85 (t, J = 8.0 Hz, 1H), 6.53 (d, J = 8.0 Hz, 1H), 6.30 (d, J = 8.0 Hz, 1H), 5.29 (d, J = 12.4 Hz, 1H), 5.18 (d, J = 6.0 Hz, 1H), 4.42-4.30 (m, 1H), 3.99 (s, 3H), 3.84-3.79 (m, 1H), 3.63 (s, 3H), 2.91-2.84 (m, 1H), 2.75-2.62 (m, 2H), 2.31-2.20 (m, 4H), 2.13 (d, J = 6.8 Hz, 4H), 2.05-1.79 (m, 6H), 1.70-1.57 (m, 7H), 1.15-1.03 (m, 2H) |
| I-163 | BAQ | ATJ | 842.1 | 11.13-11.03 (m, 1H), 10.54-10.48 (m, 1H), 8.70 (s, 1H), 8.49-8.38 (m, 2H), 8.34 (s, 1H), 8.23 (d, J = 8.0 Hz, 1H), 7.15 (s, 1H), 6.91-6.81 (m, 1H), 6.51 (d, J = 7.6 Hz, 1H), 6.43 (d, J = 8.0 Hz, 1H), 5.34-5.24 (m, 1H), 4.99-4.90 (m, 1H), 4.45-4.34 (m, 1H), 3.99 (s, 3H), 3.62 (s, 3H), 3.11 (s, 2H), 2.95-2.82 (m, 2H), 2.74-2.59 (m, 6H), 2.20-2.13 (m, 2H), 2.03-1.88 (m, 8H), 1.84-1.54 (m, 8H), 1.24-1.11 (m, 2H) |
| I-166 | BAQ | AGL | 870.6 | 12.37 (s, 1H), 11.05 (m, 1H), 8.72 (s, 1H), 8.48-8.43 (m, 1H), 8.40-8.37 (m, 1H), 8.36 (s, 1H), 8.17 (d, J = 7.6 Hz, 1H), 7.58 (s, 1H), 6.86 (t, J = 8.0 Hz, 1H), 6.51 (d, J = 8.0 Hz, 1H), 6.42 (d, J = 8.0 Hz, 1H), 5.94 (s, 1H), 5.35-5.21 (m, 1H), 4.91 (t, J = 5.6 Hz, 1H), 4.49-4.34 (m, 1H), 3.61 (s, 3H), 3.31 (s, 1H), 3.09 (t, J = 6.4 Hz, 2H), 2.94-2.83 (m, 1H), 2.70-2.65 (m, 1H), 2.65-2.56 (m, 2H), 2.33-2.25 (m, 2H), 2.24-2.16 (m, 2H), 2.10 (d, J = 7.2 Hz, 3H), 2.04-1.84 (m, 8H), 1.63 (s, 6H), 1.60-1.57 (m, 2H), 1.53-1.45 (m, 4H), 1.15-1.04(m, 2H) |
| I-167 | BAI | AWF | 766.4 | 11.10 (s, 1H), 10.80 (s, 1H), 8.68 (s, 1H), 8.32 (s, 1H), 8.19-8.11 (m, 2H), 7.85 (d, J = 7.6 Hz, 1H), 7.14 (s, 1H), 7.04-6.88 (m, 3H), 5.36 (dd, J = 5.2, 12.4 Hz, 1H), 4.45-4.32 (m, 1H), 3.99 (s, 3H), 3.64 (s, 3H), 3.50-3.37 (m, 2H), 3.17-2.83 (m, 7H), 2.77-2.59 (m, 3H), 2.54-2.52 (m, 1H), 2.20-2.24 (m, 2H), 2.02-1.96 (m, 3H), 1.95-1.86 (m, 2H), 1.82 (s, 3H), 1.76 (s, 3H), 1.75-1.55 (m, 1H), 1.28-1.09 (m, 2H) |
| I-168 | AQK | ALU | 822.4 | 11.09 (s, 1H), 10.49 (s, 1H), 8.57 (s, 1H), 8.53-8.43 (m, 2H), 8.43-8.37 (m, 1H), 8.22 (d, J = 7.6 Hz, 1H), 7.99 (s, 1H), 7.43-7.08 (m, 1H), 7.03-6.94 (m, 1H), 6.94-6.83 (m, 2H), 5.40-5.25 (m, 1H), 4.65-4.42 (m, 1H), 3.64 (s, 3H), 3.19-3.12 (m, 2H), 2.97-2.82 (m, 1H), 2.79-2.67 (m, 3H), 2.66-2.56 (m, 1H), 2.48-2.42 (m, 1H), 2.38-2.29 (m, 2H), 2.27 (s, 3H), 2.22-2.13 (m, 2H), 2.06-1.88 (m, 5H), 1.86-1.76 (m, 2H), 1.75-1.53 (m, 3H), 1.22-1.03 (m, 2H) |
| I-169 | BAI | BBA | 828.4 | 11.09 (s, 1H), 10.39 (s, 1H), 8.69 (s, 1H), 8.58 (s, 1H), 8.49-8.38 (m, 2H), 8.28-8.21 (m, 1H), 7.80 (s, 1H), 7.02-6.86 (m, 3H), 5.36 (dd, J = 5.2, 12.8 Hz, 1H), 4.56-4.45 (m, 1H), 3.64 (s, 3H), 3.12-2.81 (m, 8H), 2.75-2.67 (m, 1H), 2.64-2.58 (m, 1H), 2.41-2.3.4 (m, 1H), 2.30-2.23 (m, 1H), 2.18 (d, J = 10.4 Hz, 2H), 2.06-1.86 (m, 6H), 1.75-1.62 (m, 1H), 1.22-1.11 (m, 2H) |
| I-171 | BAI | ATJ | 774.4 | 11.09 (s, 1H), 10.50 (s, 1H), 8.69 (s, 1H), 8.48-8.44 (m, 1H), 8.43-8.37 (m, 1H), 8.33 (s, 1H), 8.21 (dd, J = 0.8, 7.6 Hz, 1H), 7.16 (s, 1H), 7.02-6.84 (m, 3H), 5.35 (dd, J = 5.2, 12.4 Hz, 1H), 4.44-4.32 (m, 1H), 3.98 (s, 3H), 3.63 (s, 3H), 3.06-2.82 (m, 7H), 2.75-2.52 (m, 4H), 2.26 (d, J = 6.8 Hz, 2H), 2.18-2.13 (m, 2H), 2.02-1.84 (m, 5H), 1.73-1.60 (m, 1H), 1.23-1.05 (m, 2H) |
| I-172 | BAI | AGL | 802.4 | 12.36 (s, 1H), 11.09 (s, 1H), 8.72 (s, 1H), 8.48-8.42 (m, 1H), 8.40-8.32 (m, 2H), 8.18-8.13 (m, 1H), 7.57 (s, 1H), 7.03-6.82 (m, 3H), 5.94 (s, 1H), 5.39-5.32 (m, 1H), 4.52-4.37 (m, 1H), 3.64 (s, 3H), 3.08-2.79 (m, 7H), 2.76-2.52 (m, 4H), 2.26 (d, J = 6.4 Hz, 2H), 2.16 (d, J = 10.8 Hz, 2H), 2.04-1.84 (m, 5H), 1.68-1.66 (m, 1H), 1.62 (s, 6H), 1.23-1.08 (m, 2H) |
| I-176 | BAI | ALU | 794.3 | 11.09 (s, 1H), 10.49 (s, 1H), 8.56 (s, 1H), 8.53-8.37 (m, 3H), 8.22 (d, J = 7.6 Hz, 1H), 7.99 (s, 1H), 7.40- |

TABLE 7-continued

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| Compounds synthesized via Method 2 with the reductive amination of various intermediate amines and aldehydes. | | | | |
| | | | | 7.09 (m, 1H), 7.03-6.86 (m, 3H), 5.36 (dd, J = 5.2, 12.4 Hz, 1H), 4.64-4.42 (m, 1H), 3.64 (s, 3H), 3.13-2.78 (m, 10H), 2.68-2.62 (m, 2H), 2.19 (d, J = 10.8 Hz, 2H), 2.07-1.91 (m, 6H), 1.78-1.68 (m, 1H), 1.24-1.14 (m, 2H) |
| I-177 | BAI | AZJ | 786.4 | 11.09 (s, 1H), 10.68 (s, 1H), 8.66 (s, 1H), 8.56 (s, 1H), 8.23-8.11 (m, 2H), 8.00 (s, 1H), 7.84 (d, J = 7.6 Hz, 1H), 7.45-7.14 (m, 1H), 7.07-6.87 (m, 3H), 5.36 (dd, J = 4.4, 12.4 Hz, 1H), 4.58-4.49 (m, 1H), 3.64 (s, 3H), 3.11-2.84 (m, 10H), 2.66 (d, J = 11.2 Hz, 2H), 2.20 (d, J = 11.6 Hz, 2H), 2.07-1.90 (m, 6H), 1.85-1.70 (m, 7H), 1.28-1.11 (m, 2H) |
| I-178 | AQK | AYL | 857.4 | 11.10 (s, 2H), 8.80 (s, 1H), 8.54-8.48 (m, 1H), 8.45-8.37 (m, 2H), 8.24 (d, J = 7.6 Hz, 1H), 7.52 (s, 1H), 7.09-6.79 (m, 3H), 5.36 (dd, J = 5.6, 12.4 Hz, 1H), 4.53-4.32 (m, 1H), 3.88 (d, J = 3.2 Hz, 4H), 3.65 (s, 3H), 3.17 (d, J = 10.4 Hz, 2H), 2.96-2.91 (m, 4H), 2.91-2.84 (m, 1H), 2.77-2.60 (m, 4H), 2.34 (dd, J = 1.6, 3.6 Hz, 2H), 2.29 (s, 3H), 2.15 (d, J = 10.8 Hz, 2H), 2.04-1.88 (m, 5H), 1.82 (d, J = 10.8 Hz, 2H), 1.75-1.55 (m, 3H), 1.25-1.00 (m, 2H) |
| I-179 | AQK | BAS | 869.5 | 11.10 (s, 1H), 10.70 (s, 1H), 8.69 (s, 1H), 8.52-8.47 (m, 1H), 8.42 (t, J = 7.6 Hz, 1H), 8.35 (s, 1H), 8.22 (dd, J = 0.8, 7.6 Hz, 1H), 7.40 (s, 1H), 7.06-6.85 (m, 3H), 5.36 (dd, J = 5.2, 12.4 Hz, 1H), 4.62 (s, 1H), 4.48-4.33 (m, 1H), 4.06 (s, 1H), 4.01 (d, J = 7.6 Hz, 1H), 3.68 (s, 1H), 3.65 (s, 3H), 3.45 (s, 2H), 3.25-3.15 (m, 5H), 2.95-2.85 (m, 1H), 2.78-2.70 (m, 2H), 2.67-2.57 (m, 2H), 2.40 (d, J = 5.2 Hz, 1H), 2.34 (s, 3H), 2.21-2.08 (m, 3H), 2.03-1.91 (m, 4H), 1.88-1.81 (m, 3H), 1.75-1.57 (m, 3H), 1.23-1.05 (m, 2H) |
| I-180 | ATH | AZS | 828.4 | 11.10 (s, 1H), 10.51 (s, 1H), 8.71-8.66 (m, 1H), 8.49-8.39 (m, 2H), 8.24 (d, J = 7.6 Hz, 1H), 7.63-7.55 (m, 1H), 7.51-7.46 (m, 1H), 7.10-7.00 (m, 2H), 6.47 (t, J = 5.6 Hz, 1H), 5.08-5.01 (m, 1H), 4.23-4.08 (m, 1H), 3.99 (s, 3H), 3.28-3.18 (m, 3H), 3.02 (s, 2H), 2.97-2.83 (m, 2H), 2.64-2.52 (m, 3H), 2.39-2.25 (m, 2H), 2.23-2.11 (m, 3H), 2.08-1.98 (m, 1H), 1.98-1.85 (m, 2H), 1.82 (d, J = 11.2 Hz, 2H), 1.70-1.49 (m, 5H), 1.47-1.21 (m, 1H), 1.21-1.05 (m, 2H) |
| I-182 | ATC | BBT | 884.2 | 12.60 (s, 1H), 11.10 (s, 1H), 8.74-8.69 (m, 1H), 8.50-8.45 (m, 1H), 8.39 (t, J = 7.8 Hz, 1H), 8.21-8.17 (m, 1H), 7.66 (s, 1H), 7.59 (dd, J = 7.2, 8.4 Hz, 1H), 7.08 (d, J = 8.8 Hz, 1H), 7.03 (d, J = 6.8 Hz, 1H), 6.48 (t, J = 5.6 Hz, 1H), 6.07-6.01 (m, 1H), 5.06 (dd, J = 5.2, 13.2 Hz, 1H), 3.26-3.19 (m, 4H), 2.95-2.84 (m, 2H), 2.64-2.56 (m, 1H), 2.53 (d, J = 1.9 Hz, 2H), 2.30-2.25 (m, 2H), 2.24-2.12 (m, 5H), 2.08 (br d, J = 6.9 Hz, 2H), 2.06-2.01 (m, 1H), 1.96-1.85 (m, 4H), 1.69 (q, J = 7.2 Hz, 2H), 1.61 (s, 6H), 1.56 (s, 4H), 1.47 (t, J = 5.2 Hz, 2H), 1.40 (dd, J = 8.2, 11.2 Hz, 2H), 1.09-0.96 (m, 2H) |
| I-183 | AML | BBT | 856.1 | 12.60 (s, 1H), 11.11 (s, 1H), 8.72 (s, 1H), 8.51-8.44 (m, 1H), 8.39 (t, J = 7.8 Hz, 1H), 8.19 (dd, J = 0.8, 7.8 Hz, 1H), 7.67 (s, 1H), 7.59 (dd, J = 7.3, 8.4 Hz, 1H), 7.07 (d, J = 6.9 Hz, 1H), 7.01 (d, J = 8.6 Hz, 1H), 6.45 (d, J = 6.5 Hz, 1H), 6.06-6.02 (m, 1H), 5.06 (dd, J = 5.2, 12.8 Hz, 1H), 4.18-4.09 (m, 1H), 2.98-2.83 (m, 2H), 2.64-2.56 (m, 1H), 2.53 (br d, J = 1.9 Hz, 2H), 2.38-2.31 (m, 4H), 2.25-2.14 (m, 4H), 2.10 (br d, J = 7.3 Hz, 2H), 2.07-2.01 (m, 1H), 1.94-1.86 (m, 2H), 1.72-1.63 (m, 4H), 1.61 (s, 6H), 1.59-1.52 (m, 4H), 1.11-0.97 (m, 2H) |
| I-184 | AML | BDN | 857.4 | 12.43 (s, 1H), 11.16-11.00 (m, 1H), 8.53-8.41 (m, 2H), 8.36 (t, J = 8.0 Hz, 1H), 8.16 (d, J = 8.0 Hz, 1H), 7.58 (t, J = 8.0 Hz, 1H), 7.26 (s, 1H), 7.08-6.95 (m, 2H), 6.44 (d, J = 6.0 Hz, 1H), 5.97-5.87 (m, 1H), 5.05 (dd, J = 5.6, 12.8 Hz, 1H), 4.16-4.08 (m, 3H), 3.09 (t, J = 12.0 Hz, 2H), 2.94-2.82 (m, 1H), 2.64-2.56 (m, 1H), 2.38-2.28 (m, 4H), 2.22 (d, J = 6.8 Hz, 2H), 2.10 (d, J = 6.4 Hz, 2H), 2.06-1.99 (m, 1H), 1.80 (d, J = 12.0 Hz, 3H), 1.72-1.60 (m, 5H), 1.57 (s, 6H), 1.55 (s, 2H), 1.20-1.08 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| I-185 | BDG | ATJ | 869.5 | 11.10 (s, 1H), 10.50 (s, 1H), 8.68 (s, 1H), 8.48-8.44 (m, 1H), 8.43-8.37 (m, 1H), 8.32 (s, 1H), 8.21 (dd, J = 0.8, 7.6 Hz, 1H), 7.58 (dd, J = 7.6, 8.4 Hz, 1H), 7.14 (s, 1H), 7.10 (d, J = 8.8 Hz, 1H), 7.03 (d, J = 7.2 Hz, 1H), 6.46 (t, J = 5.6 Hz, 1H), 5.05 (dd, J = 5.2, 12.8 Hz, 1H), 4.41-4.28 (m, 1H), 3.98 (s, 3H), 3.32-3.28 (m, 3H), 2.95-2.80 (m, 1H), 2.63-2.52 (m, 2H), 2.46-2.37 (m, 1H), 2.36-2.29 (m, 2H), 2.25 (s, 3H), 2.17-2.08 (m, 2H), 2.08-1.98 (m, 1H), 1.98-1.88 (m, 4H), 1.88-1.72 (m, 3H), 1.69-1.40 (m, 6H), 1.37-1.16 (m, 4H), 1.15-1.00 (m, 2H) |
| I-187 | AJF | BDI | 927.3 | 12.32 (s, 1H), 11.10 (s, 1H), 8.73 (s, 1H), 8.49-8.41 (m, 2H), 8.35 (s, 1H), 8.29-8.25 (m, 1H), 8.20-8.17 (m, 1H), 7.60-7.54 (m, 2H), 7.11 (d, J = 8.6 Hz, 1H), 7.03 (d, J = 7.2 Hz, 1H), 6.47 (t, J = 5.2 Hz, 1H), 5.91 (s, 1H), 5.08-5.01 (m, 1H), 4.46-4.35 (m, 1H), 2.93-2.83 (m, 1H), 2.63-2.51 (m, 6H), 2.31-2.27 (m, 1H), 2.25-2.18 (m, 2H), 2.11 (s, 4H), 2.06-2.00 (m, 1H), 1.97-1.81 (m, 7H), 1.62 (s, 6H), 1.58 (s, 2H), 1.53-1.46 (m, 4H), 1.15-1.02 (m, 2H); $^{19}$F NMR (376 MHz, DMSO-$d_6$) δ 81.10-79.27 (m, 1F), 54.16 (d, J = 150.5 Hz, 4F) |
| I-188 | ATH | BDK | 837.4 | 11.10 (s, 1H), 10.63 (s, 1H), 8.56 (s, 1H), 8.38 (s, 1H), 8.35-8.28 (m, 2H), 8.02 (dd, J = 2.0, 6.8 Hz, 1H), 7.59 (dd, J = 12, 8.4 Hz, 1H), 7.09-7.03 (m, 2H), 6.48 (t, J = 6.0 Hz, 1H), 5.05 (dd, J = 5.6, 12.8 Hz, 1H), 4.49-4.34 (m, 1H), 4.15-3.92 (m, 3H), 3.86 (s, 4H), 3.26-3.20 (m, 2H), 3.07-2.95 (m, 1H), 2.94-2.83 (m, 1H), 2.69-2.60 (m, 1H), 2.57 (s, 2H), 2.33 (m, 3H), 2.23-2.10 (m, 7H), 2.07-1.98 (m, 1H), 1.96-1.81 (m, 7H), 1.70-1.59 (m, 3H), 1.27-1.13 (m, 2H); LC-MS (ESI$^+$) m/z 837.5 (M + H)$^+$. HCl salt: $^1$H NMR (400 MHz, DMSO-$d_6$) δ 11.12 (s, 1H), 10.66 (s, 1H), 10.20-9.97 (m, 1H), 8.59 (s, 1H), 8.41 (s, 1H), 8.37-8.30 (m, 2H), 8.05 (dd, J = 2.0, 6.8 Hz, 1H), 7.61 (dd, J = 7.2, 8.4 Hz, 1H), 7.08 (dd, J = 7.6, 18.4 Hz, 2H), 6.55-6.46 (m, 1H), 5.07 (dd, J = 5.2, 12.6 Hz, 1H), 4.49-4.40 (m, 1H), 4.30-4.23 (m, 1H), 4.17-4.04 (m, 2H), 4.03-3.96 (m, 1H), 3.89 (s, 3H), 3.30-3.21 (m, 2H), 3.07 (m, 2H), 2.97-2.85 (m, 1H), 2.71-2.62 (m, 3H), 2.37-2.29 (m, 2H), 2.27-2.11 (m, 7H), 2.09-1.84 (m, 8H), 1.74-1.63 (m, 3H), 1.30-1.15 (m, 2H) |
| I-189 | AQK | BBV | 766.4 | 11.10 (s, 1H), 10.52 (s, 1H), 8.67 (s, 1H), 8.31 (s, 1H), 8.20 (s, 1H), 8.09 (d, J = 8.4 Hz, 1H), 7.90 (t, J = 8.8 Hz, 1H), 7.14 (s, 1H), 7.02-6.95 (m, 1H), 6.94-6.84 (m, 2H), 5.36 (d, J = 12.8 Hz, 1H), 4.42-4.33 (m, 1H), 4.01 (s, 3H), 3.65 (s, 3H), 3.16 (d, J = 11.2 Hz, 2H), 2.89 (d, J = 16.4 Hz, 1H), 2.78-2.63 (m, 4H), 2.59 (d, J = 2.8 Hz, 3H), 2.33 (d, J = 6.4 Hz, 2H), 2.28 (s, 3H), 2.15 (d, J = 12.0 Hz, 2H), 2.01-1.77 (m, 7H), 1.74-1.52 (m, 3H), 1.18-1.05 (m, 2H) |
| I-190 | AZK | BBA | 827.4 | 11.10 (s, 1H), 10.40 (s, 1H), 8.73-8.68 (m, 1H), 8.59 (s, 1H), 8.49-8.39 (m, 2H), 8.25 (d, J = 7.2 Hz, 1H), 7.80 (s, 1H), 7.10-6.98 (m, 3H), 5.44-5.35 (m, 1H), 4.62-4.46 (m, 1H), 3.63 (s, 3H), 3.57-3.45 (m, 3H), 3.08-3.00 (m, 1H), 2.95-2.83 (m, 3H), 2.76-2.69 (m, 1H), 2.65-2.59 (m, 1H), 2.23-2.18 (m, 2H), 2.11-1.88 (m, 11H), 1.34-1.22 (m, 2H) |
| I-191 | AXJ | ATJ | 845.5 | 11.08 (s, 1H), 10.50 (s, 1H), 8.68 (s, 1H), 8.48-8.44 (m, 1H), 8.43-8.38 (m, 1H), 8.32 (s, 1H), 8.21 (dd, J = 1.8, 7.6 Hz, 1H), 7.15 (s, 1H), 6.97-6.92 (m, 2H), 6.84 (dd, J = 1.8, 7.6 Hz, 1H), 5.35 (dd, J = 5.2, 12.8 Hz, 1H), 4.39-4.30 (m, 1H), 4.16-4.09 (m, 1H), 3.97 (s, 3H), 3.54 (s, 3H), 3.31-3.29 (m, 2H), 3.07 (d, J = 8.0 Hz, 2H), 2.93-2.83 (m, 1H), 2.75-2.67 (m, 1H), 2.64-2.58 (m, 1H), 2.37-2.32 (m, 2H), 2.15 (s, 3H), 2.14-2.09 (m, 3H), 2.04-1.82 (m, 11H), 1.65-1.54 (m, 3H), 1.12-1.02 (m, 2H) |
| I-192 | AQK | BAT | 774.5 | 11.10 (s, 1H), 10.53 (s, 1H), 9.37 (dd, J = 1.6, 7.2 Hz, 1H), 8.95 (dd, J = 1.6, 4.0 Hz, 1H), 8.69 (d, J = 7.6 Hz, 2H), 8.27 (s, 1H), 7.36-7.31 (m, 1H), 7.10 (s, 1H), 7.00-6.93 (m, 1H), 6.93-6.83 (m, 2H), 5.35 (dd, J = 5.6, 12.8 Hz, 1H), 4.39-4.30 (m, 1H), 4.02 (s, 3H), 3.64 (s, |

TABLE 7-continued

| Compounds synthesized via Method 2 with the reductive amination of various intermediate amines and aldehydes. | | | | |
|---|---|---|---|---|
| I-# | Intermediate Amine | Intermediate Aldehyde | LCMS (ES+) m/z $(M + H)^+$ | $^1$HNMR (400 MHz, DMSO-$d_6$) δ |
| | | | | 3H), 3.15 (d, J = 11.2 Hz, 2H), 2.95-2.83 (m, 1H), 2.74-2.68 (m, 2H), 2.65-2.58 (m, 1H), 2.46 (s, 2H), 2.32 (d, J = 6.8 Hz, 2H), 2.27 (s, 3H), 2.14 (d, J = 11.2 Hz, 2H), 2.02-1.86 (m, 5H), 1.80 (d, J = 10.4 Hz, 2H), 1.73-1.53 (m, 3H), 1.17-1.03 (m, 2H) |
| I-193 | BBW | AGL | 828.5 | 12.36 (s, 1H), 11.09 (s, 1H), 8.71 (s, 1H), 8.45 (d, J = 7.6 Hz, 1H), 8.40-8.34 (m, 2H), 8.15 (d, J = 8.8 Hz, 1H), 7.57 (s, 1H), 7.12 (d, J = 7.6 Hz, 1H), 7.01 (t, J = 7.6 Hz, 1H), 6.92 (d, J = 7.6 Hz, 1H), 5.95 (s, 1H), 5.35 (dd, J = 5.6, 12.8 Hz, 1H), 4.51-4.40 (m, 1H), 3.73-3.70 (m, 3H), 3.14 (d, J = 9.6 Hz, 2H), 2.93-2.82 (m, 3H), 2.77-2.63 (m, 2H), 2.37 (s, 2H), 2.17 (d, J = 9.6 Hz, 2H), 2.07 (d, J = 11.6 Hz, 2H), 2.01-1.89 (m, 7H), 1.62 (s, 7H), 1.28-1.14 (m, 2H), 1.12-1.10 (m, 1H) |
| I-194 | BBW | ATJ | 800.2 | 11.10 (s, 1H), 10.52 (s, 1H), 8.71 (s, 1H), 8.50-8.46 (m, 1H), 8.44-8.39 (m, 1H), 8.36 (s, 1H), 8.23 (dd, J = 0.8, 7.6 Hz, 1H), 7.18 (s, 1H), 7.13 (d, J = 8.0 Hz, 1H), 7.02 (t, J = 7.6 Hz, 1H), 6.93 (d, J = 7.6 Hz, 1H), 5.37 (dd, J = 5.2, 12.8 Hz, 1H), 4.46-4.33 (m, 1H), 4.00 (s, 3H), 3.73 (s, 3H), 3.11 (d, J = 9.6 Hz, 2H), 2.96-2.81 (m, 4H), 2.77-2.58 (m, 3H), 2.18 (d, J = 10.0 Hz, 2H), 2.12-1.87 (m, 11H), 1.66-1.54 (m, 1H), 1.26-1.11 (m, 2H) |
| I-195 | BBY | ATJ | 831.1 | 11.08 (s, 1H), 10.50 (s, 1H), 8.68 (s, 1H), 8.48-8.44 (m, 1H), 8.43-8.37 (m, 1H), 8.32 (s, 1H), 8.24-8.19 (m, 1H), 7.15 (s, 1H), 6.99-6.93 (m, 2H), 6.87-6.82 (m, 1H), 5.40-5.31 (m, 1H), 4.42-4.30 (m, 1H), 4.22-4.12 (m, 1H), 3.98 (s, 3H), 3.55 (s, 3H), 3.39 (s, 2H), 3.08-3.06 (m, 2H), 2.93-2.82 (m, 1H), 2.76-2.53 (m, 5H), 2.29-2.21 (m, 5H), 2.14-2.10 (m, 2H), 2.05-1.84 (m, 9H), 1.64-1.53 (m, 1H), 1.16-1.01 (m, 2H) |
| I-197 | ATC | BDN | 885.4 | 12.43 (s, 1H), 11.17-10.98 (m, 1H), 8.47 (s, 1H), 8.46-8.42 (m, 1H), 8.36 (t, J = 8.0 Hz, 1H), 8.16 (dd, J = 0.8, 8.0 Hz, 1H), 7.58 (dd, J = 7.2, 8.4 Hz, 1H), 7.26 (s, 1H), 7.07 (d, J = 8.8 Hz, 1H), 7.02 (d, J = 6.8 Hz, 1H), 6.47 (t, J = 5.6 Hz, 1H), 6.05-5.83 (m, 1H), 5.07-5.02 (m, 1H), 4.12 (d, J = 11.6 Hz, 2H), 3.24-3.19 (m, 2H), 3.11-3.06 (m, 2H), 2.94-2.82 (m, 1H), 2.63-2.55 (m, 2H), 2.31-2.14 (m, 5H), 2.09-2.07 (m, 2H), 2.05-1.98 (m, 1H), 1.93-1.89 (m, 2H), 1.80-1.77 (m, 3H), 1.72-1.63 (m, 2H), 1.56 (s, 6H), 1.55-1.51 (m, 2H), 1.47-1.44 (m, 2H), 1.41-1.36 (m, 2H), 1.20-1.04 (m, 2H) |
| I-198 | ATH | BBZ | 824.5 | 11.10 (s, 1H), 10.69 (s, 1H), 8.74-8.62 (m, 1H), 8.38-8.26 (m, 2H), 8.06-8.01 (m, 1H), 7.62-7.55 (m, 1H), 7.52-7.46 (m, 1H), 7.11-6.97 (m, 2H), 6.56-6.38 (m, 1H), 5.09-5.00 (m, 1H), 4.27-4.15 (m, 1H), 4.13-3.97 (m, 5H), 3.97-3.89 (m, 1H), 3.25-3.18 (m, 2H), 3.02 (t, J = 6.4 Hz, 2H), 2.97-2.82 (m, 2H), 2.64-2.52 (m, 2H), 2.31-2.25 (m, 1H), 2.22-2.10 (m, 6H), 2.07-1.71 (m, 6H), 1.70-1.50 (m, 5H), 1.27-1.02 (m, 2H) |
| I-199 | ATC | BCB | 911.5 | 11.29-11.23 (m, 1H), 11.09 (s, 1H), 8.77-8.72 (m, 1H), 8.51-8.46 (m, 1H), 8.41 (t, J = 8.0 Hz, 1H), 8.23 (d, J = 7.6 Hz, 1H), 7.80-7.73 (m, 1H), 7.61-7.54 (m, 1H), 7.08-7.00 (m, 2H), 6.46 (t, J = 5.6 Hz, 1H), 5.08-5.01 (m, 1H), 3.85 (s, 4H), 3.27-3.16 (m, 3H), 2.89 (d, J = 3.2 Hz, 4H), 2.85 (s, 1H), 2.64-2.52 (m, 2H), 2.41-2.19 (m, 5H), 2.14 (d, J = 7.2 Hz, 4H), 2.06-1.98 (m, 1H), 1.94-1.83 (m, 3H), 1.82-1.73 (m, 1H), 1.71-1.34 (m, 11H), 1.32-1.18 (m, 1H), 1.07-0.95 (m, 1H) |
| I-200 | ATH | BCC | 849.0 | 11.13 (m, 1H), 10.55 (s, 1H), 8.68 (s, 1H), 8.32-8.28 (m, 3H), 8.01 (m, 1H), 7.58 (m, 1H), 7.39 (s, 1H), 7.07-7.01(m, 2H), 6.49 (m, 1H), 5.07 (m, 1H), 4.34 (m, 1H), 4.11 (m, 1H), 3.22 (m, 3H), 3.11 (s, 2H), 3.01 (s, 2H), 2.50 (m, 2H), 2.20-2.10 (m, 12H), 1.88 (m, 3H), 1.85 (m, 2H), 1.74 (m, 2H), 1.65 (m, 1H), 1.10 (m, 2H), 0.94 (m, 2H), 0.78 (m, 2H) |
| I-201[b] | AJF | ATJ | 841.1 | 11.10 (s, 1H), 10.50 (s, 1H), 9.94 (s, 1H), 8.69 (s, 1H), 8.52-8.36 (m, 2H), 8.33 (s, 1H), 8.25-8.16 (m, 1H), 7.58 (dd, J = 7.2, 8.4 Hz, 1H), 7.19-7.08 (m, 2H), 7.03 (d, J = 7.2 Hz, 1H), 6.51 (s, 1H), 5.05 (dd, J = 5.2, 12.2 Hz, 1H), 4.42-4.36 (m, 1H), 3.98 (s, 3H), 3.43-3.25 (m, 4H), 3.02-2.74 (m, 5H), 2.64-2.52 (m, 3H), 2.14 |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | (d, J = 10.0 Hz, 2H), 2.09-1.99 (m, 4H), 1.99-1.83 (m, 7H), 1.72 (d, J = 13.2 Hz, 1H), 1.67-1.50 (m, 2H), 1.33-1.16 (m, 2H) |
| I-202 | AML | AXF | 855.5 | 11.10 (s, 1H), 10.73 (s, 1H), 8.72 (s, 1H), 8.47-8.44 (m, 1H), 8.43-8.37 (m, 1H), 8.31 (s, 1H), 8.23-8.19 (m, 1H), 7.61-7.55 (m, 1H), 7.18 (s, 1H), 7.06 (d, J = 7.2 Hz, 1H), 6.99 (d, J = 8.4 Hz, 1H), 6.45 (d, J = 6.4 Hz, 1H), 5.10-5.02 (m, 1H), 4.89-4.79 (m, 1H), 4.41-4.28 (m, 1H), 4.20-4.03 (m, 1H), 2.96-2.81 (m, 1H), 2.64-2.53 (m, 2H), 2.47-2.39 (m, 2H), 2.38-2.29 (m, 4H), 2.21 (d, J = 6.4 Hz, 2H), 2.12 (d, J = 10.4 Hz, 2H), 2.07-1.98 (m, 1H), 1.96-1.81 (m, 4H), 1.74-1.53 (m, 7H), 1.41 (s, 3H), 1.40 (s, 3H), 1.16-0.99 (m, 2H) |
| I-203 | AXH | AGL | 885.4 | 12.37 (s, 1H), 11.10 (s, 1H), 8.72 (s, 1H), 8.49-8.42 (m, 1H), 8.41-8.33 (m, 2H), 8.18 (s, 1H), 7.58 (s, 1H), 7.09-6.92 (m, 2H), 6.86 (dd, J = 2.4, 6.4 Hz, 1H), 5.94 (s, 1H), 5.37 (dd, J = 5.2, 12.4 Hz, 1H), 4.47-4.26 (m, 2H), 3.55 (s, 3H), 3.08 (d, J = 8.0 Hz, 3H), 2.98-2.80 (m, 2H), 2.78-2.69 (m, 3H), 2.65-2.58 (m, 1H), 2.19-2.10 (m, 4H), 2.10-1.98 (m, 7H), 1.97-1.87 (m, 4H), 1.84-1.77 (m, 2H), 1.62 (s, 7H), 1.44-1.42 (m, 2H), 1.17-1.04 (m, 2H) |
| I-204 | APZ | AXI | 867.5 | 12.33 (s, 1H), 11.09 (s, 1H), 8.76 (s, 1H), 8.35 (s, 1H), 8.28-7.89 (m, 4H), 7.59 (s, 1H), 7.36 (dd, J = 0.8, 8.0 Hz, 1H), 6.95 (d, J = 4.8 Hz, 2H), 6.88-6.81 (m, 1H), 6.38-6.25 (m, 1H), 5.41-5.30 (m, 1H), 4.46-4.36 (m, 1H), 3.55 (s, 3H), 2.92-2.84 (m, 1H), 2.83-2.77 (m, 2H), 2.76-2.68 (m, 1H), 2.65-2.58 (m, 1H), 2.31-2.17 (m, 5H), 2.15-2.08 (m, 4H), 2.04-1.83 (m, 8H), 1.74-1.68 (m, 2H), 1.65 (s, 6H), 1.56 (s, 2H), 1.48 (t, J = 4.8 Hz, 2H), 1.42-1.34 (m, 2H), 1.15-1.02 (m, 2H) |
| I-205 | AXJ | ALU | 865.5 | 11.08 (s, 1H), 10.49 (s, 1H), 8.54 (s, 1H), 8.49 (s, 1H), 8.47-8.42 (m, 1H), 8.42-8.35 (m, 1H), 8.21 (d, J = 7.8 Hz, 1H), 7.98 (s, 1H), 7.41-7.07 (m, 1H), 6.94 (q, J = 8.0 Hz, 2H), 6.83 (d, J = 7.6 Hz, 1H), 5.35 (dd, J = 5.2, 12.4 Hz, 1H), 4.50 (t, J = 11.4 Hz, 1H), 4.16-4.10 (m, 1H), 3.54 (s, 3H), 3.31 (t, J = 6.2 Hz, 2H), 3.06 (d, J = 7.8 Hz, 2H), 2.93-2.82 (m, 1H), 2.75-2.65 (m, 1H), 2.63-2.57 (m, 1H), 2.48-2.44 (m, 1H), 2.40 (t, J = 6.4 Hz, 2H), 2.26-2.12 (m, 7H), 2.06-1.87 (m, 9H), 1.71-1.55 (m, 3H), 1.19-1.02 (m, 2H) |
| I-206 | APZ | AXK | 833.6 | 12.37 (s, 1H), 11.10 (s, 1H), 8.69 (s, 1H), 8.33 (s, 1H), 8.13-8.03 (m, 1H), 7.90-7.80 (m, 1H), 7.57 (s, 1H), 6.96 (d, J = 4.8 Hz, 2H), 6.89-6.81 (m, 1H), 6.09-5.89 (m, 1H), 5.43-5.30 (m, 1H), 4.46-4.36 (m, 1H), 3.56 (s, 3H), 2.95-2.85 (m, 1H), 2.84-2.77 (m, 2H), 2.77-2.68 (m, 1H), 2.67-2.60 (m, 1H), 2.59 (d, J = 2.8 Hz, 3H), 2.32-2.20 (m, 4H), 2.17-2.10 (m, 4H), 2.05-1.98 (m, 1H), 1.96-1.86 (m, 6H), 1.76-1.69 (m, 2H), 1.68-1.53 (m, 10H), 1.52-1.45 (m, 2H), 1.43-1.36 (m, 2H), 1.15-1.05 (m, 2H) |
| I-207 | APZ | AXL | 831.6 | 12.29 (s, 1H), 11.10 (s, 1H), 8.77 (s, 1H), 8.34 (s, 1H), 7.99-7.89 (m, 1H), 7.78 (d, J = 6.8 Hz, 1H), 7.58 (s, 1H), 7.07 (d, J = 8.4 Hz, 1H), 6.96 (d, J = 4.8 Hz, 2H), 6.89-6.82 (m, 1H), 6.00 (s, 1H), 5.45-5.24 (m, 1H), 4.49-4.33 (m, 1H), 4.05 (s, 3H), 3.56 (s, 3H), 2.94-2.85 (m, 1H), 2.84-2.76 (m, 2H), 2.76-2.68 (m, 1H), 2.66-2.58 (m, 1H), 2.39-2.33 (m, 2H), 2.30-2.21 (m, 3H), 2.17-2.11 (m, 4H), 2.06-1.85 (m, 8H), 1.76-1.68 (m, 2H), 1.65 (s, 6H), 1.62-1.55 (m, 2H), 1.54-1.46 (m, 2H), 1.45-1.35 (m, 2H), 1.17-1.04 (m, 2H) |
| I-208 | ATC | AXN | 861.1 | 11.10 (s, 1H), 9.77 (s, 1H), 8.89 (s, 1H), 8.47-8.30 (m, 2H), 7.59 (dd, J = 7.2, 8.4 Hz, 1H), 7.19-6.97 (m, 3H), 6.48 (t, J = 5.6 Hz, 1H), 5.06 (dd, J = 5.6, 12.8 Hz, 1H), 4.43-4.29 (m, 1H), 3.96 (s, 3H), 3.24-3.18 (m, 4H), 2.95-2.82 (m, 1H), 2.65-2.53 (m, 4H), 2.33-2.17 (m, 5H), 2.16-1.99 (m, 6H), 1.96-1.81 (m, 7H), 1.74-1.35 (m, 10H), 1.08 (br d, J = 14.0 Hz, 2H) |
| I-209 | AFJ | AXP | 823.2 | 11.10 (s, 1H), 10.55 (s, 1H), 8.68 (s, 1H), 8.36-8.27 (m, 3H), 7.99 (dd, J = 1.2, 7.2 Hz, 1H), 7.62-7.51 (m, 1H), 7.33-6.98 (m, 4H), 6.47 (t, J = 5.6 Hz, 1H), 5.05 (dd, J = 5.2, 12.8 Hz, 1H), 4.43-4.27 (m, 1H), 3.99 (s, 3H), 3.32-3.32 (m, 2H), 2.96-2.81 (m, 1H), 2.64- |

TABLE 7-continued

Compounds synthesized via Method 2 with the reductive amination of various intermediate amines and aldehydes.

| I-# | Intermediate Amine | Intermediate Aldehyde | LCMS (ES+) m/z $(M + H)^+$ | $^1$HNMR (400 MHz, DMSO-$d_6$) δ |
|---|---|---|---|---|
| | | | | 2.52 (m, 4H), 2.31-2.19 (m, 3H), 2.12 (d, J = 7.2 Hz, 4H), 2.07-1.99 (m, 1H), 1.95-1.80 (m, 6H), 1.64-1.55 (m, 3H), 1.54-1.45 (m, 4H), 1.16-1.01 (m, 2H) |
| I-210 | AVZ | ATJ | 829.2 | 11.10 (s, 1H), 10.50 (s, 1H), 8.68 (s, 1H), 8.48-8.37 (m, 2H), 8.33 (s, 1H), 8.22 (dd, J = 0.8, 7.6 Hz, 1H), 7.58 (dd, J = 7.2, 8.4 Hz, 1H), 7.16-7.09 (m, 2H), 7.03 (d, J = 7.2 Hz, 1H), 6.60 (t, J = 5.6 Hz, 1H), 5.10-5.01 (m, 1H), 4.45-4.28 (m, 1H), 3.98 (s, 3H), 3.19 (t, J = 6.4 Hz, 2H), 2.94-2.83 (m, 1H), 2.62-2.52 (m, 4H), 2.49-2.47 (m, 3H), 2.43-2.35 (m, 2H), 2.19-2.09 (m, 2H), 2.07-2.00 (m, 1H), 1.98-1.82 (m, 7H), 1.70-1.51 (m, 2H), 1.41-1.24 (m, 2H), 1.20-1.00 (m, 4H) |
| I-211 | AOV | AXS | 761.4 | 11.10 (s, 1H), 10.70 (s, 1H), 8.70 (s, 1H), 8.30 (s, 1H), 8.02-7.94 (m, 2H), 7.62-7.52 (m, 2H), 7.17 (d, J = 8.8 Hz, 1H), 7.13 (s, 1H), 7.03 (d, J = 6.8 Hz, 1H), 6.16 (d, J = 8.4 Hz, 1H), 5.05 (dd, J = 5.2, 12.8 Hz, 1H), 4.41-4.30 (m, 1H), 4.00 (s, 3H), 2.93-2.84 (m, 1H), 2.62 (s, 3H), 2.60-2.51 (m, 3H), 2.46 (d, J = 3.6 Hz, 1H), 2.32-2.27 (m, 2H), 2.25 (s, 3H), 2.17-2.09 (m, 2H), 2.09-2.00 (m, 3H), 1.98-1.83 (m, 4H), 1.82-1.73 (m, 2H), 1.59-1.39 (m, 3H), 1.37-1.24 (m, 2H), 1.16-0.99 (m, 2H) |
| I-212 | ATC | AXU | 869.3 | 11.10 (s, 1H), 10.74 (s, 1H), 8.71 (s, 1H), 8.49-8.45 (m, 1H), 8.44-8.38 (m, 1H), 8.32 (s, 1H), 8.21-8.20 (m, 1H), 7.59 (d, J = 7.6 Hz, 1H), 7.13 (s, 1H), 7.08 (d, J = 8.4 Hz, 1H), 7.03 (d, J = 7.0 Hz, 1H), 6.48 (t, J = 5.6 Hz, 1H), 5.08-5.06 (m 1H), 4.39-4.30 (m, 1H), 4.20 (d, J = 6.4 Hz, 2H), 3.26-3.18 (m, 4H), 2.96-2.83 (m, 1H), 2.70-2.56 (m, 2H), 2.35-2.19 (m, 5H), 2.16-2.08 (m, 4H), 2.07-2.00 (m, 1H), 1.96-1.85 (m, 6H), 1.74-1.66 (m, 2H), 1.57 (s, 2H), 1.53-1.48 (m, 4H), 1.40 (d, J = 9.6 Hz, 2H), 1.14-1.02 (m, 2H) |
| I-213 | AYR | ATJ | 845.4 | 11.10 (s, 1H), 10.50 (s, 1H), 8.68 (s, 1H), 8.49-8.44 (m, 1H), 8.43-8.37 (m, 1H), 8.31 (s, 1H), 8.21 (d, J = 7.6 Hz, 1H), 7.59 (t, J = 7.6 Hz, 1H), 7.13 (s, 1H), 7.06 (d, J = 7.2 Hz, 1H), 7.02 (d, J = 8.4 Hz, 1H), 6.43 (d, J = 6.8 Hz, 1H), 5.09-5.01 (m, 1H), 4.41-4.28 (m, 1H), 3.98 (s, 3H), 3.81-3.69 (m, 2H), 3.40-3.35 (m, 4H), 2.95-2.86 (m, 1H), 2.85-2.76 (m, 2H), 2.62-2.53 (m, 2H), 2.31-2.18 (m, 5H), 2.12 (d, J = 10.4 Hz, 2H), 2.05-1.97 (m, 1H), 1.96-1.78 (m, 6H), 1.72-1.64 (m, 2H), 1.64-1.55 (m, 1H), 1.18-1.02 (m, 2H) |
| I-214 | WX | AYL | 871.4 | 11.15-11.04 (m, 2H), 8.79 (s, 1H), 8.57-8.47 (m, 1H), 8.45-8.36 (m, 2H), 8.22 (s, 1H), 7.51 (s, 1H), 7.15-6.84 (m, 3H), 5.39 (dd, J = 5.6, 12.4 Hz, 1H), 4.46-4.30 (m, 1H), 3.91-3.84 (m, 4H), 3.69 (s, 3H), 3.62 (s, 3H), 2.96-2.85 (m, 7H), 2.79-2.68 (m, 1H), 2.69-2.56 (m, 1H), 2.34-2.28 (m, 1H), 2.24-2.18 (m, 4H), 2.16-2.08 (m, 2H), 2.06-1.84 (m, 7H), 1.71-1.59 (m, 2H), 1.56-1.34 (m, 3H), 1.20-0.96 (m, 2H) |
| I-215 | ARK | AYM | 830.6 | 12.36 (s, 1H), 11.10 (s, 1H), 8.71 (s, 1H), 8.48-8.42 (m, 1H), 8.39-8.33 (m, 2H), 8.18-8.13 (m, 1H), 7.57 (s, 1H), 7.12-7.02 (m, 1H), 6.96 (t, J = 8.0 Hz, 1H), 6.91-6.86 (m, 1H), 5.94 (s, 1H), 5.38 (dd, J = 5.2, 12.4 Hz, 1H), 4.47-4.34 (m, 1H), 3.67 (s, 3H), 3.66-3.62 (m, 2H), 2.93-2.85 (m, 1H), 2.77-2.69 (m, 1H), 2.65-2.59 (m, 1H), 2.47-2.34 (m, 6H), 2.32-2.22 (m, 3H), 2.14-2.08 (m, 2H), 2.06-1.83 (m, 6H), 1.61 (s, 6H), 1.43-1.35 (m, 3H), 1.21-1.11 (m, 2H) |
| I-216 | ARN | AGL | 842.5 | 12.36 (s, 1H), 11.10 (s, 1H), 8.71 (s, 1H), 8.47-8.43 (m, 1H), 8.39-8.33 (m, 2H), 8.17-8.15 (m, 1H), 7.57 (s, 1H), 7.06 (d, J = 7.6 Hz, 1H), 6.97-6.92 (m, 1H), 6.90-6.87 (m, 1H), 5.94 (s, 1H), 5.37 (dd, J = 5.2, 12.4 Hz, 1H), 4.46-4.38 (m, 1H), 3.69 (s, 3H), 3.62 (s, 2H), 3.58-3.46 (m, 2H), 3.08 (s, 2H), 2.94-2.85 (m, 1H), 2.76-2.68 (m, 1H), 2.66-2.58 (m, 1H), 2.28-2.24 (m, 2H), 2.16-2.12 (m, 4H), 2.05-1.99 (m, 3H), 1.95-1.86 (m, 2H), 1.79-1.72 (m, 2H), 1.62 (s, 6H), 1.57-1.52 (m, 2H), 1.50-1.43 (m, 1H), 1.17-1.07 (m, 2H) |
| I-217 | ARK | AGL | 816.5 | 12.36 (s, 1H), 11.10 (s, 1H), 8.71 (s, 1H), 8.47-8.42 (m, 1H), 8.39-8.34 (m, 2H), 8.19-8.14 (m, 1H), 7.57 (s, 1H), 7.07 (d, J = 8.0 Hz, 1H), 6.96 (t, J = 7.6 Hz, 1H), 6.91-6.87 (m, 1H), 5.94 (s, 1H), 5.38 (dd, J = 5.6, |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | 12.8 Hz, 1H), 4.45-4.37 (m, 1H), 3.68 (s, 3H), 3.65 (s, 2H), 2.94-2.85 (m, 1H), 2.77-2.68 (m, 1H), 2.65-2.60 (m, 1H), 2.46-2.35 (m, 5H), 2.13 (d, J = 7.2 Hz, 4H), 2.11-2.08 (m, 1H), 2.04-1.99 (m, 1H), 1.98-1.79 (m, 5H), 1.67-1.54 (m, 8H), 1.17-1.06 (m, 2H) |
| I-218 | AJF | AYO | 853.5 | 11.07 (s, 1H), 10.86 (s, 1H), 8.64 (s, 1H), 8.36 (s, 1H), 8.28 (s, 1H), 8.15 (s, 1H), 8.10 (s, 1H), 8.06-7.97 (m, 1H), 7.95-7.84 (m, 2H), 7.55 (m, 1H), 7.13 (s, 1H), 7.08 (d, J = 8.7 Hz, 1H), 7.00 (d, J = 7.0 Hz, 1H), 6.48-6.40 (m, 1H), 5.03 (m, 1H), 4.39-4.24 (m, 1H), 4.04 (s, 3H), 3.94 (s, 3H), 2.92-2.79 (m, 1H), 2.66-2.58 (m, 1H), 2.53 (m, 2H), 2.32-2.15 (m, 5H), 2.14-2.04 (m, 4H), 2.03-1.95 (m, 1H), 1.93-1.76 (m, 6H), 1.64-1.35 (m, 8H), 1.14-0.96 (m, 2H) |
| I-219 | ANK | AYO | 881.5 | 11.06 (s, 1H), 10.85 (s, 1H), 8.62 (s, 1H), 8.34 (s, 1H), 8.26 (s, 1H), 8.19 (s, 1H), 8.09 (s, 1H), 8.04-7.95 (m, 1H), 7.94-7.84 (m, 2H), 7.54 (m, 1H), 7.11 (s, 1H), 7.06 (d, J = 8.6 Hz, 1H), 6.98 (d, J = 7.0 Hz, 1H), 6.42 (m, 1H), 5.01 (m, 1H), 4.37-4.23 (m, 1H), 4.02 (s, 3H), 3.92 (s, 3H), 2.92-2.75 (m, 1H), 2.65-2.55 (m, 1H), 2.51 (m, 1H), 2.32-2.26 (m, 1H), 2.23-2.03 (m, 9H), 2.03-1.93 (m, 1H), 1.92-1.67 (m, 8H), 1.65-1.34 (m, 7H), 1.29-1.11 (m, 4H), 1.07-0.93 (m, 2H) |
| I-220 | AYP | ATJ | 841.0 | 11.1 (s, 1H), 10.51 (s, 1H), 8.69 (s, 1H), 8.49-8.39 (m, 2H), 8.33 (s, 1H), 8.25-8.19 (m, 1H), 7.72-7.64 (m, 1H), 7.39-7.29 (m, 2H), 7.16 (s, 1H), 5.13-5.04 (m, 1H), 4.43-4.31 (m, 1H), 3.99 (s, 3H), 3.28 (s, 8H), 2.96-2.80 (m, 2H), 2.65-2.54 (m, 2H), 2.30-2.22 (m, 2H), 2.14 (d, J = 10.4 Hz, 2H), 2.10-1.79 (m, 6H), 1.68-1.48 (m, 9H) |
| I-221 | AOQ | AYR | 471.4 (M/2 + H)$^+$ | 11.80 (s, 1H), 11.09 (s, 1H), 8.88 (s, 1H), 8.60 (s, 1H), 8.33 (s, 1H), 8.22-8.09 (m, 1H), 7.62-7.53 (m, 2H), 7.11-7.02 (m, 4H), 6.92 (d, J = 8.8 Hz, 1H), 6.50 (d, J = 6.0 Hz, 1H), 6.14 (s, 1H), 5.10-5.01 (m, 1H), 4.46-4.35 (m, 1H), 4.21-4.07 (m, 2H), 3.31 (s, 2H), 3.19 (t, J = 6.0 Hz, 2H), 2.95-2.81 (m, 1H), 2.56 (s, 2H), 2.43-2.33 (m, 4H), 2.28-2.19 (m, 2H), 2.19-2.09 (m, 7H), 2.07-1.82 (m, 5H), 1.65 (s, 9H), 1.18-1.01 (m, 3H), 0.50-0.41 (m, 2H), 0.27-0.18 (m, 2H) |
| I-222 | AQZ | ATJ | 841.1 | 11.06 (s, 1H), 10.50 (s, 1H), 8.68 (s, 1H), 8.48-8.43 (m, 1H), 8.42-8.37 (m, 1H), 8.32 (s, 1H), 8.22 (dd, J = 1.0, 7.8 Hz, 1H), 7.55 (d, J = 8.4 Hz, 1H), 7.15 (s, 1H), 7.09 (br t, J = 5.2 Hz, 1H), 6.94 (s, 1H), 6.85 (dd, J = 8.0, 8.4 Hz, 1H), 5.03 (dd, J = 8.0, 12.8 Hz, 1H), 4.40-4.30 (m, 1H), 3.98 (s, 3H), 3.22-3.17 (m, 3H), 2.87 (ddd, J = 5.4, 14.2, 17.4 Hz, 1H), 2.61-2.52 (m, 3H), 2.47-2.44 (m, 1H), 2.29-2.20 (m, 2H), 2.17-2.08 (m, 4H), 2.03-1.95 (m, 1H), 1.94-1.84 (m, 6H), 1.58 ( s, 3H), 1.53-1.44 (m, 4H), 1.16-1.01 (m, 2H) |
| I-223 | AWI | ATJ | 855.4 | 11.11 (s, 1H), 10.50 (s, 1H), 8.68 (s, 1H), 8.48-8.43 (m, 1H), 8.43-8.37 (m, 1H), 8.33 (s, 1H), 8.23-8.20 (m, 1H), 7.60-7.56 (m, 1H), 7.15 (s, 1H), 7.06 (d, J = 7.2 Hz, 1H), 6.99 (d, J = 8.4 Hz, 1H), 6.43 (d, J = 6.4 Hz, 1H), 5.08-5.04 (m, 1H), 4.41-4.30 (m, 1H), 4.14-4.02 (m, 1H), 3.98 (s, 3H), 2.93-2.88 (m, 1H), 2.64-2.53 (m, 2H), 2.46-2.34 (m, 2H), 2.30-2.29 (m, 2H), 2.24 (s, 3H), 2.22-2.17 (m, 1H), 2.14-2.12 (m, 2H), 2.08-1.99 (m, 1H), 1.98-1.81 (m, 5H), 1.77-1.47 (m, 6H), 1.44-1.28 (m, 3H), 1.27-1.01 (m, 3H) |
| I-224 | AML | AWZ | 791.2 | 11.11 (s, 1H), 10.51 (s, 1H), 8.66 (s, 1H), 8.30 (s, 1H), 8.08 (dd, J = 4.0, 8.4 Hz, 1H), 7.89 (t, J = 8.8 Hz, 1H), 7.61-7.55 (m, 1H), 7.13 (s, 1H), 7.06 (d, J = 7.2 Hz, 1H), 7.00 (d, J = 8.8 Hz, 1H), 6.44 (d, J = 6.0 Hz, 1H), 5.06 (dd, J = 5.2, 12.8 Hz, 1H), 4.40-4.29 (m, 1H), 4.18-4.07 (m, 1H), 3.99 (s, 3H), 2.94-2.83 (m, 1H), 2.64-2.52 (m, 6H), 2.35-2.29 (m, 3H), 2.26-2.17 (m, 2H), 2.15-2.07 (m, 4H), 2.06-1.99 (m, 1H), 1.94-1.81 (m, 4H), 1.72-1.53 (m, 7H), 1.15-1.01 (m, 2H) |
| I-225 | AOQ | AYT | 887.5 | 11.14-11.05 (m, 1H), 8.37 (d, J = 0.8 Hz, 1H), 8.11 (t, J = 8.0 Hz, 1H), 7.87-7.77 (m, 1H), 7.66-7.53 (m, 2H), 7.07 (d, J = 7.2 Hz, 1H), 6.92 (d, J = 8.8 Hz, 1H), 6.50 (d, J = 6.4 Hz, 1H), 5.08-5.02 (m, 1H), 4.52-4.44 (m, 1H), 4.19-4.08 (m, 2H), 2.93-2.83 (m, 1H), |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 2.67 (t, J = 2.0 Hz, 1H), 2.59 (s, 3H), 2.56 (s, 1H), 2.52 (s, 5H), 2.39-2.32 (m, 5H), 2.27-2.20 (m, 2H), 2.14 (s, 6H), 2.05-1.89 (m, 6H), 1.68-1.62 (m, 2H), 1.51 (s, 6H), 1.16-1.06 (m, 2H) |
| I-226 | AZK | AGL | 801.5 | 12.34 (s, 1H), 11.07 (s, 1H), 8.70 (s, 1H), 8.45-8.40 (m, 1H), 8.37-8.32 (m, 2H), 8.16-8.11 (m, 1H), 7.55 (s, 1H), 7.08-6.89 (m, 3H), 5.92 (s, 1H), 5.36 (dd, J = 12.4, 4.8 Hz, 1H), 4.52-4.35 (m, 1H), 3.58 (s, 3H), 2.92-2.83 (m, 1H), 2.73-2.54 (m, 4H), 2.20-2.09 (m, 3H), 2.07-1.65 (m, 13H), 1.60 (s, 6H), 1.22-1.00 (m, 3H) |
| I-227 | AYV | ATJ | 831.5 | 11.09 (s, 1H), 10.5 (s, 1H), 8.68 (s, 1H), 8.47-8.45 (m, 1H), 8.43-8.38 (m, 1H), 8.32 (s, 1H), 8.23-8.21 (m, 1H), 7.61-7.56 (m, 1H), 7.15-7.09 (m, 2H), 7.02 (d, J = 12 Hz, 1H), 6.58 (t, J = 6.4 Hz, 1H), 5.08-5.03 (m, 1H), 4.40-4.32 (m, 1H), 3.98 (s, 3H), 3.77 (d, J = 10.8 Hz, 1H), 3.44-3.39 (m, 2H), 2.93-2.84 (m, 1H), 2.73 (d, J = 10.4 Hz, 1H), 2.68-2.58 (m, 5H), 2.17-2.09 (m, 4H), 2.06-1.84 (m, 6H), 1.74-1.57 (m, 4H), 1.50-1.42 (m, 2H), 1.16-1.05 (m, 2H) |
| I-229 | AVW | AGL | 815.4 | 12.37 (s, 1H), 11.10 (s, 1H), 8.72 (s, 1H), 8.50-8.42 (m, 1H), 8.41-8.33 (m, 2H), 8.19-8.12 (m, 1H), 7.58 (s, 1H), 7.10-6.91 (m, 2H), 6.84 (dd, J = 1.6, 7.2 Hz, 1H), 5.95 (s, 1H), 5.38-5.34 (m, 1H), 4.52-4.32 (m, 1H), 3.55 (s, 3H), 2.86-2.80 (m, 4H), 2.75-2.69 (m, 1H), 2.66-2.60 (m, 1H), 2.23-2.07 (m, 4H), 2.04-1.78 (m, 8H), 1.62 (s, 9H), 1.54-1.45 (m, 1H), 1.37-1.26 (m, 2H), 1.16-1.07 (m, 2H) |
| I-230 | AOQ | ATJ | 845.5 | 11.10 (s, 1H), 10.50 (s, 1H), 8.68 (s, 1H), 8.46 (d, J = 7.6 Hz, 1H), 8.40 (t, J = 7.6 Hz, 1H), 8.32 (s, 1H), 8.21 (dd, J = 0.8, 7.6 Hz, 1H), 7.58 (dd, J = 7.2, 8.4 Hz, 1H), 7.14 (s, 1H), 7.07 (d, J = 7.2 Hz, 1H), 6.91 (d, J = 8.4 Hz, 1H), 6.50 (d, J = 6.0 Hz, 1H), 5.05 (dd, J = 5.2, 12.8 Hz, 1H), 4.42-4.31 (m, 1H), 4.21-4.09 (m, 2H), 3.97 (s, 3H), 2.92-2.82 (m, 1H), 2.63-2.51 (m, 3H), 2.48-2.34 (m, 5H), 2.29-2.17 (m, 7H), 2.16-2.09 (m, 2H), 2.06-1.98 (m, 1H), 1.95-1.83 (m, 4H), 1.70-1.64 (m, 2H), 1.63-1.54 (m, 1H), 1.17-1.03 (m, 2H) |
| I-231 | AJH | AWF | 851.2 | 11.11 (s, 1H), 10.83-10.77 (m, 1H), 8.70-8.66 (m, 1H), 8.32 (s, 1H), 8.21-8.11 (m, 2H), 7.86 (d, J = 8.0 Hz, 1H), 7.59 (d, J = 8.0 Hz, 1H), 7.15 (s, 1H), 7.11 (d, J = 8.4 Hz, 1H), 7.04 (d, J = 8.0 Hz, 1H), 6.69 (s, 1H), 5.10-5.02 (m, 1H), 4.42-4.32 (m, 1H), 4.00 (s, 3H), 3.52-3.44 (m, 3H), 3.24 (d, J = 4.0 Hz, 3H), 2.71-2.65 (m, 2H), 2.36-2.30 (m, 3H), 2.19-2.10 (m, 3H), 1.98-1.86 (m, 5H), 1.86-1.79 (m, 6H), 1.77 (s, 3H) |
| I-232[c] | AJF | AWF | 833.5 | 11.10 (s, 1H), 10.79 (s, 1H), 9.32-9.18 (m, 1H), 8.67 (s, 1H), 8.31 (s, 1H), 8.20-8.10 (m, 2H), 7.85 (d, J = 7.6 Hz, 1H), 7.61-7.57 (m, 1H), 7.14-7.12 (m, 2H), 7.04 (d, J = 7.2 Hz, 1H), 6.52-6.51 (m, 1H), 5.07-5.03 (m, 1H), 4.47-4.34 (m, 1H), 3.99 (s, 3H), 3.41 (m, 2H), 3.02-2.76 (m, 5H), 2.64-2.52 (m, 5H), 2.17-2.14 (m, 2H), 2.09-1.84 (m, 10H), 1.84-1.70 (m, 8H), 1.69-1.55 (m, 2H), 1.31-1.16 (m, 2H) |
| I-233 | AYV | AGL | 859.6 | 12.34 (s, 1H), 11.06 (s, 1H), 8.71 (s, 1H), 8.46-8.44 (m, 1H), 8.38-8.36 (m, 1H), 8.34 (s, 1H), 8.15 (d, J = 7.6 Hz, 1H), 7.61-7.57 (m, 2H), 7.10 (d, J = 8.8 Hz, 1H), 7.02 (d, J = 6.8 Hz, 1H), 6.56 (t, J = 5.2 Hz, 1H), 5.90 (s, 1H), 5.09-5.02 (m, 1H), 4.46-4.37 (m, 1H), 3.77 (d, J = 10.0 Hz, 1H), 3.54-3.41 (m, 2H), 3.34-3.32 (m, 2H), 2.93-2.84 (m, 1H), 2.73 (d, J = 10.0 Hz, 1H), 2.65-2.52 (m, 2H), 2.14 (d, J = 6.8 Hz, 4H), 2.09-1.83 (m, 7H), 1.75-1.56 (m, 10H), 1.50-1.44 (m, 2H), 1.15-1.05 (m, 2H) |
| I-234 | AQS | AQO | 877.1 | 12.43 (s, 1H), 11.13 (m, 1H), 8.78 (s, 1H), 8.33 (s, 1H), 8.11 (d, J = 3.6 Hz, 2H), 7.76 (m, 1H), 7.61 (m, 2H), 7.08 (d, J = 7.2 Hz, 1H), 6.90 (d, J = 8.8 Hz, 1H), 6.49 (d, J = 5.6 Hz, 1H), 6.04 (m, 1H), 5.02 (m, 1H), 4.40-4.30 (m, 2H), 4.12 (m, 1H), 2.88 (m, 3H), 2.66-2.50 (m, 4H), 2.12 (m, 3H), 2.11 (m, 4H), 1.98 (m, 8H), 1.91 (m, 8H), 1.80 (m, 6H), 1.75 (m, 2H), 1.10 (m, 2H) |
| I-235 | WX | AYX | 832.6 | 12.35 (s, 1H), 11.13 (s, 1H), 8.76 (s, 1H), 8.34 (s, 1H), 8.04-7.90 (m, 2H), 7.69-7.62 (m, 1H), 7.57 (s, 1H), 7.12-7.05 (m, 1H), 7.01-6.94 (m, 1H), 6.88 (d, J = |

TABLE 7-continued

Compounds synthesized via Method 2 with the reductive amination of various intermediate amines and aldehydes.

| I-# | Intermediate Amine | Intermediate Aldehyde | LCMS (ES+) m/z $(M + H)^+$ | $^1$HNMR (400 MHz, DMSO-$d_6$) δ |
|---|---|---|---|---|
| | | | | 7.6 Hz, 1H), 5.94 (s, 1H), 5.47-5.31 (m, 1H), 4.47-4.31 (m, 1H), 3.69 (s, 3H), 3.62 (s, 2H), 2.94-2.83 (m, 3H), 2.77-2.59 (m, 2H), 2.36-2.31 (m, 1H), 2.28-2.23 (m, 2H), 2.19 (s, 3H), 2.16-2.08 (m, 2H), 2.05-1.82 (m, 7H), 1.77-1.65 (m, 2H), 1.64 (s, 6H), 1.56-1.47 (m, 1H), 1.43 (s, 9H), 1.42-1.34 (m, 2H), 1.14-0.99 (m, 2H) |
| I-236 | AOV | AYX | 831.2 | 12.35 (s, 1H), 11.12 (s, 1H), 8.77 (s, 1H), 8.35 (s, 1H), 8.03-7.93 (m, 2H), 7.69-7.55 (m, 3H), 7.19 (d, J = 8.8 Hz, 1H), 7.05 (d, J = 7.2 Hz, 1H), 6.18 (br d, J = 8.4 Hz, 1H), 5.94 (s, 1H), 5.06 (dd, J = 5.6, 12.8 Hz, 1H), 4.49-4.35 (m, 1H), 3.58-3.51 (m, 1H), 2.96-2.83 (m, 1H), 2.71-2.55 (m, 2H), 2.40-2.25 (m, 5H), 2.20-1.77 (m, 12H), 1.65 (s, 6H), 1.49 (br d, J = 11.6 Hz, 2H), 1.43 (s, 9H), 1.39-1.24 (m, 3H), 1.17-1.06 (m, 2H) |
| I-237 | AZA | AYY | 821.1 | 12.35 (s, 1H), 8.68 (s, 1H), 8.32 (s, 1H), 8.06 (dd, J = 4.0, 8.8 Hz, 1H), 7.84 (t, J = 8.9 Hz, 1H), 7.66-7.47 (m, 2H), 7.12 (d, J = 8.4 Hz, 1H), 7.01 (d, J = 7.2 Hz, 1H), 6.58 (s, 1H), 5.02 (dd, J = 5.2, 12.8 Hz, 1H), 4.40 (d, J = 2.8 Hz, 1H), 2.91-2.77 (m, 1H), 2.58 (d, J = 2.8 Hz, 3H), 2.28-1.38 (m, 35H), 1.15-1.05 (m, 2H) |
| I-238 | AWI | AGL | 883.3 | 12.37 (s, 1H), 11.11 (s, 1H), 8.72 (s, 1H), 8.47-8.43 (m, 1H), 8.40-8.34 (m, 2H), 8.19-8.15 (m, 1H), 7.62-7.55 (m, 2H), 7.07 (d, J = 7.2 Hz, 1H), 7.00 (d, J = 8.4 Hz, 1H), 6.44 (d, J = 6.4 Hz, 1H), 5.95 (s, 1H), 5.10-5.03 (m, 1H), 4.47-4.37 (m, 1H), 4.14-4.06 (m, 1H), 2.95-2.85 (m, 1H), 2.64-2.57 (m, 1H), 2.45-2.35 (m, 4H), 2.30-2.00 (m, 7H), 1.99-1.84 (m, 6H), 1.76-1.67 (m, 3H), 1.65-1.60 (m, 9H), 1.41-1.33 (m, 3H), 1.28-1.22 (m, 1H), 1.18-1.06 (m, 2H) |
| I-240 | AZC | AGL | 799.0 | 12.36 (s, 1H), 11.12 (s, 1H), 8.71 (s, 1H), 8.50-8.41 (m, 1H), 8.40-8.33 (m, 2H), 8.16 (d, J = 7.6 Hz, 1H), 7.56 (s, 1H), 7.21-6.97 (m, 3H), 5.94 (s, 1H), 5.39 (m, 1H), 4.45 (m, 1H), 3.67 (s, 3H), 3.60-3.38 (m, 1H), 3.23-2.82 (m, 6H), 2.77-2.61 (m, 3H), 2.53-2.51 (m, 2H), 2.14 (m, 3H), 1.98 (m, 6H), 1.62 (s, 6H), 1.24 (m, 2H) |
| I-241 | AKP | AGL | 843.2 | 12.36 (s, 1H), 8.72 (s, 1H), 8.48-8.43 (m, 1H), 8.40-8.34 (m, 2H), 8.16 (d, J = 8.0 Hz, 1H), 7.58 (s, 1H), 6.99-6.92 (m, 2H), 6.87 (d, J = 5.6 Hz, 1H), 5.31 (d, J = 12.4 Hz, 1H), 4.49-4.34 (m, 1H), 3.55 (s, 3H), 2.93-2.78 (m, 5H), 2.71-2.64 (m, 1H), 2.64-2.56 (m, 1H), 2.53 (d, J = 1.6 Hz, 3H), 2.18-2.08 (m, 4H), 2.00-1.79 (m, 7H), 1.62 (s, 10H), 1.38-1.30 (m, 2H), 1.28-1.20 (m, 1H), 1.19-1.06 (m, 4H) |
| I-242 | APY | ATJ | 801.5 | 11.09 (s, 1H), 10.50 (s, 1H), 8.68 (s, 1H), 8.48-8.43 (m, 1H), 8.43-8.38 (m, 1H), 8.33 (s, 1H), 8.22-8.20 (m, 1H), 7.16 (s, 1H), 6.96 (d, J = 4.8 Hz, 2H), 6.89-6.84 (m, 1H), 5.36 (dd, J = 5.2, 12.4 Hz, 1H), 4.41-4.31 (m, 1H), 3.98 (s, 3H), 3.56 (s, 3H), 2.96-2.81 (m, 6H), 2.65-2.58 (m, 2H), 2.17-2.10 (m, 4H), 1.95-1.83 (m, 6H), 1.77-1.73 (m, 2H), 1.66-1.58 (m, 1H), 1.57-1.49 (m, 2H), 1.38-1.30 (m, 1H), 1.29-1.18 (m, 2H), 1.16-1.03 (m, 2H) |
| I-243 | AKP | ATJ | 815.6 | 11.08 (s, 1H), 10.54-10.44 (m, 1H), 8.72-8.64 (m, 1H), 8.50-8.43 (m, 1H), 8.43-8.36 (m, 1H), 8.31 (s, 1H), 8.21 (d, J = 7.6 Hz, 1H), 7.15 (s, 1H), 7.00-6.92 (m, 2H), 6.90-6.82 (m, 1H), 5.36 (dd, J = 5.2, 12.8 Hz, 1H), 4.40-4.29 (m, 1H), 3.97 (s, 3H), 3.54 (s, 3H), 2.90-2.78 (m, 5H), 2.72-2.62 (m, 2H), 2.11 (d, J = 7.6 Hz, 4H), 2.02-1.95 (m, 1H), 1.94-1.79 (m, 6H), 1.68-1.55 (m, 5H), 1.37-1.28 (m, 2H), 1.27-1.19 (m, 1H), 1.19-1.00 (m, 4H) |
| I-244 | AZF | ATJ | 811.6 | 11.11 (s, 1H), 10.50 (s, 1H), 8.69 (s, 1H), 8.49-8.43 (m, 1H), 8.43-8.37 (m, 1H), 8.32 (s, 1H), 8.21 (dd, J = 0.8, 8.0 Hz, 1H), 7.15 (s, 1H), 7.12 (d, J = 8.0 Hz, 1H), 7.09-7.05 (m, 1H), 7.03-6.97 (m, 1H), 5.38 (dd, J = 5.2, 12.8 Hz, 1H), 4.42-4.33 (m, 1H), 3.98 (s, 3H), 3.65 (s, 3H), 3.48-3.40 (m, 2H), 3.15-3.05 (m, 2H), 2.93-2.84 (m, 1H), 2.77-2.68 (m, 1H), 2.65-2.58 (m, 1H), 2.46-2.35 (m, 2H), 2.31-2.22 (m, 1H), 2.16-2.12 (m, 2H), 2.10-1.77 (m, 8H), 1.77-1.61 (m, 2H), 1.53-1.38 (m, 2H), 1.20-1.04 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-245 | WX | ATJ | 816.5 | 11.10 (s, 1H), 10.50 (s, 1H), 8.68 (s, 1H), 8.48-8.43 (m, 1H), 8.43-8.37 (m, 1H), 8.32 (s, 1H), 8.21 (d, J = 8.0 Hz, 1H), 7.15 (s, 1H), 7.07 (d, J = 8.0 Hz, 1H), 6.96 (t, J = 8.0 Hz, 1H), 6.87 (d, J = 8.0 Hz, 1H), 5.38 (dd, J = 5.2, 12.8 Hz, 1H), 4.38-4.30 (m, 1H), 3.98 (s, 3H), 3.68 (s, 3H), 3.61 (s, 2H), 2.88 (d, J = 9.2 Hz, 3H), 2.79-2.69 (m, 1H), 2.65-2.58 (m, 1H), 2.33-2.27 (m, 1H), 2.22 (d, J = 6.8 Hz, 2H), 2.18 (s, 3H), 2.11 (d, J = 10.5 Hz, 2H), 2.05-1.92 (m, 4H), 1.91-1.80 (m, 3H), 1.67-1.59 (m, 2H), 1.55-1.47 (m, 1H), 1.44-1.33 (m, 2H), 1.13-1.00 (m, 2H) |
| I-246 | AVW | ATJ | 787.5 | 11.09 (s, 1H), 10.50 (s, 1H), 8.68 (s, 1H), 8.48-8.44 (m, 1H), 8.43-8.37 (m, 1H), 8.32 (s, 1H), 8.21 (dd, J = 1.2, 7.6 Hz, 1H), 7.15 (s, 1H), 7.00-6.92 (m, 2H), 6.83 (dd, J = 1.2, 7.6 Hz, 1H), 5.37 (dd, J = 5.2, 12.8 Hz, 1H), 4.41-4.30 (m, 1H), 3.98 (s, 3H), 3.54 (s, 3H), 2.94-2.78 (m, 6H), 2.73-2.63 (m, 2H), 2.52 (d, J = 1.6 Hz, 2H), 2.21-2.10 (m, 4H), 2.05-1.80 (m, 8H), 1.63-1.60 (m, 3H), 1.55-1.46 (m, 1H), 1.38-1.26 (m, 2H), 1.16-1.03 (m, 2H) |
| I-247 | AQK | ATJ | 802.4 | 11.10 (s, 1H), 10.51 (s, 1H), 8.70 (s, 1H), 8.51-8.39 (m, 2H), 8.35 (s, 1H), 8.26-8.20 (m, 1H), 7.17 (s, 1H), 7.03-6.85 (m, 3H), 5.40-5.29 (m, 1H), 4.52-4.30 (m, 1H), 3.99 (s, 3H), 3.65 (s, 3H), 3.20-3.15 (m, 2H), 3.00-2.82 (m, 1H), 2.78-2.72 (m, 1H), 2.63-2.54 (m, 1H), 2.33-2.29 (m, 2H), 2.27 (s, 3H), 2.21-2.13 (m, 3H), 2.04-1.95 (m, 4H), 1.94-1.87 (m, 2H), 1.83-1.77 (m, 2H), 1.73-1.52 (m, 4H), 1.17-1.08 (m, 2H) |
| I-248 | AVW | AZH | 779.5 | 11.10 (s, 1H), 9.96 (s, 1H), 9.38 (dd, J = 1.2, 7.2 Hz, 1H), 8.88 (dd, J = 1.2, 4.4 Hz, 1H), 8.72 (s, 1H), 8.51 (s, 1H), 8.32 (s, 1H), 7.94 (s, 1H), 7.33 (dd, J = 4.4, 7.2 Hz, 1H), 7.24-6.90 (m, 3H), 6.82 (d, J = 6.8 Hz, 1H), 5.37 (dd, J = 5.2, 12.4 Hz, 1H), 4.55-4.44 (m, 1H), 3.54 (s, 3H), 2.93-2.77 (m, 5H), 2.73-2.59 (m, 2H), 2.18-2.14 (m, 4H), 2.03-1.83 (m, 7H), 1.63-1.61(m, 3H), 1.55-1.43 (m, 1H), 1.32-1.30 (m, 2H), 1.19-1.03 (m, 2H) |
| I-249 | AML | AYX | 843.5 | 12.34 (s, 1H), 11.11 (s, 1H), 8.76 (s, 1H), 8.33 (s, 1H), 8.01-7.93 (m, 2H), 7.65 (dd, J = 2.0, 6.8 Hz, 1H), 7.61-7.55 (m, 2H), 7.11-6.94 (m, 2H), 6.45 (d, J = 6.4 Hz, 1H), 5.92 (s, 1H), 5.06 (dd, J = 5.2, 12.8 Hz, 1H), 4.41 (s, 1H), 4.21-4.05 (m, 1H), 2.95-2.81 (m, 1H), 2.63-2.53 (m, 2H), 2.53-2.52 (m, 2H), 2.38-2.35 (m, 1H), 2.35-2.31 (m, 2H), 2.28-2.18 (m, 2H), 2.17-2.08 (m, 4H), 2.07-1.98 (m, 1H), 1.97-1.85 (m, 4H), 1.73-1.64 (m, 4H), 1.64 (s, 6H), 1.59-1.53 (m, 2H), 1.42 (s, 9H), 1.17-1.01 (m, 2H) |
| I-250 | ATC | AZE | 879.6 | 12.43 (s, 1H), 11.10 (s, 1H), 8.76 (s, 1H), 8.35 (s, 1H), 8.33-8.23 (m, 2H), 7.97 (d, J = 7.6 Hz, 1H), 7.65-7.51 (m, 2H), 7.10-6.96 (m, 2H), 6.48 (t, J = 6.0 Hz, 1H), 6.10 (s, 1H), 5.09-5.01 (m, 1H), 4.45-4.35 (m, 1H), 3.24-3.19 (m, 3H), 2.93-2.83 (m, 1H), 2.62-2.53 (m, 2H), 2.35-1.98 (m, 15H), 1.96-1.86 (m, 6H), 1.72-1.65 (m, 2H), 1.63 (s, 6H), 1.59-1.53 (m, 2H), 1.51-1.44 (m, 2H), 1.43-1.35 (m, 2H), 1.15-1.04 (m, 2H) |
| I-251 | AJF | AQO | 861.3 | 12.45 (s, 1H), 11.11 (s, 1H), 8.79 (s, 1H), 8.35 (s, 1H), 8.14-8.09 (m, 2H), 7.80-7.75 (m, 1H), 7.62-7.56 (m, 2H), 7.12 (d, J = 8.4 Hz, 1H), 7.03 (d, J = 6.8 Hz, 1H), 6.53-6.45 (m, 1H), 6.05 (s, 1H), 5.06 (dd, J = 5.2, 18.4 Hz, 1H), 4.48-4.37 (m, 1H), 3.32-3.30 (m, 2H), 2.94-2.84 (m, 1H), 2.64-2.54 (m, 4H), 2.17-2.03 (m, 6H), 1.97-1.84 (m, 7H), 1.81 (s, 3H), 1.76 (s, 3H), 1.66-1.63 (m, 6H), 1.61-1.55 (m, 3H), 1.54-1.48 (m, 4H), 1.26-1.02 (m, 3H) |
| I-257 | BCD | ATJ | 787.4 | 10.51 (s, 1H), 8.70 (s, 1H), 8.49-8.45 (m, 1H), 8.44-8.38 (m, 1H), 8.35 (s, 1H), 8.23 (dd, J = 0.4, 7.6 Hz, 1H), 7.17 (s, 1H), 7.08-6.98 (m, 3H), 5.45 (dd, J = 5.2, 13.2 Hz, 1H), 4.48-4.31 (m, 1H), 3.99 (s, 3H), 3.61 (s, 3H), 3.31 (s, 2H), 3.23-3.07 (m, 2H), 3.04 (s, 3H), 3.00-2.92 (m, 1H), 2.83-2.69 (m, 2H), 2.54-2.52 (m, 2H), 2.21-2.14 (m, 2H), 2.07-1.68 (m, 11H), 1.21-1.14 (m, 1H), 1.25-1.11 (m, 1H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-258 | AZK | BCF | 763.6 | 11.20-10.95 (m, 1H), 10.93 (s, 1H), 8.68 (s, 1H), 8.31 (s, 1H), 8.11-7.99 (m, 2H), 7.94 (d, J = 7.6 Hz, 1H), 7.15 (s, 1H), 7.06-6.95 (m, 3H), 5.47 (s, 1H), 5.38 (d, J = 12.4 Hz, 1H), 4.43-4.32 (m, 1H), 3.99 (s, 3H), 3.60 (s, 3H), 3.22 (d, J = 9.6 Hz, 1H), 2.99 (d, J = 10.4 Hz, 2H), 2.93-2.84 (m, 1H), 2.74-2.58 (m, 2H), 2.23-2.13 (m, 4H), 2.09 (s, 2H), 1.97 (d, J = 13.6 Hz, 3H), 1.94-1.86 (m, 2H), 1.76 (s, 4H), 1.70-1.62 (m, 1H), 1.58 (s, 6H), 1.20-1.06 (m, 2H) |
| I-259 | APZ | ATJ | 841.4 | 11.09 (s, 1H), 10.50 (s, 1H), 8.69 (s, 1H), 8.49-8.43 (m, 1H), 8.43-8.37 (m, 1H), 8.32 (s, 1H), 8.21 (dd, J = 0.8, 7.6 Hz, 1H), 7.14 (s, 1H), 7.03-6.92 (m, 2H), 6.88-6.81 (m, 1H), 5.36 (dd, J = 5.2, 12.4 Hz, 1H), 4.47-4.31 (m, 1H), 3.98 (s, 3H), 3.56 (s, 3H), 2.94-2.57 (m, 10H), 2.53-2.51 (m, 1H), 2.31-2.21 (m, 1H), 2.19-2.10 (m, 2H), 2.06-1.86 (m, 7H), 1.85-1.67 (m, 5H), 1.67-1.56 (m, 2H), 1.50-1.39 (m, 2H), 1.25-1.09 (m, 2H) |
| I-260 | AZI | ATJ | 745.2 | 11.11 (s, 1H), 10.51 (s, 1H), 8.72-8.67 (m, 1H), 8.49-8.38 (m, 2H), 8.34 (s, 1H), 8.22 (dd, J = 1.2, 7.6 Hz, 1H), 7.27 (s, 1H), 7.18-7.14 (m, 1H), 7.08 (q, J = 8.0 Hz, 2H), 5.38 (dd, J = 5.6, 12.8 Hz, 1H), 4.44-4.34 (m, 1H), 4.09 (s, 2H), 3.99 (s, 3H), 3.91-3.70 (m, 2H), 3.38 (s, 3H), 3.00-2.59 (m, 6H), 2.22-2.11 (m, 2H), 2.04-1.85 (m, 5H), 1.66-1.56 (m, 1H), 1.31-1.14 (m, 2H) |
| I-261 | AZL | ALU | 793.3 | 11.09 (s, 1H), 10.50 (s, 1H), 8.58 (s, 1H), 8.52-8.37 (m, 3H), 8.23 (d, J = 7.6 Hz, 1H), 8.00 (s, 1H), 7.43-7.08 (m, 2H), 7.05-6.89 (m, 2H), 5.35 (dd, J = 5.6, 12.8 Hz, 1H), 4.63-4.44 (m, 1H), 3.05 (d, J = 9.6 Hz, 3H), 2.94-2.85 (m, 1H), 2.78-2.54 (m, 4H), 2.41-2.07 (m, 7H), 2.05-1.92 (m, 5H), 1.83-1.67 (m, 5H), 1.25-1.08 (m, 2H) |
| I-262 | AZL | ATJ | 773.3 | 11.09 (s, 1H), 10.51 (s, 1H), 8.70 (s, 1H), 8.53-8.37 (m, 2H), 8.34 (s, 1H), 8.23 (dd, J = 0.8, 7.6 Hz, 1H), 7.23-7.08 (m, 2H), 7.06-6.89 (m, 2H), 5.35 (dd, J = 5.6, 12.8 Hz, 1H), 4.48-4.27 (m, 1H), 3.99 (s, 3H), 3.35 (s, 3H), 3.05 (d, J = 10.4 Hz, 2H), 2.95-2.86 (m, 1H), 2.75-2.56 (m, 3H), 2.35-2.25 (m, 2H), 2.22-2.06 (m, 4H), 2.03-1.85 (m, 5H), 1.84-1.65 (m, 5H), 1.23-1.04 (m, 2H) |
| I-263 | AZK | ALU | 793 | 11.09 (s, 1H), 10.49 (s, 1H), 8.57 (s, 1H), 8.52-8.36 (m, 3H), 8.22 (d, J = 7.6 Hz, 1H), 7.99 (s, 1H), 7.40-7.08 (m, 1H), 7.08-6.91 (m, 3H), 5.37 (m, 1H), 4.53 (m, 1H), 3.59 (s, 3H), 3.05-2.83 (m, 4H), 2.77-2.69 (m, 1H), 2.62 (m, 1H), 2.28-2.15 (m, 4H), 2.14-1.95 (m, 7H), 1.86-1.63 (m, 5H), 1.23-1.06 (m, 2H) |
| I-264 | AZI | ALU | 765.3 | 11.12 (s, 1H), 10.5 (s, 1H), 8.59 (s, 1H), 8.50 (s, 1H), 8.48-8.39 (m, 2H), 8.24 (dd, J = 1.2, 7.6 Hz, 1H), 8.00 (s, 1H), 7.40-7.09 (m, 4H), 5.39 (dd, J = 5.6, 12.8 Hz, 1H), 4.61-4.52 (m, 1H), 4.44 (s, 2H), 4.19-4.03 (m, 2H), 3.39 (s, 3H), 3.27-3.12 (m, 2H), 2.95-2.87 (m, 1H), 2.80-2.71 (m, 1H), 2.69-2.61 (m, 1H), 2.53 (d, J = 1.6 Hz, 1H), 2.22 (d, J = 9.6 Hz, 2H), 2.06-1.91 (m, 5H), 1.76 (d, J = 5.2 Hz, 1H), 1.37-1.21 (m, 2H) |
| I-265 | APY | AGL | 829.5 | 12.37 (s, 1H), 11.10 (s, 1H), 8.72 (s, 1H), 8.49-8.42 (m, 1H), 8.40-8.34 (m, 2H), 8.20-8.13 (m, 1H), 7.58 (s, 1H), 6.97 (s, 1H), 6.96 (s, 1H), 6.90-6.84 (m, 1H), 6.21-5.68 (m, 1H), 5.45-5.30 (m, 1H), 4.49-4.37 (m, 1H), 3.57 (s, 3H), 2.92-2.89 (m, 2H), 2.86-2.80 (m, 2H), 2.79-2.62 (m, 2H), 2.16 (s, 2H), 2.15 (m, 2H), 2.08-1.80 (m, 8H), 1.76 (d, J = 10.8 Hz, 2H), 1.70-1.64 (m, 1H), 1.63 (s, 6H), 1.57-1.50 (m, 2H), 1.41-1.31 (m, 1H), 1.31-1.21 (m, 2H), 1.17-1.06 (m, 2H) |
| I-266 | BDS | ALU | 837.3 | 11.18-10.97 (m, 1H), 10.50 (s, 1H), 8.56 (s, 1H), 8.50-8.41 (m, 3H), 8.23 (dd, J = 1.2, 7.6 Hz, 1H), 7.99 (s, 1H), 7.25 (s, 1H), 7.01-6.92 (m, 3H), 5.38 (dd, J = 5.6, 12.8 Hz, 1H), 4.53-4.46 (m, 1H), 3.67 (t, J = 6.8 Hz, 2H), 3.60 (s, 3H), 3.45-3.42 (m, 1H), 3.14 (t, J = 6.8 Hz, 2H), 2.95-2.85 (m, 1H), 2.78-2.69 (m, 1H), 2.65-2.60 (m, 1H), 2.18-2.14 (m, 2H), 2.10-2.07 (m, 2H), 2.02-1.89 (m, 8H), 1.78 (d, J = 10.4 Hz, 2H), 1.70-1.54 (m, 2H), 1.44-1.38 (m, 2H), 1.14-1.06 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-267 | BDS | AGL | 845.5 | 12.37 (s, 1H), 11.09 (s, 1H), 8.72 (s, 1H), 8.48-8.43 (m, 1H), 8.39-8.35 (m, 2H), 8.16 (dd, J = 0.8, 7.6 Hz, 1H), 7.58 (s, 1H), 7.01-6.91 (m, 3H), 5.94 (s, 1H), 5.38 (dd, J = 5.6, 12.8 Hz, 1H), 4.46-4.35 (m, 1H), 3.67 (t, J = 6.8 Hz, 2H), 3.60 (s, 3H), 3.50-3.42 (m, 1H), 3.14 (t, J = 6.8 Hz, 2H), 2.95-2.85 (m, 1H), 2.78-2.69 (m, 1H), 2.68-2.58 (m, 2H), 2.18-2.06 (m, 5H), 2.04-1.98 (m, 2H), 1.90 (d, J = 11.2 Hz, 5H), 1.81-1.74 (m, 2H), 1.62 (s, 7H), 1.42 (d, J = 5.2 Hz, 2H), 1.14-1.05 (m, 2H) |
| I-268 | AVZ | AXS | 775.1 | 11.09 (s, 1H), 10.70 (s, 1H), 8.69 (s, 1H), 8.30 (s, 1H), 8.13 (s, 1H), 7.98-7.94 (m, 2H), 7.60-7.54 (m, 2H), 7.13-7.02 (m, 3H), 6.61 (m, 1H), 5.07 (m, 1H), 4.36 (m, 1H), 3.99 (s, 3H), 3.20 (m, 1H), 3.17 (m, 2H), 2.62 (m, 2H), 2.57 (m, 3H), 2.50 (m, 3H), 2.15 (m, 2H), 1.97-1.91 (m, 10H), 1.88-1.86 (m, 5H), 1.08-1.03 (m, 5H) |
| I-269 | AZP | ALU | 777.2 | 11.09 (br s, 1H), 10.49 (s, 1H), 8.56 (s, 1H), 8.49-8.44 (m, 2H), 8.43-8.38 (m, 1H), 8.22 (dd, J = 1.2, 7.6 Hz, 1H), 7.99 (s, 1H), 7.40-7.17 (m, 1H), 7.16-7.10 (m, 2H), 7.05-7.00 (m, 1H), 5.40 (dd, J = 5.2, 12.8 Hz, 1H), 4.53 (t, J = 11.6 Hz, 1H), 3.68 (s, 3H), 3.63-3.61 (m, 2H), 2.94-2.84 (m, 1H), 2.78-2.62 (m, 2H), 2.35-2.29 (m, 5H), 2.18 (d, J = 92 Hz, 2H), 2.05-1.93 (m, 5H), 1.63 (d, J = 7.2 Hz, 1H), 1.20-1.10 (m, 2H) |
| I-270 | AZF | AGL | 839.4 | 12.37 (s, 1H), 11.12 (s, 1H), 8.72 (s, 1H), 8.47-8.44 (m, 1H), 8.40-8.34 (m, 2H), 8.17 (dd, J = 1.2, 8.0 Hz, 1H), 7.58 (s, 1H), 7.14 (d, J = 8.0 Hz, 1H), 7.11-7.06 (m, 1H), 7.04-6.98 (m, 1H), 5.95 (s, 1H), 5.40 (dd, J = 5.2, 12.4 Hz, 1H), 4.49-4.40 (m, 1H), 3.66 (s, 3H), 3.30-3.09 (m, 4H), 2.95-2.85 (m, 1H), 2.78-2.59 (m, 3H), 2.56-2.52 (m, 3H), 2.16 (d, J = 8.8 Hz, 2H), 2.05-1.84 (m, 7H), 1.81-1.67 (m, 2H), 1.63 (s, 6H), 1.57-1.43 (m, 2H), 1.19 (m, 2H) |
| I-271 | AZP | AGL | 785.4 | 12.36 (s, 1H), 11.13 (s, 1H), 8.72 (s, 1H), 8.47-8.43 (m, 1H), 8.39-8.34 (m, 2H), 8.16 (dd, J = 0.8, 7.6 Hz, 1H), 7.57 (s, 1H), 7.26-7.01 (m, 3H), 5.94 (s, 1H), 5.41 (dd, J = 5.2, 12.8 Hz, 1H), 4.50-4.42 (m, 1H), 3.68 (s, 4H), 2.99-2.80 (m, 2H), 2.79-2.61 (m, 2H), 2.44-2.27 (m, 4H), 2.23-2.09 (m, 3H), 2.08-1.91 (m, 6H), 1.62 (s, 6H), 1.27-1.09 (m, 2H) |
| I-272 | AVU | ATJ | 815.5 | 11.11 (s, 1H), 10.51 (s, 1H), 8.69 (s, 1H), 8.49-8.44 (m, 1H), 8.43-8.38 (m, 1H), 8.32 (s, 1H), 8.22 (d, J = 7.6 Hz, 1H), 7.15 (s, 1H), 7.02-6.93 (m, 2H), 6.81 (dd, J = 1.2, 7.2 Hz, 1H), 5.38 (dd, J = 5.6, 12.4 Hz, 1H), 4.39-4.30 (m, 1H), 3.98 (s, 3H), 3.55 (s, 3H), 2.96-2.84 (m, 1H), 2.79-2.67 (m, 3H), 2.63 (d, J = 17.6 Hz, 1H), 2.48-2.42 (m, 1H), 2.37-2.31 (m, 2H), 2.26 (s, 3H), 2.16-2.08 (m, 2H), 2.03-1.83 (m, 5H), 1.75 (d, J = 9.6 Hz, 4H), 1.58-1.40 (m, 2H), 1.32-1.19 (m, 2H), 1.14-1.01 (m, 4H) |
| I-273 | AFJ | BDT | 773.5 | 11.09 (s, 1H), 10.59 (s, 1H), 8.75 (d, J = 4.8 Hz, 1H), 8.71 (s, 1H), 8.30 (s, 1H), 8.20 (d, J = 7.7 Hz, 1H), 8.10 (dt, J = 1.6, 7.8 Hz, 1H), 7.69 (ddd, J = 1.4, 4.8, 7.6 Hz, 1H), 7.60-7.55 (m, 1H), 7.14 (s, 1H), 7.11 (d, J = 8.6 Hz, 1H), 7.03 (d, J = 7.0 Hz, 1H), 6.47 (t, J = 5.8 Hz, 1H), 5.05 (dd, J = 5.4, 12.8 Hz, 1H), 4.39-4.29 (m, 1H), 3.99 (s, 3H), 2.93-2.82 (m, 1H), 2.63-2.52 (m, 7H), 2.30-2.19 (m, 3H), 2.15-2.07 (m, 4H), 2.06-1.99 (m, 1H), 1.94-1.81 (m, 6H), 1.62-1.46 (m, 7H), 1.14-1.01 (m, 2H) |
| I-274 | APB | ATJ | 813.4 | 11.10 (s, 1H), 10.50 (s, 1H), 8.68 (s, 1H), 8.48-8.36 (m, 2H), 8.32 (s, 1H), 8.22 (dd, J = 0.8, 7.6 Hz, 1H), 7.57 (dd, J = 7.4, 8.4 Hz, 1H), 7.15 (s, 1H), 7.09 (d, J = 8.6 Hz, 1H), 7.03 (d, J = 7.0 Hz, 1H), 6.53 (t, J = 5.8 Hz, 1H), 5.05 (dd, J = 5.4, 12.8 Hz, 1H), 4.40-4.28 (m, 1H), 3.98 (s, 3H), 3.32-3.28 (m, 6H), 2.94-2.82 (m, 1H), 2.64-2.52 (m, 3H), 2.42 (dd, J = 7.6, 15.2 Hz, 2H), 2.26-2.16 (m, 2H), 2.11 (br d, J = 8.8 Hz, 2H), 2.06-1.99 (m, 1H), 1.94-1.75 (m, 6H), 1.49-1.31 (m, 1H), 1.20-1.03 (m, 2H) |
| I-275 | APZ | BDU | 807.1 | 11.09 (s, 1H), 10.67 (s, 1H), 8.52 (d, J = 10.0 Hz, 2H), 8.04-7.90 (m, 3H), 7.57 (dd, J = 6.4, 2.4 Hz, 1H), 7.44-7.05 (m, 1H), 6.95 (d, J = 4.8 Hz, 2H), 6.87-6.79 (m, |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | 1H), 5.36 (dd, J = 12.8, 5.2 Hz, 1H), 4.49 (m, 1H), 3.55 (s, 3H), 2.93-2.84 (m, 1H), 2.83-2.76 (m, 2H), 2.73-2.62 (m, 2H), 2.60 (s, 3H), 2.54-2.52 (m, 1H), 2.25 (m, 3H), 2.19-2.07 (m, 5H), 1.92 (m, 7H), 1.76-1.61 (m, 3H), 1.56 (m, 2H), 1.51-1.43 (m, 2H), 1.43-1.33 (m, 2H), 1.16-1.02 (m, 2H) |
| I-276 | APZ | APG | 815.6 | 12.40 (s, 1H), 11.10 (s, 1H), 8.71 (s, 1H), 8.33 (s, 1H), 7.98-7.89 (m, 2H), 7.56 (s, 1H), 7.52-7.45 (m, 1H), 6.98-6.95 (m, 2H), 6.87-6.84 (m, 1H), 5.91 (s, 1H), 5.36 (dd, J = 5.2, 12.4 Hz, 1H), 4.46-4.38 (m, 1H), 3.56 (s, 3H), 2.83-2.60 (m, 10H), 2.43 (s, 3H), 2.39-2.21 (m, 2H), 2.17-2.06 (m, 3H), 2.04-1.80 (m, 7H), 1.71-1.52 (m, 11H), 1.51-1.49 (m, 2H), 1.45-1.36 (m, 2H), 1.19-1.01 (m, 2H) |
| I-277 | APZ | BDV | 793.4 | 11.22-10.95 (m, 1H), 10.59 (s, 1H), 8.75 (d, J = 4.8 Hz, 1H), 8.54 (s, 1H), 8.42 (s, 1H), 8.20 (d, J = 7.6 Hz, 1H), 8.10 (t, J = 7.6 Hz, 1H), 7.97 (s, 1H), 7.71 (d, J = 7.6 Hz, 1H), 7.41-7.09 (m, 1H), 6.96 (d, J = 4.4 Hz, 2H), 6.88-6.81 (m, 1H), 5.36 (d, J = 12.4 Hz, 1H), 4.56-4.43 (m, 1H), 3.56 (s, 3H), 2.91-2.60 (m, 5H), 2.34-2.07 (m, 9H), 2.01-1.86 (m, 7H), 1.74-1.66 (m, 2H), 1.65-1.53 (m, 3H), 1.48 (t, J = 5.2 Hz, 2H), 1.38 (d, J = 11.2 Hz, 2H), 1.17-1.02 (m, 2H) |
| I-278 | ARW | ALU | 875.4 | 11.10 (s, 1H), 10.50-10.48 (m, 1H), 8.56 (s, 1H), 8.49-8.41 (m, 3H), 8.24 (s, 1H), 7.99 (s, 1H), 7.40-7.09 (m, 1H), 6.97 (s, 2H), 6.86-6.82 (m, 1H), 5.37 (dd, J = 5.2, 12.8 Hz, 1H), 4.53-4.46 (m, 1H), 3.55 (s, 3H), 3.07-3.01 (m, 2H), 2.88 (dd, J = 4.8, 12.4 Hz, 1H), 2.69-2.59 (m, 2H), 2.26-2.16 (m, 8H), 2.00-1.81 (m, 9H), 1.59-1.42 (m, 6H), 1.28-1.06 (m, 6H) |
| I-279 | BDW | AGL | 844.3 | 12.36 (s, 1H), 11.10 (s, 1H), 8.70 (s, 1H), 8.49-8.41 (m, 1H), 8.40-8.31 (m, 2H), 8.20-8.09 (m, 1H), 7.56 (s, 1H), 7.07 (d, J = 8.0 Hz, 1H), 6.96 (t, J = 7.6 Hz, 1H), 6.87 (d, J = 7.2 Hz, 1H), 5.93 (s, 1H), 5.38 (dd, J = 12.8, 5.2 Hz, 1H), 4.46-4.32 (m, 1H), 3.68 (s, 3H), 3.64-3.56 (m, 2H), 2.95-2.81 (m, 3H), 2.78-2.62 (m, 2H), 2.52 (s, 1H), 2.21 (d, J = 12 Hz, 2H), 2.19-2.15 (m, 3H), 2.12 (d, J = 10.0 Hz, 2H), 2.06-1.97 (m, 2H), 1.97-1.85 (m, 5H), 1.61 (s, 8H), 1.50 (s, 1H), 1.44-1.30 (m, 2H), 1.13-1.00 (m, 2H) |
| I-281 | BDY | ATJ | 786.0 | 11.09 (s, 1H), 10.50 (s, 1H), 8.75-8.64 (m, 1H), 8.49-8.44 (m, 1H), 8.43-8.36 (m, 1H), 8.33 (s, 1H), 8.21 (dd, J = 7.6, 1.0 Hz, 1H), 7.15 (s, 1H), 7.00-6.91 (m, 2H), 6.81 (m, 1H), 5.34 (m, 1H), 4.44-4.33 (m, 1H), 3.98 (s, 3H), 3.78 (m, 1H), 3.62 (d, J = 1.2 Hz, 3H), 3.53 (m, 3H), 3.06 (m, 1H), 2.96-2.82 (m, 1H), 2.80-2.60 (m, 4H), 2.15 (m, 2H), 2.07-1.96 (m, 3H), 1.95-1.80 (m, 4H), 1.51 (m, 1H), 1.16 (m, 2H) |
| I-282 | BDY | AGL | 814.0 | 12.36 (s, 1H), 11.09 (s, 1H), 8.78-8.66 (m, 1H), 8.48-8.42 (m, 1H), 8.41-8.32 (m, 2H), 8.16 (d, J = 7.6 Hz, 1H), 7.65-7.50 (m, 1H), 6.98 (m, 2H), 6.84 (m, 1H), 5.94 (s, 1H), 5.34 (m, 1H), 4.62-4.35 (m, 1H), 3.85 (m, 2H), 3.63 (d, J = 1.2 Hz, 3H), 3.57 (m, 1H), 3.13 (m, 1H), 2.89 (m, 2H), 2.77-2.61 (m, 5H), 2.17 (m, 2H), 2.10-1.89 (m, 7H), 1.73-1.66 (m, 1H), 1.62 (s, 6H), 1.29-1.11 (m, 2H) |
| I-283 | BFL | ATJ | 816.5 | 10.50 (s, 1H), 8.69 (s, 1H), 8.49-8.44 (m, 1H), 8.43-8.38 (m, 1H), 8.34 (s, 1H), 8.22 (dd, J = 1.2, 7.6 Hz, 1H), 7.16 (s, 1H), 6.99-6.94 (m, 1H), 6.93-6.89 (m, 1H), 6.87 (d, J = 7.6 Hz, 1H), 5.41 (dd, J = 5.6, 12.8 Hz, 1H), 4.43-4.32 (m, 1H), 3.98 (s, 3H), 3.65 (s, 3H), 3.16 (d, J = 11.6 Hz, 2H), 3.03 (s, 3H), 3.00-2.91 (m, 1H), 2.82-2.68 (m, 4H), 2.45-2.41 (m, 1H), 2.32-2.28 (m, 2H), 2.26 (s, 3H), 2.18-2.11 (m, 2H), 2.04-1.87 (m, 5H), 1.86-1.77 (m, 2H), 1.72-1.61 (m, 2H), 1.59-1.50 (m, 1H), 1.17-1.05 (m, 2H) |
| I-284 | BDZ | ATJ | 800.1 | 11.09 (s, 1H), 10.51 (s, 1H), 8.70 (s, 1H), 8.50-8.45 (m, 1H), 8.44-8.38 (m, 1H), 8.35 (s, 1H), 8.23 (d, J = 7.6 Hz, 1H), 7.17 (s, 1H), 6.94-6.87 (m, 1H), 6.81-6.69 (m, 2H), 5.41-5.28 (m, 1H), 4.45-4.29 (m, 1H), 3.99 (s, 3H), 3.77 (s, 2H), 3.71 (s, 3H), 2.81-2.57 (m, 5H), 2.44 (d, J = 9.2 Hz, 1H), 2.36-2.11 (m, 5H), 2.04-1.80 (m, 9H), 1.57 (s, 1H), 1.29-1.04 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-285 | BDZ | AGL | 828.1 | 12.37 (s, 1H), 11.09 (s, 1H), 8.72 (s, 1H), 8.46 (d, J = 8.4 Hz, 1H), 8.40-8.35 (m, 2H), 8.19-8.15 (m, 1H), 7.58 (s, 1H), 6.94-6.86 (m, 1H), 6.80-6.68 (m, 1H), 5.95 (s, 1H), 5.40-5.30 (m, 1H), 4.53-4.39 (m, 1H), 3.78 (s, 2H), 3.71 (s, 3H), 2.80-2.74 (m, 1H), 2.69-2.66 (m, 1H), 2.47-2.40 (m, 4H), 2.27-2.13 (m, 5H), 2.04-1.80 (m, 10H), 1.63 (s, 6H), 1.26-1.11 (m, 3H) |
| I-286 | ATH | BFM | 782.5 | 11.10 (s, 1H), 8.36 (s, 1H), 8.21 (d, J = 8.0 Hz, 1H), 7.80-7.69 (m, 2H), 7.67 (s, 1H), 7.62-7.48 (m, 2H), 7.28 (d, J = 7.2 Hz, 1H), 7.14 (s, 1H), 7.04 (dd, J = 7.6, 18.8 Hz, 2H), 6.65 (d, J = 7.6 Hz, 1H), 6.48 (t, J = 5.2 Hz, 1H), 5.05 (dd, J = 5.2, 12.8 Hz, 1H), 4.40 (t, J = 11.2 Hz, 1H), 3.73 (s, 3H), 3.26 (s, 2H), 3.24-3.19 (m, 2H), 3.16 (s, 2H), 2.94-2.83 (m, 1H), 2.64-2.52 (m, 2H), 2.32 (d, J = 6.0 Hz, 2H), 2.27-2.19 (m, 2H), 2.19-2.07 (m, 3H), 2.06-1.99 (m, 1H), 1.95-1.82 (m, 4H), 1.81-1.73 (m, 2H), 1.64 (q, J = 6.8 Hz, 2H), 1.37 (d, J = 8.0 Hz, 1H), 1.18-1.02 (m, 2H) |
| I-287 | ATH | BEB | 869.5 | 12.48 (s, 1H), 11.08 (m, 1H), 8.53 (s, 1H), 8.48-8.43 (m, 1H), 8.38 (t, J = 7.6 Hz, 1H), 8.17 (d, J = 7.6 Hz, 1H), 7.64-7.49 (m, 2H), 7.11-6.98 (m, 2H), 6.48 (m, 1H), 5.86 (s, 1H), 5.05 (dd, J = 12.8, 5.6 Hz, 1H), 3.80-3.62 (m, 3H), 3.25-3.19 (m, 2H), 3.11 (s, 2H), 3.01 (s, 2H), 2.95-2.81 (m, 2H), 2.63-2.54 (m, 3H), 2.24-2.11 (m, 5H), 2.07-1.99 (m, 1H), 1.93 (m, 2H), 1.82 (m, 2H), 1.78-1.71 (m, 2H), 1.64 (m, 2H), 1.60 (s, 6H), 1.57-1.50 (m, 1H), 1.30 (m, 1H), 1.16-0.99 (m, 2H) |
| I-289 | AMZ | ATJ | 858.4 | 11.11 (s, 1H), 10.51 (s, 1H), 8.69 (s, 1H), 8.50-8.45 (m, 1H), 8.44-8.38 (m, 1H), 8.33 (s, 1H), 8.23 (d, J = 7.6 Hz, 1H), 7.16 (s, 1H), 7.10 (d, J = 8.0 Hz, 1H), 6.98 (t, J = 7.6 Hz, 1H), 6.93-6.87 (m, 1H), 5.39 (dd, J = 5.2, 12.4 Hz, 1H), 4.43-4.29 (m, 1H), 3.99 (s, 3H), 3.69 (s, 3H), 3.61 (d, J = 14.4 Hz, 4H), 2.95-2.84 (m, 2H), 2.78-2.59 (m, 5H), 2.35-2.28 (m, 5H), 2.17-2.11 (m, 2H), 2.05-1.99 (m, 1H), 1.91 (t, J = 10.4 Hz, 6H), 1.73-1.50 (m, 4H), 1.19-1.09 (m, 2H) |
| I-290 | AOQ | AZD | 931.4 | 12.32 (s, 1H), 11.09 (s, 1H), 8.73 (s, 1H), 8.50-8.40 (m, 2H), 8.35 (s, 1H), 8.27 (d, J = 7.6 Hz, 1H), 7.66-7.48 (m, 2H), 7.07 (d, J = 7.2 Hz, 1H), 6.92 (d, J = 8.4 Hz, 1H), 6.50 (d, J = 5.6 Hz, 1H), 5.91 (s, 1H), 5.09-5.00 (m, 1H), 4.47-4.35 (m, 1H), 4.21-4.08 (m, 2H), 3.36 (d, J = 6.4 Hz, 4H), 2.93-2.82 (m, 1H), 2.62-2.54 (m, 1H), 2.54-2.52 (m, 1H), 2.43-2.19 (m, 7H), 2.15 (s, 3H), 2.14-2.11 (m, 2H), 2.05-1.85 (m, 5H), 1.69-1.63 (m, 2H), 1.61 (s, 6H), 1.16-1.02 (m, 2H) |
| I-291 | AML | AZD | 913.1 | 12.32 (s, 1H), 11.10 (s, 1H), 8.74 (s, 1H), 8.49-8.40 (m, 2H), 8.36 (s, 1H), 8.27 (d, J = 7.6 Hz, 1H), 7.61-7.55 (m, 2H), 7.06 (d, J = 6.8 Hz, 1H), 7.00 (d, J = 8.8 Hz, 1H), 6.45 (d, J = 6.4 Hz, 1H), 5.91 (s, 1H), 5.09-5.02 (m, 1H), 4.46-4.35 (m, 1H), 4.16-4.08 (m, 1H), 2.94-2.83 (m, 1H), 2.63-2.55 (m, 1H), 2.55-2.52 (m, 1H), 2.48-2.44 (m, 1H), 2.39-2.29 (m, 4H), 2.29-2.18 (m, 2H), 2.13-2.12 (m, 4H), 2.06-1.99 (m, 1H), 1.97-1.83 (m, 4H), 1.72-1.64 (m, 4H), 1.62 (s, 6H), 1.57 (d, J = 4.8 Hz, 2H), 1.16-1.03 (m, 2H); $^{19}$F NMR (376 MHz, DMSO-$d_6$) δ 81.10-79.27 (m, 1F), 54.16 (d, J = 160 Hz, 4F) |
| I-292 | AUK | BBZ | 838.4 | 11.09 (s, 1H), 10.68 (s, 1H), 8.67 (s, 1H), 8.34-8.27 (m, 2H), 8.03 (dd, J = 2.4, 6.4 Hz, 1H), 7.57 (dd, J = 7.2, 8.4 Hz, 1H), 7.48 (s, 1H), 7.11 (d, J = 8.8 Hz, 1H), 7.01 (d, J = 7.2 Hz, 1H), 6.56 (t, J = 6.0 Hz, 1H), 5.05 (dd, J = 5.6, 12.8 Hz, 1H), 4.00 (s, 3H), 3.11-3.17 (m, 4H), 3.04 (s, 2H), 2.93-2.84 (m, 2H), 2.62-2.52 (m, 2H), 2.47-2.43 (m, 2H), 2.21-2.10 (m, 5H), 2.06-2.00 (m, 1H), 1.93-1.80 (m, 4H), 1.69-1.60 (m, 2H), 1.60-1.48 (m, 3H), 1.42-1.29 (m, 3H), 1.14-0.90 (m, 4H) |
| I-296 | ATH | AZV | 881.5 | 11.11 (s, 1H), 10.40 (s, 1H), 8.79 (s, 1H), 8.39-8.24 (m, 3H), 7.98 (d, J = 8.4 Hz, 1H), 7.60 (dd, J = 7.2, 8.4 Hz, 1H), 7.13-7.00 (m, 3H), 6.49 (d, J = 5.6 Hz, 1H), 5.06 (dd, J = 5.2, 12.8 Hz, 1H), 4.82-4.70 (m, 1H), 4.36 (d, J = 11.6 Hz, 1H), 3.90 (s, 2H), 3.85-3.62 (m, 4H), 3.23 (d, J = 6.4 Hz, 2H), 2.94-2.85 (m, 1H), 2.75 (d, J = 2.0 Hz, 2H), 2.70-2.54 (m, 2H), 2.36-2.28 (m, |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | 2H), 2.23-2.13 (m, 3H), 2.12 (s, 2H), 2.09-2.00 (m, 2H), 1.93-1.78 (m, 6H), 1.66 (d, J = 6.8 Hz, 2H), 1.59-1.47 (m, 1H), 1.34 (s, 6H), 1.23-1.10 (m, 2H) |
| I-297 | BEE | BEG | 924.3 | 11.06 (s, 1H), 10.85 (s, 1H), 8.77 (s, 1H), 8.55-8.51 (m, 1H), 8.50-8.45 (m, 1H), 8.33 (s, 1H), 8.19 (s, 1H), 7.55 (d, J = 8.4 Hz, 1H), 7.44 (s, 1H), 7.10 (t, J = 4.8 Hz, 1H), 6.94 (s, 1H), 6.85 (dd, J = 1.6, 8.4 Hz, 1H), 5.03 (dd, J = 5.2, 12.8 Hz, 1H), 4.43-4.31 (m, 1H), 3.28 (s, 4H), 3.17-3.14 (m, 2H), 2.88-2.82 (m, 4H), 2.61-2.55 (m, 1H), 2.42-2.36 (m, 3H), 2.27-2.20 (m, 2H), 2.14-2.07 (m, 2H), 2.03-1.95 (m, 1H), 1.91-1.84 (m, 6H), 1.80-1.73 (m, 5H), 1.67-1.52 (m, 3H), 1.46-1.34 (m, 1H), 1.18-1.04 (m, 2H) |
| I-298 | BBW | AGL | 828.5 | 12.36 (s, 1H), 11.09 (s, 1H), 8.71 (s, 1H), 8.45 (d, J = 7.6 Hz, 1H), 8.40-8.34 (m, 2H), 8.15 (d, J = 8.8 Hz, 1H), 7.57 (s, 1H), 7.12 (d, J = 7.6 Hz, 1H), 7.01 (t, J = 7.6 Hz, 1H), 6.92 (d, J = 7.6 Hz, 1H), 5.95 (s, 1H), 5.35 (dd, J = 5.6, 12.8 Hz, 1H), 4.51-4.40 (m, 1H), 3.73-3.70 (m, 3H), 3.14 (d, J = 9.6 Hz, 2H), 2.93-2.82 (m, 3H), 2.77-2.63 (m, 2H), 2.37 (s, 2H), 2.17 (d, J = 9.6 Hz, 2H), 2.07 (d, J = 11.6 Hz, 2H), 2.01-1.89 (m, 7H), 1.62 (s, 7H), 1.28-1.14 (m, 2H), 1.12-1.10 (m, 1H) |
| I-299 | APZ | AZH | 833.5 | 11.09 (s, 1H), 9.96 (s, 1H), 9.38 (dd, J = 1.6, 6.8 Hz, 1H), 8.88 (dd, J = 1.6, 4.4 Hz, 1H), 8.72 (s, 1H), 8.51 (s, 1H), 8.32 (s, 1H), 8.21 (s, 1H), 7.94 (s, 1H), 7.42-7.04 (m, 2H), 6.99-6.91 (m, 2H), 6.89-6.81 (m, 1H), 5.36 (dd, J = 5.6, 12.8 Hz, 1H), 4.55-4.43 (m, 1H), 3.55 (s, 4H), 2.94-2.78 (m, 3H), 2.75-2.62 (m, 2H), 2.29-2.10 (m, 8H), 2.02-1.89 (m, 7H), 1.75-1.66 (m, 2H), 1.57 (s, 2H), 1.48-1.38 (m, 4H), 1.19-1.00 (m, 2H) |
| I-300 | AKP | ALU | 835.6 | 11.10 (s, 1H), 10.50 (s, 1H), 8.55 (s, 1H), 8.50-8.37 (m, 3H), 8.22 (dd, J = 0.8, 7.6 Hz, 1H), 7.99 (s, 1H), 7.41-7.09 (m, 1H), 7.02-6.83 (m, 3H), 5.37 (dd, J = 5.2, 12.4 Hz, 1H), 4.52 (t, J = 11.6 Hz, 1H), 3.55 (s, 3H), 3.13 (d, J = 1.2 Hz, 4H), 2.98-2.81 (m, 3H), 2.78-2.61 (m, 2H), 2.41-2.24 (m, 2H), 2.17 (m, 2H), 2.05-1.86 (m, 5H), 1.85-1.53 (m, 5H), 1.46-1.07 (m, 7H) |
| I-302 | BBC | AJB | 898.0 | 11.09 (s, 1H), 9.50 (d, J = 6.0 Hz, 1H), 8.78 (d, J = 7.6 Hz, 1H), 8.38 (s, J = 2.8 Hz, 1H), 8.26 (m, 1H), 8.16 (s, 1H), 7.59 (m, 1H), 7.09-7.02 (m, 3H), 6.85-6.44 (m, 2H), 5.27-5.02 (m, 2H), 4.78 (m, 1H), 4.12 (m, 1H), 3.80-3.59 (m, 6H), 2.60 (m, 2H), 2.50 (m, 4H), 2.00 (m, 10H), 1.98-1.67 (m, 11H), 1.11 (m, 3H), 1.02 (m, 2H) |
| I-303 | AOQ | ATJ | 845.5 | 11.10 (s, 1H), 10.50 (s, 1H), 8.68 (s, 1H), 8.46 (d, J = 7.6 Hz, 1H), 8.40 (t, J = 7.6 Hz, 1H), 8.32 (s, 1H), 8.21 (dd, J = 0.8, 7.6 Hz, 1H), 7.58 (dd, J = 7.2, 8.4 Hz, 1H), 7.14 (s, 1H), 7.07 (d, J = 7.2 Hz, 1H), 6.91 (d, J = 8.4 Hz, 1H), 6.50 (d, J = 6.0 Hz, 1H), 5.05 (dd, J = 5.2, 12.8 Hz, 1H), 4.42-4.31 (m, 1H), 4.21-4.09 (m, 2H), 3.97 (s, 3H), 2.92-2.82 (m, 1H), 2.63-2.51 (m, 3H), 2.48-2.34 (m, 5H), 2.29-2.17 (m, 7H), 2.16-2.09 (m, 2H), 2.06-1.98 (m, 1H), 1.95-1.83 (m, 4H), 1.70-1.64 (m, 2H), 1.63-1.54 (m, 1H), 1.17-1.03 (m, 2H) |
| I-304 | AJH | APG | 833.6 | 12.39 (s, 1H), 11.30-10.82 (m, 1H), 8.69 (s, 1H), 8.33 (s, 1H), 8.01-7.86 (m, 2H), 7.67-7.44 (m, 4H), 7.14-7.01 (m, 2H), 6.68 (m, 1H), 5.92 (s, 1H), 5.05 (m, 1H), 4.48-4.30 (m, 1H), 3.22 (d, J = 6.38 Hz, 3H), 2.97-2.70 (m, 6H), 2.60-2.58 (m, 5H), 2.16-1.63 (m, 23 H), 1.18-1.04 (m, 4H) |
| I-305 | AQS | AWF | 849.6 | 11.10 (s, 1H), 10.80 (s, 1H), 8.67 (s, 1H), 8.32 (s, 1H), 8.21-8.11 (m, 2H), 7.90-7.83 (m, 1H), 7.65-7.56 (m, 1H), 7.15 (s, 1H), 7.10 (d, J = 7.0 Hz, 1H), 6.91 (d, J = 4.0 Hz, 1H), 6.50 (d, J = 5.8 Hz, 1H), 5.07 (dd, J = 5.6, 12.8 Hz, 1H), 4.39-4.29 (m, 2H), 4.12-4.11 (m, 1H), 3.99 (s, 3H), 2.89-2.73 (m, 2H), 2.72 (s, 3H), 2.36-2.33 (m, 2H), 2.18-2.14 (m, 1H), 2.12-2.10 (m, 2H), 1.90-1.84 (m, 4H), 1.82-1.78 (m, 3H), 1.77-1.76 (m, 5H), 1.74 (s, 3H), 1.68 (s, 3H), 1.52-1.45 (m, 1H), 1.22-1.11 (m, 2H), 1.09-1.05 (m, 2H) |
| I-306 | AOV | AQO | 835.1 | 12.46 (d, J = 1.6 Hz, 1H), 11.13 (s, 1H), 9.50-9.29 (m, 1H), 8.81 (s, 1H), 8.45-8.03 (m, 3H), 7.85-7.49 (m, 3H), 7.29-6.96 (m, 2H), 6.42-5.91 (m, 2H), 5.18-4.96 (m, 1H), 4.61-4.38 (m, 1H), 3.67-3.59 (m, 2H), 3.21-3.09 |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | (m, 2H), 3.01-2.84 (m, 3H), 2.80 (s, 3H), 2.16 (dd, J = 1.2, 2.8 Hz, 7H), 2.07-1.88 (m, 6H), 1.84-1.75 (m, 6H), 1.65 (s, 6H), 1.53-1.22 (m, 5H) |
| I-308 | AVZ | AYY | 821.5 | 12.35 (s, 1H), 11.08 (s, 1H), 8.69 (s, 1H), 8.33 (s, 1H), 8.07 (dd, J = 8.4, 4.0 Hz, 1H), 7.85 (t, J = 8.8 Hz, 1H), 7.63-7.54 (m, 2H), 7.11 (d, J = 8.8 Hz, 1H), 7.03 (d, J = 6.8 Hz, 1H), 6.60-6.52 (m, 1H), 6.05-5.87 (m, 1H), 5.05 (dd, J = 12.8, 5.4 Hz, 1H), 4.45-4.33 (m, 1H), 3.17 (t, J = 6.0 Hz, 2H), 2.93-2.83 (m, 1H), 2.62-2.52 (m, 6H), 2.48-2.40 (m, 1H), 2.32-2.27 (m, 1H), 2.25-2.20 (m, 2H), 2.19 (s, 3H), 2.15-2.09 (m, 2H), 2.06-2.00 (m, 1H), 1.98-1.90 (m, 3H), 1.88-1.80 (m, 3H), 1.78-1.71 (m, 2H), 1.64 (s, 6H), 1.57-1.45 (m, 2H), 1.29-1.15 (m, 2H), 1.10-0.95 (m, 4H) |
| I-309 | BBY | ALU | 851.4 | 11.08 (s, 1H), 10.49 (s, 1H), 8.55 (s, 1H), 8.48 (s, 1H), 8.47-8.44 (m, 1H), 8.43-8.37 (m, 1H), 8.24-8.21 (m, 1H), 7.98 (s, 1H), 7.39-7.08 (m, 1H), 7.00-6.92 (m, 2H), 6.89-6.81 (m, 1H), 5.40-5.31 (m, 1H), 4.57-4.44 (m, 1H), 4.20-4.13 (m, 1H), 3.55 (s, 3H), 3.40-3.39 (m, 2H), 3.07 (d, J = 7.6 Hz, 2H), 2.93-2.83 (m, 1H), 2.75-2.56 (m, 3H), 2.46 (s, 1H), 2.23-2.16 (m, 6H), 2.14 (s, 1H), 2.08-1.85 (m, 10H), 1.63-1.52 (m, 1H), 1.16-1.03 (m, 2H) |
| I-311 | AWB | AWF | 891.2 | 11.10 (s, 1H), 10.80 (s, 1H), 8.67 (s, 1H), 8.31 (s, 1H), 8.20-8.12 (m, 2H), 7.86 (d, J = 7.4 Hz, 1H), 7.61-7.54 (m, 1H), 7.15 (s, 1H), 7.12 (d, J = 8.5 Hz, 1H), 7.03 (d, J = 7.0 Hz, 1H), 6.58 (br t, J = 6.2 Hz, 1H), 5.06 (dd, J = 5.4, 12.8 Hz, 1H), 4.40-4.31 (m, 1H), 4.00 (s, 3H), 3.17 (br t, J = 6.4 Hz, 2H), 2.91-2.83 (m, 1H), 2.74-2.70 (m, 1H), 2.64-2.57 (m, 4H), 2.14 (br d, J = 7.8 Hz, 4H), 2.06-2.02 (m, 2H), 1.98-1.88 (m, 6H), 1.87 (br d, J = 1.4 Hz, 1H), 1.83 (s, 3H), 1.79 (br s, 2H), 1.77 (s, 3H), 1.77-1.73 (m, 2H), 1.63-1.52 (m, 2H), 1.44-1.36 (m, 2H), 1.18-0.97 (m, 7H) |
| I-312 | AQS | AGL | 885.4 | 12.36 (s, 1H), 11.11 (s, 1H), 8.71 (s, 1H), 8.49-8.42 (m, 1H), 8.39-8.32 (m, 2H), 8.16 (d, J = 8.4 Hz, 1H), 7.63-7.56 (m, 2H), 7.09 (d, J = 7.2 Hz, 1H), 6.90 (d, J = 8.8 Hz, 1H), 6.49 (d, J = 5.7 Hz, 1H), 5.94 (s, 1H), 5.06 (dd, J = 5.4, 12.6 Hz, 1H), 4.46-4.38 (m, 1H), 4.35-4.28 (m, 1H), 4.17-4.07 (m, 1H), 2.95-2.83 (m, 1H), 2.76-2.70 (m, 1H), 2.63-2.54 (m, 1H), 2.54-2.52 (m, 3H), 2.42-2.35 (m, 2H), 2.30-2.22 (m, 2H), 2.21-2.10 (m, 4H), 2.09-1.99 (m, 3H), 1.87-1.77 (m, 2H), 1.62 (s, 6H), 1.60-1.53 (m, 1H), 1.51-1.38 (m, 2H), 1.18-1.05 (m, 2H) |
| I-313 | AML | ATJ | 827.4 | 11.10 (s, 1H), 10.50 (s, 1H), 8.68 (s, 1H), 8.48-8.44 (m, 1H), 8.43-8.37 (m, 1H), 8.32 (s, 1H), 8.22 (d, J = 7.6 Hz, 1H), 7.58 (dd, J = 7.6, 8.4 Hz, 1H), 7.15 (s, 1H), 7.06 (d, J = 6.8 Hz, 1H), 7.00 (d, J = 8.4 Hz, 1H), 6.45 (d, J = 6.4 Hz, 1H), 5.06 (dd, J = 5.6, 12.8 Hz, 1H), 4.42-4.29 (m, 1H), 4.18-4.06 (m, 1H), 3.98 (s, 3H), 2.94-2.83 (m, 1H), 2.63-2.53 (m, 2H), 2.39-2.30 (m, 4H), 2.30-2.19 (m, 2H), 2.13 (d, J = 7.6 Hz, 4H), 2.07-1.99 (m, 1H), 1.97-1.80 (m, 4H), 1.73-1.51 (m, 7H), 1.17-1.00 (m, 2H) |
| I-314[d] | ATC | BEI | 939.1 | 11.27 (s, 1H), 11.10 (s, 1H), 8.76 (s, 1H), 8.53-8.49 (m, 1H), 8.42 (t, J = 7.6 Hz, 1H), 8.24 (dd, J = 0.8, 7.8 Hz, 1H), 7.71 (s, 1H), 7.59 (dd, J = 7.2, 8.4 Hz, 1H), 7.08 (d, J = 8.8 Hz, 1H), 7.03 (d, J = 7.2 Hz, 1H), 6.48 (t, J = 6.0 Hz, 1H), 5.06 (dd, J = 5.2, 13.2 Hz, 1H), 4.57-4.51 (m, 1H), 3.24 (m, 2H), 2.96 (d, J = 11.6 Hz, 3H), 2.91-2.84 (m, 2H), 2.78 (tm, 2H), 2.28-2.23 (m, 2H), 2.20-2.12 (m, 4H), 2.10-1.99 (m, 4H), 1.96-1.82 (m, 7H), 1.72-1.66 (m, 2H), 1.64-1.51 (m, 7H), 1.49-1.37 (m, 7H), 1.06-0.95 (m, 2H) |
| I-315 | ATH | BEJ | 833.5 | 11.10 (s, 1H), 10.70 (s, 1H), 8.57 (s, 1H), 8.37 (s, 1H), 8.23-8.10 (m, 2H), 7.86 (d, J = 7.4 Hz, 1H), 7.64-7.54 (m, 1H), 7.13-6.97 (m, 2H), 6.48 (m, 1H), 5.05 (m, 1H), 4.51-4.33 (m, 1H), 3.86 (s, 3H), 3.30-3.15 (m, 3H), 3.00-2.80 (m, 2H), 2.70-2.55 (m, 3H), 2.47 (m, 4H), 2.40-2.27 (m, 3H), 2.25-2.10 (m, 3H), 2.06-1.99 (m, 1H), 1.95-1.80 (m, 9H), 1.77 (s, 3H), 1.71-1.53 (m, 4H), 1.30-1.08 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-316 | AJF | BEL | 854.6 | 11.10 (s, 1H), 9.52 (s, 1H), 9.04 (s, 1H), 8.71-8.68 (m, 1H), 8.54 (s, 1H), 8.30 (s, 1H), 7.87 (s, 1H), 7.80 (d, J = 4.0 Hz, 1H), 7.61-7.55 (m, 1H), 7.14 (s, 1H), 7.11 (d, J = 8.4 Hz, 1H), 7.03 (d, J = 7.2 Hz, 1H), 6.47 (m, 1H), 5.08-5.00 (m, 1H), 4.38-4.31 (m, 1H), 4.01 (s, 3H), 2.95-2.81 (m, 2H), 2.61 (s, 3H), 2.61-2.60 (m, 1H), 2.59-2.53 (m, 6H), 2.21 (s, 1H), 2.13 (d, J = 11.6 Hz, 3H), 2.07-1.98 (m, 1H), 1.96-1.84 (m, 7H), 1.67-1.58 (m, 3H), 1.55-1.49 (m, 4H), 1.24-1.04 (m, 2H) |
| I-317 | BCR | ATJ | 869.5 | 11.10 (s, 1H), 10.50 (s, 1H), 8.68 (s, 1H), 8.48-8.43 (m, 1H), 8.43-8.37 (m, 1H), 8.32 (s, 1H), 8.21 (d, J = 7.6 Hz, 1H), 7.61-7.55 (m, 1H), 7.14 (s, 1H), 7.10 (d, J = 8.4 Hz, 1H), 7.03 (d, J = 6.8 Hz, 1H), 6.46 (t, J = 5.6 Hz, 1H), 5.05 (dd, J = 5.6, 12.8 Hz, 1H), 4.35 ( m, 1H), 3.98 (s, 3H), 3.44-3.40 (m, 2H), 2.88 (m, 1H), 2.63-2.56 (m, 1H), 2.53 (m, 2H), 2.34-2.25 (m, 3H), 2.22 (s, 3H), 2.12 (m, 2H), 2.07-1.99 (m, 1H), 1.97-1.72 (m, 7H), 1.69-1.39 (m, 6H), 1.34-1.15 (m, 4H), 1.13-1.01 (m, 2H) |
| I-318 | AOV | BEM | 873.4 | 11.10 (s, 1H), 10.41 (s, 1H), 8.67 (s, 1H), 8.54-8.42 (m, 2H), 8.39-8.27 (m, 2H), 8.14 (s, 1H), 7.68-7.53 (m, 1H), 7.27-7.10 (m, 2H), 7.05 (d, J = 6.8 Hz, 1H), 6.17 (d, J = 8.4 Hz, 1H), 5.07-5.03 (m, 1H), 4.48-4.31 (m, 1H), 3.98 (s, 3H), 3.62-3.48 (m, 1H), 3.21-3.13 (m, 1H), 2.96-2.81 (m, 2H), 2.69-2.51 (m, 3H), 2.46-2.38 (m, 2H), 2.36-2.30 (m, 1H), 2.23-1.83 (m, 11H), 1.75-1.46 (m, 3H), 1.43-1.27 (m, 2H), 1.23-1.06 (m, 2H). $^{19}$F NMR (376 MHz, DMSO-$d_6$) δ 81.05-79.18 (m, 1F), 53.29 (d, J = 160.4 Hz, 4F) |
| I-320 | AZK | BEN | 734.1 | 12.37 (s, 1H), 11.10 (s, 1H), 9.36 (s, 1H), 8.92 (d, J = 2.4 Hz, 1H), 8.80 (d, J = 1.2 Hz, 1H), 8.71 (s, 1H), 8.38 (s, 1H), 7.58 (s, 1H), 7.09-6.93 (m, 3H), 6.15 (s, 1H), 5.38 (dd, J = 5.2, 12.8 Hz, 1H), 4.52-4.37 (m, 1H), 3.60 (s, 3H), 3.25-3.23 (m, 1H), 3.01-2.99 (m, 2H), 2.95-2.84 (m, 1H), 2.78-2.63 (m, 2H), 2.25-2.23 (m, 2H), 2.19-2.06 (m, 4H), 2.04-1.90 (m, 5H), 1.85-1.75 (m, 4H), 1.72-1.66 (m, 1H), 1.63 (s, 6H), 1.23-1.09 (m, 2H) |
| I-321 | AML | BEO | 800.5 | 11.10 (s, 1H), 10.61 (s, 1H), 9.39 (dd, J = 1.6, 6.4 Hz, 1H), 8.96 (dd, J = 1.6, 4.0 Hz, 1H), 8.73 (d, J = 2.0 Hz, 2H), 7.58 (dd, J = 7.6, 8.4 Hz, 1H), 7.43 (s, 1H), 7.39-7.33 (m, 1H), 7.06 (d, J = 6.8 Hz, 1H), 6.99 (d, J = 8.4 Hz, 1H), 6.44 (d, J = 6.8 Hz, 1H), 5.05 (dd, J = 5.2, 12.8 Hz, 1H), 4.15-4.08 (m, 1H), 4.03 (s, 3H), 2.94-2.83 (m, 2H), 2.64-2.57 (m, 2H), 2.37-2.29 (m, 4H), 2.27-2.23 (m, 1H), 2.18-2.10 (m, 4H), 2.06-2.00 (m, 1H), 1.88 (d, J = 12.0 Hz, 2H), 1.75-1.49 (m, 10H), 1.12-0.92 (m, 2H) |
| I-322 | WX | BES | 816.6 | 12.19 (s, 1H), 11.16-11.01 (m, 1H), 8.74 (s, 1H), 8.32 (s, 1H), 7.90-7.84 (m, 2H), 7.58-7.55 (m, 2H), 7.07 (, J = 7.6 Hz, 1H), 6.98-6.93 (m, 1H), 6.87 (d, J = 8.0 Hz, 1H), 5.94 (s, 1H), 5.41-5.34 (m, 1H), 4.39-4.32 (m, 1H), 3.68 (s, 3H), 3.61 (s, 2H), 3.46-3.40 (m, 1H), 2.91-2.85 (m, 3H), 2.21 (d, J = 6.4 Hz, 3H), 2.17 (s, 3H), 2.15-2.09 (m, 3H), 2.04-1.85 (m, 10H), 1.62 (s, 6H), 1.40-1.37 (m, 1H), 1.26-1.24 (m, 2H), 1.05 (t, J = 7.2 Hz, 3H), 1.02-0.96 (m, 3H) |
| I-323 | ATH | BEU | 866.5 | 11.08 (s, 1H), 10.45 (s, 1H), 8.76 (s, 1H), 8.53-8.47 (m, 1H), 8.42 (t, J = 8.0 Hz, 1H), 8.26-8.20 (m, 1H), 7.61-7.54 (m, 1H), 7.48-7.40 (m, 1H), 7.10-7.04 (m, 1H), 7.03-6.99 (m, 1H), 6.50-6.43 (m, 1H), 5.75 (s, 1H), 5.07-5.03 (m, 1H), 4.76 (s, 1H), 3.94-3.87 (m, 2H), 3.17 (s, 1H), 3.12-3.08 (m, 2H), 3.03-2.98 (m, 2H), 2.92-2.83 (m, 2H), 2.24-2.09 (m, 8H), 2.08-1.98 (m, 2H), 1.86-1.72 (m, 4H), 1.66-1.50 (m, 4H), 1.33 (s, 6H), 1.30-1.22 (m, 1H), 1.10-0.95 (m, 2H) |
| I-324 | AZK | BEW | 706.4 | 11.10 (s, 1H), 10.52 (s, 1H), 9.44 (d, J = 1.2 Hz, 1H), 9.17 (d, J = 5.2 Hz, 1H), 8.72 (s, 1H), 8.35 (s, 1H), 8.19 (dd, J = 1.2, 5.2 Hz, 1H), 7.17 (s, 1H), 7.06-6.95 (m, 3H), 5.44-5.32 (m, 1H), 4.44-4.32 (m, 1H), 4.00 (s, 3H), 3.60 (s, 3H), 3.31-3.22 (m, 2H), 3.08-3.00 (m, 2H), 2.93-2.82 (m, 1H), 2.78-2.68 (m, 1H), 2.65- |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 2.56 (m, 1H), 2.30-2.24 (m, 2H), 2.20-2.11 (m, 4H), 2.04-1.96 (m, 3H), 1.94-1.85 (m, 2H), 1.85-1.80 (m, 3H), 1.73-1.63 (m, 1H), 1.25-1.09 (m, 2H) |
| I-325 | AZK | BEY | 709.4 | 11.09 (s, 1H), 9.35 (s, 1H), 8.67 (s, 1H), 8.56 (s, 1H), 8.30 (s, 1H), 7.12 (s, 1H), 7.04-6.95 (m, 3H), 5.42-5.33 (m, 1H), 4.42-4.31 (m, 1H), 3.96 (s, 3H), 3.59 (s, 3H), 3.06-3.02 (m Hz, 2H), 2.93-2.84 (m, 1H), 2.76-2.68 (m, 1H), 2.65-2.58 (m, 1H), 2.52 (s, 3H), 2.26 (d, J = 6.4 Hz, 2H), 2.18-2.12 (m Hz, 4H), 2.04-1.73 (m, 10H), 1.70-1.61 (m, 1H), 1.18-1.08 (m, 2H) |
| I-327 | AZK | BFA | 706.4 | 11.10 (s, 1H), 10.35 (s, 1H), 9.36 (d, J = 1.2 Hz, 1H), 8.98 (d, J = 2.4 Hz, 1H), 8.84 (dd, J = 1.6, 2.4 Hz, 1H), 8.71 (s, 1H), 8.35 (s, 1H), 7.19-7.14 (m, 1H), 7.10-6.95 (m, 3H), 5.43-5.34 (m, 1H), 4.47-4.35 (m, 1H), 4.00 (s, 3H), 3.65-3.58 (m, 3H), 2.98-2.81 (m, 1H), 2.55-2.52 (m, 6H), 2.23-2.14 (m, 3H), 2.05-1.68 (m, 12H), 1.26-1.14 (m, 2H) |
| I-328 | AZK | AXS | 719.4 | 11.10 (s, 1H), 10.71 (s, 1H), 8.70 (s, 1H), 8.31 (s, 1H), 8.02-7.94 (m, 2H), 7.55 (d, J = 6.8 Hz, 1H), 7.13 (s, 1H), 7.07-6.95 (m, 3H), 5.38 (dd, J = 12.8, 5.2 Hz, 1H), 4.49-4.28 (m, 1H), 4.00 (s, 3H), 3.61 (s, 3H), 3.25 (s, 2H), 2.97-2.81 (m, 2H), 2.77-2.65 (m, 3H), 2.62 (s, 4H), 2.52 (s, 1H), 2.16 (d, J = 11.2 Hz, 2H), 2.03-1.72 (m, 11H), 1.25-1.13 (m, 2H) |
| I-329 | AQK | BDT | 734.5 | 11.09 (s, 1H), 10.60 (s, 1H), 8.77-8.73 (m, 1H), 8.72 (s, 1H), 8.31 (s, 1H), 8.19 (d, J = 4.8 Hz, 1H), 8.10 (dt, J = 1.6, 7.6 Hz, 1H), 7.72-7.66 (m, 1H), 7.14 (s, 1H), 7.00-6.94 (m, 1H), 6.93-6.84 (m, 2H), 5.35 (dd, J = 5.6, 12.4 Hz, 1H), 4.44-4.30 (m, 1H), 3.99 (s, 3H), 3.64 (s, 3H), 3.15 (d, J = 11.2 Hz, 2H), 2.93-2.84 (m, 1H), 2.79-2.67 (m, 3H), 2.65-2.57 (m, 1H), 2.47-2.42 (m, 1H), 2.31-2.29 (m, 1H), 2.27 (s, 3H), 2.19-2.10 (m, 2H), 2.07-1.73 (m, 8H), 1.72-1.60 (m, 2H), 1.60-1.50 (m, 1H), 1.17-1.02 (m, 2H) |
| I-331 | ATH | BFB | 842.3 | 11.18-10.99 (m, 1H), 10.56 (s, 1H), 8.64 (s, 1H), 8.51-8.46 (m, 1H), 8.45-8.39 (m, 1H), 8.24 (d, J = 7.6 Hz, 1H), 7.58 (t, J = 7.6 Hz, 1H), 7.35 (s, 1H), 7.06 (d, J = 8.4 Hz, 1H), 7.02 (d, J = 7.2 Hz, 1H), 6.52-6.43 (m, 1H), 5.10-5.01 (m, 1H), 4.41 (s, 2H), 4.01 (s, 3H), 3.99-3.89 (m, 1H), 3.21 (d, J = 6.8 Hz, 2H), 3.09 (s, 2H), 3.00 (s, 2H), 2.92-2.82 (m, 1H), 2.61 (s, 2H), 2.23-2.11 (m, 5H), 2.07-1.98 (m, 1H), 1.87-1.70 (m, 6H), 1.68-1.61 (m, 2H), 1.59-1.49 (m, 2H), 1.23 (m, 1H), 1.09-0.94 (m, 2H) |
| I-332 | BFJ | ATJ | 841.1 | 11.10 (s, 1H), 10.50 (s, 1H), 8.68 (s, 1H), 8.49-8.36 (m, 2H), 8.32 (s, 1H), 8.22 (d, J = 7.6 Hz, 1H), 7.59 (t, J = 7.6 Hz, 1H), 7.14 (s, 1H), 7.09 (d, J = 8.4 Hz, 1H), 7.03 (d, J = 7.2 Hz, 1H), 6.48 (s, 1H), 5.10-5.01 (m, 1H), 4.42-4.28 (m, 1H), 3.98 (s, 3H), 3.79 (s, 2H), 3.63 (d, J = 1.2 Hz, 2H), 3.23-3.15 (m, 1H), 3.11-3.01 (m, 1H), 2.95-2.82 (m, 1H), 2.74 (s, 2H), 2.60 (d, J = 17.6 Hz, 2H), 2.29-2.19 (m, 2H), 2.13 (d, J = 92 Hz, 2H), 2.08-2.00 (m, 1H), 1.98-1.80 (m, 7H), 1.72-1.61 (m, 1H), 1.59-1.44 (m, 1H), 1.24-1.08 (m, 2H), 0.81 (d, J = 6.4 Hz, 3H) |
| I-333 | AZK | BFC | 734.5 | 12.52 (s, 1H), 11.11 (s, 1H), 9.39 (d, J = 1.2 Hz, 1H), 9.14 (d, J = 5.2 Hz, 1H), 8.73 (s, 1H), 8.39 (s, 1H), 8.20-8.19 (m, 1H), 7.58 (s, 1H), 7.03-6.99 (m, 3H), 6.19-6.17 (m, 1H), 5.40-5.36 (m, 1H), 4.48-4.42 (m, 1H), 3.60 (s, 3H), 3.25-3.21 (m, 1H), 3.01 (d, J = 10.8 Hz, 2H), 2.94-2.86 (m, 1H), 2.65-2.61 (m, 1H), 2.23 (d, J = 7.2 Hz, 2H), 2.18-2.07 (m, 4H), 2.01-1.89 (m, 6H), 1.81-1.77 (m, 4H), 1.63 (s, 7H), 1.20-1.11 (m, 2H) |
| I-334 | ATH | BFD | 827.2 | 12.04 (s, 1H), 11.10 (s, 1H), 10.58-10.32 (m, 1H), 8.60-8.54 (m, 1H), 8.50-8.44 (m, 1H), 8.44-8.36 (m, 1H), 8.21 (d, J = 7.6 Hz, 1H), 7.59 (dd, J = 7.2, 8.4 Hz, 1H), 7.27 (s, 1H), 7.12-7.00 (m, 2H), 6.52-6.43 (m, 1H), 5.08-5.01 (m, 1H), 4.08-3.98 (m, 1H), 3.95 (s, 3H), 3.94-3.80 (m, 2H), 3.29 (s, 4H), 3.26-3.20 (m, 2H), 2.95-2.83 (m, 2H), 2.80-2.70 (m, 1H), 2.63-2.53 (m, 1H), 2.22-2.14 (m, 1H), 2.14-1.97 (m, 4H), 1.93-1.78 (m, 4H), 1.70-1.61 (m, 2H), 1.60-1.48 (m, 3H), 1.17-1.03 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^{1}$HNMR (400 MHz, DMSO-$d_6$) δ |
|---|---|---|---|---|
| I-335 | BFU | ATJ | 855.5 | 11.06 (s, 1H), 10.50 (s, 1H), 8.68 (s, 1H), 8.49-8.37 (m, 2H), 8.33 (s, 1H), 8.22 (dd, J = 1.0, 7.7 Hz, 1H), 7.56 (d, J = 8.4 Hz, 1H), 7.35 (d, J = 6.0 Hz, 1H), 7.15 (s, 1H), 6.89-6.73 (m, 2H), 5.03 (dd, J = 5.4, 13.0 Hz, 1H), 4.41-4.30 (m, 1H), 3.98 (s, 3H), 3.97-3.93 (m, 1H), 2.92-2.81 (m, 1H), 2.61-2.55 (m, 1H), 2.44-2.36 (m, 2H), 2.26 (br d, J = 6.4 Hz, 3H), 2.21 (s, 3H), 2.19-2.10 (m, 3H), 2.05-1.80 (m, 7H), 1.71-1.60 (m, 3H), 1.59-1.49 (m, 3H), 1.42-1.30 (m, 3H), 1.27-1.18 (m, 2H), 1.13-1.00 (m, 2H) |
| I-336 | BFV | ATJ | 813.1 | 11.08 (s, 1H), 10.50 (s, 1H), 8.69 (s, 1H), 8.48-8.37 (m, 2H), 8.33 (s, 1H), 8.22 (dd, J = 1.0, 7.8 Hz, 1H), 7.58 (t, J = 8.0 Hz, 1H), 7.16-7.11 (m, 2H), 6.78 (d, J = 8.4 Hz, 1H), 5.05 (dd, J = 5.6, 12.8 Hz, 1H), 4.46-4.34 (m, 1H), 3.98 (s, 7H), 2.94-2.81 (m, 2H), 2.59-2.51 (m, 5H), 1.21-1.10 (m, 1H) |
| I-337 | AJF | BFK | 899.2 | 11.23-10.96 (m, 1H), 10.40 (s, 1H), 8.79 (s, 1H), 8.52-8.47 (m, 1H), 8.40 (t, J = 7.6 Hz, 1H), 8.32 (s, 1H), 8.25-8.15 (m, 2H), 7.58 (dd, J = 7.2, 8.4 Hz, 1H), 7.19-6.92 (m, 3H), 6.47 (t, J = 5.6 Hz, 1H), 5.06 (dd, J = 5.6, 12.8 Hz, 1H), 4.42-4.27 (m, 1H), 3.88 (s, 3H), 3.33 (t, J = 6.4 Hz, 2H), 2.95-2.82 (m, 1H), 2.71-2.54 (m, 1H), 2.35-1.99 (m, 10H), 1.96-1.77 (m, 7H), 1.68-1.44 (m, 8H), 1.35 (s, 7H), 1.15-0.98 (m, 3H) |
| I-369 | BKO | AWF | 779.5 | 10.79 (s, 1H), 8.67 (s, 1H), 8.32 (s, 1H), 8.19-8.16 (m, 1H), 8.14-8.11 (m, 1H), 7.85 (d, J = 7.6 Hz, 1H), 7.13 (d, J = 12.4 Hz, 2H), 7.01 (d, J = 8.0 Hz, 1H), 6.91 (d, J = 7.6 Hz, 1H), 5.40 (dd, J = 5.6, 13.2 Hz, 1H), 4.43-4.32 (m, 1H), 3.99 (s, 3H), 3.34 (s, 3H), 3.03 (s, 3H), 3.01-2.93 (m, 3H), 2.81-2.69 (m, 2H), 2.54 (br s, 1H), 2.22 (d, J = 6.0 Hz, 2H), 2.15 (d, J = 12.0 Hz, 2H), 2.06-1.85 (m, 7H), 1.83-1.71 (m, 10H), 1.70-1.60 (m, 1H), 1.20-1.05 (m, 2H) |
| I-370 | AZK | BKQ | 761.4 | 11.09 (s, 1H), 10.23 (d, J = 2.0 Hz, 1H), 8.50 (s, 1H), 8.46-8.37 (m, 3H), 8.24-8.21 (m, 1H), 7.54 (d, J = 12.0 Hz, 1H), 7.05-6.95 (m, 3H), 5.37 (dd, J = 5.2, 12.4 Hz, 1H), 4.51-4.40 (m, 1H), 3.59 (s, 3H), 3.06 (d, J = 11.2 Hz, 2H), 2.93-2.85 (m, 1H), 2.76-2.68 (m, 1H), 2.65-2.58 (m, 1H), 2.31-2.14 (m, 6H), 2.04-1.86 (m, 6H), 1.86-1.77 (m, 4H), 1.74-1.65 (m, 1H), 1.22-1.10 (m, 2H) |
| I-371[e] | AZK | BKS | 803.4 | 11.10 (s, 1H), 10.65 (s, 1H), 8.71 (s, 1H), 8.48-8.43 (m, 1H), 8.43-8.36 (m, 1H), 8.33 (s, 1H), 8.21 (dd, J = 0.8, 7.6 Hz, 1H), 7.15 (s, 1H), 7.05-6.95 (m, 3H), 5.38 (dd, J = 5.2, 12.8 Hz, 1H), 5.04-4.70 (m, 1H), 4.45-4.30 (m, 1H), 4.19 (t, J = 5.2 Hz, 2H), 3.88 (t, J = 5.2 Hz, 2H), 3.60 (s, 3H), 3.33-3.24 (m, 1H), 3.10 (d, J = 10.8 Hz, 2H), 2.94-2.84 (m, 1H), 2.77-2.68 (m, 1H), 2.66-2.58 (m, 1H), 2.41-2.34 (m, 2H), 2.31-2.21 (m, 2H), 2.20-2.11 (m, 2H), 2.03-1.80 (m, 9H), 1.76-1.64 (m, 1H), 1.24-1.08 (m, 2H) |
| I-372 | AQK | BEY | 738.5 | 11.09 (s, 1H), 9.35 (s, 1H), 8.67 (s, 1H), 8.56 (s, 1H), 8.30 (s, 1H), 7.12 (s, 1H), 7.00-6.94 (m, 1H), 6.93-6.82 (m, 2H), 5.40-5.29 (m, 1H), 4.42-4.29 (m, 1H), 4.00-3.93 (m, 3H), 3.64 (s, 3H), 3.16 (d, J = 10.4 Hz, 2H), 2.95-2.84 (m, 1H), 2.77-2.67 (m, 3H), 2.64-2.58 (m, 1H), 2.52 (s, 3H), 2.44-2.38 (m, 1H), 2.32-2.30 (m, 2H), 2.26 (s, 3H), 2.17-2.11 (m, 2H), 2.03-1.96 (m, 2H), 1.96-1.85 (m, 3H), 1.83-1.76 (m, 2H), 1.71-1.60 (m, 2H), 1.59-1.50 (m, 1H), 1.17-1.04 (m, 2H) |
| I-373 | BKT | AGL | 773.4 | 12.36 (s, 1H), 11.27-10.69 (m, 1H), 8.70 (s, 1H), 8.44 (d, J = 7.6 Hz, 1H), 8.40-8.33 (m, 2H), 8.15 (d, J = 7.6 Hz, 1H), 7.56 (s, 1H), 6.67 (s, 1H), 6.39 (s, 1H), 6.15-5.71 (m, 1H), 5.22 (dd, J = 5.2, 12.4 Hz, 1H), 4.45 (t, J = 11.2 Hz, 1H), 3.29 (s, 3H), 3.27 (s, 2H), 3.18 (d, J = 5.6 Hz, 2H), 2.93-2.84 (m, 1H), 2.70 (s, 2H), 2.62 (s, 2H), 2.16 (d, J = 8.4 Hz, 2H), 1.99-1.88 (m, 6H), 1.87-1.81 (m, 2H), 1.61 (s, 6H), 1.35-1.24 (m, 2H) |
| I-374 | AZK | BKW | 695.4 | 11.12 (s, 1H), 9.64 (s, 1H), 8.47-8.41 (m, 2H), 8.34 (s, 1H), 7.55 (s, 1H), 7.14 (s, 1H), 7.06-6.95 (m, 3H), 5.38 (dd, J = 5.2, 12.4 Hz, 1H), 4.42-4.33 (m, 1H), 3.96 (s, 3H), 3.59 (s, 3H), 3.23 (d, J = 3.6 Hz, 1H), 3.00-2.98 (m, 2H), 2.93-2.84 (m, 1H), 2.76-2.68 (m, 1H), 2.64- |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| | | | | 2.58 (m, 1H), 2.21-1.99 (m, 2H), 2.17-2.12 (m, 2H), 2.10-2.03 (m, 2H), 1.98-1.96 (m, 3H), 1.93-1.86 (m, 2H), 1.83-1.75 (m, 4H), 1.73-1.72 (m, 1H), 1.69-1.60 (m, 1H), 1.18-1.08 (m, 2H) |
| I-375 | BKY | ATJ | 805.4 | 11.03 (s, 1H), 10.50 (s, 1H), 8.69 (s, 1H), 8.48-8.44 (m, 1H), 8.43-8.38 (m, 1H), 8.33 (s, 1H), 8.22 (d, J = 7.6 Hz, 1H), 7.15 (s, 1H), 7.00 (d, J = 4.4 Hz, 2H), 6.74 (t, J = 4.4 Hz, 1H), 5.87 (dd, J = 7.2, 10.8 Hz, 1H), 4.41-4.32 (m, 1H), 4.12 (d, J = 4.8 Hz, 2H), 3.98 (s, 3H), 3.92-3.83 (m, 2H), 3.78 (s, 3H), 3.60 (t, J = 10.4 Hz, 1H), 3.30 (s, 2H), 2.94-2.83 (m, 2H), 2.72-2.63 (m, 2H), 2.33 (d, J = 3.2 Hz, 1H), 2.20 (d, J = 7.2 Hz, 2H), 2.14 (dd, J = 2.8, 8.8 Hz, 2H), 1.99-1.92 (m, 3H), 1.91-1.81 (m, 2H), 1.72-1.59 (m, 1H), 1.20-1.06 (m, 2H) |
| I-376 | BLA | ATJ | 805.4 | 11.03 (s, 1H), 10.50 (s, 1H), 8.69 (s, 1H), 8.49-8.43 (m, 1H), 8.43-8.37 (m, 1H), 8.33 (s, 1H), 8.22 (dd, J = 0.8, 7.6 Hz, 1H), 7.15 (s, 1H), 7.00 (d, J = 4.4 Hz, 2H), 6.74 (t, J = 4.4 Hz, 1H), 5.87 (dd, J = 6.4, 11.2 Hz, 1H), 4.46-4.30 (m, 1H), 4.22-4.06 (m, 2H), 3.98 (s, 3H), 3.94-3.81 (m, 2H), 3.79 (s, 3H), 3.68-3.53 (m, 1H), 2.97-2.81 (m, 2H), 2.76-2.66 (m, 1H), 2.65-2.58 (m, 1H), 2.36-2.28 (m, 2H), 2.26-1.79 (m, 10H), 1.77-1.56 (m, 1H), 1.32-1.01 (m, 2H) |
| I-377 | AZK | BMK | 761.5 | 11.85 (s, 1H), 11.10 (s, 1H), 8.33 (d, J = 2.0 Hz, 2H), 8.03-7.92 (m, 1H), 7.66 (d, J = 7.2 Hz, 1H), 7.35 (s, 1H), 7.10 (d, J = 8.4 Hz, 1H), 7.06-6.95 (m, 3H), 5.44-5.32 (m, 1H), 4.51-4.42 (m, 2H), 4.41-4.33 (m, 1H), 4.25-4.17 (m, 2H), 3.59 (s, 3H), 3.05-2.96 (m, 2H), 2.94-2.82 (m, 1H), 2.81-2.68 (m, 1H), 2.66-2.55 (m, 1H), 2.27-2.03 (m, 9H), 2.02-1.95 (m, 3H), 1.93-1.84 (m, 4H), 1.83-1.74 (m, 4H), 1.72-1.62 (m, 1H), 1.22-1.04 (m, 2H) |
| I-378 | AZK | BLB | 707.4 | 11.33-10.81 (m, 1H), 10.54 (s, 1H), 9.45 (s, 1H), 9.18 (d, J = 5.2 Hz, 1H), 8.69 (s, 1H), 8.23-8.14 (m, 1H), 7.51 (s, 1H), 7.05-6.92 (m, 3H), 5.33 (dd, J = 4.4, 10.4 Hz, 1H), 4.01 (s, 3H), 3.58 (s, 3H), 3.25-3.17 (m, 1H), 3.01-2.80 (m, 4H), 2.74-2.67 (m, 1H), 2.63-2.57 (m, 1H), 2.22-2.14 (m, 4H), 2.10-2.01 (m, 2H), 2.01-1.90 (m, 3H), 1.84-1.72 (m, 4H), 1.67-1.53 (m, 3H), 1.14-0.98 (m, 2H) |
| I-379 | AZK | BIO | 887.5 | 11.62 (s, 1H), 11.09 (s, 1H), 8.79 (s, 1H), 8.49-8.33 (m, 3H), 8.18 (d, J = 7.6 Hz, 1H), 7.65 (s, 1H), 7.07-6.92 (m, 3H), 5.42-5.33 (m, 1H), 4.55-4.36 (m, 1H), 3.95 (s, 2H), 3.93-3.86 (m, 2H), 3.59 (s, 3H), 3.00 (, J = 10.0 Hz, 2H), 2.93-2.82 (m, 1H), 2.70-2.59 (m, 2H), 2.23 (d, J = 6.4 Hz, 2H), 2.20-1.86 (m, 10H), 1.85-1.75 (m, 4H), 1.71 (s, 6H), 1.69-1.61 (m, 1H), 1.23-1.06 (m, 2H), 1.02-0.94 (m, 3H) |
| I-380 | BIL | AGL | 842.5 | 12.36 (s, 1H), 11.08 (s, 1H), 8.71 (s, 1H), 8.48-8.42 (m, 1H), 8.40-8.33 (m, 2H), 8.16 (d, J = 8.0 Hz, 1H), 7.57 (s, 1H), 6.99-6.92 (m, 1H), 6.72 (d, J = 8.0 Hz, 1H), 6.67 (d, J = 8.0 Hz, 1H), 5.94 (s, 1H), 5.40-5.28 (m, 1H), 4.49-4.34 (m, 1H), 3.61-3.55 (m, 7H), 2.91-2.80 (m, 1H), 2.74-2.66 (m, 1H), 2.64-2.56 (m, 1H), 2.35-2.28 (m, 3H), 2.17-2.10 (m, 4H), 2.00-1.88 (m, 5H), 1.83-1.74 (m, 4H), 1.70-1.55 (m, 8H), 1.15-1.00 (m, 2H) |
| I-381 | AZK | BLD | 706.5 | 11.10 (s, 1H), 10.58 (s, 1H), 9.07 (d, J = 4.8 Hz, 2H), 8.74 (s, 1H), 8.34 (s, 1H), 7.77 (t, J = 4.8 Hz, 1H), 7.16 (s, 1H), 7.05-6.95 (m, 3H), 5.38 (dd, J = 5.2, 12.8 Hz, 1H), 4.38 (dt, J = 3.6, 11.6 Hz, 1H), 3.99 (s, 3H), 3.59 (s, 3H), 3.24-3.19 (m, 1H), 3.00 (d, J = 11.2 Hz, 2H), 2.93-2.84 (m, 1H), 2.70 (dd, J = 4.4, 13.2 Hz, 1H), 2.65-2.59 (m, 1H), 2.21 (d, J = 7.2 Hz, 2H), 2.15 (d, J = 11.6 Hz, 2H), 2.08 (dt, J = 2.8, 10.8 Hz, 2H), 2.02-1.95 (m, 3H), 1.95-1.85 (m, 2H), 1.85-1.74 (m, 4H), 1.69-1.58 (m, 1H), 1.19-1.03 (m, 2H) |
| I-382 | AZK | BIQ | 859.5 | 11.72 (s, 1H), 11.09 (s, 1H), 8.76-8.73 (m, 1H), 8.46-8.31 (m, 3H), 8.13 (d, J = 8.4 Hz, 1H), 7.64 (s, 1H), 7.06-6.89 (m, 3H), 5.37 (dd, J = 5.2, 12.8 Hz, 1H), 4.52-4.34 (m, 1H), 3.82 (s, 2H), 3.59 (s, 3H), 3.25-3.22 (m, 1H), 3.04-2.96 (m, 2H), 2.93-2.84 (m, 1H), 2.75-2.60 (m, 2H), 2.23 (d, J = 7.2 Hz, 2H), 2.18- |

TABLE 7-continued

Compounds synthesized via Method 2 with the reductive amination of various intermediate amines and aldehydes.

| I-# | Intermediate Amine | Intermediate Aldehyde | LCMS (ES+) m/z $(M + H)^+$ | $^1$HNMR (400 MHz, DMSO-$d_6$) δ |
|---|---|---|---|---|
| | | | | 2.05 (m, 4H), 2.02-1.88 (m, 5H), 1.85-1.74 (m, 4H), 1.69 (s, 6H), 1.65-1.46 (m, 1H), 1.22-1.06 (m, 2H) |
| I-383 | AZK | BIP | 858.6 | 11.54 (s, 1H), 11.10 (s, 1H), 8.88 (s, 1H), 8.50-8.35 (m, 3H), 8.19 (d, J = 0.8 Hz, 1H), 7.66 (s, 1H), 7.36 (s, 1H), 7.08-6.94 (m, 3H), 6.83 (s, 1H), 5.38 (dd, J = 5.2, 12.8 Hz, 1H), 4.53-4.40 (m, 1H), 3.62 (s, 2H), 3.60 (s, 3H), 3.27-3.24 (m, 1H), 3.05-2.96 (m, 2H), 2.95-2.85 (m, 1H), 2.77-2.60 (m, 2H), 2.23 (d, J = 7.2 Hz, 2H), 2.20-2.06 (m, 4H), 2.04-1.89 (m, 5H), 1.86-1.76 (m, 4H), 1.75 (s, 6H), 1.70-1.59 (m, 1H), 1.23-1.06 (m, 2H) |
| I-384 | AQK | BBA | 856.5 | 11.09 (s, 1H), 10.39 (s, 1H), 8.71-8.65 (m, 1H), 8.59 (s, 1H), 8.49-8.39 (m, 2H), 8.26-8.23 (m, 1H), 7.80 (s, 1H), 7.00-6.94 (m, 1H), 6.93-6.84 (m, 2H), 5.41-5.30 (m, 1H), 4.54-4.45 (m, 1H), 3.64 (s, 3H), 3.16 (d, J = 12.0 Hz, 2H), 2.94-2.84 (m, 1H), 2.78-2.68 (m, 3H), 2.65-2.58 (m, 1H), 2.34-2.32 (m, 1H), 2.29 (s, 3H), 2.17 (d, J = 10.8 Hz, 2H), 2.04-1.87 (m, 6H), 1.82 (d, J = 11.2 Hz, 2H), 1.75-1.53 (m, 4H), 1.19-1.06 (m, 2H) |
| I-385 | AQK | AXF | 830.2 | 11.10 (s, 1H), 10.76-10.73 (m, 1H), 8.74 (s, 1H), 8.49-8.45 (m, 1H), 8.44-8.38 (m, 1H), 8.34 (s, 1H), 8.25-8.20 (m, 1H), 7.19 (s, 1H), 7.02-6.97 (m, 1H), 6.94-6.87 (m, 2H), 5.40-5.33 (m, 1H), 4.88-4.81 (m, 1H), 4.44-4.33 (m, 1H), 3.65 (s, 3H), 3.19 (d, J = 10.8 Hz, 2H), 2.94-2.85 (m, 1H), 2.82-2.59 (m, 6H), 2.53 (s, 1H), 2.50-2.41 (m, 3H), 2.21-2.12 (m, 2H), 2.04-1.87 (m, 7H), 1.82-1.62 (m, 3H), 1.43-1.40 (m, 6H), 1.24-1.11 (m, 2H) |
| I-386 | AZK | BIS | 802.5 | 12.57 (s, 1H), 11.10 (s, 1H), 9.37 (d, J = 5.2 Hz, 1H), 8.76 (s, 1H), 8.43 (d, J = 4.8 Hz, 1H), 8.40 (s, 1H), 7.59 (s, 1H), 7.09-6.94 (m, 3H), 6.09 (s, 1H), 5.43-5.33 (m, 1H), 4.54-4.40 (m, 1H), 3.61 (s, 3H), 2.94-2.86 (m, 1H), 2.76-2.69 (m, 1H), 2.66-2.58 (m, 2H), 2.52 ( s, 2H), 2.48-2.40 (m, 4H), 2.21-2.14 (m, 2H), 2.05-1.87 (m, 9H), 1.84-1.75 (m, 1H), 1.63 (s, 6H), 1.28-1.15 (m, 2H) |
| I-387 | AQK | BLE | 733.6 | 11.09 (s, 1H), 9.36 (s, 1H), 8.29 (s, 1H), 8.15 (s, 1H), 7.97 (d, J = 7.2 Hz, 2H), 7.62-7.50 (m, 3H), 7.07 (s, 1H), 7.01-6.84 (m, 3H), 5.40-5.30 (m, 1H), 4.43-4.32 (m, 1H), 3.89 (s, 3H), 3.64 (s, 3H), 3.16 (d, J = 11.2 Hz, 2H), 2.94-2.84 (m, 1H), 2.78-2.62 (m, 4H), 2.48-2.42 (m, 1H), 2.31 (d, J = 6.8 Hz, 2H), 2.27 (s, 3H), 2.15 (d, J = 11.2 Hz, 2H), 2.03-1.85 (m, 5H), 1.81 (d, J = 10.8 Hz, 2H), 1.73-1.60 (m, 2H), 1.59-1.50 (m, 1H), 1.18-1.04 (m, 2H) |
| I-388[f] | AZK | BLI | 856.4 | 11.10 (s, 1H), 10.50 (s, 1H), 8.70 (s, 1H), 8.48-8.46 (m, 1H), 8.43-8.39 (m, 1H), 8.36 (s, 1H), 8.22 (d, J = 8.0 Hz, 1H), 7.89 (s, 1H), 7.16 (s, 1H), 7.03-6.99 (m, 3H), 5.41-5.36 (m, 1H), 4.45-4.38 (m, 1H), 4.13-4.11 (m, 2H), 4.04-4.00 (m, 1H), 3.61 (s, 3H), 3.21-3.12 (m, 2H), 2.93-2.85 (m, 1H), 2.73-2.59 (m, 3H), 2.33-2.25 (m, 4H), 2.19-2.15 (m, 4H), 2.01-1.95 (m, 6H), 1.91-1.83 (m, 5H), 1.78-1.71 (m, 1H), 1.24-1.14 (m, 2H) |
| I-389[f] | AZK | BLM | 856.4 | 11.10 (s, 1H), 10.50 (s, 1H), 8.70 (s, 1H), 8.48-8.46 (m, 1H), 8.43-8.39 (m, 1H), 8.36 (s, 1H), 8.23 (d, J = 7.6 Hz, 1H), 7.89 (s, 1H), 7.17 (s, 1H), 7.08-6.98 (m, 3H), 5.41-5.36 (m, 1H), 4.47-4.37 (m, 1H), 4.13-4.11 (m, 2H), 4.05-4.00 (m, 1H), 3.61 (s, 3H), 3.30 (s, 2H), 2.96-2.84 (m, 1H), 2.65-2.53 (m, 3H), 2.31-2.21 (m, 4H), 2.19-2.09 (m, 4H), 2.01-1.96 (m, 6H), 1.92-1.80 (m, 6H), 1.26-1.14 (m, 2H) |
| I-390[f] | AZK | BLL | 788.4 | 11.10 (s, 1H), 10.73 (s, 1H), 8.77 (d, J = 4.4 Hz, 1H), 8.73 (s, 1H), 8.33 (s, 1H), 8.19-8.17 (m, 1H), 8.13-8.07 (m, 1H), 7.85 (s, 1H), 7.72-7.68 (m, 1H), 7.15 (s, 1H), 7.06-6.98 (m, 3H), 5.41-5.36 (m, 1H), 4.44-4.39 (m, 1H), 4.20-4.07 (m, 3H), 3.61 (s, 3H), 3.29 (s, 3H), 2.95-2.85 (m, 1H), 2.77-2.70 (m, 1H), 2.65-2.55 (m, 4H), 2.31-2.25 (m, 2H), 2.22-2.04 (m, 6H), 2.02-1.85 (m, 9H), 1.23-1.15 (m, 2H) |
| I-391[f] | AZK | BLH | 788.4 | 11.11 (s, 1H), 10.74 (s, 1H), 8.79-8.77 (m, 1H), 8.74 (s, 1H), 8.34 (s, 1H), 8.20-8.18 (m, 1H), 8.12-8.08 |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | (m, 1H), 7.86 (s, 1H), 7.72-7.62 (m, 1H), 7.16 (s, 1H), 7.07-6.98 (m, 3H), 5.42-5.35 (m, 1H), 4.49-4.35 (m, 1H), 4.20-4.01 (m, 3H), 3.63 (s, 3H), 3.30-3.28 (m, 3H), 2.93-2.86 (m, 1H), 2.77-2.69 (m, 1H), 2.67-2.53 (m, 4H), 2.30-2.26 (m, 2H), 2.24-2.09 (m, 5H), 2.06-1.90 (m, 9H), 1.24-1.15 (m, 2H) |
| I-392 | AQK | BIT | 751.5 | 11.08 (s, 1H), 9.51 (s, 1H), 8.29 (s, 1H), 8.06 (s, 1H), 7.86-7.72 (m, 2H), 7.64-7.55 (m, 1H), 7.50-7.40 (m, 1H), 7.07 (s, 1H), 7.00-6.83 (m, 3H), 5.35 (dd, J = 5.2, 12.8 Hz, 1H), 4.44-4.30 (m, 1H), 3.87 (s, 3H), 3.64 (s, 3H), 3.16 (d, J = 11.2 Hz, 2H), 2.95-2.83 (m, 1H), 2.77-2.58 (m, 4H), 2.47-2.42 (m, 1H), 2.35-2.28 (m, 2H), 2.26 (s, 3H), 2.19-2.11 (m, 2H), 2.01-1.77 (m, 7H), 1.72-1.52 (m, 3H), 1.19-1.02 (m, 2H) |
| I-393 | AQK | BIU | 798.6 | 12.06 (s, 1H), 11.08 (s, 1H), 8.65-8.59 (m, 2H), 8.35 (s, 1H), 8.20-8.10 (m, 1H), 7.55 (s, 1H), 7.01-6.95 (m, 1H), 6.94-6.83 (m, 2H), 6.06 (s, 1H), 5.40-5.30 (m, 1H), 4.51-4.32 (m, 1H), 3.64 (s, 3H), 3.20-3.10 (m, 2H), 2.94-2.82 (m, 1H), 2.79-2.70 (m, 2H), 2.64-2.56 (m, 1H), 2.46-2.39 (m, 1H), 2.35-2.24 (m, 5H), 2.20-2.10 (m, 2H), 2.06-1.72 (m, 8H), 1.71-1.50 (m, 9H), 1.19-1.04 (m, 2H) |
| I-394 | AQK | BLN | 852.5[d] | 12.47 (s, 1H), 11.09 (s, 1H), 9.09 (s, 1H), 8.71 (s, 1H), 8.50 (br d, J = 8.6 Hz, 1H), 8.42-8.35 (m, 2H), 7.58 (s, 1H), 7.03-6.95 (m, 1H), 6.94-6.85 (m, 2H), 6.11 (s, 1H), 5.36 (dd, J = 5.6, 12.3 Hz, 1H), 4.50-4.40 (m, 1H), 3.65 (s, 3H), 3.18 (d, J = 10.6 Hz, 2H), 2.95-2.85 (m, 1H), 2.79-2.71 (m, 2H), 2.69-2.59 (m, 2H), 2.49-2.27 (m, 5H), 2.16 (d, J = 10.2 Hz, 2H), 2.05-1.91 (m, 5H), 1.91-1.83 (m, 2H), 1.83-1.64 (m, 3H), 1.63 (s, 6H), 1.23-1.09 (m, 2H) |
| I-395 | AQK | BLO | 831.5 | 11.31 (s, 1H), 11.09 (s, 1H), 9.60 (s, 1H), 9.41 (s, 1H), 8.47 (s, 1H), 8.40 (s, 1H), 7.60 (s, 1H), 7.01-6.96 (m, 1H), 6.94-6.90 (m, 1H), 6.88 (d, J = 7.6 Hz, 1H), 6.21 (s, 1H), 5.36 (dd, J = 5.2, 12.6 Hz, 1H), 4.50-4.40 (m, 1H), 3.65 (s, 3H), 3.17 (d, J = 10.9 Hz, 2H), 2.93-2.85 (m, 1H), 2.77-2.71 (m, 2H), 2.70-2.58 (m, 2H), 2.35-2.31 (m, 2H), 2.28 (s, 3H), 2.20-2.12 (m, 2H), 2.03-1.89 (m, 5H), 1.85-1.77 (m, 2H), 1.75-1.65 (m, 2H), 1.65-1.63 (m, 1H), 1.62 (s, 6H), 1.60-1.53 (m, 1H), 1.20-1.08 (m, 2H) |
| I-396 | AQK | BLP | 803.2 | 11.10 (s, 1H), 10.16 (s, 1H), 9.54 (s, 1H), 9.29 (s, 1H), 8.38 (s, 1H), 8.33 (s, 1H), 7.09 (s, 1H), 7.01-6.95 (m, 1H), 6.94-6.90 (m, 1H), 6.88 (d, J = 7.6 Hz, 1H), 5.36 (dd, J = 5.2, 12.6 Hz, 1H), 4.44-4.34 (m, 1H), 3.88 (s, 3H), 3.65 (s, 3H), 3.17 (d, J = 11.3 Hz, 2H), 2.94-2.85 (m, 1H), 2.79-2.59 (m, 5H), 2.37-2.32 (m, 2H), 2.29 (s, 3H), 2.16 (d, J = 10.8 Hz, 2H), 2.05-1.93 (m, 4H), 1.93-1.79 (m, 4H), 1.75-1.64 (m, 2H), 1.62-1.52 (m, 1H), 1.19-1.07 (m, 2H) |
| I-397 | AQK | BGL | 735.5 | 11.22-10.91 (m, 1H), 10.02-9.80 (m, 1H), 9.41 (s, 1H), 9.31-9.19 (m, 2H), 8.35-8.28 (m, 1H), 8.13-8.05 (m, 1H), 7.09 (s, 1H), 7.01-6.95 (m, 1H), 6.94-6.82 (m, 2H), 5.41-5.29 (m, 1H), 4.45-4.33 (m, 1H), 3.88 (s, 3H), 3.65 (s, 3H), 3.21-3.10 (m, 2H), 2.95-2.82 (m, 1H), 2.79-2.66 (m, 3H), 2.66-2.58 (m, 1H), 2.33-2.28 (m, 2H), 2.28-2.25 (m, 3H), 2.20-2.11 (m, 2H), 1.76 (s, 8H), 1.72-1.53 (m, 3H), 1.18-1.04 (m, 2H) |
| I-398 | AQK | BIS | 831.4 | 12.57 (s, 1H), 11.09 (s, 1H), 9.36 (d, J = 5.2 Hz, 1H), 8.75 (s, 1H), 8.43 (d, J = 5.2 Hz, 1H), 8.39 (s, 1H), 7.59 (s, 1H), 7.01-6.84 (m, 3H), 6.19-5.96 (m, 1H), 5.40-5.31 (m, 1H), 4.49-4.39 (m, 1H), 3.64 (s, 3H), 3.16 (d, J = 10.4 Hz, 2H), 2.94-2.85 (m, 1H), 2.78-2.67 (m, 3H), 2.64-2.58 (m, 1H), 2.43 (s, 1H), 2.32-2.28 (m, 2H), 2.26 (s, 3H), 2.19-2.12 (m, 2H), 2.03-1.88 (m, 5H), 1.80 (d, J = 10.8 Hz, 2H), 1.71-1.60 (m, 8H), 1.58-1.51 (m, 1H), 1.18-1.06 (m, 2H) |
| I-399 | AQK | BLQ | 831.4 | 11.98 (s, 1H), 11.09 (s, 1H), 9.43 (s, 2H), 8.64 (s, 1H), 8.40 (s, 1H), 7.62 (s, 1H), 7.00-6.83 (m, 3H), 6.79-6.36 (m, 1H), 5.35 (dd, J = 5.2, 12.4 Hz, 1H), 4.47-4.41 (m, 1H), 3.64 (s, 3H), 3.16 (d, J = 11.2 Hz, 2H), 2.94-2.84 (m, 1H), 2.79-2.67 (m, 3H), 2.65-2.58 (m, 1H), 2.46-2.41 (m, 1H), 2.31-2.29 (m, 2H), 2.26 (s, 3H), |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | 2.15-2.13 (m, 2H), 2.05-1.88 (m, 5H), 1.82-1.79 (m, 2H), 1.72-1.61 (s, 8H), 1.59-1.51 (m, 1H), 1.19-1.05 (m, 2H) |
| I-400 | AQK | BLR | 752.4 | 11.10 (s, 1H), 10.42 (s, 1H), 8.78 (s, 1H), 8.70 (s, 1H), 8.33 (s, 1H), 8.31-8.25 (m, 1H), 8.05-7.98 (m, 1H), 7.16 (s, 1H), 7.03-6.95 (m, 1H), 6.94-6.85 (m, 2H), 5.36 (dd, J = 5.2, 12.8 Hz, 1H), 4.46-4.31 (m, 1H), 4.00 (s, 3H), 3.65 (s, 3H), 3.17 (d, J = 10.8 Hz, 2H), 2.97-2.84 (m, 1H), 2.81-2.59 (m, 4H), 2.48-2.42 (m, 1H), 2.32 (d, J = 6.4 Hz, 2H), 2.28 (s, 3H), 2.21-2.09 (m, 2H), 2.05-1.86 (m, 5H), 1.86-1.76 (m, 2H), 1.74-1.51 (m, 3H), 1.19-1.05 (m, 2H) |
| I-401 | AZK | BLP | 774.2 | 11.11 (s, 1H), 10.17 (s, 1H), 9.54 (s, 1H), 9.29 (s, 1H), 8.38 (s, 1H), 8.33 (s, 1H), 7.09 (s, 1H), 7.05-6.98 (m, 3H), 5.39 (dd, J = 5.4, 12.6 Hz, 1H), 4.45-4.36 (m, 1H), 3.88 (s, 3H), 3.61 (s, 3H), 3.19-3.12 (m, 2H), 2.95-2.85 (m, 1H), 2.77-2.68 (m, 1H), 2.66-2.60 (m, 1H), 2.47-2.29 (m, 4H), 2.17 (d, J = 11.2 Hz, 2H), 2.05-1.95 (m, 4H), 1.95-1.82 (m, 6H), 1.79-1.69 (m, 1H), 1.24-1.13 (m, 2H) |
| I-402 | AQK | BLS | 829.3 | 11.12 (s, 1H), 11.09 (s, 1H), 8.59 (s, 1H), 8.37 (s, 1H), 8.19 (s, 1H), 7.79 (dd, J = 1.5, 8.0 Hz, 1H), 7.64-7.59 (m, 1H), 7.56 (s, 1H), 7.54-7.49 (m, 1H), 7.00-6.94 (m, 1H), 6.93-6.84 (m, 2H), 6.21 (s, 1H), 5.35 (dd, J = 5.4, 12.6 Hz, 1H), 4.50-4.38 (m, 1H), 3.64 (s, 3H), 3.16 (br d, J = 11.2 Hz, 3H), 2.95-2.83 (m, 1H), 2.78-2.57 (m, 4H), 2.34-2.29 (m, 2H), 2.27 (s, 3H), 2.20-2.10 (m, 2H), 2.05-1.86 (m, 5H), 1.84-1.75 (m, 2H), 1.72-1.51 (m, 9H), 1.20-1.04 (m, 2H) |
| I-403[h] | AQK | BLT | 762.5 | 12.26 (s, 1H), 11.09 (s, 1H), 8.69 (d, J = 2.8 Hz, 1H), 8.66 (s, 1H), 8.27 (dd, J = 4.8, 8.8 Hz, 1H), 8.17 (s, 1H), 7.97 (dt, J = 2.8, 8.8 Hz, 1H), 7.56 (s, 1H), 7.01-6.94 (m, 1H), 6.93-6.84 (m, 2H), 6.07 (s, 1H), 5.35 (dd, J = 52, 12.8 Hz, 1H), 4.48-4.36 (m, 1H), 3.64 (s, 3H), 3.16 (d, J = 11.2 Hz, 2H), 2.93-2.84 (m, 1H), 2.78-2.67 (m, 3H), 2.65-2.58 (m, 1H), 2.47-2.41 (m, 1H), 2.36-2.30 (m, 2H), 2.27 (s, 3H), 2.19-2.09 (m, 2H), 2.04-1.86 (m, 5H), 1.85-1.76 (m, 2H), 1.72-1.53 (m, 9H), 1.19-1.04 (m, 2H) |
| I-404 | AQK | BIV | 768.4 | 11.71 (s, 1H), 11.09 (s, 1H), 9.33 (s, 1H), 8.51 (s, 1H), 8.36 (s, 2H), 7.58 (s, 1H), 6.99-6.95 (m, 1H), 6.92-6.86 (m, 2H), 6.59 (s, 1H), 5.37-3.33 (m, 1H), 4.45-4.40 (m, 1H), 3.64 (s, 3H), 3.16 (d, J = 11.6 Hz, 2H), 2.92-2.85 (m, 1H), 2.75-2.67 (m, 4H), 2.64-2.59 (m, 1H), 2.52 (s, 1H), 2.35-2.31 (m, 2H), 2.27 (s, 3H), 2.16-2.13 (m, 2H), 2.01-1.87 (m, 5H), 1.81 (d, J = 11.2 Hz, 2H), 1.71 (d, J = 3.5 Hz, 1H), 1.65 (s, 6H), 1.60-1.52 (m, 1H), 1.16-1.06 (m, 2H) |
| I-405 | AZK | BML | 775.5 | 11.17 (s, 1H), 11.10 (s, 1H), 8.59 (s, 1H), 8.30 (s, 1H), 7.96 (dd, J = 7.2, 8.0 Hz, 1H), 7.69 (d, J = 6.8 Hz, 1H), 7.10-7.05 (m, 2H), 7.05-6.95 (m, 3H), 5.38 (dd, J = 5.2, 12.8 Hz, 1H), 4.51-4.42 (m, 2H), 4.42-4.33 (m, 1H), 4.21 (t, J = 4.8 Hz, 2H), 3.61 (s, 3H), 3.27-3.12 (m, 2H), 2.95-2.85 (m, 1H), 2.77-2.64 (m, 2H), 2.64-2.52 (m, 3H), 2.49-2.38 (m, 2H), 2.29-2.21 (m, 2H), 2.20-2.14 (m, 2H), 2.04-1.84 (m, UH), 1.82-1.71 (m, 3H), 1.28-1.11 (m, 2H) |
| I-406 | AQK | BML | 804.5 | 11.16 (s, 1H), 11.09 (s, 1H), 8.58 (s, 1H), 8.30 (s, 1H), 7.99-7.90 (m, 1H), 7.69 (d, J = 6.8 Hz, 1H), 7.11-7.03 (m, 2H), 7.00-6.84 (m, 3H), 5.35 (dd, J = 5.2, 12.8 Hz, 1H), 4.52-4.41 (m, 2H), 4.40-4.29 (m, 1H), 4.22-4.21 (m, 2H), 3.64 (s, 3H), 3.16-3.13 (m, 2H), 2.94-2.84 (m, 1H), 2.77-2.66 (m, 3H), 2.65-2.58 (m, 1H), 2.46-2.40 (m, 1H), 2.30-2.28 (m, 2H), 2.27-2.19 (m, 5H), 2.17-2.11 (m, 2H), 2.04-1.85 (m, 7H), 1.83-1.72 (m, 4H), 1.70-1.60 (m, 2H), 1.58-1.49 (m, 1H), 1.18-1.02 (m, 2H) |
| I-407 | AQK | BMK | 790.6 | 11.84 (s, 1H), 11.09 (s, 1H), 8.33 (d, J = 2.0 Hz, 2H), 8.01-7.93 (m, 1H), 7.65 (d, J = 7.2 Hz, 1H), 7.34 (s, 1H), 7.09 (d, J = 8.4 Hz, 1H), 7.00-6.80 (m, 3H), 5.40-5.30 (m, 1H), 4.50-4.41 (m, 2H), 4.41-4.32 (m, 1H), 4.25-4.16 (m, 2H), 3.64 (s, 3H), 3.17-3.13 (m, 2H), 2.95-2.84 (m, 1H), 2.78-2.70 (m, 2H), 2.65-2.55 (m, |

TABLE 7-continued

| Compounds synthesized via Method 2 with the reductive amination of various intermediate amines and aldehydes. | | | | |
|---|---|---|---|---|
| I-# | Intermediate Amine | Intermediate Aldehyde | LCMS (ES+) m/z $(M + H)^+$ | $^1$HNMR (400 MHz, DMSO-$d_6$) δ |
| | | | | 1H), 2.47-2.40 (m, 1H), 2.32-2.26 (m, 2H), 2.25 (s, 3H), 2.22-2.10 (m, 4H), 2.05-1.75 (m, 10H), 1.70-1.47 (m, 3 H), 1.20-1.01 (m, 2H) |
| I-408 | AZK | BMJ | 777.5 | 11.10 (s, 1H), 11.01 (s, 1H), 8.58 (s, 1H), 8.33 (s, 1H), 8.03-7.93 (m, 1H), 7.74 (d, J = 7.2 Hz, 1H), 7.18 (s, 1H), 7.11 (d, J = 8.4 Hz, 1H), 7.05-6.94 (m, 3H), 5.37 (dd, J = 5.2, 12.4 Hz, 1H), 4.57 (t, J = 6.8 Hz, 2H), 4.42-4.32 (m, 1H), 4.27-4.20 (m, 2H), 4.08 (t, J = 6.8 Hz, 2H), 3.96-3.88 (m, 2H), 3.59 (s, 3H), 2.99 (d, J = 11.2 Hz, 2H), 2.94-2.83 (m, 1H), 2.76-2.68 (m, 1H), 2.65-2.58 (m, 1H), 2.21 (d, J = 7.2 Hz, 2H), 2.18-2.12 (m, 2H), 2.12-2.04 (m, 2H), 2.03-1.73 (m, 10H), 1.70-1.59 (m, 1H), 1.19-1.05 (m, 2H) |
| I-409 | AQK | BMJ | 806.6 | 11.09 (s, 1H), 11.01 (s, 1H), 8.58 (s, 1H), 8.33 (s, 1H), 7.98 (dd, J = 7.2, 8.4 Hz, 1H), 7.74 (d, J = 6.8 Hz, 1H), 7.18 (s, 1H), 7.11 (d, J = 8.8 Hz, 1H), 7.02-6.94 (m, 1H), 6.93-6.84 (m, 2H), 5.35 (dd, J = 5.2, 12.8 Hz, 1H), 4.57 (t, J = 6.8 Hz, 2H), 4.44-4.29 (m, 1H), 4.28-4.20 (m, 2H), 4.08 (t, J = 6.8 Hz, 2H), 3.97-3.87 (m, 2H), 3.64 (s, 3H), 3.15 (d, J = 11.2 Hz, 2H), 2.96-2.84 (m, 1H), 2.78-2.67 (m, 3H), 2.65-2.57 (m, 1H), 2.47-2.40 (m, 1H), 2.29 (d, J = 6.8 Hz, 2H), 2.26 (s, 3H), 2.19-2.10 (m, 2H), 2.03-1.76 (m, 7H), 1.72-1.49 (m, 3H), 1.18-1.03 (m, 2H) |
| I-410 | AQK | BLU | 768.4 | 12.12 (s, 1H), 11.10 (s, 1H), 8.62 (s, 1H), 8.37 (s, 1H), 8.16 (s, 1H), 8.12 (d, J = 3.2 Hz, 1H), 8.08 (d, J = 3.2 Hz, 1H), 7.57 (s, 1H), 7.01-6.84 (m, 3H), 6.26 (br s, 1H), 5.35 (dd, J = 5.4, 12.7 Hz, 1H), 4.49-4.38 (m, 1H), 3.64 (s, 3H), 3.16 (br d, J = 11.2 Hz, 3H), 2.95-2.83 (m, 1H), 2.78-2.58 (m, 4H), 2.38-2.26 (m, 5H), 2.14 (br d, J = 10.8 Hz, 2H), 2.04-1.77 (m, 7H), 1.74-1.53 (m, 9H), 1.20-1.05 (m, 2H) |
| I-411 | AQK | BLV | 829.1 | 11.73 (s, 1H), 11.10 (s, 1H), 8.67-8.62 (m, 1H), 8.41-8.32 (m, 1H), 8.08 (d, J = 2.0 Hz, 1H), 7.91-7.84 (m, 2H), 7.59 (s, 1H), 7.02-6.95 (m, 1H), 6.94-6.84 (m, 2H), 6.78-6.43 (m, 1H), 5.41-5.31 (m, 1H), 4.50-4.38 (m, 1H), 3.65 (s, 3H), 3.16 (d, J = 11.6 Hz, 2H), 2.95-2.83 (m, 1H), 2.78-2.63 (m, 4H), 2.48-2.44 (m, 1H), 2.34-2.29 (m, 2H), 2.27 (s, 3H), 2.15 (d, J = 11.2 Hz, 2H), 2.01-1.88 (m, 5H), 1.85-1.78 (m, 2H), 1.65 (s, 9H), 1.18-1.06 (m, 2H) |
| I-412 | AQK | BIW | 803.5 | 11.09 (s, 1H), 10.11 (s, 1H), 9.47 (s, 2H), 8.33 (s, 1H), 8.16 (s, 1H), 7.10 (s, 1H), 7.01-6.83 (m, 3H), 5.40-5.29 (m, 1H), 4.45-4.33 (m, 1H), 3.88 (s, 3H), 3.64 (s, 3H), 3.16 (d, J = 11.2 Hz, 2H), 2.95-2.83 (m, 1H), 2.79-2.67 (m, 3H), 2.65-2.59 (m, 1H), 2.48-2.41 (m, 1H), 2.31 (d, J = 7.2 Hz, 2H), 2.27 (s, 3H), 2.20-2.12 (m, 2H), 2.04-1.95 (m, 3H), 1.94-1.85 (m, 2H), 1.85-1.85 (m, 2H), 1.73-1.61 (m, 2H), 1.60-1.48 (m, 1H), 1.20-1.04 (m, 2H) |
| I-413 | AQK | BIQ | 803.4 | 11.09 (s, 1H), 10.31 (s, 1H), 8.91 (s, 1H), 8.48-8.38 (m, 2H), 8.35 (s, 1H), 8.24 (dd, J = 0.8, 7.6 Hz, 1H), 7.06-6.80 (m, 3H), 5.35 (dd, J = 5.2, 12.8 Hz, 1H), 4.43-4.28 (m, 1H), 4.07 (s, 3H), 3.64 (s, 3H), 3.16 (d, J = 10.4 Hz, 2H), 2.94-2.84 (m, 1H), 2.79-2.63 (m, 4H), 2.45-2.40 (m, 1H), 2.34-2.24 (m, 5H), 2.17-2.10 (m, 2H), 2.01-1.78 (m, 7H), 1.72-1.51 (m, 3H), 1.18-1.04 (m, 2H) |
| I-414 | AZK | BIQ | 774.4 | 11.10 (s, 1H), 10.32-10.31 (m, 2H), 8.92 (s, 1H), 8.50-8.38 (m, 2H), 8.38-8.34 (m, 1H), 8.24 (dd, J = 1.2, 7.6 Hz, 1H), 7.12-6.93 (m, 3H), 5.40 (dd, J = 5.6, 12.4 Hz, 1H), 4.45-4.36 (m, 1H), 4.07 (s, 3H), 3.65-3.60 (m, 5H), 3.24-3.12 (m, 2H), 3.07-3.56 (m, 2H), 2.94-2.85 (m, 1H), 2.77-2.61 (m, 2H), 2.38-2.31 (m, 2H), 2.21-2.08 (m, 4H), 2.04-1.86 (m, 6H), 1.36-1.20 (m, 2H) |
| I-415 | AZK | BLX | 773.5 | 11.68 (s, 1H), 11.16 (s, 1H), 8.93 (d, J = 7.0 Hz, 1H), 8.65 (s, 1H), 8.61-8.57 (m, 1H), 8.51 (s, 1H), 8.38 (s, 1H), 7.60 (s, 1H), 7.13-7.01 (m, 4H), 5.99 (s, 1H), 5.44 (dd, J = 4.8, 12.4 Hz, 1H), 4.54-4.44 (m, 1H), 3.66 (s, 3H), 3.50-3.48 (m, 1H), 3.13-3.05 (m, 2H), 2.99-2.92 (m, 1H), 2.83-2.76 (m, 1H), 2.75-2.71 (m, 2H), 2.35-2.29 (m, 2H), 2.25-2.19 (m, 3H), 2.09-1.99 (m, 6H), 1.90-1.86 (m, 4H), 1.69 (s, 6H), 1.61-1.53 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | $^1$HNMR (400 MHz, DMSO-$d_6$) δ |
|---|---|---|---|---|
| I-416 | AZK | BIW | 774.4 | 11.09 (s, 1H), 10.11 (s, 1H), 9.47 (s, 2H), 8.33 (s, 1H), 8.16 (s, 1H), 7.10 (s, 1H), 7.06-6.95 (m, 3H), 5.37 (dd, J = 5.2, 12.4 Hz, 1H), 4.45-4.34 (m, 1H), 3.88 (s, 3H), 3.59 (s, 3H), 3.27-3.26 (m, 1H), 3.05 (d, J = 11.2 Hz, 2H), 2.93-2.85 (m, 1H), 2.77-2.67 (m, 1H), 2.65-2.57 (m, 1H), 2.29 (d, J = 6.4 Hz, 2H), 2.23-2.11 (m, 4H), 2.05-1.96 (m, 3H), 1.96-1.86 (m, 2H), 1.86-1.75 (m, 4H), 1.72-1.63 (m, 1H), 1.21-1.09 (m, 2H) |
| I-417 | AZK | BIZ | 789.3 | 11.10 (s, 1H), 10.78 (s, 1H), 8.58 (s, 1H), 8.48-8.40 (m, 3H), 8.23 (d, J = 8.0 Hz, 1H), 8.19 (s, 1H), 7.81 (s, 1H), 7.04-6.98 (m, 3H), 5.40-5.36 (m, 1H), 4.50-4.43 (m, 1H), 3.60 (s, 3H), 3.01 (d, J = 11.2 Hz, 2H), 2.91-2.86 (m, 1H), 2.77-2.61 (m, 3H), 2.24 (d, J = 7.2 Hz, 2H), 2.19-2.08 (m, 5H), 2.01-1.90 (m, 6H), 1.81-1.77 (m, 4H), 1.71-1.67 (m, 1H), 1.20-1.11 (m, 2H) |
| I-418 | AQK | BIZ | 818.3 | 11.09 (s, 1H), 10.78 (s, 1H), 8.58 (s, 1H), 8.48-8.40 (m, 3H), 8.27-8.22 (m, 1H), 7.81 (s, 1H), 7.00-6.96 (m, 1H), 6.92-6.89 (m, 2H), 5.38-8.34 (m, 1H), 4.50-4.43 (m, 1H), 3.65 (s, 3H), 3.47-3.45 (m, 3H), 3.16 (d, J = 10.8 Hz, 2H), 2.94-2.86 (m, 1H), 2.75-2.60 (m, 4H), 2.51-2.49 (m, 1H), 2.33-2.30 (m, 2H), 2.27 (s, 3H), 2.18-2.15 (m, 2H), 2.02-1.88 (m, 5H), 1.82-1.80 (m, 2H), 1.71-1.56(m, 3H), 1.17-1.08 (m, 2H) |
| I-419[h] | AQK | BJA | 778.3 | 11.86 (s, 1H), 11.09 (s, 1H), 8.64-8.63 (m, 2H), 8.35 (s, 1H), 8.18 (s, 1H), 8.13-8.11 (m, 1H), 7.65-761 (m, 1H), 7.56 (s, 1H), 7.00-6.96 (m, 1H), 6.92-6.86 (m, 2H), 6.06 (s, 1H), 5.37-5.33 (m, 1H), 4.46-4.40 (m, 1H), 3.64 (s, 3H), 3.16 (d, J = 10.8 Hz, 2H), 2.92-2.85 (m, 1H), 2.76-2.60 (m, 4H), 2.52 ( s, 1H), 2.33 (d, J = 6.4 Hz, 2H), 2.28 (s, 3H), 2.16-2.14 (m, 2H), 2.01-1.88 (m, 5H), 1.81 (d, J = 10.8 Hz, 2H), 1.71-1.65 (m, 2H), 1.62 (s, 6H), 1.17-1.08 (m, 2H) |
| I-420[h] | AQK | BMA | 777.4 | 11.08 (s, 1H), 8.61 (s, 1H), 8.37 (s, 1H), 7.68-7.46 (m, 6H), 7.01-6.95 (m, 1H), 6.94-6.85 (m, 2H), 6.20 (s, 1H), 5.39-5.32 (m, 1H), 4.49-4.38 (m, 1H), 3.65 (s, 3H), 3.31 (s, 2H), 3.16 (d, J = 11.6 Hz, 2H), 2.95-2.84 (m, 1H), 2.79-2.70 (m, 3H), 2.66-2.59 (m, 1H), 2.33-2.28 (m, 2H), 2.27 (s, 3H), 2.16 (d, J = 10.8 Hz, 2H), 2.01-1.88 (m, 5H), 1.81 (d, J = 10.0 Hz, 2H), 1.72-1.64 (m, 2H), 1.60 (s, 6H), 1.18-1.06 (m, 2H) |
| I-421 | AQK | BJB | 850.1 | 11.36 (s, 1H), 11.09 (s, 1H), 8.83 (s, 1H), 8.69 (s, 1H), 8.49-8.47 (m, 1H), 8.43-8.40 (m, 2H), 8.34 (s, 1H), 8.23-8.21 (m, 1H), 7.00-6.96 (m, 1H), 6.92-6.86 (m, 2H), 5.37-5.33 (m, 1H), 4.63-4.54 (m, 1H), 3.64 (s, 3H), 3.29 (s, 3H), 3.16 (d, J = 10.4 Hz, 2H), 2.93-2.86 (m, 1H), 2.76-2.70 (m, 3H), 2.64-2.60 (m, 1H), 2.33-2.30 (m, 2H), 2.26 (s, 3H), 2.21-2.18 (m, 2H), 2.01-1.95 (m, 5H), 1.82-1.79 (m, 2H), 1.69-1.56 (m, 3H), 1.19-1.09 (m, 2H) |
| I-422 | AQK | BBH | 828.4 | 11.09 (s, 1H), 10.50 (s, 1H), 8.68 (d, J = 3.6 Hz, 1H), 8.48-8.30 (m, 3H), 8.21 (d, J = 5.2 Hz, 1H), 7.40 (d, J = 3.6 Hz, 1H), 7.04-6.78 (m, 3H), 5.40-5.30 (m, 1H), 4.43-4.31 (m, 1H), 4.18-4.08 (, 1H), 3.64 (s, 3H), 3.20-3.11 (m, 2H), 2.92-2.84 (m, 1H), 2.78-2.64 (m, 4H), 2.37-2.25 (m, 5H), 2.21-2.09 (m, 2H), 2.04-1.87 (m, 5H), 1.85-1.77 (m, 2H), 1.72-1.51 (m, 3H), 1.19-1.04 (m, 2H), 0.99-0.86 (m, 2H), 0.82-0.71 (m, 2H) |
| I-423 | AZK | BJB | 821.4 | 11.37 (s, 1H), 11.10 (s, 1H), 8.85 (s, 1H), 8.69 (s, 1H), 8.49-8.47 (m, 1H), 8.44-8.40 (m, 1H), 8.35 (s, 1H), 8.29 (s, 1H), 8.23 (d, J = 8.0 Hz, 1H), 7.05-6.97 (m, 3H), 5.40-5.36 (m, 1H), 4.65-4.57 (m, 1H), 3.60 (s, 3H), 3.30 (s, 3H), 3.01 (d, J = 11.2 Hz, 2H), 2.94-2.85 (m, 1H), 2.76-2.69 (m, 1H), 2.65-2.61 (m, 1H), 2.24-2.20 (m, 4H), 2.11-1.94 (m, 7H), 1.81-1.71 (m, 5H), 1.22-1.13 (m, 2H) |
| I-424[e] | AQK | BJD | 871.6 | 11.09 (s, 1H), 11.08 (s, 1H), 8.78 (s, 1H), 8.54-8.46 (m, 1H), 8.41 (t, J = 8.0 Hz, 1H), 8.37 (s, 1H), 8.25-8.20 (m, 1H), 7.44 (s, 1H), 7.03-6.85 (m, 3H), 5.45-5.25 (m, 1H), 4.72 (s, 1H), 4.50-4.32 (m, 1H), 3.86-3.71 (m, 1H), 3.65 (s, 3H), 3.22-3.12 (m, 3H), 3.10-2.99 (m, 3H), 2.97-2.85 (m, 1H), 2.82-2.69 (m, 5H), |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)+ | 1HNMR (400 MHz, DMSO-$d_6$) δ |
|---|---|---|---|---|
| | | | | 2.65-2.55 (m, 2H), 2.42-2.34 (m, 2H), 2.20-2.10 (m, 2H), 2.04-1.91 (m, 7H), 1.90-1.80 (m, 2H), 1.79-1.61 (m, 5H), 1.24-1.07 (m, 3H) |
| I-425 | AQK | AWO | 838.4 | 11.09 (s, 1H), 10.44 (s, 1H), 8.72 (s, 1H), 8.50 (s, 1H), 8.48-8.45 (m, 1H), 8.44-8.38 (m, 1H), 8.23 (d, J = 7.6 Hz, 1H), 8.15 (s, 1H), 7.60-7.16 (m, 2H), 7.01-6.94 (m, 1H), 6.93-6.84 (m, 2H), 5.35 (dd, J = 5.4, 12.6 Hz, 1H), 4.53-4.39 (m, 1H), 3.64 (s, 3H), 3.16 (m, 3H), 2.96-2.82 (m, 1H), 2.78-2.57 (m, 4H), 2.32 (m, 2H), 2.28 (s, 3H), 2.20-2.11 (m, 2H), 2.03-1.87 (m, 5H), 1.81 (m, 2H), 1.74-1.51 (m, 3H), 1.21-1.04 (m, 2H) |
| I-426 | AQK | BMI | 817.2 | 11.10 (s, 1H), 10.57 (s, 1H), 8.65 (s, 1H), 8.52-8.45 (m, 1H), 8.45-8.38 (m, 1H), 8.25 (dd, J = 0.9, 7.7 Hz, 1H), 7.37 (s, 1H), 7.01-6.95 (m, 1H), 6.94-6.84 (m, 2H), 5.36 (dd, J = 5.4, 12.6 Hz, 1H), 4.43 (s, 2H), 4.02 (s, 3H), 4.02-3.95 (m, 1H), 3.65 (s, 3H), 3.16 (br d, J = 10.8 Hz, 2H), 2.95-2.85 (m, 1H), 2.79-2.59 (m, 4H), 2.47-2.41 (m, 1H), 2.28 (d, J = 6.8 Hz, 2H), 2.25 (s, 3H), 2.04-1.96 (m, 1H), 1.91 (d, J = 11.4 Hz, 2H), 1.83-1.74 (m, 4H), 1.71-1.55 (m, 4H), 1.52-1.42 (m, 1H), 1.10-0.99 (m, 2H) |
| I-427 | AQK | BMH | 830.4 | 11.01 (s, 1H), 10.04 (s, 1H), 8.60 (s, 1H), 8.42 (s, 1H), 8.33 (s, 1H), 7.55 (d, J = 8.0 Hz, 1H), 7.50 (s, 1H), 7.40 (t, J = 8.0 Hz, 1H), 7.12-7.08 (m, 1H), 7.00-6.84 (m, 3H), 5.34 (dd, J = 5.2, 12.4 Hz, 1H), 4.46-4.33 (m, 3H), 4.25-4.12 (m, 1H), 3.89-3.83 (m, 1H), 3.79-3.73 (m, 1H), 3.64 (s, 3H), 3.25-3.21 (m, 2H), 3.18-3.11 (m, 4H), 2.92-2.83 (m, 1H), 2.76-2.69 (m, 2H), 2.65-2.56 (m, 2H), 2.46-2.38 (m, 2H), 2.35-2.26 (m, 2H), 2.25 (s, 3H), 2.16-2.09 (m, 2H), 2.07-1.87 (m, 6H), 1.85-1.74 (m, 2H), 1.69-1.51 (m, 3H), 1.16-1.06 (m, 2H) |
| I-428 | AQK | BMD | 829.5 | 11.74 (s, 1H), 11.09 (s, 1H), 8.63 (s, 1H), 8.36 (s, 1H), 8.23-8.14 (m, 1H), 7.91 (d, J = 1.6 Hz, 1H), 7.85 (d, J = 1.6 Hz, 2H), 7.59 (s, 1H), 7.00-6.94 (m, 1H), 6.92-6.85 (m, 2H), 5.35 (dd, J = 5.6, 12.8 Hz, 1H), 4.47-4.37 (m, 1H), 3.86 (s, 1H), 3.64 (s, 3H), 3.57 (s, 1H), 3.15 (d, J = 12.0 Hz, 2H), 2.96-2.82 (m, 1H), 2.77-2.66 (m, 3H), 2.65-2.57 (m, 1H), 2.32 (dd, J = 1.6, 3.6 Hz, 2H), 2.28 (s, 3H), 2.14 (d, J = 12.0 Hz, 2H), 2.02-1.86 (m, 5H), 1.81 (d, J = 9.6 Hz, 2H), 1.67 (s, 1H), 1.64 (s, 6H), 1.60-1.53 (m, 1H), 1.11 (q, J = 12.0 Hz, 2H) |
| I-429 | AQK | BMG | 830.6 | 11.09 (s, 1H), 10.04 (s, 1H), 8.60 (s, 1H), 8.42 (s, 1H), 8.33 (s, 1H), 7.56 (d, J = 7.6 Hz, 1H), 7.51 (s, 1H), 7.40 (t, J = 8.0 Hz, 1H), 7.12-7.09 (m, 1H), 7.01-6.94 (m, 1H), 6.93-6.89 (m, 1H), 6.87 (d, J = 7.6 Hz, 1H), 5.37-5.27 (m, 1H), 4.49-4.32 (m, 3H), 4.21-4.18 (m, 1H), 3.95-3.83 (m, 1H), 3.80-3.71 (m, 1H), 3.64 (s, 3H), 3.39 (m, 1H), 3.22-3.20 (m, 2H), 3.17-3.15 (m, 3H), 2.94-2.83 (m, 1H), 2.77-2.69 (m, 2H), 2.68-2.55 (m, 3H), 2.33-2.32 (m, 2H), 2.28 (s, 3H), 2.25-2.23 (m, 1H), 2.15-2.12 (m, 2H), 2.09-1.87 (m, 6H), 1.83-1.80 (m, 2H), 1.72-1.51 (m, 3H), 1.19-1.04 (m, 2H) |
| I-468 | AQK | BNX | 820.6 | 11.09 (s, 1H), 10.51 (s, 1H), 8.53 (d, J = 2.8 Hz, 1H), 8.50-8.44 (m, 2H), 8.44-8.38 (m, 1H), 8.23 (d, J = 7.6 Hz, 1H), 7.01-6.94 (m, 1H), 6.93-6.84 (m, 2H), 5.37-5.33 (m, 1H), 4.51-4.40 (m, 1H), 4.07 (d, J = 0.8 Hz, 3H), 3.64 (s, 3H), 3.15 (d, J = 11.2 Hz, 3H), 2.95-2.84 (m, 1H), 2.76-2.61 (m, 4H), 2.31 (d, J = 6.8 Hz, 2H), 2.27 (s, 3H), 2.20-2.11 (m, 2H), 2.03-1.88 (m, 5H), 1.80 (d, J = 11.2 Hz, 2H), 1.73-1.54 (m, 3H), 1.18-1.04 (m, 2H) |
| I-469 | AQK | BNY | 838.3 | 11.09 (s, 1H), 10.53 (s, 1H), 8.50-8.40 (m, 2H), 8.28-8.22 (m, 2H), 7.00-6.95 (m, 1H), 6.94-6.85 (m, 2H), 5.35 (dd, J = 5.2, 12.4 Hz, 1H), 4.52-4.44 (m, 1H), 4.10 (d, J = 1.2 Hz, 3H), 3.65 (s, 3H), 3.58 (m, 1H), 3.17-3.15 (m, 1H), 2.90 (m, 1H), 2.72-2.69 (m, 2H), 2.62 (m, 2H), 2.30 (m, 2H), 2.26 (s, 3H), 2.08-1.94 (m, 8H), 1.87-1.74 (m, 3H), 1.72-1.52 (m, 4H), 1.18-1.10 (m, 2H) |
| I-470 | AQK | BNZ | 820.3 | 11.10 (s, 1H), 10.51 (s, 1H), 8.54 (s, 1H), 8.49-8.44 (m, 1H), 8.44-8.39 (m, 1H), 8.23 (d, J = 7.6 Hz, 1H), |

TABLE 7-continued

Compounds synthesized via Method 2 with the reductive amination of various intermediate amines and aldehydes.

| I-# | Intermediate Amine | Intermediate Aldehyde | LCMS (ES+) m/z (M + H)$^+$ | $^1$HNMR (400 MHz, DMSO-$d_6$) δ |
|---|---|---|---|---|
| | | | | 7.06 (d, J = 1.2 Hz, 1H), 7.01-6.96 (m, 1H), 6.94-6.85 (m, 2H), 5.36 (dd, J = 5.2, 12.8 Hz, 1H), 4.50-4.37 (m, 1H), 3.99 (s, 3H), 3.65 (s, 3H), 3.17 (d, J = 11.2 Hz, 3H), 2.97-2.84 (m, 1H), 2.80-2.63 (m, 4H), 2.42 (s, 2H), 2.36 (s, 3H), 2.08-1.93 (m, 7H), 1.86 (d, J = 10.4 Hz, 2H), 1.76-1.54 (m, 3H), 1.22-1.10 (m, 2H) |
| I-471 | AQK | BKQ | 790.5 | 11.09 (s, 1H), 10.23 (d, J = 2.4 Hz, 1H), 8.50 (s, 1H), 8.47-8.37 (m, 3H), 8.22 (dd, J = 1.2, 7.6 Hz, 1H), 7.54 (d, J = 12.0 Hz, 1H), 7.01-6.94 (m, 1H), 6.94-6.84 (m, 2H), 5.35 (dd, J = 5.6, 12.8 Hz, 1H), 4.51-4.40 (m, 1H), 3.64 (s, 3H), 3.17 (d, J = 11.6 Hz, 2H), 2.94-2.85 (m, 1H), 2.79-2.71 (m, 2H), 2.70-2.65 (m, 1H), 2.64-2.60 (m, 1H), 2.60-2.54 (m, 1H), 2.43-2.35 (m, 2H), 2.33 (s, 3H), 2.20-2.12 (m, 2H), 2.03-1.93 (m, 4H), 1.92-1.79 (m, 3H), 1.75-1.64 (m, 2H), 1.64-1.52 (m, 1H), 1.21-1.08 (m, 2H) |
| I-472 | AZK | BOA | 843.4 | 11.22 (s, 1H), 11.17-11.00 (m, 1H), 8.73 (s, 1H), 8.54-8.49 (m, 1H), 8.46-8.42 (m, 1H), 8.26 (d, J = 7.6 Hz, 1H), 7.62 (s, 1H), 7.25-7.20 (m, 1H), 7.01 (d, J = 6.8 Hz, 1H), 6.98-6.95 (m, 1H), 5.37 (dd, J = 4.8, 12.4 Hz, 1H), 4.46 (s, 2H), 4.06-3.98 (m, 1H), 3.88-3.82 (m, 4H), 3.59 (s, 3H), 2.97 (d, J = 10.4 Hz, 2H), 2.92 (s, 4H), 2.66-2.58 (m, 2H), 2.18 (d, J = 6.8 Hz, 2H), 2.10-1.96 (m, 4H), 1.92 (d, J = 12.8 Hz, 2H), 1.82-1.73 (m, 6H), 1.66-1.49 (m, 4H), 1.12-0.98 (m, 2H) |
| I-473 | AZK | BOB | 855.6 | 11.17-11.01 (m, 1H), 10.74 (s, 1H), 8.58 (s, 1H), 8.52-8.47 (m, 1H), 8.43 (d, J = 8.0 Hz, 1H), 8.24 (d, J = 6.8 Hz, 1H), 7.47 (s, 1H), 7.05-6.95 (m, 3H), 5.41-5.33 (m, 1H), 4.62 (s, 1H), 4.43 (s, 2H), 4.14-4.07 (m, 1H), 4.07-3.97 (m, 1H), 3.93 (d, J = 7.6 Hz, 1H), 3.68 (d, J = 6.4 Hz, 1H), 3.59 (s, 3H), 3.00-2.95 (m, 2H), 2.64-2.60 (m, 2H), 2.18 (d, J = 6.0 Hz, 2H), 2.09-1.96 (m, 5H), 1.95-1.85 (m, 4H), 1.83-1.72 (m, 7H), 1.66-1.49 (m, 4H), 1.13-1.00 (m, 2H) |
| I-474 | BAI | BOA | 844.4 | 11.23 (s, 1H), 11.09 (s, 1H), 8.73 (s, 1H), 8.54-8.49 (m, 1H), 8.46-8.40 (m, 1H), 8.29-8.25 (m, 1H), 7.62 (s, 1H), 7.01-6.92 (m, 2H), 6.88 (d, J = 7.2 Hz, 1H), 5.40-5.30 (m, 1H), 4.46 (s, 2H), 4.06-3.99 (m, 1H), 3.87-3.84 (m, 4H), 3.63 (s, 3H), 3.00-2.84 (m, 12H), 2.22 (d, J = 8.0 Hz, 2H), 2.04-1.89 (m, 4H), 1.83-1.72 (m, 3H), 1.68-1.53 (m, 4H), 1.11-1.03 (m, 2H) |
| I-475 | AZK | BOC | 855.4 | 10.75 (s, 1H), 8.58 (s, 1H), 8.52-8.47 (m, 1H), 8.44-8.42 (m, 1H), 8.25 (d, J = 6.8 Hz, 1H), 7.47 (s, 1H), 7.06-6.93 (m, 3H), 5.42-5.32 (m, 1H), 4.62 (s, 1H), 4.43 (s, 2H), 4.10 (s, 1H), 4.05-3.98 (m, 1H), 3.93 (d, J = 8.0 Hz, 1H), 3.68 (d, J = 6.0 Hz, 1H), 3.59 (s, 3H), 3.00-2.94 (m, 2H), 2.92-2.84 (m, 1H), 2.65-2.63 (m, 2H), 2.20-2.15 (m, 2H), 2.09-2.00 (m, 4H), 1.95-1.85 (m, 4H), 1.84-1.69 (m, 7H), 1.69-1.46 (m, 4H), 1.14-1.01 (m, 2H) |
| I-476 | AQK | BOE | 831.1 | 11.09 (s, 1H), 10.31 (s, 1H), 8.49-8.35 (m, 2H), 8.25-8.19 (m, 2H), 7.04-6.94 (m, 2H), 6.93-6.84 (m, 2H), 5.35 (dd, J = 5.2, 12.4 Hz, 1H), 4.00 (s, 2H), 3.93 (s, 3H), 3.63 (s, 3H), 3.14 (d, J = 11.2 Hz, 2H), 2.94-2.84 (m, 1H), 2.79-2.74 (m, 1H), 2.74-2.68 (m, 2H), 2.65-2.58 (m, 1H), 2.46-2.38 (m, 2H), 2.26-2.18 (m, 5H), 2.02-1.96 (m, 1H), 1.91-1.82 (m, 2H), 1.81-1.72 (m, 4H), 1.70-1.58 (m, 2H), 1.55-1.45 (m, 2H), 1.43-1.34 (m, 1H), 1.30 (s, 6H), 1.05-0.91 (m, 2H) |
| I-477 | AZK | BOE | 802.1 | 11.09 (s, 1H), 10.31 (s, 1H), 8.47-8.36 (m, 2H), 8.26-8.18 (m, 2H), 7.06-6.93 (m, 4H), 5.37 (dd, J = 5.6, 12.0 Hz, 1H), 3.99 (s, 2H), 3.93 (s, 3H), 3.58 (s, 3H), 3.19-3.15 (m, 1H), 3.01-2.93 (m, 2H), 2.91-2.81 (m, 1H), 2.80-2.68 (m, 2H), 2.65-2.57 (m, 1H), 2.18-2.10 (m, 2H), 2.07-2.00 (m, 2H), 2.00-1.95 (m, 1H), 1.91-v1.83 (m, 2H), 1.82-1.70 (m, 6H), 1.56-1.42 (m, 3H), 1.30 (s, 6H), 1.07-0.92 (m, 2H) |

TABLE 7-continued

Compounds synthesized via Method 2 with the reductive amination of various intermediate amines and aldehydes.

| I-# | Intermediate Amine | Intermediate Aldehyde | LCMS (ES+) m/z $(M + H)^+$ | $^1$HNMR (400 MHz, DMSO-$d_6$) δ |
|---|---|---|---|---|
| I-488 | AZK | BJL | 738.4 | 11.76 (s, 1H), 11.09 (s, 1H), 8.74-8.62 (m, 1H), 8.60-8.56 (m, 1H), 8.19 (s, 1H), 7.61 (s, 1H), 7.11-6.89 (m, 3H), 6.19 (s, 1H), 5.37 (m, 1H), 3.60-3.56 (m, 4H), 3.03-2.83 (m, 5H), 2.73-2.56 (m, 3H), 2.33 (m, 1H), 2.23-2.14 (m, 4H), 2.12-1.90 (m, 6H), 1.85-1.72 (m, 4H), 1.66-1.56 (m, 8H), 1.14-1.00 (m, 2H) |

For Method 2, when the amine is the HCl salt, TEA was added to free base the salt, followed by HOAc to adjust the pH to 3-4 or 5-7. KOAc could also be used in place of the TEA/HOAc combination. Method 2 was run anywhere from 0.5-48 hrs and the reaction temperature was run from −15° C. to rt. The final products were isolated under standard purification techniques including reverse HPLC, silica gel chromatography, and prep-TLC with appropriate solvent conditions. [a]Coupling was achieved with tetraethoxytitanium at rt for 12 hrs. Then $NaBH_3CN$ was added and the reaction mixture was stirred at rt for 1.5 hrs. [b] Precursor to AJF was dissolved in $H_2O$ and ACN, then deprotected using 1M HCl for 15 min and the solution was then lyophilized to give the final compound. C After the coupling, the product was treated with aq. HCl (1N) in ACN at 0° C. for 30 min to form the HCl salt of the product. [d] Coupling product was deprotected with 2M HCl solution at rt for 2 hrs and purified by prep-HPLC. [be]The product of the coupling was deprotected with TFA in ACN at rt for 30 min. The final product was purified by prep-HPLC. [cf]The product of the coupling was deprotected with pyridine;hydrofluoride in THE at 80° C. for 1 hr. Then the final product was purified by prep-HPLC. [d]LCMS measured as $(M+Na)^+$. [eh]LCMS measured as $(M-18)^+$.

Example 3 (Method 4). Synthesis of N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-methoxy-indazol-5-yl]-2-(trifluoromethyl)imidazo[1,5-a]pyrimidine-8-carboxamide (I-430)

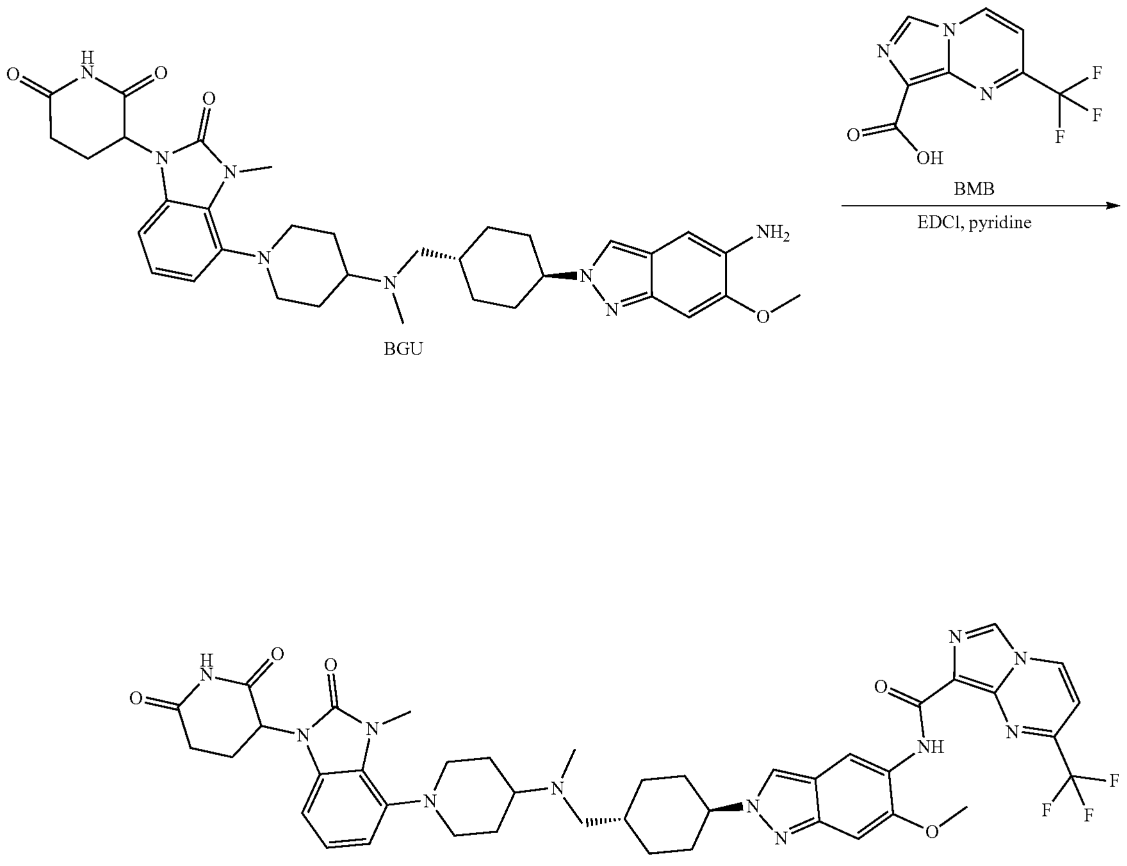 [SMILES: COc1cc2nn([C@H]3CC[C@H](CN(C)C4CCN(c5cccc6c5n(C)c(=O)n6C5CCC(=O)NC5=O)CC4)CC3)cc2cc1N ; O=C(O)c1ncn2ccc(C(F)(F)F)nc12 ; COc1cc2nn([C@H]3CC[C@H](CN(C)C4CCN(c5cccc6c5n(C)c(=O)n6C5CCC(=O)NC5=O)CC4)CC3)cc2cc1NC(=O)c1ncn2ccc(C(F)(F)F)nc12]

To a solution of 3-[4-[4-[[4-(5-amino-6-methoxy-indazol-2-yl)cyclohexyl]methyl-methyl-amino]- 1-piperidyl]-3-methyl-2-oxo-benzimidazol-1-yl]piperidine-2,6-dione (70.0 mg, 105 umol, HCl, Intermediate BGU) and 2-(trifluoromethyl)imidazo[1,5-a]pyrimidine-8-carboxylic acid (40.0 mg, 138 umol, 80% purity, Intermediate BMB) in pyridine (0.5 mL) was added EDCI (30.2 mg, 158 umol). The reaction mixture was stirred at 20° C. for 2 hrs. On completion, the reaction mixture was quenched with water (0.5 mL), then the residue was concentrated in vacuo. The crude product was purified by reversed-phase (0.1% FA condition) and then re-purified by Prep-HPLC (column: Phenomenex Synergi C18 150*25*10 um;mobile phase: [water(0.225% FA)-ACN]; B %: 17%-44%, 9 min) to give the title compound (12.7 mg, 13% yield, 97% purity, FA salt) as a yellow solid. $^1$H NMR (400 MHz, DMSO-$d_6$) δ 11.10 (s, 1H), 10.10 (s, 1H), 9.22 (d, J=7.2 Hz, 1H), 8.75 (d, J=8.4 Hz, 2H), 8.31 (s, 1H), 7.48 (d, J=7.2 Hz, 1H), 7.13 (s, 1H), 7.01-6.96 (m, 1H), 6.94-6.90 (m, 1H), 6.88 (d, J=8.4 Hz, 1H), 5.39-5.32 (m, 1H), 4.40-4.35 (m, 1H), 3.99 (s, 3H), 3.65 (s, 3H), 3.19-3.15 (m, 2H), 2.92-2.86 (m, 1H), 2.77-2.72 (m, 2H), 2.67-2.63 (m, 1H), 2.48-2.44 (m, 1H), 2.33-2.31 (m, 2H), 2.27 (s, 3H), 2.19-2.14 (m, 2H), 2.04-1.95 (m, 4H), 1.93-1.87 (m, 2H), 1.83-1.79 (m, 2H), 1.70-1.64 (m, 2H), 1.58-1.53 (m, 1H), 1.16-1.08 (m, 2H), LC-MS (ESI$^+$) m/z 842.6 (M+H)$^+$.

TABLE 8

Compounds synthesized via Method 4 with the coupling of various amines and acids.

| I-# | Intermediate Amine | Intermediate Acid | LCMS (ES+) m/z (M + H)$^+$ | $^1$HNMR (400 MHz, DMSO-d6) δ |
|---|---|---|---|---|
| I-431 | BGU | BMF | 799.6 | 11.09 (s, 1H), 9.35 (s, 1H), 8.52 (s, 1H), 8.29-8.26 (m, 2H), 7.10 (s, 1H), 7.00-6.84 (m, 3H), 5.38-5.31 (m, 1H), 4.65-4.52 (m, 1H), 4.44-4.30 (m, 1H), 3.95 (s, 3H), 3.64 (s, 3H), 3.15 (d, J = 11.2 Hz, 2H), 2.93-2.84 (m, 1H), 2.75-2.69 (m, 2H), 2.65-2.59 (m, 1H), 2.53-2.52 (m, 1H), 2.43 (s, 1H), 2.30 (d, J = 6.8 Hz, 2H), 2.26 (s, 3H), 2.13 (d, J = 12.0 Hz, 2H), 2.02-1.93 (m, 3H), 1.92-1.84 (m, 2H), 1.80 (d, J = 10.8 Hz, 2H), 1.71-1.60 (m, 2H), 1.59-1.51 (m, 1H), 1.48 (s, 3H), 1.46 (s, 3H), 1.18-1.02 (m, 2H) |

[a]The reaction was run anywhere from 1-2 hrs at rt. The final products were isolated under standard purification techniques including reverse HPLC and prep-TLC with appropriate solvent conditions.

Example 4 (Method 5). Synthesis of 3-chloro-N-[2-[4-[[[1-[1-(2,6-dioxo-3-piperidyl)-3-methyl-2-oxo-benzimidazol-4-yl]-4- piperidyl]-methyl-amino]methyl]cyclohexyl]-6-methoxy-indazol-5-yl]pyridine-2-carboxamide (I-432)

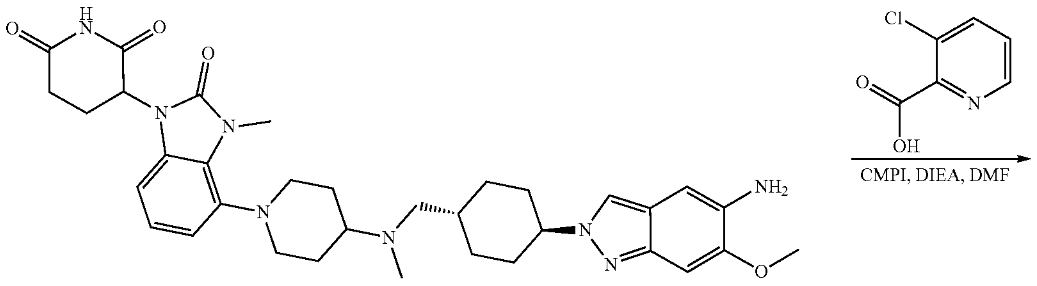

BGU

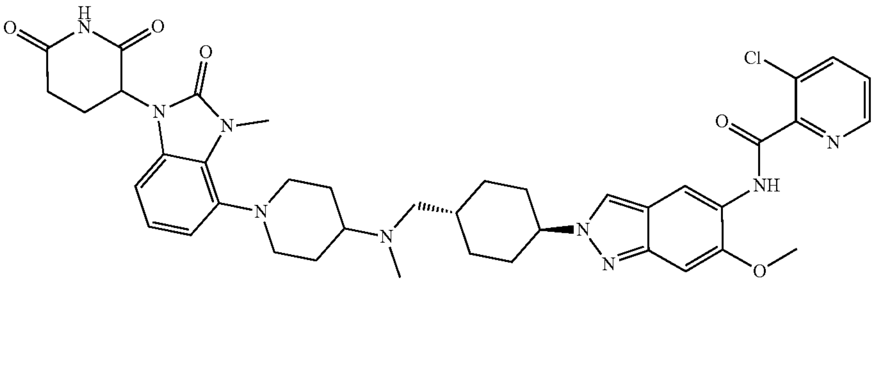

To a solution of 3-[4-[4-[[4-(5-amino-6-methoxy-indazol-2-yl)cyclohexyl]methyl-methyl-amino]-1-piperidyl]-3-methyl-2-oxobenzimidazol-1-yl]piperidine-2,6-dione (50.0 mg, 67.3 umol, Intermediate BGU) and 3-chloropyridine-2-carboxylic acid (CAS #57266-69-0, 10.6 mg, 67.3 umol) in DMF (1 mL) was added CMPI (20.6 mg, 80.8 umol) and DIEA (26.1 mg, 202 umol). The mixture was stirred at 25° C. for 2 hours. On completion, the reaction mixture was quenched by addition $H_2O$ (0.5 mL) at 25° C., and concentrated in vacuo. The residue was purified by prep-HPLC (column: Shim-pack C18 150*25*10 um; mobile phase: [water(0.225% FA)-ACN]; B %: 22%-42%, 10 min) to give the title compound (28.1 mg, 51% yield, FA salt) as a off-white solid. $^1$H NMR (400 MHz, DMSO-$d_6$) δ 11.09 (s, 1H), 10.30 (s, 1H), 8.67-8.66 (m, 1H), 8.61-8.60 (m, 1H), 8.31 (s, 1H), 8.14-8.11 (m, 2H), 7.68-7.65 (m, 1H), 7.11 (s, 1H), 7.00-6.96 (m, 1H), 6.93-6.87 (m, 2H), 5.38-5.33 (m, 1H), 4.38 (t, J=11.6 Hz, 1H), 3.94 (s, 3H), 3.65 (s, 3H), 3.29 (s, 3H), 3.18 (d, J=10.4 Hz, 2H), 2.93-2.85 (m, 1H), 2.78-2.70 (m, 3H), 2.64-2.60 (m, 1H), 2.39 (s, 2H), 2.16 (d, J=12.0 Hz, 2H), 2.01-1.94 (m, 4H), 1.88 (d, J=13.6 Hz, 3H), 1.75-1.64 (m, 3H), 1.16-1.10 (m, 2H); LC-MS (ESI$^+$) m/z 768.4 (M+H)$^+$.

TABLE 9

Compounds synthesized via Method 5 with the coupling of various amines and acids.

| I-# | Intermediate Amine | Intermediate Acid | LCMS (ES+) m/z (M + H)$^+$ | 1HNMR (400 MHz, DMSO-d6) δ |
|---|---|---|---|---|
| I-433 | BGU | 3,4-dichlorobenzoic acid (CAS# 51-44-5) | 801.2 | 11.10 (s, 1H), 9.68 (s, 1H), 8.30 (s, 1H), 8.22 (s, 1H), 8.01 (s, 1H), 7.95 (d, J = 8.0 Hz, 1H), 7.82 (d, J = 8.4 Hz, 1H), 7.08 (s, 1H), 7.01-6.96 (m, 1H), 6.94-6.86 (m, 2H), 5.42-5.31 (m, 1H), 4.45-4.34 (m, 1H), 3.88 (s, 3H), 3.66 (s, 3H), 3.17 (d, J = 11.2 Hz, 2H), 2.96-2.84 (m, 1H), 2.78-2.67 (m, 3H), 2.66-2.59 (m, 1H), 2.47 (s, 1H), 2.31 (d, J = 6.4 Hz, 2H), 2.27 (s, 3H), 2.16 (d, J = 12.4 Hz, 2H), 2.01-1.78 (m, 7H), 1.73-1.53 (m, 3H), 1.19-1.06 (m, 2H) |
| I-434 | BGU | 3-fluoropyridine-2-carboxylic acid (CAS# 152126-31-3) | 752.4 | 11.09 (s, 1H), 10.39 (s, 1H), 8.66 (s, 1H), 8.62-8.56 (m, 1H), 8.32 (s, 1H), 8.01-7.93 (m, 1H), 7.83-7.75 (m, 1H), 7.17-7.10 (m, 1H), 7.02-6.95 (m, 1H), 6.94-6.84 (m, 2H), 5.36 (dd, J = 5.2, 12.8 Hz, 1H), 4.48-4.29 (m, 1H), 4.03-3.91 (m, 3H), 3.65 (s, 3H), 3.17 (d, J = 11.2 Hz, 2H), 2.97-2.84 (m, 1H), 2.81-2.58 (m, 5H), 2.46-2.38 (m, 2H), 2.38-2.27 (m, 3H), 2.21-2.10 (m, 2H), 2.05-1.80 (m, 7H), 1.78-1.54 (m, 3H), 1.21-1.07 (m, 2H) |
| I-435 | BGU | 2,3-dichlorobenzoic acid CAS# 50-45-3) | 801.4 | 11.09 (s, 1H), 9.70 (s, 1H), 8.30 (s, 1H), 8.26 (s, 1H), 7.74 (dd, J = 1.6, 7.6 Hz, 1H), 7.58-7.51 (m, 1H), 7.50-7.42 (m, 1H), 7.05 (s, 1H), 7.01-6.94 (m, 1H), 6.94-6.85 (m, 2H), 5.35 (dd, J = 5.2, 12.8 Hz, 1H), 4.45-4.30 (m, 1H), 3.85 (s, 3H), 3.69-3.62 (m, 3H), 3.16 (d, J = 11.2 Hz, 2H), 2.96-2.82 (m, 1H), 2.80-2.57 (m, 4H), 2.45 (s, 1H), 2.32 (d, J = 6.8 Hz, 2H), 2.27 (s, 3H), 2.20-2.09 (m, 2H), 2.04-1.76 (m, 7H), 1.74-1.49 (m, 3H), 1.20-1.01 (m, 2H) |
| I-436 | BGU | thiazole-5-carboxylic acid (CAS# 14527-41-4) | 740.3 | 11.09 (s, 1H), 9.74 (s, 1H), 9.29 (s, 1H), 8.70 (s, 1H), 8.30 (s, 1H), 8.20 (s, 1H), 7.93-7.91 (m, 1H), 7.07 (s, 1H), 6.99-6.96 (m, 1H), 6.92-6.86 (m, 2H), 5.37-5.33 (m, 1H), 4.42-4.35 (m, 1H), 3.87 (s, 3H), 3.64 (s, 3H), 3.16 (d, J = 11.2 Hz, 2H), 2.92-2.85 (m, 1H), 2.75-2.70 (m, 2H), 2.64-2.60 (m, 1H), 2.32-2.30 (m, 2H), 2.26 (s, 3H), 2.16-2.13 (m, 2H), 2.01-1.89 (m, 6H), 1.83-1.79 (m, 2H), 1.67-1.56 (m, 3H), 1.13-1.08 (m, 2H) |
| I-437 | BGU | 3,5-difluoropyridine-2-carboxylic acid (CAS# 745784-04-7) | 770.2 | 11.09 (s, 1H), 10.20 (s, 1H), 8.70 (d, J = 2.4 Hz, 1H), 8.63 (s, 1H), 8.32 (s, 1H), 8.22-8.15 (m, 1H), 7.14 (s, 1H), 7.00-6.95 (m, 1H), 6.93-6.86 (m, 2H), 5.39-5.32(m, 1H), 4.43-4.32 (m, 1H), 3.97 (s, 3H), 3.65 (s, 3H), 3.16 (d, J = 10.8 Hz, 3H), 2.93-2.85 (m, 1H), 2.77-2.67 (m, 3H), 2.66-2.59 (m, 1H), 2.31 (d, J = 6.8 Hz, 2H), 2.27 (s, 3H), 2.15 (d, J = 11.2 Hz, 2H), 2.02-1.78 (m, 7H), 1.72-1.51 (m, 3H), 1.18-1.04 (m, 2H) |
| I-438 | BGU | 2-chlorobenzoic acid (CAS# 118-91-2) | 767.2 | 11.09 (s, 1H), 9.48 (s, 1H), 8.30 (s, 1H), 8.29 (s, 1H), 7.64-7.60 (m, 1H), 7.58-7.53 (m, 1H), 7.53-7.50 (m, 1H), 7.49-7.43 (m, 1H), 7.06 (s, 1H), 7.01-6.95 (m, 1H), 6.94-6.86 (m, 2H), 5.44-5.30 (m, 1H), 4.46-4.32 (m, 1H), 3.87 (s, 3H), 3.65 (s, 3H), 3.16 (d, J = 11.2 Hz, 3H), 2.93-2.85 (m, 1H), 2.76-2.61 (m, 4H), 2.31 (d, J = 6.8 Hz, 2H), 2.27 (s, 3H), 2.20-2.11 (m, 2H), 2.03-1.88 (m, 5H), 1.81 (d, J = 11.6 Hz, 2H), 1.69-1.53 (m, 3H), 1.17-1.06 (m, 2H) |
| I-439 | BGU | thiazole-2-carboxylic acid (CAS# 14190-59-1) | 740.4 | 11.09 (s, 1H), 9.83 (s, 1H), 8.54 (s, 1H), 8.34 (s, 1H), 8.17 (d, J = 3.2 Hz, 1H), 8.12 (d, J = 3.2 Hz, 1H), 7.16 (s, 1H), 7.02-6.95 (m, 1H), 6.95-6.83 (m, 2H), 5.36 (dd, J = 5.2, 12.8 Hz, 1H), 4.45-4.32 (m, 1H), |

TABLE 9-continued

| Compounds synthesized via Method 5 with the coupling of various amines and acids. | | | | |
|---|---|---|---|---|
| I-# | Intermediate Amine | Intermediate Acid | LCMS (ES+) m/z (M + H)+ | 1HNMR (400 MHz, DMSO-d6) δ |
| | | | | 3.98 (s, 3H), 3.65 (s, 3H), 3.16 (d, J = 11.2 Hz, 2H), 2.96-2.83 (m, 1H), 2.77-2.57 (m, 4H), 2.49-2.41 (m, 1H), 2.39-2.23 (m, 5H), 2.20-2.08 (m, 2H), 2.05-1.76 (m, 7H), 1.75-1.48 (m, 3H), 1.20-1.03 (m, 2H) |
| I-440[a, b] | BLZ | BLY | 781.5 | 11.45 (s, 1H), 11.09 (s, 1H), 8.52 (s, 1H), 8.31 (s, 1H), 8.10 (s, 1H), 7.52 (s, 1H), 7.02-6.94 (m, 1H), 6.94-6.85 (m, 2H), 6.02 (s, 1H), 5.35 (dd, J = 5.2, 12.8 Hz, 1H), 4.48-4.36 (m, 1H), 3.91 (s, 3H), 3.64 (s, 3H), 3.17 (d, J = 11.6 Hz, 2H), 2.95-2.83 (m, 1H), 2.78-2.66 (m, 3H), 2.63-2.57 (m, 1H), 2.45-2.39 (m, 2H), 2.35 (s, 3H), 2.19-2.10 (m, 2H), 2.04-1.79 (m, 8H), 1.77-1.63 (m, 3H), 1.61 (s, 6H), 1.21-1.07 (m, 2H) |
| I-441 | BGU | BLY | 771.5 | 11.26-10.88 (m, 1H), 9.29 (s, 1H), 8.54 (s, 1H), 8.28 (s, 1H), 8.15 (s, 1H), 7.11 (s, 1H), 7.00-6.94 (m, 1H), 6.93-6.83 (m, 2H), 5.39-5.29 (m, 1H), 4.43-4.30 (m, 1H), 3.95 (s, 3H), 3.94 (s, 3H), 3.64 (s, 3H), 3.15 (d, J = 11.2 Hz, 2H), 2.93-2.82 (m, 1H), 2.76-2.69 (m, 2H), 2.64-2.57 (m, 1H), 2.45-2.40 (m, 1H), 2.29 (d, J = 6.8 Hz, 2H), 2.25 (s, 3H), 2.17-2.10 (m, 2H), 2.02-1.76 (m, 8H), 1.71-1.60 (m, 2H), 1.59-1.49 (m, 1H), 1.17-1.04 (m, 2H) |
| I-442 | BGU | 3-(trifluoromethyl)benzoic acid (CAS# 454-92-2) | 801.5 | 11.09 (s, 1H), 9.76 (s, 1H), 8.32-8.26 (m, 3H), 8.06-7.94 (m, 2H), 7.78 (t, J = 7.6 Hz, 1H), 7.08 (s, 1H), 7.02-6.84 (m, 3H), 5.35 (dd, J = 5.2, 12.4 Hz, 1H), 4.44-4.31 (m, 1H), 3.87 (s, 3H), 3.64 (s, 3H), 3.20-3.13 (m, 2H), 2.97-2.82 (m, 1H), 2.78-2.69 (m, 2H), 2.58 (s, 1H), 2.47-2.39 (m, 2H), 2.30 (d, J = 6.4 Hz, 2H), 2.26 (s, 3H), 2.19-2.11 (m, 2H), 2.01-1.85 (m, 5H), 1.80 (d, J = 11.6 Hz, 2H), 1.73-1.61 (m, 2H), 1.59-1.50 (m, 1H), 1.17-1.05 (m, 2H) |
| I-443 | BGU | 4-(trifluoromethyl)benzoic acid (CAS# 328-90-5) | 801.5 | 11.09 (s, 1H), 9.66 (s, 1H), 8.30 (s, 1H), 8.16 (d, J = 7.8 Hz, 2H), 8.09 (s, 1H), 7.91 (d, J = 8.4 Hz, 2H), 7.08 (s, 1H), 7.02-6.82 (m, 3H), 5.43-5.29 (m, 1H), 4.45-4.33 (m, 1H), 3.88 (s, 3H), 3.64 (s, 3H), 3.16 (d, J = 11.2 Hz, 2H), 2.95-2.83 (m, 1H), 2.77-2.60 (m, 4H), 2.47-2.42 (m, 1H), 2.30 (d, J = 6.8 Hz, 2H), 2.26 (s, 3H), 2.15 (d, J = 12.8 Hz, 2H), 2.00-1.77 (m, 7H), 1.72-1.53 (m, 3H), 1.17-1.04 (m, 2H) |
| I-444[a, b] | BLZ | benzoic acid (CAS# 185556-56-3) | 743.4 | 11.62 (s, 1H), 11.10 (s, 1H), 8.69 (s, 1H), 8.35 (s, 1H), 7.97-7.91 (m, 2H), 7.64-7.56 (m, 4H), 7.01-6.96 (m, 1H), 6.94-6.86 (m, 2H), 6.53 (s, 1H), 5.42-5.28 (m, 1H), 4.48-4.40 (m, 1H),3.65 (s, 3H),3.19 (d, J = 12.0 Hz, 2H), 2.94-2.85 (m, 1H), 2.82-2.56 (m, 6H), 2.45-2.35 (m, 3H), 2.22-2.11 (m, 2H), 2.04-1.82 (m, 8H), 1.81-1.68 (m, 3H), 1.65 (s, 6H), 1.17 (d, J = 11.6 Hz, 2H) |
| I-445 | BGU | 4-fluorobenzoic acid (CAS# 456-22-4) | 751.4 | 11.09 (s, 1H), 9.44 (s, 1H), 8.29 (s, 1H), 8.08 (s, 1H), 8.10-8.00 (m, 2H), 7.41-7.33 (m, 2H), 7.08 (s, 1H), 7.02-6.95 (m, 1H), 6.93-6.85 (m, 2H), 5.40-5.30 (m, 1H), 4.45-4.32 (m, 1H), 3.88 (s, 3H), 3.65 (s, 3H), 3.20-3.12 (m, 2H), 2.95-2.83 (m, 1H), 2.79-2.71 (m, 2H), 2.65-2.57 (m, 1H), 2.48-2.44 (m, 1H), 2.33-2.29 (m, 2H), 2.27 (s, 3H), 2.20-2.13 (m, 2H), 2.06-1.75 (m, 8H), 1.73-1.53 (m, 3H), 1.20-1.03 (m, 2H) |
| I-446[b] | BLZ | 3-(trifluoromethyl)benzoic acid (CAS# 454-92-2) | 811.5 | 11.81 (s, 1H), 11.09 (s, 1H), 8.67 (s, 1H), 8.37 (s, 1H), 8.24-8.16 (m, 2H), 8.01 (d, J = 7.6 Hz, 1H), 7.90-7.82 (m, 1H), 7.59 (s, 1H), 7.00-6.94 (m, 1H), 6.94-6.84 (m, 2H), 6.78-6.31 (m, 1H), 5.35 (dd, J = 5.2, 12.8 Hz, 1H), 4.48-4.37 (m, 1H), 3.64(s, 3H), 3.16 (d, J = 11.2 Hz, 2H), 2.95-2.84 (m, 1H), 2.78-2.65 (m, 3H), 2.65-2.58 (m, 1H), 2.47-2.41 (m, 1H), 2.33-2.28 (m, 2H), 2.26 (s, 3H), 2.19-2.11 (m, 2H), 2.04-1.95 (m, 3H), 1.94-1.86 (m, 2H), 1.80 (d, J = 11.2 Hz, 2H), 1.71-1.55 (m, 9H), 1.21-1.06 (m, 2H) |
| I-447[a, b] | BLZ | 2-(trifluoromethyl)thiazole-4-carboxylic acid (CAS# 915030-08-9) | 818.3 | 12.00 (s, 1H), 11.09 (s, 1H), 8.82 (s, 1H), 8.61 (s, 1H), 8.37 (s, 1H), 7.56 (s, 1H), 7.01-6.96 (m, 1H), 6.94-6.86 (m, 2H),6.12(s, 1H), 5.41-5.31 (m, 1H), 4.51-4.38 (m, 1H), 3.65 (s, 3H), 3.17 (d, J = 10.4 Hz, 2H), 2.96-2.83 (m, 1H), 2.79-2.58 (m, 4H), |

TABLE 9-continued

Compounds synthesized via Method 5 with the coupling of various amines and acids.

| I-# | Intermediate Amine | Intermediate Acid | LCMS (ES+) m/z (M + H)$^+$ | 1HNMR (400 MHz, DMSO-d6) δ |
|---|---|---|---|---|
| | | | | 2.36-2.30 (m, 2H), 2.28 (s, 3H), 2.20-2.11 (m, 2H), 2.04-1.78 (m, 8H), 1.77-1.63 (m, 3H), 1.62 (s, 6H), 1.21-1.06 (m, 2H) |
| I-448[a] | BLZ | 6-(trifluoromethyl)pyridazine-3-carboxylic acid (CAS# 1192155-05-7) | 831.2 | 12.85 (s, 1H), 11.09 (s, 1H), 8.78 (s, 1H), 8.65-8.61 (m, 1H), 8.52 (d, J = 8.8 Hz, 1H), 8.40 (s, 1H), 7.60 (s, 1H), 6.97 (d, J = 8.0 Hz, 1H), 6.94-6.84 (m, 2H), 6.29 (s, 1H), 5.42-5.28 (m, 1H),4.51-4.37 (m, 1H), 3.65 (s, 3H), 3.16 (d, J = 11.2 Hz, 2H), 2.94-2.85 (m, 1H), 2.84-2.53 (m, 5H), 2.31 (d, J = 6.8 Hz, 2H), 2.27 (s, 3H), 2.16 (d, J = 11.2 Hz, 2H), 2.07-1.71 (m, 8H), 1.65 (s, 6H), 1.62-1.48 (m, 2H), 1.13 (d, J = 12.4 Hz, 2H) |
| I-449[a] | BLZ | 4-(trifluoromethyl)benzoic acid (CAS# 328-90-5) | 829.4 | 11.79 (s, 1H), 11.10 (s, 1H), 8.68 (s, 1H), 8.38 (s, 1H), 8.11 (s, 2H), 7.98 (d, J = 8.0 Hz, 2H), 7.59 (s, 1H), 7.04-6.96 (m, 1H), 6.95-6.87 (m, 2H), 6.59 (s, 1H), 5.45-5.29 (m, 1H), 4.55-4.36 (m, 1H), 3.66 (s, 3H), 3.30 (s, 3H), 3.23-3.18 (m, 2H), 2.93-2.84 (m, 1H), 2.83-2.70 (m, 3H), 2.70-2.59 (m, 3H), 2.21-2.14 (m, 2H), 2.06-1.85 (m, 8H), 1.83-1.70 (m, 3H), 1.66 (s, 6H), 1.26-1.12 (m, 2H) |
| I-450 | BGU | 2-(trifluoromethyl)thiazole-4-carboxylic acid (CAS# 915030-08-9) | 808.5 | 11.09 (s, 1H), 9.75 (s, 1H), 8.86 (s, 1H), 8.55 (s, 1H), 8.33 (s, 1H), 7.14 (s, 1H), 7.03-6.82 (m, 3H), 5.36 (dd, J =5.6, 12.8 Hz, 1H), 4.46-4.31 (m, 1H), 3.96 (s, 3H), 3.65 (s, 3H), 3.17 (d, J = 11.2 Hz, 2H), 2.94-2.83 (m, 1H), 2.79-2.56 (m, 5H), 2.39 (d, J = 3.6 Hz, 2H), 2.33 (s, 3H), 2.15 (d, J = 11.2 Hz, 2H), 2.03-1.80 (m, 7H), 1.76-1.54 (m, 3H), 1.21-1.02 (m, 2H) |
| I-451[b] | BLZ | 3-fluorobenzoic acid (CAS# 455-38-9) | 761.5 | 11.83-11.53 (m, 1H), 11.41-10.58 (m, 1H), 8.66 (s, 1H), 8.35 (s, 1H), 7.76 (d, J = 8.0 Hz, 1H), 7.70-7.60 (m, 2H), 7.58 (s, 1H), 7.50-7.45 (m, 1H), 7.01-6.84 (m, 3H), 6.78-6.28 (m, 1H), 5.34 (dd, J = 5.6, 12.8 Hz, 1H), 4.48-4.37 (m, 1H), 3.64 (s, 3H), 3.16 (d, J = 10.4 Hz, 2H), 2.96-2.81 (m, 1H), 2.79-2.66 (m, 3H), 2.64-2.57 (m, 1H), 2.46-2.41 (m, 1H), 2.30 (d, J = 6.4 Hz, 2H), 2.26 (s, 3H), 2.18-2.10 (m, 2H), 2.02-1.87 (m, 5H), 1.83-1.76 (m, 2H), 1.70-1.55 (m, 9H), 1.17-1.05 (m, 2H) |
| I-452 | BGU | 6-(trifluoromethyl)pyridazine-3-carboxylic acid (CAS# 1192155-05-7) | 803.5 | 11.09 (s, 1H), 10.67 (s, 1H), 8.70 (s, 1H), 8.66-8.60 (m, 1H), 8.58-8.51 (m, 1H), 8.37 (s, 1H), 7.18 (s, 1H), 7.00-6.95 (m, 1H), 6.93-6.85 (m, 2H), 5.35 (dd, J = 5.6, 12.8 Hz, 1H), 4.44-4.34 (m, 1H), 4.01 (s, 3H), 3.65 (s, 3H), 3.16 (d, J = 10.8 Hz, 2H), 2.93-2.84 (m, 1H), 2.75-2.70 (m, 2H), 2.64-2.58 (m, 1H), 2.46-2.42 (m, 1H), 2.30 (d, J = 6.8 Hz, 2H), 2.26 (s, 3H), 2.19-2.12 (m, 2H), 2.04-1.85 (m, 6H), 1.83-1.77 (m, 2H), 1.72-1.62 (m, 2H), 1.60-1.51 (m, 1H), 1.18-1.06 (m, 2H) |
| I-453 | BGU | 3-chlorobenzoic acid (CAS# 535-80-8) | 767.4 | 11.09 (s, 1H),9.57(s, 1H), 8.30(s, 1H), 8.04 (s, 1H), 8.00 (s, 1H), 7.93 (d, J = 7.2 Hz, 1H), 7.67 (d, J = 7.2 Hz, 1H), 7.60-7.54 (m, 1H), 7.07 (s, 1H), 7.01-6.95 (m, 1H), 6.94-6.85 (m, 2H), 5.42-5.25 (m, 1H), 4.44-4.31 (m, 1H), 3.87 (s, 3H), 3.65 (s, 3H), 3.19-3.14 (m, 2H), 2.94-2.83 (m, 1H), 2.77-2.59 (m, 4H), 2.31 (d, J = 6.8 Hz, 2H), 2.27 (s, 3H), 2.15 (d, J = 11.6 Hz, 2H), 2.05-1.76 (m, 8H), 1.73-1.54 (m, 3H), 1.17-1.05 (m, 2H) |
| I-454 | BGU | 4-chlorobenzoic acid (CAS# 74-11-3) | 767.4 | 11.09 (s, 1H), 9.49 (s, 1H), 8.29 (s, 1H), 8.08 (s, 1H), 7.99 (d, J = 8.4 Hz, 2H), 7.60 (d, J = 8.4 Hz, 2H), 7.07 (s, 1H), 7.01-6.95 (m, 1H), 6.93-6.84 (m, 2H), 5.42-5.28 (m, 1H), 4.45-4.31 (m, 1H), 3.88 (s, 3H), 3.65 (s, 3H), 3.18-3.14 (m, 2H), 2.92-2.85 (m, 1H), 2.76-2.59 (m, 4H), 2.31 (d, J = 6.8 Hz, 2H), 2.27 (s, 3H), 2.18-2.13 (m, 2H), 2.02-1.78 (m, 8H), 1.71-1.56 (m, 3H), 1.16-1.06 (m, 2H) |
| I-455 | BGU | 3,4-difluorobenzoic acid (CAS# 455-86-7) | 769.4 | 11.09 (s, 1H), 9.57 (s, 1H), 8.30 (s, 1H), 8.05-8.01 (m, 2H), 7.88-7.85 (m, 1H), 7.64-7.58 (m, 1H), 7.06 (s, 1H), 7.01-6.97 (m, 1H), 6.93-6.88 (m, 2H), 5.36 (dd, J = 5.6, 12.4 Hz, 1H), 4.43-4.37 (m, 1H), 3.87 (s, 3H), 3.65 (s, 3H), 3.30 (s, 3H), 3.20-3.17 (m, 2H), 2.94-2.85 (m, 2H), 2.82-2.70 (m, 3H), 2.64-2.60 (m, 2H), 2.18-2.16 (m, 3H), 2.04-1.84 (m, 10H), 1.27-1.07 (m, 2H) |

TABLE 9-continued

Compounds synthesized via Method 5 with the coupling of various amines and acids.

| I-# | Intermediate Amine | Intermediate Acid | LCMS (ES+) m/z (M + H)+ | 1HNMR (400 MHz, DMSO-d6) δ |
|---|---|---|---|---|
| I-456 | BGU | 2-(trifluoromethyl)pyridine-4-carboxylic acid (CAS# 131747-41-6) | 802.5 | 11.08 (s, 1H), 10.05 (s, 1H), 8.97 (d, J = 4.8Hz, 1H), 8.34 (s, 1H), 8.31 (s, 1H), 8.19 (d, J = 4.8 Hz, 1H), 8.01 (s, 1H), 7.08 (s, 1H), 7.01-6.78 (m, 3H), 5.40-5.30(m, 1H), 4.46-4.31 (m, 1H), 3.86(s, 3H), 3.64 (s, 3H), 3.20-3.10 (m, 2H), 2.93-2.84 (m, 1H), 2.78-2.70 (m, 2H), 2.63-2.56 (m, 1H), 2.46-2.40 (m, 1H), 2.31-2.27 (m, 2H), 2.25 (s, 3H), 2.20-2.10 (m, 2H), 2.05-1.83 (m, 6H), 1.82-1.75 (m, 2H), 1.71-1.61 (m, 2H), 1.59-1.48 (m, 1H), 1.19-1.03 (m, 2H) |
| I-457 | BGU | 2,4-difluorobenzoic acid (CAS# 1583-58-0) | 769.4 | 11.09 (s, 1H), 9.46 (d, J = 8.8 Hz, 1H), 8.47 (s, 1H), 8.30 (s, 1H), 8.02-7.94 (m, 1H), 7.51-7.43 (m, 1H), 7.31-7.23 (m, 1H), 7.10 (s, 1H), 7.01-6.95 (m, 1H), 6.93-6.85 (m, 2H), 5.40-5.29 (m, 1H), 4.45-4.27 (m, 1H), 3.92 (s, 3H), 3.65 (s, 3H), 3.16 (d, J = 10.4 Hz, 2H), 2.93-2.84 (m, 1H), 2.76-2.58 (m, 4H), 2.31 (d, J =7.2 Hz, 2H), 2.27 (s, 3H), 2.15 (d, J = 10.8 Hz, 2H), 2.05-1.77 (m, 8H), 1.70-1.53 (m, 3H), 1.18-1.04 (m, 2H) |
| I-458 | BGU | 3,5-dichlorobenzoic acid (CAS# 51-36-5) | 801.4 | 11.09 (s, 1H), 9.75 (s, 1H), 8.31 (s, 1H), 8.00-7.95 (m, 3H), 7.87 (t, J = 1.6 Hz, 1H), 7.07 (s, 1H), 7.01-6.96 (m, 1H), 6.94-6.86 (m, 2H), 5.41-5.30 (m, 1H), 4.46-4.32 (m, 1H), 3.86 (s, 3H), 3.65 (s, 3H), 3.20-3.15 (m, 2H), 2.94-2.83 (m, 1H), 2.80-2.58 (m, 5H), 2.42-2.27 (m, 4H), 2.20-2.12 (m, 2H), 2.05-1.79 (m, 8H), 1.76-1.57 (m, 3H), 1.19-1.08 (m, 2H) |
| I-459 | BGU | 2,5-difluorobenzoic acid (CAS# 2991-28-8) | 769.3 | 11.09 (s, 1H), 9.56 (d, J = 9.2 Hz, 1H), 8.45 (s, 1H), 8.31 (s, 1H), 7.74-7.59 (m, 1H), 7.54-7.41 (m, 2H), 7.10 (s, 1H), 7.01-6.81 (m, 3H), 5.40-5.29 (m, 1H), 4.44-4.31 (m, 1H), 3.92 (s, 3H), 3.64 (s, 3H), 3.18-3.13 (m, 2H), 2.94-2.86 (m, 1H), 2.77-2.68 (m, 4H), 2.33-2.30 (m, 2H), 2.26 (s, 3H), 2.18-2.12 (m, 2H), 2.02-1.78 (m, 8H), 1.73-1.54 (m, 3H), 1.19-1.06 (m, 2H) |
| I-460 | BGU | 2,6-difluorobenzoic acid (CAS# 385-00-2) | 769.5 | 11.41-10.72 (m, 1H), 9.92 (s, 1H), 8.29 (d, J = 2.8 Hz, 2H), 7.61-7.49 (m, 1H), 7.25-7.15 (m, 2H), 7.05 (s, 1H), 7.01-6.85 (m, 3H), 5.40-5.29 (m, 1H), 4.43-4.30 (m, 1H), 3.85 (s, 3H), 3.64 (s, 3H), 3.18-3.12 (m, 2H), 2.92-2.84 (m, 1H), 2.75-2.66 (m, 4H), 2.33-2.25 (m, 5H), 2.19-2.11 (m, 2H), 2.01-1.78 (m, 8H), 1.72-1.54 (m, 3H), 1.16-1.06 (m, 2H) |
| I-461 | BGU | 2,3-difluorobenzoic acid (CAS# 4519-39-5) | 769.4 | 11.02 (br s, 1H), 9.57 (d, J = 5.6 Hz, 1H), 8.39 (s, 1H), 8.30 (s, 1H), 7.67-7.61 (m, 2H), 7.38-7.34 (m, 1H), 7.09 (s, 1H), 6.99-6.95 (m, 1H), 6.91-6.90 (m, 1H), 6.85 (d, J = 7.6 Hz, 1H), 5.30 (dd, J = 4.8, 12.4 Hz, 1H), 4.41-4.35 (m, 1H), 3.91 (s, 3H), 3.64 (s, 3H), 3.16 (d, J = 11.6 Hz, 2H), 2.89-2.81 (m, 1H), 2.75-2.69 (m, 2H), 2.62-2.57 (m, 1H), 2.29 (d, J = 6.8 Hz, 2H), 2.26 (s, 3H), 2.15 (d, J = 11.6 Hz, 2H), 1.99-1.94 (m, 4H), 1.91-1.88 (m, 2H), 1.81-1.79(m, 2H), 1.73-1.50 (m, 4H), 1.15-1.07 (m, 2H) |
| I-462 | BGU | BMC | 831.7 | 11.09 (s, 1H), 10.81 (s, 1H), 8.65 (s, 1H), 8.29 (s, 1H), 7.75 (dd, J = 7.6, 8.2 Hz, 1H), 7.38 (d, J = 7.2 Hz, 1H), 7.11 (s, 1H), 6.97 (d, J = 8.0 Hz, 1H), 6.94-6.83 (m, 3H), 5.35 (dd, J = 5.2, 12.5 Hz, 1H), 4.95 (s, 1H), 4.75 (s, 1H), 4.45-4.30 (m, 1H), 3.98 (s, 3H), 3.89 (d, J = 7.2 Hz, 1H), 3.74 (d, J = 7.6 Hz, 1H), 3.65 (s, 3H), 3.59 (d, J = 10.0 Hz, 1H), 3.38-3.38 (m, 2H), 3.18 (d, J = 12.0 Hz, 2H), 2.93-2.84 (m, 1H), 2.79-2.70 (m, 3H), 2.69-2.66 (m, 1H), 2.64-2.63 (m, 1H), 2.60-2.59 (m, 1H), 2.44-2.43 (m, 1H), 2.15 (d, J = 12.0 Hz, 2H), 2.11-2.08 (m, 9H), 2.02-1.86 (m, 9H), 1.80-1.71 (m, 2H), 1.70 (d, J = 2.8 Hz, 1H), 1.22-1.10 (m, 2H) |
| I-463 | BGU | BJE | 831.6 | 11.08 (s, 1H), 10.81 (s, 1H), 8.64 (s, 1H), 8.29 (s, 1H), 7.79-7.70 (m, 1H), 7.38 (d, J = 7.2 Hz, 1H), 7.12 (s, 1H), 7.00-6.95 (m, 1H), 6.93-6.83 (m, 3H), 5.35 (dd, J = 5.2. 12.8 Hz, 1H), 4.95 (s, 1H), 4.75 (s, 1H), 4.42-4.29 (m, 1H), 3.97 (s, 3H), 3.89 (m, 1H), 3.74 (d, J = 7.2 Hz, 1H), 3.64 (s, 3H), 3.59 (m, 1H), 3.15 (m, 2H), 2.96-2.81 (m, 1H), 2.78-2.60 (m, |

TABLE 9-continued

| Compounds synthesized via Method 5 with the coupling of various amines and acids. | | | | |
|---|---|---|---|---|
| I-# | Intermediate Amine | Intermediate Acid | LCMS (ES+) m/z $(M + H)^+$ | 1HNMR (400 MHz, DMSO-d6) δ |
| | | | | 4H), 2.35-2.22 (m, 6H), 2.17-2.11 (m, 2H), 2.04-1.75 (m, 10H), 1.74-1.48 (m, 3H), 1.17-1.04 (m, 2H) |
| I-464 | BGU | 6-cyanopyridine-2-carboxylic acid (CAS# 872602-74-9) | 759.5 | 11.09 (s, 1H), 10.31 (s, 1H), 8.66 (s, 1H), 8.47-8.43 (m, 1H), 8.37-8.30 (m, 3H), 7.16 (s, 1H), 7.01-6.95 (m, 1H), 6.93-6.86 (m, 2H), 5.35 (dd, J = 5.2, 12.8 Hz, 1H), 4.44-4.33 (m, 1H), 4.00 (s, 3H), 3.65 (s, 3H), 3.18 (d, J = 12.0 Hz, 2H), 2.93-2.84 (m, 1H), 2.79-2.69 (m, 3H), 2.66-2.56 (m, 2H), 2.53-2.51 (tn, 2H), 2.39 (br s, 3H), 2.16 (d, J = 12.0 Hz, 2H), 2.02-1.92 (m, 4H), 1.88 (d, J = 12 Hz, 3H), 1.78-1.59 (m, 3H), 1.22-1.09 (m, 2H) |
| I-465 | BGU | BME | 805.6 | 11.09 (s, 1H), 9.38(s, 1H), 8.54(s, 1H),8.51 (s, 1H), 8.27 (s, 1H), 7.11 (s, 1H), 7.01-6.94 (m, 1H), 6.94-6.90 (m, 1H), 6.87 (d, J = 7.6 Hz, 1H), 5.34 (dd, J = 5.2, 12.4 Hz, 1H), 4.41-4.33 (m, 1H), 4.00 (s, 3H), 3.95 (s, 3H), 3.64 (s, 3H), 3.16 (d, J = 11.6 Hz, 2H), 2.92-2.85 (m, 1H), 2.78-2.63 (m, 4H), 2.39-2.35 (m, 2H), 2.34-2.32 (m, 1H), 2.30 (s, 3H), 2.18-2.10 (m, 2H), 2.02-1.90 (m, 4H), 1.90-1.79 (m, 3H), 1.74-1.63 (m, 2H), 1.62-1.55 (m, 1H), 1.18-1.06 (m, 2H) |

The reaction was run anywhere from 0.5-2 hrs at rt. The final products were isolated under standard purification techniques including reverse HPLC and prep-TLC with appropriate solvent conditions. [a]Instead of CMPI, HATU and DIEA in DMF was used for the coupling at rt for 1 hr. The product was purified by prep-HPLC. [b] LCMS measured as $(M-18)^+$.

Example 5. IRAK4 MSD Degradation in OCI-LY10

Degradation of IRAK4 in OCI-LY10 was quantitatively measured using Meso Scale Discovery technology. OCI-LY10 cells were seeded in 96-well plates (Corning 3799) with a density of 300,000 cells per well in 100 μL fresh media. Compounds were then added to the assay plates with a final top concentration of 1 to 10 μM in a 1:3 dilution series with total of 8 doses. The assay plates were then incubated for 4 to 24 hours at 37° C. under 5% C02. The assay plates were then centrifuged for 5 minutes and the cell pellets were treated with 100 L/well RIPA lysis buffer (Boston BioProducts BP-115D) with proteinase inhibitors. To prepare MSD assay plates (Meso Scale Discovery Catalog number L15XA-3), the plates were coated with 2 g/mL capture antibody (mouse Anti-IRAK4 antibody [2H9], ab119942) in PBS, at 40 μL/well. The plates were then incubated overnight at 4° C., washed 3 times with 150 μL/well TBST buffer (Cell Signaling Technology, Catalog number 9997S) and blocked with 150 μL/well blocking buffer (Meso Scale Discovery Catalog number R93BA-4). Cell lysates were then added to MSD assay plates and the plates were incubated at room temperature for 1 hour. The plates were then washed 3 times with 150 μL/well TBST buffer and 25 μL/well primary detection antibody (rabbit Anti-IRAK4 antibody [Y279], from Abcam. Catalog number ab32511, 1 μg/mL). The assay plates were then incubated at room temperature for 1 hour, washed 3 times with 150 μL/well TBST buffer and 25 μL/well secondary detection antibody, SULFO-TAG anti-rabbit antibody were added (anti rabbit antibody from Meso Scale Discovery, Catalog number R32AB-1, 1 μg/mL). The assay plates were then incubated at room temperature for 1 hour, washed 3 times with 150 μL/well TBST buffer, and 150 μL/well MSD reading buffer (Meso Scale Discovery catalog number R92TC-2) was added. The plates were then analyzed by a MSD reader (Meso Scale Discovery, Model Quick Plex SQ 120). The data was then analyzed by software Prism 7.0 from GraphPad and the dose-depended IRAK4 degradation were fit using a three-parameter logistic equation to calculate $DC_{50}$.

IRAK4 MSD degradation results in OCI-LY10 cells for compounds of the invention are presented in Table 10. The letter codes for IRAK4 $DC_5n$ include: A (<0.05 μM); B (0.05-0.1 μM); C (0.1-0.5 μM); D (0.5-1.0 μM); and E (>1.0 μM).

TABLE 10

| IRAK4 MSD Degradation in OCI-LY10 Results | | |
|---|---|---|
| Compound # | IRAK4 degradation in OCI-LY10 at 4 hrs: $DC_{50}$ (μM) | IRAK4 degradation in OCI-LY10 at 24 hrs: $DC_{50}$ (μM) |
| I-1 | — | C |
| I-31 | — | B |
| I-32 | — | A |
| I-33 | — | B |
| I-34 | D | — |
| I-35 | — | A |
| I-40 | B | — |
| I-41 | — | A |
| I-42 | — | A |
| I-43 | A | — |
| I-44 | A | — |
| I-45 | B | — |
| I-46 | — | B |
| I-47 | — | A |
| I-48 | A | — |
| I-49 | B | — |
| I-50 | A | — |
| I-52 | B | — |
| I-53 | A | — |
| I-54 | B | — |
| I-55 | A | — |
| I-56 | A | — |

TABLE 10-continued

IRAK4 MSD Degradation in OCI-LY10 Results

| Compound # | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-57 | A | — |
| I-58 | — | B |
| I-59 | — | B |
| I-60 | A | — |
| I-61 | A | — |
| I-62 | A | — |
| I-63 | A | B |
| I-64 | — | A |
| I-65 | — | A |
| I-66 | A | — |
| I-67 | A | — |
| I-68 | — | B |
| I-69 | — | B |
| I-70 | — | D |
| I-71 | — | B |
| I-72 | A | — |
| I-73 | B | — |
| I-74 | A | — |
| I-75 | A | — |
| I-76 | — | C |
| I-77 | — | B |
| I-78 | — | B |
| I-79 | — | C |
| I-80 | A | — |
| I-81 | B | — |
| I-82 | A | — |
| I-83 | D | — |
| I-84 | A | — |
| I-85 | A | — |
| I-86 | D | — |
| I-87 | — | D |
| I-88 | — | B |
| I-89 | — | B |
| I-90 | — | C |
| I-91 | — | B |
| I-92 | — | B |
| I-93 | A | B |
| I-94 | A | — |
| I-95 | B | — |
| I-96 | A | — |
| I-97 | A | — |
| I-98 | A | — |
| I-99 | B | — |
| I-100 | A | — |
| I-101 | A | — |
| I-102 | A | — |
| I-103 | B | — |
| I-104 | B | — |
| I-105 | A | — |
| I-106 | A | — |
| I-107 | A | — |
| I-108 | B | — |
| I-109 | B | — |
| I-110 | A | — |
| I-111 | B | — |
| I-112 | B | — |
| I-113 | B | — |
| I-114 | B | — |
| I-115 | A | — |
| I-116 | A | — |
| I-117 | B | — |
| I-118 | — | B |
| I-119 | — | B |
| I-120 | — | B |
| I-121 | — | B |
| I-122 | — | B |
| I-123 | — | B |
| I-124 | — | A |
| I-125 | — | B |
| I-126 | — | B |
| I-127 | — | B |
| I-128 | — | B |
| I-129 | — | B |
| I-130 | — | B |

TABLE 10-continued

IRAK4 MSD Degradation in OCI-LY10 Results

| Compound # | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-131 | — | B |
| I-132 | A | — |
| I-133 | A | — |
| I-134 | B | — |
| I-135 | B | — |
| I-136 | — | B |
| I-137 | — | C |
| I-138 | — | B |
| I-139 | — | A |
| I-140 | — | B |
| I-141 | — | B |
| I-142 | — | D |
| I-143 | — | D |
| I-144 | A | — |
| I-145 | B | — |
| I-146 | A | — |
| I-147 | D | — |
| I-148 | D | — |
| I-149 | A | — |
| I-150 | D | — |
| I-151 | B | — |
| I-152 | B | — |
| I-153 | A | — |
| I-154 | B | — |
| I-155 | A | — |
| I-156 | B | — |
| I-157 | B | — |
| I-158 | A | — |
| I-159 | — | A |
| I-160 | B | — |
| I-161 | — | D |
| I-162 | A | — |
| I-163 | B | — |
| I-164 | A | — |
| I-165 | A | — |
| I-166 | A | — |
| I-167 | B | — |
| I-168 | A | — |
| I-169 | B | — |
| I-171 | A | — |
| I-172 | A | — |
| I-174 | A | — |
| I-175 | A | — |
| I-176 | A | — |
| I-177 | B | — |
| I-178 | A | — |
| I-179 | A | — |
| I-180 | — | C |
| I-181 | — | D |
| I-182 | — | D |
| I-183 | — | B |
| I-184 | — | B |
| I-185 | — | B |
| I-186 | — | D |
| I-187 | — | B |
| I-188 | — | B |
| I-189 | A | — |
| I-196 | — | D |
| I-197 | — | D |
| I-198 | — | B |
| I-199 | — | D |
| I-200 | — | B |
| I-201 | A | B |
| I-202 | — | B |
| I-203 | A | — |
| I-204 | B | — |
| I-205 | B | — |
| I-206 | A | — |
| I-207 | B | — |
| I-208 | — | C |
| I-209 | — | A |
| I-210 | — | B |
| I-211 | — | A |
| I-212 | — | C |

TABLE 10-continued

IRAK4 MSD Degradation in OCI-LY10 Results

| Compound # | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-213 | — | C |
| I-214 | B | — |
| I-218 | — | B |
| I-219 | — | B |
| I-220 | — | B |
| I-221 | — | A |
| I-222 | — | B |
| I-223 | — | B |
| I-224 | — | A |
| I-225 | — | D |
| I-226 | A | — |
| I-227 | — | B |
| I-228 | A | — |
| I-229 | A | — |
| I-230 | — | B |
| I-231 | — | B |
| I-232 | — | B |
| I-233 | — | A |
| I-234 | — | B |
| I-235 | A | — |
| I-236 | — | B |
| I-238 | — | A |
| I-239 | A | — |
| I-242 | A | — |
| I-247 | A | — |
| I-249 | — | B |
| I-250 | — | B |
| I-251 | — | B |
| I-254 | — | A |
| I-255 | — | A |
| I-256 | — | D |
| I-257 | D | — |
| I-258 | A | — |
| I-259 | B | — |
| I-260 | A | — |
| I-261 | A | — |
| I-262 | A | — |
| I-263 | A | — |
| I-264 | A | — |
| I-265 | A | — |
| I-266 | B | — |
| I-267 | A | — |
| I-268 | — | B |
| I-273 | — | B |
| I-274 | — | B |
| I-276 | A | — |
| I-277 | A | — |
| I-278 | B | — |
| I-279 | A | — |
| I-281 | A | — |
| I-282 | A | — |
| I-283 | D | — |
| I-284 | B | — |
| I-285 | B | — |
| I-286 | — | B |
| I-287 | — | B |
| I-289 | B | — |
| I-290 | — | B |
| I-291 | — | A |
| I-292 | — | B |
| I-293 | B | — |
| I-295 | B | — |
| I-296 | — | B |
| I-297 | — | C |
| I-299 | A | — |
| I-300 | B | — |
| I-302 | — | B |
| I-304 | — | A |
| I-305 | — | B |
| I-306 | — | A |
| I-308 | — | B |
| I-309 | B | — |
| I-310 | D | — |
| I-311 | — | B |

TABLE 10-continued

IRAK4 MSD Degradation in OCI-LY10 Results

| Compound # | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-312 | — | A |
| I-313 | — | A |
| I-314 | — | C |
| I-315 | — | B |
| I-316 | — | B |
| I-317 | — | B |
| I-318 | — | B |
| I-319 | — | D |
| I-320 | A | — |
| I-321 | — | A |
| I-322 | A | — |
| I-324 | A | — |
| I-325 | A | — |
| I-326 | — | D |
| I-327 | A | — |
| I-328 | A | — |
| I-329 | A | — |
| I-330 | — | D |
| I-331 | — | B |
| I-332 | — | A |

Example 6. Cell viability Assay with OCI-LY10 and SUDHL-2

Compound-mediated viability effect on OCI-LY10 or SUDHL-2 was quantitatively determined using the CellTiter-Glo® Luminescent Cell Viability Assay kit from Promega (Catalog number G7570) following manufacturer's recommended procedures. Briefly, OCI-LY10 or SUDHL-2 cells were seeded into 384 well plates (Grenier Bio-One, Catalog number 781080) with a density of 10,000 cells per well. Compounds were then added to the assay plate with final top concentration of 10 M and 1:3 dilution series with total of 9 doses. The final DMSO concentration was normalized to 0.2%. The assay plates were incubated at 37° C. for 4 days under 5% $CO_2$. Then the assay plate was equilibrated at room temperature for 10 minutes. To determine cell viability, L CellTiter Glo reagent was added to each well and the assay plate was centrifuged at 1000 rpm for 30 second, incubated at room temperature for 10 min, and analyzed by detecting the luminescence using a multimode plate reader (EnVision 2105, PerkinElmer). The data was then analyzed by software Prism 7.0 from GraphPad and the dose response curves were fit using a three-parameter logistic equation to calculate $IC_{50}$.

CTG Cell Viability Assay—OCI-LY10 and SUDHL-2 results for compounds of the invention are presented in Table 11. The letter codes for IRAK4 $IC_{50}$ include: A (<0.05 μM); B (0.05-0.1 μM); C (0.1-0.5 μM); D (0.5-1.0 μM); and E (>1.0 μM).

TABLE 11

CTG Cell Viability Assay Results

| Compound # | CTG Cell Viability Assay - OCI-LY10: $IC_{50}$ (μM) | CTG Cell Viability Assay - SUDHL-2: $IC_{50}$ (μM) |
|---|---|---|
| I-63 | B | C |
| I-93 | A | C |
| I-201 | A | E |
| I-247 | E | — |

Example 7: Quantification of Ikaros and Aiolos Degradation

Degradation of Ikaros (protein product of gene IKZF1) and Aiolos (protein product of gene IKZF3) were determined by quantitative immunoblotting as follows. OCI-LY10 cells, $2\times10^6$ cells/well, were treated with listed concentrations of IRAK4 degraders or control compounds in 6 well plates for 6 h. Cells were collected, washed with cold PBS, lysed in RIPA buffer (Boston BioProducts BP-115D) with protease/phosphatase inhibitor cocktail (Roche 05892791001/Roche 04906837001) and centrifuged at 13000 RPM for 20 min to precipitate insoluble material. The supernatant fraction was diluted in SDS-PAGE loading buffer (Beyotime Bio P0015) and 20 L of each sample was resolved on 4-12% Bis-Tris SDS-PAGE gels (Novex, WG1402BOX). Resolved samples were transferred to nitrocellulose membranes by wet electro-transfer method at 250 mV for 1.5 h. The membrane was blocked with LICOR blocking buffer (LI-COR, 927-50000) for 1 hour, washed three times with TBST (CST #9997S) for 5 minutes each and incubated with primary antibody prepared in block buffer with 0.1% Tween-20 (Solarbio, P8220) at 4° C. overnight. Ikaros antibody was rabbit monoclonal D6N9Y (CST #14859), at 1:1000 dilution. Aiolos antibody was rabbit monoclonal D1C1E (CST #15103), at 1:1000 dilution. Signal was normalized to mouse anti-beta-Actin monoclonal 8H10D10 (CST #3700) used at 1:10,000 dilution. After incubation in primary antibodies, membranes were washed three times with TBST, 5 minutes each, incubated with fluorescently labeled secondary antibodies anti-rabbit IgG (Licor, 926-32211) at 1:5000 dilution; anti-mouse IgG (LI-COR, 926-68070) at 1:5000 dilution, for 1 hour at RT. After incubation in secondary, membranes were washed three times with TBST, 5 minutes each and read on LICOR Odyssey imager. Data was reported as signal for Ikaros or Aiolos relative to signal for actin, and normalized to DMSO-treated control.

Ikaros and Aiolos degradation assay results in OCI-LY10 cells for compounds of the invention are presented in Table 12. The letter codes for Ikaros and Aiolos $DC_{50}$ include: A (<0.05 μM); B (0.05-0.1 μM); C (0.1-0.5 μM); D (0.5-1.0 μM); and E (>1.0 μM).

TABLE 12

Ikaros and Aiolos Degradation Assay Results

| Compound # | Ikros Degradation in OCI-LY10: $DC_{50}$ (μM) | Aiolos Degradation in OCI-LY10: $DC_{50}$ (μM) |
|---|---|---|
| I-63 | A | A |
| I-93 | A | A |
| I-201 | B | A |

Example 8. Syntheses of 6-(1,1-difluoroethyl)-N-[2-[4-[[2-[2-[[2-[(3R)-2,6-dioxo- 3-piperidyl]-1,3-dioxo-isoindolin-4-yl]amino]ethyl]-7-azaspiro[3.5]nonan-7-yl]methyl]cyclohexyl]-6-methoxy-indazol-5-yl]pyridine-2-carboxamide (1-128) and 6-(1,1-Difluoroethyl)-N-[2-[4-[[2-[2-[[2-[(3S)-2,6-dioxo-3-piperidyl]-1,3-dioxo-isoindolin-4-yl]amino]ethyl]-7-azaspiro[3.5]nonan-7-yl]methyl]cyclohexyl]-6-methoxy-indazol-5-yl]pyridine-2-carboxamide (1-129)

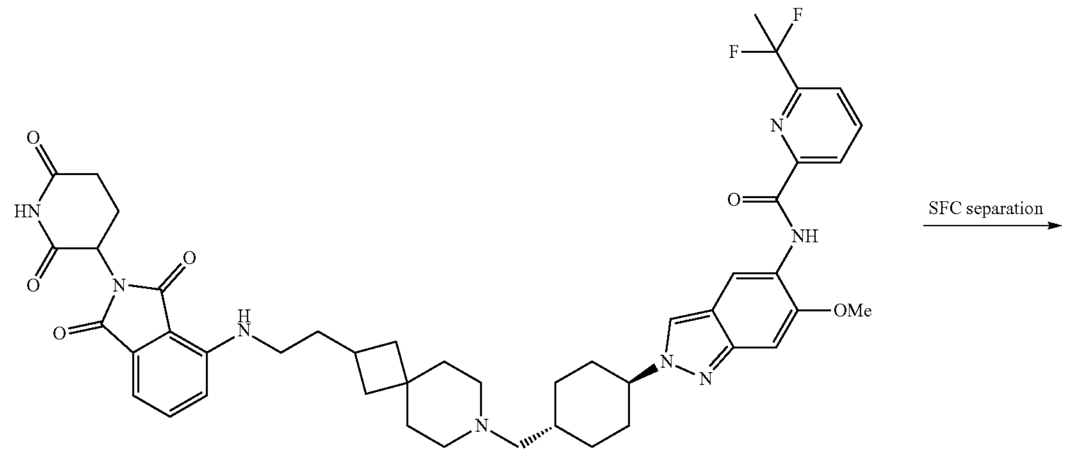

-continued

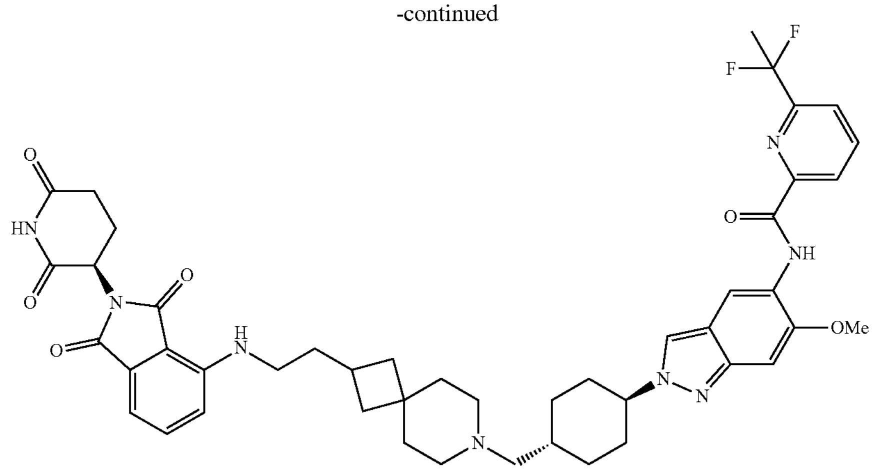

I-128

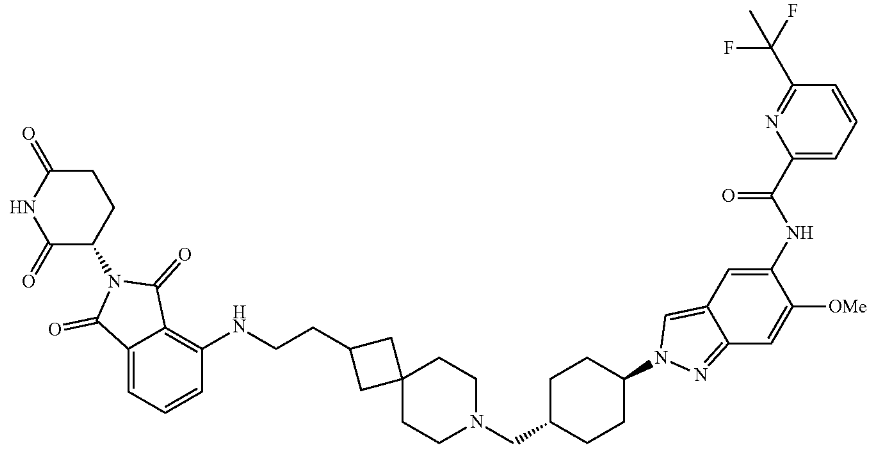

I-129

The reactant of 6-(1,1-difluoroethyl)-N-[2-[4-[[2-[2-[[2-(2,6-dioxo-3-piperidyl)-1,3-dioxo-isoindolin- 4-yl]amino]ethyl]-7-azaspiro[3.5]nonan-7-yl]methyl]cyclohexyl]-6-methoxy-indazol-5-yl]pyridine-2-carboxamide (1.90 g, 2.12 mmol, FA salt, I-63) was separated by SFC (column: DAICEL CHIRALPAK AS (250 mm*30 mm, 10 um); mobile phase: [0.1% $NH_3$.$H_2O$ IPA]; B %: 60%-60%, 7.0 min; 180 min) and purified by reverse phase (0.1% FA) to give the two title compounds. The first peak, 6-(1,1-difluoroethyl)-N-[2-[4-[[2-[2-[[2-[(3R)-2,6-dioxo- 3-piperidyl]-1,3-dioxo-isoindolin-4-yl]amino]ethyl]-7-azaspiro[3.5]nonan-7-yl]methyl]cyclohexyl]-6-methoxy-indazol-5-yl]pyridine-2-carboxamide (560 mg, 58% yield, 100% ee, FA salt) was obtained as yellow solid. $^1$H NMR (400 MHz, DMSO-$d_6$) δ 11.09 (s, 1H), 10.67 (s, 1H), 8.67 (s, 1H), 8.40-8.22 (m, 3H), 8.01 (dd, J=2.4, 6.8 Hz, 1H), 7.58 (dd, J=7.2, 8.4 Hz, 1H), 7.15 (s, 1H), 7.10-6.95 (m, 2H), 6.47 (t, J=5.6 Hz, 1H), 5.05 (dd, J=5.2, 12.8 Hz, 1H), 4.48-4.25 (m, 1H), 3.99 (s, 3H), 3.24-3.18 (m, 2H), 2.94-2.82 (m, 1H), 2.63-2.53 (m, 2H), 2.49-2.45 (m, 1H), 2.36-2.22 (m, 4H), 2.22-2.09 (m, 7H), 2.07-1.98 (m, 1H), 1.98-1.79 (m, 6H), 1.74-1.65 (m, 2H), 1.64-1.53 (m, 3H), 1.52-1.44 (m, 2H), 1.43-1.33 (m, 2H), 1.16-0.97 (m, 2H); LC-MS (ESI$^+$) m/z 851.4 $(M+H)^+$. The second peak, 6-(1,1-Difluoroethyl)-N-[2-[4-[[2-[2-[[2-[(3S)-2,6-dioxo-3-piperidyl]-1,3-dioxo-isoindolin-4-yl]amino]ethyl]-7-azaspiro[3.5]nonan-7-yl]methyl]cyclohexyl]-6-methoxy-indazol-5-yl]pyridine-2-carboxamide (646 mg, 67% yield, 98.6% ee, FA salt) was obtained as yellow solid. $^1$H NMR (400 MHz, DMSO-$d_6$) δ 11.09 (s, 1H), 10.67 (s, 1H), 8.67 (s, 1H), 8.37-8.24 (m, 3H), 8.01 (dd, J=2.4, 6.8 Hz, 1H), 7.58 (dd, J=7.2, 8.4 Hz, 1H), 7.20-6.96 (m, 3H), 6.47 (t, J=5.6 Hz, 1H), 5.05 (dd, J=5.2, 12.8 Hz, 1H), 4.40-4.29 (m, 1H), 3.99 (s, 3H), 3.23-3.19 (m, 2H), 2.94-2.82 (m, 1H), 2.64-2.53 (m, 2H), 2.49-2.45 (m, 1H), 2.41-2.31 (m, 2H), 2.30-2.23 (m, 2H), 2.22-2.09 (m, 7H), 2.07-1.99 (m, 1H), 1.98-1.79 (m, 6H), 1.74-1.54 (m, 5H), 1.53-1.46 (m, 2H), 1.45-1.32 (m, 2H), 1.17-0.99 (m, 2H); LC-MS (ESI$^+$) m/z 851.4 $(M+H)^+$.

Example 9. Syntheses of N-[2-[4-[[2-[[[2-[(3R)-2,6-dioxo-3-piperidyl]-1,3-dioxo-isoindolin-4-yl]amino]methyl]-7- azaspiro[3.5]nonan-7-yl]methyl]cyclohexyl]-6-methoxy-indazol-5-yl]-6-(trifluoromethyl)pyridine-2-carboxamide (I-130) and N-[2-[4-[[2-[[[2-[(3S)-2,6-dioxo-3-piperidyl]-1,3-dioxo-isoindolin-4-yl]amino]methyl]-7-azaspiro[3.5]nonan-7-yl]methyl]cyclohexyl]-6-methoxy-indazol-5-yl]-6-(trifluoromethyl)pyridine-2-carboxamide (I-131)
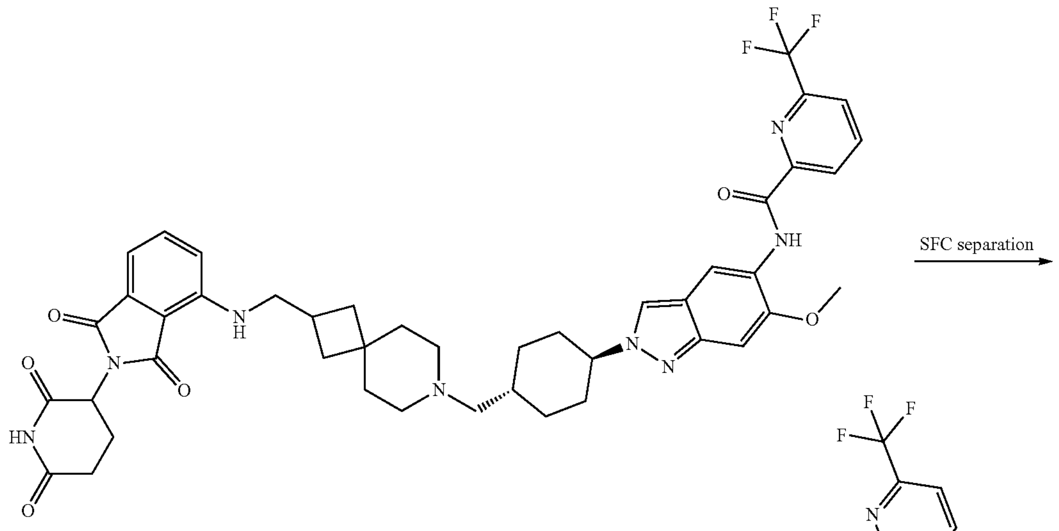
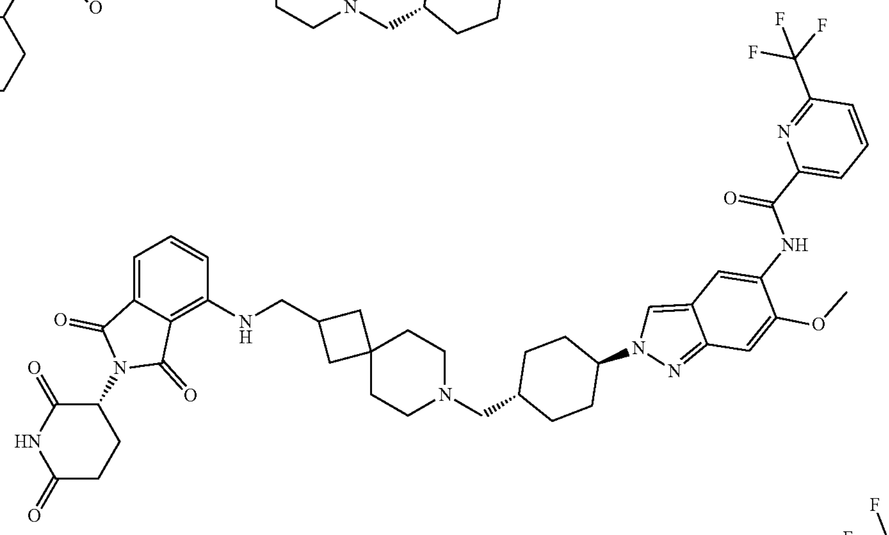
I-130
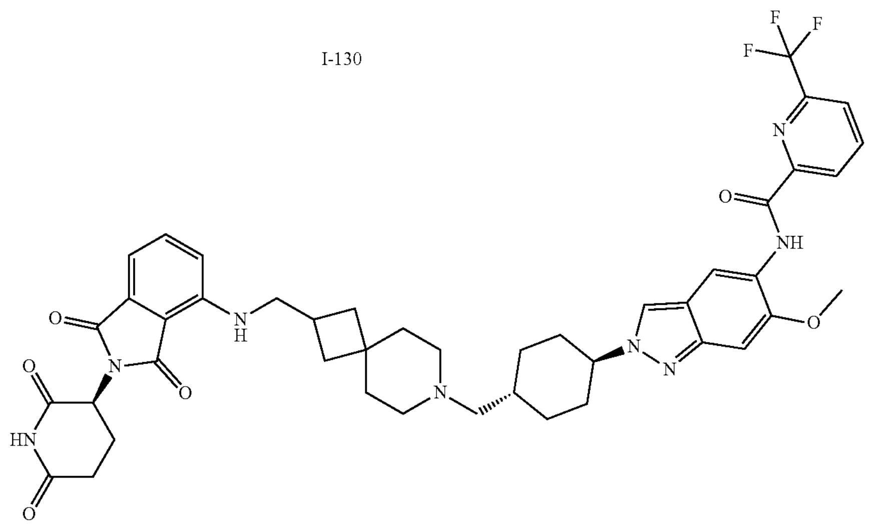
I-131

N-[2-[4-[[2-[[[2-(2,6-dioxo-3-piperidyl)-1,3-dioxo-isoindolin-4 yl]amino]methyl]-7-azaspiro[3.5]nonan-7-yl]methyl]cyclohexyl]-6-methoxy-indazol-5-yl]-6-(trifluoromethyl)pyridine-2-carboxamide (1.60 g, 1.90 mmol, I-201) was separated by SFC (column: DAICEL CHIRALPAK AS (250 mm*30 mm,10 um);mobile phase: [0.1% $NH_3.H_2O$ IPA]) to give two isomers. The first fraction, N-[2-[4-[[2-[[[2-[(3R)-2,6-dioxo-3-piperidyl]-1,3-dioxo-isoindolin-4-yl]amino]methyl]-7-azaspiro[3.5]nonan-7-yl]methyl]cyclohexyl]-6-methoxy-indazol-5-yl]-6-(trifluoromethyl) pyridine-2-carboxamide (0.8 g, 50.00% yield) was obtained as yellow solid. Then the solid was purified by reverse phase to give N-[2-[4-[[2-[[[2-[(3R)-2,6-dioxo-3-piperidyl]-1,3-dioxo-isoindolin-4-yl]amino]methyl]-7- azaspiro[3.5] nonan-7-yl]methyl]cyclohexyl]-6-methoxy-indazol-5-yl]-6-(trifluoromethyl)pyridine-2-carboxamide (151 mg, 20% yield, tR=0.974) as yellow solid. $^1$H NMR (400 MHz, DMSO-$d_6$) δ11.10 (s, 1H), 10.50 (s, 1H), 8.68 (s, 1H), 8.48-8.43 (m, 1H), 8.43-8.37 (m, 1H), 8.31 (s, 1H), 8.23-8.19 (m, 1H), 7.61-7.54 (m, 1H), 7.14 (s, 1H), 7.10 (d, J=8.8 Hz, 1H), 7.02 (d, J=7.2 Hz, 1H), 6.46 (t, J=5.6 Hz, 1H), 5.09-5.01 (m, 1H), 4.40-4.28 (m, 1H), 3.97 (s, 3H), 3.32-3.25 (m, 2H), 2.94-2.83 (m, 1H), 2.64-2.51 (m, 3H), 2.40-2.21 (m, 4H), 2.19-2.09 (m, 4H), 2.07-2.00 (m, 1H), 1.95-1.80 (m, 6H), 1.62-1.56 (m, 3H), 1.54-1.44 (m, 4H), 1.16-1.00 (m, 2H); LC-MS (ESI$^+$) m/z 841.5 $(M+H)^+$. The second fraction, N-[2-[4-[[2-[[[2-[(3S)-2,6-dioxo-3-piperidyl]-1,3-dioxo-isoindolin-4-yl]amino]methyl]-7-azaspiro[3.5] nonan-7-yl]methyl]cyclohexyl]-6-methoxy-indazol-5-yl]-6-(trifluoromethyl)pyridine-2-carboxamide (0.8 g, 50% yield) was obtained as yellow solid (458 mg, 53% yield, tR=1.81). $^1$H NMR (400 MHz, DMSO-$d_6$) δ 11.10 (s, 1H), 10.49 (s, 1H), 8.67 (s, 1H), 8.48-8.42 (m, 1H), 8.42-8.35 (m, 1H), 8.30 (s, 1H), 8.22-8.19 (m, 1H), 7.57 (dd, J=7.2, 8.4 Hz, 1H), 7.13 (s, 1H), 7.09 (d, J=8.8 Hz, 1H), 7.02 (d, J=7.2 Hz, 1H), 6.44 (t, J=5.6 Hz, 1H), 5.04 (dd, J=5.4, 12.8 Hz, 1H), 4.40-4.27 (m, 1H), 3.97 (s, 3H), 3.31 (t, J=6.4 Hz, 2H), 2.94-2.81 (m, 1H), 2.64-2.51 (m, 3H), 2.49-2.26 (m, 4H), 2.22 (d, J=6.8 Hz, 2H), 2.10 (d, J=10.0 Hz, 2H), 2.06-1.97 (m, 1H), 1.97-1.78 (m, 6H), 1.70-1.55 (m, 3H), 1.56-1.42 (m, 4H), 1.16-1.02 (m, 2H); LC-MS (ESI$^+$) m/z 841.5 $(M+H)^+$.

Example 10. Syntheses of 6-(1,1-Difluoroethyl)-N-[2-[4-[[6-[2-[[2-[(3R)-2,6-dioxo-3-piperidyl]-1,3-dioxo-isoindolin-4- yl]amino]ethyl]-2-azaspiro[3.3]heptan-2-yl]methyl]cyclohexyl]-6-methoxy-indazol-5-yl]pyridine-2-carboxamide (I-254) and 6-(1,1-Difluoroethyl)-N-[2-[4-[[6-[2-[[2-[(3S)-2,6-dioxo-3-piperidyl]-1,3-dioxo-isoindolin-4-yl]amino]ethyl]-2-azaspiro[3.3]heptan-2-yl]methyl]cyclohexyl]-6-methoxy-indazol-5-yl]pyridine-2-carboxamide (I-255)

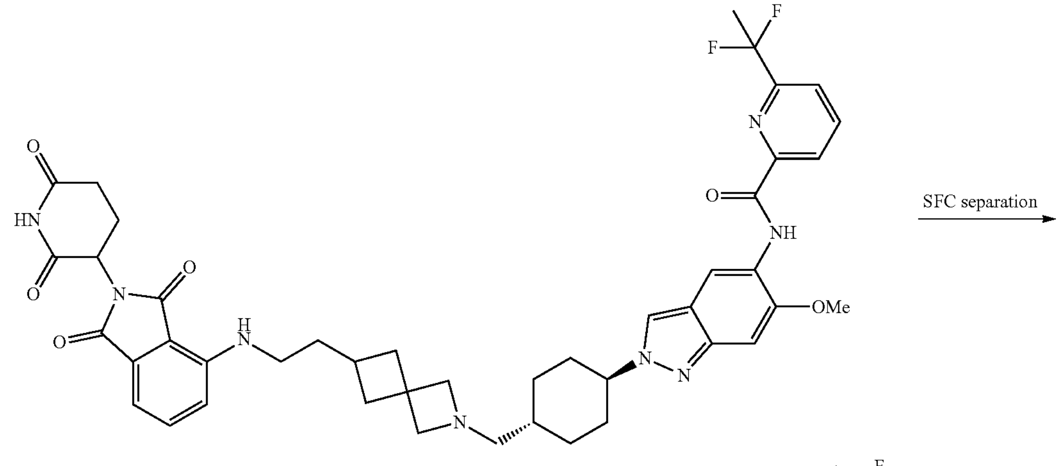

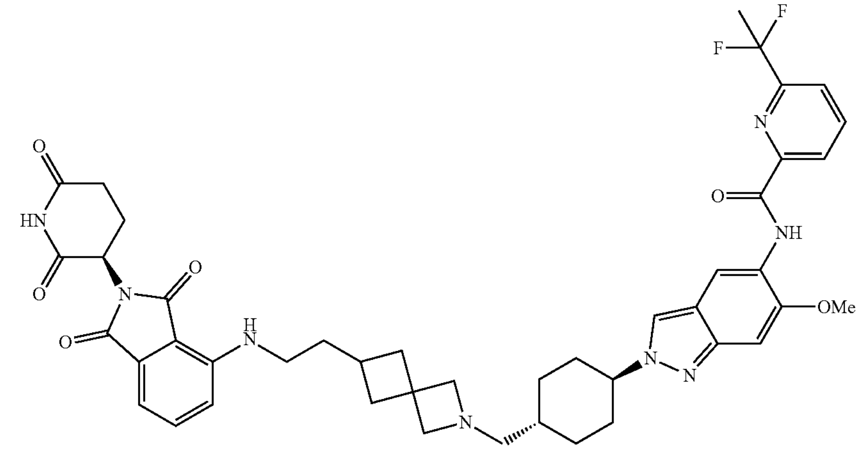

I-254

-continued

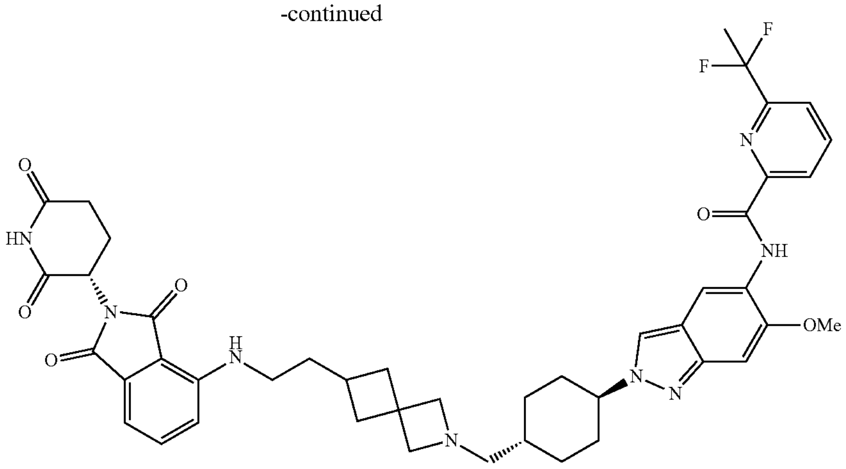

I-255

6-(1,1-difluoroethyl)-N-[2-[4-[[6-[2-[[2-(2,6-dioxo-3-piperidyl)-1,3-dioxo-isoindolin-4-yl]amino]ethyl]-2-azaspiro[3.3]heptan-2-yl]methyl]cyclohexyl]-6-methoxy-indazol-5-yl]pyridine-2-carboxamide (500 mg, 581 umol, HCl salt, I-93) was separated by SFC (column: DAICEL CHIRALPAK AD (250 mm*30 mm,10 um); mobile phase: [0.1% $NH_3H_2O$ IPA]) to give two isomers. The two fractions flow into a 1% solution of formic acid, respectively. The first fraction: 6-(1,1-Difluoroethyl)-N-[2-[4-[[6-[2-[[2-[(3R)-2,6-dioxo-3-piperidyl]-1,3-dioxo-isoindolin-4-yl]amino]ethyl]-2-azaspiro[3.3]heptan-2-yl]methyl]cyclohexyl]-6-methoxy-indazol-5-yl]pyridine-2-carboxamide (0.25 g, 50% yield) was obtained as yellow solid. Then the solid was purified by prep-HPLC (column: Phenomenex Synergi C18 150*25*10 um; mobile phase: [water (0.225% FA)-ACN]) to give the title compound (152 mg, 60% yield, FA salt, tR=1.09) as yellow solid. $^1$H NMR (400 MHz, DMSO-$d_6$) δ 11.10 (s, 1H), 10.66 (s, 1H), 8.66 (s, 1H), 8.34-8.26 (m, 3H), 8.01 (dd, J=2.0, 6.8 Hz, 1H), 7.58 (dd, J=7.2, 8.4 Hz, 1H), 7.14 (s, 1H), 7.10-6.98 (m, 2H), 6.47 (t, J=5.9 Hz, 1H), 5.05 (dd, J=5.2, 12.8 Hz, 1H), 4.38-4.26 (m, 1H), 3.99 (s, 3H), 3.27-3.17 (m, 4H), 3.13 (s, 2H), 2.95-2.83 (m, 1H), 2.64-2.53 (m, 2H), 2.36-2.27 (m, 2H), 2.25-2.14 (m, 5H), 2.13-2.06 (m, 3H), 2.05-1.98 (m, 1H), 1.94-1.79 (m, 4H), 1.79-1.72 (m, 2H), 1.64 (q, J=6.8 Hz, 2H), 1.41-1.29 (m, 1H), 1.17-1.01 (m, 2H); LC-MS (ESI$^+$) m/z 823.4 (M+H)$^+$. The second fraction: 6-(1,1-Difluoroethyl)-N-[2-[4-[[6-[2-[[2-[(3S)-2,6-dioxo-3-piperidyl]-1,3-dioxo-isoindolin-4-yl]amino]ethyl]-2-azaspiro[3.3]heptan-2-yl]methyl]cyclohexyl]-6-methoxy-indazol-5-yl]pyridine-2-carboxamide (0.25 g, 50% yield) was obtained as yellow solid. Then the solid was purified by prep-HPLC (column: Phenomenex Synergi C18 150*25*10 um; mobile phase: [water (0.225% FA)-ACN]) to give the title compound (162 mg, 64% yield, FA salt, tR=1.77) as yellow solid. $^1$H NMR (400 MHz, DMSO-$d_6$) δ 11.10 (s, 1H), 10.66 (s, 1H), 8.66 (s, 1H), 8.34-8.27 (m, 3H), 8.01 (dd, J=2.0, 6.8 Hz, 1H), 7.58 (dd, J=7.2, 8.4 Hz, 1H), 7.14 (s, 1H), 7.04 (dd, J=7.8, 16.0 Hz, 2H), 6.47 (t, J=6.0 Hz, 1H), 5.05 (dd, J=5.2, 12.8 Hz, 1H), 4.39-4.25 (m, 1H), 3.99 (s, 3H), 3.26-3.17 (m, 4H), 3.10 (s, 2H), 2.94-2.82 (m, 1H), 2.64-2.52 (m, 2H), 2.27 (d, J=6.8 Hz, 2H), 2.24-2.14 (m, 5H), 2.13-2.06 (m, 3H), 2.06-1.98 (m, 1H), 1.92-1.79 (m, 4H), 1.78-1.70 (m, 2H), 1.64 (q, J=6.8 Hz, 2H), 1.41-1.27 (m, 1H), 1.16-1.00 (m, 2H); LC-MS (ESI$^+$) m/z 823.4 (M+H)$^+$.

Example 11. Synthesis of N-(2-((1r,4r)-4-(((5-(1-(2,6-dioxopiperidin-3-yl)-3-methyl-2-oxo-2,3-dihydro-1H-benzo[d] imidazol-5-yl)pent-4-yn-1-yl)(methyl)amino)methyl)cyclohexyl)-6-(2-hydroxypropan-2-yl)-2H-indazol-5-yl)-6-(trifluoromethyl)picolinamide (I-67)

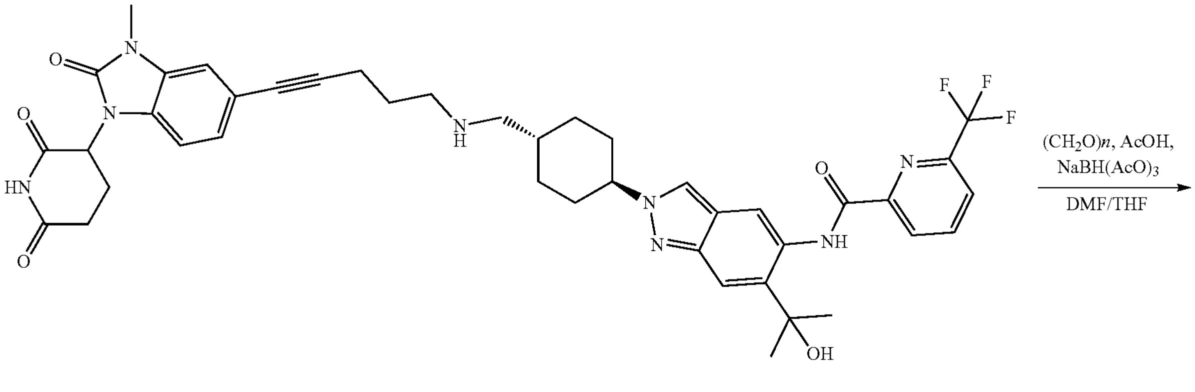

-continued

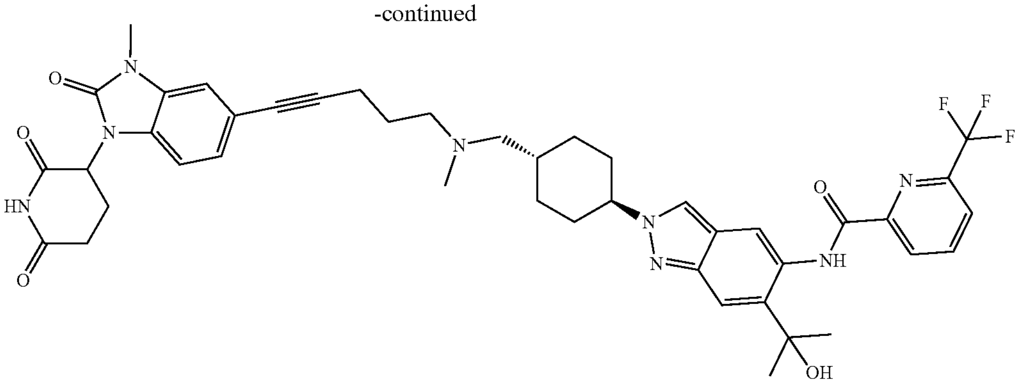

I-67

To a solution of N-[2-[4-[[5-[1-(2,6-dioxo-3-piperidyl)-3-methyl-2-oxo-benzimidazol-5-yl]pent-4-ynylamino]methyl]cyclohexyl]-6-(1-hydroxy-1-methyl-ethyl)indazol-5-yl]-6-(trifluoromethyl)pyridine-2-carboxamide (0.150 g, 187 umol, I-61), formaldehyde (28.1 mg, 938 umol) in DMF (3.0 mL) and THE (9.0 mL) was added TEA (19.0 mg, 187 umol). Subsequently, HOAc (22.5 mg, 375 umol) was added and the mixture was stirred at 40° C. for 0.5 hr. After that, $NaBH(OAc)_3$ (198 mg, 938 umol) was added and the mixture was stirred at 25° C. for 12 hrs. On completion, the reaction mixture was quenched with water (0.1 mL) and concentrated in vacuo. The residue was purified by prep-HPLC (column: Waters Xbridge 150*25 mm*5 um; mobile phase: [water (10 mM $NH_4HCO_3$)-ACN]; B %: 44%-74%, 10 min) to give the title compound (21.0 mg, 13% yield) as off-white solid. $^1H$ NMR (400 MHz, DMSO-$d_6$) δ 12.4 (s, 1H), 11.16-11.07 (m, 1H), 8.69 (s, 1H), 8.47-8.43 (m, 1H), 8.36 (t, J=7.6 Hz, 1H), 8.31 (s, 1H), 8.16 (d, J=8.0, 1H), 7.55 (s, 1H), 7.24 (s, 1H), 7.10 (s, 2H), 5.94 (s, 1H), 5.40-5.33 (m, 1H), 4.44-4.37 (m, 1H), 3.40 (s, 3H), 2.45-2.38 (m, 6H), 2.18 (s, 3H), 2.17-2.09 (m, 4H), 2.04-1.94 (m, 4H), 1.89 (dd, J=3.2, 11.6 Hz, 2H), 1.71-1.66 (m, 2H), 1.61 (s, 6H), 1.61-1.58 (m, 4H), 1.15-1.06 (m, 2H); LC-MS (ESI$^+$) m/z 813.4 (M+H)$^+$.

Example 12. Synthesis of 4-[[7-[[4-[8,8-Dimethyl-6-[6-(trifluoromethyl)-2-pyridyl]pyrazolo[3,4-g][3,1]benzoxazin- 2-yl]cyclohexyl]methyl]-7-azaspiro[3.5]nonan-2-yl]amino]-2-(2,6-dioxo-3-piperidyl)isoindoline-1,3-dione (I-127)

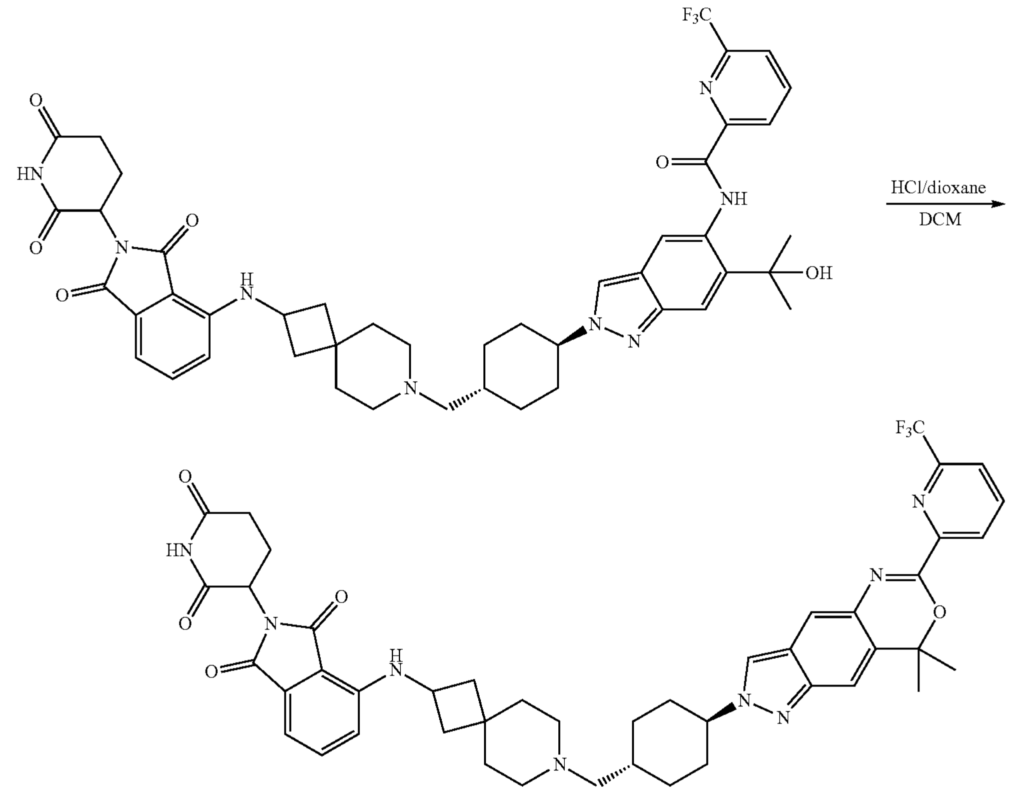

I-127

To a solution of N-[2-[4-[[2-[[2-(2,6-dioxo-3-piperidyl)-1,3-dioxo-isoindolin-4-yl]amino]-7-azaspiro [3.5]nonan-7-yl]methyl]cyclohexyl]-6-(1-hydroxy-1-methyl-ethyl)indazol-5-yl]-6-(trifluoromethyl)pyridine-2-carboxamide (100 mg, 116 umol, I-35) in DCM (3 mL) was added HCl/dioxane (4 M, 584 uL). The mixture was stirred at 25° C. for 16 hrs. On completion, the reaction was concentrated in vacuo to give a residue. The residue was purified by prep-HPLC (column: Phenomenex Synergi C18 150*25*10 um; mobile phase: [water (0.225% FA)-ACN]) to give the title compound (57.1 mg, 53% yield) as yellow solid. $^1$H NMR (400 MHz, DMSO-$d_6$) δ 11.11 (s, 1H), 8.47 (d, J=8.0 Hz, 1H), 8.41 (s, 1H), 8.25 (t, J=8.0 Hz, 1H), 8.06 (d, J=7.2 Hz, 1H), 7.63 (d, J=7.2 Hz, 2H), 7.59 (dd, J=7.2, 8.4 Hz, 1H), 7.07 (d, J=6.8 Hz, 1H), 7.01 (d, J=8.4 Hz, 1H), 6.45 (d, J=6.4 Hz, 1H), 5.06 (dd, J=5.2, 12.8 Hz, 1H), 4.50-4.38 (m, 1H), 4.17-4.08 (m, 1H), 2.94-2.85 (m, 1H), 2.64-2.54 (m, 2H), 2.43-2.31 (m, 4H), 2.30-2.18 (m, 2H), 2.13 (d, J=7.2 Hz, 4H), 2.07-2.00 (m, 1H), 1.99-1.85 (m, 4H), 1.75 (s, 6H), 1.71-1.60 (m, 5H), 1.57 (t, J=5.2 Hz, 2H), 1.18-1.04 (m, 2H); LC-MS (ESI$^+$) m/z 837.4 (M+H)$^+$.

Example 13. Synthesis of N-(2-((1r,4r)-4-(((5-(1-(2,6-dioxopiperidin-3-yl)-3-methyl-2-oxo-2,3-dihydro-1H-benzo[d]imidazol-4-yl)pent-4-yn-1-yl)(methyl)amino)methyl)cyclohexyl)-6-(2-hydroxypropan-2-yl)-2H-indazol-5-yl)-6-(trifluoromethyl)picolinamide (I-228)

To a solution of N-[2-[4-[[5-[1-(2, 6-dioxo-3-piperidyl)-3-methyl-2-oxo-benzimidazol-4-yl]pent-4- ynylamino] methyl]cyclohexyl]-6-(1-hydroxy-1-methyl-ethyl)indazol-5-yl]-6-(trifluoromethyl)pyridine-2-carboxamide (0.15 g, 186 umol, I-60) in DMF (2 mL) and THE (8 mL) was added HOAc (11.2 mg, 186 umol) and $(CH_2O)_n$(112 mg, 3.72 mmol) under $N_2$ atmosphere. The mixture was stirred at 0° C. for 0.5 hr, then $NaBH(OAc)_3$ (985 mg, 4.65 mmol) was added. The mixture was stirred at 0° C. for 1.5 hr. On completion, the reaction was added 0.2 mL of $H_2O$, then concentrated under reduced pressure to give a residue. The residue was purified by Prep-HPLC (column: Waters Xbridge 150*25 mm*5 um;mobile phase: [water(10 mM $NH_4HCO3$)-ACN];B %: 46%-76%, 10 min) to give the title compound (85.3 mg, 56% yield) as an off-white solid. $^1$H NMR (400 MHz, DMSO-$d_6$) δ 12.36 (s, 1H), 11.29-10.97 (m, 1H), 8.70 (s, 1H), 8.51-8.10 (m, 4H), 7.57 (s, 1H), 7.15-6.94 (m, 3H), 5.94 (d, J=1.6 Hz, 1H), 5.37 (dd, J=5.2, 12.8 Hz, 1H), 4.44-4.39 (m, 1H), 3.66 (s, 3H), 2.91-2.82 (m, 1H), 2.77-2.66 (m, 1H), 2.44 (t, J=6.8 Hz, 3H), 2.22-2.07 (m, 7H), 2.03-1.51 (m, 16H), 1.19-1.02 (m, 2H). LC-MS (ESI$^+$) m/z 813.5 (M+H)$^+$.

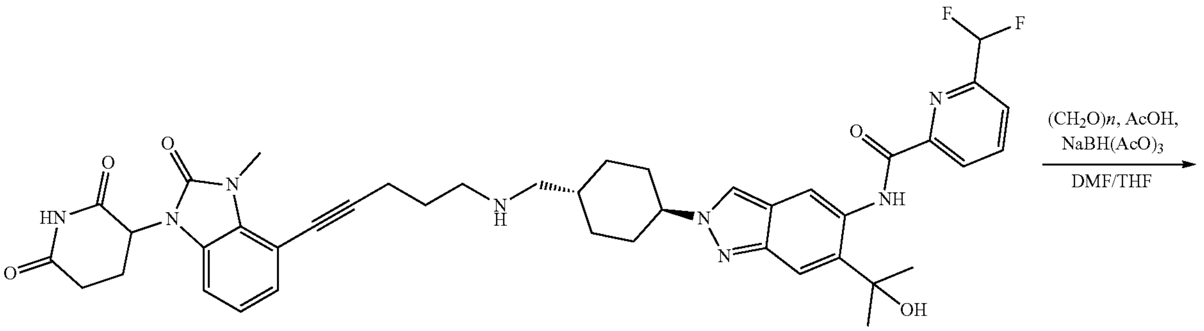

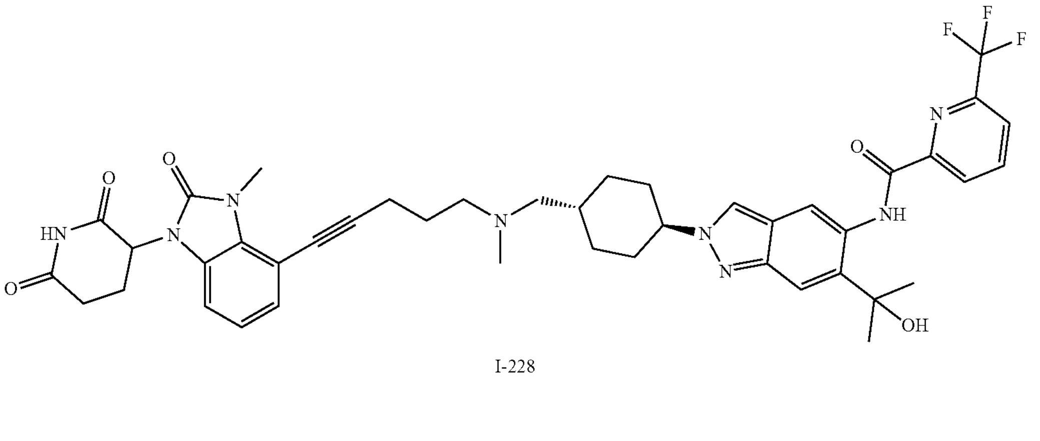

I-228

Examples 14. Syntheses of N-[6-(difluoromethyl)-2-[4-[[[4-[1-(2,6-dioxo-3-piperidyl)-3-methyl-2-oxo-benzimidazol-4- yl]cyclohexyl]-methyl-amino] methyl]cyclohexyl]indazol-5-yl]-6-(trifluoromethyl) pyridine-2-carboxamide (I-164) and N-[6-(difluoromethyl)-2-[4-[[[4-[1-(2,6-dioxo-3-piperidyl)-3-methyl-2-oxo-benzimidazol-4-yl] cyclohexyl]-methyl-amino]methyl]cyclohexyl] indazol-5-yl]-6-(trifluoromethyl)pyridine-2-carboxamide (I-165)
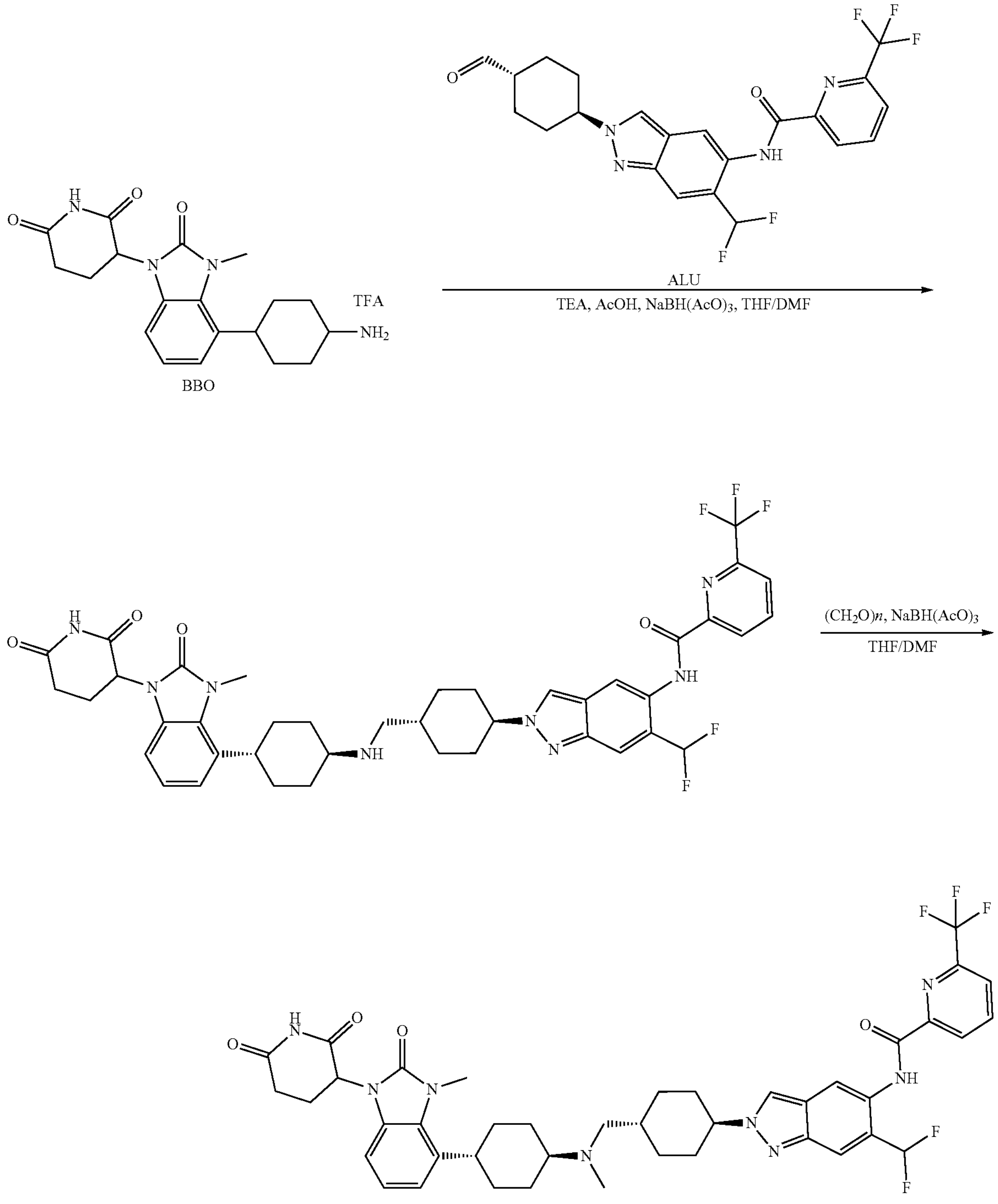
I-164

-continued

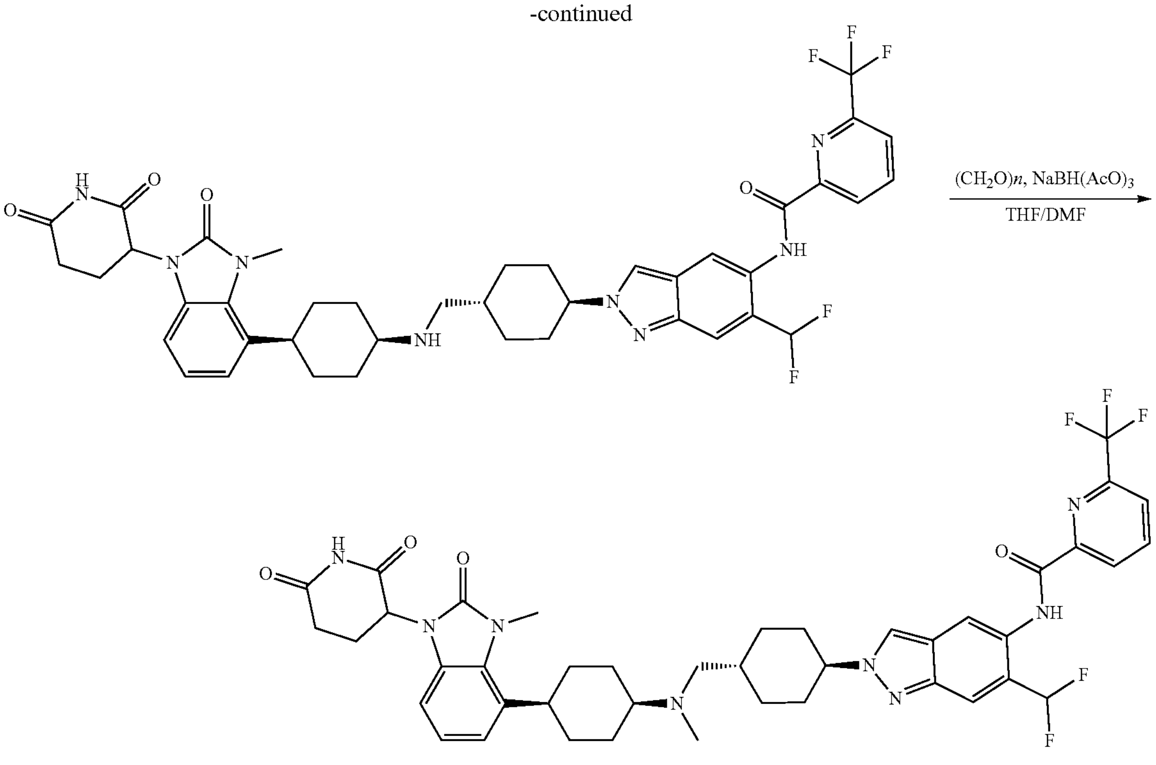

I-165

Step 1—N-(6-(difluoromethyl)-2-((1R,4r)-4-((((1r,4R)-4-(1-(2,6-dioxopiperidin-3-yl)-3-methyl-2-oxo-2,3-dihydro-1H-benzo[d]imidazol-4-yl)cyclohexyl)amino)methyl)cyclohexyl)-2H-indazol-5-yl)-6-(trifluoromethyl)picolinamide and N-(6-(difluoromethyl)-2-((1R,4r)-4-((((1s,4S)-4-(1-(2,6-dioxopiperidin-3-yl)-3-methyl-2-oxo-2,3-dihydro-1H-benzo[d]imidazol-4-yl)cyclohexyl)amino)methyl)cyclohexyl)-2H-indazol-5-yl)-6-(trifluoromethyl)picolinamide To a solution of 3-[4-(4-aminocyclohexyl)-3-methyl-2-oxo-benzimidazol-1-yl]piperidine-2,6-dione (348 mg, 740 umol, TFA, Intermediate BBO) in THF (2.0 mL) and DMF (1.0 mL) was added TEA (99.8 mg, 986.27 umol) till pH=8-9. Then HOAc (296 ug, 4.93 umol) was added till pH=5-7, and N-[6-(difluoromethyl)-2-(4-formylcyclohexyl)indazol-5-yl]-6-(trifluoromethyl)pyridine-2-carboxamide (230 mg, 493 umol, Intermediate ALU) was added. The mixture was stirred at −10° C. for 0.5 hr. Then $NaBH(OAc)_3$ (209 mg, 987 umol) was added and stirred at −10° C. for 1 hr. On completion, the reaction mixture was quenched by $H_2O$ (0.2 mL), and concentrated in vacuo to give a residue. The residue was purified by Prep-HPLC (FA condition; column: Unisil 3-100 C18 Ultra 150*50 mm*3 um;mobile phase: [water(0.225% FA)-ACN];B %: 25%-55%, 10 min) to give the title compound (200 mg, 50% yield) as white solid. The racemic N-[6-(difluoromethyl)-2-[4-[[[4-[1-(2,6-dioxo-3-piperidyl)-3-methyl-2-oxo-benzimidazol-4-yl]cyclohexyl]amino]methyl]cyclohexyl]indazol-5-yl]-6-(trifluoromethyl)pyridine-2-carboxamide (150 mg, 186 umol) was separated by Prep-HPLC (basic condition; column: Waters Xbridge 150*25 mm*5 um; mobile phase: [water(10 mM $NH_4HCO_3$)-ACN];B %: 35%-65%, 10 min) to give two title compounds. N-(6-(difluoromethyl)-2-((1R,4r)-4-((((1r,4R)-4-(1-(2,6-dioxopiperidin-3-yl)-3-methyl-2-oxo-2,3-dihydro-1H-benzo[d]imidazol-4-yl)cyclohexyl)amino)methyl)cyclohexyl)-2H-indazol-5-yl)-6-(trifluoromethyl)picolinamide (70 mg, 47% yield) was isolated as white solid. $^1$H NMR (400 MHz, DMSO-$d_6$) δ 11.09 (br s, 1H), 10.51 (s, 1H), 8.59 (s, 1H), 8.51-8.39 (m, 3H), 8.23 (dd, J=0.8, 7.6 Hz, 1H), 8.01 (s, 1H), 7.41-7.10 (m, 1H), 7.08-6.94 (m, 3H), 5.38 (dd, J=5.2, 12.4 Hz, 1H), 4.59-4.50 (m, 1H), 3.60 (s, 3H), 3.31-3.21 (m, 2H), 2.94-2.82 (m, 2H), 2.77-2.67 (m, 1H), 2.67-2.59 (m, 1H), 2.46 (d, J=6.4 Hz, 2H), 2.21 (d, J=9.6 Hz, 2H), 2.09-1.87 (m, 9H), 1.67-1.52 (m, 5H), 1.27-1.14 (m, 2H). N-(6-(difluoromethyl)-2-((1R,4r)-4-((((1s,4S)-4-(1-(2,6-dioxopiperidin-3-yl)-3-methyl-2-oxo-2,3-dihydro-1H-benzo[d]imidazol-4-yl)cyclohexyl)amino)methyl)cyclohexyl)-2H-indazol-5-yl)-6-(trifluoromethyl)picolinamide (60 mg, 40% yield) was isolated as white solid. $^1$H NMR (400 MHz, DMSO-$d_6$) δ 11.18 (br s, 1H), 10.56 (s, 1H), 8.64 (s, 1H), 8.57-8.47 (m, 3H), 8.29 (d, J=7.2 Hz, 1H), 8.06 (s, 1H), 7.46-7.30 (m, 1H), 7.09-7.01 (m, 3H), 5.44 (dd, J=5.2, 12.4 Hz, 1H), 4.64-4.54 (m, 1H), 3.65 (s, 3H), 3.34-3.23 (m, 2H), 3.00-2.91 (m, 1H), 2.79-2.68 (m, 3H), 2.28-2.22 (m, 2H), 2.14-1.92 (m, 10H), 1.80-1.49 (m, 4H), 1.40-1.25 (m, 4H). Absolute stereochemistry was assigned arbitrarily.

Step 2—N-[6-(difluoromethyl)-2-[4-[[[4-[1-(2,6-dioxo-3-piperidyl)-3-methyl-2-oxo-benzimidazol-4-yl]cyclohexyl]-methyl-amino]methyl]cyclohexyl]indazol-5-yl]-6-(trifluoromethyl)pyridine-2-carboxamide To a solution of N-[6-(difluoromethyl)-2-[4-[[[4-[1-(2,6-dioxo-3-piperidyl)-3-methyl-2-oxo- benzimidazol-4-yl]cyclohexyl]amino]methyl]cyclohexyl]indazol-5-yl]-6-(trifluoromethyl)pyridine-2-carboxamide (60.0 mg, 74.3 umol) in THE (2.0 mL) and DMF (1.0 mL) was added TEA (7.53 mg, 74.4 umol, 10.4 uL) until the pH=8-9. Then HOAc (4.47 mg, 74.4 umol, 4.25 uL) was added until the pH=5-7, then $(CH_2O)_n$(22.3 mg, 744 umol) was added. The mixture was stirred at 25° C. for 1 hr. Then $NaBH(OAc)_3$ (31.5 mg, 149 umol) was added and stirred at 25° C. for 1 hr. The reaction was stirred at 25° C. for 18 hrs. On completion, the reaction mixture was quenched by $H_2O$ (0.2 mL), filtered and concentrated in vacuo to give a residue. The residue was purified by Prep-HPLC (column: Waters Xbridge 150*25 mm*5 um;mobile phase: [water(10 mM $NH_4HCO_3$)-ACN];B %: 55%-85%, 10 min) to give the title compound (20.0 mg, 33% yield) as white solid. $^1H$ NMR (400 MHz, DMSO-$d_6$) δ 11.07 (s, 1H), 10.49 (s, 1H), 8.56 (s, 1H), 8.51-8.36 (m, 3H), 8.22 (dd, J=0.8, 7.6 Hz, 1H), 7.99 (s, 1H), 7.40-7.09 (m, 1H), 7.05-6.92 (m, 3H), 5.37 (dd, J=5.6, 12.4 Hz, 1H), 4.58-4.48 (m, 1H), 3.59 (s, 3H), 3.37-3.34 (m, 1H), 3.30 (s, 2H), 2.94-2.83 (m, 1H), 2.77-2.58 (m, 2H), 2.28-2.21 (m, 4H), 2.21 (s, 3H), 2.05-2.00 (m, 4H), 1.99-1.88 (m, 4H), 1.70-1.67 (m, 1H), 1.64-1.52 (m, 4H), 1.25-1.08 (m, 2H); LC-MS ($ESI^+$) m/z 821.3 $(M+H)^+$.

Step 3—N-[6-(difluoromethyl)-2-[4-[[[4-[1-(2,6-dioxo-3-piperidyl)-3-methyl-2-oxo-benzimidazol-4-yl]cyclohexyl]-methyl-amino]methyl]cyclohexyl]indazol-5-yl]-6-(trifluoromethyl)pyridine-2-carboxamide To a solution of N-[6-(difluoromethyl)-2-[4-[[[4-[1-(2,6-dioxo-3-piperidyl)-3-methyl-2-oxo- benzimidazol-4-yl]cyclohexyl]amino]methyl]cyclohexyl]indazol-5-yl]-6-(trifluoromethyl)pyridine-2-carboxamide (60.0 mg, 74.4 umol) in THE (2.0 mL) and DMF (1.0 mL) was added TEA (7.53 mg, 74.37 umol, 10.4 uL) until the pH=8-9. Then HOAc (4.47 mg, 74.4 umol, 4.25 uL) was added until the pH=5-7, then $(CH_2O)_n$(22.3 mg, 744 umol) was added. The mixture was stirred at 25° C. for 3 hr. Then $NaBH(OAc)_3$ (31.5 mg, 149 umol) was added and stirred at 25° C. for 12 hr. The mixture was stirred at 25° C. for 12 hr. On completion, the reaction mixture was quenched by water (0.2 mL), filtered and concentrated in vacuo to give a residue. The residue was purified by prep-HPLC (column: Waters Xbridge 150*25 mm*5 um;mobile phase: [water(10 mM $NH_4HCO_3$)-ACN];B %: 40%-70%, 10 min) to give the title compound (15.0 mg, 25% yield) as white solid. $^1H$ NMR (400 MHz, DMSO-$d_6$) δ 11.19-10.97 (m, 1H), 10.50 (s, 1H), 8.57 (s, 1H), 8.52-8.45 (m, 2H), 8.44-8.38 (m, 1H), 8.25-8.21 (m, 1H), 8.00 (s, 1H), 7.42-7.09 (m, 1H), 7.04-6.93 (m, 3H), 5.38 (dd, J=5.2, 12.4 Hz, 1H), 4.60-4.44 (m, 1H), 3.60 (s, 3H), 3.31 (s, 2H), 3.21 (t, J=11.2 Hz, 1H), 2.95-2.83 (m, 1H), 2.78-2.67 (m, 1H), 2.66-2.59 (m, 1H), 2.34-2.28 (m, 2H), 2.26 (s, 3H), 2.19-2.16 (m, 2H), 2.00-1.97 (m, 4H), 1.94-1.84 (m, 4H), 1.64-1.44 (m, 5H), 1.20-1.02 (m, 2H); LC-MS ($ESI^+$) m/z 821.3 $(M+H)^+$.

Example 15. Synthesis of N-((2R)-2-((2-(2-(1-(2,6-dioxopiperidin-3-yl)-3-methyl-2-oxo-2,3-dihydro-1H-benzo[d] imidazol-4-yl)ethyl)-7-azaspiro[3.5] nonan-7-yl)methyl)-2-methyl-6-morpholino-2,3-dihydrobenzofuran-5-yl)pyrazolo[1,5-a]pyrimidine-3-carboxamide (I-173)

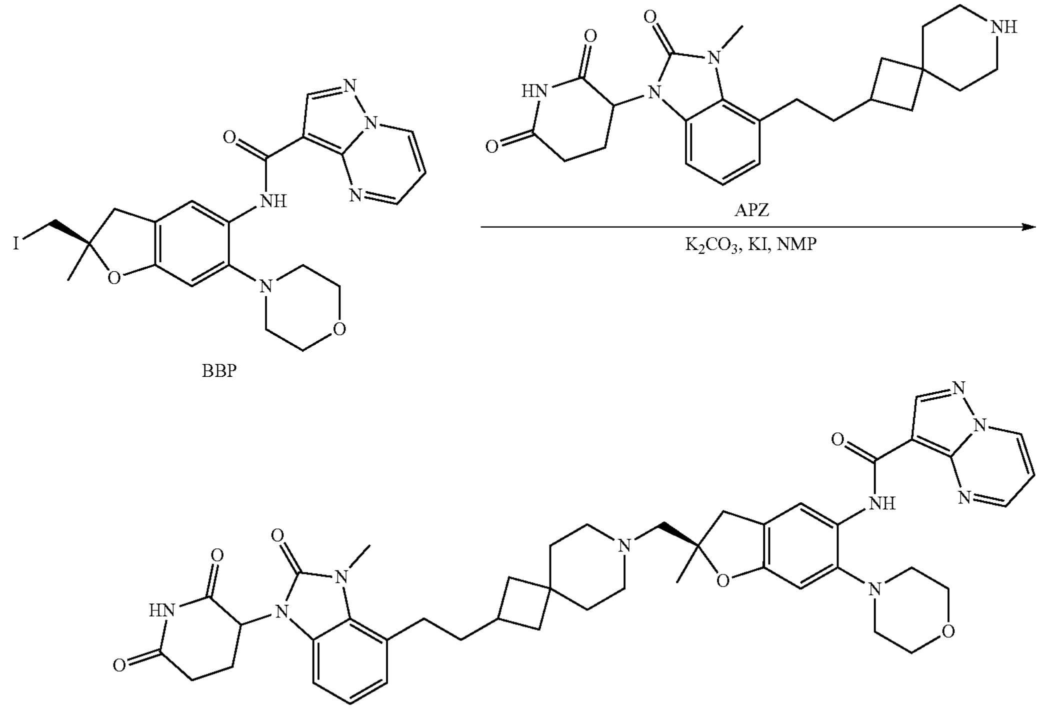

APZ

BBP

I-173

To a mixture of N-[(2R)-2-(iodomethyl)-2-methyl-6-morpholino-3H-benzofuran-5-yl]pyrazolo[1,5-a] pyrimidine-3-carboxamide (50.0 mg, 96.2 umol, Intermediate BBP) and 3-[4-[2-(7-azaspiro[3.5]nonan-2-yl)ethyl]-3-methyl-2-oxo-benzimidazol-1-yl]piperidine-2,6-dione (79.0 mg, 192 umol, Intermediate APZ) in NMP (0.5 mL) was added $K_2CO_3$ (39.9 mg, 288 umol) and KI (47.9 mg, 288 umol), and the mixture was stirred at 110° C. for 4 hrs under microwave condition. On completion, the reaction was filtered. The filtrate was purified by Prep-HPLC (column: Phenomenex Gemini-NX C18 75*30 mm*3 um;mobile phase: [water(0.225% FA)-ACN];B %: 10%-40%, 7 min) to give the title compound (2.4 mg, 3% yield, FA salt) as a yellow solid. LC-MS (ESI$^+$) m/z 802.7 $(M+H)^+$. $^1H$ NMR (400 MHz, $CDCl_3$) δ 10.47 (s, 1H), 8.84 (dd, J=1.6, 7.2 Hz, 1H), 8.79 (s, 1H), 8.77 (dd, J=1.6, 4.0 Hz, 1H), 7.49-7.43 (m, 1H), 7.34-7.31 (m, 1H), 7.07 (dd, J=4.0, 7.2 Hz, 1H), 7.01-6.95 (m, 1H), 6.86 (d, J=7.2 Hz, 1H), 6.67-6.64 (m, 1H), 6.63 (s, 1H), 5.24-5.16 (m, 1H), 3.98-3.92 (m, 4H), 3.66 (s, 3H), 3.25 (d, J=15.6 Hz, 1H), 2.94-2.91 (m, 4H), 2.56-2.38 (m, 6H), 2.27-2.18 (m, 3H), 2.00-1.92 (m, 2H), 1.75-1.73 (m, 2H), 1.51-1.48 (m, 2H), 1.44 (s, 3H), 1.39-1.33 (m, 3H), 1.28-1.23 (m, 1H).

Example 16. Syntheses of N-[2-[4-[[[4-[1-(2,6-dioxo-3-piperidyl)-3-methyl-2-oxo-benzimidazol-4-yl]cyclohexyl]- methyl-amino]methyl]cyclohexyl]-6-(1-hydroxy-1-methyl-ethyl)indazol-5-yl]-6-(trifluoromethyl)pyridine-2-carboxamide (I-174) and N-[2-[4-[[[4-[1-(2,6-dioxo-3-piperidyl)-3-methyl-2-oxo- benzimidazol-4-yl]cyclohexyl]-methyl-amino]methyl]cyclohexyl]-6-(1-hydroxy-1-methyl-ethyl)indazol-5-yl]-6-(trifluoromethyl)pyridine-2-carboxamide (I-175)

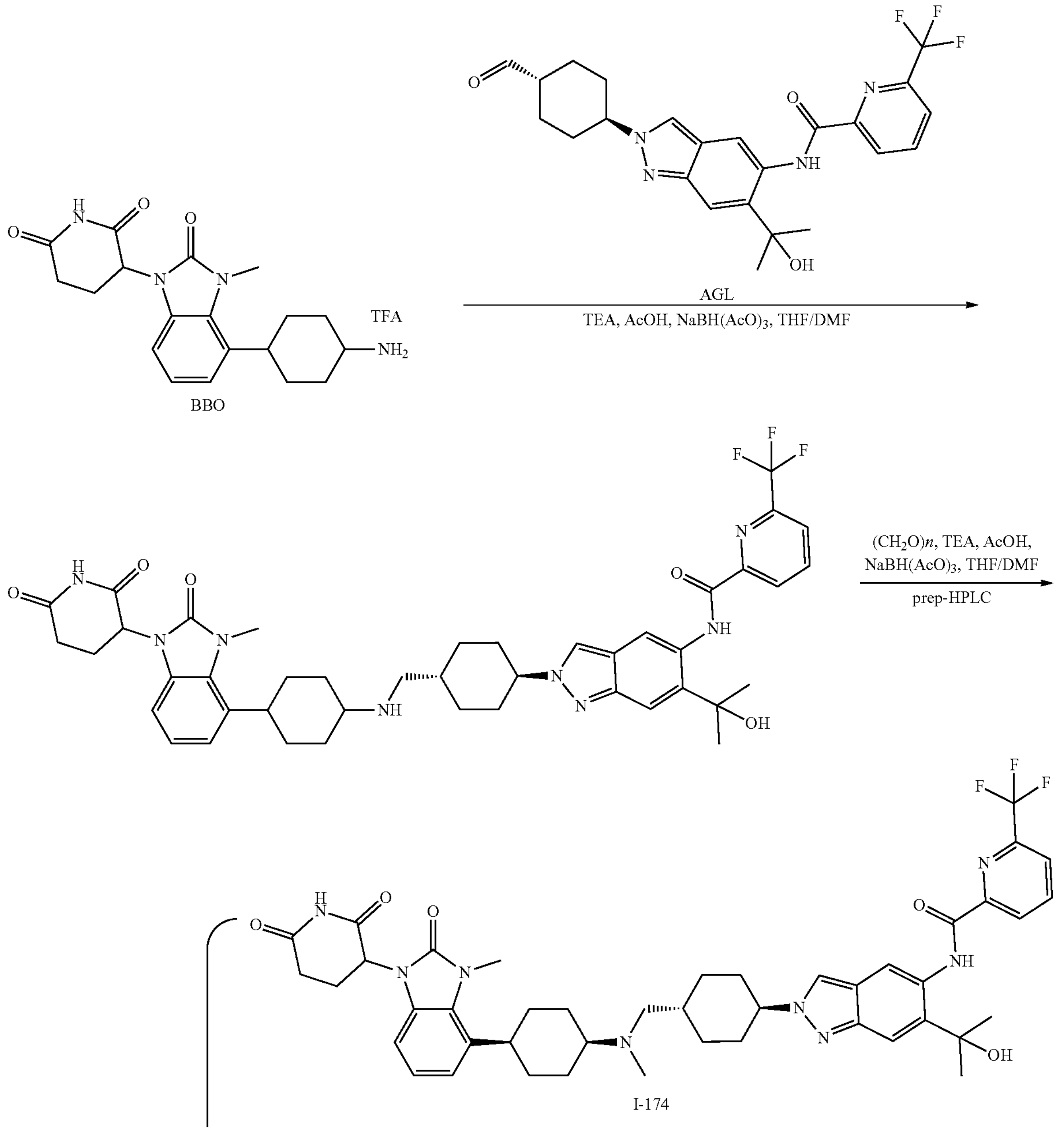

BBO

I-174

-continued

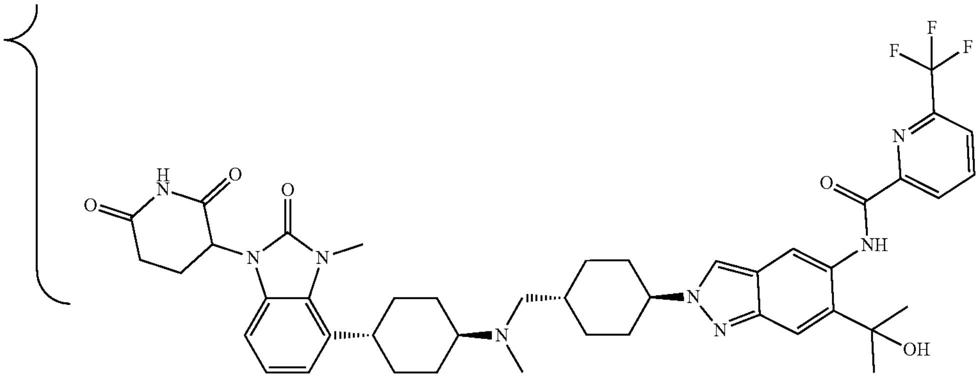

I-175

Step 1—N-[2-[4-[[[4-[1-(2,6-dioxo-3-piperidyl)-3-methyl-2-oxo-benzimidazol-4-yl]cyclohexyl]amino]methyl]cyclohexyl]-6-(1-hydroxy-1-methyl-ethyl)indazol-5-yl]-6-(trifluoromethyl)pyridine-2-carboxamide To a solution of 3-[4-(4-aminocyclohexyl)-3-methyl-2-oxo-benzimidazol-1-yl]piperidine-2,6-dione (744 mg, 1.58 mmol, TFA salt, Intermediate BBO) in THE (2.0 mL) and DMF (1.0 mL) was added TEA (213 mg, 2.11 mmol, 293 uL) until the pH=8-9, and then HOAc (633 ug, 10.5 umol) was added until the pH=5-7. Then N-[2-(4-formylcyclohexyl)-6-(1-hydroxy-1-methyl-ethyl)indazol-5-yl]-6- (trifluoromethyl)pyridine-2-carboxamide (500 mg, 1.05 mmol, Intermediate AGL) was added and the mixture was stirred at −10° C. for 0.5 hr. Then $NaBH(OAc)_3$ (447 mg, 2.11 mmol) was added and stirred at −10° C. for 1 hr. On completion, the reaction mixture was quenched by $H_2O$ (0.5 mL), filtered and concentrated in vacuo to give a residue. The residue was purified by Prep-HPLC (column: Phenomenex luna C18 150*40 mm*15 um;mobile phase: [water(0.225% FA)-ACN];B %: 22%-52%, 9 min) to give an impure product, which was re-purified by Prep-HPLC (neutral condition; column: Waters Xbridge C18 150*50 mm*10 um;mobile phase: [water(10 mM $NH_4HCO_3$)-ACN];B %: 38%-58%, 11.5 min) to give the title compound (450 mg, 52% yield) as yellow solid. LC-MS ($ESI^+$) m/z 815.9 $(M+H)^+$.

Step 2—N-[2-[4-[[[4-[1-(2,6-dioxo-3-piperidyl)-3-methyl-2-oxo-benzimidazol-4-yl]cyclohexyl]-methyl-amino]methyl]cyclohexyl]-6-(1-hydroxy-1-methyl-ethyl)indazol-5-yl]-6-(trifluoromethyl)pyridine-2-carboxamide and N-[2-[4-[[[4-[1-(2,6-dioxo-3-piperidyl)-3-methyl-2-oxo- benzimidazol-4-yl]cyclohexyl]-methyl-amino]methyl]cyclohexyl]-6-(1-hydroxy-1-methyl-ethyl)indazol-5-yl]-6-(trifluoromethyl)pyridine-2-carboxamide To a solution of N-[2-[4-[[[4-[1-(2,6-dioxo-3-piperidyl)-3-methyl-2-oxo-benzimidazol-4-yl]cyclohexyl]amino]methyl]cyclohexyl]-6-(1-hydroxy-1-methyl-ethyl)indazol-5-yl]-6-(trifluoromethyl)pyridine-2-carboxamide (400 mg, 491 umol) in THE (6.0 mL) and DMF (3.0 mL) was added TEA (99.3 mg, 982 umol, 137 uL) till pH=8-9. Then HOAc (29.4 mg, 490 umol, 28.0 uL) was added until the pH=5-7, then $(CH_2O)n$ (148 mg, 4.91 mmol, 135 uL) was added. The mixture was stirred at 25° C. for 1 hr. Then $NaBH(OAc)_3$ (104 mg, 491 umol, 3 batches) was added three times and stirred at 25° C. for 17 hr. On completion, the reaction mixture was quenched by water (0.2 mL), filtered and concentrated in vacuo to give a residue. The residue was purified by Prep-HPLC (column: Waters Xbridge C18 150*50 mm*10 um;mobile phase: [water(10 mM $NH_4HCO_3$)-ACN];B %: 50%-80%, 11.5 min) to give the title compounds N-[2-[4-[[[4-[1-(2,6-dioxo-3-piperidyl)-3-methyl-2-oxo-benzimidazol-4-yl]cyclohexyl]- methyl-amino]methyl]cyclohexyl]-6-(1-hydroxy-1-methyl-ethyl)indazol-5-yl]-6-(trifluoromethyl)pyridine-2-carboxamide (36.6 mg, 8% yield) as yellow solid: $^1H$ NMR (400 MHz, DMSO-$d_6$) δ 12.38 (s, 1H), 11.07 (br s, 1H), 8.72 (s, 1H), 8.49-8.43 (m, 1H), 8.41-8.34 (m, 2H), 8.17 (d, J=7.6 Hz, 1H), 7.58 (s, 1H), 7.06-6.92 (m, 3H), 5.96 (s, 1H), 5.38 (dd, J=5.2, 12.8 Hz, 1H), 4.49-4.38 (m, 1H), 3.60 (s, 3H), 3.32-3.16 (m, 2H), 2.95-2.83 (m, 1H), 2.77-2.67 (m, 1H), 2.66-2.59 (m, 1H), 2.30 (d, J=6.4 Hz, 2H), 2.26 (s, 3H), 2.15 (d, J=10.8 Hz, 2H), 2.04-1.89 (m, 7H), 1.86 (d, J=11.2 Hz, 2H), 1.63 (s, 6H), 1.61-1.43 (m, 5H), 1.18-1.03 (m, 2H); LC-MS ($ESI^+$) m/z 829.4 $(M+H)^+$; and N-[2-[4-[[[4-[1-(2,6-dioxo-3-piperidyl)-3-methyl-2-oxo- benzimidazol-4-yl]cyclohexyl]-methyl-amino]methyl]cyclohexyl]-6-(1-hydroxy-1-methyl-ethyl)indazol-5-yl]-6-(trifluoromethyl)pyridine-2-carboxamide (132 mg, 32% yield) as off white solid. $^1H$ NMR (400 MHz, DMSO-$d_6$) δ 12.37 (s, 1H), 11.08 (br s, 1H), 8.72 (s, 1H), 8.48-8.44 (m, 1H), 8.42-8.34 (m, 2H), 8.17 (d, J=7.6 Hz, 1H), 7.59 (s, 1H), 7.07-6.92 (m, 3H), 5.95 (s, 1H), 5.38 (dd, J=5.2, 12.8 Hz, 1H), 4.52-4.40 (m, 1H), 3.61 (s, 3H), 3.32 (s, 2H), 2.96-2.83 (m, 1H), 2.76-2.60 (m, 2H), 2.26 (d, J=8.8 Hz, 2H), 2.22 (s, 3H), 2.17 (s, 2H), 2.11-2.00 (m, 5H), 1.99-1.89 (m, 4H), 1.74-1.67 (m, 1H), 1.63 (s, 6H), 1.61-1.54 (m, 4H), 1.24-1.11 (m, 2H); LC-MS ($ESI^+$) m/z 829.3 $(M+H)^+$. The stereochemistry of the isomers was assigned arbitrarily.

Example 17. Synthesis of N-[2-[4-[[2-[3-[3-[2-[(2S)-1-[(2S)-2-cyclohexyl-2-[[(2S)-2-(methylamino)propanoyl]amino]acetyl]pyrrolidin-2-yl]thiazole-4-carbonyl]phenoxy]propyl]-7-azaspiro[3.5]nonan-7-yl]methyl]cyclohexyl]-6-methoxy-indazol-5-yl]-6-(trifluoromethyl)pyridine-2-carboxamide (I-181)
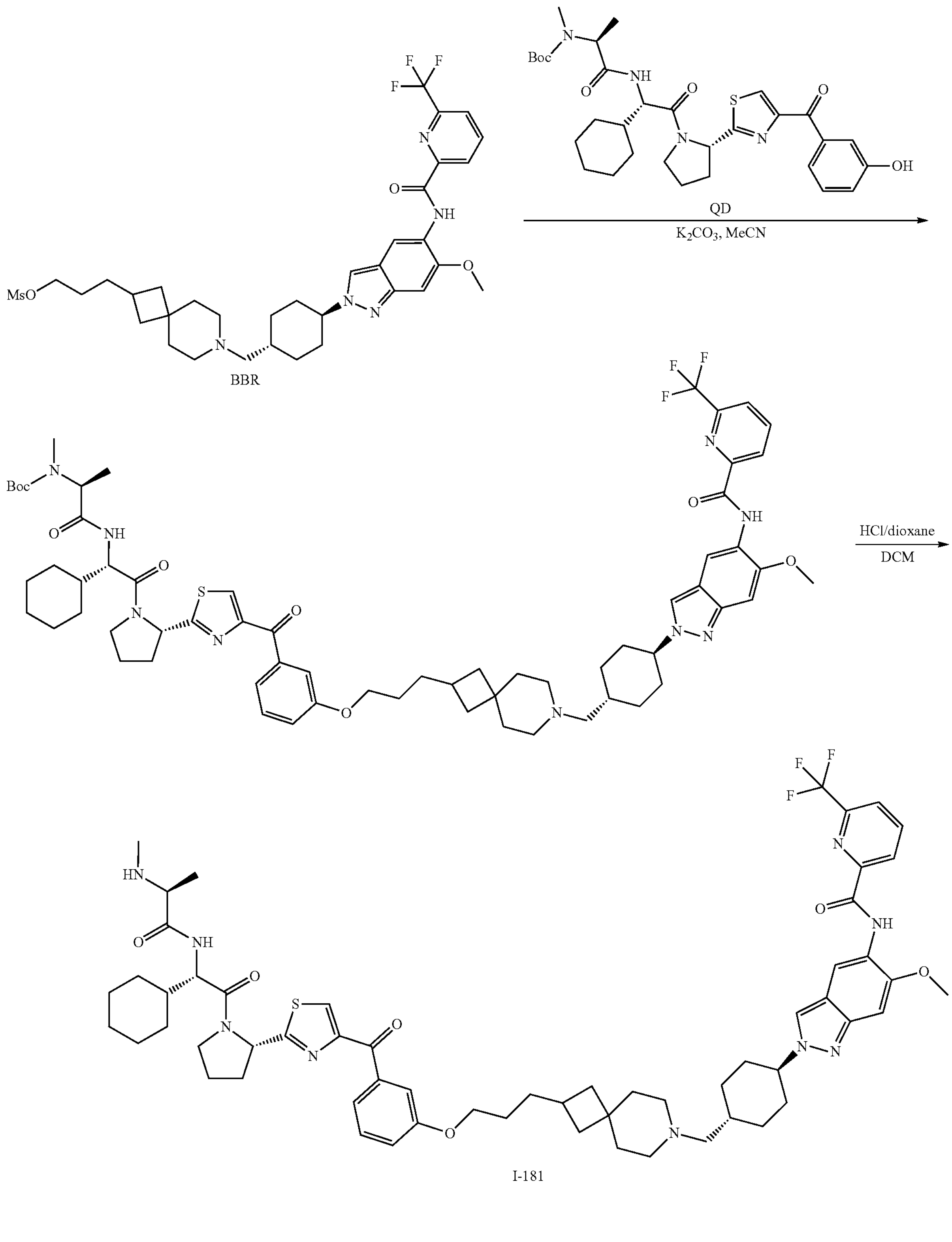
I-181

Step 1—Tert-butyl N-[(1S)-2-[[(1S)-1-cyclohexyl-2-[(2S)-2-[4-[3-[3-[7-[[4-[6-methoxy-5-[[6- (trifluoromethyl)pyridine-2-carbonyl]amino]indazol-2-yl]cyclohexyl]methyl]-7-azaspiro[3.5]nonan-2-yl]propoxy]benzoyl]thiazol-2-yl]pyrrolidin-1-yl]-2-oxo-ethyl]amino]-1-methyl-2-oxo-ethyl]-N-methyl-carbamate To a solution of 3-[7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propyl methanesulfonate (200 mg, 289 umol, Intermediate BBR) and tert-butyl N-[(1S)-2-[[(1S)-1-cyclohexyl-2-[(2S)-2-[4-(3-hydroxybenzoyl)thiazol-2-yl]pyrrolidin-1-yl]-2-oxo-ethyl]amino]-1-methyl-2-oxo-ethyl]-N-methyl-carbamate (190 mg, 318 umol, Intermediate QD) in MeCN (8.0 mL) was added $K_2CO_3$ (79.9 mg, 578 umol), and the reaction mixture was stirred at 80° C. for 12 hours. On completion, the reaction mixture was concentrated in vacuo to give a residue. The residue was purified by reverse phase (0.1% FA condition) to give the title compound (300 mg, 86% yield) as a light yellow solid. LC-MS (ESI+) m/z 1194.7 $(M+1)^+$.

Step 2—N-[2-[4-[[2-[3-[3-[2-[(2S)-1-[(2S)-2-cyclohexyl-2-[[(2S)-2-(methylamino)propanoyl]amino]acetyl]pyrrolidin-2-yl]thiazole-4-carbonyl]phenoxy]propyl]-7-azaspiro[3.5]nonan-7-yl]methyl]cyclohexyl]-6-methoxy-indazol-5-yl]-6-(trifluoromethyl)pyridine-2-carboxamide To a solution of tert-butyl N-[(1S)-2-[[(1S)-1-cyclohexyl-2-[(2S)-2-[4-[3-[3-[7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propoxy]benzoyl]thiazol-2-yl]pyrrolidin-1-yl]-2-oxo-ethyl]amino]-1-methyl-2-oxo-ethyl]-N-methyl-carbamate (300 mg, 251 umol) in DCM (5 mL) was added HCl/dioxane (4 M, 4 mL), and the reaction mixture was stirred at 25° C. for 1 hr. On completion, the reaction mixture was concentrated in vacuo to give a residue. The residue was purified by prep-HPLC (column: Phenomenex Synergi C18 150*25*10 um; mobile phase: [water(0.225% FA)-ACN];B %: 22%-52%, 10 min) to give the title compound (174 mg, 62.9% yield) as a white solid. 1H NMR (400 MHz, DMSO-$d_6$) δ 10.50 (s, 1H), 8.68 (s, 1H), 8.52-8.43 (m, 2H), 8.43-8.37 (m, 1H), 8.31 (s, 1H), 8.25-8.15 (m, 3H), 7.68-7.58 (m, 2H), 7.48-7.42 (m, 1H), 7.25-7.18 (m, 1H), 7.14 (s, 1H), 5.43-5.34 (m, 1H), 4.50-4.45 (m, 1H), 4.36-4.32 (m, 1H), 4.02-3.98 (m, 2H), 3.98 (s, 3H), 3.84-3.75 (m, 2H), 3.75-3.60 (m, 1H), 3.30 (q, J=6.4 Hz, 1H), 2.41-2.31 (m, 2H), 2.29 (s, 3H), 2.27-2.20 (m, 3H), 2.20-2.15 (m, 3H), 2.14-1.99 (m, 4H), 1.94-1.81 (m, 6H), 1.76-1.57 (m, 9H), 1.56-1.43 (m, 6H), 1.36-1.27 (m, 2H), 1.24-1.12 (m, 4H), 1.11-0.87 (m, 6H); LC-MS (ESI+) m/z 1094.6 $(M+1)^+$.

Example 18. Synthesis of (3S)-2-[(2S)-3,3-Dimethyl-2-[[(2S)-2-(methylamino)propanoyl]amino]butanoyl]-7-[3- [7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propoxy]-N-[(1R)-tetralin-1-yl]-3,4-dihydro-1H-isoquinoline-3-carboxamide (I-186)

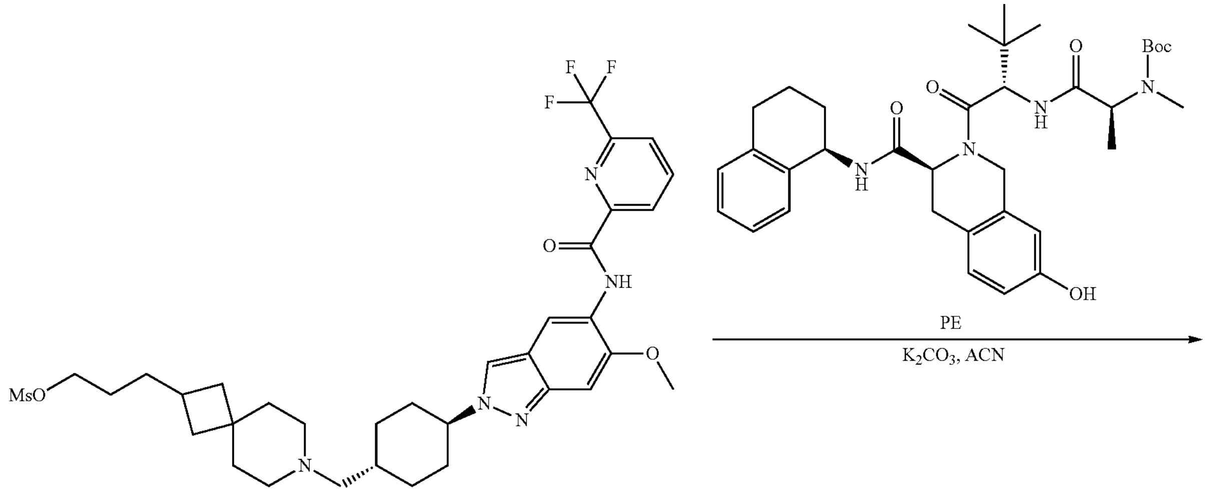

BBr

-continued

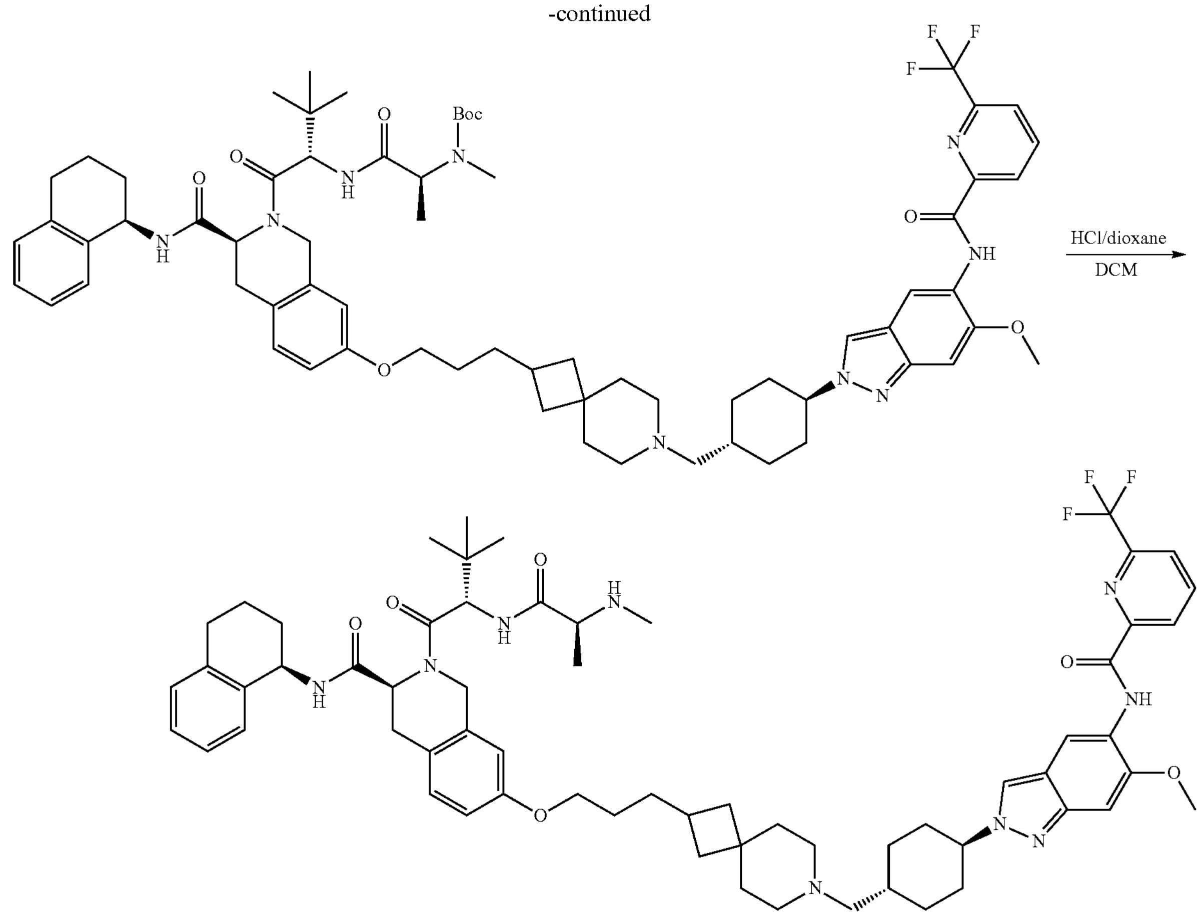

I-186

Step 1—Tert-butyl N-[(1S)-2-[[(1S)-1-[(3S)-7-[3-[7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate To a solution of 3-[7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propyl methanesulfonate (50.0 mg, 72.2 umol, Intermediate BBR) and tert-butyl N-[(1S)-2-[[(1S)-1-[(3S)-7-hydroxy-3-[[(1R)-tetralin-1-yl]carbamoyl]-3,4-dihydro-1H-soquinoline-2-carbonyl]-2,2-dimethyl-propyl]amino]-1-methyl-2-oxo-ethyl]-N— methyl-carbamate (49.3 mg, 79.5 umol, Intermediate PE) in ACN (2 mL) was added $K_2CO_3$ (49.9 mg, 361 umol) at 25° C. The reaction mixture was stirred at 80° C. for 24 hours. On completion, the mixture was filtered and the filtrate was concentrated in vacuo. The residue was purified by prep-HPLC (column: 3_Phenomenex Luna C18 75*30 mm*3 um; mobile phase: [water (0.225% FA)-ACN]; B %: 47%-67%, 8 min) to give the title compound (23.0 mg, 26% yield) as a white solid. LC-MS ($ESI^+$) m/z 1216.5 $(M+H)^+$.

Step 2—(3S)-2-[(2S)-3,3-Dimethyl-2-[[(2S)-2-(methylamino)propanoyl]amino]butanoyl]-7-[3- [7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propoxyl-N-[(1R)-tetralin-1-yl]-3,4-dihydro-1H-isoquinoline-3-carboxamide To a solution of tert-butyl N-[(1S)-2-[[(1S)-1-[(3S)-7-[3-[7-[[4-[6-methoxy-5-[[6-(trifluoromethyl)pyridine-2-carbonyl]amino]indazol-2-yl]cyclohexyl]methyl]-7-azaspiro[3.5]nonan-2-yl]propoxy]-3-[[(1R)-tetralin-1-yl]carbamoyl]-3,4-dihydro-1H-isoquinoline-2-carbonyl]-2,2-dimethyl-propyl]amino]-1-methyl-2-oxo-ethyl]-N-methyl-carbamate (23.0 mg, 18.9 umol) in DCM (2 mL) was added HCl/dioxane (4 M, 1 mL) at 25° C. The mixture was stirred at 25° C. for 1 hour. On completion, the reaction mixture was concentrated in vacuo. The residue was purified by prep-HPLC (column: 3_Phenomenex Luna C18 75*30 mm*3 um; mobile phase: [water(0.225% FA)-ACN]; B %: 30%-50%, 8 min) to give the title compound (11.9 mg, 54% yield, FA salt) as a white solid. $^1H$ NMR (400 MHz, DMSO-$d_6$) δ 10.50 (s, 1H), 8.68 (s, 1H), 8.48-8.44 (m, 1H), 8.43-8.38 (m, 1H), 8.32 (s, 1H), 8.22 (dd, J=1.2, 8.0 Hz, 1H), 8.20-8.15 (m, 1H), 7.94-7.85 (m, 1H), 7.15 (s, 1H), 7.12-7.00 (m, 5H), 6.89-6.78 (m, 1H), 6.77-6.74 (m, 1H), 4.97-4.84 (m, 2H), 4.78-4.61 (m, 2H), 4.42-4.31 (m, 1H), 3.98 (s, 3H), 3.91 (t, J=6.0 Hz, 2H), 3.00-2.91 (m, 3H), 2.74-2.69 (m, 1H), 2.27-2.19 (m, 3H), 2.17 (s, 2H), 2.12 (s, 3H), 2.11-2.06 (m, 4H), 1.95-1.79 (m, 9H), 1.65-1.42 (m, 12H), 1.35-1.28 (m, 2H), 1.10 (d, J=6.8 Hz, 3H), 1.08-1.01 (m, 9H), 0.94 (s, 3H); LC-MS ($ESI^+$) m/z 1116.4 $(M+H)^+$.

Example 19. Synthesis of N-((2R)-2-(((3-((1r,3R)-3-((2-(2,6-Dioxopiperidin-3-yl)-1,3-dioxoisoindolin-4-yl)amino) cyclobutoxy)propyl)(methyl)amino) methyl)-2-methyl-6-morpholino-2,3-dihydrobenzofuran-5-yl)-6-(trifluoromethyl) picolinamide (I-256)

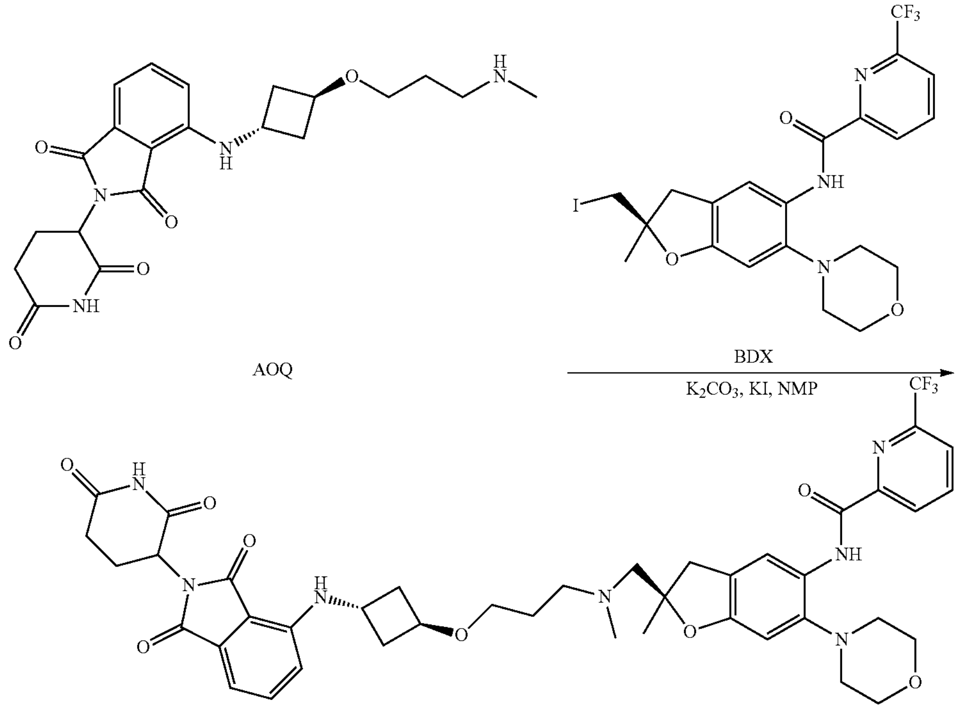

AOQ

BDX

I-256

The mixture of 2-(2,6-dioxopiperidin-3-yl)-4-(((1r,3r)-3-(3-(methylamino)propoxy)cyclobutyl)amino) isoindoline-1,3-dione (45.4 mg, 109 umol, Intermediate AOQ), (R)—N-(2-(iodomethyl)-2-methyl-6-morpholino-2,3-dihydrobenzofuran-5-yl)-6-(trifluoromethyl)picolinamide (30.0 mg, 54.8 umol, Intermediate BDX), $K_2CO_3$ (22.7 mg, 164 umol), and KI (18.2 mg, 109 umol) in NMP (1 mL) was stirred at 110° C. for 8 hrs under MW. On completion, the reaction mixture was added water drop-wise. The residue was purified by Prep-HPLC (column: Phenomenex luna C18 150*25 mm*10 um; mobile phase: [water (0.225% FA)-ACN]; B %: 23%-53%, 9 min) to give the title compound (3.35 mg, 7% yield) as a yellow solid. $^1$H NMR (400 MHz, DMSO-$d_6$) δ 11.21-11.03 (m, 1H), 10.83 (s, 1H), 8.45-8.41 (m, 1H), 8.40-8.34 (m, 2H), 8.19 (d, J=7.6 Hz, 1H), 7.55 (t, J=7.2 Hz, 1H), 7.03 (d, J=6.8 Hz, 1H), 6.87 (d, J=7.6 Hz, 1H), 6.77 (s, 1H), 6.45 (d, J=4.8 Hz, 1H), 5.06 (d, J=12.8 Hz, 1H), 4.15-4.04 (m, 2H), 3.85-3.76 (m, 4H), 3.29-3.23 (m, 3H), 2.93-2.89 (m, 1H), 2.87 (s, 1H), 2.82 (s, 4H), 2.68 (s, 1H), 2.66-2.60 (m, 1H), 2.57 (d, J=4.8 Hz, 4H), 2.36-2.31 (m, 3H), 2.27 (s, 3H), 2.23-2.16 (m, 2H), 2.06-2.00 (m, 1H), 1.67-1.56 (m, 2H), 1.36 (s, 3H). LC-MS (ESI$^+$) m/z 834.6 $(M+H)^+$.

Example 20. Synthesis of N-[2-[4-[[1-(2,6-dioxo-3-piperidyl)-3-methyl-2-oxo-benzimidazol-4-yl] methyl]cyclohexyl]-6- methoxy-indazol-5-yl]-6-(trifluoromethyl)pyridine-2-carboxamide (I-288)

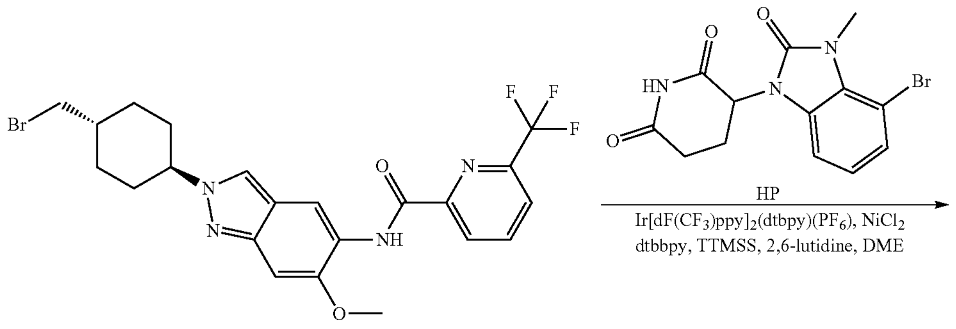

HP

BEC

-continued

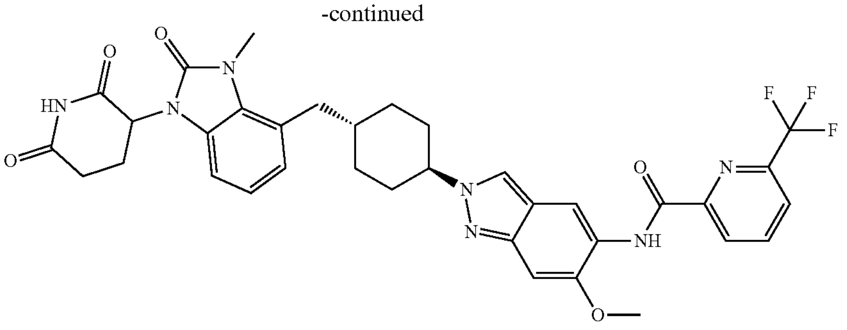

I-288

To a solution of N-[2-[4-(bromomethyl)cyclohexyl]-6-methoxy-indazol-5-yl]-6-(trifluoromethyl)pyridine-2-carboxamide (340 mg, 664 umol, Intermediate BEC) and 3-(4-bromo-3-methyl-2-oxo-benzimidazol-1-yl) piperidine-2,6-dione (172 mg, 511 umol, Intermediate TIP) in DME (1.5 mL) was added Jr[dF($CF_3$)ppy]$_2$(dtbpy)($PF_6$) (3.36 mg, 5.11 umol,), $NiCl_2$-dtbbpy (1.02 mg, 2.56 umol), TTMSS (127 mg, 511 umol) and 2,6-lutidine (109 mg, 1.02 mmol). The vial was sealed and placed under nitrogen and the reaction was stirred and irradiated with a 34 W blue LED lamp (7 cm away), with cooling fan to keep the reaction temperature at 25° C. for 14 hr. On completion, the mixture was quenched with water (0.5 mL), filtered and concentrated to give a residue. The residue was purified by Prep-HPLC (column: Phenomenex luna C18 150*40 mm*15 um;mobile phase: [water(0.225% FA)-ACN];B %: 52%-82%, 11 min) to give the title compound (1.14 mg, 0.3% yield) as an off-white solid. $^1$H NMR (400 MHz, DMSO-$d_6$) δ 11.22-11.01 (m, 1H), 10.50 (s, 1H), 8.68 (s, 1H), 8.49-8.45 (m, 1H), 8.50-8.45 (m, 1H), 8.44-8.39 (m, 1H), 8.31 (s, 1H), 8.25-8.22 (m, 1H), 7.15 (s, 1H), 7.02-6.97 (m, 2H), 6.88 (dd, J=2.0, 6.8 Hz, 1H), 5.43-5.34 (m, 1H), 4.47-4.36 (m, 1H), 3.98 (s, 3H), 3.60 (s, 3H), 3.18 (s, 1H), 2.87 (d, J=6.8 Hz, 2H), 2.78-2.67 (m, 1H), 2.18-2.11 (m, 1H), 2.05-1.96 (m, 2H), 1.88 (d, J=11.2 Hz, 4H), 1.70-1.61 (m, 1H), 1.42-1.32 (m, 2H); LC-MS (ESI+) m/z 690.3 (M+1)$^+$.

Example 21. Synthesis of N-[2-[4-[[[1-(2,6-dioxo-3-piperidyl)-3-methyl-2-oxo-benzimidazol-4-yl]-methyl-amino]methyl]cyclohexyl]-6-(1-hydroxy-1-methyl-ethyl)indazol-5-yl]-6-(trifluoromethyl)pyridine-2-carboxamide (I-310)

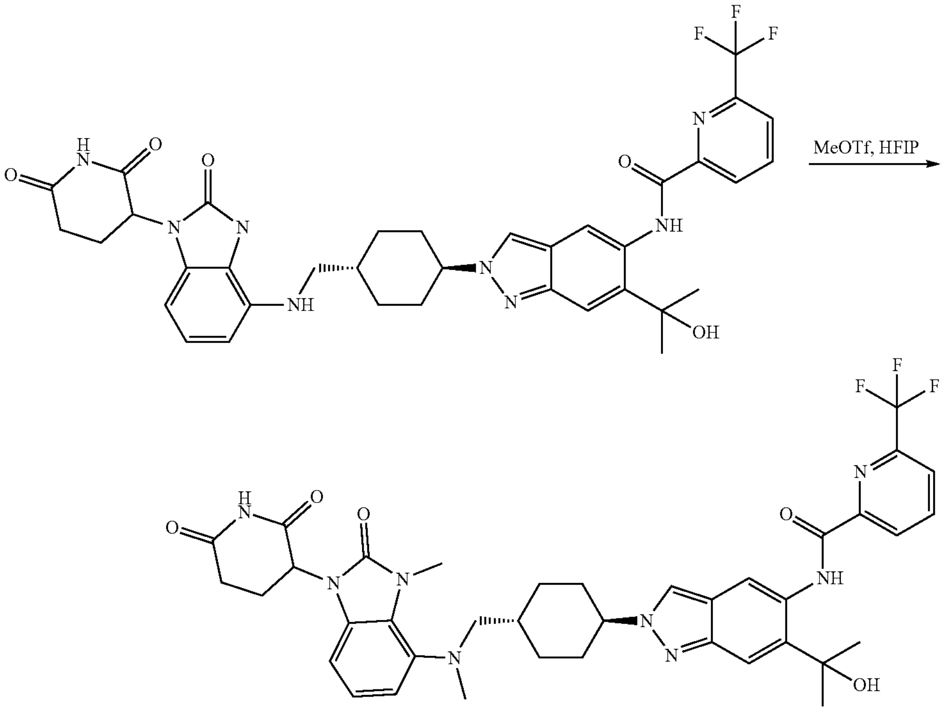

I-310

To a solution of N-[2-[4-[[[1-(2,6-dioxo-3-piperidyl)-3-methyl-2-oxo-benzimidazol-4-yl]amino]methyl]cyclohexyl]-6-(1-hydroxy-1-methyl-ethyl)indazol-5-yl]-6-(trifluoromethyl)pyridine-2-carboxamide (100 mg, 136 umol, I-147) in 1,1,1,3,3,3-hexafluoropropan-2-ol (0.50 mL) was added methyl trifluoromethanesulfonate (22.4 mg, 136 umol) at 0° C. The reaction mixture was stirred at 20° C. for 1 hr. On completion, the reaction mixture was concentrated in vacuo. The residue was purified by prep-HPLC (column: Phenomenex Synergi C18 150*25*10 um;mobile phase: [water(0.225% FA) -ACN];B %: 46%-76%, 10 min) to give the title compound (33.1 mg, 33% yield, 100% purity) as a yellow solid. $^{1}$H NMR (400 MHz, DMSO-$d_6$) δ 12.35 (s, 1H), 11.10 (d, J=3.2 Hz, 1H), 8.69 (s, 1H), 8.47-8.41 (m, 1H), 8.39-8.33 (m, 2H), 8.16 (d, J=7.6 Hz, 1H), 7.55 (s, 1H), 7.05-6.96 (m, 2H), 6.89 (d, J=7.6 Hz, 1H), 5.94 (s, 1H), 5.41-5.32 (m, 1H), 4.49-4.37 (m, 1H), 3.66 (s, 3H), 2.89 (d, J=6.4 Hz, 2H), 2.75-2.68 (m, 1H), 2.65 (s, 3H), 2.54-2.52 (m, 2H), 2.18-2.10 (m, 2H), 2.05-1.97 (m, 3H), 1.94-1.82 (m, 2H), 1.76-1.65 (m, 1H), 1.61 (s, 6H), 1.31-1.19 (m, 2H); LC-MS (ESI$^+$) m/z 747.3 (M+H)$^+$.

Example 22. Synthesis of N-((2S)-2-((2-(2-((2-(2,6-dioxopiperidin-3-yl)-1,3-dioxoisoindolin-4-yl)amino)ethyl)-7- azaspiro[3.5]nonan-7-yl)methyl)-2-methyl-6-morpholino-2,3-dihydrobenzofuran-5-yl)-6-(trifluoromethyl)picolinamide (I-319)

To a solution of N-[(2S)-2-(iodomethyl)-2-methyl-6-morpholino-3H-benzofuran-5-yl]-6-(trifluoro methyl)pyridine-2-carboxamide (80.0 mg, 146 umol, Intermediate BDQ) and 4-[2-(7-azaspiro[3.5]nonan-2-yl) ethylamino]-2-(2,6-dioxo-3-piperidyl)isoindoline-1,3-dione (135 mg, 292 umol, HCl salt, Intermediate ATC) in NMP (3.0 mL) was added $K_2CO_3$ (80.8 mg, 585 umol) and KI (73 mg, 438 umol) under $N_2$. The mixture was stirred at 120° C. for 2 hours under microwave condition. On completion, the reaction mixture was filtered and concentrated in vacuo to give a residue. The residue was purified by Prep-HPLC (HCl: column: 3_Phenomenex Luna C18 75*30 mm*3 um; mobile phase: [water (0.05% HCl)-ACN]; B %: 42%-62%, 6.5 min) to give the title compound (22.6 mg, 18% yield) as a yellow solid. $^{1}$H NMR (400 MHz, DMSO-$d_6$) δ 10.82 (s, 1H), 8.72 (s, 2H), 8.45-8.31 (m, 3H), 8.20 (m, 1H), 7.59 (m, 1H), 7.08-7.02 (m, 2H), 6.74 (m, 1H), 6.48 (m, 1H), 5.15 (m, 1H), 4.11-4.03 (m, 2H), 3.79 (s, 4H), 3.24-3.20 (m, 3H), 2.94-2.78 (m, 11H), 2.50 (m, 1H), 1.97 (m, 4H), 1.72-1.63 (m, 6H), 1.47-1.34 (m, 5H). LC-MS (ESI$^+$) m/z 844.1 (M+H)$^+$.

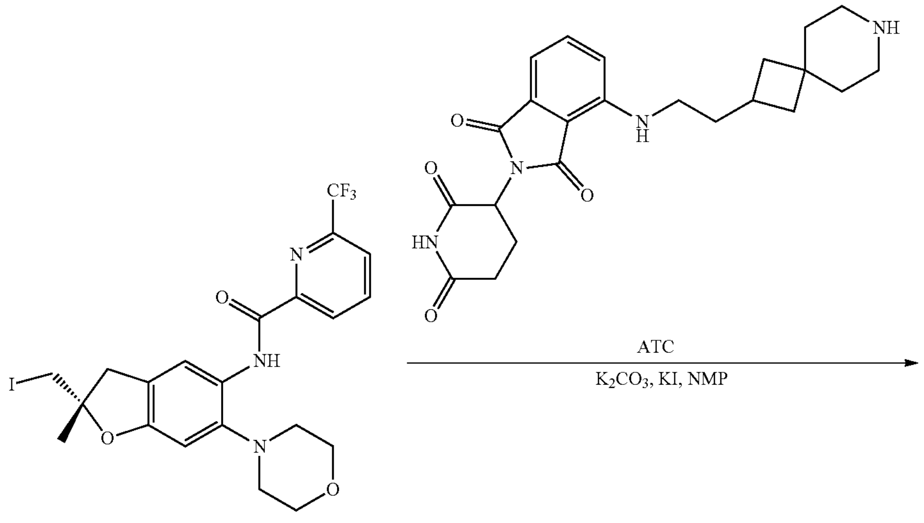

BDQ

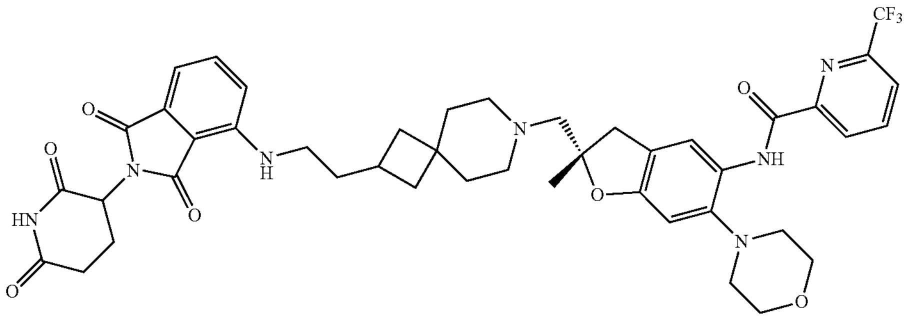

I-319

Example 23. Synthesis of N-[(2R)-2-[[3-[3-[[2-(2,6-dioxo-3-piperidyl)-1,3-dioxo-isoindolin-4-yl]amino]cyclobutoxy]propyl-methyl-amino]methyl]-2-methyl-6-morpholino-3H-benzofuran-5-yl]pyrazolo[1,5-a]pyrimidine-3-carboxamide (I-161)

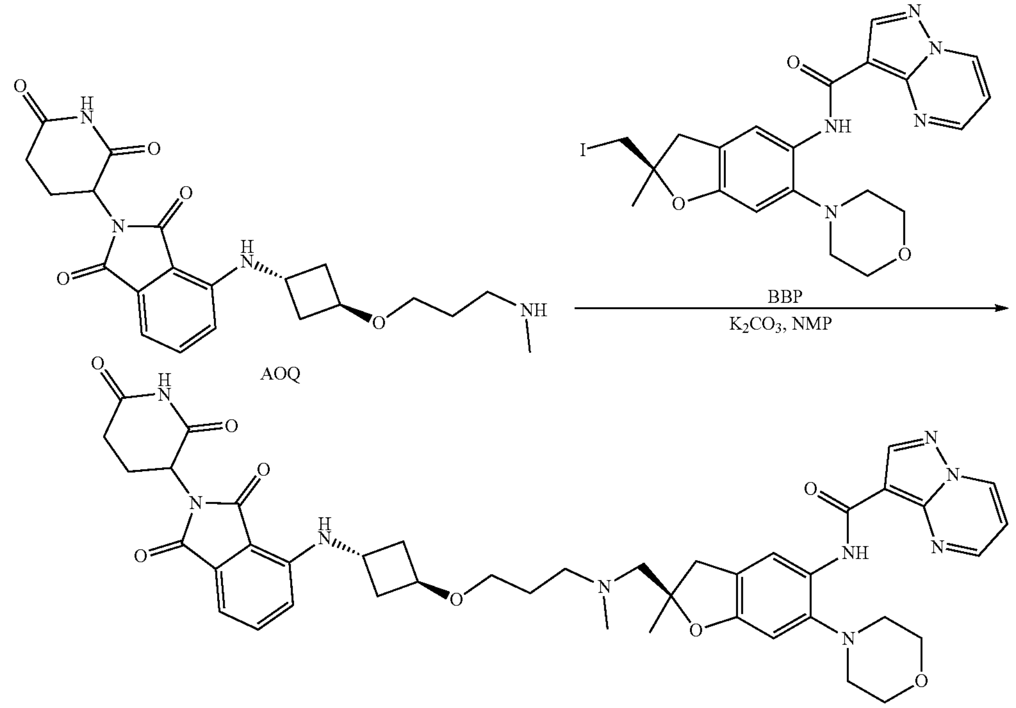

I-161

A mixture of N-[(2R)-2-(iodomethyl)-2-methyl-6-morpholino-3H-benzofuran-5-yl]pyrazolo[1,5-a] pyrimidine-3-carboxamide (20.0 mg, 38.5 umol, Intermediate BBP), 2-(2,6-dioxo-3-piperidyl)-4- [[3-[3-(methylamino)propoxy]cyclobutyl]amino]isoindoline-1,3-dione (31.9 mg, 77.0 umol, Intermediate AOQ), $K_2CO_3$ (15.9 mg, 115 umol) and KI (19.1 mg, 115 umol) in NMP (1 mL) was stirred at 110° C. for 4 hours under microwave condition. On completion, after cooled to 25° C., then the mixture was filtered. The filtrate was purified by Prep-HPLC (column: Phenomenex Gemini-NX C18 75*30 mm*3 um;mobile phase:[water (0.225% FA)-ACN]; B %:7%-37%, 7 min) to give the title compound (5.50 mg, 14% yield, FA salt) as yellow solid. $^1$H NMR (400 MHz, DMSO-$d_6$) δ 11.10 (s, 1H), 10.40 (s, 1H), 9.32 (dd, J=1.6, 7.2 Hz, 1H), 8.89 (m, 1H), 8.64 (s, 1H), 8.31 (s, 1H), 7.51 (t, J=7.6 Hz, 1H), 7.30 (dd, J=4.0, 7.2 Hz, 1H), 7.00 (d, J=7.2 Hz, 1H), 6.84 (d, J=8.4 Hz, 1H), 6.69 (s, 1H), 6.42 (d, J=4.0 Hz, 1H), 5.07-5.01 (m, 1H), 4.07 (dd, J=5.6, 12.0 Hz, 2H), 3.81 (t, J=4.0 Hz, 4H), 3.60 (m, 1H), 3.31 (s, 3H), 2.96-2.74 (m, 7H), 2.36-2.27 (m, 1H), 2.26 (s, 3H), 2.21-2.13 (m, 2H), 2.07-2.00 (m, 1H), 1.76 (m 1H), 1.65-1.53 (m, 2H), 1.34 (s, 2H), 1.38-1.29 (m, 1H); LCMS (ESI+) m/z 806.3 $(M+H)^+$.

Example 24. Synthesis of N-[(2R)-2-[[2-[2-[[2-(2,6-dioxo-3-piperidyl)-1,3-dioxo-isoindolin-4-yl]amino]ethyl]-7-azaspiro[3.5]nonan-7-yl]methyl]-2-methyl-6-morpholino-3H-benzofuran-5-yl]-6-(trifluoromethyl)pyridine-2-carboxamide (I-326)

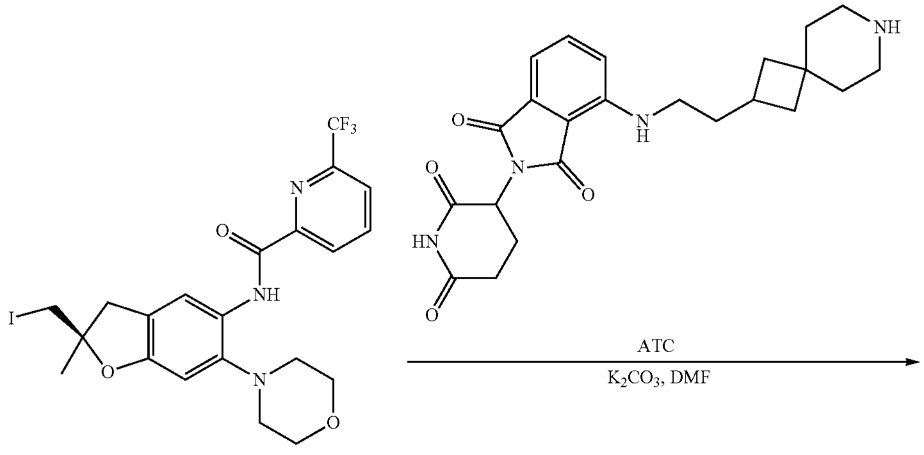

BDX

-continued

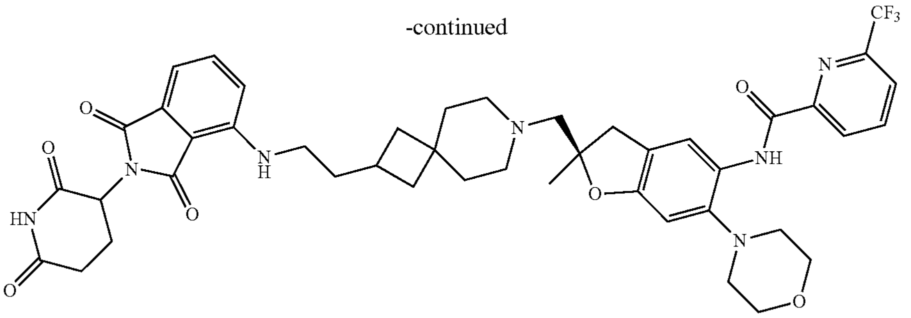

I-326

A mixture of N-[(2R)-2-(iodomethyl)-2-methyl-6-morpholino-3H-benzofuran-5-yl]-6-(trifluoromethyl)pyridine-2-carboxamide (100 mg, 182 umol, Intermediate BDX), 4-[2-(7-azaspiro[3.5]nonan-2-yl)ethylamino]-2-(2,6- dioxo-3-piperidyl)isoindoline-1,3-dione (155 mg, 365 umol, Intermediate ATC), K2CO3 (75.7 mg, 548 umol) and KI (90.9 mg, 548 umol) in NMP (1 mL) was stirred at 110° C. for 4 hours. The reaction mixture was filtered. The filtrate was purified by prep-HPLC (column: Phenomenex Synergi C18 150*25*10 um; mobile phase: [water (0.225% FA)-ACN]; B %: 30%-60%, 10 min) to give the title compound (22.9 mg, 6% yield, FA) as yellow solid. $^1$H NMR (400 MHz, DMSO-$d_6$) δ 11.08 (s, 1H), 10.83 (s, 1H), 8.48-8.43 (m, 1H), 8.39 (t, J=8.0 Hz, 1H), 8.35 (s, 1H), 8.24-8.18 (m, 1H), 7.58 (dd, J=7.2, 8.4 Hz, 1H), 7.11-6.97 (m, 2H), 6.79 (s, 1H), 6.46 (t, J=5.6 Hz, 1H), 5.04 (dd, J=5.6, 12.8 Hz, 1H), 3.80 (m, 4H), 3.30 (m, 2H), 3.25-3.16 (m, 4H), 2.97-2.86 (m, 2H), 2.84-2.78 (m, 4H), 2.62-2.55 (m, 2H), 2.52 (m, 4H), 2.28-2.18 (m, 2H), 2.05-2.00 (m, 1H), 1.96-1.86 (m, 2H), 1.70-1.65 (m, 2H), 1.59-1.42 (m, 4H), 1.38 (s, 3H); LC-MS (ESI+) m/z 844.4 (M+H)$^+$.

Example 25. Synthesis of N-[(2S)-2-[[3-[3-[[2-(2,6-dioxo-3-piperidyl)-1,3-dioxo-isoindolin-4-yl]amino]cyclobutoxy]propyl-methyl-amino]methyl]-2-methyl-6-morpholino-3H-benzofuran-5-yl]-6-(trifluoromethyl)pyridine-2-carboxamide (I-330)

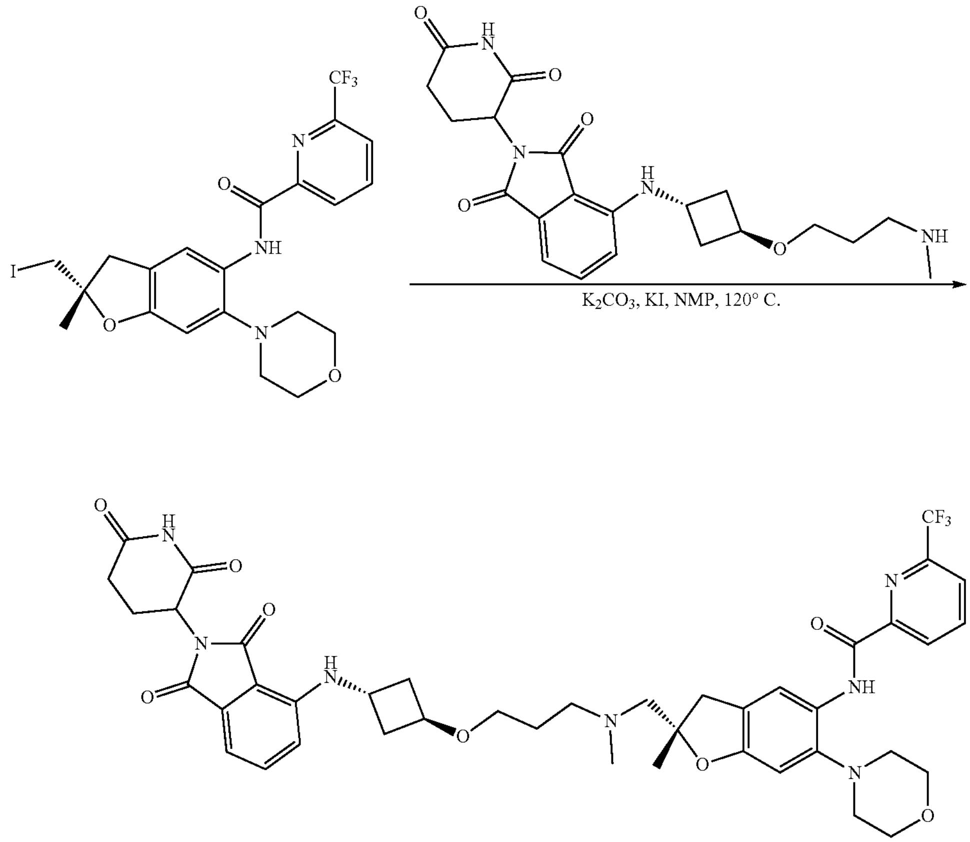

I-330

A mixture of N-[(2S)-2-(iodomethyl)-2-methyl-6-morpholino-3H-benzofuran-5-yl]-6-(trifluoromethyl)pyridine-2-carboxamide (26.4 mg, 48.2 umol, Intermediate BDQ), 2-(2,6-dioxo-3-piperidyl)-4-[[3- [3-(methylamino)propoxy] cyclobutyl]amino]isoindoline-1,3-dione (40.0 mg, 96.5 umol, free based, Intermediate AOQ), $K_2CO_3$ (20.0 mg, 144 umol,) and KI (24.0 mg, 144 umol) in NMP (2 mL) was stirred at 120° C. for 8 hrs under microwave. On completion, the reaction mixture was filtered. The filtrate was purified prep-HPLC (column: Phenomenex Synergi C18 150*25*10 um; mobile phase: [water (0.225% FA)-ACN]; B %: 24%-54%, 10 min) to give the title compound (7.80 mg, 17% yield, FA) as yellow solid. $^1H$ NMR (400 MHz, DMSO-$d_6$) δ 11.10 (s, 1H), 10.81 (s, 1H), 8.45-8.39 (m, 1H), 8.38-8.33 (m, 2H), 8.17 (d, J=7.6 Hz, 1H), 7.57-7.50 (m, 1H), 7.02 (d, J=7.2 Hz, 1H), 6.85 (d, J=8.8 Hz, 1H), 6.76 (s, 1H), 6.44 (d, J=5.2 Hz, 1H), 5.05 (dd, J=5.6, 12.8 Hz, 1H), 4.08 (m, 2H), 3.81-3.75 (m, 4H), 3.26 (m, 2H), 2.93-2.85 (m, 2H), 2.83-2.77 (m, 4H), 2.63-2.53 (m, 4H), 2.46 (m, 1H), 2.35-2.28 (m, 4H), 2.26 (s, 3H), 2.17 (m, 3H), 2.06-1.99 (m, 1H), 1.59 (m, 2H), 1.35 (s, 3H); LCMS (ESI+) m/z 834.3 $(M+H)^+$.

Example 26. Synthesis of N-[(2R)-2-[[2-[2-[[2-(2,6-dioxo-3-piperidyl)-1,3-dioxo-isoindolin-4-yl]amino] ethyl]-7-azaspiro[3.5]nonan-7-yl]methyl]-2-methyl-6-morpholino-3H-benzofuran-5-yl]pyrazolo[1,5-a] pyrimidine-3-carboxamide (I-196)

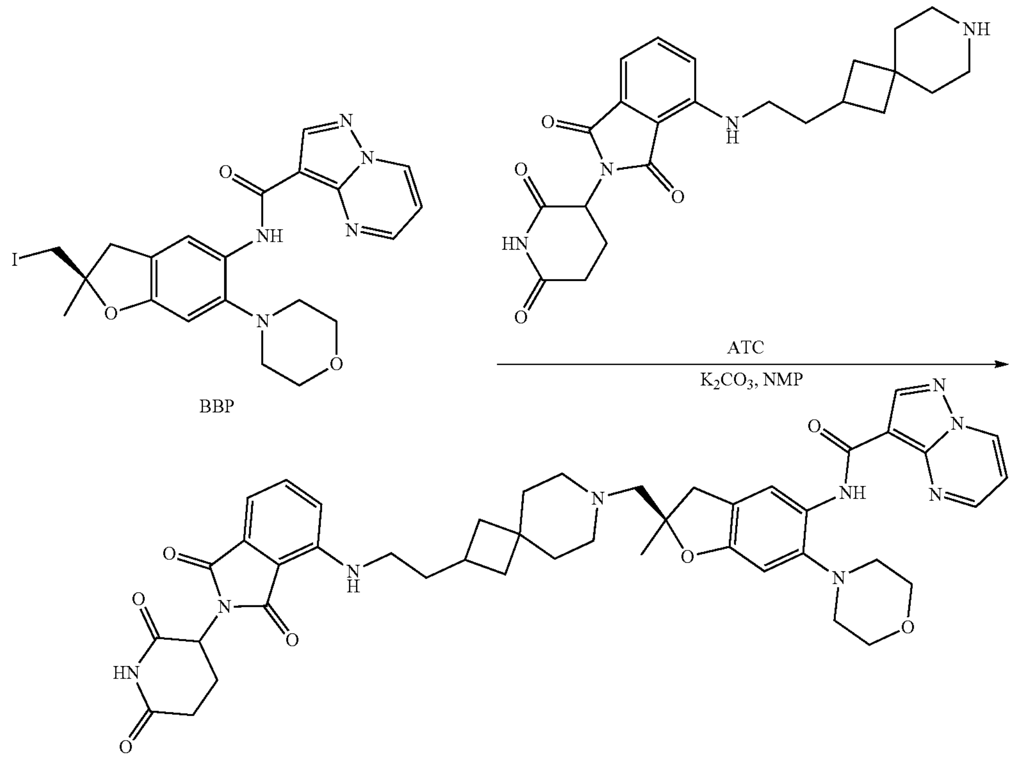

BBP

I-196

A mixture solution of N-[(2R)-2-(iodomethyl)-2-methyl-6-morpholino-3H-benzofuran-5-yl]pyrazolo[1,5-a] pyrimidine-3-carboxamide (24.4 mg, 47.1 umol, Intermediate BBP), 4-[2-(7-azaspiro[3.5]nonan-2-yl) ethylamino]-2-(2,6-diox o-3-piperidyl)isoindoline-1,3-dione (20.0 mg, 47.1 umol, Intermediate ATC) and $K_2CO_3$ (13.0 mg, 94.2 umol) in NMP (1 mL) was stirred at 110° C. for 3 hours under microwave. The reaction mixture was filtered. The filtrate was purified by prep-HPLC (column: Phenomenex luna C18 150*25 mm*10 um; mobile phase: [water(0.225% FA)-ACN];B %: 22%-52%, 10 min) to give the title compound (1.59 mg, 3% yield, FA salt) as yellow solid. $^1H$ NMR (400 MHz, $CDCl_3$) δ 10.46 (s, 1H), 8.84 (dd, J=1.6, 7.2 Hz, 1H), 8.79 (s, 1H), 8.77 (dd, J=1.6, 4.0 Hz, 1H), 8.43 (s, 1H), 7.49 (t, J=7.6 Hz, 1H), 7.12-7.04 (m, 2H), 6.87 (d, J=8.8 Hz, 1H), 6.64 (d, J=10.4 Hz, 1H), 6.17 (m, 1H), 4.94-4.88 (m, 1H), 3.97-3.93 (m, 4H), 3.30-3.17 (m, 3H), 2.92 (m, 5H), 2.90-2.73 (m, 4H), 2.71-2.50 (m, 6H), 2.32-2.26 (m, 1H), 2.14 (m, 1H), 2.01-1.96 (m, 2H), 1.75 (m, 2H), 1.67 (m, 2H), 1.56 (m, 2H), 1.47 (d, J=1.6 Hz, 3H), 1.43-1.38 (m, 2H); LCMS $(ESI^+)$ m/z 816.2 $(M+H)^+$.

Example 27. Synthesis of N-(2-((1r,4r)-4-(hydroxymethyl)cyclohexyl)-5-methoxybenzo[d]oxazol-6-yl)-6-(trifluoro methyl)picolinamide (I-280)

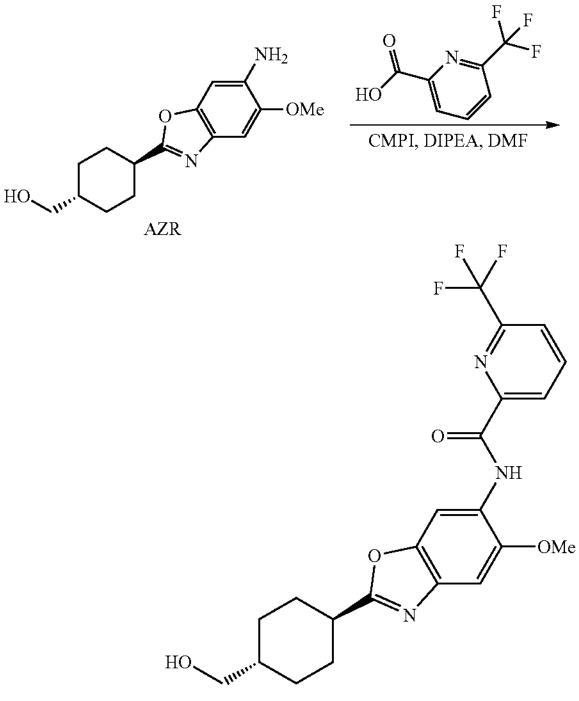

AZR

I-280

To a mixture of ((1r,4r)-4-(6-amino-5-methoxybenzo[d]oxazol-2-yl)cyclohexyl)methanol (30.0 mg, 108 umol, Intermediate AZR), DIPEA (14.0 mg, 108 umol, 18.9 uL) in DMF (1 mL) was added CMPI (33.2 mg, 130 umol) and 6-(trifluoromethyl)picolinic acid (20.7 mg, 108 umol, CAS #131747-42-7). The reaction mixture was stirred at 25° C. for 1 hour. On completion, the reaction mixture was quenched with water (0.05 mL) and concentrated in vacuo. The residue was purified by prep-HPLC (column: Phenomenex Synergi C18 150*25*10 um; mobile phase: [water (0.225% FA)-ACN]; B %: 48%-78%, 10 min) to give the title compound (28.2 mg, 57% yield) as white solid. $^1$H NMR (400 MHz, DMSO-$d_6$) δ 10.49 (s, 1H), 8.66 (s, 1H), 8.49-8.44 (m, 1H), 8.43-8.38 (m, 1H), 8.24-8.20 (m, 1H), 7.48 (s, 1H), 4.45 (t, J=5.2 Hz, 1H), 3.98 (s, 3H), 3.27 (t, J=5.2 Hz, 2H), 2.94-2.83 (m, 1H), 2.22-2.11 (m, 2H), 1.90-1.81 (m, 2H), 1.64-1.50 (m, 2H), 1.49-1.36 (m, 1H), 1.17-1.00 (m, 2H); LC-MS (ESI$^+$) m/z 450.2 (M+H)$^+$.

Example 28. Synthesis of N-[2-[4-[6-[[1-(2,6-dioxo-3-piperidyl)-3-methyl-2-oxo-benzimidazol-4-yl]methyl]- 2,6-diazaspiro[3.3]heptane-2-carbonyl]cyclohexyl]-6-(1-hydroxy-1-methyl-ethyl)indazol-5-yl]-6-(trifluoromethyl)pyridine-2-carboxamide (I-45)

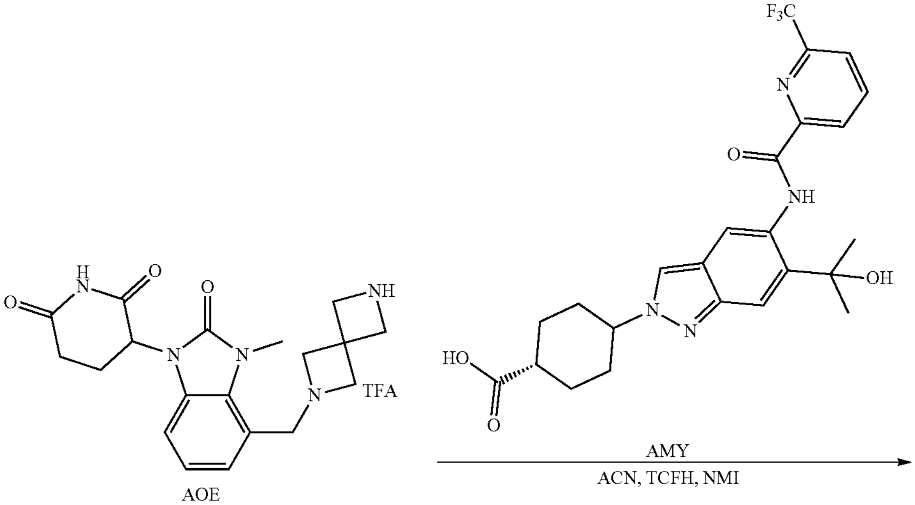

AOE

AMY

-continued

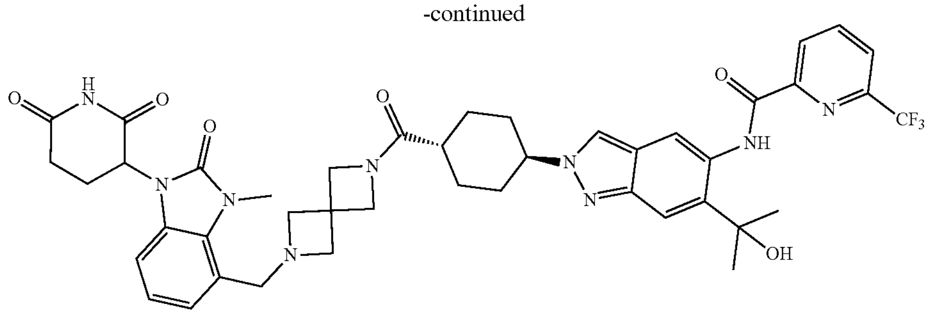

I-45

To a solution of 4-[6-(1-hydroxy-1-methyl-ethyl)-5-[[6-(trifluoromethyl)pyridine-2-carbonyl]amino]indazol-2-yl] cyclohexanecarboxylic acid (10.1 mg, 20.6 umol, Intermediate AMY) in ACN (1 mL) was added 1-methylimidazole (4.25 mg, 51.7 umol) and [chloro(dimethylamino)methylene]-dimethyl- ammonium;hexafluorophosphate (6.96 mg, 24.8 umol) and the reaction mixture was stirred at 25° C. for 10 min. Then 3-[4-(2,6-diazaspiro[3.3]heptan-2-ylmethyl)-3-methyl-2-oxo-benzimidazol-1-yl]piperidine-2,6-dione (10.0 mg, 20.6 umol, TFA salt, Intermediate AOE) was added and stirred at 25° C. for 5 hrs. On completion, the reaction mixture was washed with water (10 mL) and extracted by EA (3×10 mL). The combined organic layer was dried over by $Na_2SO_4$ and filtrated. The filtrate was concentrated in vacuo. The residue was purified by Prep-HPLC (column: Phenomenex Synergi C18 150*25*10 um;mobile phase: [water(0.225% FA)-ACN];B %: 15%-45%, 10 min) to give the title compound (6.39 mg, 35% yield) as white solid. $^1H$ NMR (400 MHz, DMSO-$d_6$) δ 12.35 (s, 1H), 11.11 (s, 1H), 8.70 (s, 1H), 8.46-8.42 (m, 1H), 8.40-8.31 (m, 2H), 8.17-8.12 (m, 1H), 7.56 (s, 1H), 7.20-6.85 (m, 3H), 5.94 (s, 1H), 5.44-5.32 (m, 1H), 4.54-4.41 (m, 1H), 4.29 (s, 2H), 3.92 (s, 2H), 3.85-3.69 (m, 1H), 3.63 (s, 3H), 2.93-2.83 (m, 1H), 2.78-2.67 (m, 1H), 2.65 (d, J=4.0 Hz, 1H), 2.62-2.52 (m, 3H), 2.31-2.23 (m, 1H), 2.13 (d, J=9.2 Hz, 2H), 2.05-1.78 (m, 6H), 1.61 (s, 6H), 1.60-1.48 (m, 3H), LC-MS ($ESI^+$) m/z 842.5 $(M+H)^+$.

Example 29. Synthesis of N-[2-[4-[1-(2,6-dioxo-3-piperidyl)-3-methyl-2-oxo-benzimidazol-4-yl]cyclohexyl]-6-methoxy -indazol-5-yl]-6-(trifluoromethyl) pyridine-2-carboxamide (I-354)

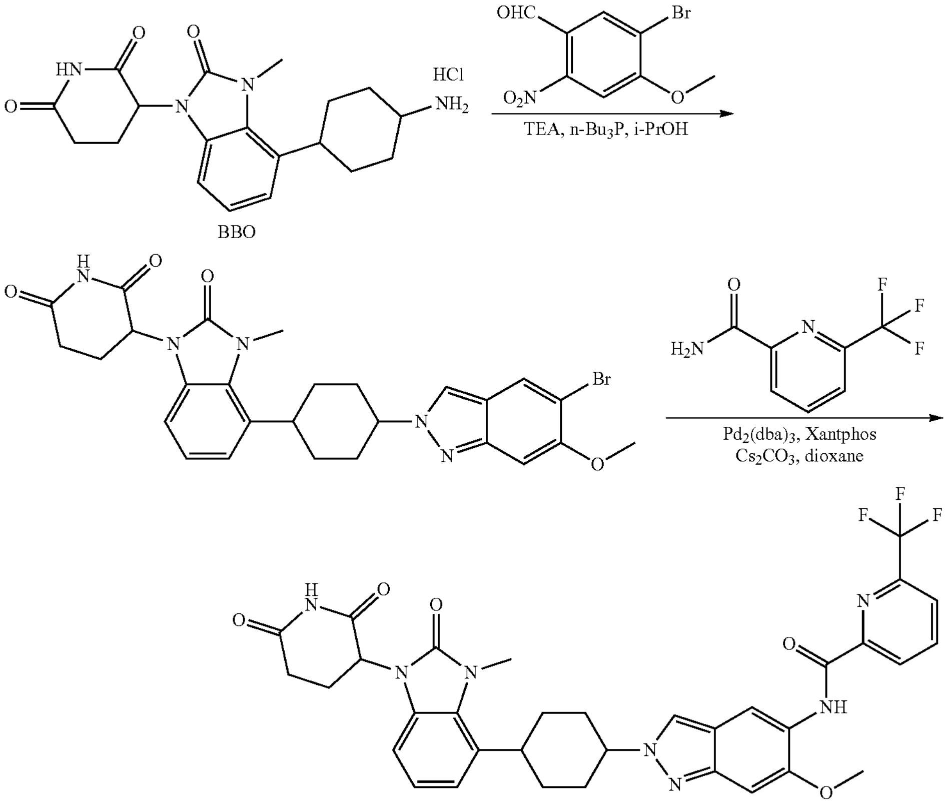

Step 1—3-[4-[4-(5-Bromo-6-methoxy-indazol-2-yl) cyclohexyl]-3-methyl-2-oxo-benzimidazol-1- yl]piperidine-2,6-dione To a solution of 3-[4-(4-aminocyclohexyl)-3-methyl-2-oxo-benzimidazol-1-yl]piperidine-2,6-dione (300 mg, 842 umol, Intermediate BBO) in IPA (10 mL) was added 5-bromo-4-methoxy-2-nitro-benzaldehyde (100 mg, 385 umol, synthesized via Steps 1-2 of Intermediate ATE). The reaction mixture was stirred at 80° C. for 4 hrs, then the mixture was cooled to 20° C. and tributylphosphane (233 mg, 1.15 mmol) was added into the above mixture. The reaction mixture was stirred at 80° C. for 12 hrs. On completion, the mixture was diluted with water (50 mL), then extracted with EA (2×50 mL). The combined organic layer was washed with brine (50 mL), and concentrated in vacuo. The residue was purified by reverse phase (0.1% FA condition) to give the title compound (100 mg, 46% yield) as a yellow solid. LC-MS (ESI+) m/z 566.1 (M+H)+.

Step 2—N-[2-[4-[1-(2,6-dioxo-3-piperidyl)-3-methyl-2-oxo-benzimidazol-4-yl]cyclohexyl]-6-methoxy -indazol-5-yl]-6-(trifluoromethyl)pyridine-2-carboxamide A mixture of 3-[4-[4-(5-bromo-6-methoxy-indazol-2-yl) cyclohexyl]-3-methyl-2-oxo-benzimidazol-1-yl]piperidine-2,6-dione (80.0 mg, 141 umol), 6-(trifluoromethyl)pyridine-2-carboxamide (29.5 mg, 155 umol, Intermediate ATI), $Cs_2CO_3$ (92.0 mg, 282 umol), $Pd_2(dba)_3$ (12.9 mg, 14.1 umol) and Xantphos (16.3 mg, 28.3 umol) in dioxane (2 mL) was de-gassed and then heated at 80° C. for 24 hrs. On completion, the mixture was concentrated in vacuo. The residue was purified by reverse phase (0.1% FA condition) and then re-purified by prep-HPLC (column: Phenomenex Gemini NX-C18(75*30 mm*3 um); mobile phase: [water (10 mM $NH_4HCO_3$)-ACN];B %: 36%-66%, 8 min) to give the title compound (4.00 mg, 4.2% yield,) as a yellow solid. $^1H$ NMR (400 MHz, DMSO-$d_6$) δ 11.03 (s, 1H), 10.53 (s, 1H), 8.74 (s, 1H), 8.54 (s, 1H), 8.50-8.45 (m, 1H), 8.44-8.39 (m, 1H), 8.22 (d, J=7.2 Hz, 1H), 7.24 (s, 1H), 6.94 (d, J=3.2 Hz, 2H), 6.86-6.80 (m, 1H), 5.42-5.29 (m, 1H), 4.82-4.75 (m, 1H), 4.01 (s, 3H), 3.64 (s, 3H), 2.90-2.85 (m, 1H), 2.69-2.64 (m, 4H), 2.20-2.12 (m, 2H), 2.03-1.95 (m, 1H), 1.86-1.74 (m, 4H), 1.28-1.18 (m, 1H); LC-MS (ESI+) m/z 676.3 (M+H)+.

Example 30. Synthesis of N-[2-[4-[[[1-[1-(2,6-dioxo-3-piperidyl)-3-methyl-2-oxo-benzimidazol-4-yl]-4-piperidyl]- methyl-amino]methyl]cyclohexyl]-6-methoxy-indazol-5-yl]-2-(trifluoromethyl) pyrimidine-4-carboxamide (I-366)

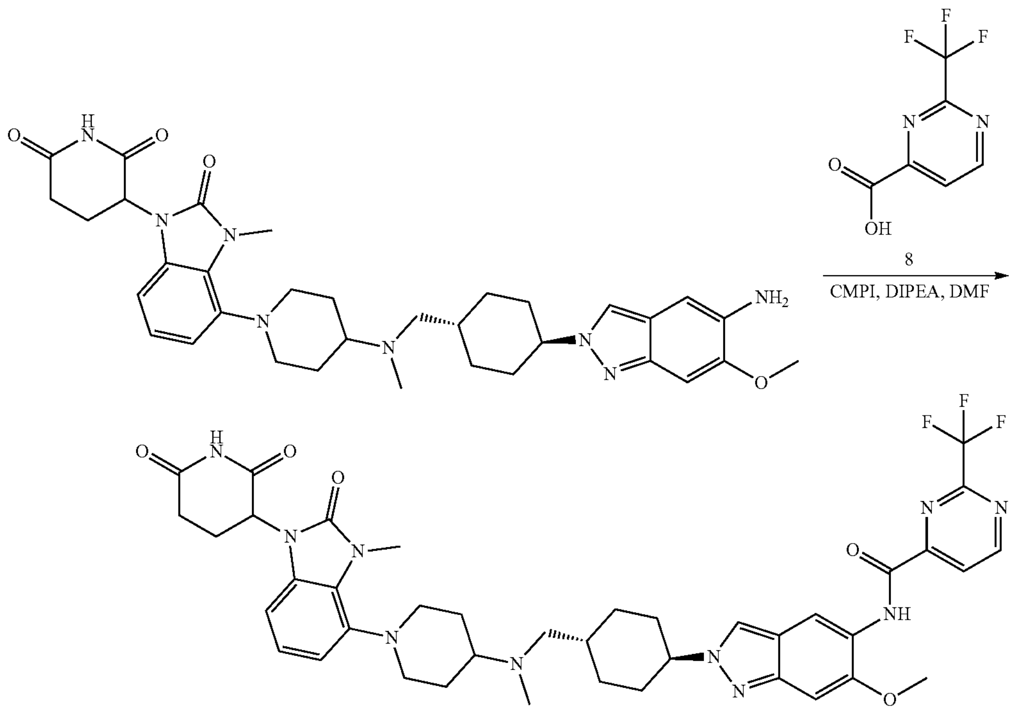

To a solution of 3-[4-[4-[[4-(5-amino-6-methoxy-indazol-2-yl)cyclohexyl]methyl-methyl-amino]-1- piperidyl]-3-methyl-2-oxo-benzimidazol-1-yl]piperidine-2,6-dione (60.0 mg, 80.8 umol, TFA salt, Intermediate BGU) and 2-(trifluoromethyl)pyrimidine-4-carboxylic acid (15.5 mg, 80.8 umol, Intermediate BIR) in DMF (1.5 mL) was added DIPEA (52.2 mg, 404 umol) and CMPI (24.8 mg, 96.9 umol). The reaction mixture was stirred at 20° C. for 0.5 hr. On completion, the mixture was acidified with FA to pH=6-7, concentrated in vacuo. The residue was purified by prep-HPLC (column: Phenomenex luna C18 150*25 mm*10 um; mobile phase: [water (0.225% FA)-ACN]; B %: 21%-51%, 10 min) to give the title compound (36.2 mg, 53% yield, FA salt) as a yellow solid. $^1H$ NMR (400 MHz, DMSO-$d_6$) δ 11.09 (s, 1H), 10.46 (s, 1H), 9.39 (d, J=5.2 Hz, 1H), 8.68 (s, 1H), 8.43 (d, J=5.2 Hz, 1H), 8.36 (s, 1H), 7.18 (s, 1H), 7.01-6.84 (m, 3H), 5.35 (dd, J=5.2, 12.8 Hz, 1H), 4.47-4.31 (m, 1H), 3.99 (s, 3H), 3.64 (s, 3H), 3.17-3.14 (m, 2H), 2.95-2.82 (m, 1H), 2.75-2.57 (m, 4H), 2.38-2.31 (m, 2H), 2.29 (s, 3H), 2.20-2.10 (m, 2H), 2.05-1.50 (m, 11H), 1.21-1.02 (m, 2H); LC-MS (ESI+) m/z 803.5 $(M+H)^+$.

Example 31. Synthesis of N-[2-[4-[[[1-[1-(2,6-dioxo-3-piperidyl)-3-methyl-2-oxo-benzimidazol-4-yl]-4-piperidyl]- methyl-amino]methyl]cyclohexyl]-6-methoxy-indazol-5-yl]-6-(trifluoromethyl) pyrazine-2-carboxamide (I-367)

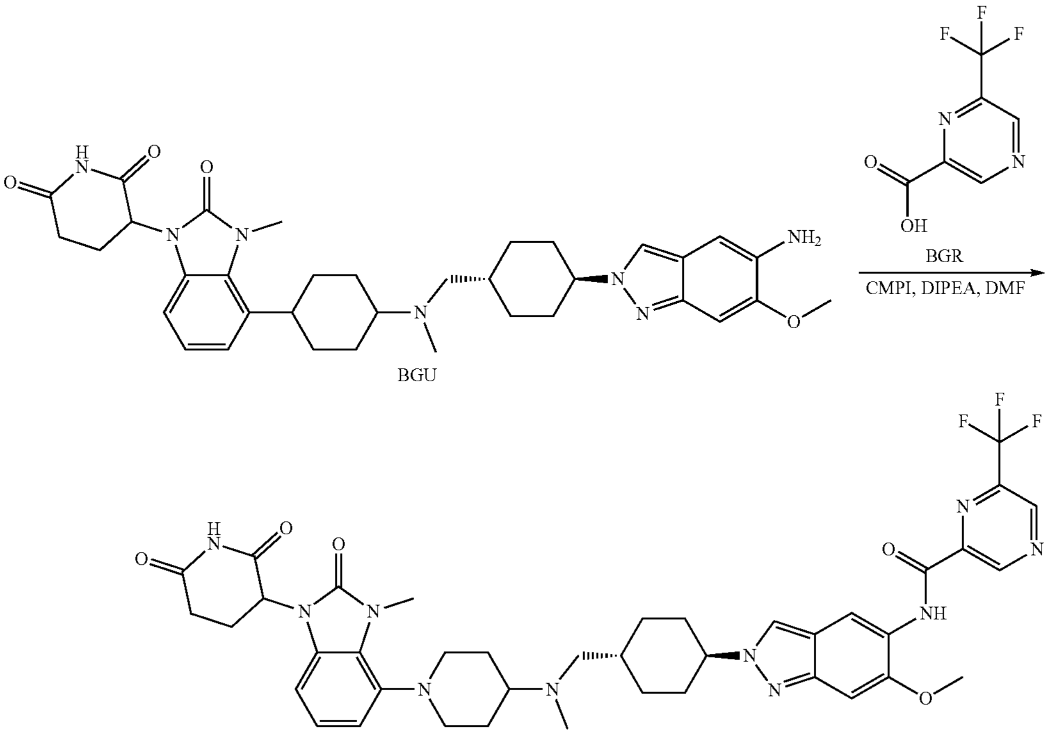

BGU

To a solution of 3-[4-[4-[[4-(5-amino-6-methoxy-indazol-2-yl)cyclohexyl]methyl-methyl-amino]-1-piperidyl]-3-methyl-2-oxo-benzimidazol-1-yl]piperidine-2,6-dione (50.0 mg, 67.3 umol, TFA salt, Intermediate BGU) and 6-(trifluoromethyl)pyrazine-2-carboxylic acid (12.9 mg, 67.3 umol, Intermediate BGR) in DMF (1.5 mL) was added DIPEA (43.5 mg, 337 umol) and CMPI (20.6 mg, 80.8 umol). The reaction mixture was stirred at 20° C. for 0.5 hr. On completion, the mixture was acidified with FA to pH=6-7, then concentrated in vacuo. The residue was purified by prep-HPLC (column: Phenomenex Synergi C18 150*25*10 um; mobile phase: [water (0.225% FA)-ACN]; B %: 24%-44%, 10 min) to give the title compound (47.6 mg, 83% yield, FA salt) as a yellow solid. $^1H$ NMR (400 MHz, DMSO-$d_6$) δ 11.09 (s, 1H), 10.23 (s, 1H), 9.62 (s, 1H), 9.50 (s, 1H), 8.65 (s, 1H), 8.36 (s, 1H), 7.17 (s, 1H), 7.02-6.84 (m, 3H), 5.35 (dd, J=5.2, 12.4 Hz, 1H), 4.44-4.32 (m, 1H), 3.98 (s, 3H), 3.64 (s, 3H), 3.16 (d, J=10.8 Hz, 2H), 2.93-2.83 (m, 1H), 2.77-2.61 (m, 4H), 2.30 (d, J=6.4 Hz, 2H), 2.26 (s, 3H), 2.18-2.11 (m, 2H), 2.04-1.75 (m, 8H), 1.71-1.50 (m, 3H), 1.17-1.03 (m, 2H); LC-MS (ESI+) m/z 803.5 $(M+H)^+$.

Example 32. Syntheses of N-[2-[4-[[[1-[1-[(3S)-2,6-dioxo-3-piperidyl]-3-methyl-2-oxo-benzimidazol-4-yl]-4-piperidyl]-methyl-amino]methyl]cyclohexyl]-6-methoxy-indazol-5-yl]-6-(trifluoromethyl) pyridine-2-carboxamide (I-466) and N-[2-[4-[[[1-[1-[(3R)-2,6-dioxo-3-piperidyl]-3-methyl-2-oxo-benzimidazol-4-yl]-4-piperidyl]-methyl-amino] methyl]cyclohexyl]-6-methoxy-indazol-5-yl]-6-(trifluoromethyl)pyridine-2-carboxamide (I-467)

indazol-5-yl]-6-(trifluoromethyl)pyridine-2-carboxamide (541 mg, 77% yield, 97.1% ee) as a yellow solid. $^1$H NMR (400 MHz, DMSO-$d_6$) δ 11.09 (s, 1H), 10.50 (s, 1H), 8.69 (s, 1H), 8.50-8.29 (m, 3H), 8.20 (dd, J=0.8, 7.6 Hz, 1H), 7.15 (s, 1H), 7.01-6.94 (m, 1H), 6.92-6.83 (m, 2H), 5.35 (dd, J=5.2, 12.4 Hz, 1H), 4.42-4.31 (m, 1H), 3.98 (s, 3H), 3.64 (s, 3H), 3.15 (d, J=11.2 Hz, 2H), 2.96-2.82 (m, 1H), 2.78-2.58 (m, 4H), 2.58-2.47 (m, 1H), 2.36-2.30 (m, 2H), 2.28 (s, 3H), 2.14 (d, J=11.6 Hz, 2H), 2.05-1.74 (m, 7H), 1.72-1.48 (m, 3H), 1.22-0.97 (m, 2H); LC-MS (ESI$^+$) m/z 802.4

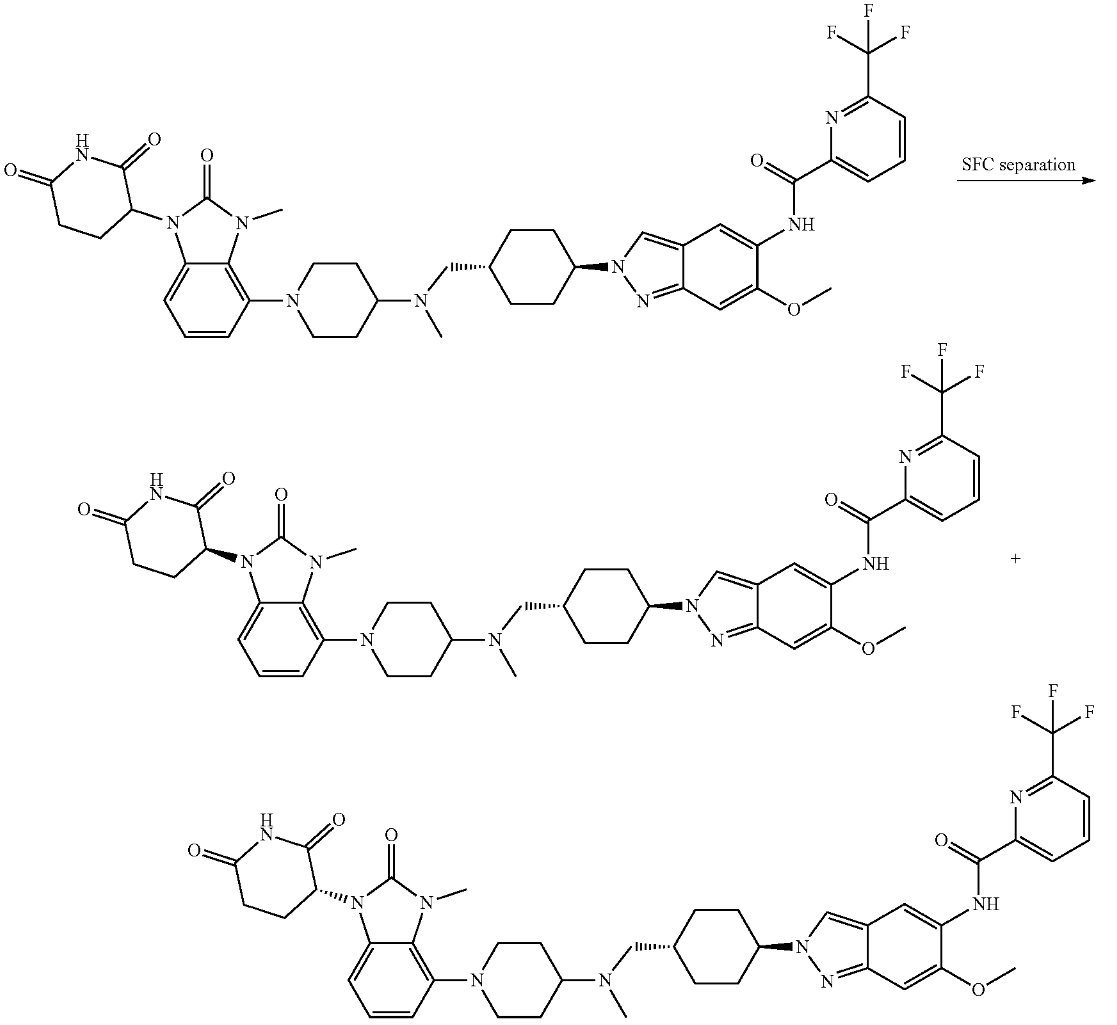

N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-methoxy-indazol-5-yl]-6-(trifluoromethyl)pyridine-2-carboxamide (1.50 g, 1.87 mmol, I-247) was separated by SFC (column: Daicel Chiralpack AD (250 mm*30 mm,10 um); mobile phase: [0.1% $NH_3H_2O$ IPA]; B %: 50%-50%, 6.7 min; 260 minmin) to give two isomers. The first fraction, N-[2-[4-[[[1-[1-[(3S)-2,6-dioxo-3-piperidyl]-3-methyl-2-oxo-benzimidazol-4-yl]-4-piperidyl]-methyl-amino]methyl]cyclohexyl]-6-methoxy-indazol-5-yl]-6-(trifluoromethyl)pyridine-2-carboxamide (0.700 g, 47% yield) was isolated as a yellow solid. Then the solid was purified by reverse phase to give the N-[2-[4-[[[1-[1-[(3S)-2,6-dioxo-3-piperidyl]-3-methyl-2-oxo-benzimidazol-4-yl]-4-piperidyl]-methyl-amino]methyl]cyclohexyl]-6-methoxy- (M+H)$^+$. The second fraction, N-[2-[4-[[[1-[1-[(3R)-2,6-dioxo-3-piperidyl]-3-methyl-2-oxo-benzimidazol-4-yl]-4-piperidyl]-methyl-amino]methyl]cyclohexyl]-6-methoxy-indazol-5-yl]-6-(trifluoromethyl)pyridine-2-carboxamide (0.700 g, 47% yield) was isolated as a yellow solid. Then the solid was purified by reverse phase to give N-[2-[4-[[[1-[1-[(3R)-2,6-dioxo-3-piperidyl]-3-methyl-2-oxo-benzimidazol-4-yl]-4-piperidyl]-methyl-amino]methyl]cyclohexyl]-6-methoxy-indazol-5-yl]-6-(trifluoromethyl)pyridine-2-carboxamide (531 mg, 76% yield, 96.3% ee) as a yellow solid. $^1$H NMR (400 MHz, DMSO-$d_6$) δ 11.09 (s, 1H), 10.50 (s, 1H), 8.68 (s, 1H), 8.47-8.43 (m, 1H), 8.43-8.35 (m, 1H), 8.32 (s, 1H), 8.20 (dd, J=0.8, 7.6 Hz, 1H), 7.15 (s, 1H), 7.01-6.94 (m, 1H), 6.93-6.82 (m, 2H), 5.35 (dd, J=5.2, 12.4 Hz, 1H), 4.43-4.29 (m, 1H), 3.97 (s, 3H), 3.64 (s, 3H), 3.14

(d, J=11.2 Hz, 2H), 2.94-2.81 (m, 1H), 2.78-2.57 (m, 4H), 2.53-2.50 (m, 1H), 2.31 (d, J=6.8 Hz, 2H), 2.26 (s, 3H), 2.18-2.07 (m, 2H), 2.04-1.48 (m, 10H), 1.21-0.95 (m, 2H); LC-MS ($ESI^+$) m/z 802.4 $(M+H)^+$. The absolute configuration of the stereoisomers was arbitrarily assigned.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I-k-15:

I-k-15

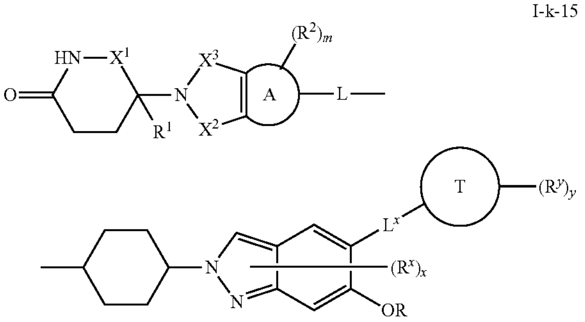

or a pharmaceutically acceptable salt thereof, wherein:

each $R^x$ is independently hydrogen, $C_{1-6}$ alkyl, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —$C(O)NR_2$, —$C(S)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$N^+(O^-)R_2$, —$OP(O)R_2$, —$OP(O)(OR)_2$, —$OP(O)(OR)NR_2$, —$OP(O)(NR_2)_2$, —$P(O)R_2$, —$SiR_3$, —$Si(OR)R_2$, or

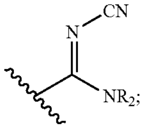

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^y$ is independently hydrogen, $C_{1-6}$ alkyl, halogen, —CN, —$NO_2$, —OR, —SR, —$NR_2$, —$S(O)_2R$, —$S(O)_2NR_2$, —S(O)R, —$CFR_2$, —$CF_2R$, —$CF_3$, —$CR_2(OR)$, —$CR_2(NR_2)$, —C(O)R, —C(O)OR, —$C(O)NR_2$, —$C(S)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, —$SiR_3$, —$SF_5$, or

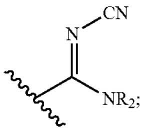

or a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur;

Ring T is phenyl,

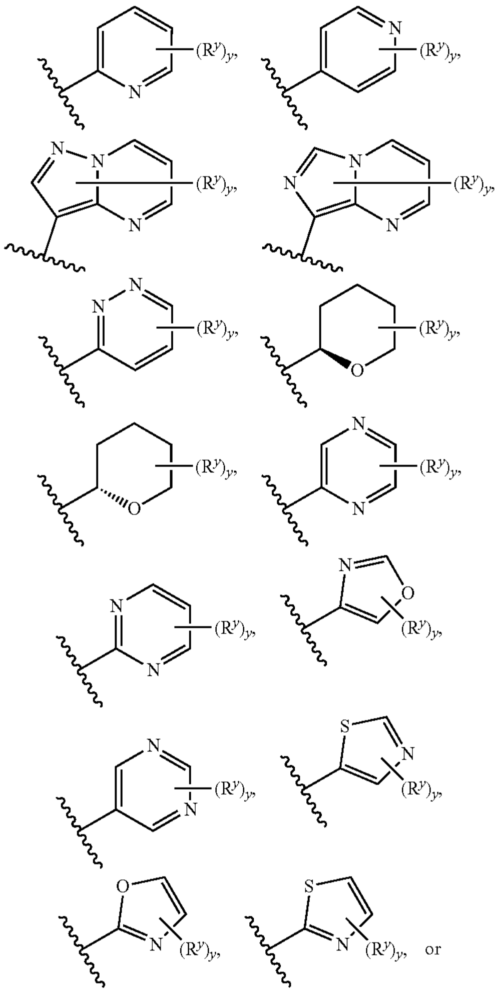

or

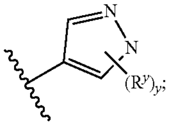

$L^x$ is —C(O)N(H)—;

x is 0, 1, 2, 3 or 4;

y is 0, 1, 2, 3 or 4;

L is a covalent bond or a bivalent, saturated or unsaturated, straight or branched $C_{1-50}$ hydrocarbon chain, wherein 0-6 methylene units of L are independently replaced by -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

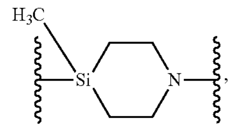,
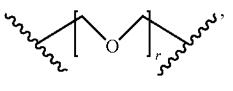,
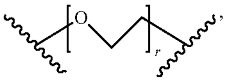,
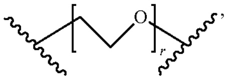,
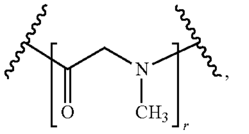, or
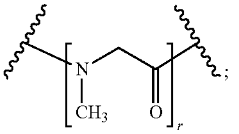;

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, and sulfur;

r is 0, 1, 2, 3, 4, 5, 6, 7, 8, 9, or 10; and $X^1$ is —C(O)—;

$X^2$ is —C(O)—;

$X^3$ is —$CH_2$— or —C(O)—;

$R^1$ is hydrogen or $C_{1-4}$ aliphatic;

each of $R^2$ is independently hydrogen, halogen, $C_{1-4}$ aliphatic or —O$C_{1-4}$ aliphatic;

Ring A is a fused ring selected from a 6-membered aryl containing 0-1 nitrogen atoms; and m is 0, 1, 2, 3 or 4.

2. The compound claim 1, wherein L is a bivalent, saturated or unsaturated, straight or branched $C_{1-30}$ hydrocarbon chain, wherein 0-6 methylene units of L are independently replaced by -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, or —N(R)C(O)O—.

3. The compound of claim 1, wherein said compound is selected from

I-63

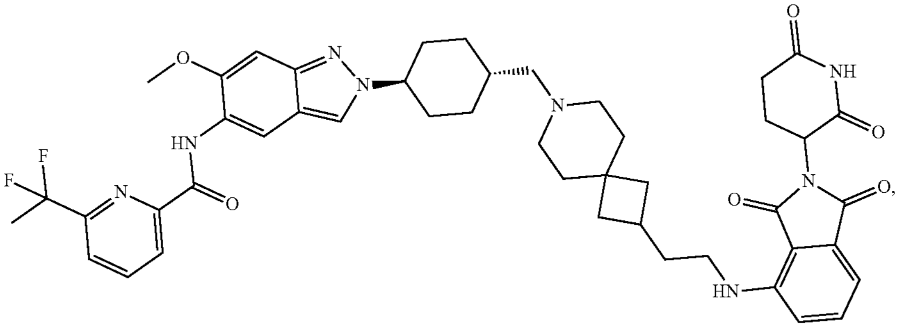

I-68

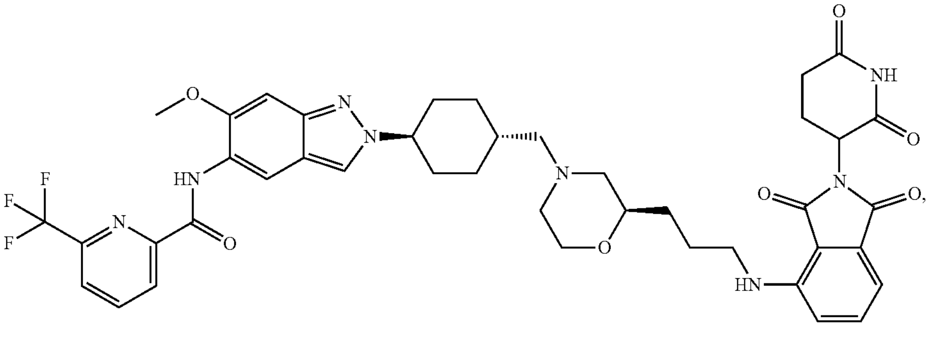

-continued
I-69
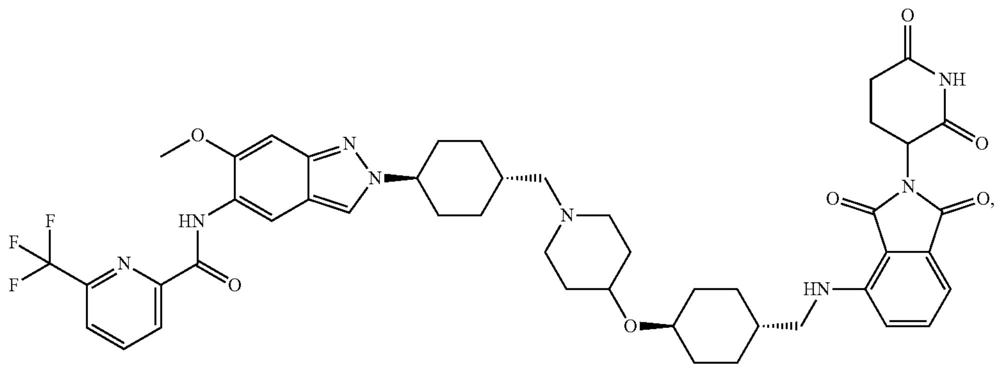
I-71
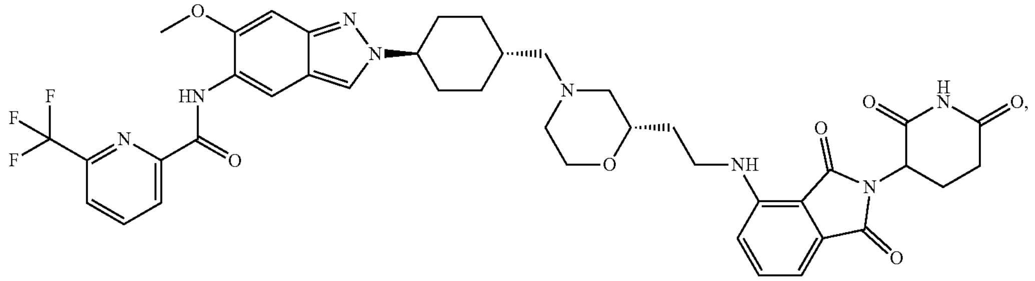
I-76
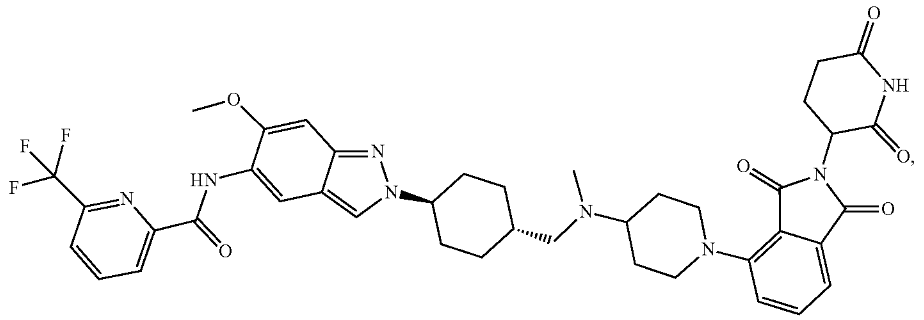
I-77
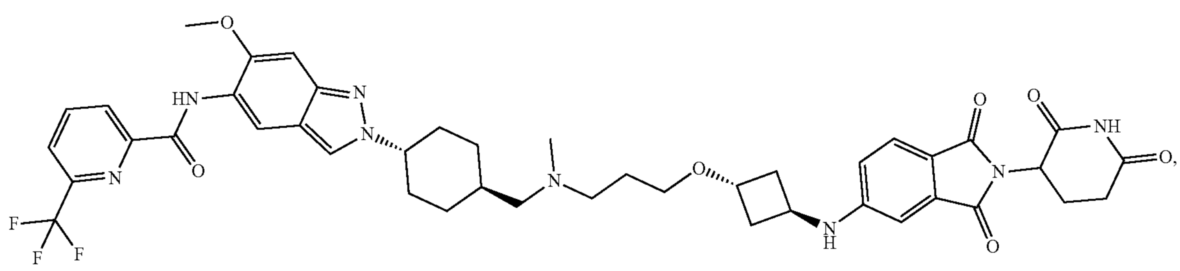
I-78
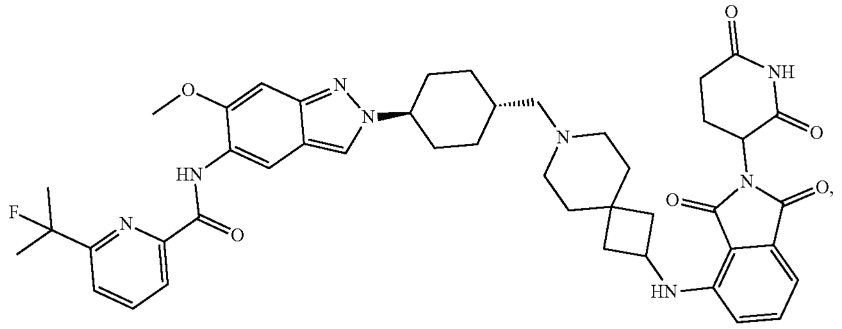

-continued
I-88
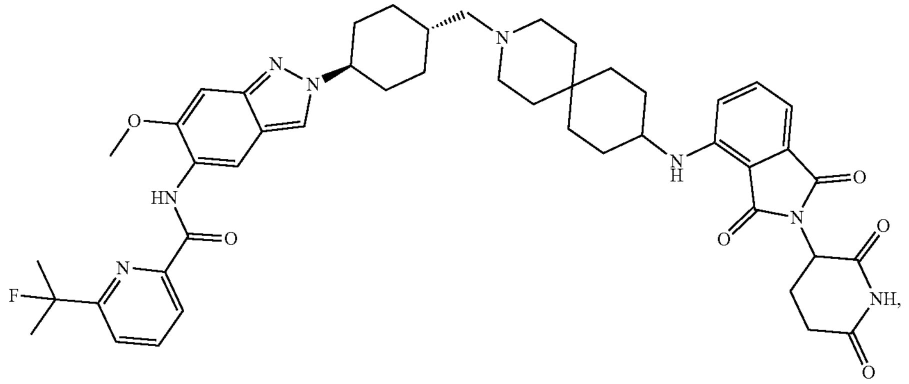
I-89
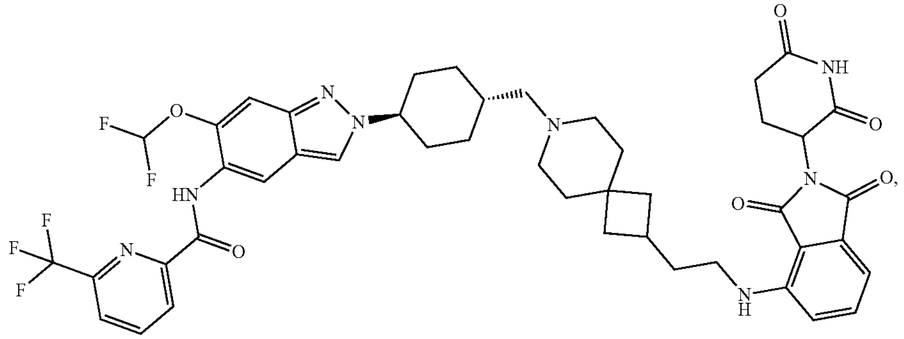
I-90
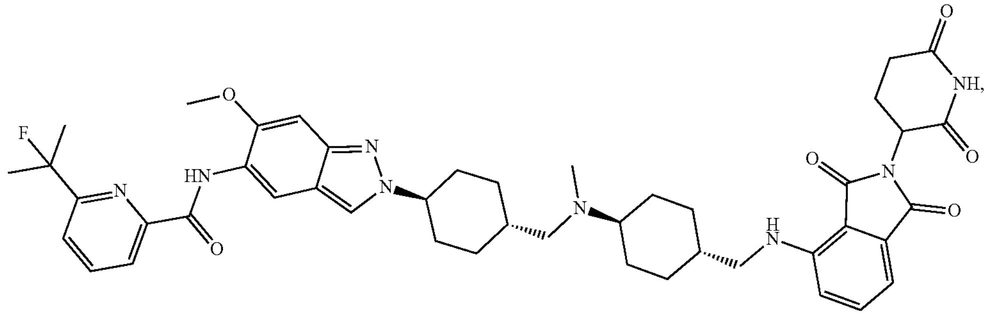
I-91
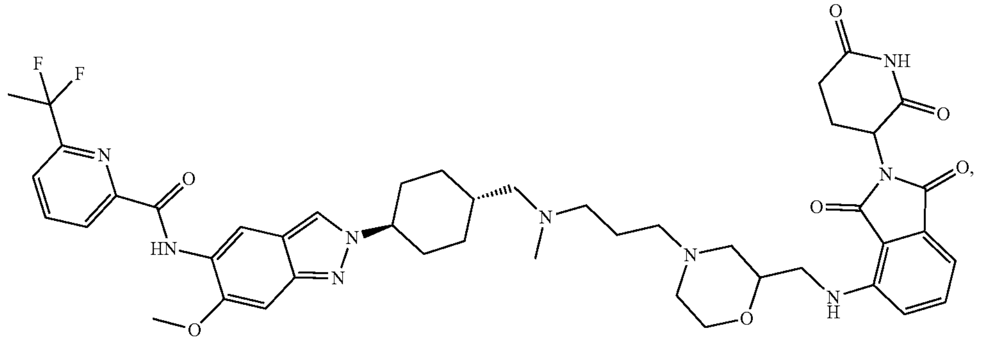

-continued
I-92
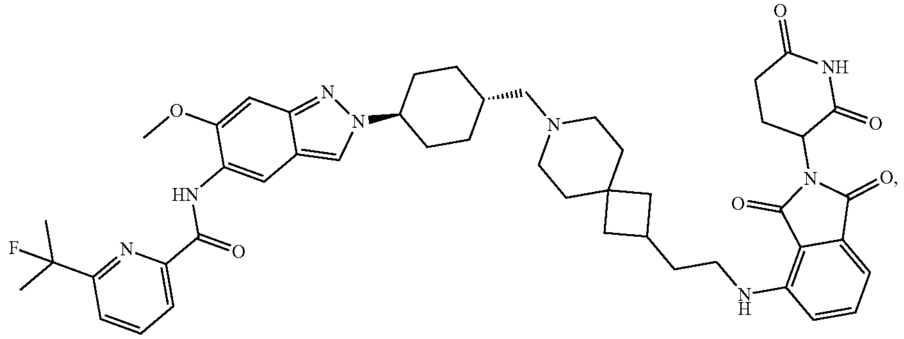
I-93
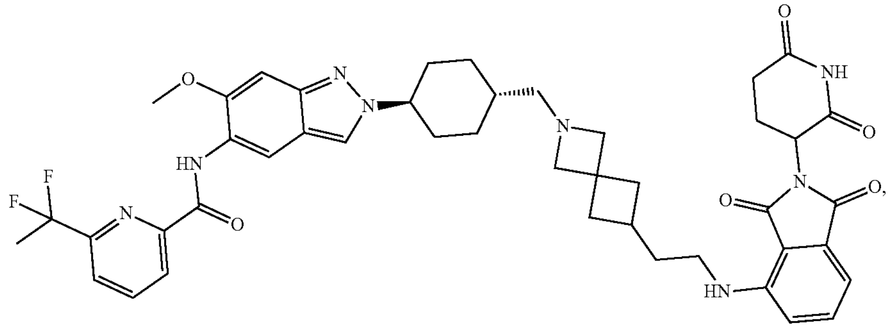
I-118
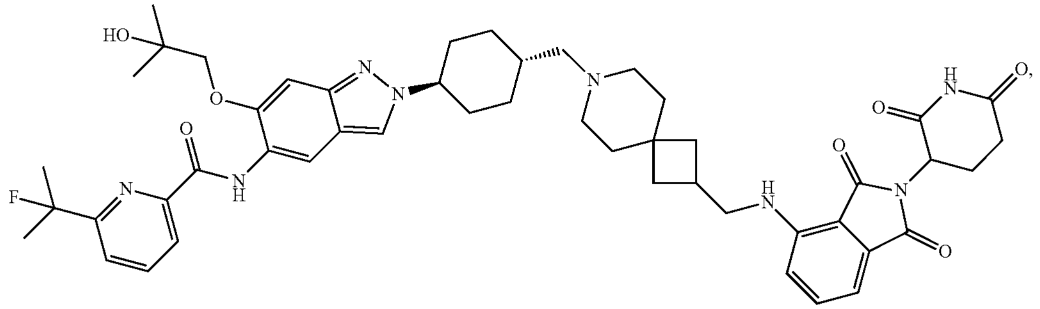
I-119
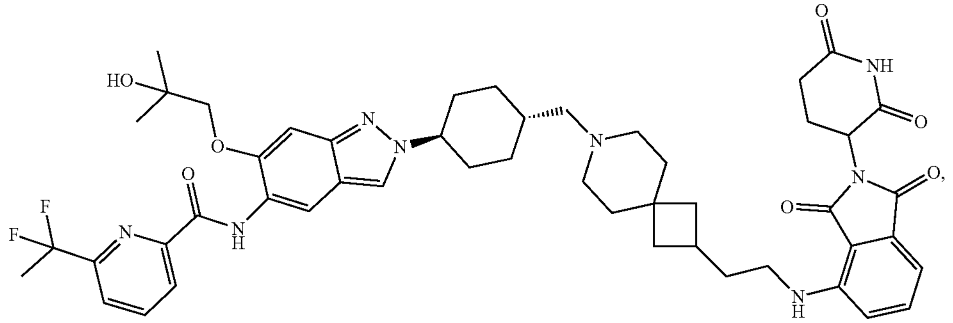
I-121
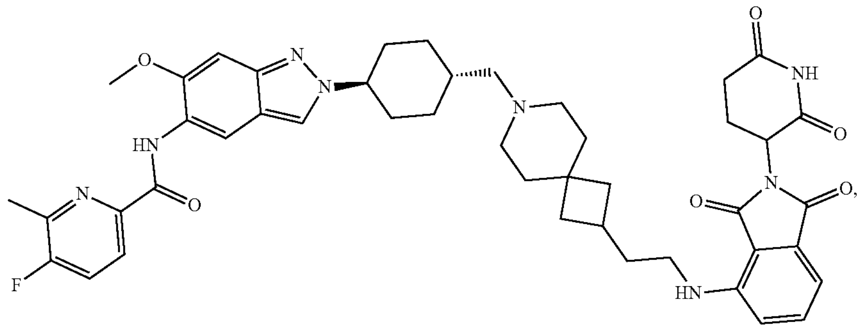

-continued
I-122
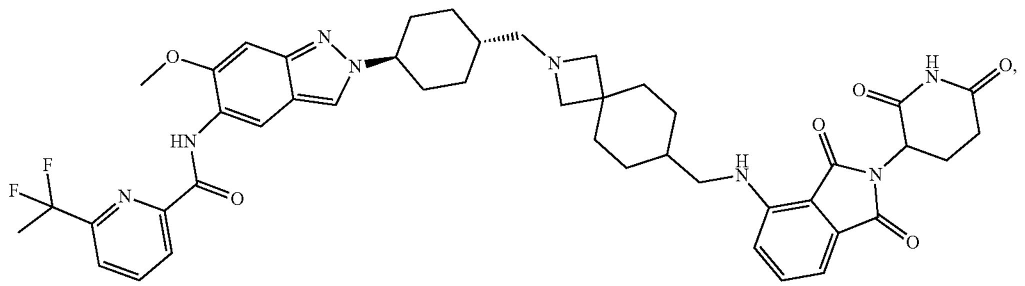
I-125
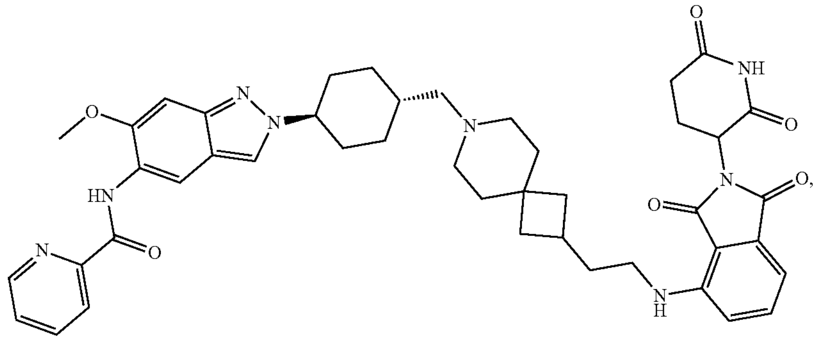
I-128
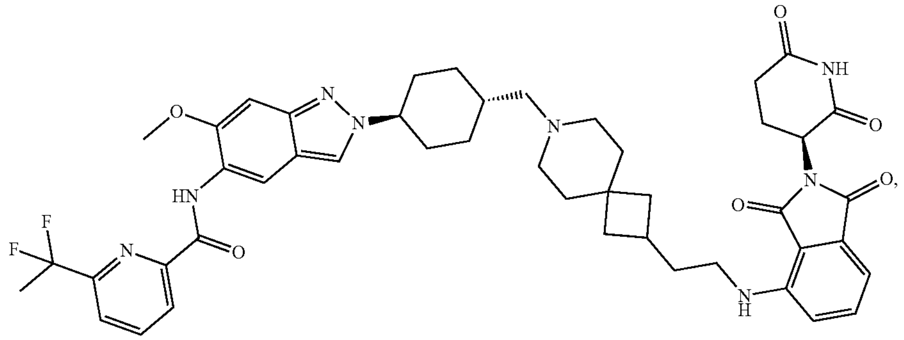
I-129
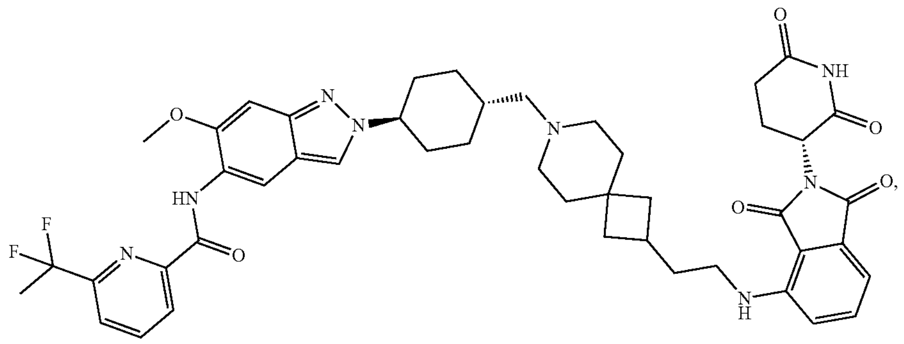

-continued
I-130
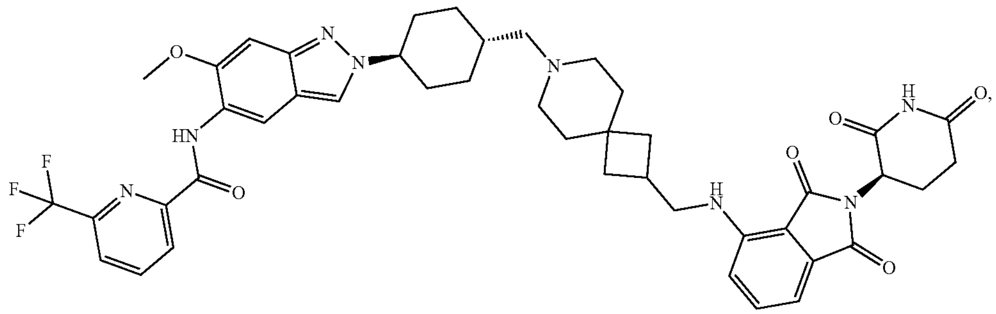
I-131
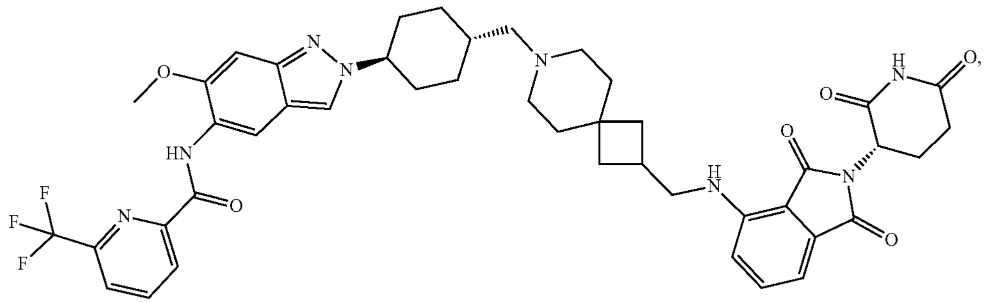
I-136
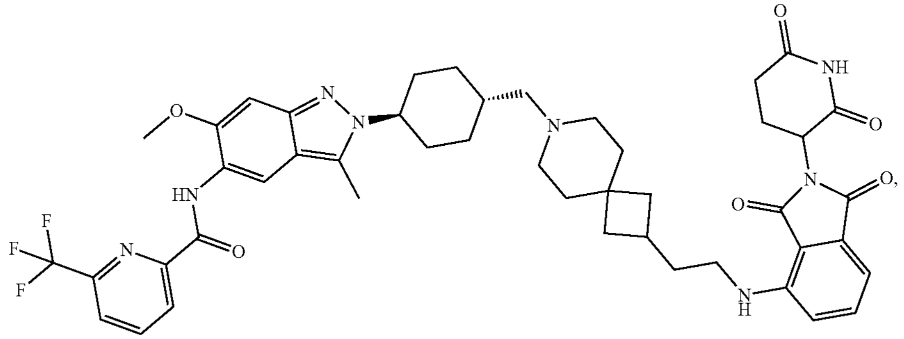
I-138
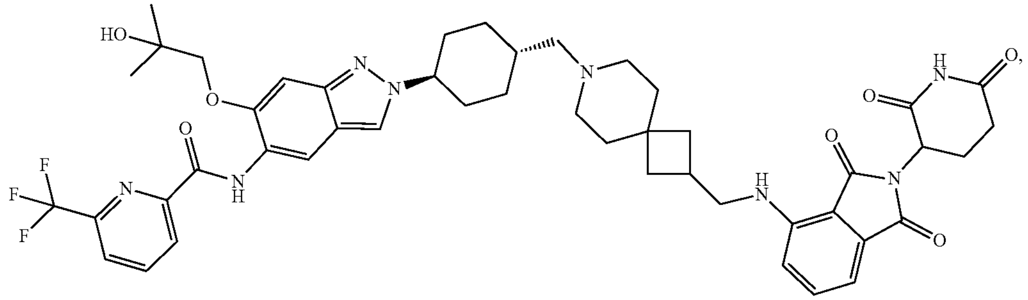
I-139
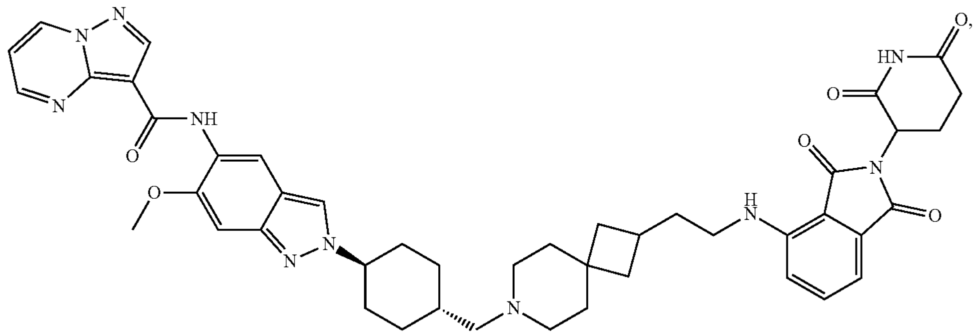

-continued
I-140
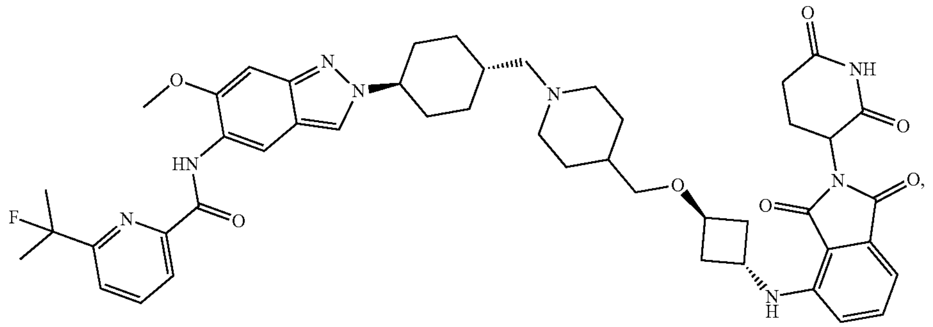
I-210
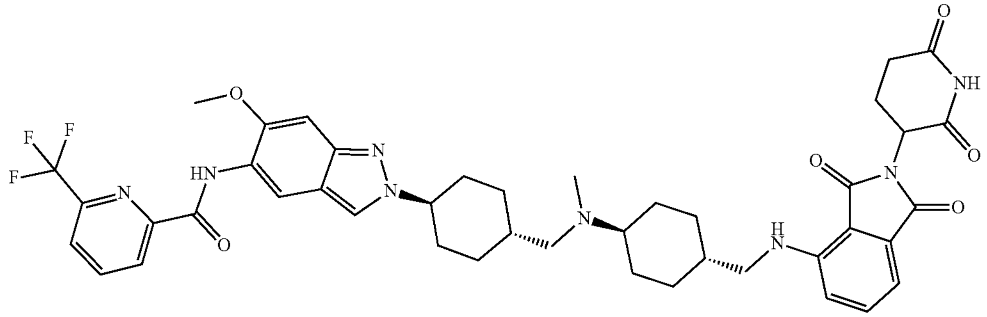
I-211
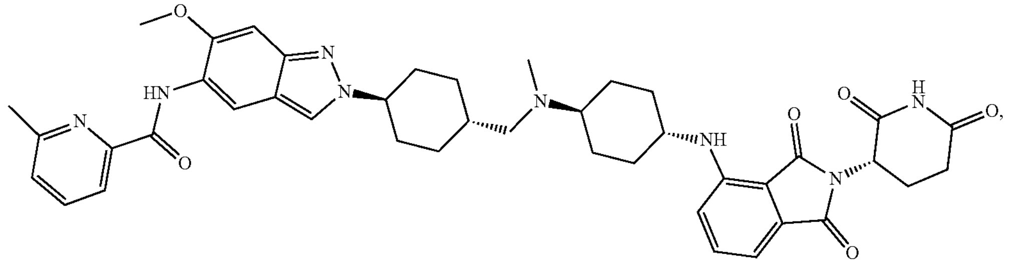
I-212
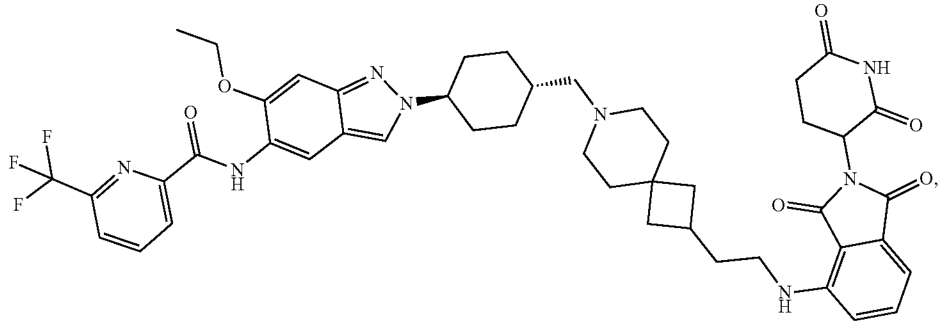
I-213
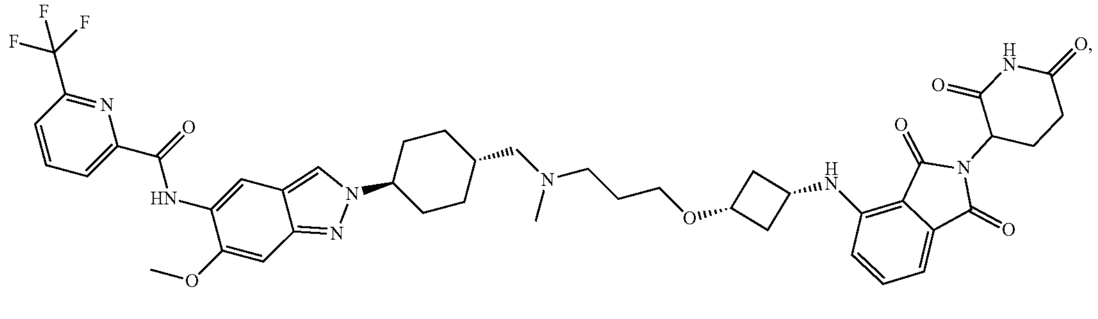

-continued
I-220
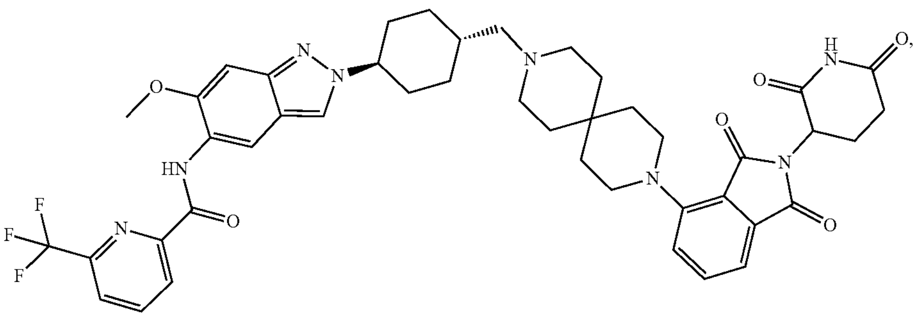
I-222
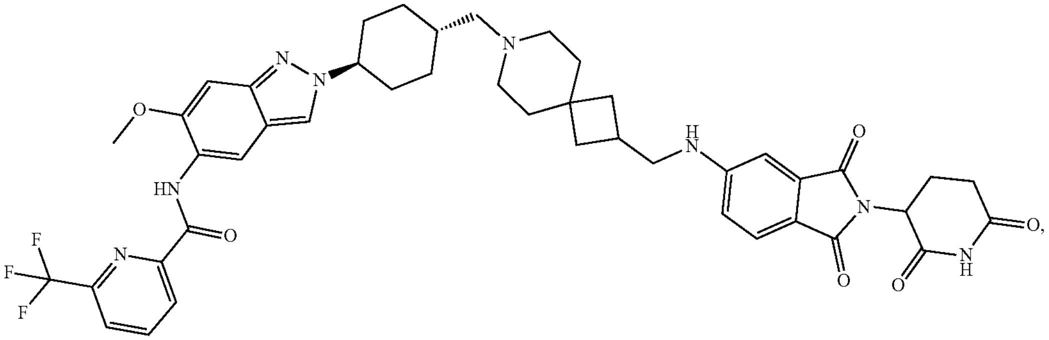
I-223
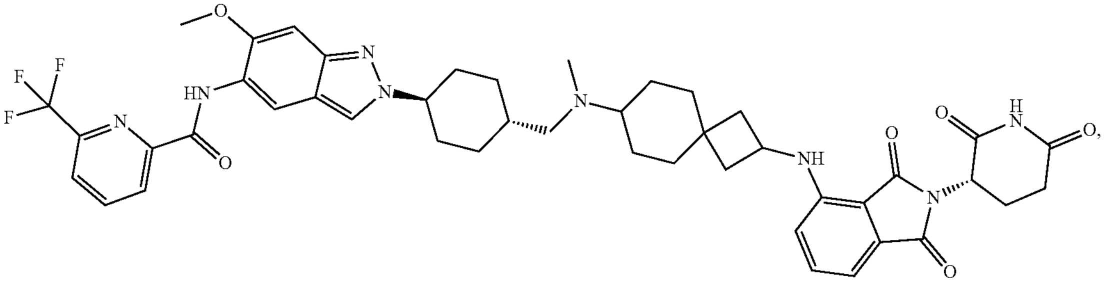
I-224
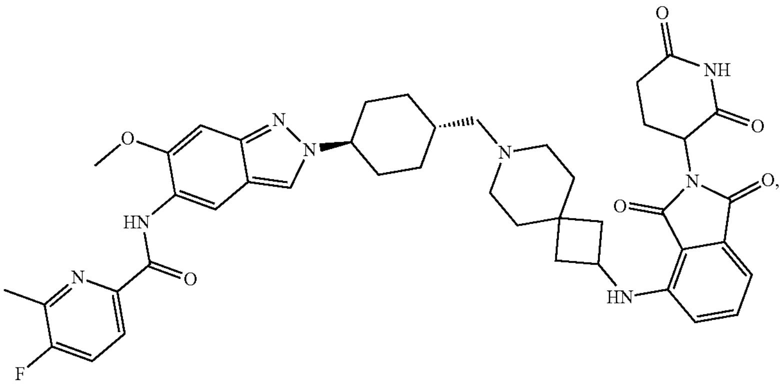

-continued
I-305
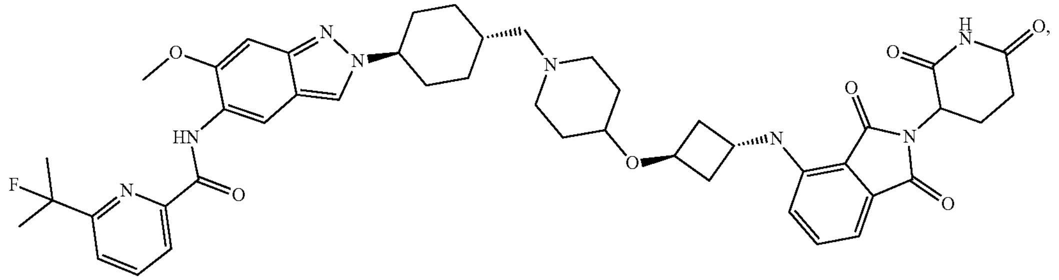
I-311
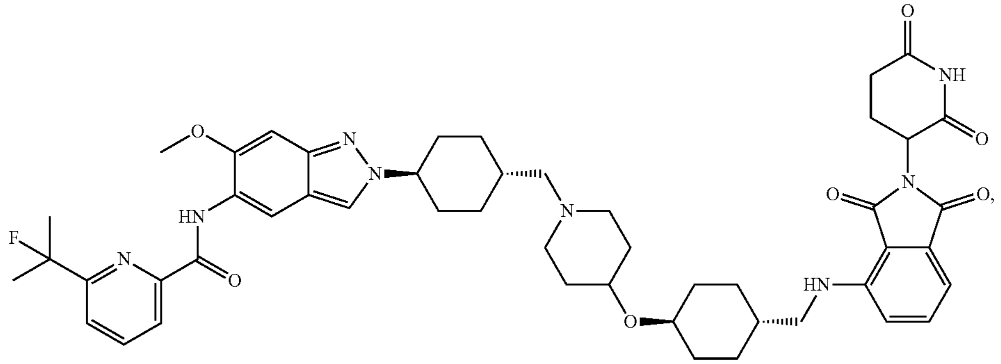
I-313
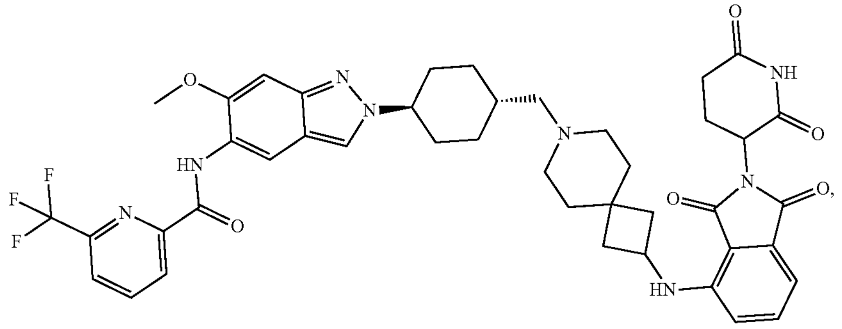
I-315
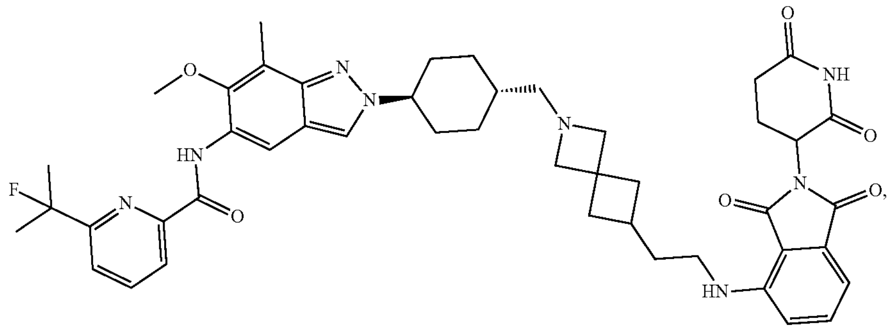

I-141
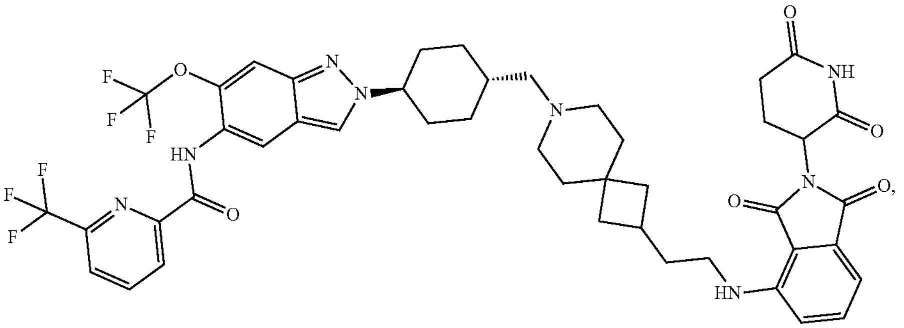
I-142
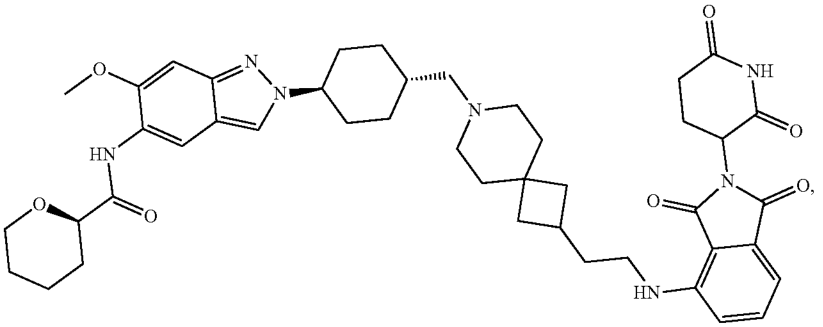
I-143
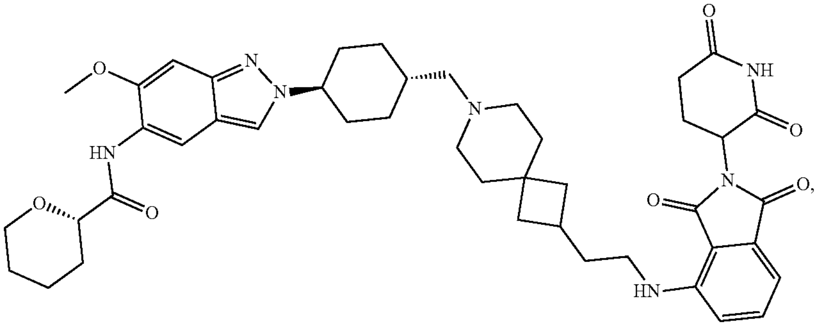
I-159
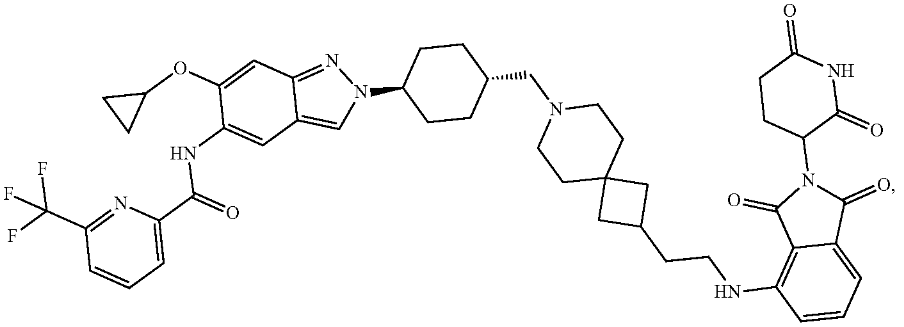
I-185
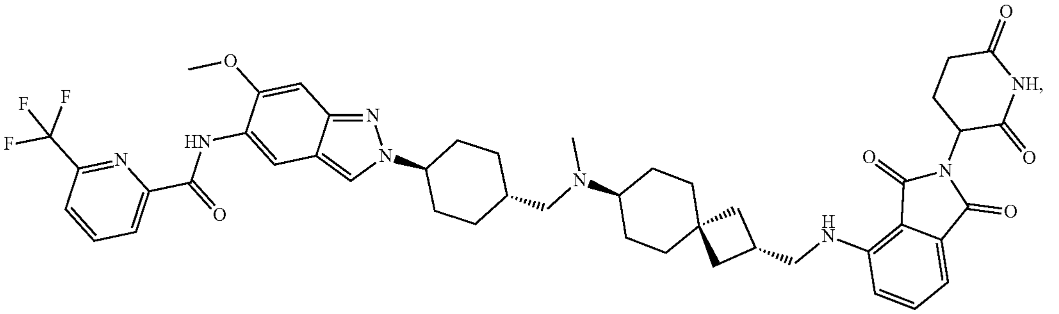

-continued
I-188
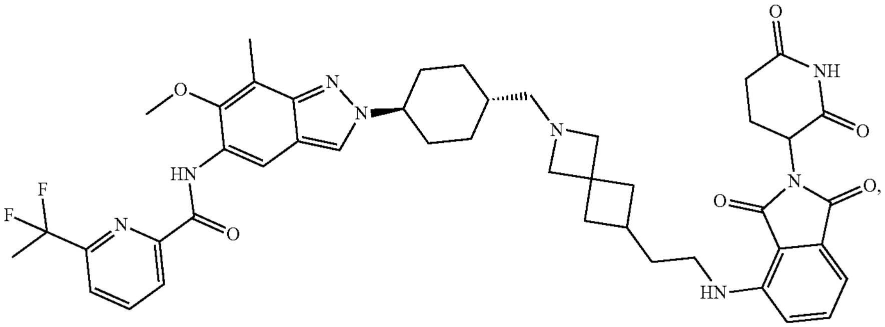
I-200
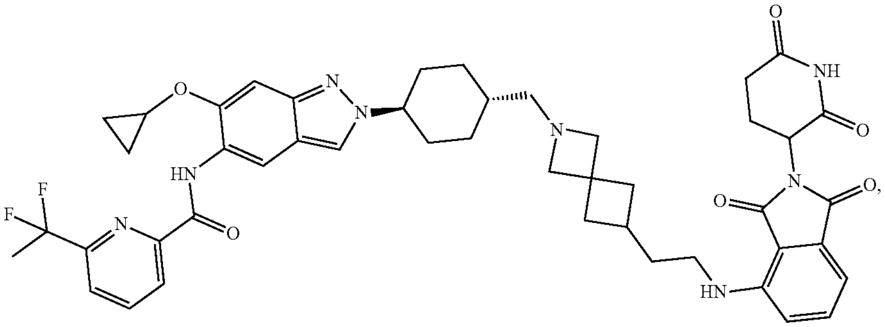
I-201
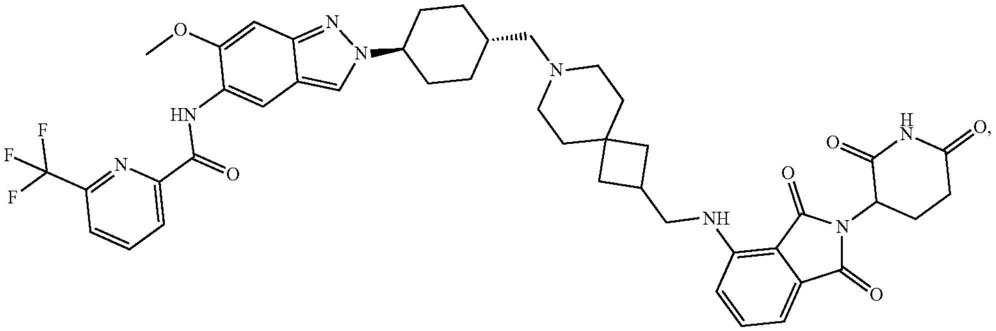
I-202
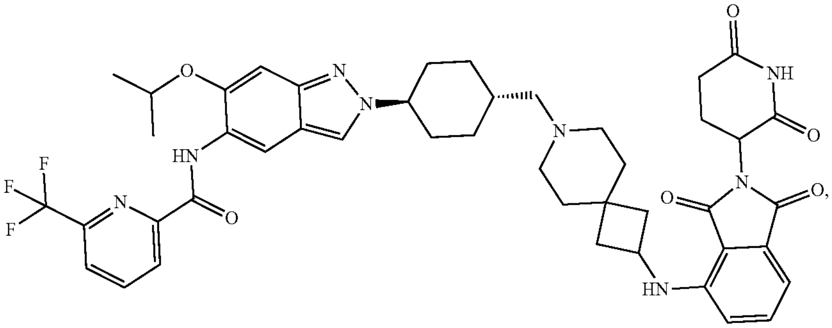

-continued
I-208
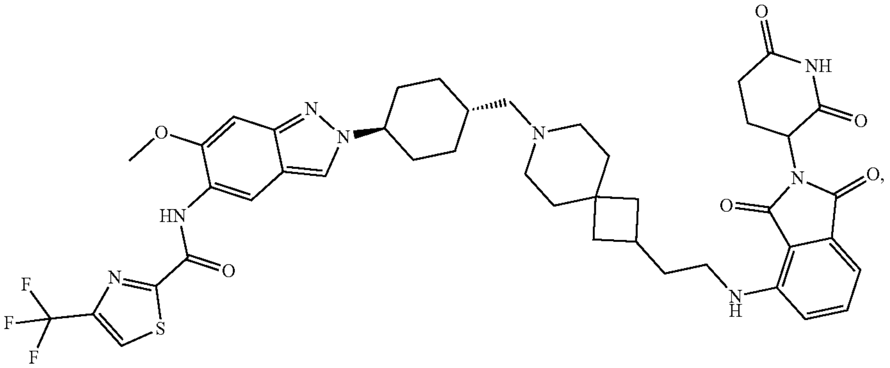
I-209
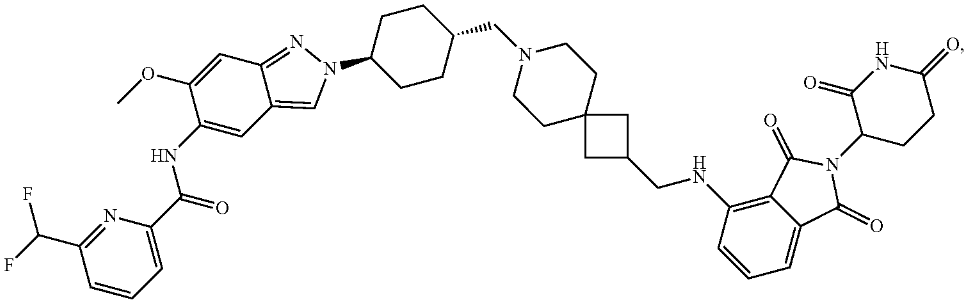
I-210
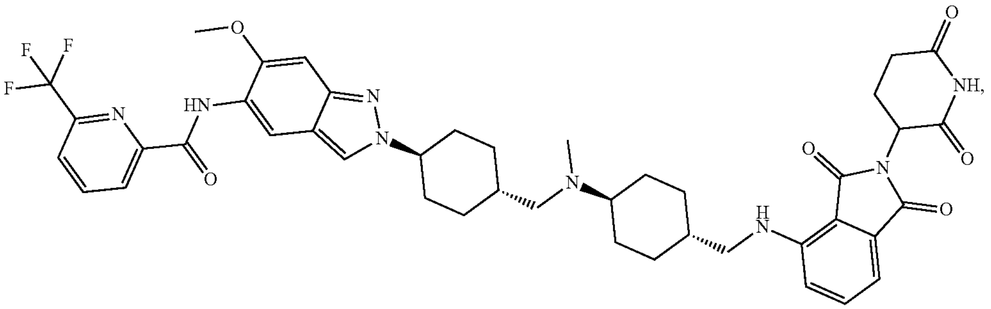
I-211
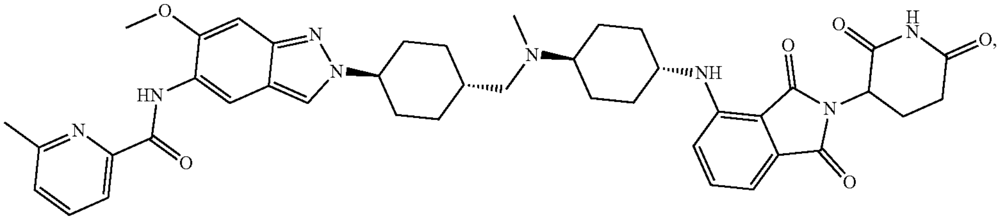
I-212
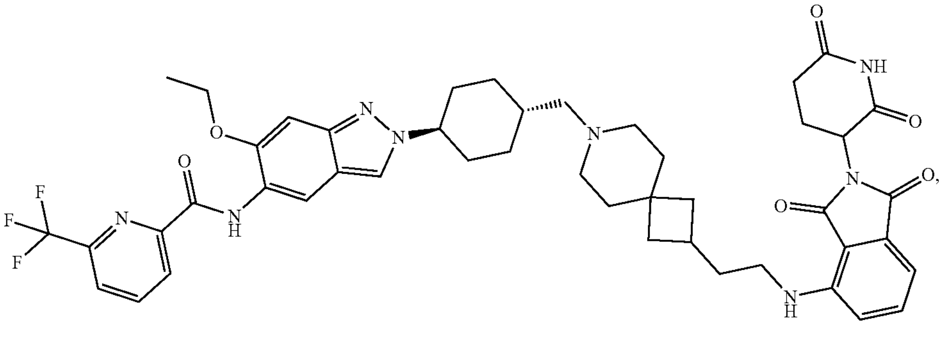

-continued
I-213
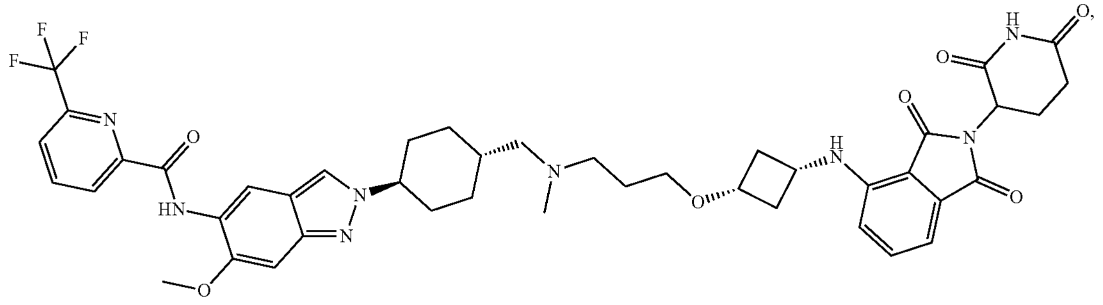
I-218
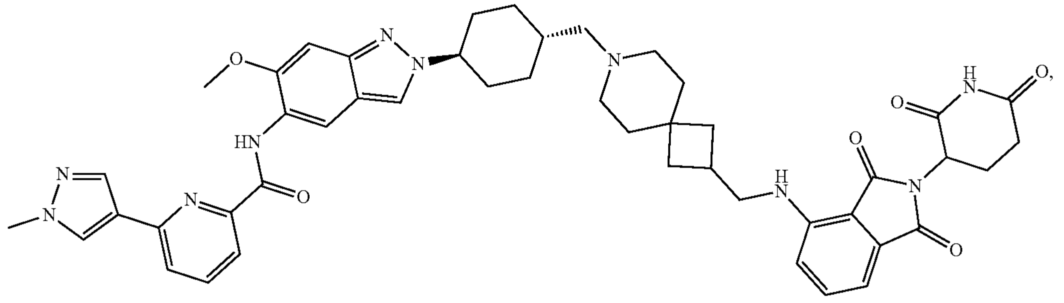
I-219
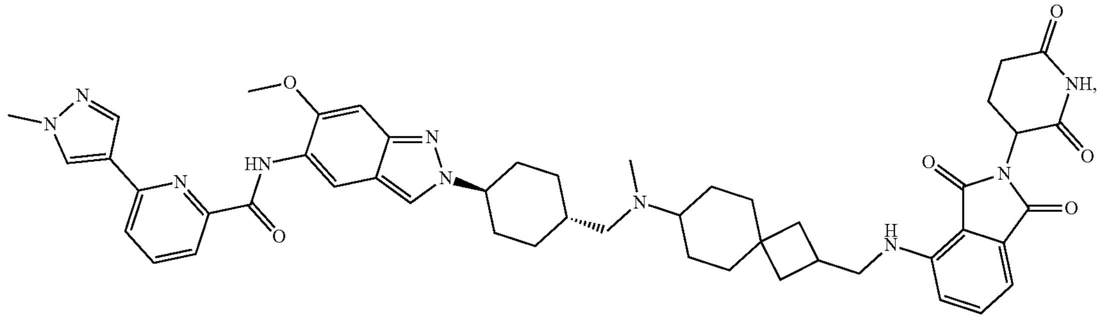
I-220
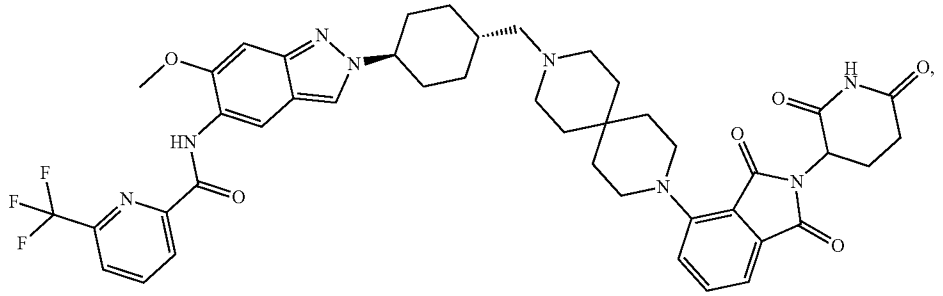
I-222
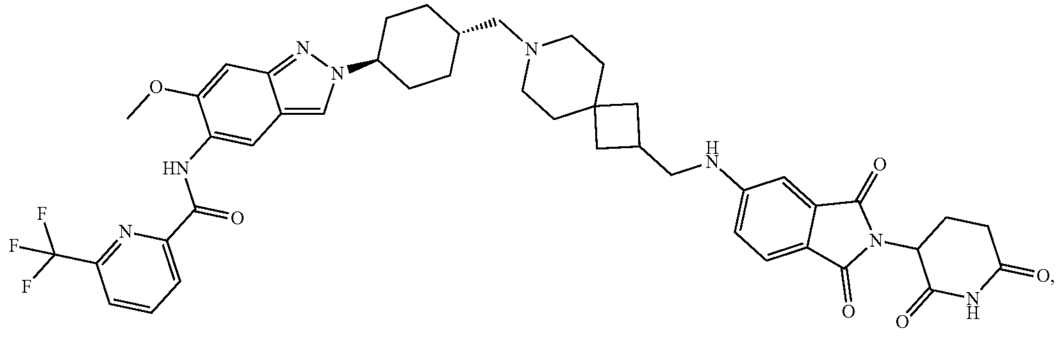

-continued
I-223
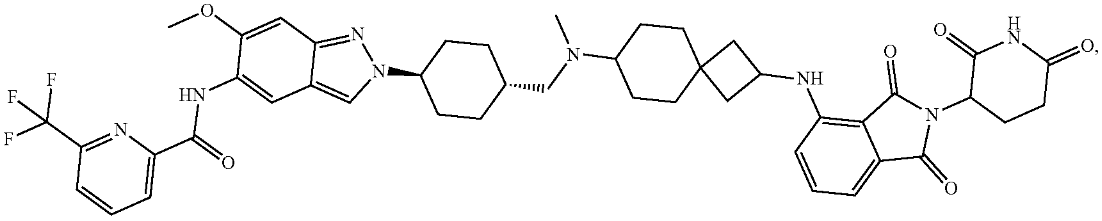
I-224
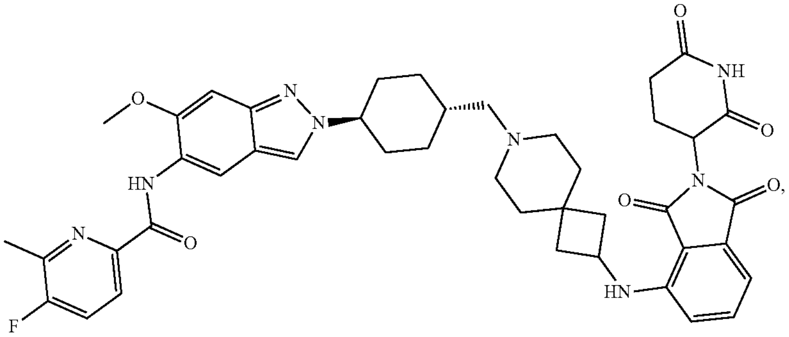
I-227
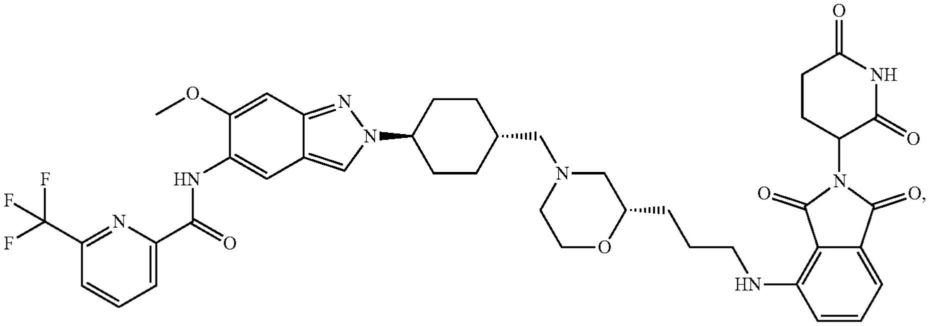
I-230
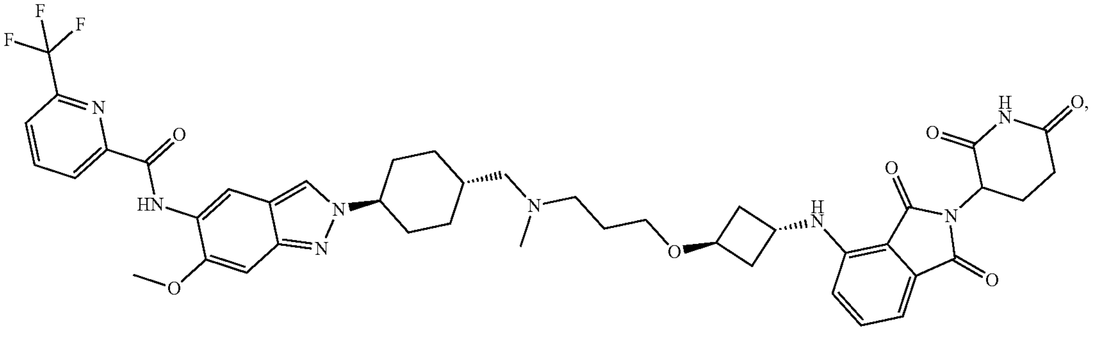
I-231
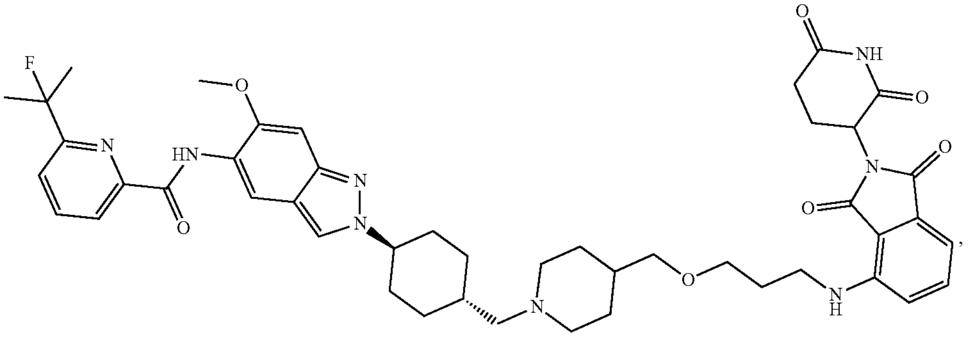

-continued
I-232
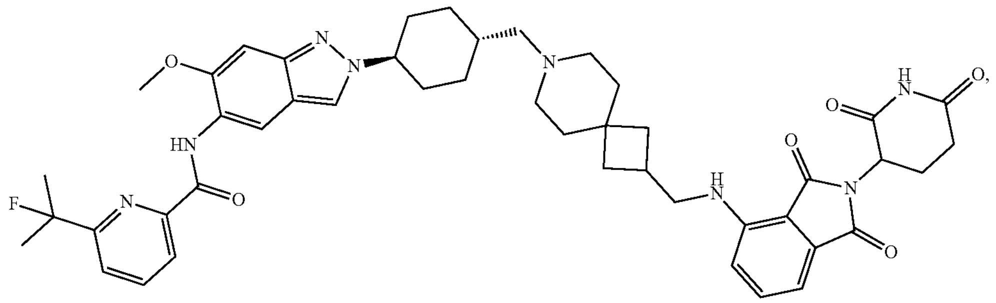
I-233
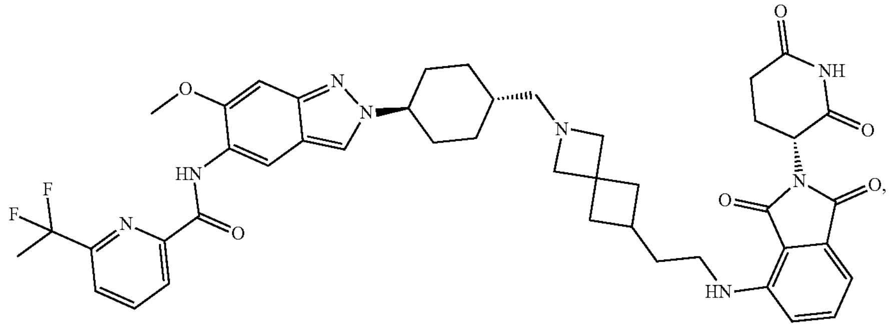
I-255
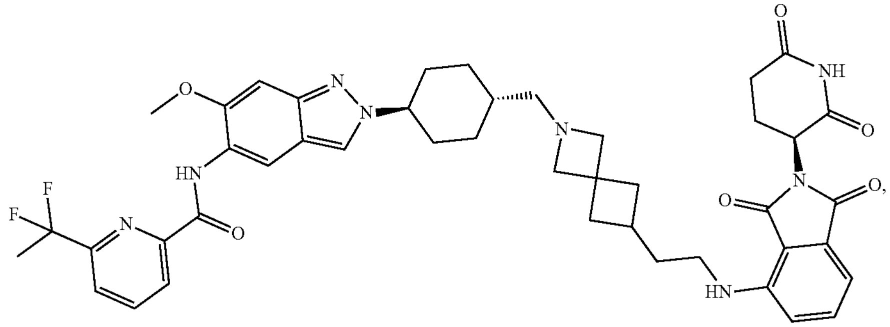
I-273
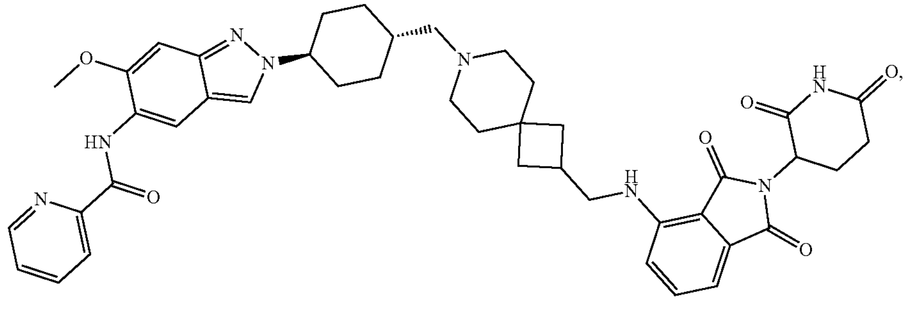
I-274
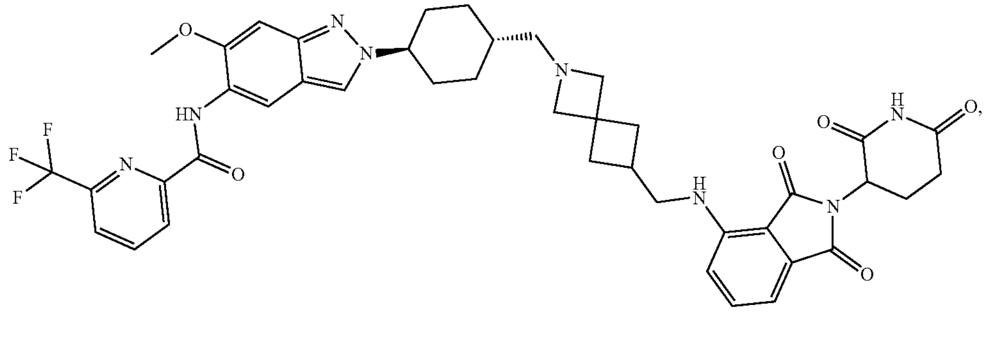

I-296
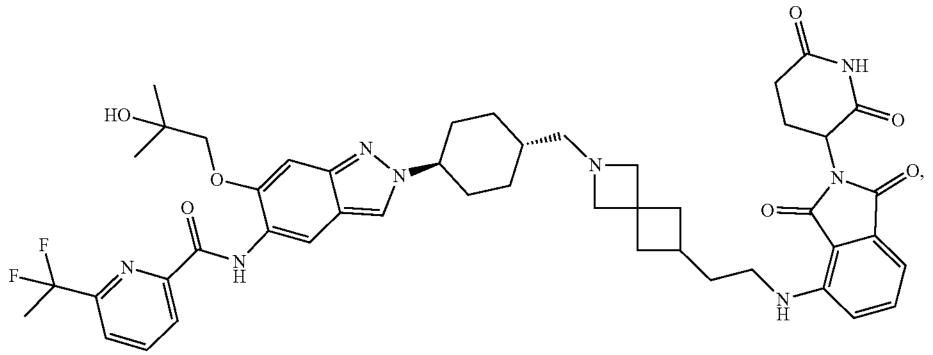
I-303
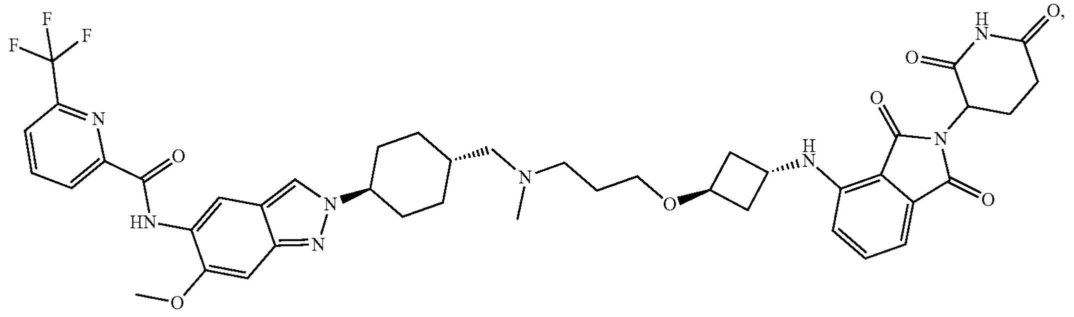
I-305
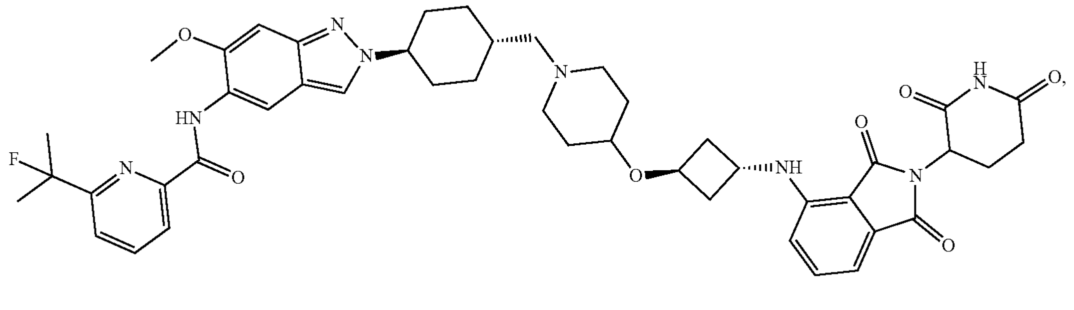
I-311
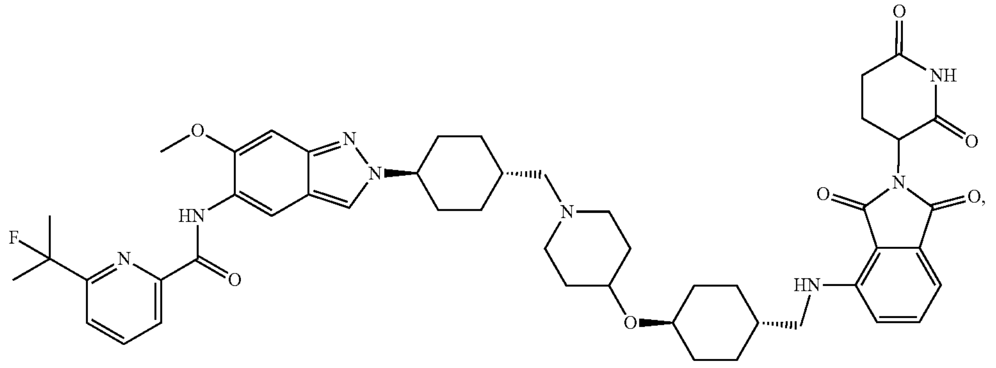

-continued
I-313
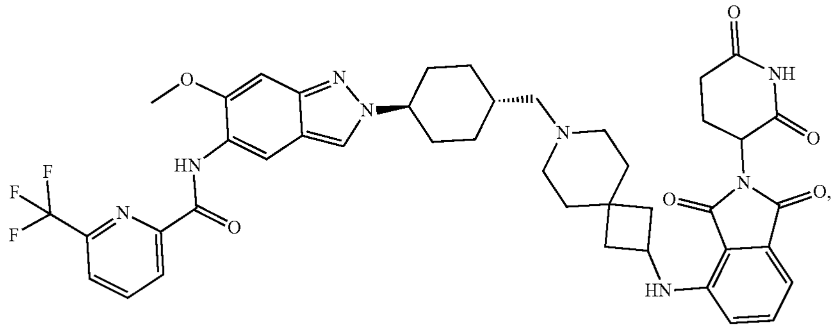
I-315
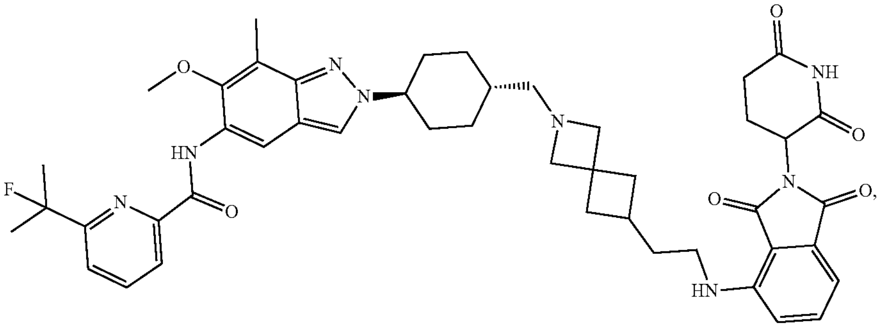
I-316
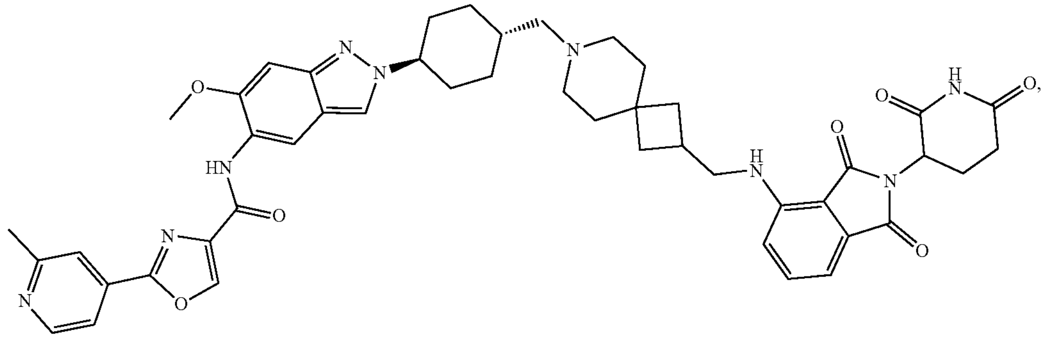
I-317
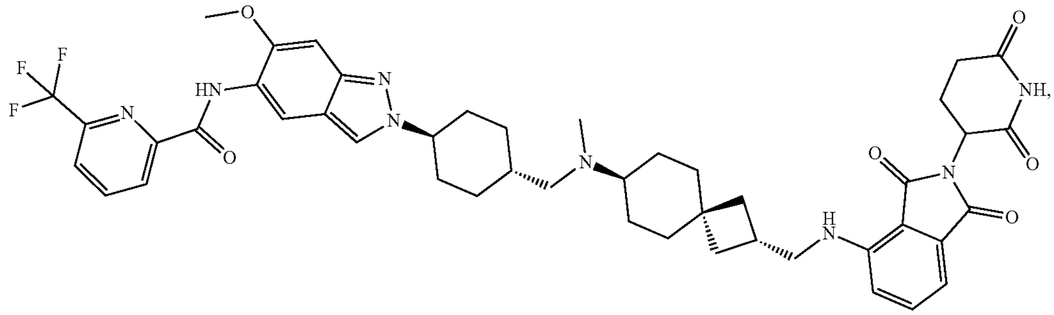
I-318
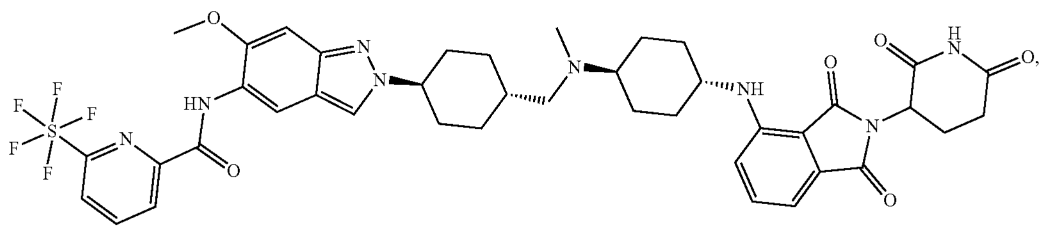

-continued
I-332
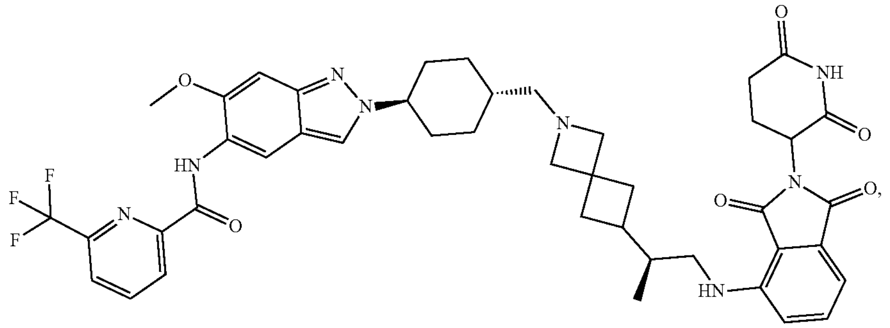
I-335
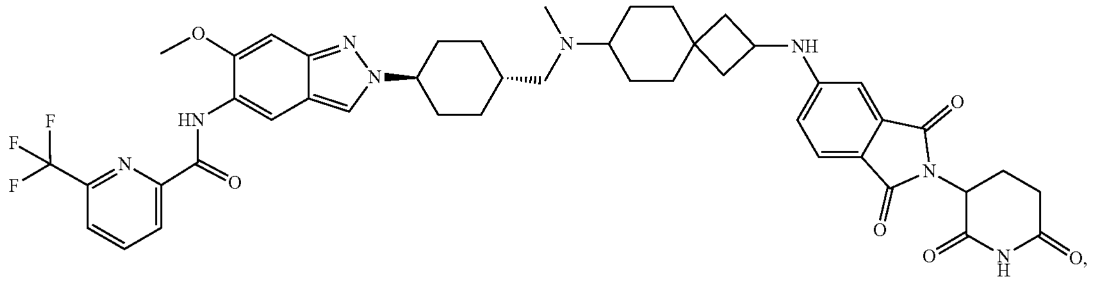
I-336
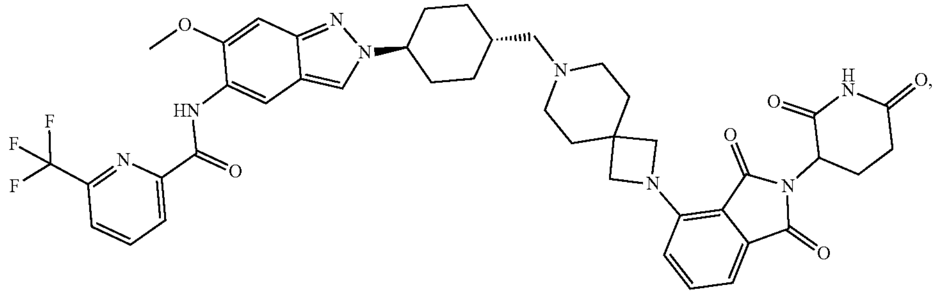
I-337
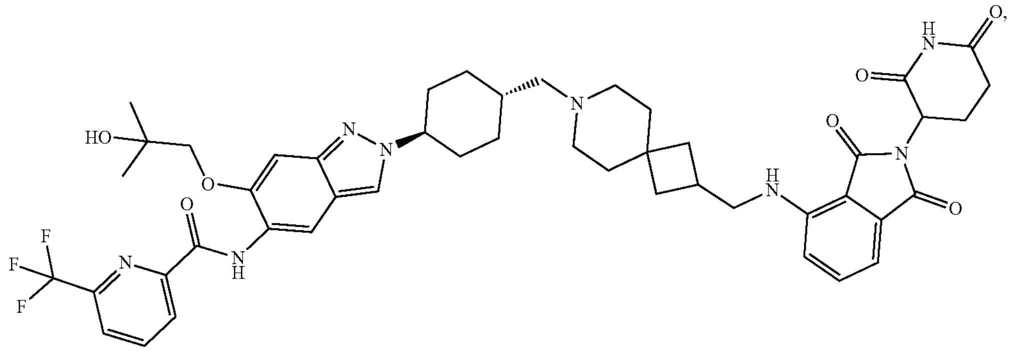
I-338
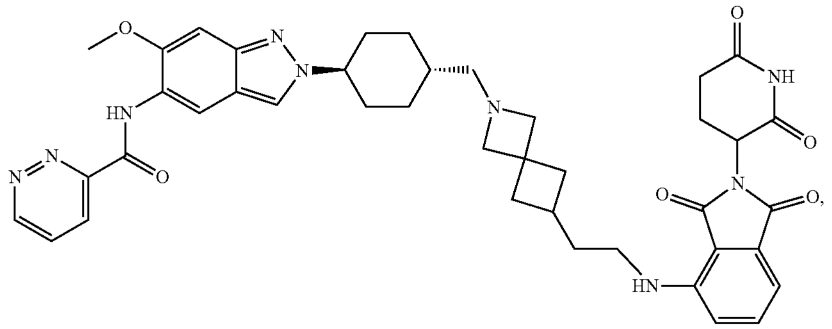

-continued
I-344
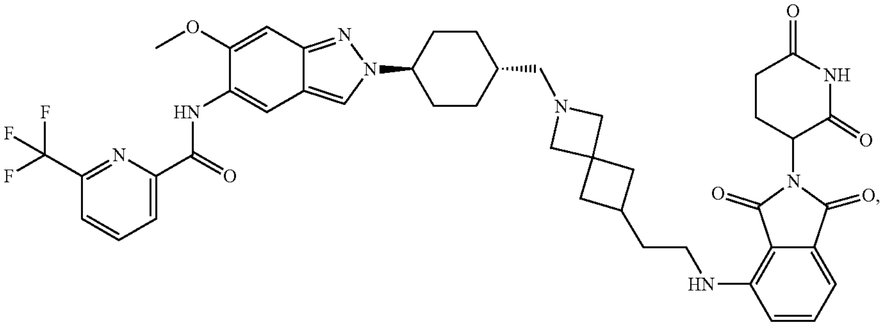
I-346
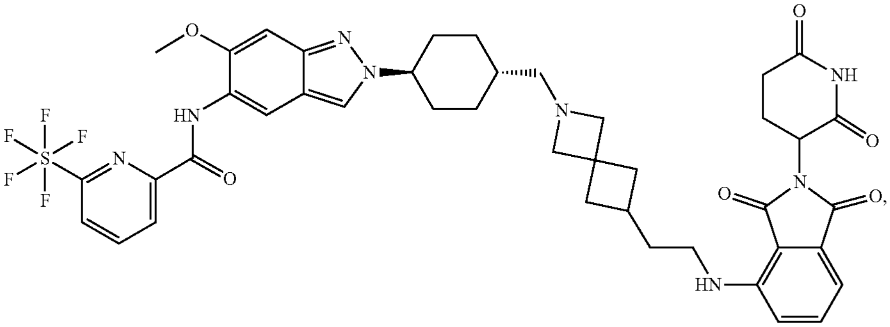
and
I-347
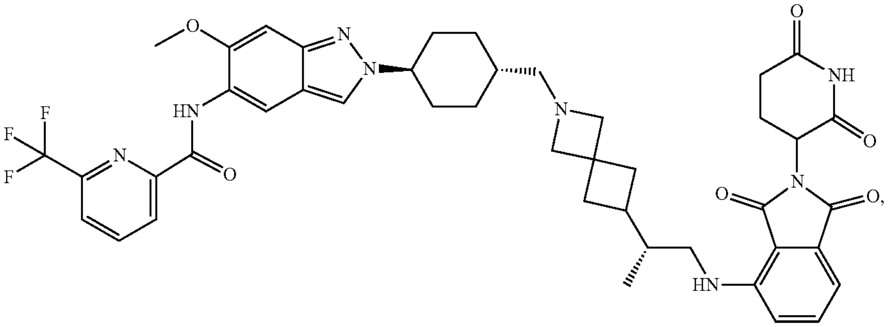
or a pharmaceutically acceptable salt thereof.
4. A pharmaceutical composition comprising a compound of claim 1, and a pharmaceutically acceptable carrier, adjuvant, or vehicle.
5. The compound of claim 1, wherein Ring T is phenyl,
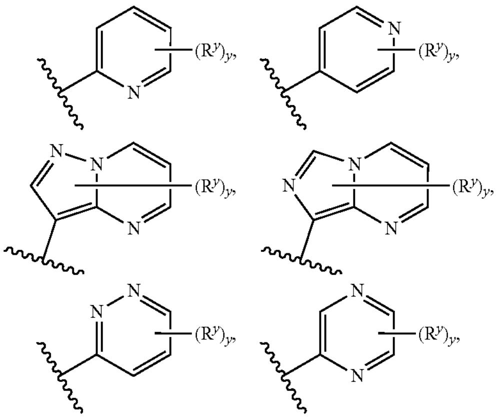
-continued
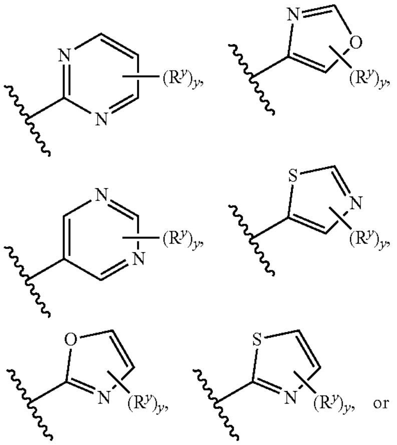
or
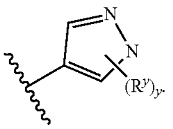

6. The compound of claim 1, wherein $R^x$ is hydrogen, $C_{1-6}$ alkyl, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, or —N(R)$S(O)_2R$.

7. The compound of claim 1, wherein $R^y$ is hydrogen, $C_{1-6}$alkyl, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(S)$NR_2$, —C(O)N(R)OR, —OC(O)R, —OC(O)$NR_2$, —N(R)C(O)OR, —N(R)C(O)R, or —N(R)$S(O)_2R$.

8. The compound of claim 1, wherein $R^y$ is fluoro, chloro, —CN, —$CF_2Me$, —$CFMe_2$, methyl, or —$OCF_3$.

9. The compound of claim 1, wherein x is 0 or 1.

10. The compound of claim 1, wherein m is 0 or 1.

11. The compound of claim 1, wherein Ring A is a 6-membered aryl.

12. The compound of claim 1, wherein said compound is any one of the following formulae:

I-k-4

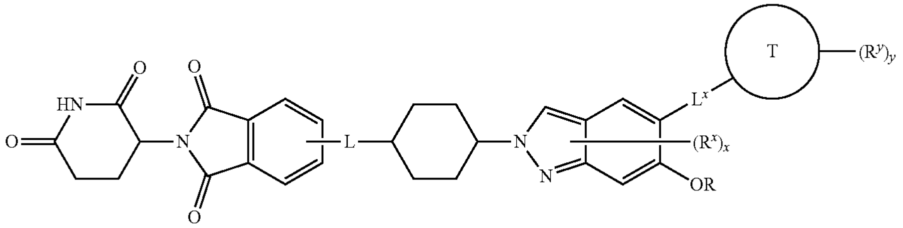

I-k-5

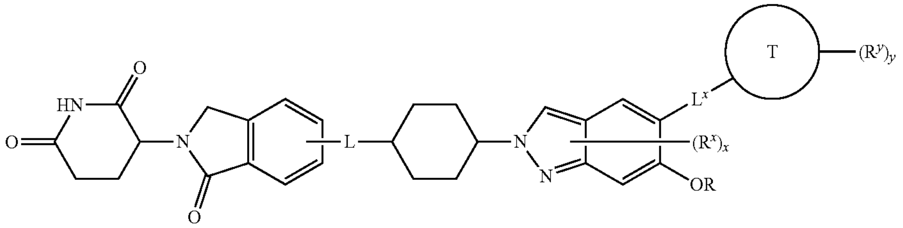

I-k-8

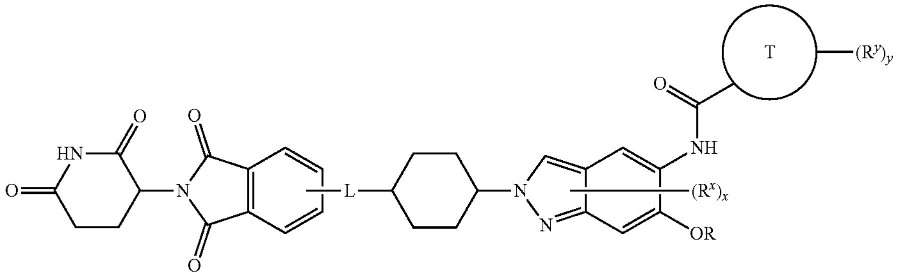

I-k-9

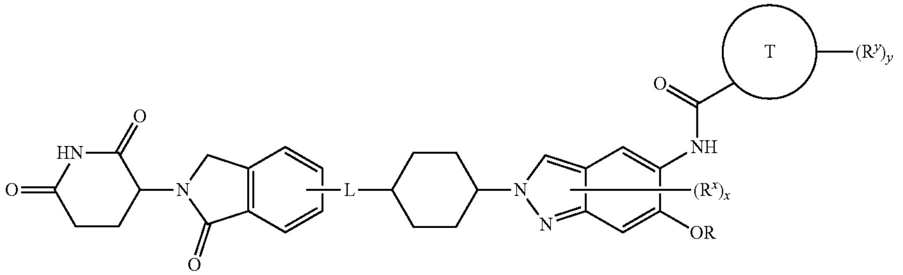

I-k-10

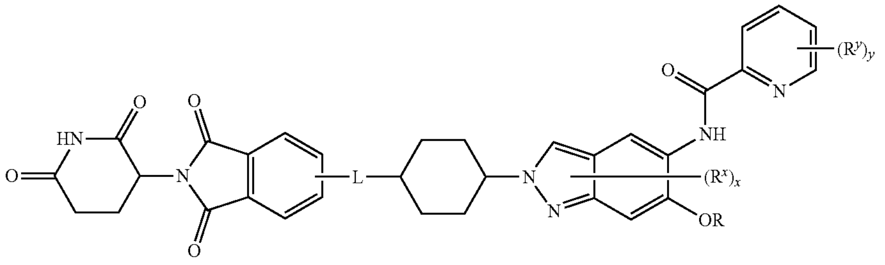

-continued
I-k-11
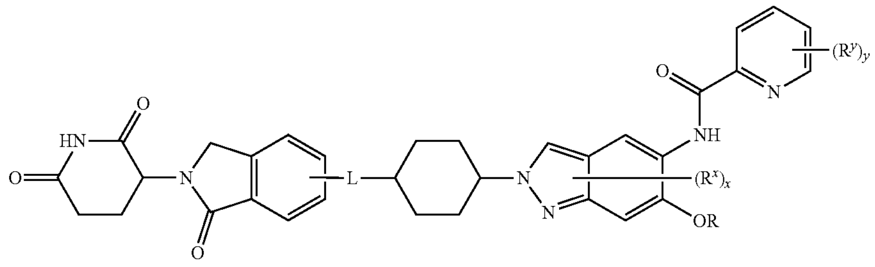
or a pharmaceutically acceptable salt thereof.
13. The compound of claim 1, wherein
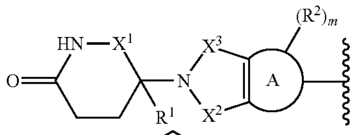
is
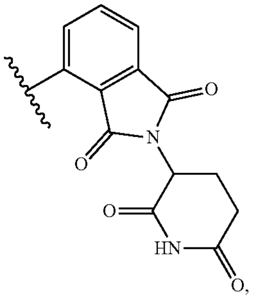
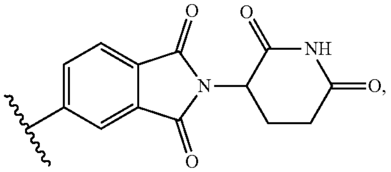
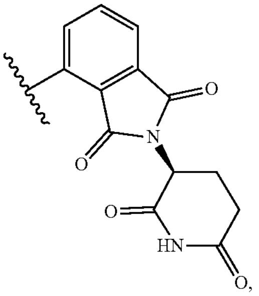
-continued
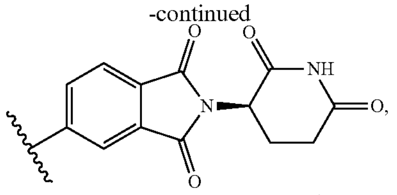
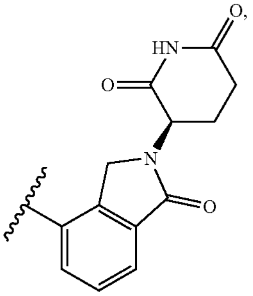
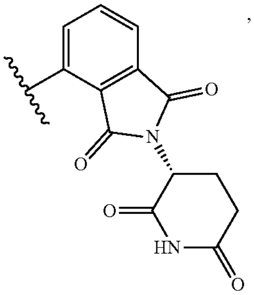
,
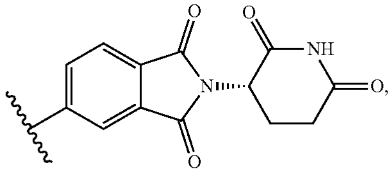
or
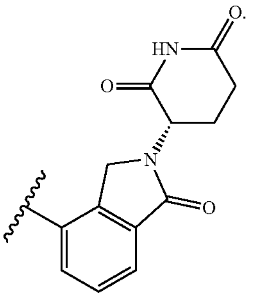 [SMILES: *c1cccc2c1CN([C@H]1CCC(=O)NC1=O)C2=O]
14. The compound of claim 1, wherein L is
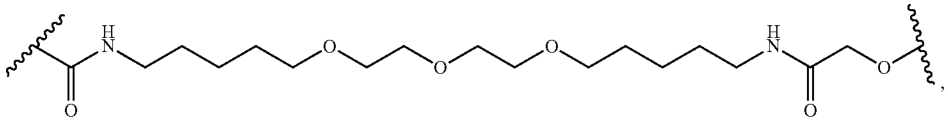
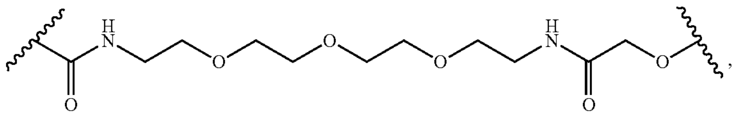

-continued
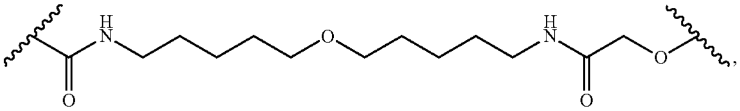,
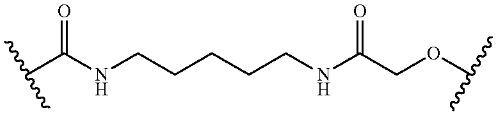,
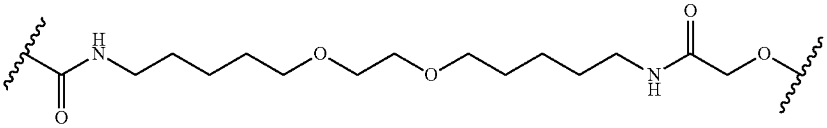,
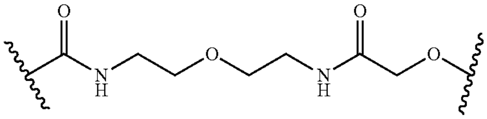, 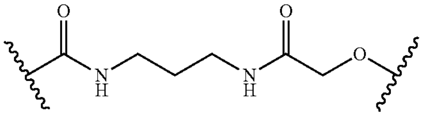,
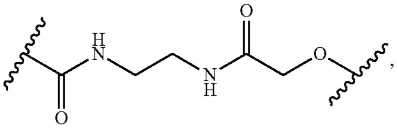, 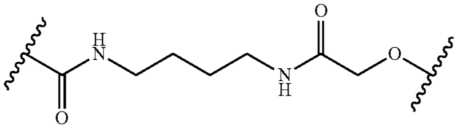,
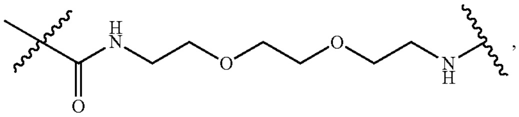, 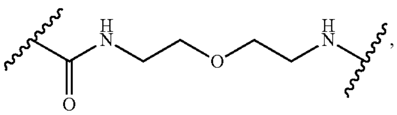,
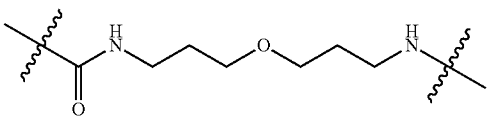, 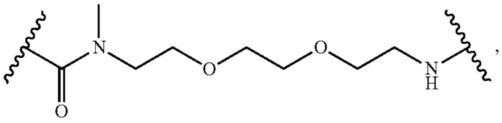,
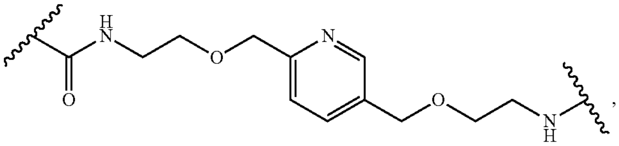, 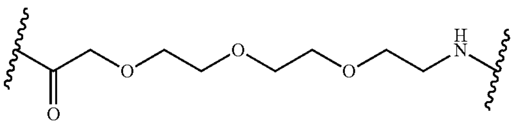,
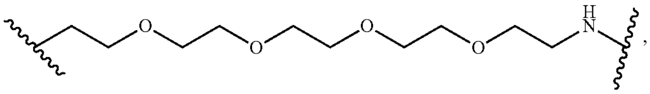, 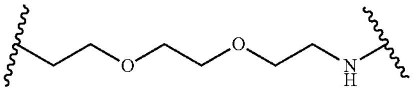,
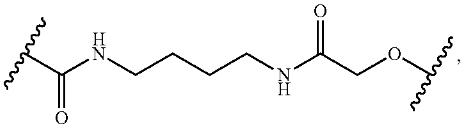, 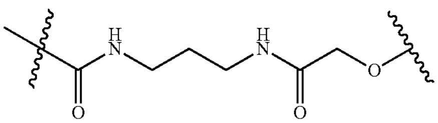,
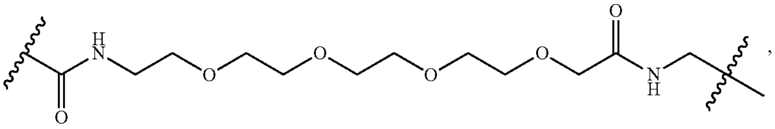,
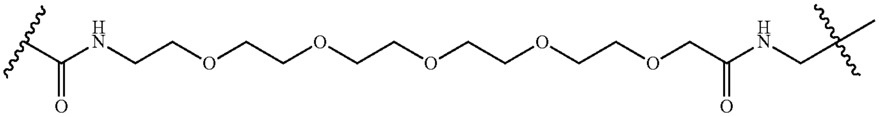,
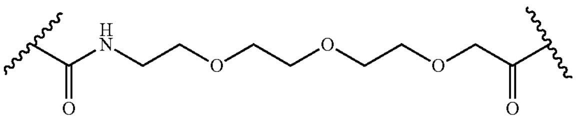,
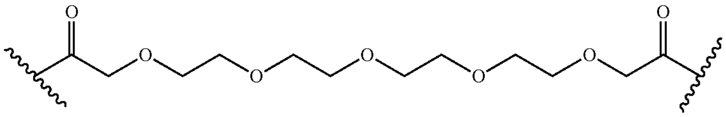, -continued
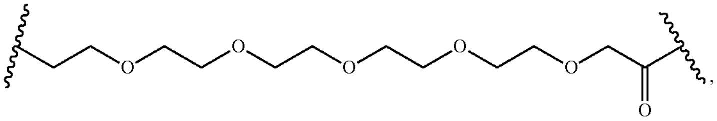,
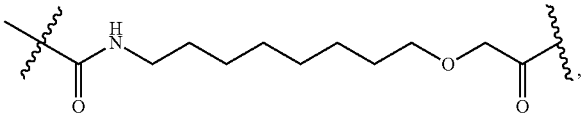, 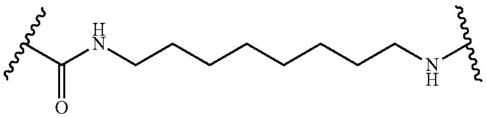,
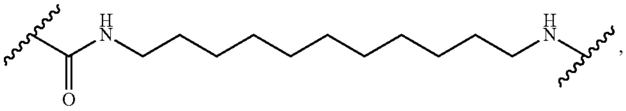, 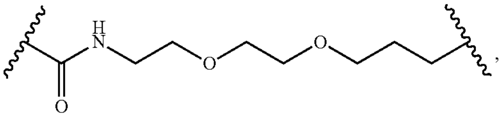,
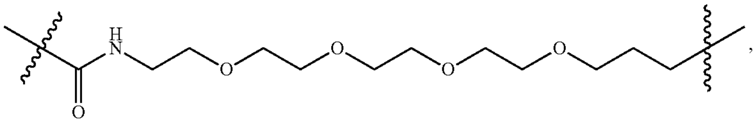,
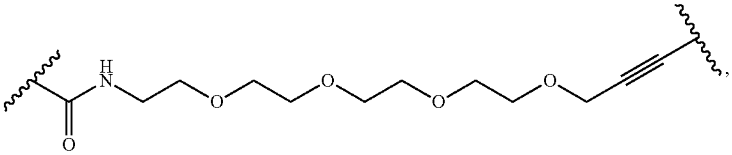,
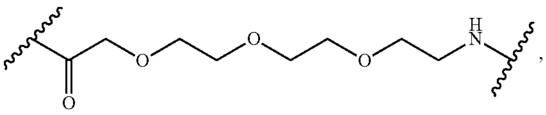, 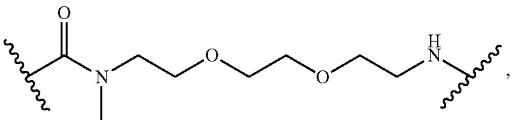,
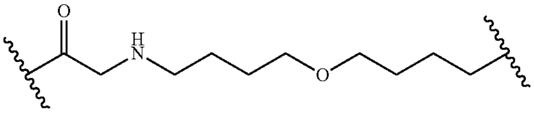, 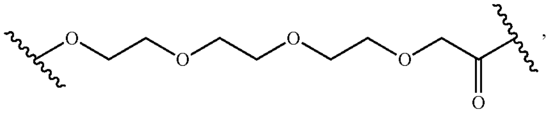,
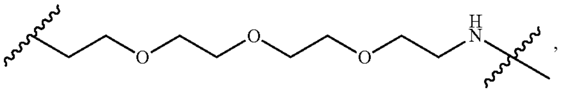,
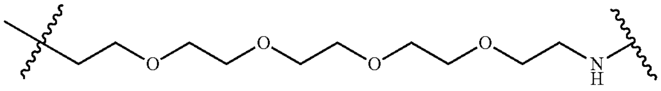, 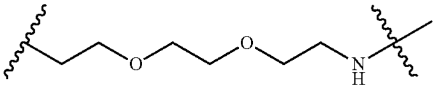,
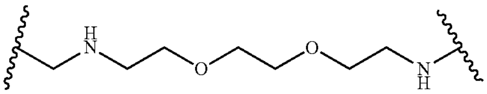, 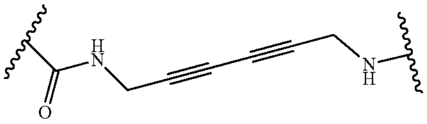,
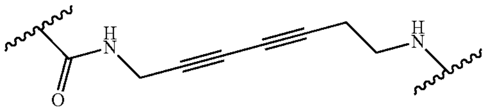, 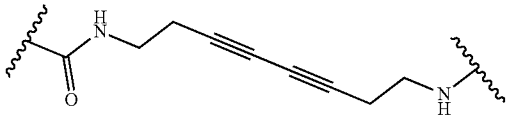,
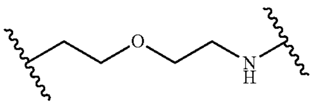, 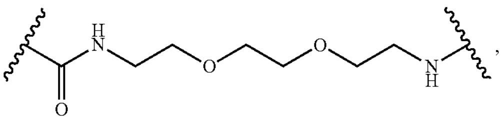,
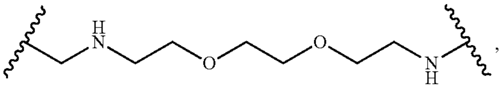, 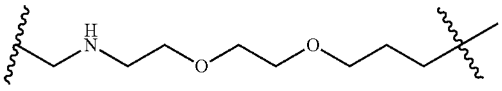,
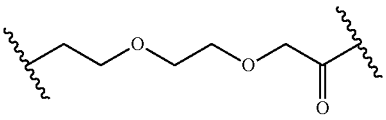, 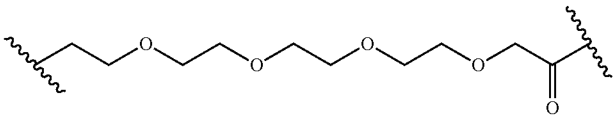, -continued
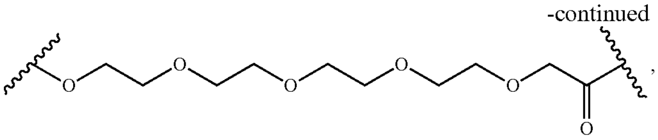,
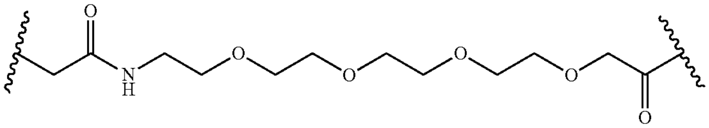,
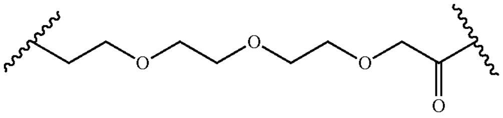, 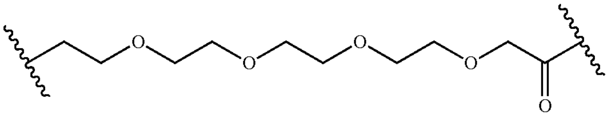,
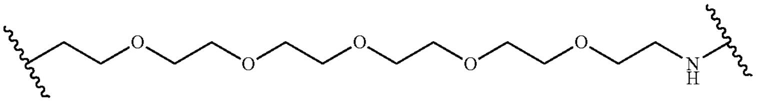,
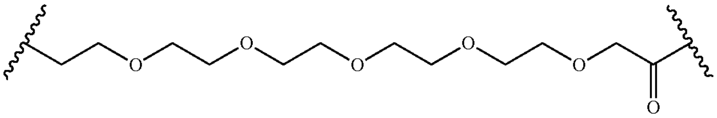, 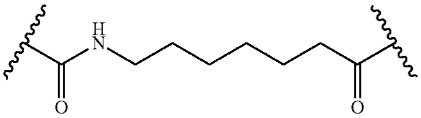,
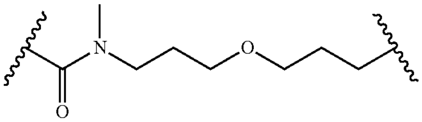, 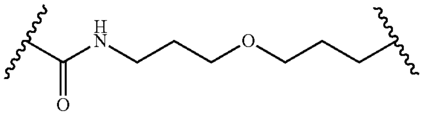,
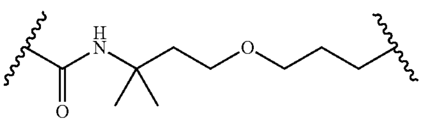, 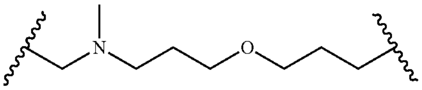,
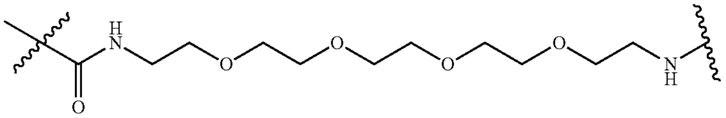,
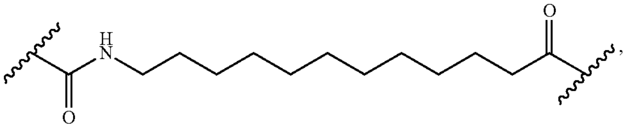,
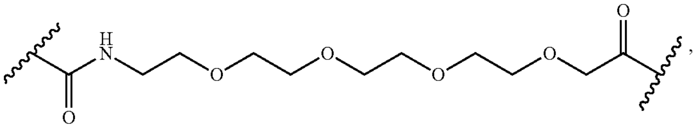,
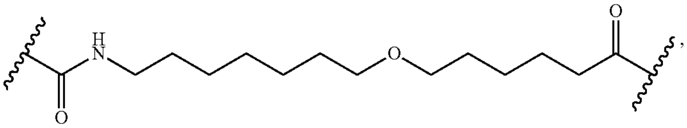, 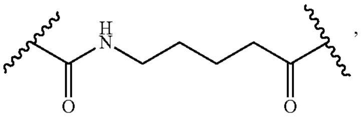,
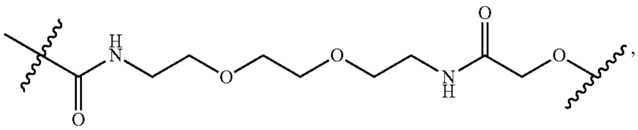,
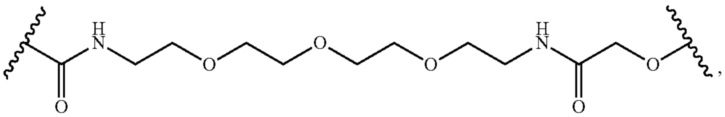,
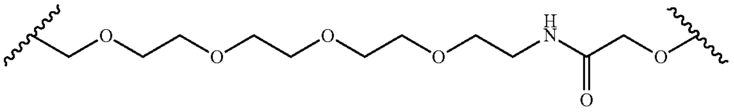, -continued
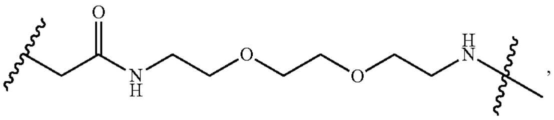 ,
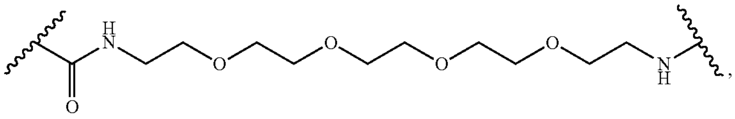 ,
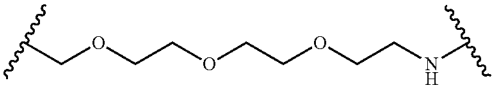 ,
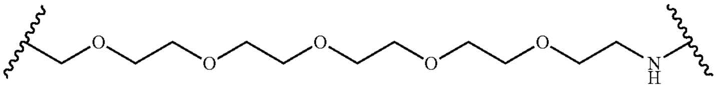 ,
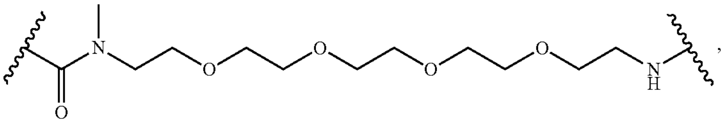 ,
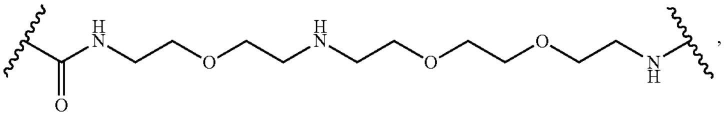 ,
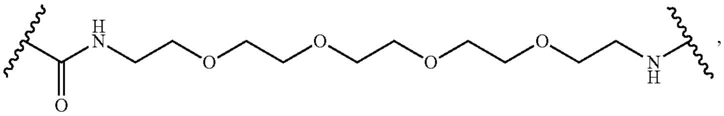 ,
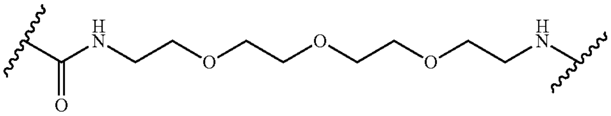 , 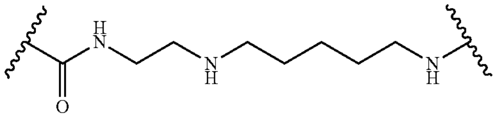 ,
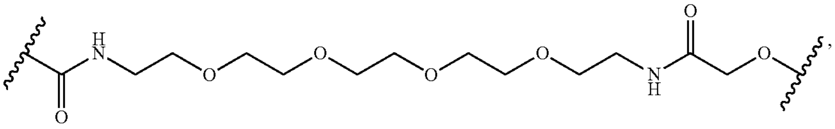 ,
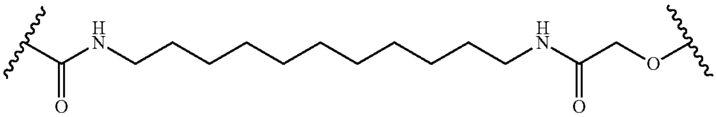 ,
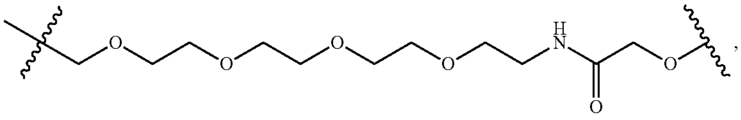 ,
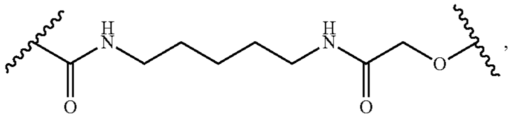 ,
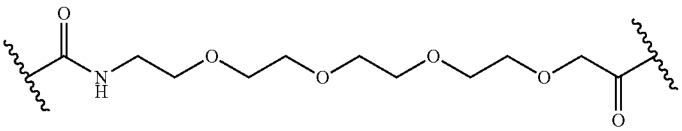 ,
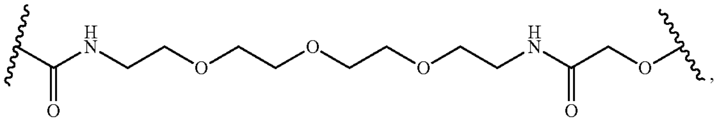 , -continued
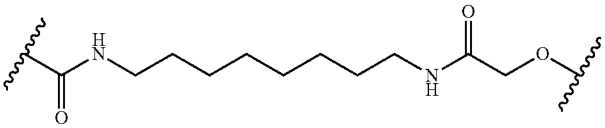, 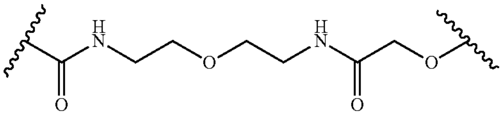,
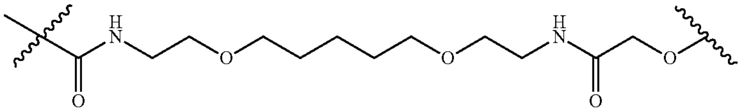,
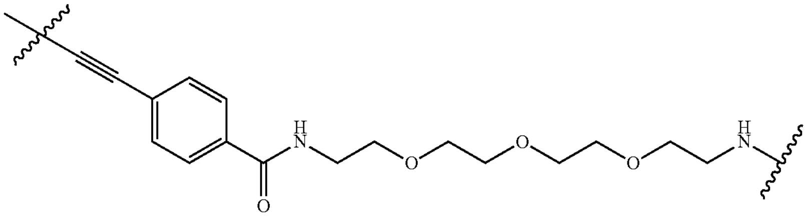,
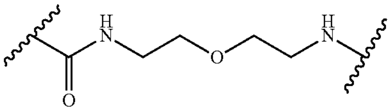, 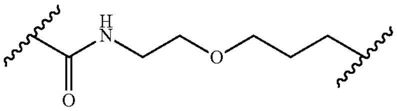,
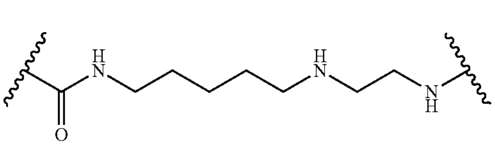, 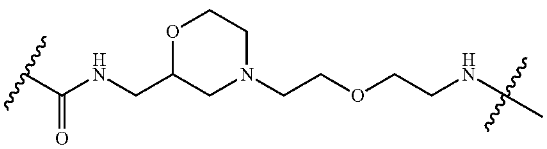,
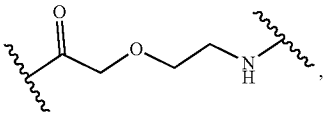, 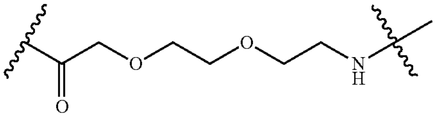,
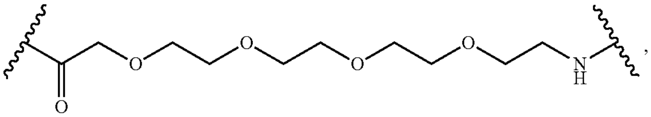,
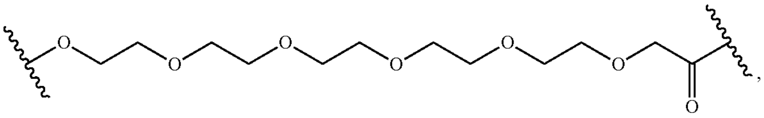,
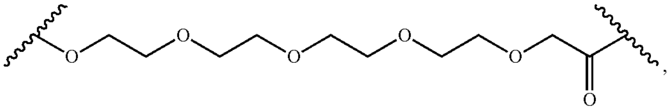,
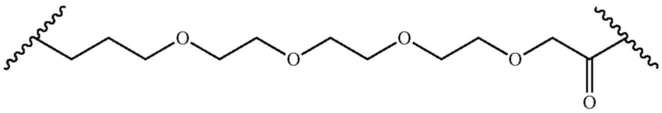,
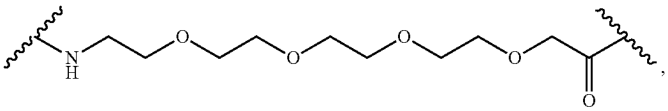, 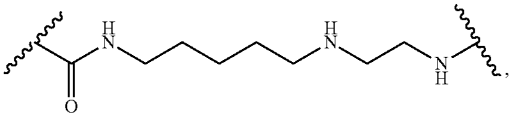,
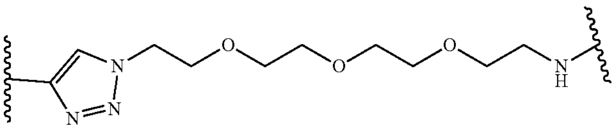,
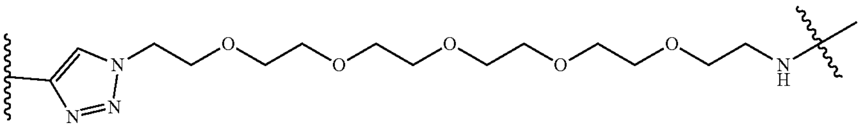, -continued
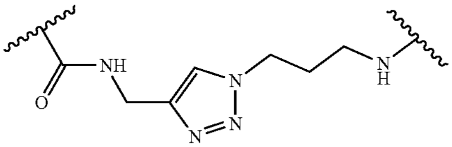,
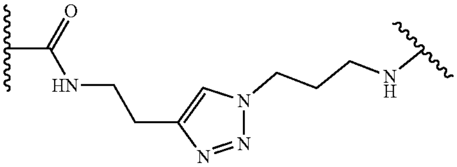,
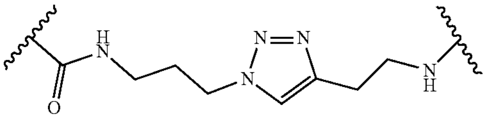,
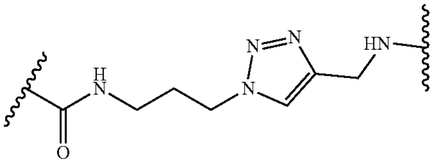,
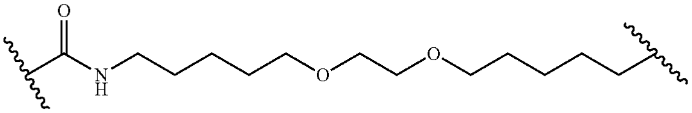,
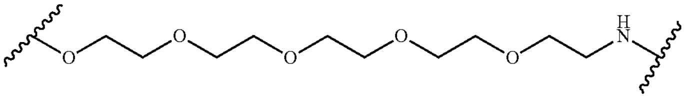,
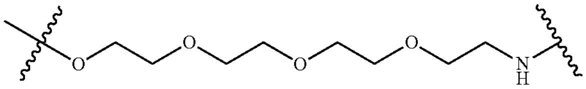,
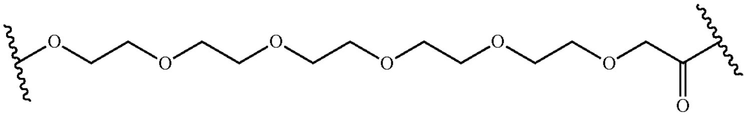,
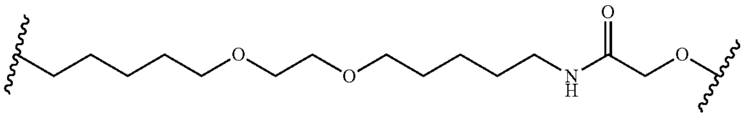,
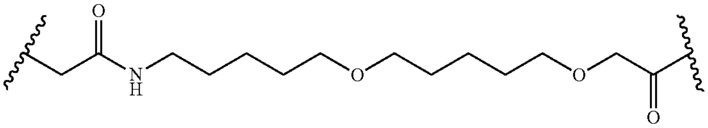,
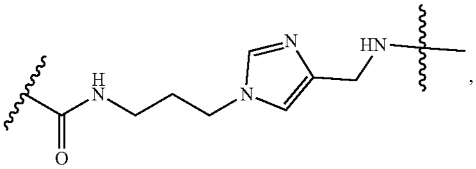,
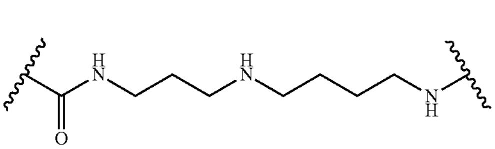,
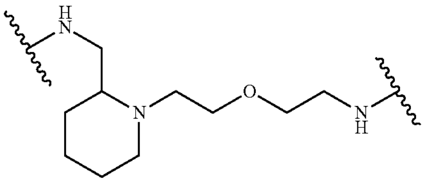,
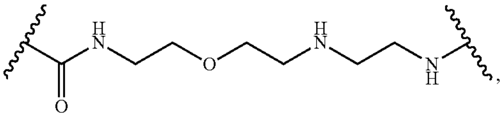,
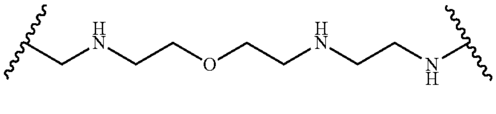,
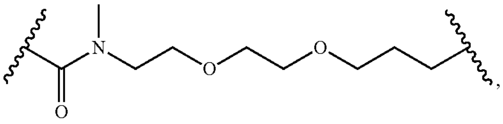,
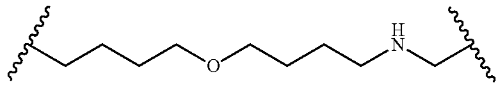,
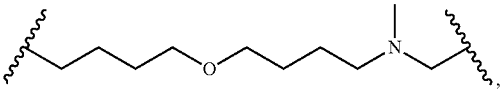,
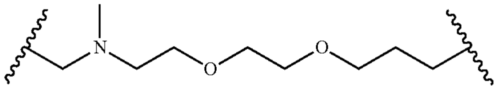, -continued
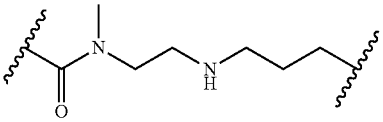,
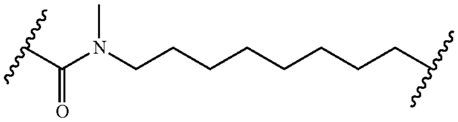,
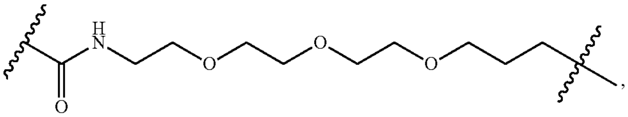,
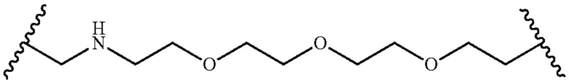,
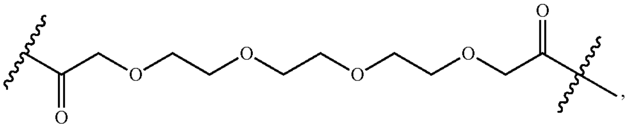,
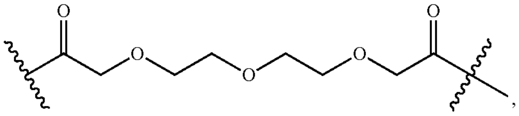,
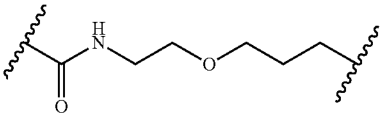,
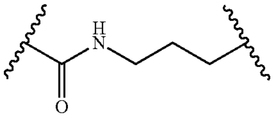,
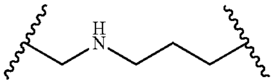,
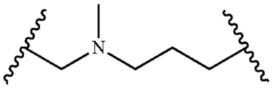,
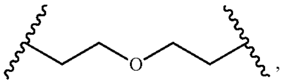,
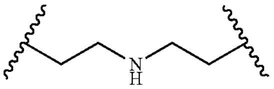,
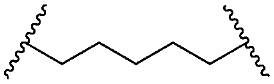,
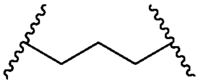,
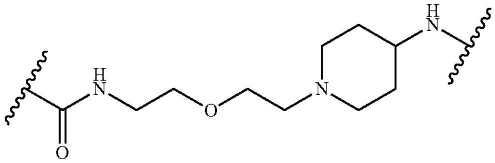,
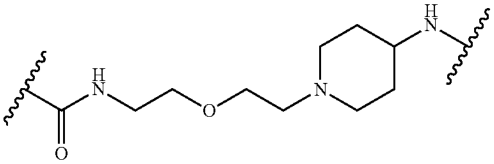,
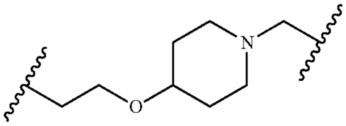,
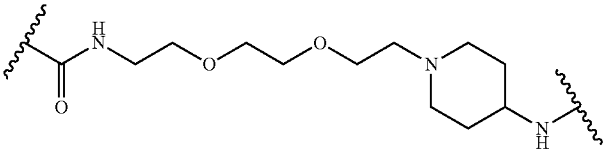,
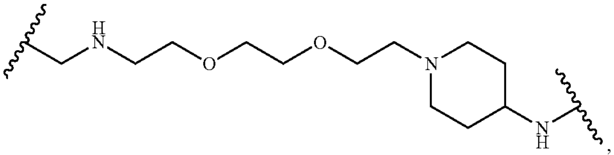,
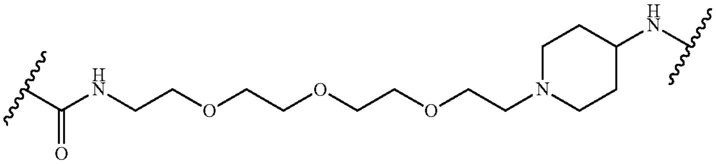,
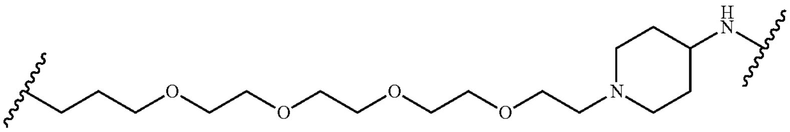, -continued
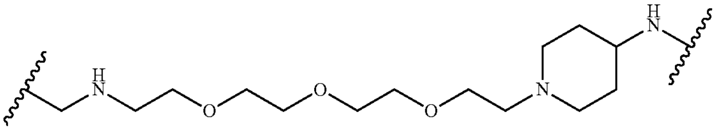,
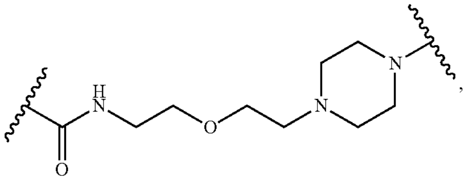,
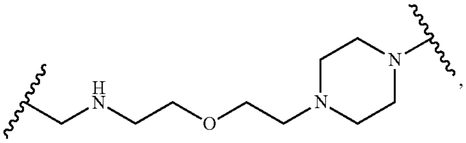,
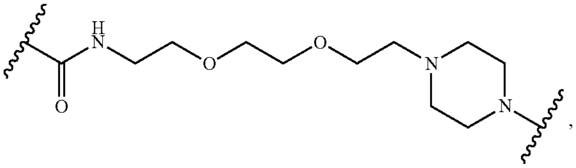,
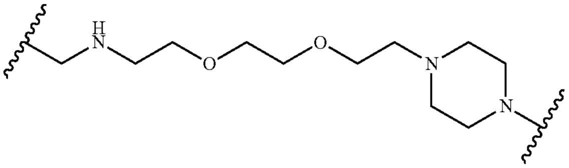,
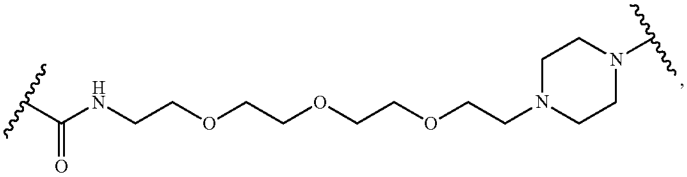,
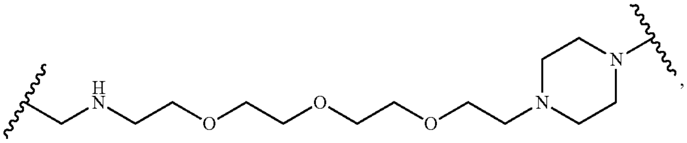,
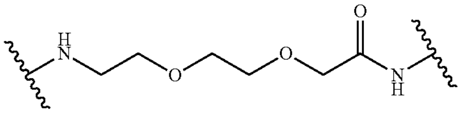,
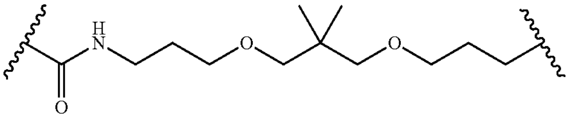,
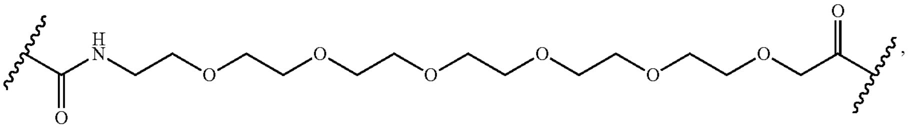,
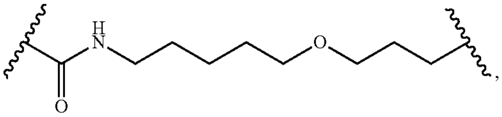,
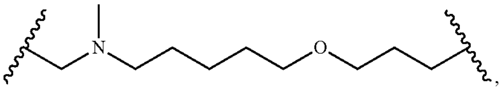,
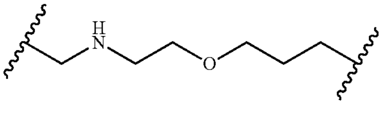,
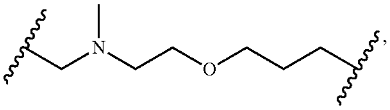,
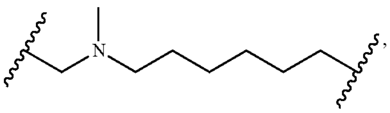,
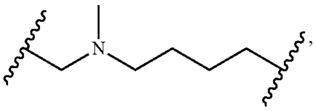,
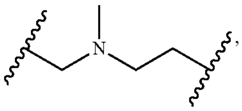,
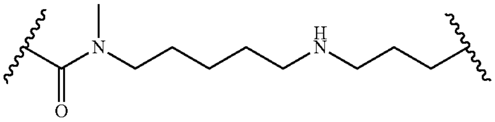,
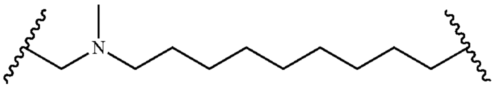,
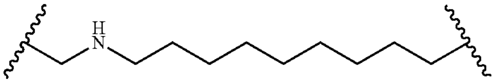,
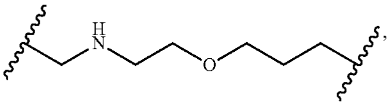,
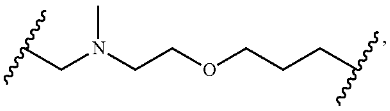,
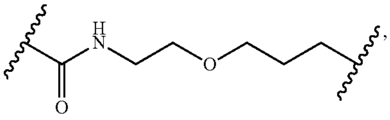, -continued
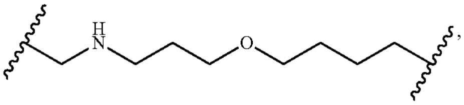,
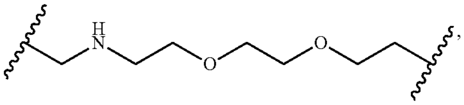,
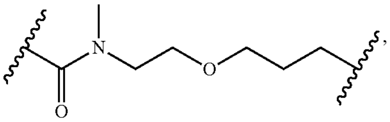,
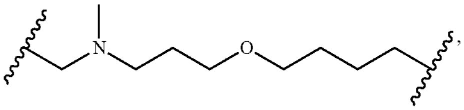,
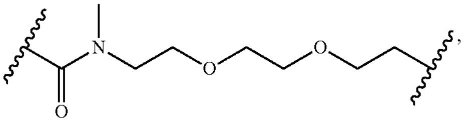,
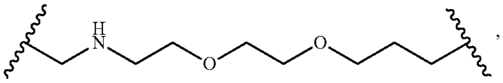,
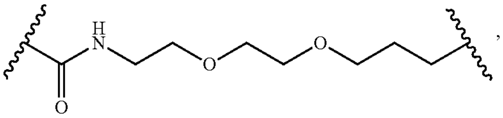,
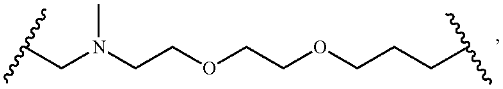,
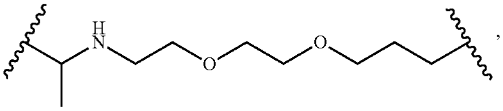,
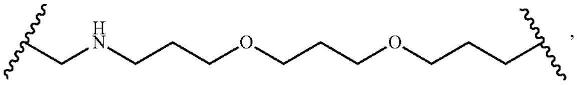,
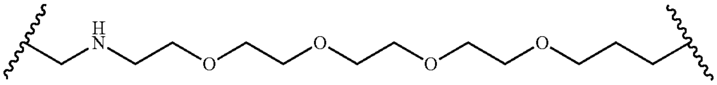,
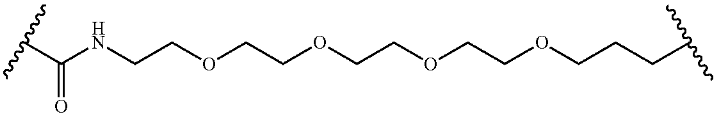,
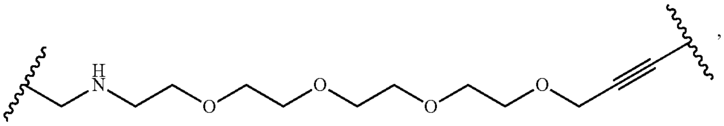,
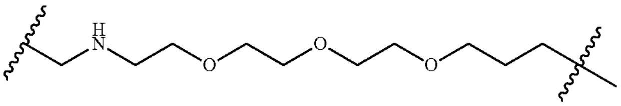,
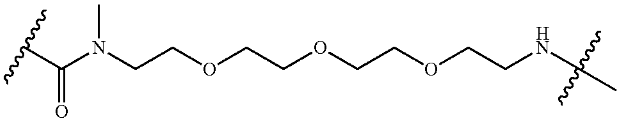,
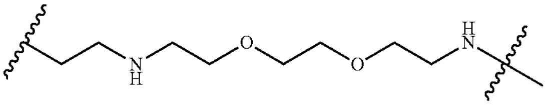,
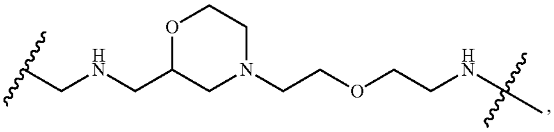,
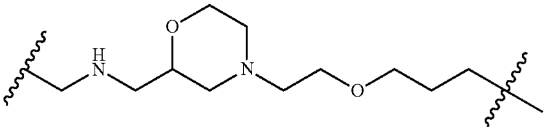,
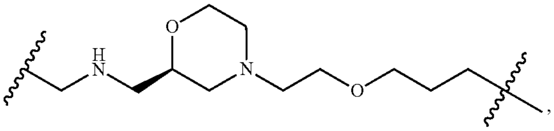,
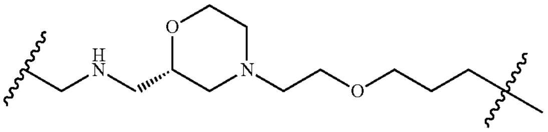,
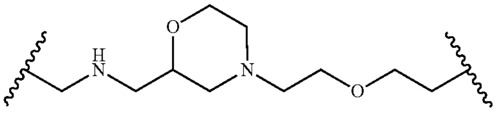,
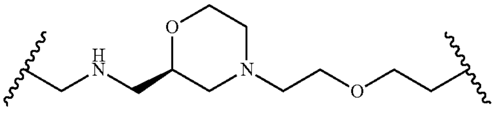,
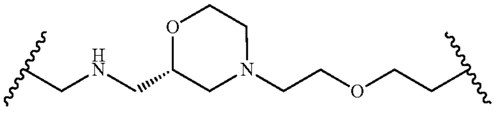, -continued
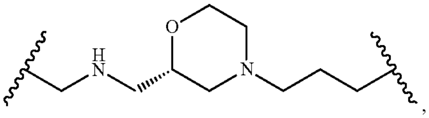, 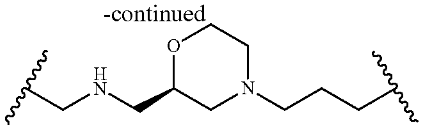,
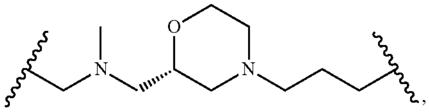, 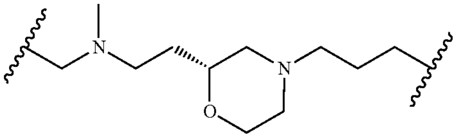,
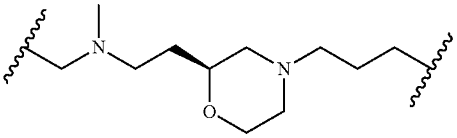, 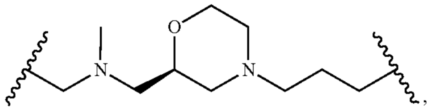,
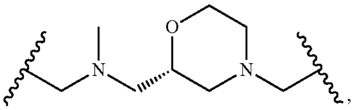, 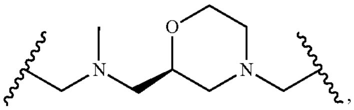,
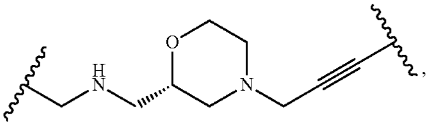, 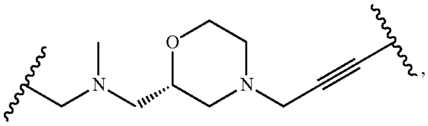,
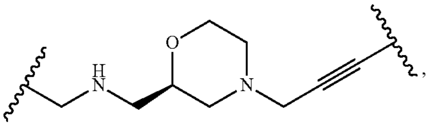, 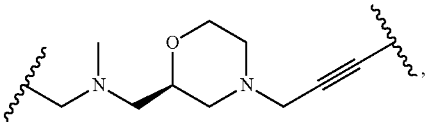,
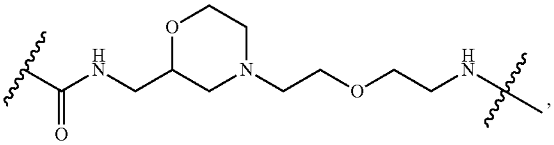, 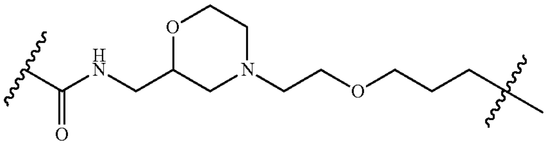,
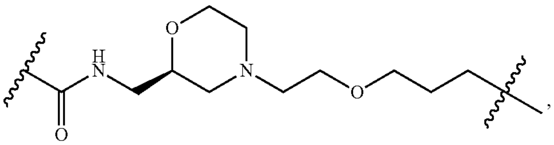, 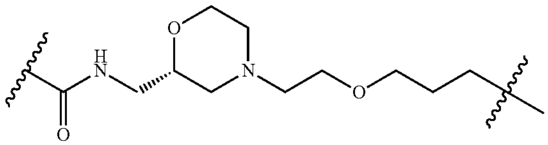,
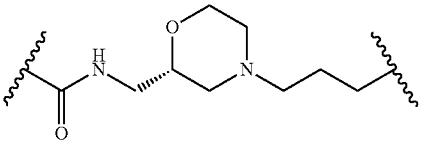, 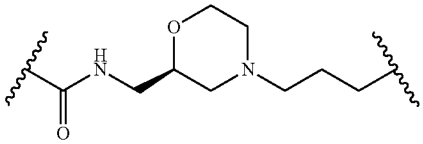,
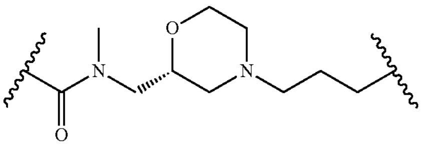, 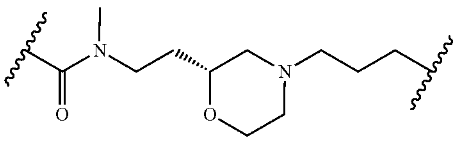,
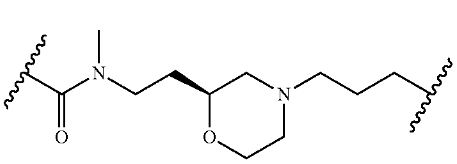, 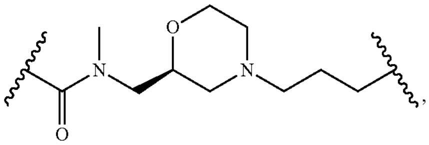,
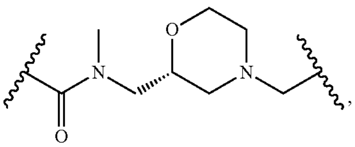, 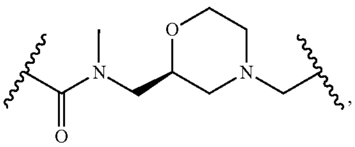, 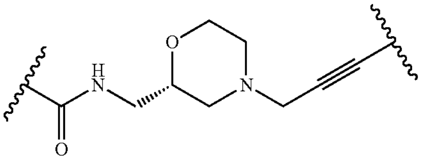, -continued
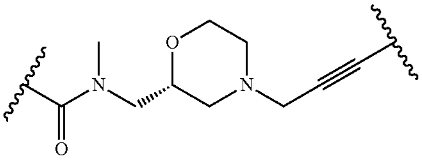,
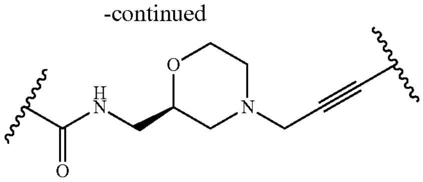,
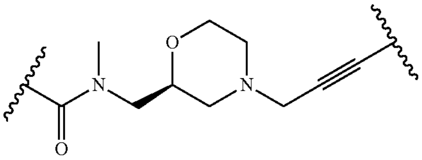,
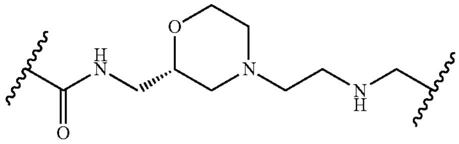,
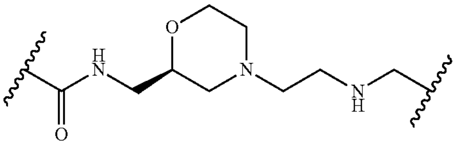,
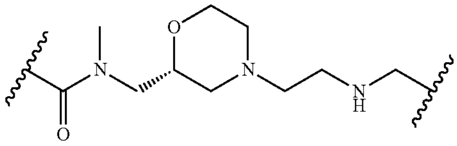,
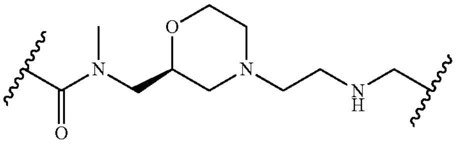,
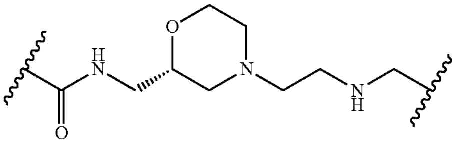,
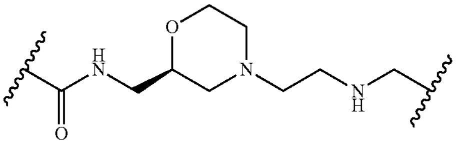,
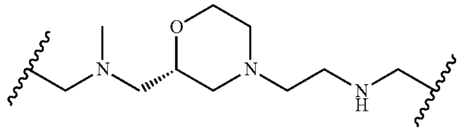,
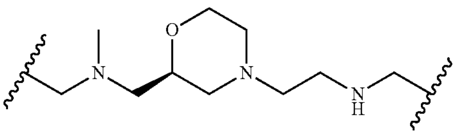,
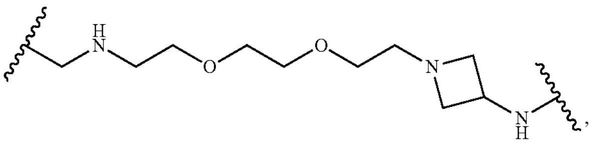,
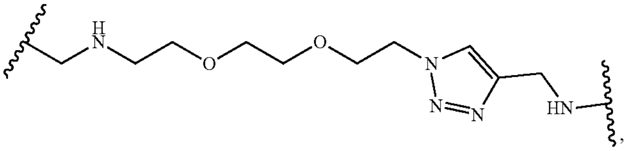,
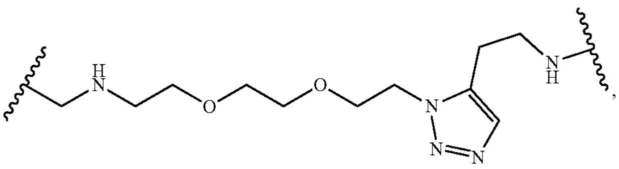,
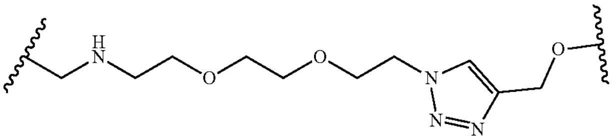,
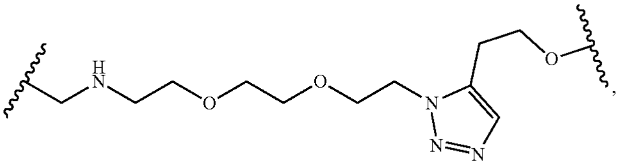,
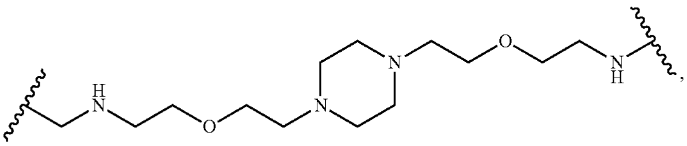, -continued
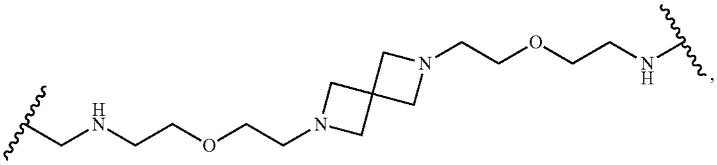,
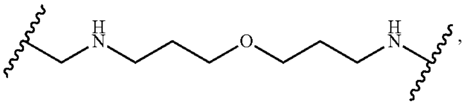, 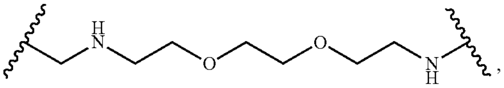,
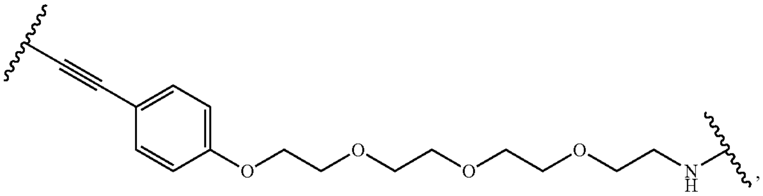,
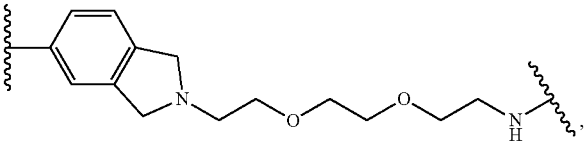, 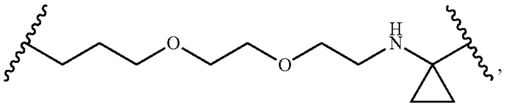,
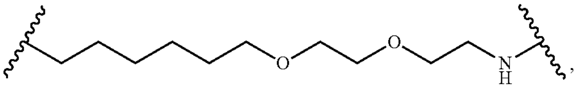, 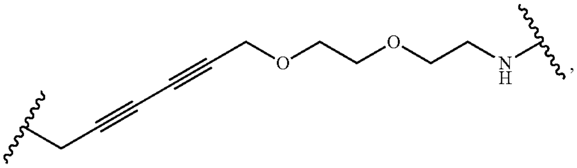,
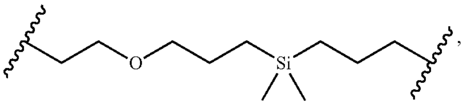, 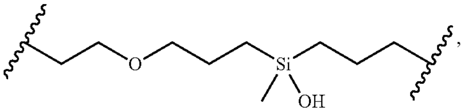,
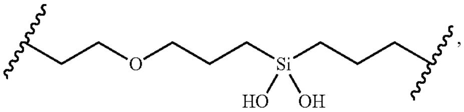, 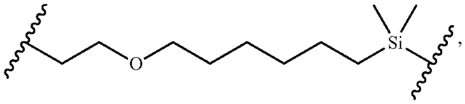,
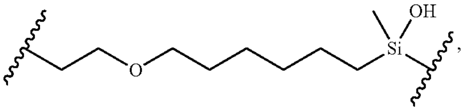, 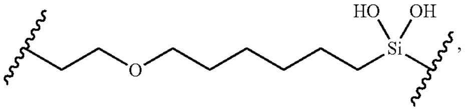,
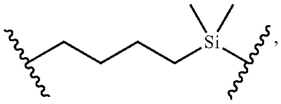, 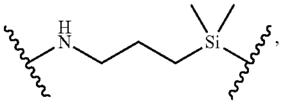, 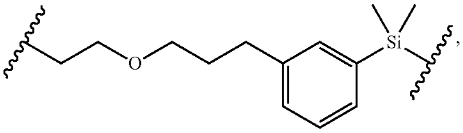,
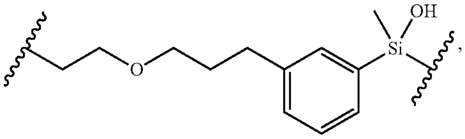, 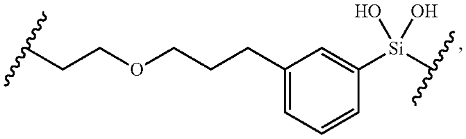,
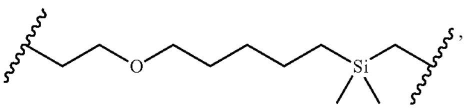, 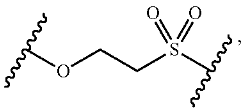,
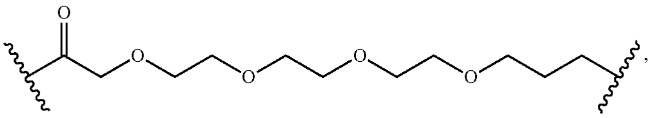, 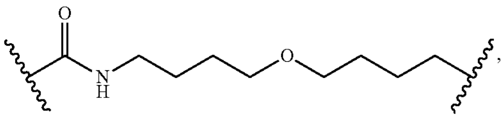, -continued
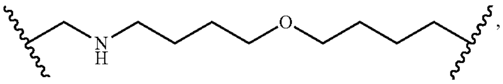, 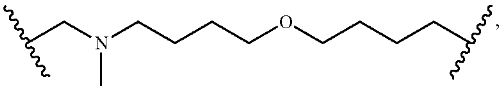,
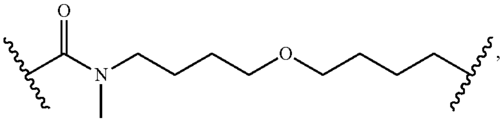, 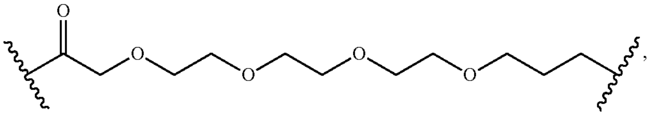,
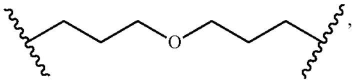, 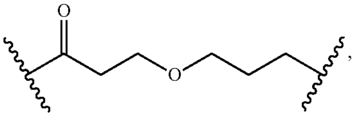, 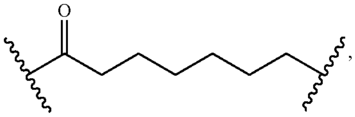,
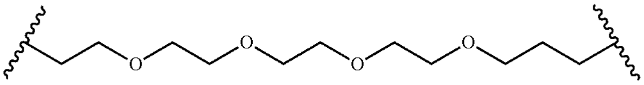,
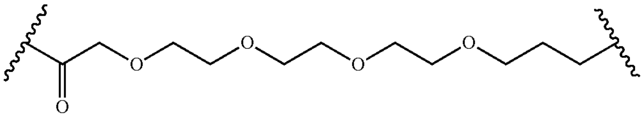,
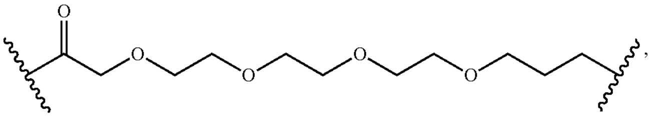, 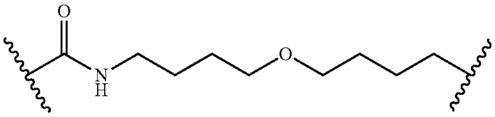,
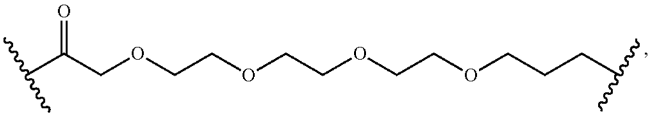, 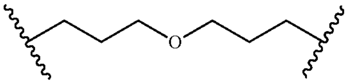,
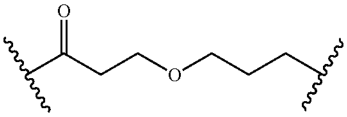, 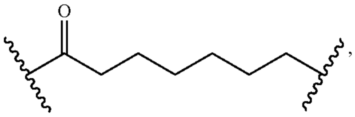,
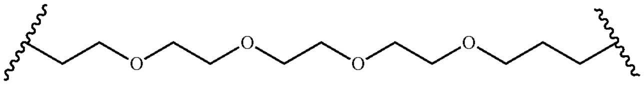,
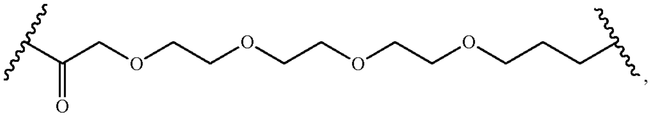, 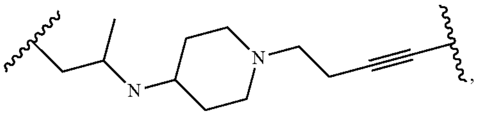,
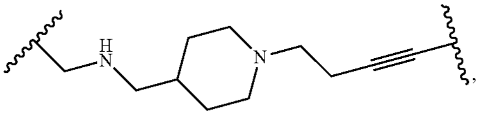, 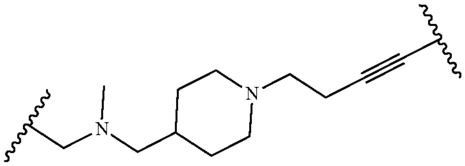,
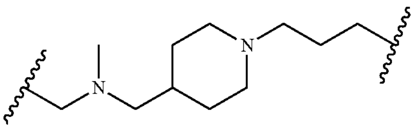, 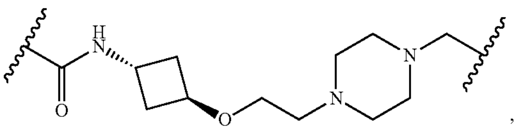,
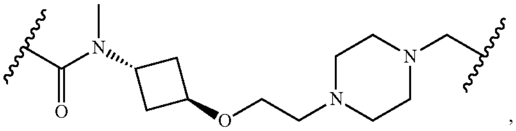, 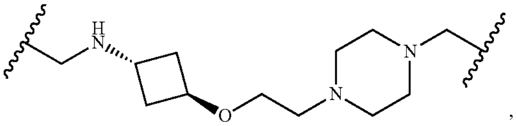, -continued
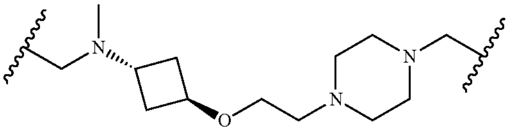,
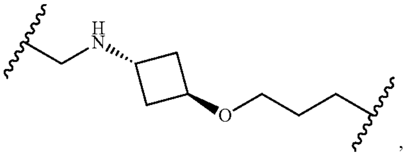,
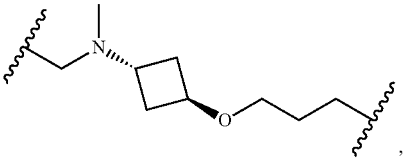,
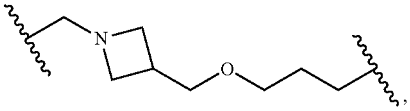,
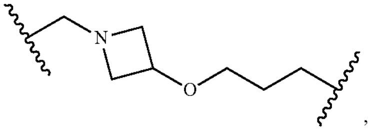,
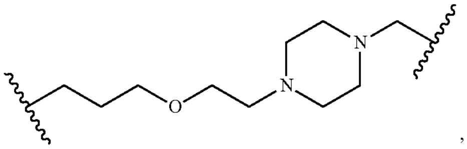,
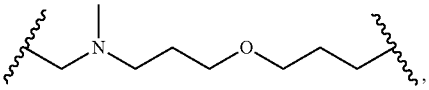,
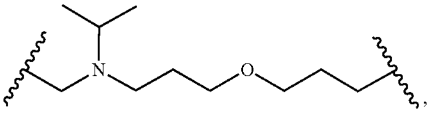,
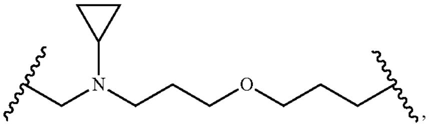,
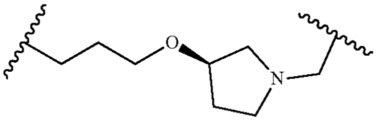,
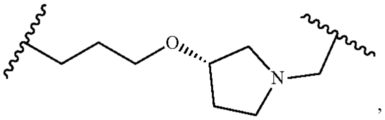,
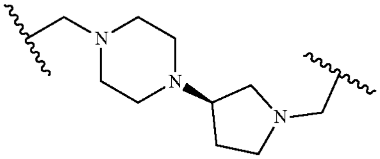,
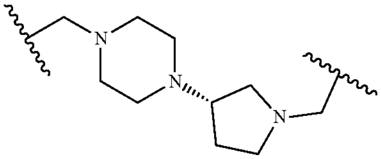,
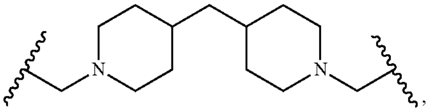,
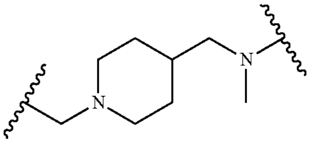,
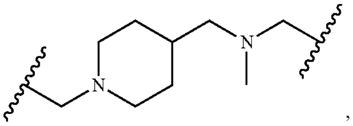,
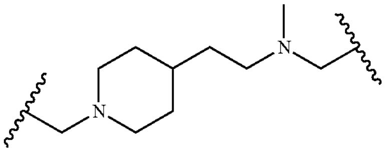,
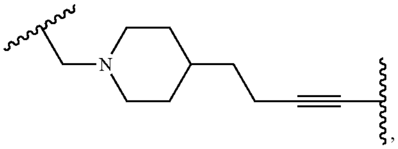,
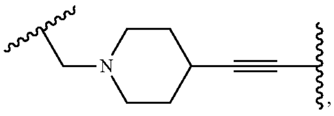,
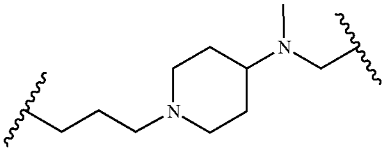,
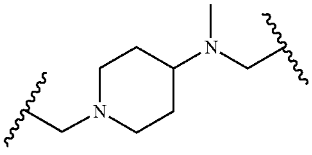,
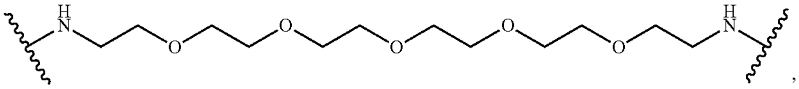,
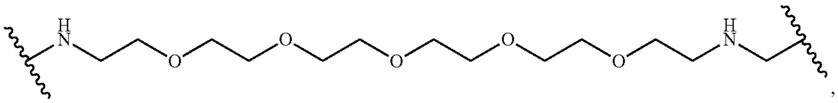,
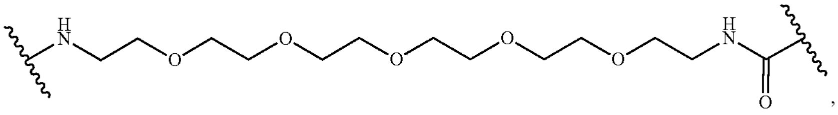, -continued
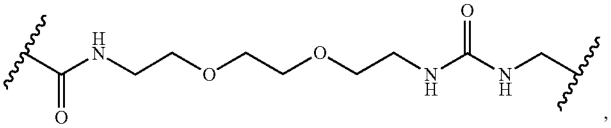,
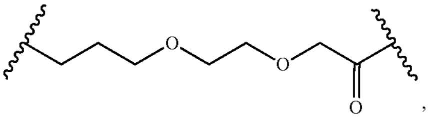,
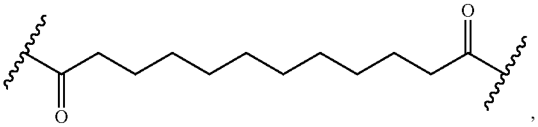,
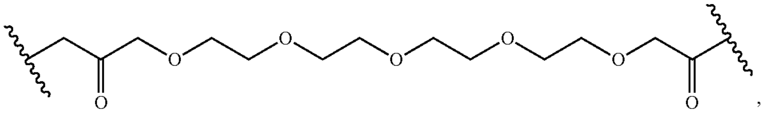,
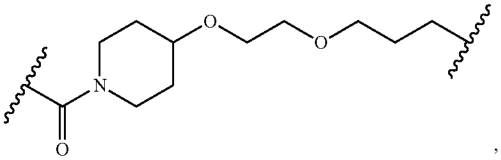,
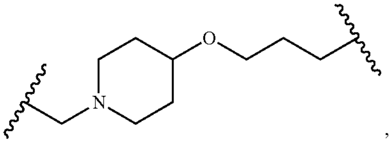,
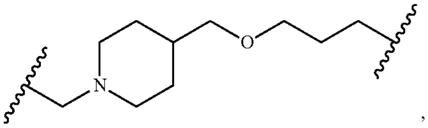,
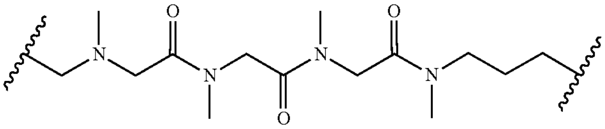,
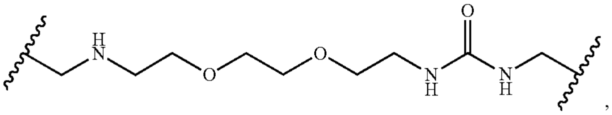,
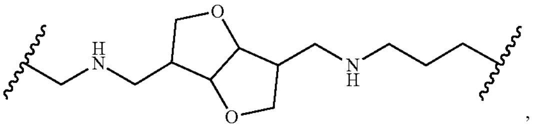,
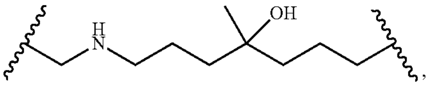,
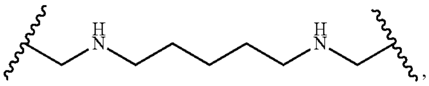,
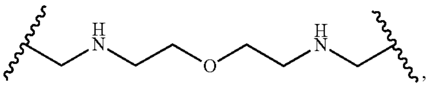,
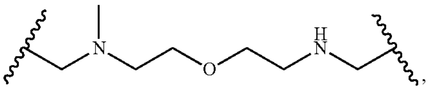,
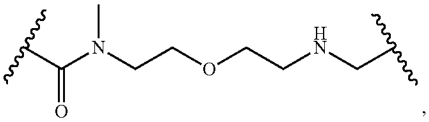,
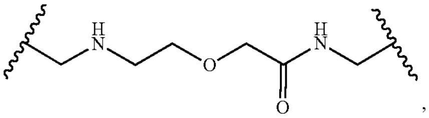,
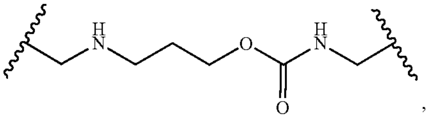,
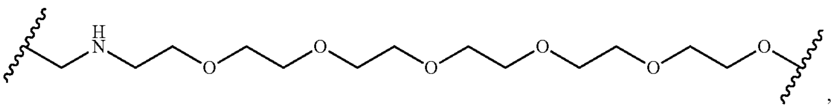,
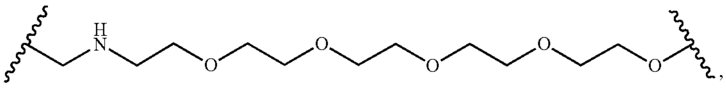,
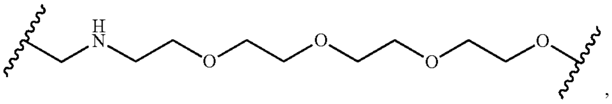,
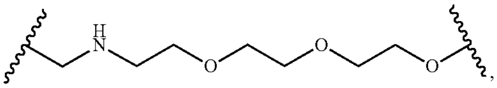,
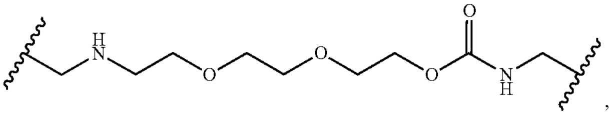,
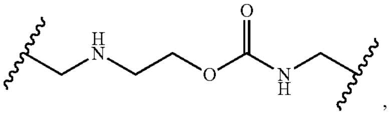, -continued
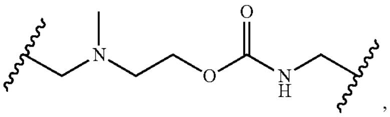 ,
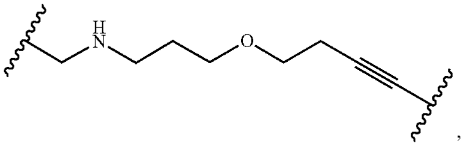 ,
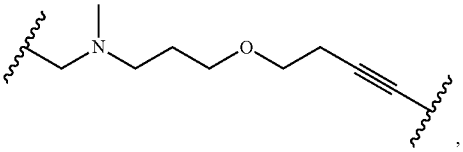 ,
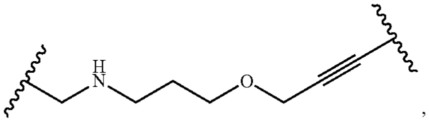 ,
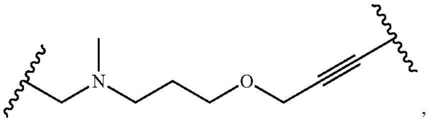 ,
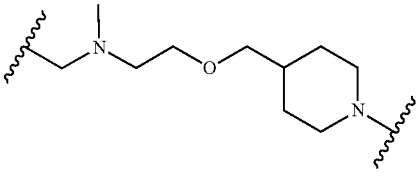 ,
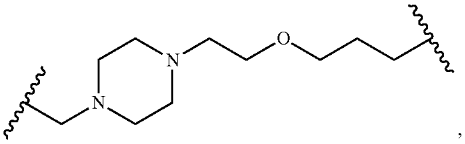 ,
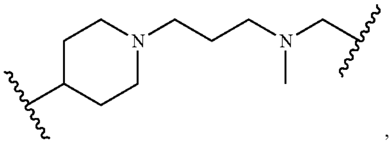 ,
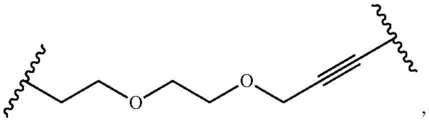 ,
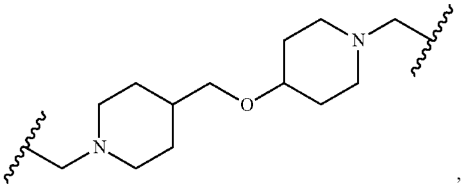 ,
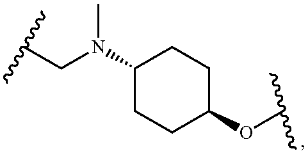 ,
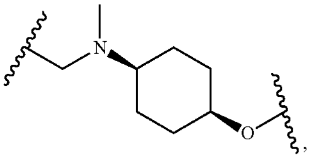 ,
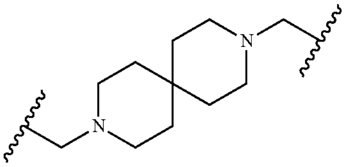 ,
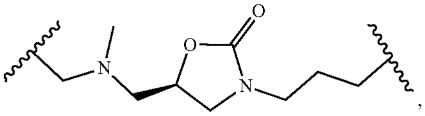 ,
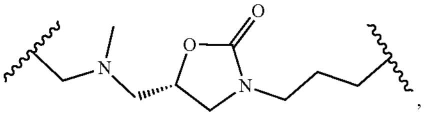 ,
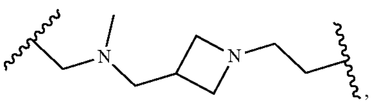 ,
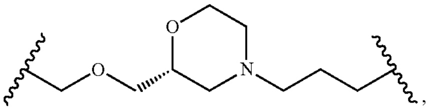 ,
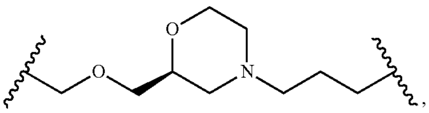 ,
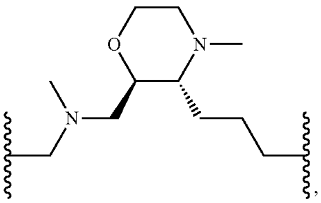 ,
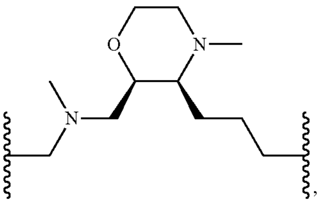 ,
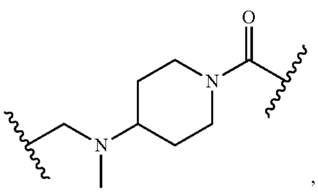 ,
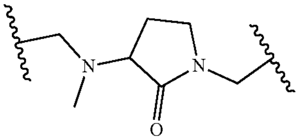 ,
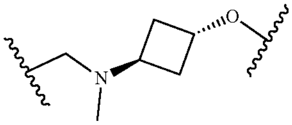 , -continued
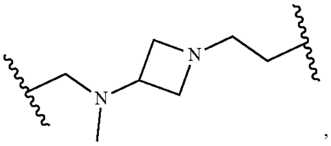, 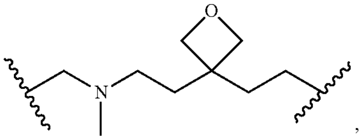, 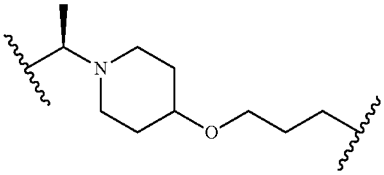,
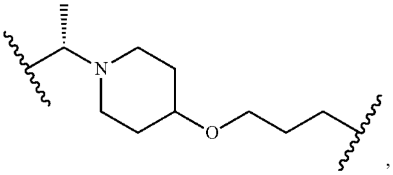, 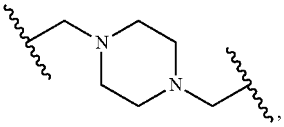, 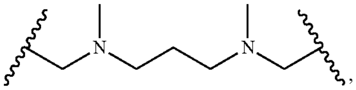,
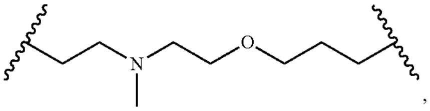, 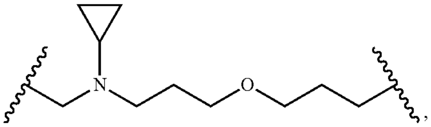,
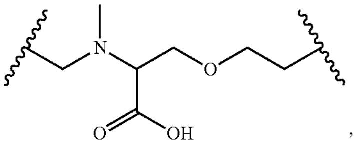, 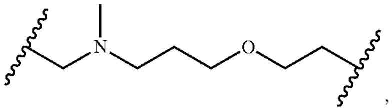,
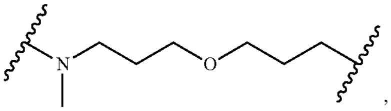, 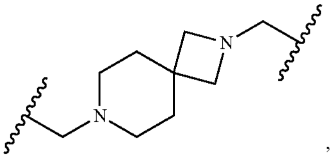, 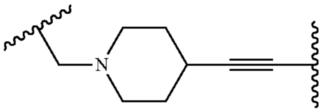,
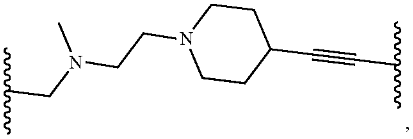, 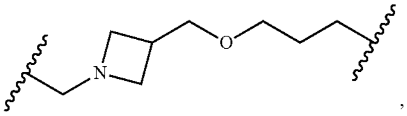, 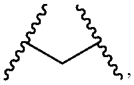, 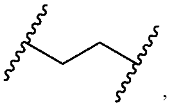,
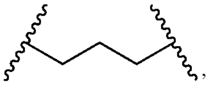, 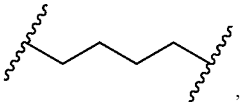, 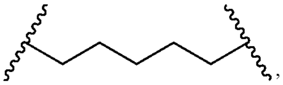, 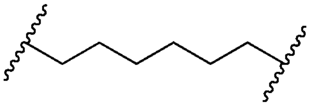,
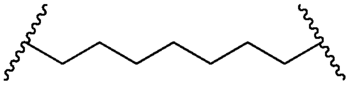, 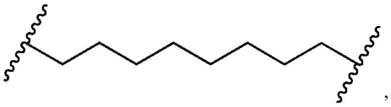,
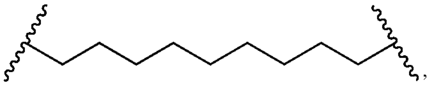, 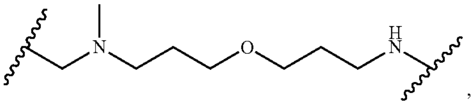,
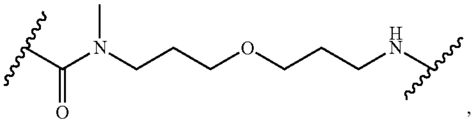, 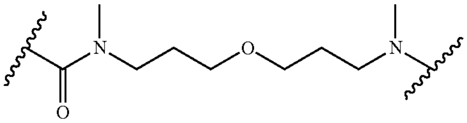,
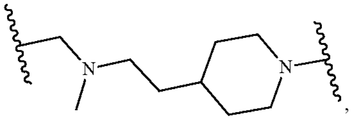, 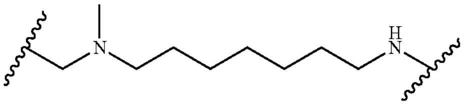,
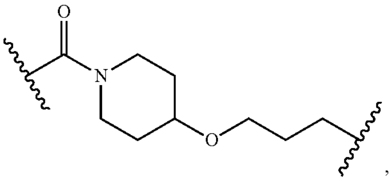, 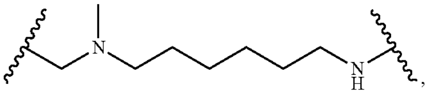, -continued
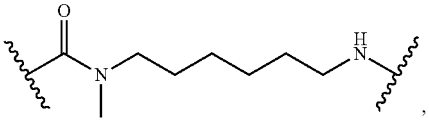 , 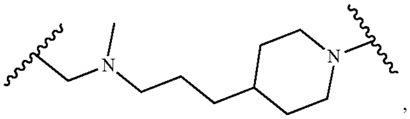 ,
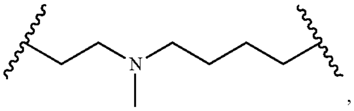 , 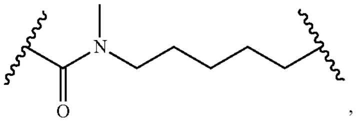 ,
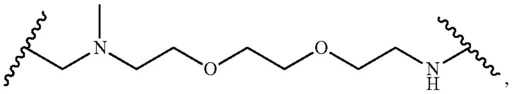 , 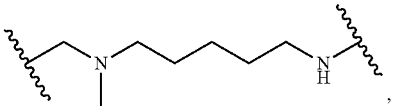 ,
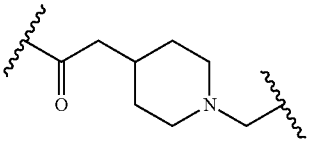 , 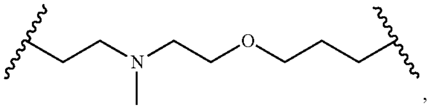 ,
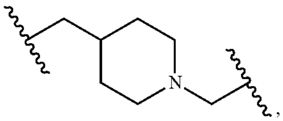 , 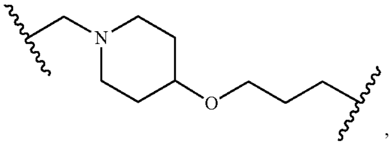 , 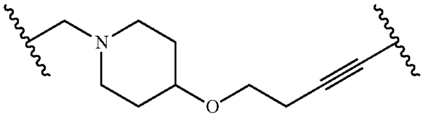 ,
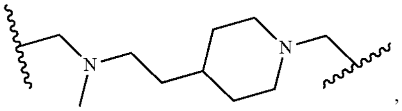 , 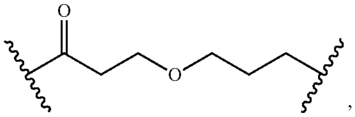 , 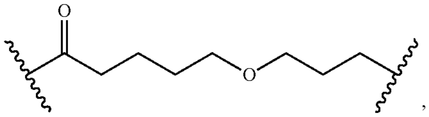 ,
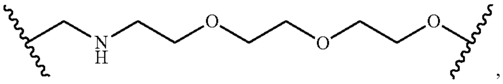 , 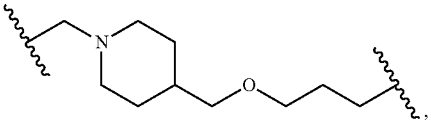 ,
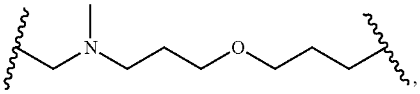 , 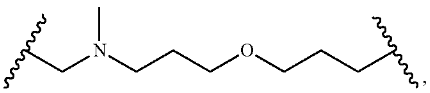 , 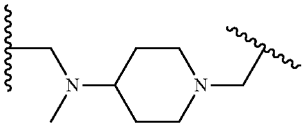 ,
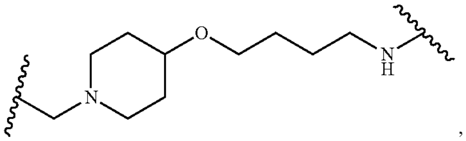 , 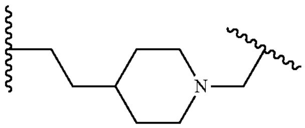 , 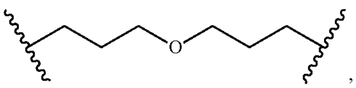 ,
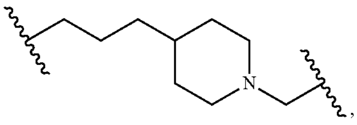 , 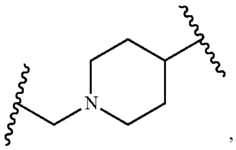 , 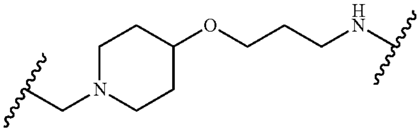 ,
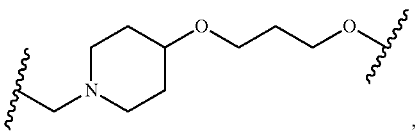 , 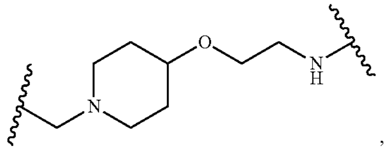 ,
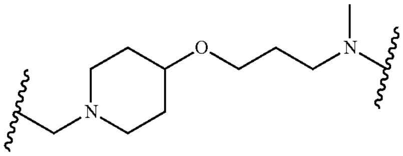 , 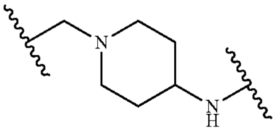 , 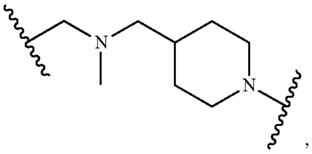 , -continued
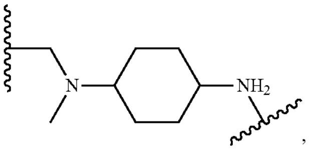, 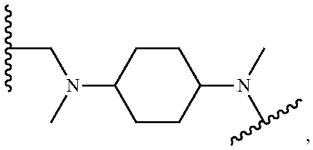, 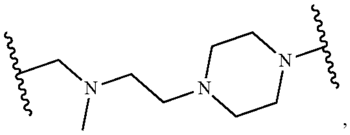,
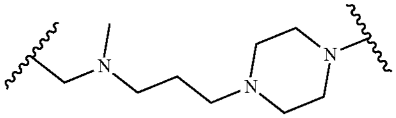, 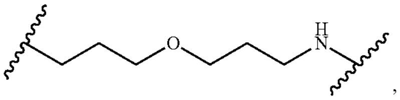, 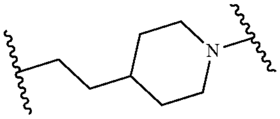,
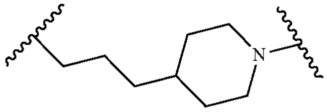, 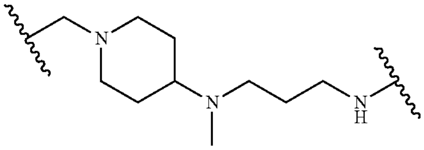,
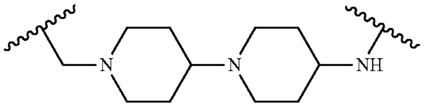, 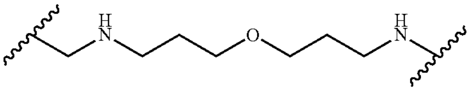,
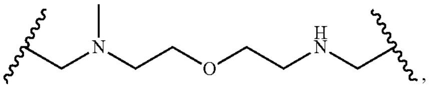, 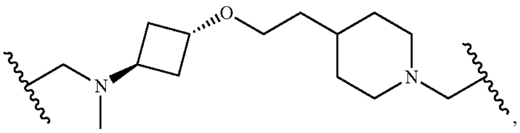,
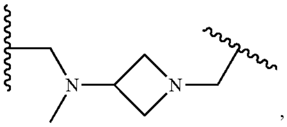, 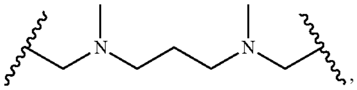, 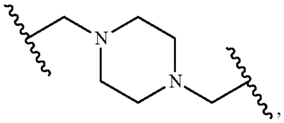,
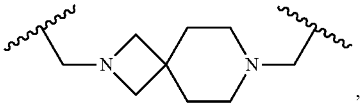, 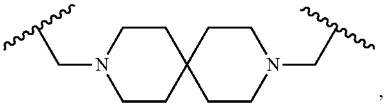,
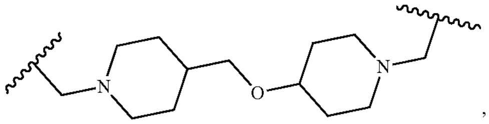, 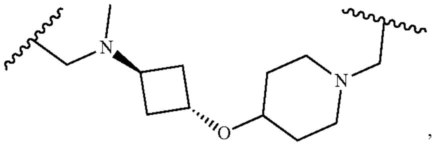,
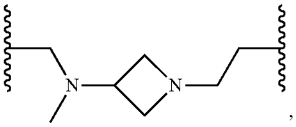, 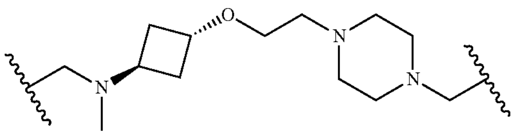,
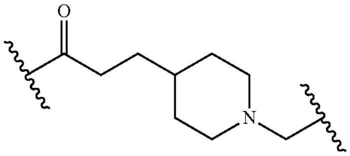, 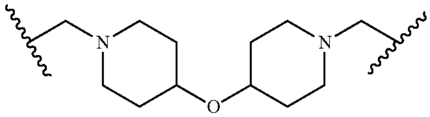, 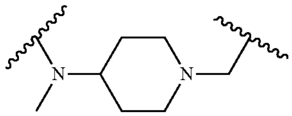,
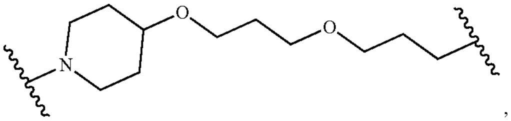, 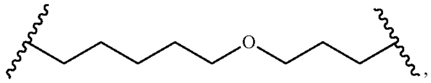,
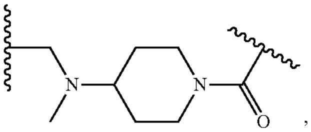, 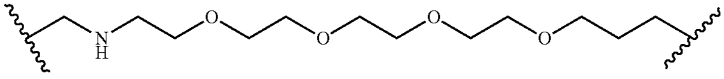, -continued
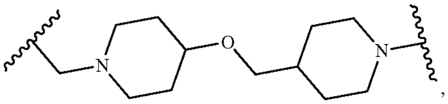,
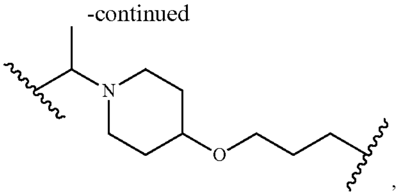,
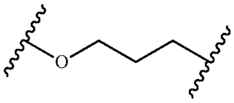,
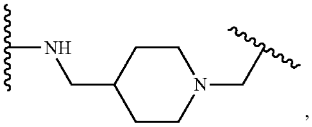,
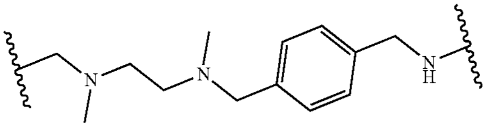,
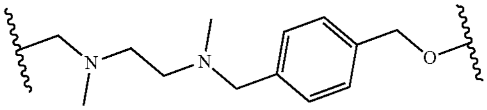,
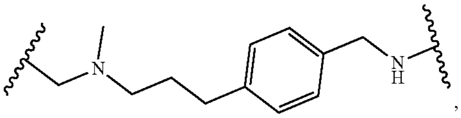,
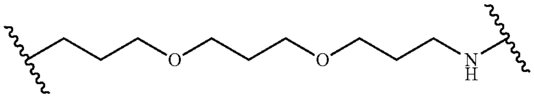,
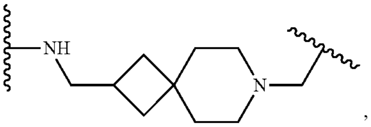,
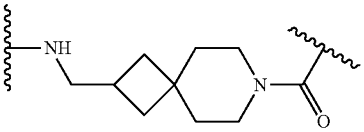,
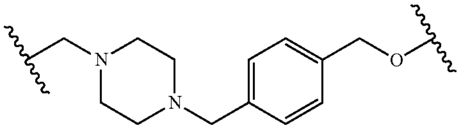,
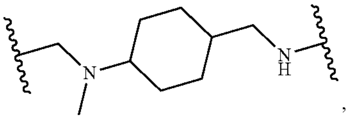,
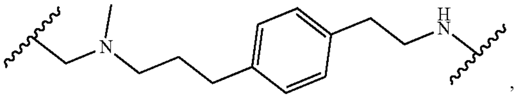,
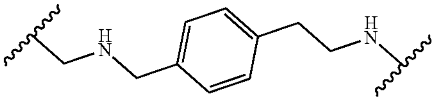,
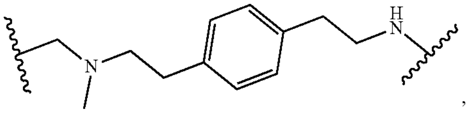,
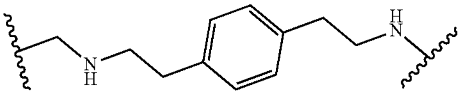,
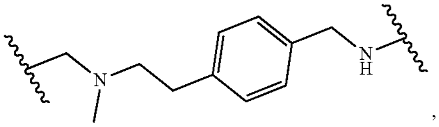,
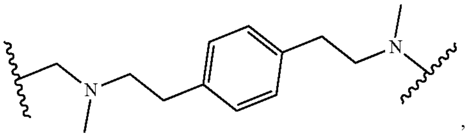,
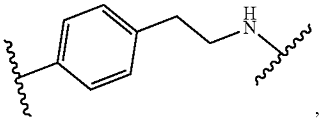,
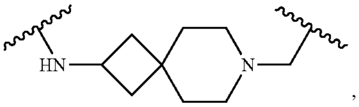,
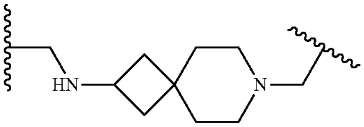,
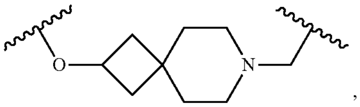,
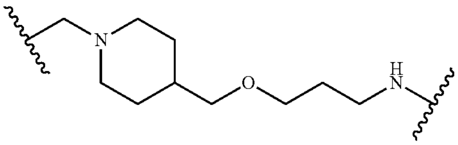,
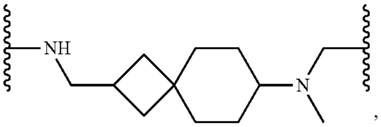,
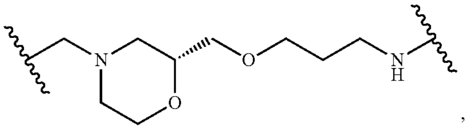,
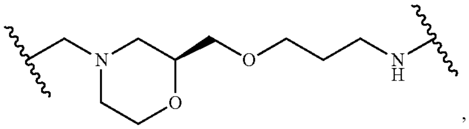,
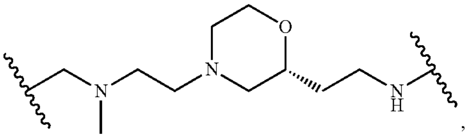,
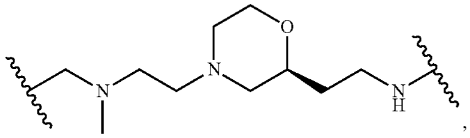, -continued
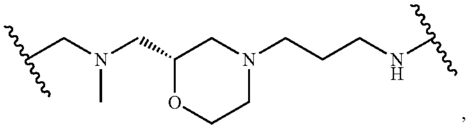,
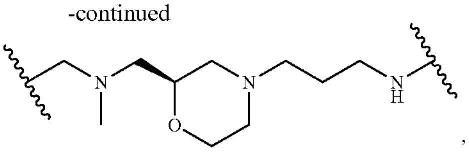,
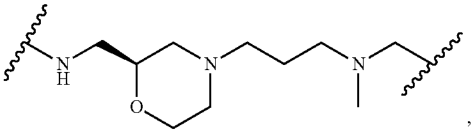,
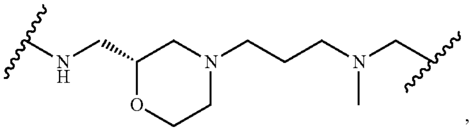,
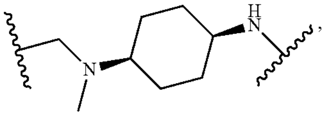,
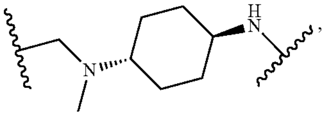,
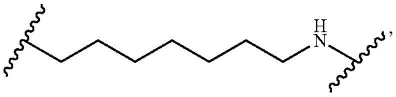,
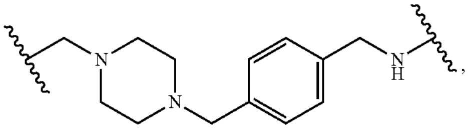,
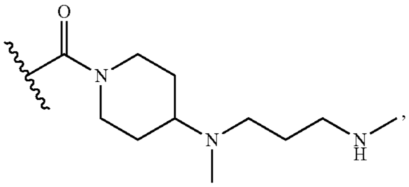,
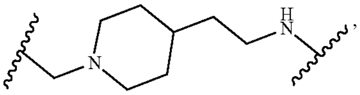,
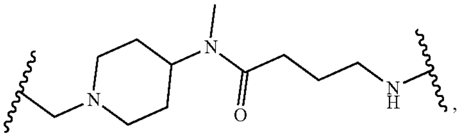,
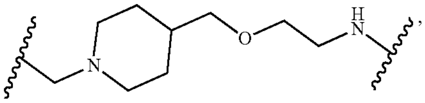,
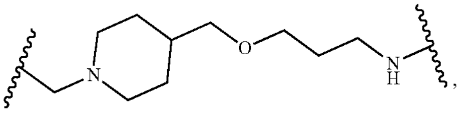,
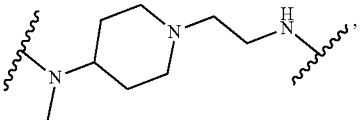,
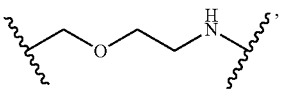,
-continued
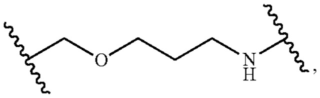,
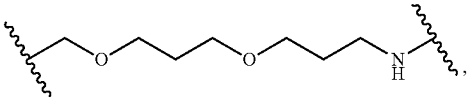,
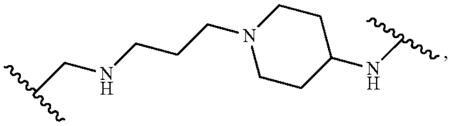,
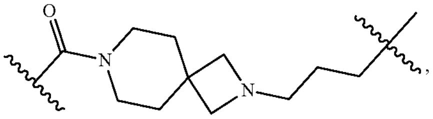,
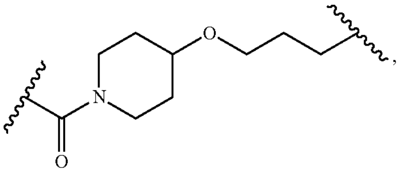,
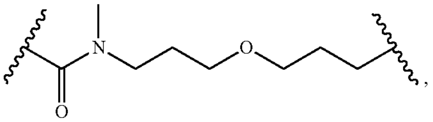,
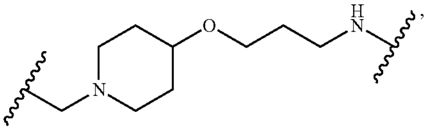,
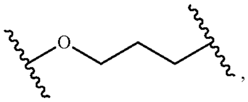,
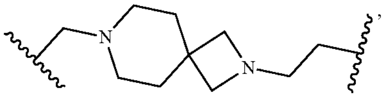,
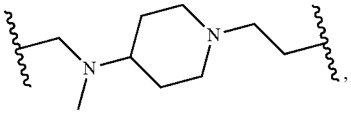,
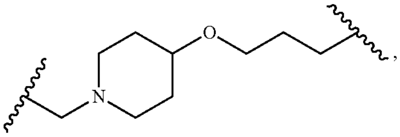, -continued
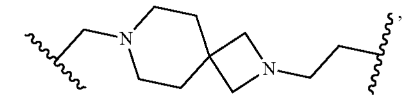,
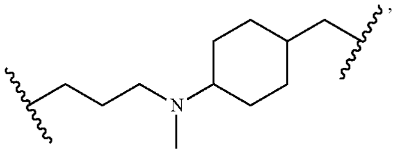,
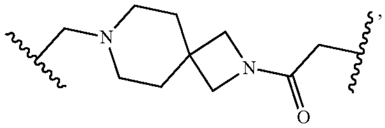,
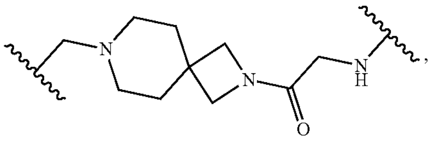,
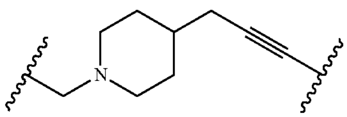,
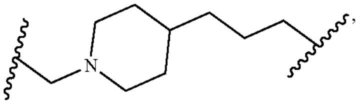,
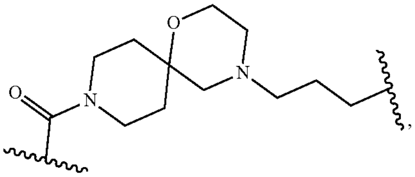,
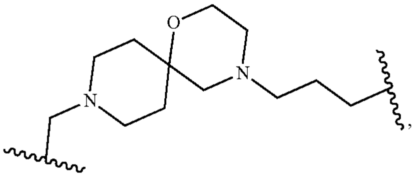,
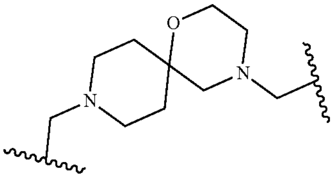,
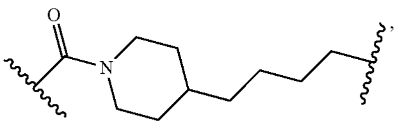,
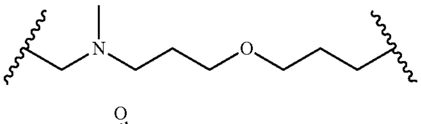,
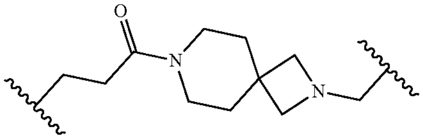,
-continued
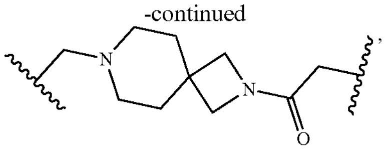,
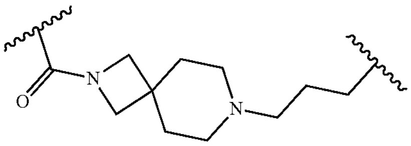,
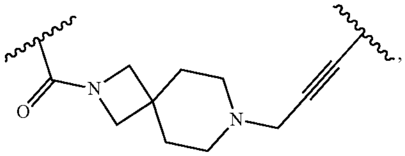,
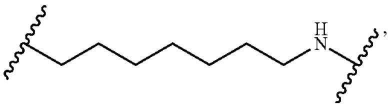,
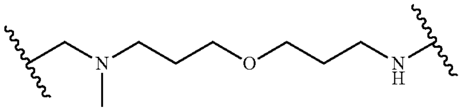,
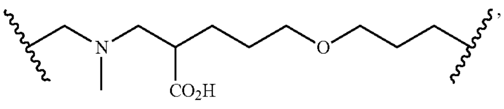,
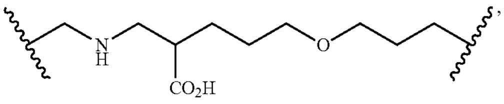,
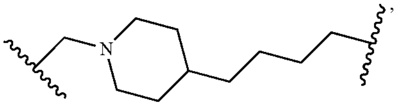,
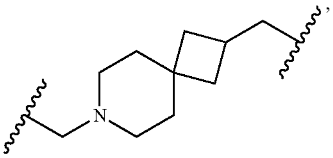,
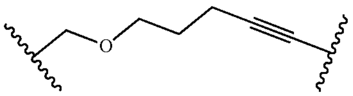,
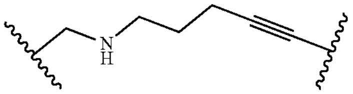,
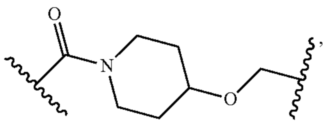,
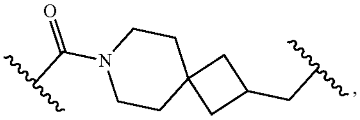,
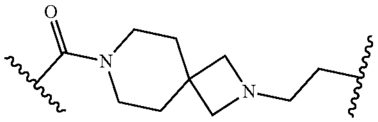, -continued
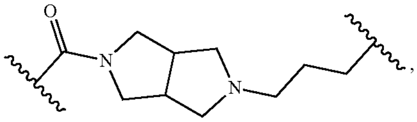,
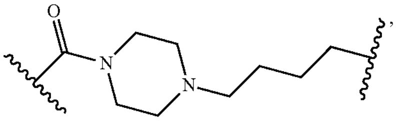,
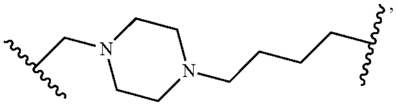,
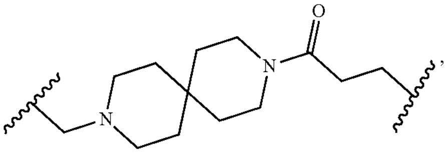,
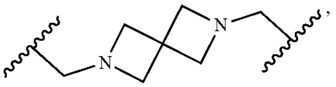,
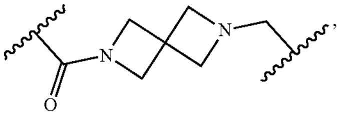,
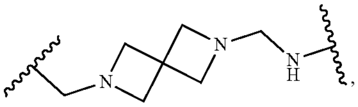,
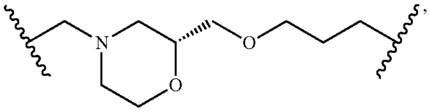,
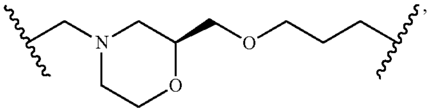,
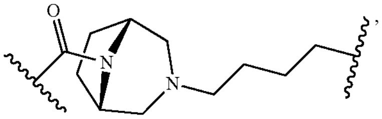,
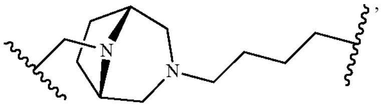,
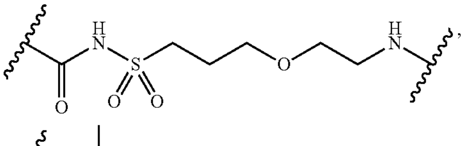,
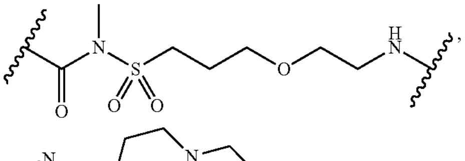,
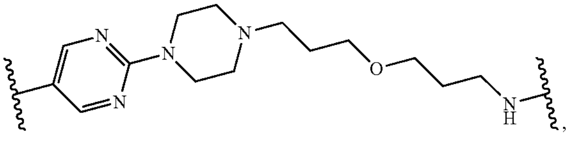,
-continued
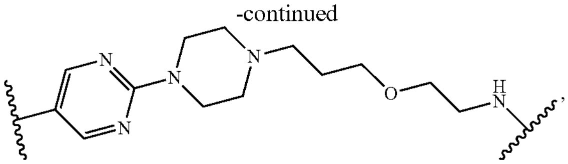,
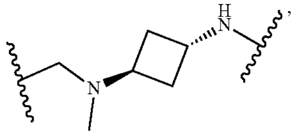,
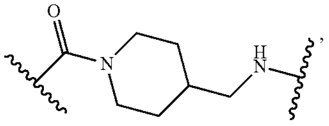,
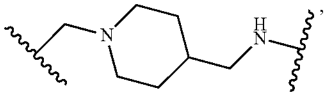,
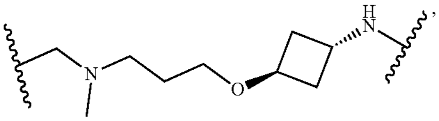,
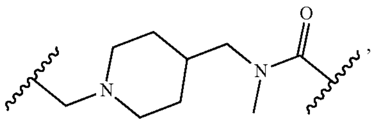,
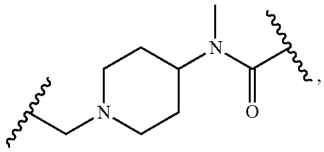,
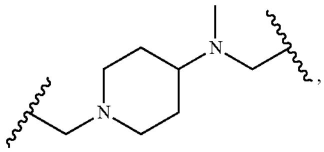,
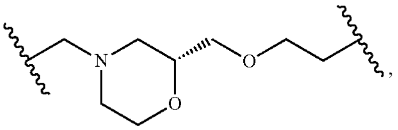,
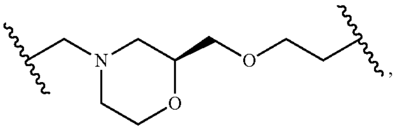,
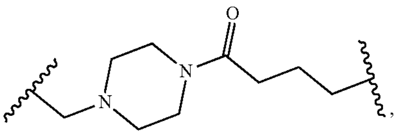,
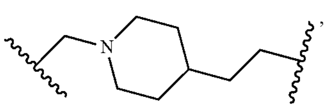,
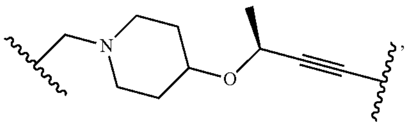, -continued
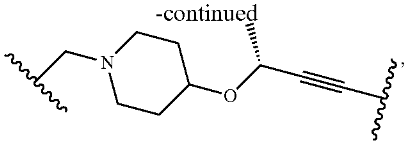,
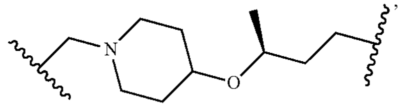,
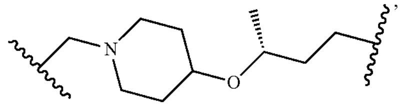,
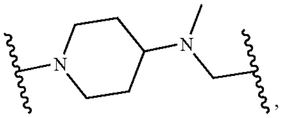,
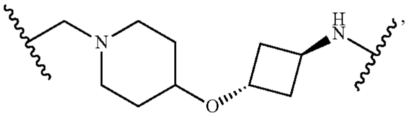,
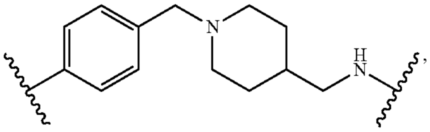,
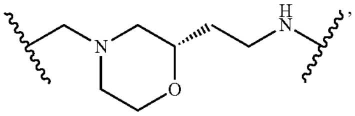,
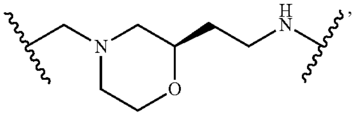,
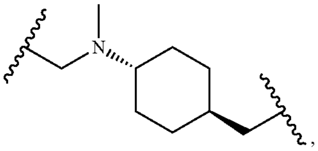,
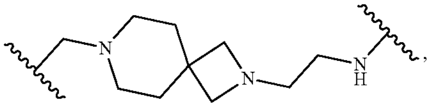,
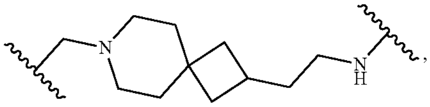,
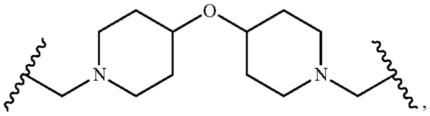,
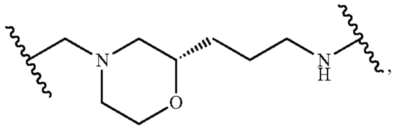,
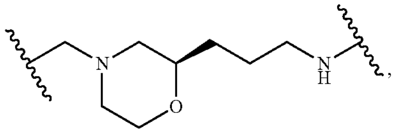,
-continued
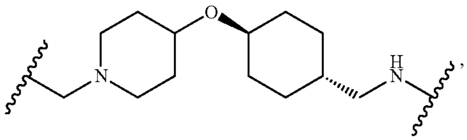,
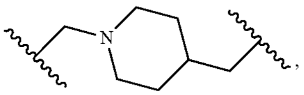,
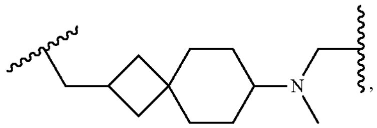,
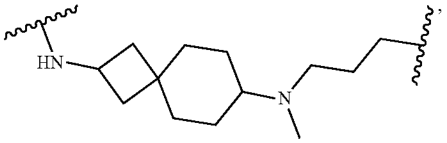,
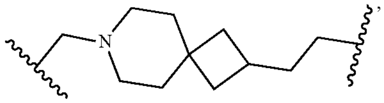,
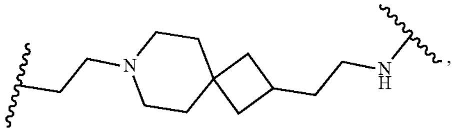,
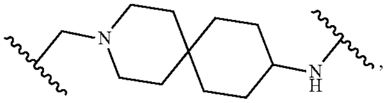,
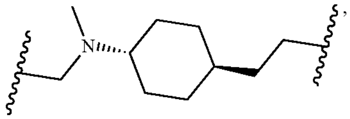,
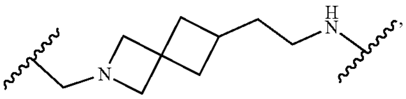,
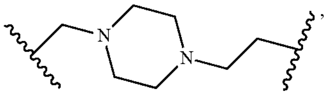, 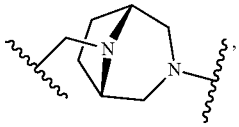,
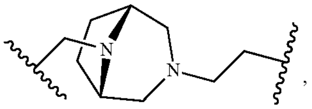, 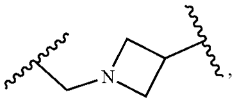,
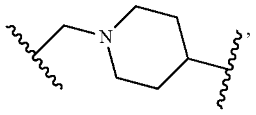, 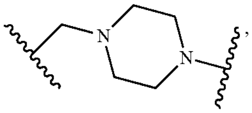,
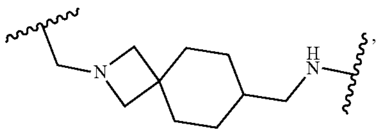,
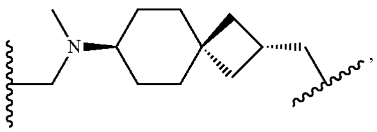, -continued
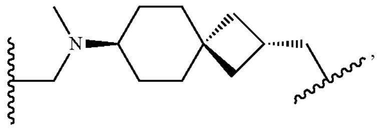
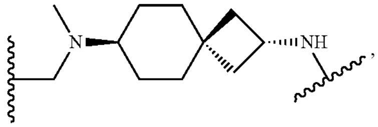
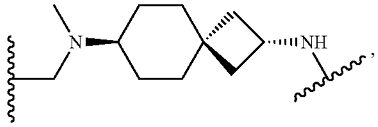
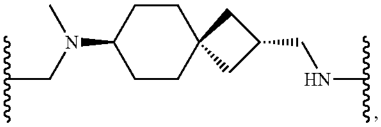
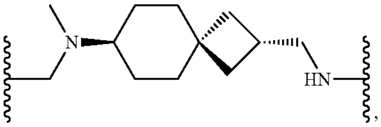
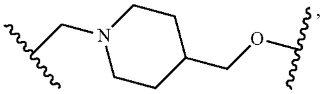
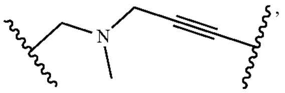
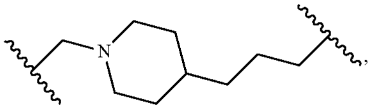
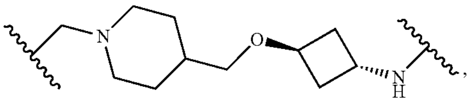
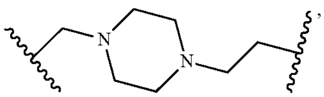
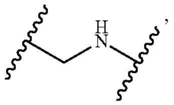
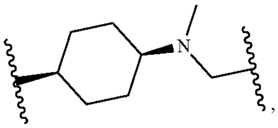
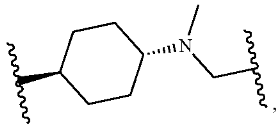
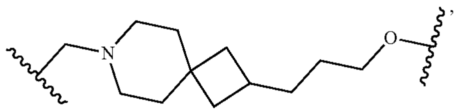
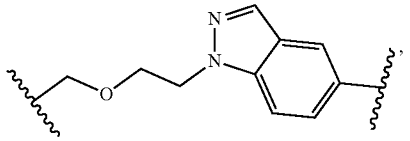
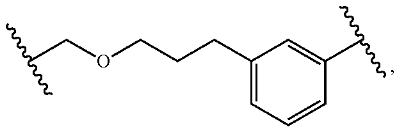
-continued
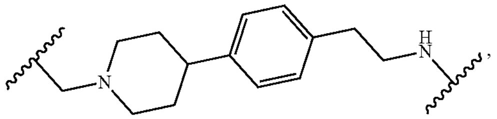
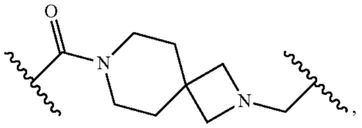
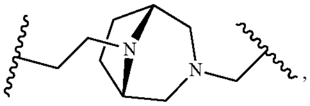
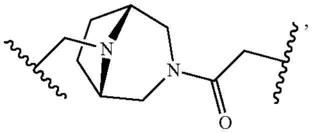
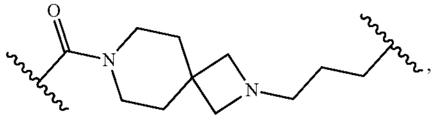
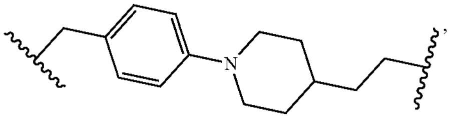
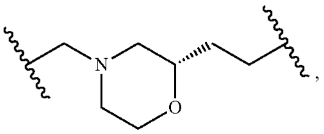
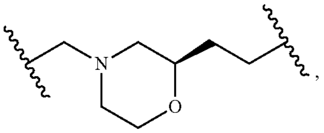
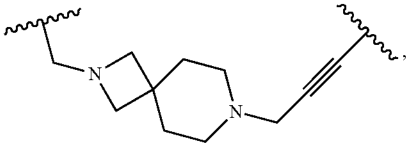
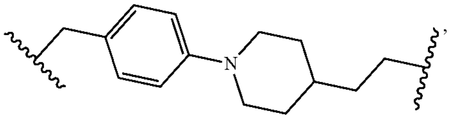
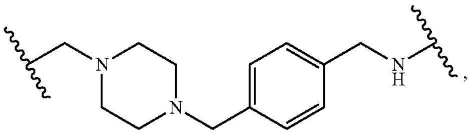
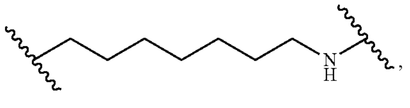
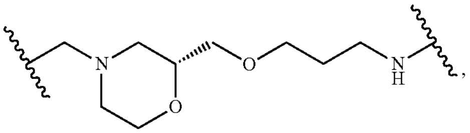

-continued
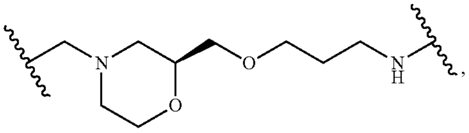
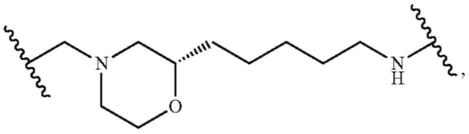
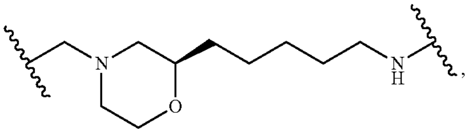
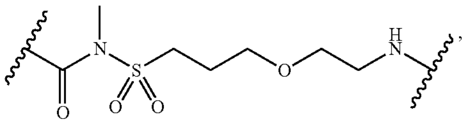
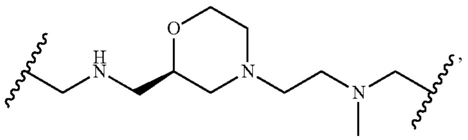
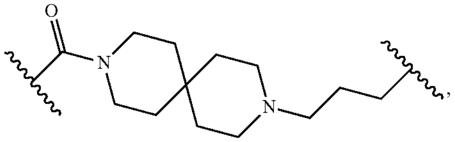
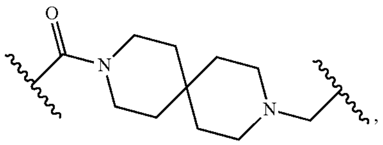
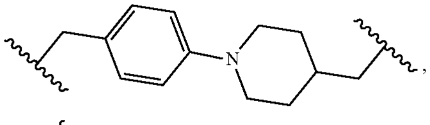
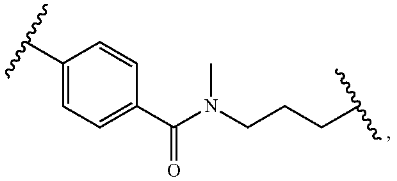
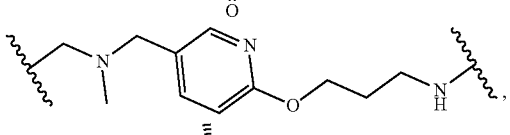
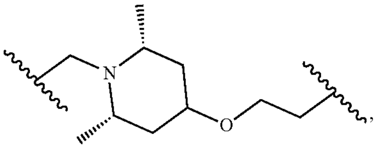
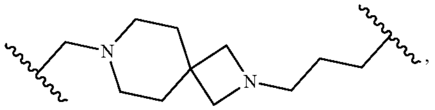
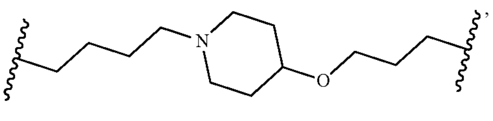
-continued
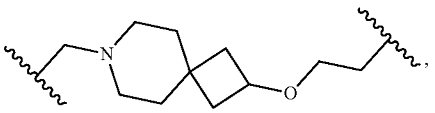
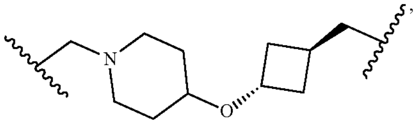
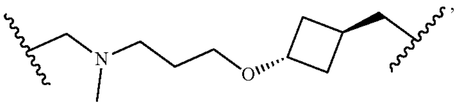
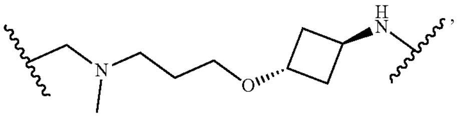
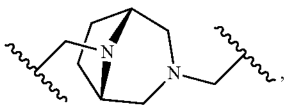
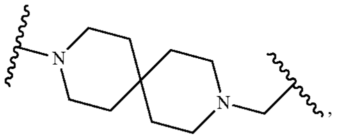
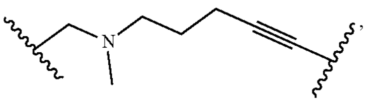
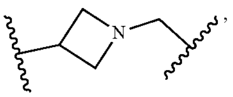
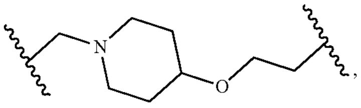
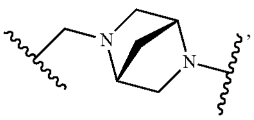
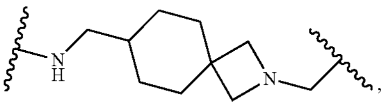
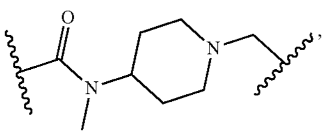
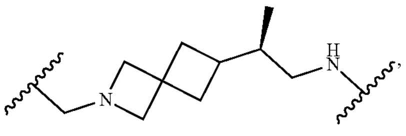
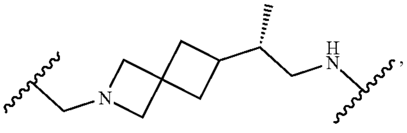

-continued
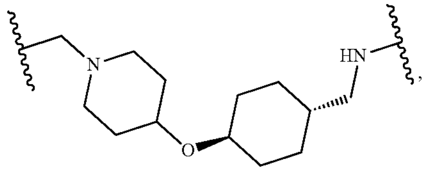
,
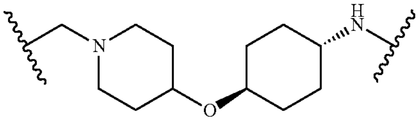
,
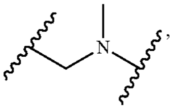
,
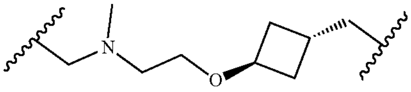
,
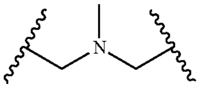
,
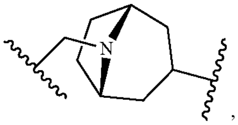
,
-continued
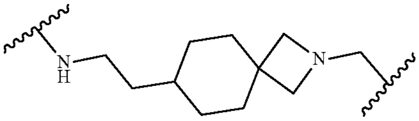
,
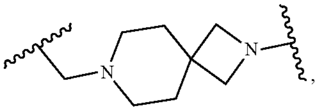
,
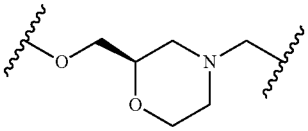
, or
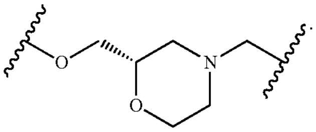
.
* * * * *